(12) United States Patent
Nasveschuk et al.

(10) Patent No.: US 12,421,220 B2
(45) Date of Patent: Sep. 23, 2025

(54) BICYCLIC-SUBSTITUTED GLUTARIMIDE CEREBLON BINDERS

(71) Applicant: C4 THERAPEUTICS, INC., Watertown, MA (US)

(72) Inventors: Christopher G. Nasveschuk, Stoneham, MA (US); Kiel Lazarski, Boston, MA (US); Yanke Liang, Belmont, MA (US); Alexander W. Hird, Belmont, MA (US); Ning Yin, Lexington, MA (US); Andrew Charles Good, Bideford (GB); Hongwei Huang, Bedford, MA (US); Scott Joseph Eron, Waltham, MA (US); Gesine Kerstin Veits, Somerville, MA (US)

(73) Assignee: C4 THERAPEUTICS, INC., Watertown, MA (US)

( * ) Notice: Subject to any disclaimer, the term of this patent is extended or adjusted under 35 U.S.C. 154(b) by 0 days.

(21) Appl. No.: 18/972,557

(22) Filed: Dec. 6, 2024

(65) Prior Publication Data

US 2025/0122179 A1   Apr. 17, 2025

Related U.S. Application Data

(63) Continuation of application No. PCT/US2023/024622, filed on Jun. 6, 2023.

(60) Provisional application No. 63/349,509, filed on Jun. 6, 2022.

(51) Int. Cl.
| | |
|---|---|
| *C07D 413/04* | (2006.01) |
| *A61K 31/4709* | (2006.01) |
| *A61K 31/496* | (2006.01) |
| *A61K 31/5377* | (2006.01) |
| *A61K 31/5383* | (2006.01) |
| *A61K 31/5415* | (2006.01) |
| *C07D 401/04* | (2006.01) |
| *C07D 401/14* | (2006.01) |
| *C07D 413/14* | (2006.01) |
| *C07D 417/14* | (2006.01) |
| *C07D 487/10* | (2006.01) |
| *C07D 498/04* | (2006.01) |

(52) U.S. Cl.
CPC ........ *C07D 413/04* (2013.01); *A61K 31/4709* (2013.01); *A61K 31/496* (2013.01); *A61K 31/5377* (2013.01); *A61K 31/5383* (2013.01); *A61K 31/5415* (2013.01); *C07D 401/04* (2013.01); *C07D 401/14* (2013.01); *C07D 413/14* (2013.01); *C07D 417/14* (2013.01); *C07D 487/10* (2013.01); *C07D 498/04* (2013.01)

(58) Field of Classification Search
CPC .................................................. C07D 413/04
USPC ..................................................... 514/210.21
See application file for complete search history.

(56) References Cited

U.S. PATENT DOCUMENTS

| | | |
|---|---|---|
| 5,635,517 A | 6/1997 | Muller et al. |
| 6,306,663 B1 | 10/2001 | Kenten et al. |
| 7,041,298 B2 | 5/2006 | Deshaies et al. |
| 7,208,157 B2 | 4/2007 | Deshaies et al. |
| 2013/0190340 A1 | 7/2013 | Hedstrom et al. |
| 2014/0302523 A1 | 10/2014 | Crews et al. |
| 2014/0356322 A1 | 12/2014 | Crews et al. |
| 2015/0274738 A1 | 10/2015 | Gray et al. |
| 2015/0291562 A1 | 10/2015 | Crew et al. |
| 2016/0058872 A1 | 3/2016 | Crew et al. |
| 2016/0176916 A1 | 6/2016 | Bradner et al. |
| 2018/0085465 A1 | 3/2018 | Bradner et al. |
| 2019/0076539 A1 | 3/2019 | Phillips et al. |
| 2021/0009559 A1 | 1/2021 | Henderson et al. |
| 2021/0177825 A1 | 6/2021 | Burnette et al. |

FOREIGN PATENT DOCUMENTS

| | | |
|---|---|---|
| WO | WO 2002/059106 A1 | 8/2002 |
| WO | WO 2008/027542 A2 | 3/2008 |
| WO | WO 2008/033567 A1 | 3/2008 |
| WO | WO 2008/039489 A2 | 4/2008 |
| WO | WO 2008/115516 A2 | 9/2008 |
| WO | WO 2009/042177 A1 | 4/2009 |
| WO | WO 2010/053732 A1 | 5/2010 |
| WO | WO 2010/107485 A1 | 9/2010 |
| WO | WO 2015/160845 A1 | 10/2015 |
| WO | WO 2016/065139 A1 | 4/2016 |
| WO | WO 2016/105518 A1 | 6/2016 |
| WO | WO 2016/118666 A1 | 7/2016 |
| WO | WO 2016/149668 A1 | 9/2016 |
| WO | WO 2016/191178 A1 | 12/2016 |
| WO | WO 2016/197032 A1 | 12/2016 |
| WO | WO 2016/197114 A1 | 12/2016 |

(Continued)

OTHER PUBLICATIONS

Agafonov, Roman et al., Poster Presentation titled "Quantitative and high throughput method for measuring complex formation between target proteins and E3 ubiquitin ligase" EMBO, Sep. 16, 2017.

(Continued)

*Primary Examiner* — Kahsay Habte

(74) *Attorney, Agent, or Firm* — Knowles Intellectual Property Strategies, LLC

(57) ABSTRACT

This invention provides Degron compounds which bind to cereblon which is a component of the E3 ubiquitin ligase. The Degrons provided herein can be used to modulate the activity of cereblon either alone or as covalently linked to a Tail. Alternatively, the Degron can be linked to a Targeting Ligand which binds to a Target Protein for protein degradation.

26 Claims, 501 Drawing Sheets

(56) References Cited

FOREIGN PATENT DOCUMENTS

| WO | WO 2017/007612 A1 | 1/2017 |
|---|---|---|
| WO | WO 2017/024317 A2 | 2/2017 |
| WO | WO 2017/024318 A1 | 2/2017 |
| WO | WO 2017/024319 A1 | 2/2017 |
| WO | WO 2017/079267 A1 | 5/2017 |
| WO | WO 2017/161119 A1 | 9/2017 |
| WO | WO 2017/176708 A1 | 10/2017 |
| WO | WO 2017/201069 A1 | 11/2017 |
| WO | WO 2017/201449 A1 | 11/2017 |
| WO | WO 2018/053354 A1 | 3/2018 |
| WO | WO 2018/071606 A1 | 4/2018 |
| WO | WO 2018/085247 A1 | 5/2018 |
| WO | WO 2018/102067 A2 | 6/2018 |
| WO | WO 2018/102725 A1 | 6/2018 |
| WO | WO 2018/118598 A1 | 6/2018 |
| WO | WO 2018/118947 A1 | 6/2018 |
| WO | WO 2018/119357 A1 | 6/2018 |
| WO | WO 2018/119441 A1 | 6/2018 |
| WO | WO 2018/119448 A1 | 6/2018 |
| WO | WO 2018/140809 A1 | 8/2018 |
| WO | WO 2018/144649 A1 | 8/2018 |
| WO | WO 2018/169777 A1 | 9/2018 |
| WO | WO 2018/183411 A1 | 10/2018 |
| WO | WO 2018/189554 A1 | 10/2018 |
| WO | WO 2018/191199 A1 | 10/2018 |
| WO | WO 2019/060693 A1 | 3/2019 |
| WO | WO 2019/060742 A1 | 3/2019 |
| WO | WO 2019/140387 A1 | 7/2019 |
| WO | WO 2019/152440 A1 | 8/2019 |
| WO | WO 2019/165229 A1 | 8/2019 |
| WO | WO 2019/199816 A1 | 10/2019 |
| WO | WO 2019/213005 A1 | 11/2019 |
| WO | WO 2020/006262 A1 | 1/2020 |
| WO | WO 2020/006264 A1 | 1/2020 |
| WO | WO 2020/006265 A1 | 1/2020 |
| WO | WO 2020/010227 A1 | 1/2020 |
| WO | WO 2020/023851 A1 | 1/2020 |
| WO | WO 2020/041331 A1 | 2/2020 |
| WO | WO 2020/051564 A1 | 3/2020 |
| WO | WO 2020/081450 A1 | 4/2020 |
| WO | WO 2021/162493 A1 | 8/2021 |

OTHER PUBLICATIONS

Bartlett et al., "The evolution of thalidomide and its IMiD derivatives as anticancer agents" Nat. Rev. Cancer, 4, 314-322, Apr. 1, 2004.
Berndsen et al., "New insights into ubiquitin E3 ligase mechanism" Nat. Struct. Mol. Biol., 21, 301-307, Jan. 28, 2014.
Bondeson et al., "Catalytic in Vivo Protein Knockdown by Small-Molecule Protacs" Nat. Chem. Biol., 11, 611-617, May 8, May 8, 2015.
Buckley et al., "HaloPROTACS: Use of Small Molecule PROTACS to Induce Degradation of HaloTag Fusion Proteins" ACS Chemical Biology, 10:1831-1837, Jun. 12, 2015.
Buckley et al., "Small-Molecule Control of Intracellular Protein Levels through Modulation of the Ubiquitin Proteasome System" Angewandte Reviews, 53:2312-2330, Jan. 12, 2014.
Chamberlain et al., "Structure of the human cereblon-DDB1-lenalidomide complex reveals basis for responsiveness to thalidomide analogs" Nature Structural and Molecule Biology, 21(9):803-809, Aug. 2014.
Crew, C. M., "Targeting the undruggable proteome: the small molecules of my dreams" Chemistry and Biology, 17(6):551-555, Jun. 25, 2010.
Deshaies et al., "Ring domain E3 ubiquitin ligases" Ann. Rev. Biochem., 78:399-434, Jul. 7, 2009.
Elam, W.A., et al, Poster Presentation titled "Application of Biophysical Techniques to the Targeted Protein Degradation Therapeutic Strategy" Sep. 24, 2017.
Faden et al., "Generic tools for conditionally altering protein abundance and phenotypes on demand" Biol. Chem., 395(7-8):737-762, Jul. 8, 2014.
Fischer et al., "Structure of the DDB1-CRBN E3 ubiquitin ligase in complex with thalidomide" Nature, 512:49-53, Jul. 16, 2014.
Fischer et al., "The Molecular Basis of CRL4DDB2/CSA Ubiquitin Ligase Architecture, Targeting, and Activation" Cell, 147:1024-1039, Nov. 23, 2011.
Fisher et al., "Targeted protein degradation and the enzymology of degraders" Current Opinion of Chemical Biology, 44, 47-55, Jun. 2018.
Henderson, C., Presentation titled "Development of AchillesTAG degradation systems and their application to control CAR-T activity" ChemBio in the hub, Cambridge, MA. Oct. 22, 2018.
International Search Report and Written Opinion for PCT/US23/24622, 10 pages, mailed on Nov. 2, 2023.
Kronke et al., "Lenalidomide Causes Selective Degradation of IKZF1 and IKZF3 in Multiple Myeloma Cells" Science, 343(6168):301-305, Jan. 17, 2014.
Kronke et al., "Lenalidomide induces ubiquitination and degradation of CDK1[alpha] in del(5q) MDS" Nature, 523(7559):183-188, Jul. 1, 2015.
Nasveschuk, C., Presentation titled "Advances in the Medicinal Chemistry of Targeted Protein Degradation" Aug. 7, 2018.
Patel, J., Poster Presentation titled "Diverse Utility of Targeted Protein Degradation at C4 Therapeutics" Sep. 17, 2017.
Phillips, A., Presentation titled "Targeted Protein Degradation" Applied Pharmaceutical Chemistry, Cambridge, MA. Apr. 5, 2018.
Phillips, A., Presentation titled "Small molecule driven targeted protein degradation" ChemBio in the hub, Cambridge, MA. Oct. 22, 2018.
Schneekloth et al., "Targeted Intracellular Protein Degradation Induced by a Small Molecule: En Route to Chemical Proteomics" Bioorganic and Medicinal Chemistry Letters, 18:5904-5908, Jul. 31, 2008.
Terpos, E. et al., "Pomalidomide: a novel drug to treat relapsed and refractory multiple myeloma" Oncotargets and Therapy, 6:531, 2013.
Toure et al., "Small-Molecule Protacs: New Approaches to Protein Degradation" Angew. Chem. Int. Ed., 55, 1966-1973, Jan. 12, 2016.
Vieux, Ellen et al., Poster Presentation titled "Measuring Small Molecule Induced Ubiquitination of Proteins" EMBO, Sep. 18, 2017.
Winter et al., "Drug Development. Phthalimide Conjugation as a Strategy for in Vivo Target Protein Degradation" Science, 348, 1376-1381, May 21, 2015.
Zeid, Rhamy, Presentation titled "Targeted protein degradation as a novel therapeutic approach" Gordon Research Conference, Jun. 26, 2017.
Zhou et al., "Harnessing the Ubiquitination Machinery to Target the Degradation of Specific Cellular Proteins" Mol. Cell, 6, 751-756, Sep. 2000.
U.S. Pat. No. 11,802,131, B2, U.S. Appl. No. 16/809,336, Norcross et al., Mar. 4, 2020.
U.S. Pat. No. 10,646,575, B2, U.S. Appl. No. 16/186,339, Phillips et al., May 12, 2020.
U.S. Pat. No. 10,660,968, B2, U.S. Appl. No. 16/186,334, Phillips et al., May 26, 2020.
U.S. Pat. No. 10,849,982, B2, U.S. Appl. No. 16/186,341, Phillips et al., Dec. 1, 2020.
U.S. Pat. No. 10,905,768, B1, U.S. Appl. No. 16/872,225, Phillips et al., Feb. 2, 2021.
U.S. Pat. No. 11,185,592, B2, U.S. Appl. No. 16/882,236, Phillips et al., Nov. 30, 2021.
U.S. Pat. No. 11,254,672, B2, U.S. Appl. No. 16/809,325, Norcross et al., Feb. 22, 2022.
U.S. Pat. No. 11,401,256, B2, U.S. Appl. No. 16/809,345, Norcross et al., Jul. 13, 2022.
U.S. Pat. No. 11,407,732, B1, U.S. Appl. No. 17/498,617, Henderson et al., Aug. 9, 2022.
U.S. Pat. No. 11,459,335, B2, U.S. Appl. No. 16/721,650, Phillips et al., Sep. 14, 2022.

(56) References Cited

OTHER PUBLICATIONS

U.S. Pat. No. 11,524,949, B2, U.S. Appl. No. 16/874,475, Phillips et al., Dec. 13, 2022.
U.S. Pat. No. 11,584,748, B2, U.S. Appl. No. 17/072,896, Nasveschuk et al., Feb. 1, 2023.
U.S. Pat. No. 11,623,929, B2, U.S. Appl. No. 17/103,621, Nasveschuk et al., Mar. 22, 2023.
U.S. Pat. No. 11,673,902, B2, U.S. Appl. No. 17/843,769, Nasveschuk et al., Jun. 13, 2023.
U.S. Pat. No. 11,691,972, B2, U.S. Appl. No. 17/541,035, Nasveschuk et al., Jul. 4, 2023.
U.S. Pat. No. 11,787,802, B2, U.S. Appl. No. 17/576,582, Norcross et al., Oct. 17, 2023.
U.S. Pat. No. 11,753,397, B2, U.S. Appl. No. 17/031,550, Henderson et al., Aug. 23, 2023.
U.S. Pat. No. 11,992,531, B2, U.S. Appl. No. 17/107,781, Phillips et al., May 28, 2024.
U.S. Pat. No. 12,048,747, B2, U.S. Appl. No. 17/121,389, Phillips et al., Jul. 30, 2024.
U.S. Pat. No. 12,048,748, B2, U.S. Appl. No. 17/524,558, Phillips et al., Jul. 30, 2024.
U.S. Pat. No. 12,049,464, B2, U.S. Appl. No. 17/901,775, Nasveschuk et al., Jul. 30, 2024.
U.S. Pat. No. 12,076,405, B2, U.S. Appl. No. 17/164,446, Phillips et al., Sep. 3, 2024.
U.S. Pat. No. 12,091,397, B2, U.S. Appl. No. 17/878,753, Norcross et al., Sep. 17, 2024.
U.S. Pat. No. 12,157,735, B2, U.S. Appl. No. 17/965,569, Nasveschuk et al., Dec. 3, 2024.
U.S. Pat. No. 12,180,225, B2, U.S. Appl. No. 17/959,144, Phillips et al., filed Dec. 31, 2024.
U.S. Pat. No. 12,227,504, B2, U.S. Appl. No. 18/100,992, Nasveschuk et al., Feb. 18, 2025.
US, 2022/0372016, A1, U.S. Appl. No. 17/351,935, Phillips et al., filed Nov. 24, 2022.
US, 2023/0019060, A1, U.S. Appl. No. 17/465,583, Nasveschuk et al., filed Jan. 19, 2023.
US, 2023/0082430, A1, U.S. Appl. No. 17/723,199, Henderson et al., Mar. 16, 2023.
US, 2023/0145336, A1, U.S. Appl. No. 18/084,380, Nasveschuk et al., May 11, 2023.
US, 2023/0190760, A1, U.S. Appl. No. 18/106,893, Proia et al., filed Jun. 22, 2023.
US, 2023/0233692, A1, U.S. Appl. No. 18/105,735, Henderson et al., Jul. 27, 2023.
US, 2023/0339902, A1, U.S. Appl. No. 18/134,985, Nasveschuk et al., Oct. 26, 2023.
US, 2023/0357180, A1, U.S. Appl. No. 18/079,815, Phillips et al., Nov. 9, 2023.
US, 2023/0372496, A1, U.S. Appl. No. 18/134,971, Nasveschuk et al., Nov. 23, 2023.
US, 2024/0018118, A1, U.S. Appl. No. 18/134,990, Nasveschuk et al., Jan. 18, 2024.
US, 2024/0018156, A1, U.S. Appl. No. 18/117,978, Nasveschuk et al., filed Jan. 18, 2024.
US, 2024/0076300, A1, U.S. Appl. No. 18/144,800, Nasveschuk et al., Mar. 7, 2024.
US, 2024/0109889, A1, U.S. Appl. No. 18/370,186, Norcross et al., Apr. 4, 2024.
US, 2024/0158418, A1, U.S. Appl. No. 18/516,589, Nasveschuk et al., May 16, 2024.
US, 2024/0199581, A1, U.S. Appl. No. 18/534,395, Nasveschuk et al., Dec. 8, 2023.
US, 2024/0199638, A1, U.S. Appl. No. 18/385,277, Norcross et al., Jun. 20, 2024.
US, 2024/0245677, A1, U.S. Appl. No. 18/600,097, Jackson et al., Jul. 25, 2024.
US, 2024/0391912, A1, U.S. Appl. No. 18/797,261, Henderson et al., Nov. 28, 2024.
US, 2024/0398959, A1, U.S. Appl. No. 18/642,602, Phillips et al., Dec. 5, 2024.
US, 2025/0057957, A1, U.S. Appl. No. 18/774,801, Phillips et al., Feb. 20, 2025.
US, 2025/0084055, A1, U.S. Appl. No. 18/806,363, Norcross et al., filed Mar. 13, 2025.
US, 2025/0084081, A1, U.S. Appl. No. 18/945,284, Nasveschuk et al., Mar. 13, 2025.
US, 2025/0101037, A1, U.S. Appl. No. 18/973,867, Phillips et al., filed Mar. 27, 2025.
US, 2025/0115580, A1, U.S. Appl. No. 18/980,700, Nasveschuk et al., Apr. 10, 2025.
US, 2025/0121069, A1, U.S. Appl. No. 18/775,662, Phillips et al., Apr. 17, 2025.
US, 2025/0121070, A1, U.S. Appl. No. 18/979,247, Nasveschuk et al., Apr. 17, 2025.
U.S. Appl. No. 18/774,794, filed Jul. 16, 2024, Philips et al.
U.S. Appl. No. 19/053,297, filed Feb. 13, 2025, Nasveschuk et al.

FIG. 1Q
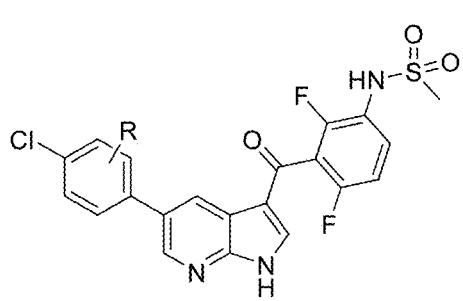
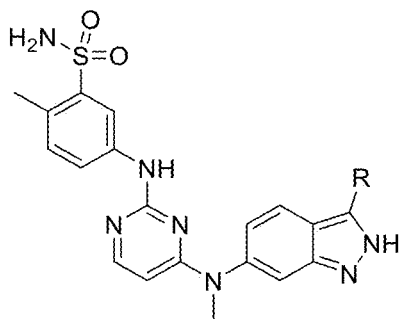
FIG. 1R
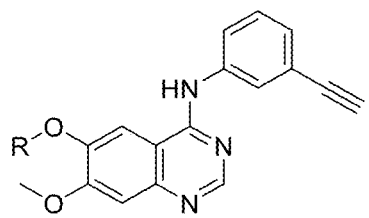
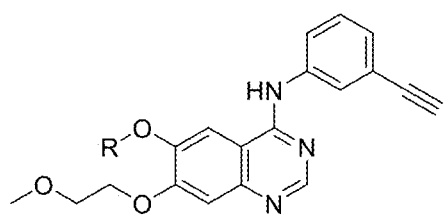
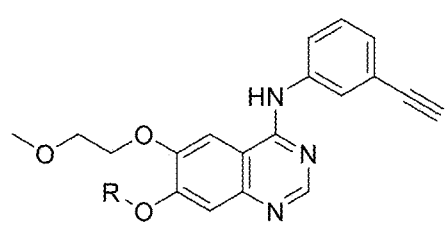
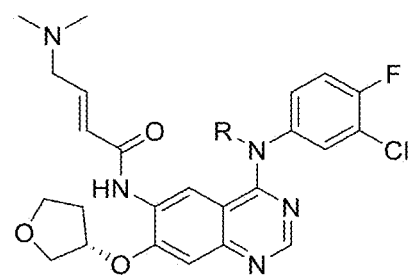
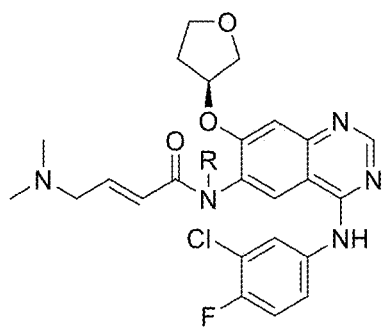
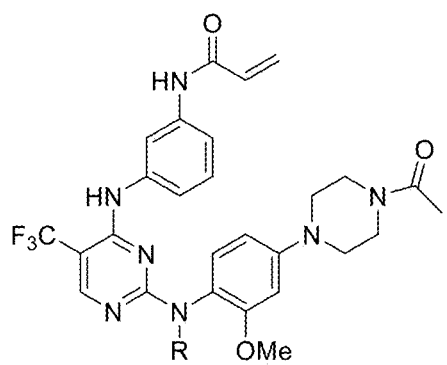

FIG. 1EE
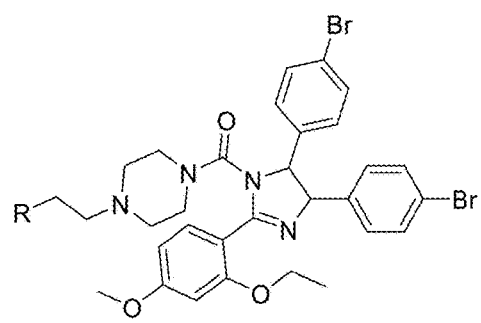
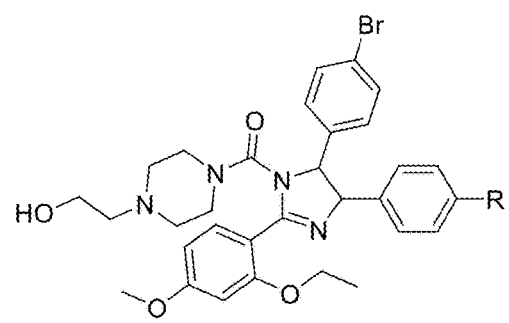
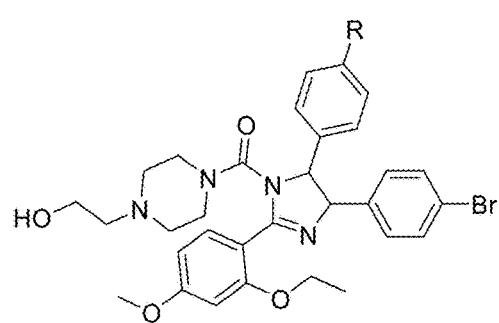
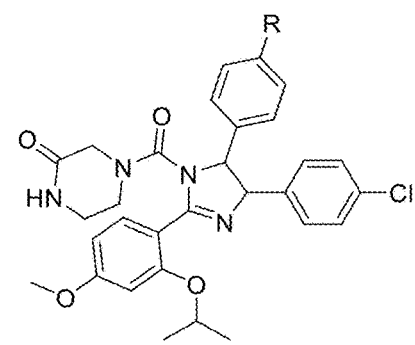
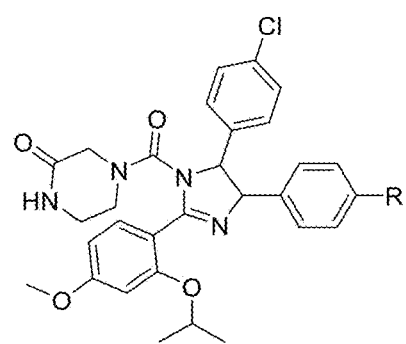
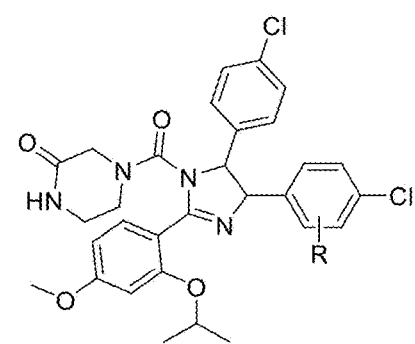
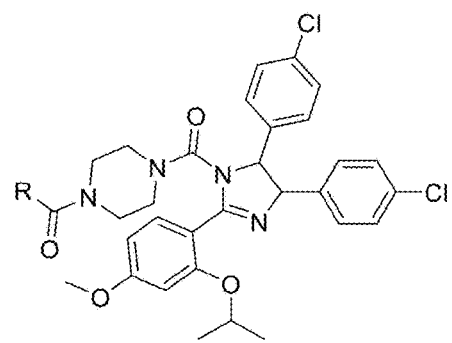
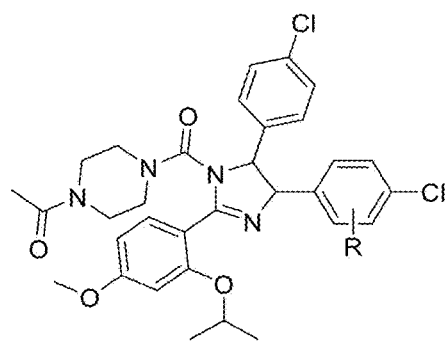

FIG. 1RR
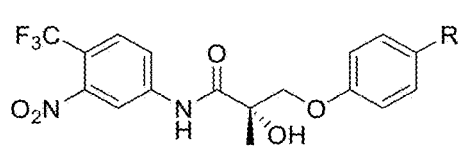
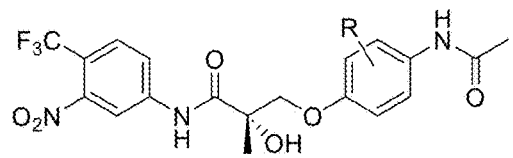
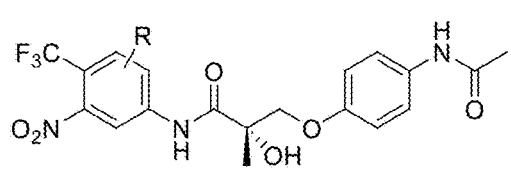
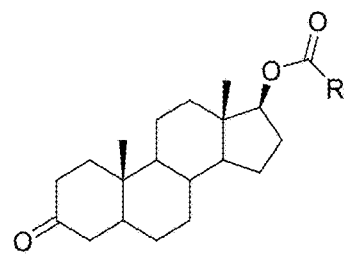
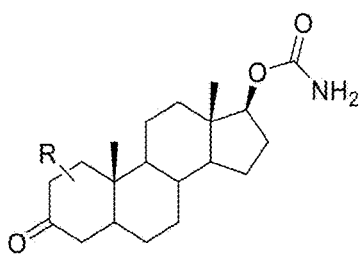
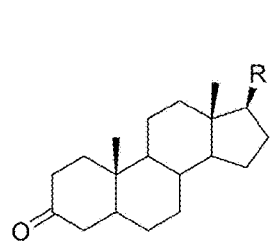
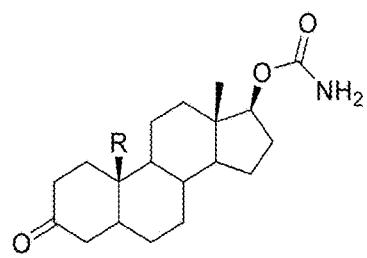
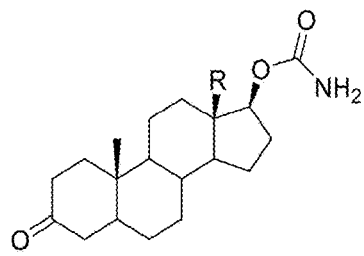
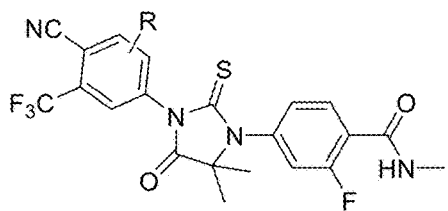
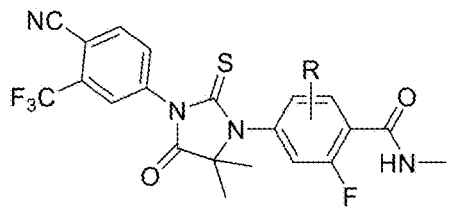
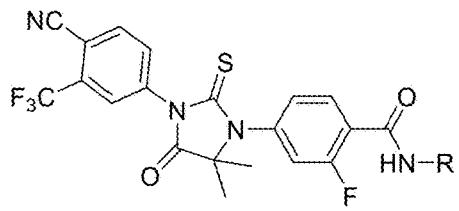
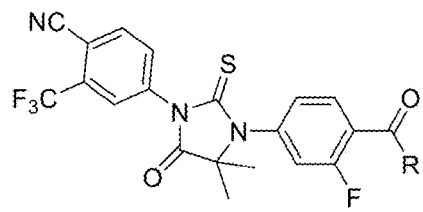
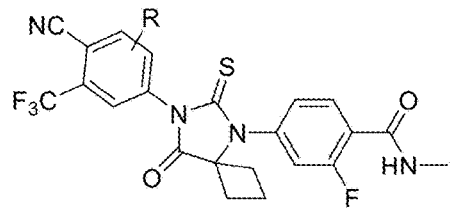

FIG. 1TT
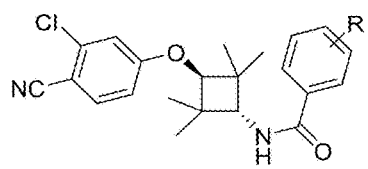
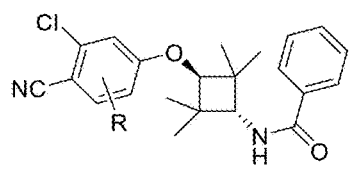
FIG. 1UU
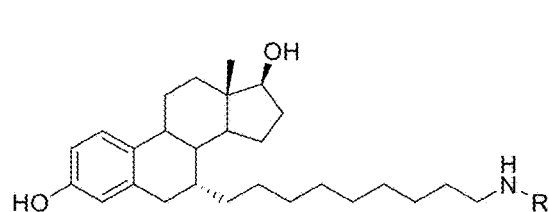
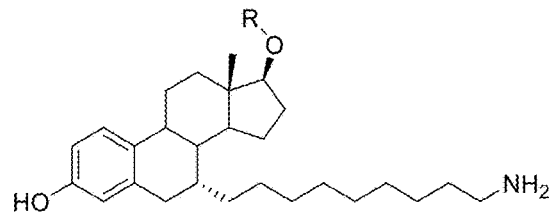
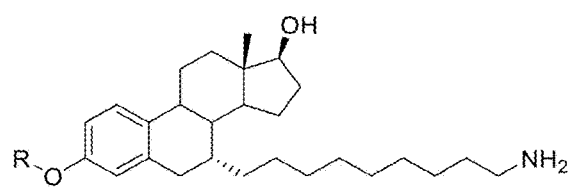
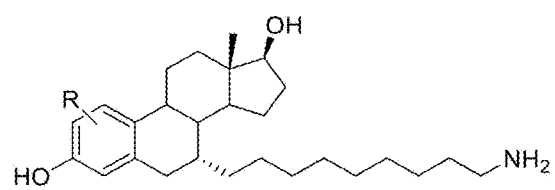
FIG. 1VV
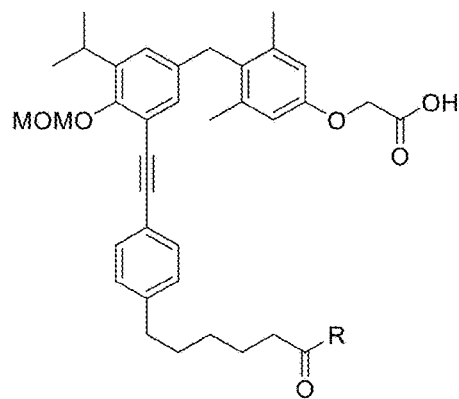
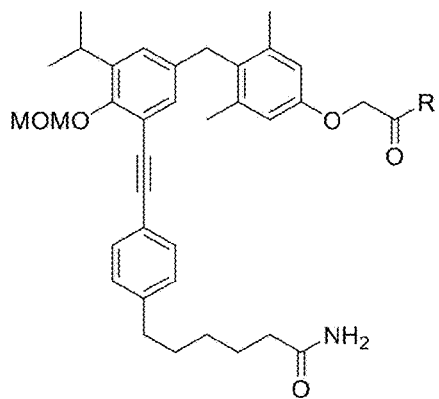

FIG. 1WW
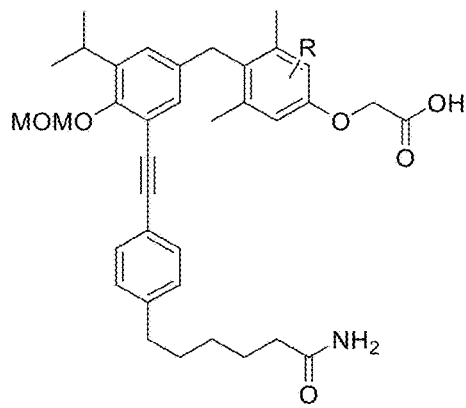
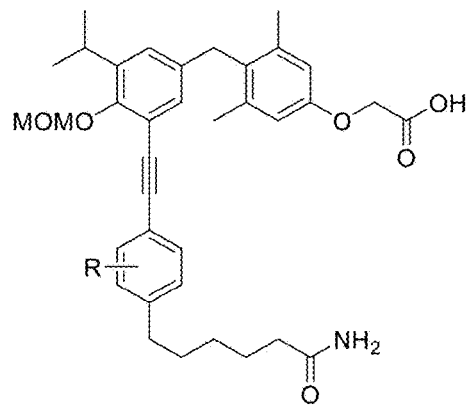
FIG. 1XX
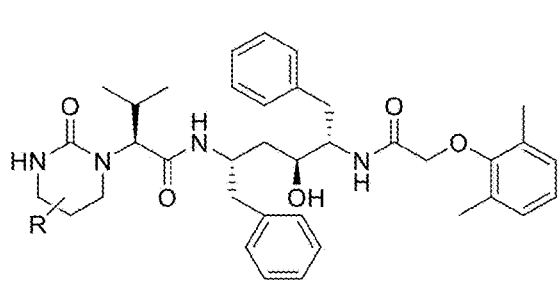
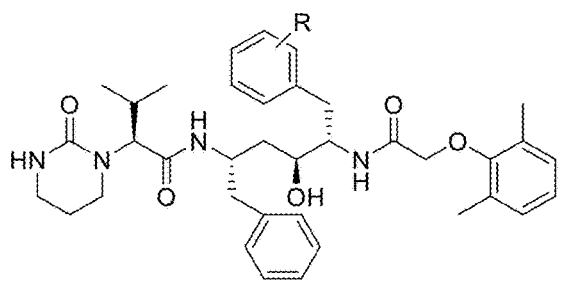
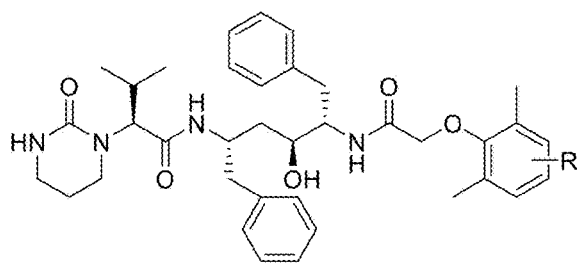
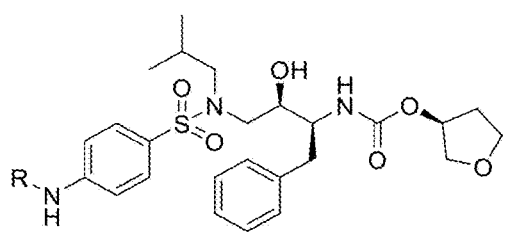
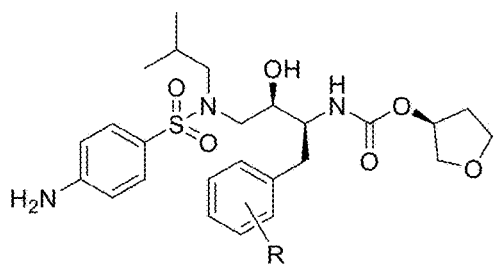
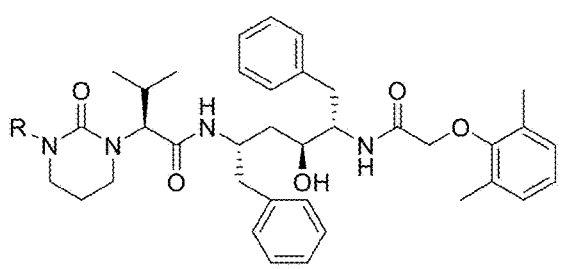

FIG. 1AAA
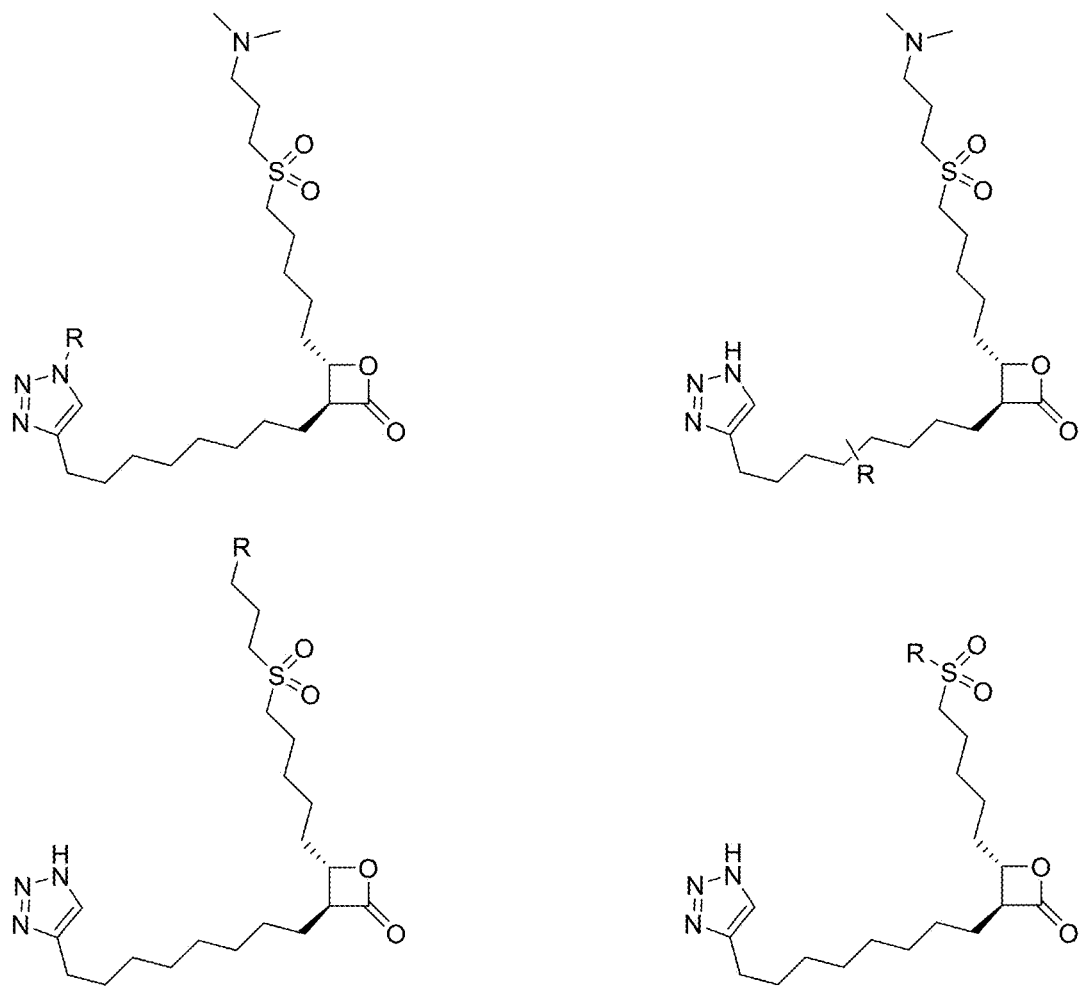
FIG. 1BBB
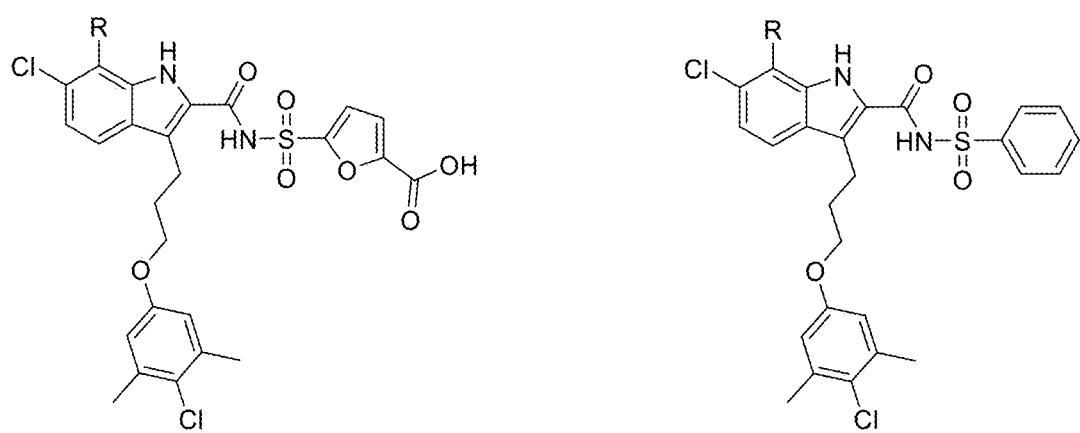

FIG. 1CCC
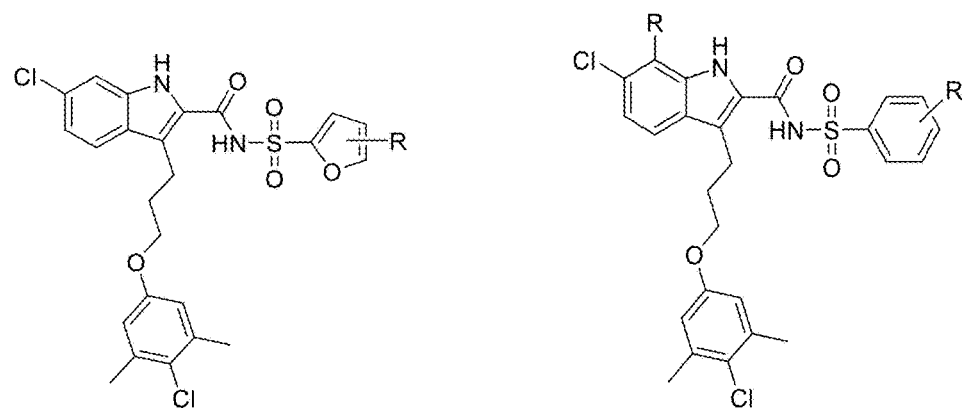
FIG. 1DDD
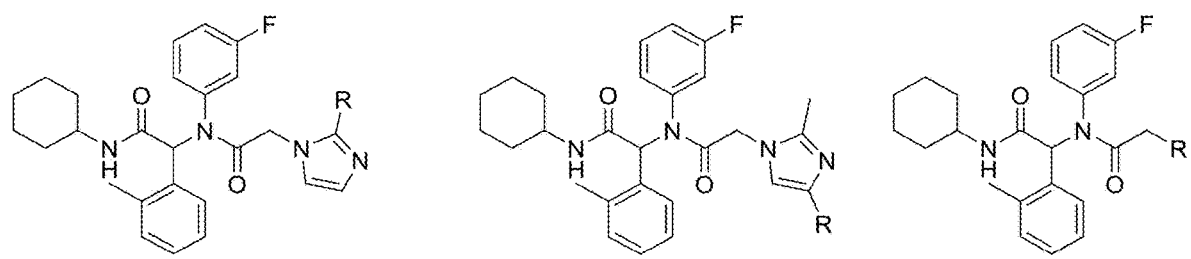
FIG. 1EEE
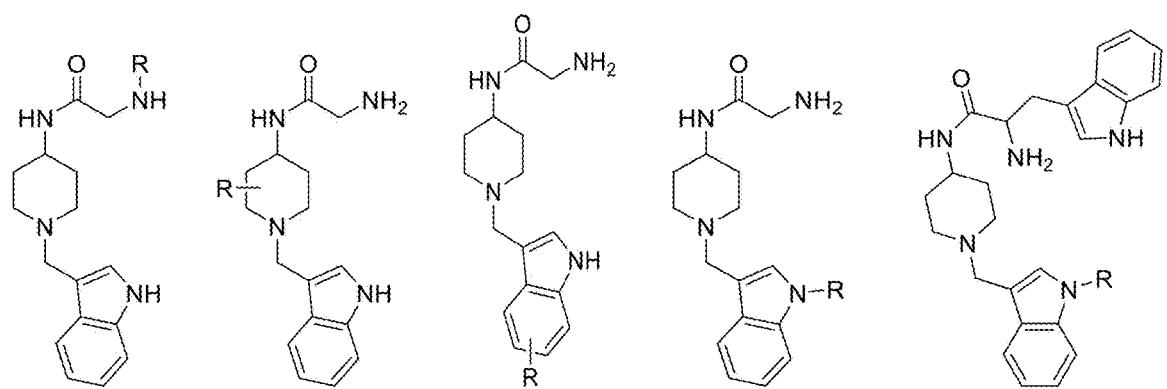

FIG. 1FFF
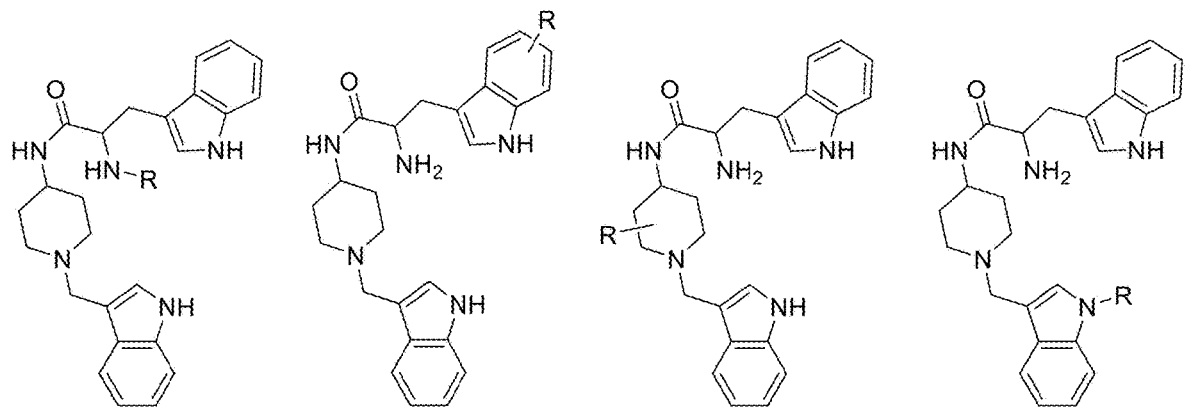
FIG. 1GGG
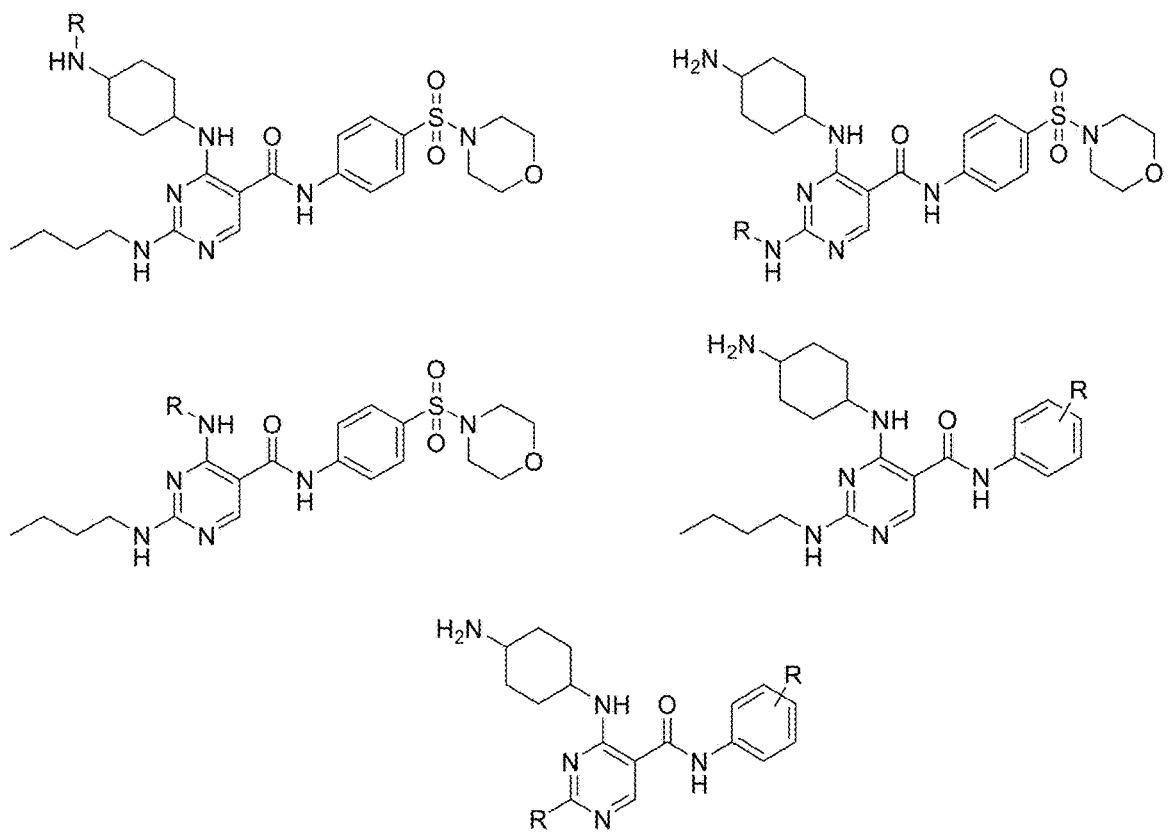

FIG. 1HHH
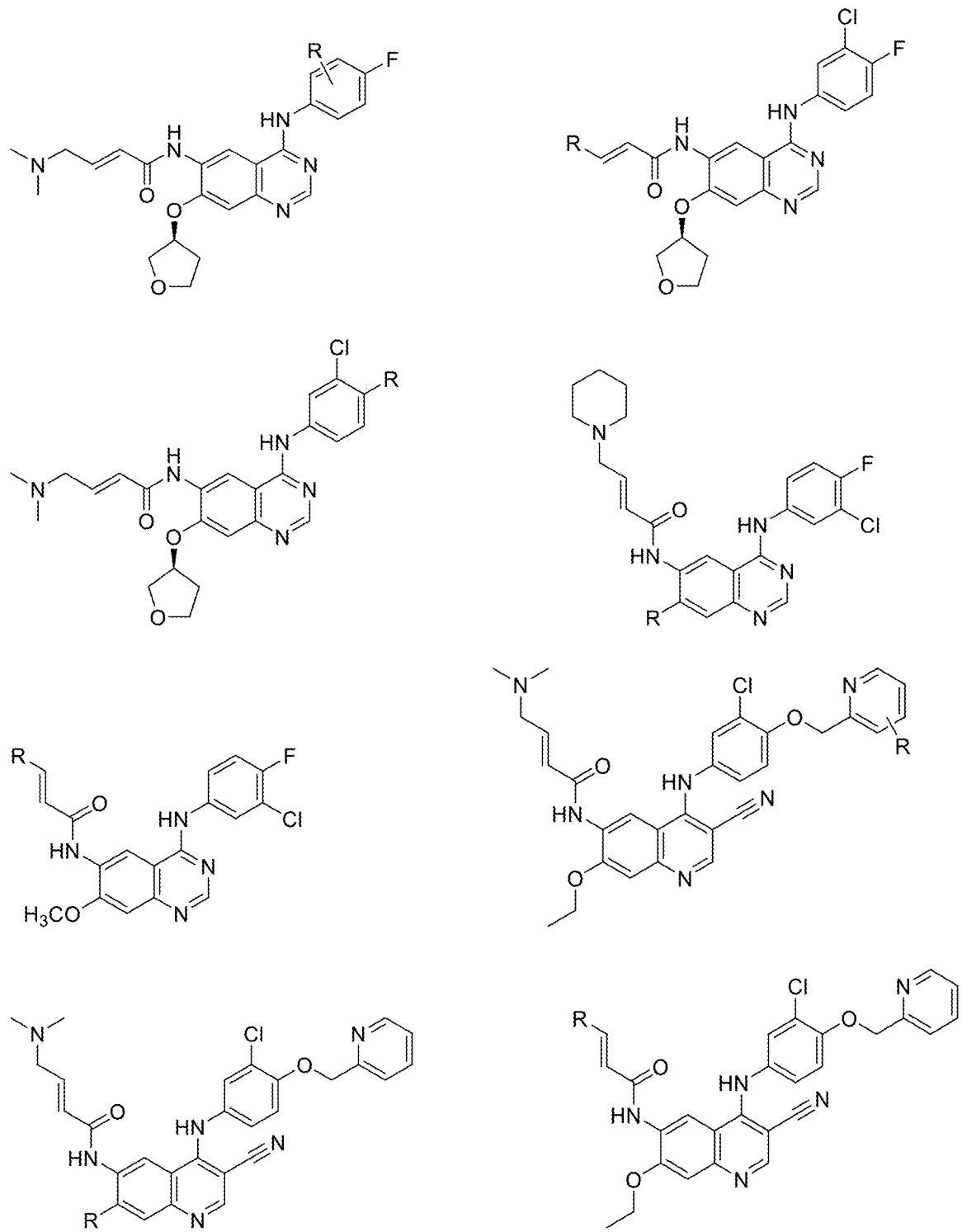

FIG. 1III
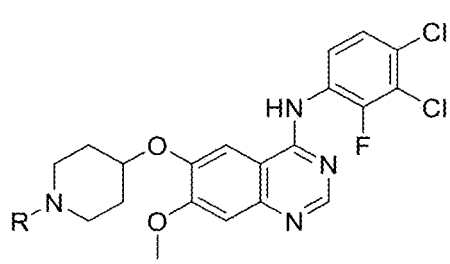
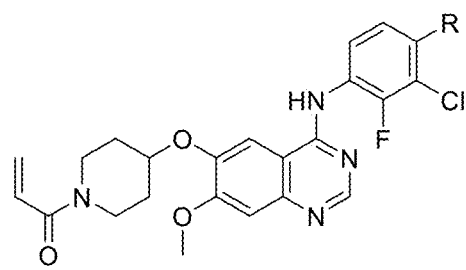
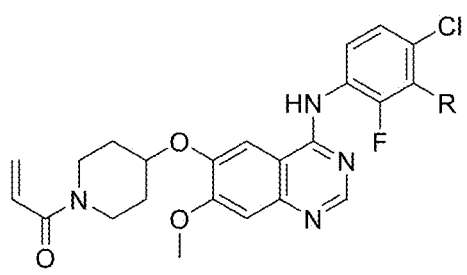
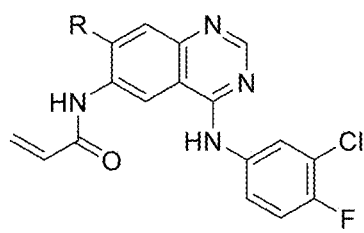
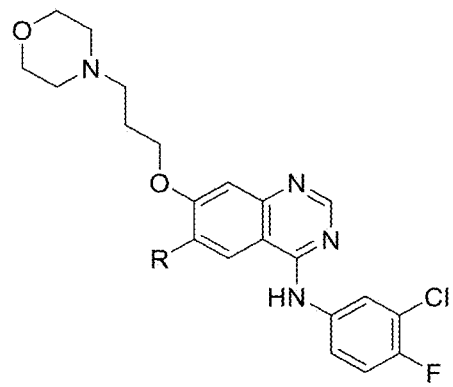
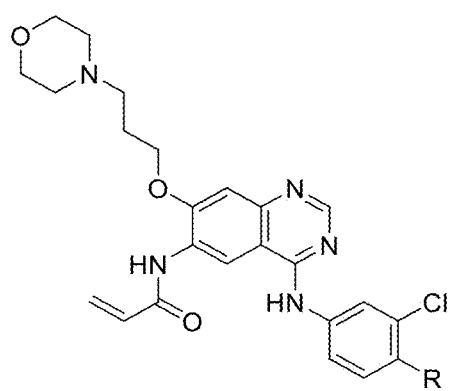

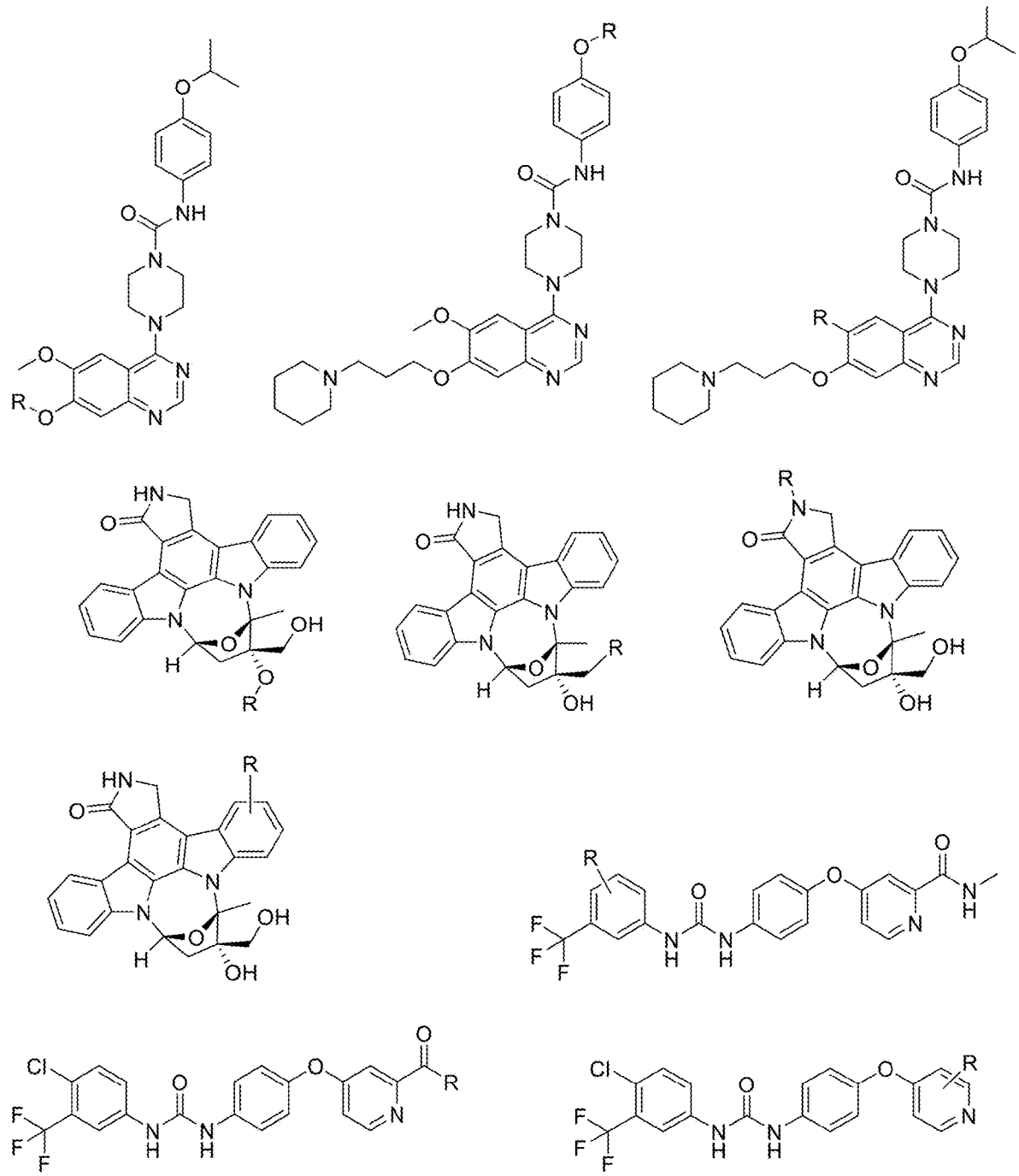
FIG. 1JJJ

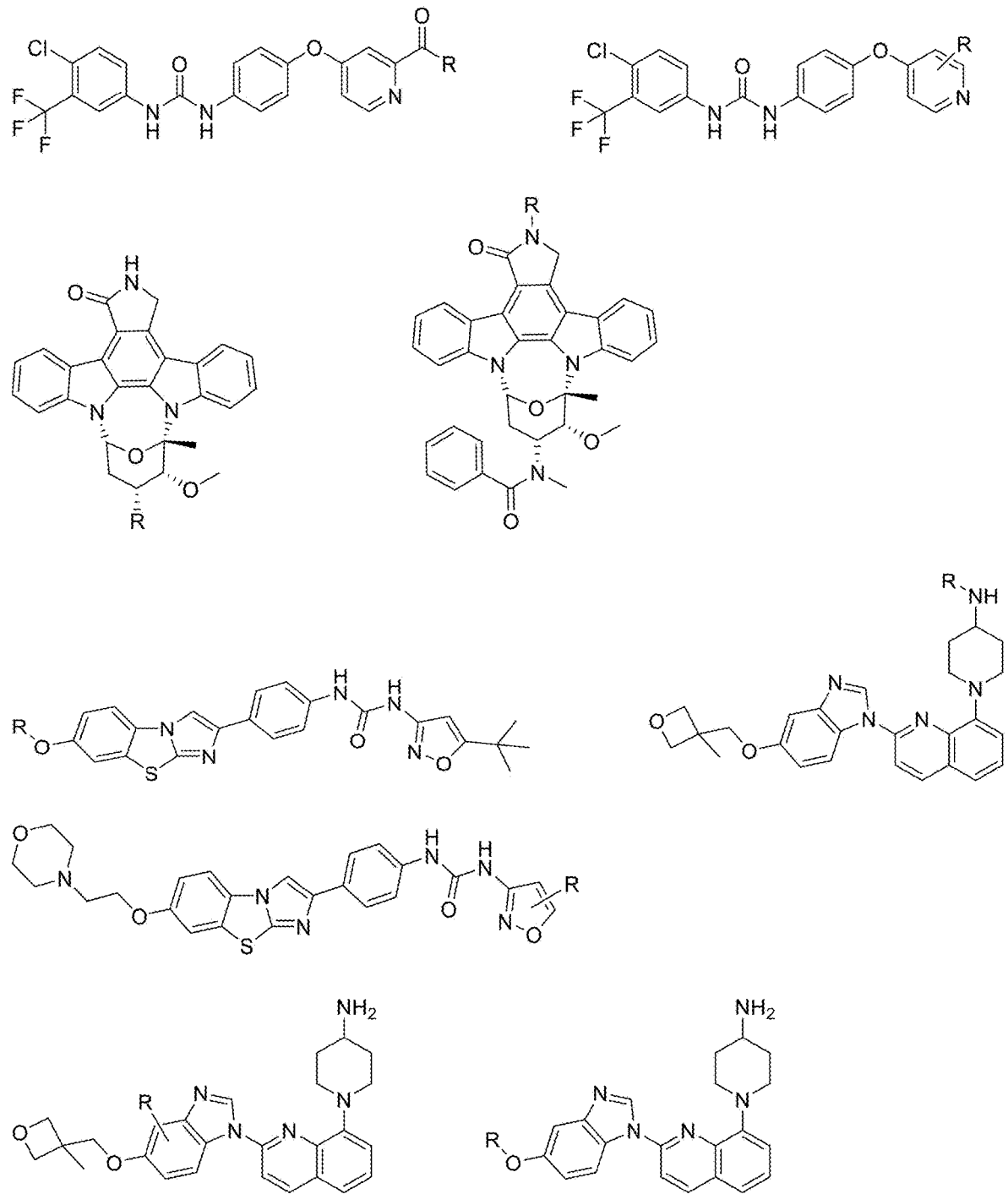
FIG. 1KKK

FIG. 1LLL
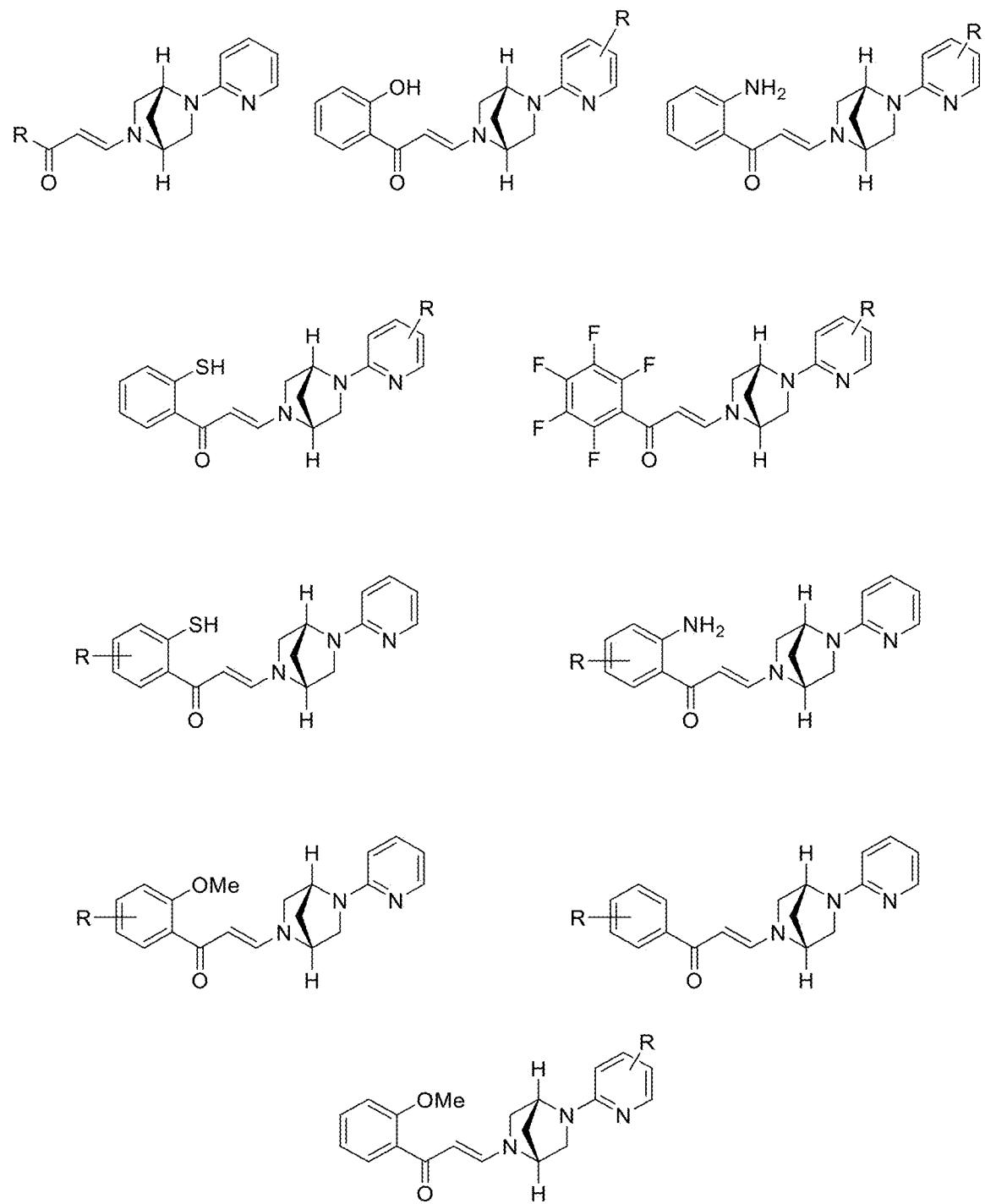

FIG. 2F
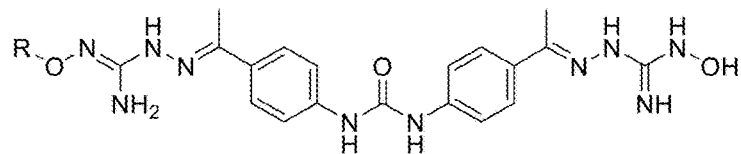
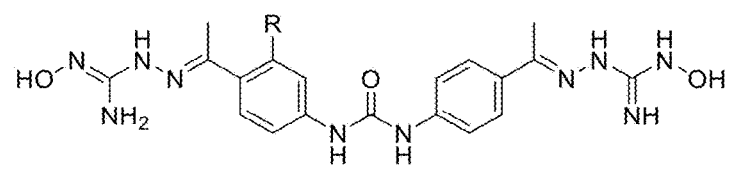
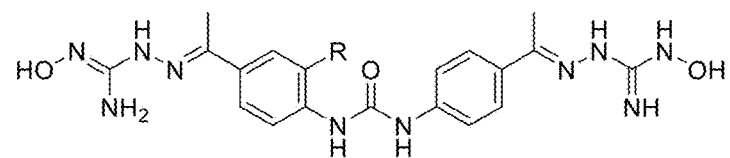
FIG. 2G
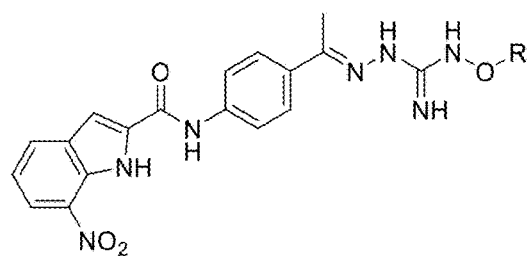
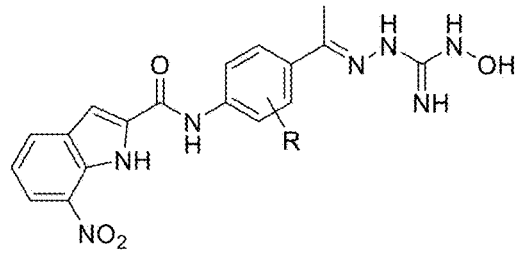
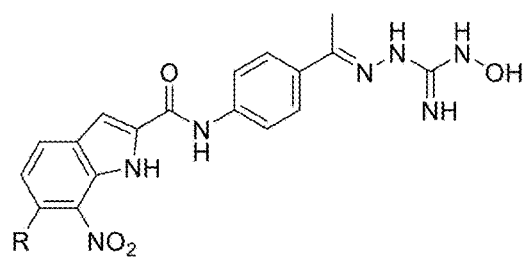
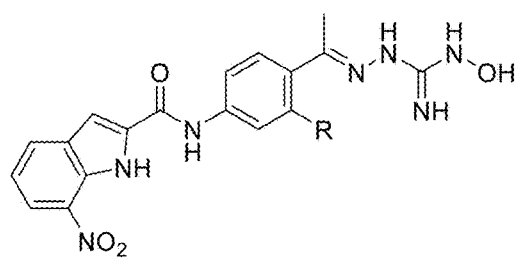
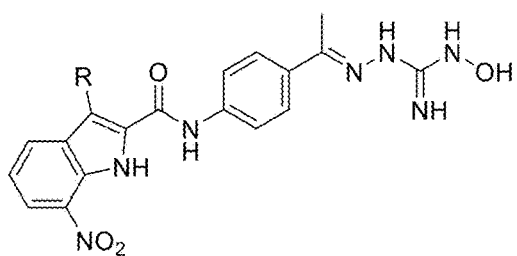
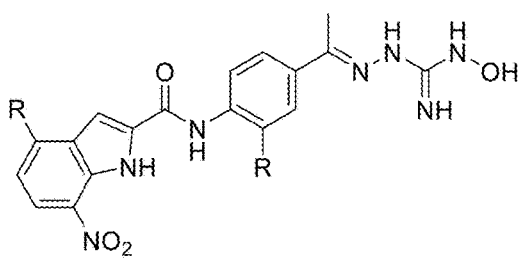

FIG. 2I
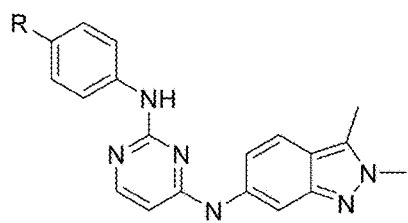
derivatized pazopanib
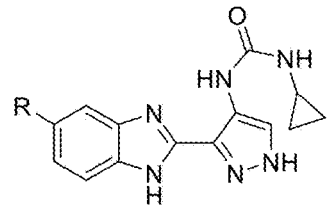
derivatized AT-9283
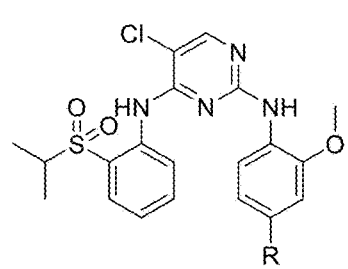
derivatized TAE684
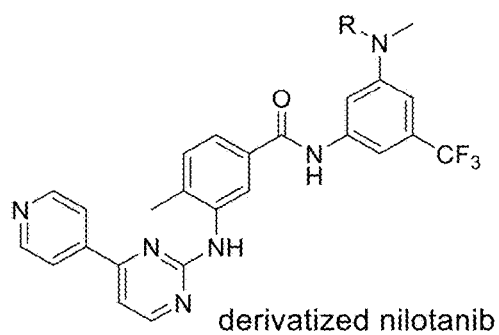
derivatized nilotanib
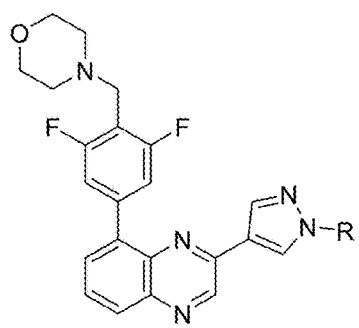
derivatized NVP-BSK805
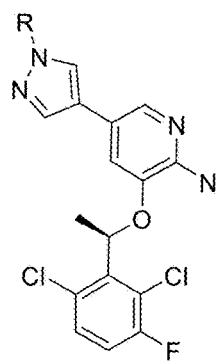
derivatized Crizotinib
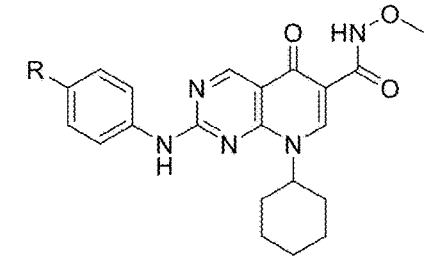
derivatized JNJ FMS
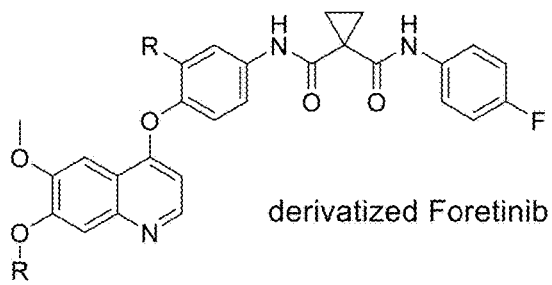
derivatized Foretinib
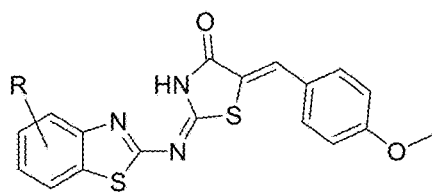
derivatized inhibitor of SHP-2 Domain of Tyrosine Phospatase derivatized PTP1B derivatized inhibitor of BRAF (BRAFV600E)/MEK derivatized mTORC1/2 kinase inhibitor OSI-027 derivatized c-Kit/KDR kinase inhibitor OSI-930 derivatized IGF1R/IR kinase inhibitor OSI-906

FIG. 2W
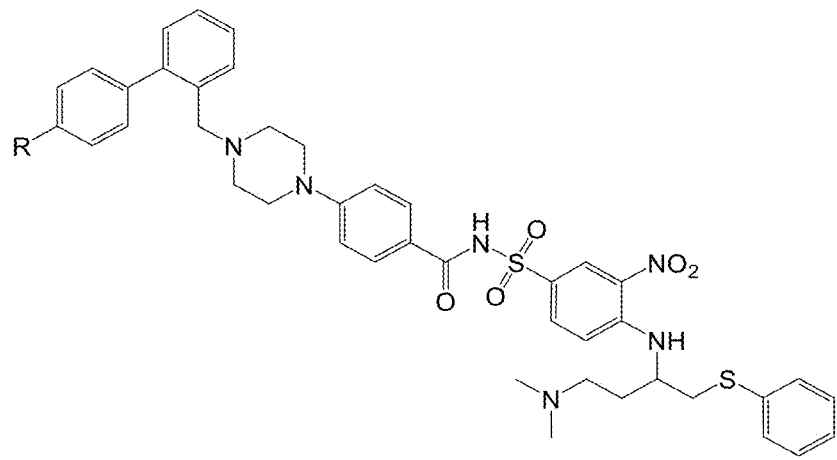
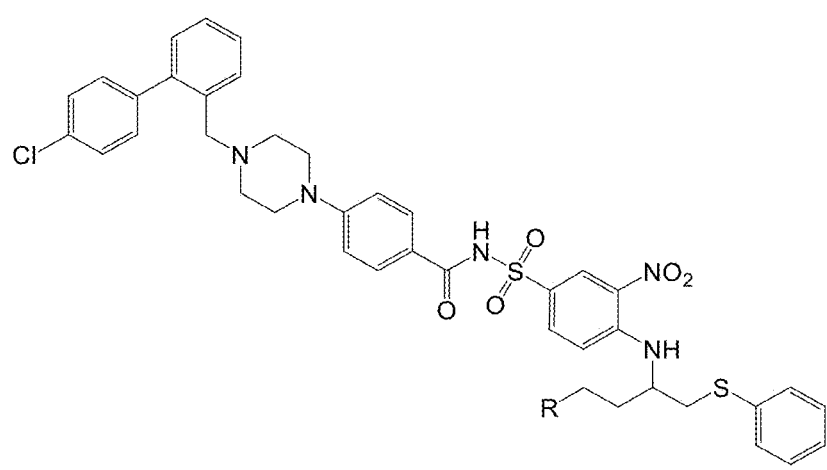
FIG. 2X
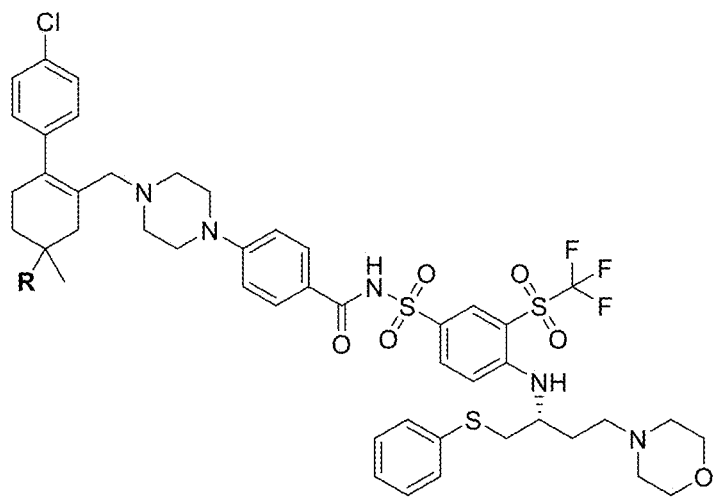
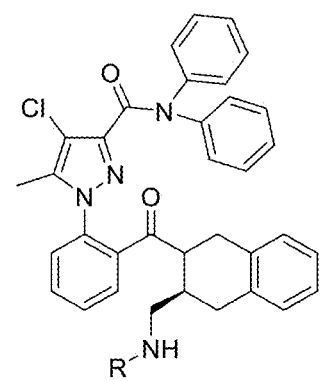

FIG. 2Y
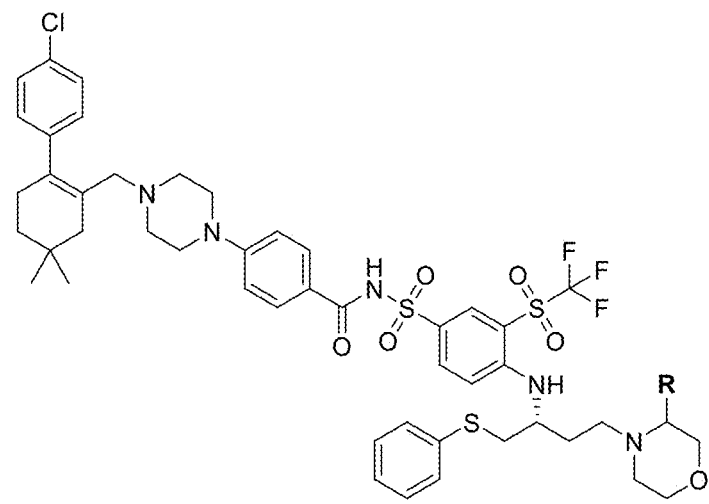
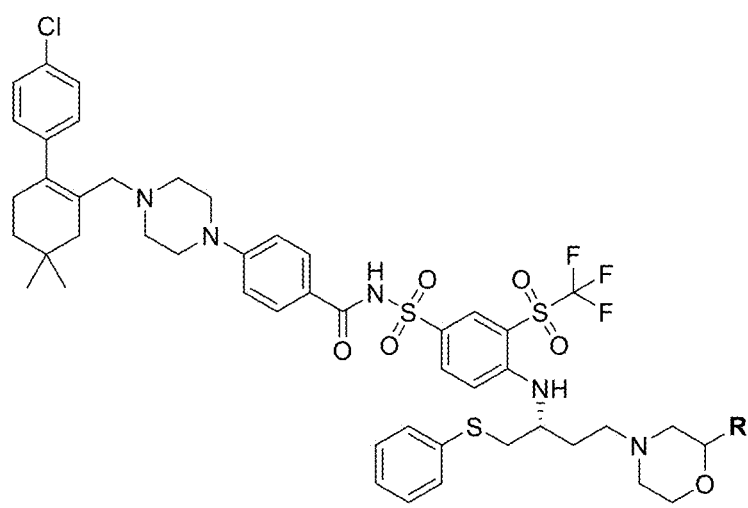
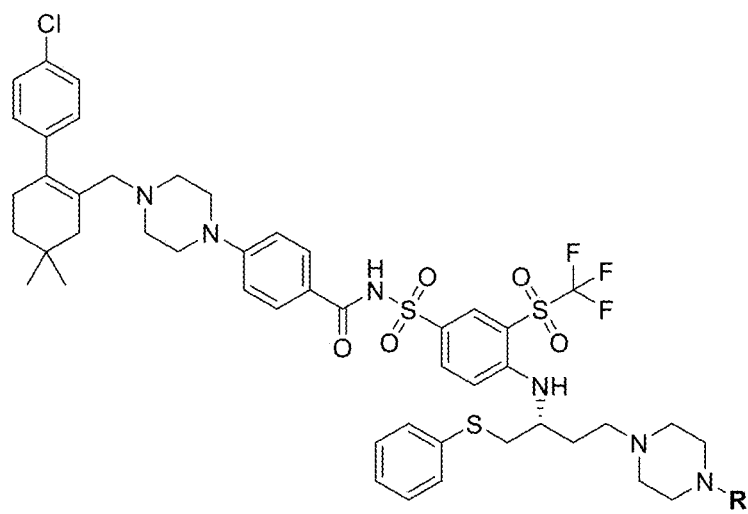

FIG. 2Z
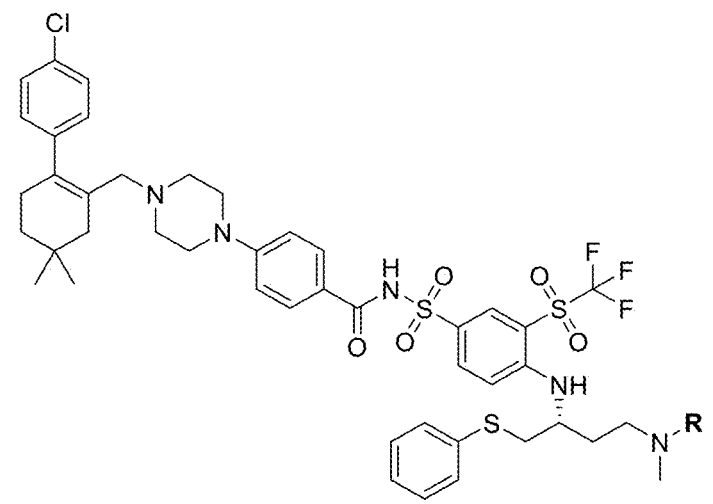
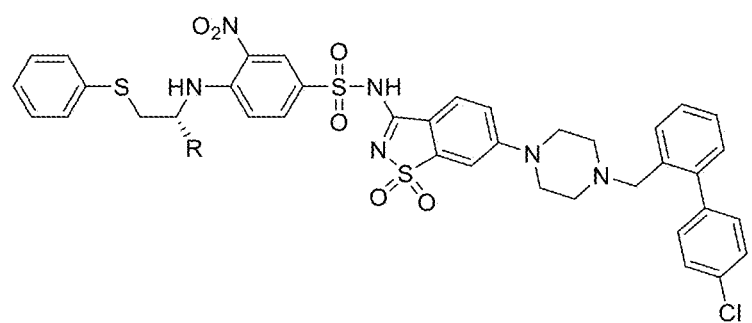
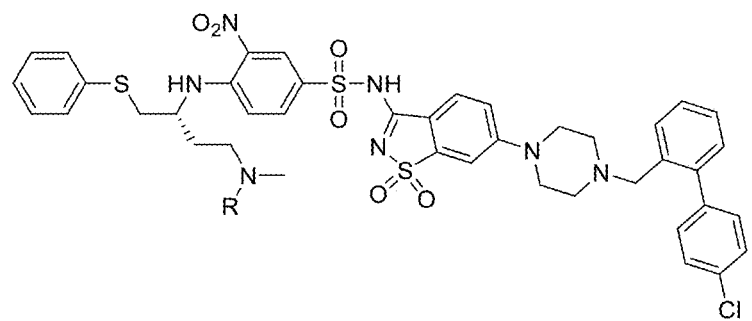

FIG. 2RR
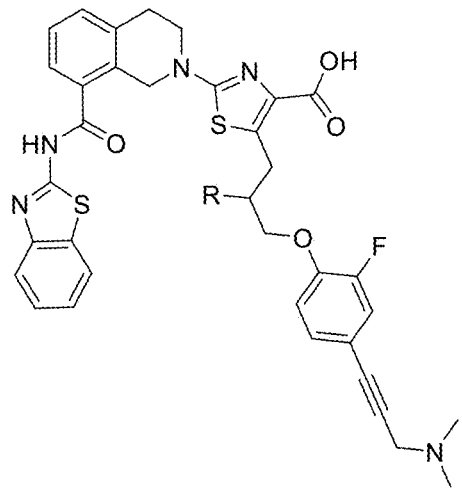
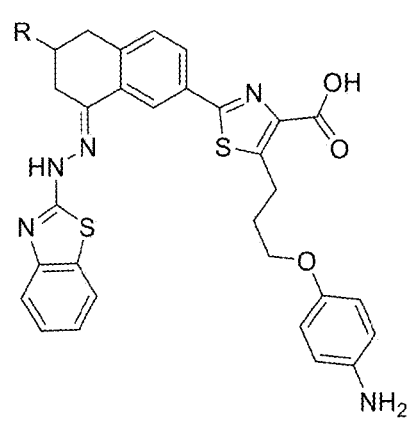
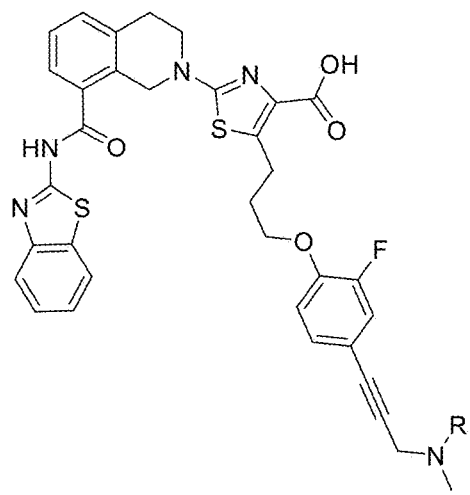
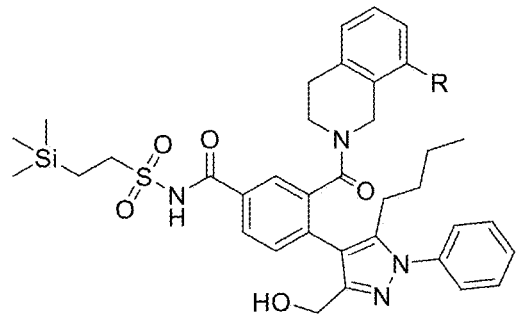
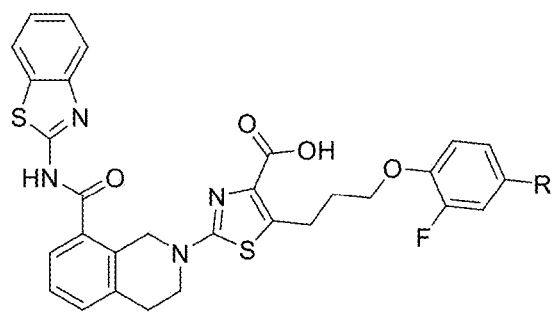
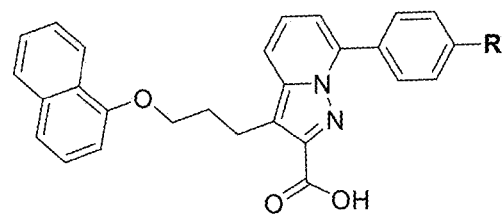

FIG. 2AAA
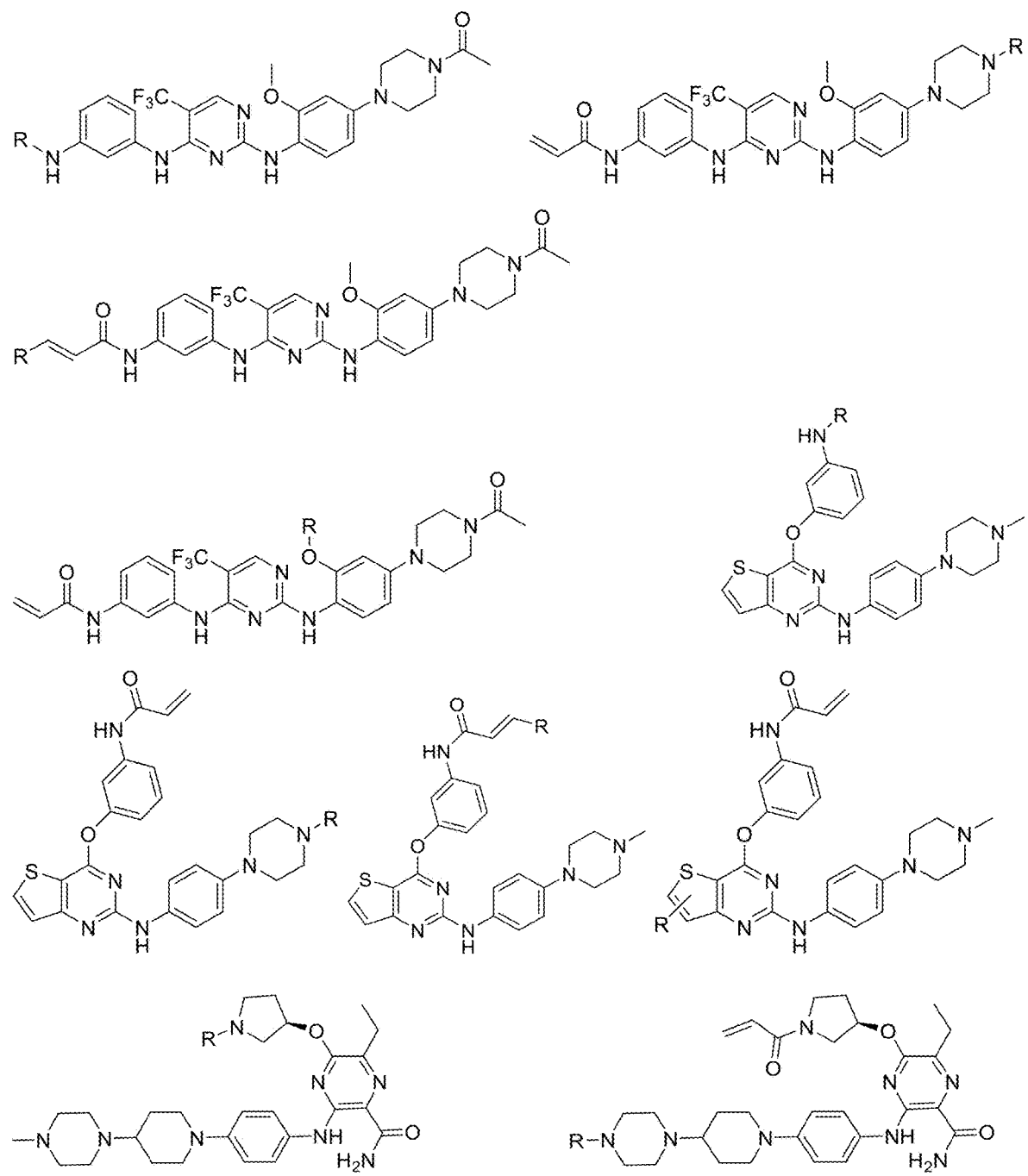

FIG. 2BBB
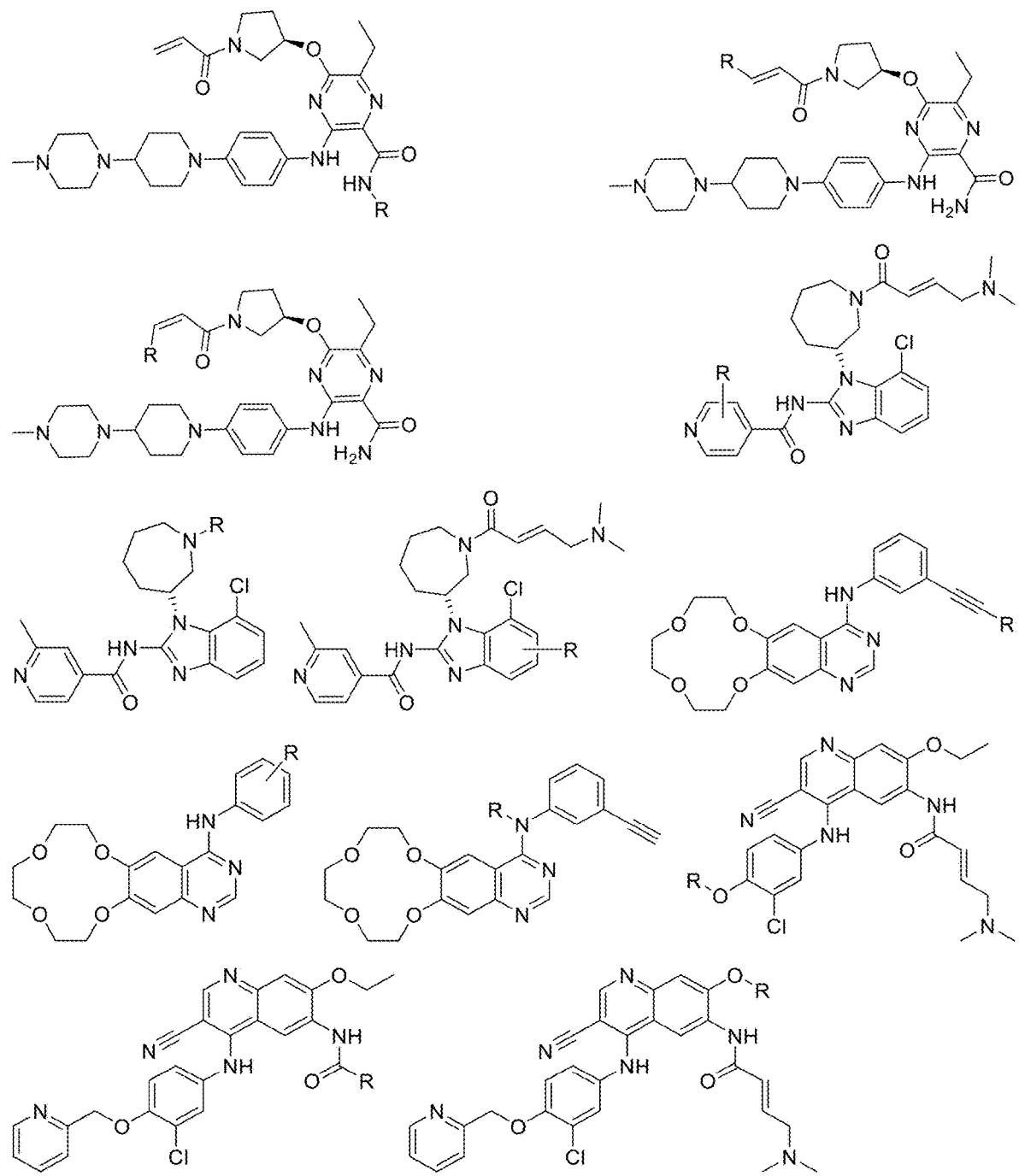

FIG. 2CCC
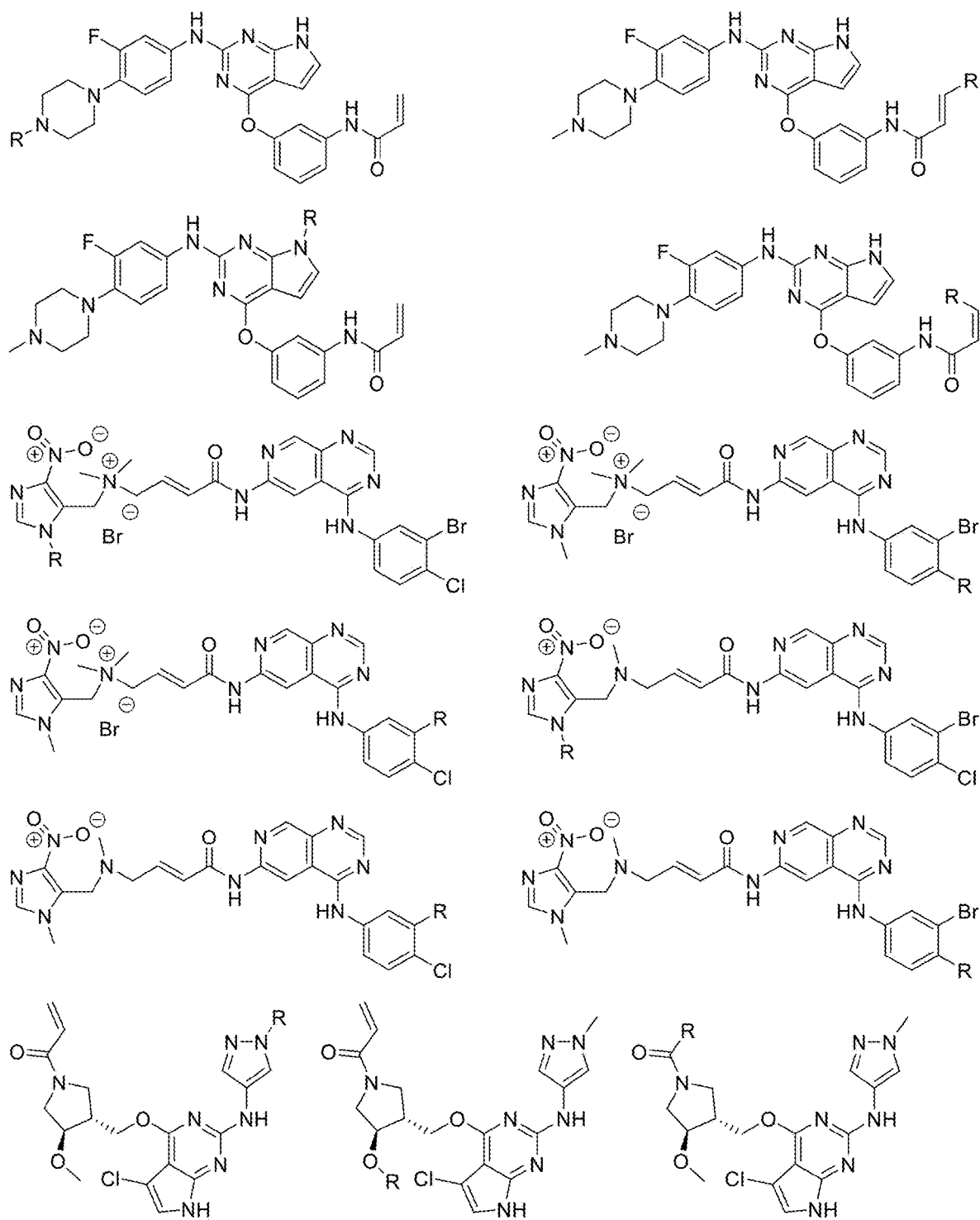

FIG. 2DDD
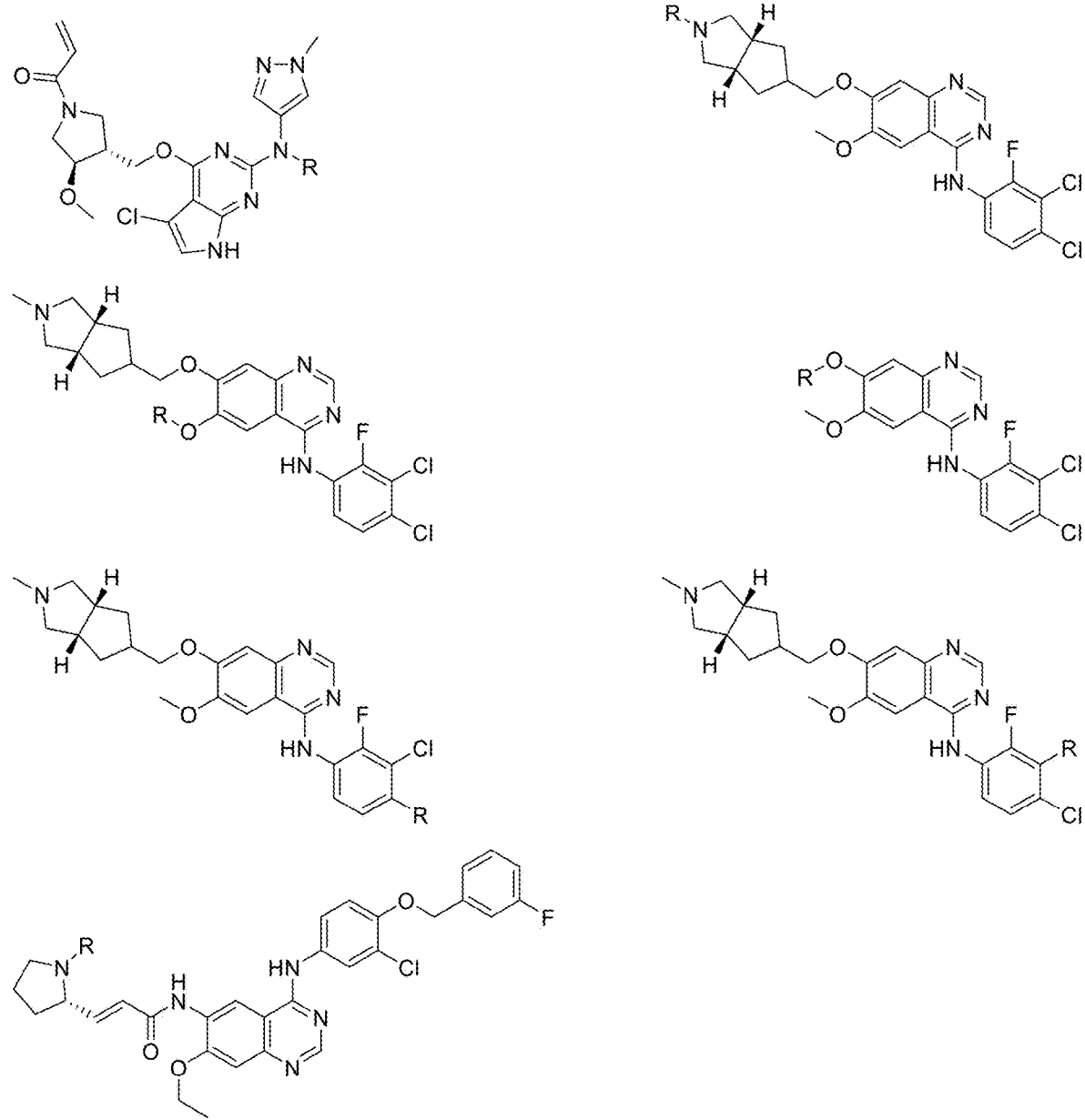

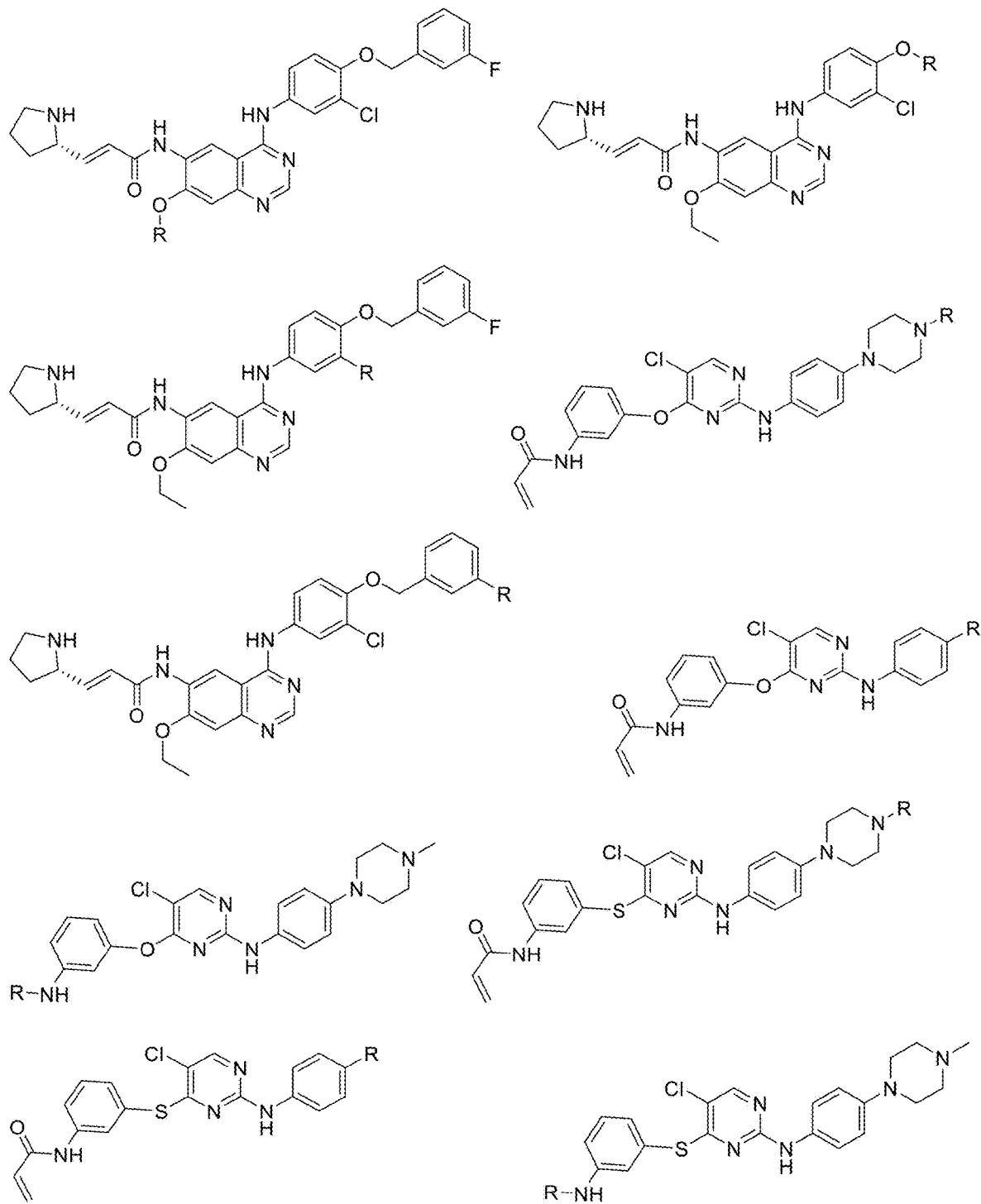
FIG. 2EEE

FIG. 2FFF
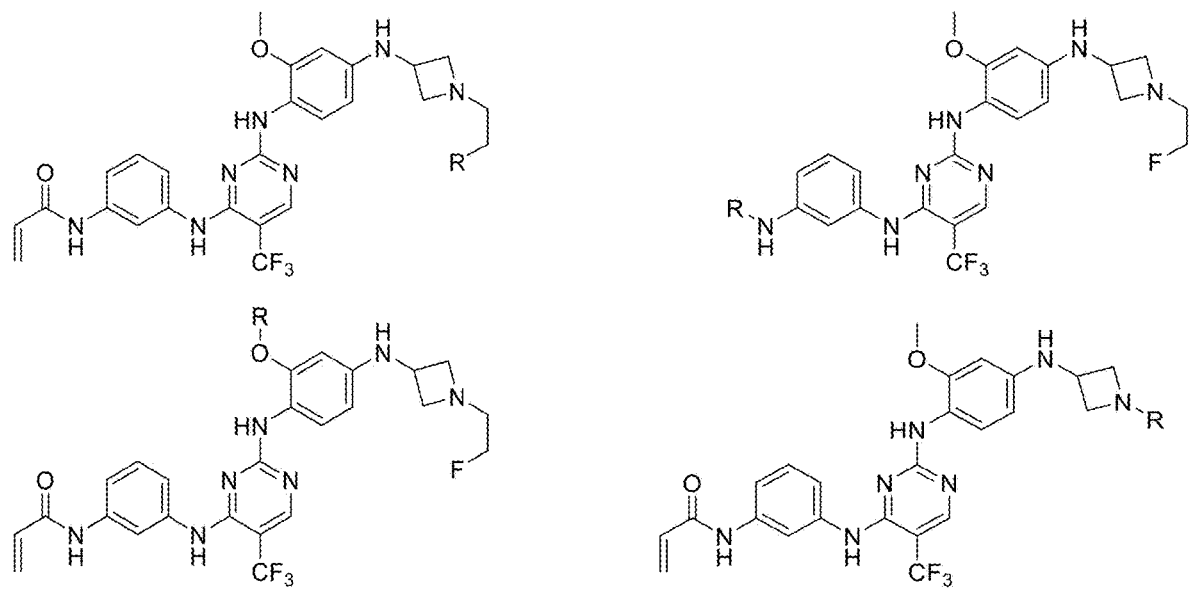
FIG. 2GGG
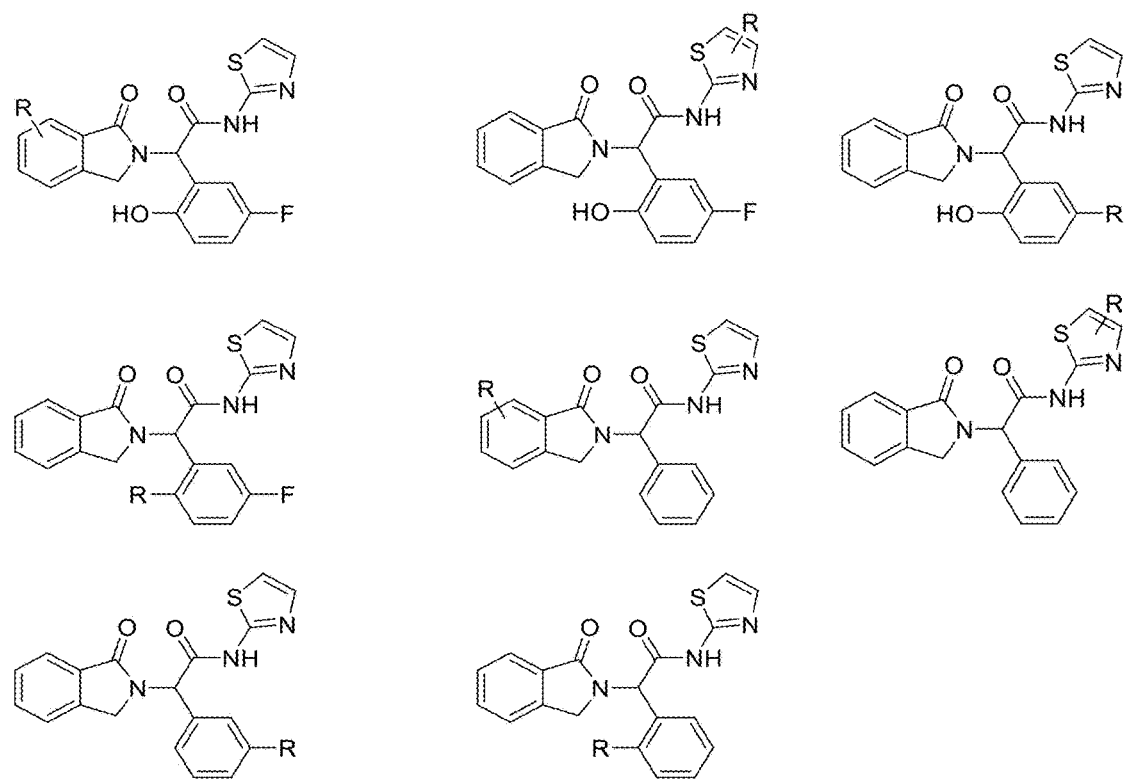

FIG. 2HHH
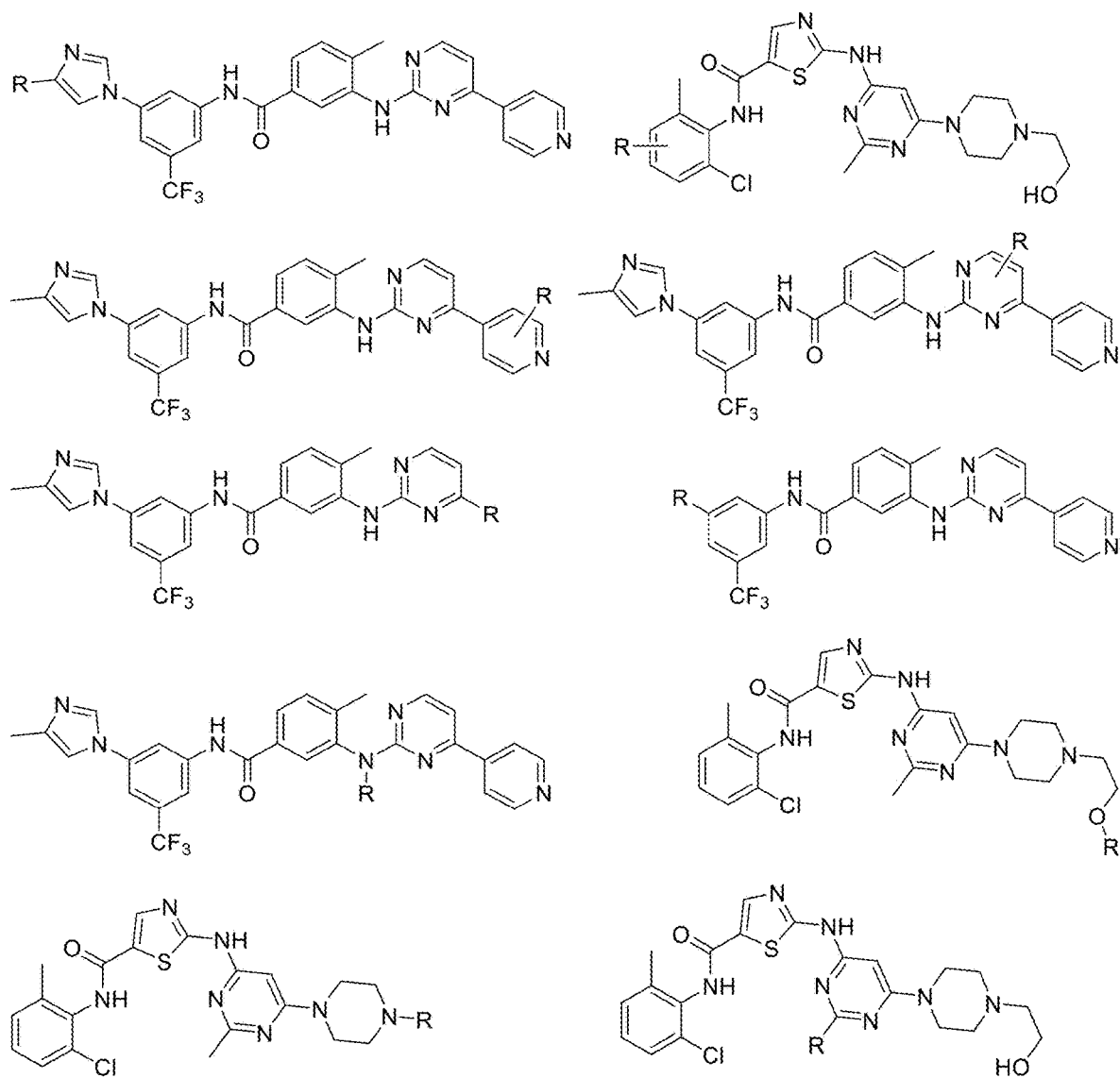

FIG. 2III
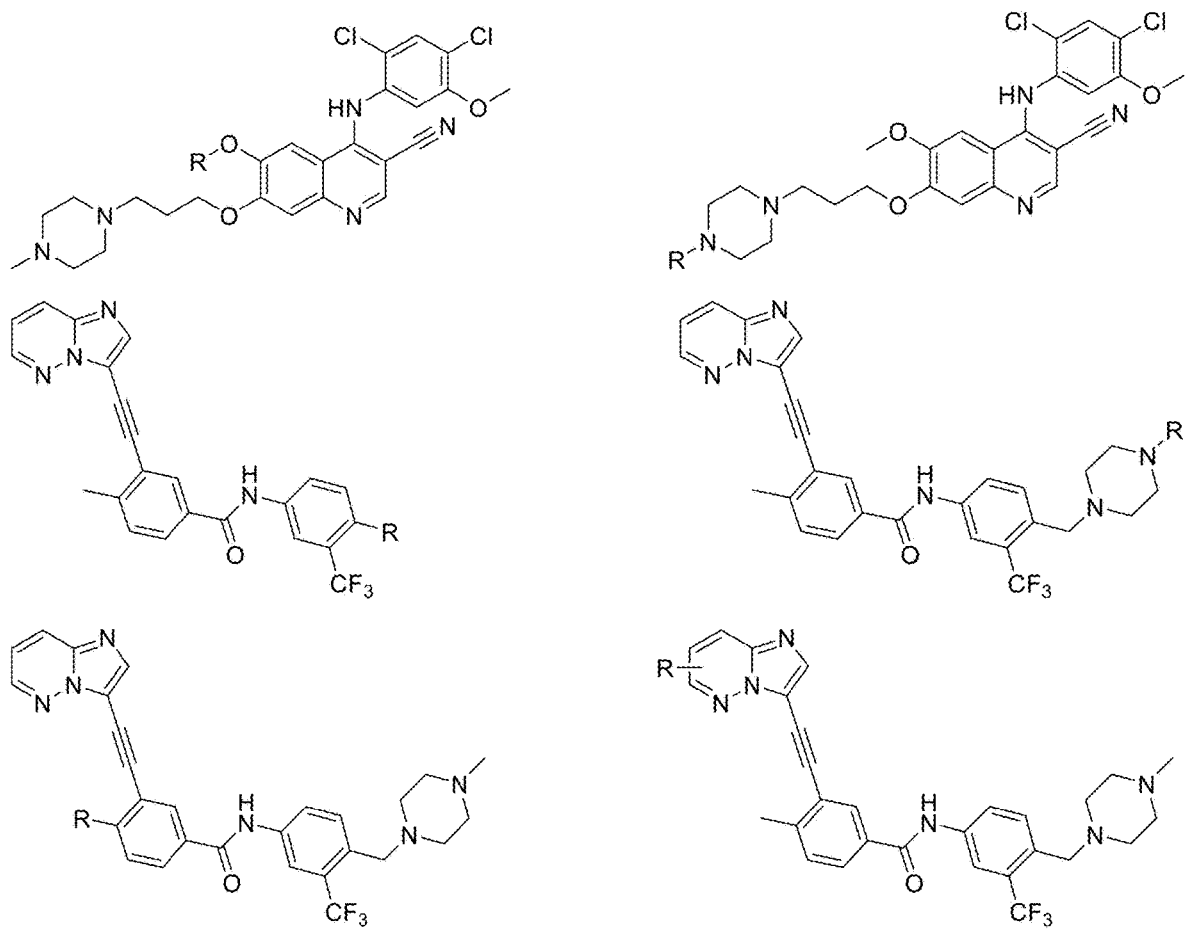
FIG. 2JJJ
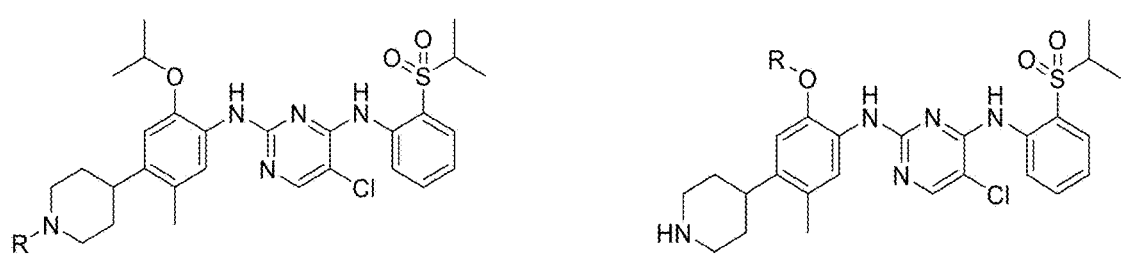

FIG. 2KKK
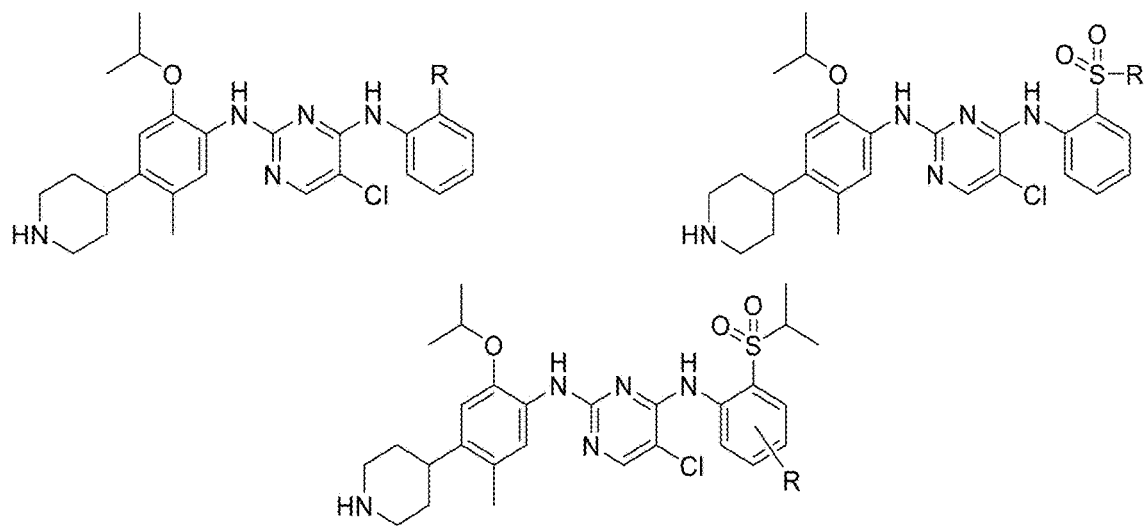
FIG. 2LLL
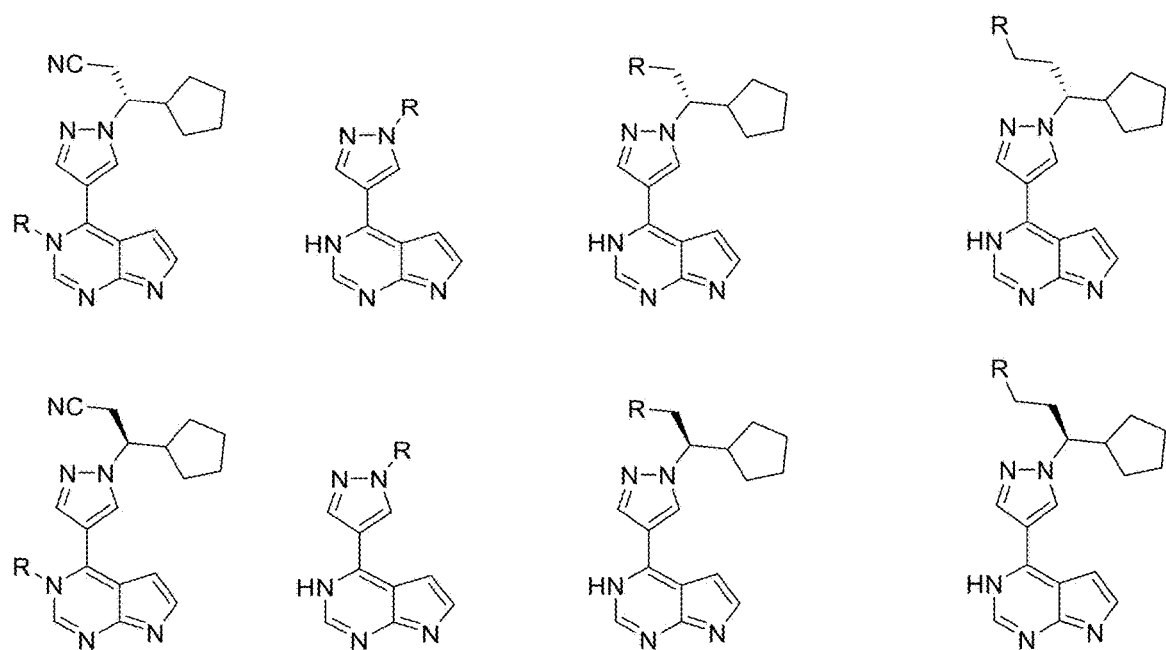

FIG. 2MMM
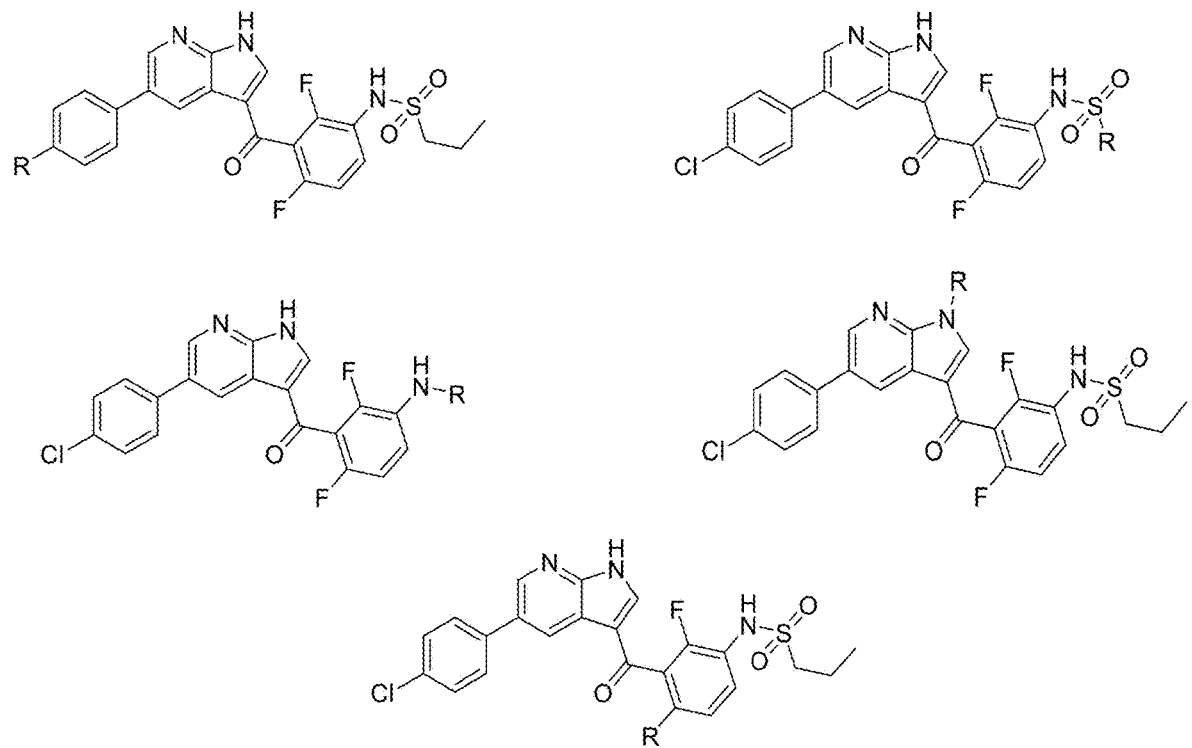
FIG. 2NNN
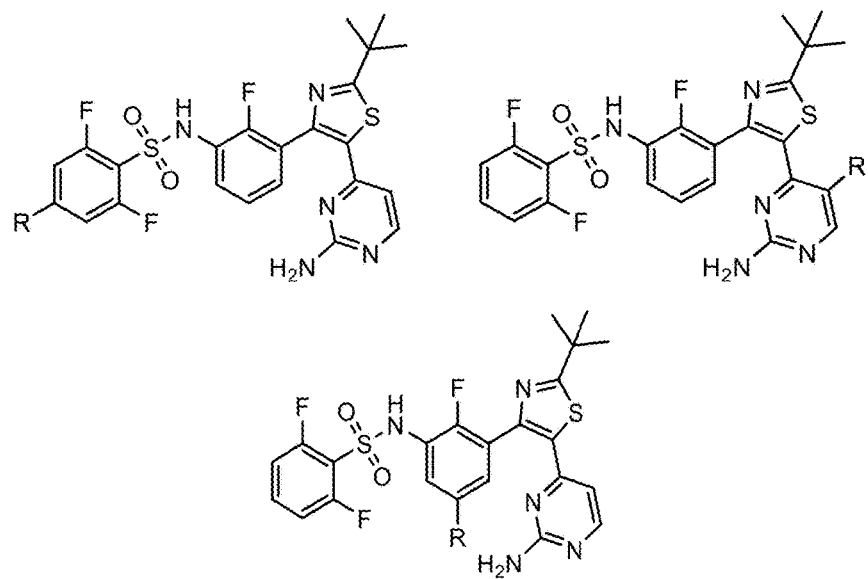

FIG. 2OOO
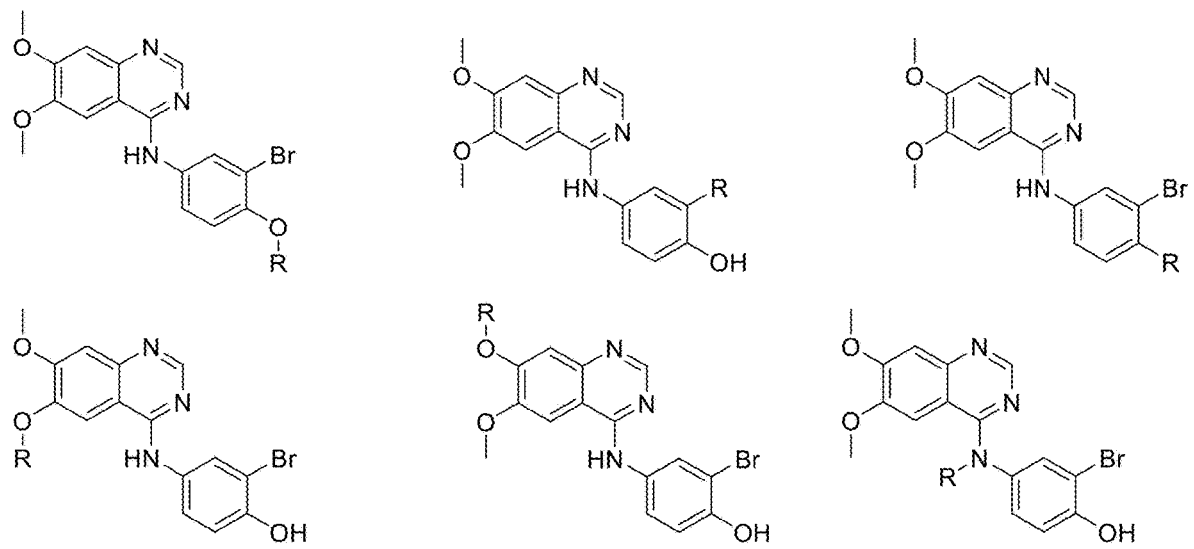
FIG. 2PPP
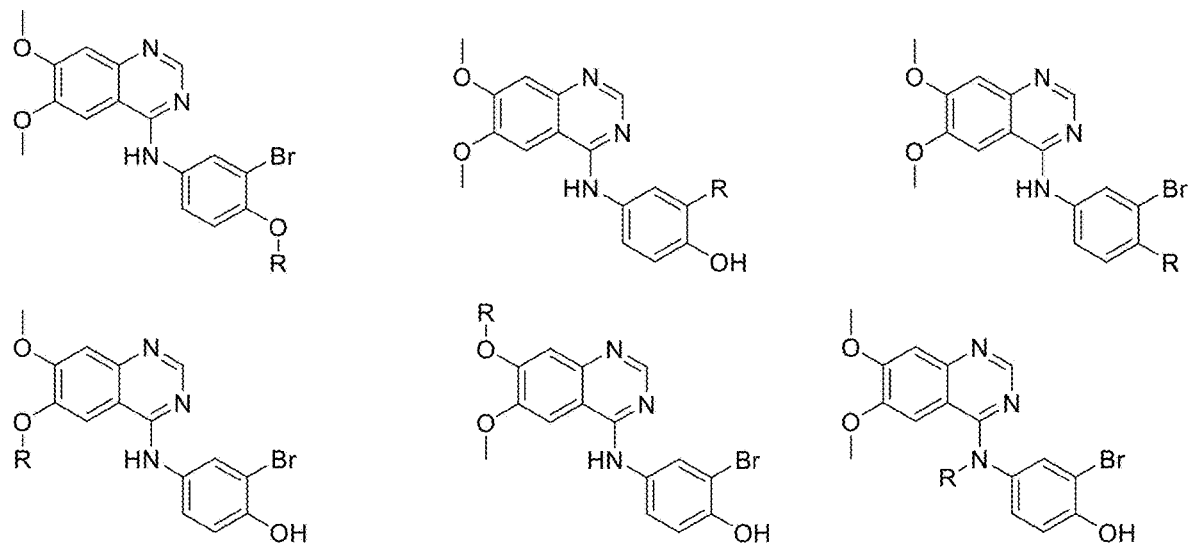

FIG. 2QQQ
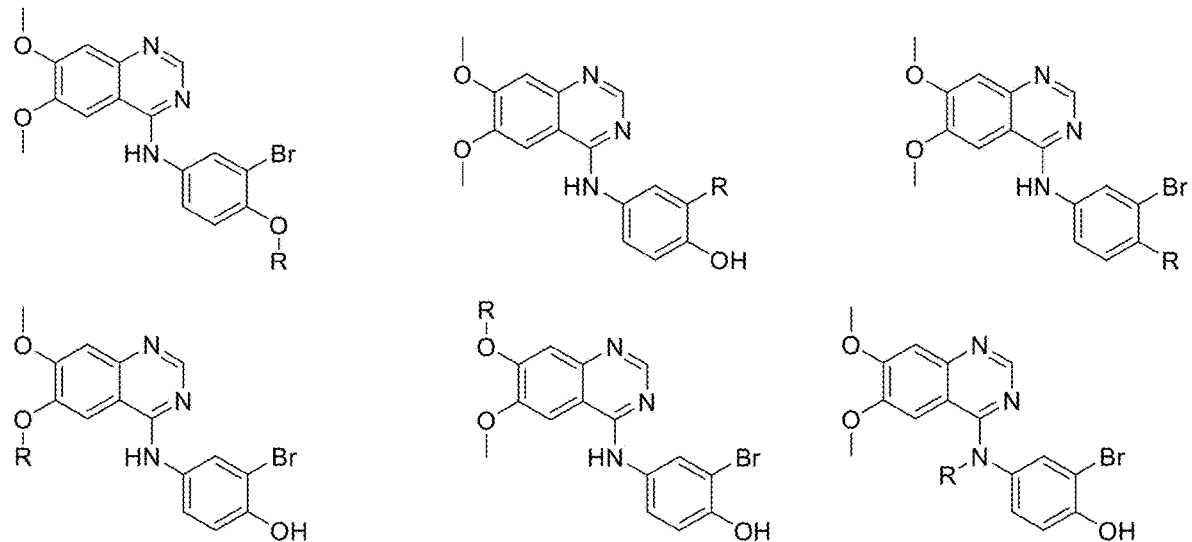
FIG. 2RRR
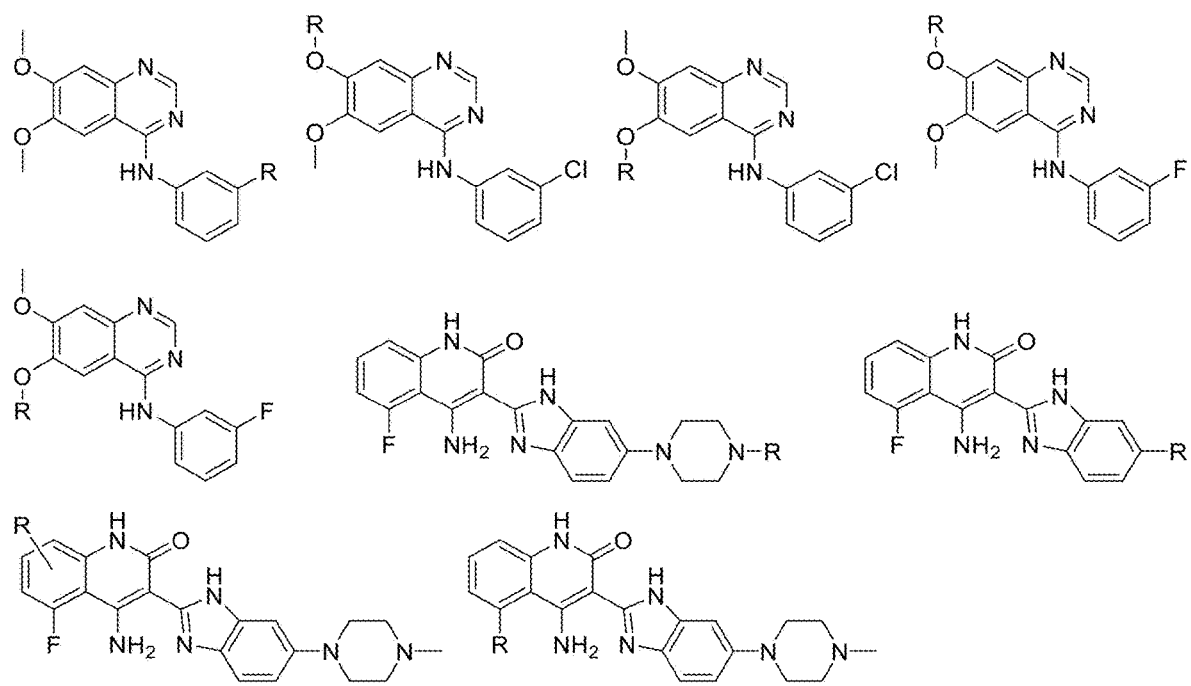

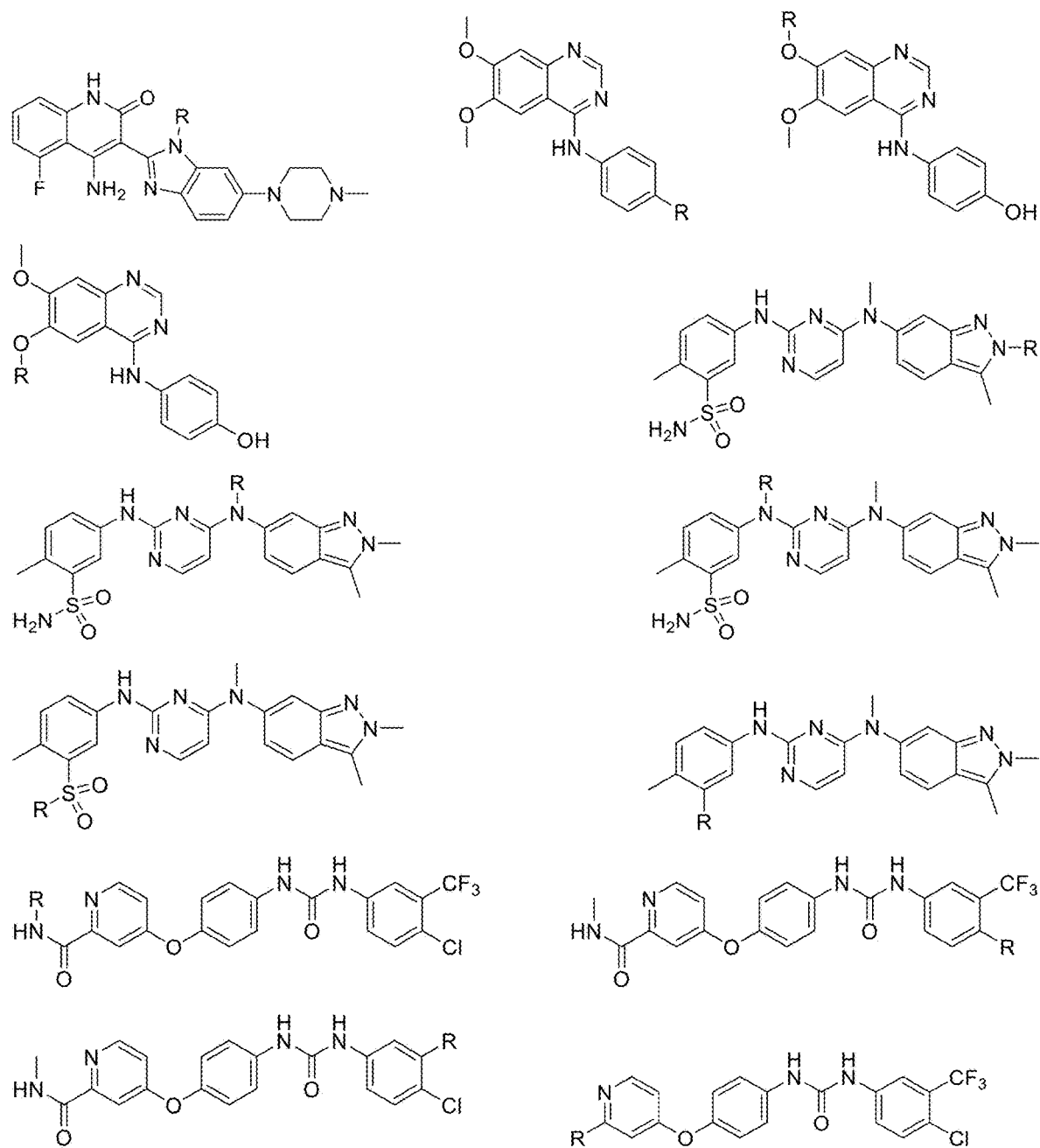
FIG. 2SSS

FIG. 2TTT
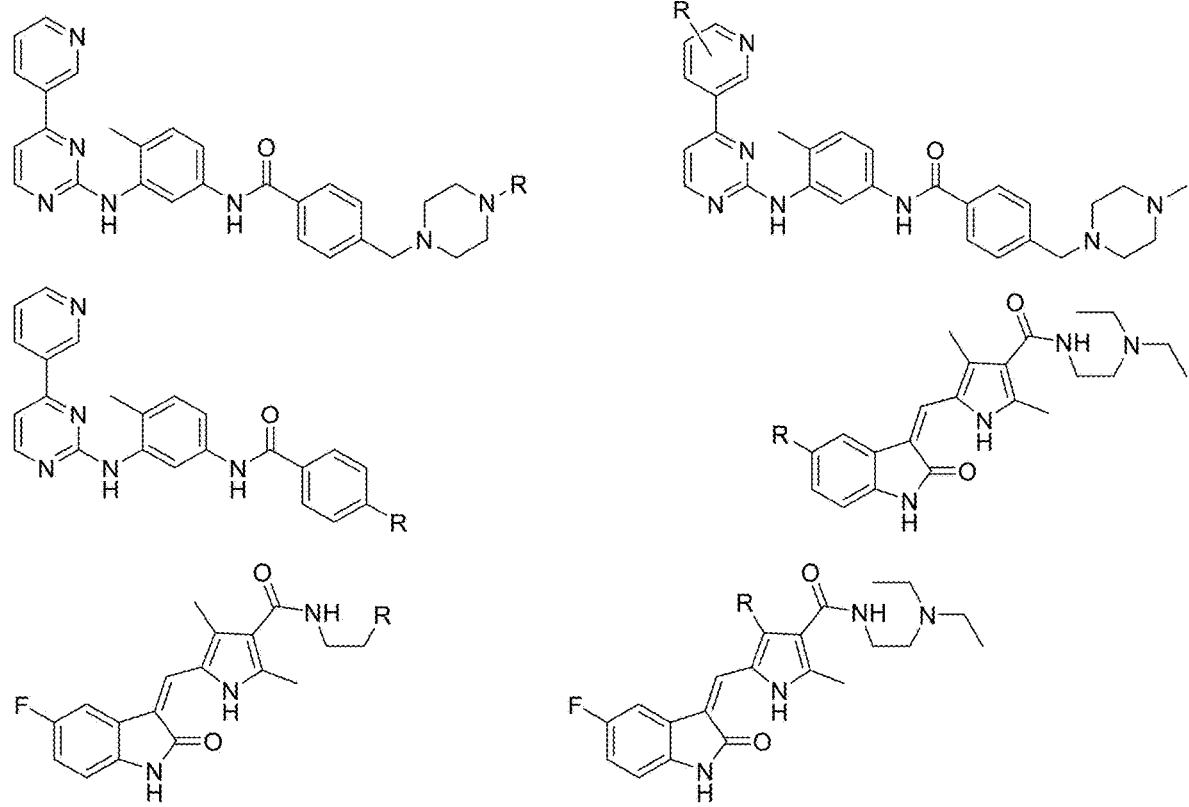
FIG. 2UUU
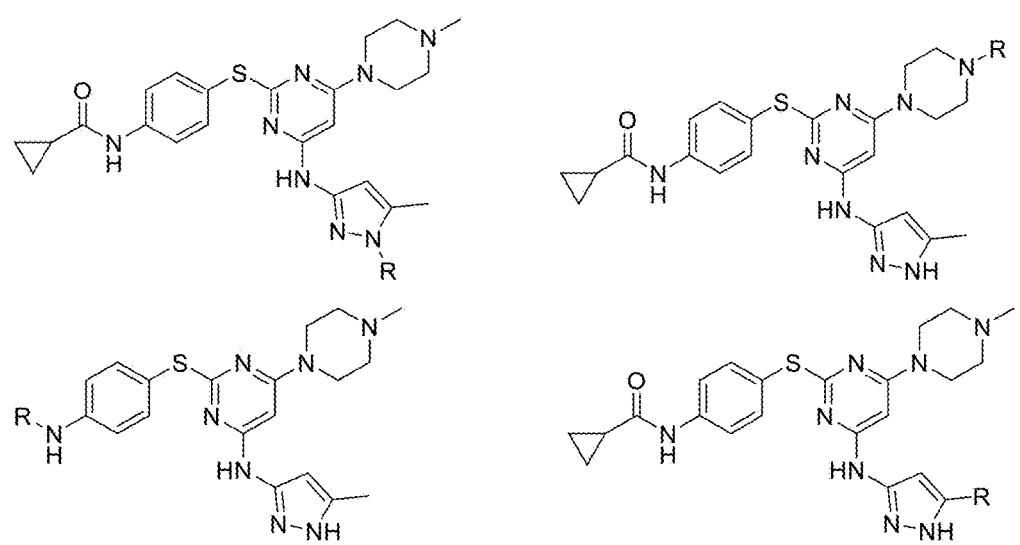

FIG. 2VVV
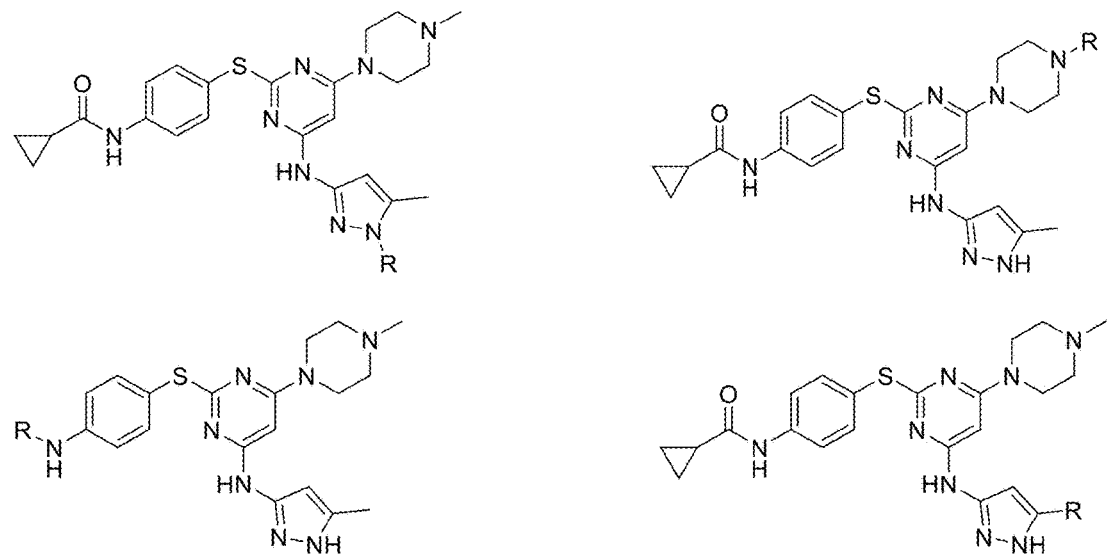
FIG. 2WWW
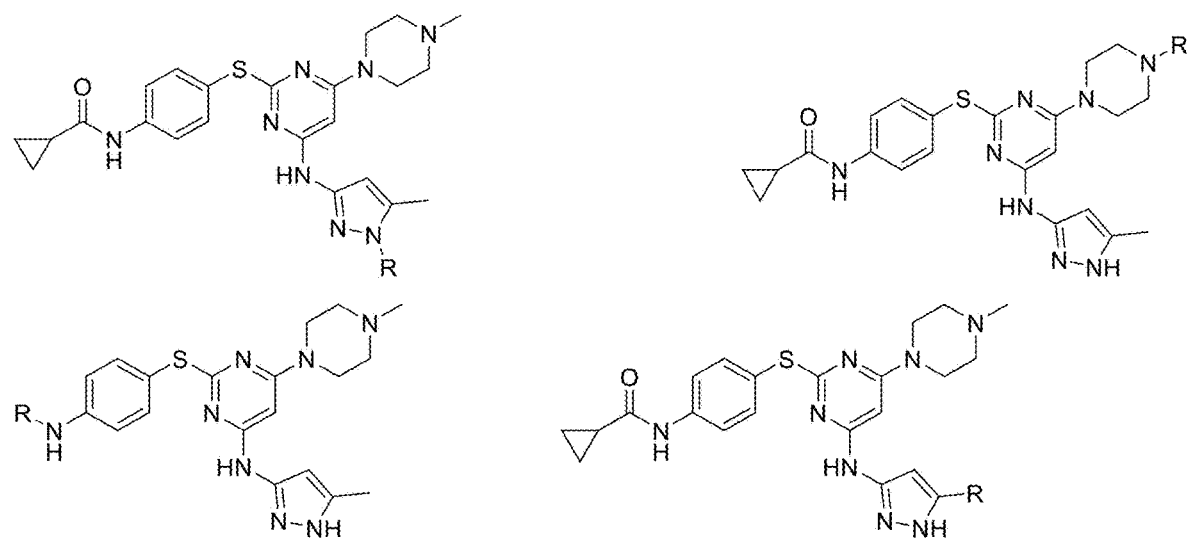

FIG. 2XXX
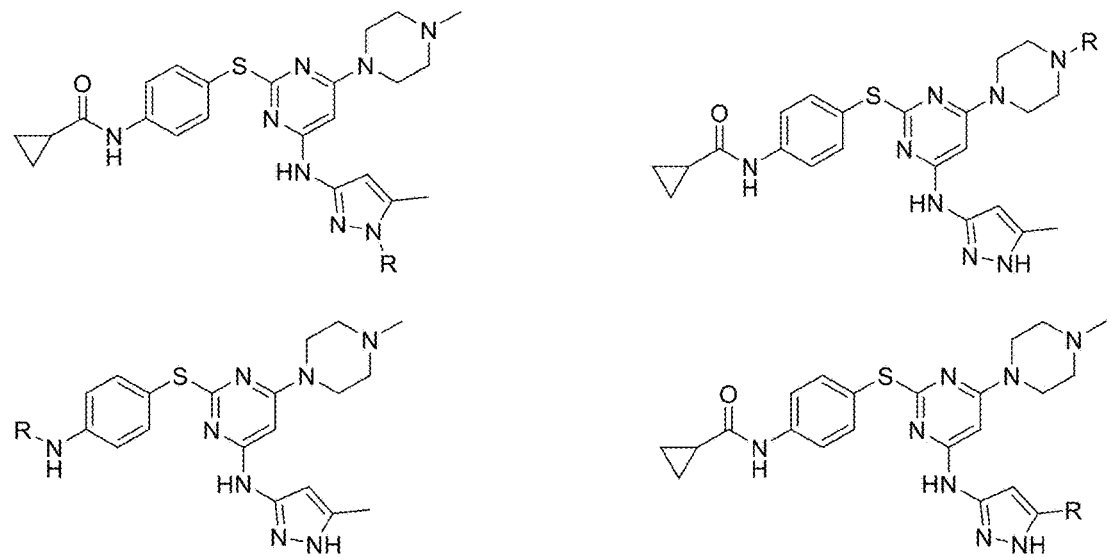
FIG. 2YYY
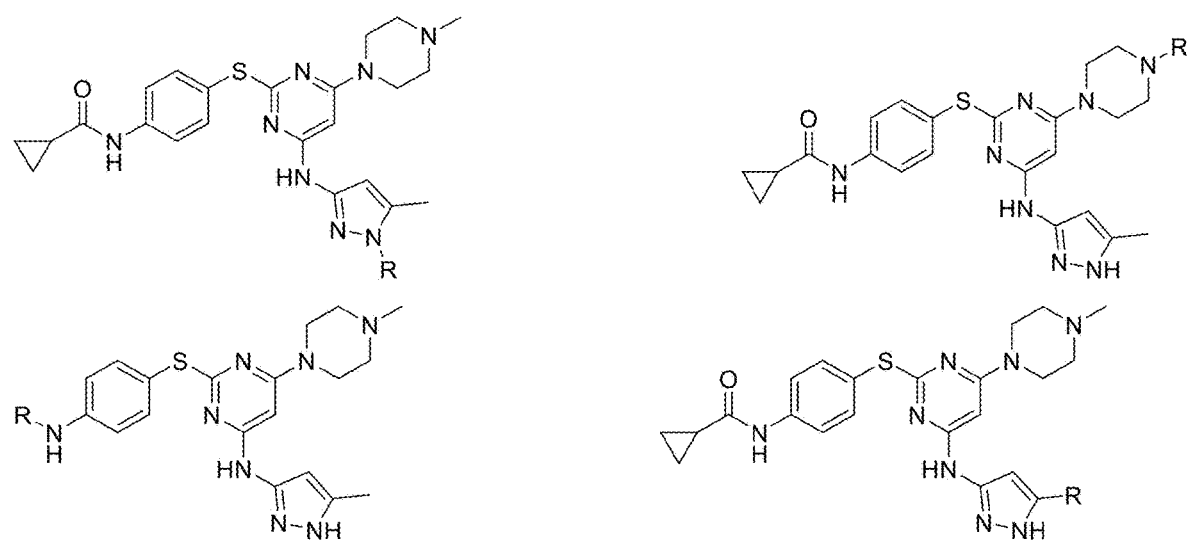

FIG. 2ZZZ
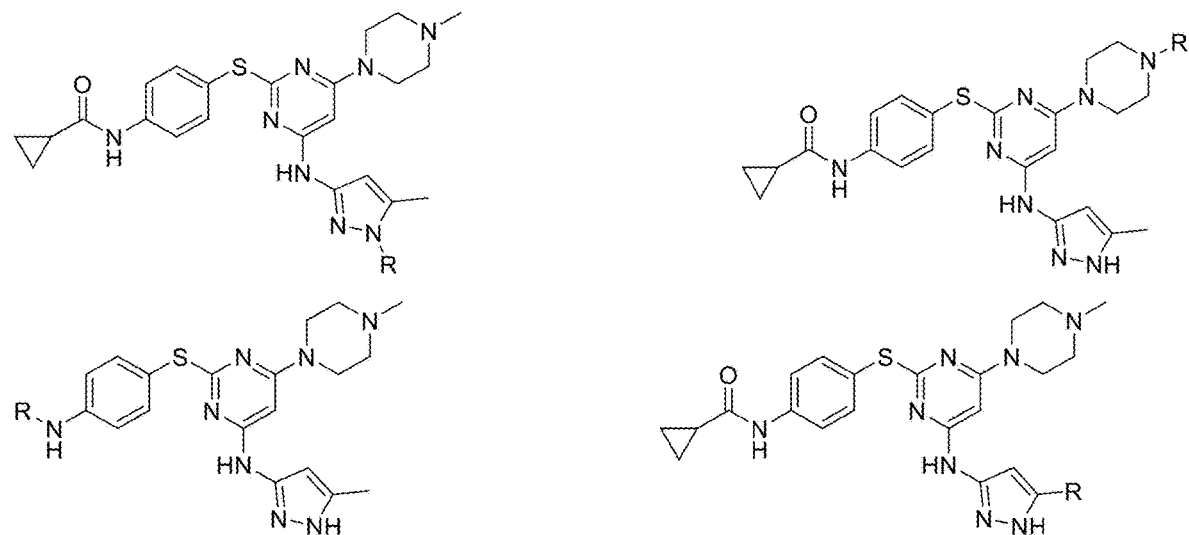
FIG. 2AAAA
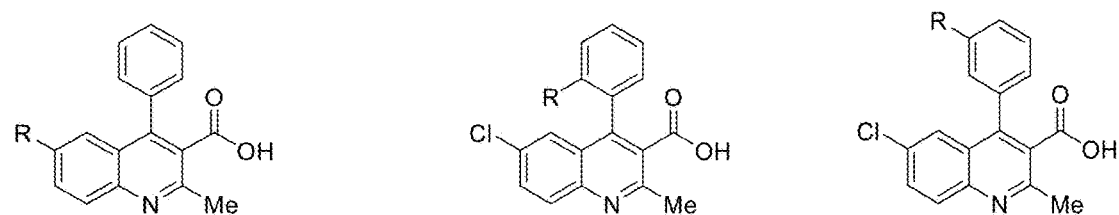
FIG. 2BBBB
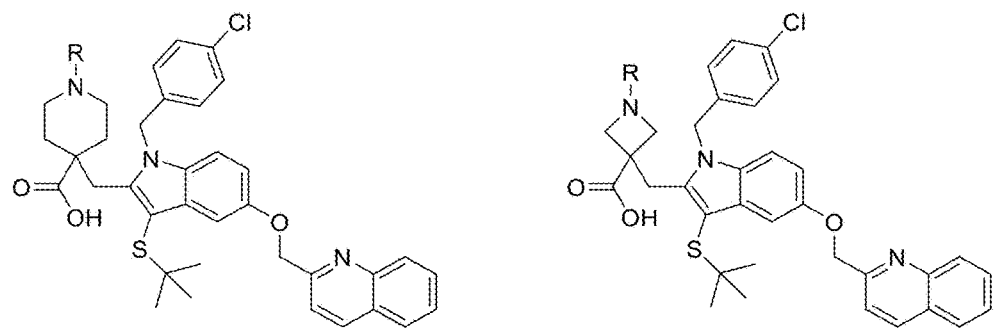

FIG. 2CCCC
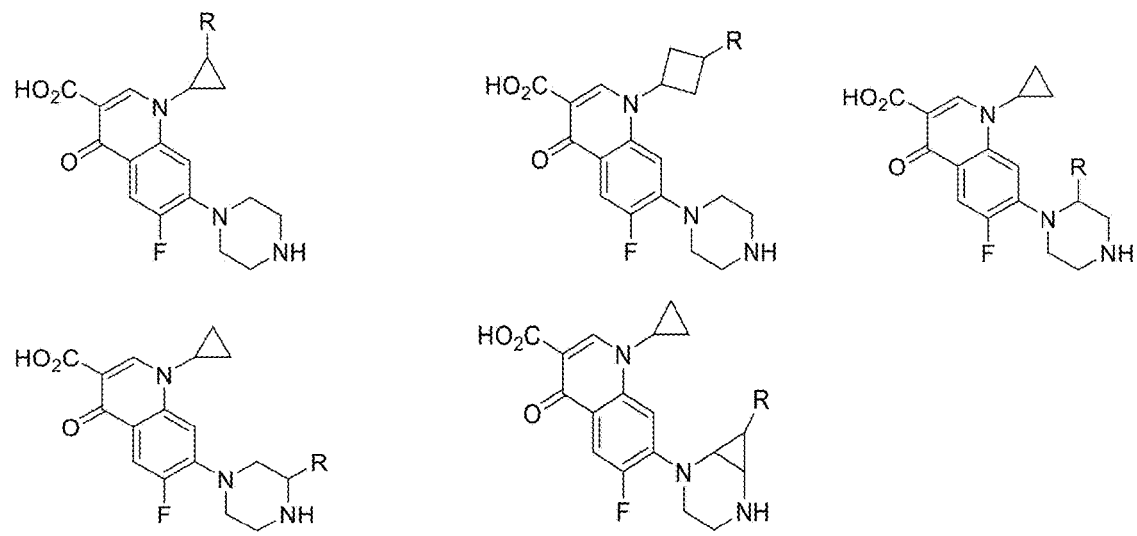
FIG. 2DDDD
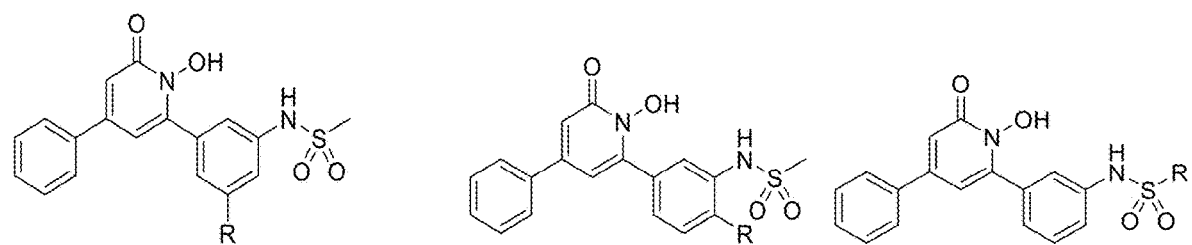
FIG. 2EEEE
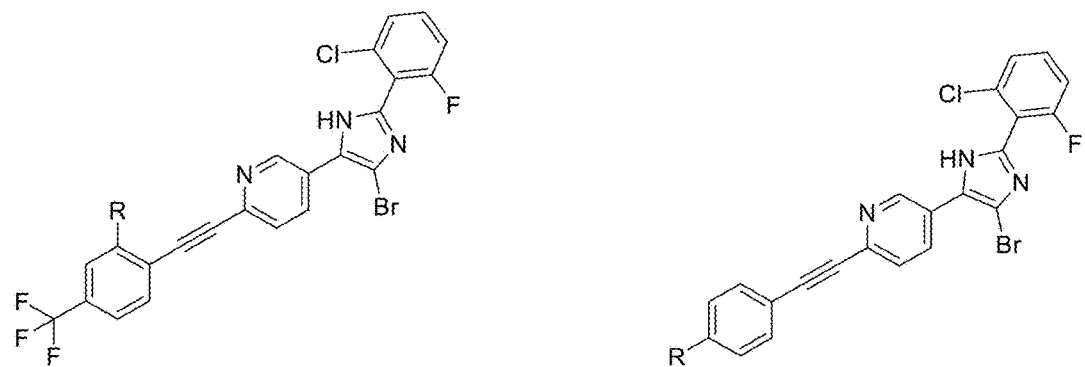

FIG. 2FFFF
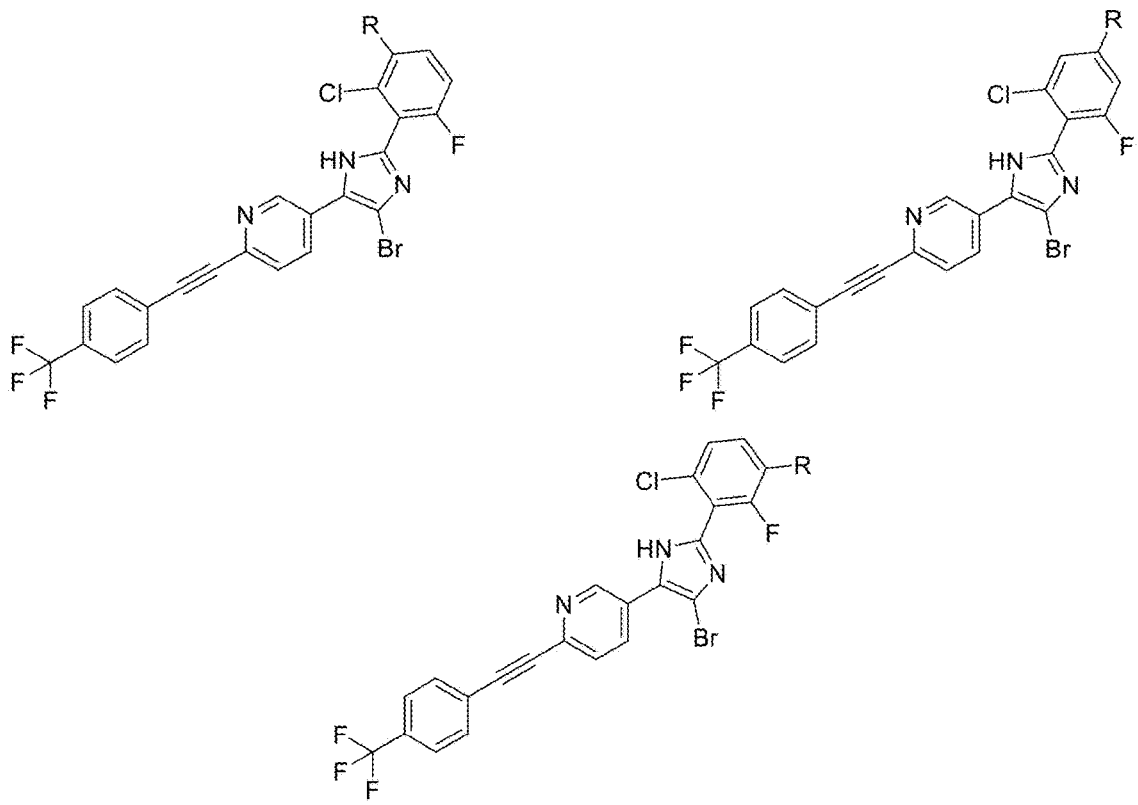
FIG. 2GGGG
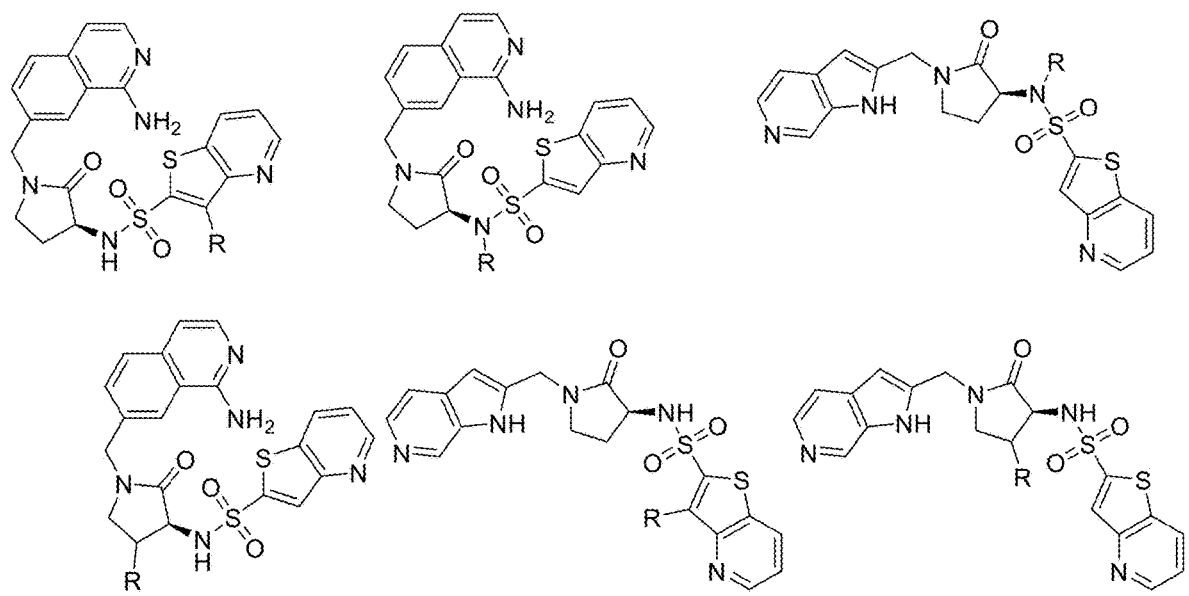

FIG. 2HHHH
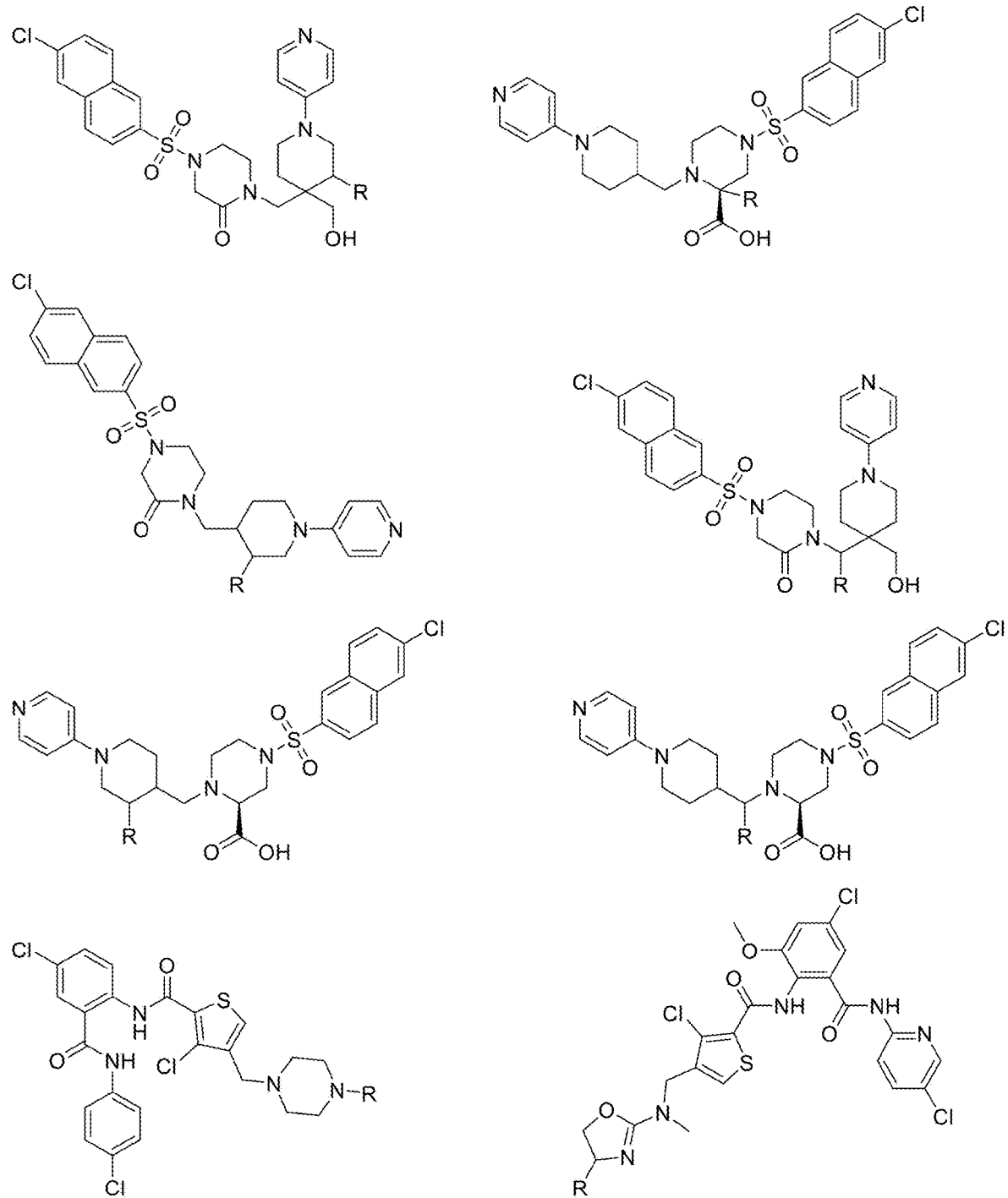

FIG. 2IIII
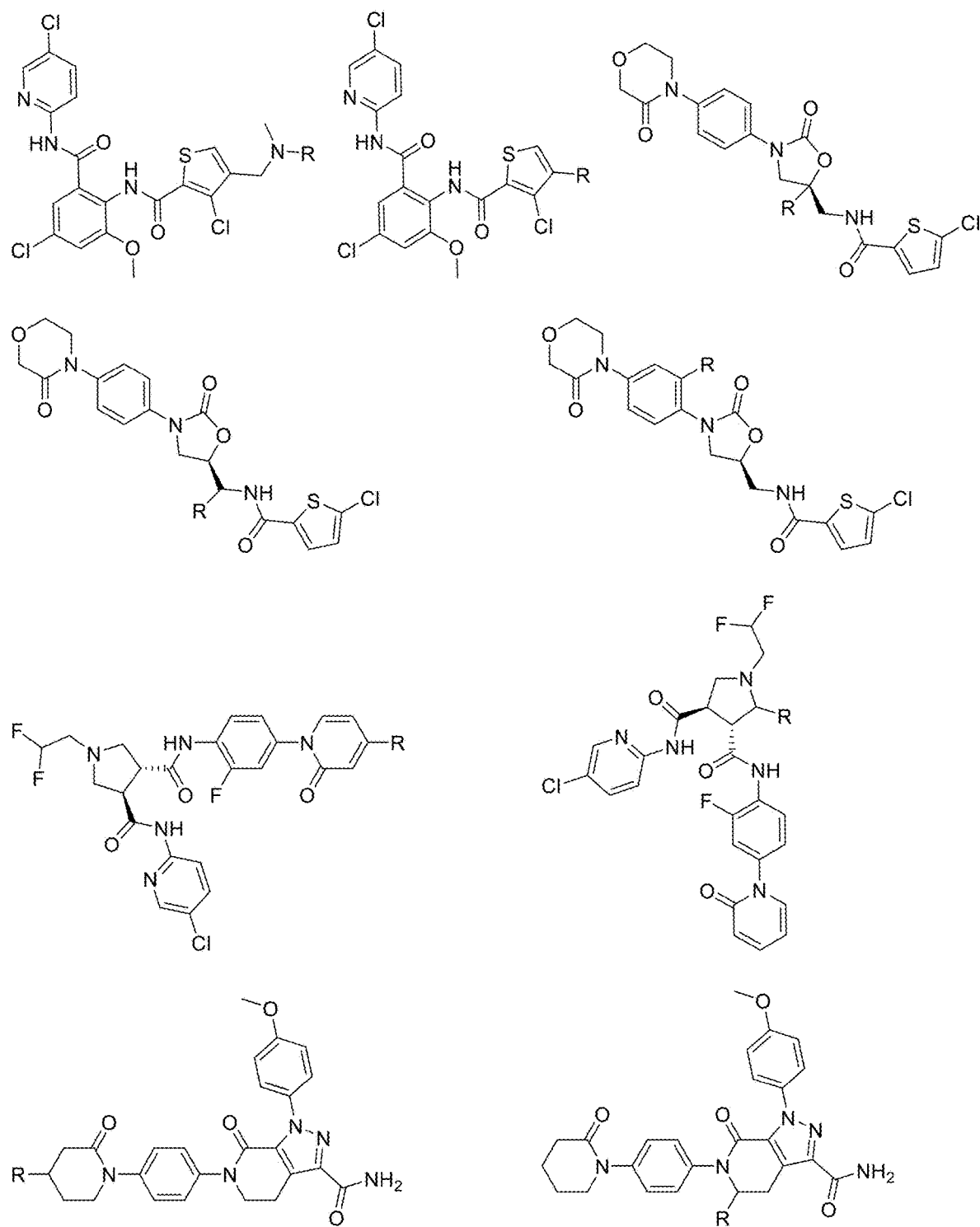

FIG. 2JJJJ
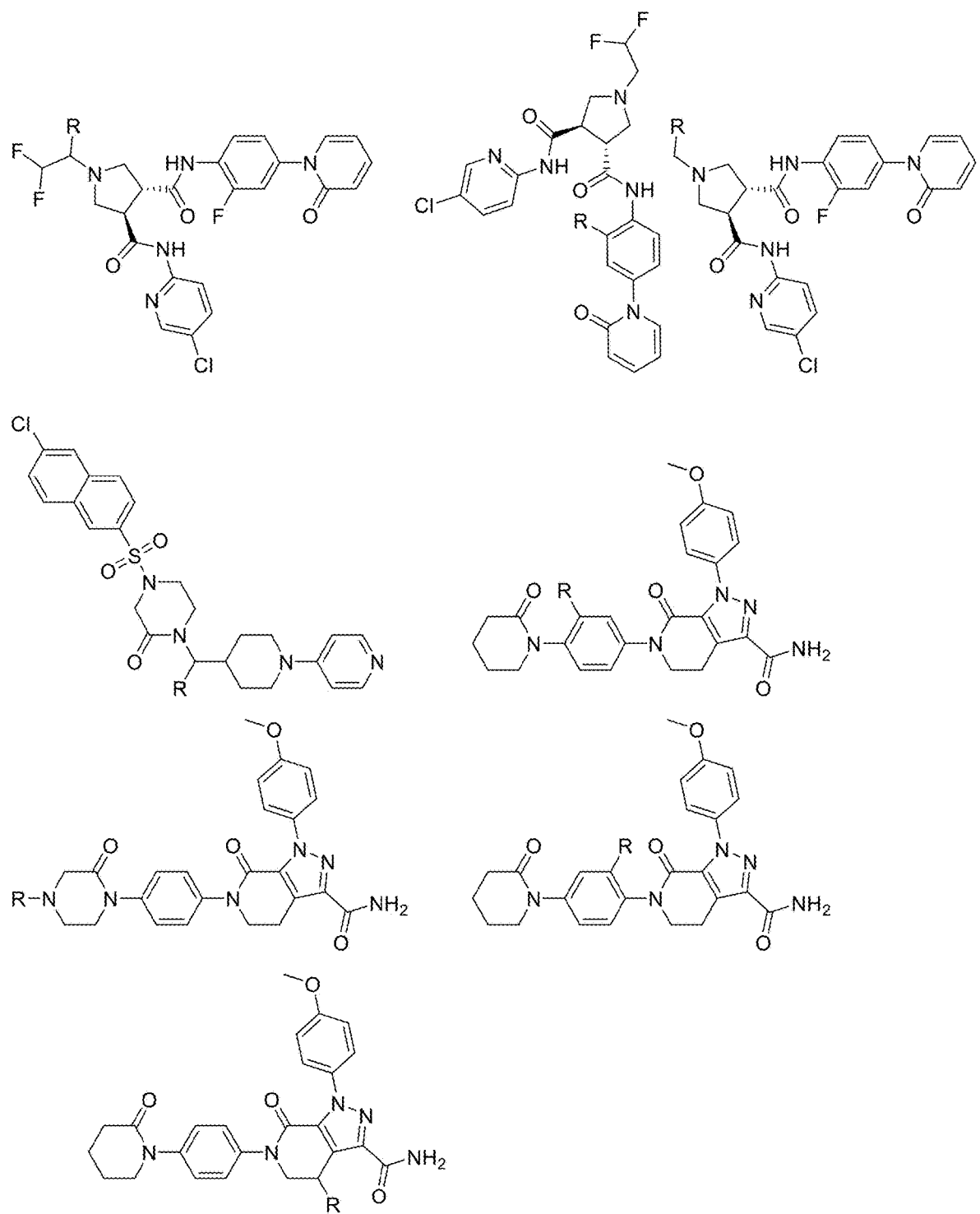

FIG. 2KKKK
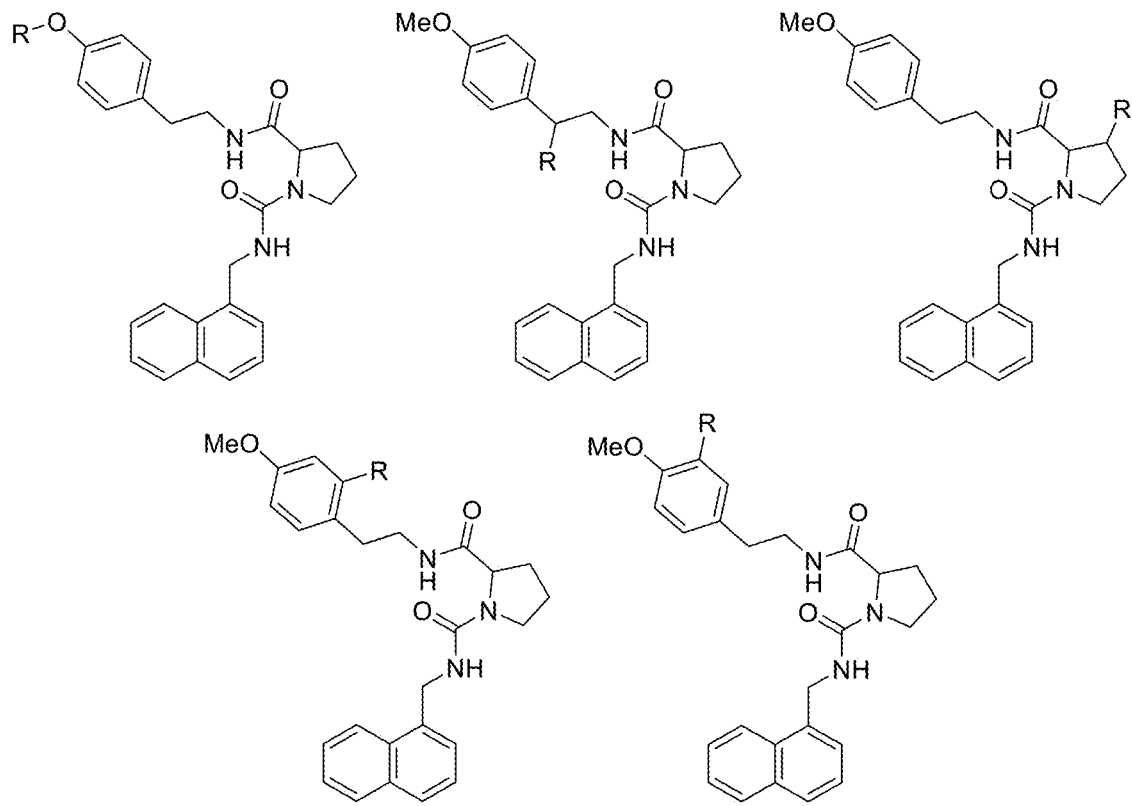
FIG. 2LLLL
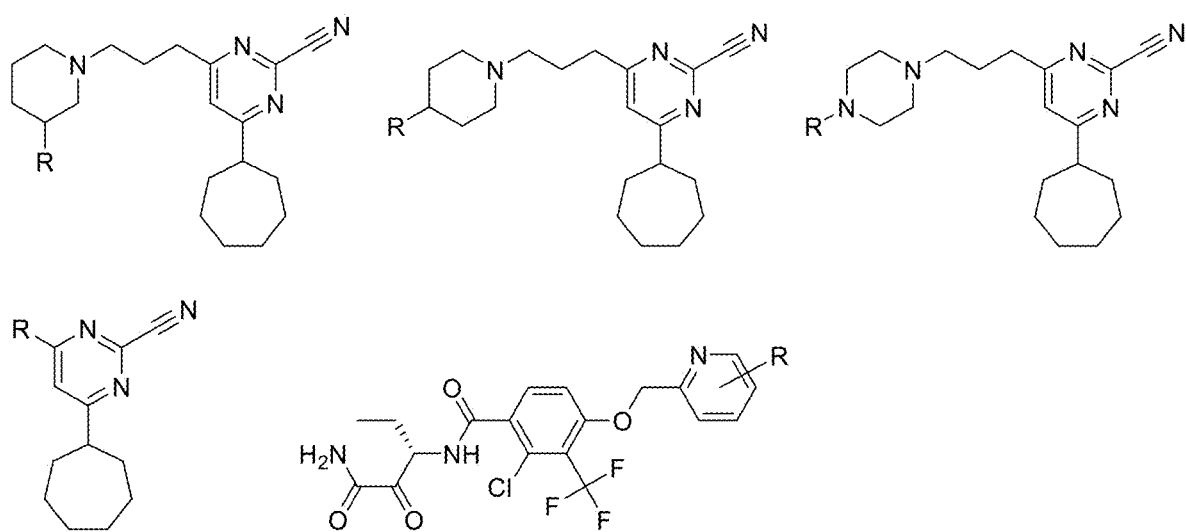

FIG. 2MMMM
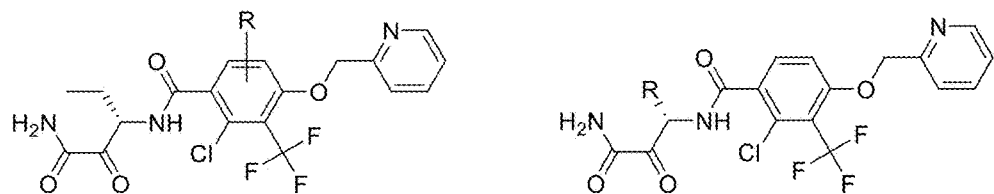
FIG. 2NNNN
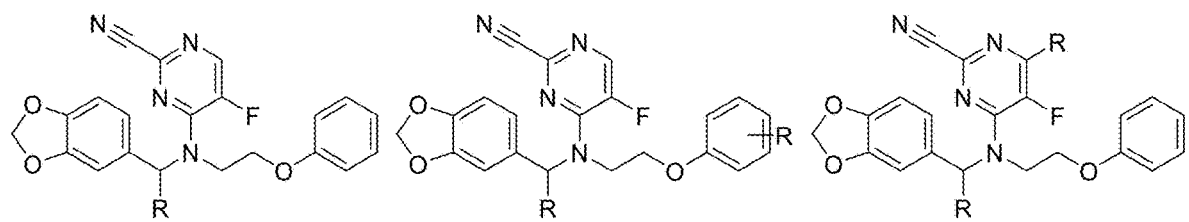
FIG. 2OOOO
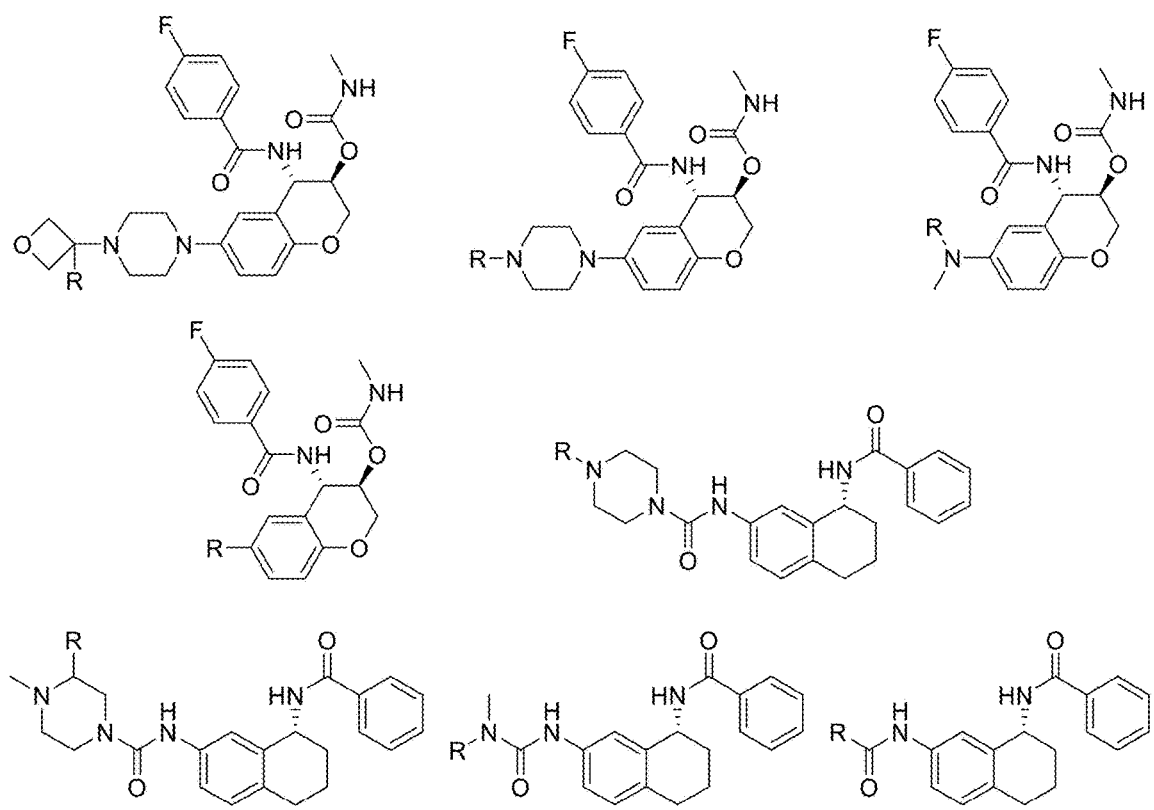

FIG. 2PPPP
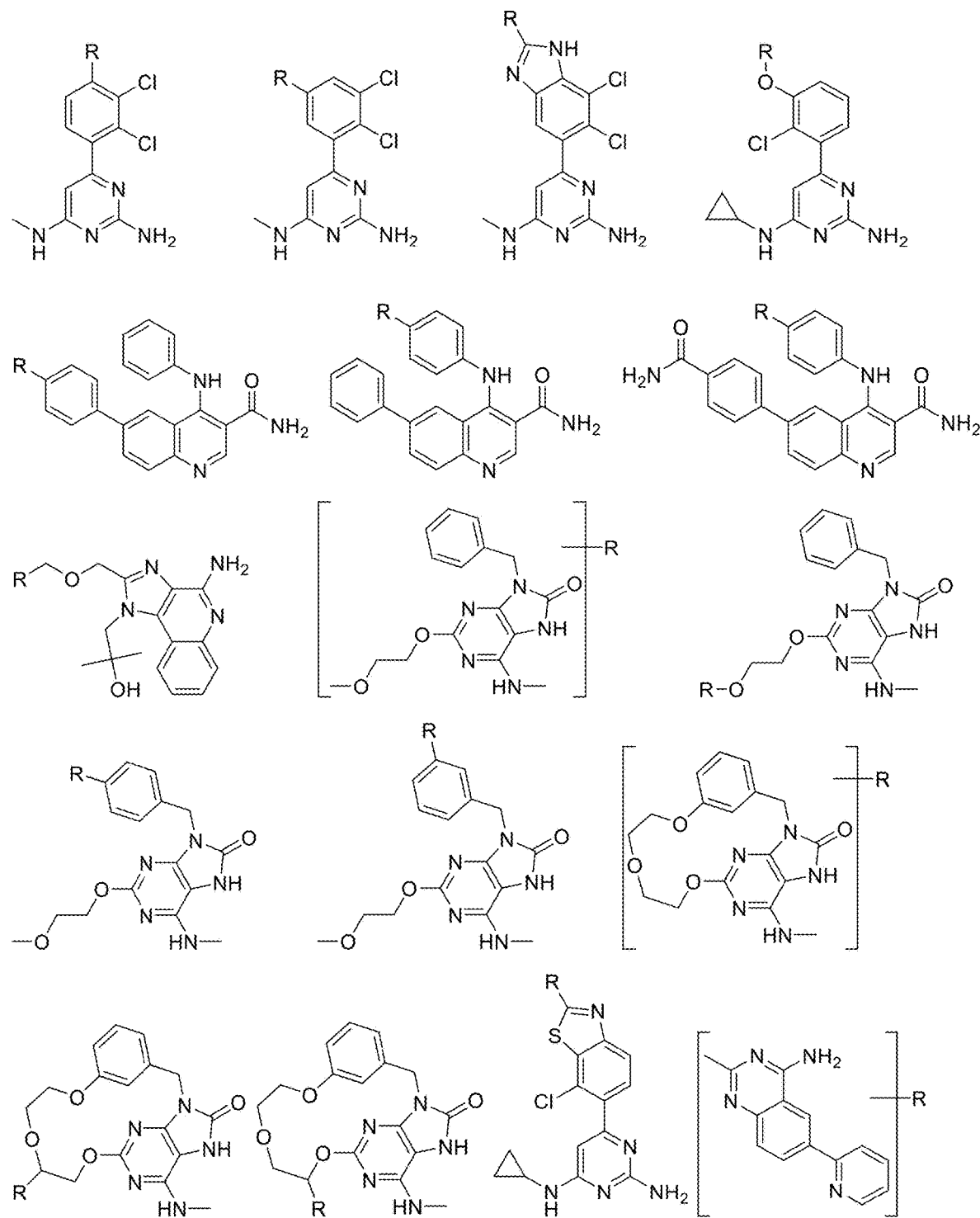

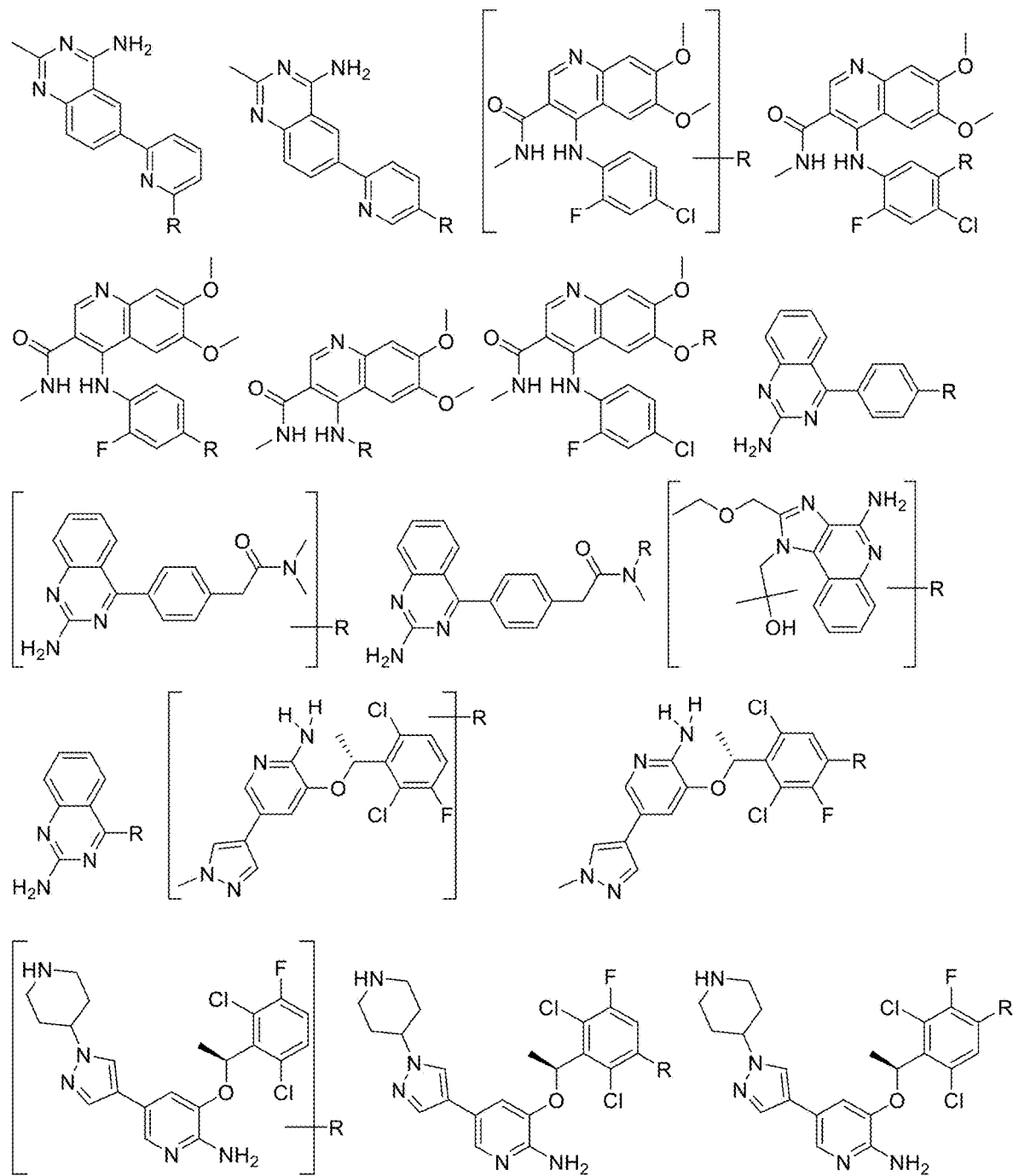
FIG. 2QQQQ

FIG. 2RRRR
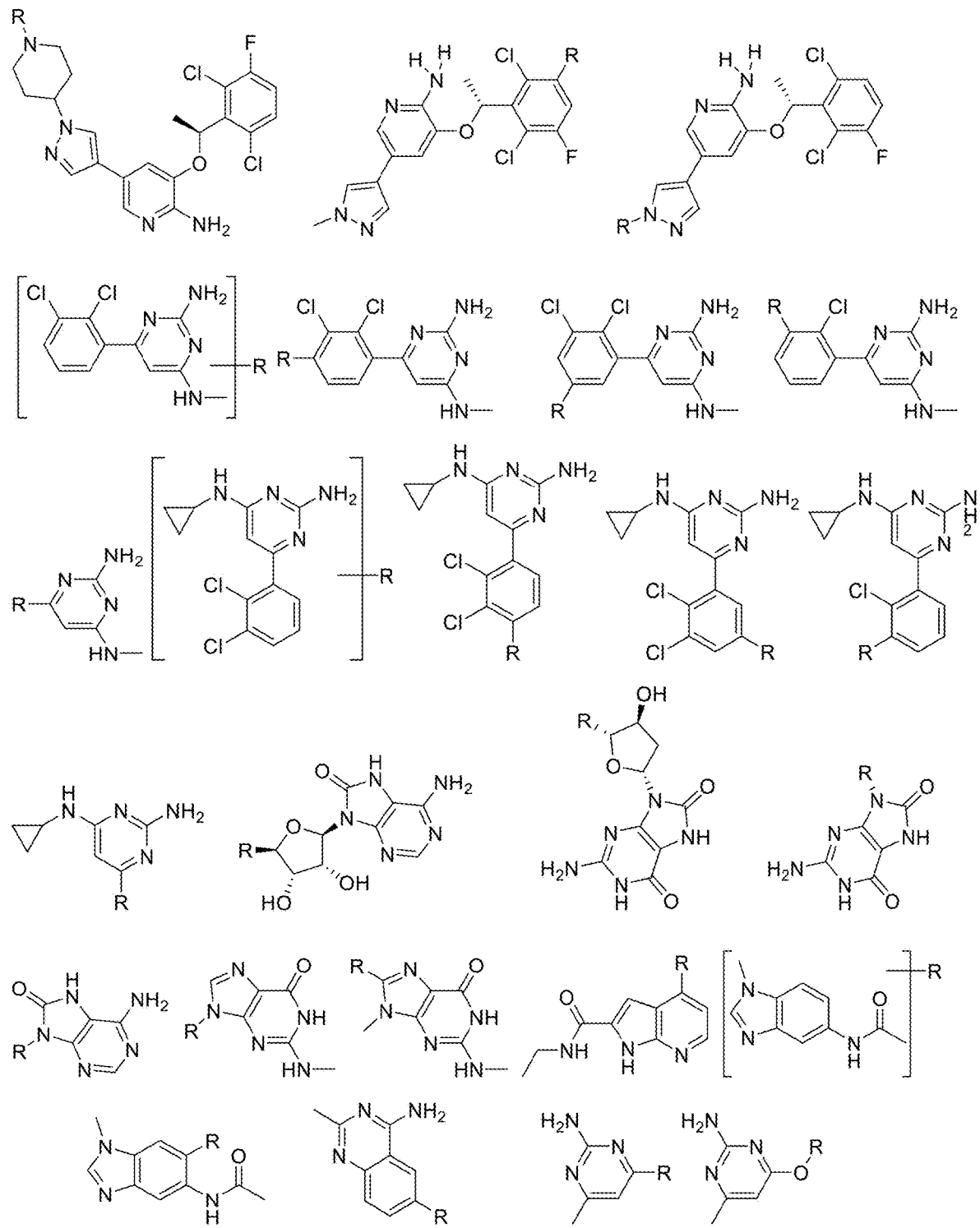

FIG. 2SSSS
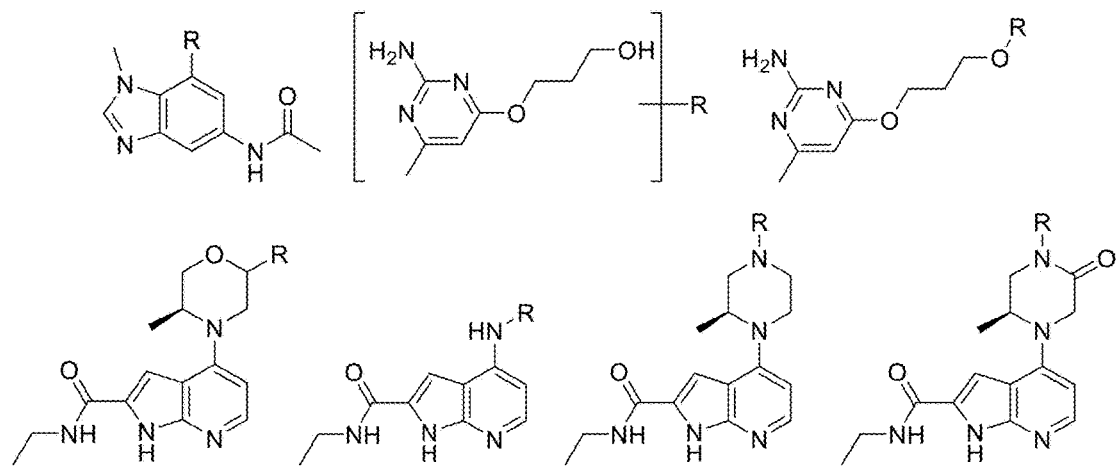
FIG. 2TTTT
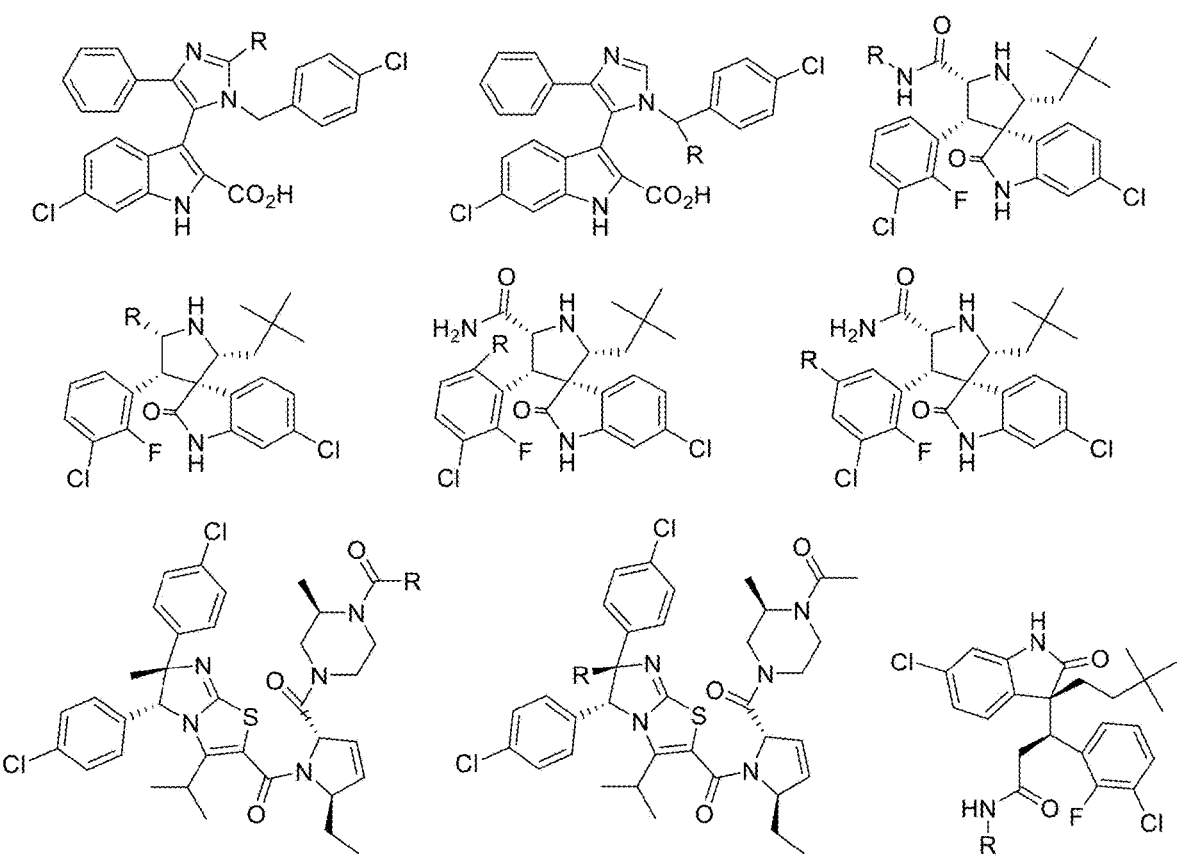

FIG. 2UUUU
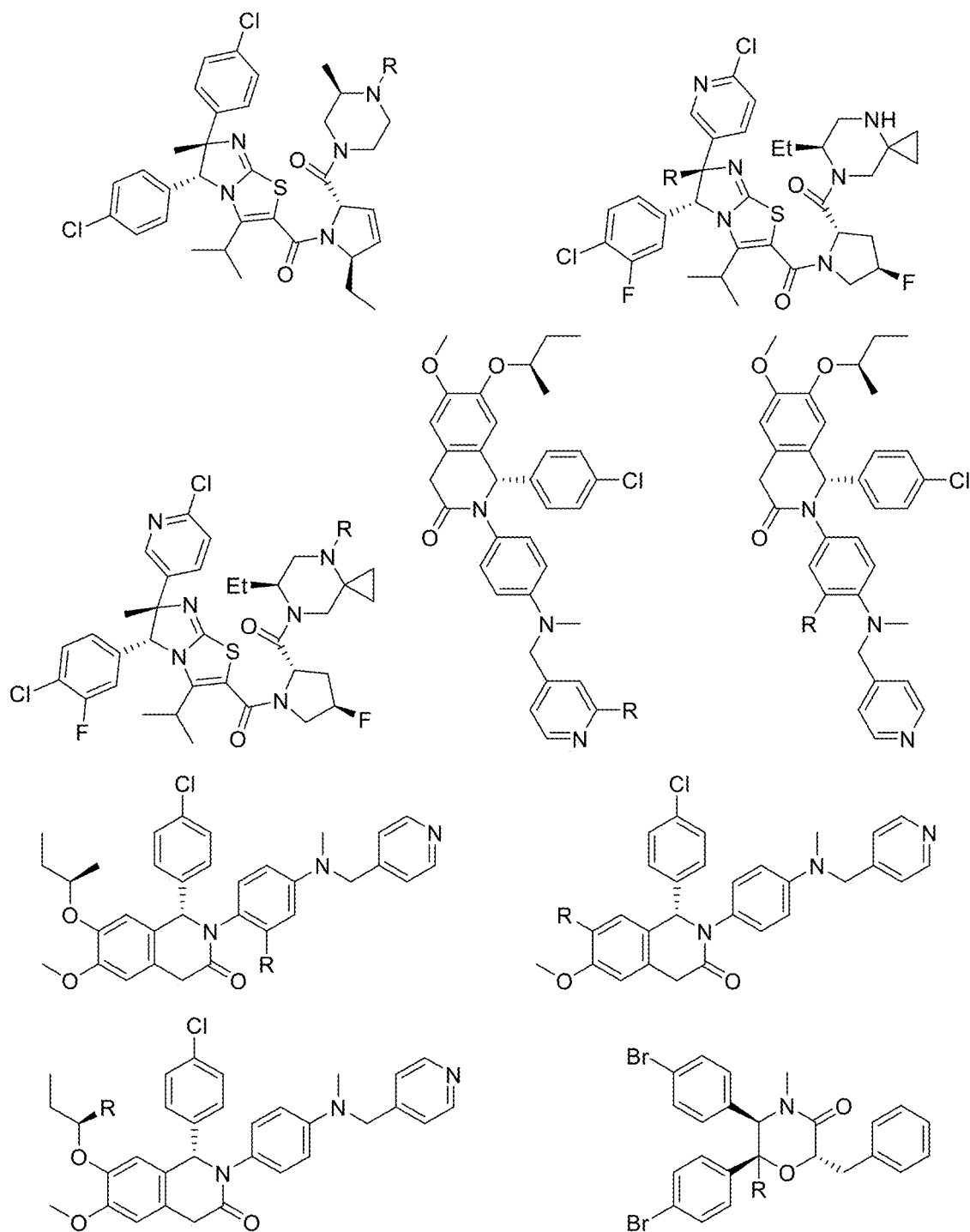

FIG. 2VVVV
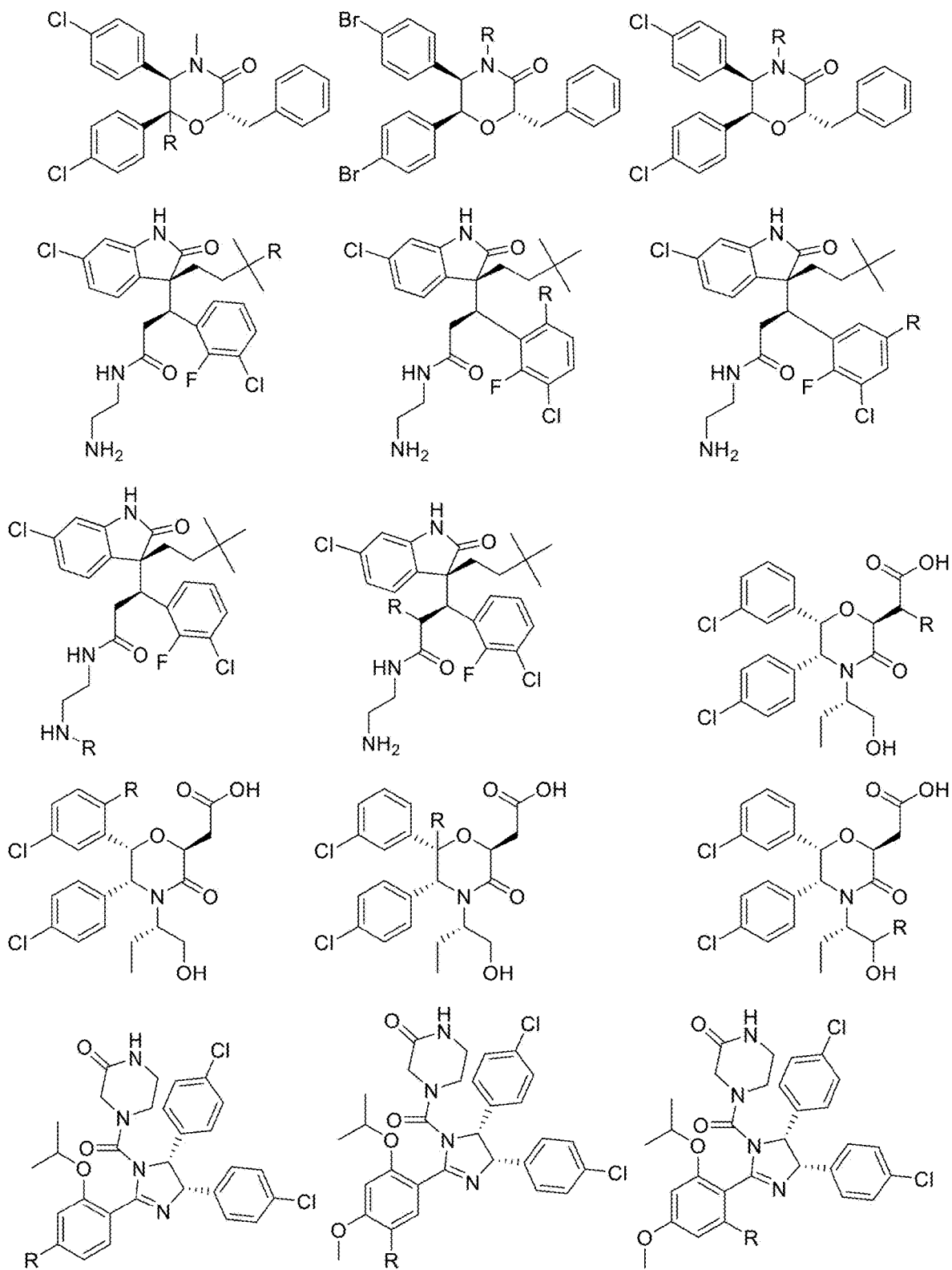

FIG. 2WWWW
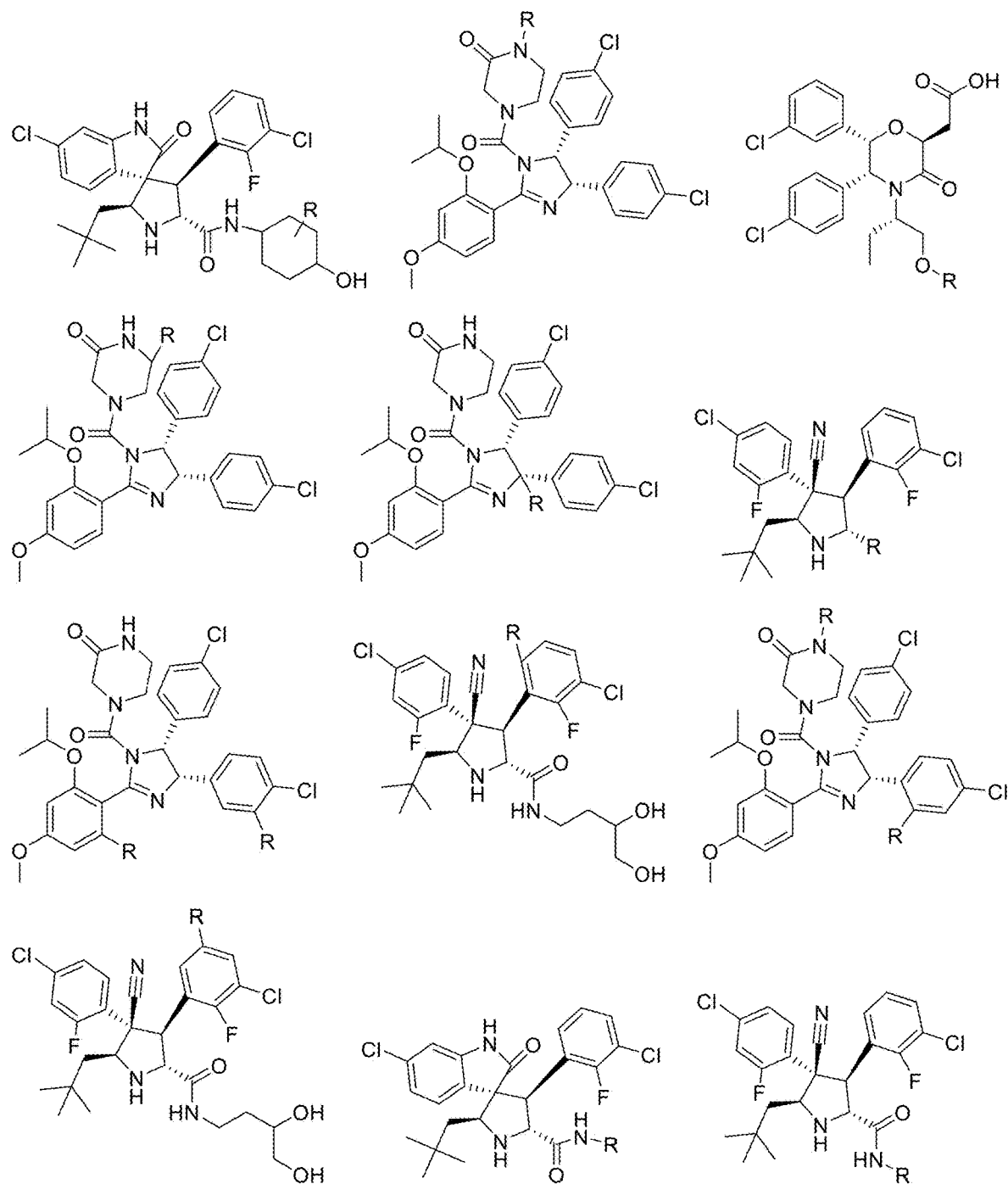

FIG. 2XXXX
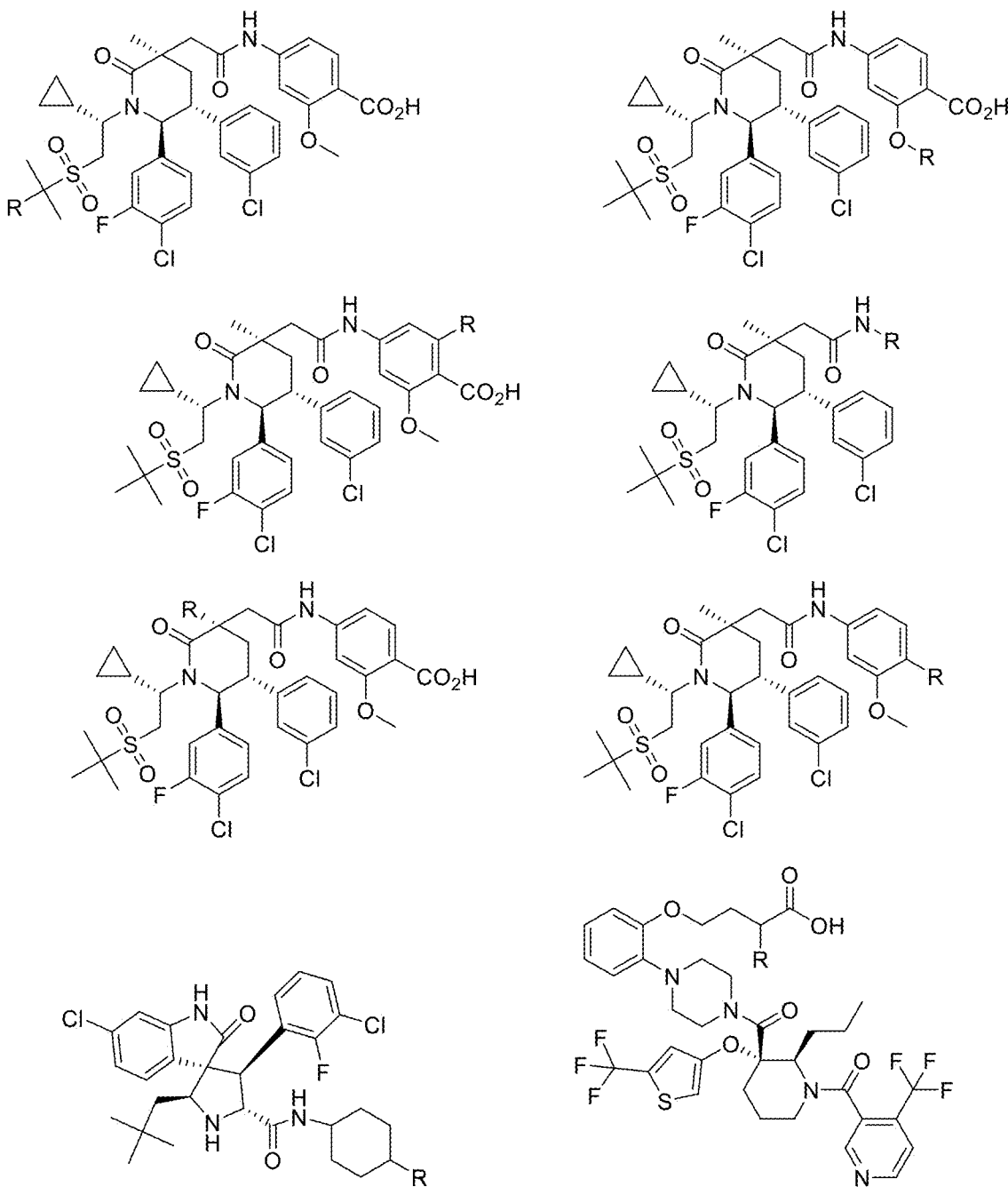

FIG. 2YYYY
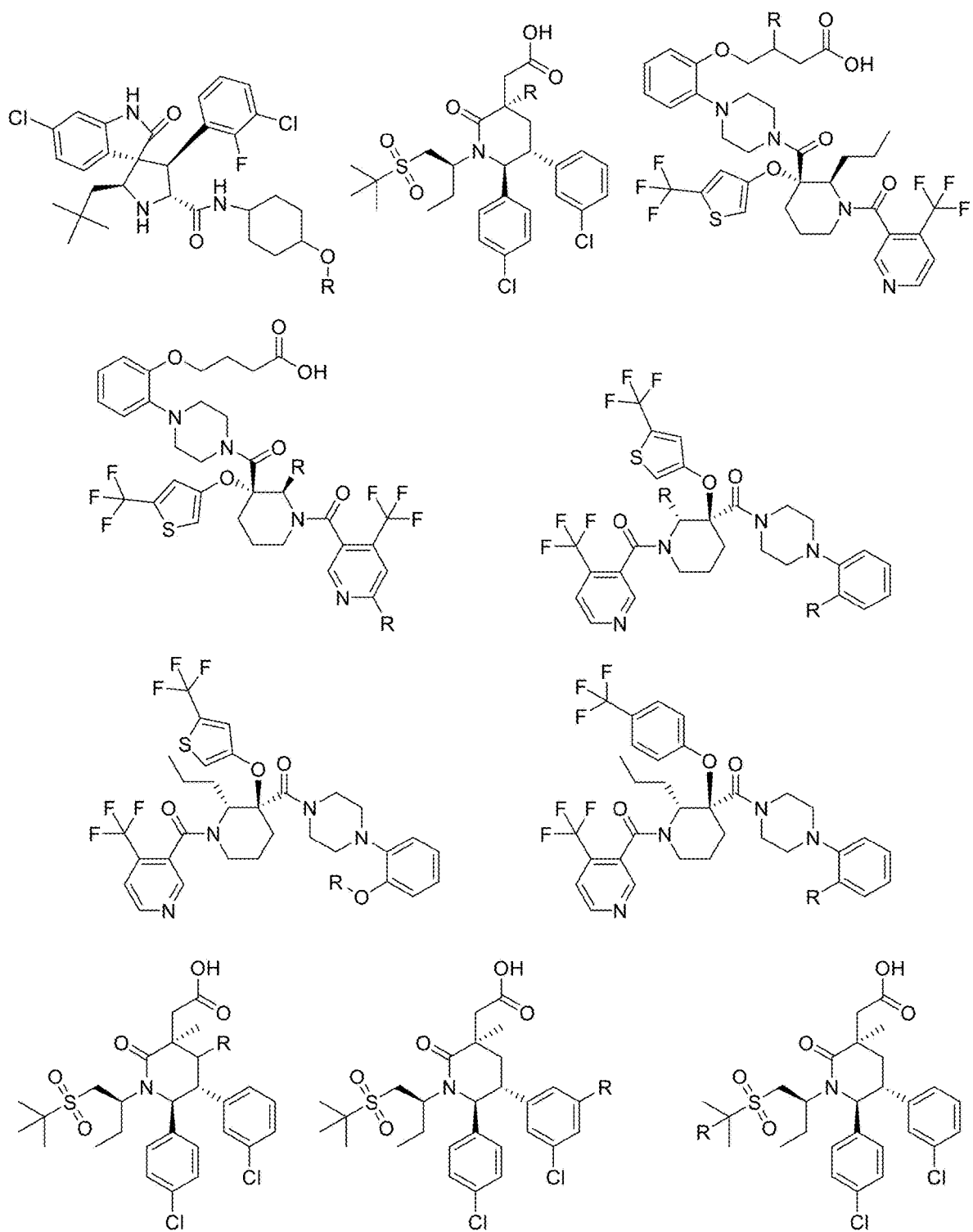

FIG. 2ZZZZ
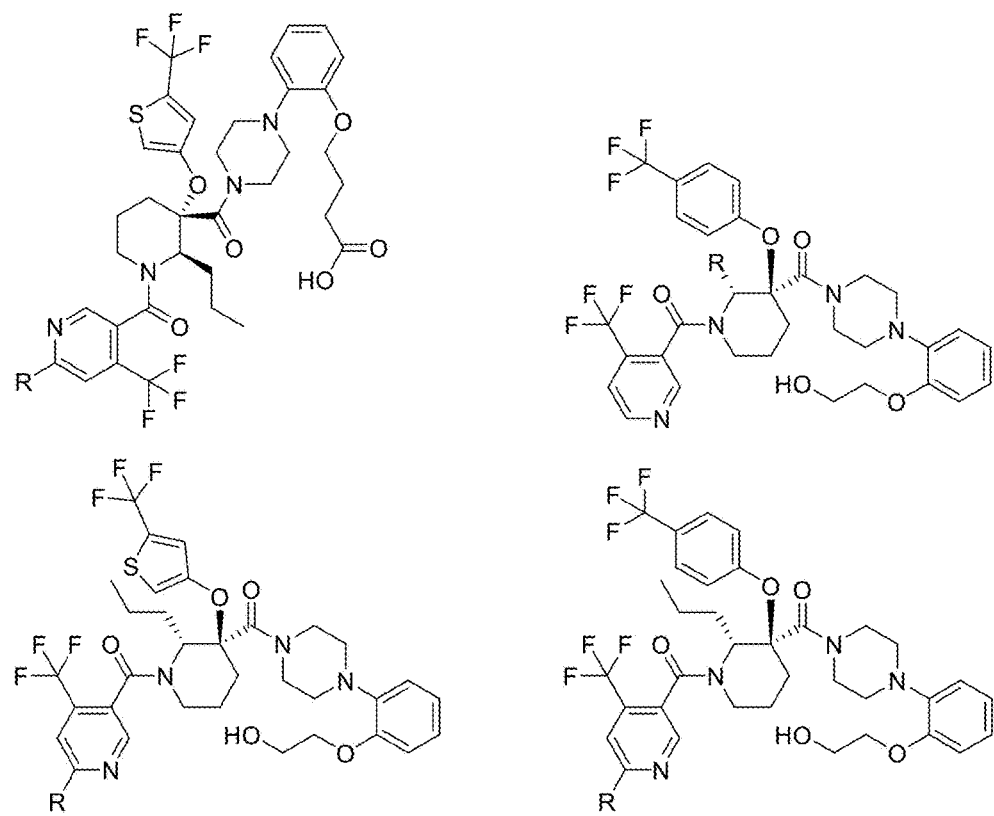
FIG. 2AAAAA
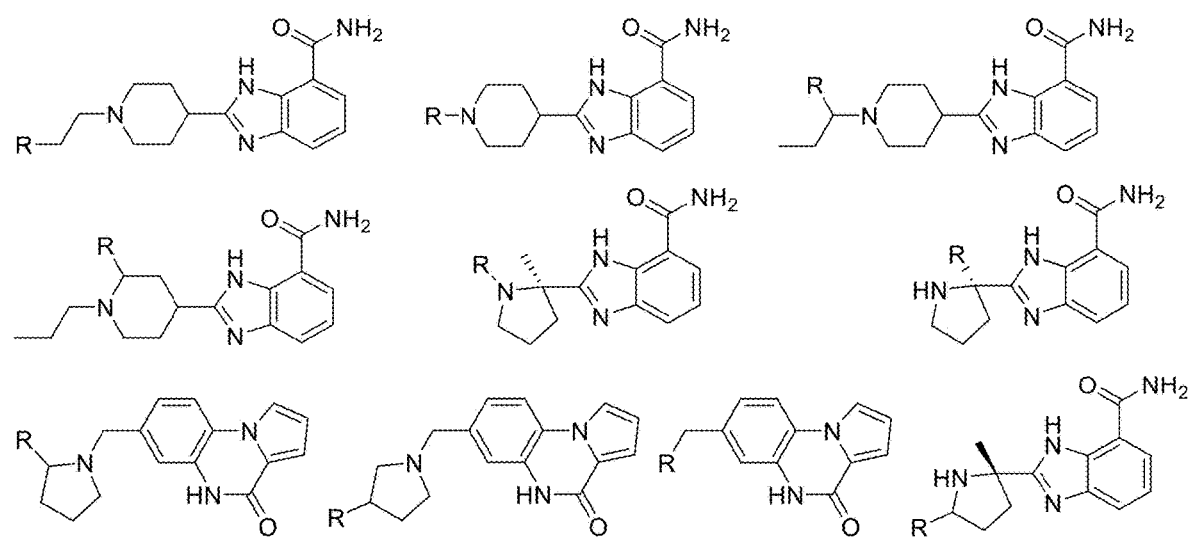

FIG. 2BBBBB

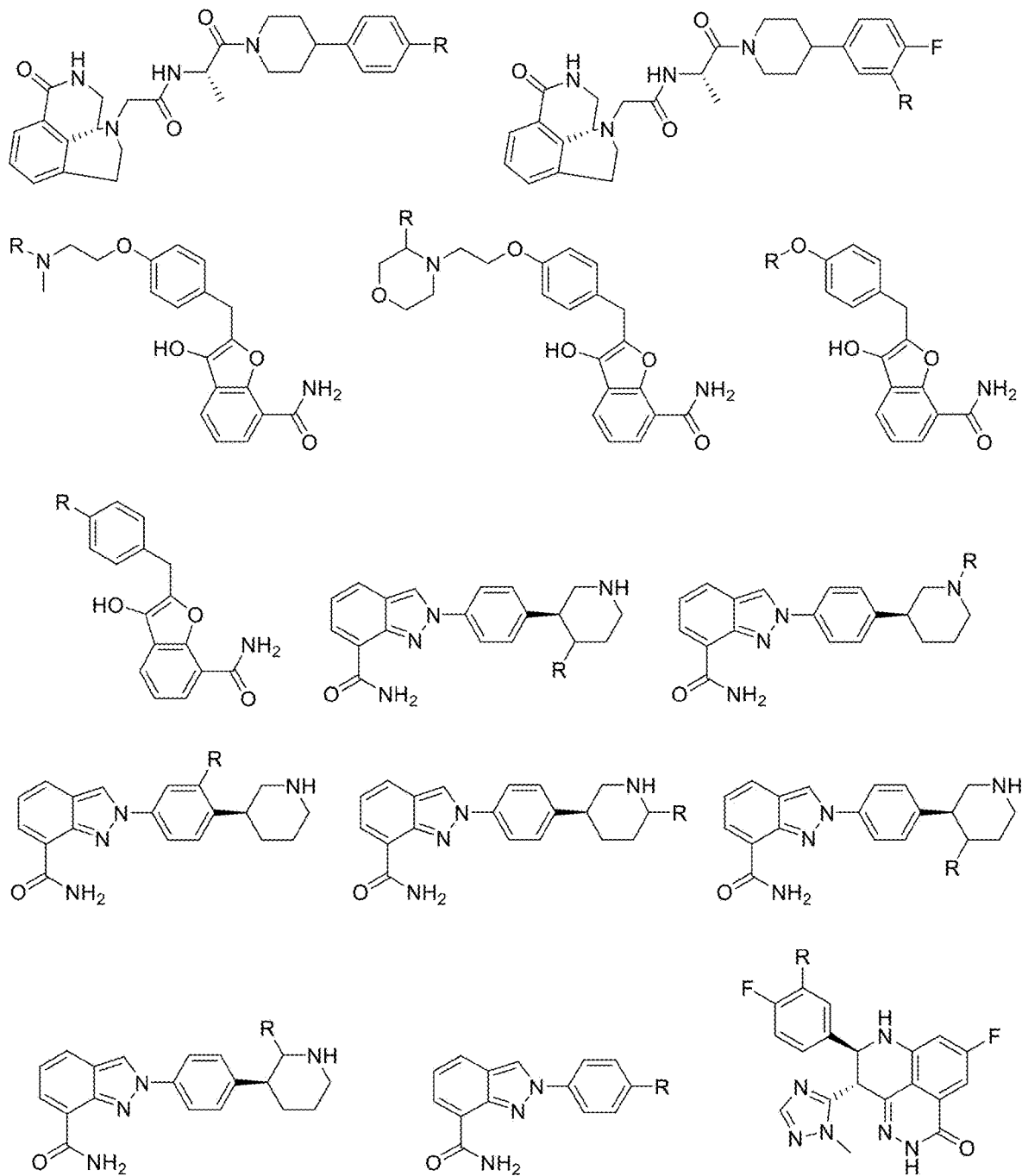
FIG. 2CCCCC

FIG. 2DDDDD
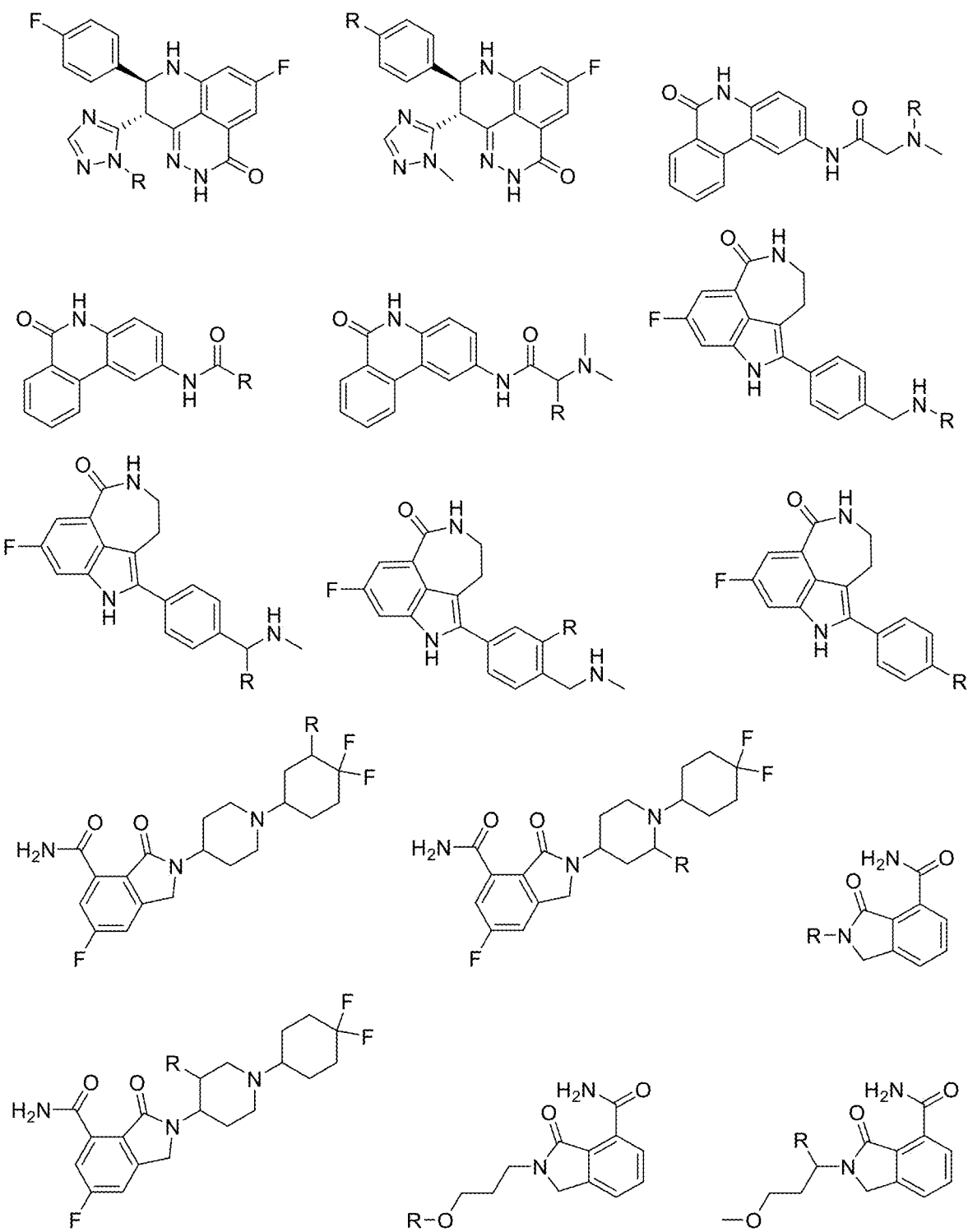

FIG. 2EEEEE
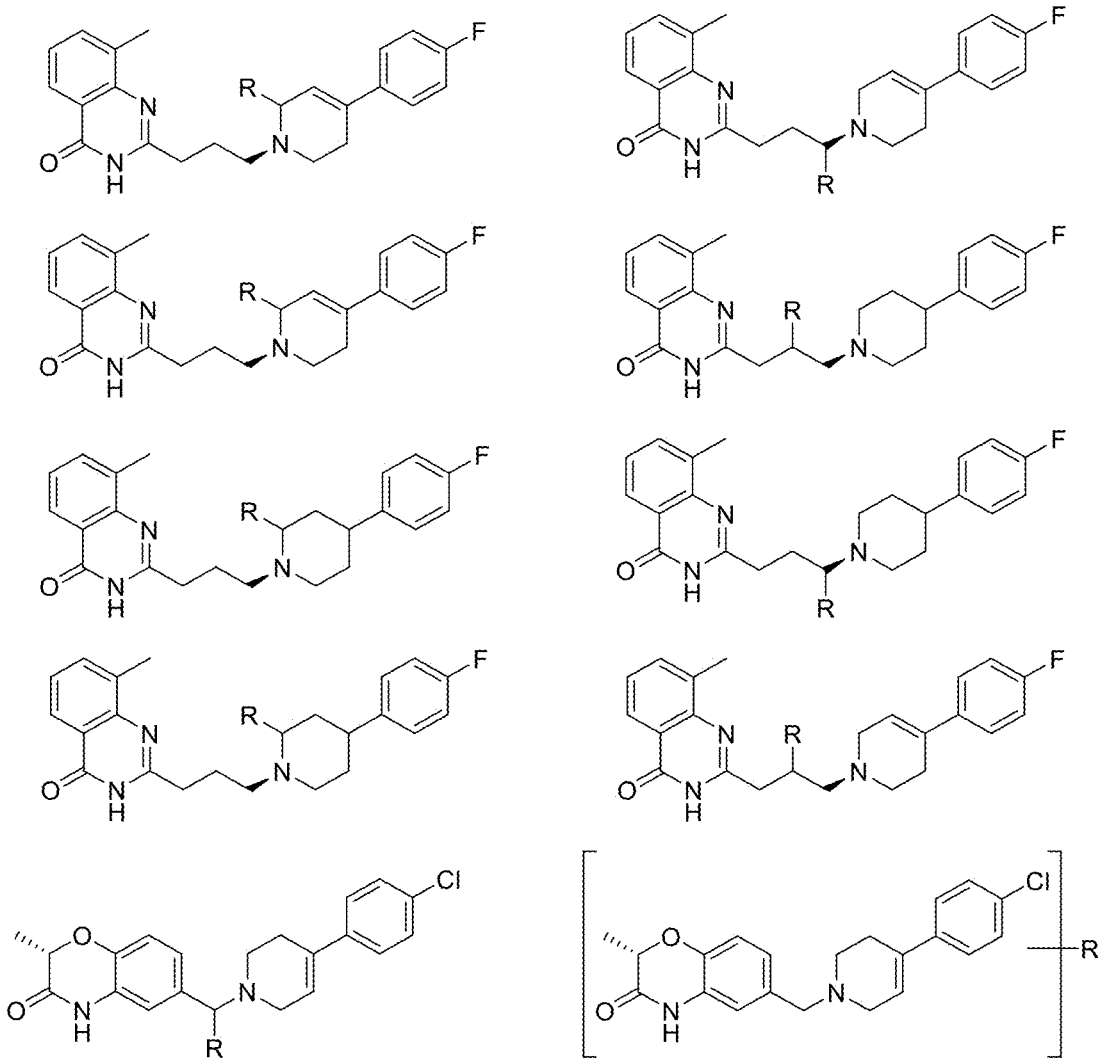
FIG. 2FFFFF
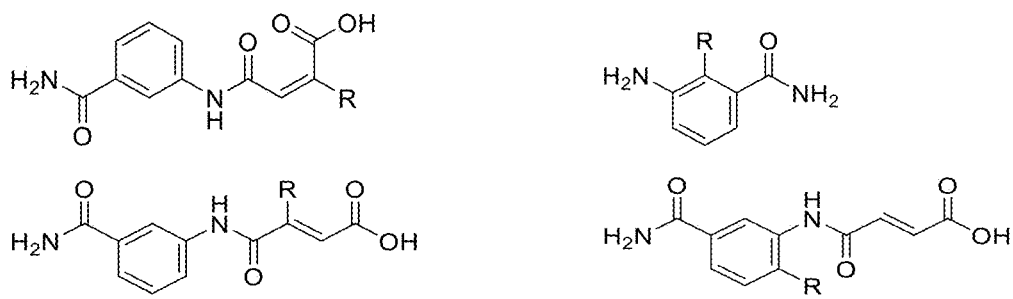

FIG. 2GGGGG
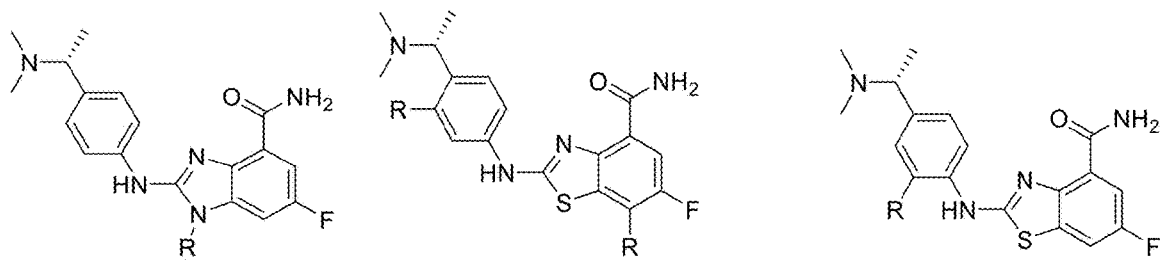
FIG. 2HHHHH
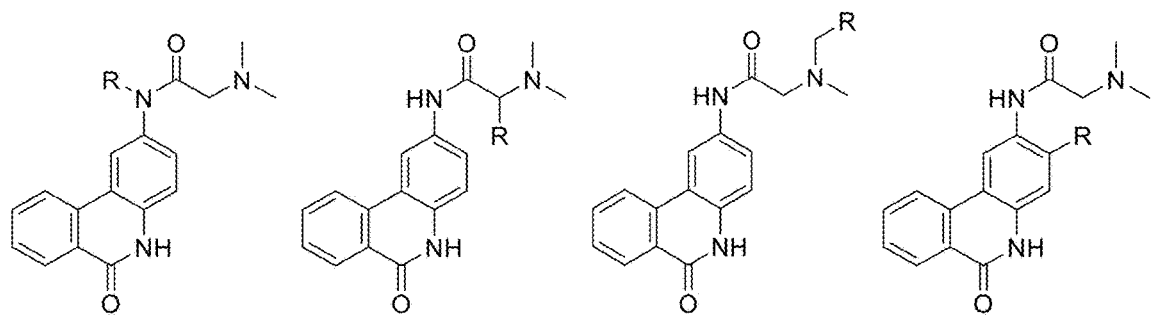
FIG. 2IIIII
FIG. 2JJJJJ
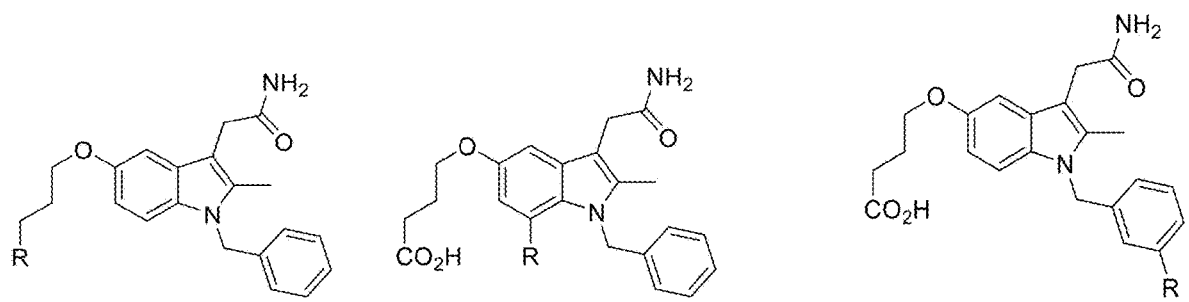

FIG. 2KKKKK
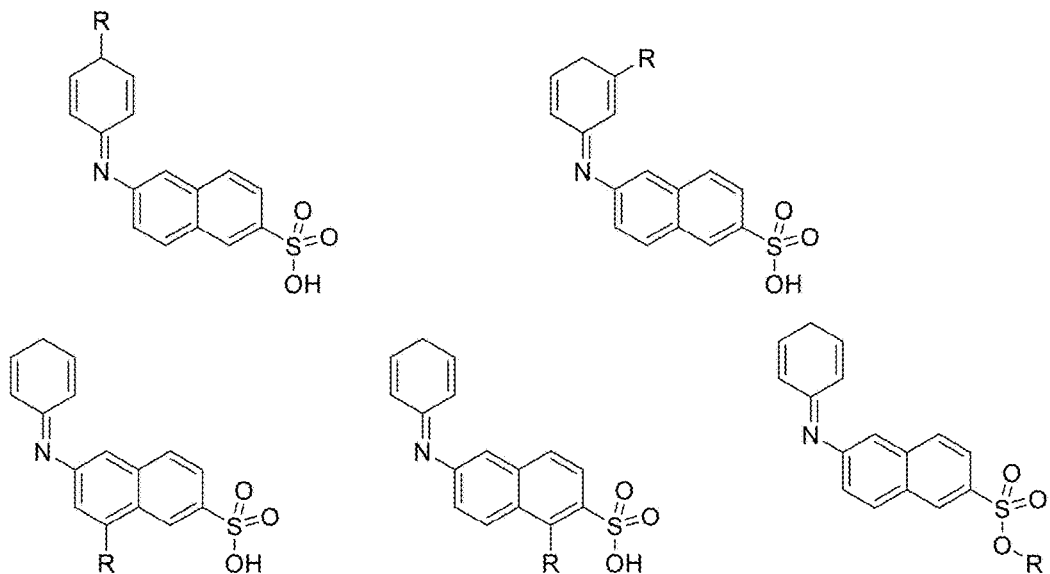
FIG. 2LLLLL
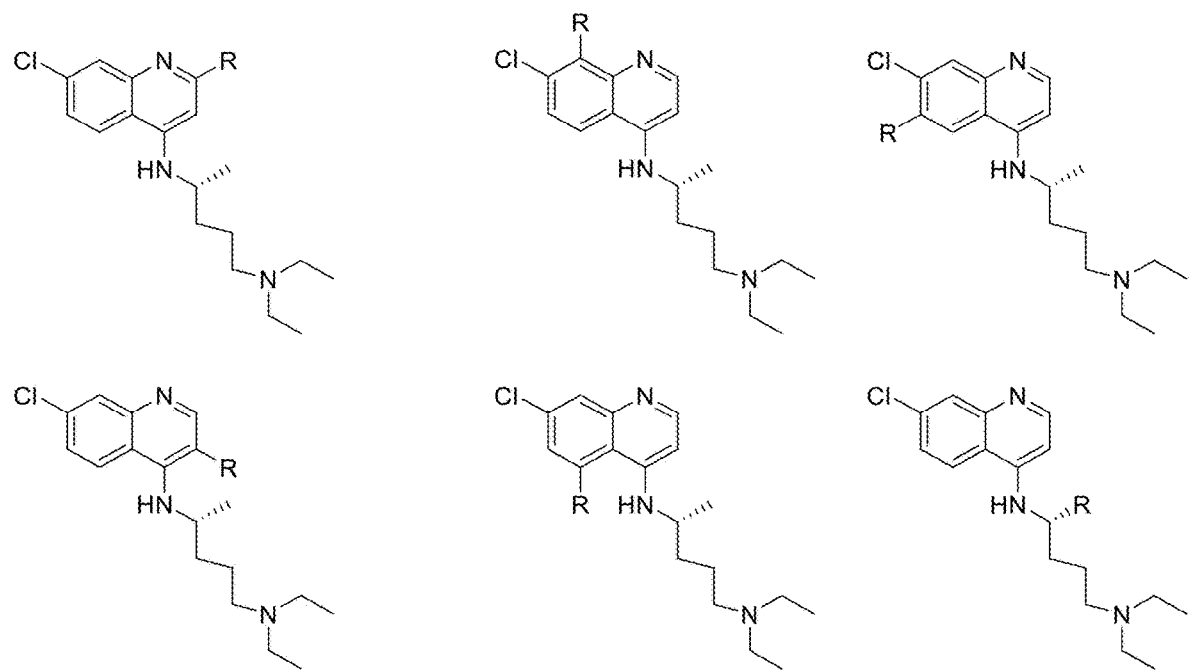

FIG. 2MMMMM
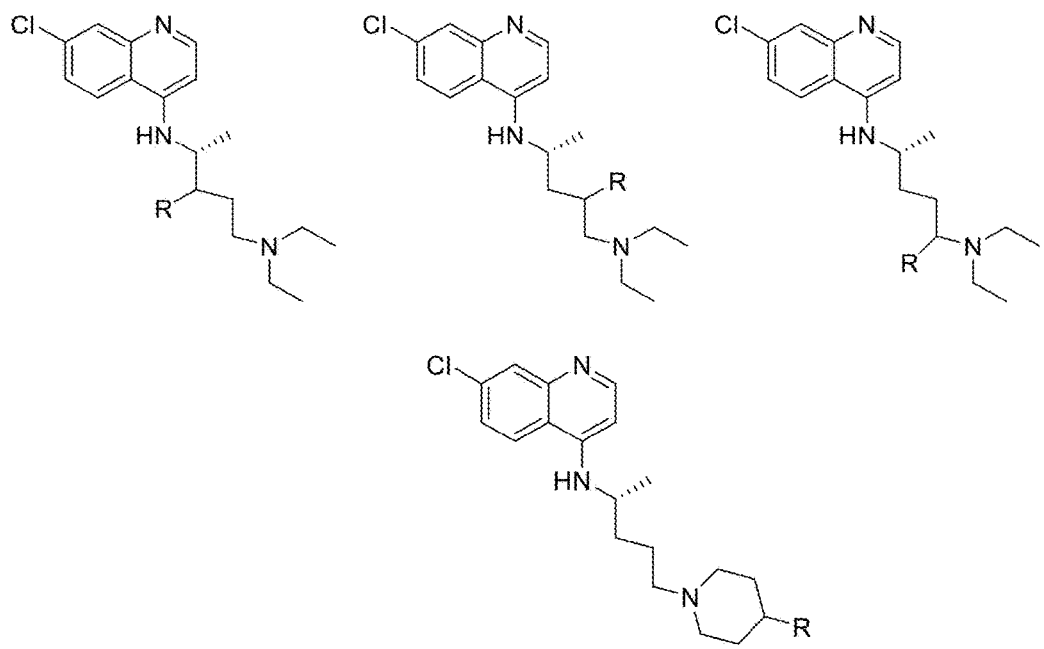
FIG. 2NNNNN
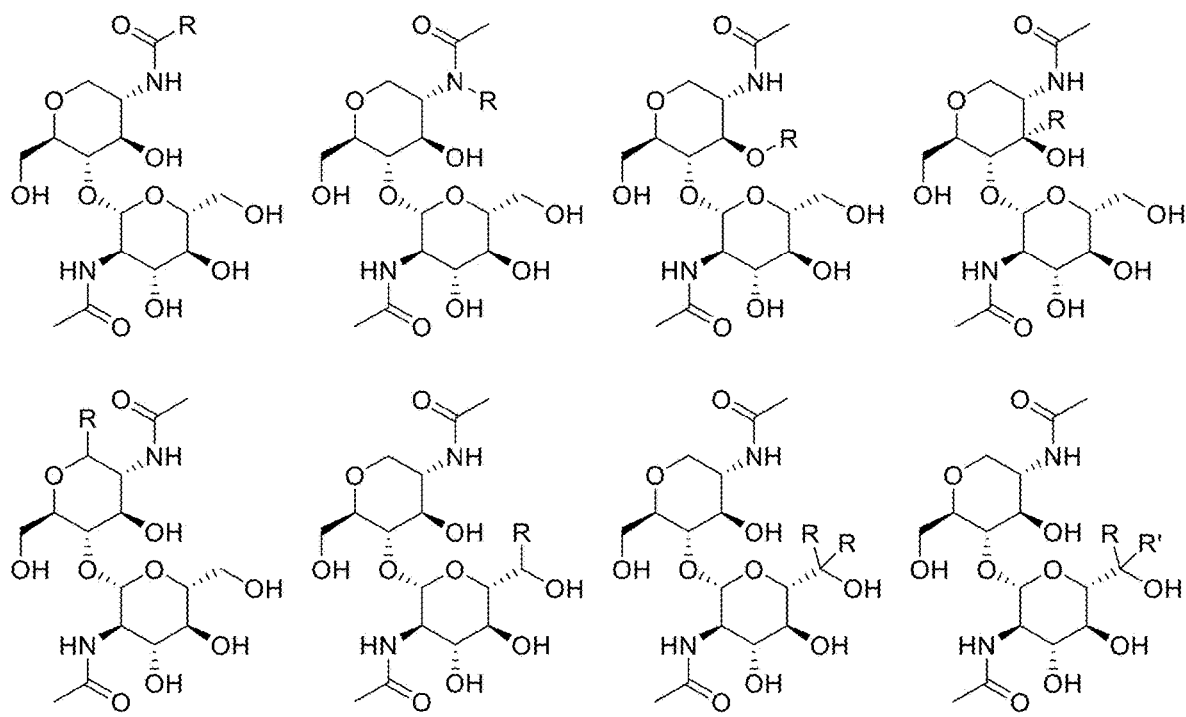

FIG. 2OOOOO
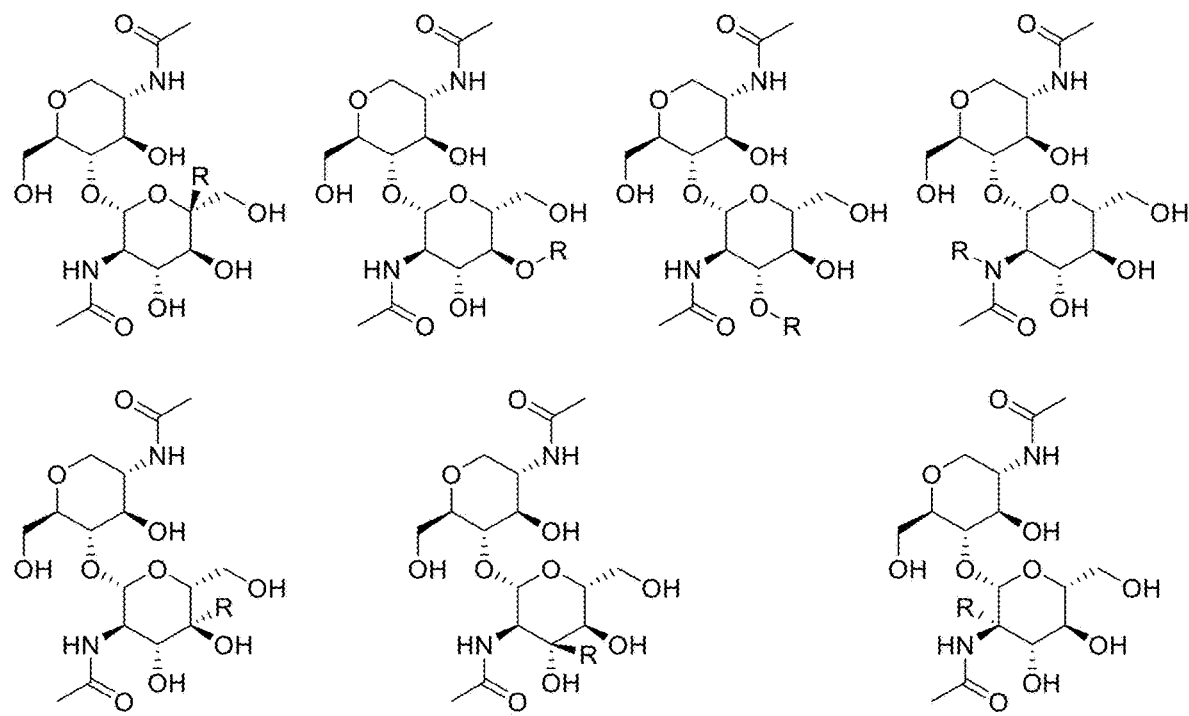
FIG. 2PPPPP
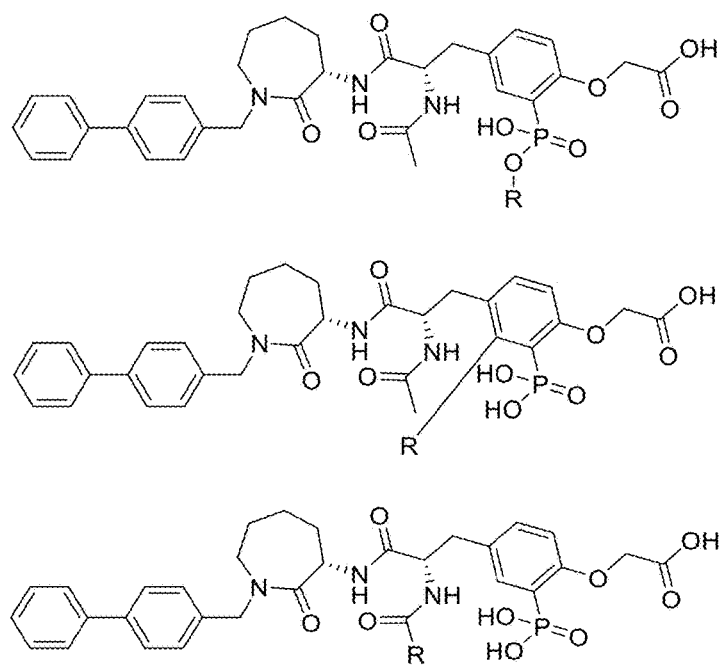

FIG. 2QQQQQ
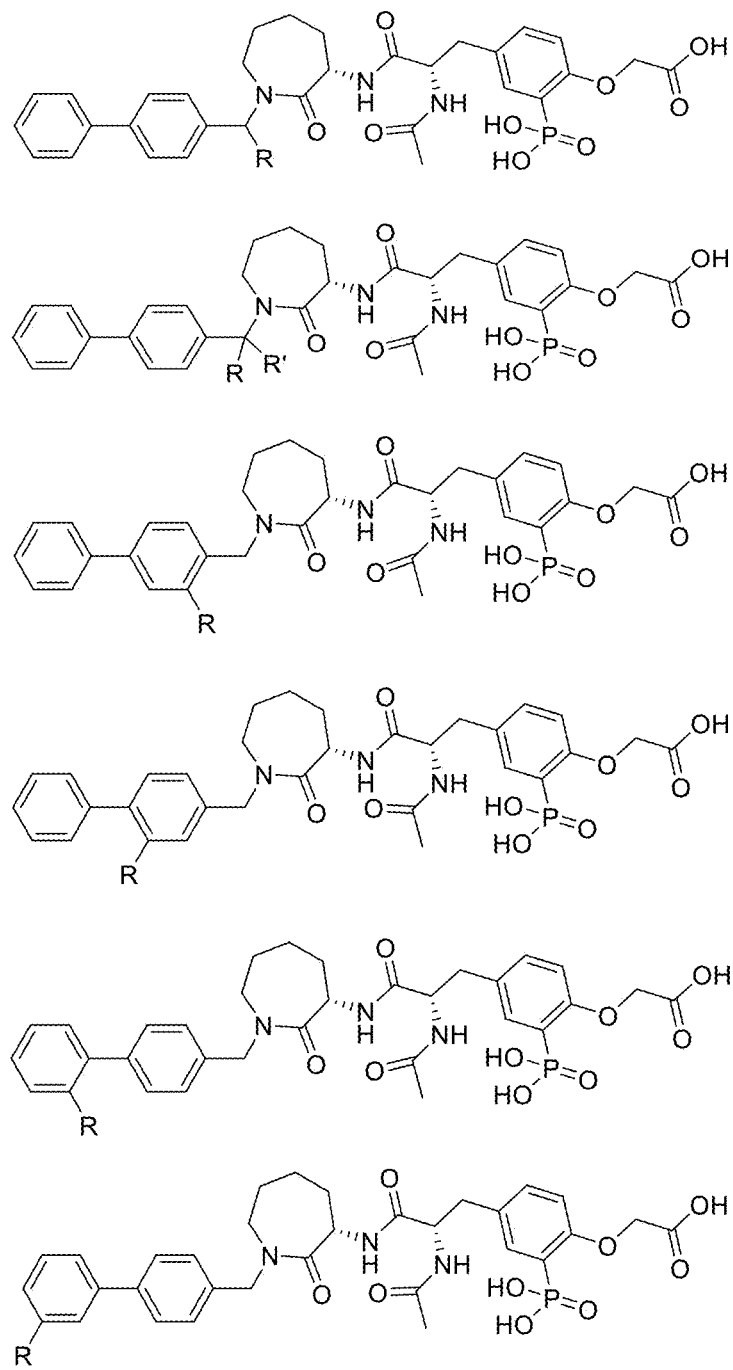

FIG. 2RRRRR
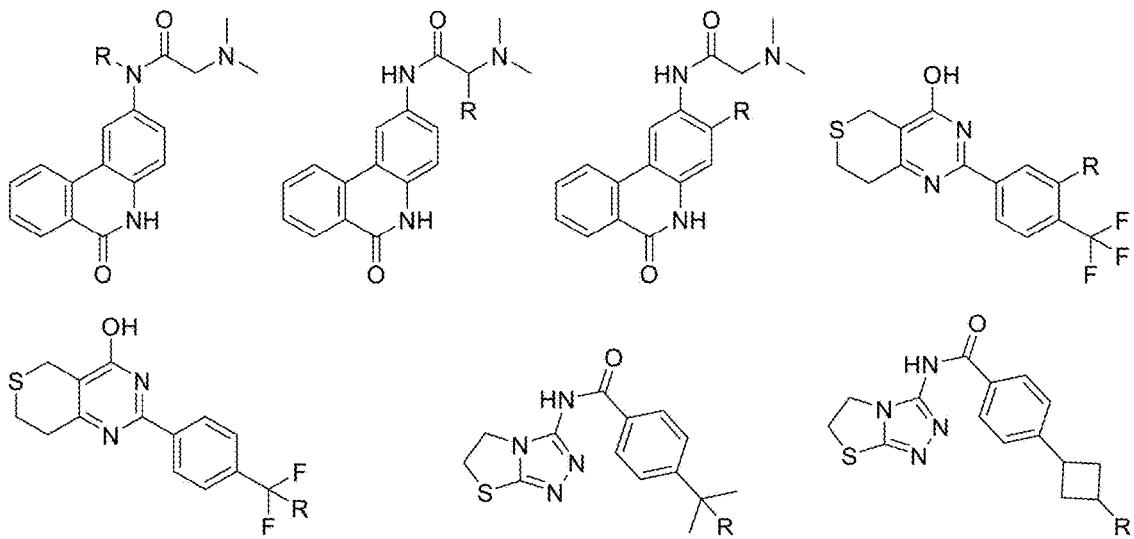
FIG. 2SSSSS
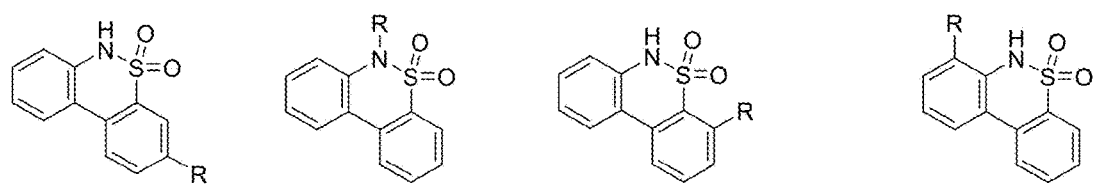
FIG. 2TTTTT
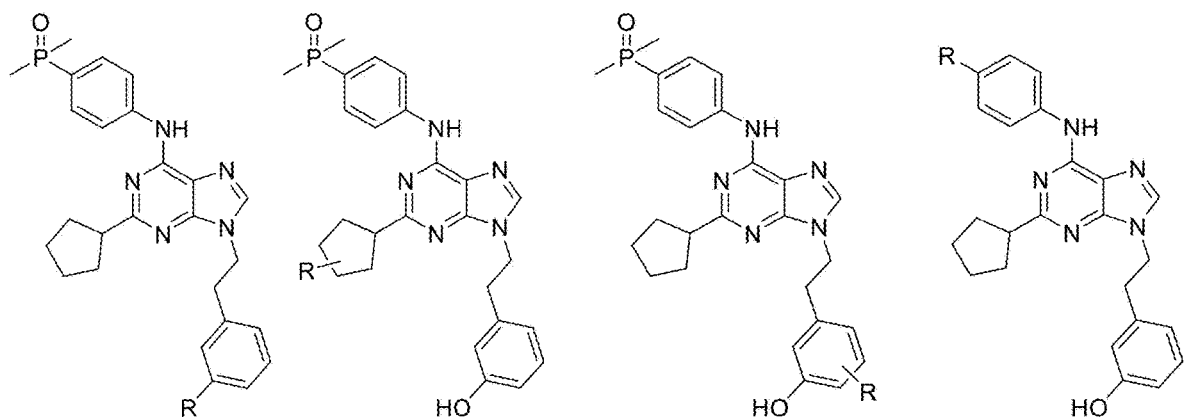

FIG. 2UUUUU
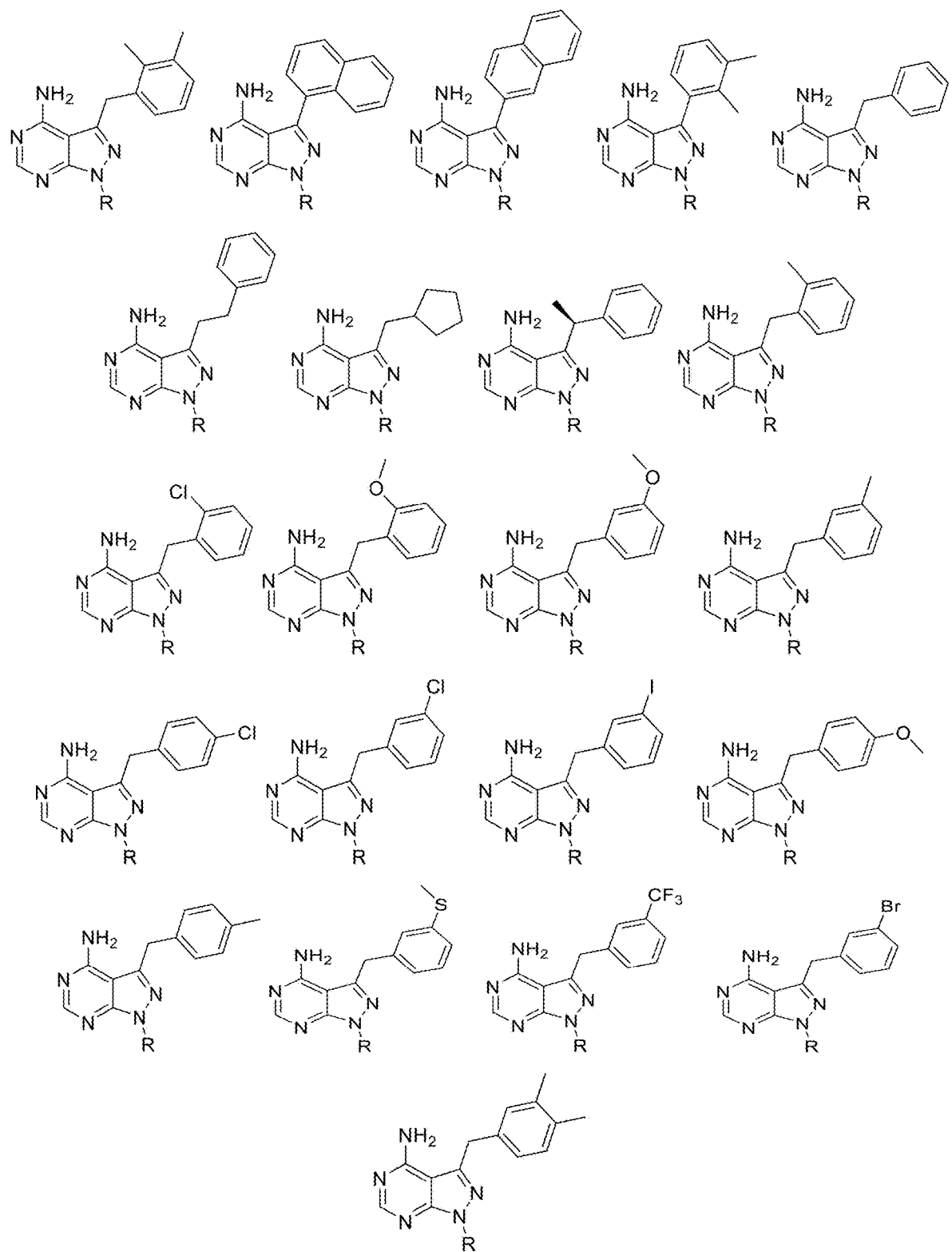

FIG. 2VVVVV
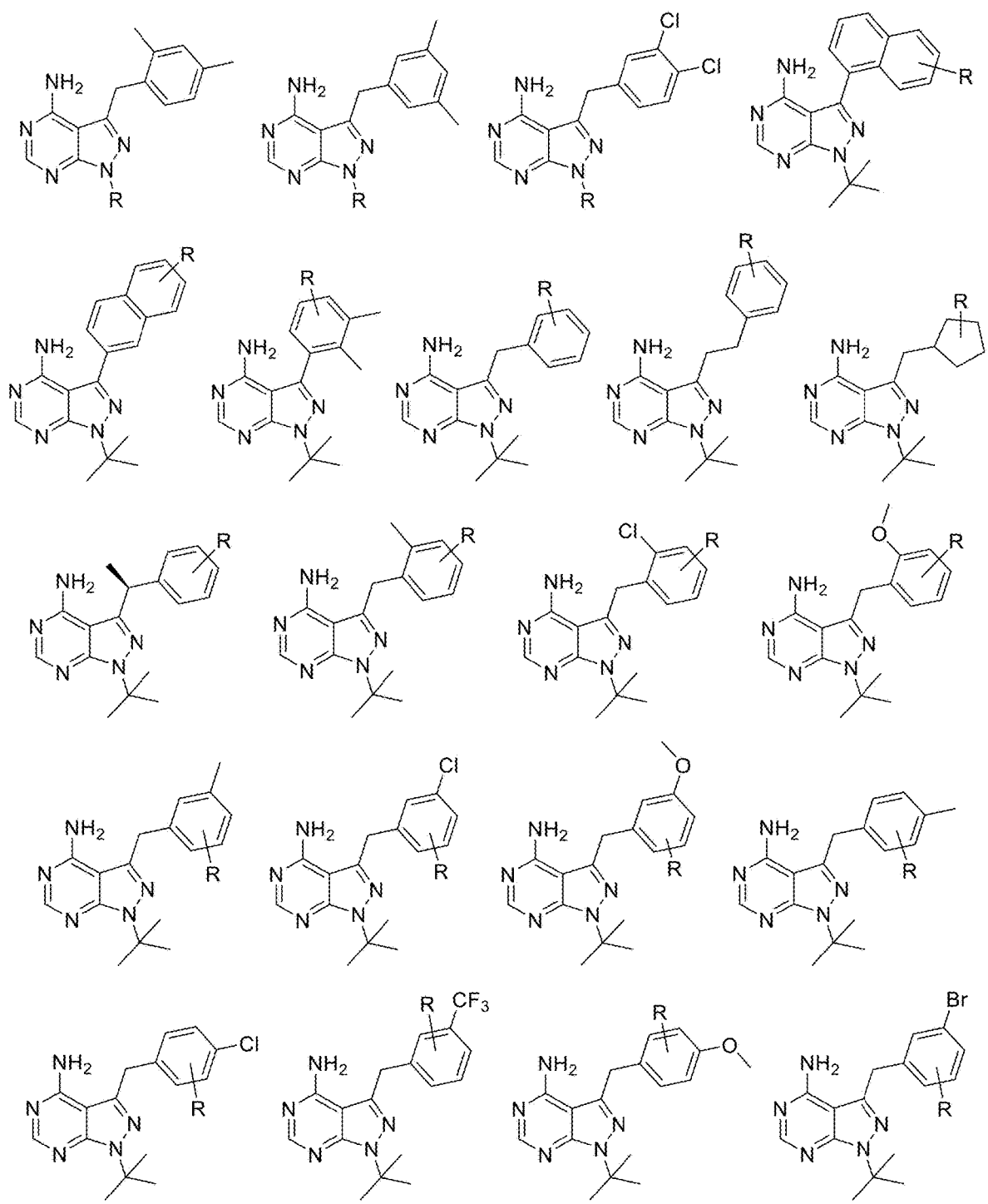

FIG. 2WWWWW
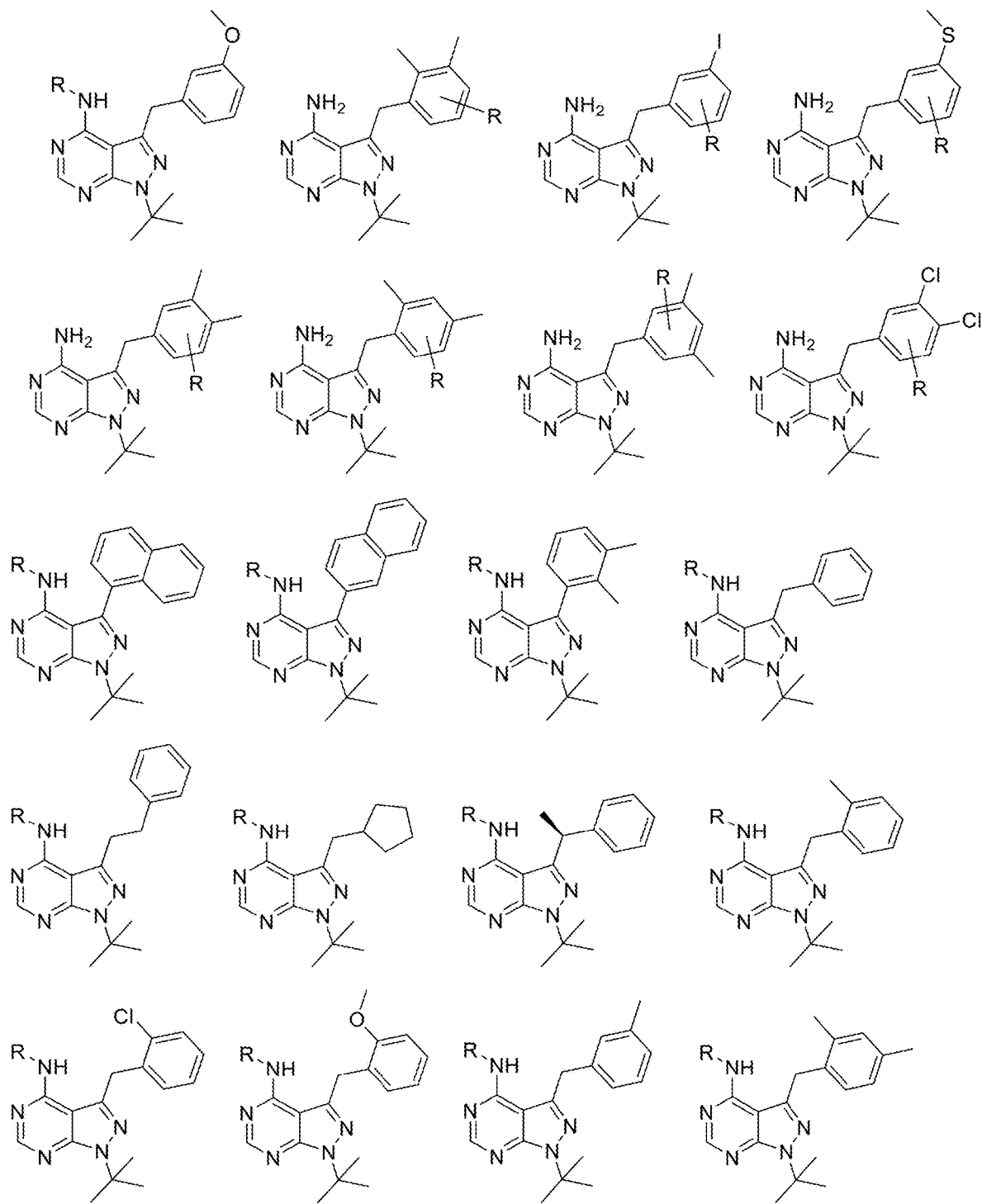

FIG. 2XXXXX
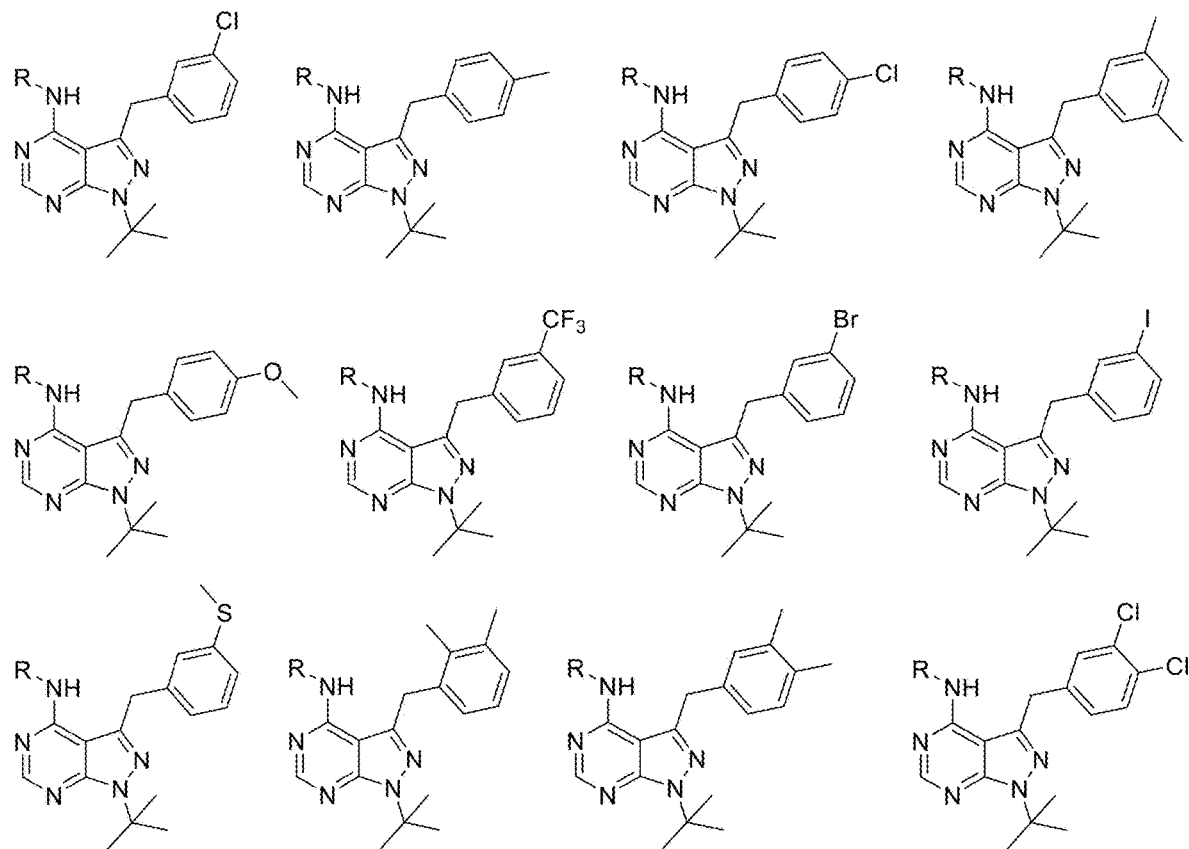
FIG. 2YYYYY
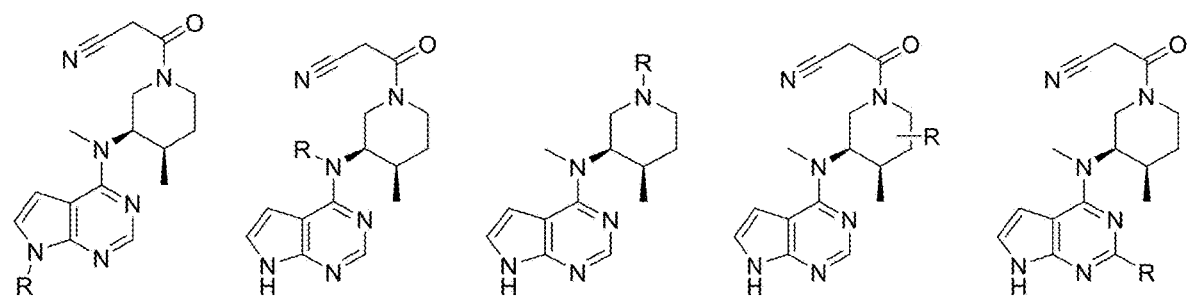

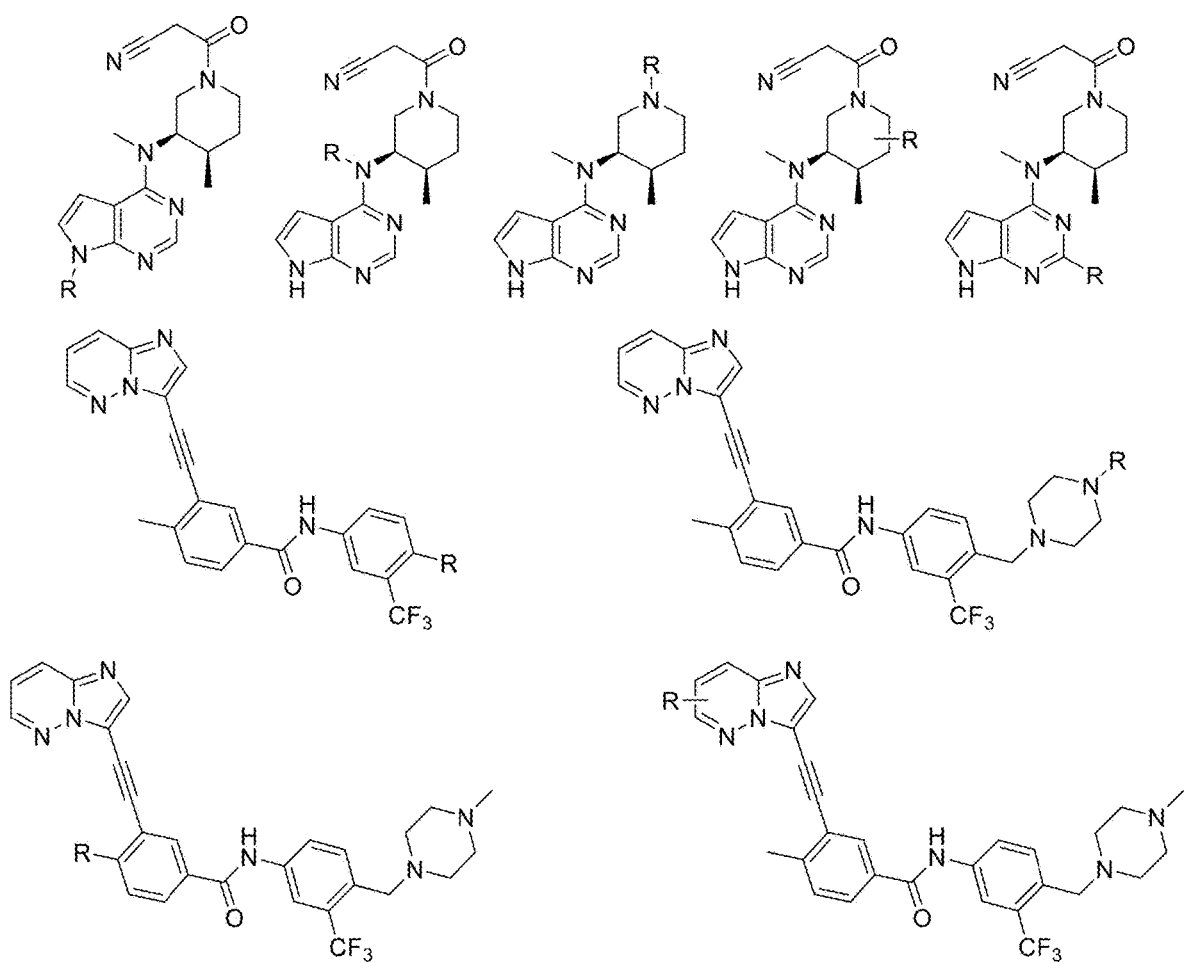
FIG. 2ZZZZZ

FIG. 3C
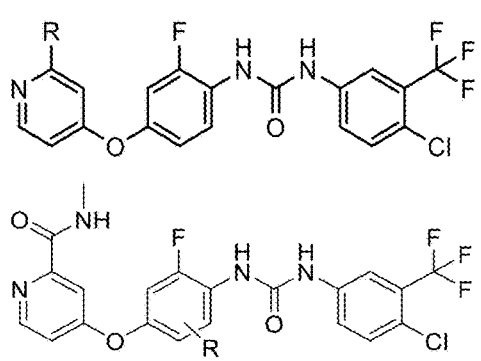
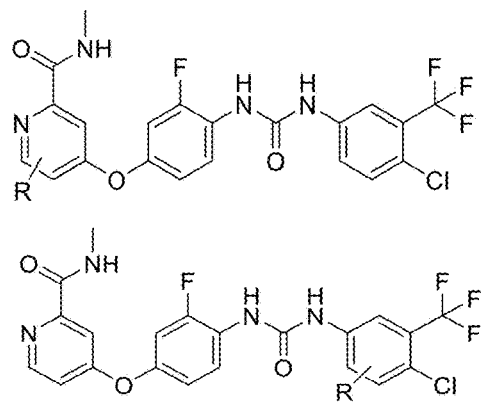
FIG. 3D
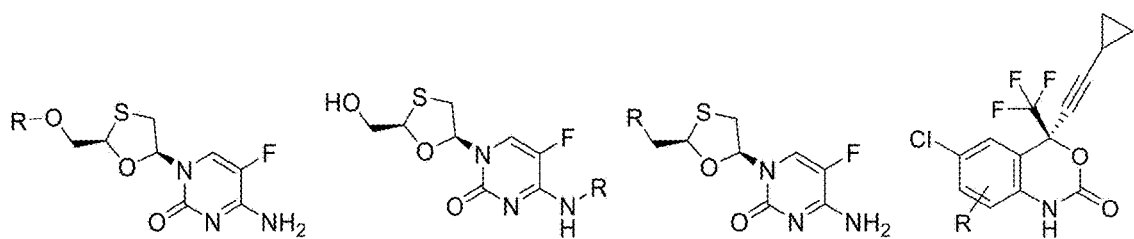
FIG. 3E
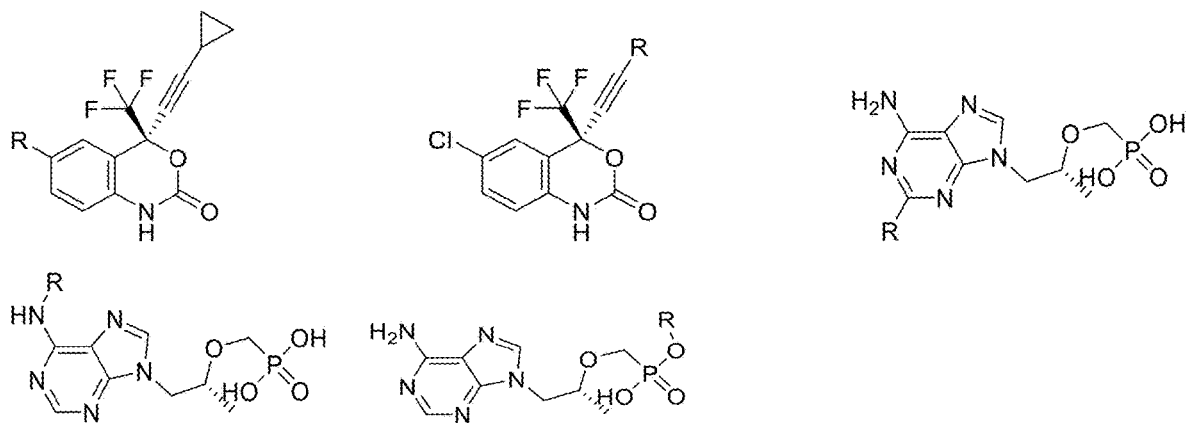

FIG. 3I
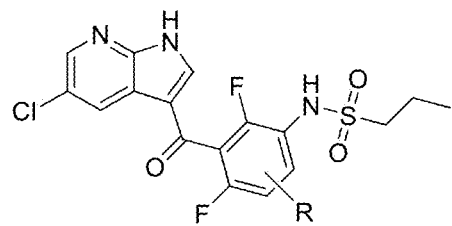 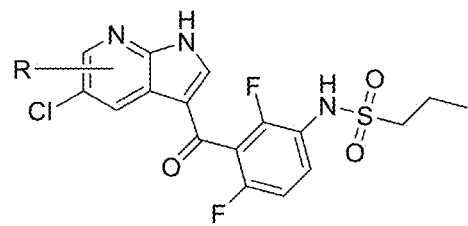
FIG. 3J
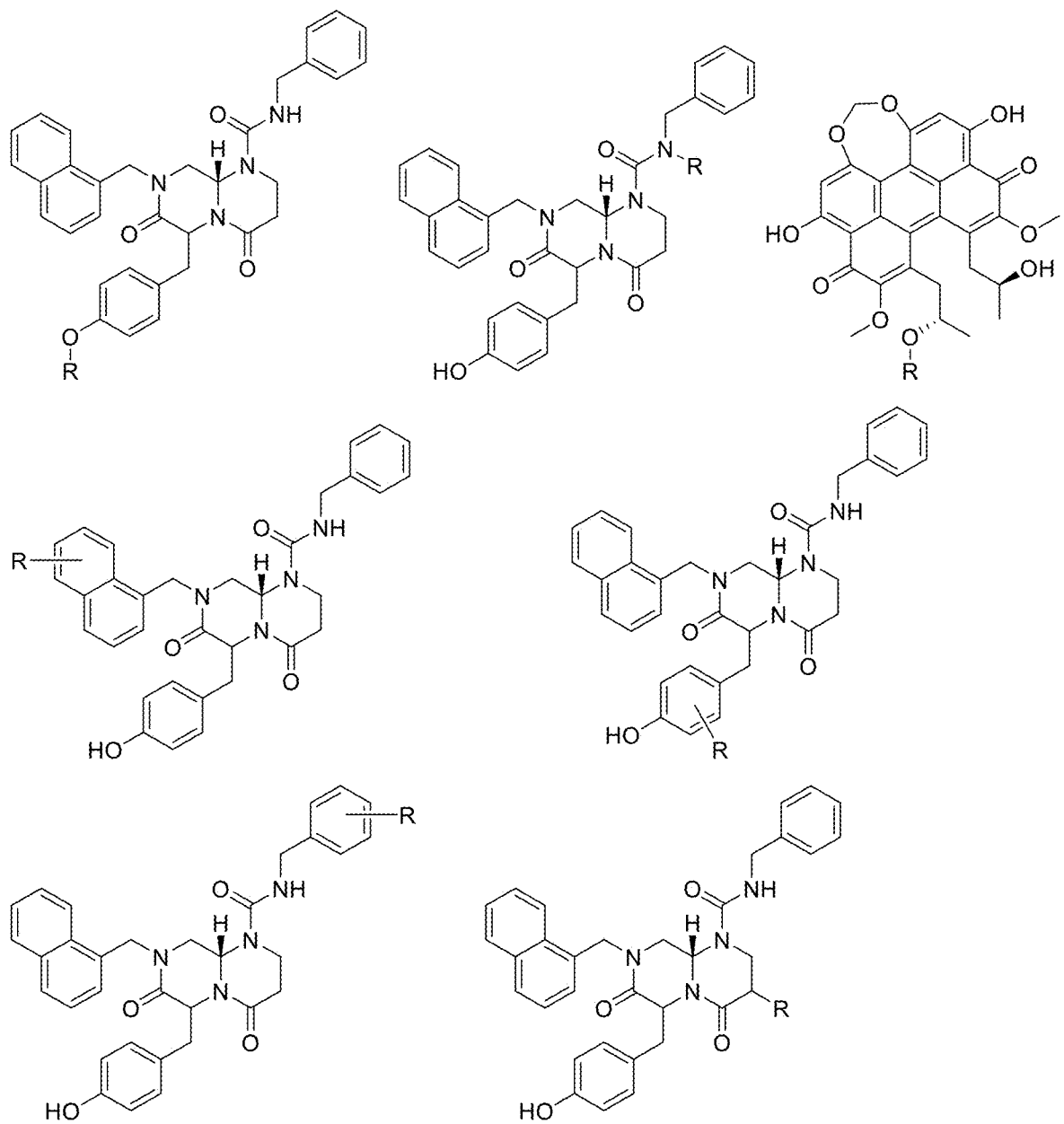

FIG. 3CC
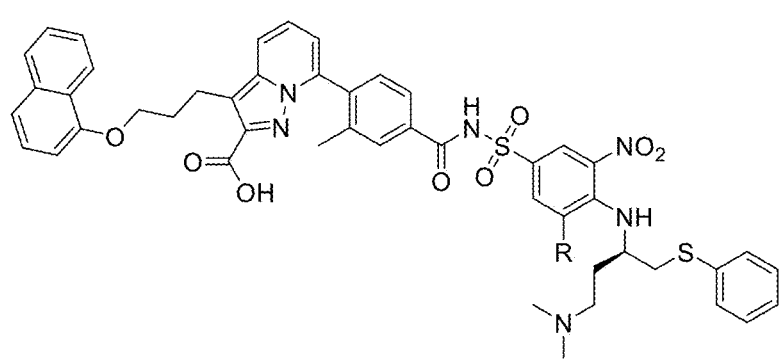
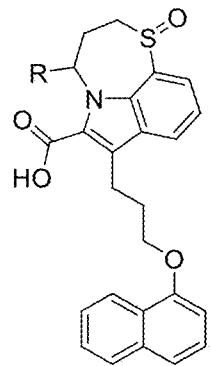
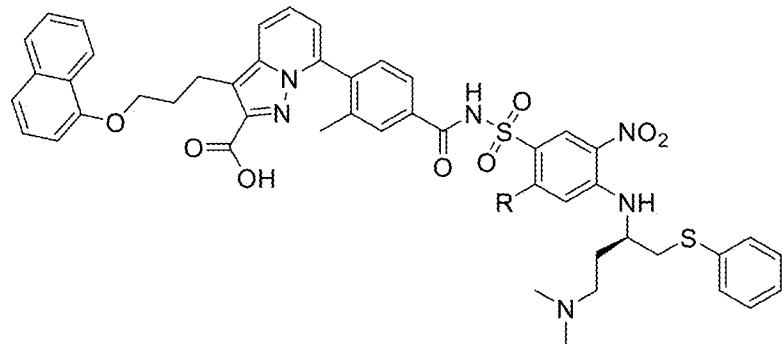
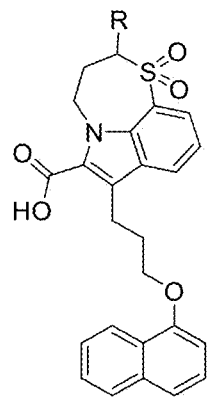
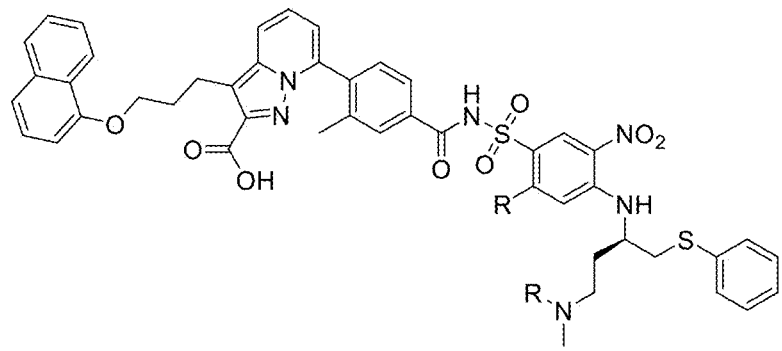
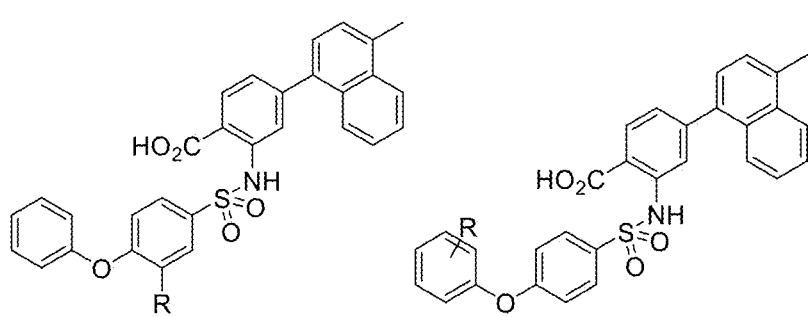
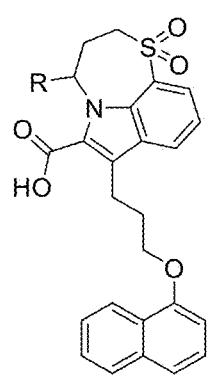

FIG. 3FF
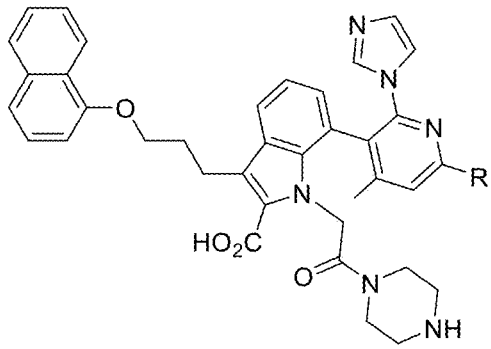
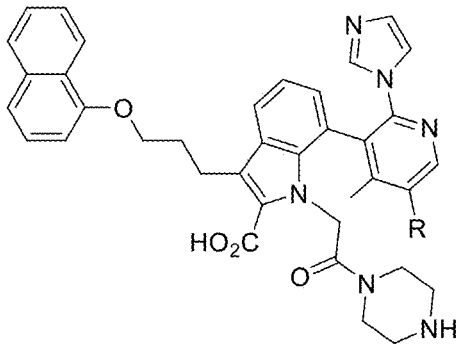
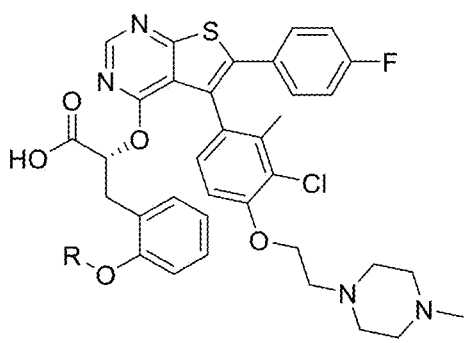
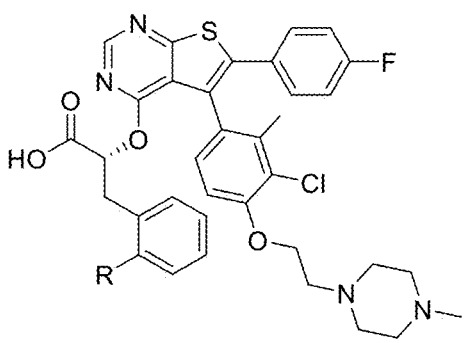
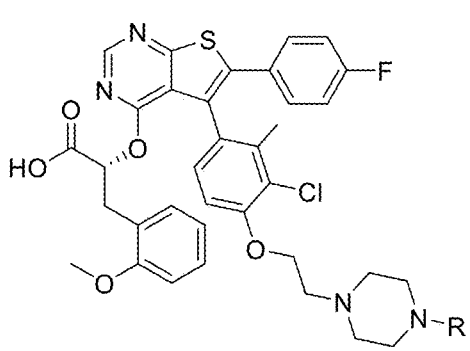
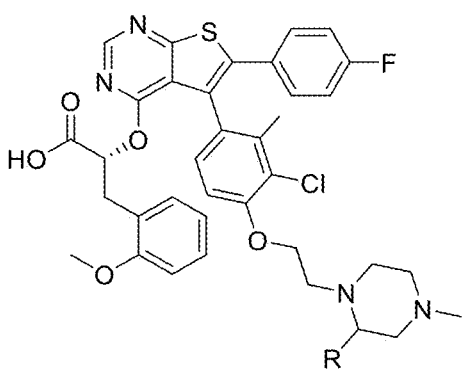
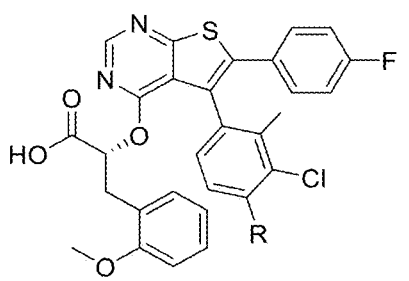
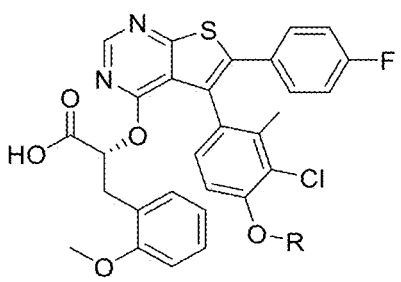

FIG. 3GG
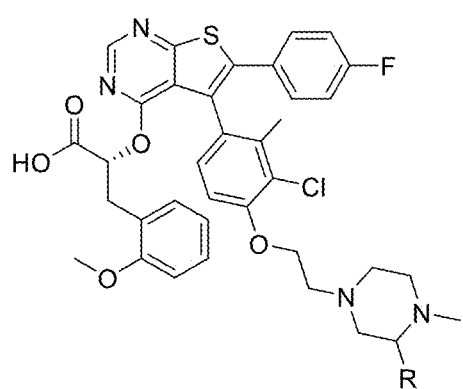
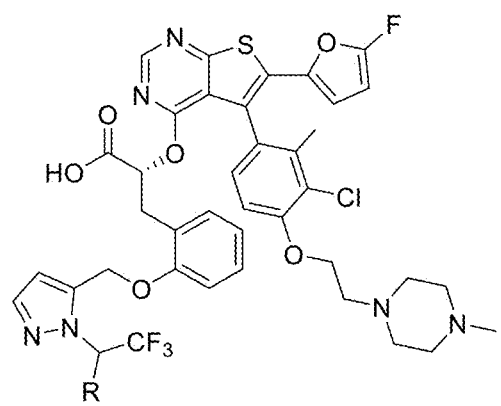
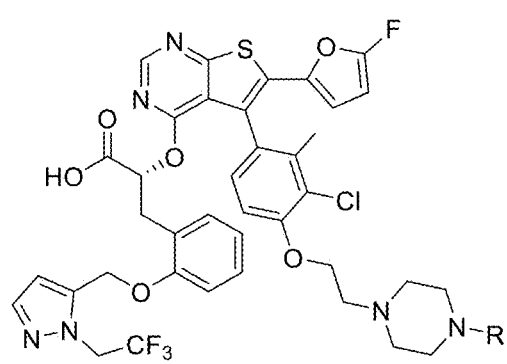
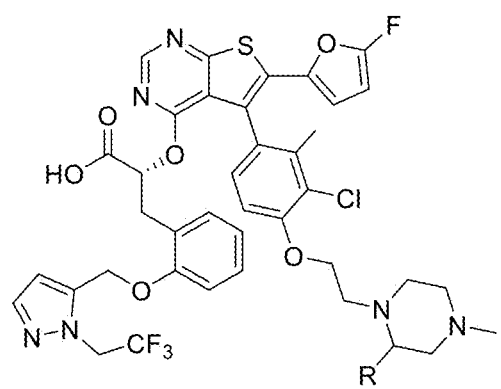
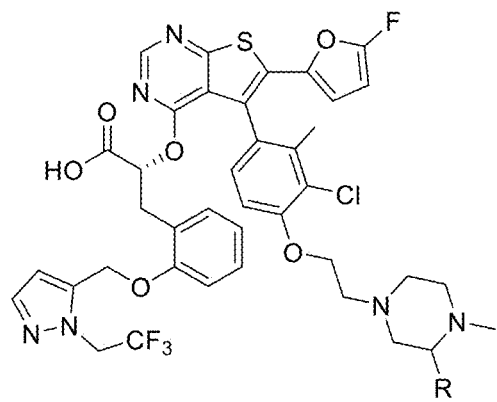
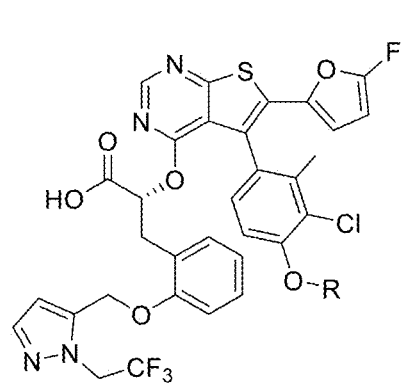

FIG. 3II
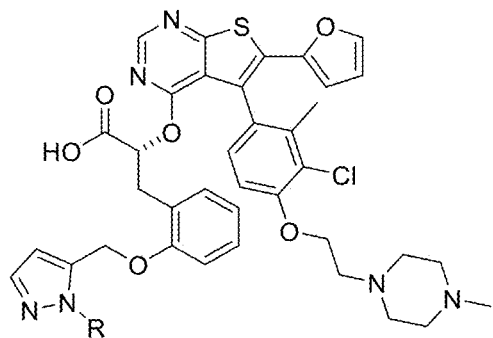
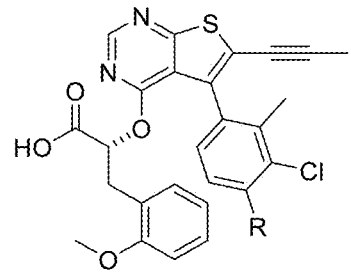
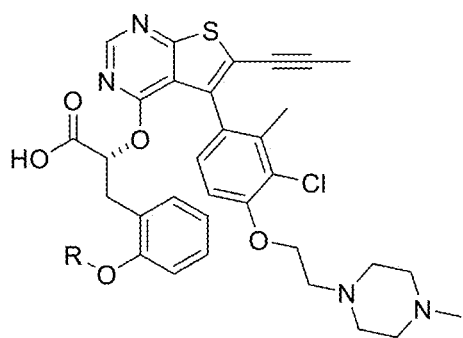
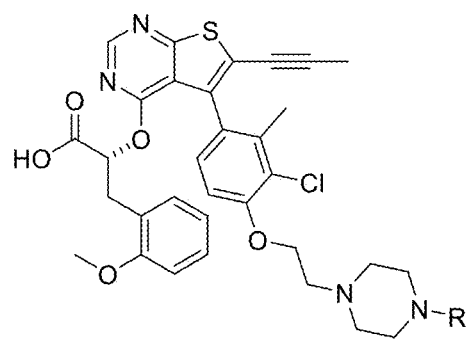
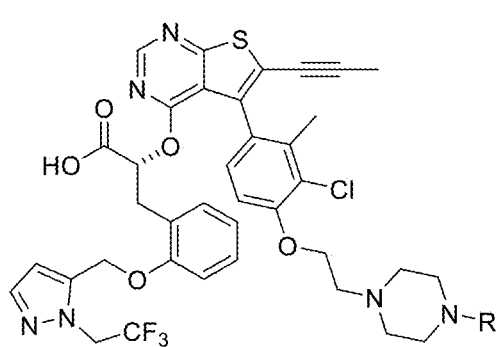
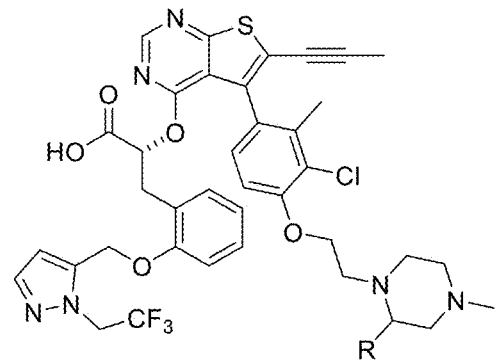
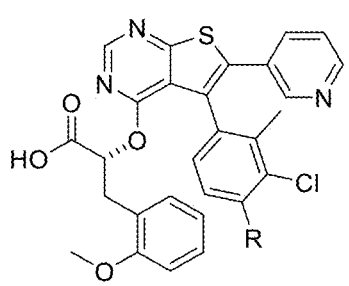
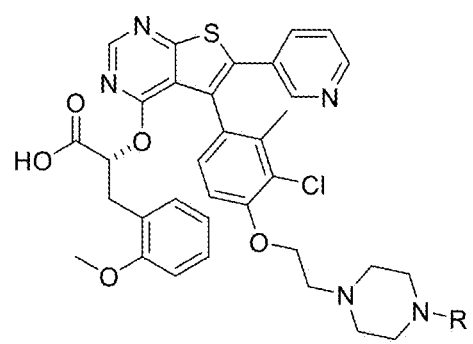

FIG. 3JJ
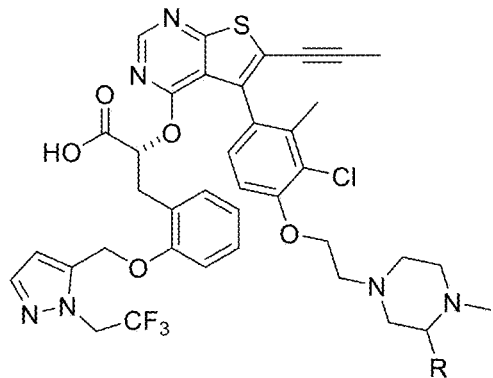
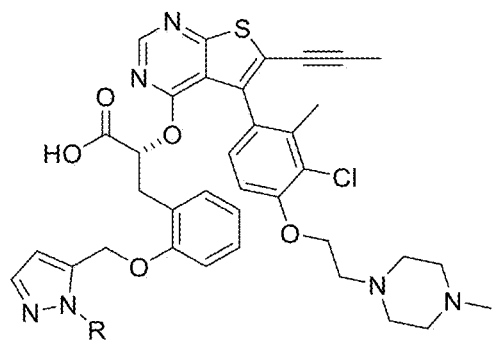
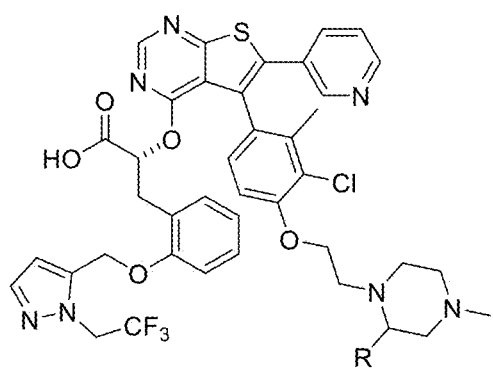
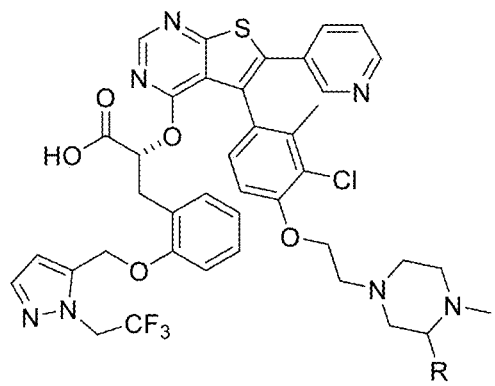
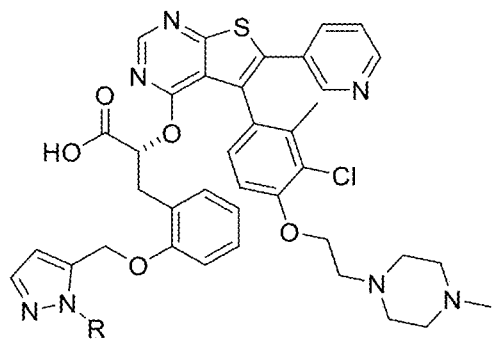
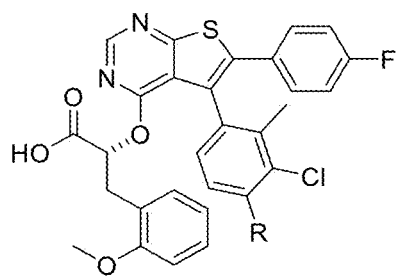
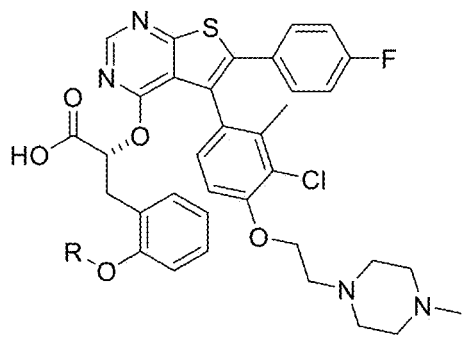
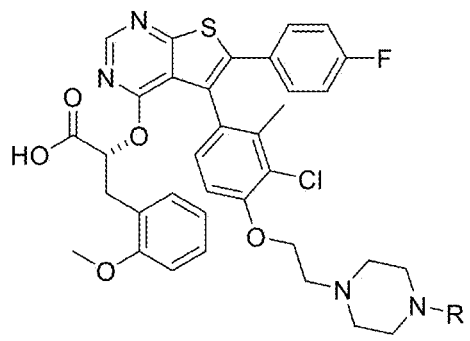

FIG. 3KK
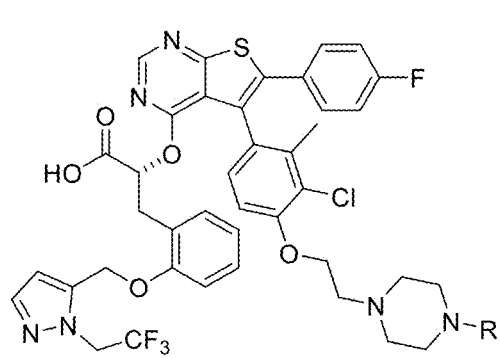
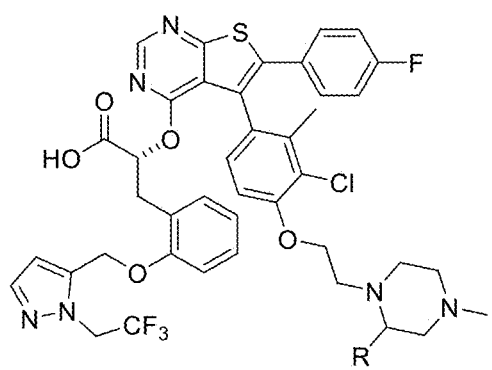
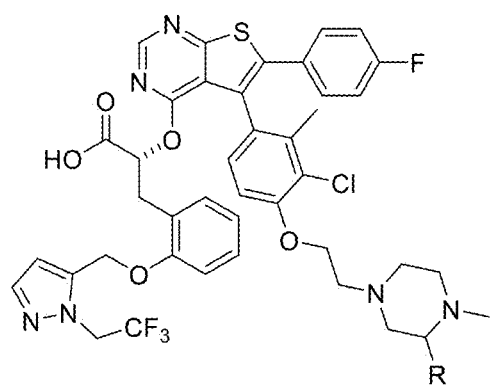
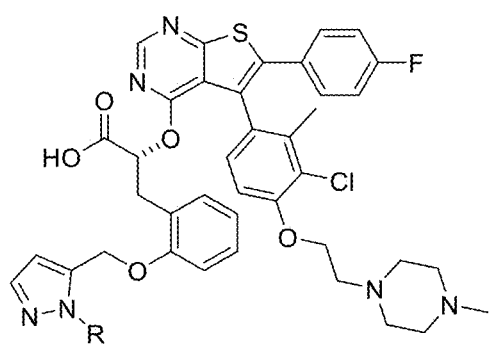
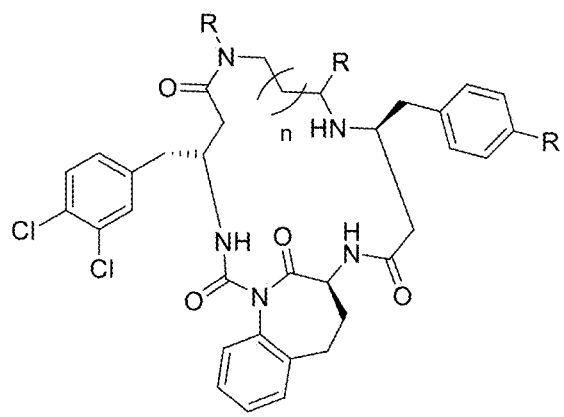
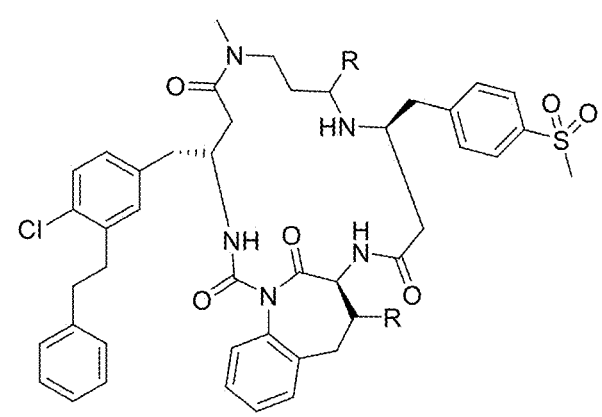

FIG. 3NN
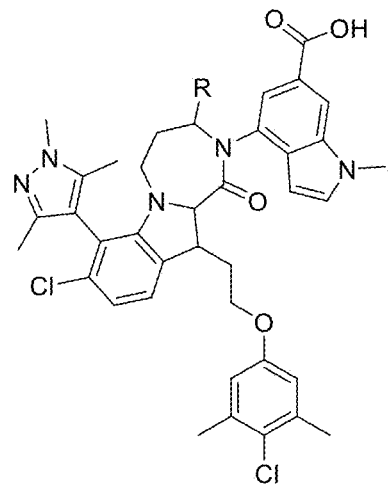
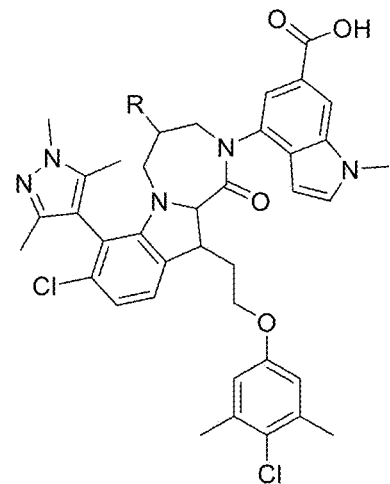
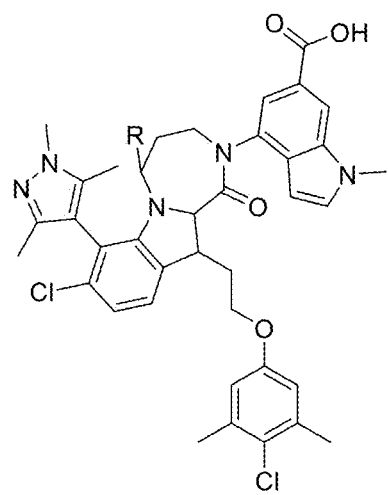
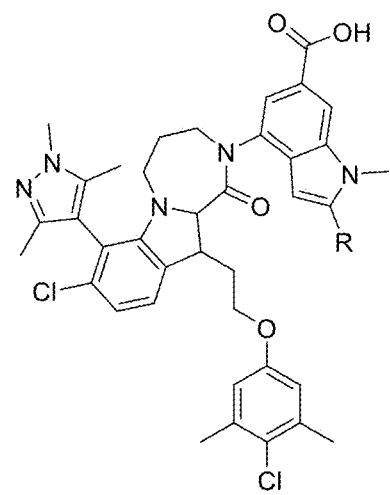
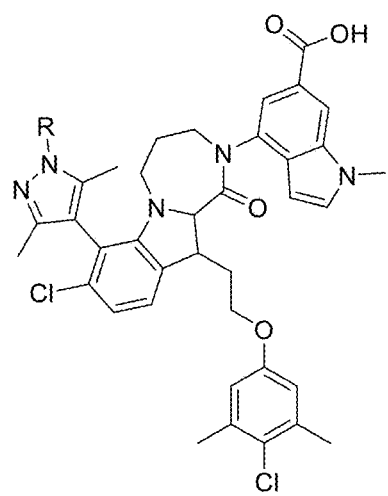
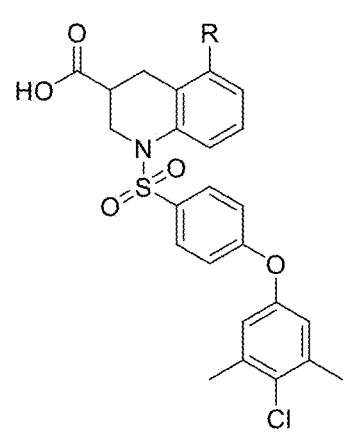

FIG. 3AAA
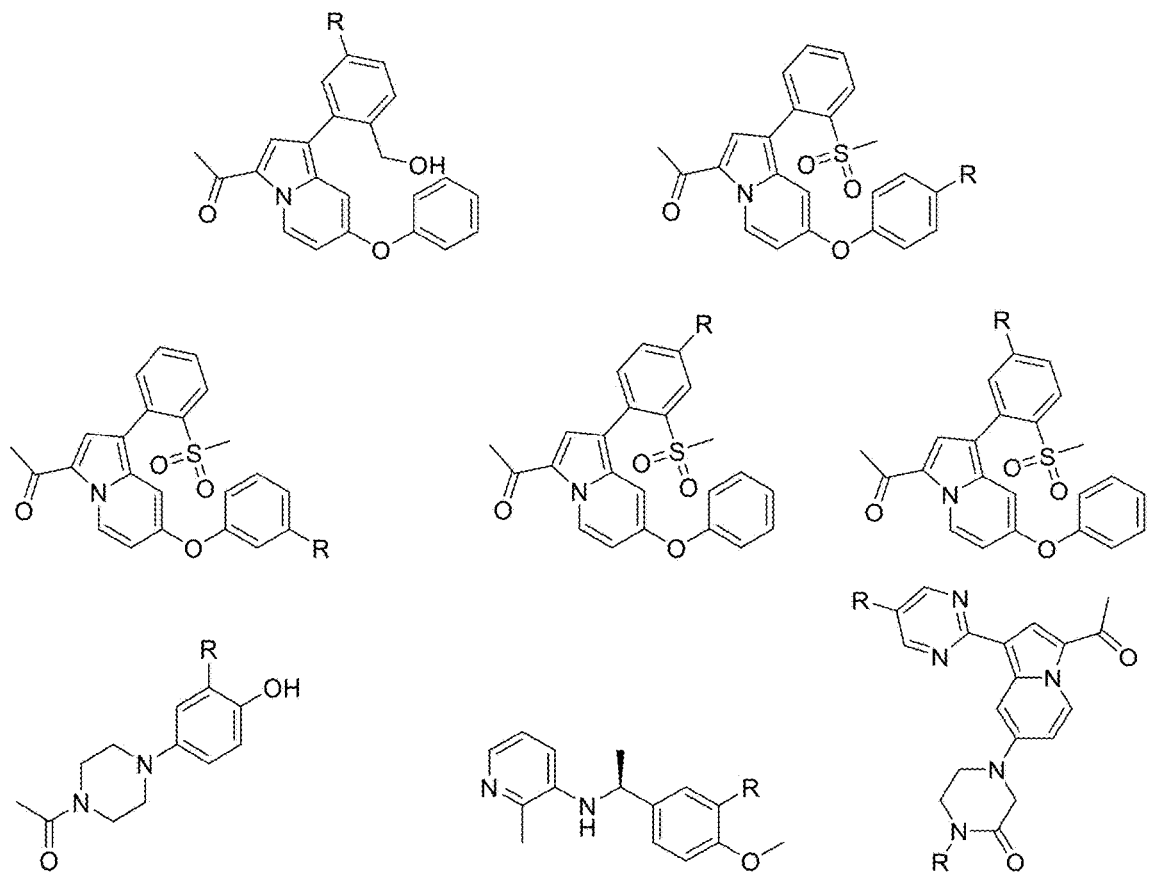
FIG. 3BBB
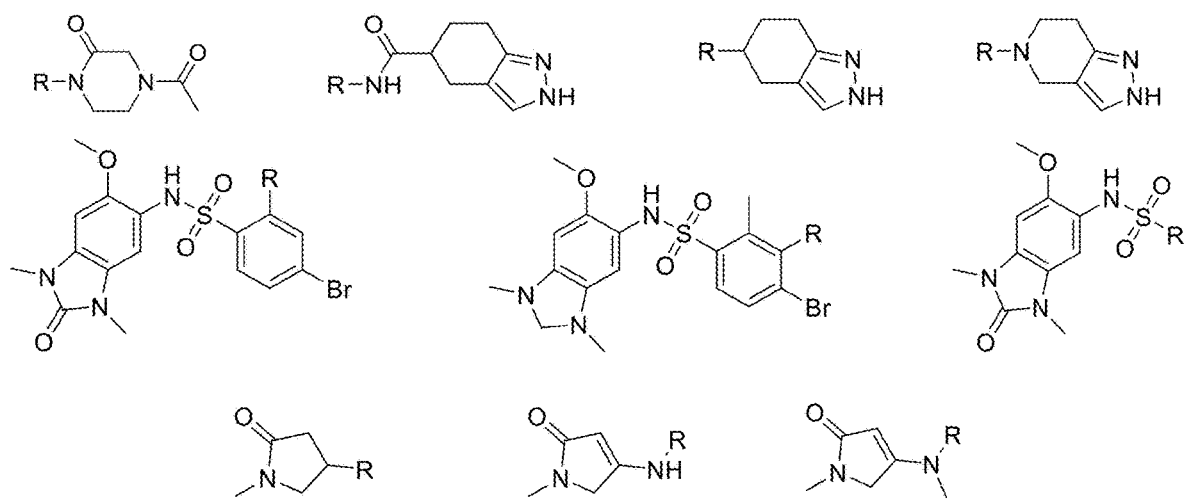

FIG. 3CCC
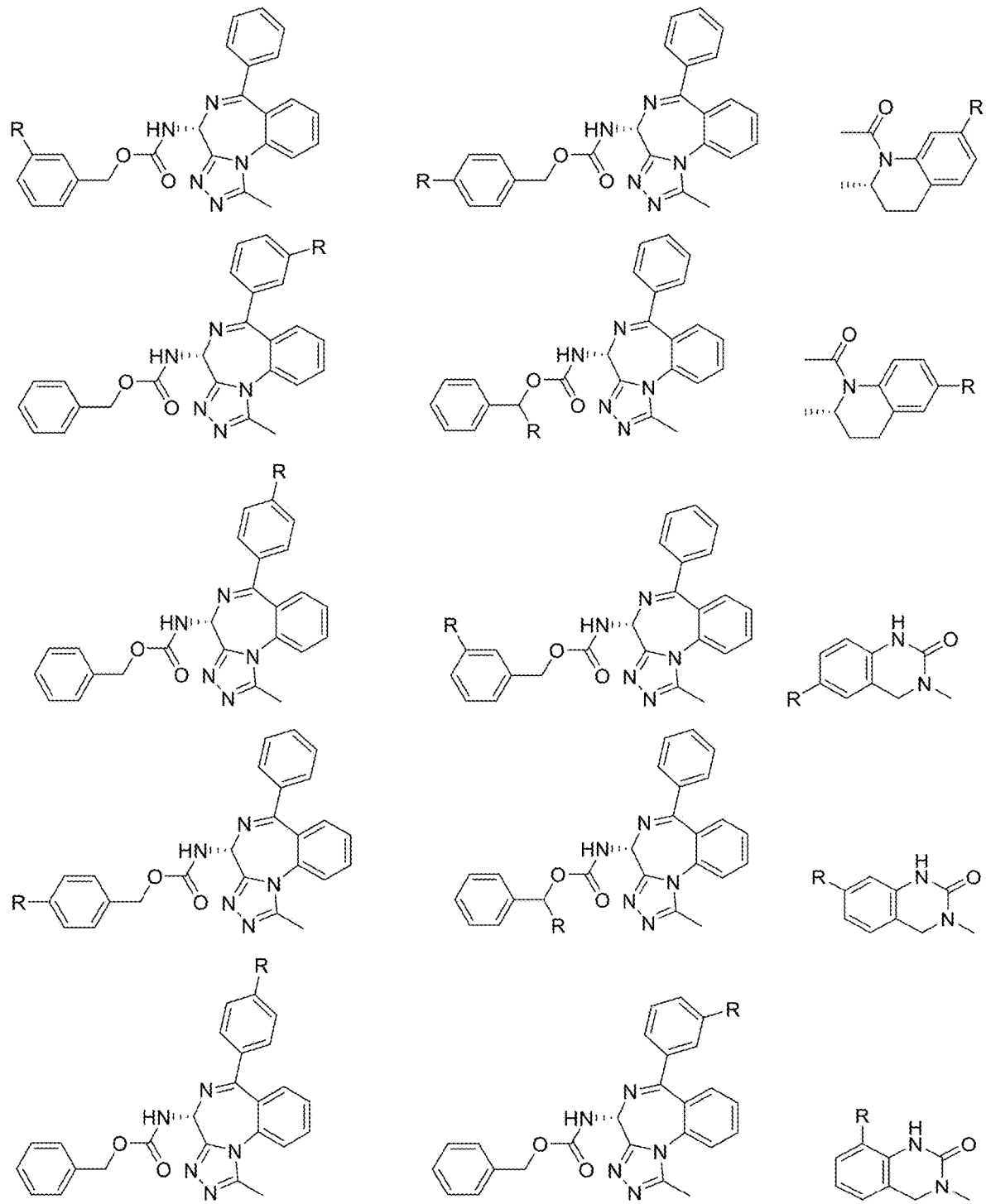

FIG. 3DDD
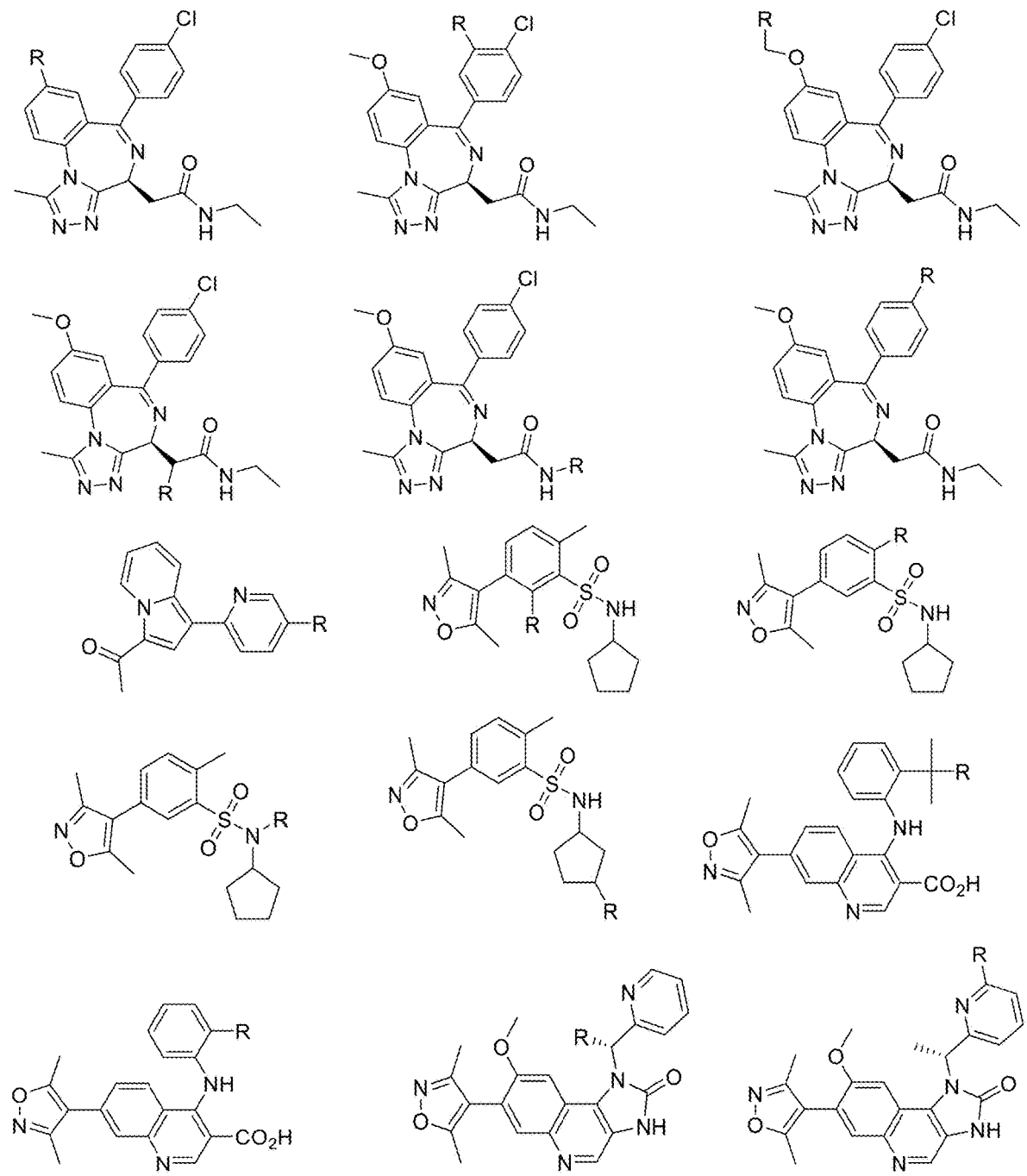

FIG. 3EEE
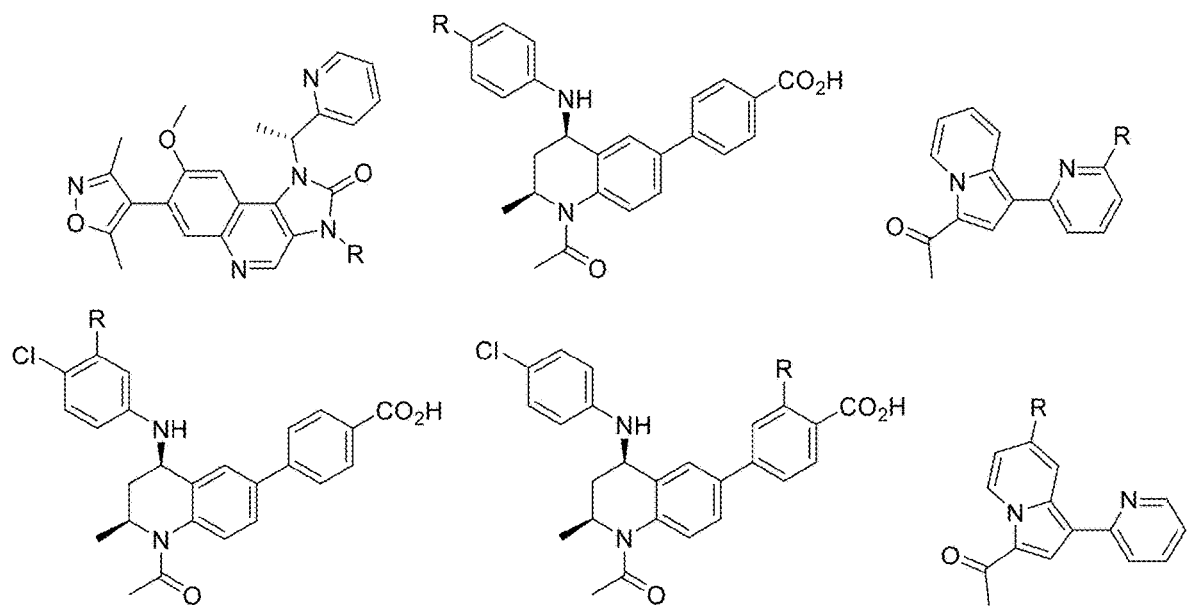
FIG. 3FFF
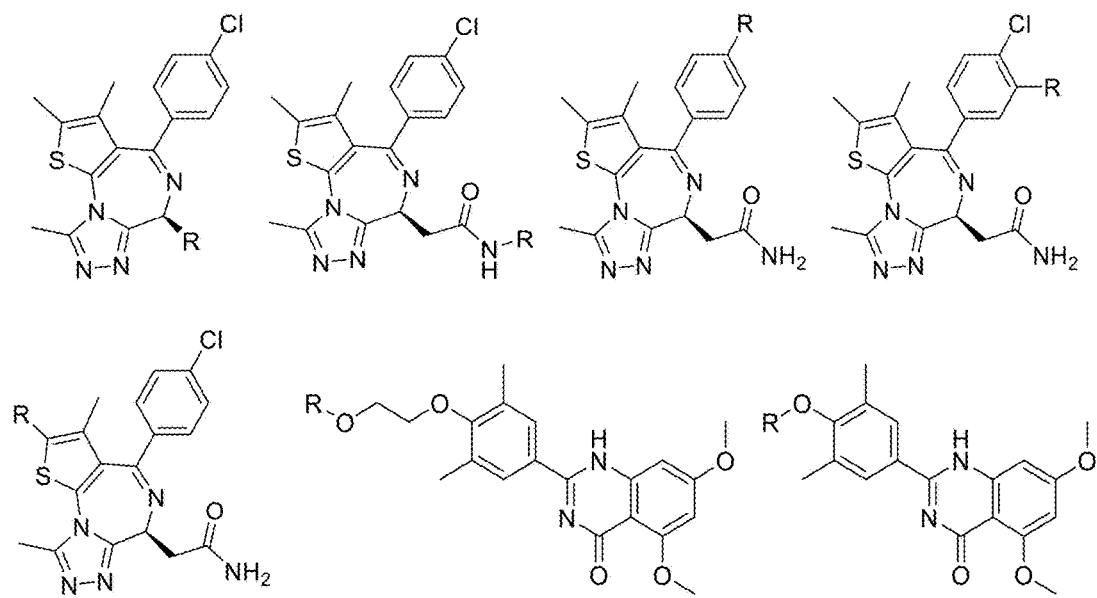

FIG. 3GGG
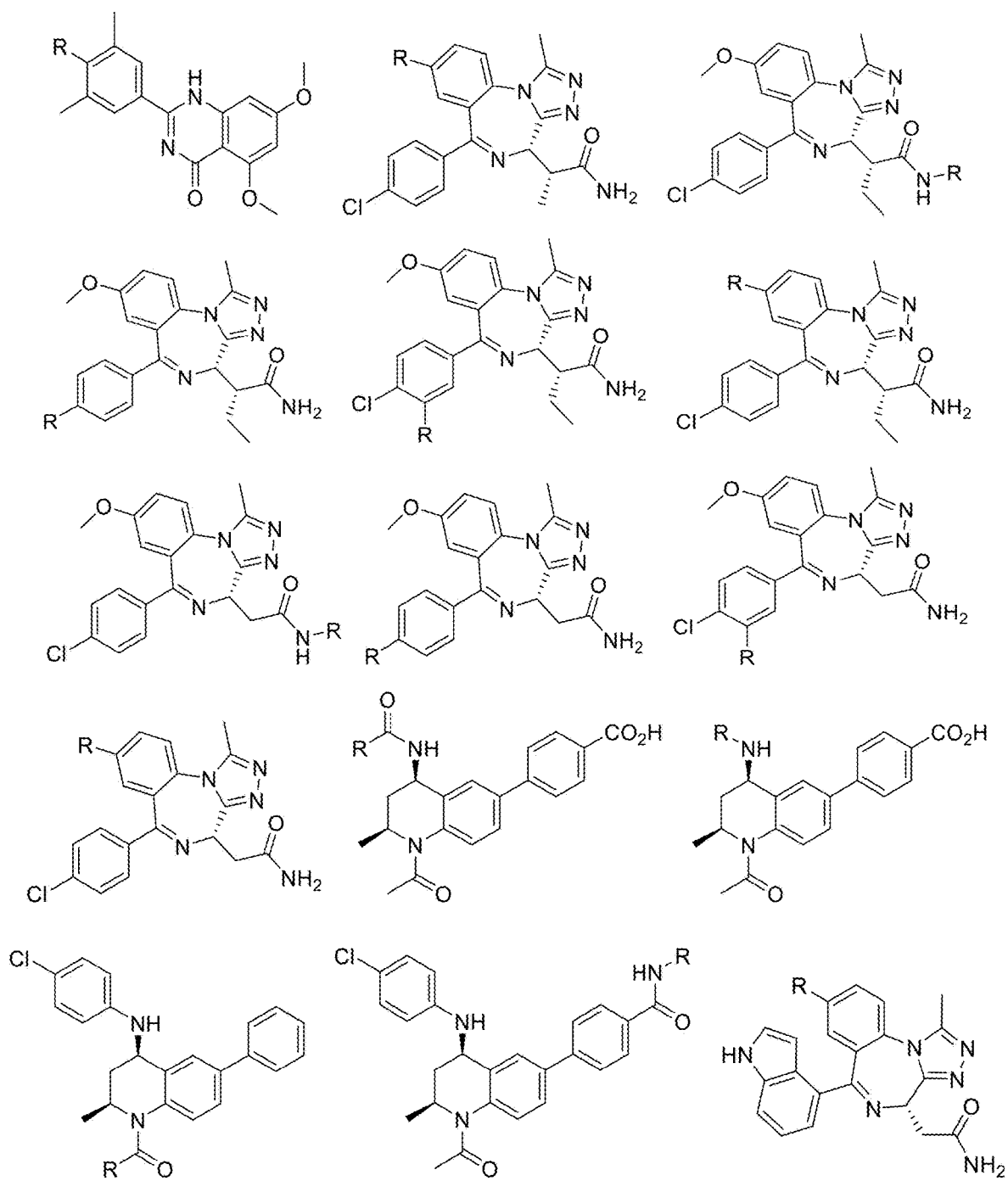

FIG. 3HHH
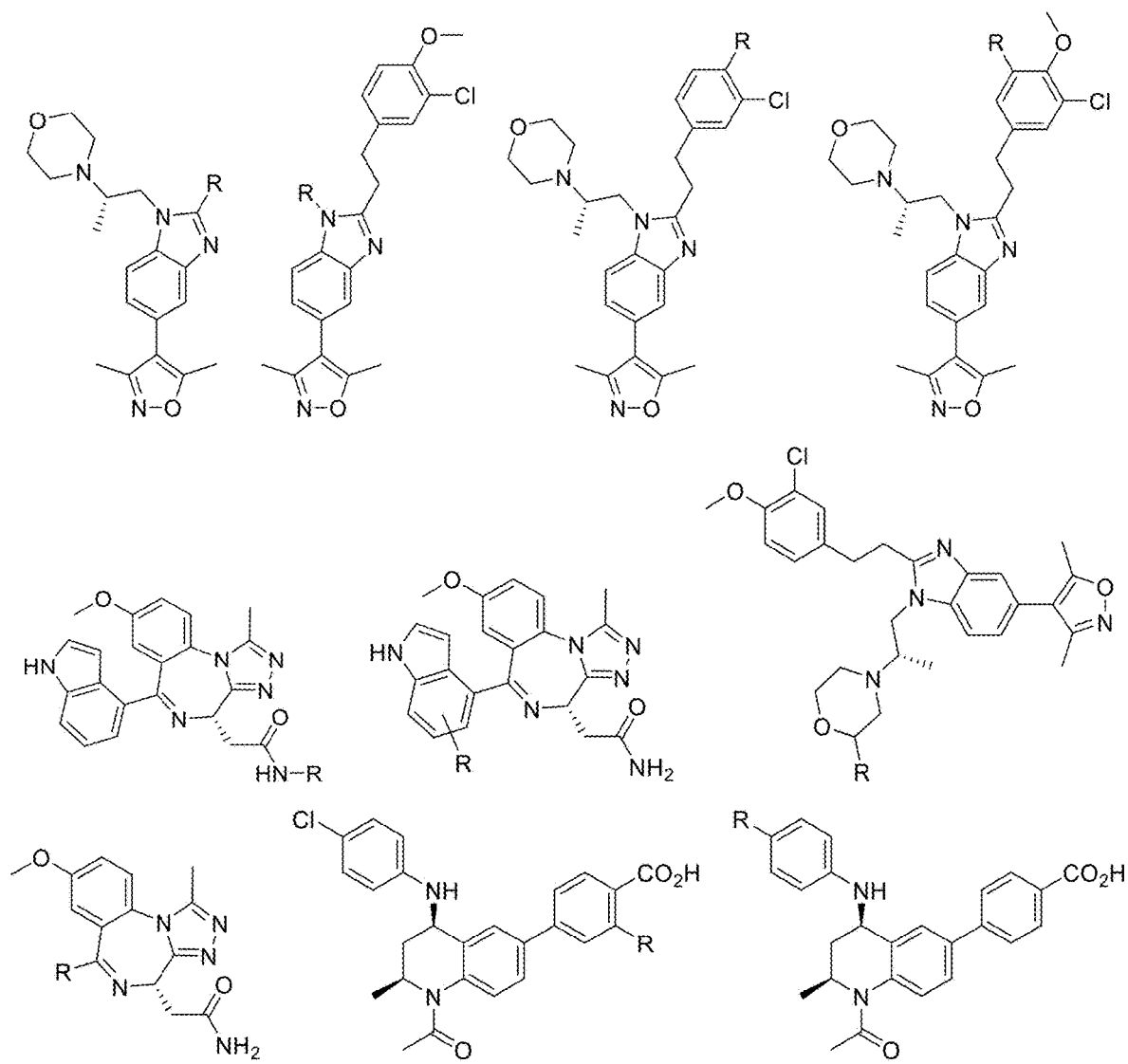
FIG. 3III
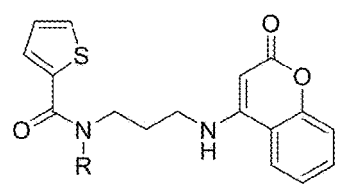 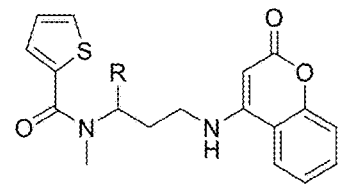

FIG. 3JJJ
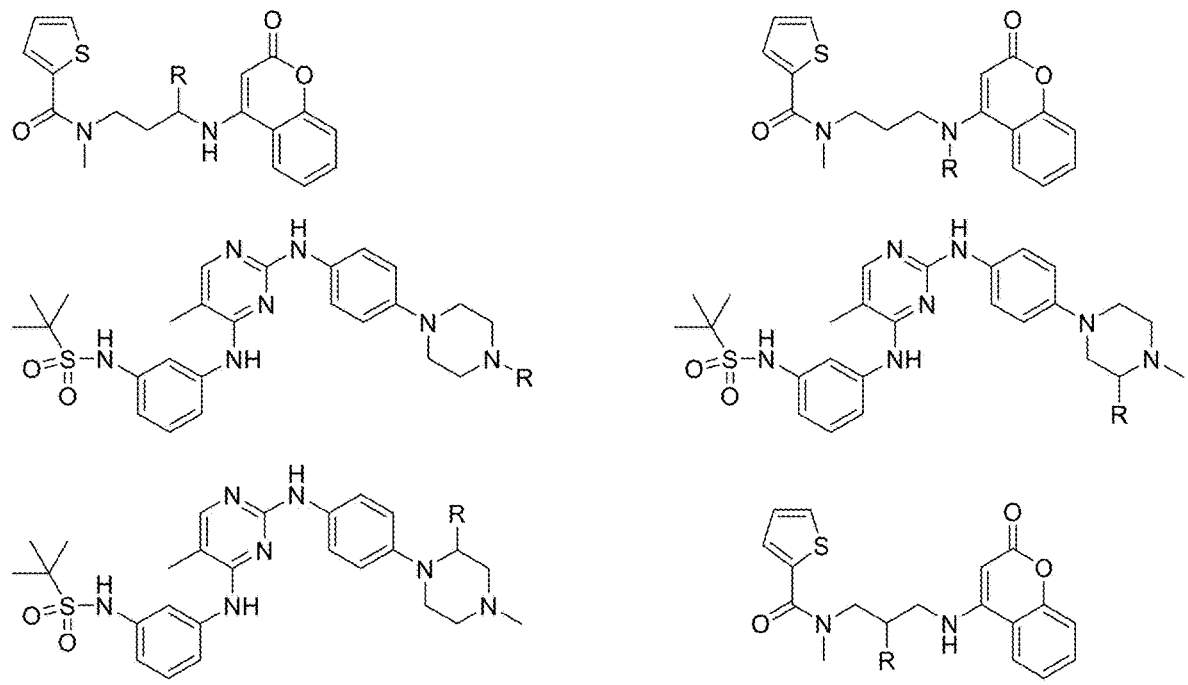
FIG. 3KKK
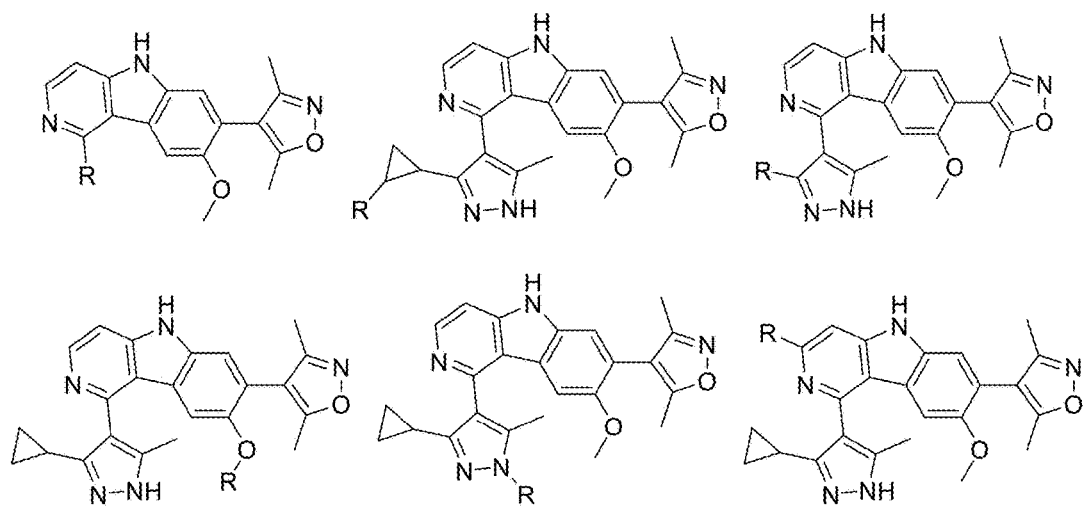

FIG. 3LLL
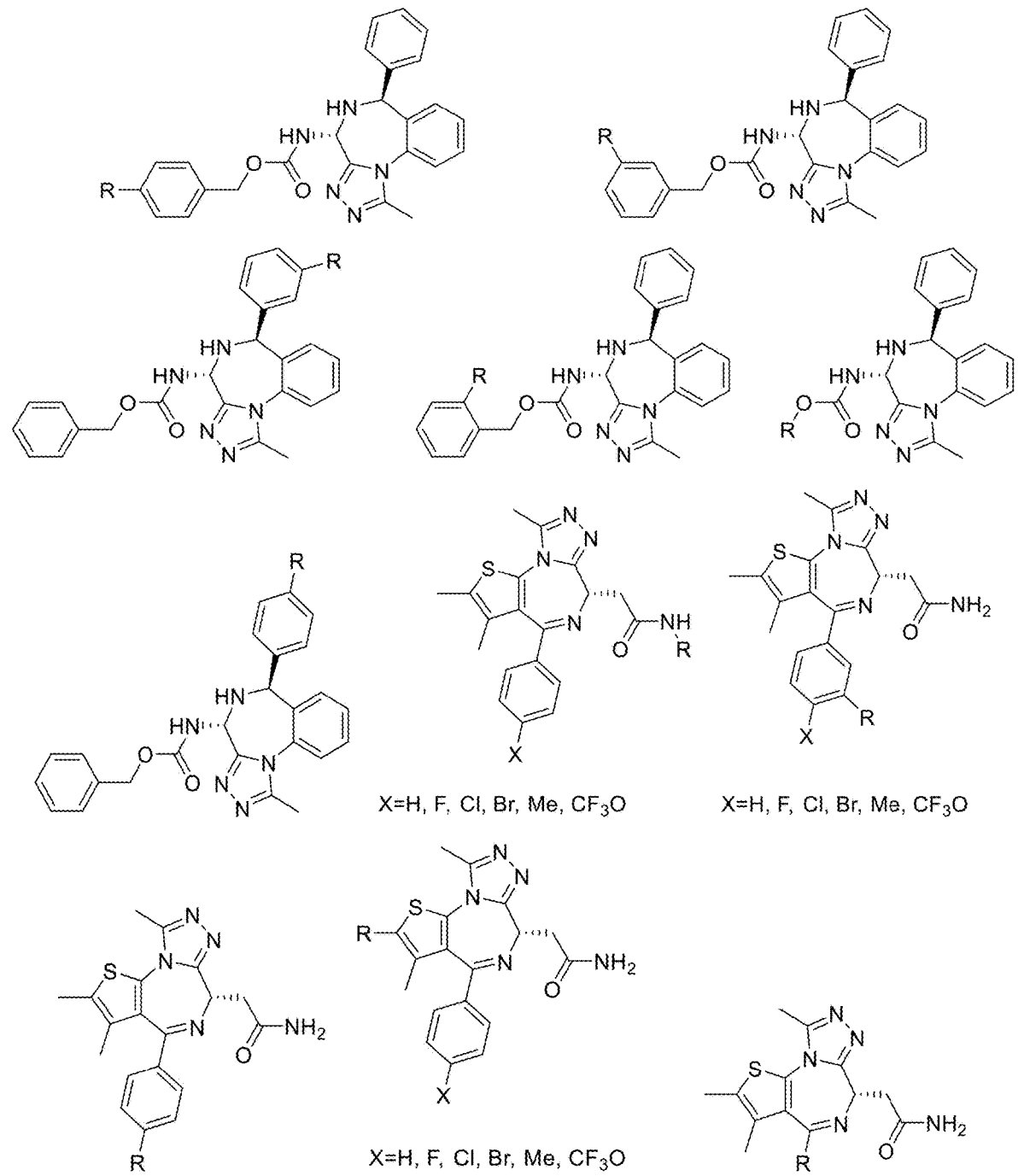

FIG. 3MMM
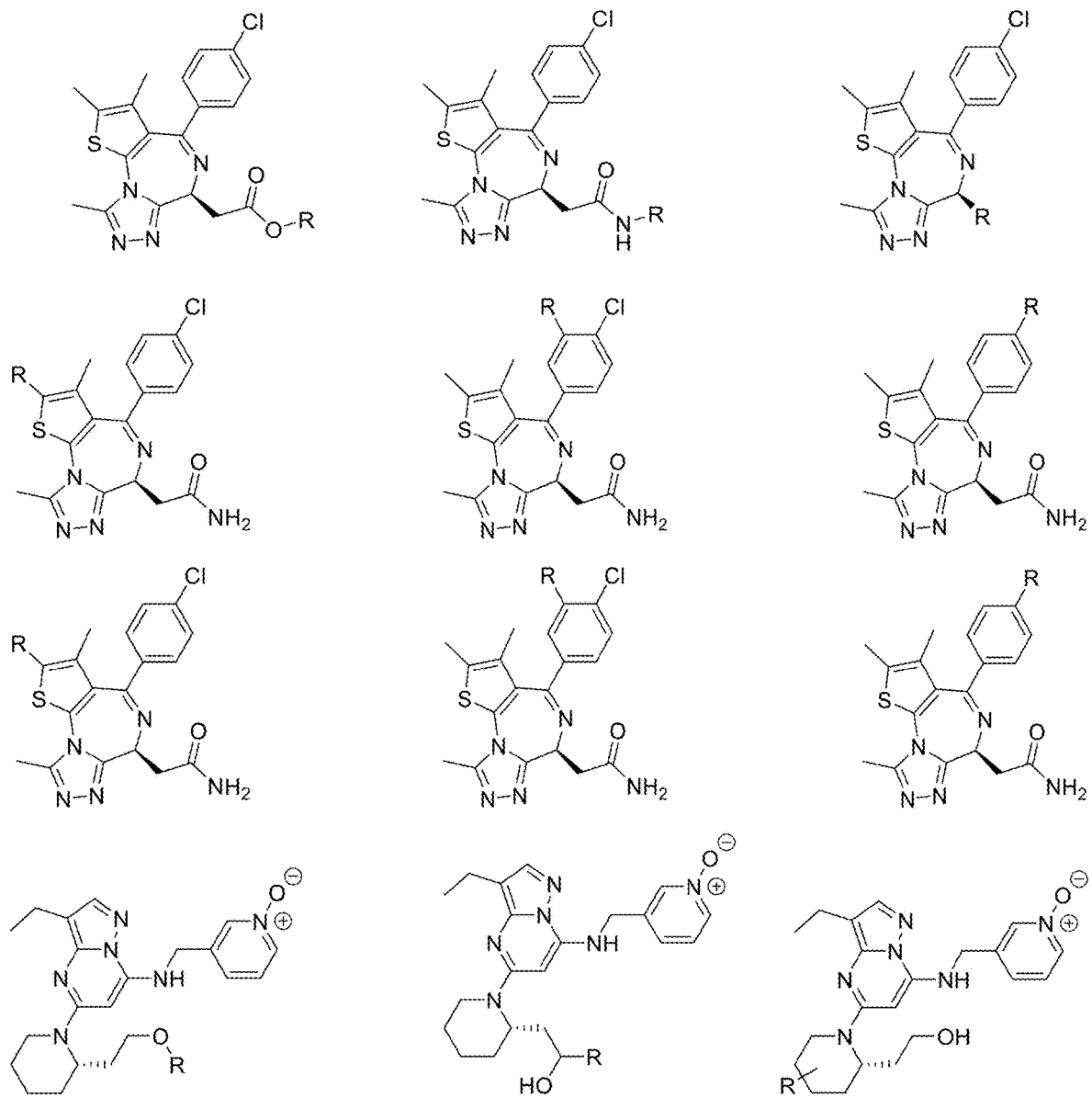
FIG. 3NNN
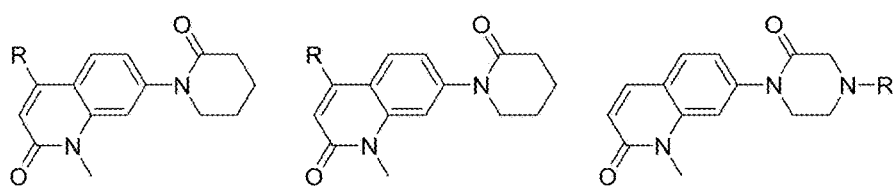

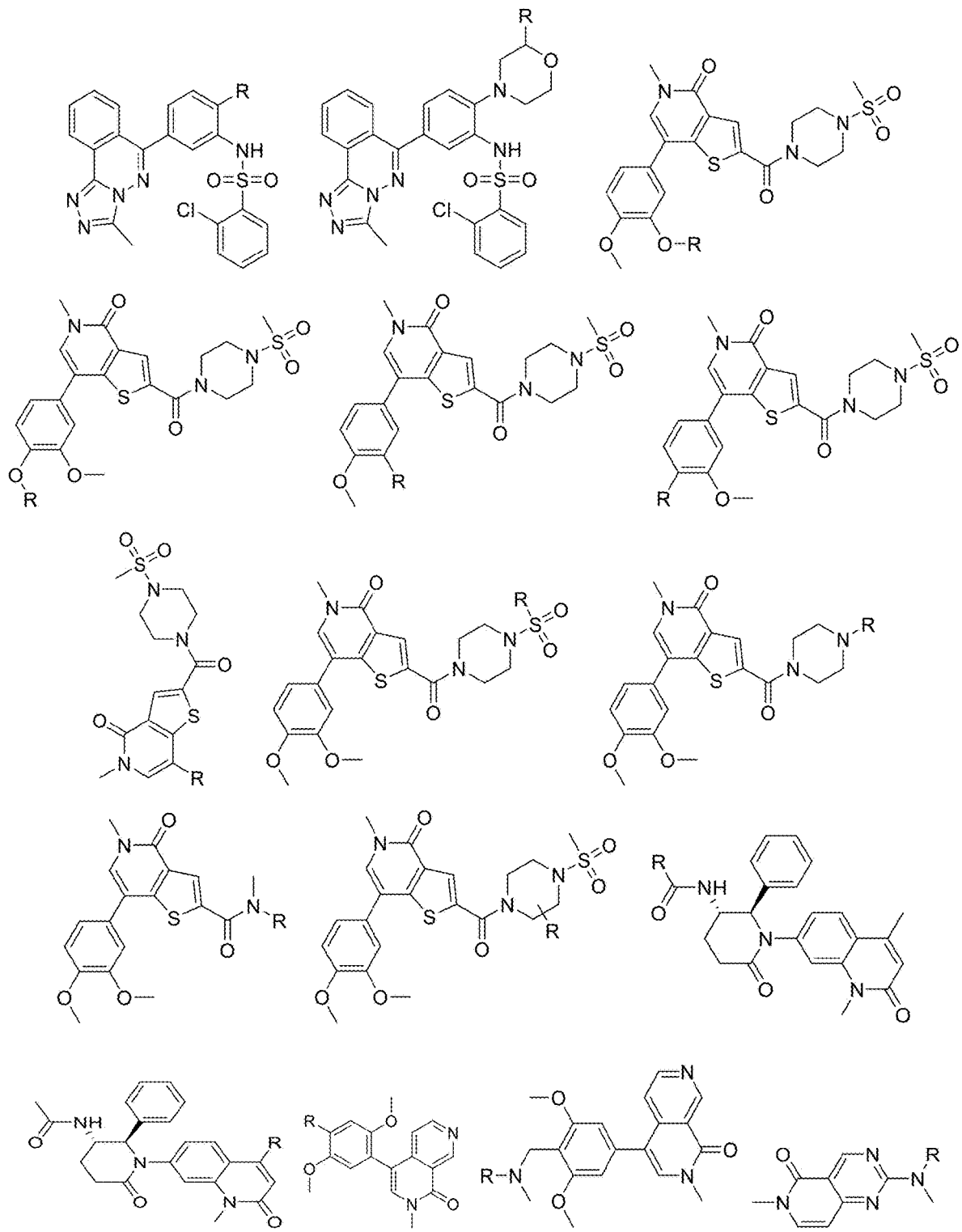
FIG. 3000

FIG. 3PPP
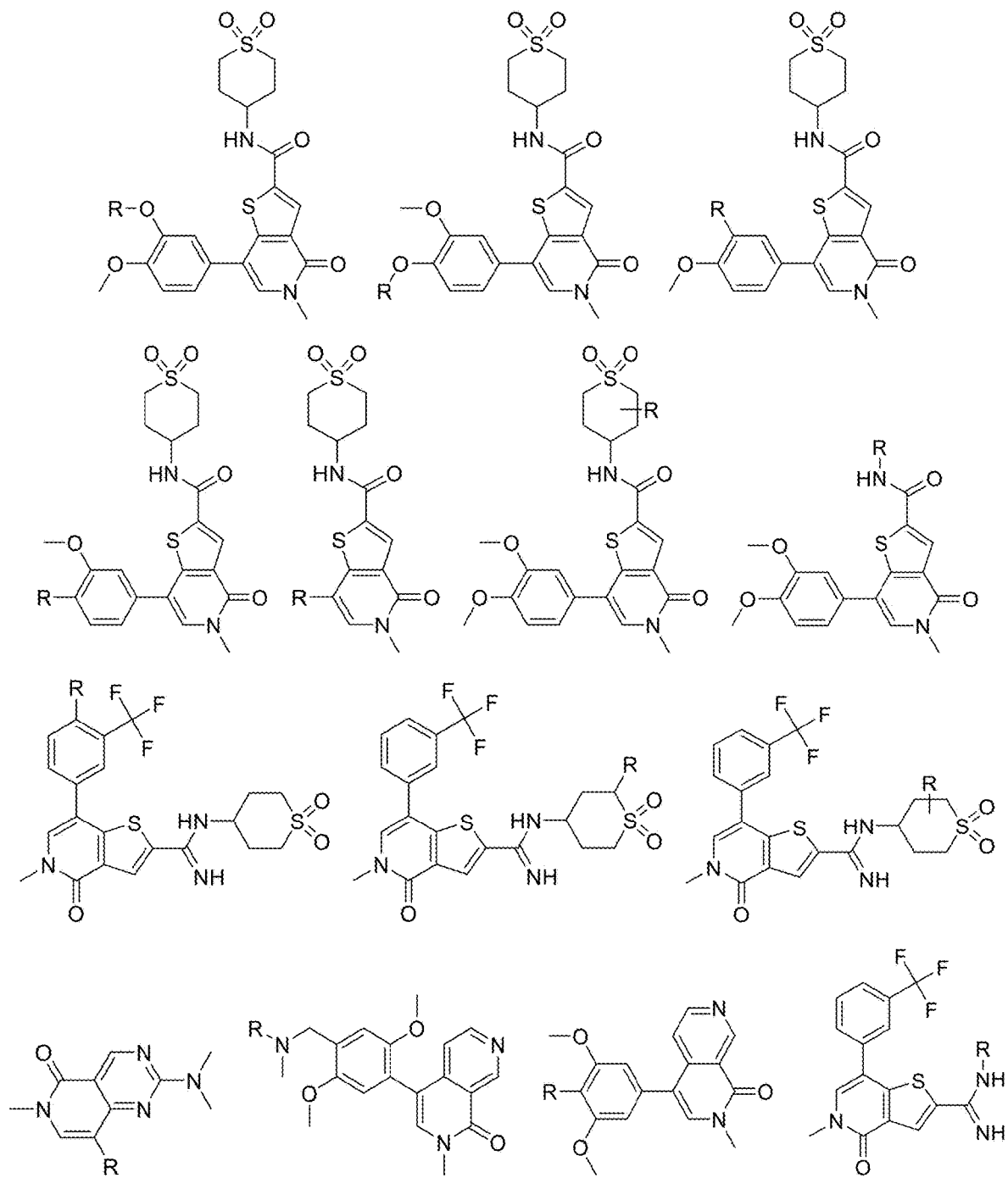

FIG. 3QQQ
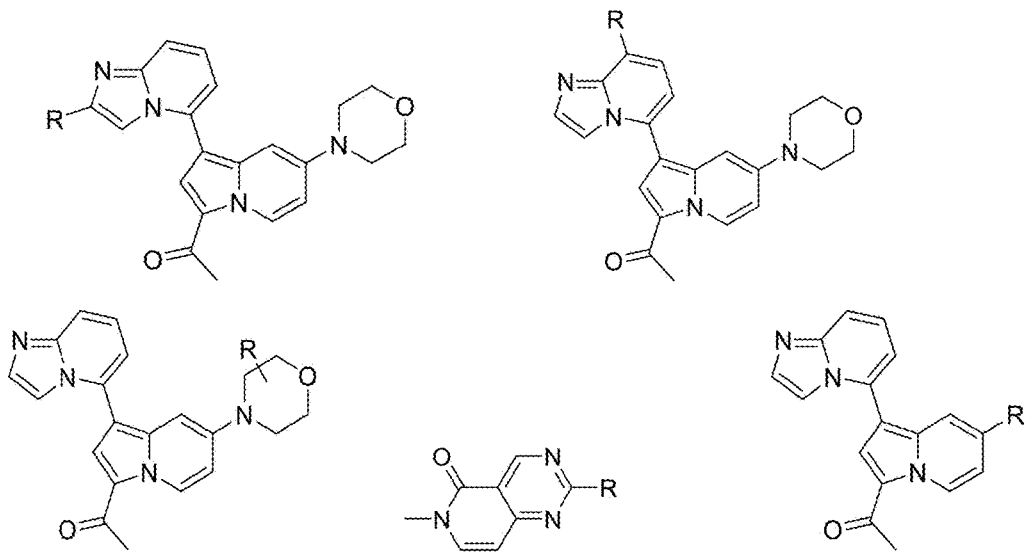
FIG. 3RRR
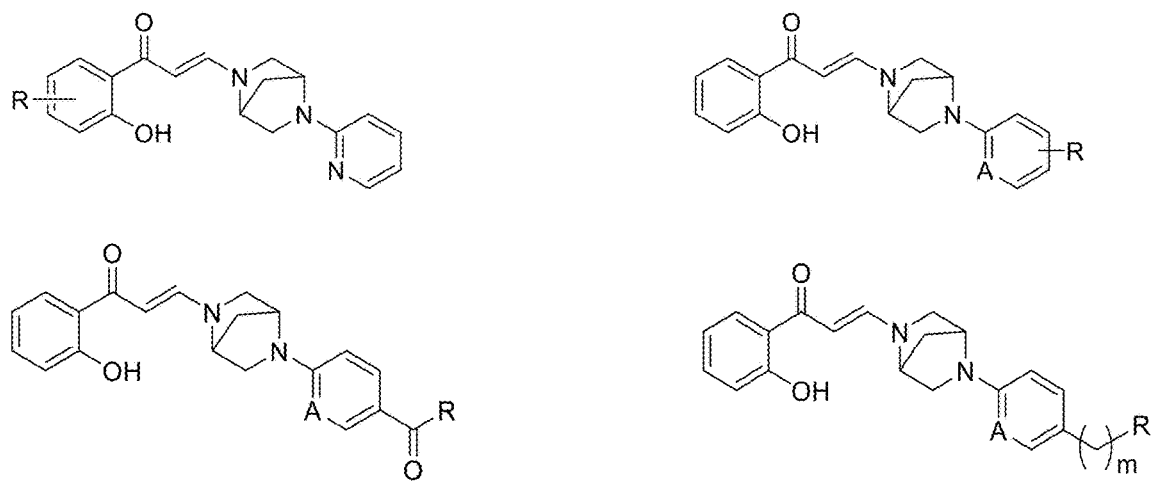
FIG. 3SSS
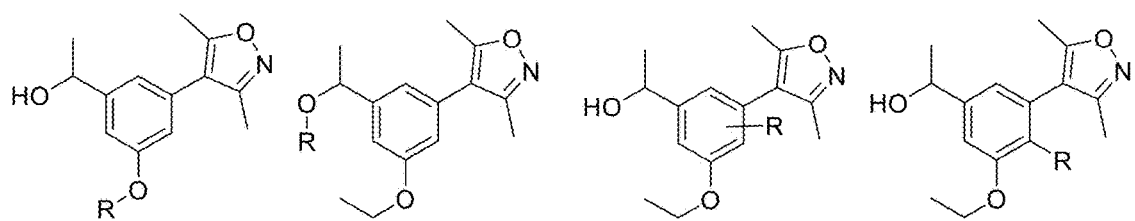

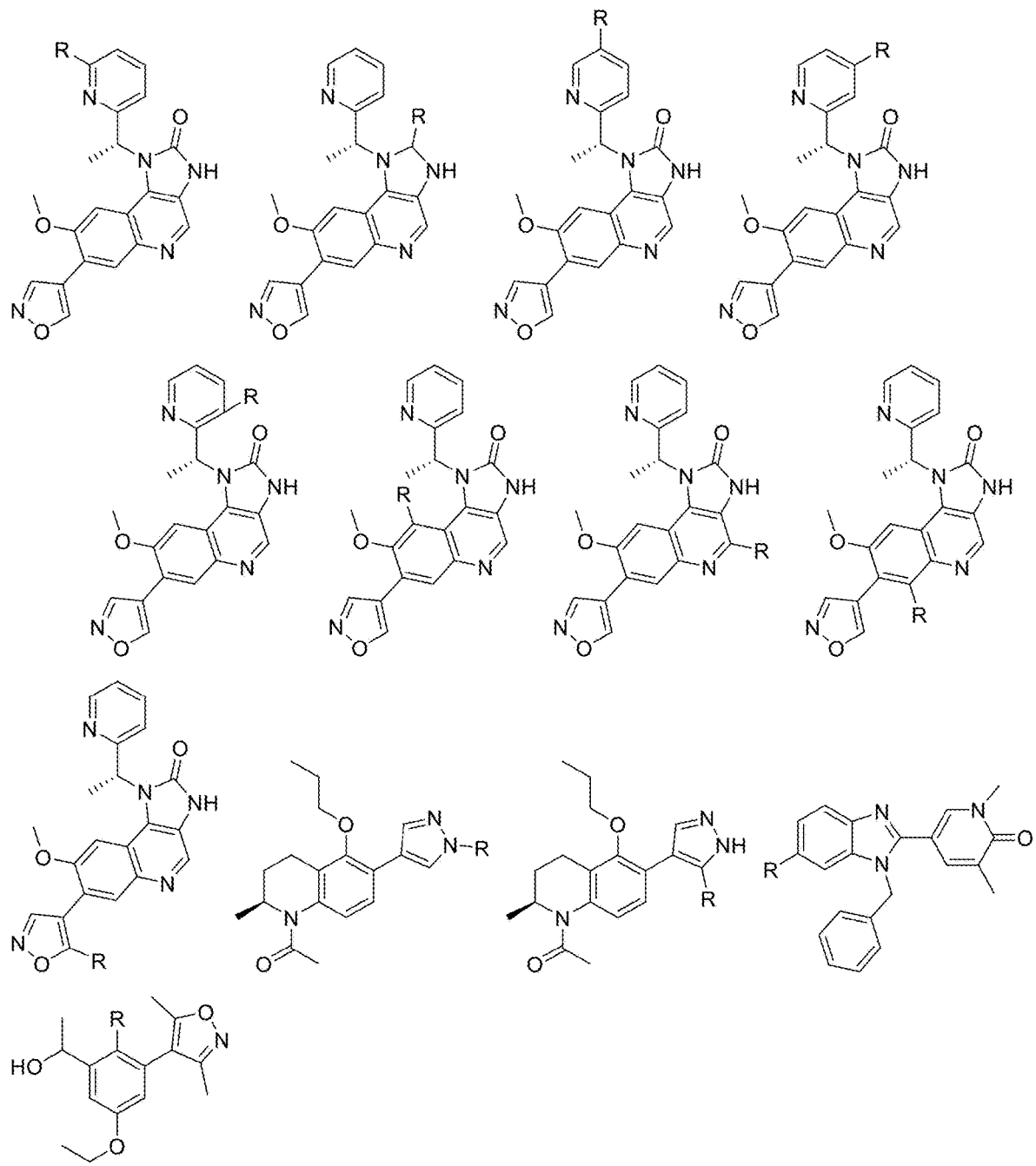
FIG. 3TTT

FIG. 3UUU
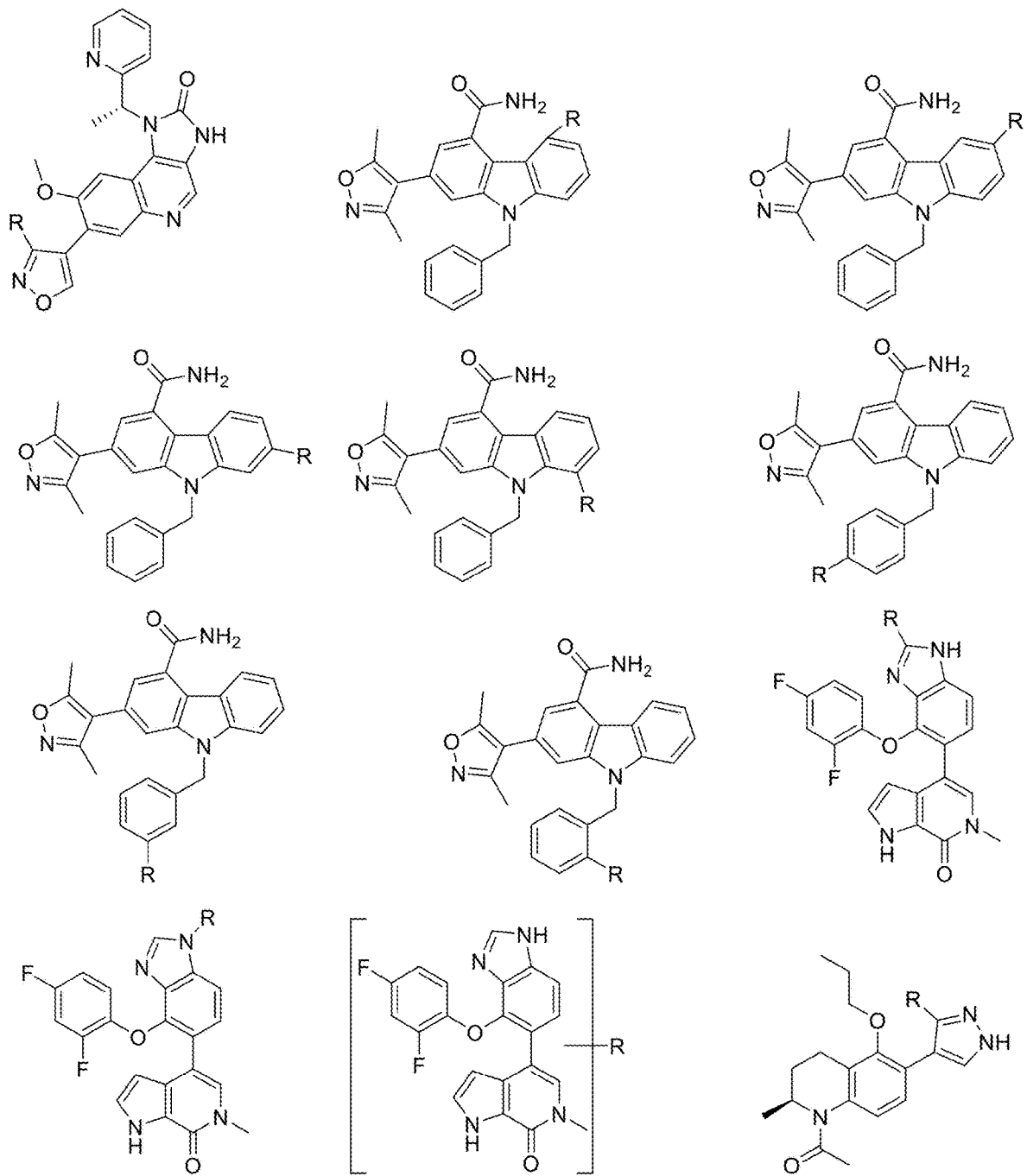

FIG. 3VVV
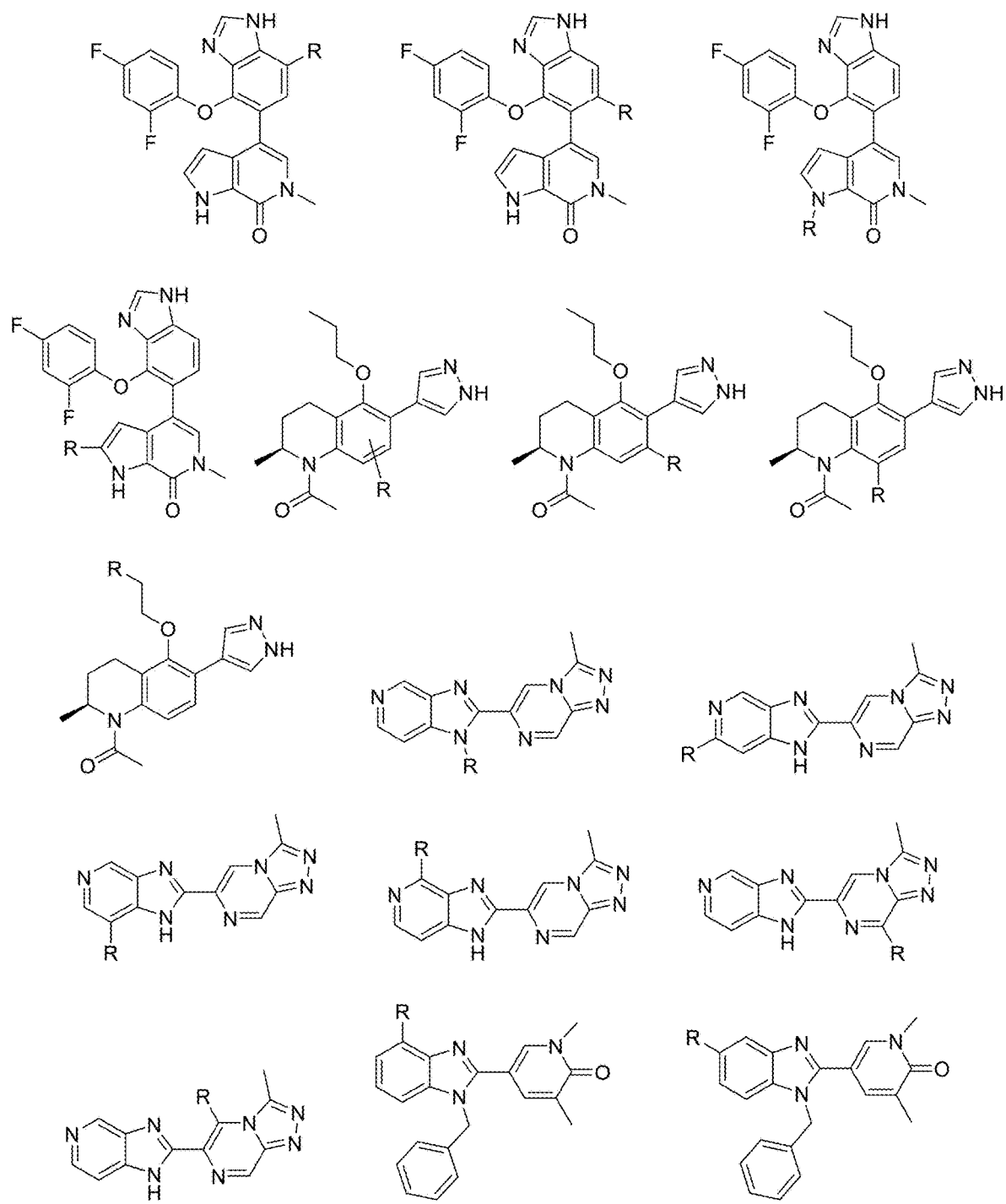

FIG. 3WWW
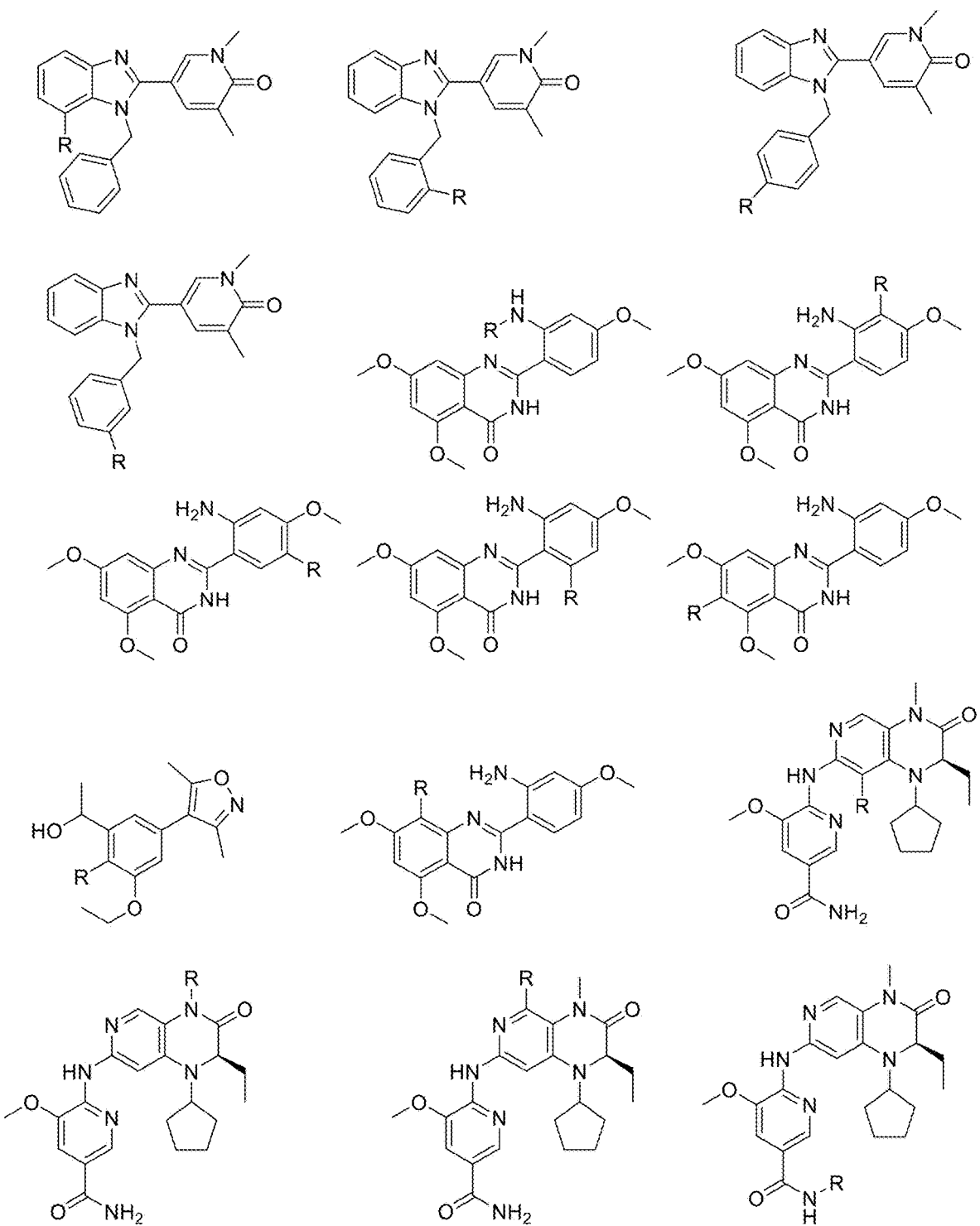

FIG. 3XXX
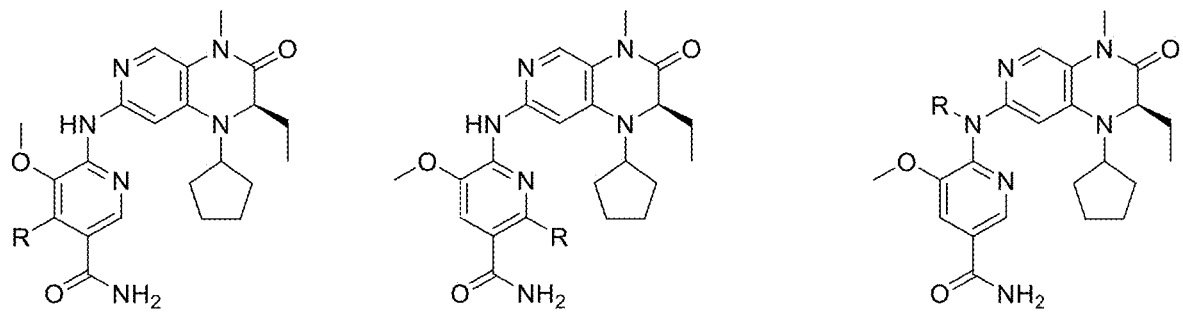
FIG. 3YYY
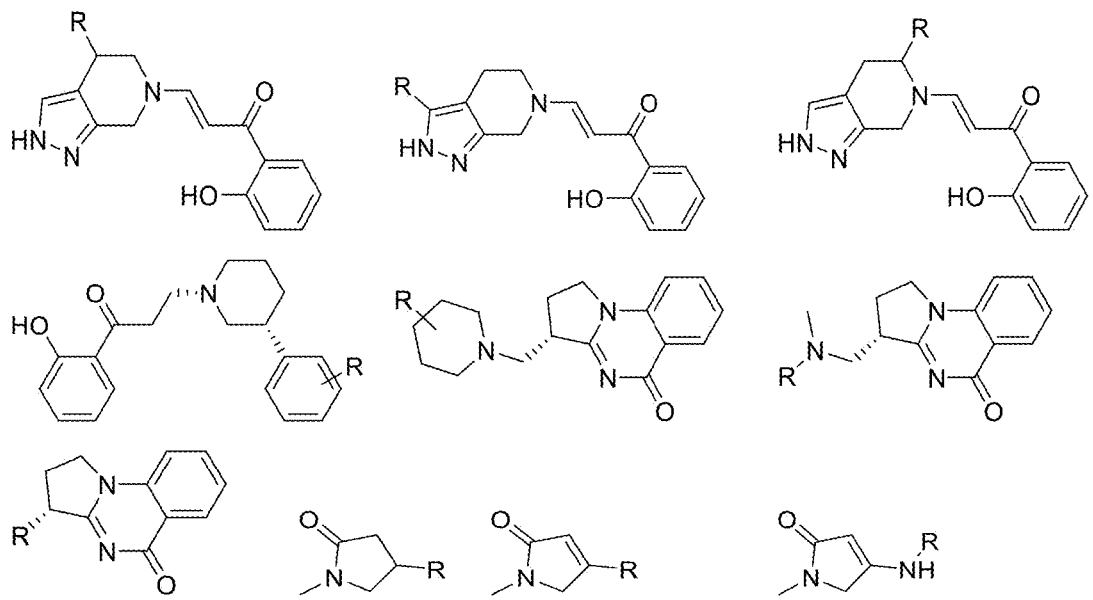
FIG. 3ZZZ
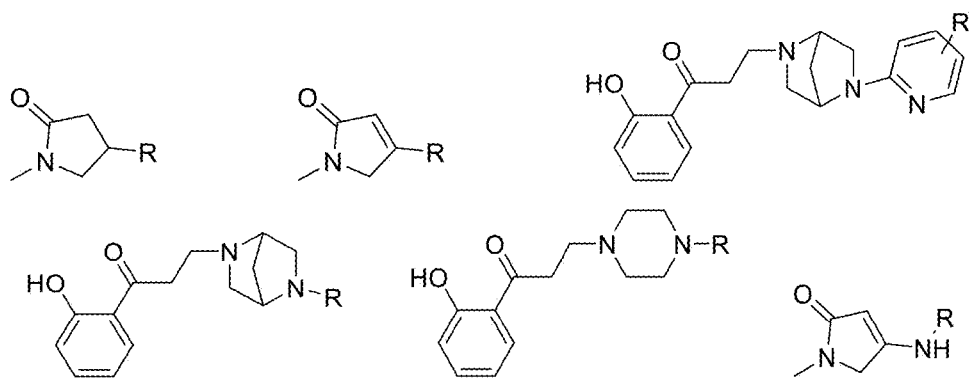

FIG. 3AAAA
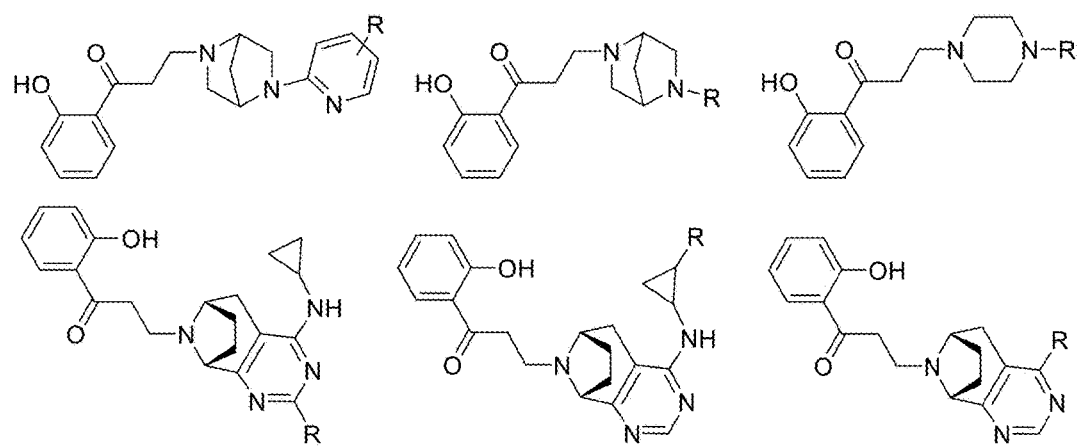
FIG. 3BBBB
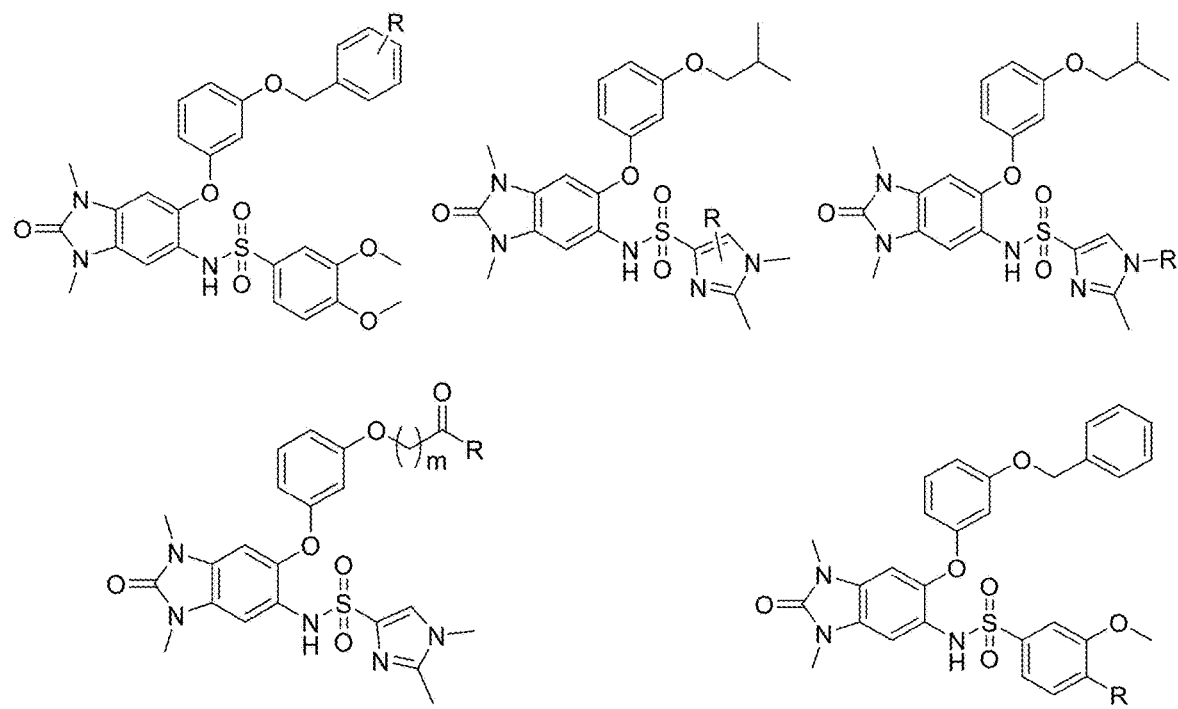

FIG. 3CCCC
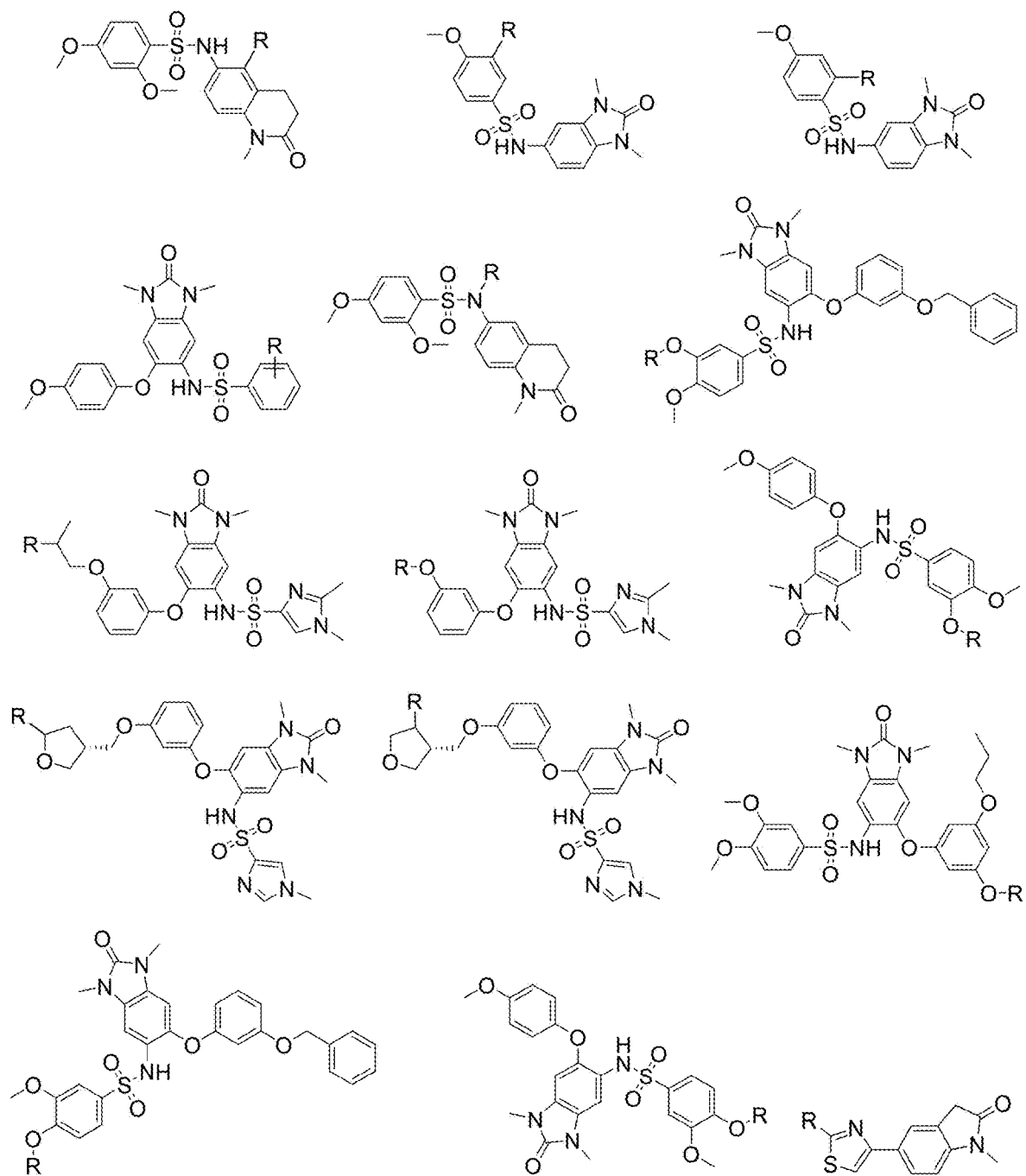

FIG. 3DDDD
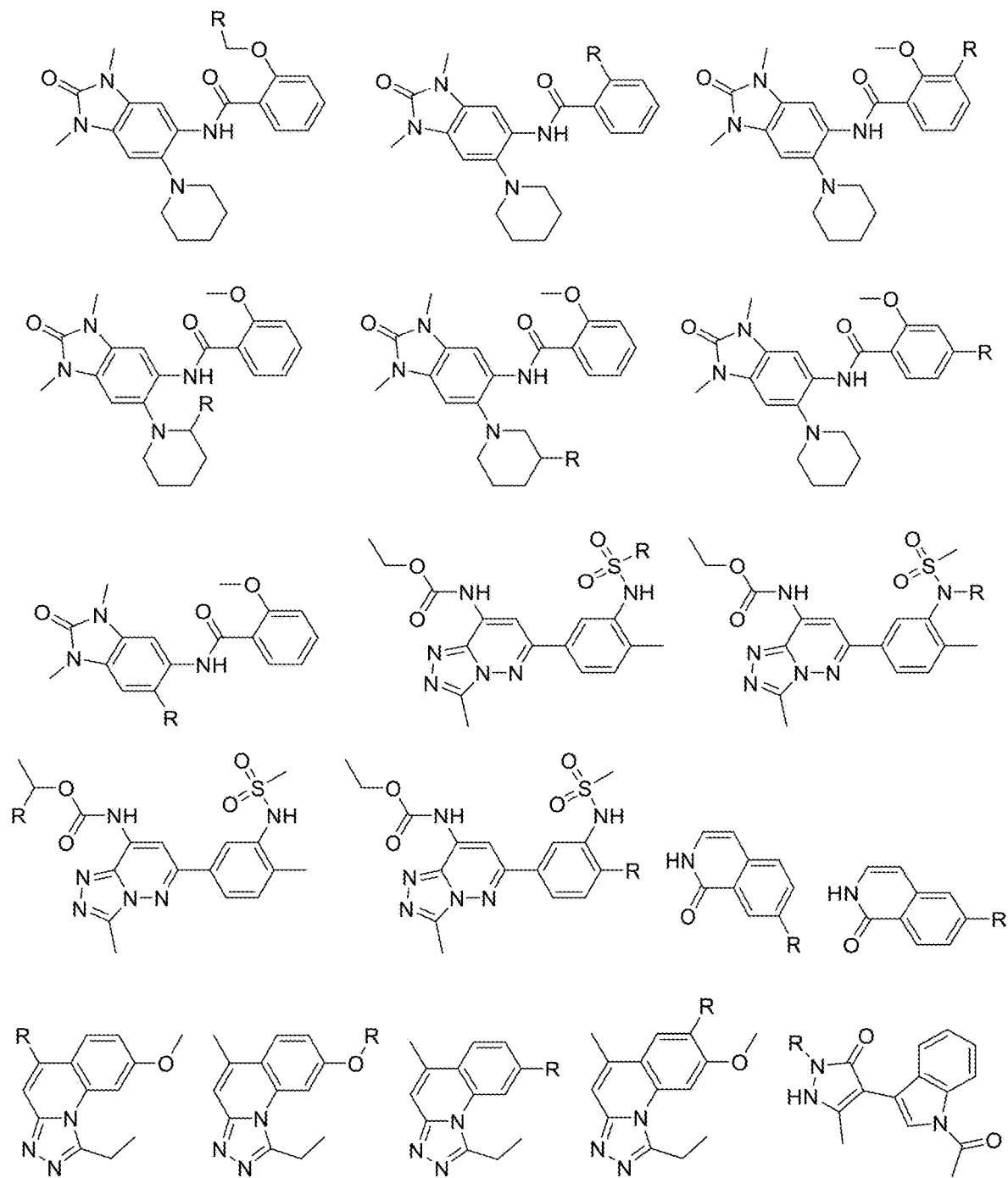

FIG. 3EEEE
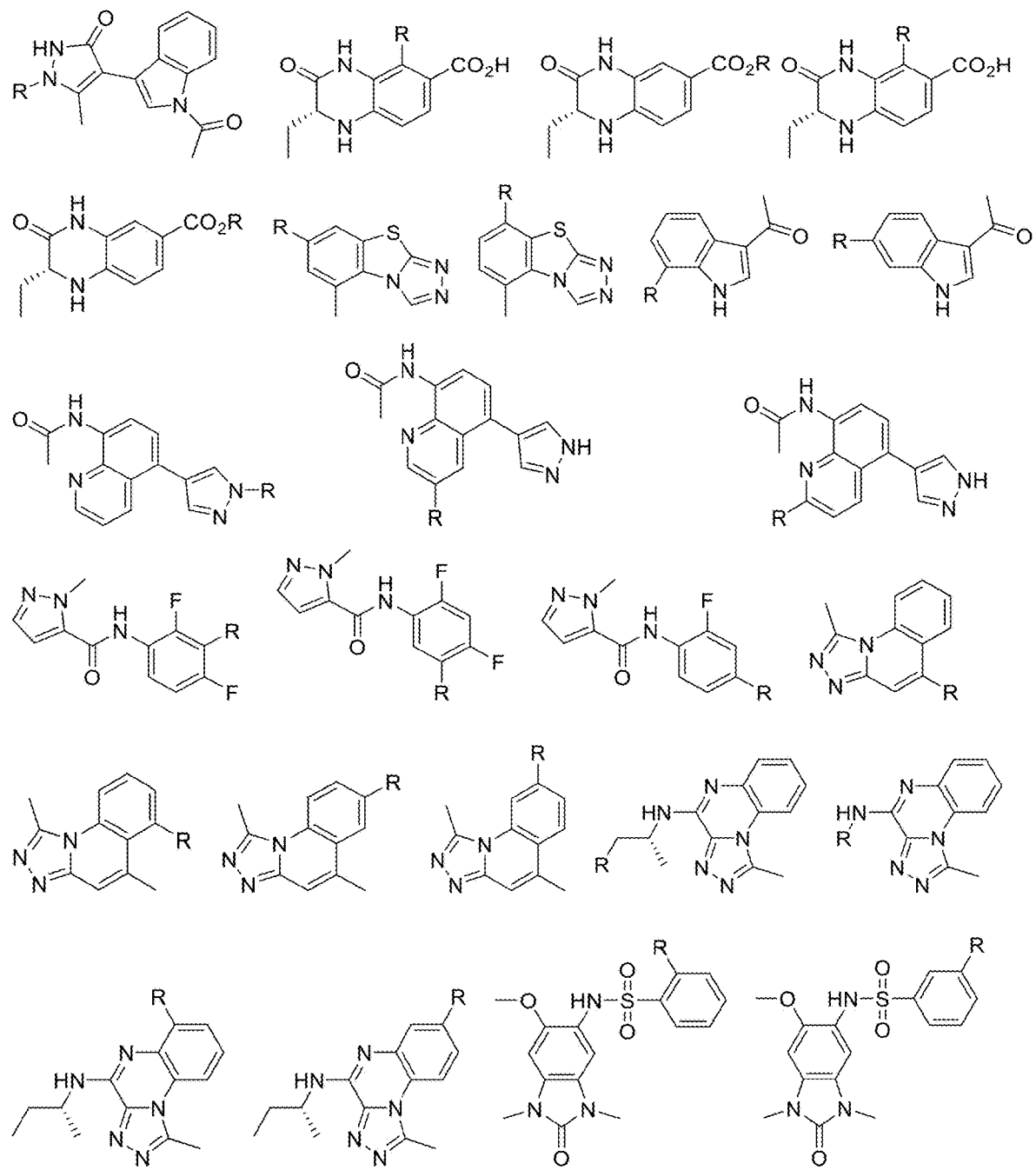

FIG. 3FFFF
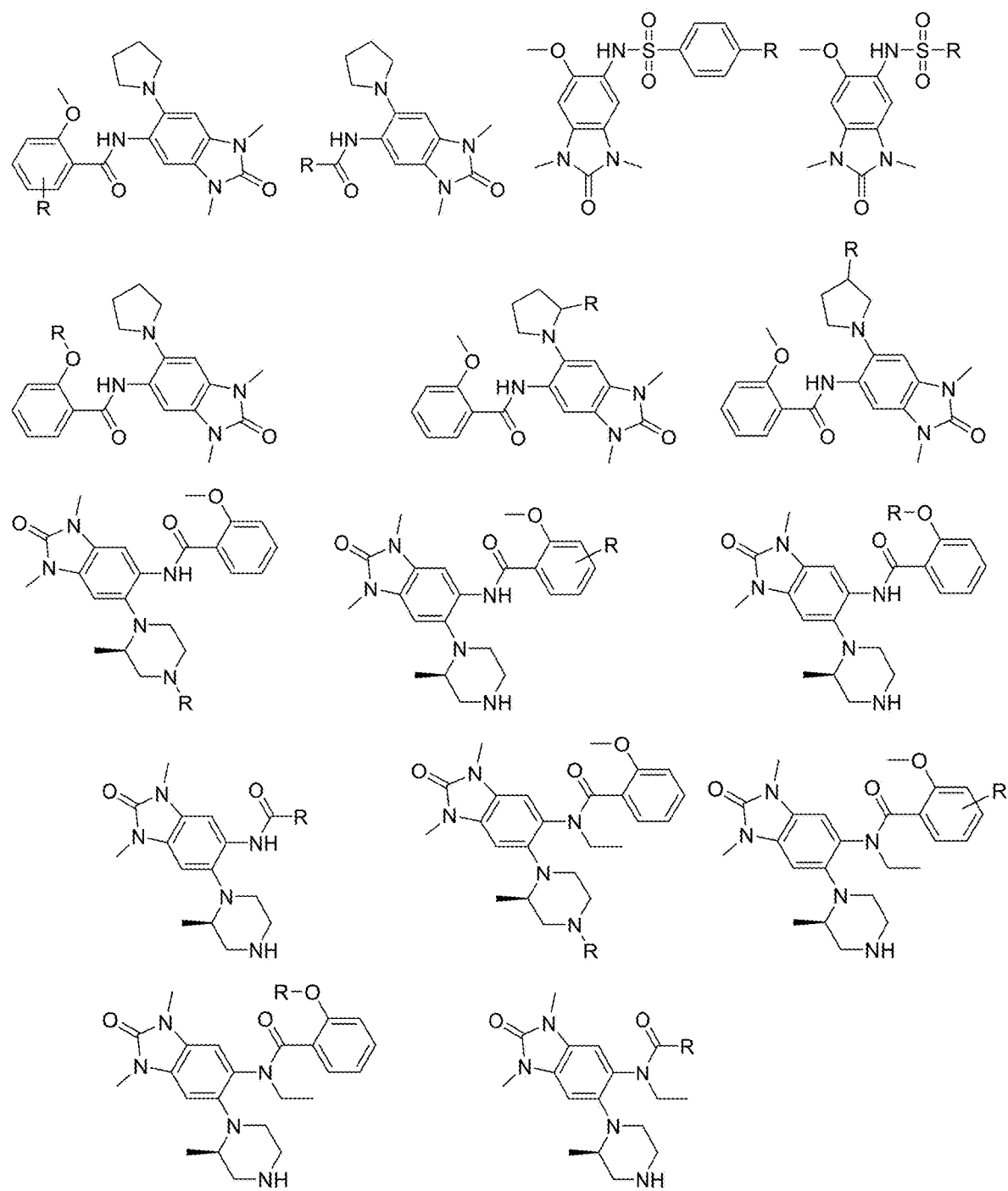

FIG. 3GGGG
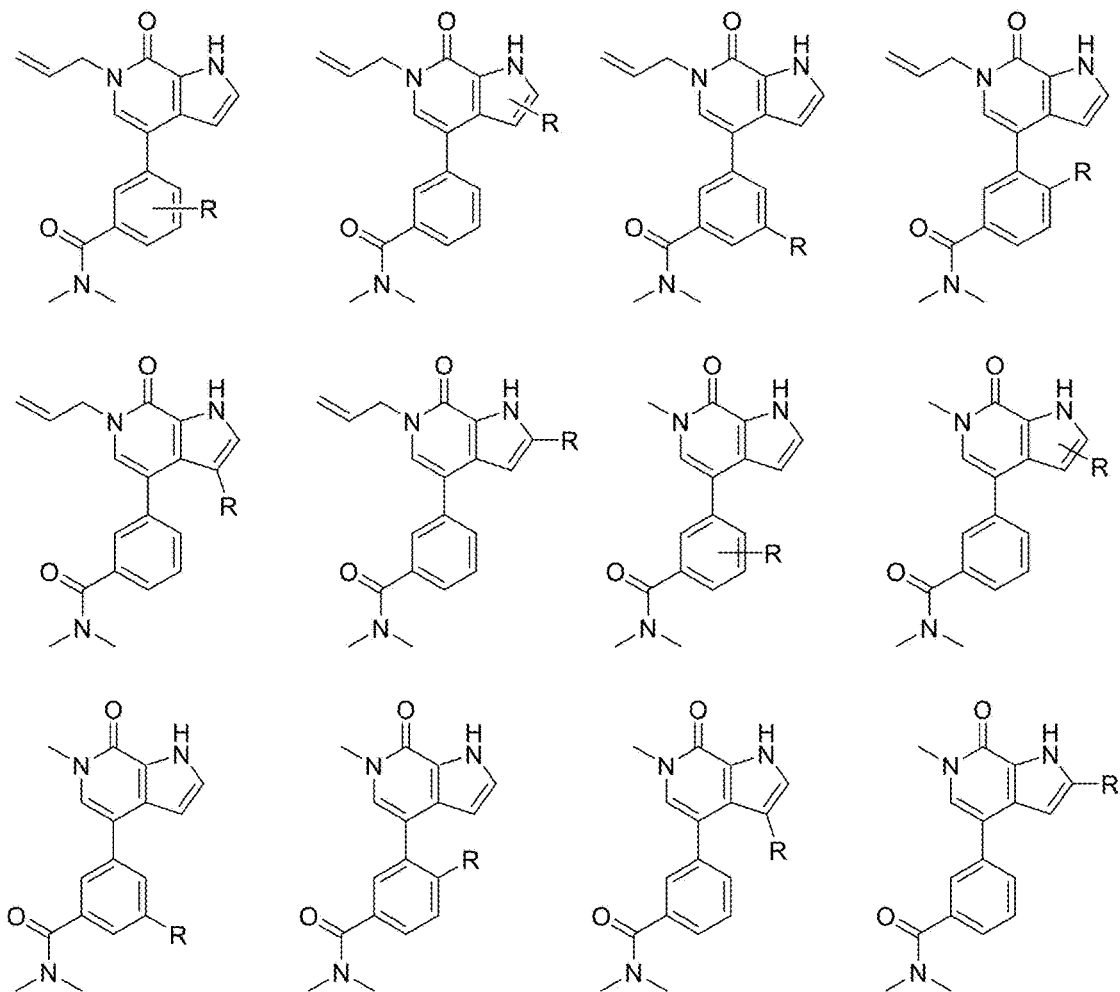
FIG. 3HHHH
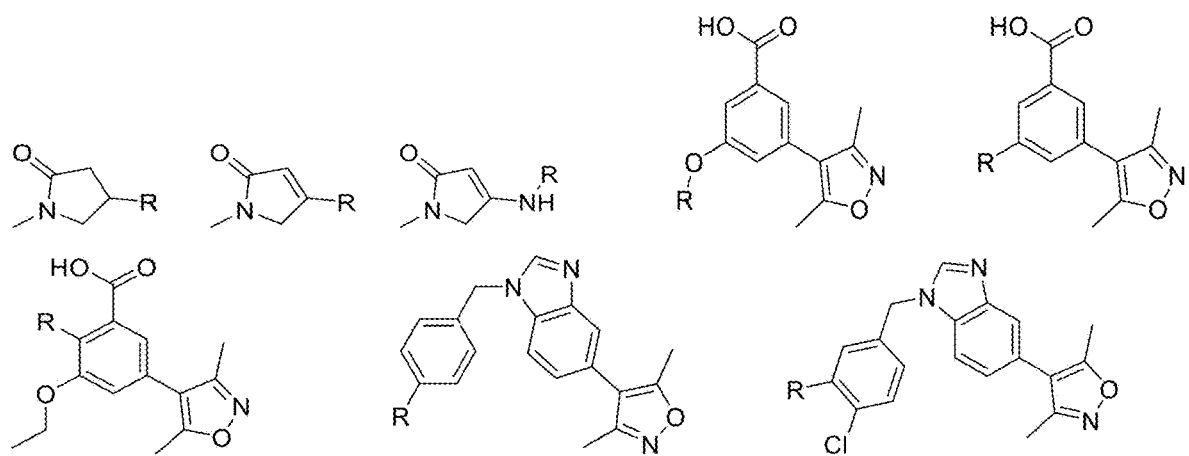

FIG. 3IIII
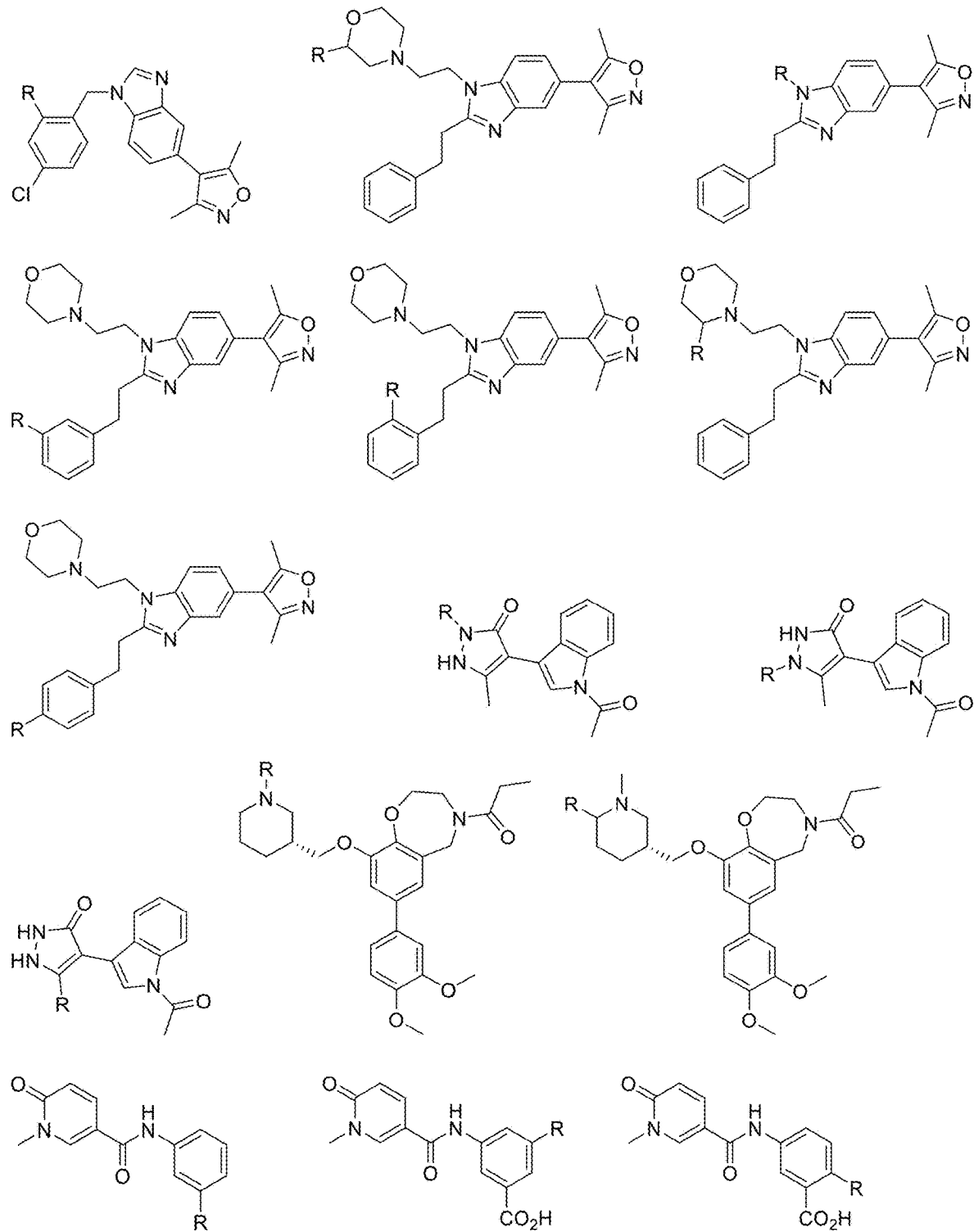

FIG. 3JJJJ
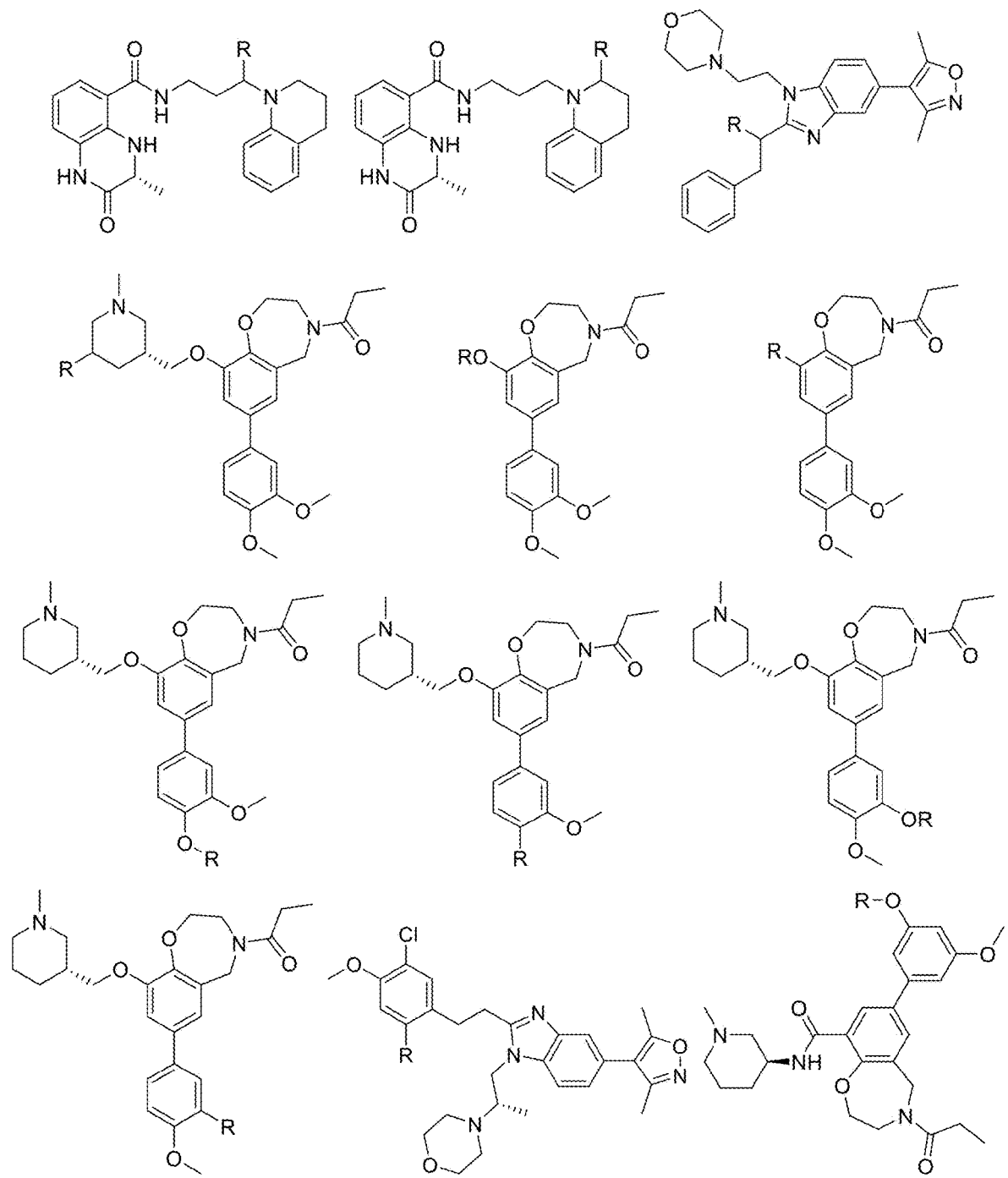

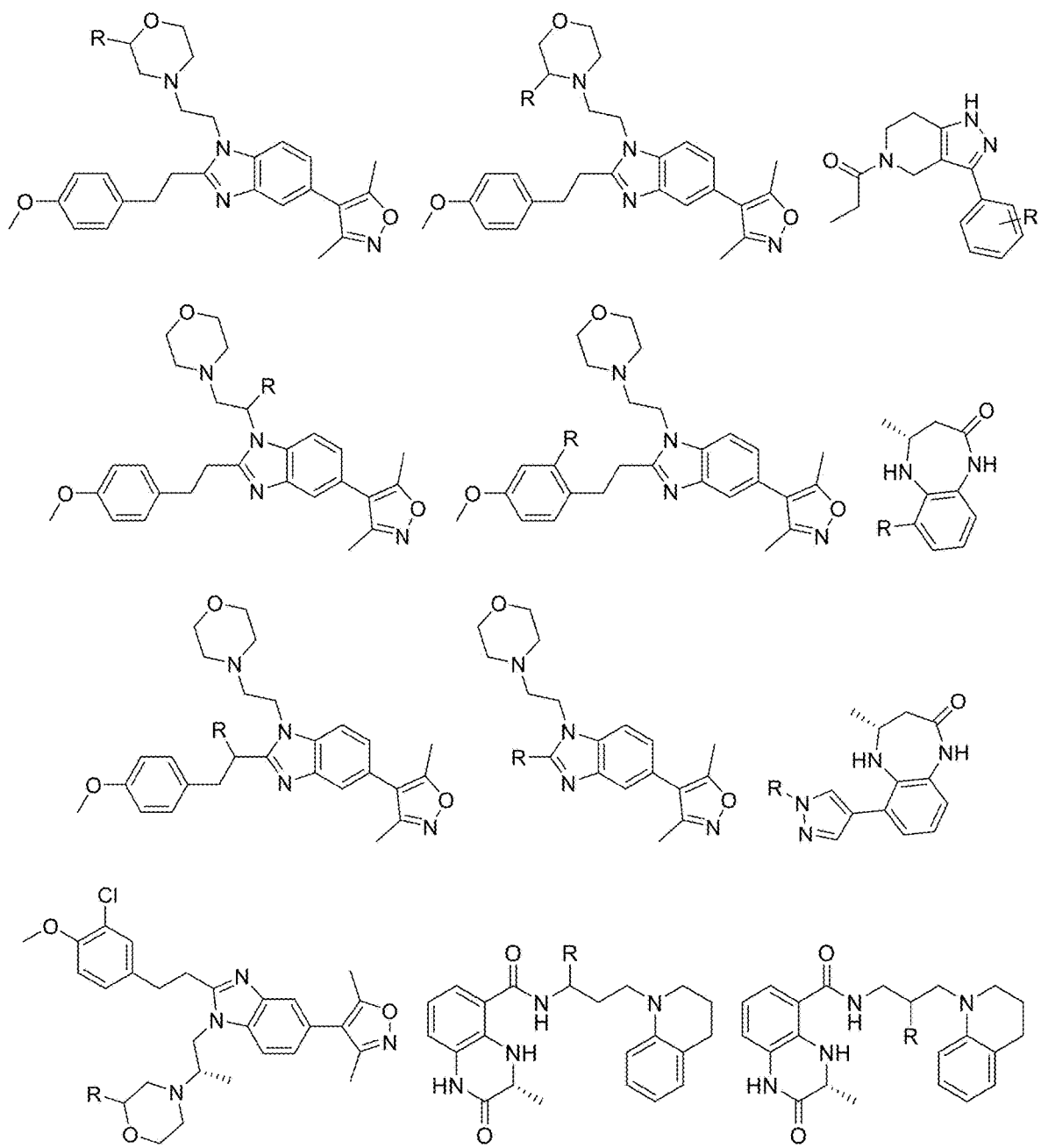
FIG. 3KKKK

FIG. 3LLLL
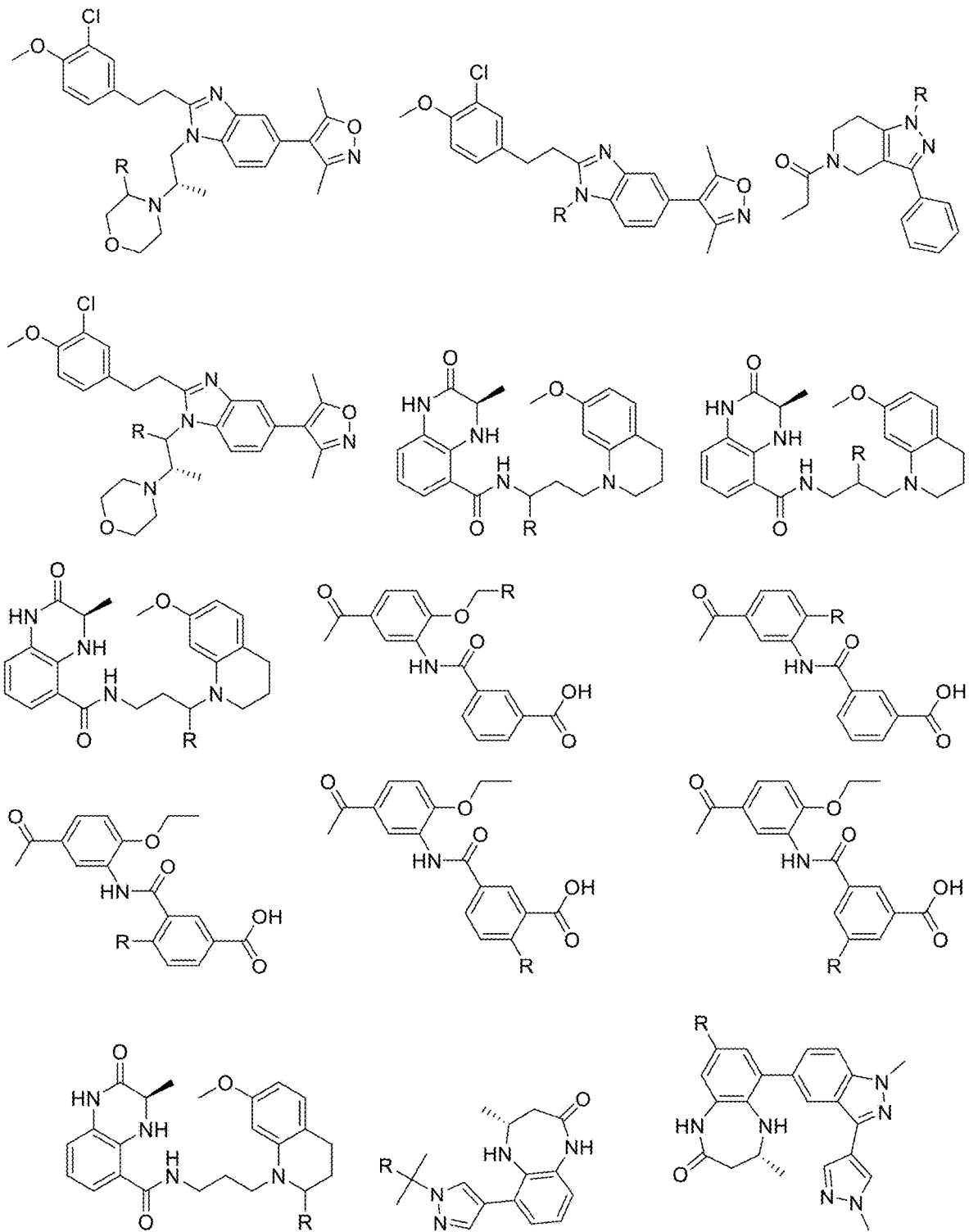

FIG. 3MMMM
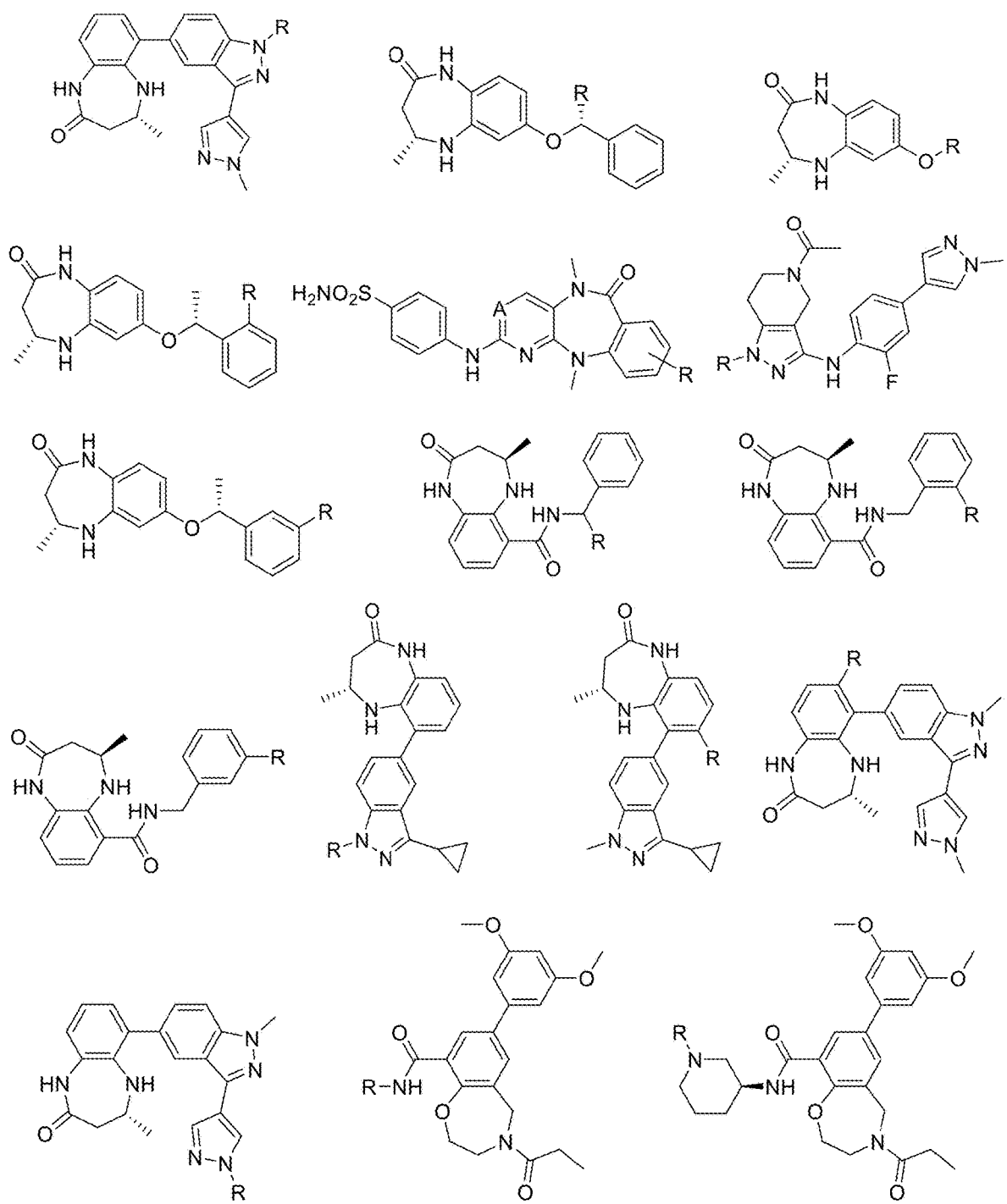

FIG. 3NNNN
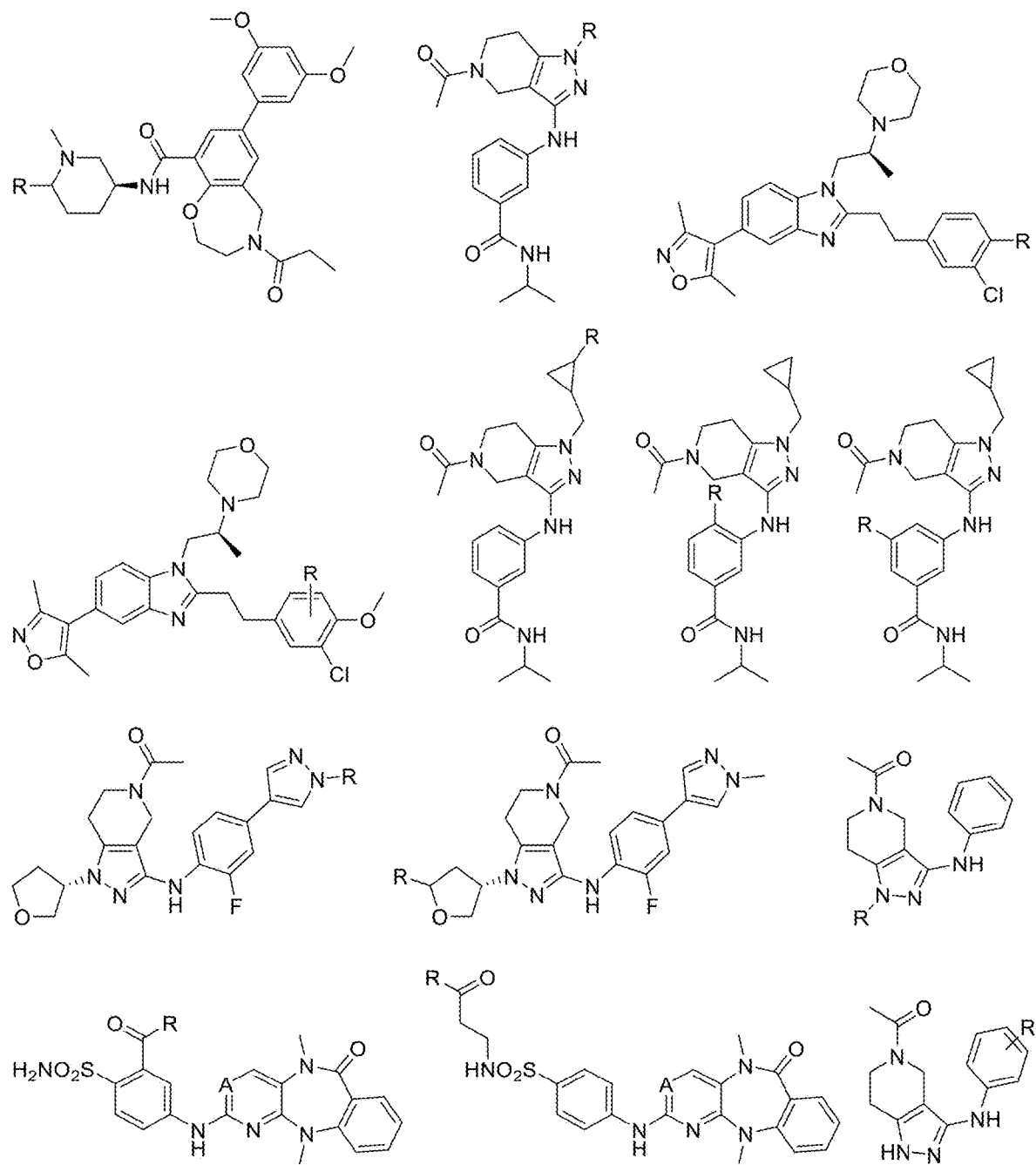

FIG. 3OOOO
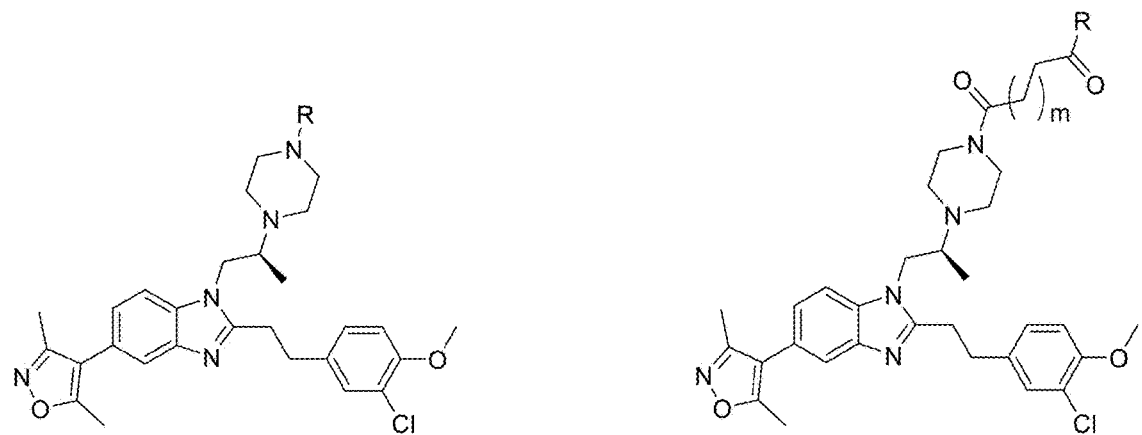
FIG. 3PPPP
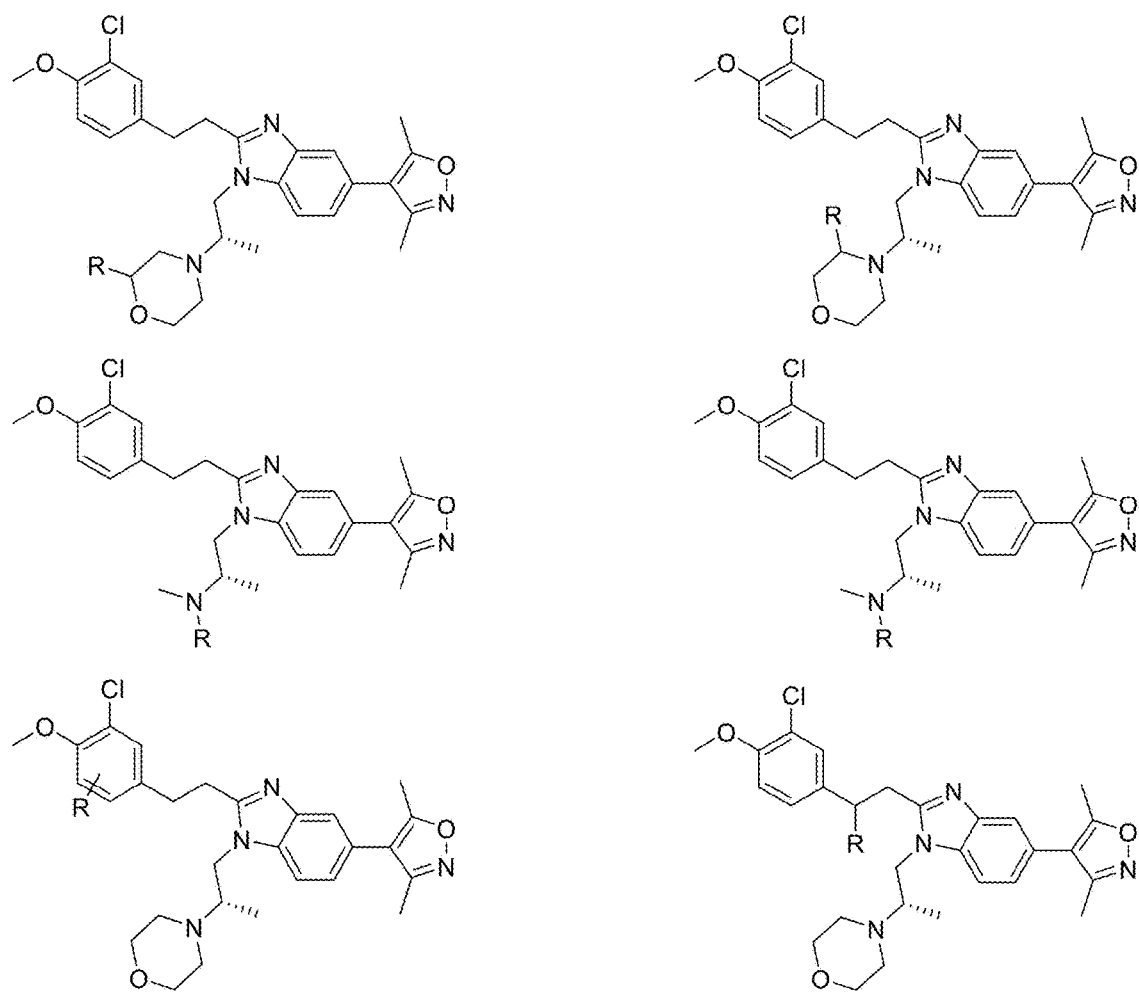

FIG. 3QQQQ
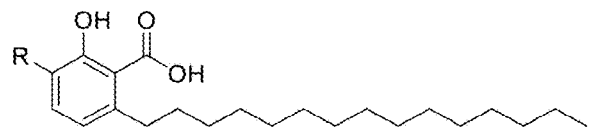
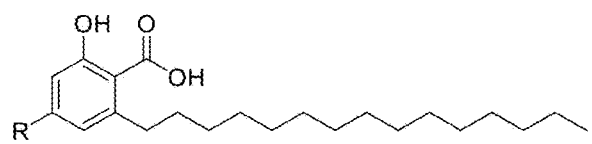
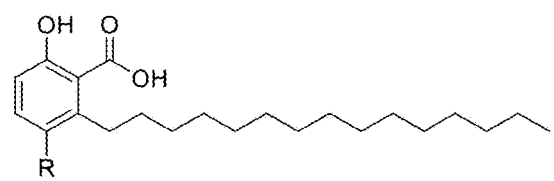
FIG. 3RRRR
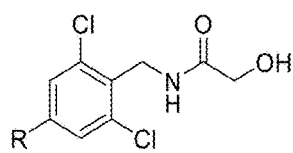
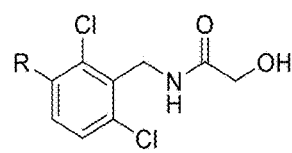
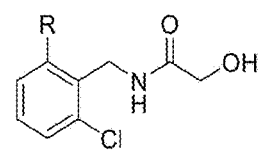
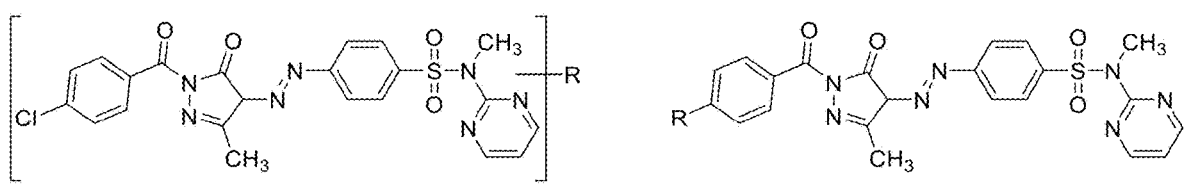
FIG. 3SSSS
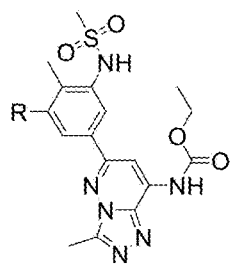
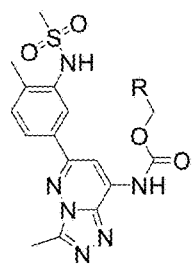
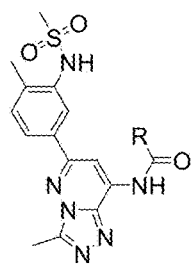
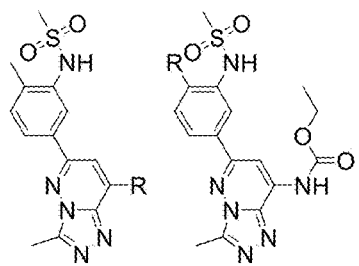

FIG. 3TTTT
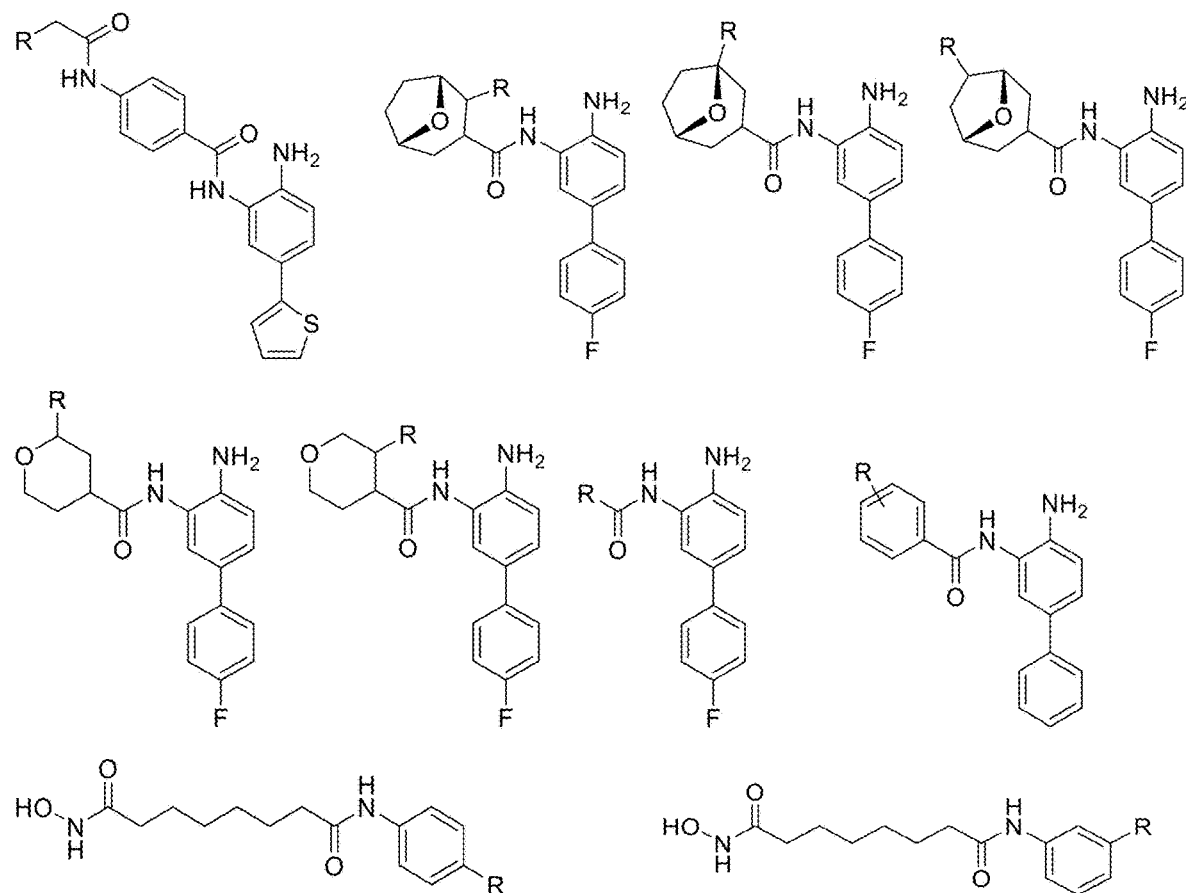
FIG. 3UUUU
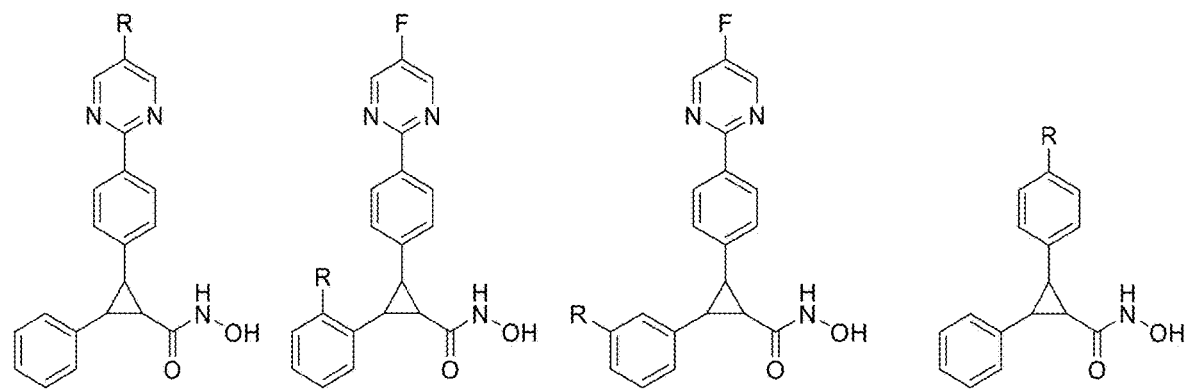

FIG. 3VVVV
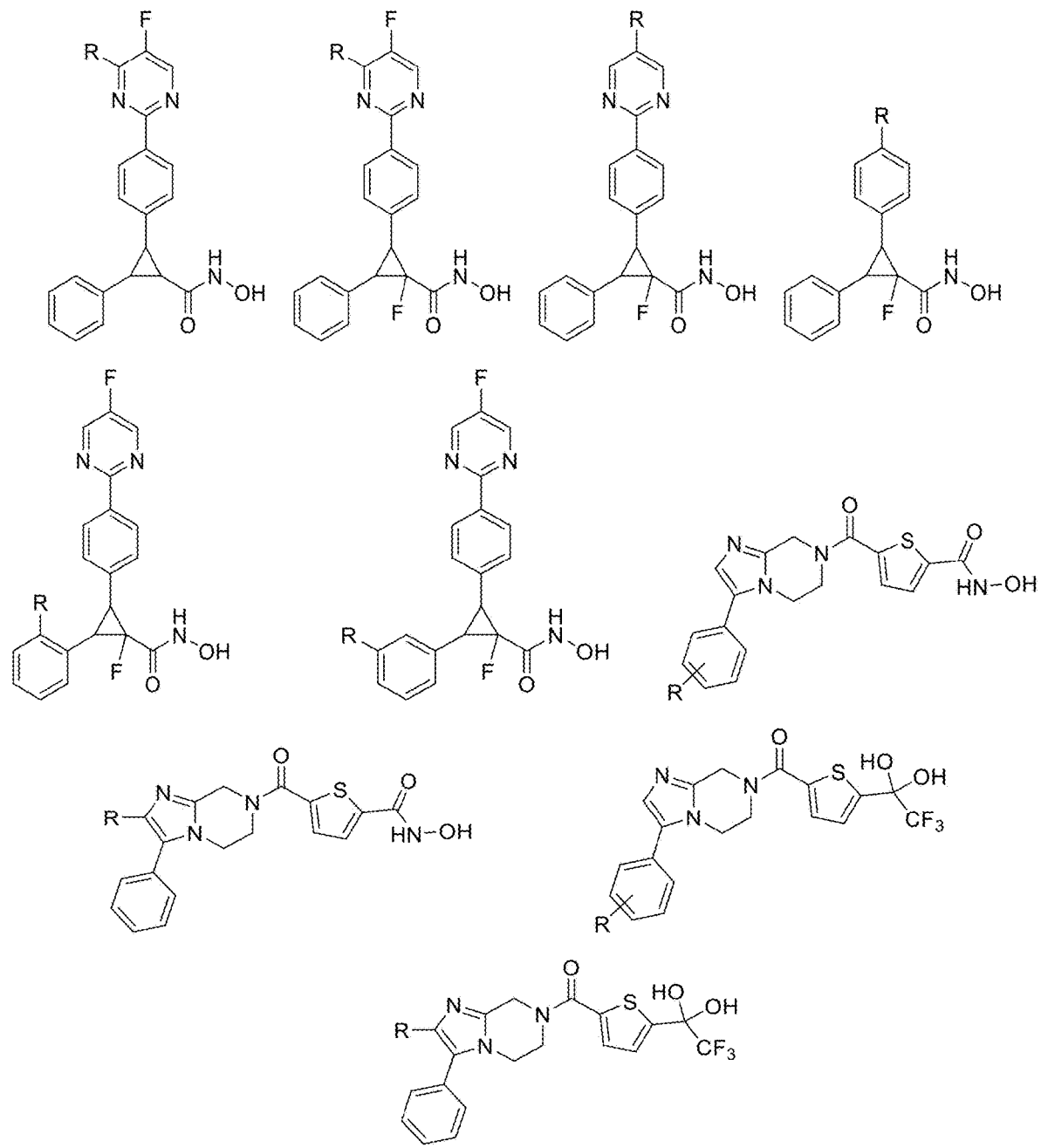

FIG. 3WWWW
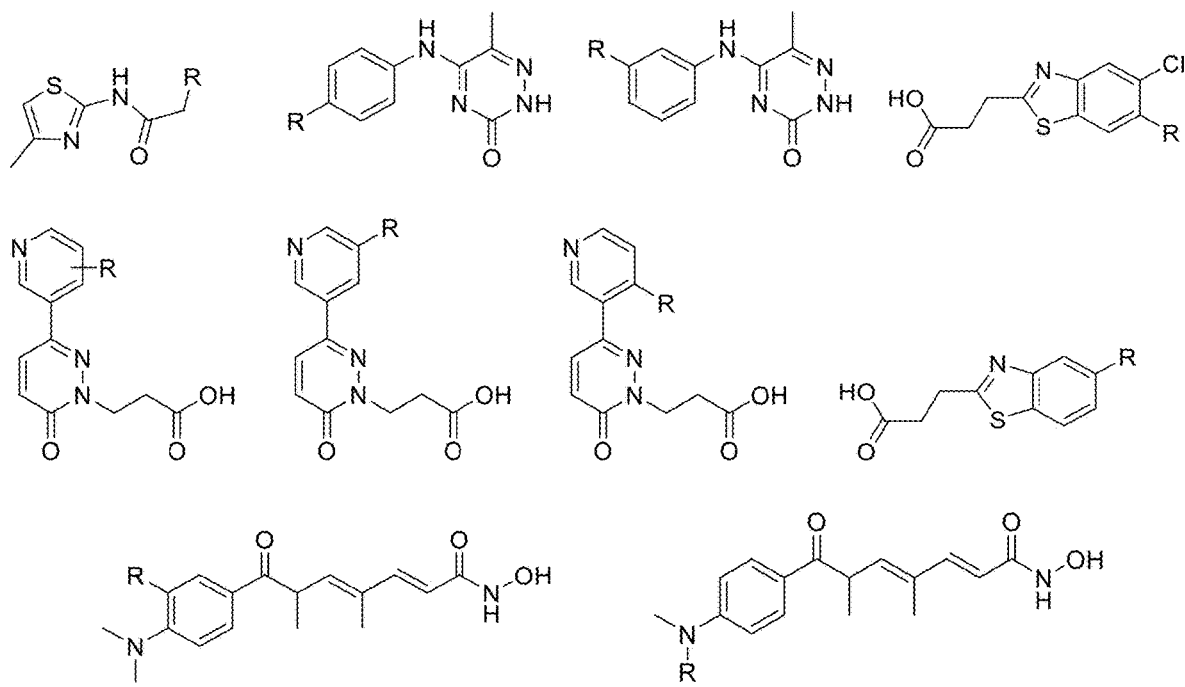
FIG. 3XXXX
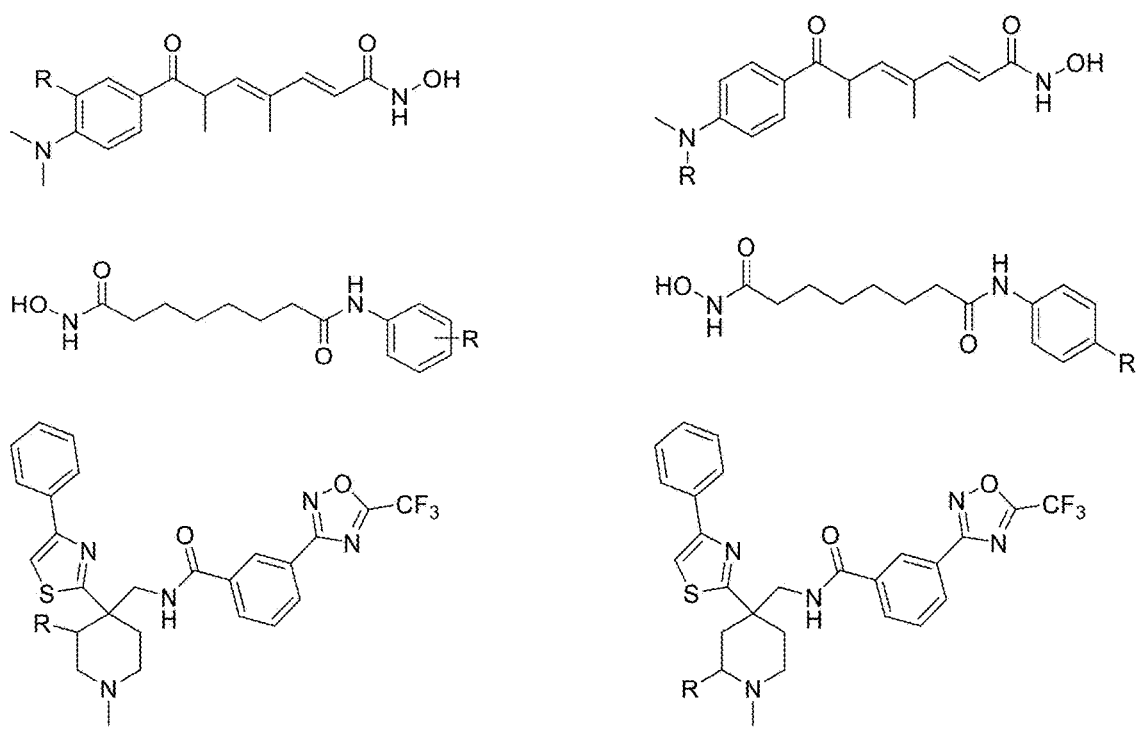

FIG. 3YYYY
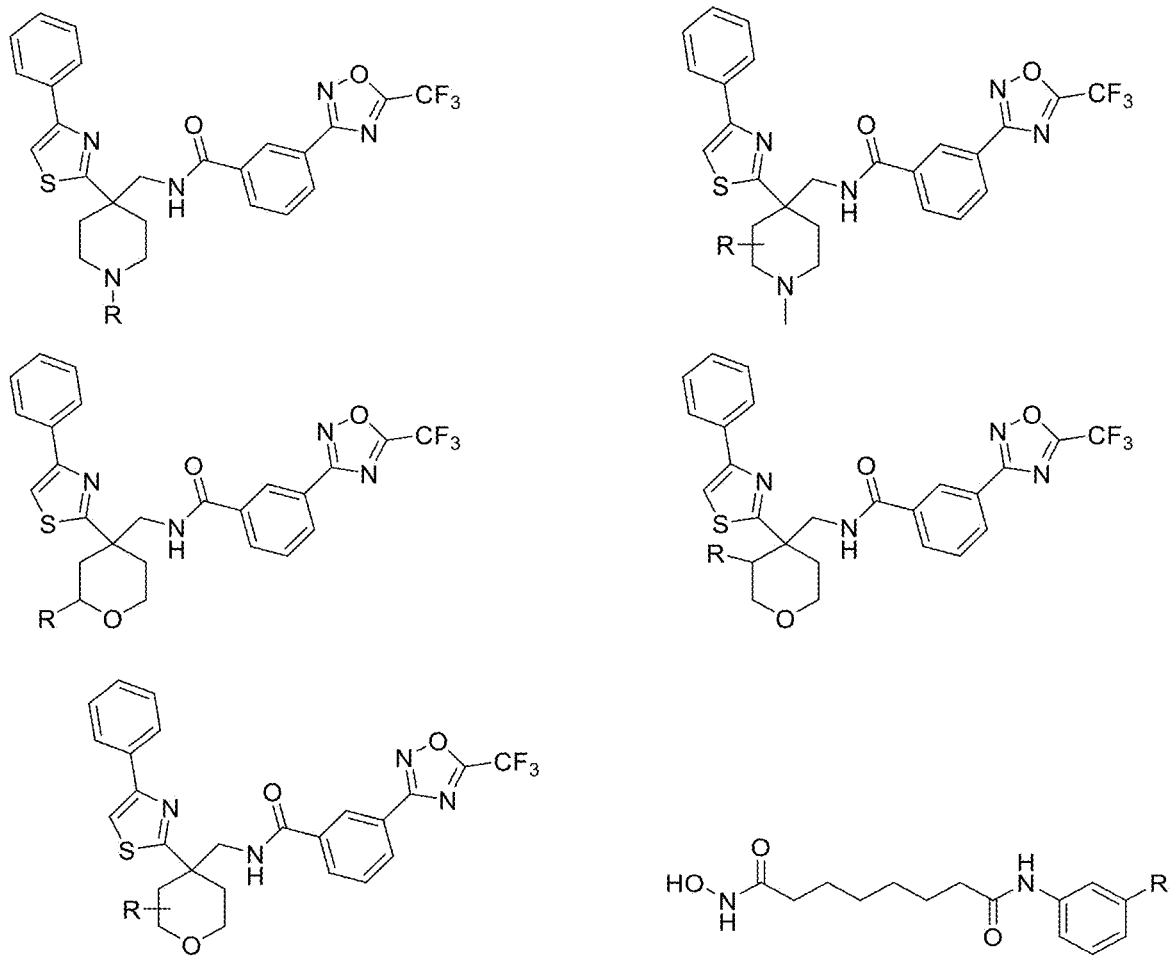
FIG. 3ZZZZ
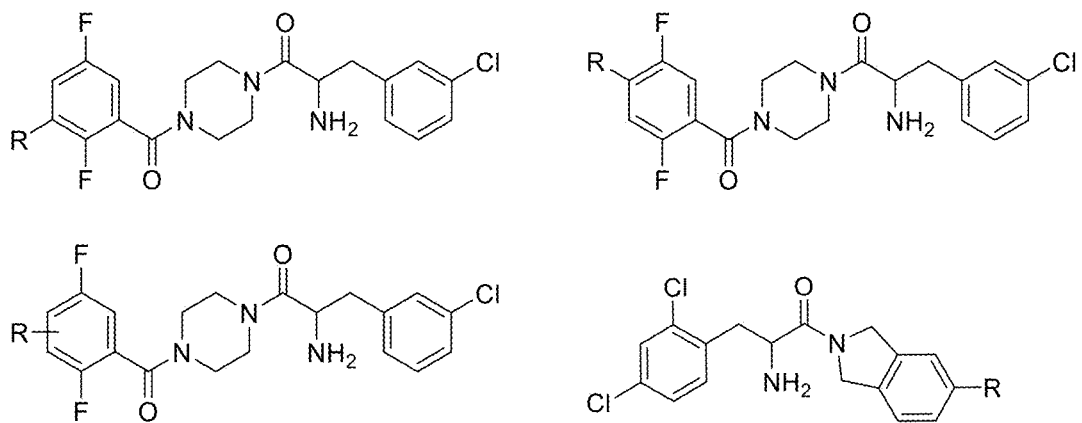

FIG. 3AAAAA
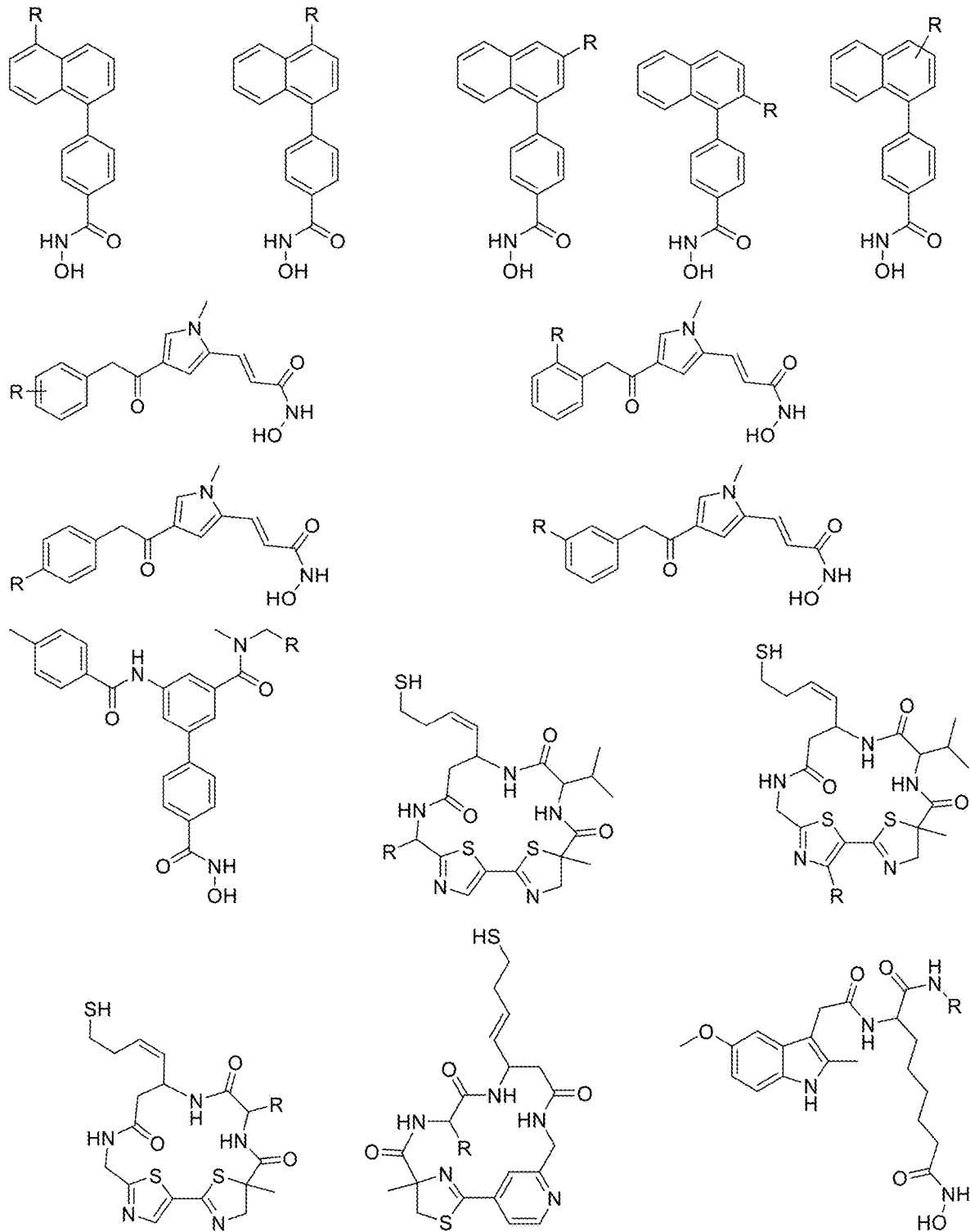

FIG. 3BBBBB
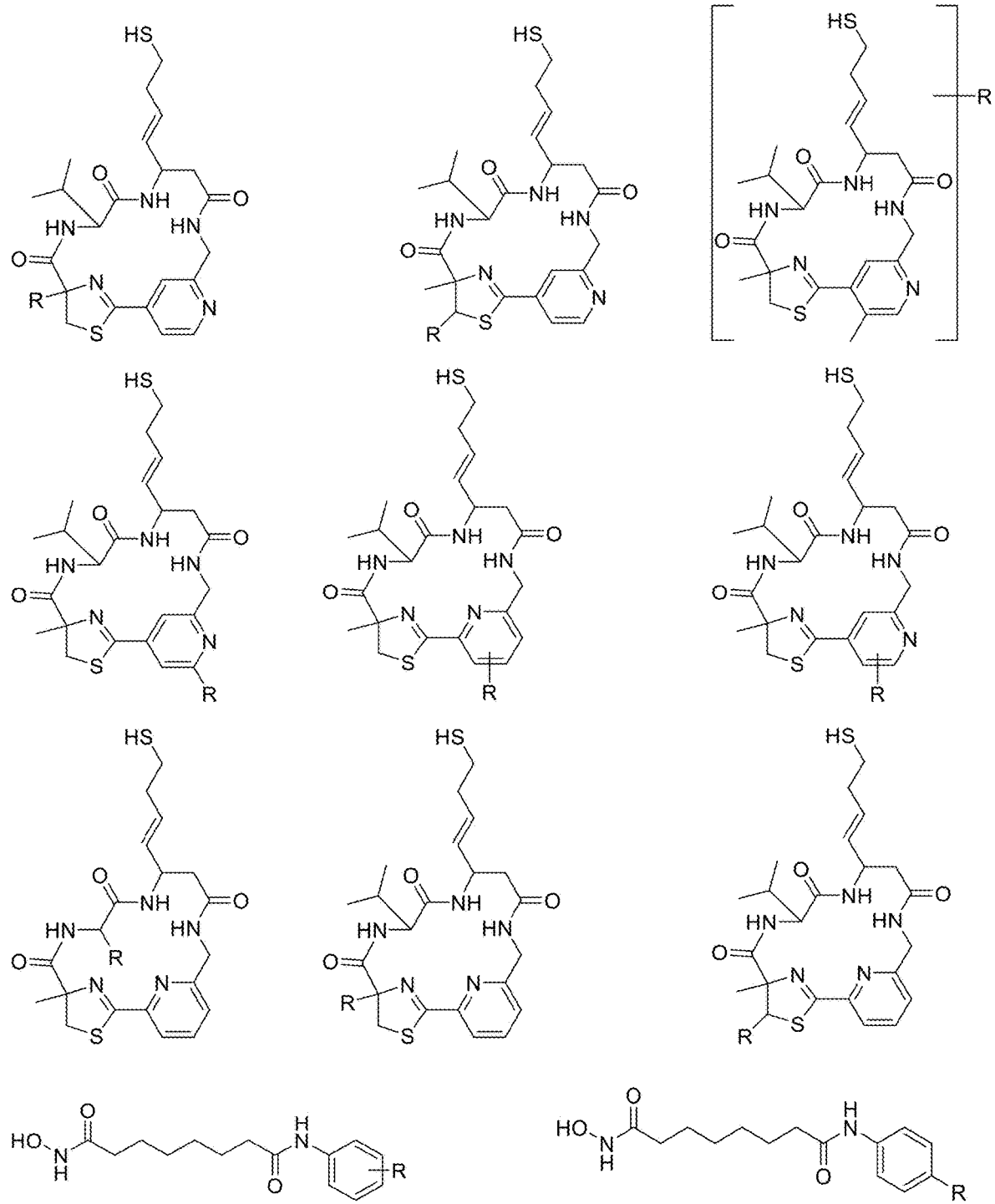

FIG. 3CCCCC
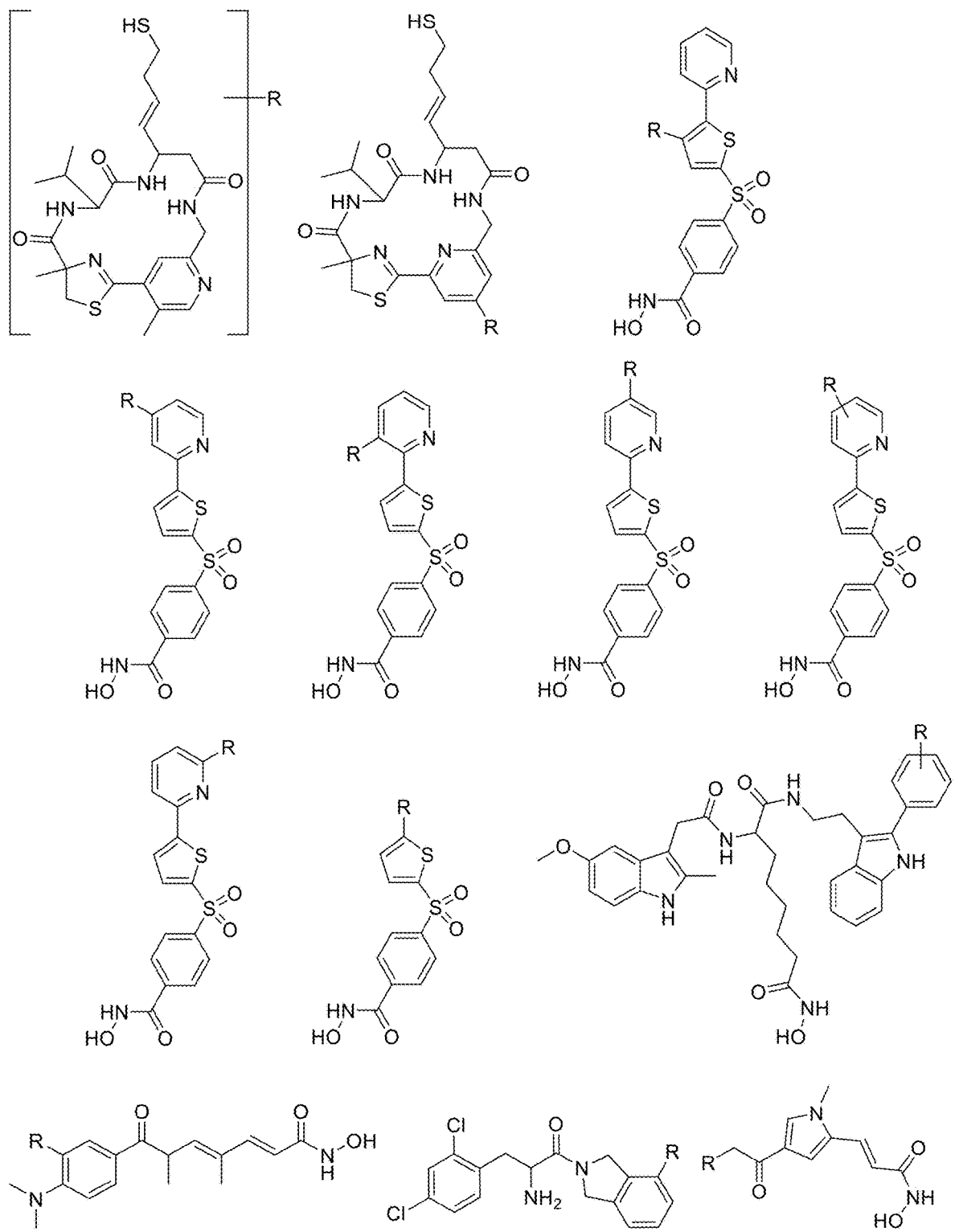

FIG. 3DDDDD
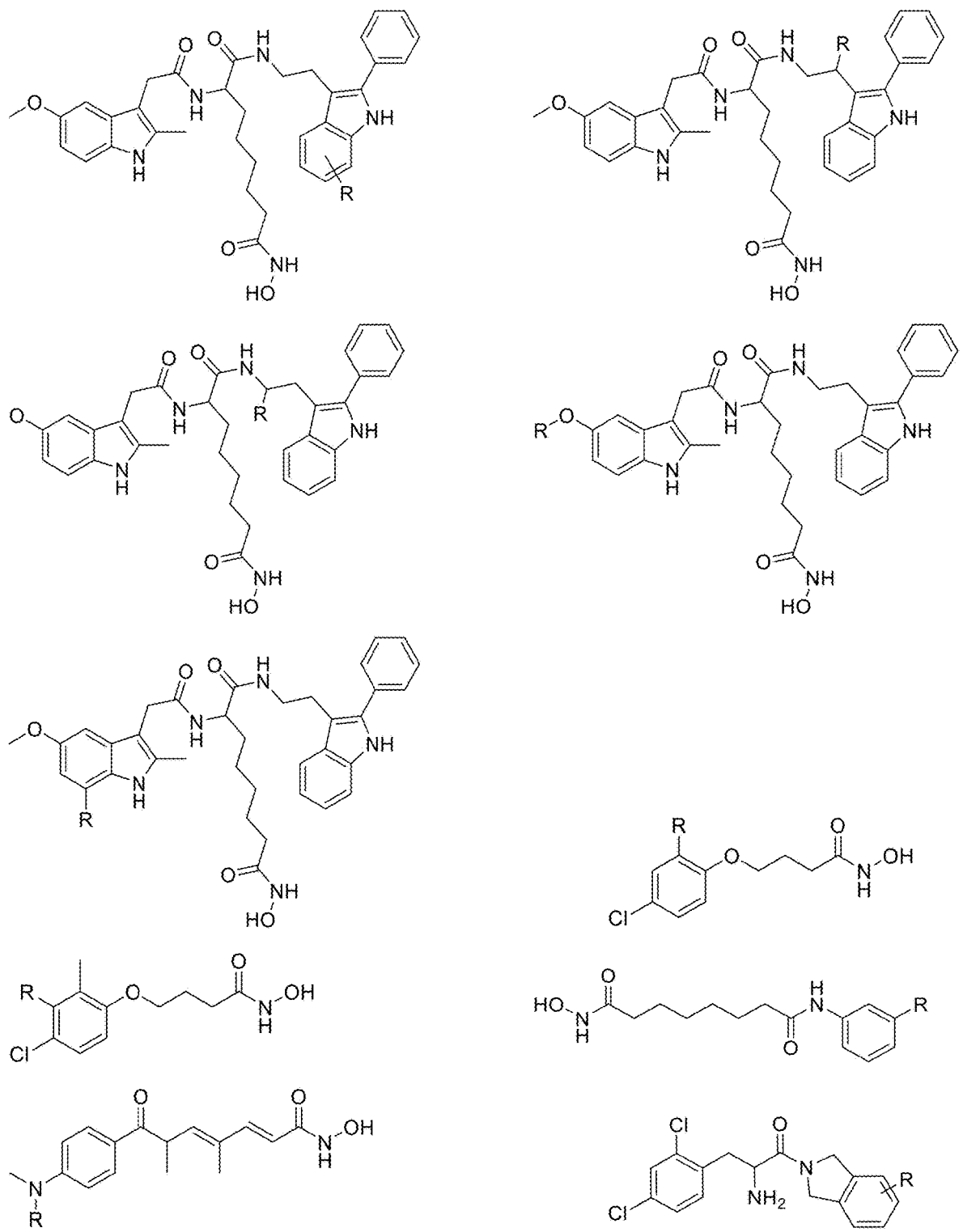

FIG. 3EEEEE
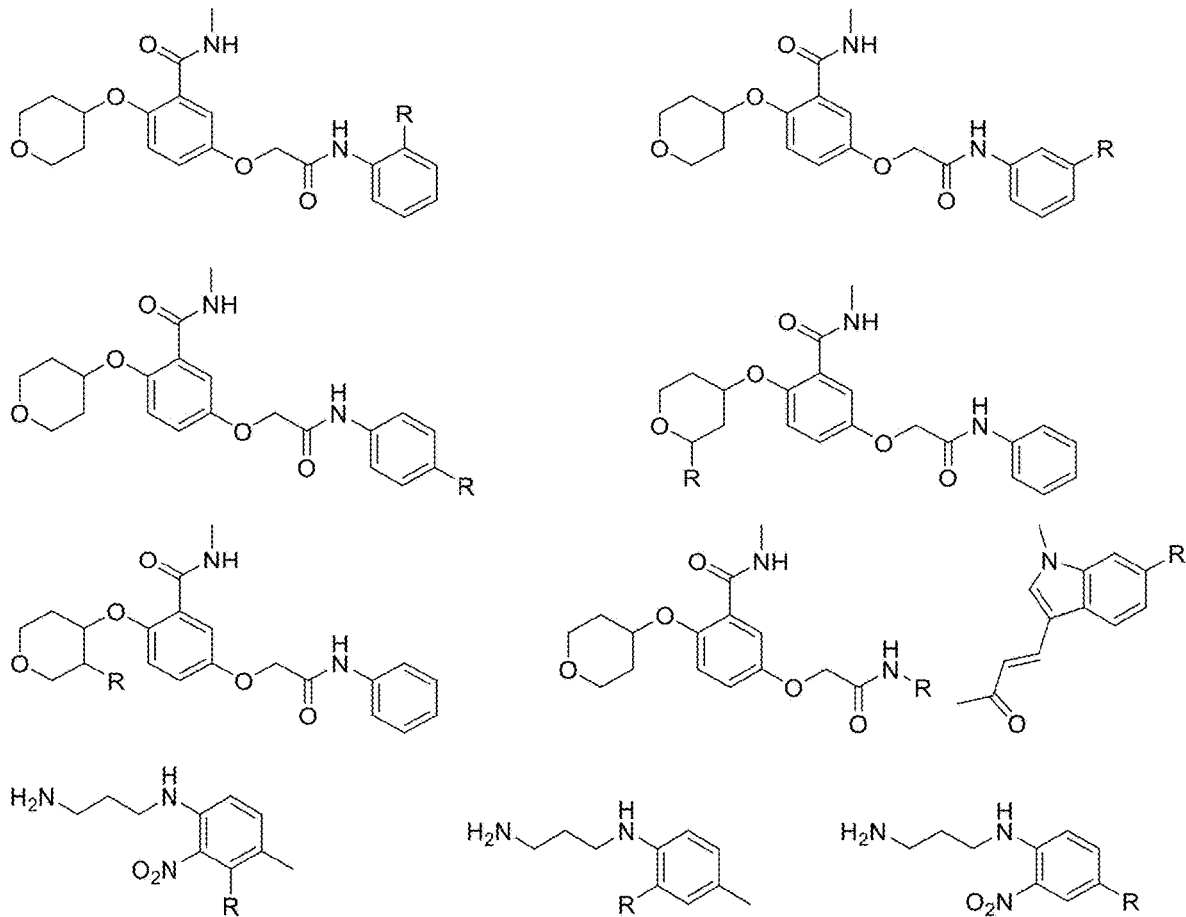
FIG. 3FFFFF
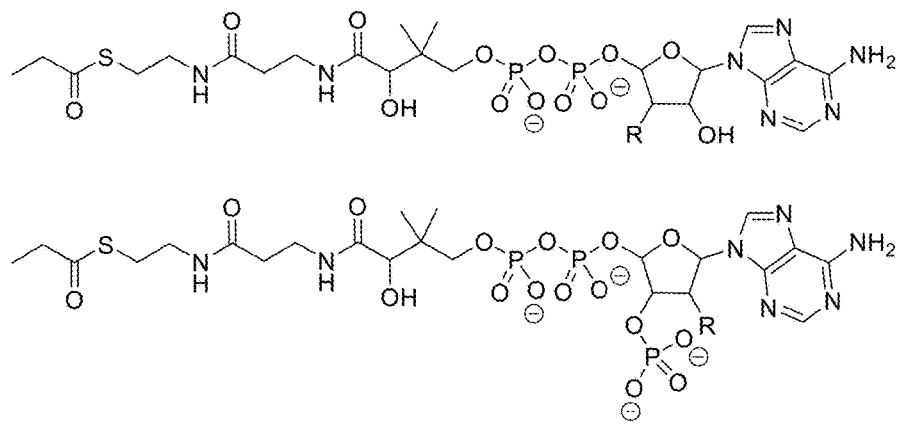

FIG. 3GGGGG
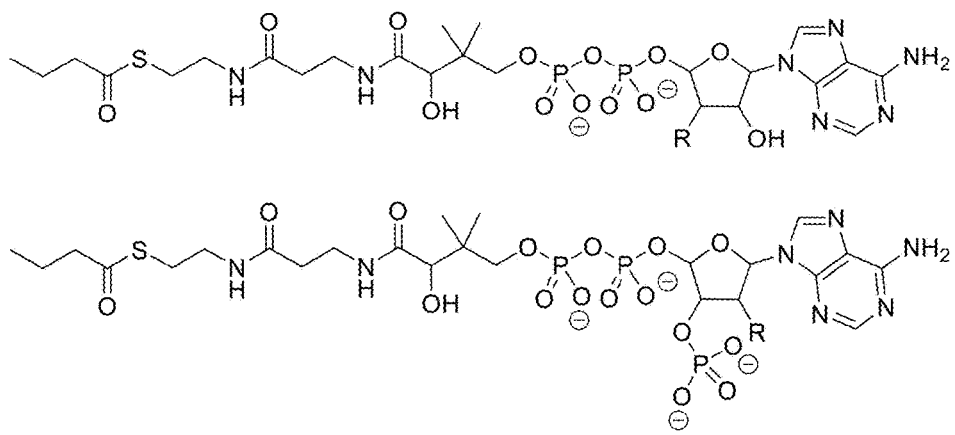
FIG. 3HHHHH
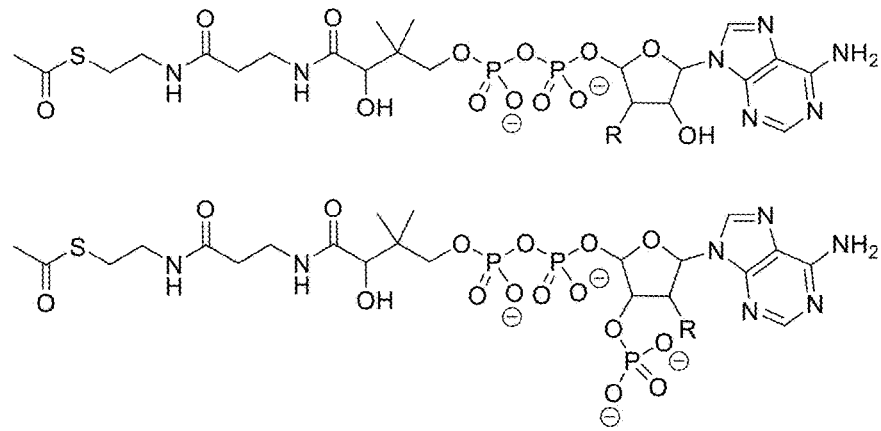
FIG. 3IIIII
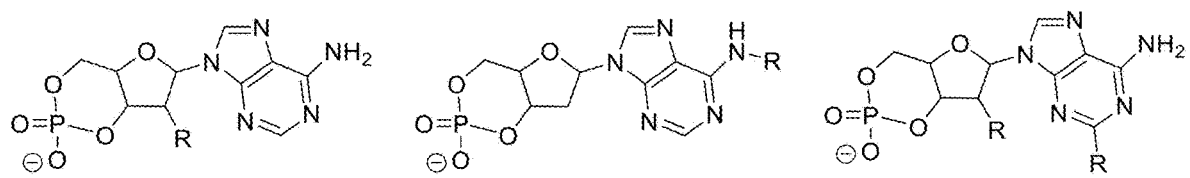

FIG. 3JJJJJ
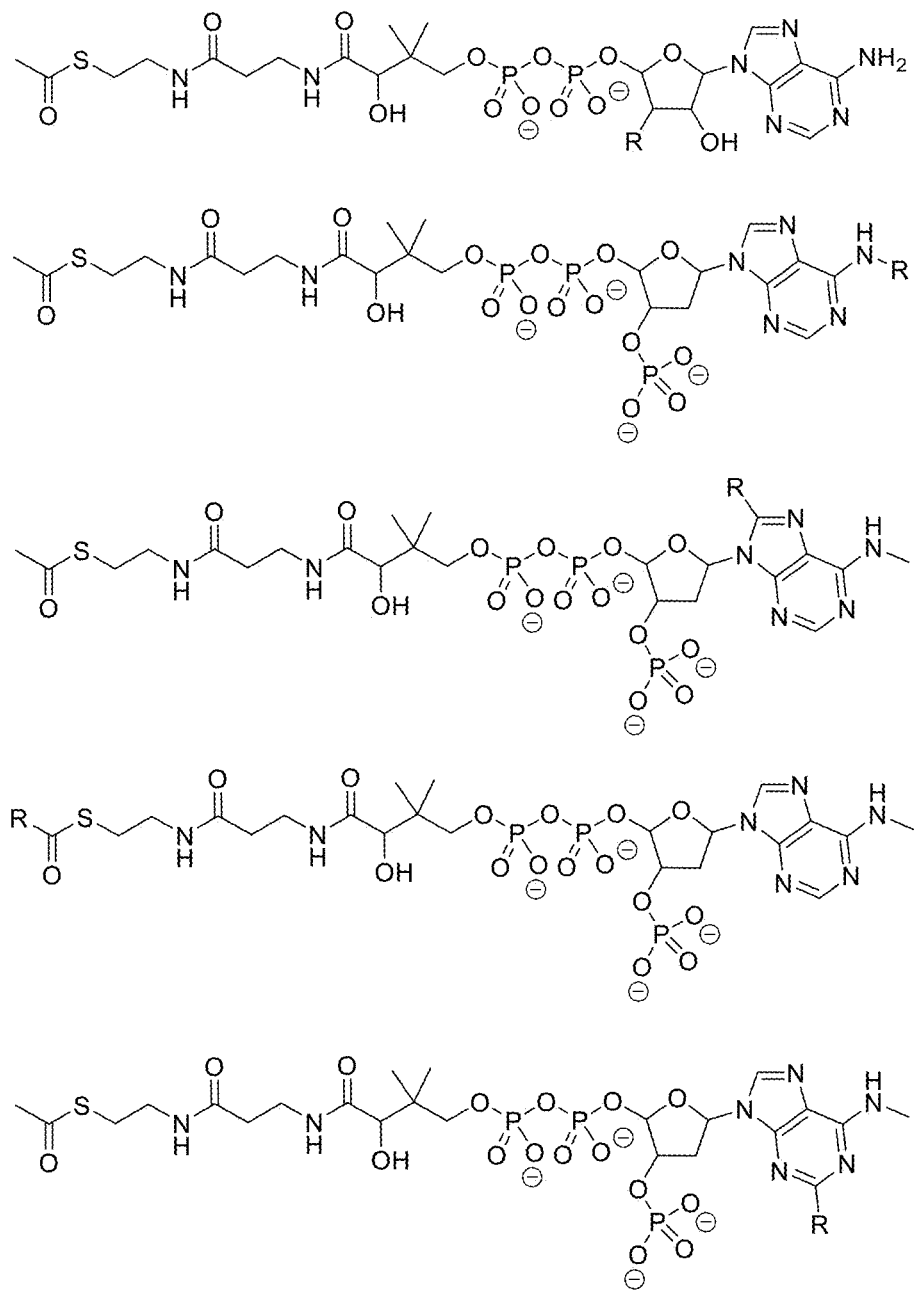

FIG. 3KKKKK
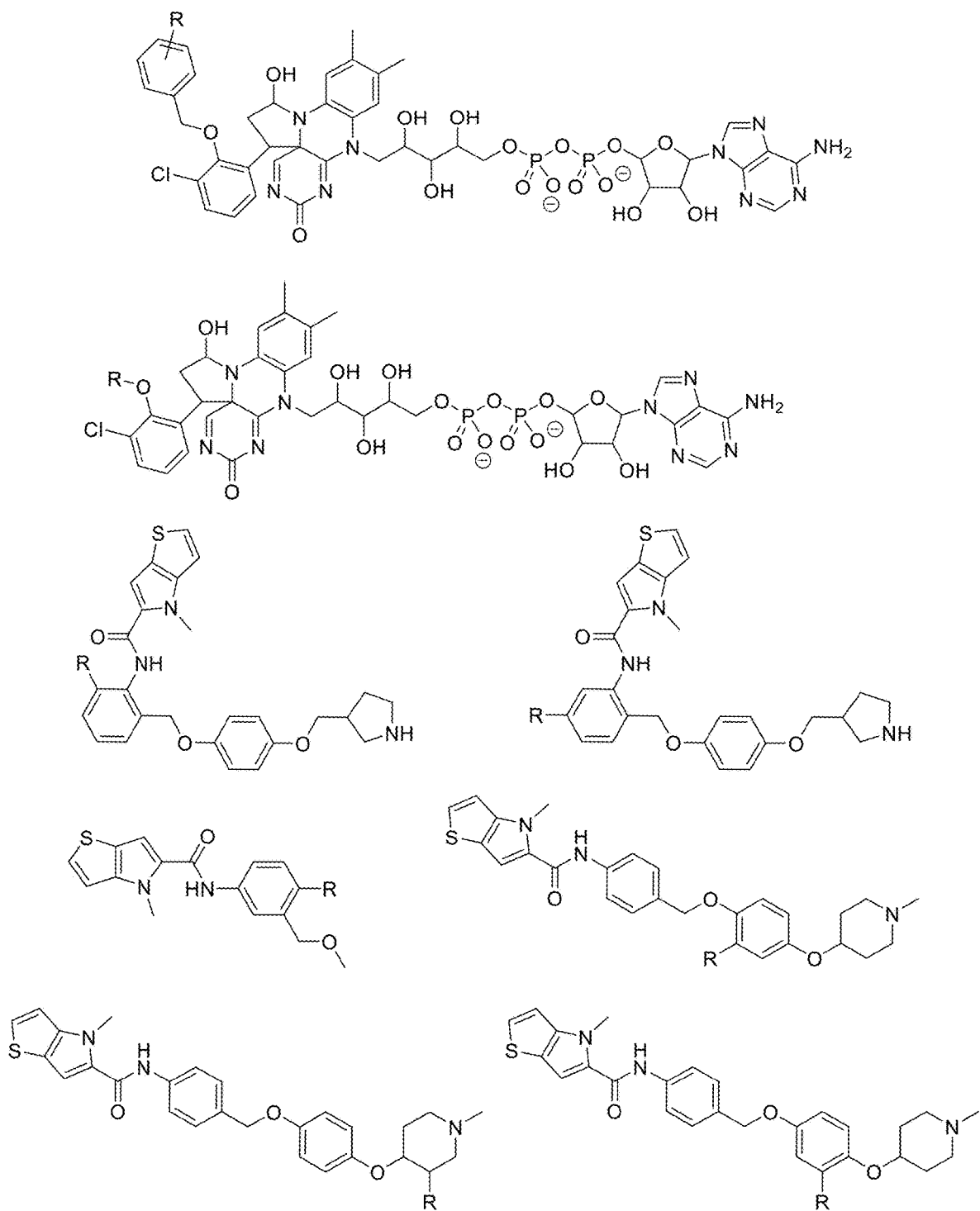

FIG. 3LLLLL
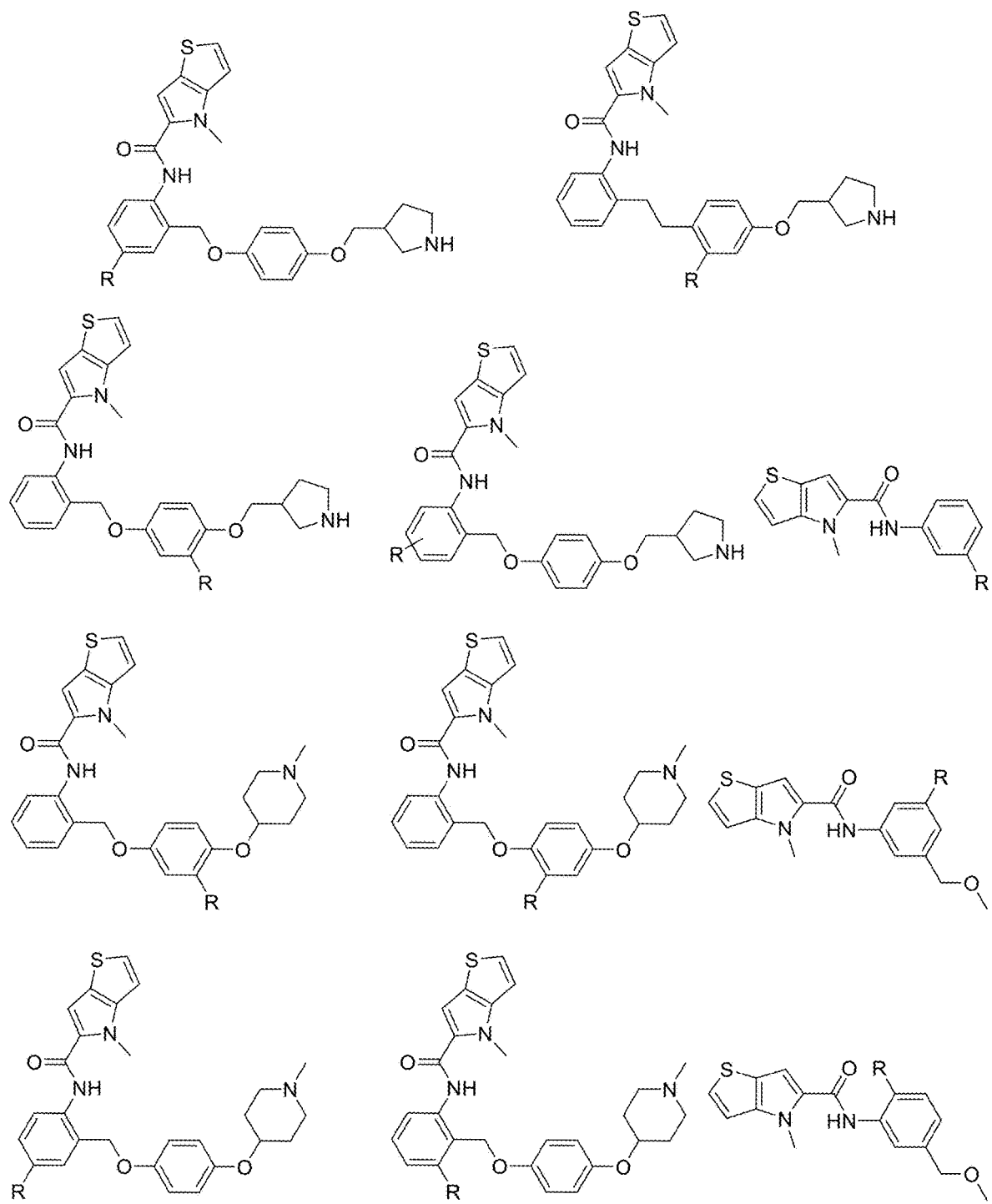

FIG. 3MMMMM
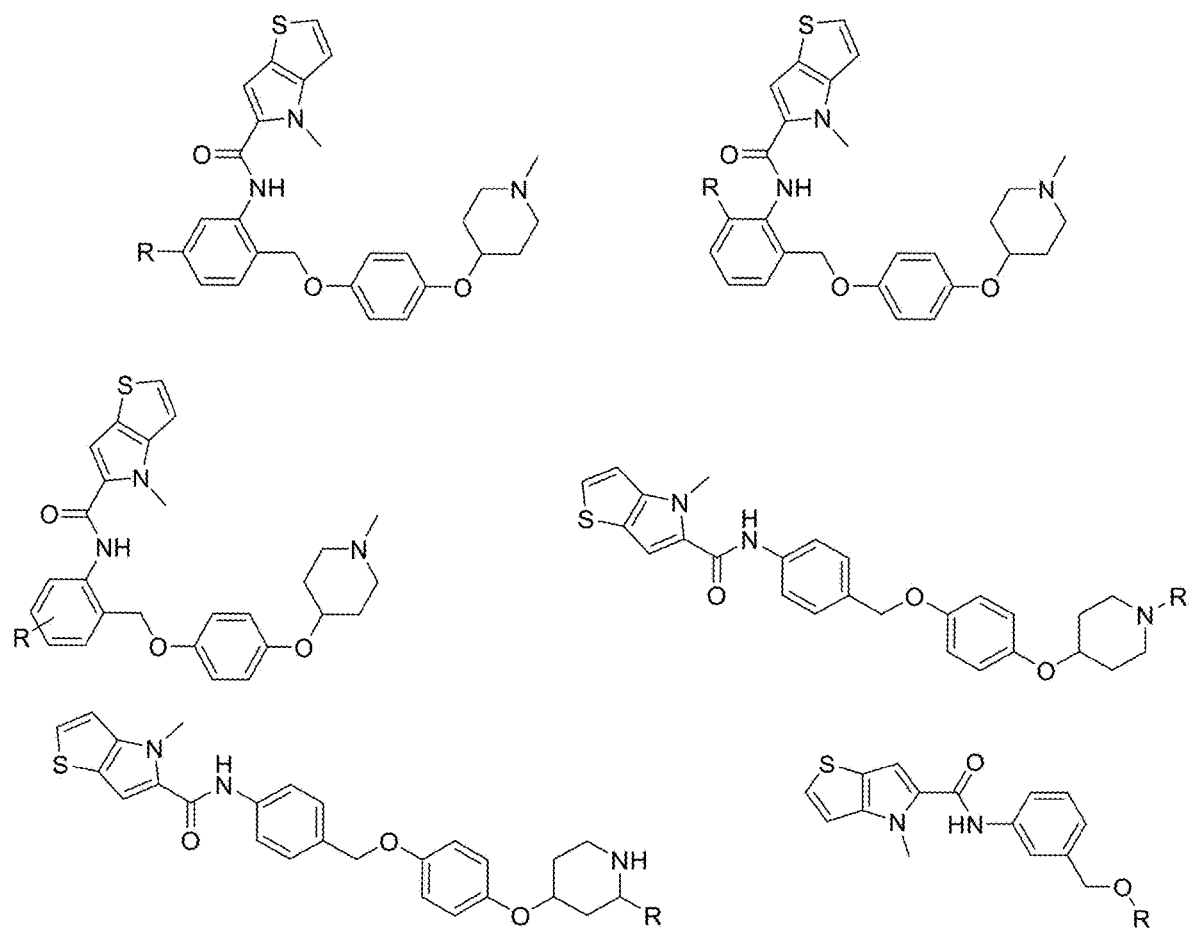
FIG. 3NNNNN
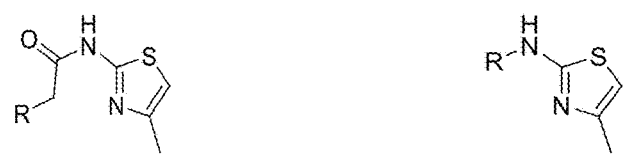

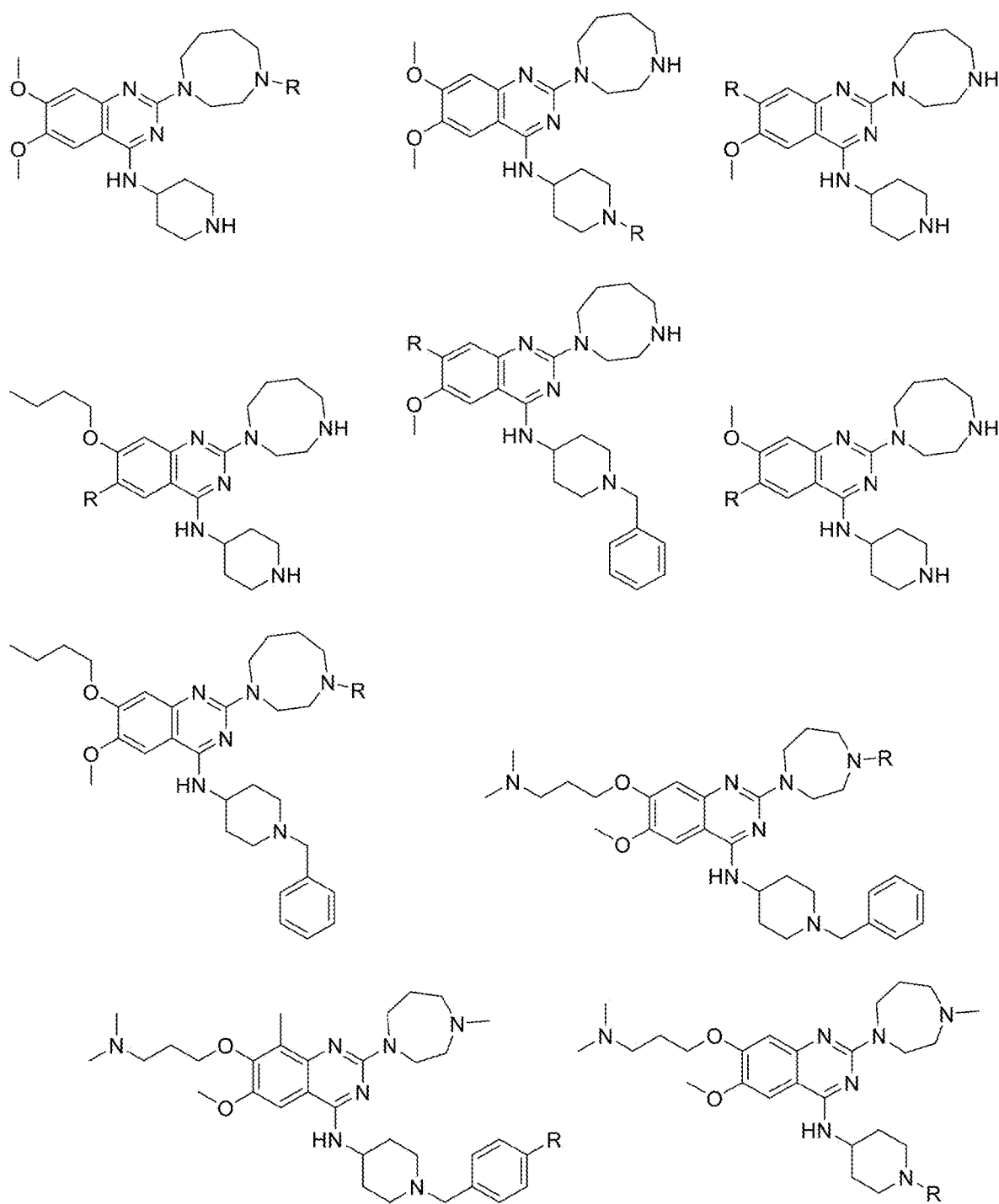
FIG. 300000

FIG. 3PPPPP
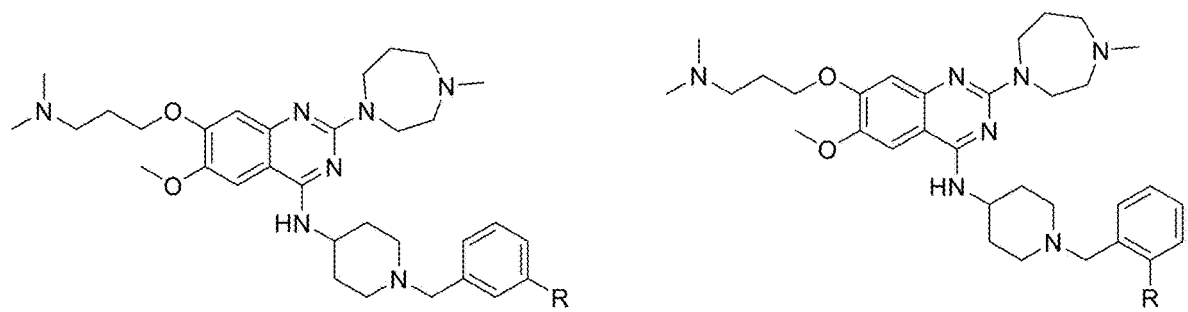
FIG. 3QQQQQ
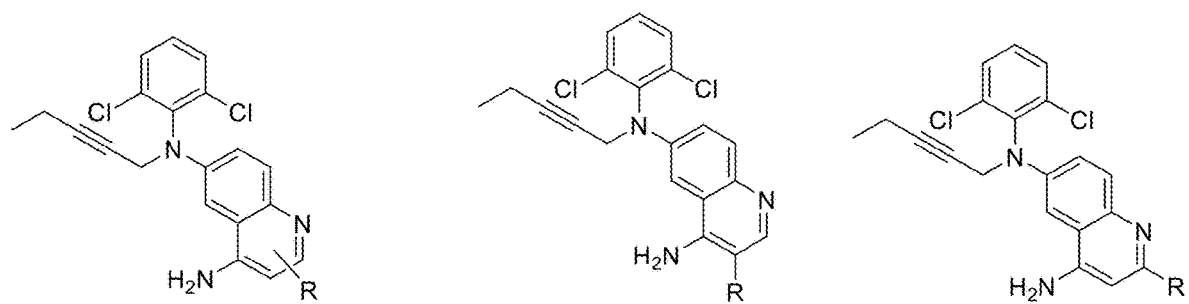
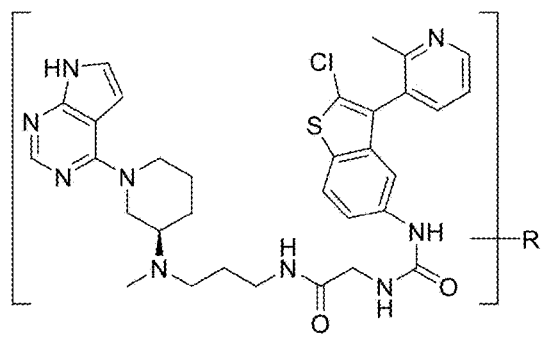

FIG. 3RRRRR

FIG. 3SSSSS
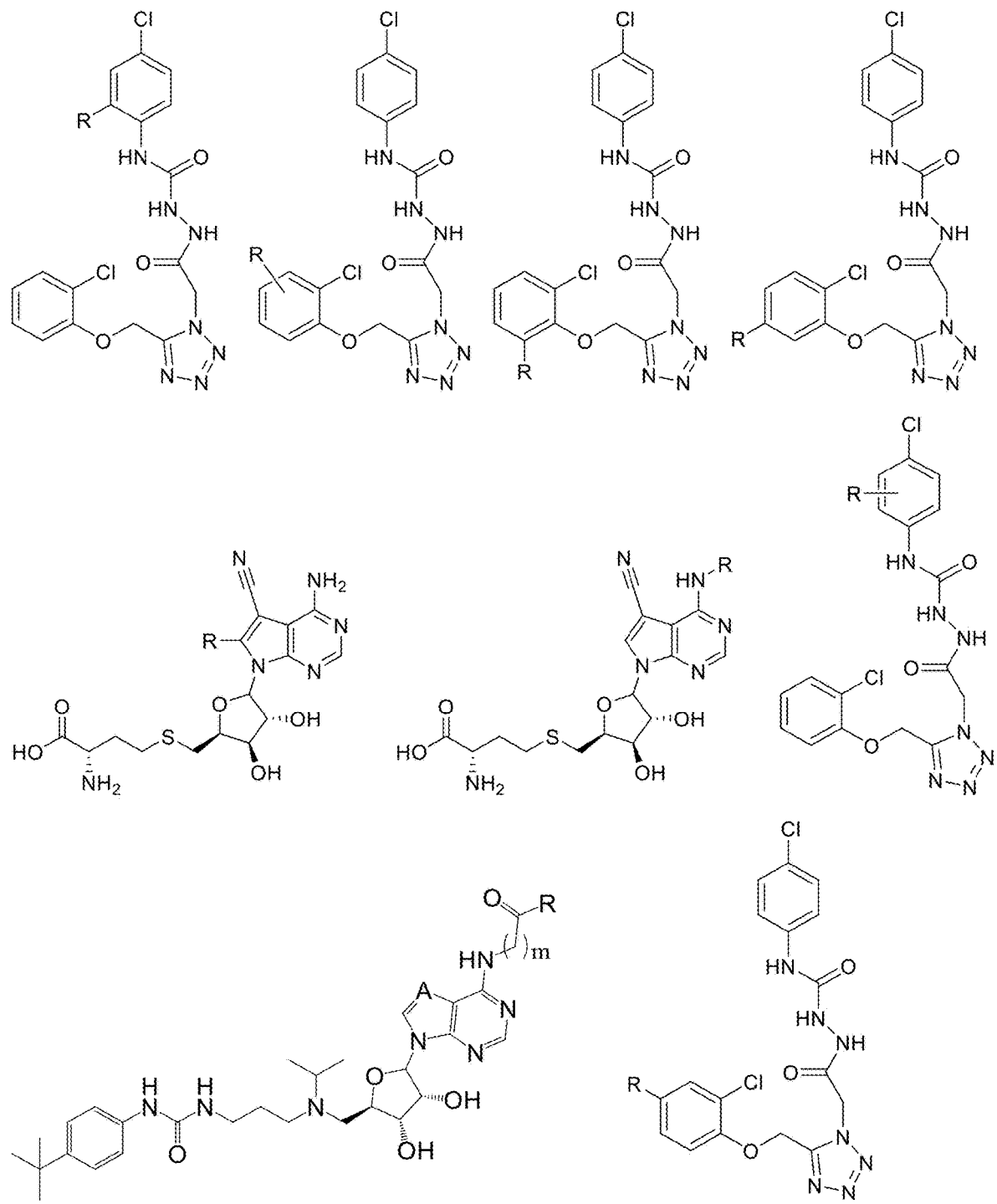

FIG. 3TTTTT
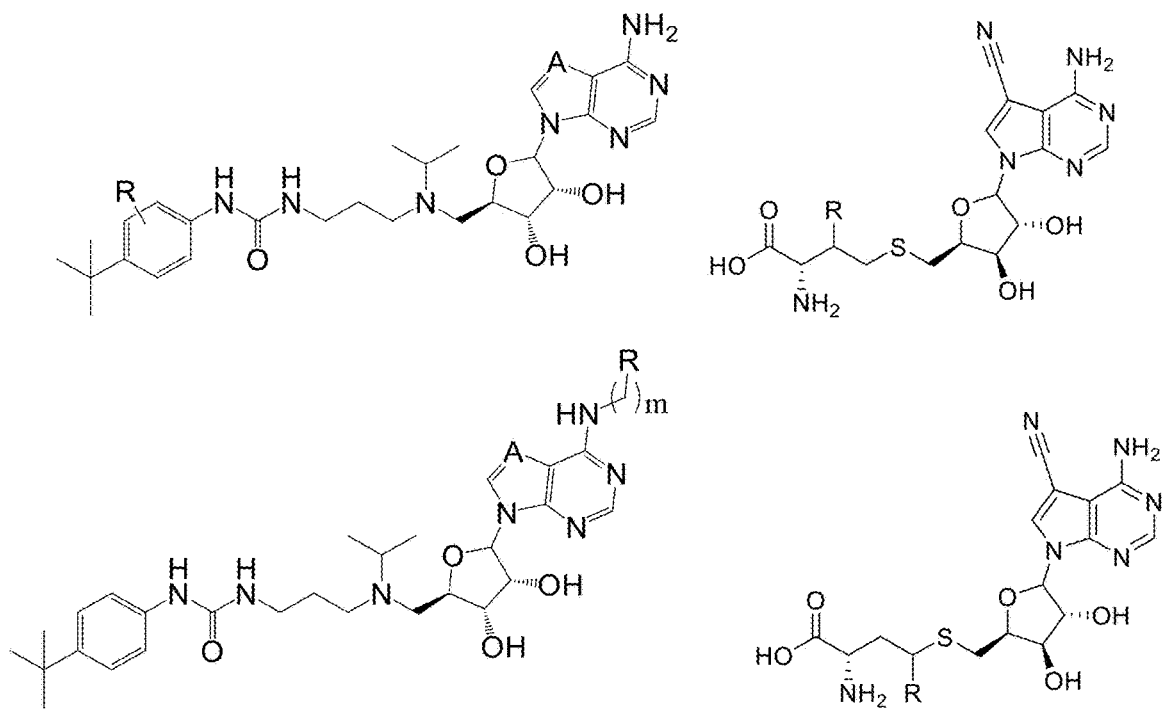
FIG. 3UUUUU
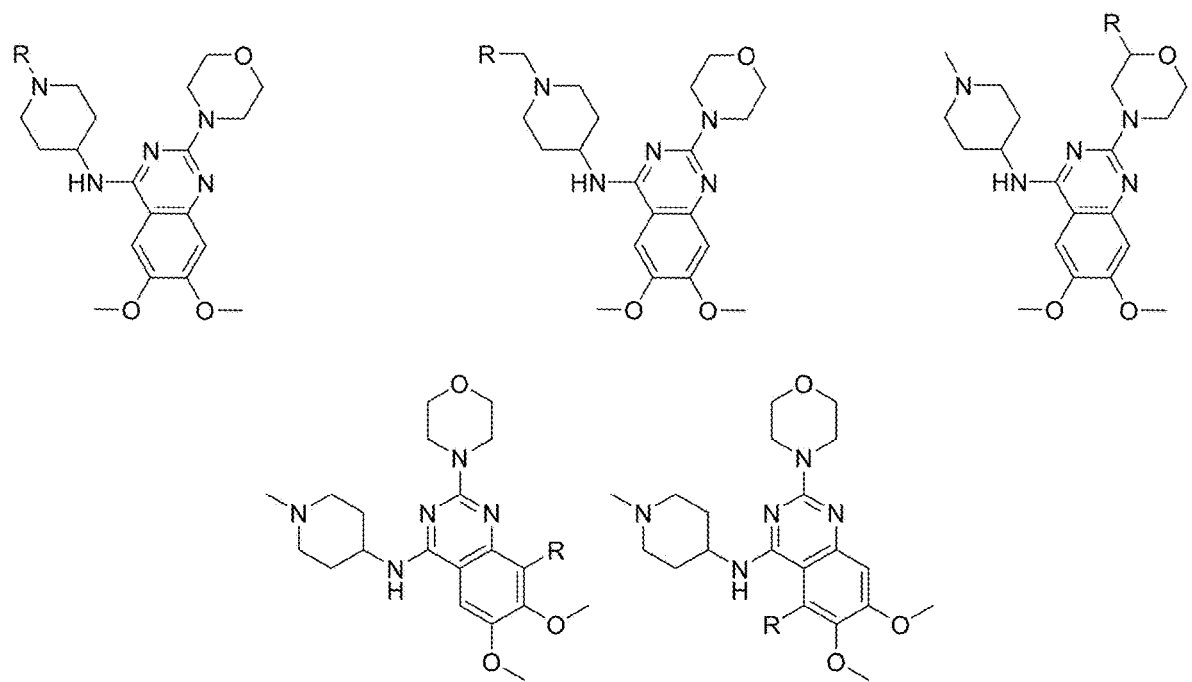

FIG. 3VVVVV
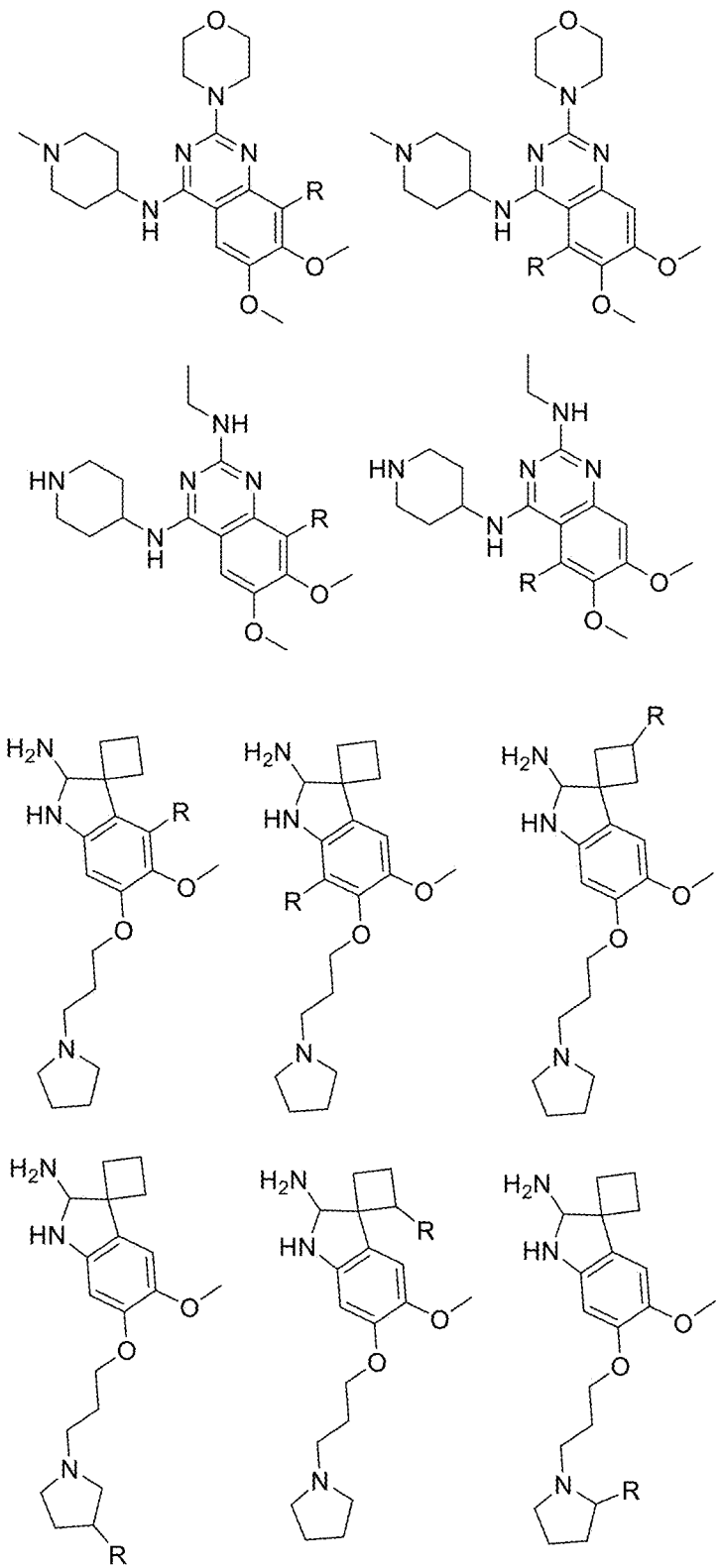

FIG. 3WWWWW
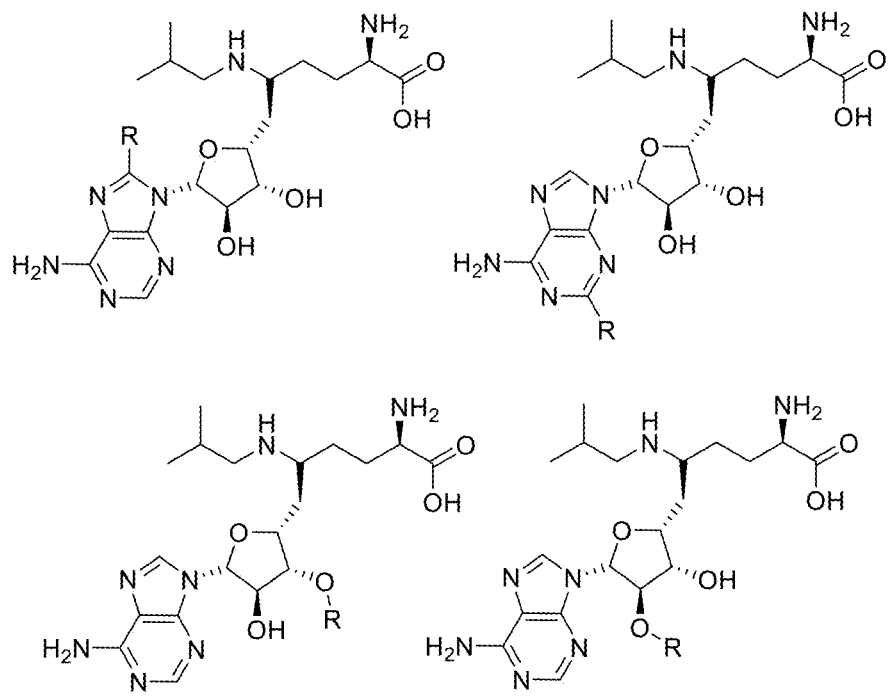
FIG. 3XXXXX
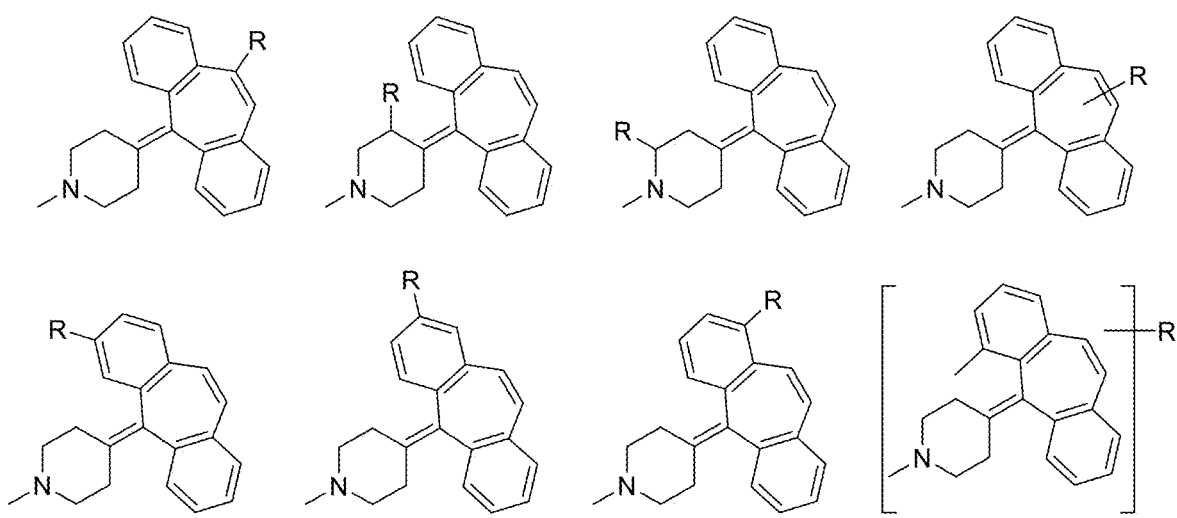

FIG. 3YYYYY
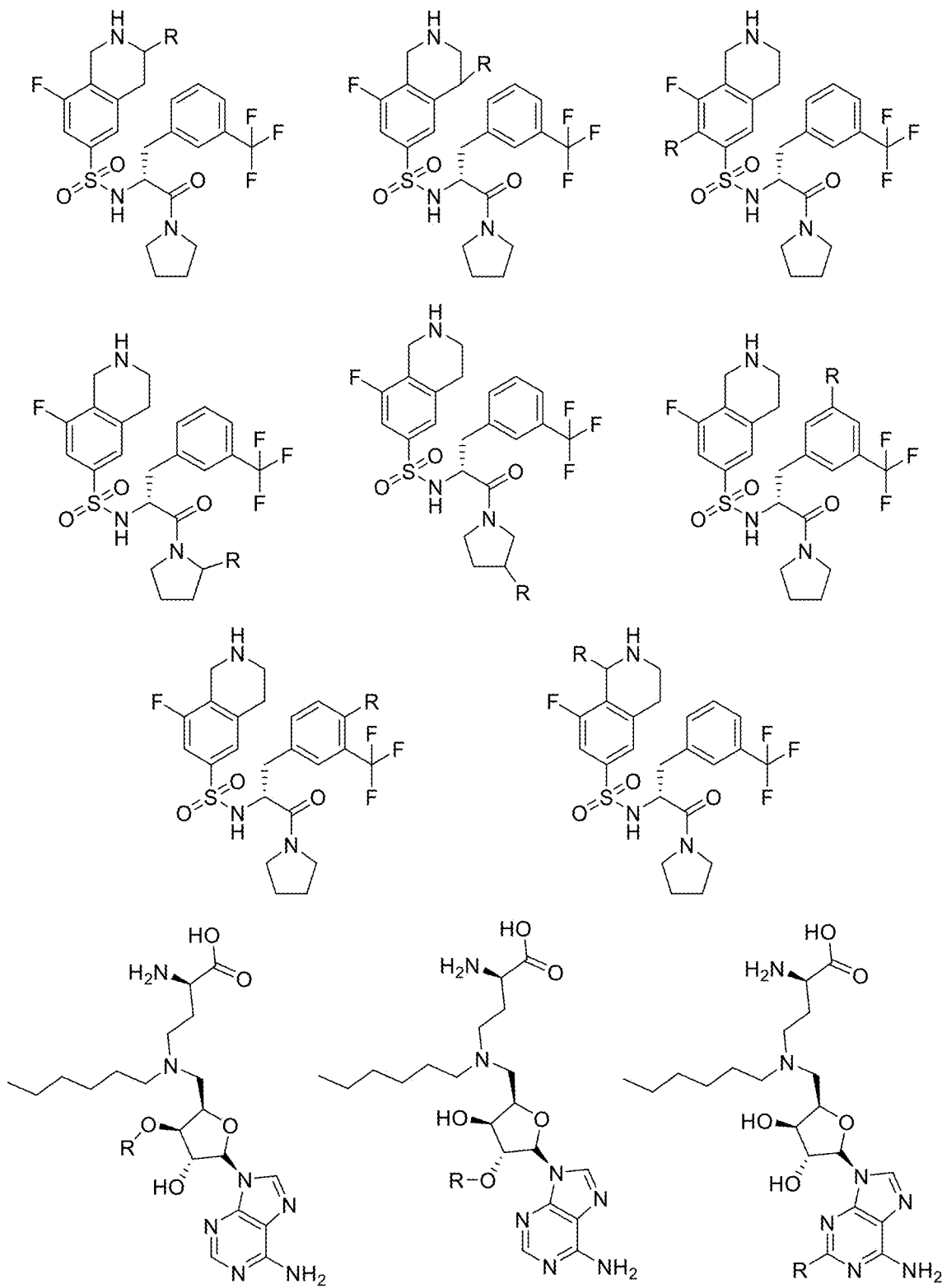

FIG. 3ZZZZZ
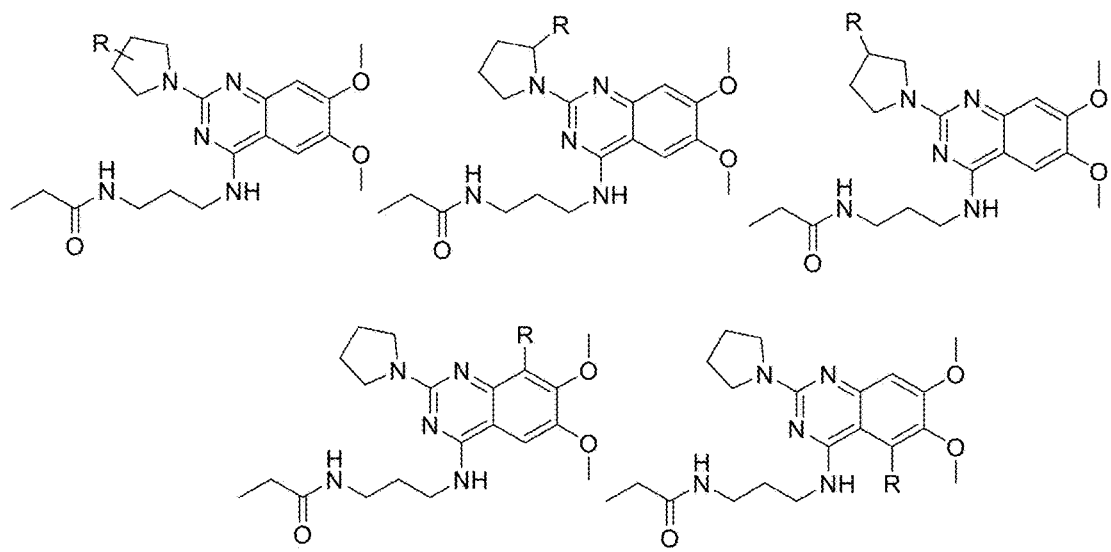
FIG. 4A
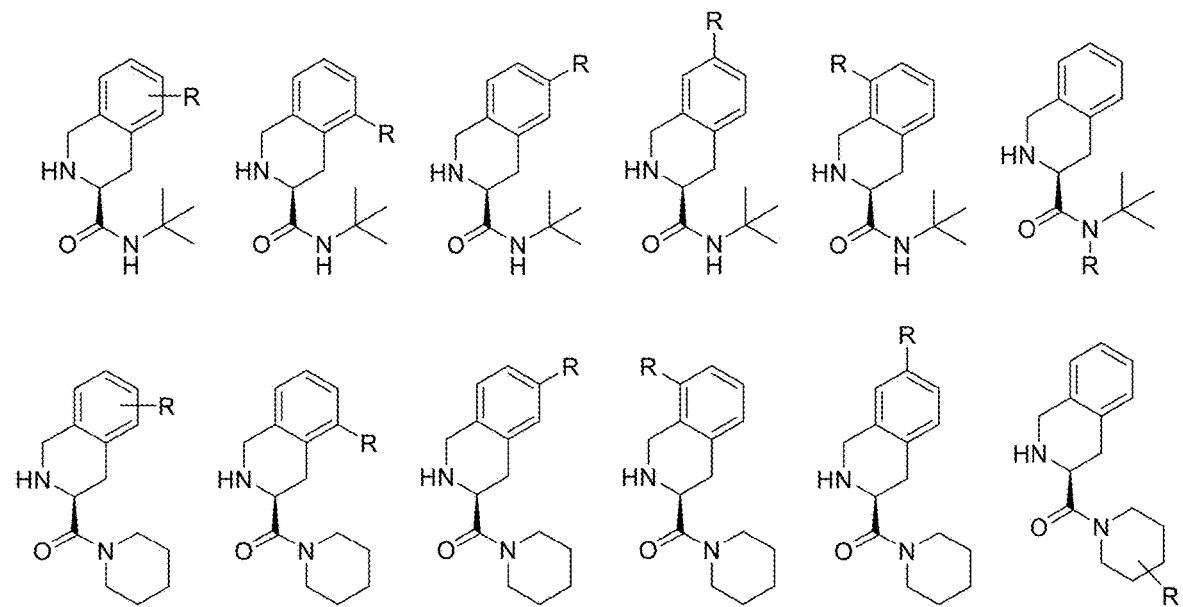

FIG. 5L
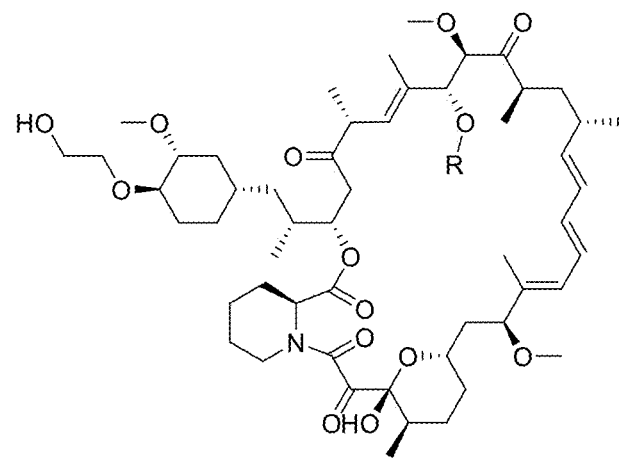
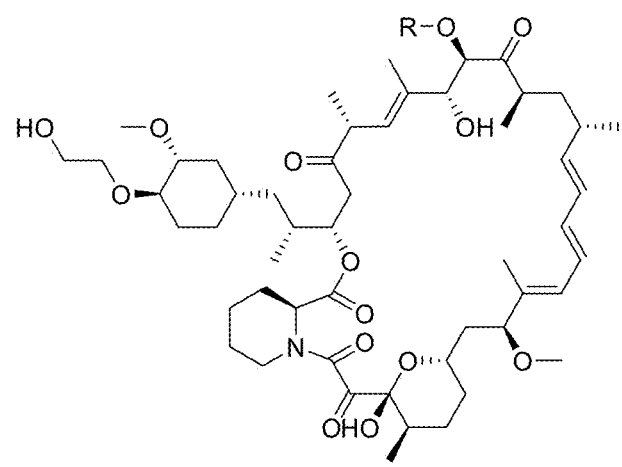
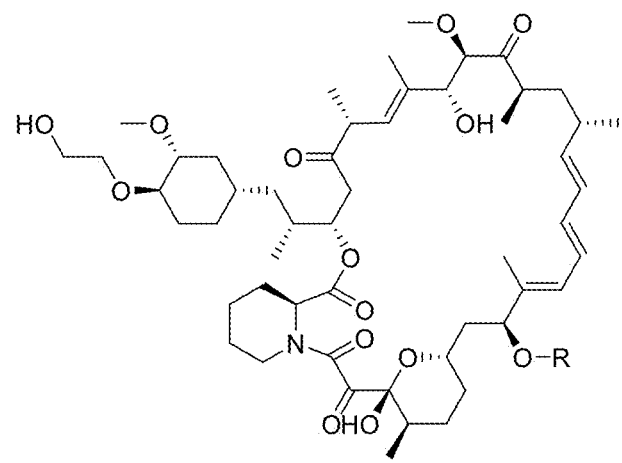

FIG. 5M
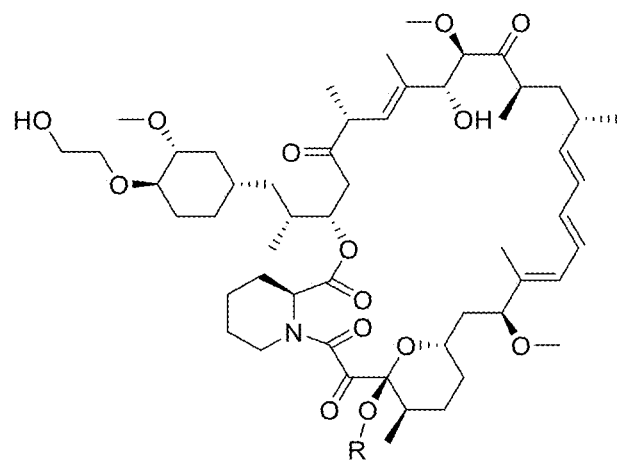
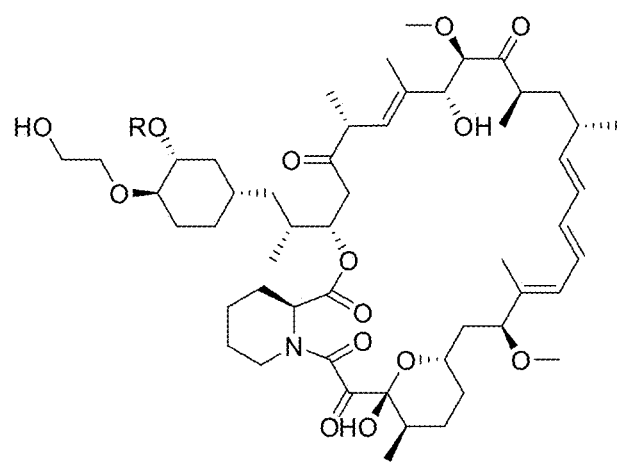
FIG. 5N
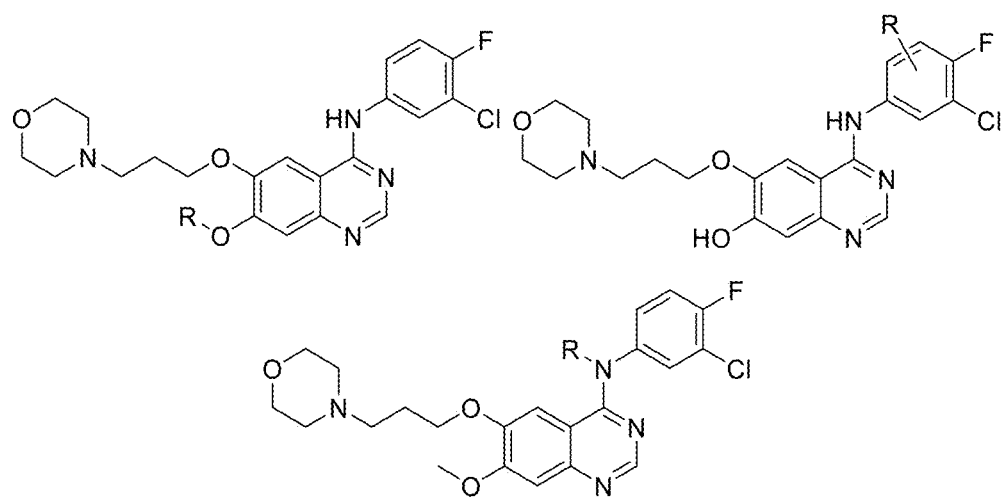

FIG. 5JJ
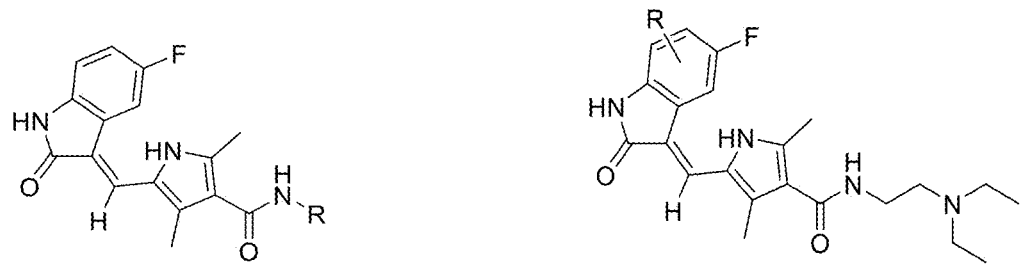
FIG. 5KK
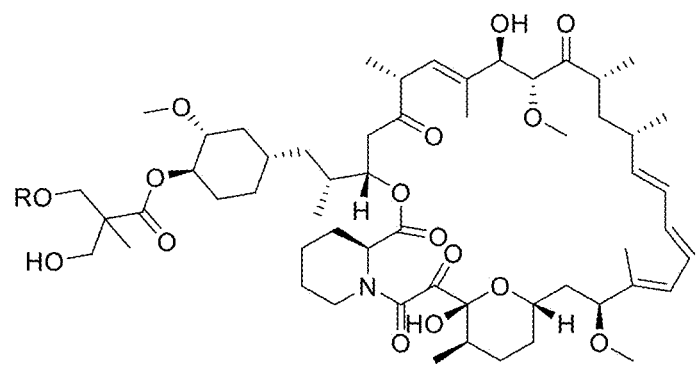
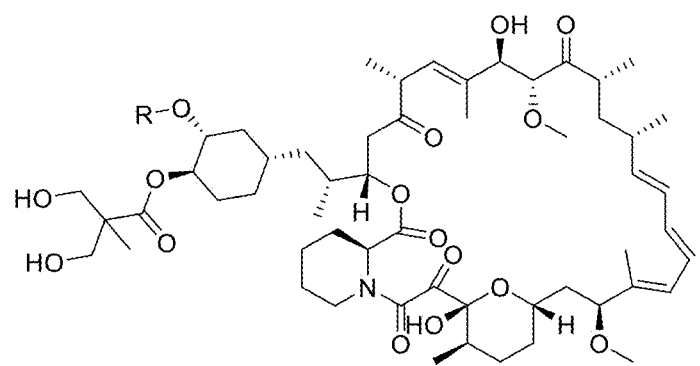

FIG. 6N
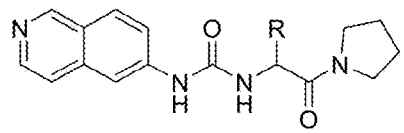 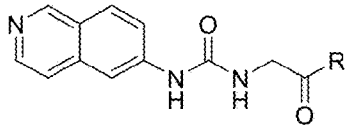
FIG. 6O
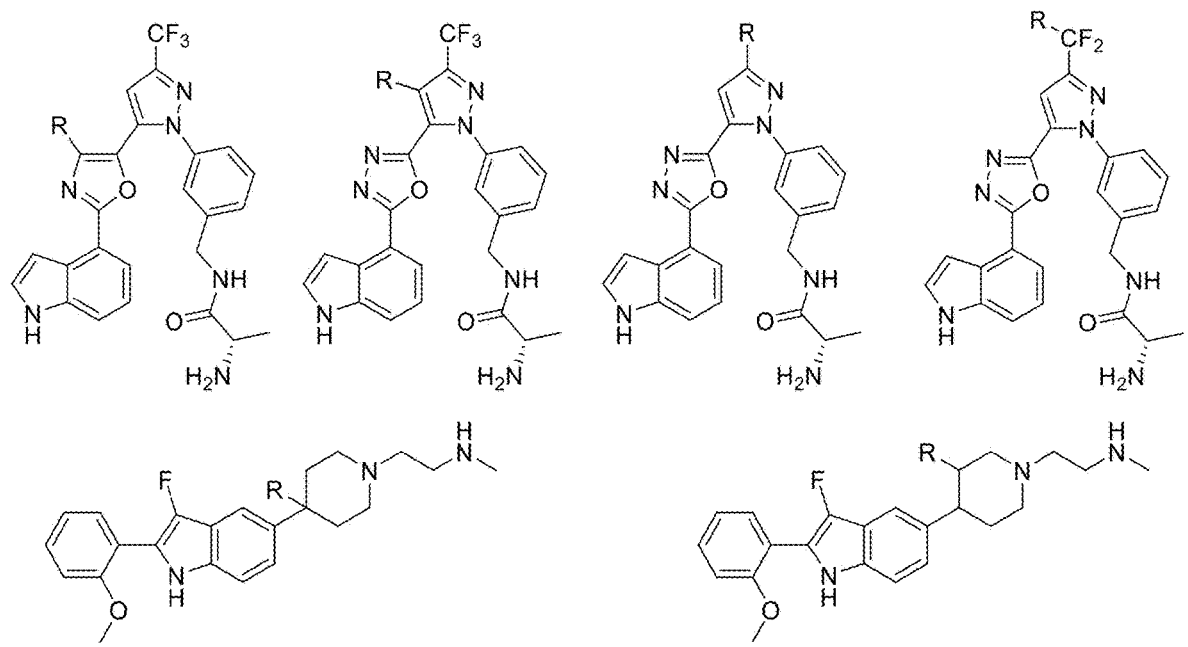
FIG. 6P
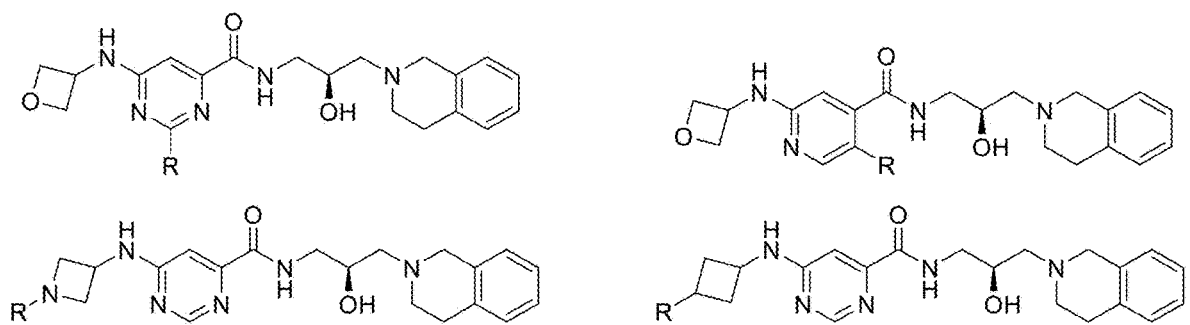

X=H, F, Cl, Br, Me, CF$_3$O

FIG. 8S
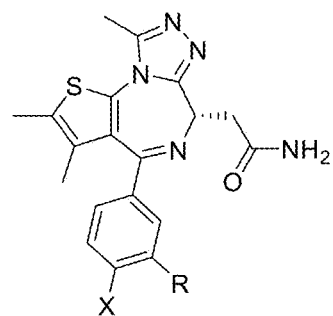
X=H, F, Cl, Br, Me, CF₃O
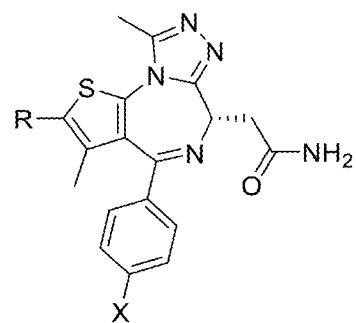
X=H, F, Cl, Br, Me, CF₃O
FIG. 8T
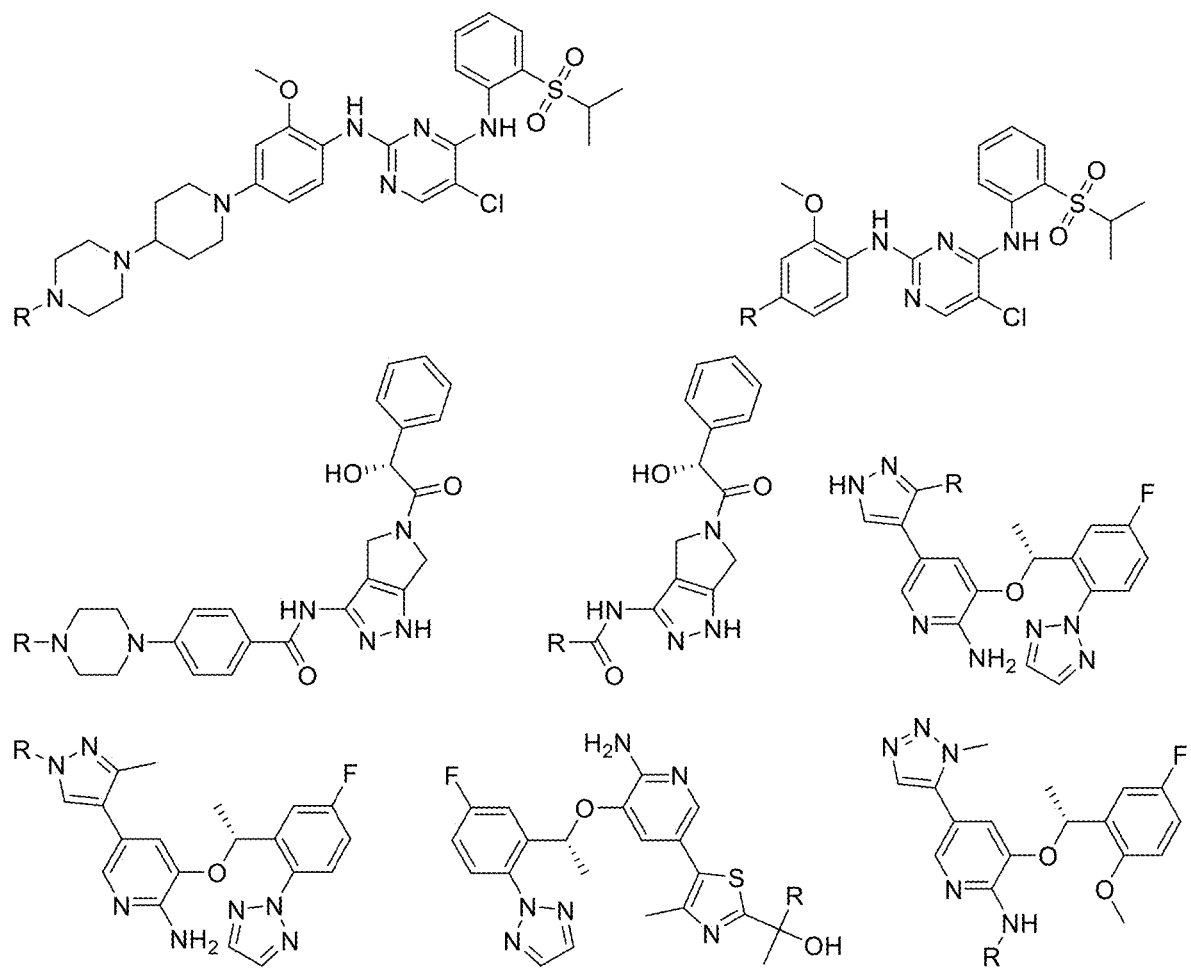

FIG. 8AAA
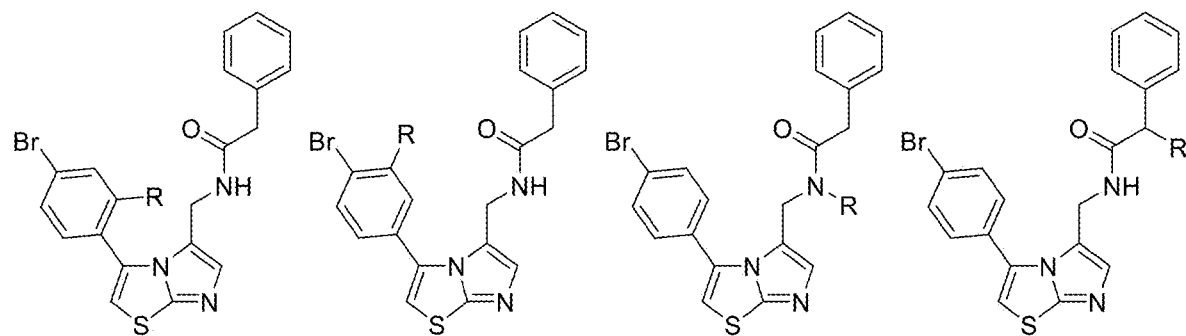
FIG. 8BBB
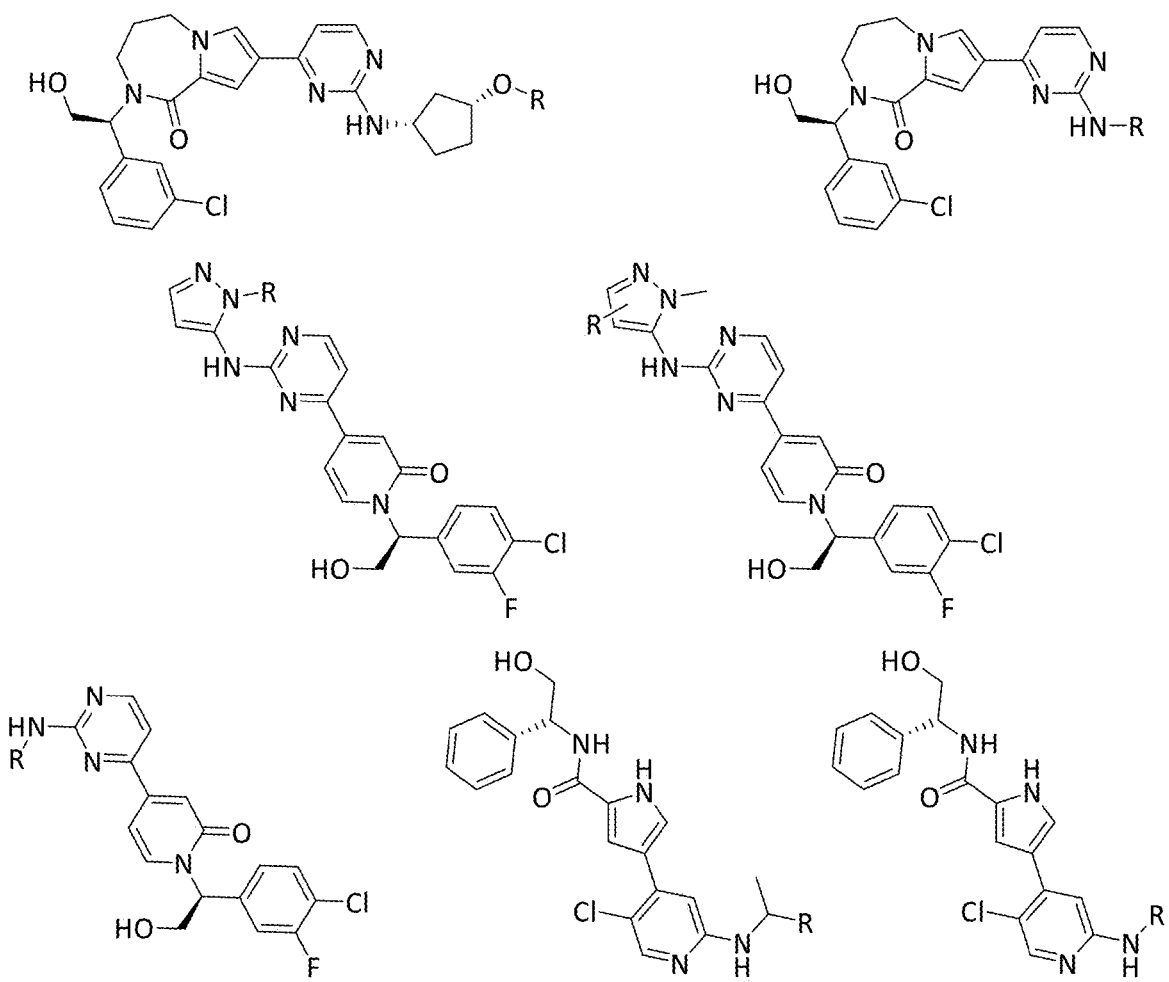

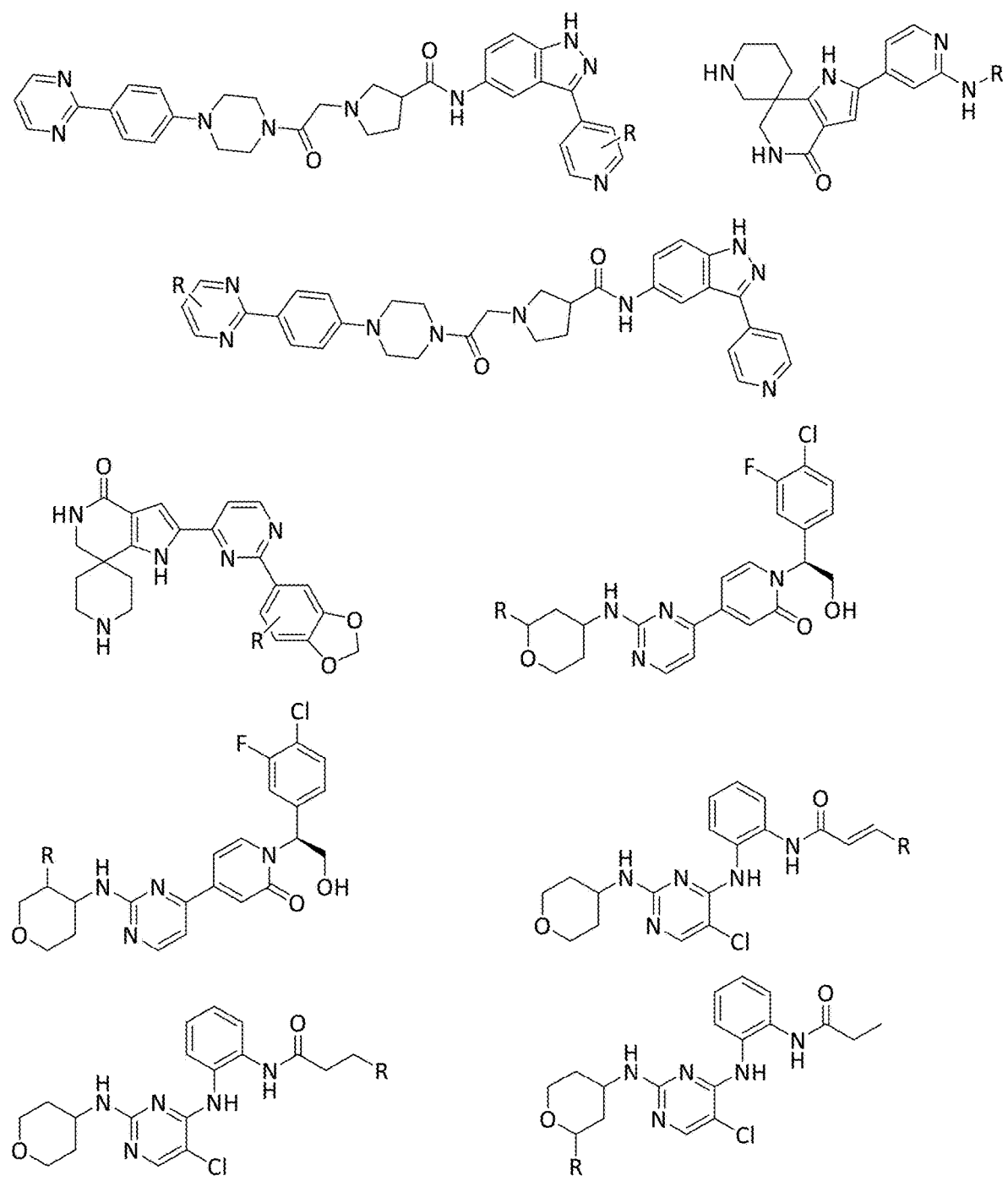
FIG. 8CCC

FIG. 8DDD
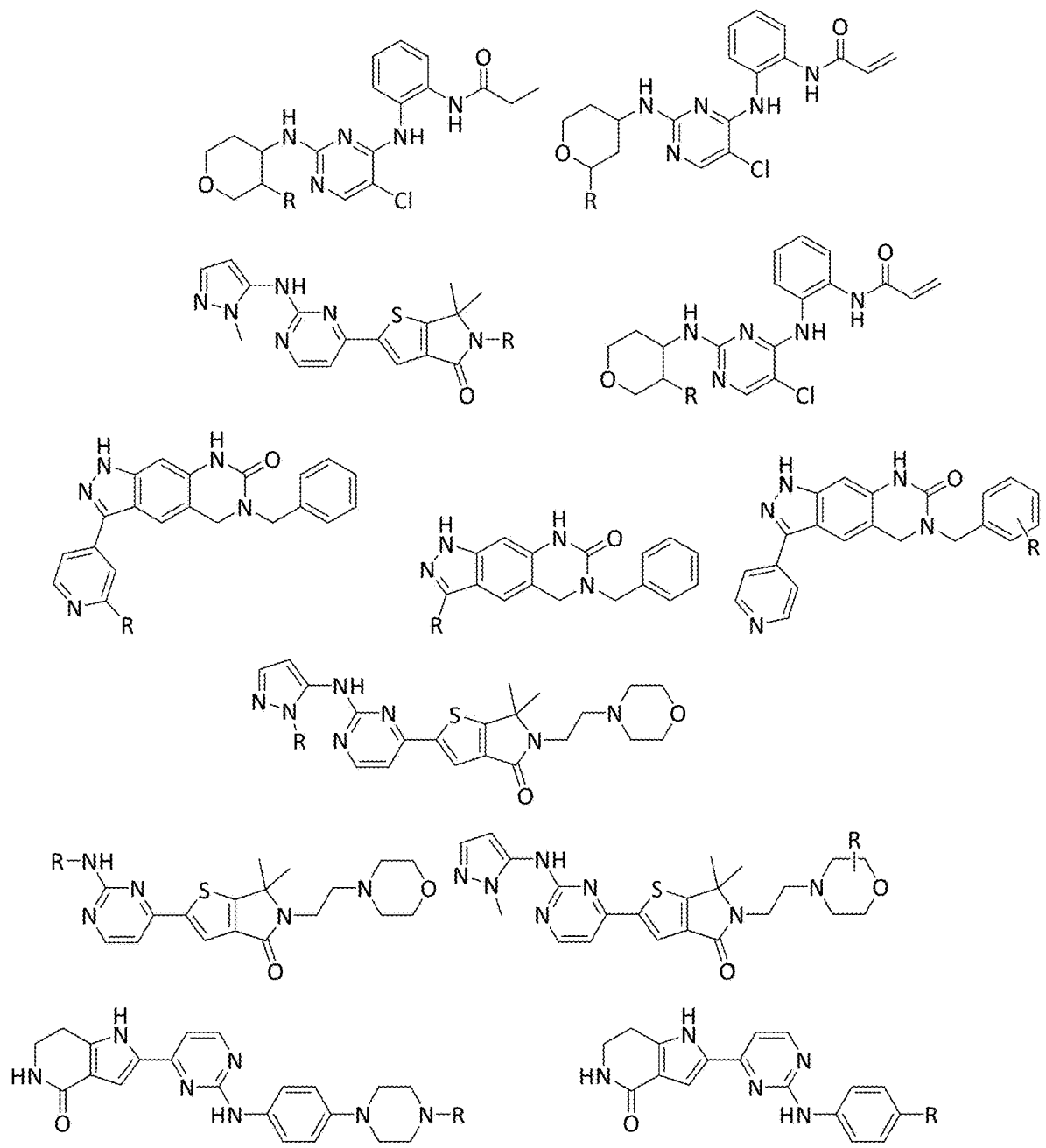

FIG. 8EEE
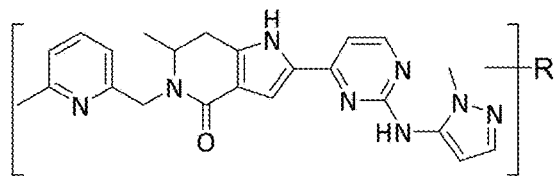
FIG. 8FFF
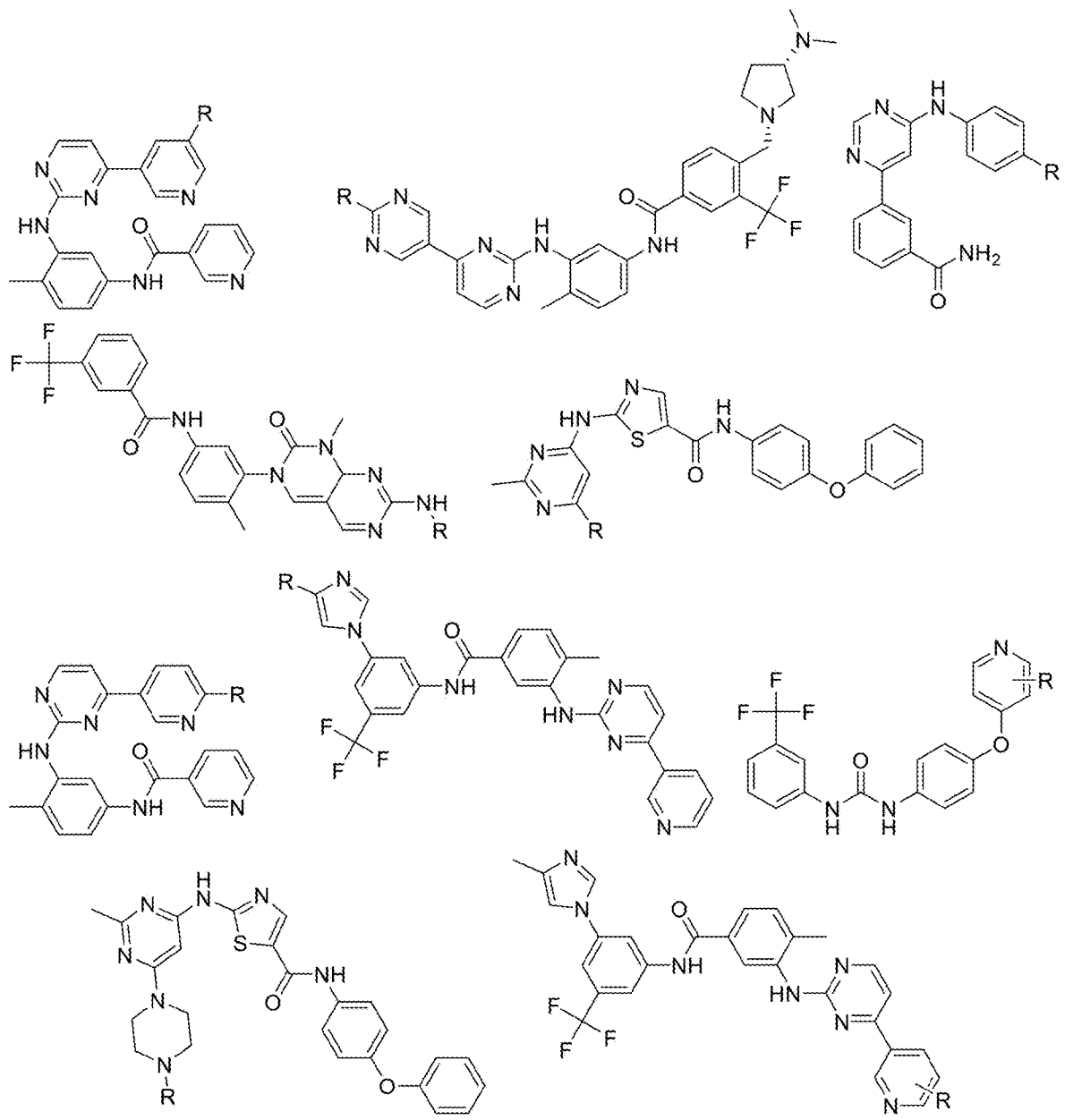

FIG. 8GGG
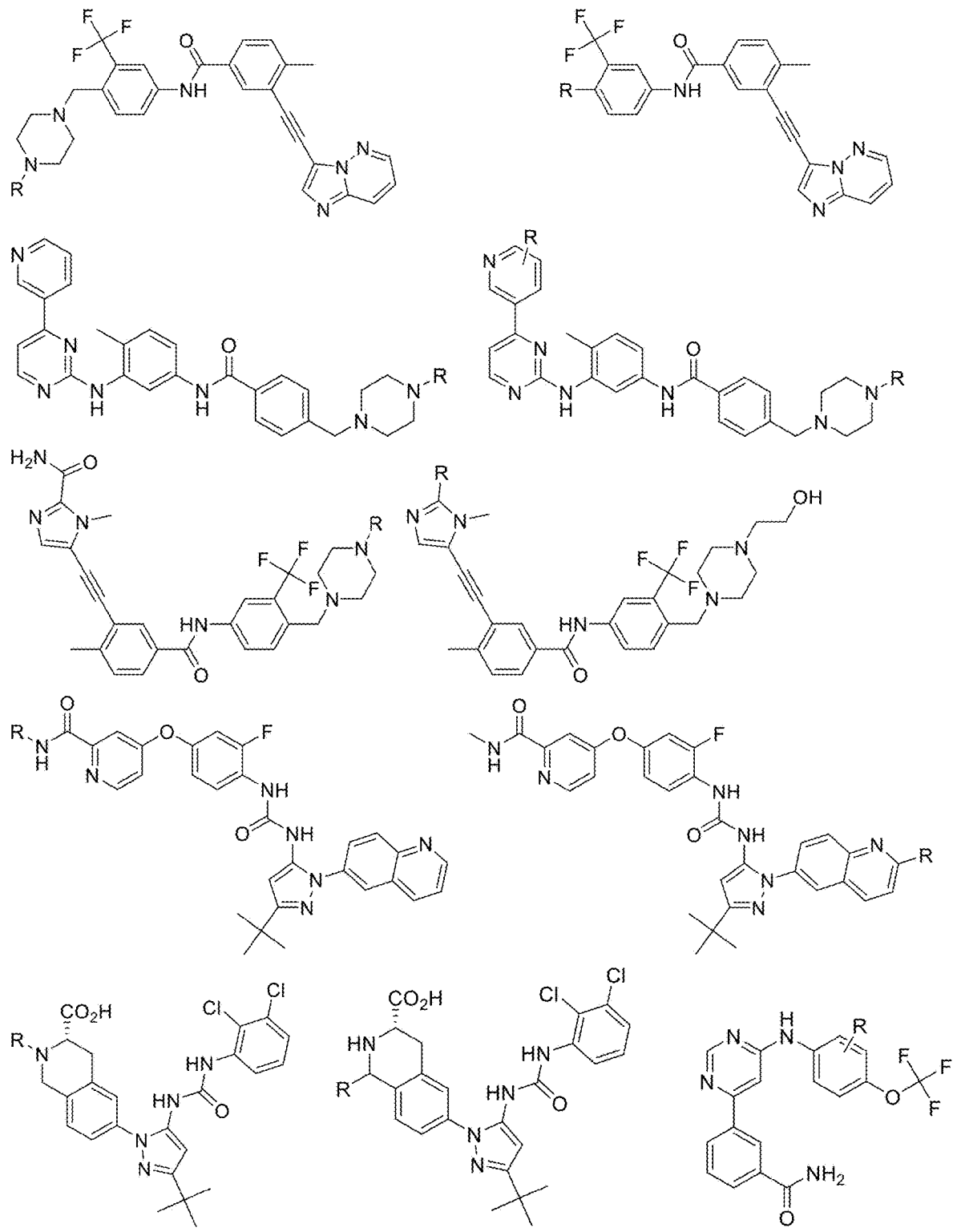

FIG. 8HHH
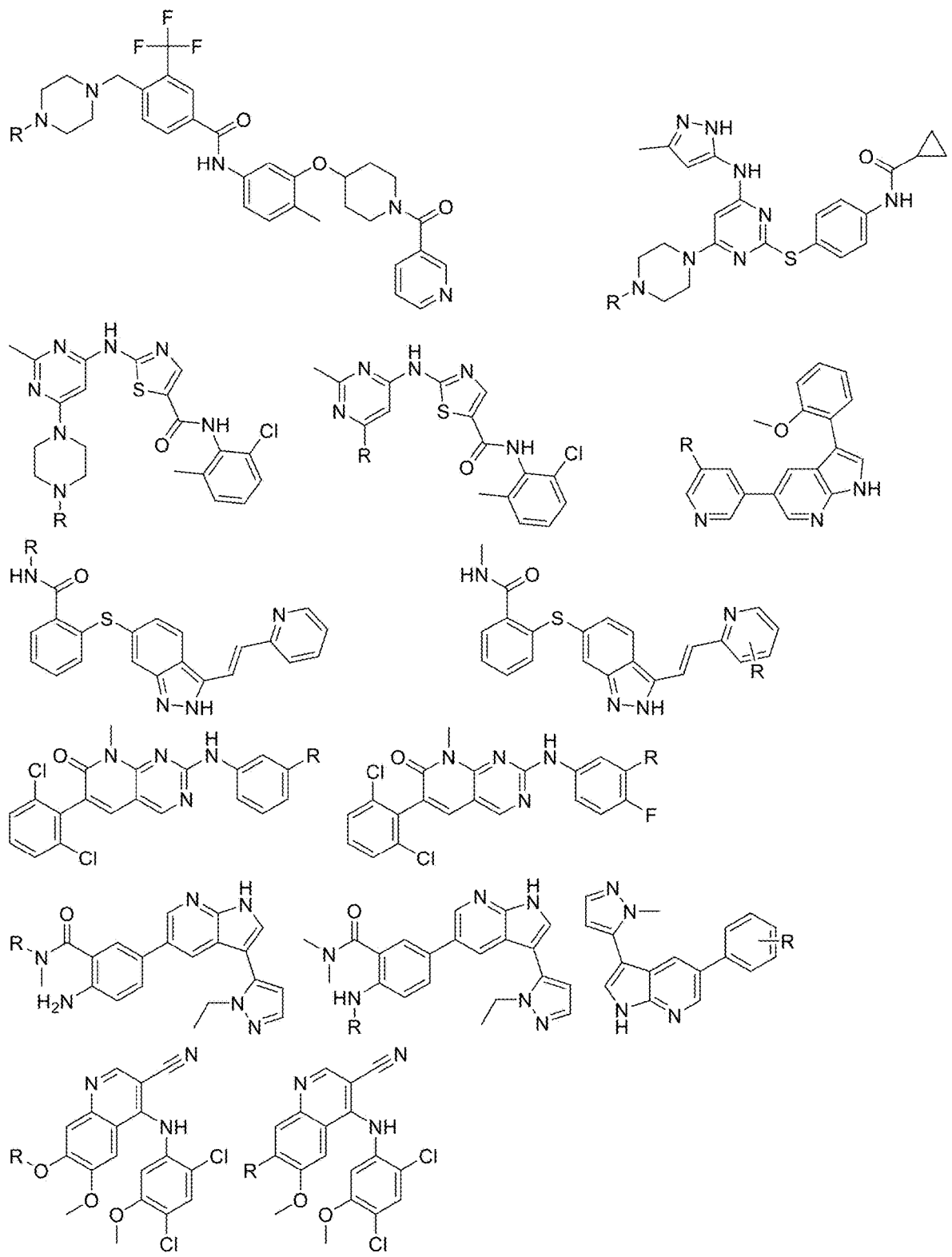

FIG. 8III
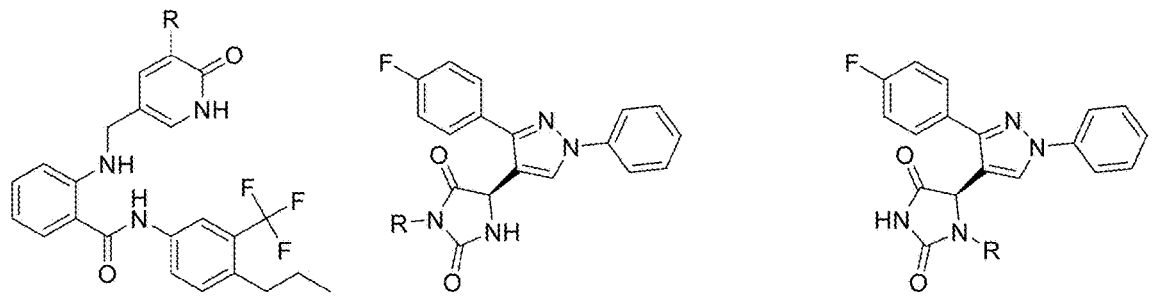
FIG. 8JJJ
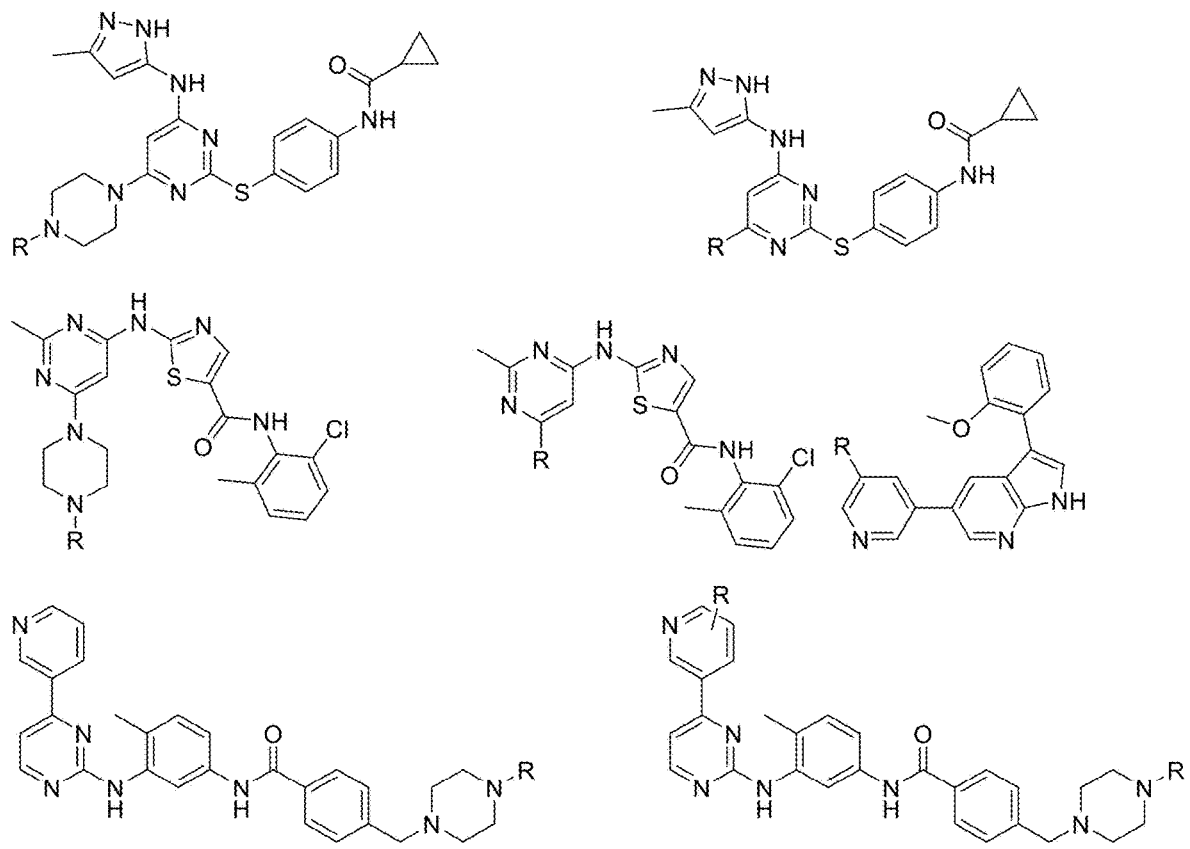

FIG. 8KKK
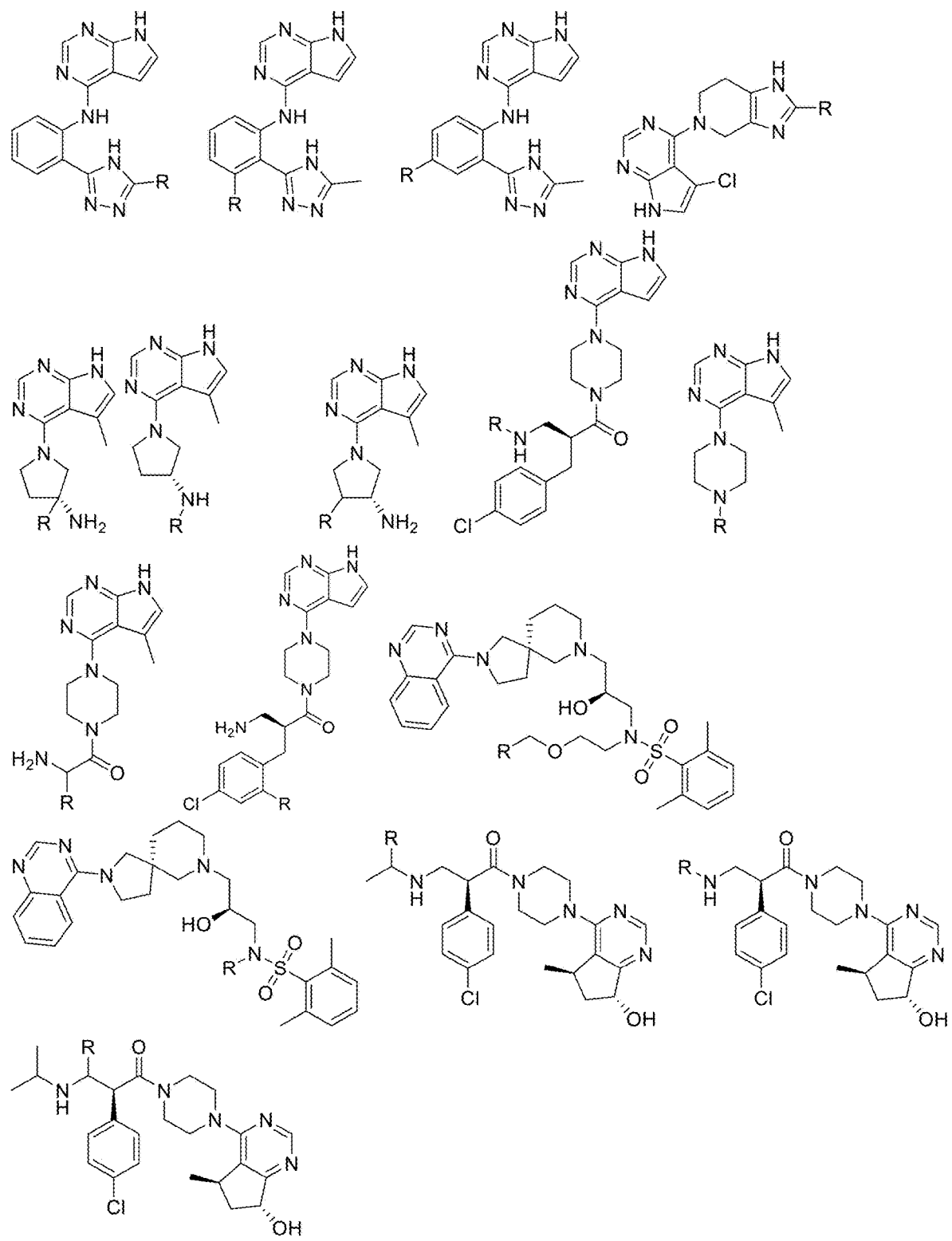

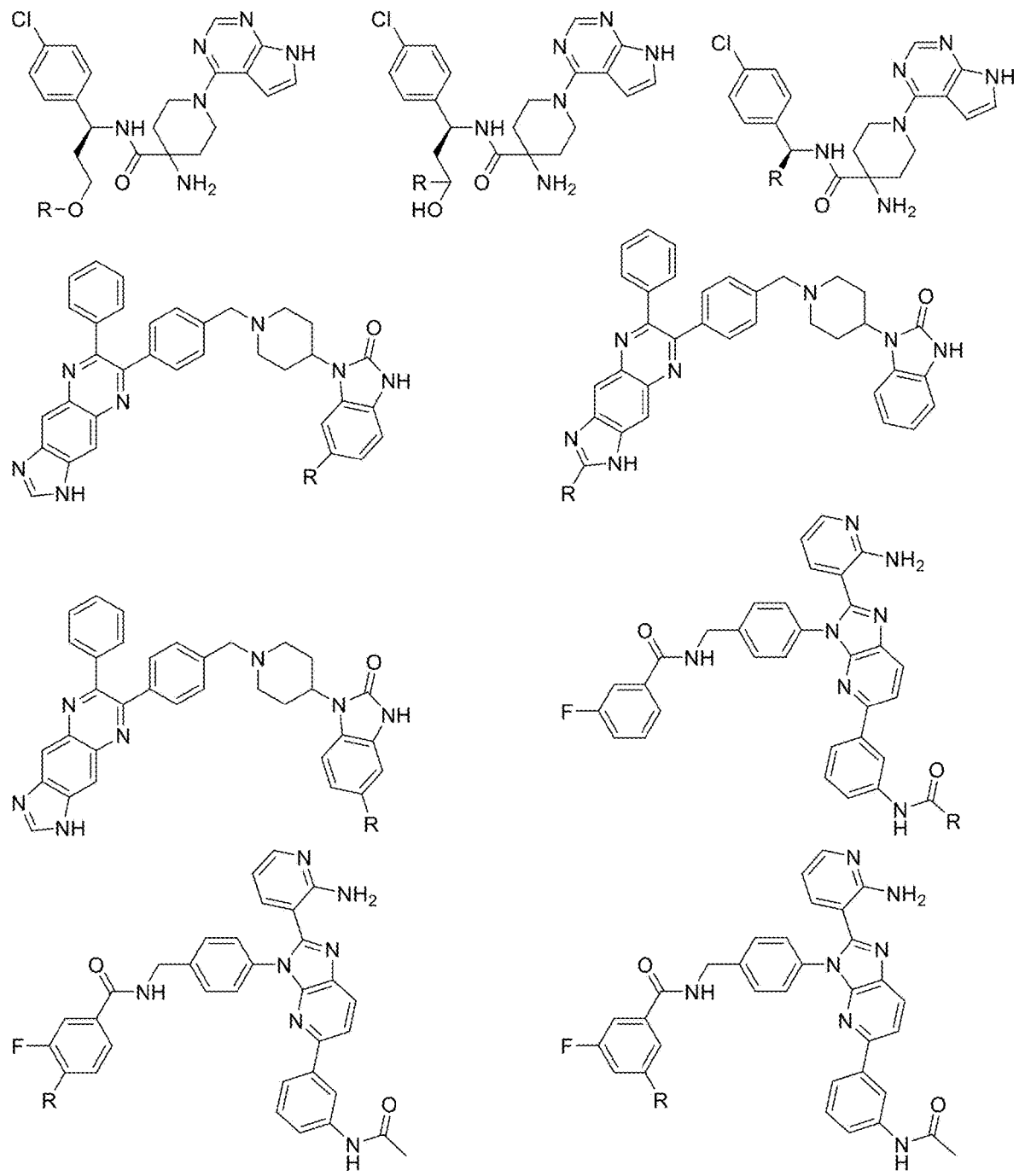
FIG. 8LLL

FIG. 8MMM
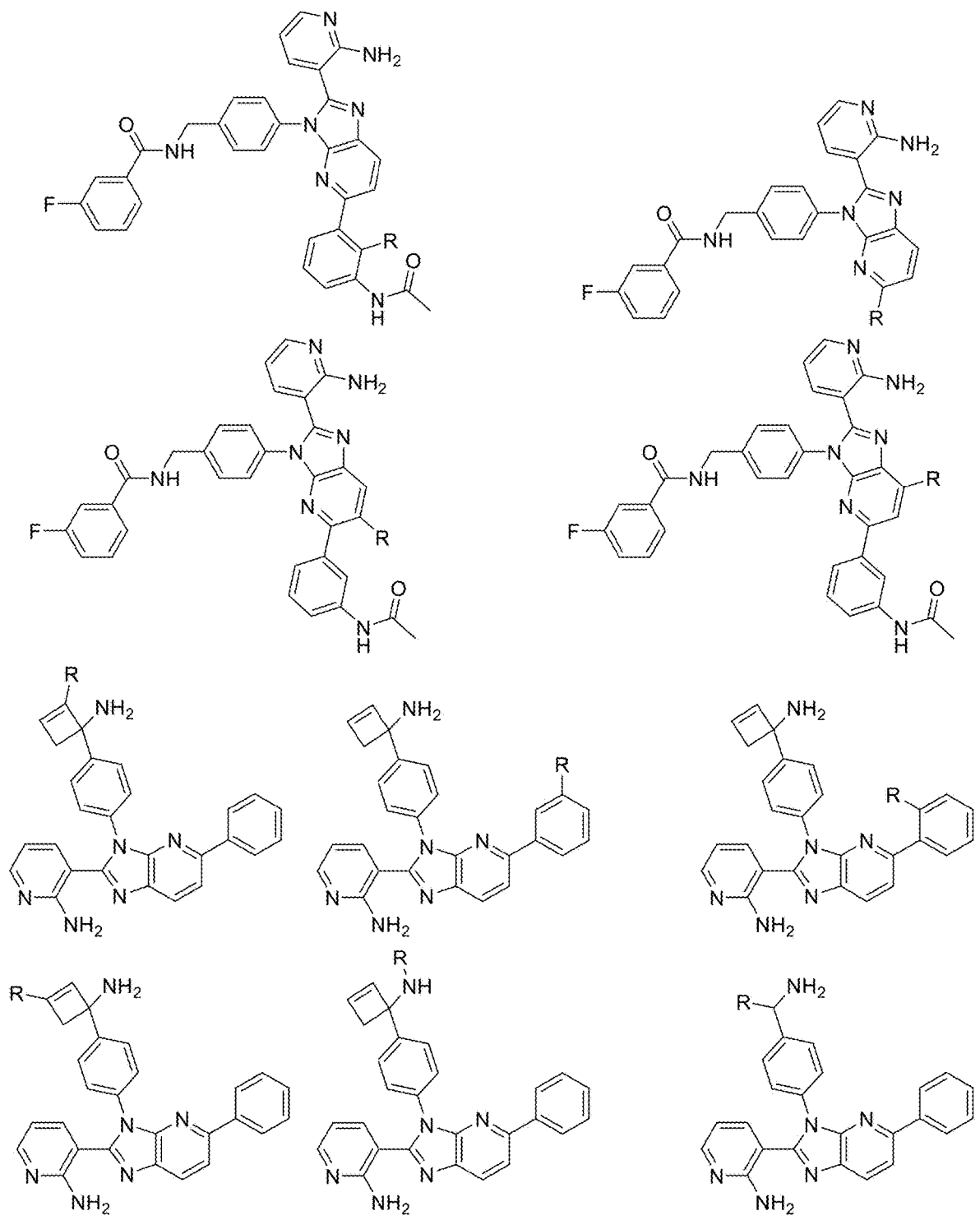

FIG. 8NNN

FIG. 8OOO
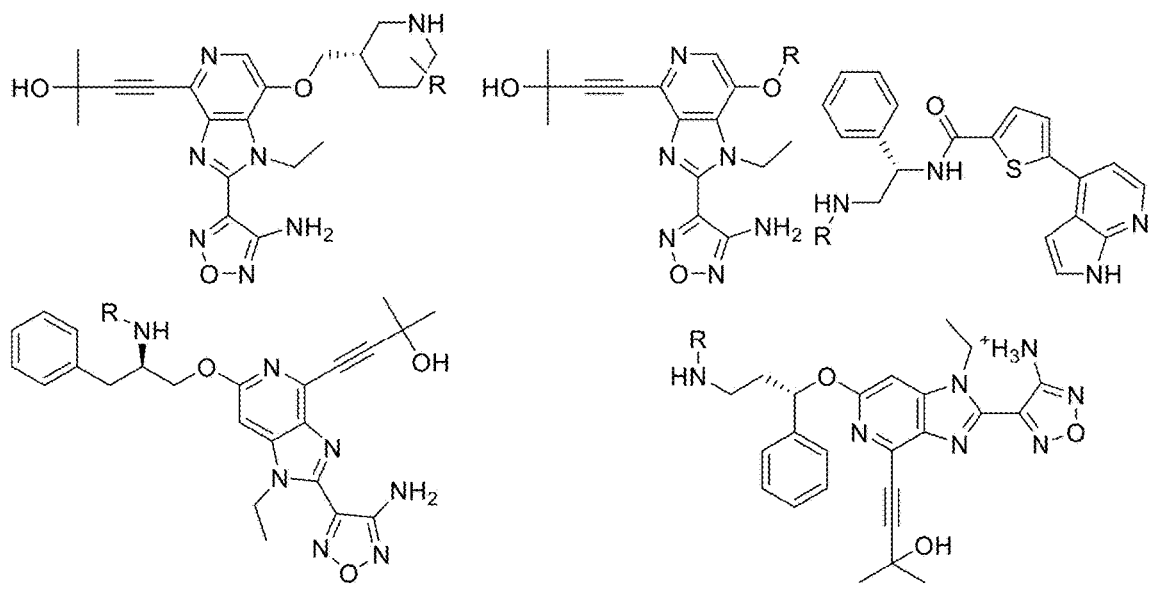
FIG. 8PPP
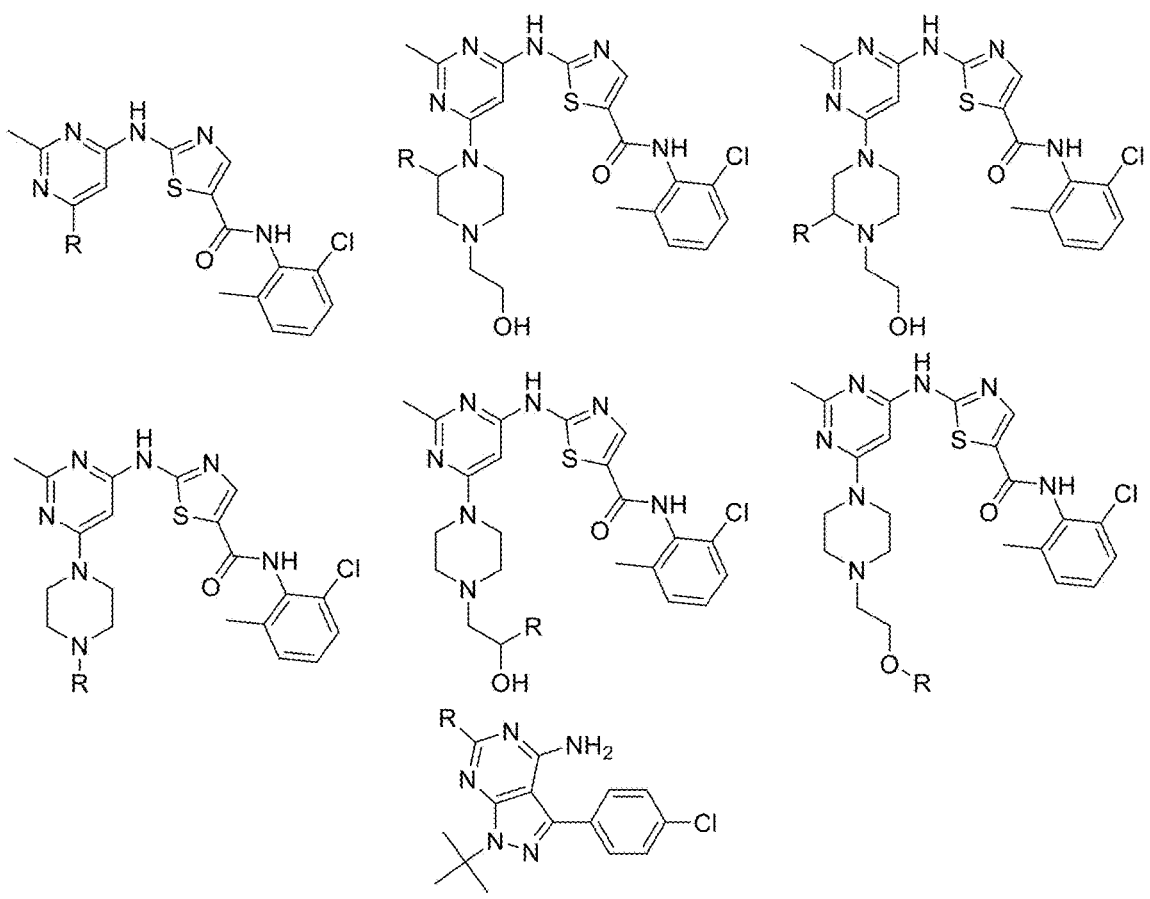

FIG. 8QQQ
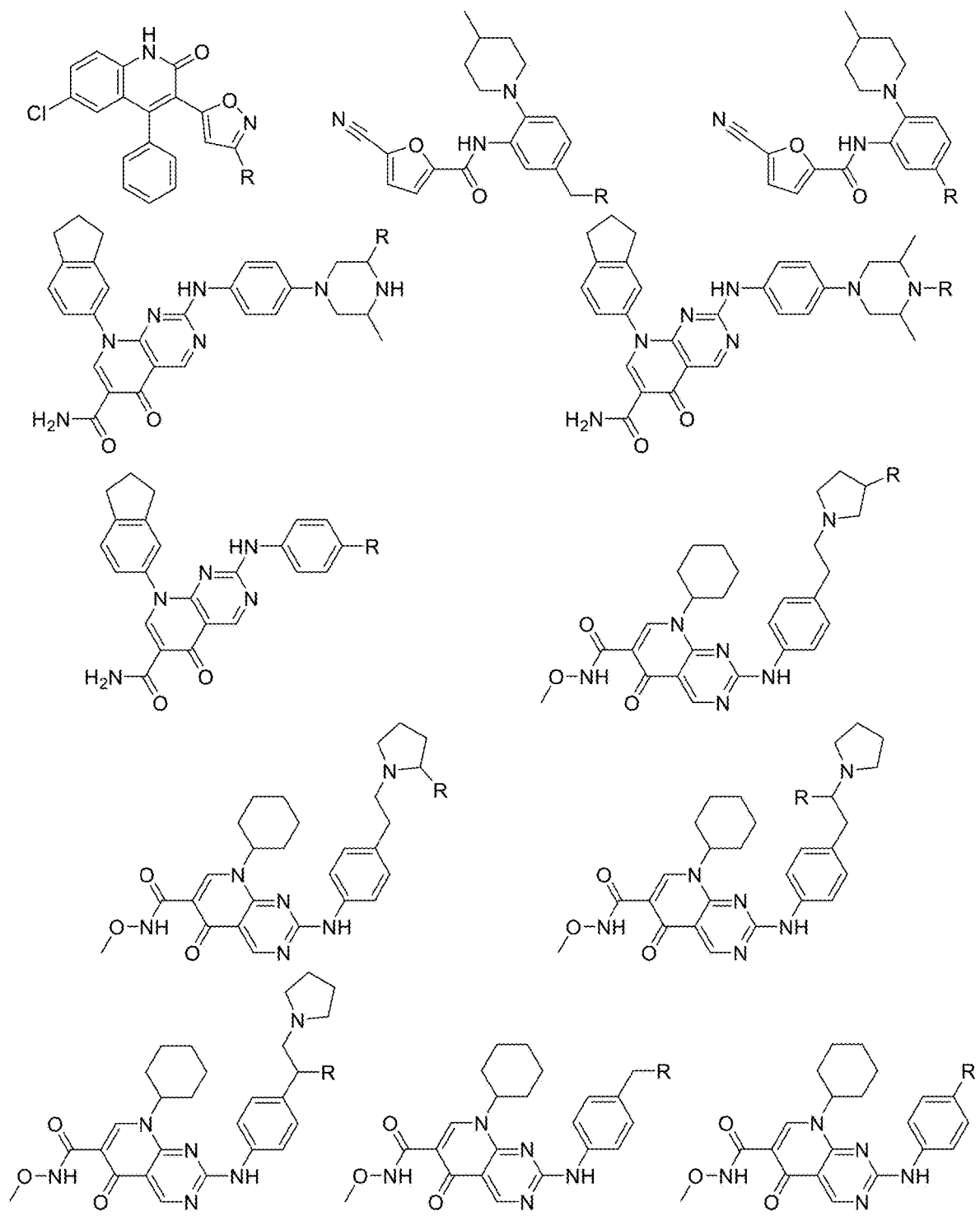

FIG. 8RRR
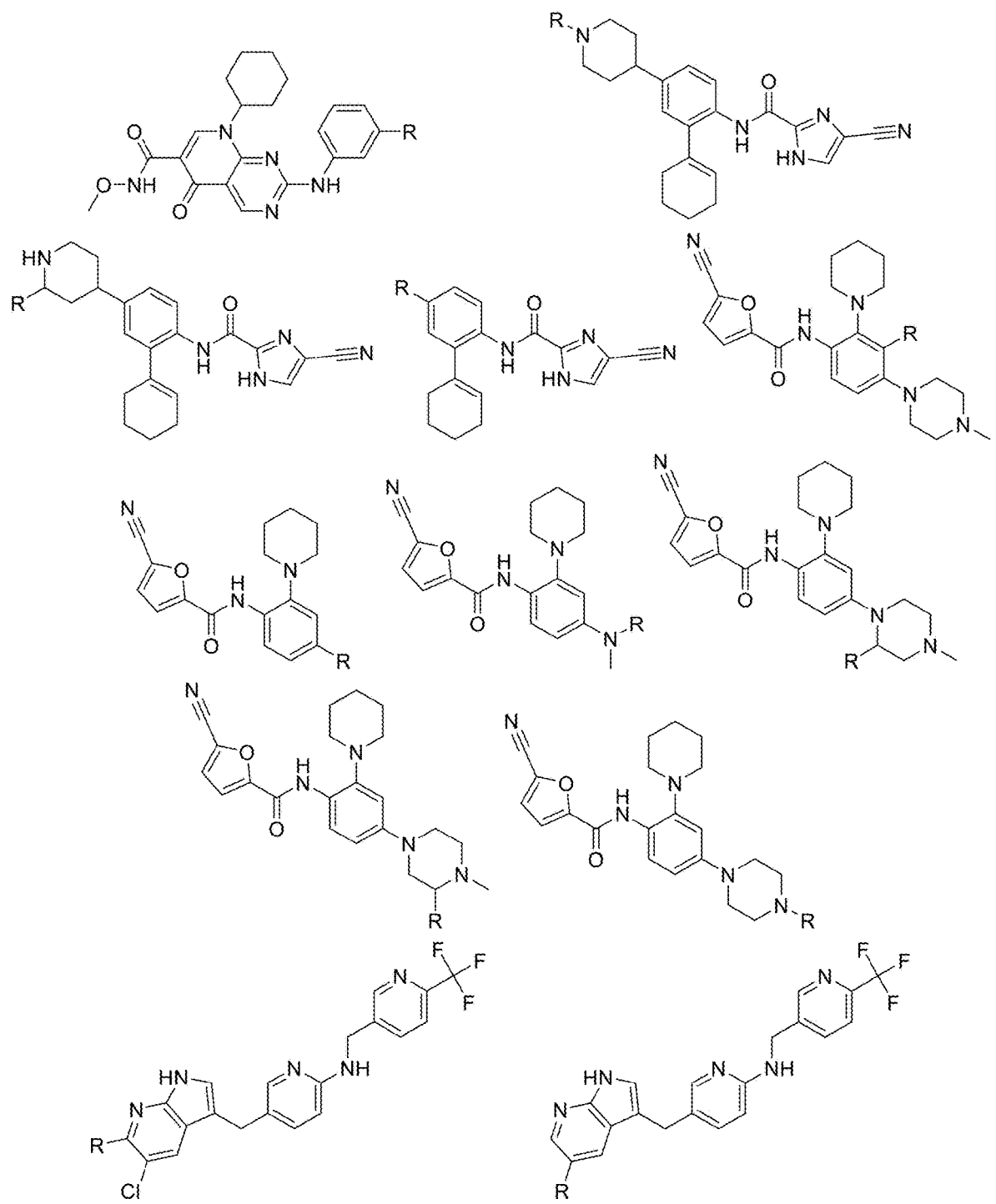

FIG. 8SSS
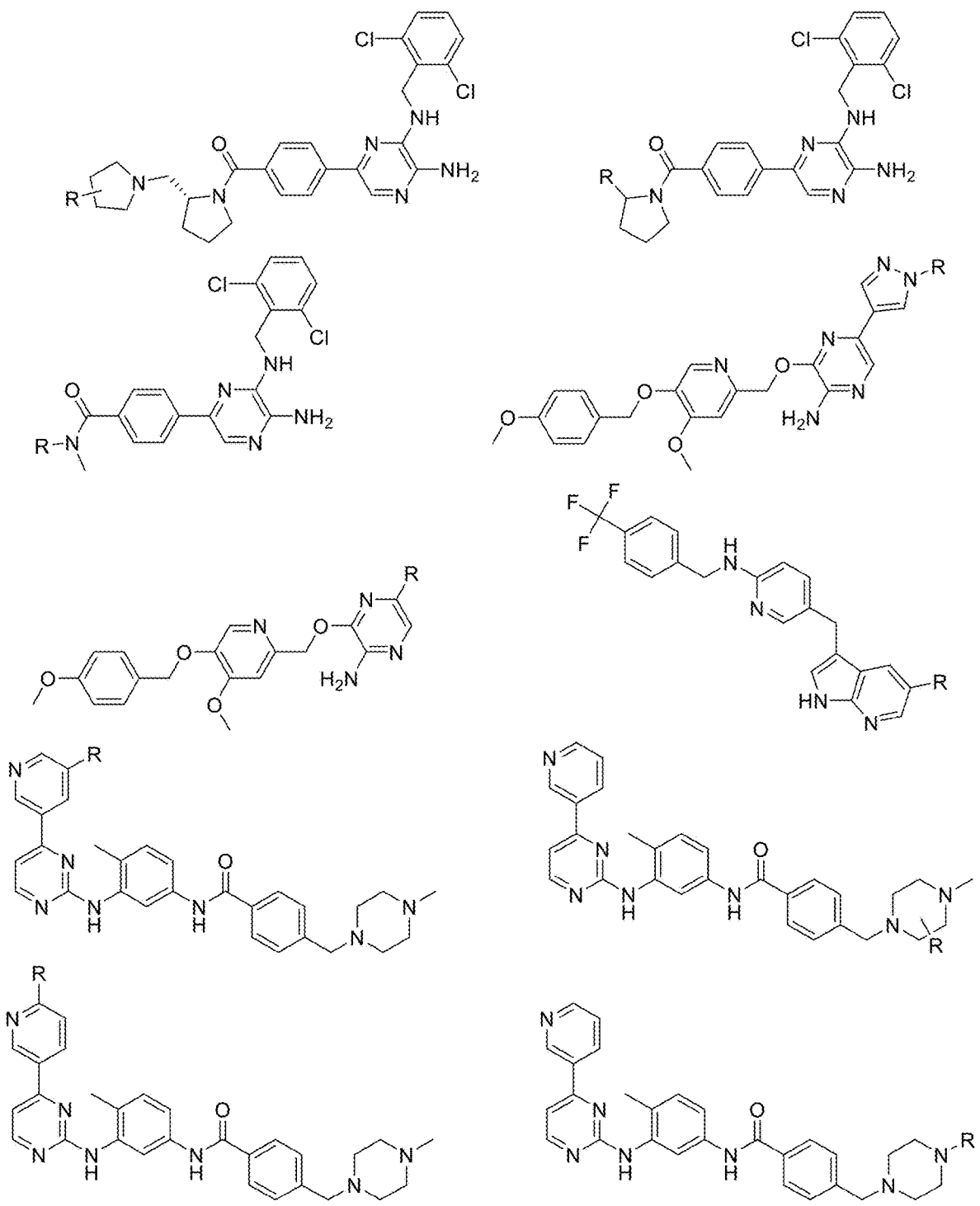

FIG. 8TTT
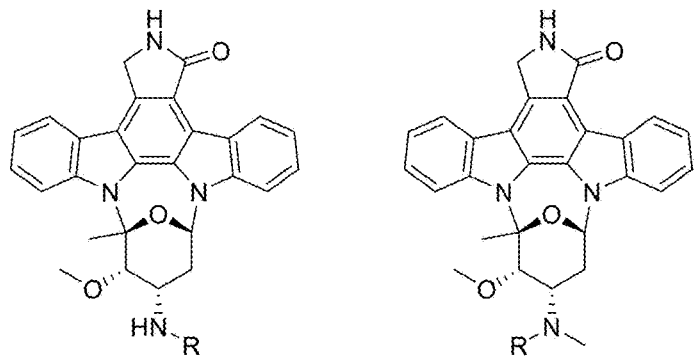
FIG. 8UUU
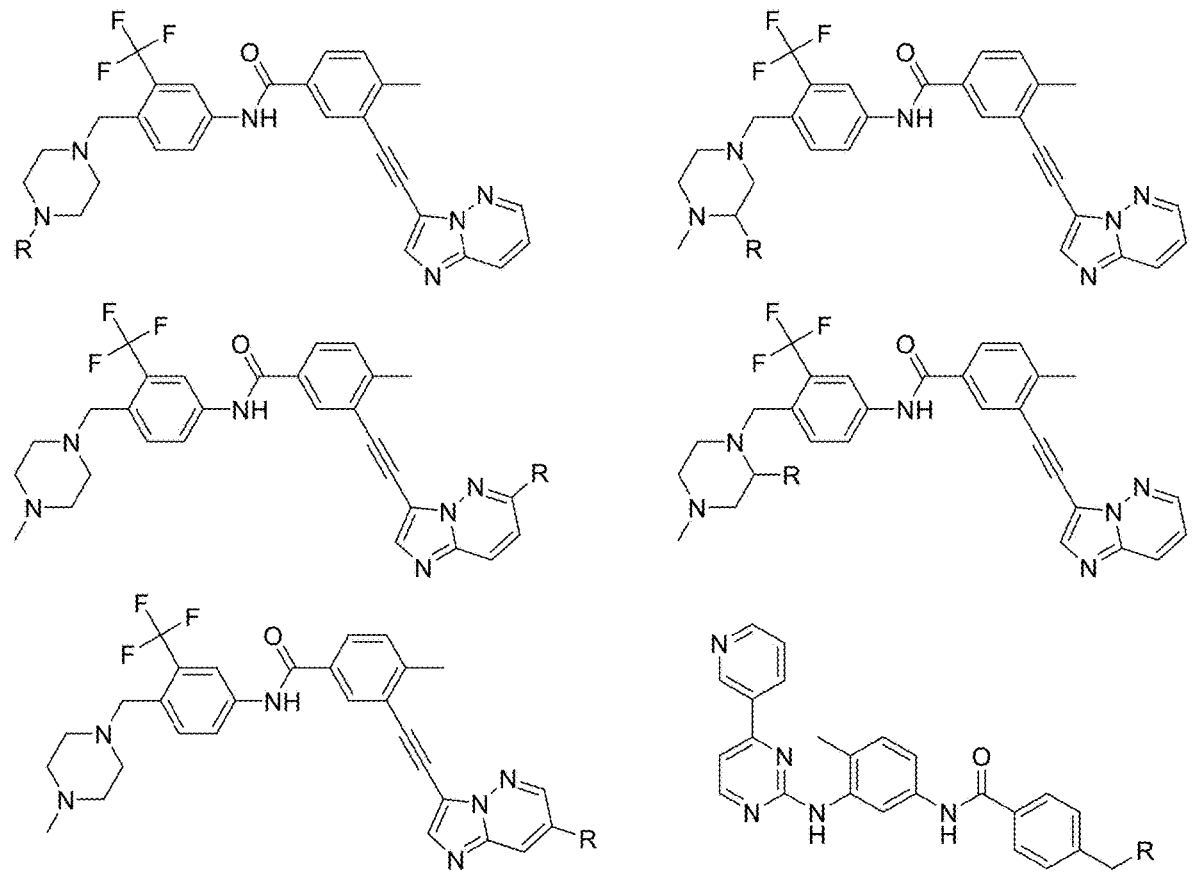

FIG. 8VVV
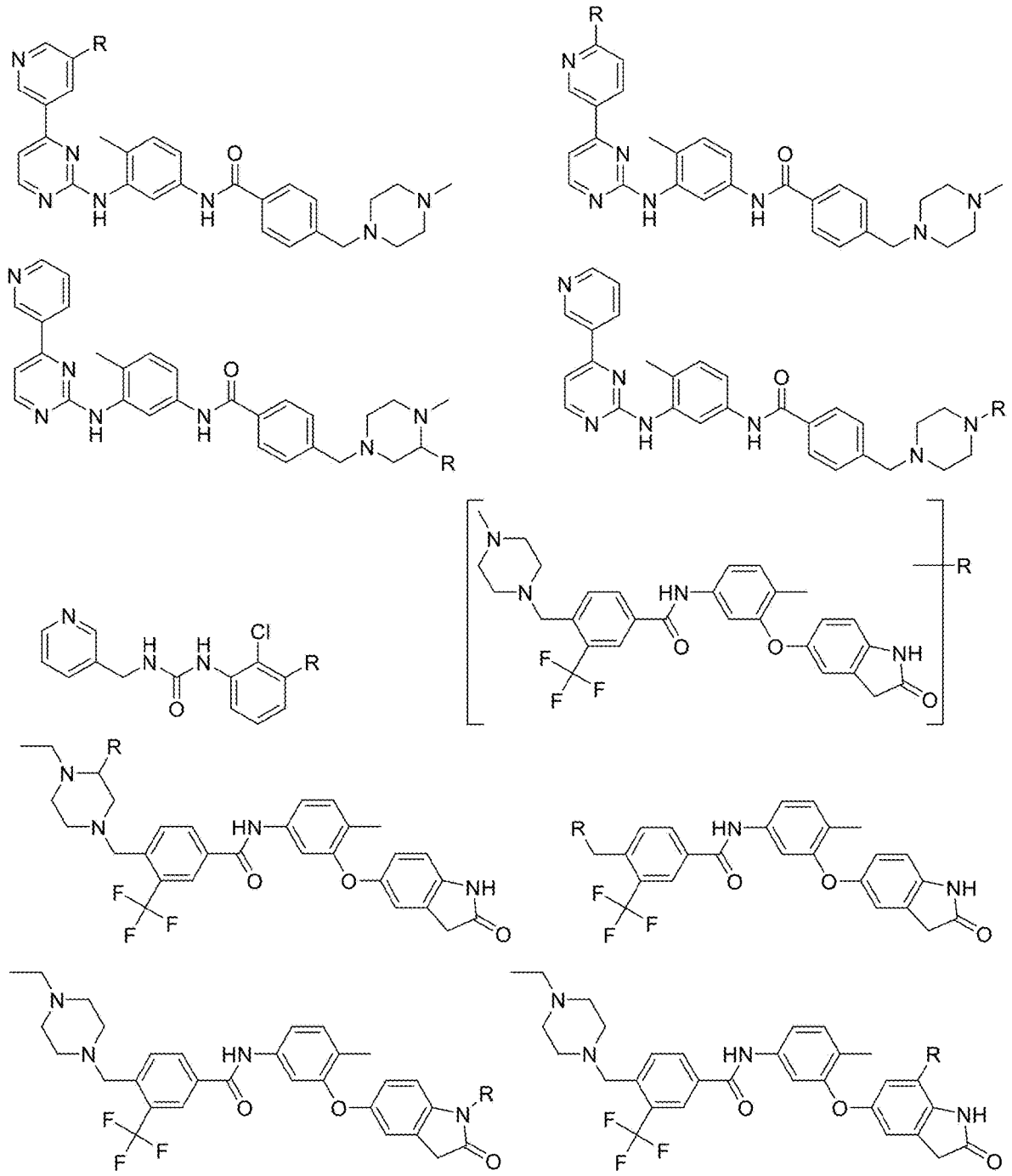

FIG. 8WWW
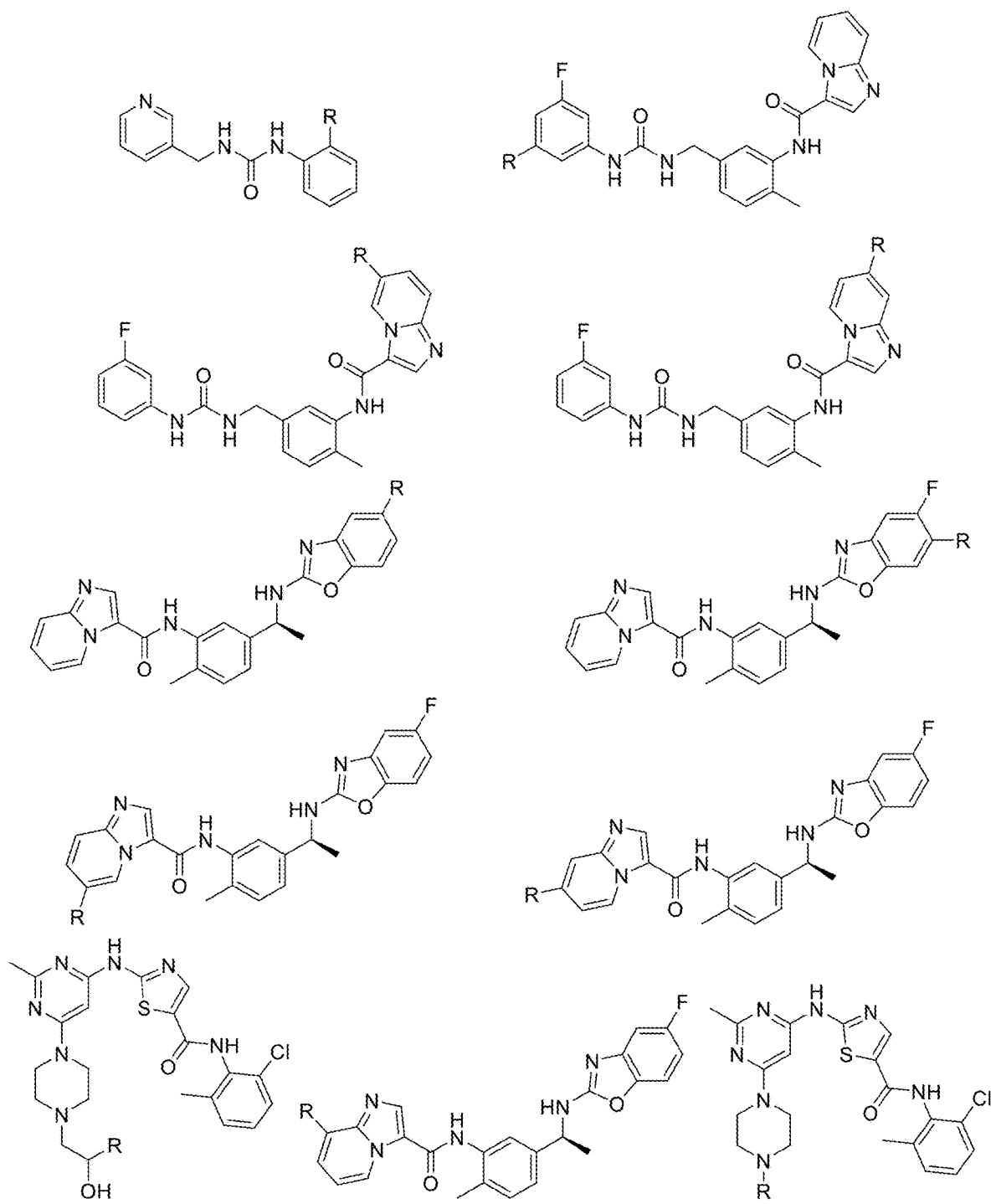

FIG. 8XXX
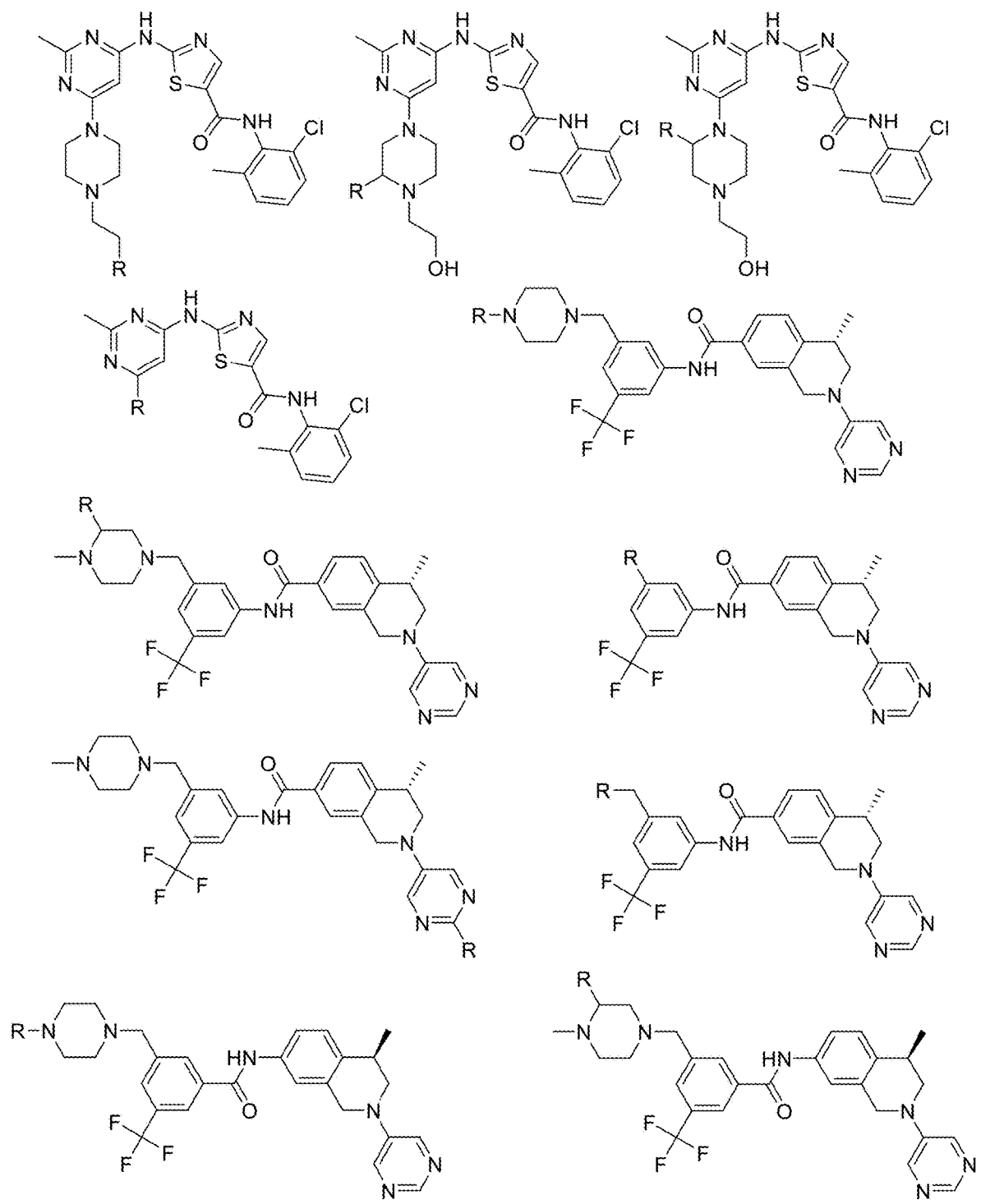

FIG. 8YYY
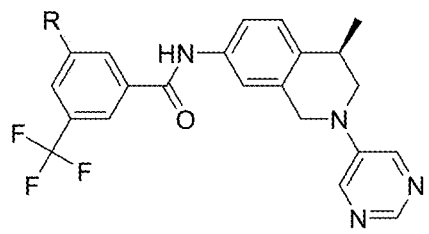
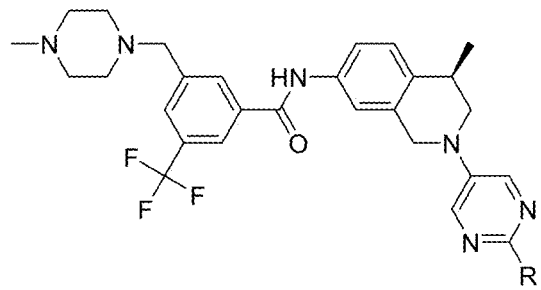
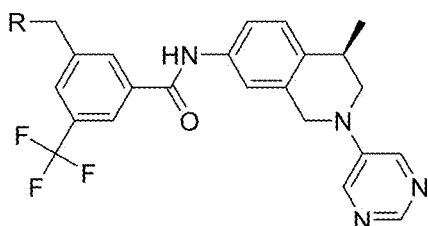
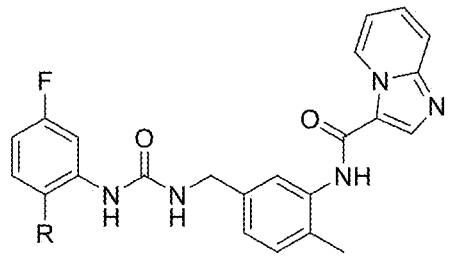
FIG. 8ZZZ
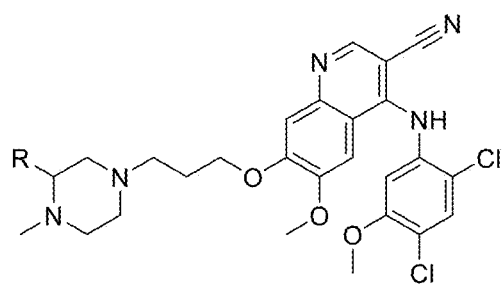
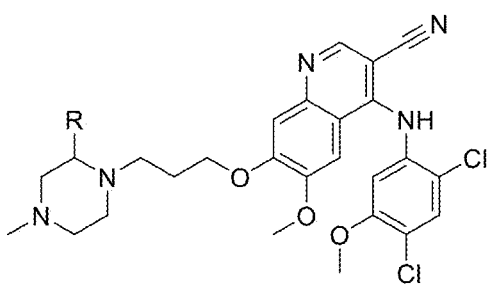
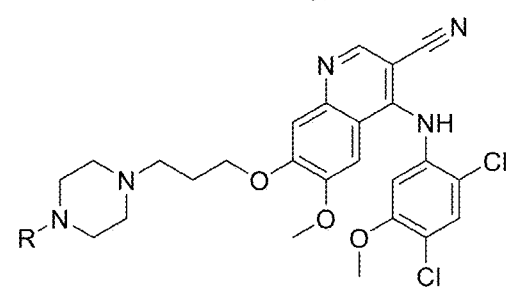
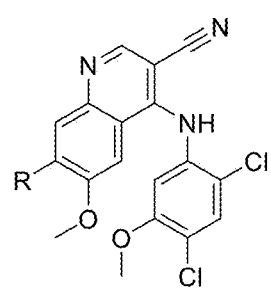
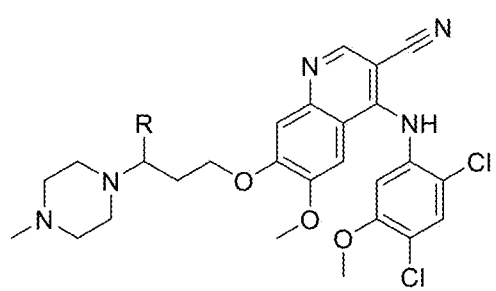
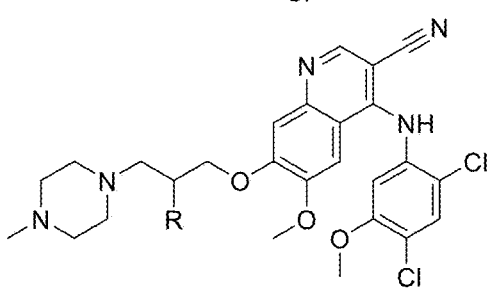

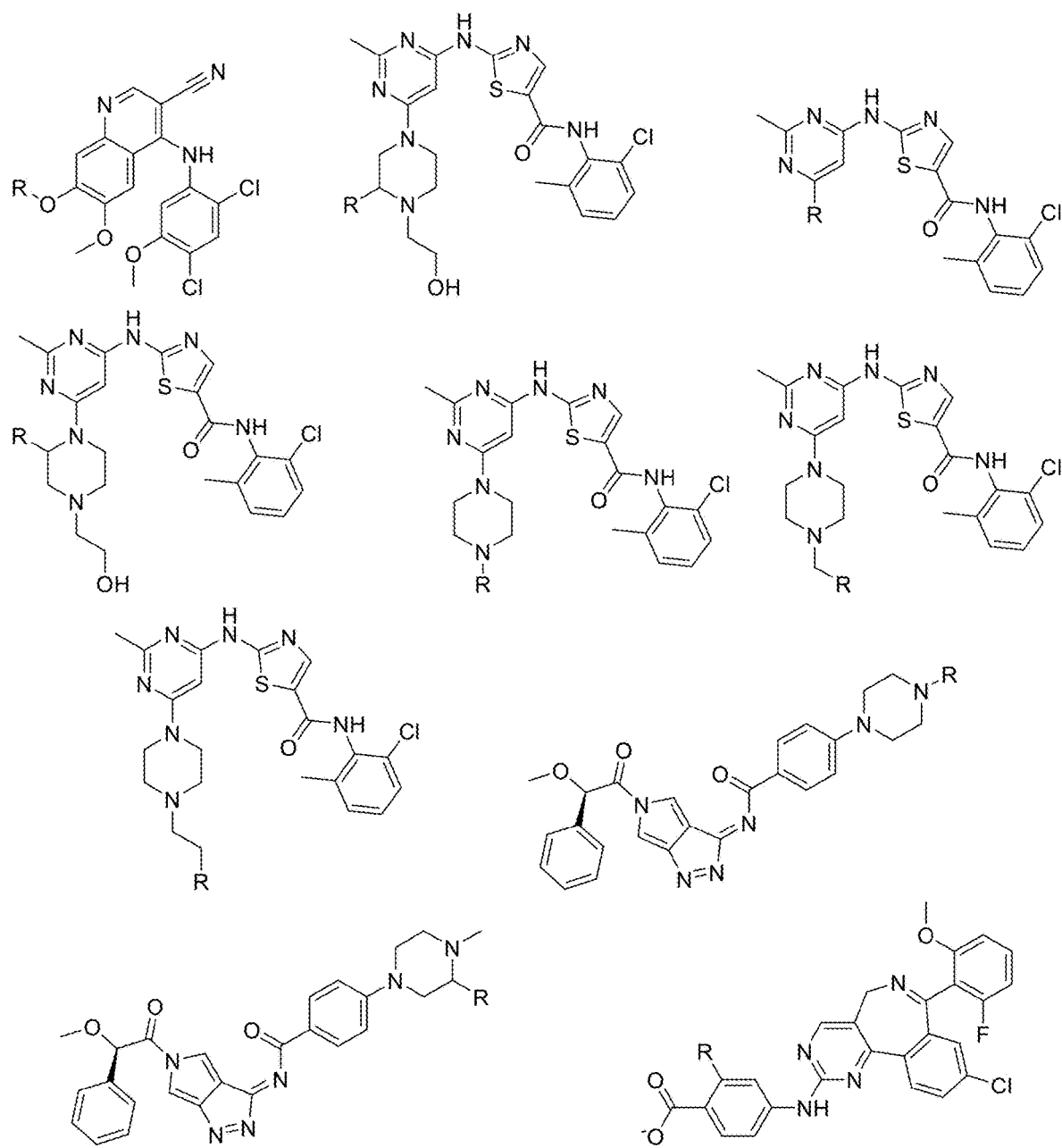
FIG. 8AAAA

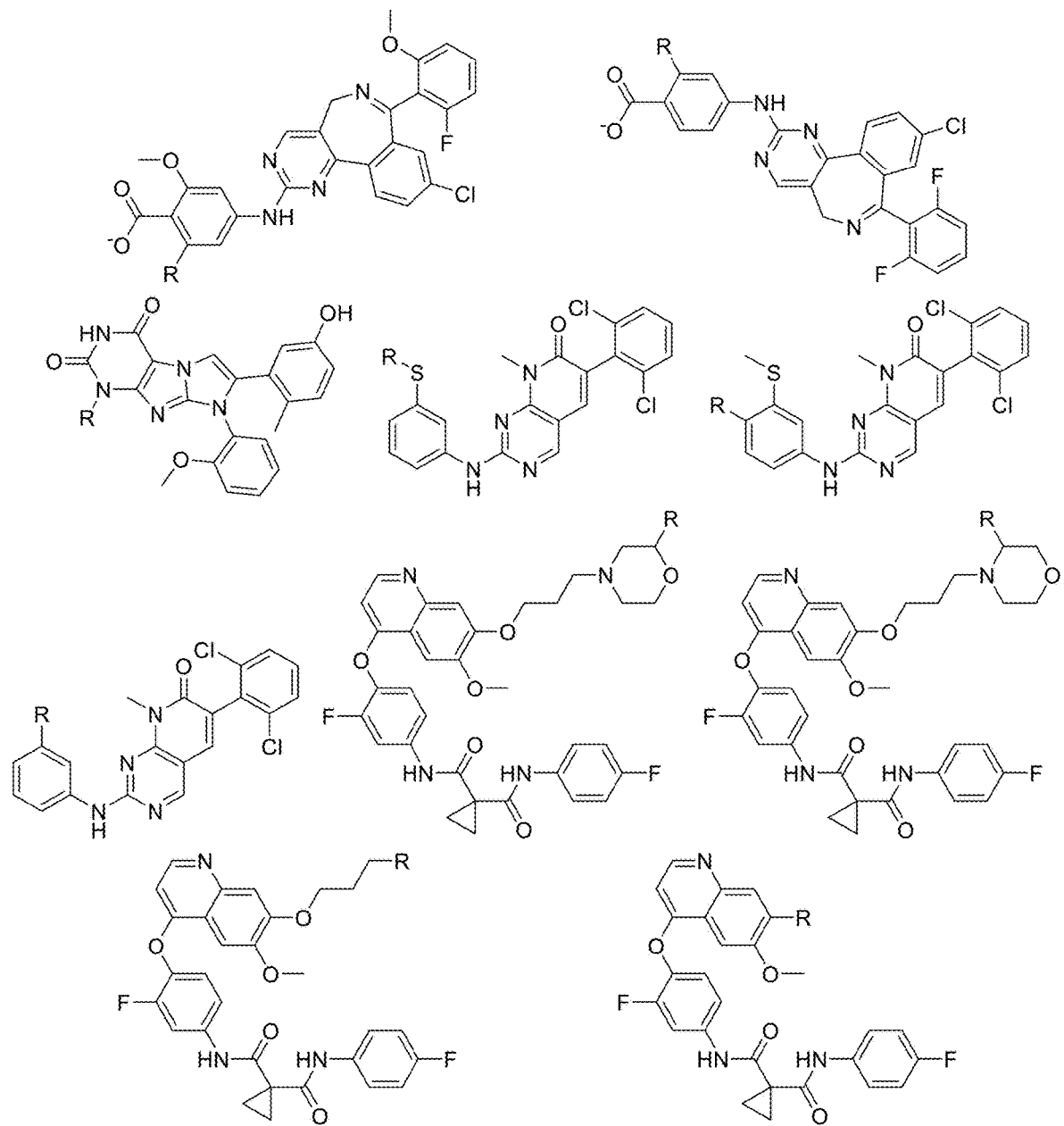
FIG. 8BBBB

FIG. 8CCCC
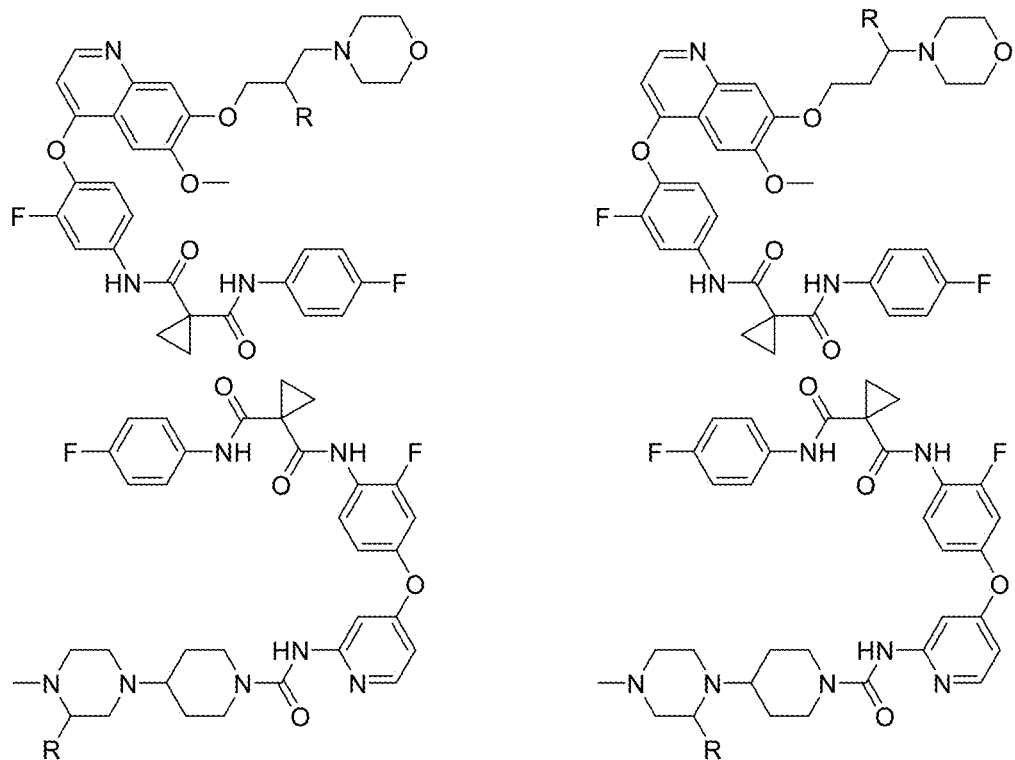
FIG. 8DDDD
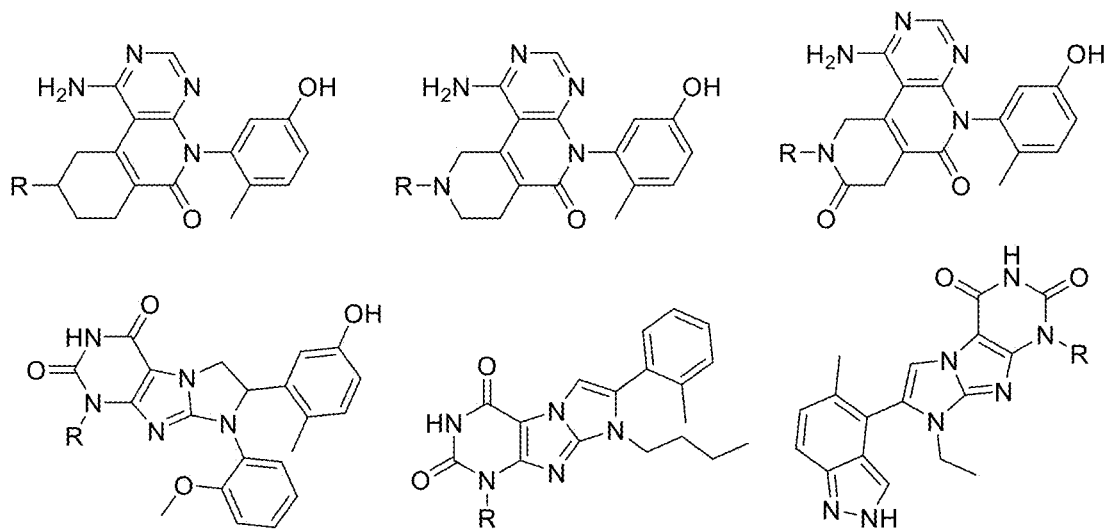

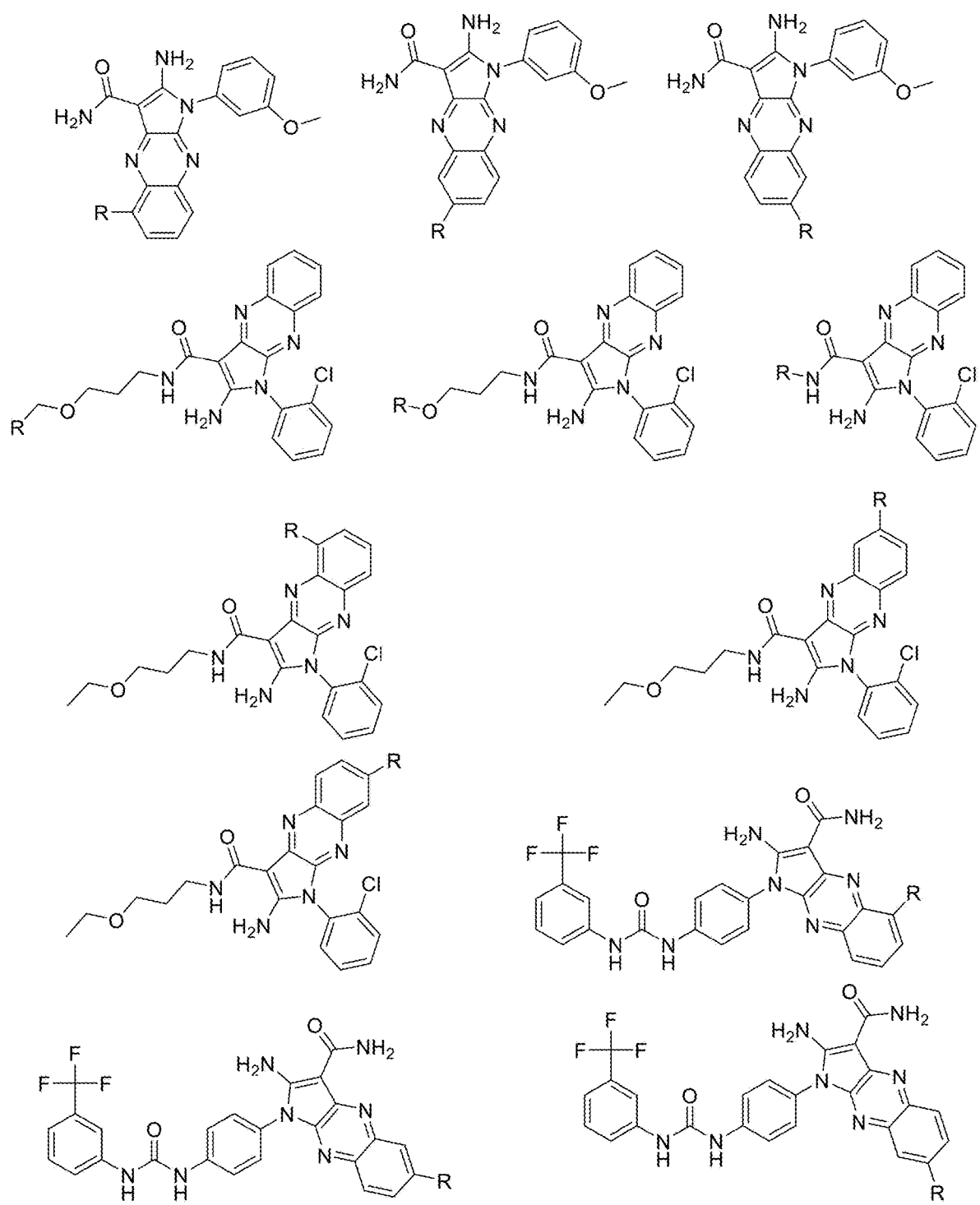
FIG. 8EEEE

FIG. 8FFFF
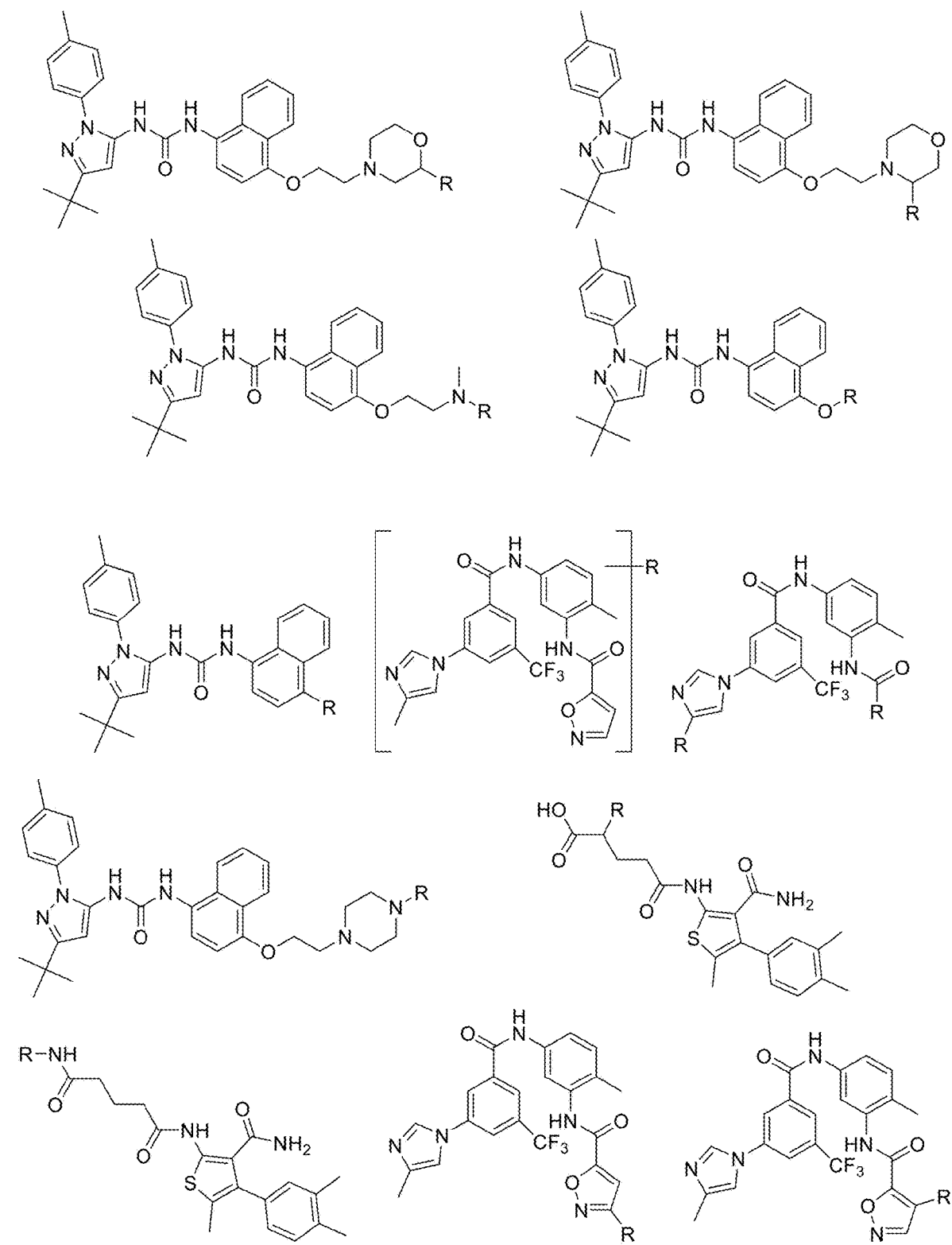

FIG. 8GGGG
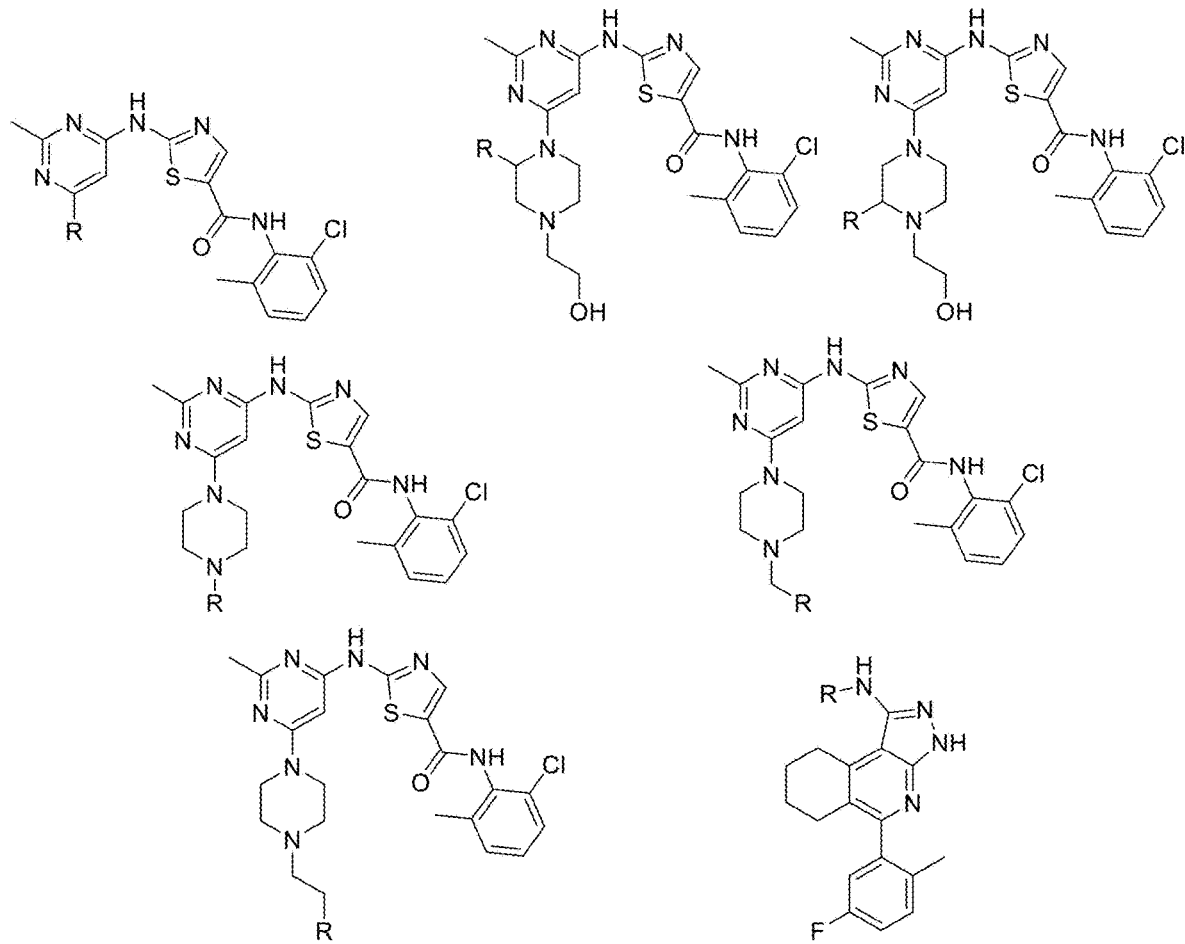
FIG. 8HHHH
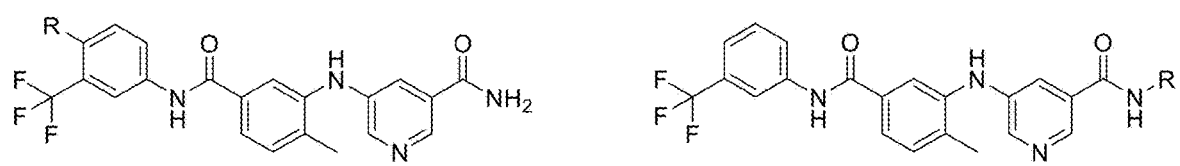
FIG. 8IIII
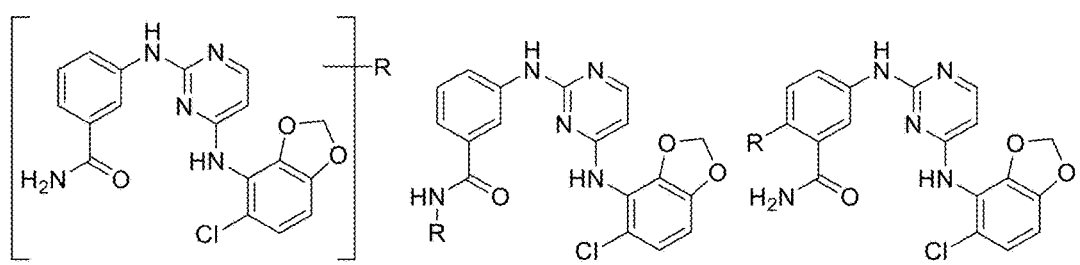

FIG. 8JJJJ
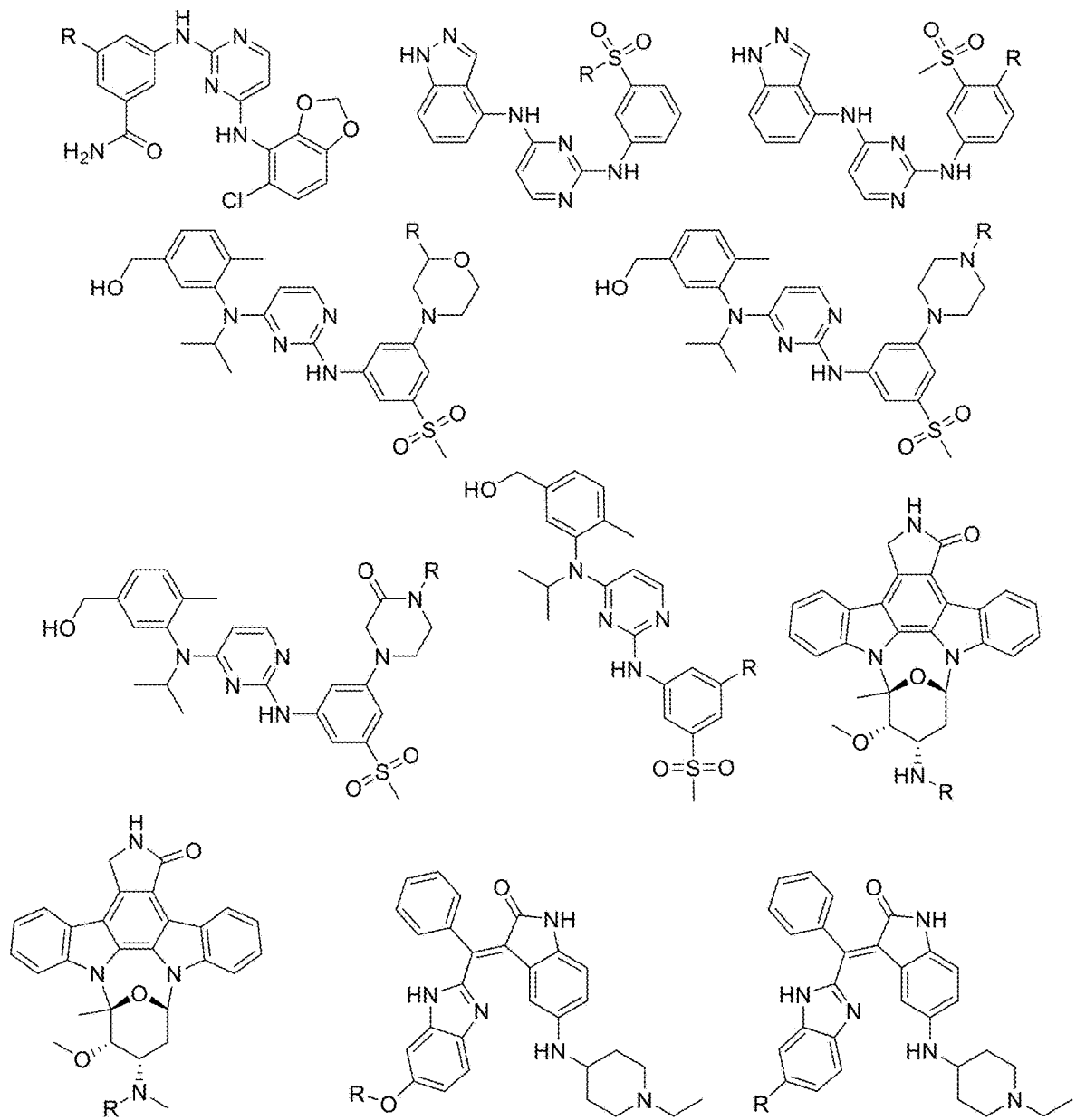

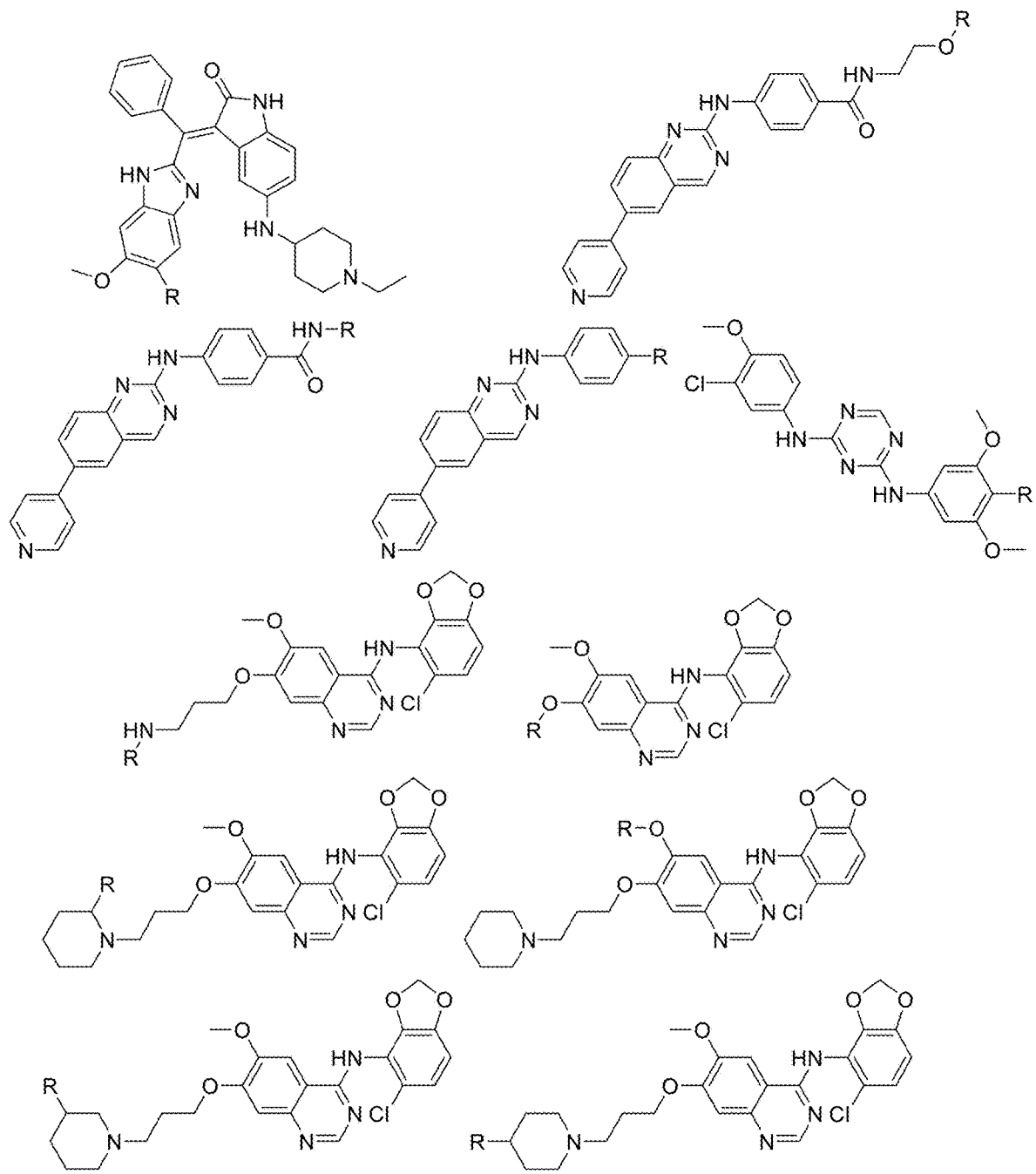
FIG. 8KKKK

FIG. 8LLLL
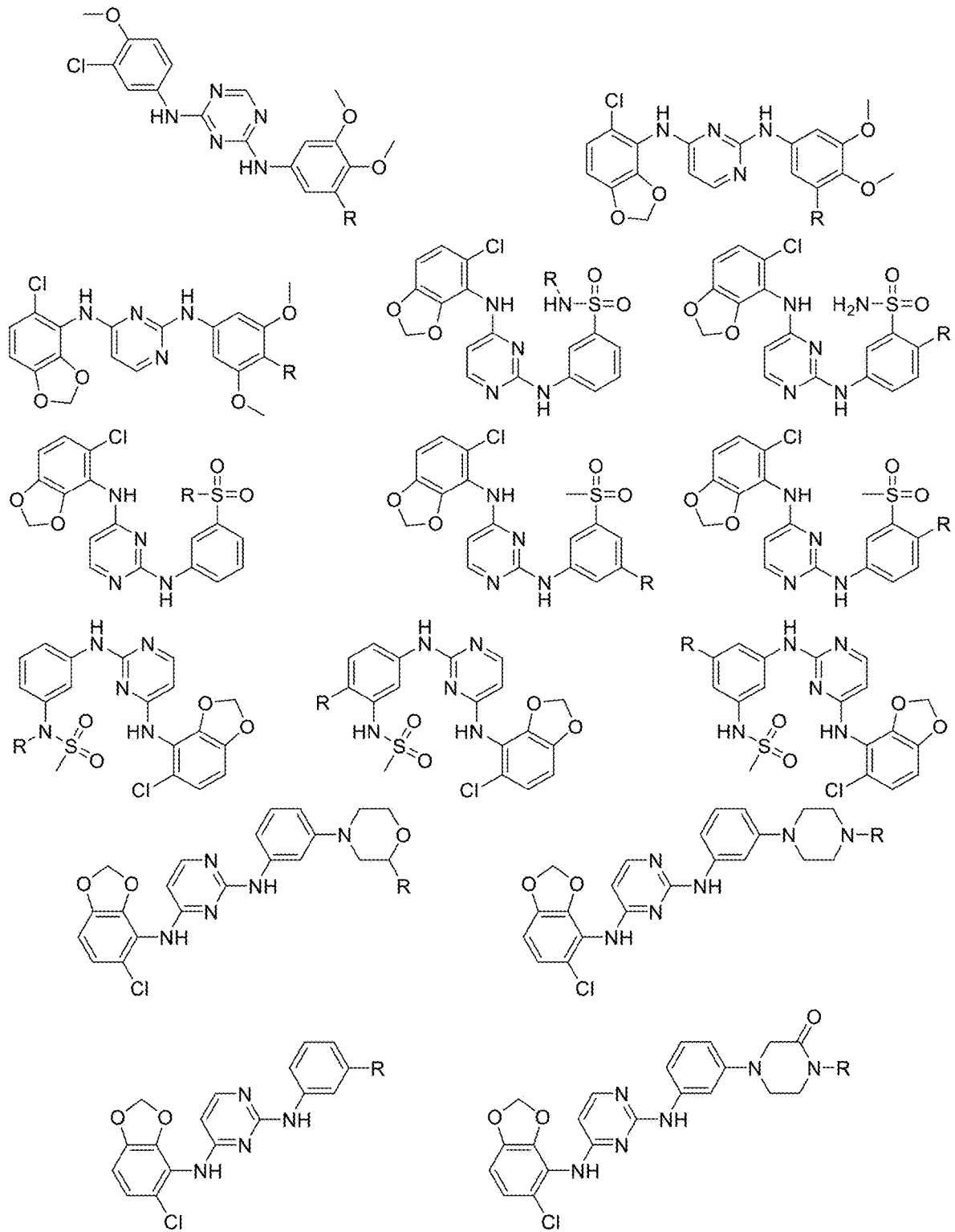

FIG. 8MMMM
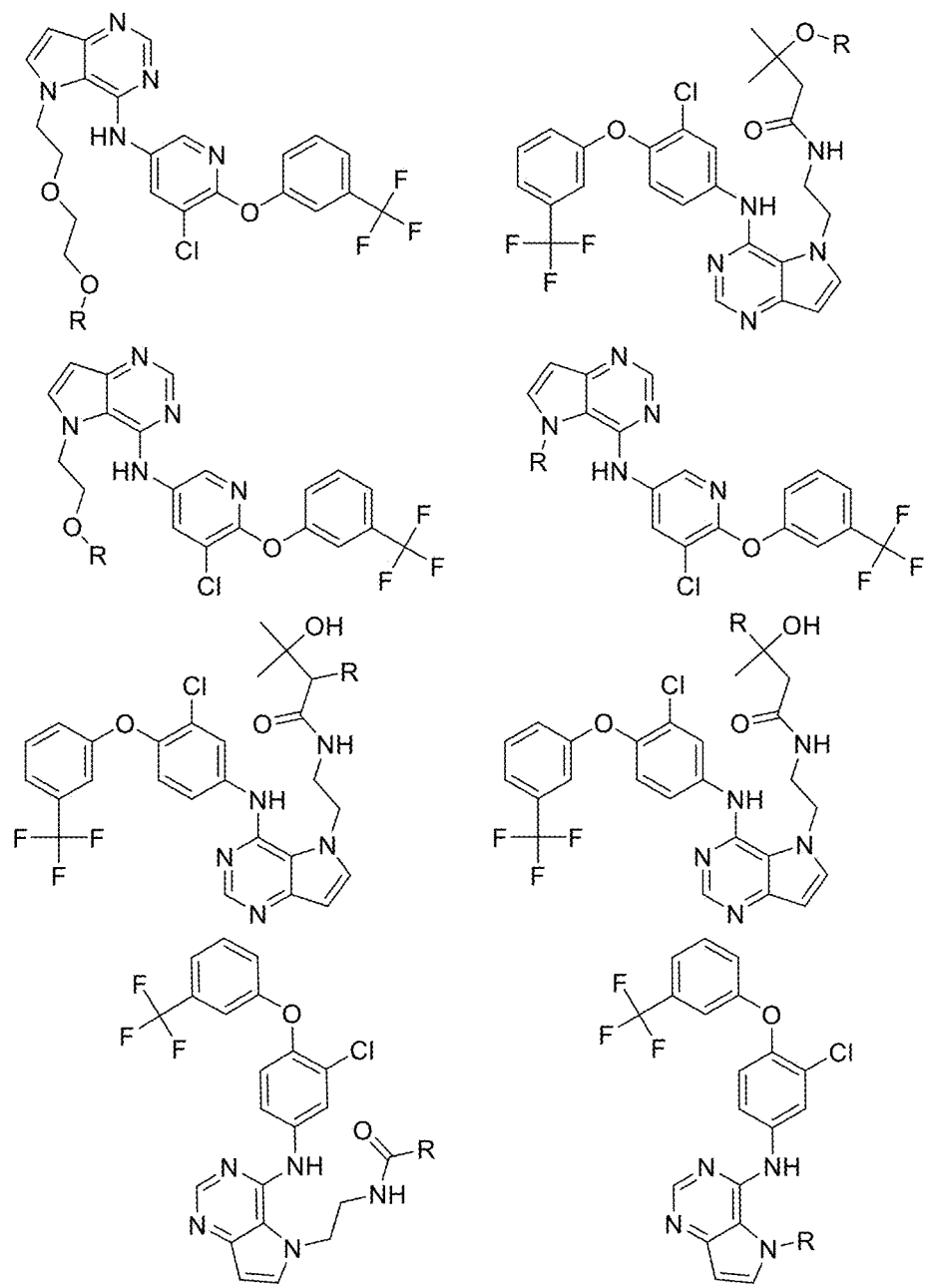

FIG. 8NNNN
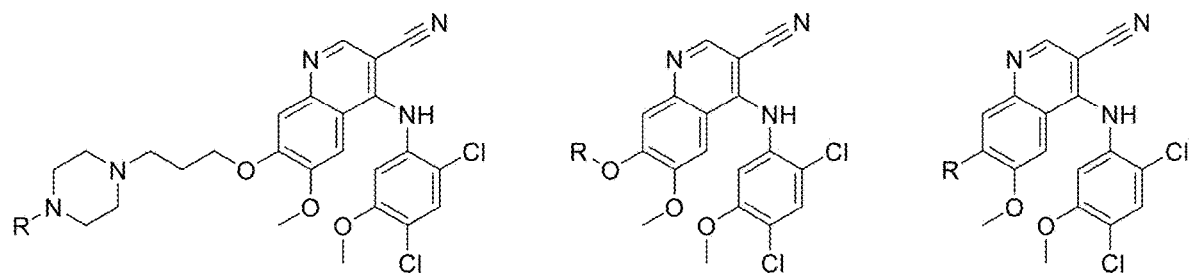
FIG. 8OOOO
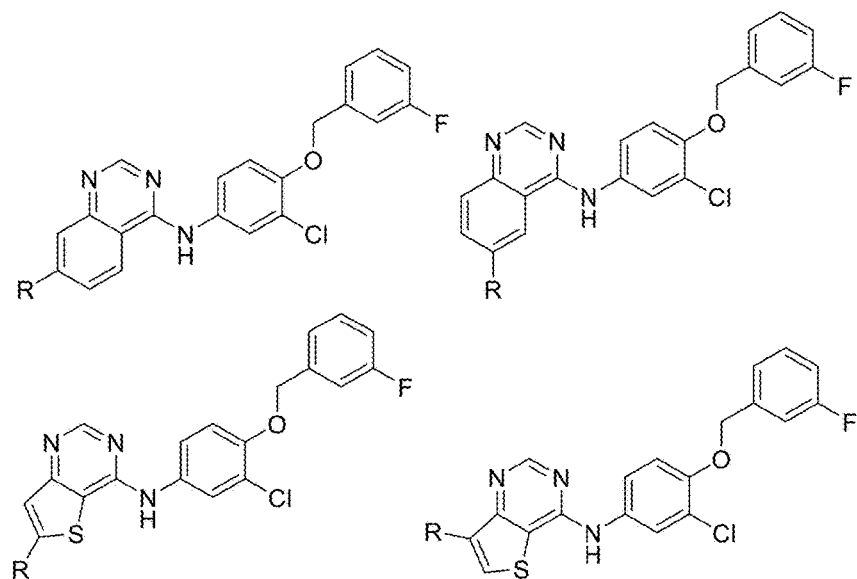
FIG. 8PPPP
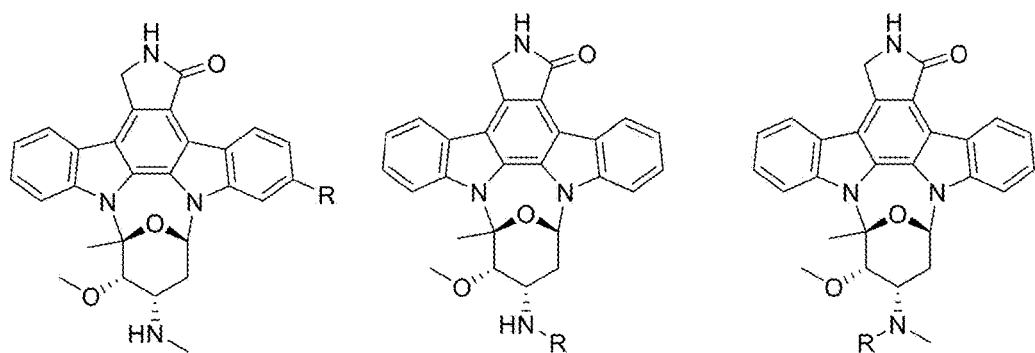

FIG. 8QQQQ
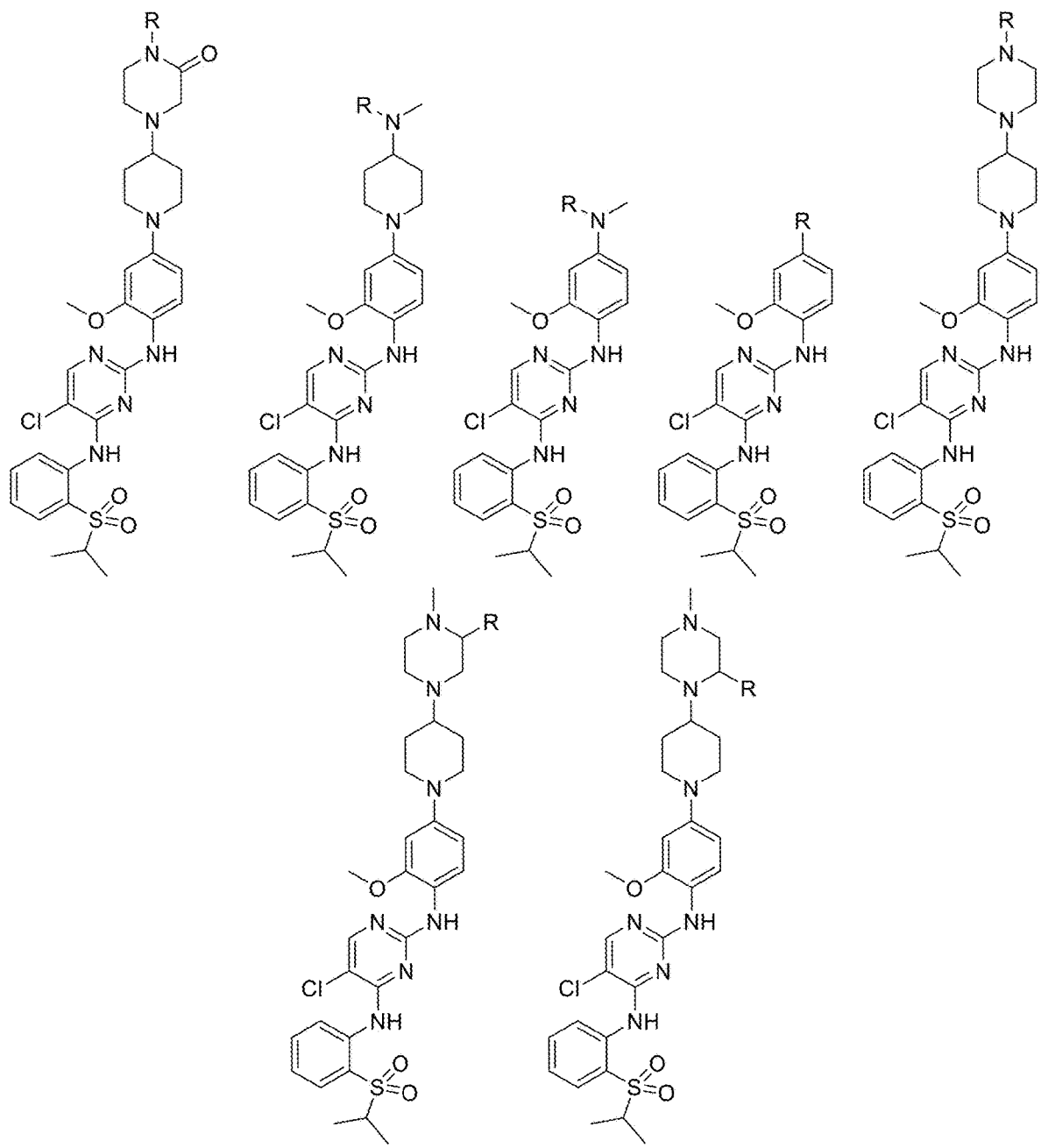

FIG. 8RRRR
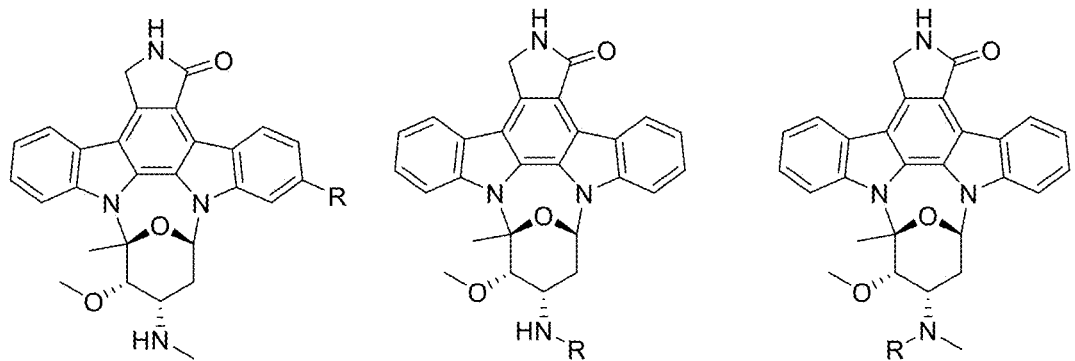
FIG. 8SSSS
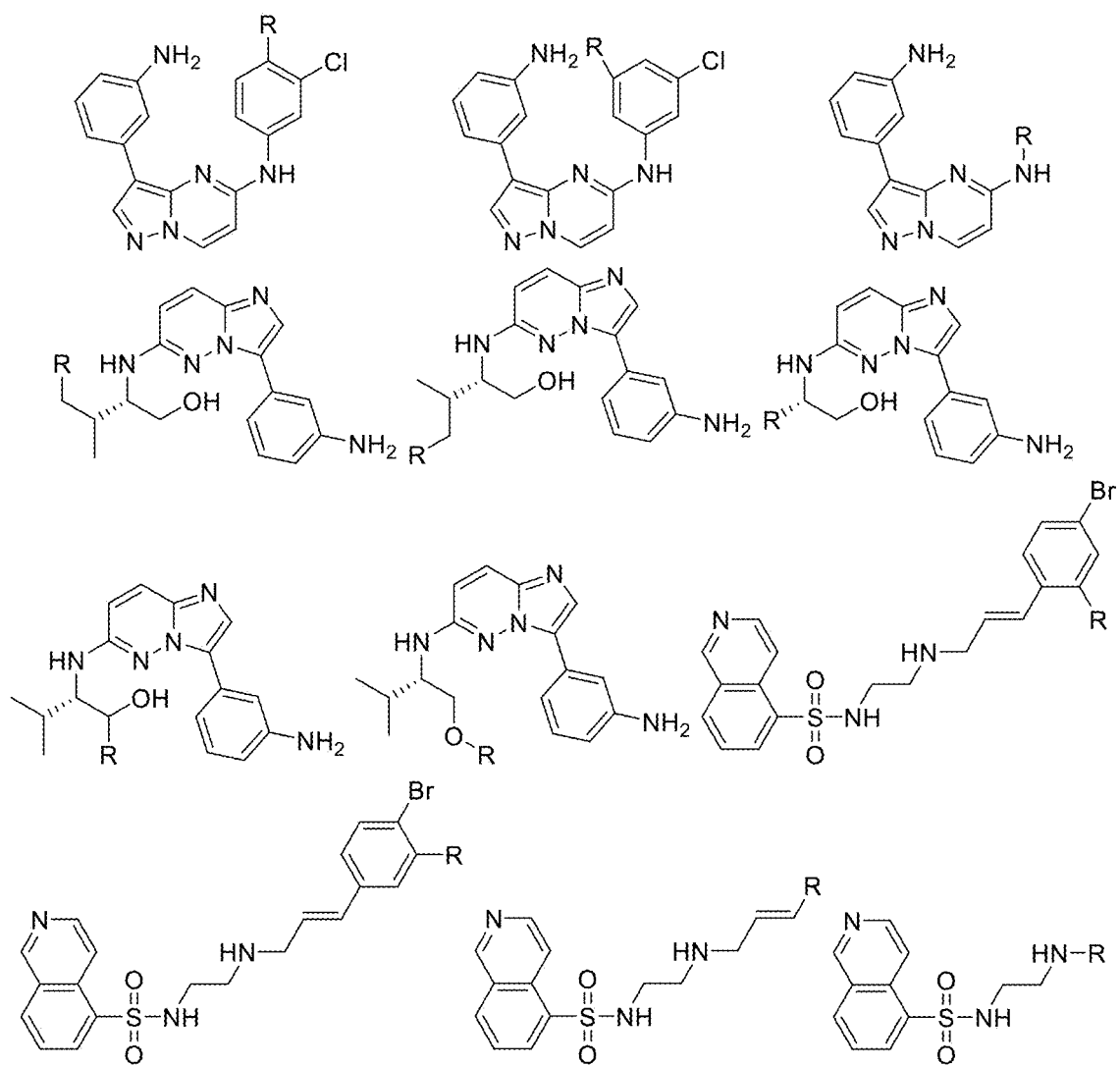

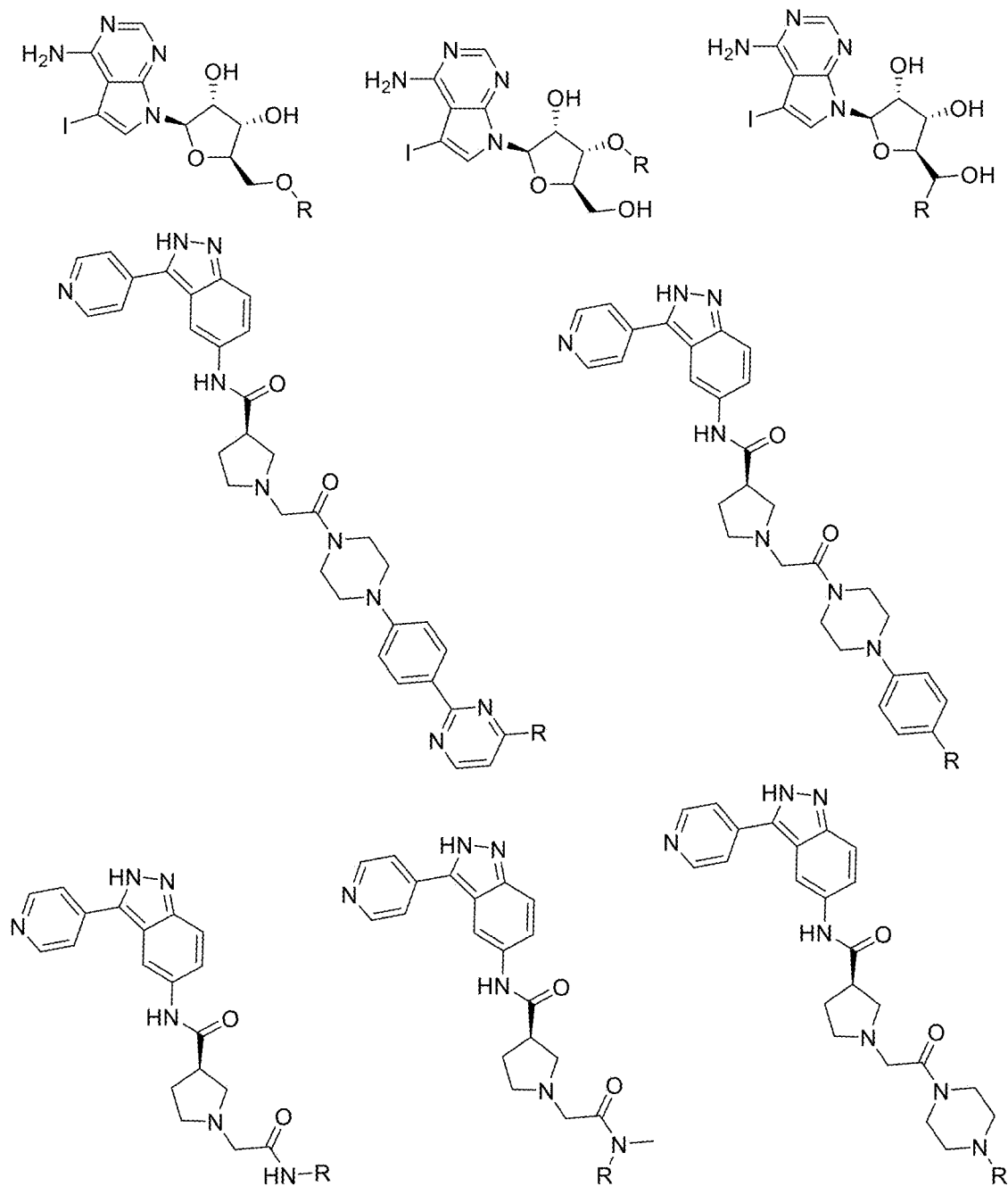
FIG. 8TTTT

FIG. 8UUUU
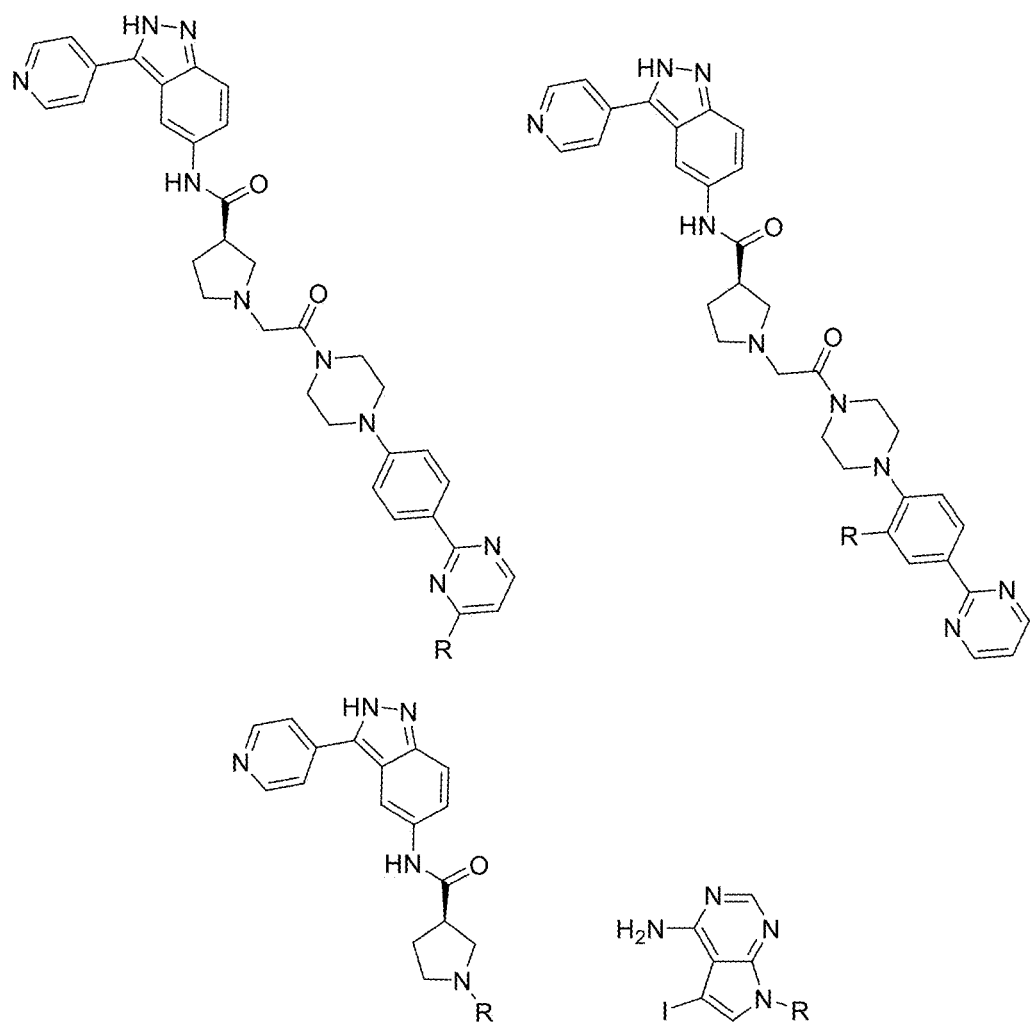

FIG. 8VVVV
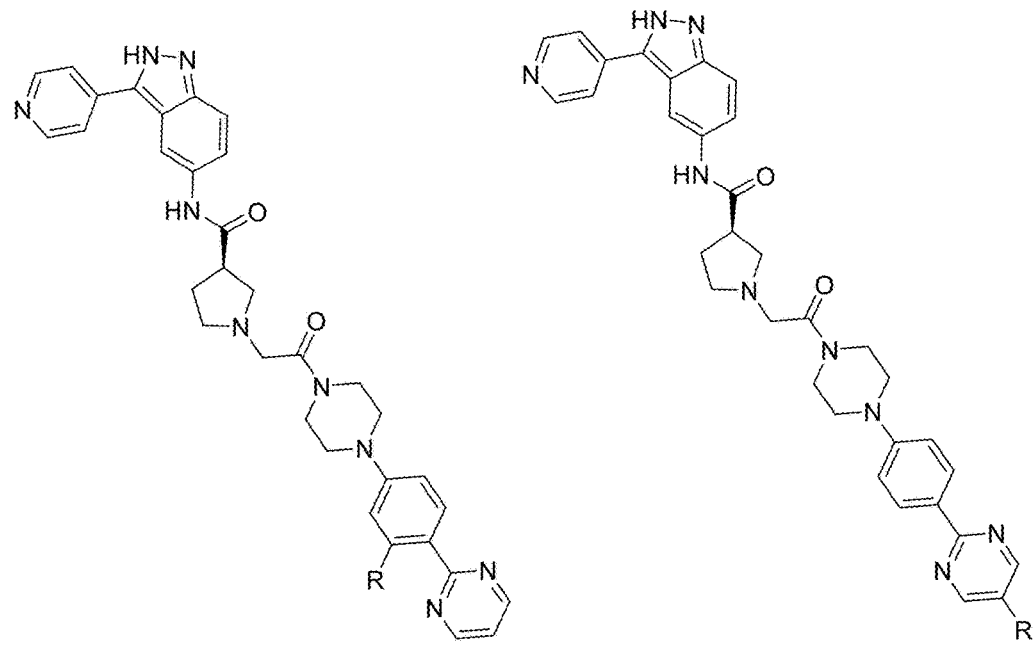
FIG. 8WWWW
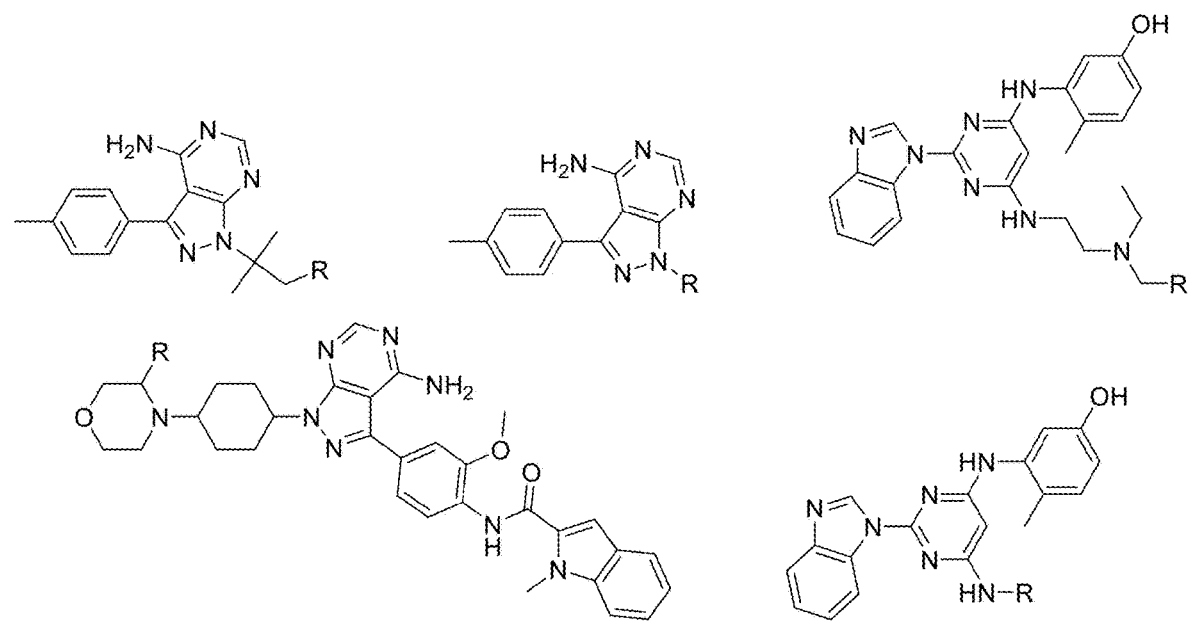

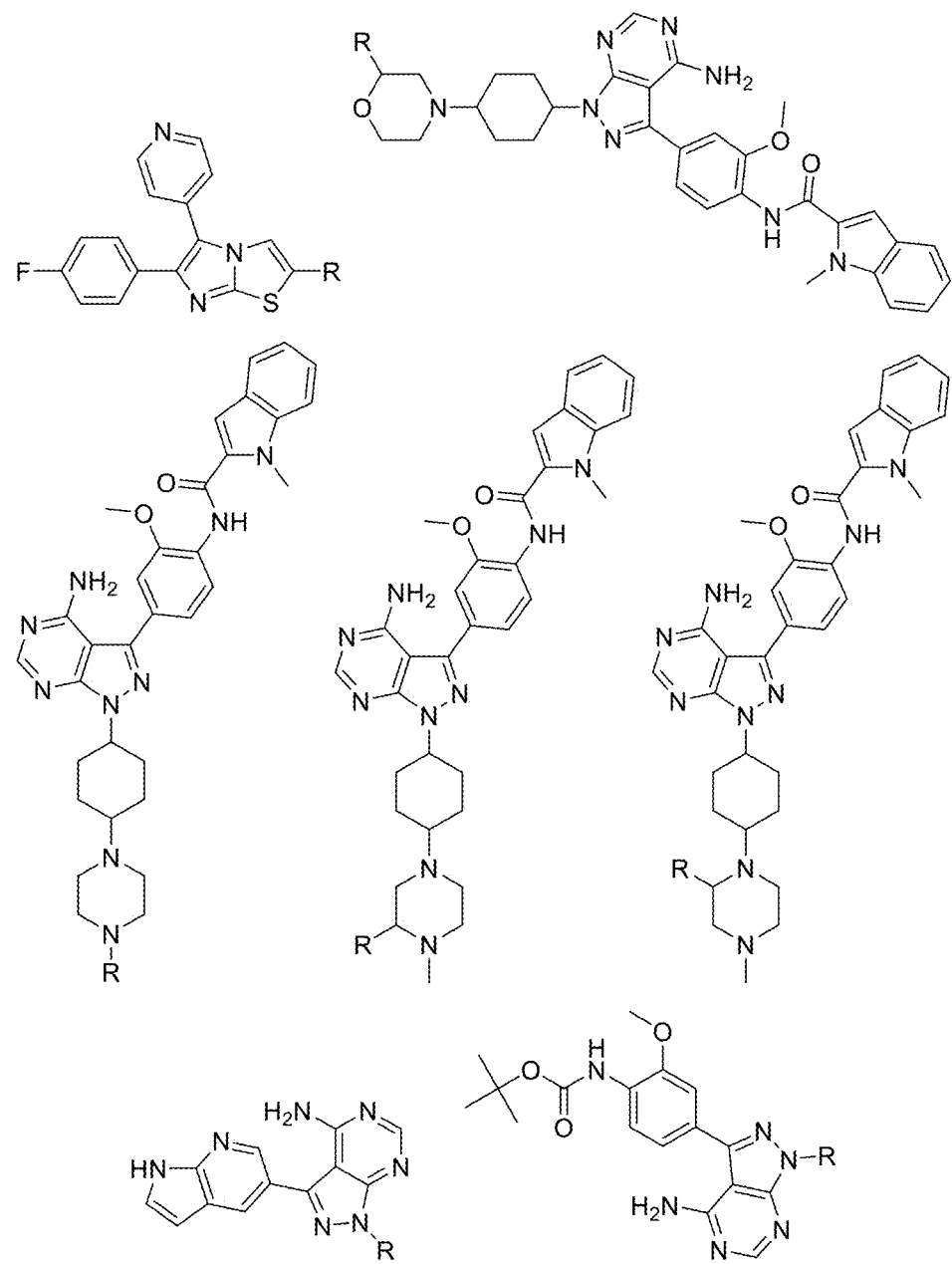
FIG. 8XXXX

FIG. 8YYYY
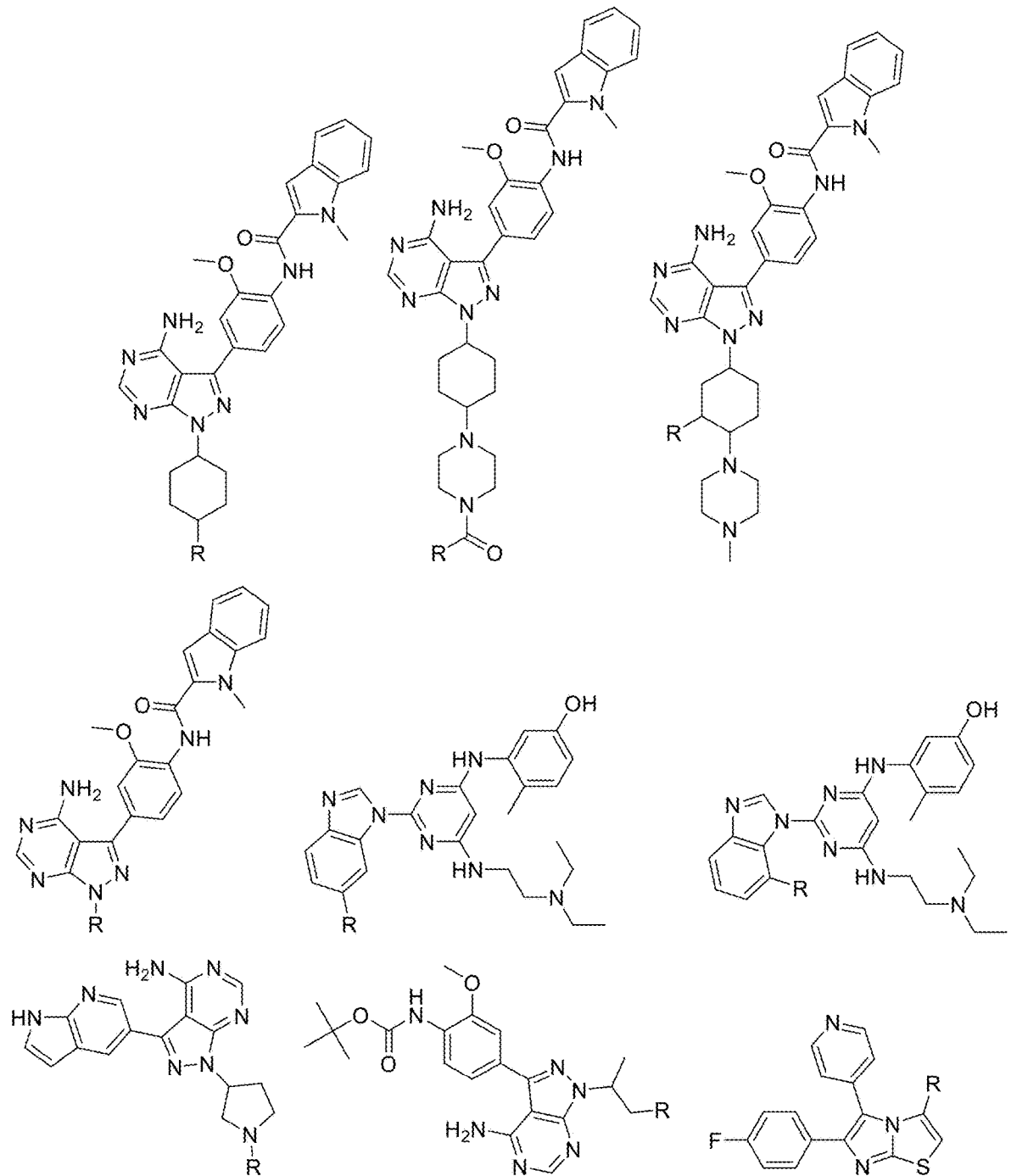

FIG. 8ZZZZ
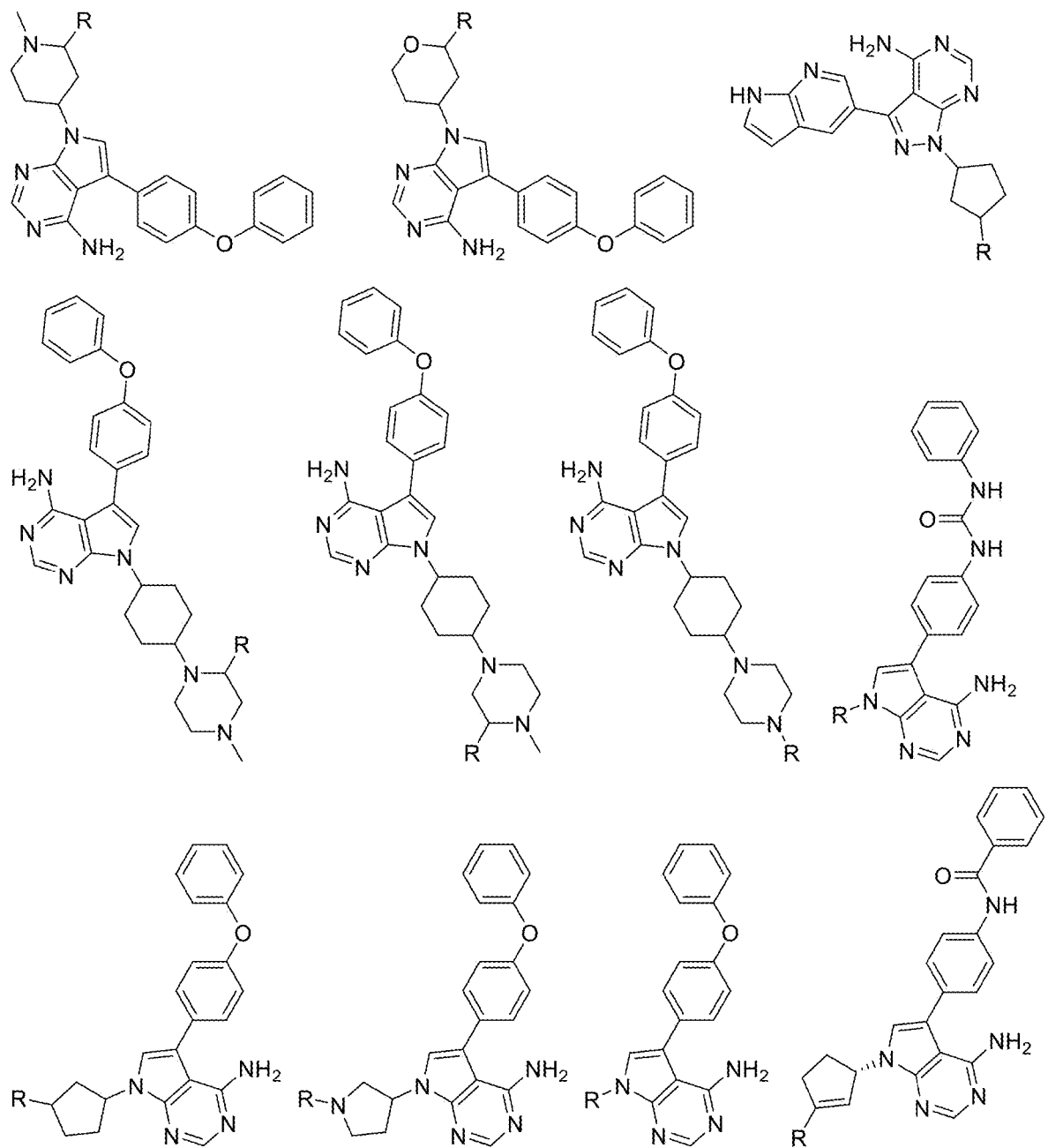

FIG. 8AAAAA
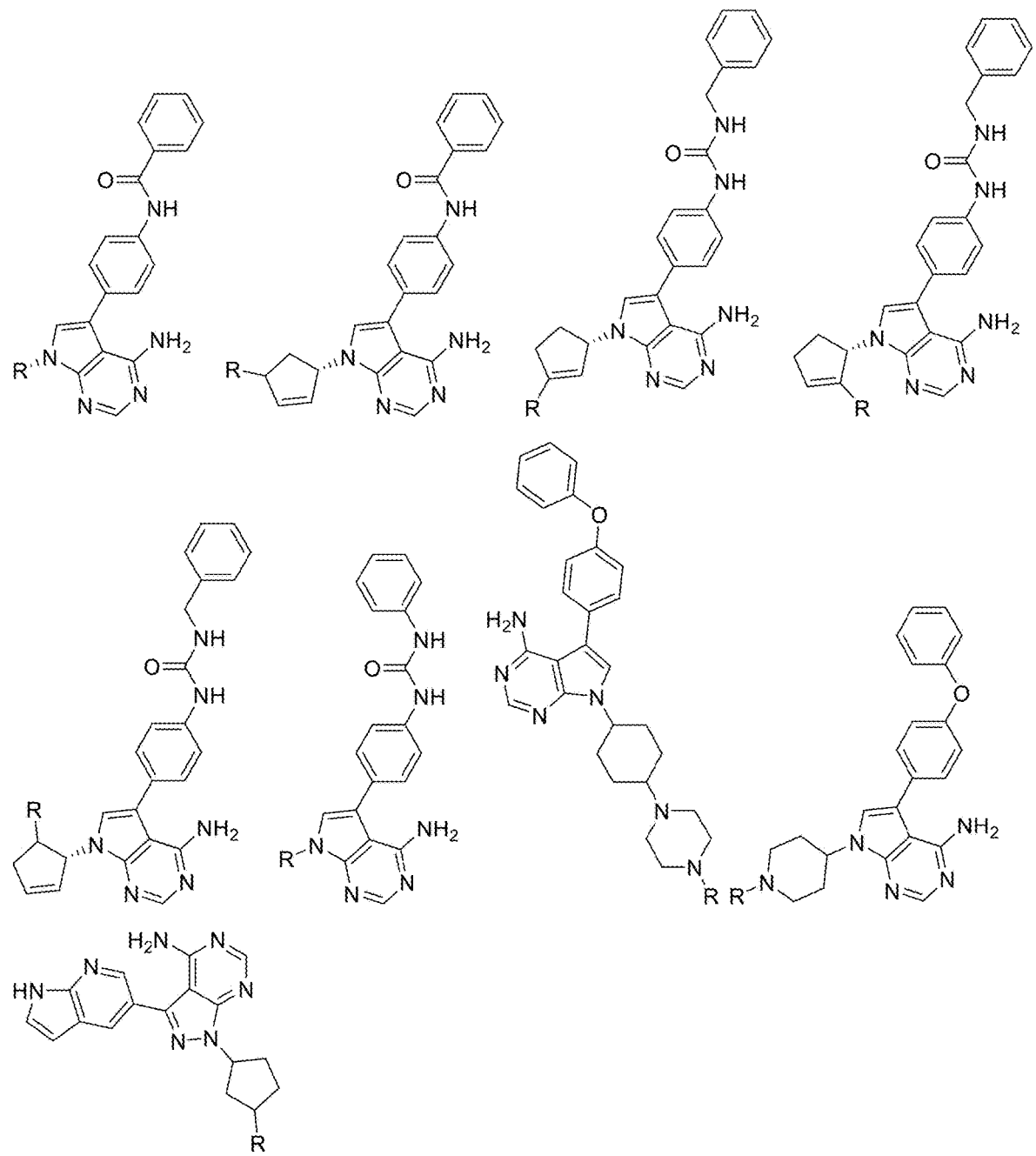

FIG. 8BBBBB
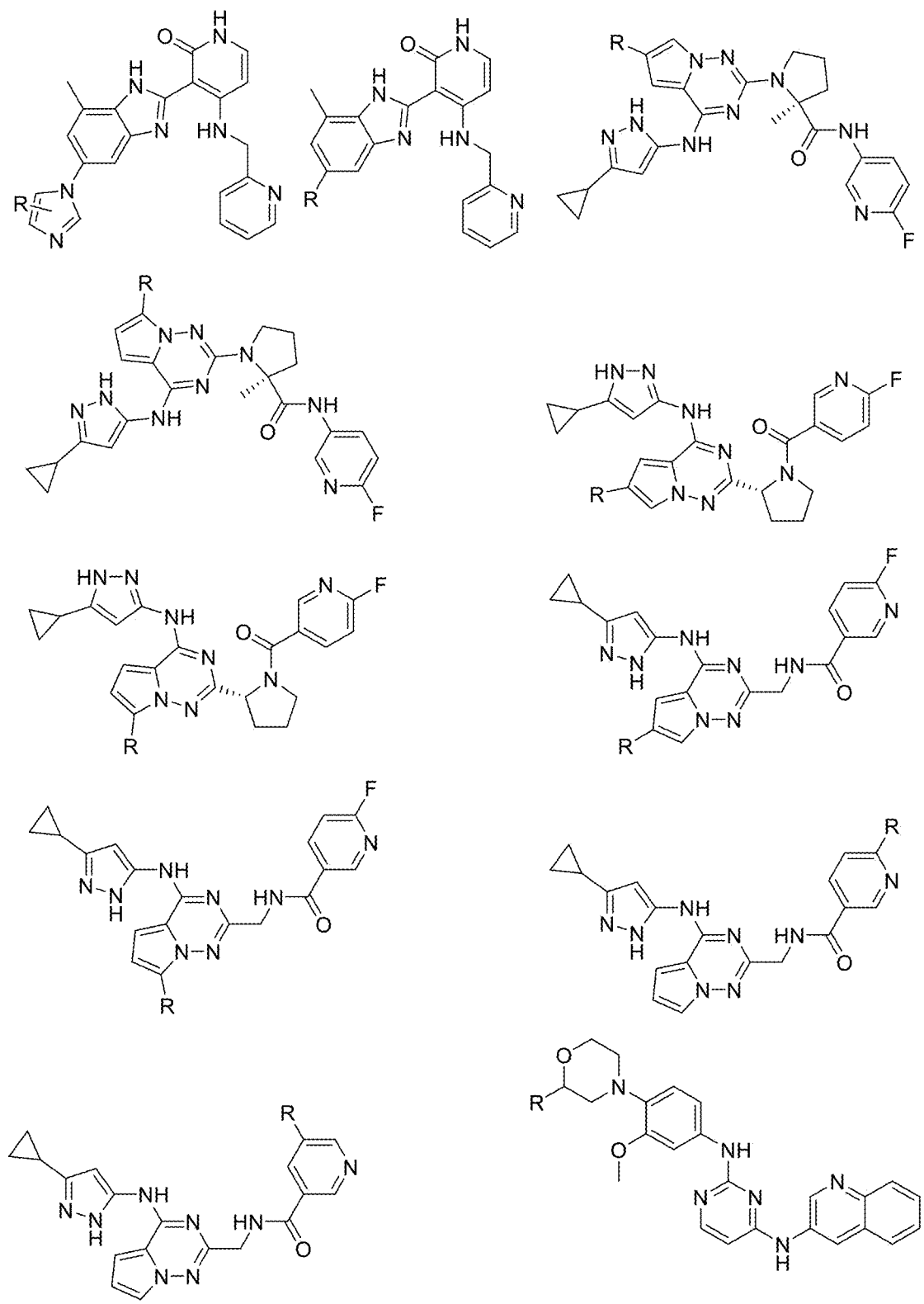

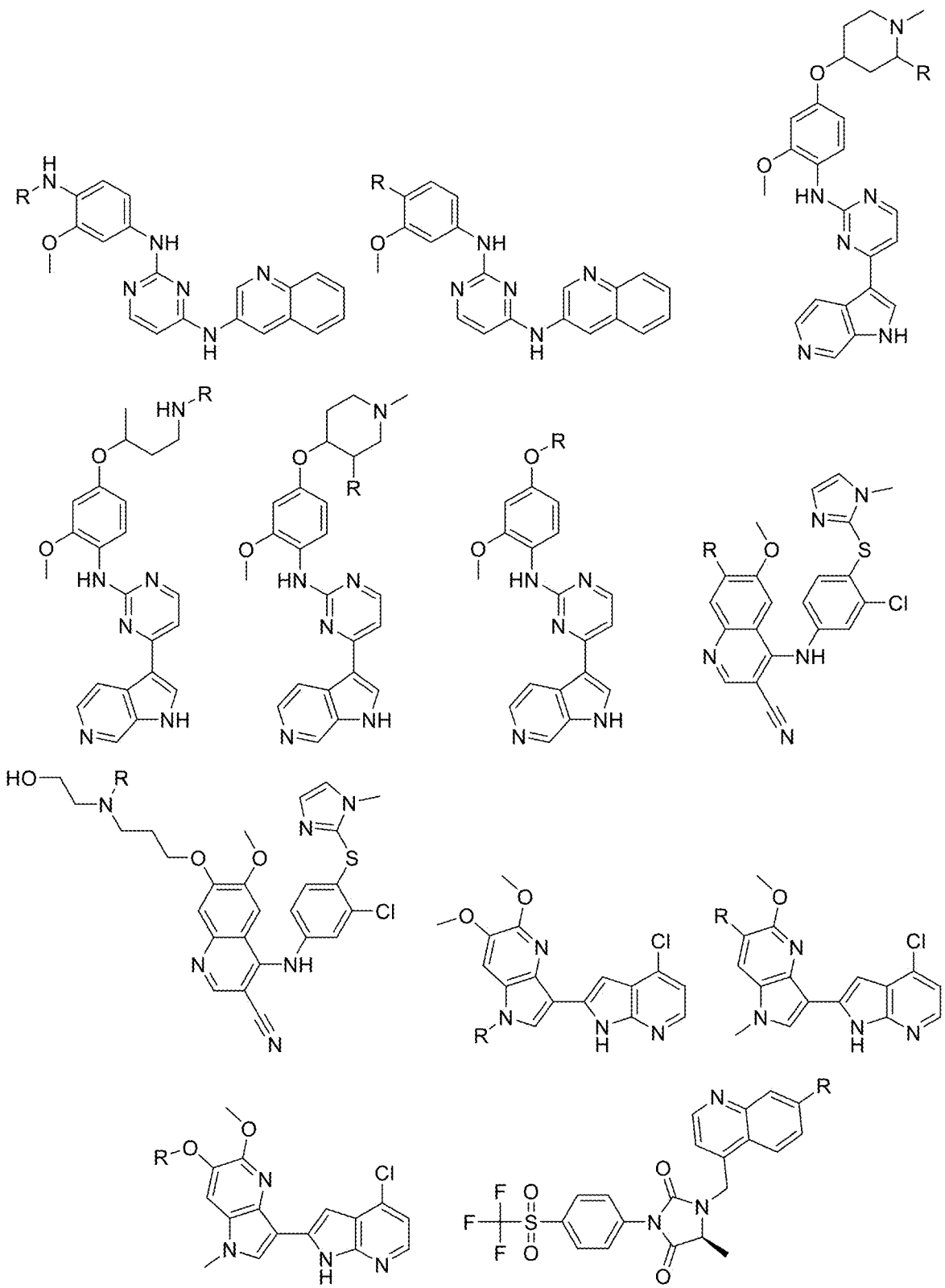

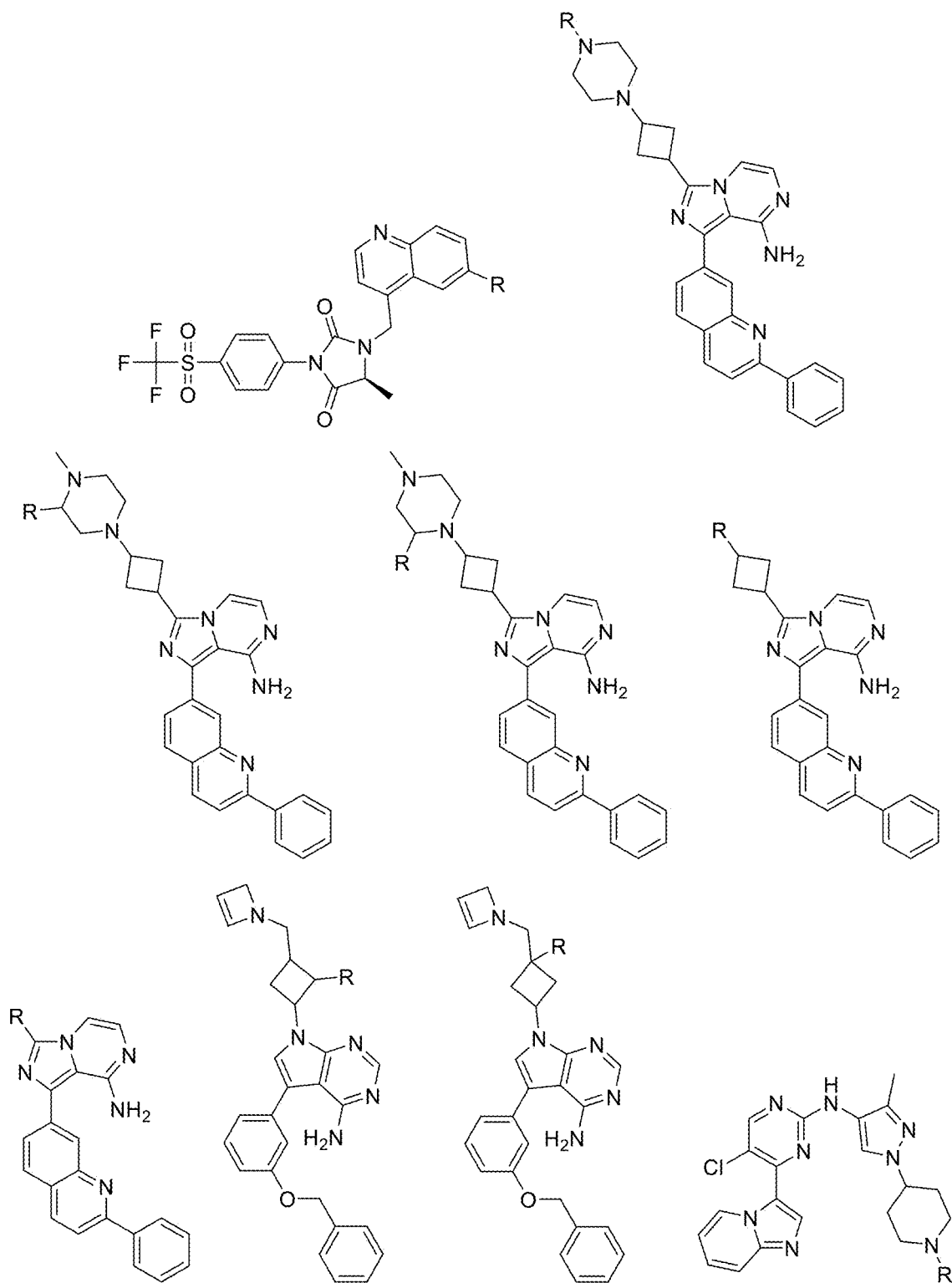
FIG. 8DDDDD

FIG. 8EEEEE
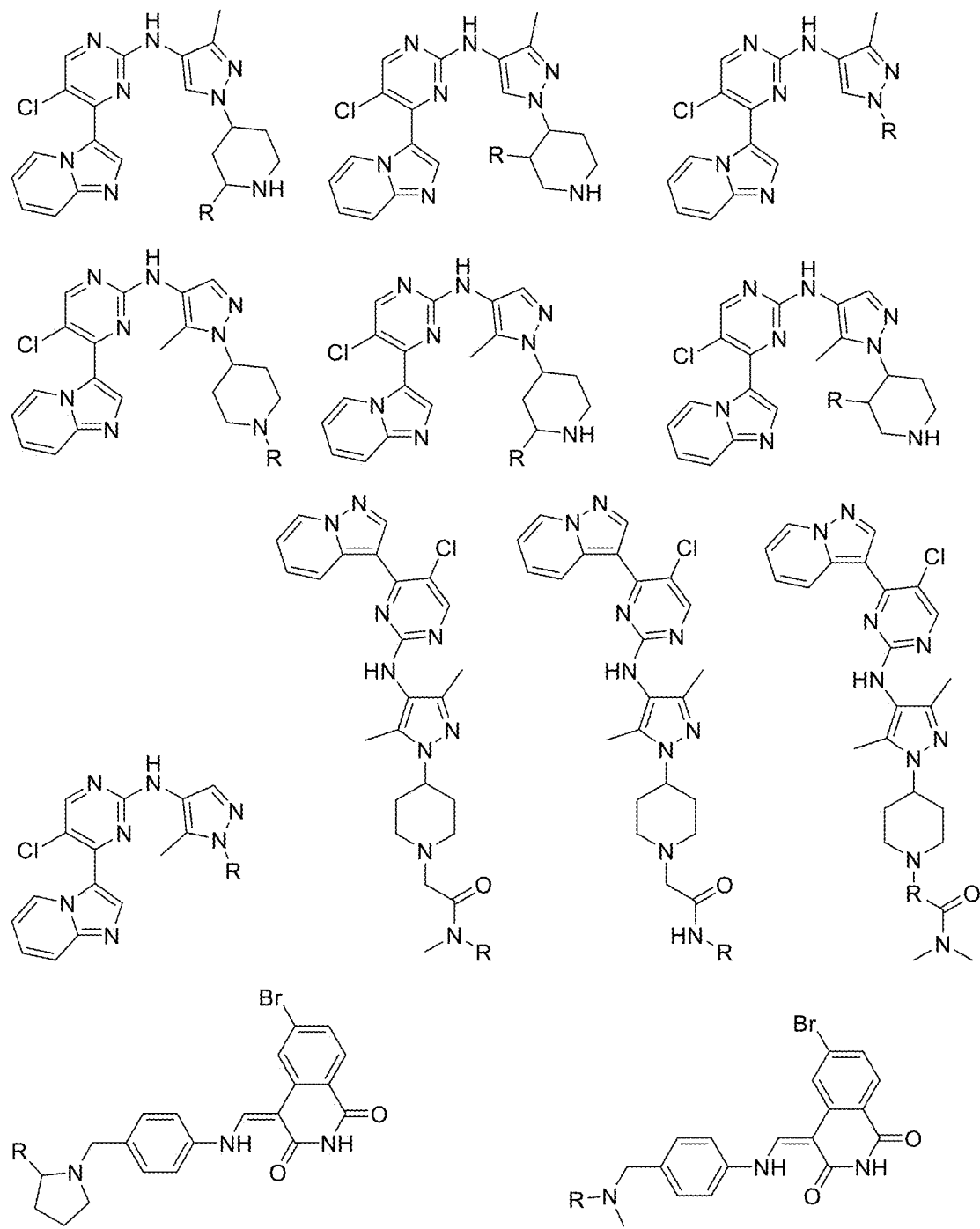

FIG. 8FFFFF
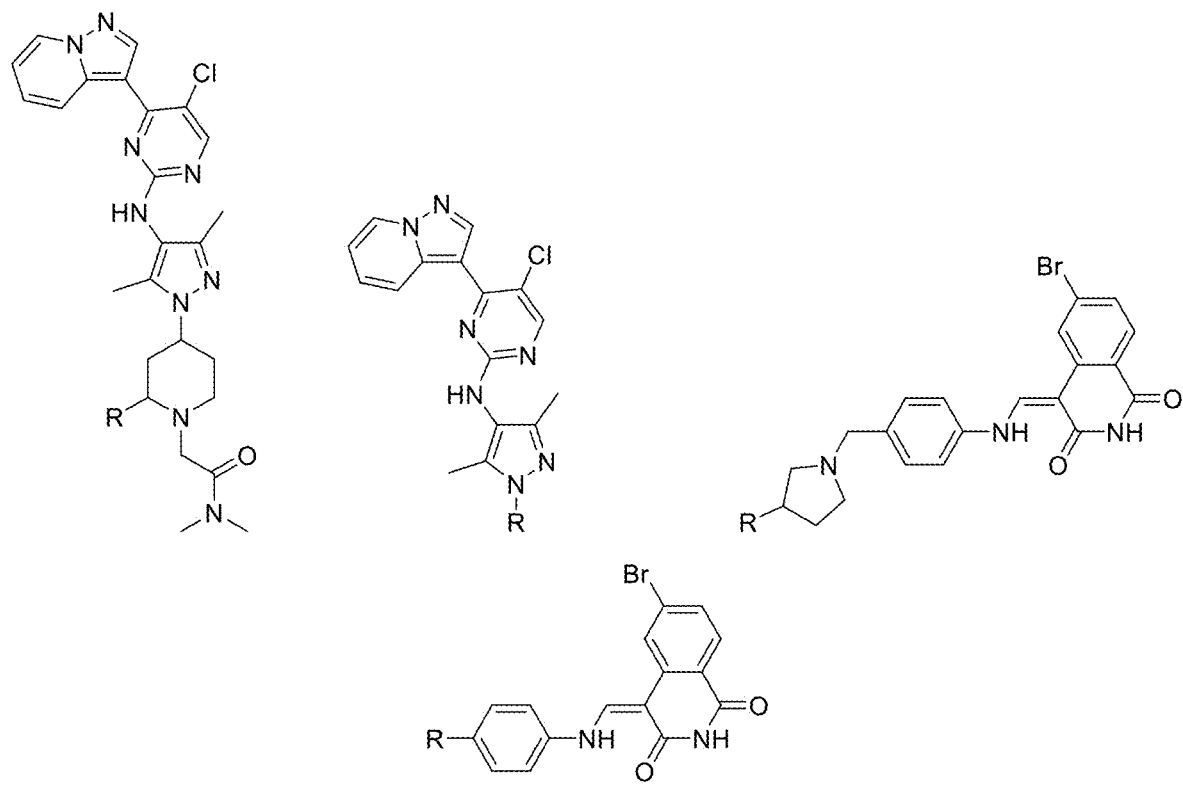
FIG. 8GGGGG
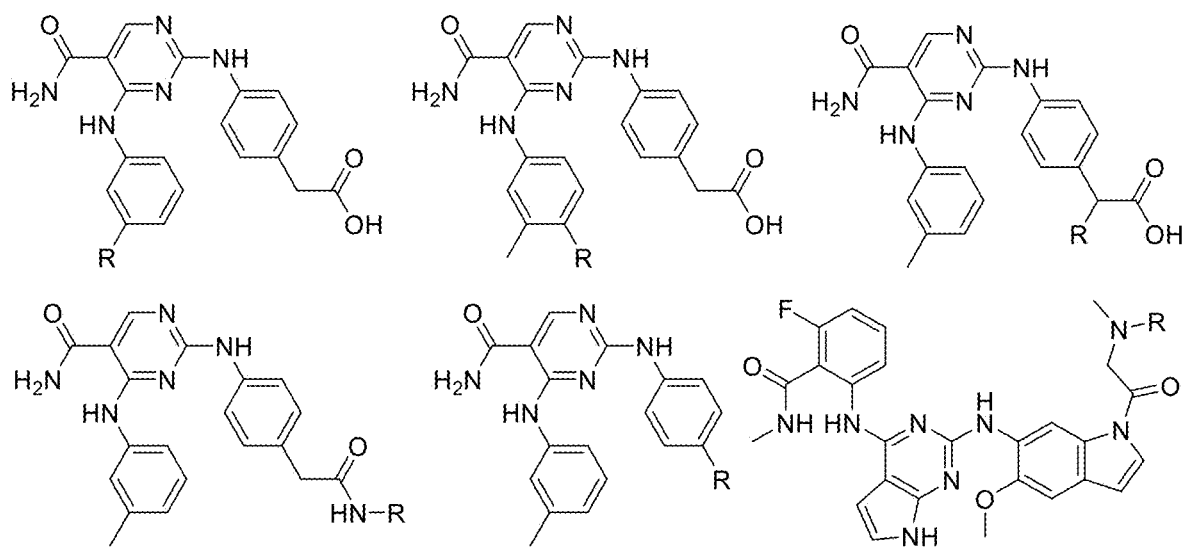

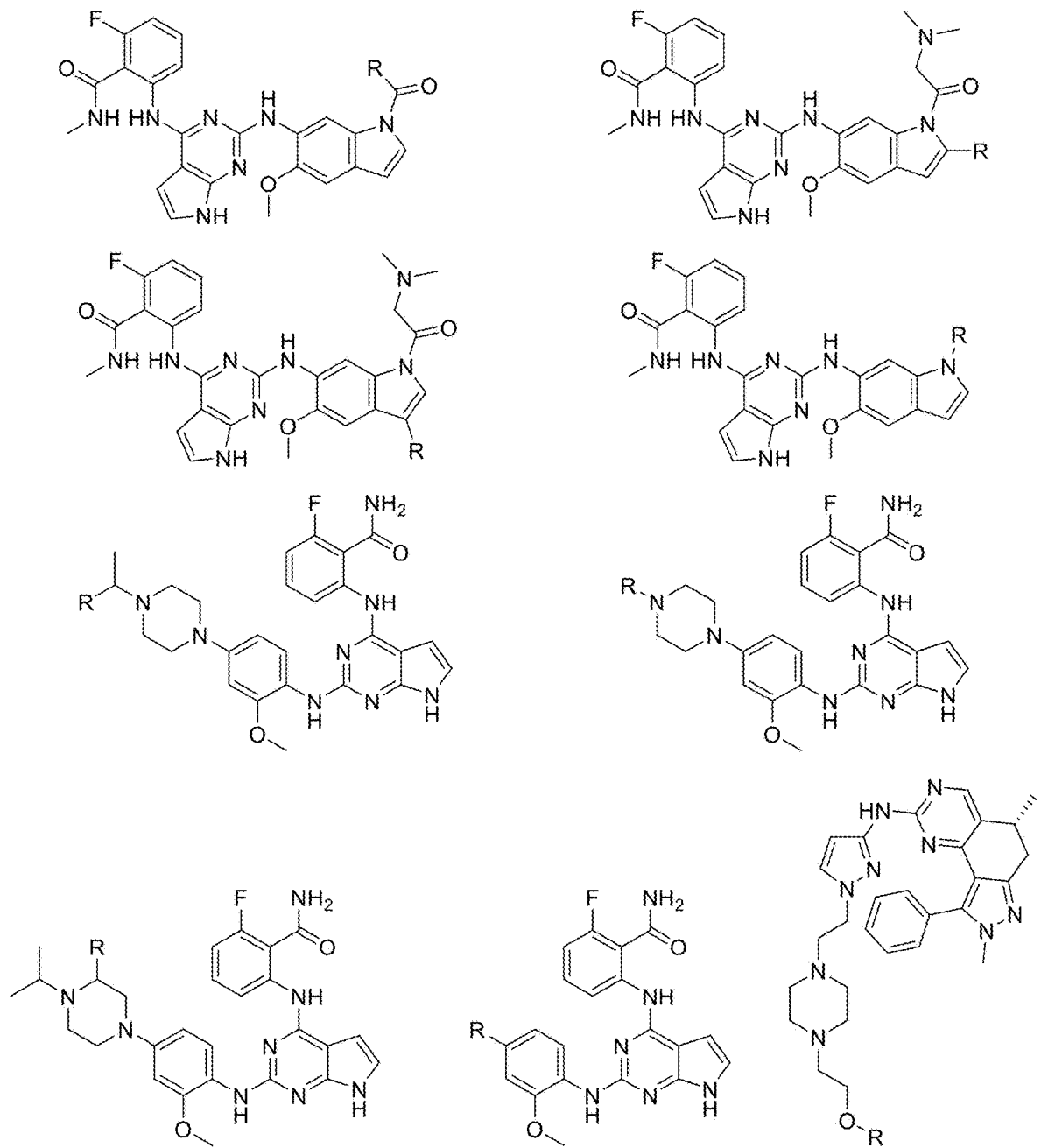
FIG. 8HHHHH

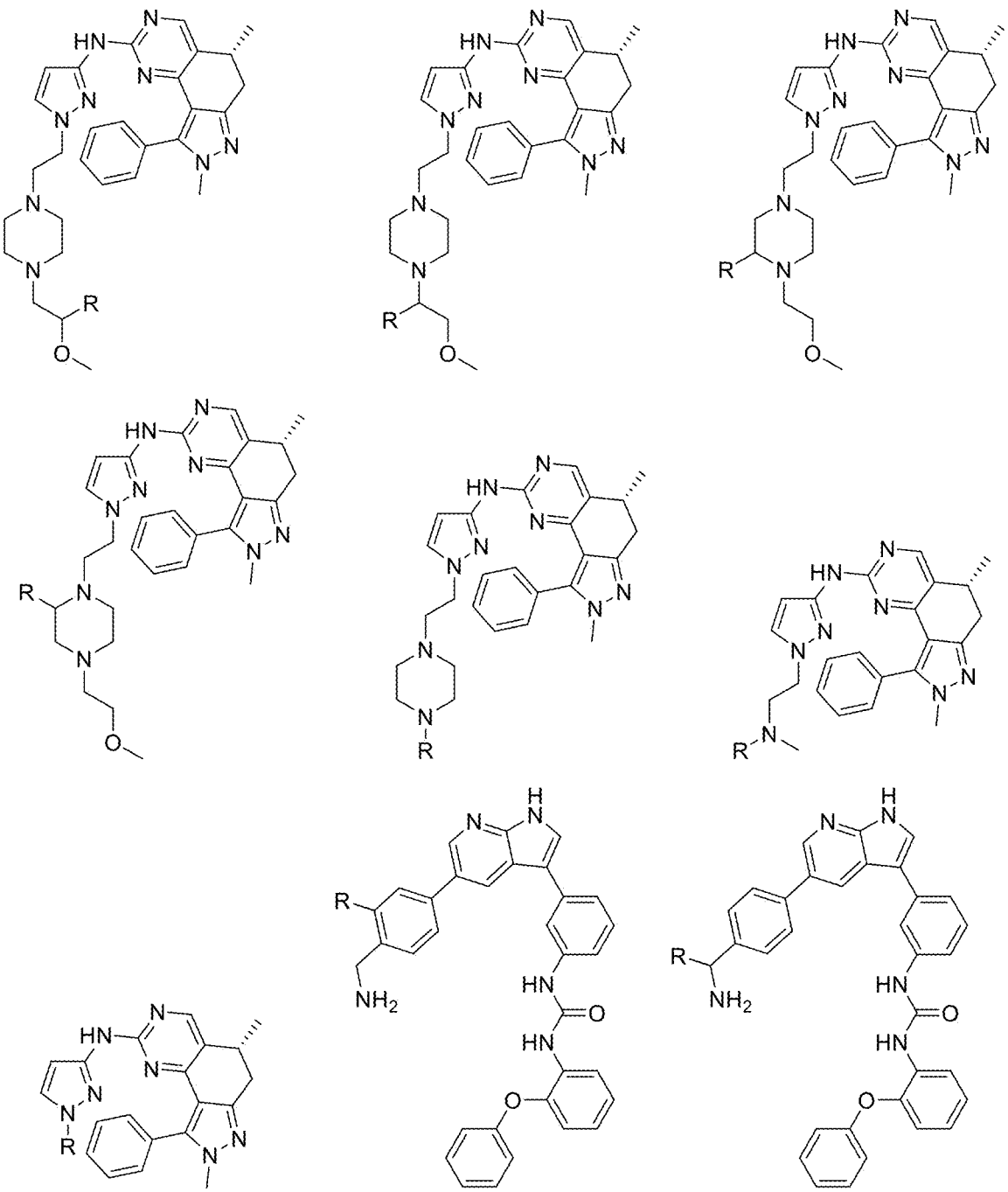
FIG. 8IIIII

FIG. 8JJJJJ
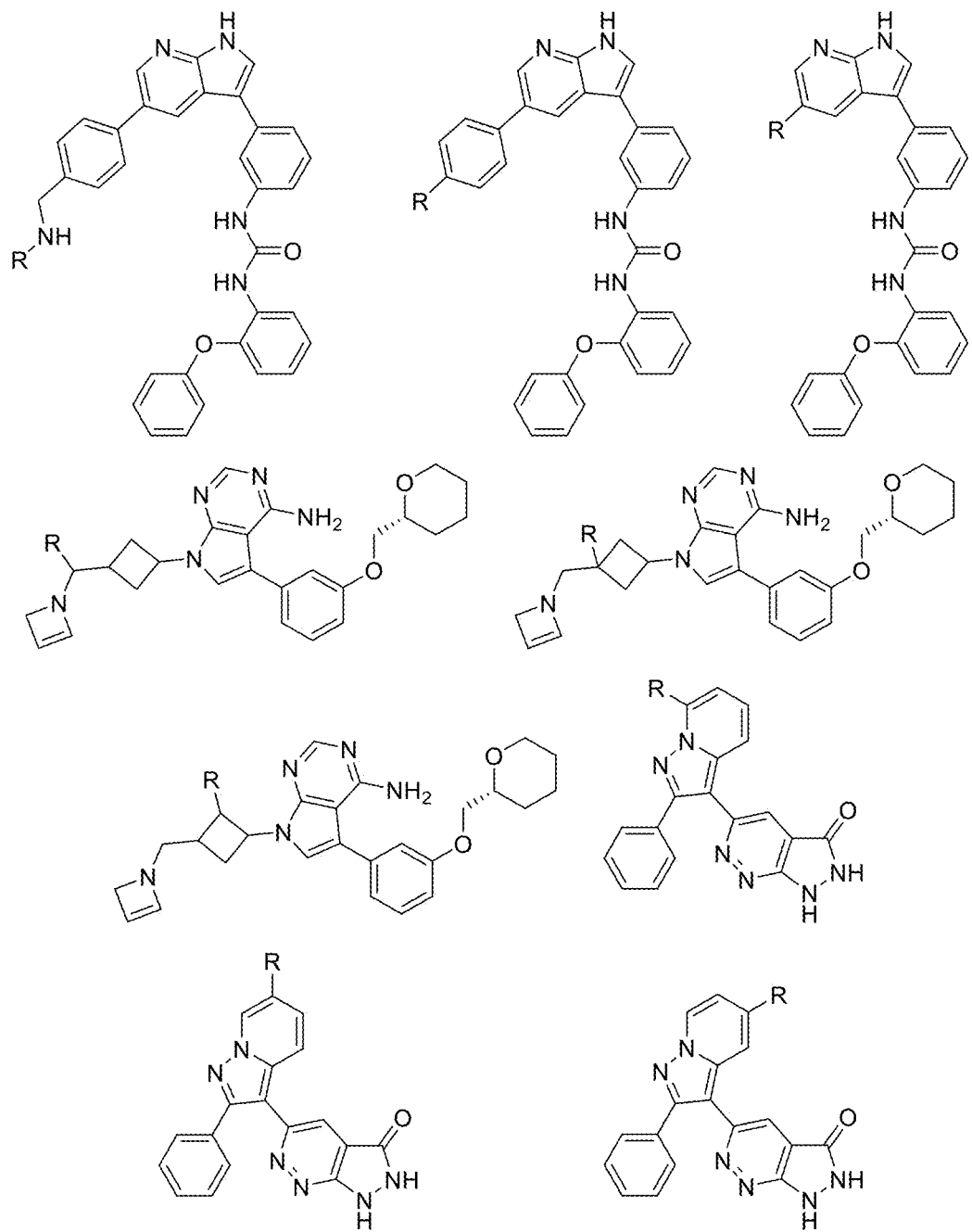

FIG. 8KKKKK
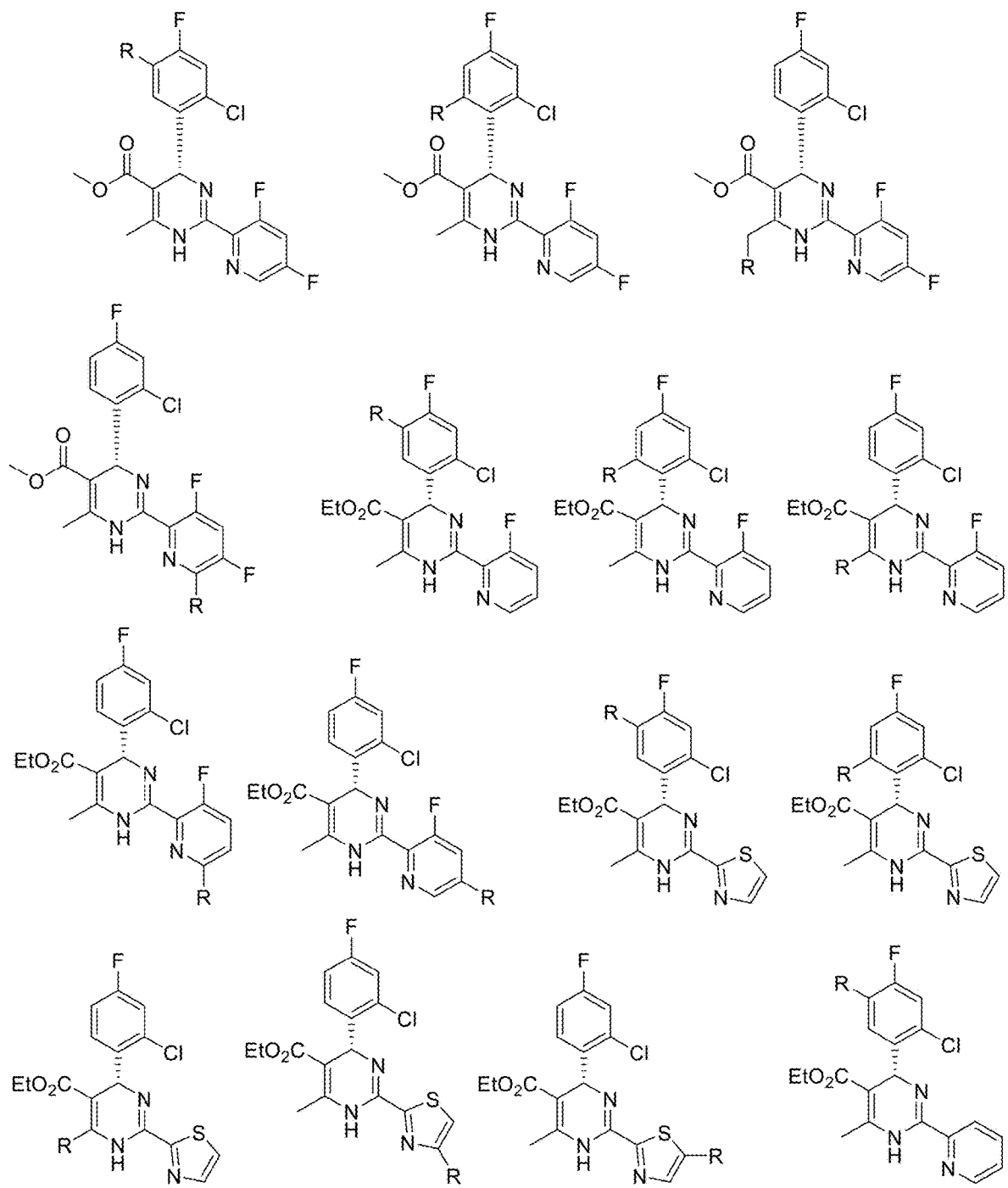

FIG. 8LLLLL
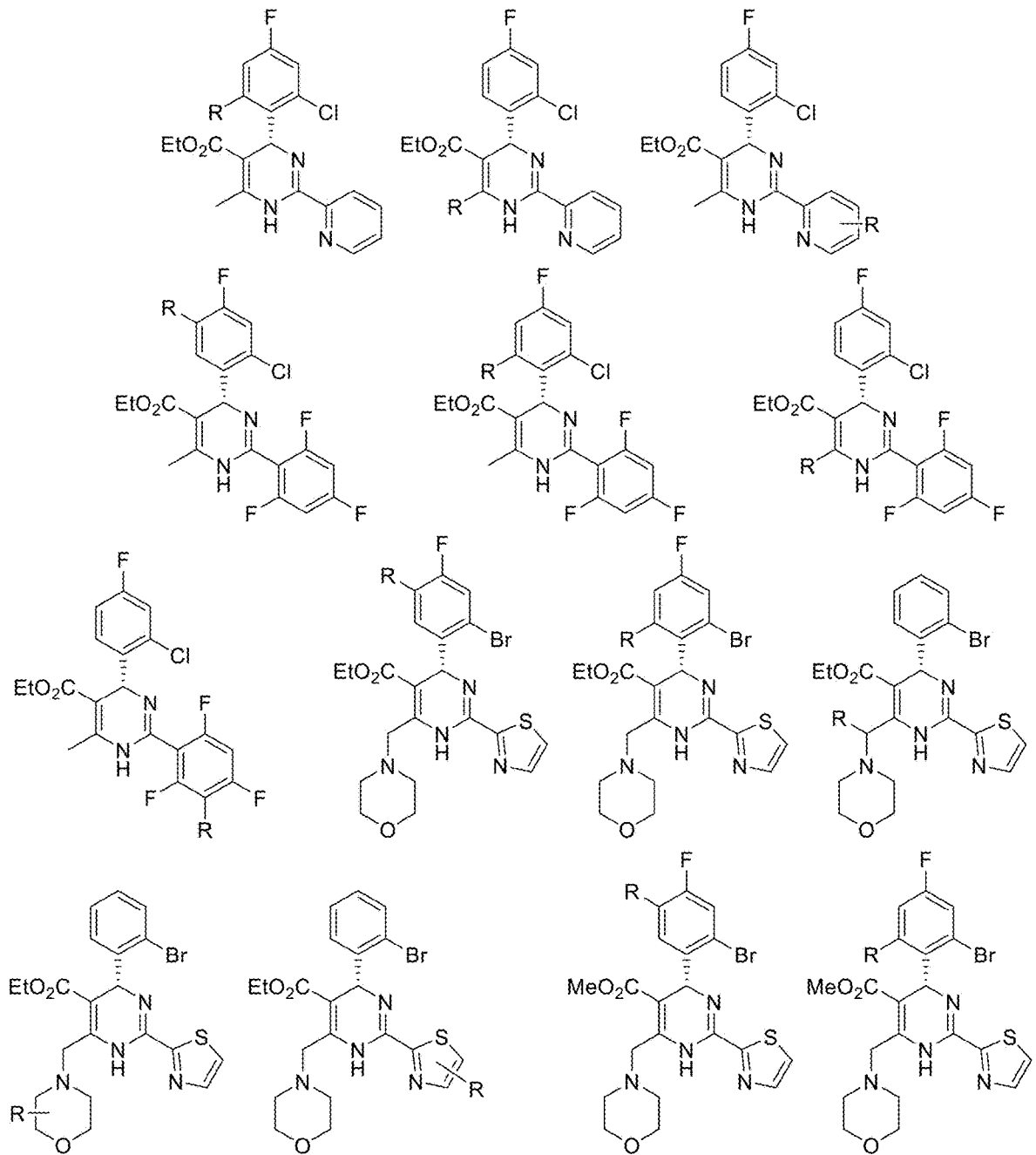

FIG. 8MMMMM
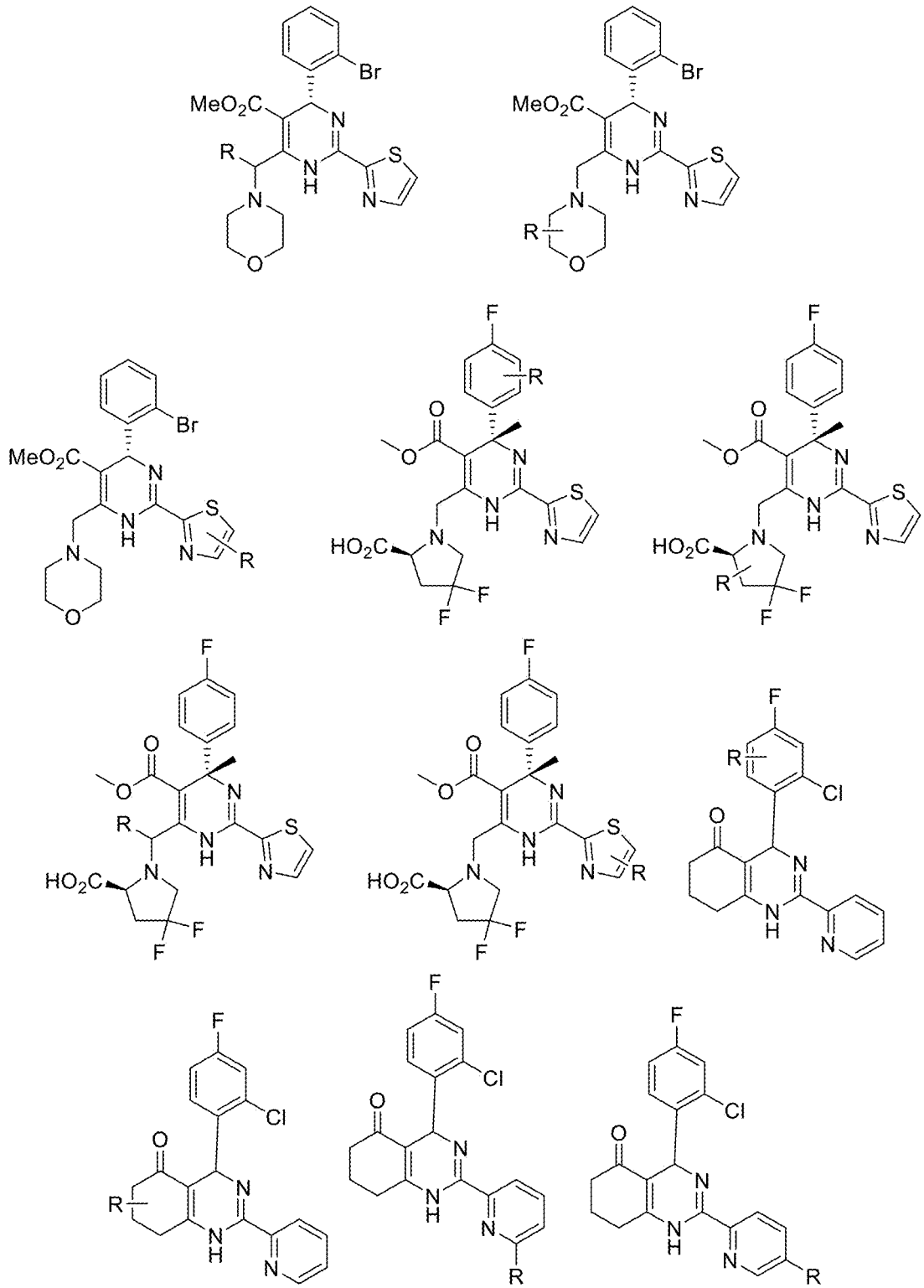

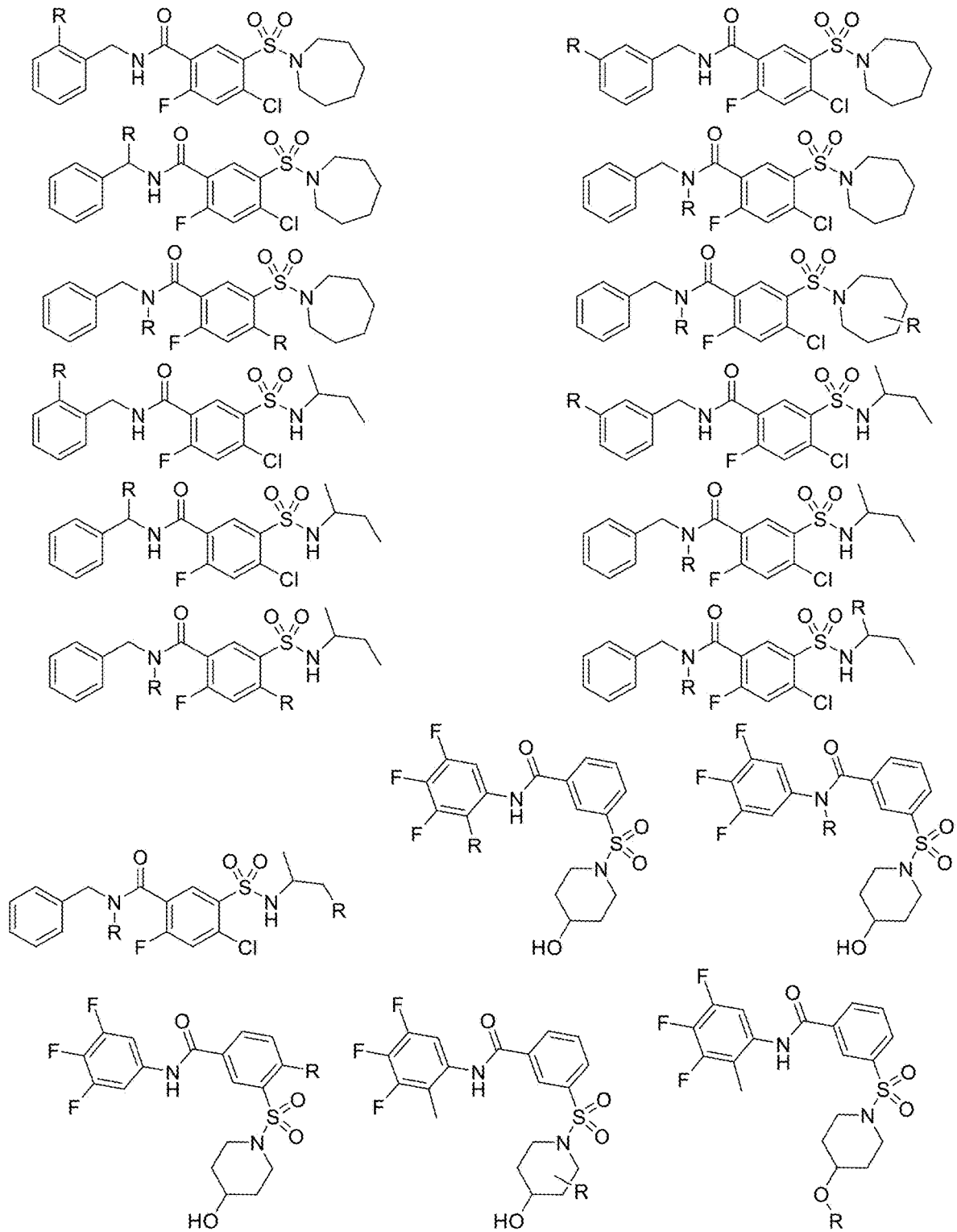
FIG. 8NNNNN

FIG. 800000
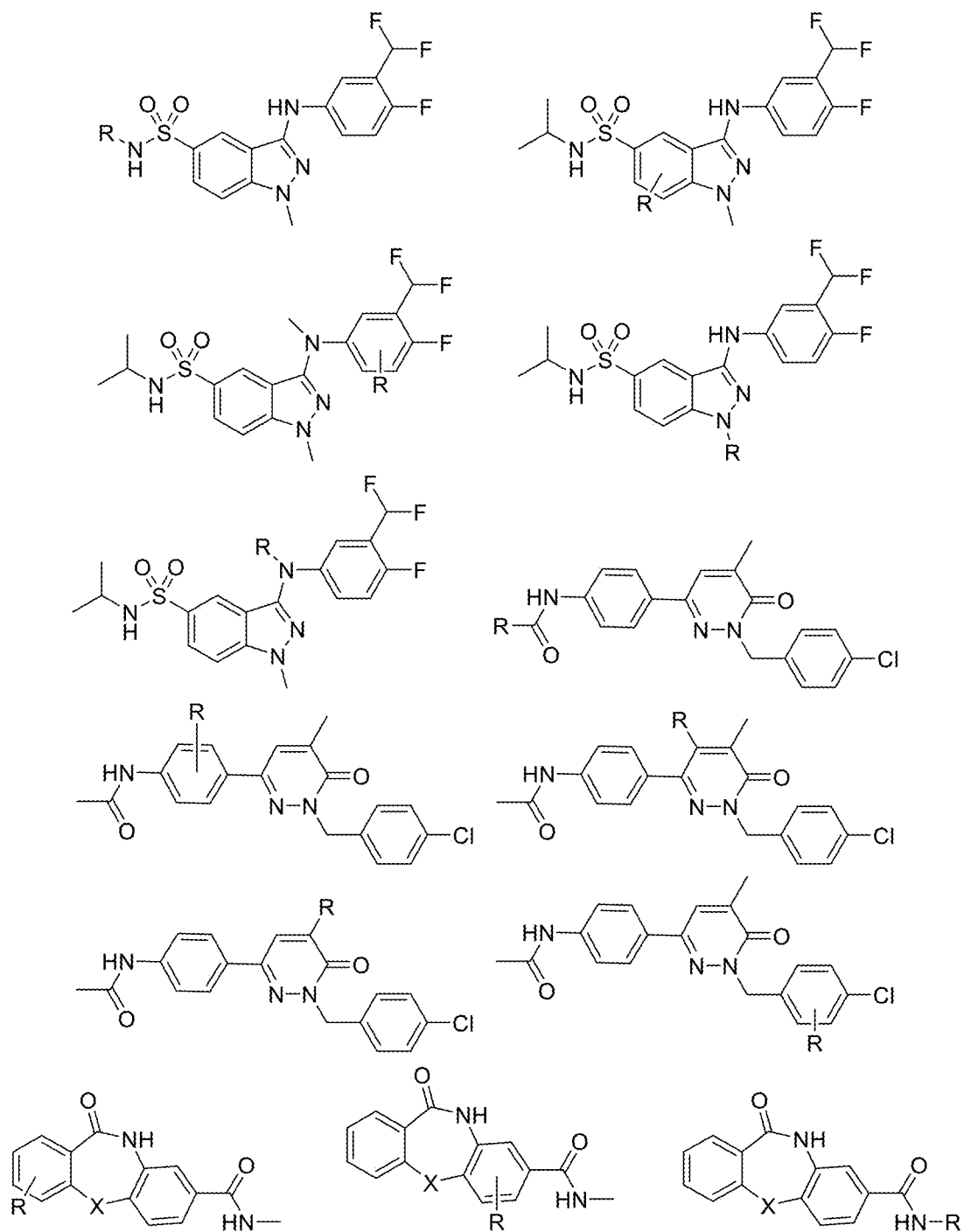

FIG. 8PPPPP
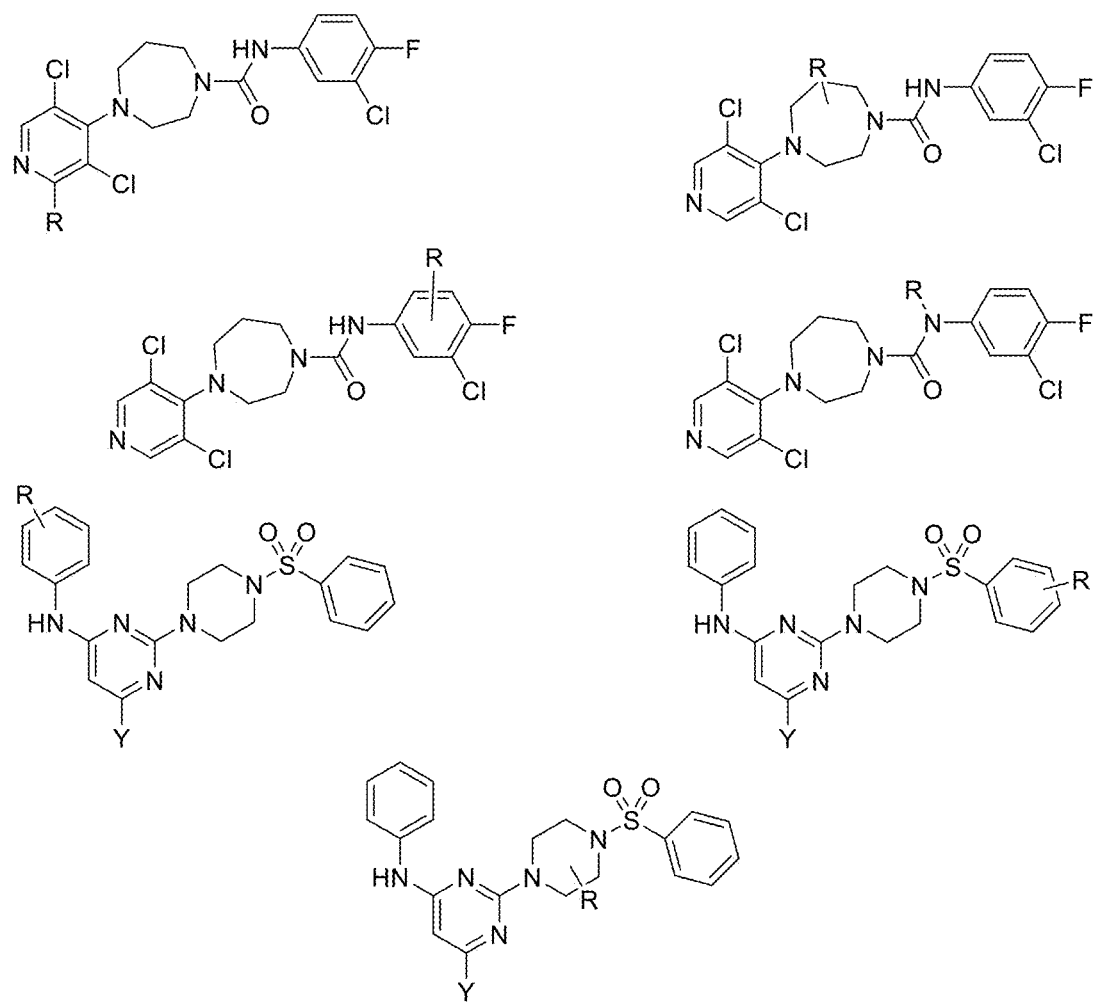

FIG. 63
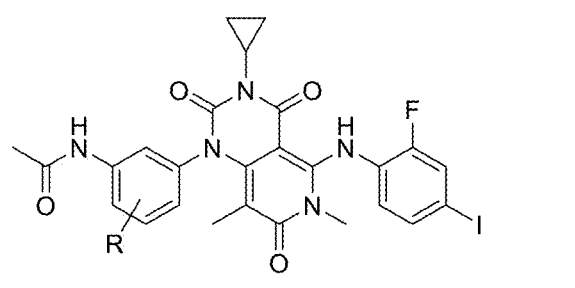
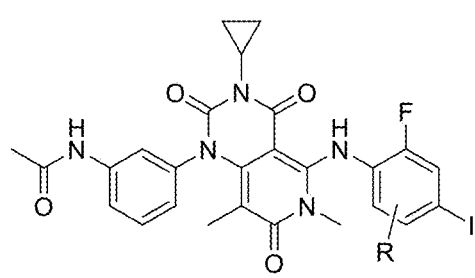
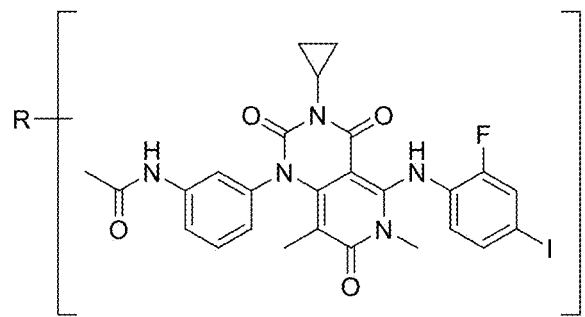
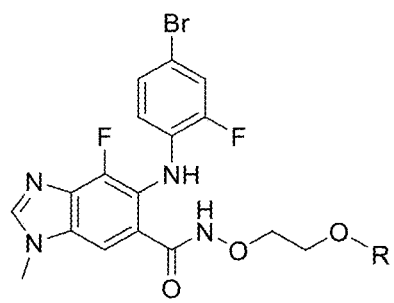
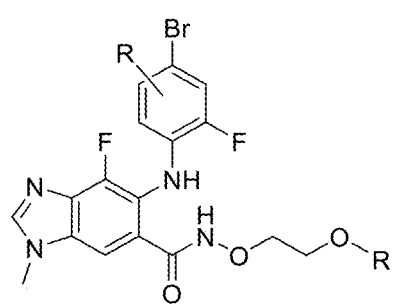
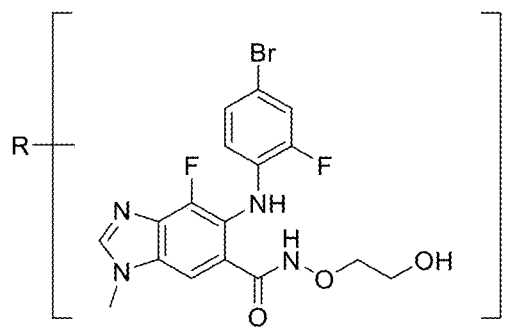

FIG. 71
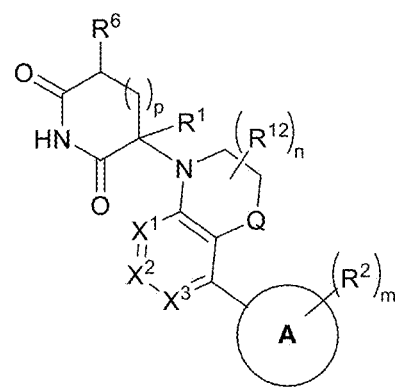
(IA)
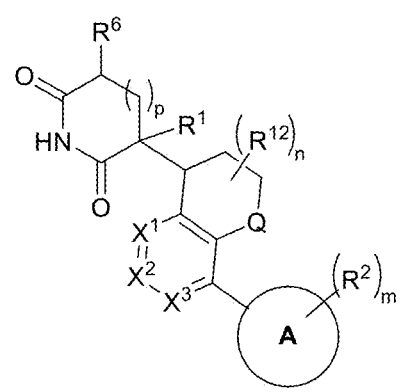
(IIA)
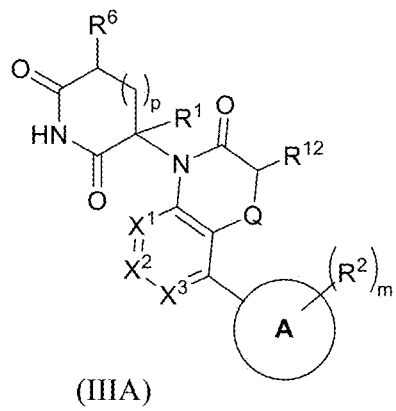
(IIIA)
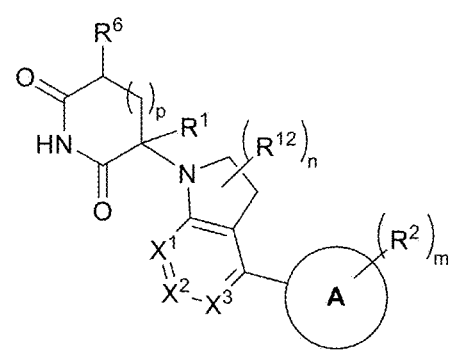
(IVA)

BICYCLIC-SUBSTITUTED GLUTARIMIDE CEREBLON BINDERS

CROSS REFERENCE TO RELATED APPLICATIONS

This application is a continuation of International Patent Application No. PCT/US2023/024622, filed in the U. S. Receiving Office on Jun. 6, 2023, which claims the benefit of U. S. Provisional Application 63/349,509, filed on Jun. 6, 2022. The entirety of each of these applications is hereby incorporated by reference for all purposes.

FIELD OF THE INVENTION

This invention provides Degron compounds which bind to cereblon which is a component of the E3 ubiquitin ligase. The Degrons provided herein can be used to modulate the activity of cereblon either alone or as covalently linked to a Tail. Alternatively, the Degron can be linked to a Targeting Ligand which binds to a Target Protein for protein degradation.

BACKGROUND OF THE INVENTION

Protein degradation is a highly regulated and essential process that maintains cellular homeostasis. The selective identification and removal of damaged, misfolded, or excess proteins is achieved via the ubiquitin-proteasome pathway (UPP). The UPP is central to the regulation of almost all cellular processes, including antigen processing, apoptosis, biogenesis of organelles, cell cycling, DNA transcription and repair, differentiation and development, immune response and inflammation, neural and muscular degeneration, morphogenesis of neural networks, modulation of cell surface receptors, ion channels and the secretory pathway, the response to stress and extracellular modulators, ribosome biogenesis and viral infection.

Covalent attachment of multiple ubiquitin molecules by an E3 ubiquitin ligase to a terminal lysine residue marks the protein for proteasome degradation, where the protein is digested into small peptides and eventually into its constituent amino acids that serve as building blocks for new proteins. Defective proteasomal degradation has been linked to a variety of clinical disorders including Alzheimer's disease, Parkinson's disease, Huntington's disease, muscular dystrophies, cardiovascular disease, and cancer among others.

The drug thalidomide and its analogs lenalidomide and pomalidomide have garnered interest as immunomodulators and antineoplastics, especially in multiple myeloma (Kim S A et. al., "A novel cereblon modulator for targeted protein degradation", Eur J Med Chem. 2019 Mar. 15; 166:65-74; R. Verma et. al., "Identification of a Cereblon-Independent Protein Degradation Pathway in Residual Myeloma Cells Treated with Immunomodulatory Drugs" Blood (2015) 126 (23): 913. Liu Y, et al., "A novel effect of thalidomide and its analogs: suppression of cereblon ubiquitination enhances ubiquitin ligase function" FASEB J. 2015 December; 29(12):4829-39; Martiniani, R. et al. "Biological activity of lenalidomide and its underlying therapeutic effects in multiple myeloma" Adv Hematol, 2012, 2012:842945; and Terpos, E. et al. "Pomalidomide: a novel drug to treat relapsed and refractory multiple myeloma" Oncotargets and Therapy, 2013, 6:531). While the exact therapeutic mechanism of action of thalidomide, lenalidomide and pomalidomide is unknown, the compounds exhibit activity. Thalidomide and its analogues have been found to bind to the ubiquitin ligase cereblon and redirect its ubiquitination activity (see Ito, T. et al. "Identification of a primary target of thalidomide teratogenicity" Science, 2010, 327:1345). Cereblon forms part of an E3 ubiquitin ligase complex which interacts with damaged DNA binding protein 1, forming an E3 ubiquitin ligase complex with Cullin 4 and the E2-binding protein ROC1 (known as RBX1) where it functions as a substrate receptor to select proteins for ubiquitination. The binding of lenalidomide to cereblon facilitates subsequent binding of cereblon to Ikaros and Aiolos, leading to their ubiquitination and degradation by the proteasome (see Lu, G. et al. "The myeloma drug lenalidomide promotes the cereblon-dependent destruction of Ikaros proteins" Science, 2014, 343:305-309; Kronke, J. et al. "Lenalidomide causes selective degradation of IKZF1 and IKZF3 in multiple myeloma cells" Science, 2014, 343:301-305).

The disclosure that thalidomide binds to the cereblon E3 ubiquitin ligase led to research to investigate incorporating thalidomide and certain derivatives into compounds for the targeted destruction of proteins. Celgene has disclosed imides for similar uses, including those in U.S. Pat. Nos. 6,045,501; 6,315,720; 6,395,754; 6,561,976; 6,561,977; 6,755,784; 6,869,399; 6,908,432; 7,141,018; 7,230,012; 7,820,697; 7,874,984; 7,959,566; 8,204,763; 8,315,886; 8,589,188; 8,626,531; 8,673,939; 8,735,428; 8,741,929; 8,828,427; 9,056,120; 9,101,621; 9,101,622; 9,587,281; 9,857,359; and 10,092,555.

Patent applications filed by C4 Therapeutics, Inc., that describe compounds capable of binding to an E3 ubiquitin ligase and a target protein for degradation include: WO/2023/055952 titled "Neurotrophic Tyrosine Receptor Kinase (NTRK) Degrading Compounds"; WO/2023/039208 titled "Selected Compounds for Targeted Degradation of BRD9"; WO/2023/283610 titled "Compounds for Targeting Degradation of IRAK4 Proteins"; WO/2023/283372 titled "Compounds for Targeting Degradation of IRAK4 Proteins"; WO/2022/251539 titled "EGFR Degraders to Treat Cancer Metastasis to the Brain or CNS"; WO/2022/081928 titled "Tricyclic Heterobifunctional Compounds for Degradation of Targeted Proteins"; WO/2022/081927 titled "Tricyclic Compounds to Degrade Neosubstrates for Medical Therapy"; WO/2022/081925 titled "Tricyclic Ligands for Degradation of IKZF2 or IKZF4"; WO/2022/032132 titled "Advantageous Therapies for Disorders Mediated by Ikaros or Aiolos"; WO/2021/255213 titled "Heterobifunctional Compounds as Degraders of BRAF"; WO/2021/255212 titled "BRAF Degraders"; WO/2021/178920 titled "Compounds for Targeted Degradation of BRD9"; WO/2021/127561 titled "Isoindolinone And Indazole Compounds For The Degradation Of EGFR"; WO/2021/086785 titled "Bifunctional Compounds"; WO/2021/083949 titled "Bifunctional Compounds for the Treatment of Cancer"; WO/2020/210630 titled "Tricyclic Degraders of Ikaros and Aiolos"; WO/2020/181232 titled "Heterocyclic Compounds for Medical Treatment"; WO/2020/132561 titled "Targeted Protein Degradation"; WO/2019/236483 titled "Spirocyclic Compounds"; WO2020/051235 titled "Compounds for the degradation of BRD9 or MTH1"; WO/2019/191112 titled "Cereblon binders for the Degradation of Ikaros"; WO/2019/204354 titled "Spirocyclic Compounds"; WO/2019/099868 titled "Degraders and Degrons for Targeted Protein Degradation"; WO/2018/237026 titled "N/O-Linked Degrons and Degronimers for Protein Degradation"; WO 2017/197051 titled "Amine-Linked C3-Glutarimide Degronimers for Target Protein Degradation"; WO 2017/

197055 titled "Heterocyclic Degronimers for Target Protein Degradation"; WO 2017/197036 titled "Spirocyclic Degronimers for Target Protein Degradation"; WO 2017/197046 titled "C3-Carbon Linked Glutarimide Degronimers for Target Protein Degradation"; and WO 2017/197056 titled "Bromodomain Targeting Degronimers for Target Protein Degradation."

Other examples of patent applications that describe protein degrading compounds include: WO 2015/160845; WO 2016/105518; WO 2016/118666; WO 2016/149668; WO 2016/197032; WO 2016/197114; WO 2017/007612; WO 2017/011371; WO 2017/011590; WO 2017/030814; WO 2017/046036; WO2017/079267; WO 2017/176708; WO 2017/176957; WO 2017/180417; WO 2018/053354; WO 2018/071606; WO 2018/102067; WO 2018/102725; WO 2018/118598; WO 2018/119357; WO 2018/119441; WO 2018/119448; WO 2018/140809; WO 2018/144649; WO 2018/119448; WO 2018/226542; WO 2019/023553; WO 2019/060693; WO 2019/060742; WO 2019/140380; WO 2019/140387; WO 2019/195201; WO 2019/199816; WO 2019/099926; WO 2019/195609; WO 2020/023851; WO 2020/041331; WO 2020/051564; WO 2021/053495; WO 2021/053555; WO 2021/162493; WO 2022/012622; WO 2022/174269; WO 2022/174269; WO 2022/236058; WO 2023/278759; WO 2023/044046; WO 2023/076161; WO 2023/049790; and WO 2023/076556.

It is an object of the present invention to provide new compounds, methods, compositions, and methods of manufacture that are useful to degrade selected proteins in vivo.

SUMMARY OF THE INVENTION

Cereblon binding compounds (Degrons) with specific bicyclic substituents at the C3 position of glutarimide are provided. These specific bicyclic substituents correspond to the bicycles of Formulas IA, IIA, IIIA, IVA, VA, VIA, VIIA, VIIIA, IXA, XA, XIA, XIIA, XIIIA, XIVA, XVA, and XVIA below as well as the embodiments described herein.

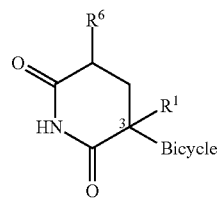

The described Degrons can be used to treat disorders mediated by cereblon or mediated by a protein which is degraded by cereblon when a Degron described herein binds to cereblon. Alternatively, a Degron described herein can be used as an intermediate to synthesize a heterobifunctional compound for targeted protein degradation (a Degrader). In certain aspects the Degron includes a linking moiety (a Tail) which can react with an appropriately prepared Targeting Ligand or Targeting Ligand precursor to form a Degrader. Degraders are also provided which include a Degron described herein which can be directly attached to a Targeting Ligand or attached to the Targeting Ligand with a Linker.

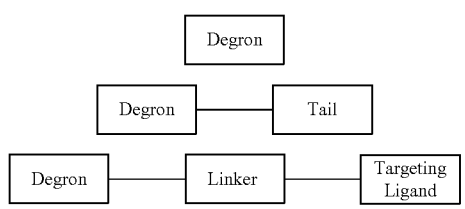

A Degron compound can be a "molecular glue" that can bind to the cereblon E3 ligase thereby creating a new surface on the E3 ligase, resulting in an enhancement of interaction and binding with a targeted protein. As a result of this interaction, the targeted protein may be ubiquitinated by the cereblon E3 ligase and degraded by the proteasome. In some embodiments, the cereblon binding affinity of the Degron enables degradation of the protein associated with a disease, such as, but not limited to, cancer and as described in more detail below.

For example, a compound of Formula IA is a Degron and can thus be used as a therapeutically active compound that changes the surface of cereblon, an intermediate to make a Degrader, or as part of a heterobifunctional compound to degrade a target protein (a Degrader).

In certain aspects, a Degron compound of Formula IA, Formula IIA, Formula IIIA, Formula IVA, Formula VA, Formula VIA, Formula VIIA, Formula VIIIA, Formula IXA, Formula XA, Formula XIA, Formula XIIA, Formula XIIIA, Formula XIVA, Formula XVA, or Formula XVIA is provided:

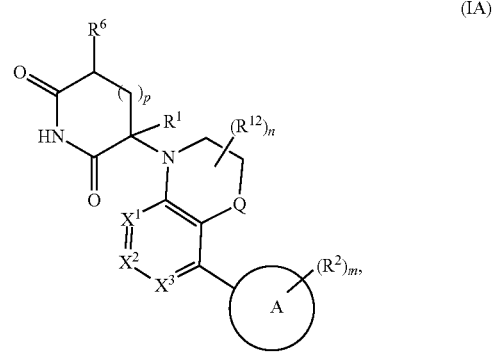

(IA)

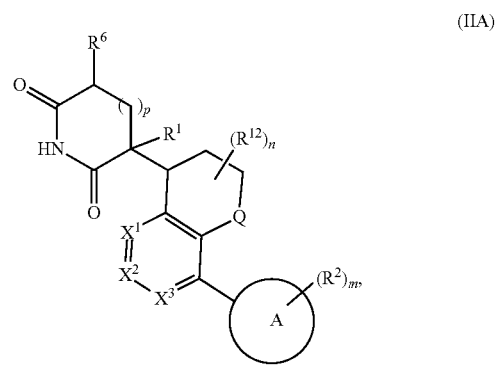

(IIA)

-continued
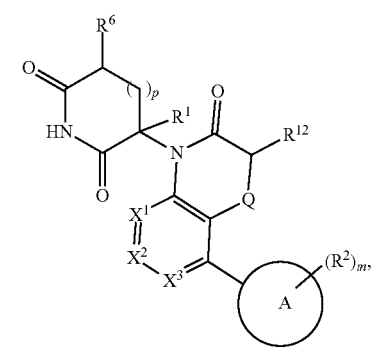
(IIIA)
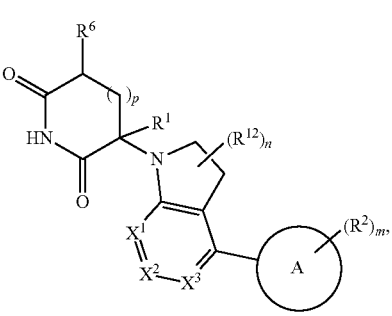
(IVA)
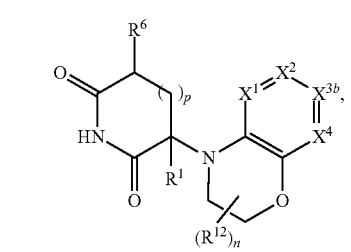
(VA)
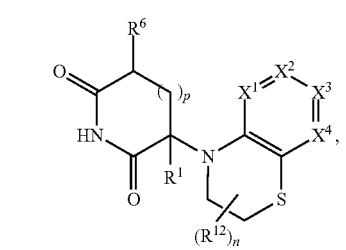
(VIA)
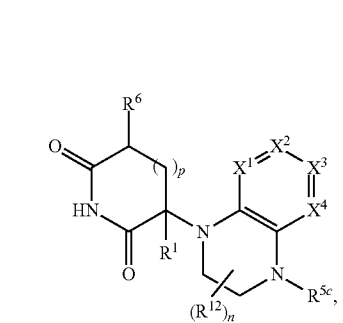
(VIIA)
-continued
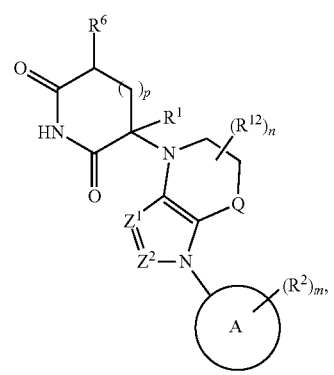
(VIIIA)
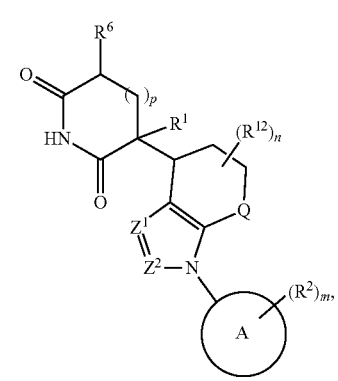
(IXA)
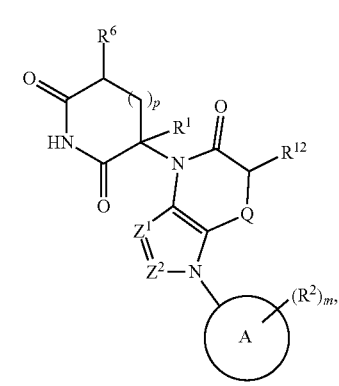
(XA)
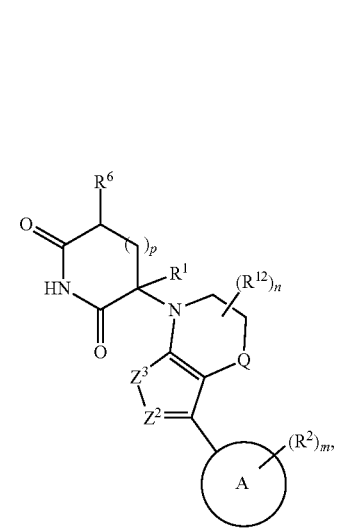
(XIA)

-continued (XIIA)
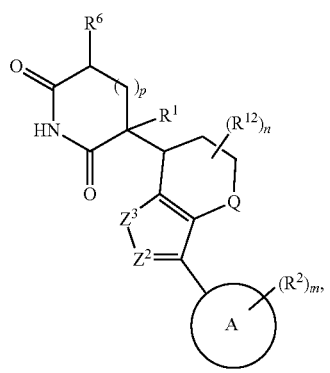

(XIIIA)
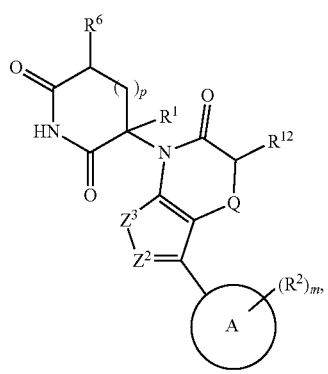

(XIVA)
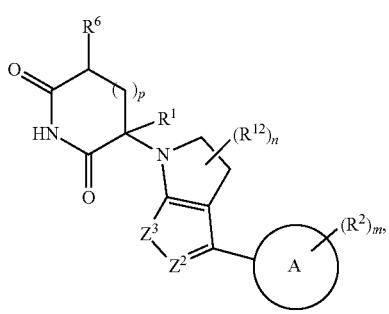

(XVA)
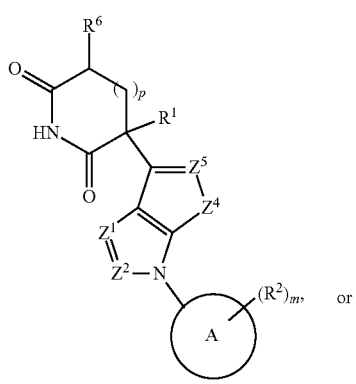

(XVIA)
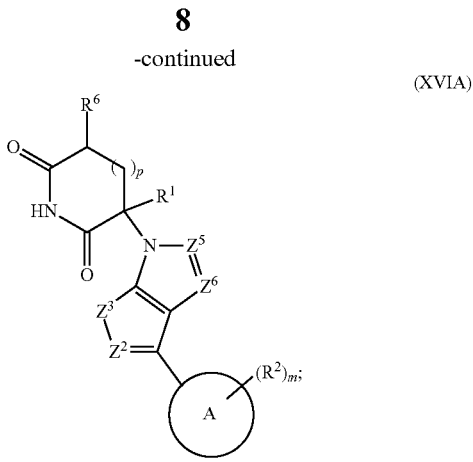

or a pharmaceutically acceptable salt, N-oxide, isotopic derivative or prodrug thereof, optionally in a pharmaceutically acceptable carrier to form a pharmaceutical composition;

wherein:

m is 0, 1, 2, 3, or 4;
in certain embodiments m is 0 or 1;
n is 0, 1, 2, or 3;
in certain embodiments n is 0, 1, or 2;
p is 0 or 1;
in certain embodiments p is 1;
Q is O, S, $NR^{17}$, or $CR^{17}R^{18}$;
in certain embodiments Q is O, $NR^{17}$, or $CH_2$;
in certain embodiments Q is O;
$X^1$, $X^2$, and $X^3$ are independently selected from the group consisting of N, CH, and $CR^5$;
in certain embodiments no more than one of $X^1$, $X^2$, and $X^3$ are selected to be N;
$X^3b$ is N, CH, or $CR^{5b}$;
in certain embodiments $X^3b$ is CH;
$X^4$ is N, CH, or $CR^5$;
in certain embodiments $X^4$ is CH or $CR^5$;
$Z^1$, $Z^2$, $Z^5$, and $Z^6$ are independently selected from the group consisting of CH, $CR^5$, and N;
$Z^3$ and $Z^4$ are independently selected from the group consisting of S, O, NH, and $NR^{17}$;
Ⓐ is a cycloalkyl, heterocycle, or heteroaryl;
in certain embodiments Ⓐ is

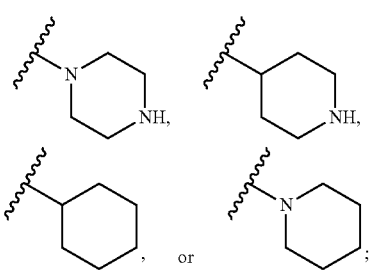

$R^1$ and $R^6$ are independently selected from hydrogen, alkyl, alkenyl, alkynyl, and halogen; or $R^1$ and $R^6$ are combined to form a $CH_2$ or $CH_2CH_2$ bridge;
each $R^2$ is independently selected from hydrogen, alkyl, haloalkyl, alkenyl, alkynyl, aryl, heteroaryl, heterocycle, and —$C(O)R^9$, each of which except hydrogen is optionally substituted with 1, 2, 3, or 4 substituents independently selected from $R^{10}$;

each $R^5$ is independently selected from hydrogen, alkyl, haloalkyl, alkenyl, alkynyl, halogen, aryl, heteroaryl, heterocycle, cyano, nitro, —$NR^7R^8$, —$OR^7$, —$SR^7$, —$C(O)R^9$, —$C(S)R^9$, —$S(O)R^9$, —$S(O)_2R^9$, —$OC(O)R^9$, —$OC(S)R^9$, —$OS(O)R^9$, —$OS(O)_2R^9$, —$SC(O)R^9$, —$OS(O)_2R^9$, —$NR^7C(O)R^9$, —$NR^7C(S)R^9$, —$NR^7S(O)R^9$, —$NR^7S(O)_2R^9$, —$P(O)(R^9)_2$, —$SP(O)(R^9)_2$, —$NR^7P(O)(R^9)_2$, and —$OP(O)(R^9)_2$; each of which except hydrogen, halogen, cyano, and nitro is optionally substituted with 1, 2, 3, or 4 substituents independently selected from $R^{10}$;

$R^{5b}$ is selected from hydrogen, alkyl, alkenyl, alkynyl, aryl, heteroaryl, heterocycle, —C(O)alkyl, —$C(S)R^9$, —$S(O)R^9$, and —$S(O)_2R^9$; each of which except hydrogen is optionally substituted with 1, 2, 3, or 4 substituents independently selected from $R^{10}$;

$R^{5c}$ is selected from hydrogen, alkyl, alkenyl, alkynyl, halogen, aryl, heteroaryl, heterocycle, cyano, nitro, —$OR^7$, —$SR^7$, —$C(O)R^{9b}$, —$C(S)R^9$, —$S(O)R^9$, —$S(O)_2R^9$, —$OC(O)R^9$, —$OC(S)R^9$, —$OS(O)R^9$, —$OS(O)_2R^9$, —$SC(O)R^9$, —$OS(O)_2R^9$, —$NR^7C(O)R^9$, —$NR^7C(S)R^9$, —$NR^7S(O)R^9$, —$NR^7S(O)_2R^9$, —$P(O)(R^9)_2$, —$SP(O)(R^9)_2$, —$NR^7P(O)(R^9)_2$, and —$OP(O)(R^9)_2$; each of which except hydrogen, halogen, cyano, and nitro is optionally substituted with 1, 2, 3, or 4 substituents independently selected from $R^{10}$;

$R^7$ and $R^8$ at each instance are independently selected from hydrogen, alkyl, haloalkyl, alkenyl, alkynyl, aryl, heteroaryl, heterocycle; and $C(O)R^{14}$ each of which except hydrogen is optionally substituted with 1, 2, 3, or 4 substituents independently selected from $R^{16}$; each $R^9$ is independently selected from hydrogen, alkyl, haloalkyl, alkenyl, alkynyl, aryl, heteroaryl, heterocycle, —$NR^7R^8$, —$OR^7$, and —$SR^7$ each of which is optionally substituted with 1, 2, 3, or 4 substituents independently selected from $R^{10}$;

$R^{9b}$ is independently selected from hydrogen, alkyl, haloalkyl, alkenyl, alkynyl, aryl, heteroaryl, heterocycle, —$NR^7R^8$, and —$SR^7$ each of which is optionally substituted with 1, 2, 3, or 4 substituents independently selected from $R^{10}$;

each $R^{10}$ is independently selected from hydrogen, alkyl, haloalkyl, alkenyl, alkynyl, halogen, aryl, heteroaryl, heterocycle, cyano, nitro, —$NR^{11}R^{13}$, —$OR^{11}$, —$SR^{11}$, —$C(O)R^{14}$, —$C(S)R^{14}$, —$S(O)R^{14}$, —$S(O)_2R^{14}$, —$OC(O)R^{14}$, —$OC(S)R^{14}$, —$OS(O)R^{14}$, —$OS(O)_2R^{14}$, —$NR^1C(O)R^{14}$, —$NR^{11}C(S)R^{14}$, —$NR^{11}S(O)R^{14}$, —$NR^{11}S(O)_2R^{14}$, —$P(O)(R^{14})_2$, —$NR^{11}P(O)(R^{14})_2$, and —$OP(O)(R^{14})_2$; each of which except hydrogen, halogen, cyano, and nitro is optionally substituted with 1, 2, 3, or 4 substituents independently selected from $R^{15a}$;

$R^{11}$ and $R^{13}$ at each instance are independently selected from hydrogen, alkyl, haloalkyl, alkenyl, alkynyl, aryl, heteroaryl, heterocycle, —$C(O)R^{14}$, —$C(S)R^{14}$, —$S(O)R^{14}$, —$S(O)_2R^{14}$, and —$P(O)(R^{14})_2$; each of which is optionally substituted with 1, 2, 3, or 4 substituents independently selected from $R^{15b}$;

each $R^{12}$ is independently selected from hydrogen, alkyl, haloalkyl, alkenyl, alkynyl, halogen, aryl, heteroaryl, heterocycle, cyano, nitro, —$NR^{11}R^{13}$, —$OR^{11}$, and —$SR^{11}$; each of which except hydrogen, halogen, cyano, and nitro is optionally substituted with 1, 2, 3, or 4 substituents independently selected from $R^{15c}$;

each $R^{14}$ is independently selected from hydrogen, alkyl, haloalkyl, alkenyl, alkynyl, aryl, heteroaryl, heterocycle, amino, hydroxyl, alkoxy, —N(H)(alkyl), and —N(alkyl)$_2$ each of which except hydrogen is optionally substituted with 1, 2, 3, or 4 substituents independently selected from $R^{15d}$;

$R^{15a}$, $R^{15b}$, $R^{15c}$, $R^{15d}$, $R^{15e}$, $R^{15f}$, and $R^{15g}$ at each instance is independently selected from hydrogen, alkyl, haloalkyl, alkenyl, alkynyl, halogen, aryl, heteroaryl, heterocycle, cyano, nitro, amino, hydroxyl, alkoxy, —N(H)(alkyl), and —N(alkyl)$_2$;

each $R^{16}$ is independently selected from hydrogen, alkyl, haloalkyl, alkenyl, alkynyl, halogen, aryl, heteroaryl, heterocycle, cyano, nitro, —$NR^{11}R^{13}$, —$OR^{11}$, —$SR^{11}$, —$C(O)R^{14}$, —$C(S)R^{14}$, —$S(O)R^{14}$, —$S(O)_2R^{14}$, —$OC(O)R^{14}$, —$OC(S)R^{14}$, —$OS(O)R^{14}$, —$OS(O)_2R^{14}$, —$NR^1C(O)R^{14}$, —$NR^{11}C(S)R^{14}$, —$NR^{11}S(O)R^{14}$, —$NR^{11}S(O)_2R^{14}$, —$P(O)(R^{14})_2$, —$NR^{11}P(O)(R^{14})_2$, and —$OP(O)(R^{14})_2$; each of which except hydrogen, halogen, cyano, and nitro is optionally substituted with 1, 2, 3, or 4 substituents independently selected from $R^{15e}$;

$R^{17}$ is selected from hydrogen, alkyl, haloalkyl, alkenyl, alkynyl, halogen, aryl, heteroaryl, heterocycle, —$C(O)R^{14}$, —$C(S)R^{14}$, —$S(O)R^{14}$, —$S(O)_2R^{14}$, and —$P(O)(R^{14})$; each of which except hydrogen is optionally substituted with 1, 2, 3, or 4 substituents independently selected from $R^{15f}$; and $R^{18}$ is selected from hydrogen, alkyl, haloalkyl, alkenyl, alkynyl, halogen, aryl, heteroaryl, heterocycle, cyano, nitro, —$NR^{11}R^{13}$, —$OR^{11}$, —$SR^{11}$, —$OC(O)R^{14}$, —$OC(S)R^{14}$, —$OS(O)R^{14}$, —$OS(O)_2R^{14}$, —$NR^1C(O)R^{14}$—$NR^{11}C(S)R^{14}$, —$NR^1S(O)R^{14}$, —$NR^{11}S(O)_2R^{14}$, —$P(O)(R^{14})_2$, —$NR^{11}P(O)(R^{14})_2$, and —$OP(O)(R^{14})_2$; each of which except hydrogen, halogen, cyano, and nitro is optionally substituted with 1, 2, 3, or 4 substituents independently selected from $R^{15g}$.

In certain aspects, a Degron of Formula XVIIAa, Formula XVIIAb, Formula XVIIAc, Formula XVIIAd, or Formula XVIIAe is provided:

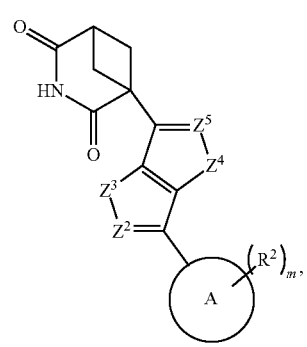

(XVIIAa)

-continued (XVIIAb)
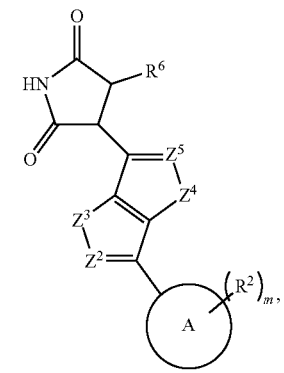

(XVIIAc)
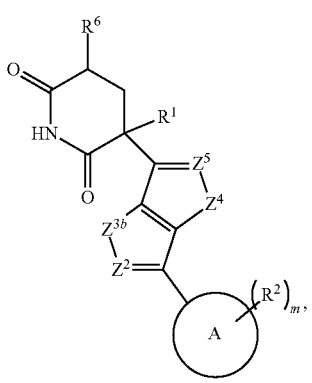

(XVIIAd)
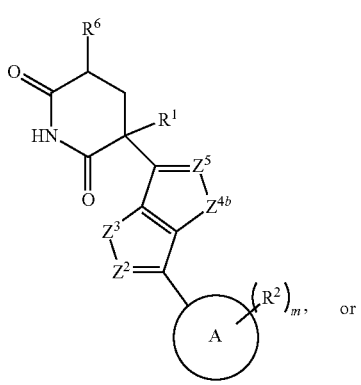 or (XVIIAe)
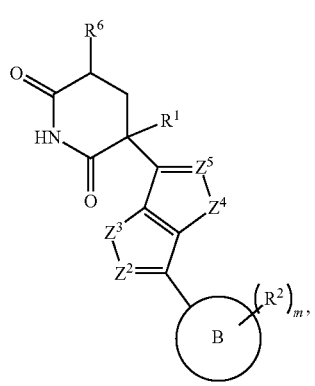

or a pharmaceutically acceptable salt, N-oxide, isotopic derivative or prodrug thereof, optionally in a pharmaceutically acceptable carrier to form a pharmaceutical composition;

wherein:
$Z^3b$ is selected from O, NH, and $NR^{17}$;
$Z^{4b}$ is selected from S, NH, and $NR^{17}$; and
Ⓑ is a 5-membered heterocycle, 5-membered heteroaryl, pyrimidinyl, pyridazinyl, or pyrazinyl;
and all other variables are as defined herein.

The Degron as described herein can be used alone (i.e., not as part of a Degrader) as an in vivo binder of cereblon, which can be administered to a host, for example, a human, in need thereof, in an effective amount, optionally as a pharmaceutically acceptable salt, and optionally in a pharmaceutically acceptable composition, for any therapeutic indication which can be treated by modulating the function or activity of the cereblon-containing E3 ubiquitin ligase protein complex, including but not limited to uses known for the cereblon binders thalidomide, pomalidomide, and lenalidomide. The binding of a Degron described herein to cereblon can induce a change in the protein confirmation of cereblon that allows for the degradation of a Target Protein. In certain embodiments a Degron described herein is a "molecular glue" that causes the targeted degradation of a Target Protein, for example, a protein with a C2H2 zinc finger degron motif.

Non-limiting examples of proteins that can be degraded or downregulated by a Degron include ARID2, CDK1, CDK12-cyclin K, CDK13, CK1alpha, CSNK1A1, Cyclin K, E4F1, FAM83F, GSPT1, GSPT2, GZF1, IKZF1, IKZF2, IKZF3, IKZF4, ILF2, Myc, ODC1, p63, PDE6D, AB28, RARalpha-ZBTB16, RBM23, RBM39, RBM39, RNF166, SALL4, WBP4, ZBTB16, ZBTB16-RARalpha, ZBTB39, ZFP91, ZFP91, ZFP91, ZMYM2-FGFR1, ZMYM2-FLT3, ZNF198, ZNF276, ZNF276, ZNF517, ZNF582, ZNF653, ZNF654, ZNF692, ZNF787, ZNF827, and ZNF98. In certain embodiments the Target Protein degraded by a Degron of the present invention is selected from ARID2, aromatase; b-catenin, CDK12, NRF2, PDE6D, CK1alpha, cyclin K, GSPT1, FAM83, ILF2, ZBTB16, and ZMYM2. In certain embodiments the Target Protein degraded by a Degron of the present invention is selected from IKZF1, IKZF2, IKZF3, and IKZF4.

Non-limiting examples of disorders which can be treated with a Degron described herein include abnormal cell proliferation, including a tumor or cancer, or a myelo- or lymphoproliferative disorder such as B- or T-cell lymphomas, multiple myeloma, Waldenstrom's macroglobulinemia, Wiskott-Aldrich syndrome, or a post-transplant lymphoproliferative disorder; an immune disorder, including autoimmune disorders such as Addison disease, Celiac disease, dermatomyositis, Graves disease, thyroiditis, multiple sclerosis, pernicious anemia, reactive arthritis, lupus, or type I diabetes; a disease of cardiologic malfunction including hypercholesterolemia; an infectious disease including viral or bacterial infections; and inflammatory conditions including asthma, chronic peptic ulcers, tuberculosis, rheumatoid arthritis, periodontitis, ulcerative colitis, Crohn's disease, or hepatitis.

In certain embodiments a Degron described herein is used to degrade a protein that mediates multiple myeloma, colorectal cancer, Hodgkin's lymphoma, or Non-Hodgkin's lymphoma.

In certain embodiments, the Degron described herein can activate, decrease, or change the natural activity of cereblon. Additional non-limiting examples of uses for cereblon binders are for treating multiple myeloma, a hematological disorder such as myelodysplastic syndrome, cancer, tumors, abnormal cellular proliferation, HIV/AIDS, Crohn's disease, sarcoidosis, graft-versus-host disease, rheumatoid arthritis, Behcet's disease, tuberculosis, and myelofibrosis.
In other aspects the Degron has a Tail moiety. For example, a Degron of Formula:
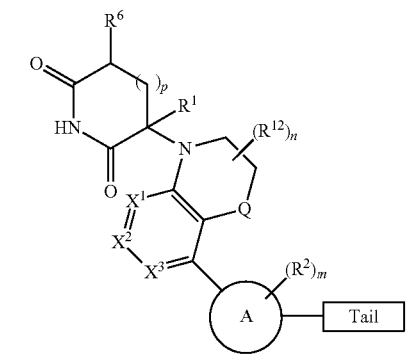
(IB)
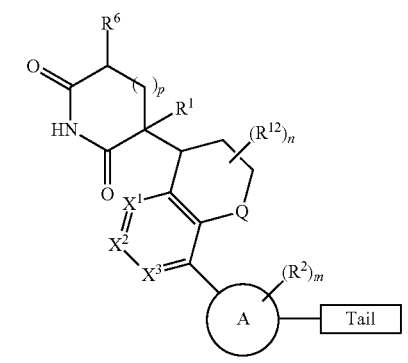
(IIB)
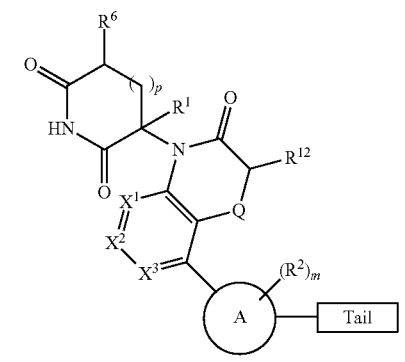
(IIIB)
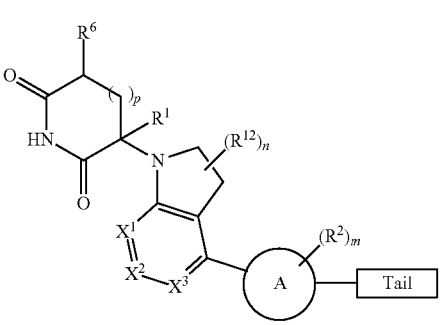
(IVB)
-continued
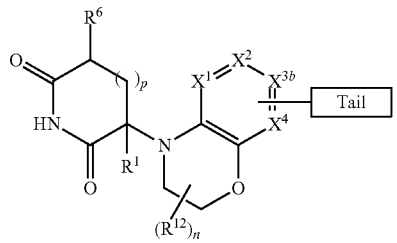
(VB)
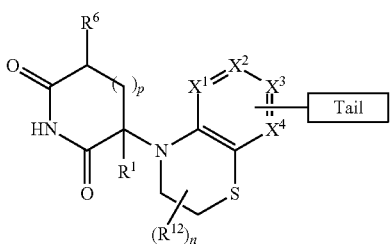
(VIB)
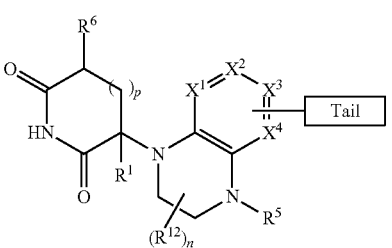
(VIIB)
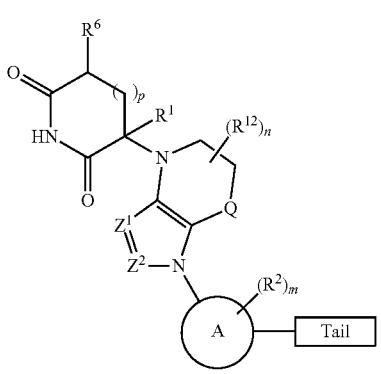
(VIIIB)
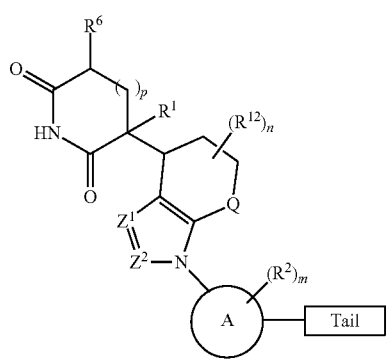
(IXB)

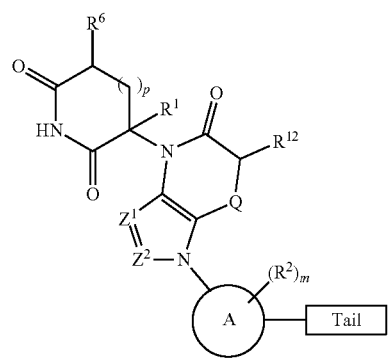
(XB)
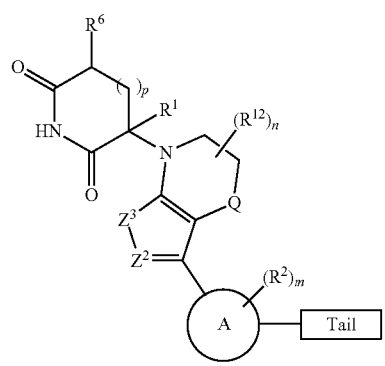
(XIB)
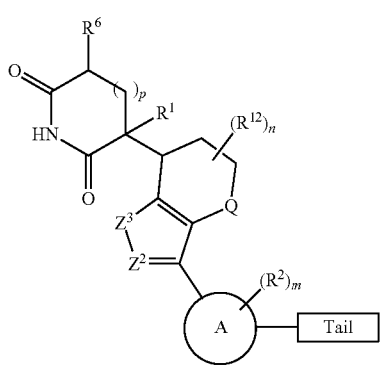
(XIIB)
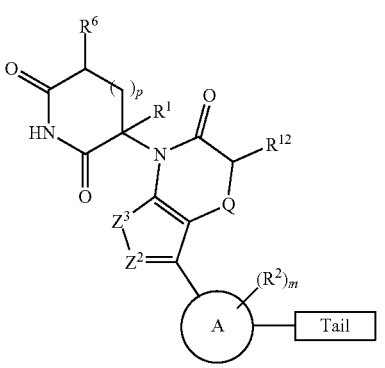
(XIIIB)
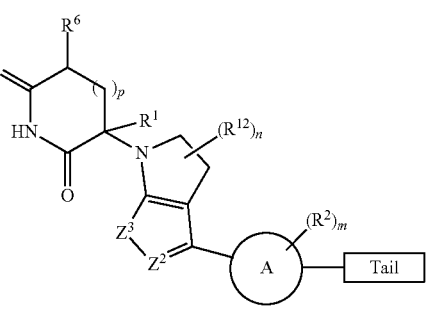
(XIVB)
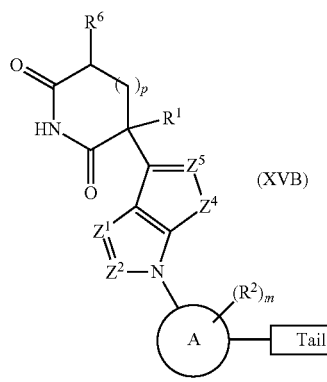
(XVB)
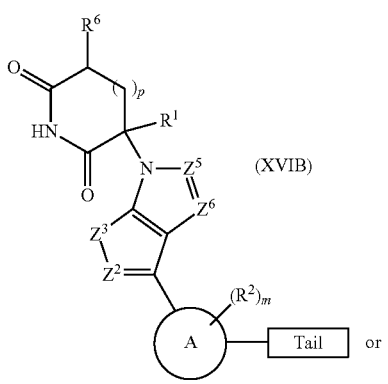
(XVIB)
or
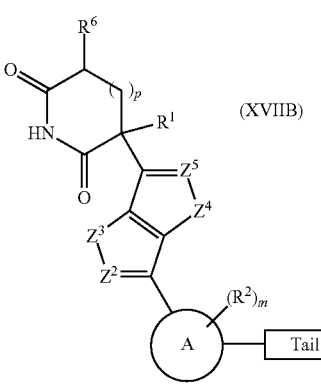
(XVIIB);

or a pharmaceutically acceptable salt thereof;
wherein:

Tail is selected from

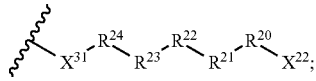

X$^{31}$ and X$^{32}$ are independently at each occurrence selected from bond, heterocycle, aryl, heteroaryl, bicycle, —NR$^{27}$—, —CR$^{40}$R$^{41}$—, —O—, —C(O)—, —C(NR$^{27}$)—, —C(S)—, —S(O)—, —S(O)$_2$— and —S—; each of which heterocycle, aryl, heteroaryl, and bicycle is substituted with 1, 2, 3, or 4 substituents independently selected from R$^{40}$, and X$^{22}$ is selected such that a compound sufficiently stable or the intended use results; and wherein X$^{22}$ is R$^5$;

R$^{20}$, R$^{21}$, R$^{22}$, R$^{23}$, and R$^{24}$ are independently at each occurrence selected from the group consisting of a bond, alkyl, —C(O)—, —C(O)O—, —OC(O)—, —SO$_2$—, —S(O)—, —C(S)—, —C(O)NR$^{27}$—, —NR$^{27}$C(O)—, —O—, —S—, —NR$^{27}$—, —C(R$^{40}$R$^{40}$)—, —P(O)(OR$^{26}$)O—, —P(O)(OR$^{26}$)—, bicycle, alkene, alkyne, haloalkyl, alkoxy, aryl, heterocycle, aliphatic, heteroaliphatic, heteroaryl, lactic acid, glycolic acid, and carbocycle; each of which is optionally substituted with 1, 2, 3, or 4 substituents independently selected from R$^{40}$;

R$^{26}$ is independently at each occurrence selected from the group consisting of hydrogen, alkyl, arylalkyl, heteroarylalkyl, alkene, alkyne, aryl, heteroaryl, heterocycle, aliphatic and heteroaliphatic;

R$^{27}$ is independently at each occurrence selected from the group consisting of hydrogen, alkyl, aliphatic, heteroaliphatic, heterocycle, aryl, heteroaryl, —C(O)(aliphatic, aryl, heteroaliphatic or heteroaryl), —C(O)O(aliphatic, aryl, heteroaliphatic, or heteroaryl), alkene, and alkyne; and R$^{40}$ is independently at each occurrence selected from the group consisting of hydrogen, R$^{27}$, alkyl, alkene, alkyne, fluoro, bromo, chloro, hydroxyl, alkoxy, azide, amino, cyano, —NH(aliphatic, including alkyl), —N(aliphatic, including alkyl)$_2$, —NHSO$_2$(aliphatic, including alkyl), —N(aliphatic, including alkyl)SO$_2$alkyl, —NHSO$_2$(aryl, heteroaryl or heterocycle), —N(alkyl)SO$_2$(aryl, heteroaryl or heterocycle), —NHSO$_2$alkenyl, —N(alkyl)SO$_2$alkenyl, —NHSO$_2$alkynyl, —N(alkyl)SO$_2$alkynyl, haloalkyl, aliphatic, heteroaliphatic, aryl, heteroaryl, heterocycle, and cycloalkyl.

In certain embodiments (A) when used in a bivalent structure is

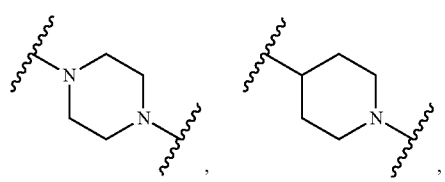

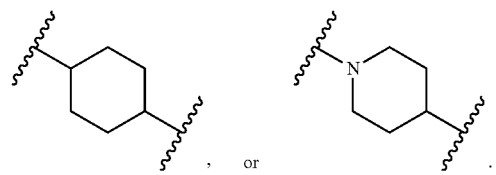

In certain aspects, a Degrader compound of Formula I, Formula II, Formula III, Formula IV, Formula V, Formula VI, or Formula VII is provided:

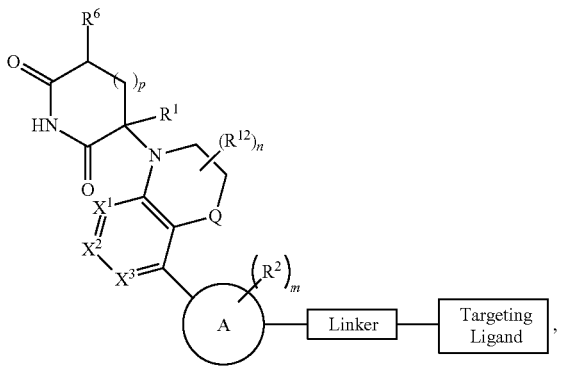

(I)

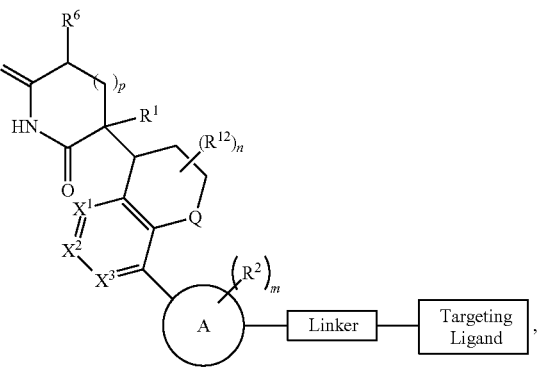

(II)

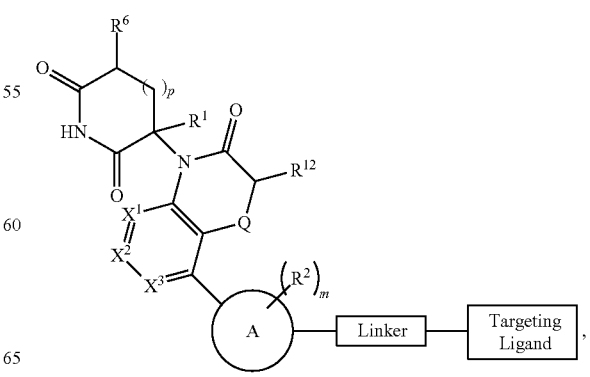

(III)

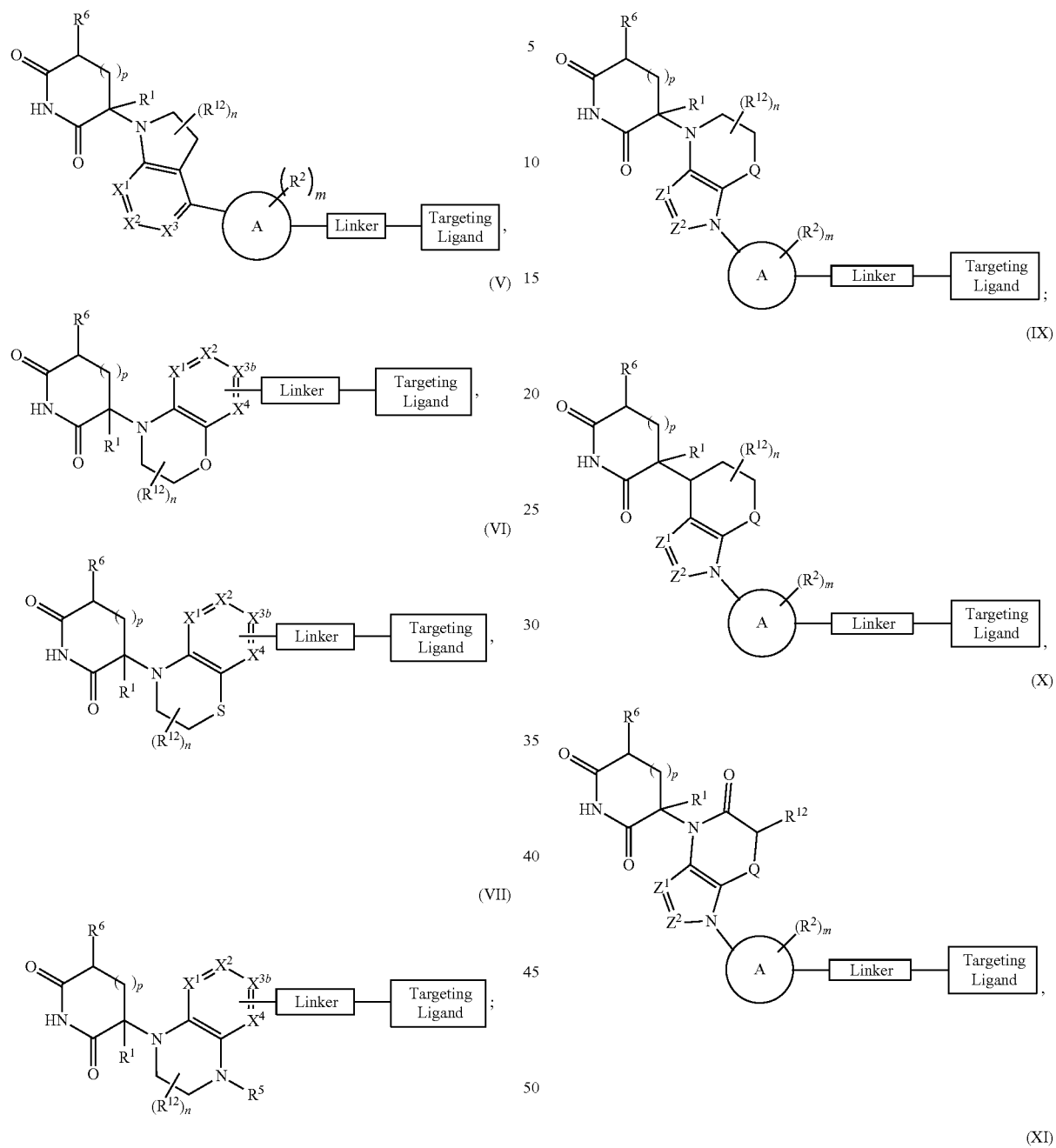

or a pharmaceutically acceptable salt thereof;
  wherein:
  Targeting Ligand is a moiety that binds to a Target Protein;
  Target Protein is a selected protein that causes or contributes to a disease; and
  Linker is a bivalent linking group;
  and wherein all other variables are as defined herein.

In other aspects, a Degrader compound of Formula VIII, Formula IX, Formula X, Formula XI, Formula XII, Formula XIV, Formula XV, Formula XVI, or Formula XVII is provided:

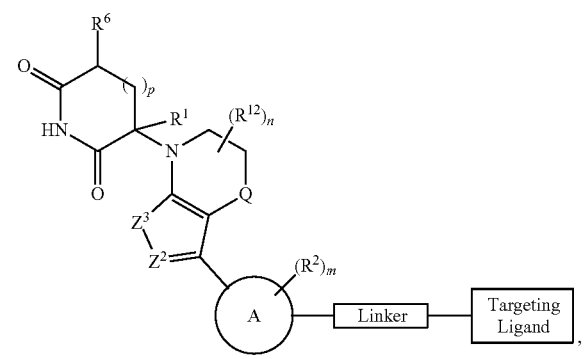

(XII)

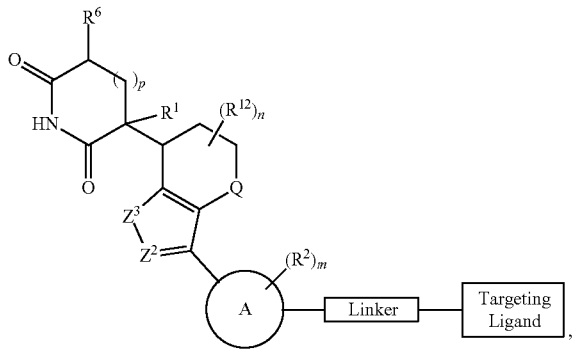

(XIII)

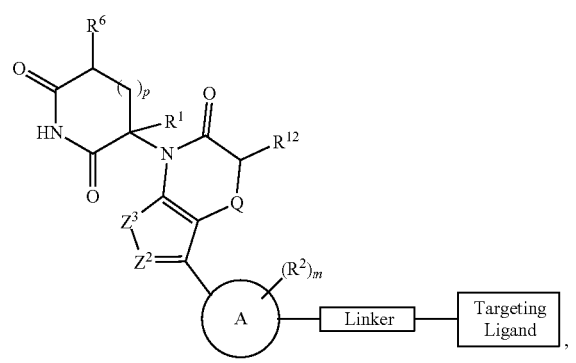

(XIV)

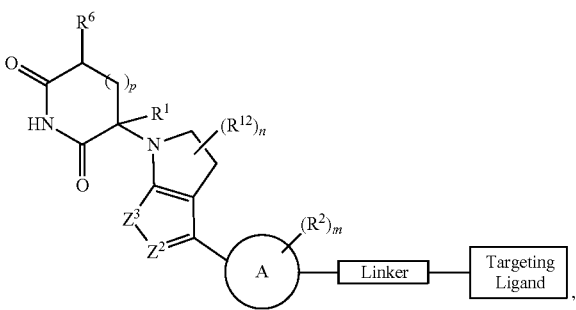

(XV)

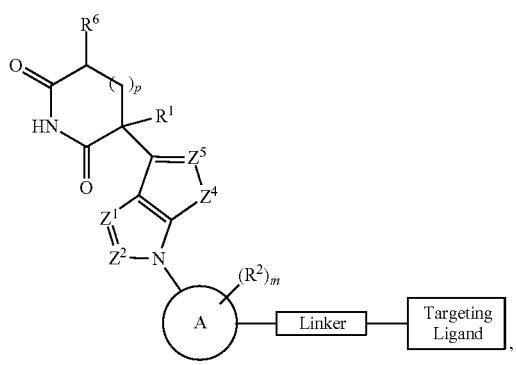

(XVI)

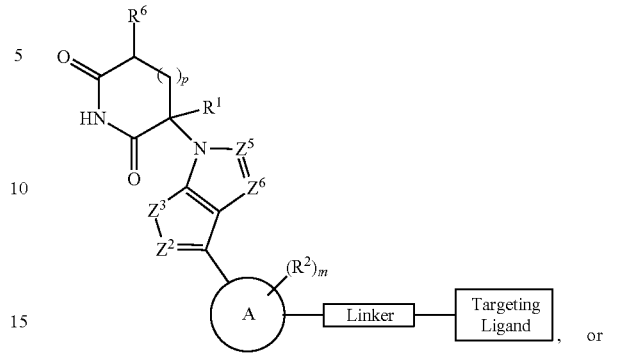

, or (XVII)

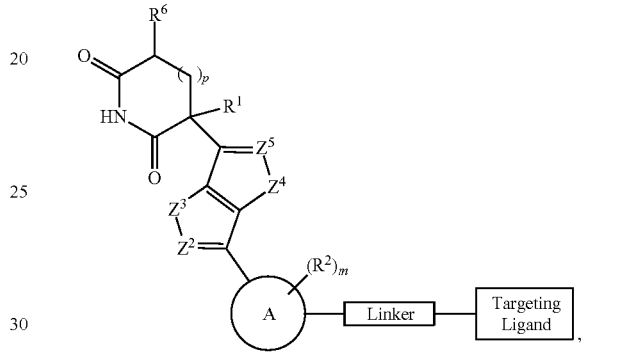

, or a pharmaceutically acceptable salt, N-oxide, isotopic derivative or prodrug thereof, optionally in a pharmaceutically acceptable carrier to form a pharmaceutical composition;
wherein:
Targeting Ligand is a chemical moiety that binds to a Target Protein;
Target Protein is a selected protein that causes or contributes to a disease; and
Linker is a bivalent linking group;
and wherein all other variables are as defined herein.

In certain aspects the Targeting Ligand is a means for binding a Target Protein, wherein the Targeting Ligand is a chemical moiety. In certain embodiments the term Targeting Ligand as used in a Formula or claim of the present invention is defined as a mean-plus-function according to 35 U. S. C. 112(f). In certain embodiments the Targeting Ligand is a chemical moiety described in this patent application, for example, a chemical moiety described in the Figures.

The structure of the Degrader is typically selected such that it is sufficiently stable to sustain a shelf life of at least two, three, four, or five months under ambient conditions. To accomplish this, each of the R groups described herein must be sufficiently stable to sustain the corresponding desired shelf life of at least two, three, four, or five months under ambient conditions. One of ordinary skill in the art is well aware of the stability of chemical moieties and can avoid those that are not stable or are too reactive under appropriate conditions.

Also, all R groups, with or without optional substituents, should be interpreted in a manner that does not include redundancy (i.e., as known in the art, alkyl substituted with alkyl is redundant; however, for example, alkoxy substituted with alkoxy is not redundant).

A Degrader provided herein or its pharmaceutically acceptable salt or its pharmaceutically acceptable composition can be used to treat a disorder which is mediated by the selected Target Protein that binds to the Targeting Ligand. Therefore, in some embodiments a method to treat a host with a disorder mediated by the Target Protein is provided that includes administering an effective amount of the Degrader or its pharmaceutically acceptable salt described herein to the host, typically a human, optionally in a pharmaceutically acceptable composition.

In certain embodiments, the selected Target Protein is derived from a gene that has undergone an amplification, translocation, rearrangement, a copy number variation, alteration, deletion, mutation, or inversion event which causes or is caused by a medical disorder. In certain aspects, the selected Target Protein has been post-translationally modified by one, or combinations, of phosphorylation, acetylation, acylation including propionylation and crotylation, N-linked glycosylation, amidation, hydroxylation, methylation, poly-methylation, O-linked glycosylation, pyroglutamoylation, myristoylation, farnesylation, geranylation, ubiquitination, sumoylation, or sulfation which causes or is caused by a medical disorder. In another embodiment, the Target Protein can be covalently modified by a Targeting Ligand that has been functionalized to create a covalent bond with the Target Protein, and the covalent bond can be irreversible or reversible.

One non-limiting example of a disorder treatable by such compounds is abnormal cellular proliferation, such as a tumor or cancer, wherein the Target Protein is an oncogenic protein or a signaling mediator of an abnormal cellular proliferative pathway and its degradation decreases abnormal cell growth.

Compounds and methods are presented for the treatment of a patient with a disorder mediated by a protein that is targeted for selective degradation that includes administering an effective amount of one or a combination of the Degrons or Degraders of the present invention described herein to a human patient in need thereof, optionally in a pharmaceutically acceptable carrier (composition).

In certain embodiments, the disorder is selected from a neoplasm, tumor, cancer, abnormal cellular proliferation, immune disorder, inflammatory disorder, graft-versus-host rejection, viral infection, bacterial infection, an amyloid-based proteinopathy, a proteinopathy, or fibrotic disorder.

In one embodiment, the present invention provides Degrons which are covalently linked to a Targeting Ligand through a Linker which can be of varying length and functionality. In one embodiment the resulting Degron-Linker-Targeting Ligand compound is used to treat a disorder described herein. In one embodiment, the Degron is linked directly to the Targeting Ligand (i.e., the Linker is a bond).

In certain embodiments, the Linker can be any chemically stable group that attaches the Degron to the Targeting Ligand. Examples of Linkers are provided in Section IV (Linkers). In a typical embodiment, the Linker has a chain of 2 to 14, 15, 16, 17, 18, 19, or 20 or more carbon atoms of which one or more carbon atoms can be replaced by a heteroatom such as O, N, S, or P, as long as the resulting molecule has a stable shelf life for at least two months, three months, six months, or one year as part of a pharmaceutically acceptable dosage form, and itself is pharmaceutically acceptable.

In certain embodiments, the chain has 2, 3, 4, 5, 6, 7, 8, 9, 10, 11, 12, 13, or 14 contiguous atoms in the chain. For example, the chain may include 1 or more ethylene glycol units, and in some embodiments, may have at least 2, 3, 4, 5, 6, 7, 8, 9, or 10 or more contiguous, partially contiguous, or non-contiguous ethylene glycol units in the Linker. In certain embodiments, the chain has at least 1, 2, 3, 4, 5, 6, 7, or 8 branches which can be independently alkyl, heteroalkyl, aryl, heteroaryl, alkenyl, or alkynyl substituents, which in one embodiment, each branch has 10, 8, 6, 4, 3, 2, or 1 carbon.

In one embodiment, the Target Protein is a protein that is not druggable in the classic sense in that it does not have a binding pocket or an active site that can be inhibited or otherwise bound and cannot be easily allosterically controlled. In another embodiment, the Target Protein is a protein that is druggable in the classic sense. Examples of Target Proteins are provided below.

In certain embodiments, the present invention provides the administration of an effective amount of a Degron or Degrader compound to treat a patient, for example, a human, having an infectious disease, wherein the therapy targets a Target Protein of the infectious agent or a Target Protein of the host (Degrader), or acts via binding to cereblon or its E3 Ubiquitin Ligase (Degron), or acts through an independent mechanism, optionally in combination with another bioactive agent.

The disease state or condition may be caused by a microbial agent or other exogenous agent such as a virus (as non-limiting examples, HIV, HBV, HCV, HSV, HPV, RSV, CMV, Ebola, SARS-CoV2, Flavivirus, Pestivirus, Rotavirus, Influenza, Coronavirus, EBV, viral pneumonia, drug-resistant viruses, Bird Flu, RNA virus, DNA virus, adenovirus, poxvirus, Picornavirus, Togavirus, Orthomyxovirus, Retrovirus, or Hepadnovirus), bacteria (including but not limited to Gram-negative, Gram-positive, Atypical, *Staphylococcus, Streptococcus, E. Coli, Salmonella, Helicobacter pylori*, meningitis, gonorrhea, Chlamydiaceae, Mycoplasmataceae, etc.), fungus, protozoa, helminth, worm, prion, parasite, or other microbe.

In certain embodiments, the Degron or Degrader compound has at least one desired isotopic substitution of an atom, at an amount above the natural abundance of the isotope, i.e., enriched.

In one embodiment, the Degron or Degrader compound includes a deuterium or multiple deuterium atoms.

Compounds of the present invention may offer important clinical benefits to patients, in particular for the treatment of the disease states and conditions modulated by the proteins of interest.

Unless otherwise defined, all technical and scientific terms used herein have the same meaning as commonly understood by one of ordinary skill in the art to which this application belongs. In the specification, singular forms also include the plural unless the context clearly dictates otherwise. Although methods and materials similar or equivalent to those described herein can be used in the practice or testing of the present application, suitable methods and materials are described below. All publications, patent applications, patents, and other references mentioned herein are incorporated by reference. The references cited herein are not admitted to be prior art to the claimed application. In the case of conflict, the present specification, including definitions, will control. In addition, the materials, methods, and examples are illustrative only and are not intended to be limiting.

Other features and advantages of the present application will be apparent from the following detailed description and claims.

The present invention therefore includes at least the following features:
(a) A Degron compound as described herein, or a pharmaceutically acceptable salt, isotopic derivative, or prodrug thereof,
(b) The use of a Degron compound or a pharmaceutically acceptable salt thereof, isotopic derivative or prodrug thereof as described herein as a molecular glue to bind to cereblon, resulting in the degradation of a Target Protein;
(c) A Degron with a Tail, or a pharmaceutically acceptable salt, isotopic derivative (including a deuterated derivative), or prodrug thereof or a therapeutic use thereof,
(d) A Degrader compound as described herein, or a pharmaceutically acceptable salt, isotopic derivative (including a deuterated derivative), or prodrug thereof,
(e) A Degrader compound or a pharmaceutically acceptable salt, isotopic derivative (including a deuterated derivative), or prodrug thereof for the treatment of a disorder that is mediated by a Target Protein, wherein the compound includes a Targeting Ligand for the Target Protein, and wherein the Degron is optionally linked to the Targeting Ligand through a Linker;
(f) Use of a Degron compound in an effective amount in the treatment of a patient, typically a human, with a disorder that responds to such treatment, including by altering the cereblon-based ubiquitination of a protein, such as for example, abnormal cellular proliferation such as a tumor or cancer, an immune or autoimmune or inflammatory disorder, a cardiologic disorder, an infectious disease, or other disorder that responds to such treatment;
(g) Use of a Degrader compound in an effective amount in the treatment of a patient, typically a human, with any of the disorders described herein mediated by a Target Protein, including abnormal cellular proliferation such as a tumor or cancer, an immune or autoimmune or inflammatory disorder, a cardiologic disorder, an infectious disease, or other disorder that responds to such treatment;
(h) Use of a Degron or Degrader or a pharmaceutically acceptable salt, isotopic derivative (including a deuterated derivative), or prodrug thereof in the manufacture of a medicament for the treatment of a medical disorder, as further described herein;
(i) A method for manufacturing a medicament intended for the therapeutic treatment of a disorder in a host characterized in that a Degron or Degrader is used in the manufacture;
(j) A Degron or Degrader or a pharmaceutically acceptable salt, isotopic derivative (including a deuterated derivative), or prodrug thereof that is useful in the treatment of an abnormal cellular proliferation such as cancer in a host, including any of the cancers described herein;
(k) Use of a Degron or Degrader compound or a pharmaceutically acceptable salt, isotopic derivative (including a deuterated derivative), or prodrug thereof in the manufacture of a medicament for the treatment of an abnormal cellular proliferation such as cancer, including any of the cancers described herein;
(l) A method for manufacturing a medicament intended for the therapeutic use of treating an abnormal cellular proliferation such as cancer, including any of the cancers in a host described herein, characterized in that a Degron or Degrader is used in the manufacture;
(m) A Degron or Degrader compound or a pharmaceutically acceptable salt, isotopic derivative (including a deuterated derivative), or prodrug thereof that is useful in the treatment of a tumor in a host, including any of the tumors described herein;
(n) Use of a Degron or Degrader compound or a pharmaceutically acceptable salt, isotopic derivative (including a deuterated derivative), or prodrug thereof that is useful in the treatment of a tumor in a host, including any of the tumors described herein;
(o) A method of manufacturing a medicament intended for the therapeutic treatment of a tumor in a host, including any of the tumors described herein, characterized in that a Degron or Degrader compound is used in the manufacture;
(p) A Degron or Degrader compound or a pharmaceutically acceptable salt, isotopic derivative (including a deuterated derivative), or prodrug thereof in the manufacture of a medicament for the treatment of an immune, autoimmune, or inflammatory disorder in a host;
(q) Use of a Degron or Degrader compound or a pharmaceutically acceptable salt, isotopic derivative, or prodrug thereof in the manufacture of a medicament for the treatment of an immune, autoimmune, or inflammatory disorder in a host;
(r) A method for manufacturing a medicament intended for the therapeutic treatment of an immune, autoimmune, or inflammatory disorder in a host, characterized in that a Degron or Degrader compound is used in the manufacture;
(s) A Degron or Degrader compound or a pharmaceutically acceptable salt, isotopic derivative, or prodrug thereof that is useful in the treatment of an infection, including a viral infection in a host, for example HIV, HBV, HCV, SARS-CoV2, and RSV;
(t) Use of a Degron or Degrader compound or a pharmaceutically acceptable salt, isotopic derivative (including a deuterated derivative), or prodrug thereof in the manufacture of a medicament for the treatment of an infection, including a viral infection in a host, for example HIV, HBV, HCV, SARS-CoV2, and RSV;
(u) A method for manufacturing a medicament intended for the therapeutic treatment of an infection, including a viral infection in a host for example HIV, HBV, HCV, SARS-CoV2, and RSV, characterized in that a Degron or Degrader compound is used in the manufacture;
(v) A pharmaceutical formulation comprising an effective host-treating amount of a Degron or Degrader compound or a pharmaceutically acceptable salt, isotopic derivative, or prodrug thereof with a pharmaceutically acceptable carrier or diluent;
(w) A Degron or Degrader compound as described herein as a mixture of enantiomers or diastereomers (as relevant), including as a racemate;
(x) A Degron or Degrader compound as described herein in enantiomerically or diastereomerically (as relevant) enriched form, including an isolated enantiomer or diastereomer (i.e., greater than 85, 90, 95, 97, or 99% pure); and
(y) A process for the preparation of therapeutic products that contain an effective amount of a Degron or Degrader compound or a pharmaceutically acceptable salt, isotopic derivative, or prodrug thereof optionally with a pharmaceutically acceptable carrier or diluent.

BRIEF DESCRIPTION OF THE FIGURES

FIG. 1R-1S provides non-limiting examples of Tyrosine Kinase Targeting Ligands wherein R represents exemplary points at which the Linker can be attached.

FIG. 1AA provides non-limiting examples of mTORC1 and/or mTORC2 Targeting Ligands wherein R represents exemplary points at which the Linker can be attached.

FIG. 1BB-1CC provide non-limiting examples of Mast/stem cell growth factor receptor (SCFR), also known as c-KIT receptor, Targeting Ligands wherein R represents exemplary points at which the Linker can be attached.

FIG. 1DD provides non-limiting examples of IGF1R and/or IR Targeting Ligands wherein R represents exemplary points at which the Linker can be attached.

FIG. 1EE-1FF provide non-limiting examples of HDM2 and/or MDM2 Targeting Ligands wherein R represents exemplary points at which the Linker can be attached.

FIG. 1GG-1MM provide non-limiting examples of BET Bromodomain-Containing Protein Targeting Ligands wherein R represents exemplary points at which the Linker can be attached.

FIG. 1NN provides non-limiting examples of HDAC Targeting Ligands wherein R represents exemplary points at which the Linker can be attached.

FIG. 1OO provides non-limiting examples of RAF Receptor Targeting Ligands wherein R represents exemplary points at which the Linker can be attached.

FIG. 1PP provides non-limiting examples of FKBP Receptor Targeting Ligands wherein R represents exemplary points at which the Linker can be attached.

FIG. 1QQ-1TT provide non-limiting examples of Androgen Receptor Targeting Ligands wherein R represents exemplary points at which the Linker can be attached.

FIG. 1UU provides non-limiting examples of Estrogen Receptor Targeting Ligands wherein R represents exemplary points at which the Linker can be attached.

FIG. 1VV-1WW provide non-limiting examples of Thyroid Hormone Receptor Targeting Ligands wherein R represents exemplary points at which the Linker can be attached.

FIG. 1XX provides non-limiting examples of HIV Protease Targeting Ligands wherein R represents exemplary points at which the Linker can be attached.

FIG. 1YY provides non-limiting examples of HIV Integrase Targeting Ligands wherein R represents exemplary points at which the Linker can be attached.

FIG. 1ZZ provides non-limiting examples of HCV Protease Targeting Ligands wherein R represents exemplary points at which the Linker can be attached.

FIG. 1AAA provides non-limited examples of AP1 and/or AP2 Targeting Ligands wherein R represents exemplary points at which the Linker can be attached.

FIG. 1BBB-1CCC provide non-limiting examples of MCL-1 Targeting Ligands wherein R represents exemplary points at which the Linker can be attached.

FIG. 1DDD provides non-limiting examples of IDH1 Targeting Ligands wherein R represents exemplary points at which the Linker can be attached.

FIG. 1EEE-1FFF provide non-limiting examples of RAS or RASK Targeting Ligands wherein R represents exemplary points at which the Linker can be attached.

FIG. 1GGG provides non-limiting examples of MERTK or MER Targeting Ligands wherein R represents exemplary points at which the Linker can be attached.

FIG. 1HHH-1III provide non-limiting examples of EGFR Targeting Ligands wherein R represents exemplary points at which the Linker can be attached.

FIG. 1JJJ-1KKK provide non-limiting examples of FLT3 Targeting Ligands wherein R represents exemplary points at which the Linker can be attached.

FIG. 1LLL provides non-limiting examples of SMARCA2 Targeting Ligands wherein R represents exemplary points at which the Linker can be attached.

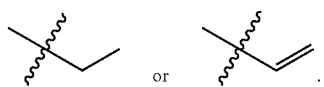

Figure 1A:
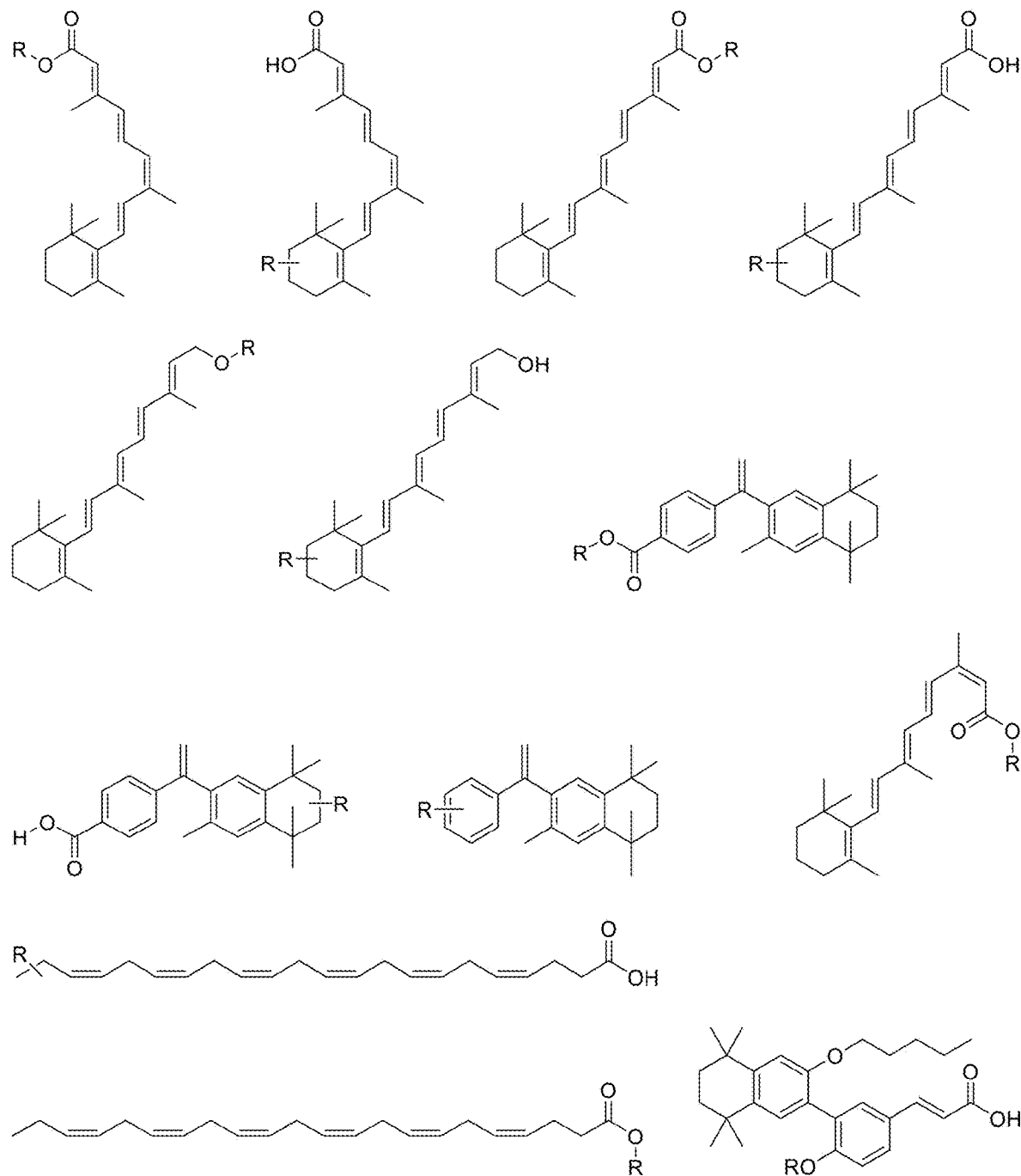
FIG. 1A-1C provide non-limiting examples of Retinoid X Receptor (RXR) Targeting Ligands wherein R represents exemplary points at which the Linker can be attached.
Figure 1B:
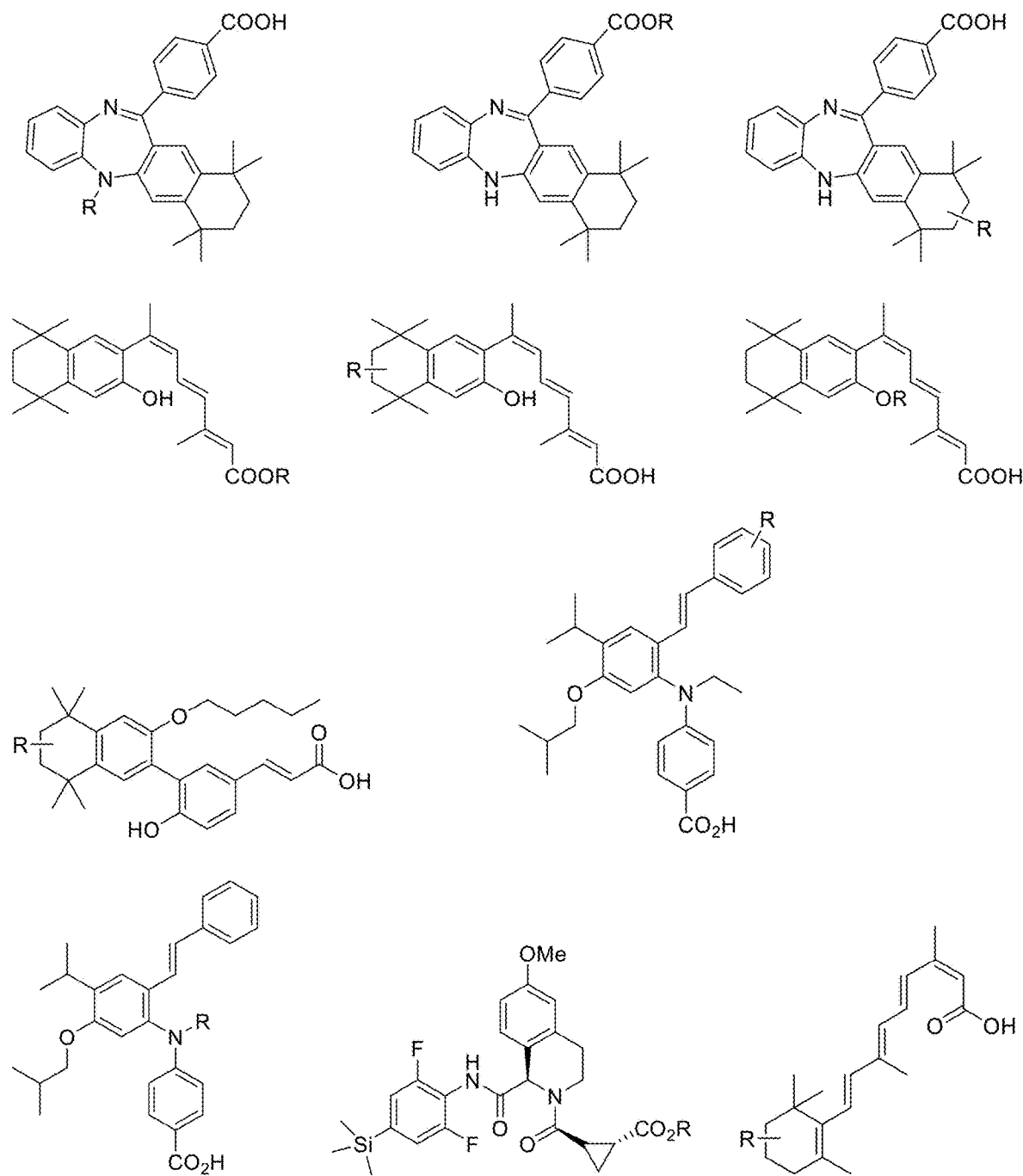
Figure 1C:
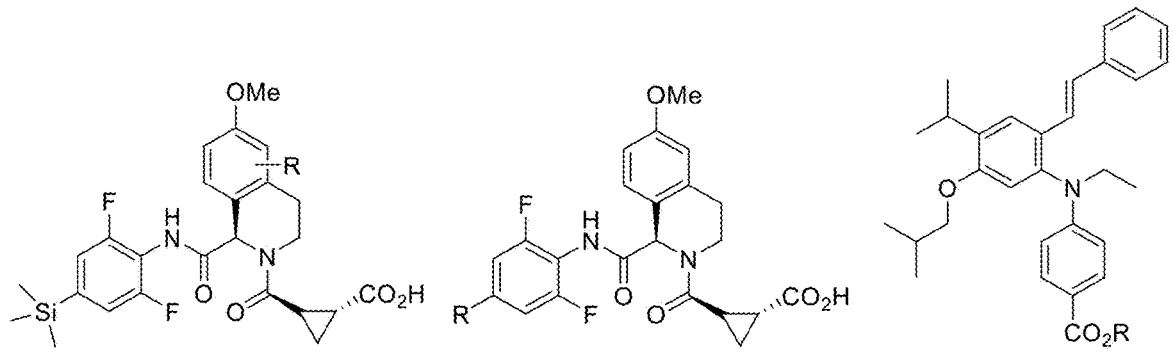
Figure 1D:
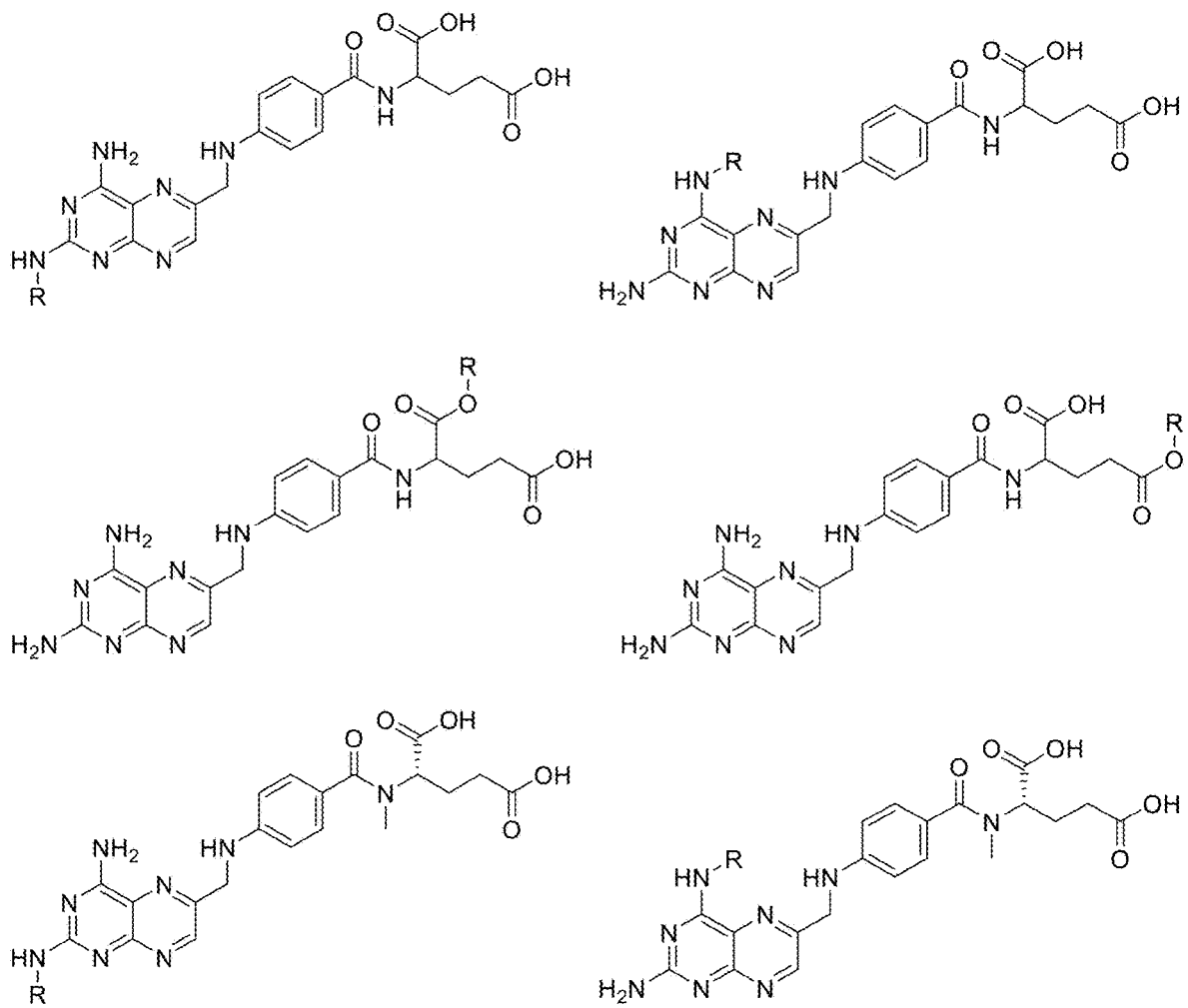
FIG. 1D-1F provide non-limiting examples of general Dihydrofolate reductase (DHFR) Targeting Ligands wherein R represents exemplary points at which the Linker can be attached.
Figure 1E:
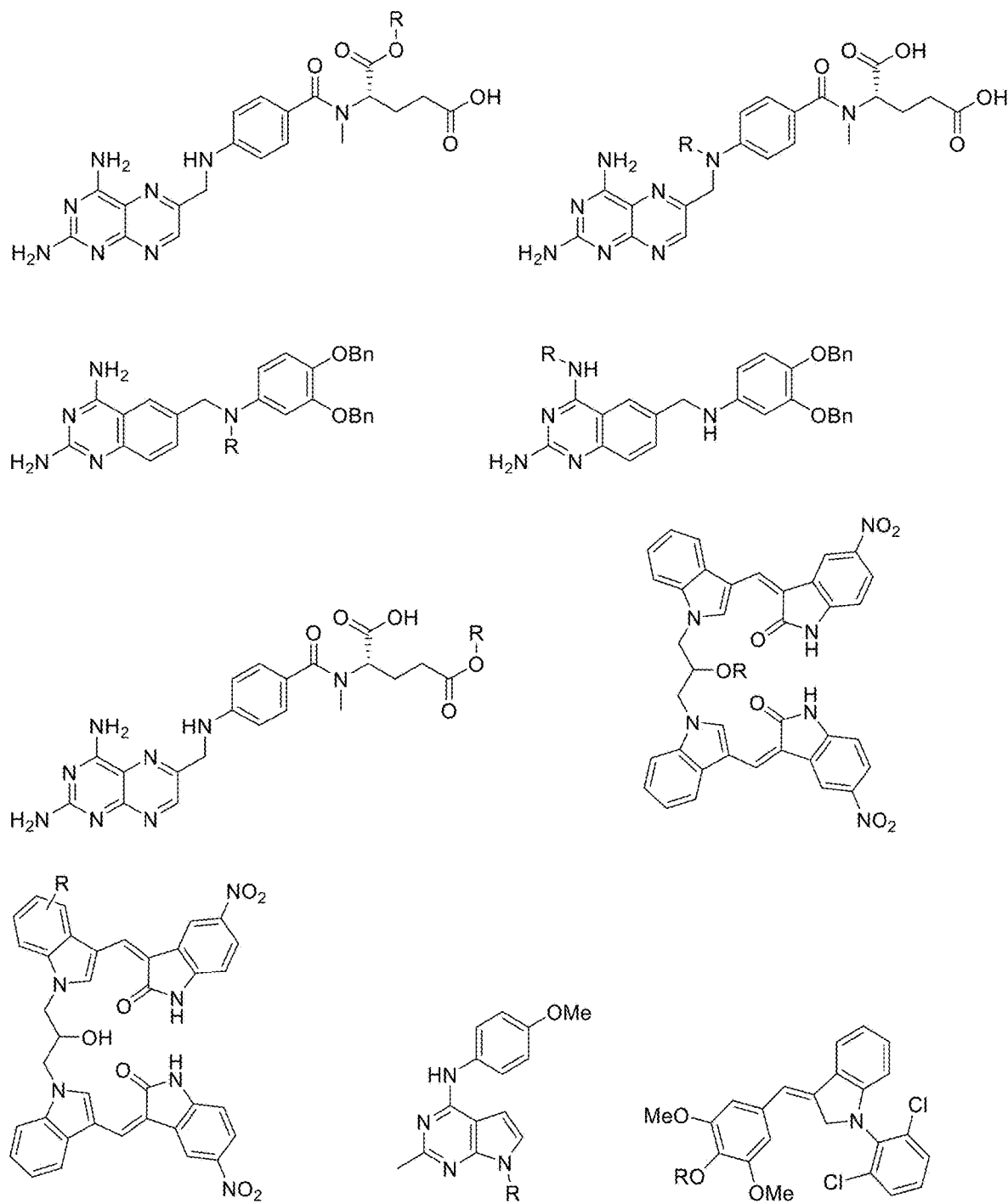
Figure 1F:
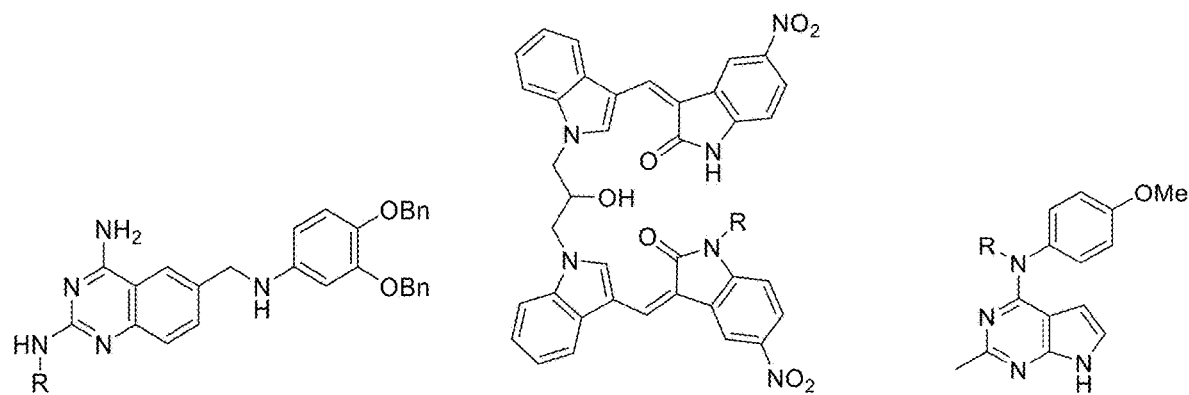
Figure 1G:
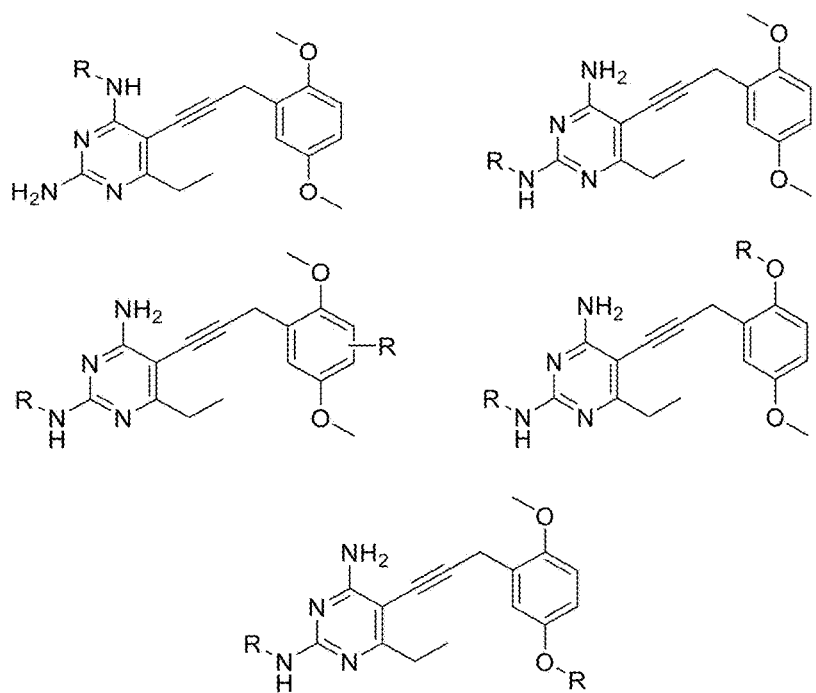
FIG. 1G provides non-limiting examples of *Bacillus anthracis* Dihydrofolate reductase (BaDHFR) Targeting Ligands wherein R represents exemplary points at which the Linker can be attached.
Figure 1H:
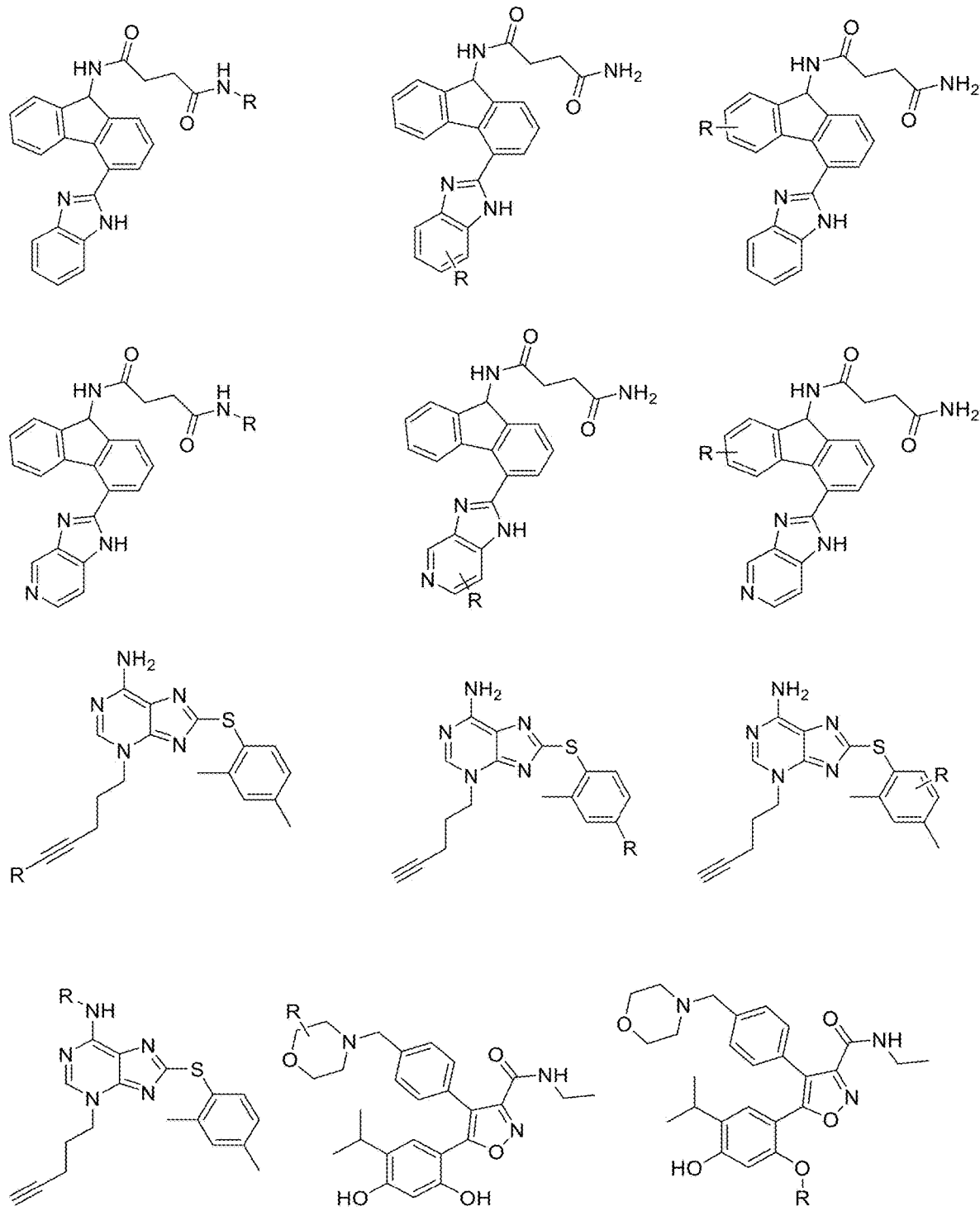
FIG. 1H-1J provide non-limiting examples of Heat Shock Protein 90 (HSP90) Targeting Ligands wherein R represents exemplary points at which the Linker can be attached.
Figure 1I:
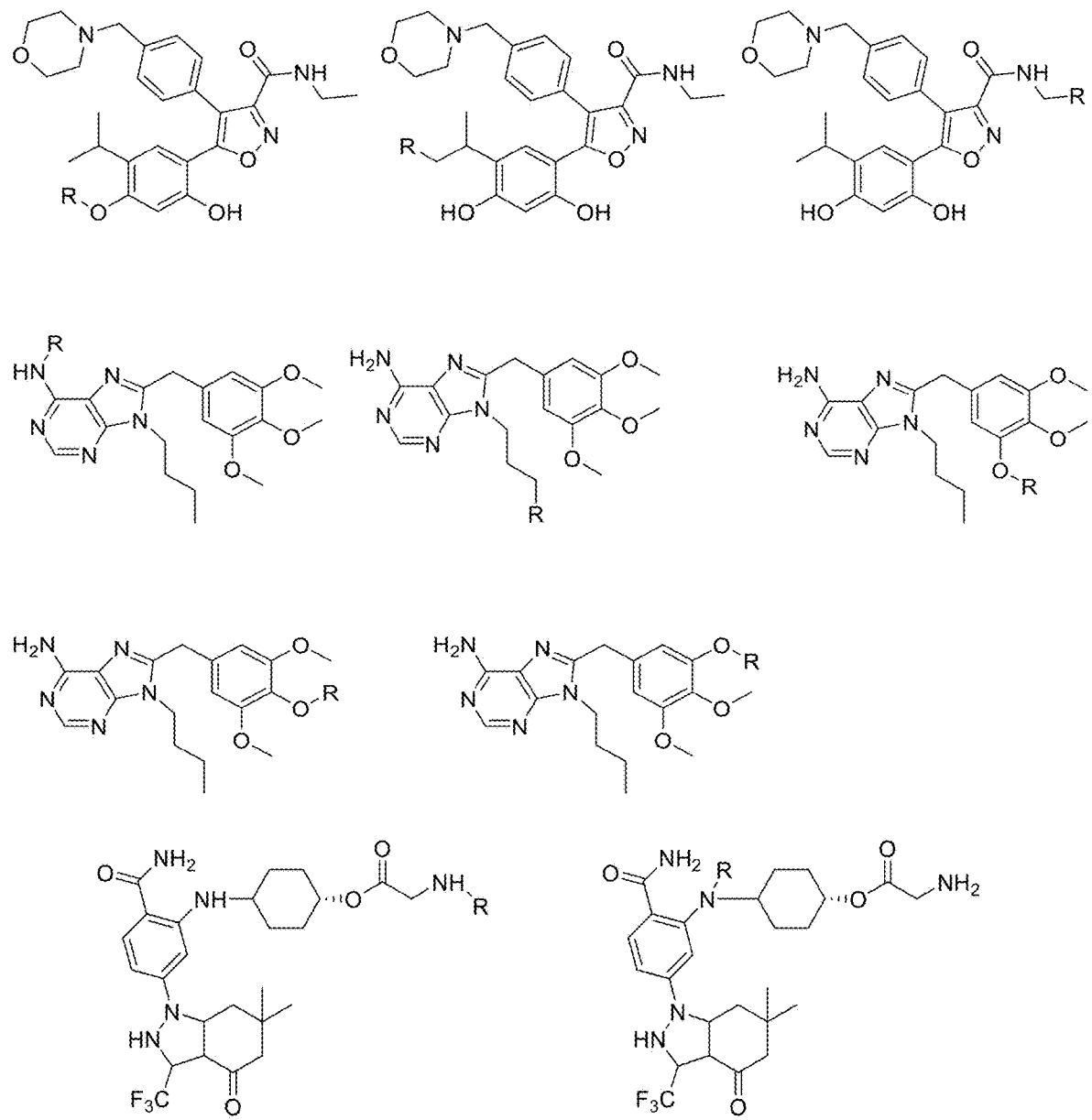
Figure 1J:
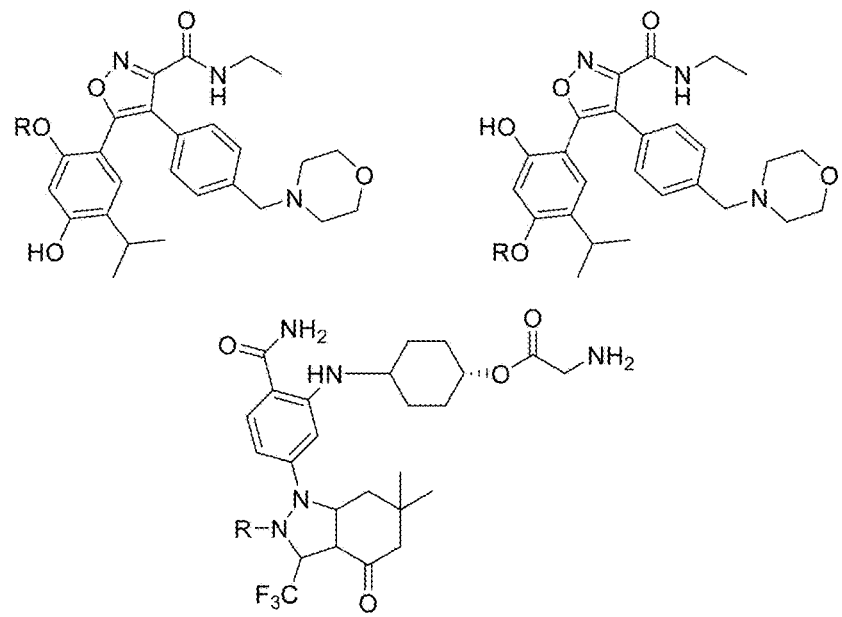
Figure 1K:
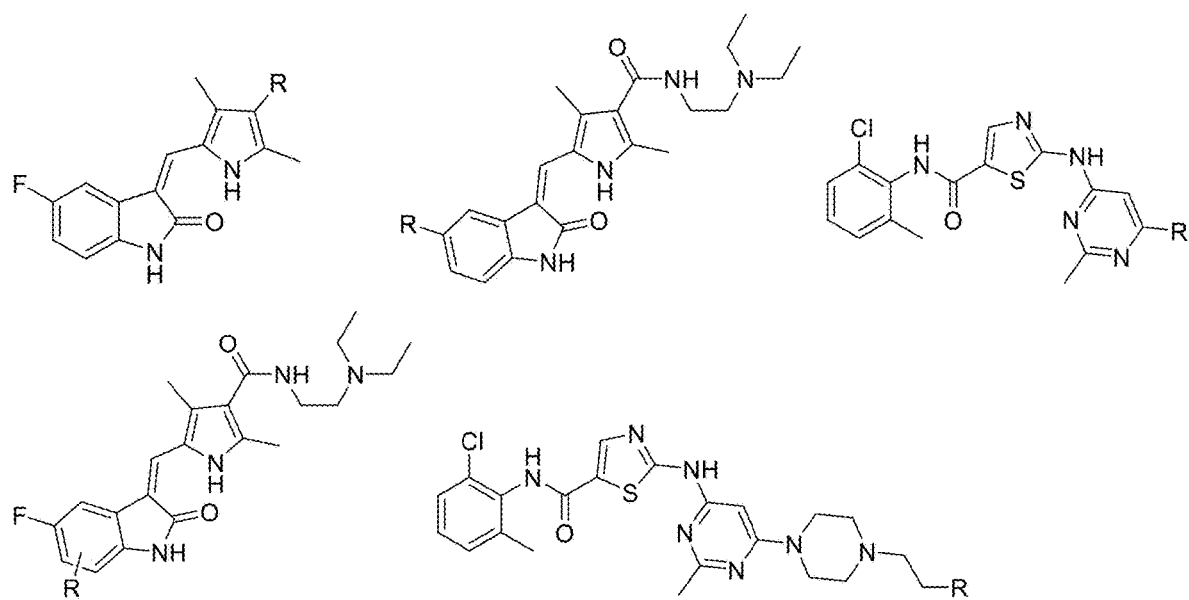
FIG. 1K-1Q provide non-limiting examples of General Kinase and Phosphatase Targeting Ligands wherein R represents exemplary points at which the Linker can be attached.
Figure 1L:
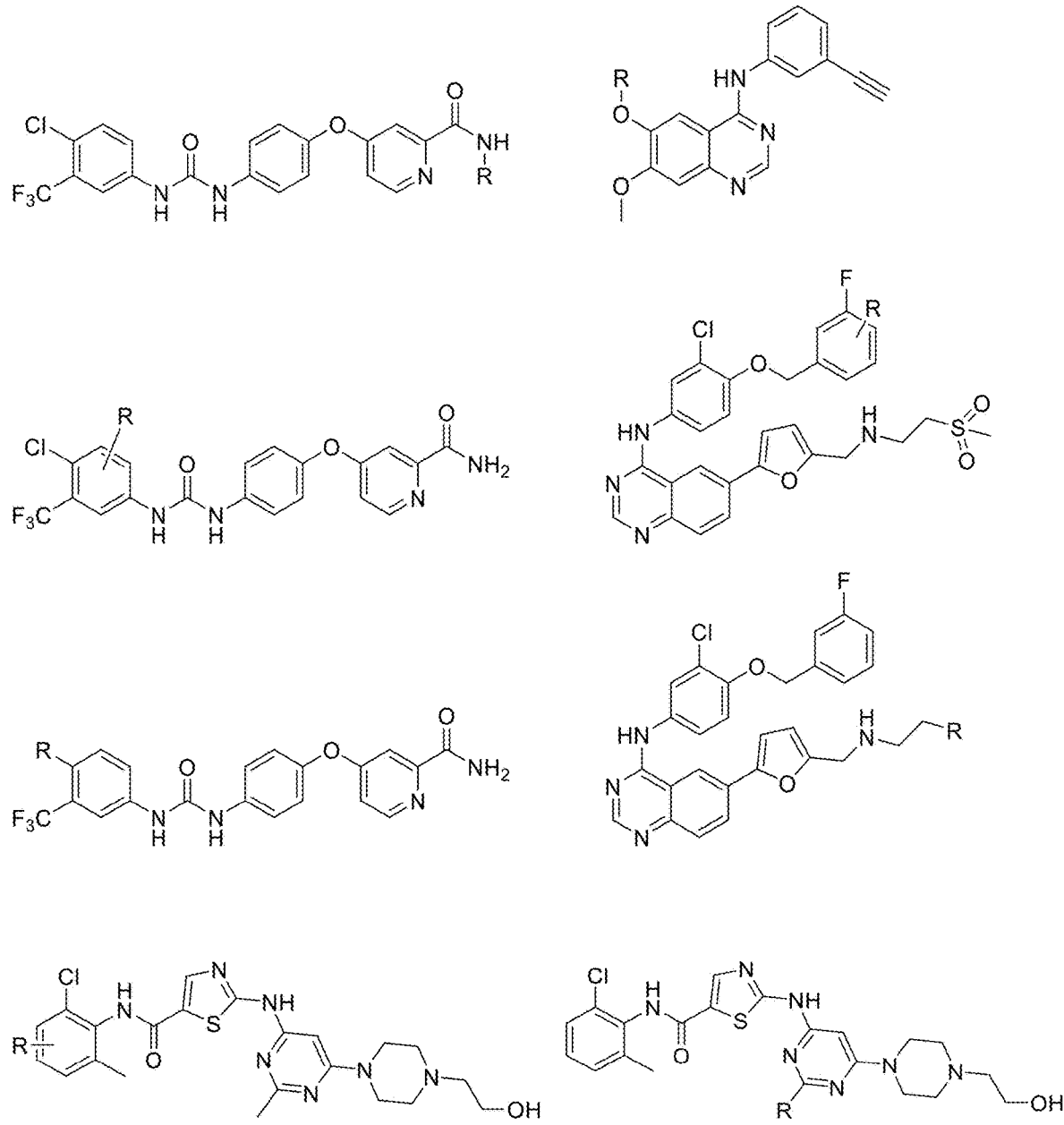
Figure 1M:
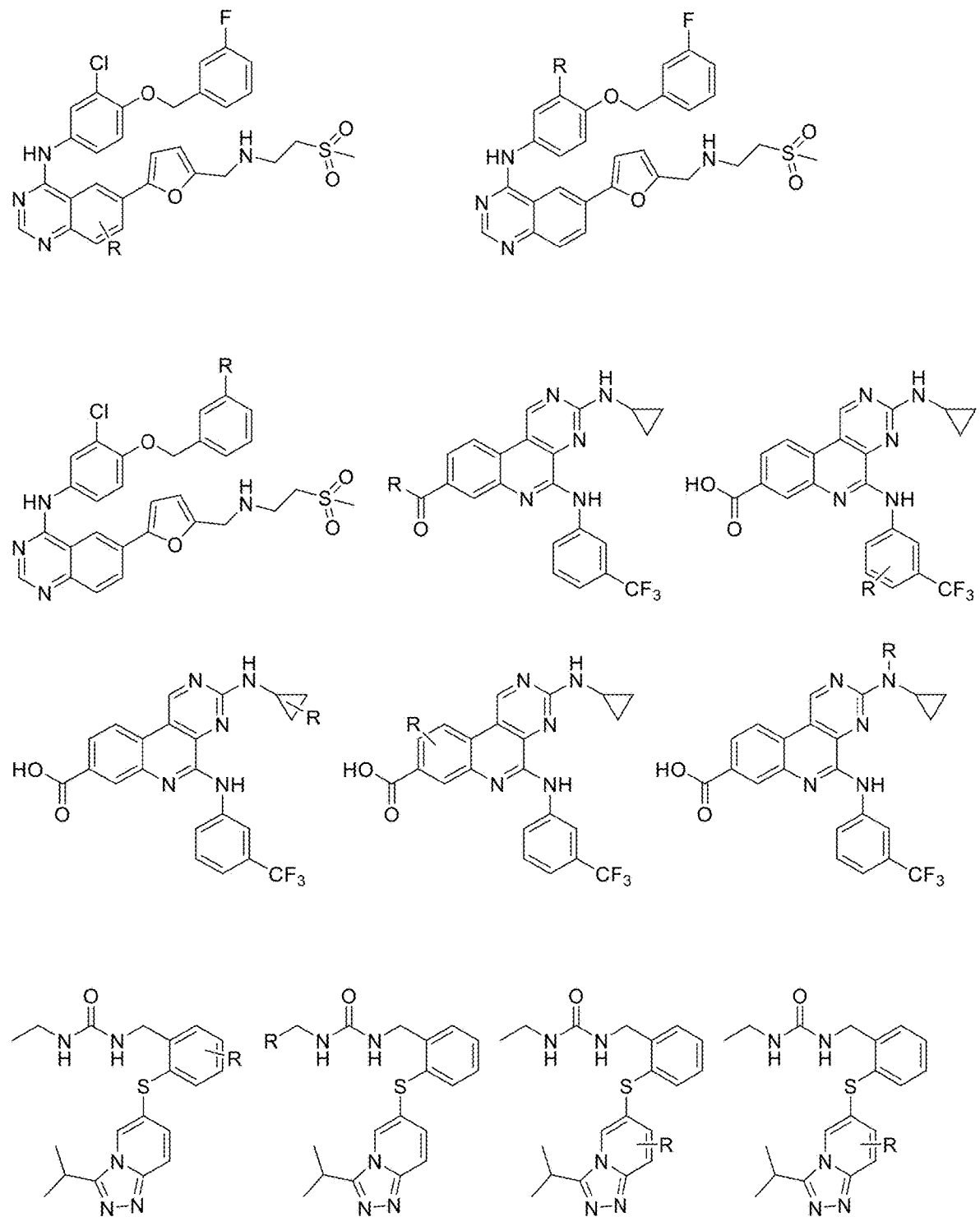
Figure 1N:
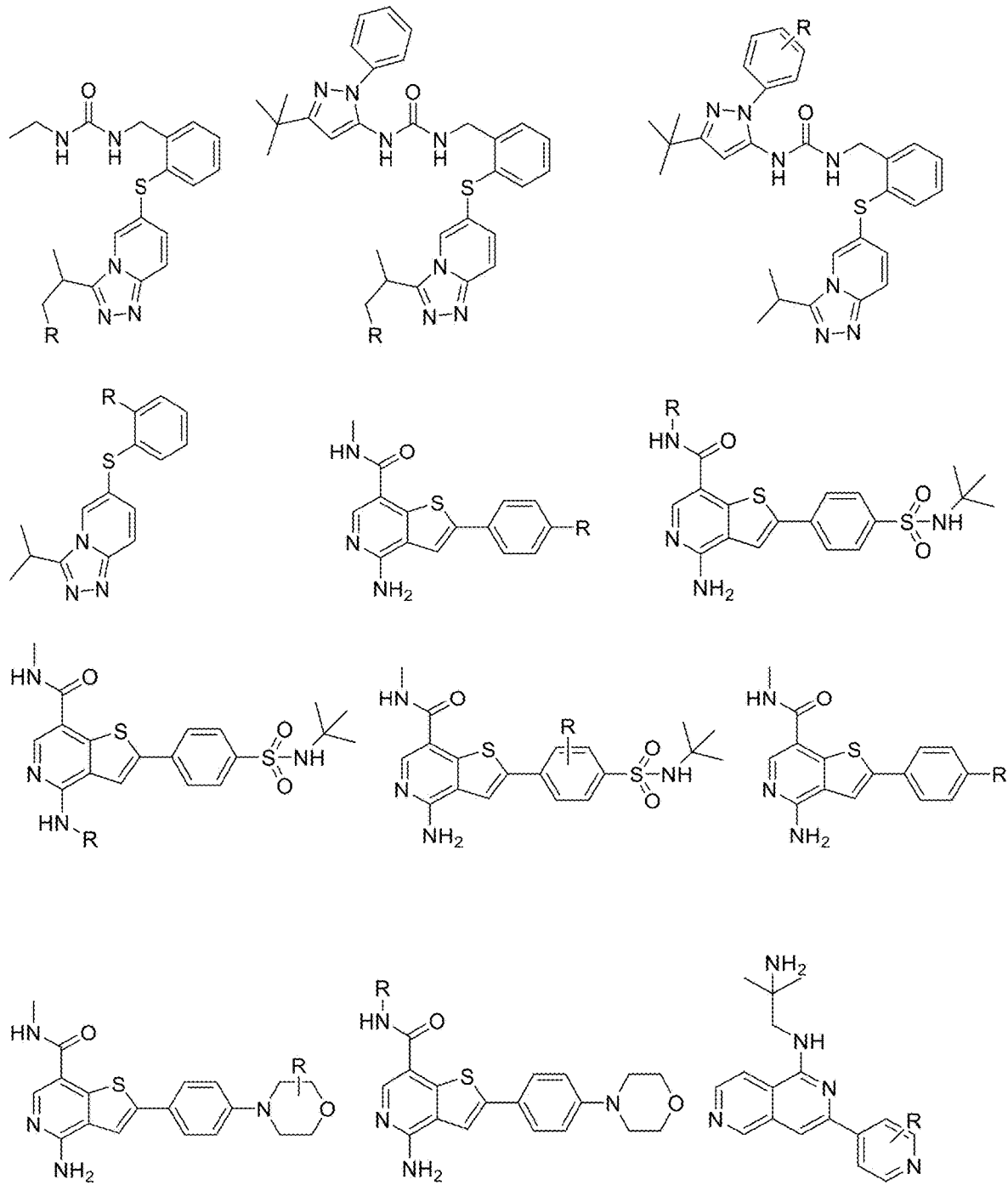
Figure 1O:
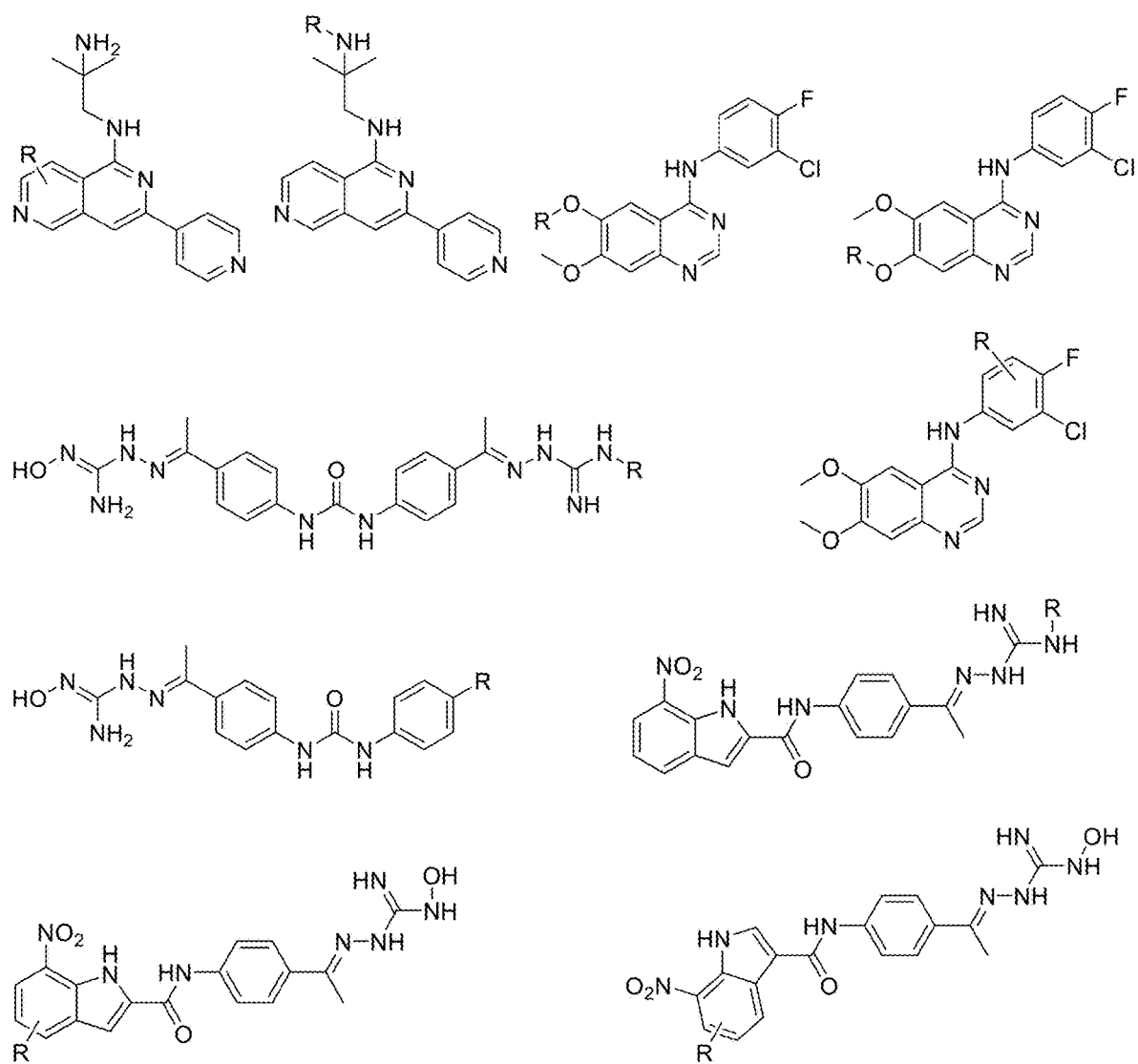
Figure 1P:
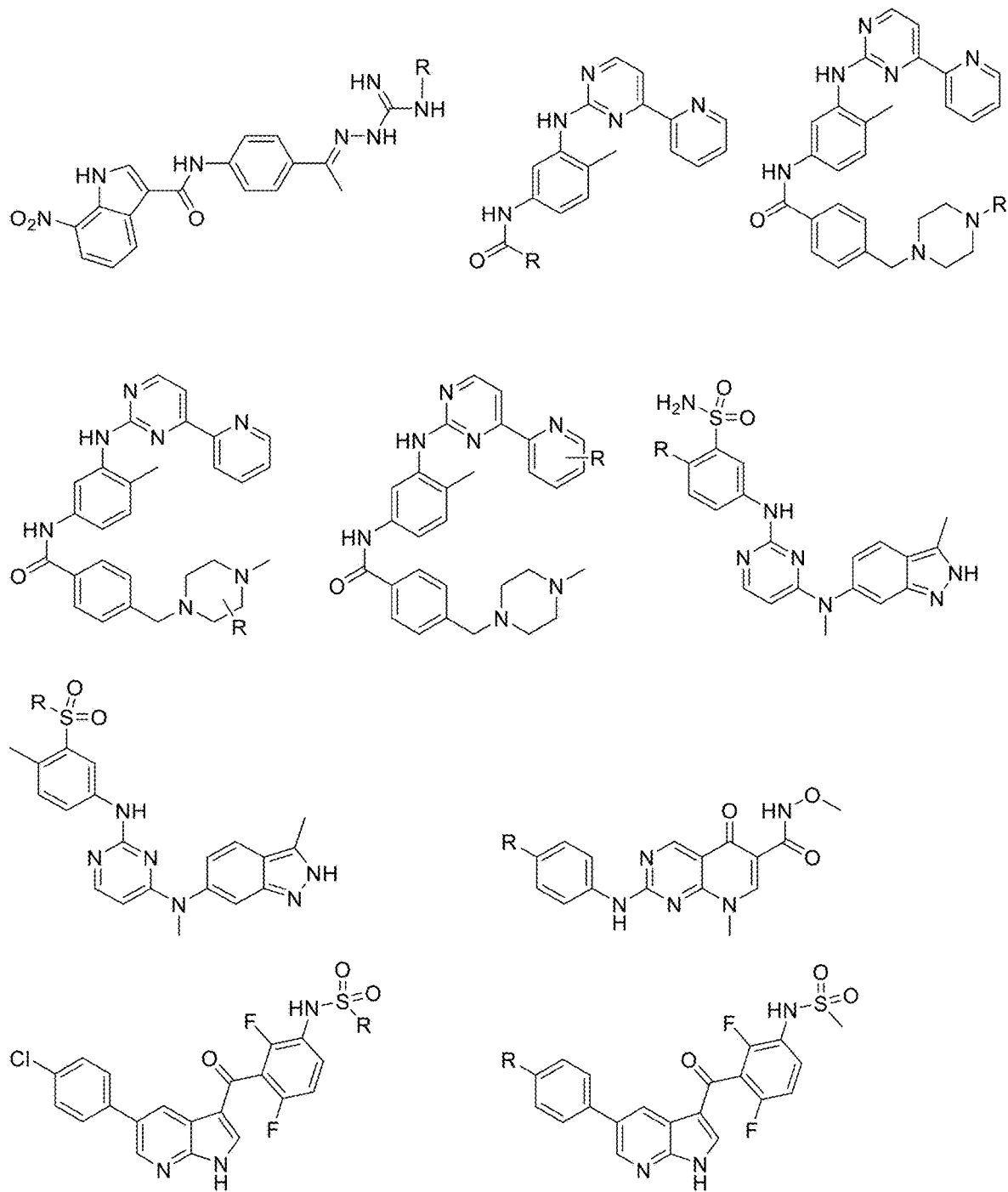
Figure 1S:
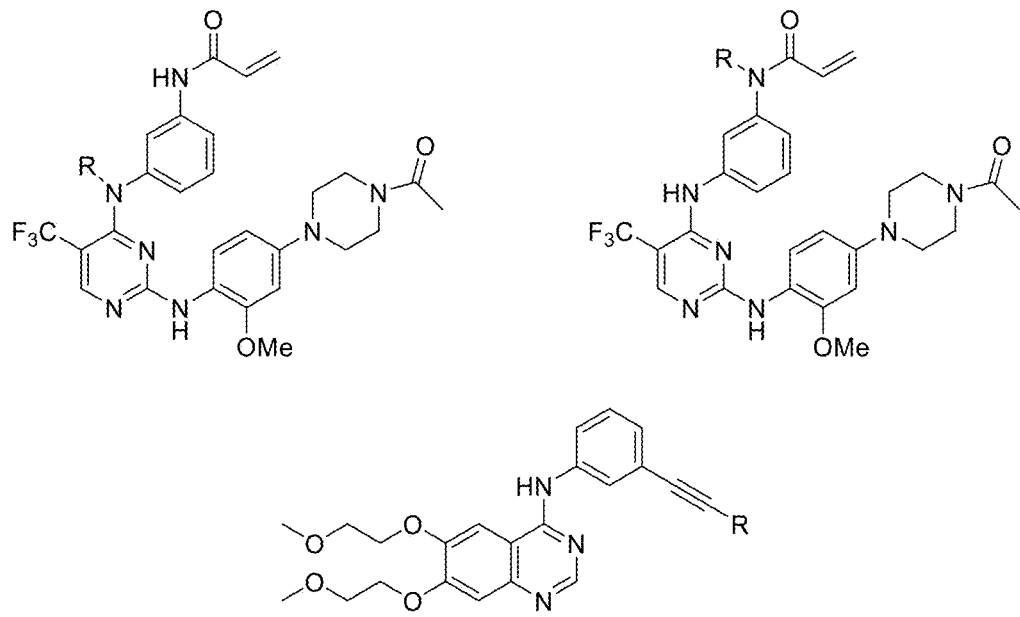
Figure 1T:
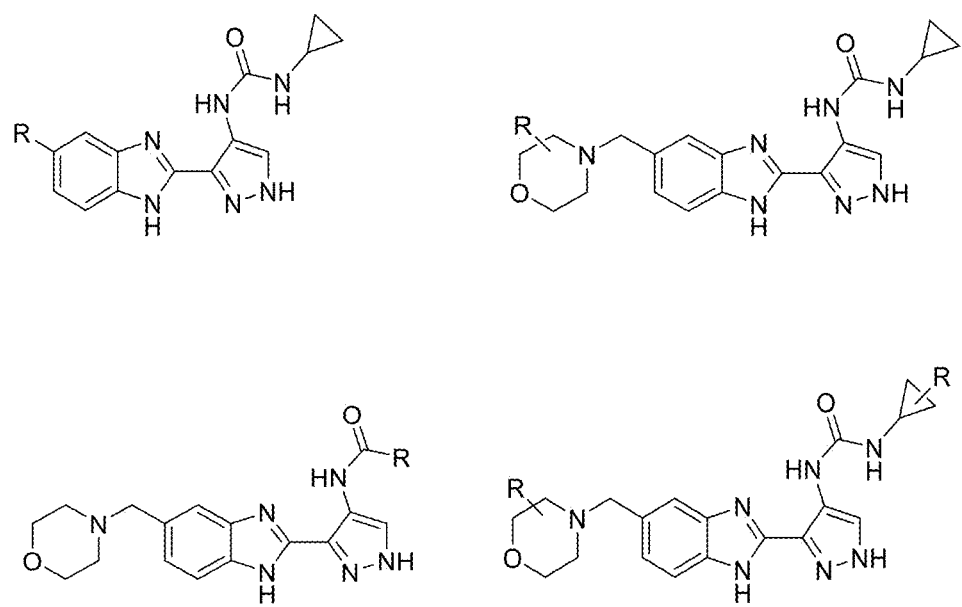
FIG. 1T provides non-limiting examples of Aurora Kinase Targeting Ligands wherein R represents exemplary points at which the Linker can be attached.
Figure 1U:
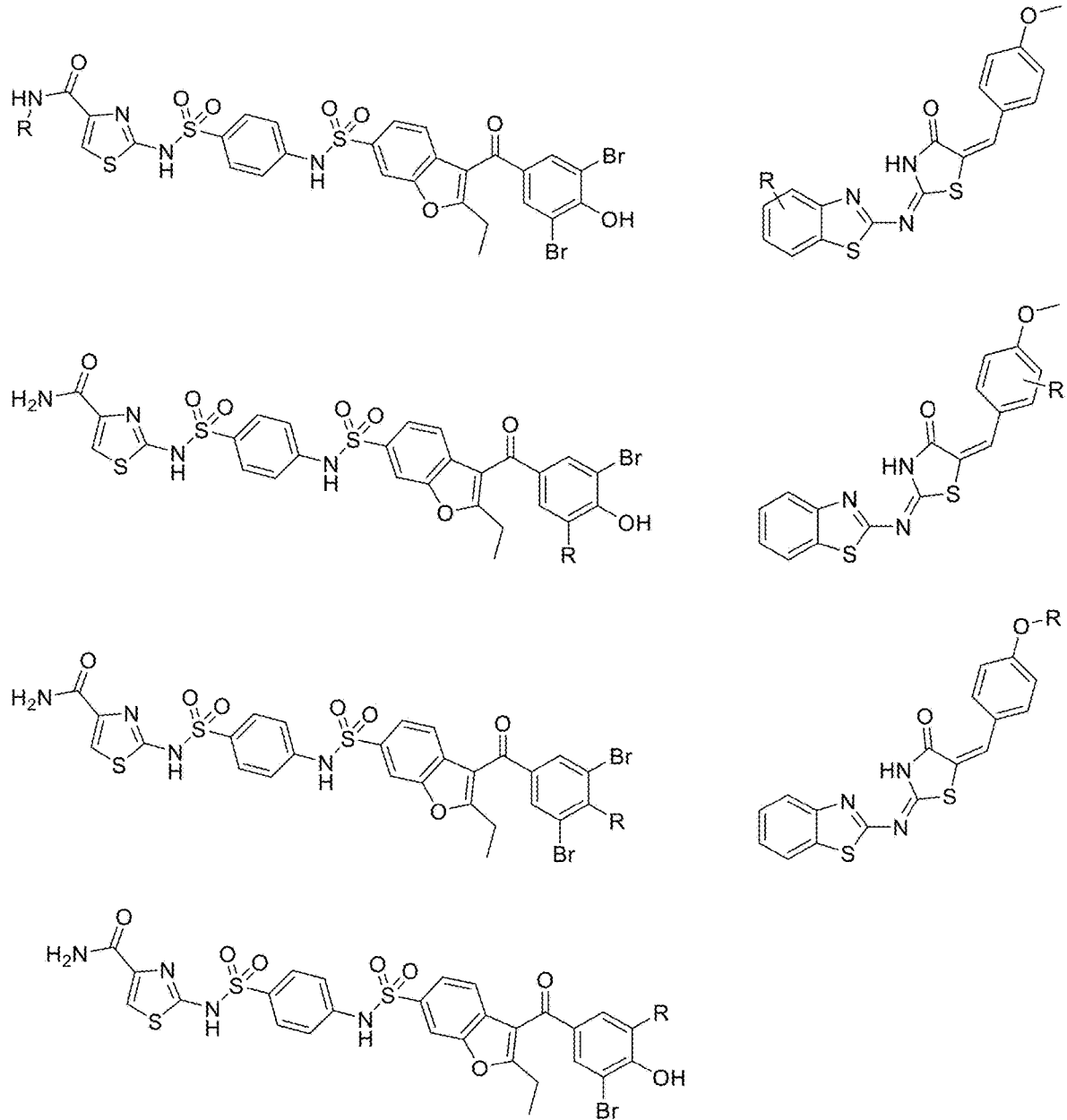
FIG. 1U provides non-limiting examples of Protein Tyrosine Phosphatase Targeting Ligands wherein R represents exemplary points at which the Linker can be attached.
Figure 1V:
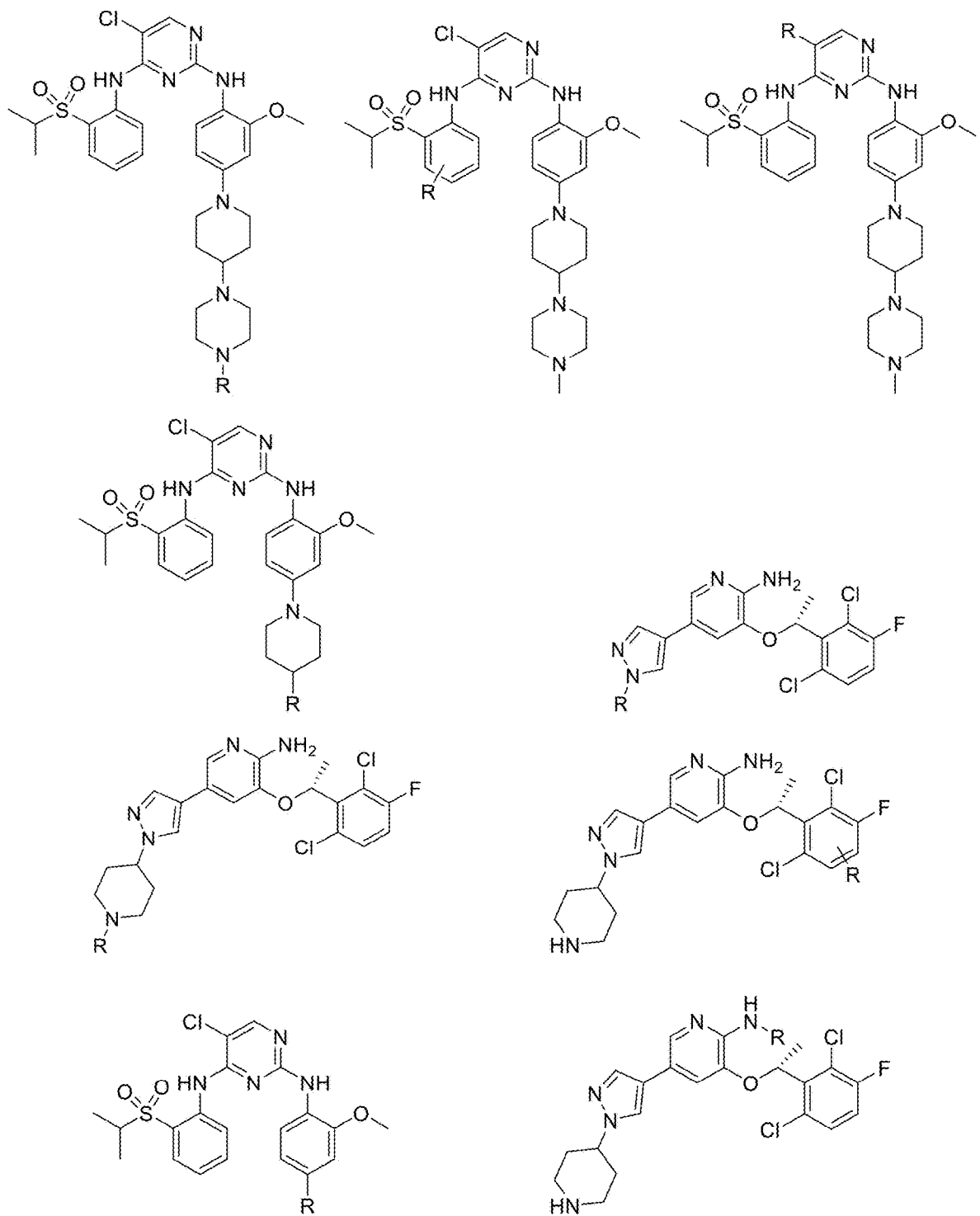
FIG. 1V provides non-limiting examples of ALK Targeting Ligands wherein R represents exemplary points at which the Linker can be attached.
Figure 1W:
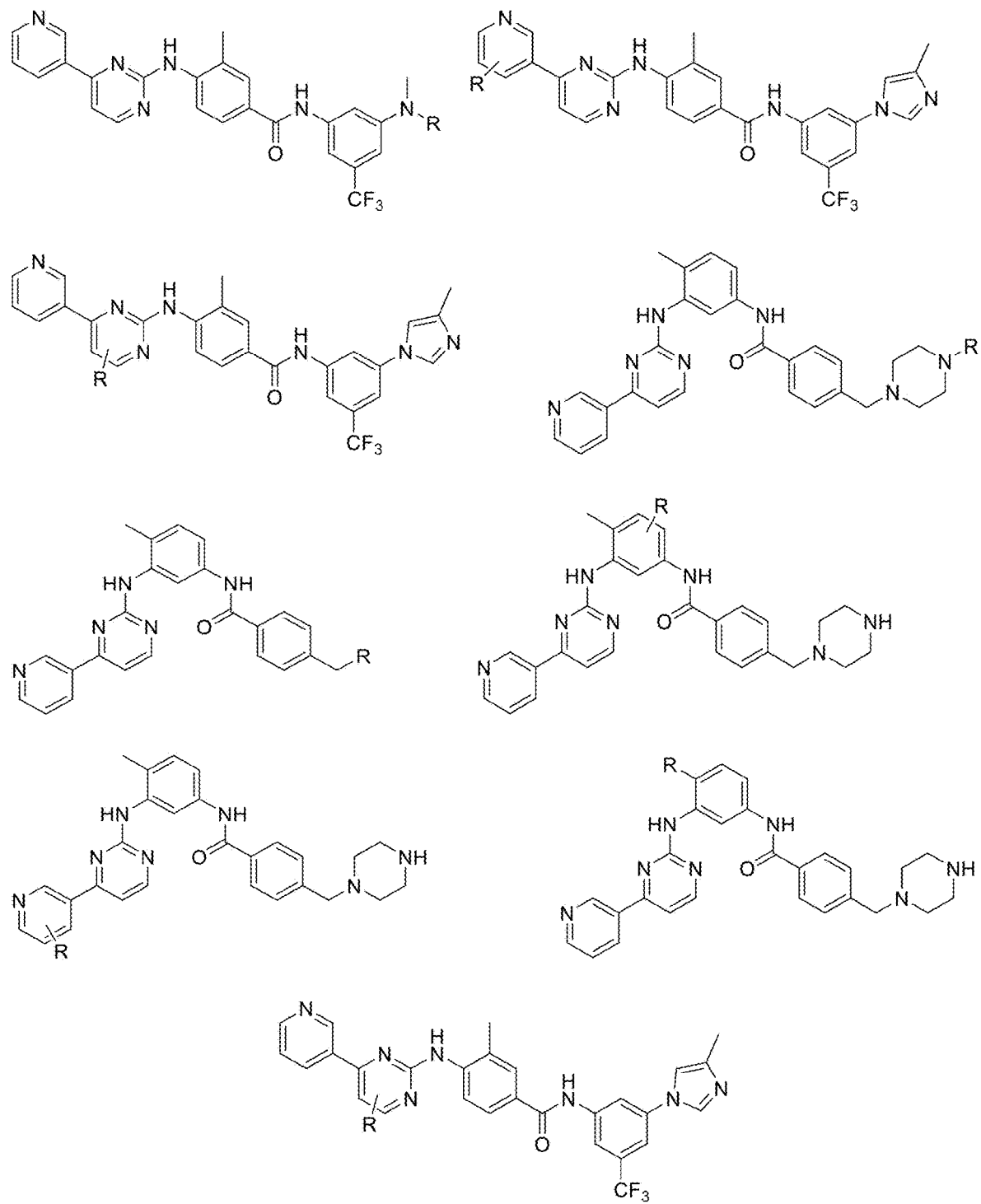
FIG. 1W provides non-limiting examples of ABL Targeting Ligands wherein R represents exemplary points at which the Linker can be attached.
Figure 1X:
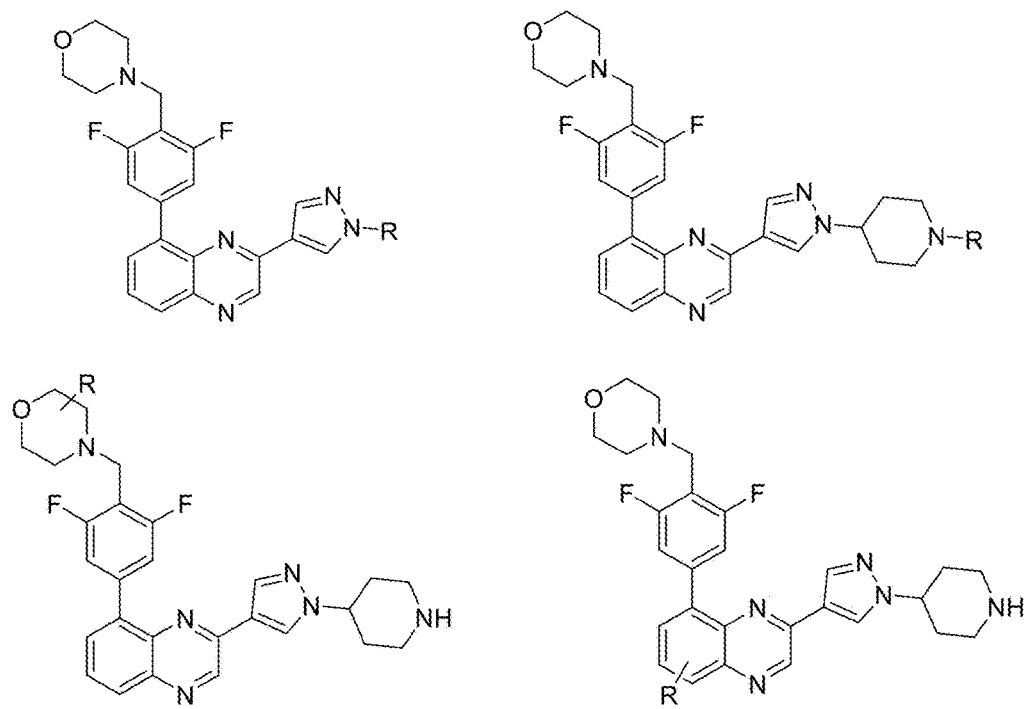
FIG. 1X provides non-limiting examples of JAK2 Targeting Ligands wherein R represents exemplary points at which the Linker can be attached.
Figure 1Y:
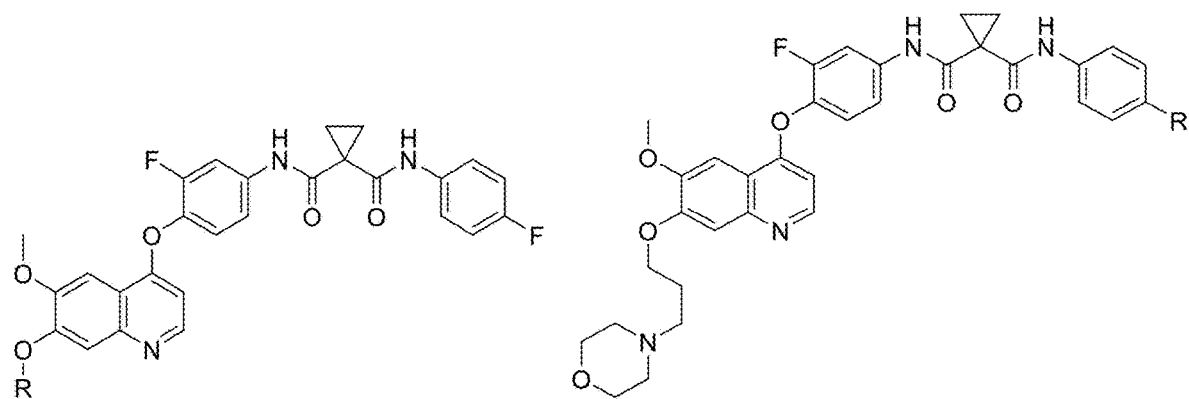
FIG. 1Y-1Z provide non-limiting examples of MET Targeting Ligands wherein R represents exemplary points at which the Linker can be attached.
Figure 1Z:
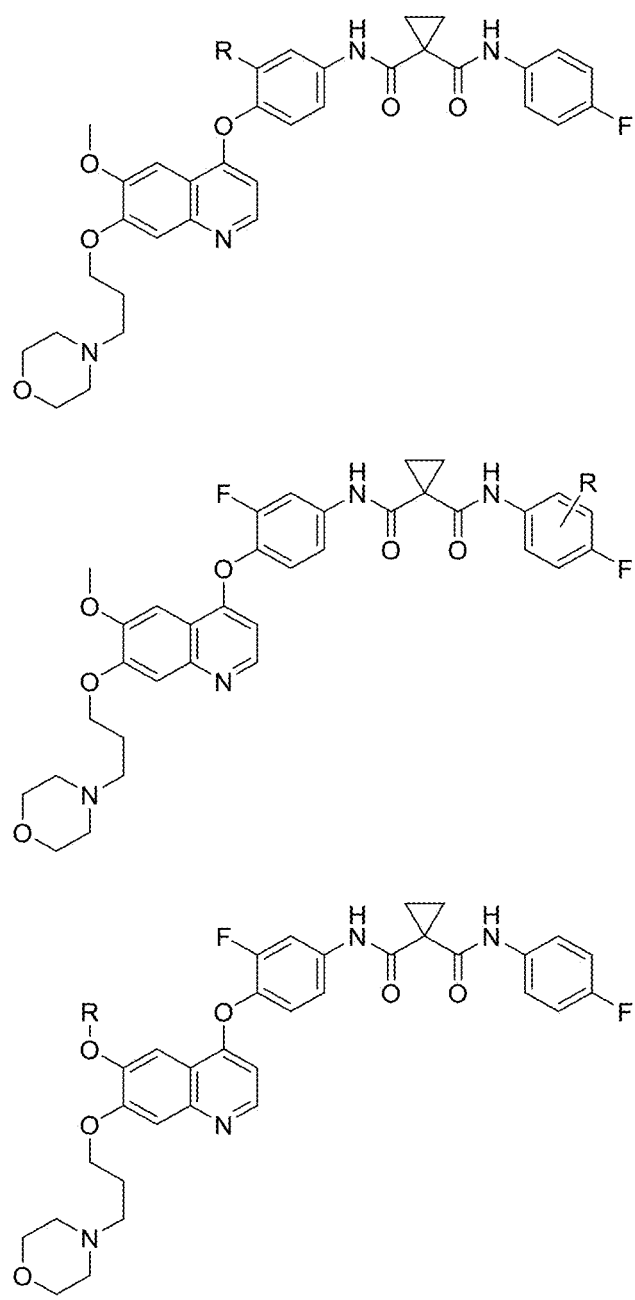
Figure 1A:
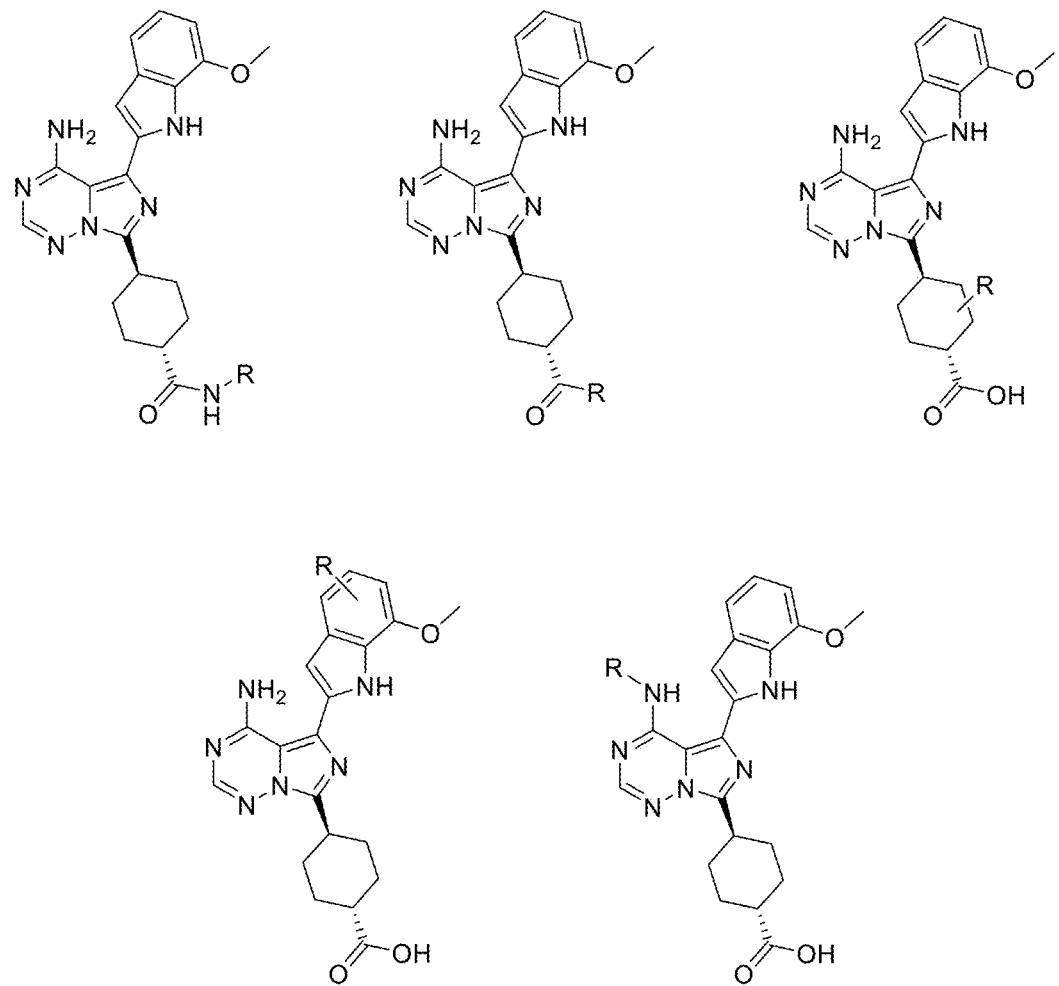
Figure 1B:
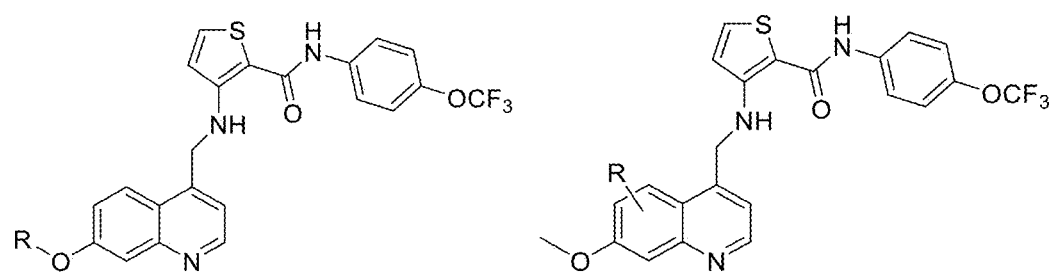
Figure 1C:
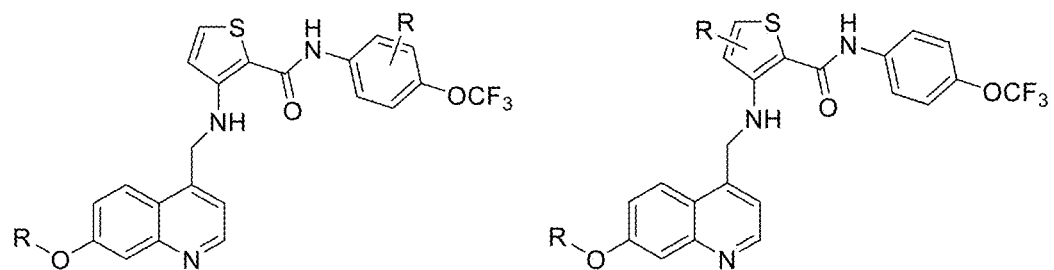
Figure 1D:
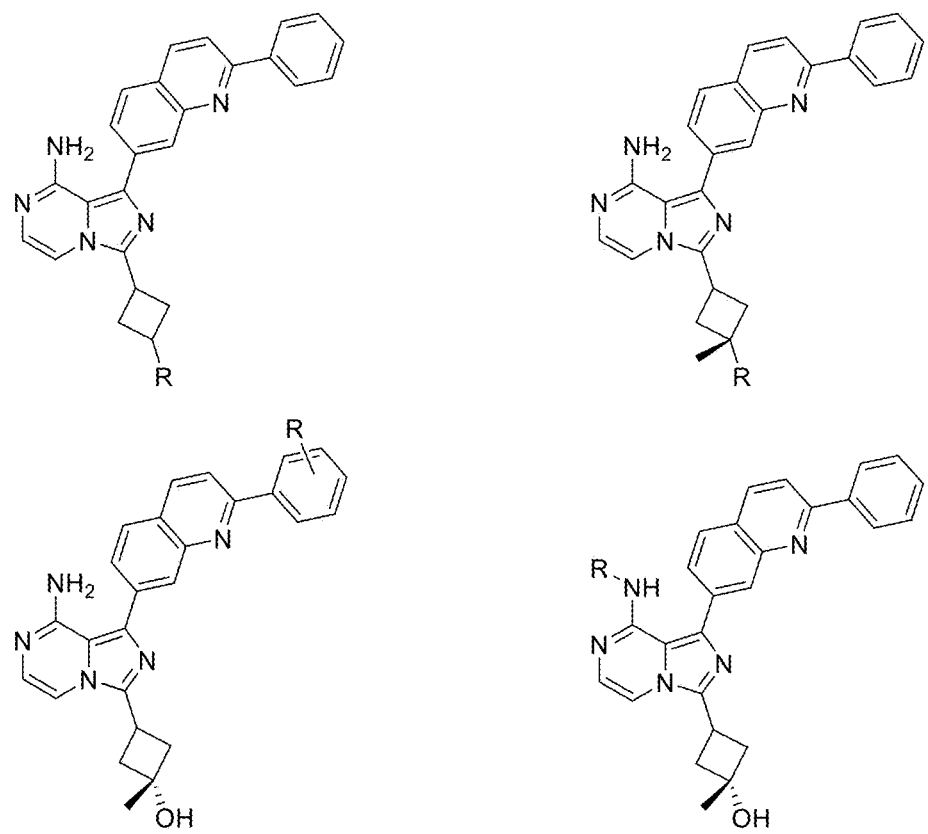
Figure 1F:
Figure 1G:
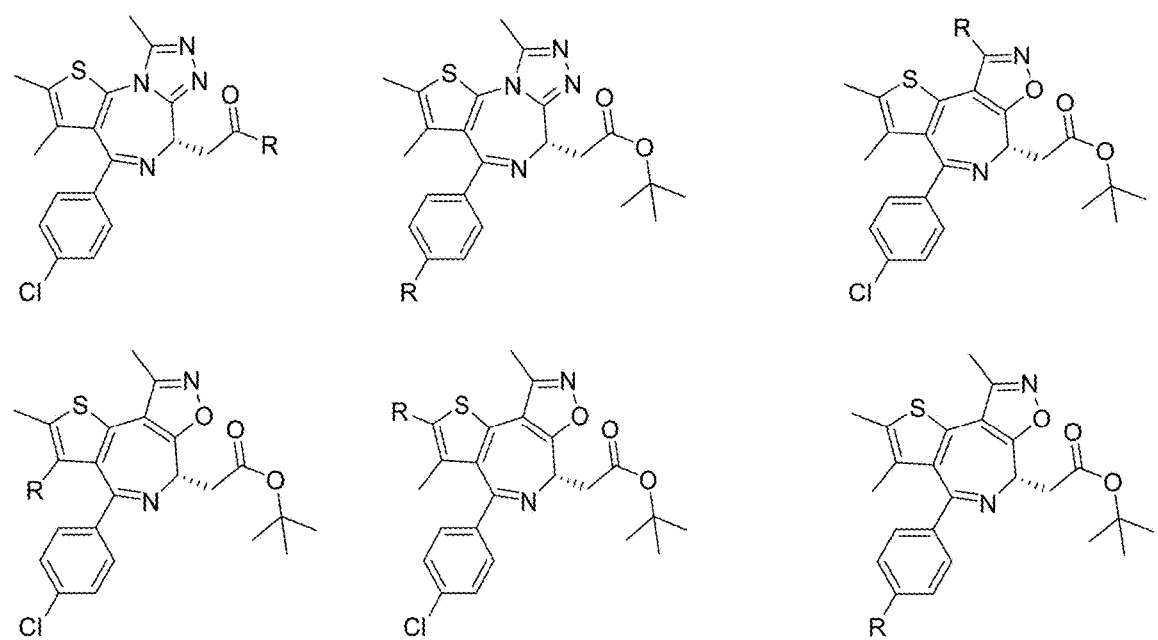
Figure 1H:
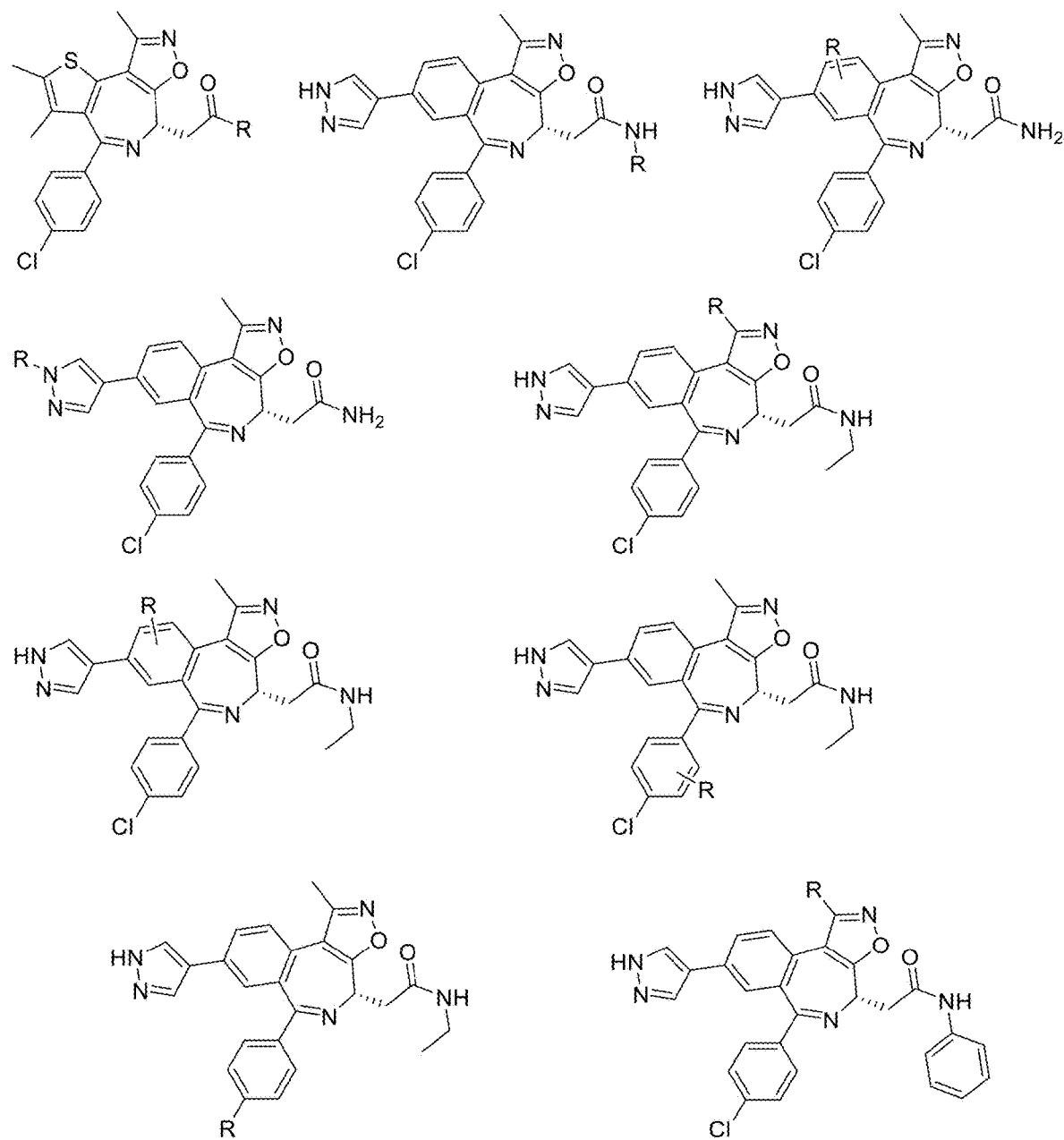
Figure 1I:
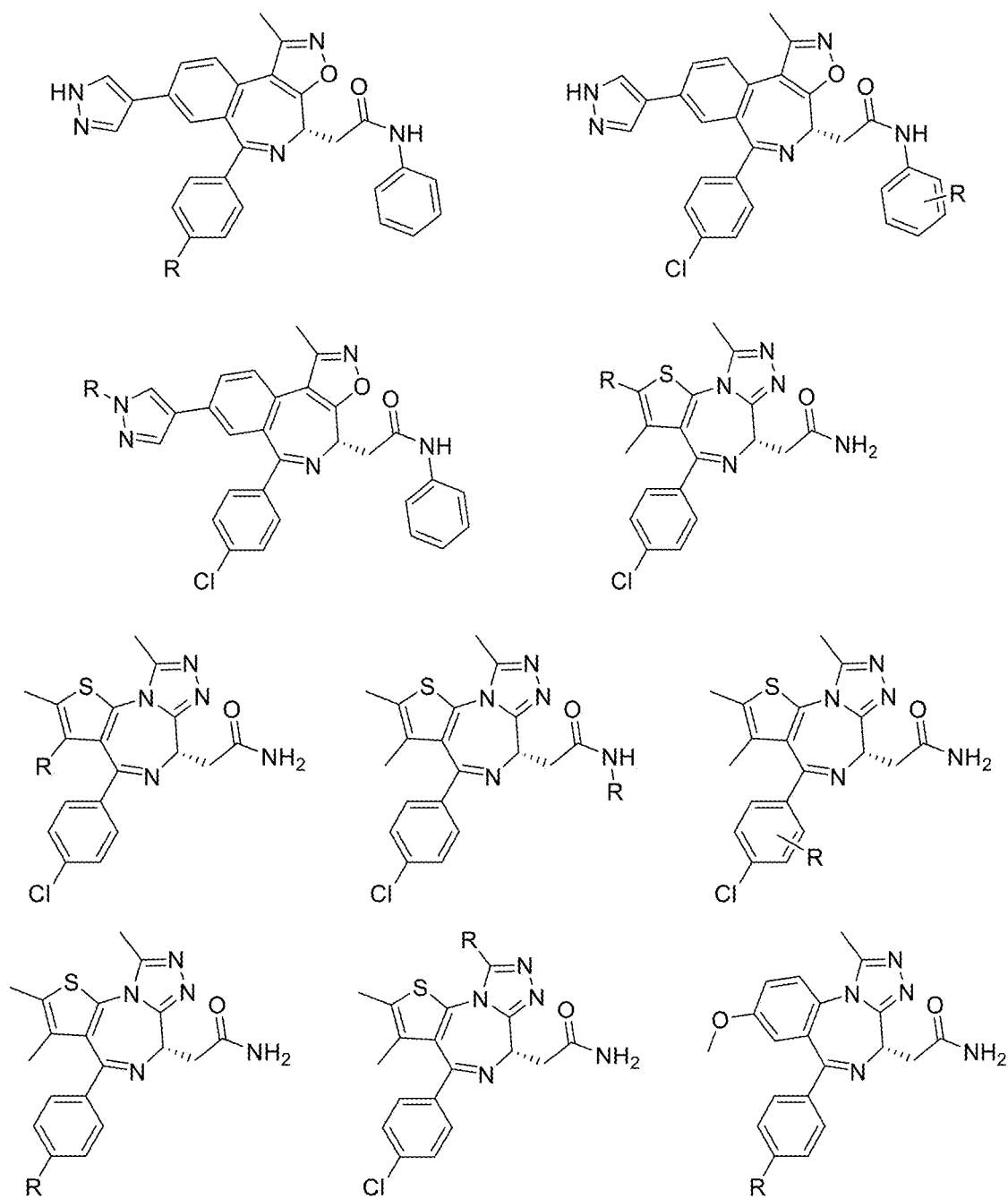
Figure 1J:
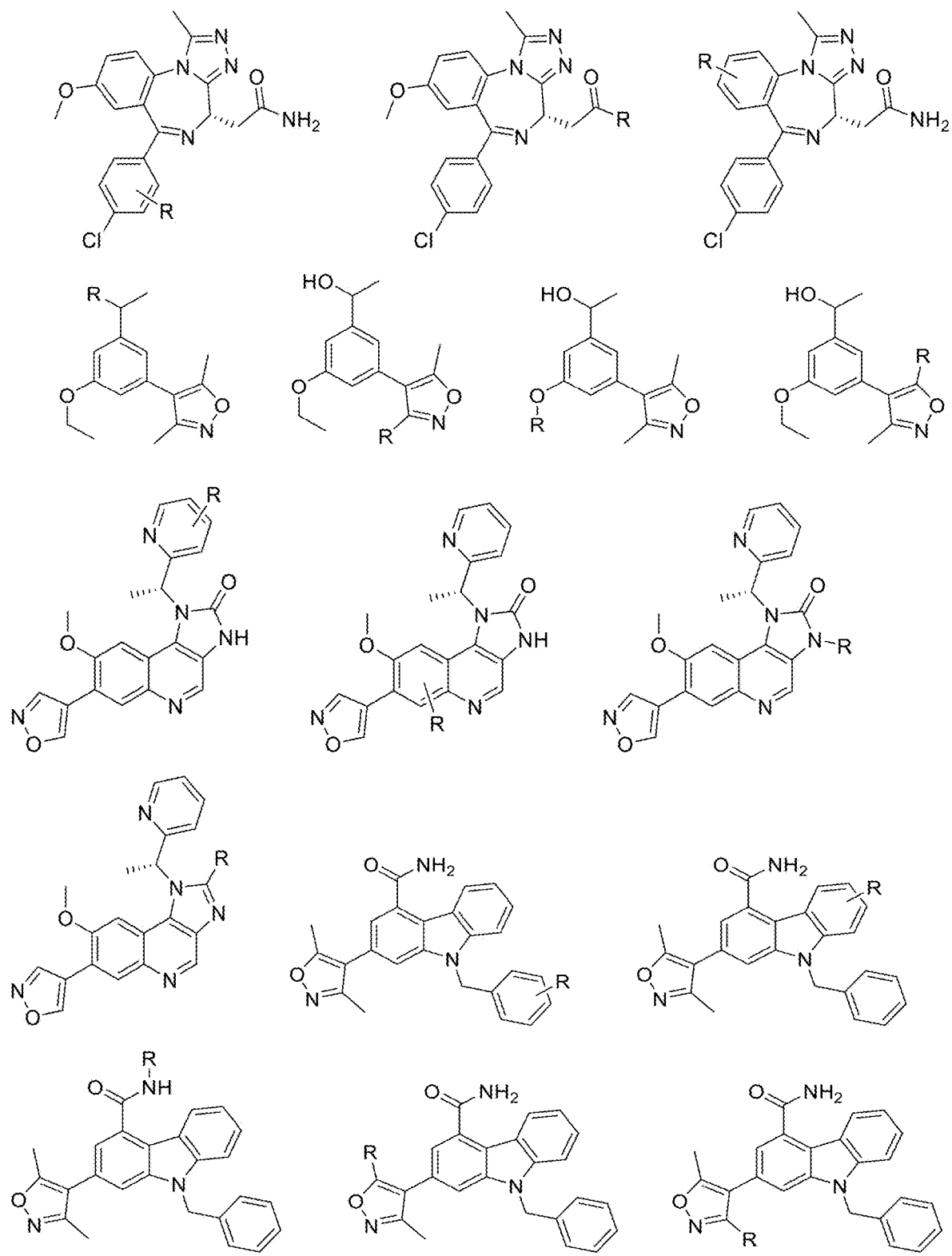
Figure 1K:
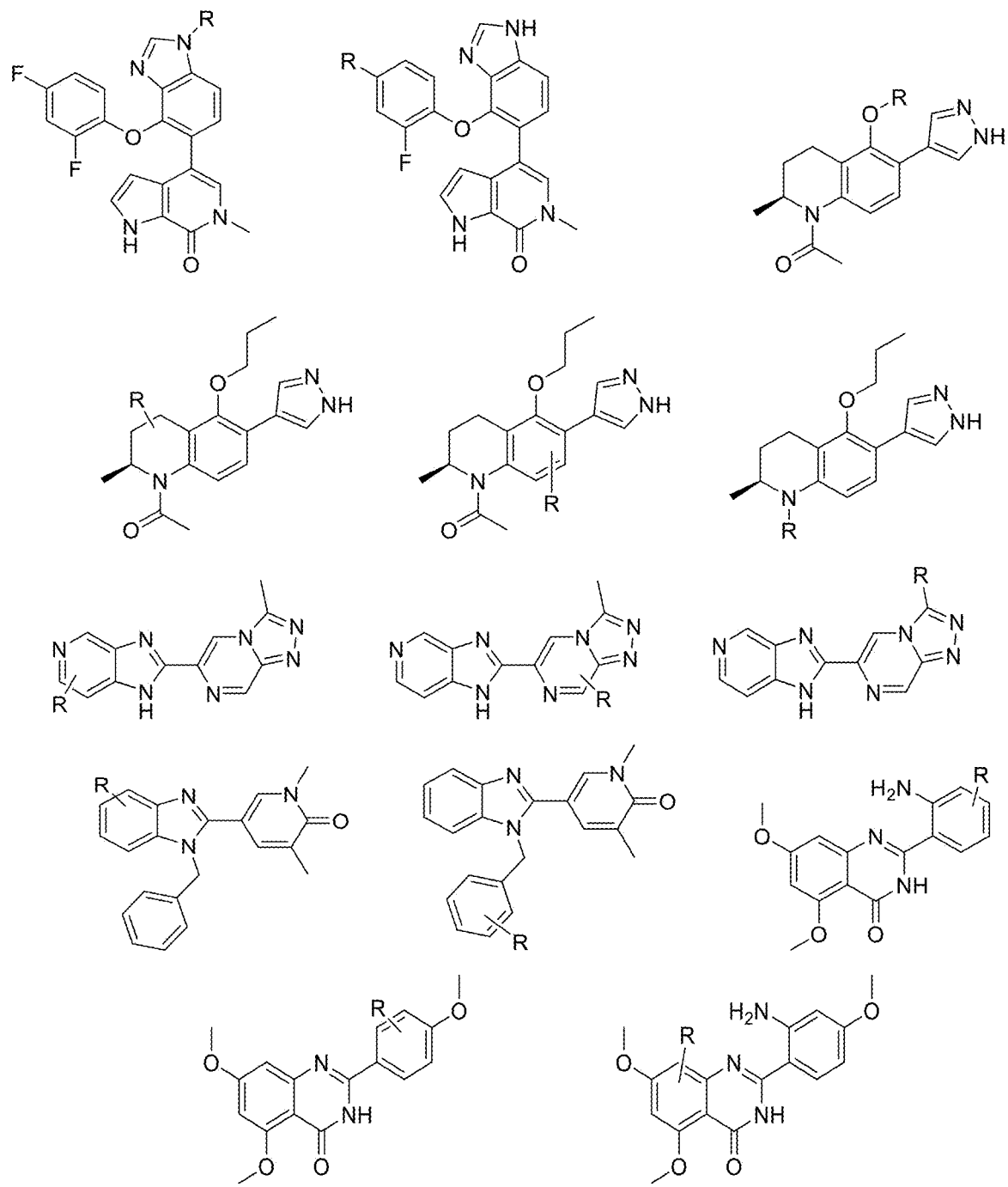
Figure 1L:
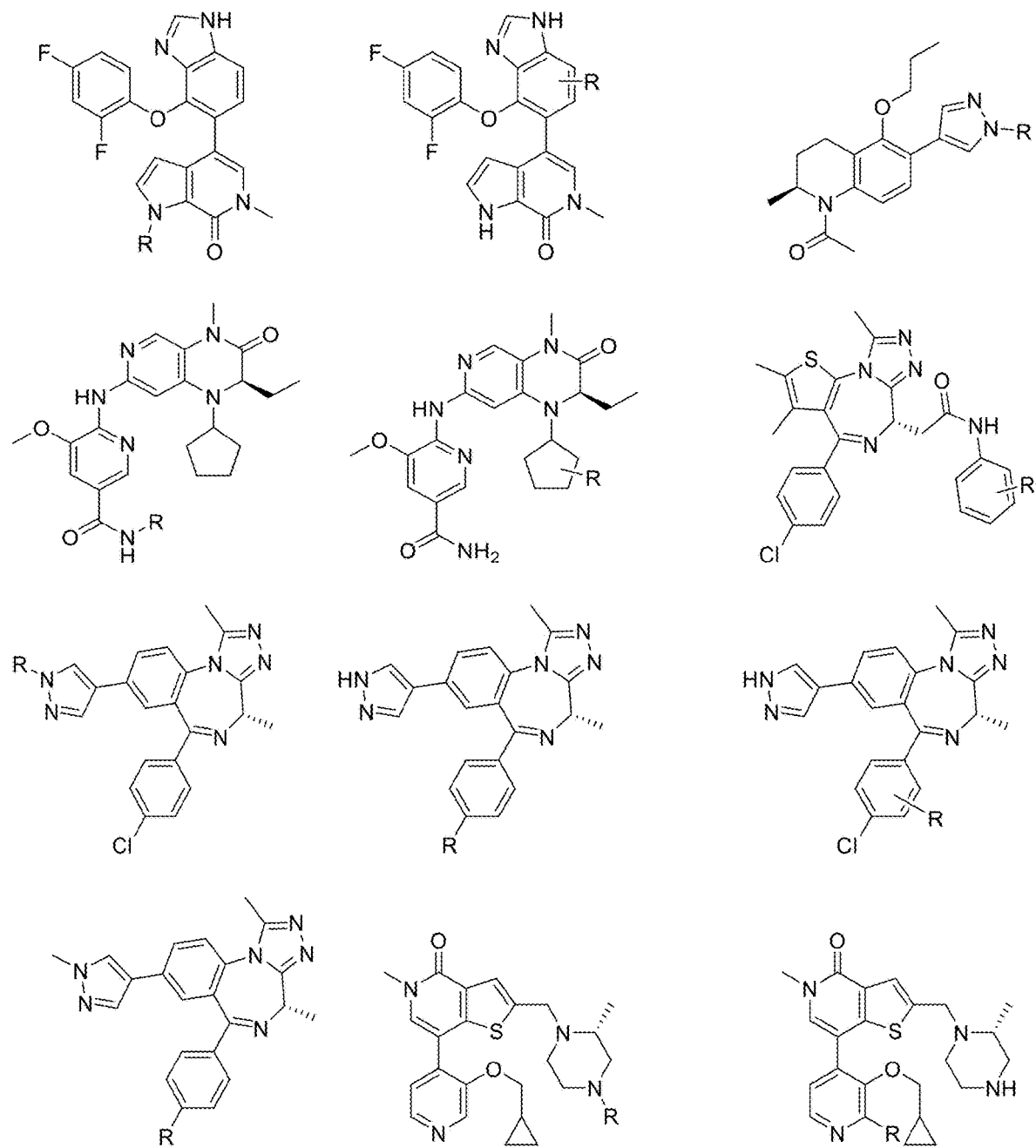
Figure 1M:
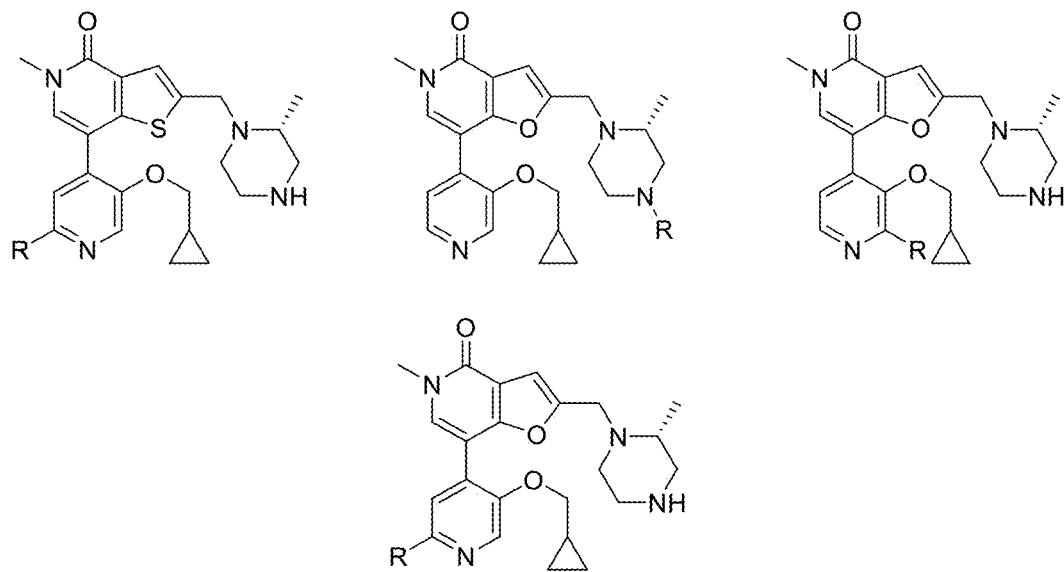
Figure 1N:
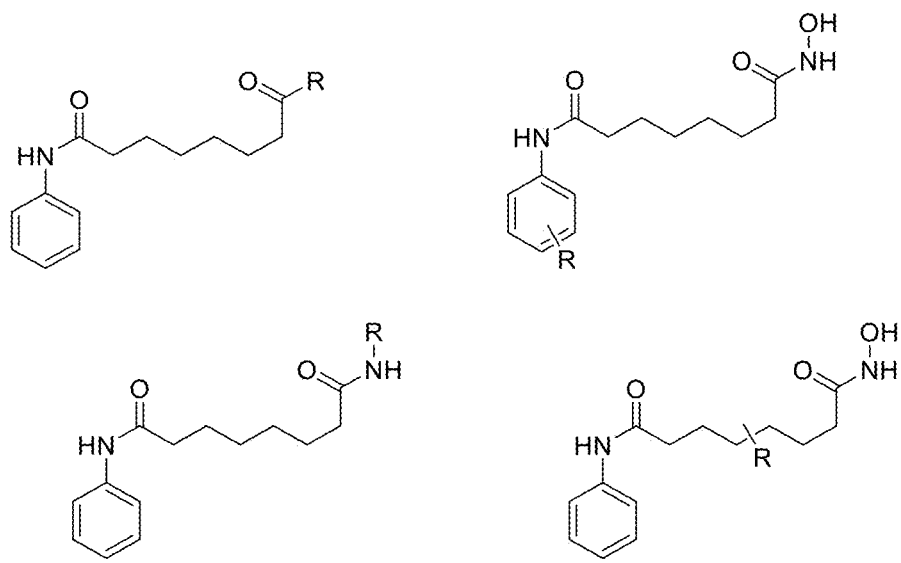
Figure 100:
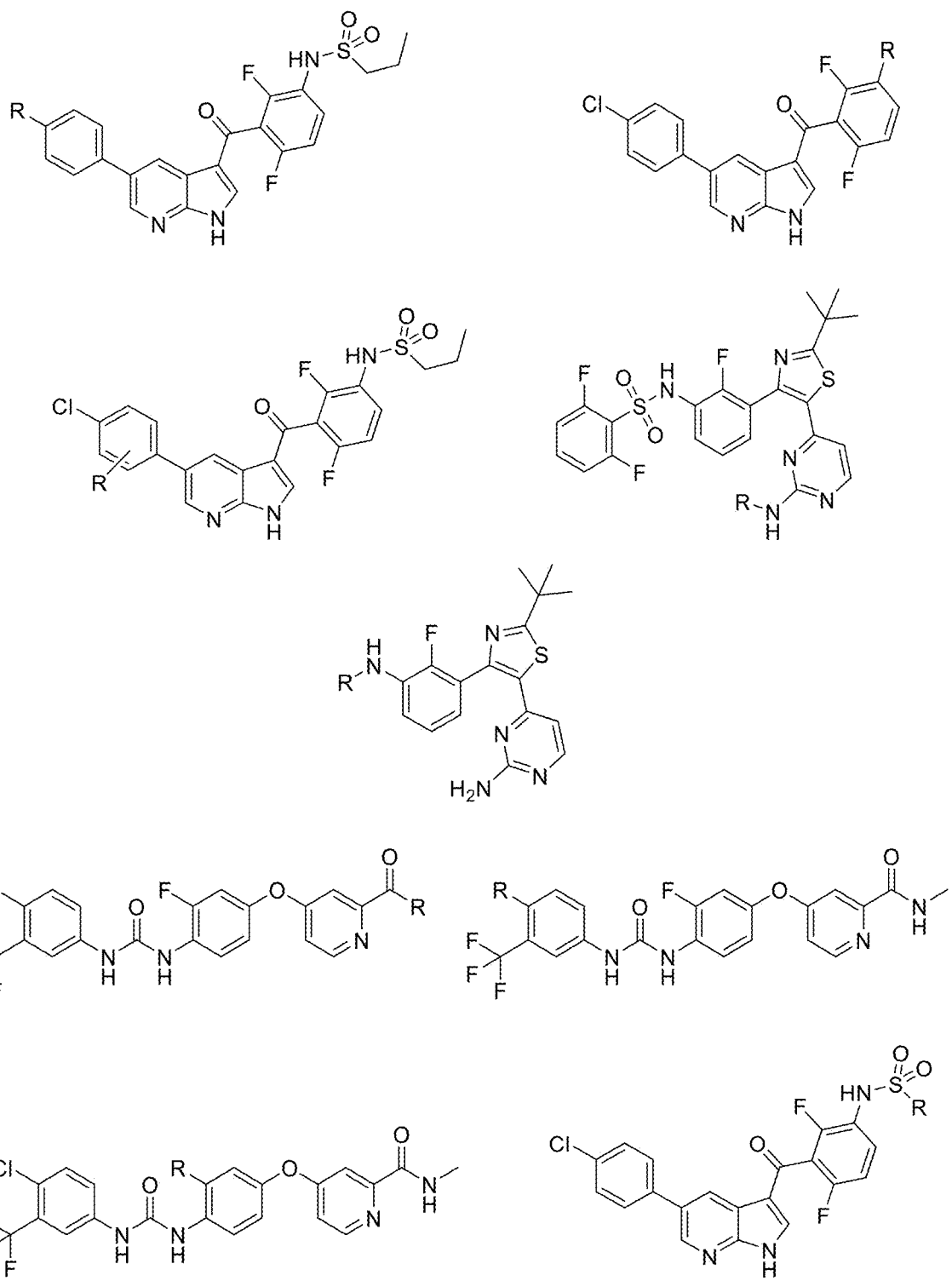
Figure 1P:
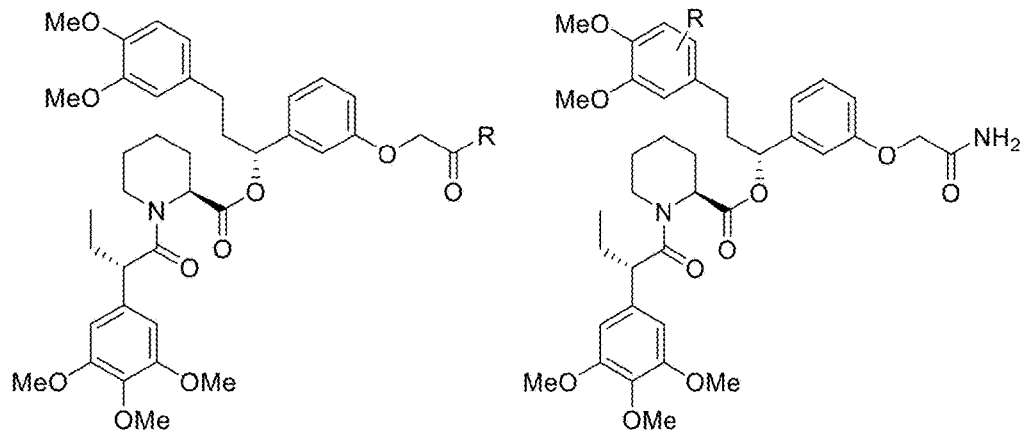
Figure 1Q:
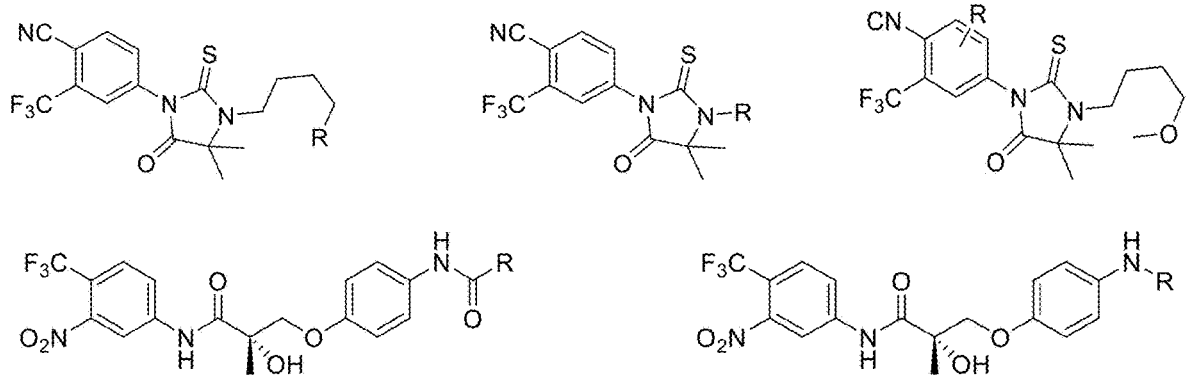
Figure 1S:
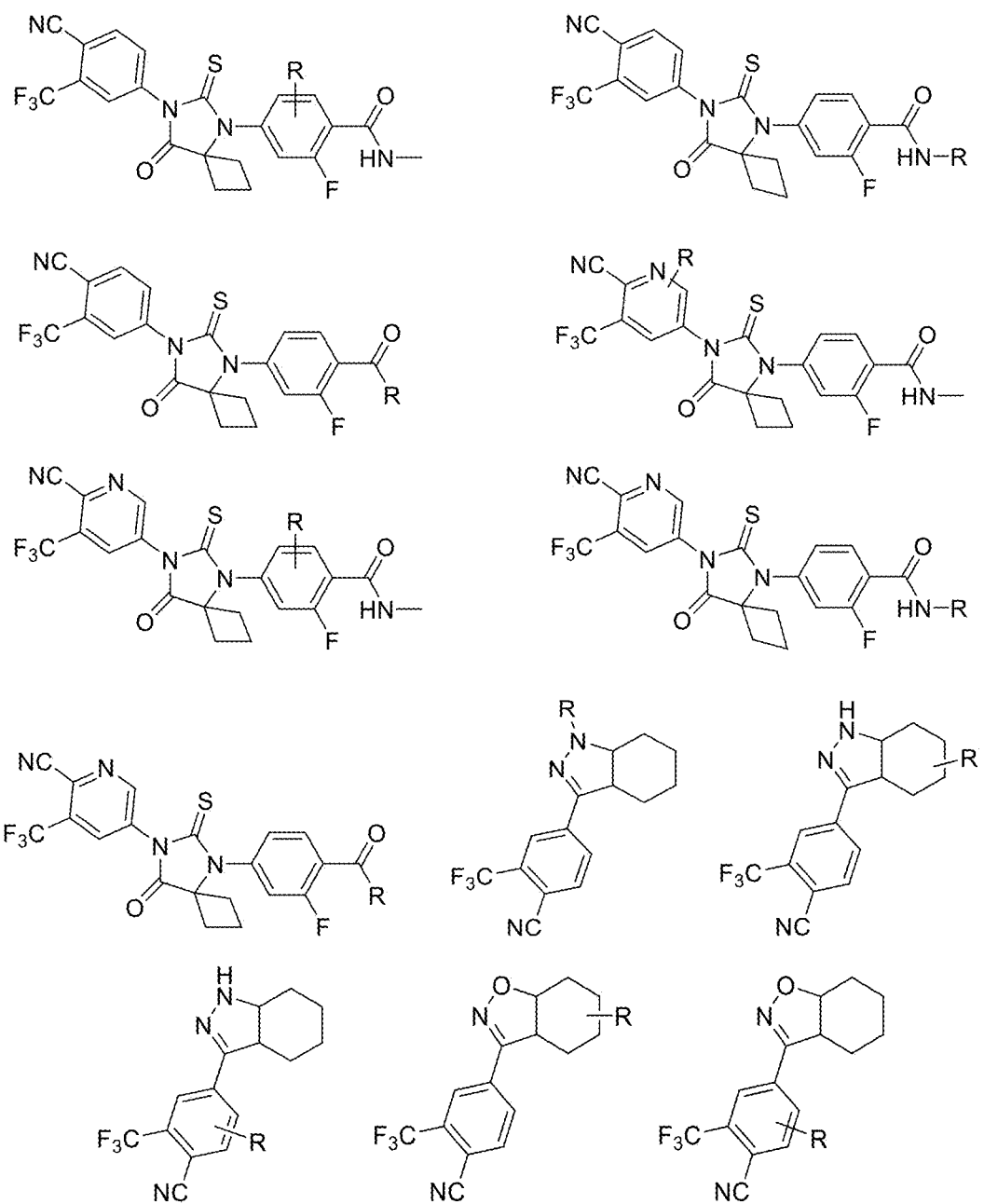
Figure 1Y:
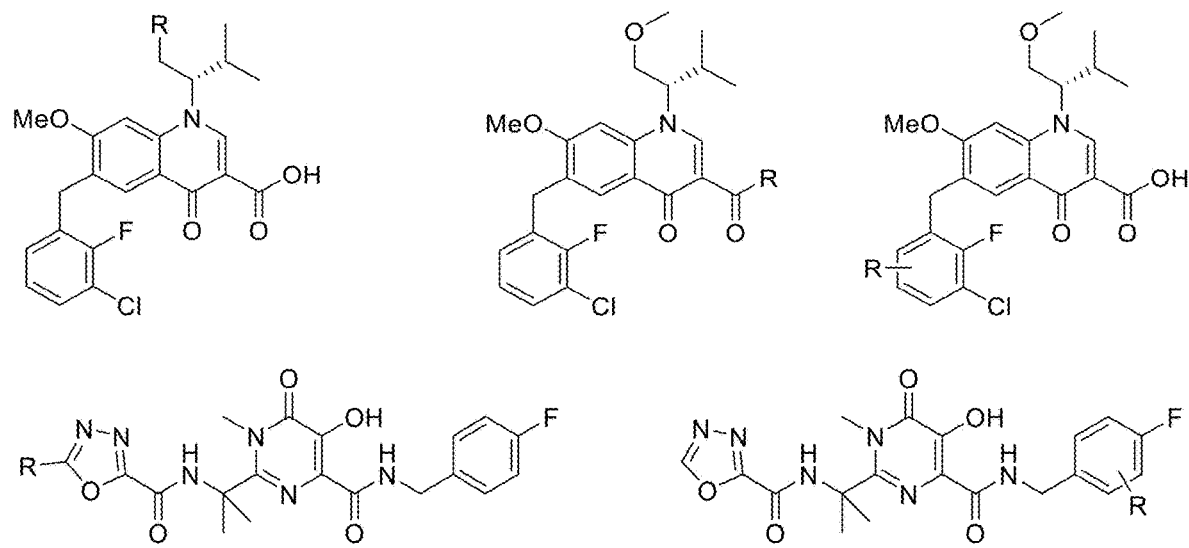
Figure 1Z:
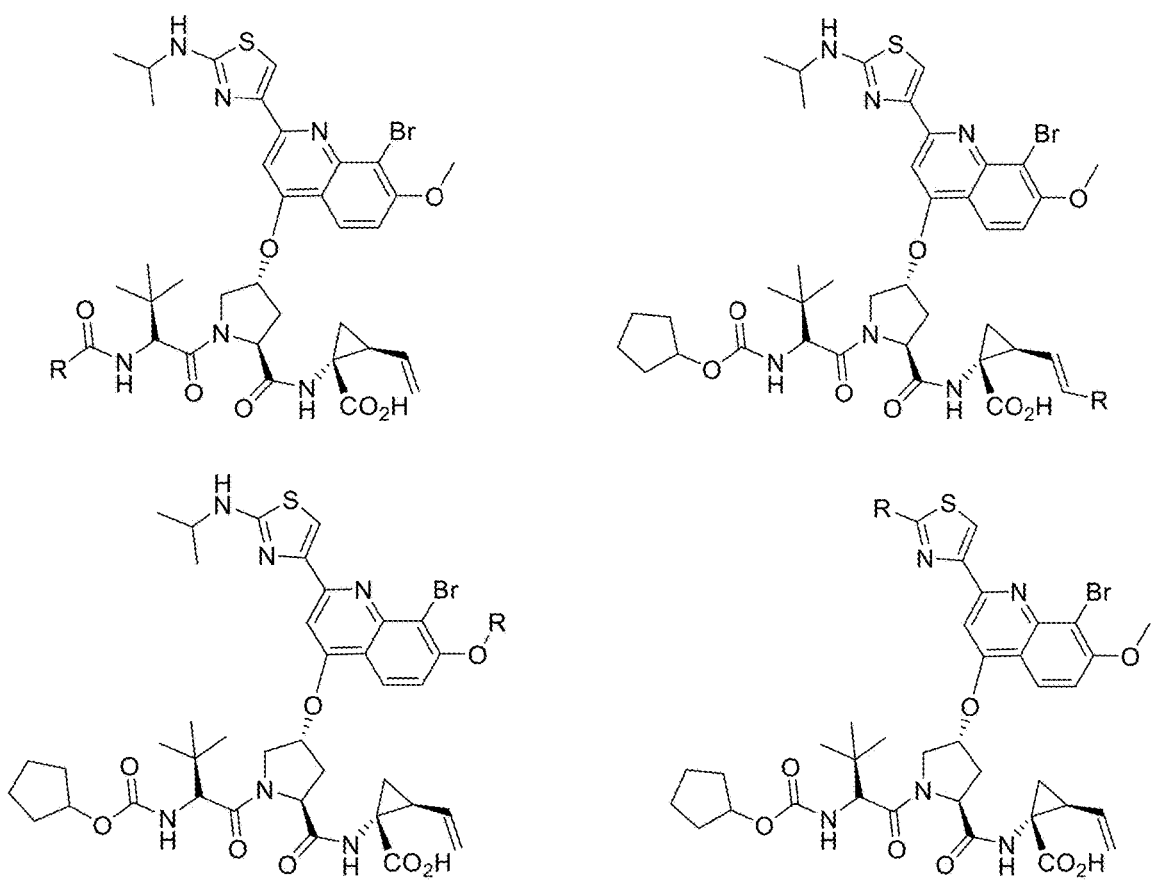
Figure 2A:
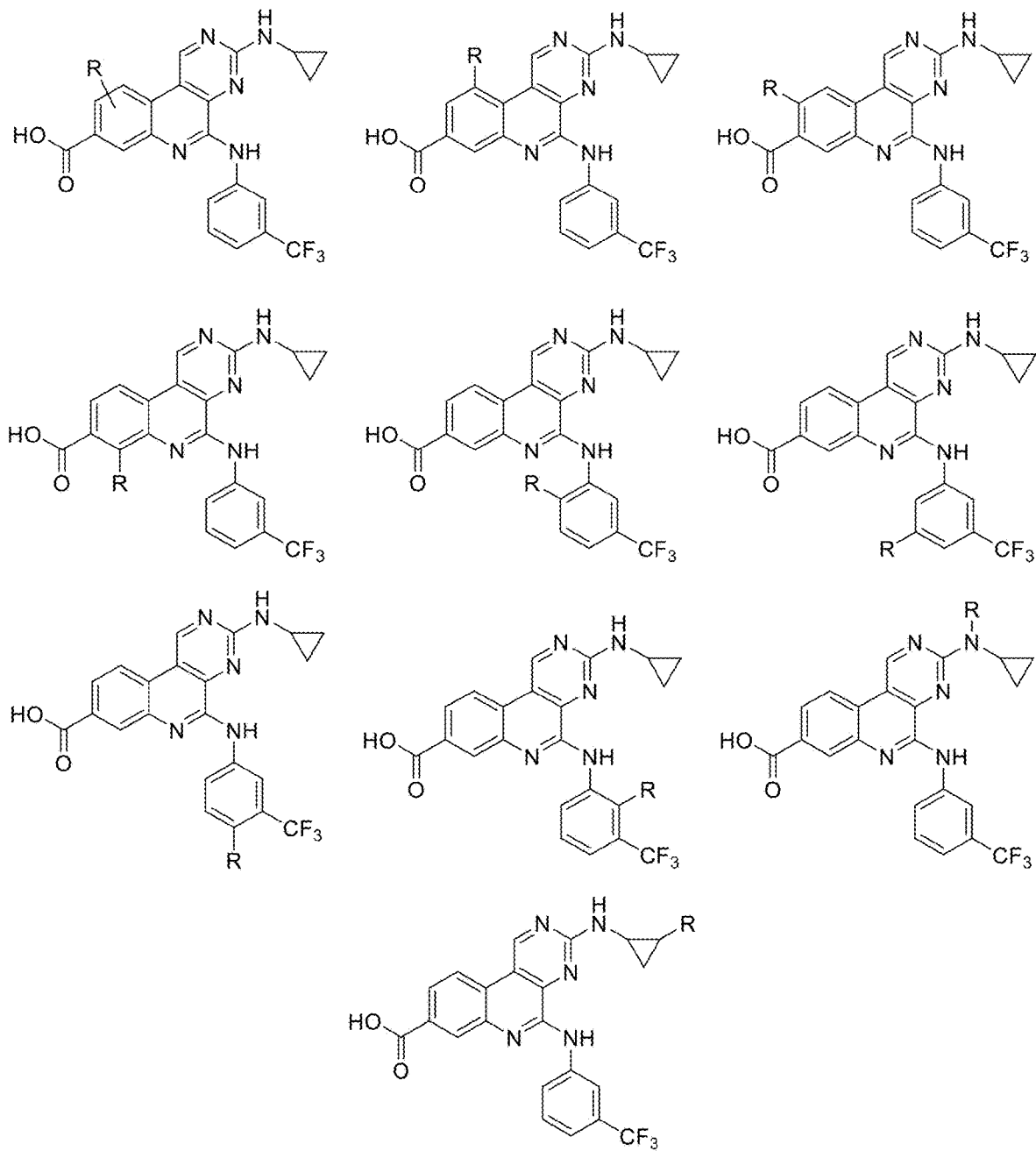
FIG. 2A provides non-limiting examples of the kinase inhibitor Targeting Ligands U09-CX-5279 (derivatized) wherein R represents exemplary points at which the Linker can be attached.
Figure 2B:
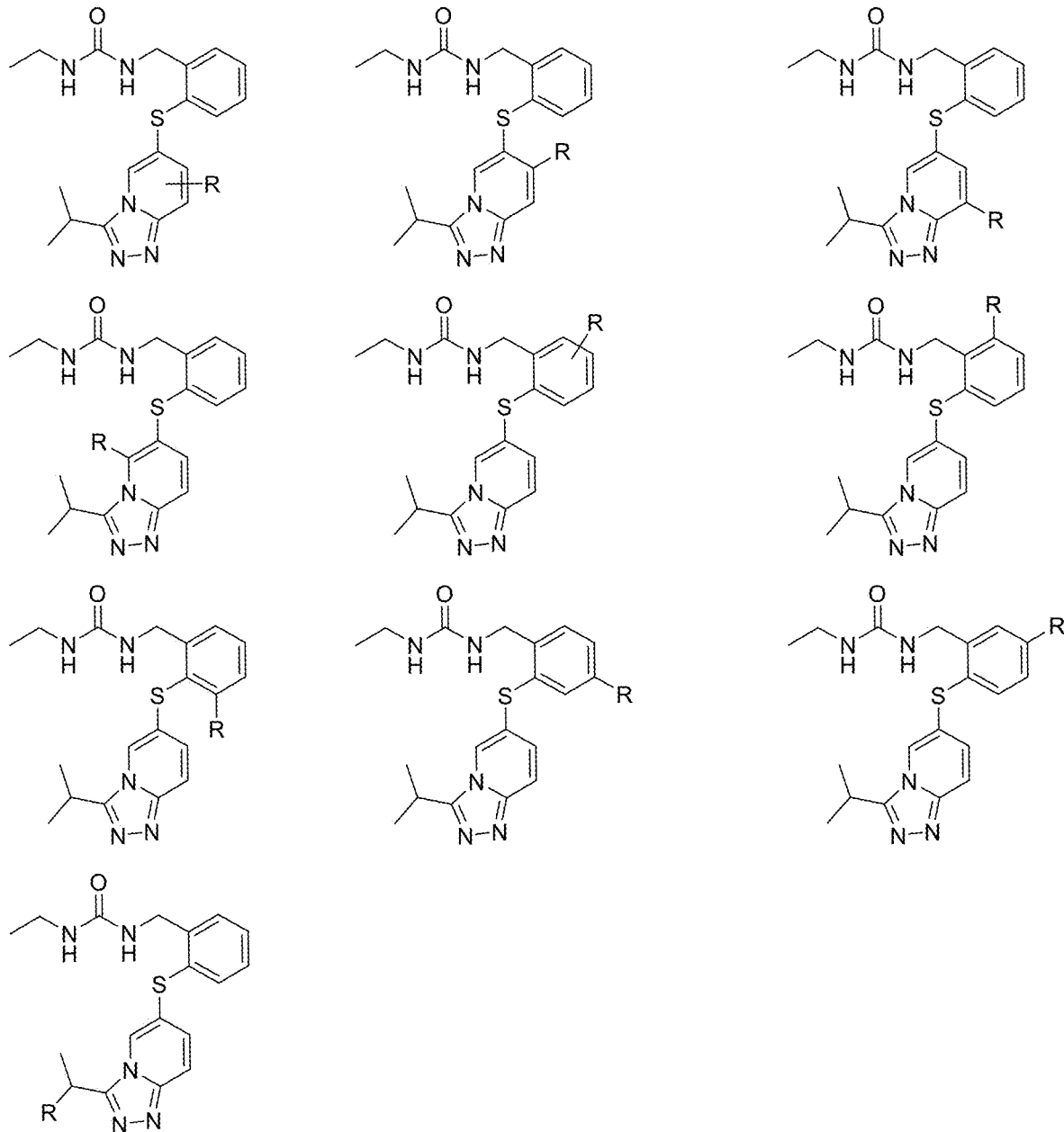
FIG. 2B-2C provide non-limiting examples of kinase inhibitor Targeting Ligands, including the kinase inhibitor compounds Y1W and Y1X (derivatized) wherein R represents exemplary points at which the Linker can be attached. For additional examples and related ligands, see, the kinase inhibitors identified in Millan et al. "Design and Synthesis of Inhaled P38 Inhibitors for the Treatment of Chronic Obstructive Pulmonary Disease" *J. Med. Chem.*, 54: 7797 (2011).
Figure 2C:
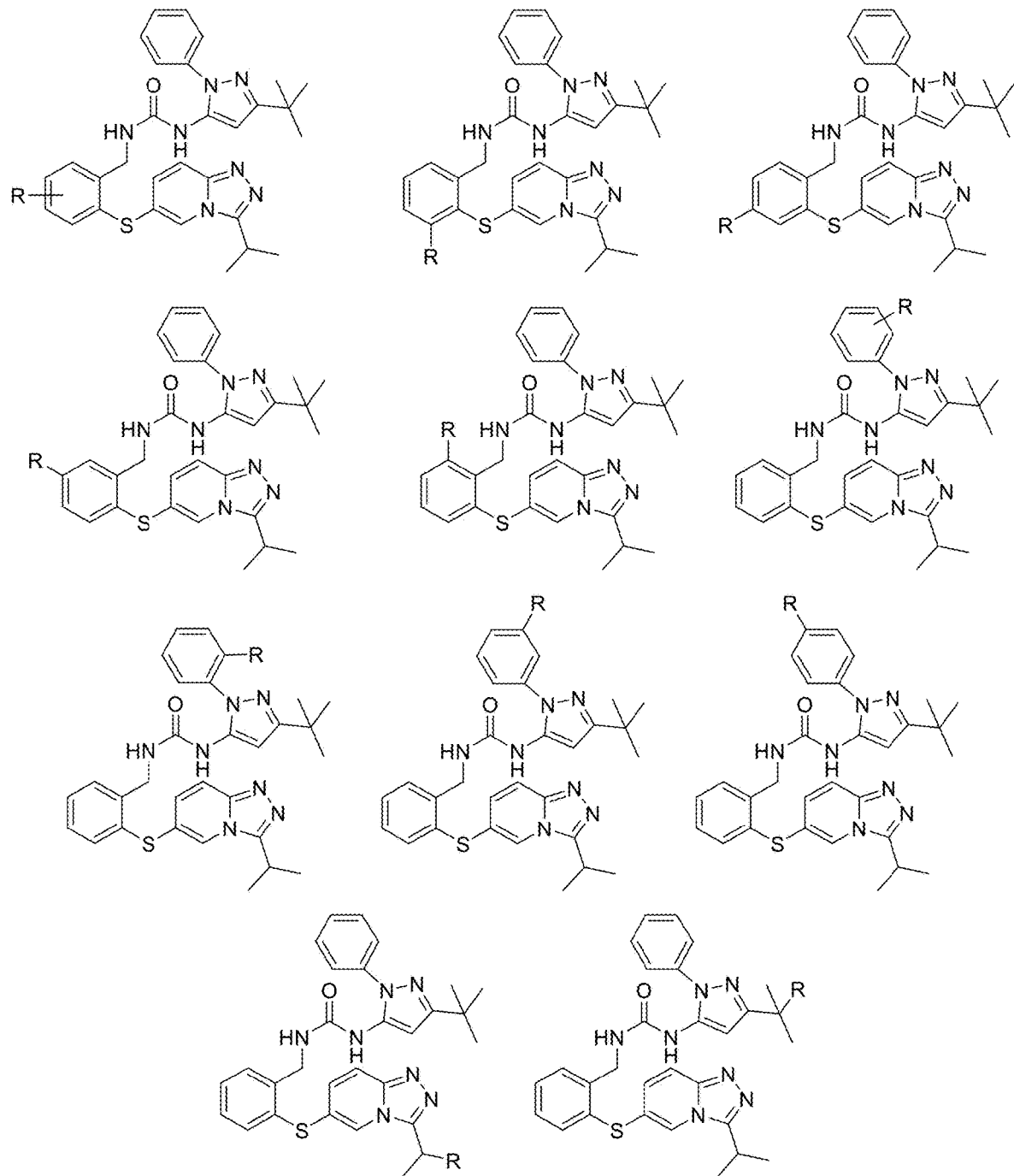
Figure 2D:
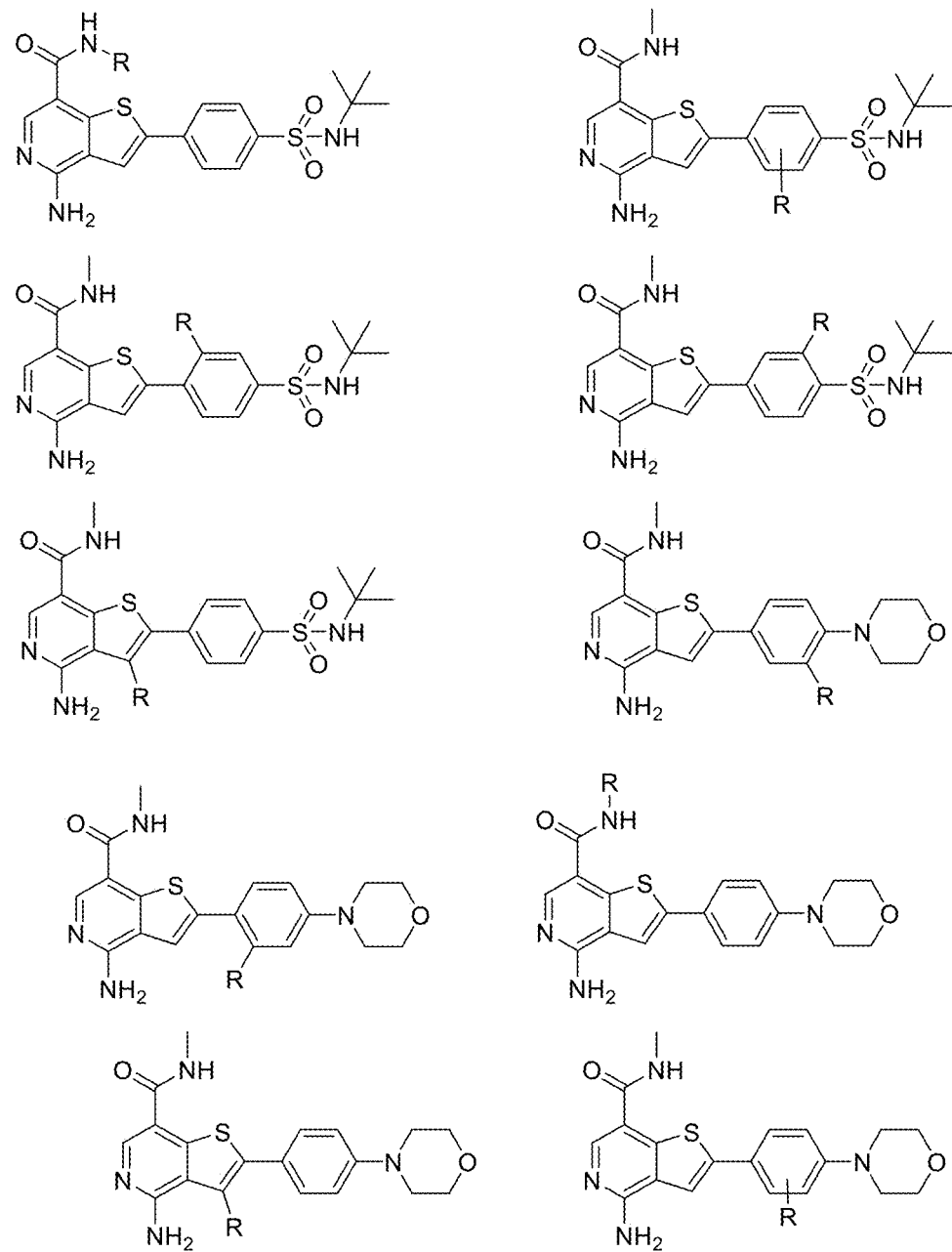
FIG. 2D provides non-limiting examples of kinase inhibitor Targeting Ligands, including the kinase inhibitor compounds 6TP and OTP (derivatized) wherein R represents exemplary points at which the Linker can be attached. For additional examples and related ligands, see, the kinase inhibitors identified in Schenkel et al. "Discovery of Potent and Highly Selective Thienopyridine Janus Kinase 2 Inhibitors" *J. Med. Chem.*, 54 (24): 8440-8450 (2011).
Figure 2E:
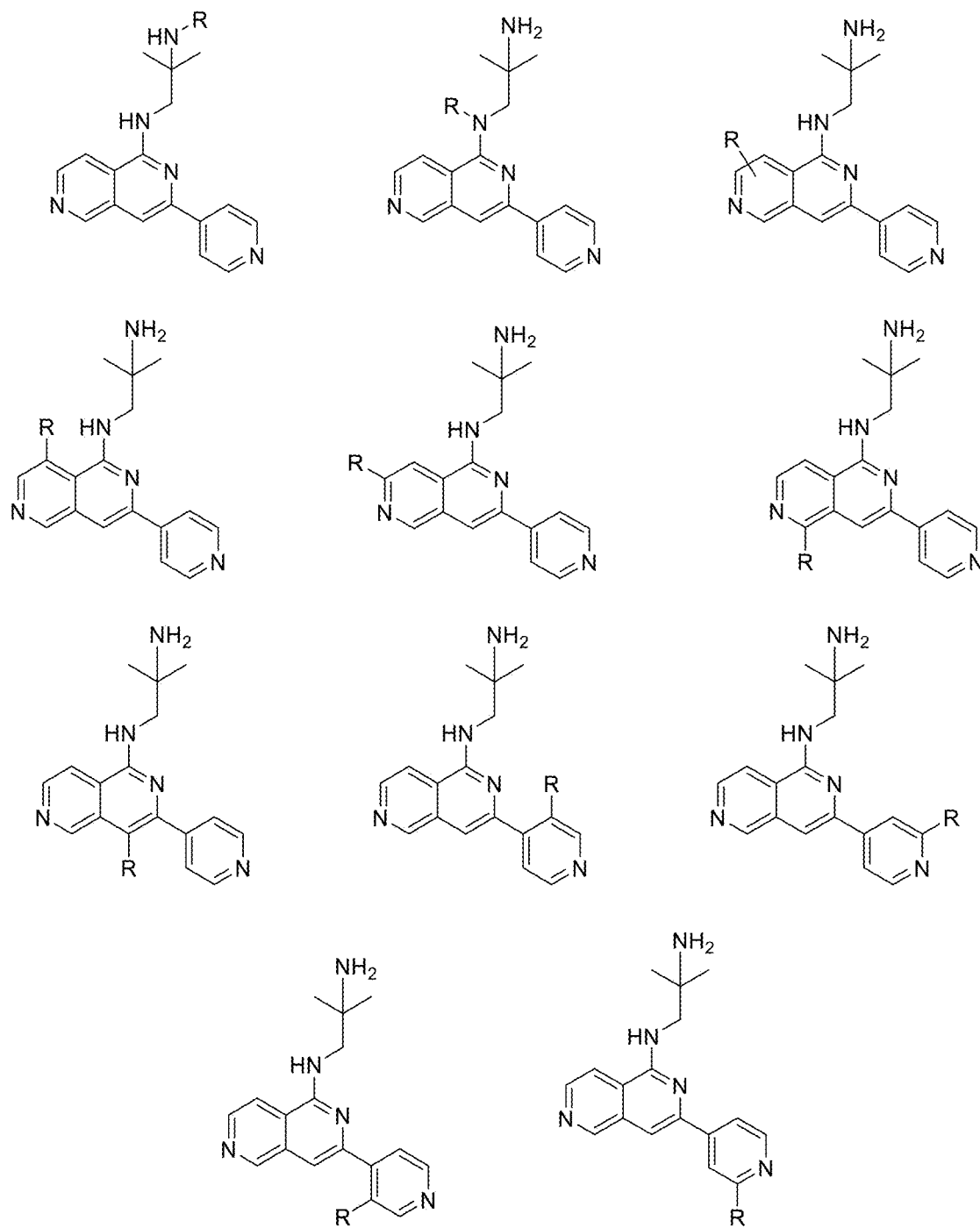
FIG. 2E provides non-limiting examples of kinase inhibitor Targeting Ligands, including the kinase inhibitor compound 07U wherein R represents exemplary points at which the Linker can be attached. For additional examples and related ligands, see, the kinase inhibitors identified in Van Eis et al. "2 6-Naphthyridines as potent and selective inhibitors of the novel protein kinase C isozymes" *Biorg. Med. Chem. Lett.*, 21(24): 7367-72 (2011).
Figure 2H:
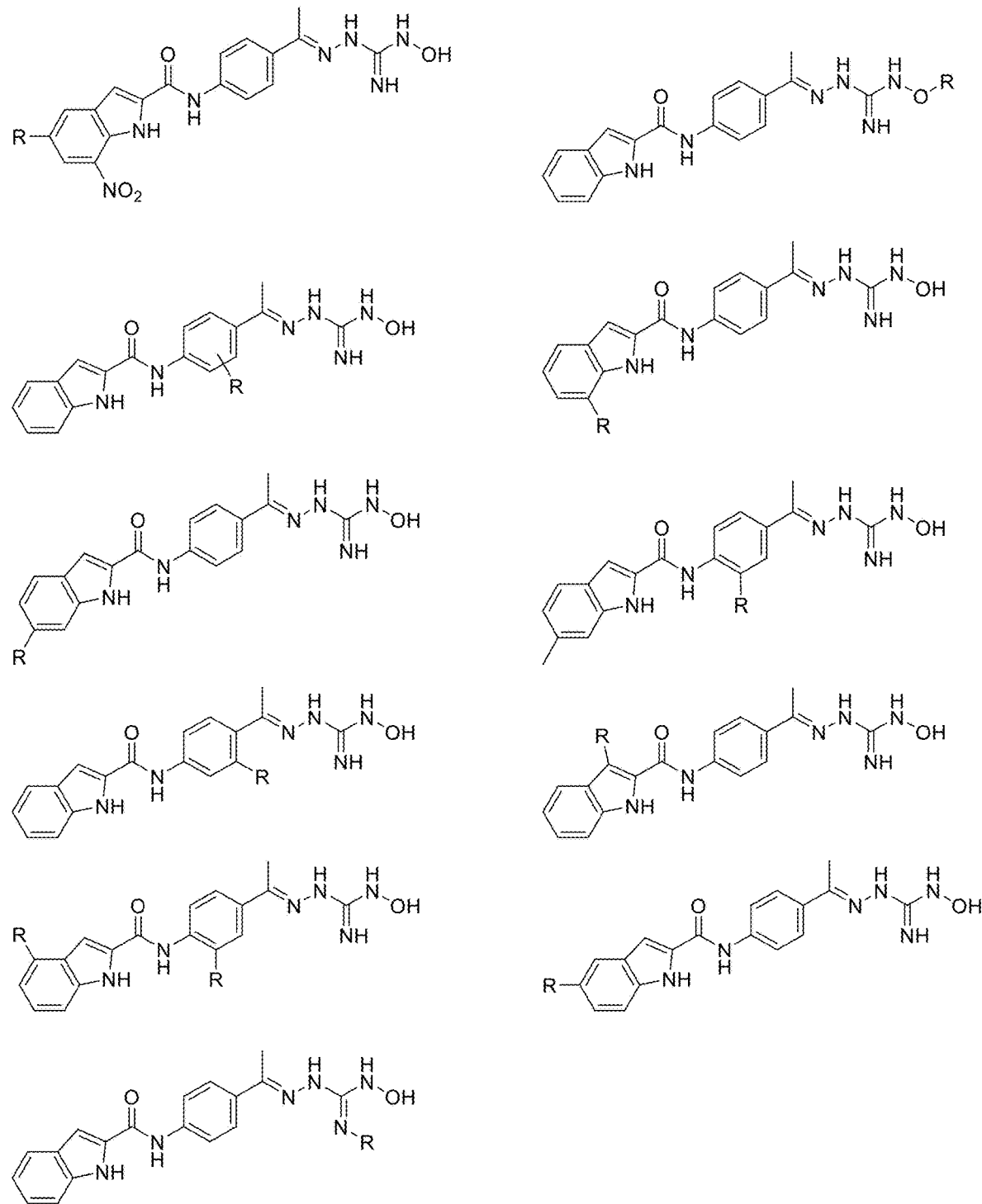
FIG. 2G-2H provide non-limiting examples of kinase inhibitor Targeting Ligands, including the kinase inhibitors XK9 and NXP (derivatized) wherein R represents exemplary points at which the Linker can be attached. For additional examples and related ligands, see, the kinase inhibitors identified in Lountos et al. "Structural Characterization of Inhibitor Complexes with Checkpoint Kinase 2 (Chk2) a Drug Target for Cancer Therapy" *J. Struct. Biol.*, 176: 292 (2011).
Figure 2J:
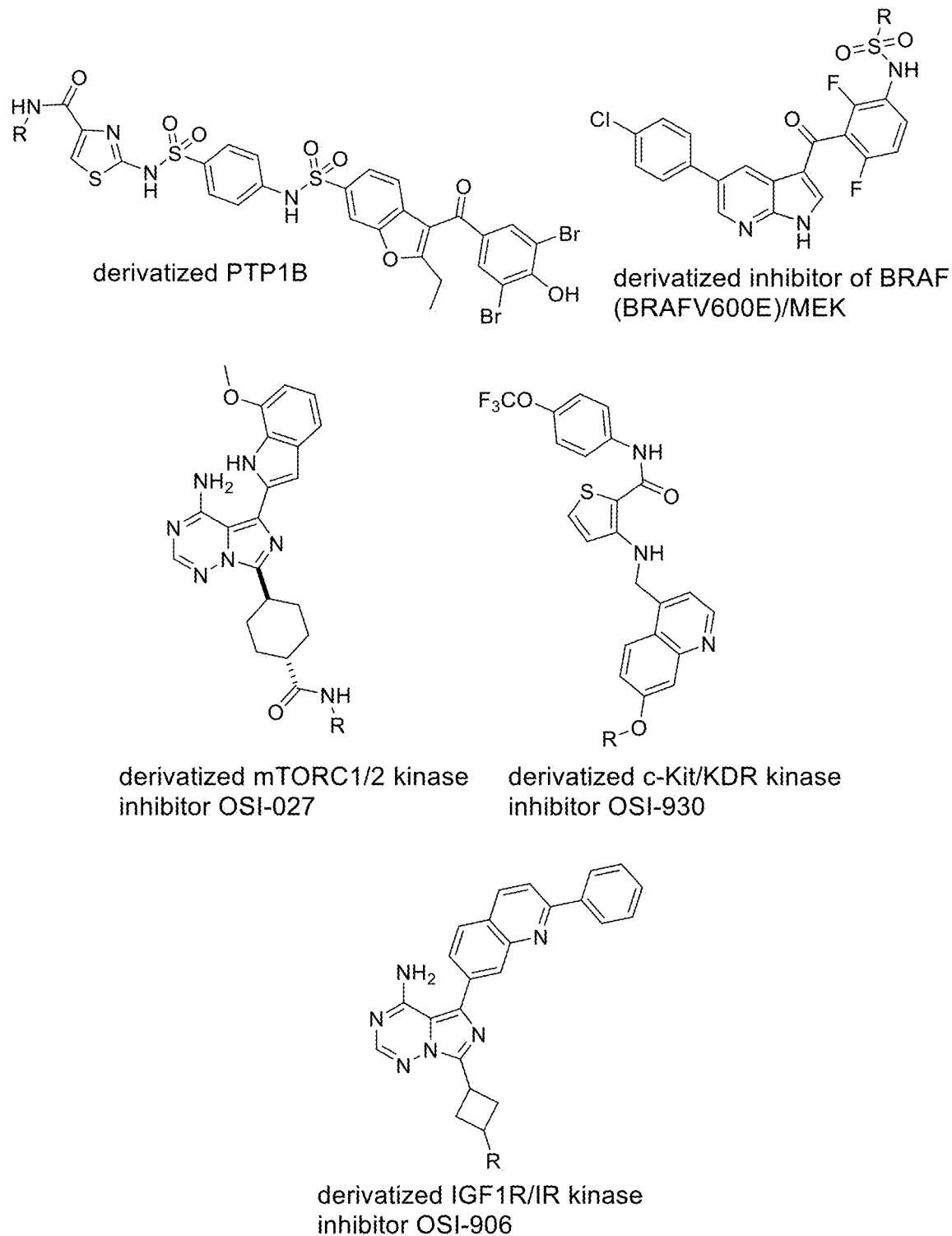
FIG. 2I-2J provide non-limiting examples of kinase inhibitor Targeting Ligands wherein R represents exemplary points at which the spacer r is attached.
Figure 2K:
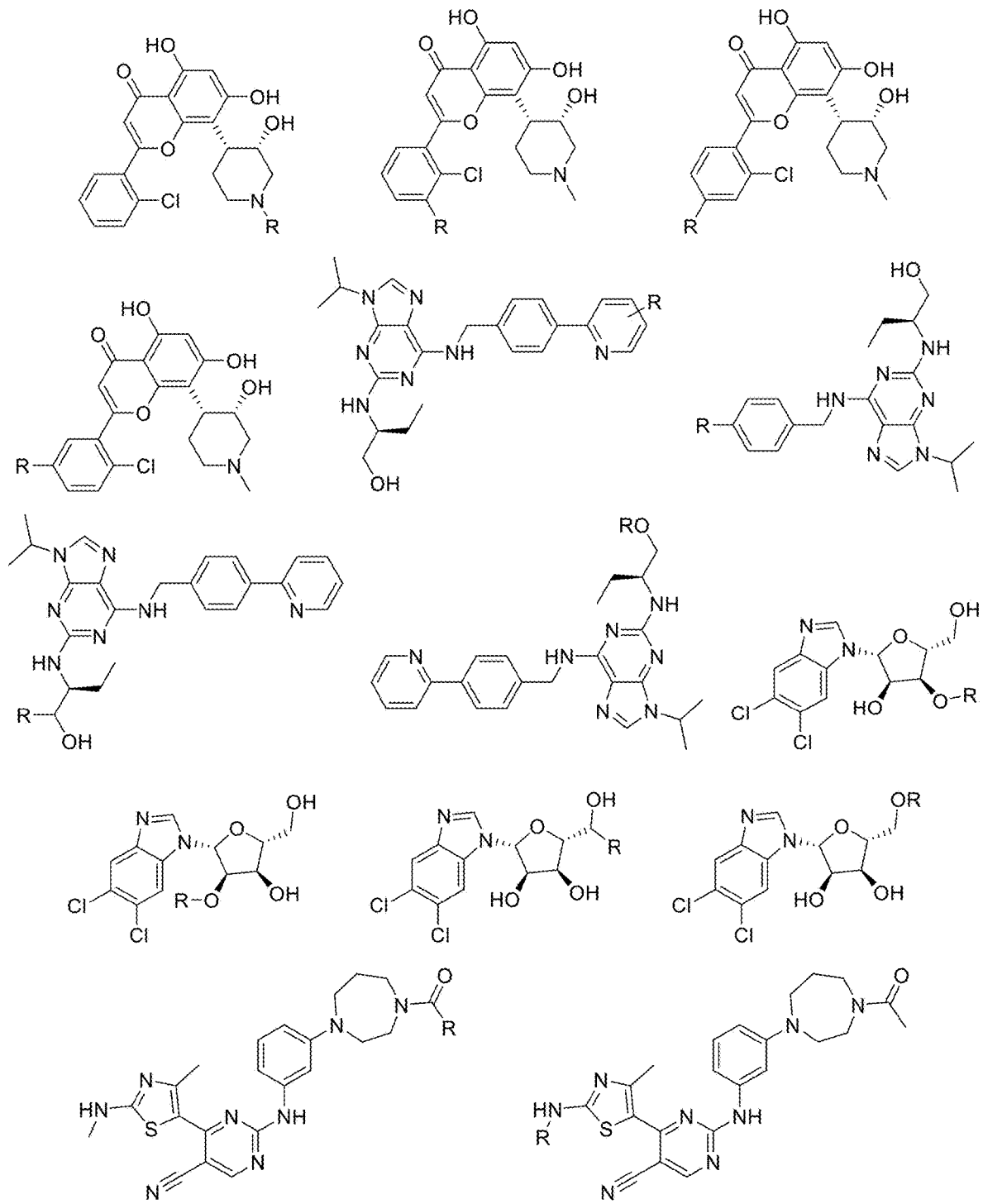
FIG. 2K-2M provide non-limiting examples of Cyclin Dependent Kinase 9 (CDK9) Targeting Ligands wherein R represents exemplary points at which the Linker can be attached. For additional examples and related ligands, see, Baumli et al. "The structure of P-TEFb (CDK9/cyclin T1) its complex with flavopiridol and regulation by phosphorylation." *Embo J.*, 27: 1907-1918 (2008); Bettayeb et al. "CDK Inhibitors Roscovitine and CR8 Trigger Mcl-1 Down-Regulation and Apoptotic Cell Death in Neuroblastoma Cells." *Genes Cancer*, 1: 369-380 (2010); Baumli et a. "Halogen bonds form the basis for selective P-TEFb inhibition by DRB." *Chem. Biol.* 17: 931-936 (2010); Hole et al. "Comparative Structural and Functional Studies of 4-(Thiazol-5-Yl)-2-(Phenylamino)Pyrimidine-5-Carbonitrile Cdk9 Inhibitors Suggest the Basis for Isotype Selectivity." *J. Med. Chem.* 56: 660 (2013); Lucking et al. "Identification of the potent and highly selective PTEFb inhibitor BAY 1251152 for the treatment of cancer—From p.o. to i.v. application via scaffold hops." Lucking et al. U. AACR Annual Meeting, Apr. 1-5, 2017 Washington, D. C. USA.
Figure 2L:
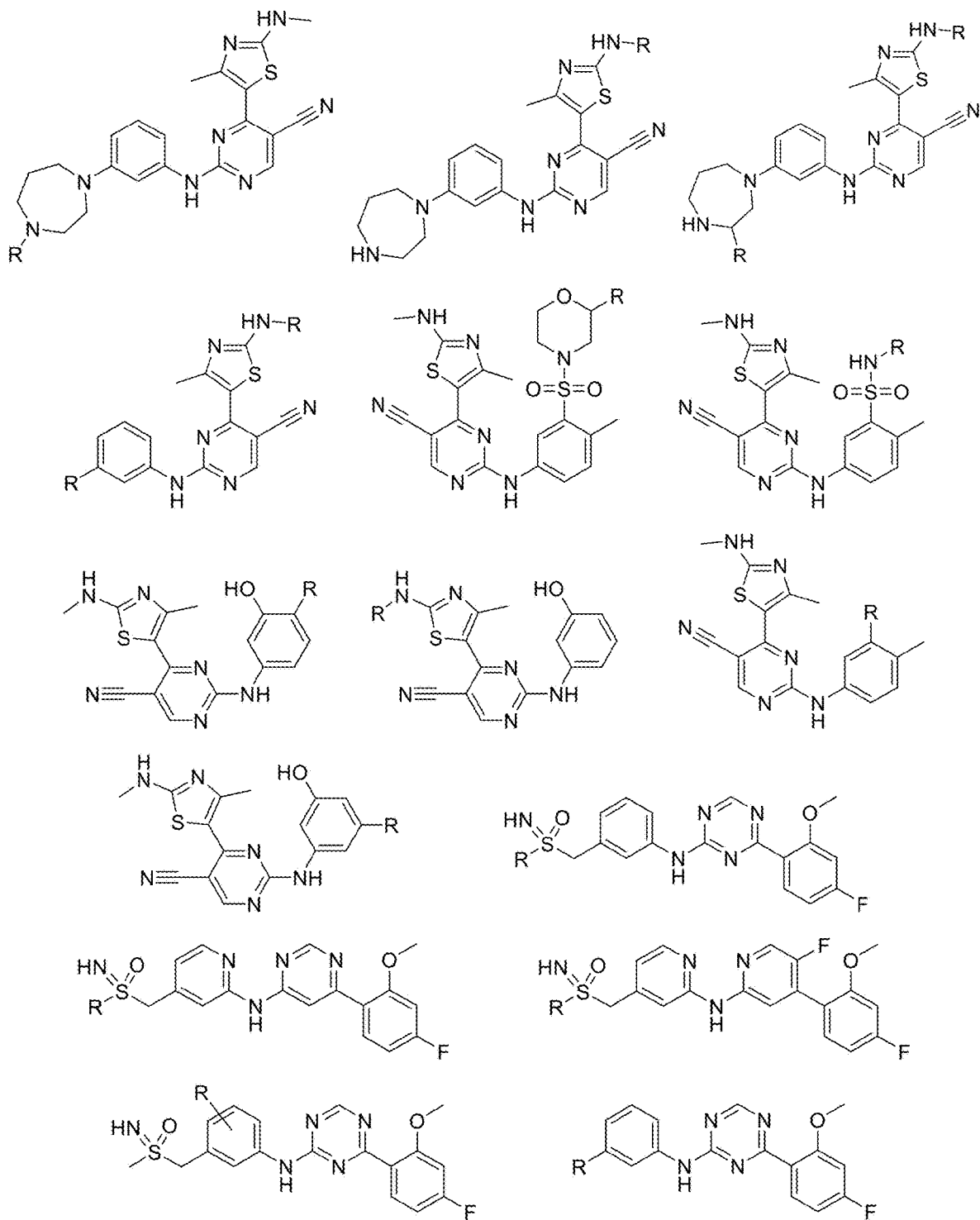
Figure 2M:
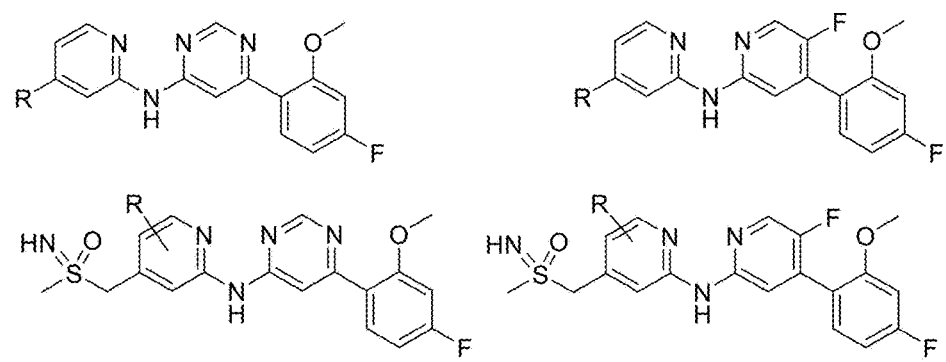
Figure 2N:
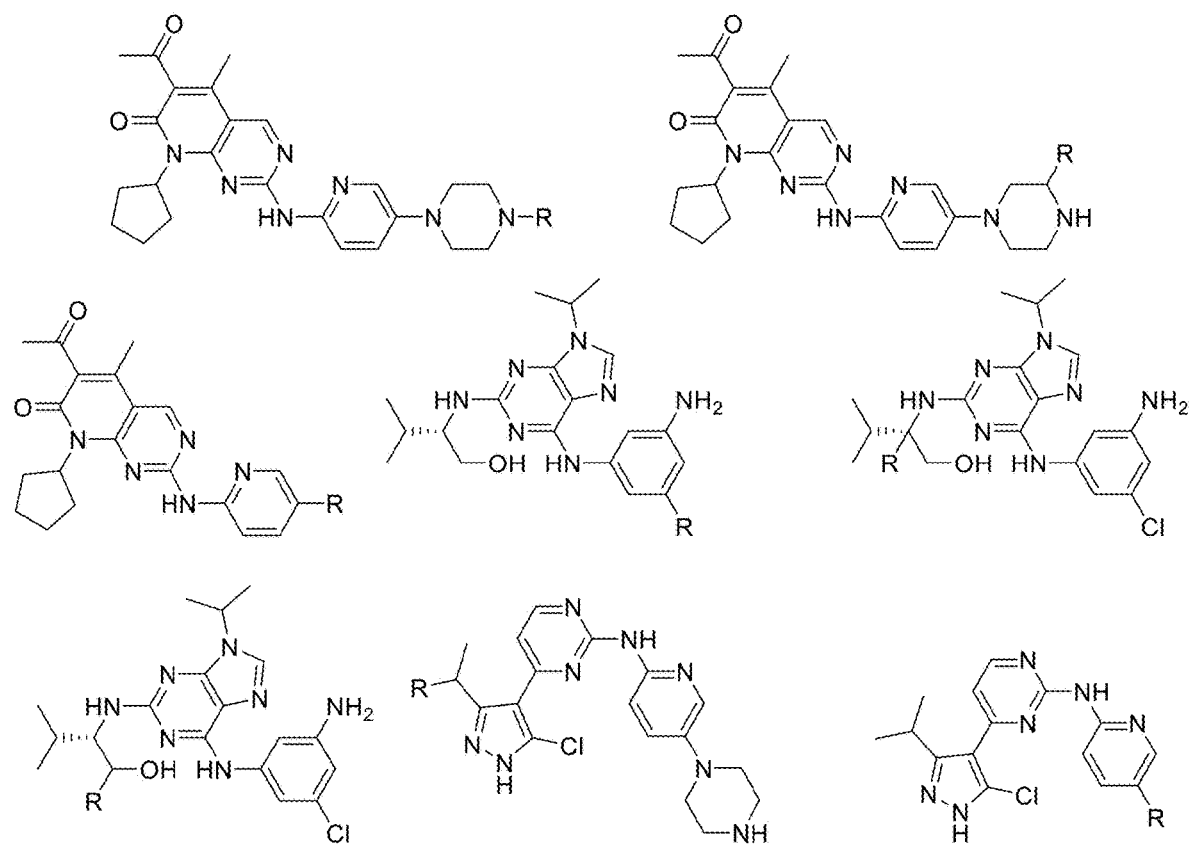
FIG. 2N-2P provide non-limiting examples of Cyclin Dependent Kinase 4/6 (CDK4/6) Targeting Ligands wherein R represents exemplary points at which the Linker can be attached. For additional examples and related ligands, see, Lu H.; Schulze-Gahmen U.: "Toward understanding the structural basis of cyclin-dependent kinase 6 specific inhibition." *J. Med. Chem.*, 49: 3826-3831 (2006); 4-(Pyrazol-4-yl)-pyrimidines as selective inhibitors of cyclin-dependent kinase 4/6. Cho et al. (2010) *J. Med. Chem.* 53: 7938-7957; Cho Y. S. et al. "Fragment-Based Discovery of 7-Azabenzimidazoles as Potent Highly Selective and Orally Active CDK4/6 Inhibitors." ACS Med *Chem Lett* 3: 445-449 (2012); Li Z. et al. "Discovery of AMG 925 a FLT3 and CDK4 dual kinase inhibitor with preferential affinity for the activated state of FLT3." *J. Med. Chem.* 57: 3430-3449 (2014); Chen P. et al. "Spectrum and Degree of CDK Drug Interactions Predicts Clinical Performance." *Mol. Cancer Ther.* 15: 2273-2281 (2016).
Figure 2O:
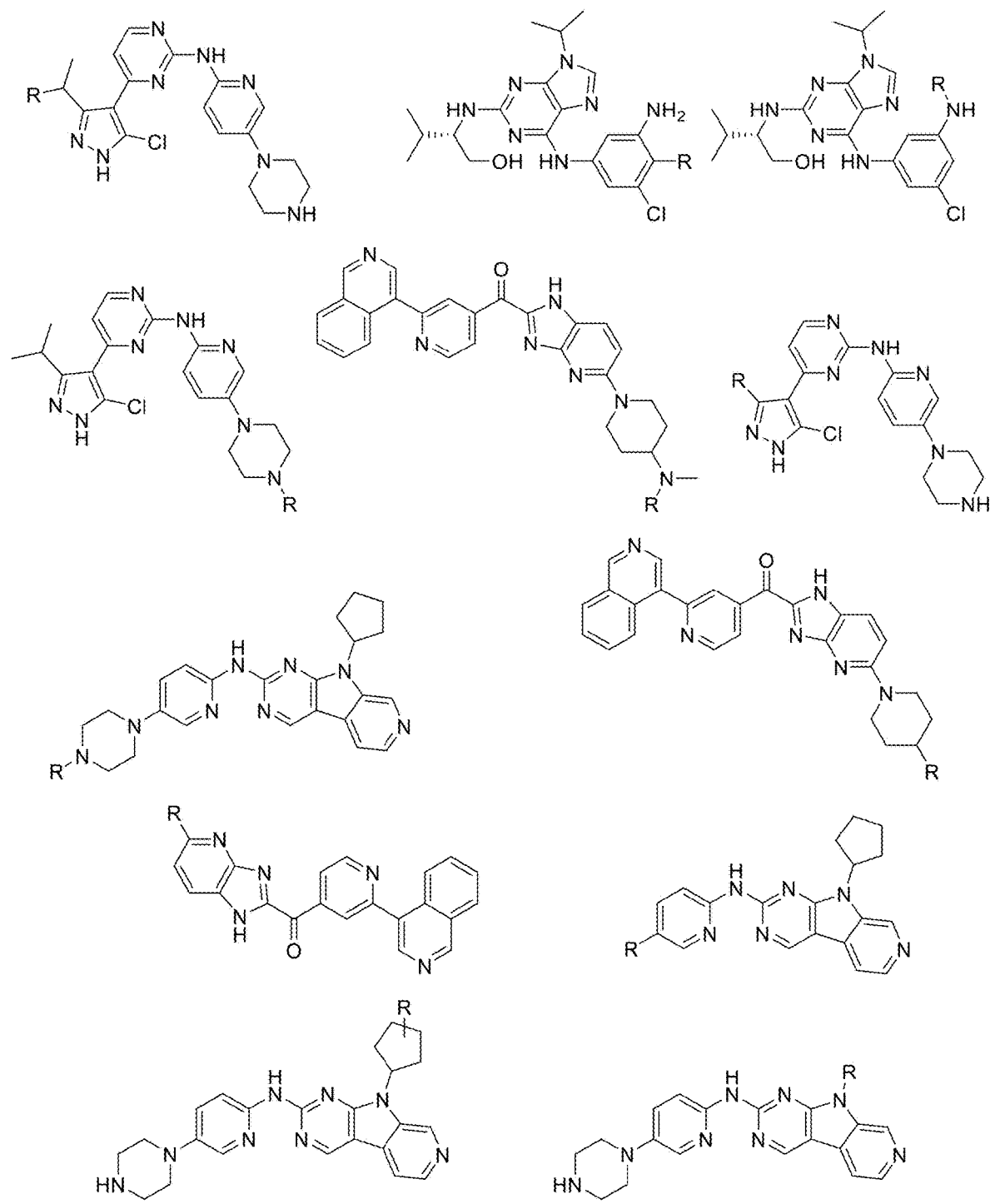
Figure 2P:
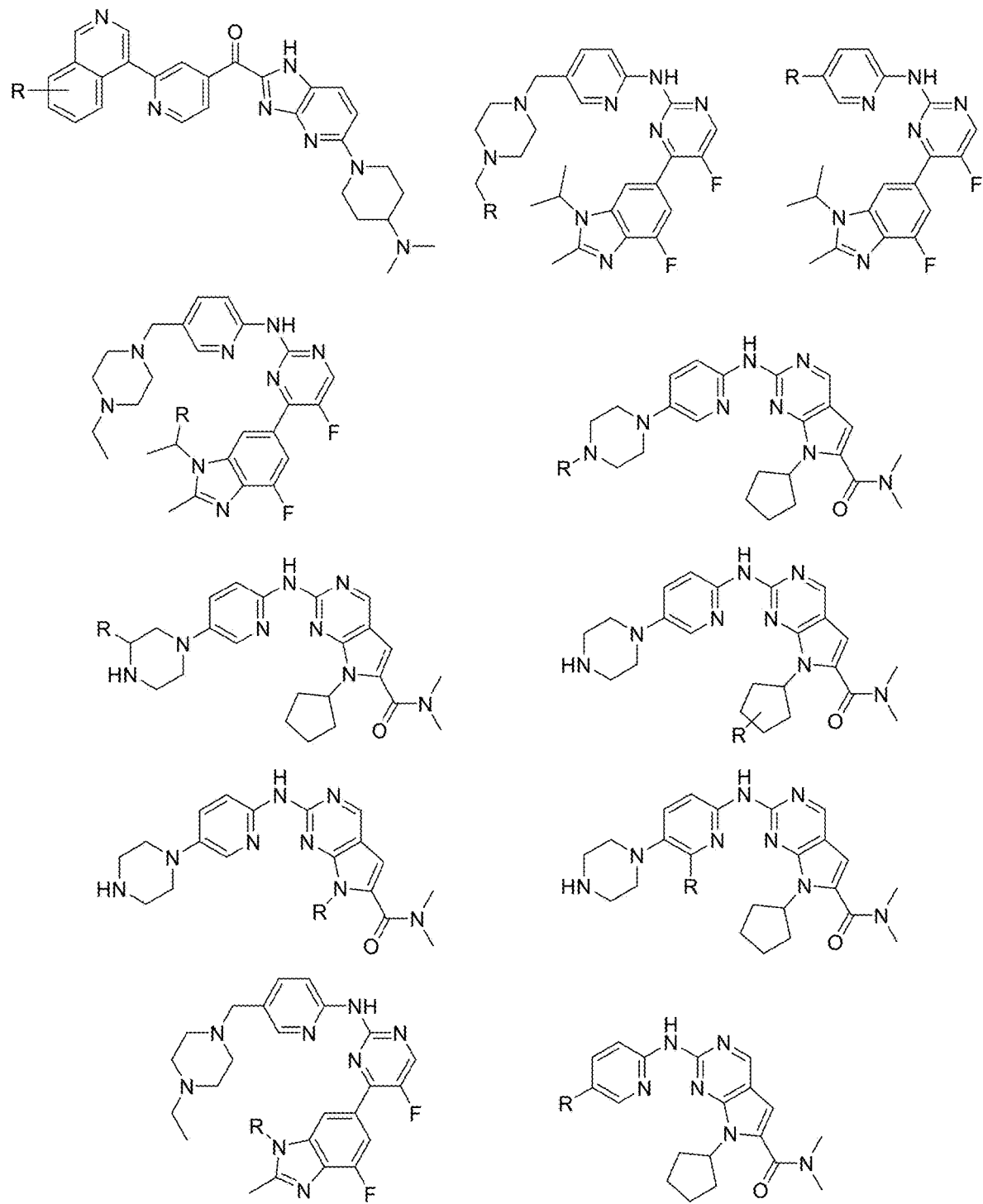
Figure 2Q:
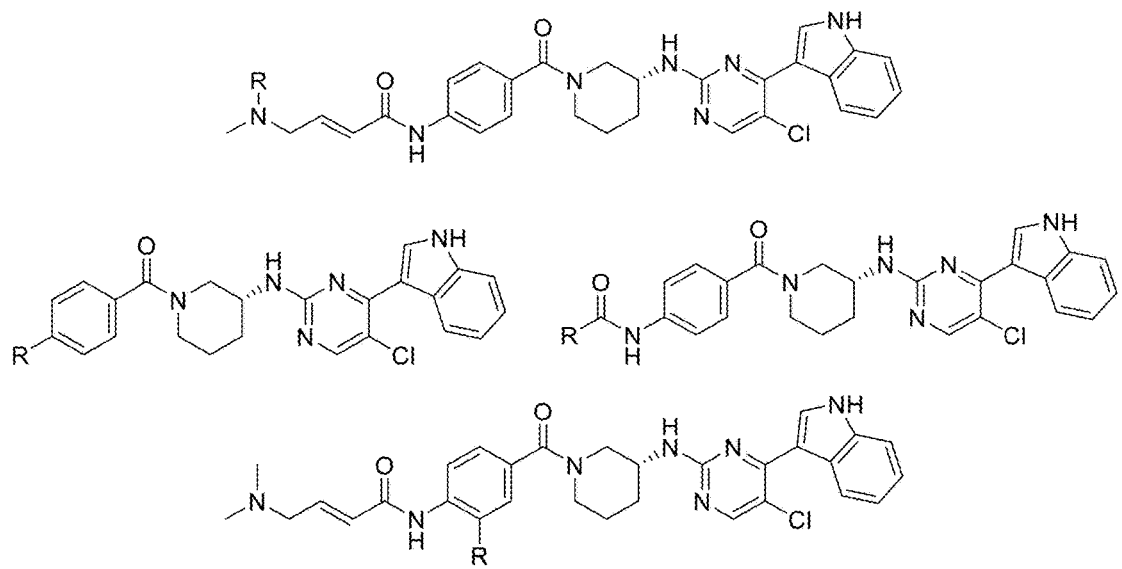
FIG. 2Q provides non-limiting examples of Cyclin Dependent Kinase 12 and/or Cyclin Dependent Kinase 13 Targeting Ligands wherein R represents exemplary points at which the Linker can be attached. For additional examples and related ligands, see, Zhang T. et al. "Covalent Targeting of Remote Cysteine Residues to Develop Cdk12 and Cdk13 Inhibitors." *Nat. Chem. Biol.* 12: 876 (2016).
Figure 2R:
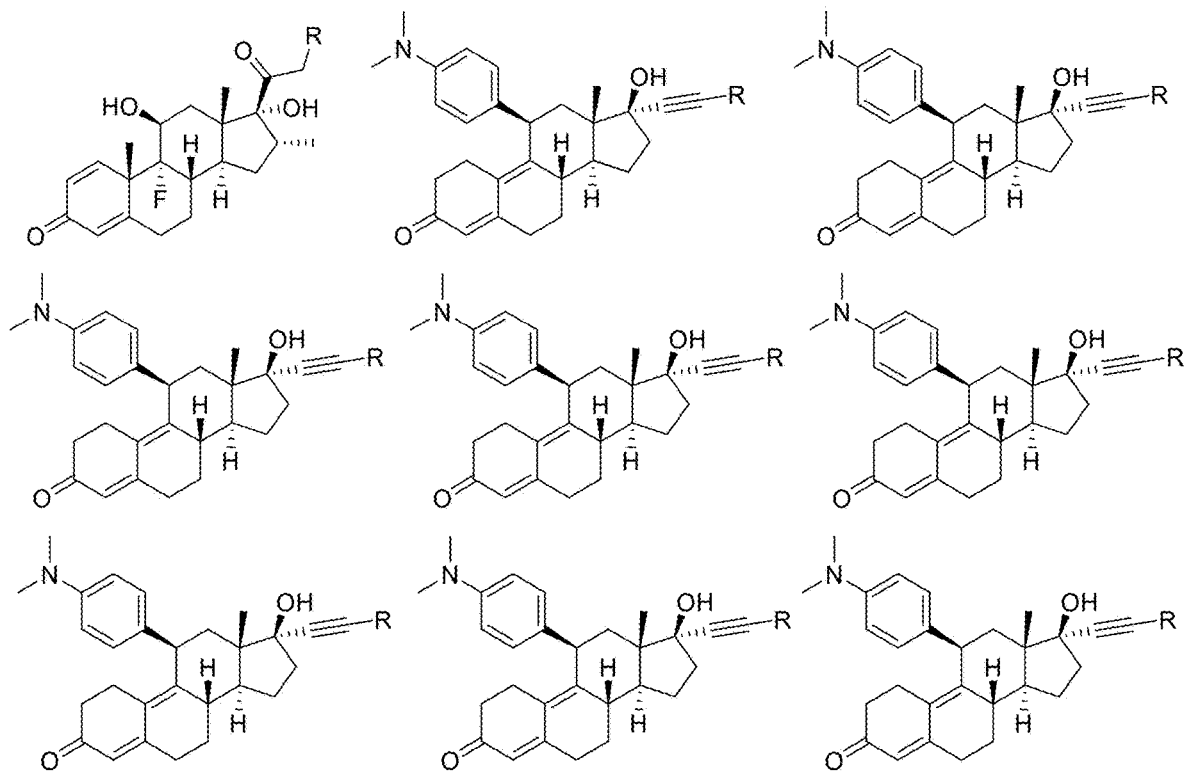
FIG. 2R-2S provide non-limiting examples of Glucocorticoid Receptor Targeting Ligands wherein R represents exemplary points at which the Linker can be attached.
Figure 2S:
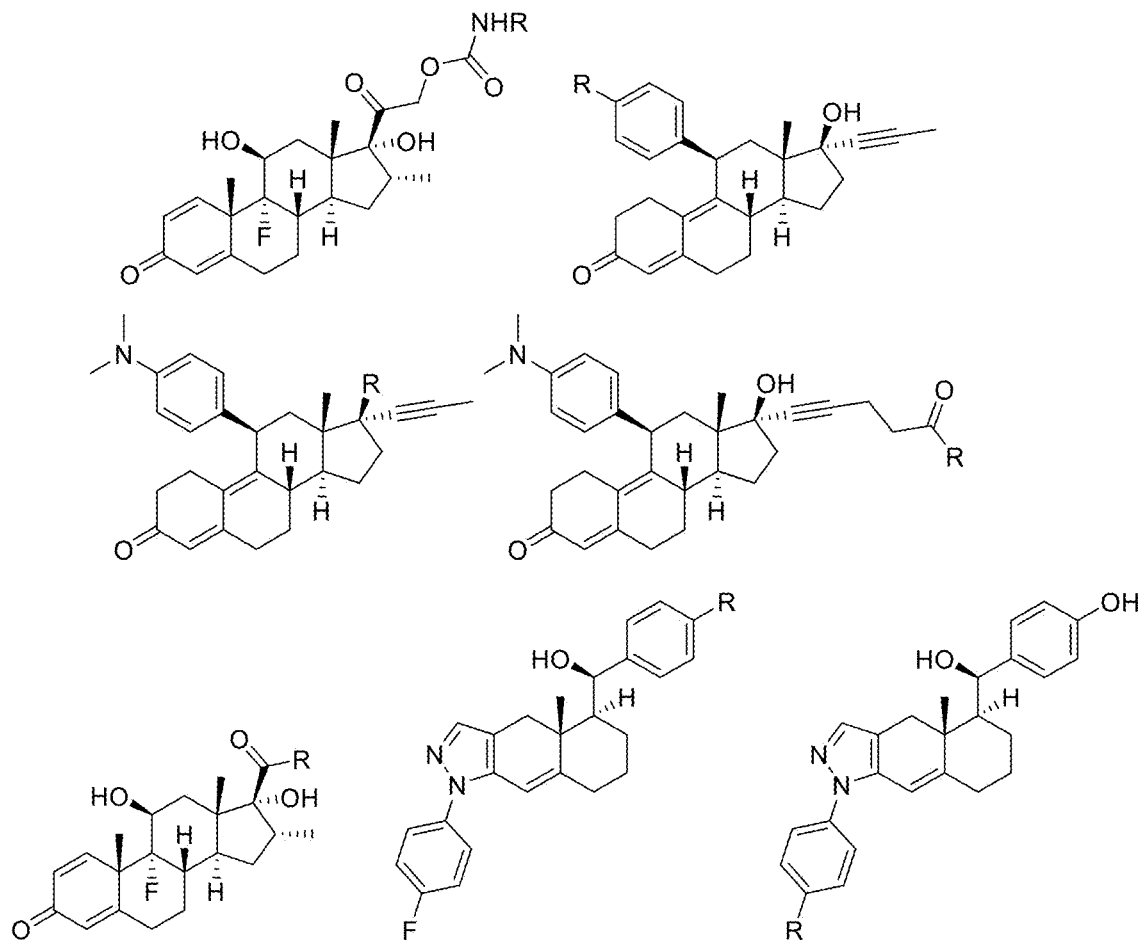
Figure 2T:
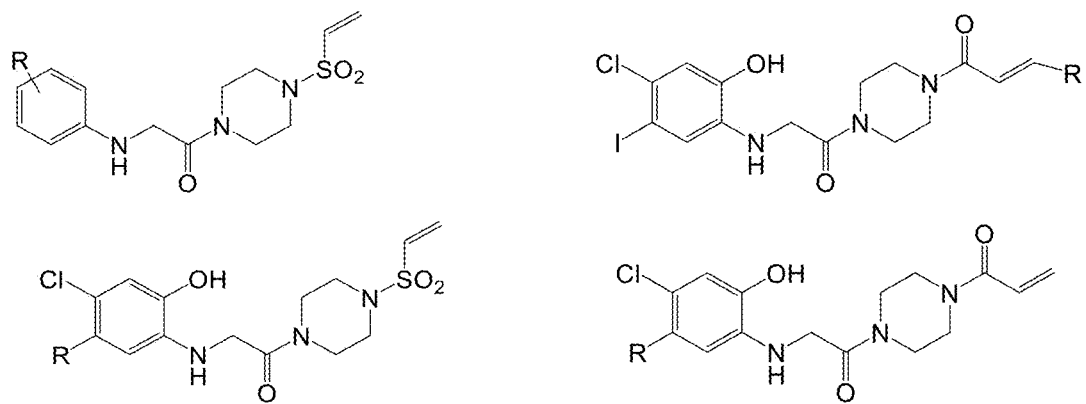
FIG. 2T-2U provide non-limiting examples of RasG12C Targeting Ligands wherein R represents exemplary points at which the Linker can be attached.
Figure 2U:
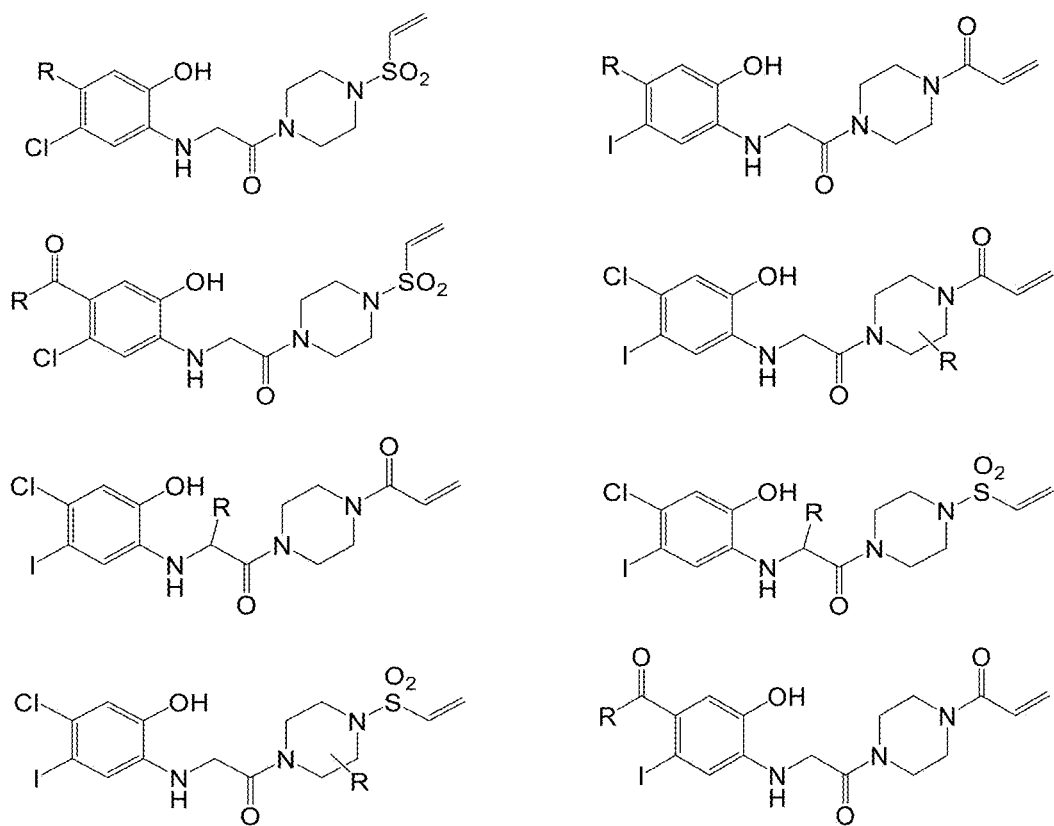
Figure 2V:
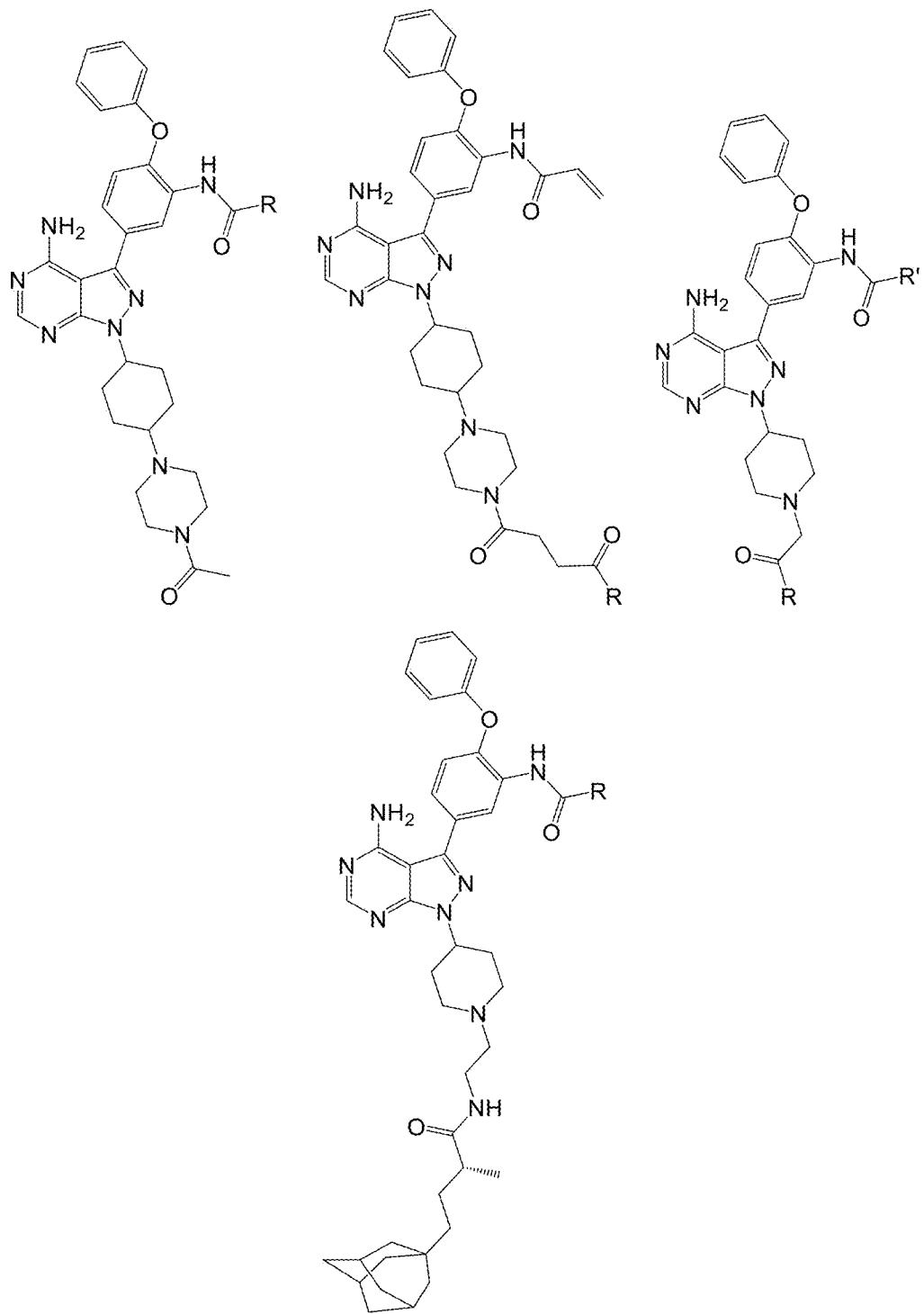
FIG. 2V provides non-limiting examples of Her3 Targeting Ligands wherein R represents exemplary points at which the Linker can be attached and R" is
Figure 2A:
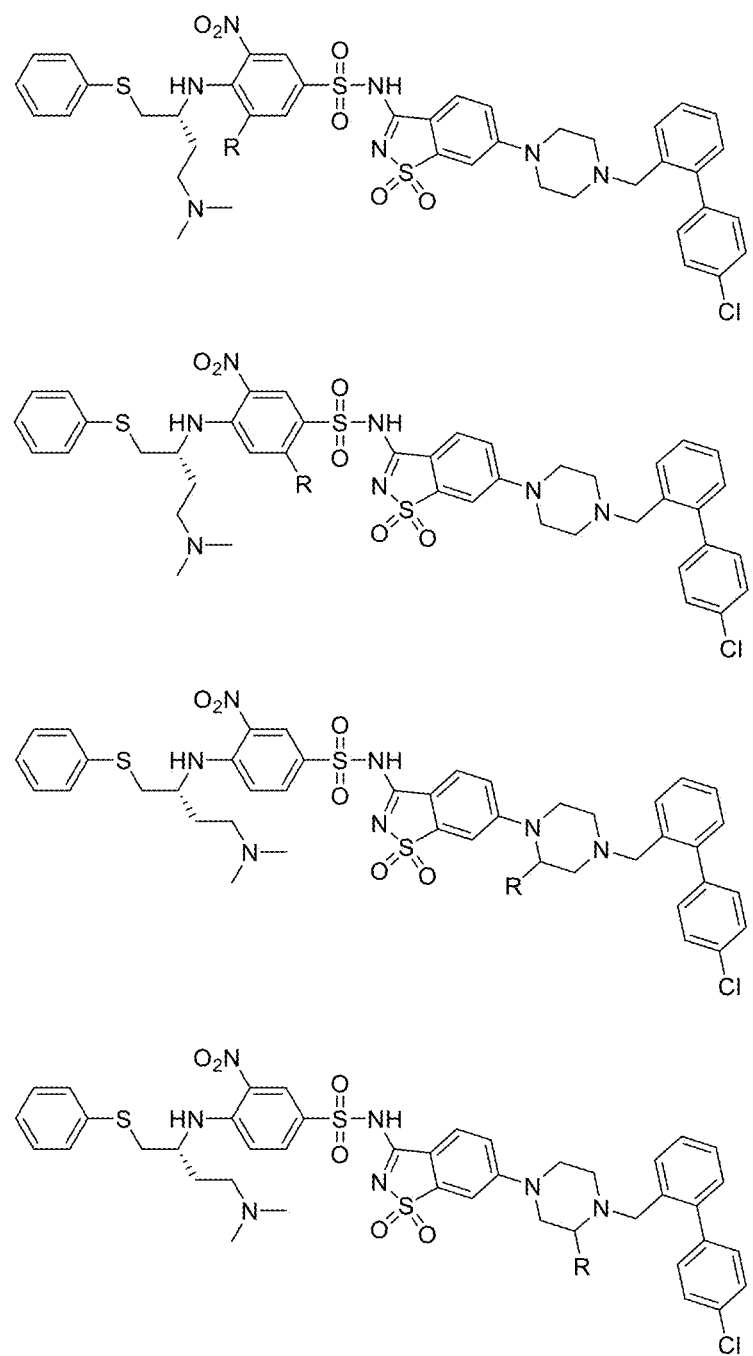
Figure 2B:
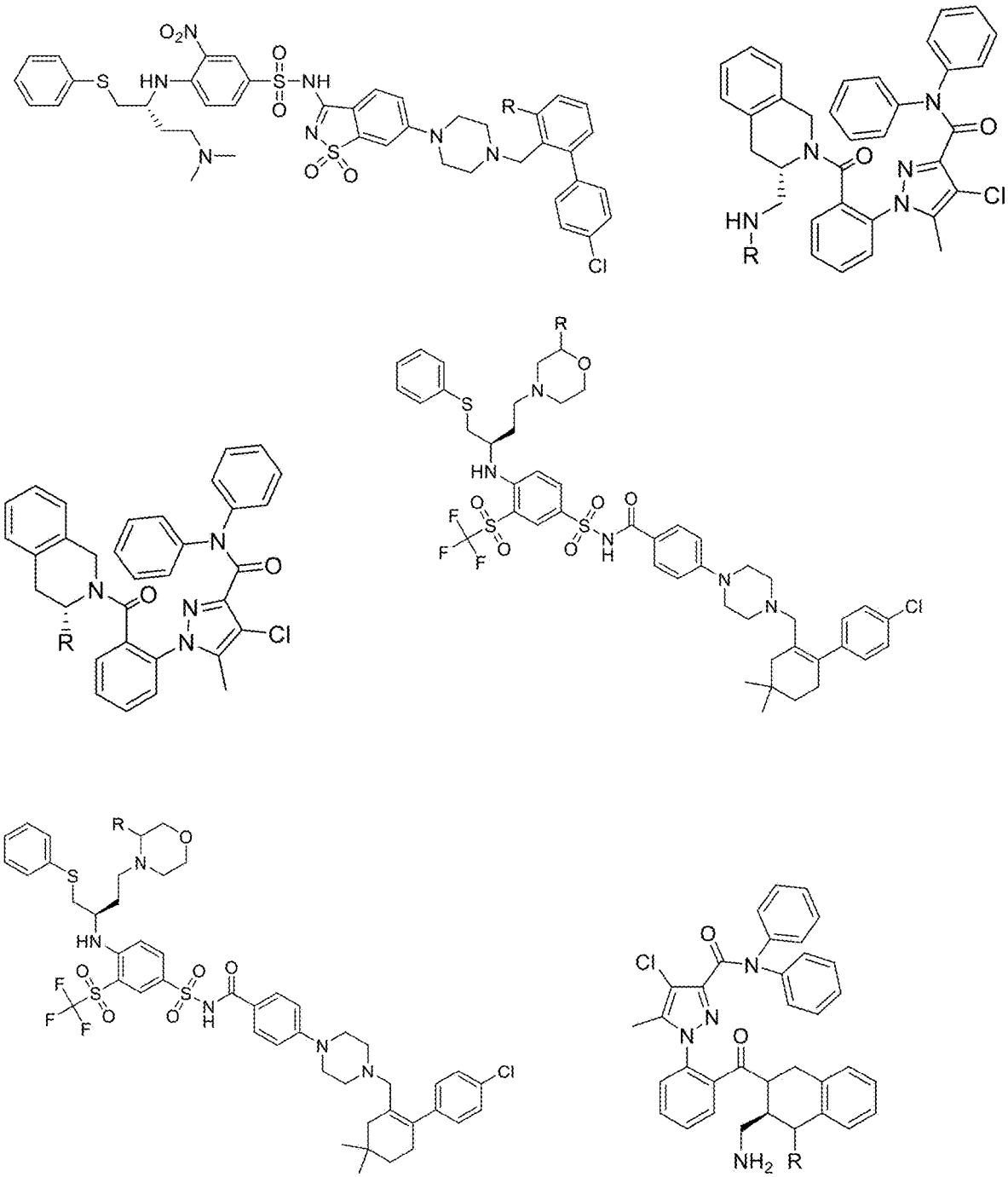
Figure 2C:
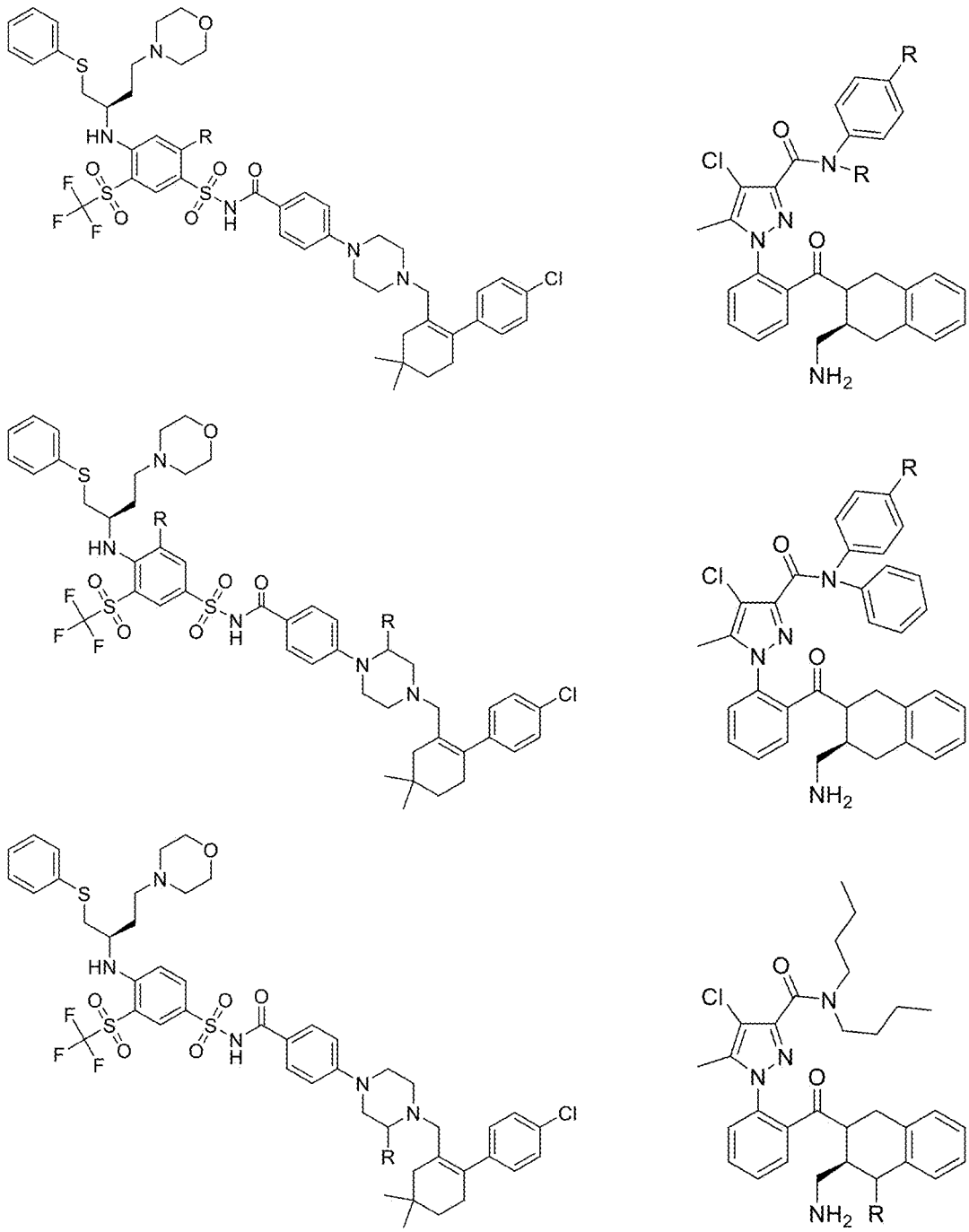
Figure 2D:
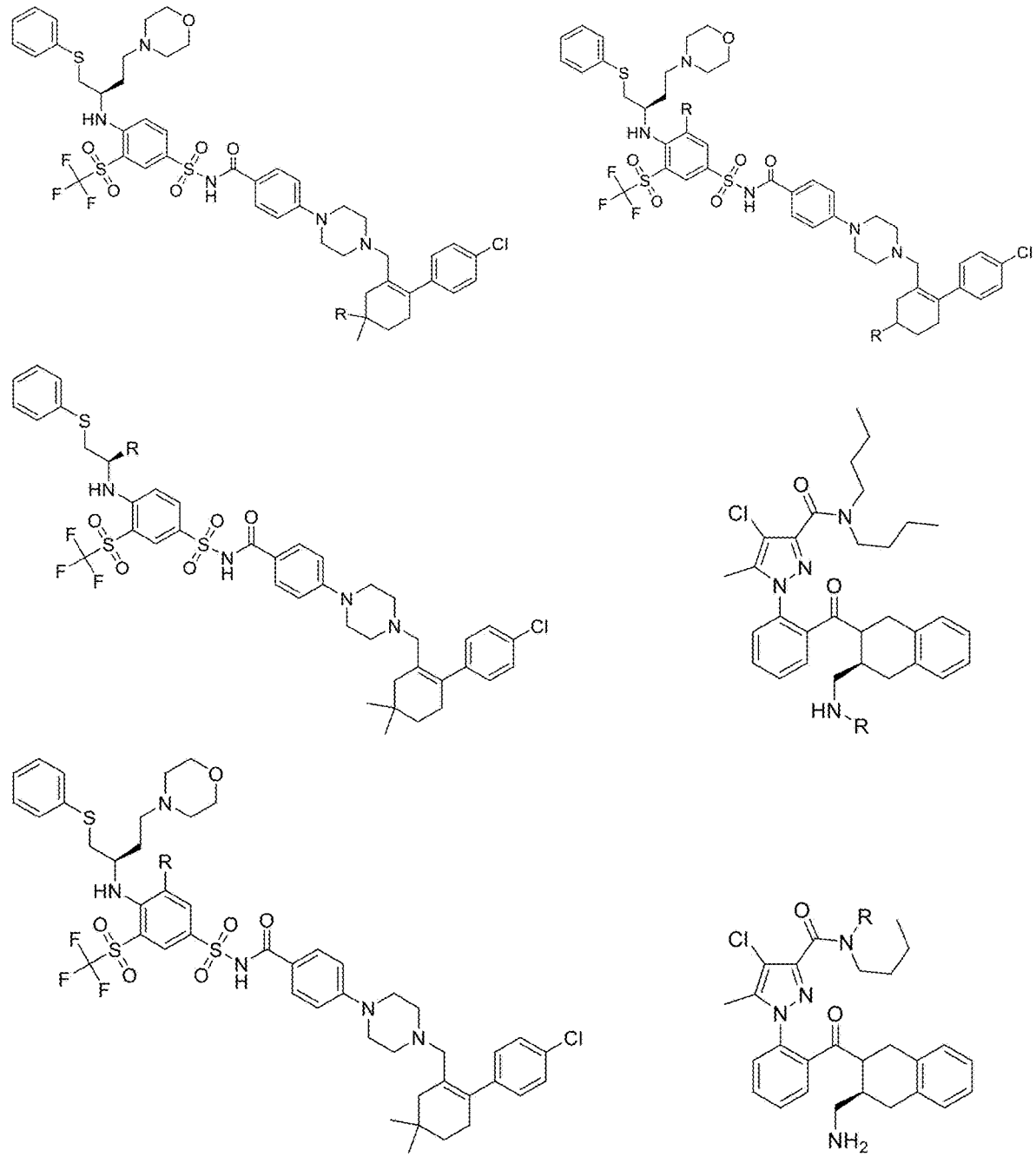
Figure 2E:
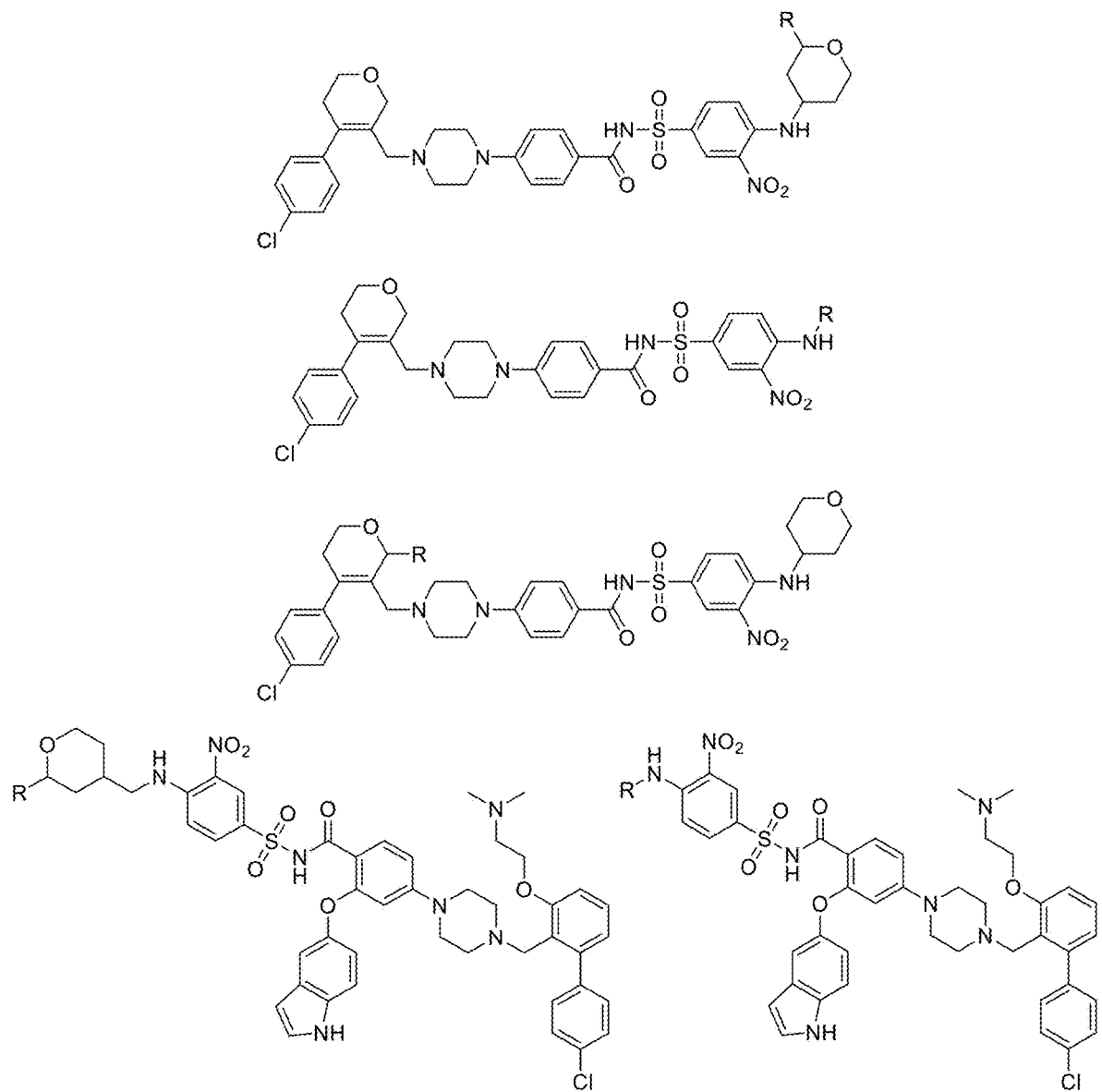
Figure 2F:
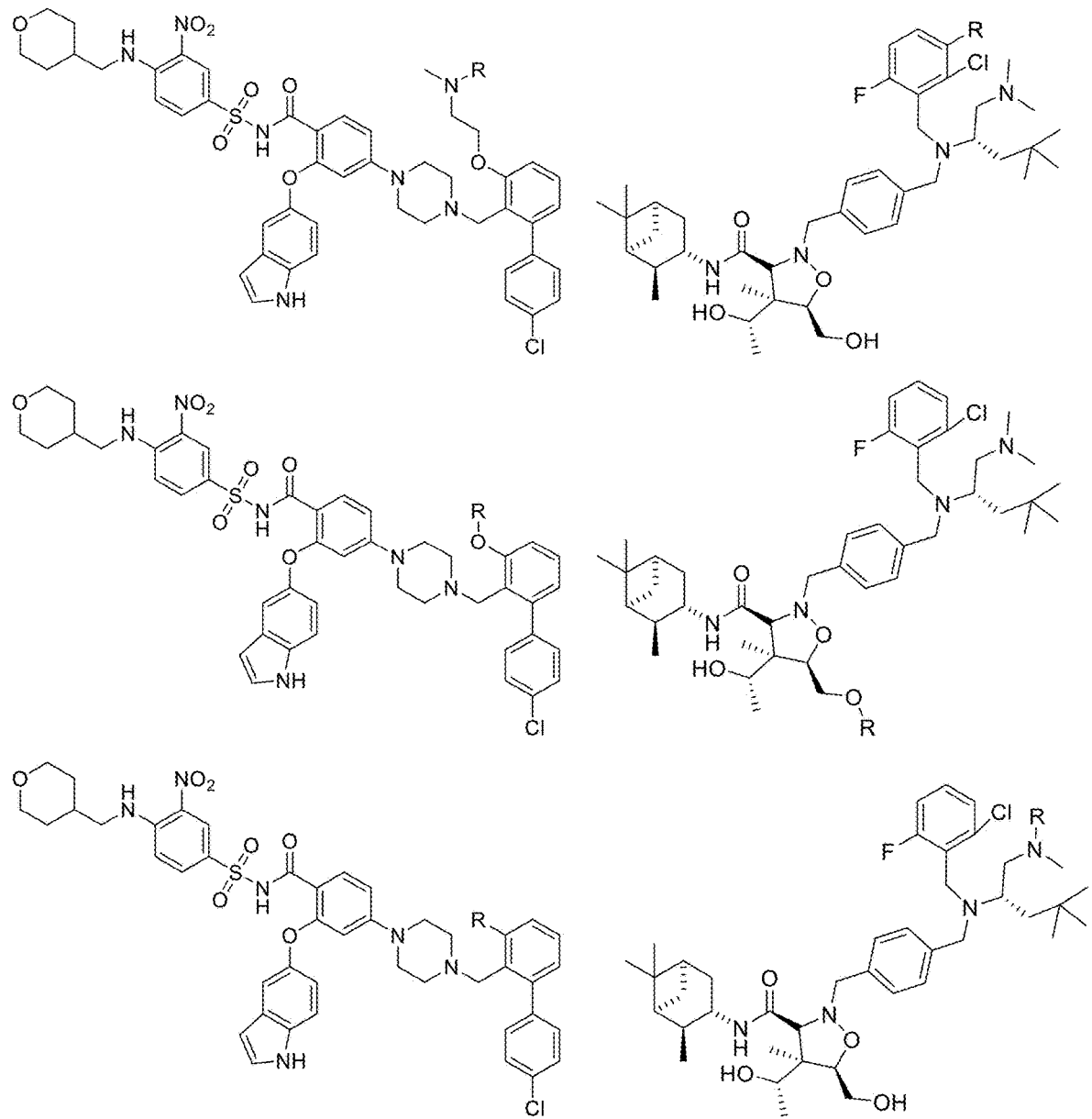
FIG. 2F provides non-limiting examples of kinase inhibitor Targeting Ligands, including the kinase inhibitor compound YCF, wherein R represents exemplary points at which the Linker can be attached. For additional examples and related ligands, see, the kinase inhibitors identified in Lountos et al. "Structural Characterization of Inhibitor Complexes with Checkpoint Kinase 2 (Chk2) a Drug Target for Cancer Therapy" *J. Struct. Biol.*, 176: 292 (2011).
Figure 2G:
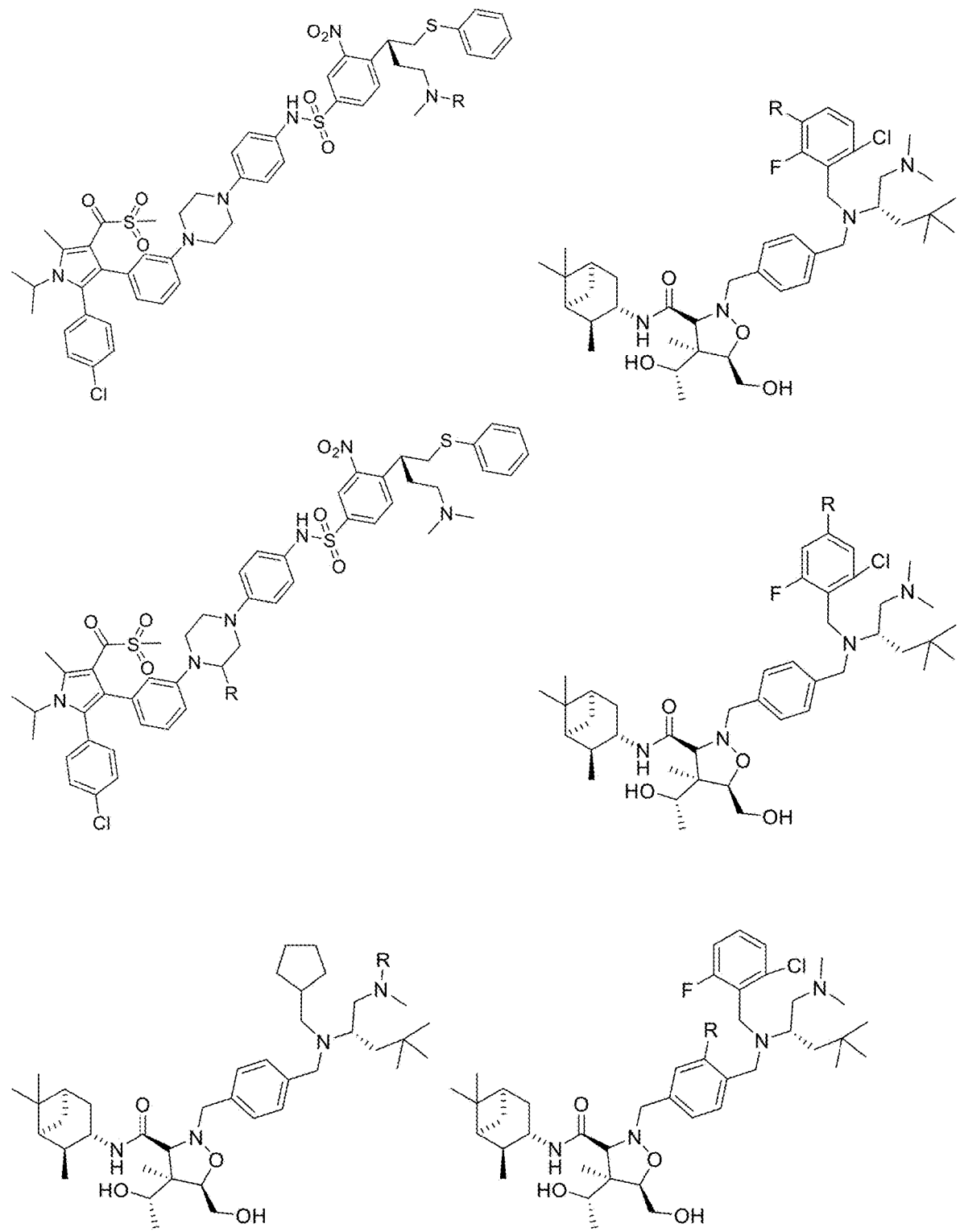
Figure 2H:
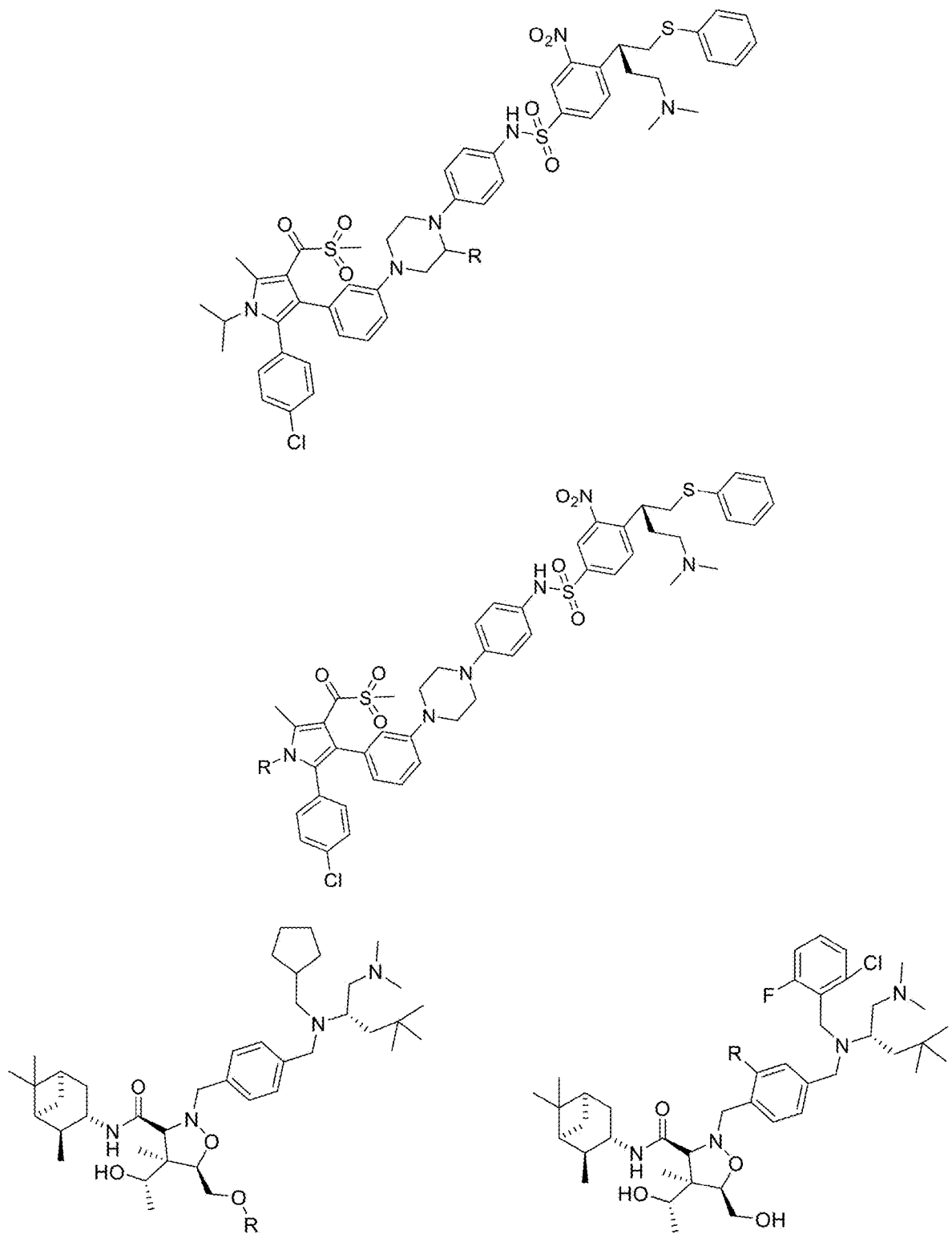
Figure 2I:
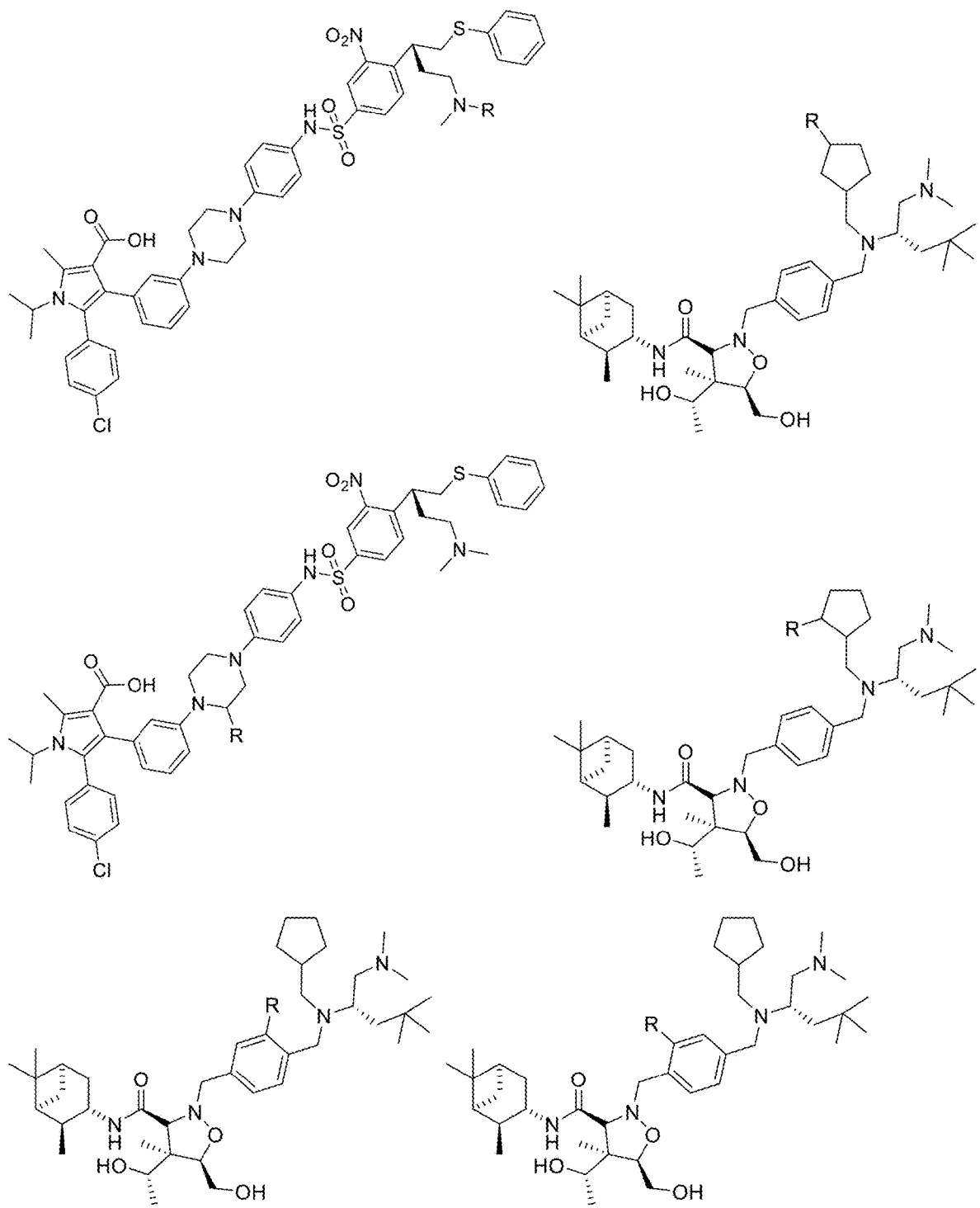
Figure 2J:
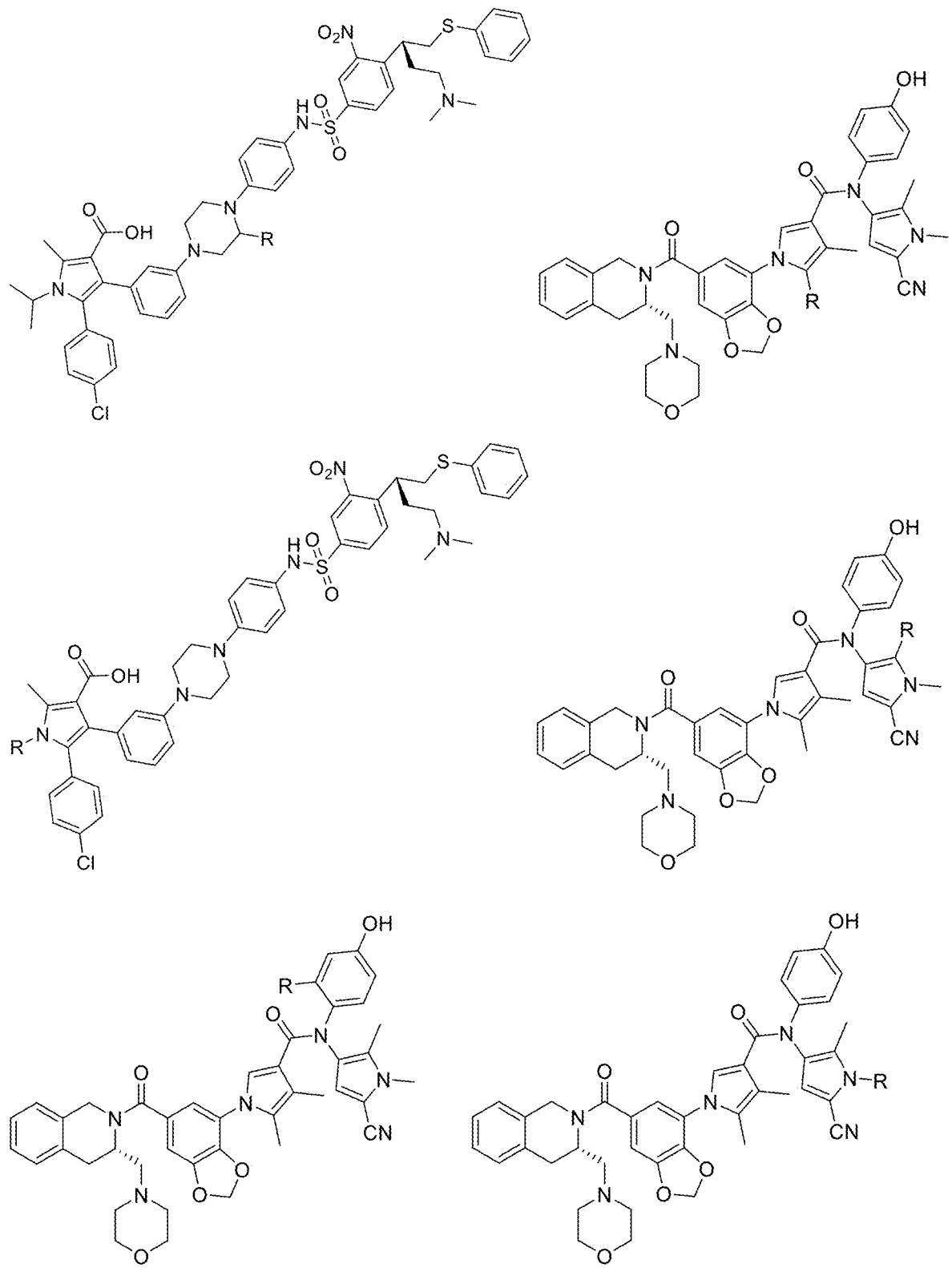
Figure 2K:
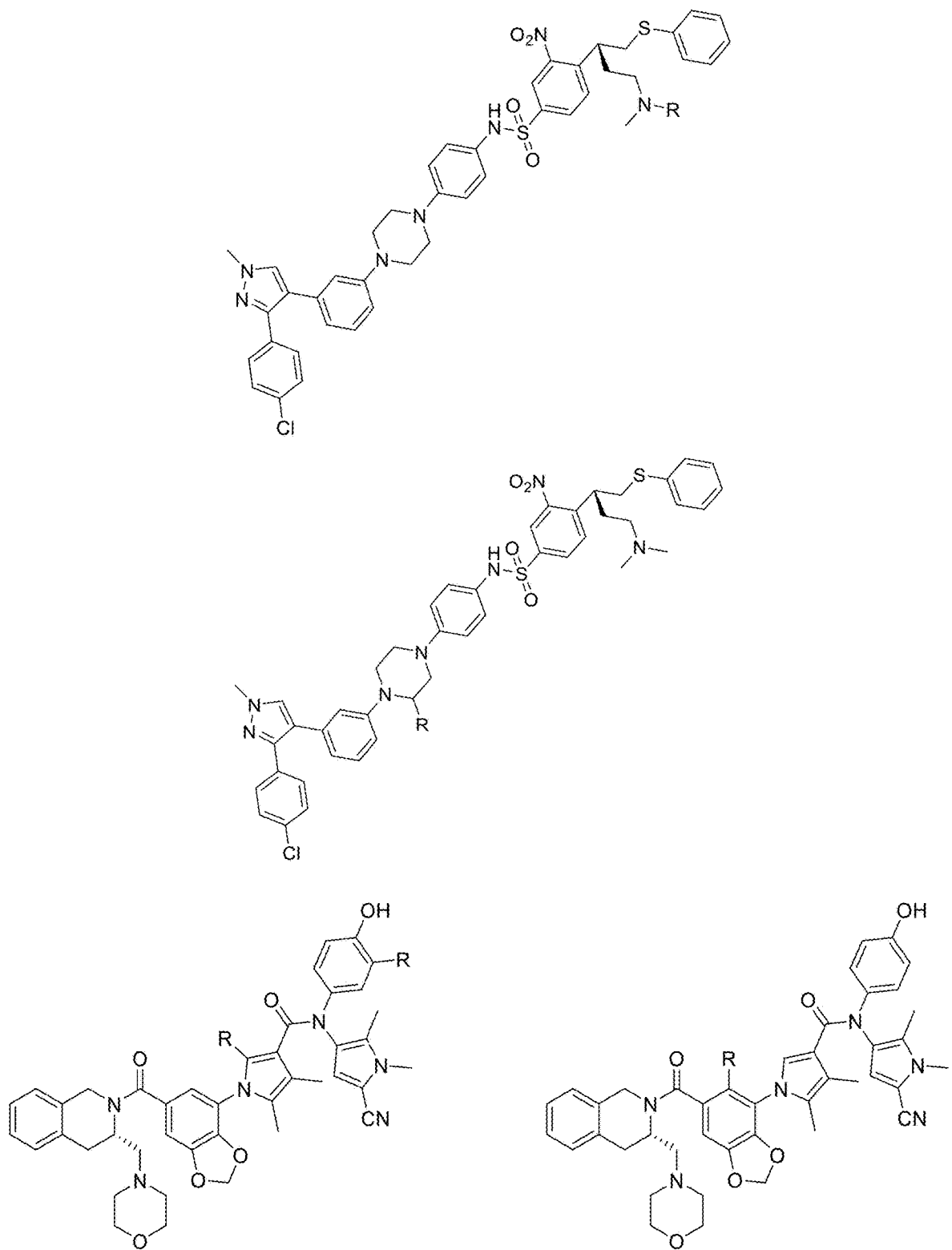
Figure 2L:
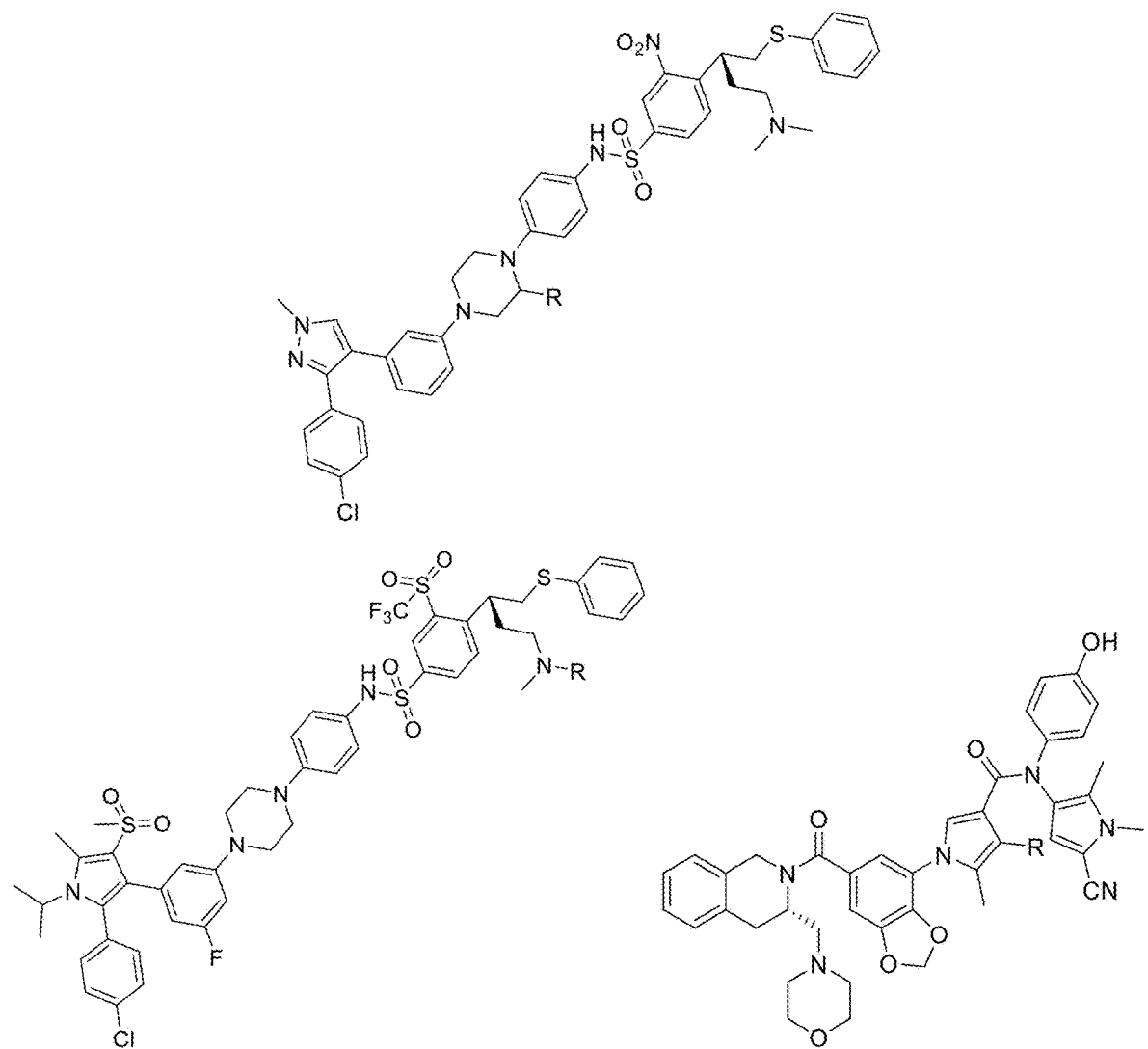
Figure 2M:
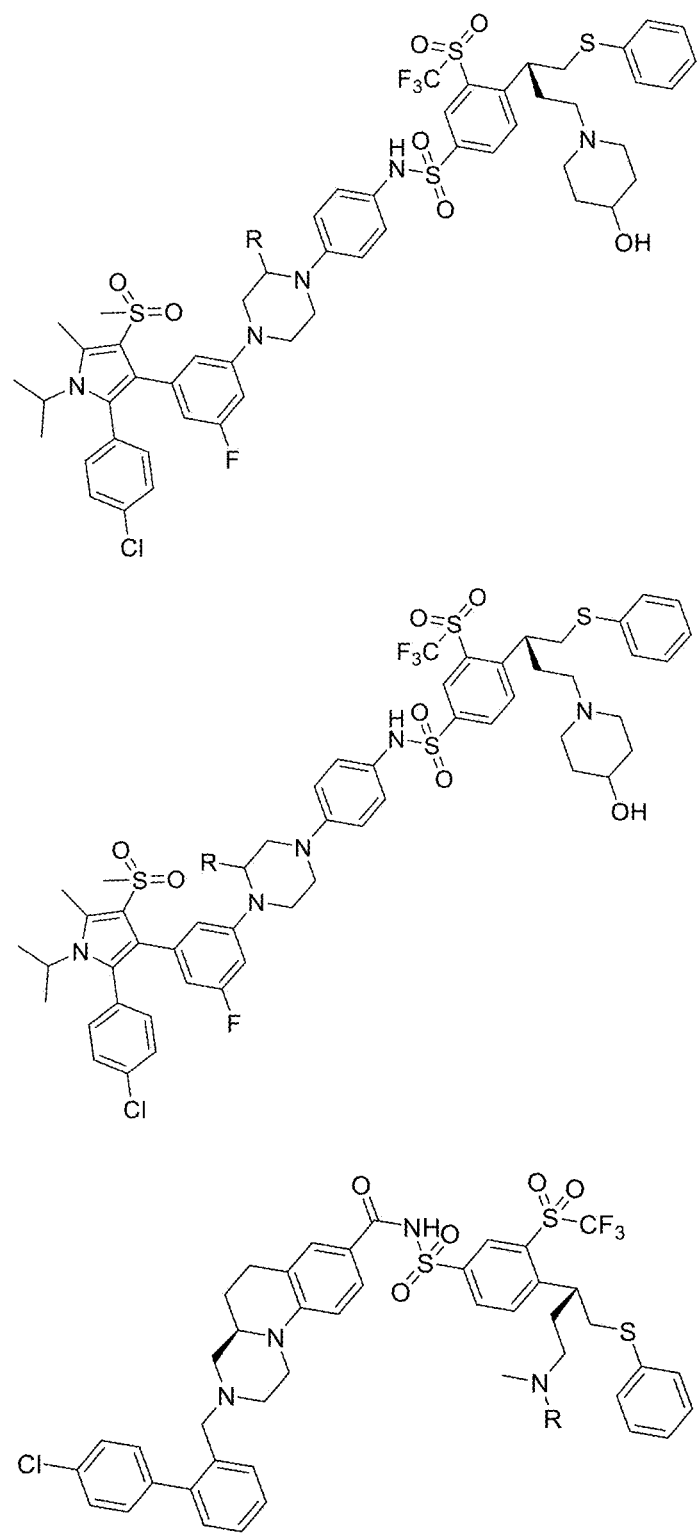
Figure 2N:
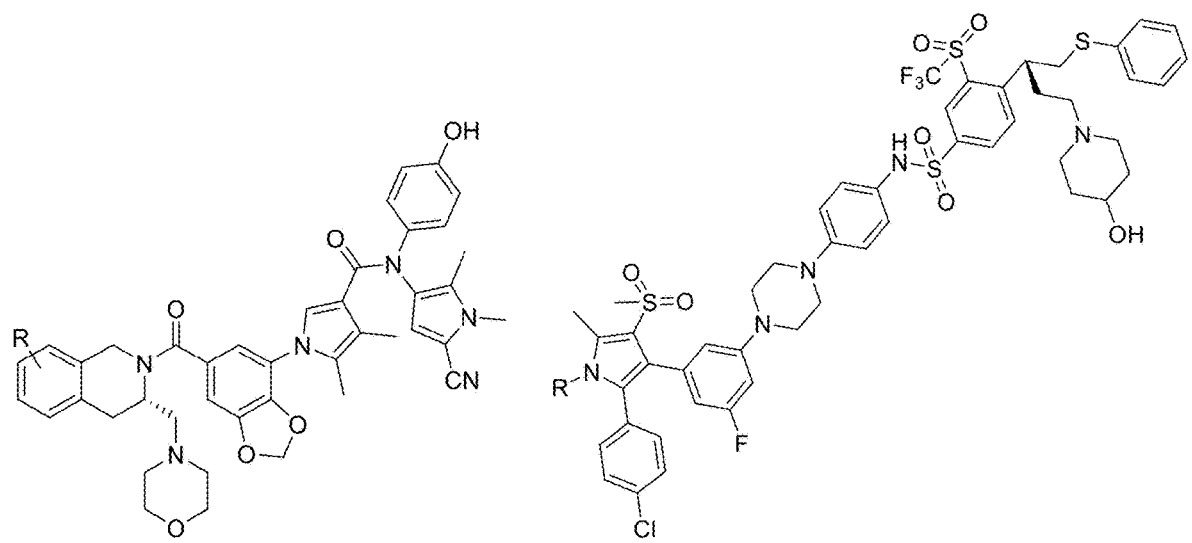
Figure 2O:
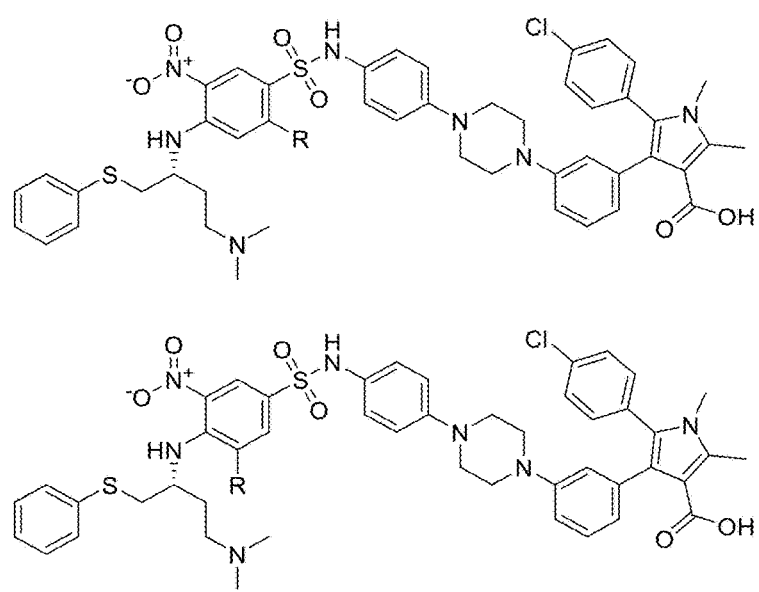
Figure 2P:
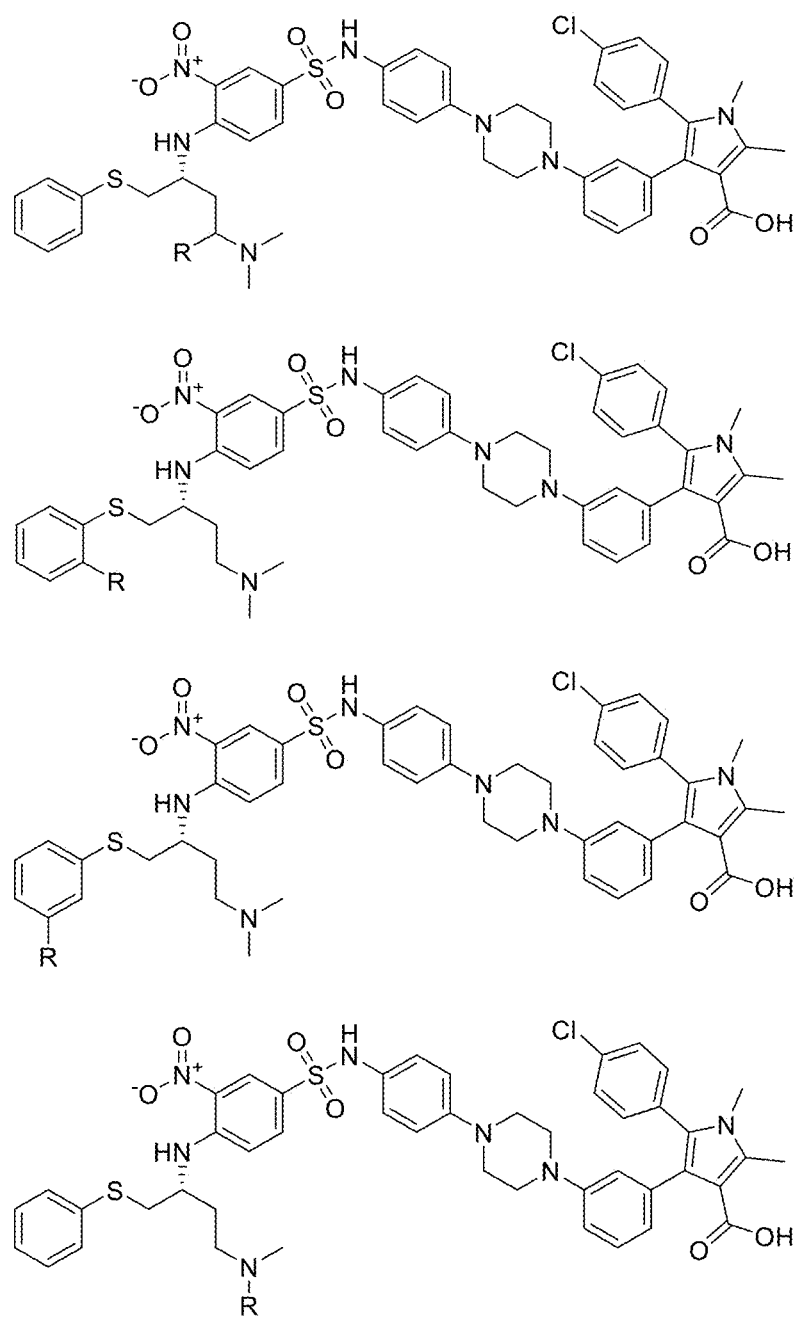
Figure 2Q:
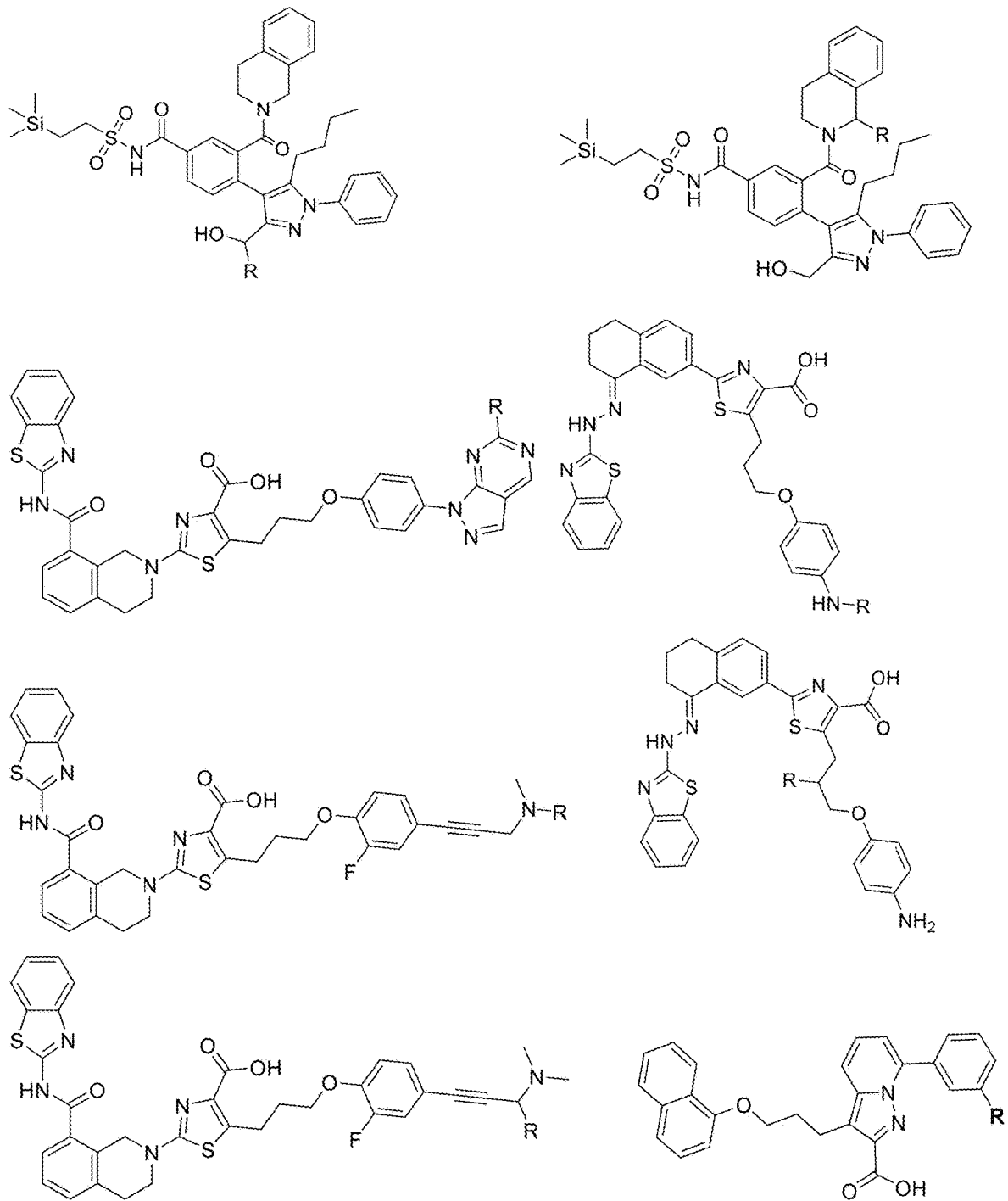
Figure 2S:
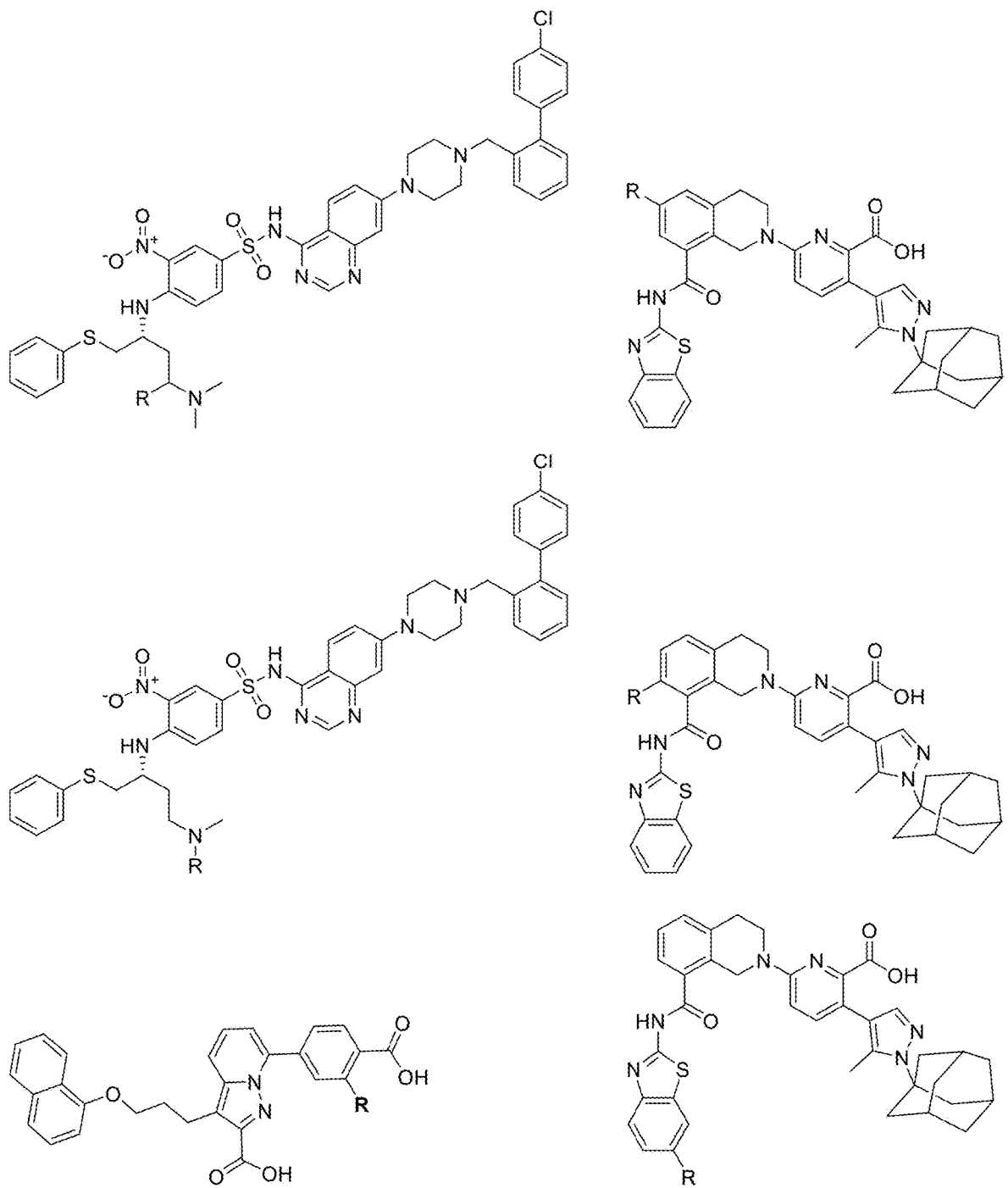
Figure 2T:
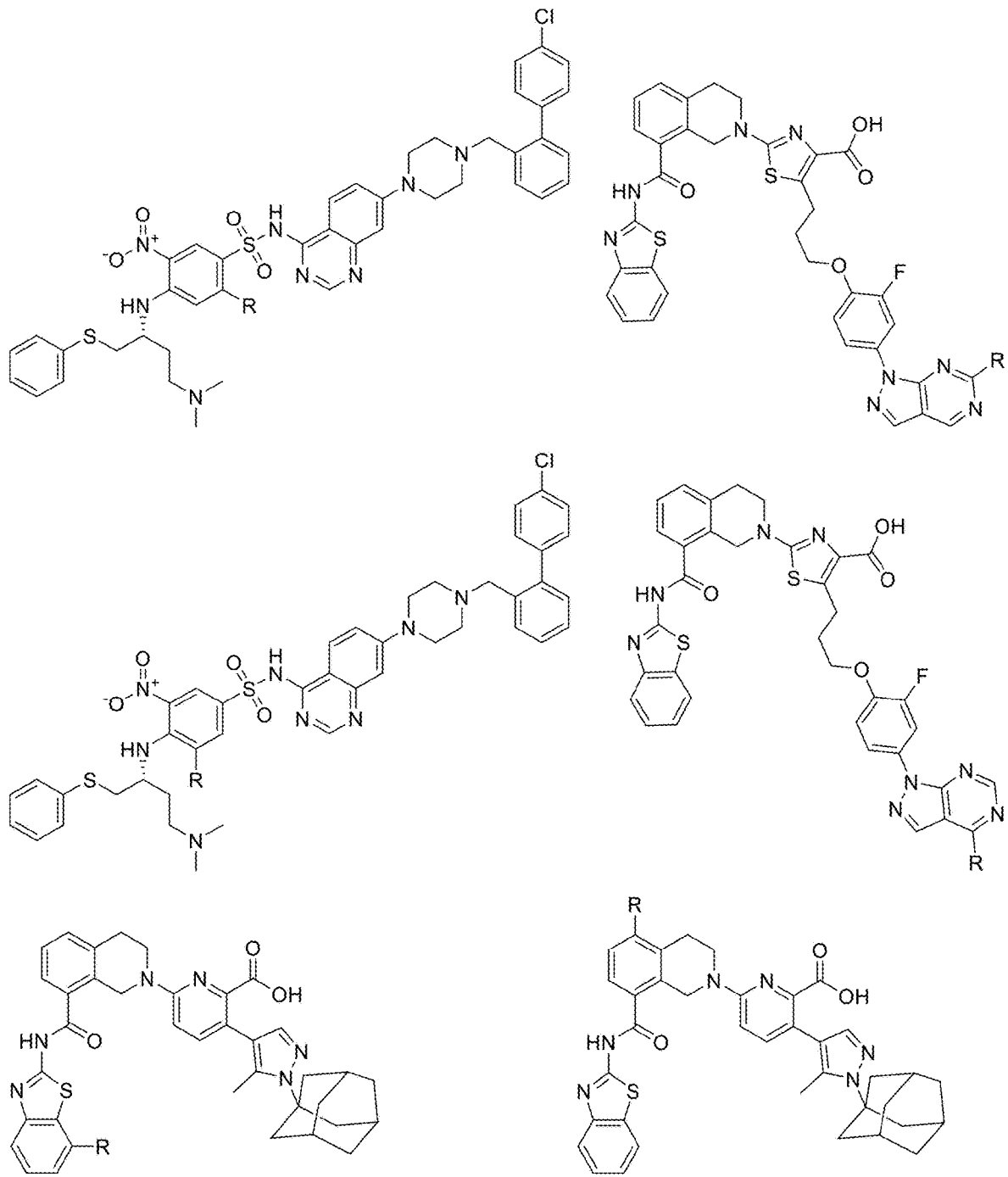
Figure 2U:
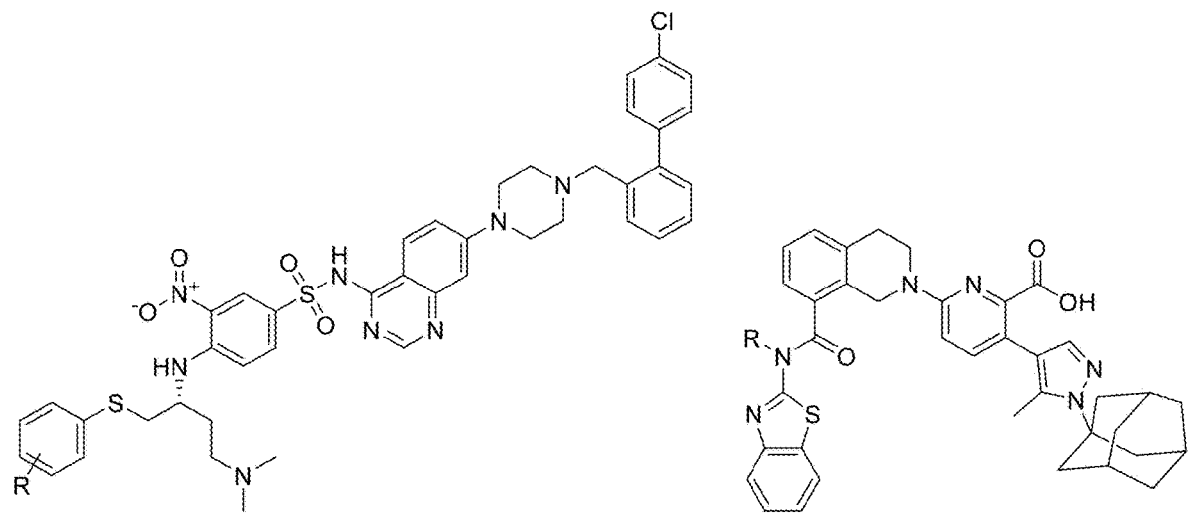
Figure 2V:
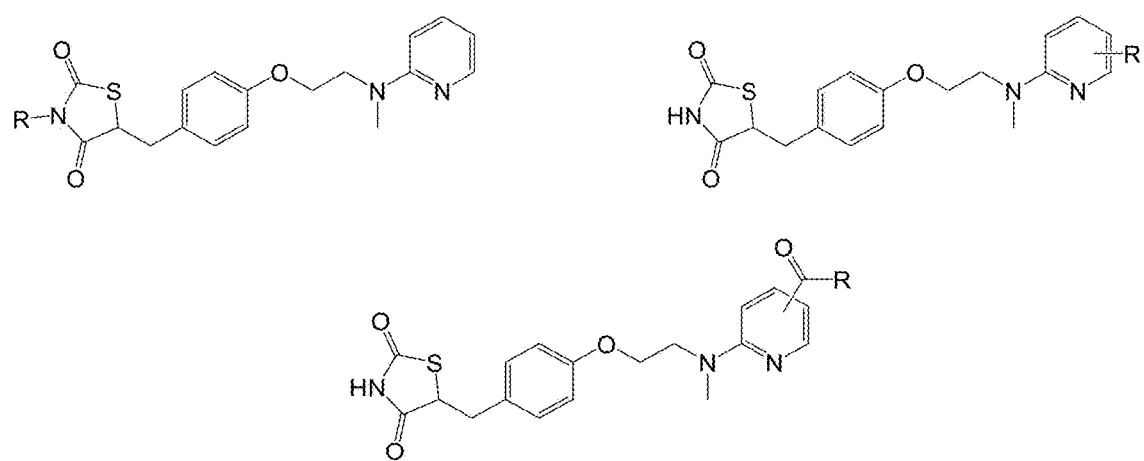
Figure 2W:
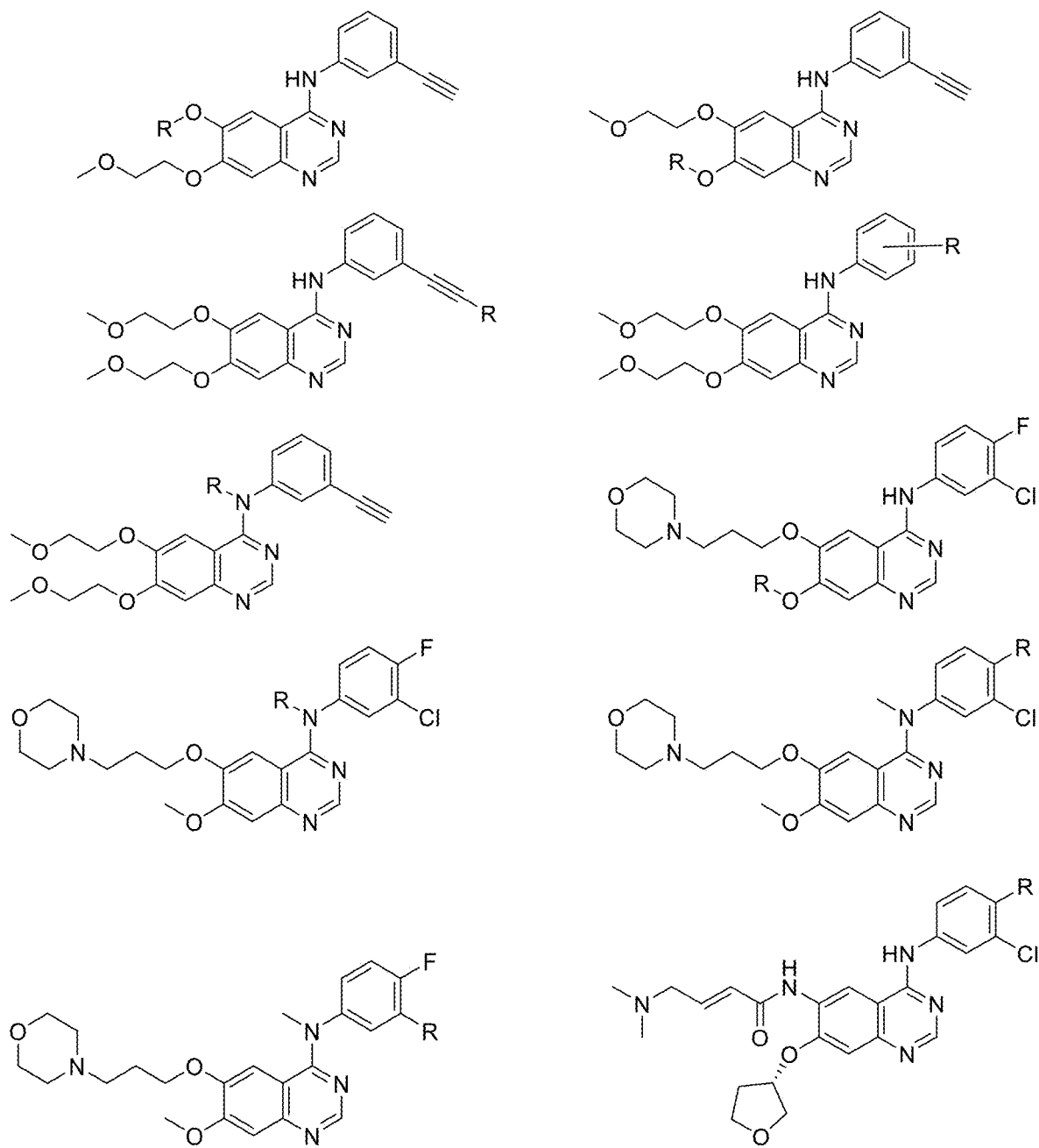

FIG. 2W provides non-limiting examples of Bcl-2 or Bcl-XL Targeting Ligands wherein R represents exemplary points at which the Linker can be attached.

Figure 2X:
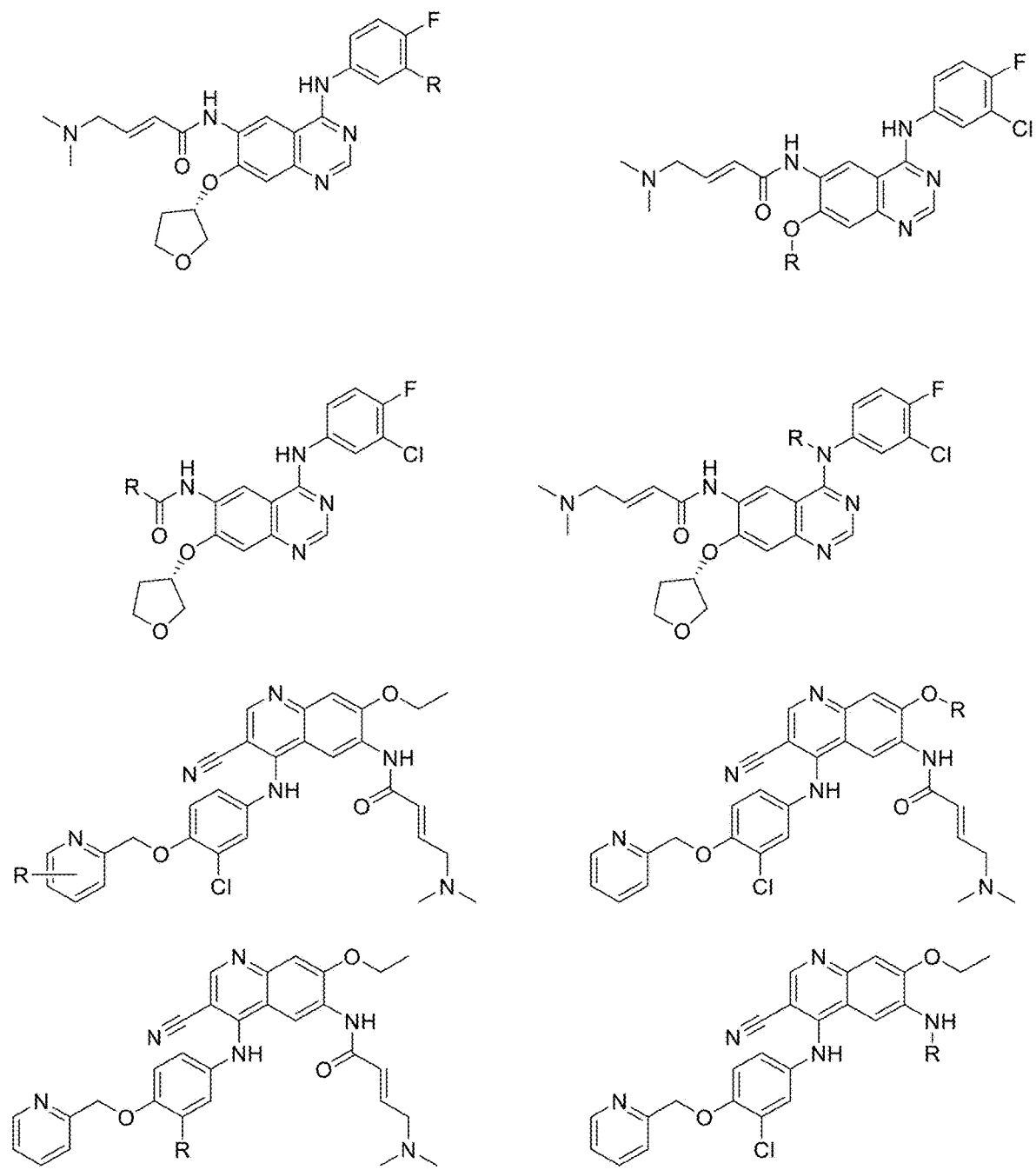

FIG. 2X-2NN provide non-limiting examples of BCL2 Targeting Ligands wherein R represents exemplary points at which the Linker can be attached. For additional examples and related ligands, see, Toure B. B. et al. "The role of the acidity of N-heteroaryl sulfonamides as inhibitors of bcl-2 family protein-protein interactions." *ACS Med Chem Lett*, 4: 186-190 (2013); Porter J. e.t al. "Tetrahydroisoquinoline Amide Substituted Phenyl Pyrazoles as Selective Bcl-2 Inhibitors" *Bioorg. Med. Chem. Lett.* 19: 230 (2009); Souers A. J. et al. "ABT-199 a potent and selective BCL-2 inhibitor achieves antitumor activity while sparing platelets." *Nature Med.* 19: 202-208 (2013); Angelo Aguilar et al. "A Potent and Highly Efficacious Bcl-2/Bcl-xL Inhibitor" *J Med Chem.* 56(7): 3048-3067 (2013); Longchuan Bai et al. "BM-1197: A Novel and Specific Bcl-2/Bcl-xL Inhibitor Inducing Complete and Long-Lasting Tumor Regression In Vivo" *PLoS ONE* 9(6): e99404; Fariba Ne'matil et al. "Targeting Bcl-2/Bcl-XL Induces Antitumor Activity in Uveal Melanoma Patient-Derived Xenografts" *PLoS ONE* 9(1): e80836; WO2015011396 titled "Novel derivatives of indole and pyrrole method for the production thereof and pharmaceutical compositions containing same"; WO2008060569A1 titled "Compounds and methods for inhibiting the interaction of Bcl proteins with binding partners"; "Inhibitors of the anti-apoptotic Bcl-2 proteins: a patent review" *Expert Opin. Ther. Patents* 22(1):2008 (2012); and, Porter et al. "Tetrahydroisoquinoline amide substituted phenyl pyrazoles as selective Bcl-2 inhibitors" *Bioorg Med Chem Lett.*, 19(1):230-3 (2009).

FIG. 2OO-2UU provide non-limiting examples of BCL-XL Targeting Ligands wherein R represents exemplary points at which the Linker can be attached. For additional examples and related ligands, see, Zhi-Fu Tao et al. "Discovery of a Potent and Selective BCL-XL Inhibitor with in Vivo Activity" *ACS Med. Chem. Lett.*, 5: 1088-1093 (2014); Joel D. Leverson et al. "Exploiting selective BCL-2 family inhibitors to dissect cell survival dependencies and define improved strategies for cancer therapy" *Science Translational Medicine*, 7:279ra40 (2015); and, the crystal structure PDB 3ZK6 (Guillaume Lessene et al. "Structure-guided design of a selective BCL-XL inhibitor" *Nature Chemical Biology* 9: 390-397 (2013))

FIG. 2VV provides non-limiting examples of PPAR-gamma Targeting Ligands wherein R represents exemplary points at which the Linker can be attached.

FIG. 2WW-2YY provide non-limiting examples of EGFR Targeting Ligands that target the EGFR L858R mutant, including erlotinib, gefitnib, afatinib, neratinib, and dacomitinib, wherein R represents exemplary points at which the Linker can be attached.

Figure 2Y:
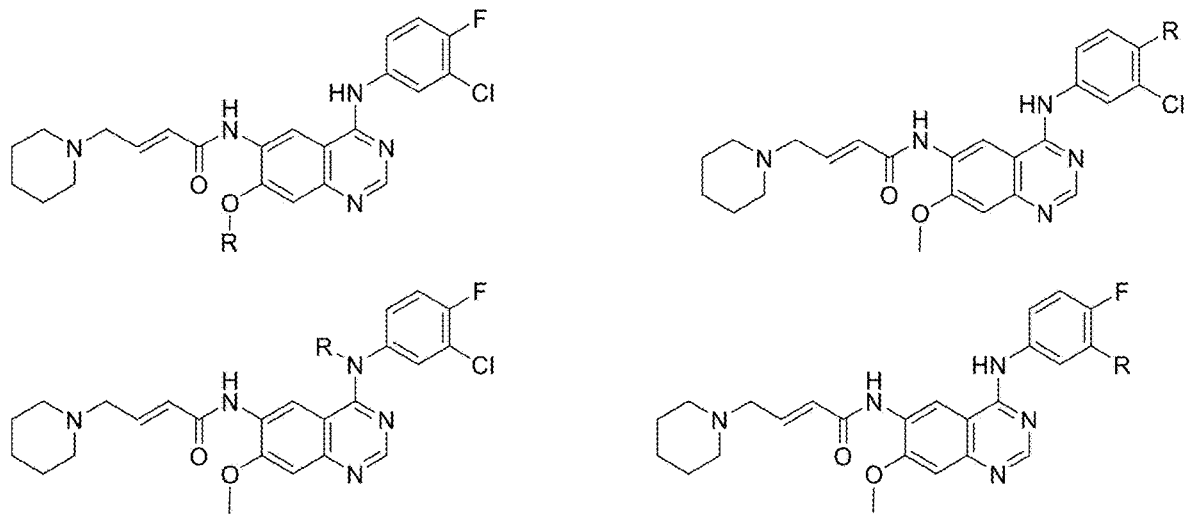
Figure 2Z:
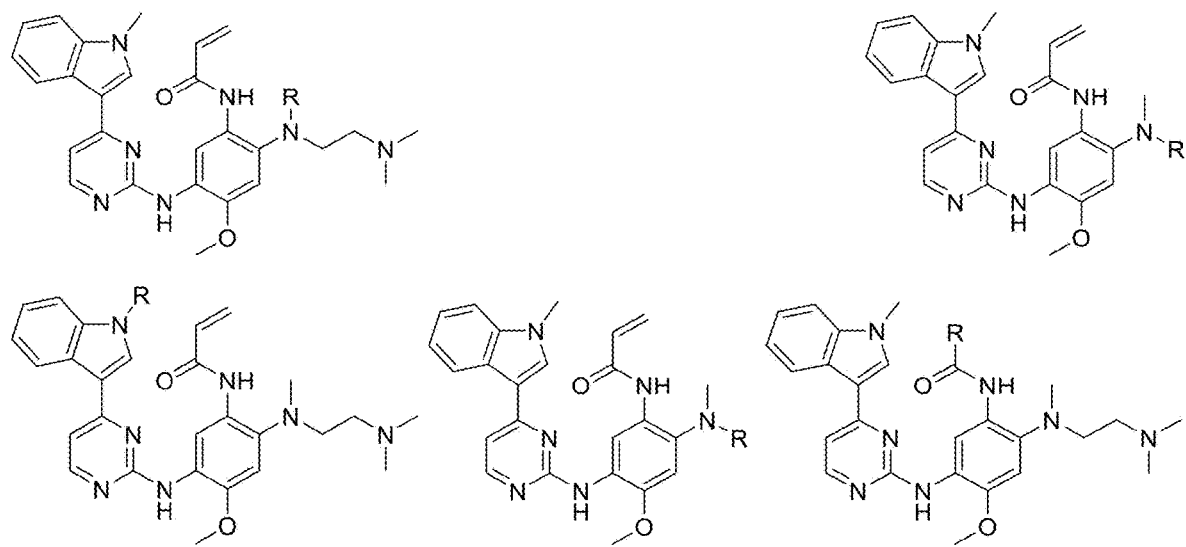

FIG. 2ZZ-2FFF provide non-limiting examples of EGFR Targeting Ligands that target the EGFR T790M mutant, including osimertinib, rociletinib, olmutinib, naquotinib, nazartinib, PF-06747775, Icotinib, Neratinib Avitinib, Tarloxotinib, PF-0645998, Tesevatinib, Transtinib, WZ-3146, WZ8040, and CNX-2006, wherein R represents exemplary points at which the Linker can be attached.

FIG. 2GGG provides non-limiting examples of EGFR Targeting Ligands that target the EGFR C797S mutant, including EAI045, wherein R represents exemplary points at which the Linker can be attached.

FIG. 2HHH provides non-limiting examples of BCR-ABL Targeting Ligands that target the BCR-ABL T315I mutant including Nilotinib and Dasatinib, wherein R represents exemplary points at which the Linker can be attached. See for example, the crystal structure PDB 3CS9.

FIG. 2III provides non-limiting examples of Targeting Ligands that target BCR-ABL, including Nilotinib, Dasatinib Ponatinib and Bosutinib, wherein R represents exemplary points at which the Linker can be attached.

FIG. 2JJJ-2KKK provide non-limiting examples of ALK Targeting Ligands that target the ALK L 1196M mutant including Ceritinib, wherein R represents exemplary points at which the Linker can be attached. See for example, the crystal structure PDB 4MKC.

FIG. 2LLL provides non-limiting examples of JAK2 Targeting Ligands that target the JAK2V617F mutant, including Ruxolitinib, wherein R represents exemplary points at which the Linker can be attached.

FIG. 2MMM provides non-limiting examples of BRAF Targeting Ligands that target the BRAF V600E mutant including Vemurafenib, wherein R represents exemplary points at which the Linker can be attached. For additional examples and related ligands, see, the crystal structure PBD 3OG7.

FIG. 2NNN provides non-limiting examples of BRAF Targeting Ligands, including Dabrafenib, wherein R represents exemplary points at which the Linker can be attached.

FIG. 2OOO provides non-limiting examples of LRRK2 Targeting Ligands that target the LRRK2 R1441C mutant wherein R represents exemplary points at which the Linker can be attached.

FIG. 2PPP provides non-limiting examples of LRRK2 Targeting Ligands that target the LRRK2 G2019S mutant wherein R represents exemplary points at which the Linker can be attached.

FIG. 2QQQ provides non-limiting examples of LRRK2 Targeting Ligands that target the LRRK2 I2020T mutant wherein R represents exemplary points at which the Linker can be attached.

FIG. 2RRR-2TTT provide non-limiting examples of PDGFRa Targeting Ligands that target the PDGFRa T674I mutant, including AG-1478, CHEMBL94431, Dovitinib, erlotinib, gefitinib, imatinib, Janex 1, Pazopanib, PD153035, Sorafenib, Sunitinib, and WHI-P180, wherein R represents exemplary points at which the Linker can be attached.

FIG. 2UUU provides non-limiting examples of RET Targeting Ligands that target the RET G691S mutant, including tozasertib, wherein R represents exemplary points at which the Linker can be attached.

FIG. 2VVV provides non-limiting examples of RET Targeting Ligands that target the RET R749T mutant, including tozasertib, wherein R represents exemplary points at which the Linker can be attached.

FIG. 2WWW provides non-limiting examples of RET Targeting Ligands that target the RET E762Q mutant, including tozasertib, wherein R represents exemplary points at which the Linker can be attached.

FIG. 2XXX provides non-limiting examples of RET Targeting Ligands that target the RET Y791F mutant, including tozasertib, wherein R represents exemplary points at which the Linker can be attached.

FIG. 2YYY provides non-limiting examples of RET Targeting Ligands that target the RET V804M mutant, including tozasertib, wherein R represents exemplary points at which the Linker can be attached.

FIG. 2ZZZ provides non-limiting examples of RET Targeting Ligands that target the RET M918T mutant, including tozasertib, wherein R represents exemplary points at which the Linker can be attached.

FIG. 2AAAA provides non-limiting examples of Fatty Acid Binding Protein Targeting Ligands wherein R represents exemplary points at which the Linker can be attached.

FIG. 2BBBB provides non-limiting examples of 5-Lipoxygenase Activating Protein (FLAP) Targeting Ligands wherein R represents exemplary points at which the Linker can be attached.

FIG. 2CCCC provides non-limiting examples of Kringle Domain V 4BVV Targeting Ligands wherein R represents exemplary points at which the Linker can be attached.

FIG. 2DDDD provides non-limiting examples of Lactoylglutathione Lyase Targeting Ligands wherein R represents exemplary points at which the Linker can be attached.

FIG. 2EEEE-2FFFF provide non-limiting examples of mPGES-1 Targeting Ligands wherein R represents exemplary points at which the Linker can be attached.

FIG. 2GGGG-2JJJJ provide non-limiting examples of Factor Xa Targeting Ligands wherein R represents exemplary points at which the Linker can be attached. For additional examples and related ligands, see, Maignan S. et al. "Crystal structures of human factor Xa complexed with potent inhibitors." *J. Med Chem.* 43: 3226-3232 (2000); Matsusue T. et al. "Factor Xa Specific Inhibitor that Induces the Novel Binding Model in Complex with Human Fxa." (to be published); the crystal structures PDB liqh, liqi, liqk, and ligm; Adler M. et al. "Crystal Structures of Two Potent Nonamidine Inhibitors Bound to Factor Xa." *Biochemistry* 41: 15514-15523 (2002); Roehrig S. et al. "Discovery of the Novel Antithrombotic Agent 5-Chloro-N-({(5S)-2-Oxo-3-[4-(3-Oxomorpholin-4-Yl)Phenyl]-1 3-Oxazolidin-5-Yl}Methyl)Thiophene-2-Carboxamide (Bay 59-7939): An Oral Direct Factor Xa Inhibitor." *J. Med Chem.* 48: 5900 (2005); Anselm L. et al. "Discovery of a Factor Xa Inhibitor (3R 4R)-1-(2 2-Difluoro-Ethyl)-Pyrrolidine-3 4-Dicarboxylic Acid 3-[(5-Chloro-Pyridin-2-Yl)-Amide]4-{[2-Fluoro-4-(2-Oxo-2H-Pyridin-1-Yl)-Phenyl]-Amide} as a Clinical Candidate." *Bioorg. Med Chem.* 20: 5313 (2010); and, Pinto D. J. et al. "Discovery of 1-(4-Methoxyphenyl)-7-oxo-6-(4-(2-oxopiperidin-1-yl)phenyl)-4 5 6 7-tetrahydro-1H-pyrazolo[3 4-c]pyridine-3-carboxamide (Apixaban BMS-562247) a Highly Potent Selective Efficacious and Orally Bioavailable Inhibitor of Blood Coagulation Factor Xa." *J. Med Chem.* 50: 5339-5356 (2007).

FIG. 2KKKK provides non-limiting examples of Kallikrein 7 Targeting Ligands wherein R represents exemplary points at which the Linker can be attached. For additional examples and related ligands, see, Maibaum J. et al. "Small-molecule factor D inhibitors targeting the alternative complement pathway." *Nat. Chem. Biol.* 12: 1105-1110 (2016).

FIG. 2LLLL-2MMMM provide non-limiting examples of Cathepsin K Targeting Ligands wherein R represents exemplary points at which the Linker can be attached. For additional examples and related ligands, see, Rankovic Z. et al. "Design and optimization of a series of novel 2-cyanopyrimidines as cathepsin K inhibitors" *Bioorg. Med Chem. Lett.* 20: 1524-1527 (2010); and, Cai J. et al. "Trifluoromethylphenyl as P2 for ketoamide-based cathepsin S inhibitors." *Bioorg. Med Chem. Lett.* 20: 6890-6894 (2010).

FIG. 2NNNN provides non-limiting examples of Cathepsin L Targeting Ligands wherein R represents exemplary points at which the Linker can be attached. For additional examples and related ligands, see, Kuhn B. et al. "Prospective Evaluation of Free Energy Calculations for the Prioritization of Cathepsin L Inhibitors." *J. Med Chem.* 60: 2485-2497 (2017).

FIG. 2OOOO provides non-limiting examples of Cathepsin S Targeting Ligands wherein R represents exemplary points at which the Linker can be attached. For additional examples and related ligands, see, Jadhav P. K. et al. "Discovery of Cathepsin S Inhibitor LY3000328 for the Treatment of Abdominal Aortic Aneurysm" *ACS Med Chem. Lett.* 5: 1138-1142." (2014).

FIG. 2PPPP-2SSSS provide non-limiting examples of MTH1 Targeting Ligands wherein R represents exemplary points at which the Linker can be attached. For additional examples and related ligands, see, Kettle J. G. et al. "Potent and Selective Inhibitors of Mth1 Probe its Role in Cancer Cell Survival." *J. Med Chem.* 59: 2346 (2016); Huber K. V. M. et al. "Stereospecific Targeting of Mth1 by (S)-Crizotinib as an Anticancer Strategy." *Nature* 508: 222 (2014); Gad H. et al. "MTH1 inhibition eradicates cancer by preventing sanitation of the dNTP pool." *Nature* 508: 215-221 (2014); Nissink J. W. M. et al. "Mth1 Substrate Recognition—an Example of Specific Promiscuity." *Plos One* 11: 51154 (2016); and, Manuel Ellermann et al. "Novel class of potent and selective inhibitors efface MTH1 as broad-spectrum cancer target." AACR National Meeting Abstract 5226, 2017.

FIG. 2TTTT-2ZZZZ provide non-limiting examples of MDM2 and/or MDM4 Targeting Ligands wherein R represents exemplary points at which the Linker can be attached. For additional examples and related ligands, see, Popowicz G. M. et al. "Structures of low molecular weight inhibitors bound to MDMX and MDM2 reveal new approaches for p53-MDMX/MDM2 antagonist drug discovery." *Cell Cycle*, 9 (2010); Miyazaki M. et al. "Synthesis and evaluation of novel orally active p53-MDM2 interaction inhibitors." *Bioorg. Med Chem.* 21: 4319-4331 (2013); Miyazaki M. et al. "Discovery of DS-5272 as a promising candidate: A potent and orally active p53-MDM2 interaction inhibitor." *Bioorg Med Chem.* 23: 2360-7 (2015); Holzer P. et al. "Discovery of a Dihydroisoquinolinone Derivative (NVP-CGM097): A Highly Potent and Selective MDM2 Inhibitor Undergoing Phase 1 Clinical Trials in p53 wt Tumors." *J. Med Chem.* 58: 6348-6358 (2015); Gonzalez-Lopez de Turiso F. et al. "Rational Design and Binding Mode Duality of MDM2-p53 Inhibitors." *J. Med. Chem.* 56: 4053-4070 (2013); Gessier F. et al. "Discovery of dihydroisoquinolinone derivatives as novel inhibitors of the p53-MDM2 interaction with a distinct binding mode." *Bioorg. Med Chem. Lett.* 25: 3621-3625 (2015); Fry D. C. et al. "Deconstruction of a nutlin: dissecting the binding determinants of a potent protein-protein interaction inhibitor." *ACS Med Chem Lett* 4: 660-665 (2013); Ding Q. et al. "Discovery of RG7388 a Potent and Selective p53-MDM2 Inhibitor in Clinical Development." *J. Med Chem.* 56: 5979-5983 (2013); Wang S. et al. "SAR405838: an optimized inhibitor of MDM2-p53 interaction that induces complete and durable tumor regression." *Cancer Res.* 74: 5855-5865 (2014); Rew Y. et al. "Discovery of AM-7209 a Potent and Selective 4-Amidobenzoic Acid Inhibitor of the MDM2-p53 Interaction." *J. Med Chem.* 57: 10499-10511 (2014); Bogen S. L. et al. "Discovery of Novel 3 3-Disubstituted Piperidines as Orally Bioavailable Potent and Efficacious HDM2-p53 Inhibitors." *ACS Med Chem. Lett.* 7: 324-329 (2016); and, Sun D. et al. "Discovery of AMG 232 a Potent Selective and Orally Bioavailable MDM2-p53 Inhibitor in Clinical Development." *J. Med Chem.* 57: 1454-1472 (2014).

FIG. 2AAAAA-2EEEEE provide non-limiting examples of PARP1, PARP2, and/or PARP3 Targeting Ligands wherein R represents exemplary points at which the Linker can be attached. For additional examples and related ligands, see, Iwashita A. et al. "Discovery of quinazolinone and quinoxaline derivatives as potent and selective poly(ADP-ribose) polymerase-1/2 inhibitors." *Febs Lett.* 579: 1389-1393 (2005); the crystal structure PDB 2RCW (PARP complexed with A861695, Park C. H.); the crystal structure PDB 2RD6 (PARP complexed with A861696, Park C. H.); the crystal structure PDB 3GN7; Miyashiro J. et al. "Synthesis and SAR of novel tricyclic quinoxalinone inhibitors of poly(ADP-ribose)polymerase-1 (PARP-1)" *Bioorg. Med Chem. Lett.* 19: 4050-4054 (2009); Gandhi V. B. et al. "Discovery and SAR of substituted 3-oxoisoindoline-4-carboxamides as potent inhibitors of poly(ADP-ribose) polymerase (PARP) for the treatment of cancer." *Bioorg. Med Chem. Lett.* 20: 1023-1026 (2010); Penning T. D. et al. "Optimization of phenyl-substituted benzimidazole carboxamide poly(ADP-ribose) polymerase inhibitors: identification of (S)-2-(2-fluoro-4-(pyrrolidin-2-yl)phenyl)-1H-benzimidazole-4-carboxamide (A-966492) a highly potent and efficacious inhibitor." *J. Med Chem.* 53: 3142-3153 (2010); Ye N. et al. "Design, Synthesis, and Biological Evaluation of a Series of Benzo[de][1 7]naphthyridin-7(8H)-ones Bearing a Functionalized Longer Chain Appendage as Novel PARP1 Inhibitors." *J. Med Chem.* 56: 2885-2903 (2013); Patel M. R. et al. "Discovery and Structure-Activity Relationship of Novel 2 3-Dihydrobenzofuran-7-carboxamide and 2 3-Dihydrobenzofuran-3(2H)-one-7-carboxamide Derivatives as Poly(ADP-ribose)polymerase-1 Inhibitors." *J. Med Chem.* 57: 5579-5601 (2014); Thorsell A. G. et al. "Structural Basis for Potency and Promiscuity in Poly(ADP-ribose) Polymerase (PARP) and Tankyrase Inhibitors." *J. Med Chem.* 60:1262-1271 (2012); the crystal structure PDB 4RV6 ("Human ARTD1 (PARP1) catalytic domain in complex with inhibitor Rucaparib", Karlberg T. et al.); Papeo G. M. E. et al. "Discovery of 2-[1-(4 4-Difluorocyclohexyl)Piperidin-4-Yl]-6-Fluoro-3-Oxo-2 3-Dihydro-1H-Isoindole-4-Carboxamide (Nms-P118): A Potent Orally Available and Highly Selective Parp-1 Inhibitor for Cancer Therapy." *J. Med Chem.* 58: 6875 (2015); Kinoshita T. et al. "Inhibitor-induced structural change of the active site of human poly (ADP-ribose) polymerase." *Febs Lett.* 556: 43-46 (2004); and, Gangloff A. R. et al. "Discovery of novel benzo[b][1 4]oxazin-3(4H)-ones as poly(ADP-ribose)polymerase inhibitors." *Bioorg. Med Chem. Lett.* 23: 4501-4505 (2013).

FIG. 2FFFFF-2GGGGG provide non-limiting examples of PARP14 Targeting Ligands wherein R represents exemplary points at which the Linker can be attached.

FIG. 2HHHHH provides non-limiting examples of PARP15 Targeting Ligands wherein R represents exemplary points at which the Linker can be attached.

FIG. 2IIIII provides non-limiting examples of PDZ domain Targeting Ligands wherein R represents exemplary points at which the spacer(s) are attached.

FIG. 2JJJJJ provides non-limiting examples of Phospholipase A2 domain Targeting Ligands wherein R represents exemplary points at which the Linker can be attached.

FIG. 2KKKKK provides non-limiting examples of Protein S100-A7 2WOS Targeting Ligands wherein R represents exemplary points at which the Linker can be attached.

FIG. 2LLLLL-2MMMMM provide non-limiting examples of Saposin-B Targeting Ligands wherein R represents exemplary points at which the Linker can be attached.

FIG. 2NNNNN-2OOOOO provide non-limiting examples of Sec7 Targeting Ligands wherein R represents exemplary points at which the Linker can be attached.

FIG. 2PPPPP-2QQQQQ provide non-limiting examples of SH2 domain of pp60 Src Targeting Ligands wherein R represents exemplary points at which the Linker can be attached.

FIG. 2RRRRR provides non-limiting examples of Tank1 Targeting Ligands wherein R represents exemplary points at which the Linker can be attached.

FIG. 2SSSSS provides non-limiting examples of Ubc9 SUMO E2 ligase SF6D Targeting Ligands wherein R represents exemplary points at which the Linker can be attached.

FIG. 2TTTTT provides non-limiting examples of Src Targenting Ligands, including AP23464, wherein R represents exemplary points at which the Linker can be attached.

FIG. 2UUUUU-2XXXXX provide non-limiting examples of Src-AS1 and/or Src AS2 Targeting Ligands wherein R represents exemplary points at which the Linker can be attached.

FIG. 2YYYYY provides non-limiting examples of JAK3 Targeting Ligands, including Tofacitinib, wherein R represents exemplary points at which the Linker can be attached.

FIG. 2ZZZZZ provides non-limiting examples of ABL Targeting Ligands, including Tofacitinib and Ponatinib, wherein R represents exemplary points at which the Linker can be attached.

Figure 3A:
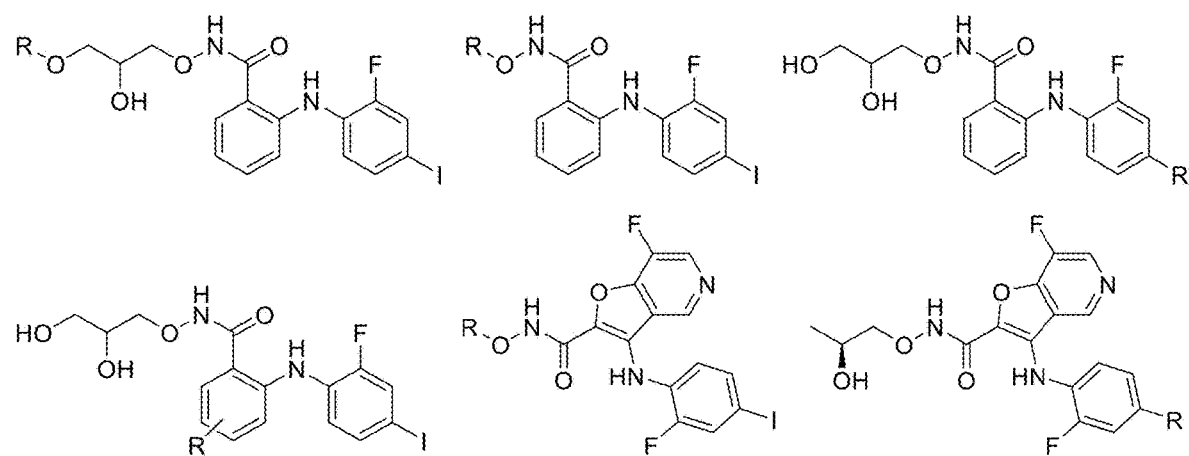
Figure 3B:
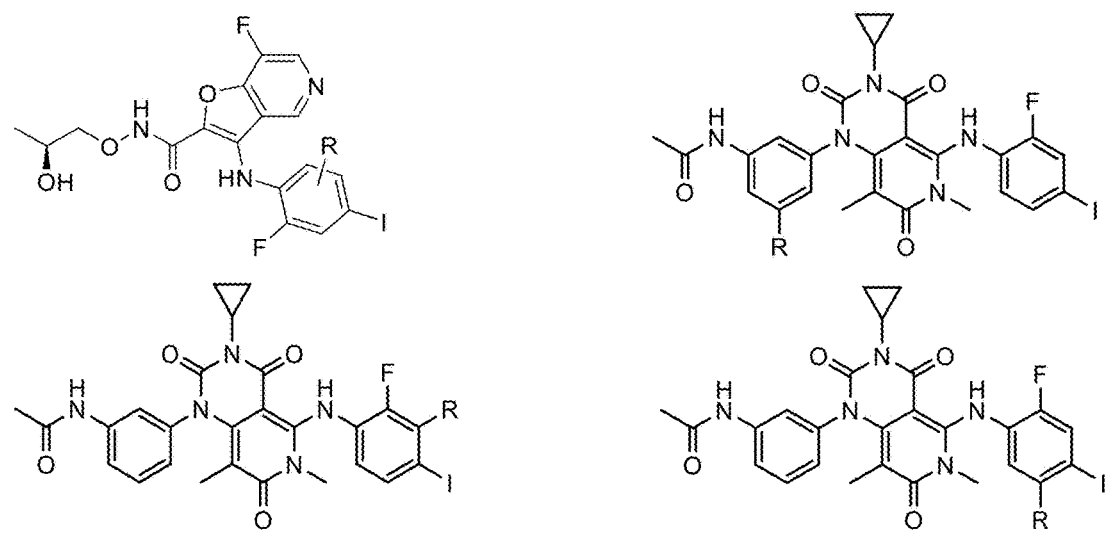

FIG. 3A-3B provide non-limiting examples of MEK1 Targeting Ligands, including PD318088, Trametinib and G-573, wherein R represents exemplary points at which the Linker can be attached.

FIG. 3C provides non-limiting examples of KIT Targeting Ligands, including Regorafenib, wherein R represents exemplary points at which the Linker can be attached.

Figure 3F:
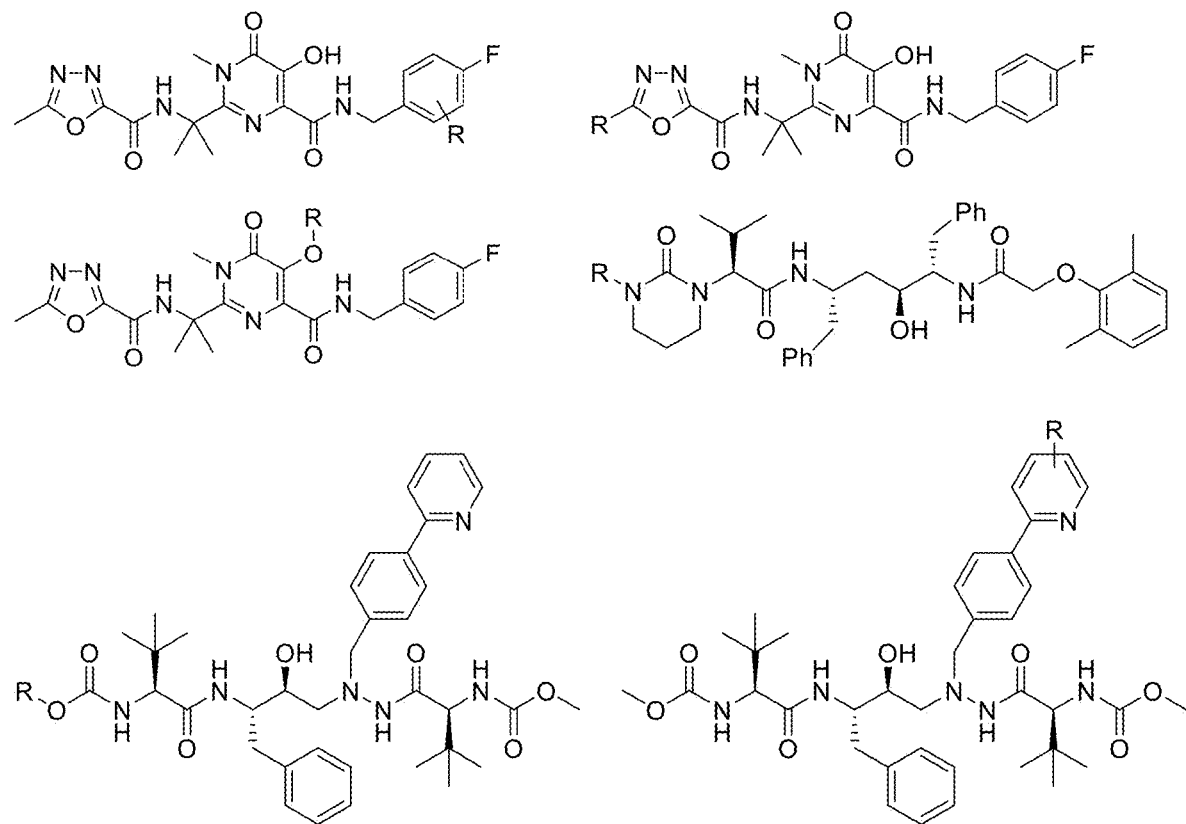
Figure 3G:
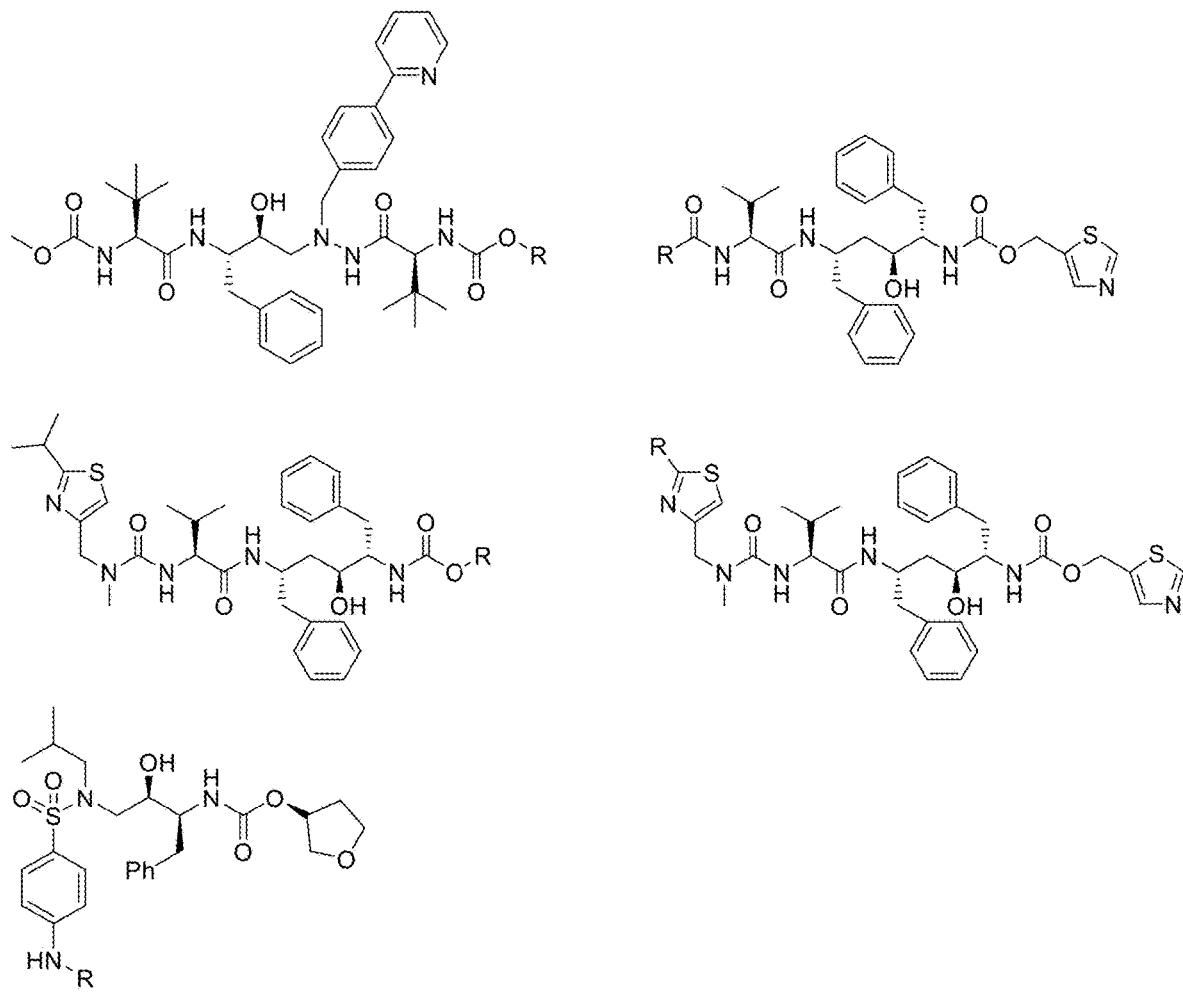
Figure 3H:
Figure 3K:
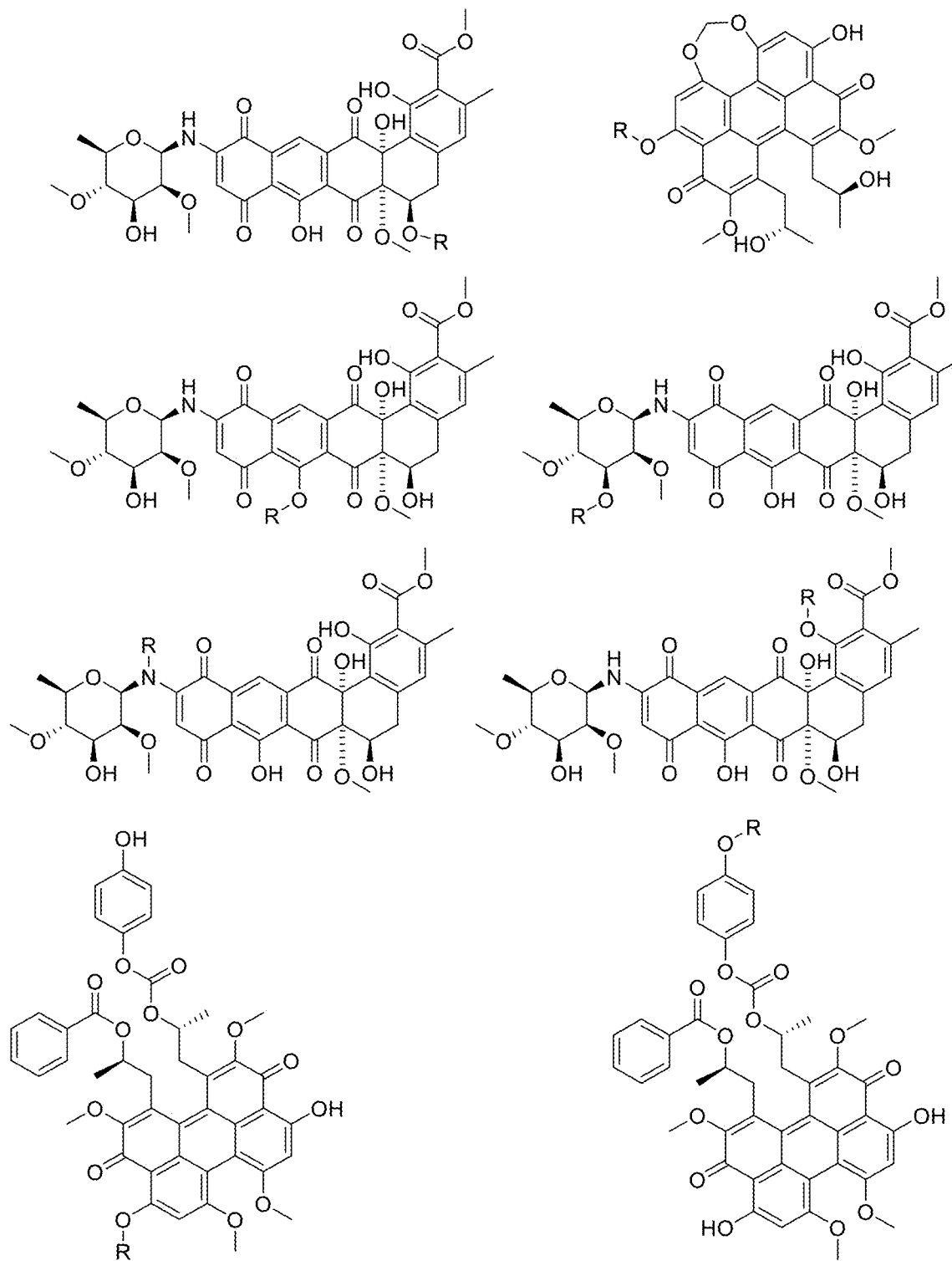
Figure 3L:
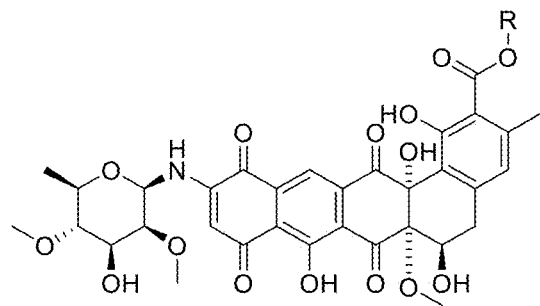
Figure 3M:
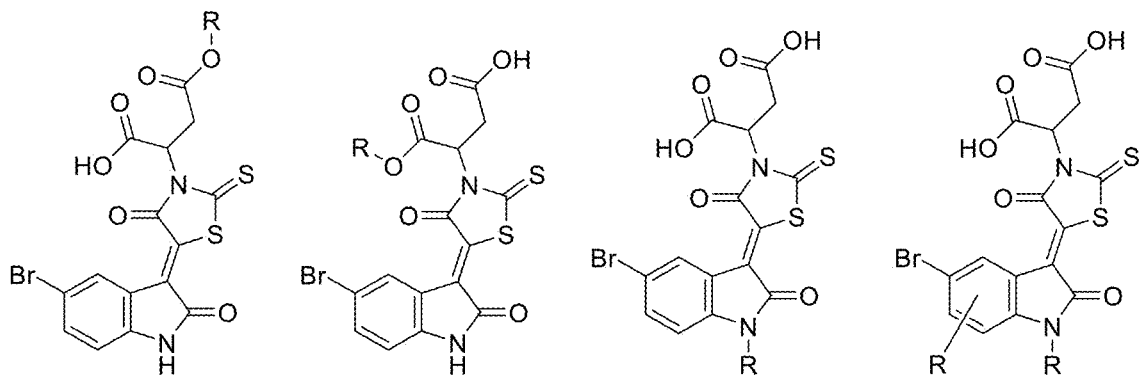
Figure 3N:
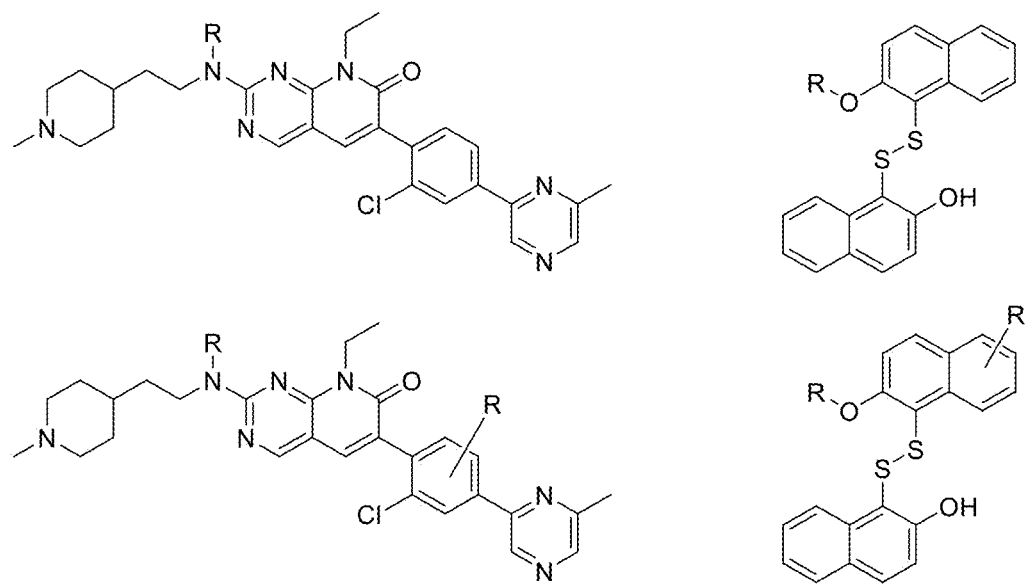
Figure 3O:
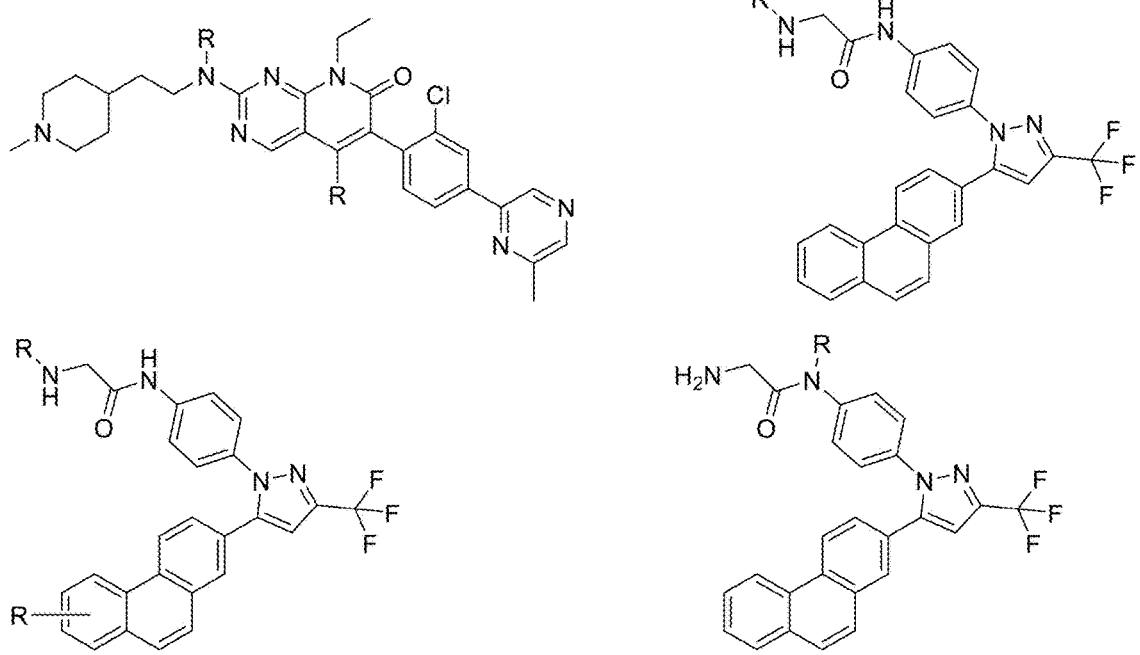
Figure 3P:
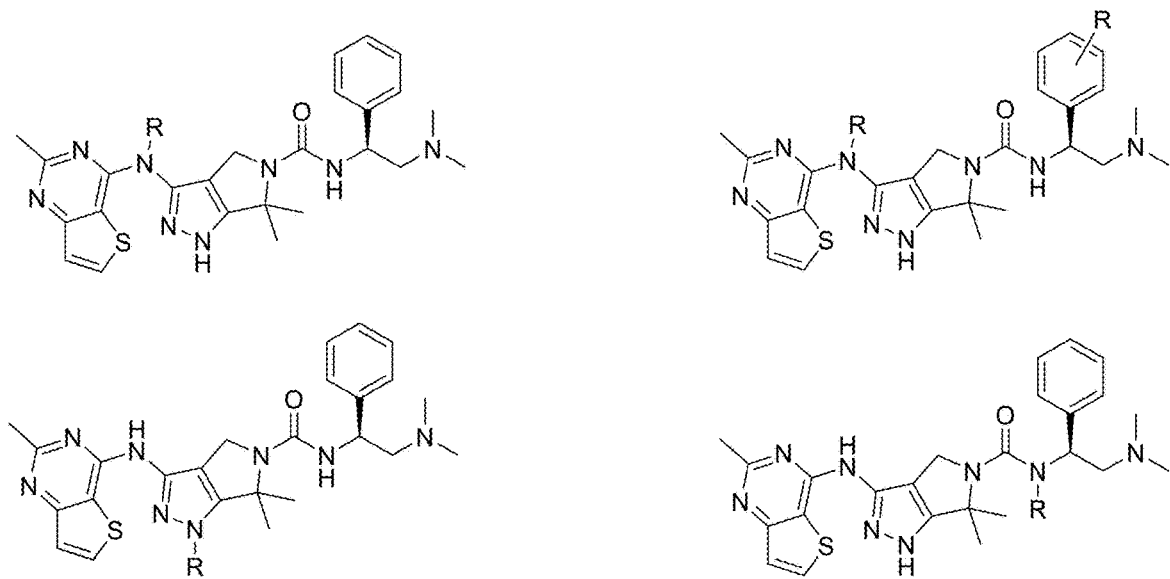
Figure 3Q:
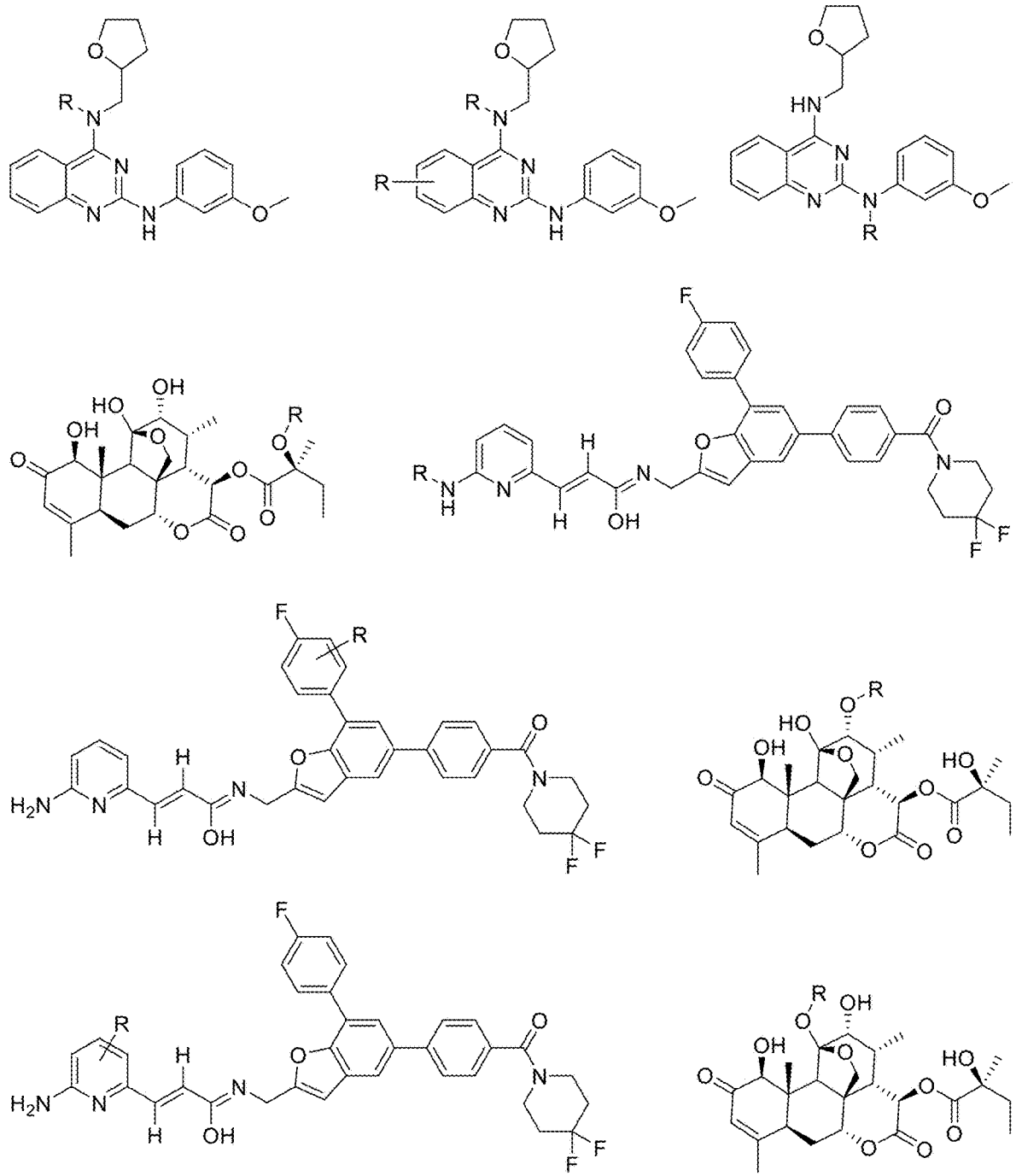
Figure 3R:
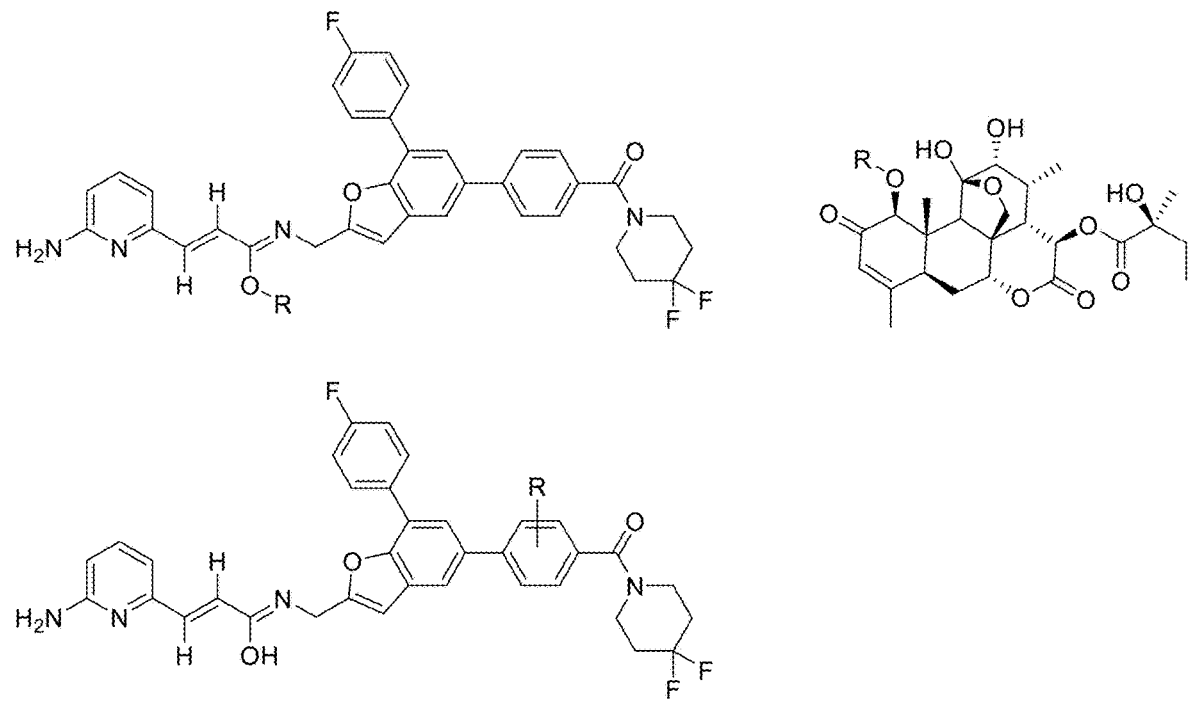
Figure 3S:
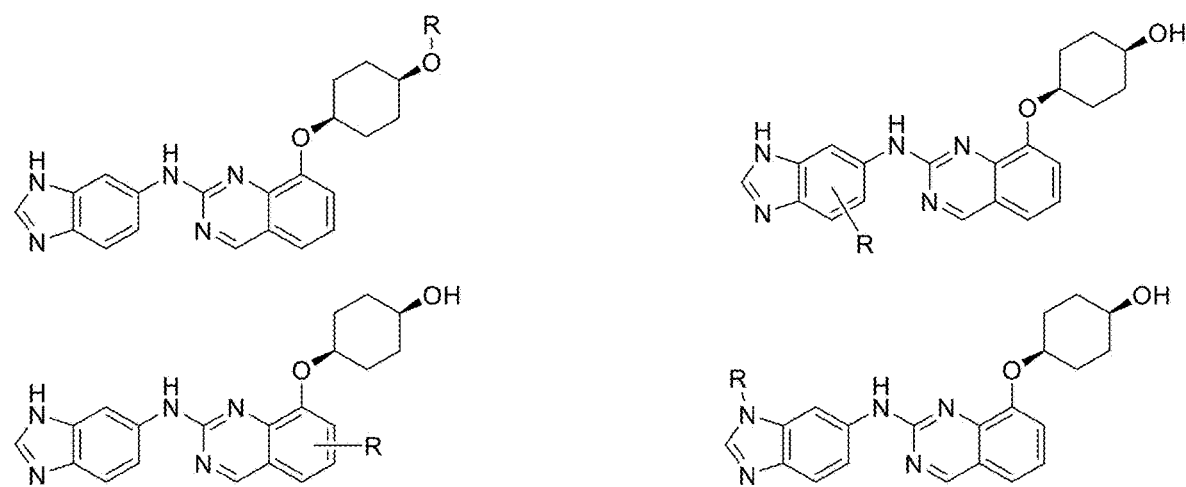
Figure 3T:
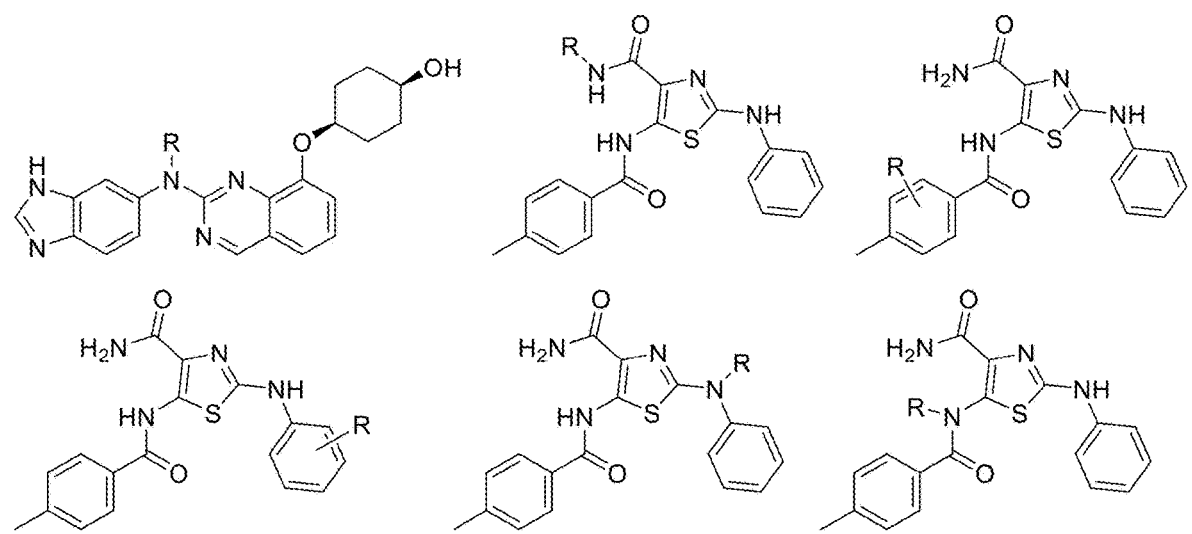
Figure 3U:
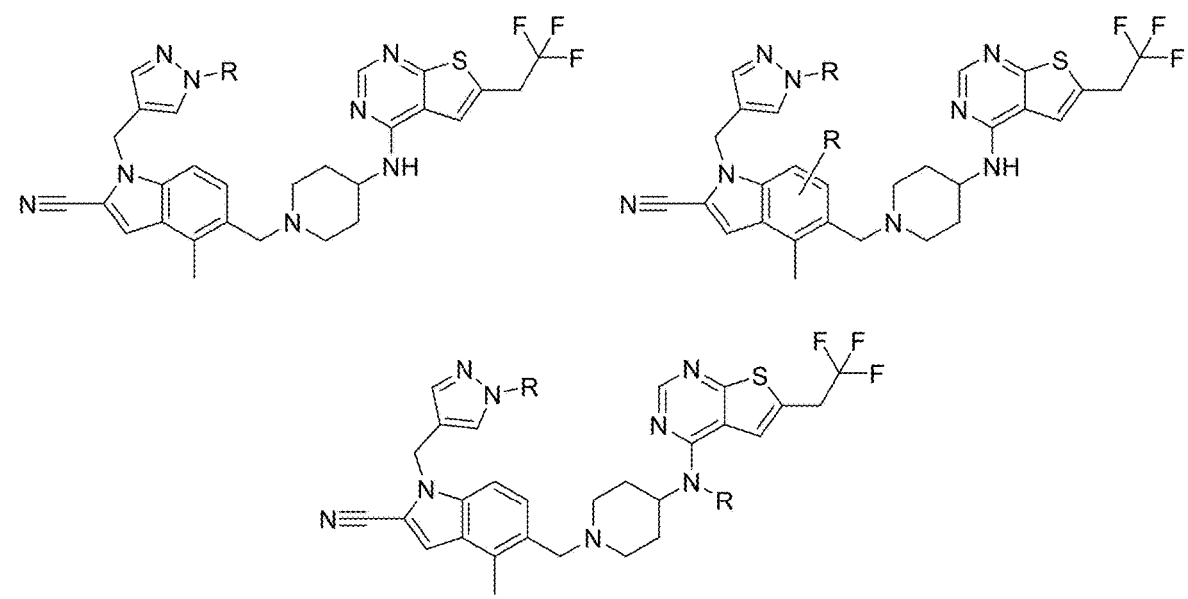
Figure 3V:
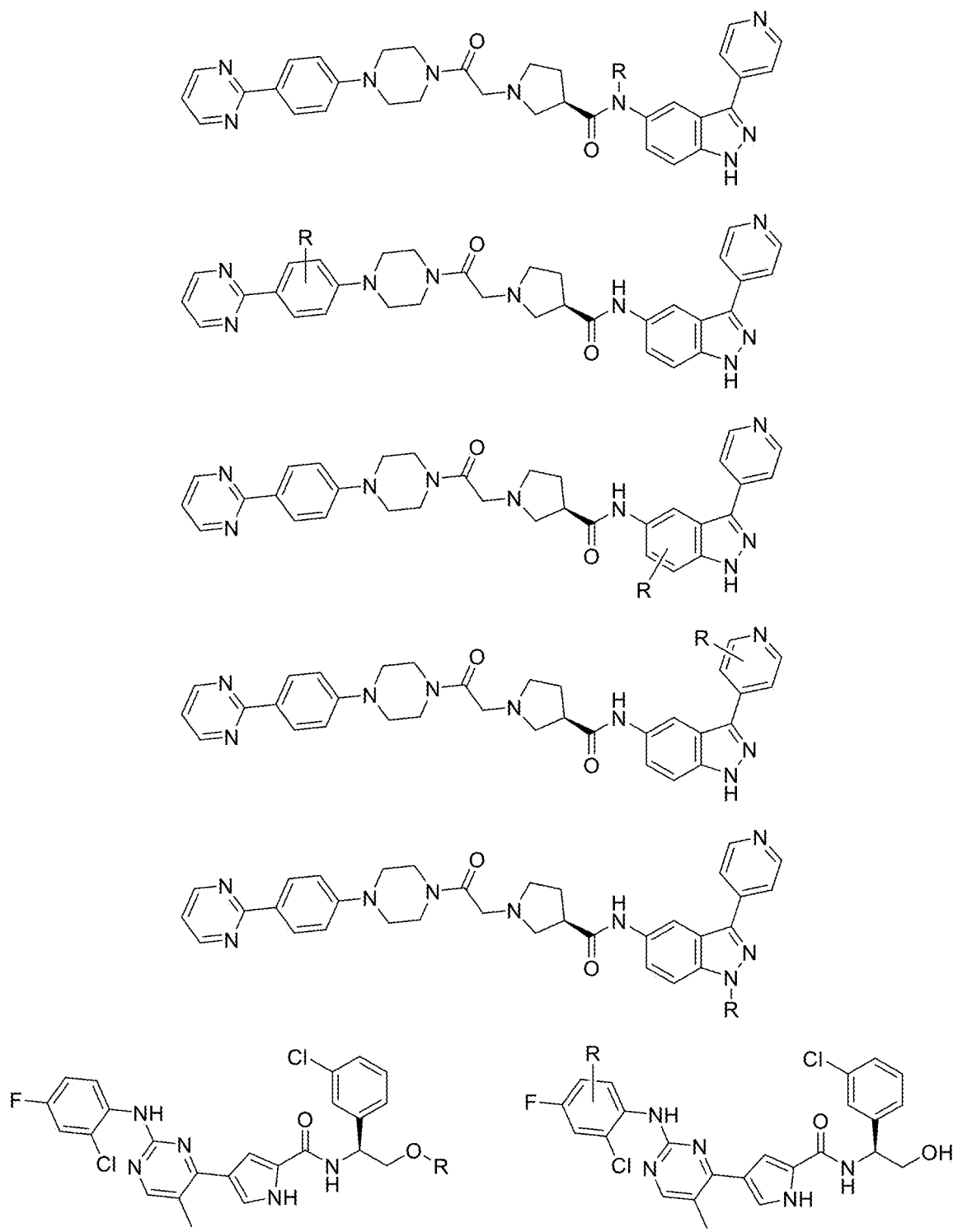
Figure 3W:
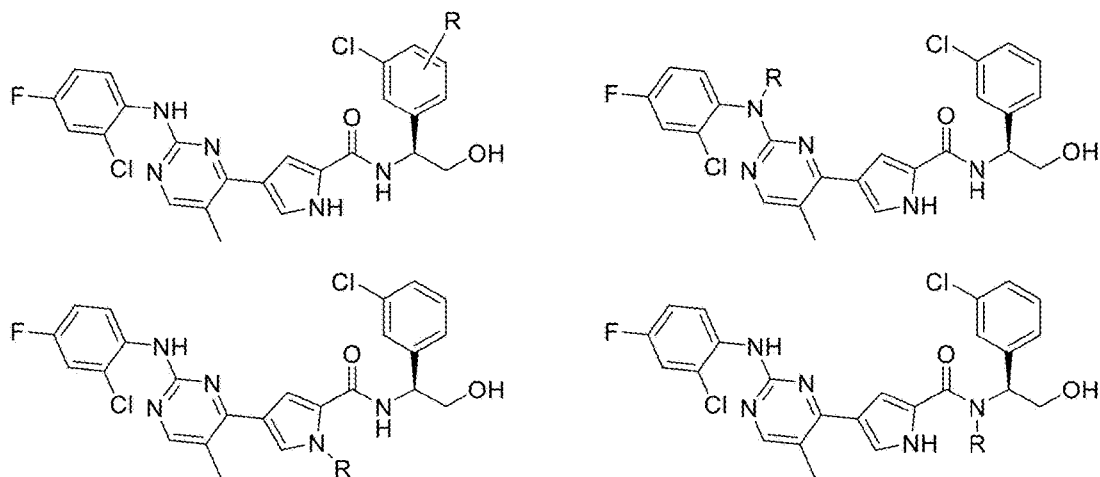
Figure 3X:
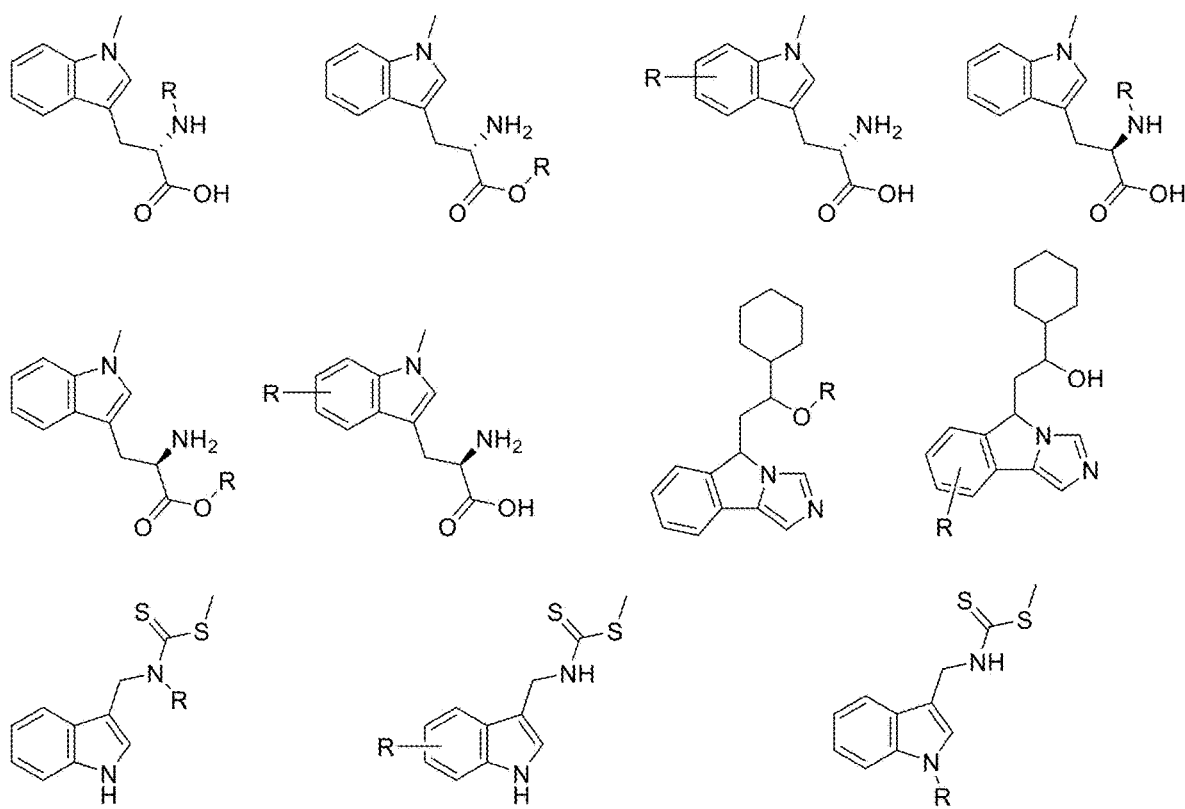
Figure 3Y:
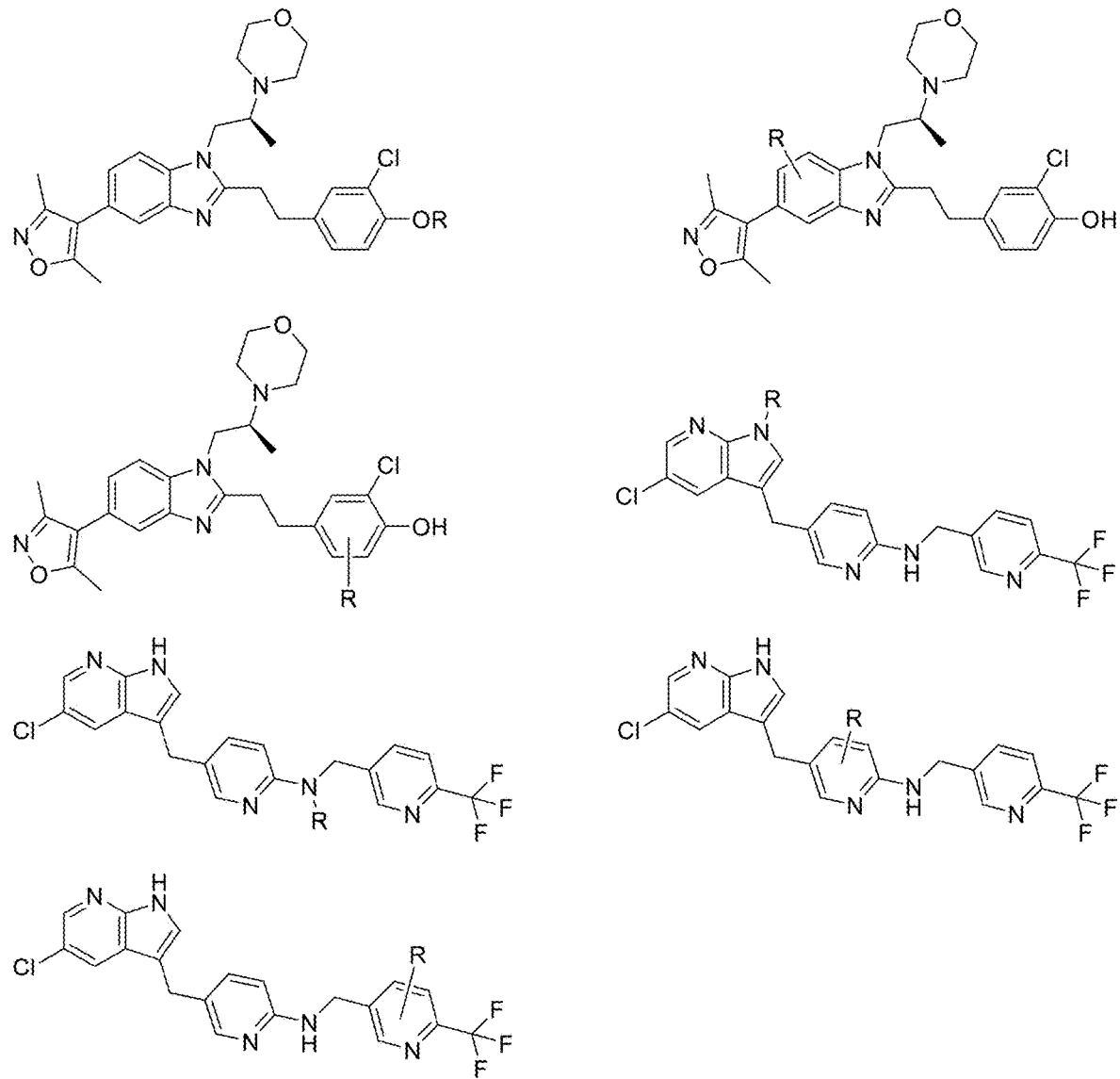
Figure 3Z:
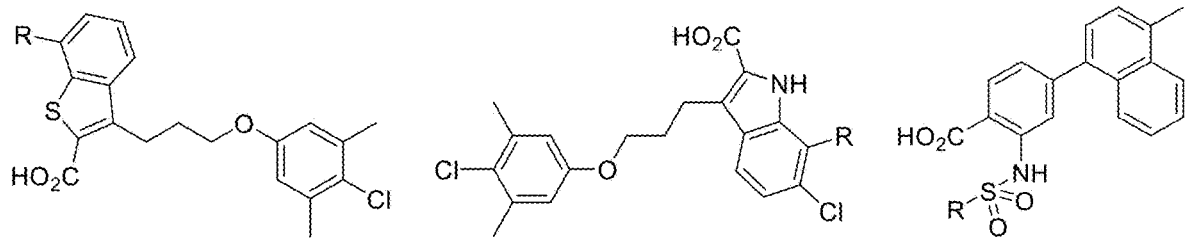
Figure 3A:
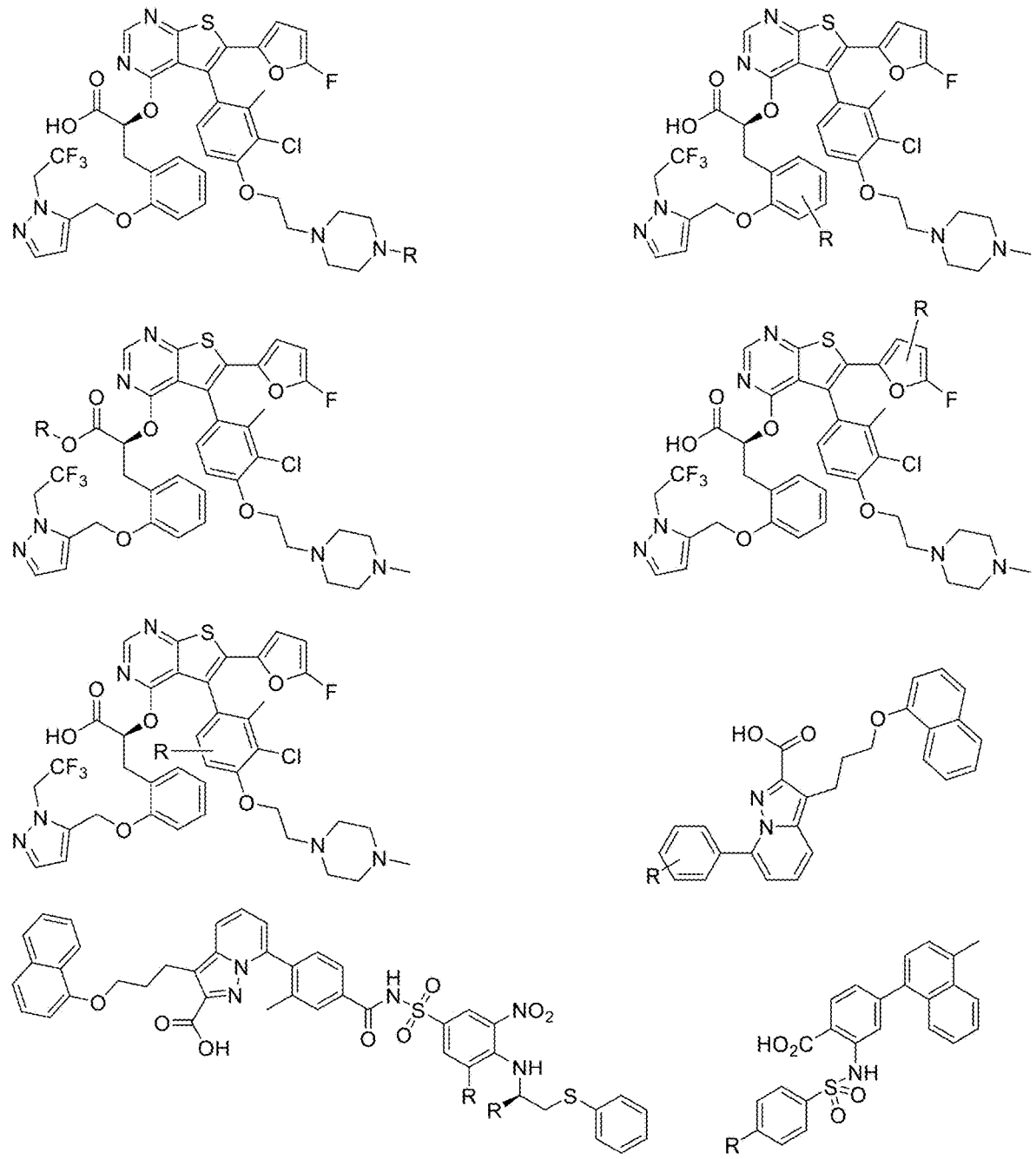
Figure 3B:
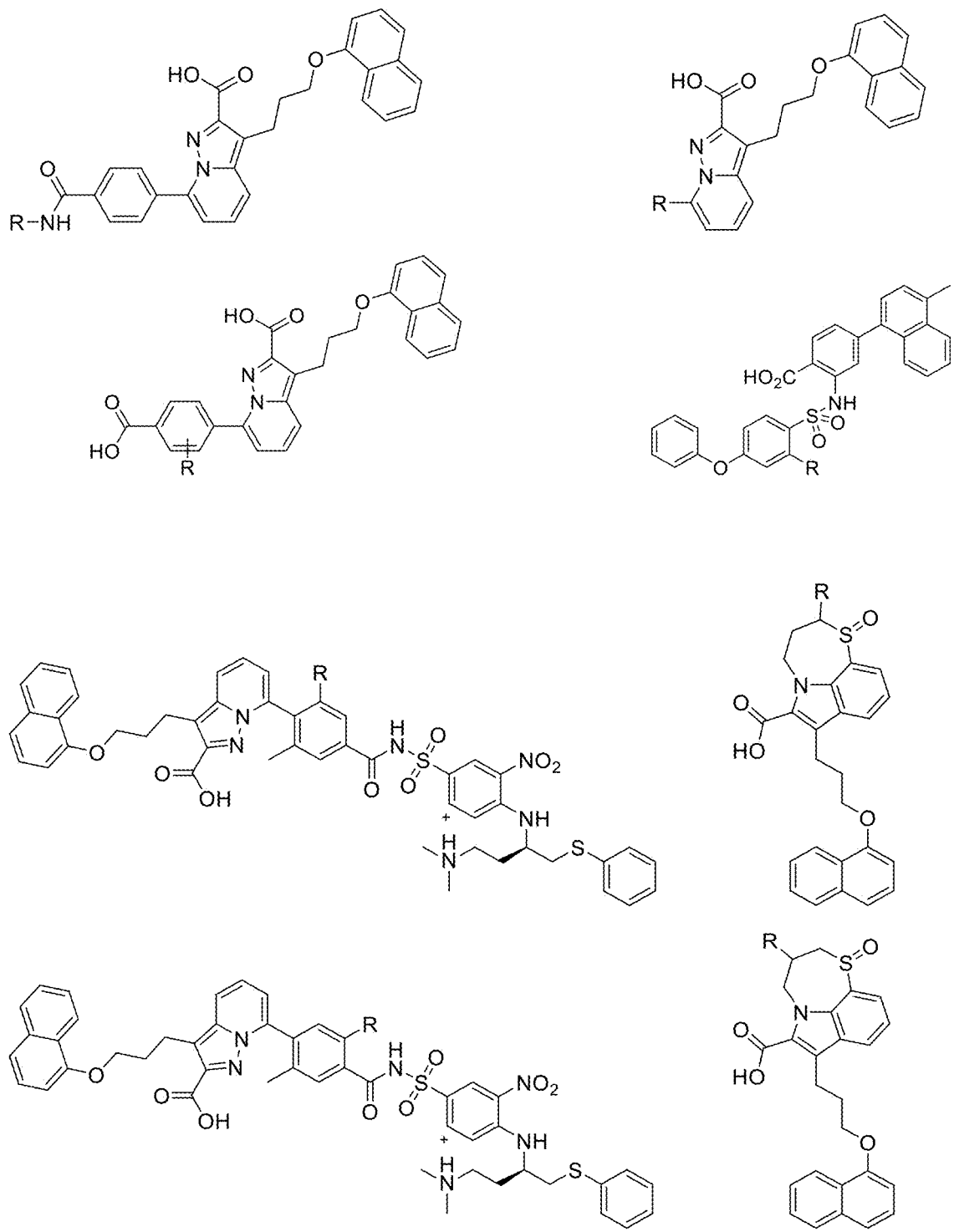
Figure 3D:
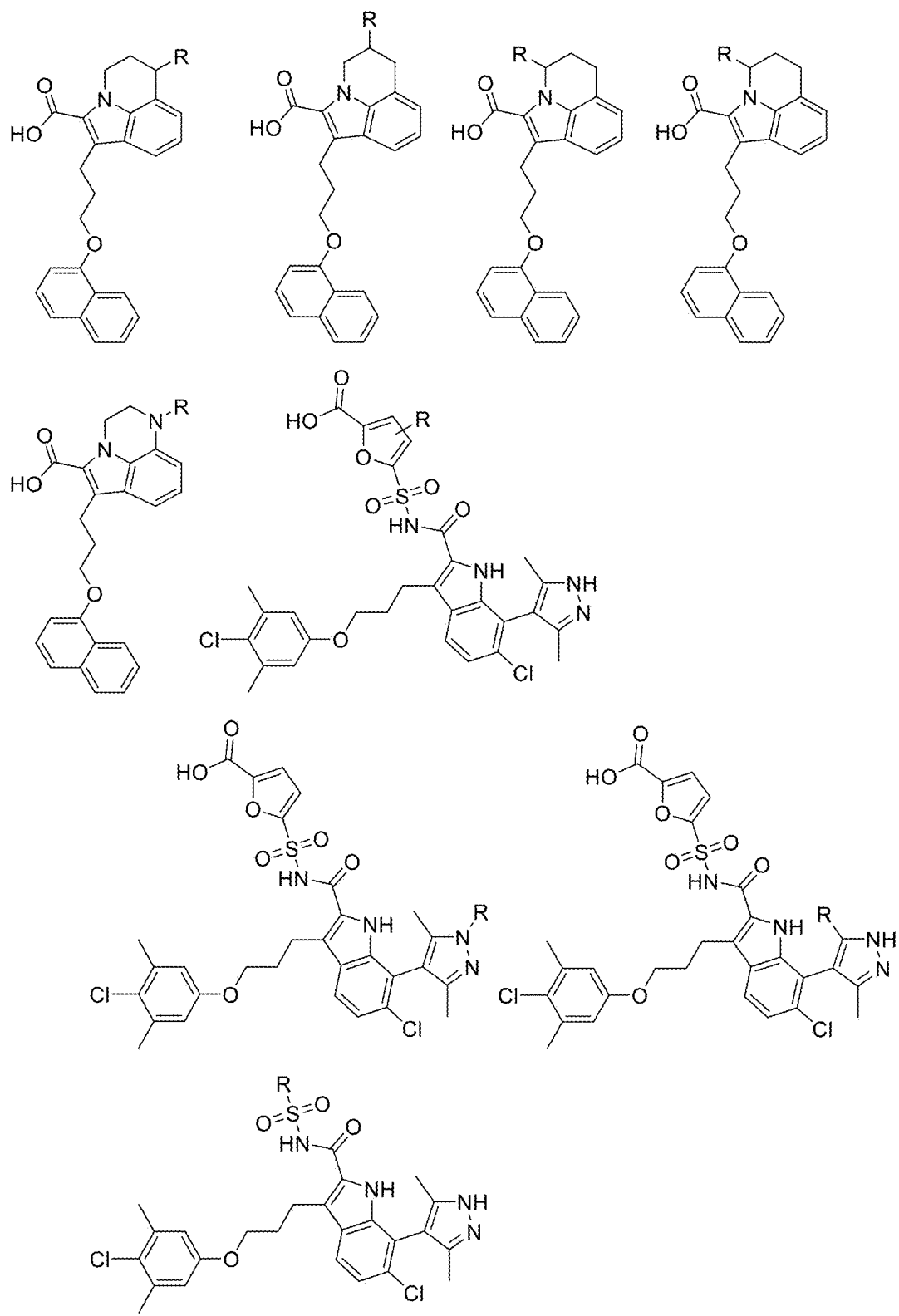
Figure 3E:
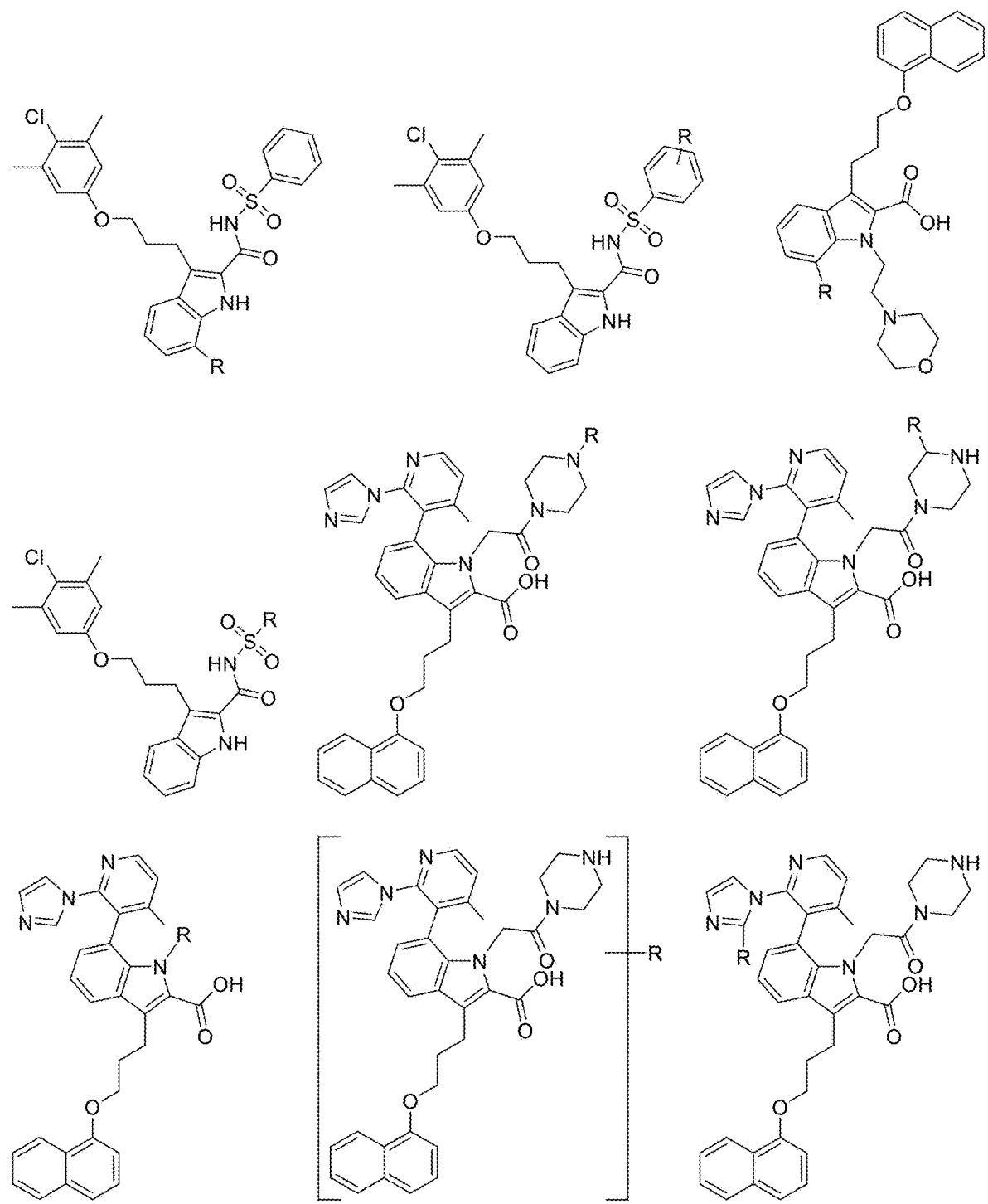
Figure 3H:
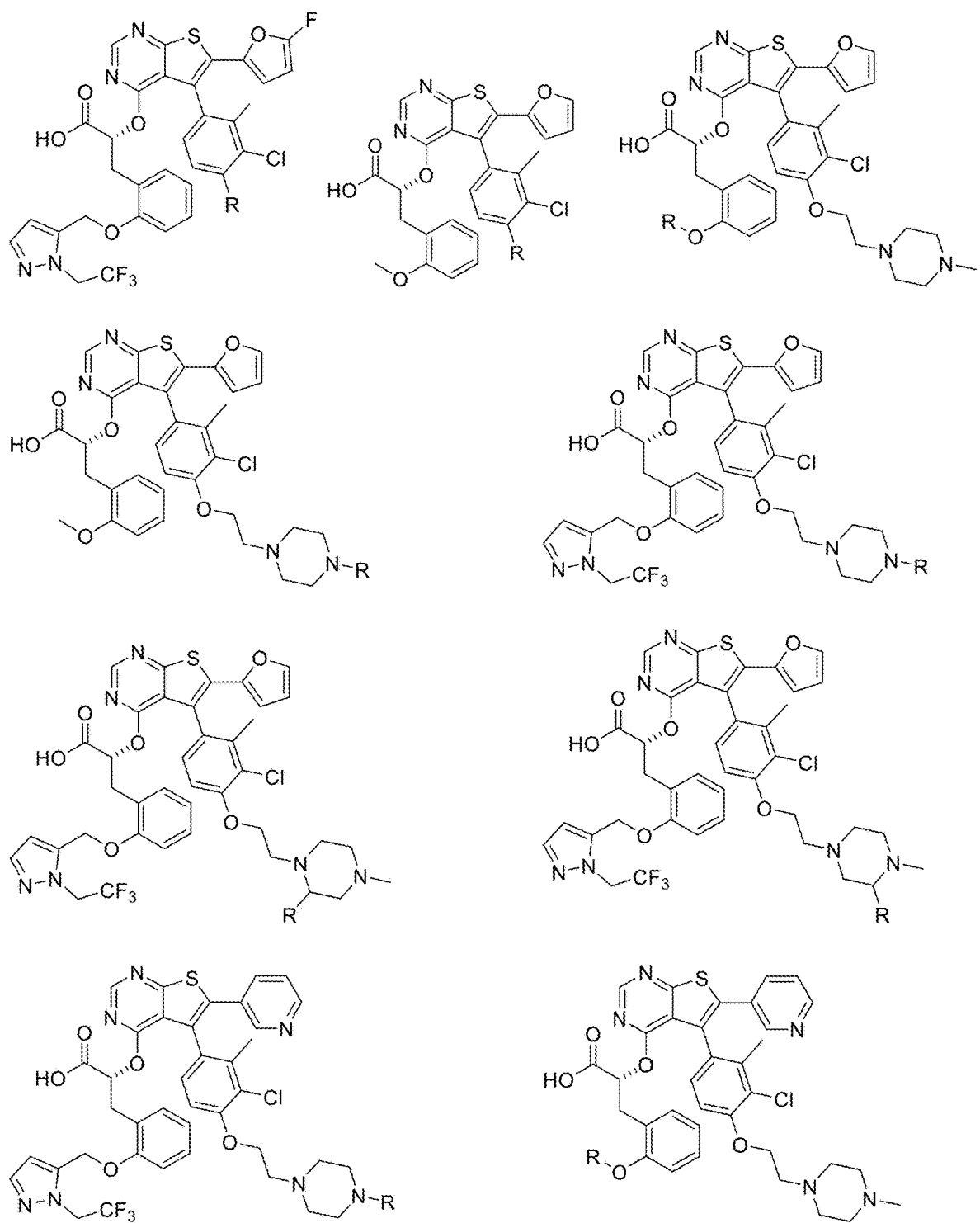
Figure 3L:
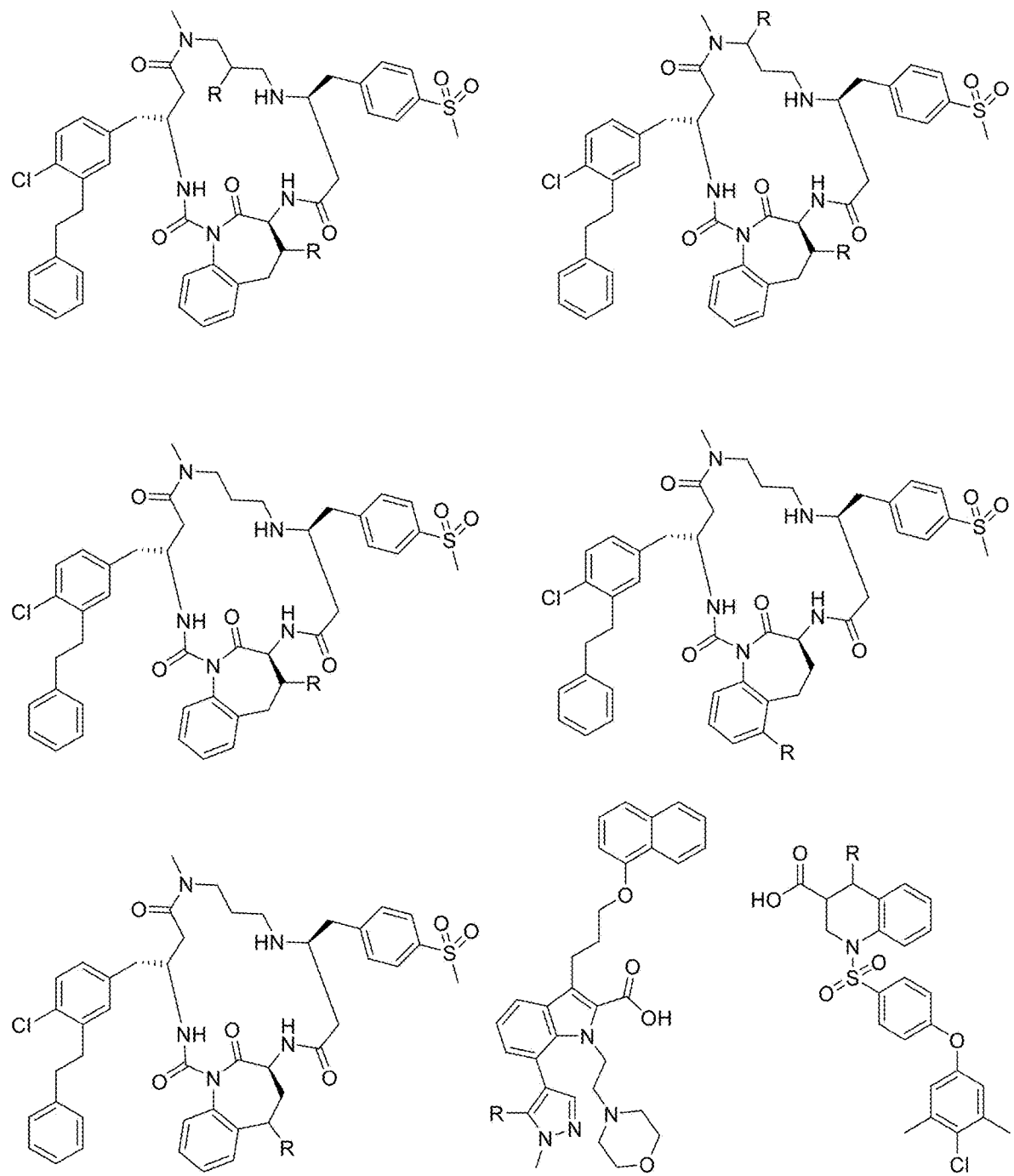
Figure 3M:
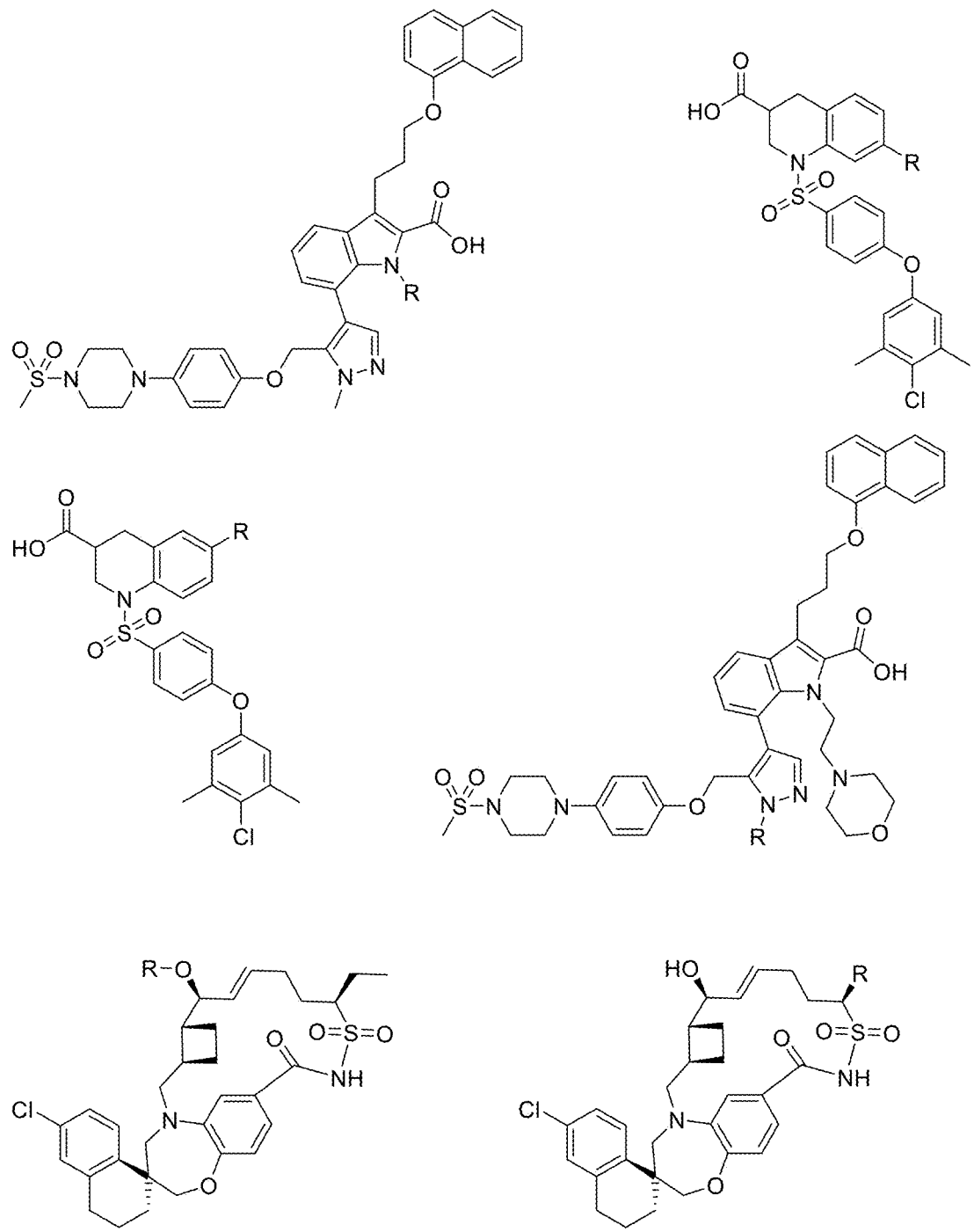
Figure 3O:
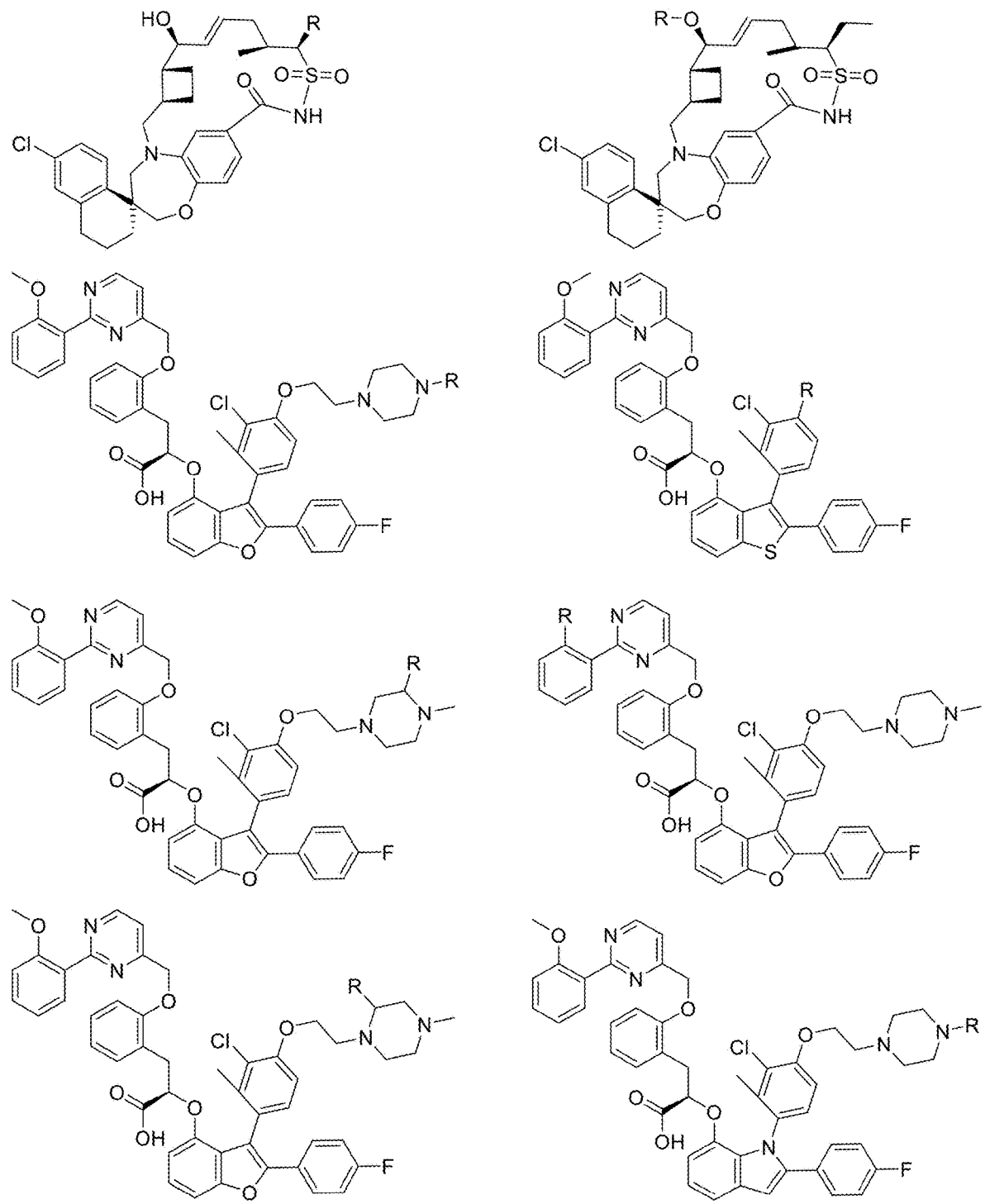
Figure 3P:
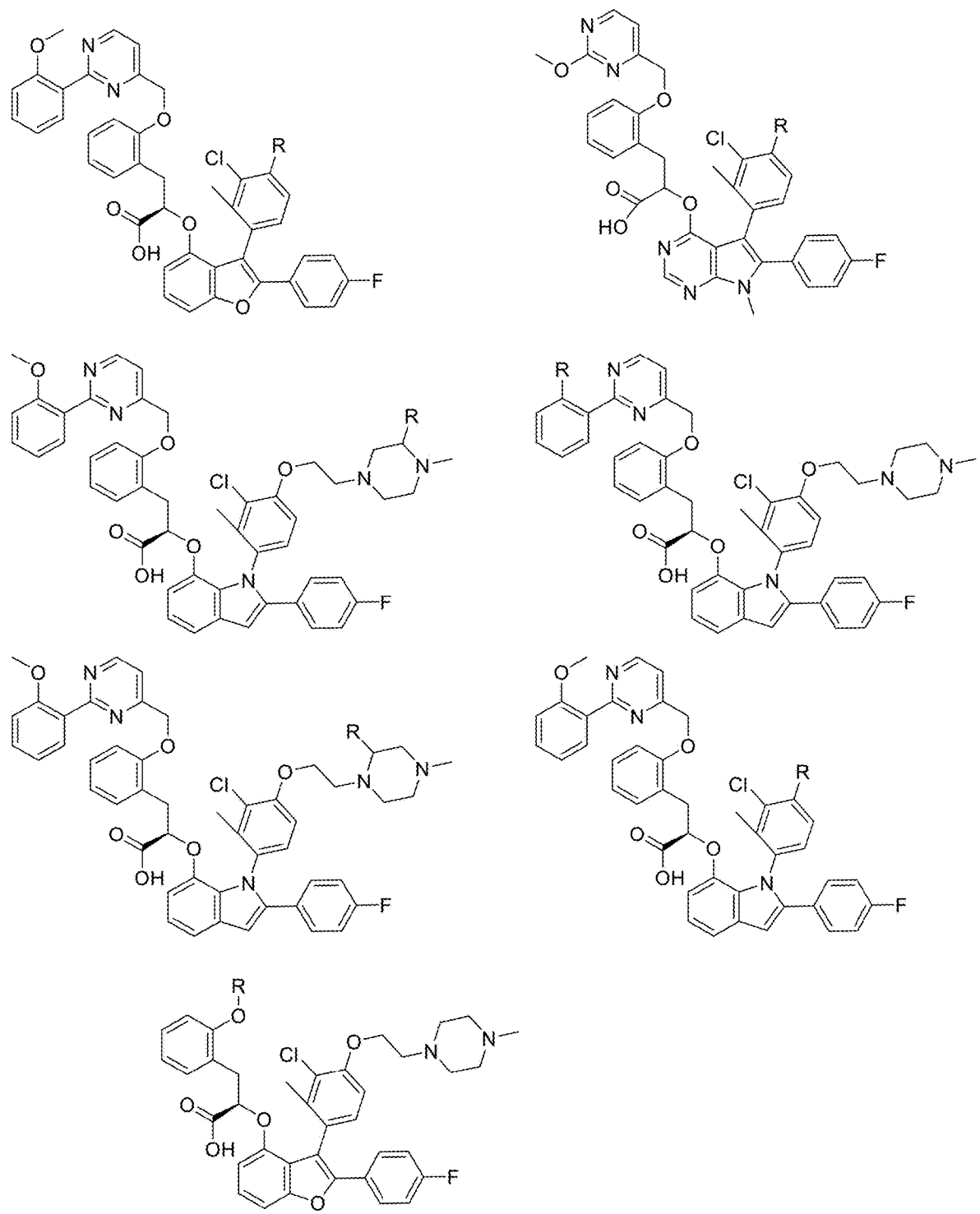
Figure 3Q:
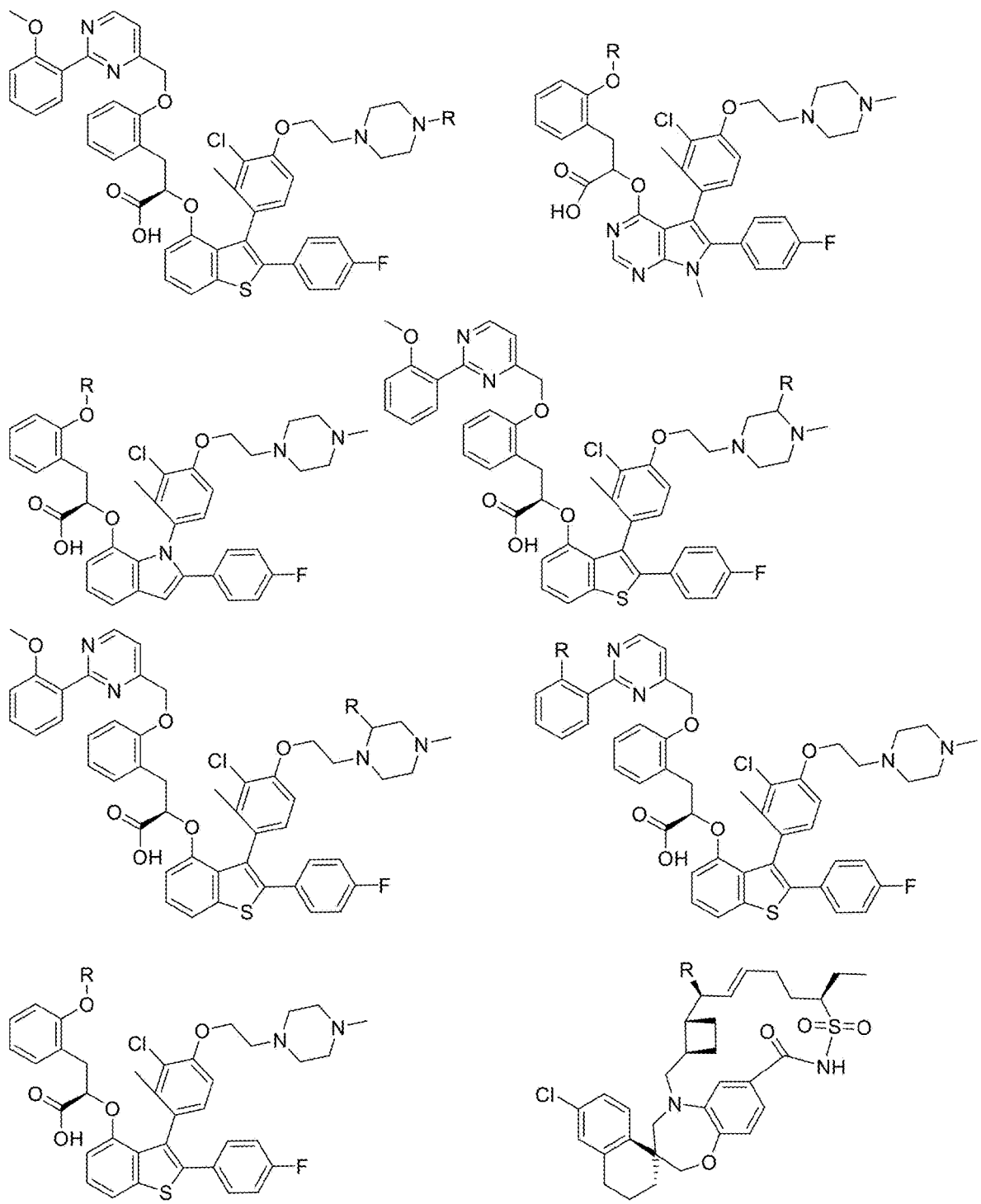
Figure 3R:
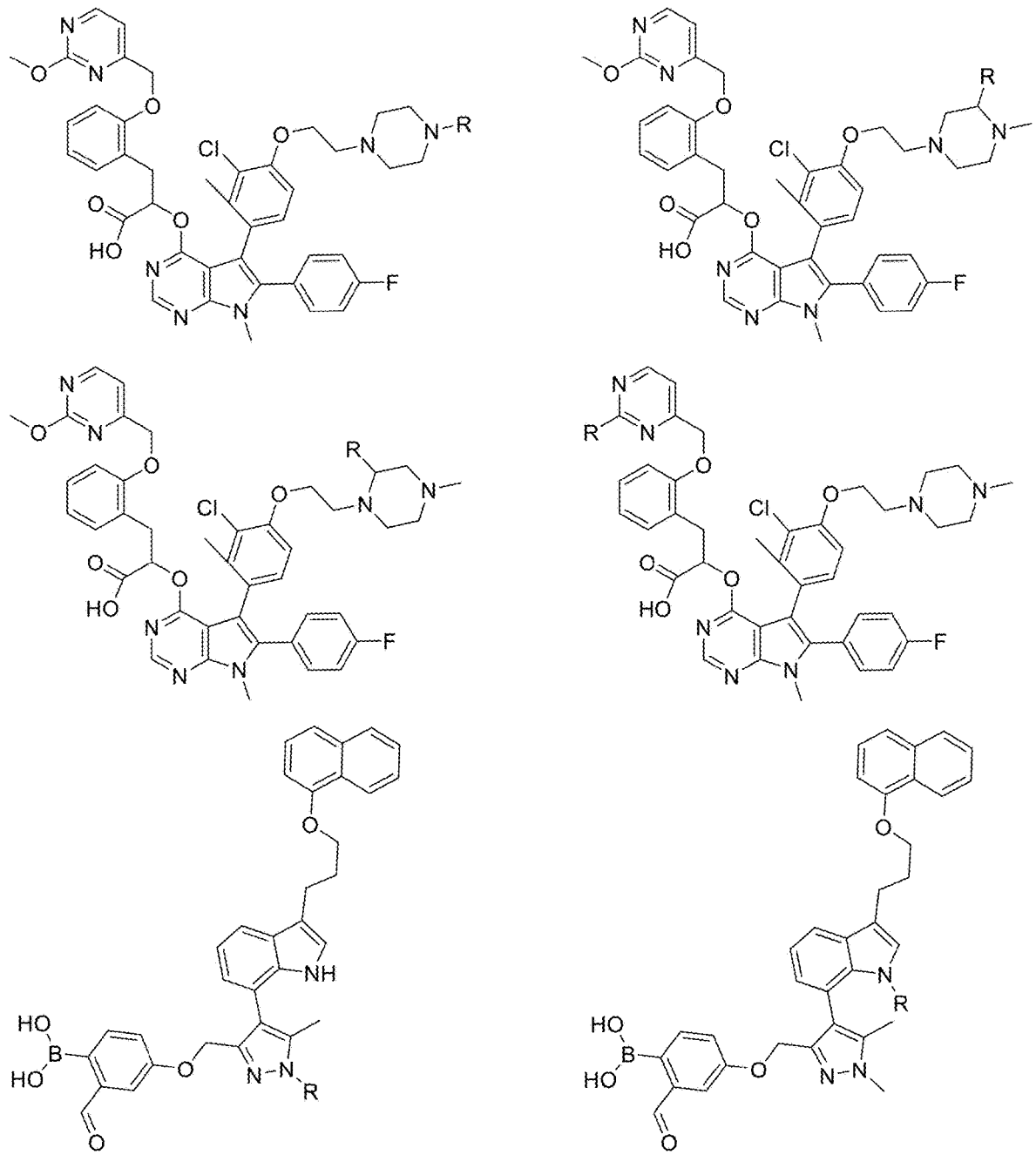
Figure 3S:
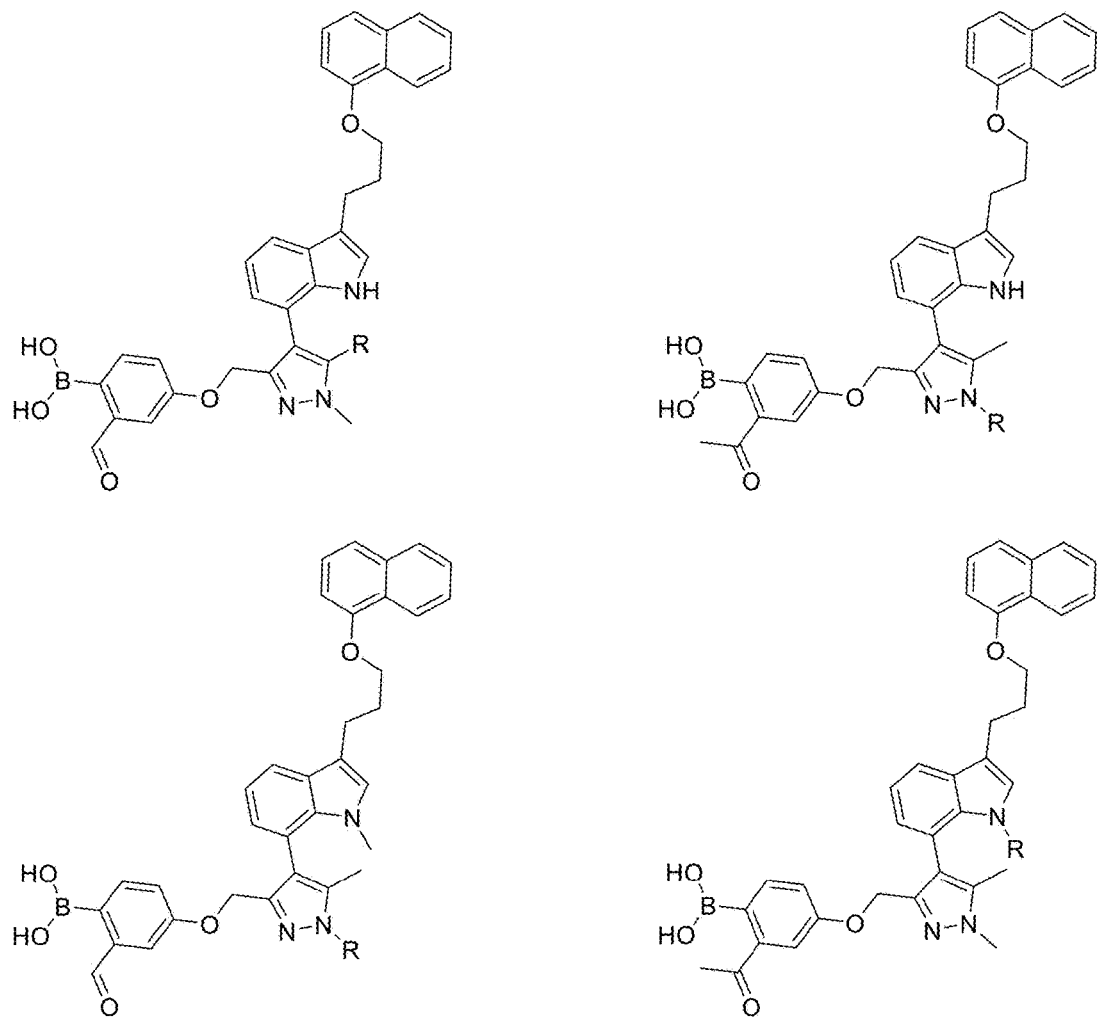
Figure 3T:
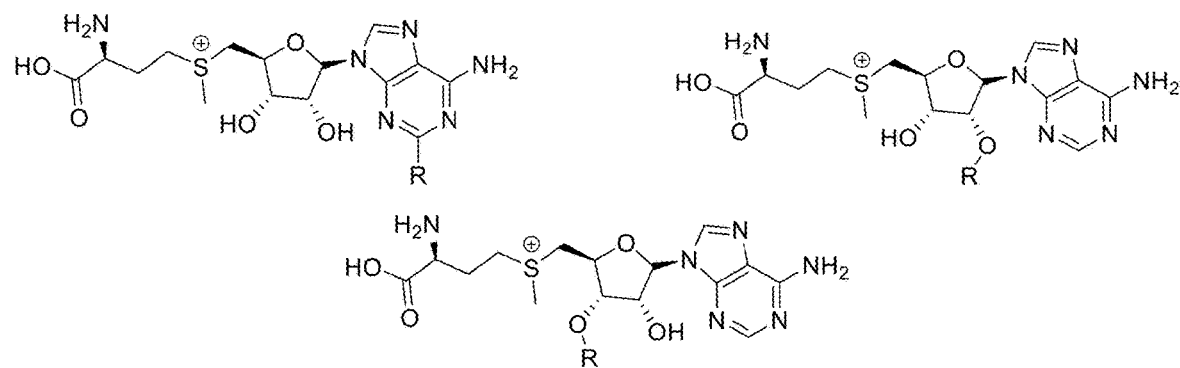
Figure 3U:
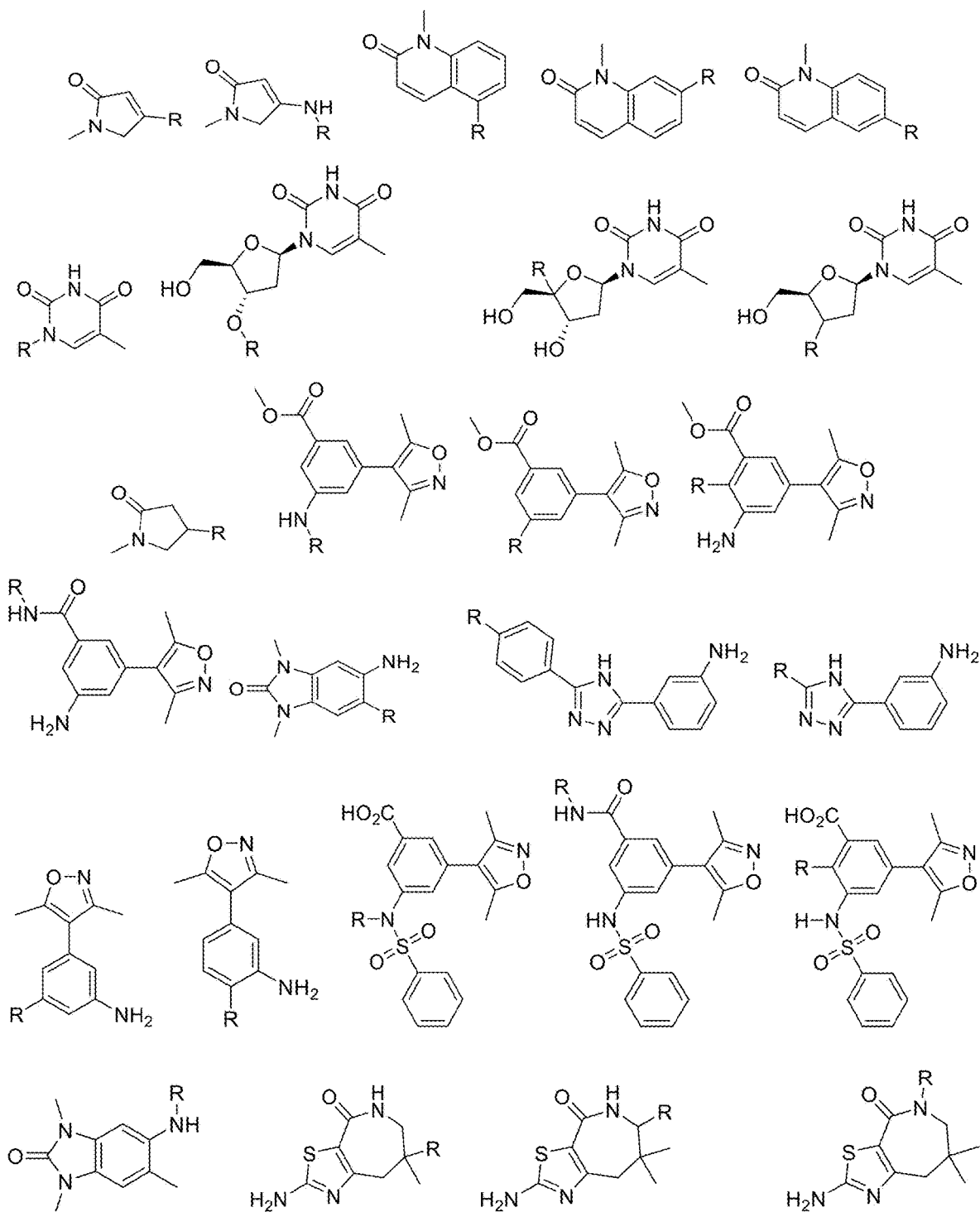
Figure 3V:
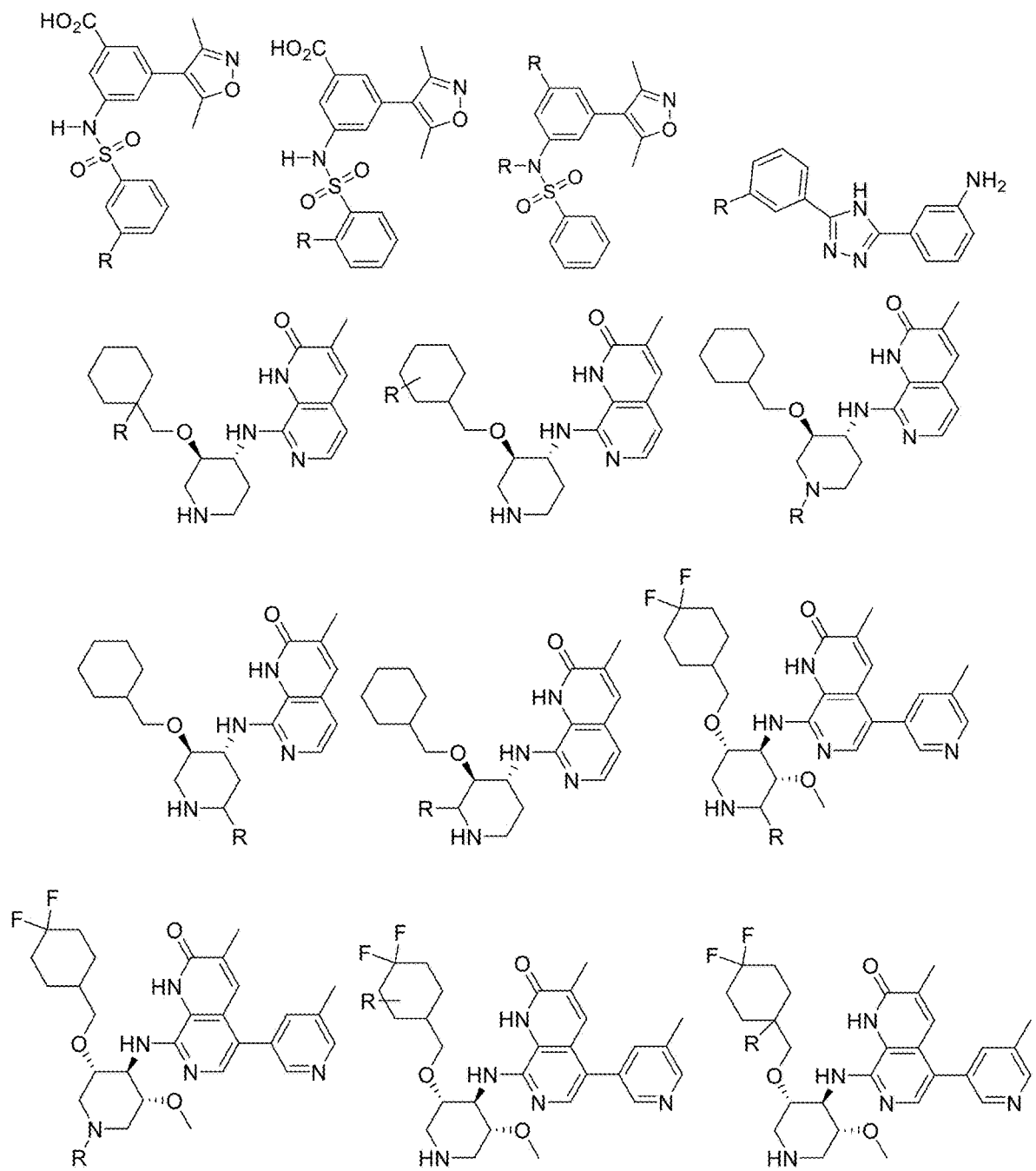
Figure 3W:
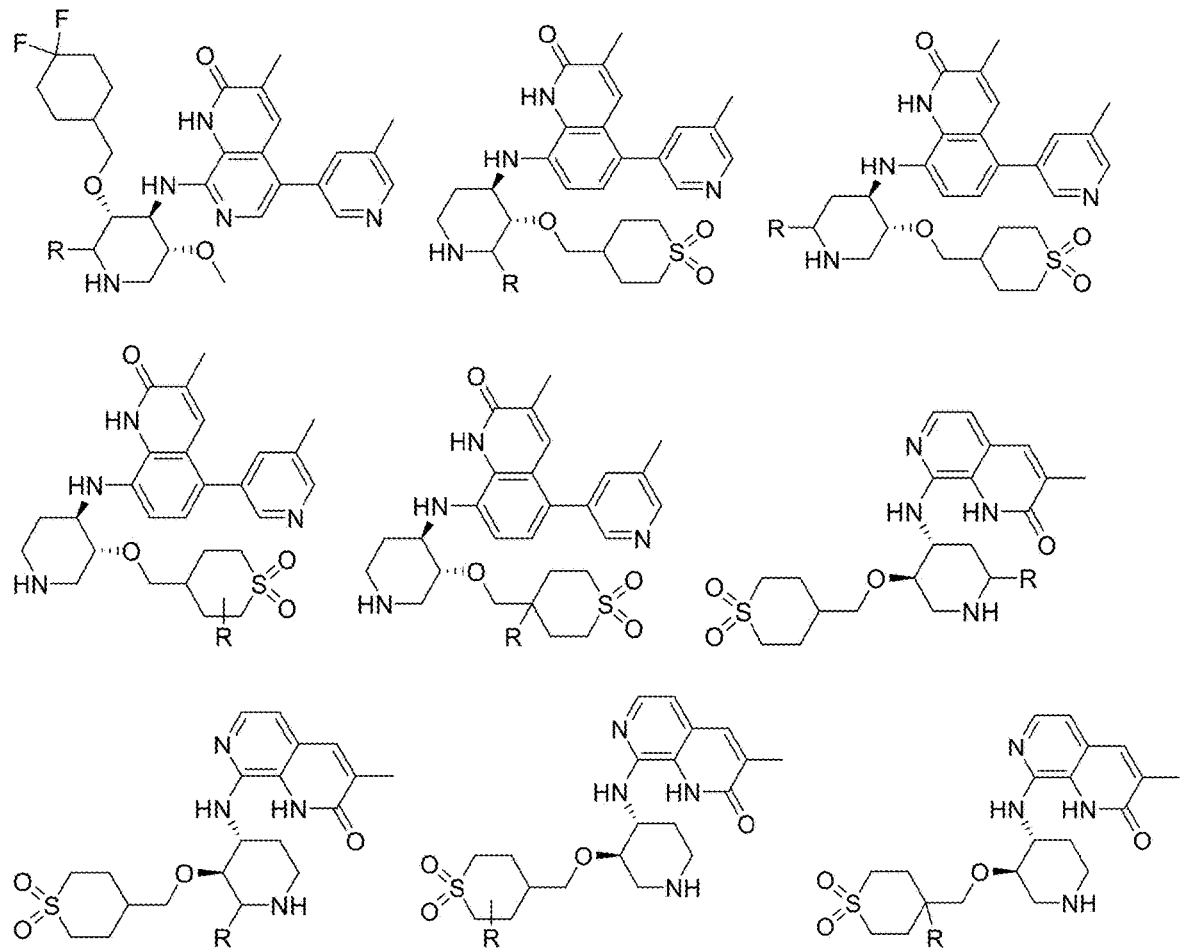
Figure 3X:
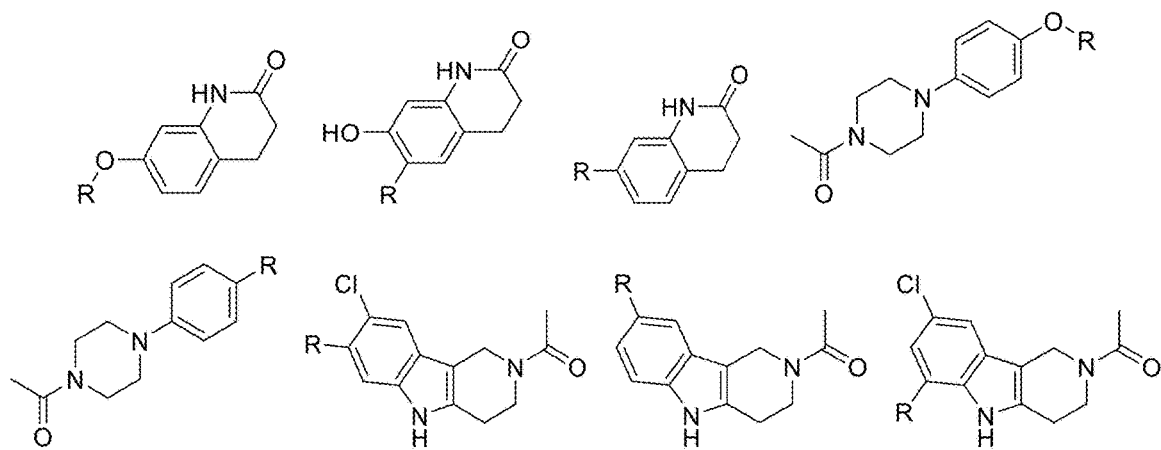
Figure 3Y:
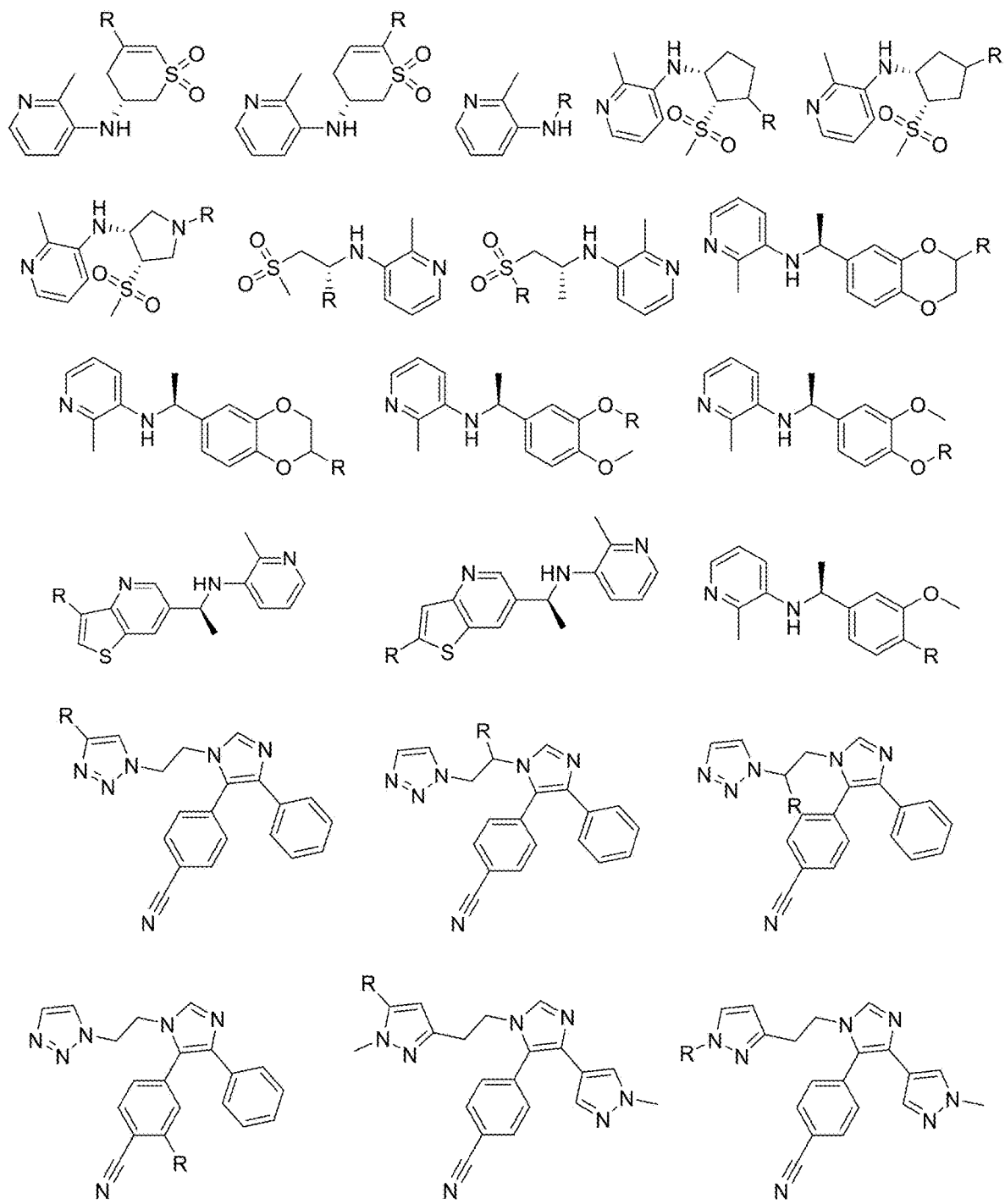
Figure 3Z:
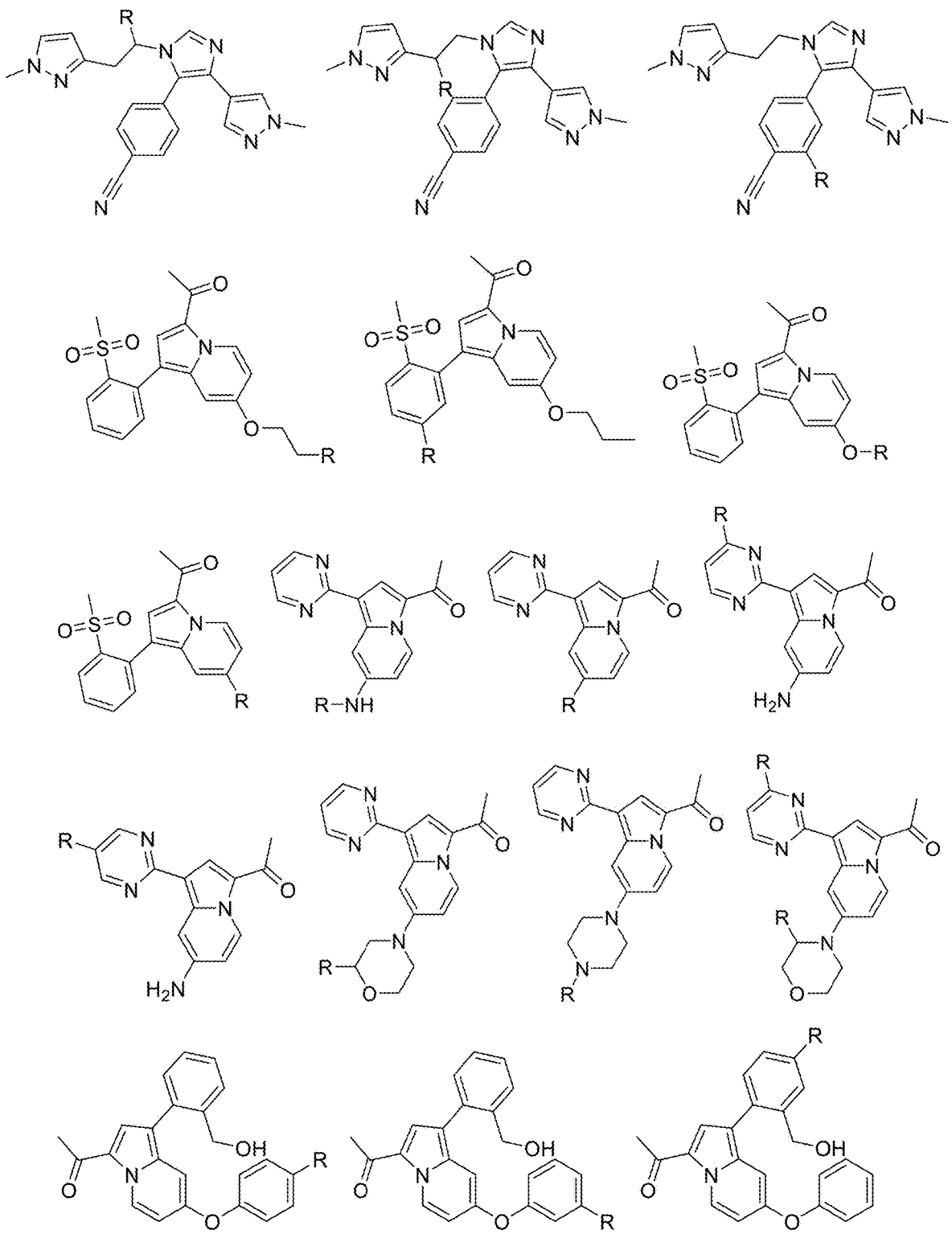

FIG. 3D-3E provide non-limiting examples of HIV Reverse Transcriptase Targeting Ligands, including Efavirenz, Tenofovir, Emtricitabine, Ritonavir, Raltegravir, and Atazanavir, wherein R represents exemplary points at which the Linker can be attached.

FIG. 3F-3G provide non-limiting examples of HIV Protease Targeting Ligands, including Ritonavir, Raltegravir, and Atazanavir, wherein R represents exemplary points at which the Linker can be attached.

FIG. 3H-3I provide non-limiting examples of KSR1 Targeting Ligands wherein R represents exemplary points at which the Linker can be attached.

FIG. 3J-3L provide non-limiting examples of CTNNB1 Targeting Ligands wherein R represents exemplary points at which the Linker can be attached. (See "Direct Targeting of b-Catenin by a Small Molecule Stimulates Proteasomal Degradation and Suppresses Oncogenic Wnt/b-Catenin Signaling" Cell Rep 2016, 16(1), 28; "Rational Design of Small-Molecule Inhibitors for β-Catenin/T-Cell Factor Protein-Protein Interactions by Bioisostere Replacement" ACS Chem Biol 2013, 8, 524; and "Allosteric inhibitor of 0-catenin selectively targets oncogenic Wnt signaling in colon cancer" Sci Rep 2020, 10, 8096).

FIG. 3M provides non-limiting examples of BCL6 Targeting Ligands wherein R represents exemplary points at which the Linker can be attached.

FIG. 3N-3O provide non-limiting examples of PAK1 Targeting Ligands wherein R represents exemplary points at which the Linker can be attached.

FIG. 3P-3R provide non-limiting examples of PAK4 Targeting Ligands wherein R represents exemplary points at which the Linker can be attached.

FIG. 3S-3T provide non-limiting examples of TNIK Targeting Ligands wherein R represents exemplary points at which the Linker can be attached.

FIG. 3U provides non-limiting examples of MEN1 Targeting Ligands wherein R represents exemplary points at which the Linker can be attached.

FIG. 3V-3W provide non-limiting examples of ERK1 Targeting Ligands wherein R represents exemplary points at which the Linker can be attached.

FIG. 3X provides non-limiting examples of IDO1 Targeting Ligands wherein R represents exemplary points at which the Linker can be attached.

FIG. 3Y provides non-limiting examples of CBP Targeting Ligands wherein R represents exemplary points at which the Linker can be attached.

FIG. 3Z-3SS provide non-limiting examples of MCL1 Targeting Ligands wherein R represents exemplary points at which the Linker can be attached. For additional examples and related ligands, see, Tanaka Y. et al "Discovery of potent Mcl-1/Bcl-xL dual inhibitors by using a hybridization strategy based on structural analysis of target proteins." *J. Med. Chem.* 56: 9635-9645 (2013); Friberg A. et al. "Discovery of potent myeloid cell leukemia 1 (Mcl-1) inhibitors using fragment-based methods and structure-based design." *J. Med. Chem.* 56: 15-30 (2013); Petros A. M. et al "Fragment-based discovery of potent inhibitors of the anti-apoptotic MCL-1 protein." *Bioorg. Med. Chem. Lett.* 24: 1484-1488 (2014); Burke J. P. et al. "Discovery of tricyclic indoles that potently inhibit mcl-1 using fragment-based methods and structure-based design." J. Med. Chem. 58: 3794-3805 (2015); Pelz N. F. et al. "Discovery of 2-Indole-acylsulfonamide Myeloid Cell Leukemia 1 (Mcl-1) Inhibitors Using Fragment-Based Methods." *J. Med. Chem.* 59: 2054-2066 (2016); Clifton M. C. et al. "A Maltose-Binding Protein Fusion Construct Yields a Robust Crystallography Platform for MCL1." *Plos One* 10: e0125010-e0125010 (2015); Kotschy A et al. "The MCL1 inhibitor S63845 is tolerable and effective in diverse cancer models. *Nature* 538:477-482 (2016); EP 2886545 A1 titled "New thienopyrimidine derivatives a process for their preparation and pharmaceutical compositions containing them"; Jeffrey W. Johannes et al. "Structure Based Design of Non-Natural Peptidic Macrocyclic Mcl-1 Inhibitors" *ACS Med. Chem. Lett.* (2017); DOI: 10.1021/acsmedchemlett.6b00464; Bruncko M. et al. "Structure-Guided Design of a Series of MCL-1 Inhibitors with High Affinity and Selectivity." J. Med. Chem. 58: 2180-2194 (2015); Taekyu Lee et al. "Discovery and biological characterization of potent myeloid cell leukemia-1 inhibitors." *FEBS Letters* 591: 240-251 (2017); Chen L. et al. "Structure-Based Design of 3-Carboxy-Substituted 1 2 3 4-Tetrahydroquinolines as Inhibitors of Myeloid Cell Leukemia-1 (Mcl-1)." *Org. Biomol. Chem.* 14:5505-5510 (2016); US 2016/0068545 titled "Tetrahydronaphthalene derivatives that inhibit mcl-1 protein"; WO 2016207217 A1 titled "Preparation of new bicyclic derivatives as pro-apoptotic agents"; Gizem Akgay et al. "Inhibition of Mcl-1 through covalent modification of a noncatalytic lysine side chain" *Nature Chemical Biology* 12: 931-936 (2016).

FIG. 3TT provides non-limiting examples of ASH1L Targeting Ligands wherein R represents exemplary points at which the Linker can be attached. See for example, the crystal structure PDB 4YNM ("Human ASH1L SET domain in complex with S-adenosyl methionine (SAM)" Rogawski D. S. et al.) FIG. 3UU-3WW provide non-limiting examples of ATAD2 Targeting Ligands wherein R represents exemplary points at which the Linker can be attached. For additional examples and related ligands, see, Chaikuad A. et al. "Structure-based approaches towards identification of fragments for the low-drugability ATAD2 bromodomain" *Med Chem Comm* 5: 1843-1848 (2014); Poncet-Montange G. et al. "Observed bromodomain flexibility reveals histone peptide- and small molecule ligand-compatible forms of ATAD2." *Biochem. J.* 466: 337-346 (2015); Harner M. J. et al. "Fragment-Based Screening of the Bromodomain of ATAD2." *J. Med. Chem.* 57: 9687-9692 (2014); Demont E. H. et al. "Fragment-Based Discovery of Low-Micromolar Atad2 Bromodomain Inhibitors." *J. Med Chem.* 58: 5649 (2015); and, Bamborough P. et al. "Structure-Based Optimization of Naphthyridones into Potent Atad2 Bromodomain Inhibitors." *J. Med Chem.* 58: 6151 (2015).

FIG. 3XX-3AAA provide non-limiting examples of BAZ2A and BAZ2B Targeting Ligands wherein R represents exemplary points at which the Linker can be attached. For additional examples and related ligands, see, the crystal structure PDB 4CUU ("Human Baz2B in Complex with Fragment-6 N09645" Bradley A. et al.); the crystal structure PDB 5CUA ("Second Bromodomain of Bromodomain Adjacent to Zinc Finger Domain Protein 2B (BAZ2B) in complex with 1-Acetyl-4-(4-hydroxyphenyl)piperazine". Bradley A. et al.); Ferguson F. M. et al. "Targeting low-drugability bromodomains: fragment based screening and inhibitor design against the BAZ2B bromodomain." *J. Med Chem.* 56: 10183-10187 (2013); Marchand J. R. et al. "Derivatives of 3-Amino-2-methylpyridine as BAZ2B Bromodomain Ligands: In Silico Discovery and in Crystallo Validation." *J. Med Chem.* 59: 9919-9927 (2016); Drouin L. et al. "Structure Enabled Design of BAZ2-ICR A Chemical Probe Targeting the Bromodomains of BAZ2A and BAZ2B." *J. Med Chem.* 58: 2553-2559 (2015); Chen P. et al. "Discovery and characterization of GSK2801 a selective chemical probe for the bromodomains BAZ2A and BAZ2B." *J. Med. Chem.* 59:1410-1424 (2016).

FIG. 3BBB provides non-limiting examples of BRD1 Targeting Ligands wherein R represents exemplary points at which the Linker can be attached. For additional examples and related ligands, see, the crystal structure PDB 5AME ("the Crystal Structure of the Bromodomain of Human Surface Epitope Engineered Brd1A in Complex with 3D Consortium Fragment 4-Acetyl-Piperazin-2-One Pearce", N. M. et al.); the crystal structure PDB 5AMF ("Crystal Structure of the Bromodomain of Human Surface Epitope Engineered Brd1A in Complex with 3D Consortium Fragment Ethyl 4 5 6 7-Tetrahydro-1H-Indazole-5-Carboxylate", Pearce N. M. et al.); the crystal structure PDB 5FG6 ("the Crystal structure of the bromodomain of human BRD1 (BRPF2) in complex with OF-1 chemical probe.", Tallant C. et al.); Filippakopoulos P. et al. "Histone recognition and large-scale structural analysis of the human bromodomain family." *Cell,* 149: 214-231 (2012).

FIG. 3CCC-3EEE provide non-limiting examples of BRD2 Bromodomain 1 Targeting Ligands wherein R represents exemplary points at which the Linker can be attached. For additional examples and related ligands, see, the crystal structure PDB 2ydw; the crystal structure PDB 2yek; the crystal structure PDB 4a9h; the crystal structure PDB 4a9f, the crystal structure PDB 4a9i; the crystal structure PDB 4a9m; the crystal structure PDB 4akn; the crystal structure PDB 4alg, and the crystal structure PDB 4uyf.

FIG. 3FFF-3HHH provide non-limiting examples of BRD2 Bromodomain 2 Targeting Ligands wherein R represents exemplary points at which the Linker can be attached. For additional examples and related ligands, see, the crystal structure PDB 3oni; Filippakopoulos P. et al. "Selective Inhibition of BET Bromodomains." *Nature* 468: 1067-1073 (2010); the crystal structure PDB 4jlp; McLure K. G. et al. "RVX-208: an Inducer of ApoA-I in Humans is a BET Bromodomain Antagonist." *Plos One* 8: e83190-e83190 (2013); Baud M. G. et al. "Chemical biology. A bump-and-hole approach to engineer controlled selectivity of BET bromodomain chemical probes" *Science* 346: 638-641 (2014); Baud M. G. et al. "New Synthetic Routes to Triazolo-benzodiazepine Analogues: Expanding the Scope of the Bump-and-Hole Approach for Selective Bromo and Extra-Terminal (BET) Bromodomain Inhibition" *J. Med. Chem.* 59: 1492-1500 (2016); Gosmini R. et al. "The Discovery of I-Bet726 (Gsk1324726A) a Potent Tetrahydroquinoline ApoaI Up-Regulator and Selective Bet Bromodomain Inhibitor" *J. Med. Chem.* 57: 8111 (2014); the crystal structure PDB 5EK9 ("Crystal structure of the second bromodomain of human BRD2 in complex with a hydroquinolinone inhibitor", Tallant C. et al); the crystal structure PDB 5BT5; the crystal structure PDB 5dfd; Baud M. G. et al. "New Synthetic Routes to Triazolo-benzodiazepine Analogues: Expanding the Scope of the Bump-and-Hole Approach for Selective Bromo and Extra-Terminal (BET) Bromodomain Inhibition" *J. Med. Chem.* 59: 1492-1500 (2016).

FIG. 3III-3JJJ provide non-limiting examples of BRD4 Bromodomain 1 Targeting Ligands wherein R represents exemplary points at which the Linker can be attached. For additional examples and related ligands, see, the crystal structure PDB 5WUU and the crystal structure PDB 5F5Z.

FIG. 3KKK-3LLL provide non-limiting examples of BRD4 Bromodomain 2 Targeting Ligands wherein R represents exemplary points at which the Linker can be attached. For additional examples and related ligands, see, Chung C. W. et al. "Discovery and Characterization of Small Molecule Inhibitors of the Bet Family Bromodomains" *J. Med. Chem.* 54: 3827 (2011) and Ran X. et al. "Structure-Based Design of gamma-Carboline Analogues as Potent and Specific BET Bromodomain Inhibitors" *J. Med. Chem.* 58: 4927-4939 (2015).

FIG. 3MMM provides non-limiting examples of BRDT Targeting Ligands wherein R represents exemplary points at which the Linker can be attached. For additional examples and related ligands, see, the crystal structure PDB 4flp and the crystal structure PDB 4kcx.

FIG. 3NNN-3QQQ provide non-limiting examples of BRD9 Targeting Ligands wherein R represents exemplary points at which the Linker can be attached. For additional examples and related ligands, see, the crystal structure PDB 4ngn; the crystal structure PDB 4uit; the crystal structure PDB 4uiu; the crystal structure PDB 4uiv; the crystal structure PDB 4z6h; the crystal structure PDB 4z6i; the crystal structure PDB 5e9v; the crystal structure PDB 5eul; the crystal structure PDB 5flh; the crystal structure PDB 5fp2, ("Structure-Based Design of an in Vivo Active Selective BRD9 Inhibitor" *J Med Chem.*, 2016, 59(10), 4462; and WO2016139361).

FIG. 3RRR provides non-limiting examples of SMARCA4 PB1 and/or SMARCA2 Targeting Ligands wherein R represents exemplary points at which the Linker can be attached, A is N or CH, and m is 0 1 2 3 4 5 6 7 or 8.

FIG. 3SSS-3XXX provide non-limiting examples of additional Bromodomain Targeting Ligands wherein R represents exemplary points at which the Linker can be attached. For additional examples and related ligands, see, Hewings et al. "3 5-Dimethylisoxazoles Act as Acetyl-lysine Bromodomain Ligands." *J. Med. Chem.* 54 6761-6770 (2011); Dawson et al. "Inhibition of BET Recruitment to Chromatin as an Effective Treatment for MLL-fusion Leukemia." *Nature,* 478, 529-533 (2011); US 2015/0256700; US 2015/0148342; WO 2015/074064; WO 2015/067770; WO 2015/022332; WO 2015/015318; and, WO 2015/011084.

FIG. 3YYY provides non-limiting examples of PB1 Targeting Ligands wherein R represents exemplary points at which the Linker can be attached. For additional examples and related ligands, see, the crystal structure PDB 3mb4; the crystal structure PDB 4qOn; and, the crystal structure PDB 5fh6.

FIG. 3ZZZ provides non-limiting examples of SMARCA4 Targeting Ligands wherein R represents exemplary points at which the Linker can be attached. For additional examples and related ligands, see, the crystal structure 3uvd and the crystal structure 5dkd.

FIG. 3AAAA provides non-limiting examples of SMARCA2 Targeting Ligands wherein R represents exemplary points at which the Linker can be attached. For additional examples and related ligands, see, the crystal structure 5dkc and the crystal structure 5dkh; and WO2020023657, US20200038378, WO2020010227, WO2020078933, WO2019207538, WO2016138114, WO2020035779, and "Discovery of Orally Active Inhibitors of Brahma Homolog (BRM)/SMARCA2 ATPase Activity for the Treatment of Brahma Related Gene 1 (BRG1)/SMARCA4-Mutant Cancers" *J Med Chem* 2018, 61, 10155.

FIG. 3BBBB provides non-limiting examples of TRIM24 (TIF1a) and/or BRPF1 Targeting Ligands wherein R represents exemplary points at which the Linker can be attached and m is 0 12 3 4 5 6 7 or 8.

FIG. 3CCCC provides non-limiting examples of TRIM24 (TIF1a) Targeting Ligands wherein R represents exemplary points at which the Linker can be attached. For additional examples and related ligands, see, Palmer W. S. et al. "Structure-Guided Design of IACS-9571: a Selective High-Affinity Dual TRIM24-BRPF1 Bromodomain Inhibitor." *J. Med. Chem.* 59: 1440-1454 (2016).

FIG. 3DDDD-3FFFF provide non-limiting examples of BRPF1 Targeting Ligands wherein R represents exemplary points at which the Linker can be attached. For additional examples and related ligands, see, the crystal structure PDB 4uye; the crystal structure PDB 5c7n; the crystal structure PDB 5c87; the crystal structure PDB 5c89; the crystal structure PDB 5d7x; the crystal structure PDB 5dya; the crystal structure PDB 5epr; the crystal structure PDB 5eql; the crystal structure PDB 5etb; the crystal structure PDB 5ev9; the crystal structure PDB 5eva; the crystal structure PDB 5ewv; the crystal structure PDB 5eww; the crystal structure PDB 5ffy; the crystal structure PDB 5fg5; and, the crystal structure PDB 5g4r.

FIG. 3GGGG provides non-limiting examples of CECR2 Targeting Ligands wherein R represents exemplary points at which the Linker can be attached. For additional examples and related ligands, see, Moustakim M. et al. *Med. Chem. Comm.* 7:2246-2264 (2016) and Crawford T. et al. *Journal of Med. Chem.* 59; 5391-5402 (2016).

FIG. 3HHHH-3OOOO provide non-limiting examples of CREBBP Targeting Ligands wherein R represents exemplary points at which the Linker can be attached, A is N or CH, and m is 0 1 2 3 4 5 6 7 or 8. For additional examples and related ligands, see, the crystal structure PDB 3pld; the crystal structure PDB 3svh; the crystal structure PDB 4nr4; the crystal structure PDB 4nr5; the crystal structure PDB 4ts8; the crystal structure PDB 4nr6; the crystal structure PDB 4nr7; the crystal structure PDB 4nyw; the crystal structure PDB 4nyx; the crystal structure PDB 4tqn; the crystal structure PDB 5cgp; the crystal structure PDB 5dbm; the crystal structure PDB 5ep7; the crystal structure PDB 5i83; the crystal structure PDB 5i86; the crystal structure PDB 5i89; the crystal structure PDB 5i8g; the crystal structure PDB 5j0d; the crystal structure PDB 5ktu; the crystal structure PDB 5ktw; the crystal structure PDB 5ktx; the crystal structure PDB 5tb6.

FIG. 3PPPP provides non-limiting examples of EP300 Targeting Ligands wherein R represents exemplary points at which the Linker can be attached. For additional examples and related ligands, see, the crystal structure PDB 5BT3.

FIG. 3QQQQ provides non-limiting examples of PCAF Targeting Ligands wherein R represents exemplary points at which the Linker can be attached. See for example, M. Ghizzoni et al. *Bioorg. Med Chem.* 18: 5826-5834 (2010).

FIG. 3RRRR provides non-limiting examples of PHIP Targeting Ligands wherein R represents exemplary points at which the Linker can be attached. For additional examples and related ligands, see, *Mol Cancer Ther.* 7(9): 2621-2632 (2008).

FIG. 3SSSS provides non-limiting examples of TAF1 and TAF1L Targeting Ligands wherein R represents exemplary points at which the Linker can be attached. For additional examples and related ligands, see, Picaud S. et al. *Sci Adv* 2: e1600760-e1600760 (2016).

FIG. 3TTTT provides non-limiting examples of Histone Deacetylase 2 (HDAC2) Targeting Ligands wherein R represents exemplary points at which the Linker can be attached. For additional examples and related ligands, see, Lauffer B. E. *J. Biol. Chem.* 288: 26926-26943 (2013); Wagner F. F. *Bioorg. Med Chem.* 24: 4008-4015 (2016); Bressi *J. C. Bioorg. Med Chem. Lett.* 20: 3142-3145 (2010); and, Lauffer B. E. *J. Biol. Chem.* 288: 26926-26943 (2013).

FIG. 3UUUU-3VVVV provide non-limiting examples of Histone Deacetylase 4 (HDAC4) Targeting Ligands wherein R represents exemplary points at which the Linker can be attached. For additional examples and related ligands, see, Burli R. W. *J. Med Chem.* 56: 9934 (2013); Luckhurst C. A. *ACS Med Chem. Lett.* 7: 34 (2016); Bottomley M. J. J. *Biol. Chem.* 283: 26694-26704 (2008).

FIG. 3WWWW provides non-limiting examples of Histone Deacetylase 6 Targeting Ligands wherein R represents exemplary points at which the Linker can be attached. For additional examples and related ligands, see, Harding R. J. (to be published); Hai Y. *Nat. Chem. Biol.* 12: 741-747, (2016); and, Miyake Y. *Nat. Chem. Biol.* 12: 748 (2016).

FIG. 3XXXX-3YYYY provide non-limiting examples of Histone Deacetylase 7 Targeting Ligands wherein R represents exemplary points at which the Linker can be attached. For additional examples and related ligands, see, Lobera M.

*Nat. Chem. Biol.* 9: 319 (2013) and Schuetz A. *J. Biol. Chem.* 283: 11355-11363 (2008).

FIG. 3ZZZZ-3DDDDD provide non-limiting examples of Histone Deacetylase 8 Targeting Ligands wherein R represents exemplary points at which the Linker can be attached. For additional examples and related ligands, see, Whitehead L. Biol. *Med. Chem.* 19: 4626-4634 (2011); Tabackman A. A. *J. Struct. Biol.* 195: 373-378 (2016); Dowling D. P. *Biochemistry* 47, 13554-13563 (2008); Somoza J. R. *Biochemistry* 12, 1325-1334 (2004); Decroos C. *Biochemistry* 54: 2126-2135 (2015); Vannini A. *Proc. Natl Acad. Sci.* 101: 15064 (2004); Vannini A. *EMBO Rep.* 8: 879 (2007); the crystal structure PDB 5BWZ; Decroos A. *ACS Chem. Biol.* 9: 2157-2164 (2014); Somoza J. R. *Biochemistry* 12: 1325-1334 (2004); Decroos C. *Biochemistry* 54: 6501-6513 (2015); Decroos A. *ACS Chem. Biol.* 9: 2157-2164 (2014); and, Dowling D. P. *Biochemistry* 47: 13554-13563 (2008).

FIG. 3EEEEE provides non-limiting examples of Histone Acetyltransferase (KAT2B) Targeting Ligands wherein R represents exemplary points at which the Linker can be attached. For additional examples and related ligands, see, Chaikuad A. *J. Med. Chem.* 59: 1648-1653 (2016); the crystal structure PDB 1ZS5; and, Zeng L. *J. Am. Chem. Soc.* 127: 2376-2377 (2005).

FIG. 3FFFFF-3GGGGG provide non-limiting examples of Histone Acetyltransferase (KAT2A) Targeting Ligands wherein R represents exemplary points at which the Linker can be attached. For additional examples and related ligands, see, Ringel A. E. *Acta Crystallogr. D. Struct. Biol.* 72: 841-848 (2016).

FIG. 3HHHHH provides non-limiting examples of Histone Acetyltransferase Type B Catalytic Unit (HAT1) Targeting Ligands wherein R represents exemplary points at which the Linker can be attached. For additional examples and related ligands, see, the crystal structure PDB 2POW.

FIG. 3IIIII provides non-limiting examples of Cyclic AMP-dependent Transcription Factor (ATF2) Targeting Ligands wherein R represents exemplary points at which the Linker can be attached.

FIG. 3JJJJJ provides non-limiting examples of Histone Acetyltransferase (KAT5) Targeting Ligands wherein R represents exemplary points at which the Linker can be attached.

FIG. 3KKKKK-3MMMMM provide non-limiting examples of Lysine-specific histone demethylase 1A (KDM1A) Targeting Ligands wherein R represents exemplary points at which the Linker can be attached. For additional examples and related ligands, see, Mimasu S. *Biochemistry* 49: 6494-6503 (2010); Sartori L. *J. Med. Chem.* 60:1673-1693 (2017); and, Vianello P. *J. Med. Chem.* 60: 1693-1715 (2017).

FIG. 3NNNNN provides non-limiting examples of HDAC6 Zn Finger Domain Targeting Ligands wherein R represents exemplary points at which the Linker can be attached.

FIG. 3OOOOO-3PPPPP provide non-limiting examples of general Lysine Methyltransferase Targeting Ligands wherein R represents exemplary points at which the Linker can be attached.

FIG. 3QQQQQ-3TTTTT provide non-limiting examples of DOT1L Targeting Ligands wherein R represents exemplary points at which the Linker can be attached, A is N or CH, and m is 0 1 2 3 4 5 6 7 or 8. For additional examples and related ligands, see, the crystal structure PDB 5MVS ("Dot1L in complex with adenosine and inhibitor CPD1" Mobitz, H. et al., *ACS Med Chem Lett.*, 2017, 8: 338-343); the crystal structure PDB 5MW3, 5MW4 ("Dot1L in complex inhibitor CPD7" Be C. et al.); the crystal structure PDB 5DRT ("Dot1L in complex inhibitor CPD2" Chen, C., et al., *ACS Med Chem Lett.*, 2016, 7: 735-740); the crystal structure PDB 5DRY ("Dot1L in complex with CPD3", Chen, C., et al., *ACS Med Chem Lett.*, 2016, 7: 735-740), the crystal structure of PDB 5DSX ("Dot1L in complex with CPD10", Chen, C., et al., *ACS Med Chem Lett.*, 2016, 7: 735-740), the crystal structure PDB 5DT2 ("Dot1L in complex with CPD11", Chen, C., et al., *ACS Med Chem Lett.*, 2016, 7: 735-740), the crystal structure PDB 5JUW "(Dot1L in complex with SS148" Yu W. et al. Structural Genomics Consortium), the crystal structure PDB 6TE6 ("Dot1L in complex with an inhibitor, compound 3", Stauffer, F., et al., *ACS Med Chem Lett.*, 2019, 10: 1655-1660).

FIG. 3UUUUU provides non-limiting examples of EHMT1 Targeting Ligands wherein R represents exemplary points at which the Linker can be attached. For additional examples and related ligands, see, the crystal structure PDB 5TUZ ("EHMT1 in complex with inhibitor MS0124", Babault N. et al.).

FIG. 3VVVVV provides non-limiting examples of EHMT2 Targeting Ligands wherein R represents exemplary points at which the Linker can be attached. For additional examples and related ligands, see, the crystal structure PDB 5TUY ("EHMT2 in complex with inhibitor MS0124", Babault N. et al.); the PDB crystal structure 5TTF ("EHMT2 in complex with inhibitor MS012", Dong A. et al.); the PDB crystal structure 3RJW (Dong A. et al., Structural Genomics Consortium); the PDB crystal structure 3K5K; Liu F. et al. *J. Med. Chem.* 52: 7950-7953 (2009); and, the PDB crystal structure 4NVQ ("EHMT2 in complex with inhibitor A-366" Sweis R. F. et al.).

FIG. 3WWWWW provides non-limiting examples of SETD2 Targeting Ligands wherein R represents exemplary points at which the Linker can be attached. For additional examples and related ligands, see, the PDB crystal structure 5LSY ("SETD2 in complex with cyproheptadine", Tisi D. et al.); Tisi D. et al. *ACS Chem. Biol.* 11: 3093-3105 (2016); the crystal structures PDB 5LSS, 5LSX, 5LSZ, 5LT6, 5LT7, and 5LT8; the PDB crystal structure 4FMU; and, Zheng W. et al. *J. Am. Chem. Soc.* 134: 18004-18014 (2012).

FIG. 3XXXXX-3YYYYY provide non-limiting examples of SETD7 Targeting Ligands wherein R represents exemplary points at which the Linker can be attached. For additional examples and related ligands, see, the PDB crystal structure 5AYF ("SETD7 in complex with cyproheptadine." Niwa H. et al.); the PDB crystal structure 4JLG ("SETD7 in complex with (R)-PFI-2", Dong A. et al.); the PDB crystal structure 4JDS (Dong A. et. al Structural Genomics Consortium); the PDB crystal structure 4E47 (Walker J. R. et al. Structural Genomics Consortium; the PDB crystal structure 3VUZ ("SETD7 in complex with AAM-1." Niwa H. et al.); the PDB crystal structure 3VVO; and, Niwa H et al. *Acta Crystallogr. Sect.D* 69: 595-602 (2013).

FIG. 3ZZZZZ provides non-limiting examples of SETD8 Targeting Ligands wherein R represents exemplary points at which the Linker can be attached. For additional examples and related ligands, see, the PDB crystal structure 5TH7 ("SETD8 in complex with MS453", Yu W. et al.) and the PDB crystal structure 5T5G (Yu W et. al.; to be published).

Figure 4B:
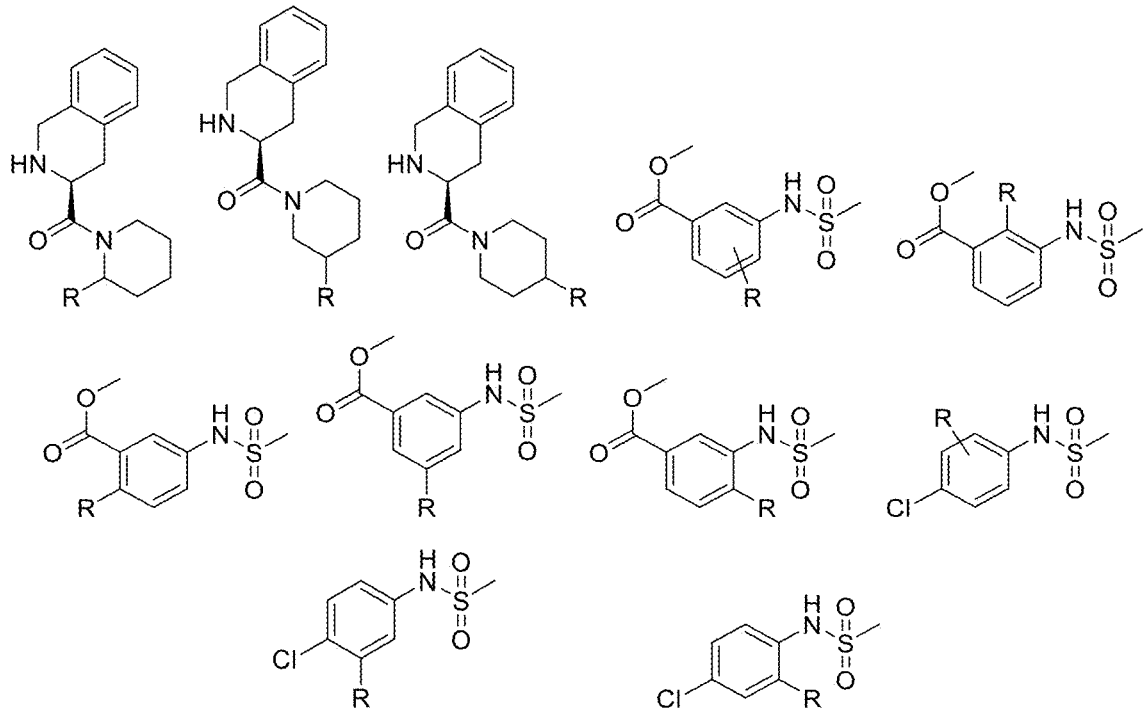
Figure 4C:
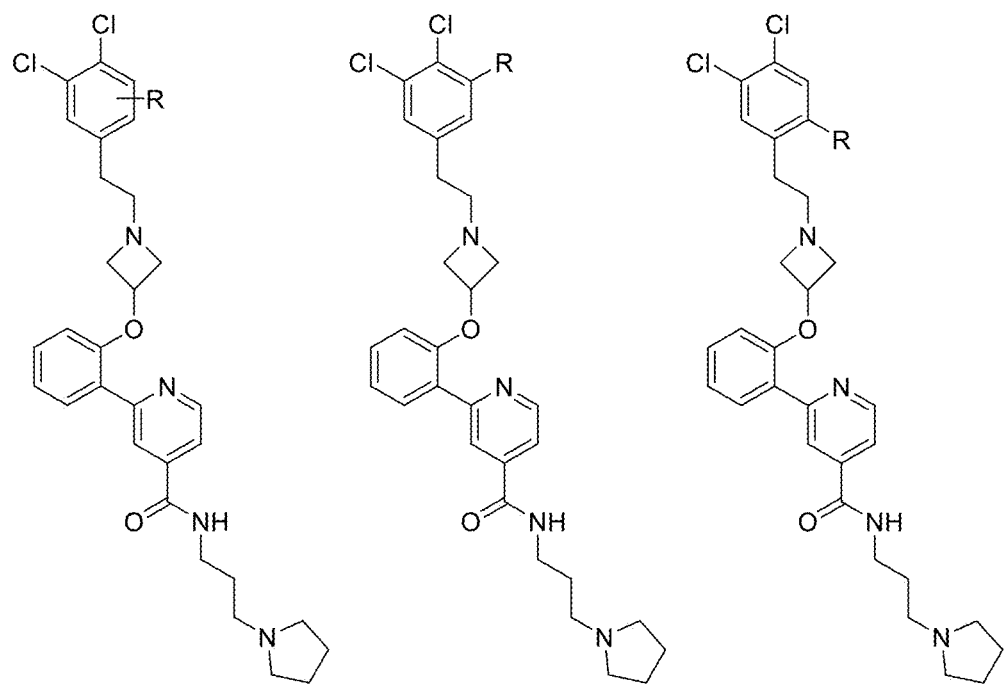
Figure 4D:
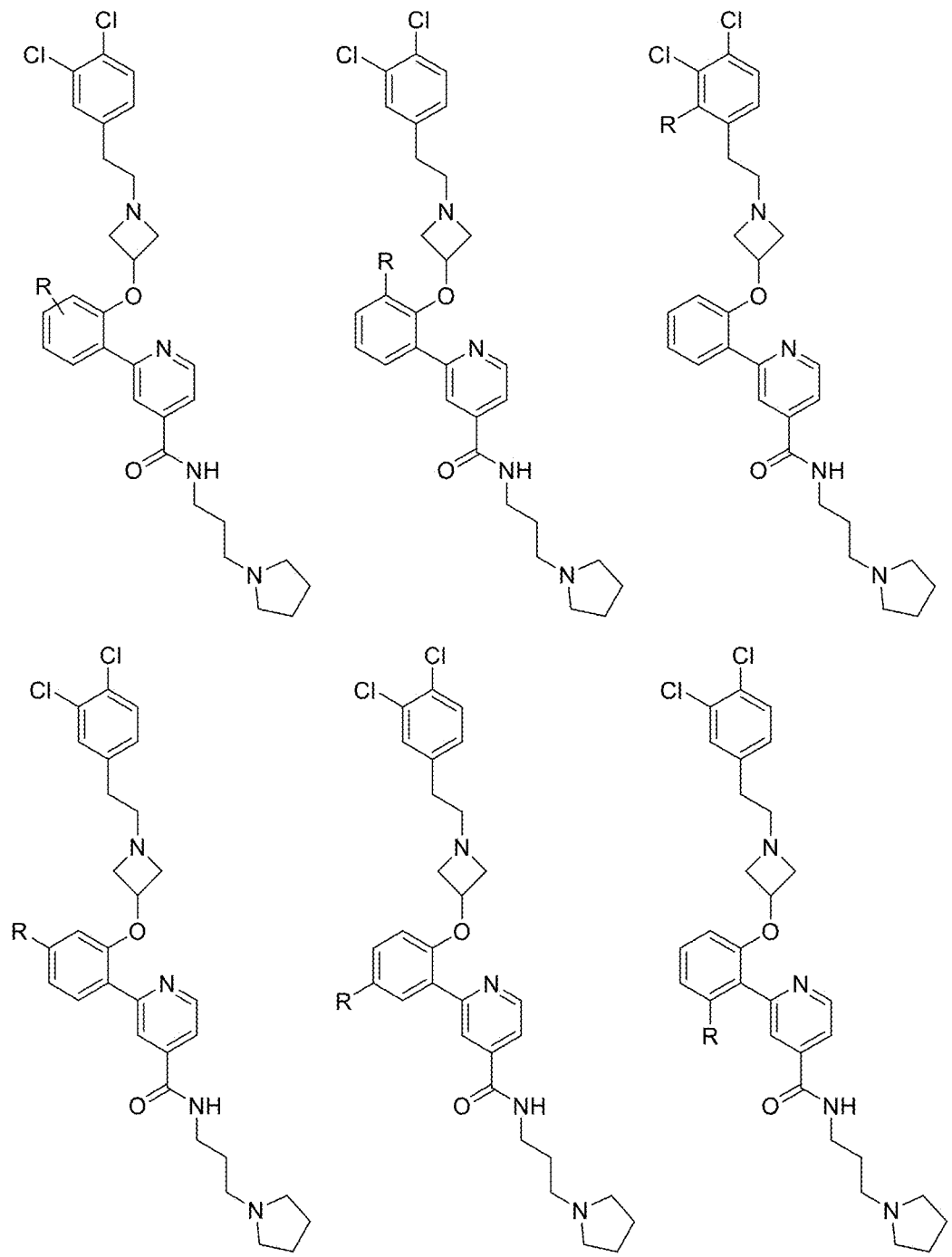
Figure 4E:
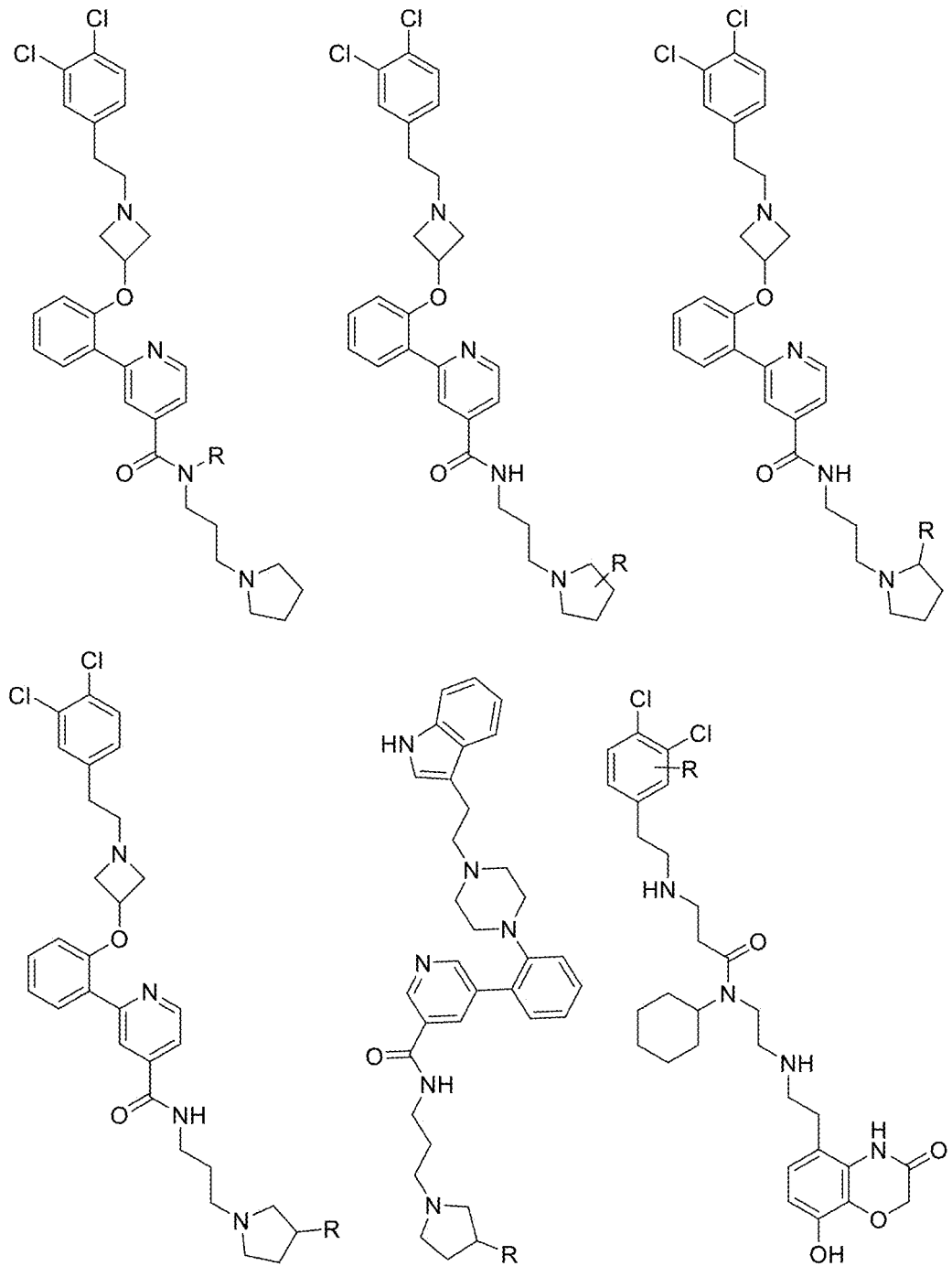
Figure 4F:
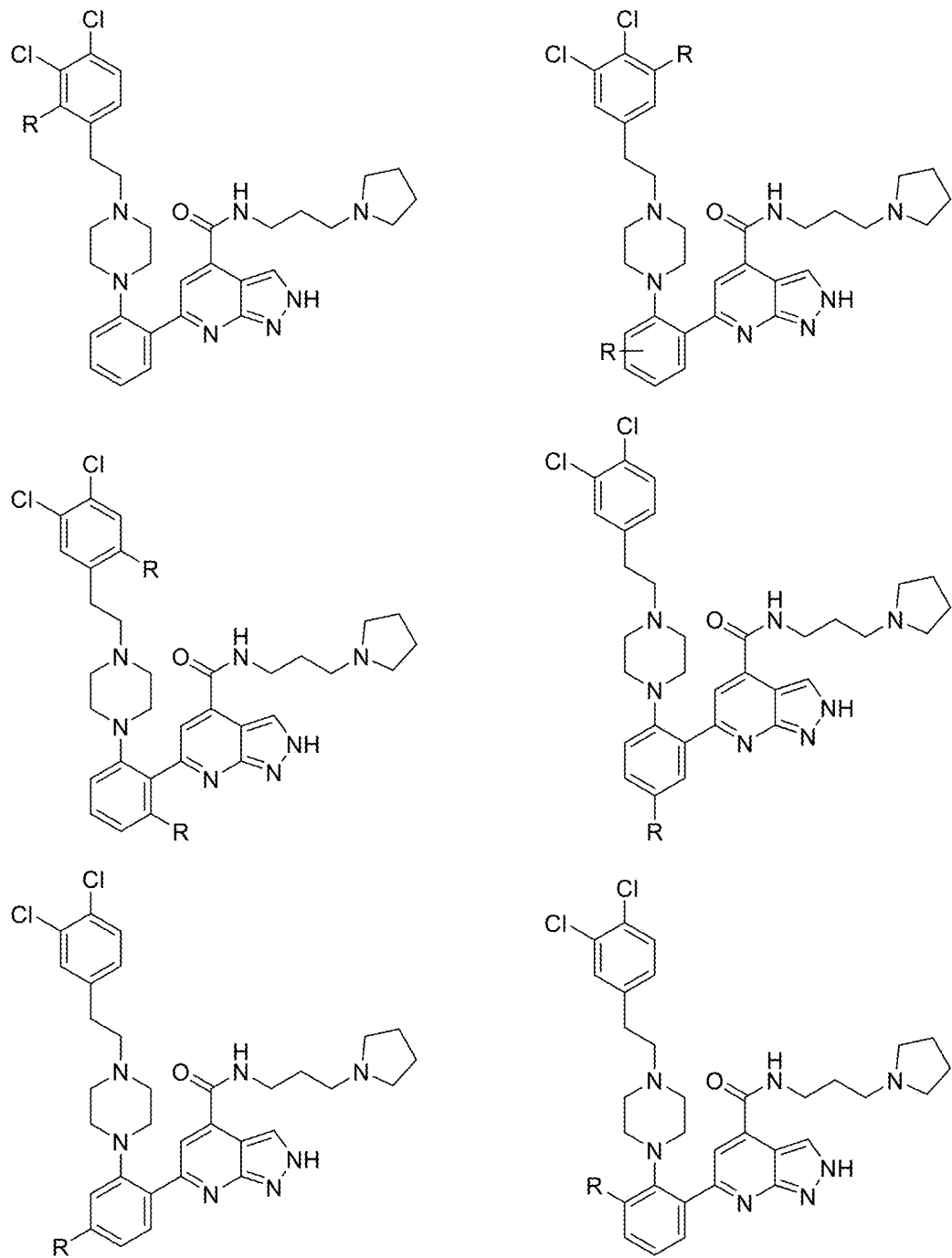
Figure 4G:
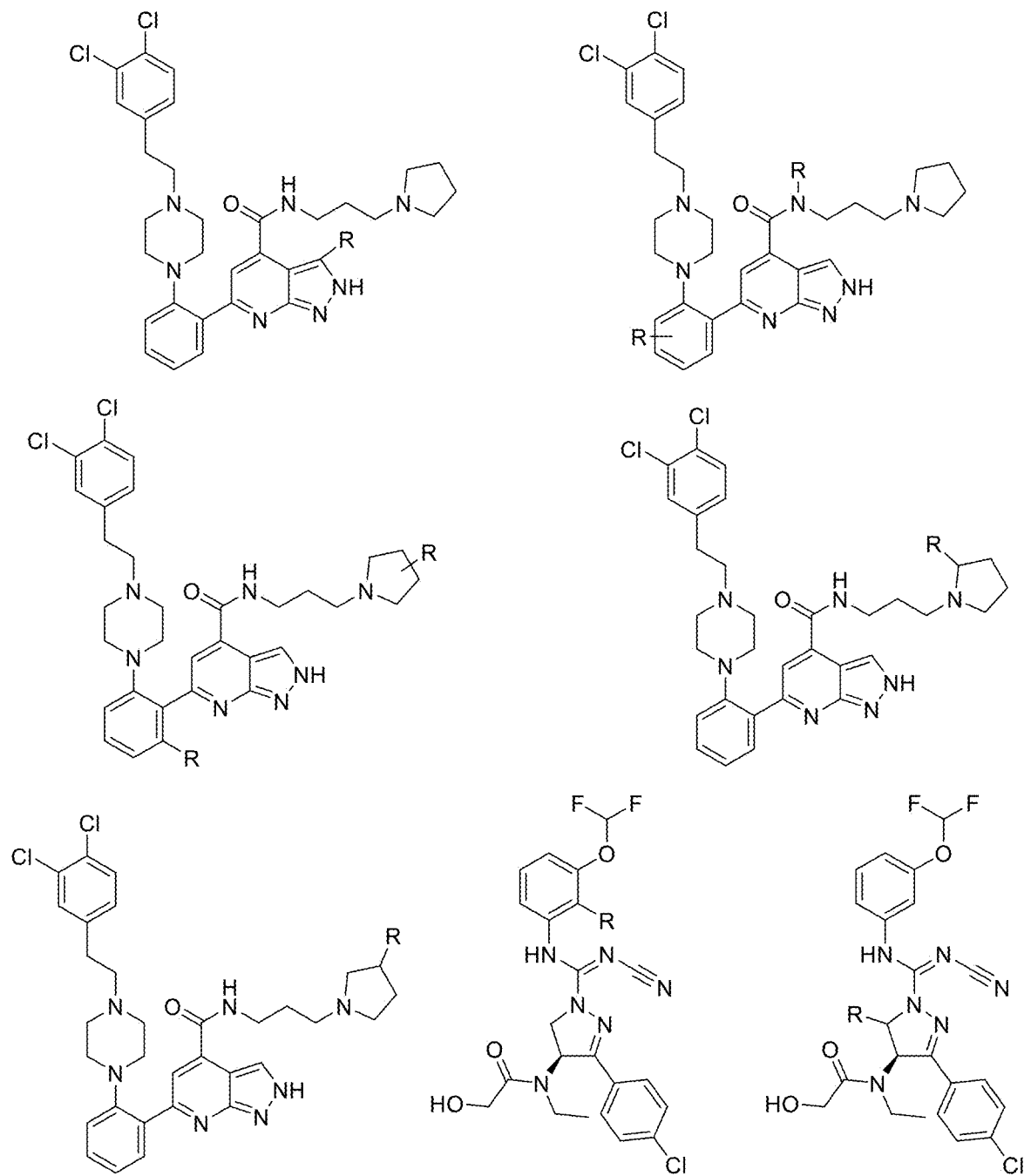
Figure 4H:
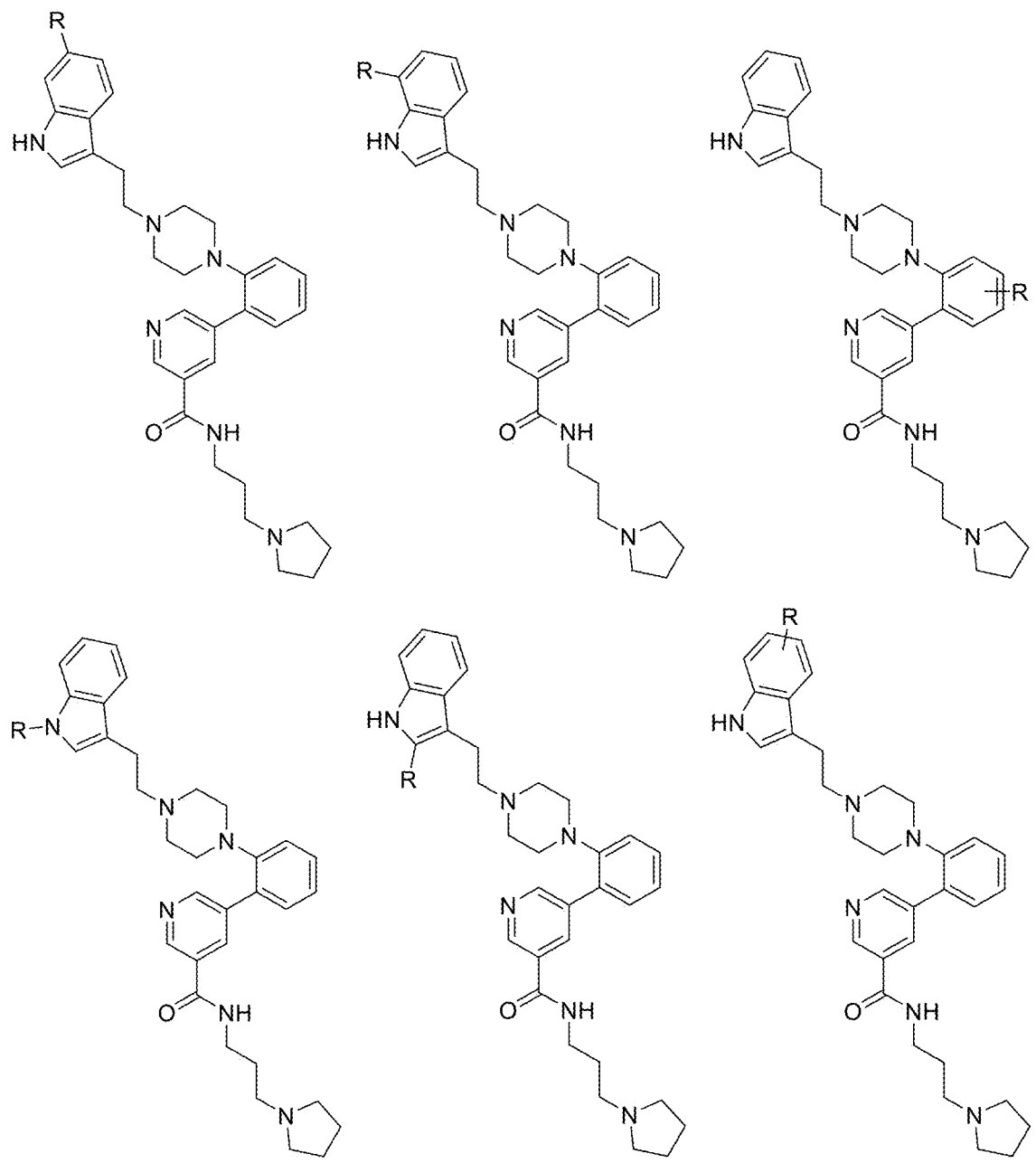
Figure 4I:
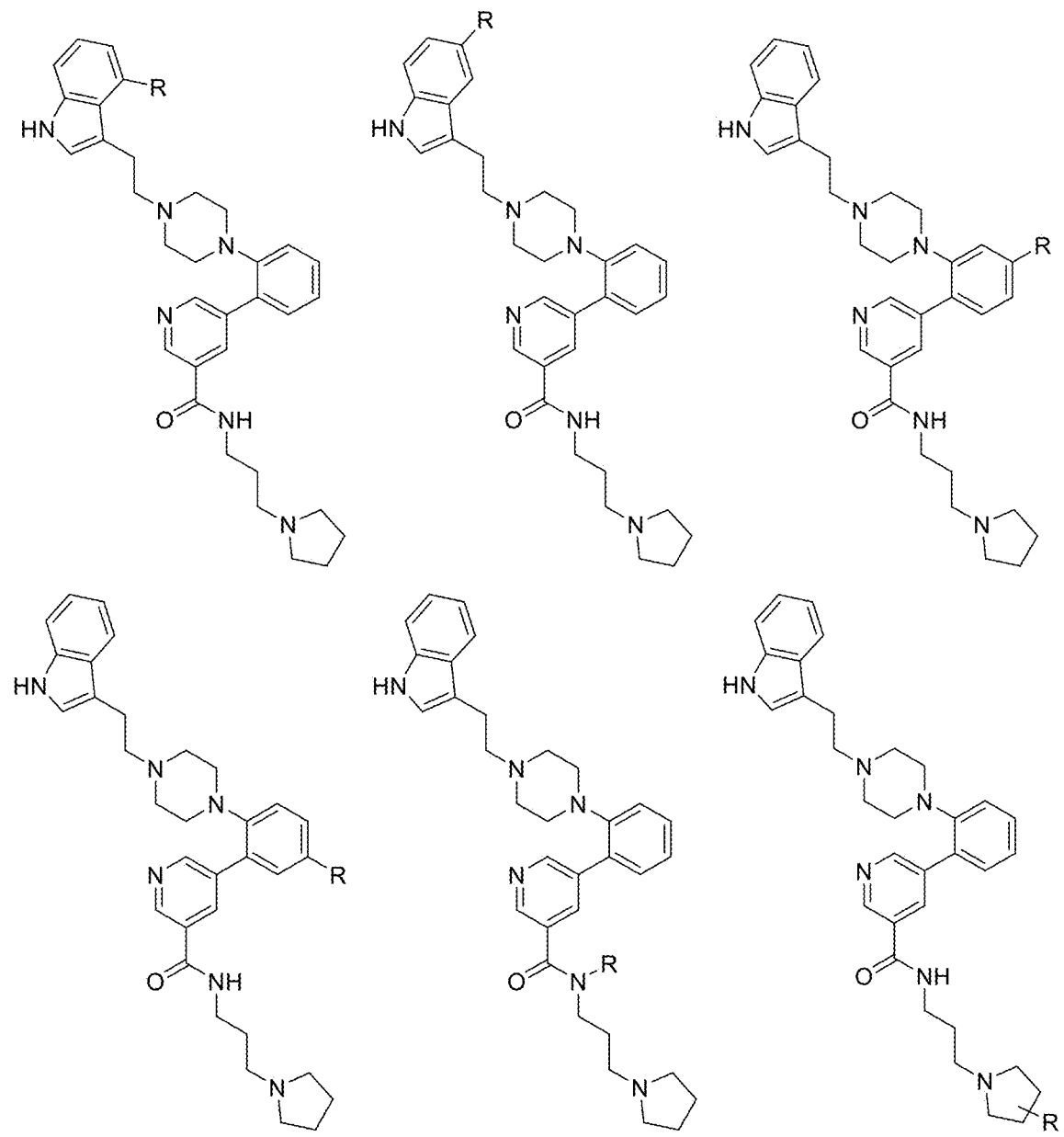
Figure 4J:
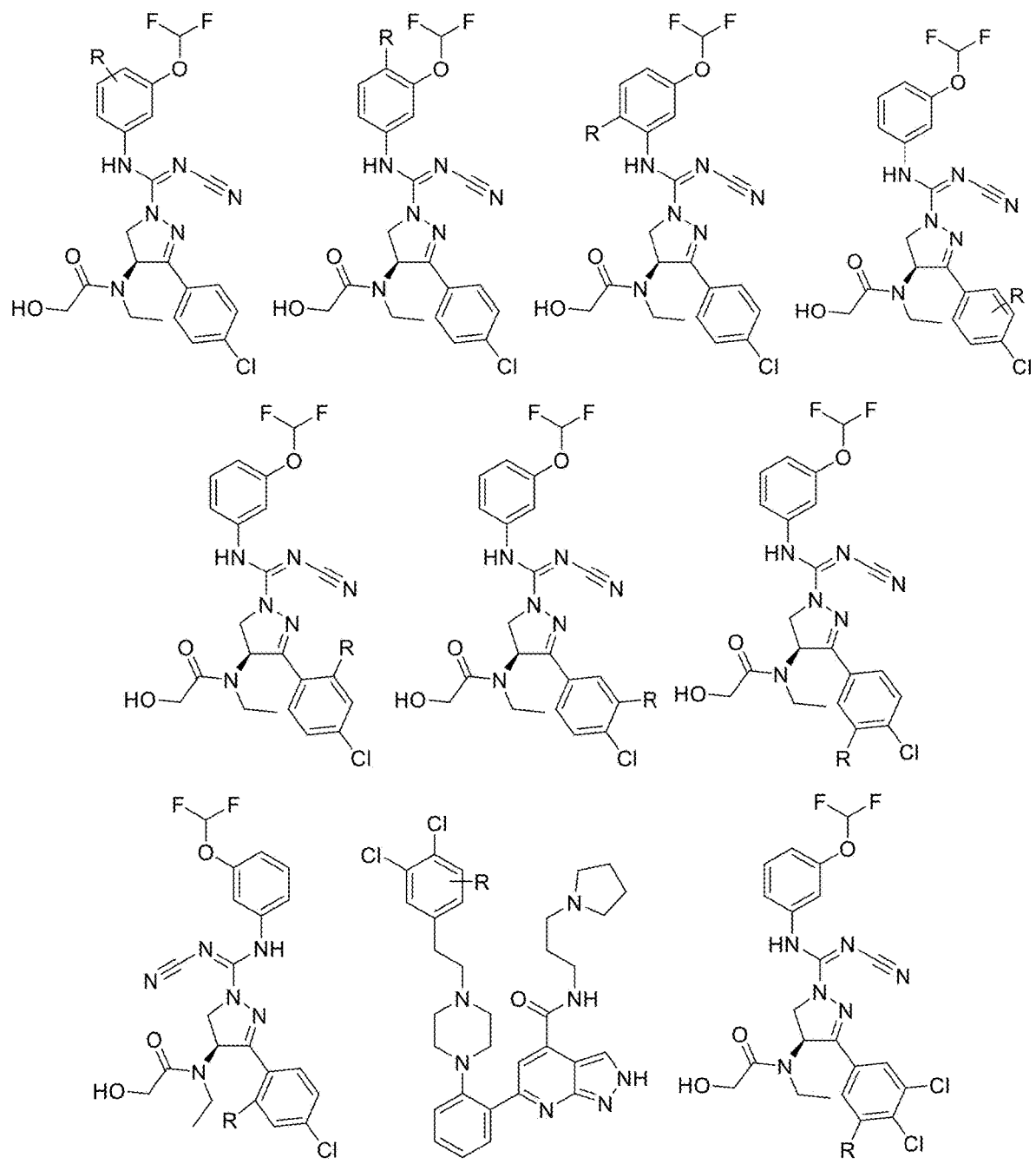
Figure 4K:
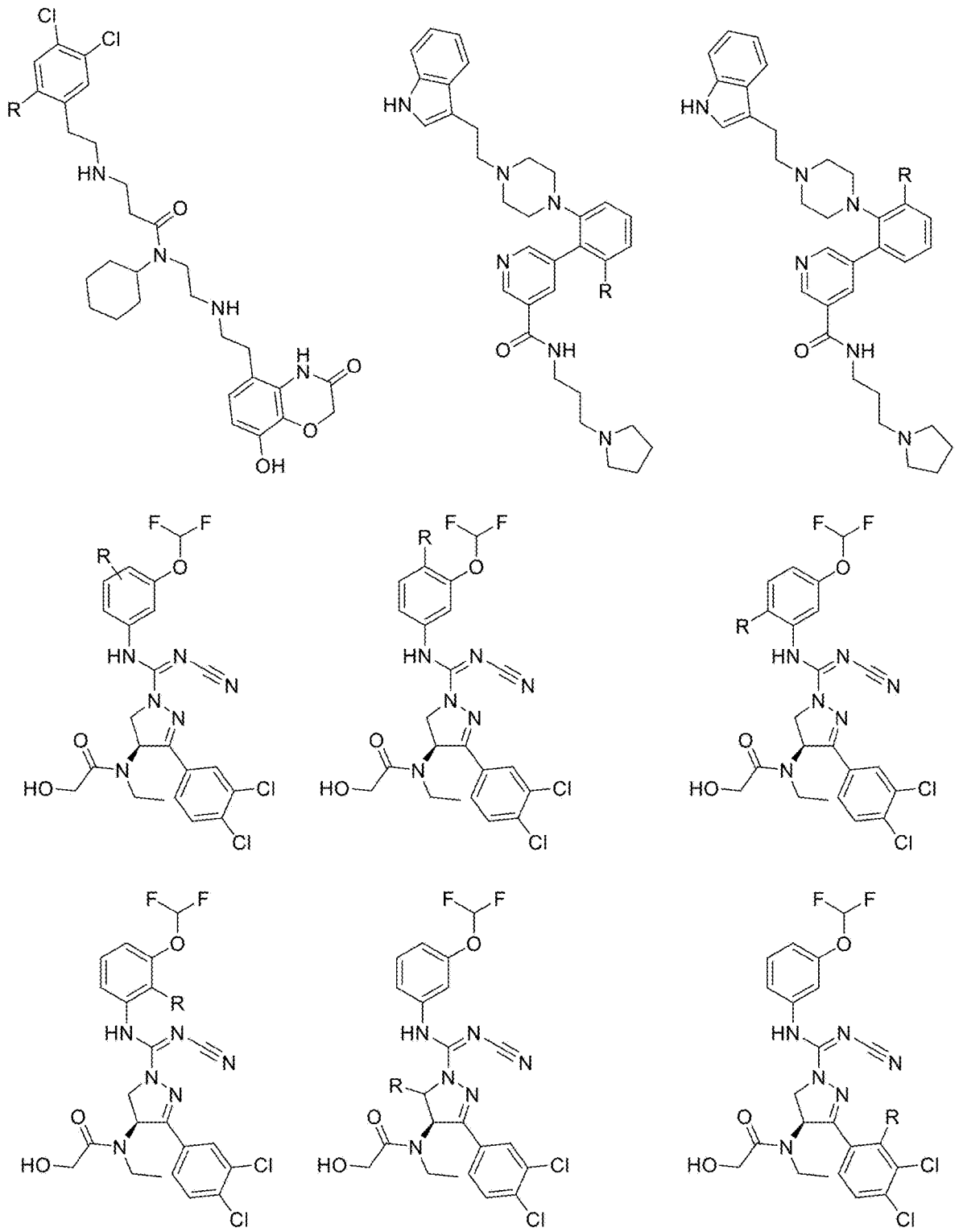
Figure 4L:
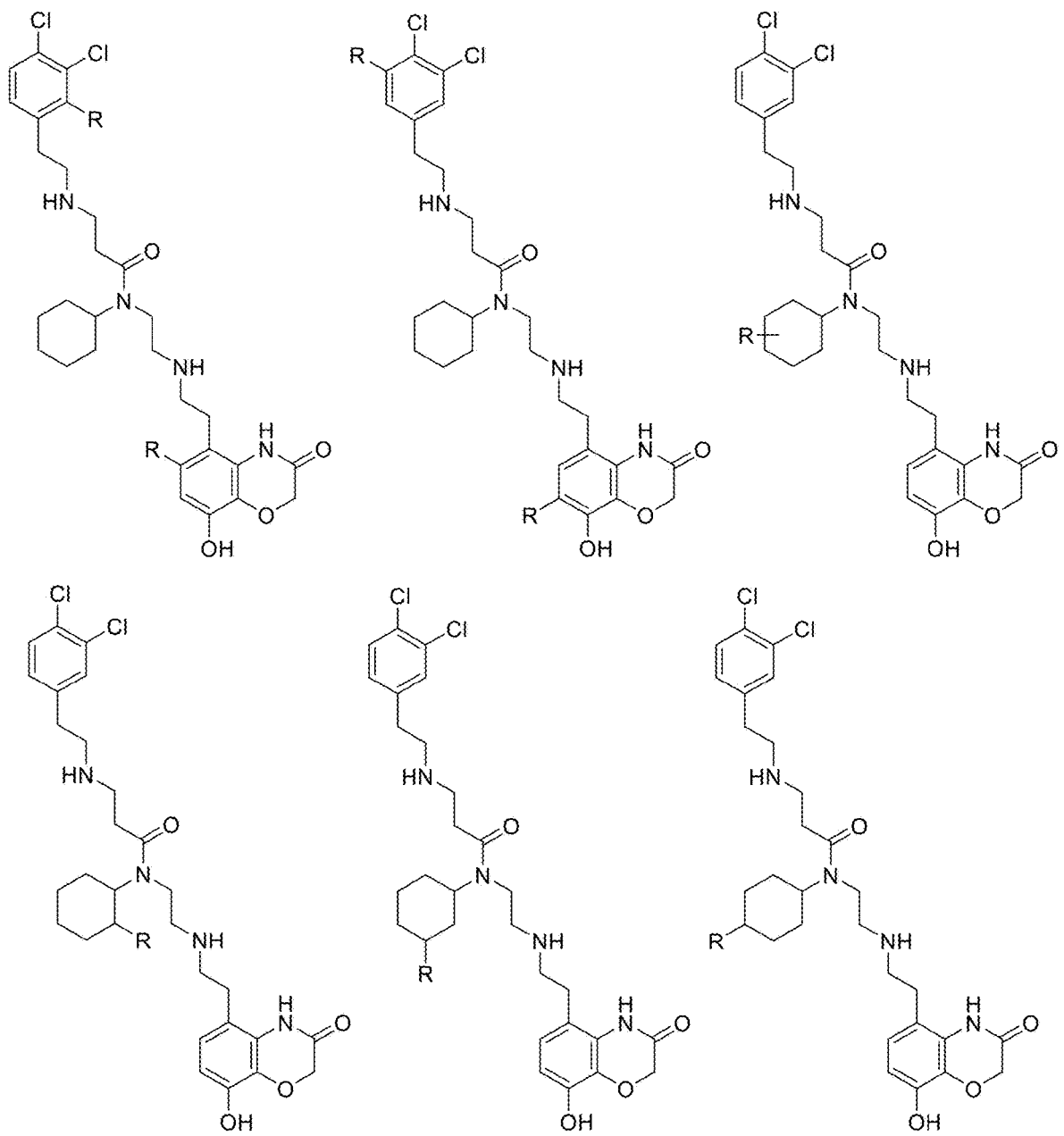
Figure 4M:
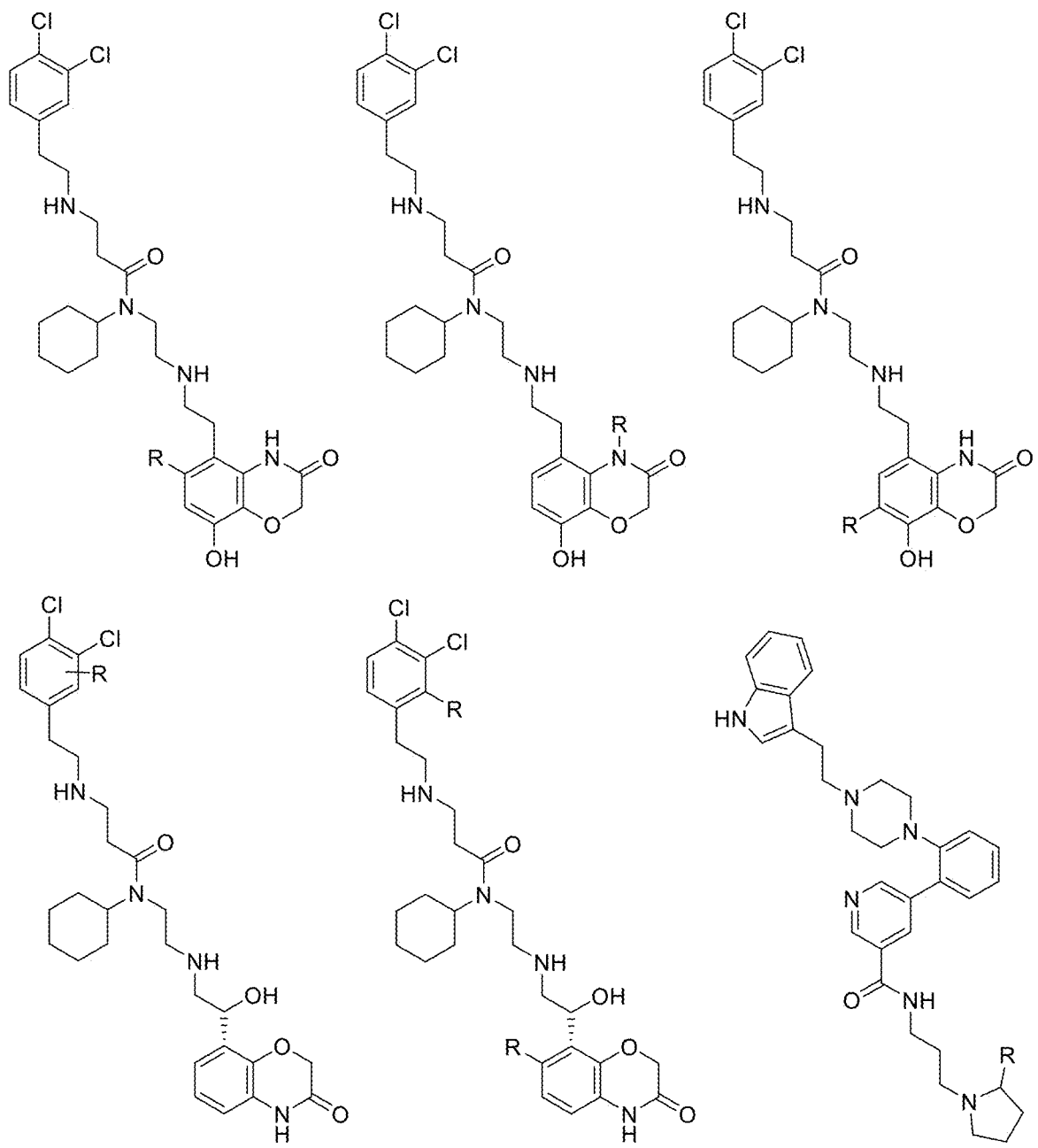
Figure 4N:
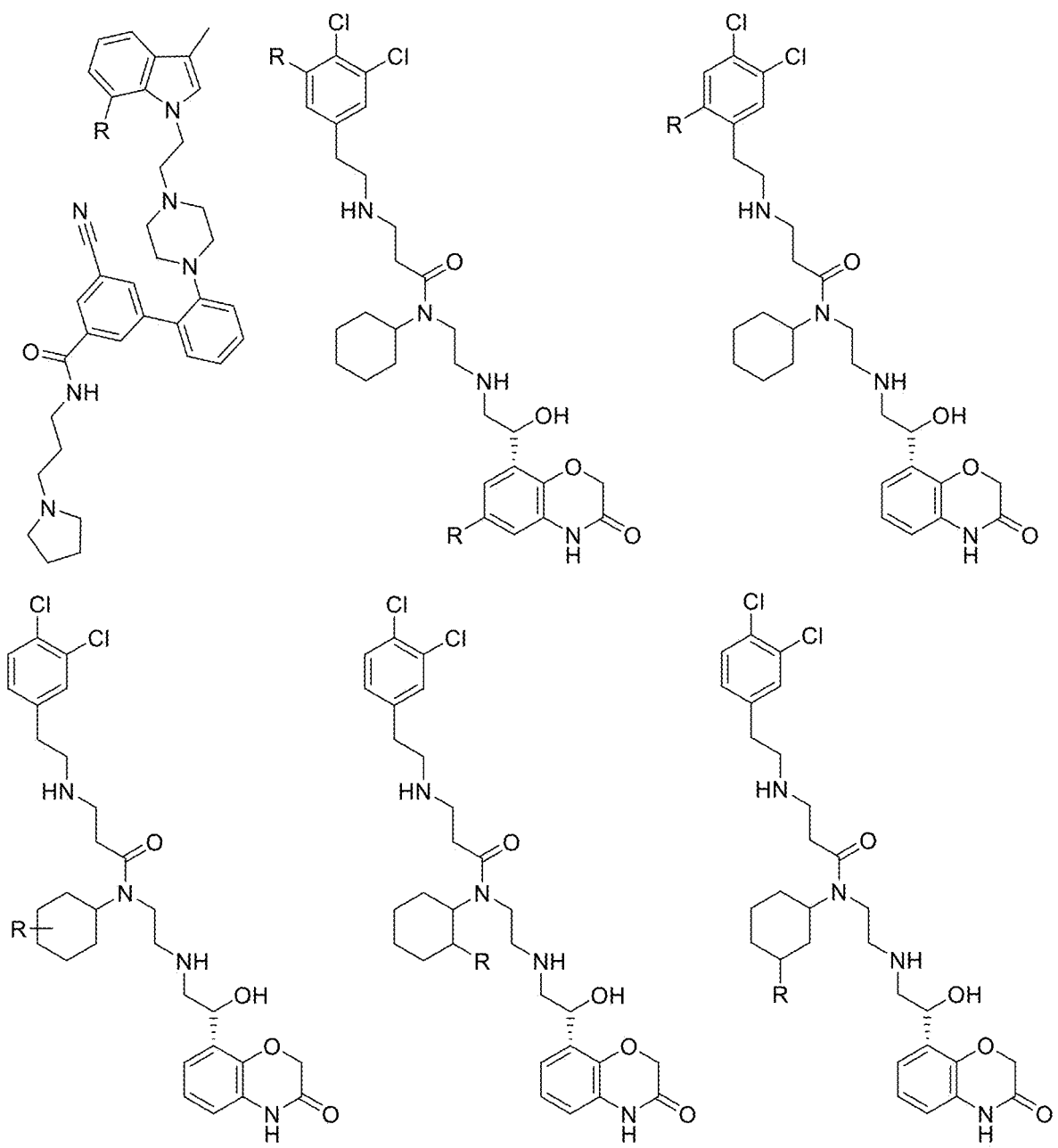
Figure 4O:
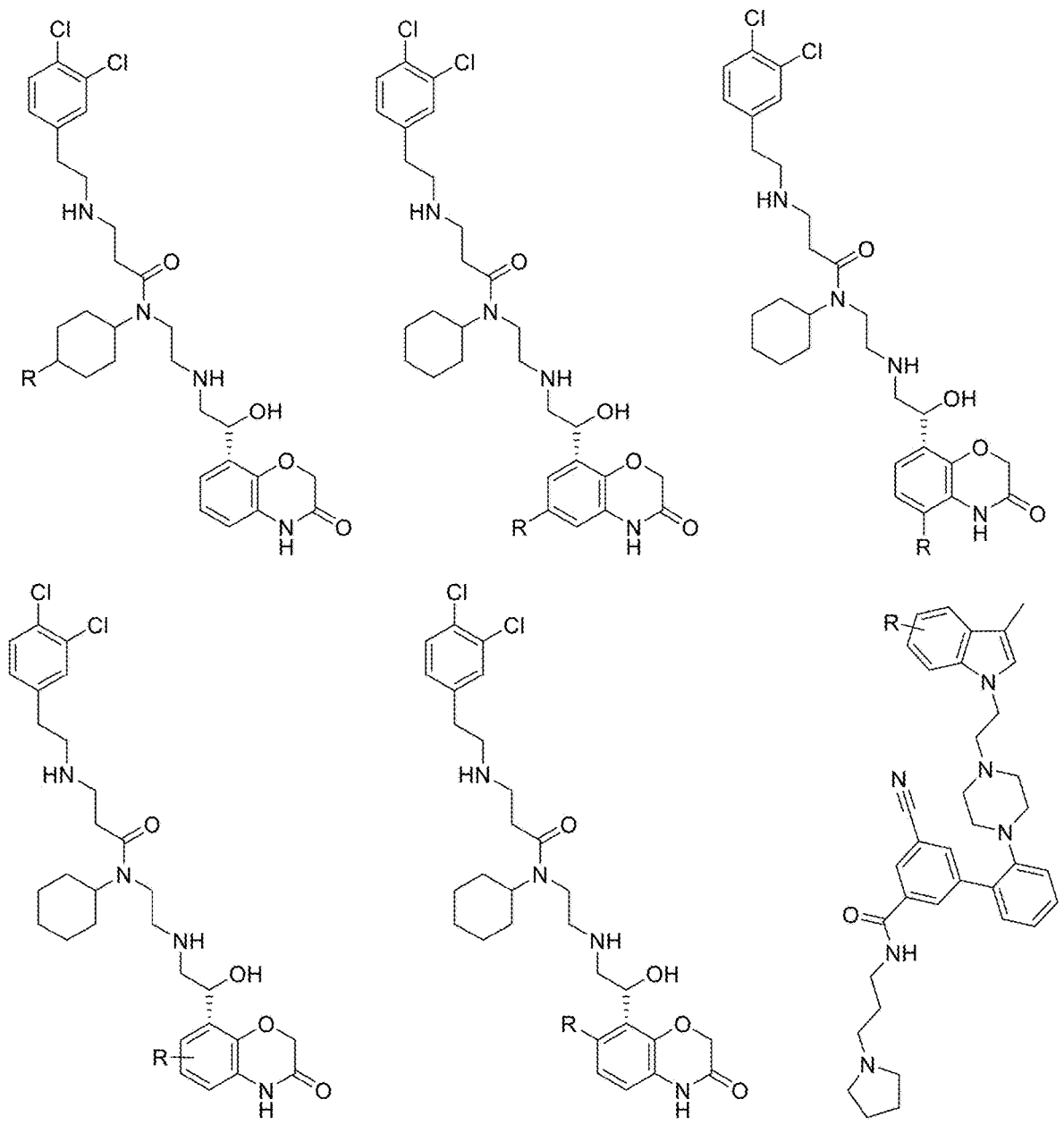
Figure 4P:
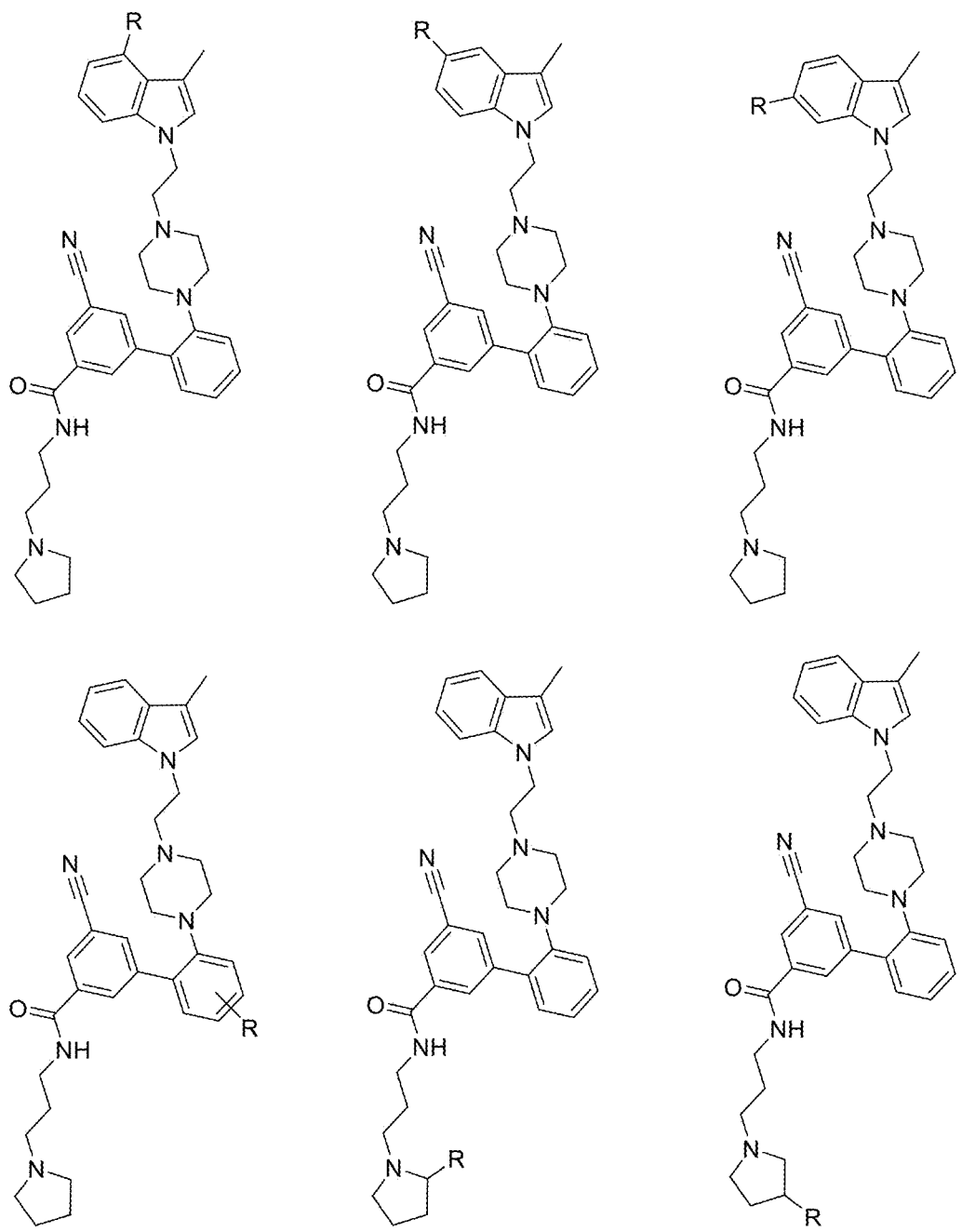
Figure 4Q:
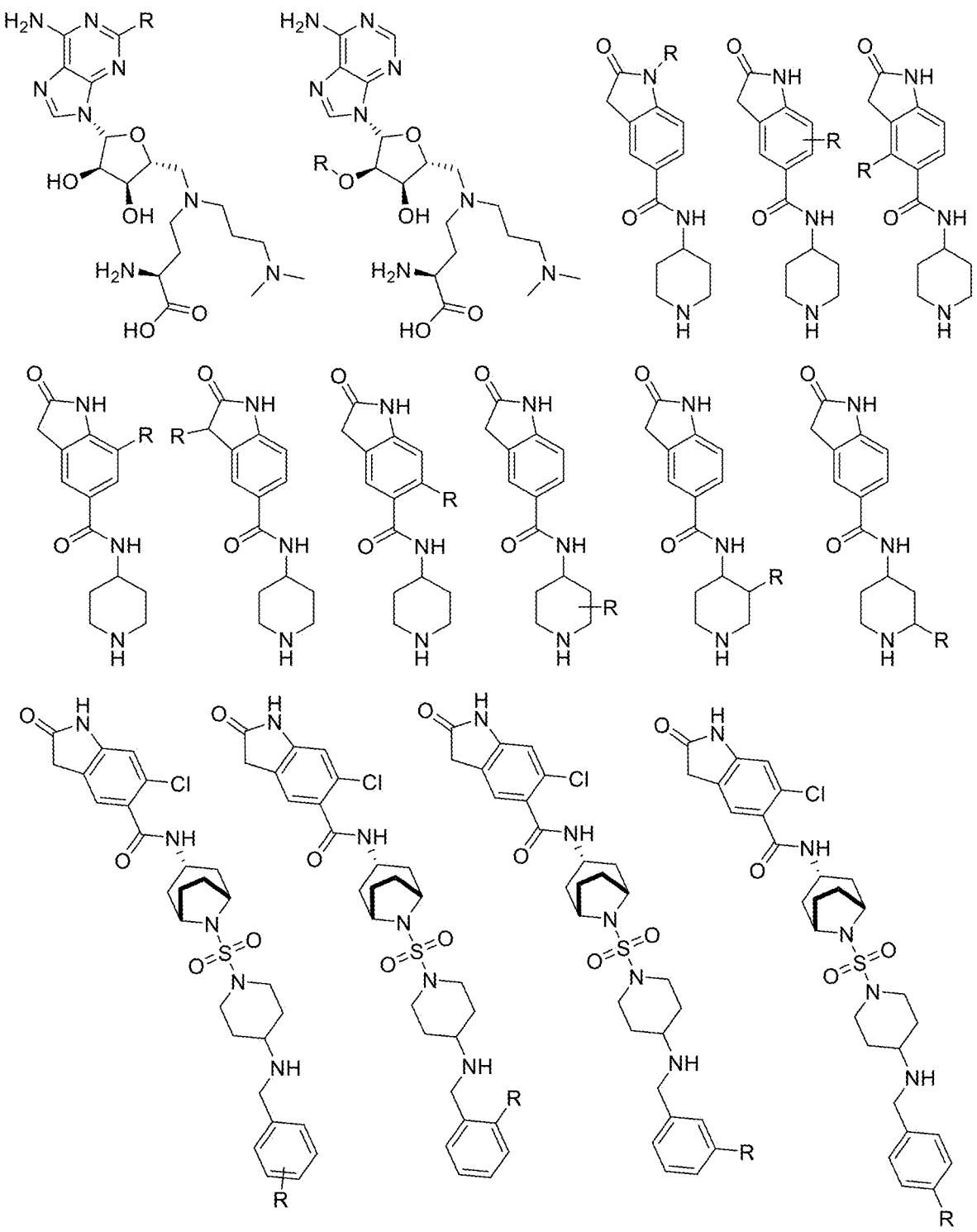
Figure 4R:
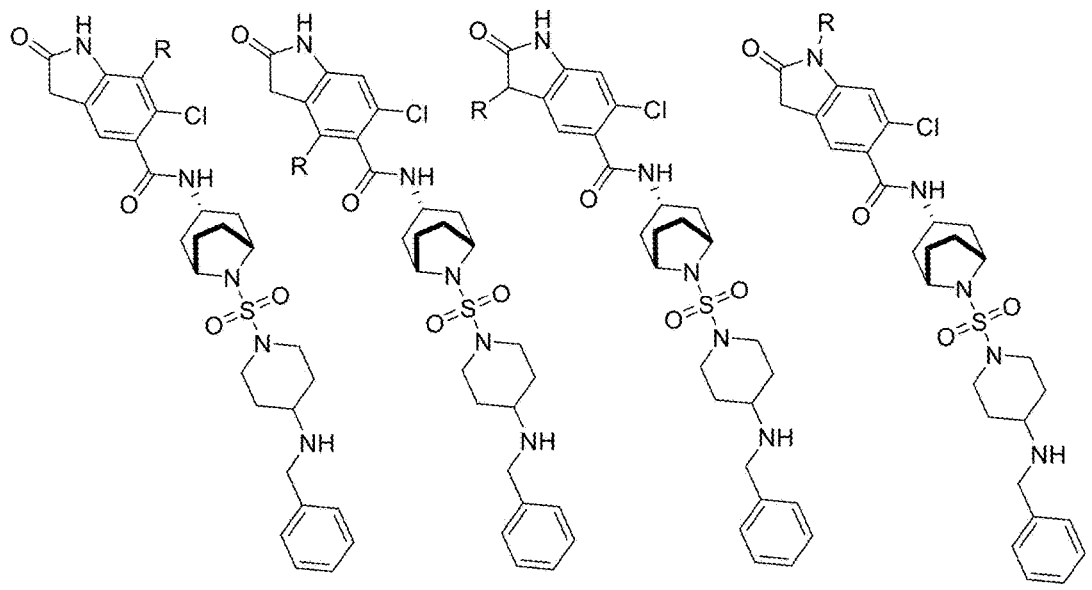
Figure 4S:
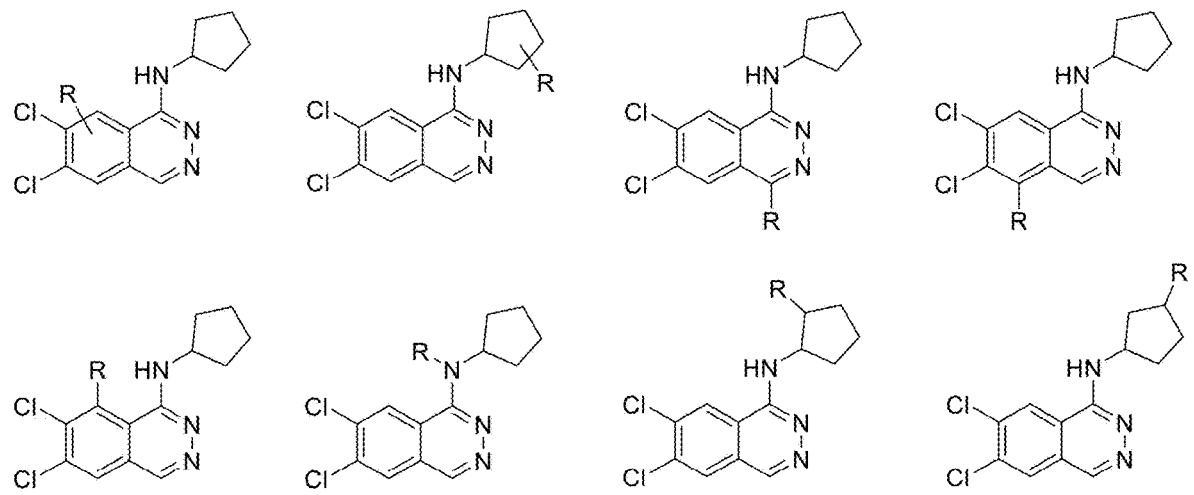
Figure 4T:
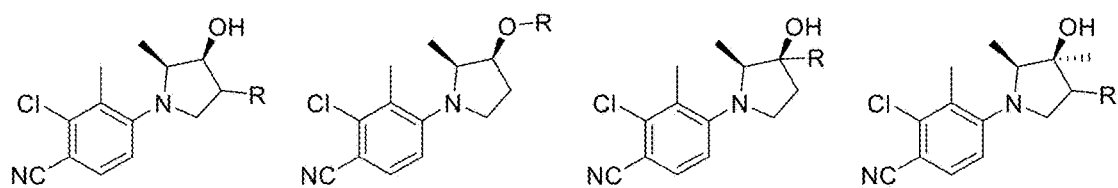
Figure 4U:
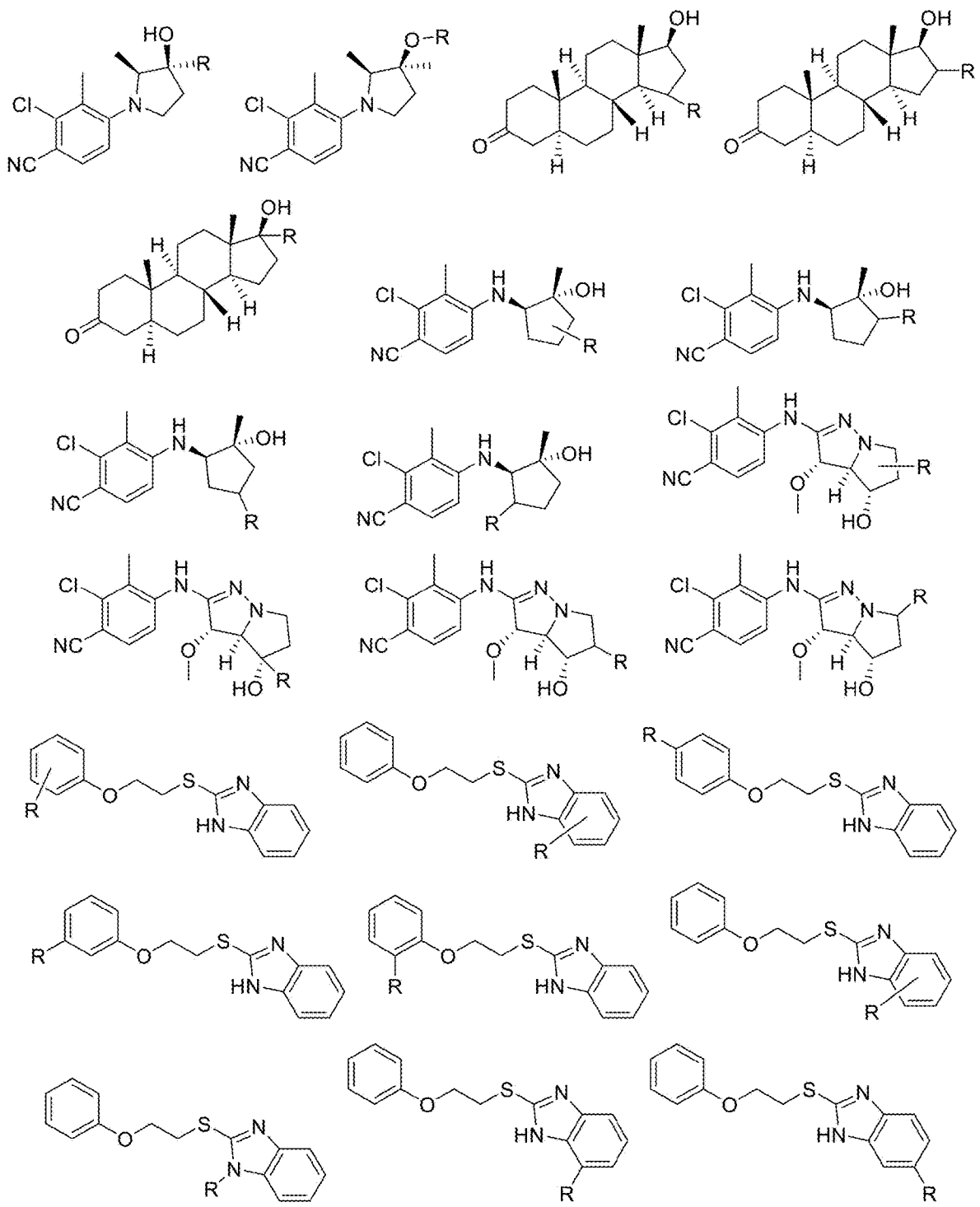
Figure 4V:
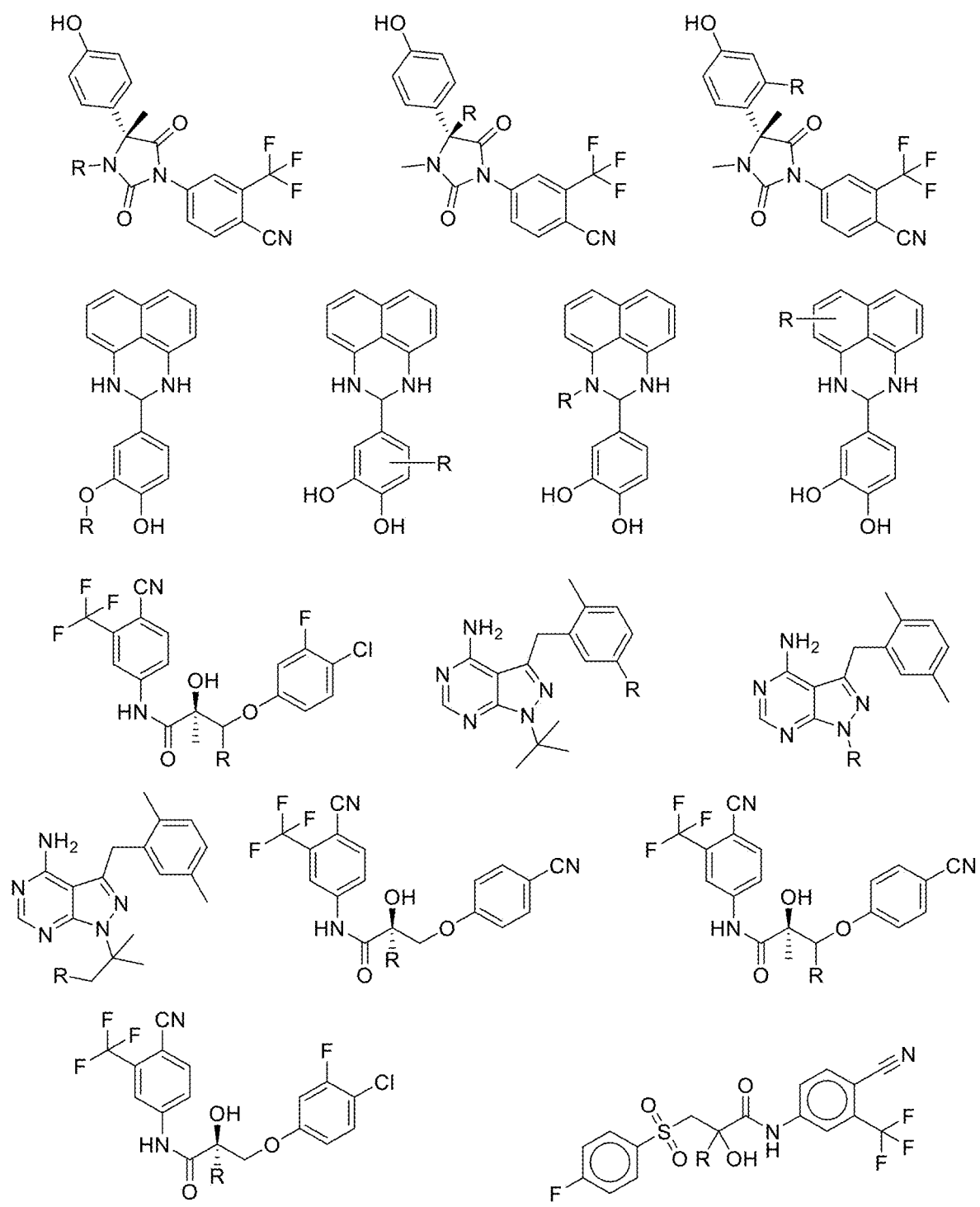
Figure 4W:
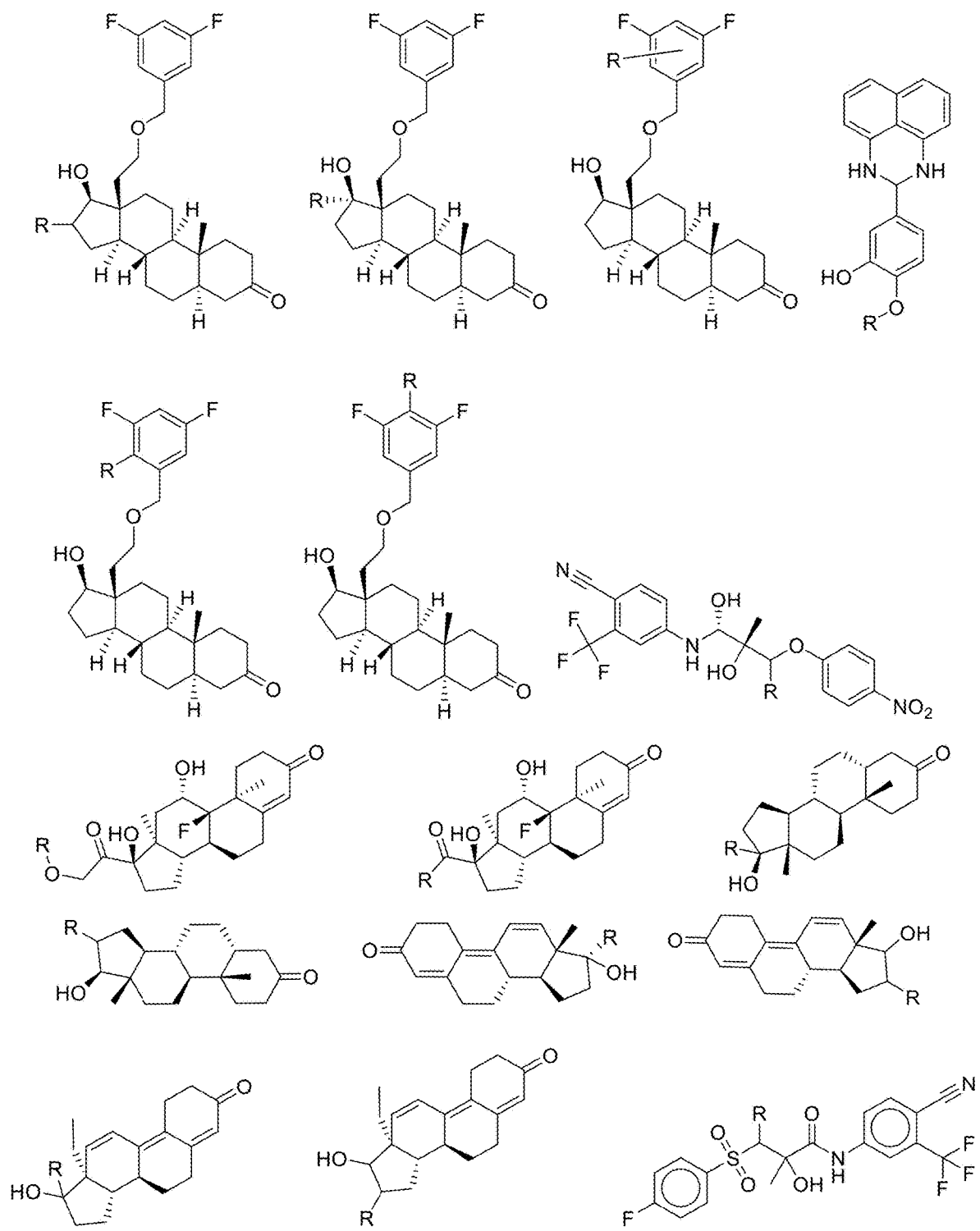
Figure 4X:
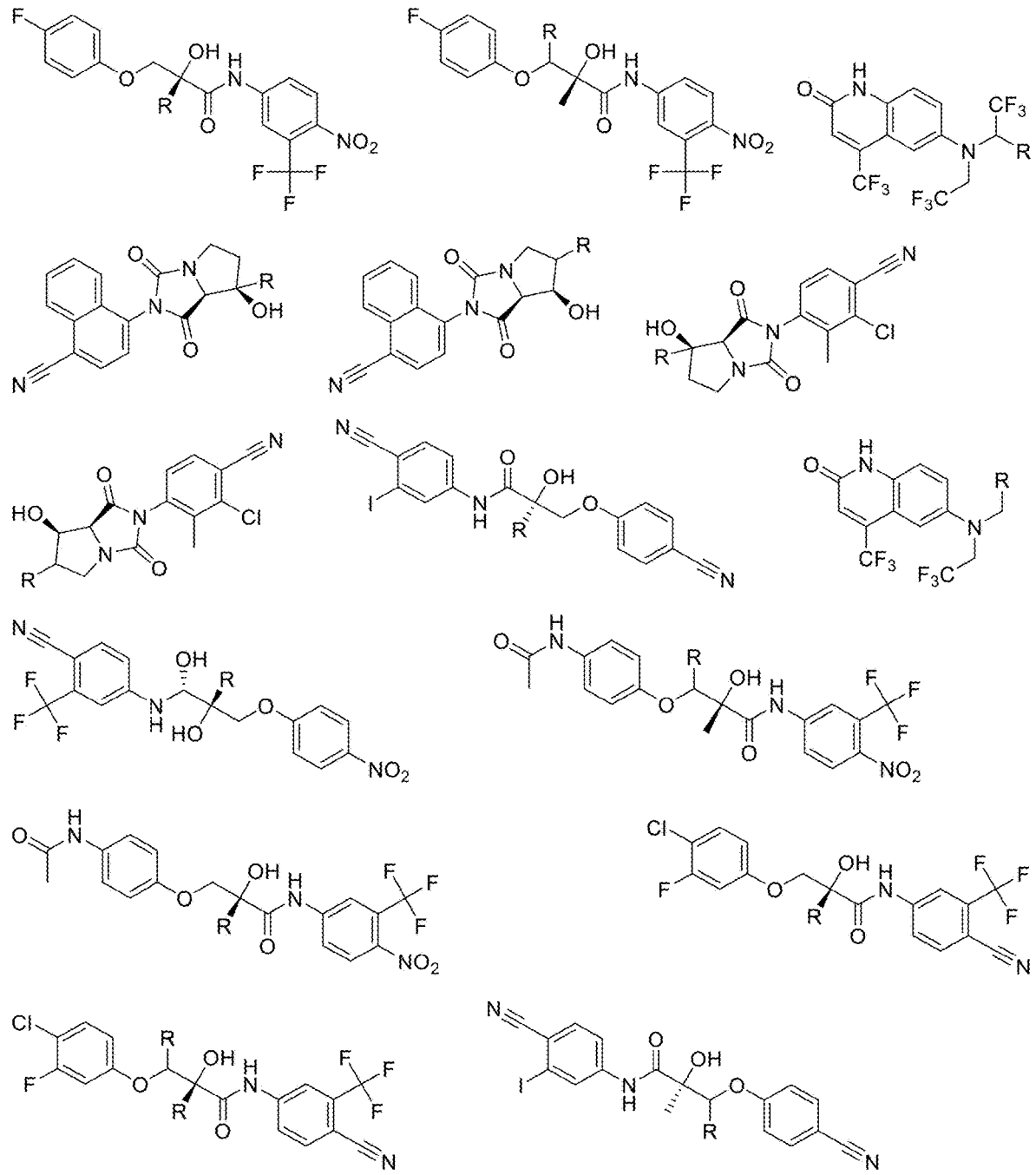
Figure 4Y:
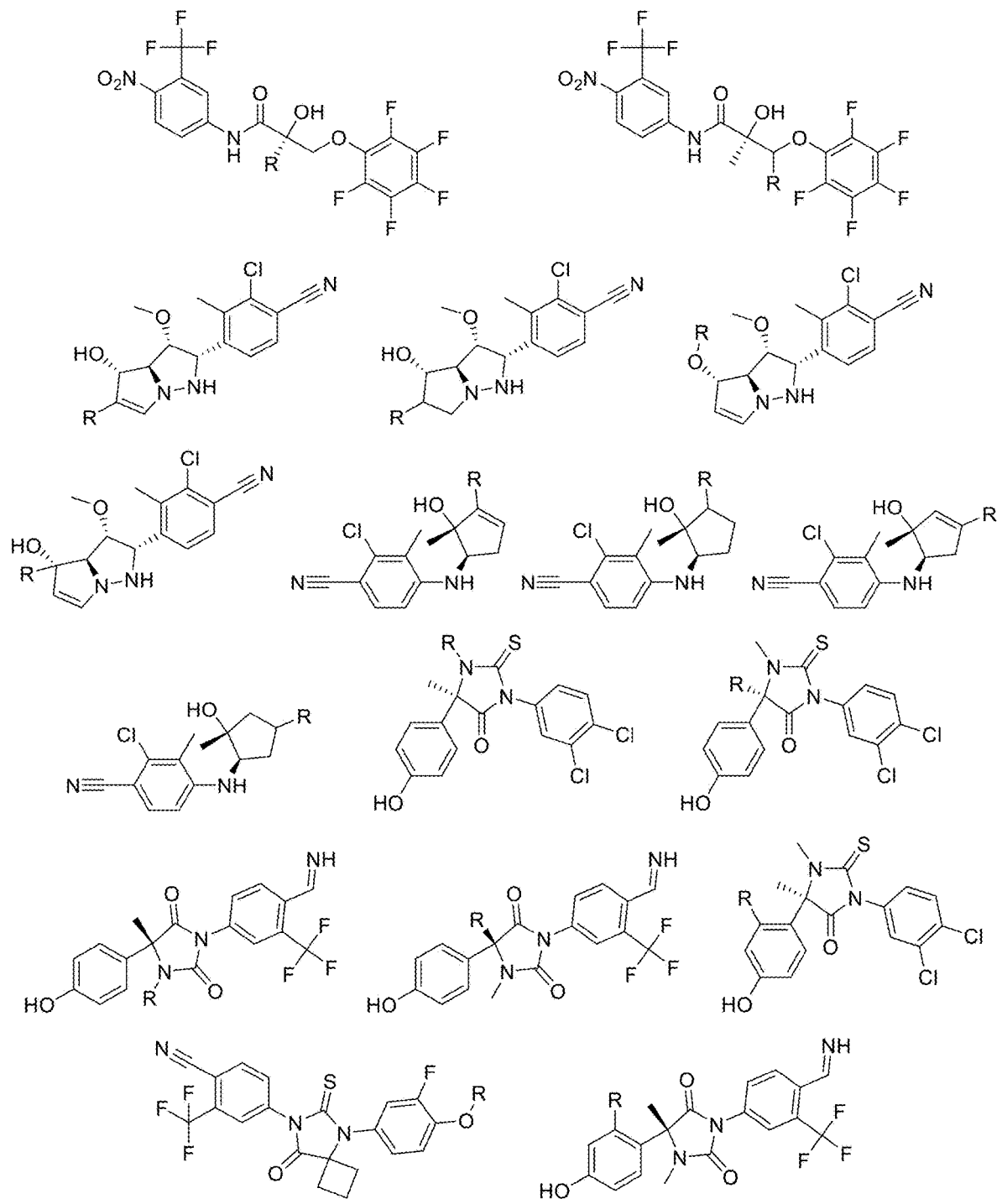
Figure 4Z:
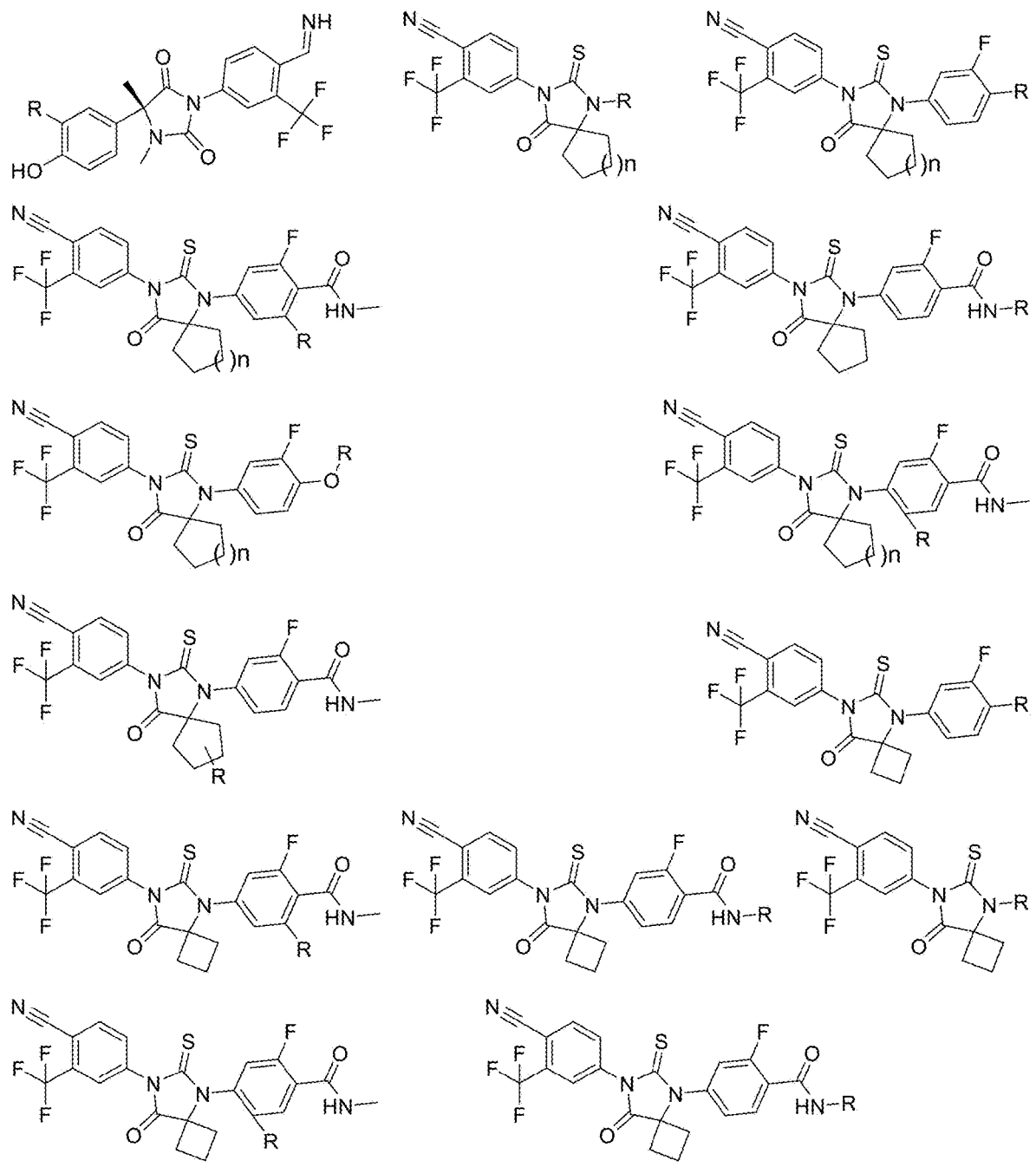
Figure 4A:
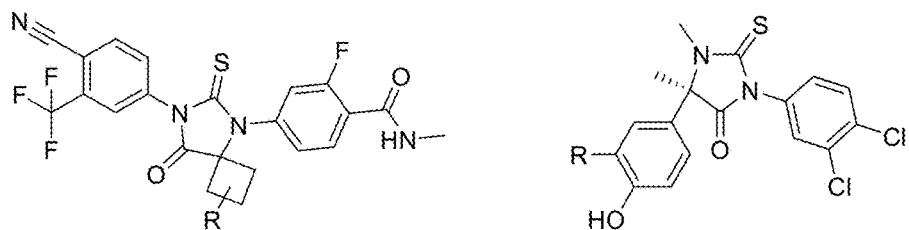
Figure 4B:
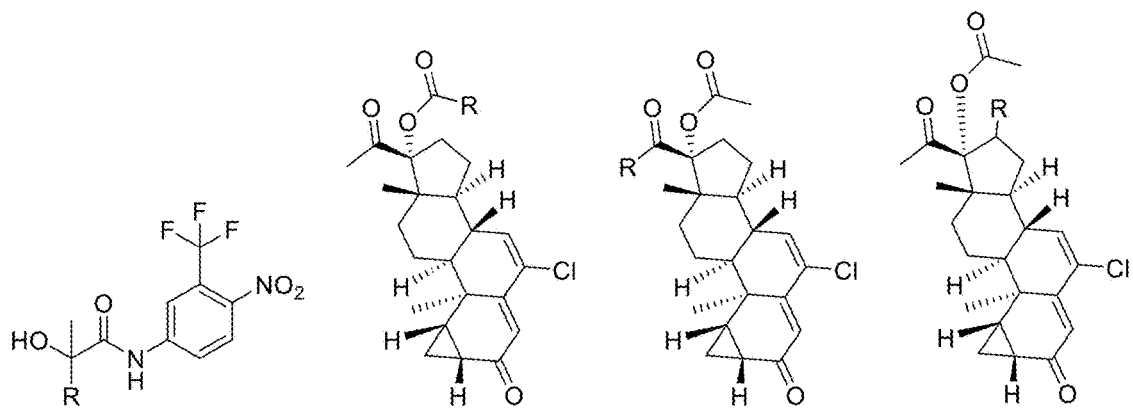
Figure 4C:
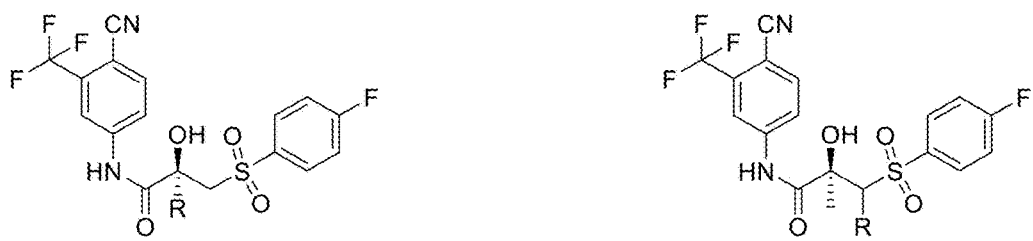
Figure 4D:
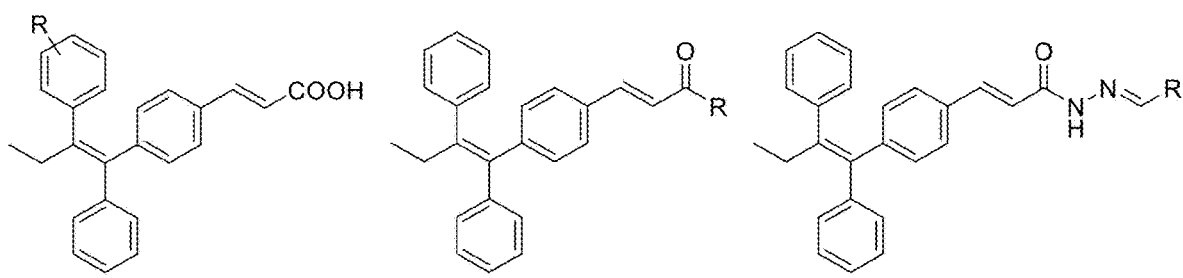
Figure 4E:
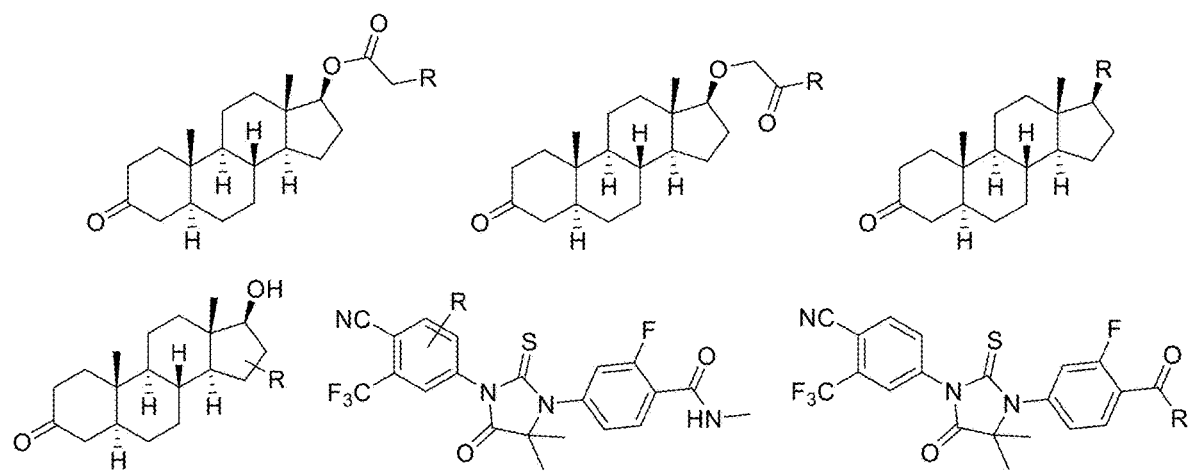

FIG. 4A-4B provides non-limiting examples of SETDB1 Targeting Ligands wherein R represents exemplary points at which the Linker can be attached. For additional examples and related ligands, see, the PDB crystal structure 5KE2 ("SETDB1 in complex with inhibitor XST06472A", Iqbal A. et al.); the PDB crystal structure 5KE3 ("SETDB1 in complex with fragment MRT0181a", Iqbal A. et al.); the PDB crystal structure 5KH6 ("SETDB1 in complex with fragment methyl 3-(methylsulfonylamino)benzoate", Walker J. R. et al. Structural Genomics Consortium); and, the PDB crystal structure 5KCO ("SETDB1 in complex with [N]-(4-chlorophenyl)methanesulfonamide", Walker J. R. et al.) FIG. 4C-4P provides non-limiting examples of SMYD2 Targeting Ligands wherein R represents exemplary points at which the Linker can be attached. For additional examples and related ligands, see, the PDB crystal structure 5KJK ("SMYD2 in complex with inhibitor AZ13450370", Cowen S. D. et al.); the PDB crystal structure 5KJM ("SMYD2 in complex with AZ931", Cowen S. D. et al.); the PDB crystal structure 5KJN ("SMYD2 in complex with AZ506", Cowen S. D. et al.); the PDB crystal structure 5ARF ("SMYD2 in complex with N-[3-(4-chlorophenyl)-1-{N'-cyano-N-[3-(difluoromethoxy)phenyl]carbamimidoyl}-4 5-dihydro-1H-pyrazol-4-YL]-N-ethyl-2-hydroxyacetamide", Eggert E. et al.); the PDB crystal structure 5ARG ("SMYD2 in complex with BAY598", Eggert E. et al.); the PDB crystal structure 4YND ("SMYD2 in complex with A-893", Sweis R. F. et al.); the PDB crystal structure 4WUY ("SMYD2 in complex with LLY-507", Nguyen H. et al.); and, the PDB crystal structure 3S7B ("N-cyclohexyl-N~3~-[2-(3 4-dichlorophenyl)ethyl]-N-(2-{[2-(5-hydroxy-3-oxo-3 4-dihydro-2H-1 4-benzoxazin-8-yl)ethyl]amino}ethyl)-beta-alaninamide", Ferguson A. D. et al.).

FIG. 4Q-4R provide non-limiting examples of SMYD3 Targeting Ligands wherein R represents exemplary points at which the Linker can be attached. For additional examples and related ligands, see, the crystal structure 5H17 ("SMYD3 in complex with 5'-{[(3S)-3-amino-3-carboxypropyl][3-(dimethylamino)propyl]amino}-5'-deoxyadenosine", Van Aller G. S. et al.); the crystal structure 5CCL ("SMYD3 in complex with oxindole compound", Mitchell L. H. et al.); and, the crystal structure 5CCM ("Crystal structure of SMYD3 with SAM and EPZ030456").

FIG. 4S provides non-limiting examples of SUV4-20H1 Targeting Ligands wherein R represents exemplary points at which the Linker can be attached. For additional examples and related ligands, see, the PDB crystal structure 5CPR ("SUV4-20H1 in complex with inhibitor A-196", Bromberg K. D. et al.).

FIG. 4T-4AA provide non-limiting examples of Wild Type Androgen Receptor Targeting Ligands wherein R represents exemplary points at which the Linker can be attached. For additional examples and related ligands, see, the PDB crystal structures 5T8E and 5T8J ("Androgen Receptor in complex with 4-(pyrrolidin-1-yl)benzonitrile derivatives", Asano M. et al.); Asano M. et al. *Bioorg. Med Chem. Lett.* 27: 1897-1901 (2017); the PDB crystal structure 5JJM ("Androgen Receptor", Nadal M. et al.); the PDB crystal structure 5CJ6 ("Androgen Receptor in complex with 2-Chloro-4-[[(1R 2R)-2-hydroxy-2-methyl-cyclopentyl] amino]-3-methyl-benzonitrile derivatives", Saeed A. et al.); the PDB crystal structure 4QL8 ("Androgen Receptor in complex with 3-alkoxy-pyrrolo[1 2-b]pyrazolines derivatives", Ullrich T. et al.); the PDB crystal structure 4HLW ("Androgen Receptor Binding Function 3 (BF3) Site of the Human Androgen Receptor through Virtual Screening", Munuganti R. S. et al.); the PDB crystal structure 3V49 ("Androgen Receptor lbd with activator peptide and sarm inhibitor 1", Nique F. et al.); Nique F. et al. *J. Med Chem.* 55: 8225-8235 (2012); the PDB crystal structure 2YHD ("Androgen Receptor in complex with AF2 small molecule inhibitor", Axerio-Cilies P. et al.); the PDB crystal structure 3RLJ ("Androgen Receptor ligand binding domain in complex with SARM S-22", Bohl C. E. et al.); Bohl C. E. et al. *J. Med Chem.* 54: 3973-3976 (2011); the PDB crystal structure 3B5R ("Androgen Receptor ligand binding domain in complex with SARM C-31", Bohl C. E. et al.); Bohl C. E. et al. *Bioorg. Med Chem. Lett.* 18: 5567-5570 (2008); the PDB crystal structure 2PIP ("Androgen Receptor ligand binding domain in complex with small molecule", Estebanez-Perpina E. et al.); Estebanez-Perpina. E. *Proc. Natl. Acad Sci.* 104:16074-16079 (2007); the PDB crystal structure 2PNU ("Androgen Receptor ligand binding domain in complex with EM5744", Cantin L. et al.); and, the PDB crystal structure 2HVC ("Androgen Receptor ligand binding domain in complex with LGD2226", Wang F. et al.). For additional related ligands, see, Matias P. M. et al. "Structural Basis for the Glucocorticoid Response in a Mutant Human Androgen Receptor (Ar(Ccr)) Derived from an Androgen-Independent Prostate Cancer." *J. Med Chem.* 45: 1439 (2002); Sack J. S. et al. "Crystallographic structures of the ligand-binding domains of the androgen receptor and its T877A mutant complexed with the natural agonist dihydrotestosterone." *Proc. Natl. Acad Sci.* 98: 4904-4909 (2001); He B. et al. "Structural basis for androgen receptor interdomain and coactivator interactions suggests a transition in nuclear receptor activation function dominance." *Mol. Cell* 16: 425-438 (2004); Pereira de Jesus-Tran K. "Comparison of crystal structures of human androgen receptor ligand-binding domain complexed with various agonists reveals molecular determinants responsible for binding affinity." *Protein Sci.* 15: 987-999 (2006); Bohl C. E. et al. "Structural Basis for Accommodation of Nonsteroidal Ligands in the Androgen Receptor." *Mol Pharmacol.* 63(1): 211-23 (2003); Sun C. et al. "Discovery of potent orally-active and muscle-selective androgen receptor modulators based on an N-aryl-hydroxybicyclohydantoin scaffold." *J. Med Chem.* 49: 7596-7599 (2006); Nirschl A. A. et al. "N-aryl-oxazolidin-2-imine muscle selective androgen receptor modulators enhance potency through pharmacophore reorientation." *J. Med Chem.* 52: 2794-2798 (2009); Bohl C. E. et al. "Effect of B-ring substitution pattern on binding mode of propionamide selective androgen receptor modulators." *Bioorg. Med Chem. Lett.* 18: 5567-5570 (2008); Ullrich T. et al. "3-alkoxy-pyrrolo[1 2-b]pyrazolines as selective androgen receptor modulators with ideal physicochemical properties for transdermal administration." *J. Med Chem.* 57: 7396-7411 (2014); Saeed A. et al. "2-Chloro-4-[[(1R 2R)-2-hydroxy-2-methyl-cyclopentyl] amino]-3-methyl-benzonitrile: A Transdermal Selective Androgen Receptor Modulator (SARM) for Muscle Atrophy." *J. Med Chem.* 59: 750-755 (2016); Nique et al. "Discovery of diarylhydantoins as new selective androgen receptor modulators." *J. Med Chem.* 55: 8225-8235 (2012); and, Michael E. Jung et al. "Structure-Activity Relationship for Thiohydantoin Androgen Receptor Antagonists for Castration-Resistant Prostate Cancer (CRPC)." *J. Med Chem.* 53: 2779-2796 (2010).

FIG. 4BB provides non-limiting examples of Mutant T877A Androgen Receptor Targeting Ligands wherein R represents exemplary points at which the Linker can be attached. For additional examples and related ligands, see, the PDB crystal structure 4OGH ('Androgen Receptor T877A-AR-LBD", Hsu C. L. et al.) and the PDB crystal structure 2OZ7 ("Androgen Receptor T877A-AR-LBD", Bohl C. E. et al.).

FIG. 4CC provides non-limiting examples of Mutant W741L Androgen Receptor Targeting Ligands wherein R represents exemplary points at which the Linker can be attached. For additional examples and related ligands, see, the PDB crystal structure 4OJB ("Androgen Receptor T877A-AR-LBD", Hsu C. L. et al.).

FIG. 4DD-4EE provide non-limiting examples of Estrogen and/or Androgen Targeting Ligands wherein R represents exemplary points at which the Linker can be attached.

Figure 5A:
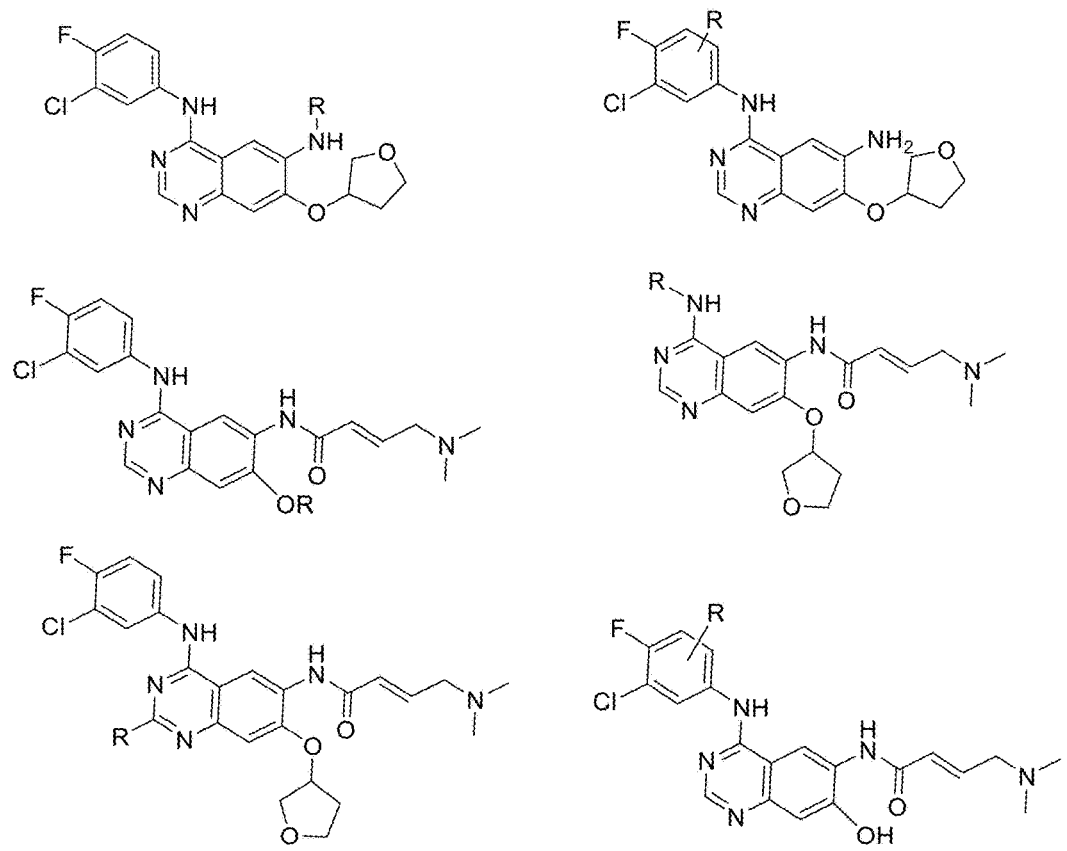

FIG. 5A provides non-limiting examples of Afatinib, a Targeting Ligand for the EGFR and ErbB2/4 receptors. R represents exemplary points at which the Linker can be attached.

Figure 5B:
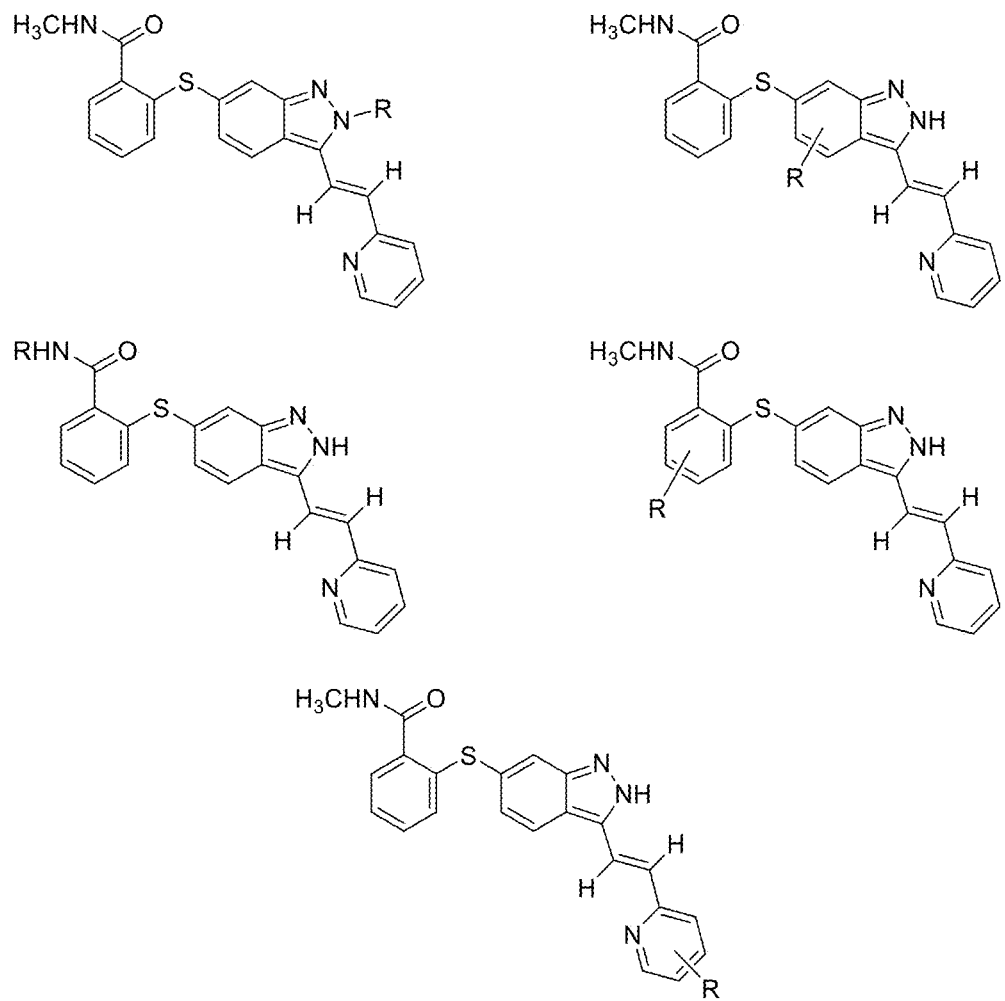

FIG. 5B provides non-limiting examples of Axitinib, a Targeting Ligand for the VEGFR1/2/3, PDGFRβ, and Kit receptors. R represents exemplary points at which the Linker can be attached.

Figure 5C:
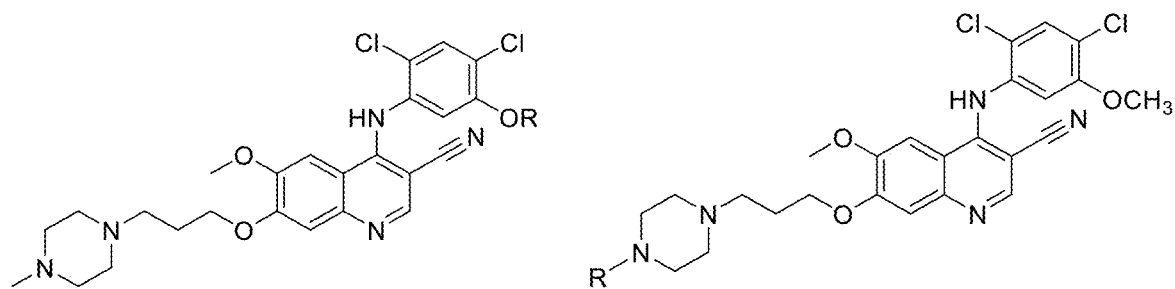
Figure 5D:
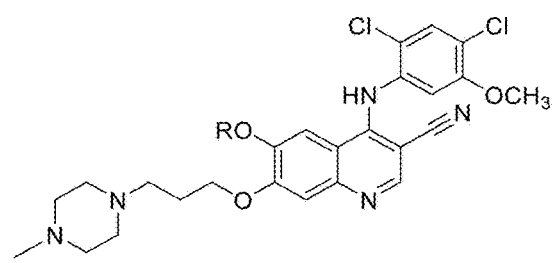

FIG. 5C-5D provide non-limiting examples of Bosutinib, a Targeting Ligand for the BCR-Abl, Src, Lyn and Hck receptors. R represents exemplary points at which the Linker can be attached.

Figure 5E:
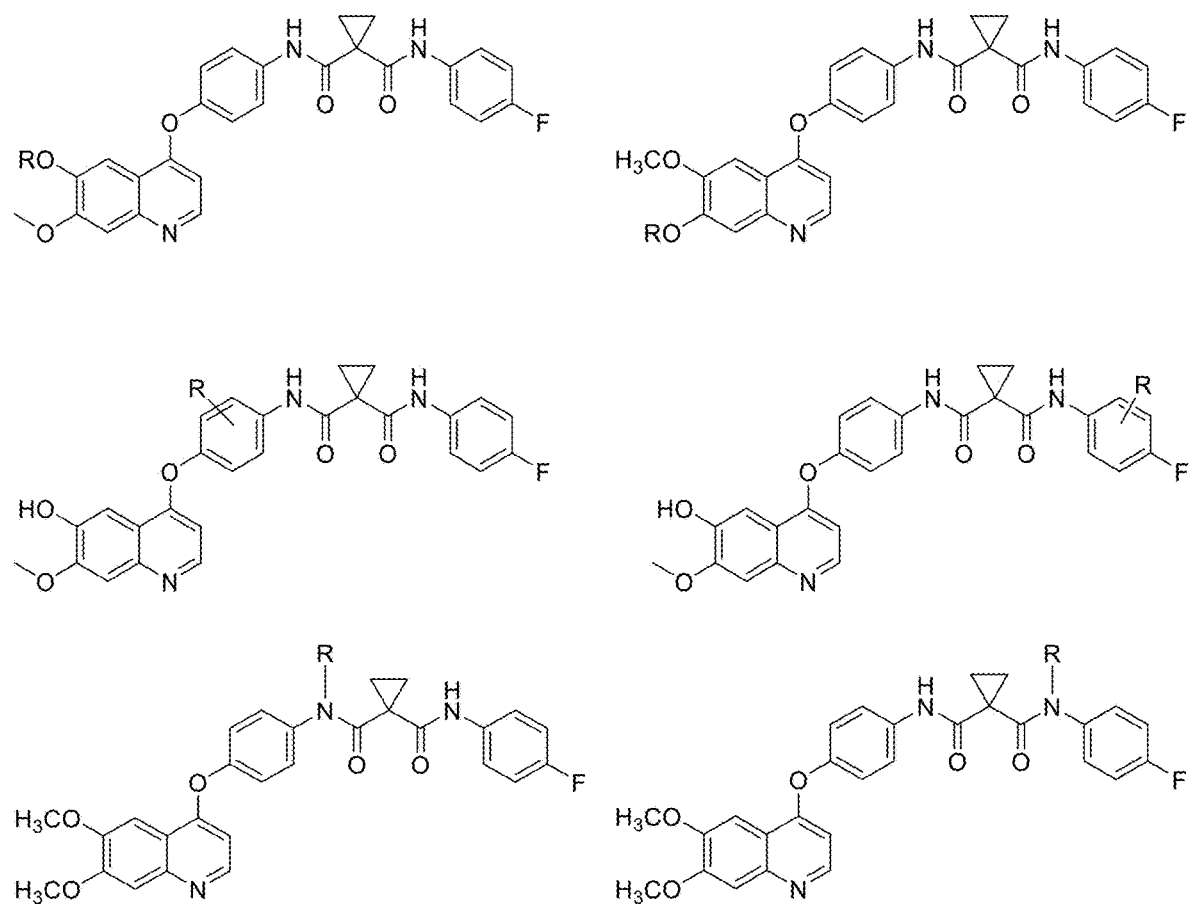

FIG. 5E provides non-limiting examples of Cabozantinib, a Targeting Ligand for the RET, c-Met, VEGFR1/2/3, Kit, TrkB, Flt3, Axl, and Tie 2 receptors. R represents exemplary points at which the Linker can be attached.

Figure 5F:
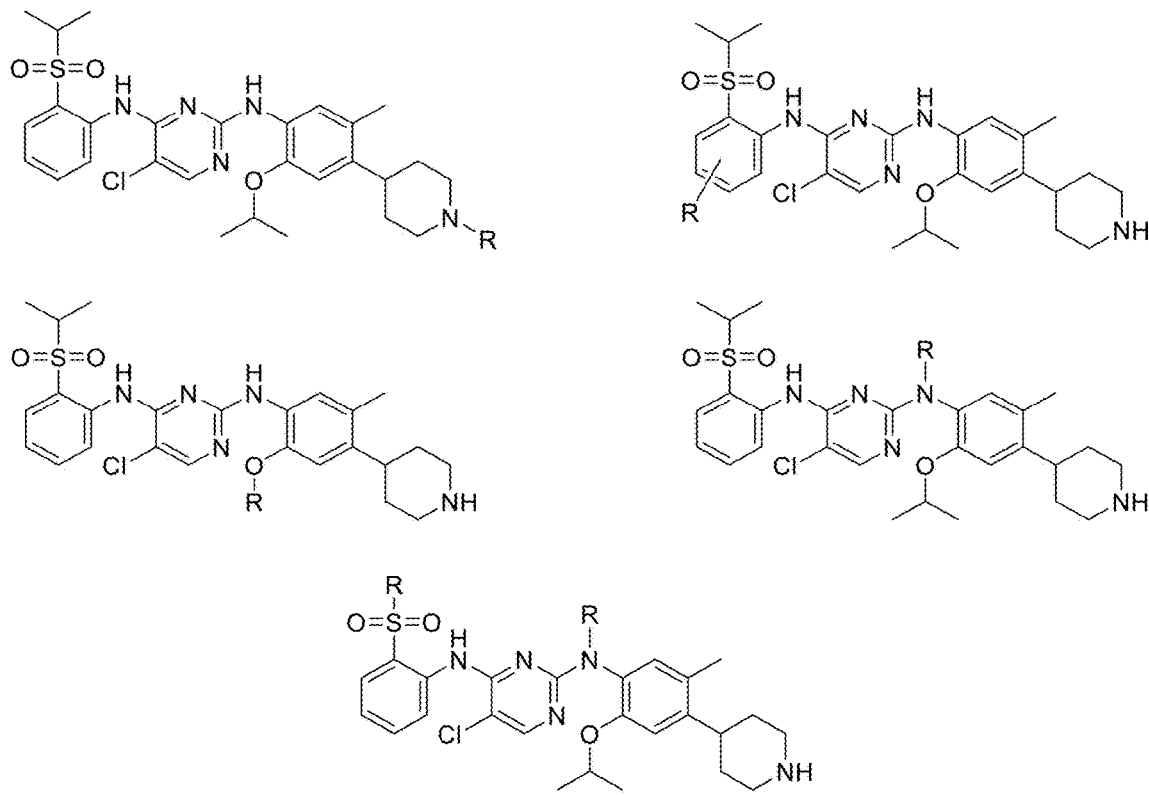

FIG. 5F provides non-limiting examples of Ceritinib, a Targeting Ligand for the ALK, IGF-1R, InsR, and ROS1 receptors. R represents exemplary points at which the Linker can be attached.

Figure 5G:
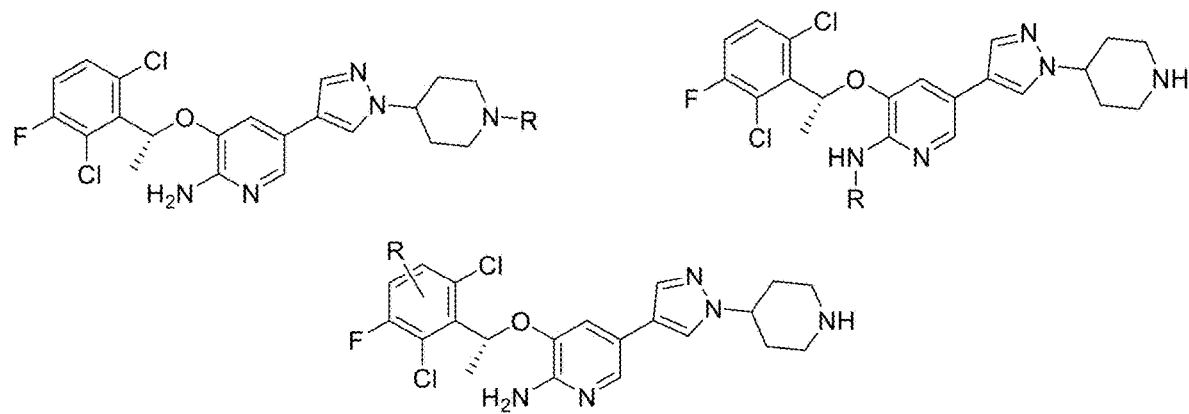

FIG. 5G provides non-limiting examples of Crizotinib, a Targeting Ligand for the ALK, c-Met, HGFR, ROS1, and MST1R receptors. R represents exemplary points at which the Linker can be attached.

Figure 5H:
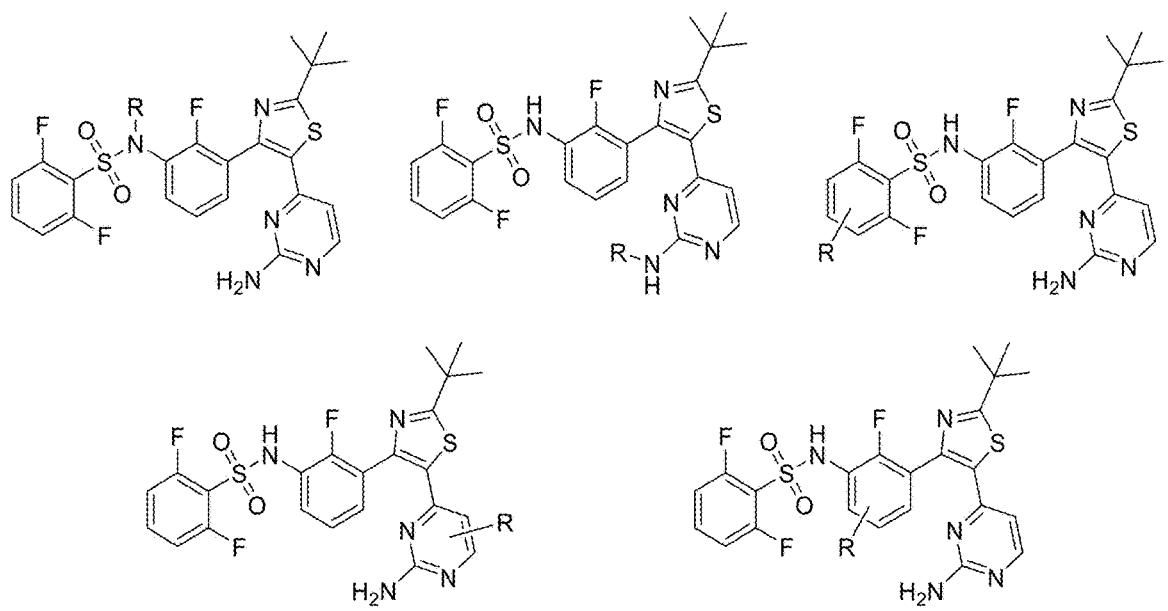

FIG. 5H provides non-limiting examples of Dabrafenib, a Targeting Ligand for the B-Raf receptor. R represents exemplary points at which the Linker can be attached.

Figure 5I:
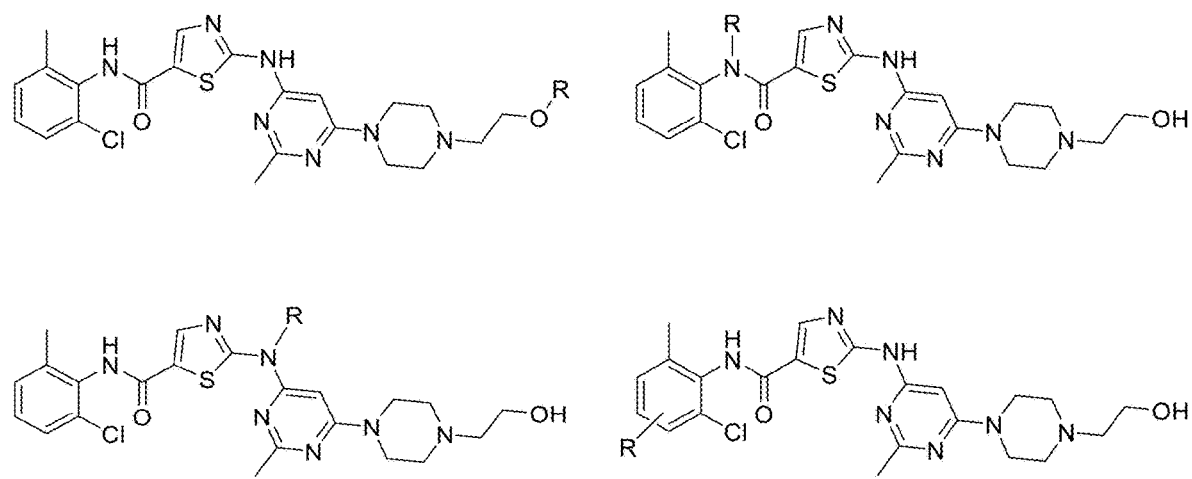

FIG. 5I provides non-limiting examples of Dasatinib, a Targeting Ligand for the BCR-Abl, Src, Lck, Lyn, Yes, Fyn, Kit, EphA2, and PDGFRβ receptors. R represents exemplary points at which the Linker can be attached.

Figure 5J:
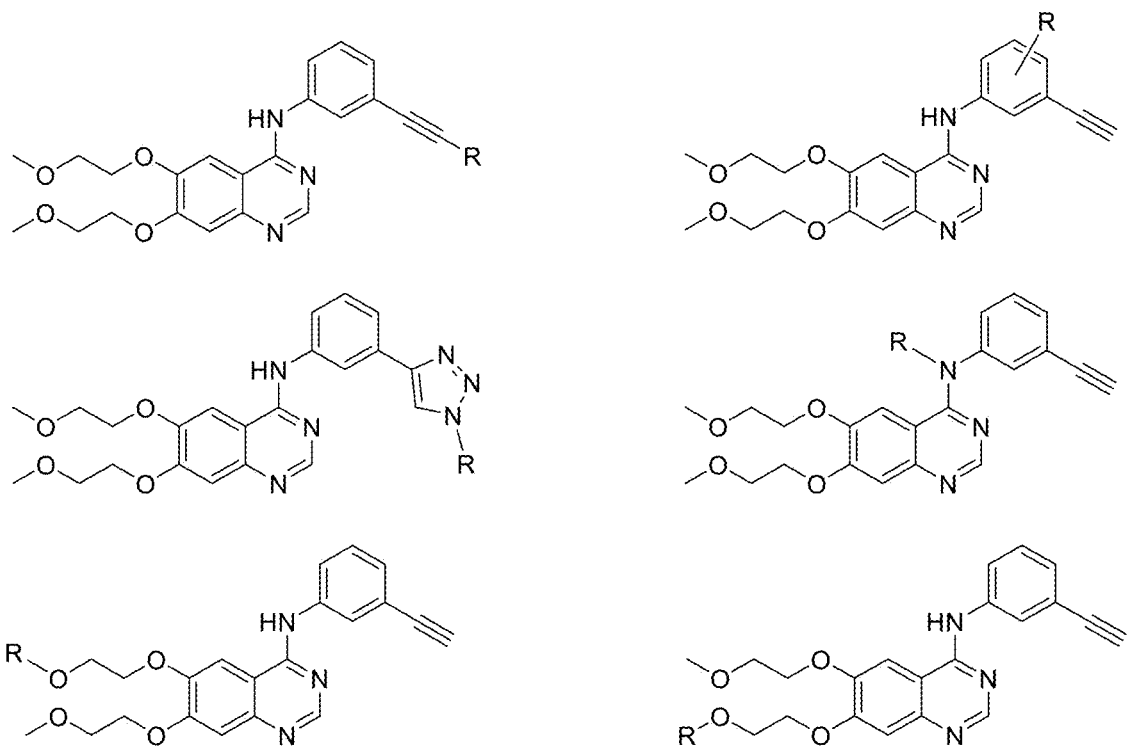

FIG. 5J provides non-limiting examples of Erlotinib, a Targeting Ligand for the EGFR receptor. R represents exemplary points at which the Linker can be attached.

Figure 5K:
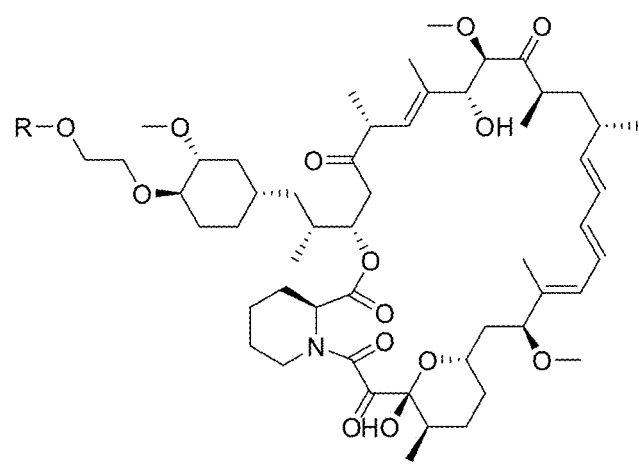
Figure 5O:
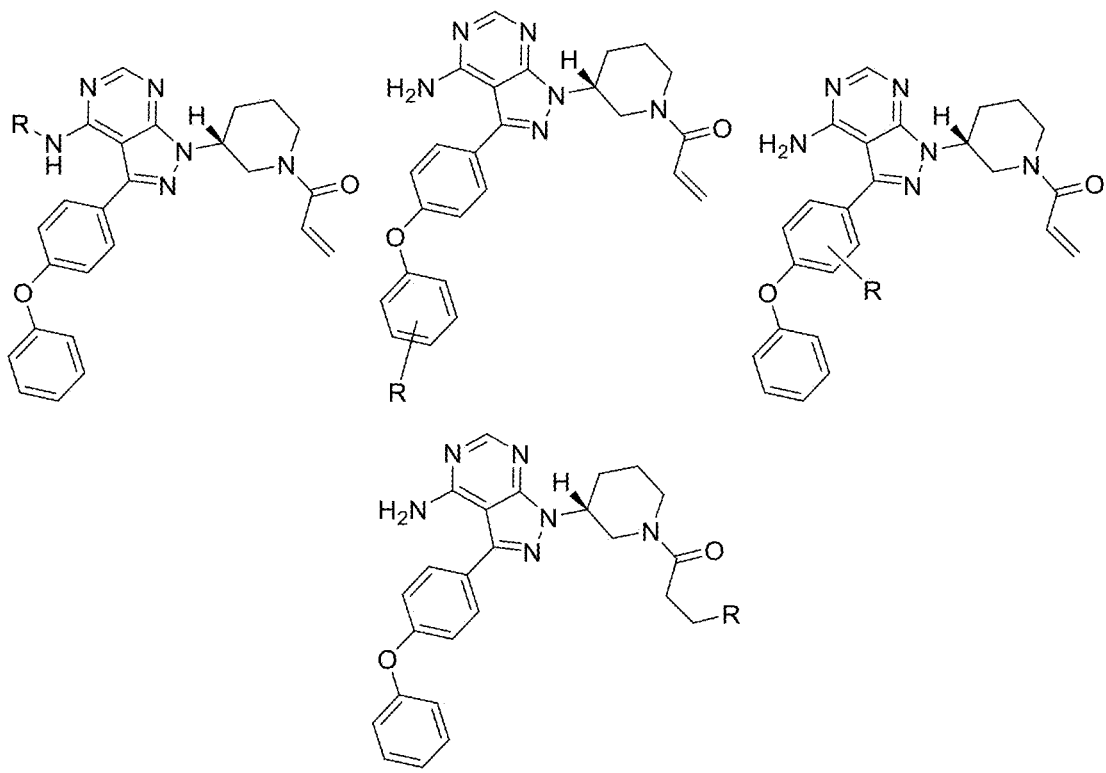
Figure 5P:
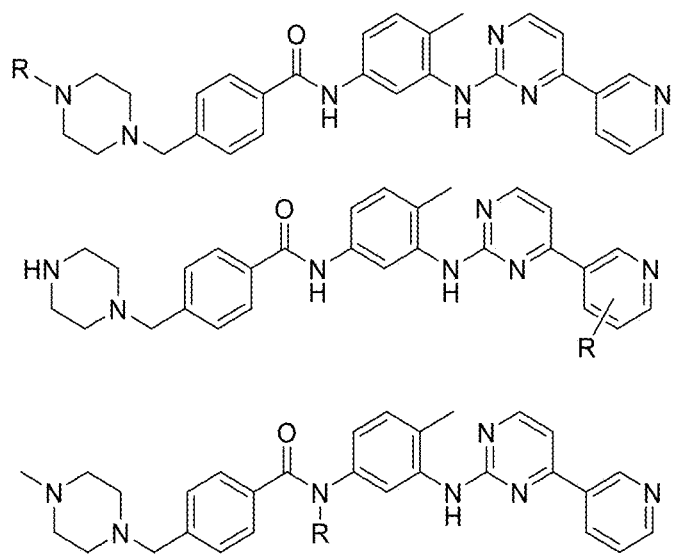
Figure 5Q:
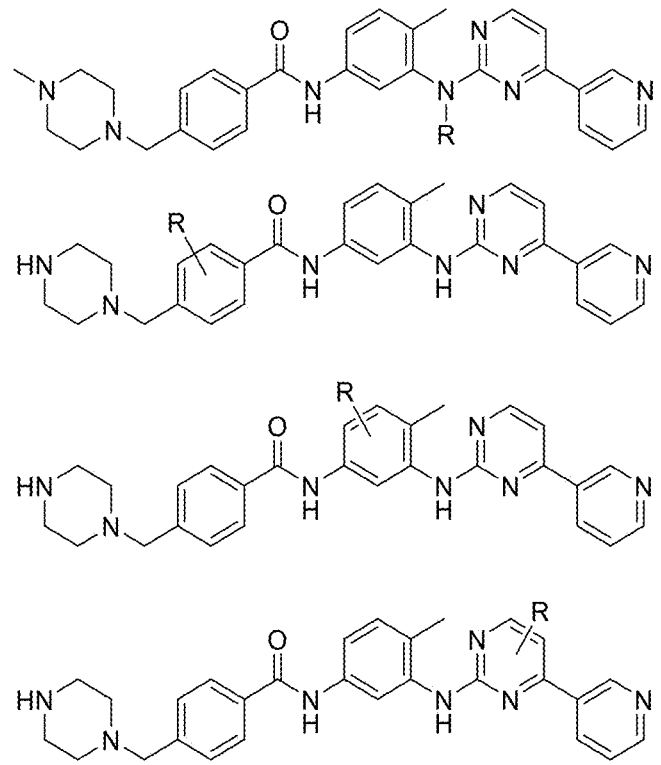
Figure 5R:
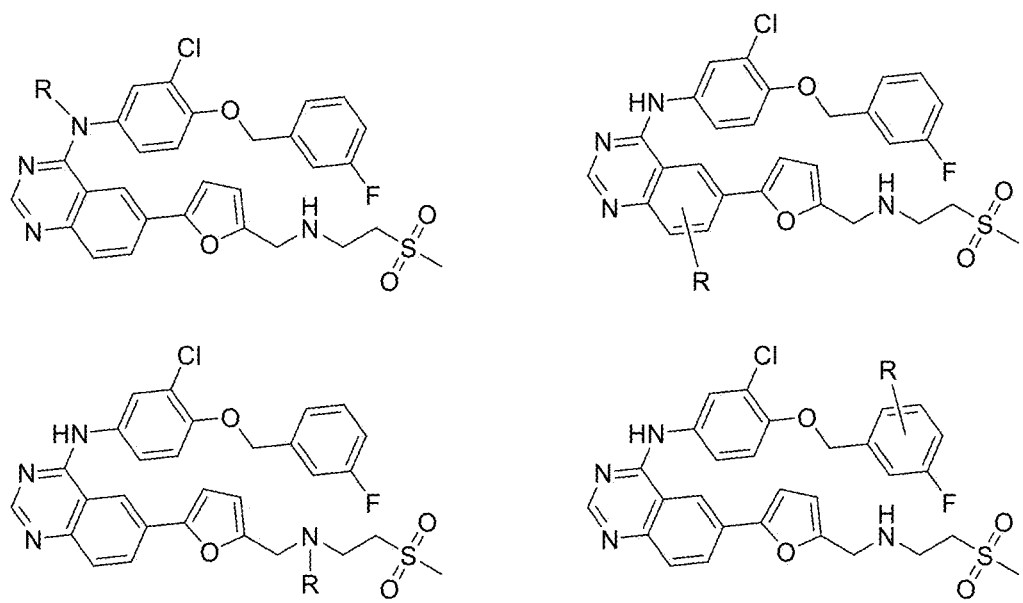
Figure 5S:
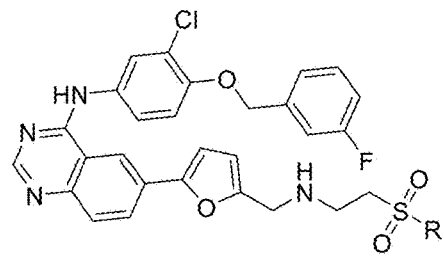
Figure 5T:
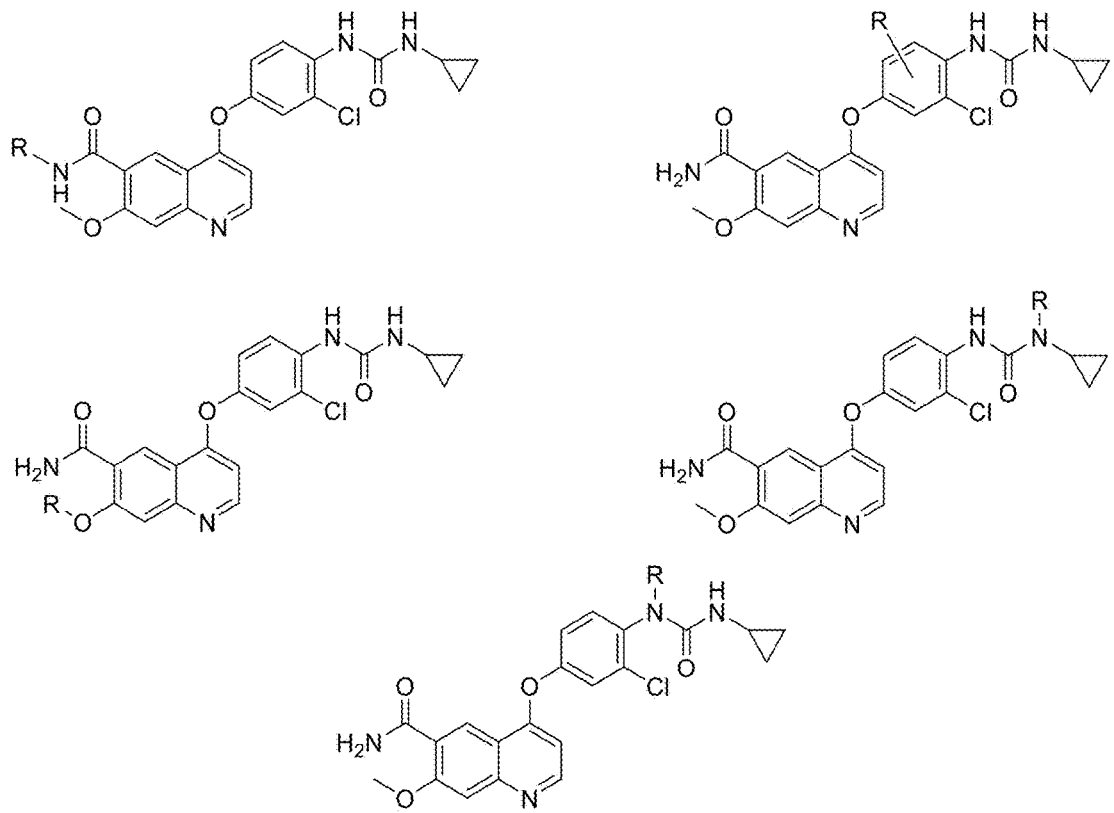
Figure 5U:
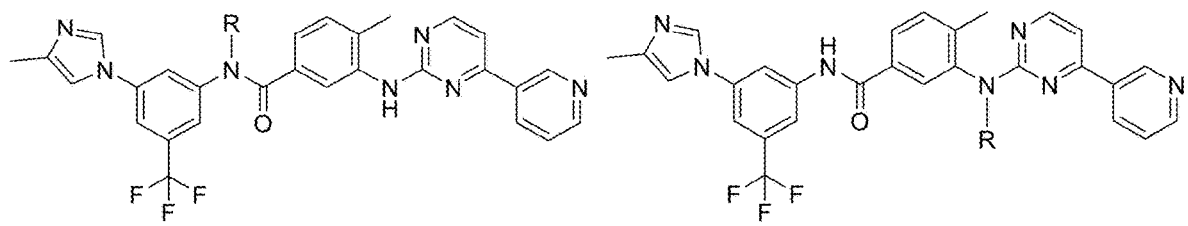
Figure 5V:
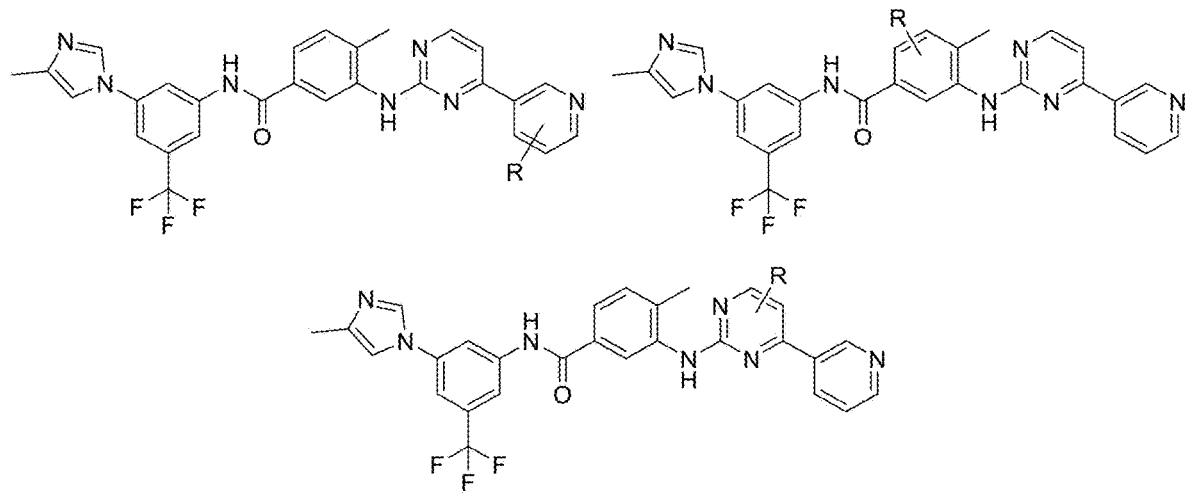
Figure 5W:
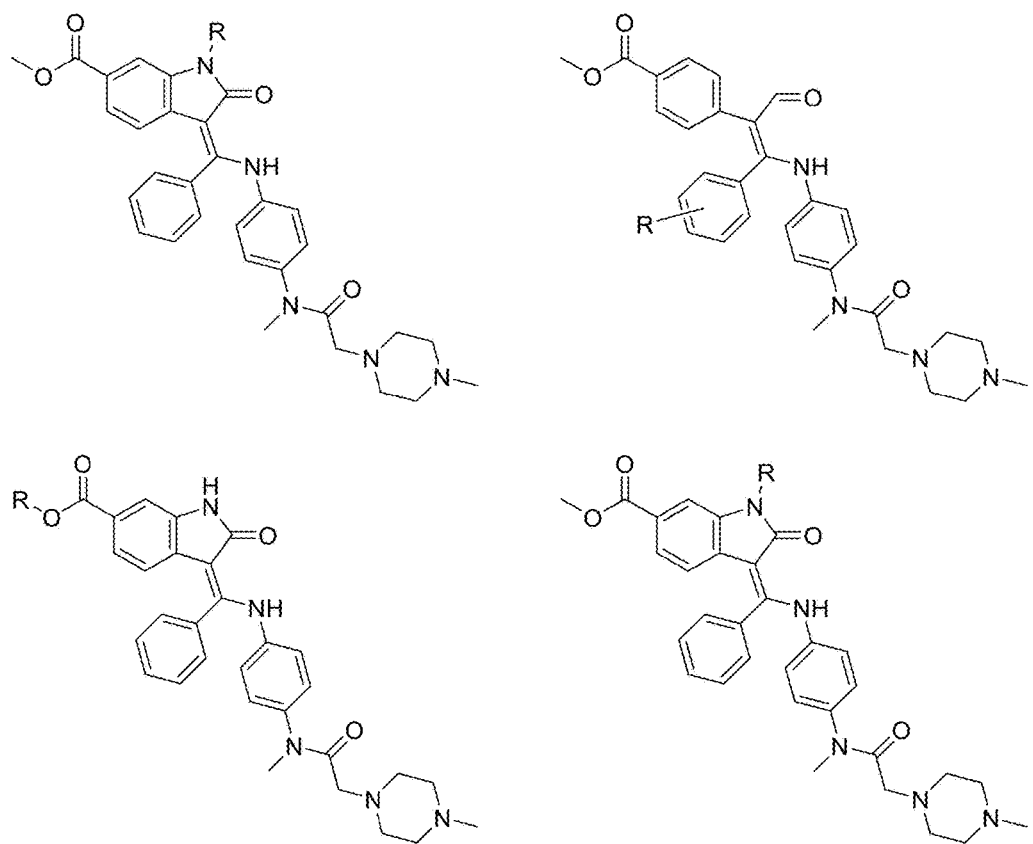
Figure 5X:
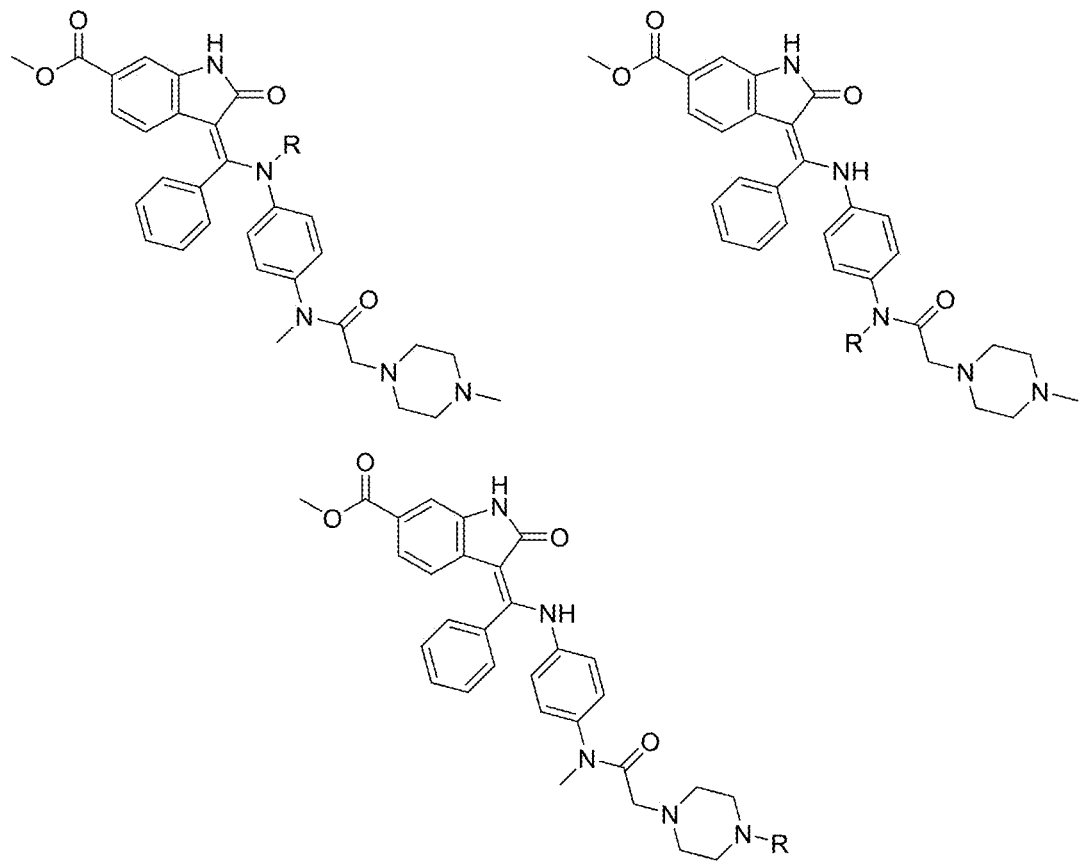
Figure 5Y:
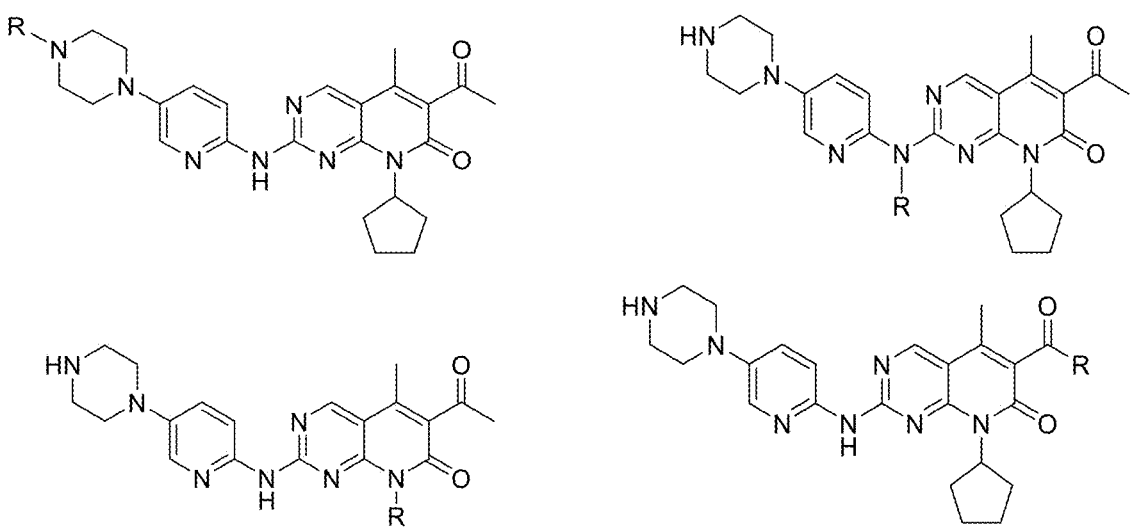
Figure 5Z:
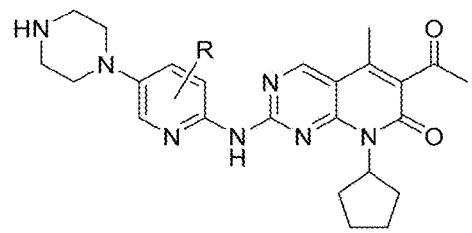
Figure 5A:
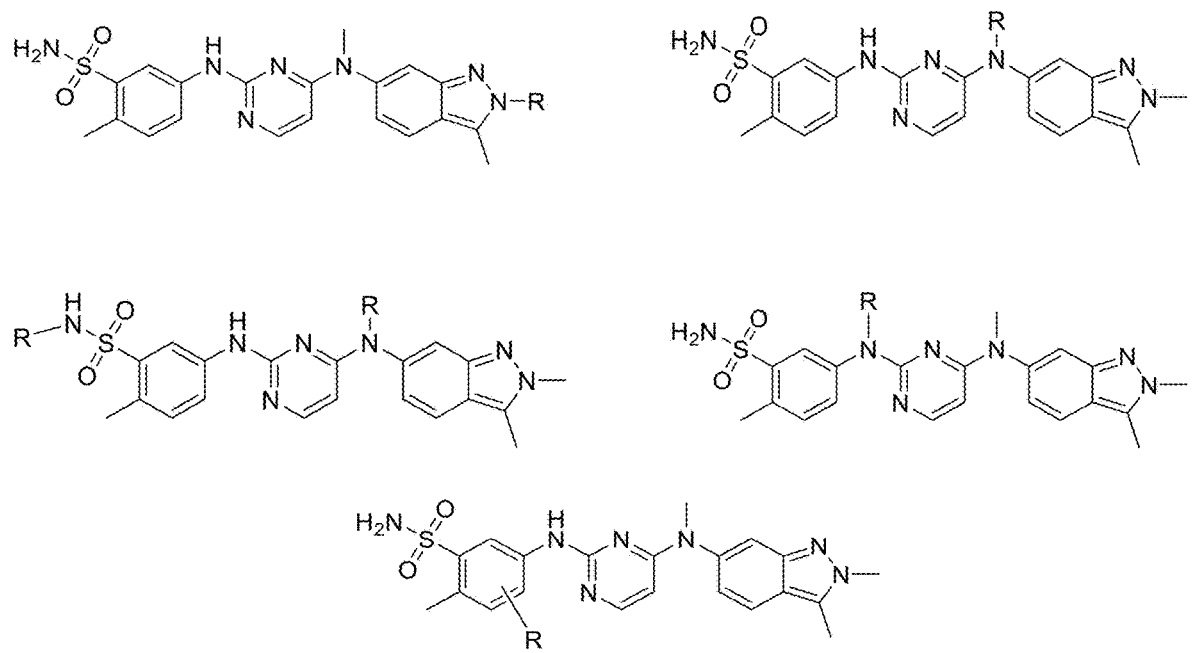
Figure 5B:
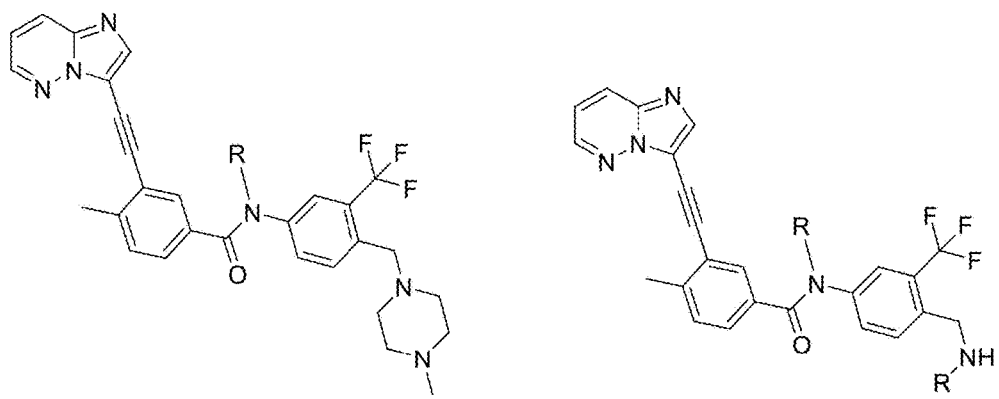
Figure 5C:
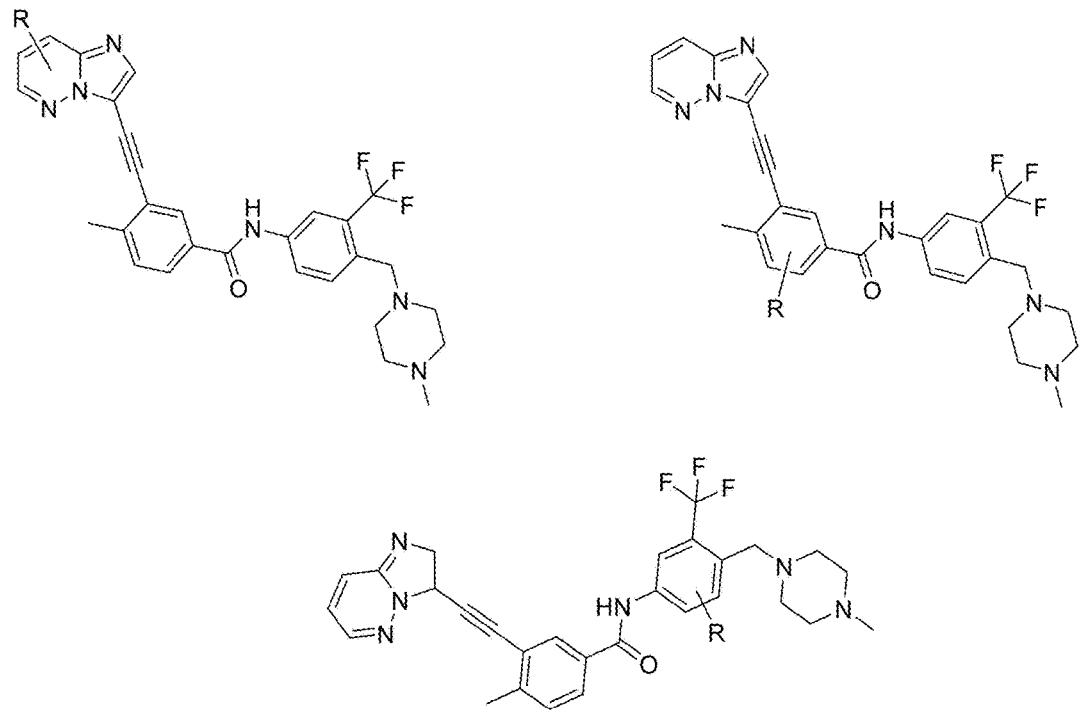
Figure 5D:
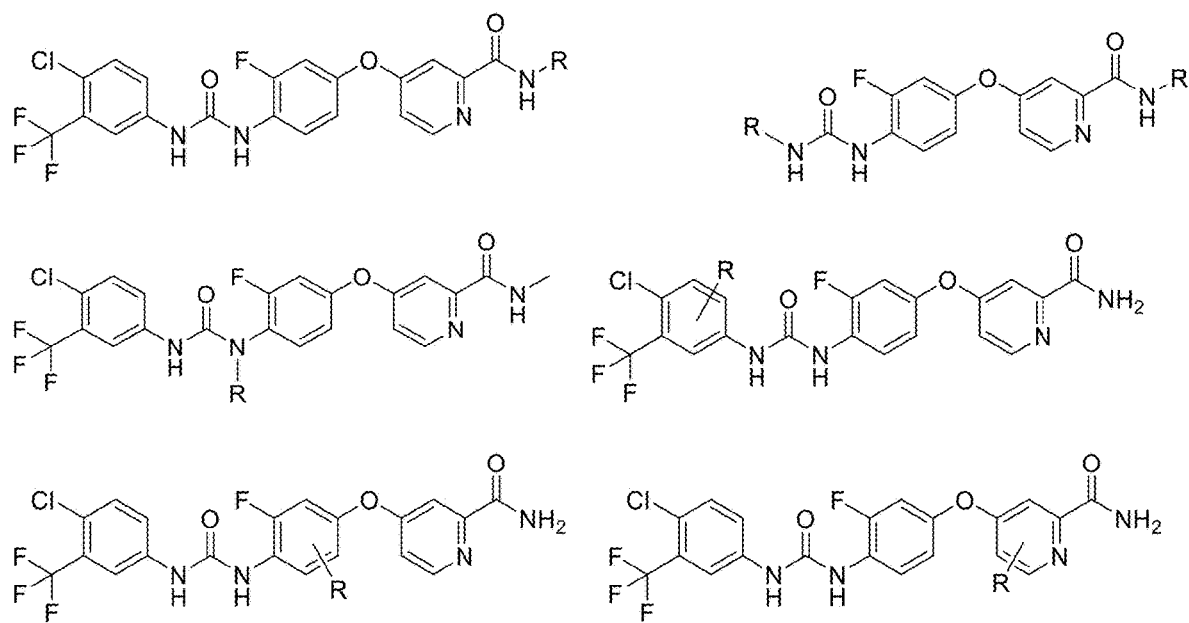
Figure 5E:
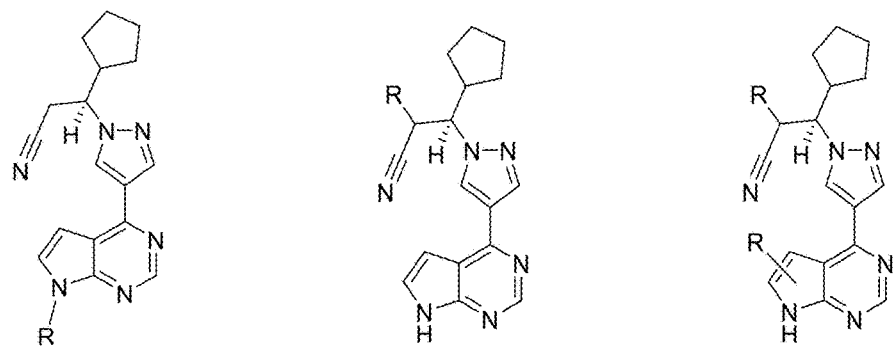
Figure 5F:
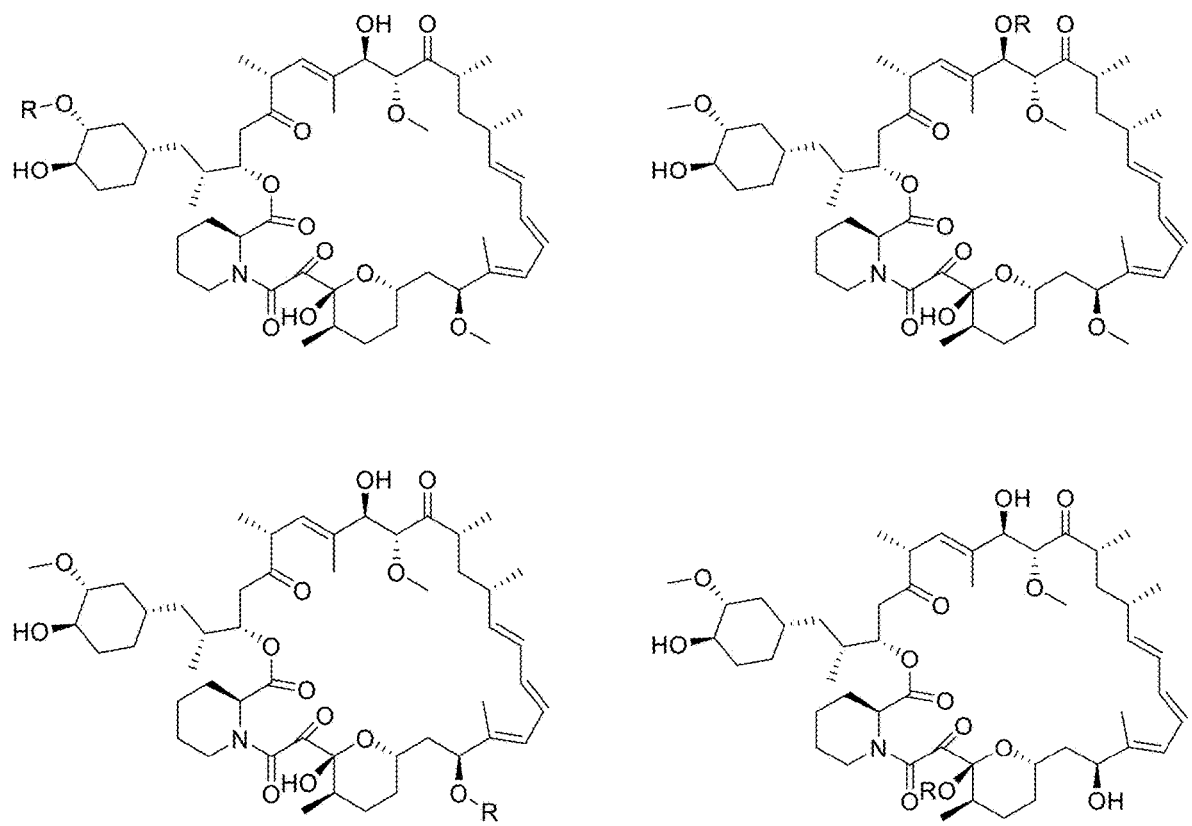
Figure 5G:
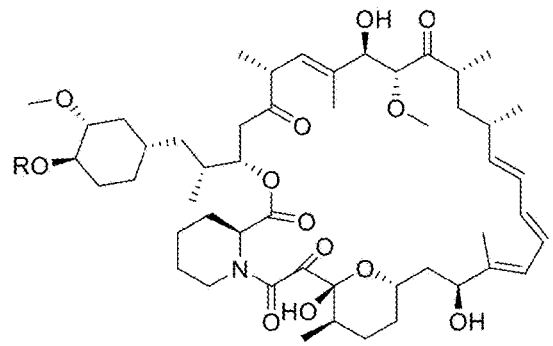
Figure 5H:
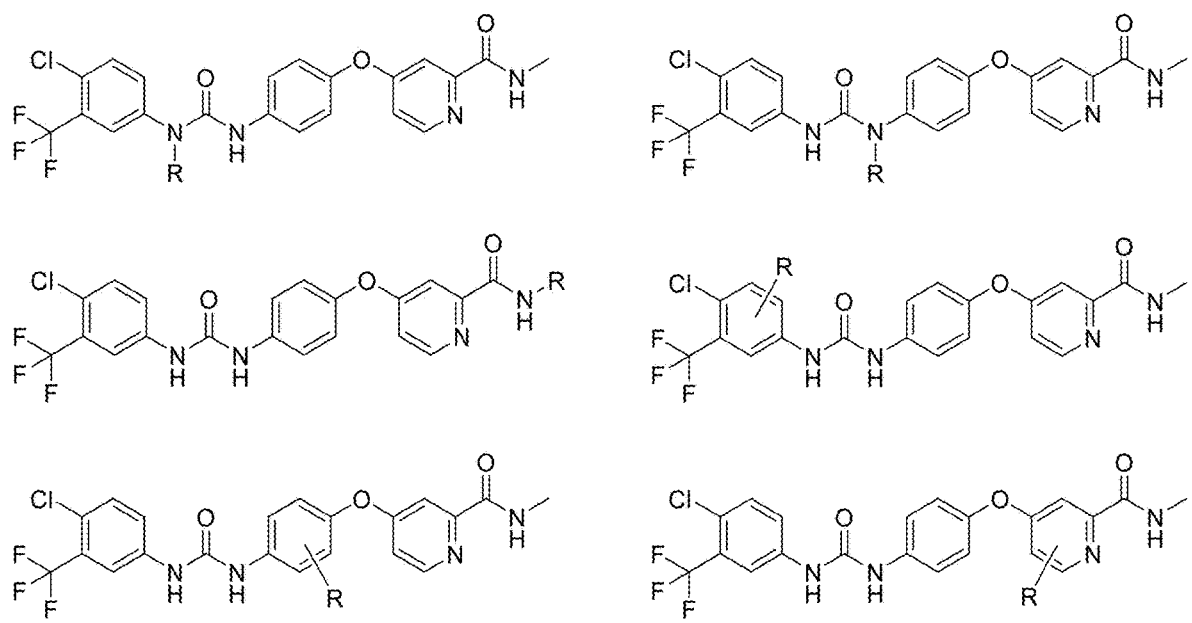
Figure 5I:
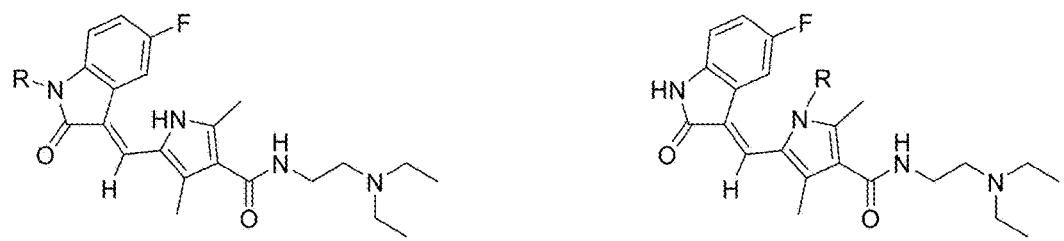
Figure 5L:
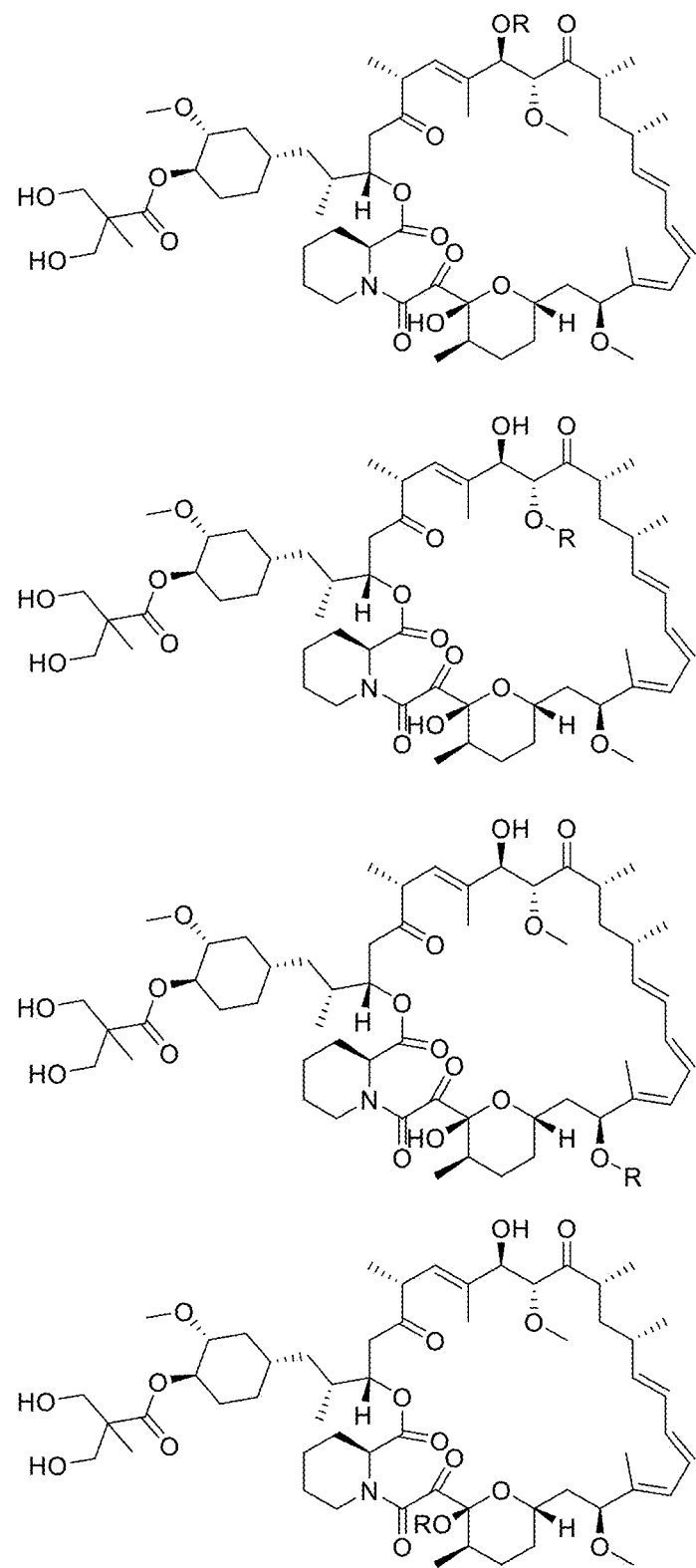
Figure 5M:
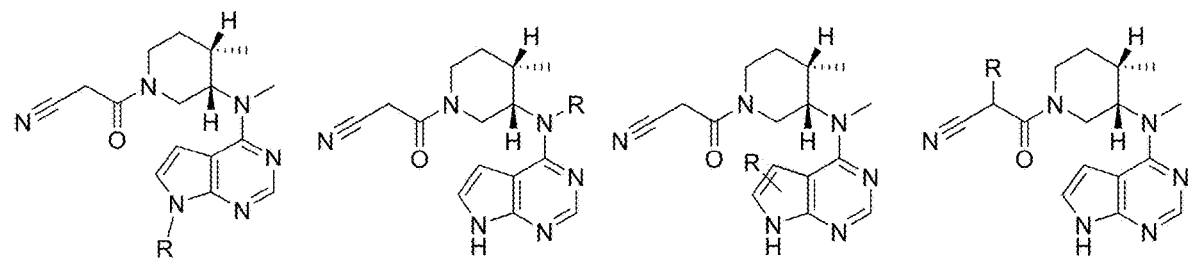

FIG. 5K-5M provide non-limiting examples of Everolimus, a Targeting Ligand for the HER2 breast cancer receptor, the PNET receptor, the RCC receptors, the RAML receptor, and the SEGA receptor. R represents exemplary points at which the Linker can be attached.

Figure 5N:
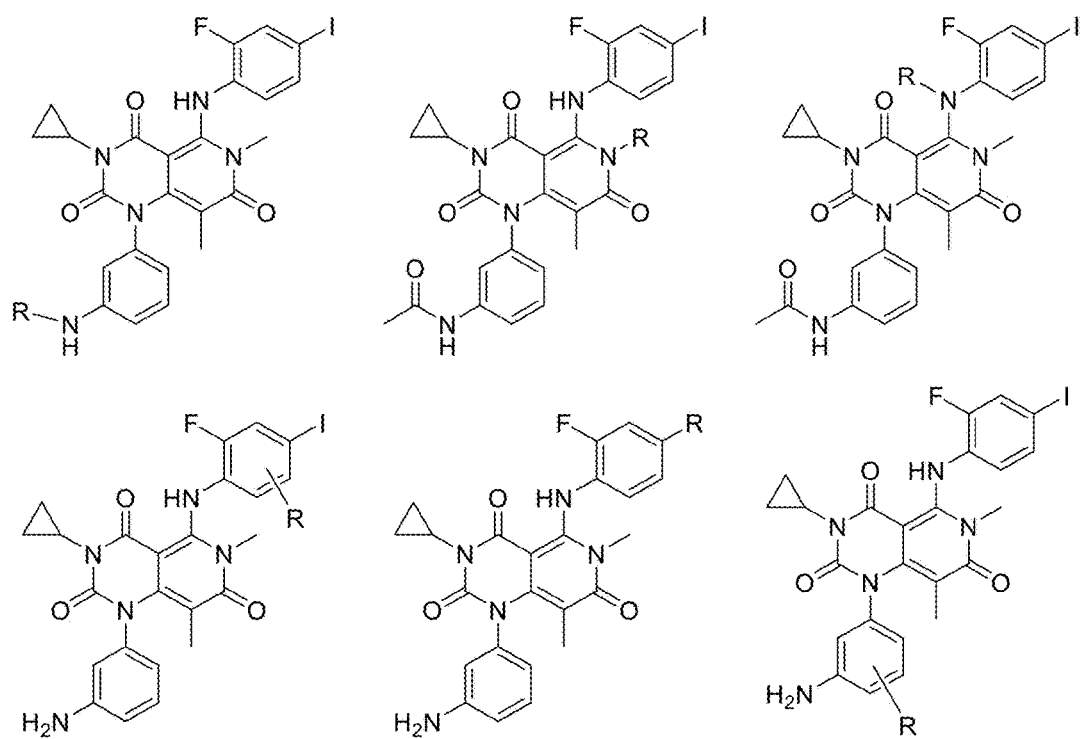
Figure 5O:
Figure 5P:
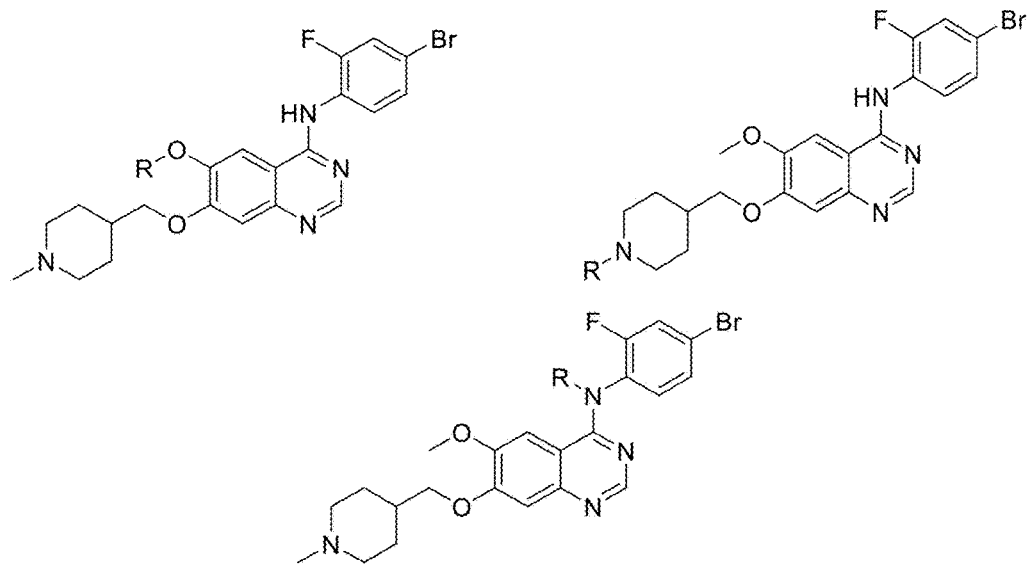
Figure 5Q:
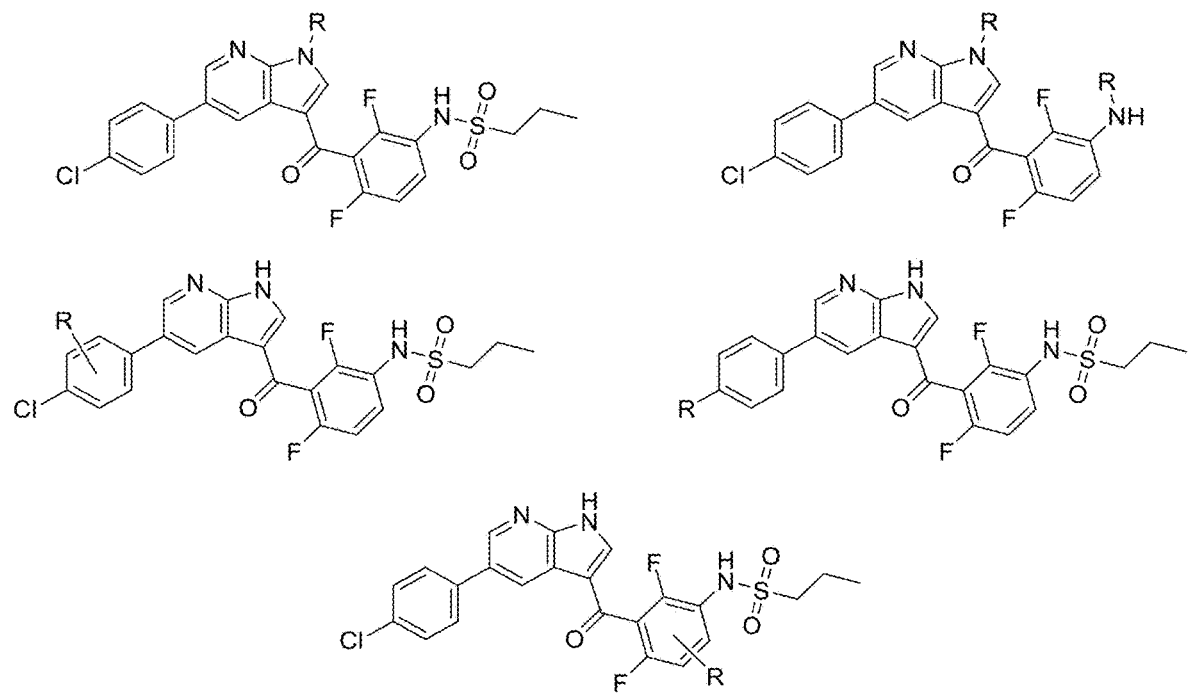
Figure 5R:
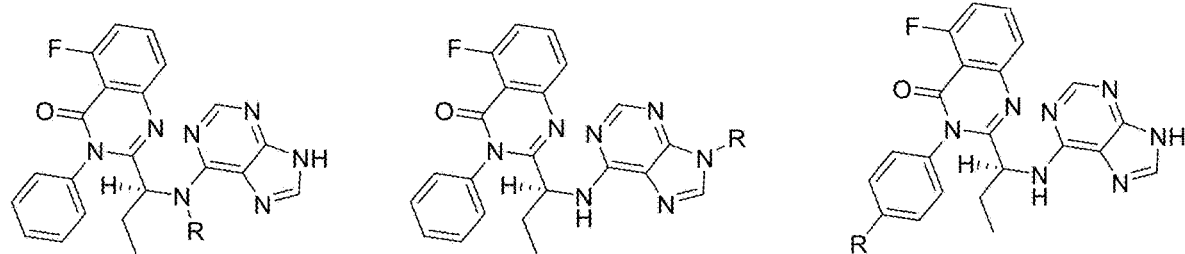
Figure 5S:
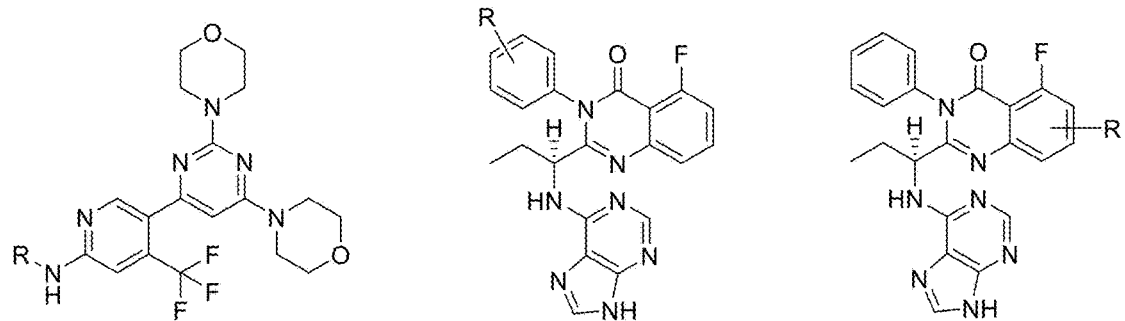
Figure 5T:
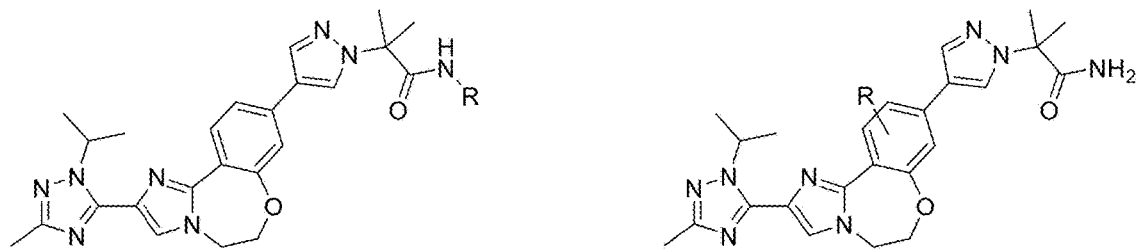
Figure 5U:
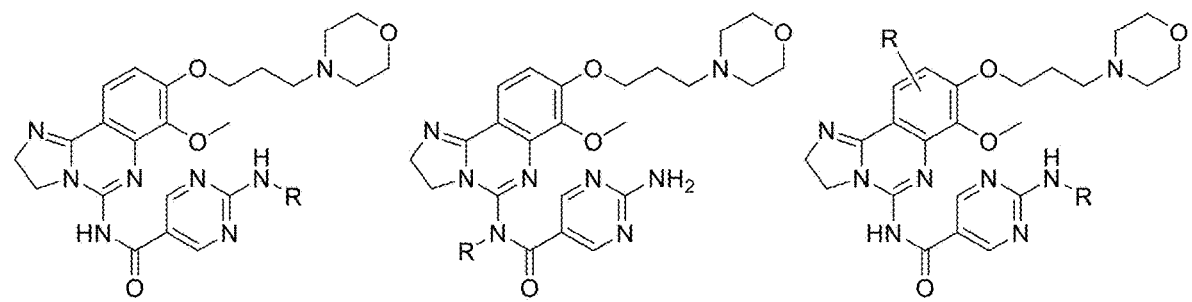
Figure 5V:
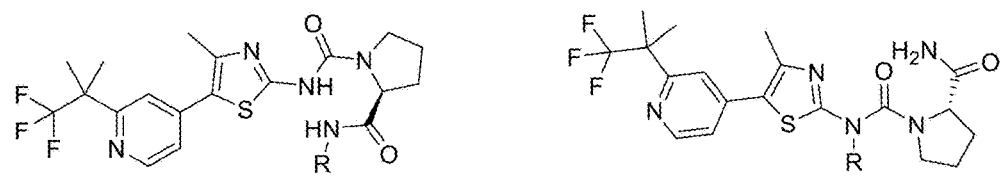
Figure 5W:
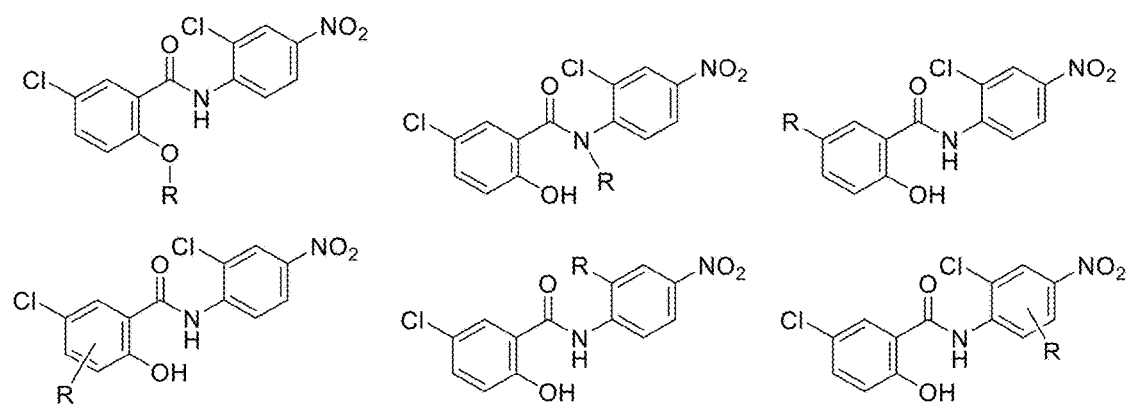

FIG. 5N provides non-limiting examples of Gefitinib, a Targeting Ligand for the EGFR and PDGFR receptors. R represents exemplary points at which the Linker can be attached.

FIG. 5O provides non-limiting examples of Ibrutinib, a Targeting Ligand for the BTK receptor. R represents exemplary points at which the Linker can be attached.

FIG. 5P-5Q provide non-limiting examples of Imatinib, a Targeting Ligand for the BCR-Abl, Kit, and PDGFR receptors. R represents exemplary points at which the Linker can be attached.

FIG. 5R-5S provide non-limiting examples of Lapatinib, a Targeting Ligand for the EGFR and ErbB2 receptors. R represents exemplary points at which the Linker can be attached.

FIG. 5T provides non-limiting examples of Lenvatinib, a Targeting Ligand for the VEGFR1/2/3, FGFR1/2/3/4, PDGFRα, Kit, and RET receptors. R represents exemplary points at which the Linker can be attached.

FIG. 5U-5V provide non-limiting examples of Nilotinib, a Targeting Ligand for the BCR-Abl, PDGRF, and DDR1 receptors. R represents exemplary points at which the Linker can be attached.

FIG. 5W-5X provide non-limiting examples of Nintedanib, a Targeting Ligand for the FGFR1/2/3, Flt3, Lck, PDGFRa/p, and VEGFR1/2/3 receptors. R represents exemplary points at which the Linker can be attached.

FIG. 5Y-5Z provide non-limiting examples of Palbociclib, a Targeting Ligand for the CDK4/6 receptor. R represents exemplary points at which the Linker can be attached.

FIG. 5AA provides non-limiting examples of Pazopanib, a Targeting Ligand for the VEGFR1/2/3, PDGFRa/p, FGFR1/3, Kit, Lck, Fms, and Itk receptors. R represents exemplary points at which the Linker can be attached.

FIG. 5BB-5CC provide non-limiting examples of Ponatinib, a Targeting Ligand for the BCR-Abl, T315I VEGFR, PDGFR, FGFR, EphR, Src family kinases, Kit, RET, Tie2, and Flt3 receptors. R represents exemplary points at which the Linker can be attached.

FIG. 5DD provides non-limiting examples of Regorafenib, a Targeting Ligand for the VEGFR1/2/3, BCR-Abl, B-Raf, B-Raf (V600E), Kit, PDGFRa/p, RET, FGFR1/2, Tie2, and Eph2A. R represents exemplary points at which the Linker can be attached.

FIG. 5EE provides non-limiting examples of Ruxolitinib, a Targeting Ligand for the JAK1/2 receptors. R represents exemplary points at which the Linker can be attached.

FIG. 5FF-5GG provide non-limiting examples of Sirolimus, a Targeting Ligand for the FKBP12/mTOR receptors. R represents exemplary points at which the Linker can be attached.

FIG. 5HH provides non-limiting examples of Sorafenib, a Targeting Ligand for the B-Raf, CDK8, Kit, Flt3, RET, VEGFR1/2/3, and PDGFR receptors. R represents exemplary points at which the Linker can be attached.

FIG. 5II-5JJ provide non-limiting examples of Sunitinib, a Targeting Ligand for PDGFRa/p, VEGFR1/2/3, Kit, Flt3, CSF-1R, RET. R represents exemplary points at which the Linker can be attached.

FIG. 5KK-5LL provide non-limiting examples of Temsirolimus, a Targeting Ligand FKBP12/mTOR. R represents exemplary points at which the Linker can be attached.

FIG. 5MM provides non-limiting examples of Tofacitinib, a Targeting Ligand for JAK3 receptors. R represents exemplary points at which the Linker can be attached.

FIG. 5NN provides non-limiting examples of Trametinib, a Targeting Ligand for the MEK1/2 receptors. R represents exemplary points at which the Linker can be attached.

FIG. 5OO-5PP provide non-limiting examples of Vandetanib, a Targeting Ligand for the EGFR, VEGFR, RET, Tie2, Brk, and EphR. R represents exemplary points at which the Linker can be attached.

FIG. 5QQ provides non-limiting examples of Vemurafenib, a Targeting Ligand for the A/B/C-Raf, KSR1, and B-Raf (V600E) receptors. R represents exemplary points at which the Linker can be attached.

FIG. 5RR provides non-limiting examples of Idelasib, a Targeting Ligand for the PI3Ka receptor. R represents exemplary points at which the Linker can be attached.

FIG. 5SS provides non-limiting examples of Buparlisib, a Targeting Ligand for the PI3Ka receptor. R represents exemplary points at which the Linker can be attached.

FIG. 5TT provides non-limiting examples of Taselisib, a Targeting Ligand for the PI3Ka receptor. R represents exemplary points at which the Linker can be attached.

FIG. 5UU provides non-limiting examples of Copanlisib, a Targeting Ligand for the PI3Ka. R represents exemplary points at which the Linker can be attached.

FIG. 5VV provides non-limiting examples of Alpelisib, a Targeting Ligand for the PI3Ka. R represents exemplary points at which the Linker can be attached.

FIG. 5WW provides non-limiting examples of Niclosamide, a Targeting Ligand for the CNNTB1. R represents exemplary points at which the Linker can be attached.

Figure 6A:
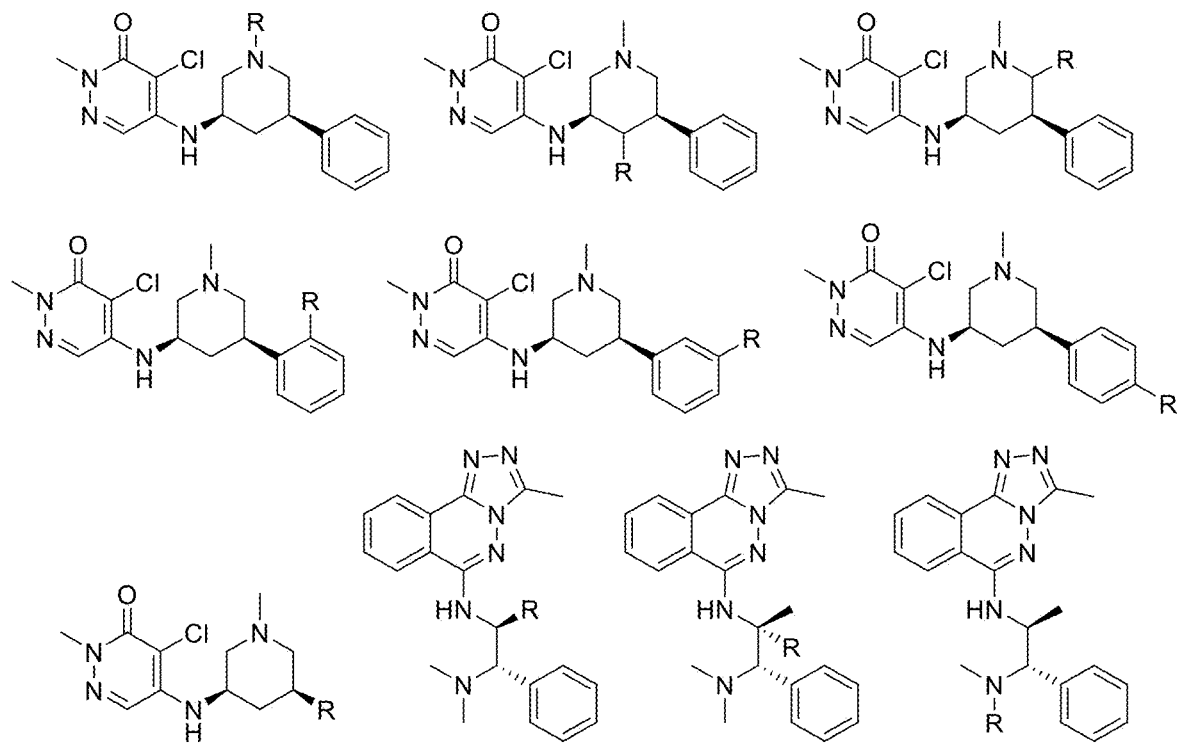
Figure 6B:
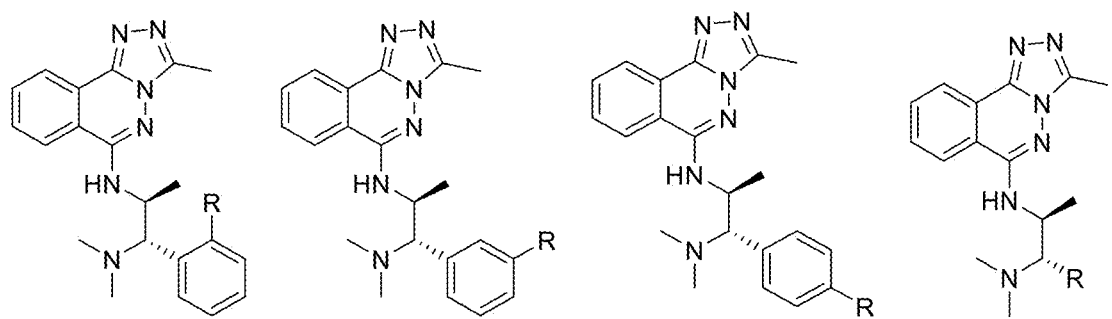

FIG. 6A-6B provide nonlimiting examples of the BRD4 Bromodomains of PCAF and GCN5 receptors 1 Targeting Ligands wherein R represents exemplary points at which the Linker can be attached. For additional examples and related ligands, see, the PDB crystal structure 5tpx ("Discovery of a PCAF Bromodomain Chemical Probe"); Moustakim, M., et al. *Angew. Chem. Int. Ed. Engl.* 56: 827 (2017); the PDB crystal structure 5mlj ("Discovery of a Potent, Cell Penetrant, and Selective p300/CBP-Associated Factor (PCAF)/General Control Nonderepressible 5 (GCN5) Bromodomain Chemical Probe"); and, Humphreys, P. G. et al. *J Med. Chem.* 60: 695 (2017).

Figure 6C:
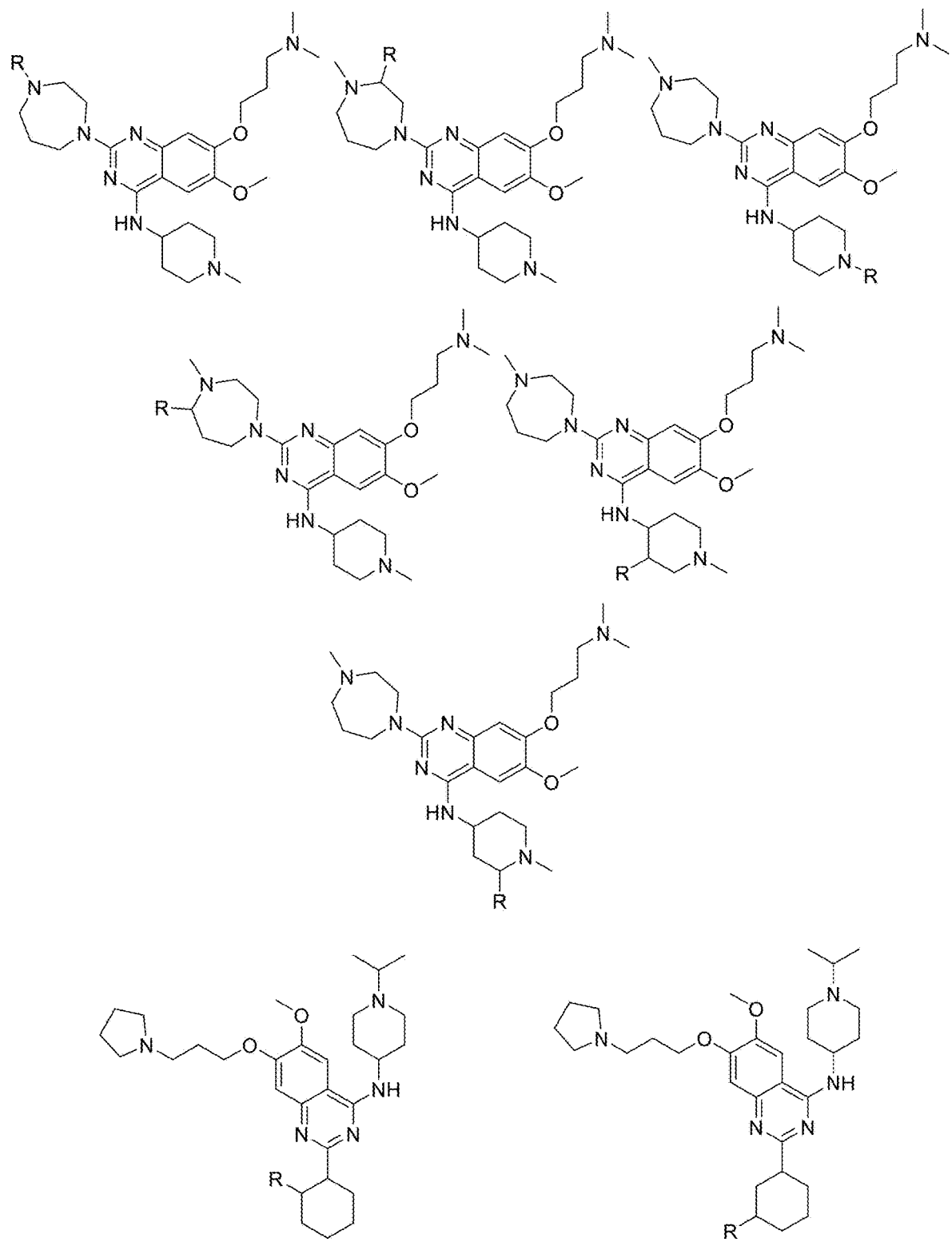
Figure 6D:
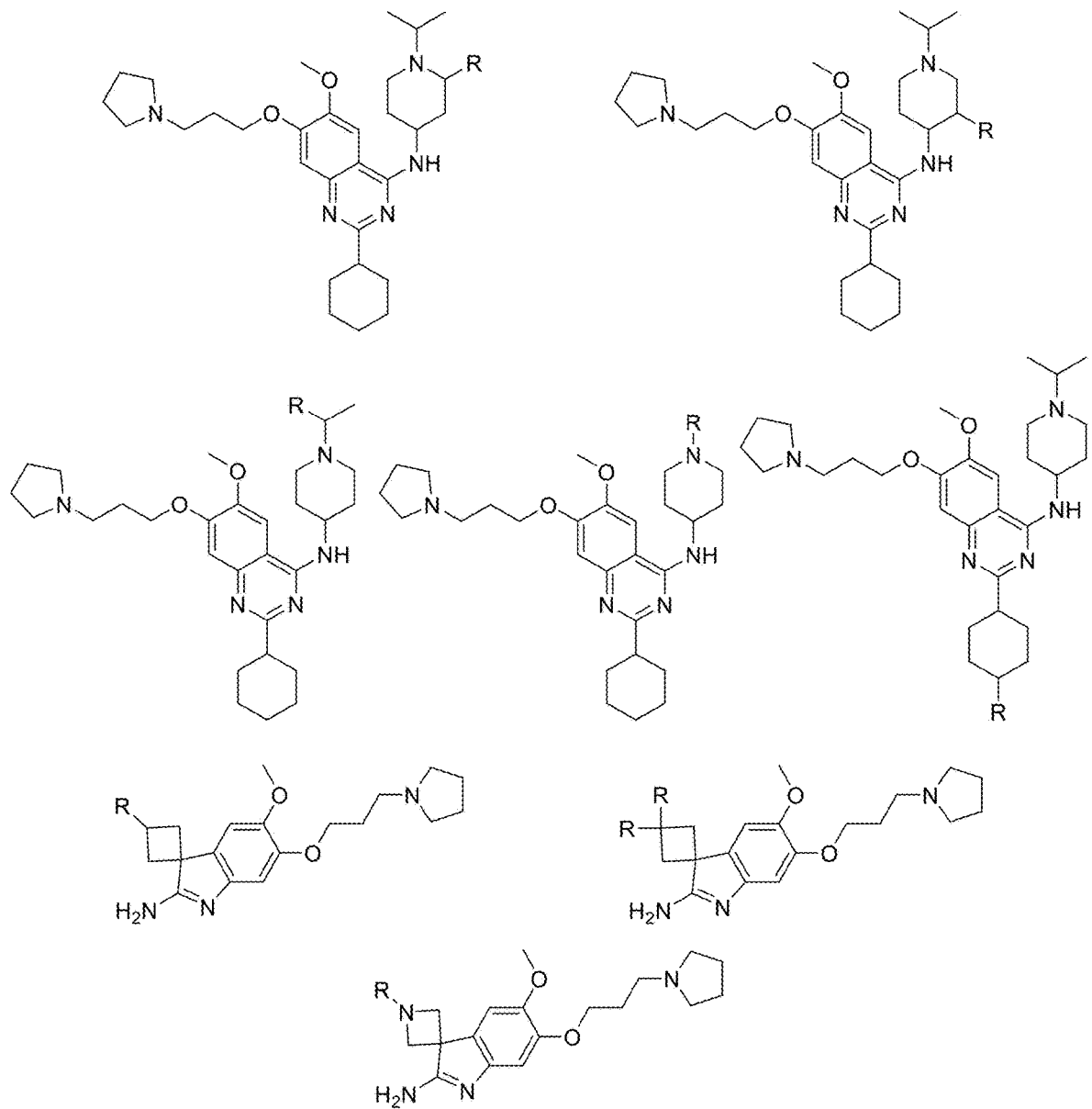

FIG. 6C-6D provide nonlimiting examples of G9a (EHMT2) Targeting Ligands wherein R represents exemplary points at which the Linker can be attached. For additional examples and related ligands, see, the PDB crystal structure 3k5k; ("Discovery of a 2,4-diamino-7-aminoalkoxyquinazoline as a potent and selective inhibitor of histone lysine methyltransferase G9a"); Liu, F. et al. *J. Med. Chem.* 52: 7950 (2009); the PDB crystal structure 3rjw ("A chemical probe selectively inhibits G9a and GLP methyltransferase activity in cells"); Vedadi, M. et al. *Nat. Chem. Biol.* 7: 566 (2011); the PDB crystal structure 4nvq ("Discovery and development of potent and selective inhibitors of histone methyltransferase g9a"); and, Sweis, R. F. et al. *ACS Med Chem Lett* 5: 205 (2014).

Figure 6E:
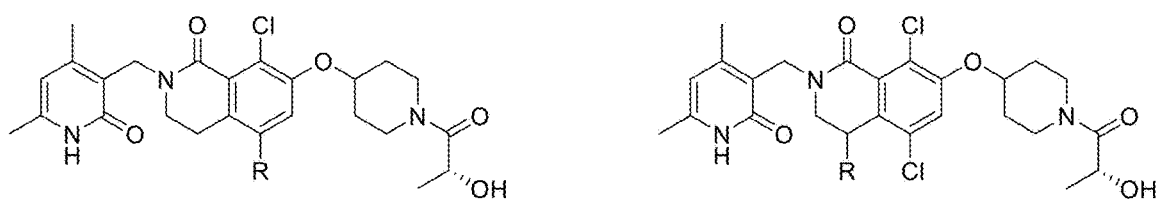
Figure 6F:
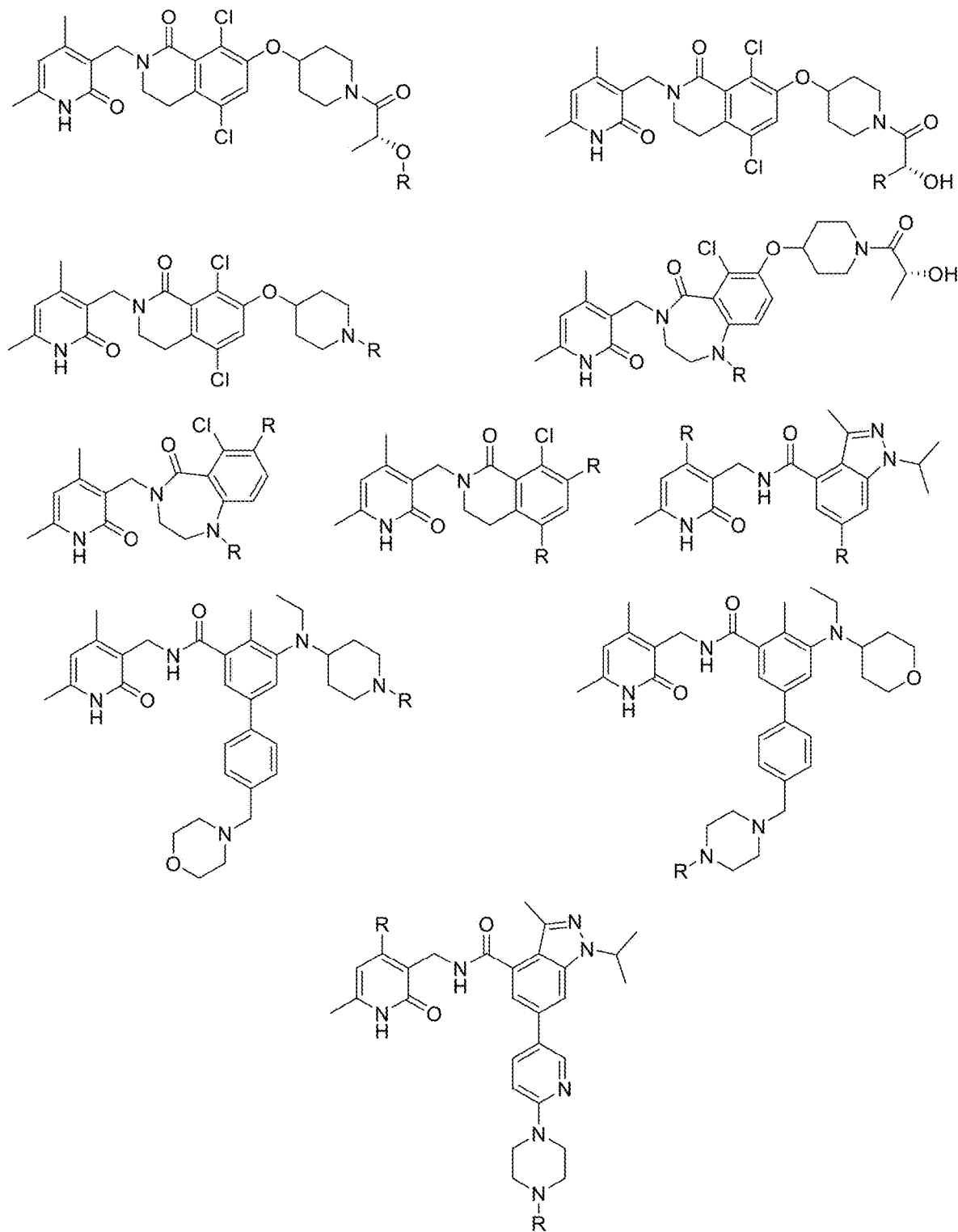
Figure 6G:
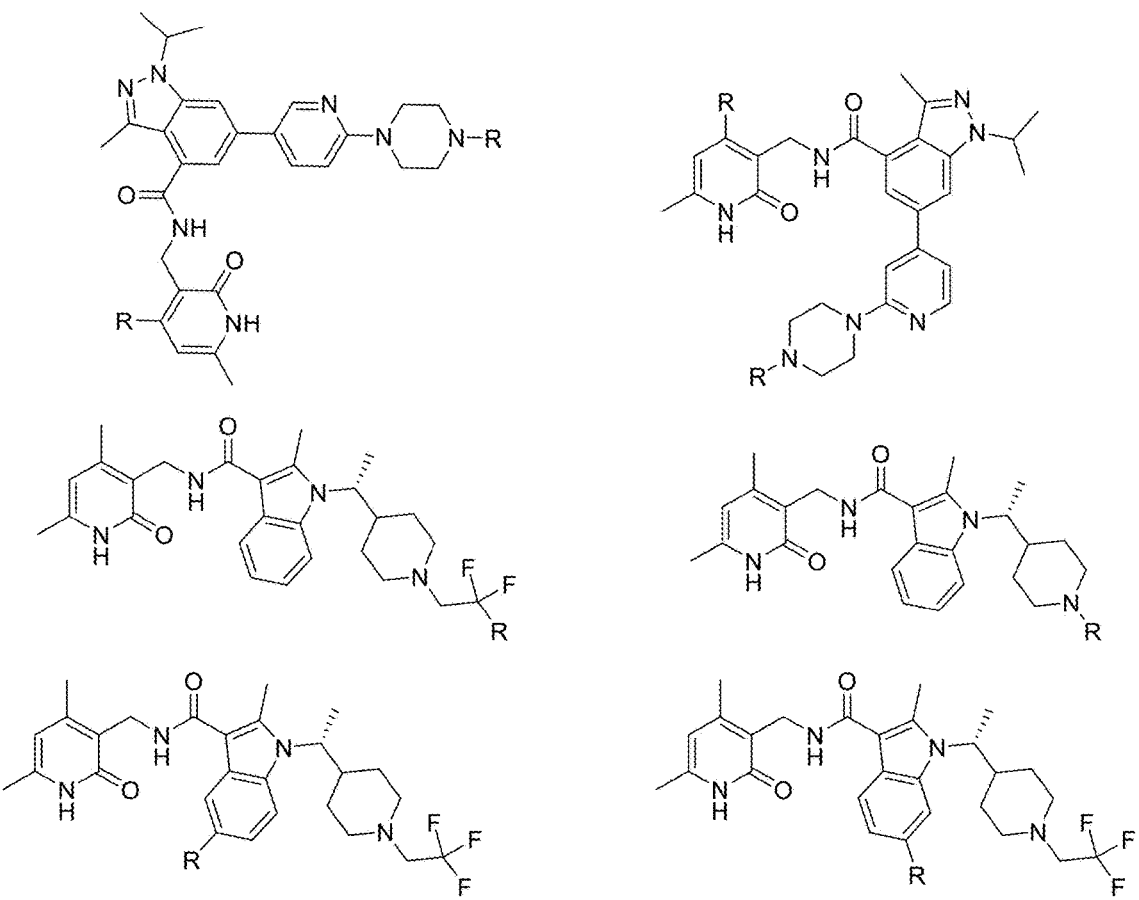

FIG. 6E-6G provide nonlimiting examples of EZH2 Targeting Ligands wherein R represents exemplary points at which the Linker can be attached. For additional examples and related ligands, see, the PDB crystal structure 5ij8 ("Polycomb repressive complex 2 structure with inhibitor reveals a mechanism of activation and drug resistance"); Brooun, A. et al. *Nat Commun* 7: 11384 (2016); the PDB crystal structure 5ls6 ("Identification of (R)—N-((4-Methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide (CPI-1205), a Potent and Selective Inhibitor of Histone Methyltransferase EZH2, Suitable for Phase I Clinical Trials for B-Cell Lymphomas"); Vaswani, R. G. et al. *J. Med. Chem.* 59: 9928 (2016); and, the PDB crystal structures 5ij8 and 5ls6.

Figure 6H:
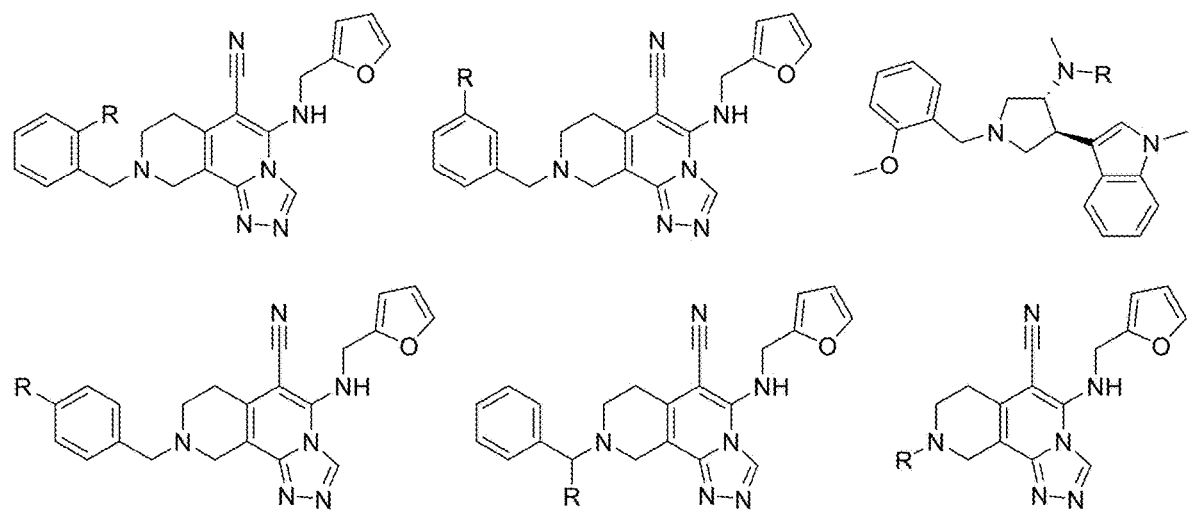
Figure 6I:
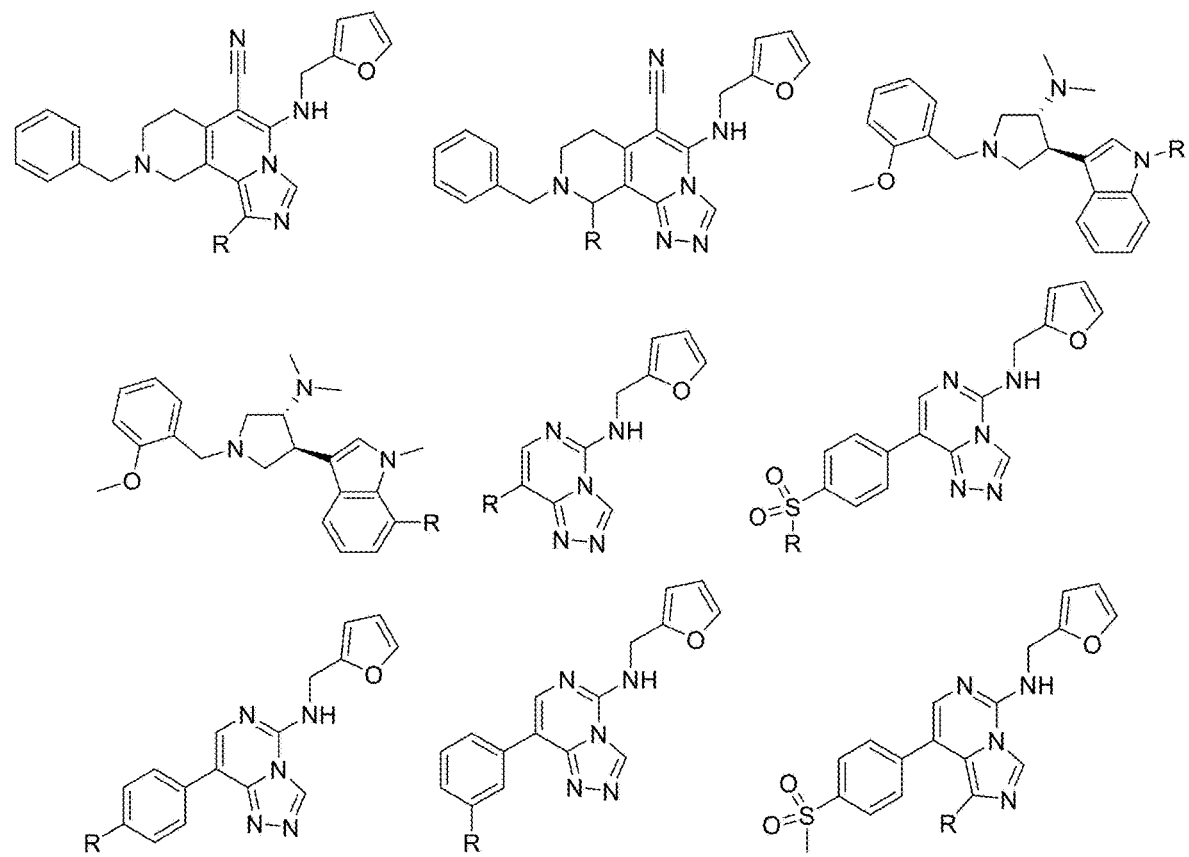

FIG. 6H-6I provide non-limiting examples of EED Targeting Ligands wherein R represents exemplary points at which the Linker can be attached. For additional examples and related ligands, see, the PDB crystal structures 5hl5 and 5hl9 ("Discovery and Molecular Basis of a Diverse Set of Polycomb Repressive Complex 2 Inhibitors Recognition by EED"); Li, L. et al. *PLoS ONE* 12: e0169855 (2017); and, the PDB crystal structure 5hl9.

Figure 6J:
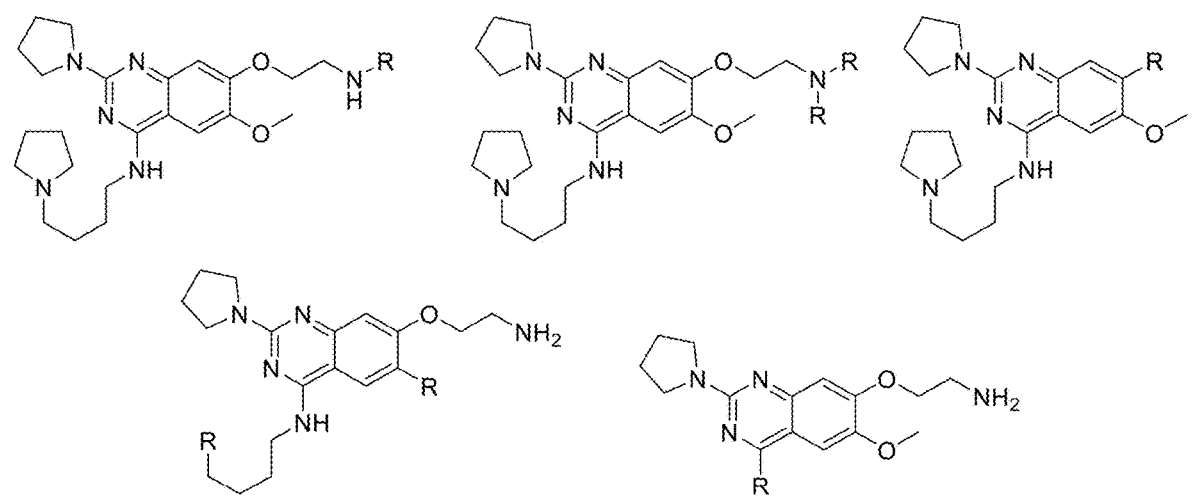

FIG. 6J provides non-limiting examples of KMT5A (SETD8) Targeting Ligands wherein R represents exemplary points at which the Linker can be attached. See for example, the PDB crystal structure 5t5g.

Figure 6K:
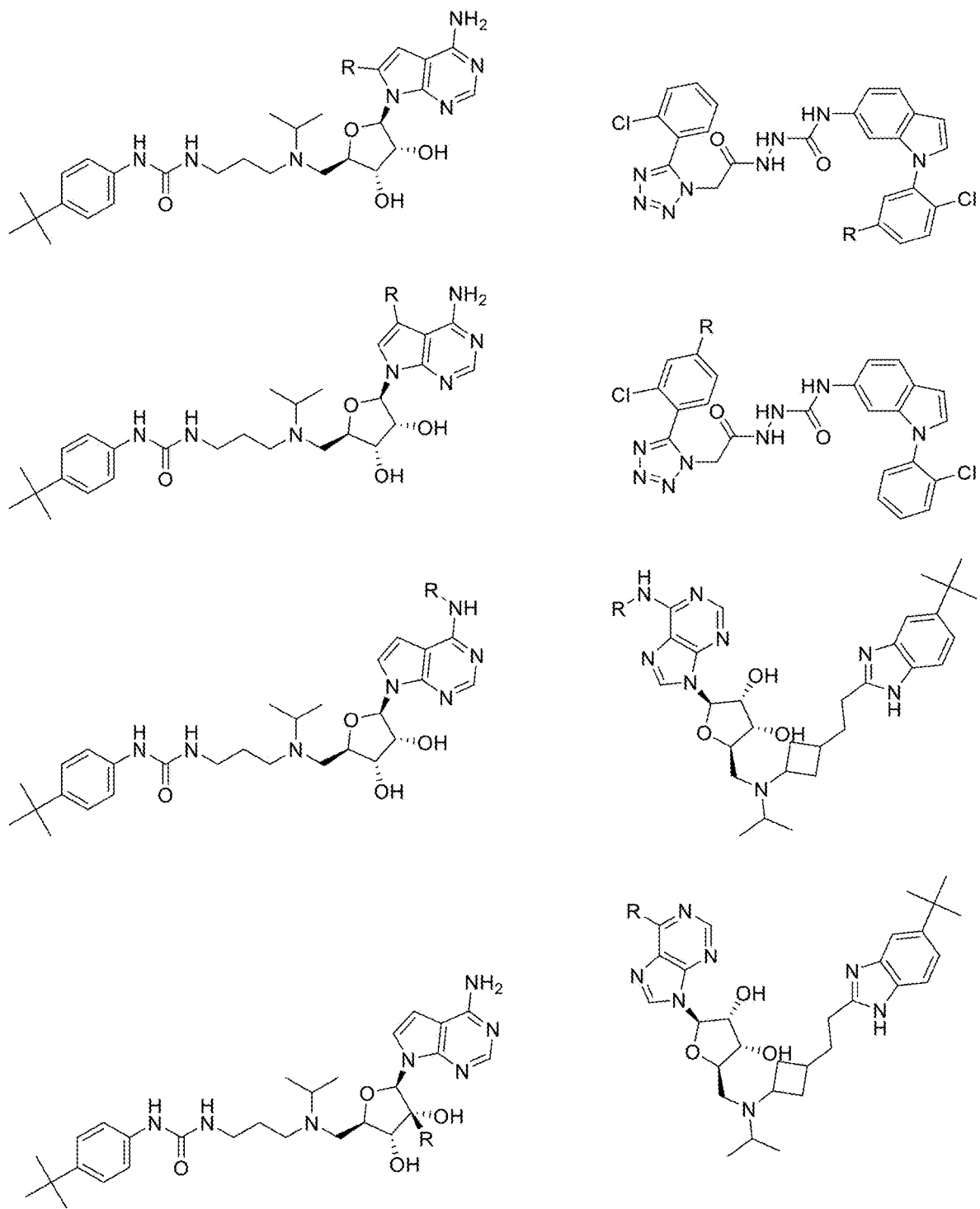
Figure 6L:
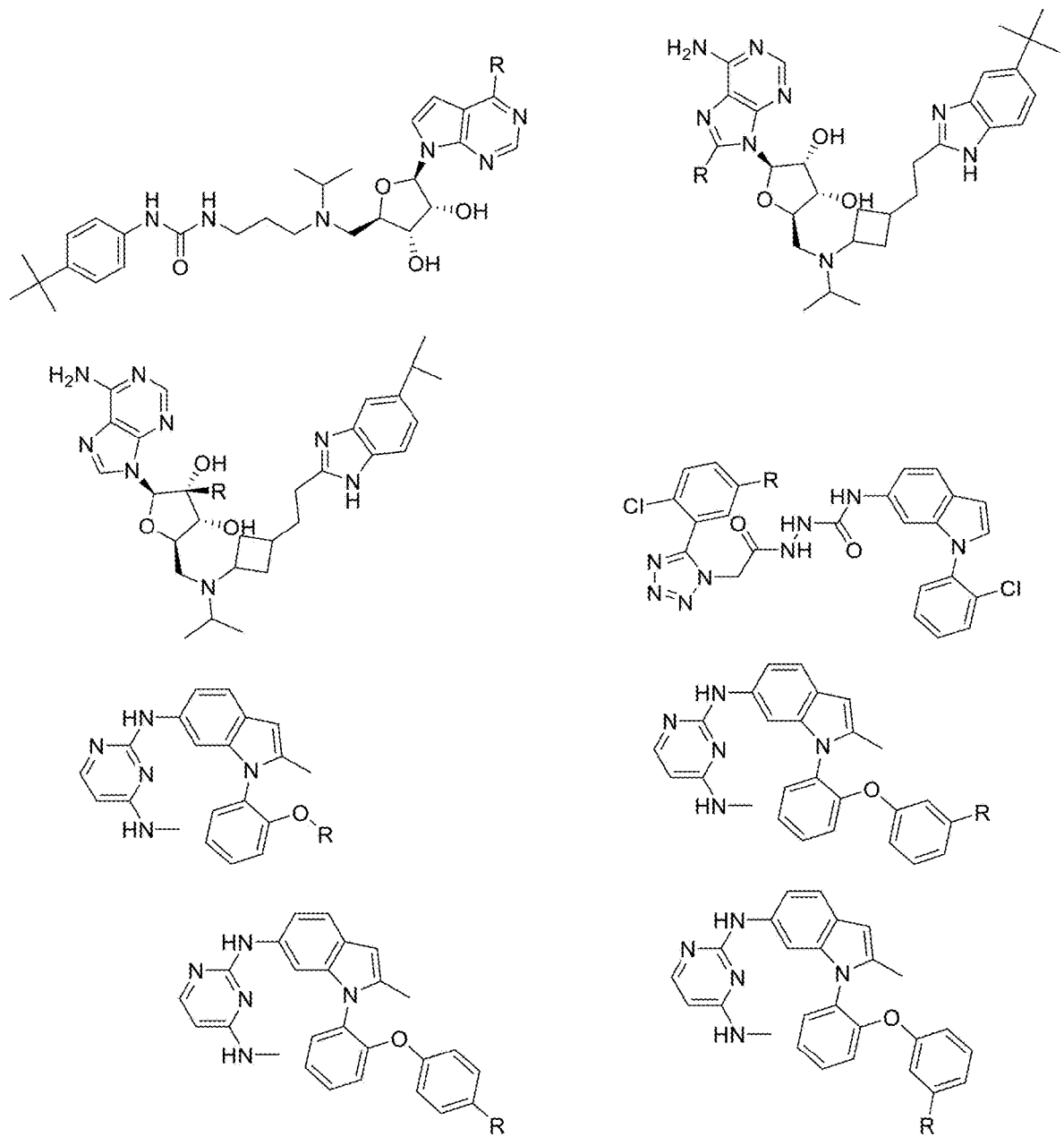

FIG. 6K-6L provide non-limiting examples of DOT1L Targeting Ligands wherein R represents exemplary points at which the Linker can be attached. For additional examples and related ligands, see, the PDB crystal structure 4eki ("Conformational adaptation drives potent, selective and durable inhibition of the human protein methyltransferase DOT1L"); Basavapathruni, A. et al. *Chem. Biol. Drug Des.* 80: 971 (2012); the PDB crystal structure 4hra ("Potent inhibition of DOT1L as treatment of MLL-fusion leukemia"); Daigle, S. R. et al. *Blood* 122: 1017 (2013); the PDB crystal structure 5dry ("Discovery of Novel Dot1L Inhibitors through a Structure-Based Fragmentation Approach") Chen, C. et al. *ACS Med. Chem. Lett.* 7: 735 (2016); the PDB crystal structure 5dt2 ("Discovery of Novel Dot1L Inhibitors through a Structure-Based Fragmentation Approach"); and, Chen, C. et al. *ACS Med. Chem. Lett.* 7: 735 (2016).

Figure 6M:
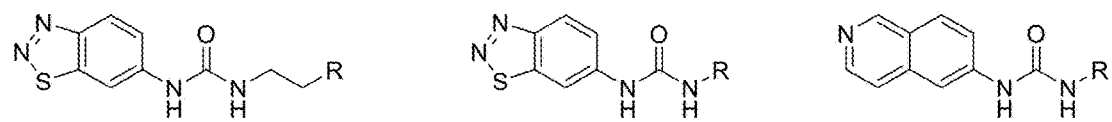

FIG. 6M-6N provide nonlimiting examples of PRMT3 Targeting Ligands wherein R represents exemplary points at which the Linker can be attached. For additional examples and related ligands, see, the PDB crystal structure 3smq ("An allosteric inhibitor of protein arginine methyltransferase 3"); Siarheyeva, A. et al. *Structure* 20: 1425 (2012); PDB crystal structure 4ryl ("A Potent, Selective and Cell-Active Allosteric Inhibitor of Protein Arginine Methyltransferase 3 (PRMT3)"); and Kaniskan, H. U. et al. *Angew. Chem. Int. Ed. Engl.* 54: 5166 (2015).

FIG. 6O provides non-limiting examples of CARM1 (PRMT4) Targeting Ligands wherein R represents exemplary points at which the Linker can be attached. For additional examples and related ligands, see, the PDB crystal structures 2ylx and 2ylw and related ligands described in "Structural Basis for Carm1 Inhibition by Indole and Pyrazole Inhibitors." Sack, J. S. et al. *Biochem. J.* 436: 331 (2011).

FIG. 6P provides non-limiting examples of PRMT5 Targeting Ligands wherein R represents exemplary points at which the Linker can be attached. For additional examples and related ligands, see, the PDB crystal structure 4x61 and related ligands described in "A selective inhibitor of PRMT5 with in vivo and in vitro potency in MCL models". Chan-Penebre, E. *Nat. Chem. Biol.* 11: 432 (2015).

Figure 6Q:
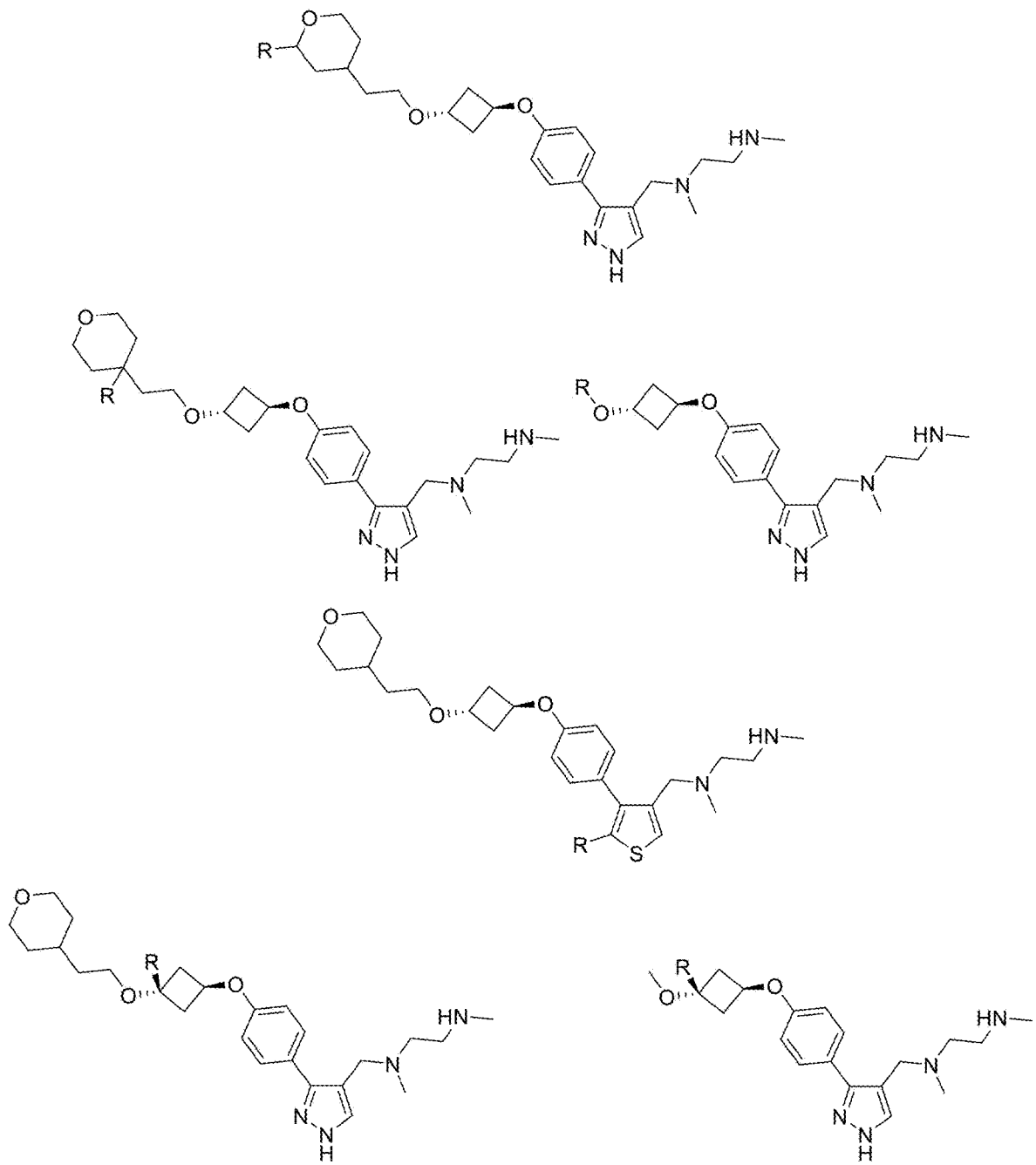

FIG. 6Q provides non-limiting examples of PRMT6 Targeting Ligands wherein R represents exemplary points at which the Linker can be attached. For additional examples and related ligands, see, the PDB crystal structure 4y30 and related ligands described in "Aryl Pyrazoles as Potent Inhibitors of Arginine Methyltransferases: Identification of the First PRMT6 Tool Compound". Mitchell, L. H. et al. *ACS Med Chem. Lett.* 6: 655 (2015).

Figure 6R:
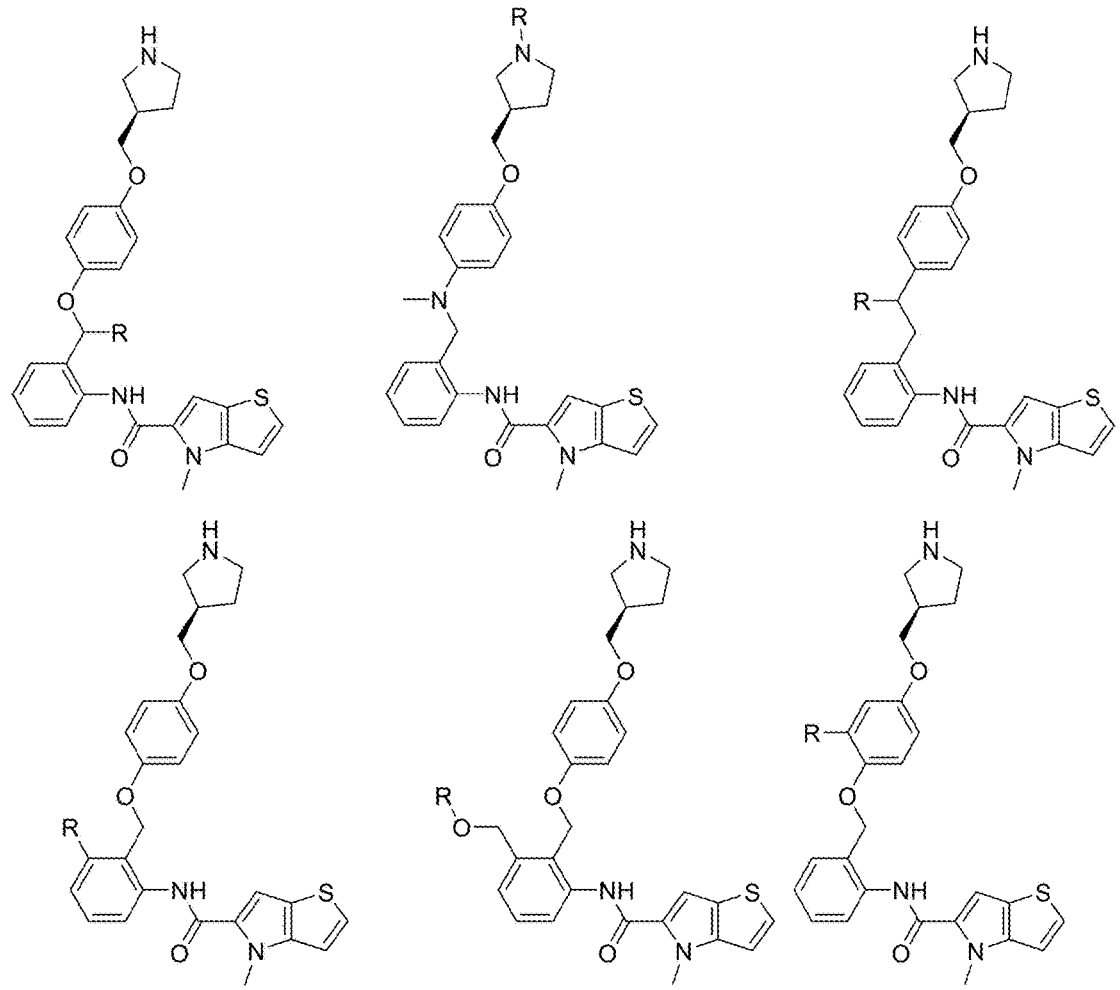

FIG. 6R provides non-limiting examples of LSD1 (KDM1A) Targeting Ligands wherein R represents exemplary points at which the Linker can be attached. For additional examples and related ligands, see, the PDB crystal structure 5lgu and related ligands described in "Thieno [3,2-b]pyrrole-5-carboxamides as New Reversible Inhibitors of Histone Lysine Demethylase KDM1A/LSD1. Part 2: Structure-Based Drug Design and Structure-Activity Relationship". Vianello, P. et al. *J. Med Chem.* 60: 1693 (2017).

Figure 6S:
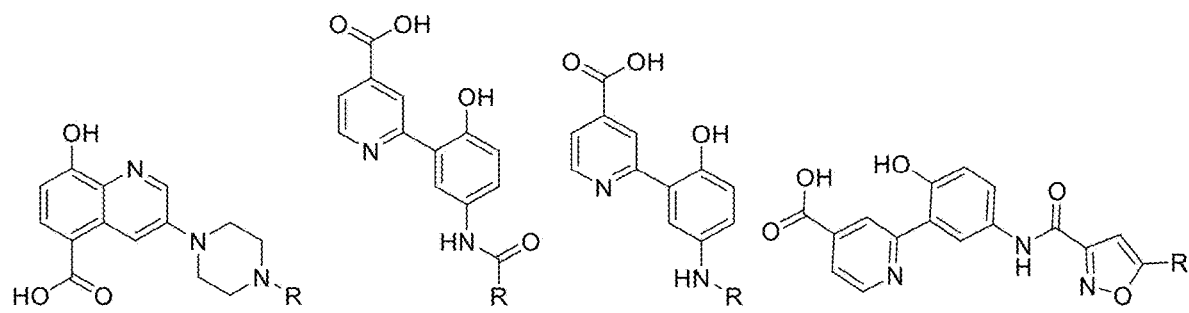
Figure 6T:
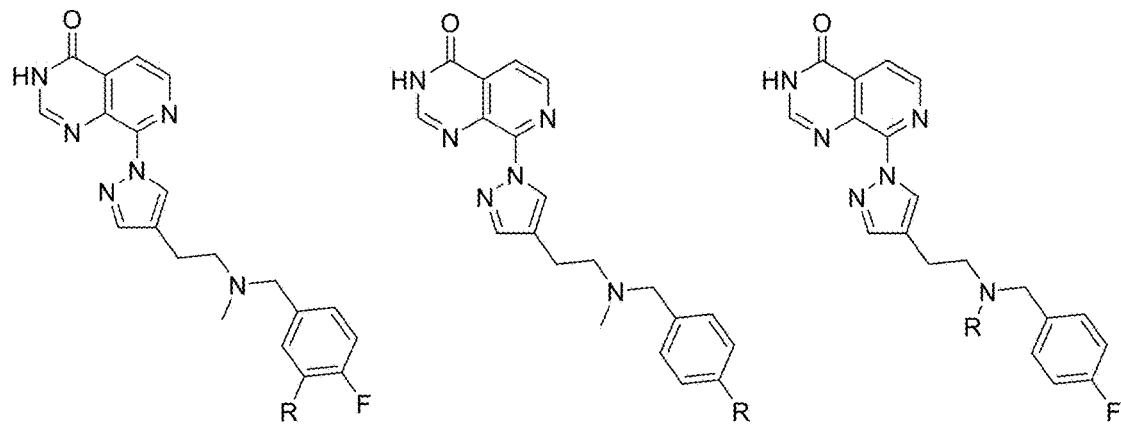

FIG. 6S-6T provides non-limiting examples of KDM4 Targeting Ligands wherein R represents exemplary points at which the Linker can be attached. For additional examples and related ligands, see, the PDB crystal structure 3rvh; the PDB crystal structure 5a7p and related ligands described in "Docking and Linking of Fragments to Discover Jumonji Histone Demethylase Inhibitors." Korczynska, M., et al. *J. Med Chem.* 59: 1580 (2016); and, the PDB crystal structure 3f3c and related ligands described in "8-Substituted Pyrido [3,4-d]pyrimidin-4(3H)-one Derivatives As Potent, Cell Permeable, KDM4 (JMJD2) and KDM5 (JARID1) Histone Lysine Demethylase Inhibitors." Bavetsias, V. et al. *J Med Chem.* 59: 1388 (2016).

Figure 6U:
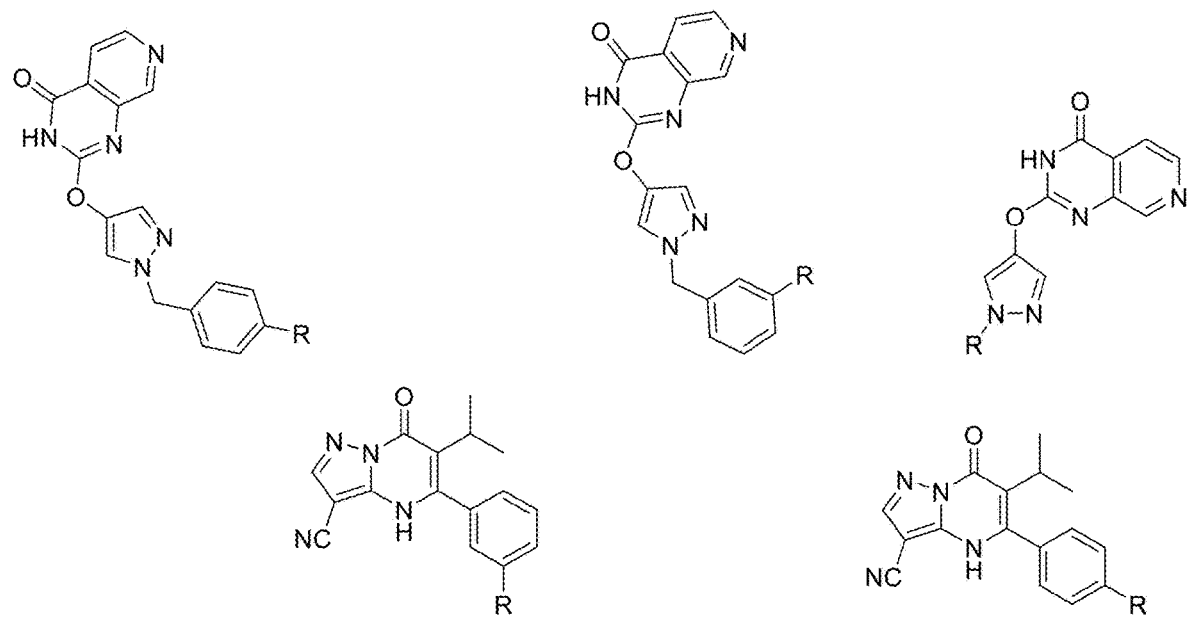

FIG. 6U provides non-limiting examples of KDM5 Targeting Ligands wherein R represents exemplary points at which the Linker can be attached. For additional examples and related ligands, see, the PDB crystal structure 3fun and related ligands described in "Structural Analysis of Human Kdm5B Guides Histone Demethylase Inhibitor Development". Johansson, C. et al. *Nat. Chem. Biol.* 12: 539 (2016) and the PDB crystal structure 5ceh and related ligands described in "An inhibitor of KDM5 demethylases reduces survival of drug-tolerant cancer cells". Vinogradova, M. et al. *Nat. Chem. Biol.* 12: 531 (2016).

Figure 6V:
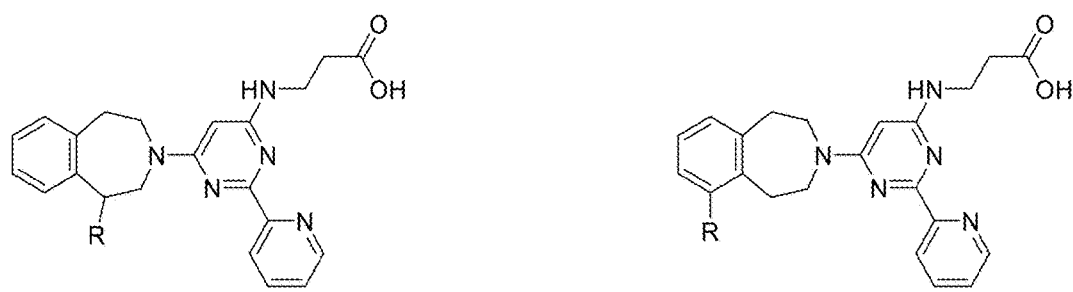
Figure 6W:
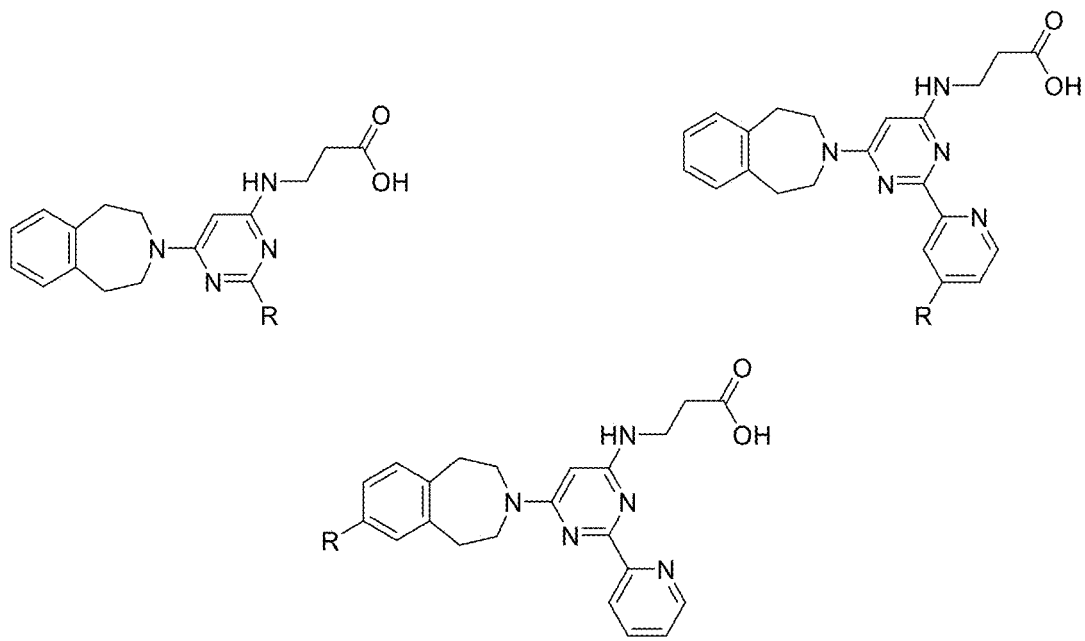

FIG. 6V-6W provide non-limiting examples of KDM6 Targeting Ligands wherein R represents exemplary points at which the Linker can be attached. For additional examples and related ligands, see, the PDB crystal structure 4ask and related ligands described in "A Selective Jumonji H3K27 Demethylase Inhibitor Modulates the Proinflammatory Macrophage Response". Kruidenier, L. et al. *Nature* 488: 404 (2012).

Figure 6X:
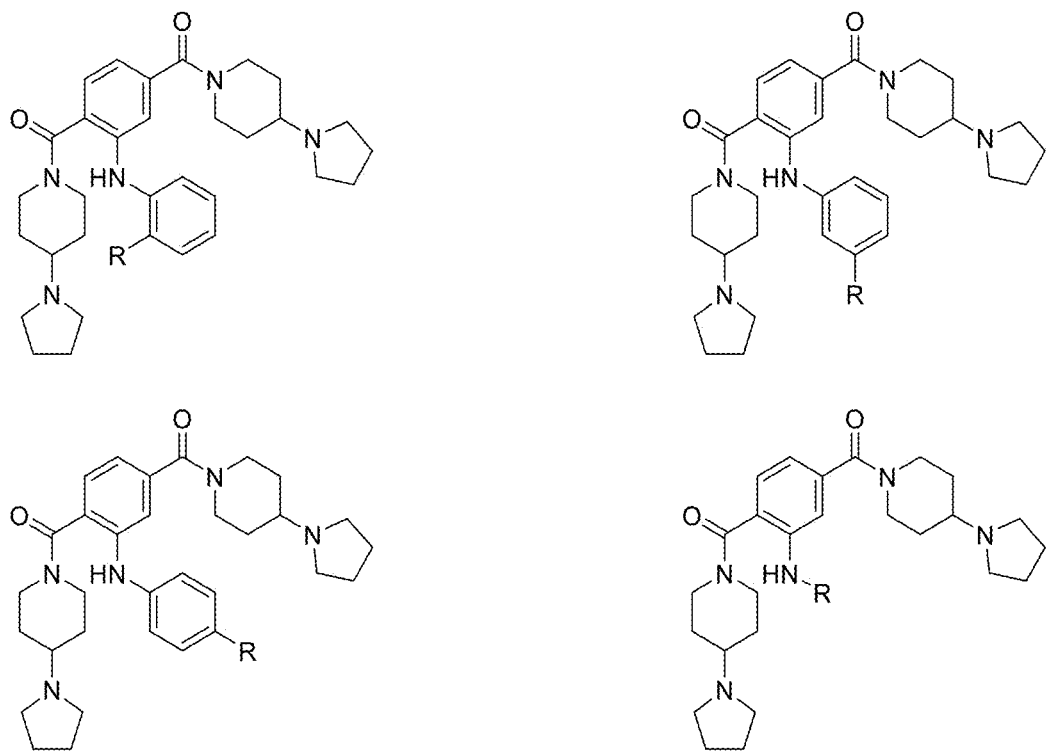

FIG. 6X provides non-limiting examples of L3MBTL3 targeting ligands wherein R represents exemplary points at which the Linker can be attached. See for example, the PDB crystal structure 4fl6.

Figure 6Y:
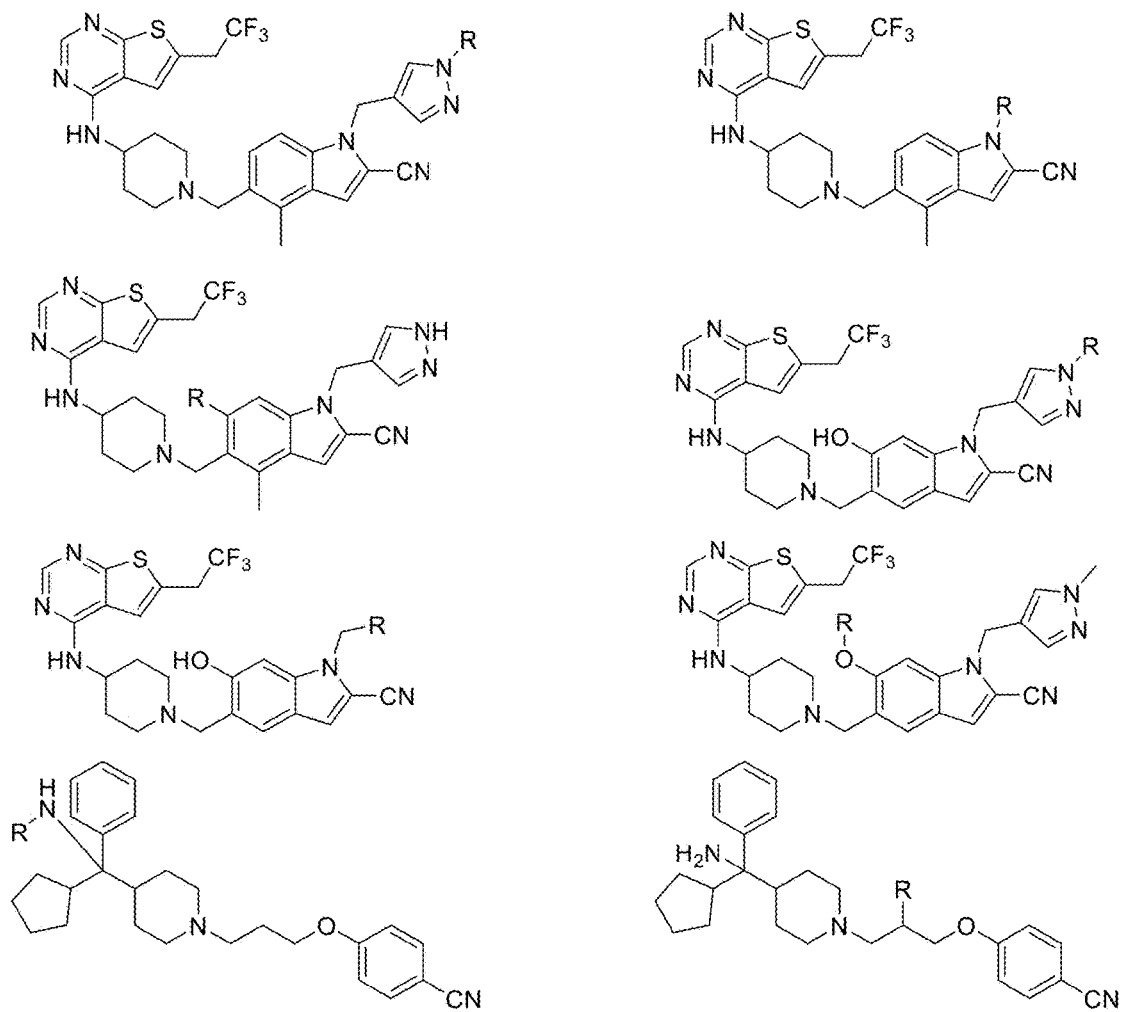

FIG. 6Y provides non-limiting examples of Menin Targeting Ligands wherein R represents exemplary points at which the Linker can be attached. For additional examples and related ligands, see, the PDB crystal structure 4×5y and related ligands described in "Pharmacologic Inhibition of the Menin-MLL Interaction Blocks Progression of MLL Leukemia In Vivo" Borkin, D. et al. *Cancer Cell* 27: 589 (2015) and the PDB crystal structure 4og8 and related ligands described in "High-Affinity Small-Molecule Inhibitors of the Menin-Mixed Lineage Leukemia (MLL) Interaction Closely Mimic a Natural Protein-Protein Interaction" He, S. et al. *J. Med. Chem.* 57: 1543 (2014).

Figure 6Z:
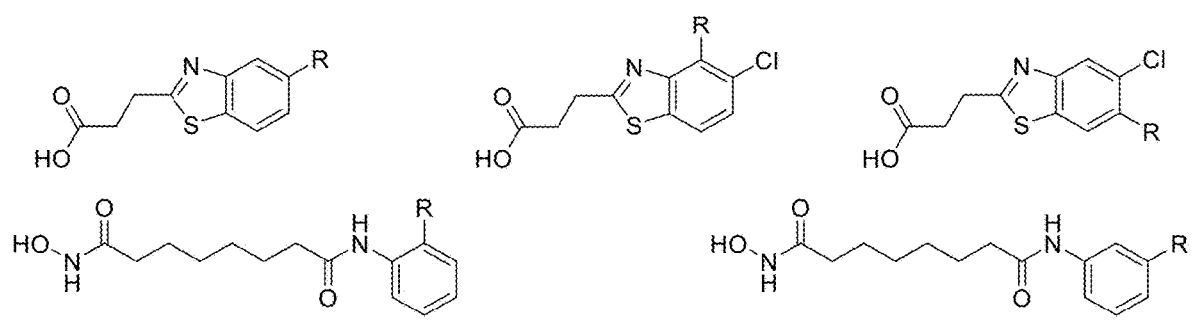
Figure 6A:
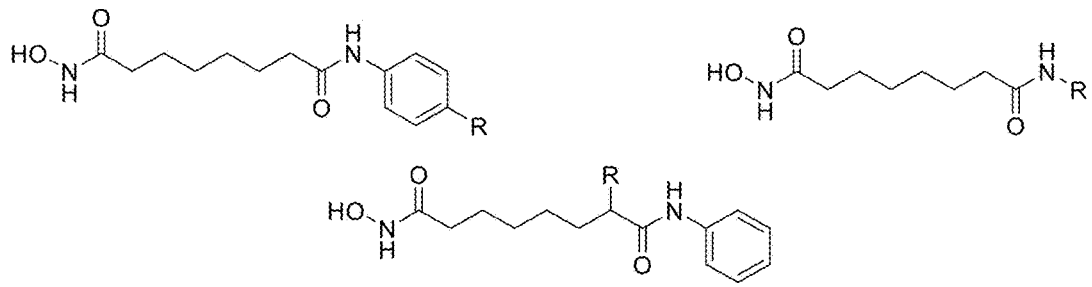
Figure 6B:
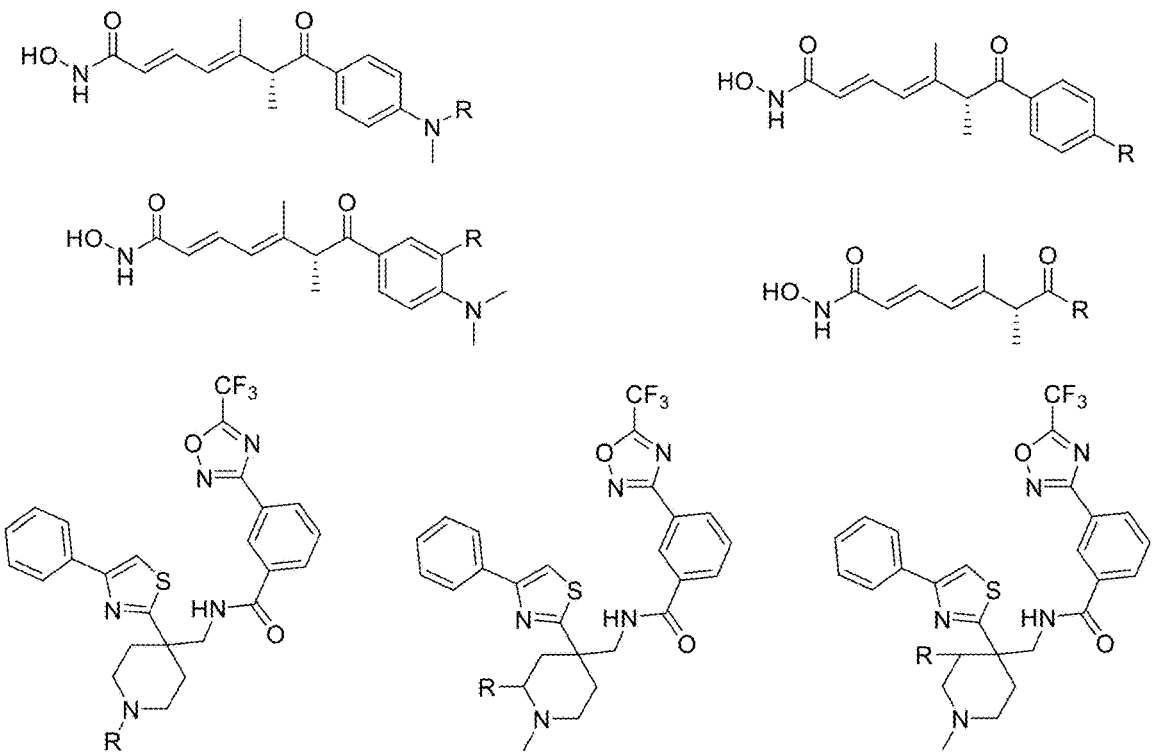

FIG. 6Z-6AA provide non-limiting examples of HDAC6 Targeting Ligands wherein R represents exemplary points at which the Linker can be attached. See for example, the PDB crystal structures 5kh3 and 5eei.

FIG. 6BB provides non-limiting examples of HDAC7 Targeting Ligands wherein R represents exemplary points at which the Linker can be attached. For additional examples and related ligands, see, the PDB crystal structure 3c10 and related ligands described in "Human HDAC7 harbors a class IIa histone deacetylase-specific zinc binding motif and cryptic deacetylase activity." Schuetz, A. et al. *J. Biol. Chem.* 283: 11355 (2008) and the PDB crystal structure PDB 3zns and related ligands described in "Selective Class IIa Histone Deacetylase Inhibition Via a Non-Chelating Zinc Binding Group". Lobera, M. et al. *Nat. Chem. Biol.* 9: 319 (2013).

Figure 7A:
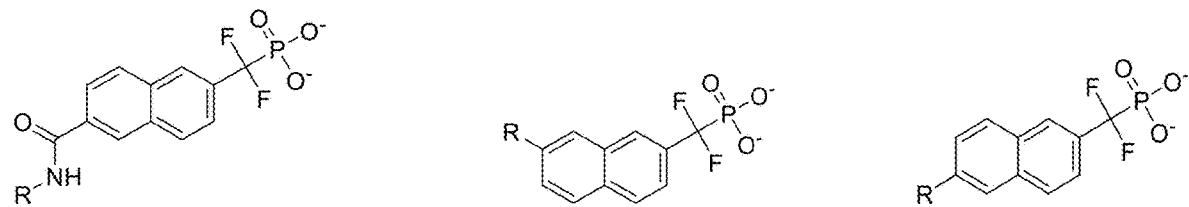
Figure 7B:
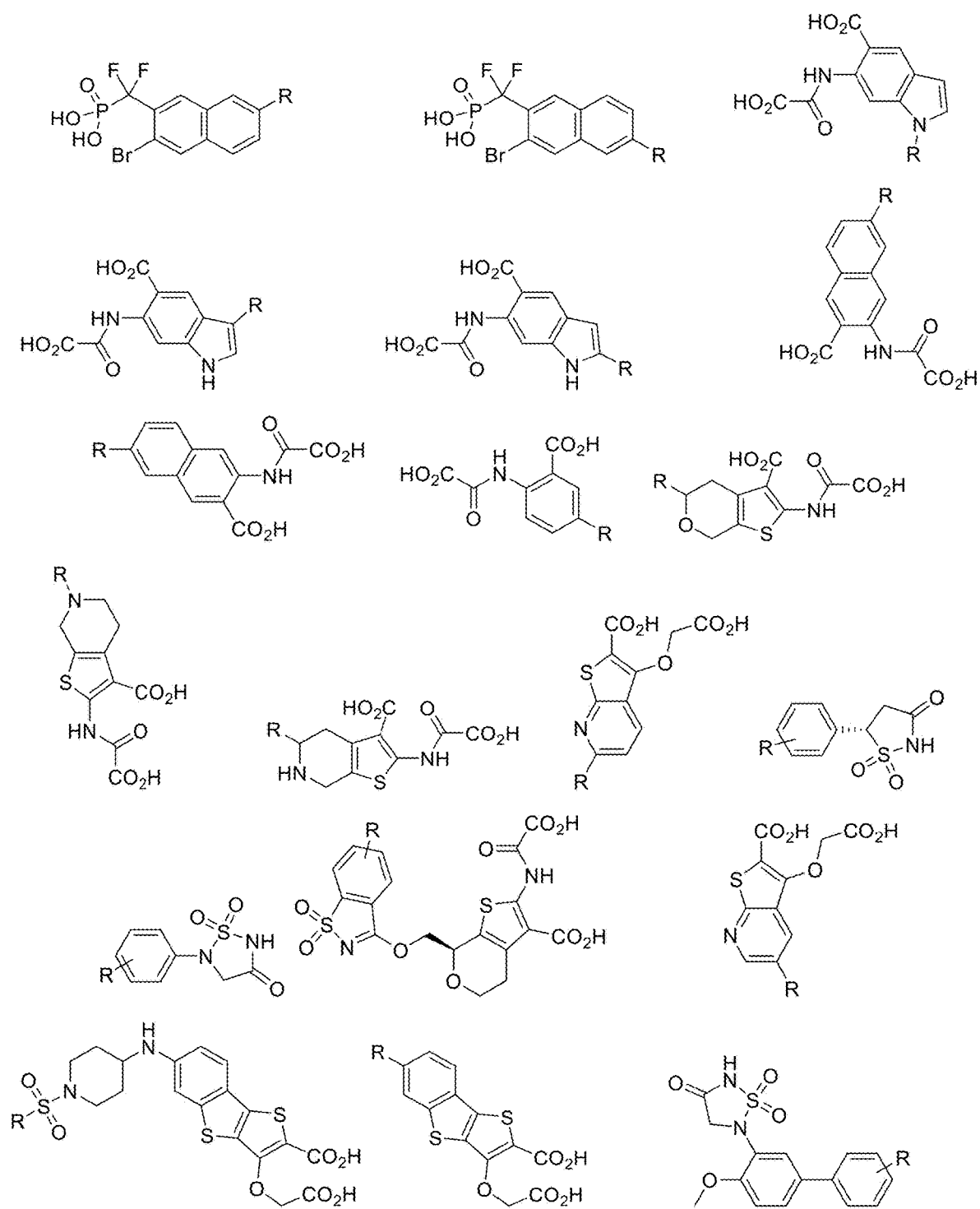
Figure 7C:
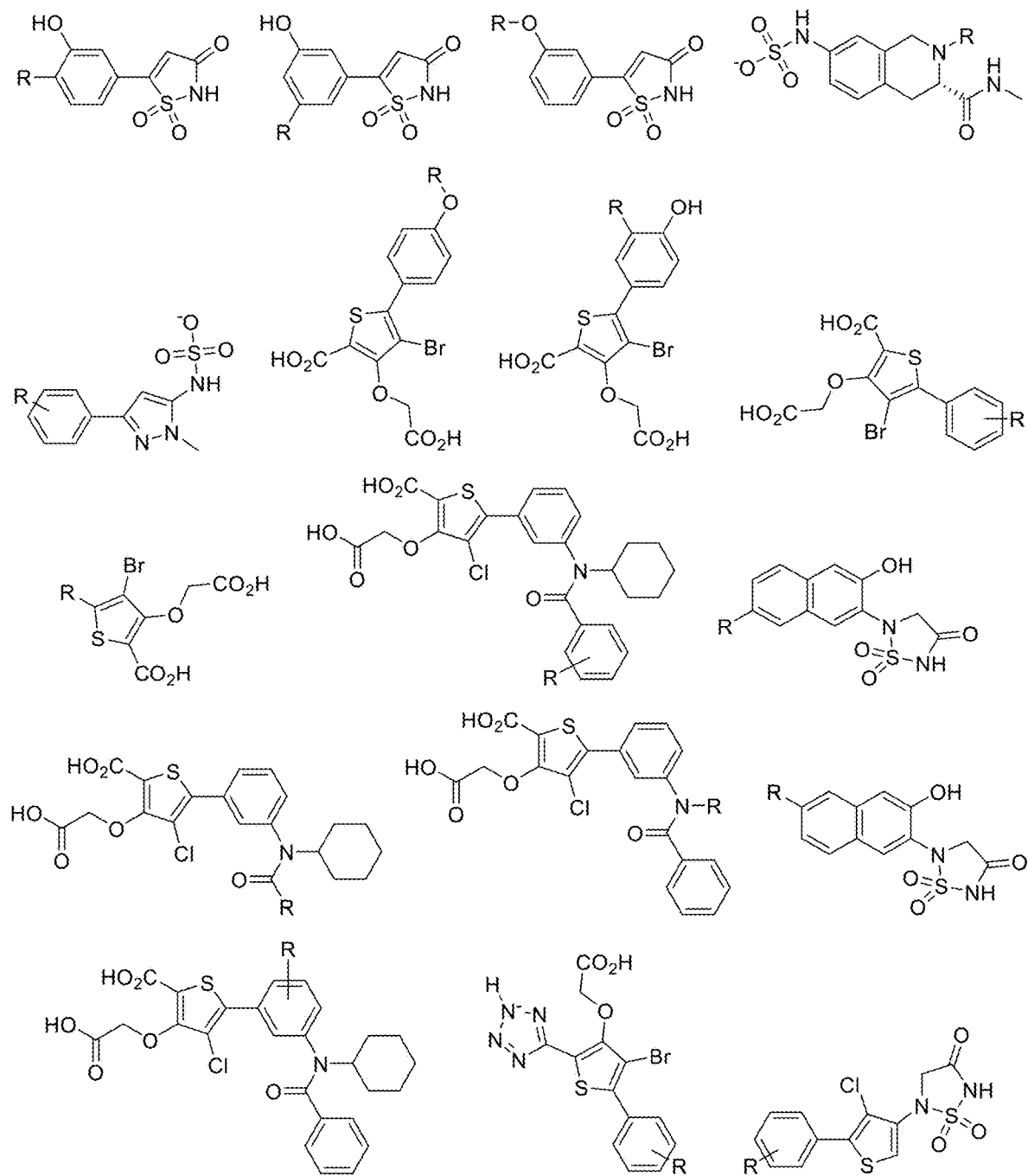

FIG. 7A-7C provide non-limiting examples of Protein Tyrosine Phosphatase, Non-Receptor Type 1, PTP1B Targeting Ligands wherein R represents exemplary points at which the Linker can be attached. For additional examples and related ligands, see, the PDB crystal structure 1bzj described in "Structural basis for inhibition of the protein tyrosine phosphatase 1B by phosphotyrosine peptide mimetics" Groves, M. R. et al. *Biochemistry* 37: 17773-17783 (1998); the PDB crystal structure 3cwe described in "Discovery of [(3-bromo-7-cyano-2-naphthyl)(difluoro)methyl] phosphonic acid, a potent and orally active small molecule PTP1B inhibitor". Han Y, Bioorg*Med Chem Lett.* 18:3200-5 (2008); the PDB crystal structures 2azr and 2b07 described in "Bicyclic and tricyclic thiophenes as protein tyrosine phosphatase 1B inhibitors." Moretto, A. F. et al. *Bioorg. Med Chem.* 14: 2162-2177 (2006); the PDB crystal structures PDB 2bgd, 2bge, 2cm7, 2cm8, 2cma, 2cmb, 2cmc described in ""Structure-Based Design of Protein Tyrosine Phosphatase-1B Inhibitors". Black, E. et al. *Bioorg. Med Chem. Lett.* 15: 2503 (2005) and "Structural Basis for Inhibition of Protein-Tyrosine Phosphatase 1B by Isothiazolidinone Heterocyclic Phosphonate Mimetics." Ala, P. J. et al. *J. Biol. Chem.* 281: 32784 (2006); the PDB crystal structures 2f6t and 2f6w described in "1,2,3,4-Tetrahydroisoquinolinyl sulfamic acids as phosphatase PTP1B inhibitors". Klopfenstein, S. R. et al. *Bioorg. Med Chem. Lett.* 16: 1574-1578 (2006); the PDB crystal structures 2h4g, 2h4k, 2hbl described in ""Monocyclic thiophenes as protein tyrosine phosphatase 1B inhibitors: Capturing interactions with Asp48." Wan, Z. K. et al. *Bioorg. Med Chem. Lett.* 16: 4941-4945 (2006); the PDB crystal structures 2zn7 described in "Structure-based optimization of protein tyrosine phosphatase-1 B inhibitors: capturing interactions with arginine 24". Wan, Z. K. et al. *Chem Med Chem.* 3:1525-9 (2008); the PDB crystal structure 2nt7, 2nta described in "Probing acid replacements of thiophene PTP1B inhibitors." Wan, Z. K. et al. *Bioorg. Med. Chem. Lett.* 17: 2913-2920 (2007); and, WO 2008148744 A1 assigned to Novartis AG titled "Thiadiazole derivatives as antidiabetic agents". See also, the PDB crystal structures 1c84, 1c84, 1c85, 1c86, 1c88, 118g and described in ""2-(oxalylamino)-benzoic acid is a general, competitive inhibitor of protein-tyrosine phosphatases". Andersen, H. S. et al. *J. Biol. Chem.* 275: 7101-7108 (2000); "Structure-based design of a low molecular weight, nonphosphorus, nonpeptide, and highly selective inhibitor of protein-tyrosine phosphatase 1B." Iversen, L. F. et al. *J. Biol. Chem.* 275: 10300-10307 (2000); and, "Steric hindrance as a basis for structure-based design of selective inhibitors of protein-tyrosine phosphatases". Iversen, L. F. et al. *Biochemistry* 40: 14812-14820 (2001).

Figure 7D:
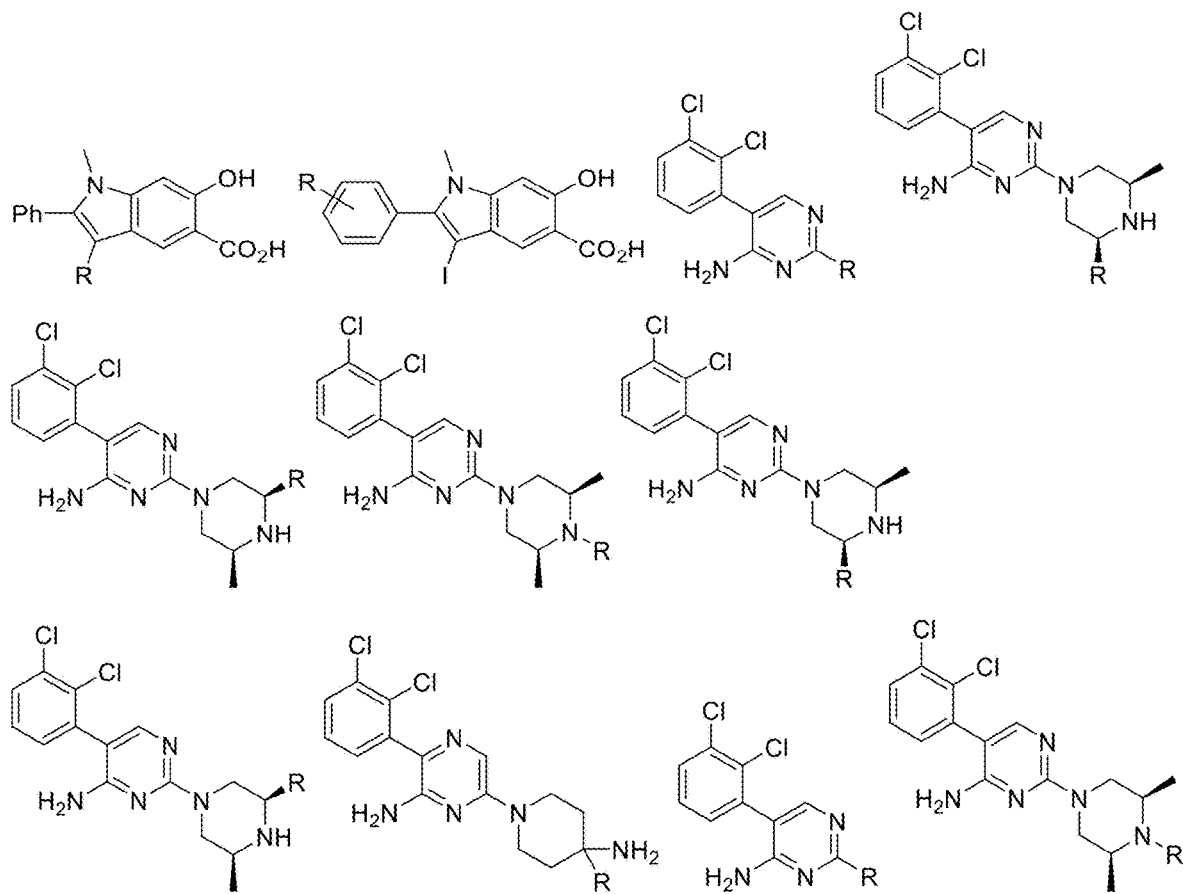

FIG. 7D provides non-limiting examples of Tyrosine-protein phosphatase non-receptor type 11, SHP2 Targeting Ligands wherein R represents exemplary points at which the Linker can be attached. For additional examples and related ligands, see, the crystal structures PDB 4pvg and 3O5x and described in "Salicylic acid based small molecule inhibitor for the oncogenic Src homology-2 domain containing protein tyrosine phosphatase-2 (SHP2)." Zhang, X. et al. *J. Med Chem.* 53: 2482-2493 (2010); and, the crystal structure PDB 5ehr and related ligands described in "Allosteric Inhibition of SHP2: Identification of a Potent, Selective, and Orally Efficacious Phosphatase Inhibitor." Garcia Fortanet, J. et al. *J. Med. Chem.* 59: 7773-7782 (2016). Also, see the crystal structure PDB 5ehr described in "Allosteric Inhibition of SHP2: Identification of a Potent, Selective, and Orally Efficacious Phosphatase Inhibitor." Garcia Fortanet, J. et al. *J. Med. Chem.* 59: 7773-7782 (2016) and "Allosteric inhibition of SHP2 phosphatase inhibits cancers driven by receptor tyrosine kinases." Chen, Y. P. et al. *Nature* 535: 148-152 (2016).

Figure 7E:
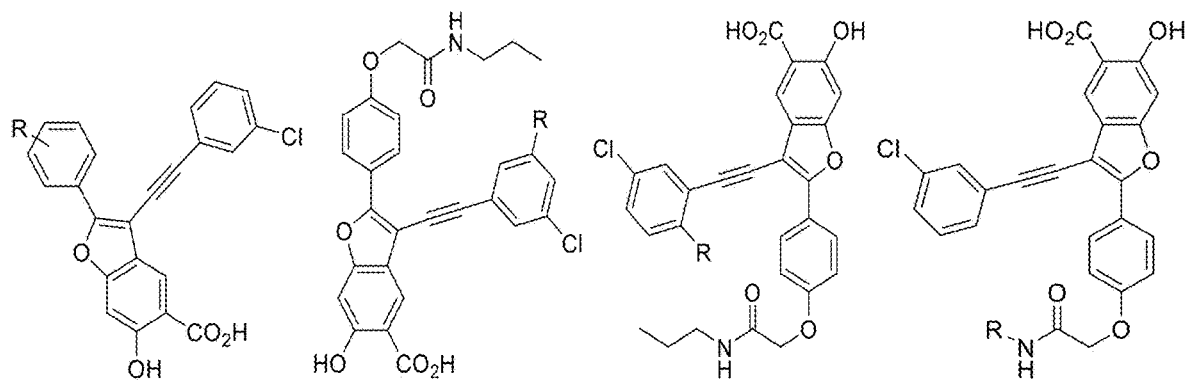

FIG. 7E provides non-limiting examples of Tyrosine-protein phosphatase non-receptor type 22 Targeting Ligands wherein R represents exemplary points at which the Linker can be attached. For additional examples and related ligands, see, the crystal structure PDB 4j51 described in "A Potent and Selective Small-Molecule Inhibitor for the Lymphoid-Specific Tyrosine Phosphatase (LYP), a Target Associated with Autoimmune Diseases." He, Y. et al. *J. Med. Chem.* 56: 4990-5008 (2013).

Figure 7F:
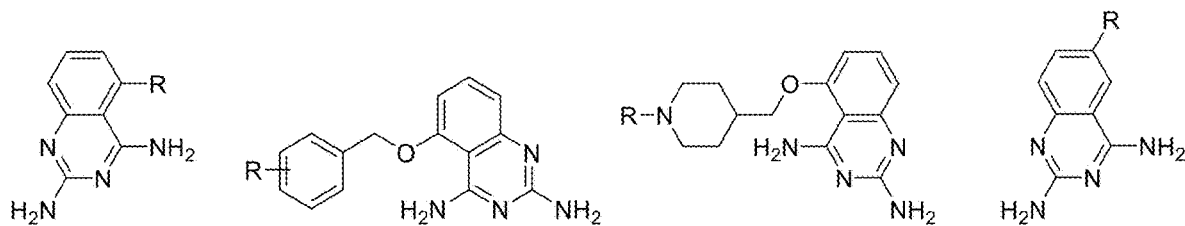

FIG. 7F provides non-limiting examples of Scavenger mRNA-decapping enzyme DcpS Targeting Ligands wherein R represents exemplary points at which the Linker can be attached. For additional examples and related ligands, see, the crystal structures PDB 3bl7, 3bl9, 3bla, 4qde, 4qdv, 4qeb and related ligands described in "DcpS as a therapeutic target for spinal muscular atrophy." Singh, J. et al. *ACS Chem. Biol.* 3: 711-722 (2008).

Figure 8A:
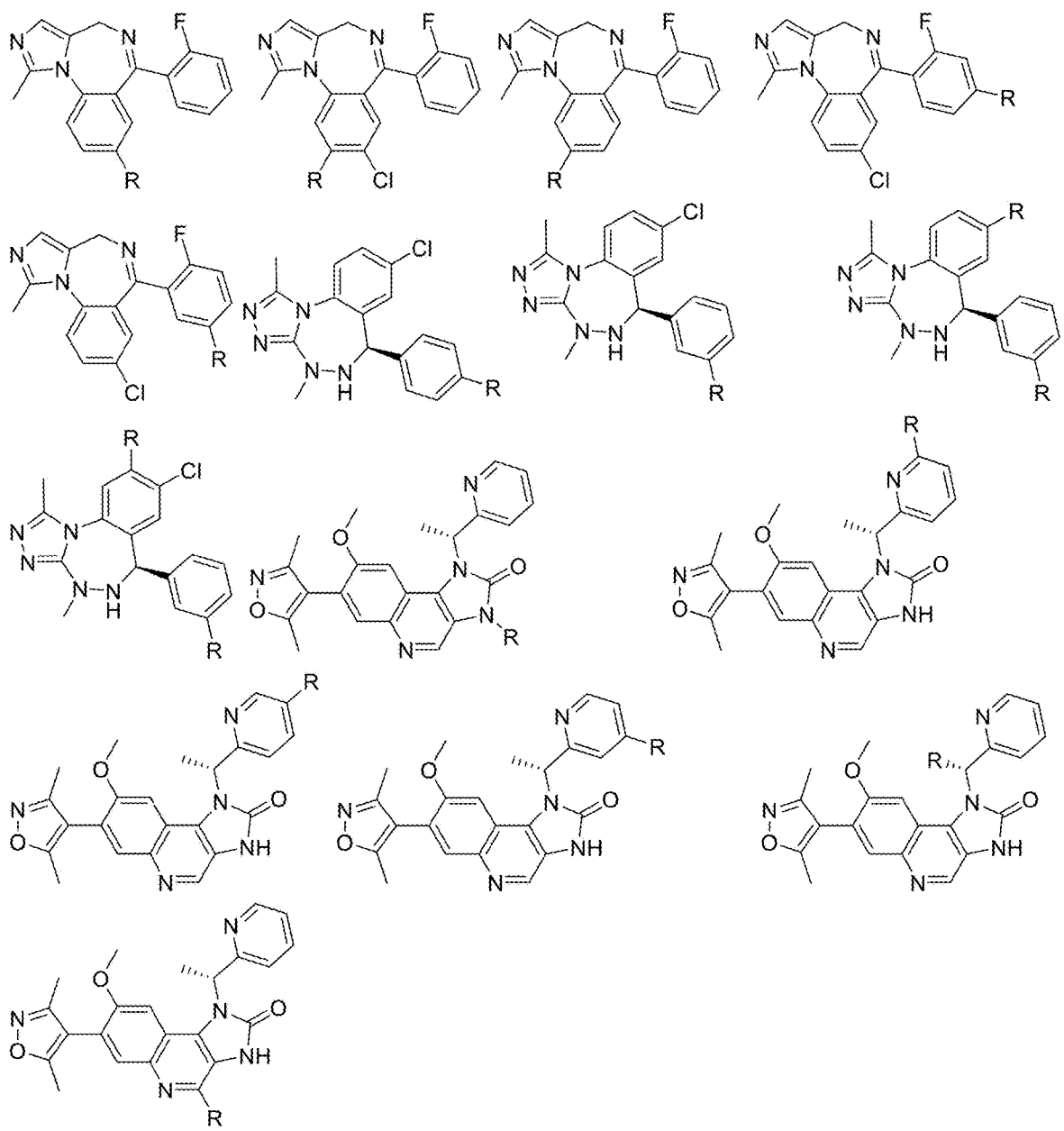
Figure 8B:
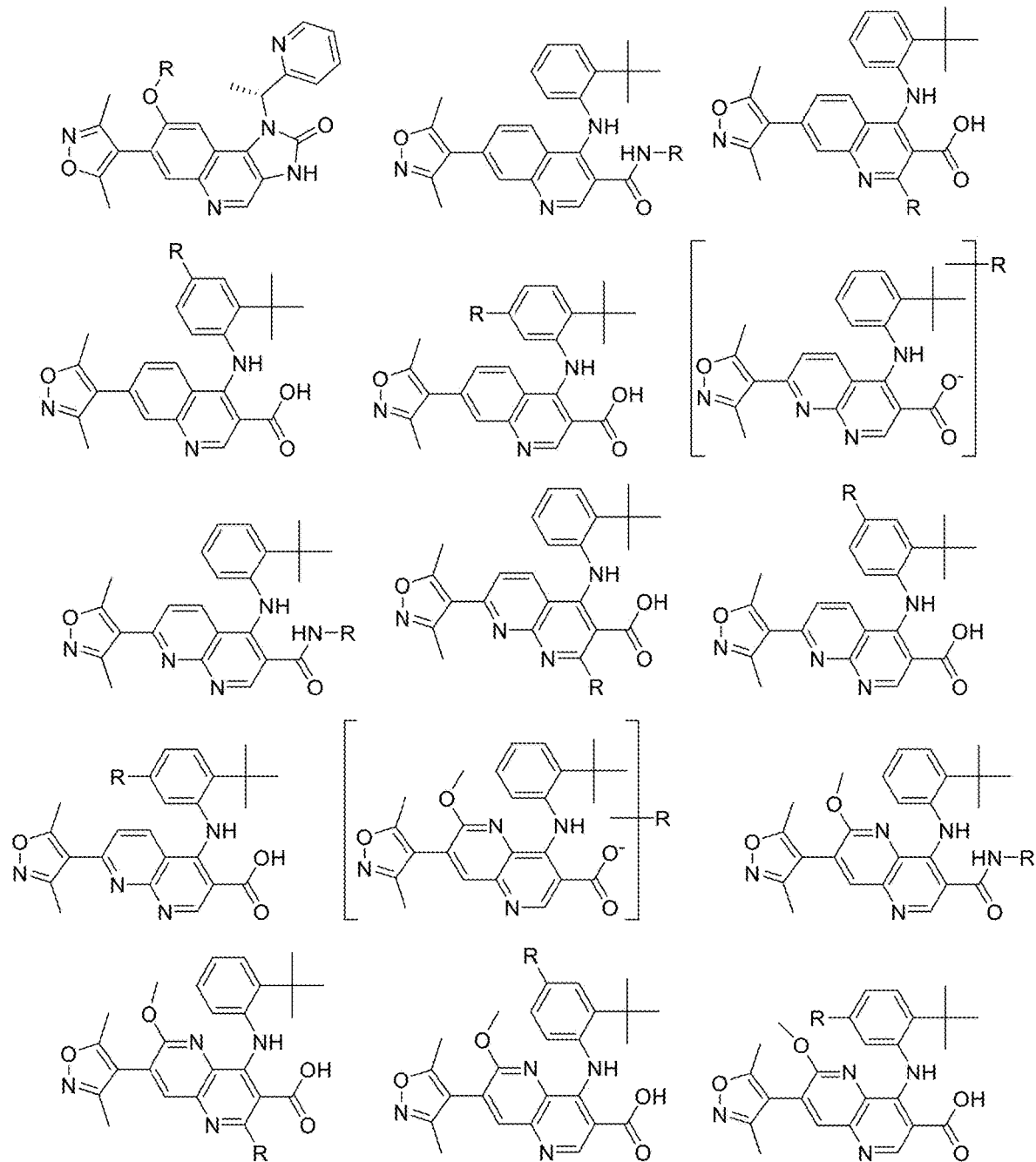
Figure 8C:
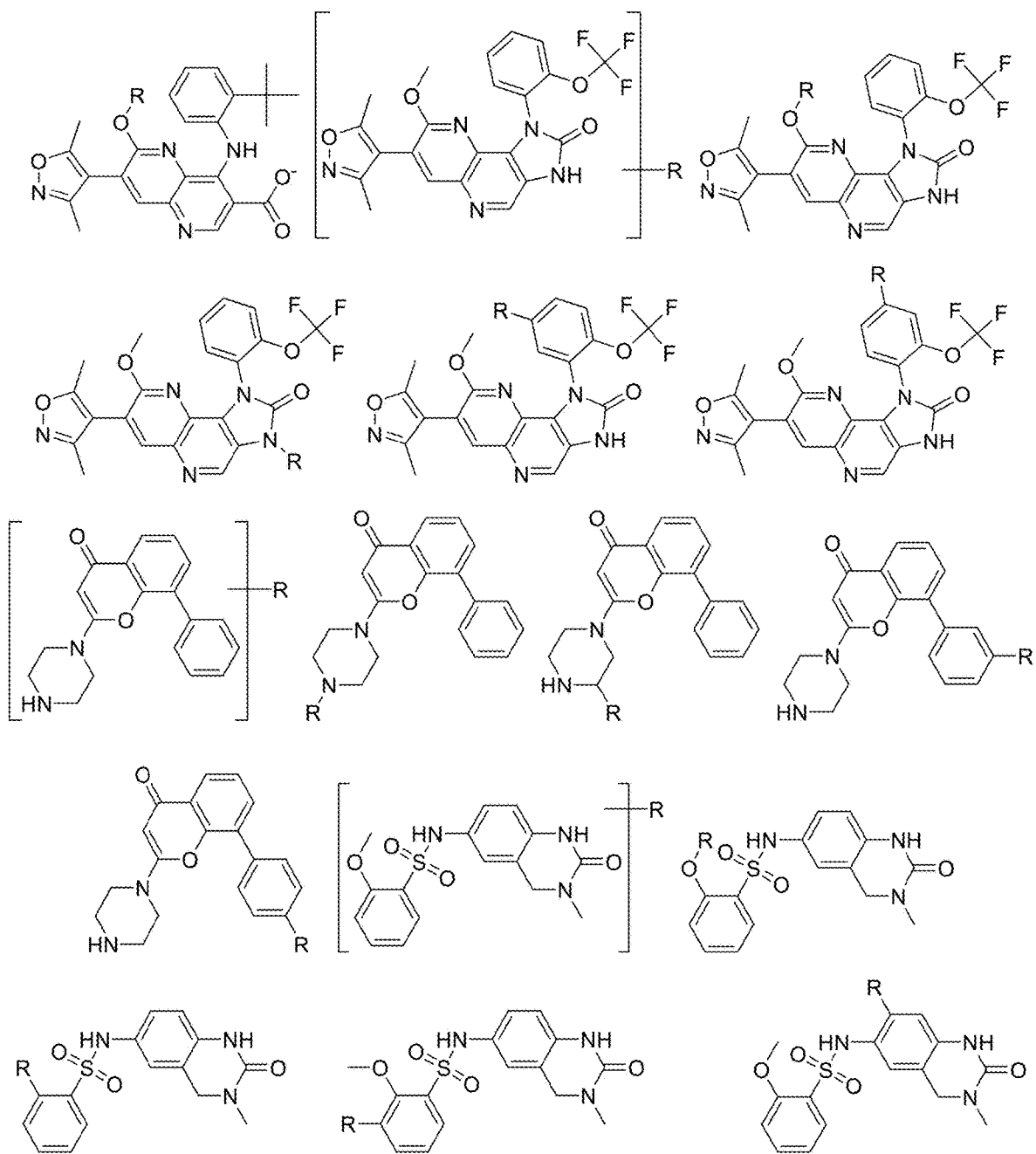
Figure 8D:
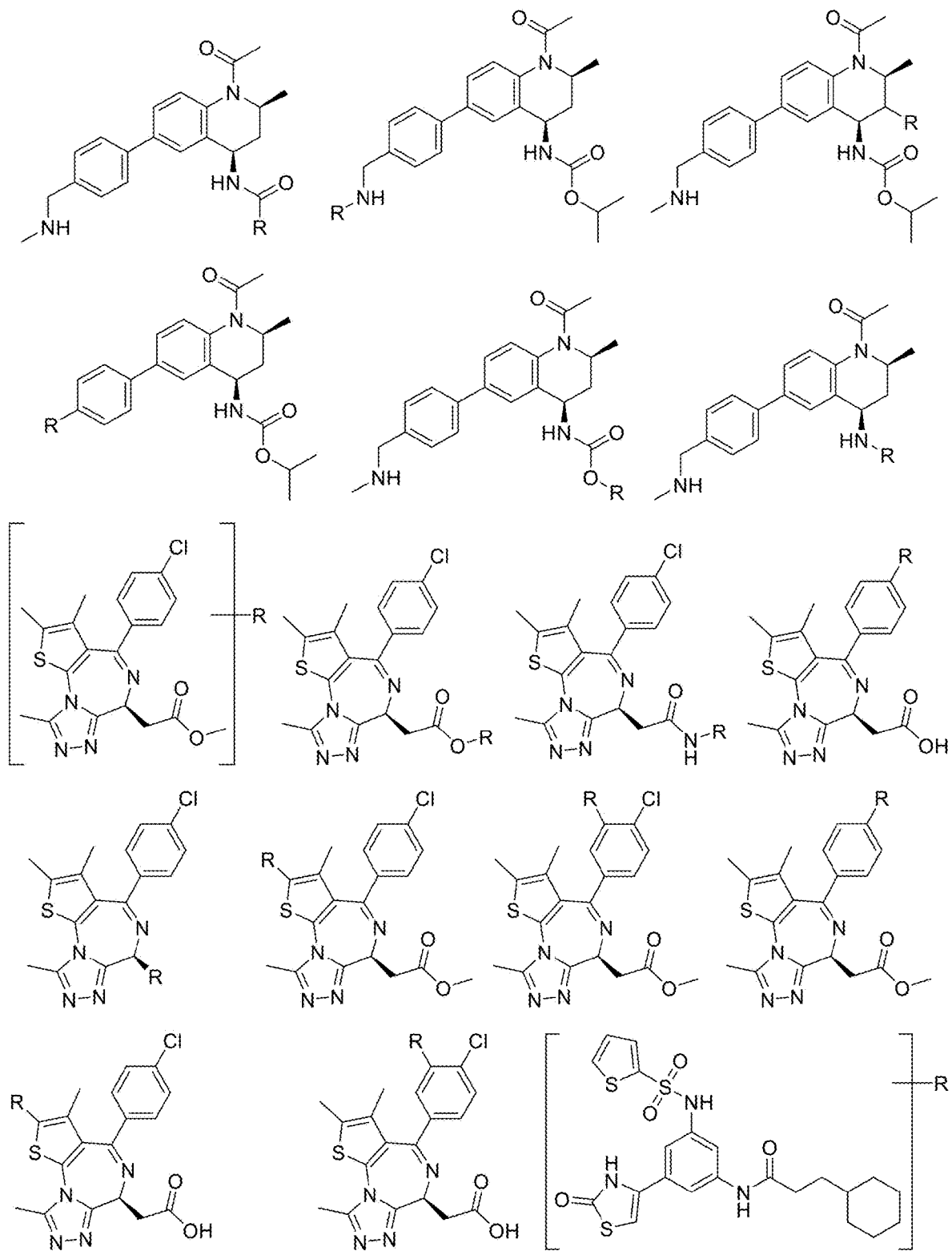
Figure 8E:
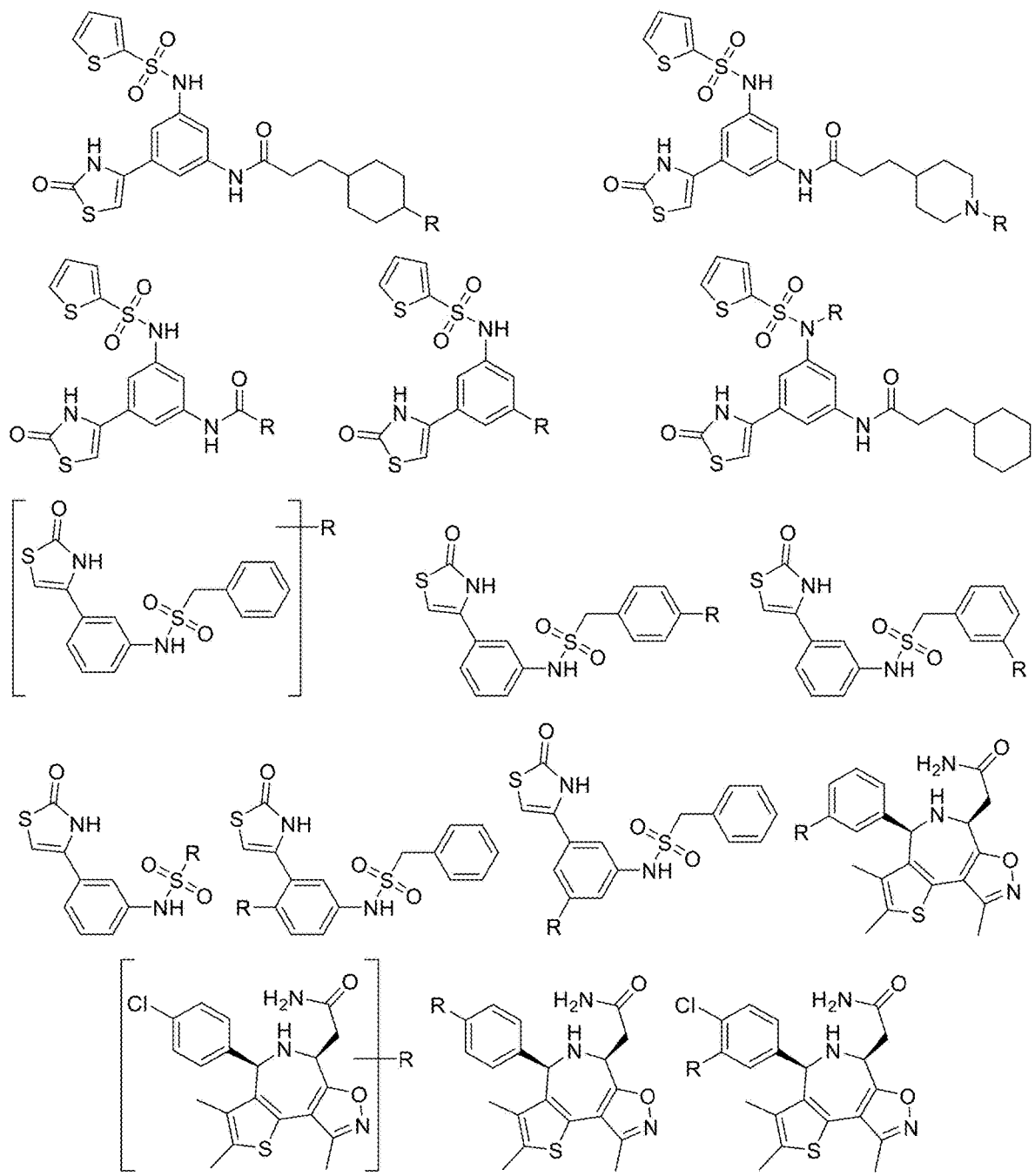
Figure 8F:
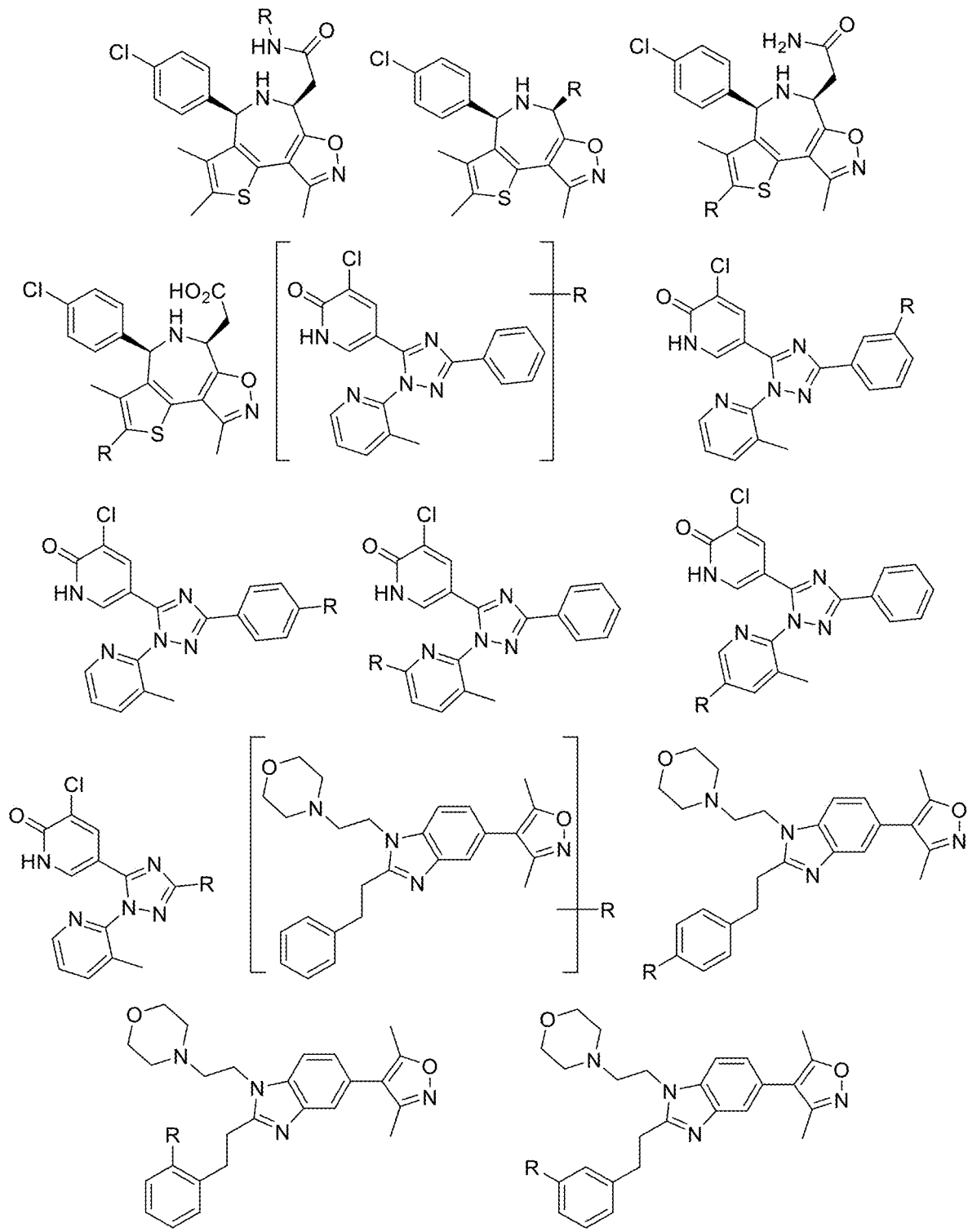
Figure 8G:
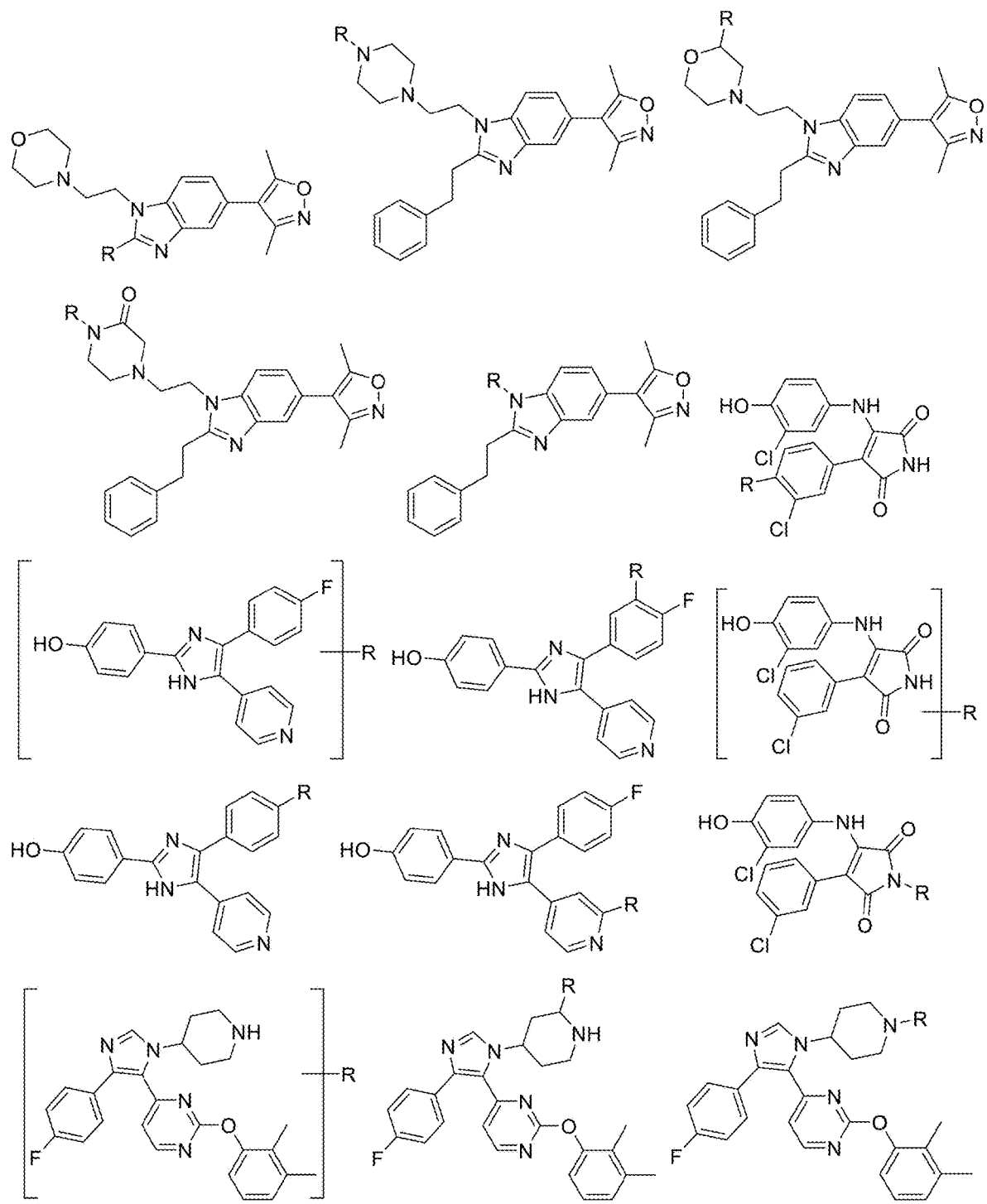
Figure 8H:
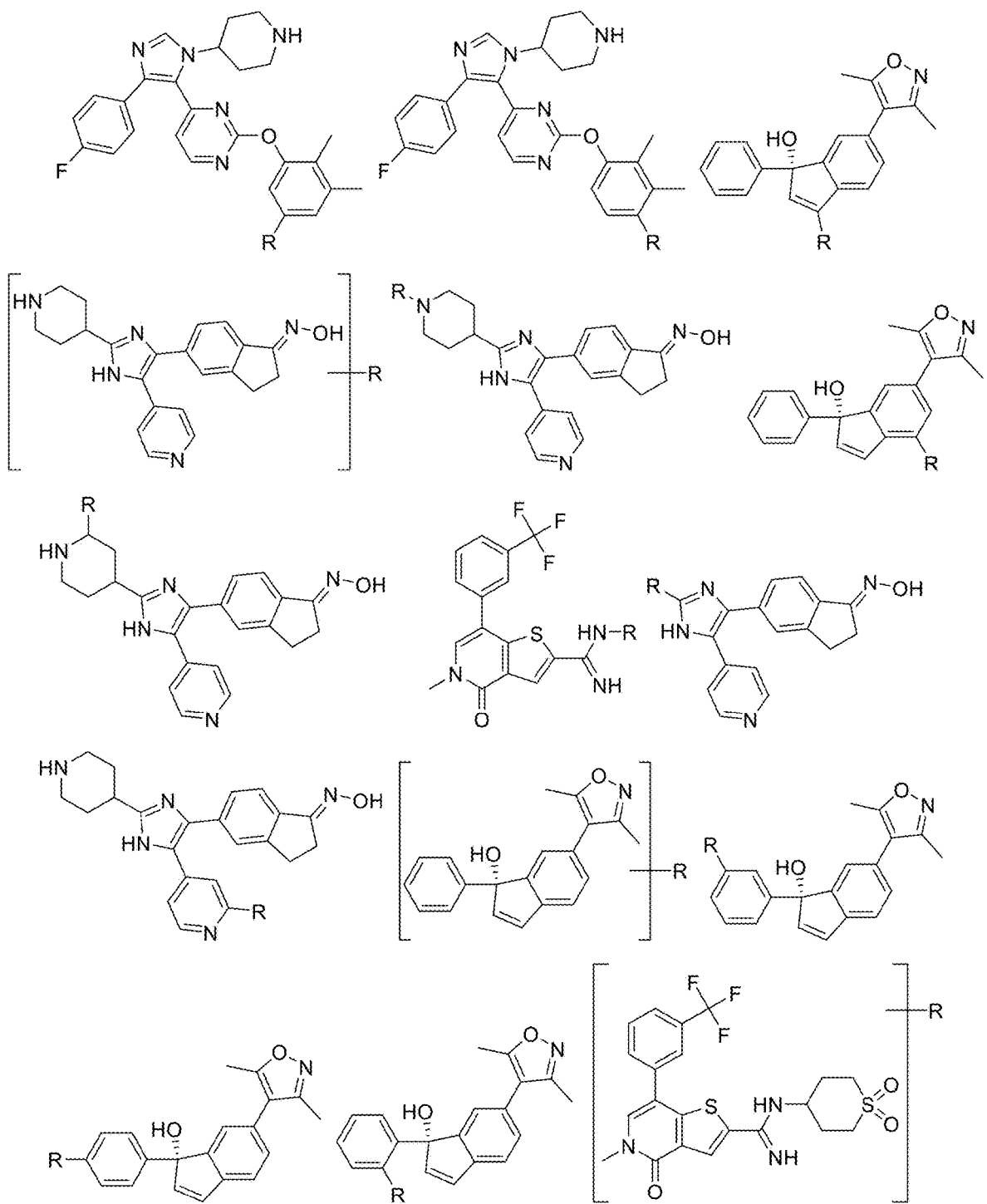
Figure 8I:
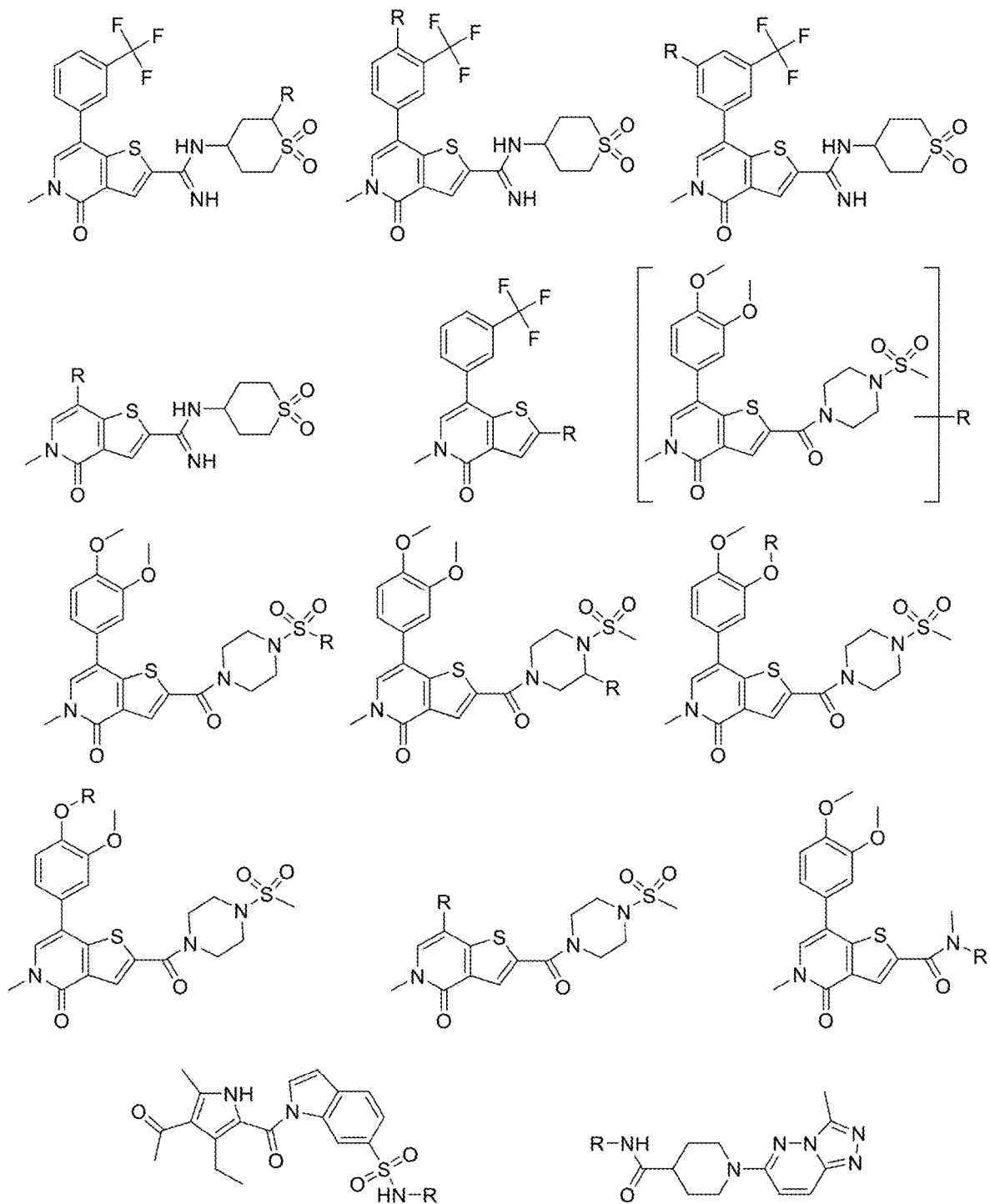
Figure 8J:
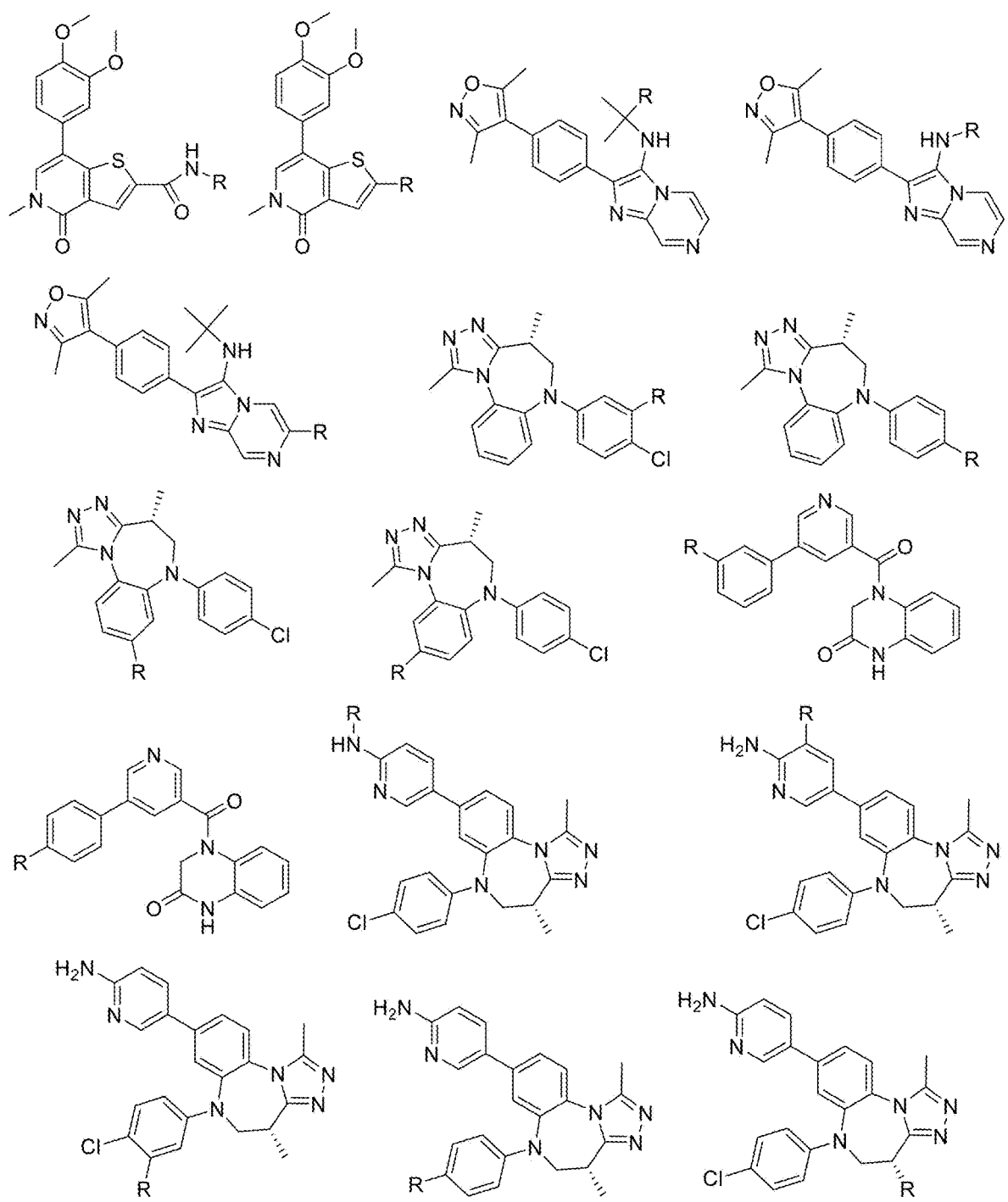
Figure 8K:
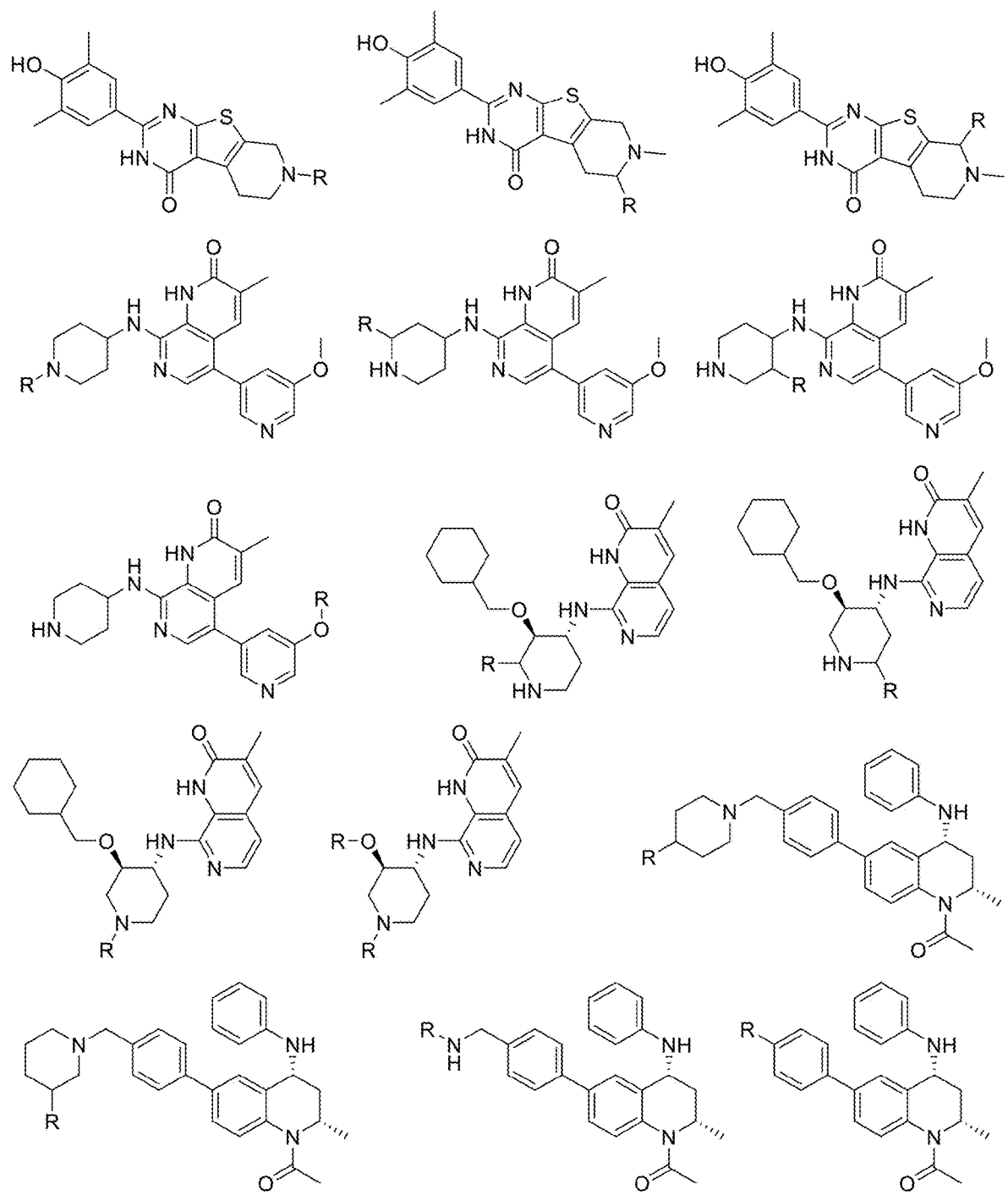
Figure 8L:
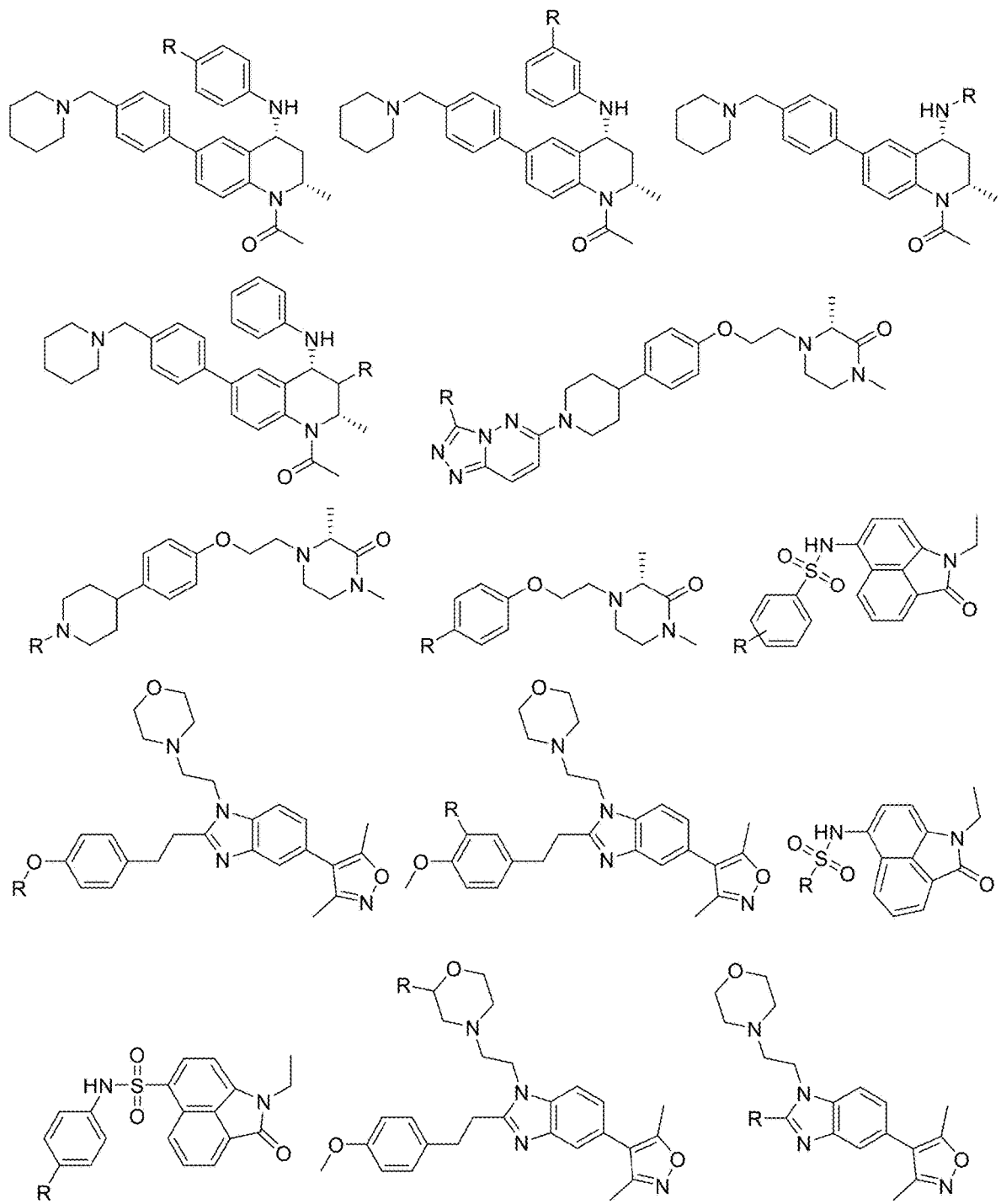
Figure 8M:
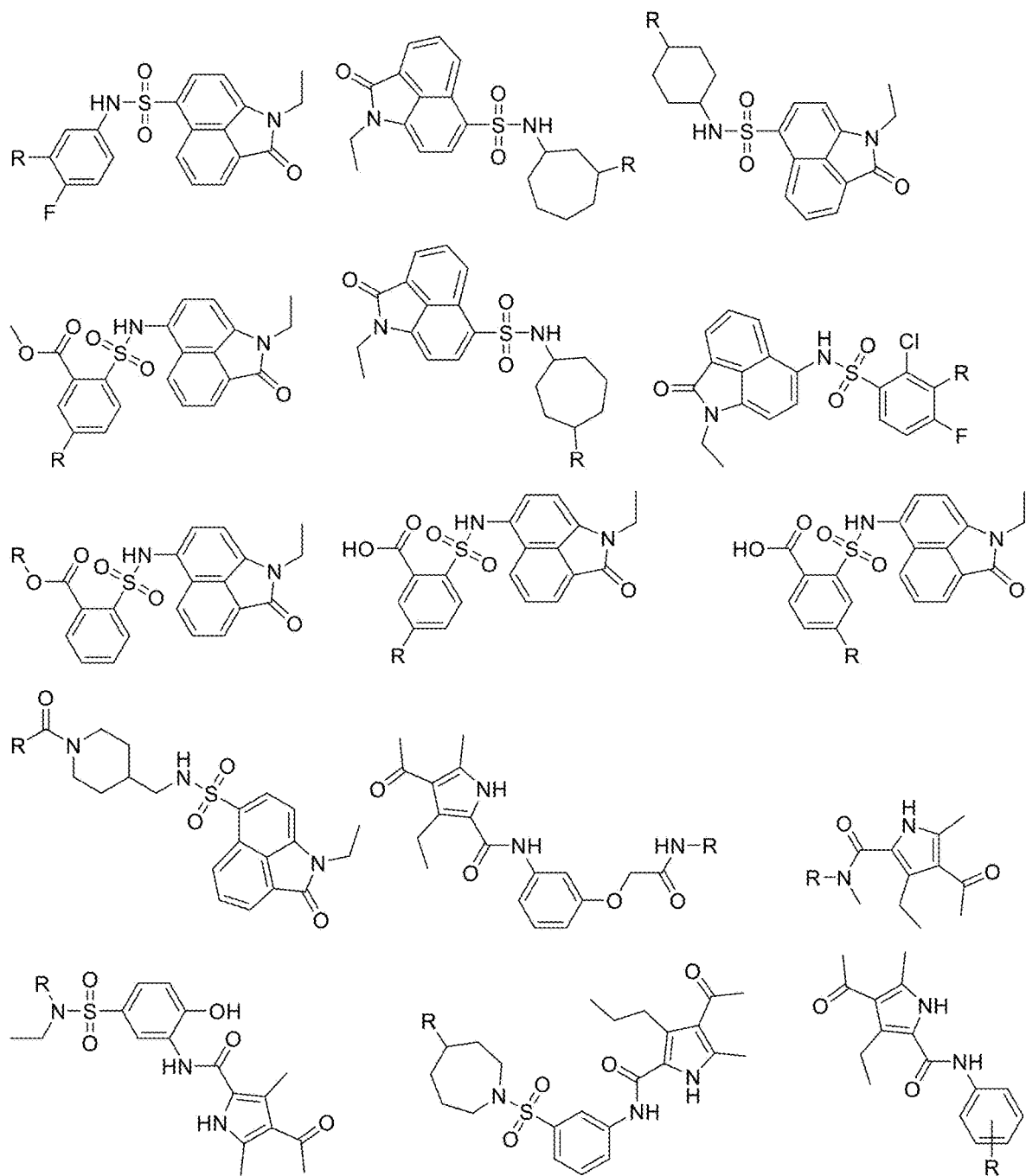
Figure 8N:
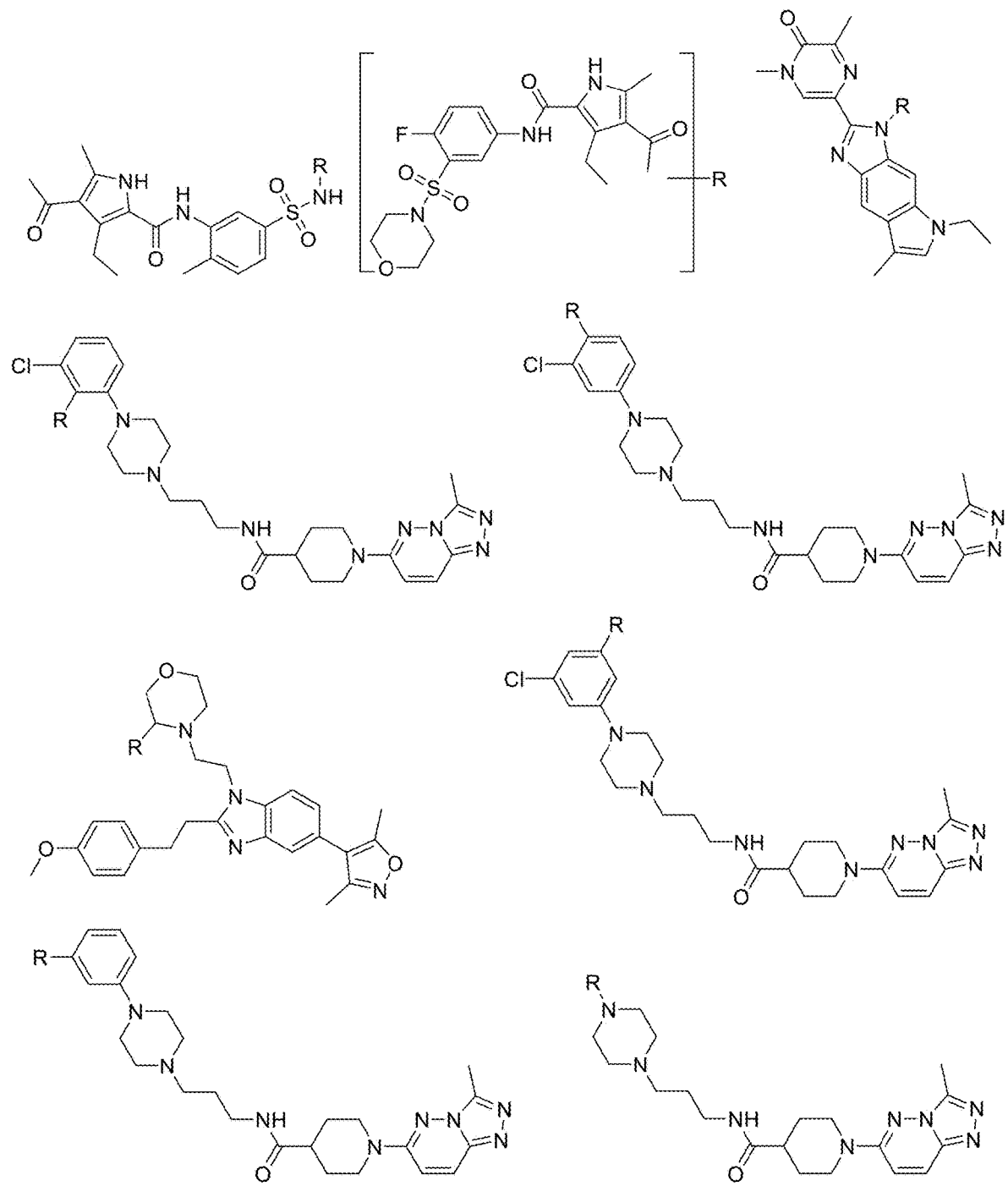
Figure 8O:
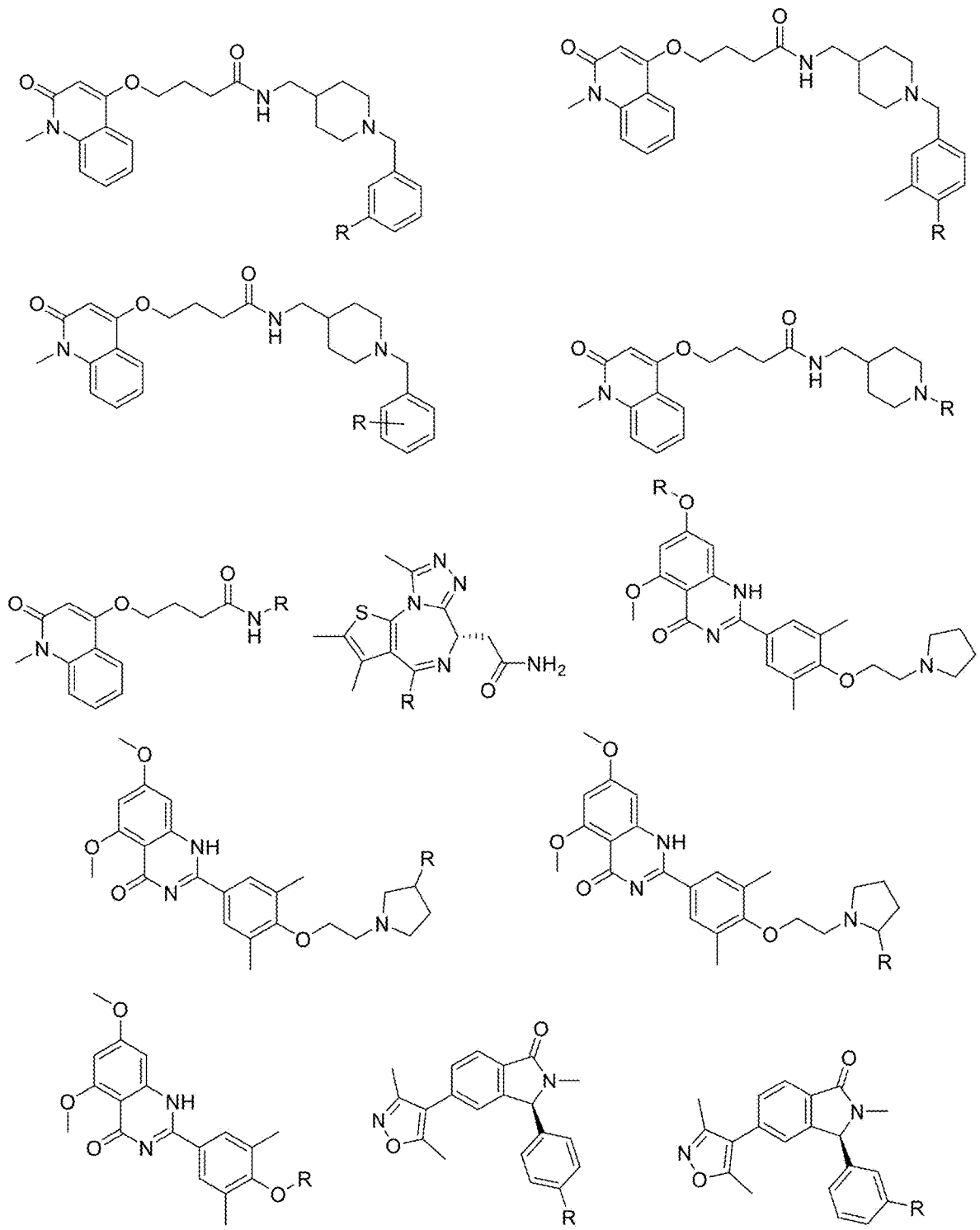
Figure 8P:
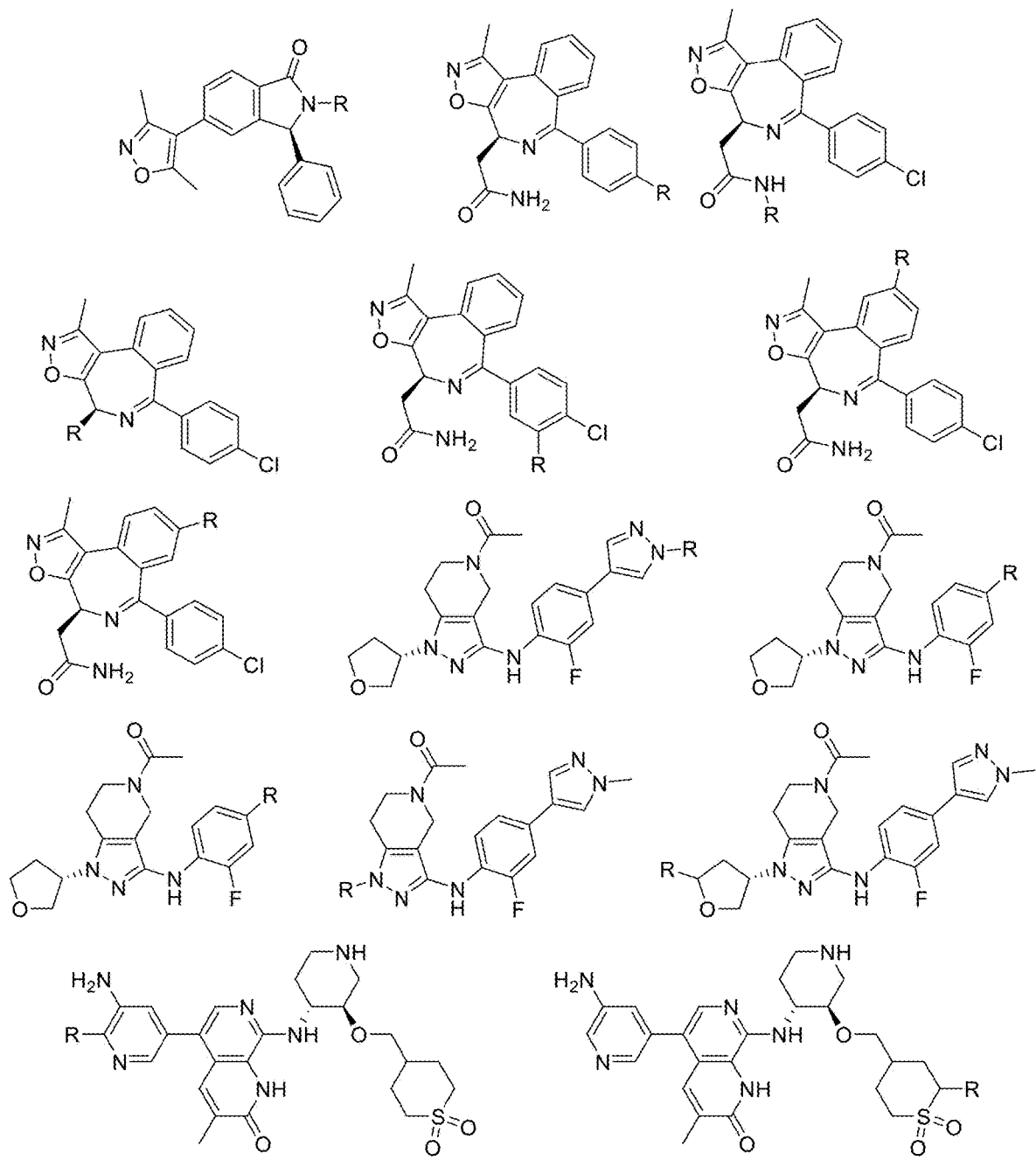
Figure 8Q:
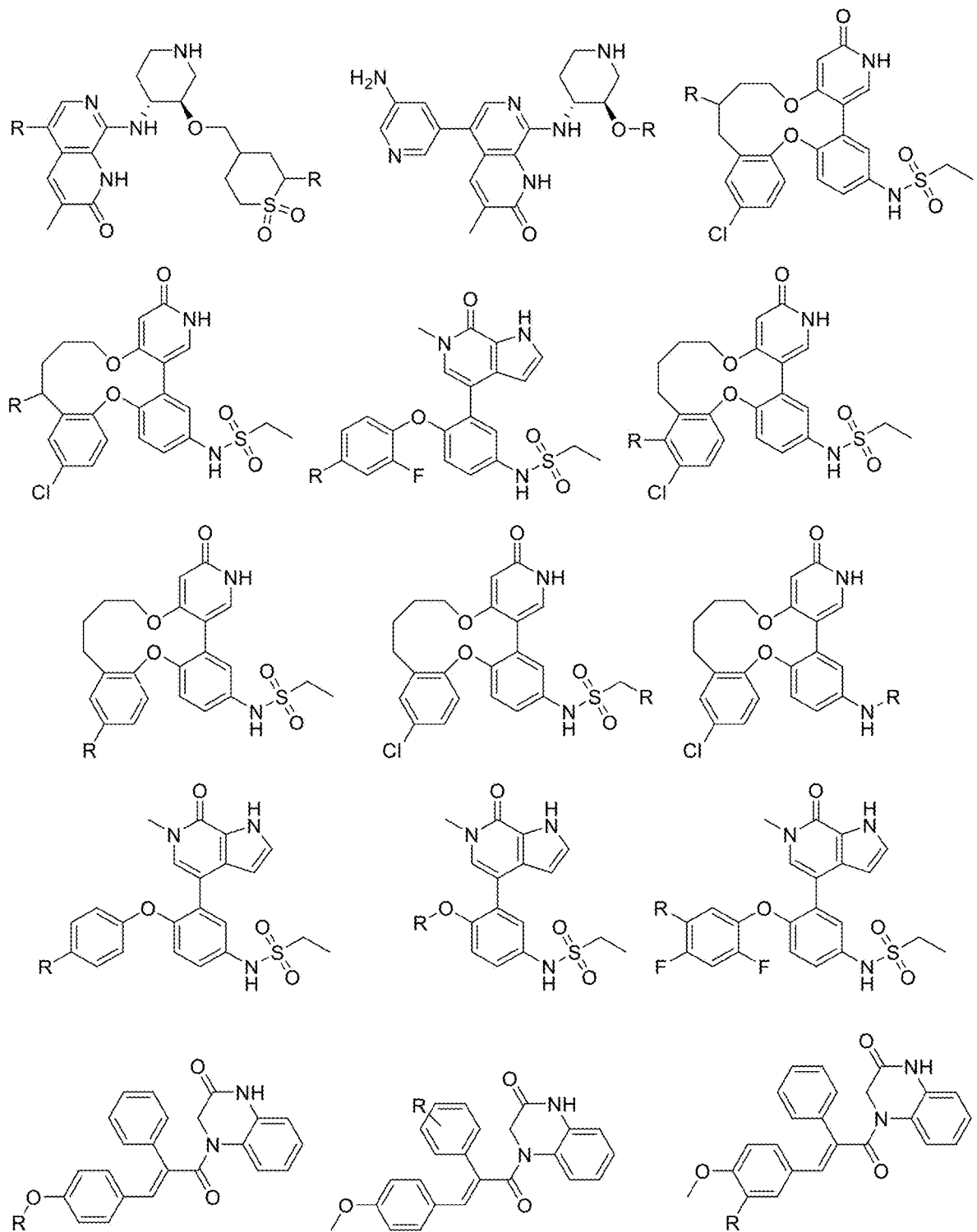
Figure 8R:
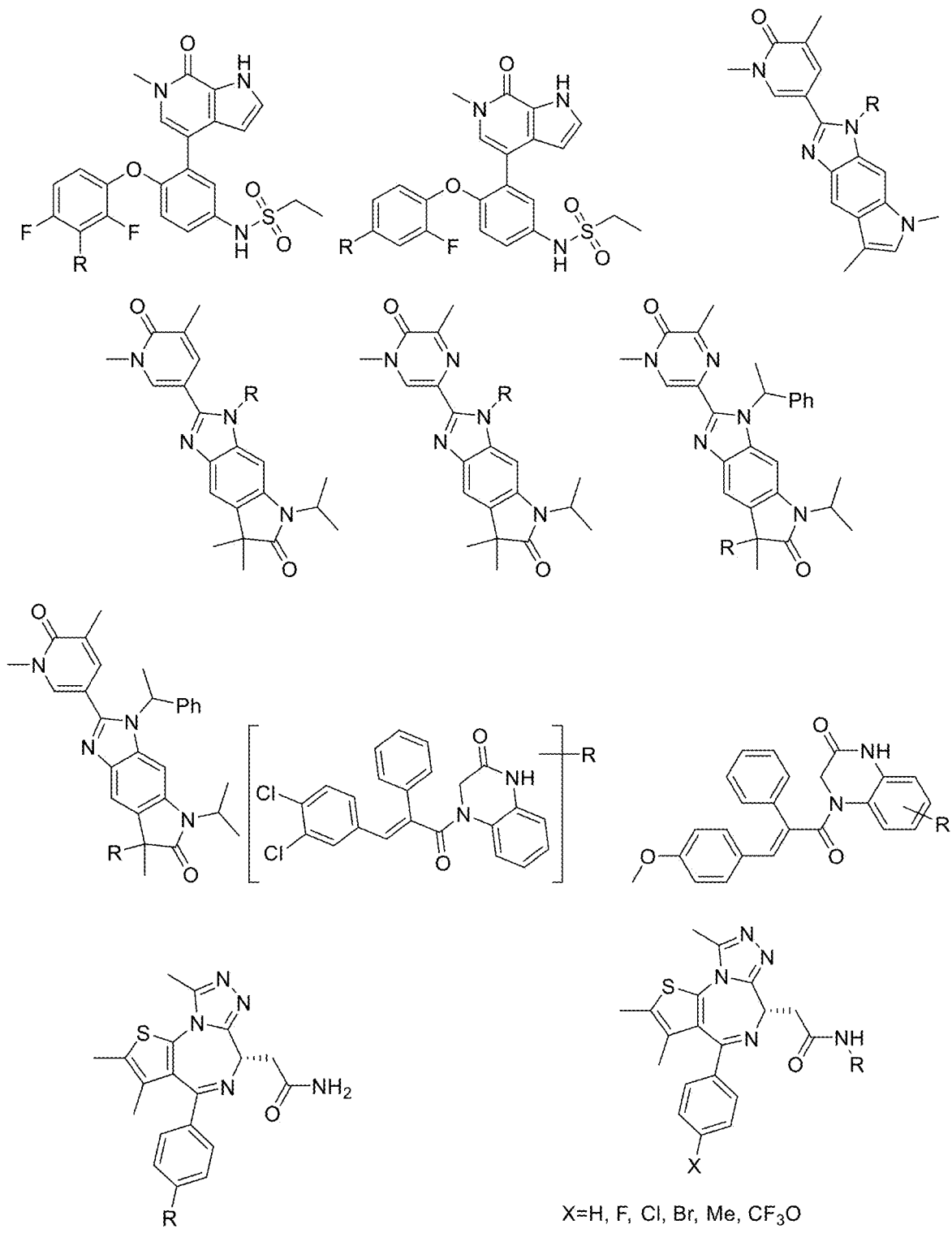
Figure 8U:
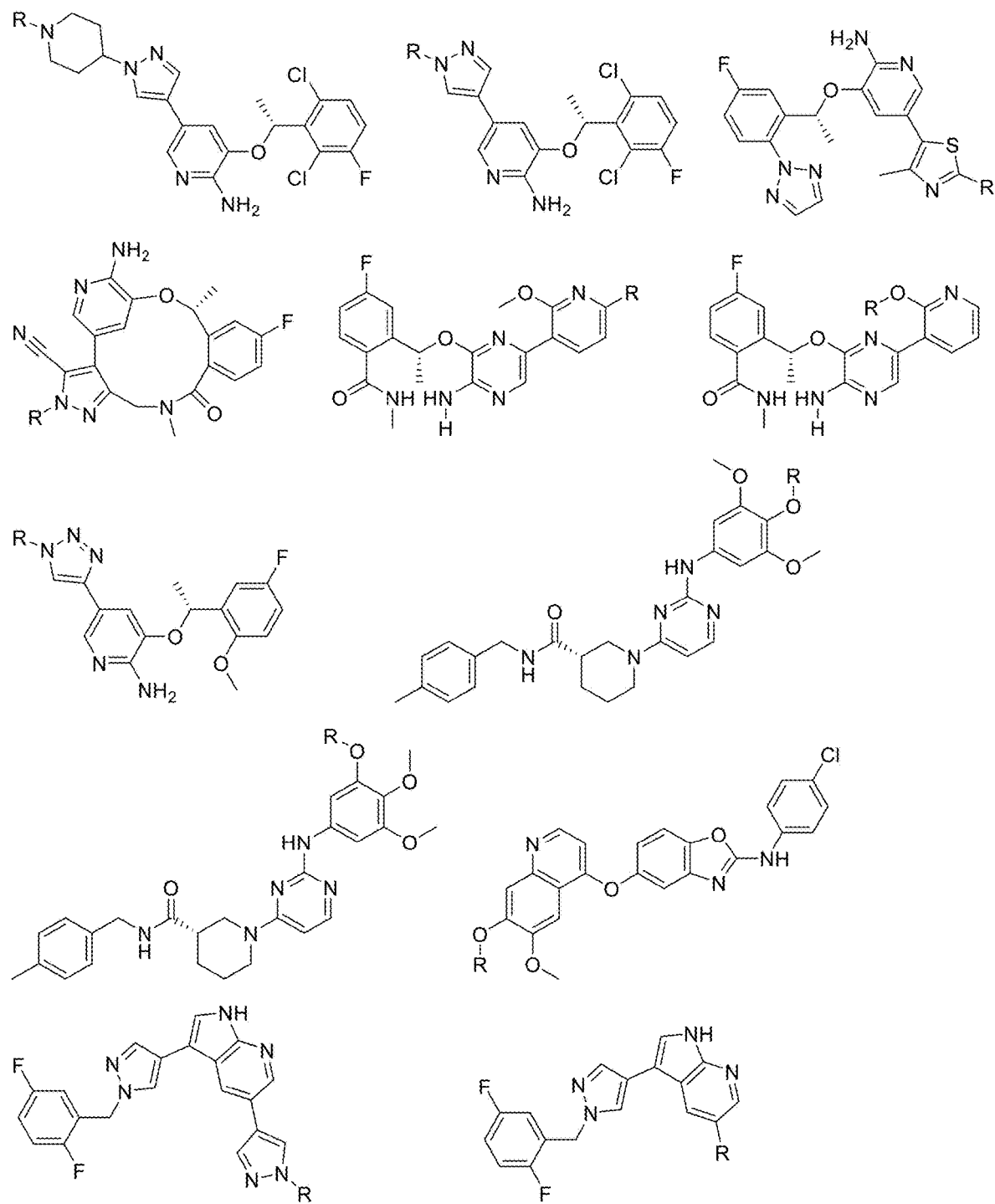
Figure 8V:
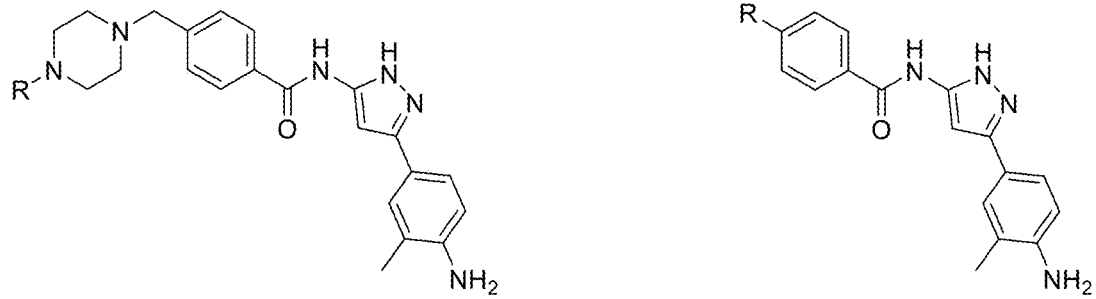
Figure 8W:
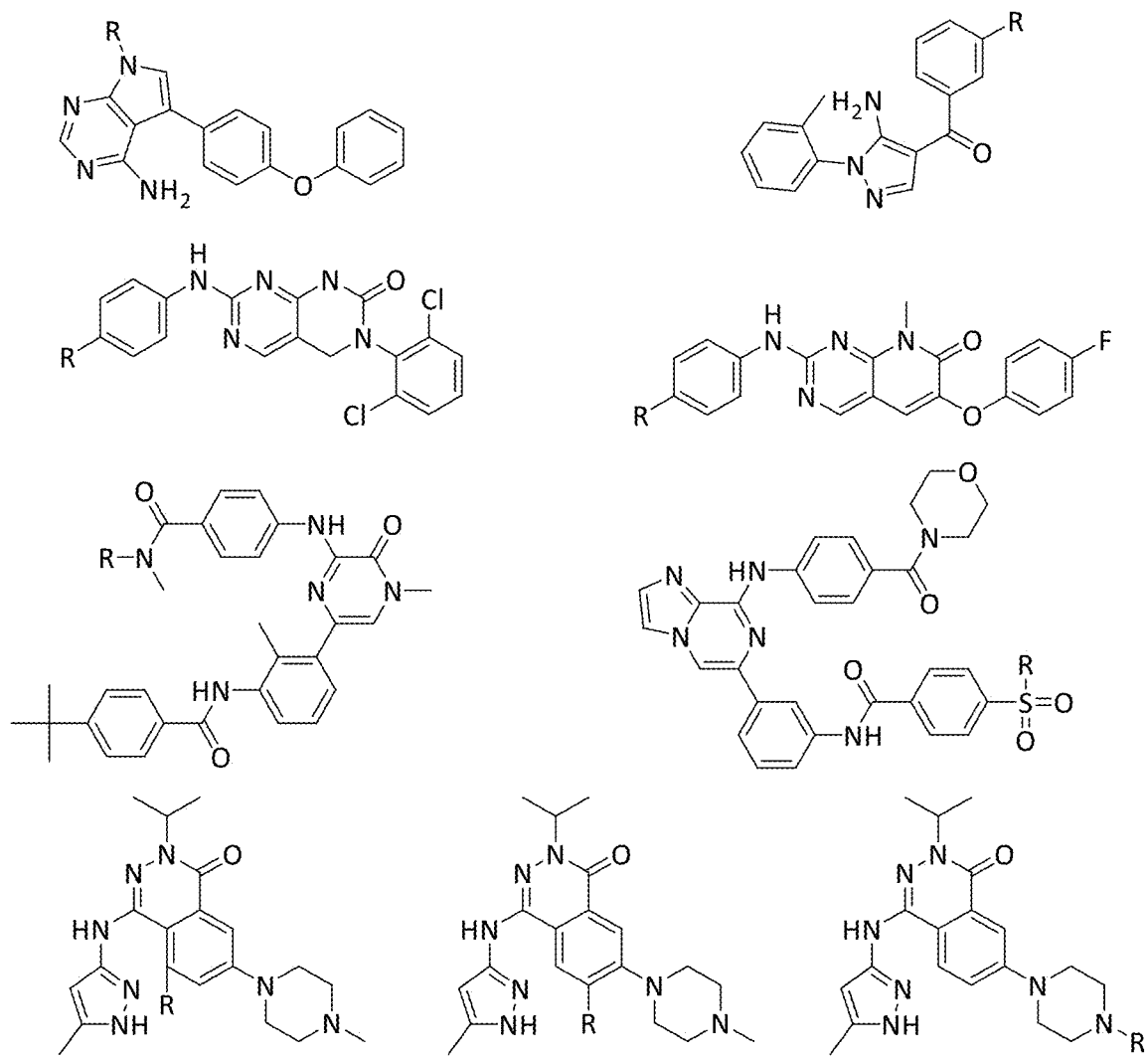
Figure 8X:
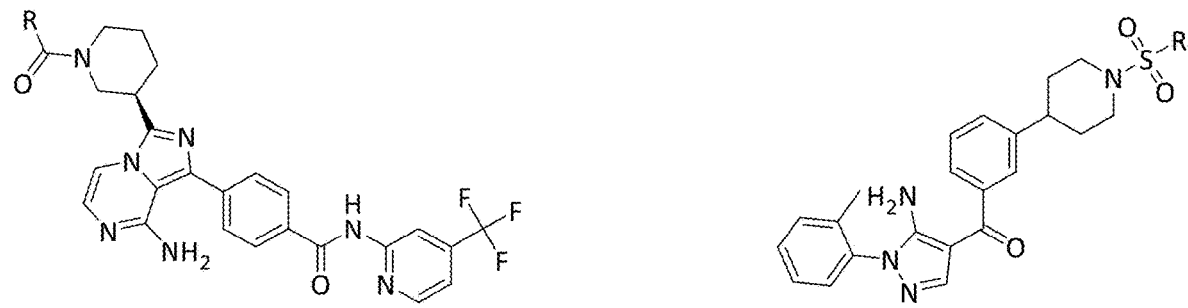
Figure 8Y:
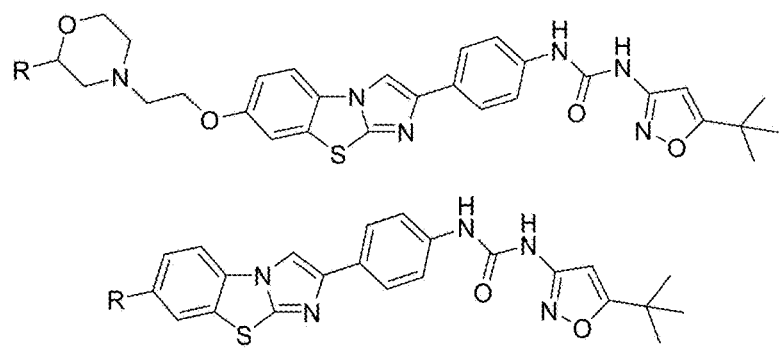
Figure 8Z:
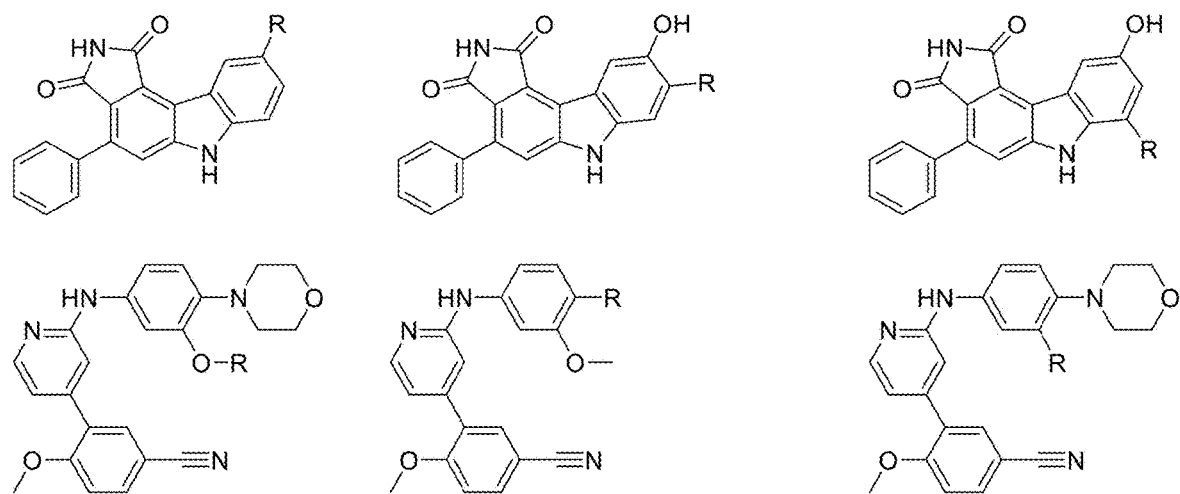
Figure 8A:
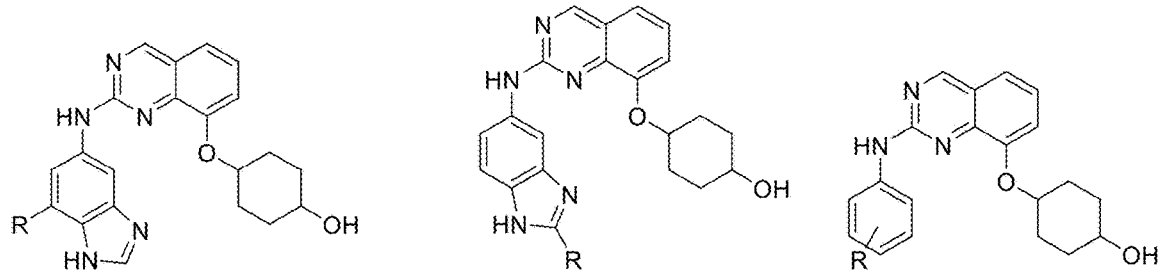
Figure 8B:
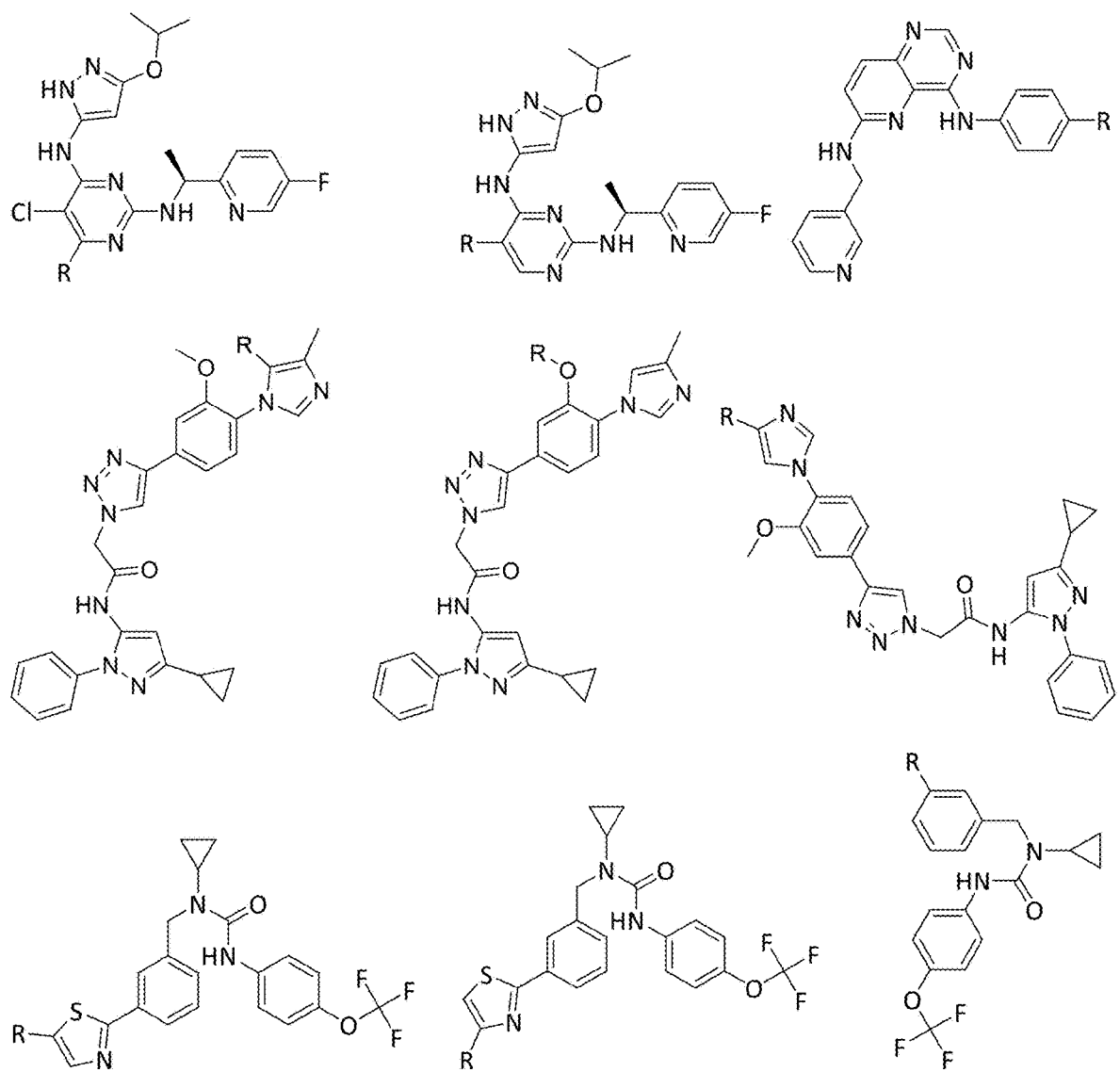
Figure 8C:
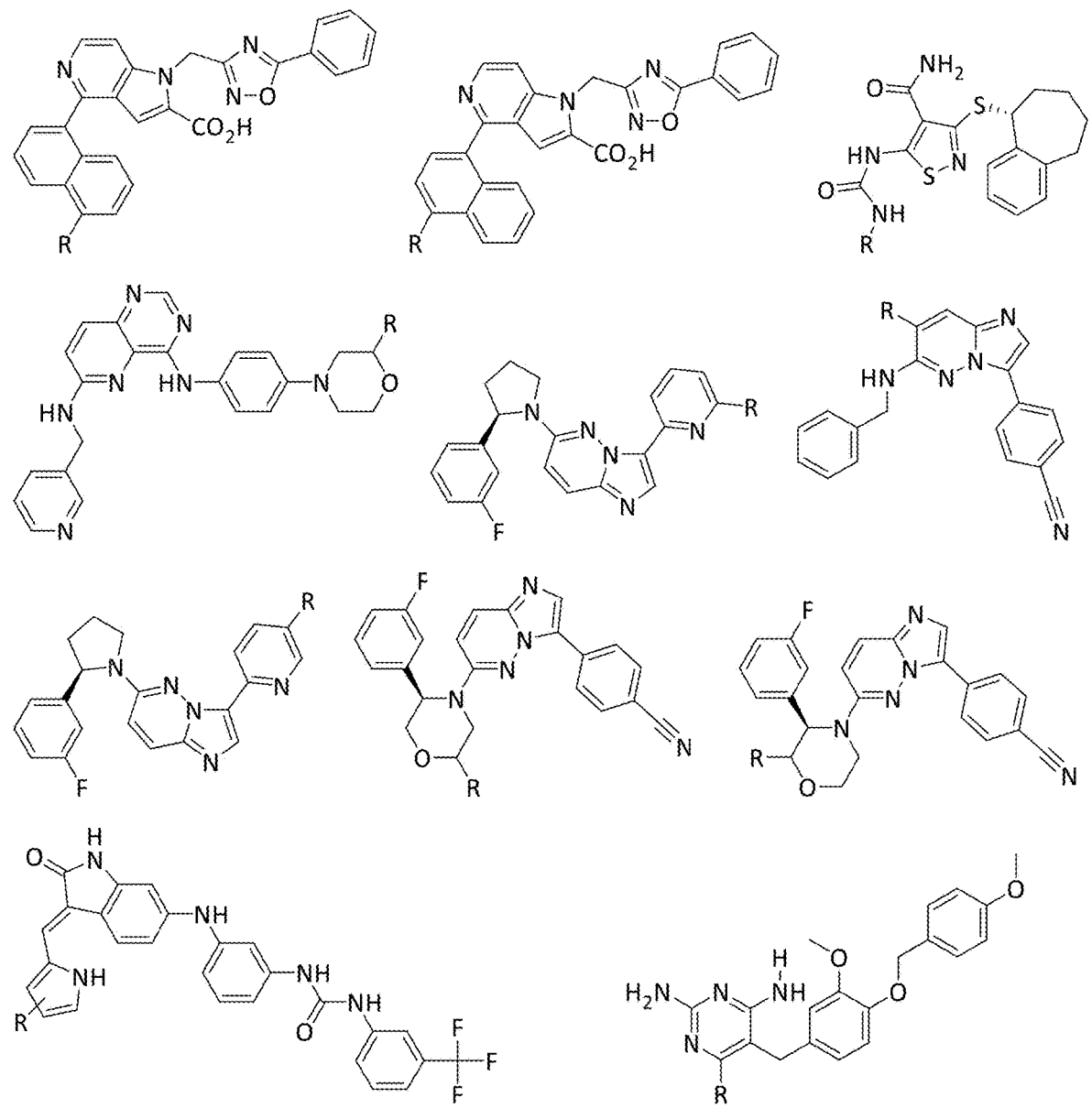
Figure 8D:
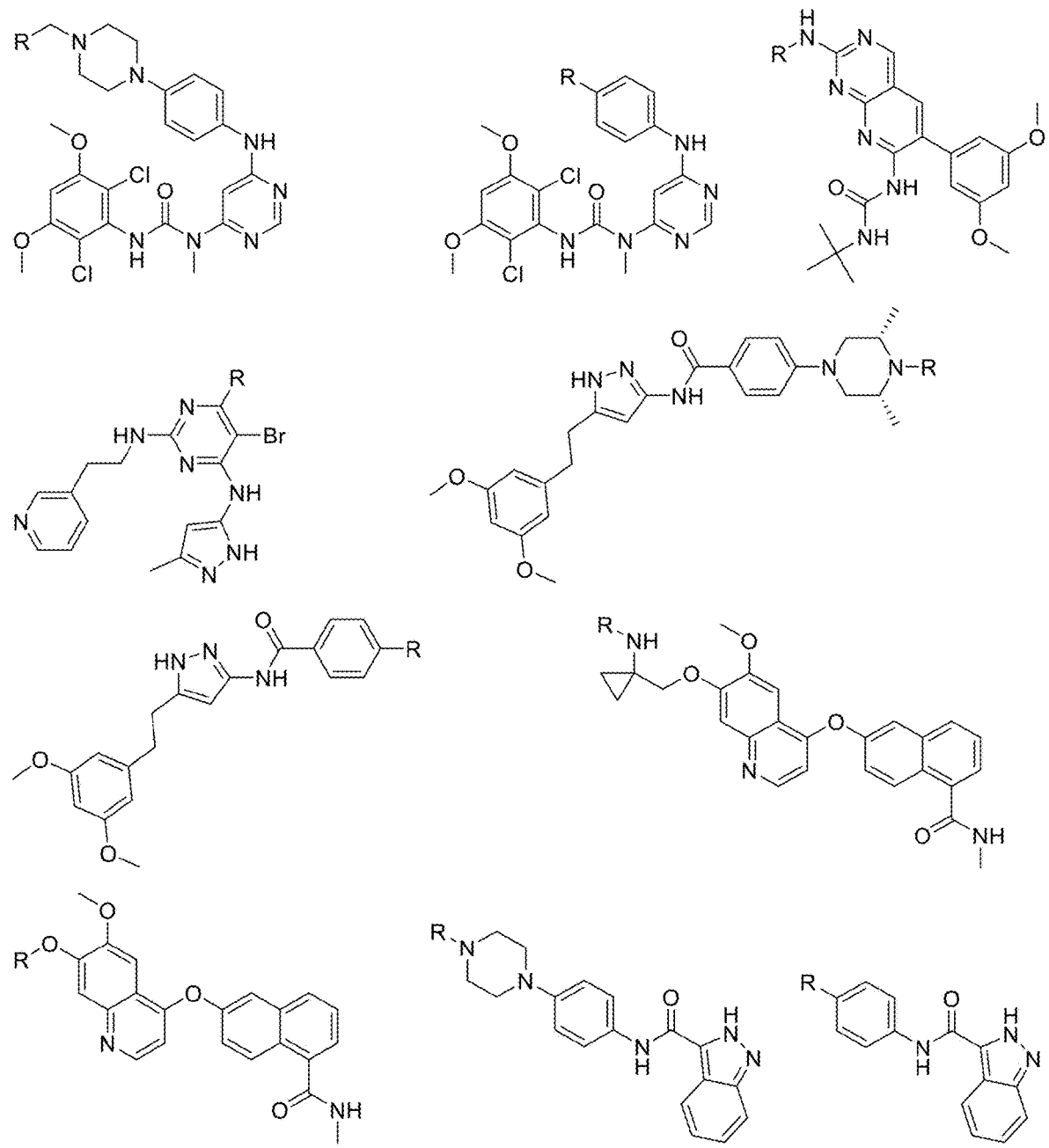
Figure 8E:
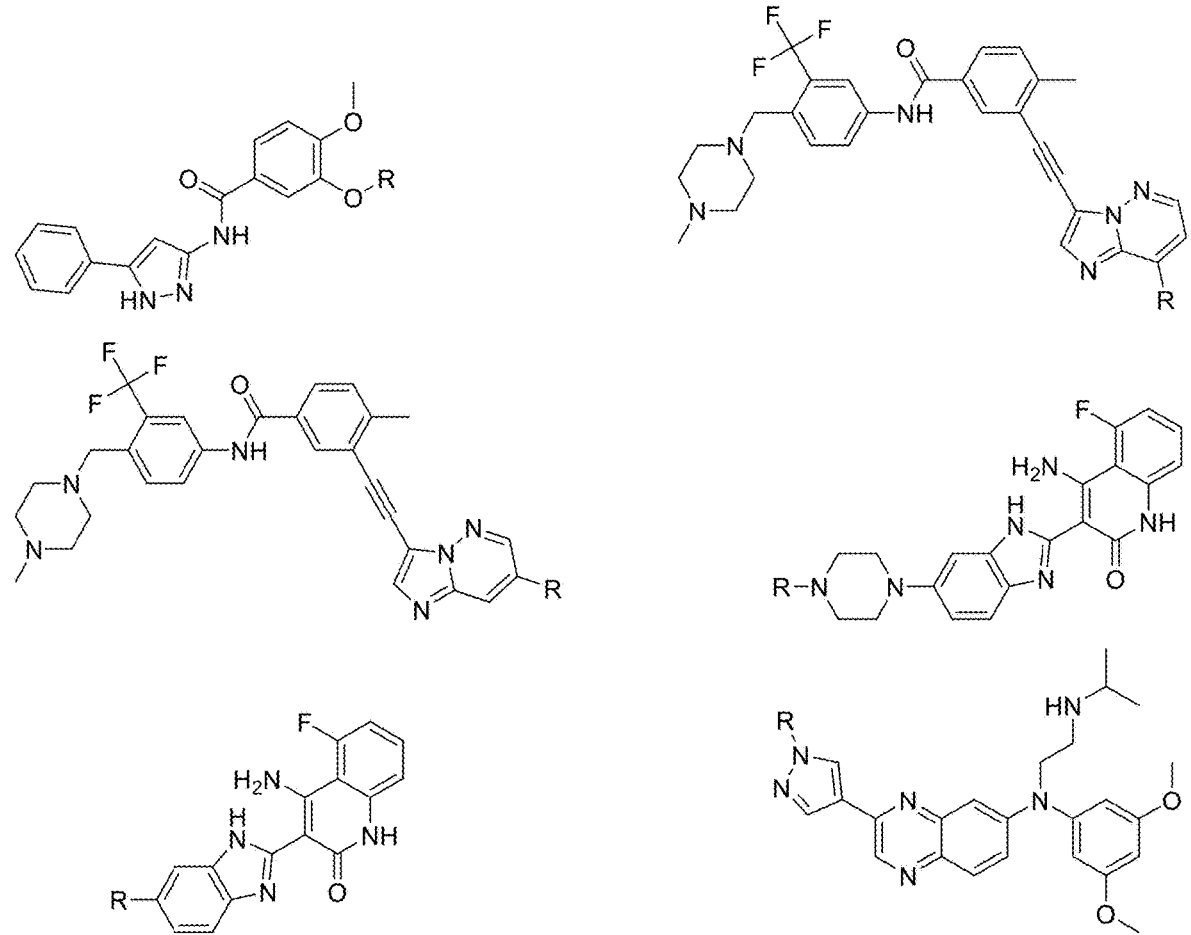
Figure 8F:
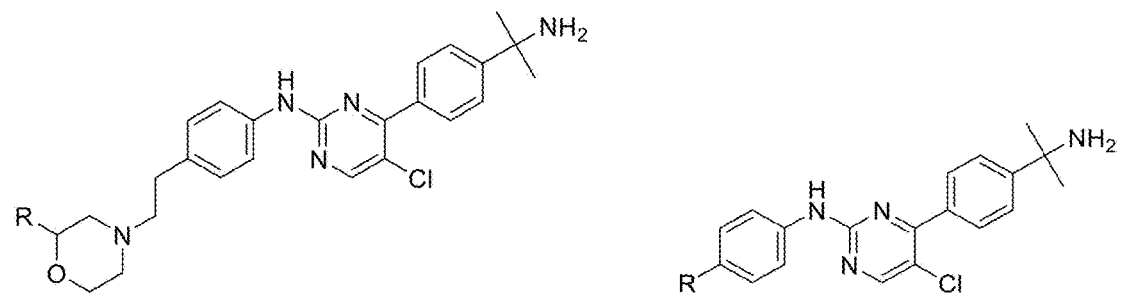
Figure 8G:
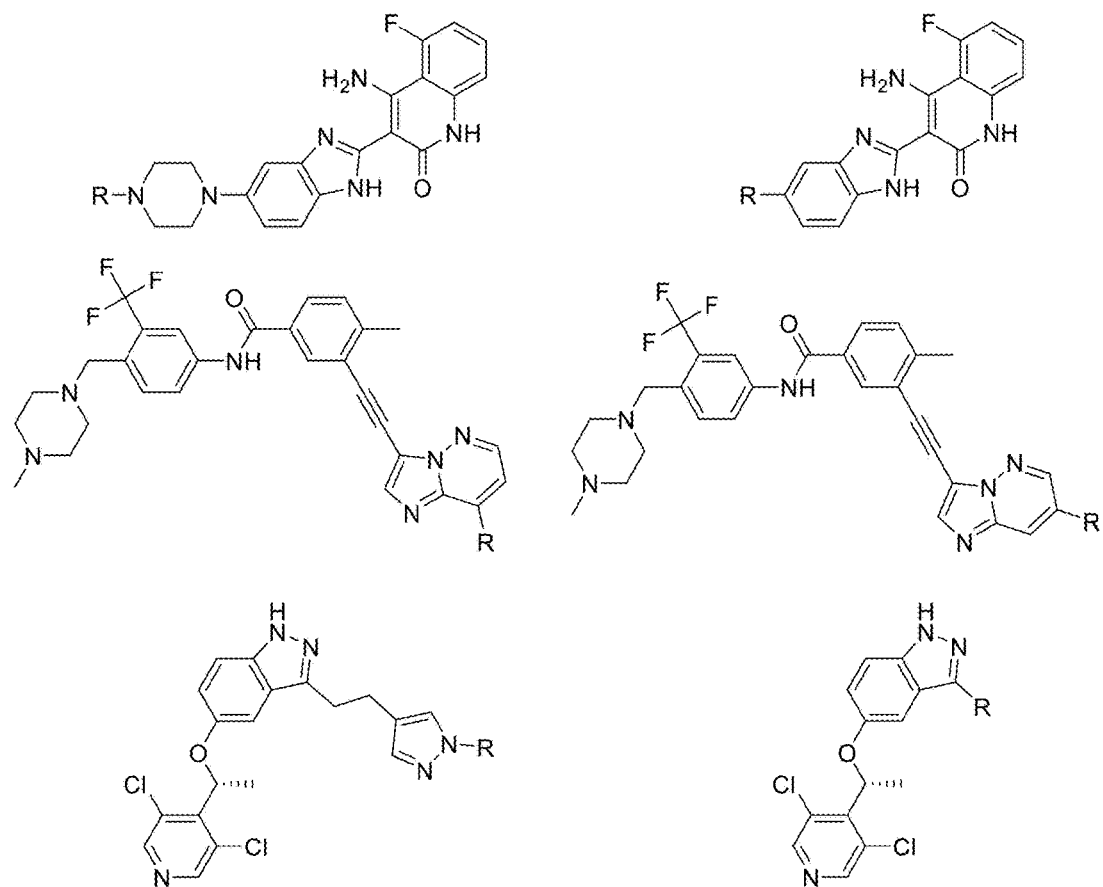
Figure 8H:
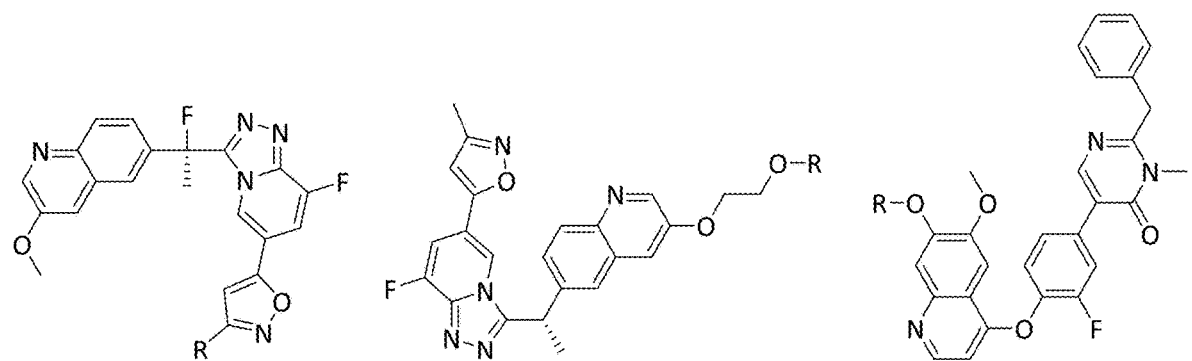
Figure 8I:
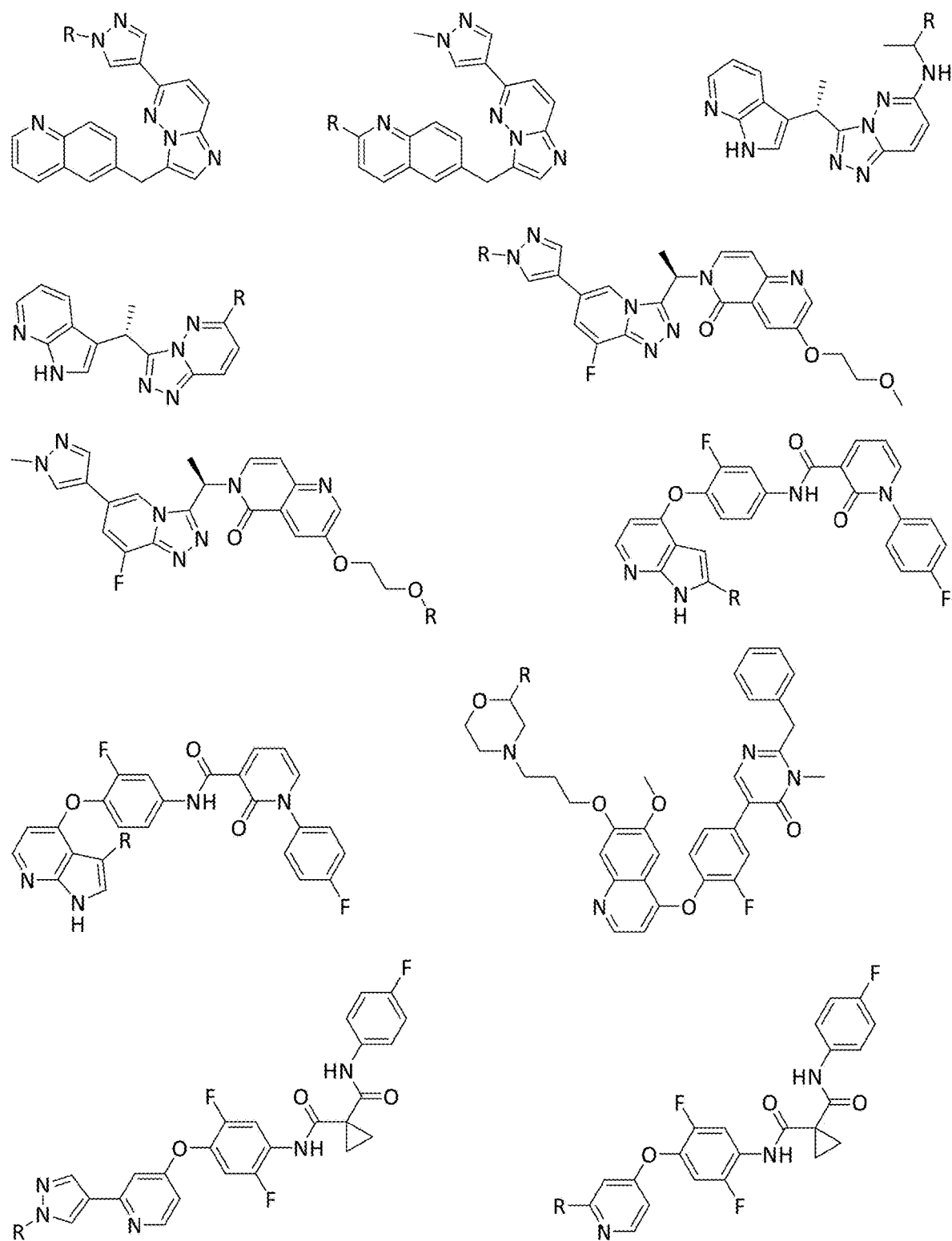
Figure 8J:
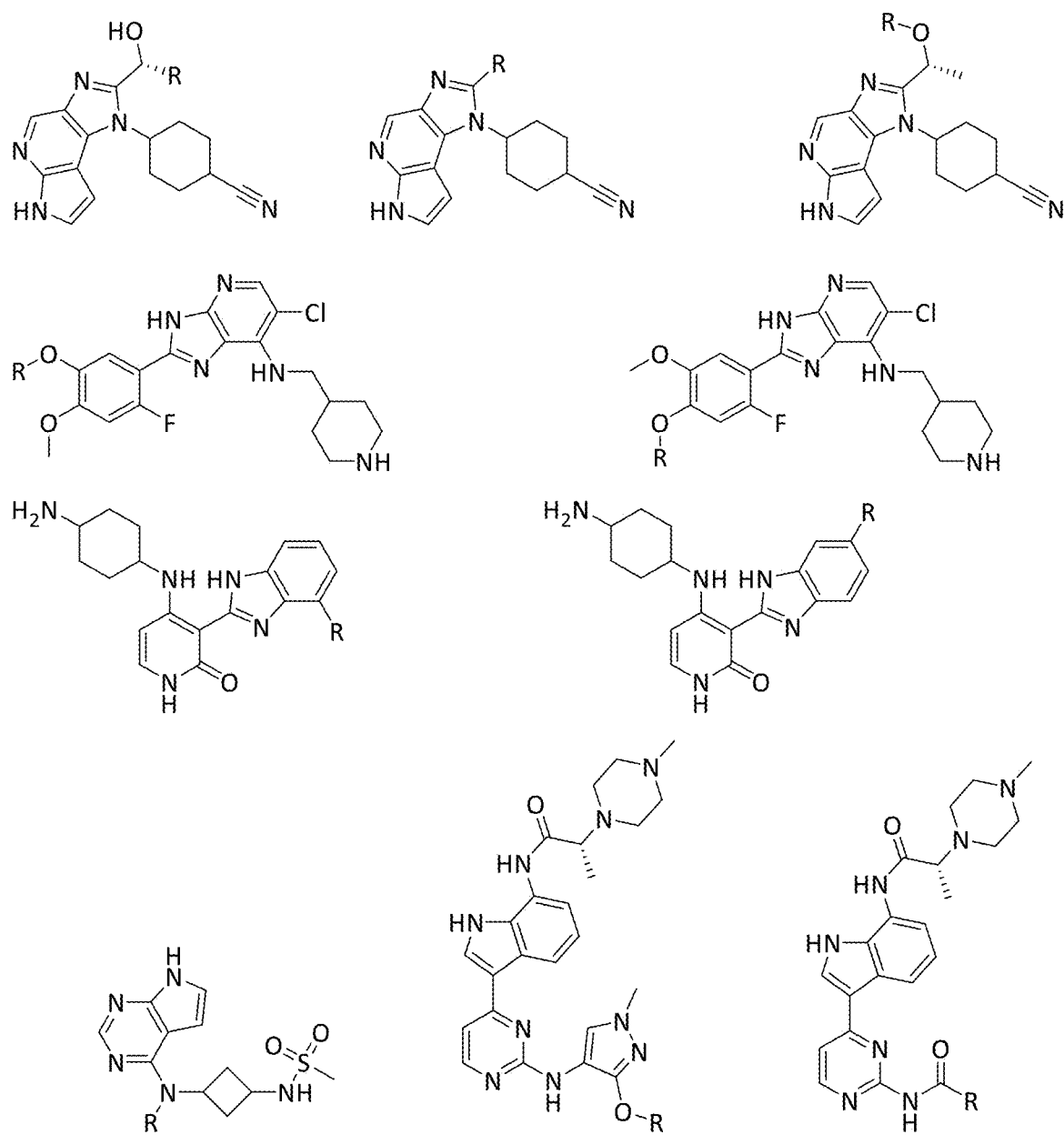
Figure 8K:
Figure 8L:
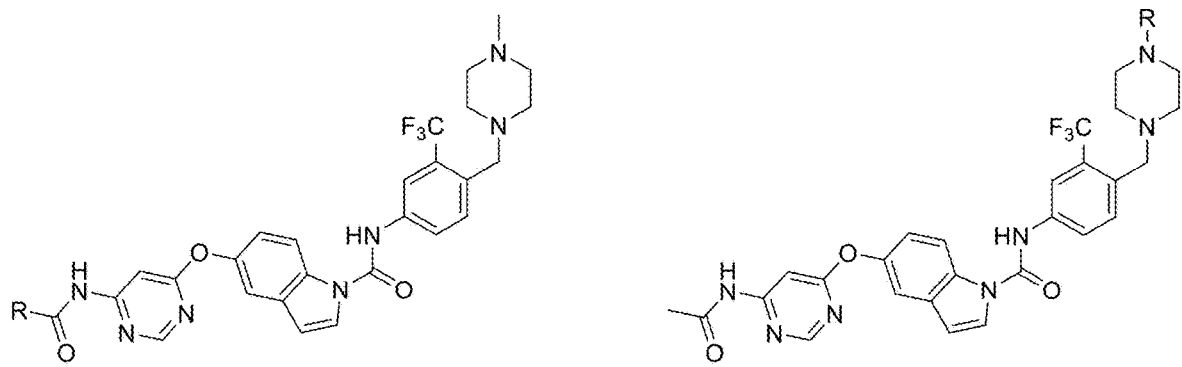
Figure 8M:
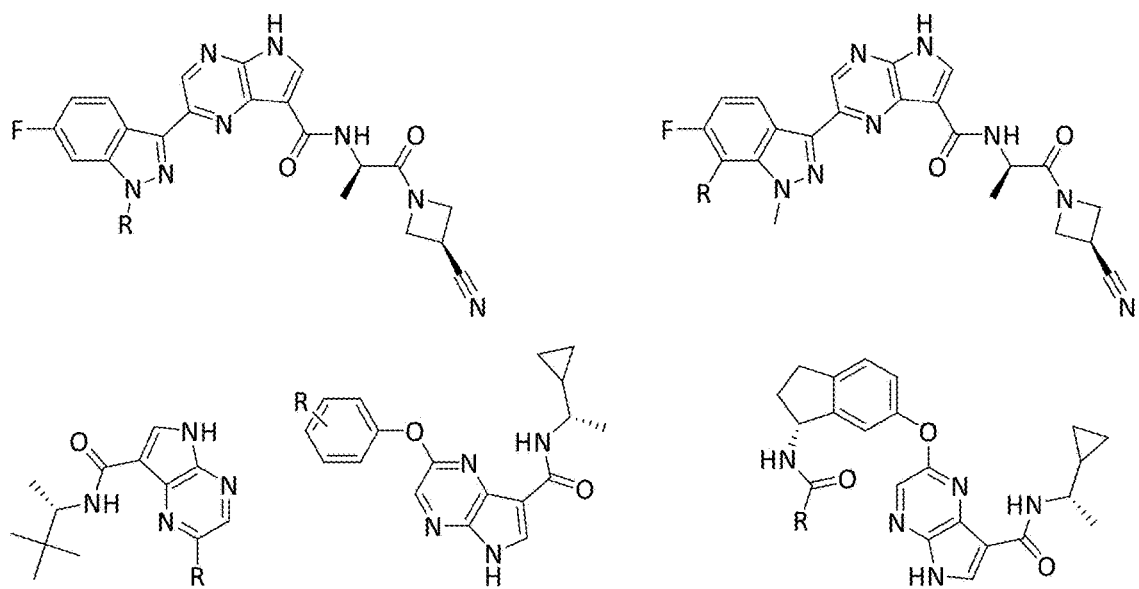
Figure 8N:
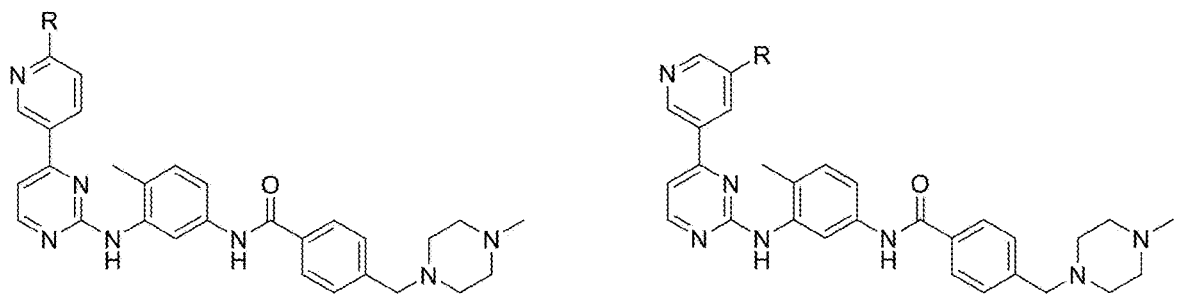
Figure 8O:
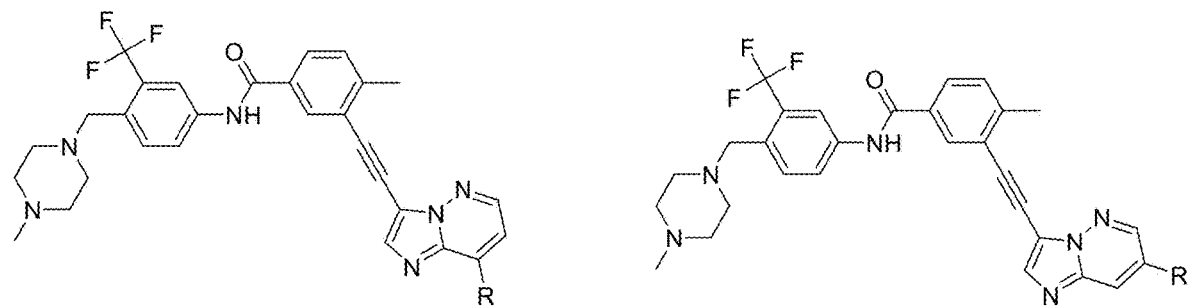
Figure 8P:
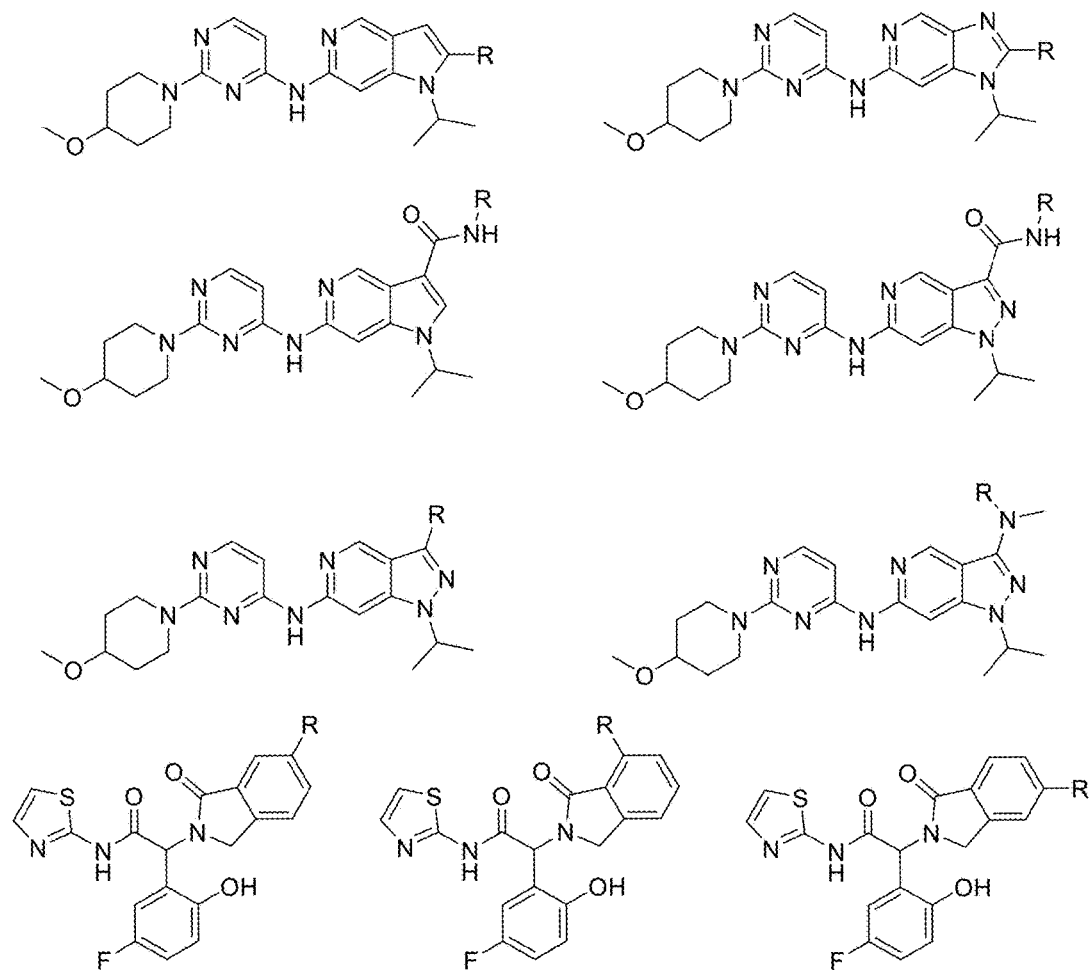
Figure 8Q:
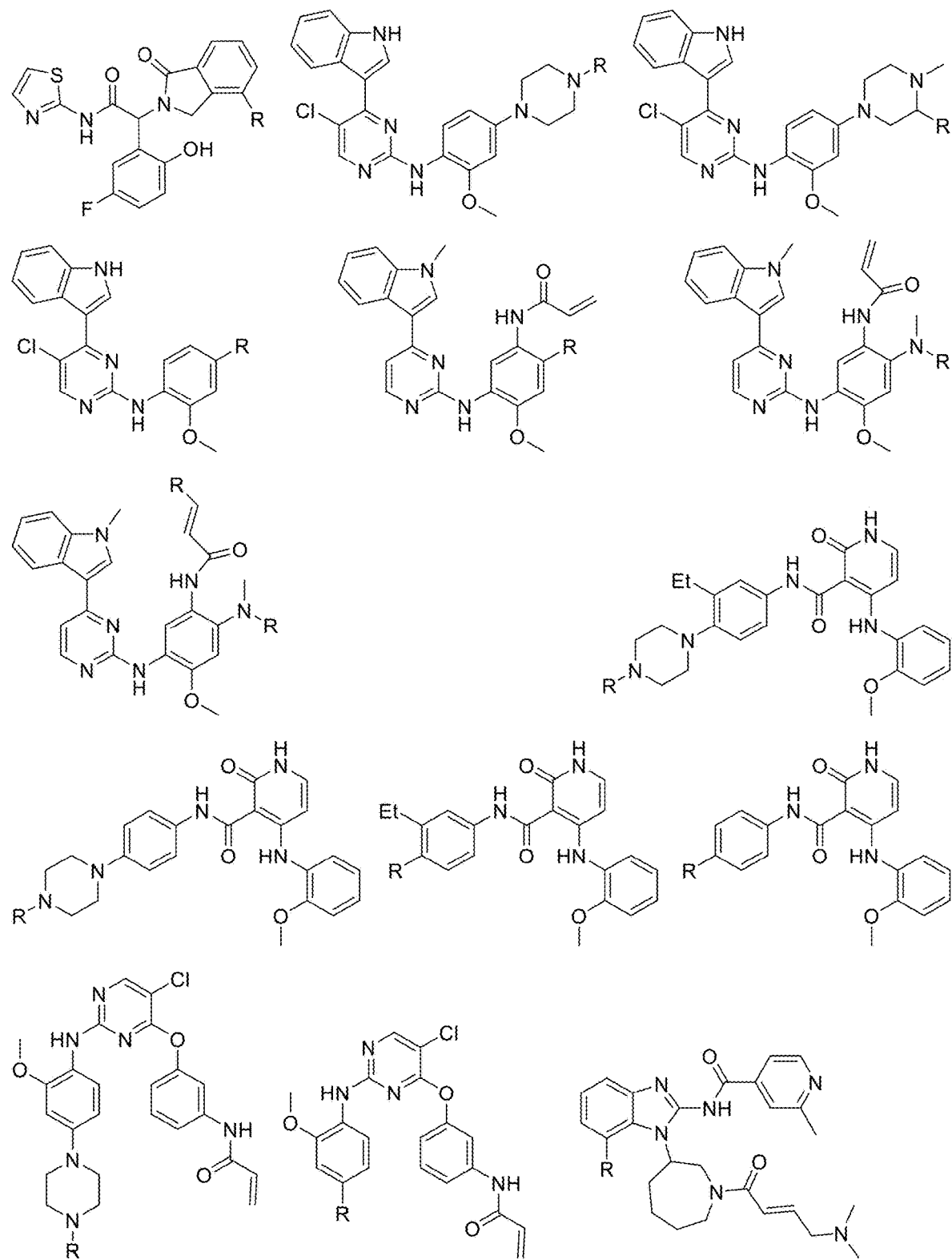
Figure 8R:
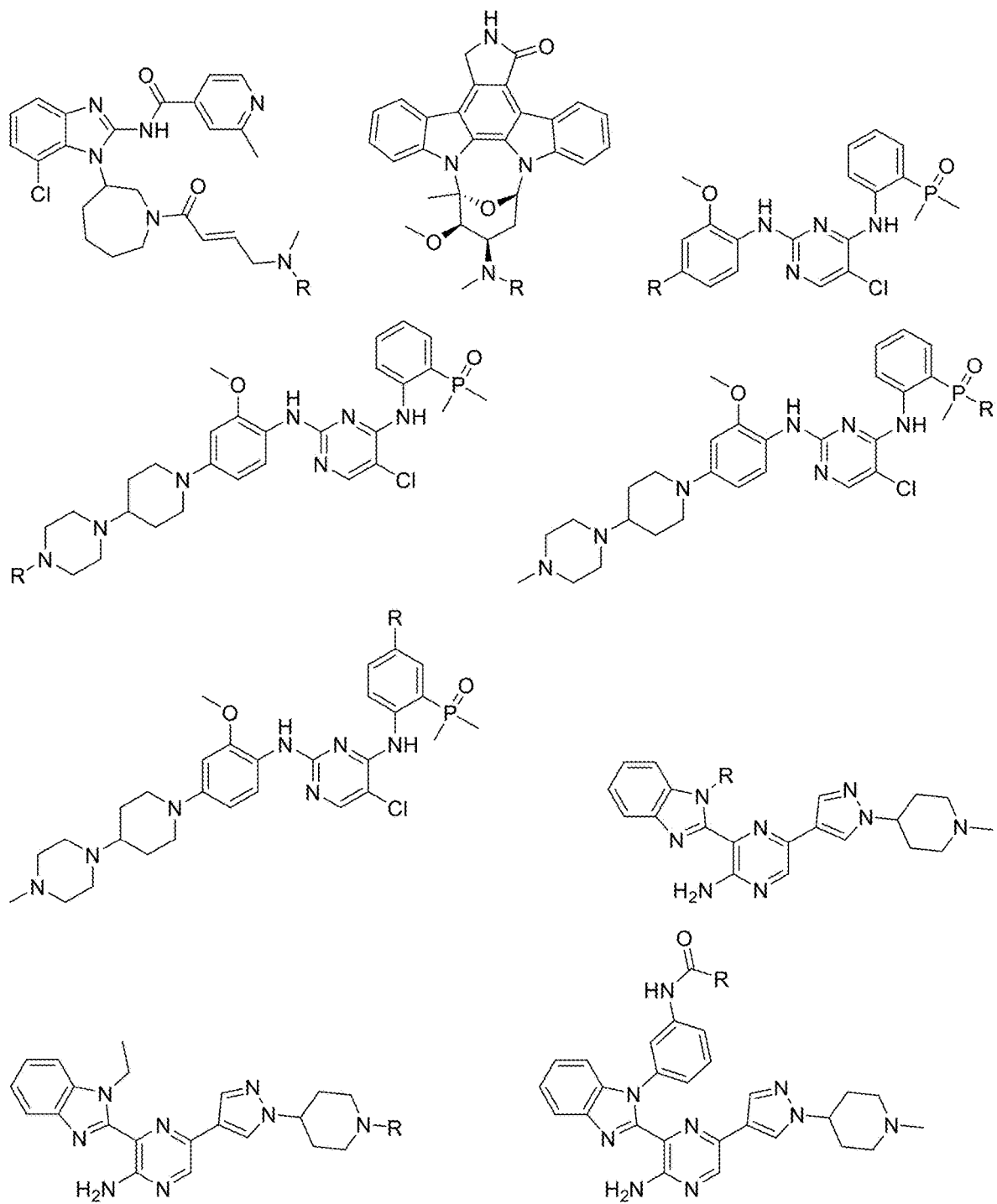
Figure 8S:
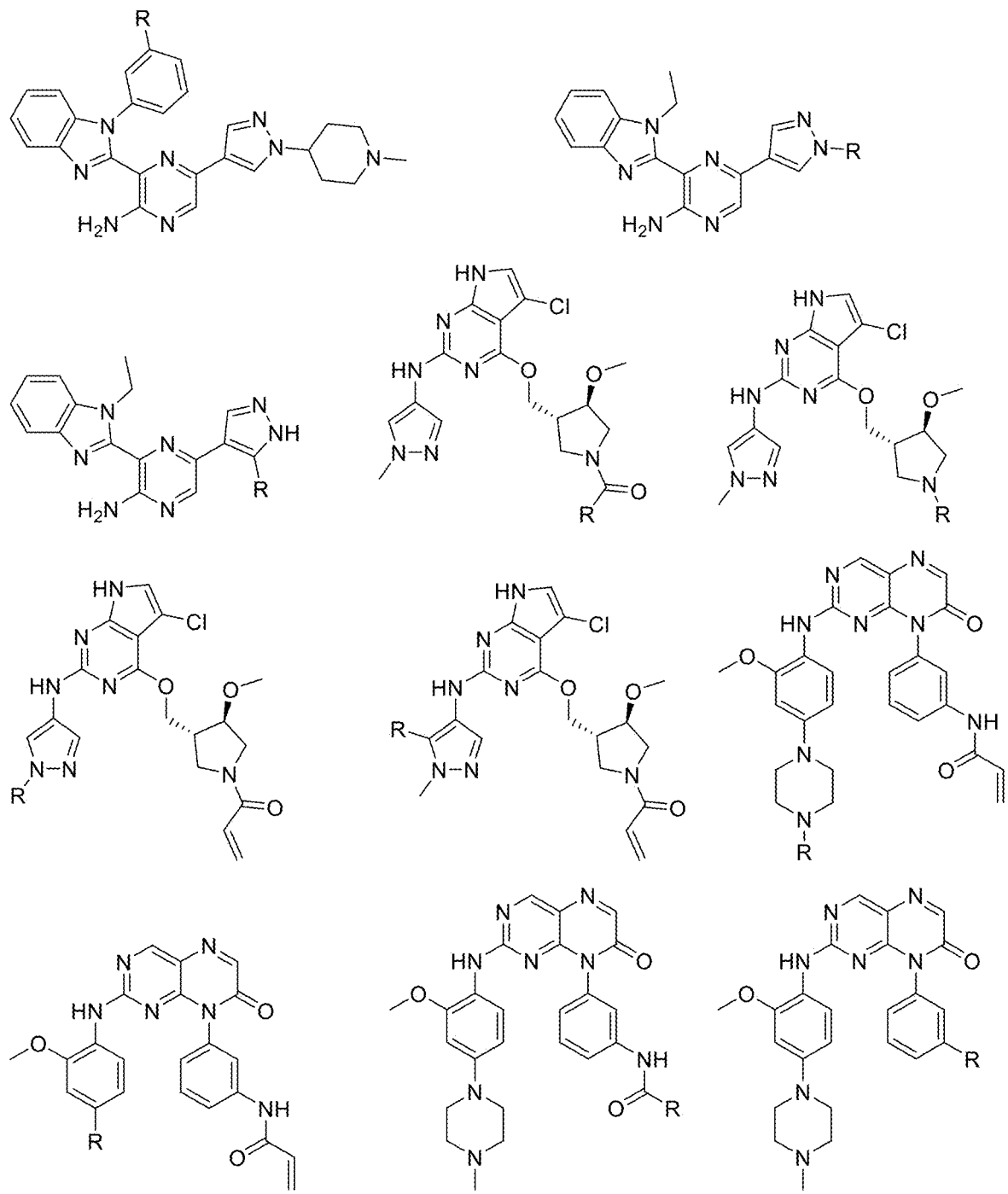

FIG. 8A-8S provide non-limiting examples of BRD4 Bromodomain 1 Targeting Ligands wherein R represents exemplary points at which the Linker can be attached. For additional examples and related ligands, see, the crystal structures PDB 3u5k and 3u5l and related ligands in Filippakopoulos, P. et al. "Benzodiazepines and benzotriazepines as protein interaction inhibitors targeting bromodomains of the BET family", Bioorg. Med. Chem. 20: 1878-1886 (2012); the crystal structure PDB 3u5l; the crystal structure PDB 3zyu and related ligands described in Dawson, M. A. et al. "Inhibition of Bet Recruitment to Chromatin as an Effective Treatment for Mll-Fusion Leukaemia." Nature 478: 529 (2011); the crystal structure PDB 4bwl and related ligands described in Mirguet, O. et al. "Naphthyridines as Novel Bet Family Bromodomain Inhibitors." Chemmedchem 9: 589 (2014); the crystal structure PDB 4cfl and related ligands described in Dittmann, A. et al. "The Commonly Used Pi3-Kinase Probe Ly294002 is an Inhibitor of Bet Bromodomains" ACS Chem. Biol. 9: 495 (2014); the crystal structure PDB 4e96 and related ligands described in Fish, P. V. et al. "Identification of a chemical probe for bromo and extra C-terminal bromodomain inhibition through optimization of a fragment-derived hit." J. Med. Chem. 55: 9831-9837 (2012); the crystal structure PDB 4clb and related ligands described in Atkinson, S. J. et al. "The Structure Based Design of Dual Hdac/Bet Inhibitors as Novel Epigenetic Probes." Medchemcomm 5: 342 (2014); the crystal structure PDB 4f3i and related ligands described in Zhang, G. et al. "Down-regulation of NF-{kappa}B Transcriptional Activity in HIV-associated Kidney Disease by BRD4 Inhibition." J. Biol. Chem. 287: 28840-28851 (2012); the crystal structure PDB 4hxl and related ligands described in Zhao, L. "Fragment-Based Drug Discovery of 2-Thiazolidinones as Inhibitors of the Histone Reader BRD4 Bromodomain." J. Med. Chem. 56: 3833-3851 (2013); the crystal structure PDB 4hxs and related ligands described in Zhao, L. et al. "Fragment-Based Drug Discovery of 2-Thiazolidinones as Inhibitors of the Histone Reader BRD4 Bromodomain." J. Med. Chem. 56: 3833-3851 (2013); the crystal structure PDB 4lrg and related ligands described in Gehling, V. S. et al. "Discovery, Design, and Optimization of Isoxazole Azepine BET Inhibitors." ACS Med Chem Lett 4: 835-840 (2013); the crystal structure PDB 4mep and related ligands described in Vidler, L. R. "Discovery of Novel Small-Molecule Inhibitors of BRD4 Using Structure-Based Virtual Screening." et al. J. Med. Chem. 56: 8073-8088 (2013); the crystal structures PDB 4nr8 and PDB 4c77 and related ligands described in Ember, S. W. et al. "Acetyllysine Binding Site of Bromodomain-Containing Protein 4 (BRD4) Interacts with Diverse Kinase Inhibitors". ACS Chem. Biol. 9: 1160-1171 (2014); the crystal structure PDB 4o7a and related ligands described in Ember, S. W. et al. "Acetyl-lysine Binding Site of Bromodomain-Containing Protein 4 (BRD4) Interacts with Diverse Kinase Inhibitors." ACS Chem. Biol. 9: 1160-1171 (2014); the crystal structure PDB 4o7b and related ligands described in "Acetyl-lysine Binding Site of Bromodomain-Containing Protein 4 (BRD4) Interacts with Diverse Kinase Inhibitors." Ember, S. W. et al. (2014) ACS Chem. Biol. 9: 1160-1171; the crystal structure PDB 4o7c and related ligands described in Ember, S. W. et al. "Acetyl-lysine Binding Site of Bromodomain-Containing Protein 4 (BRD4) Interacts with Diverse Kinase Inhibitors". ACS Chem. Biol. 9: 1160-1171 (2014); the crystal structure PDB 4gpj; and the crystal structure PDB 4uix and related ligands described in Theodoulou, N. H. et al. "The Discovery of I-Brd9, a Selective Cell Active Chemical Probe for Bromodomain Containing Protein 9 Inhibition". J. Med. Chem. 59: 1425 (2016); the crystal structure PDB 4uiz and related ligands described in Theodoulou, N. H., et al. "The Discovery of I-Brd9, a Selective Cell Active Chemical Probe for Bromodomain Containing Protein 9 Inhibition". J. Med Chem. 59: 1425 (2016); the crystal structure PDB 4wiv and related ligands described in McKeown, M R. et al. "Biased multicomponent reactions to develop novel bromodomain inhibitors." J. Med Chem. 57: 9019-9027 (2014); the crystal structure PDB 4×2i and related ligands described in Taylor, A. M. et al. "Discovery of Benzotriazolo[4,3-d][1,4]diazepines as Orally Active Inhibitors of BET Bromodomains." ACS Med Chem. Lett. 7: 145-150 (2016); the crystal structure PDB 4yh3; And related ligands described in Duffy, B. C. "Discovery of a new chemical series of BRD4(1) inhibitors using protein-ligand docking and structure-guided design." Bioorg. Med Chem. Lett. 25: 2818-2823 (2015); the crystal structure PDB 4yh4 and related ligands described in Duffy, B. C. "Discovery of a new chemical series of BRD4 (1) inhibitors using protein-ligand docking and structure-guided design." Bioorg. Med Chem. Lett. 25: 2818-2823 (2015); the crystal structure PDB 4zlq and related ligands described in Taylor, A. M. "Discovery of Benzotriazolo[4, 3-d][1,4]diazepines as Orally Active Inhibitors of BET Bromodomains." ACS Med Chem. Lett. 7: 145-150 (2016); the crystal structure PDB 4zwl; the crystal structure PDB 5a5s and related ligands described in Demont, E. H. "Fragment-Based Discovery of Low-Micromolar Atad2 Bromodomain Inhibitors. J. Med Chem. 58: 5649 (2015); the crystal structure PDB 5a85 and related ligands described in Bamborough, P. "Structure-Based Optimization of Naphthyridones Into Potent Atad2 Bromodomain Inhibitors" J. Med Chem. 58: 6151 (2015); the crystal structure PDB 5acy and related ligands described in Sullivan, J. M. "Autism-Like Syndrome is Induced by Pharmacological Suppression of Bet Proteins in Young Mice." J. Exp. Med 212: 1771 (2015); the crystal structure PDB 5ad2 and related ligands described in Waring, M. J. et al. "Potent and Selective Bivalent Inhibitors of Bet Bromodomains". Nat. Chem. Biol. 12: 1097 (2016); the crystal structure PDB 5cfw and related ligands described in Chekler, E. L. et al. "Transcriptional Profiling of a Selective CREB Binding Protein Bromodomain Inhibitor Highlights Therapeutic Opportunities." Chem. Biol. 22: 1588-1596 (2015); the crystal structure PDB 5cqt and related ligands described in Xue, X. et al. "Discovery of Benzo[cd]indol-2(1H)-ones as Potent and Specific BET Bromodomain Inhibitors: Structure-Based Virtual Screening, Optimization, and Biological Evaluation". J. Med Chem. 59: 1565-1579 (2016); the crystal structure PDB 5d3r and related ligands described in Hugle, M. et al. "4-Acyl Pyrrole Derivatives Yield Novel Vectors for Designing Inhibitors of the Acetyl-Lysine Recognition Site of BRD4(1)". J. Med Chem. 59: 1518-1530 (2016); the crystal structure PDB 5dlx and related ligands described in Milhas, S. et al. "*Protein-Protein Interaction Inhibition (2P21)-Oriented Chemical Library Accelerates Hit Discovery*." (2016) ACS Chem. Biol. 11: 2140-2148; the crystal structure PDB 5dlz and related ligands described in Milhas, S. et al. "Protein-Protein Interaction Inhibition (2P21)-Oriented Chemical Library Accelerates Hit Discovery." ACS Chem. Biol. 11: 2140-2148 (2016); the crystal structure PDB 5dw2 and related ligands described in Kharenko, O. A. et al. "RVX-297—a novel BD2 selective inhibitor of BET bromodomains." Biochem. Biophys. Res. Commun. 477: 62-67 (2016); the crystal structure PDB 5dlx; the crystal structure PDB 5his and related ligands described in Albrecht, B. K. et al. "Identification of a Benzoisoxazoloazepine Inhibitor (CPI-0610) of the Bromodomain and Extra-Terminal (BET)

Family as a Candidate for Human Clinical Trials." *J. Med Chem.* 59: 1330-1339 (2016); the crystal structure PDB 5ku3 and related ligands described in Crawford, T. D. et al. "Discovery of a Potent and Selective in Vivo Probe (GNE-272) for the Bromodomains of CBP/EP300 ". *J. Med Chem.* 59: 10549-10563 (2016); the crystal structure PDB 51j2 and related ligands described in Bamborough, P. et al. "A Chemical Probe for the ATAD2 Bromodomain." *Angew. Chem. Int. Ed Engl.* 55: 11382-11386 (2016); the crystal structure PDB 5dlx and related ligands described in Wang, L. "Fragment-based, structure-enabled discovery of novel pyridones and pyridone macrocycles as potent bromodomain and extra-terminal domain (BET) family bromodomain inhibitors". *J. Med Chem.* 10.1021/acs.jmedchem.7b00017 (2017); WO 2015169962 A1 titled "Benzimidazole derivatives as BRD4 inhibitors and their preparation and use for the treatment of cancer" assigned to Boehringer Ingelheim International GmbH, Germany; and, WO 2011143669 A2 titled "*Azolodiazepine derivatives and their preparation, compositions and methods for treating neoplasia, inflammatory disease and other disorders*" assigned to Dana-Farber Cancer Institute, Inc, USA.

Figure 8T:
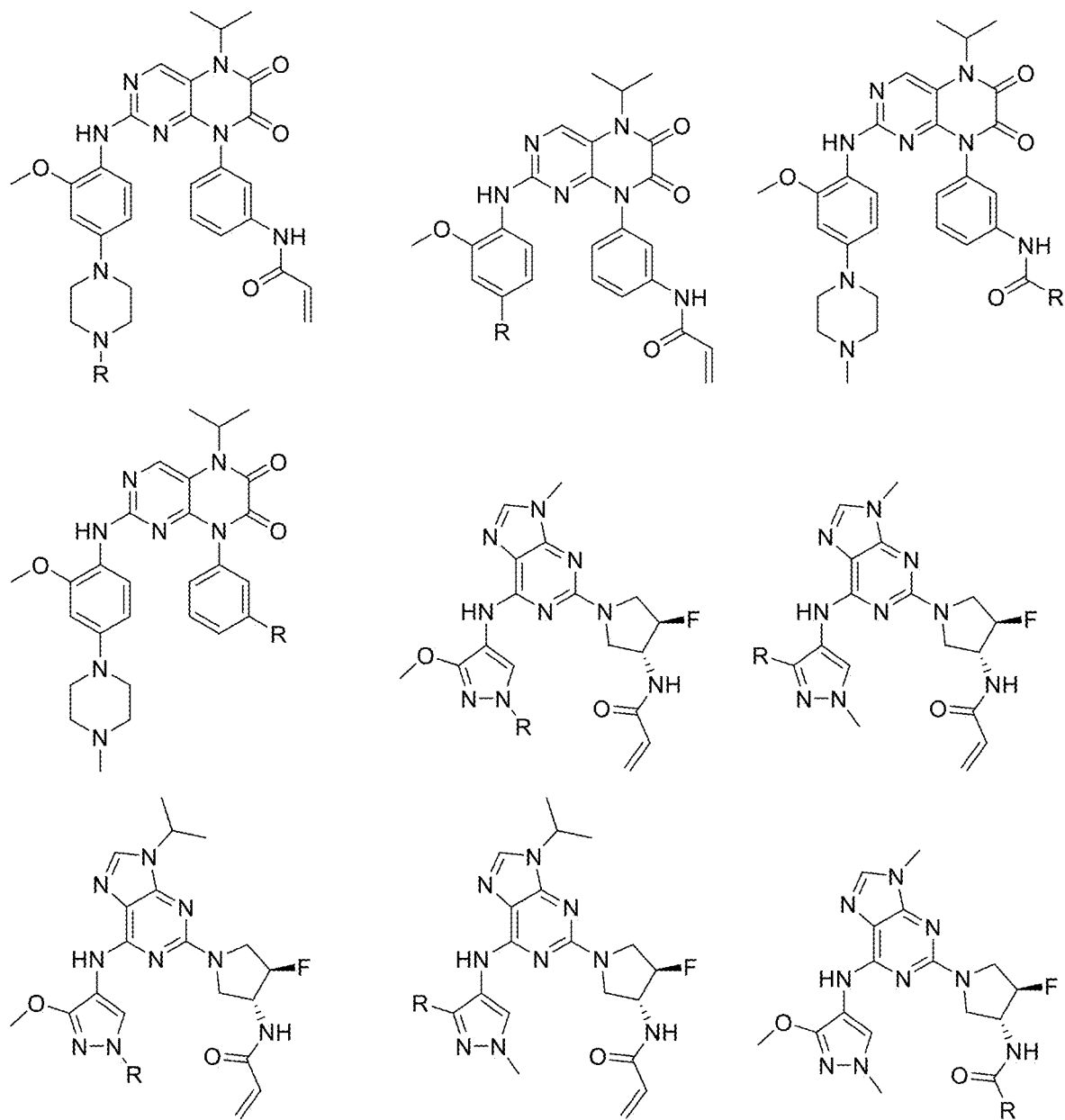
Figure 8U:
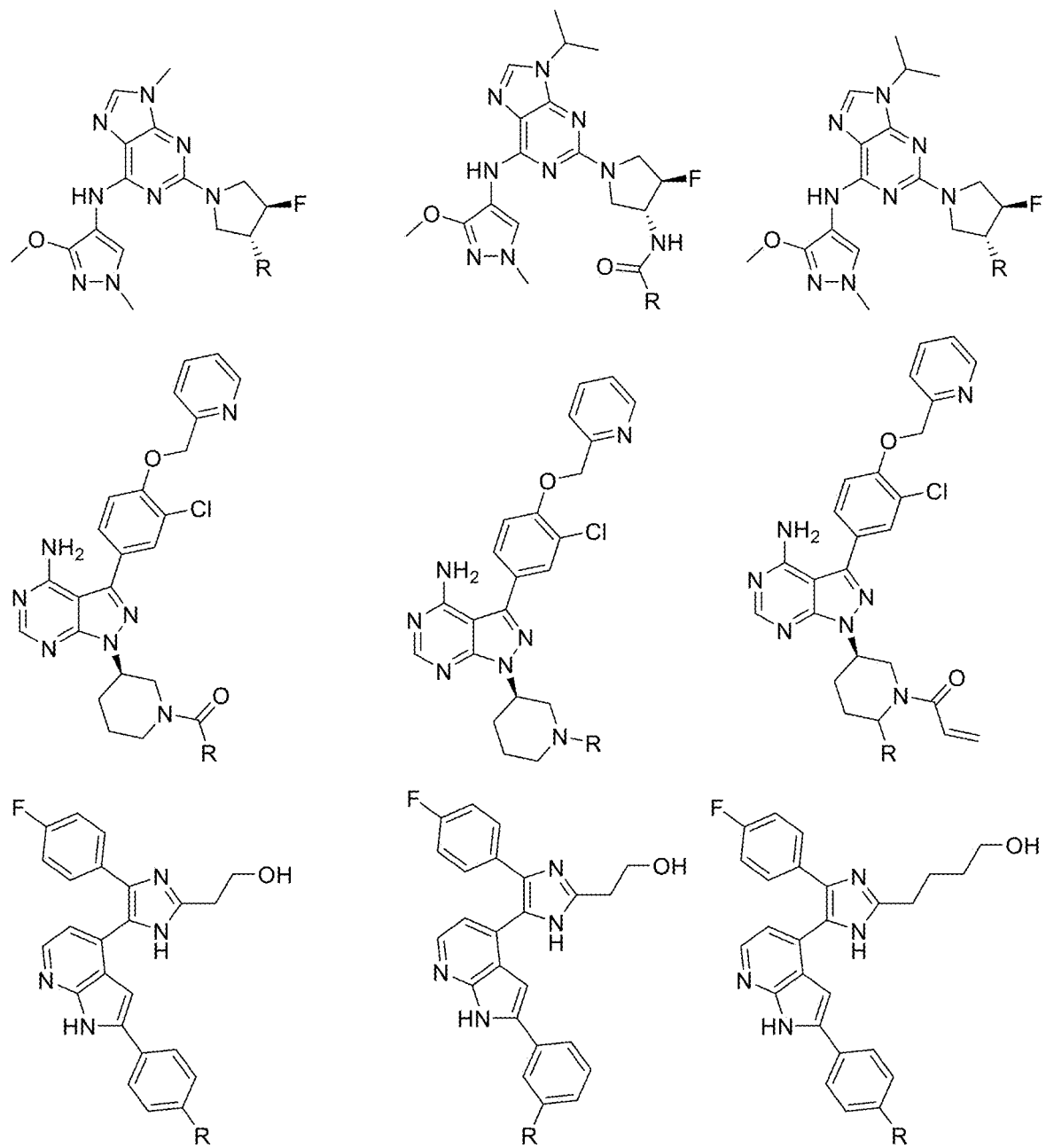
Figure 8V:
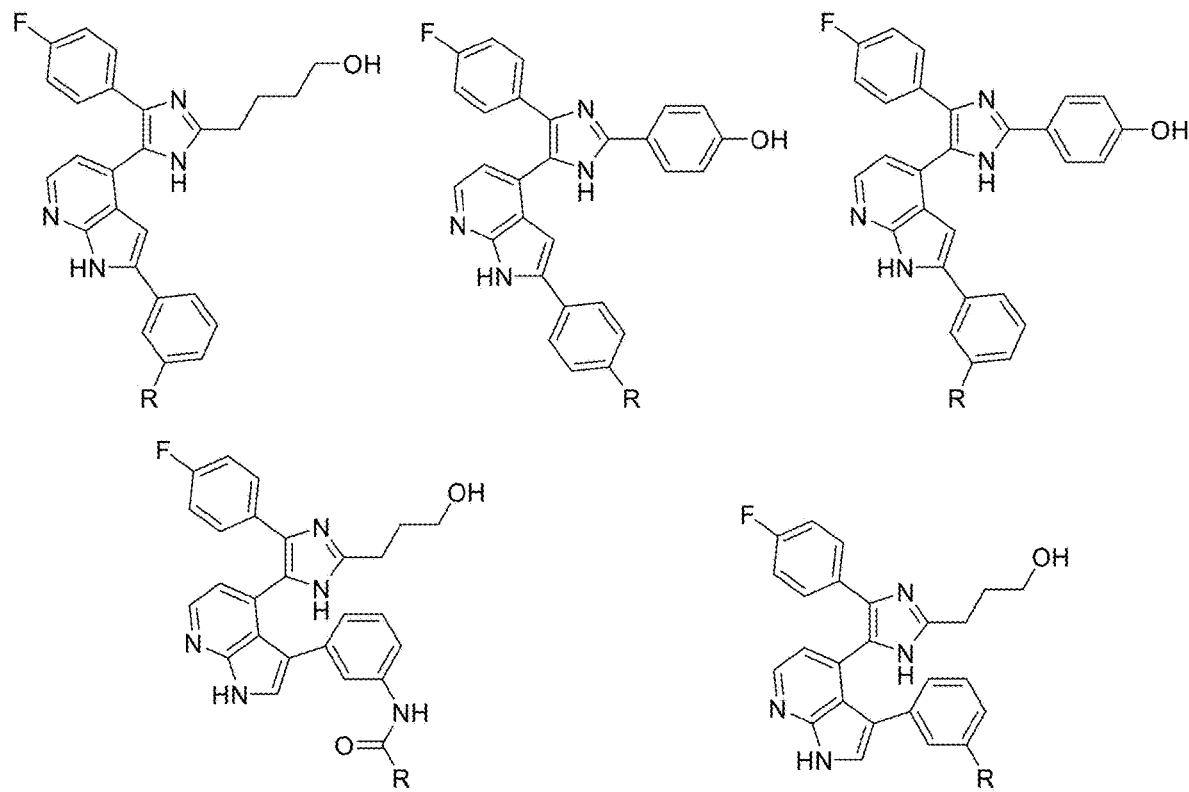
Figure 8W:
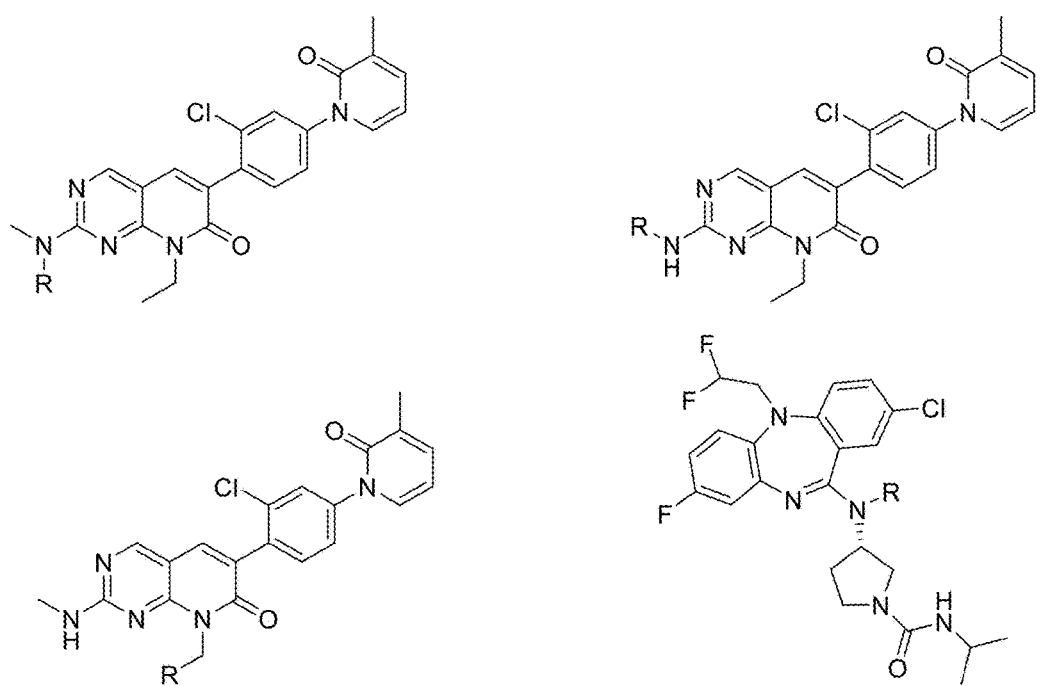
Figure 8X:
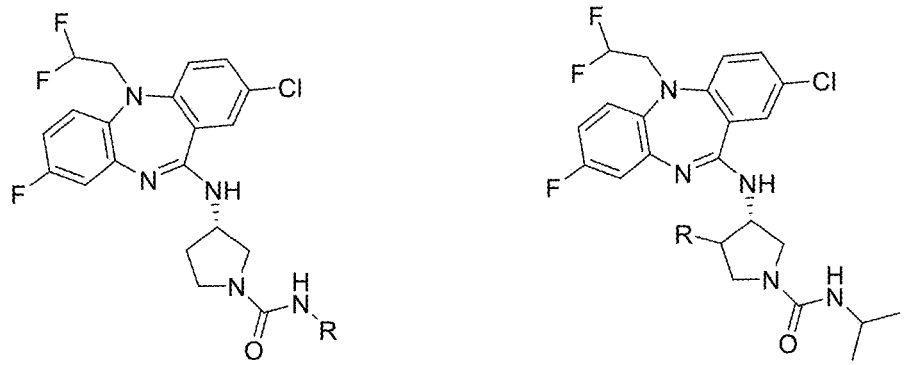
Figure 8Y:
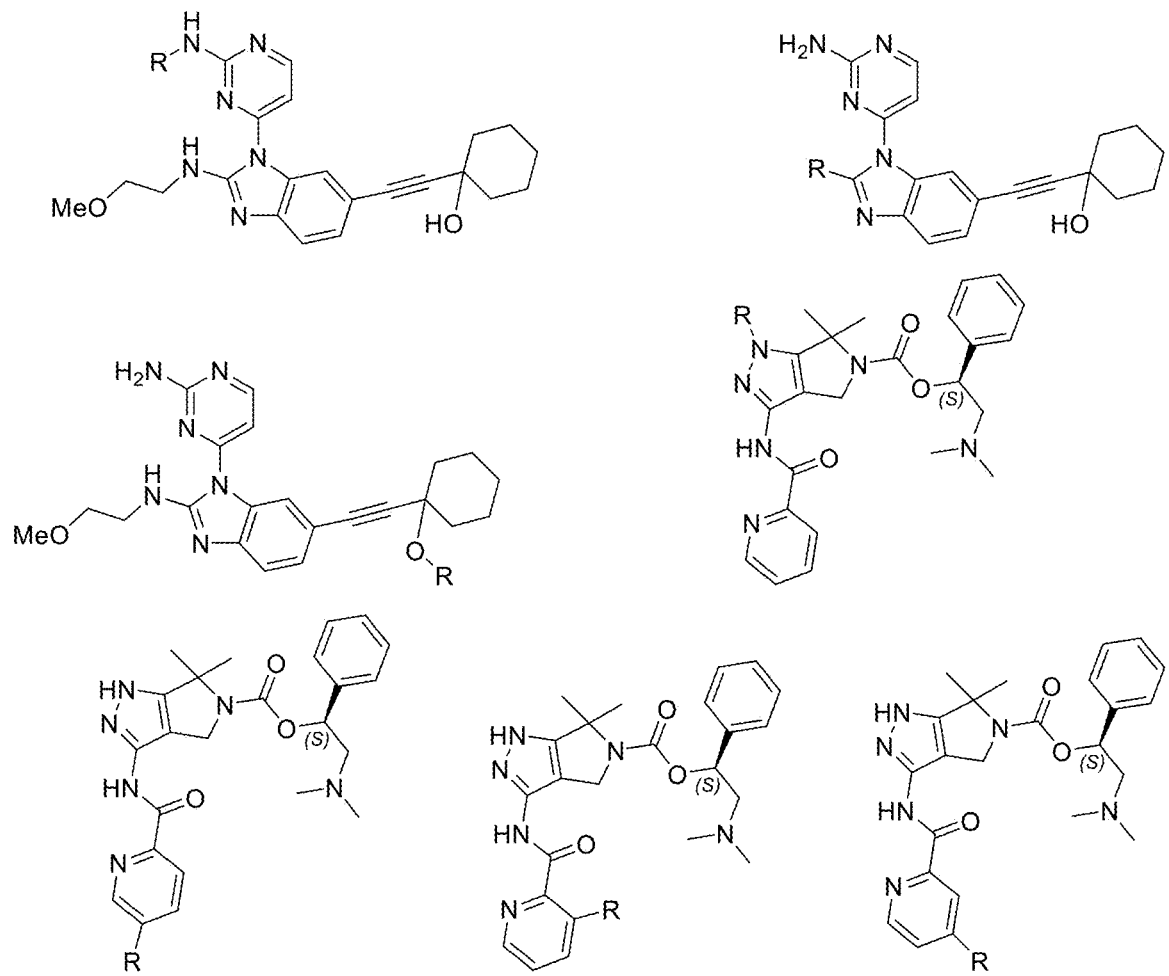
Figure 8Z:
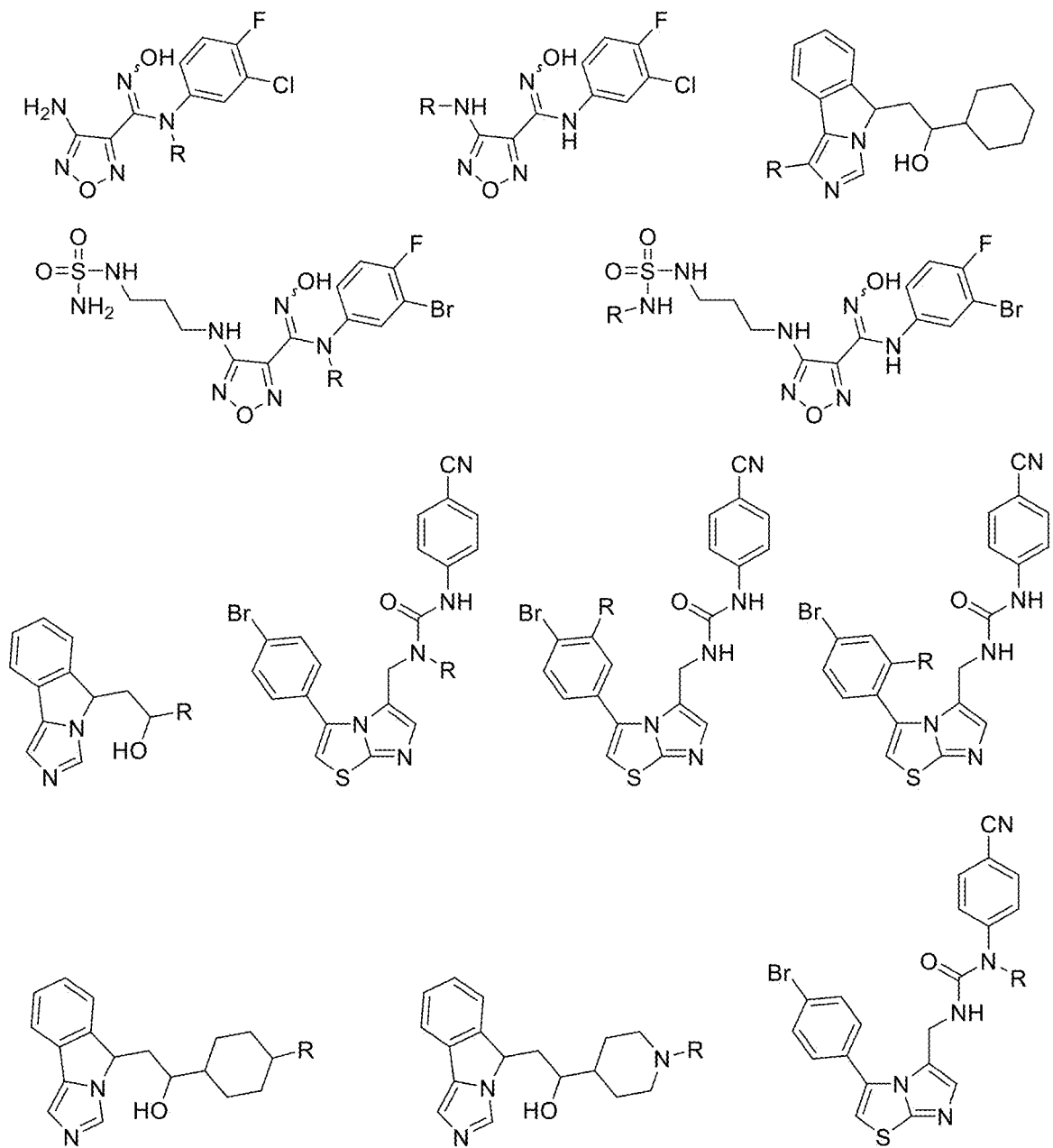

FIG. 8T-8V provide non-limiting examples of ALK Targeting Ligands wherein R represents exemplary points at which the Linker can be attached. For additional examples and related ligands, see, the crystal structures PDB 2xb7 and 2xba and related ligands described in Bossi, R. T. et al. "Crystal Structures of Anaplastic Lymphoma Kinase in Complex with ATP Competitive Inhibitors" *Biochemistry* 49: 6813-6825 (2010); the crystal structures PDB 2yfx, 4ccb, 4ccu, and 4cd0 and related ligands described in Huang, Q. et al. "Design of Potent and Selective Inhibitors to Overcome Clinical Anaplastic Lymphoma Kinase Mutations Resistant to Crizotinib." *J. Med Chem.* 57: 1170 (2014); the crystal structures PDB, 4cli, 4cmo, and 4cnh and related ligands described in Johnson, T. W. et al. "Discovery of (10R)-7-Amino-12-Fluoro-2,10,16-Trimethyl-15-Oxo-10,15,16,17-Tetrahydro-2H-8,4-(Metheno)Pyrazolo[4,3-H][2,5,11]Benzoxadiazacyclotetradecine-3-Carbonitrile (Pf-06463922), a Macrocyclic Inhibitor of Alk/Rosl with Pre-Clinical Brain Exposure and Broad Spectrum Potency Against Alk-Resistant Mutations." *J. Med Chem.* 57: 4720 (2014); the crystal structure PDB 4fny and related ligands described in Epstein, L. F. et al. "The R1275Q Neuroblastoma Mutant and Certain ATP-competitive Inhibitors Stabilize Alternative Activation Loop Conformations of Anaplastic Lymphoma Kinase." *J. Biol. Chem.* 287: 37447-37457 (2012). the crystal structure PDB 4dce and related ligands described in Bryan, M. C. et al "Rapid development of piperidine carboxamides as potent and selective anaplastic lymphoma kinase inhibitors. "*J. Med Chem.* 55: 1698-1705 (2012); the crystal structure PDB 4joa and related ligands described in Gummadi, V. R. et al. "Discovery of 7-azaindole based anaplastic lymphoma kinase (ALK) inhibitors: wild type and mutant (L1196M) active compounds with unique binding mode." (2013) *Bioorg. Med Chem. Lett.* 23: 4911-4918; and, the crystal structure PDB 5iui and related ligands described in Tu, C. H. et al. "Pyrazolylamine Derivatives Reveal the Conformational Switching between Type I and Type II Binding Modes of Anaplastic Lymphoma Kinase (ALK)." *J. Med Chem.* 59: 3906-3919 (2016).

FIG. 8W-8X provide non-limiting examples of BTK Targeting Ligands wherein R represents exemplary points at which the Linker can be attached. For additional examples and related ligands, see, the crystal structure PDB 3gen, 3piz and related ligands described in Marcotte, D. J. et al. "Structures of human Bruton's tyrosine kinase in active and inactive conformations suggest a mechanism of activation for TEC family kinases." *Protein Sci.* 19: 429-439 (2010) and Kuglstatter, A. et al. "Insights into the conformational flexibility of Bruton's tyrosine kinase from multiple ligand complex structures" *Protein Sci.* 20: 428-436" (2011); the crystal structure PDB 3ocs, 4ot6 and related ligands described in Lou, Y. et al. "Structure-Based Drug Design of RN486, a Potent and Selective Bruton's Tyrosine Kinase (BTK) Inhibitor, for the Treatment of Rheumatoid Arthritis" *J. Med Chem.* 58: 512-516 (2015); the crystal structures PDB 5fbn and 5fbo and related ligands described in Liu, J. et al. "Discovery of 8-Amino-imidazo[1,5-a]pyrazines as Reversible BTK Inhibitors for the Treatment of Rheumatoid Arthritis." *ACS Med Chem. Lett.* 7: 198-203 (2016); the crystal structure PDB 3pix and related ligands described in Kuglstatter, A. et al. "Insights into the conformational flexibility of Bruton's tyrosine kinase from multiple ligand complex structures." *Protein Sci.* 20: 428-436 (2011); and, the crystal structure PDB 3pij and related ligands described in Bujacz, A. et al. "Crystal structures of the apo form of beta-fructofuranosidase from *Bifidobacterium longum* and its complex with fructose. "*Febs J.* 278: 1728-1744 (2011).

FIG. 8Y provides non-limiting examples of FLT3 Targeting Ligands wherein R represents exemplary points at which the Linker can be attached. For additional examples and related ligands, see, the crystal structures PDB 4xuf and 4rt7 and related ligands described in Zorn, J. A. et al. "Crystal Structure of the FLT3 Kinase Domain Bound to the Inhibitor Quizartinib (AC220)". *Plos One* 10: e0121177-e0121177 (2015).

FIG. 8Z-8AA provide non-limiting examples of TNIK Targeting Ligands wherein R represents exemplary points at which the Linker can be attached. For additional examples and related ligands, see, the crystal structure PDB 2x7f; the crystal structures PDB 5ax9 and 5d7a; and, related ligands described in Masuda, M. et al. "TNIK inhibition abrogates colorectal cancer stemness." *Nat Commun* 7: 12586-12586 (2016).

FIG. 8BB-8CC provide non-limiting examples of NTRK1, NTRK2, and NTRK3 Targeting Ligands wherein R represents exemplary points at which the Linker can be attached. For additional examples and related ligands, see, the crystal structure PDB 4aoj and related ligands described in Wang, T. et al. "Discovery of Disubstituted Imidazo[4,5-B]Pyridines and Purines as Potent Trka Inhibitors." *ACS Med. Chem. Lett.* 3: 705 (2012); the crystal structures PDB 4pmm, 4pmp, 4pms and 4pmt and related ligands described in Stachel, S. J. et al. "Maximizing diversity from a kinase screen: identification of novel and selective pan-Trk inhibitors for chronic pain." *J. Med. Chem.* 57: 5800-5816 (2014); the crystal structures PDB 4yps and 4yne and related ligands described in Choi, H. S. et al. "(R)-2-Phenylpyrrolidine Substituted Imidazopyridazines: A New Class of Potent and Selective Pan-TRK Inhibitors." ACS Med. *Chem. Lett.* 6: 562-567 (2015); the crystal structures PDB 4at5 and 4at3 and related ligands described in Bertrand, T. et al. "The Crystal Structures of Trka and Trkb Suggest Key Regions for Achieving Selective Inhibition." J. *Mol. Biol.* 423: 439 (2012); and, the crystal structures PDB 3v5q and 4ymj and related ligands described in Albaugh, P. et al. "Discovery of GNF-5837, a selective TRK Inhibitor with efficacy in rodent cancer tumor models." ACS Med. *Chem. Lett.* 3: 140-145 (2012) and Choi, H. S. et al. "(R)-2-Phenylpyrrolidine Substitute Imidazopyridazines: a New Class of Potent and Selective Pan-TRK Inhibitors." ACS Med *Chem Lett* 6: 562-567 (2015).

FIG. 8DD-8EE provide non-limiting examples of FGFR1 Targeting Ligands wherein R represents exemplary points at which the Linker can be attached. For additional examples and related ligands, see, the crystal structures PDB 3tto and 2fgi and related ligands described in Brison, Y. et al. "Functional and structural characterization of alpha-(1-2) branching sucrase derived from DSR-E glucansucrase." *J. Biol. Chem.* 287: 7915-7924 (2012) and Mohammadi, M. et al. "Crystal structure of an angiogenesis inhibitor bound to the FGF receptor tyrosine kinase domain." *EMBO J.* 17: 5896-5904 (1998); the crystal structure PDB 4fb3; the crystal structure PDB 4rwk and related ligands described in Harrison, C. et al. "Polyomavirus large T antigen binds symmetrical repeats at the viral origin in an asymmetrical manner." *J. Virol.* 87: 13751-13759 (2013); the crystal structure PDB 4rwl and related ligands described in Sohl, C. D. et al. "Illuminating the Molecular Mechanisms of Tyrosine Kinase Inhibitor Resistance for the FGFR1 Gatekeeper Mutation: The Achilles' Heel of Targeted Therapy." *ACS Chem. Biol.* 10: 1319-1329 (2015); the crystal structure PDB 4uwc; the crystal structure PDB 4v01 and related ligands described in Tucker, J. A. et al. "Structural Insights Into Fgfr Kinase Isoform Selectivity: Diverse Binding Modes of Azd4547 and Ponatinib in Complex with Fgfrl and Fgfr4." *Structure* 22: 1764 (2014); the crystal structure PDB 5a46 and related ligands described in Klein, T. et al. "Structural and Dynamic Insights Into the Energetics of Activation Loop Rearrangement in Fgfrl Kinase." *Nat. Commun.* 6: 7877 (2015); and, the crystal structure PDB 5ew8 and related ligands described in Patani, H. et al. "Landscape of activating cancer mutations in FGFR kinases and their differential responses to inhibitors in clinical use." *Oncotarget* 7: 24252-24268 (2016).

FIG. 8FF provides non-limiting examples of FGFR2 and FGFR3 Targeting Ligands wherein R represents exemplary points at which the Linker can be attached. For additional examples and related ligands, see, the crystal structure PDB 2pvf and related ligands described in Chen, H. et al. "A molecular brake in the kinase hinge region regulates the activity of receptor tyrosine kinases." *Mol. Cell* 27: 717-730 (2007); and "Structure-based drug design of 1,3,5-triazine and pyrimidine derivatives as novel FGFR3 inhibitors with high selectivity over VEGFR2" *Bioorg Med Chem* 2020, 28, 115453.

FIG. 8GG provides non-limiting examples of FGFR4 Targeting Ligands wherein R represents exemplary points at which the Linker can be attached. For additional examples and related ligands, see, the crystal structure PDB 4tyi and related ligands described in Lesca, E. et al. "Structural analysis of the human fibroblast growth factor receptor 4 kinase." *J. Mol. Biol.* 426: 3744-3756 (2014).

FIG. 8HH-8II provide non-limiting examples of MET Targeting Ligands wherein R represents exemplary points at which the Linker can be attached. For additional examples and related ligands, see, the crystal structures PDB 3qti and 3zcl; the crystal structures PDB 4xmo, 4xyf, and 3zcl and related ligands described in Peterson, E. A. et al. "Discovery of Potent and Selective 8-Fluorotriazolopyridine c-Met Inhibitors." *J. Med Chem.* 58: 2417-2430 (2015) and Cui, J. J. et al. "Lessons from (S)-6-(1-(6-(1-Methyl-1H-Pyrazol-4-Yl)-[1,2, 4]Triazolo[4,3-B]Pyridazin-3-Yl)Ethyl)Quinoline (Pf-04254644), an Inhibitor of Receptor Tyrosine Kinase C-met with High Protein Kinase Selectivity But Broad Phosphodiesterase Family Inhibition Leading to Myocardial Degeneration in Rats." *J. Med Chem.* 56: 6651 (2013); the crystal structure PDB 5eyd and related ligands described in Boezio, A. A. et al. "Discovery of (R)-6-(1-(8-Fluoro-6-(1-methyl-1H-pyrazol-4-yl)-[1,2,4]triazolo[4,3-a]pyridin-3-yl)ethyl)-3-(2-methoxyethoxy)-1,6-naphthyridin-5(6H)-one (AMG 337), a Potent and Selective Inhibitor of MET with High Unbound Target Coverage and Robust In Vivo Antitumor Activity." *J. Med Chem.* 59: 2328-2342 (2016); the crystal structure PDB 3ce3 and related ligands described in Kim, K. S. et al. "Discovery of pyrrolopyridine-pyridone based inhibitors of Met kinase: synthesis, X-ray crystallographic analysis, and biological activities." *J. Med Chem.* 51: 5330-5341 (2008); the crystal structure PDB 2rfn and related ligands described in Bellon, S. F. et al. "c-Met inhibitors with novel binding mode show activity against several hereditary papillary renal cell carcinoma-related mutations." *J. Biol. Chem.* 283: 2675-2683 (2008); and, the crystal structure PDB 5dg5 and related ligands described in Smith, B. D. et al "Altiratinib Inhibits Tumor Growth, Invasion, Angiogenesis, and Microenvironment-Mediated Drug Resistance via Balanced Inhibition of MET, TIE2, and VEGFR2.". *Mol. Cancer Ther.* 14: 2023-2034 (2015).

FIG. 8JJ provides non-limiting examples of JAK1 Targeting Ligands wherein R represents exemplary points at which the Linker can be attached. For additional examples and related ligands, see, the crystal structure PDB 4ivd and related ligands described in Zak, M. et al. "Identification of C-2 Hydroxyethyl Imidazopyrrolopyridines as Potent JAK1 Inhibitors with Favorable Physicochemical Properties and High Selectivity over JAK2." *J. Med Chem.* 56: 4764-4785 (2013); the crystal structure PDB 5ele and related ligands described in Vasbinder, M. M. et al. "Identification of azabenzimidazoles as potent JAK1 selective inhibitors." *Bioorg. Med Chem. Lett.* 26: 60-67 (2016); the crystal structure PDB 5hx8 and related ligands described in Simov, V., et al. "Structure-based design and development of (benz)imidazole pyridones as JAK1-selective kinase inhibitors." *Bioorg. Med Chem. Lett.* 26: 1803-1808 (2016); the crystal structure PDB 5hx8 and related ligands described in Caspers, N. L. et al. "Development of a high-throughput crystal structure-determination platform for JAK1 using a novel metal-chelator soaking system". *Acta Crystallogr. Sect. F* 72: 840-845 (2016); and, Kettle, J. G. "Discovery of the JAK1 selective kinase inhibitor AZD4205", AACR National Meeting, April 2017.

FIG. 8KK-8LL provide non-limiting examples of JAK2 Targeting Ligands wherein R represents exemplary points at which the Linker can be attached. For additional examples and related ligands, see, the crystal structure PDB 3ugc and related ligands described in Andraos, R. et al. "Modulation of activation-loop phosphorylation by JAK inhibitors is binding mode dependent." *Cancer Discov* 2: 512-523 (2012); the crystal structures PDB 5cf4, 5cf5, 5cf6 and 5cf8 and related ligands described in Hart, A. C. et al. "Structure-Based Design of Selective Janus Kinase 2 Imidazo[4,5-d]pyrrolo[2,3-b]pyridine Inhibitors." *ACS Med Chem. Lett.* 6: 845-849 (2015); the crystal structure PDB 5aep and related ligands described in Brasca, M. G. et al "Novel Pyrrole Carboxamide Inhibitors of Jak2 as Potential Treatment of Myeloproliferative Disorders" *Bioorg. Med Chem.* 23: 2387 (2015); the crystal structures PDB 4ytf, 4yth and 4yti and related ligands described in Farmer, L. J. et al. "Discovery of VX-509 (Decernotinib): A Potent and Selective Janus Kinase 3 Inhibitor for the Treatment of Autoimmune Diseases." *J. Med Chem.* 58: 7195-7216 (2015); the crystal structure PDB 4ytf, 4yth, 4yti and related ligands described in Menet, C. J. et al. "Triazolopyridines as Selective JAK1 Inhibitors: From Hit Identification to GLPG0634." *J. Med Chem.* 57: 9323-9342 (2014); the crystal structure PDB 4ji9 and related ligands described in Siu, M. et al. "2-Amino-

[1,2,4]triazolo[1,5-a]pyridines as JAK2 inhibitors." *Bioorg. Med Chem. Lett.* 23: 5014-5021 (2013); and, the crystal structures PDB 3io7 and 3iok and related ligands described in Schenkel, L. B. et al. "Discovery of potent and highly selective thienopyridine janus kinase 2 inhibitors." *J. Med. Chem.* 54: 8440-8450 (2011).

FIG. 8MM provides non-limiting examples of JAK3 Targeting Ligands wherein R represents exemplary points at which the Linker can be attached. For additional examples and related ligands, see, the crystal structure PDB 3zc6 and related ligands described in Lynch, S. M. et al. "Strategic Use of Conformational Bias and Structure Based Design to Identify Potent Jak3 Inhibitors with Improved Selectivity Against the Jak Family and the Kinome." *Bioorg. Med Chem. Lett.* 23: 2793 (2013); and, the crystal structures PDB 4hvd, 4i6q, and 3zep and related ligands described in Soth, M. et al. "3-Amido Pyrrolopyrazine JAK Kinase Inhibitors: Development of a JAK3 vs JAK1 Selective Inhibitor and Evaluation in Cellular and in Vivo Models." *J. Med Chem.* 56: 345-356 (2013) and Jaime-Figueroa, S. et al. "Discovery of a series of novel 5H-pyrrolo[2,3-b]pyrazine-2-phenyl ethers, as potent JAK3 kinase inhibitors." *Bioorg. Med Chem. Lett.* 23: 2522-2526 (2013).

FIG. 8NN-8OO provide non-limiting examples of KIT Targeting Ligands wherein R represents exemplary points at which the Linker can be attached. For additional examples and related ligands, see, the crystal structure PDB 1t46 and related ligands described in Mol, C. D. et al. "Structural basis for the autoinhibition and STI-571 inhibition of c-Kit tyrosine kinase." *J. Biol. Chem.* 279: 31655-31663 (2004); and, the crystal structure PDB 4u0i and related ligands described in Garner, A. P. et al. "Ponatinib Inhibits Polyclonal Drug-Resistant KIT Oncoproteins and Shows Therapeutic Potential in Heavily Pretreated Gastrointestinal Stromal Tumor (GIST) Patients." *Clin. Cancer Res.* 20: 5745-5755 (2014).

FIG. 88PP-8VV provide non-limiting examples of EGFR Targeting Ligands wherein R represents exemplary points at which the Linker can be attached. For additional examples and related ligands, see, the crystal structures PDB 5hcy, 4rj4, and 5cav; Heald, R., "Noncovalent Mutant Selective Epidermal Growth Factor Receptor Inhibitors: A Lead Optimization Case Study", *J. Med Chem.* 58, 8877-8895 (2015); Hanano, E. J., "Discovery of Selective and Noncovalent Diaminopyrimidine-Based Inhibitors of Epidermal Growth Factor Receptor Containing the T790M Resistance Mutation. "*J. Med Chem.,* 57, 10176-10191 (2014); Chan, B. K. et al. "Discovery of a Noncovalent, Mutant-Selective Epidermal Growth Factor Receptor Inhibitor "*J. Med Chem.* 59, 9080 (2016); the crystal structure PDB 5d41 and related ligands described in Jia, Y. et al., "Overcoming EGFR (T790M) and EGFR(C797S) resistance with mutant-selective allosteric inhibitors "*Nature* 534, 129 (2016); Ward, R. A. "Structure- and reactivity-based development of covalent inhibitors of the activating and gatekeeper mutant forms of the epidermal growth factor receptor (EGFR)" *J. Med Chem.* 56, 7025-7048 (2013); the crystal structure PDB 4zau and related ligands described in "Discovery of a Potent and Selective EGFR Inhibitor (AZD9291) of Both Sensitizing and T790M Resistance Mutations That Spares the Wild Type Form of the Receptor "*J. Med Chem.,* 57 (20), 8249-8267 (2014); the crystal structure PDB 5em7 and related ligands described in Bryan, M. C. et al. "Pyridones as Highly Selective, Noncovalent Inhibitors of T790M Double Mutants of EGFR "*ACS Med Chem. Lett.,* 7 (1), 100-104 (2016); the crystal structure PDB 3IKA and related ligands described in Zhou, W. et al. "Novel mutant-selective EGFR kinase inhibitors against EGFR T790M" *Nature* 462(7276), 1070-1074 (2009); the crystal structure see PDB 5feq and related ligands described in Lelais, G., J. "Discovery of (R,E)-N-(7-Chloro-1-(1-[4-(dimethylamino)but-2-enoyl] azepan-3-yl)-1H-benzo[d]imidazol-2-yl)-2-methylisonicotinamide (EGF816), a Novel, Potent, and WT Sparing Covalent Inhibitor of Oncogenic (L858R, exl9del) and Resistant (T790M) EGFR Mutants for the Treatment of EGFR Mutant Non-Small-Cell Lung Cancers" *Med Chem.,* 59 (14), 6671-6689 (2016); Lee, H.-J. "Noncovalent Wild-type-Sparing Inhibitors of EGFR T790M" *Cancer Discov.* 3(2): 168-181 (2013); the crystal structure PDB 5j7h and related ligands described in Huang, W-S. et al. "Discovery of Brigatinib (AP26113), a Phosphine Oxide-Containing, Potent, Orally Active Inhibitor of Anaplastic Lymphoma Kinase." *J. Med Chem.* 59: 4948-4964 (2016); the crystal structure PDB 4v0g and related ligands described in Hennessy, E. J. et al. "Utilization of Structure-Based Design to Identify Novel, Irreversible Inhibitors of EGFR Harboring the T790M Mutation." *ACS. Med Chem. Lett.* 7: 514-519 (2016); the crystal structure PDB 5hg7 and related ligands described in Cheng, H. "Discovery of 1-{(3R,4R)-3-[({5-Chloro-2-[(1-methyl-1H-pyrazol-4-yl)amino]-7H-pyrrolo[2,3-d]pyrimidin-4-yl}oxy)methyl]-4-methoxypyrrolidin-1-yl}prop-2-en-1-one (PF-06459988), a Potent, WT Sparing, Irreversible Inhibitor of T790M-Containing EGFR Mutants." *J. Med Chem.* 59: 2005-2024 (2016); Hao, Y. "Discovery and Structural Optimization of N5-Substituted 6,7-Dioxo-6,7-dihydropteridines as Potent and Selective Epidermal Growth Factor Receptor (EGFR) Inhibitors against L858R/T790M Resistance Mutation. "*J. Med Chem.* 59: 7111-7124 (2016); the crystal structure PDB 5ug8, 5ug9, and 5ugc and related ligands described in Planken, S. "Discovery of N-((3R,4R)-4-Fluoro-1-(6-((3-methoxy-1-methyl-1H-pyrazol-4-yl) amino)-9-methyl-9H-purin-2-yl)pyrrolidine-3-yl)acrylamide (PF-06747775) through Structure-Based Drug Design: A High Affinity Irreversible Inhibitor Targeting Oncogenic EGFR Mutants with Selectivity over Wild-Type EGFR." *J. Med Chem.* 60: 3002-3019 (2017); the crystal structure PDB 5gnk and related ligands described in Wang, A. "Discovery of (R)-1-(3-(4-Amino-3-(3-chloro-4-(pyridin-2-ylmethoxy) phenyl)-1H-pyrazolo[3,4-d]pyrimidin-1-yl)piperidin-1-yl) prop-2-en-1-one (CHMFL-EGFR-202) as a Novel Irreversible EGFR Mutant Kinase Inhibitor with a Distinct Binding Mode." *J. Med Chem.* 60: 2944-2962 (2017); and, Juchum, M. "Trisubstituted imidazoles with a rigidized hinge binding motif act as single digit nM inhibitors of clinically relevant EGFR L858R/T790M and L858R/T790M/C797S mutants: An example of target hopping." *J. Med Chem.* DOI: 10.1021/acs.jmedchem.7b00178 (2017).

FIG. 8WW-8XX provide non-limiting examples of PAKI Targeting Ligands wherein R represents exemplary points at which the Linker can be attached. For additional examples and related ligands, see, Rudolph, J. et al. "Chemically Diverse Group I p21-Activated Kinase(PAK) Inhibitors Impart Acute Cardiovascular Toxicity with a Narrow Therapeutic Window." *J. Med Chem.* 59, 5520-5541 (2016) and Karpov A S, et al. ACS Med *Chem Lett.* 22; 6(7):776-81 (2015).

FIG. 8YY provides non-limiting examples of PAK4 Targeting Ligands wherein R represents exemplary points at which the Linker can be attached. For additional examples and related ligands, see, Staben S T, et al. *J Med Chem.* 13; 57(3):1033-45 (2014) and Guo, C. et al. "Discovery of pyrroloaminopyrazoles as novel PAK inhibitors" *J. Med Chem.* 55, 4728-4739 (2012).

FIG. 8ZZ-8AAA provide non-limiting examples of IDO Targeting Ligands wherein R represents exemplary points at which the Linker can be attached. For additional examples and related ligands, see, Yue, E. W.; et al. "Discovery of potent competitive inhibitors of indoleamine 2,3-dioxygenase with in vivo pharmacodynamic activity and efficacy in a mouse melanoma model." *J. Med Chem.* 52, 7364-7367 (2009); Tojo, S.; et al. "Crystal structures and structure, and activity relationships of imidazothiazole derivatives as IDO1 inhibitors." *ACS Med. Chem. Lett.* 5, 1119-1123 (2014); Mautino, M. R. et al. "NLG919, a novel indoleamine-2,3-dioxygenase (IDO)-pathway inhibitor drug candidate for cancer therapy" Abstract 491, AACR 104th Annual Meeting 2013; Apr. 6-10, 2013; Washington, DC; and, WO2012142237 titled "Fused imidazole derivatives useful as IDO inhibitors".

FIG. 8BBB-8EEE provide non-limiting examples of ERK1 and ERK2 Targeting Ligands wherein R represents exemplary points at which the Linker can be attached. For additional examples and related ligands, see, the crystal structures PDB 5K4I and 5K4J and related ligands described in Blake, J. F. et al. "Discovery of (S)-1-(1-(4-Chloro-3-fluorophenyl)-2-hydroxyethyl)-4-(2-((1-methyl-1H-pyrazol-5-yl)amino)pyrimidin-4-yl)pyridin-2(1H)-one (GDC-0994), an Extracellular Signal-Regulated Kinase 1/2 (ERK1/2) Inhibitor in Early Clinical Development" *J. Med. Chem.* 59: 5650-5660 (2016); the crystal structure PDB 5BVF and related ligands described in Bagdanoff, J. T. et al. "Tetrahydropyrrolo-diazepenones as inhibitors of ERK2 kinase" *Bioorg. Med. Chem. Lett.* 25, 3788-3792 (2015); the crystal structure PDB 4QYY and related ligands described in Deng, Y. et al. "Discovery of Novel, Dual Mechanism ERK Inhibitors by Affinity Selection Screening of an Inactive Kinase" *J. Med. Chem.* 57: 8817-8826 (2014); the crystal structures PDB 5HD4 and 5HD7 and the related ligands described in Jha, S. et al. "Dissecting Therapeutic Resistance to ERK Inhibition" *Mol. Cancer Ther.* 15: 548-559 (2016); the crystal structure PDB 4XJ0 and related ligands described in Ren, L. et al. "Discovery of highly potent, selective, and efficacious small molecule inhibitors of ERK1/2." *J. Med Chem.* 58: 1976-1991 (2015); the crystal structures PDB 4ZZM, 4ZZN, 4ZZO and related ligands described in Ward, R. A. et al. "Structure-Guided Design of Highly Selective and Potent Covalent Inhibitors of Erk1/2." *J. Med Chem.* 58: 4790 (2015); Burrows, F. et al. "KO-947, a potent ERK inhibitor with robust preclinical single agent activity in MAPK pathway dysregulated tumors" Poster #5168, AACR National Meeting 2017; Bhagwat, S. V. et al. "Discovery of LY3214996, a selective and novel ERK1/2 inhibitor with potent antitumor activities in cancer models with MAPK pathway alterations." AACR National Meeting 2017; the crystal structures PDB 3FHR and 3FXH and related ligands described in Cheng, R. et al. "High-resolution crystal structure of human Mapkap kinase 3 in complex with a high affinity ligand" *Protein Sci.* 19: 168-173 (2010); the crystal structures PDB 5NGU, 5NHF, 5NHH, 5NHJ, 5NHL, 5NHO, 5NHP, and 5NHV and related ligands described in Ward, R. A. et al. "Structure-Guided Discovery of Potent and Selective Inhibitors of ERK1/2 from a Modestly Active and Promiscuous Chemical Start Point." *J. Med Chem.* 60, 3438-3450 (2017); the crystal structures PDB 3SHE and 3R1N and related ligands described in Oubrie, A. et al. "Novel ATP competitive MK2 inhibitors with potent biochemical and cell-based activity throughout the series." *Bioorg. Med. Chem. Lett.* 22: 613-618 (2012); "Structure-Guided Design of Potent and Selective Pyrimidylpyrrole Inhibitors of Extracellular Signal-Regulated Kinase (ERK) Using Conformational Control" *J Med Chem* 2009, 52(20), 6362; WO2015051341; "Discovery of a Potent and Selective Oral Inhibitor of ERK1/2 (AZD0364) That Is Efficacious in Both Monotherapy and Combination Therapy in Models of Non-small Cell Lung Cancer (NSCLC)" *J Med Chem* 2019, 62(24), 11004; and "ERK Inhibitor LY3214996 Targets ERK Pathway-Driven Cancers: A Therapeutic Approach Toward Precision Medicine" *Mol Cancer Ther* 2020, 19, 325.

FIG. 8FFF-8III provide non-limiting examples of ABL1 Targeting Ligands wherein R represents exemplary points at which the Linker can be attached. For additional examples and related ligands, see, the crystal structure PDB 1fpu and 2e2b and related ligands described in Schindler, T., et al. "Structural mechanism for STI-571 inhibition of abelson tyrosine kinase", *Science* 289: 1938-1942 (2000); and Horio, T. et al. "Structural factors contributing to the Abl/Lyn dual inhibitory activity of 3-substituted benzamide derivatives", *Bioorg. Med. Chem. Lett.* 17: 2712-2717 (2007); the crystal structures PDB 2hzn and 2hiw and related ligands described in Cowan-Jacob, S. W. et al. "Structural biology contributions to the discovery of drugs to treat chronic myelogenous leukemia", *Acta Crystallog. Sect. D* 63: 80-93 (2007) and Okram, B. et al. "A general strategy for creating", *Chem. Biol.* 13: 779-786 (2006); the crystal structure PDB 3cs9 and related ligands described in Weisberg, E. et al. "Characterization of AMN107, a selective inhibitor of native and mutant Bcr-Abl", *Cancer Cell* 7: 129-14 (2005); the crystal structure PDB 3ik3 and related ligands described in O'Hare, T. et al. "AP24534, a pan-BCR-ABL inhibitor for chronic myeloid leukemia, potently inhibits the T315I mutant and overcomes mutation-based resistance", Cancer Cell 16: 401-412 (2009); the crystal structure PDB 3mss and related ligands described in Jahnke, W. et al. "Binding or bending: distinction of allosteric Abl kinase agonists from antagonists by an NMR-based conformational assay", *J. Am. Chem. Soc.* 132: 7043-7048 (2010); the crystal structure PDB 3oy3 and related ligands described in Zhou, T. et al. "Structural Mechanism of the Pan-BCR-ABL Inhibitor Ponatinib (AP24534): Lessons for Overcoming Kinase Inhibitor Resistance", *Chem. Biol. Drug Des.* 77: 1-11 (2011); the crystal structures PDB 3qri and 3qrk and related ligands described in Chan, W. W. et al. "Conformational Control Inhibition of the BCR-ABL1 Tyrosine Kinase, Including the Gatekeeper T315I Mutant, by the Switch-Control Inhibitor DCC-2036", Cancer Cell 19: 556-568 (2011); the crystal structure PDB 5hu9 and 2f4j and related ligands described in Liu, F. et al. "Discovery and characterization of a novel potent type II native and mutant BCR-ABL inhibitor (CHMFL-074) for Chronic Myeloid Leukemia (CML)", *Oncotarget* 7: 45562-45574 (2016) and Young, M. A. et al. "Structure of the kinase domain of an imatinib-resistant Abl mutant in complex with the Aurora kinase inhibitor VX-680", *Cancer Res.* 66: 1007-1014 (2006); the crystal structure PDB 2gqg and 2qoh and related ligands described in Tokarski, J. S. et al. "The Structure of Dasatinib (BMS-354825) Bound to Activated ABL Kinase Domain Elucidates Its Inhibitory Activity against Imatinib-Resistant ABL Mutants", *Cancer Res.* 66: 5790-5797 (2006); and Zhou, T. et al. "Crystal Structure of the T315I Mutant of Abl Kinase", *Chem. Biol. DrugDes.* 70: 171-181 (2007); the crystal structure PDB 2gqg and 2qoh and related ligands described in Tokarski, J. S. et al. "The Structure of Dasatinib (BMS-354825) Bound to Activated ABL Kinase Domain Elucidates Its Inhibitory Activity against Imatinib-Resistant ABL Mutants", *Cancer Res.* 66: 5790-5797 (2006) and Zhou, T. et al. "Crystal Structure of the T315I Mutant of Abl Kinase",

*Chem. Biol. Drug Des.* 70: 171-181 (2007); the crystal structure PDB 2gqg and 2qoh and related ligands described in Tokarski, J. S. et al. "The Structure of Dasatinib (BMS-354825) Bound to Activated ABL Kinase Domain Elucidates Its Inhibitory Activity against Imatinib-Resistant ABL Mutants", *Cancer Res.* 66: 5790-5797 (2006) and Zhou, T. et al. "Crystal Structure of the T315I Mutant of Abl Kinase", *Chem. Biol. Drug Des.* 70: 171-181(2007); the crystal structures PDB 3dk3 and 3dk8 and related ligands described in Berkholz, D. S. et al. "Catalytic cycle of human glutathione reductase near 1 A resolution" *J. Mol. Biol.* 382: 371-384 (2008); the crystal structure PDB 3ue4 and related ligands described in Levinson, N. M. et al. "Structural and spectroscopic analysis of the kinase inhibitor bosutinib and an isomer of bosutinib binding to the abl tyrosine kinase domain", *Plos One* 7: e29828-e29828 (2012); the crystal structure PDB 4cy8 and related ligands described in Jensen, C. N. et al. "Structures of the Apo and Fad-Bound Forms of 2-Hydroxybiphenyl 3-Monooxygenase (Hbpa) Locate Activity Hotspots Identified by Using Directed Evolution", *Chembiochem* 16: 968 (2015); the crystal structure PDB 2hz0 and related ligands described in Cowan-Jacob, S. W. et al. "Structural biology contributions to the discovery of drugs to treat chronic myelogenous leukaemia", *Acta Crystallogr D Biol Crystallogr.* 63(Pt 1):80-93 (2007); the crystal structure PDB 3pyy and related ligands described in Yang, J. et al. "Discovery and Characterization of a Cell-Permeable, Small-Molecule c-Abl Kinase Activator that Binds to the Myristoyl Binding Site", *Chem. Biol.* 18: 177-186 (2011); and, the crystal structure PDB 5k5v and related ligands described in Kim, M. K., et al. "Structural basis for dual specificity of yeast N-terminal amidase in the N-end rule pathway", *Proc. Natl. Acad Sci. U.S.A.* 113: 12438-12443 (2016).

FIG. 8JJJ provide non-limiting examples of ABL2 Targeting Ligands wherein R represents exemplary points at which the Linker can be attached. For additional examples and related ligands, see, the crystal structure PDB 2xyn and related ligands described in Salah, E. et al. "Crystal Structures of Abl-Related Gene (Abl2) in Complex with Imatinib, Tozasertib (Vx-680), and a Type I Inhibitor of the Triazole Carbothioamide Class", *J. Med Chem.* 54: 2359 (2011); the crystal structure PDB 4xli and related ligands described in Ha, B. H. et al. "Structure of the ABL2/ARG kinase in complex with dasatinib" *Acta Crystallogr. Sect. F* 71: 443-448 (2015); and the crystal structure PDB 3gvu and related ligands described in Salah, E. et al. "*The crystal structure of human ABL2 in complex with Gleevec*", to be published.

FIG. 8KKK-8MMM provide non-limiting examples of AKT 1 Targeting Ligands wherein R represents exemplary points at which the Linker can be attached. For additional examples and related ligands, see, Lippa, B. et al. "Synthesis and structure based optimization of novel Akt inhibitors Bioorg. *Med Chem. Lett.* 18: 3359-3363 (2008); Freeman-Cook, K. D. et al. "Design of selective, ATP-competitive inhibitors of Akt", *J. Med Chem.* 53: 4615-4622 (2010); Blake, J. F. et al "Discovery of pyrrolopyrimidine inhibitors of Akt", *Bioorg. Med Chem. Lett.* 20: 5607-5612 (2010); Kallan, N. C. et al. "Discovery and SAR of spirochromane Akt inhibitors", *Bioorg. Med Chem. Lett.* 21: 2410-2414 (2011); Lin, K "An ATP-Site On-Off Switch That Restricts Phosphatase Accessibility of Akt", *Sci. Signal.* 5: ra37-ra37 (2012); Addie, M. et al. "Discovery of 4-Amino-N-[(1S)-1-(4-chlorophenyl)-3-hydroxypropyl]-1-(7H-pyrrolo[2,3-d] pyrimidin-4-yl)piperidine-4-carboxamide (AZD5363), an Orally Bioavailable, Potent Inhibitor of Akt Kinases", *J. Med Chem.* 56: 2059-2073 (2013); Wu, W. I., et al. "Crystal structure of human AKT1 with an allosteric inhibitor reveals a new mode of kinase inhibition. *Plos One* 5: 12913-12913 (2010); Ashwell, M. A. et al. "Discovery and optimization of a series of 3-(3-phenyl-3H-imidazo[4,5-b]pyridin-2-yl)pyridin-2-amines: orally bioavailable, selective, and potent ATP-independent Akt inhibitors", *J. Med Chem.* 55: 5291-5310 (2012); and, Lapierre, J. M. et al. "Discovery of 3-(3-(4-(1-Aminocyclobutyl)phenyl)-5-phenyl-3H-imidazo[4,5-b] pyridin-2-yl)pyridin-2-amine (ARQ 092): An Orally Bioavailable, Selective, and Potent Allosteric AKT Inhibitor", *J. Med Chem.* 59: 6455-6469 (2016).

FIG. 8NNN-8OOO provide non-limiting examples of AKT2 Targeting Ligands wherein R represents exemplary points at which the Linker can be attached. For additional examples and related ligands, see, the crystal structured PDB 2jdo and 2jdr and related ligands described in Davies, T. G. et al. "A Structural Comparison of Inhibitor Binding to Pkb, Pka and Pka-Pkb Chimera", *J. Mol. Biol.* 367: 882 (2007); the crystal structure PDB 2uw9 and related ligands described in Saxty, G. et al "Identification of Inhibitors of Protein Kinase B Using Fragment-Based Lead Discovery", *J. Med Chem.* 50: 2293-2296 (2007); the crystal structure PDB 2x39 and 2xh5 and related ligands described in Mchardy, T. et al. "Discovery of 4-Amino-1-(7H-Pyrrolo[2, 3-D]Pyrimidin-4-Yl)Piperidine-4-Carboxamides as Selective, Orally Active Inhibitors of Protein Kinase B (Akt)", *J. Med Chem.* 53: 2239d (2010); the crystal structure PDB 3d03 and related ligands described in Hadler, K. S. et al. "Substrate-promoted formation of a catalytically competent binuclear center and regulation of reactivity in a glycerophosphodiesterase from *Enterobacter aerogenes*', *J. Am. Chem. Soc.* 130: 14129-14138 (2008); and, the crystal structures PDB 3e87, 3e8d and 3e88 and related ligands described in Rouse, M. B. et al. "Aminofurazans as potent inhibitors of AKT kinase" *Bioorg. Med Chem. Lett.* 19: 1508-1511 (2009).

FIG. 8PPP provides non-limiting examples of BMX Targeting Ligands wherein R represents exemplary points at which the Linker can be attached. For additional examples and related ligands, see, the crystal structures PDB 3sxr and 3sxr and related ligands described in Muckelbauer, J. et al. "X-ray crystal structure of bone marrow kinase in the x chromosome: a Tec family kinase", *Chem. Biol. Drug Des.* 78: 739-748 (2011).

FIG. 8QQQ-8SSS provide non-limiting examples of CSF1R Targeting Ligands wherein R represents exemplary points at which the Linker can be attached. For additional examples and related ligands, see, the crystal structures PDB 2iOv and 2ilm and related ligands described in Schubert, C. et al. "Crystal structure of the tyrosine kinase domain of colony-stimulating factor-1 receptor (cFMS) in complex with two inhibitors", *J. Biol. Chem.* 282: 4094-4101 (2007); the crystal structure PDB 3b ea and related ligands described in Huang, H. et al. "Design and synthesis of a pyrido[2,3-d]pyrimidin-5-one class of anti-inflammatory FMS inhibitors", *Bioorg. Med Chem. Lett.* 18: 2355-2361 (2008); the crystal structure PDB 3dpk and related ligands described in M. T., McKay, D. B. Overgaard, "Structure of the Elastase of *Pseudomonas aeruginosa* Complexed with Phosphoramidon", to be published; the crystal structures PDB 3krj and 3krl and related ligands described in Illig, C. R. et al. "Optimization of a Potent Class of Arylamide Colony-Stimulating Factor-1 Receptor Inhibitors Leading to Anti-inflammatory Clinical Candidate 4-Cyano-N-[2-(1-cyclohexen-1-yl)-4-[1-[(dimethylamino)acetyl]-4-piperidinyl] phenyl]-1H-imidazole-2-carboxamide (JNJ-28312141", *J. Med. Chem.* 54: 7860-7883 (2011); the crystal structure PDB 4r7h and related ligands described in Tap, W. D. et al. "Structure-Guided Blockade of CSF1R Kinase in Tenosynovial Giant-Cell Tumor: *N Engl J Med* 373: 428-437 (2015); the crystal structure PDB 31cd and 31coa and related ligands described in Meyers, M. J. et al. "Structure-based drug design enables conversion of a DFG-in binding CSF-1R kinase inhibitor to a DFG-out binding mod", *Bioorg. Med. Chem. Lett.* 20: 1543-1547 (2010); the crystal structure PDB 4hw7 and related ligands described in Zhang, C. et al. "Design and pharmacology of a highly specific dual FMS and KIT kinase inhibitor", *Proc. Natl. Acad. Sci. USA* 110: 5689-5694 (2013); and, the crystal structure PDB 4r7i and related ligands described in Tap, W. D. et al. "Structure-Guided Blockade of CSF1R Kinase in Tenosynovial Giant-Cell Tumor", *N Engl J Med* 373: 428-437 (2015).

FIG. 8TTT provides non-limiting examples of CSK Targeting Ligands wherein R represents exemplary points at which the Linker can be attached. For additional examples and related ligands, see, Levinson, N. M. et al. "Structural basis for the recognition of c-Src by its inactivator Csk", *Cell* 134: 124-134 (2008).

FIG. 8UUU-8YYY provide non-limiting examples of DDR1 Targeting Ligands wherein R represents exemplary points at which the Linker can be attached. For additional examples and related ligands, see, the crystal structures PDB 3zos and 4bkj and related ligands described in Canning, P. et al. "Structural Mechanisms Determining Inhibition of the Collagen Receptor Ddr1 by Selective and Multi-Targeted Type II Kinase Inhibitors", *J. Mol. Biol.* 426: 2457 (2014); the crystal structure PDB 4ckr and related ligands described in Kim, H. et al. "Discovery of a Potent and Selective Ddr1 Receptor Tyrosine Kinase Inhibitor", *ACS Chem. Biol.* 8: 2145 (2013); the crystal structure PDB 5b vk, 5b vn and 5b vw and related ligands described in Murray, C. W et al. "Fragment-Based Discovery of Potent and Selective DDR1/2 Inhibitors", ACS Med. Chem. Lett. 6: 798-803 (2015); the crystal structure PDB 5fdp and related ligands described in Wang, Z. et al. "Structure-Based Design of Tetrahydroisoquinoline-7-carboxamides as Selective Discoidin Domain Receptor 1 (DDR1) Inhibitors", *J. Med. Chem.* 59: 5911-5916 (2016); and, the crystal structure PDB 5fdx and related ligands described in Bartual, S. G. et al. "Structure of DDR1 receptor tyrosine kinase in complex with D2164 inhibitor at 2.65 Angstroms resolution", to be published.

FIG. 8ZZZ-8CCCC provide non-limiting examples of EPHA2 Targeting Ligands wherein R represents exemplary points at which the Linker can be attached. For additional examples and related ligands, see, the crystal structures PDB 5i9x, 5i9y, 5ia0 and 5ia1 and related ligands described in Heinzlmeir, S. et al. "Chemical Proteomics and Structural Biology Define EPHA2 Inhibition by Clinical Kinase Drug", *ACS Chem. Biol.* 11: 3400-3411 (2016); the crystal structure PDB 5i9z and related ligands described in Heinzlmeir, S. et al. "Crystal Structure of Ephrin A2 (EphA2) Receptor Protein Kinase with danusertib (PHA739358)", *ACS Chem Biol* 11 3400-3411 (2016); and, the crystal structures PDB 5ia2, 5ia3, 5ia4, and 5ia5 and related ligands described in Heinzlmeir, S. et al. "Chemical Proteomics and Structural Biology Define EPHA2 Inhibition by Clinical Kinase Drug", *ACS Chem. Biol.* 11: 3400-3411 (2016).

FIG. 8DDDD-8FFFF provide non-limiting examples of EPHA3 Targeting Ligands wherein R represents exemplary points at which the Linker can be attached. For additional examples and related ligands, see, the crystal structure PDB 4g2f and related ligands described in Zhao, H. et al. "Discovery of a novel chemotype of tyrosine kinase inhibitors by fragment-based docking and molecular dynamics", *ACS Med. Chem. Lett.* 3: 834-838 (2012); the crystal structure PDB 4gk2 and 4gk3 and related ligands described in Lafleur, K. et al. "Optimization of Inhibitors of the Tyrosine Kinase EphB4. 2. Cellular Potency Improvement and Binding Mode Validation by X-ray Crystallography", *J. Med. Chem.* 56: 84-96 (2013); the crystal structure PDB 4gk3 and related ligands described in Lafleur, K. et al. "Optimization of Inhibitors of the Tyrosine Kinase EphB4. 2. Cellular Potency Improvement and Binding Mode Validation by X-ray Crystallography", *J. Med. Chem.* 56: 84-96 (2013); the crystal structure PDB 4p4c and 4p5q and related ligands described in Unzue, A. et al. "Pyrrolo[3,2-b]quinoxaline Derivatives as Types I1/2 and II Eph Tyrosine Kinase Inhibitors: Structure-Based Design, Synthesis, and in Vivo Validation", *J. Med. Chem.* 57: 6834-6844 (2014); the crystal structure PDB 4p5z and related ligands described in Unzue, A. et al. "Pyrrolo[3,2-b]quinoxaline Derivatives as Types I1/2 and II Eph Tyrosine Kinase Inhibitors: Structure-Based Design, Synthesis, and in Vivo Validation", *J. Med Chem.* 57: 6834-6844 (2014); the crystal structure PDB 4twn and related ligands described in Dong, J. et al. "Structural Analysis of the Binding of Type I, I1/2, and II Inhibitors to Eph Tyrosine Kinases", ACS Med. Chem. Lett. 6: 79-83 (2015); the crystal structure PDB 3dzq and related ligands described in Walker, J. R. "Kinase Domain of Human Ephrin Type-A Receptor 3 (Epha3) in Complex with ALW-II-38-3", to be published.

FIG. 8GGGG provides non-limiting examples of EPHA4 Targeting Ligands wherein R represents exemplary points at which the Linker can be attached. For additional examples and related ligands, see, the crystal structure PDB 2y60 and related ligands described in Clifton, I. J. et al. "The Crystal Structure of Isopenicillin N Synthase with Delta((L)-Alpha-Aminoadipoyl)-(L)-Cysteinyl-(D)-Methionine Reveals Thioether Coordination to Iron", *Arch. Biochem. Biophys.* 516: 103 (2011) and the crystal structure PDB 2xyu and related ligands described in Van Linden, O. P et al. "Fragment Based Lead Discovery of Small Molecule Inhibitors for the Epha4 Receptor Tyrosine Kinase", *Eur. J. Med Chem.* 47: 493 (2012).

FIG. 8IIII-8LLLL provides non-limiting examples of EPHA7 Targeting Ligands wherein R represents exemplary points at which the Linker can be attached. For additional examples and related ligands, see, the crystal structure PDB 3dko and related ligands described in Walker, J. R. et al. "Kinase domain of human ephrin type-a receptor 7 (epha7) in complex with ALW-II-49-7", to be published.

FIG. 8IIII-8LLLL provide non-limiting examples of EPHB4 Targeting Ligands wherein R represents exemplary points at which the Linker can be attached. For additional examples and related ligands, see, the crystal structure PDB 2vx1 and related ligands described in Bardelle, C. et al. "Inhibitors of the Tyrosine Kinase Ephb4. *Part 2*: Structure-Based Discovery and Optimization of 3,5-Bis Substituted Anilinopyrimidines", *Bioorg. Med Chem. Lett.* 18: 5717 (2008); the crystal structure PDB 2x9f and related ligands described in Bardelle, C. et al. "Inhibitors of the Tyrosine Kinase Ephb4. *Part 3*: Identification of Non-Benzodioxole-Based Kinase Inhibitors", *Bioorg. Med. Chem. Lett.* 20: 6242-6245 (2010); the crystal structure PDB 2xvd and related ligands described in Barlaam, B. et al. "Inhibitors of the Tyrosine Kinase Ephb4. Part 4: Discovery and Optimization of a Benzylic Alcohol Series", *Bioorg. Med Chem. Lett.* 21: 2207 (2011); the crystal structure PDB 3zew and related ligands described in Overman, R. C. et al. "Completing the Structural Family Portrait of the Human Ephb Tyrosine Kinase Domains", *Protein Sci.* 23: 627 (2014); the crystal structure PDB 4aw5 and related ligands described in Kim, M. H. et al. "The Design, Synthesis, and Biological Evaluation of Potent Receptor Tyrosine Kinase Inhibitors", *Bioorg. Med Chem. Lett.* 22: 4979 (2012); the crystal structure PDB 4bb4 and related ligands described in Vasbinder, M. M. et al. "Discovery and Optimization of a Novel Series of Potent Mutant B-Raf V600E Selective Kinase Inhibitors" *J. Med Chem.* 56: 1996.", (2013); the crystal structures PDB 2vwu, 2vwv and 2vww and related ligands described in Bardelle, C. et al "Inhibitors of the Tyrosine Kinase Ephb4. *Part* 1: Structure-Based Design and Optimization of a Series of 2,4-Bis-Anilinopyrimidines", *Bioorg. Med Chem. Lett.* 18: 2776-2780 (2008); the crystal structures PDB 2vwx, 2vwy, and 2vwz and related ligands described in Bardelle, C. et al. "Inhibitors of the Tyrosine Kinase Ephb4. *Part* 2: Structure-Based Discovery and Optimization of 3,5-Bis Substituted Anilinopyrimidines", *Bioorg. Med Chem. Lett.* 18: 5717 (2008); and, the crystal structure PDB 2vxo and related ligands described in Welin, M. et al. "Substrate Specificity and Oligomerization of Human Gmp Synthetas", *J. Mol. Biol.* 425: 4323 (2013).

FIG. 8MMMM provides non-limiting examples of ERBB2 Targeting Ligands wherein R represents exemplary points at which the Linker can be attached. For additional examples and related ligands, see, the crystal structure and related ligands described in Aertgeerts, K. et al "Structural Analysis of the Mechanism of Inhibition and Allosteric Activation of the Kinase Domain of HER2 Protein", *J. Biol. Chem.* 286: 18756-18765 (2011) and the crystal structure and related ligands described in Ishikawa, T. et al. "Design and Synthesis of Novel Human Epidermal Growth Factor Receptor 2 (HER2)/Epidermal Growth Factor Receptor (EGFR) Dual Inhibitors Bearing a Pyrrolo[3,2-d]pyrimidine Scaffold" *J. Med Chem.* 54: 8030-8050 (2011).

FIG. 8NNNN provides non-limiting examples of ERBB3 Targeting Ligands wherein R represents exemplary points at which the Linker can be attached. For additional examples and related ligands, see, Littlefield, P. et al. "An ATP-Competitive Inhibitor Modulates the Allosteric Function of the HER3 Pseudokinase", *Chem. Biol.* 21: 453-458 (2014).

FIG. 8OOOO provides non-limiting examples ERBB4 Targeting Ligands wherein R represents exemplary points at which the Linker can be attached. For additional examples and related ligands, see, Qiu, C. et al. "Mechanism of Activation and Inhibition of the HER4/ErbB4 Kinase", *Structure* 16: 460-467 (2008) and Wood, E. R. et al. "6-Ethynylthieno[3,2-d]- and 6-ethynylthieno[2,3-d]pyrimidin-4-anilines as tunable covalent modifiers of ErbB kinases", Proc. *Natl. Acad. Sci. Usa* 105: 2773-2778 (2008).

FIG. 8PPPP-8QQQQ provide non-limiting examples of FES Targeting Ligands wherein R represents exemplary points at which the Linker can be attached. For additional examples and related ligands, see, Filippakopoulos, P. et al "Structural Coupling of SH2-Kinase Domains Links Fes and Abl Substrate Recognition and Kinase Activation." *Cell* 134: 793-803 (2008) and Hellwig, S. et al. "Small-Molecule Inhibitors of the c-Fes Protein-Tyrosine Kinase", *Chem. Biol.* 19: 529-540 (2012).

FIG. 8RRRR provides non-limiting examples of FYN Targeting Ligands wherein R represents exemplary points at which the Linker can be attached. For additional examples and related ligands, see, Kinoshita, T. et. al. "Structure of human Fyn kinase domain complexed with staurosporine", *Biochem. Biophys. Res. Commun.* 346: 840-844 (2006).

FIG. 8SSSS-8VVVV provide non-limiting examples of GSG2 (Haspin) Targeting Ligands wherein R represents exemplary points at which the Linker can be attached. For additional examples and related ligands, see, the crystal structures PDB 3e7v, PDB 3f2n, 3fmd and related ligands described in Filippakopoulos, P. et al. "Crystal Structure of Human Haspin with a pyrazolo-pyrimidine ligand", to be published; the crystal structure PDB 3iq7 and related ligands described in Eswaran, J. et al. "Structure and functional characterization of the atypical human kinase haspin", *Proc. Natl. Acad. Sci. USA* 106: 20198-20203 (2009); and, the crystal structure PDB 4qtc and related ligands described in Chaikuad, A. et al. "A unique inhibitor binding site in ERK1/2 is associated with slow binding kinetics", *Nat. Chem. Biol.* 10: 853-860 (2014).

FIG. 8WWWW-8AAAAA provide non-limiting examples of HCK Targeting Ligands wherein R represents exemplary points at which the Linker can be attached. For additional examples and related ligands, see, the crystal structure PDB 1qcf and related ligands described in Schindler, T. et al. "Crystal structure of Hck in complex with a Src family-selective tyrosine kinase inhibitor", *Mol. Cell* 3: 639-648 (1999); the crystal structure PDB 2c0i and 2c0t and related ligands described in Burchat, A. et al. "Discovery of A-770041, a Src-Family Selective Orally Active Lck Inhibitor that Prevents Organ Allograft Rejection", *Bioorg. Med. Chem. Lett.* 16: 118 (2006); the crystal structure PDB 2hk5 and related ligands described in Sabat, M. et al. "The development of 2-benzimidazole substituted pyrimidine based inhibitors of lymphocyte specific kinase (Lck)", *Bioorg. Med Chem. Lett.* 16: 5973-5977 (2006); the crystal structures PDB 3vry, 3vs3, 3vs6, and 3vs7 and related ligands described in Saito, Y. et al. "A Pyrrolo-Pyrimidine Derivative Targets Human Primary AML Stem Cells in Vivo", *Sci Transl Med* 5: 181ra52-181ra52 (2013); and, the crystal structure PDB 4lud and related ligands described in Parker, L. J. et al "Kinase crystal identification and ATP-competitive inhibitor screening using the fluorescent ligand SKF86002 ", *Acta Crystallogr.*, Sect.D 70: 392-404 (2014).

FIG. 8BBBBB-8FFFFF provide non-limiting examples of IGF1R Targeting Ligands wherein R represents exemplary points at which the Linker can be attached. For additional examples and related ligands, see, the crystal structure PDB 2oj9 and related ligands described in Velaparthi, U. et al. "Discovery and initial SAR of 3-(1H-benzo[d]imidazol-2-yl)pyridin-2(1H)-ones as inhibitors of insulin-like growth factor 1-receptor (IGF-1R)", *Bioorg. Med Chem. Lett.* 17: 2317-2321 (2007); the crystal structure PDB 3i81 and related ligands described in Wittman, M. D. et al. "Discovery of a 2,4-disubstituted pyrrolo[1,2-f][1,2,4]triazine inhibitor (BMS-754807) of insulin-like growth factor receptor (IGF-1R) kinase in clinical development.", *J. Med Chem.* 52: 7360-7363 (2009); the crystal structure PDB 3nw5 and related ligands described in Sampognaro, A. J. et al. "Proline isosteres in a series of 2,4-disubstituted pyrrolo[1,2-f][1,2,4]triazine inhibitors of IGF-1R kinase and IR kinase", *Bioorg. Med. Chem. Lett.* 20: 5027-5030 (2010); the crystal structure PDB 3qqu and related ligands described in Buchanan, J. L. et al. "Discovery of 2,4-bis-arylamino-1,3-pyrimidines as insulin-like growth factor-1 receptor (IGF-1R) inhibitors", *Bioorg. Med Chem. Lett.* 21: 2394-2399 (2011); the crystal structure PDB 4d2r and related ligands described in Kettle, J. G. et al. "Discovery and Optimization of a Novel Series of Dyrk1B Kinase Inhibitors to Explore a Mek Resistance Hypothesis". *J. Med Chem.* 58: 2834 (2015); the crystal structure PDB 3fxq and related ligands described in Monferrer, D. et al. "Structural studies on the full-length LysR-type regulator TsaR from Comamonas *testosteroni* T-2 reveal a novel open conformation of the tetrameric LTTR fold", *Mol. Microbiol.* 75: 1199-1214 (2010); the crystal structure PDB 5fxs and related ligands described in Degorce, S. et al. "Discovery of Azd9362, a Potent Selective Orally Bioavailable and Efficacious Novel Inhibitor of Igf-R1", to be published; the crystal structure PDB 2zm3 and related ligands described in Mayer, S. C. et al. "Lead identification to generate isoquinolinedione inhibitors of insulin-like growth factor receptor (IGF-1R) for potential use in cancer treatment", *Bioorg. Med Chem. Lett.* 18: 3641-3645 (2008); the crystal structure PDB 3f5p and related ligands described in "Lead identification to generate 3-cyanoquinoline inhibitors of insulin-like growth factor receptor (IGF-1R) for potential use in cancer treatment" *Bioorg. Med Chem. Lett.* 19: 62-66 (2009); the crystal structure PDB 3lvp and related ligands described in Nemecek, C. et al. "Design of Potent IGF1-R Inhibitors Related to Bis-azaindoles" *Chem. Biol. DrugDes.* 76: 100-106 (2010); the crystal structure PDB 3o23 and related ligands described in Lesuisse, D. et al. "Discovery of the first non-ATP competitive IGF-1R kinase inhibitors: Advantages in comparison with competitive inhibitors", *Bioorg. Med Chem. Lett.* 21: 2224-2228 (2011); the crystal structure PDB 3d94 and related ligands described in Wu, J. et al. "Small-molecule inhibition and activation-loop trans-phosphorylation of the IGF1 receptor", *Embo J.* 27: 1985-1994 (2008); and, the crystal structure PDB 5hzn and related ligands described in Stauffer, F. et al. "Identification of a 5-[3-phenyl-(2-cyclic-ether)-methylether]-4-aminopyrrolo[2,3-d]pyrimidine series of IGF-1R inhibitors", *Bioorg. Med Chem. Lett.* 26: 2065-2067 (2016).

FIG. 8GGGGG-8JJJJJ provide non-limiting examples of INSR Targeting Ligands wherein R represents exemplary points at which the Linker can be attached. For additional examples and related ligands, see, the crystal structure PDB 2z8c and related ligands described in Katayama, N. et al. "Identification of a key element for hydrogen-bonding patterns between protein kinases and their inhibitors", *Proteins* 73: 795-801 (2008); the crystal structure PDB 3ekk and related ligands described in Chamberlain, S. D. et al. "Discovery of 4,6-bis-anilino-1H-pyrrolo[2,3-d]pyrimidines: Potent inhibitors of the IGF-1R receptor tyrosine kinase", (2009) *Bioorg. Med Chem. Lett.* 19: 469-473; the crystal structure PDB 3ekn and related ligands described in Chamberlain, S. D. et al. "Optimization of 4,6-bis-anilino-1H-pyrrolo[2,3-d]pyrimidine IGF-1R tyrosine kinase inhibitors towards JNK selectivity", *Bioorg. Med Chem. Lett.* 19: 360-364 (2009); the crystal structure PDB 5els and related ligands described in Sanderson, M. P. et al. "BI 885578, a Novel IGF1R/INSR Tyrosine Kinase Inhibitor with Pharmacokinetic Properties That Dissociate Antitumor Efficacy and Perturbation of Glucose Homeostasis" *Mol. Cancer Ther.* 14: 2762-2772 ", (2015); the crystal structure PDB 3eta and related ligands described in Patnaik, S. et al. "Discovery of 3,5-disubstituted-1H-pyrrolo[2,3-b]pyridines as potent inhibitors of the insulin-like growth factor-1 receptor (IGF-1R) tyrosine kinase", *Bioorg. Med Chem. Lett.* 19: 3136-3140 (2009); the crystal structure PDB 5hhw and related ligands described in Stauffer, F. et al. "Identification of a 5-[3-phenyl-(2-cyclic-ether)-methylether]-4-aminopyrrolo[2,3-d]pyrimidine series of IGF-1R inhibitors", *Bioorg. Med. Chem. Lett.* 26: 2065-2067 (2016); and, the crystal structure PDB 4ibm and related ligands described in Anastassiadis, T. et al. "A highly selective dual insulin receptor (IR)/insulin-like growth factor 1 receptor (IGF-1R) inhibitor derived from an extracellular signal-regulated kinase (ERK) inhibitor", *J. Biol. Chem.* 288: 28068-28077 (2013).

FIG. 8KKKKK-8PPPPP provide non-limiting examples of HBV Targeting Ligands wherein R represents exemplary points at which the Linker can be attached, Y is methyl or isopropyl, and X is N or C. For additional examples and related ligands, see, Weber, O.; et al. "Inhibition of human hepatitis B virus (HBV) by a novel non-nucleosidic compound in a transgenic mouse model." *Antiviral Res.* 54, 69-78 (2002); Deres, K.; et al. "Inhibition of hepatitis B virus replication by drug-induced depletion of nucleocapsids." *Science,* 299, 893-896 (2003); Stray, S. J.; Zlotnick, A. "BAY 41-4109 has multiple effects on Hepatitis B virus capsid assembly." *J. Mol. Recognit.* 19, 542-548 (2006); Stray, S. J.; et al. "heteroaryldihydropyrimidine activates and can misdirect hepatitis B virus capsid assembly." *Proc. Natl. Acad. Sci. U. S. A,* 102, 8138-8143 (2005); Guan, H.; et al. "The novel compound Z060228 inhibits assembly of the HBV capsid." *Life Sci.* 133, 1-7 (2015); Wang, X. Y.; et al. "In vitro inhibition of HBV replication by a novel compound, GLS4, and its efficacy against adefovir-dipivoxil-resistant HBV mutations." *Antiviral Ther.* 17, 793-803 (2012); Klumpp, K.; et al. "High-resolution crystal structure of a hepatitis B virus replication inhibitor bound to the viral core protein." 112, 15196-15201 (2015); Qiu, Z.; et al. "Design and synthesis of orally bioavailable 4-methyl heteroaryldihydropyrimidine based hepatitis B virus (HBV) capsid inhibitors." *J. Med. Chem.* 59, 7651-7666 (2016); Zhu, X.; et al. "2,4-Diaryl-4,6,7,8-tetrahydroquinazolin-5 (1H)-one derivatives as anti-HBV agents targeting at capsid assembly." *Bioorg. Med. Chem. Lett.* 20, 299-301 (2010); Campagna, M. R.; et al. "Sulfamoylbenzamide derivatives inhibit the assembly of hepatitis B virus nucleocapsids." *J. Virol.* 87, 6931-6942 (2013); Campagna, M. R.; et al. "Sulfamoylbenzamide derivatives inhibit the assembly of hepatitis B virus nucleocapsids." *J. Virol.* 87, 6931-6942 (2013); WO 2013096744 A1 titled "Hepatitis B antiviral agents"; WO 2015138895 titled "Hepatitis B core protein allosteric modulators"; Wang, Y. J.; et al. "A novel pyridazinone derivative inhibits hepatitis B virus replication by inducing genome-free capsid formation." Antimicrob. Agents Chemother. 59, 7061-7072 (2015); WO 2014033167 titled "Fused bicyclic sulfamoyl derivatives for the treatment of hepatitis"; U. S. 20150132258 titled "Azepane derivatives and methods of treating hepatitis B infections"; and, WO 2015057945 "Hepatitis B viral assembly effector".

Figure 9:
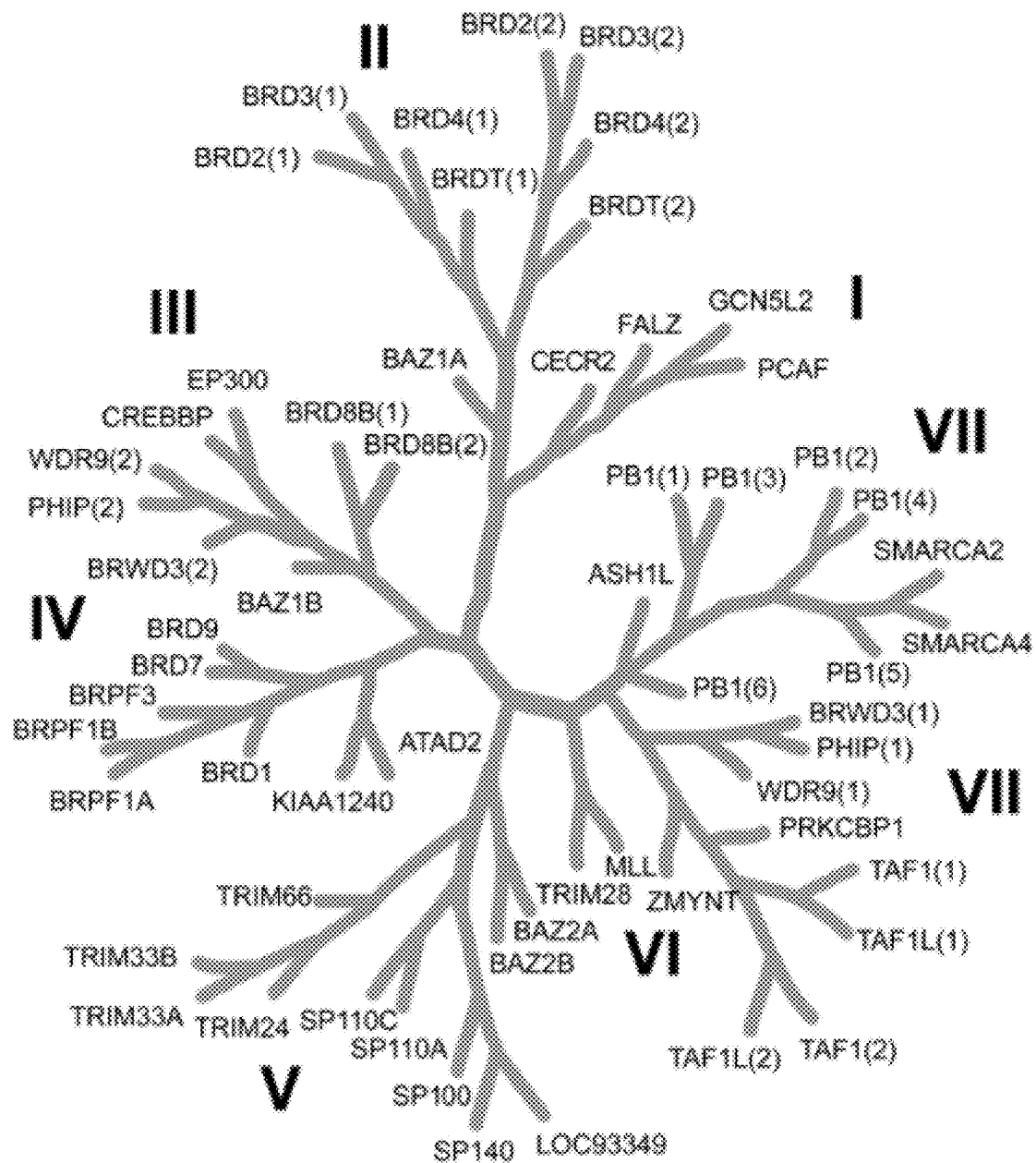

FIG. 9 is a dendrogram of the human bromodomain family of proteins organized into eight sub families, which are involved in epigenetic signaling and chromatin biology. Any of the proteins of the bromodomain family in FIG. 9 can be selected as a Target Protein according to the present invention.

Figure 10A:
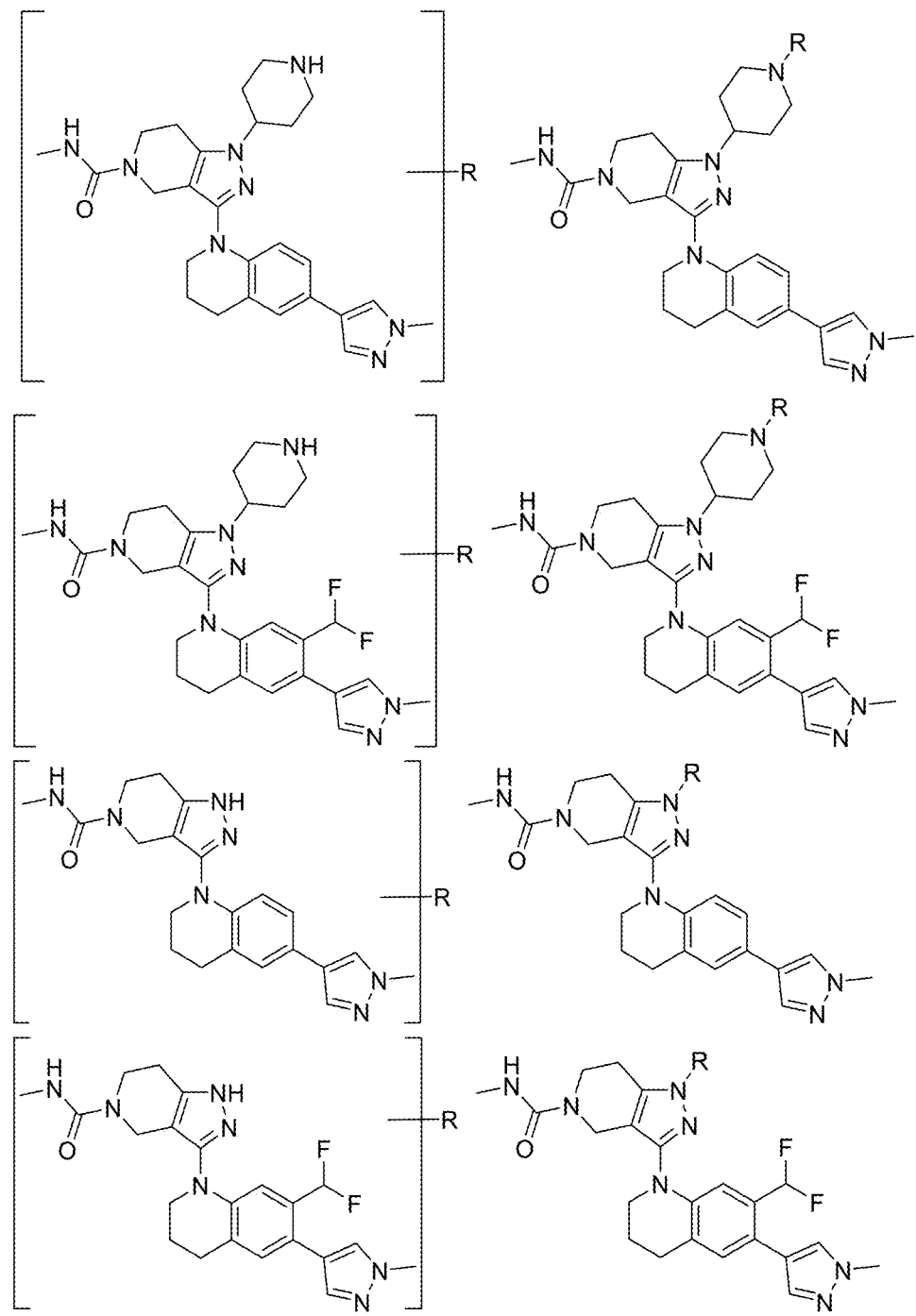
Figure 10B:
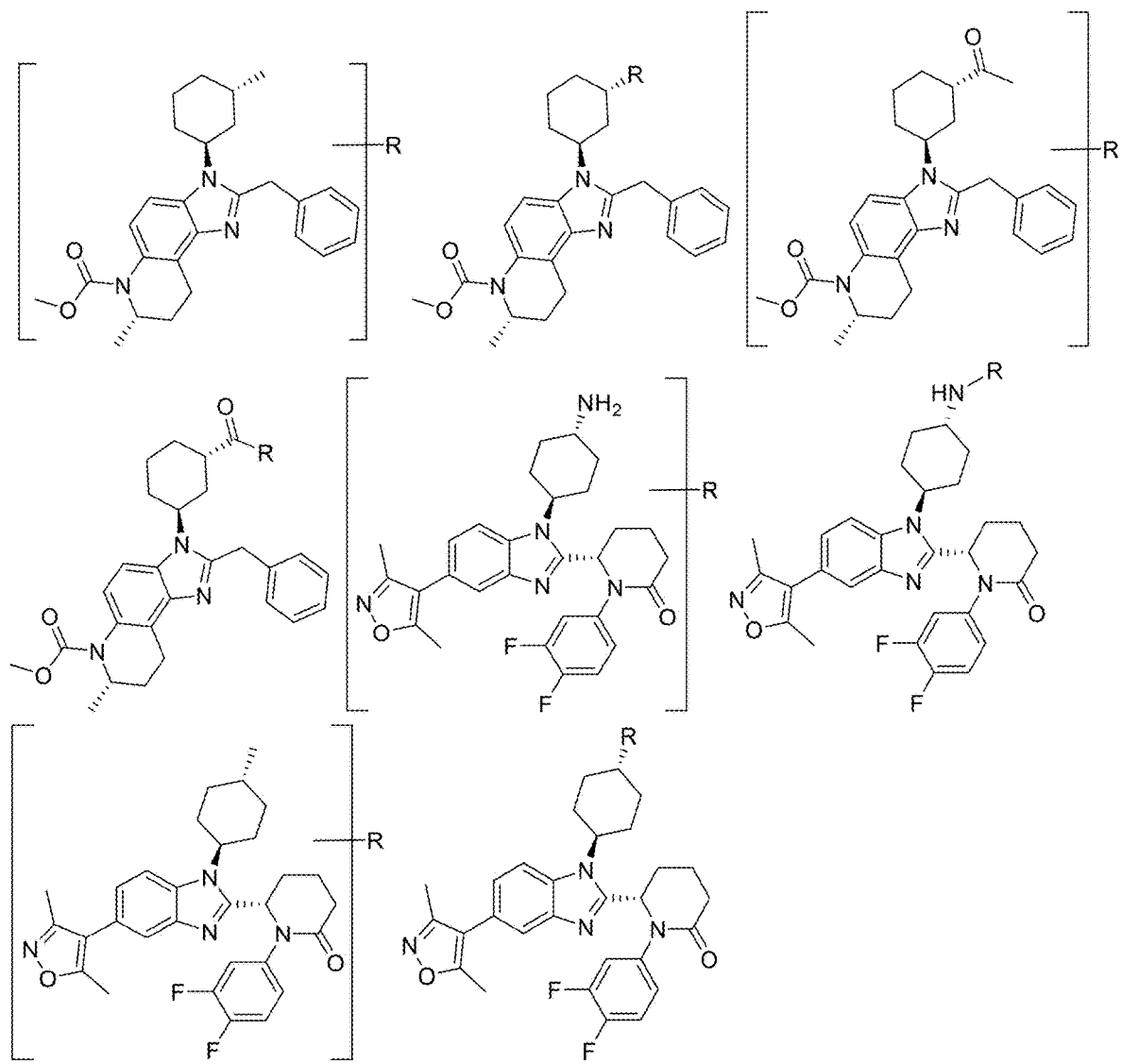

FIG. 10A and FIG. 10B provide non-limiting examples of CBP and/or P300 Targeting Ligands, wherein R represents exemplary points at which the Linker can be attached. For example additional examples of Targeting Ligands see "GNE-781, A Highly Advanced Potent and Selective Bromodomain Inhibitor of Cyclic Adenosine Monophosphate Response Element Binding Protein, Binding Protein (CBP)" *J Med Chem* 2017, 60(22), 9162; CCS-1477, WO2018073586; FT-7051, and WO2019055869.

Figure 11A:
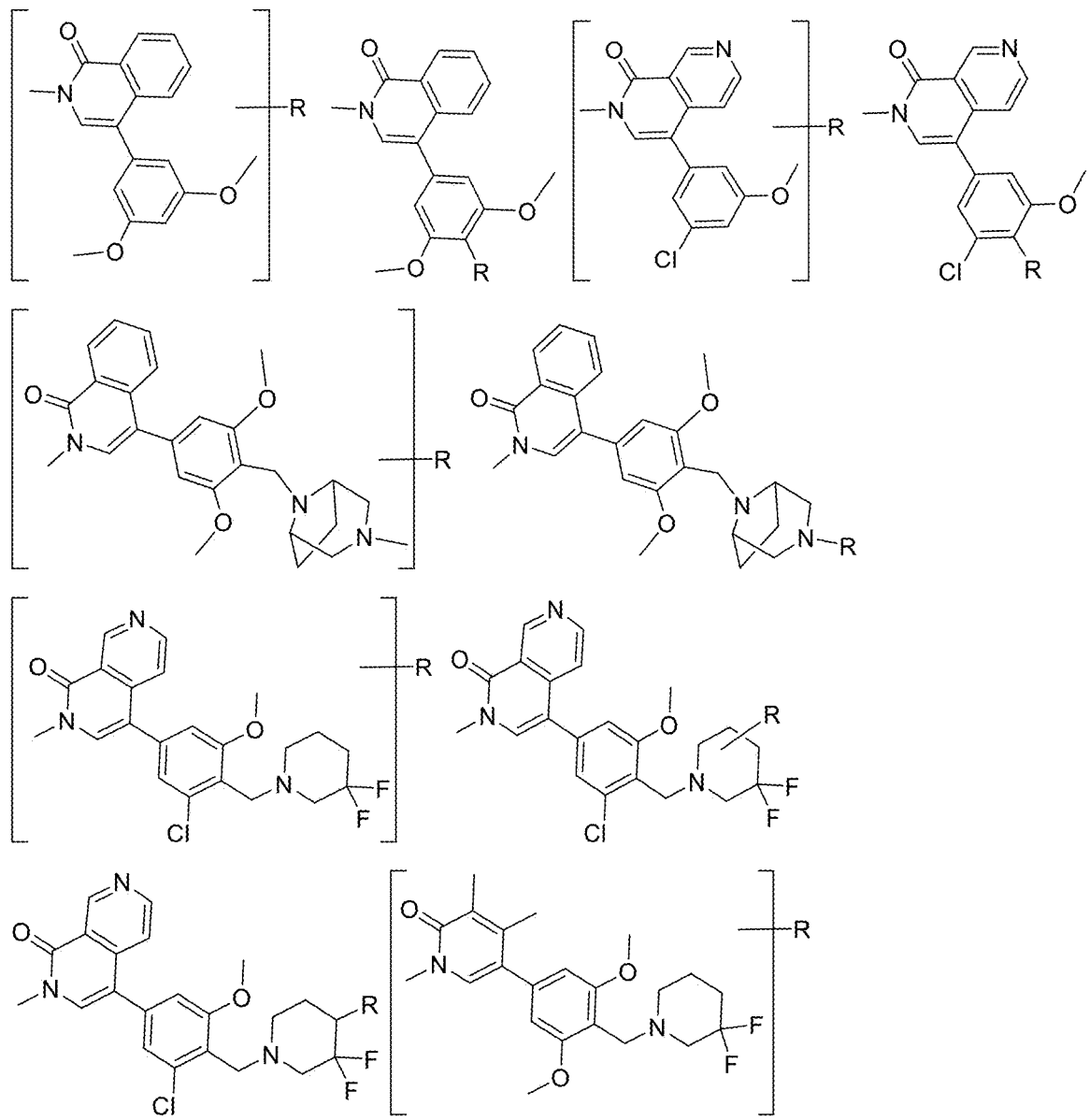
Figure 11B:
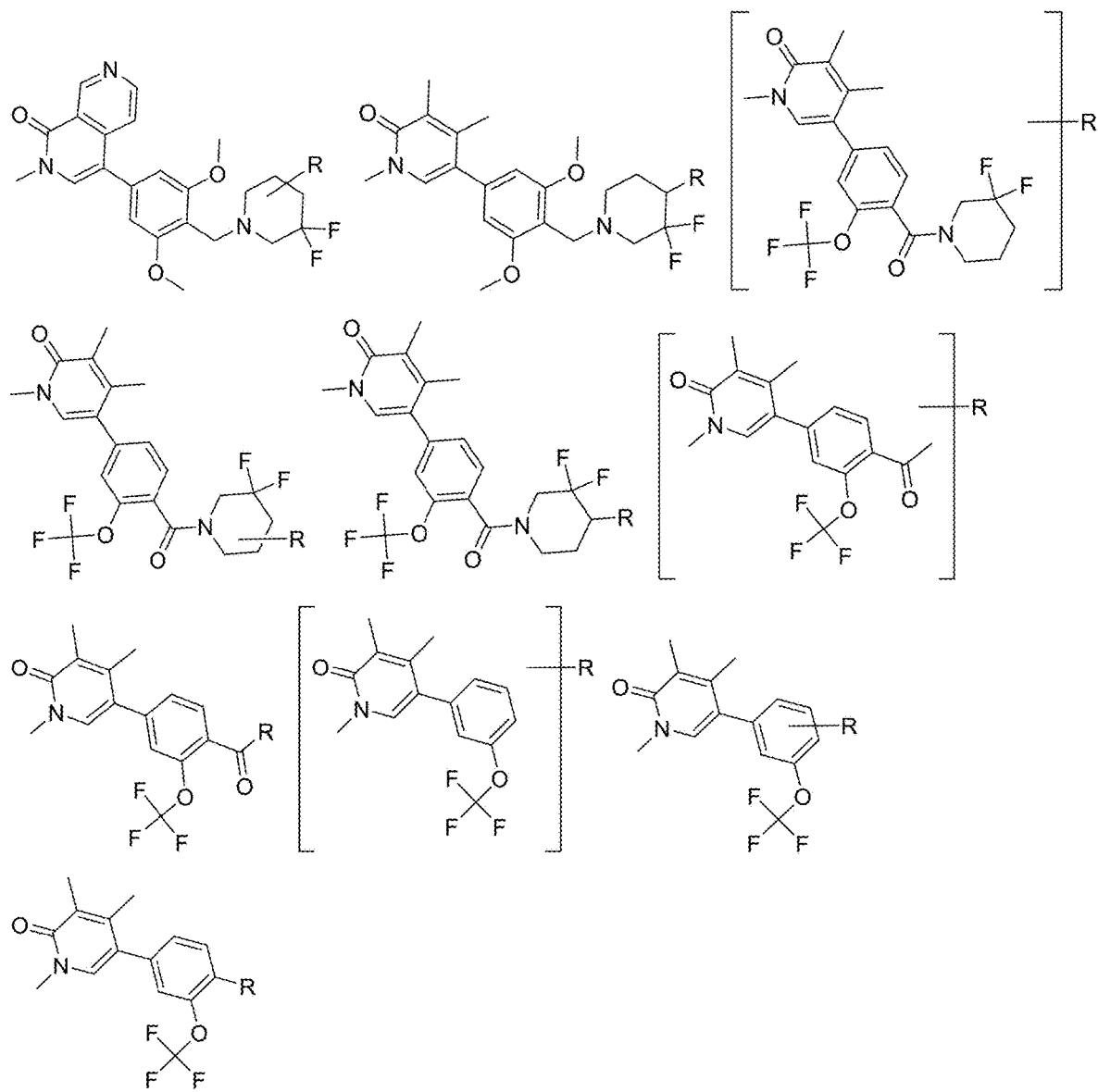

FIGS. 11A and 11B provide non-limiting examples of BRD9 Targeting Ligands wherein R is the point at which the Linker is attached. For additional examples see: "Structure-Based Design of an in Vivo Active Selective BRD9 Inhibitor" *J Med Chem* 2016, 59(10), 4462; WO2016139361.

Figure 12A:
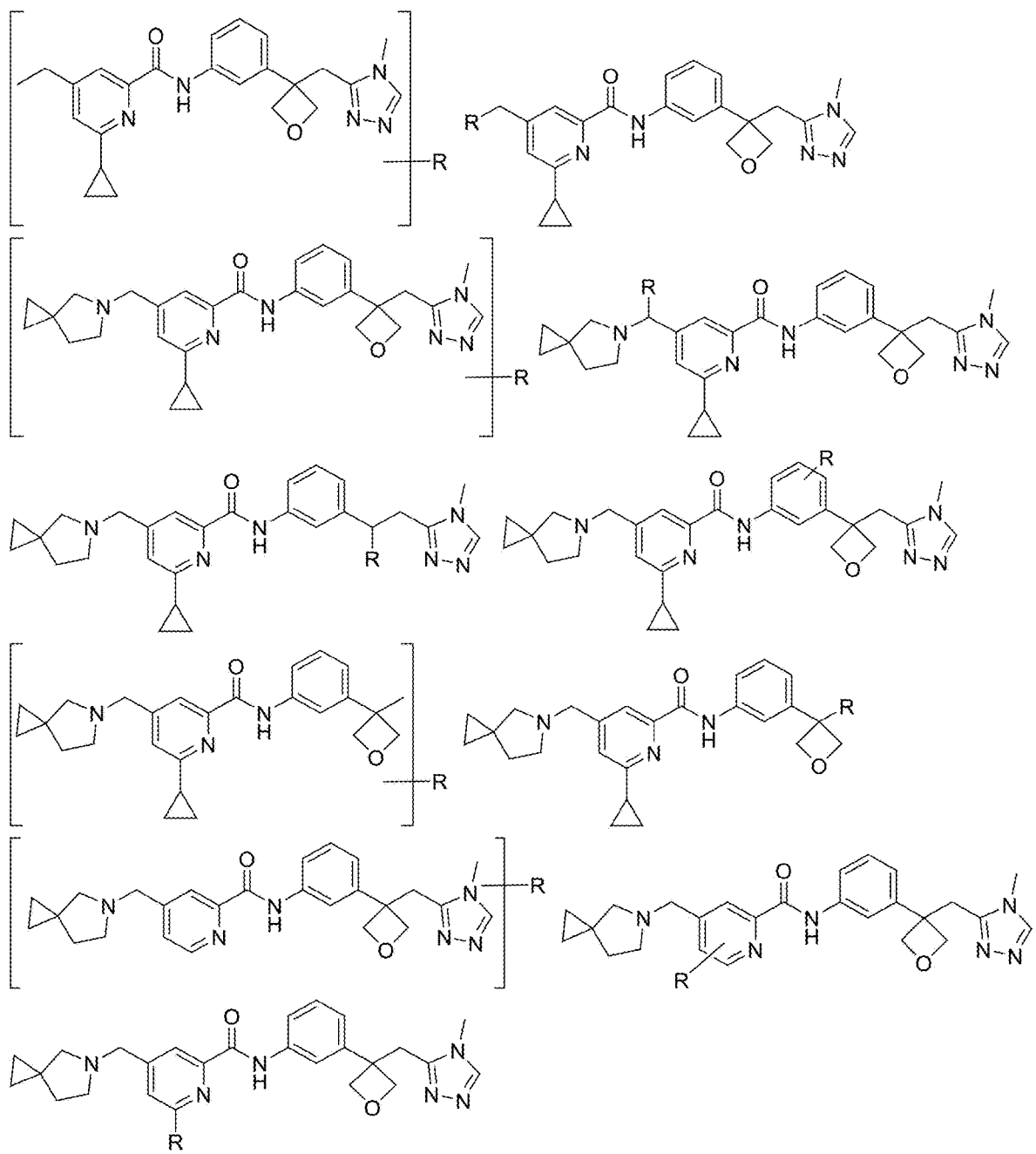
Figure 12B:
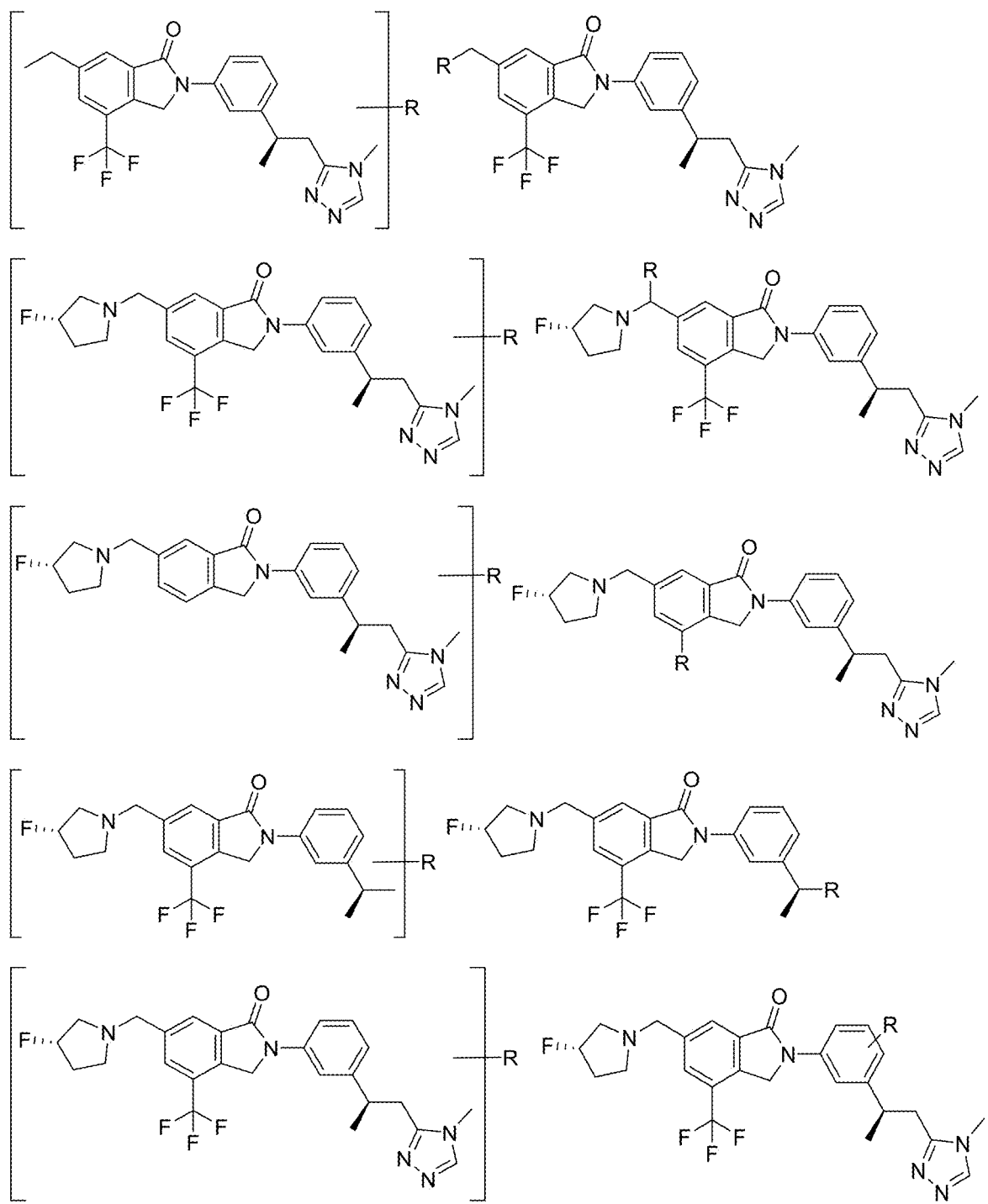
Figure 12C:
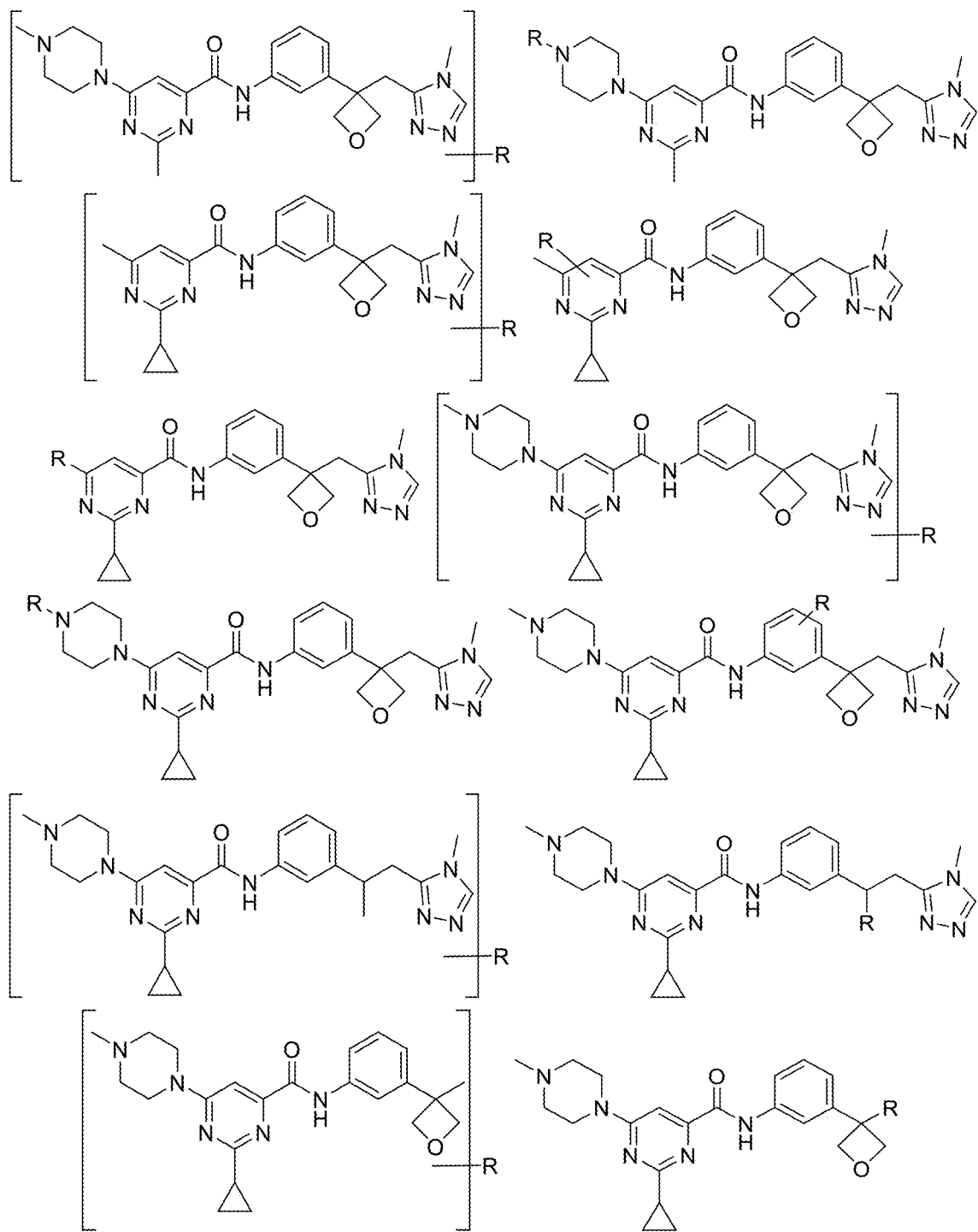

FIG. 12A-12C provide non-limiting examples of CBL-B Targeting Ligands, wherein R represents exemplary points at which the Linker can be attached. For additional examples, see WO201914800).

Figure 13:
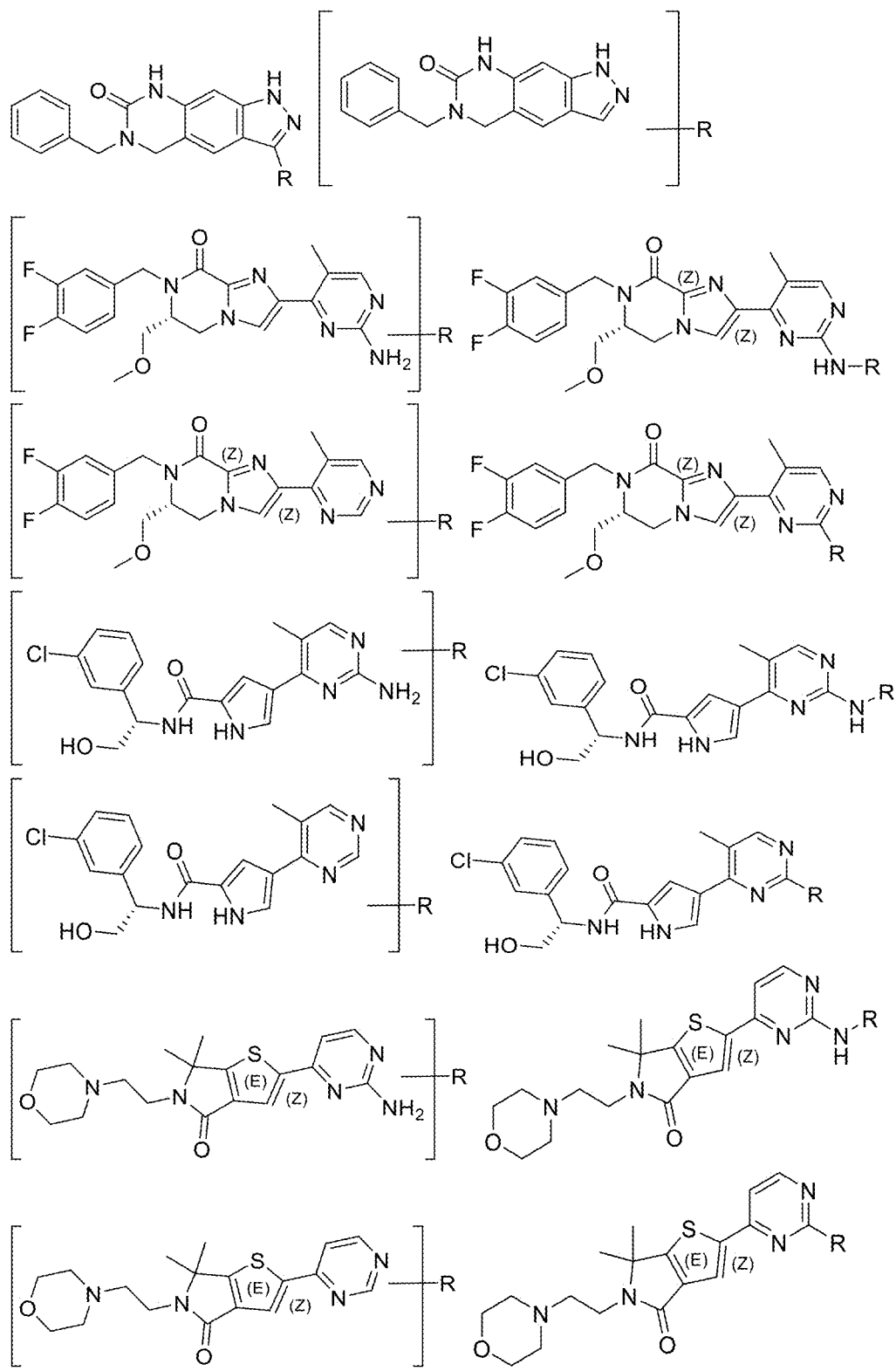

FIG. 13 provides non-limiting examples of ERK Targeting Ligands wherein R is the point at which the Linker is attached. For additional examples see: "*Structure-Guided Design of Potent and Selective Pyrimidylpyrrole Inhibitors of Extracellular Signal-Regulated Kinase (ERK) Using Conformational Control*" J Med Chem 2009, 52(20), 6362; WO2015051341; "*Discovery of a Potent and Selective Oral Inhibitor of ERK1 2 (AZD0364) That Is Efficacious in Both Monotherapy and Combination Therapy in Models of Nonsmall Cell Lung Cancer (NSCLC)*" J Med Chem 2019, 62(24), 11004; "*ERK Inhibitor LY3214996 Targets ERK Pathway-Driven Cancers: A Therapeutic Approach Toward Precision Medicine*" Mol Cancer Ther 2020, 19, 325.

Figure 14A:
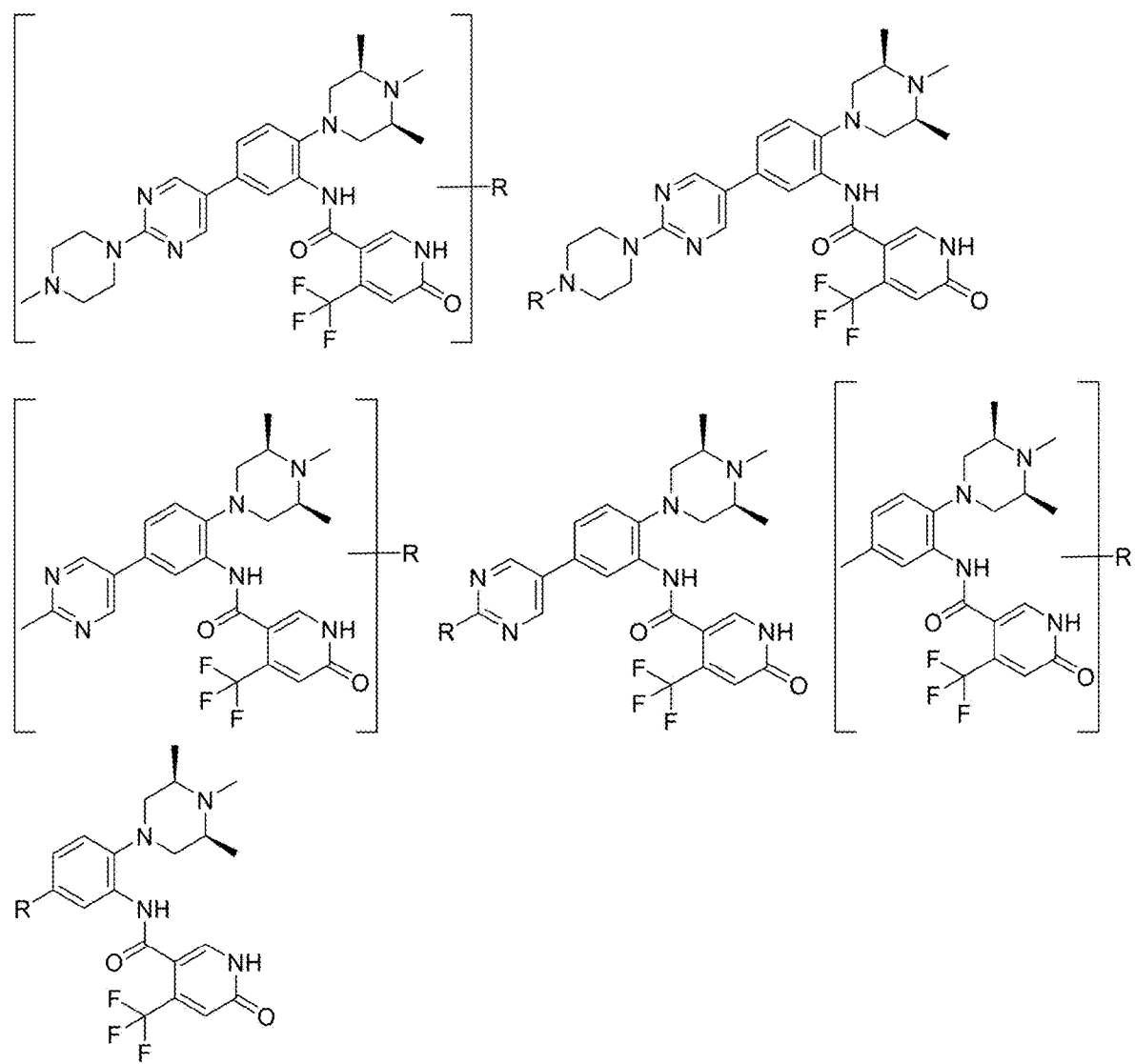
Figure 14B:
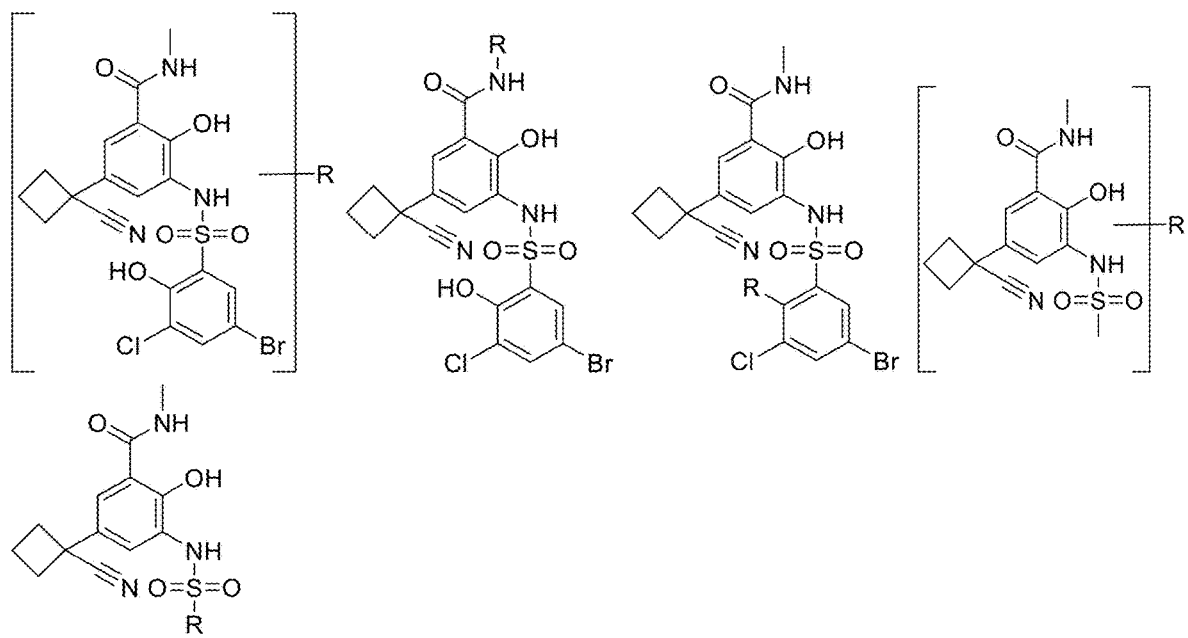
Figure 14C:
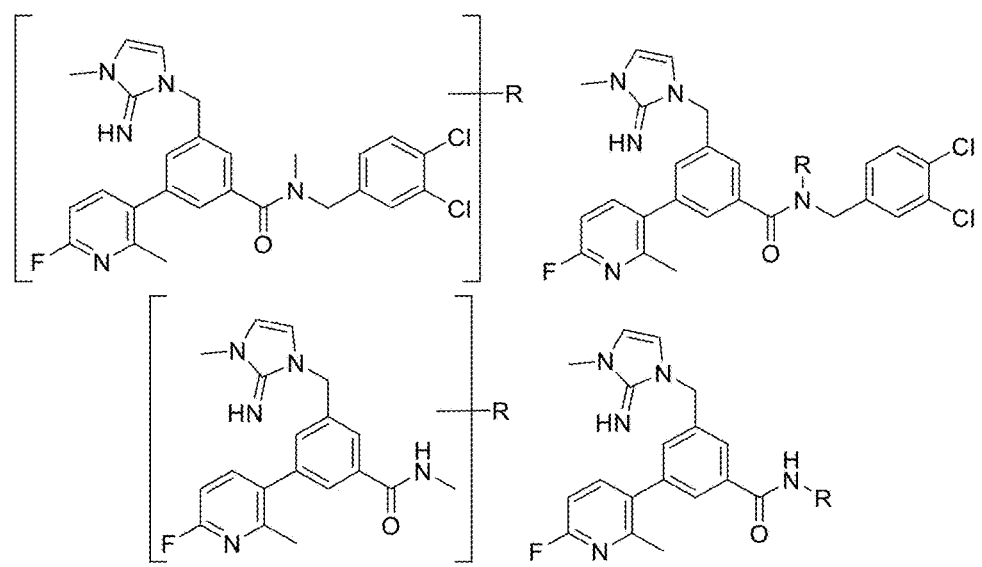

FIG. 14A-14C provide non-limiting examples of WDR5 Targeting Ligands, wherein R represents exemplary points at which the Linker can be attached. For additional examples see "Structure-Based Optimization of a Small Molecule Antagonist of the Interaction Between WD Repeat-Containing Protein 5 (WDR5) and Mixed-Lineage Leukemia 1 (MLL1)" J Med Chem 2016, 59(6), 2478; WO2017147700; "Displacement of WDR5 from Chromatin by a WIN Site Inhibitor with Picomolar Affinity" Cell Rep 2019, 26(11), 2916; "Discovery and Optimization of Salicylic Acid-Derived Sulfonamide Inhibitors of the WD Repeat-Containing Protein 5-MYC Protein-Protein Interaction" J Med Chem 2019, 62(24), 11232).

Figure 15:
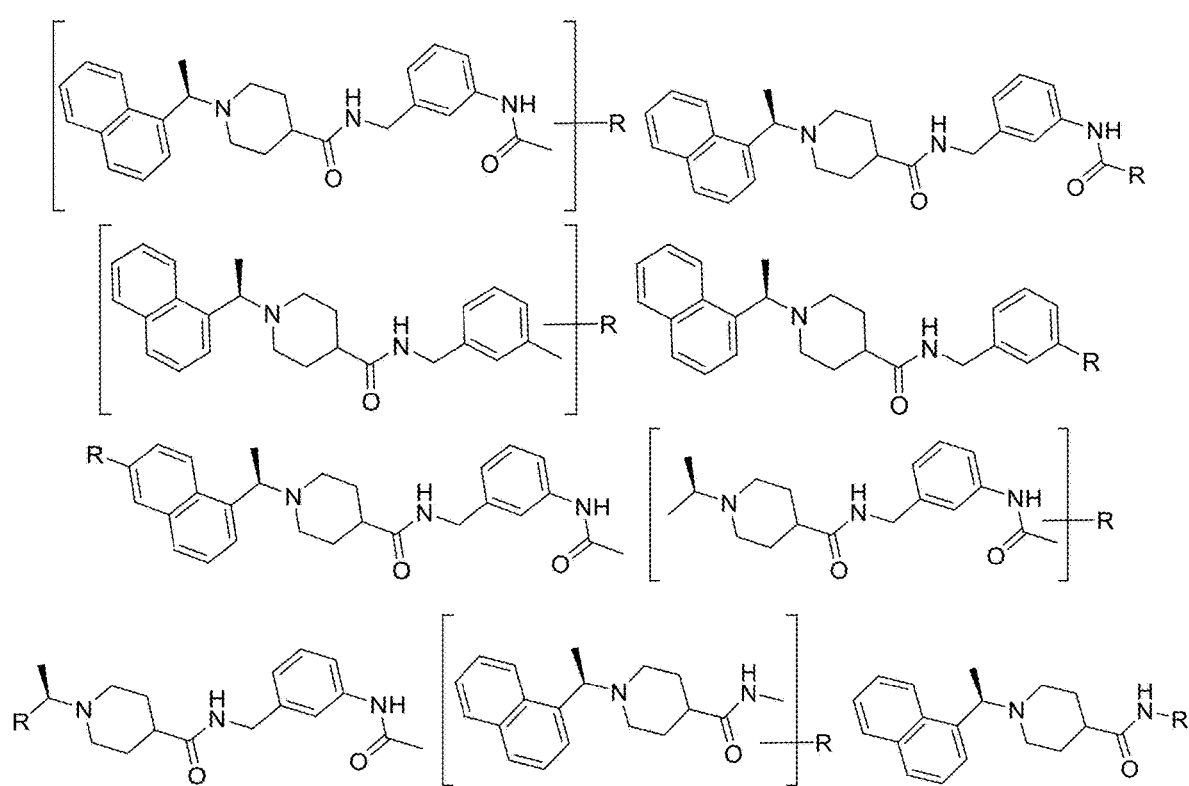

FIG. 15 provides non-limiting examples of NSP3 Targeting Ligands, wherein R represents exemplary points at which the Linker can be attached. For additional examples see: "Severe Acute Respiratory Syndrome Coronavirus Papain-like Novel Protease Inhibitors: Design, Synthesis, Protein-Ligand X-ray Structure and Biological Evaluation", J Med Chem 2010, 53, 4968; "X-ray Structural and Biological Evaluation of a Series of Potent and Highly Selective Inhibitors of Human Coronavirus Papain-like Proteases", J Med Chem 2014, 57, 2393).

Figure 16:
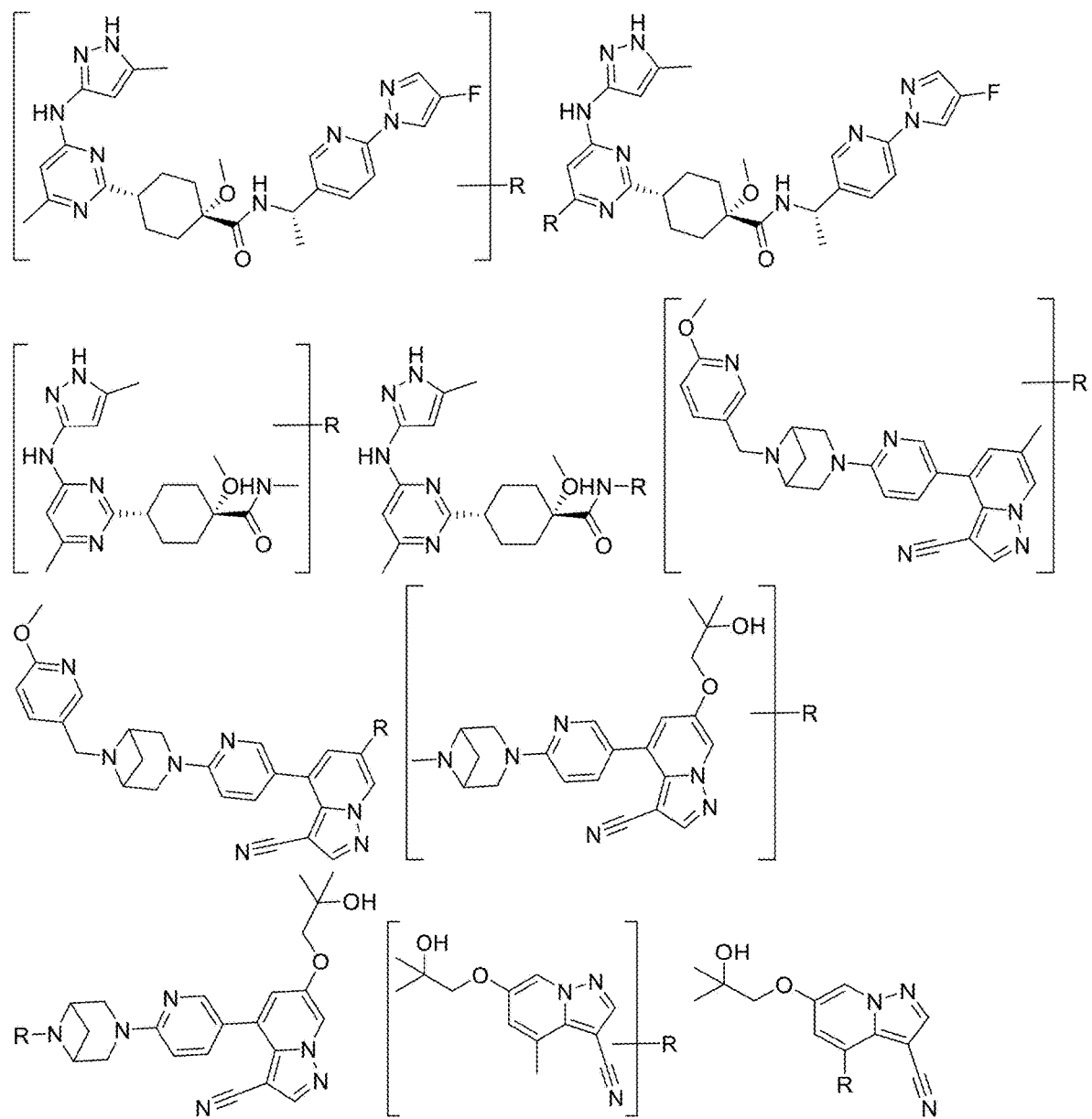

FIG. 16 provides non-limiting examples of RET Targeting Ligands, wherein R represents exemplary points at which the Linker can be attached. For additional examples see: Pralsetinib "Precision Targeted Therapy with BLU-667 for RET-Driven Cancers" Cancer Discovery, 2018, 8(7), 836; Selpercatinib, WO2018071447; "A Pyrazolo[3,4-d]pyrimidin-4-amine Derivative Containing an Isoxazole Moiety Is a Selective and Potent Inhibitor of RET Gatekeeper Mutants" J Med Chem, 2016, 59, 358).

Figure 17A:
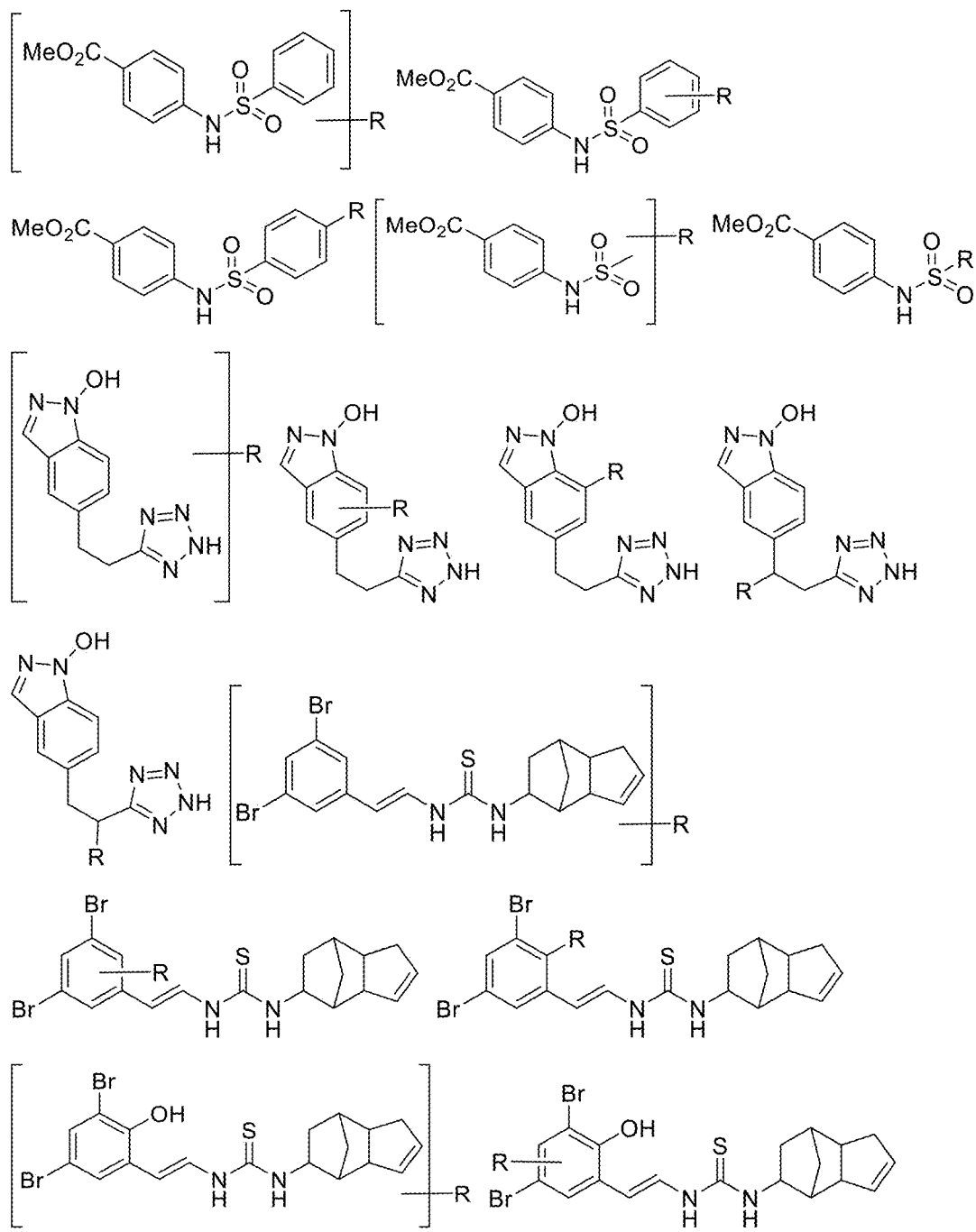
Figure 17B:
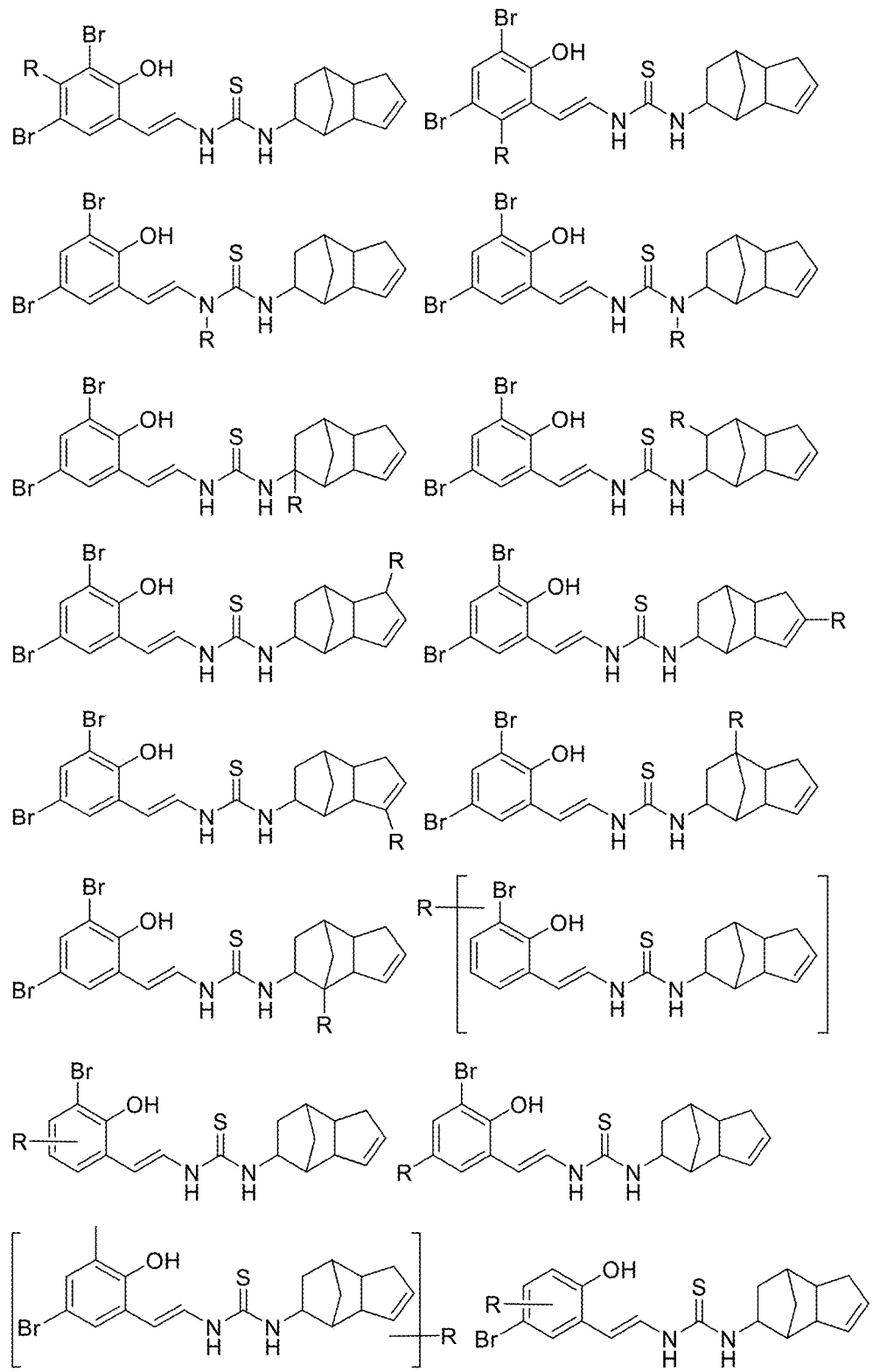
Figure 17C:
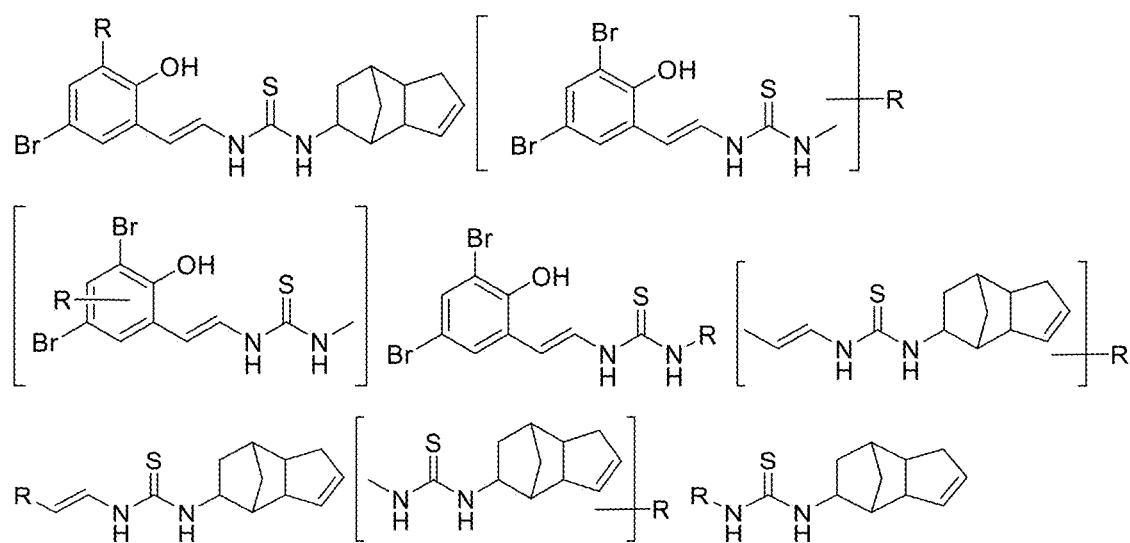

FIG. 17A-17C provide non-limiting examples of CTNNB1 Targeting Ligands wherein R is the point at which the Linker is attached. For additional examples see: "Direct Targeting of b-Catenin by a Small Molecule Stimulates Proteasomal Degradation and Suppresses Oncogenic Wnt/b-Catenin Signaling" CellRep 2016, 16(1), 28 "Rational Design of Small-Molecule Inhibitors for O-Catenin/T-Cell Factor Protein-Protein Interactions by Bioisostere Replacement" *ACS Chem Biol* 2013, 8, 524, and "Allosteric inhibitor of 0-catenin selectively targets oncogenic Wnt signaling in colon cancer" *Sci Rep* 2020, 10, 8096.

Figure 18A:
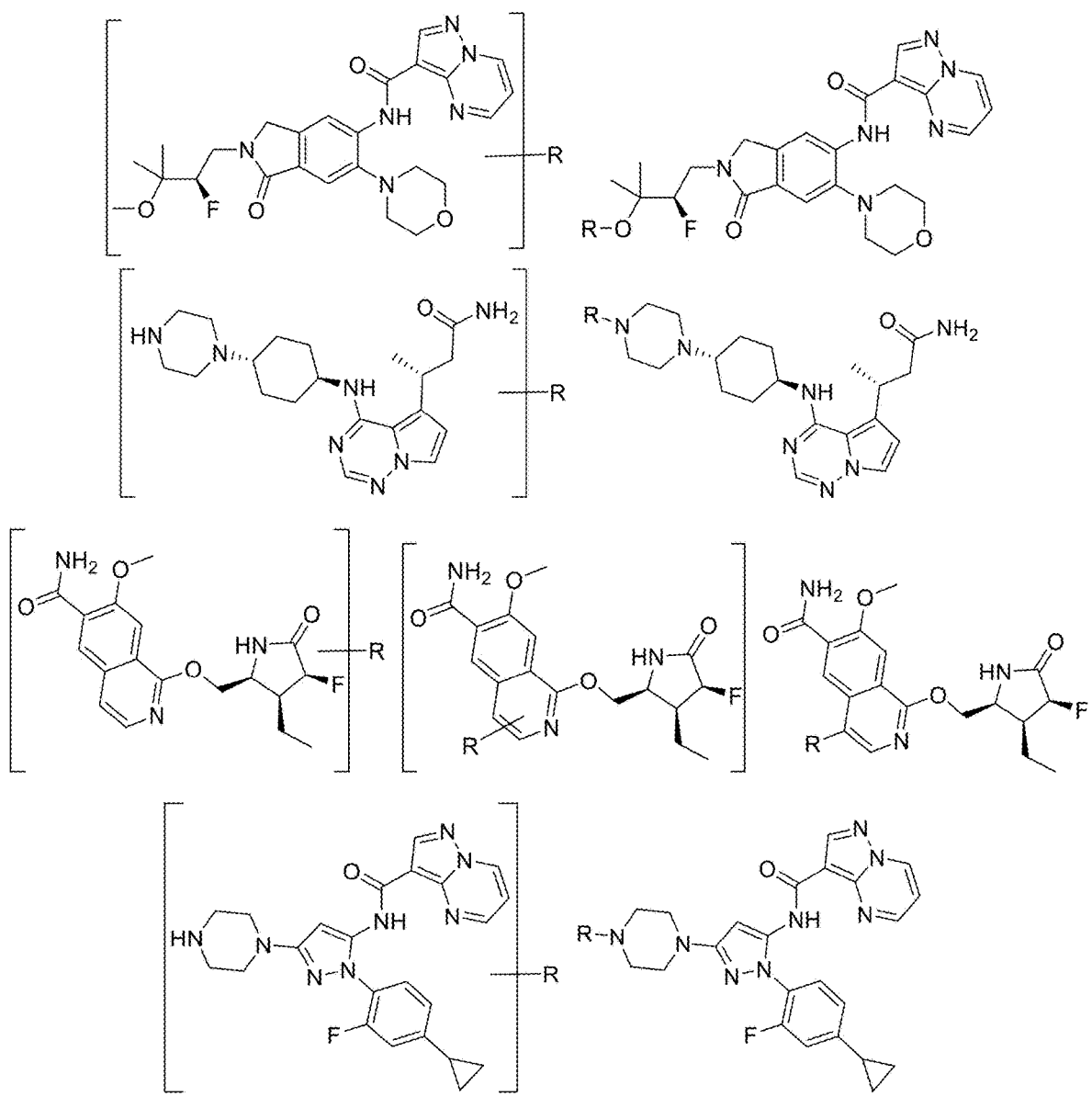
Figure 18B:
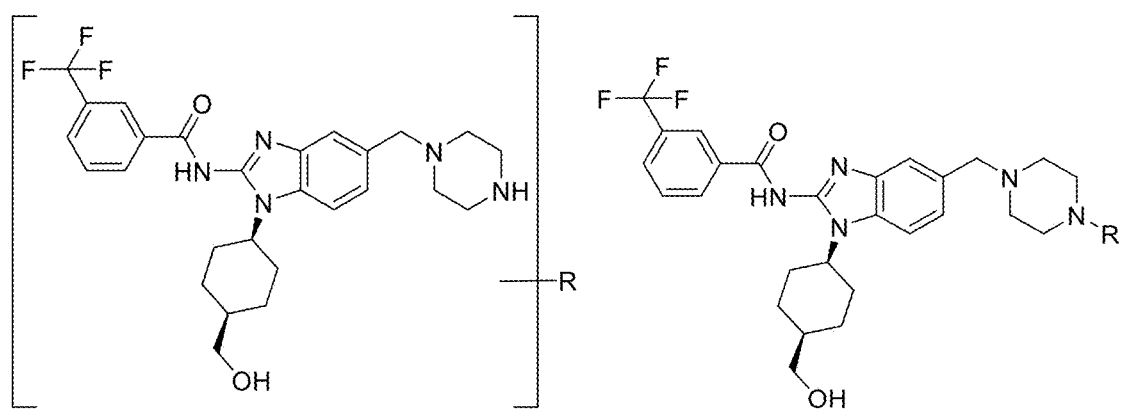
Figure 18C:
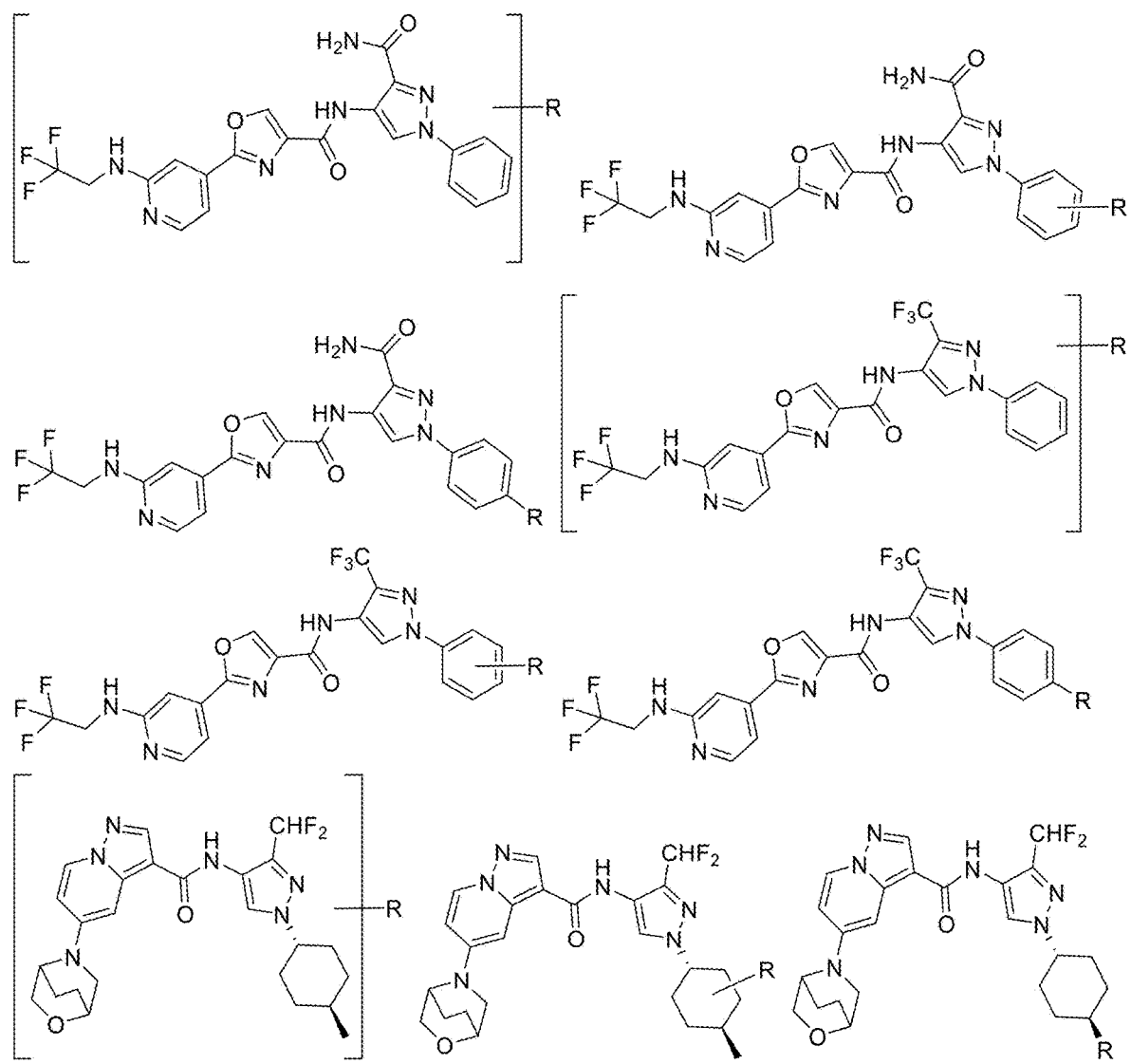
Figure 19A:
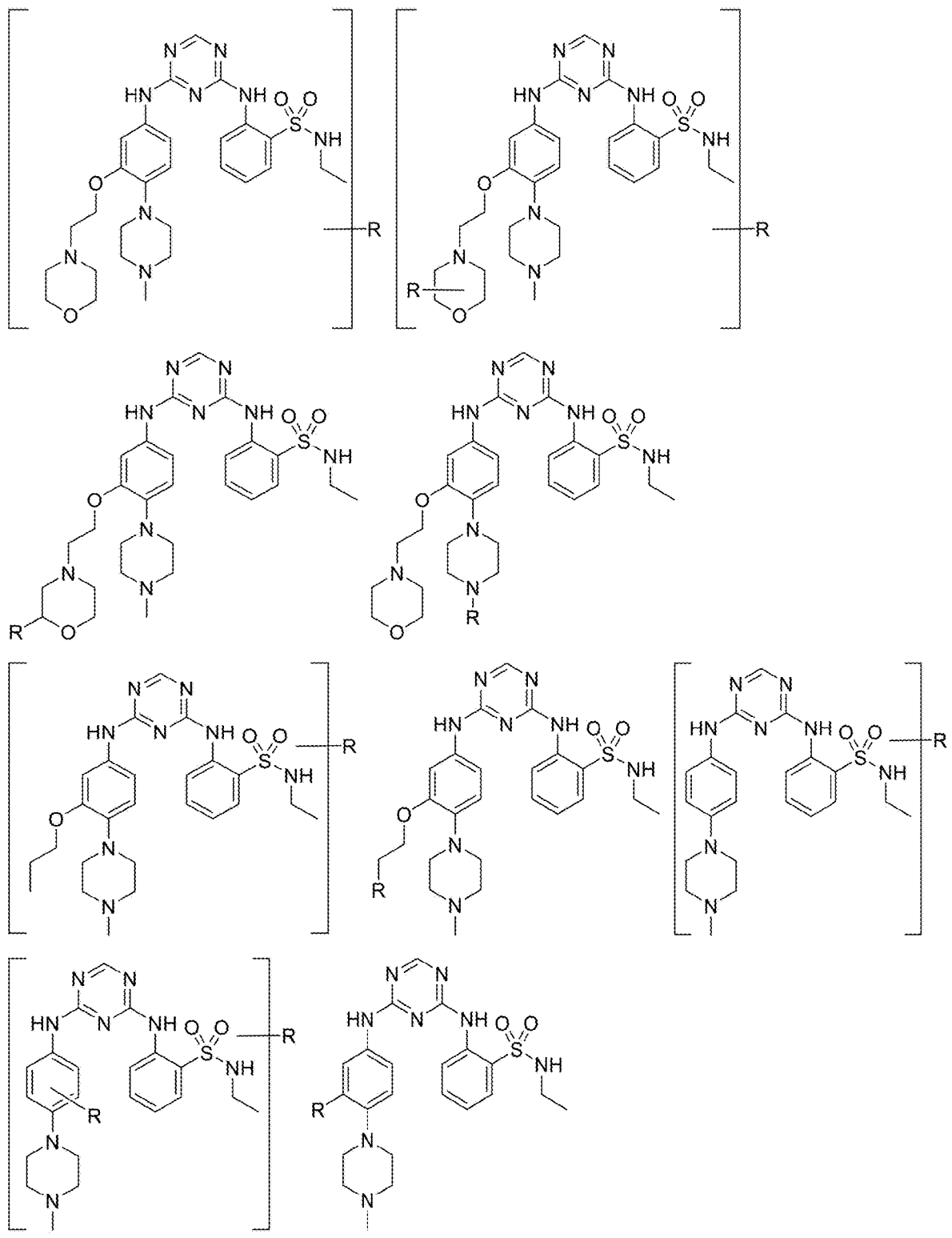
Figure 19B:
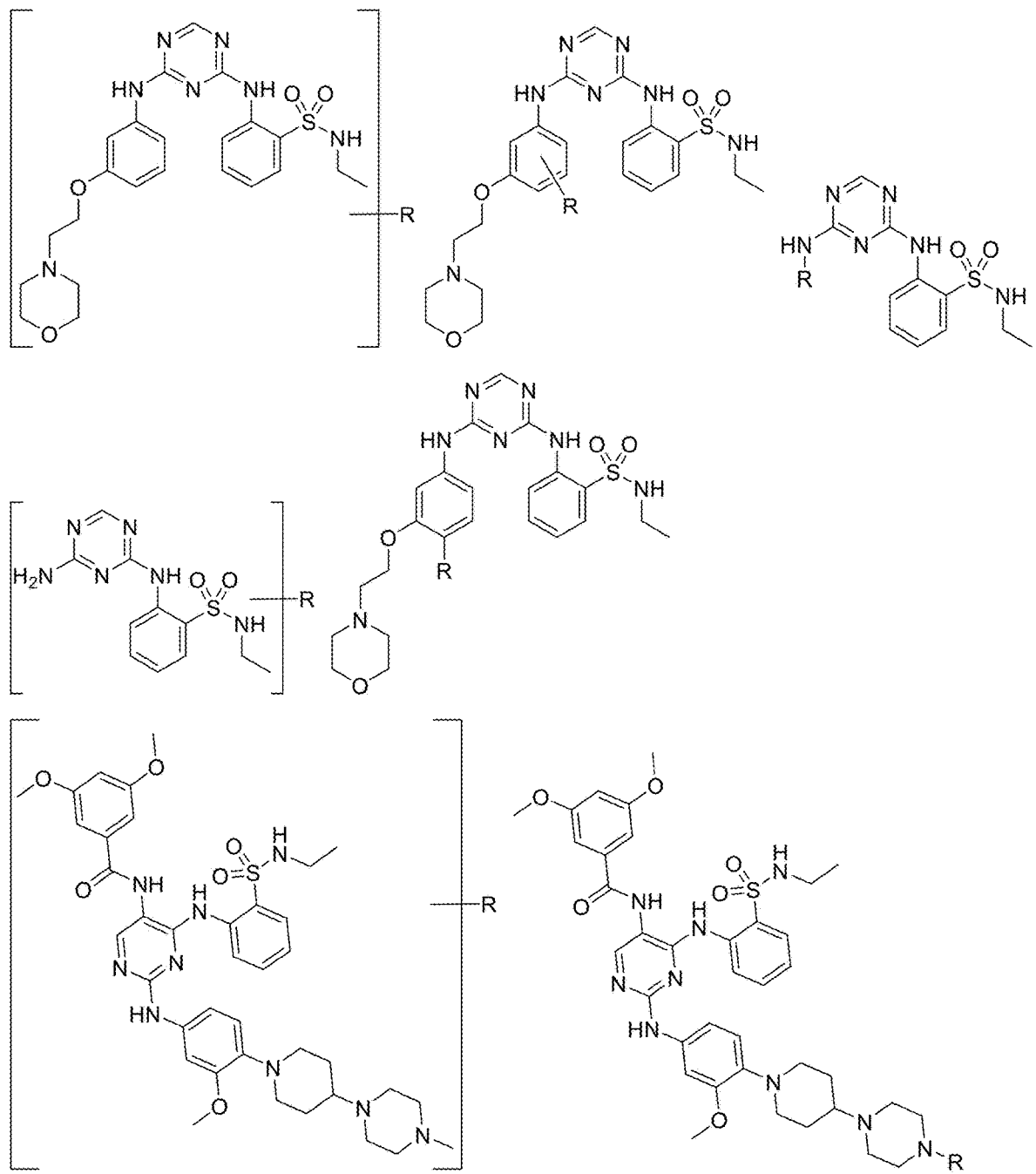
Figure 19C:
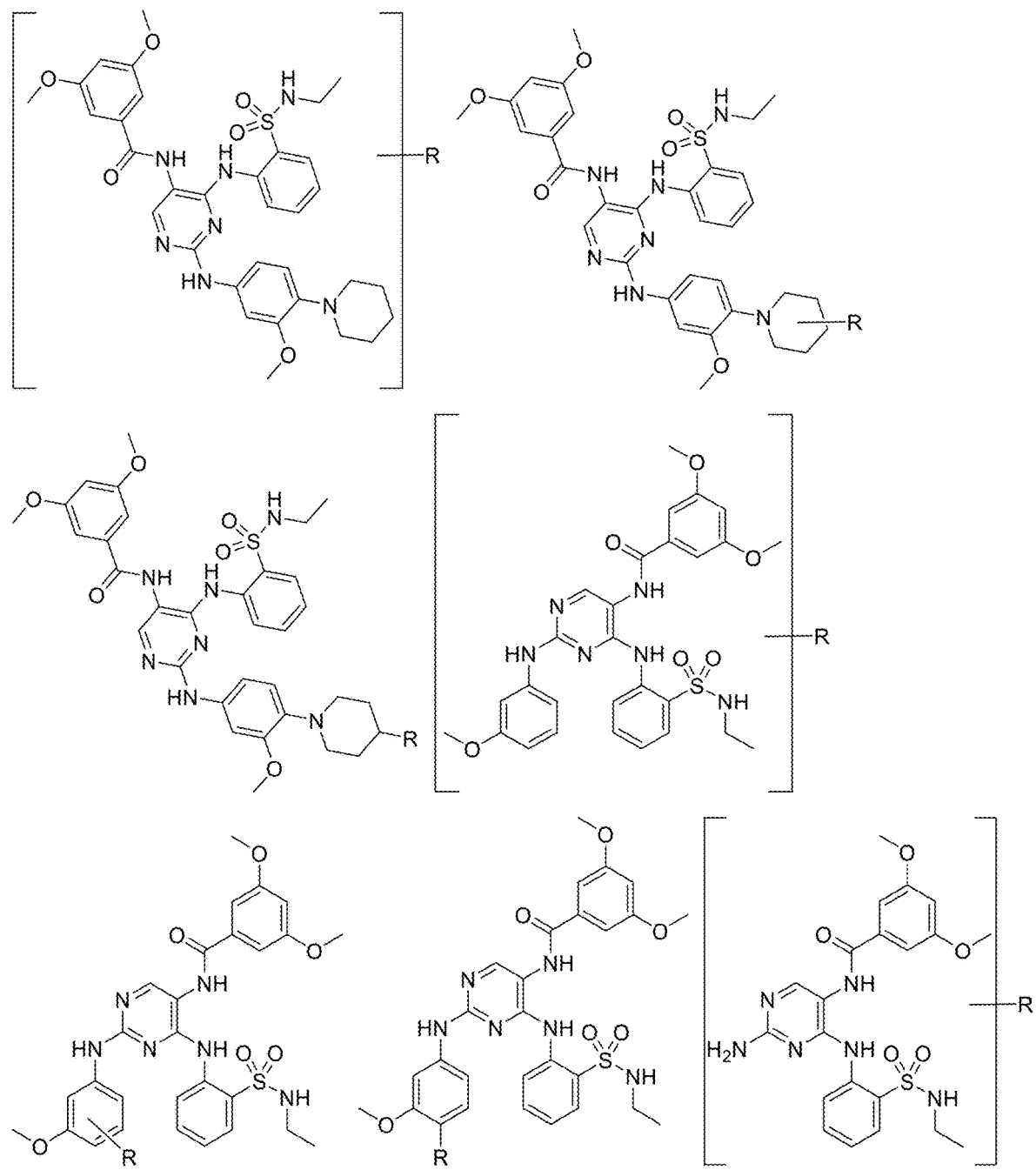
Figure 19D:
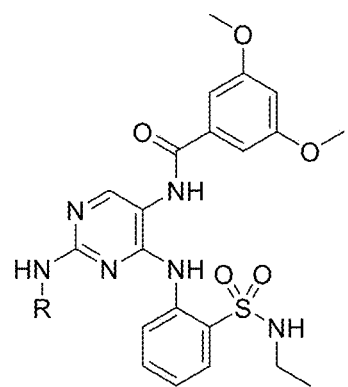
Figure 20A:
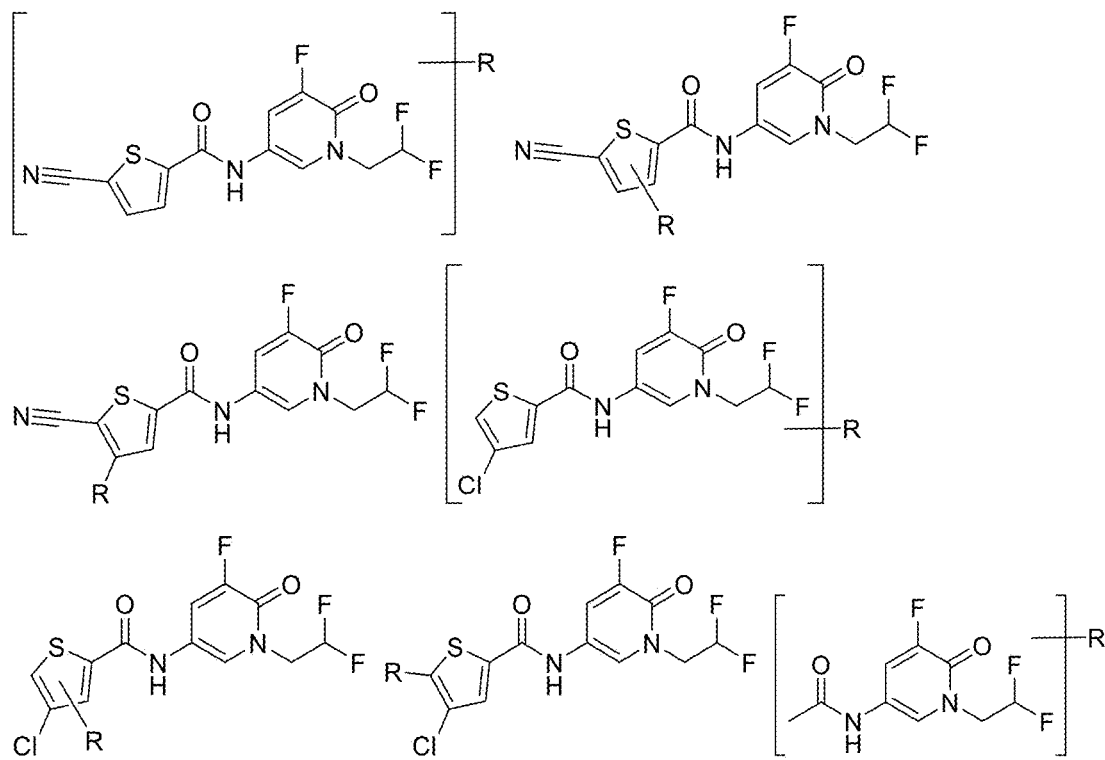
Figure 20B:
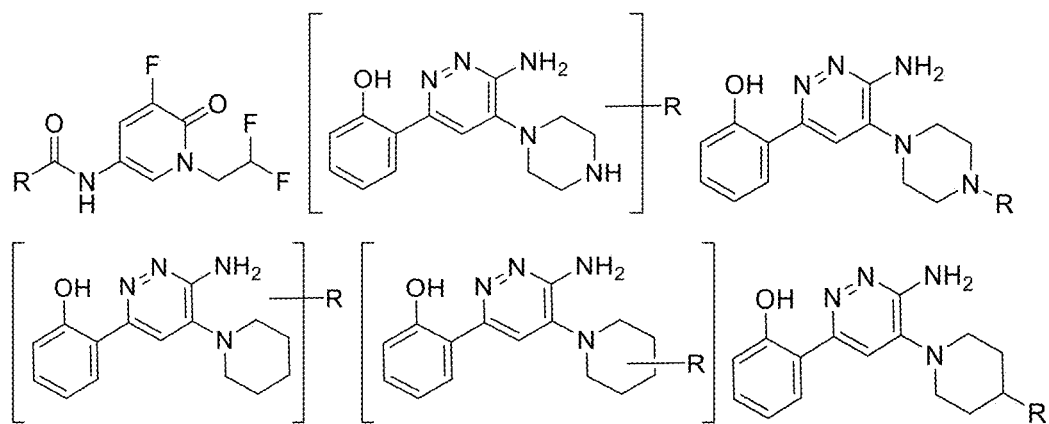
Figure 20C:
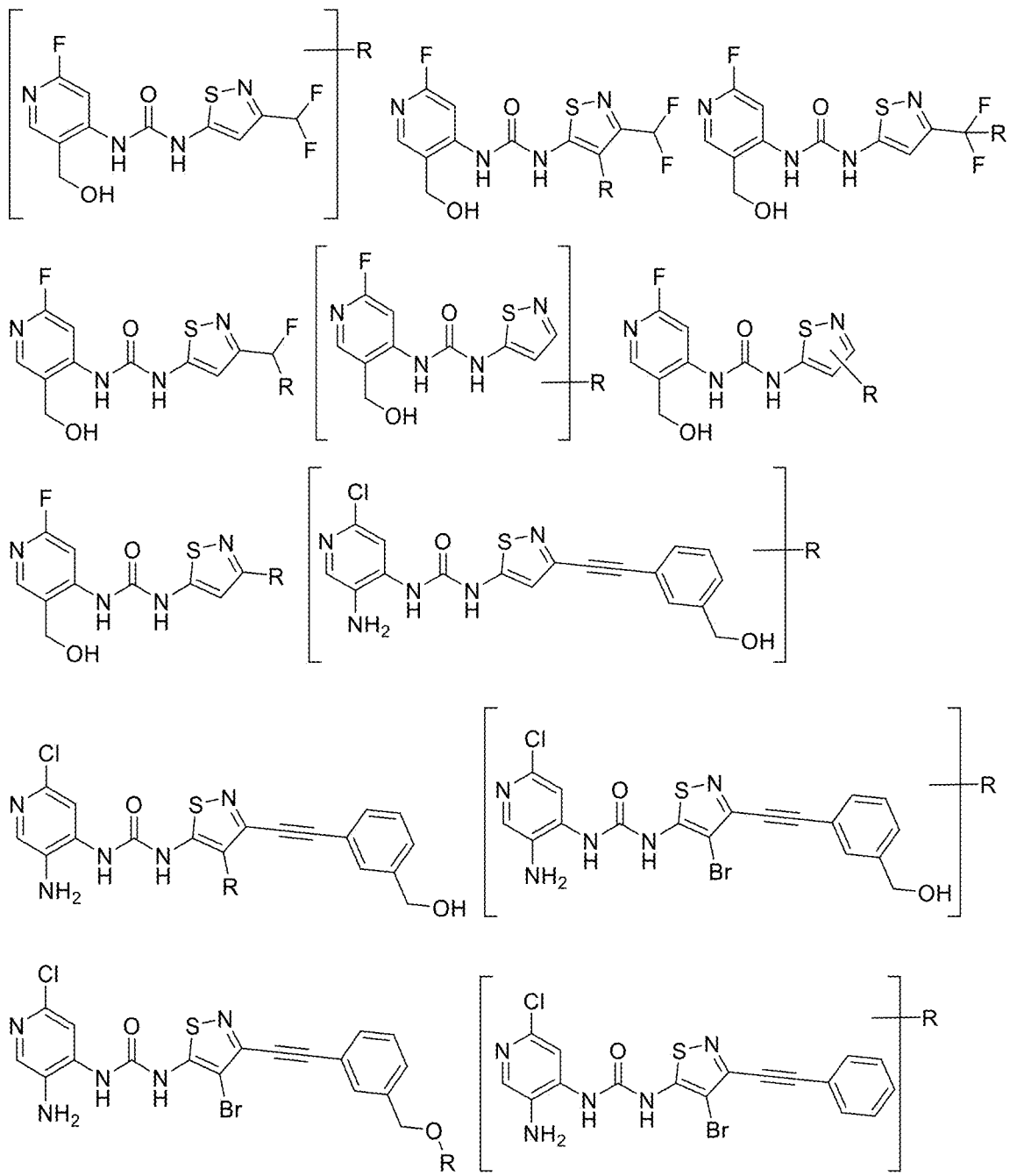
Figure 20D:
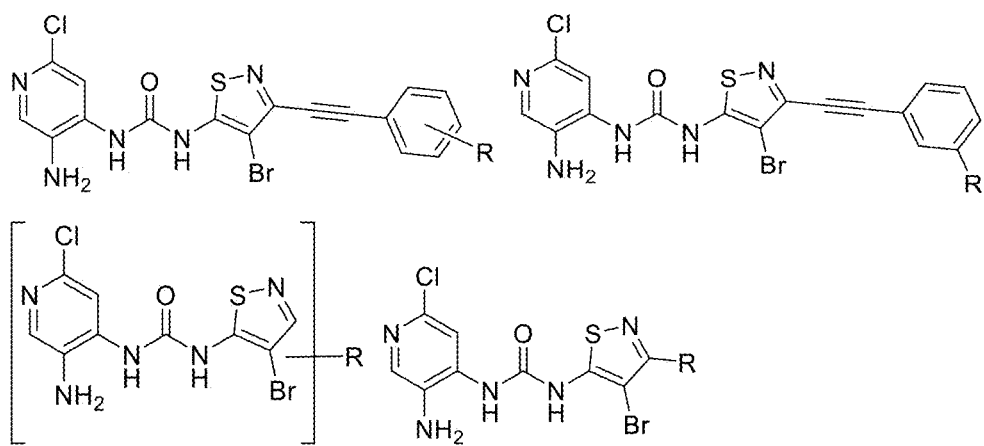
Figure 21A:
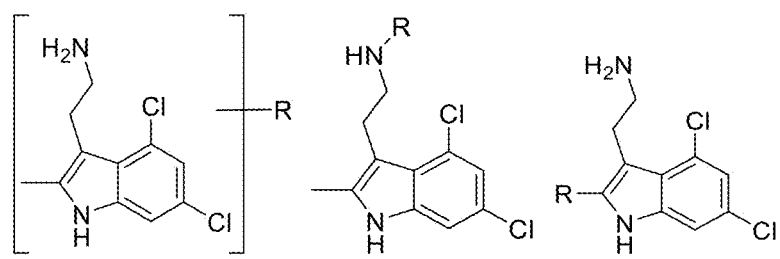
Figure 21B:
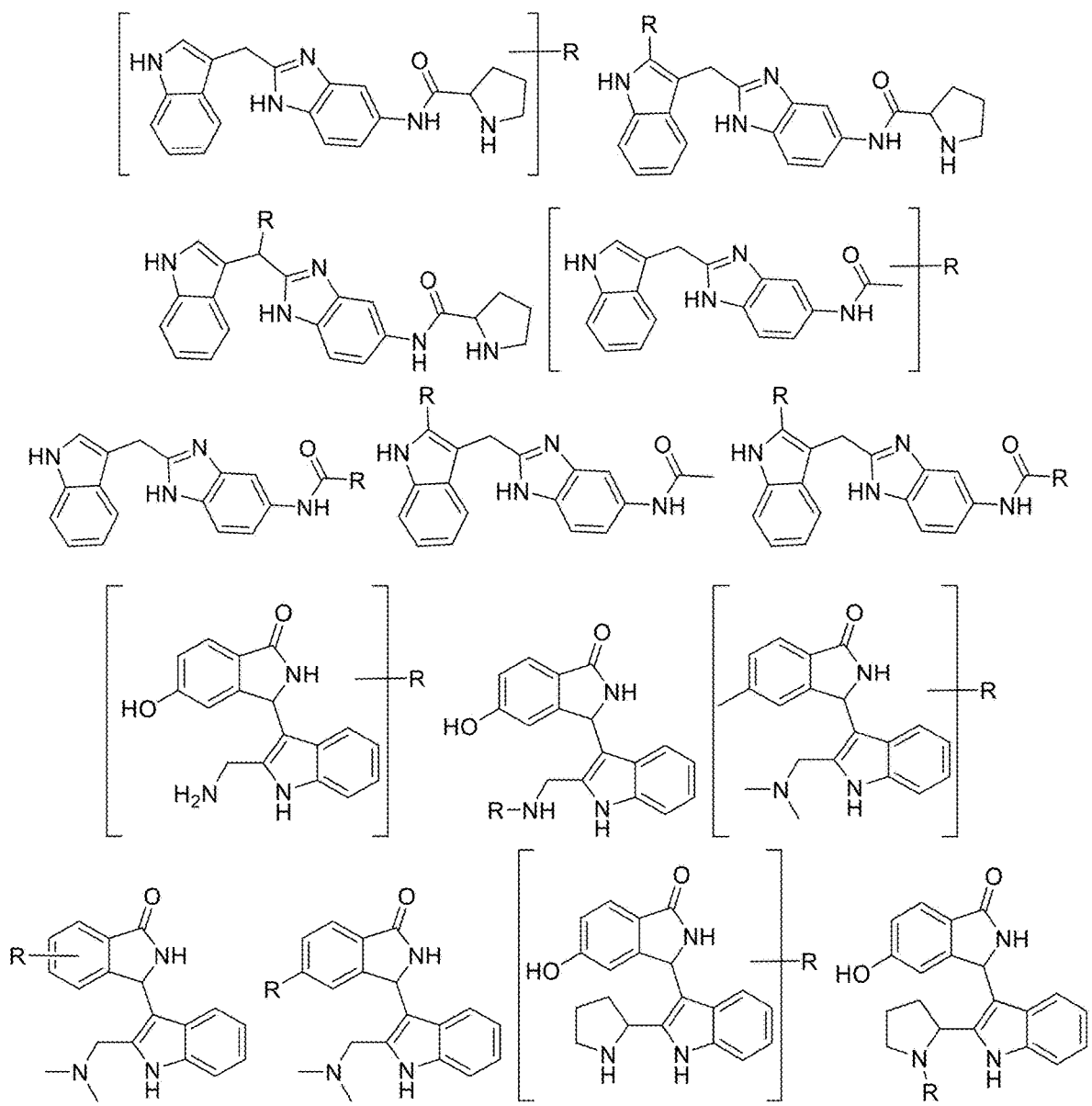
Figure 21C:
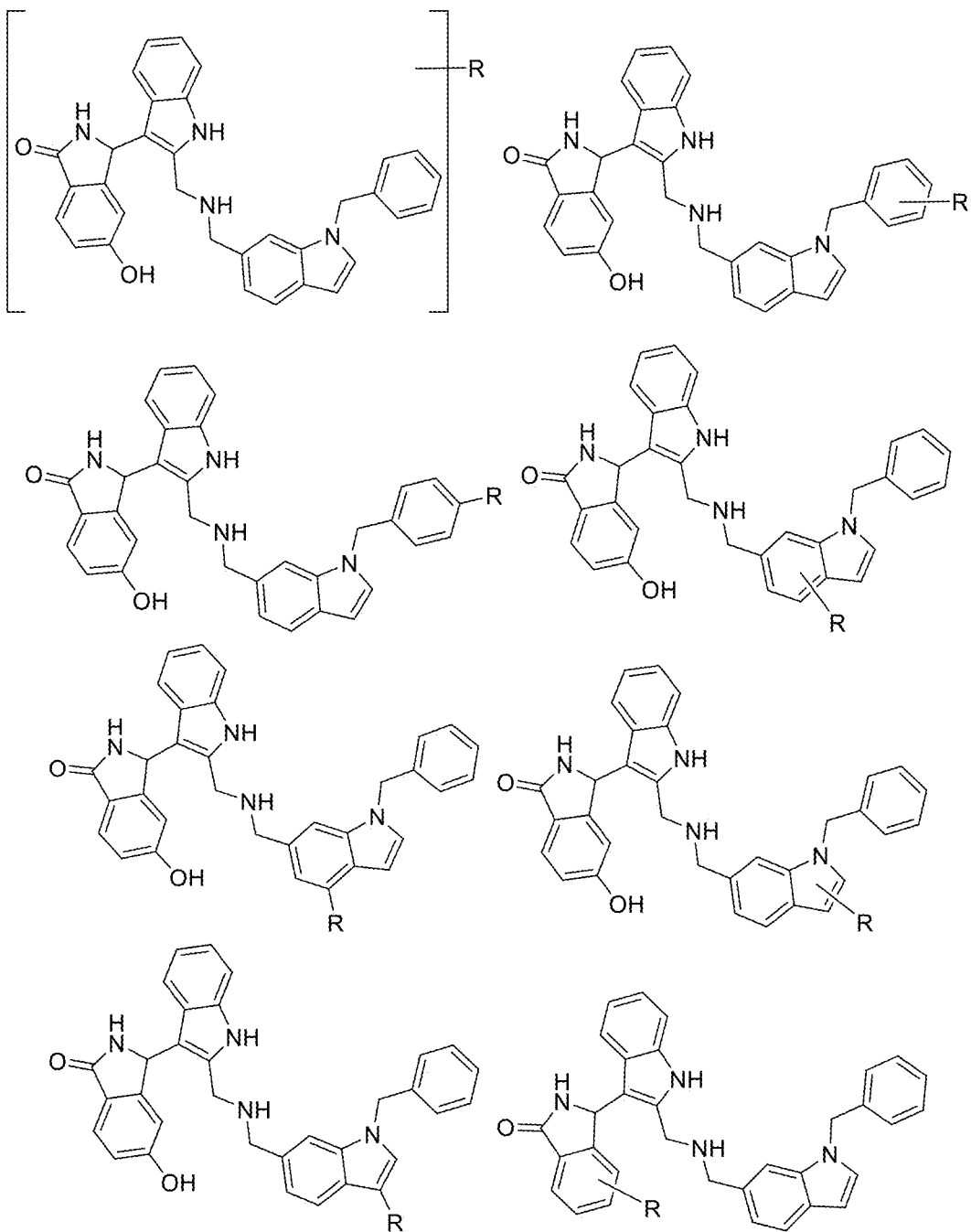
Figure 21D:
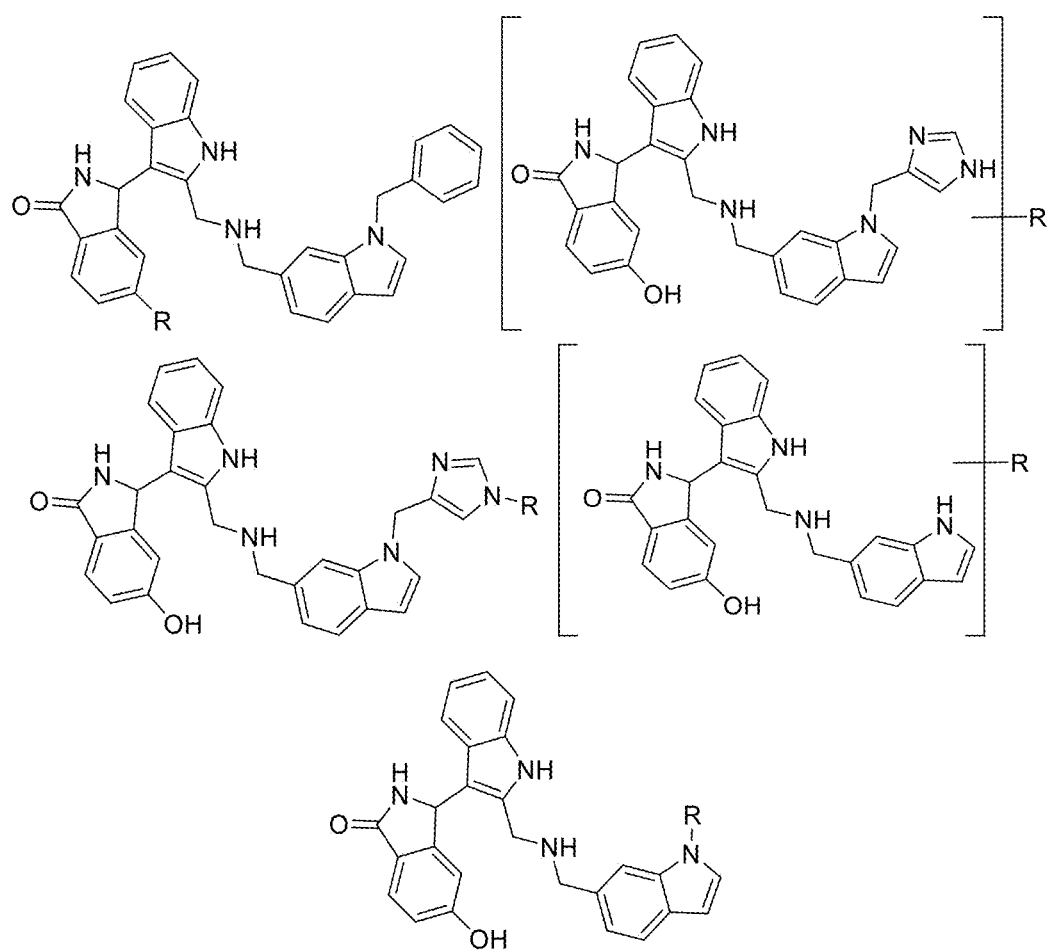
Figure 21E:
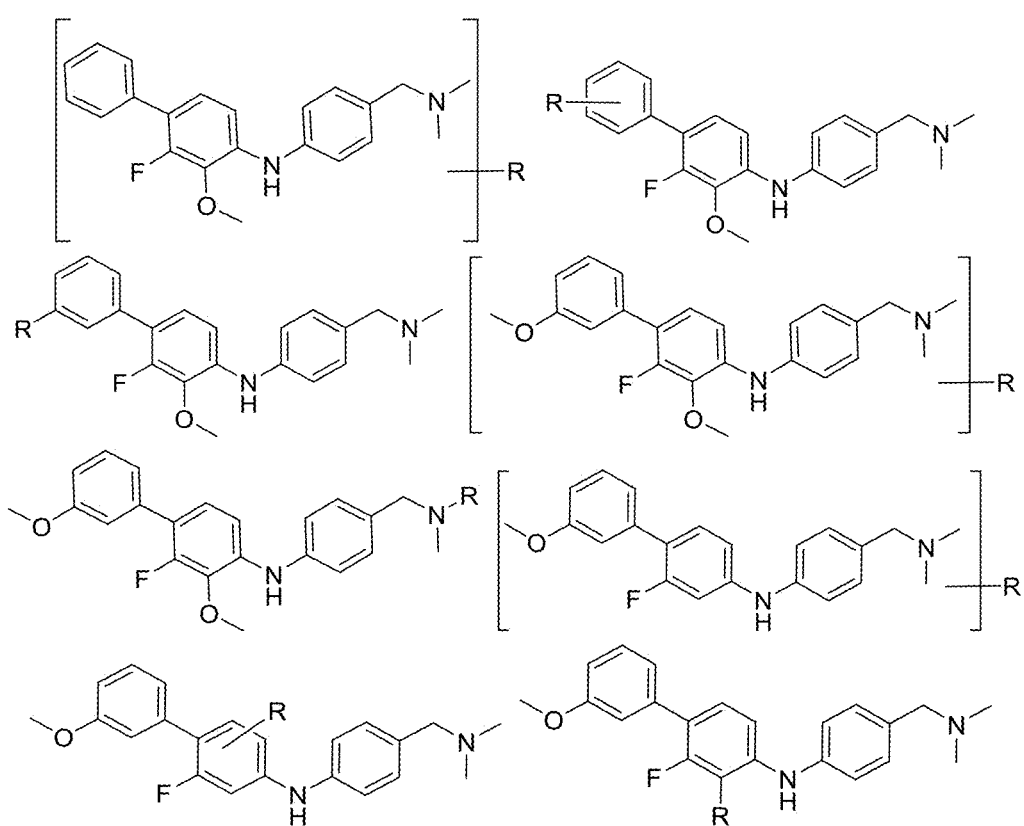
Figure 21F:
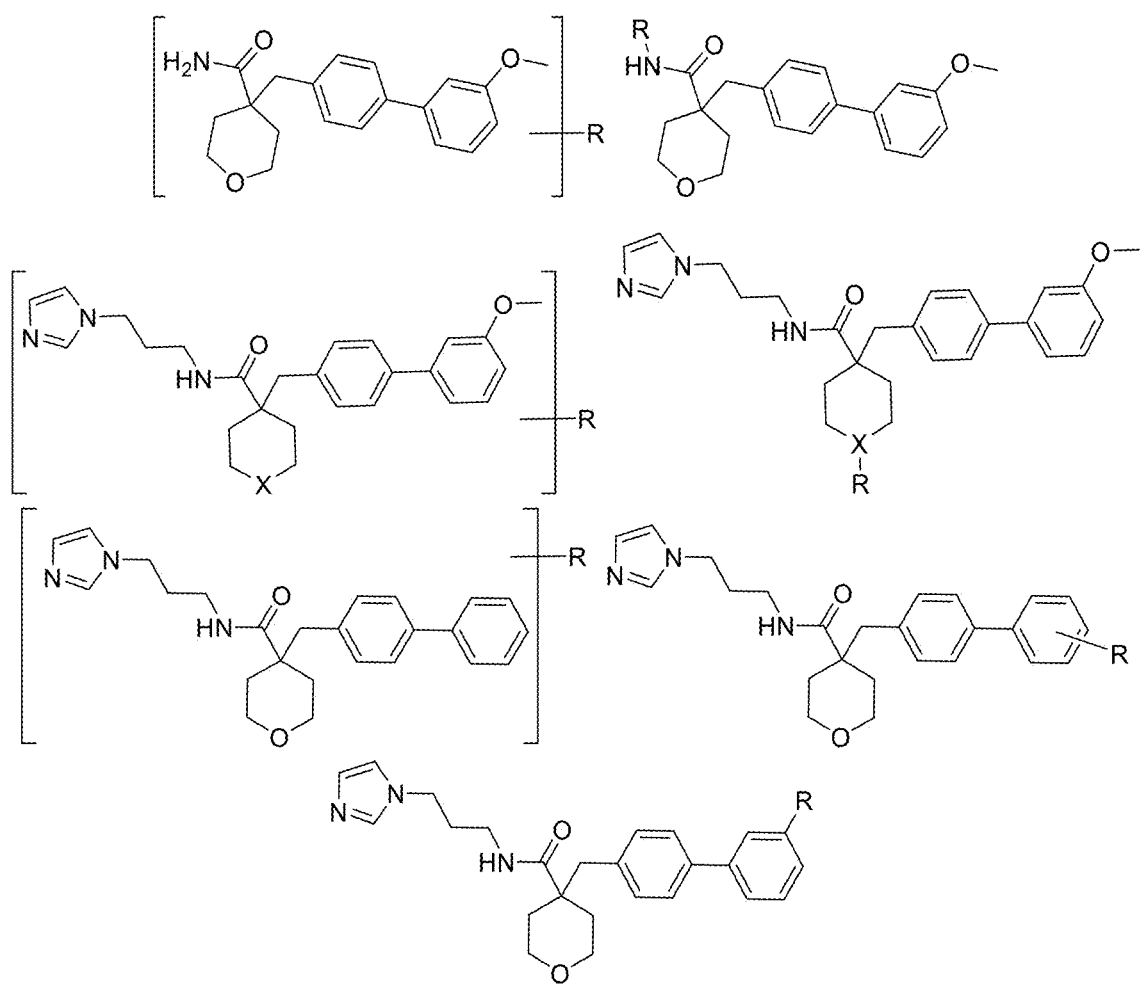
Figure 21G:
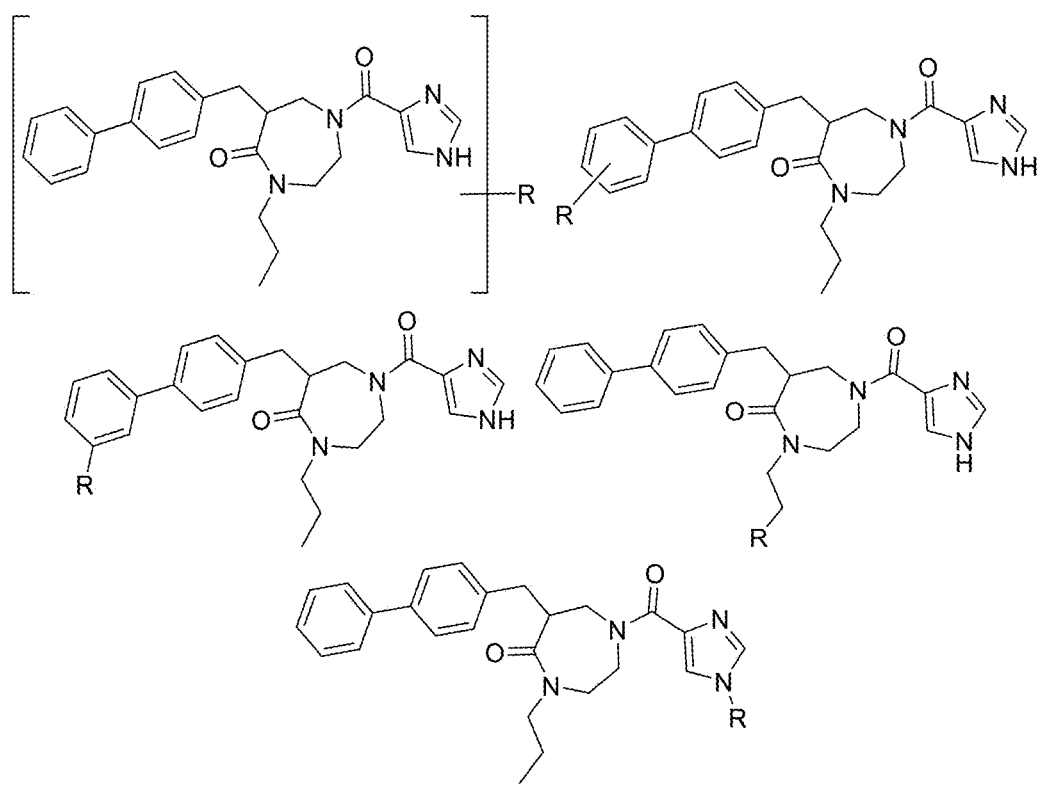
Figure 21H:
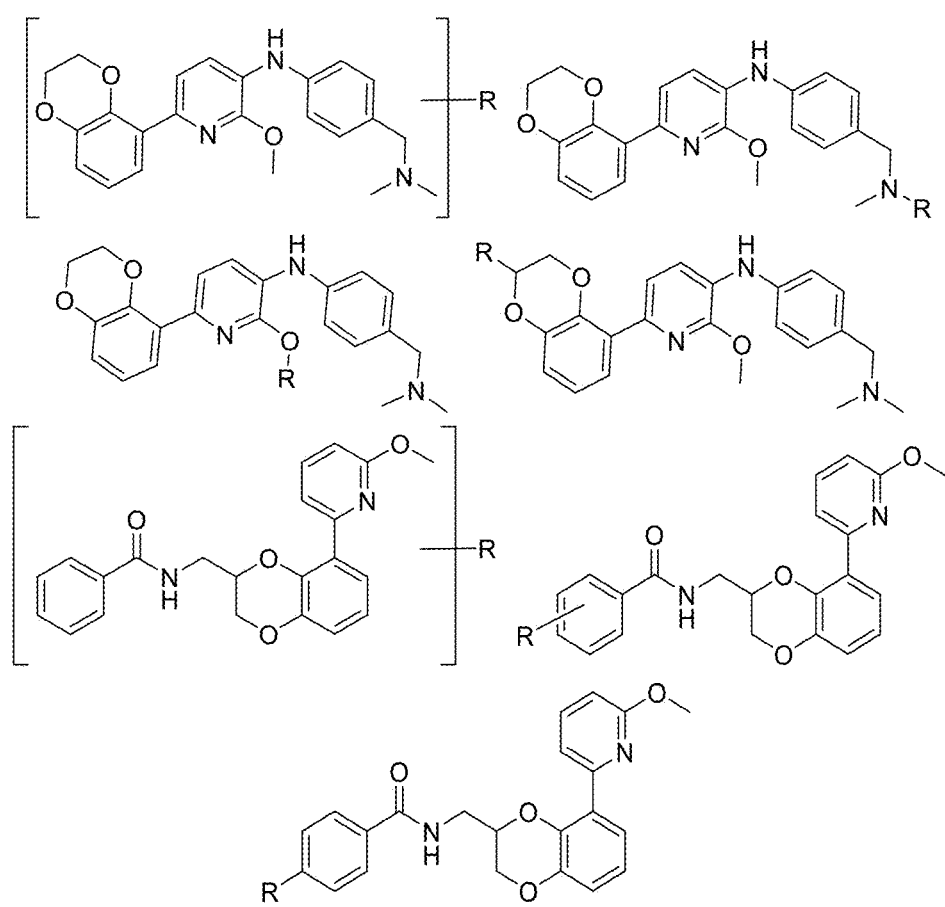
Figure 21I:
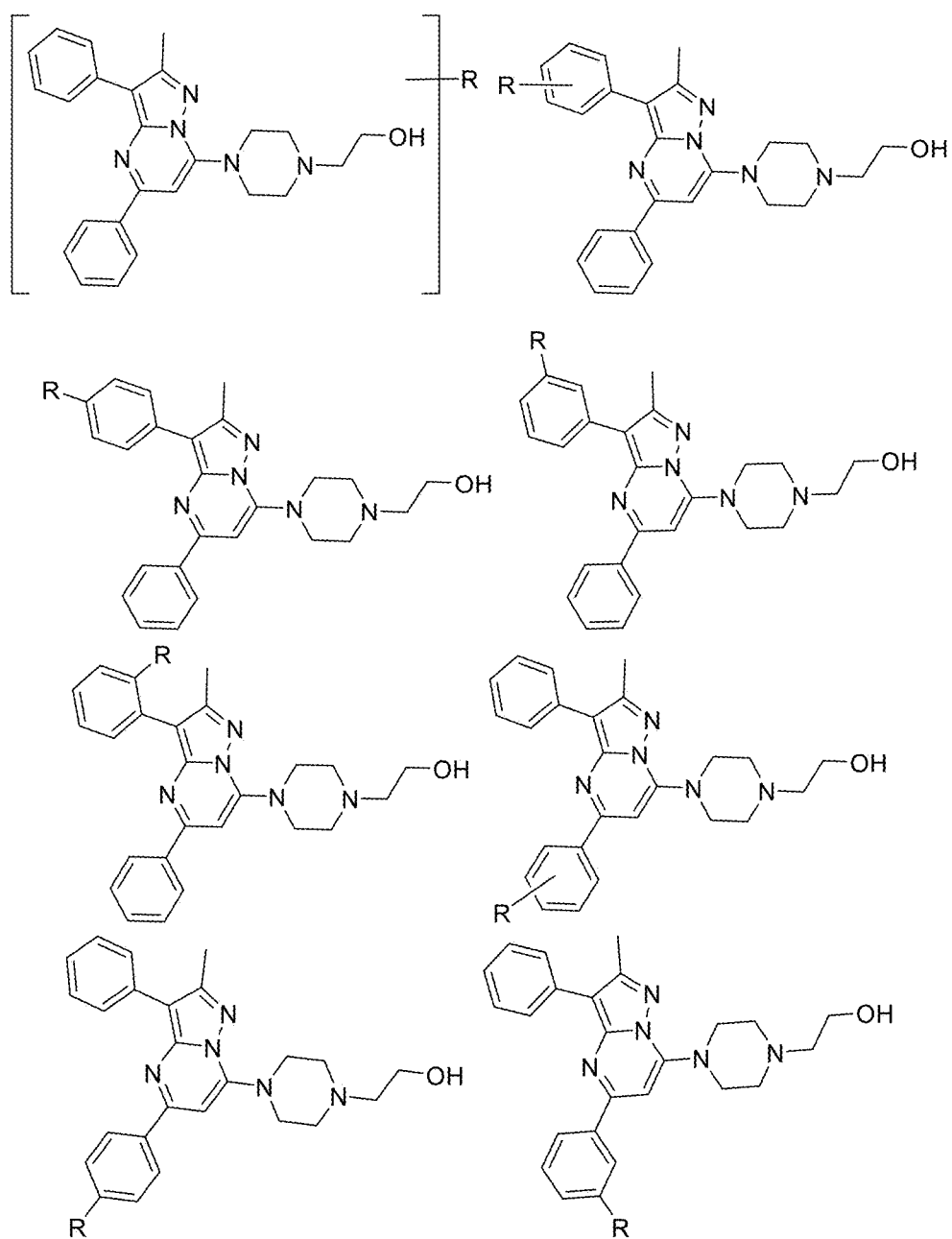
Figure 21J:
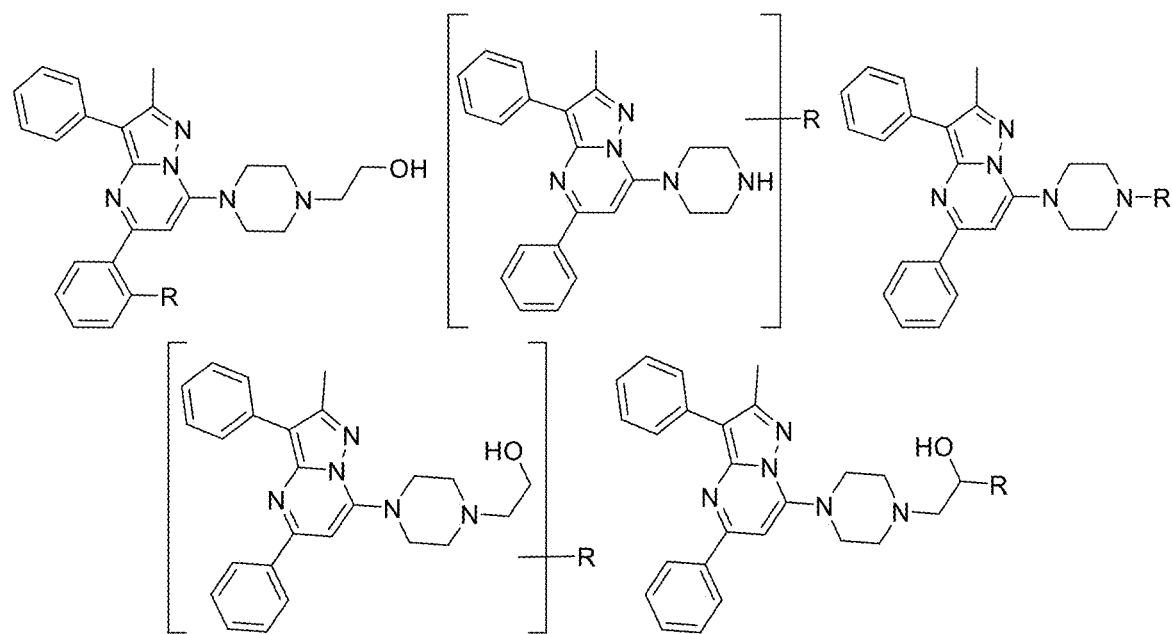

FIG. 18A-18C provide non-limiting examples of IRAK4 Targeting Ligands, wherein R represents exemplary points at which the Linker can be attached. For additional examples and related ligands see crystal structures PDB 6UYA, 4YP8, 5UIU, and 6F3I in the respective references (Rajapaksa N. S. et al. "Discovery of Potent Benzolactam IRAK4 Inhibitors with Robust in Vivo Activity." ACS Med. Chem. Lett. 11: 327-333 (2020); McElroy W. T. et al. "Potent and Selective Amidopyrazole Inhibitors of IRAK4 That Are Efficacious in a Rodent Model of Inflammation." ACS Med. Chem. Lett. 6: 677-682 (2015); Nunes J. et al. "Targeting IRAK4 for Degradation with PROTACs" ACS Med. Chem. Lett. 10: 1081-1085 (2019); 4); Degorce S. L. et al. "Optimization of permeability in a series of pyrrolotriazine inhibitors of IRAK4". Bioorg. Med. Chem. 26: 913-924 (2018); WO2019099926 and WO2019133531.

FIG. 19A-19D provide non-limiting examples of FGFR2 and FGFR3 Targeting Ligands wherein R is the point at which the Linker is attached. For additional examples see: "Structure-based drug design of 1,3,5-triazine and pyrimidine derivatives as novel FGFR3 inhibitors with high selectivity over VEGFR2" *BioorgMed Chem* 2020, 28, 115453.

FIG. 20A-20D provide non-limiting examples of SMARCA2 Targeting Ligands wherein R is the point at which the Linker is attached. For additional examples see: WO2020023657, US20200038378, WO2020010227, WO2020078933, WO2019207538, WO2016138114, "Discovery of Orally Active Inhibitors of Brahma Homolog (BRM)/SMARCA2 ATPase Activity for the Treatment of Brahma Related Gene 1 (BRG1)/SMARCA4-Mutant Cancers" *J Med Chem* 2018, 61, 10155; 2) WO2020035779.

FIG. 21A-21J provide non-limiting examples of NRAS Targeting Ligands, wherein R represents exemplary points at which the Linker can be attached. For additional examples, see "Small-molecule Ligands Bing to a Distinct Pocket in Ras and Inhibit SOS-Mediated Nucleotide Exchange Activity" *PNAS* 2012 109 (14) 5299-5304; the crystal structure PDB 4EPY. ("Discovery of Small Molecules that Bind to K-Ras and Inhibit Sos-Mediated Activation" Angew. Chem. Int. Ed 2012, 51, 6140-6143); the crystal structure PDB 6GQY, 6GQT, ("Structure-based development of new RAS-effector inhibitors from a combination of active and inactive RAS-binding compounds" 2019 PNAS 116 (7), 2545-2550); the crystal structure PDB 6FA4, 1HE8, ("Small molecule inhibitors of RAS-effector protein interactions derived using an intracellular antibody fragment" 2018 Nature Communications 9(1), 3169); and "Discovery of High-Affinity Noncovalent Allosteric KRAS Inhibitors That Disrupt Effector Binding" ACS Omega 2019, 4, 2921-2930.

Figure 22:
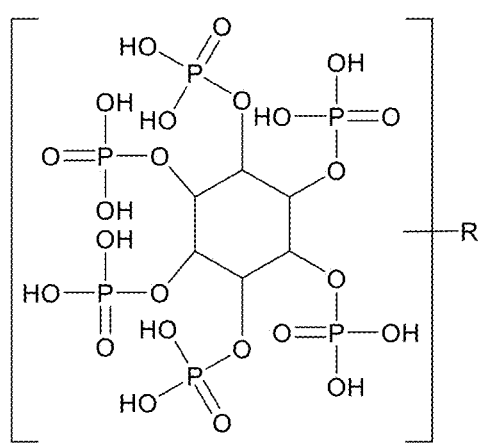

FIG. 22 provides a non-limiting example of an ADAR Targeting Ligand, wherein R represents exemplary points at which the Linker can be attached. For additional examples, see the crystal structure PDB 6VFF, (Thuy-Boun, A. S., et al, Nucleic Acids Res, 2020, 48, 7958-7972); and the crystal structures PDB 5HP2, 5HP3, 5ED1, 5ED2 (Mathews, M. M, et al., Nat Struct Mol Biol., 2016, 23, 426-433).

Figure 23:

FIG. 23 provides non-limiting examples of NSD2 or WHSC1 Targeting Ligands, wherein R represents exemplary points at which the Linker can be attached. For additional examples, see the crystal structure PDB 6XCG (Zhou, M. Q, et al., "Histone-lysine N-methyltransferase NSD2-PWWP1 with compound UNC6934", to be published); the crystal structure PDB 6UE6 (Liu, Y et al., "PWWP1 domain of NSD2 in complex with MR837", to be published); the crystal structure PDB 5LSS, 5LSU, 5LSX, 5LSY, 5LSZ, 5LT6,5LT7, 5LT8 (Tisi, D., et al, "Structure of the Epigenetic Oncogene MMSET and Inhibition by N-Alkyl Sinefungin Derivatives.", ACS Chem Biol., 2016, 11: 3093-3105).

Figure 24:
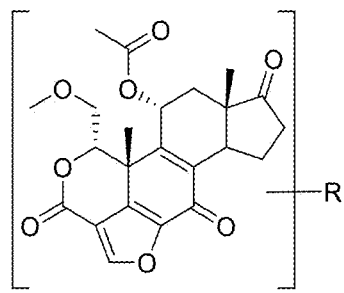

FIG. 24 provides non-limiting example of PI3KCA Targeting Ligands, wherein R represents exemplary points at which the Linker can be attached. For additional examples, see the crystal structure PDB 3HHM, 3HIZ (Mandelker, D., et al., "A frequent kinase domain mutation that changes the interaction between PI3K{alpha} and the membrane.", Proc Natl Acad Sci USA., 2009, 106: 16996-17001).

Figure 25:
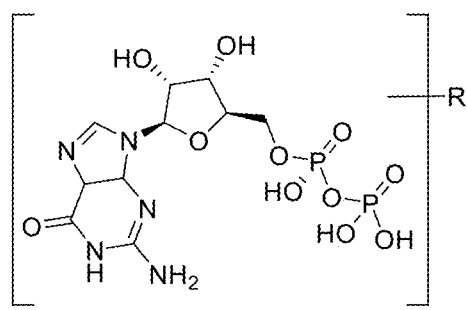

FIG. 25 provides a non-limiting example of a RIT1 Targeting Ligand, wherein R represents exemplary points at which the Linker can be attached. For additional examples, see the crystal structure PDB 4KLZ (Shah, D. M., et al., "Inhibition of Small GTPases by Stabilization of the GDP Complex, a Novel Approach applied to Rit1, a Target for Rheumatoid Arthritis", to be published).

Figure 26:
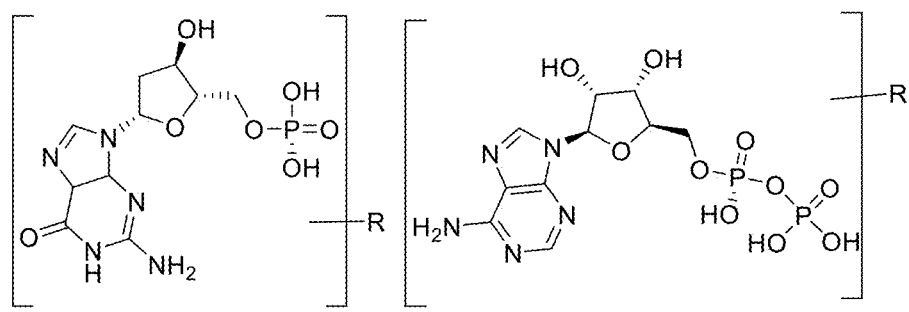

FIG. 26 provides non-limiting examples of WRN Targeting Ligands, wherein R represents exemplary points at which the Linker can be attached. For additional examples, see the crystal structure PDB 2FC0 (Perry, J. J., et al., "WRN exonuclease structure and molecular mechanism imply an editing role in DNA end processing.'", Nat Struct Mol Biol., 2006, 13: 414-422); and the crystal structure PDB 6YHR (Newman, J. A., et al., "Crystal structure of Werner syndrome helicase", to be published).

Figure 27:
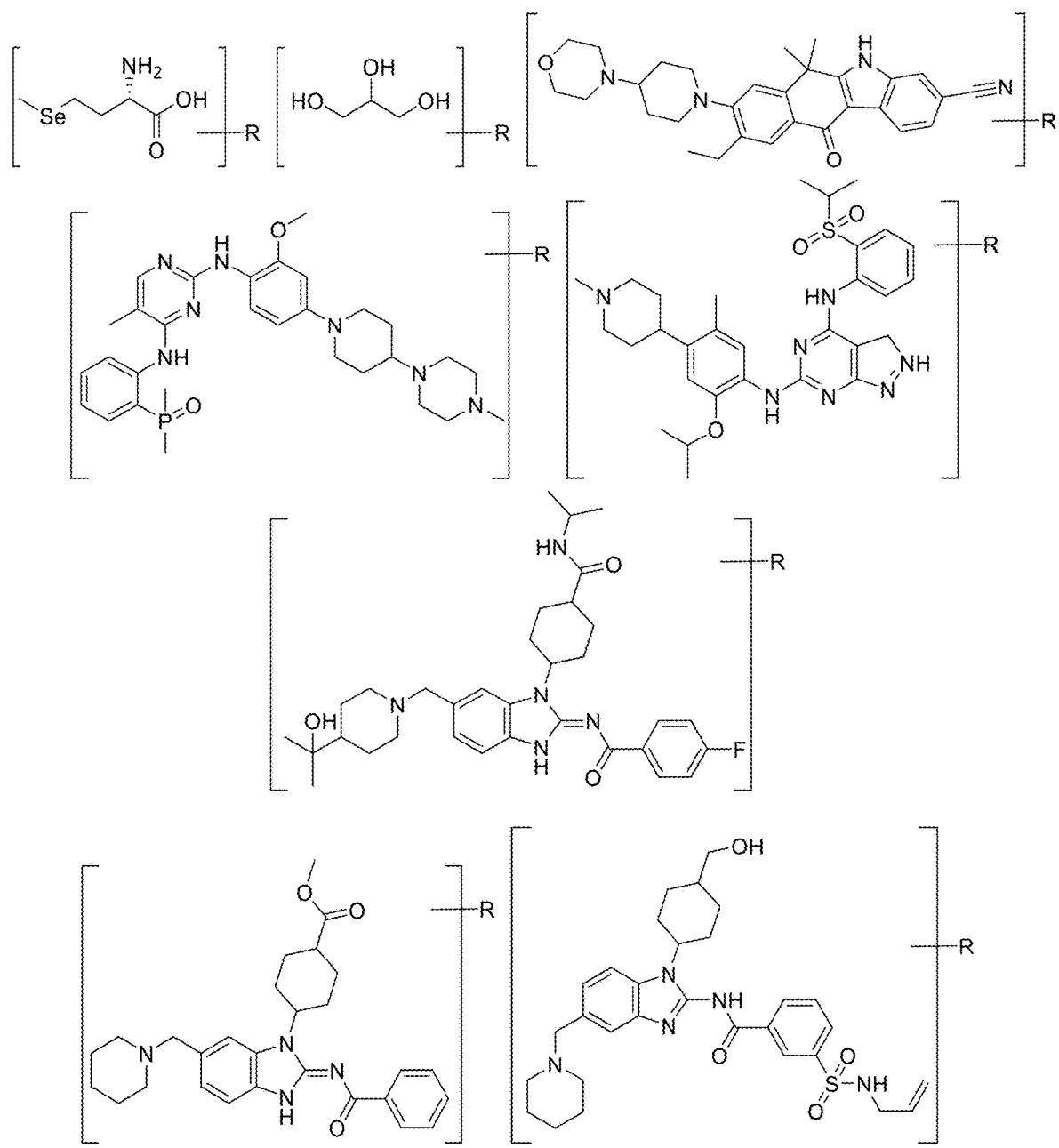

FIG. 27 provides non-limiting examples of ALK-fusion Targeting Ligands, for example EML4-ALK or NMP-ALK, wherein R represents exemplary points at which the Linker can be attached. For additional examples, see the crystal structure PDB 4CGB, 4CGC (Richards, M. W., et al., "Microtubule Association of Eml Proteins and the Eml4-Alk Variant 3 Oncoprotein Require an N-Terminal Trimerization Domain", Biochem J., 2015, 467: 529); the crystal structure PDB 3AOX (Sakamoto, H., et al., "CH5424802, a selective ALK inhibitor capable of blocking the resistant gatekeeper mutant", Cancer Cell, 2011, 19: 679-690); the crystal structure PDB 6MX8 (Huang, W. S., et al., "Discovery of Brigatinib (AP26113), a Phosphine Oxide-Containing, Potent, Orally Active Inhibitor of Anaplastic Lymphoma Kinase", J Med Chem., 2016, 59: 4948-4964); 4Z55 (Michellys, P. Y., et al., "Design and synthesis of novel selective anaplastic lymphoma kinase inhibitors.", Bioorg Med Chem Lett., 2016, 26: 1090-1096); and the crystal structures PDB 4FOB, 4FOC, 4FOD (Lewis, R. T., et al, "The Discovery and Optimization of a Novel Class of Potent, Selective, and Orally Bioavailable Anaplastic Lymphoma Kinase (ALK) Inhibitors with Potential Utility for the Treatment of Cancer.", J Med Chem., 2012, 55: 6523-6540).

Figure 28:
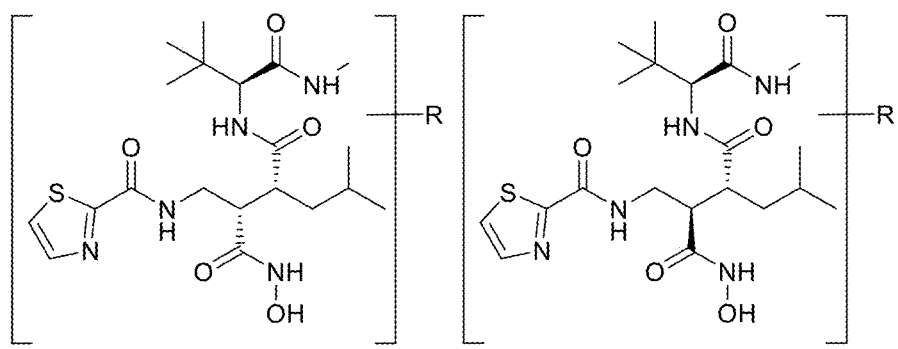

FIG. 28 provides non-limiting examples of BAP1 Targeting Ligands, wherein R represents exemplary points at which the Linker can be attached. For additional examples, see the crystal structure PDB 2W12, 2W13, 2W14, 2W15 (Lingott, T. J. et al., "High-Resolution Crystal Structure of the Snake Venom Metalloproteinase Bap1 Complexed with a Peptidomimetic: Insight into Inhibitor Binding", Biochemistry, 2009, 48: 6166).

Figure 29:
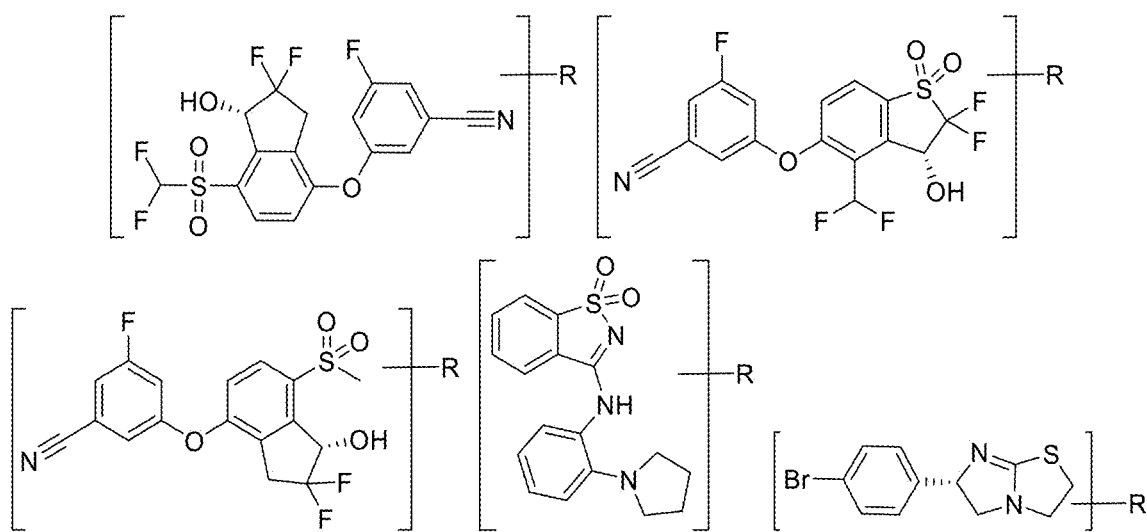

FIG. 29 provides non-limiting examples of EPAS1 or HIF2α Targeting Ligands, wherein R represents exemplary points at which the Linker can be attached. For additional examples, see the crystal structure PDB 5UFP (Cho, H., et al., "On-target efficacy of a HIF-2 alpha antagonist in preclinical kidney cancer models.", Nature, 2016, 539: 107-111); the crystal structure PDB 6D09 Du, X, ("Crystal structure of PT1940 bound to HIF2a-B*:ARNT-B* complex", to be published); the crystal structure PDB 5TBM (Wallace, E. M., et al.," A Small-Molecule Antagonist of HIF2 alpha Is Efficacious in Preclinical Models of Renal Cell Carcinoma.", Cancer Res., 2016, 76: 5491-5500); and the crystal structure PDB 6E3S, 6E3T, 6E3U (Wu, D., et al., "Bidirectional modulation of HIF-2 activity through chemical ligands.", Nat Chem Biol., 2019, 15: 367-376).

Figure 30A:
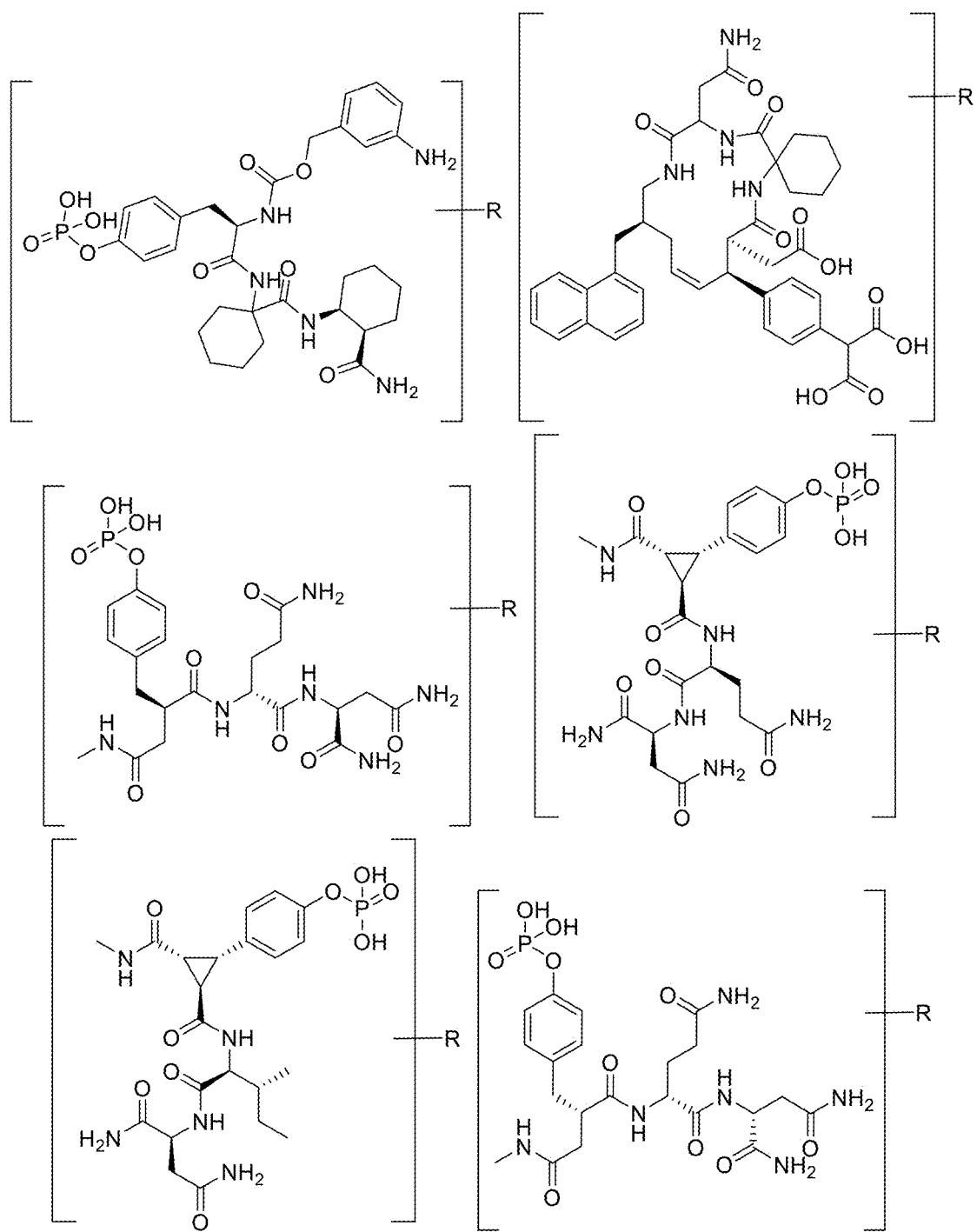
Figure 30B:
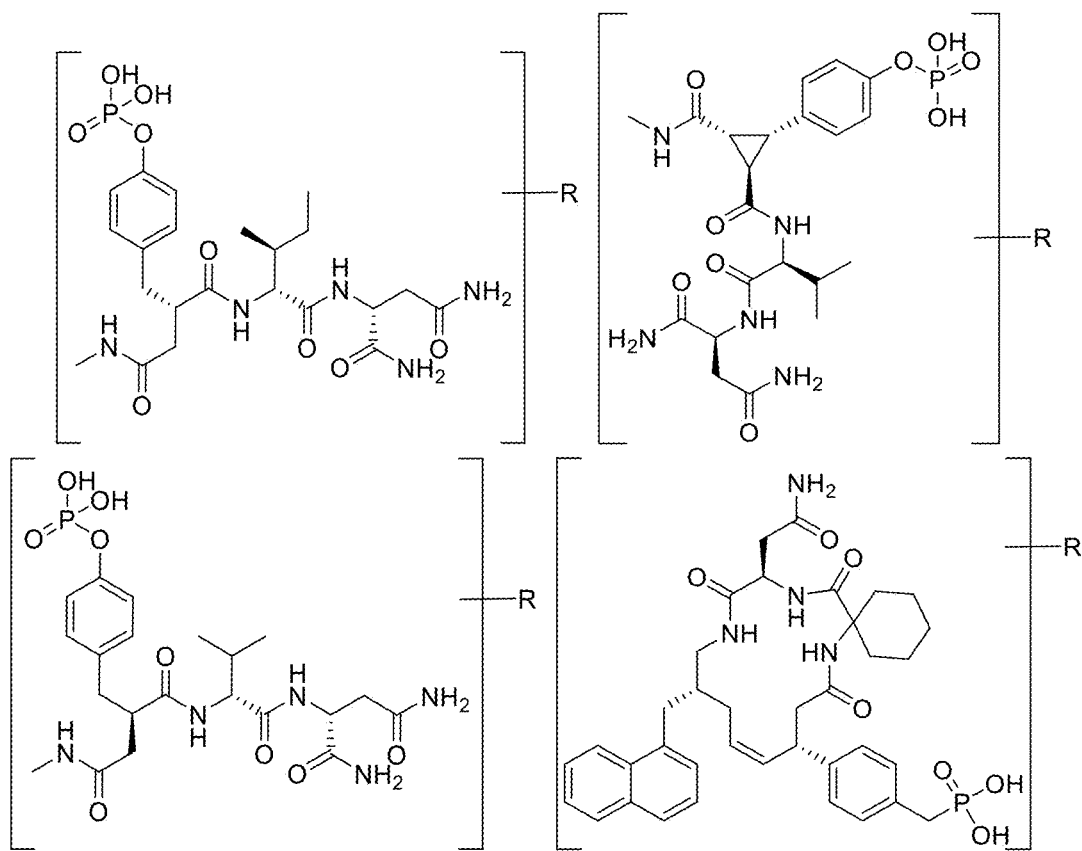

FIG. 30A and FIG. 30B provide non-limiting examples of GRB2 Targeting Ligands, wherein R represents exemplary points at which the Linker can be attached. For additional examples, see the crystal structure PDB 1CJ1 (Furet, P., et al., "Structure-based design, synthesis, and X-ray crystallography of a high-affinity antagonist of the Grb2-SH2 domain containing an asparagine mimetic", J Med Chem., 1999, 42: 2358-2363); the crystal structure PDB 2AOA, 2AOB (Phan, J., et al., "Crystal Structures of a High-affinity Macrocyclic Peptide Mimetic in Complex with the Grb2 SH2 Domain", J Mol Biol., 2005, 353: 104-115); the crystal structure PDB 3KFJ, 3IN7, 3TMJ, 3TMD, 3IN8 (Delorbe, J. E., et al., "Thermodynamic and Structural Effects of Conformational Constraints in Protein-Ligand Interactions. Entropic Paradoxy Associated with Ligand Preorganization.", J Am Chem Soc., 2009, 131: 16758-16770); the crystal structure PDB 2HUW, 3C71 (Benfield, A. P., et al., "Ligand Preorganization May Be Accompanied by Entropic Penalties in Protein-Ligand Interactions.", Angew Chem Int Ed Engl., 2006, 45: 6830-6835); and the crystal structure PDB 1XON (Ogura, K et al., "NMR structure of growth factor receptor binding protein SH2 domain complexed with the inhibitor", to be published).

Figure 31:
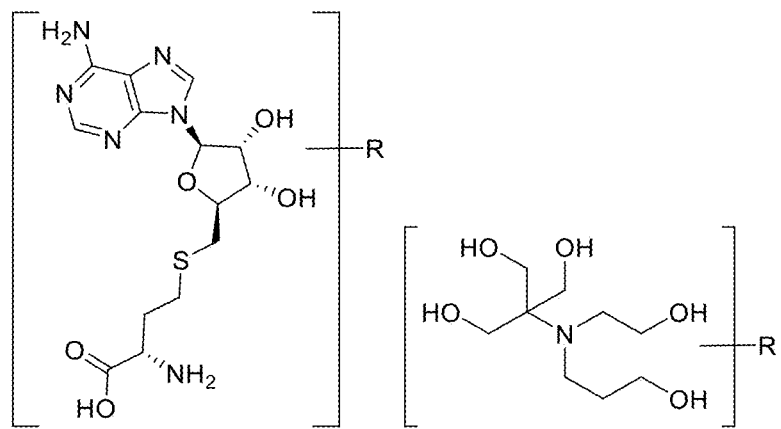

FIG. 31 provides non-limiting examples of KMT2D or MLL2/MLL4Targeting Ligands, wherein R represents exemplary points at which the Linker can be attached. For additional examples, see the crystal structure PDB 7BRE (Li, Y., et al., "Crystal Structure of MLL2 Complex Guides the Identification of a Methylation Site on P53 Catalyzed by KMT2 Family Methyltransferases.", Structure, 2020); the crystal structure PDB 4ZAP (Zhang, Y., et al., "Evolving Catalytic Properties of the MLL Family SET Domain.", Structure, 2015, 23: 1921-1933); the crystal structure PDB 6KIZ (Xue, H., et al., "Structural basis of nucleosome recognition and modification by MLL methyltransferases.", Nature, 2019, 573: 445-449); and the crystal structures PDB 3UVK (Zhang, P., et al., "The plasticity of WDR5 peptide-binding cleft enables the binding of the SET1 family of histone methyltransferases.", Nucleic Acids Res., 2012, 40: 4237-4246).

Figure 32:
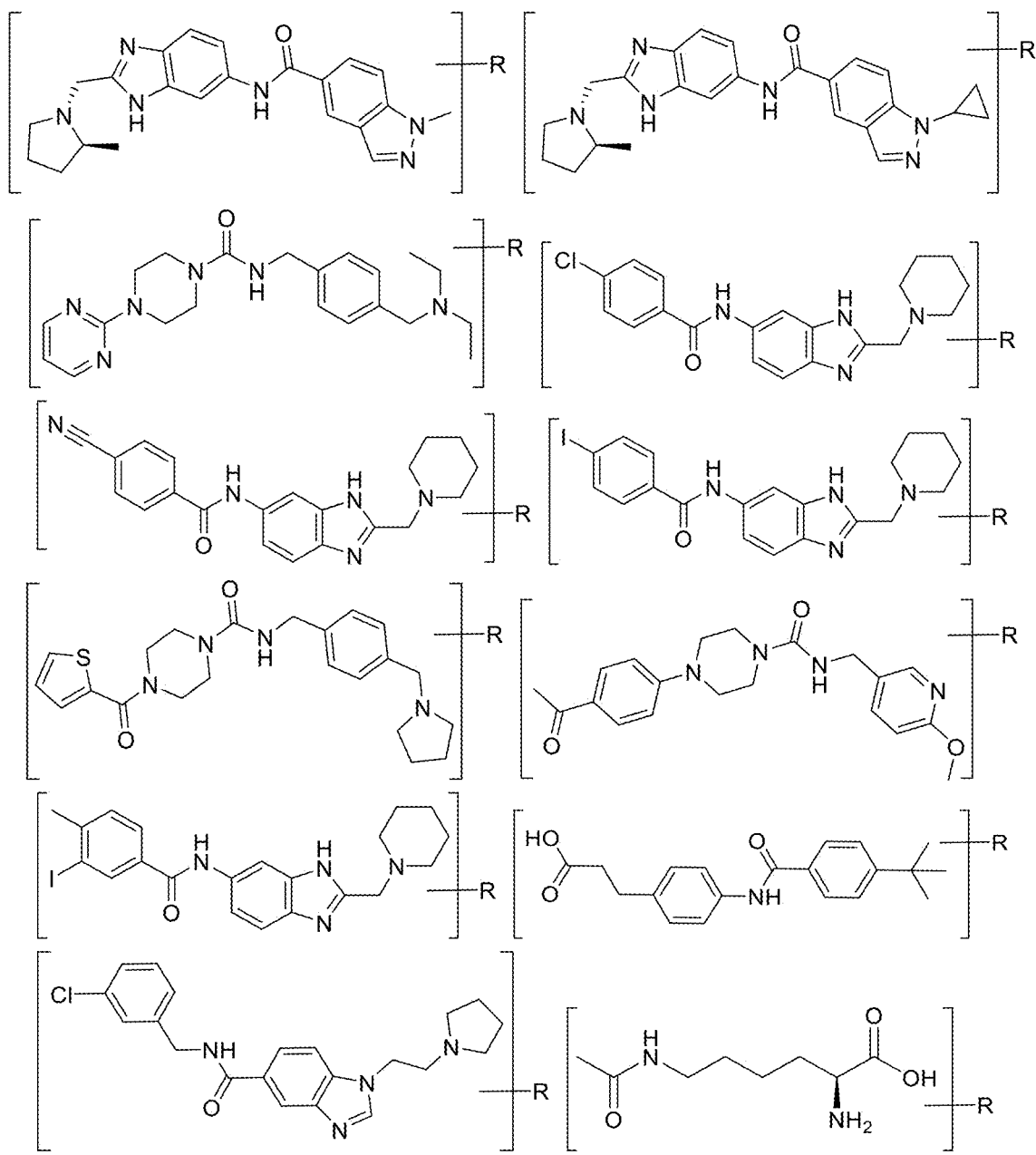

FIG. 32 provides non-limiting examples of MLLT1 or ENL Targeting Ligands, wherein R represents exemplary points at which the Linker can be attached. For additional examples, see the crystal structure PDB 6HT0, 6HT1 (Moustakin, M. et al., "Discovery of an MLLT1/3 YEATS Domain Chemical Probe", Angew Chem Int Ed Engl., 2018, 57: 16302-16307); the crystal structures PDB 6T1I, 6T1J, 6TIL, 6T1M, 6T1N, 6T10 (Ni, X., et al., "Structural Insights into Interaction Mechanisms of Alternative Piperazine-urea YEATS Domain Binders in MLLT1", ACS Med Chem Lett., 2019, 10: 1661-1666); and the crystal structures PDB 6HPW, 6HPY, 6HPX, 6HPZ (Heidenreich, D., et al., "Structure-Based Approach toward Identification of Inhibitory Fragments for Eleven-Nineteen-Leukemia Protein (ENL)", J Med Chem., 2018, 61: 10929-10934).

Figure 33:
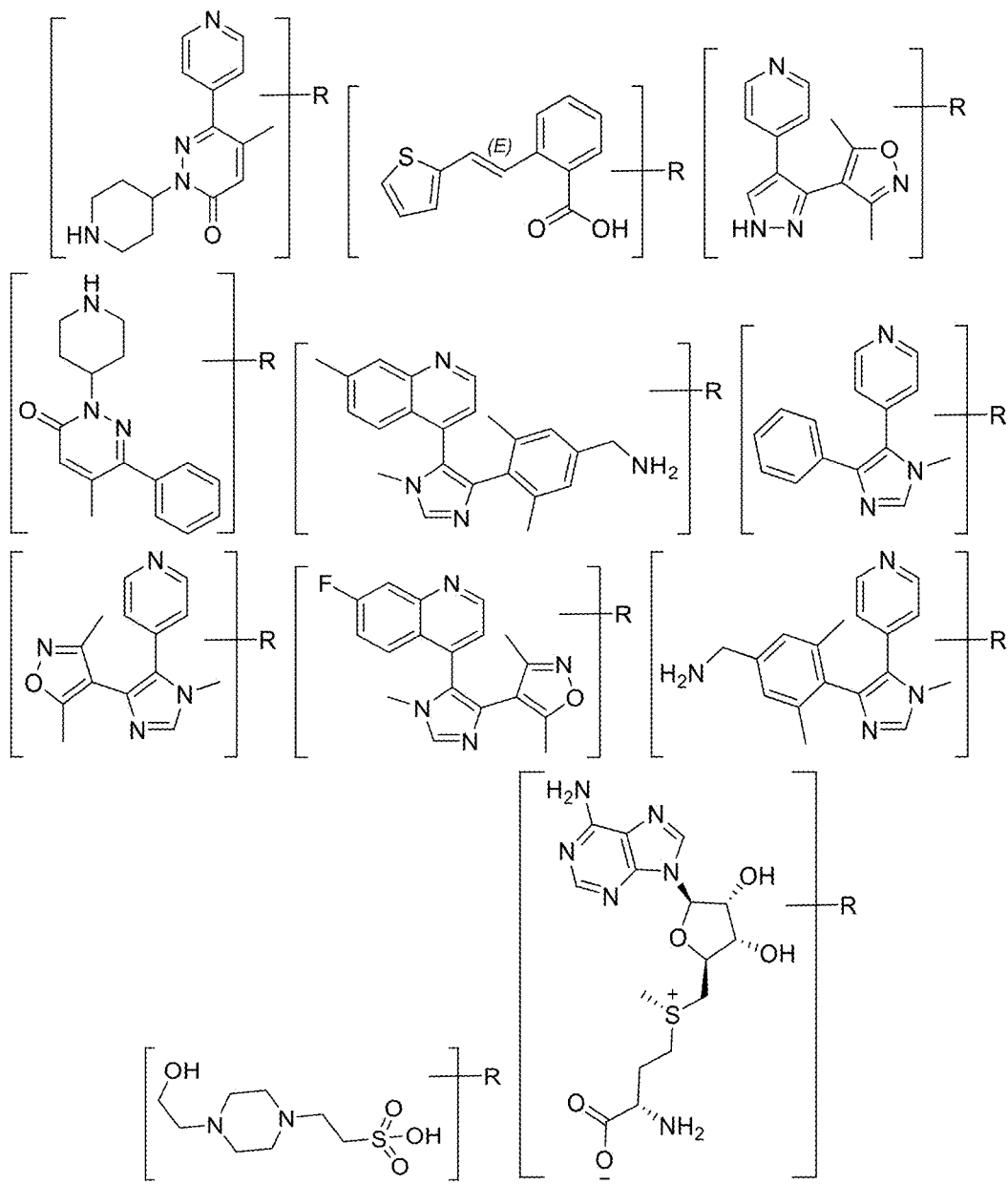

FIG. 33 provides non-limiting examples of NSD3 Targeting Ligands, wherein R represents exemplary points at which the Linker can be attached. For additional examples, see the crystal structure PDB 6G24, 6G25, 6G29, 6G2B, 6G2C, 6G2E, 6G2F, 6G20, 6G3T (Bottcher, J., et al., "Fragment-based discovery of a chemical probe for the PWWP1 domain of NSD3", Nat Chem Biol., 2019, 15: 822-829); the crystal structure PDB 5UPD (Tempel, W., et al., "Methyltransferase domain of human Wolf-Hirschhorn Syndrome Candidate 1-Like protein 1 (WHSC1L1)", to be published); and the crystal structure PDB 6CEN (Morrison, M. J., et al., "Identification of a peptide inhibitor for the histone methyltransferase WHSC1", PLoS One, 2018, 13: e0197082-e0197082).

Figure 34:
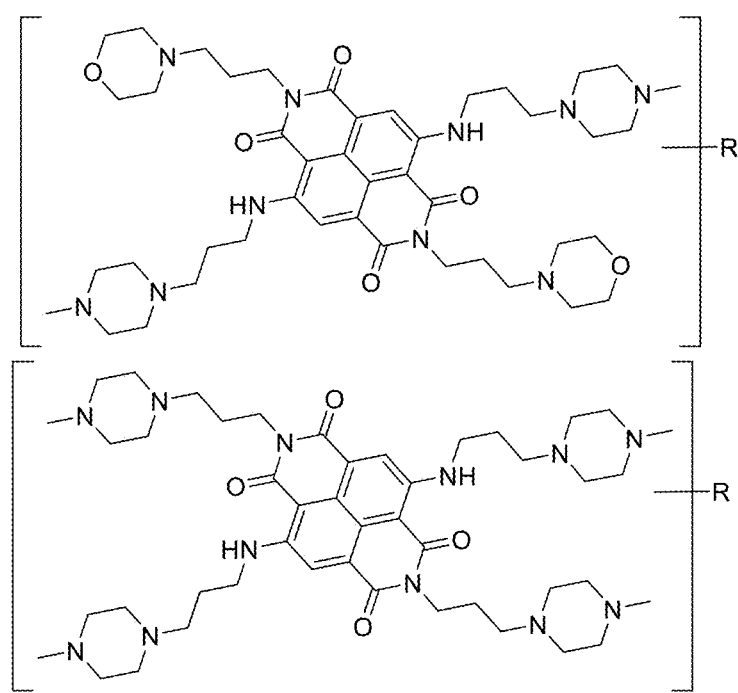

FIG. 34 provides non-limiting examples of PPM1D or WIP1 Targeting Ligands, wherein R represents exemplary points at which the Linker can be attached. For additional examples, see the crystal structure PDB 3UYH, ADA3, 4DAQ (Micco, M., et al., "Structure-based design and evaluation of naphthalene diimide g-quadruplex ligands as telomere targeting agents in pancreatic cancer cells", J Med Chem., 2013, 56: 2959-2974).

Figure 35A:
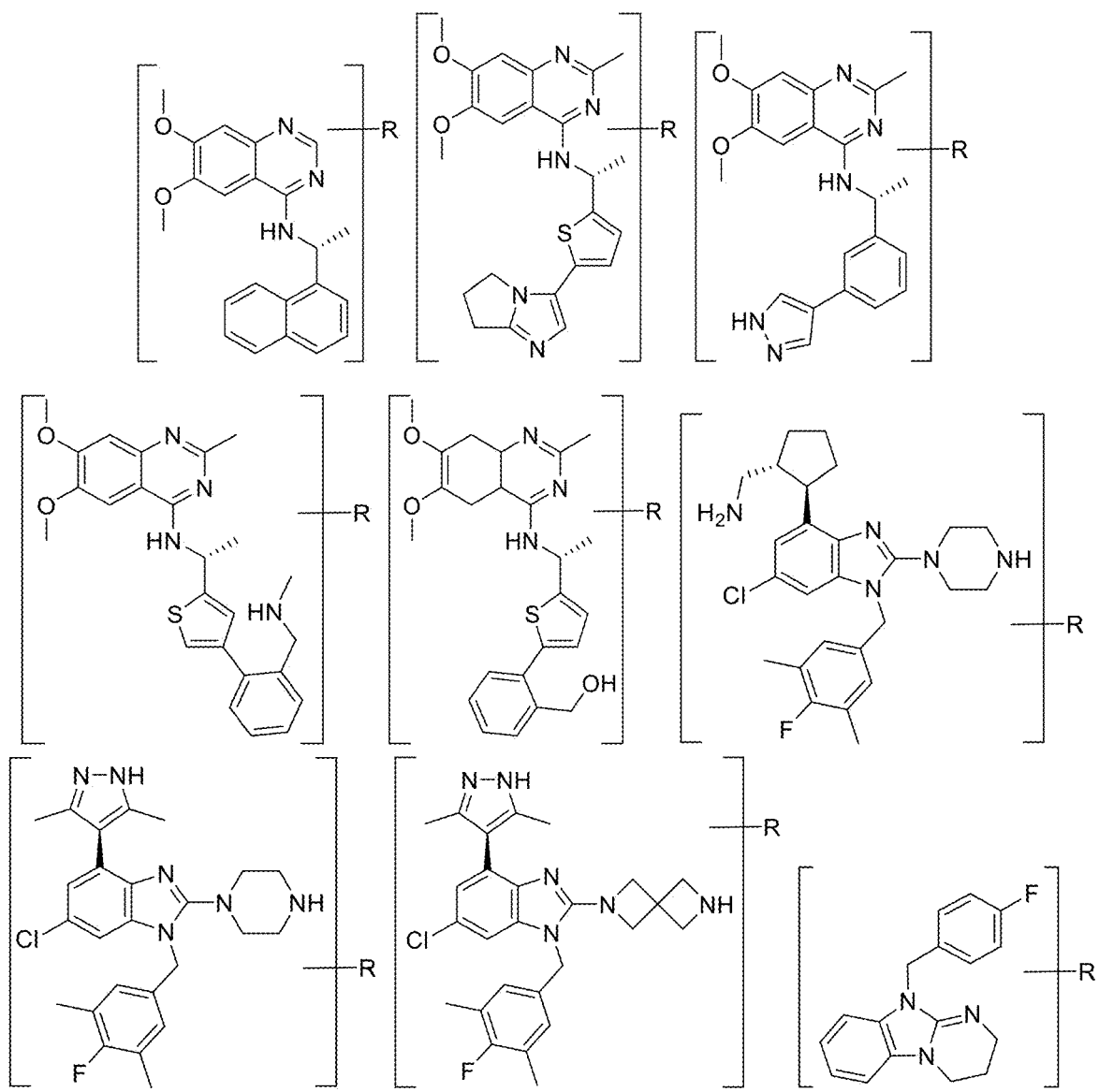
Figure 35B:
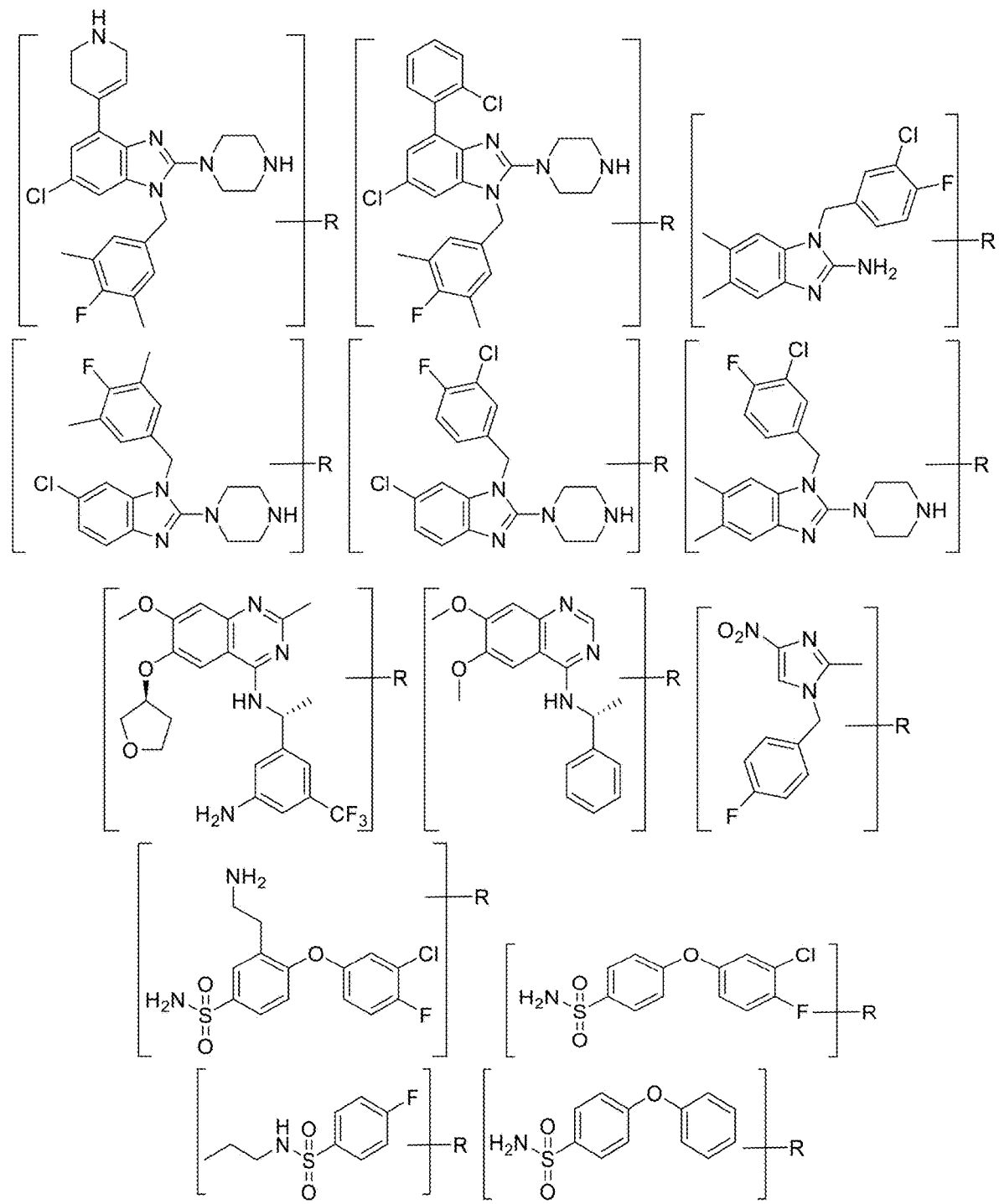

FIG. 35A-35B provide non-limiting examples of SOS1 Targeting Ligands, wherein R represents exemplary points at which the Linker can be attached. For additional examples, see the crystal structure PDB 5OVE, 5OVF, 5OVG, 5OVH, 5OVI, (Hillig, R. C., et al., "Discovery of potent SOS1 inhibitors that block RAS activation via disruption of the RAS-SOS1 interaction", Proc Natl Acad Sci USA., 2019, 116: 2551-2560); the crystal structure PDB 6F08 (Ballone, A., et al., "Structural characterization of 14-3-3 zeta in complex with the human Son of sevenless homolog 1 (SOS1)", J Struct Biol., 2018, 202: 210-215); the crystal structure PDB 6D5E, 6D5G, 6D5H, 6D5J, 6D5L, 6D5M, 6D5V, 6D5W, 6D55, 6D59, (Hodges, T. R. et al., "Discovery and Structure-Based Optimization of Benzimidazole-Derived Activators of SOS1-Mediated Nucleotide Exchange on RAS", J Med Chem., 2018, 61: 8875-8894); the crystal structure PDB 6SCM, 6SFR (Kessler, D., et al., "SOS1 in Complex with Inhibitor BI-3406", to be published); the crystal structure PDB 6V94, 6V9J, 6V9L, 6V9M, 6V9N (Sarkar, D., et al., "Discovery of Sulfonamide-Derived Agonists of SOS1-Mediated Nucleotide Exchange on RAS Using Fragment-Based Methods.", J Med Chem., 2020, 63: 8325-8337).

Figure 36A:
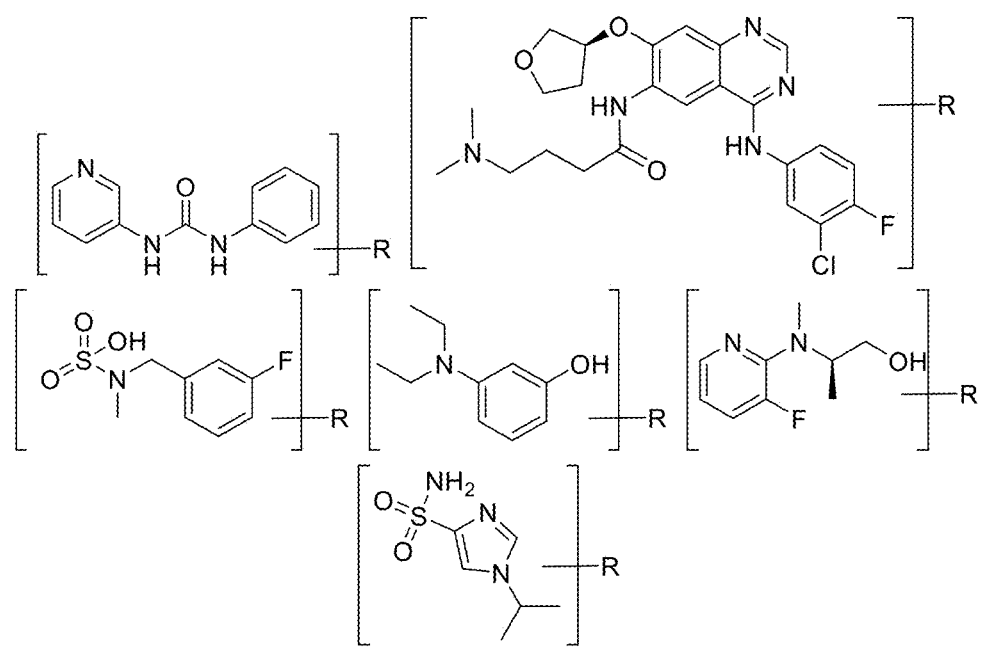

FIG. 36A provides non-limiting examples of TBXT or Brachyury Targeting Ligands, wherein R represents exemplary points at which the Linker can be attached. For additional examples, see the crystal structure PDB 5QS6, 5QSC, 5QSE, 5QSF, 5QRW, (Newman, J. A., et al., "Pan-DDA analysis group deposition", to be published); and the crystal structure PBD 6ZU8 (Newman, J. A., et al., "Crystal structure of human Brachyury G177D variant in complex with Afatinib", to be published).

Figure 37A:
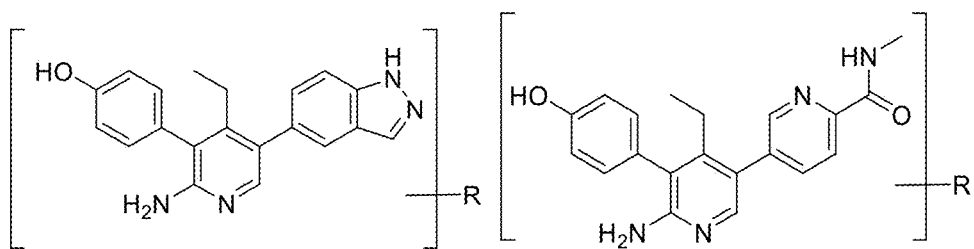
Figure 37B:
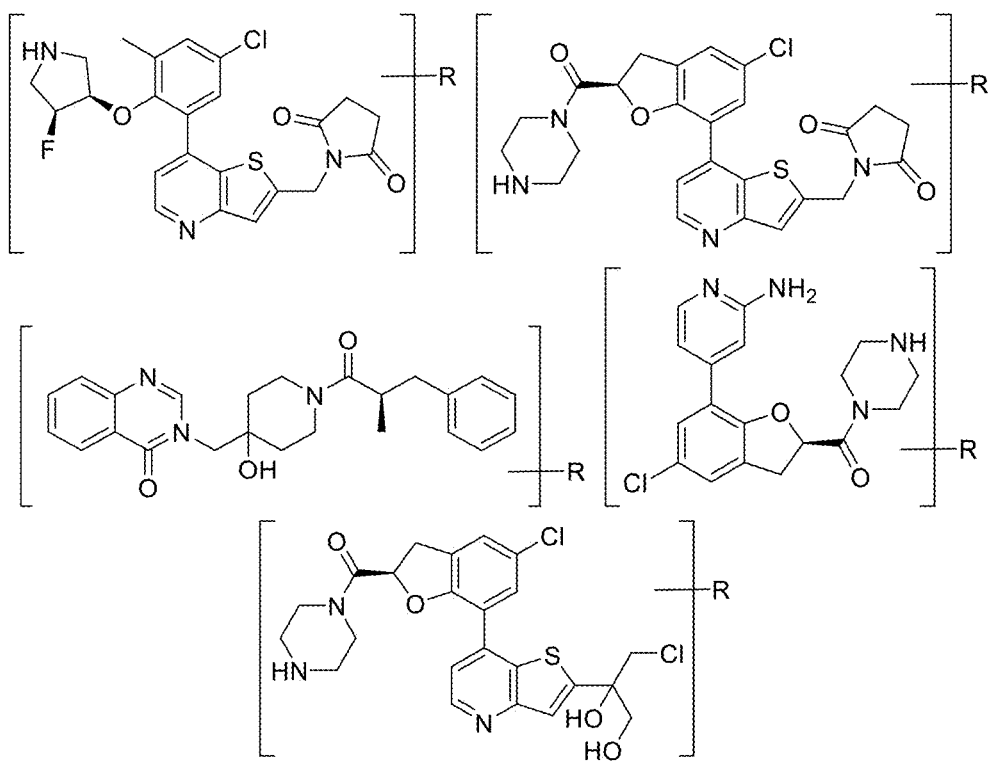
Figure 37C:
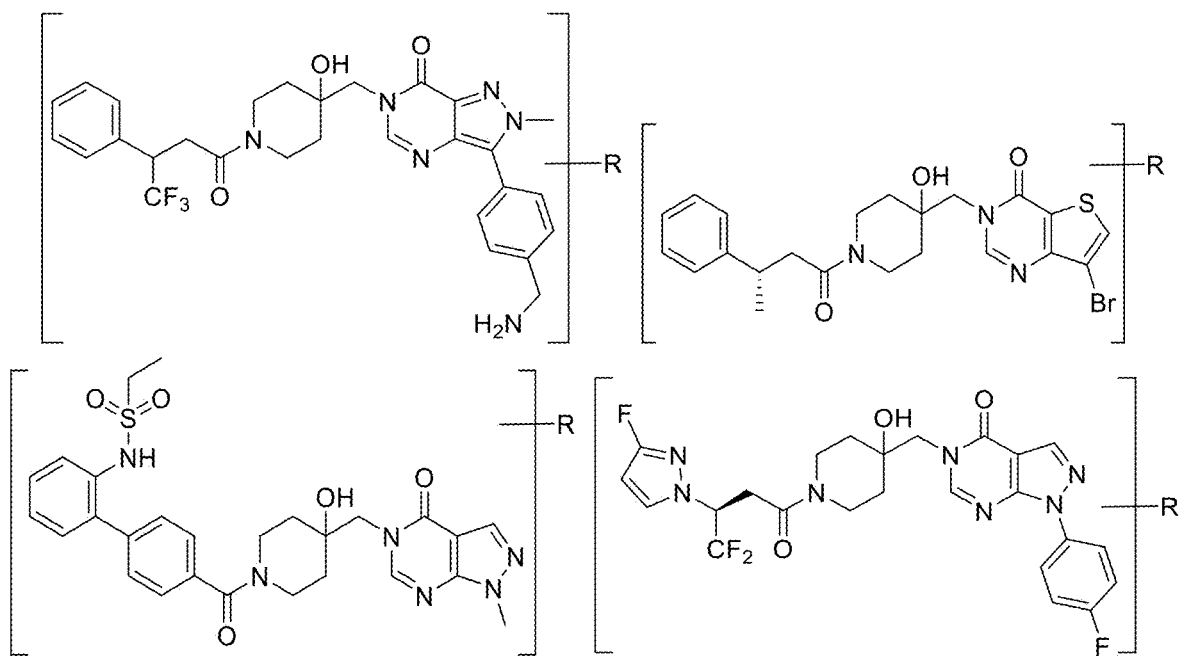

FIG. 37A-37C provide non-limiting examples of USP7 Targeting Ligands, wherein R represents exemplary points at which the Linker can be attached. For additional examples, see the crystal structure PDB 5UQV, 5UQX (Kategaya, L., et al., "USP7 small-molecule inhibitors interfere with ubiquitin binding", Nature, 2017, 550: 534-538); the crystal structures PDB 6VN2, 6VN3, 6VN4, 6VN5, 6VN6 (Leger, P. R., et al., "Discovery of Potent, Selective, and Orally Bioavailable Inhibitors of USP7 with In Vivo Antitumor Activity.", J Med Chem., 2020, 63: 5398-5420); and the crystal structures PDB 5N9R, 5N9T (Gavory, G., et al., "Discovery and characterization of highly potent and selective allosteric USP7 inhibitors.", Nat Chem Biol., 2018, 14: 118-125); and the crystal structure PDB 5NGE, 5NGF (Turnbull, A. P., et al., "Molecular basis of USP7 inhibition by selective small-molecule inhibitors", Nature, 2017, 550: 481-486).

Figure 38:
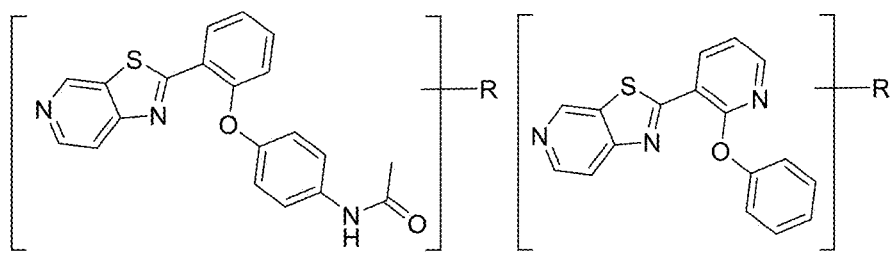

FIG. 38 provides non-limiting examples of BKV and JCV Targeting Ligands, wherein R represents exemplary points at which the Linker can be attached. For additional examples, see the crystal structure PDB 5J4V, 5J4Y (Bonafoux, D., et al., "Fragment-Based Discovery of Dual JC Virus and BK Virus Helicase Inhibitors.", J Med Chem., 2016, 59: 7138-7151).

Figure 39:
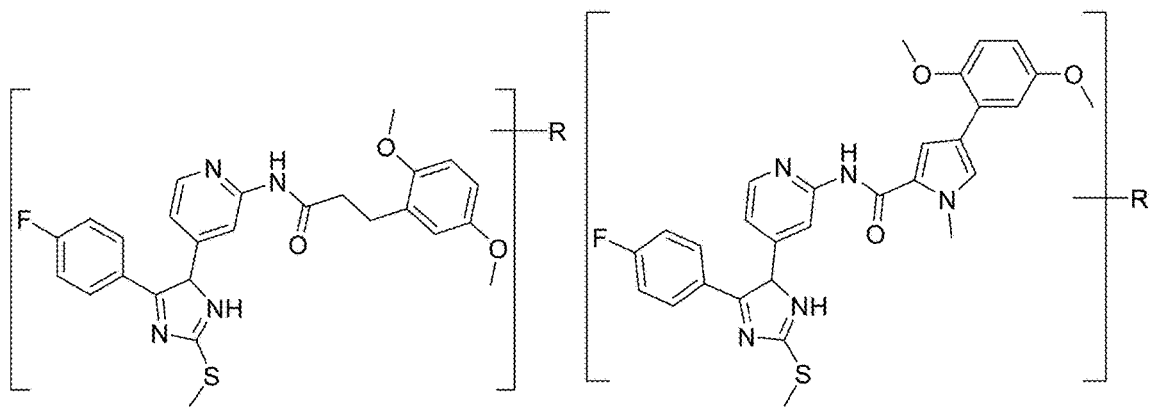

FIG. 39 provides non-limiting examples of CK1α (Casein kinase 1 alpha) Targeting Ligands, wherein R represents exemplary points at which the Linker can be attached. For additional examples, see the crystal structure PDB 5ML5, 5MQV (Halekotte, J., et al., "Optimized 4,5-Diarylimidazoles as Potent/Selective Inhibitors of Protein Kinase CK1 delta and Their Structural Relation to p38 alpha MAPK.", Molecules, 2017,22).

Figure 40:
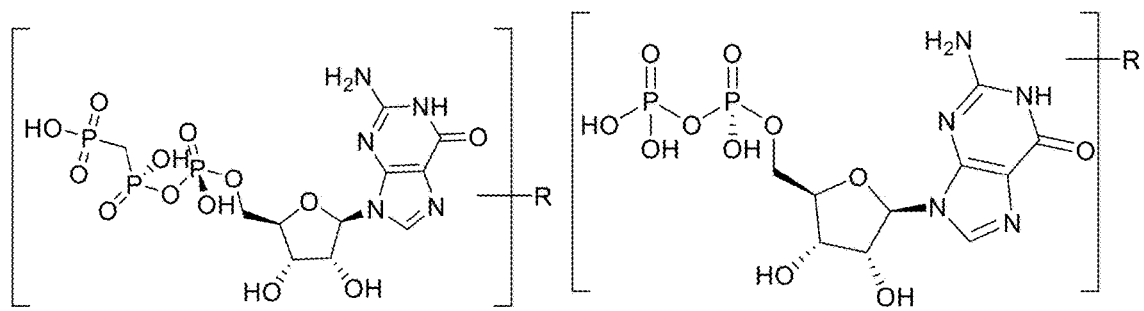

FIG. 40 provides non-limiting examples of GSPT1/ERF3 Targeting Ligands, wherein R represents exemplary points at which the Linker can be attached. For additional examples, see the crystal structure PDB 5LZT, 5LZS, 5LZV, 5LZU, 5LZX, 5LZW, 5LZZ, 5LZY (Shao, S., et al., "Decoding Mammalian Ribosome-mRNA States by Translational GTPase Complexes", Cell, 2016, 167: 1229-1240.e15).

Figure 41:
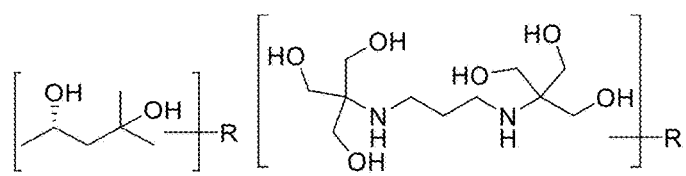

FIG. 41 provides non-limiting examples of IFZV Targeting Ligands, wherein R represents exemplary points at which the Linker can be attached. For additional examples, see the crystal structure PDB (Iyer, S., et al., "The crystal structure of human placenta growth factor-1 (PlGF-1), an angiogenic protein, at 2.0 A resolution.", J Biol Chem., 2001, 276: 12153-12161); and the crystal structure PDB IRV6 (Christinger, H. W., et al., "The crystal structure of placental growth factor in complex with domain 2 of vascular endothelial growth factor receptor-1", J Biol Chem., 2004, 279: 10382-10388).

Figure 42:
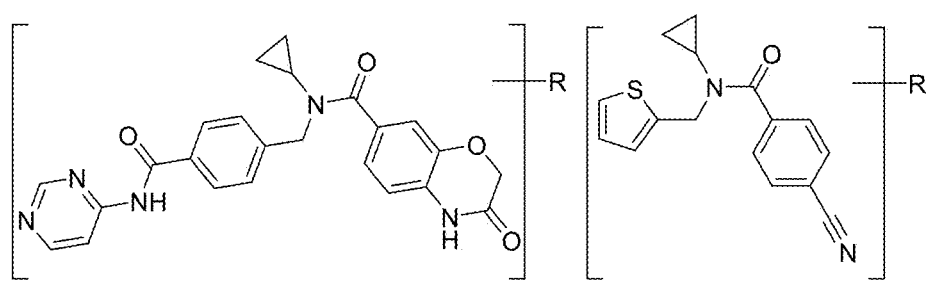

FIG. 42 provides non-limiting examples of NSD2 Targeting Ligands, wherein R represents exemplary points at which the Linker can be attached. For additional examples, see the crystal structure PDB 6XCG (Zhou, M. Q., "Histone-lysine N-methyltransferase NSD2-PWWP1 with compound UNC6934", to be published); and the crystal structure PDB 6UE6 (Liu, Y., et al., "PWWP1 domain of NSD2 in complex with MR837", to be published).

Figure 43:
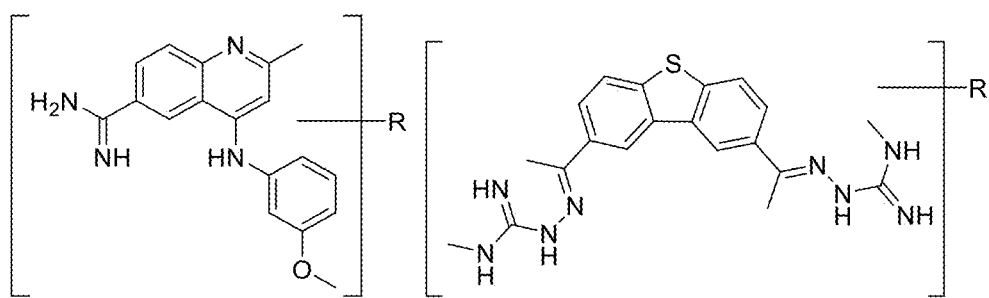

FIG. 43 provides non-limiting examples of TAU Targeting Ligands, wherein R represents exemplary points at which the Linker can be attached. For additional examples, see the crystal structure PDB 6VA2, 6VA3 (Chen, J. L. et al., "Design, Optimization, and Study of Small Molecules That Target Tau Pre-mRNA and Affect Splicing.", J Am Chem Soc., 2020, 142: 8706-8727).

Figure 44:
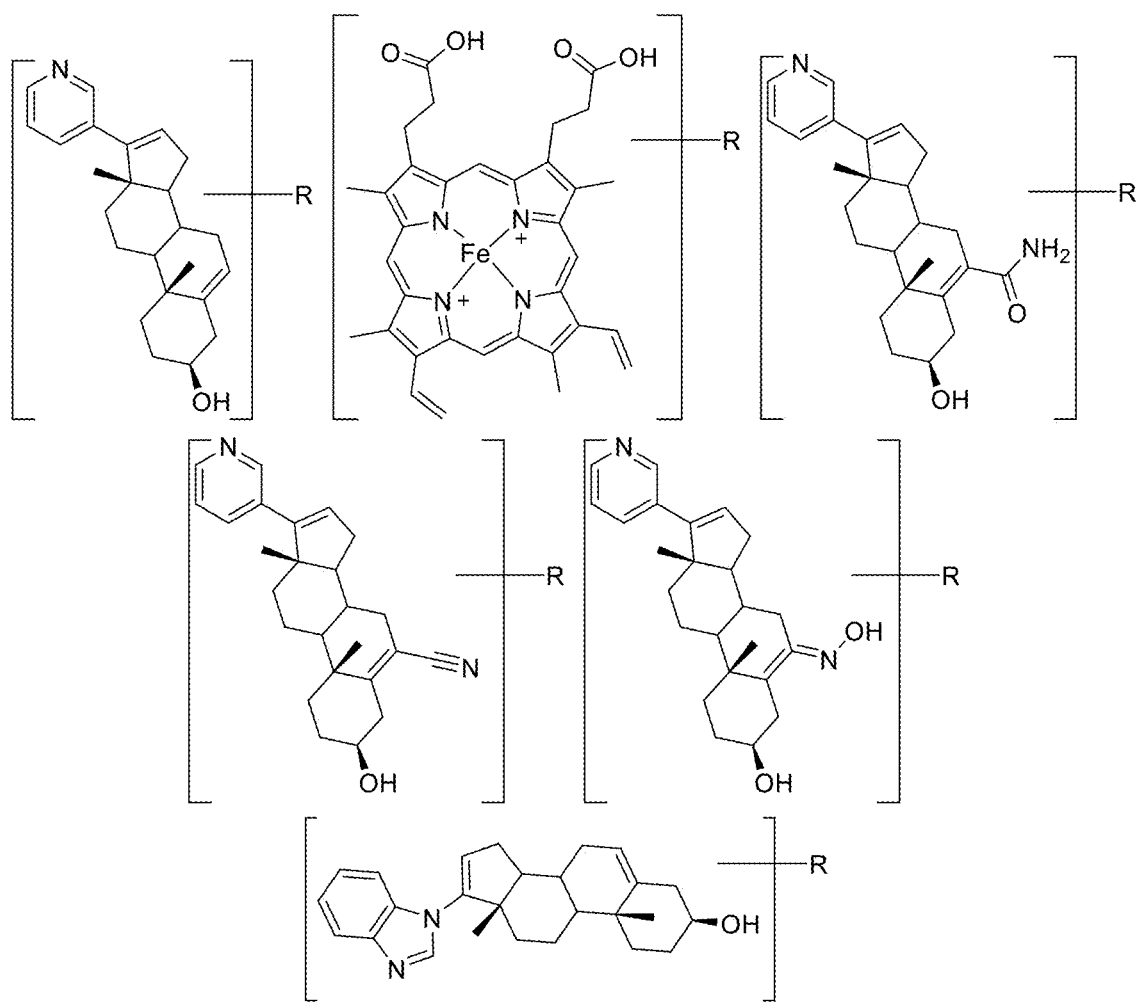

FIG. 44 provides non-limiting examples of CYP17A1 Targeting Ligands, wherein R represents exemplary points at which the Linker can be attached. For additional examples, see the crystal structure PDB 3RUK, 3SWZ (Devore, N. M. et al., "Structures of cytochrome P450 17A1 with prostate cancer drugs abiraterone and TOK-001", Nature, 2012, 482: 116-119); and the crystal structure PDB 6CHI, 6CIZ, (Fehl, C., et al., "Structure-Based Design of Inhibitors with Improved Selectivity for Steroidogenic Cytochrome P450 17A1 over Cytochrome P450 21A2", J Med Chem., 2018, 61: 4946-4960).

Figure 45:
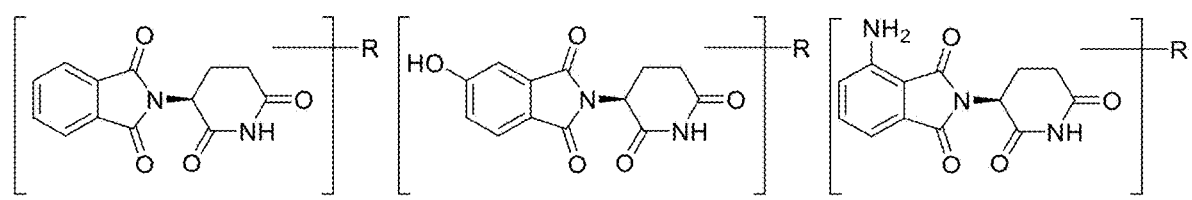

FIG. 45 provides non-limiting examples SALL4 Targeting Ligands, wherein R represents exemplary points at which the Linker can be attached. For additional examples, see the crystal structure PDB 7BQU, 7BQV (Furihata, H., et al., "Structural bases of IMiD selectivity that emerges by 5-hydroxythalidomide", Nat Commun., 2020, 11: 4578-4578); and the crystal structure PDB 6UML (Matyskiela, M. E., et al., "Crystal structure of the SALL4-pomalidomide-cereblon-DDB1 complex", Nat Struct Mol Biol., 2020, 27: 319-322).

Figure 46:
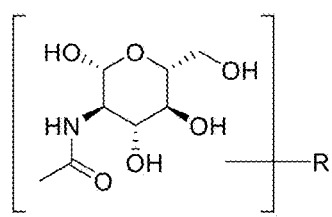

FIG. 46 provides non-limiting examples of FAM38 Targeting Ligands, wherein R represents exemplary points at which the Linker can be attached. For additional examples, see the crystal structure PDB 6KG7 (Wang, L., et al., "Structure and mechanogating of the mammalian tactile channel PIEZO2.", Nature, 2019, 573: 225-229).

Figure 47:
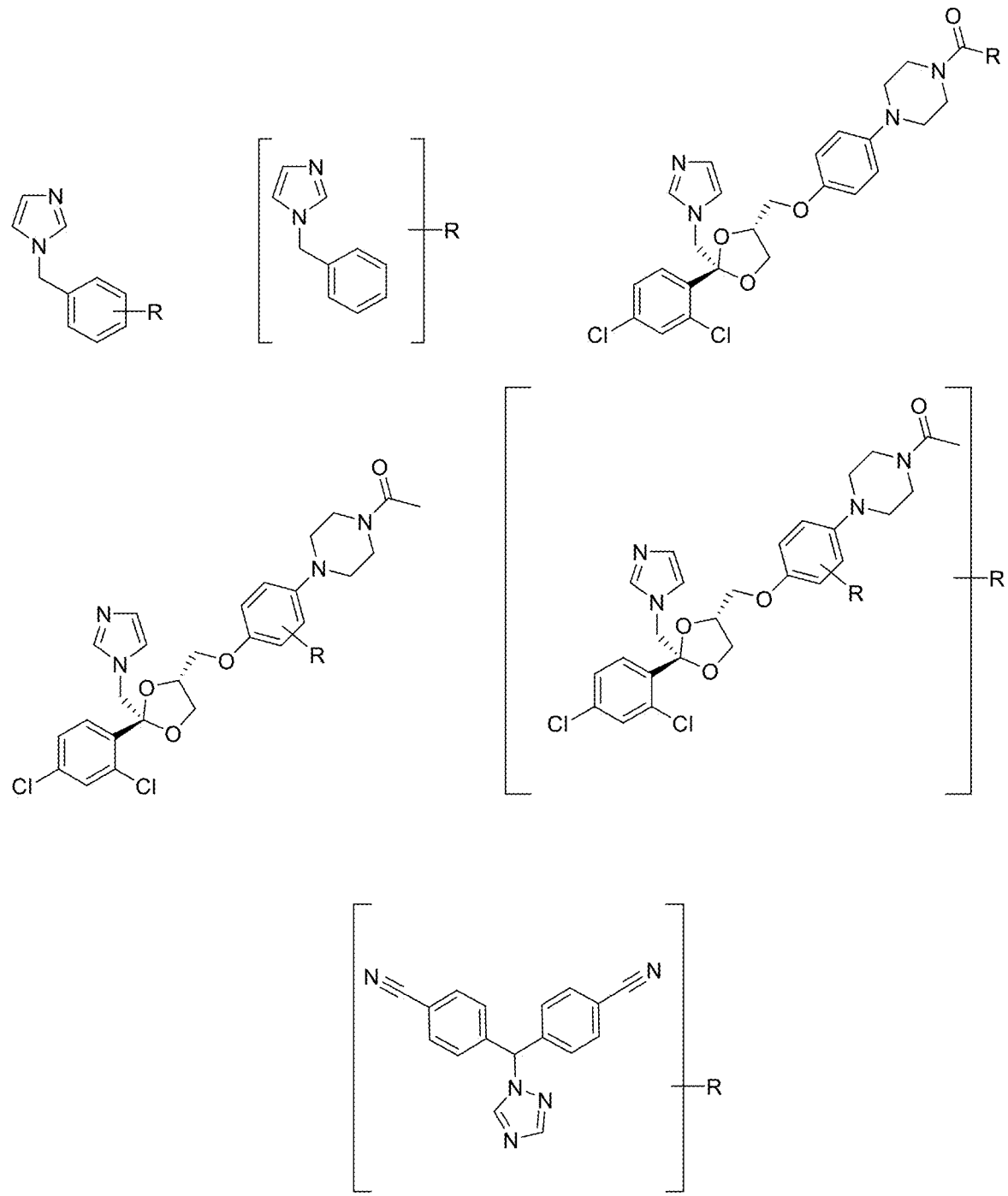

FIG. 47 provides non-limiting examples of CYP20A1 Targeting Ligands, wherein R represents exemplary points at which the Linker can be attached. For additional examples, see Durairaj et al. *Biological Chemistry*, 2020, 401(3), 361-365.

Figure 48:
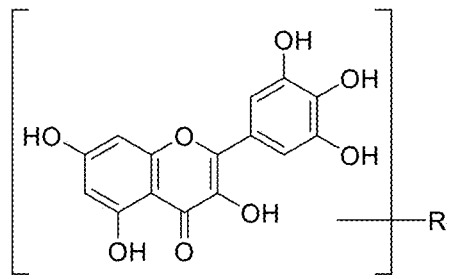

FIG. 48 provides non-limiting examples of HTT Targeting Ligands, wherein R represents exemplary points at which the Linker can be attached. For additional examples, see the crystal structure PDB 5XI1 (Khan, E., et al., "Myricetin Reduces Toxic Level of CAG Repeats RNA in Huntington's Disease (HD) and Spino Cerebellar Ataxia (SCAs).", ACS Chem Biol., 2018, 13: 180-188).

Figure 49:
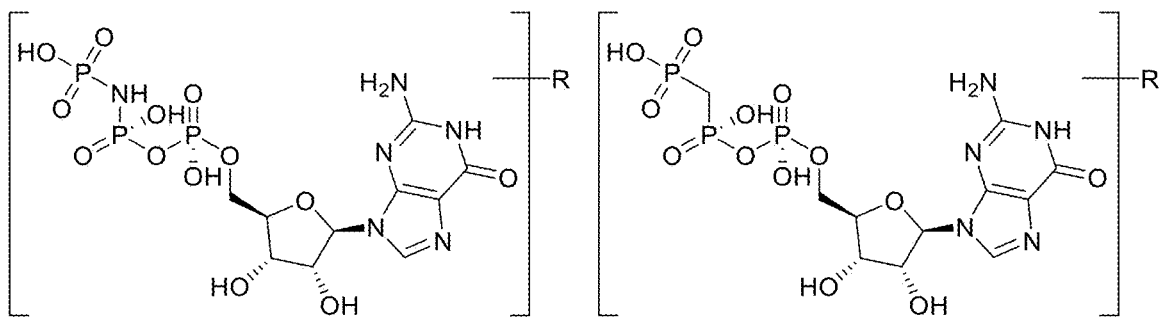

FIG. 49 provides non-limiting examples of KRAS Targeting Ligands, wherein R represents exemplary points at which the Linker can be attached. For additional examples, see the crystal structure PDB 6CU6 (Hobbs, G. A., et al., "Atypical KRASG12RMutant Is Impaired in PI3K Signaling and Macropinocytosis in Pancreatic Cancer.", Cancer Discov., 2020, 10: 104-123); the crystal structure PDB 6GJ5, 6GJ6, 6GJ8, 6JG7, ("Drugging an Undruggable Pocket on KRAS" PNAS 2019 116 (32) 15823-15829); and the crystal structure PDB 6BP1 (Lu, J., et al., "KRAS Switch Mutants D33E and A59G Crystallize in the State 1 Conformation.", Biochemistry, 2018, 57: 324-333).

Figure 50:
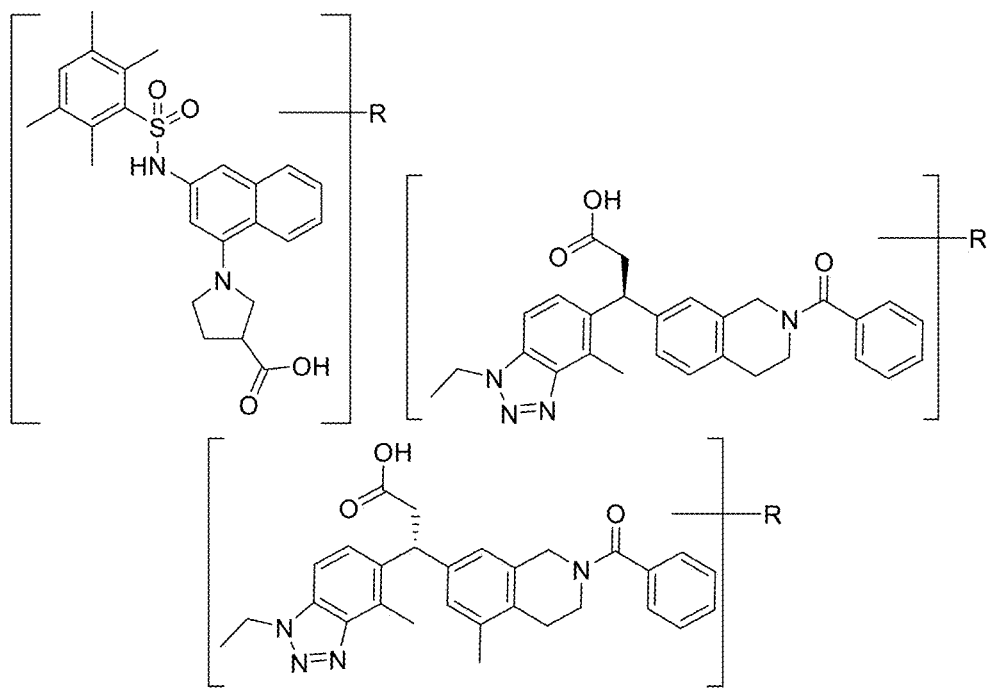

FIG. 50 provides non-limiting examples of NRF2 (NFE2L2) Targeting Ligands, wherein R represents exemplary points at which the Linker can be attached. For additional examples, see the crystal structure PDB 5CGJ (Winkel, A. F., et al., "Characterization of RA839, a Non-covalent Small Molecule Binder to Keap1 and Selective Activator of Nrf2 Signaling.", J Biol Chem., 2015, 290: 28446-28455); and 6TYM, 6TYP (Ma, B., et al., "Design, synthesis and identification of novel, orally bioavailable non-covalent Nrf2 activators", Bioorg Med Chem Lett., 2020, 30: 126852-126852).

Figure 51:
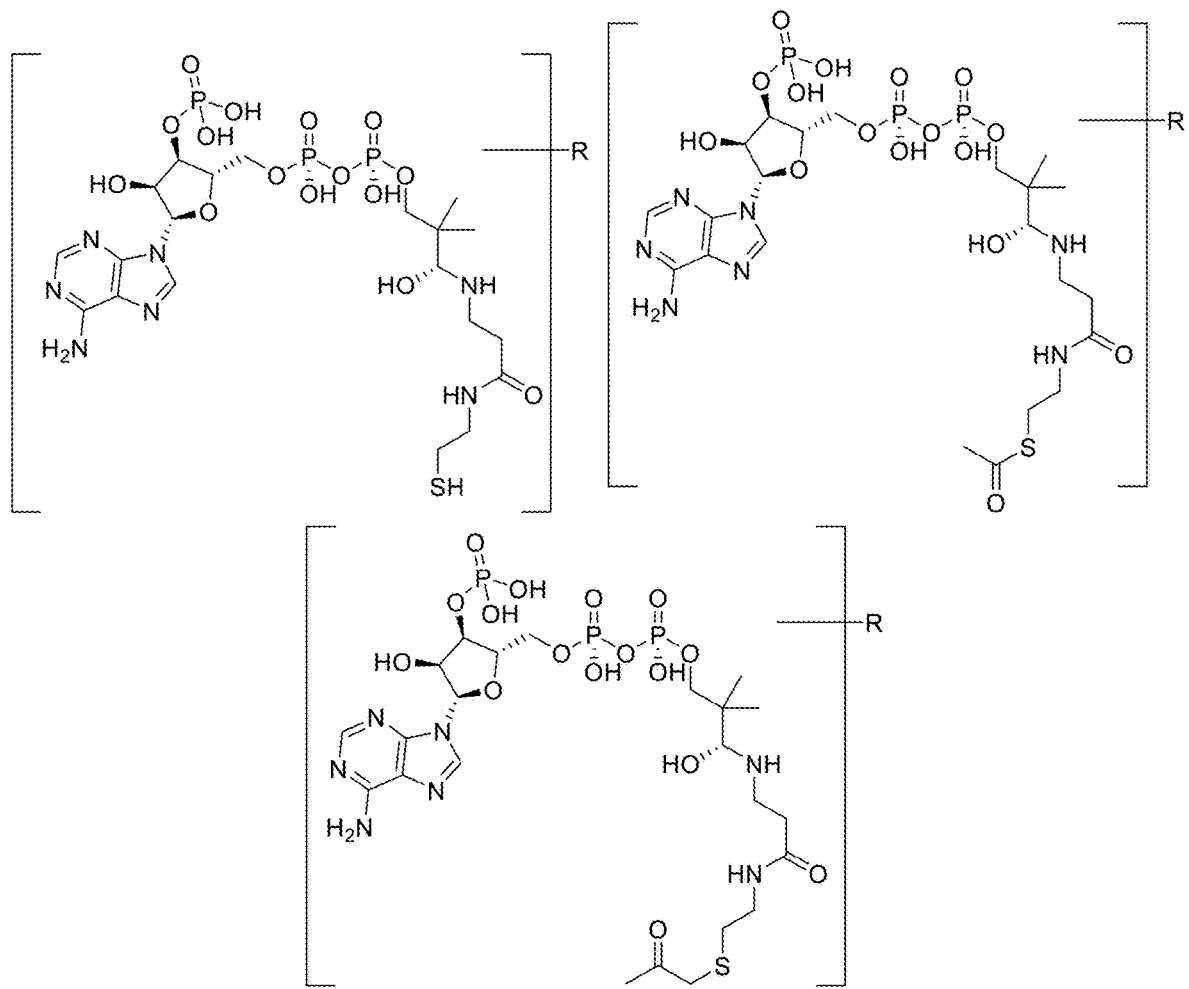

FIG. 51 provides non-limiting examples of P300 Targeting Ligands, wherein R represents exemplary points at which the Linker can be attached. For additional examples, see the crystal structure PDB 4PZR, 4PZS, 4PZT (Maksimoska, J., et al., "Structure of the p300 Histone Acetyltransferase Bound to Acetyl-Coenzyme A and Its Analogues", Biochemistry, 2014, 53: 3415-3422); and the crystal structure PDB 6PGU (Gardberg, A. S., et al., "Make the right measurement: Discovery of an allosteric inhibition site for p300-HAT", Struct Dyn., 2019, 6: 054702-054702).

Figure 52:
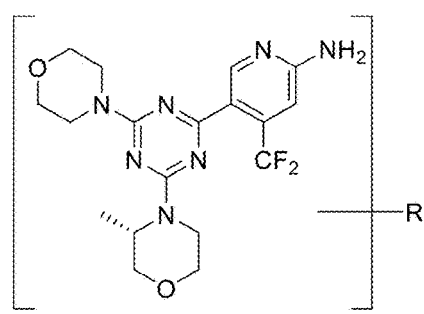

FIG. 52 provides non-limiting examples of PIK3CA Targeting Ligands, wherein R represents exemplary points at which the Linker can be attached. For additional examples, see the crystal structure PDB 6OAC (Rageot, D., et al., "(S)-4-(Difluoromethyl)-5-(4-(3-methylmorpholino)-6-morpholino-1,3,5-triazin-2-yl)pyridin-2-amine (PQR530), a Potent, Orally Bioavailable, and Brain-Penetrable Dual Inhibitor of Class I PI3K and mTOR Kinase", J Med Chem., 2019, 62: 6241-6261); and the crystal structure PDB 5SX8, 5SWP (Miller, M. S. et al., "Identification of allosteric binding sites for PI3K alpha oncogenic mutant specific inhibitor design.", Bioorg Med Chem., 2017, 25: 1481-1486).

Figure 53:
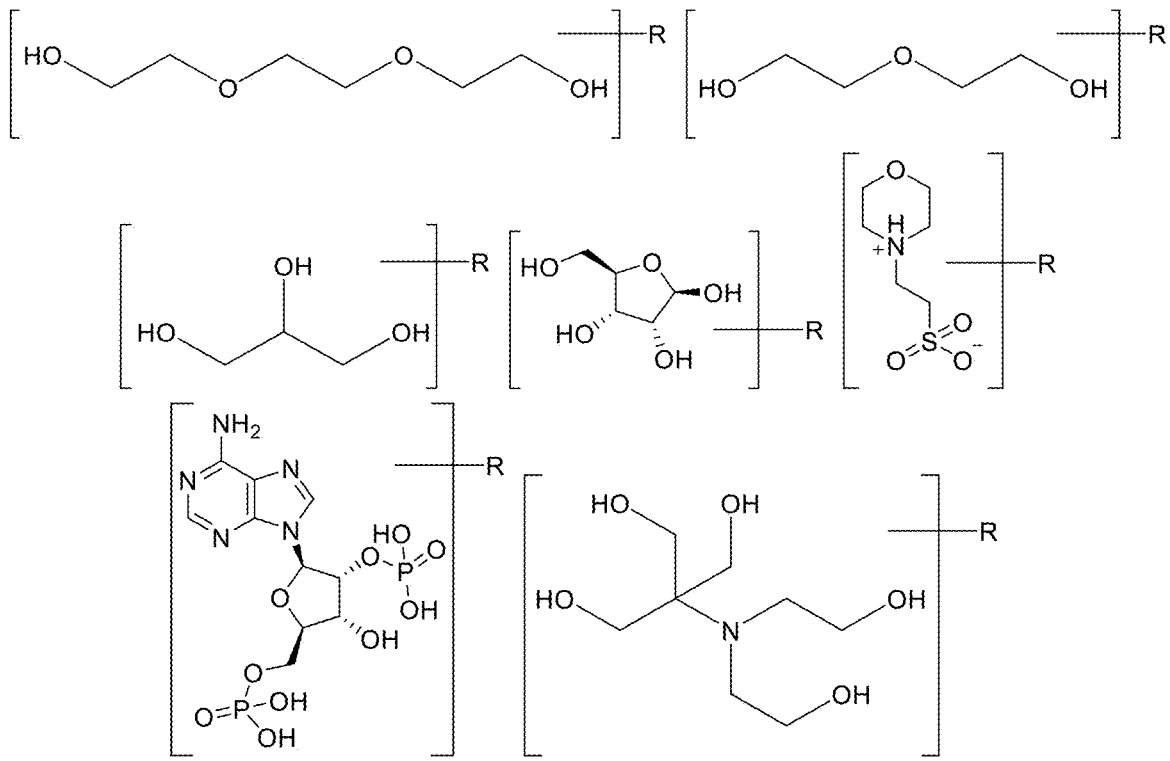

FIG. 53 provides non-limiting examples of SARM1 Targeting Ligands, wherein R represents exemplary points at which the Linker can be attached. For additional examples, see the crystal structure PDB 6QWV (Sporny, M., et al., "Structural Evidence for an Octameric Ring Arrangement of SARM1", J Mol Biol., 2019, 431: 3591-3605); and the crystal structure PDB 6O0Q, 6O0R, 6O0T, 6O0V, 6O0W (Horsefield, S., et al., "NAD+ cleavage activity by animal and plant TIR domains in cell death pathways", Science, 2019, 365: 793-799).

Figure 54:
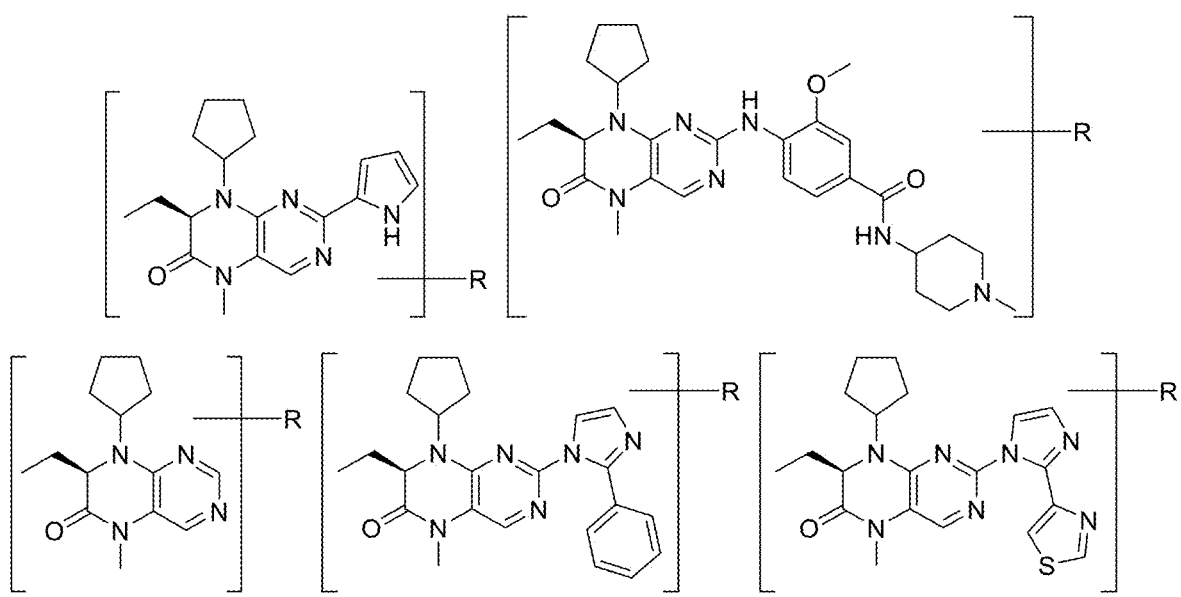

FIG. 54 provides non-limiting examples of SNCA Targeting Ligands, wherein R represents exemplary points at which the Linker can be attached. For additional examples, see the crystal structure PDB 4I5M, 4I5P, 4I6B, 4I6F, 4I6H (Aubele, D. L., et al., "Selective and brain-permeable polo-like kinase-2 (Plk-2) inhibitors that reduce alpha-synuclein phosphorylation in rat brain", Chem Med Chem., 2013, 8: 1295-1313).

Figure 55:
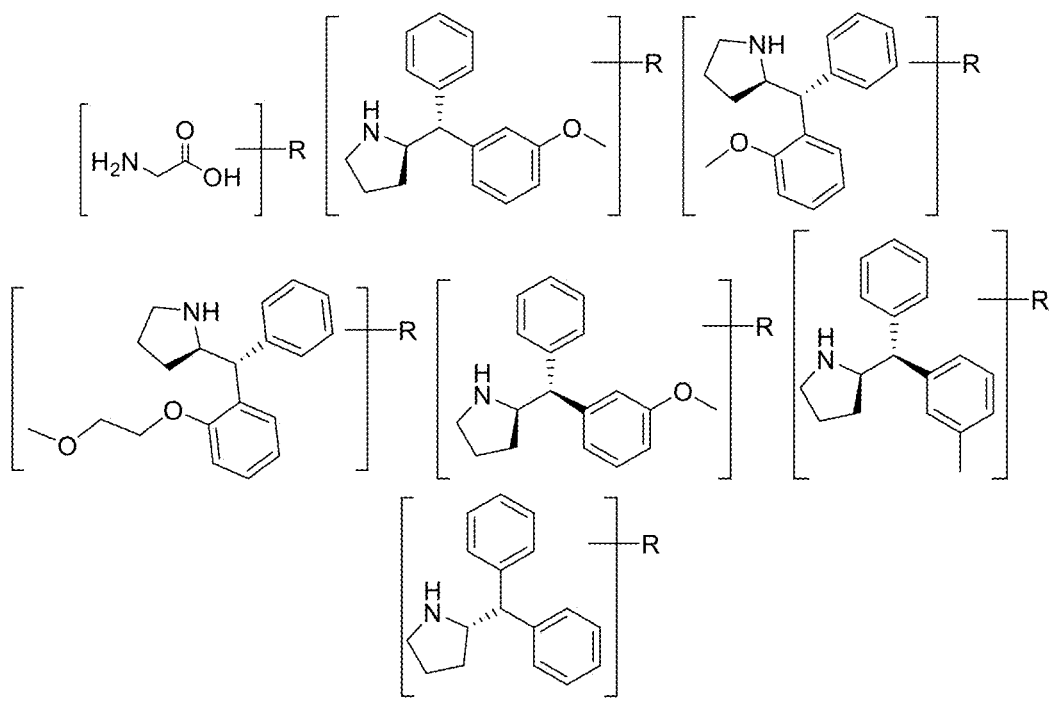

FIG. 55 provides non-limiting examples of MAPT Targeting Ligands, wherein R represents exemplary points at which the Linker can be attached. For example, the crystal structure PDB 6VI3, 6VHL (Arakhamia, T., et al., "Post-translational Modifications Mediate the Structural Diversity of Tauopathy Strains", Cell, 2020, 180: 633-644.e12); and the crystal structure PDB 6FAU, 6FAV, 6FAW, 6FBW, 6FBY, 6FI4, 6FI5 (Andrei, S. A., et al., "Inhibition of 14-3-3/Tau by Hybrid Small-Molecule Peptides Operating via Two Different Binding Modes.", ACS Chem Neurosci., 2018, 9: 2639-2654).

Figure 56:
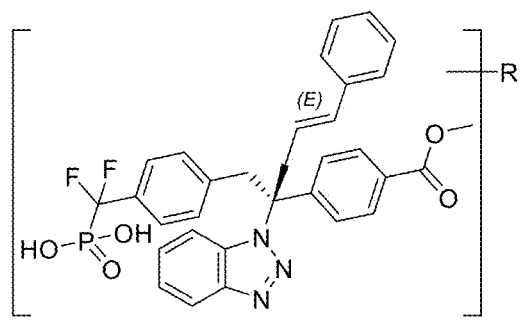

FIG. 56 provides non-limiting examples of PTPN2 or TCPTP Targeting Ligands, wherein R represents exemplary points at which the Linker can be attached. For example, the crystal structure PDB 2FJN, 2FJM (Asante-Appiah, E., et al., "Conformation-assisted inhibition of protein-tyrosine phosphatase-1B elicits inhibitor selectivity over T-cell protein-tyrosine phosphatase", J Biol Chem., 2006, 281: 8010-8015).

Figure 57:
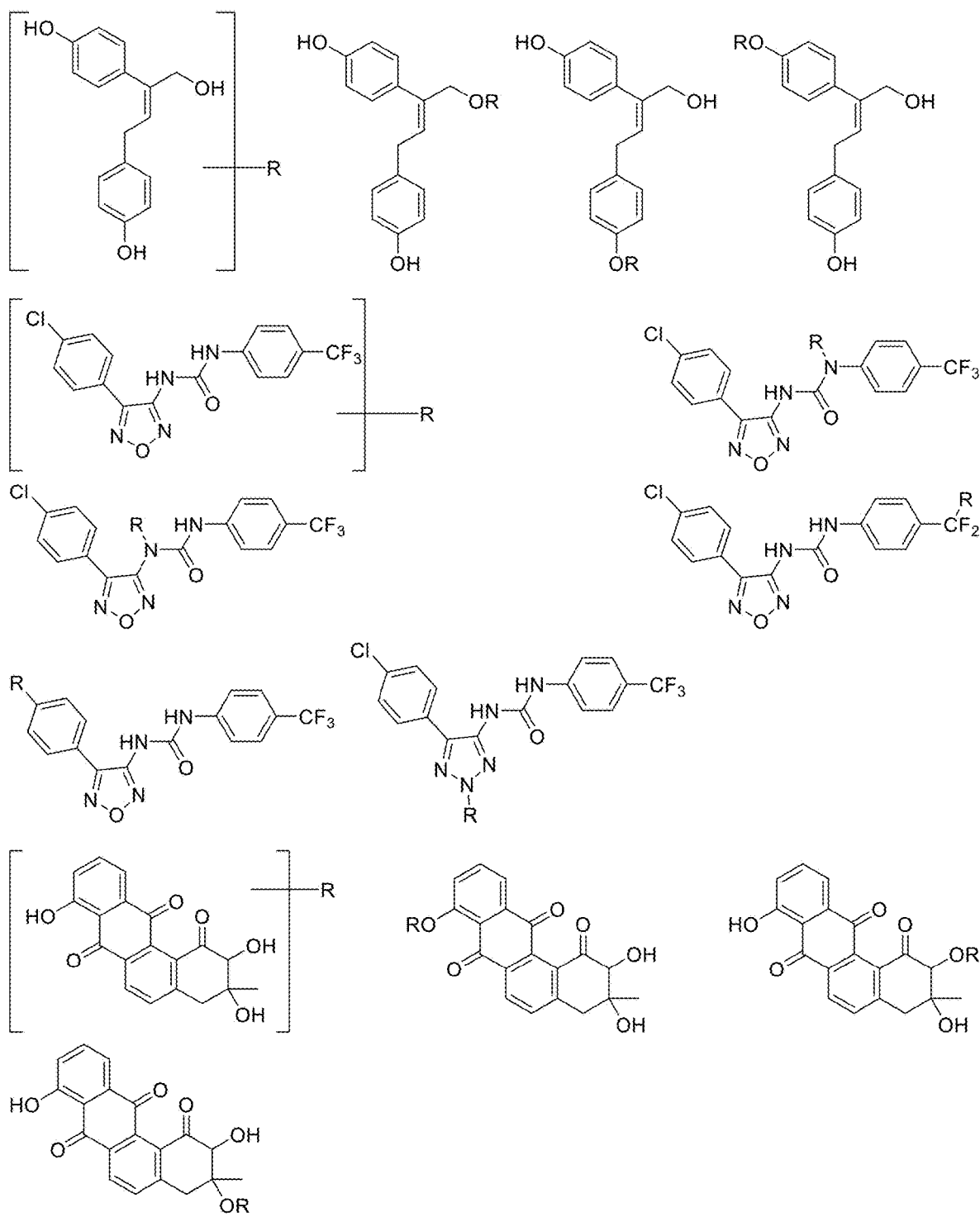

FIG. 57 provides non-limiting examples of STAT3 Targeting Ligands, wherein R represents exemplary points at which the Linker can be attached. The examples shown here derive from compounds in Zheng, W. et al. *MMPP Attenuates Non-Small Cell Lung Cancer Growth by Inhibiting the STAT3 DNA-Binding Activity via Direct Binding to the STAT3 DNA-Binding Domain, Theranostics* 2017, 7(18): 4632 and US2006/0247318. For additional examples, see Yang, L. et al. *Novel Activators and Small-Molecule Inhibitors of STAT3 in Cancer, Cytokine & Growth Factor Reviews* 2019, 49, 10-22.

Figure 58:
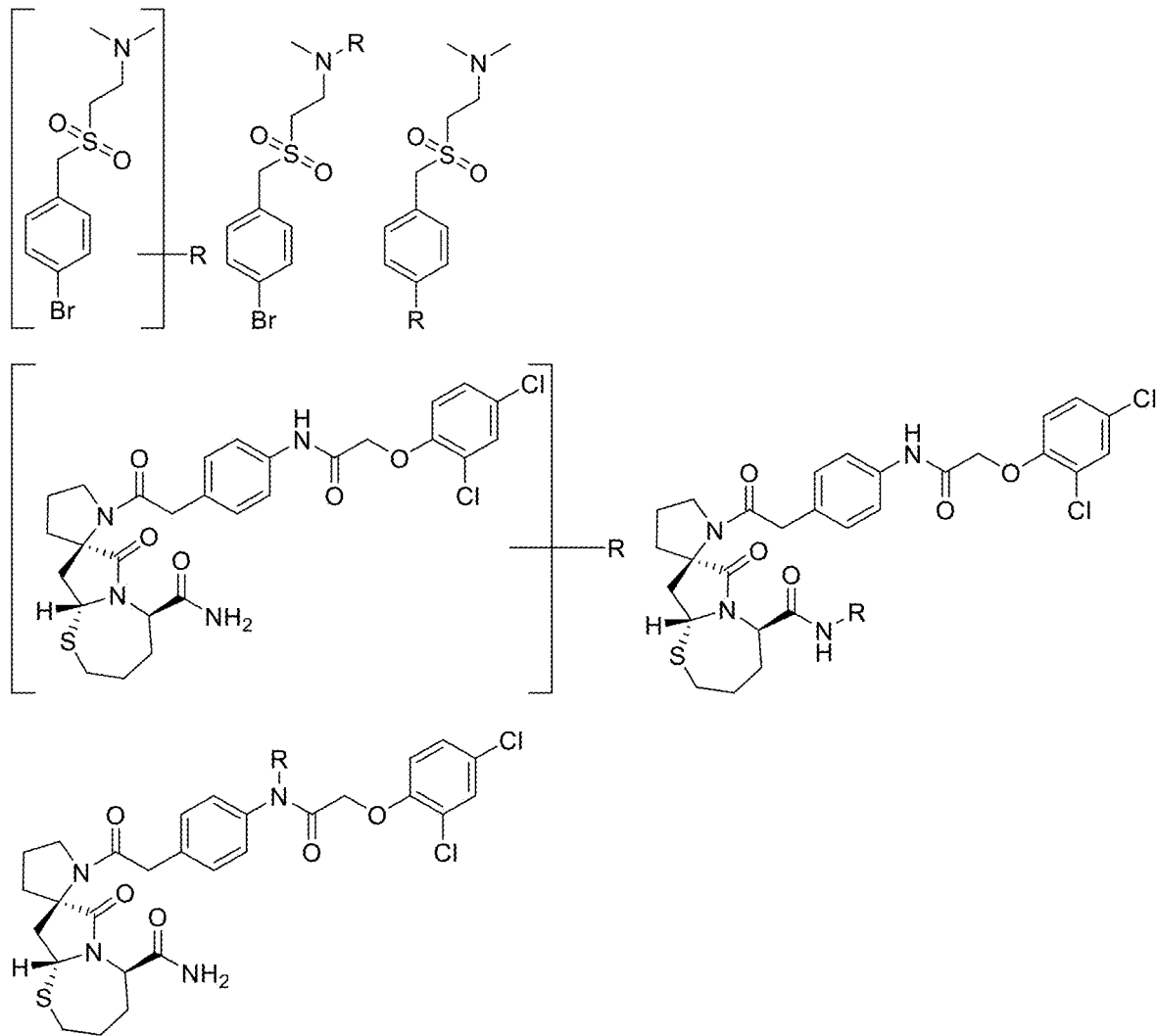

FIG. 58 provides non-limiting examples of MyD88 Targeting Ligands, wherein R represents exemplary points at which the Linker can be attached. The examples shown here derive from compounds in Sucking, C. et al *Small Molecule Analogues of the parasitic worm product ES-62 interact with the TIR domain of MyD88 to inhibitpro-inflammatory signaling* (2018) 8:2123 and Loiarro, M. et al *Pivotal Advance: Inhibition of MyD88 dimerization and recruitment of IRAK1 and IRAK4 by a novel peptidomimetic compound. Journal of Leukocyte Biology,* (2007) 82: 801-810.

Figure 59:
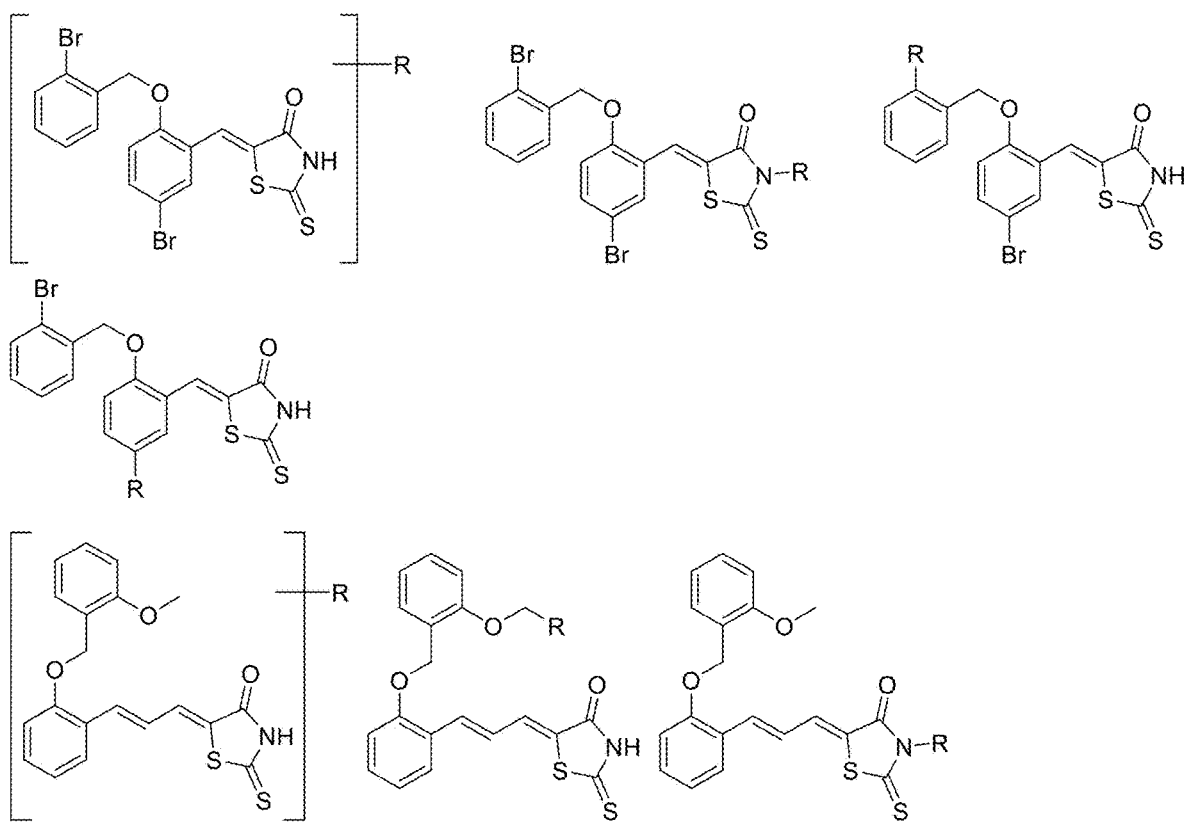

FIG. 59 provides non-limiting examples of PTP4A3 Targeting Ligands, wherein R represents exemplary points at which the Linker can be attached. The examples shown here derive from compounds in Ahn, J. et al *Synthesis and Biological Evaluation of RhodanineD derivatives as PRL-3Inhibitors Bioorganic & Medicinal Chemistry Letters* (2006) 16(11):2996-2999 and Min, G. et al *Rhodanine-Based PRL-3 Inhibitors Blocked the Migration and Invasion of Metastatic Cancer Cells Bioorganic & Medicinal Chemistry Letters* (2013) 23(13):3769-3774. For additional examples, see Tasker, N. et al *Tapping the Therapeutic Potential of Protein Tyrosine Phosphatase 4A with Small Molecule Inhibitors Bioorganic & Medicinal Chemistry Letters* (2019) 29(16):2008-2015.

Figure 60:
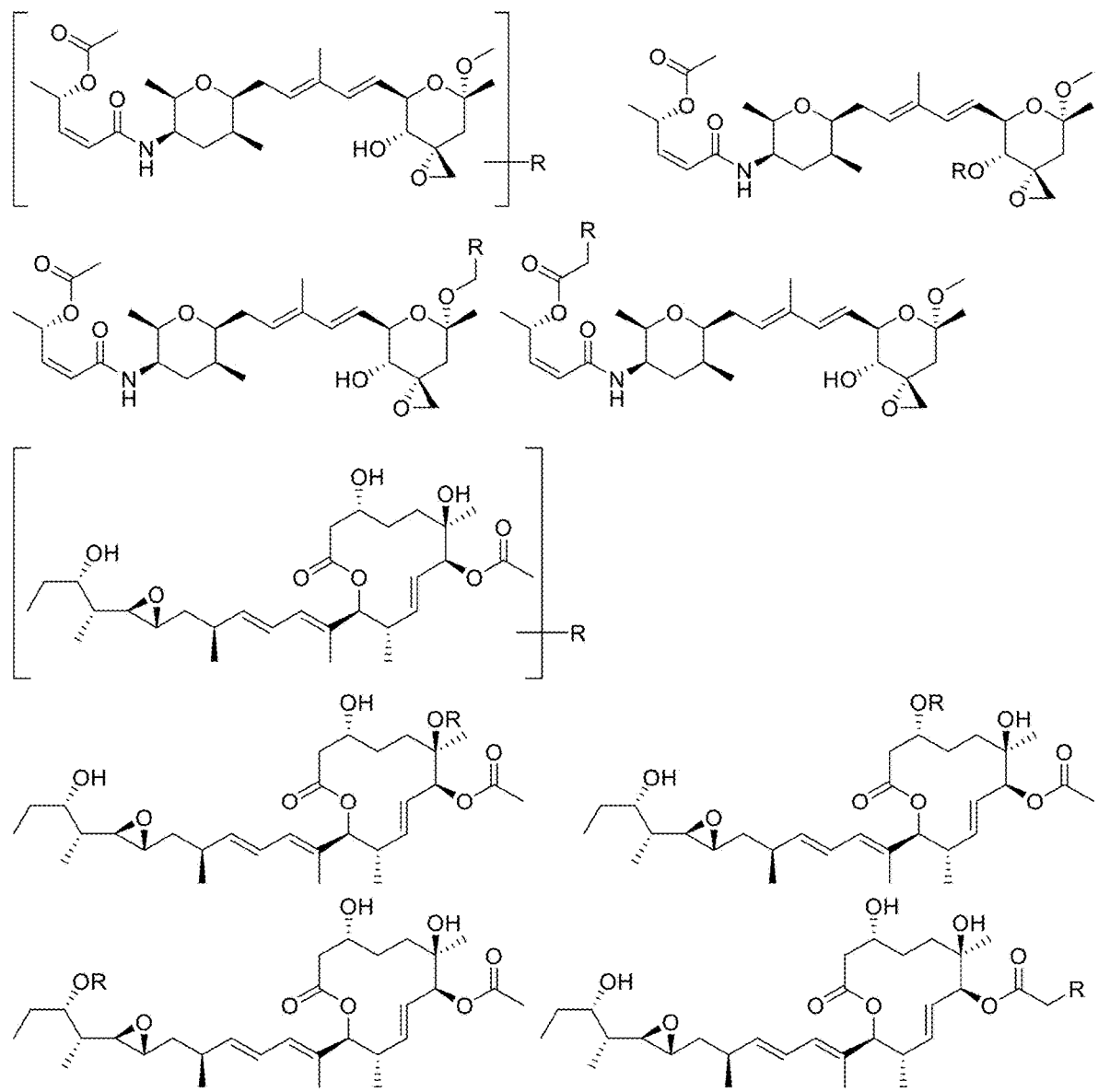

FIG. 60 provides non-limiting examples of SF3B1 Targeting Ligands, wherein R represents exemplary points at which the Linker can be attached. The examples shown here derive from compounds in Kaida, D. et al *Spliceostatin A Targets SF3b and Inhibits Both Splicing and Nuclear Reten-*

*tion of pre-mRNA Nature Chemical Biology* (2007) 3:576-583 and Kotake, Y. et al *Splicing Factor SF3b as a Target of the Antitumor Natural Product Pladienolide Nature Chemical Biology* (2007) 3:570-575. For additional examples, see Effenberger, K. et al *Modulating Splicing with Small Molecular Inhibitors of the Spliceosome* WIREs RNA (2016) 8:e1381.

Figure 61:
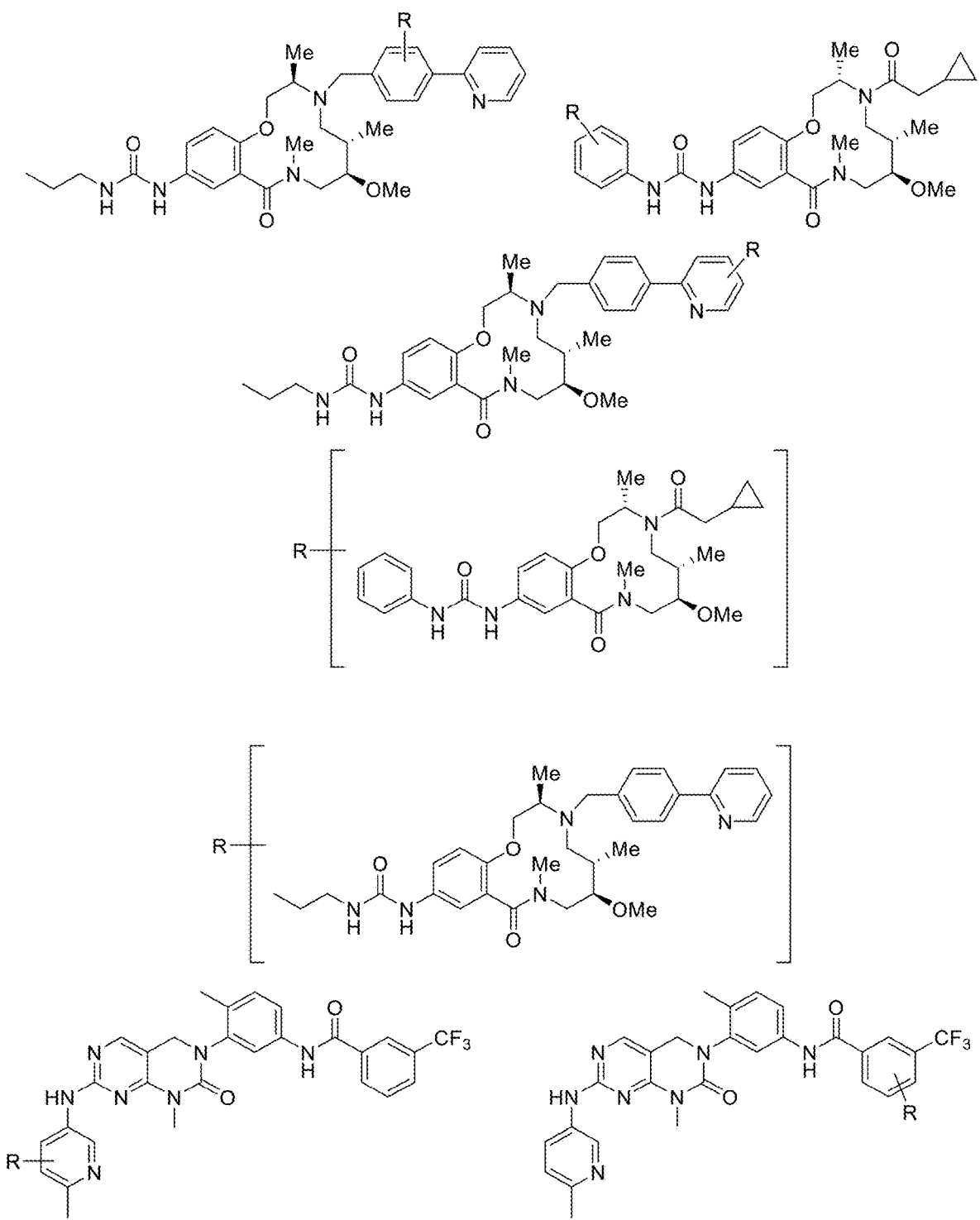

FIG. 61 provides non-limiting examples of ARID1B and ARID2 Targeting Ligands, wherein R represents exemplary points at which the Linker can be attached. For additional examples, see Chory et al. *ACS Chemical Biology* 2020, 15(6), 1685.

Figure 62:
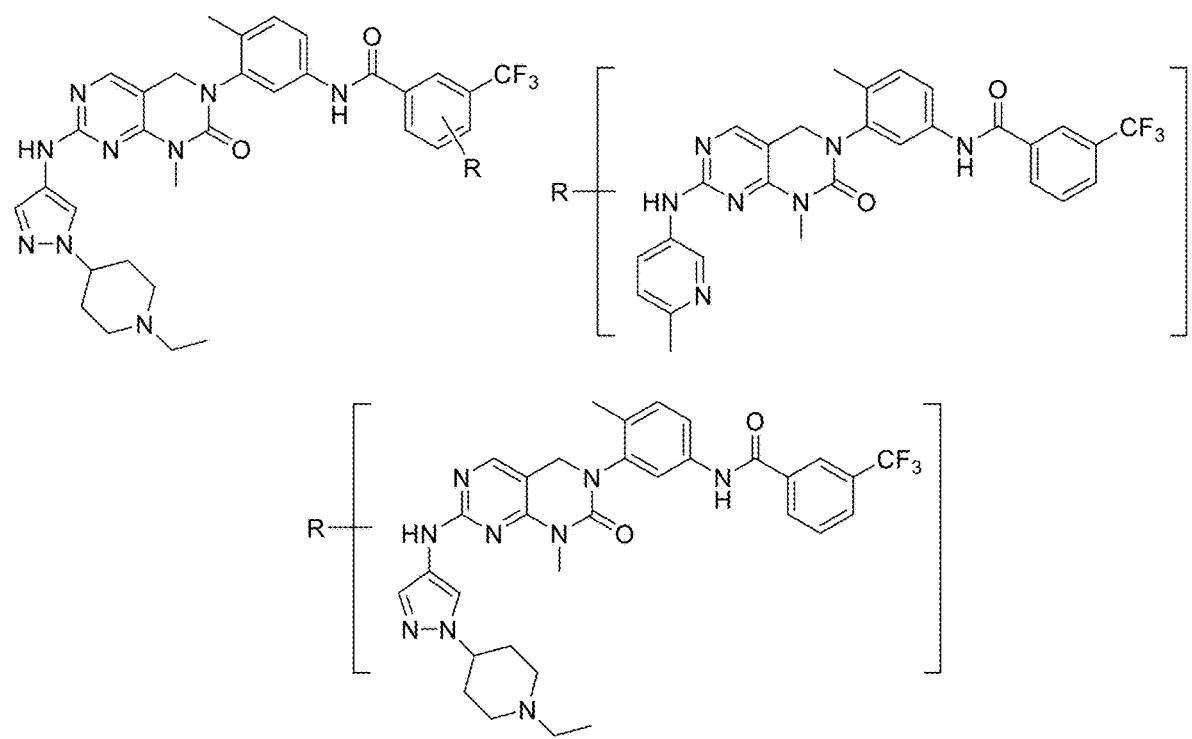
Figure 64A:
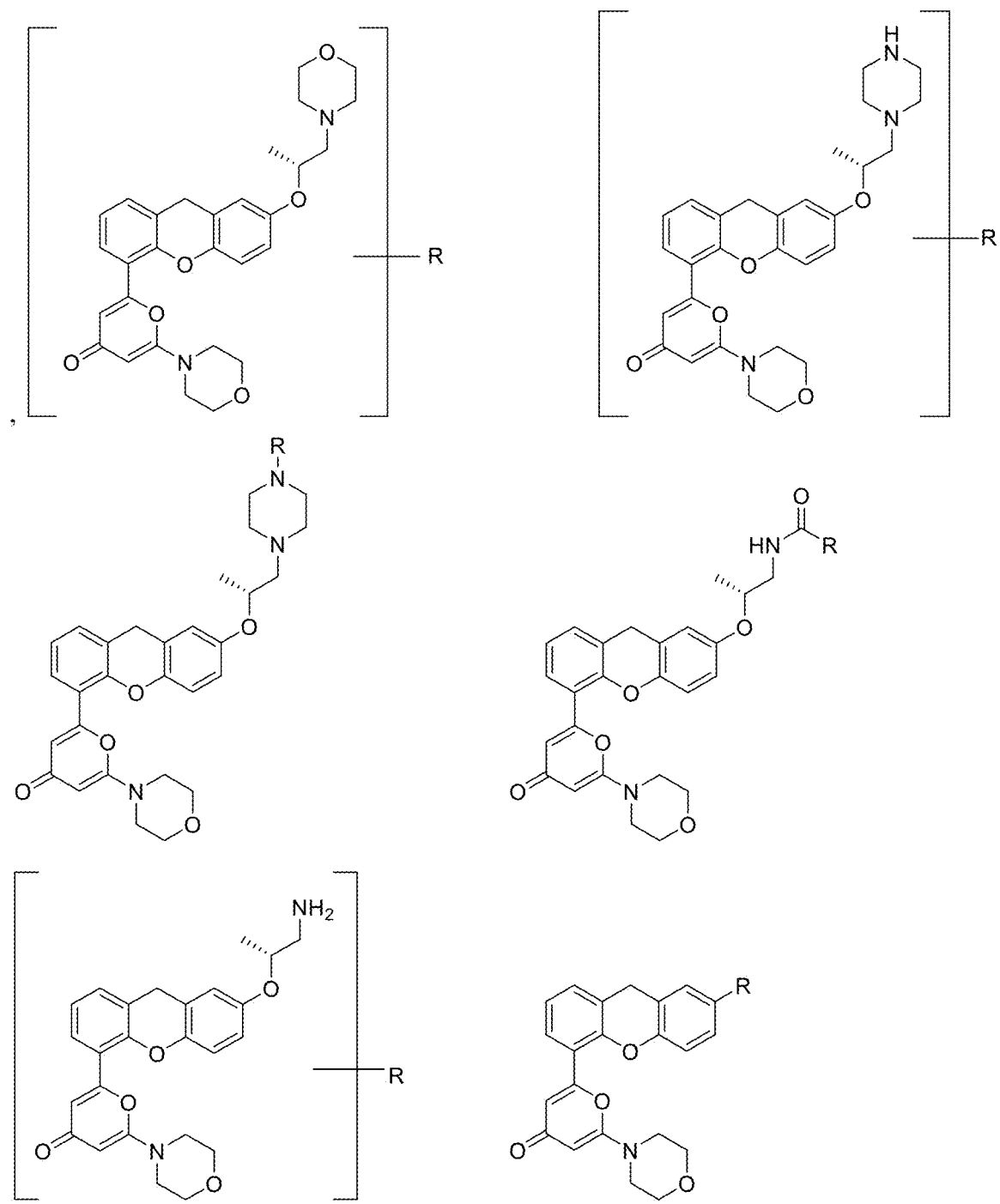
Figure 64B:
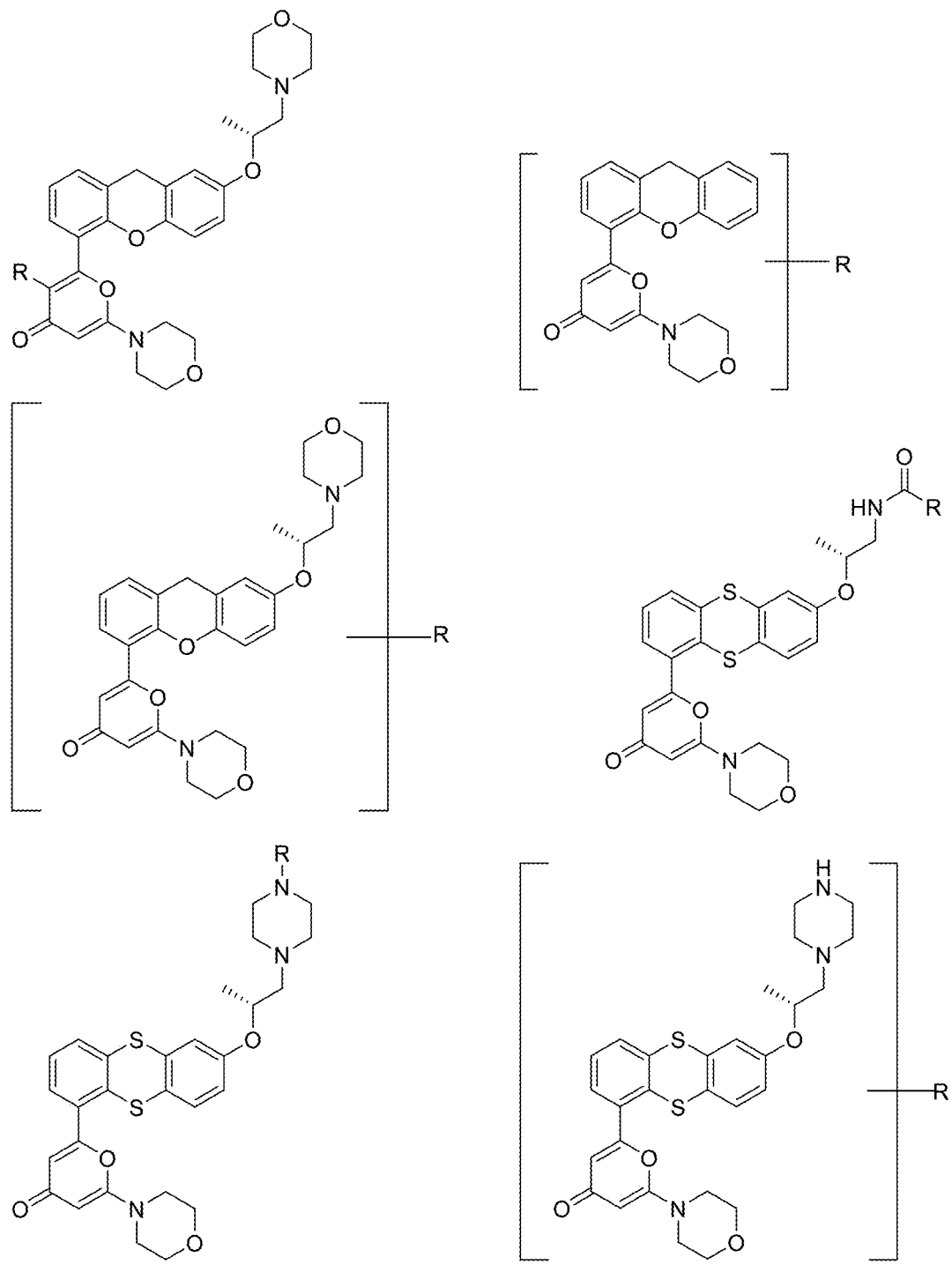
Figure 64C:
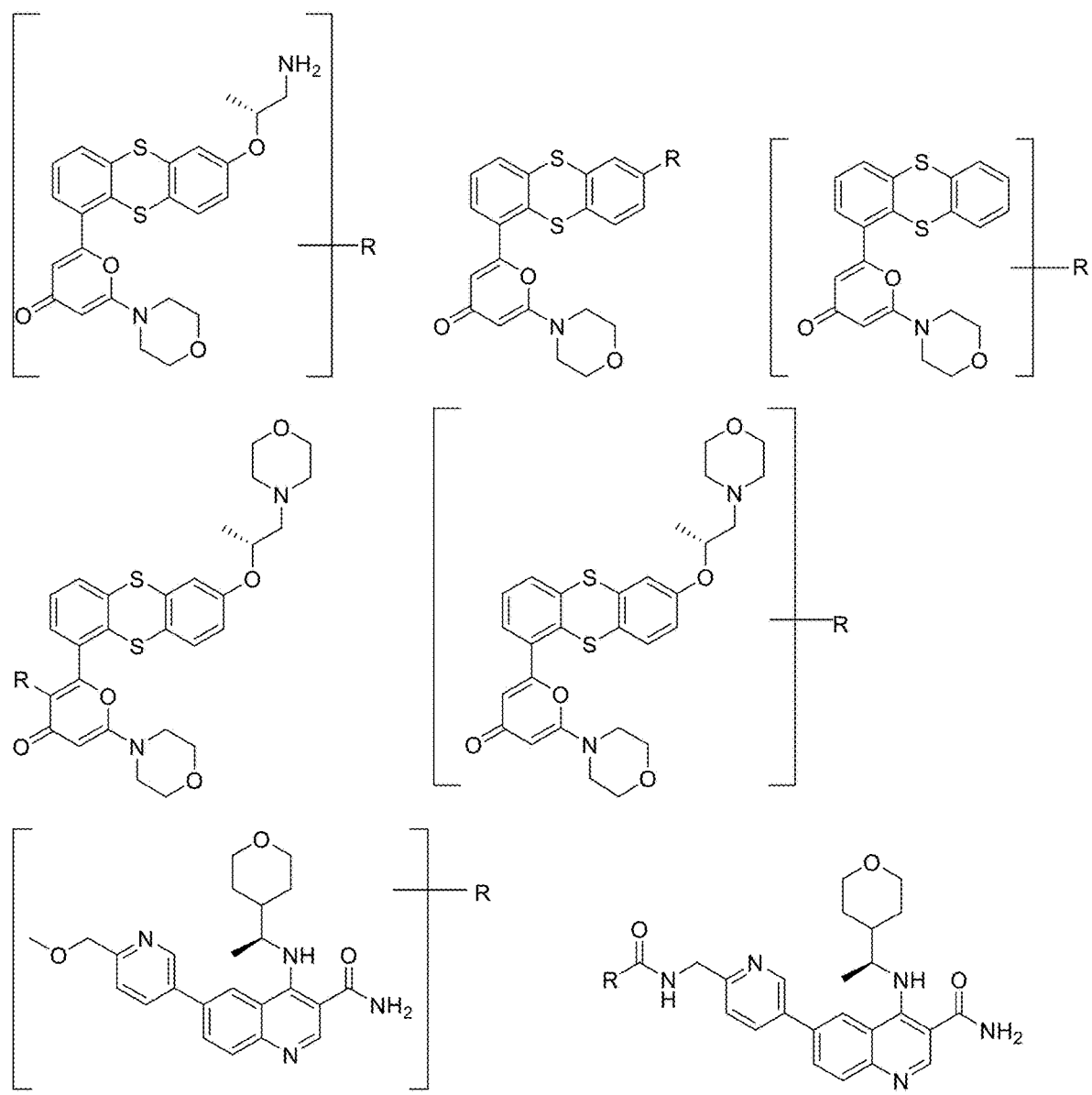
Figure 64D:
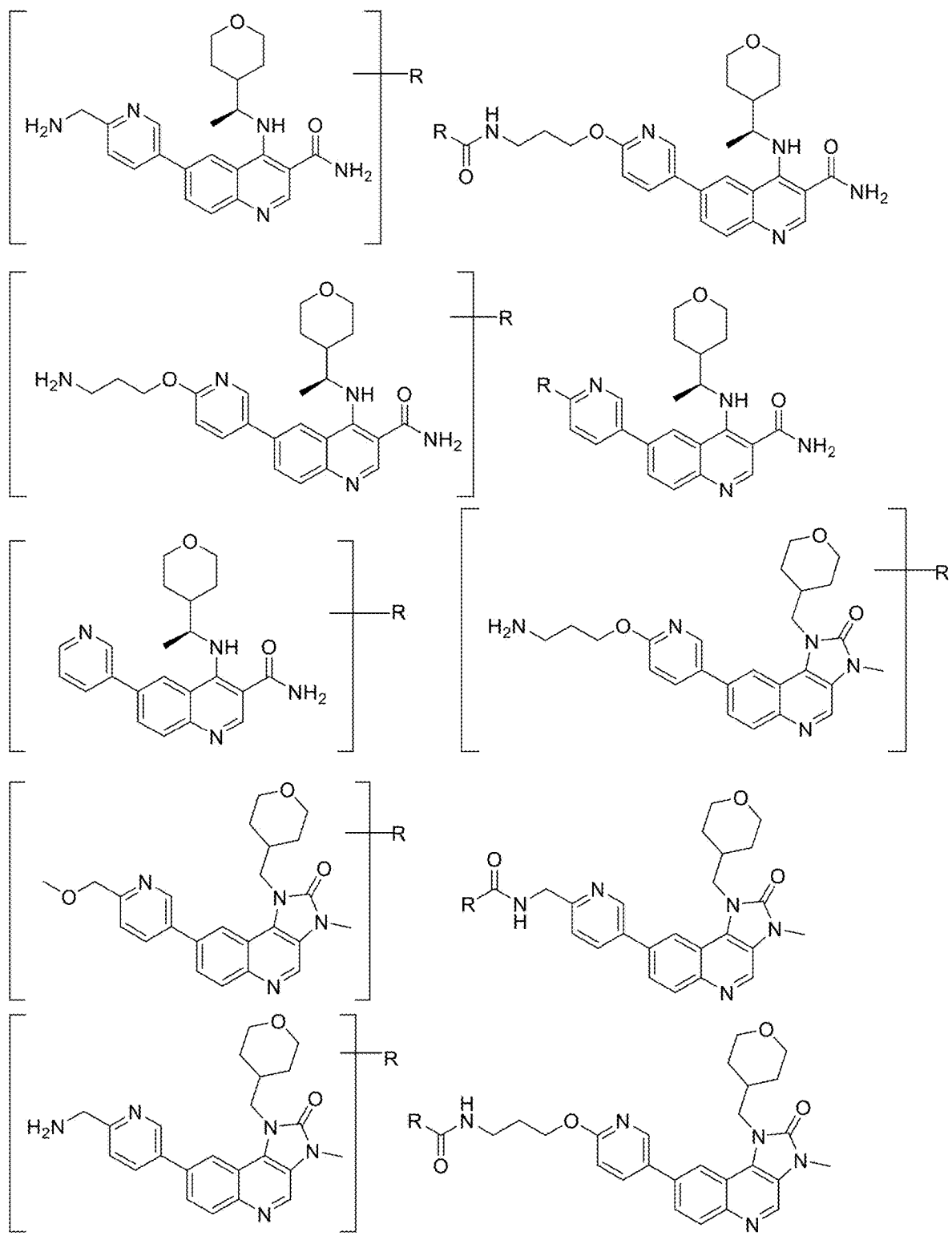
Figure 64E:
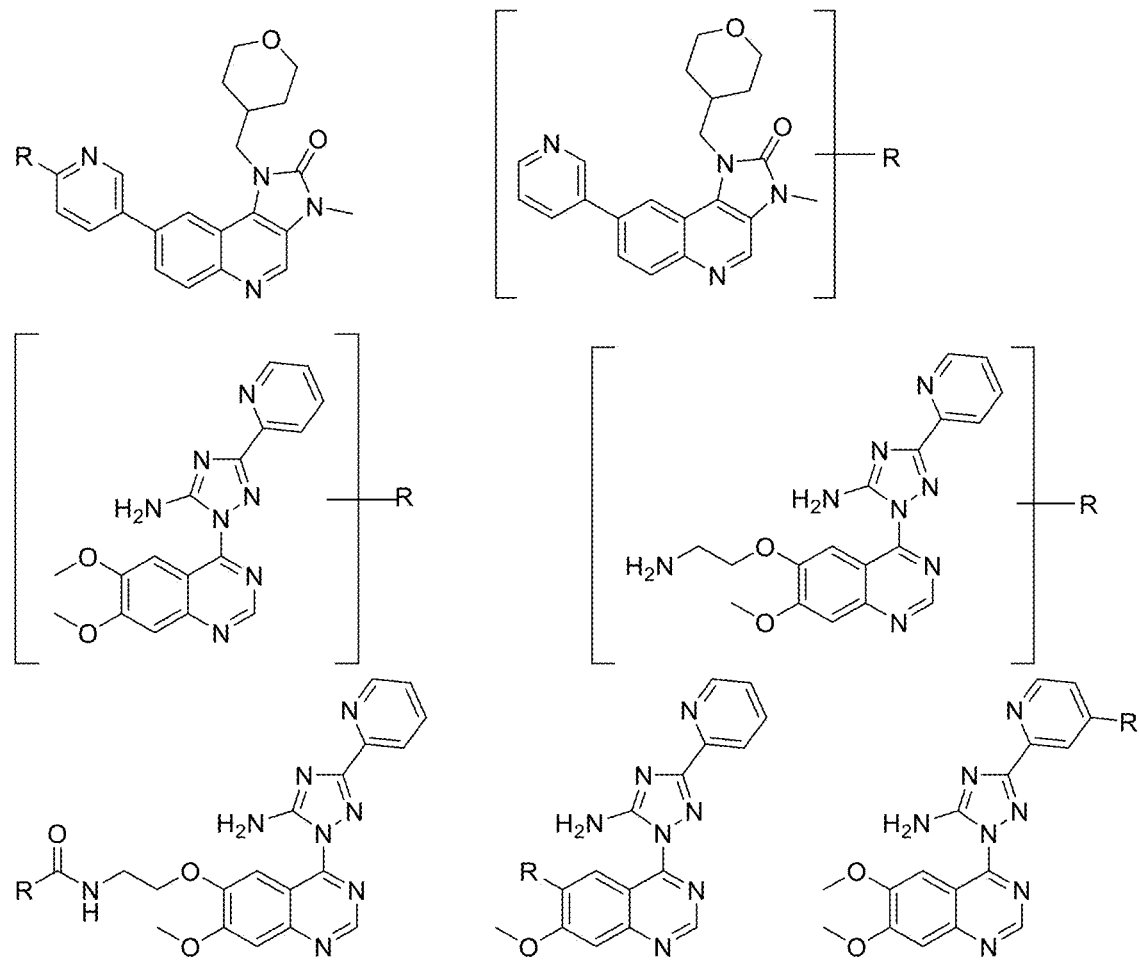

FIG. 62 provides non-limiting examples of Class II BRAF Mutant Targeting Ligands, wherein R represents exemplary points at which the Linker can be attached. For additional examples, see Cho et al. *Biochemical and Biophysical Research Communications* 2020, 352(2), 315.

FIG. 63 provides non-limiting examples of $NRAS^{Q61K}$ Targeting Ligands, wherein R represents exemplary points at which the Linker can be attached. For additional examples, see Song et al. *Am J Cancer Res* 2017, 7(4), 831 and Johnson et al. *Curr Treat Options Oncol.* 2015, 16(4), 15.

FIG. 64A-64E provide non-limiting examples of ataxia telangiectasia-mutated (ATM) kinase Targeting Ligands wherein R represents exemplary points at which the Linker is attached. Additional examples are provided in *J Med Chem,* 2019, 62: 2988-3008.

Figure 65A:
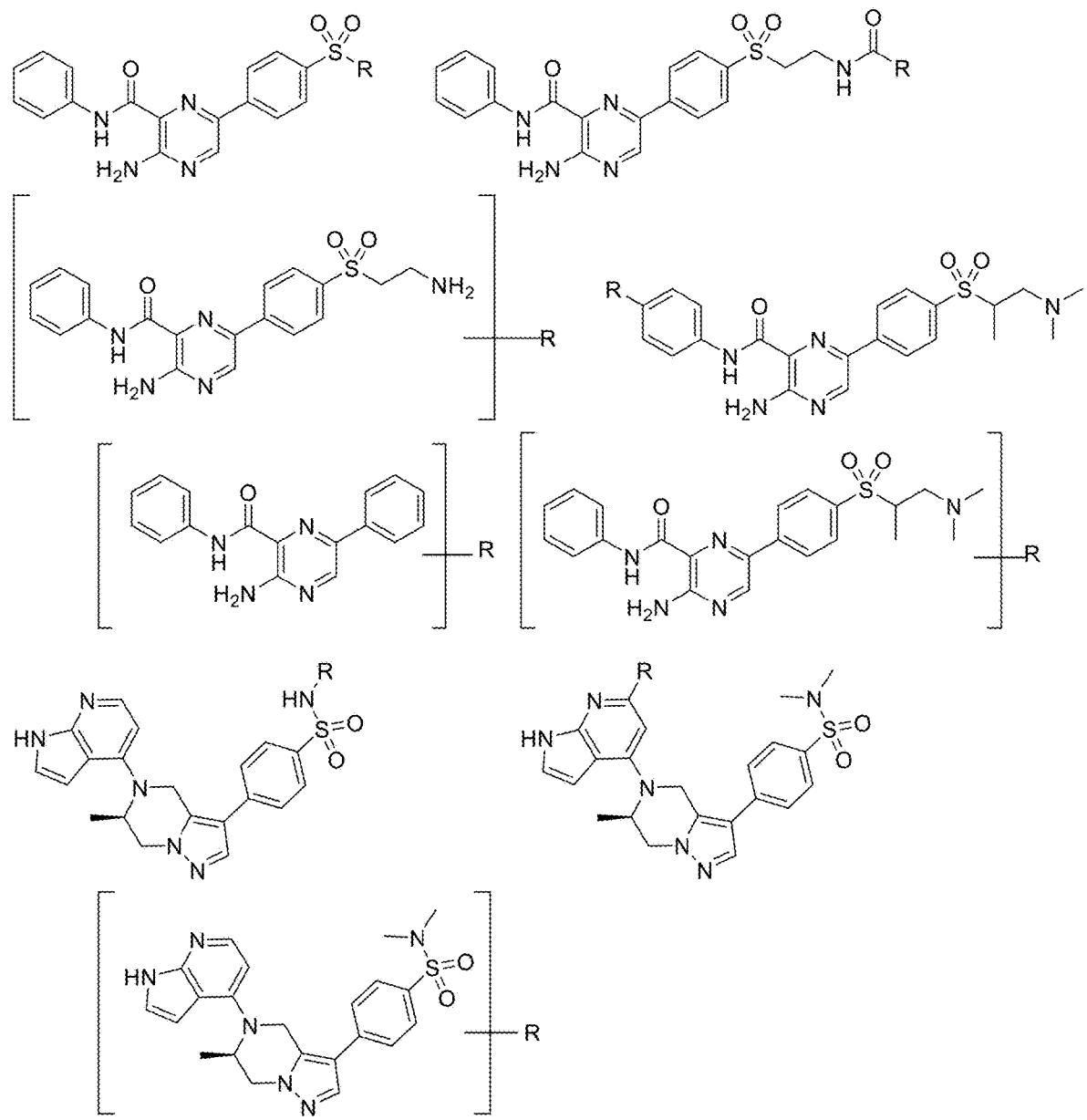
Figure 65B:
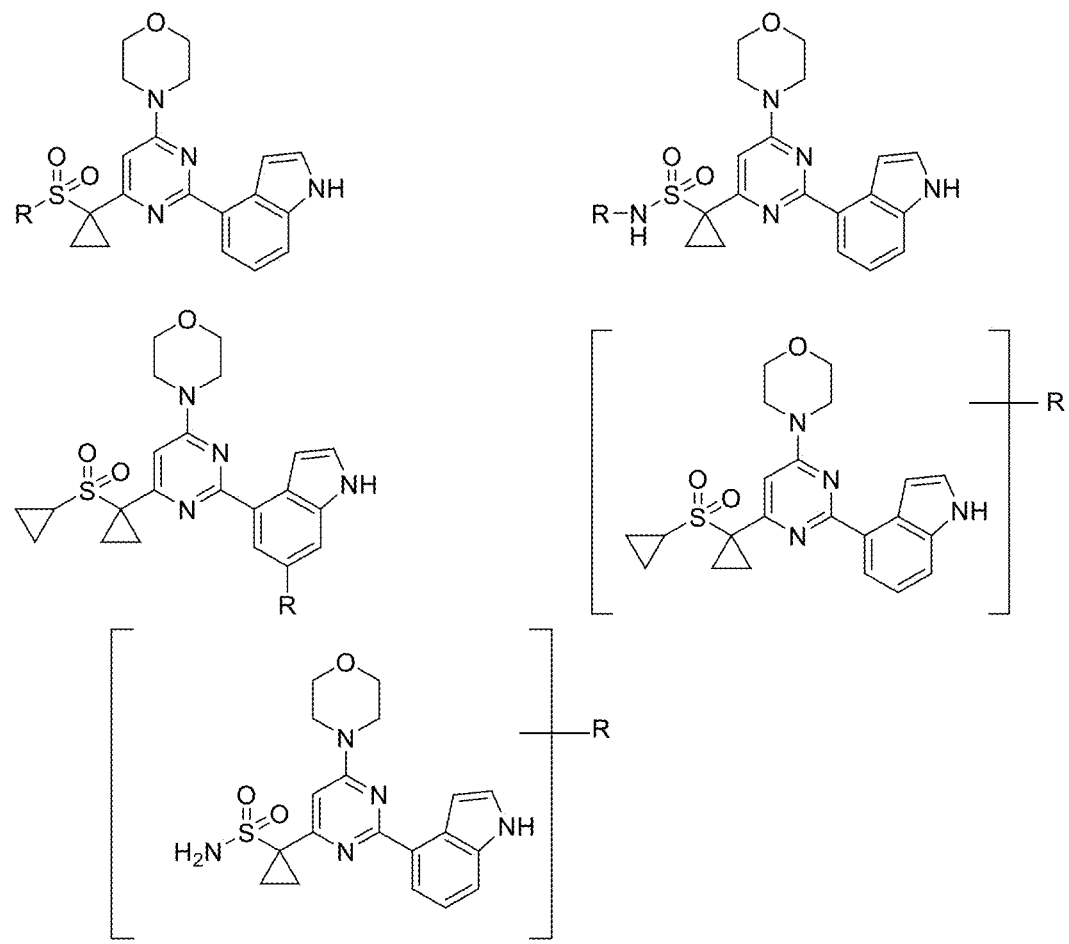

FIG. 65A-65B provide non-limiting examples of ATR Targeting Ligands wherein R represents exemplary points at which the Linker is attached. Additional examples are provided in *Journal of Molecular Biology* Volume 429, Issue 11, 2 Jun. 2017, Pages 1684-1704.

Figure 66A:
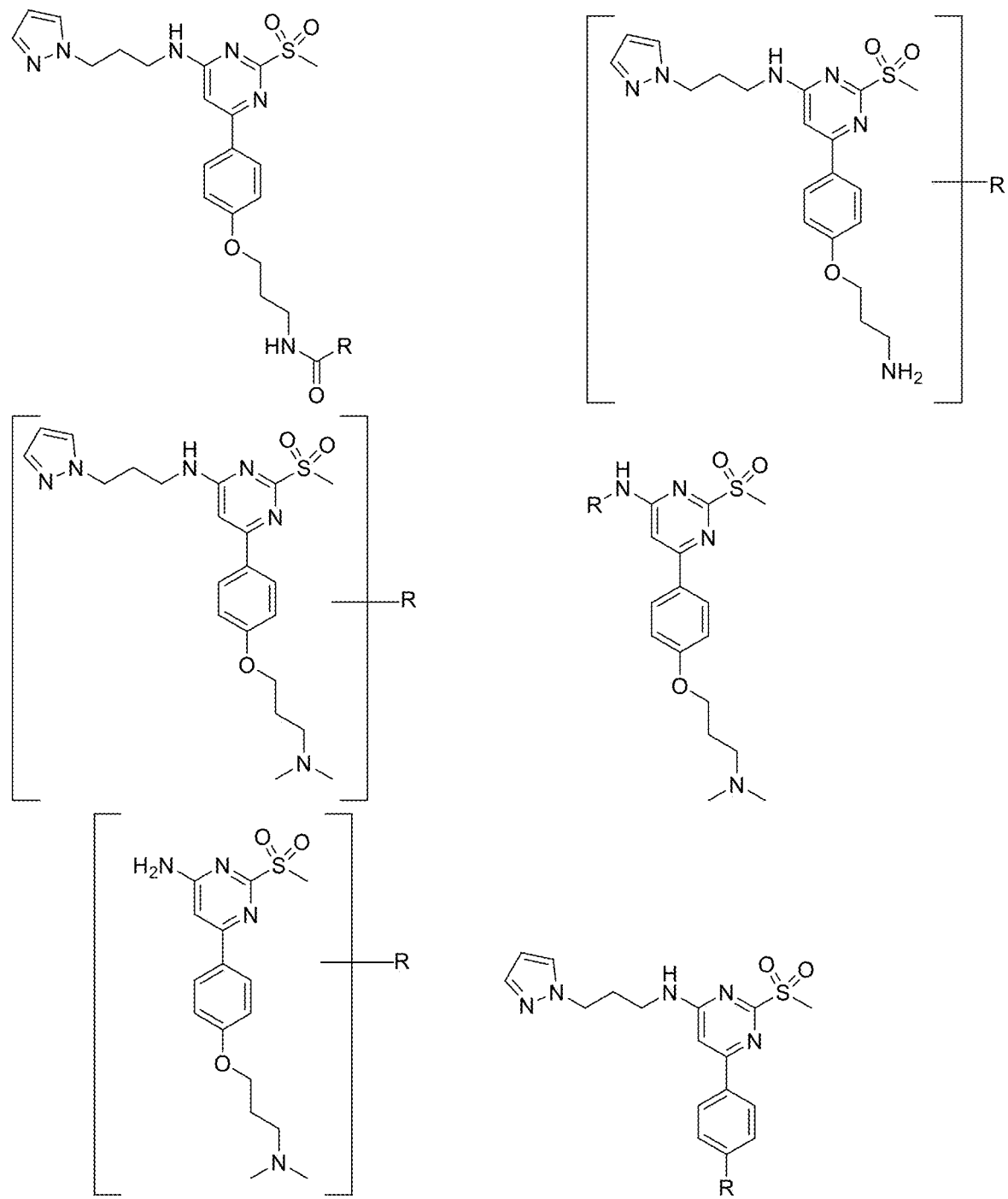
Figure 66B:
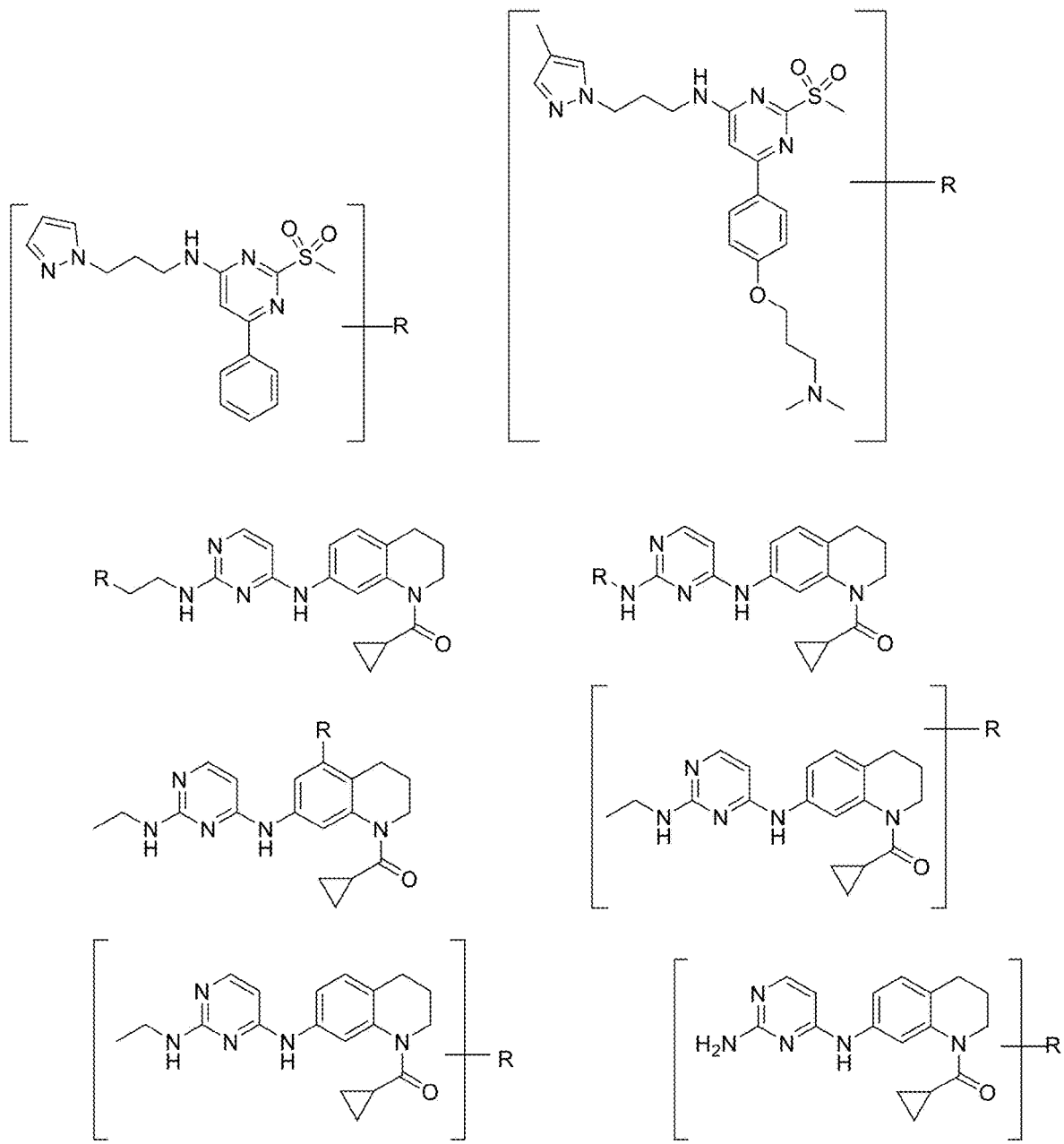
Figure 66C:
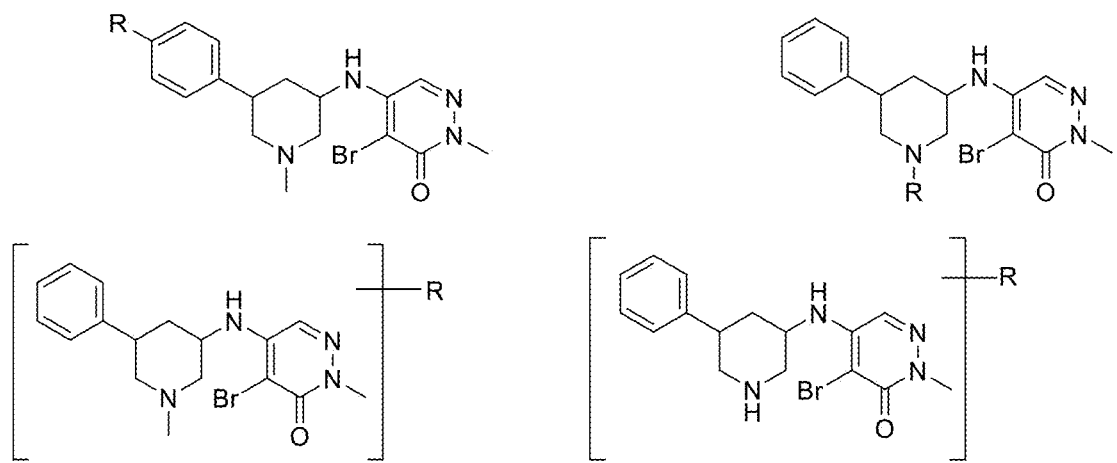

FIG. 66A-66C provide non-limiting examples of BPTF Targeting Ligands wherein R represents exemplary points at which the Linker is attached. Additional examples are provided in Organic & Biomolecular Chemistry 2020, 18(27): 5174-5182.

Figure 67A:
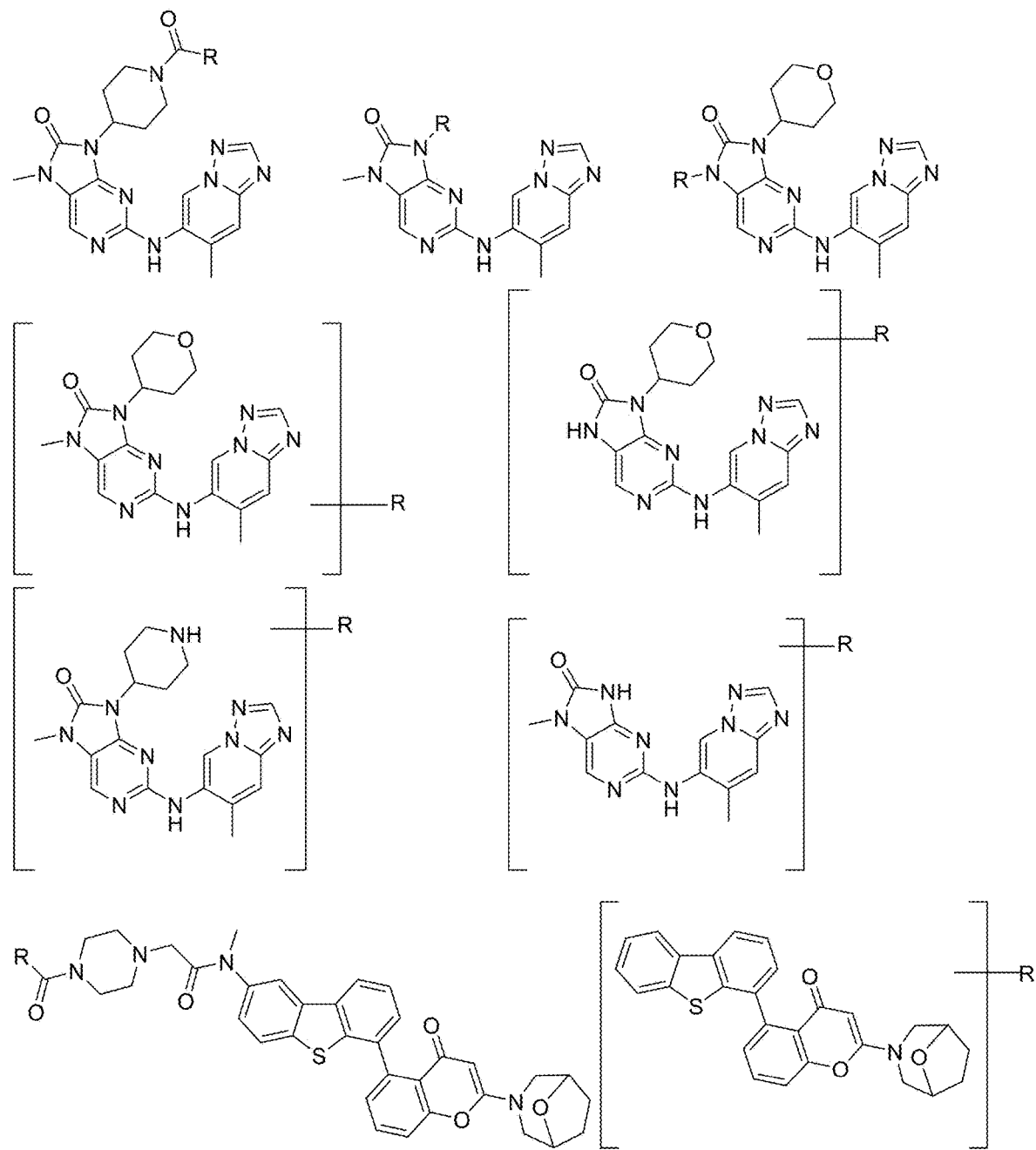
Figure 67B:
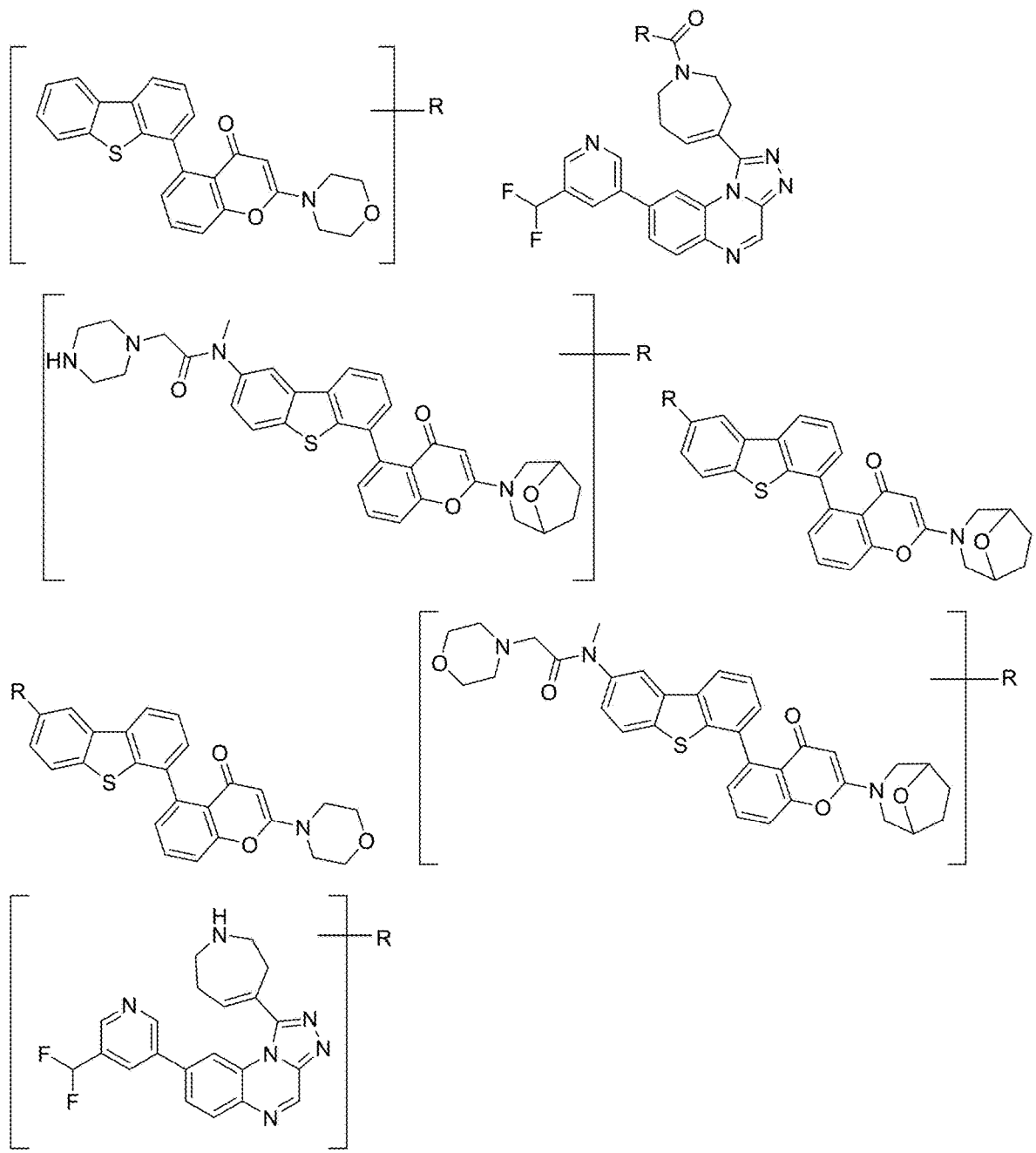

FIG. 67A-67B provide non-limiting examples of DNA-PK Targeting Ligands wherein R represents exemplary points at which the Linker is attached. Additional examples are provided in J. Med. Chem. 2020, 63, 7, 3461-3471.

Figure 68A:
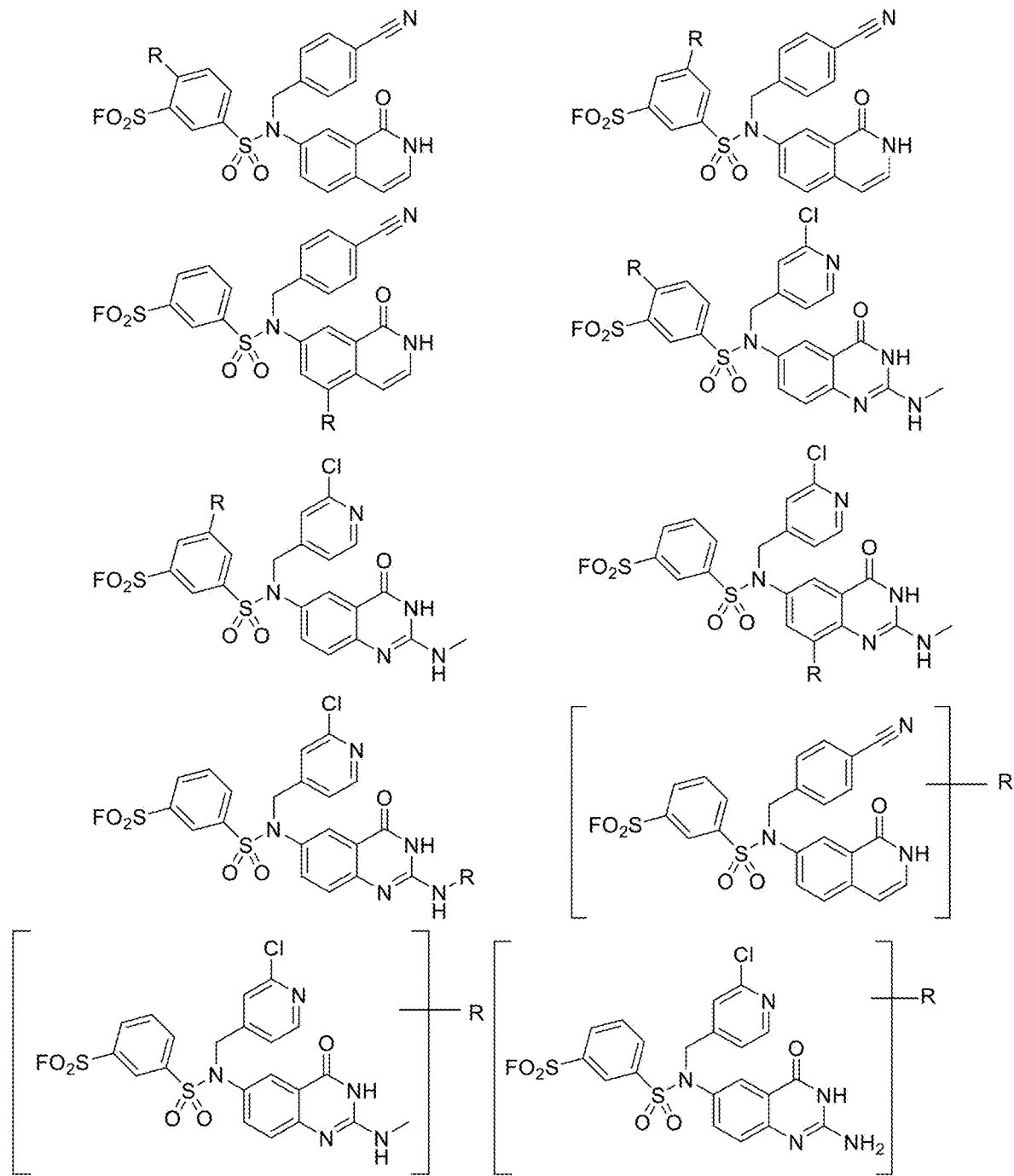
Figure 68B:
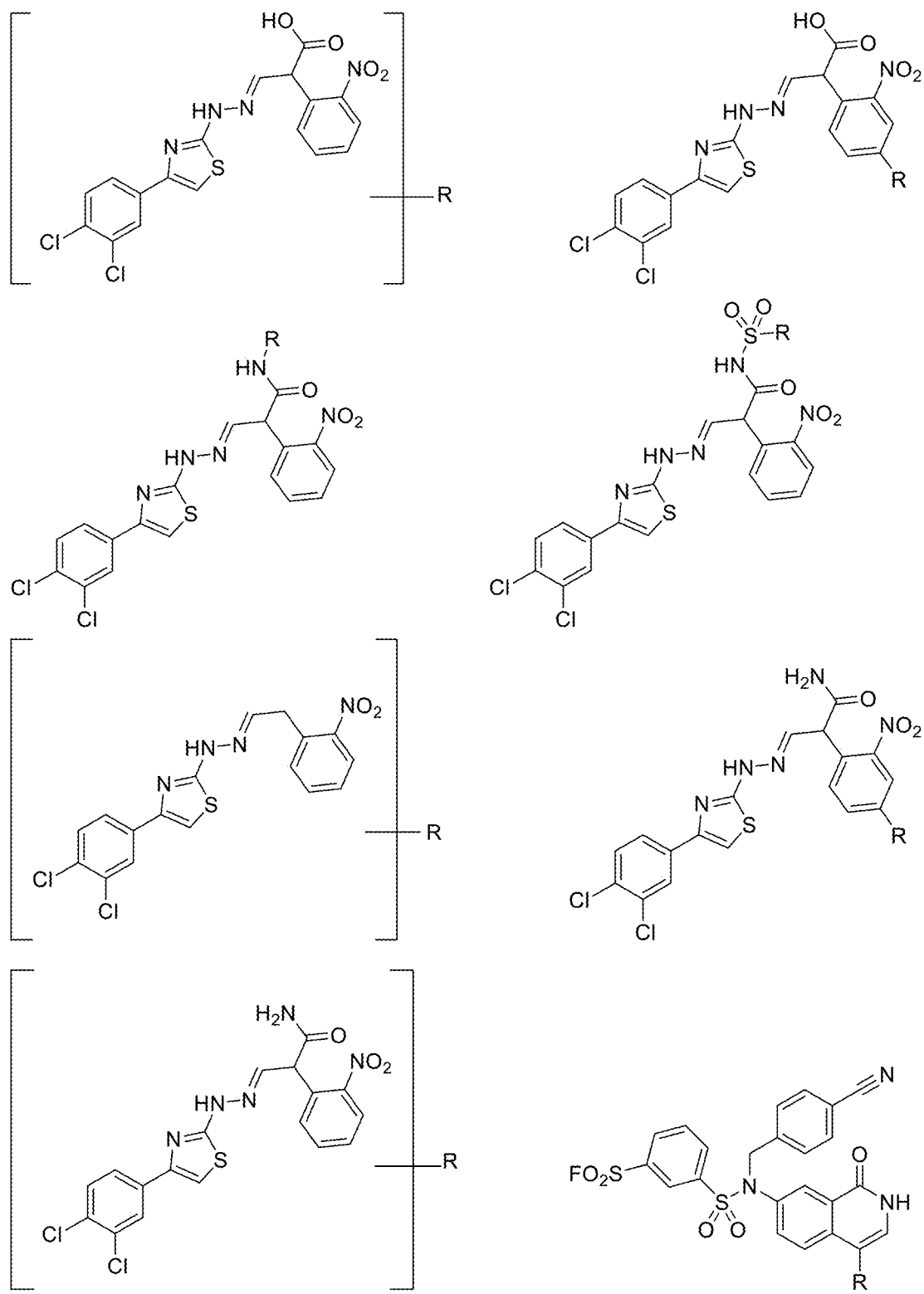

FIG. 68A-68B provide non-limiting examples of elf4E Targeting Ligands wherein R represents exemplary points at which the Linker is attached. Additional examples are provided in J. Am. Chem. Soc. 2020, 142, 4960-4964.

Figure 69:
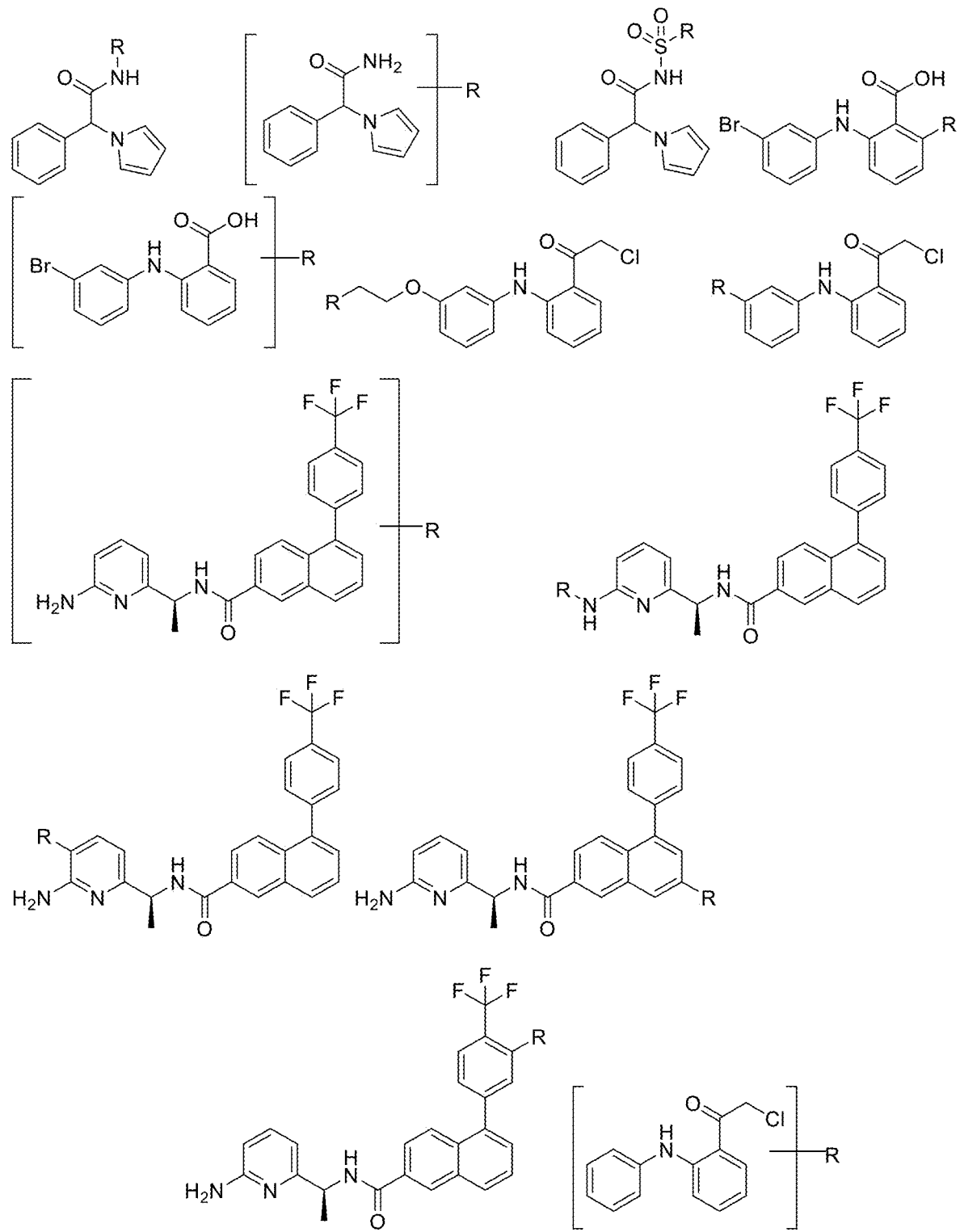

FIG. 69 provides non-limiting examples of TEAD, for example, TEAD1, TEAD2, TEAD3, and/or TEAD4 Targeting Ligands wherein R represents exemplary points at which the Linker is attached.

Figure 70:
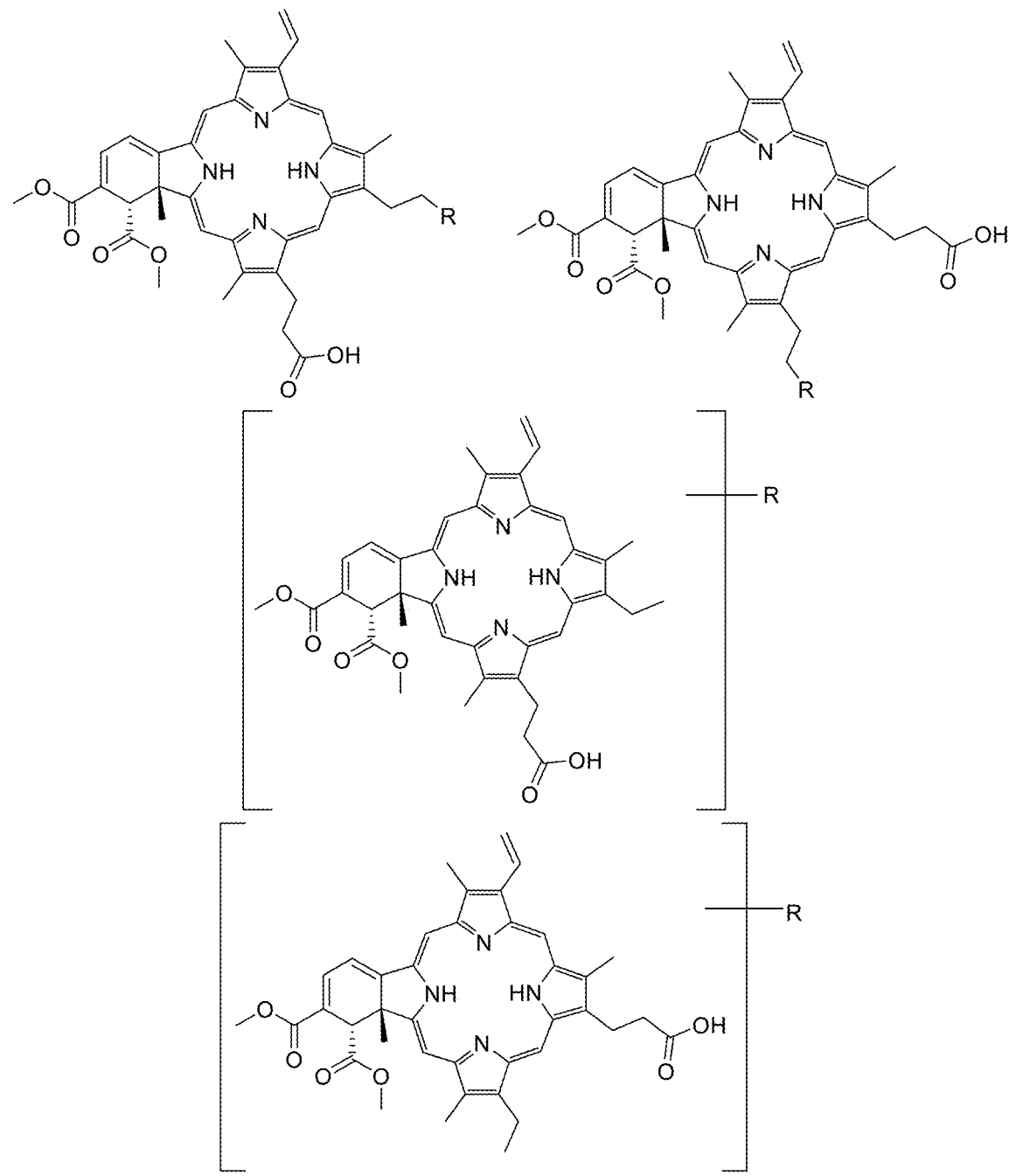

FIG. 70 provides non-limiting examples of YAP Targeting Ligands wherein R represents exemplary points at which the Linker is attached.

FIG. 71 provides non-limiting examples of Degron formulas of the present invention.

Figure 72:
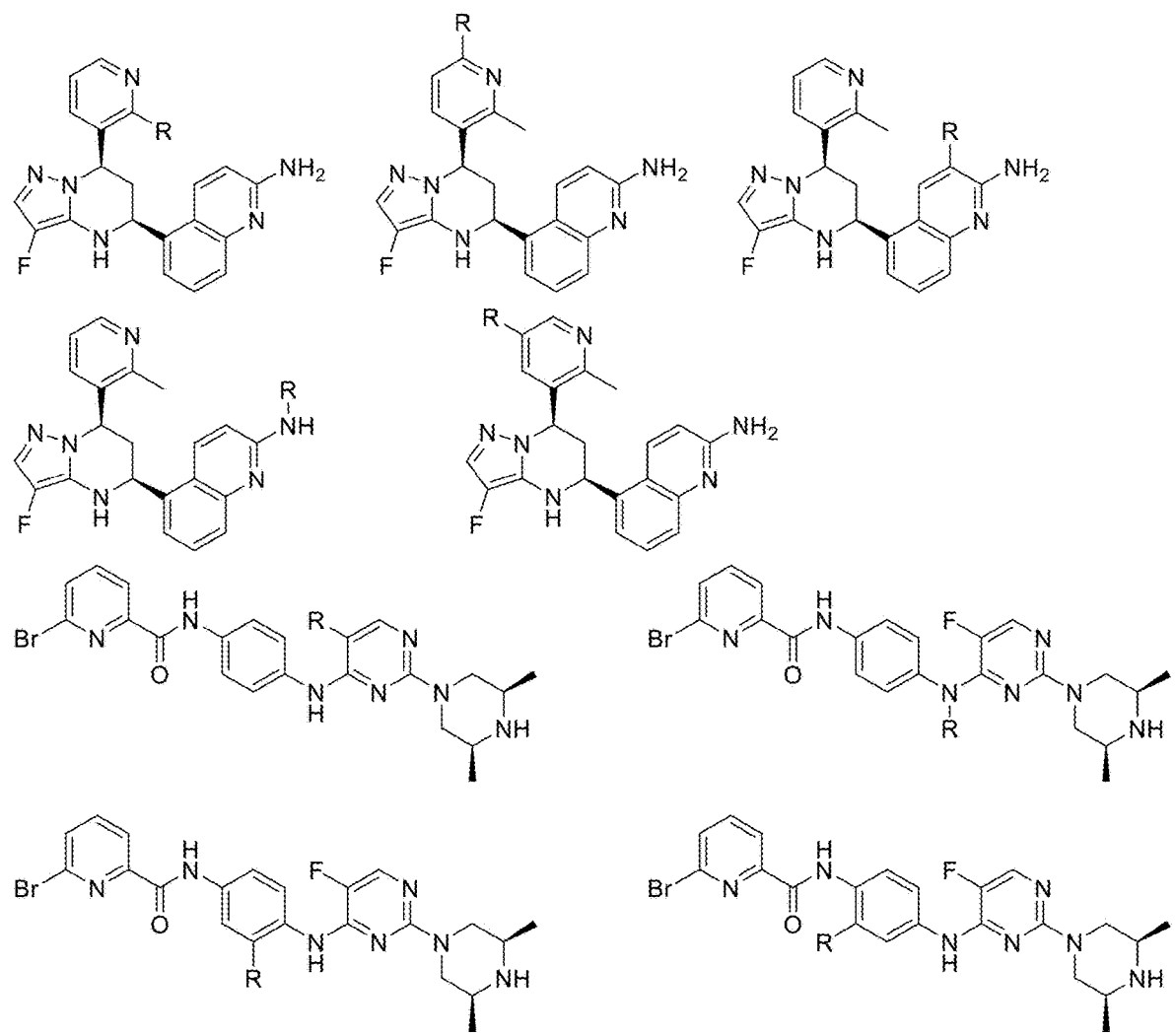

FIG. 72 provides non-limiting examples of B-cell lymphoma 6 protein (BCL6) Targeting Ligands wherein R represents exemplary points at which the Linker is attached. Additional examples are provided in J. Bio. Chem. 2021, 297, 2, 100928 and Cancer Lett. 2022, 529, 100-111.

Figure 73A:
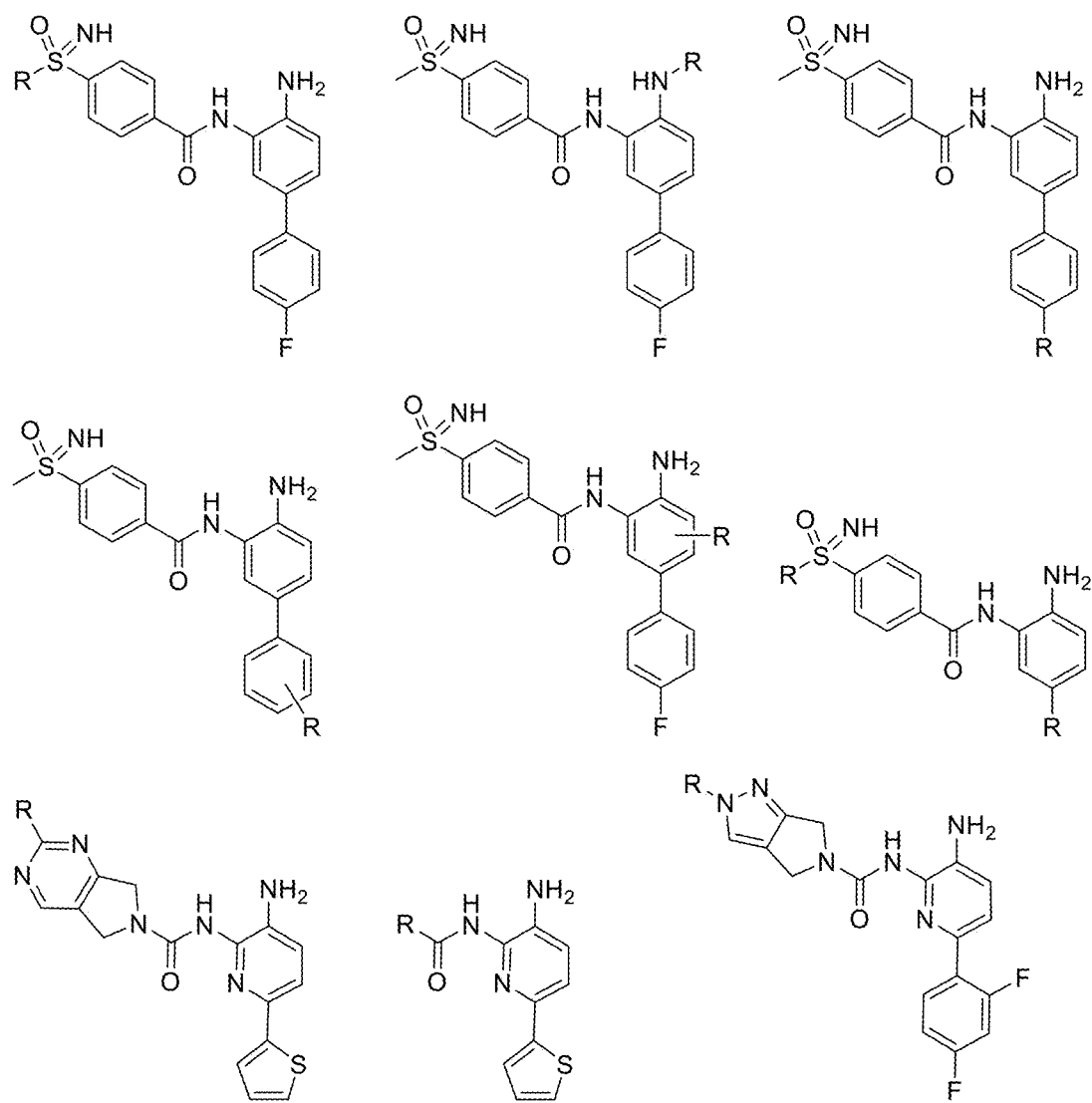
Figure 73B:
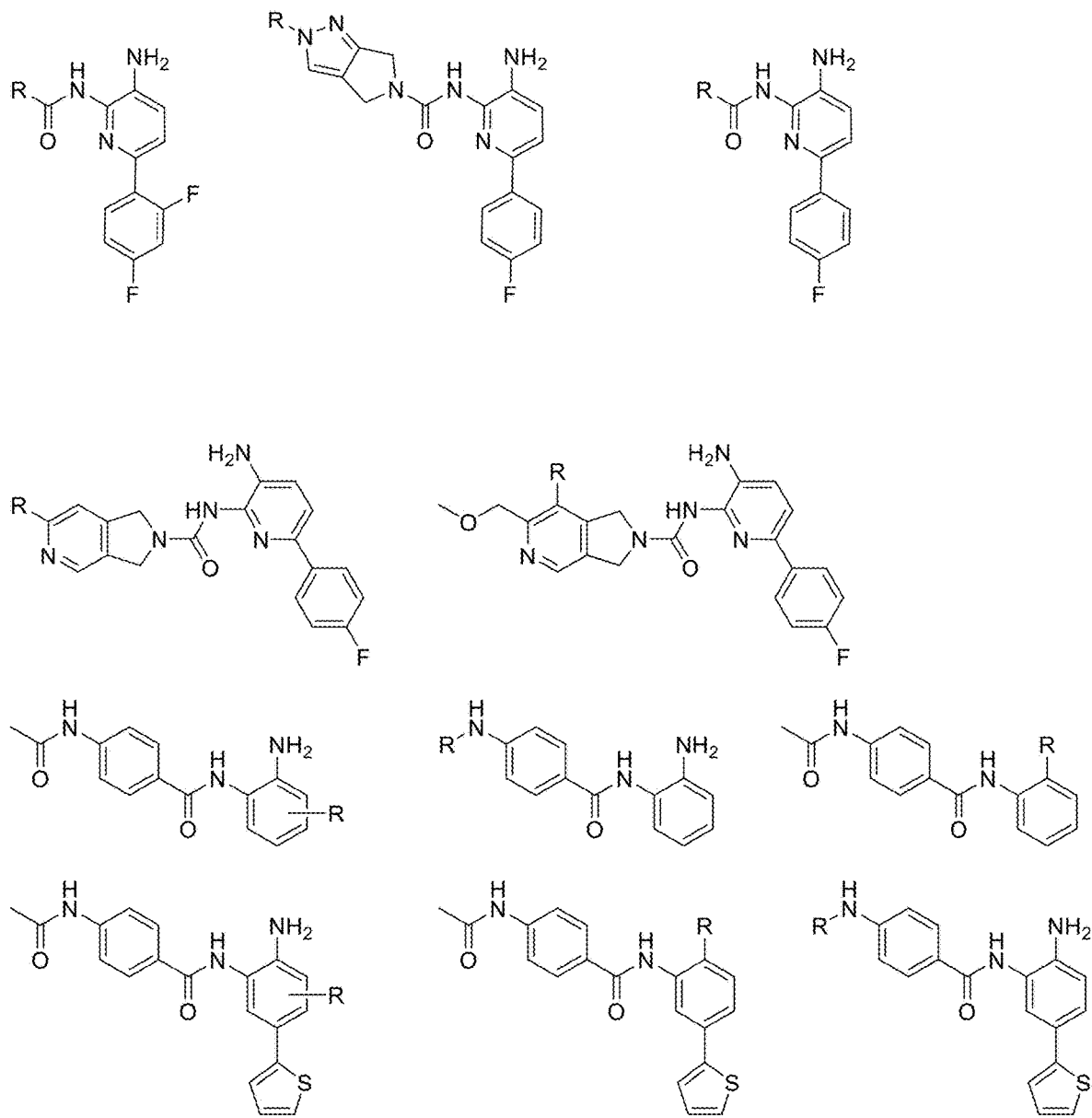
Figure 74A:
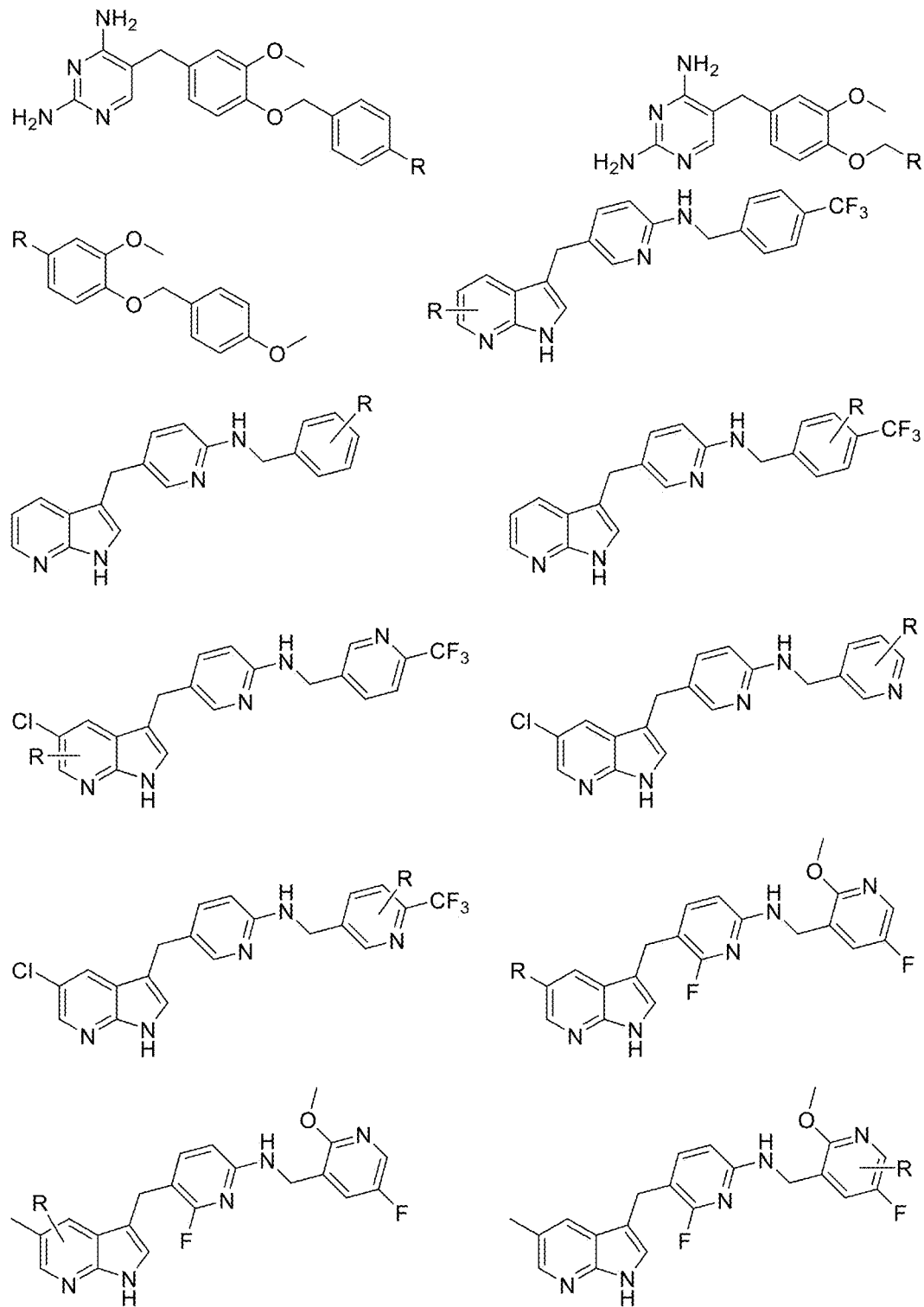
Figure 74B:
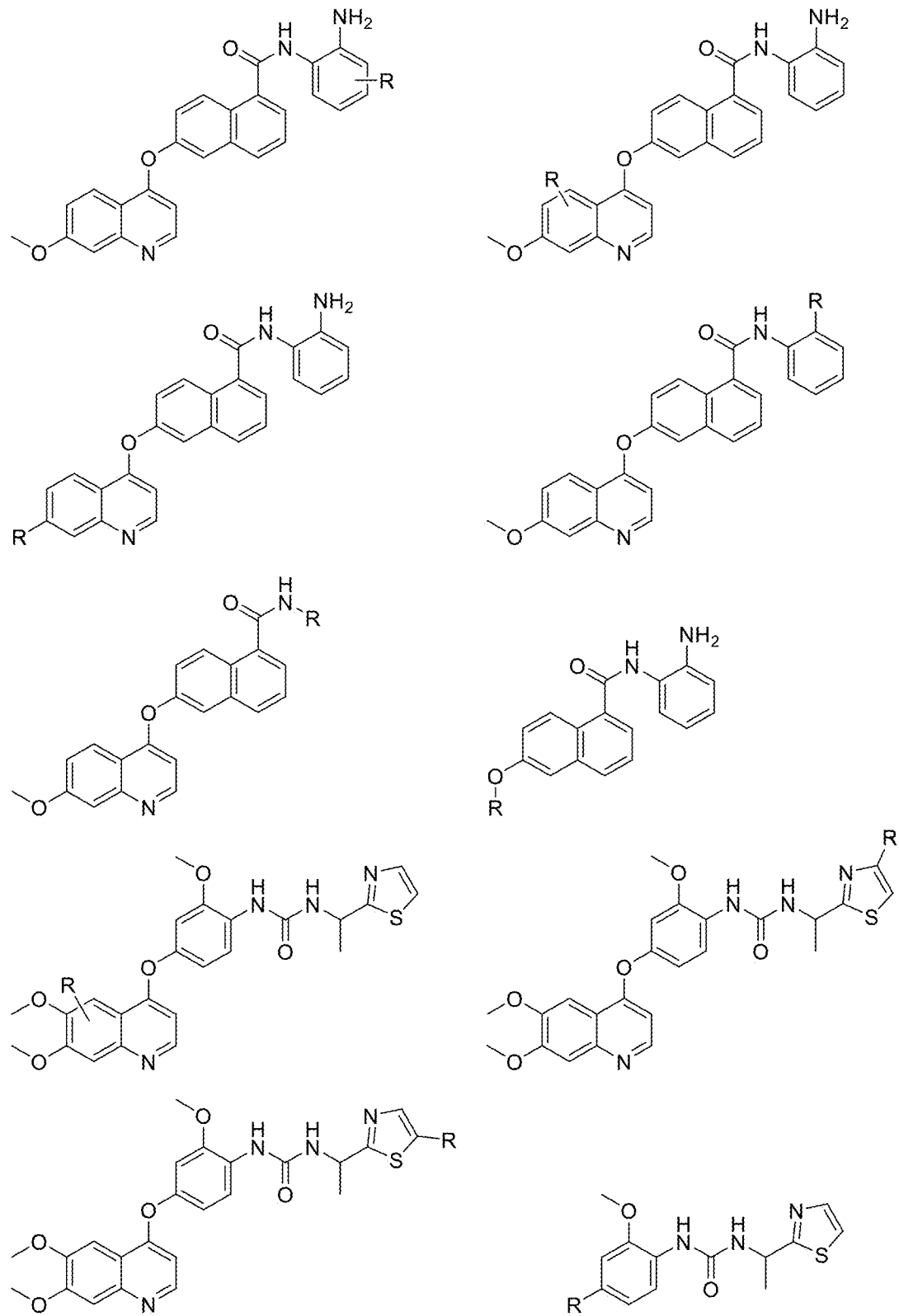
Figure 74C:
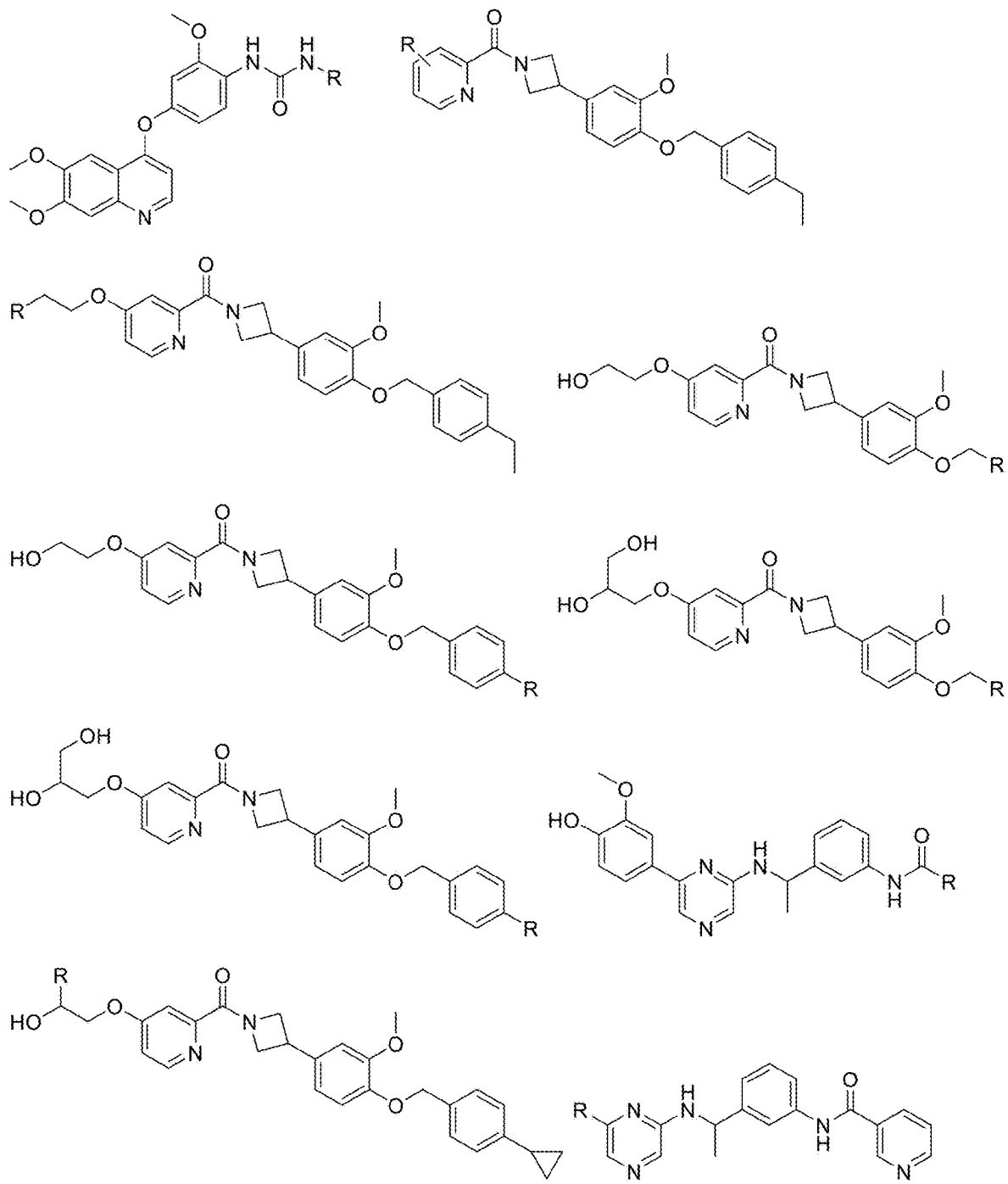
Figure 74D:
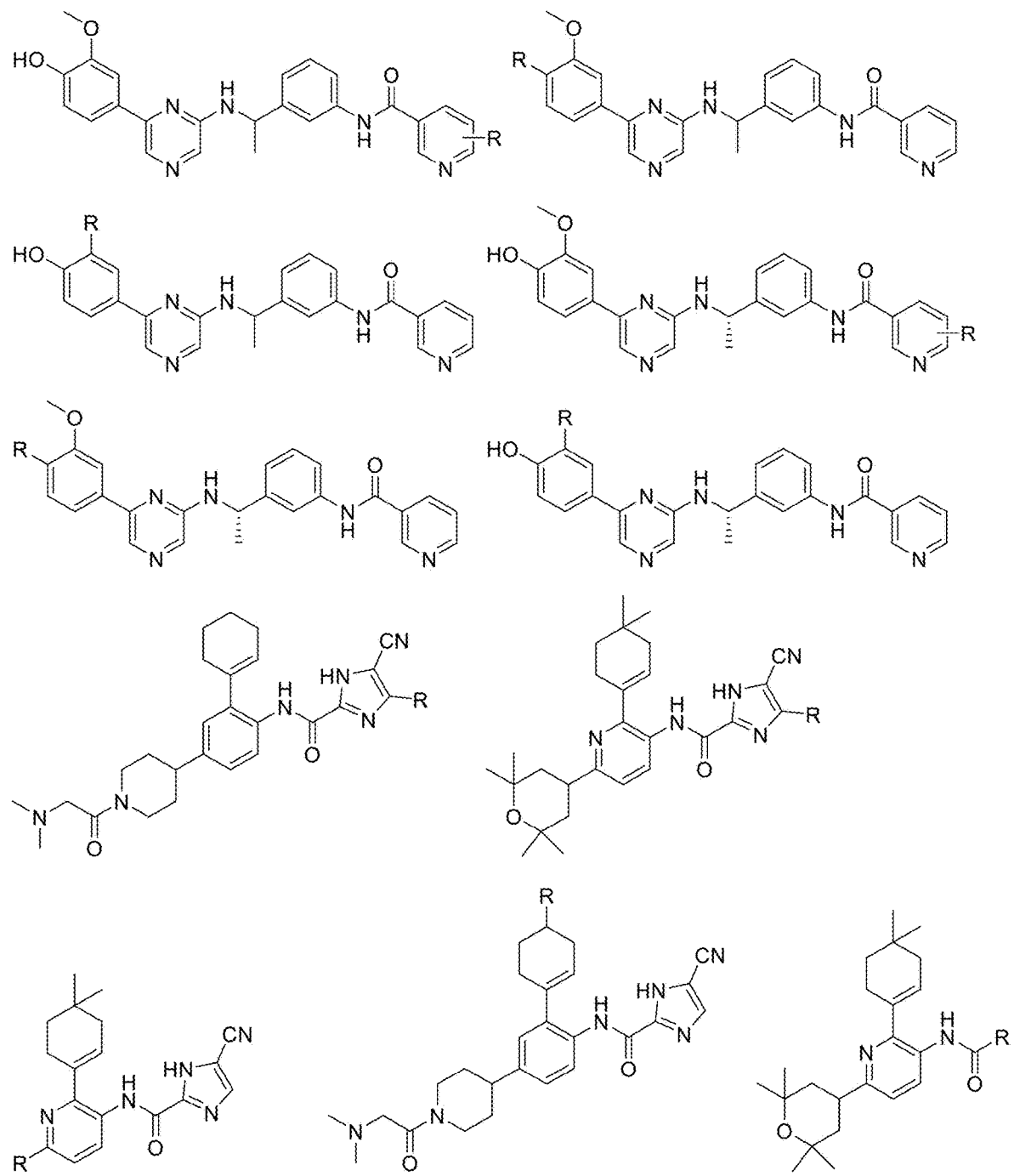
Figure 74E:
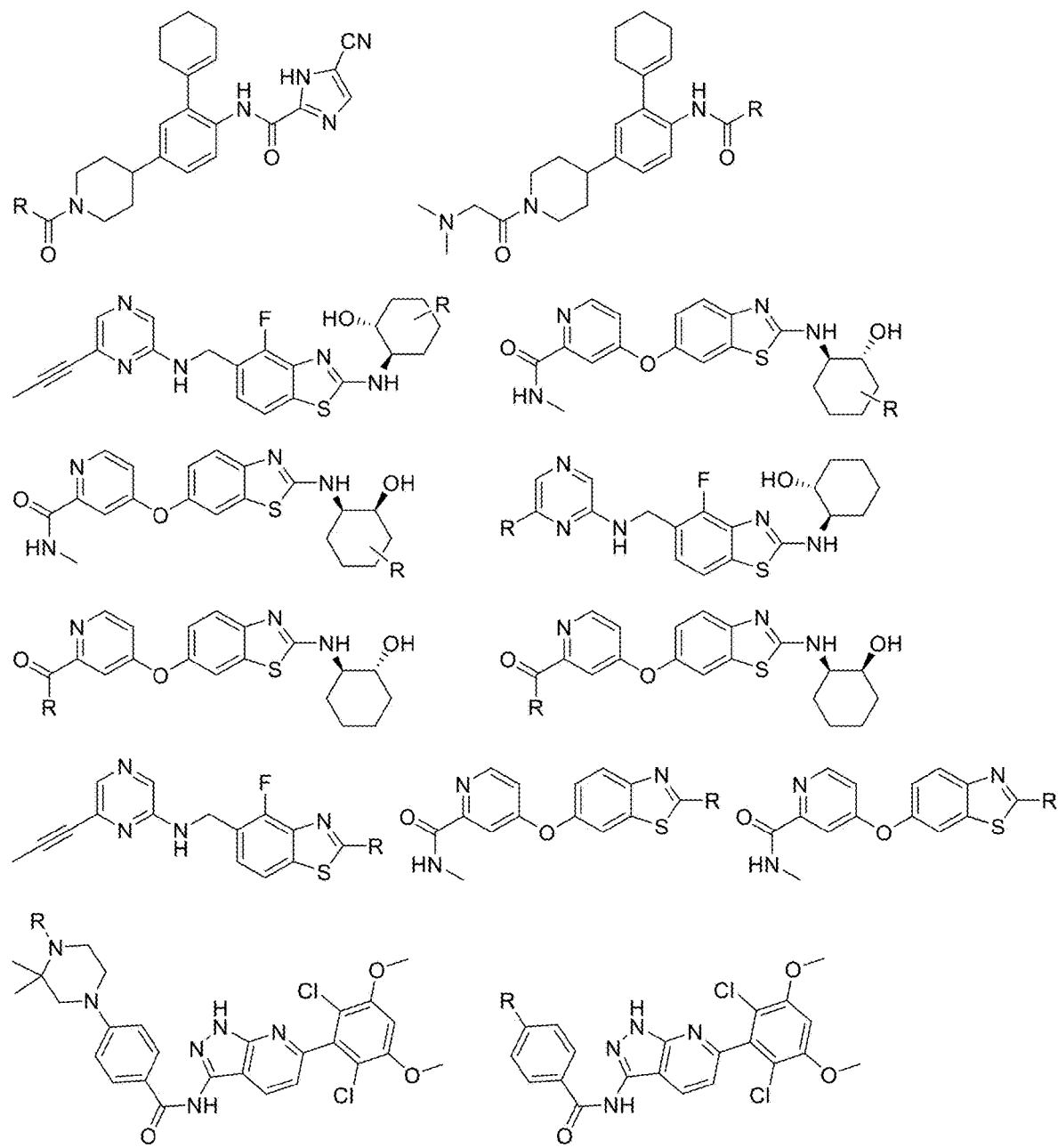
Figure 74F:
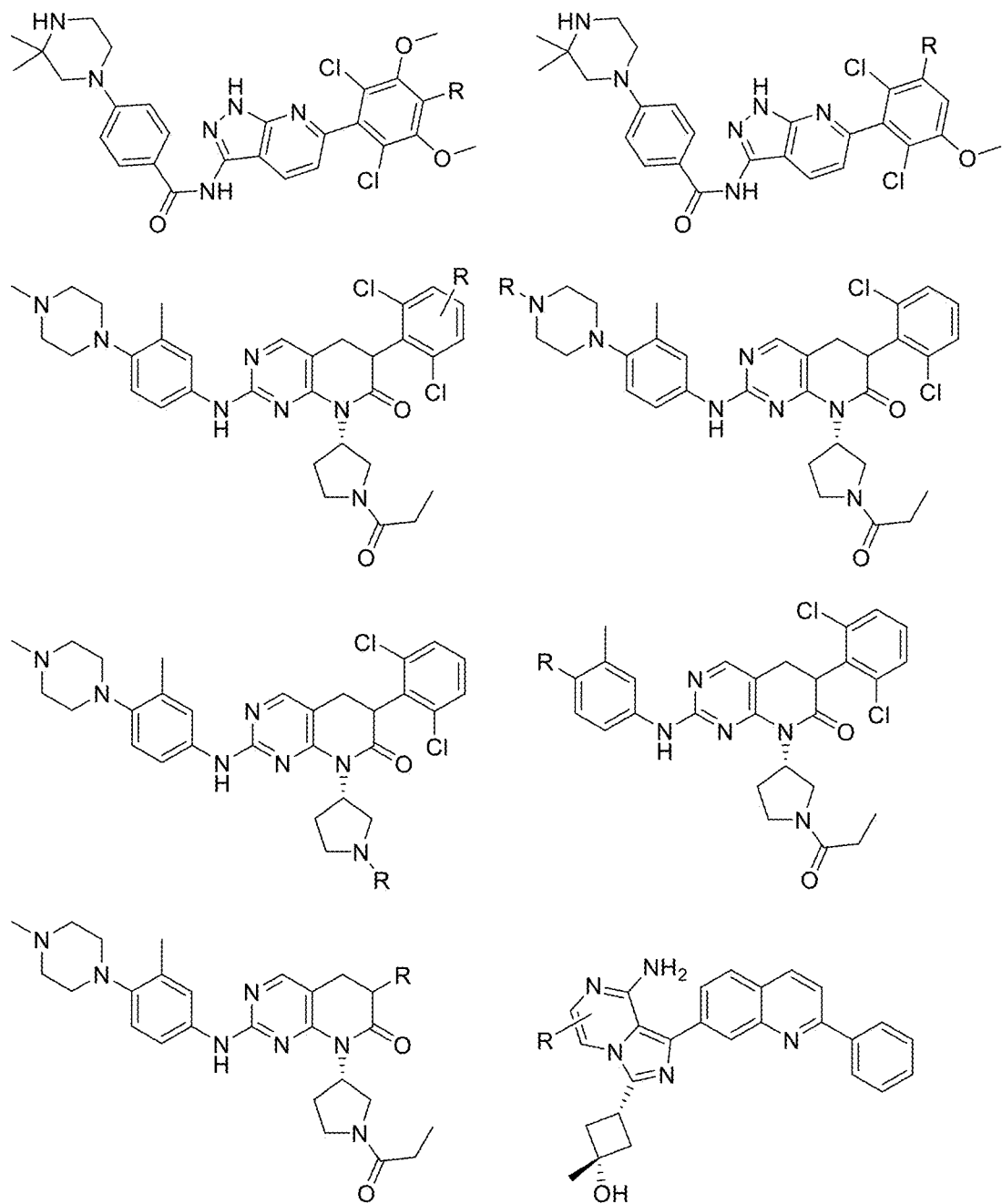
Figure 74G:
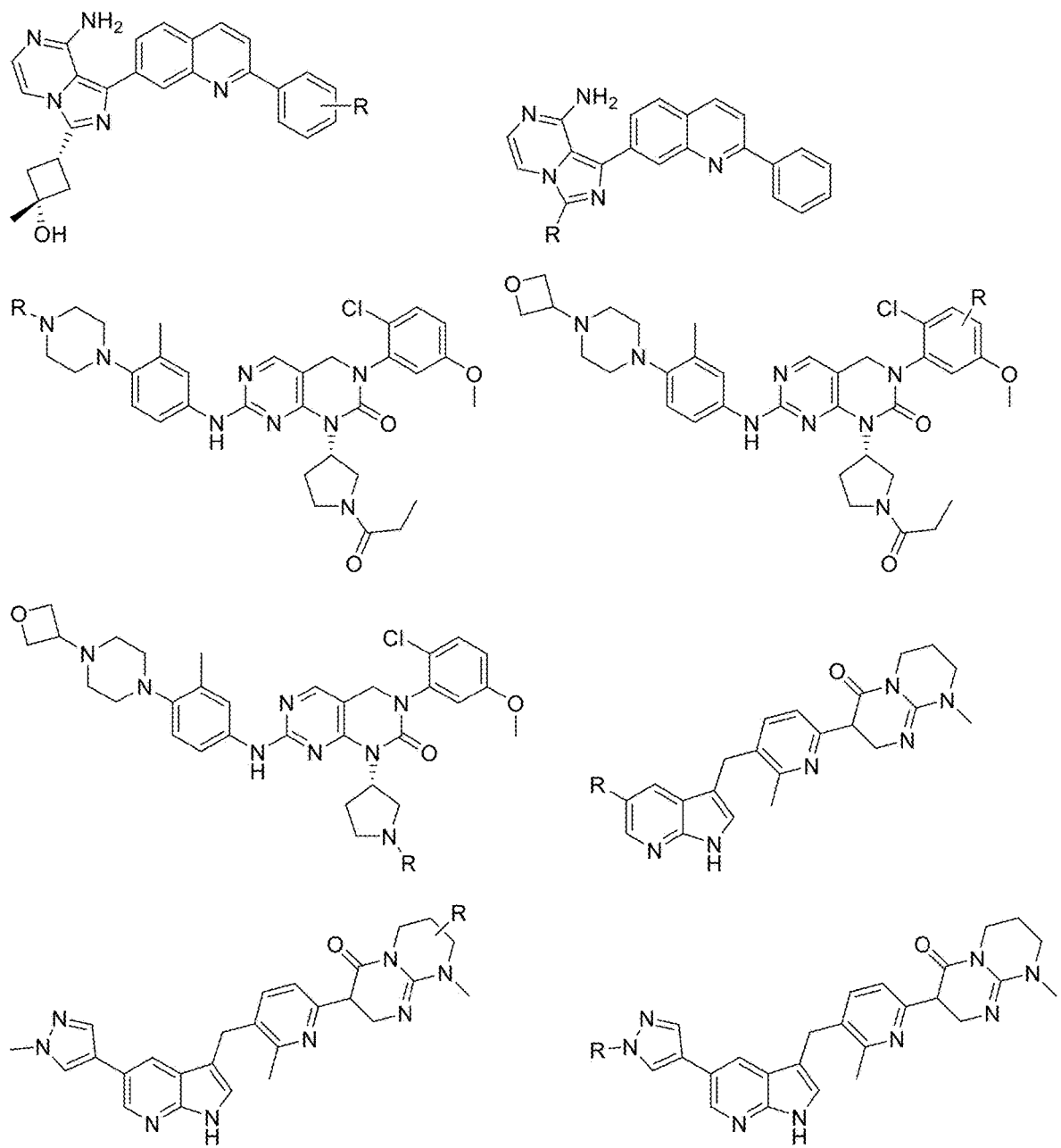
Figure 74H:
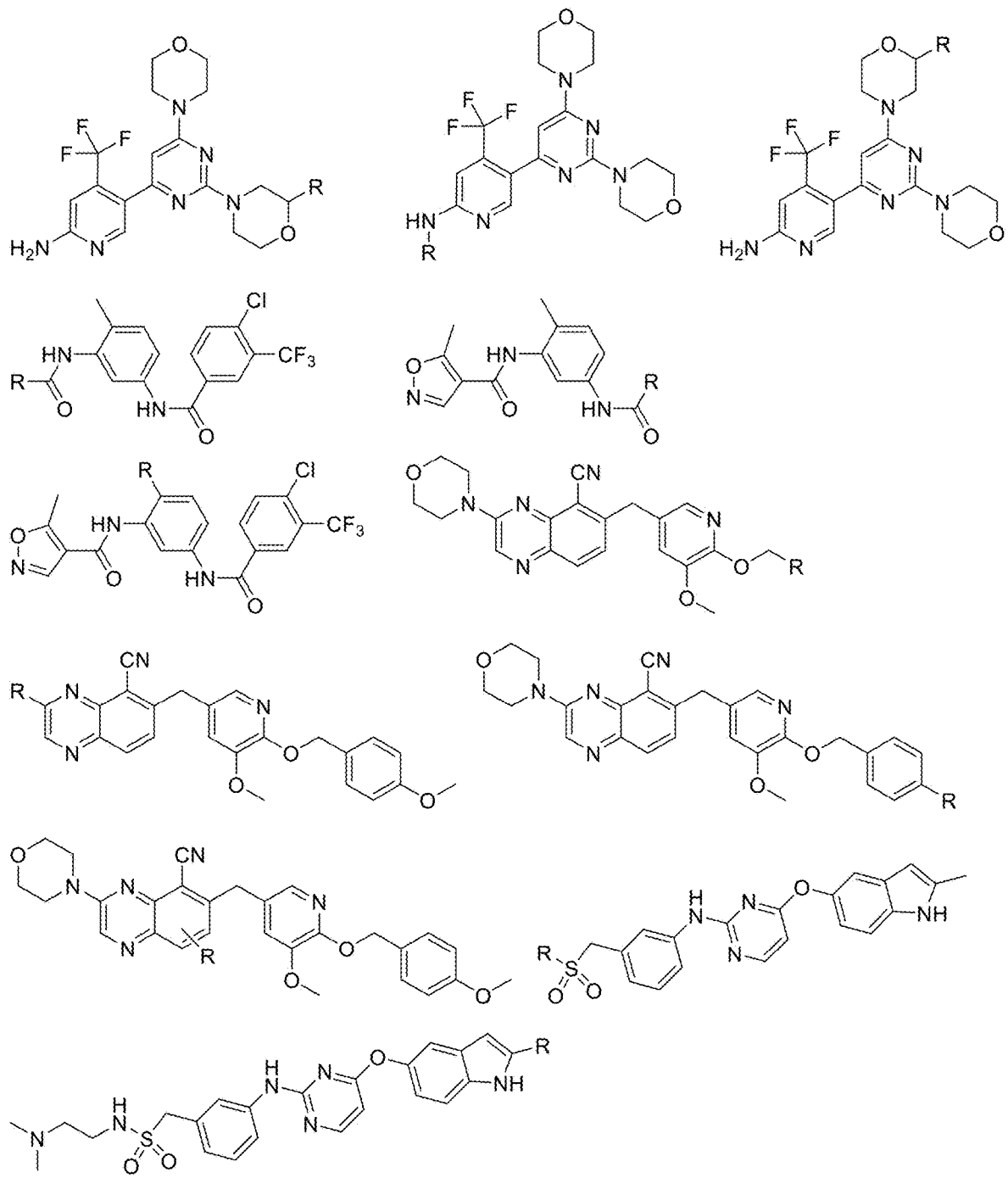
Figure 74I:
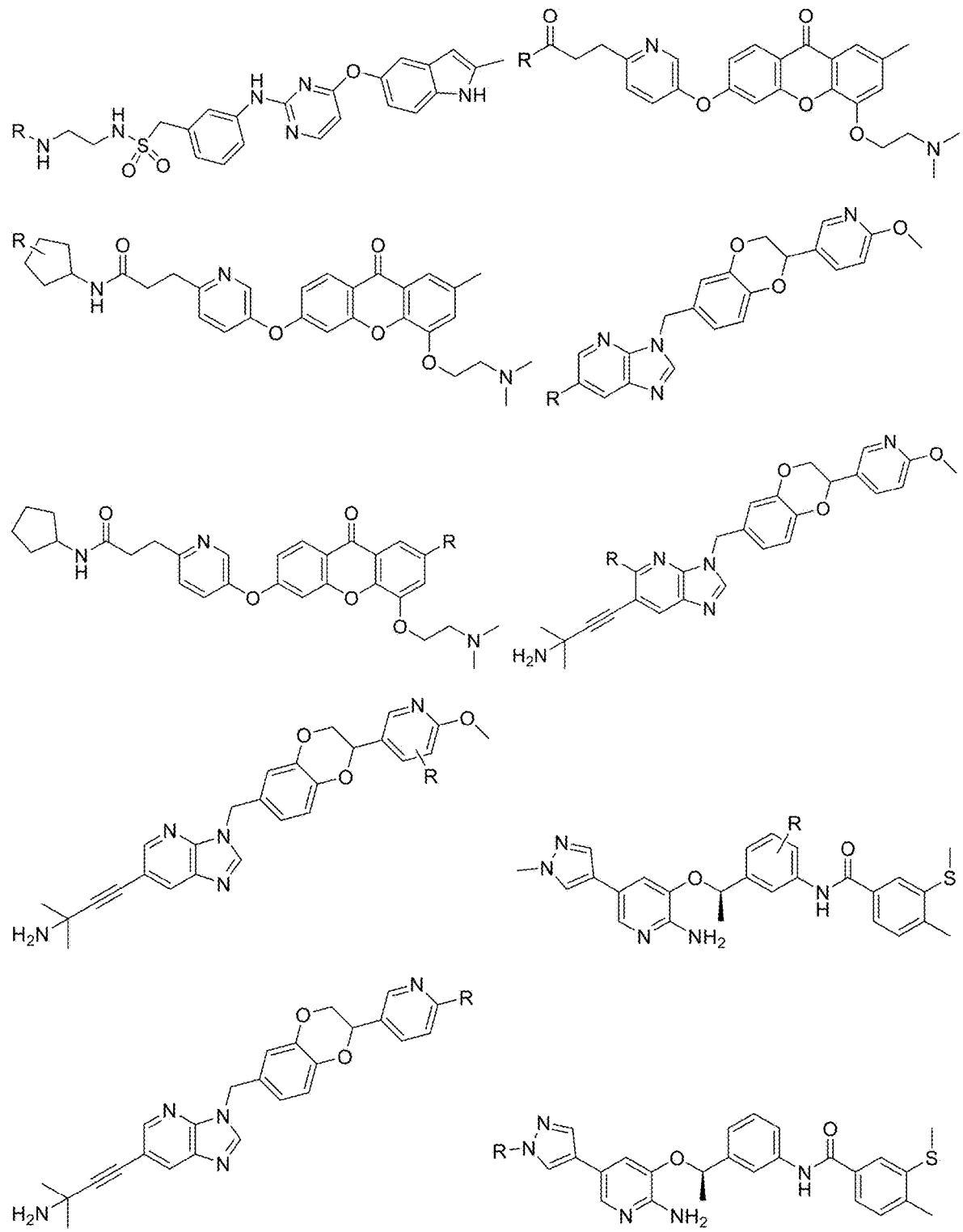
Figure 74J:
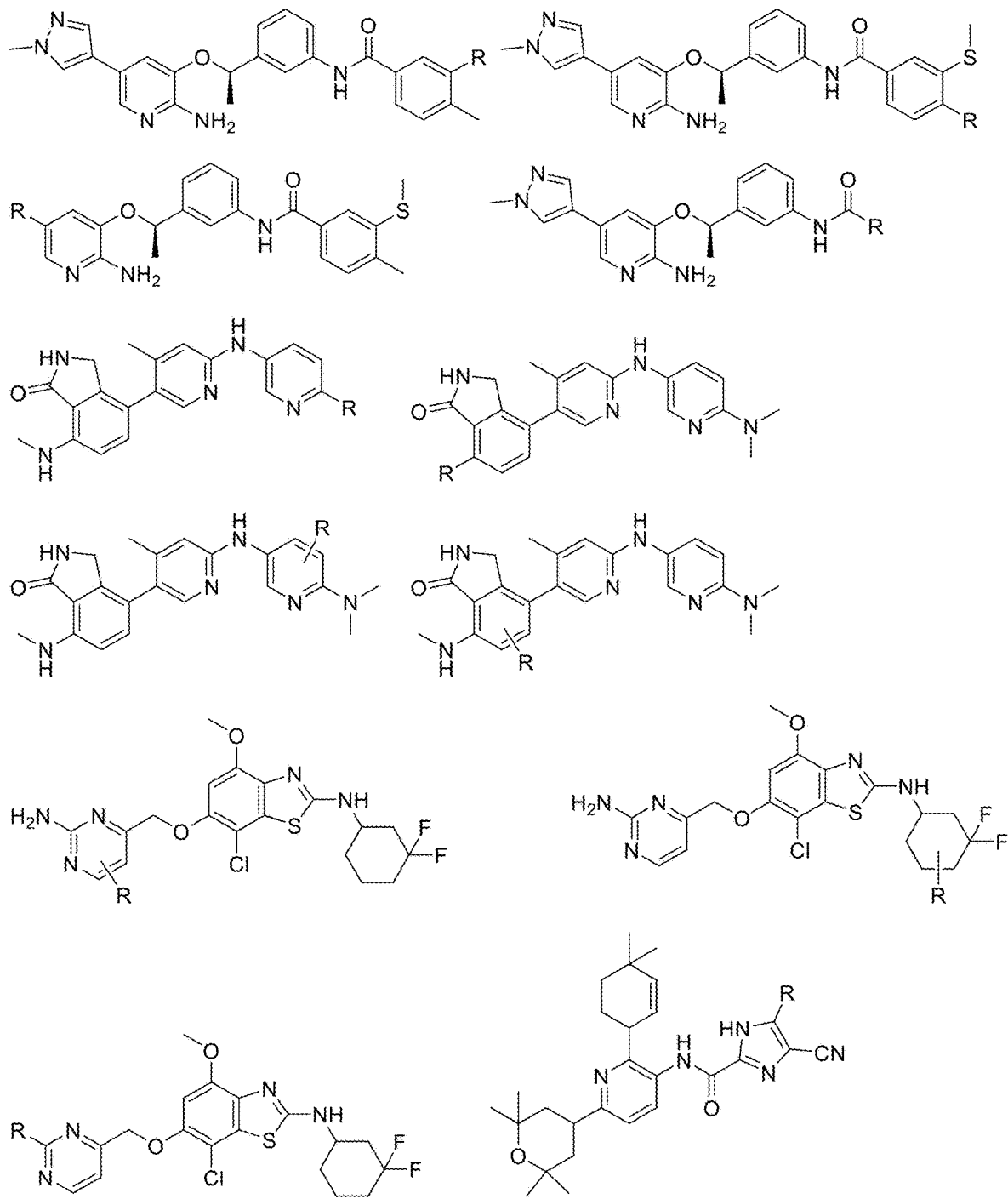
Figure 74K:
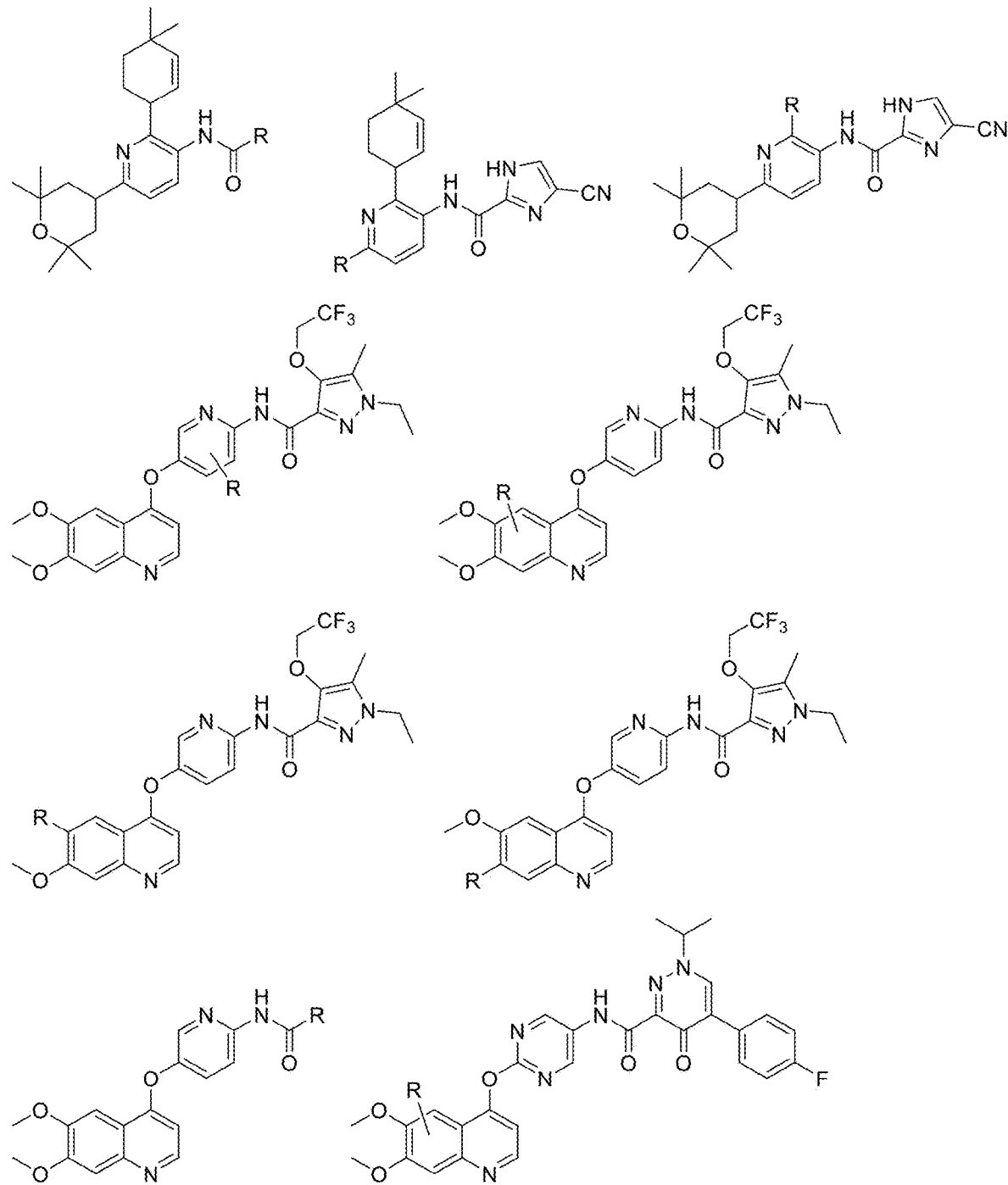
Figure 74L:
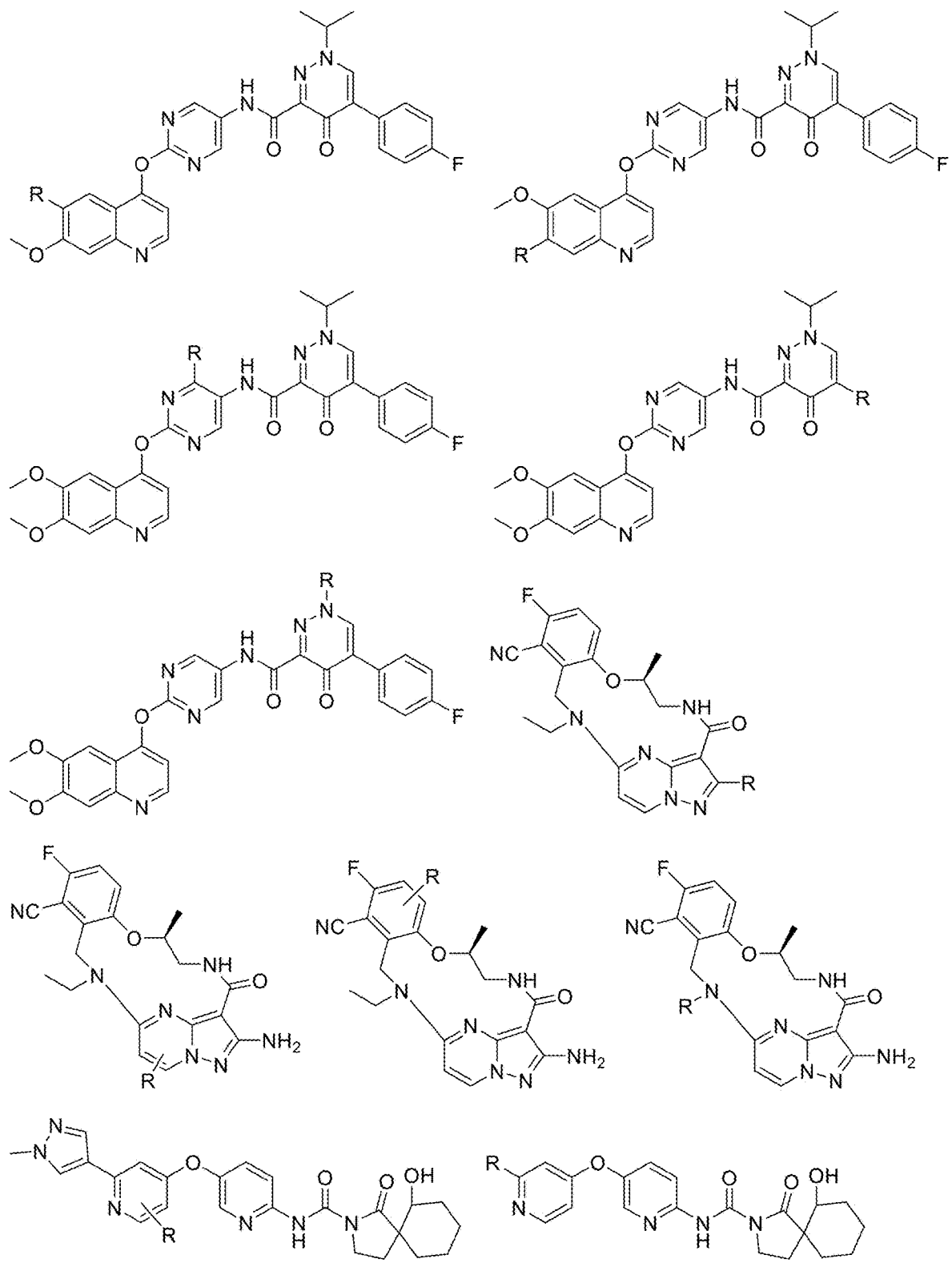
Figure 74M:
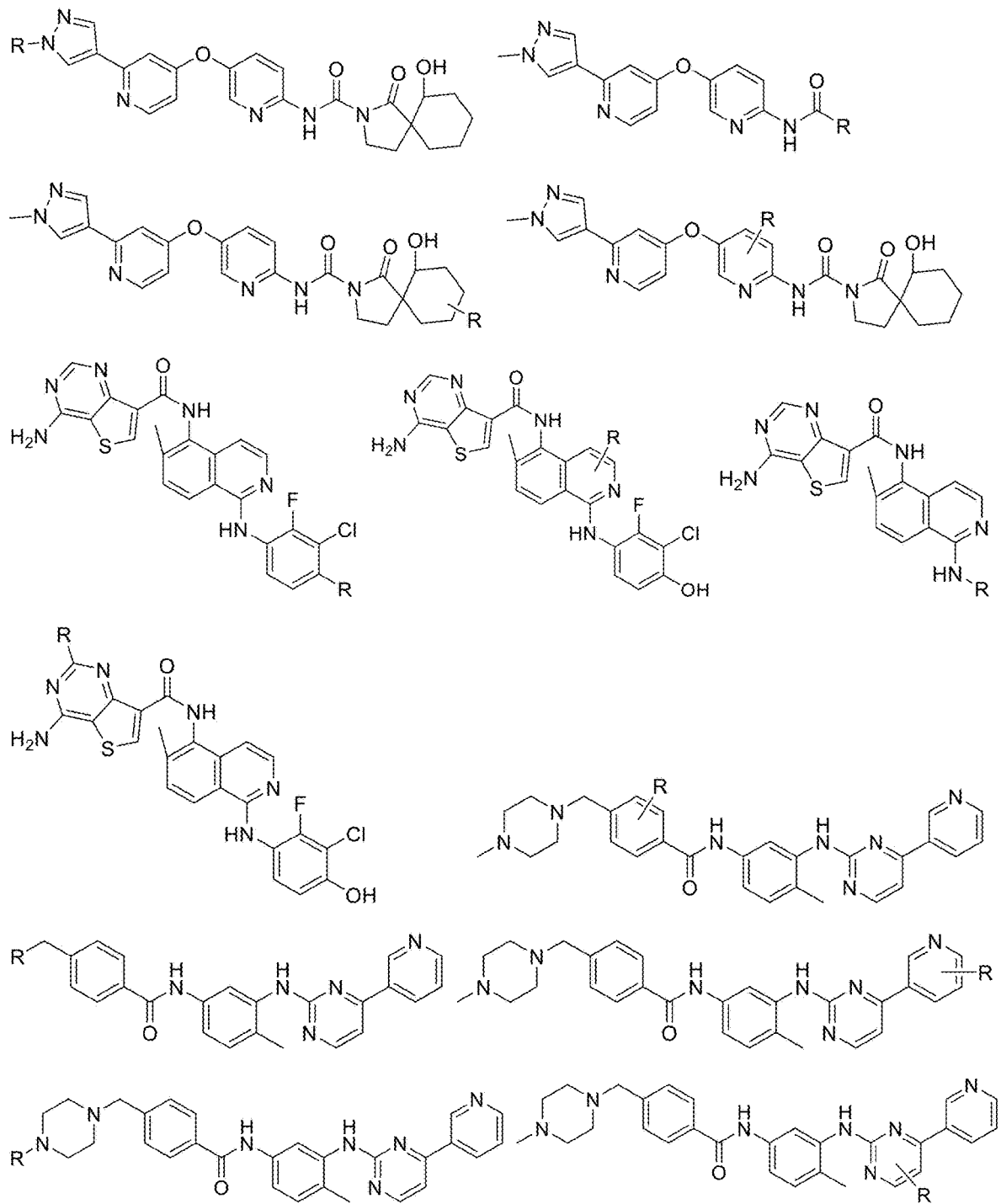

FIG. 73A and FIG. 73B provide non-limiting examples of HDAC-co-repressor of repressor element-1 silencing transcription factor (CoREST) Targeting Ligands or CoREST Complex Targeting Ligands wherein R represents exemplary points at which the Linker can be attached. Additional examples are provided in ACS Chem. Neurosci. 2019, 10, 1729-1743.

FIG. 74A-74M provide non-limiting examples of colony stimulating factor 1 receptor (CSF1R) Targeting Ligands wherein R represents exemplary points at which the Linker can be attached. Additional examples are provided in Expert Opin. on Ther. Pat. 2021, 31, 2, 107-117 and Nature Communications 2019, 10, 3758. Crystal structures related to these Targeting Ligands include PDB code 3krj and PDB code 4r7h.

Figure 75A:
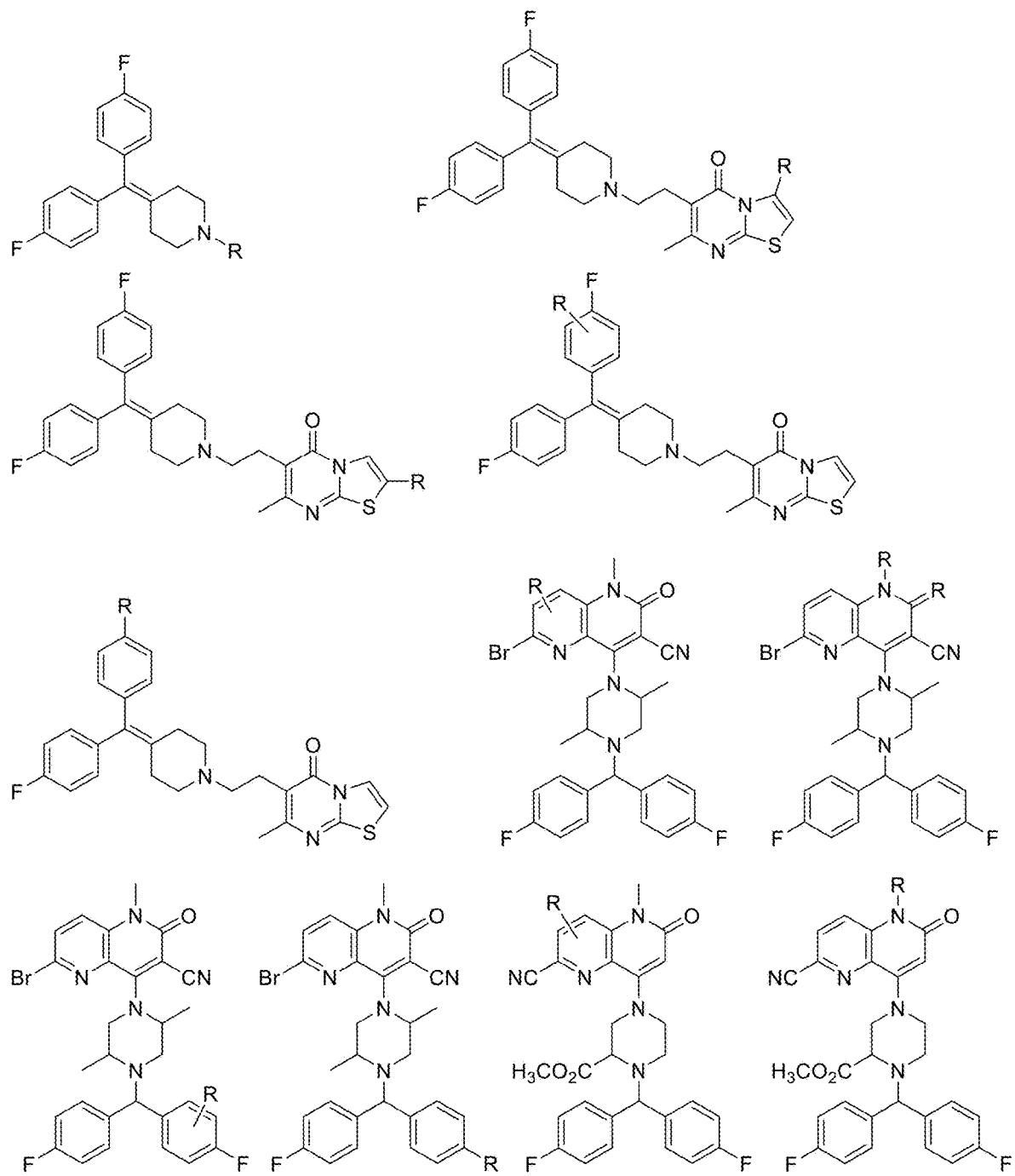
Figure 75B:
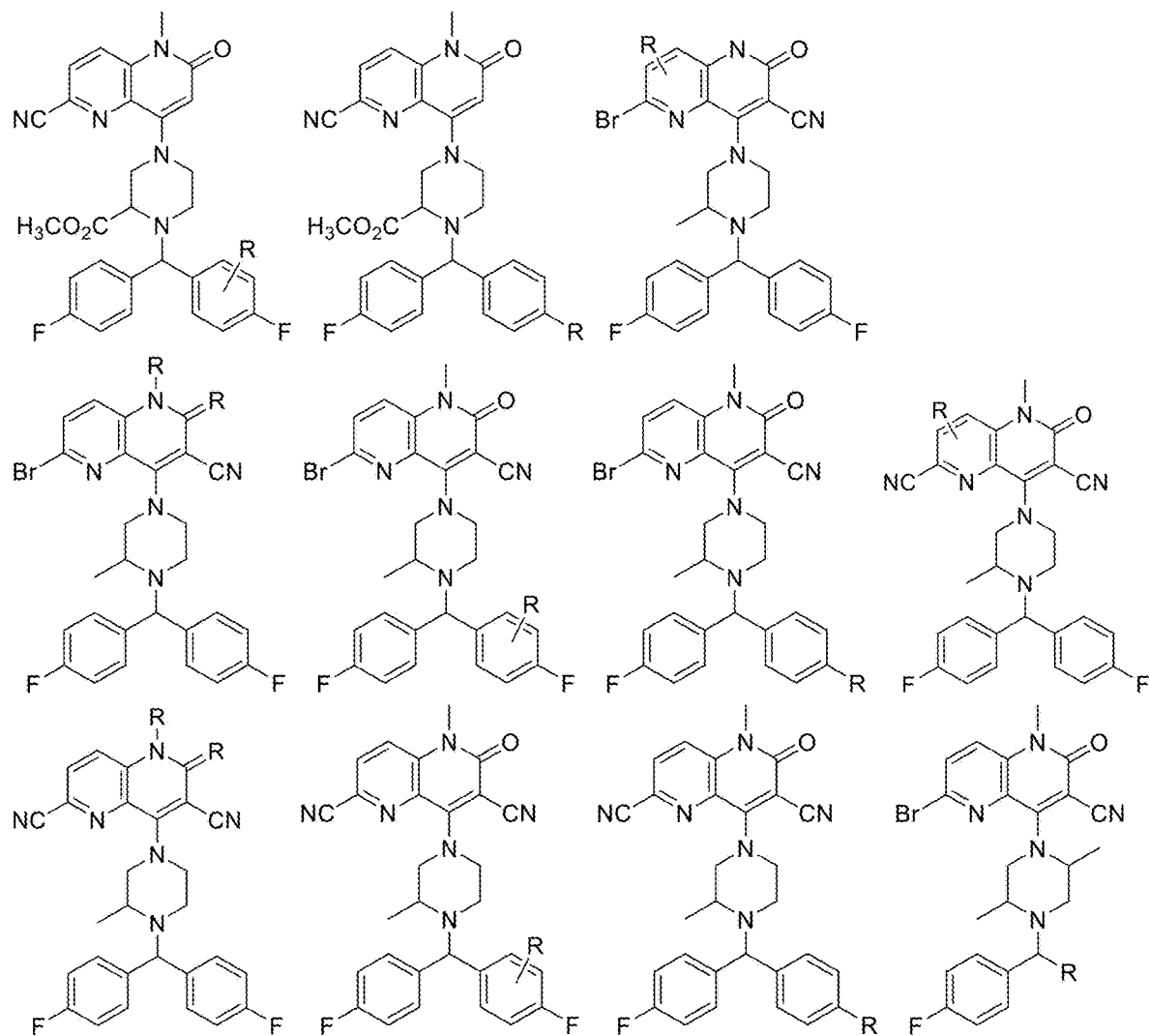

FIG. 75A and FIG. 75B provide non-limiting examples of diacylglycerol kinase (DGK) Targeting Ligands wherein R represents exemplary points at which the Linker can be attached. Additional examples are provided in Cell Chem. Biol. 2017, 24, 870-880, WO2022/187406, and WO2021/127554.

Figure 76:
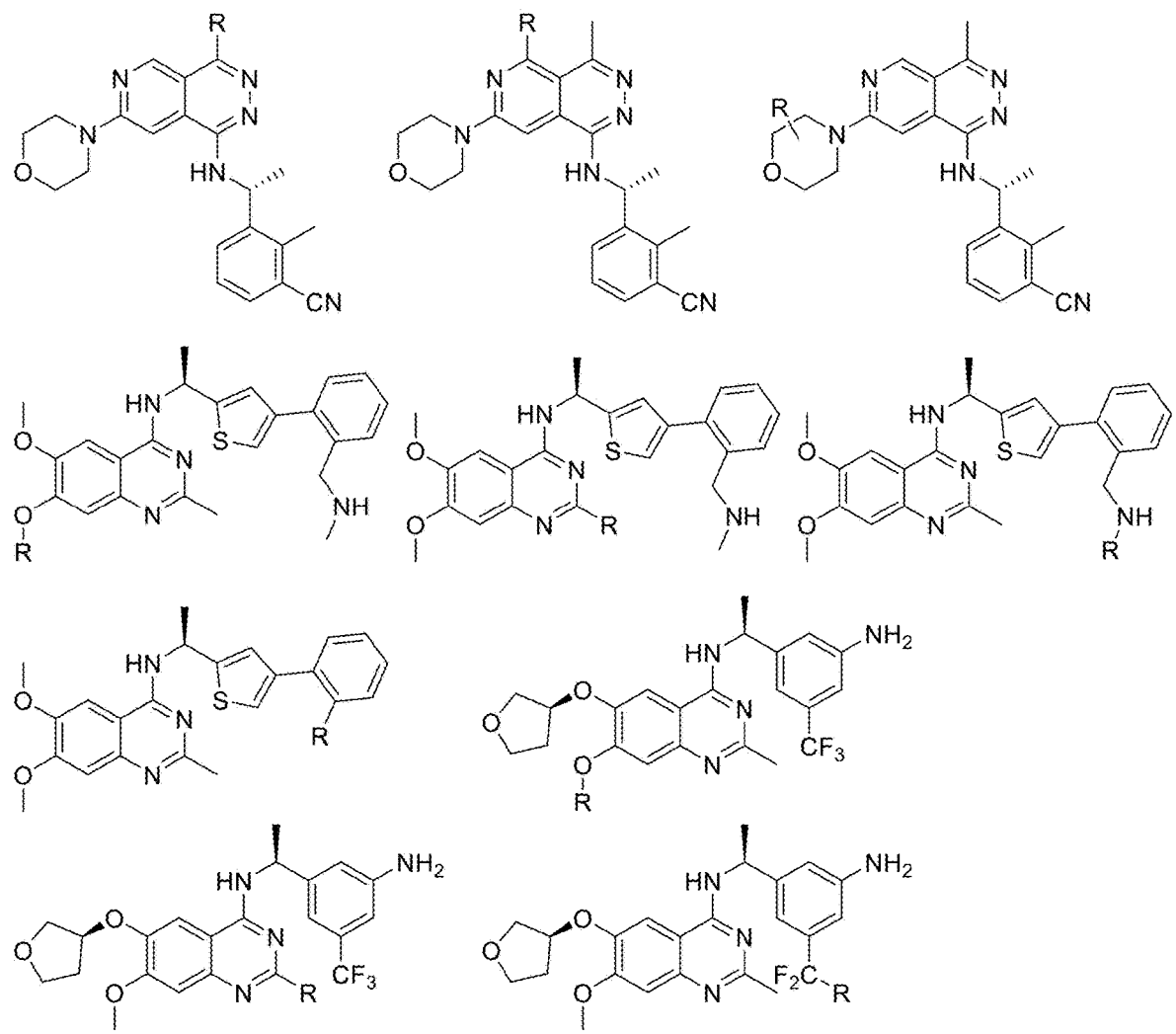

FIG. 76 provides non-limiting examples of son of sevenless homolog 1 (SOS1) Targeting Ligands wherein R represents exemplary points at which the Linker can be attached. Crystal structures related to these Targeting Ligands include 5ovi, 6scm, and 7ukr.

Figure 77:
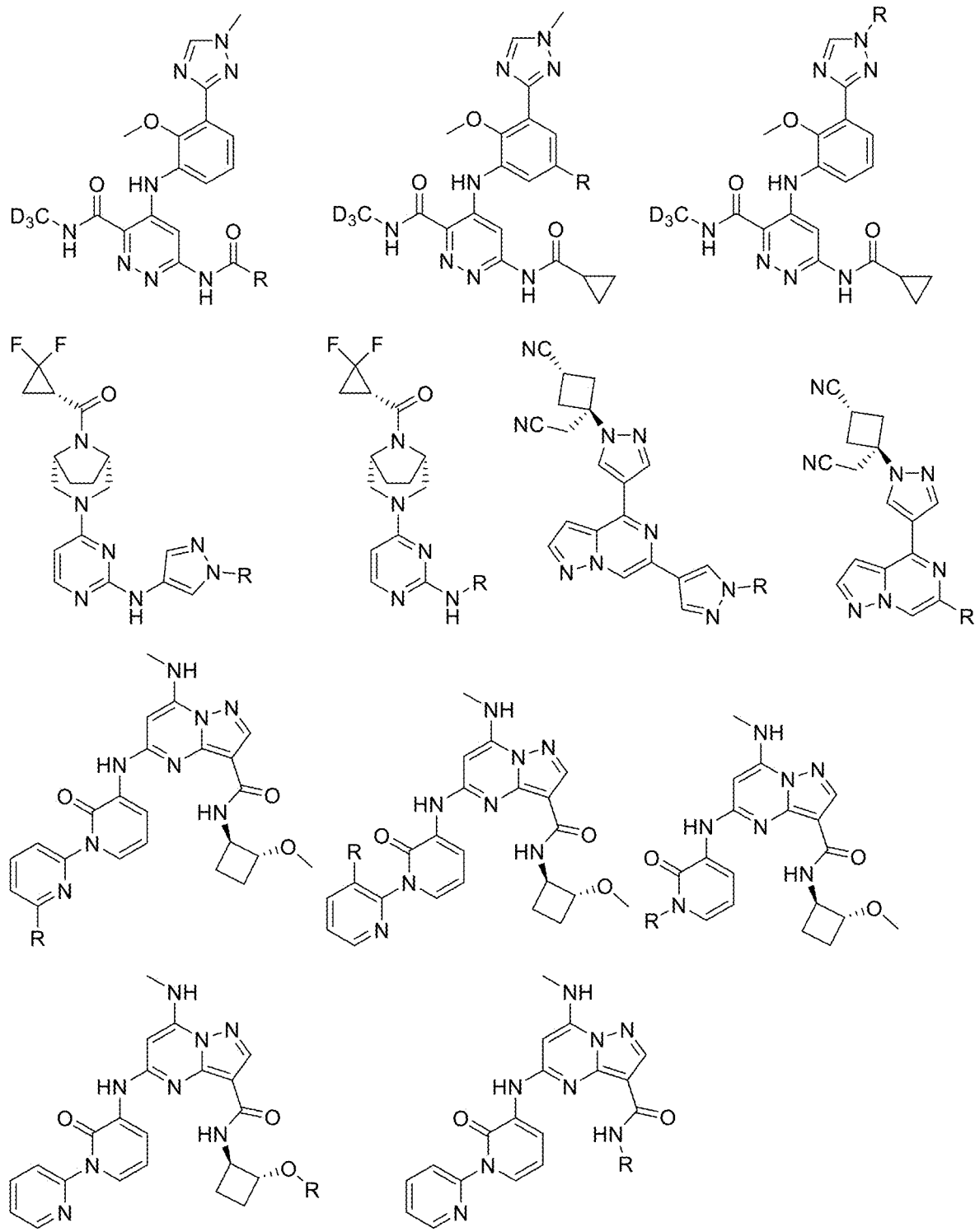

FIG. 77 provides non-limiting examples of tyrosine kinse 2 (TYK2) Targeting Ligands wherein R represents exemplary points at which the Linker can be attached. Additional examples are provided in J. Med. Chem. 2023, 66, 4378-4416.

Figure 78:
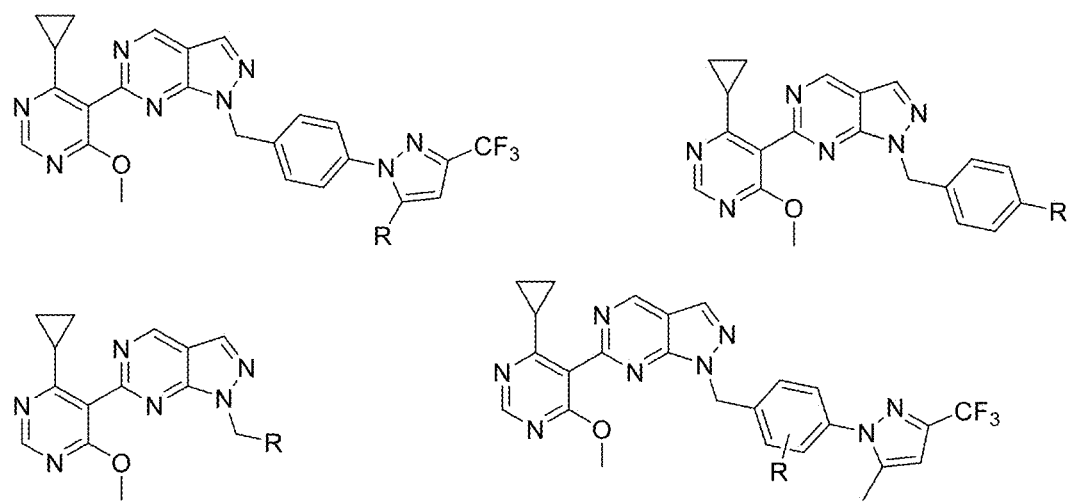
Figure 79A:
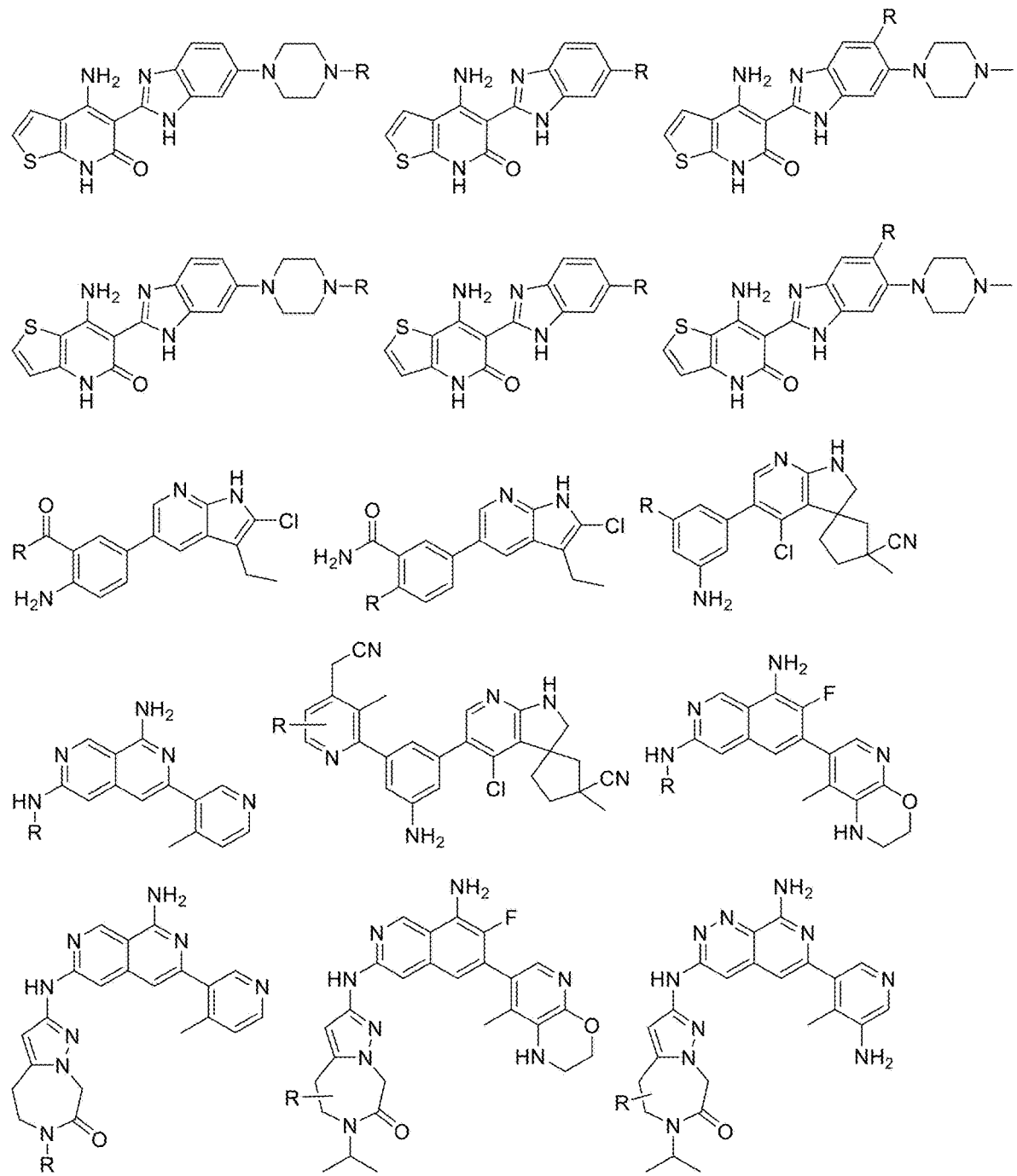
Figure 79B:
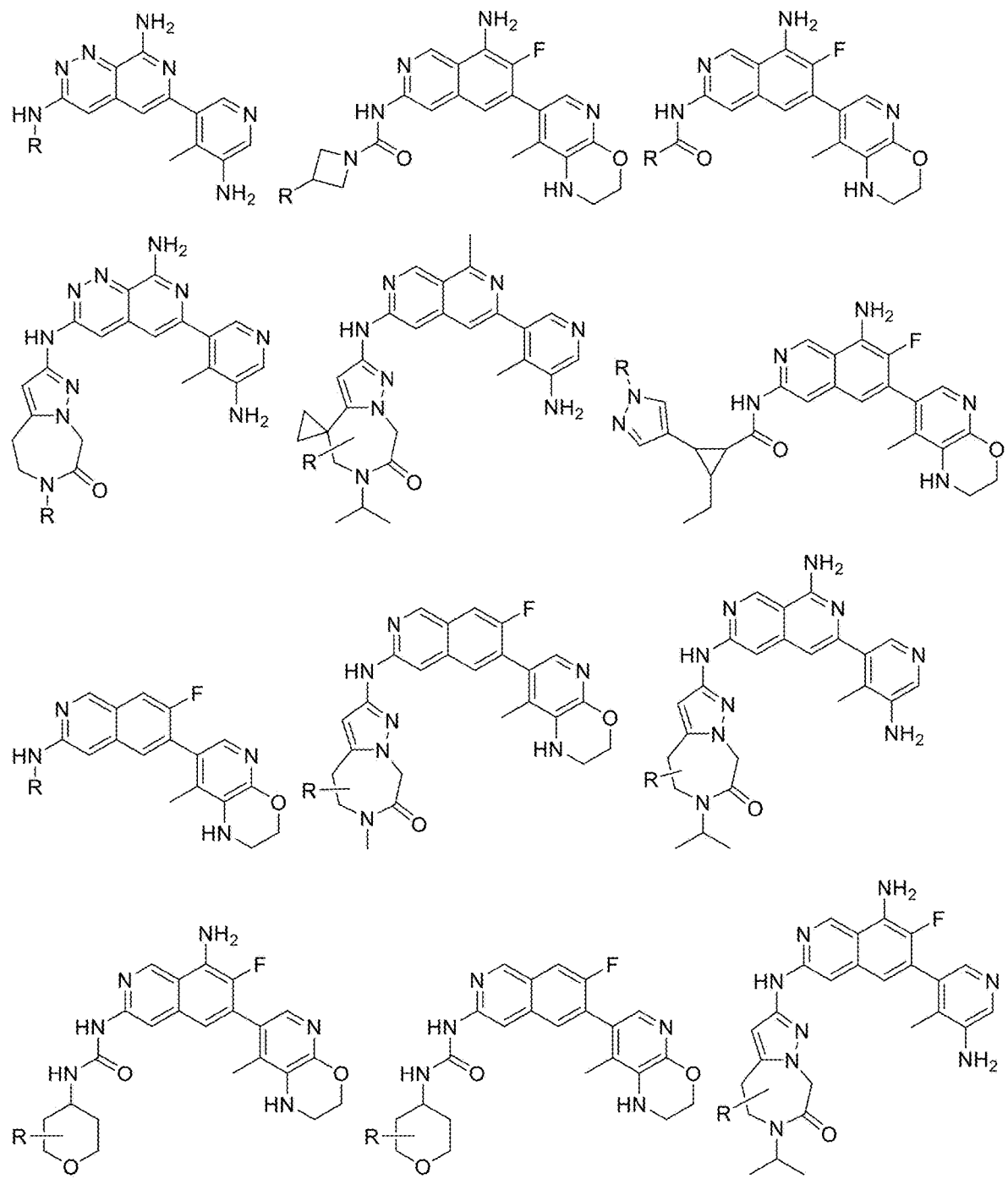
Figure 79C:
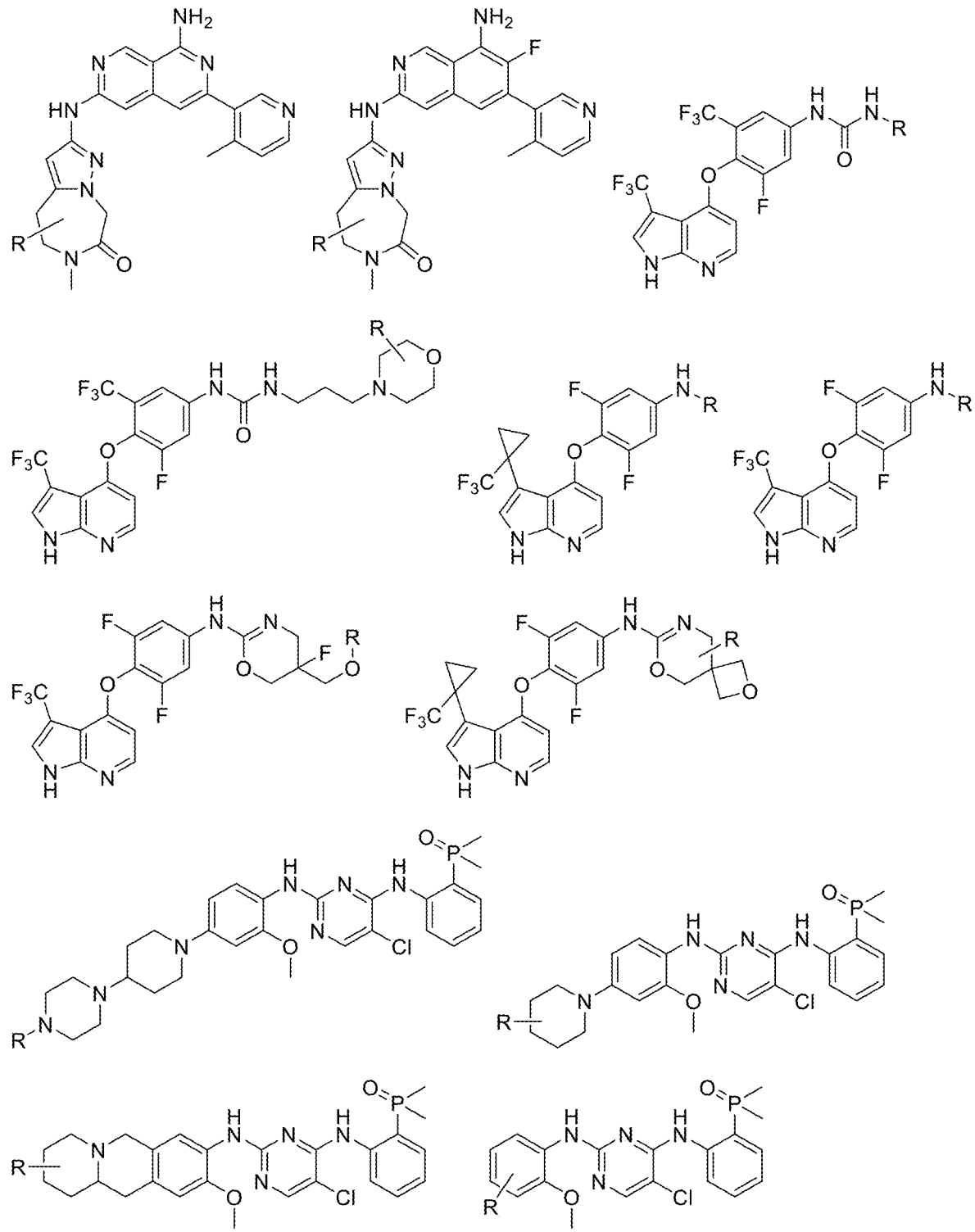
Figure 79D:
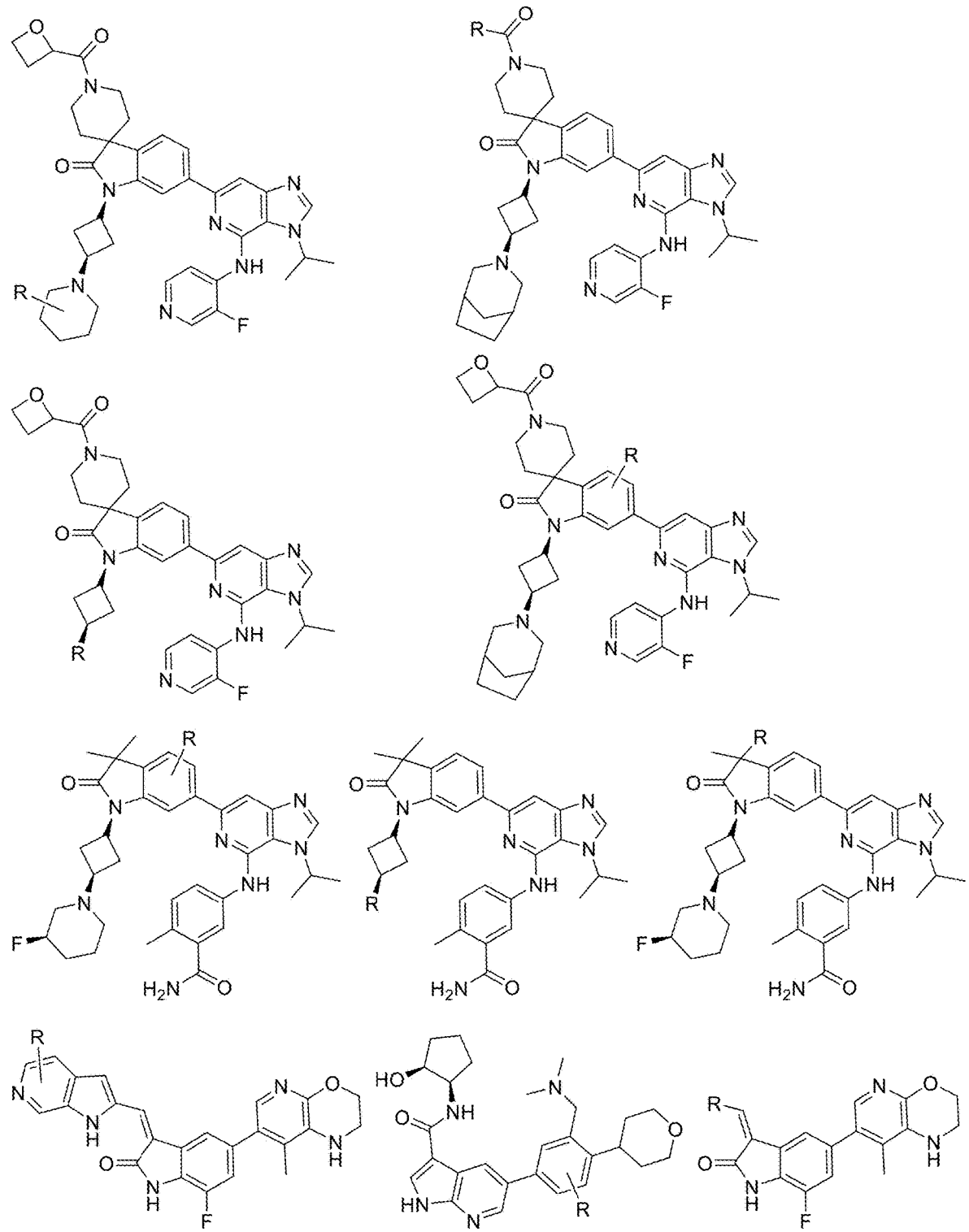
Figure 79E:
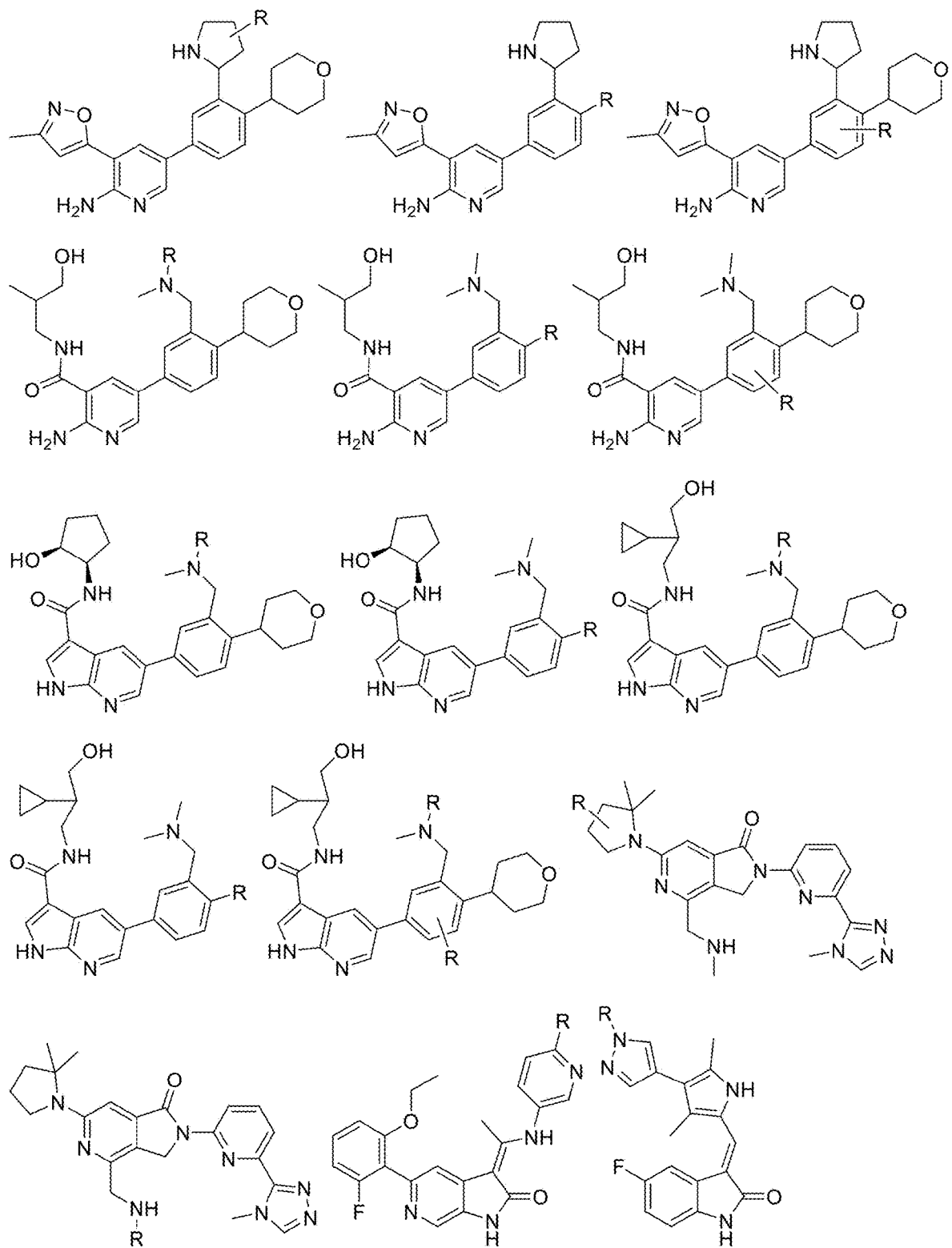
Figure 79F:
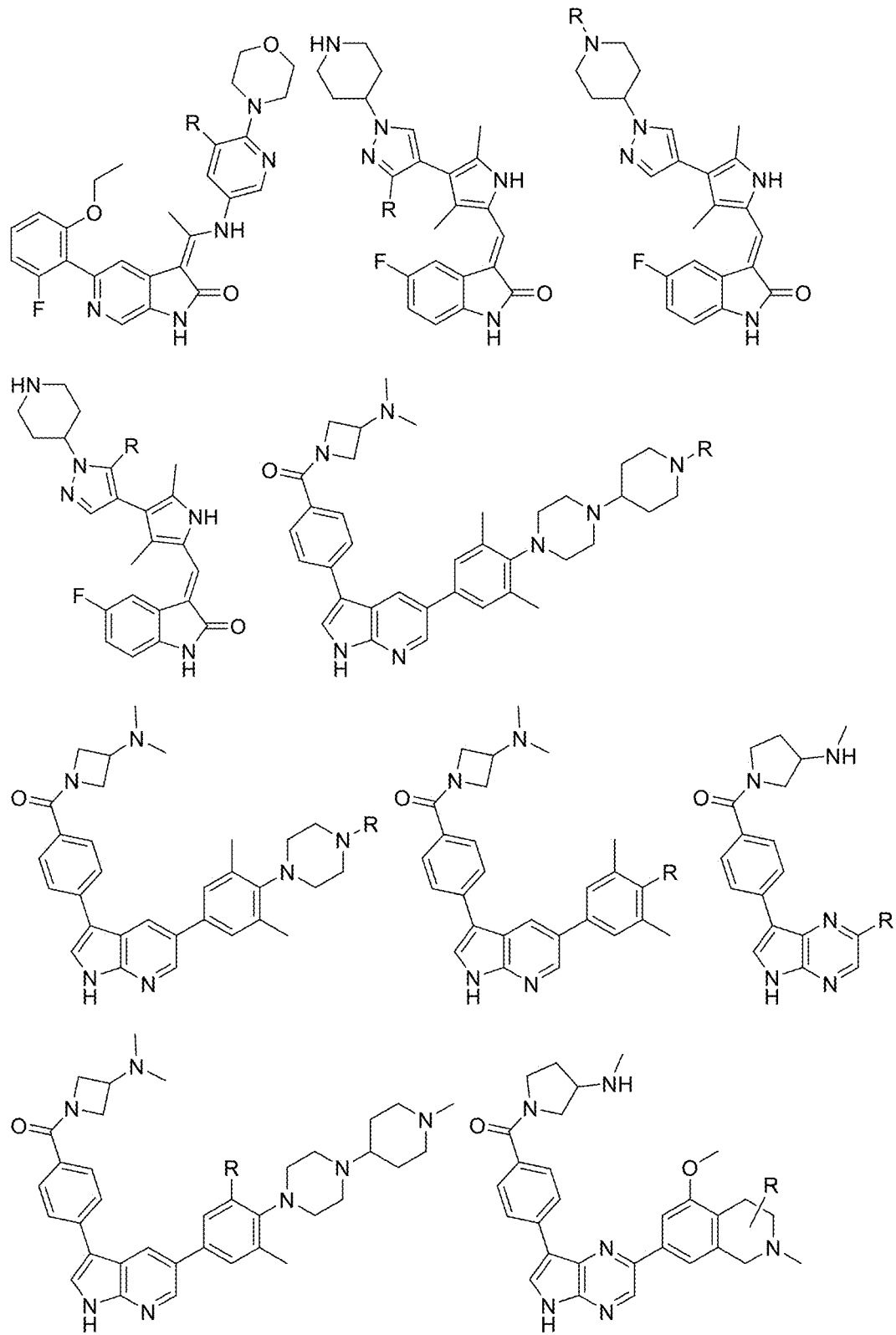
Figure 79G:
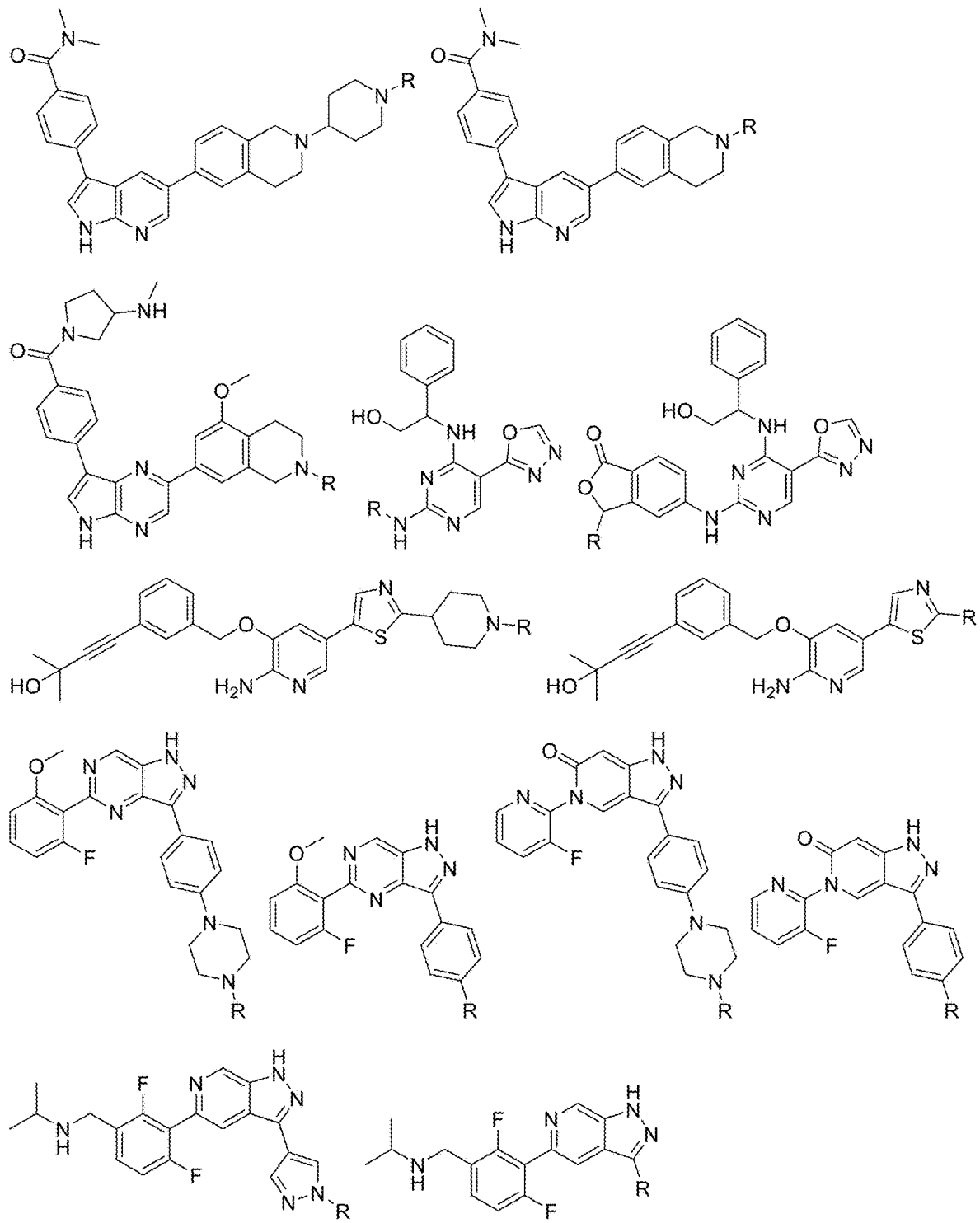
Figure 79H:
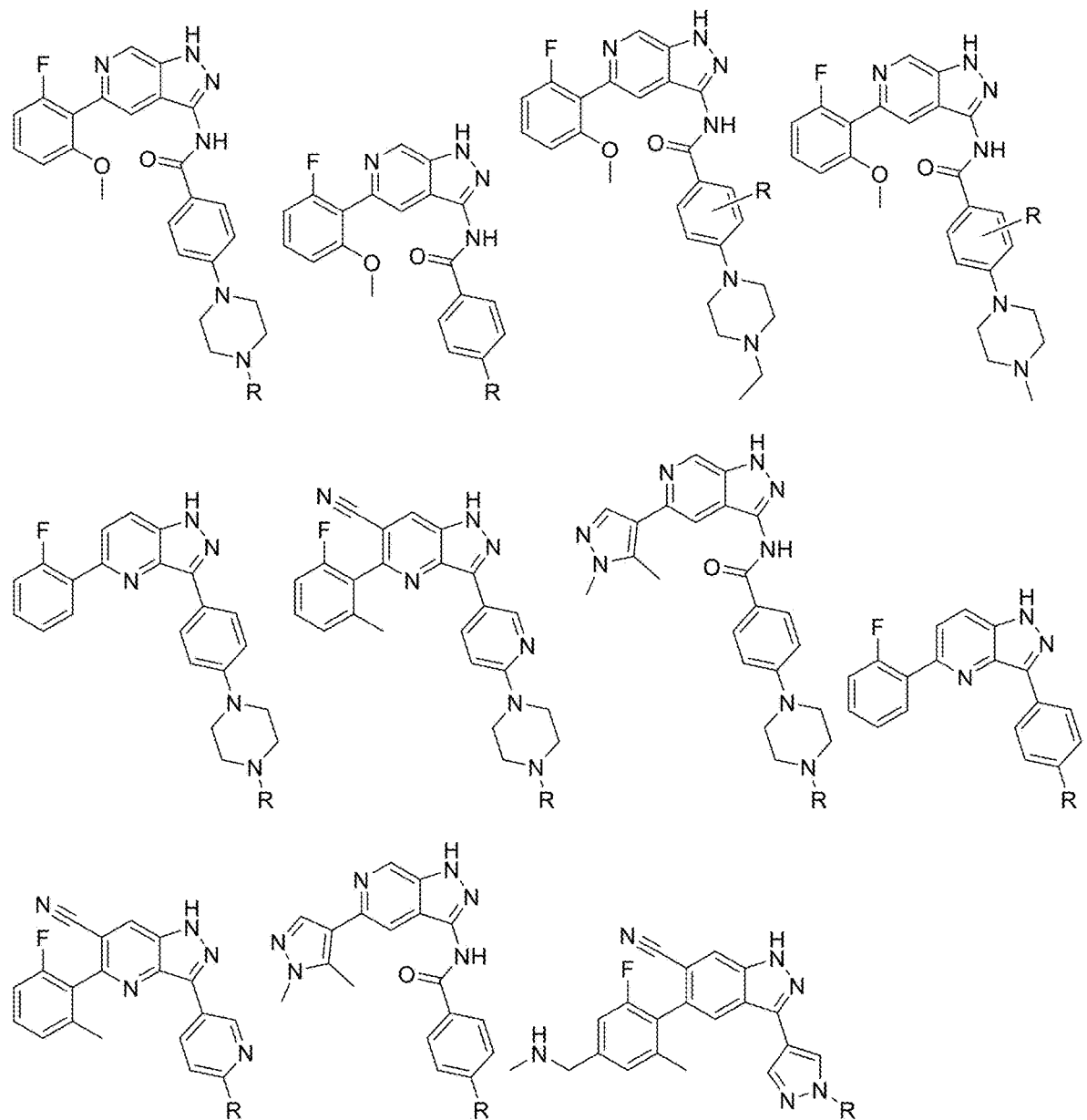
Figure 79I:
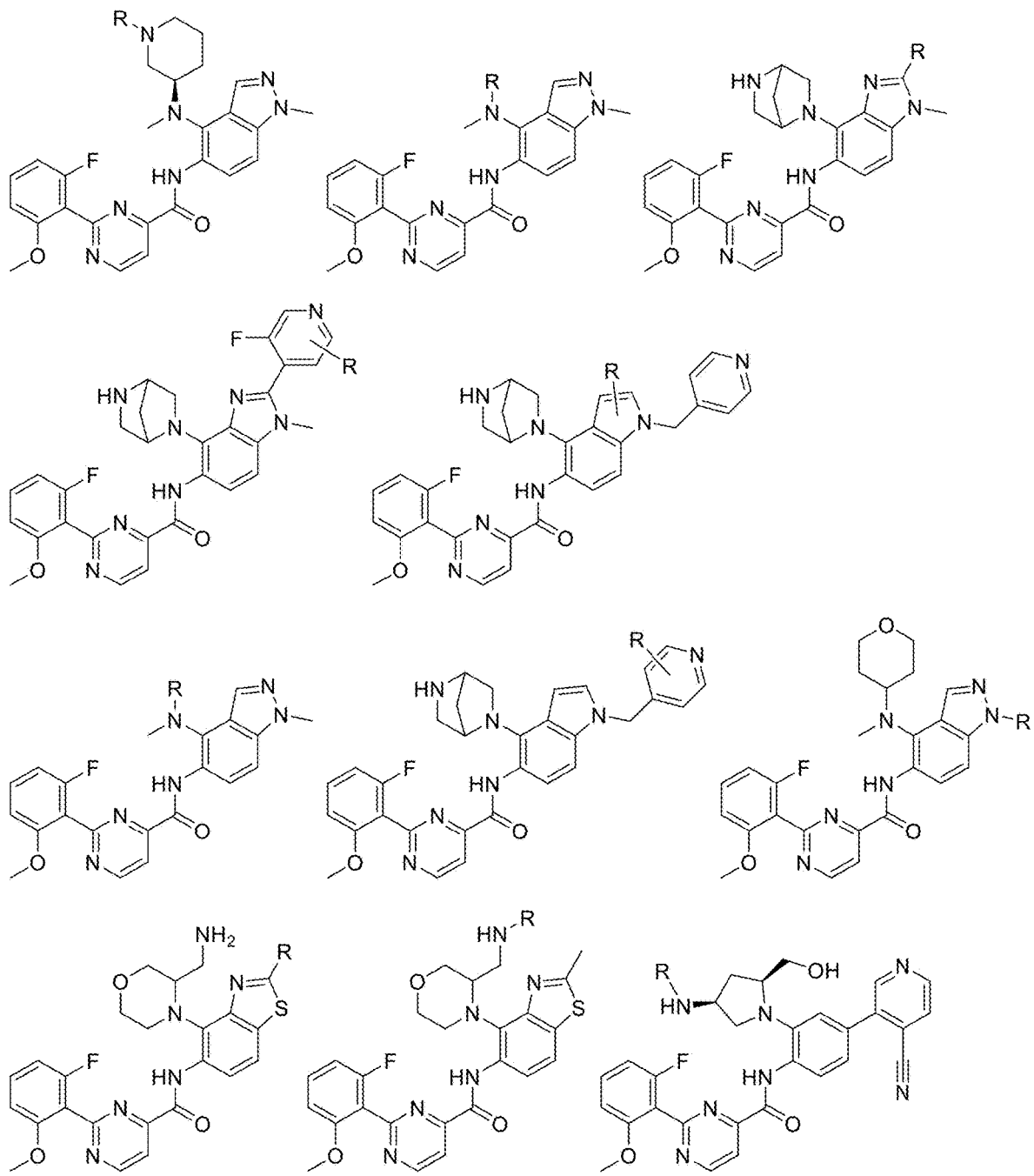
Figure 79J:
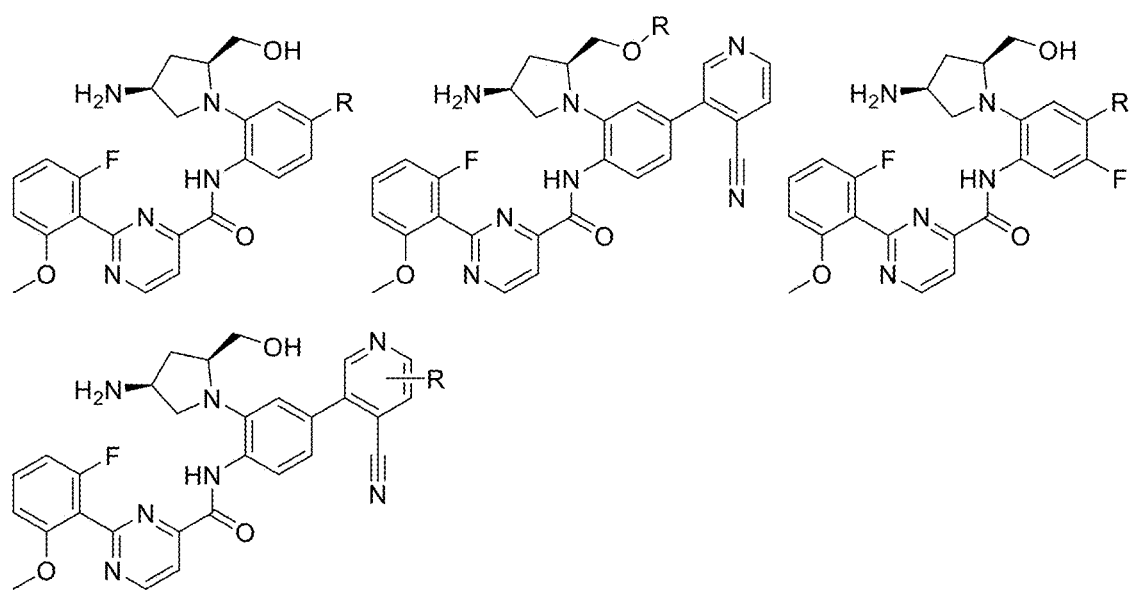

FIG. 78 provides non-limiting examples of ubiquitin specific peptidase 1 (USP1) Targeting Ligands wherein R represents exemplary points at which the Linker can be attached. Additional examples are provided in WO2021/163530.

FIG. 79A-79J provide non-limiting examples of hematopoietic progenitor kinase (HPK1) Targeting Ligands wherein R represents exemplary points at which the Linker can be attached. Additional examples are provided in Expert Opin. on Ther. Pat. 2021, 31, 10, 893-910.

DETAILED DESCRIPTION OF THE INVENTION

I. Definitions

Compounds are described using standard nomenclature. Unless defined otherwise, all technical and scientific terms used herein have the same meaning as is commonly understood by one of skill in the art to which this invention belongs.

The compounds in any of the Formulas described herein may be in the form of a racemate, enantiomer, mixture of enantiomers, diastereomer, mixture of diastereomers, tautomer, N-oxide, isomer; such as rotamer, as if each is specifically described unless specifically excluded by context.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed.

The present invention includes Degron and Degrader compounds with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine and iodine such as $^2$H, $^3$H, $^{11}$C, $^{13}$C, $^{14}$C, $^{15}$N, $^{17}$O, $^{18}$O, $^{18}$F $^{31}$P, $^{32}$P, $^{35}$S, $^{36}$Cl, and $^{125}$I respectively. In one non-limiting embodiment, isotopically labelled compounds can be used in metabolic studies (with, for example $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be any appropriate location of a Degron or Degrader compound.

In one non-limiting embodiment, the substitution of a hydrogen atom for a deuterium atom occurs within one or more groups selected from any of R's or variables described herein, Linker, and Targeting Ligand. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The compound of the present invention may form a solvate with a solvent (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvents are water, ethanol, isopropanol, dimethyl sulfoxide, acetone and other common organic solvents. The term "hydrate" refers to a molecular complex comprising a compound of the invention and water. Pharmaceutically acceptable solvates in accordance with the invention include those wherein the solvent may be isotopically substituted, e.g. $D_2O$, $d_6$-acetone, $d_6$-DMSO. A solvate can be in a liquid or solid form.

A dash ("—") that is not between two letters or symbols is used to indicate a point of attachment for a substituent. For example, —(C=O)NH$_2$ is attached through carbon of the carbonyl (C=O) group. "Alkyl" is a branched or straight chain saturated aliphatic hydrocarbon group. In one non-limiting embodiment, the alkyl group contains from 1 to about 12 carbon atoms, more generally from 1 to about 6 carbon atoms or from 1 to about 4 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species and therefore each subset is considered separately disclosed. For example, the term $C_1$-$C_4$alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. The term "alkyl" also encompasses cycloalkyl or carbocyclic groups. For example, when a term is used that includes "alk" then "cycloalkyl" or "carbocyclic" can be considered part of the definition, unless unambiguously excluded by the context. For example and without limitation, the terms alkyl, alkoxy, haloalkyl, etc. can all be considered to include the cyclic forms of alkyl, unless unambiguously excluded by context.

In one embodiment "alkyl" is a $C_1$-$C_{10}$alkyl, $C_1$-$C_9$alkyl, $C_1$-$C_8$alkyl, $C_1$-$C_7$alkyl, $C_1$-$C_6$alkyl, $C_1$-$C_5$alkyl, $C_1$-$C_4$alkyl, $C_1$-$C_3$alkyl, or $C_1$-$C_2$alkyl.

In one embodiment "alkyl" has one carbon.
In one embodiment "alkyl" has two carbons.
In one embodiment "alkyl" has three carbons.
In one embodiment "alkyl" has four carbons.
In one embodiment "alkyl" has five carbons.
In one embodiment "alkyl" has six carbons.

Non-limiting examples of "alkyl" include: methyl, ethyl, propyl, butyl, pentyl, and hexyl.

Additional non-limiting examples of "alkyl" include: isopropyl, isobutyl, isopentyl, and isohexyl.

Additional non-limiting examples of "alkyl" include: sec-butyl, sec-pentyl, and sec-hexyl.

Additional non-limiting examples of "alkyl" include: tert-butyl, tert-pentyl, and tert-hexyl.

Additional non-limiting examples of "alkyl" include: neopentyl, 3-pentyl, and active pentyl.

In one embodiment "cycloalkyl" is a $C_3$-$C_5$cycloalkyl, $C_3$-$C_7$cycloalkyl, $C_3$-$C_6$cycloalkyl, $C_3$-$C_5$cycloalkyl, $C_3$-$C_4$cycloalkyl, $C_4$-$C_5$cycloalkyl, $C_5$-$C_8$cycloalkyl, or $C_6$-$C_8$cycloalkyl.

In one embodiment "cycloalkyl" has three carbons.
In one embodiment "cycloalkyl" has four carbons.
In one embodiment "cycloalkyl" has five carbons.
In one embodiment "cycloalkyl" has six carbons.
In one embodiment "cycloalkyl" has seven carbons.
In one embodiment "cycloalkyl" has eight carbons.
In one embodiment "cycloalkyl" has nine carbons.
In one embodiment "cycloalkyl" has ten carbons.

Non-limiting examples of "cycloalkyl" include: cyclopropyl, cyclobutyl, cyclopentyl, cyclohexyl, cycloheptyl, cyclooctyl, and cyclodecyl.

Additional non-limiting examples of "cycloalkyl" include dihydro-indene and tetrahydronaphthalene wherein the point of attachment for each group is on the cycloalkyl ring.

For example:

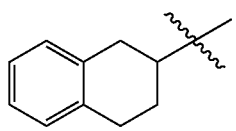 [SMILES: *C1CCc2ccccc2C1]

is an "cycloalkyl" group.
However,

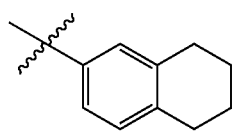 [SMILES: *c1ccc2c(c1)CCCC2]

is an "aryl" group.

"Alkenyl" is a linear or branched aliphatic hydrocarbon groups having one or more carbon-carbon double bonds that may occur at a stable point along the chain. The specified ranges as used herein indicate an alkenyl group having each member of the range described as an independent species, as described above for the alkyl moiety. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "7' alkenyl geometry. The term "Alkenyl" also encompasses cycloalkyl or carbocyclic groups possessing at least one point of unsaturation.

"Alkynyl" is a branched or straight chain aliphatic hydrocarbon group having one or more carbon-carbon triple bonds that may occur at any stable point along the chain. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. The term "Alkynyl" also encompasses cycloalkyl or carbocyclic groups possessing at least one triple bond.

"Alkylene" is a bivalent saturated hydrocarbon. Alkylenes, for example, can be a 1, 2, 3, 4, 5, 6, 7 to 8 carbon moiety, 1 to 6 carbon moiety, or an indicated number of carbon atoms, for example $C_1$-$C_2$alkylene, $C_1$-$C_3$alkylene, $C_1$-$C_4$alkylene, $C_1$-$C_5$alkylene, or $C_1$-$C_6$alkylene.

"Alkenylene" is a bivalent hydrocarbon having at least one carbon-carbon double bond. Alkenylenes, for example, can be a 2 to 8 carbon moiety, 2 to 6 carbon moiety, or an indicated number of carbon atoms, for example $C_2$-$C_4$alkenylene.

"Alkynylene" is a bivalent hydrocarbon having at least one carbon-carbon triple bond. Alkynylenes, for example, can be a 2 to 8 carbon moiety, a 2 to 6 carbon moiety, or an indicated number of carbon atoms, for example $C_2$-$C_4$alkynylene.

"Halo" and "Halogen" refers to fluorine, chlorine, bromine or iodine.

"Haloalkyl" is a branched or straight-chain alkyl groups substituted with 1 or more halo atoms described above, up to the maximum allowable number of halogen atoms. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

In one embodiment "haloalkyl" is a $C_1$-$C_{10}$haloalkyl, $C_1$-$C_9$haloalkyl, $C_1$-$C_8$haloalkyl, $C_1$-$C_7$haloalkyl, $C_1$-$C_6$haloalkyl, $C_1$-$C_5$haloalkyl, $C_1$-$C_4$haloalkyl, $C_1$-$C_3$haloalkyl, and $C_1$-$C_2$haloalkyl.

In one embodiment "haloalkyl" has one carbon.

In one embodiment "haloalkyl" has one carbon and one halogen.

In one embodiment "haloalkyl" has one carbon and two halogens.

In one embodiment "haloalkyl" has one carbon and three halogens.

In one embodiment "haloalkyl" has two carbons.

In one embodiment "haloalkyl" has three carbons.

In one embodiment "haloalkyl" has four carbons.

In one embodiment "haloalkyl" has five carbons.

In one embodiment "haloalkyl" has six carbons.

Non-limiting examples of "haloalkyl" include:

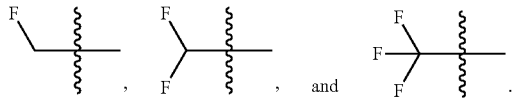

Additional non-limiting examples of "haloalkyl" include:

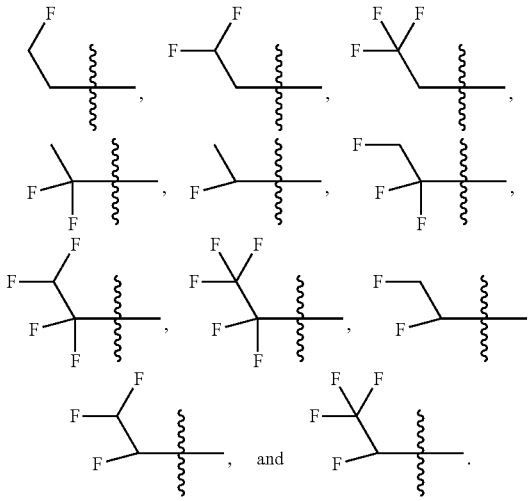

Additional non-limiting examples of "haloalkyl" include:

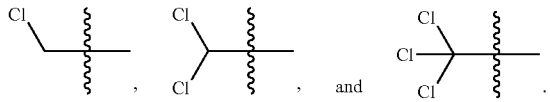

Additional non-limiting examples of "haloalkyl" include:

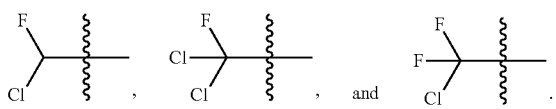

"Chain" indicates a linear chain to which all other chains, long or short or both, may be regarded as being pendant. Where two or more chains could equally be considered to be the main chain, "chain" refers to the one which leads to the simplest representation of the molecule.

"Haloalkoxy" indicates a haloalkyl group as defined herein attached through an oxygen bridge (oxygen of an alcohol radical).

"Heterocycloalkyl" is an alkyl group as defined herein substituted with a heterocyclo group as defined herein.

"Arylalkyl" is an alkyl group as defined herein substituted with an aryl group as defined herein.

Non-limiting examples of "arylalkyl" include:

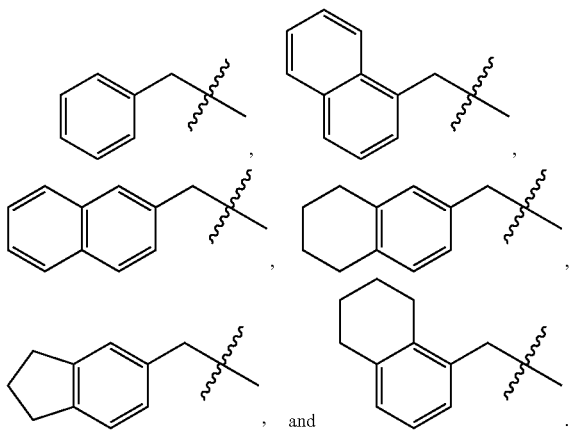

In one embodiment "arylalkyl" is

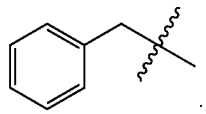 [SMILES: *Cc1ccccc1]

In one embodiment the "arylalkyl" refers to a 2 carbon alkyl group substituted with an aryl group.

Non-limiting examples of "arylalkyl" include:

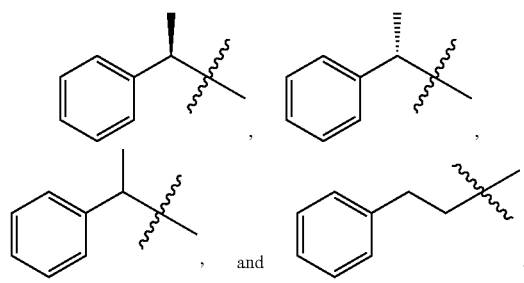

In one embodiment the "arylalkyl" refers to a 3 carbon alkyl group substituted with an aryl group.

"Heteroarylalkyl" is an alkyl group as defined herein substituted with a heteroaryl group as defined herein.

As used herein, "aryl" refers to a radical of a monocyclic or polycyclic (e.g., bicyclic or tricyclic) 4n+2 aromatic ring system (e.g., having 6, 10, or 14 7L electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. The one or more fused carbocyclyl or heterocyclyl groups can be 4 to 7 or 5 to 7-membered saturated or partially unsaturated carbocyclyl or heterocyclyl groups that optionally contain 1, 2, or 3 heteroatoms independently selected from nitrogen, oxygen, phosphorus, sulfur, silicon and boron, to form, for example, a 3,4-methylenedioxyphenyl group. In one non-limiting embodiment, aryl groups are pendant. An example of a pendant ring is a phenyl group substituted with a phenyl group. In certain embodiments, the aryl group is an unsubstituted $C_{6-14}$ aryl.

In one embodiment "aryl" is a 6 carbon aromatic group (phenyl).

In one embodiment "aryl" is a 10 carbon aromatic group (napthyl).

In one embodiment "aryl" is a 6 carbon aromatic group fused to a heterocycle wherein the point of attachment is the aryl ring. Non-limiting examples of "aryl" include indoline, tetrahydroquinoline, tetrahydroisoquinoline, and dihydrobenzofuran wherein the point of attachment for each group is on the aromatic ring.

For example

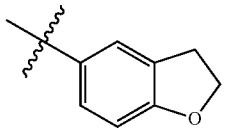 [SMILES: *c1ccc2c(c1)CCO2]

is an "aryl" group.

However,

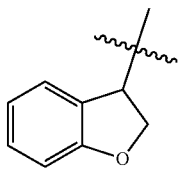 [SMILES: *C1COc2ccccc21]

is a "heterocycle" group.

In one embodiment "aryl" is a 6 carbon aromatic group fused to a cycloalkyl wherein the point of attachment is the aryl ring. Non-limiting examples of "aryl" include dihydroindene and tetrahydronaphthalene wherein the point of attachment for each group is on the aromatic ring.

For example

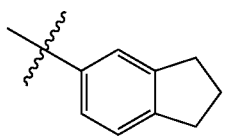 [SMILES: *c1ccc2c(c1)CCC2]

is an "aryl" group.
However,

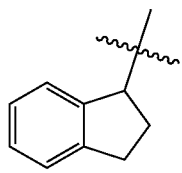 [SMILES: *C1CCc2ccccc21]

is a "cycloalkyl" group.

The term "heterocyclyl", "heterocycle", and "heterocyclo" includes saturated, and partially saturated heteroatom-containing ring radicals, where the heteroatoms may be selected from nitrogen, sulfur and oxygen. Heterocyclic rings comprise monocyclic 3, 4, 5, 6, 7, 8, 9, or 10 membered rings, as well as 5, 6, 7, 8, 9, 10, 11, 12, 13, 14, 15, or 16 membered bicyclic ring systems (which can include bridged fused and spiro-fused bicyclic ring systems). It does not include rings containing —O—O—, —O—S— or —S—S— portions.

Examples of saturated heterocyclo groups include saturated 3, 4, 5, or 6-membered heteromonocyclic groups containing 1, 2, 3, or 4 nitrogen atoms [e.g. pyrrolidinyl, imidazolidinyl, piperidinyl, pyrrolinyl, piperazinyl]; saturated 3, 4, 5, or 6-membered heteromonocyclic group containing 1 or 2 oxygen atoms and 1, 2, or 3 nitrogen atoms [e.g. morpholinyl]; saturated 3, 4, 5, or 6-membered heteromonocyclic group containing 1 or 2 sulfur atoms and 1, 2, or 3 nitrogen atoms [e.g., thiazolidinyl]. Examples of partially saturated heterocyclyl radicals include but are not limited to, dihydrothienyl, dihydropyranyl, dihydrofuryl, and dihydrothiazolyl.

Examples of partially saturated and saturated heterocyclo groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1),-benzo[d]isothiazol-6-yl, dihydropyranyl, dihydrofuryl, isoquinolin-1(2H)-onyl, benzo[d]oxazol-2(3H)-onyl, 1,3-dihydro-2H-benzo[d]midazol-2-onyl, benzo[d]thiazole-2(3H)-onyl, 1,2-dihydro-3H-pyrazol-3-onyl, 2(1H)-pyridinonyl, 2-piperazinonyl, indolinyl, and dihydrothiazolyl.

The term "heterocyclyl", "heterocycle", and "heterocyclo" groups also include moieties where heterocyclic radicals are fused/condensed with aryl or heteroaryl radicals: such as unsaturated condensed heterocyclic group containing 1, 2, 3, 4, or 5 nitrogen atoms, for example, indoline, isoindoline, unsaturated condensed heterocyclic group containing 1 or 2 oxygen atoms and 1, 2, or 3 nitrogen atoms, unsaturated condensed heterocyclic group containing 1 or 2 sulfur atoms and 1, 2, or 3 nitrogen atoms, and saturated, partially unsaturated and unsaturated condensed heterocyclic group containing 1 or 2 oxygen or sulfur atoms.

In one embodiment "heterocycle" refers to a cyclic ring with one nitrogen and 3, 4, 5, 6, 7, or 8 carbon atoms.

In one embodiment "heterocycle" refers to a cyclic ring with one nitrogen and one oxygen and 3, 4, 5, 6, 7, or 8 carbon atoms.

In one embodiment "heterocycle" refers to a cyclic ring with two nitrogens and 3, 4, 5, 6, 7, or 8 carbon atoms.

In one embodiment "heterocycle" refers to a cyclic ring with one oxygen and 3, 4, 5, 6, 7, or 8 carbon atoms.

In one embodiment "heterocycle" refers to a cyclic ring with one sulfur and 3, 4, 5, 6, 7, or 8 carbon atoms.

Non-limiting examples of "heterocycle" include aziridine, oxirane, thiirane, azetidine, 1,3-diazetidine, oxetane, and thietane.

Additional non-limiting examples of "heterocycle" include pyrrolidine, 3-pyrroline, 2-pyrroline, pyrazolidine, and imidazolidine.

Additional non-limiting examples of "heterocycle" include tetrahydrofuran, 1,3-dioxolane, tetrahydrothiophene, 1,2-oxathiolane, and 1,3-oxathiolane.

Additional non-limiting examples of "heterocycle" include piperidine, piperazine, tetrahydropyran, 1,4-dioxane, thiane, 1,3-dithiane, 1,4-dithiane, morpholine, and thiomorpholine.

Additional non-limiting examples of "heterocycle" include indoline, tetrahydroquinoline, tetrahydroisoquinoline, and dihydrobenzofuran wherein the point of attachment for each group is on the heterocyclic ring.

For example,

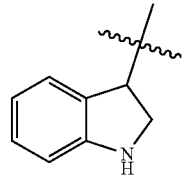 [SMILES: *C1CNc2ccccc21]

is a "heterocycle" group.
However,

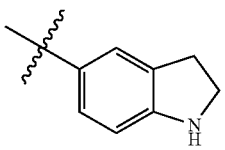 [SMILES: *c1ccc2c(c1)CCN2]

is an "aryl" group.
Non-limiting examples of "heterocycle" also include:

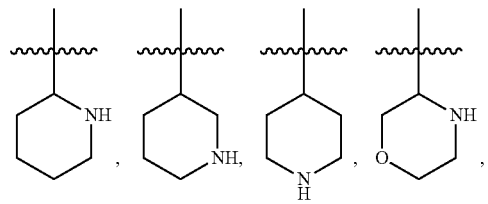

-continued

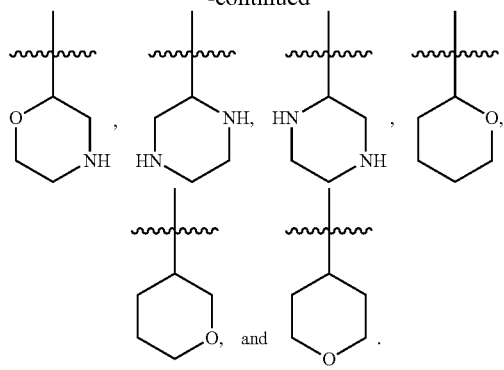

Additional non-limiting examples of "heterocycle" include:

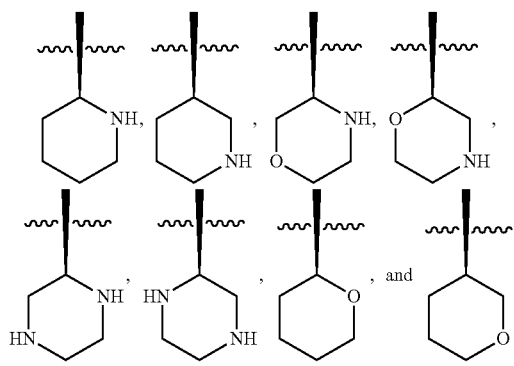

Additional non-limiting examples of "heterocycle" include:

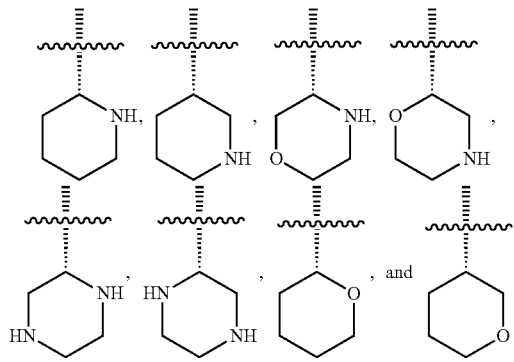

Non-limiting examples of "heterocycle" also include:

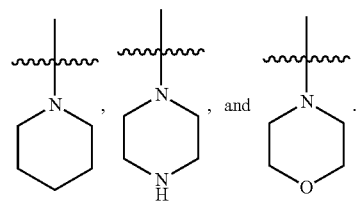

Non-limiting examples of "heterocycle" also include:

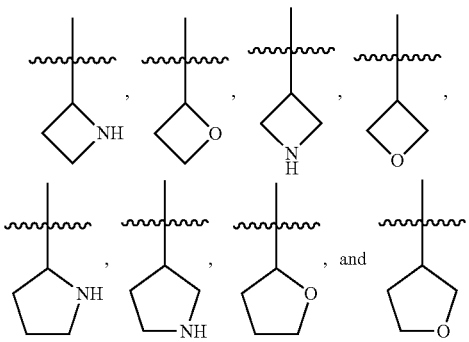

Additional non-limiting examples of "heterocycle" include:

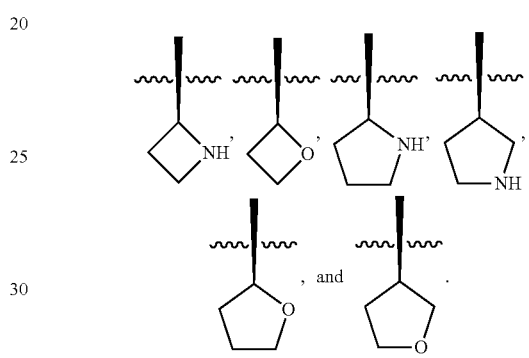

Additional non-limiting examples of "heterocycle" include:

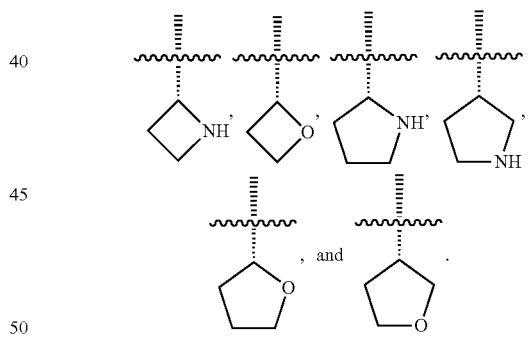

The term "heteroaryl" denotes a monocyclic or polycyclic (e.g., bicyclic or tricyclic) 4n+2 aromatic ring system (e.g., having 6, 10, or 14 π electrons shared in a cyclic array) and 1, 2, 3, 4, 5, or 6, heteroatoms independently selected from O, N, and S, wherein the ring nitrogen and sulfur atom(s) are optionally oxidized, and nitrogen atom(s) are optionally quarternized. Examples include but are not limited to, unsaturated 5 to 6 membered heteromonocyclyl groups containing 1, 2, 3, or 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl]; unsaturated 5- or 6-membered heteromonocyclic groups containing an oxygen atom, for example, pyranyl, 2-furyl, 3-furyl, etc.; unsaturated 5- or 6-membered heteromonocyclic groups containing a sulfur atom, for example, 2-thienyl, 3-thienyl, etc.; unsaturated 5- or 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 or 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl]. Additional examples include 8-, 9-, or 10-membered heteroaryl bicyclic groups such as indazolyl, indolyl, imidazo[1,5-a]pyridinyl, benzimidazolyl, 4(3H)-quinazolinonyl, quinolinyl, isoquinolinyl, isoindolyl, thienothienyl, indolizinyl, benzofuranyl, isobenzofuranyl, benzothienyl, isobenzothienyl, benzoxazolyl, benzothiazolyl, purinyl, coumarinyl, cinnolinyl, and triazolopyridinyl.

In one embodiment "heteroaryl" is a 5 membered aromatic group containing 1, 2, 3, or 4 nitrogen atoms.

Non-limiting examples of 5 membered "heteroaryl" groups include pyrrole, furan, thiophene, pyrazole, imidazole, triazole, tetrazole, isoxazole, oxazole, oxadiazole, oxatriazole, isothiazole, thiazole, thiadiazole, and thiatriazole.

Additional non-limiting examples of 5 membered "heteroaryl" groups include:

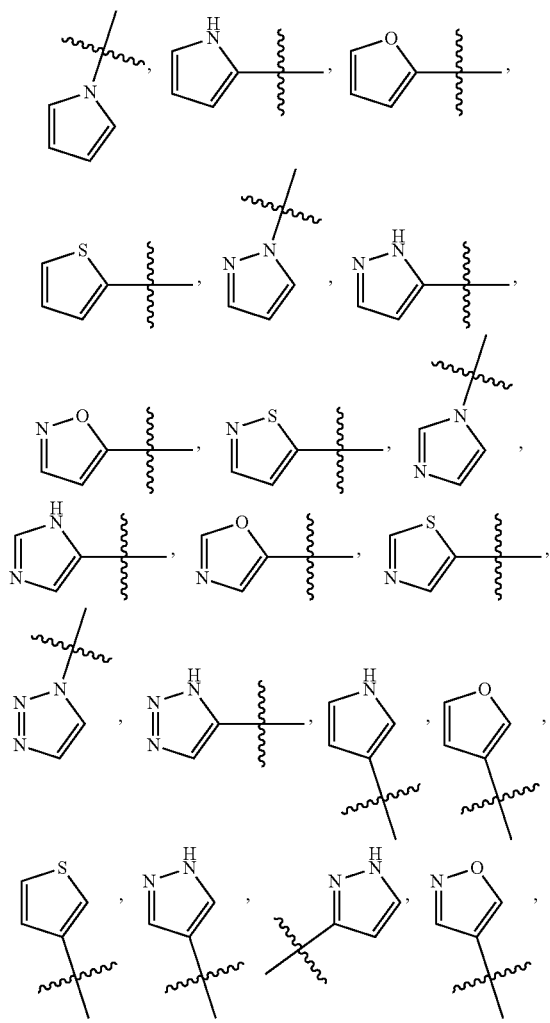

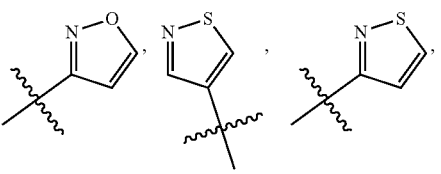

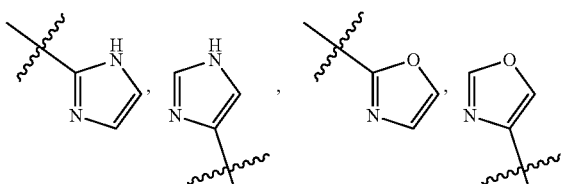

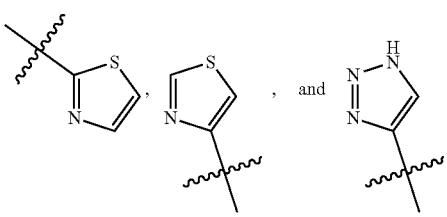

In one embodiment "heteroaryl" is a 6 membered aromatic group containing 1, 2, or 3 nitrogen atoms (i.e. pyridinyl, pyridazinyl, triazinyl, pyrimidinyl, and pyrazinyl).

Non-limiting examples of 6 membered "heteroaryl" groups with 1 or 2 nitrogen atoms include:

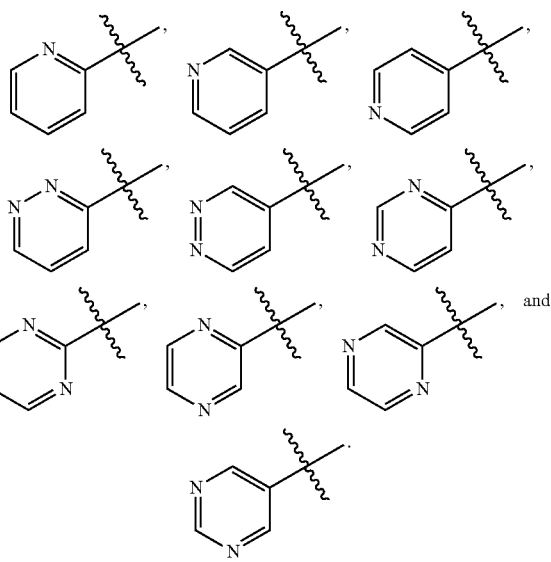

In one embodiment "heteroaryl" is a 9 membered bicyclic aromatic group containing 1 or 2 atoms selected from nitrogen, oxygen, and sulfur.

Non-limiting examples of "heteroaryl" groups that are bicyclic include indole, benzofuran, isoindole, indazole, benzimidazole, azaindole, azaindazole, purine, isobenzofuran, benzothiophene, benzoisoxazole, benzoisothiazole, benzooxazole, and benzothiazole.

Additional non-limiting examples of "heteroaryl" groups that are bicyclic include:

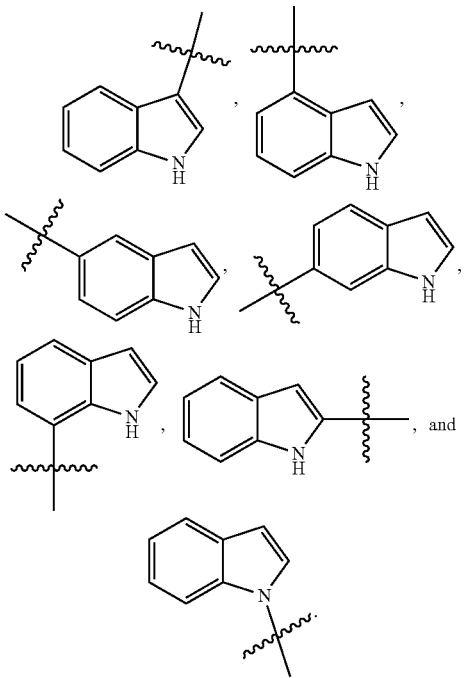

Additional non-limiting examples of "heteroaryl" groups that are bicyclic include:

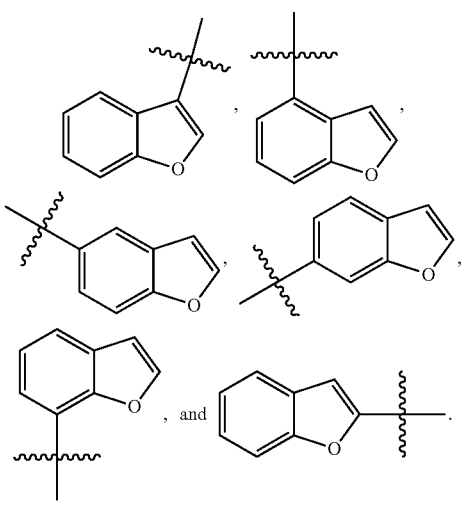

Additional non-limiting examples of "heteroaryl" groups that are bicyclic include:

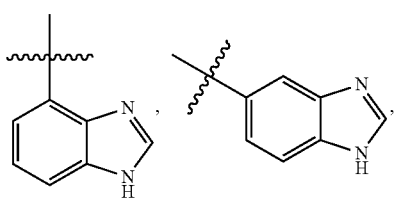

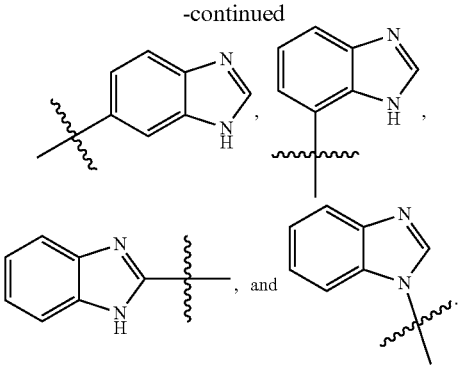

In one embodiment "heteroaryl" is a 10 membered bicyclic aromatic group containing 1 or 2 atoms selected from nitrogen, oxygen, and sulfur.

Non-limiting examples of "heteroaryl" groups that are bicyclic include quinoline, isoquinoline, quinoxaline, phthalazine, quinazoline, cinnoline, and naphthyridine.

Additional non-limiting examples of "heteroaryl" groups that are bicyclic include:

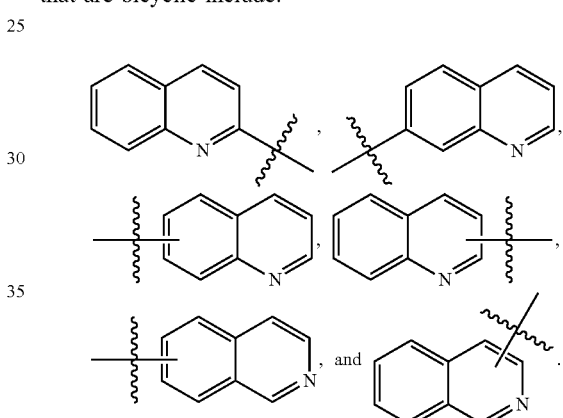

In one embodiment a group described herein that can be substituted with 1, 2, 3, or 4 substituents is substituted with one substituent.

In one embodiment a group described herein that can be substituted with 1, 2, 3, or 4 substituents is substituted with two substituents.

In one embodiment a group described herein that can be substituted with 1, 2, 3, or 4 substituents is substituted with three substituents.

In one embodiment a group described herein that can be substituted with 1, 2, 3, or 4 substituents is substituted with four substituents.

"Aliphatic" refers to a saturated or unsaturated, straight, branched, or cyclic hydrocarbon. "Aliphatic"" is intended herein to include, but is not limited to, alkyl, alkenyl, alkynyl, cycloalkyl, cycloalkenyl, and cycloalkynyl moieties, and thus incorporates each of these definitions. In one embodiment, "aliphatic" is used to indicate those aliphatic groups having 1-20 carbon atoms. The aliphatic chain can be, for example, mono-unsaturated, di-unsaturated, tri-unsaturated, or polyunsaturated, or alkynyl. Unsaturated aliphatic groups can be in a cis or trans configuration. In one embodiment, the aliphatic group contains from 1 to about 12 carbon atoms, more generally from 1 to about 6 carbon atoms or from 1 to about 4 carbon atoms.

In one embodiment, the aliphatic group contains from 1 to about 8 carbon atoms. In certain embodiments, the aliphatic group is $C_1$-$C_2$, $C_1$-$C_3$, $C_1$-$C_4$, $C_1$-$C_5$ or $C_1$-$C_6$. The specified ranges as used herein indicate an aliphatic group having each member of the range described as an independent species. For example, the term $C_1$-$C_6$ aliphatic as used herein indicates a straight or branched alkyl, alkenyl, or alkynyl group having from 1, 2, 3, 4, 5, or 6 carbon atoms and is intended to mean that each of these is described as an independent species. For example, the term $C_1$-$C_4$ aliphatic as used herein indicates a straight or branched alkyl, alkenyl, or alkynyl group having from 1, 2, 3, or 4 carbon atoms and is intended to mean that each of these is described as an independent species. In one embodiment, the aliphatic group is substituted with one or more functional groups that results in the formation of a stable moiety.

The term "heteroaliphatic" refers to an aliphatic moiety that contains at least one heteroatom in the chain, for example, an amine, carbonyl, carboxy, oxo, thio, phosphate, phosphonate, nitrogen, phosphorus, silicon, or boron atoms in place of a carbon atom. In one embodiment, the only heteroatom is nitrogen. In one embodiment, the only heteroatom is oxygen. In one embodiment, the only heteroatom is sulfur.

"Heteroaliphatic" is intended herein to include, but is not limited to, heteroalkyl, heteroalkenyl, heteroalkynyl, heterocycloalkyl, heterocycloalkenyl, and heterocycloalkynyl moieties. In one embodiment, "heteroaliphatic" is used to indicate a heteroaliphatic group (cyclic, acyclic, substituted, unsubstituted, branched or unbranched) having 1-20 carbon atoms. Nonlimiting examples of heteroaliphatic moieties are polyethylene glycol, polyalkylene glycol, amide, polyamide, polylactide, polyglycolide, thioether, ether, alkyl-heterocycle-alkyl, —O-alkyl-O-alkyl, alkyl-O-haloalkyl, etc.

A "dosage form" means a unit of administration of an active agent. Examples of dosage forms include tablets, capsules, injections, suspensions, liquids, emulsions, implants, particles, spheres, creams, ointments, suppositories, inhalable forms, transdermal forms, buccal, sublingual, topical, gel, mucosal, and the like. A "dosage form" can also include an implant, for example an optical implant.

An "effective amount" as used herein, means an amount which provides a therapeutic or prophylactic benefit.

As used herein "endogenous" refers to any material from or produced inside an organism, cell, tissue or system.

As used herein, the term "exogenous" refers to any material introduced from or produced outside an organism, cell, tissue or system.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

"Parenteral" administration of a pharmaceutical composition includes, e.g., subcutaneous (s.c.), intravenous (i.v.), intramuscular (i.m.), intrasternal injection, or infusion techniques.

As used herein, the terms "peptide," "polypeptide," and "protein" are used interchangeably, and refer to a compound comprised of amino acid residues covalently linked by peptide bonds. A protein or peptide must contain at least two amino acids, and the maximum number of amino acids present within the protein or peptide's sequence is typically comparable to up to that found in nature. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

To "treat" a disease as the term is used herein, means to reduce the frequency or severity of at least one sign or symptom of a disease or disorder experienced by a subject (i.e. palliative treatment) or to decrease a cause or effect of the disease or disorder (i.e. disease-modifying treatment).

Throughout this disclosure, various aspects of the invention can be presented in a range format. It should be understood that the description in range format is merely for convenience and should not be construed as a limitation on the scope of the invention. The description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

As used herein, "pharmaceutical compositions" are compositions comprising at least one active agent, and at least one other substance, such as a carrier. "Pharmaceutical combinations" are combinations of at least two active agents which may be combined in a single dosage form or provided together in separate dosage forms with instructions that the active agents are to be used together to treat any disorder described herein.

As used herein, "pharmaceutically acceptable salt" is a derivative of the disclosed compound in which the parent compound is modified by making inorganic and organic, non-toxic, acid or base addition salts thereof. The salts of the present compounds can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds further include solvates of the compounds and of the compound salts.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like, or using a different acid that produces the same counterion. Lists of additional suitable salts may be found, e.g., in *Remington's Pharmaceutical Sciences,* 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

A "pharmaceutically acceptable excipient" means an excipient that is useful in preparing a pharmaceutical composition/combination that is generally safe, non-toxic and neither biologically nor otherwise inappropriate for administration to a host, typically a human. In one embodiment, an excipient is used that is acceptable for veterinary use.

A "patient" or "host" or "subject" is a human or non-human animal in need of treatment or prevention of any of the disorders as specifically described herein, for example that is modulated by a natural (wild-type) or modified (non-wild type) protein that can be degraded according to the present invention, resulting in a therapeutic effect. Typically, the host is a human. A "host" may alternatively refer to for example, a mammal, primate (e.g., human), cow, sheep, goat, horse, dog, cat, rabbit, rat, mice, fish, bird and the like.

A "therapeutically effective amount" of a pharmaceutical composition/combination of this invention means an amount effective, when administered to a host, to provide a therapeutic benefit such as an amelioration of symptoms or reduction or diminution of the disease itself.

II. Compounds of the Present Invention

In certain aspects, a Degron compound of Formula IAa, Formula IAb, or Formula IAc is provided:

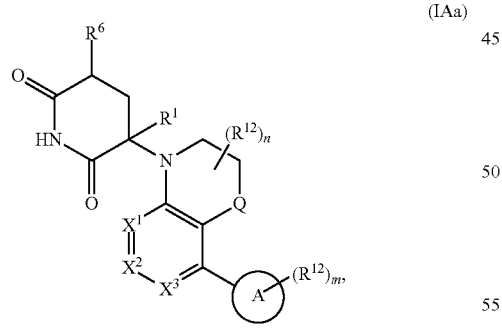
(IAa)

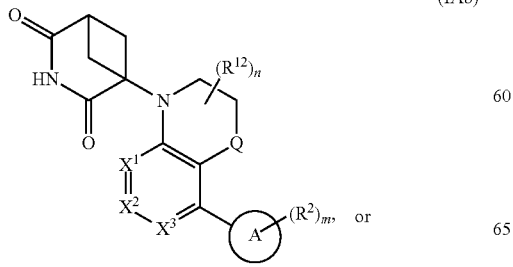
(IAb), or

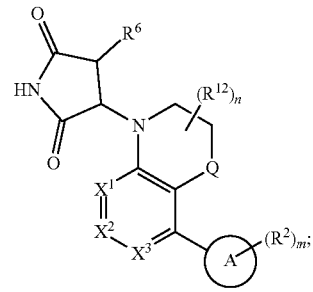
(IAc)

or a pharmaceutically acceptable salt, N-oxide, isotopic derivative or prodrug thereof, optionally in a pharmaceutically acceptable carrier to form a pharmaceutical composition;

wherein all variables are defined as above.

In certain aspects, the Degron compound of the present invention is selected from

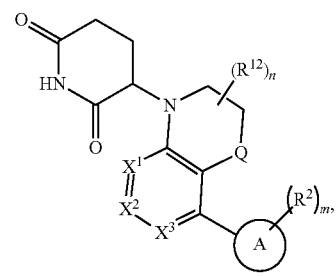

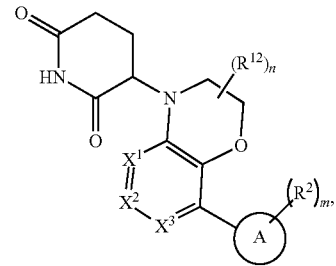

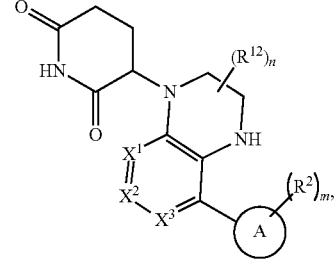

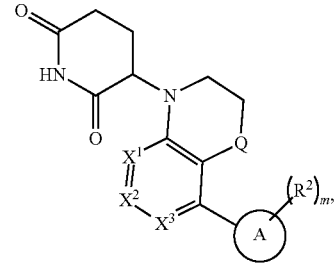

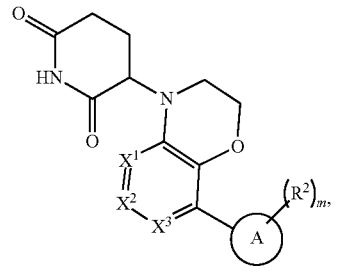
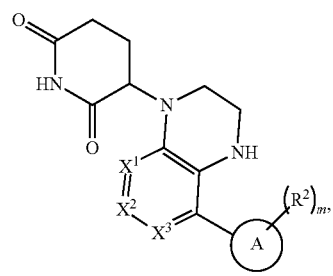
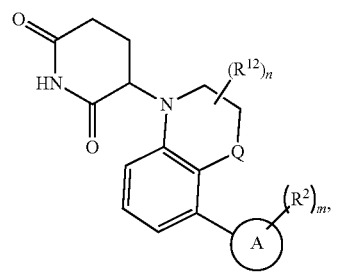
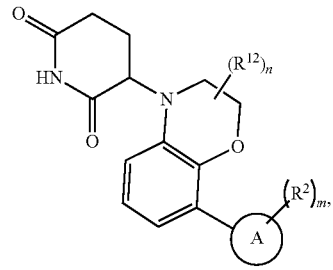
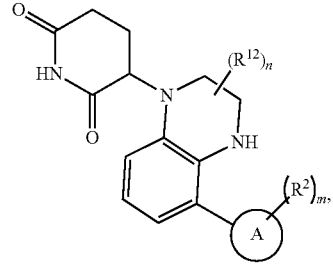
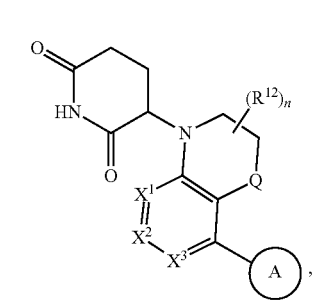
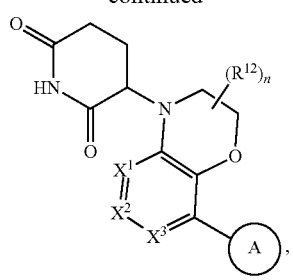
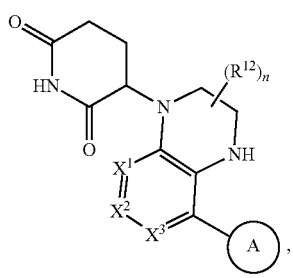
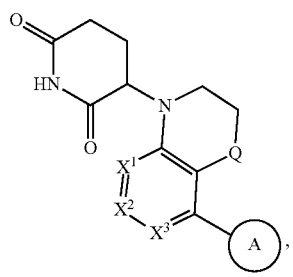
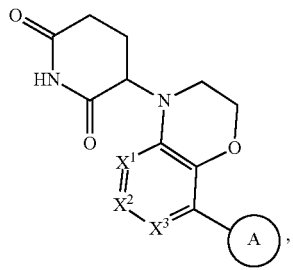
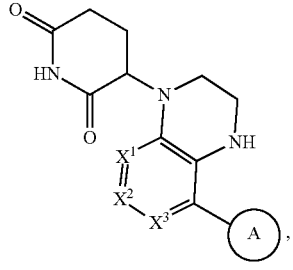
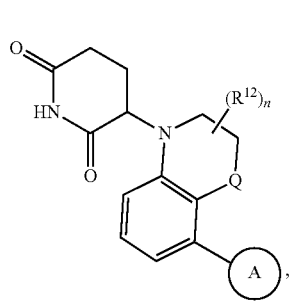

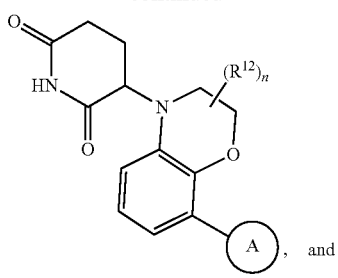, and
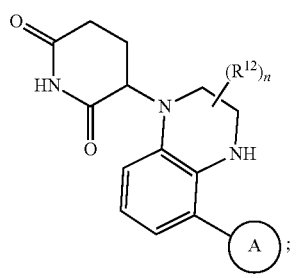;
or a pharmaceutically acceptable salt thereof.
In certain aspects, the Degron compound of the present invention is selected from
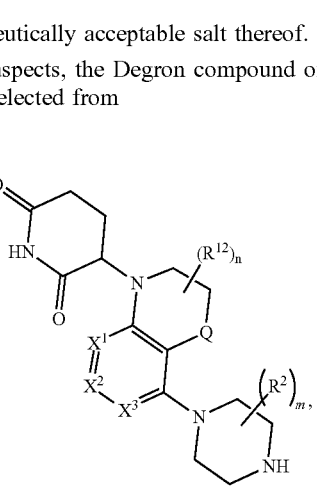
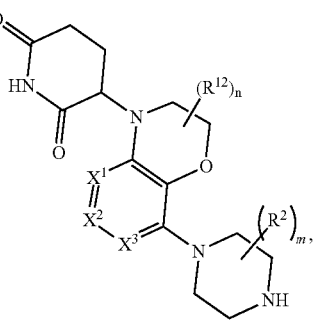
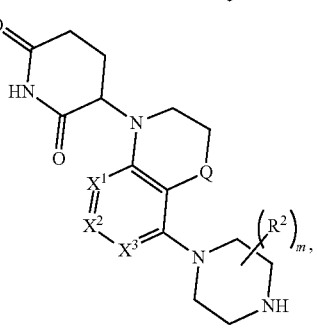
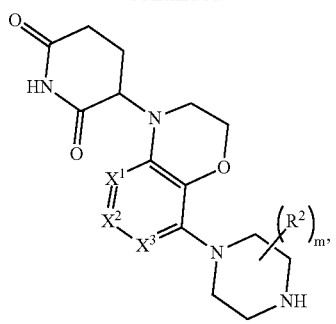
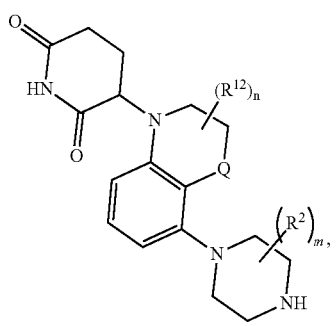
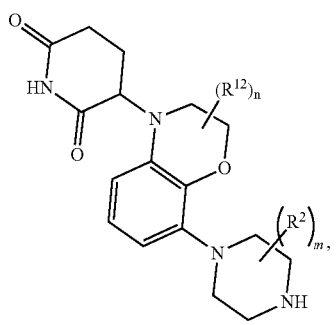
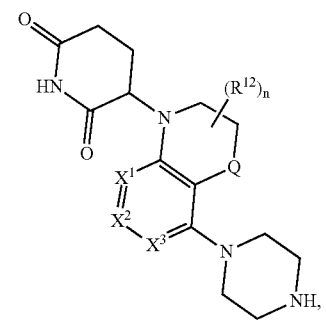
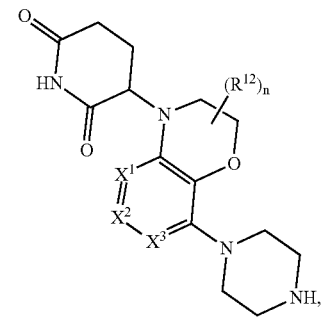

-continued
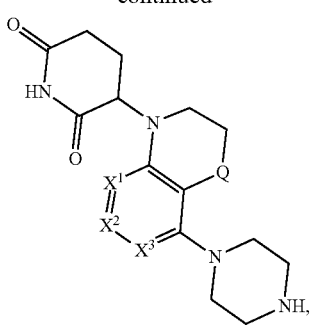
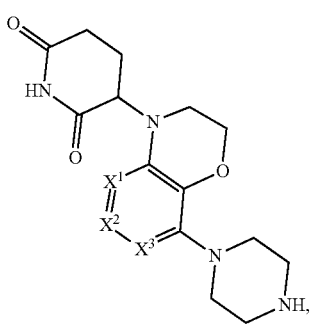
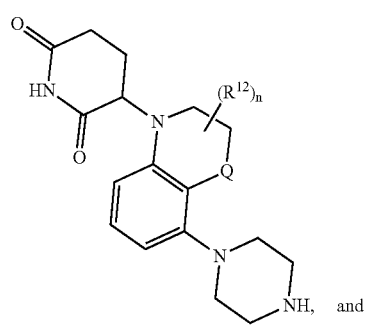
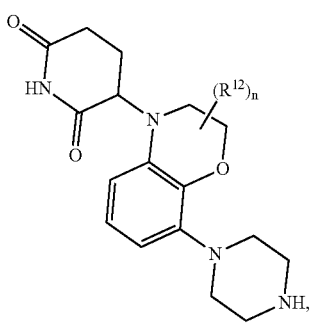
or a pharmaceutically acceptable salt thereof.
In certain aspects, the Degron compound of the present invention is selected from
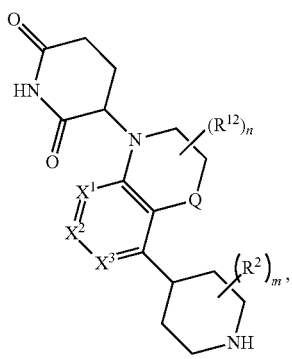
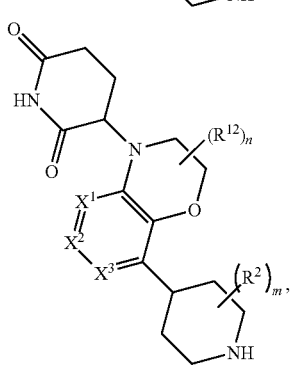
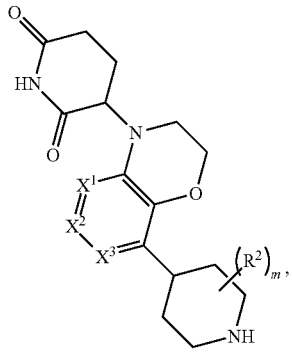

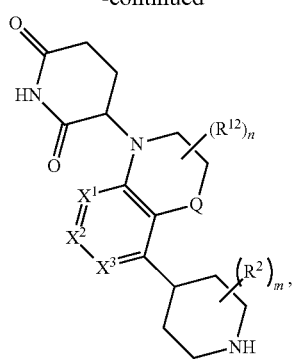
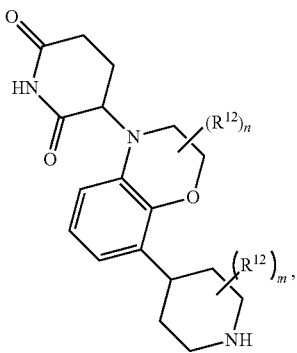
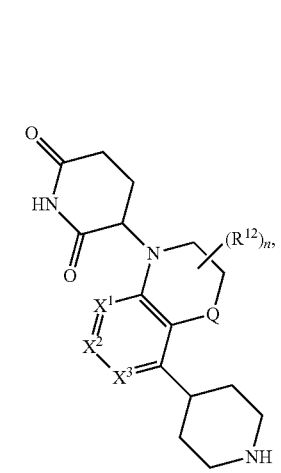
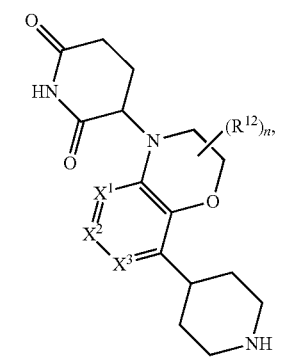
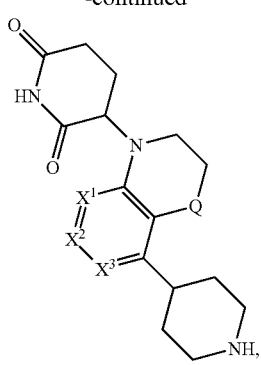
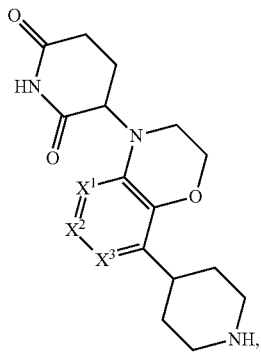
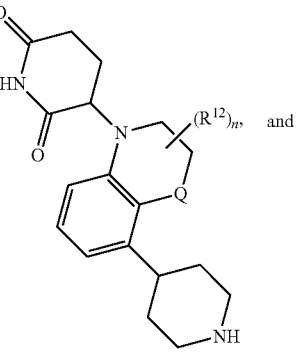
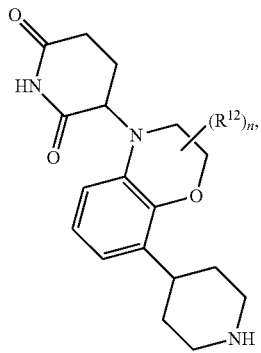
or a pharmaceutically acceptable salt thereof.

In certain aspects, the Degron compound of the present invention is selected from
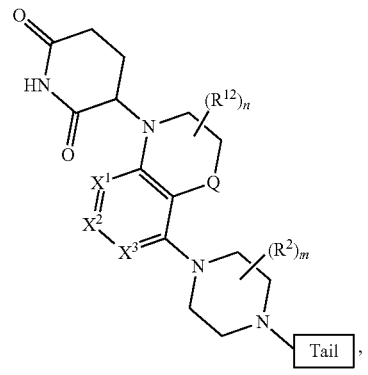
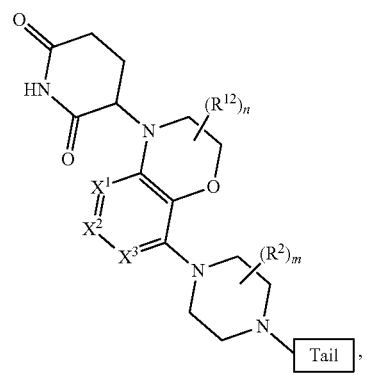
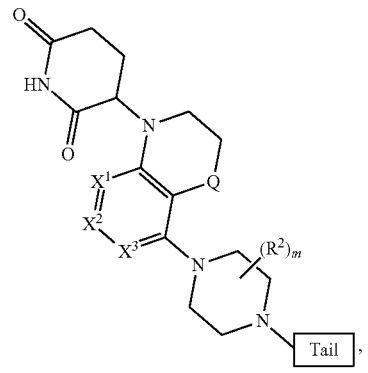
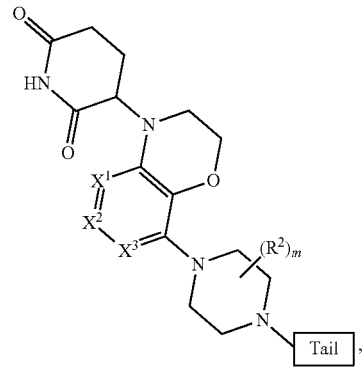
-continued
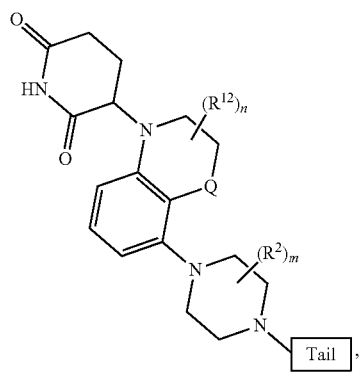
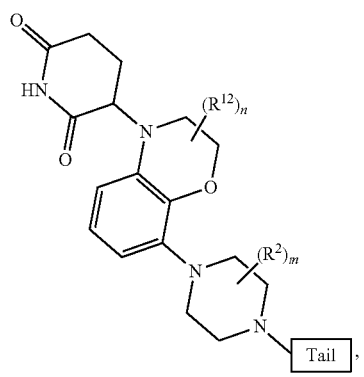
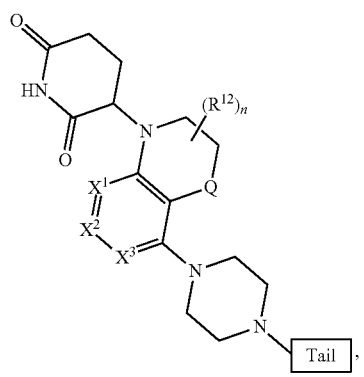
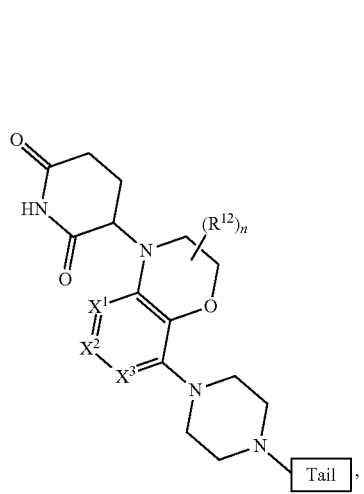

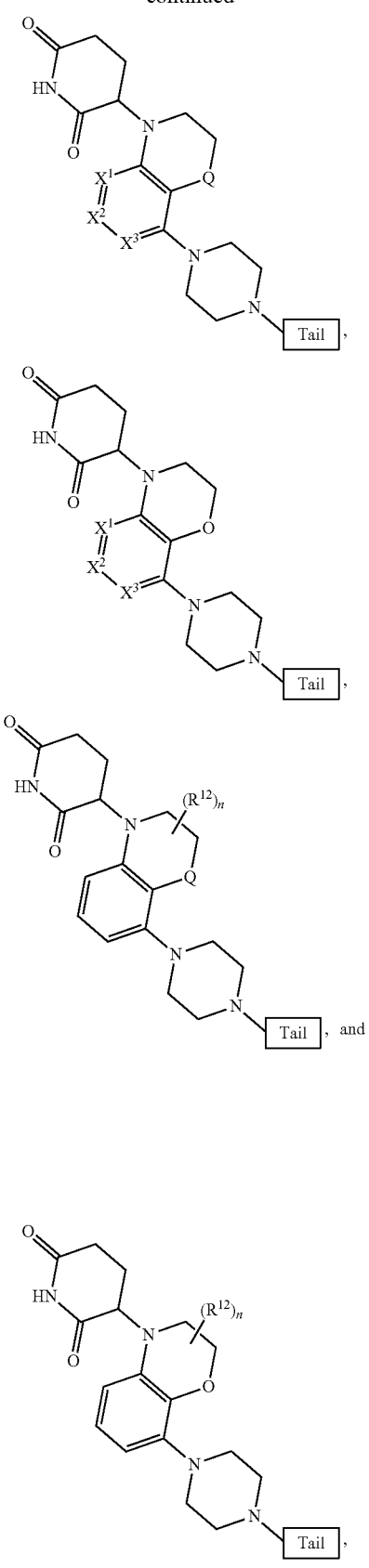
or a pharmaceutically acceptable salt thereof.
In certain aspects, the Degron compound of the present invention is selected from
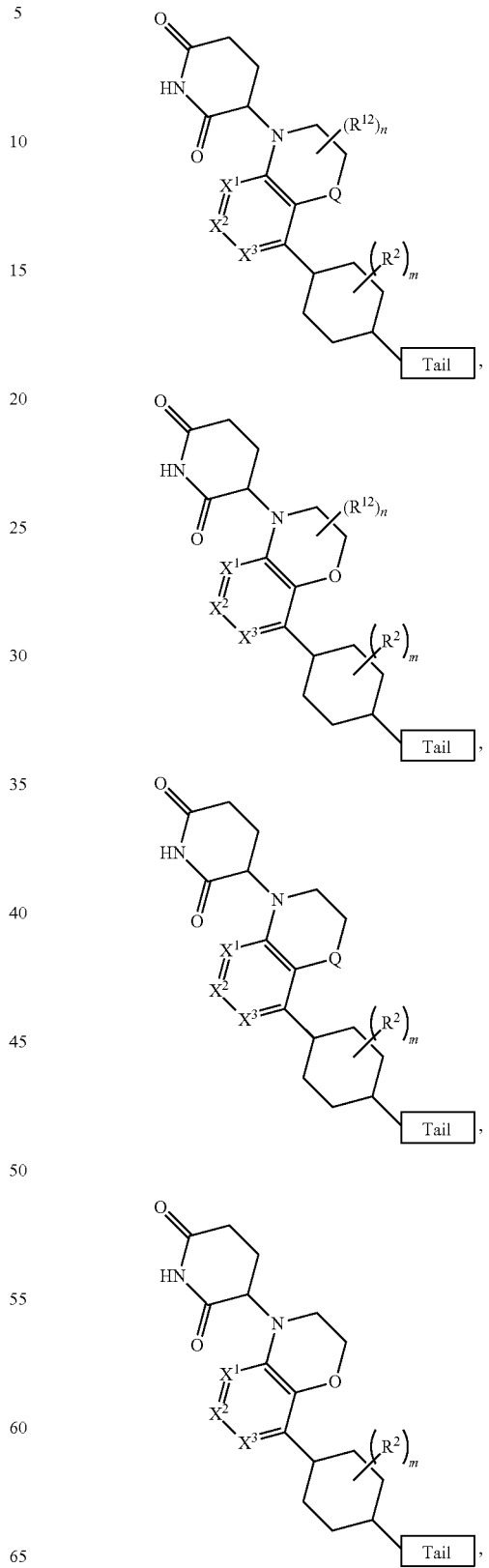

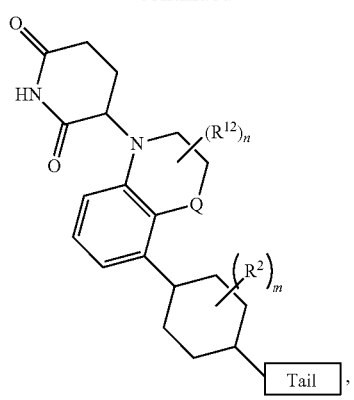
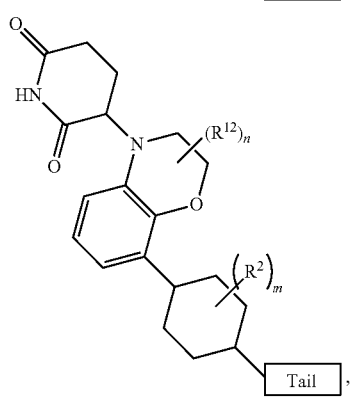
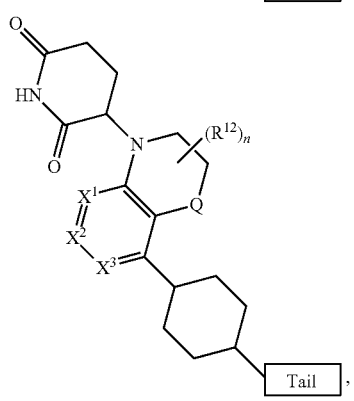
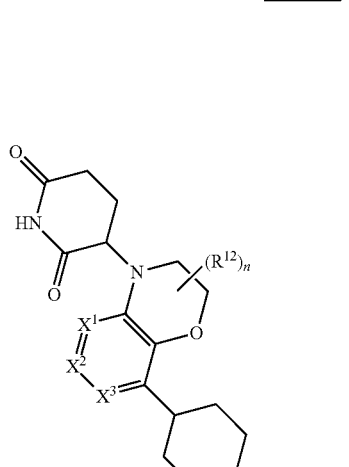
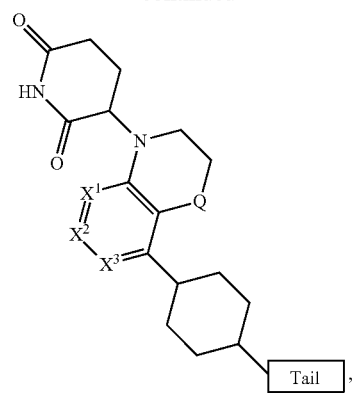
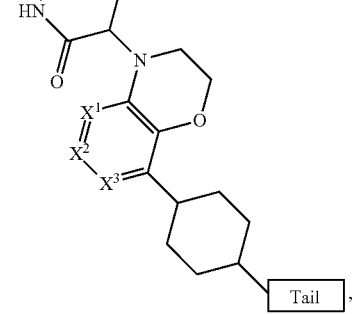
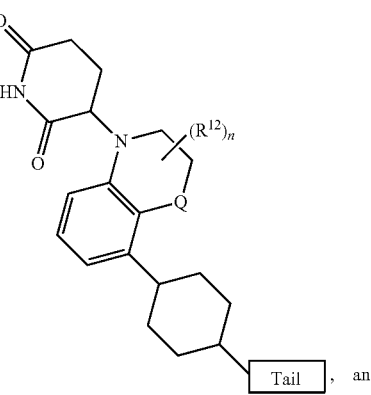
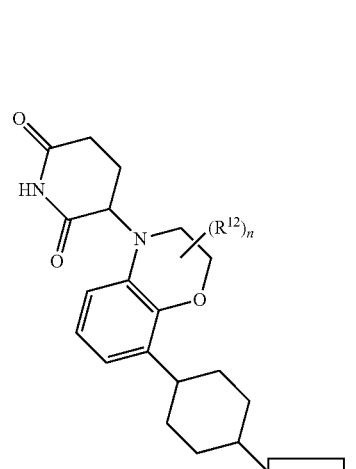, and
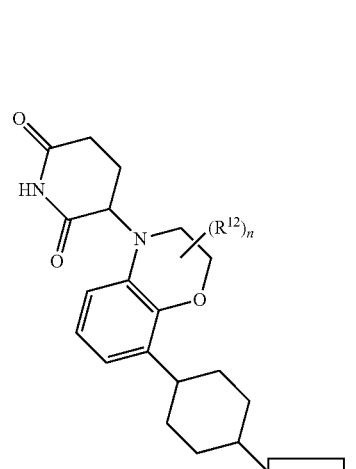,
or a pharmaceutically acceptable salt thereof.

In another aspect, a Degron compound of Formula IIAa, Formula IIAb, or Formula IIAc is provided:

(IIAa)

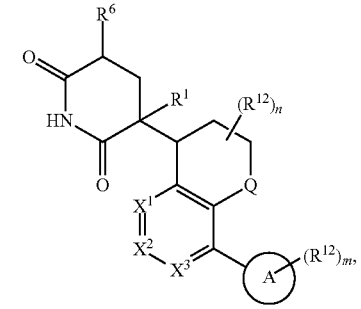

(IIAb)

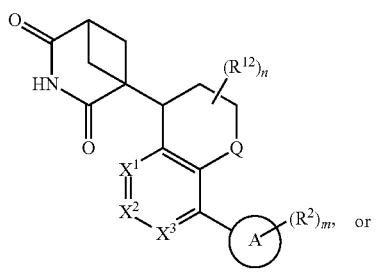

(IIAc)

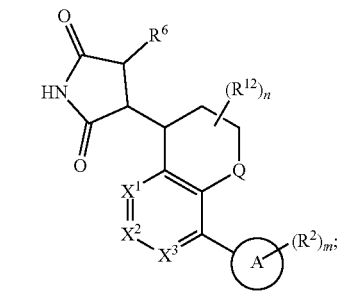

or a pharmaceutically acceptable salt, N-oxide, isotopic derivative or prodrug thereof, optionally in a pharmaceutically acceptable carrier to form a pharmaceutical composition;

wherein all variables are defined as above.

In another aspect, a Degron compound of Formula IIIAa, Formula IIIAb, or Formula IIIAc is provided:

(IIIAa)

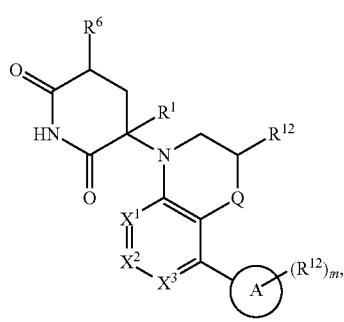

(IIIAb)

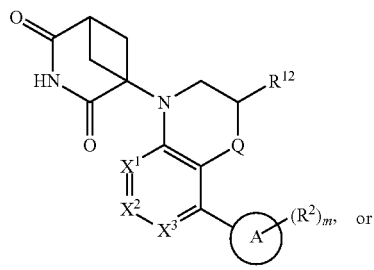

(IIIAc)

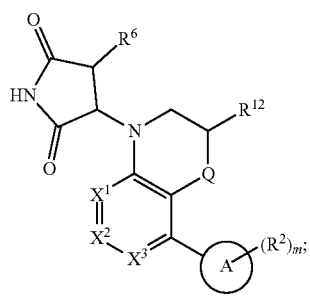

or a pharmaceutically acceptable salt, N-oxide, isotopic derivative or prodrug thereof, optionally in a pharmaceutically acceptable carrier to form a pharmaceutical composition;

wherein all variables are defined as above.

In another aspect, a Degron compound of Formula IVAa, Formula IVAb, or Formula IVAc is provided:

(IVAa)

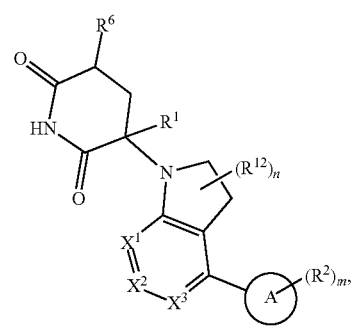

(IVAb)

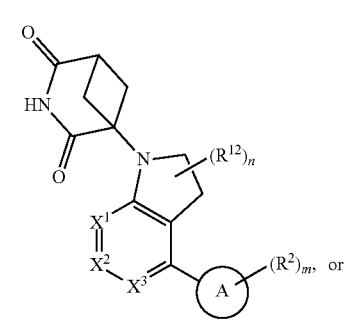

113
-continued (IVAc)

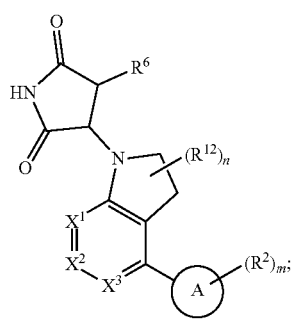

or a pharmaceutically acceptable salt, N-oxide, isotopic derivative or prodrug thereof, optionally in a pharmaceutically acceptable carrier to form a pharmaceutical composition;

wherein all variables are defined as above.

In certain embodiments the compound of the present invention is of Formula:

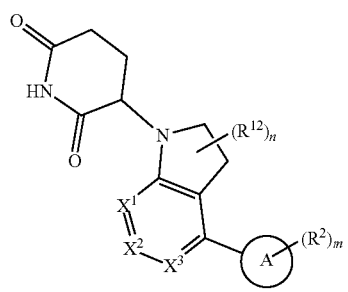

or a pharmaceutically acceptable salt thereof.

In certain embodiments the compound of the present invention is of Formula:

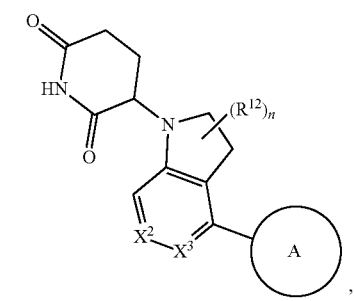

,

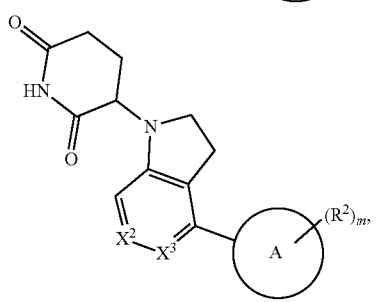

,

114
-continued

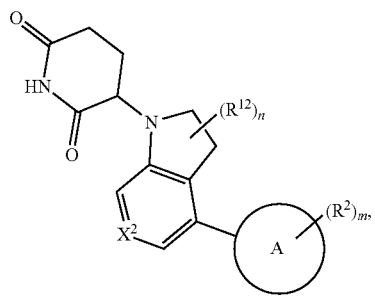

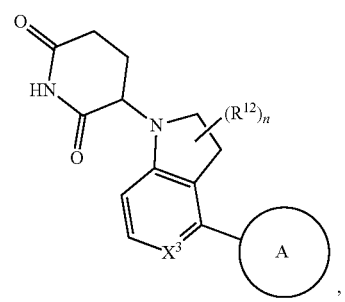

,

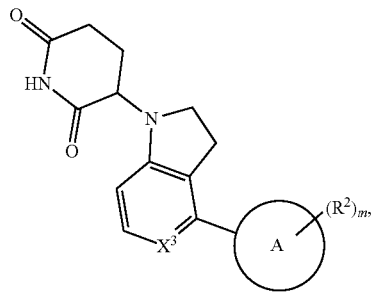

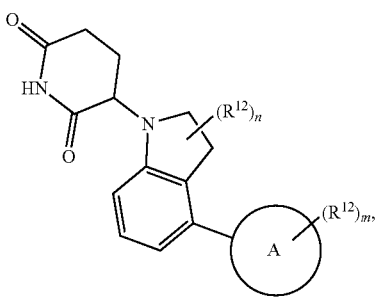

,

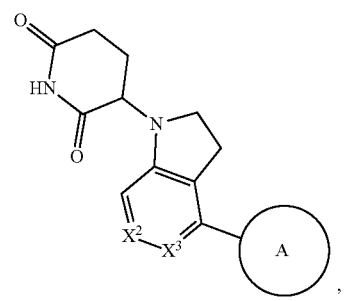

,

-continued

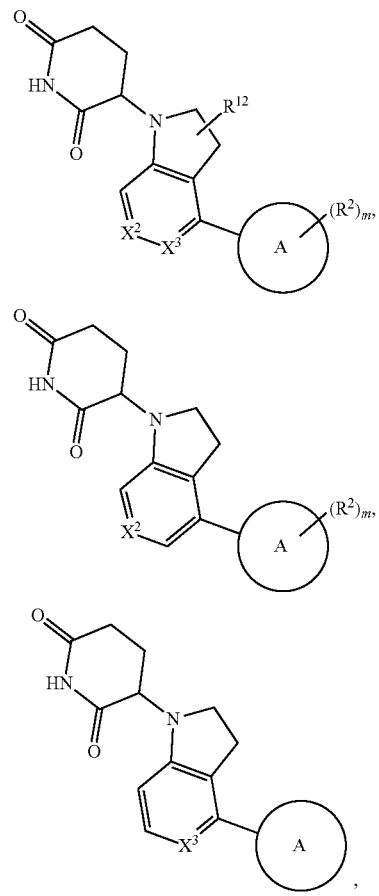

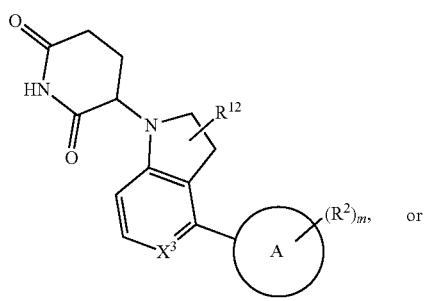

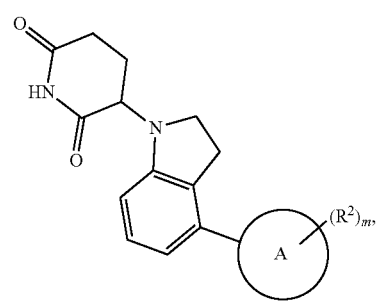

or a pharmaceutically acceptable salt thereof.

In another aspect, a Degron compound of Formula VAa, Formula VAb, or Formula VAc:

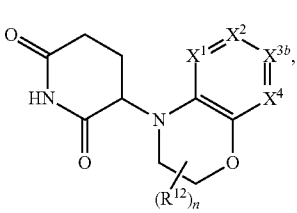
VAa

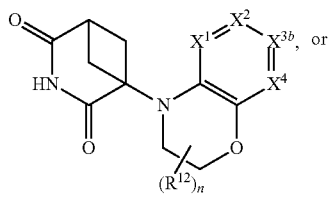
VAb

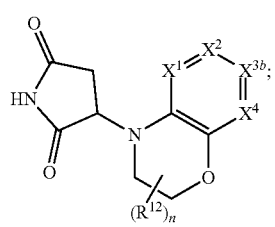
VAc or a pharmaceutically acceptable salt, N-oxide, isotopic derivative or prodrug thereof, optionally in a pharmaceutically acceptable carrier to form a pharmaceutical composition;

wherein all variables are defined as above.

In another aspect, a Degron compound of Formula VIAa, Formula VIAb, or Formula VIAc:

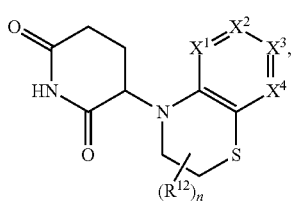
VIAa

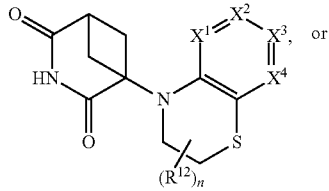
VIAb

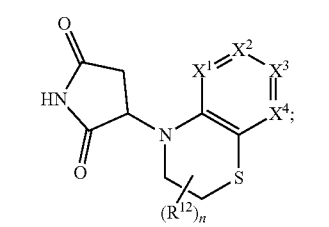
VIAc or a pharmaceutically acceptable salt, N-oxide, isotopic derivative or prodrug thereof, optionally in a pharmaceutically acceptable carrier to form a pharmaceutical composition;

wherein all variables are defined as above.

In another aspect, a Degron compound of Formula VIIAa, Formula VIIAb, or Formula VIIAc is provided:

VIIAa
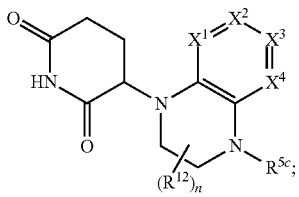

VIIAb
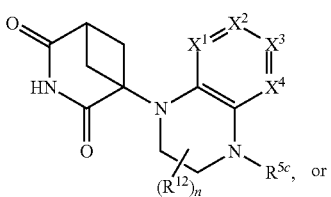

VIIAc
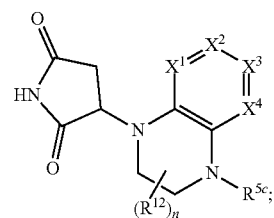

or a pharmaceutically acceptable salt, N-oxide, isotopic derivative or prodrug thereof, optionally in a pharmaceutically acceptable carrier to form a pharmaceutical composition;

wherein all variables are defined as above.

In another aspect, a Degron compound of Formula VIIIAa, Formula VIIIAb, or Formula VIIIAc is provided:

VIIIAa
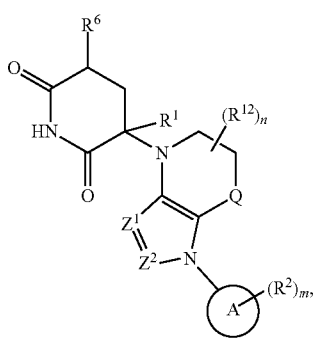

VIIIAb
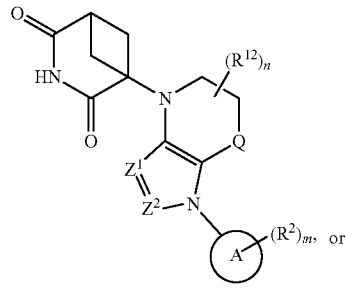

VIIIAc
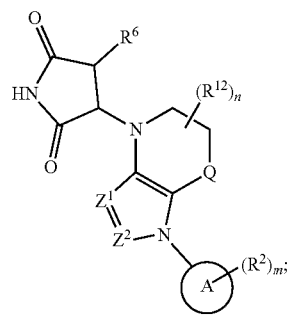

or a pharmaceutically acceptable salt, N-oxide, isotopic derivative or prodrug thereof, optionally in a pharmaceutically acceptable carrier to form a pharmaceutical composition;

wherein all variables are defined as above.

In certain aspects, a Degron compound of Formula IXAa, Formula IXAb, or Formula IXAc is provided:

IXAa
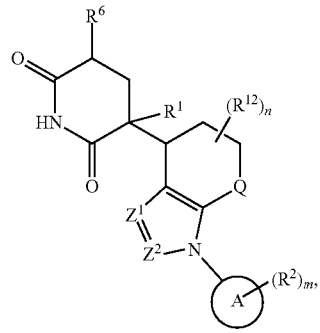

IXAb
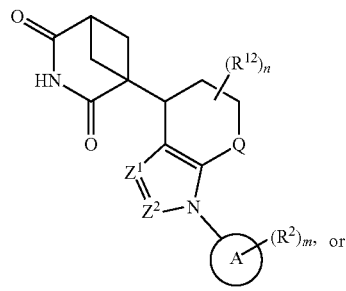

IXAc

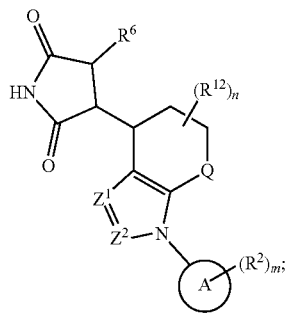

or a pharmaceutically acceptable salt, N-oxide, isotopic derivative or prodrug thereof, optionally in a pharmaceutically acceptable carrier to form a pharmaceutical composition;

wherein all variables are defined as above.

In certain aspects, a Degron compound of Formula XAa, Formula XAb, or Formula XAc is provided:

XAa

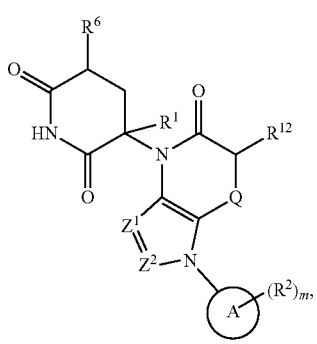

XAb

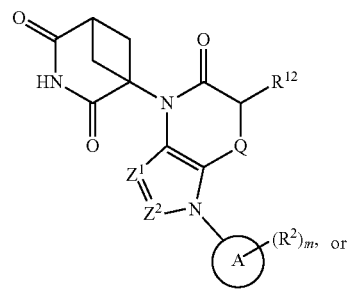

XAc

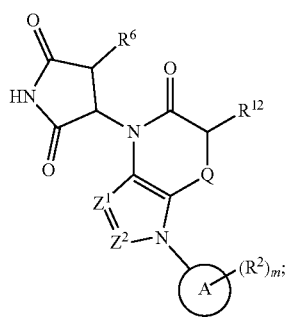

or a pharmaceutically acceptable salt, N-oxide, isotopic derivative or prodrug thereof, optionally in a pharmaceutically acceptable carrier to form a pharmaceutical composition;

wherein all variables are defined as above.

In certain aspects, a Degron compound of Formula XIAa, Formula XIAb, or Formula XIAc is provided:

XIAa

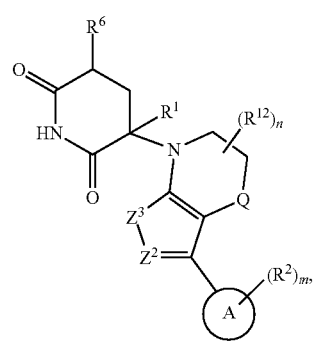

XIAb

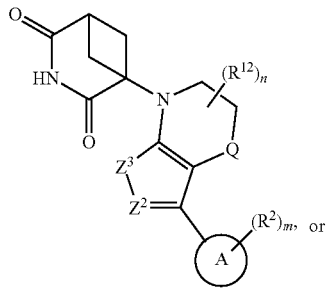

XIAc

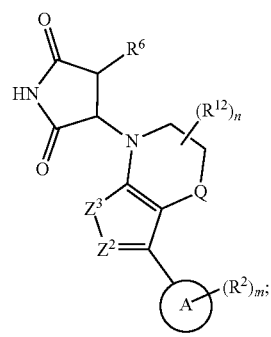

or a pharmaceutically acceptable salt, N-oxide, isotopic derivative or prodrug thereof, optionally in a pharmaceutically acceptable carrier to form a pharmaceutical composition;

wherein all variables are defined as above.

In certain aspects, a Degron compound of Formula XIIAa, Formula XIIAb, or Formula XIIAc is provided:

XIIAa
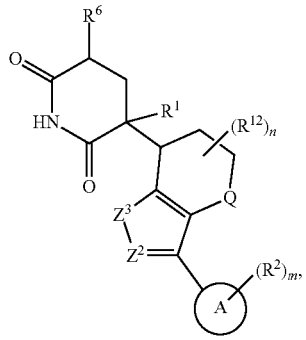

XIIAb
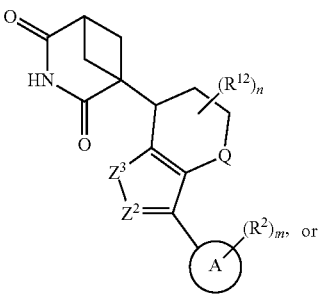

XIIAc
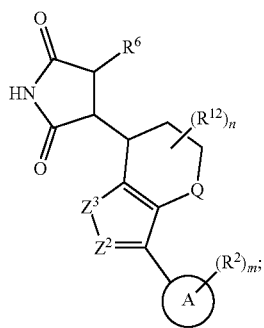

or a pharmaceutically acceptable salt, N-oxide, isotopic derivative or prodrug thereof, optionally in a pharmaceutically acceptable carrier to form a pharmaceutical composition;

wherein all variables are defined as above.

In certain aspects, a Degron compound of Formula XIIIAa, Formula XIIIAb, or Formula XIIIAc is provided:

XIIIAa
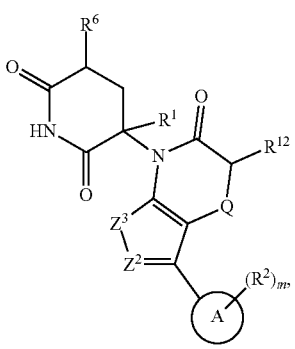

XIIIAb
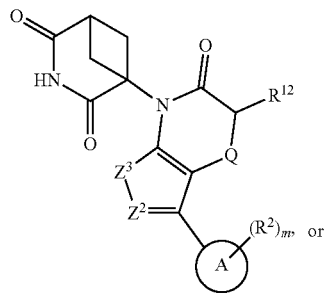

XIIIAc
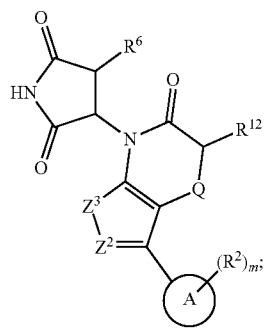

or a pharmaceutically acceptable salt, N-oxide, isotopic derivative or prodrug thereof, optionally in a pharmaceutically acceptable carrier to form a pharmaceutical composition;

wherein all variables are defined as above.

In certain aspects, a Degron compound of Formula XIVAa, Formula XIVAb, or Formula XIVAc is provided:

XIVAa
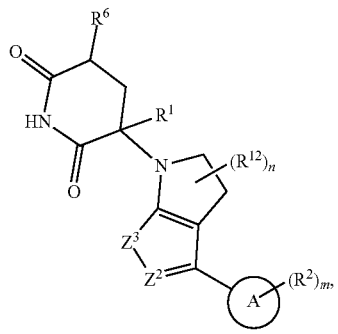

XIVAb
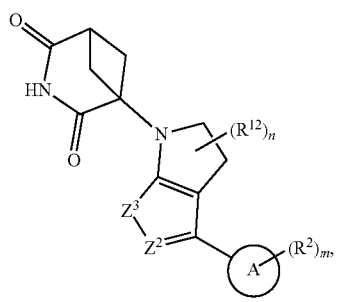

-continued

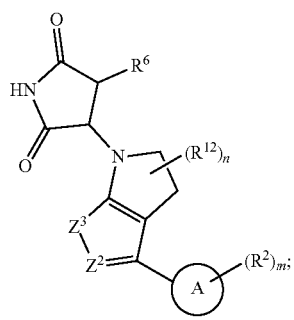

XIVAc or a pharmaceutically acceptable salt, N-oxide, isotopic derivative or prodrug thereof, optionally in a pharmaceutically acceptable carrier to form a pharmaceutical composition;

wherein all variables are defined as above.

In certain aspects, a Degron compound of Formula XVAa, XVAb, or XVAc is provided:

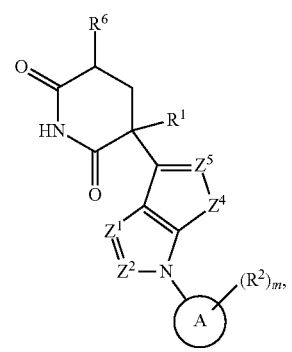

XVAa

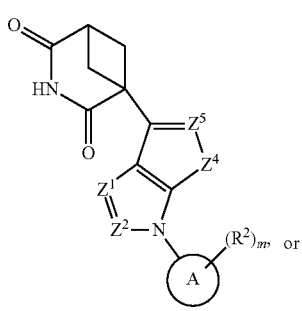

XVAb

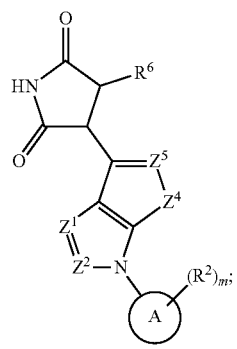

XVAc or a pharmaceutically acceptable salt, N-oxide, isotopic derivative or prodrug thereof, optionally in a pharmaceutically acceptable carrier to form a pharmaceutical composition;

wherein all variables are defined as above.

In certain aspects, a Degron compound of Formula XVIAa, XVIAb, or XVIAc is provided:

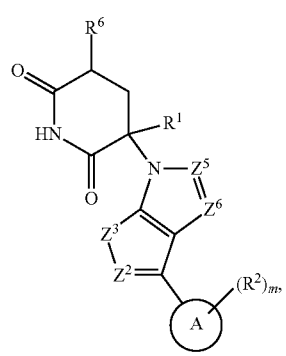

XVIAa

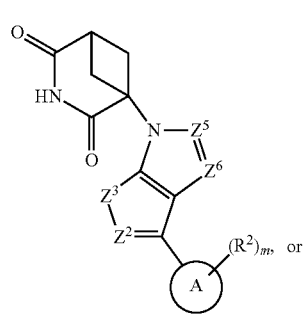

XVIAb

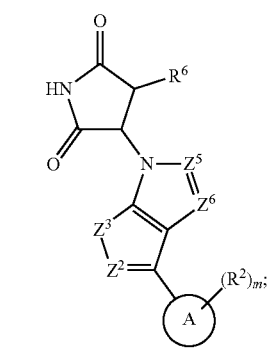

XVIAc or a pharmaceutically acceptable salt, N-oxide, isotopic derivative or prodrug thereof, optionally in a pharmaceutically acceptable carrier to form a pharmaceutical composition;

wherein all variables are defined as above.

In certain aspects, a Degron compound of Formula XVI-IAa, Formula XVIIAb, Formula XVIIAc, Formula XVIIAd, or Formula XVIIAe is provided:

(XVIIAa)

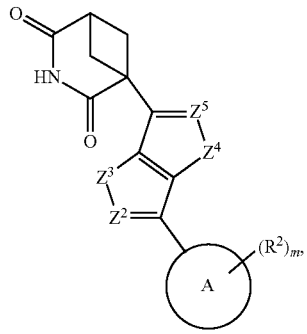

(XVIIAb)

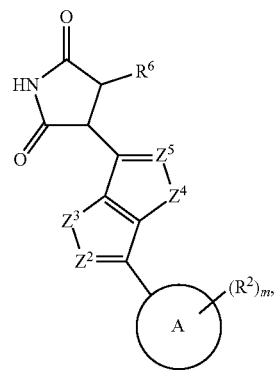

(XVIIAc)

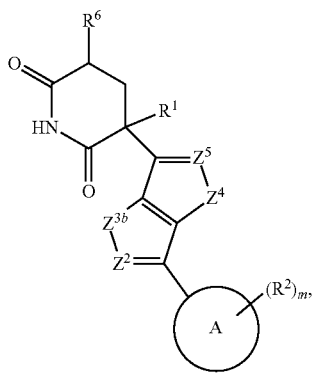

(XVIIAd)

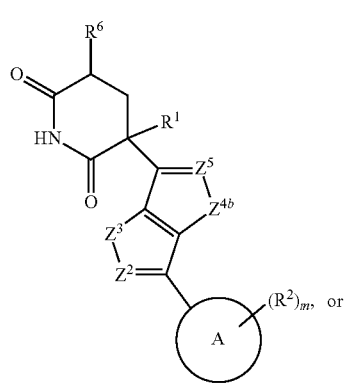

-continued (XVIIAe)

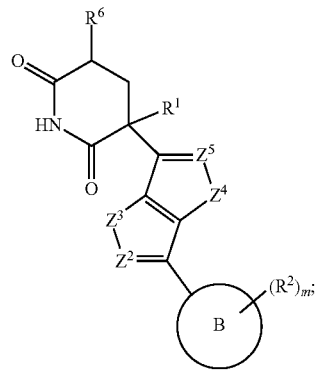

or a pharmaceutically acceptable salt, N-oxide, isotopic derivative or prodrug thereof, optionally in a pharmaceutically acceptable carrier to form a pharmaceutical composition;

wherein all variables are defined as above.

In certain embodiments, the present invention is a compound of Formula IA:

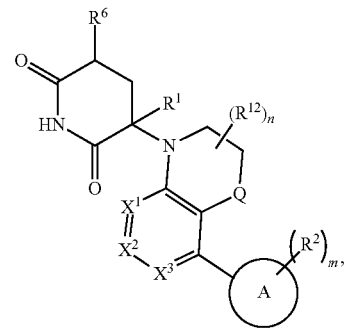

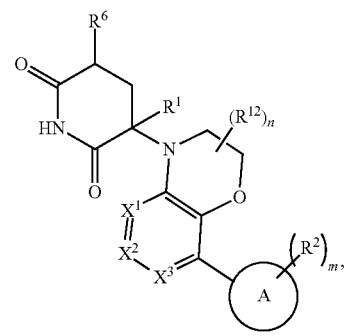

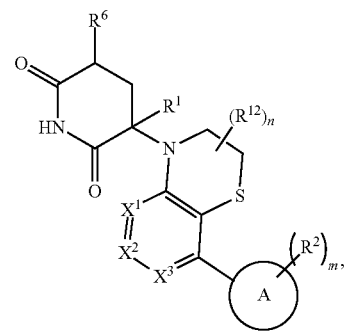

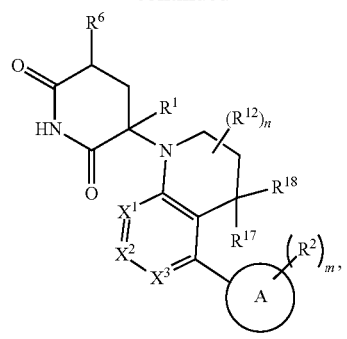
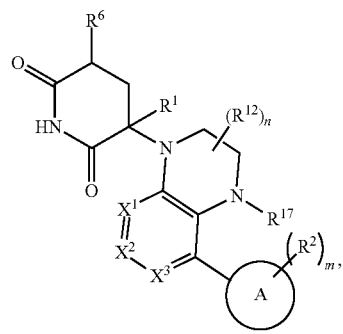
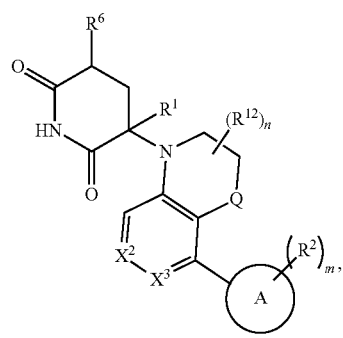
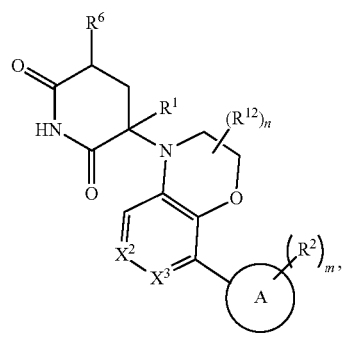
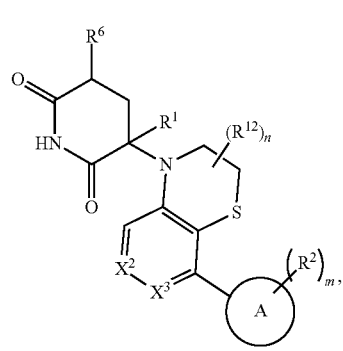
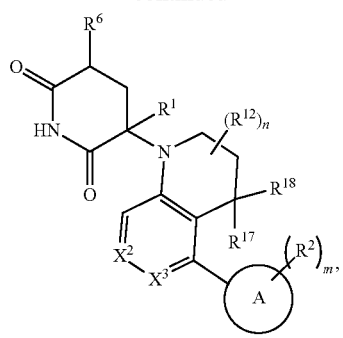
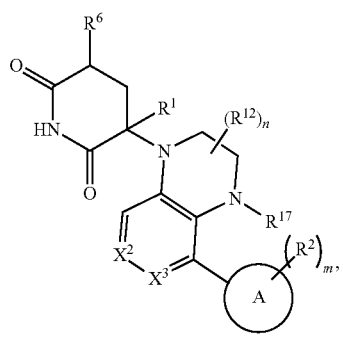
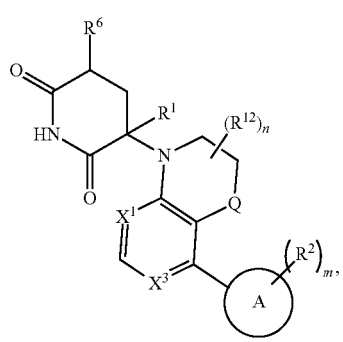
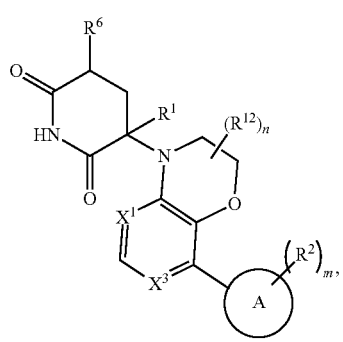
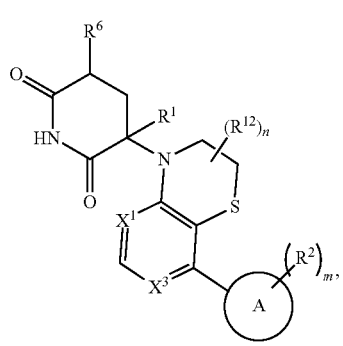

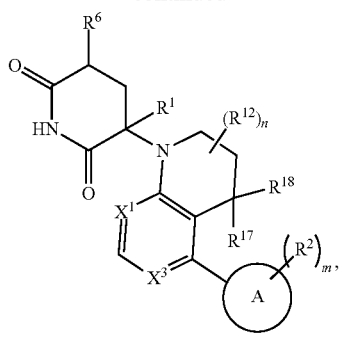
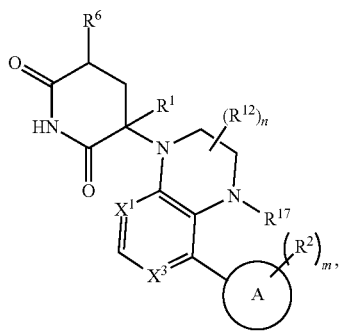
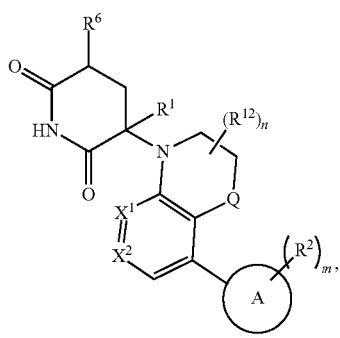
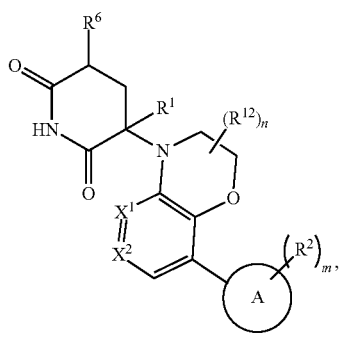

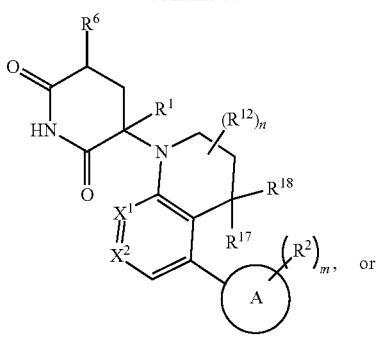
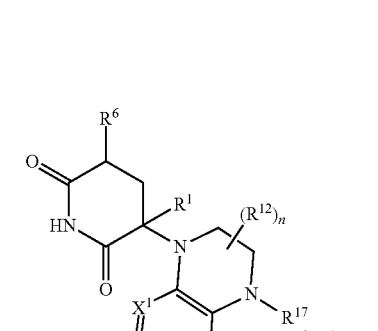, or
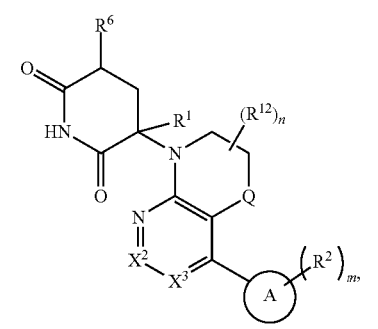
or a pharmaceutically acceptable salt thereof.
In certain embodiments, the compound of the present invention is selected from:
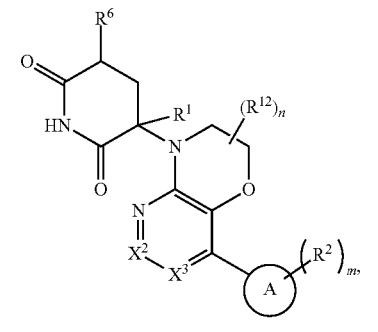

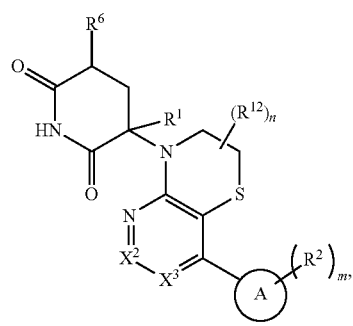
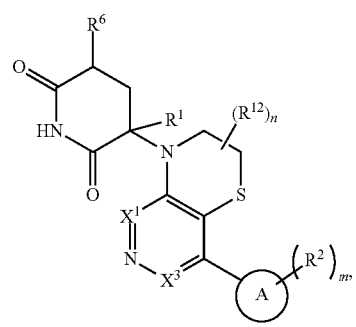
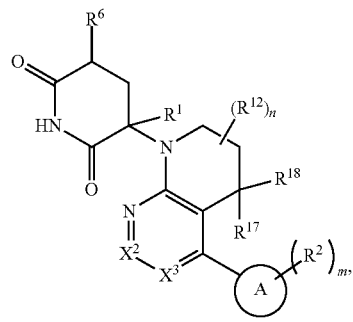
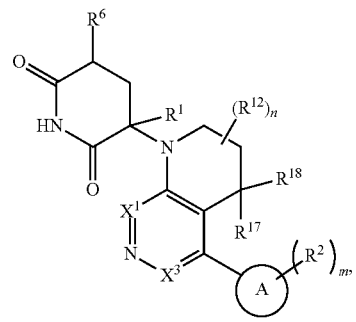
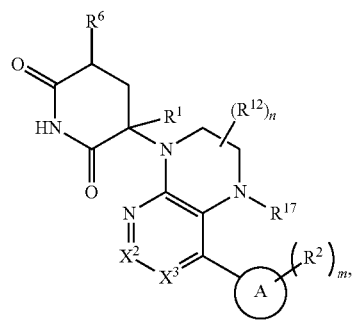
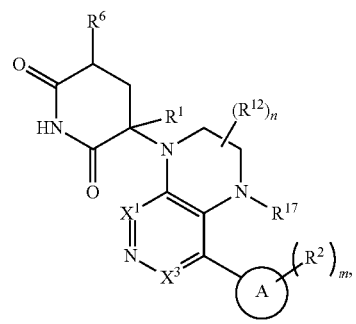
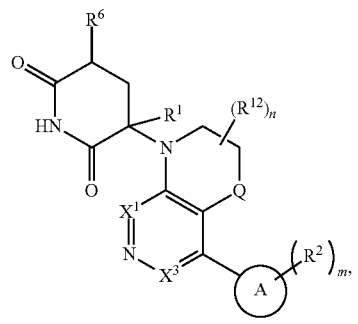
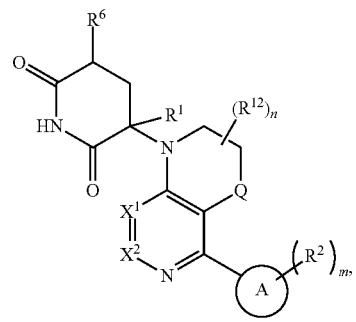
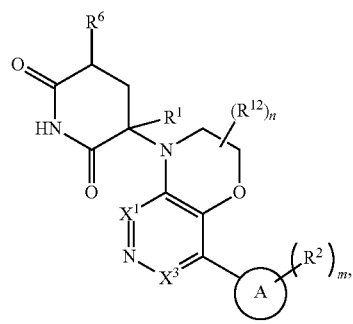
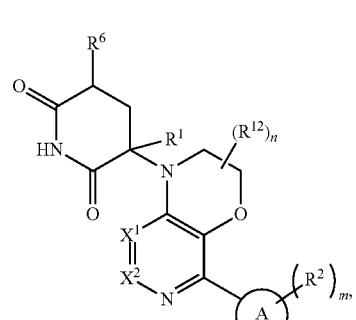

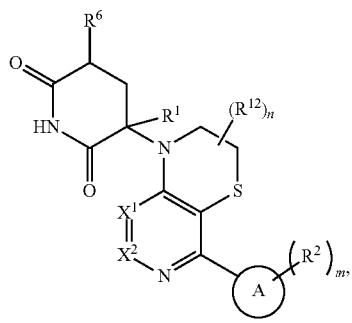
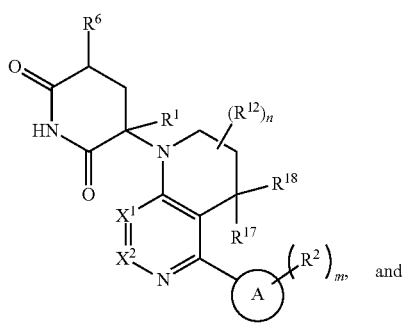
and
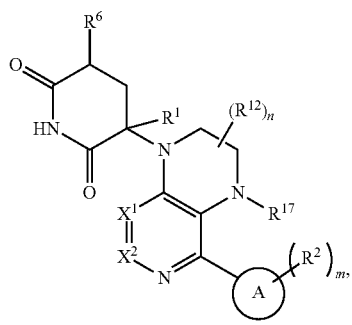
or a pharmaceutically acceptable salt thereof.
In certain embodiments, the compound of the present invention is a compound of Formula IIA selected from:
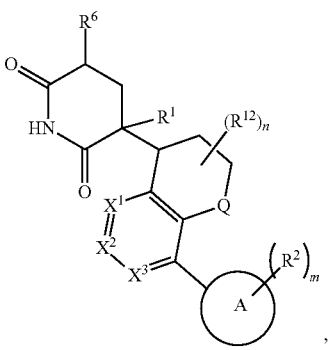
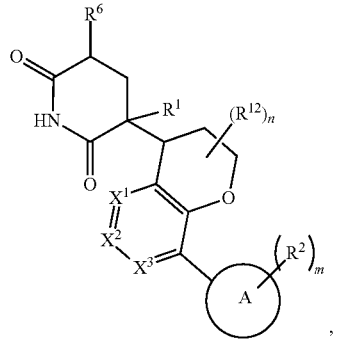
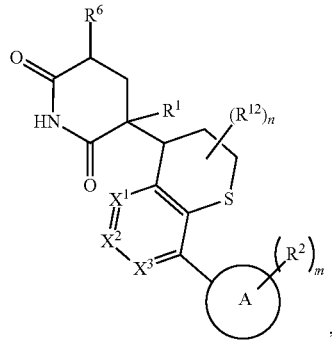
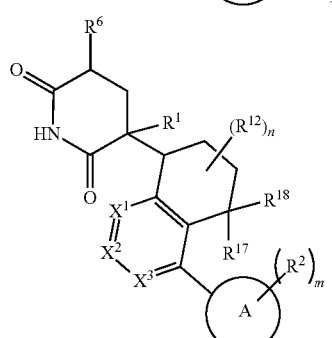
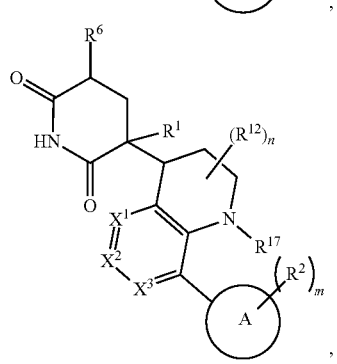
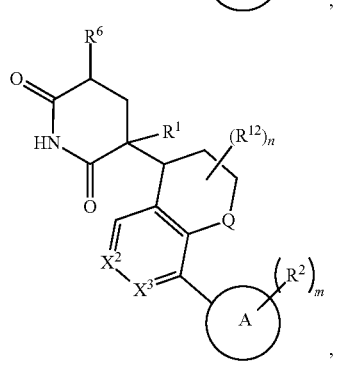

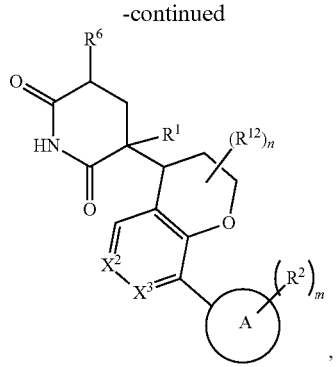
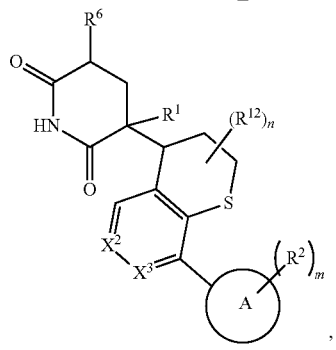
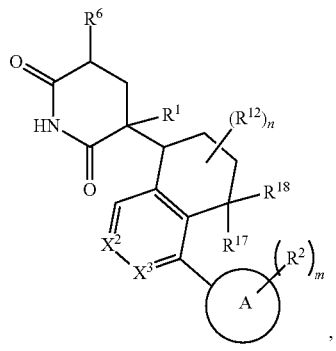
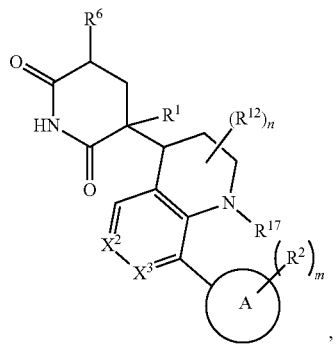
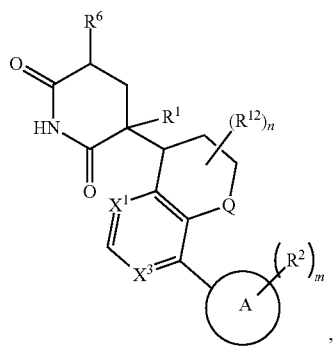
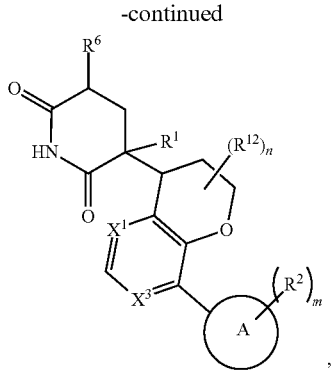
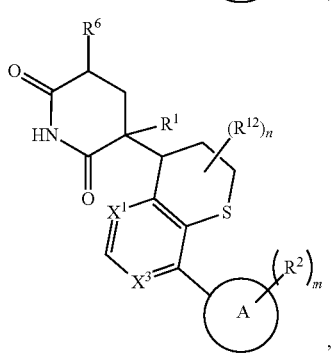
, and
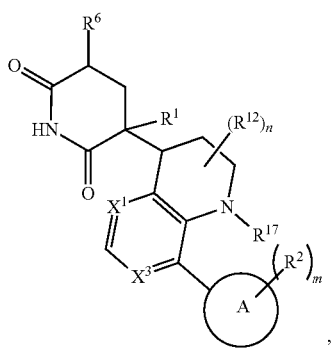
or a pharmaceutically acceptable salt thereof.

In certain embodiments, the compound of the present invention is selected from:
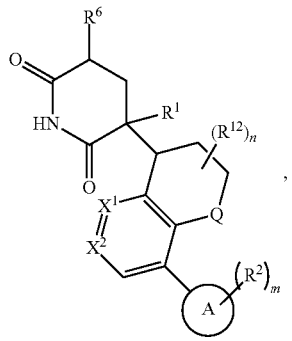
,
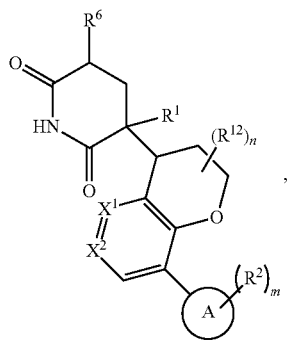
,
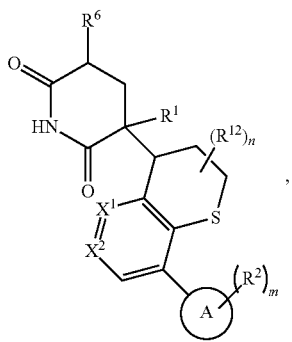
,
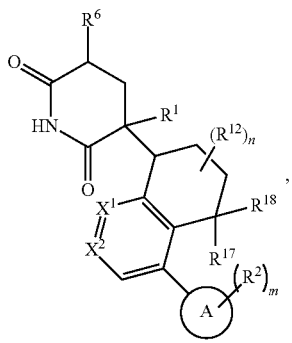
,
-continued
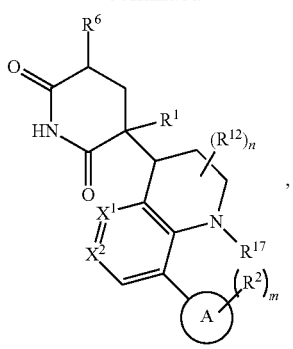
,
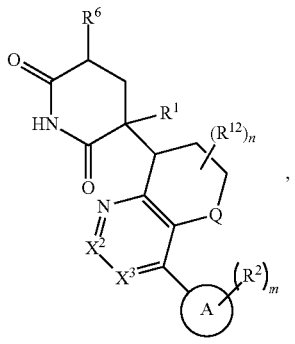
,
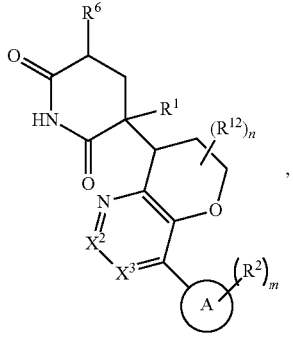
,
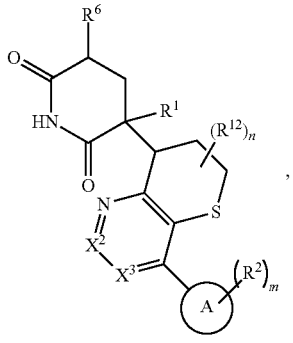
,
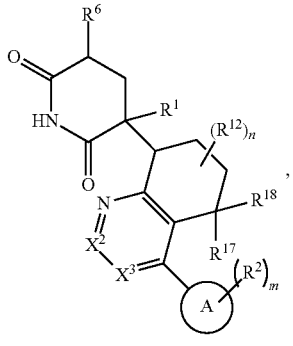
, -continued
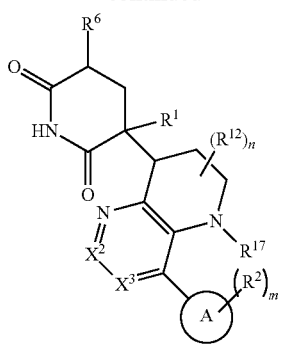,
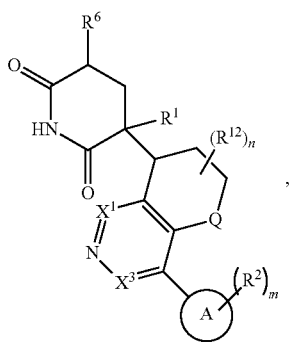,
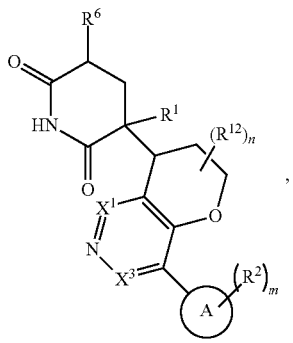,
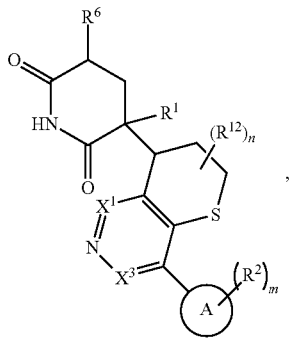,
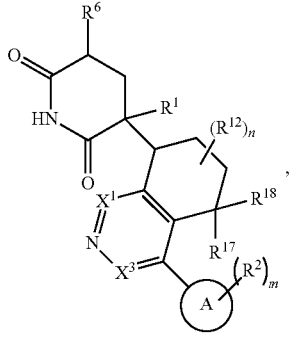,
-continued
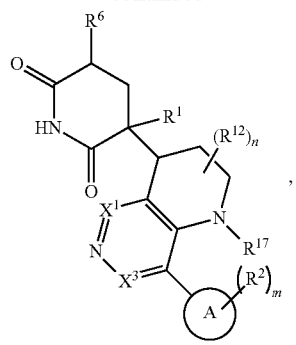,
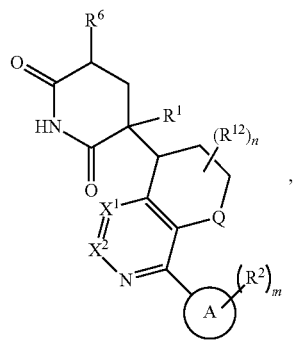,
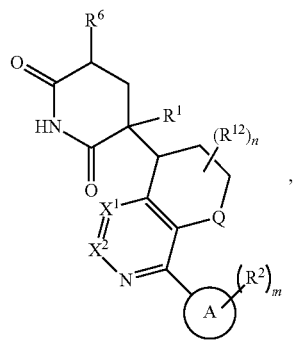,
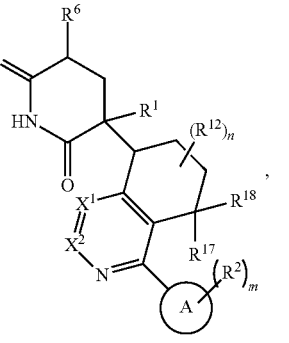,
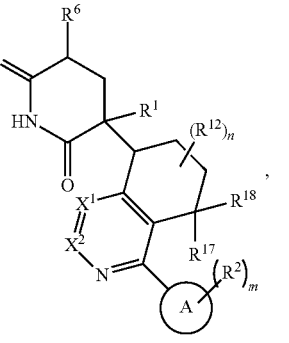, and -continued
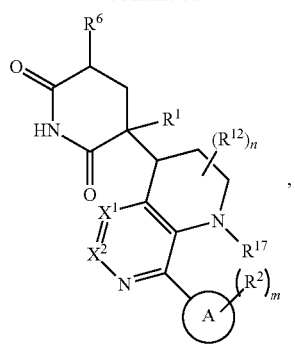
or a pharmaceutically acceptable salt thereof.
In certain embodiments, the compound of the present invention is a compound of Formula IIIA selected from:
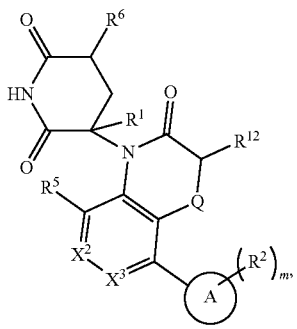
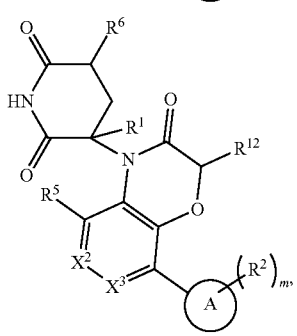
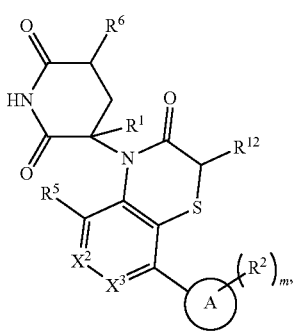
-continued
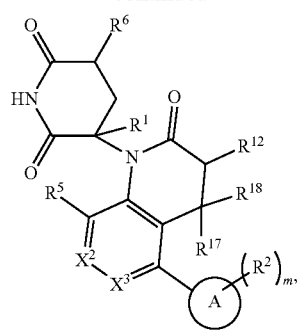
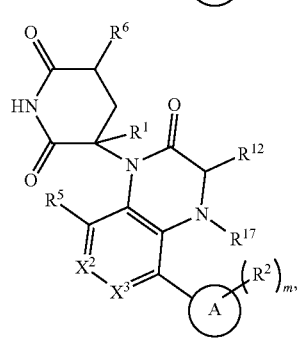
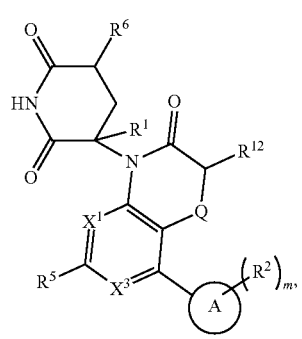
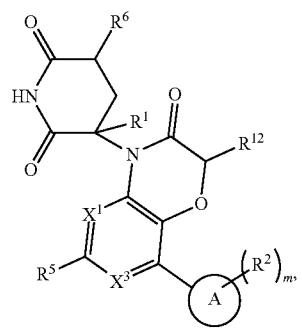
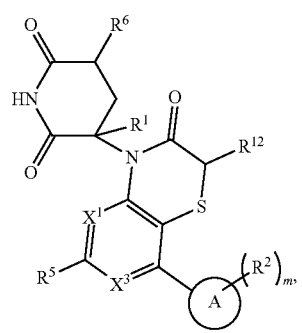

-continued
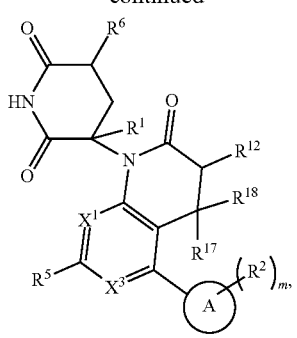
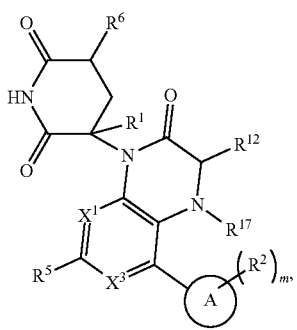
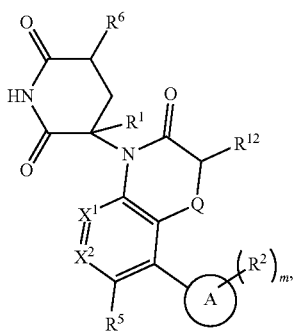
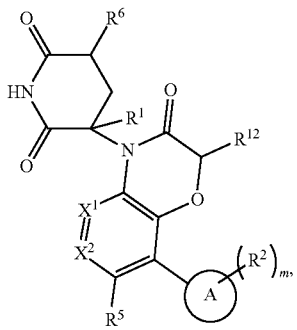
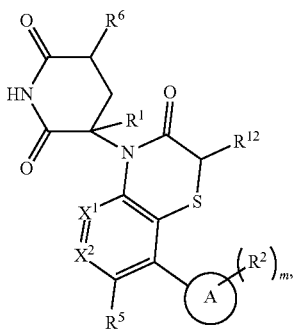
-continued
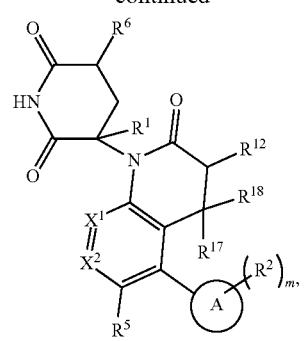
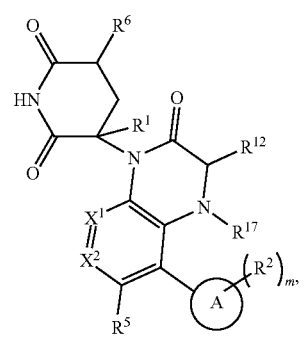
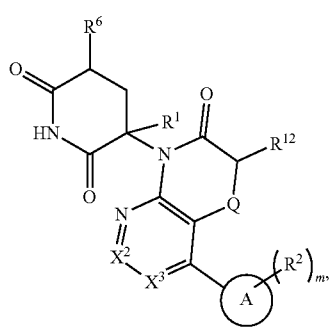
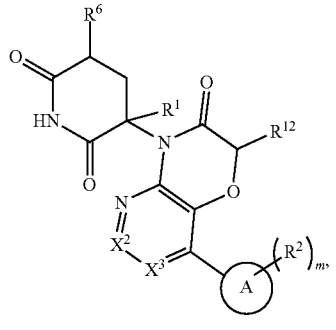
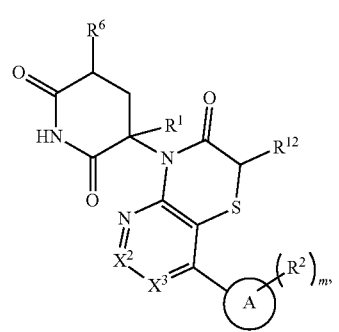

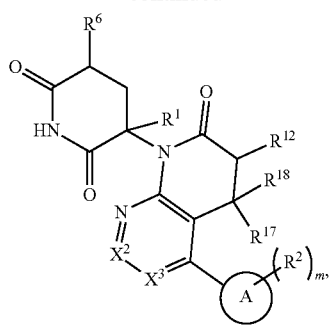
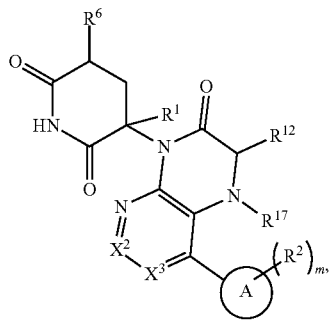
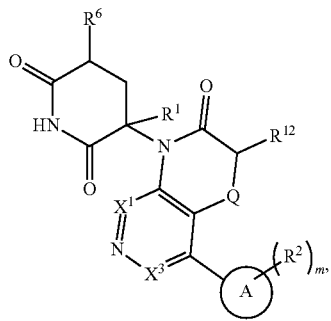
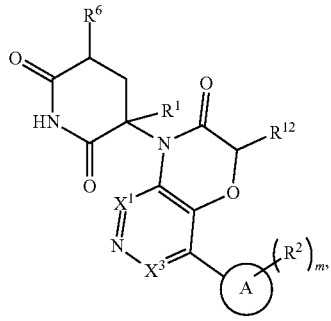
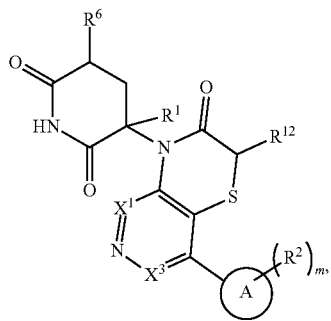
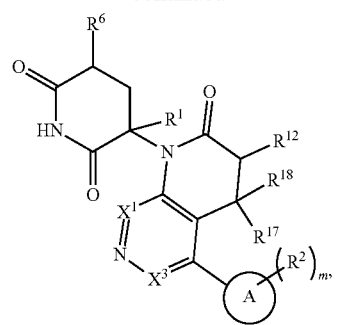
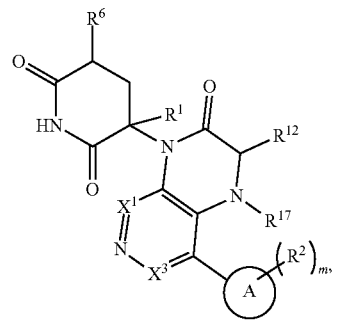
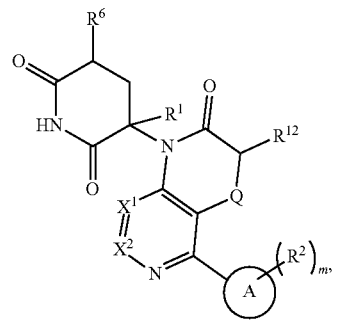
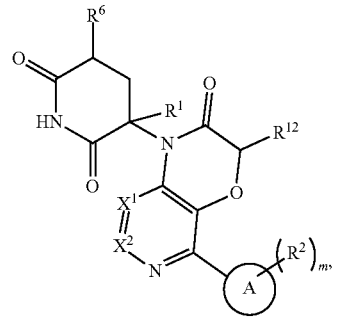
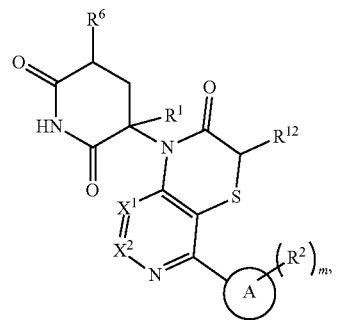

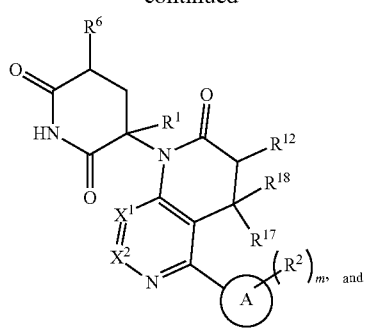
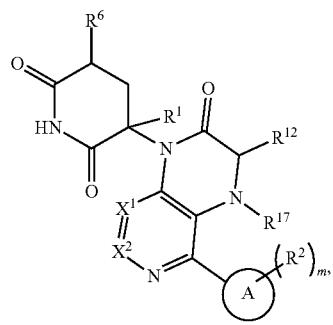
or a pharmaceutically acceptable salt thereof.
In certain embodiments, the compound of the present invention is selected from:
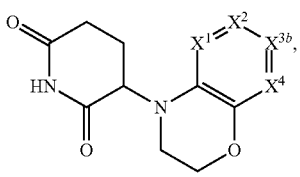
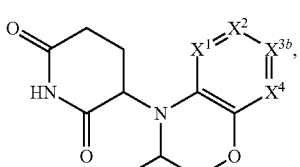
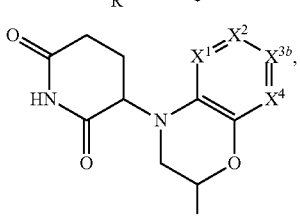
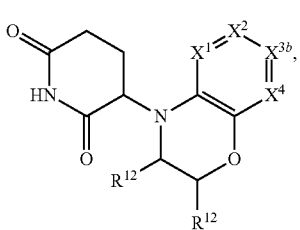
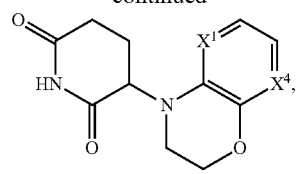
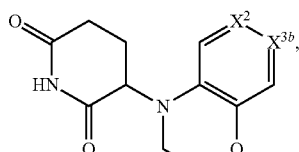
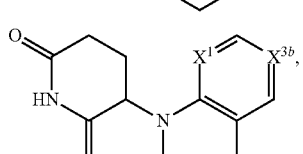
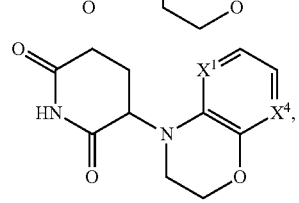
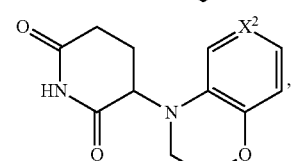
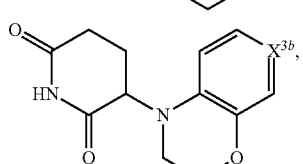
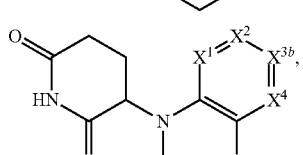
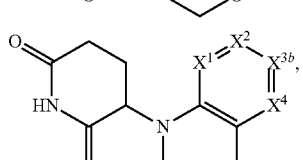
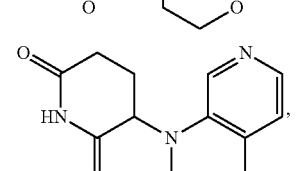
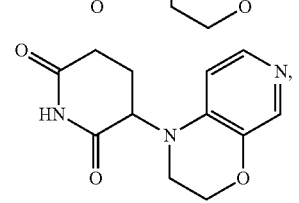

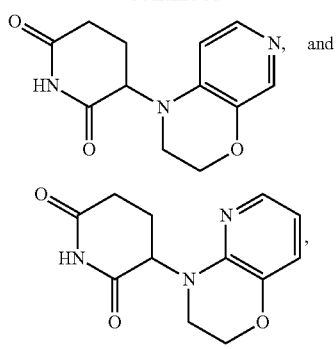

or a pharmaceutically acceptable salt thereof.

In certain embodiments, the compound of the present invention is selected from:

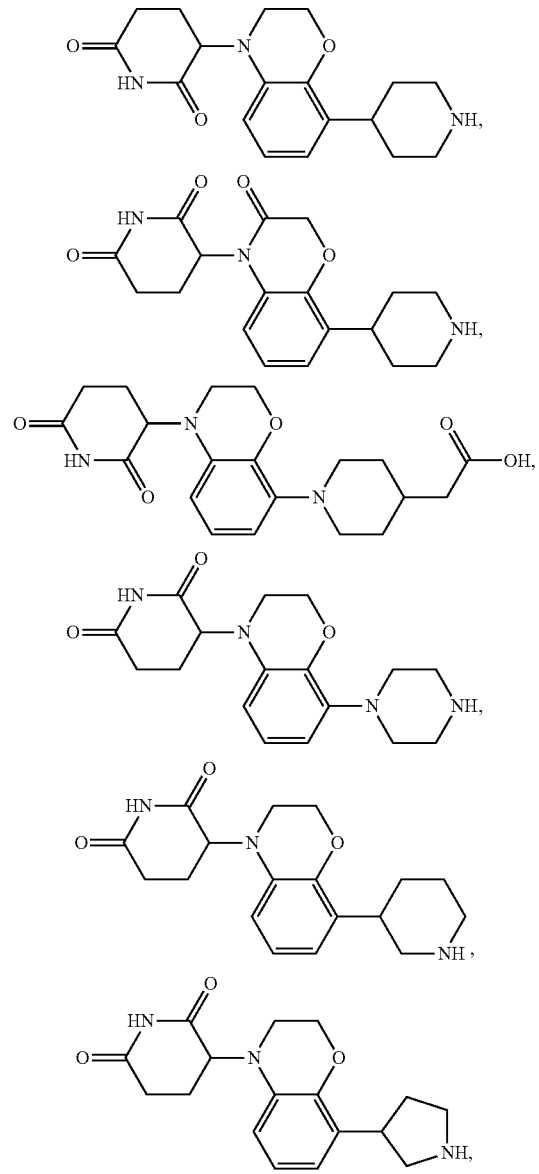

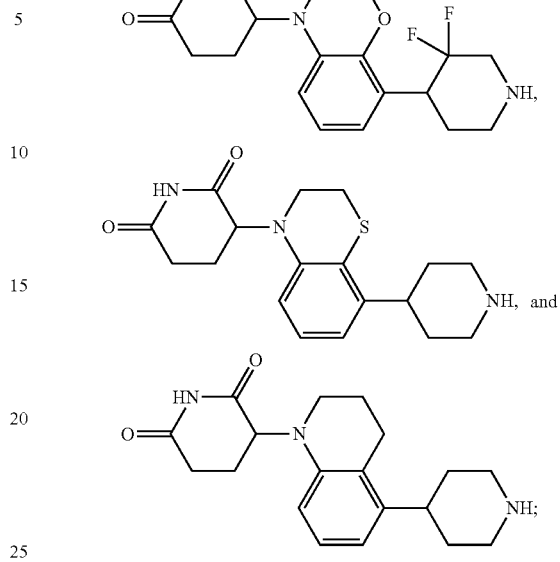

or a pharmaceutically acceptable salt thereof.

In another aspect, a Degrader compound of Formula I, Formula II, Formula III, Formula IV, Formula V, Formula VI, Formula VII, Formula VIII, Formula IX, Formula X, Formula XI, Formula XII, Formula XIII, Formula XIV, Formula XV, Formula XVI, or Formula XVII is provided:

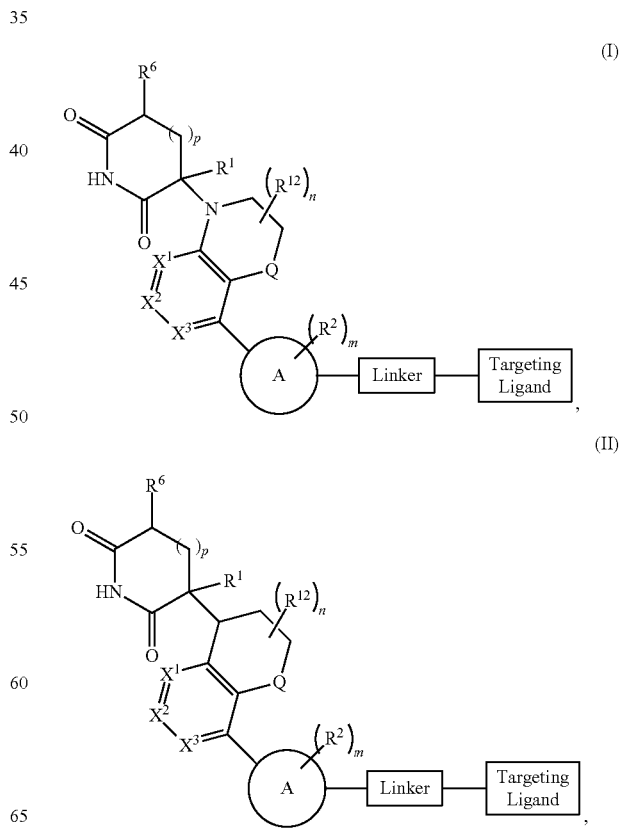

(III)
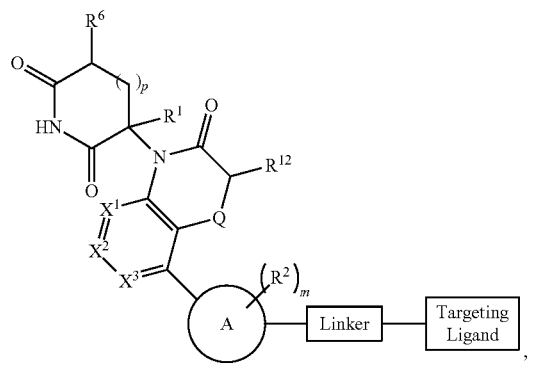
(IV)
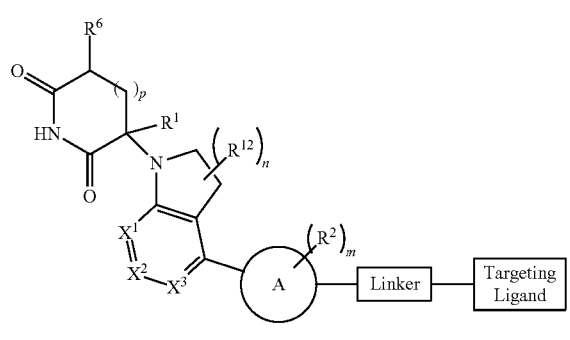
(V)
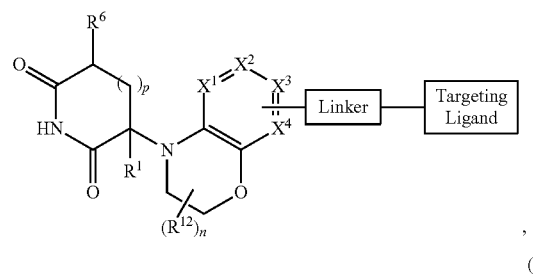
(VI)
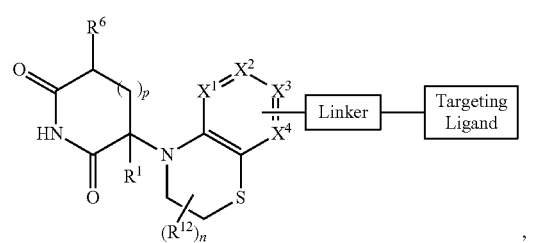
(VII)
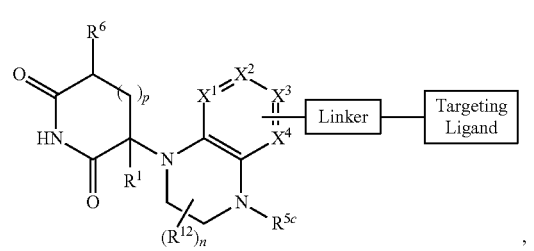
(VIII)
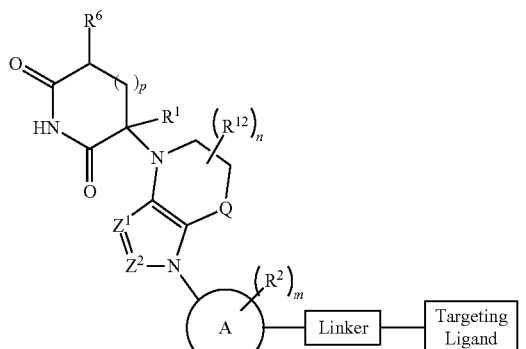
(IX)
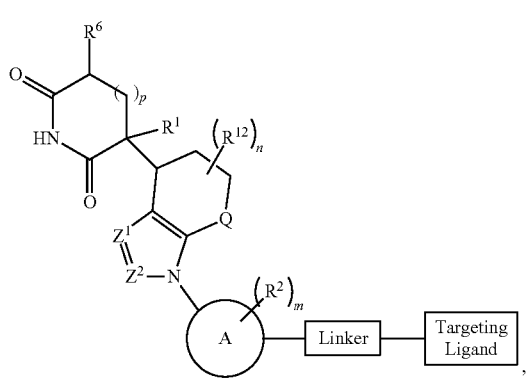
(X)
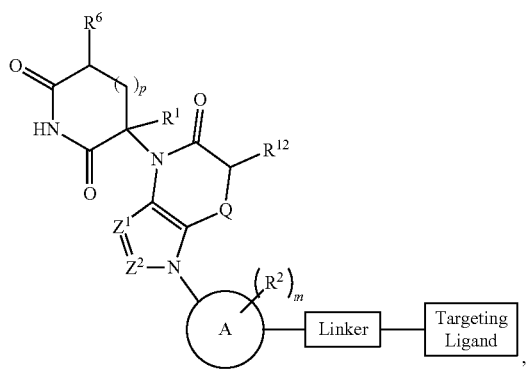
(XI)
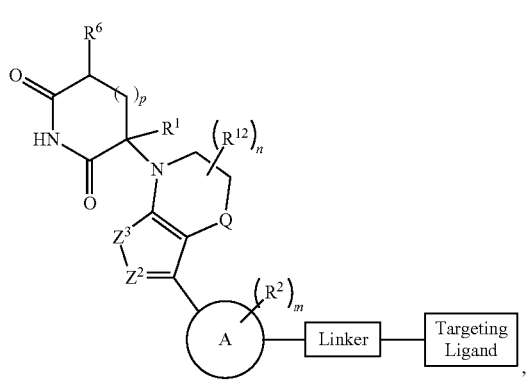

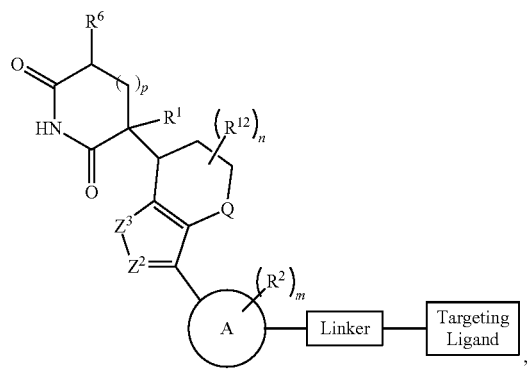
(XII)
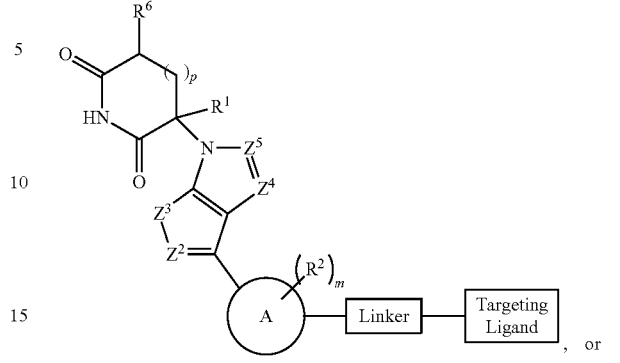
(XVI)
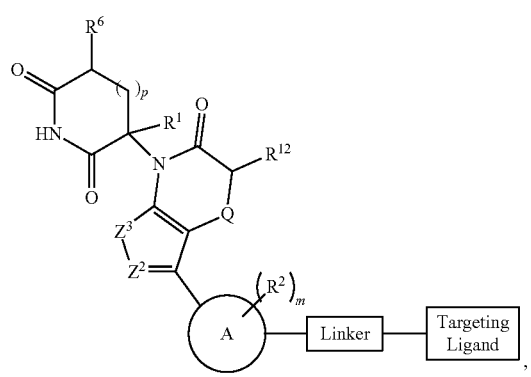
(XIII)
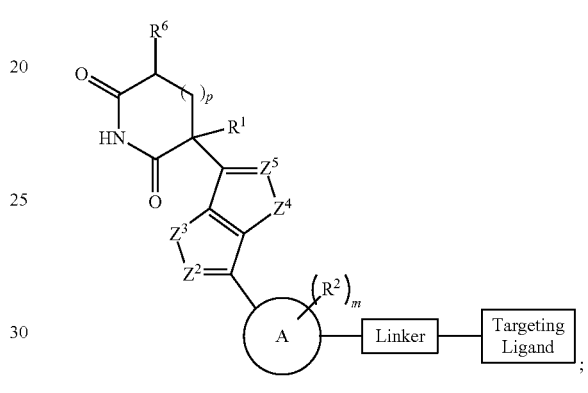
(XVII)
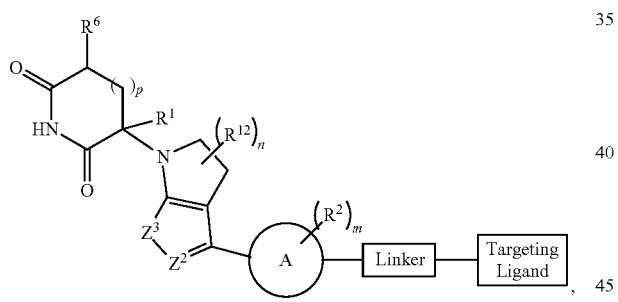
(XIV)
or a pharmaceutically acceptable salt, N-oxide, isotopic derivative or prodrug thereof, optionally in a pharmaceutically acceptable carrier to form a pharmaceutical composition;
wherein all variables are defined as above.
In certain embodiments, (A) is selected from:
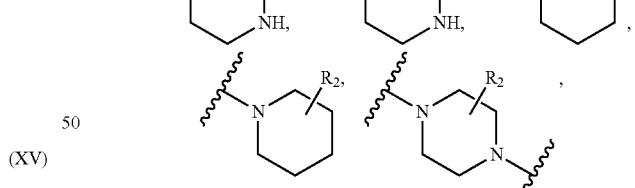
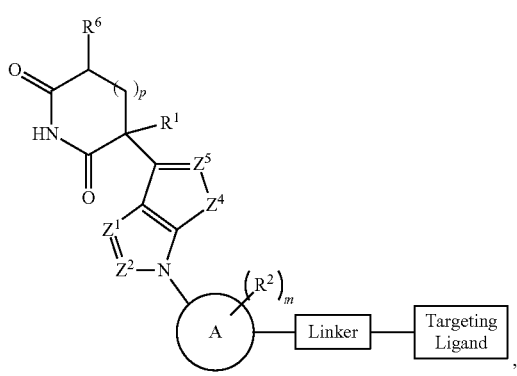
(XV)
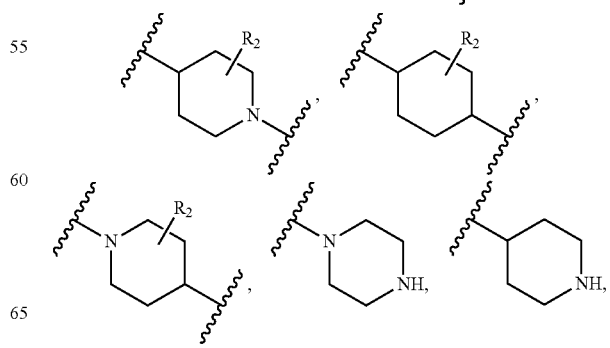

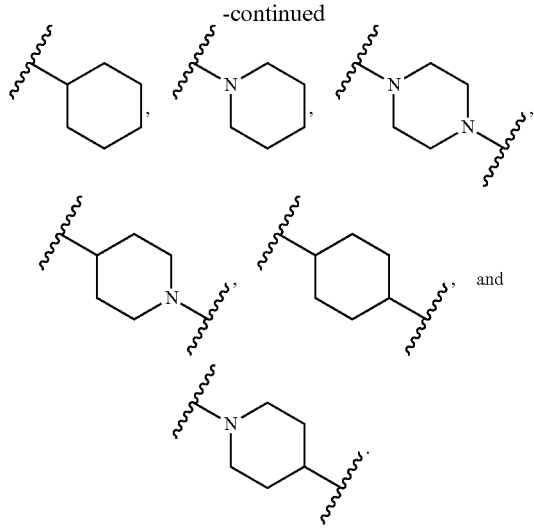
In certain embodiments, Ⓐ is selected from:
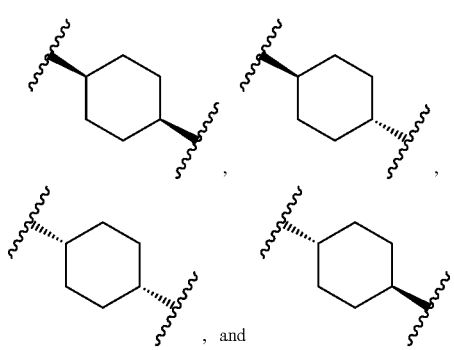
In certain embodiments, Ⓐ is selected from:
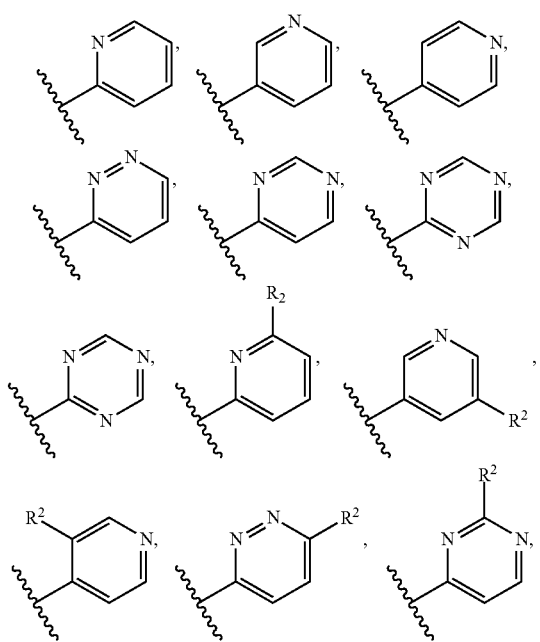
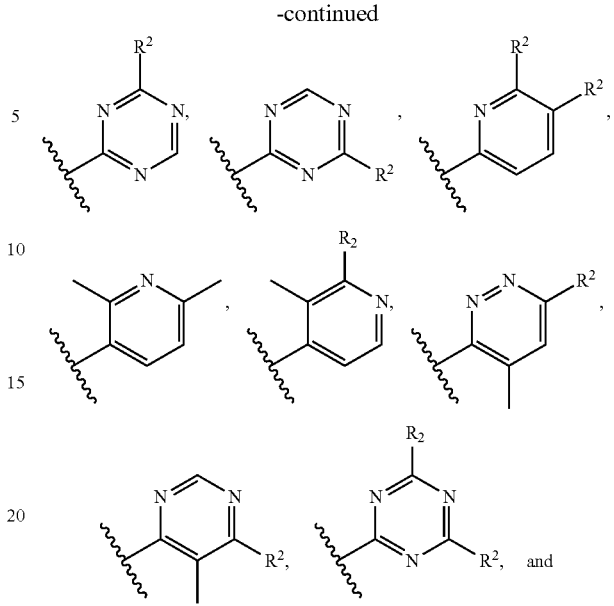
In certain embodiments, Ⓐ is selected from:
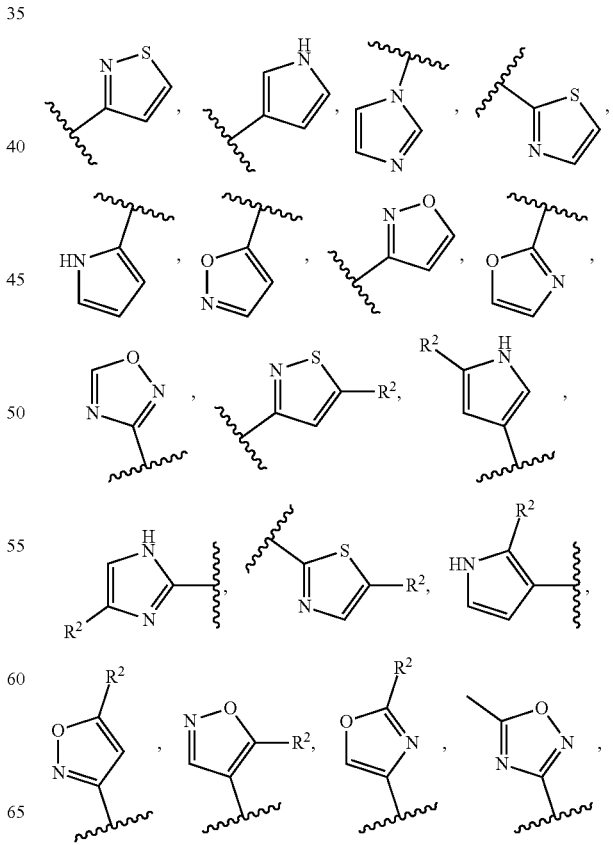

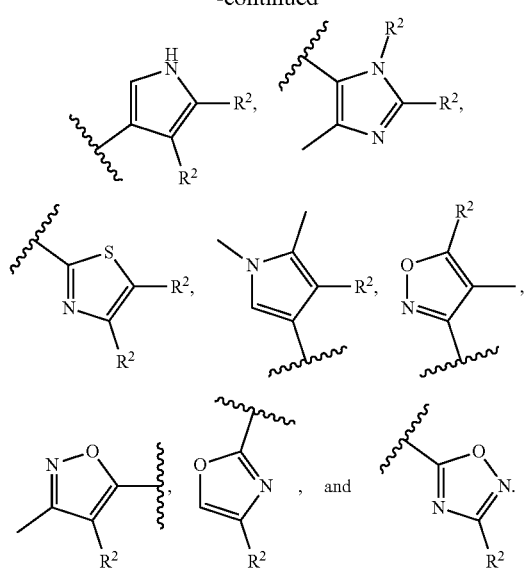
In certain embodiments, the compound of the present invention is a compound of Formula VA selected from:
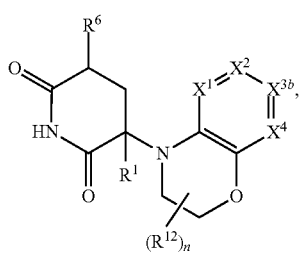
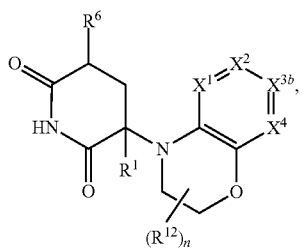
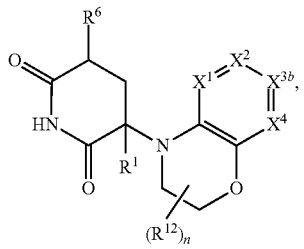
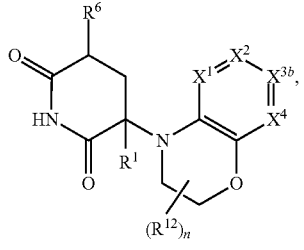
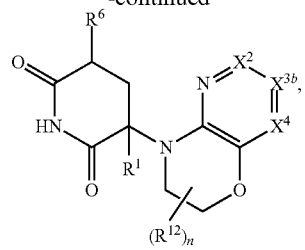
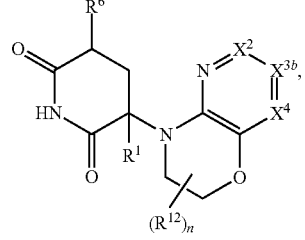
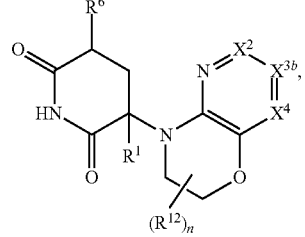
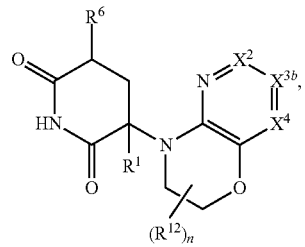
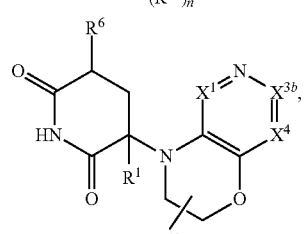
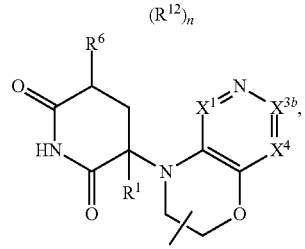
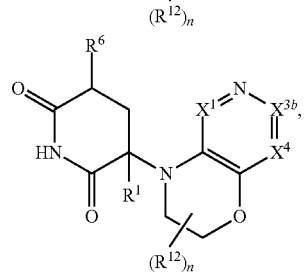

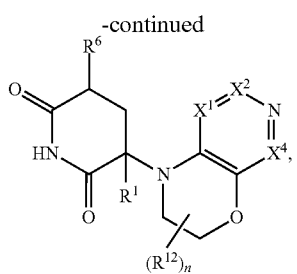
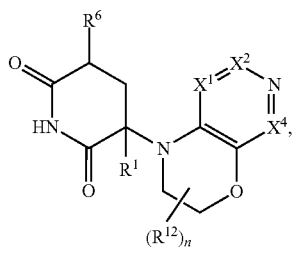
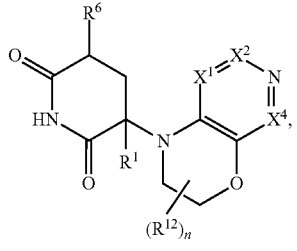
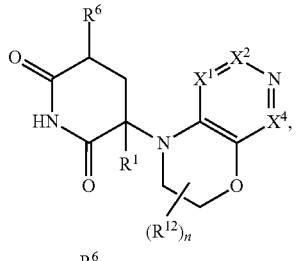
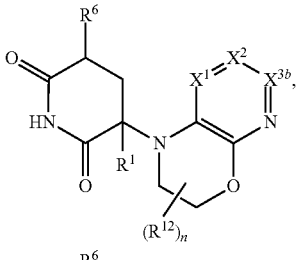
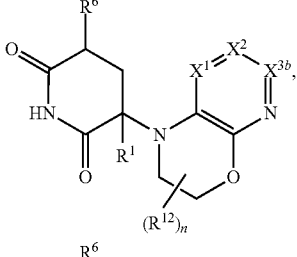
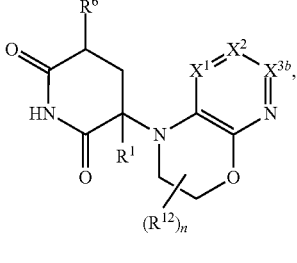
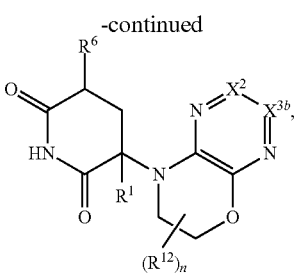
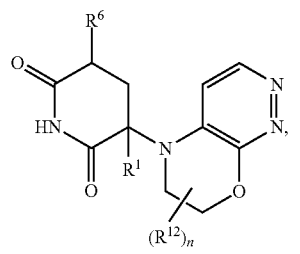
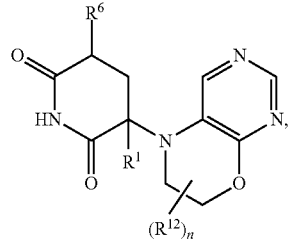
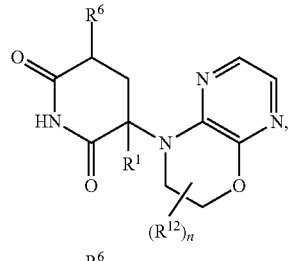
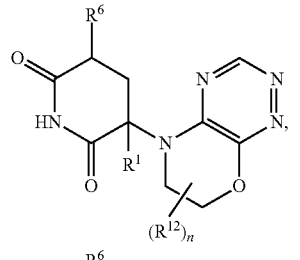
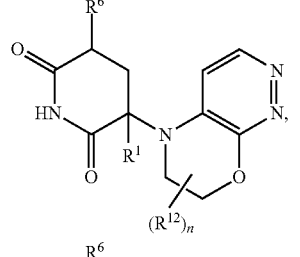
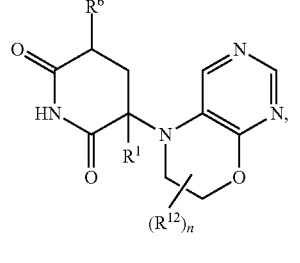

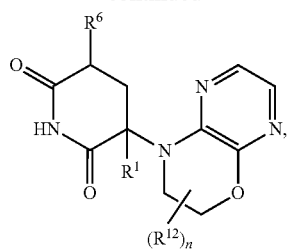

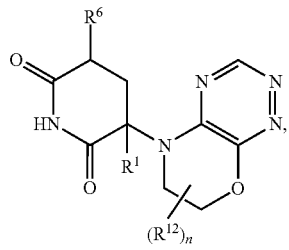

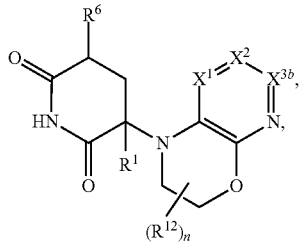

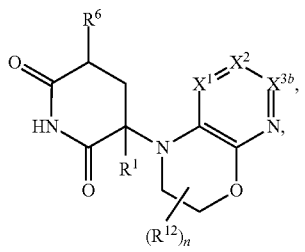

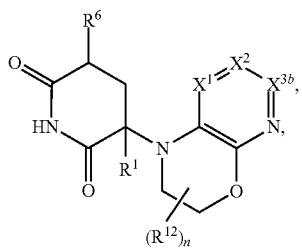

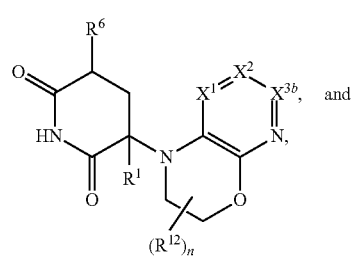

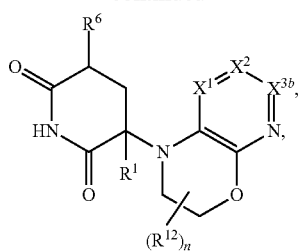

or a pharmaceutically acceptable salt thereof.

In certain embodiments a Degrader compound of Formula:

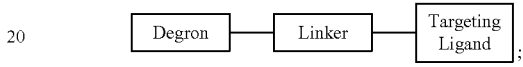

is provided wherein the Degron is a Degron described herein, and the attachment point to Linker is on the bicycle, A-ring, or B-ring. In preferred embodiments the Degron is attached to Linker on the A-ring.

Alternative Linker, A-Ring, and B-Ring Locations

In an alternative aspect, a compound is provided wherein the A-ring, B-ring, or Linker is bonded one position to the left or right of its drawn location. Where the prior linking position was a carbon on an aromatic ring the carbon can be replaced with $X^5$, wherein $X^5$ is N, CH, or $CR^5$.

For example, in this aspect the compound of Formula I may be:

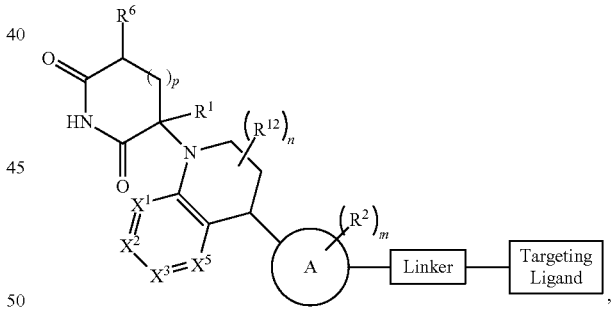

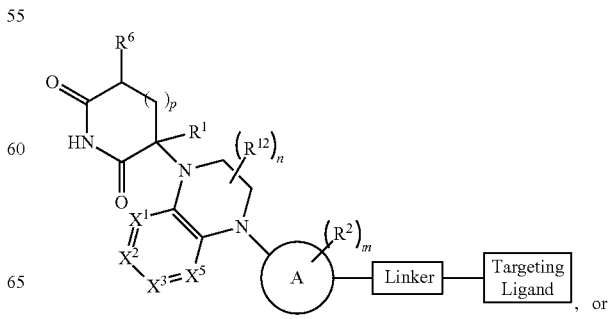

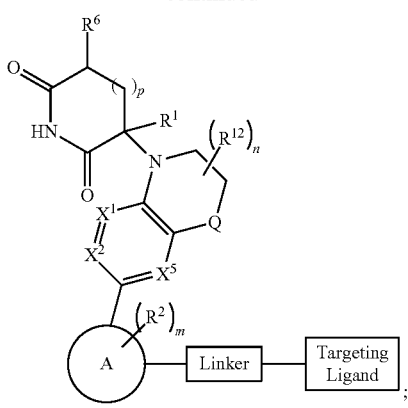
or a pharmaceutically acceptable salt thereof.
Additional non-limiting formulas of this aspect include:
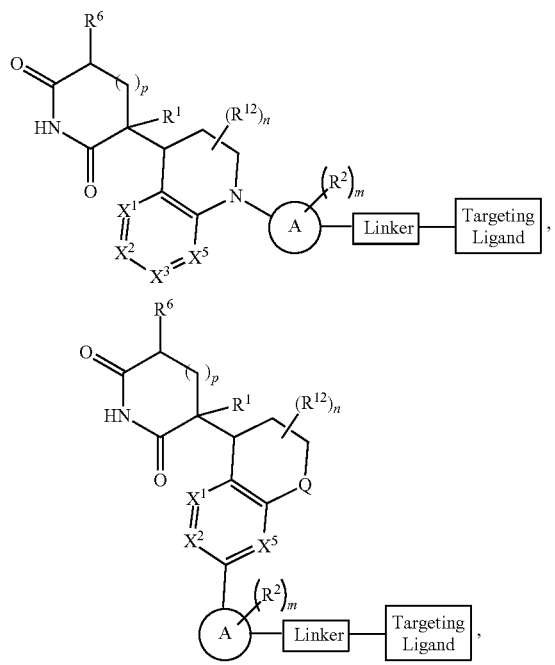
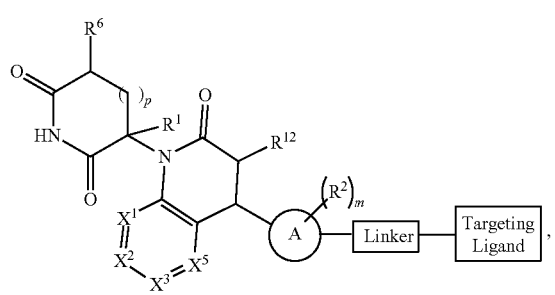
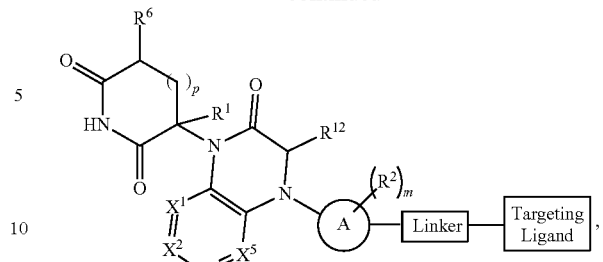
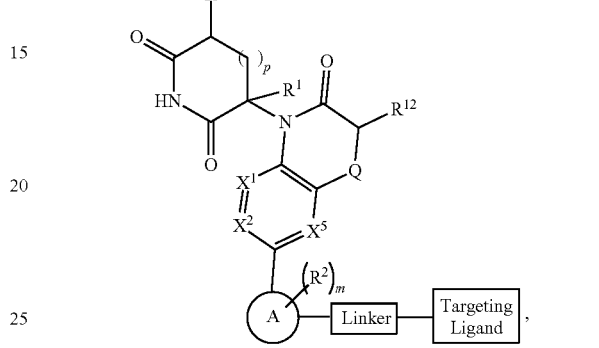
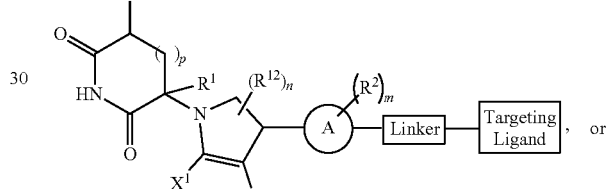
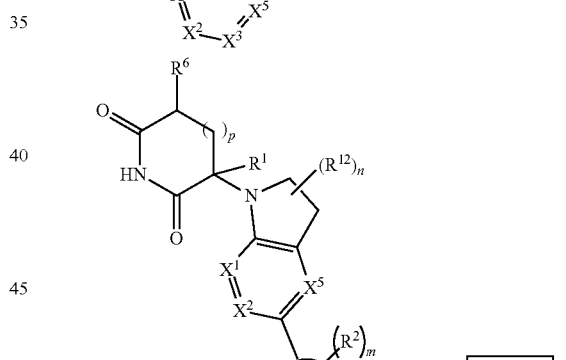
or a pharmaceutically acceptable salt thereof.
Additional non-limiting formulas of this aspect include.
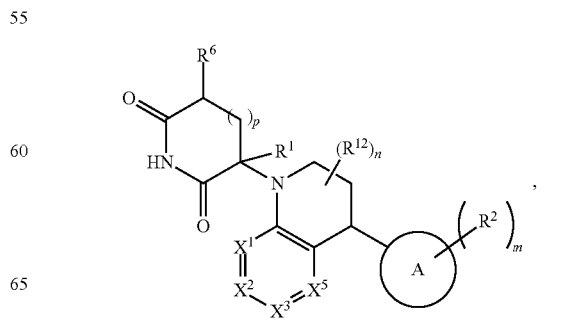

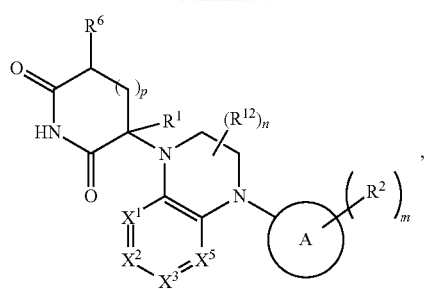
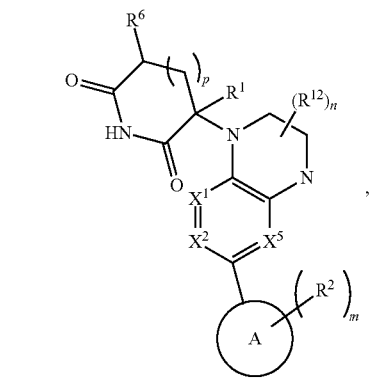
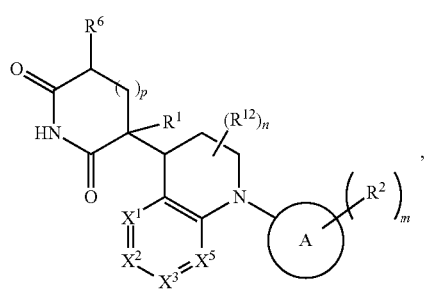
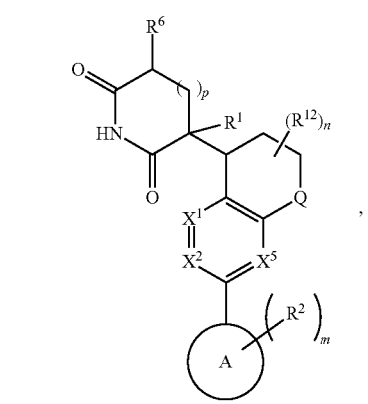
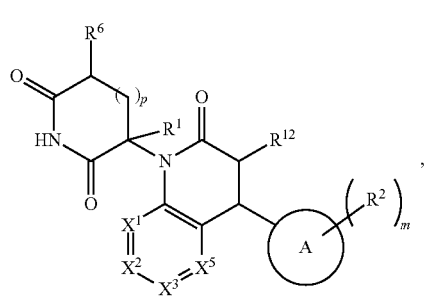
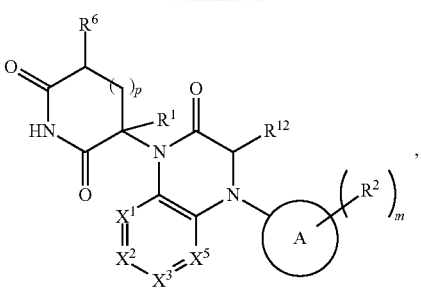
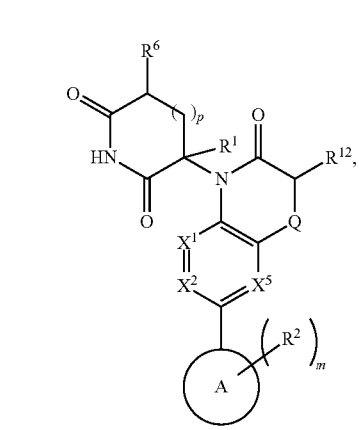
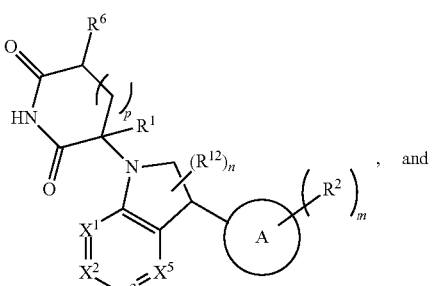, and
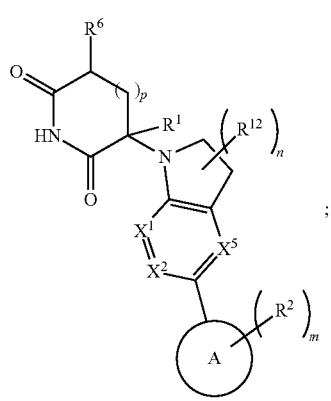;
or a pharmaceutically acceptable salt thereof.

In certain embodiments the compound of the present invention is of Formula
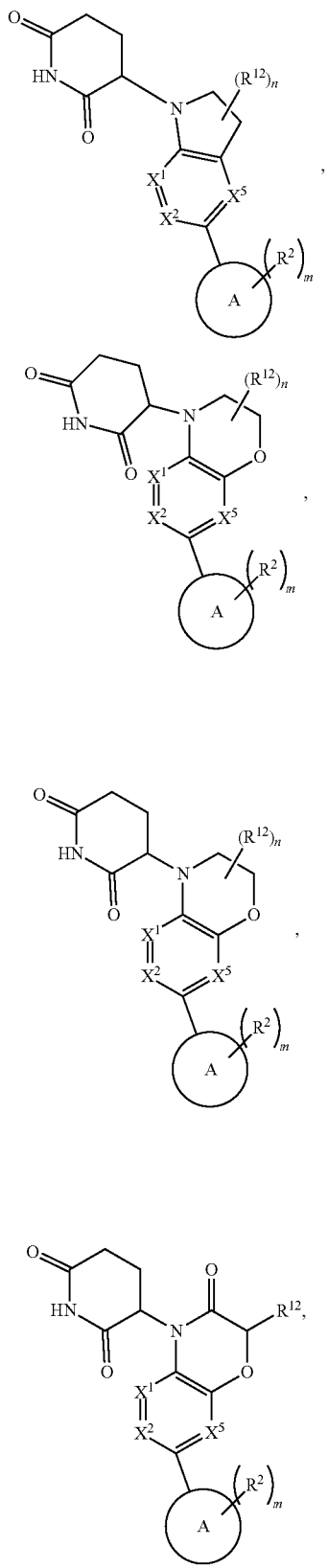
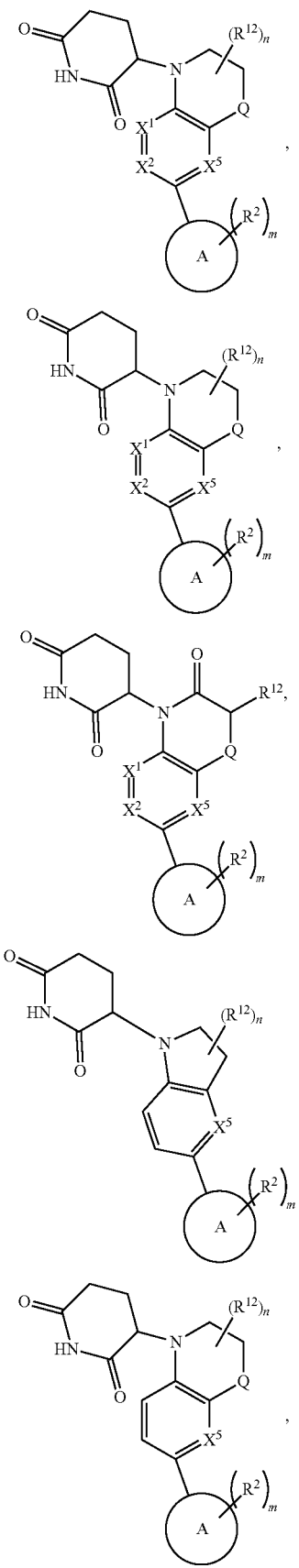

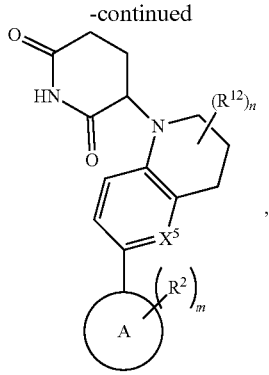
,
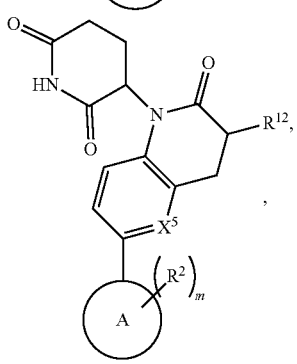
,
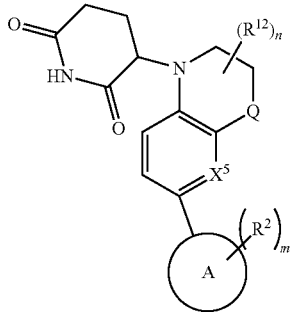
,
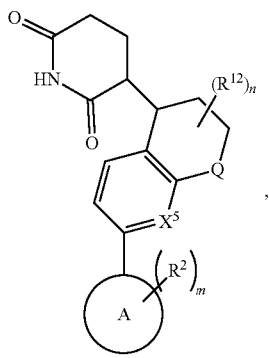
,
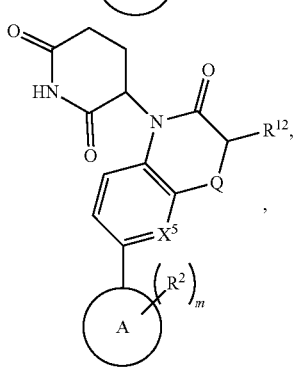
,
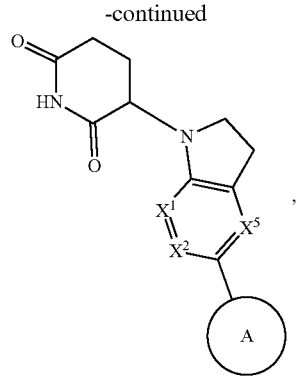
,
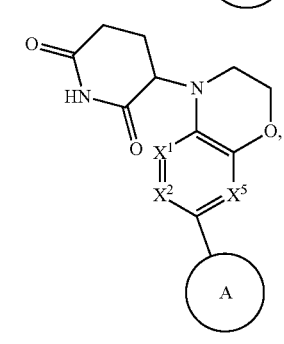
,
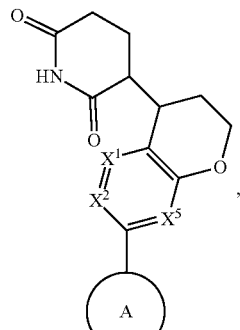
,
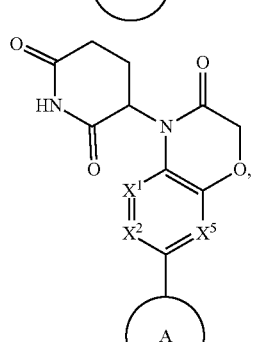
,
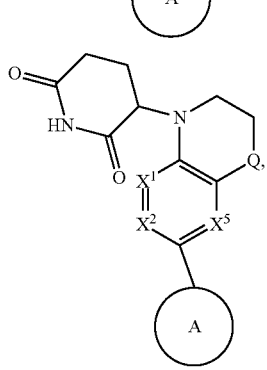
,

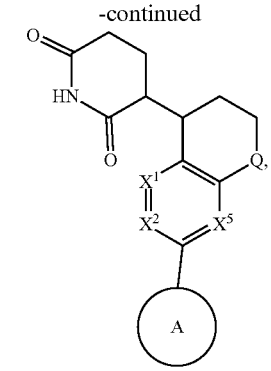
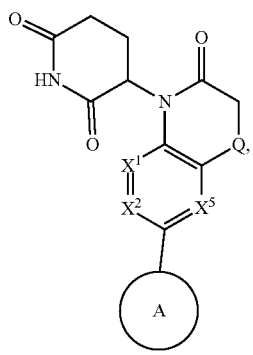
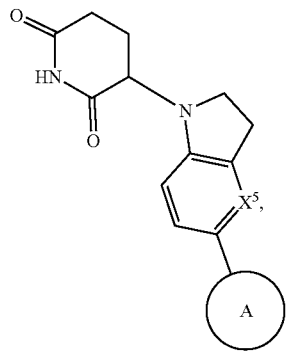
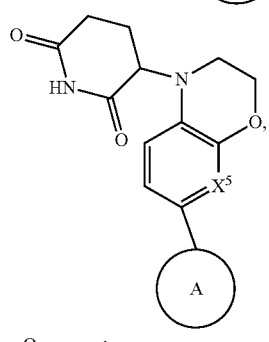
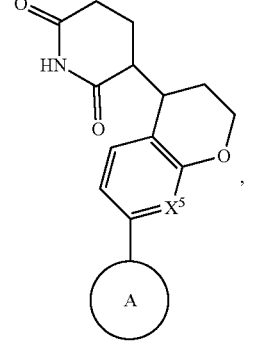
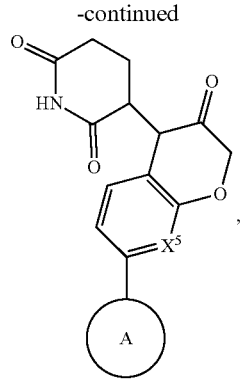
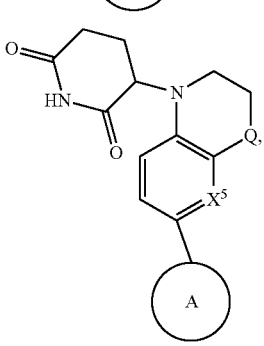
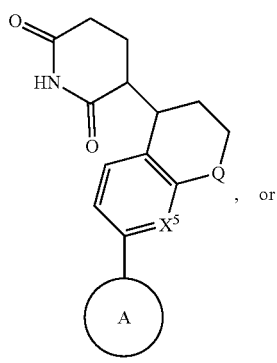
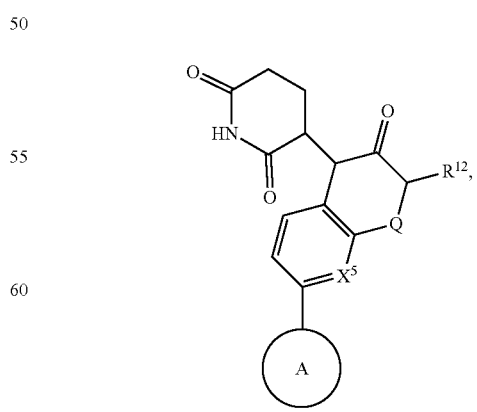
or a pharmaceutically acceptable salt thereof.

In certain embodiments the compound of the present invention is of Formula
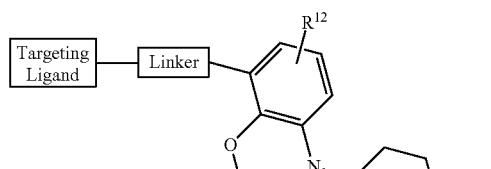
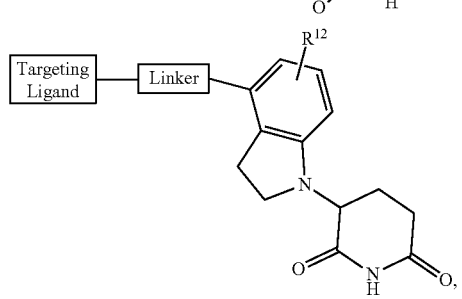
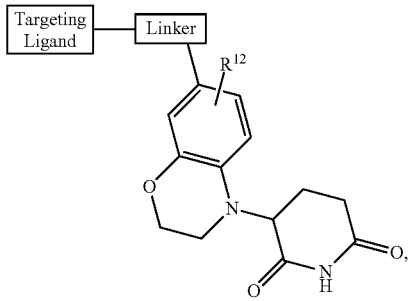
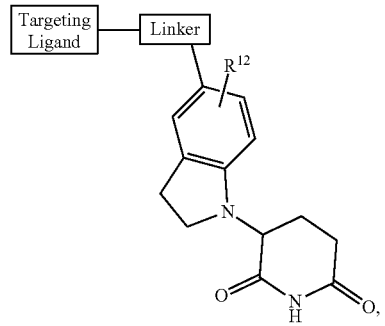
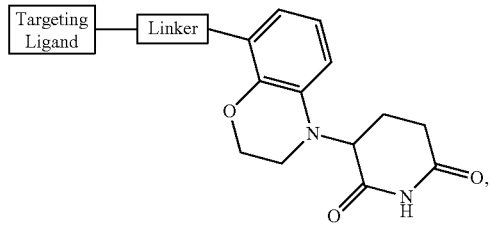
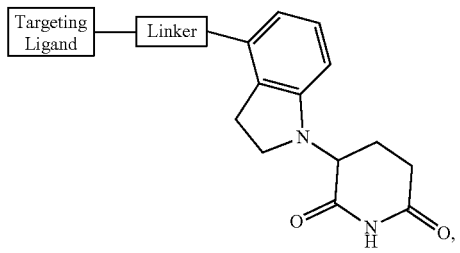
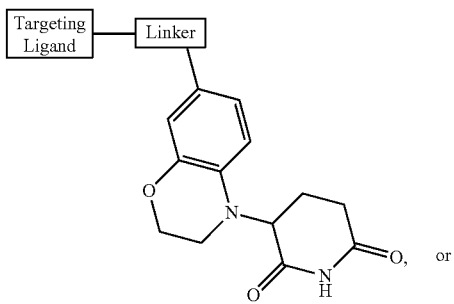
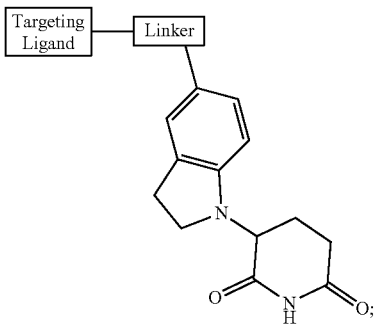
or a pharmaceutically acceptable salt thereof.
In certain embodiments the compound of the present invention is of Formula
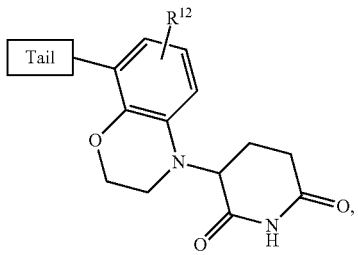
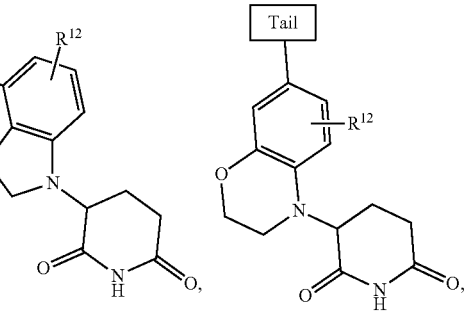
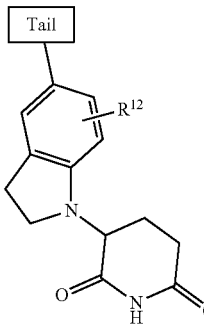

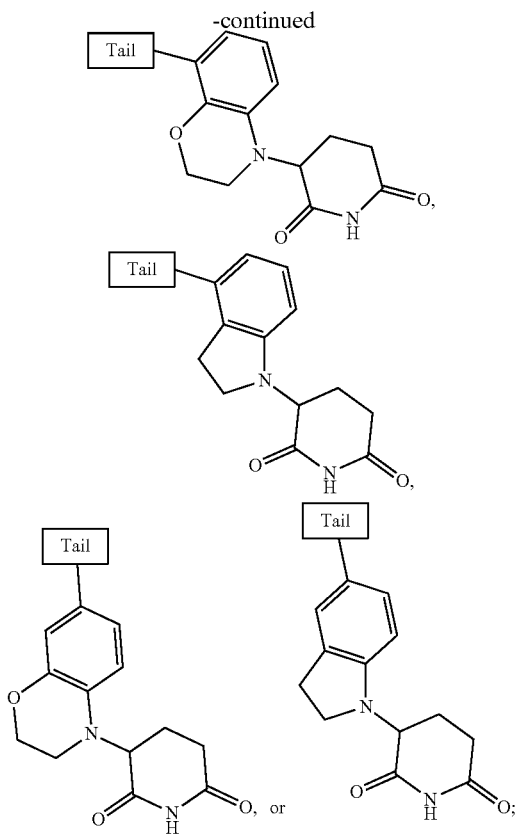

or a pharmaceutically acceptable salt thereof.

Embodiments of $R^1$

In certain embodiments, $R^1$ is hydrogen.
In certain embodiments, $R^1$ is alkyl.
In certain embodiments, $R^1$ is alkenyl.
In certain embodiments, $R^1$ is alkynyl.
In certain embodiments, $R^1$ is halogen.

Embodiments of $R^2$

In certain embodiments, $R^2$ is hydrogen.
In certain embodiments, $R^2$ is alkyl.
In certain embodiments, $R^2$ is haloalkyl.
In certain embodiments, $R^2$ is alkenyl.
In certain embodiments, $R^2$ is alkynyl.
In certain embodiments, $R^2$ is aryl.
In certain embodiments, $R^2$ is heteroaryl.
In certain embodiments, $R^2$ is heterocycle.
In certain embodiments, $R^2$ is —C(O)$R^9$.

Embodiments of $R^5$

In certain embodiments, $R^5$ is hydrogen.
In certain embodiments, $R^5$ is alkyl.
In certain embodiments, $R^5$ is haloalkyl.
In certain embodiments, $R^5$ is alkenyl.
In certain embodiments, $R^5$ is alkynyl.
In certain embodiments, $R^5$ is halogen.
In certain embodiments, $R^5$ is aryl.
In certain embodiments, $R^5$ is heteroaryl.
In certain embodiments, $R^5$ is heterocycle.
In certain embodiments, $R^5$ is cyano.
In certain embodiments, $R^5$ is nitro.
In certain embodiments, $R^5$ is —N$R^7R^8$.
In certain embodiments, $R^5$ is —O$R^7$.
In certain embodiments, $R^5$ is —S$R^7$.
In certain embodiments, $R^5$ is —C(O)$R^9$.
In certain embodiments, $R^5$ is —C(S)$R^9$.
In certain embodiments, $R^5$ is —S(O)$R^9$.
In certain embodiments, $R^5$ is —S(O)$_2R^9$.
In certain embodiments, $R^5$ is —OC(S)$R^9$.
In certain embodiments, $R^5$ is —N$R^7$S(O)$R^9$.
In certain embodiments, $R^5$ is —N$R^7$S(O)$_2R^9$.
In certain embodiments, $R^5$ is —P(O)($R^9$)$_2$.
In certain embodiments, $R^5$ is SP(O)($R^9$)$_2$.
In certain embodiments, $R^5$ is N$R^7$P(O)($R^9$)$_2$.
In certain embodiments, $R^5$ is —OP(O)($R^9$)$_2$.

Embodiments of $R^{5b}$

In certain embodiments, $R^{5b}$ is hydrogen.
In certain embodiments, $R^{5b}$ is alkyl.
In certain embodiments, $R^{5b}$ is alkenyl.
In certain embodiments, $R^{5b}$ is alkynyl.
In certain embodiments, $R^{5b}$ is aryl.
In certain embodiments, $R^{5b}$ is heteroaryl.
In certain embodiments, $R^{5b}$ is heterocycle.
In certain embodiments, $R^{5b}$ is —C(O)alkyl.
In certain embodiments, $R^{5b}$ is —C(S)$R^9$.
In certain embodiments, $R^{5b}$ is —S(O)$R^9$.
In certain embodiments, $R^{5b}$ is —S(O)$_2R^9$.

Embodiments of $R^{5c}$

In certain embodiments, $R^{5c}$ is hydrogen.
In certain embodiments, $R^{5c}$ is alkyl.
In certain embodiments, $R^{5c}$ is haloalkyl.
In certain embodiments, $R^{5c}$ is alkenyl.
In certain embodiments, $R^{5c}$ is alkynyl.
In certain embodiments, $R^{5c}$ is halogen.
In certain embodiments, $R^{5c}$ is aryl.
In certain embodiments, $R^{5c}$ is heteroaryl.
In certain embodiments, $R^{5c}$ is heterocycle.
In certain embodiments, $R^{5c}$ is cyano.
In certain embodiments, $R^{5c}$ is nitro.
In certain embodiments, $R^{5c}$ is —O$R^7$.
In certain embodiments, $R^{5c}$ is —S$R^7$.
In certain embodiments, $R^{5c}$ is —C(O)$R^9$.
In certain embodiments, $R^{5c}$ is —C(S)$R^9$.
In certain embodiments, $R^{5c}$ is —S(O)$R^9$.
In certain embodiments, $R^{5c}$ is —S(O)$_2R^9$.
In certain embodiments, $R^{5c}$ is —OC(S)$R^9$.
In certain embodiments, $R^{5c}$ is —N$R^7$S(O)$R^9$.
In certain embodiments, $R^{5c}$ is —N$R^7$S(O)$_2R^9$.
In certain embodiments, $R^{5c}$ is —P(O)($R^9$)$_2$.
In certain embodiments, $R^{5c}$ is SP(O)($R^9$)$_2$.
In certain embodiments, $R^{5c}$ is N$R^7$P(O)($R^9$)$_2$.
In certain embodiments, $R^{5c}$ is —OP(O)($R^9$)$_2$.

Embodiments of $R^6$

In certain embodiments, $R^6$ is hydrogen.
In certain embodiments, $R^6$ is alkyl.
In certain embodiments, $R^6$ is alkenyl.
In certain embodiments, $R^6$ is alkynyl.
In certain embodiments, $R^6$ is halogen.

Embodiments of $R^7$

In certain embodiments, $R^7$ is hydrogen.
In certain embodiments, $R^7$ is alkyl.

In certain embodiments, $R^7$ is haloalkyl.
In certain embodiments, $R^7$ is alkenyl.
In certain embodiments, $R^7$ is alkynyl.
In certain embodiments, $R^7$ is aryl.
In certain embodiments, $R^7$ is heteroaryl.
In certain embodiments, $R^7$ is heterocycle.
In certain embodiments, $R^7$ is $C(O)R^{14}$.

Embodiments of $R^1$

In certain embodiments, $R^8$ is hydrogen.
In certain embodiments, $R^8$ is alkyl.
In certain embodiments, $R^8$ is haloalkyl.
In certain embodiments, $R^8$ is alkenyl.
In certain embodiments, $R^8$ is alkynyl.
In certain embodiments, $R^8$ is aryl.
In certain embodiments, $R^8$ is heteroaryl.
In certain embodiments, $R^8$ is heterocycle.
In certain embodiments, $R^8$ is $C(O)R^{14}$.

Embodiments of $R^9$

In certain embodiments, $R^9$ is hydrogen.
In certain embodiments, $R^9$ is alkyl.
In certain embodiments, $R^9$ is haloalkyl.
In certain embodiments, $R^9$ is alkenyl.
In certain embodiments, $R^9$ is alkynyl.
In certain embodiments, $R^9$ is aryl.
In certain embodiments, $R^9$ is heteroaryl.
In certain embodiments, $R^9$ is heterocycle.
In certain embodiments, $R^9$ is —$NR^7R^8$.
In certain embodiments, $R^9$ is —$OR^7$.
In certain embodiments, $R^9$ is —$SR^7$.

Embodiments of $R^{10}$

In certain embodiments, $R^{10}$ is hydrogen.
In certain embodiments, $R^{10}$ is alkyl.
In certain embodiments, $R^{10}$ is haloalkyl.
In certain embodiments, $R^{10}$ is alkenyl.
In certain embodiments, $R^{10}$ is alkynyl.
In certain embodiments, $R^{10}$ is haloalkyl.
In certain embodiments, $R^{10}$ is halogen.
In certain embodiments, $R^{10}$ is aryl.
In certain embodiments, $R^{10}$ is haloalkyl.
In certain embodiments, $R^{10}$ is hydrogen.
In certain embodiments, $R^{10}$ is alkyl.
In certain embodiments, $R^{10}$ is heteroaryl.
In certain embodiments, $R^{10}$ is heterocycle.
In certain embodiments, $R^{10}$ is cyano.
In certain embodiments, $R^{10}$ is nitro.
In certain embodiments, $R^{10}$ is —$N^{11}R^{13}$.
In certain embodiments, $R^{10}$ is —$OR^{11}$.
In certain embodiments, $R^{10}$ is —$SR^{11}$.
In certain embodiments, $R^{10}$ is —$C(O)R^{14}$.
In certain embodiments, $R^{10}$ is —$C(S)R^{14}$.
In certain embodiments, $R^{10}$ is —$S(O)R^{14}$.
In certain embodiments, $R^{10}$ is —$S(O)_2R^{14}$.
In certain embodiments, $R^{10}$ is —$NR^{11}S(O)_2R^{14}$.
In certain embodiments, $R^{10}$ is —$P(O)(R^{14})_2$.
In certain embodiments, $R^{10}$ is —$NR^{11}P(O)(R^{14})_2$.
In certain embodiments, $R^{10}$ is —$OP(O)(R^{14})_2$.

Embodiments of $R^{11}$

In certain embodiments, $R^{11}$ is hydrogen.
In certain embodiments, $R^{11}$ is alkyl.

In certain embodiments, $R^{11}$ is haloalkyl.
In certain embodiments, $R^{11}$ is alkenyl.
In certain embodiments, $R^{11}$ is alkynyl.
In certain embodiments, $R^{11}$ is aryl.
In certain embodiments, $R^{11}$ is heteroaryl.
In certain embodiments, $R^{11}$ is heterocycle.
In certain embodiments, $R^{11}$ is —$C(O)R^{14}$.
In certain embodiments, $R^{11}$ is —$C(S)R^{14}$.
In certain embodiments, $R^{11}$ is —$S(O)R^{14}$.
In certain embodiments, $R^{11}$ is —$S(O)_2R^{14}$.
In certain embodiments, $R^{11}$ is —$P(O)(R^{14})_2$.

Embodiments of $R^2$

In certain embodiments, $R^{12}$ is hydrogen.
In certain embodiments, $R^{12}$ is alkyl.
In certain embodiments, $R^{12}$ is haloalkyl.
In certain embodiments, $R^{12}$ is alkenyl.
In certain embodiments, $R^{12}$ is alkynyl.
In certain embodiments, $R^{12}$ is alkynyl.
In certain embodiments, $R^{12}$ is halogen.
In certain embodiments, $R^{12}$ is aryl.
In certain embodiments, $R^{12}$ is heterocycle.
In certain embodiments, $R^{12}$ is heteroaryl.
In certain embodiments, $R^{12}$ is cyano.
In certain embodiments, $R^{12}$ is nitro.
In certain embodiments, $R^{12}$ is —$NR^{11}R^{13}$.
In certain embodiments, $R^{12}$ is —$OR^{11}$.
In certain embodiments, $R^{12}$ is —$SR^{11}$.

Embodiments of $R^3$

In certain embodiments, $R^{13}$ is hydrogen.
In certain embodiments, $R^{13}$ is alkyl.
In certain embodiments, $R^{13}$ is haloalkyl.
In certain embodiments, $R^{13}$ is alkenyl.
In certain embodiments, $R^{13}$ is alkynyl.
In certain embodiments, $R^{13}$ is aryl.
In certain embodiments, $R^{13}$ is heteroaryl.
In certain embodiments, $R^{13}$ is heterocycle.
In certain embodiments, $R^{13}$ is —$C(O)R^{14}$.
In certain embodiments, $R^{13}$ is —$C(S)R^{14}$.
In certain embodiments, $R^{13}$ is —$S(O)R^{14}$.
In certain embodiments, $R^{13}$ is —$S(O)_2R^{14}$.
In certain embodiments, $R^{13}$ is —$P(O)(R^{14})_2$.

Embodiments of $R^4$

In certain embodiments, $R^{14}$ is hydrogen.
In certain embodiments, $R^{14}$ is alkyl.
In certain embodiments, $R^{14}$ is haloalkyl.
In certain embodiments, $R^{14}$ is alkenyl.
In certain embodiments, $R^{14}$ is alkynyl.
In certain embodiments, $R^{14}$ is aryl.
In certain embodiments, $R^{14}$ is heteroaryl.
In certain embodiments, $R^{14}$ is heterocycle.
In certain embodiments, $R^{14}$ is amino.
In certain embodiments, $R^{14}$ is hydroxyl.
In certain embodiments, $R^{14}$ is alkoxy.
In certain embodiments, $R^{14}$ is —N(H)(alkyl).
In certain embodiments, $R^{14}$ is —N(alkyl)$_2$.

Embodiments of $R^{15a}$

In certain embodiments, $R^{15a}$ is hydrogen.
In certain embodiments, $R^{15a}$ is alkyl.
In certain embodiments, $R^{15a}$ is haloalkyl.

Embodiments of $R^{5b}$

In certain embodiments, $R^{15a}$ is alkenyl.
In certain embodiments, $R^{15a}$ is alkynyl.
In certain embodiments, $R^{15a}$ is halogen.
In certain embodiments, $R^{15a}$ is aryl.
In certain embodiments, $R^{15a}$ is heteroaryl.
In certain embodiments, $R^{15a}$ is heterocycle.
In certain embodiments, $R^{15a}$ is cyano.
In certain embodiments, $R^{15a}$ is nitro.
In certain embodiments, $R^{5a}$ is amino.
In certain embodiments, $R^{15a}$ is hydroxyl.
In certain embodiments, $R^{15a}$ is alkoxy.
In certain embodiments, $R^{15a}$ is —N(H)(alkyl).
In certain embodiments, $R^{15a}$ is —N(alkyl)$_2$.

Embodiments of $R^{5b}$

In certain embodiments, $R^{15b}$ is hydrogen.
In certain embodiments, $R^{15b}$ is alkyl.
In certain embodiments, $R^{15b}$ is haloalkyl.
In certain embodiments, $R^{15b}$ is alkenyl.
In certain embodiments, $R^{15b}$ is alkynyl.
In certain embodiments, $R^{15b}$ is halogen.
In certain embodiments, $R^{15b}$ is aryl.
In certain embodiments, $R^{5b}$ is heteroaryl.
In certain embodiments, $R^{5b}$ is heterocycle.
In certain embodiments, $R^{15b}$ is cyano.
In certain embodiments, $R^{15b}$ is nitro.
In certain embodiments, $R^{15b}$ is amino.
In certain embodiments, $R^{15b}$ is hydroxyl.
In certain embodiments, $R^{15b}$ is alkoxy.
In certain embodiments, $R^{15b}$ is —N(H)(alkyl).
In certain embodiments, $R^{15b}$ is —N(alkyl)$_2$.

Embodiments of $R^{15c}$

In certain embodiments, $R^{15c}$ is hydrogen.
In certain embodiments, $R^{15c}$ is alkyl.
In certain embodiments, $R^{15c}$ is haloalkyl.
In certain embodiments, $R^{15c}$ is alkenyl.
In certain embodiments, $R^{15c}$ is alkynyl.
In certain embodiments, $R^{15c}$ is halogen.
In certain embodiments, $R^{15c}$ is aryl.
In certain embodiments, $R^{15c}$, is heteroaryl.
In certain embodiments, $R^{15c}$ is heterocycle.
In certain embodiments, $R^{15c}$, is cyano.
In certain embodiments, $R^{15c}$ is nitro.
In certain embodiments, $R^{15c}$, is amino.
In certain embodiments, $R^{15c}$ is hydroxyl.
In certain embodiments, $R^{15c}$, is alkoxy.
In certain embodiments, $R^{15c}$ is —N(H)(alkyl).
In certain embodiments, $R^{15c}$, is —N(alkyl)$_2$.

Embodiments of $R^{5d}$

In certain embodiments, $R^{15d}$ is hydrogen.
In certain embodiments, $R^{15d}$ is alkyl.
In certain embodiments, $R^{15d}$ is haloalkyl.
In certain embodiments, $R^{15d}$ is alkenyl.
In certain embodiments, $R^{15d}$ is alkynyl.
In certain embodiments, $R^{15d}$ is halogen.
In certain embodiments, $R^{15d}$ is aryl.
In certain embodiments, $R^{15d}$ is heteroaryl.
In certain embodiments, $R^{15d}$ is heterocycle.
In certain embodiments, $R^{15d}$ is cyano.
In certain embodiments, $R^{15d}$ is nitro.
In certain embodiments, $R^{15d}$ is amino.
In certain embodiments, $R^{15d}$ is hydroxyl.
In certain embodiments, $R^{15d}$ is alkoxy.
In certain embodiments, $R^{15d}$ is —N(H)(alkyl).
In certain embodiments, $R^{15d}$ is —N(alkyl)$_2$.

Embodiments of $R^{15e}$

In certain embodiments, $R^{15e}$ is hydrogen.
In certain embodiments, $R^{15e}$ is alkyl.
In certain embodiments, $R^{15e}$ is haloalkyl.
In certain embodiments, $R^{15e}$ is alkenyl.
In certain embodiments, $R^{15e}$ is alkynyl.
In certain embodiments, $R^{15e}$ is halogen.
In certain embodiments, $R^{15e}$ is aryl.
In certain embodiments, $R^{15e}$ is heteroaryl.
In certain embodiments, $R^{15e}$ is heterocycle.
In certain embodiments, $R^{15e}$ is cyano.
In certain embodiments, $R^{15e}$ is nitro.
In certain embodiments, $R^{15e}$ is amino.
In certain embodiments, $R^{15e}$ is hydroxyl.
In certain embodiments, $R^{15e}$ is alkoxy.
In certain embodiments, $R^{15e}$ is —N(H)(alkyl).
In certain embodiments, $R^{15e}$ is —N(alkyl)$_2$.

Embodiments of $R^{5f}$

In certain embodiments, $R^{15f}$ is hydrogen.
In certain embodiments, $R^{15f}$ is alkyl.
In certain embodiments, $R^{15f}$ is haloalkyl.
In certain embodiments, $R^{15f}$ is alkenyl.
In certain embodiments, $R^{15f}$ is alkynyl.
In certain embodiments, $R^{15f}$ is halogen.
In certain embodiments, $R^{15f}$ is aryl.
In certain embodiments, $R^{15f}$ is heteroaryl.
In certain embodiments, $R^{15f}$ is heterocycle.
In certain embodiments, $R^{15f}$ is cyano.
In certain embodiments, $R^{15f}$ is nitro.
In certain embodiments, $R^{15f}$ amino.
In certain embodiments, $R^{15f}$ is hydroxyl.
In certain embodiments, $R^{15f}$ is alkoxy.
In certain embodiments, $R^{15f}$ is —N(H)(alkyl).
In certain embodiments, $R^{15f}$ is —N(alkyl)$_2$.

Embodiments of $R^{15g}$

In certain embodiments, $R^{15g}$ is hydrogen.
In certain embodiments, $R^{15g}$ is alkyl.
In certain embodiments, $R^{15g}$ is haloalkyl.
In certain embodiments, $R^{15g}$ is alkenyl.
In certain embodiments, $R^{15g}$ is alkynyl.
In certain embodiments, $R^{15g}$ is halogen.
In certain embodiments, $R^{15g}$ is aryl.
In certain embodiments, $R^{15g}$ is heteroaryl.
In certain embodiments, $R^{15g}$ is heterocycle.
In certain embodiments, $R^{15g}$ is cyano.
In certain embodiments, $R^{15g}$ is nitro.
In certain embodiments, $R^{15g}$ is amino.
In certain embodiments, $R^{15g}$ is hydroxyl.
In certain embodiments, $R^{15g}$ is alkoxy.
In certain embodiments, $R^{15g}$ is —N(H)(alkyl).
In certain embodiments, $R^{15g}$ is —N(alkyl)$_2$.

Embodiments of $R^{16}$

In certain embodiments, $R^{16}$ is hydrogen.
In certain embodiments, $R^{16}$ is alkyl.
In certain embodiments, $R^{16}$ is haloalkyl.
In certain embodiments, $R^{16}$ is alkenyl.

In certain embodiments, $R^{16}$ is alkynyl.
In certain embodiments, $R^{16}$ is halogen.
In certain embodiments, $R^{16}$ is aryl.
In certain embodiments, $R^{16}$ is heteroaryl.
In certain embodiments, $R^{16}$ is heterocycle.
In certain embodiments, $R^{16}$ is cyano.
In certain embodiments, $R^{16}$ is nitro.
In certain embodiments, $R^{16}$ is —NR$^{11}$R$^{11}$.
In certain embodiments, $R^{16}$ is —OR$^{11}$.
In certain embodiments, $R^{16}$ is —SR$^{11}$.
In certain embodiments, $R^{16}$ is —C(O)R$^{14}$.
In certain embodiments, $R^{16}$ is —OC(S)R$^{14}$
In certain embodiments, $R^{16}$ is —OS(O)R$^{14}$.
In certain embodiments, $R^{16}$ is OS(O)R$^{14}$.
In certain embodiments, $R^{16}$ is —OS(O)$_2$R$^{14}$.
In certain embodiments, $R^{16}$ is —NR$^{11}$C(O)R$^{14}$.
In certain embodiments, $R^{16}$ is —NR$^{11}$C(S)R$^{14}$.
In certain embodiments, $R^{16}$ is —NR$^{11}$S(O)R$^{14}$.
In certain embodiments, $R^{16}$ is —P(O)(R$^{14}$)$_2$.
In certain embodiments, $R^{16}$ is —NR$^{11}$P(O)(R$^{14}$)$_2$.
In certain embodiments, $R^{16}$ is —OP(O)(R$^{14}$).

Embodiments of $R^{17}$

In certain embodiments, $R^{17}$ is hydrogen.
In certain embodiments, $R^{17}$ is alkyl.
In certain embodiments, $R^{17}$ is haloalkyl.
In certain embodiments, $R^{17}$ is alkenyl.
In certain embodiments, $R^{17}$ is alkynyl.
In certain embodiments, $R^{17}$ is halogen.
In certain embodiments, $R^{17}$ is aryl.
In certain embodiments, $R^{17}$ is heteroaryl.
In certain embodiments, $R^{17}$ is heterocycle.
In certain embodiments, $R^{17}$ is —C(O)R$^{14}$.
In certain embodiments, $R^{17}$ is —C(S)R$^{14}$.
In certain embodiments, $R^{17}$ is —S(O)R$^{14}$.
In certain embodiments, $R^{17}$ is S(O)$_2$R$^{14}$.
In certain embodiments, $R^{17}$ is —P(O)(R$^{14}$).

Embodiments of $R^{18}$

In certain embodiments, $R^{18}$ is hydrogen.
In certain embodiments, $R^{18}$ is alkyl.
In certain embodiments, $R^{18}$ is haloalkyl.
In certain embodiments, $R^{18}$ is alkenyl.
In certain embodiments, $R^{18}$ is alkynyl.
In certain embodiments, $R^{18}$ is halogen.
In certain embodiments, $R^{18}$ is aryl.
In certain embodiments, $R^{18}$ is heteroaryl.
In certain embodiments, $R^{18}$ is heterocycle.
In certain embodiments, $R^{18}$ is cyano.
In certain embodiments, $R^{18}$ is nitro.
In certain embodiments, $R^{18}$ is —NRR$^{13}$.
In certain embodiments, $R^{18}$ is —OR$^{11}$.
In certain embodiments, $R^{18}$ is —SR$^{11}$.
In certain embodiments, $R^{18}$ is —OC(O)R$^{14}$.
In certain embodiments, $R^{18}$ is —OC(S)R$^{14}$.
In certain embodiments, $R^{18}$ is —OS(O)R$^{14}$.
In certain embodiments, $R^{18}$ is OS(O)$_2$R$^{14}$.
In certain embodiments, $R^{18}$ is —NR$^{11}$C(O)R$^{14}$.
In certain embodiments, $R^{18}$ is —NR$^{11}$C(S)R$^{14}$.
In certain embodiments, $R^{18}$ is —P(O)(R$^{14}$)$_2$.
In certain embodiments, $R^{18}$ is NR$^{11}$P(O)(R$^{14}$)$_2$.
In certain embodiments, $R^{18}$ is —OP(O)(R$^{14}$)$_2$.

In one embodiment Targeting Ligand is a small molecule that binds to a Targeted Protein.

In one embodiment the Targeted Protein is a mediator of abnormal cellular proliferation in a host in need of such therapy.

Examples of the Degrader compound according to the present invention are:

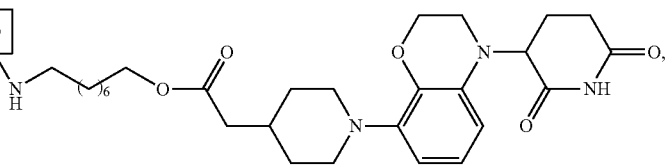

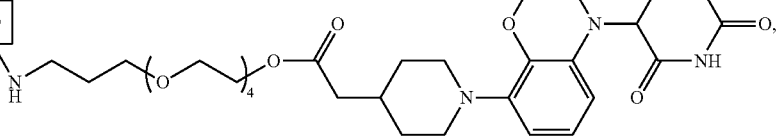

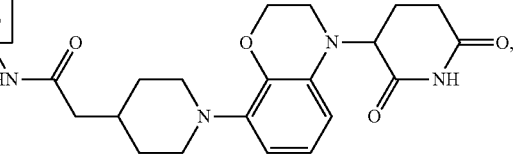

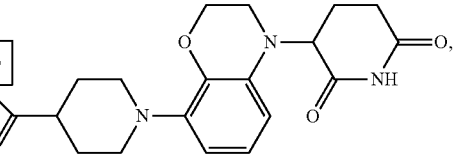

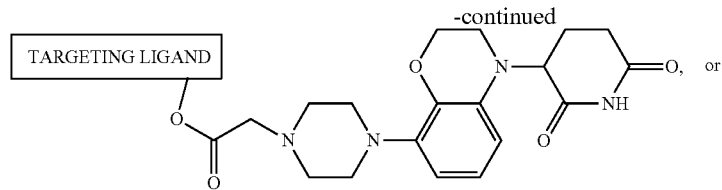

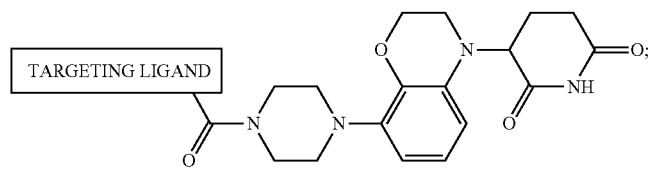

or a pharmaceutically acceptable salt thereof.

In another aspect, a compound is provided of Formula I-A or Formula I-B:

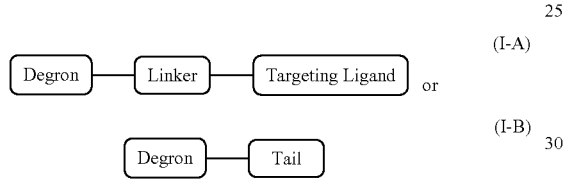

wherein Linker is a bond or a bivalent or multivalent chemical group that attaches the Degron to the Targeting Ligand as described herein;

Tail is selected from -(Tail) as defined herein. Tail is covalently attached to at least one Degron and is not attached to a Targeting Ligand.

Targeting Ligand is a molecule that binds to a Target Protein, wherein the Target Protein is a mediator of a disease in a host;

The Degron compound, for example, can be selected from the following moieties, wherein there is an open valence that covalently connects to the tail, and wherein the open valence is typically not on the glutarimide moiety. In certain embodiments, the tail is covalently attached to the Degron on the non-fused phenyl ring at the para, meta or ortho position. In alternative embodiments, the tail is covalently bound on the fused phenyl or heteroaryl ring.

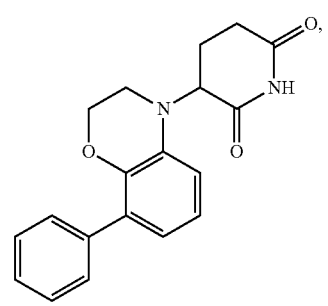

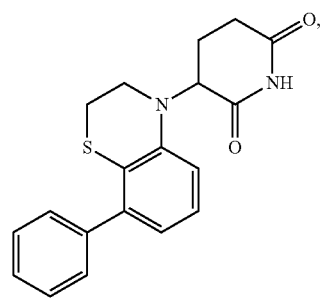

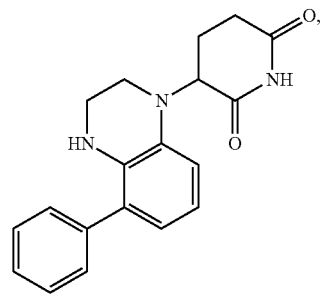

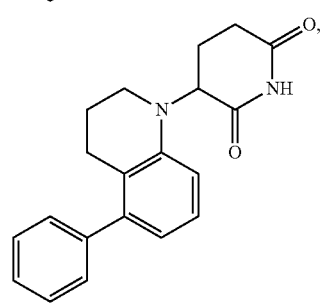

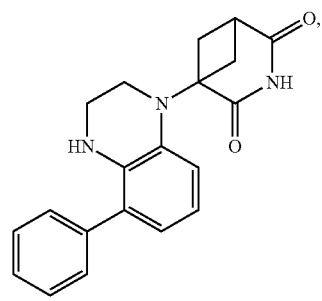

185
-continued
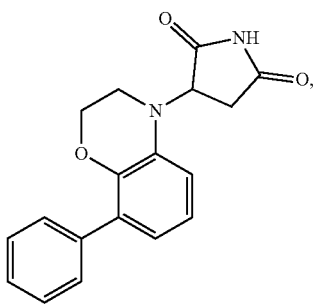
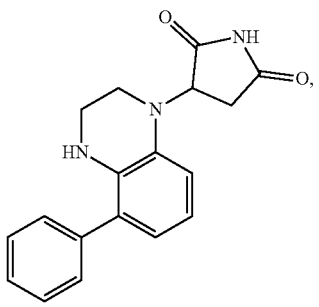
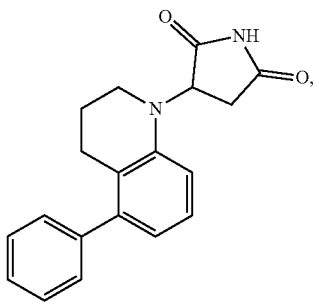
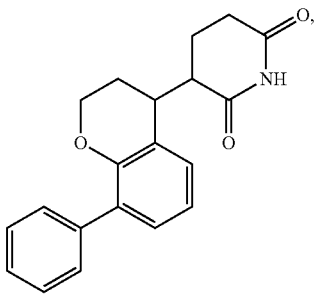
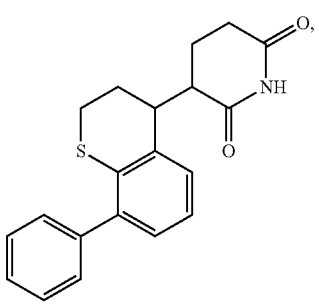
186
-continued
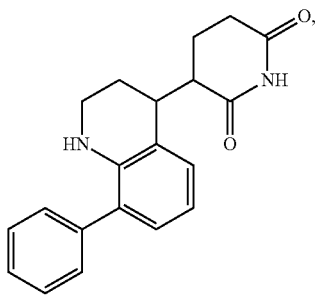
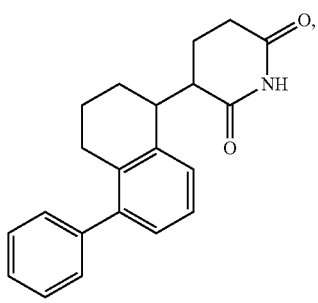
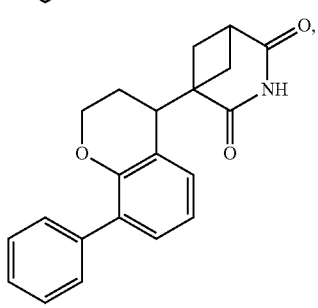
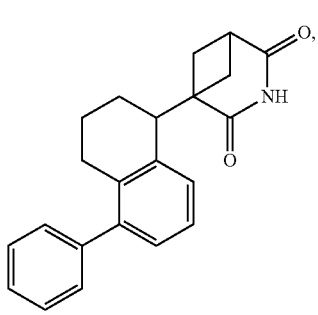
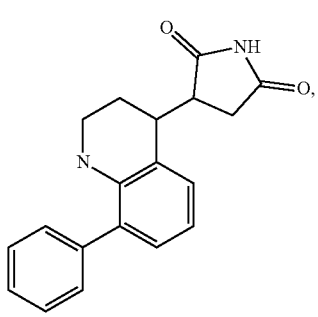

187
-continued
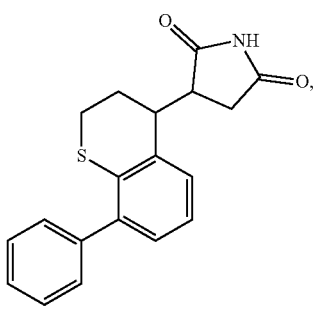
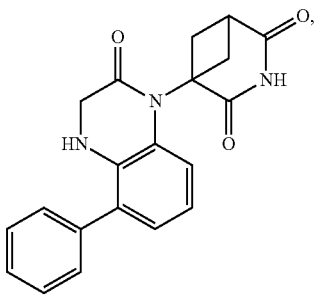
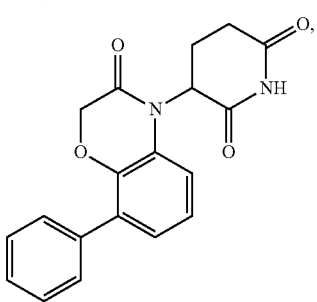
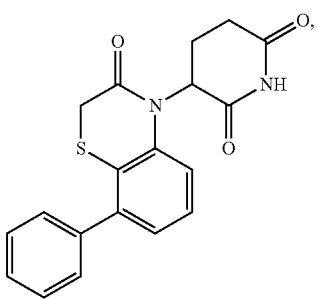
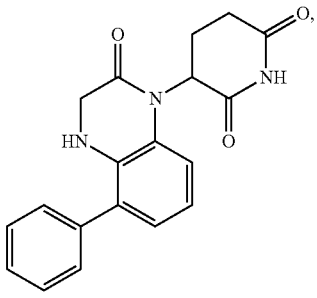
188
-continued
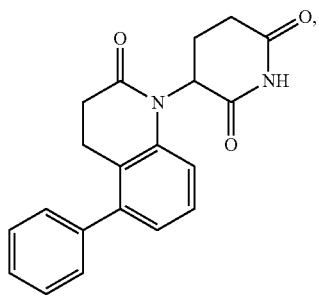
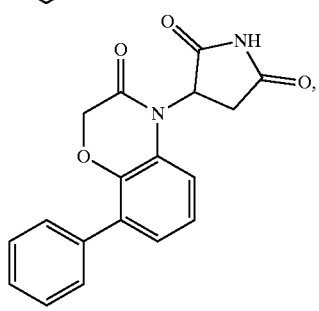
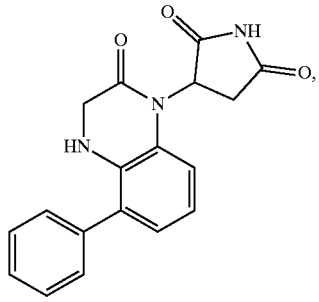
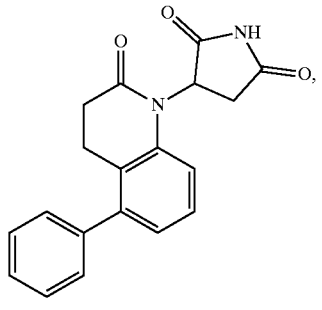
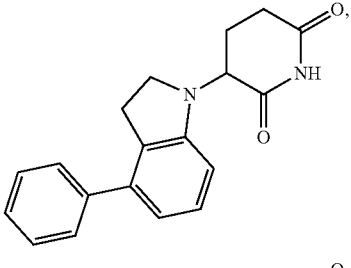

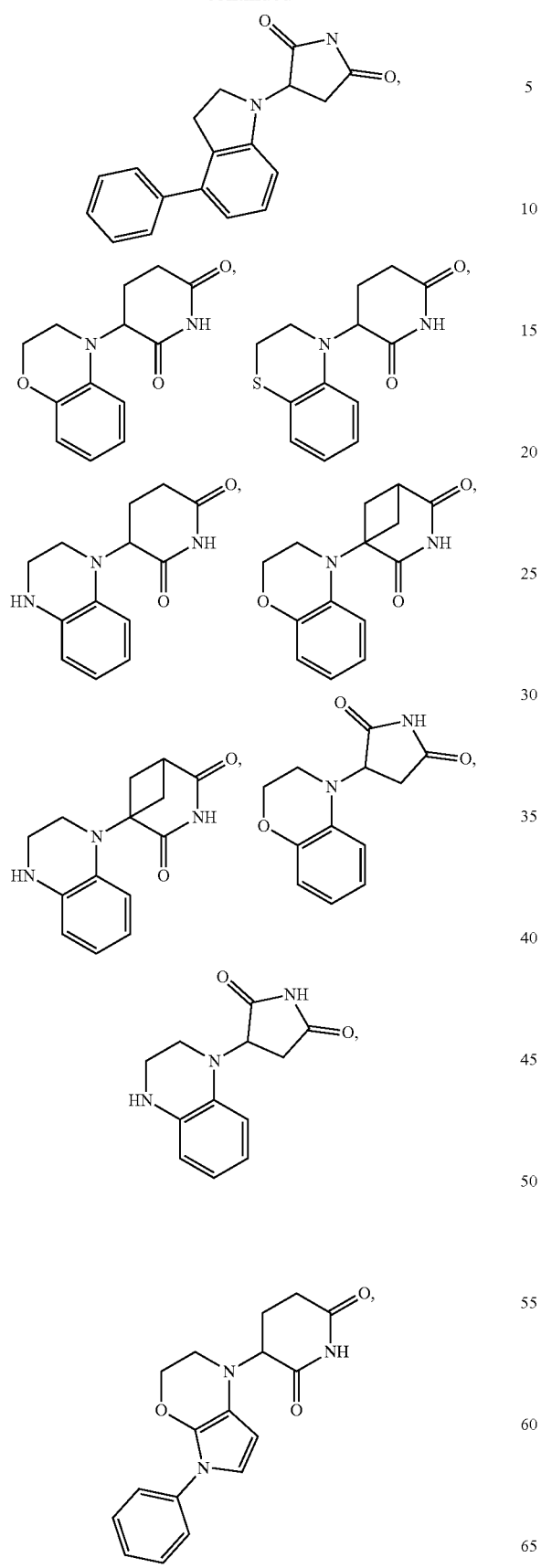
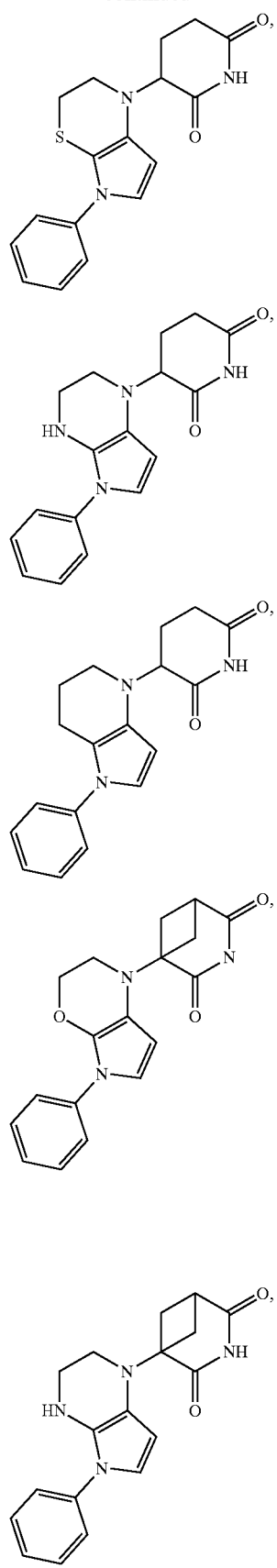

191
-continued
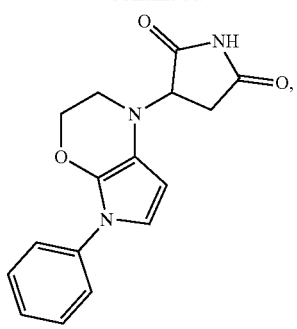
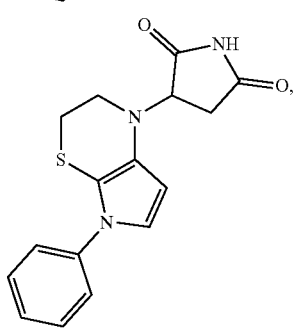
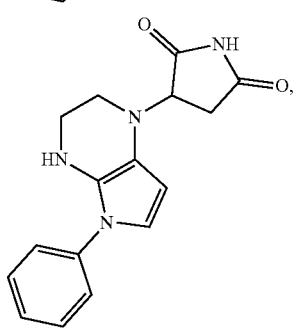
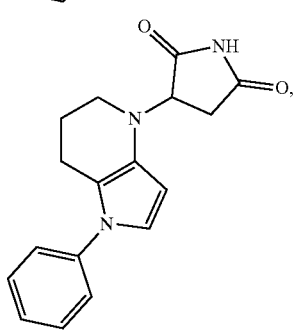
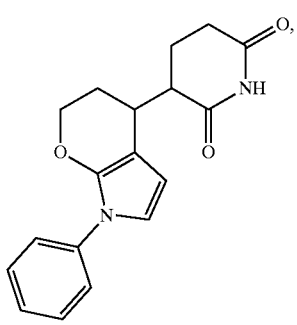
192
-continued
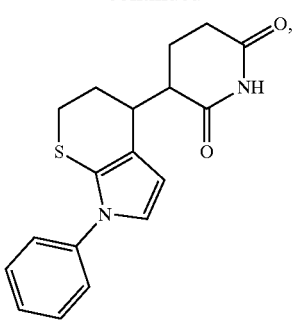
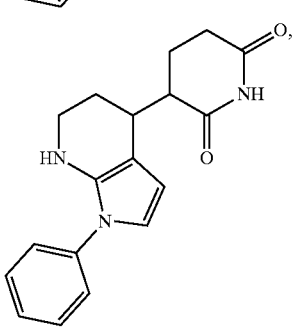
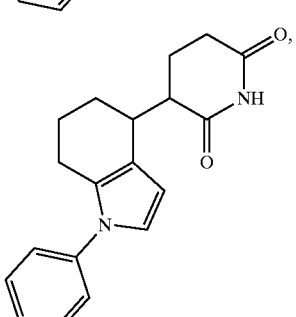
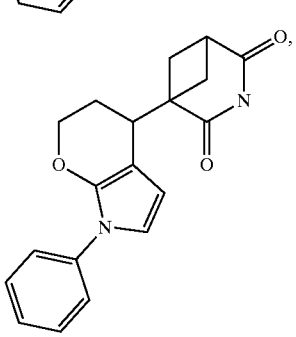
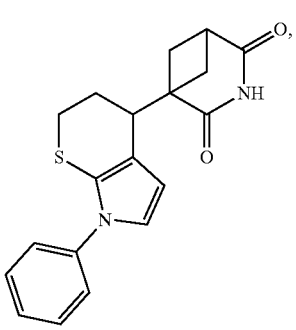

193
-continued
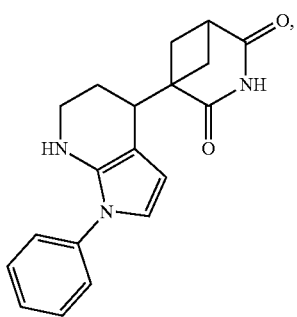
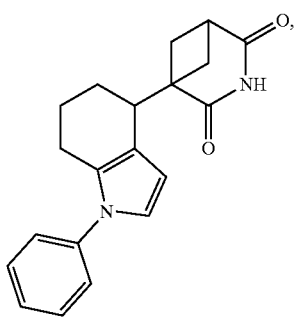
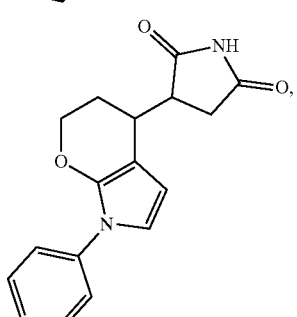
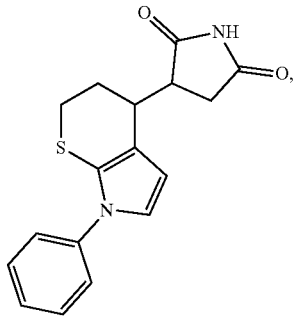
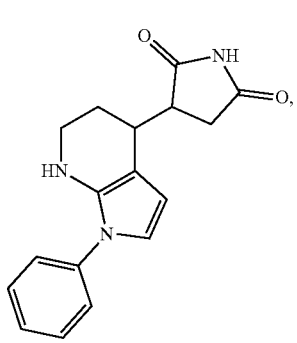
194
-continued
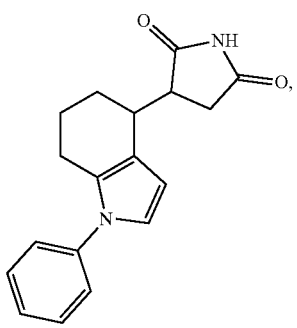
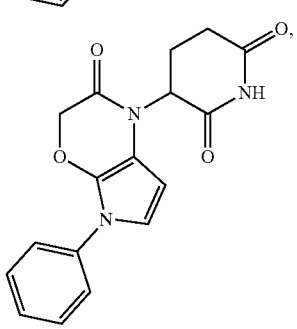
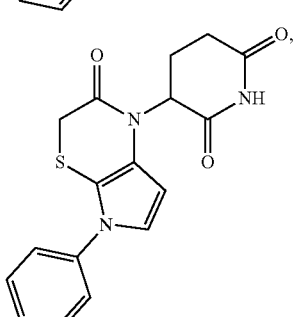
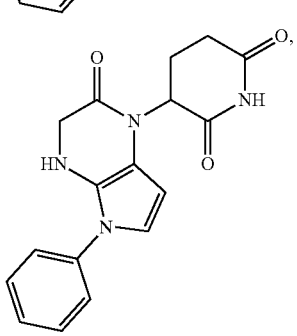
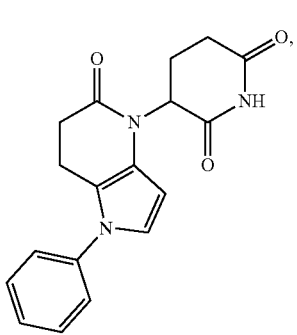

-continued
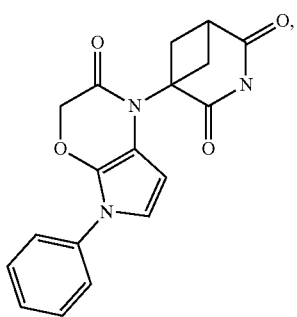
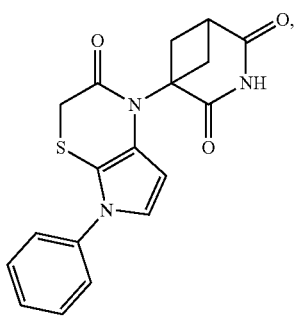
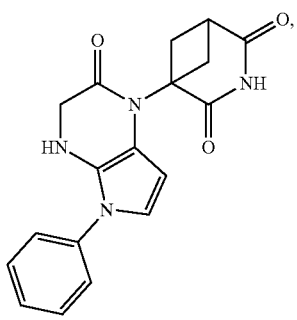
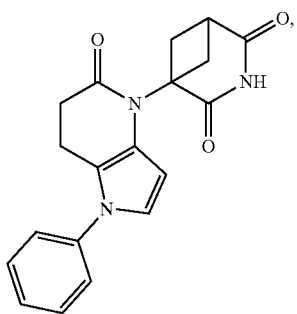
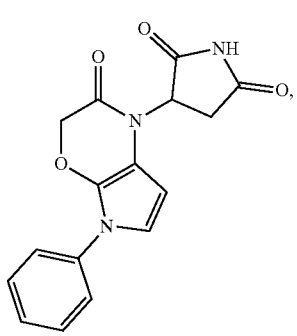
-continued
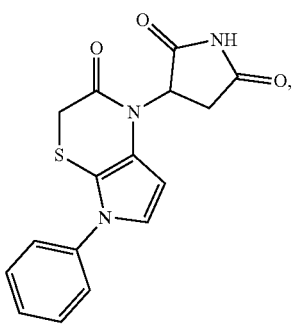
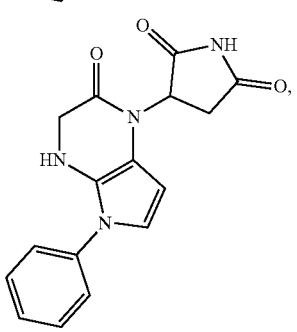
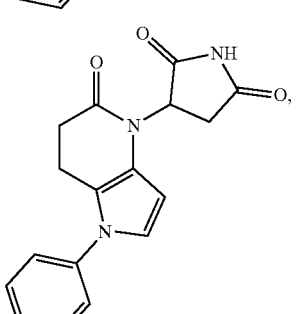
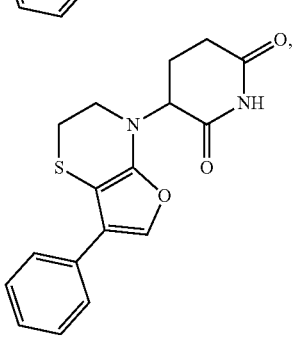
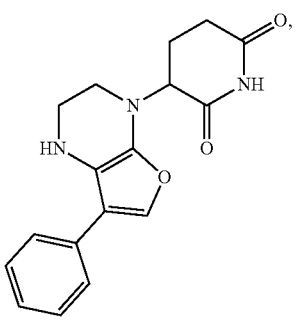

197
-continued
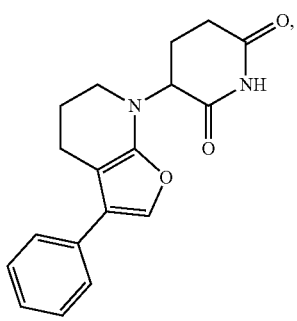
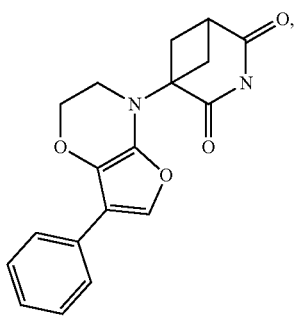
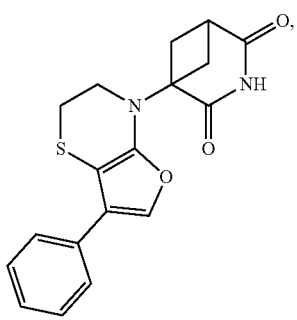
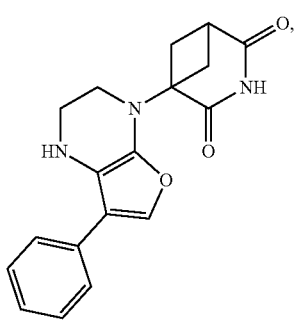
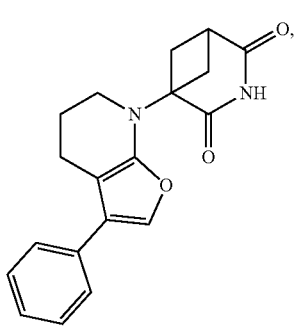
198
-continued
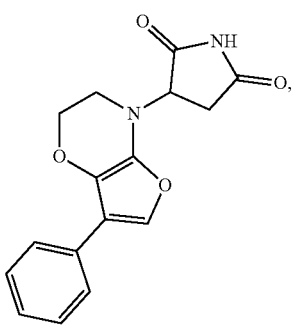
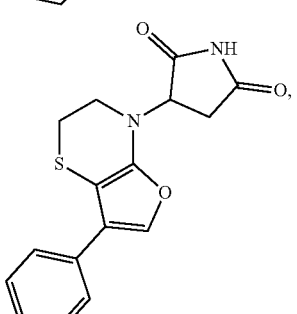
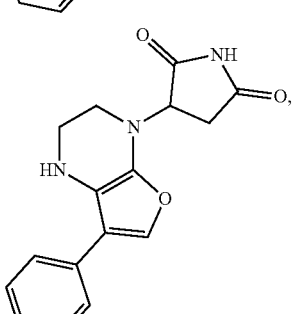
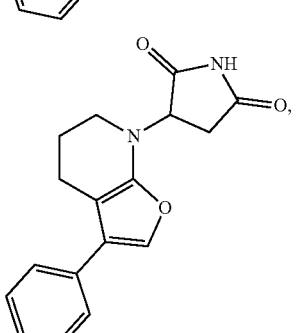
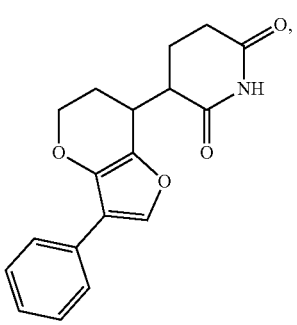

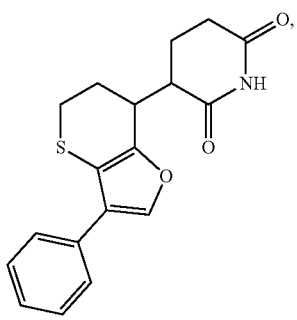
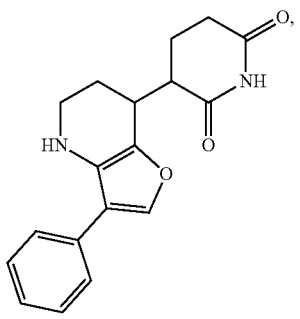
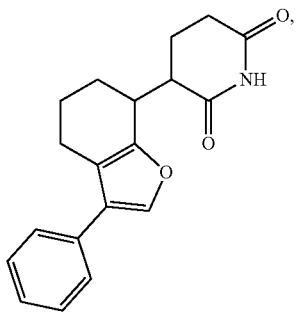
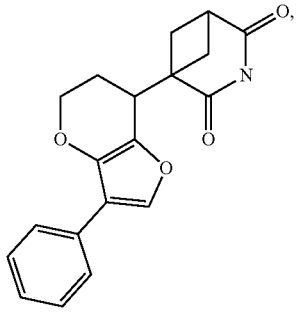
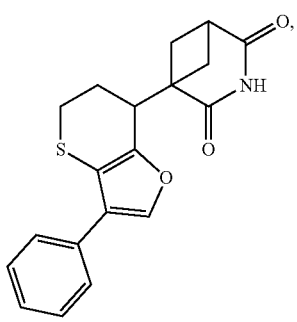
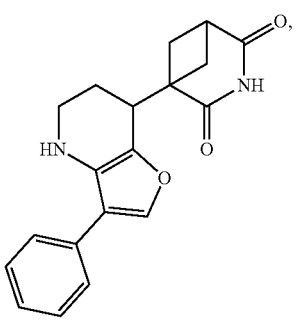
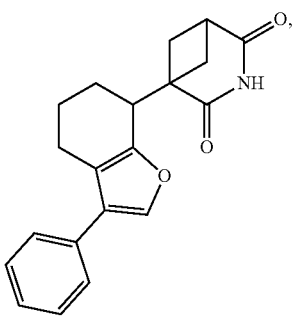
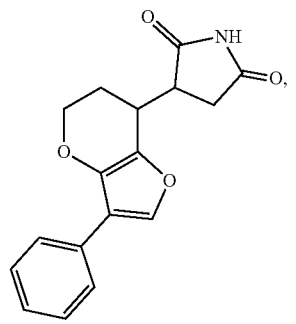
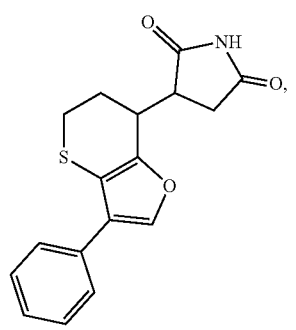
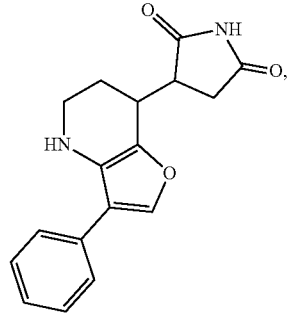

201
-continued
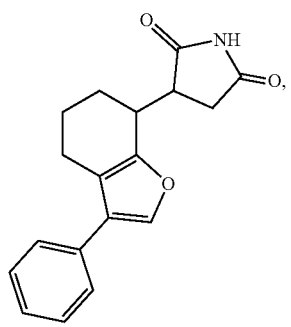
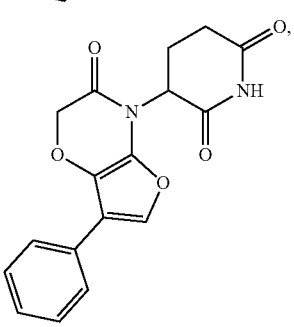
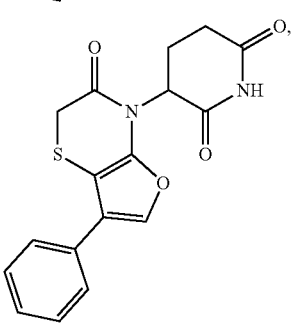
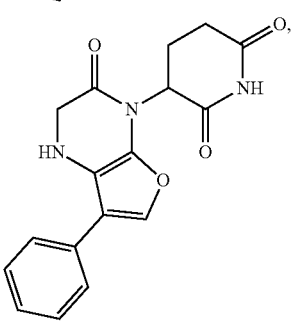
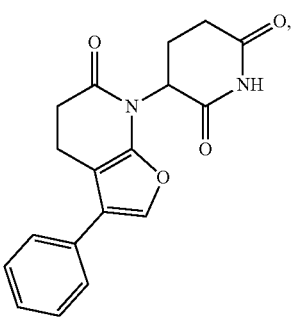
202
-continued
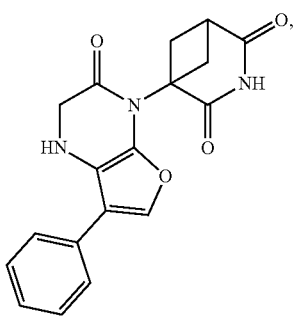
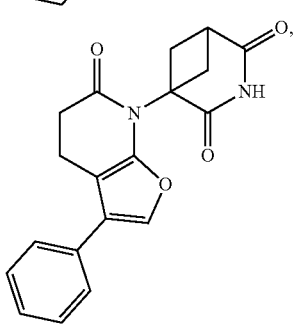
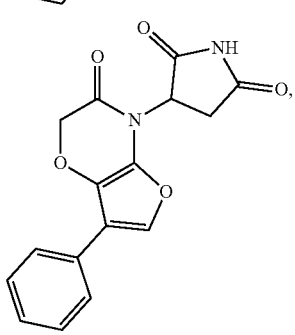
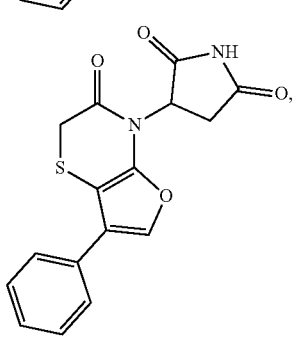
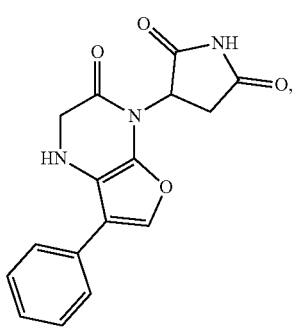

203
-continued

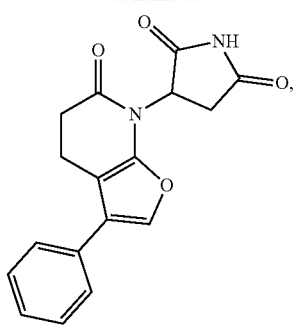

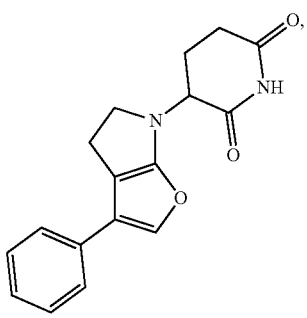

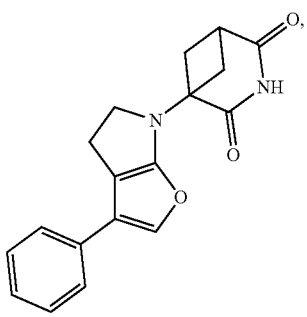

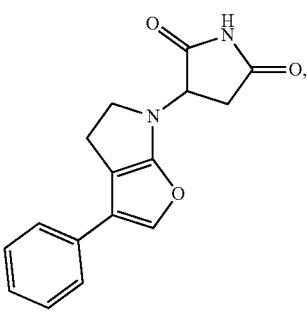

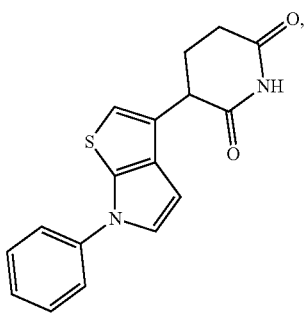

204
-continued

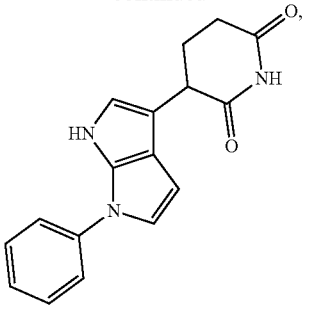

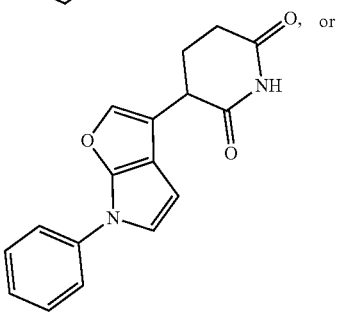

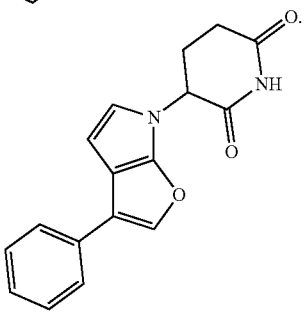

III. Linkers

A Linker is included in the Degrader compounds. Linker is a bond or a chemically stable bivalent group that attaches a Degron to a Targeting Ligand. In some embodiments, Linker can have a closed valence, and thus will contain one or more covalent bonds to ensure a complete valence, which may be to one or more hydrogen atoms, or in the case of carboxyl, sulfonyl, thiol, thiophenol, alcohol, or phenol groups can also be the deprotonated species and salts thereof, and for amines can also be the ammonium species and salts thereof.

Linker as described herein can be used in either direction, i.e., either the left end is linked to the Degron and the right end to the Target Linker, or the left end is linked to the Target Linker and the right end is linked to the Degron. In some embodiments, Linker is a bivalent chemical group. According to the invention, any desired linker can be used as long as the resulting compound has a stable shelf life for at least 2 months, 3 months, 6 months or 1 year as part of a pharmaceutically acceptable dosage form, and itself is pharmaceutically acceptable.

In a typical embodiment, the Linker has a chain of 2 to 14, 15, 16, 17, 18 or 20 or more carbon atoms of which one or more carbons can be replaced by a heteroatom such as O, N, S, or P. In certain embodiments the chain has 2, 3, 4, 5, 6, 7, 8, 9, 10, 11, 12, 13, 14, 15, 16, 17, 18, 19 or 20 contiguous atoms in the chain. For example, the chain may include 1 or more ethylene glycol units that can be contiguous, partially contiguous or non-contiguous (for example, 2, 3, 4, 5, 6, 7, 8, 9, 10, 11 or 12 ethylene glycol units). In certain embodiments the chain has at least 1, 2, 3, 4, 5, 6, 7, or 8 contiguous chains which can have branches which can be independently alkyl, heteroalkyl, aryl, heteroaryl, alkenyl, or alkynyl, aliphatic, heteroaliphatic, cycloalkyl or heterocyclic substituents.

In other embodiments, the linker can include or be comprised of one or more of ethylene glycol, propylene glycol, lactic acid and/or glycolic acid. In general, propylene glycol adds hydrophobicity, while propylene glycol adds hydrophilicity. Lactic acid segments tend to have a longer half-life than glycolic acid segments. Block and random lactic acid-co-glycolic acid moieties, as well as ethylene glycol and propylene glycol, are known in the art to be pharmaceutically acceptable and can be modified or arranged to obtain the desired half-life and hydrophilicity. In certain aspects, these units can be flanked or interspersed with other moieties, such as aliphatic, including alkyl, heteroaliphatic, aryl, heteroaryl, heterocyclic, cycloalkyl, etc., as desired to achieve the appropriate drug properties.

In some embodiments, Linker is a moiety selected from Formula LI, Formula LII, Formula LIII, Formula LIV, Formula LV, Formula LVI, and Formula LVII:

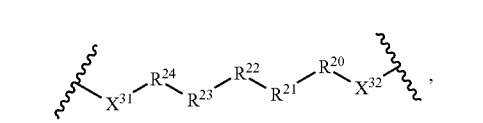
(LI)

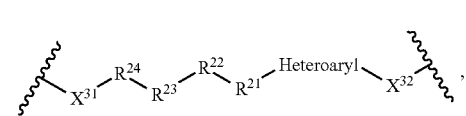
(LII)

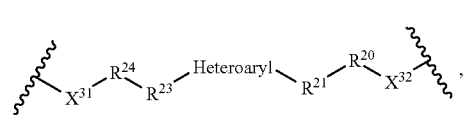
(LIII)

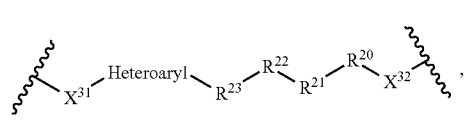
(LIV)

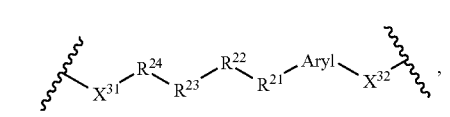
(LV)

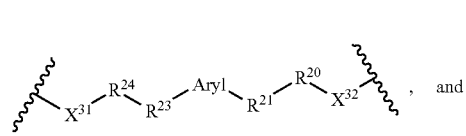
(LVI), and

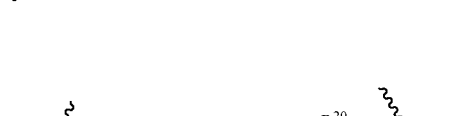
(LVII)

wherein all variables are defined as above.

In other embodiments, the Linker is a moiety selected from Formula LVIII, LIX, and LX:

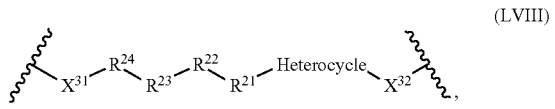
(LVIII)

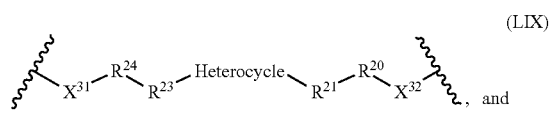
(LIX), and

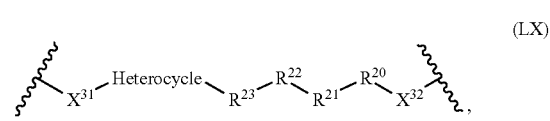
(LX)

wherein all variables are defined as above.

In other embodiments of LVIII, LIX and LX, a carbocyclic ring is used in place of the heterocycle.

The following are non-limiting examples of Linkers that can be used in this invention. Based on this elaboration, those of skill in the art will understand how to use the full breadth of Linkers that will accomplish the goal of the invention.

As certain non-limiting examples, Formula LI, Formula LII, Formula LIII, Formula LIV, Formula LV, Formula LVI, or Formula LVII include:

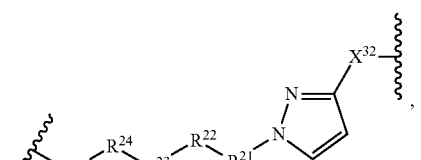

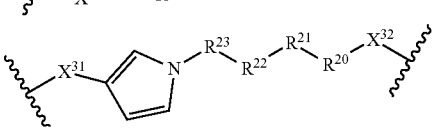

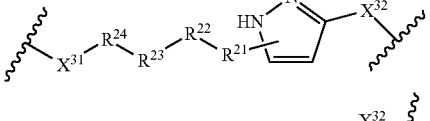

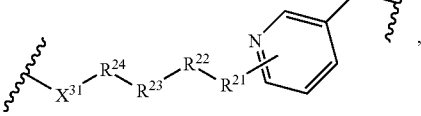

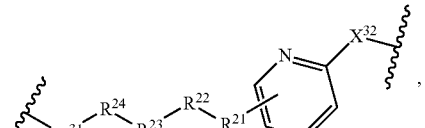

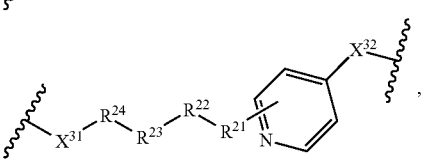

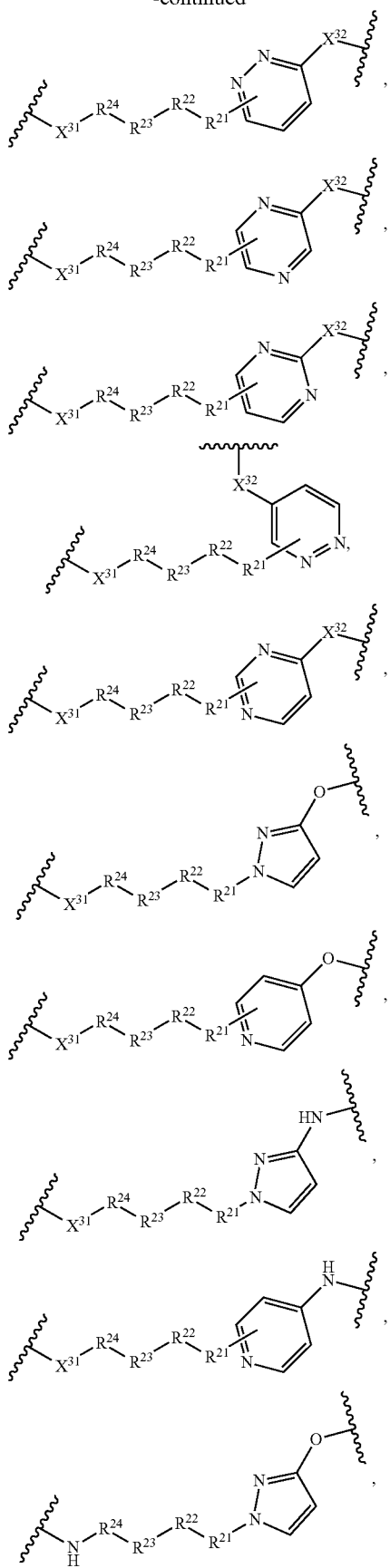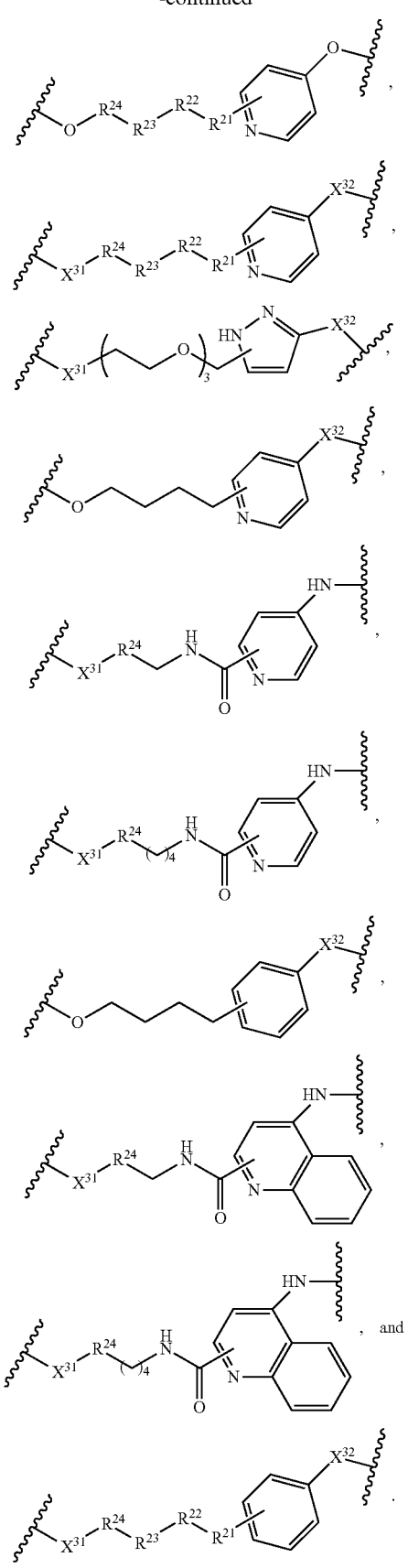

In an additional embodiment $R^{21}$, $R^{22}$, $R^{23}$, or $R^{24}$ is selected from:
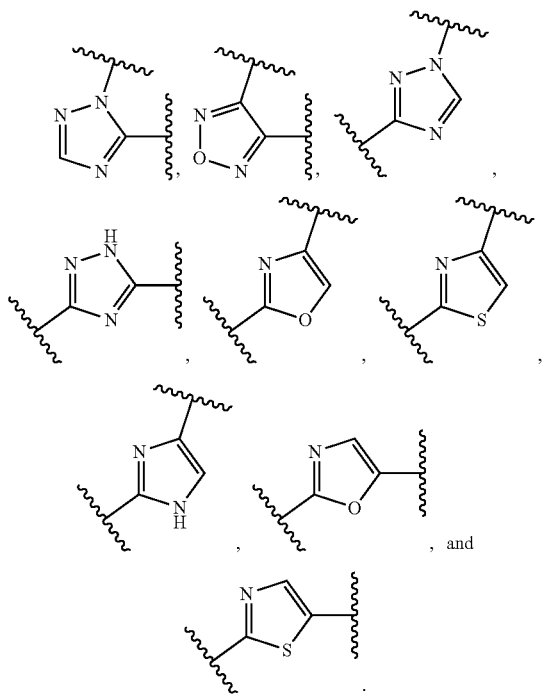
In an additional embodiment Linker is selected from:
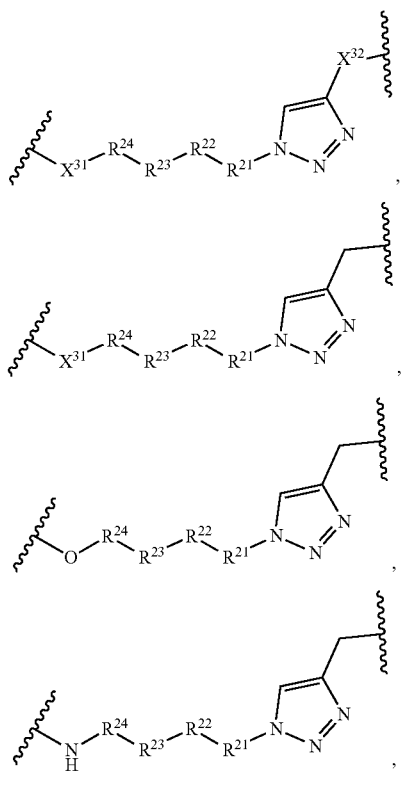
-continued
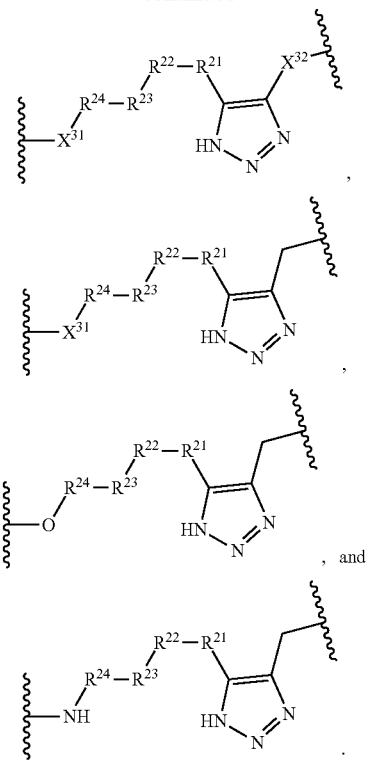
In one embodiment $X^1$ is attached to the Targeting Ligand. In another embodiment $X^2$ is attached to the Targeting Ligand.
Non-limiting examples of moieties of $R^{20}$, $R^{21}$, $R^{22}$, $R^{23}$, and $R^{24}$ include:
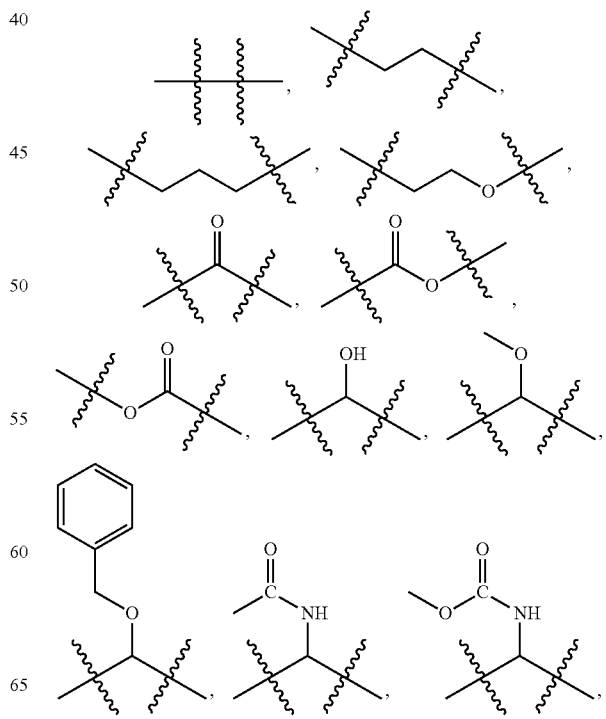

-continued
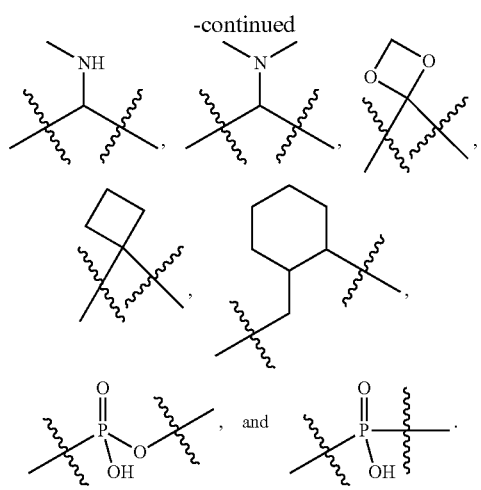
Additional non-limiting examples of moieties of $R^{20}$, $R^{21}$, $R^{22}$, $R^{23}$, and $R^{24}$ include:
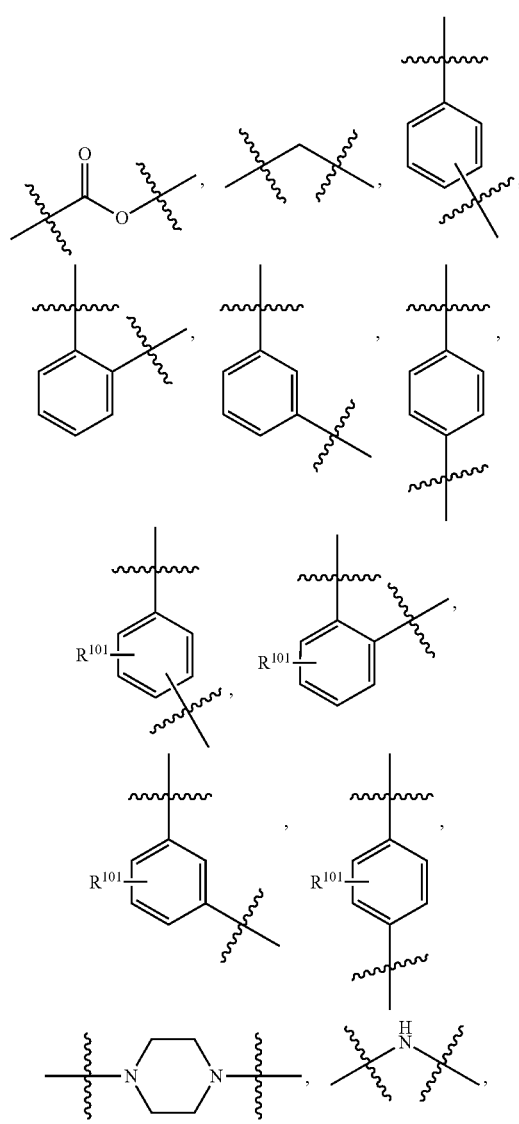
-continued
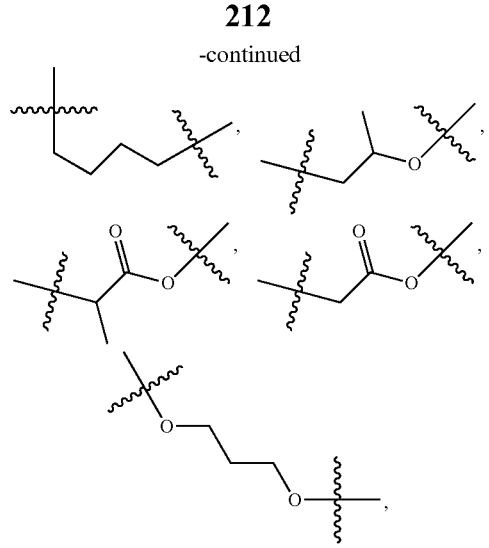
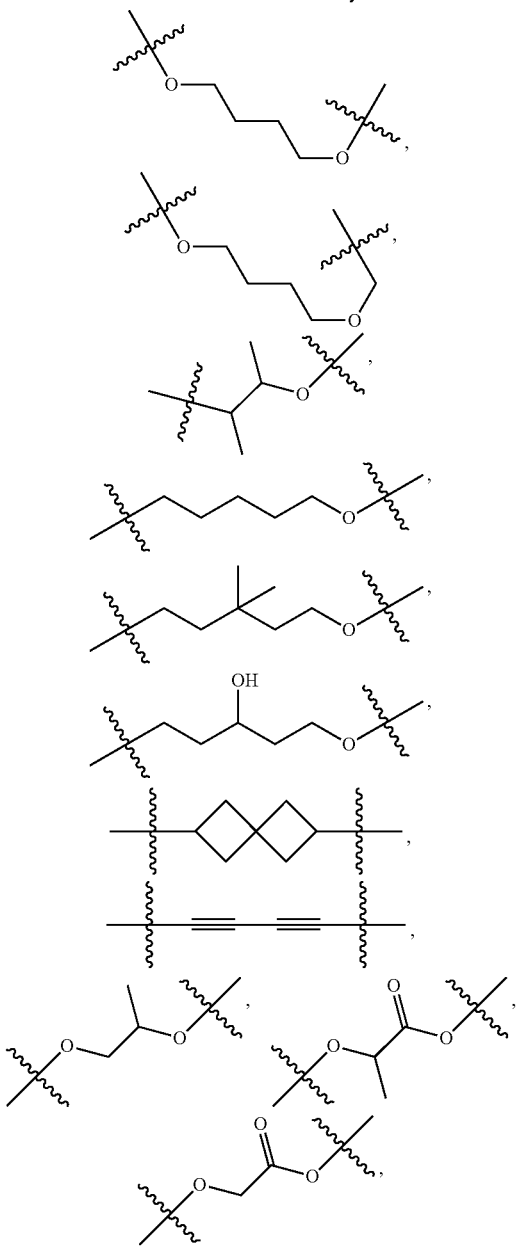

-continued

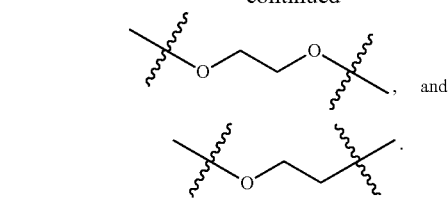

Additional non-limiting examples of moieties of $R^{20}$, $R^{21}$, $R^{22}$, $R^{23}$, and $R^{24}$ include:

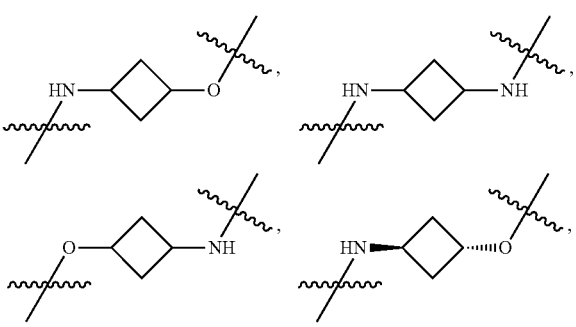

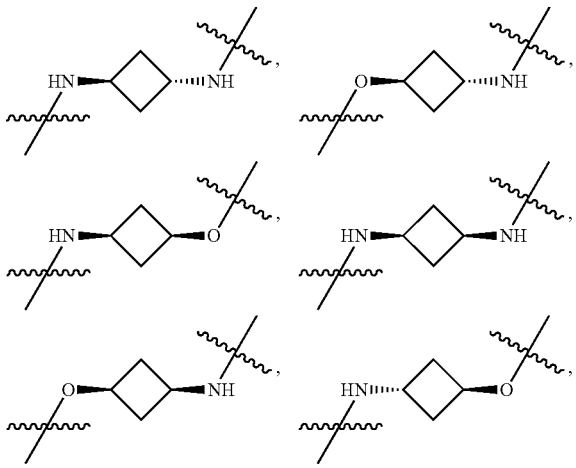

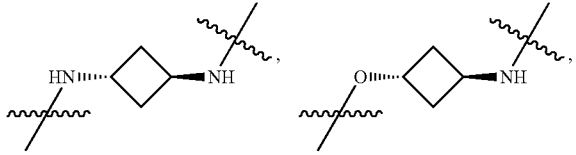

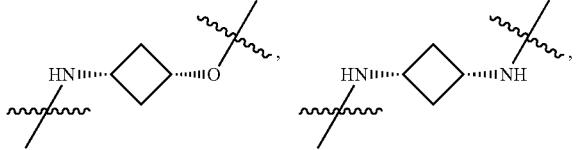

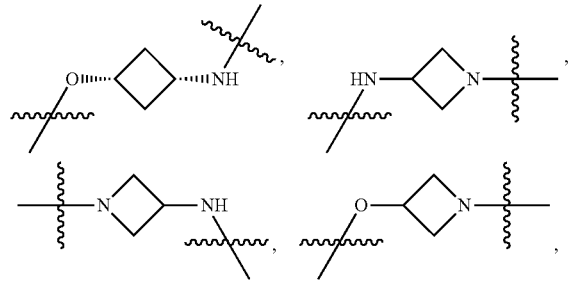

-continued

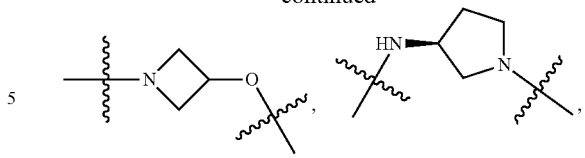

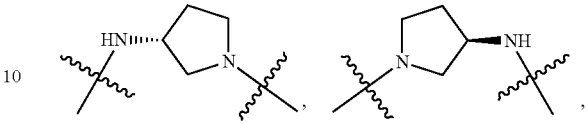

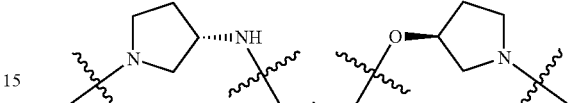

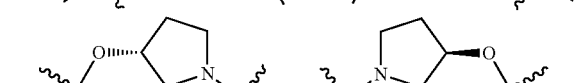

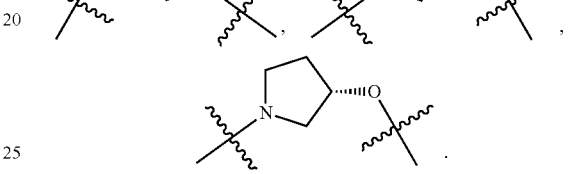

In additional embodiments, the Linker moiety is an (poly) ethylene glycol having at least 1, at least 2, at least 3, at least 4, at least 5, at least 6, at least 7, at least 8, at least 9, at least 10, ethylene glycol units, or alkyl groups interspersed with O, N, S, P or Si atoms. In certain embodiments, Linker is flanked, substituted, or interspersed with an aryl, phenyl, benzyl, alkyl, alkylene, or heterocycle group. In certain embodiments, Linker may be asymmetric or symmetrical.

In some embodiments, Linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units. In any of the embodiments of the compounds described herein, Linker group may be any suitable moiety as described herein.

In additional embodiments, Linker is selected from the group consisting of:

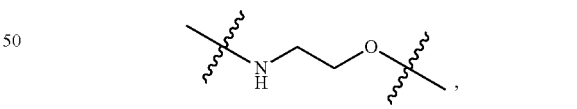

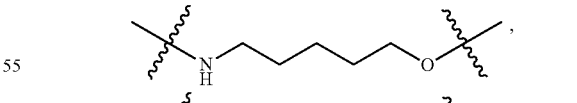

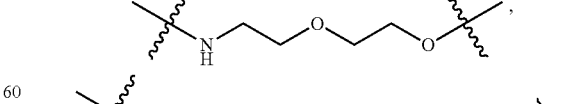

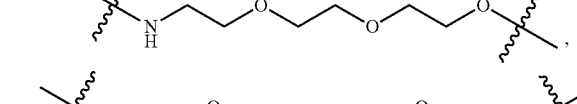

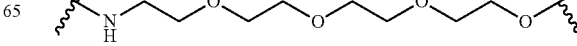

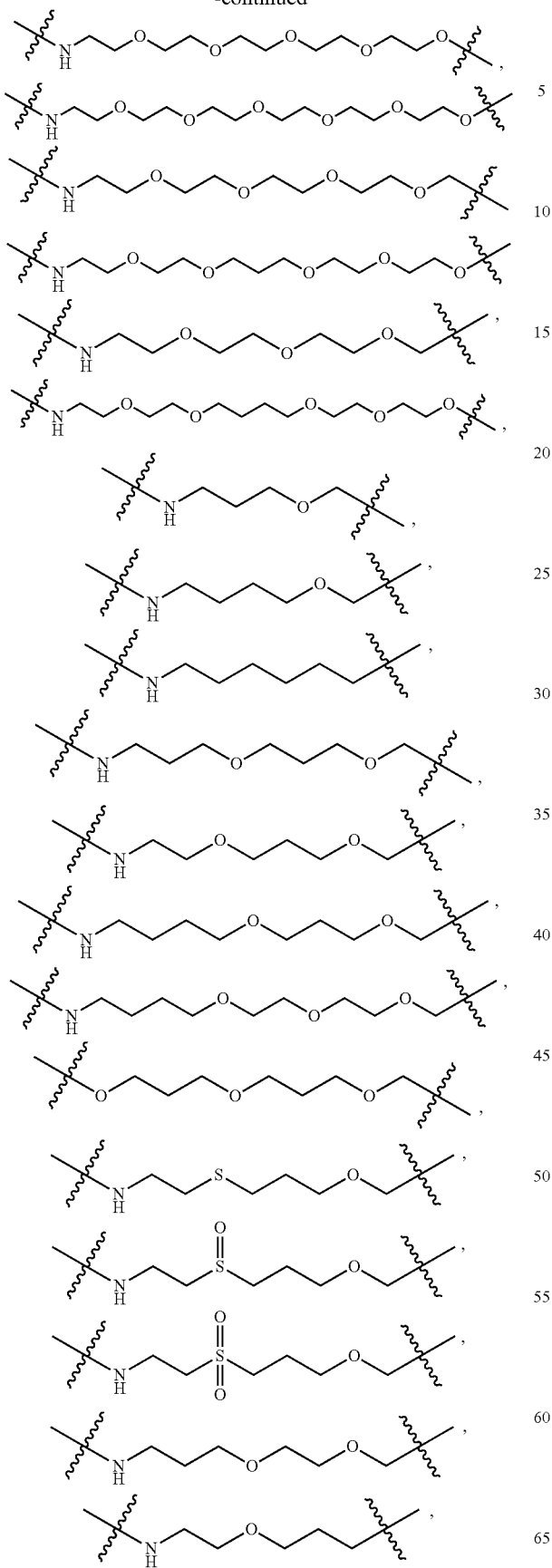
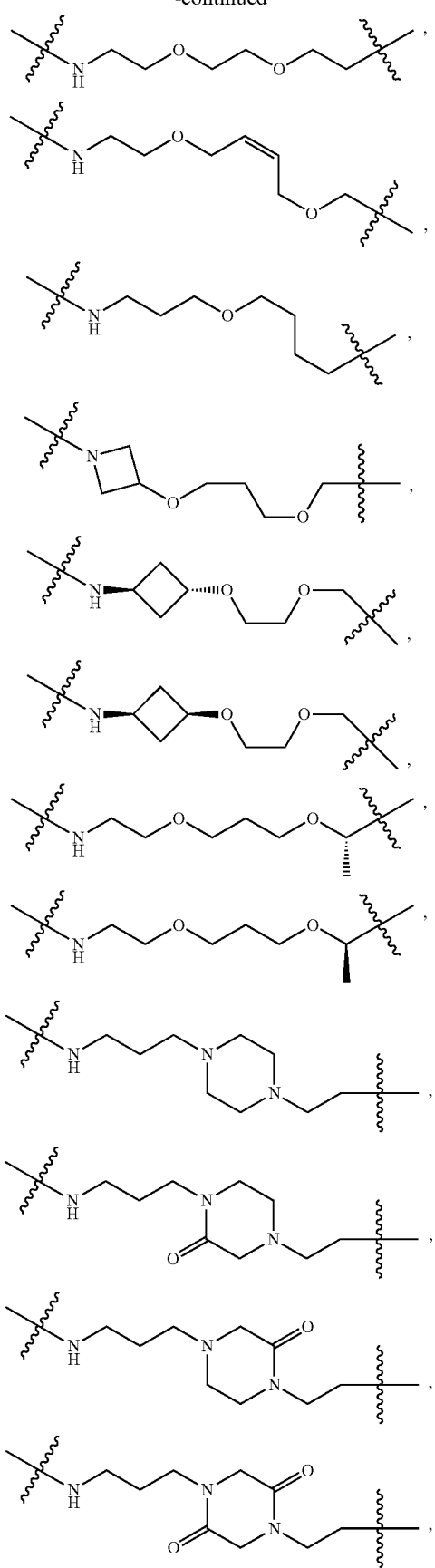

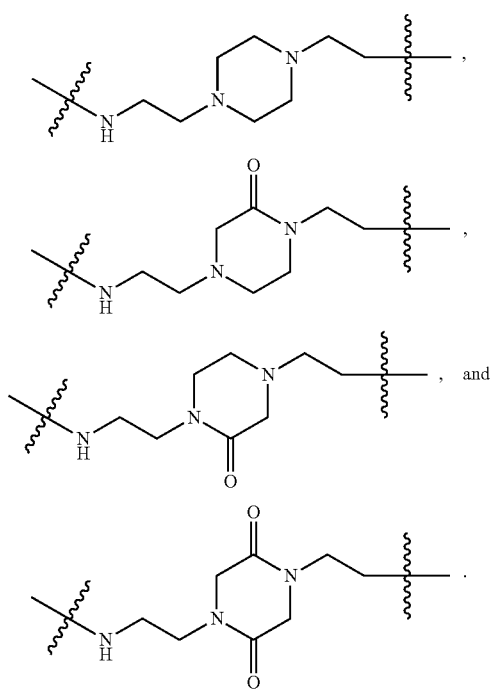
In additional embodiments, Linker is selected from the group consisting of:
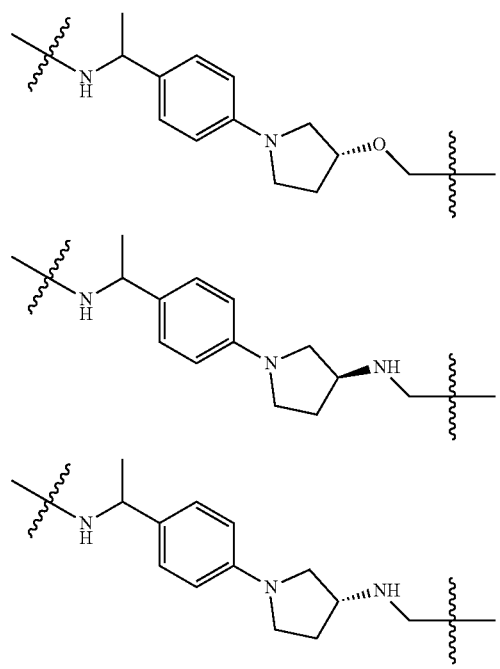
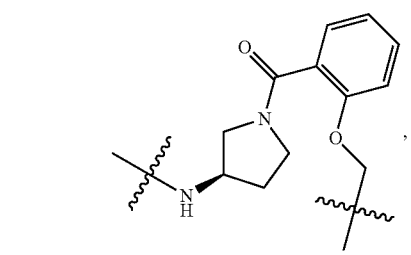
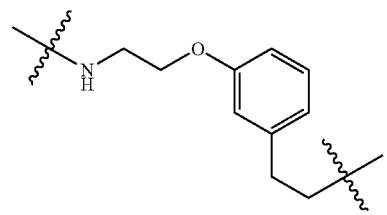
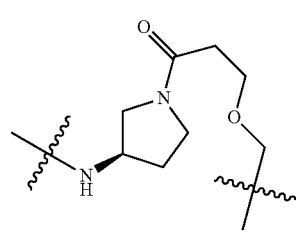
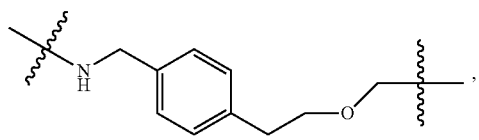
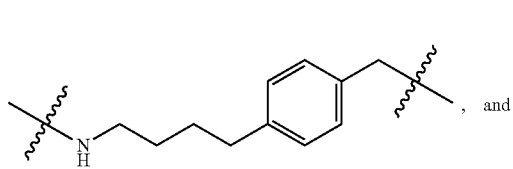

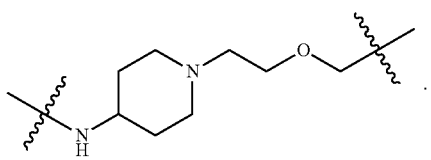
In additional embodiments, Linker is selected from the group consisting of:
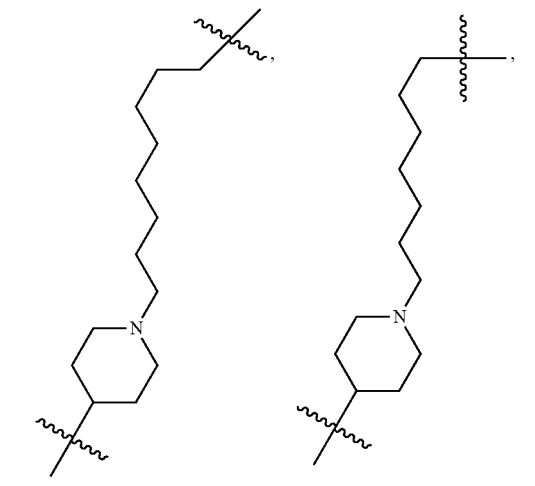
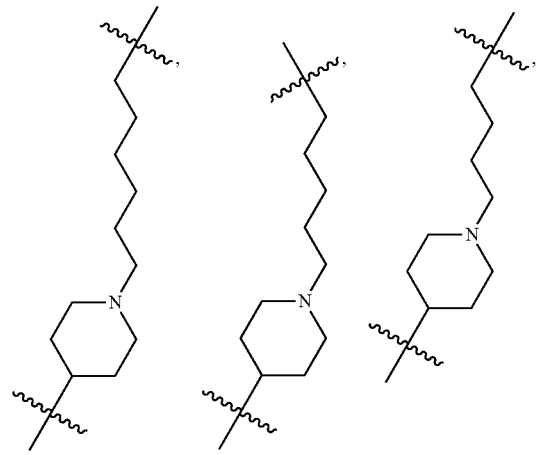
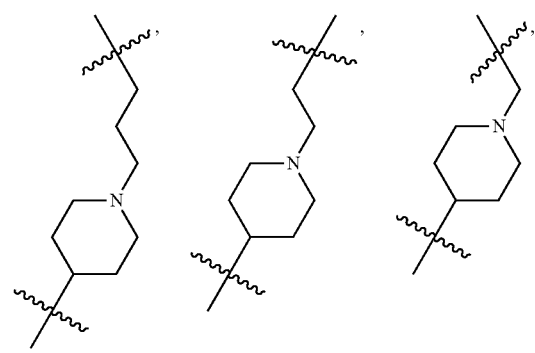
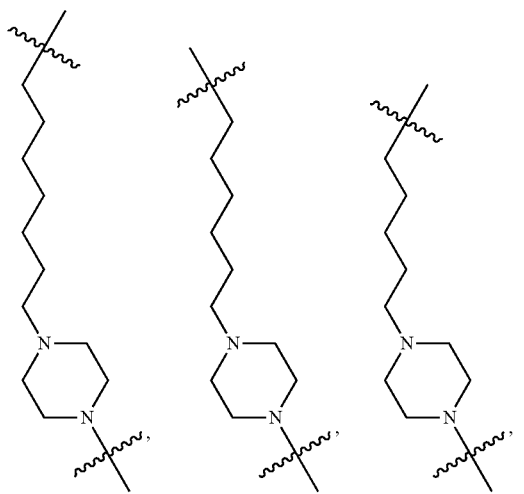
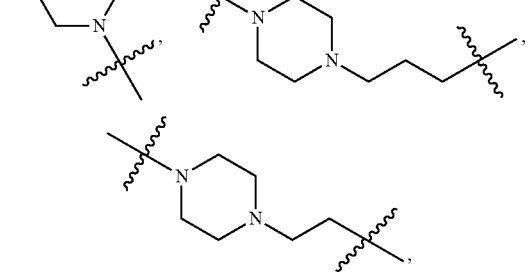
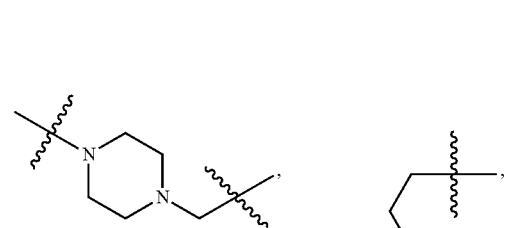
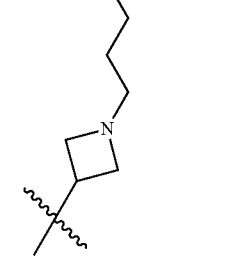

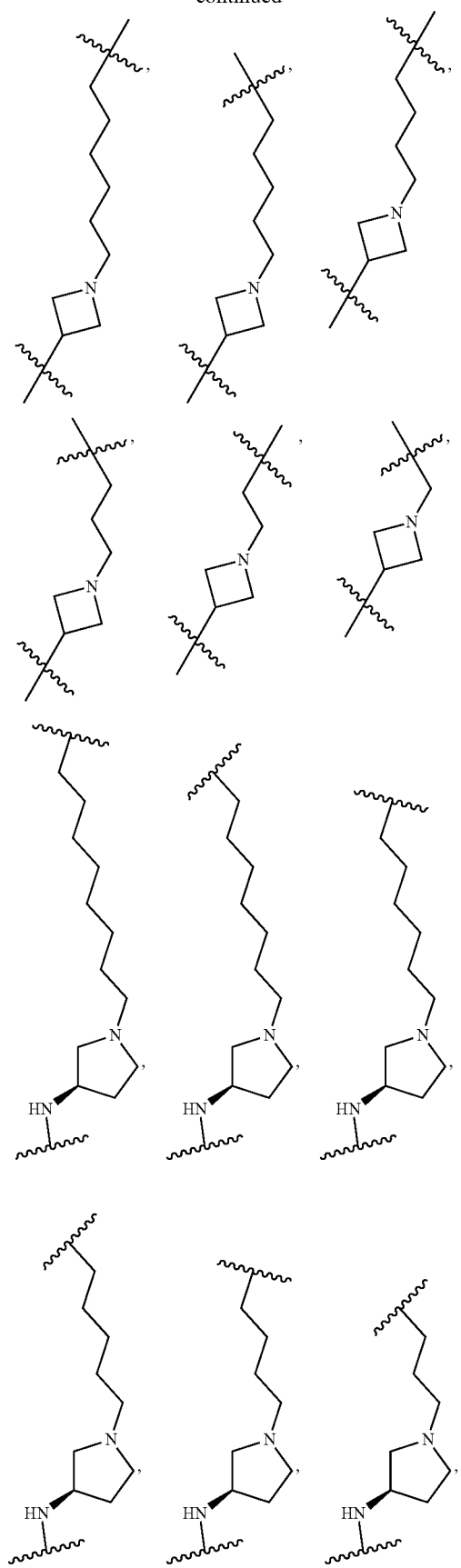
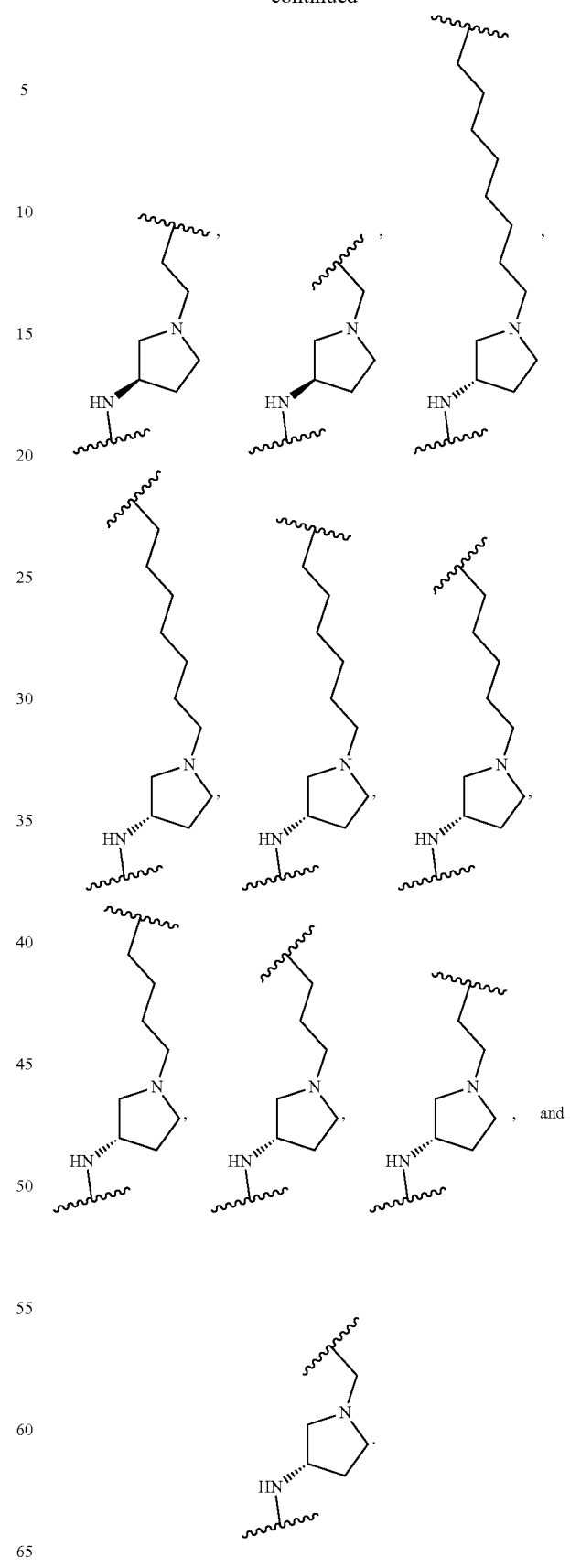

In additional embodiments, Linker is selected from the group consisting of:
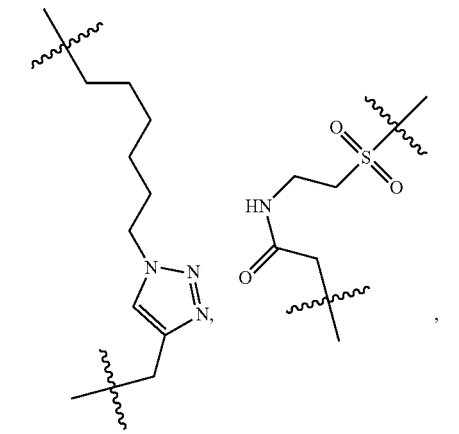
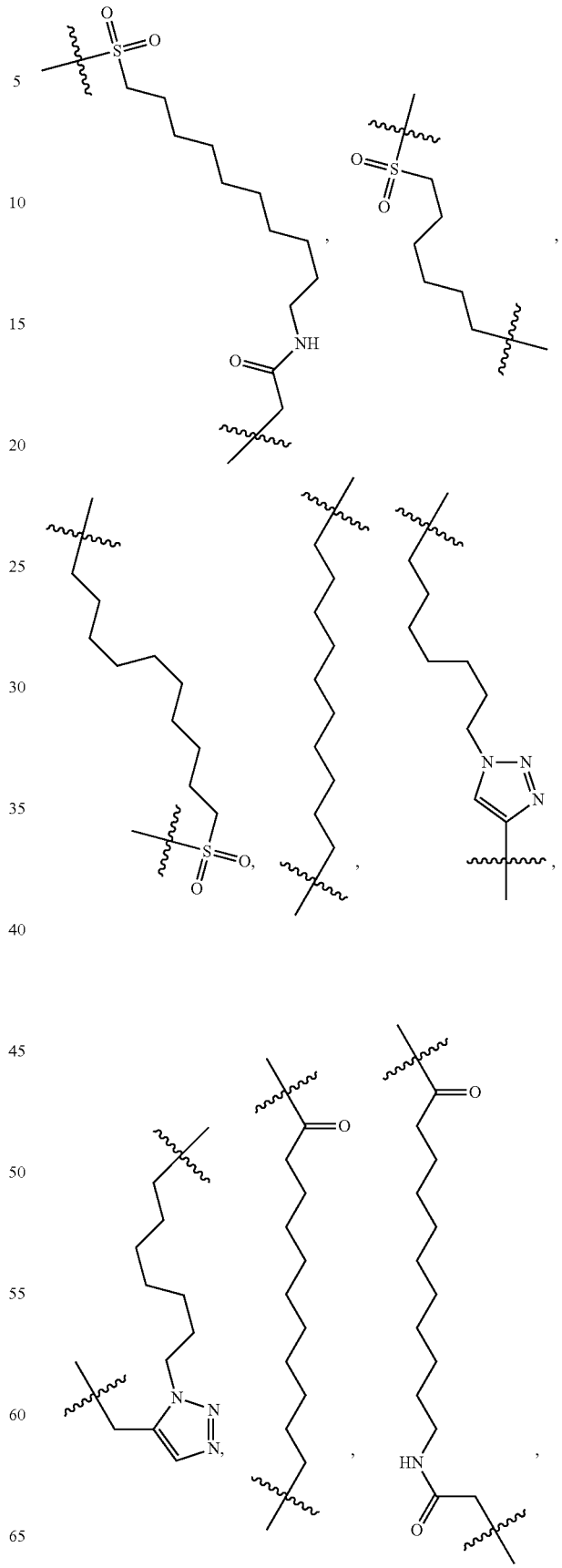

225
-continued
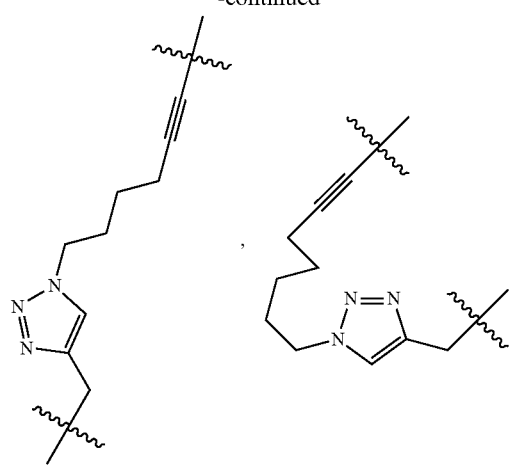
,
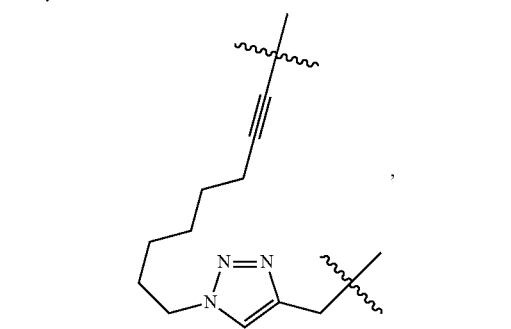
,
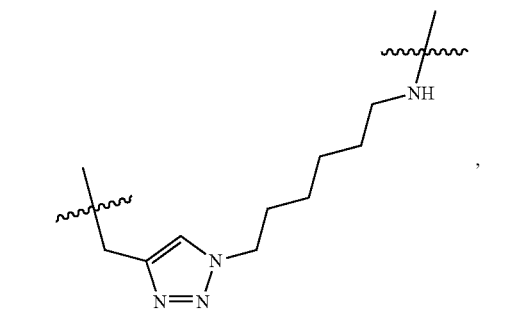
,
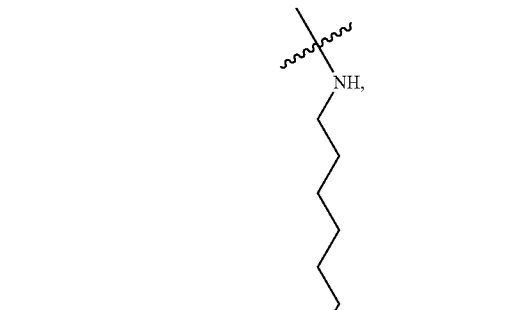
,
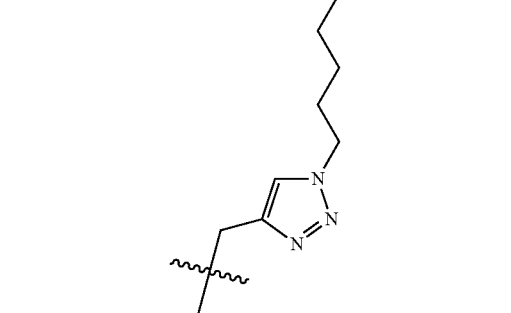
226
-continued
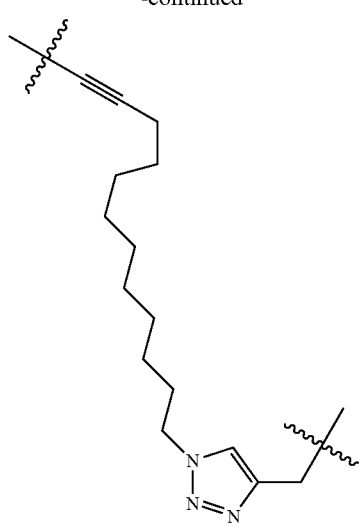
,
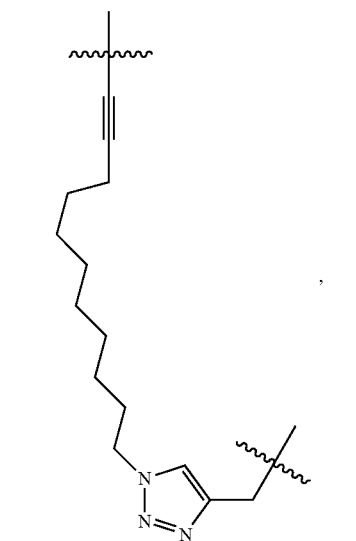
,
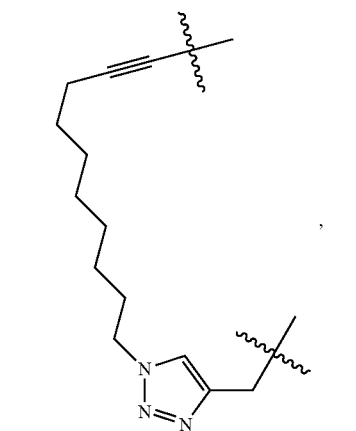
, 227
-continued
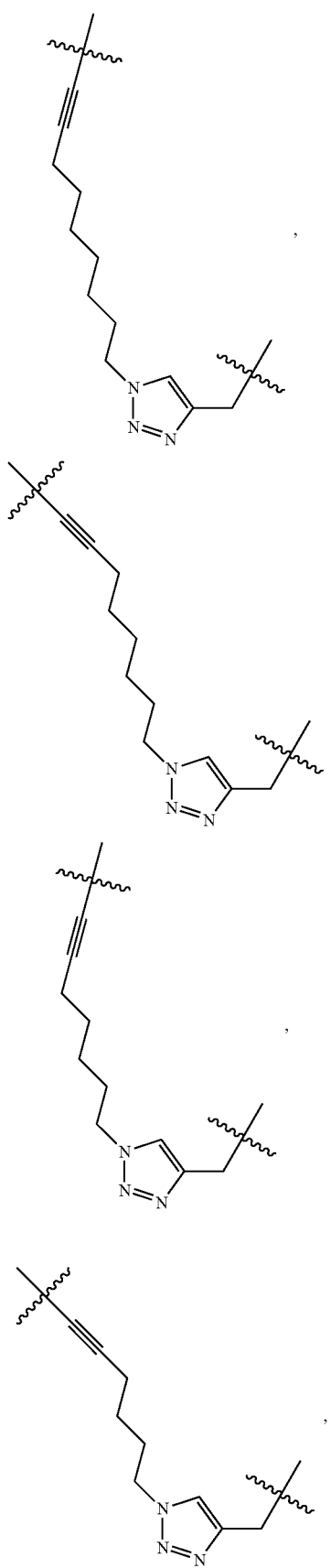
228
-continued
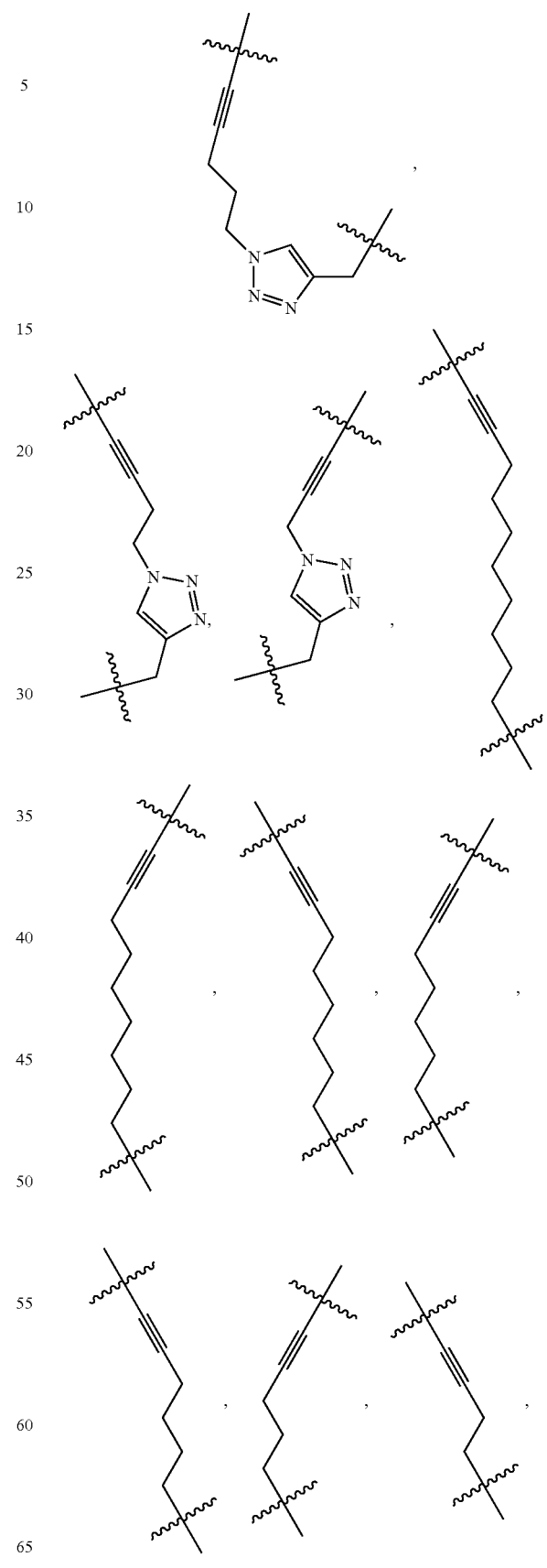

229
-continued
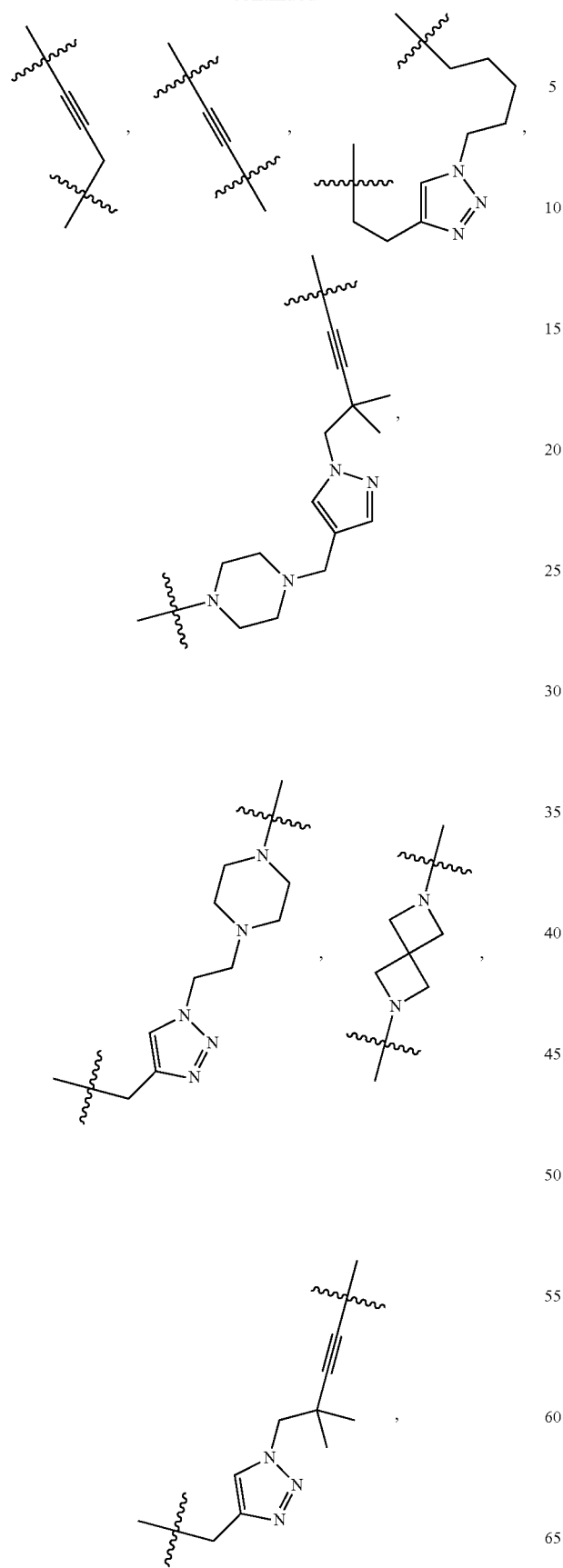
230
-continued
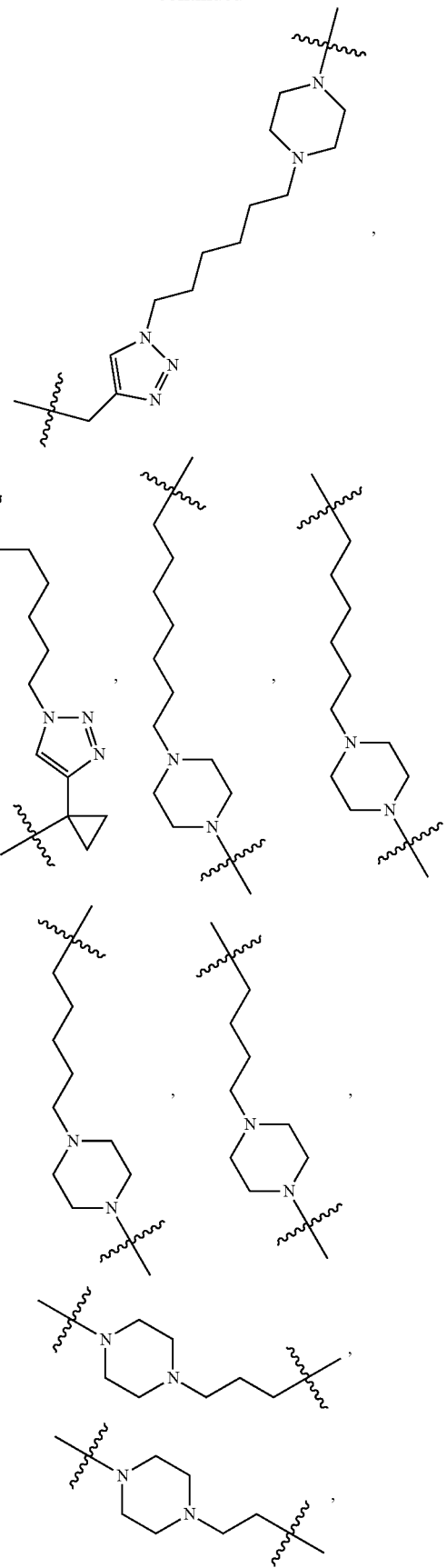

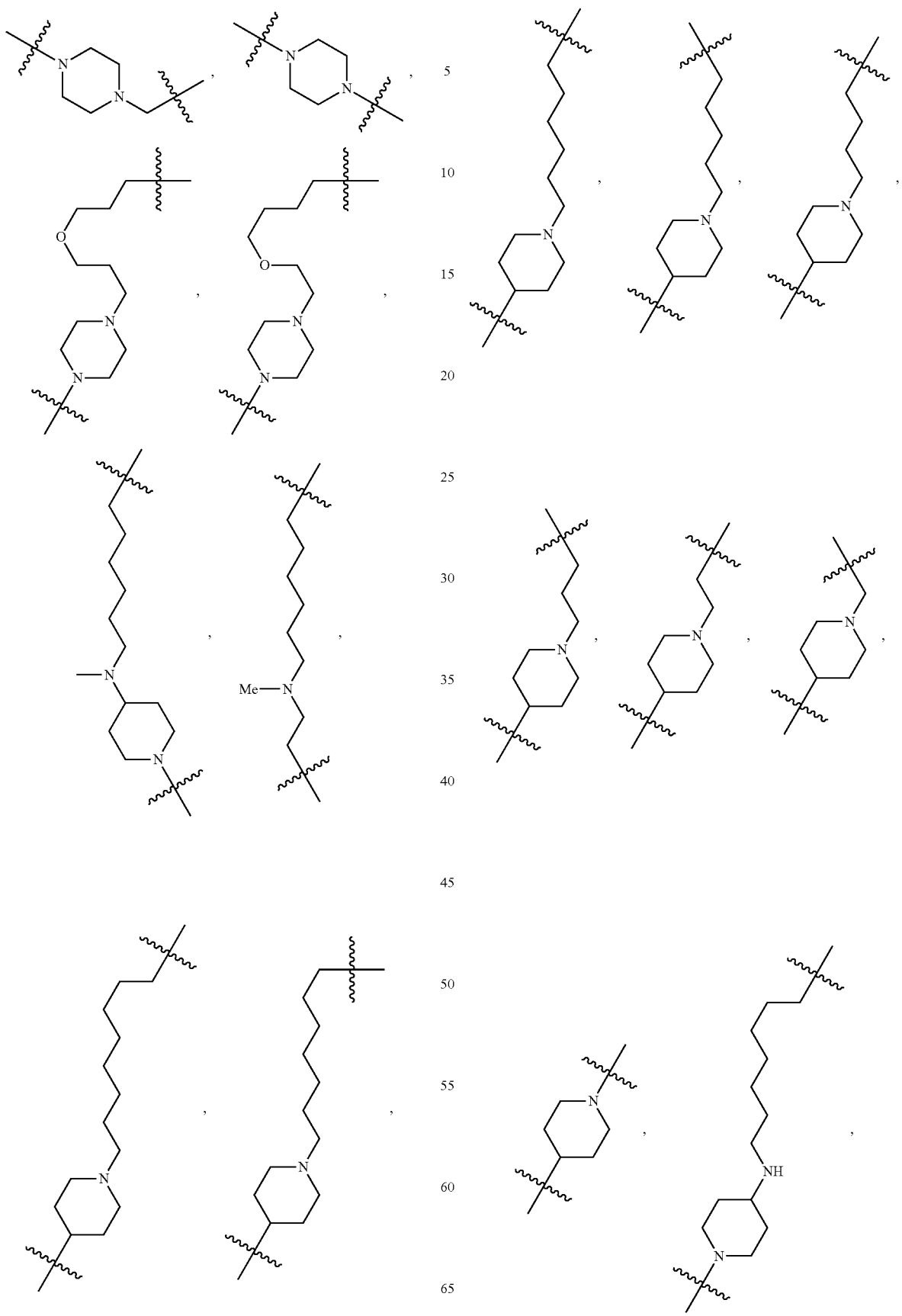

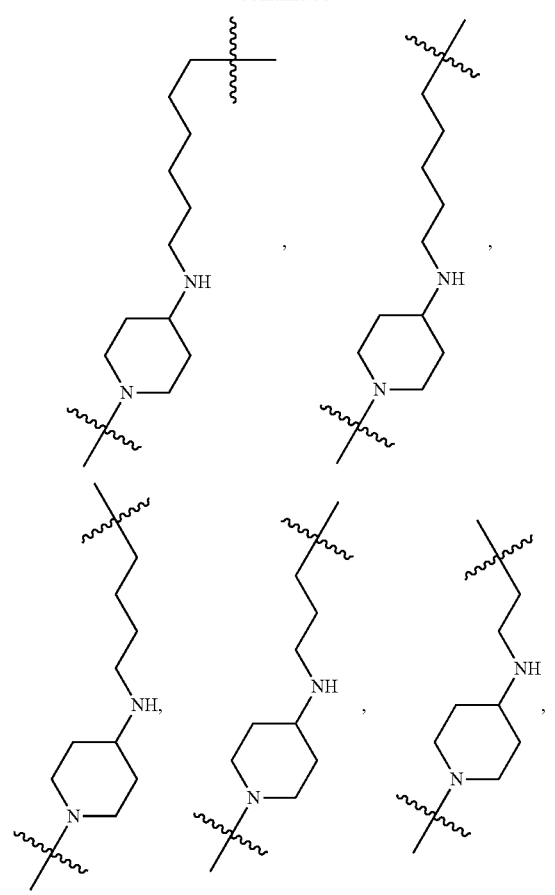
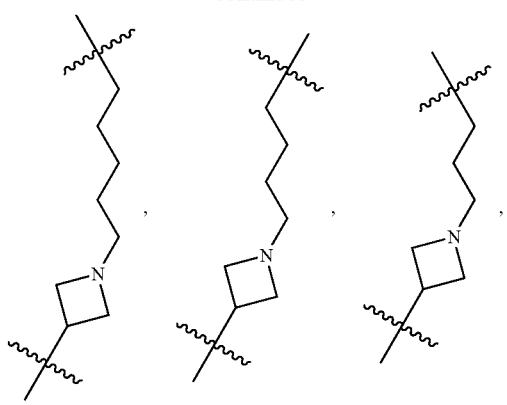
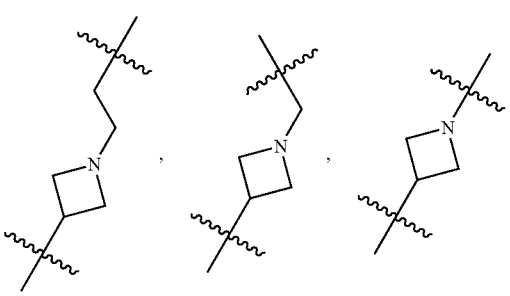
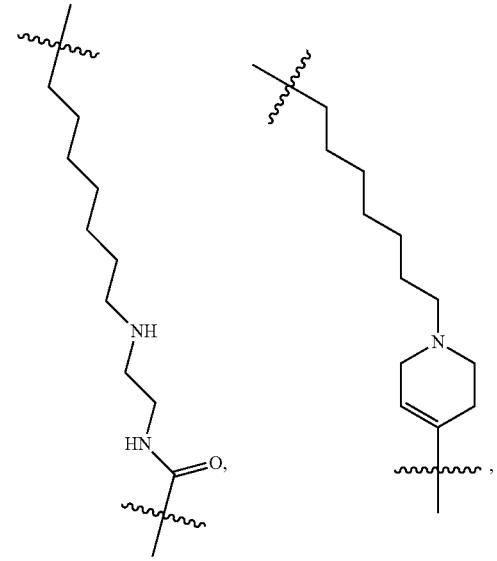
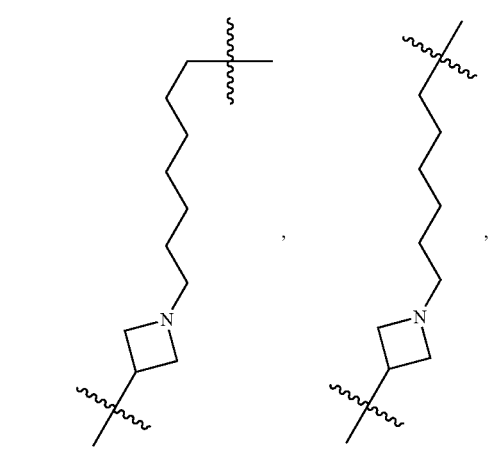

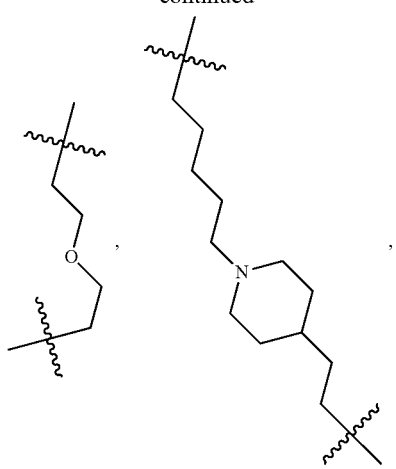
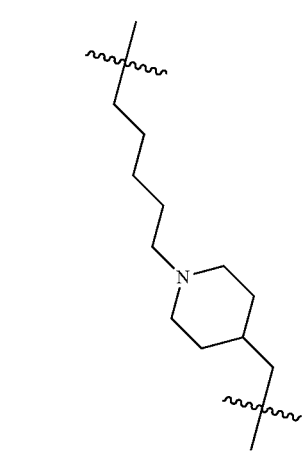
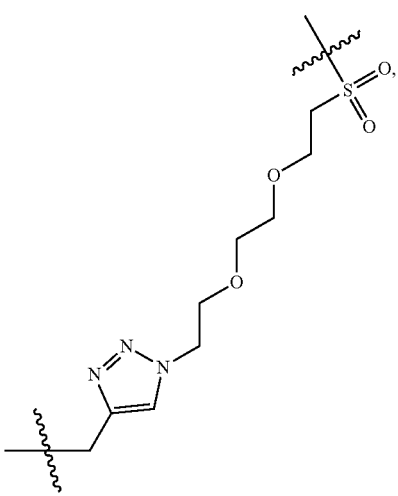
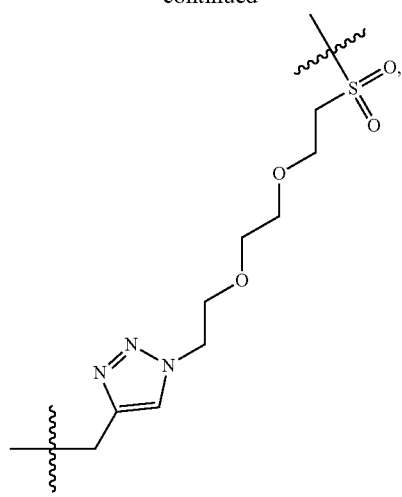
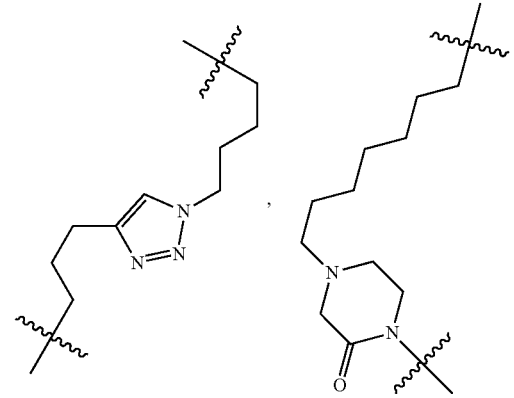
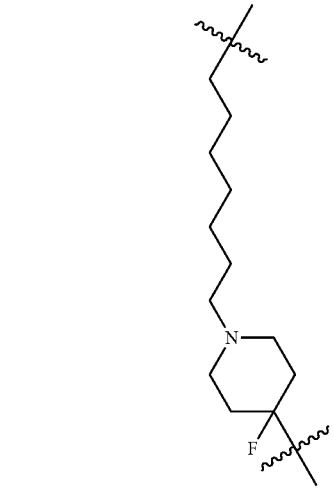
In additional embodiments, Linker is selected from the group consisting of:
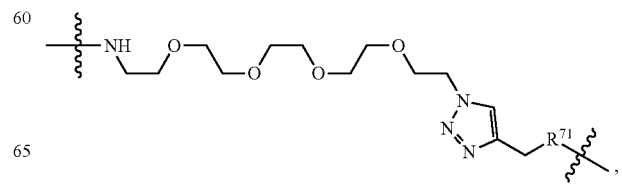

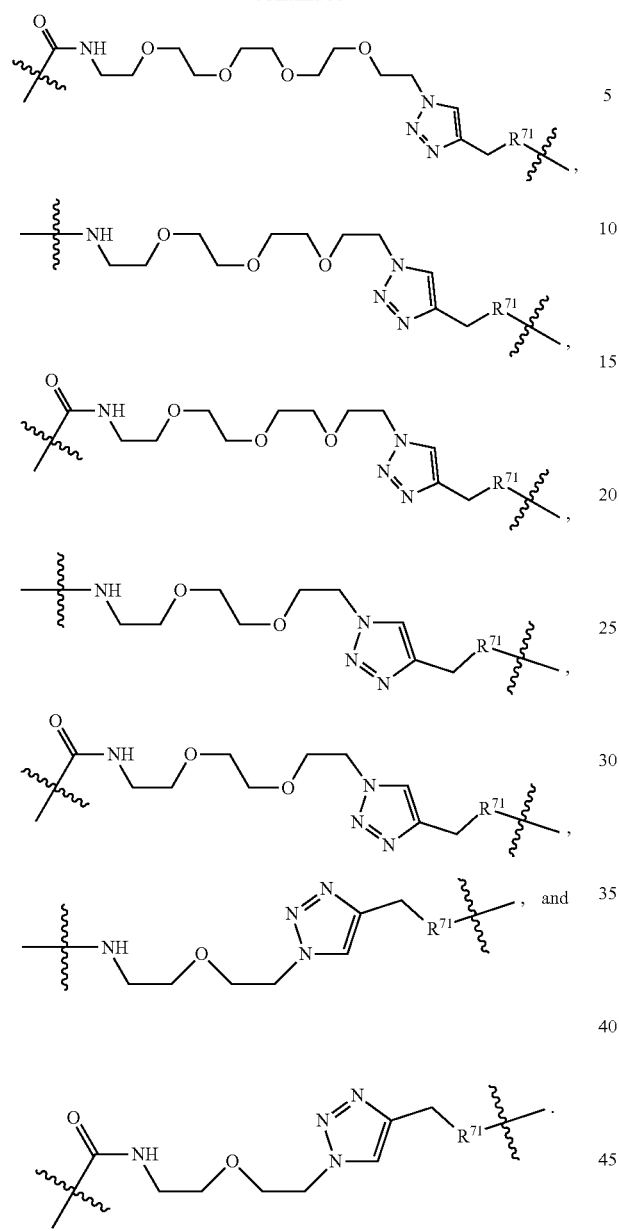
In additional embodiments, Linker is selected from the group consisting of:
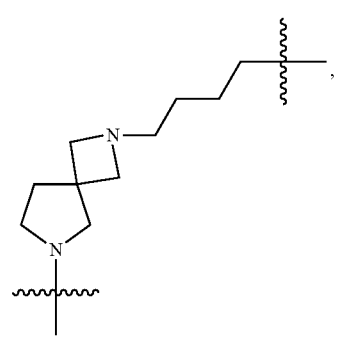
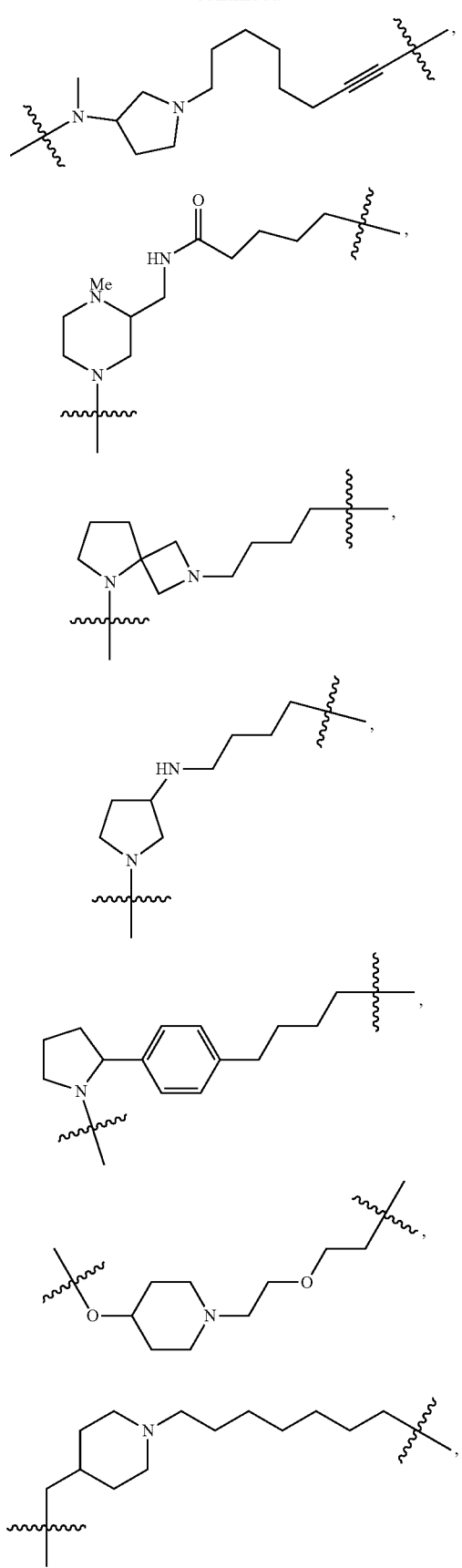

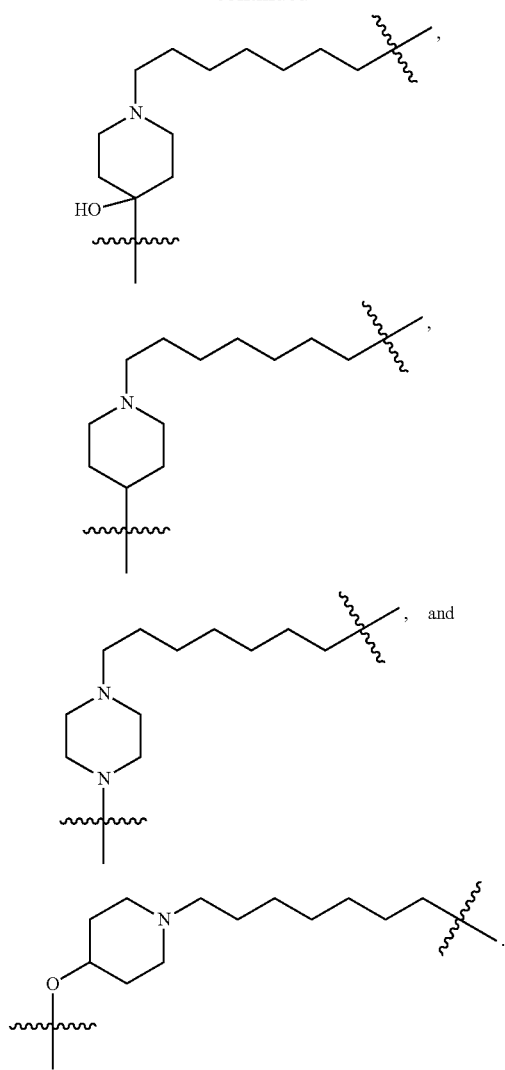
In additional embodiments, Linker is selected from the group consisting of:
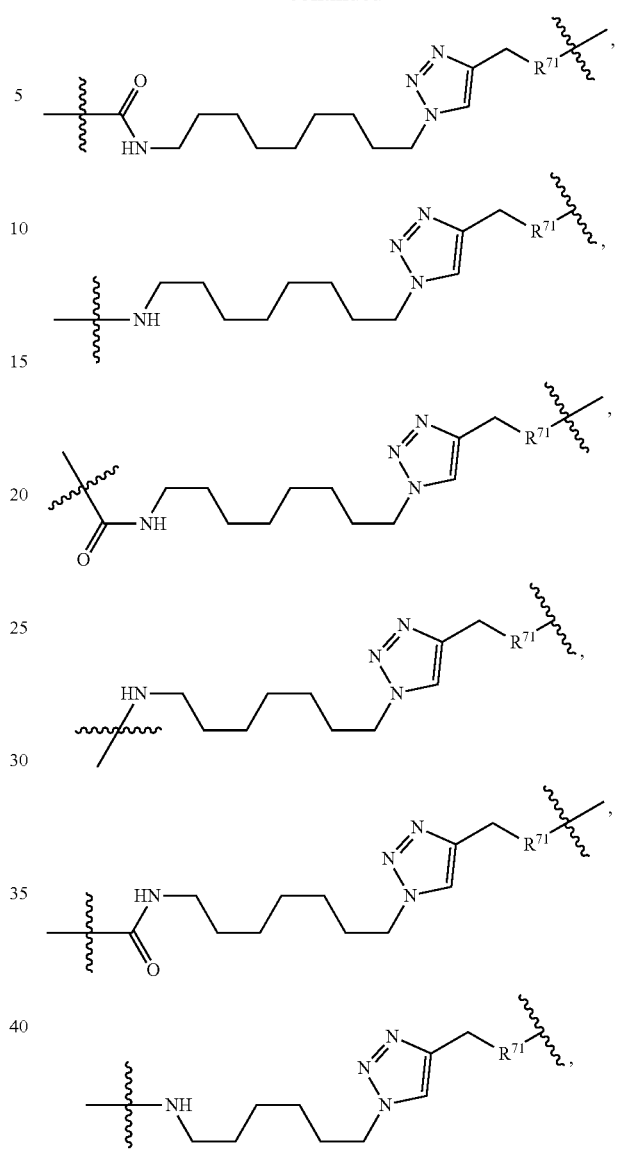

-continued
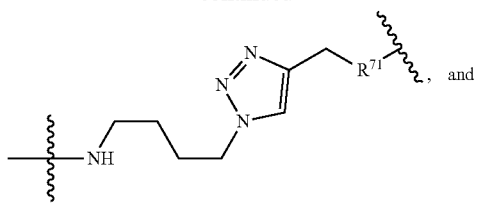, and
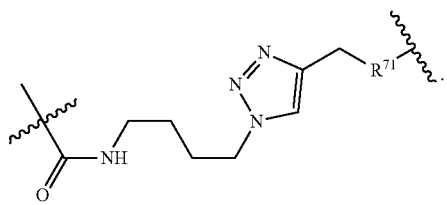.
In additional embodiments, Linker is selected from the group consisting of:
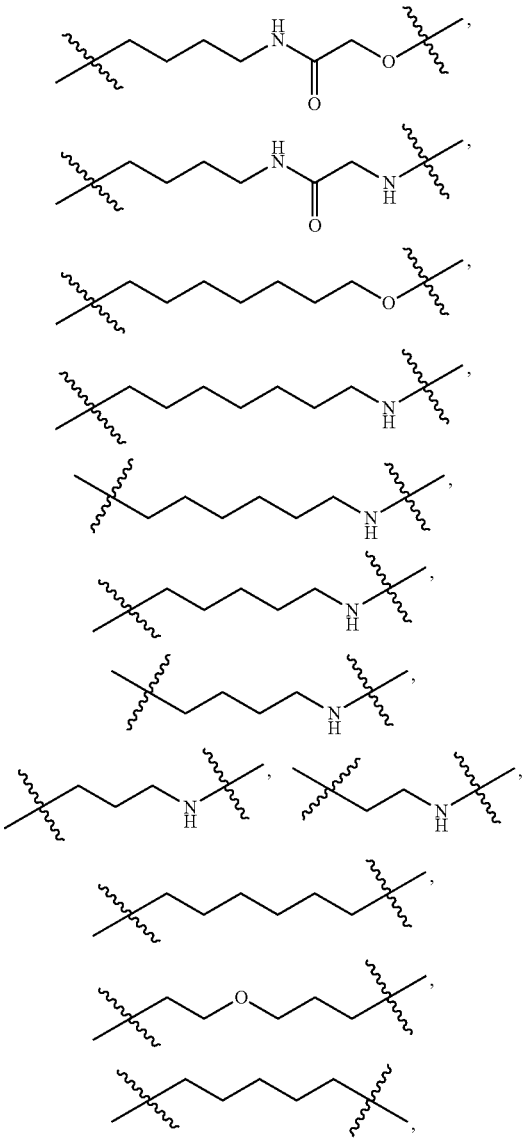
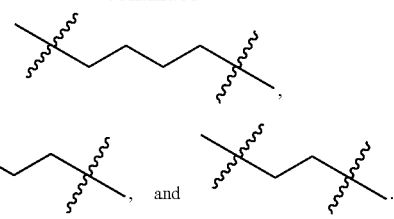, and 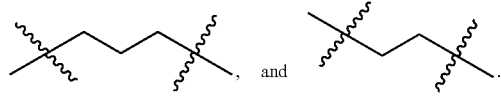.
In additional embodiments, Linker is selected from:
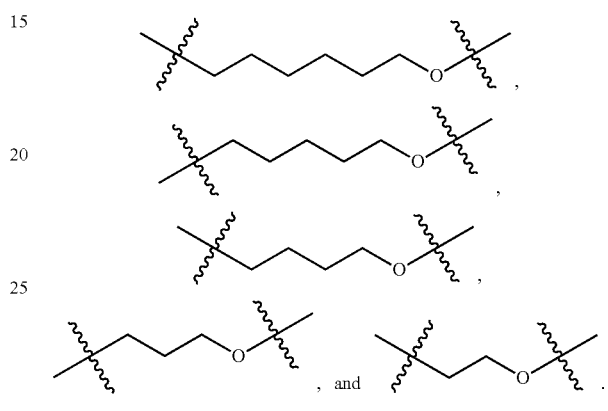
In certain embodiments, Linker is selected from the group consisting of:
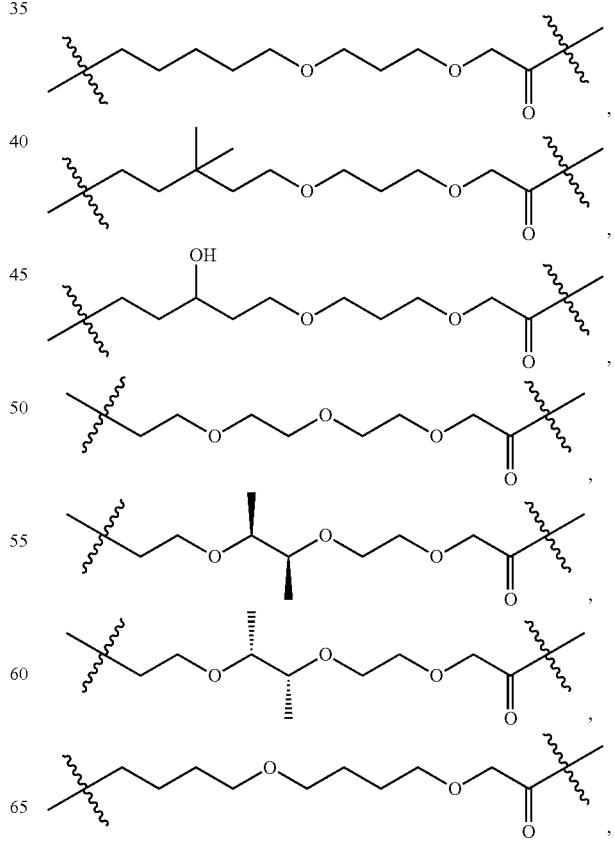

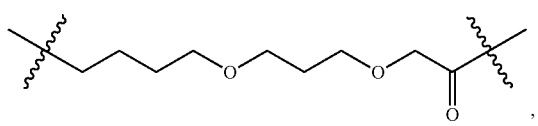
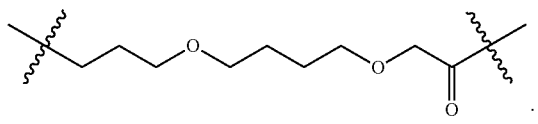
In certain embodiments Linker is selected from the group consisting of:
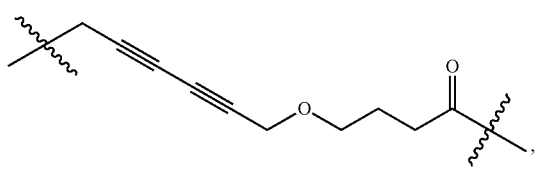
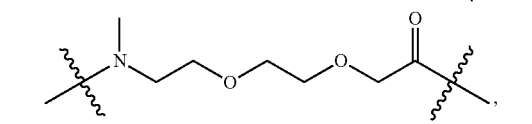
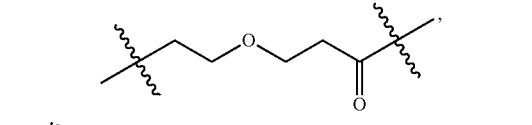
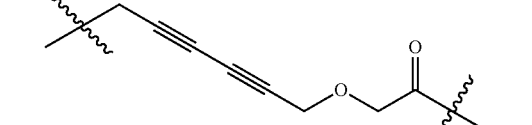
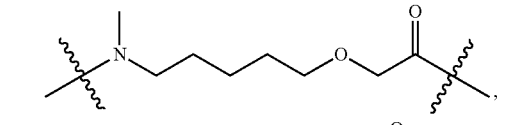
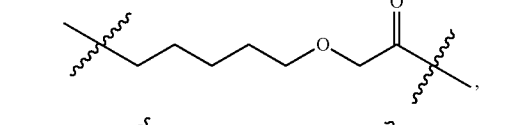
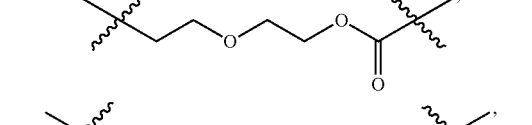
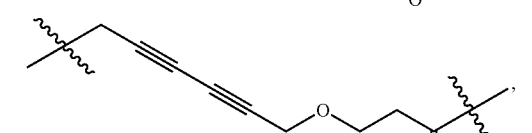
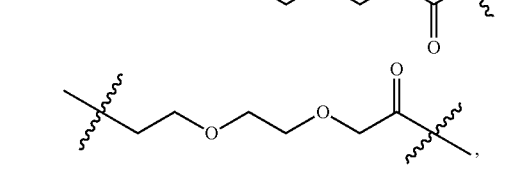
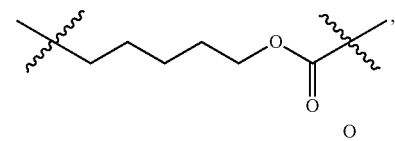
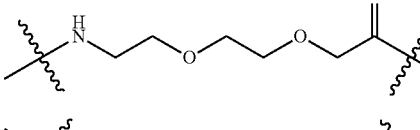
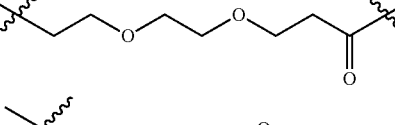
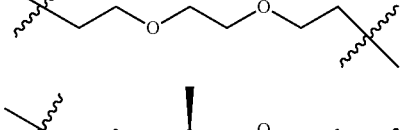
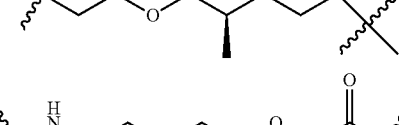
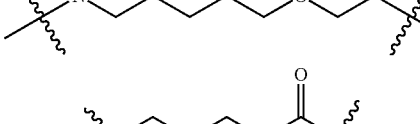
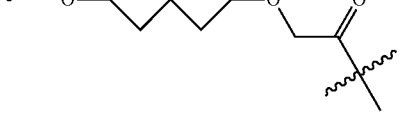
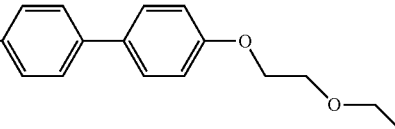
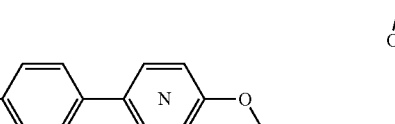
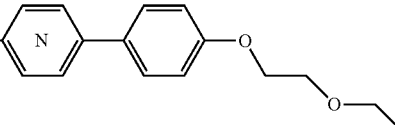
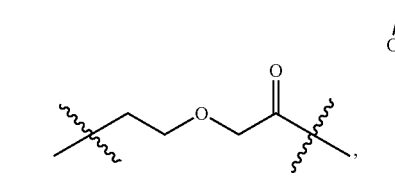

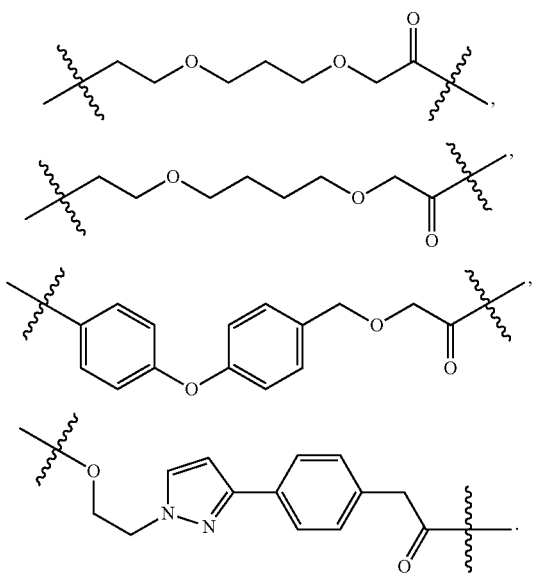
In the above structures
represents
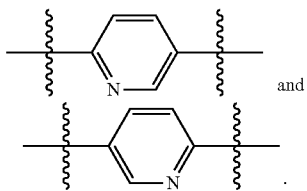
and
In certain embodiments, Linker can be a 4-24 carbon atom linear chain, wherein one or more the carbon atoms in the linear chain can be replaced or substituted with oxygen, nitrogen, amide, fluorinated carbon, etc., such as the following:
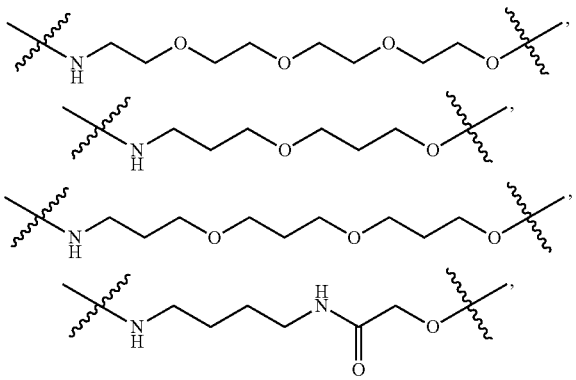
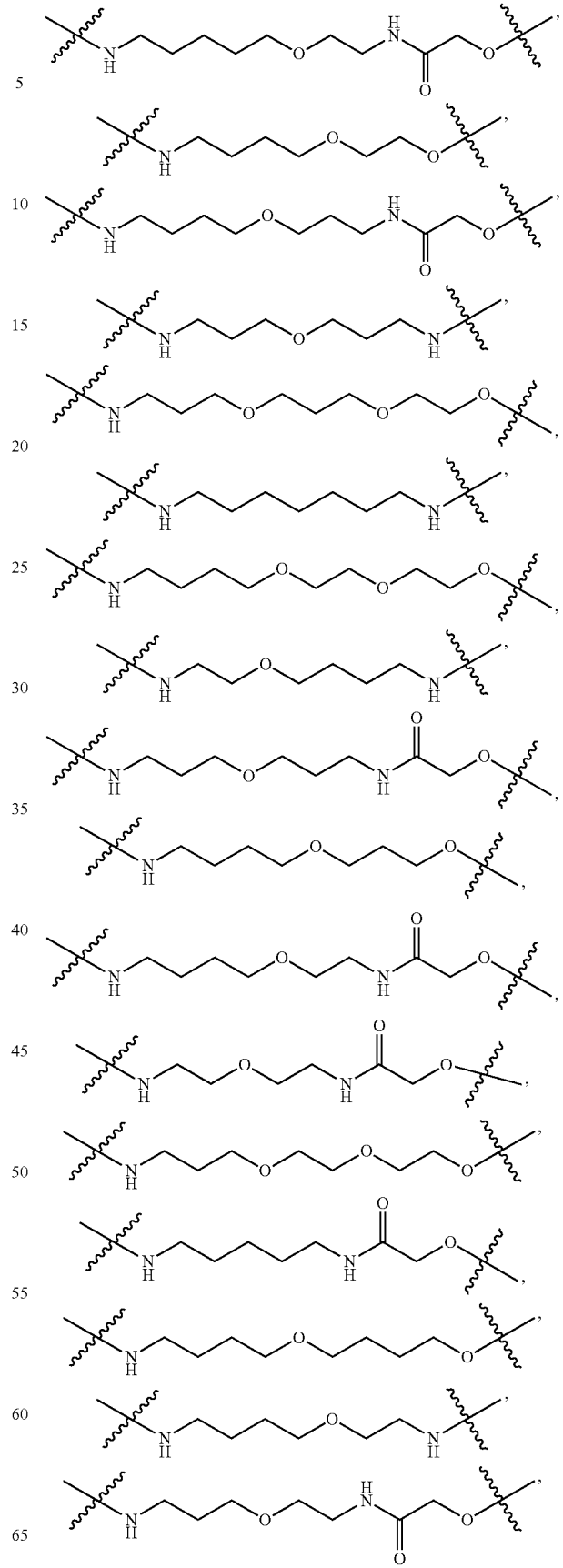

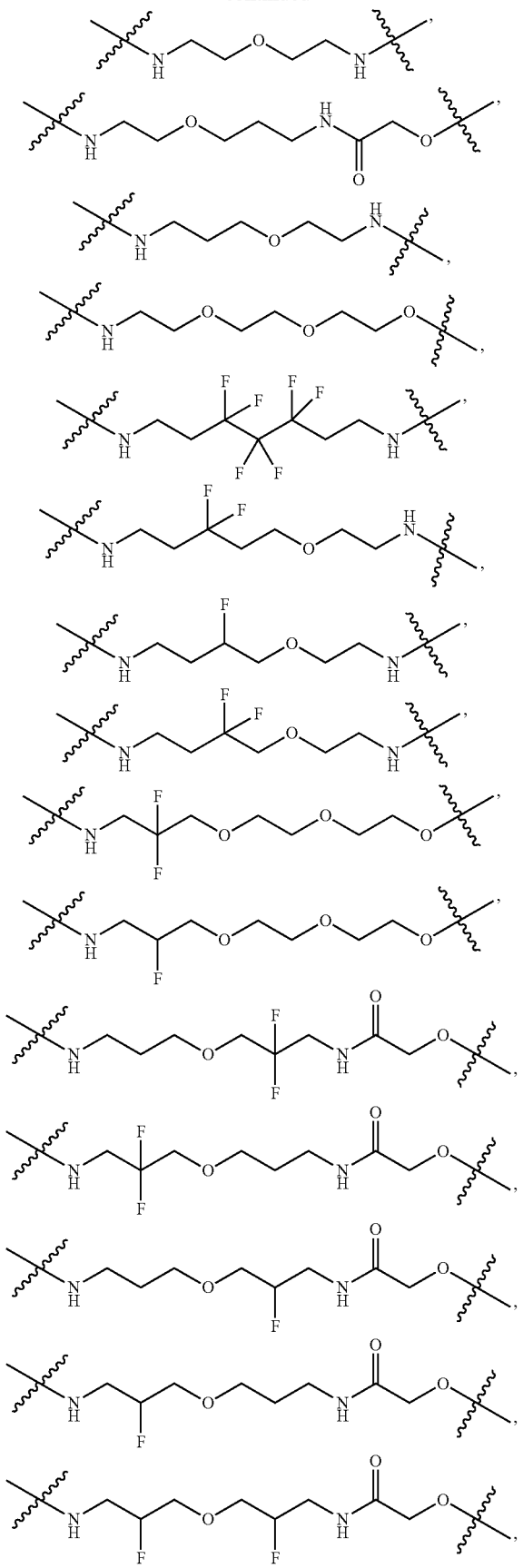

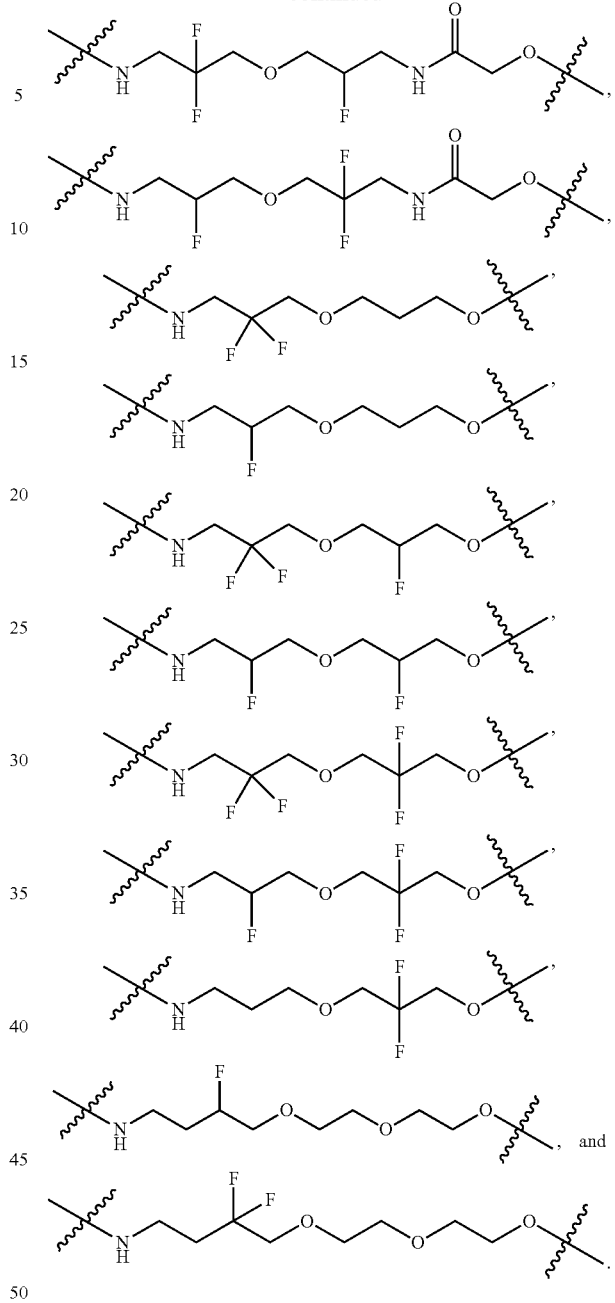

In certain embodiments, Linker can be a nonlinear chain, and can be, or include, aliphatic or aromatic or heteroaromatic cyclic moieties.

In certain embodiments, Linker may include contiguous, partially contiguous or non-contiguous ethylene glycol unit groups ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units, for example, 1, 2, 3, 4, 6, 6, 7, 8, 9, 10, 11 or 12 ethylene glycol units.

In certain embodiments, Linker may have 1, 2, 3, 4, 5, 6, 7, 8, 9, 10, 11, 12, 13, 14, or 15 fluorine substituents. In another embodiment Linker is perfluorinated. In yet another embodiment Linker is a partially or fully fluorinated poly ether. Nonlimiting examples of fluorinated Linker moieties include:

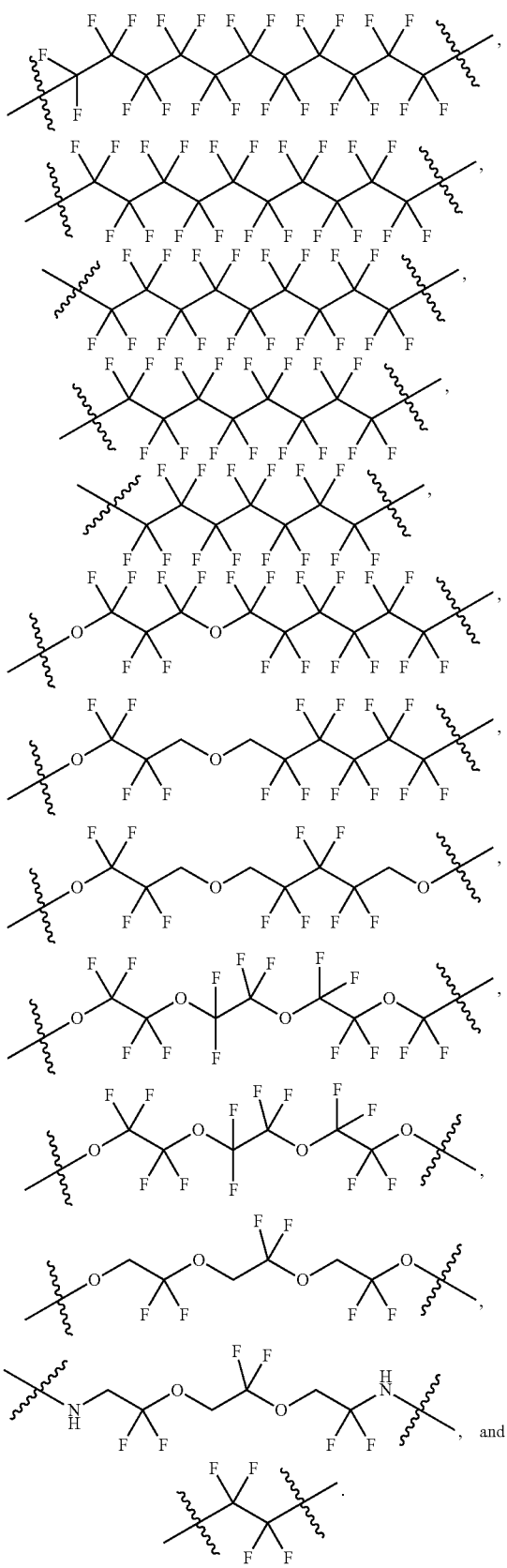

In certain embodiments, where the Target Ligand binds more than one protein (i.e., is not completely selective), selectivity may in some cases be enhanced by varying Linker length where the ligand binds some of its targets in different binding pockets, e.g., deeper or shallower binding pockets than others. Therefore, the length can be adjusted as desired.

In another embodiment, -Linker-Targeting Ligand is -Tail, wherein Tail is a monovalent group. In one embodiment, Tail is covalently attached to at least one Degron and is not attached to a Targeting Ligand. In another embodiment, -Linker-Targeting Ligand is -(Linker)$^C$, wherein -(Linker)$^C$ is covalently attached to a Targeting Ligand and one or more additional Targeting Ligands and/or Degrons.

In one embodiment, -Tail is selected from

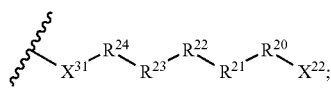

wherein all variables are defined as above.

In one embodiment, Tail is a moiety selected from Formula TI, Formula TII, Formula TIII, Formula TIV, Formula TV, Formula TVI, and Formula TVII:

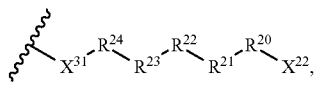 (TI)

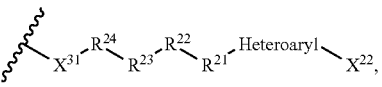 (TII)

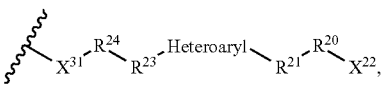 (TIII)

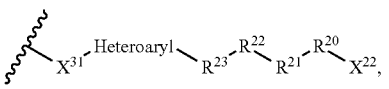 (TIV)

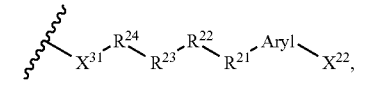 (TV)

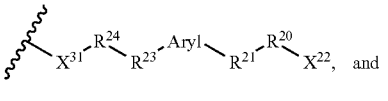 (TVI)

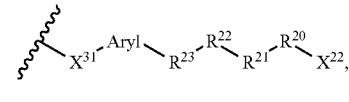 (TVII)

wherein all variables are defined as above.

In an additional embodiment, -(Tail) is a moiety selected from Formula TVIII, TIX, and TX:

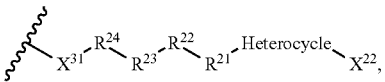 (TVIII)

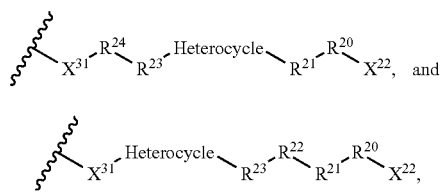

wherein all variables are defined as above. In other embodiments of TVIII, TIX and TX, a carbocyclic ring is used in place of the heterocycle.

The following are non-limiting examples of -(Tail) moieties that can be used in this invention. Based on this elaboration, those of skill in the art will understand how to use the full breadth of -(Tail) moieties that will accomplish the goal of the invention.

As certain non-limiting examples, Formula TI, Formula TII, Formula TIII, Formula TIV, Formula TV, Formula TVI, or Formula TVII include:

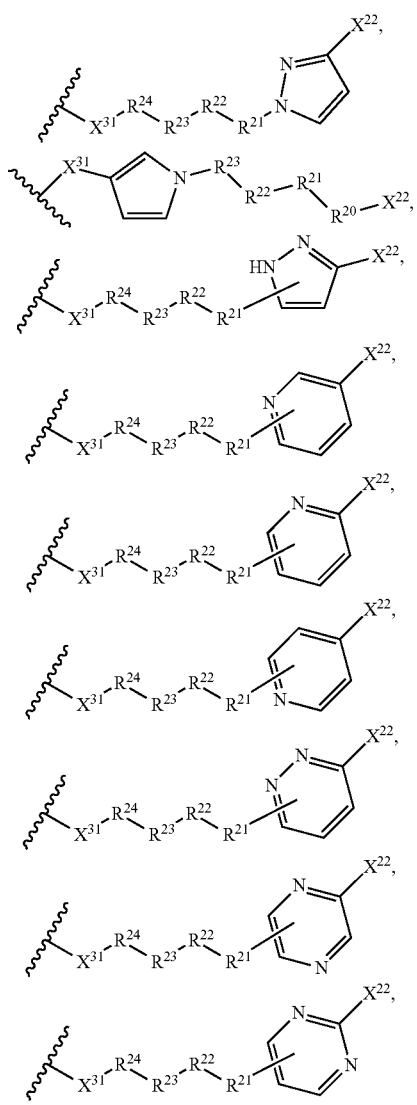

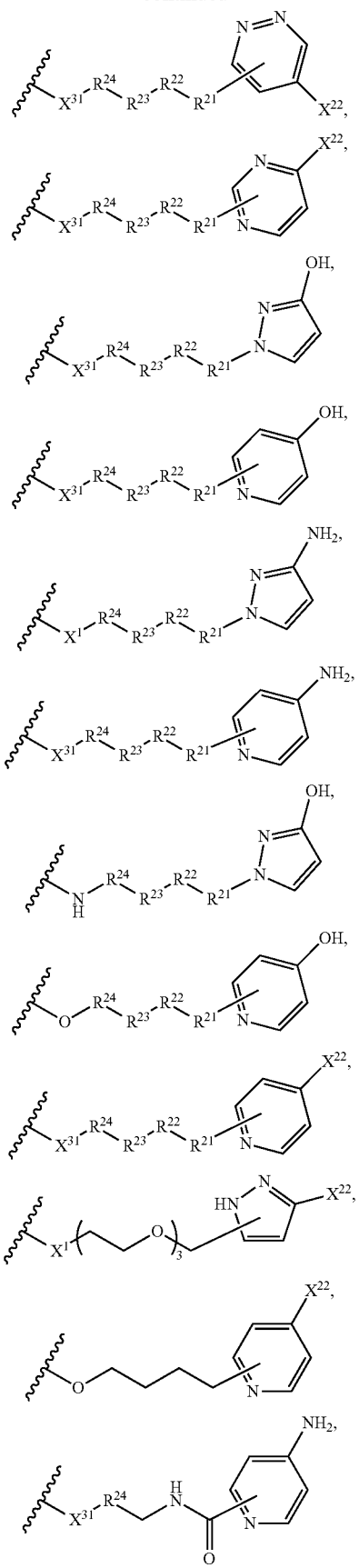

-continued
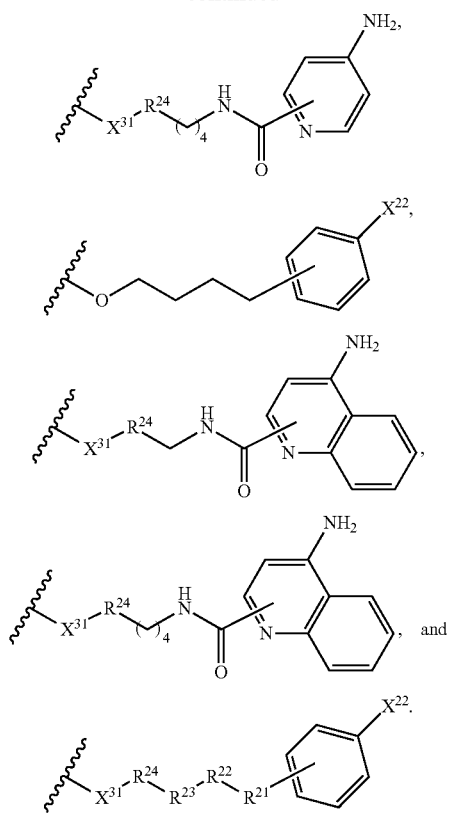
In an additional embodiment -(Tail) can be selected from the group consisting of:
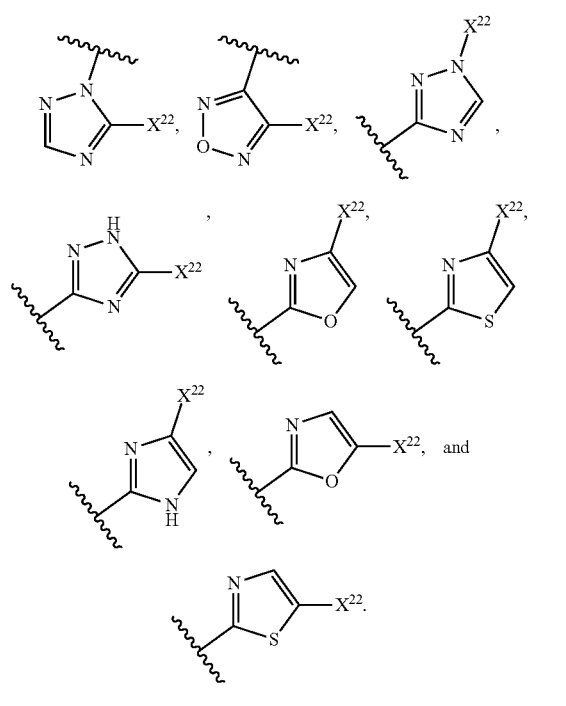
In an additional embodiment -(Tail) is selected from the group consisting of:
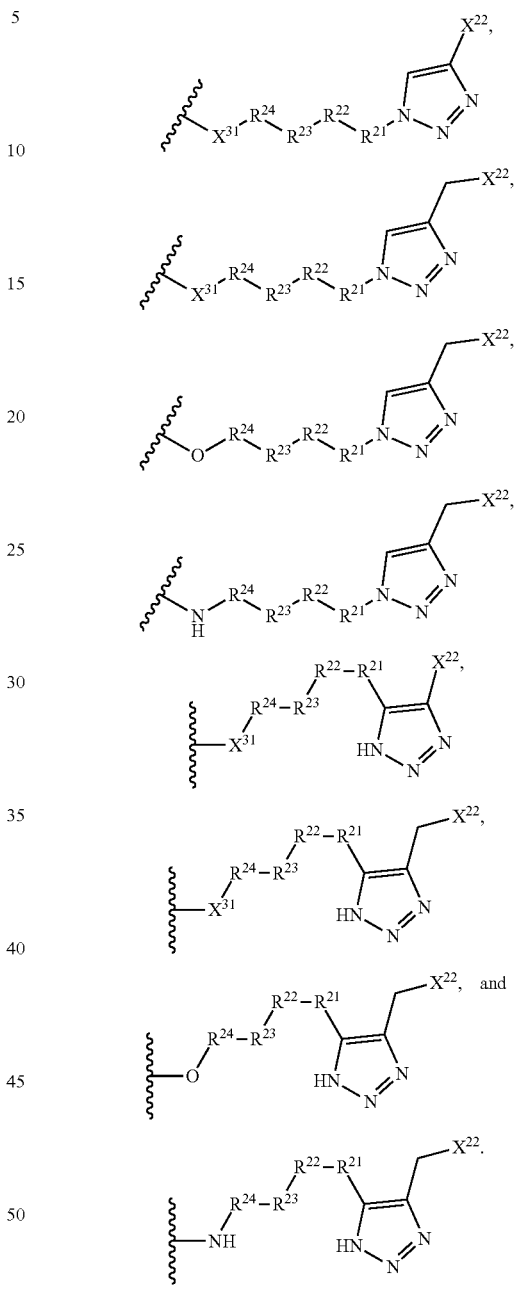
Non-limiting examples of moieties of $R^{20}$, $R^{21}$, $R^{22}$, $R^{23}$, and $R^{24}$ include:
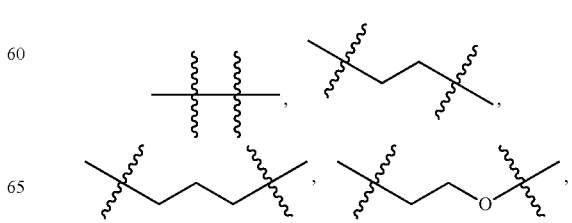

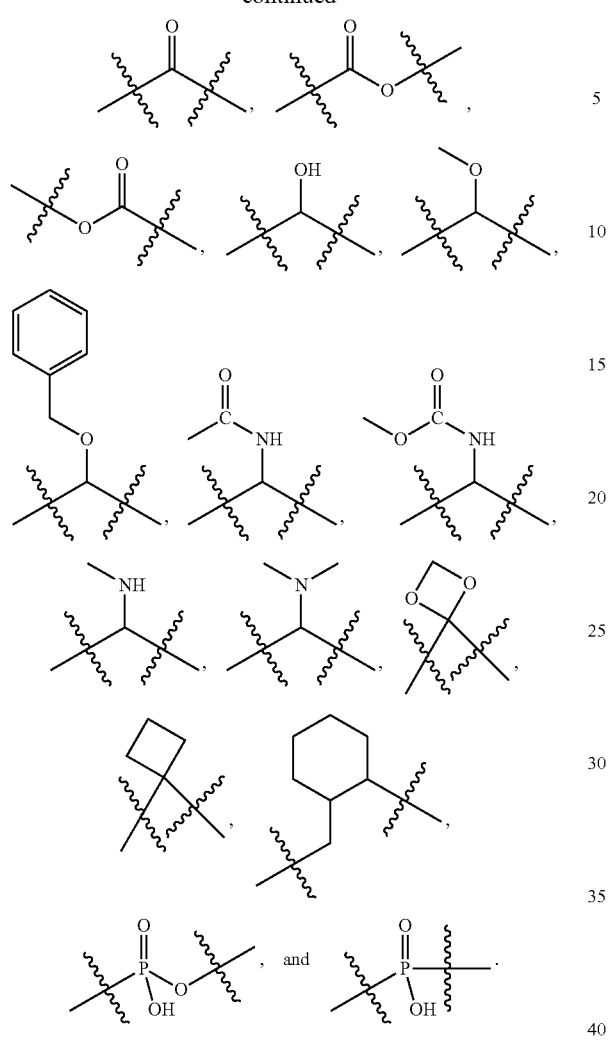
Additional non-limiting examples of moieties of $R^{20}$, $R^{21}$, $R^{22}$, $R^{23}$ and $R^{24}$ include:
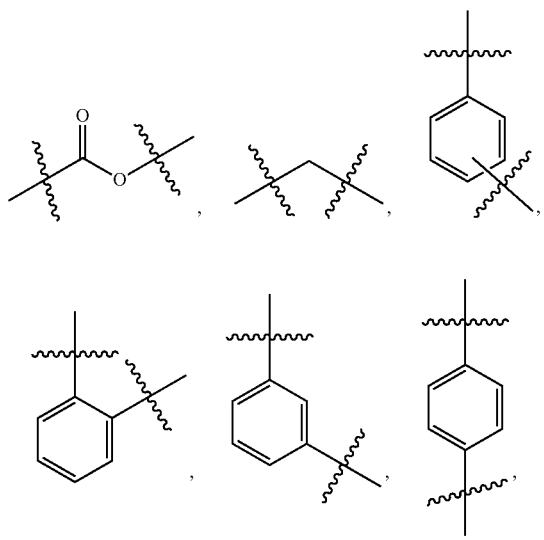
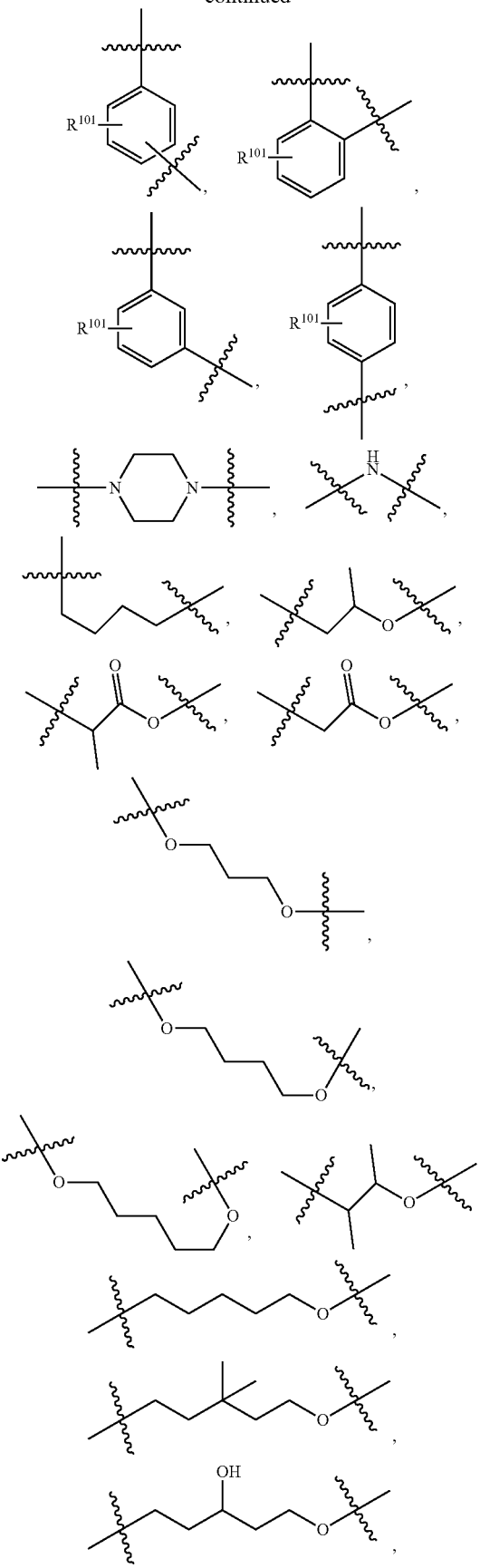

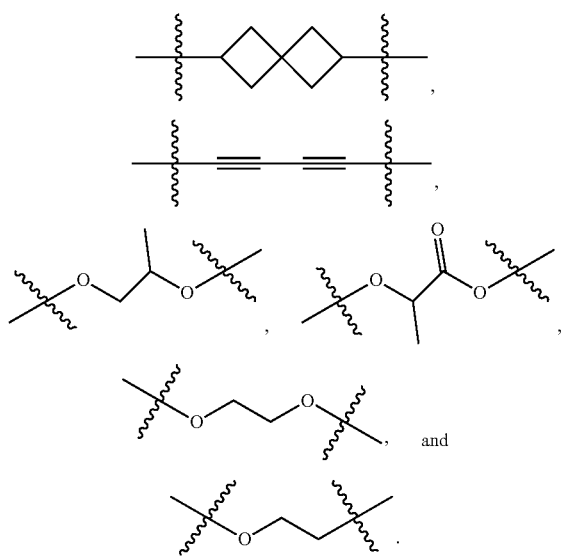

Additional non-limiting examples of moieties of $R^{20}R^{21}$, $R^{22}$, $R^{23}$, and $R^{24}$ include:

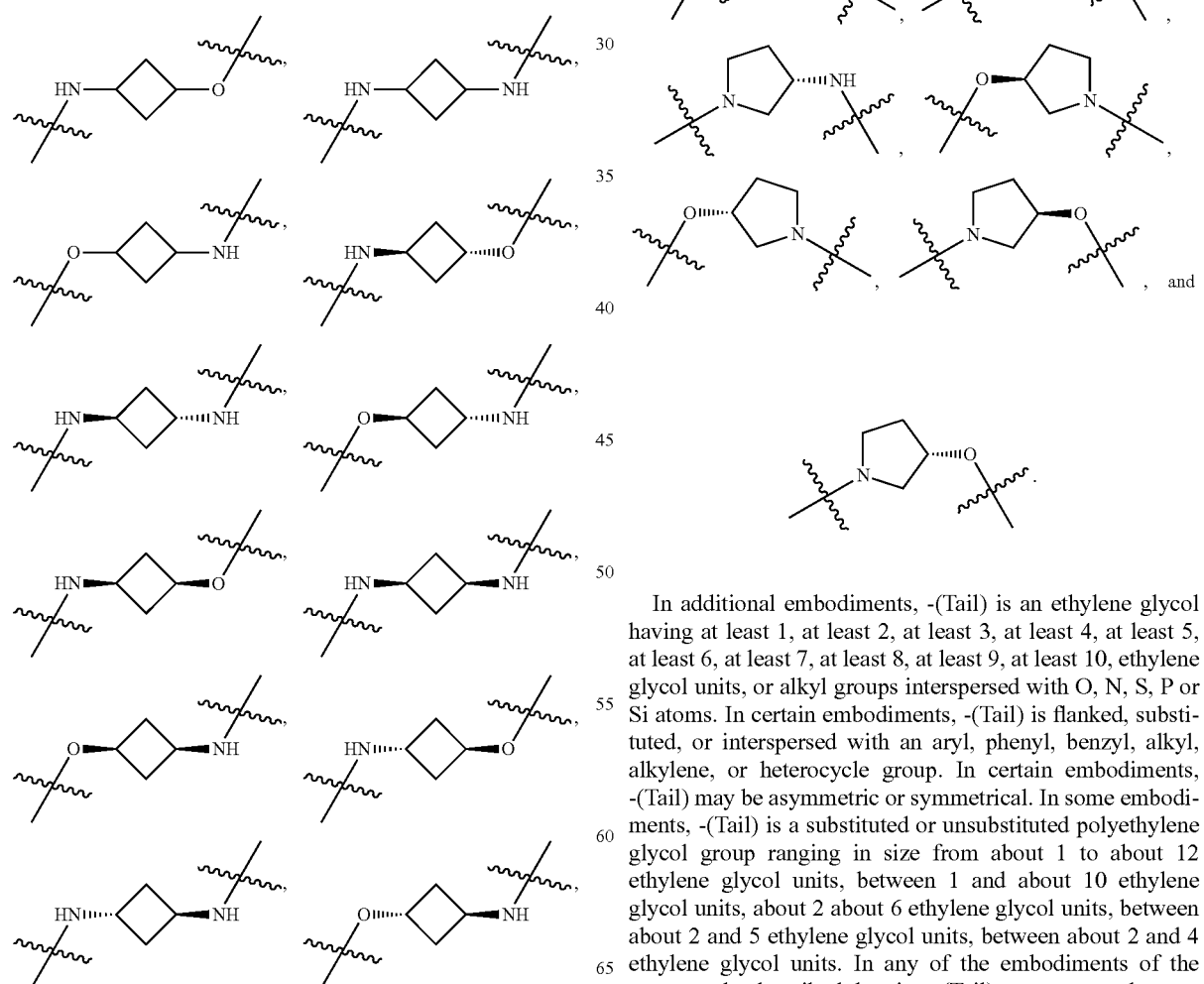

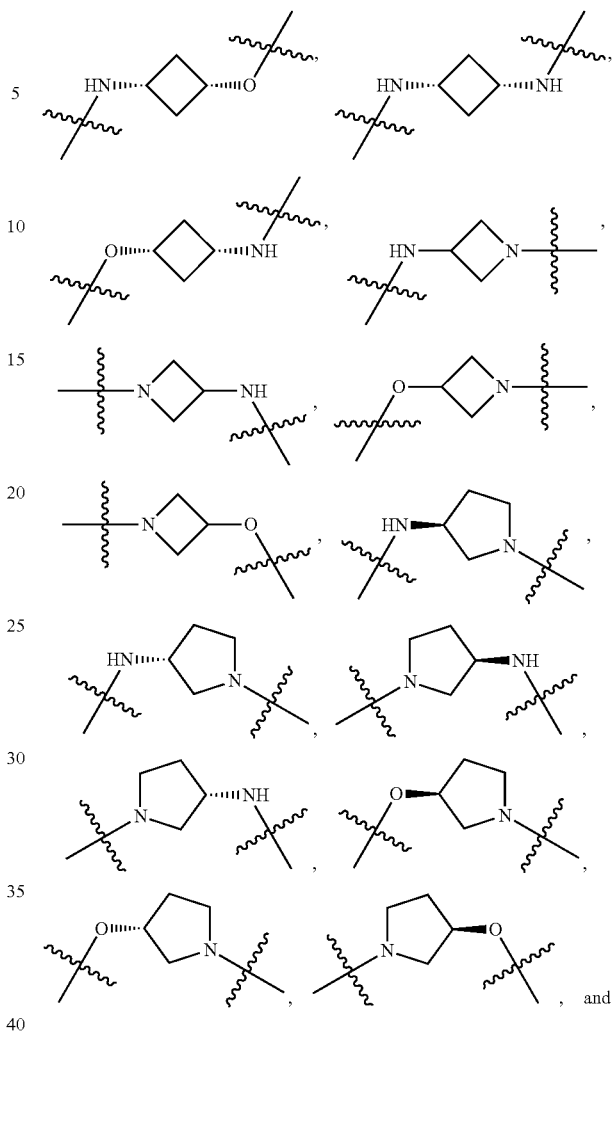

In additional embodiments, -(Tail) is an ethylene glycol having at least 1, at least 2, at least 3, at least 4, at least 5, at least 6, at least 7, at least 8, at least 9, at least 10, ethylene glycol units, or alkyl groups interspersed with O, N, S, P or Si atoms. In certain embodiments, -(Tail) is flanked, substituted, or interspersed with an aryl, phenyl, benzyl, alkyl, alkylene, or heterocycle group. In certain embodiments, -(Tail) may be asymmetric or symmetrical. In some embodiments, -(Tail) is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units. In any of the embodiments of the compounds described herein, -(Tail) group may be any suitable moiety as described herein.

In additional embodiments, -(Tail) is selected from the group consisting of:
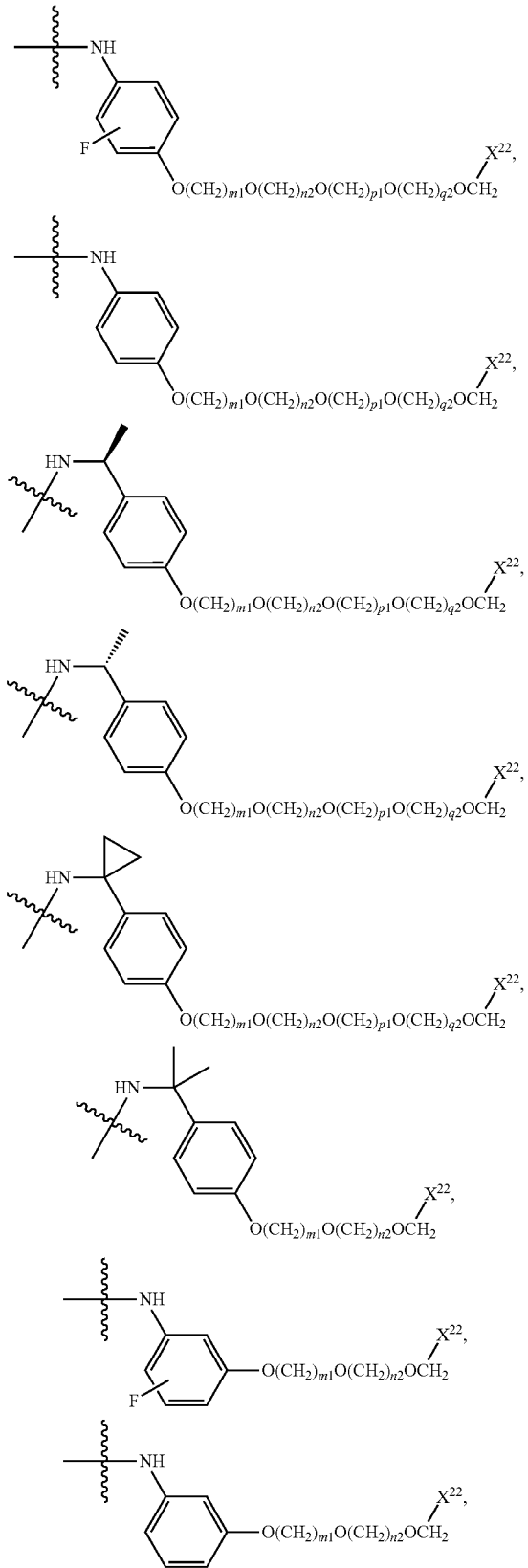
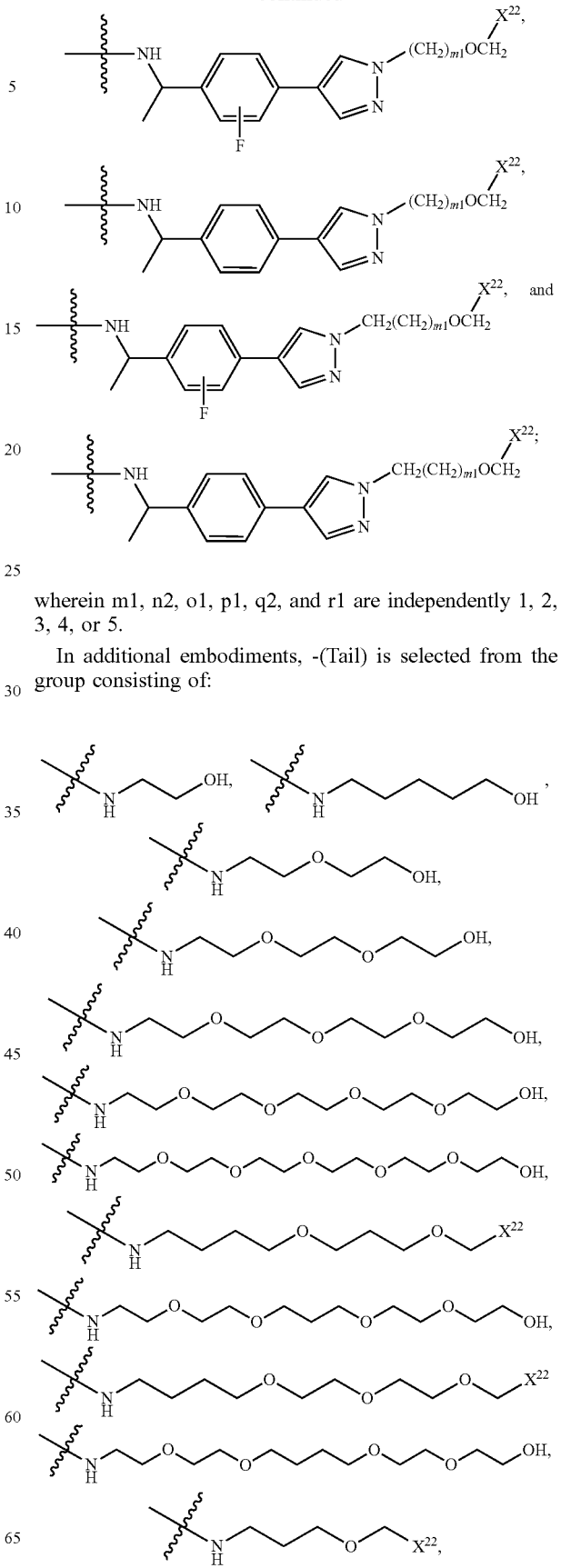
wherein m1, n2, o1, p1, q2, and r1 are independently 1, 2, 3, 4, or 5.
In additional embodiments, -(Tail) is selected from the group consisting of:

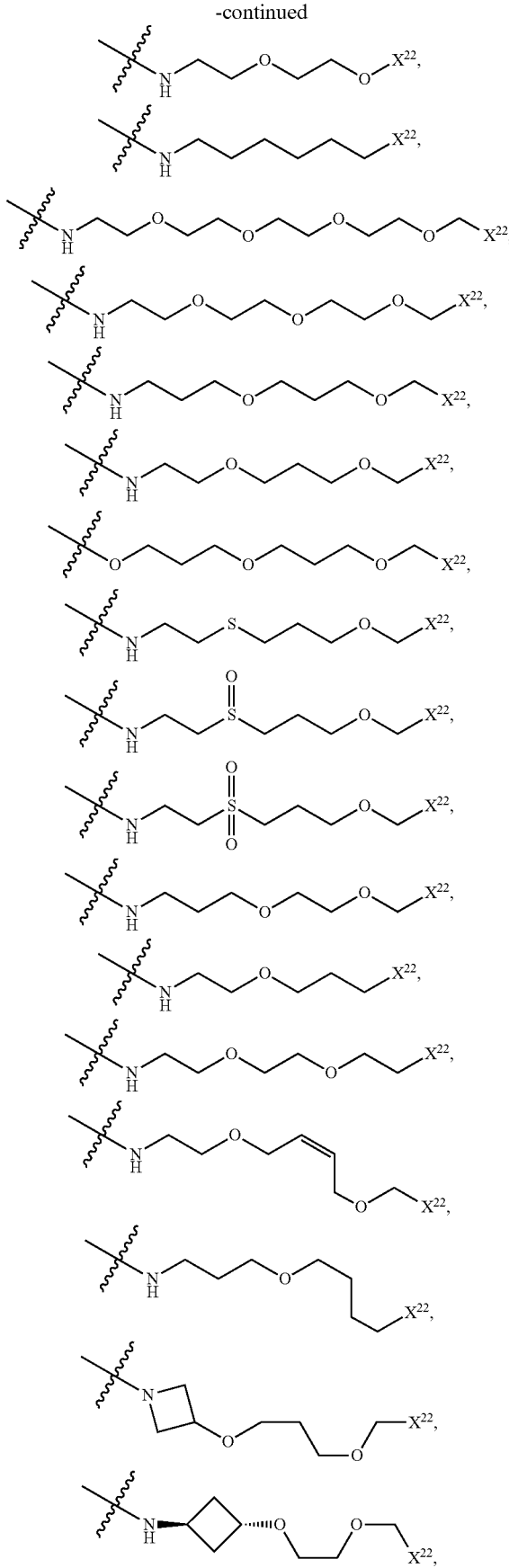
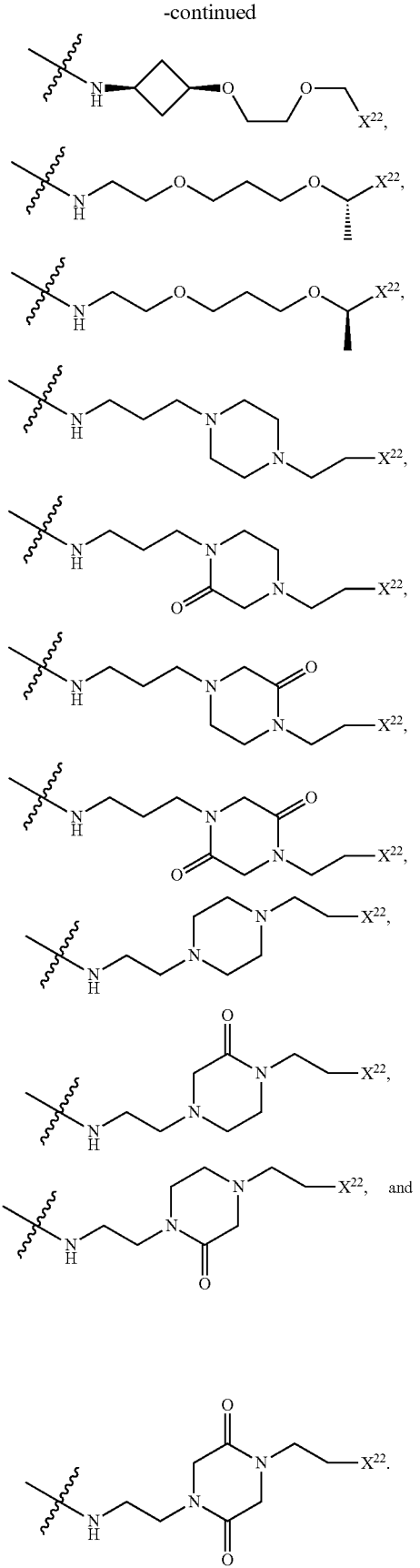

In additional embodiments, -(Tail) is selected from the group consisting of:
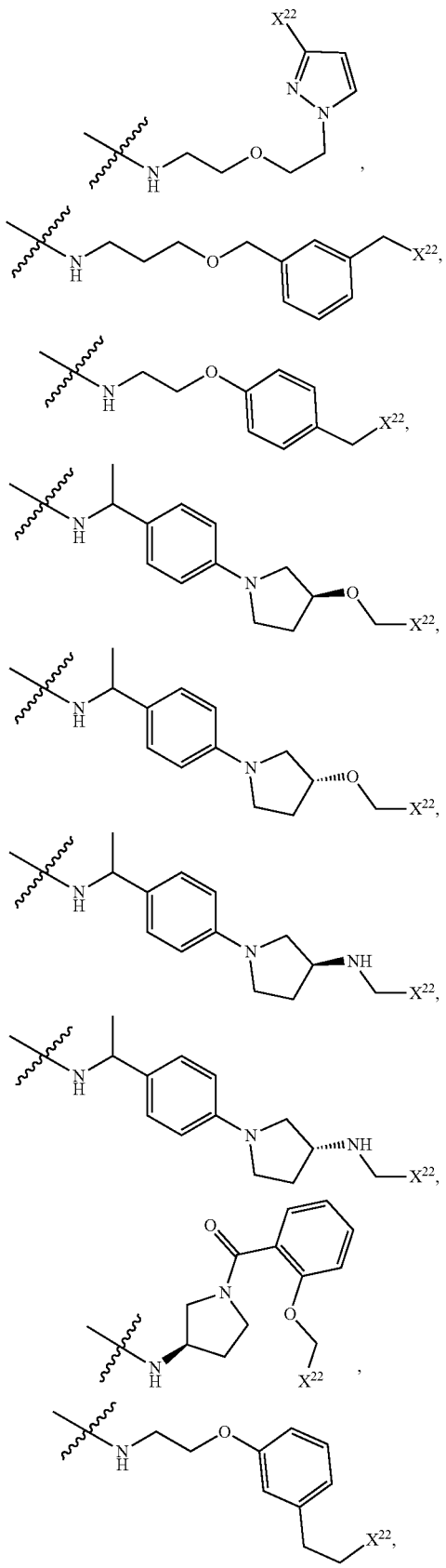
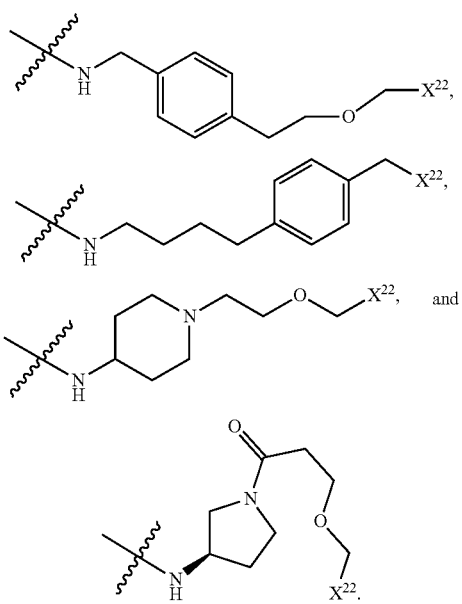
In additional embodiments, -(Tail) is selected from the group consisting of:
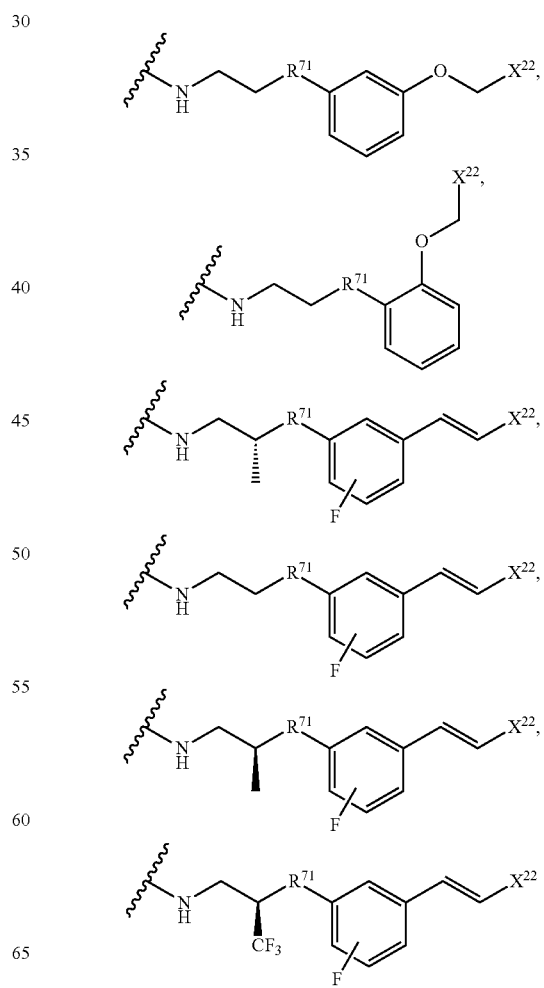

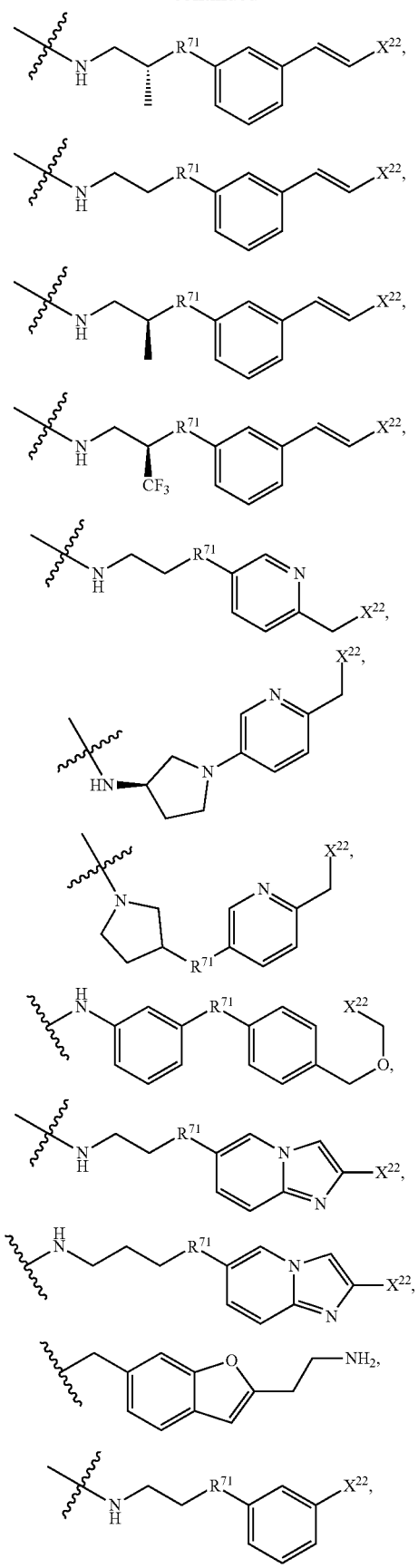
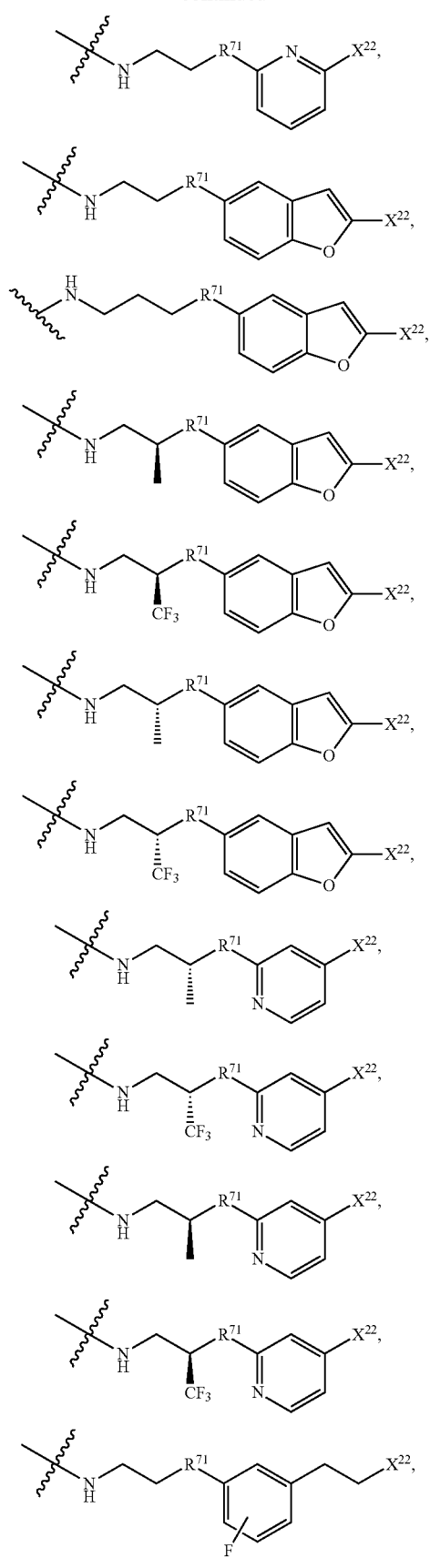

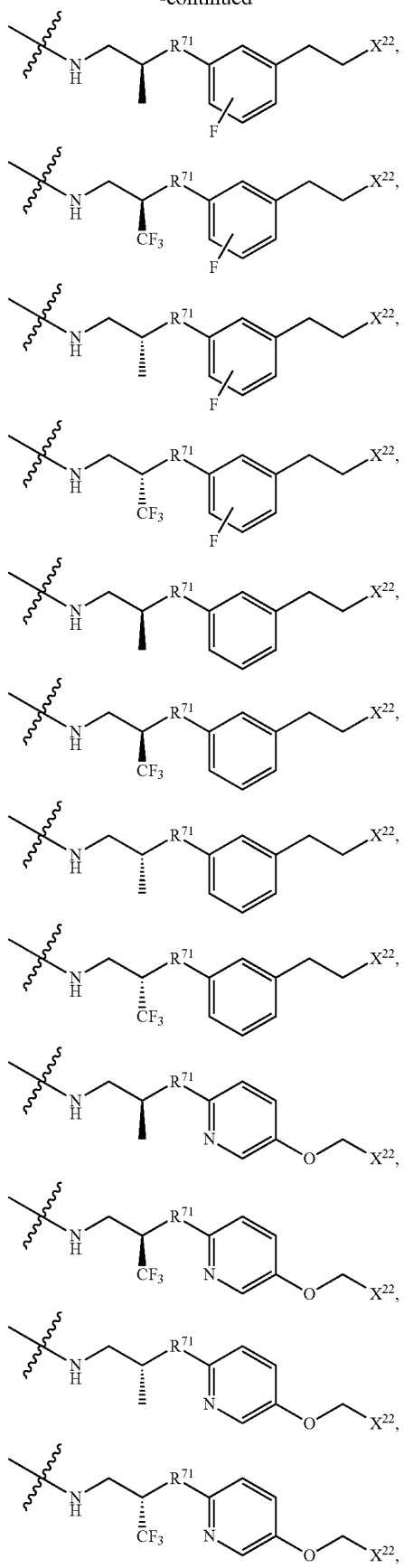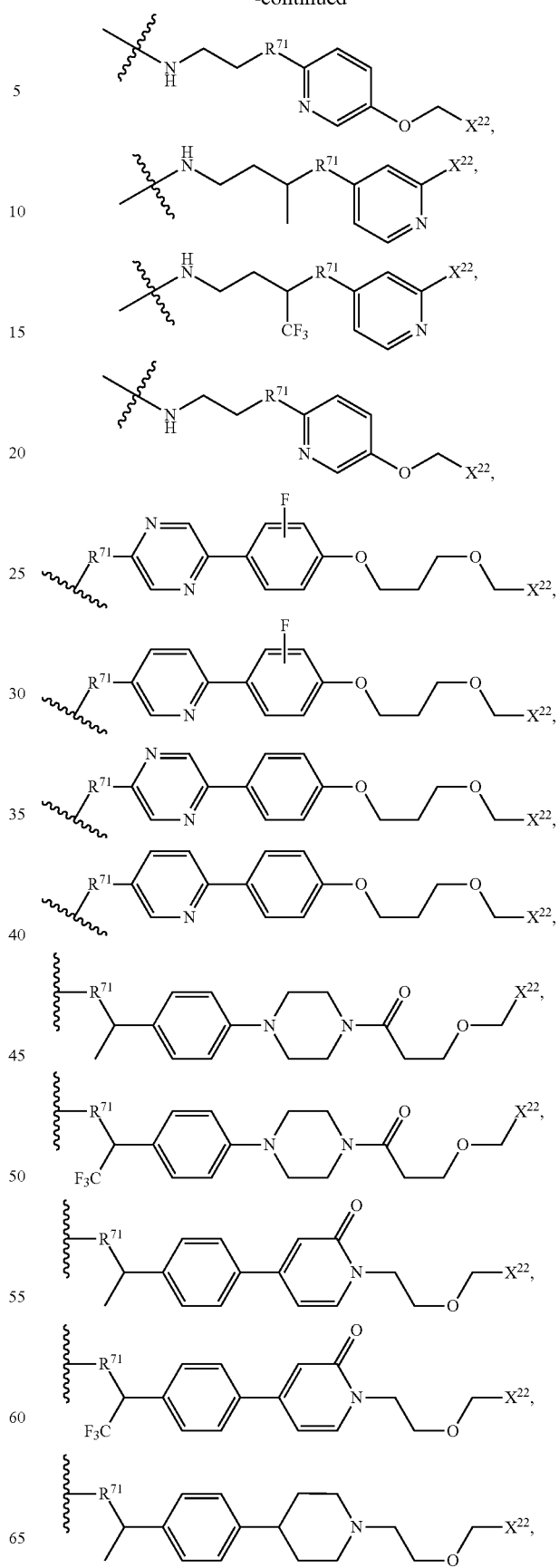

269
-continued
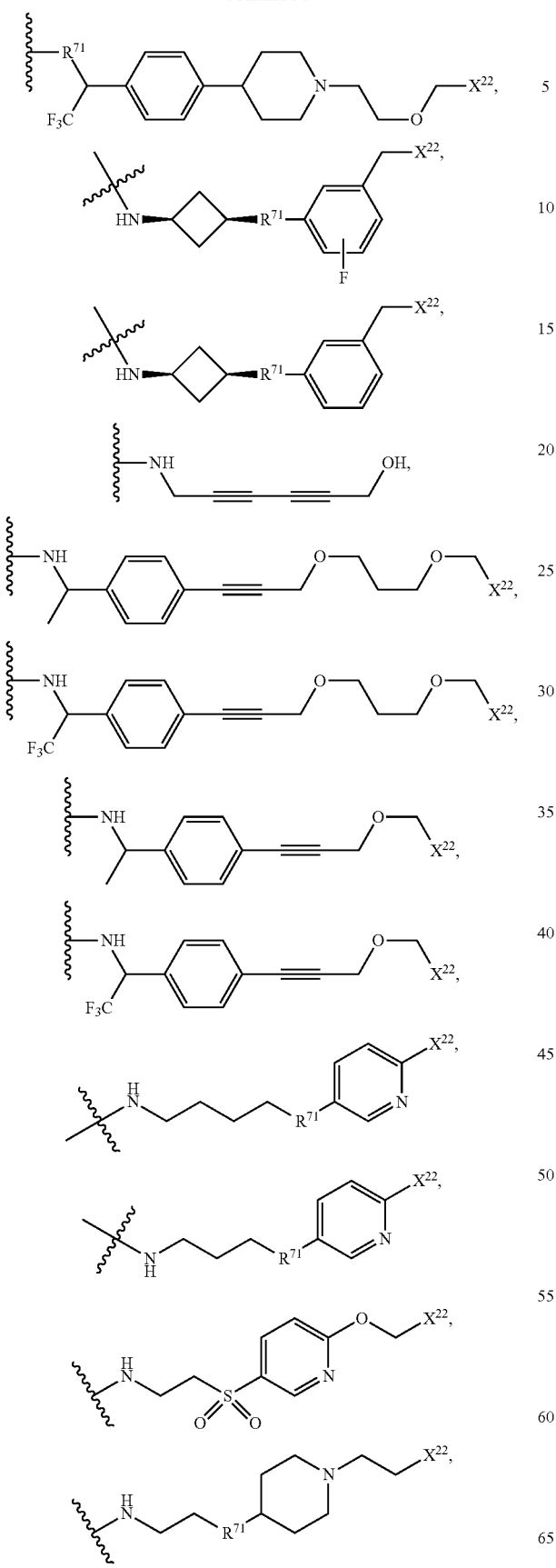
270
-continued
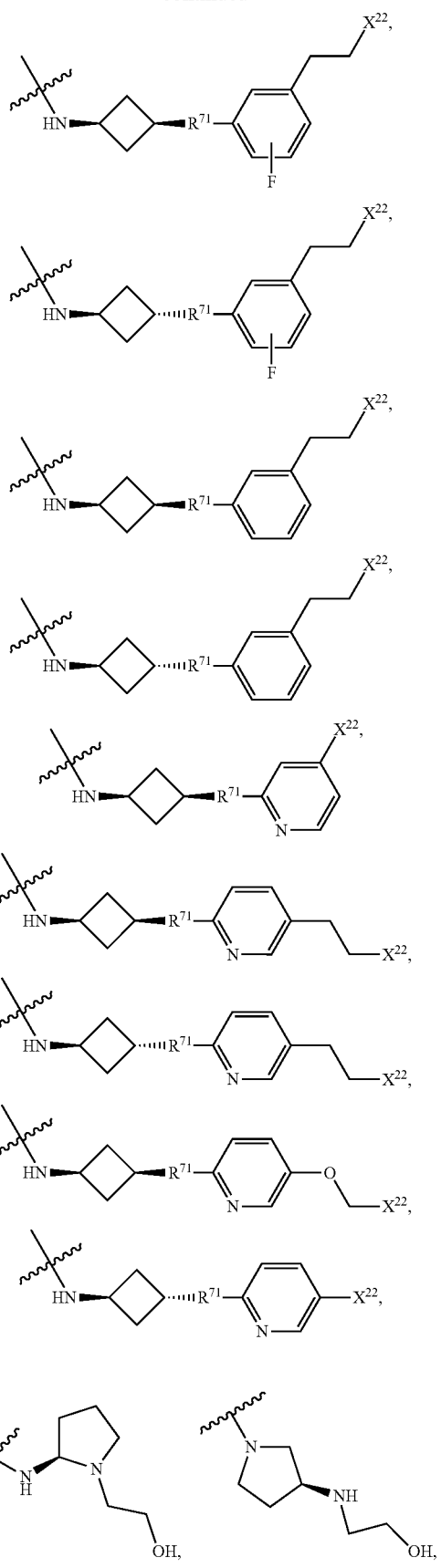

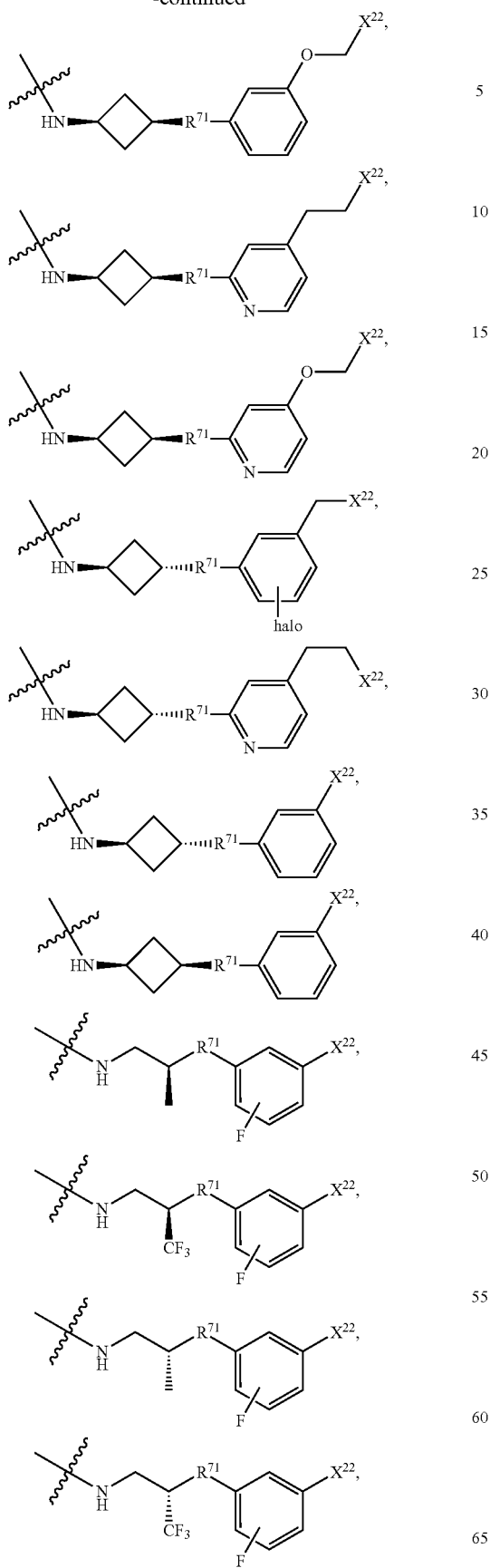
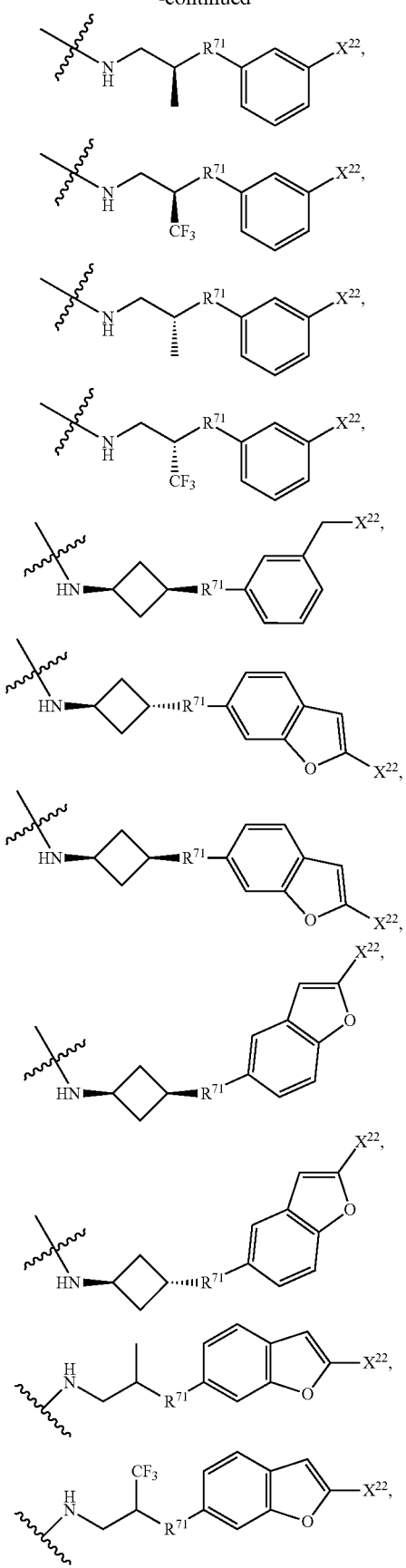

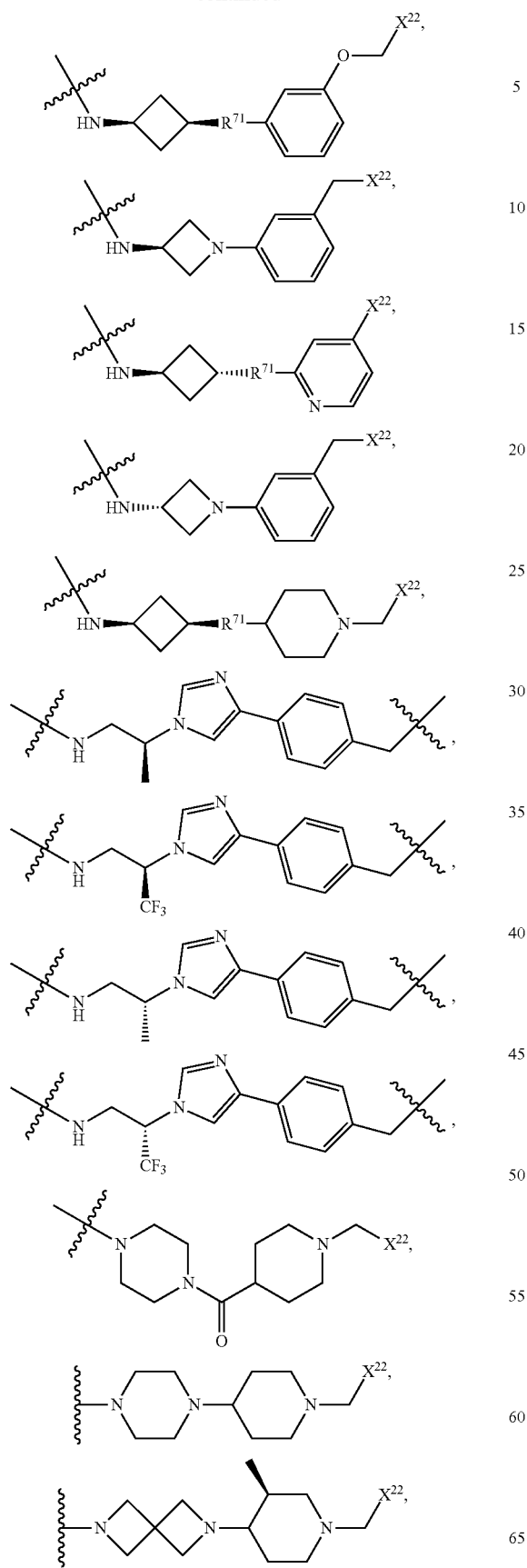
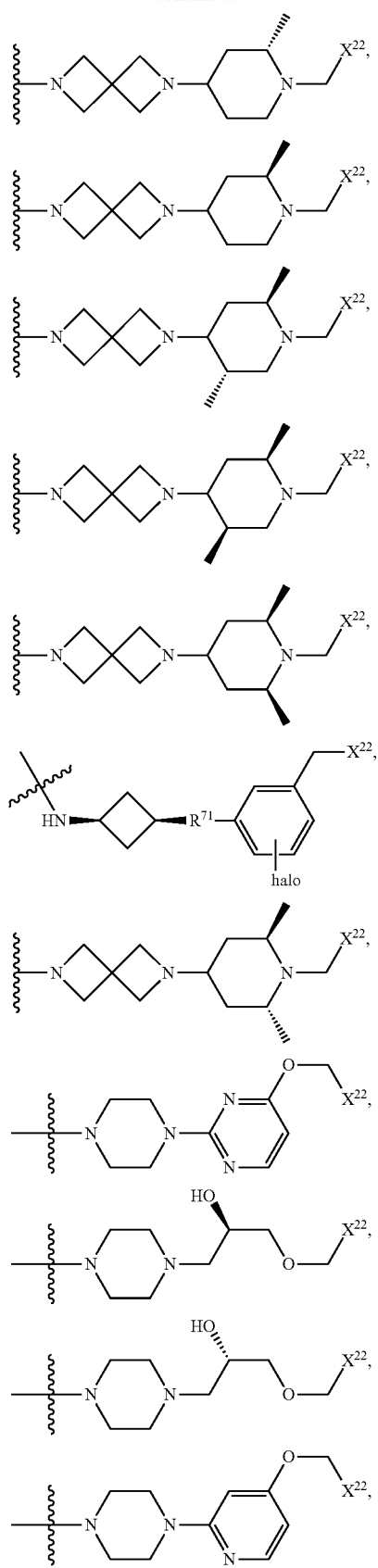

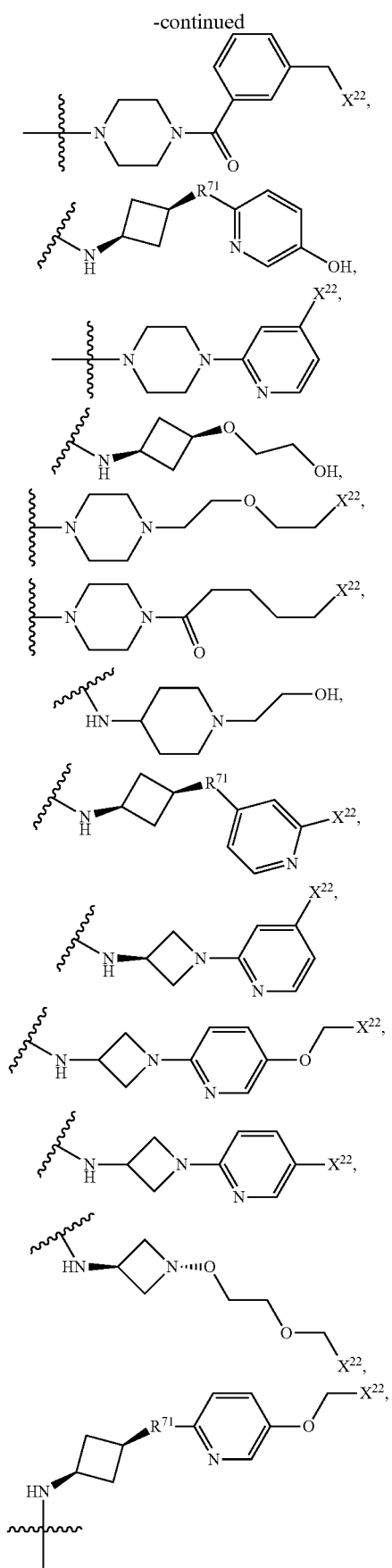
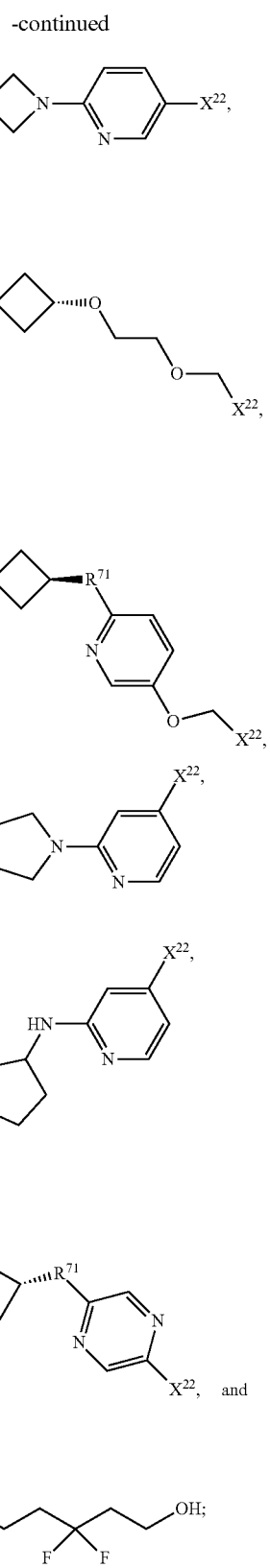
wherein $R^{71}$ is —O—, —NH, Nalkyl, heteroaliphatic, aliphatic, or —NMe.

In additional embodiments, -(Tail) is selected from the group consisting of
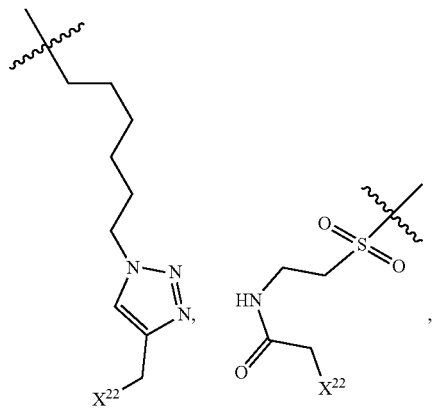
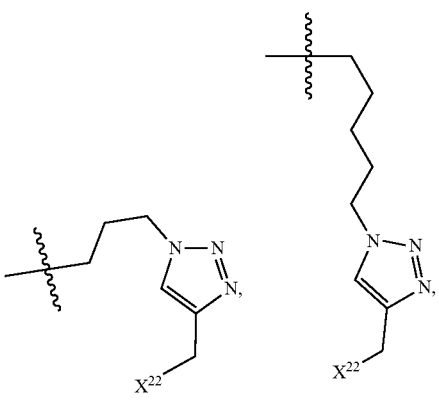
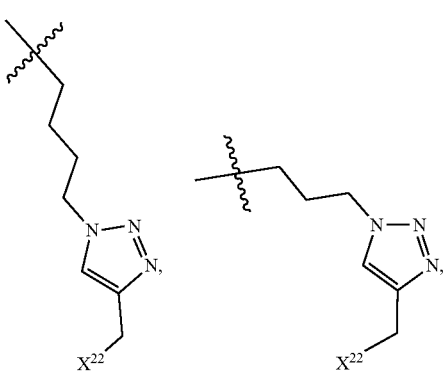
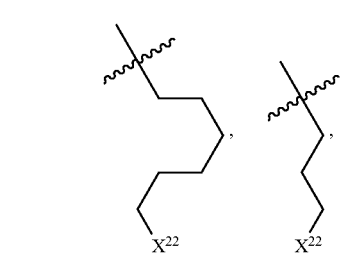
-continued
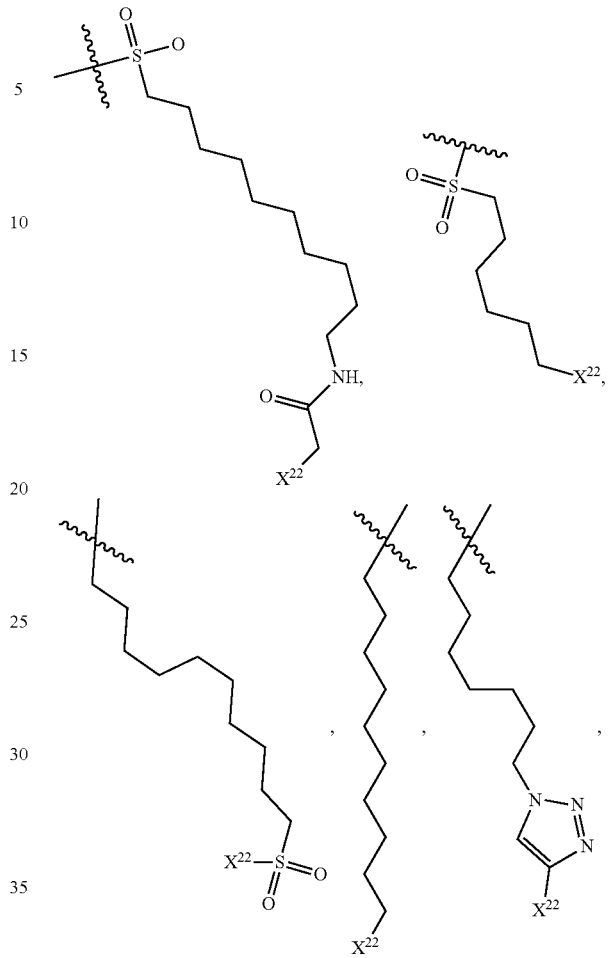
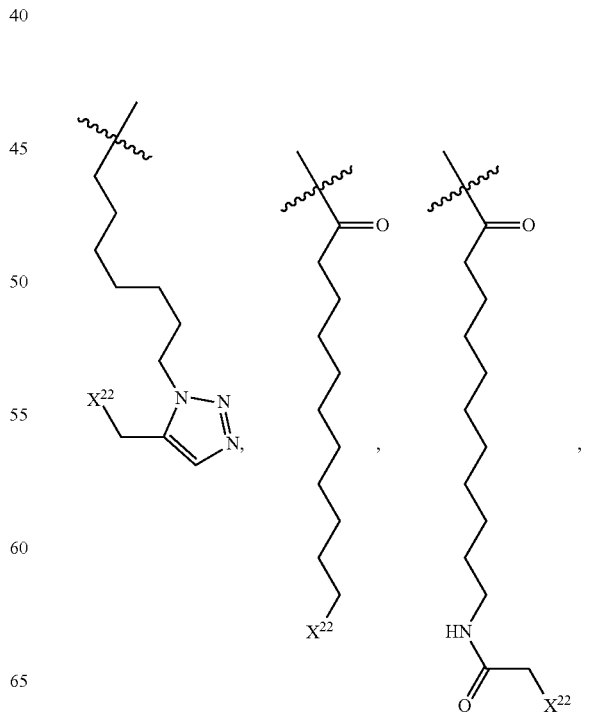

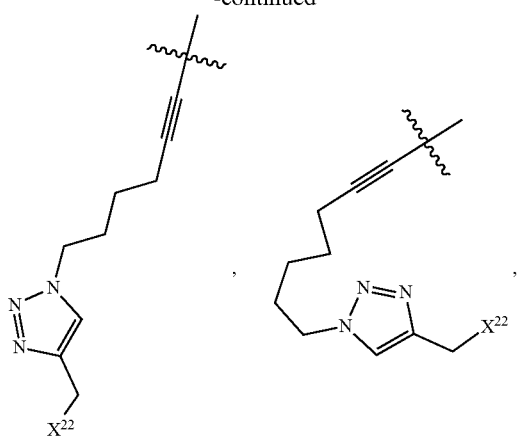
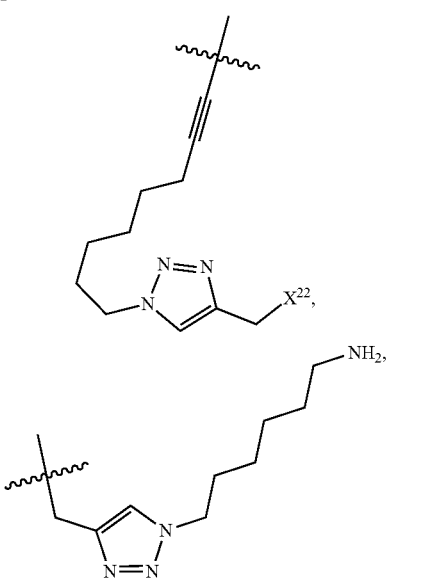
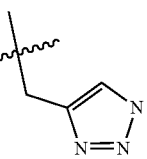
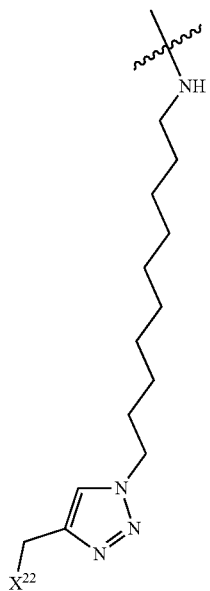
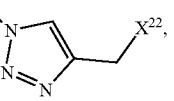
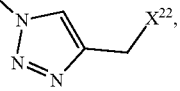
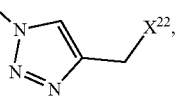

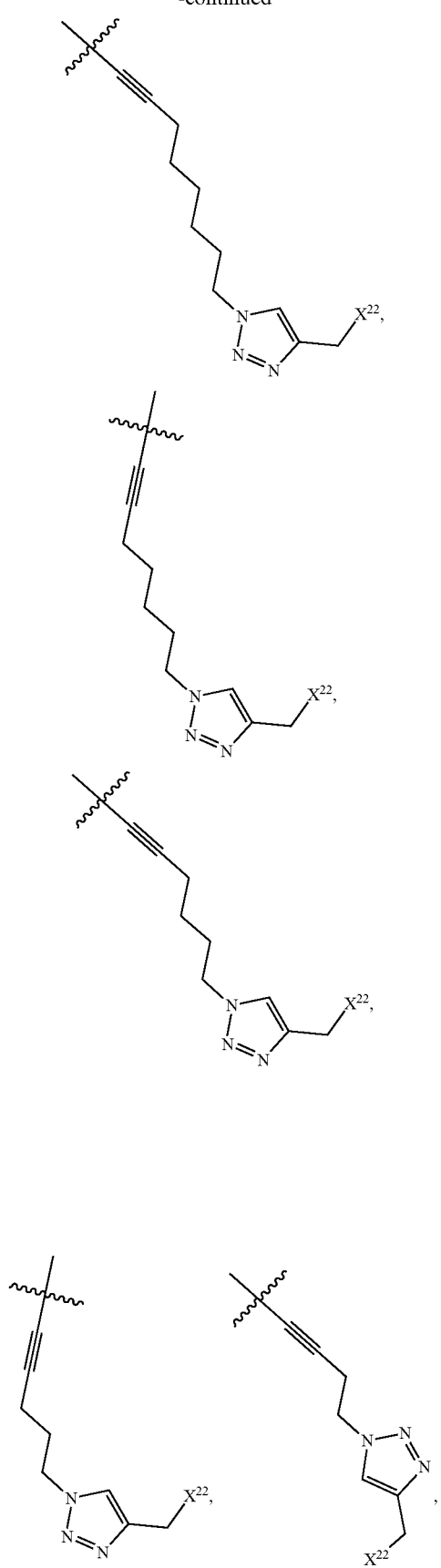
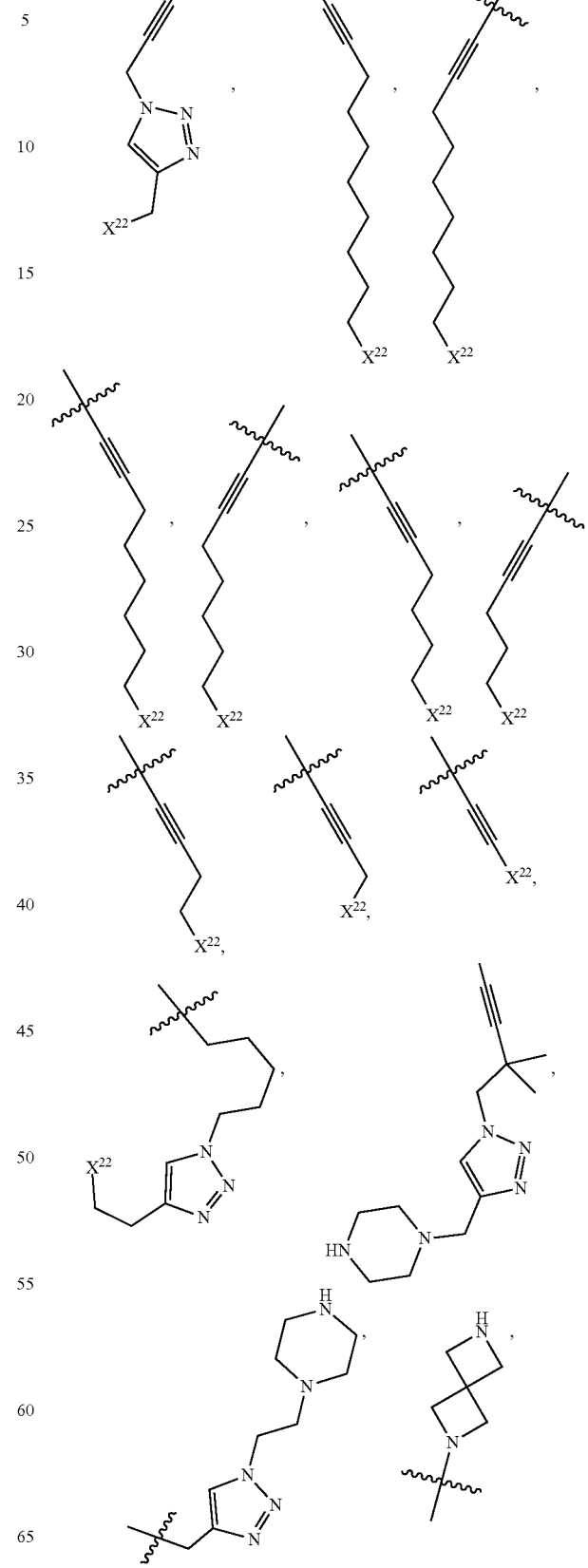

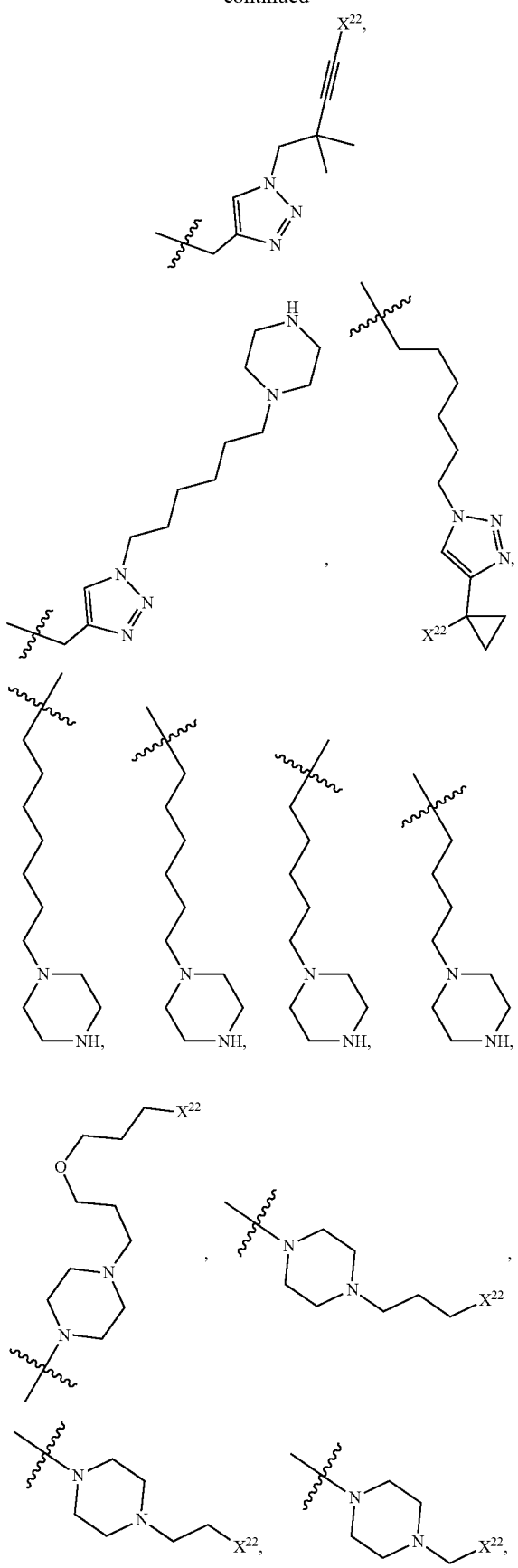
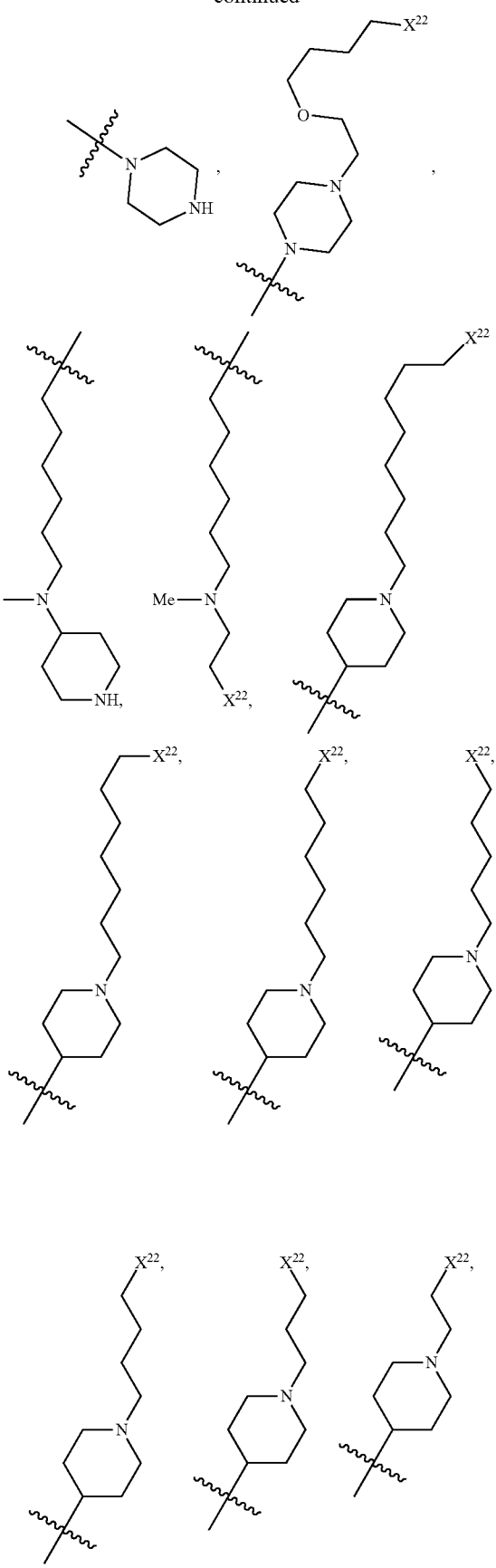

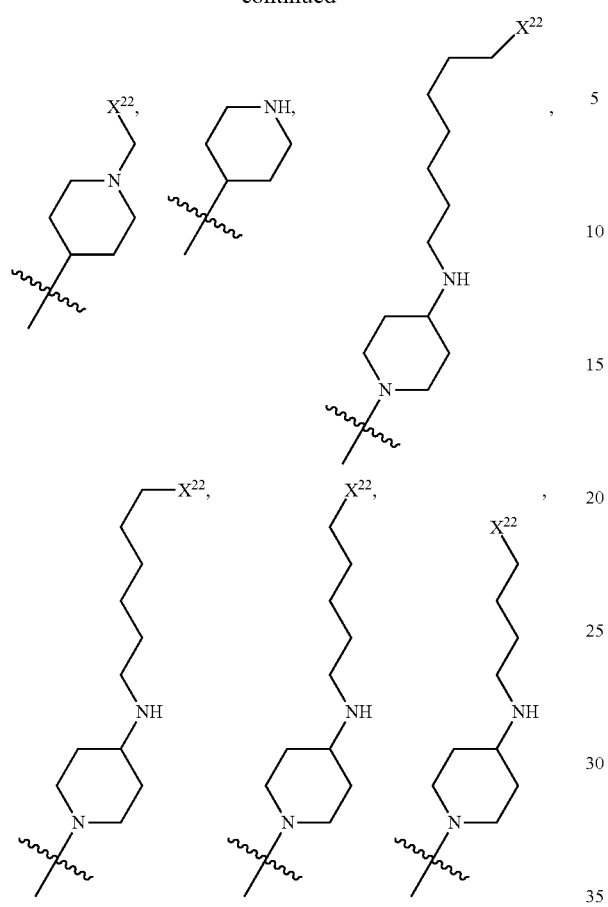
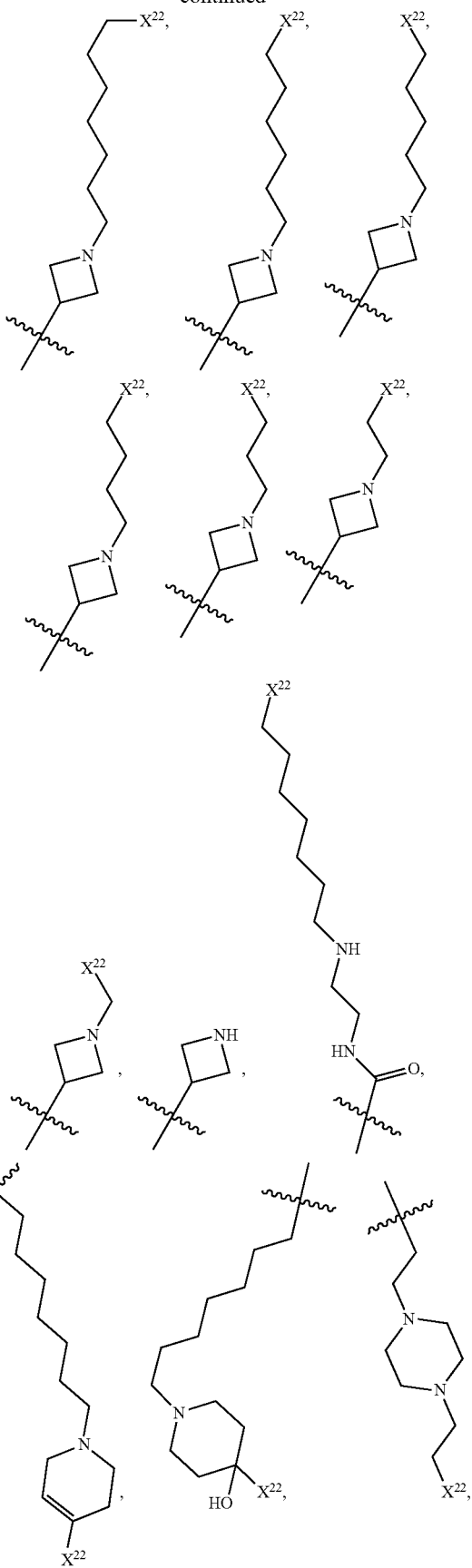

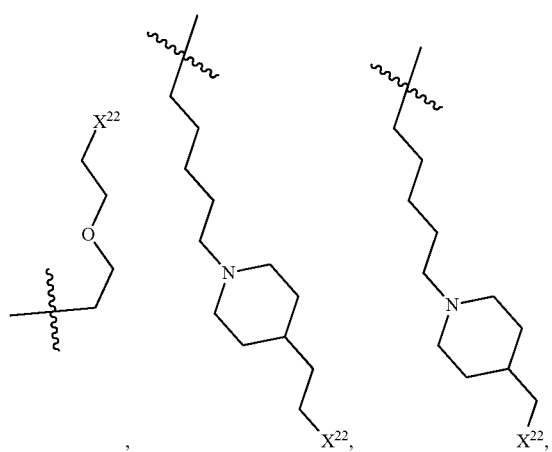
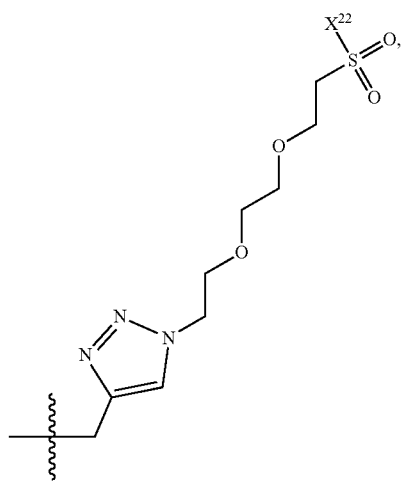
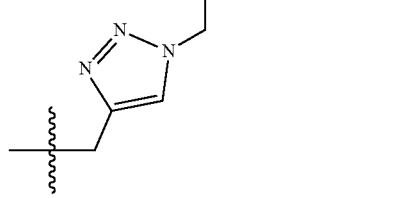
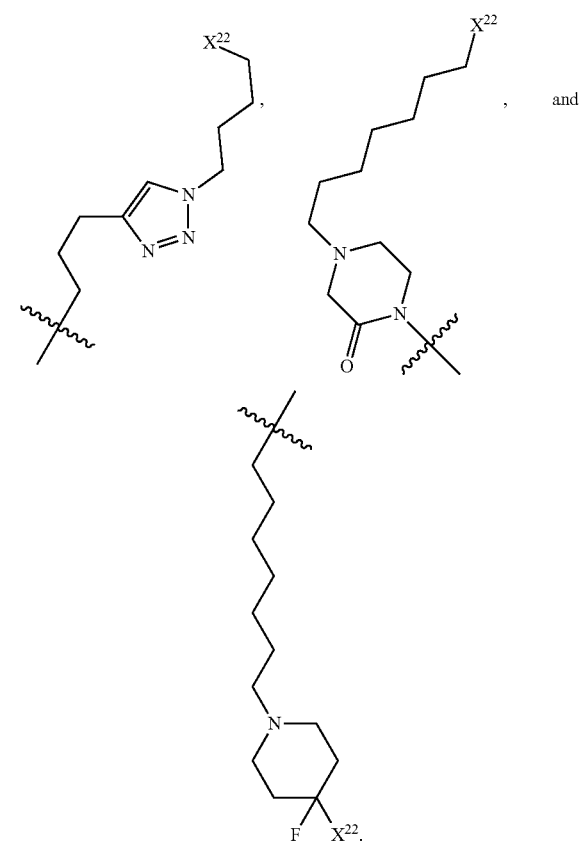
In additional embodiments, -(Tail) is selected from the group consisting of:
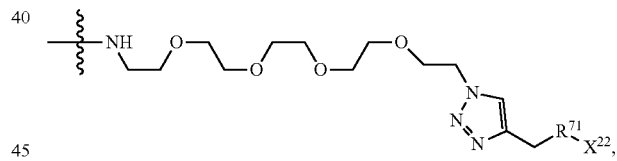
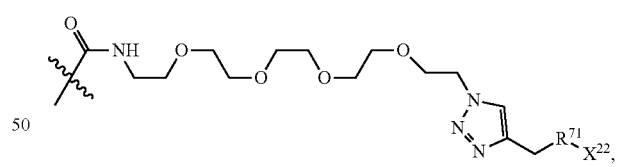
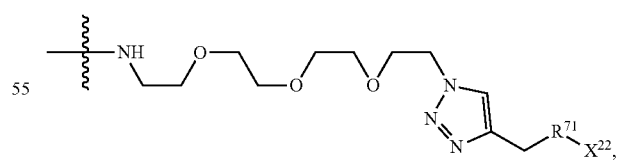
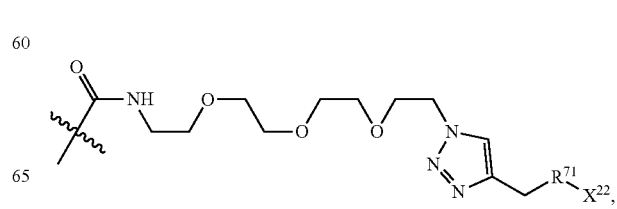

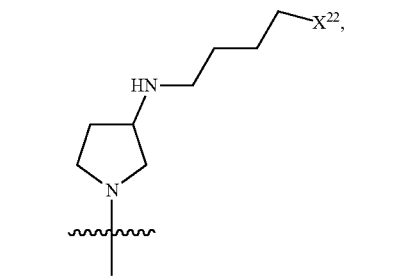
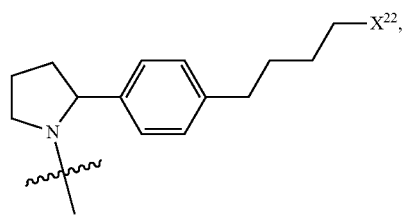
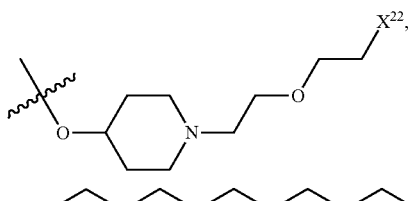
In additional embodiments, -(Tail) is selected from the group consisting of
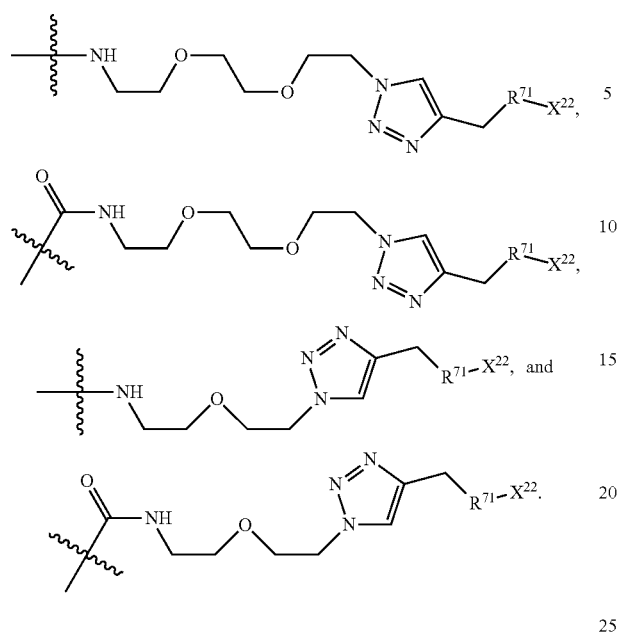
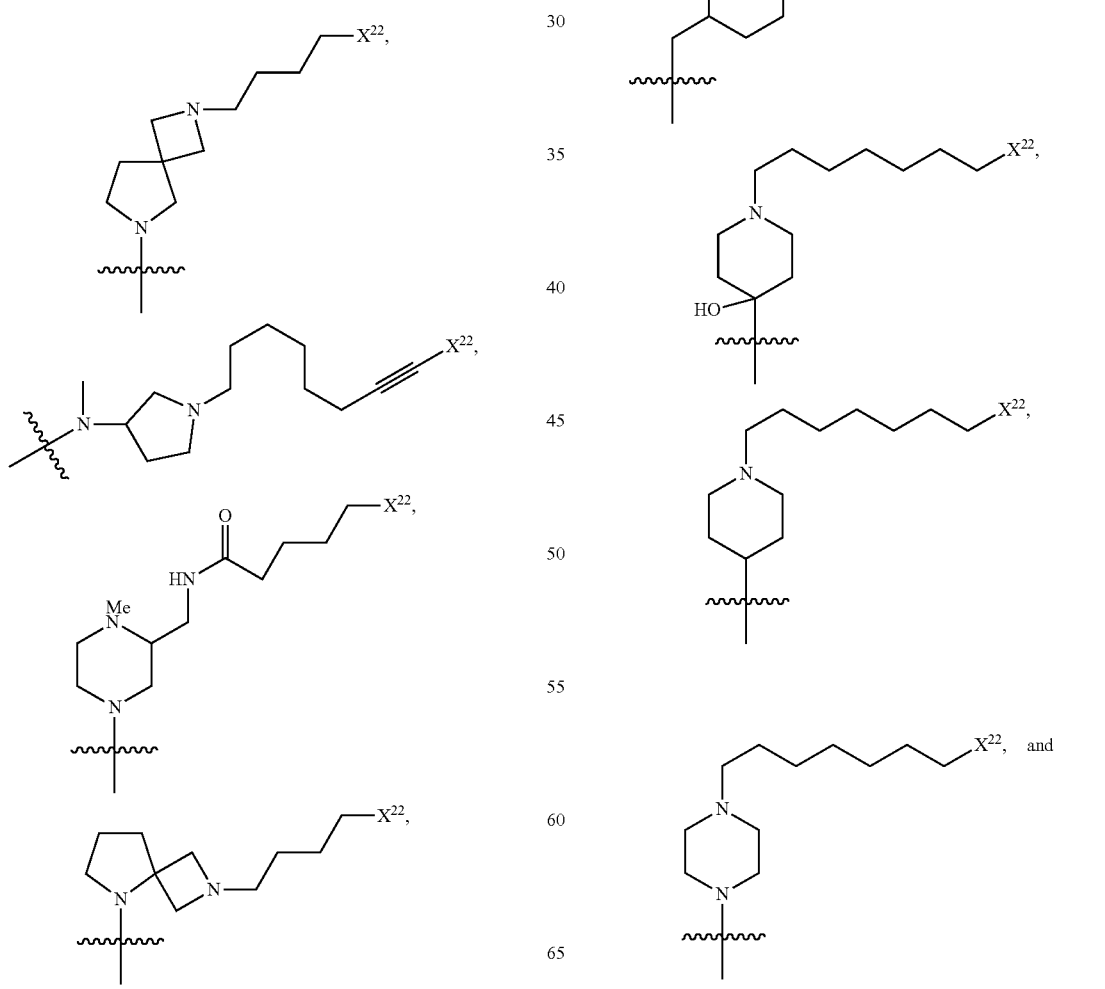

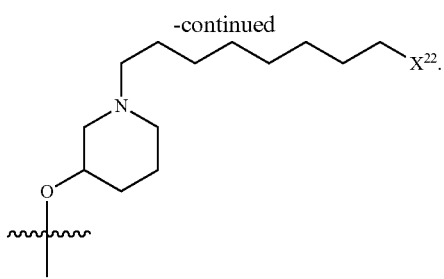
In additional embodiments, -(Tail) is selected from the group consisting of:
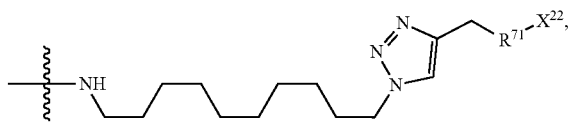
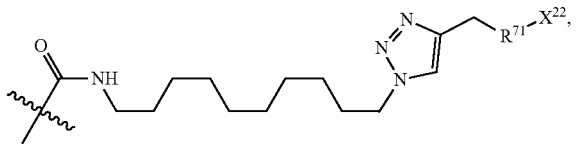
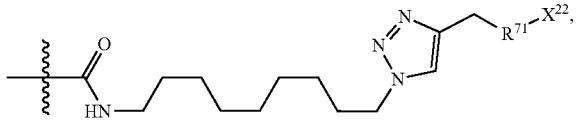
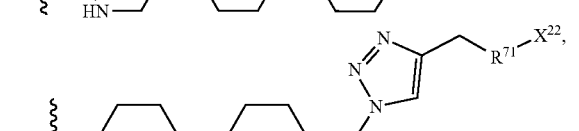
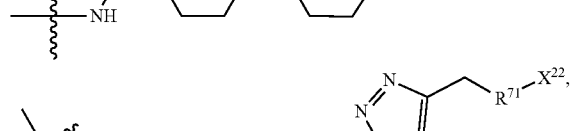
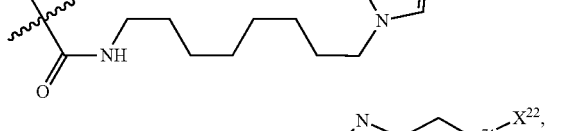

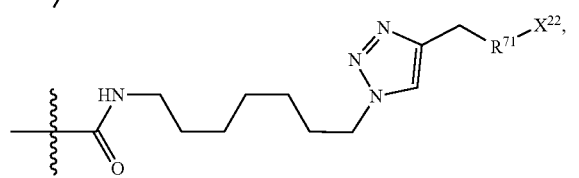
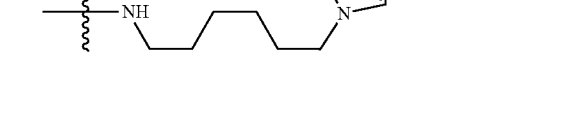
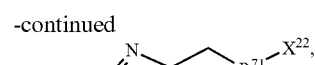
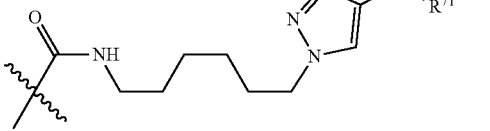
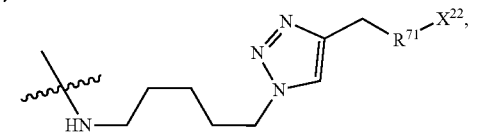
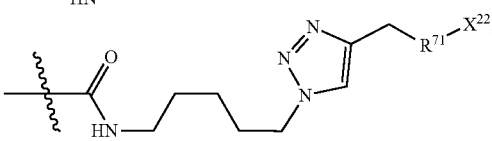

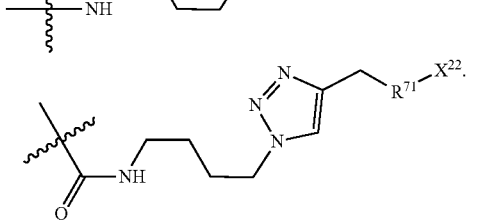
In additional embodiments, -(Tail) is selected from the group consisting of: PGP-158C$_3$
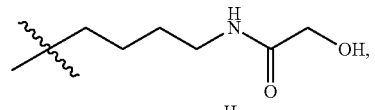
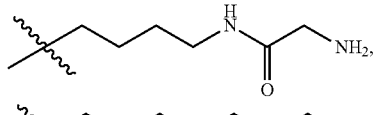

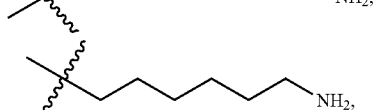
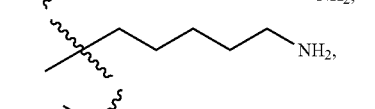
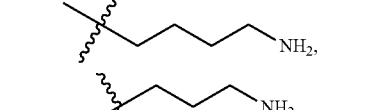
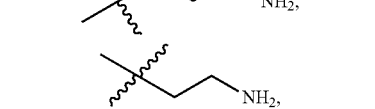
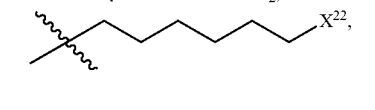

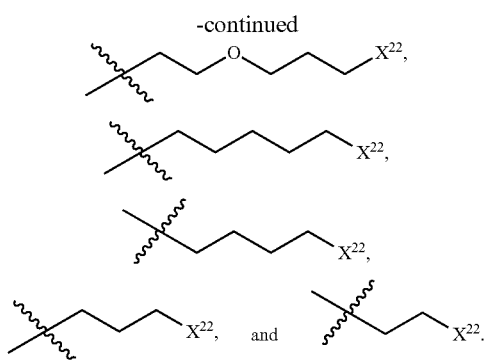
In the above embodiments $X^{22}$ is selected such that a compound that is sufficiently stable for the intended use results.
In additional embodiments, -(Tail) is selected from the group consisting of:
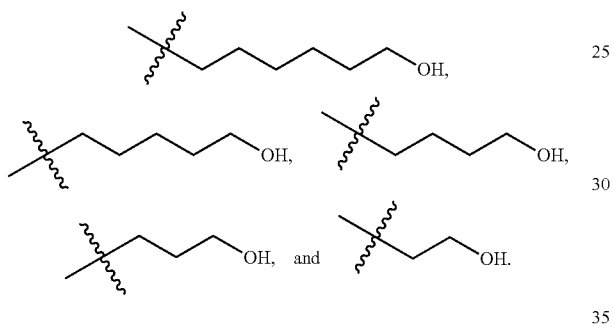
In certain embodiments, -(Tail) is selected from the group consisting of:
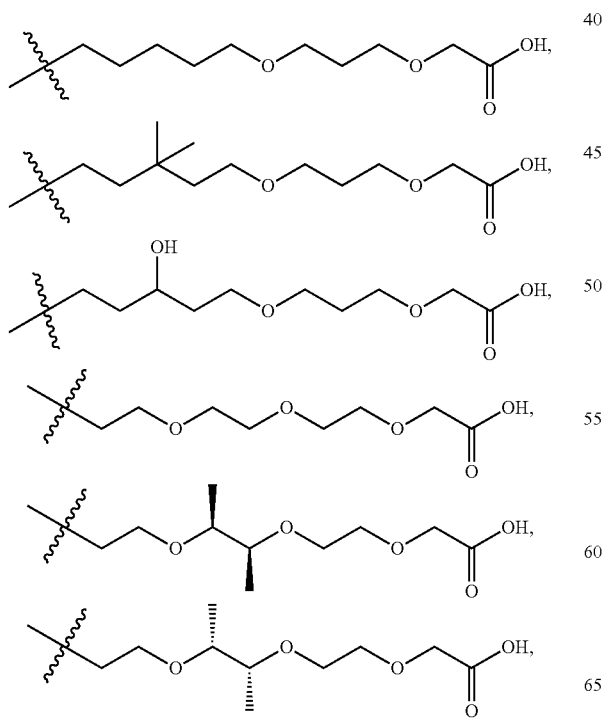
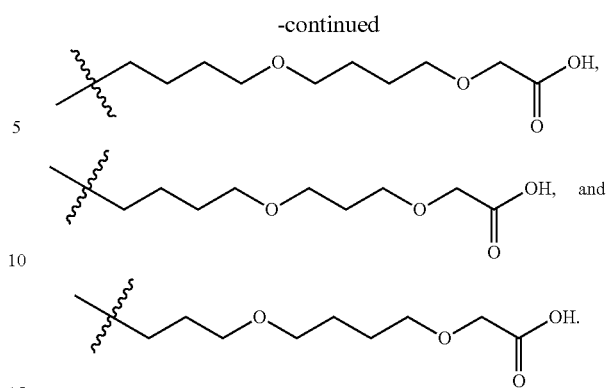
In certain embodiments -(Tail) is selected from the group consisting of:
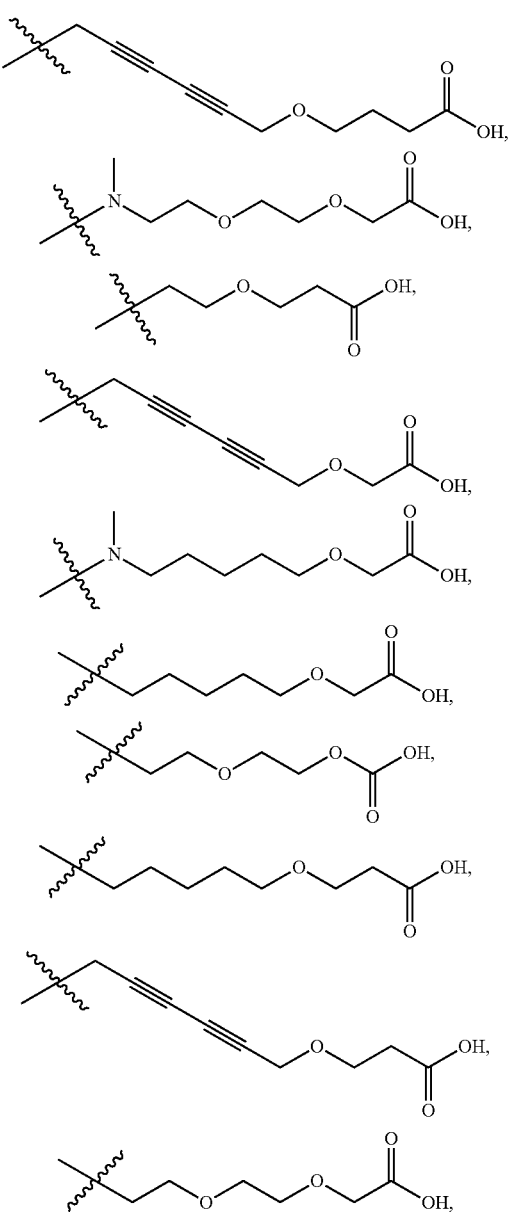

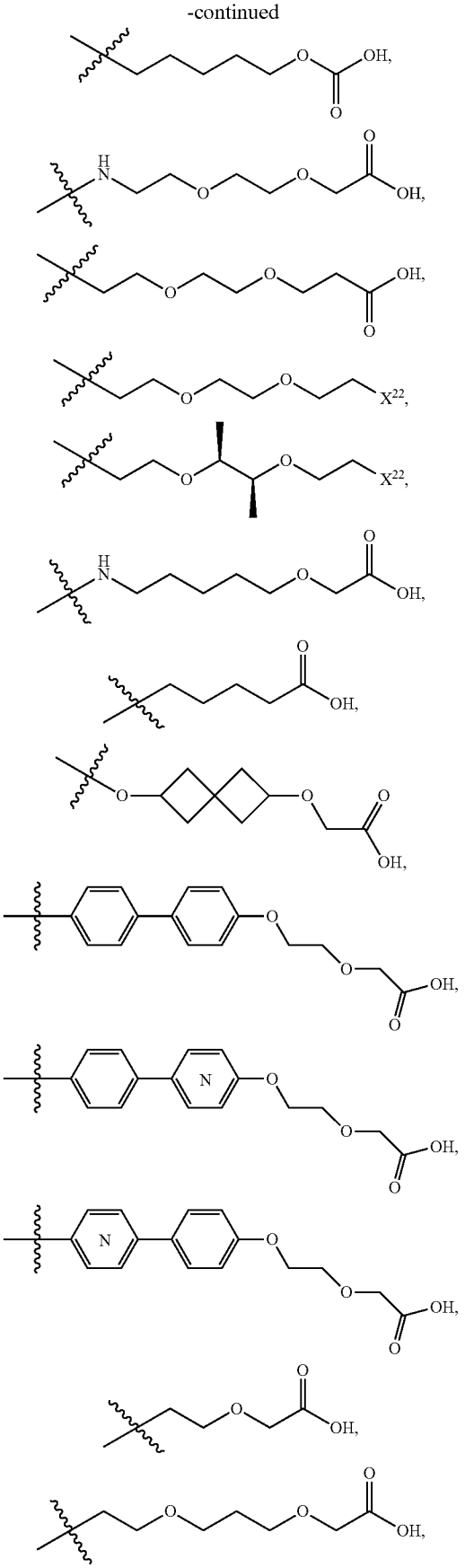
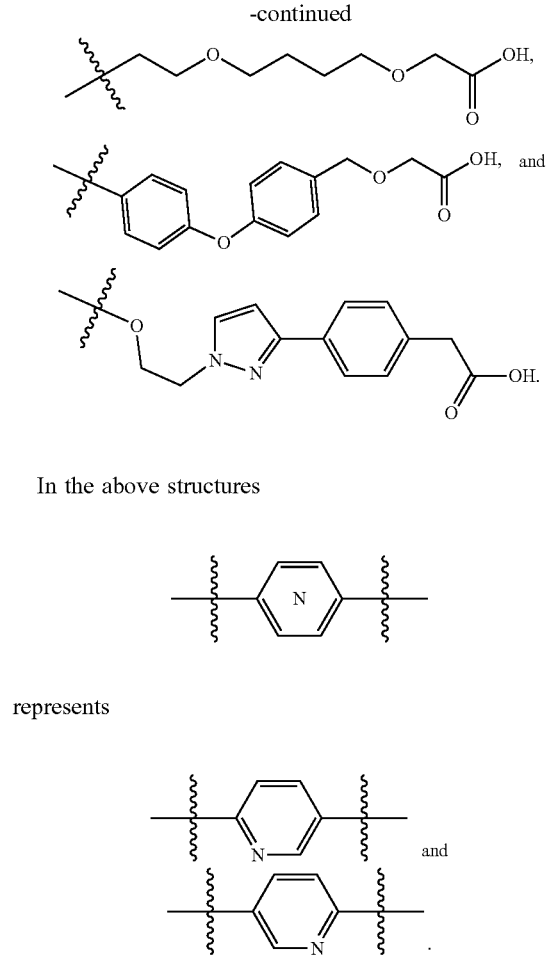
In the above structures
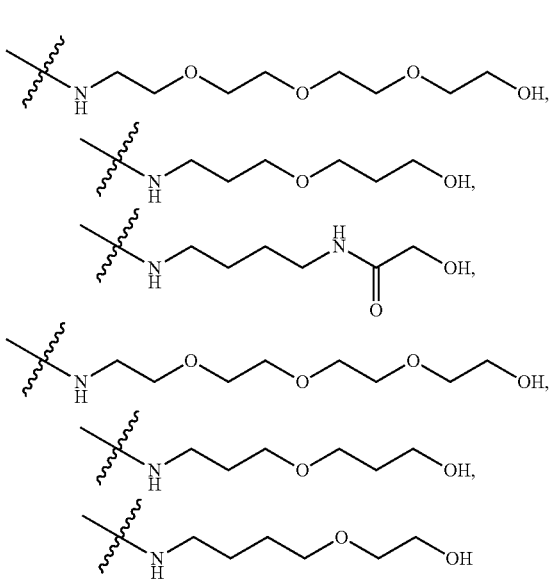
represents
and
.
In certain embodiments, -(Tail) can be a 4-24 carbon atom linear chains, wherein one or more the carbon atoms in the linear chain can be replaced or substituted with oxygen, nitrogen, amide, fluorinated carbon, etc., such as the following:

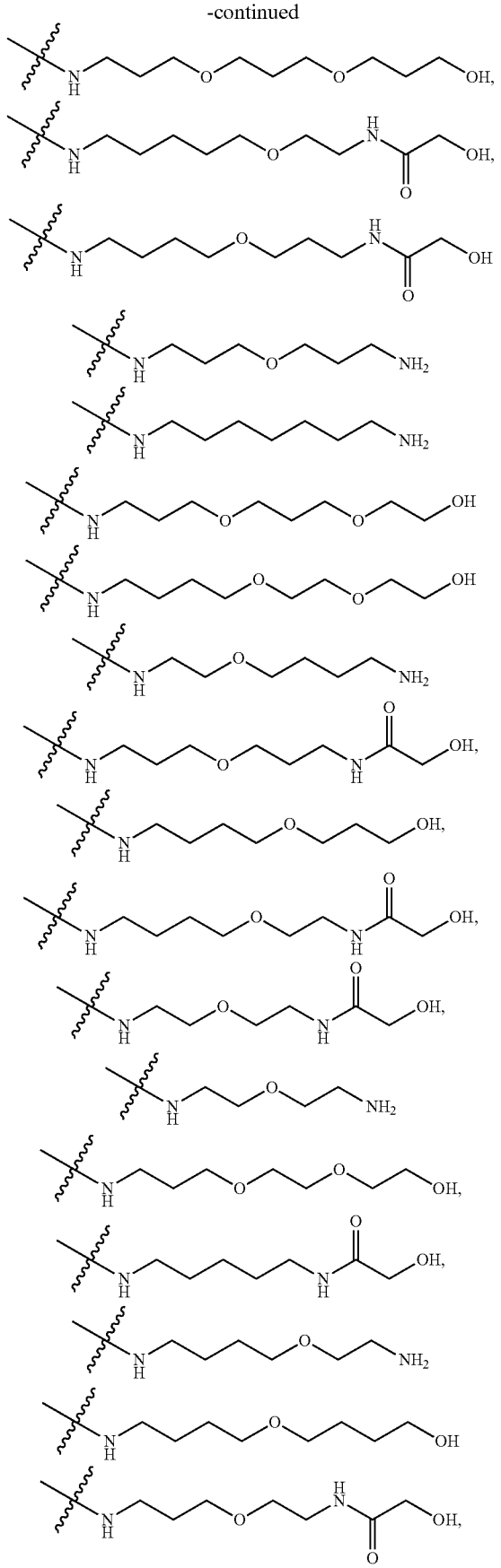
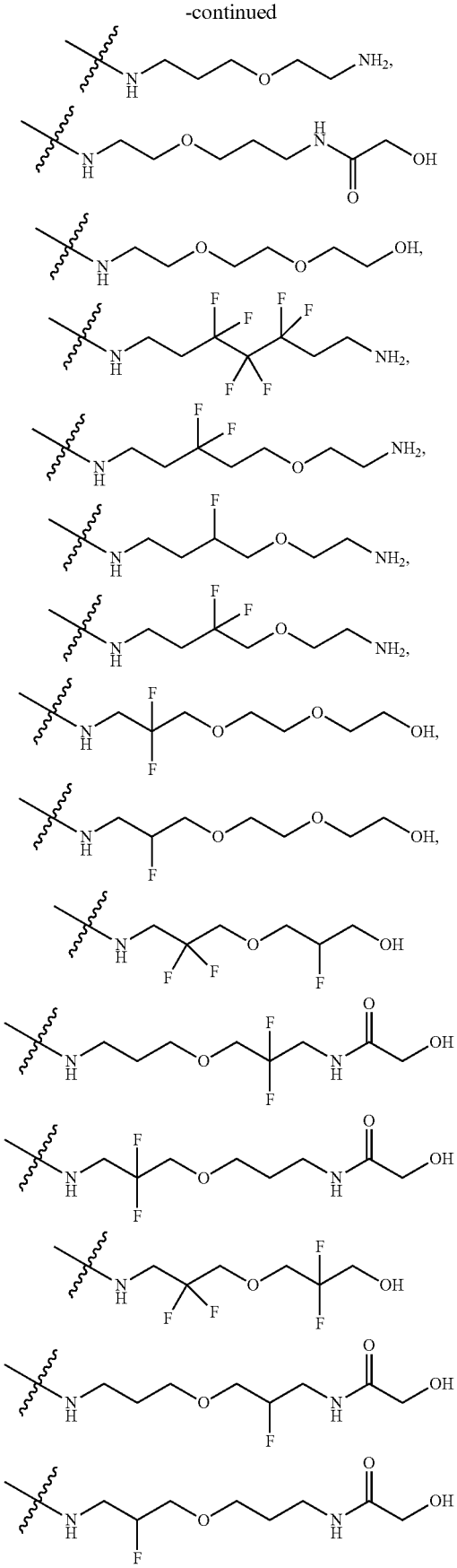

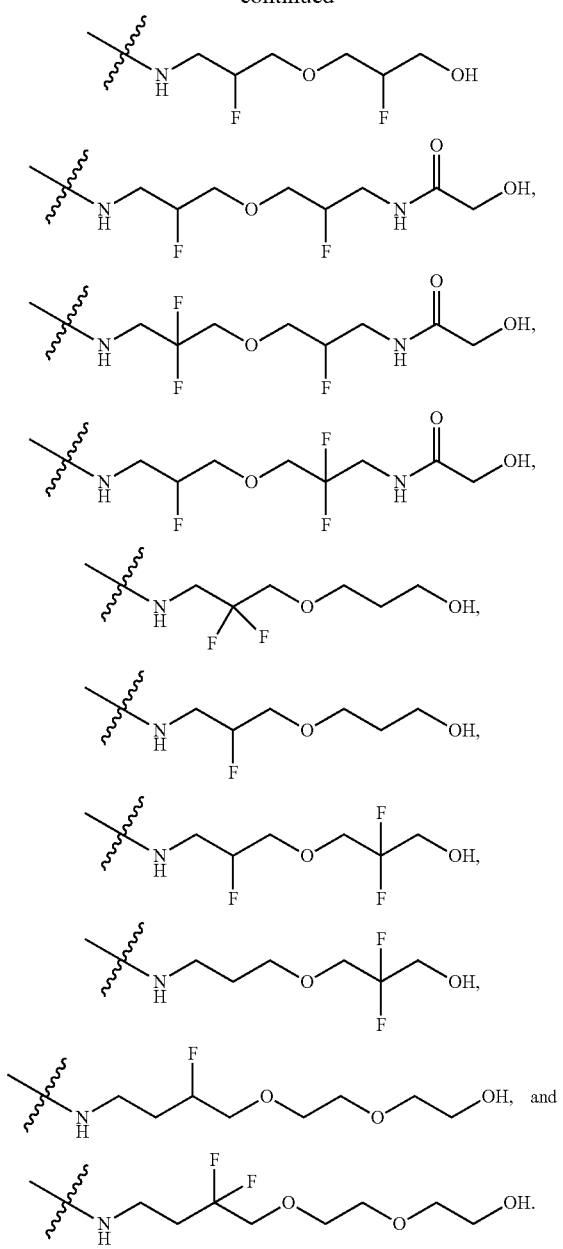

In certain embodiments, Tail can be a nonlinear chain, and can be, or include, aliphatic or aromatic or heteroaromatic cyclic moieties.

In certain embodiments, Tail may include contiguous, partially contiguous or non-contiguous ethylene glycol unit groups ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units, for example, 1, 2, 3, 4, 6, 6, 7, 8, 9, 10, 11 or 12 ethylene glycol units.

In certain embodiments, Tail may have 1, 2, 3, 4, 5, 6, 7, 8, 9, 10, 11, 12, 13, 14, or 15 fluorine substituents. In another embodiment Tail is perfluorinated. In yet another embodiment -Tail is a partially or fully fluorinated poly ether. Nonlimiting examples of fluorinated Tail moieties include:

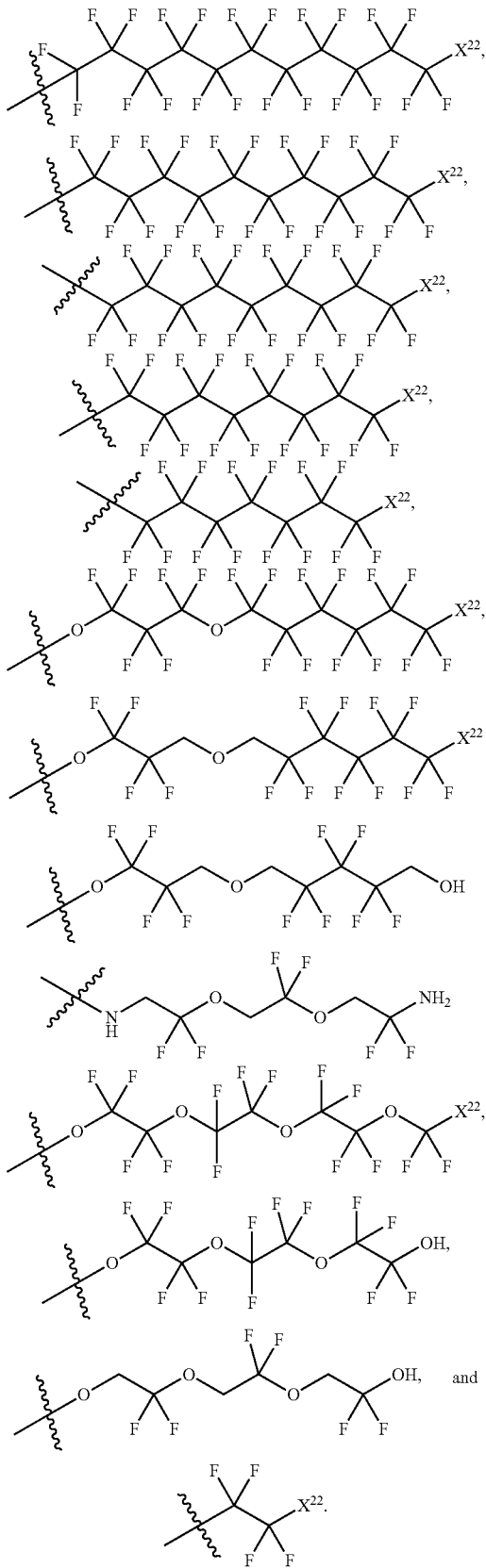

In certain embodiments, the length can be adjusted as desired or as found necessary for the desired application.

IV. Target Proteins

Degradation of cellular proteins is required for cell homeostasis and normal cell function, such as proliferation, differentiation and cell death. When this system becomes dysfunctional or does not identify and abate abnormal protein behavior in vivo, a disease state can arise in a host, such as a human. A large range of proteins can cause, modulate or amplify diseases in vivo, as well known to those skilled in the art, published in literature and patent filings as well as presented in scientific presentations.

Therefore, in some embodiments, a selected Degrader compound of the present invention can be administered in an effective amount to a host in need thereof to degrade a Target Protein that mediates a disorder to be treated. The selected protein target may modulate a disorder in a human via a mechanism of action such as modification of a biological pathway, pathogenic signaling or modulation of a signal cascade or cellular entry.

In other embodiments a selected Degron compound of the present invention can be administered in an effective amount to a host in need thereof to degrade a Target Protein that mediates a disorder to be treated. The selected protein target for degradation with a Degron may modulate a disorder in a human via a mechanism of action such as modification of a biological pathway, pathogenic signaling or modulation of a signal cascade or cellular entry.

In one embodiment, the Target Protein is a protein that is not druggable in the classic sense in that it does not have a binding pocket or an active site that can be inhibited or otherwise bound, and cannot be easily allosterically controlled. In another embodiment, the Target Protein is a protein that is druggable in the classic sense, yet for therapeutic purposes, degradation of the protein is preferred to inhibition.

The Target Protein is recruited with a Targeting Ligand, which is a ligand for the Target Protein. Typically the Targeting Ligand binds the Target Protein in a non-covalent fashion. In another embodiment, the Target Protein is covalently bound to the Degron in a manner that can be irreversible or reversible.

In some embodiments, the selected Target Protein is expressed from a gene that has undergone an amplification, translocation, deletion, or inversion event which causes or is caused by a medical disorder. In certain aspects, the selected Target Protein has been post-translationally modified by one, or a combination, of phosphorylation, acetylation, acylation including propionylation and crotylation, N-linked glycosylation, amidation, hydroxylation, methylation and polymethylation, O-linked glycosylation, pyroglutamoylation, myristoylation, farnesylation, geranylgeranylation, ubiquitination, sumoylation, or sulfation which causes or is caused by a medical disorder.

As contemplated herein, the present invention includes a Degrader with a Targeting Ligand that binds to a Target Protein of interest. The Target Protein is any amino acid sequence to which a Degrader can be bound which by degradation thereof, causes a beneficial therapeutic effect in vivo.

In one embodiment, the Target Protein is a non-endogenous peptide such as that from a pathogen or toxin. In another embodiment, the Target Protein can be an endogenous protein that mediates a disorder. The endogenous protein can be either the normal form of the protein or an aberrant form. For example, the Target Protein can be a mutant protein found in cancer cells, or a protein, for example, where a partial, or full, gain-of-function or loss-of-function is encoded by nucleotide polymorphisms. In some embodiments, the Degrader targets the aberrant form of the protein and not the normal form of the protein.

In another embodiment, the Target Protein can mediate an inflammatory disorder or an immune disorder, including an auto-immune disorder.

In one embodiment, the Target Protein is a non-endogenous protein from a virus, as non-limiting examples, HIV, HBV, HCV, RSV, HPV, CMV, SARS-CoV2, flavivirus, pestivirus, coronavirus, noroviridae, etc.

In one embodiment, the Target Protein is a non-endogenous protein from a bacteria, which may be for example, a gram positive bacteria, gram negative bacteria or other, and can be a drug-resistant form of bacteria.

In one embodiment, the Target Protein is a non-endogenous protein from a fungus. In one embodiment, the Target Protein is a non-endogenous protein from a prion. In one embodiment, the Target Protein is a protein derived from a eukaryotic pathogen, for example a protist, helminth, etc.

In one aspect, the Target Protein mediates chromatin structure and function. The Target Protein may mediate an epigenetic action such as DNA methylation or covalent modification of histones. An example is histone deacetylase (HDAC 1, 2, 3, 4, 5, 6, 7, 8, 9, 10 or 11). Alternatively, the Target Protein may be a bromodomain, which are readers of lysine acetylation (for example, BRD1, 2, 3, 4, 5, 6, 7, 8, 9 and T. FIG. 9 illustrates the proteins of the bromodomain family, which, for example, can act as Target Proteins according to the present invention.

Other nonlimiting examples of Target Proteins are a structural protein, receptor, enzyme, cell surface protein, a protein involved in apoptotic signaling, aromatase, helicase, mediator of a metabolic process (anabolism or catabolism), antioxidant, protease, kinase, oxidoreductase, transferase, hydrolase, lyase, isomerase, ligase, enzyme regulator, signal transducer, structural molecule, binding activity (protein, lipid carbohydrate), cell motility protein, membrane fusion protein, cell communication mediator, regulator of biological processes, behavioral protein, cell adhesion protein, protein involved in cell death, protein involved in transport (including protein transporter activity, nuclear transport, ion transporter, channel transporter, carrier activity, permease, secretase or secretion mediator, electron transporter, chaperone regulator, nucleic acid binding, transcription regulator, extracellular organization and biogenesis regulator, and translation regulator).

In some embodiments, the Target Protein is a modulator of a signaling cascade related to a known disease state. In another embodiment, the Target Protein mediates a disorder by a mechanism different from modulating a signaling cascade. Any protein in a eukaryotic system or a microbial system, including a virus, bacteria or fungus, as otherwise described herein, are targets for proteasomal degradation using the present invention. The Target Protein may be a eukaryotic protein, and in some embodiments, a human protein.

In certain embodiments, the Target Protein is RXR, DHFR, Hsp90, a kinase, HDM2, MDM2, BET bromodomain-containing protein, HDAC, IDH1, Mcl-1, human lysine methyltransferase, a nuclear hormone receptor, aryl hydrocarbon receptor (AHR), RAS, RAF, FLT, SMARC, KSR, NF2L, CTNB, CBLB, BCL.

In one embodiment, a bromodomain containing protein has histone acetyl transferase activity.

In one embodiment, the bromodomain containing protein is BRD2, BRD3, BRD4, BRDT or ASH1L.

In one embodiment, the bromodomain containing protein is a non-BET protein.

In one embodiment, the non-BET protein is BRD7 or BRD9.

In one embodiment, the FLT is not FLT 3. In one embodiment, the RAS is not RASK. In one embodiment, the RAF is not RAF1. In one embodiment, the SMARC is not SMARC2. In one embodiment, the KSR is not KSR1. In one embodiment, the NF2L is not NF2L2. In one embodiment, the CTNB is not CTNB1. In one embodiment, the BCL is not BCL6.

In some embodiments, the Target Protein is selected from: EGFR, FLT3, RAF1, SMARCA2, KSR1, NF2L2, CTNB1, CBLB, BCL6, and RASK.

In other embodiments, the Target Protein is not selected from: EGFR, FLT3, RAF1, SMARCA2, KSR1, NF2L2, CTNB1, CBLB, BCL6, and RASK.

In certain embodiments, the Targeting Ligand is an EGFR ligand, a FLT3 ligand, a RAF1 ligand, a SMARCA2 ligand, a KSR1 ligand, a NF2L2 ligand, a CTNB1 ligand, a CBLB ligand, a BCL6 ligand, or a RASK ligand.

In other embodiments, the Targeting Ligand is not an EGFR ligand, a FLT3 ligand, a RAF1 ligand, a SMARCA2 ligand, a KSR1 ligand, a NF2L2 ligand, a CTNB1 ligand, a CBLB ligand, a BCL6 ligand, or a RASK ligand.

The present invention may be used to treat a wide range of disease states and/or conditions, including any disease state and/or condition in which a protein is dysregulated and where a patient would benefit from the degradation of proteins.

For example, a Target Protein can be selected that is a known target for a human therapeutic, and the therapeutic can be used as the Targeting Ligand when incorporated into the Degrader according to the present invention. These include proteins which may be used to restore function in a polygenic disease, including for example B7.1 and B7, TINFR1m, TNFR2, NADPH oxidase, Bcl2/Bax and other partners in the apoptosis pathway, C5a receptor, HMG-CoA reductase, PDE V phosphodiesterase type, PDE IV phosphodiesterase type 4, PDE I, PDEII, PDEIII, squalene cyclase inhibitor, CXCR1, CXCR2, nitric oxide (NO) synthase, cyclo-oxygenase 1, cyclo-oxygenase 2, 5HT receptors, dopamine receptors, G Proteins, e.g., Gq, histamine receptors, 5-lipoxygenase, tryptase serine protease, thymidylate synthase, purine nucleoside phosphorylase, GAPDH trypanosomal, glycogen phosphorylase, Carbonic anhydrase, chemokine receptors, JAW STAT, RXR and similar, HIV 1 protease, HIV 1 integrase, influenza, neuraminidase, hepatitis B reverse transcriptase, sodium channel, multi drug resistance (MDR), protein P-glycoprotein (and MRP), tyrosine kinases, CD23, CD124, tyrosine kinase p56 lck, CD4, CD5, IL-2 receptor, IL-1 receptor, TNF-alphaR, ICAM1, Cat+ channels, VCAM, VLA-4 integrin, selectins, CD40/CD40L, neurokinins and receptors, inosine monophosphate dehydrogenase, p38 MAP Kinase, Ras/Raf/MER/ERK pathway, interleukin-1 converting enzyme, caspase, HCV, NS3 protease, HCV NS3 RNA helicase, glycinamide ribonucleotide formyl transferase, rhinovirus 3C protease, herpes simplex virus-1 (HSV-I), protease, cytomegalovirus (CMV) protease, poly (ADP-ribose) polymerase, cyclin dependent kinases, vascular endothelial growth factor, oxytocin receptor, microsomal transfer protein inhibitor, bile acid transport inhibitor, 5 alpha reductase inhibitors, angiotensin 11, glycine receptor, noradrenaline reuptake receptor, endothelin receptors, neuropeptide Y and receptor, estrogen receptors, androgen receptors, adenosine receptors, adenosine kinase and AMP deaminase, purinergic receptors (P2Y1, P2Y2, P2Y4, P2Y6, P2X1-7), farnesyltransferases, geranylgeranyl transferase, TrkA a receptor for NGF, beta-amyloid, tyrosine kinase Flk-IIKDR, vitronectin receptor, integrin receptor, Her-2/neu, telomerase inhibition, cytosolic phospholipaseA2 and EGF receptor tyrosine kinase. Additional protein targets include, for example, ecdysone 20-monooxygenase, ion channel of the GABA gated chloride channel, acetylcholinesterase, voltage-sensitive sodium channel protein, calcium release channel, and chloride channels. Still further Target Proteins include Acetyl-CoA carboxylase, adenylosuccinate synthetase, protoporphyrinogen oxidase, and enolpyruvylshikimate-phosphate synthase.

In certain embodiments, the Target Protein is derived from a kinase to which the Targeting Ligand is capable of binding or binds including, but not limited to, a tyrosine kinase (e.g., AATK, ABL, ABL2, ALK, AXL, BLK, BMX, BTK, CSF1R, CSK, DDR1, DDR2, EGFR, EPHA1, EPHA2, EPHA3, EPHA4, EPHA5, EPHA6, EPHA7, EPHA8, EPHA10, EPHB1, EPHB2, EPHB3, EPHB4, EPHB6, ERBB2, ERBB3, ERBB4, FER, FES, FGFR1, FGFR2, FGFR3, FGFR4, FGR, FLT1, FLT3, FLT4, FRK, FYN, GSG2, HCK, IGF1R, ILK, INSR, INSRR, IRAK4, ITK, JAK1, JAK2, JAK3, KDR, KIT, KSR1, LCK, LMTK2, LMTK3, LTK, LYN, MATK, MERTK, MET, MLTK, MST1R, MUSK, NPR1, NTRK1, NTRK2, NTRK3, PDGFRA, PDGFRB, PLK4, PTK2, PTK2B, PTK6, PTK7, RET, ROR1, ROR2, ROS1, RYK, SGK493, SRC, SRMS, STYK1, SYK, TEC, TEK, TEX14, TIE1, TNK1, TNK2, TNNI3K, TXK, TYK2, TYRO3, YES1, or ZAP70).

In certain embodiments, the Target Protein is derived from a kinase to which the Targeting Ligand is capable of binding or binds including, but not limited to, a serine/threonine kinase (e.g., casein kinase 2, protein kinase A, protein kinase B, protein kinase C, Raf kinases, CaM kinases, AKT1, AKT2, AKT3, ALK1, ALK2, ALK3, ALK4, Aurora A, Aurora B, Aurora C, CHK1, CHK2, CLK1, CLK2, CLK3, DAPK1, DAPK2, DAPK3, DMPK, ERK1, ERK2, ERK5, GCK, GSK3, HIPK, KHS1, LKB1, LOK, MAPKAPK2, MAPKAPK, MNK1, MSSK1, MST1, MST2, MST4, NDR, NEK2, NEK3, NEK6, NEK7, NEK9, NEK11, PAK1, PAK2, PAK3, PAK4, PAK5, PAK6, PIM1, PIM2, PLK1, RIP2, RIP5, RSK1, RSK2, SGK2, SGK3, SIK1, STK33, TAO1, TAO2, TGF-beta, TLK2, TSSK1, TSSK2, ULK1, or ULK2).

In certain embodiments, the Target Protein is derived from a kinase to which the Targeting Ligand is capable of binding or binds including, but not limited to a cyclin dependent kinase for example CDK1, CDK2, CDK3, CDK4, CDK5, CDK6, CDK7, CDK8, CDK9, CDK10, CDK11, CDK12, or CDK13.

In certain embodiments, the Target Protein is derived from a kinase to which the Targeting Ligand is capable of binding or binds including, but not limited to a leucine-rich repeat kinase (e.g., LRRK2).

In certain embodiments, the Target Protein is derived from a kinase to which the Targeting Ligand is capable of binding or binds including, but not limited to a lipid kinase (e.g., PIK3CA, PIK3CB) or a sphingosine kinase (e.g. S1P).

In certain embodiments, the Target Protein is derived from a BET bromodomain-containing protein to which the Targeting Ligand is capable of binding or binds including, but not limited to, ASH1L, ATAD2, BAZ1A, BAZ1B, BAZ2A, BAZ2B, BRD1, BRD2, BRD3, BRD4, BRD5, BRD6, BRD7, BRD8, BRD9, BRD10, BRDT, BRPF1, BRPF3, BRWD3, CECR2, CREBBP, EP300, FALZ, GCN5L2, KIAA1240, LOC93349, MLL, PB1, PCAF, PHIP, PRKCBP1, SMARCA2, SMARCA4, SP100, SP110, SP140, TAF1, TAF1L, TIF1a, TRIM28, TRIM33, TRIM66, WDR9, ZMYND11, and MLL4. In certain embodiments, a BET bromodomain-containing protein is BRD4.

In certain embodiments, the Target Protein is derived from a nuclear protein to which the Targeting Ligand is capable of binding or binds including, but not limited to, BRD2, BRD3, BRD4, Antennapedia Homeodomain Protein, BRCA1, BRCA2, CCAAT-Enhanced-Binding Proteins, histones, Polycomb-group proteins, High Mobility Group Proteins, Telomere Binding Proteins, FANCA, FANCD2, FANCE, FANCF, hepatocyte nuclear factors, Mad2, NF-kappa B, Nuclear Receptor Coactivators, CREB-binding protein, p55, p107, p130, Rb proteins, p53, c-fos, c-jun, c-mdm2, c-myc, and c-rel.

In certain embodiments, the Target Protein is a member of the Retinoid X Receptor (RXR) family and the disorder treated is a neuropsychiatric or neurodegenerative disorder. In certain embodiments, the Target Protein is a member of the Retinoid X Receptor (RXR) family and the disorder treated is schizophrenia.

In certain embodiments, the Target Protein is dihydrofolate reductase (DHFR) and the disorder treated is cancer. In certain embodiments, the Target Protein is dihydrofolate reductase (DHFR) and the disorder treated is microbial.

In certain embodiments, the Target Protein is dihydrofolate reductase from *Bacillus anthracis* (BaDHFR) and the disorder treated is anthrax.

In certain embodiments, the Target Protein is Heat Shock Protein 90 (HSP90) and the disorder treated is cancer.

In certain embodiments, the Target Protein is a kinase or phosphatase and the disorder treated is cancer.

In certain embodiments, the Target Protein is HDM2 and or MDM2 and the disorder treated is cancer.

In certain embodiments, the Target Protein is a BET bromodomain containing protein and the disorder treated is cancer.

In certain embodiments, the Target Protein is a lysine methyltransferase and the disorder treated is cancer.

In certain embodiments, the Target Protein belongs to the RAF family and the disorder treated is cancer.

In certain embodiments, the Target Protein belongs to the FKBP family and the disorder treated is an autoimmune disorder. In certain embodiments, the Target Protein belongs to the FKBP family and the disorder treated is organ rejection. In certain embodiments, the Target Protein belongs to the FKBP family and the compound is given prophylactically to prevent organ failure.

In certain embodiments, the Target Protein is an androgen receptor and the disorder treated is cancer.

In certain embodiments, the Target Protein is an estrogen receptor and the disorder treated is cancer.

In certain embodiments, the Target Protein is a viral protein and the disorder treated is a viral infection. In certain embodiments, the Target Protein is a viral protein and the disorder treated is HIV, HPV, SARS-CoV2, or HCV.

In certain embodiments, the Target Protein is an AP-1 or AP-2 transcription factor and the disorder treated is cancer.

In certain embodiments, the Target Protein is a HIV protease and the disorder treated is a HIV infection. In certain embodiments, the Target Protein is a HIV integrase and the disorder treated is a HIV infection. In certain embodiments, the Target Protein is a HCV protease and the disorder treated is a HCV infection. In certain embodiments, the treatment is prophylactic and the Target Protein is a viral protein.

In certain embodiments, the Target Protein is a member of the histone deacetylase (HDAC) family and the disorder is a neurodegenerative disorder. In certain embodiments, the Target Protein is a member of the histone deacetylase (HDAC) family and the disorder is Huntingon's, Parkinson's, Kennedy disease, amyotropic lateral sclerosis, Rubinstein-Taybi syndrome, or stroke.

In certain embodiments, Targeting Ligand forms a covalent bond with the Target Protein. Non-limiting examples of Target Proteins and Targeting Ligands utilizing a covalent bond include those described in "Covalent Inhibitors Design and Discovery" Eur J Med Chem. 2017 Sep. 29; 138:96-114. doi: 10.1016/j.ejmech.2017.06.019. "Lysine-Targeting Covalent Inhibitors." Angew Chem Int Ed Engl. 2017 Aug. 29. doi: 10.1002/anie.201707630; "Inhibition of Mcl-1 Through Covalent Modification of a Noncatalytic Lysine Side Chain." Nat Chem Biol. 2016 November; 12(11):931-936; "Proteome-wide Map of Targets of T790M-EGFR-Directed Covalent Inhibitors" Cell Chem. Biol. 2016 November: 24:1-13; "Global Profiling of Lysine Reactivity and Ligandability in the Human Proteome" Nat. Chem. 2017 Jul. 31, doi:10.1038/nchem.2826; "The Resurgence of Covalent Drugs" Nat. Rev. Drug Disc. 2011 10, 307-217; U.S. Pat. Nos. 8,008,309; and 9,790,226.

In other embodiments, the Target Protein is selected from DOTL1, CBP, WDR5, BRAF, KRAS, MCL1, PTPN2, HER2, and SHOC2. In another embodiment, the Target Protein is selected from UCHL1, USP6, USP14, and USP30. In another embodiment, the Target Protein is selected from USP1, USP2, USP4, USP6, USP7, USP8, USP9x, USP10, USP11, USP13, USP14, USP17, and USP28.

In some embodiments, the Target Protein is selected from 4QL1, 3SMR, 5EAL, 6DAK, 6DAR, and 6DAS.

In certain embodiments, the Target Protein as referred to herein is named by the gene that expresses it. The person skilled in the art will recognize that when a gene is referred to as a Target Protein, the protein encoded by the gene is the Target Protein. For example, ligands for the protein SMCA2 which is encoded by SMARCA2 are referred to as SMARCA2 Targeting Ligands.

Degradation of target proteins through "molecular glue" interactions have been investigated by many researchers. An example review of the field is Dong et al. "Molecular Glues for Targeted Protein Degradation: From Serendipity to Rational Discovery" *J. Med. Chem.* 2021, 64, 15, 10606-10620. See also, for example, Cao et al. "Defining molecular glues with a dual-nanobody cannabidiol sensor" *Nature Communications,* 2022, 13:815.

In certain embodiments a degron of the present invention degrades the target protein using a molecular glue mechanism. Research in the area of targeted protein degradation includes systemic studies of the "degrome" of zinc finger proteins. The C2H2 zinc finger degrome is present on several different target proteins (See, for example: Sievers et al. "Defining the human C2H2 zinc finger degrome targeted by thalidomide analogs through CRBN" *Science,* 2018, 362, eaat0572).

In certain embodiments, the Target Protein is ARID2. Yamamoto has shown that ARID2 can be a substrate for targeted protein degradation. ARID2 has been associated with poor prognosis and chemoresistant residual disease in multiple myeloma (Yamamoto et al. "ARID2 is a pomalidomide-dependent CRL4CRBN substrate in multiple myeloma cells" *Nature Chemical Biology,* 2020; 16, 1208-1217.

In certain embodiments, the Target Protein is aromatase. Aromatase has been identified as a substrate of cereblon and may be related to thrombocytopenia induced by treatment with pomalidomide or lenalidomide. See for example, Tochigi et al. "Aromatase is a novel neo-substrate of cereblon responsible for immunomodulatory drugs-induced thrombocytopenia" *Blood* (2020); 135, 24, 2146-2158. In certain embodiments a Degron described herein does not have aromatase degradation activity.

In certain embodiments, the Target Protein is CDK12. CDK12 binding with a degrading compound has been shown to facilitate the degradation of cyclin K. Degradation of cyclin K may be useful in the treatment of proliferative diseases such as cancer. See for example, Mayor-Ruiz et al. "Rational discovery of molecular glue degraders via scalable chemical profiling" *Nature Chemical Biology*, 2020, 16, 1199-1207; Slabicki et al. "The CDK8 inhibitor CR8 acts as a molecular glue degrader that depletes cyclin K", *Nature*, 2020, 585, 293-297; and Lv et al. "discovery of a molecular glue promoting CDK12-DDB1 interaction to trigger Cyclin K degradation" *BioRxiv*, 2020; doi:10.1101/2020.06.10.144303.

In certain embodiments, the Target Protein is casein kinase 1α (CK1α). CK1α degradation has been associated with myelodysplastic syndrome. Targeted protein degradation of CK1a has been shown by Teng et al. "Development of PDE6D and CK1α Degraders through Chemical Derivatization of FPFT-2216" *J. Med. Chem.* 2022 65, 1, 747-756.

In certain embodiments, the Target Protein is p63. The teratogenic effects of thalidomide have been associated with degradation of p63 isoforms. Compounds for the degradation of TAp63α and ΔNp63α have been developed. See, for example, Asatsyna-Okumura et al. "p63 is a cereblon substrate involved in thalidomide teratogenicity" *Nature Chemical Biology*, 2019, 15, 1077-1084.

In certain embodiments, the Target Protein is G1 to S phase transition protein (GSPT1). Targeted degradation has been demonstrated to lower GSPT 1 levels, exhibiting an antiproliferative effect. See, for example, Powell et al. "Selective Degradation of GSPT1 by Cereblon Modulators Identified via a Focused Combinatorial Library" *ACS Chem Biol.*, 2020, 15, 2722-2730; and Hansen et al. "Protein Degradation via CRL4CRBN Ubiquitin Ligase: Discovery and Structure-Activity Relationships of Novel Glutarimide Analogs That Promote Degradation of Aiolos and/or GSPT1" *J. Med. Chem.* 2018, 61, 2, 492-503.

In certain embodiments, the Target Protein is FAM83F. FAM83F has been implicated in oncogenesis, specifically esophageal squamous cell carcinoma, lung adenocarcinoma, glioma, and thyroid carcinoma. FAM83F degradation has been demonstrated to reduce the level of CK1α. See, for example, Dunbar et al. "IMiDs induce FAM83F degradation via an interaction with CK1α to attenuate Wnt signalling" *BioRxiv*, doi:10.1101/2020.05.25.114660.

In certain embodiments, the Target Protein is RBM39. Targeted degraders of RBM39 have been investigated in clinical studies involving solid tumors. Genetics studies indicate RBM39 may be involved in acute myeloid leukemia. Degradation of RBM39 is mediated though a molecular glue interaction with DCAF15. See, for example, Faust et al. "Structural complementarity facilitates E7820-mediated degradation of RBM39 by DCAF15", *Nature Chemical Biology*, 2020, 16, 7-14.

In certain embodiments, the Target Protein is SALL4. SALL4 has been implicated as one of the targets for thalidomide which resulted in the teratogenic effects of thalidomide. Hydroxythalidomide, a major metabolite of thalidomide, has been demonstrated to induce the degradation of SALL4 through complex formation with CRBN. For example, see Furihata et al. "Structural bases of IMiD selectivity that emerges by 5-hydroxythalidomide" *Nature Communications*, 2020, 11, 4748.

In certain embodiments, the Target Protein is interleukin enhancer-binding factor 2 (ILF2). TLF2 forms a heterodimer with ILF3 and regulates gene expression and cancer cell growth. Cancers regulated by ILF2 include breast cancer, gastric cancer, liver cancer, and non-small cell lung cancer. Targeted protein degraders of TLF2 have been shown to reliably induce the degradation of TLF2. See, for example, Lian et al. "Cereblon Promotes the Ubiquitination and Proteasomal Degradation of Interleukin Enhancer-Binding Factor 2" *The Protein Journal*, 2020, doi:10.1007/s10930-020-09918-9.

In certain embodiments, the Target Protein is promyelocytic leukemia zinc finger protein (PLZF and ZBTB16). ZBTB16, a CRBN neosubstrate, has been implicated in regulating spermatogenesis, immune function, and hematopoiesis. In particular, acute promyelocytic leukemia Targeted protein degraders of ZBTB16 have been disclosed in, for example, Matyskiela et al. "Cereblon Modulators Target ZBTB16 and Its Oncogenic Fusion Partners for Degradation via Distinct Structural Degrons" *ACS Chem. Biol.* 2020, 15, 12, 3149-3158.

In certain embodiments, the Target Protein is ZMYM2. ZMYM2 is a zinc-finger protein which has been implicated in a chimeric fusion gene with FGFR1. These fusions can lead to myeloid lymphoid neoplasms and acute leukemia. Researchers have developed compounds which target ZMYM2 and facilitate its degradation through ubiquitination. For example, see Renneville et al. "Avadomide Induces Degradation of ZMYM2 Fusion Oncoproteins in Hematologic Malignancies" *Blood Cancer Discovery*, 2021, 2, 250-265.

In other embodiments, the Target Protein is selected from ARID2, CDK1, CDK12-cyclin K, CDK13, CK1alpha, CSNK1A1, Cyclin K, E4F1, FAM83F, GSPT1, GSPT2, GZF1, IKZF1, IKZF2, IKZF3, IKZF4, ILF2, Myc, ODC1, p63, PDE6D, AB28, RARalpha-ZBTB16, RBM23, RBM39, RBM39, RNF166, SALL4, WBP4, ZBTB16, ZBTB16-RARalpha, ZBTB39, ZFP91, ZFP91, ZFP91, ZMYM2-FGFR1, ZMYM2-FLT3, ZNF198, ZNF276, ZNF276, ZNF517, ZNF582, ZNF653, ZNF654, ZNF692, ZNF787, ZNF827, and ZNF98.

V. Targeting Ligands

In certain aspects, the Targeting Ligand is a ligand which covalently or non-covalently binds to a Target Protein which has been selected for proteasomal degradation by the selected Degrader. A Targeting Ligand is a molecule or moiety (for example a peptide, nucleotide, antibody, antibody fragment, aptamer, biomolecule or other chemical structure) that binds to a Target Protein, and wherein the Target Protein is a mediator of disease in a host as described in detail below. Exemplary Target Ligands are provided in FIGS. 1A-8PPPPP and FIGS. 10-70.

In some embodiments, the Targeting Ligand binds to an endogenous protein which has been selected for degradation as a means to achieve a therapeutic effect on the host. Illustrative Targeting Ligands include: RXR ligands, DHFR ligands, Hsp90 inhibitors, kinase inhibitors, HDM2 and MDM2 inhibitors, compounds targeting Human BET bromodomain-containing proteins, HDAC inhibitors, ligands of MerTK, ligands of IDH1, ligands of Mcl-1, ligands of SMARCA2, ligands of EGFR, ligands of RAF, ligands of cRAF, human lysine methyltransferase inhibitors, angiogenesis inhibitors, nuclear hormone receptor compounds, immunosuppressive compounds, and compounds targeting the aryl hydrocarbon receptor (AHR), among numerous others. Targeting Ligands also considered to include their pharmaceutically acceptable salts, prodrugs and isotopic derivatives.

In certain aspects, the Targeting Ligand binds to a dehalogenase enzyme in a patient or subject or in a diagnostic assay and is a haloalkane (preferably a $C_1$-$C_{10}$ alkyl group which is substituted with at least one halo group, preferably a halo group at the distal end of the alkyl group (i.e., away from the Linker)). In still other embodiments, the Targeting Ligand is a haloalkyl group, wherein said alkyl group generally ranges in size from about 1 or 2 carbons to about 12 carbons in length, often about 2 to 10 carbons in length, often about 3 carbons to about 8 carbons in length, more often about 4 carbons to about 6 carbons in length. The haloalkyl groups are generally linear alkyl groups (although branched-chain alkyl groups may also be used) and are end-capped with at least one halogen group, preferably a single halogen group, often a single chloride group. Haloalkyl PT, groups for use in the present invention are preferably represented by the chemical structure —$(CH_2)_v$-Halo where v is any integer from 2 to about 12, often about 3 to about 8, more often about 4 to about 6. Halo may be any halogen, but is preferably $C_1$ or Br, more often $C_1$.

In certain embodiments, the Targeting Ligand is a retinoid X receptor (RXR) agonist or antagonist. Non-limiting examples include retinol, retinoic acid, bexarotene, docosahexenoic acid, compounds disclosed in WO 9929324, the publication by Canan Koch et al. (*J. Med. Chem.* 1996, 39, 3229-3234) titled "Identification of the First Retinoid X Receptor Homodimer Antagonist", WO 9712853, EP 0947496A1, WO 2016002968, and analogs thereof.

In certain embodiments, the Targeting Ligand is a DHFR agonist or antagonist. Non-limiting examples include folic acid, methotrexate, 8,10-dideazatetrahydrofolate compounds disclosed by Tian et al. (*Chem. Biol. Drug Des.* 2016, 87, 444-454) titled "Synthesis, Antifolate and Anticancer Activities of N5-Substituted 8,10-Dideazatetrahydrofolate Analogues", compounds prepared by Kaur et al. (*Biorg. Med. Chem. Lett.* 2016, 26, 1936-1940) titled "Rational Modification of the Lead Molecule: Enhancement in the Anticancer and Dihydrofolate Reductase Inhibitory Activity", WO 2016022890, compounds disclosed by Zhang et al. (*Int. J. Antimicrob. Agents* 46, 174-182) titled "New Small-Molecule Inhibitors of Dihydrofolate Reductase Inhibit *Streptococcus Mutans*", modified trimethoprim analogs developed by Singh et al. (*J. Med. Chem.* 2012, 55, 6381-6390) titled "Mechanism Inspired Development of Rationally Designed Dihydrofolate Reductase Inhibitors as Anticancer Agents", WO20111153310, and analogs thereof.

In certain embodiments, the Targeting Ligand derived from estrogen, an estrogen analog, SERM (selective estrogen receptor modulator), a SERD (selective estrogen receptor degrader), a complete estrogen receptor degrader, or another form of partial or complete estrogen antagonist or agonist. Examples are the partial anti-estrogens raloxifene and tamoxifen and the complete antiestrogen fulvestrant.

Non-limiting examples of anti-estrogen compounds are provided in WO2013/090921, WO 2014/203129, WO 2014/203132, and US2013/0178445 assigned to Olema Pharmaceuticals, and U.S. Pat. Nos. 9,078,871, 8,853,423, and 8,703,810, as well as US 2015/0005286, WO 2014/205136, and WO 2014/205138.

Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestrant; aromatase inhibitors such as aminoglutethimide, testolactone, anastrozole, exemestane, fadrozole, formestane, and letrozole; and antigonadotropins such as leuprorelin, cetrorelix, allylestrenol, chloromadinone acetate, cyproterone acetate, delmadinone acetate, dydrogesterone, medroxyprogesterone acetate, megestrol acetate, nomegestrol acetate, norethisterone acetate, progesterone, and spironolactone.

Other estrogenic ligands that can be used according to the present invention are described in U.S. Pat. Nos. 4,418,068; 5,478,847; 5,393,763; and 5,457,117, WO2011/156518, U.S. Pat. Nos. 8,455,534 and 8,299,112, 9,078,871; 8,853, 423; 8,703,810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/ 0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780, 497, 5,880,137, WO 2012/048058 and WO 2007/087684.

In certain embodiments, the Targeting Ligand is a HSP90 inhibitor identified in Vallee et al. (*J. Med. Chem.* 2011, 54, 7206-7219) titled "Tricyclic Series of Heat Shock Protein 90 (Hsp90) Inhibitors Part I: Discovery of Tricyclic Imidazo [4,5-C]Pyridines as Potent Inhibitors of the Hsp90 Molecular Chaperone", including YKB (N-[4-(3H-imidazo[4,5-C] Pyridin-2-yl)-9H-Fluoren-9-yl]-succinamide), a HSP90 inhibitors (modified) identified in Brough et al. (*J. Med. Chem.* 2008, 51, 196-218) titled "4,5-Diarylisoxazole Hsp90 Chaperone Inhibitors: Potential Therapeutic Agents for the Treatment of Cancer", including compound 2GJ (5-[2,4-dihydroxy-5-(1-methylethyl)phenyl]-n-ethyl-4-[4-(morpholin-4-ylmethyl)phenyl]isoxazole-3-carboxamide), the HSP90 inhibitor geldanamycin ((4E,6Z,8S,9S,10E,12S, 13R,14S,16R)-13-hydroxy-8,14,19-trimethoxy-4,10,12,16-tetramethyl-3,20,22-trioxo-2-azabicyclo[16.3.1](derivatized) or any of its derivatives (e.g. 17-alkylamino-17-desmethoxygeldanamycin ("17-AAG") or 17-(2-dimethylaminoethyl)amino-17-desmethoxygeldanamycin ("17-DMAG")), or a HSP90 inhibitor (modified) identified in Wright et al. (*Chem. Biol.* 2004, 11, 775-785) titled "Structure-Activity Relationships in Purine-Based Inhibitor Binding to Hsp90 Isoforms", including the HSP90 inhibitor PU3.

Other non-limiting examples of Hsp90 Targeting Ligands include SNX5422 currently in phase I clinical trials Reddy et al. (*Clin. Lymphoma Myeloma Leuk.* 2013, 13, 385-391) titled "Phase I Trial of the Hsp90 Inhibitor Pf-04929113 (Snx5422) in Adult Patients with Recurrent, Refractory Hematologic Malignancies", or NVP-AUY922 whose anticancer activity was assessed by Jensen et al. (*Breast Cancer Research: BCR* 2008, 10, $R^{33}$—$R^{33}$) titled "Nvp-Auy922: A Small Molecule Hsp90 Inhibitor with Potent Antitumor Activity in Preclinical Breast Cancer Models".

In certain embodiments, the Targeting Ligand is a kinase inhibitor identified in Millan et al. (*J. Med Chem.* 2011, 54, 7797-7814) titled "Design and Synthesis of Inhaled P38 Inhibitors for the Treatment of Chronic Obstructive Pulmonary Disease", including the kinase inhibitors Y1W and Y1X, a kinase inhibitor identified in Schenkel et al. (*J. Med Chem.* 2011, 54, 8440-8450) titled "Discovery of Potent and Highly Selective Thienopyridine Janus Kinase 2 Inhibitors", including the compounds 6TP and OTP, a kinase inhibitor identified in van Eis et al. (*Biorg. Med Chem. Lett.* 2011, 21, 7367-7372) titled "2,6-Naphthyridines as Potent and Selective Inhibitors of the Novel Protein Kinase C Isozymes", including the kinase inhibitors 07U and YCF identified in Lountos et al. (*J. Struct. Biol.* 2011, 176, 292-301) titled "Structural Characterization of Inhibitor Complexes with Checkpoint Kinase 2 (Chk2), a Drug Target for Cancer Therapy", including the kinase inhibitors XK9 and NXP, afatinib, fostamatinib, gefitinib, lenvatinib, vandetanib, Gleevec, pazopanib, AT-9283, TAE684, nilotanib, NVP-BSK805, crizotinib, JNJ FMS, foretinib, OSI-027, OSI-930, or OSI-906.

In certain embodiments, the Targeting Ligand is a HDM2/MDM2 inhibitor identified in Vassilev et al. (*Science* 2004, 303, 844-848) titled "In Vivo Activation of the P53 Pathway by Small-Molecule Antagonists of Mdm2", and Schneekloth et al. (*Bioorg. Med Chem. Lett.* 2008, 18, 5904-5908) titled "Targeted Intracellular Protein Degradation Induced by a Small Molecule: En Route to Chemical Proteomics", including the compounds nutlin-3, nutlin-2, and nutlin-1.

In certain embodiments, the Targeting Ligand is a Human BET Bromodomain Targeting Ligand identified in Filippakopoulos et al. (*Nature* 2010, 468, 1067-1073) titled "Selective Inhibition of Bet Bromodomains" such as JQ1; a ligand identified in Nicodeme et al. (*Nature* 2010, 468, 1119-1123) titled "Suppression of Inflammation by a Synthetic Histone Mimic"; Chung et al. (*J. Med. Chem.* 2011, 54, 3827-3838) titled "Discovery and Characterization of Small Molecule Inhibitors of the Bet Family Bromodomains"; a compound disclosed in Hewings et al. (*J. Med. Chem.* 2011, 54, 6761-6770) titled "3,5-Dimethylisoxazoles Act as Acetyl-Lysine-Mimetic Bromodomain Ligands"; a ligand identified in Dawson et al. (*Nature* 2011, 478, 529-533) titled "Inhibition of Bet Recruitment to Chromatin as an Effective Treatment for MLL-Fusion Leukaemia"; or a ligand identified in the following patent applications US 2015/0256700, US 2015/0148342, WO 2015/074064, WO 2015/067770, WO 2015/022332, WO 2015/015318, and WO 2015/011084.

In certain embodiments, the Targeting Ligand is a HDAC Targeting Ligand identified in Finnin et al. (*Nature* 1999, 401, 188-193) titled "Structures of a Histone Deacetylase Homologue Bound to the Tsa and Saha Inhibitors", or a ligand identified as Formula (I) in PCT WO0222577.

In certain embodiments, the Targeting Ligand is a Human Lysine Methyltransferase ligand identified in Chang et al. (*Nat Struct Mol Biol* 2009, 16, 312-317) titled "Structural Basis for G9a-Like Protein Lysine Methyltransferase Inhibition by Bix-01294", a ligand identified in Liu et al. (*J Med Chem* 2009, 52, 7950-7953) titled "Discovery of a 2,4-Diamino-7-Aminoalkoxyquinazoline as a Potent and Selective Inhibitor of Histone Lysine Methyltransferase G9a", azacitidine, decitabine, or an analog thereof.

In certain embodiments, the Targeting Ligand is an angiogenesis inhibitor. Non-limiting examples of angiogenesis inhibitors include: GA-1, estradiol, testosterone, ovalicin, fumagillin, and analogs thereof.

In certain embodiments, the Targeting Ligand is an immunosuppressive compound. Non-limiting examples of immunosuppressive compounds include: AP21998, hydrocortisone, prednisone, prednisolone, methylprednisolone, beclometasone dipropionate, methotrexate, ciclosporin, tacrolimus, actinomycin, and analogues thereof.

In certain embodiments, the Targeting Ligand is an Aryl Hydrocarbon Receptor (AHR) ligand. Non-limiting examples of AHR ligands include: apigenin, SR1, LGC006, and analogues thereof.

In certain embodiments, the Targeting Ligand is a MerTK or Mer Targeting ligand. Non-limiting examples of MerTK Targeting Ligands are included in WO2013/177168 and WO2014/085225, both titled "Pyrimidine Compounds for the Treatment of Cancer" filed by Wang, et al.

In certain embodiments, the Targeting Ligand is an EGFR ligand. In certain embodiments the Targeting Ligand is an EGRF ligand selected from Afatinib, Dacomitinib, Neratinib, Poziotinib, and Canertinib, or derivatives thereof.

In certain embodiments, the Targeting Ligand is a FLT3 Ligand. In certain embodiments, the Targeting Ligand is a FLT3 ligand selected from Tandutinib, Lestaurtinib, Sorafenib, Midostaurin, Quizartinib, and Crenolanib.

In certain embodiments, the Targeting Ligand is a RAF inhibitor. In certain embodiments the Targeting Ligand is a RAF inhibitor selected from Dabrafenib, Regorafenib, and Vemurafenib.

In certain embodiments the Targeting Ligand is a cRAF inhibitor.

In some embodiments, the Targeting Ligand is an Ubc9 SUMO E2 ligase 5F6D Targeting Ligand including but not limited to those described in "Insights into the Allosteric Inhibition of the SUMO E2 Enzyme Ubc9." Hewitt, W. M., et. al. (2016) Angew. Chem. Int. Ed. Engl. 55: 5703-5707.

In another embodiment, the Targeting Ligand is a Tank1 Targeting Ligand including but not limited to those described in "Structure of human tankyrase 1 in complex with small-molecule inhibitors PJ34 and XAV939." Kirby, C. A., Cheung, A., Fazal, A., Shultz, M. D., Stams, T, (2012) *Acta Crystallogr., Sect. F* 68: 115-118; and "Structure-Efficiency Relationship of [1,2,4]Triazol-3-ylamines as Novel Nicotinamide Isosteres that Inhibit Tankyrases." Shultz, M. D., et al. (2013) *J. Med. Chem.* 56: 7049-7059.

In another embodiment, the Targeting Ligand is a SH2 domain of pp60 Src Targeting Ligand including but not limited to those described in "Requirements for Specific Binding of Low Affinity Inhibitor Fragments to the SH2 Domain of pp60Src Are Identical to Those for High Affinity Binding of Full Length Inhibitors," Gudrun Lange, et al., *J. Med. Chem.* 2003, 46, 5184-5195.

In another embodiment, the Targeting Ligand is a Sec7 domain Targeting Ligand including but not limited to those described in "The Lysosomal Protein Saposin B Binds Chloroquine," Huta, B. P., et al., (2016) Chemmedchem 11: 277.

In another embodiment, the Targeting Ligand is a Saposin-B Targeting Ligand including but not limited to those described in "The structure of cytomegalovirus immune modulator UL141 highlights structural Ig-fold versatility for receptor binding" I. Nemcovicova and D. M. Zajonc Acta Cryst. (2014). D70, 851-862.

In another embodiment, the Targeting Ligand is a Protein 5100-A7 20WS Targeting Ligand including but not limited to those described in "2WOS STRUCTURE OF HUMAN S100A7 IN COMPLEX WITH 2,6 ANS" DOI: 10.2210/pdb2wos/pdb; and "Identification and Characterization of Binding Sites on S100A7, a Participant in Cancer and Inflammation Pathways." Leon, R., Murray, et al., (2009) Biochemistry 48: 10591-10600.

In another embodiment, the Targeting Ligand is a Phospholipase A2 Targeting Ligand including but not limited to those described in "Structure-based design of the first potent and selective inhibitor of human non-pancreatic secretory phospholipase A2" Schevitz, R. W., et al., Nat. Struct. Biol. 1995, 2, 458-465.

In another embodiment, the Targeting Ligand is a PHIP Targeting Ligand including but not limited to those described in "A Poised Fragment Library Enables Rapid Synthetic Expansion Yielding the First Reported Inhibitors of PHIP(2), an Atypical Bromodomain" Krojer, T.; et al. Chem. Sci. 2016, 7, 2322-2330.

In another embodiment, the Targeting Ligand is a PDZ Targeting Ligand including but not limited to those described in "Discovery of Low-Molecular-Weight Ligands for the AF6 PDZ Domain" Mangesh Joshi, et al. Angew. Chem. Int. Ed. 2006, 45, 3790-3795.

In another embodiment, the Targeting Ligand is a PARP15 Targeting Ligand including but not limited to those described in "Structural Basis for Lack of ADP-ribosyltransferase Activity in Poly(ADP-ribose) Polymerase-13/Zinc Finger Antiviral Protein." Karlberg, T., et al., (2015) J. Biol. Chem. 290: 7336-7344.

In another embodiment, the Targeting Ligand is a PARP14 Targeting Ligand including but not limited to those described in "Discovery of Ligands for ADP-Ribosyltransferases via Docking-Based Virtual Screening" Andersson, C. D., et al. (2012) J. Med. Chem. 55: 7706-7718; "Family-wide chemical profiling and structural analysis of PARP and tankyrase inhibitors" Wahlberg, E., et al. (2012) Nat. Biotechnol. 30: 283-288; "Discovery of Ligands for ADP-Ribosyltransferases via Docking-Based Virtual Screening" Andersson, C. D., et al. (2012) J. Med. Chem. 55: 7706-7718.

In another embodiment, the Targeting Ligand is a MTH1 Targeting Ligand including but not limited to those described in "MTH1 inhibition eradicates cancer by preventing sanitation of the dNTP pool" Helge Gad, et. al. Nature, 2014, 508, 215-221.

In another embodiment, the Targeting Ligand is a mPGES-1 Targeting Ligand including but not limited to those described in "Crystal Structures of mPGES-1 Inhibitor Complexes Form a Basis for the Rational Design of Potent Analgesic and Anti-Inflammatory Therapeutics." Luz, J. G., et al., (2015) J. Med. Chem. 58: 4727-4737.

In another embodiment, the Targeting Ligand is a FLAP-5-lipoxygenase-activating protein Targeting Ligand including but not limited to those described in "Crystal structure of inhibitor-bound human 5-lipoxygenase-activating protein" Ferguson, A. D., McKeever, B. M., Xu, S., Wisniewski, D., Miller, D. K., Yamin, T. T., Spencer, R. H., Chu, L., Ujjainwalla, F., Cunningham, B. R., Evans, J. F., Becker, J. W. (2007) *Science* 317: 510-512.

In another embodiment, the Targeting Ligand is a FA Binding Protein Targeting Ligand including but not limited to those described in "A Real-World Perspective on Molecular Design." Kuhn, B.; et al. *J. Med. Chem.* 2016, 59, 4087-4102.

In another embodiment, the Targeting Ligand is a BCL2 Targeting Ligand including but not limited to those described in "ABT-199, a potent and selective BCL-2 inhibitor, achieves antitumor activity while sparing platelets." Souers, A. J., et al. (2013) NAT. MED. (N.Y.) 19: 202-208.

In another embodiment, the Targeting Ligand is a NF2L2 Targeting Ligand.

In another embodiment, the Targeting Ligand is a CTNNB1 Targeting Ligand.

In another embodiment, the Targeting Ligand is a CBLB Targeting Ligand.

In another embodiment, the Targeting Ligand is a BCL6 Targeting Ligand.

In another embodiment, the Targeting Ligand is a RASK Targeting Ligand.

In another embodiment, the Targeting Ligand is a TNIK Targeting Ligand.

In another embodiment, the Targeting Ligand is a MEN1 Targeting Ligand.

In another embodiment, the Targeting Ligand is a PI3Ka Targeting Ligand.

In another embodiment, the Targeting Ligand is a IDO1 Targeting Ligand.

In another embodiment, the Targeting Ligand is a MCL1 Targeting Ligand.

In another embodiment, the Targeting Ligand is a PTPN2 Targeting Ligand.

In another embodiment, the Targeting Ligand is a HER2 Targeting Ligand.

In another embodiment, the Targeting Ligand is an EGFR Targeting Ligand. In one embodiment the Targeting Ligand is selected from erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer). The linker can be placed on these Targeting Ligands in any location that does not interfere with the Ligands binding to EGFR.

Non-limiting examples of Linker binding locations are provided in the below tables. In one embodiment, the EGFR Targeting Ligand binds the L858R mutant of EGFR. In another embodiment, the EGFR Targeting Ligand binds the T790M mutant of EGFR. In another embodiment, the EGFR Targeting Ligand binds the C797G or C797S mutant of EGFR. In one embodiment, the EGFR Targeting Ligand is selected from erlotinib, gefitinib, afatinib, neratinib, and dacomitinib and binds the L858R mutant of EGFR. In another embodiment, the EGFR Targeting Ligand is selected from osimertinib, rociletinib, olmutinib, naquotinib, nazartinib, PF-06747775, Icotinib, Neratinib, Avitinib, Tarloxotinib, PF-0645998, Tesevatinib, Transtinib, WZ-3146, WZ8040, and CNX-2006 and binds the T790M mutant of EGFR. In another embodiment, the EGFR Targeting Ligand is EAI045 and binds the C797G or C797S mutant of EGFR.

In one embodiment, the protein target and Targeting Ligand pair are chosen by screening a library of ligands. Such a screening is exemplified in "Kinase Inhibitor Profiling Reveals Unexpected Opportunities to Inhibit Disease-Associated Mutant Kinases" by Duong-Ly et al.; Cell Reports 14, 772-781 Feb. 2, 2016.

In one embodiment, the protein target and Targeting Ligand pair are discovered by screening promiscuous kinase binding ligands for context-specific degradation. Non-limiting examples of targeting ligands are shown below and are found in "Optimized Chemical Proteomics Assay for Kinase Inhibitor Profiling" Guillaume Médard, Fiona Pachl, Benjamin Ruprecht, Susan Klaeger, Stephanie Heinzlmeir, Dominic Helm, Huichao Qiao, Xin Ku, Mathias Wilhelm, Thomas Kuehne, Zhixiang Wu, Antje Dittmann, Carsten Hopf, Karl Kramer, and Bernhard Kuster J. Proteome Res., 2015, 14(3), pp 1574-1586:

315    316
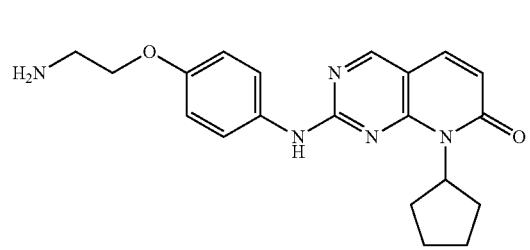
VI16743
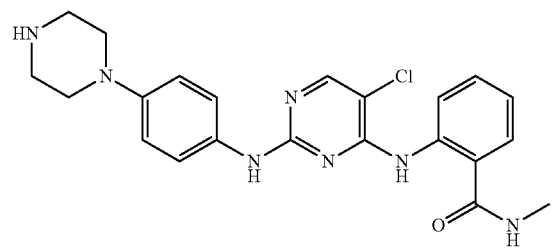
CTx-0294885
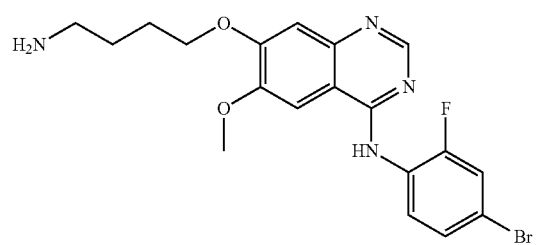
Vandetanib
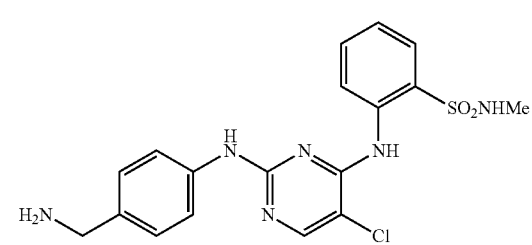
CTx-related
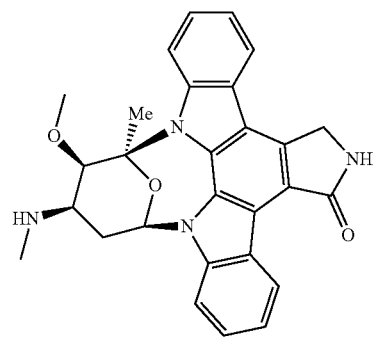
Staurosporine
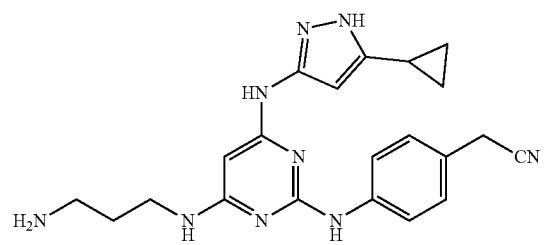
DOI: 10.1021/acschembio.5b00847
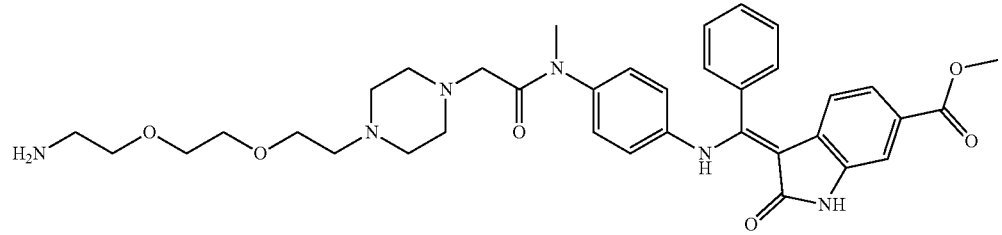
Nintedanib
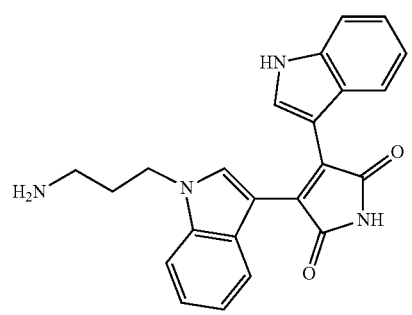
bisindolylmaleimide III
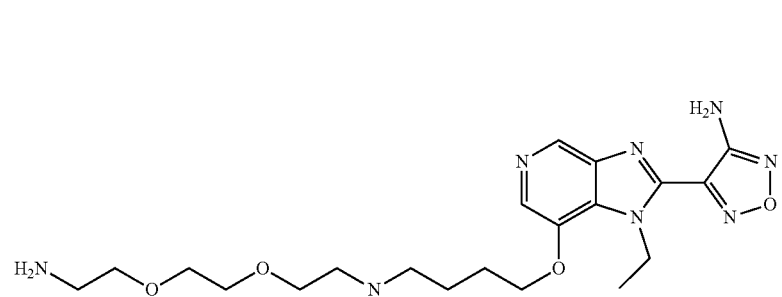
AKT probe -continued
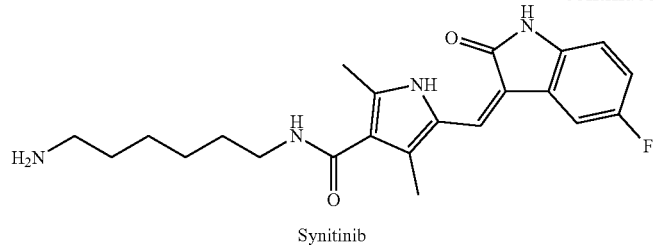
Synitinib
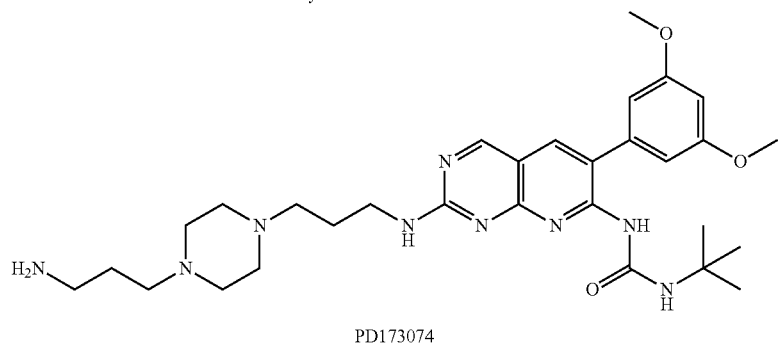
PD173074
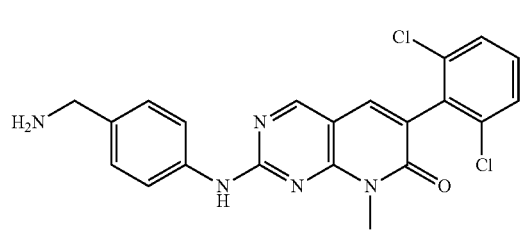
PD173955
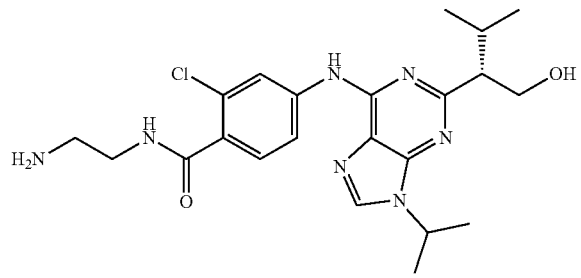
Puralanol B
CZC8004
These ligands can be attached to linkers as shown below:
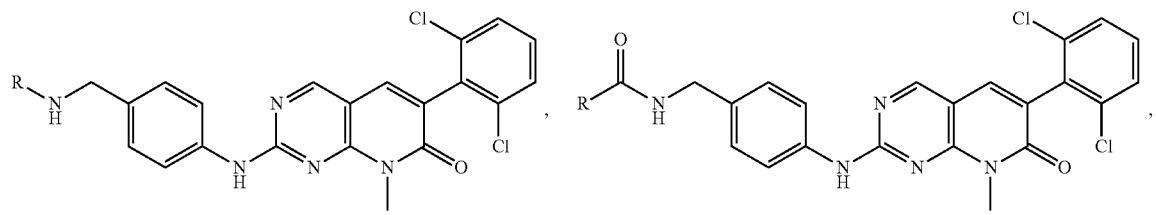
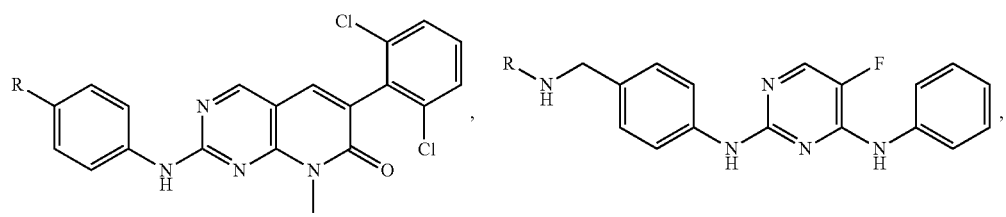

-continued
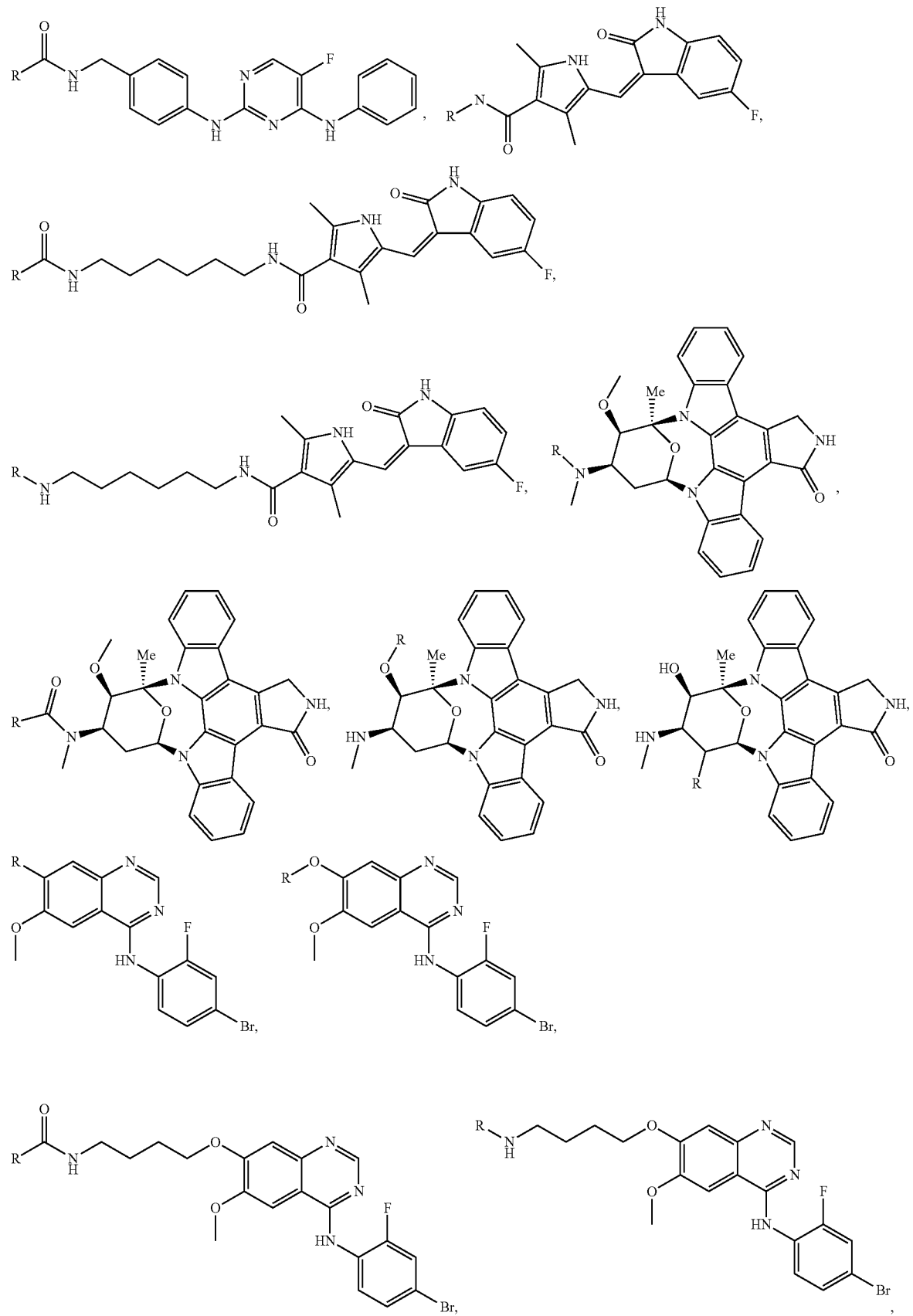

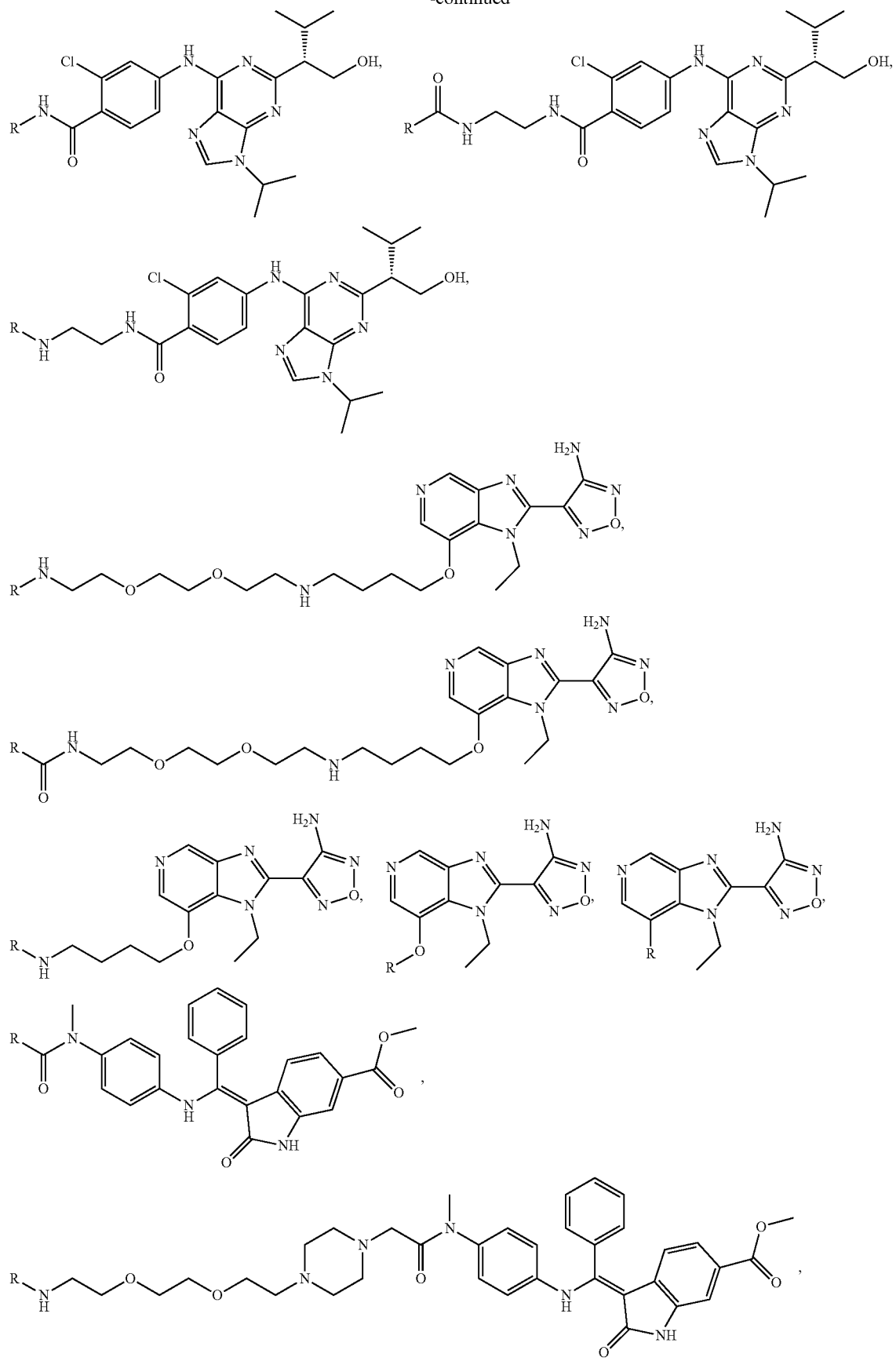

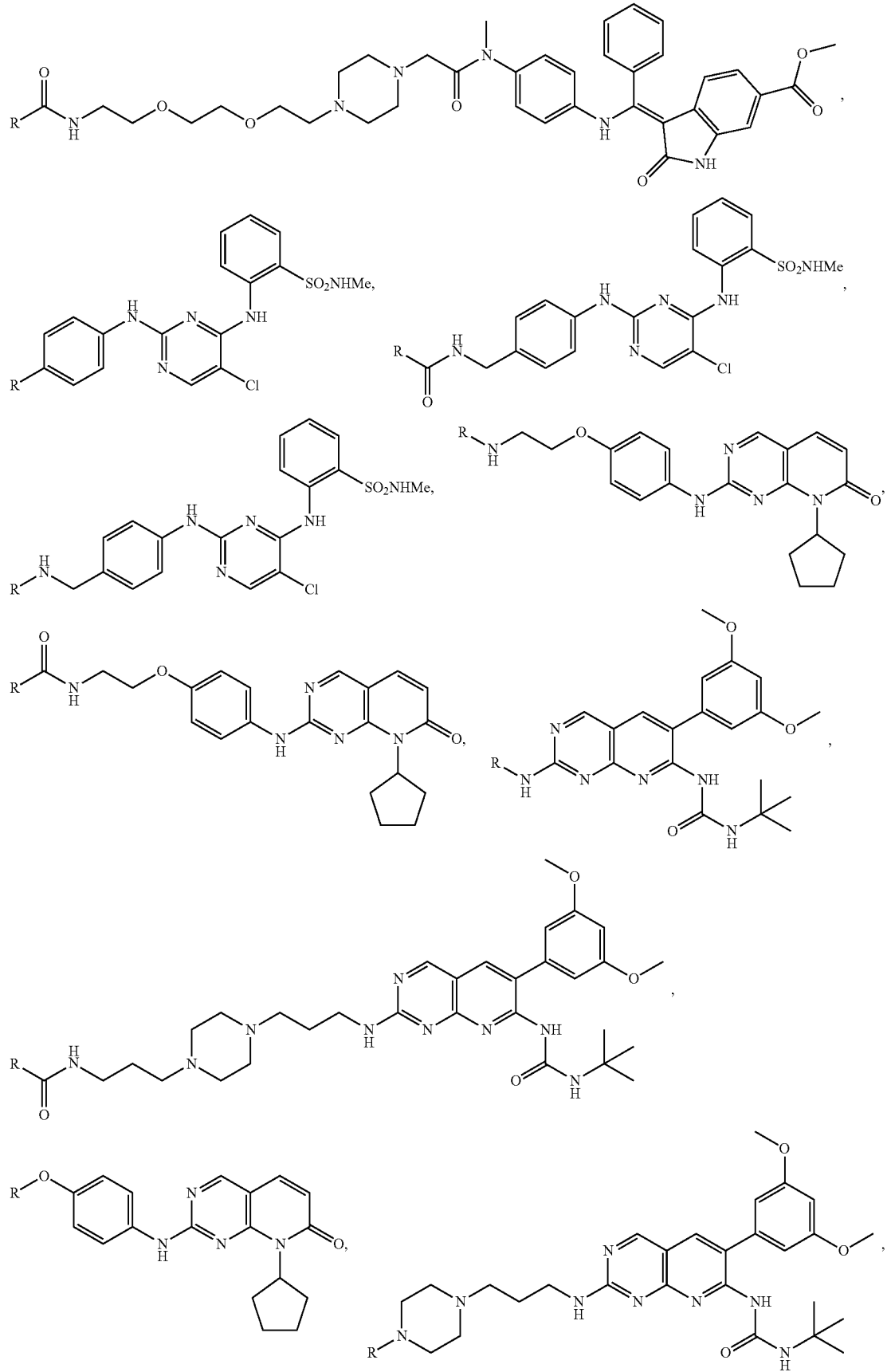

-continued
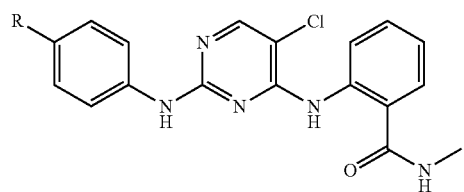
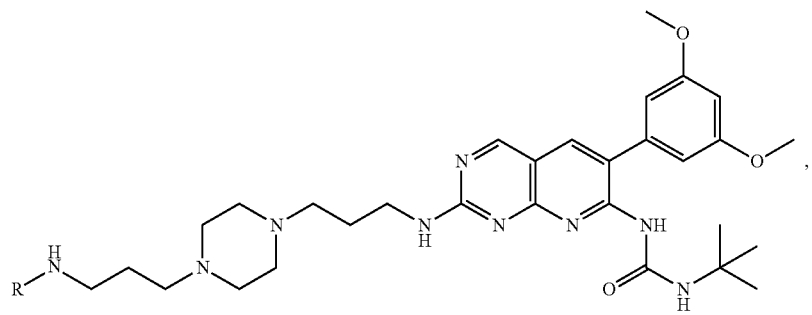
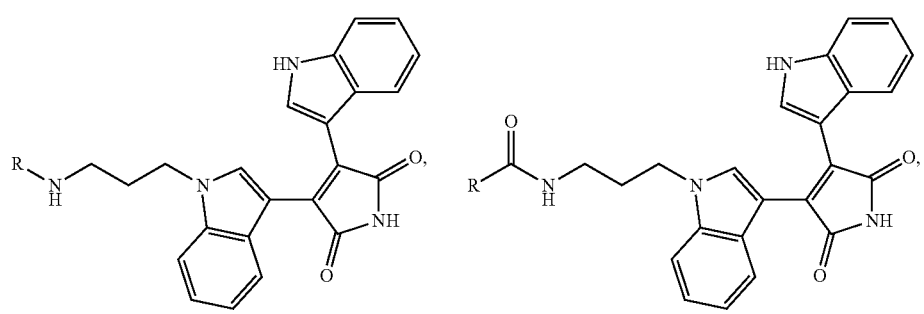
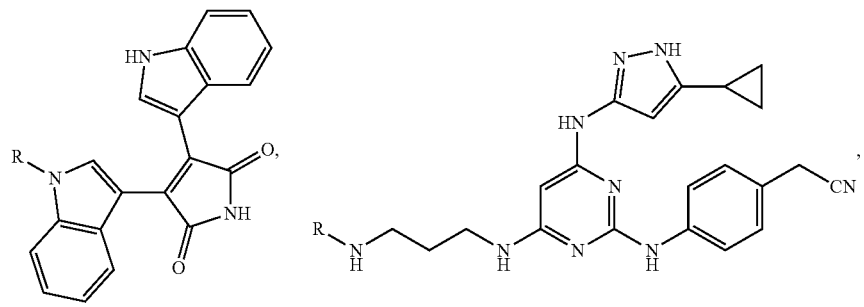
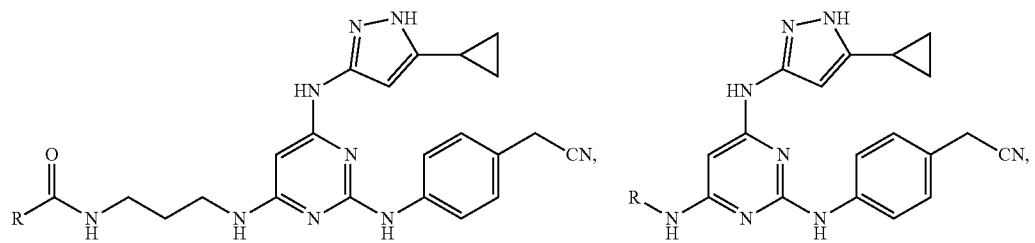
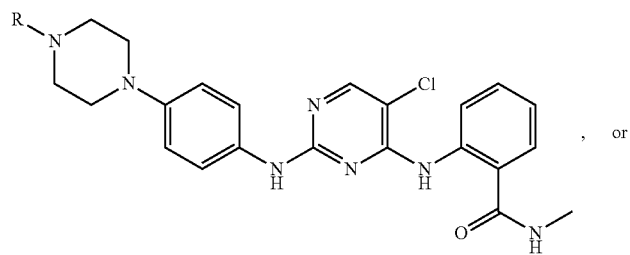, or

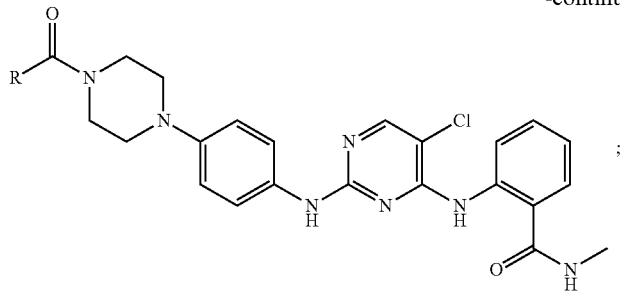

wherein:

R is the point at which the Linker is attached.

In another embodiment, the Targeting Ligand is selected from a DOTL1-Ligand, a CBP Ligand, an ERK1 Ligand, an ERK2 Ligand, a JAK2 Ligand, an FGFR3 Ligand, an FGFR4 Ligand, a WDR5 Ligand, a PAK4 Ligand, a BRAF Ligand, a KRAS Ligand, a BTK Ligand, and a SHOC2 Ligand. In another embodiment, the Targeting Ligand is selected from a UCHL1 Ligand, a USP1 Ligand, a USP2 Ligand, a USP4 Ligand, a USP6 Ligand, a USP7 Ligand, a USP8 Ligand, a USP9x Ligand, a USP10 Ligand, a USP 11 Ligand, a USP13 Ligand, a USP14 Ligand, a USP17 Ligand, and a USP28 Ligand.

In certain aspects the Targeting Ligand is a CSF1R Targeting Ligand.

In certain aspects the Targeting Ligand is a DGK Targeting Ligand.

In certain aspects the Targeting Ligand is a HPK1Targeting Ligand.

In certain aspects the Targeting Ligand is a BCL6Targeting Ligand.

In certain aspects the Targeting Ligand is a SOS1 Targeting Ligand.

In certain aspects the Targeting Ligand is a TYK2 Targeting Ligand.

In certain aspects the Targeting Ligand is a USP1 Targeting Ligand.

In certain aspects the Targeting Ligand is a Co-REST Targeting Ligand.

In certain embodiments the Targeting Ligand is a TYK2 Targeting Ligand of Formula:

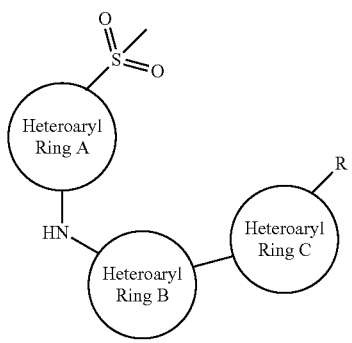

or

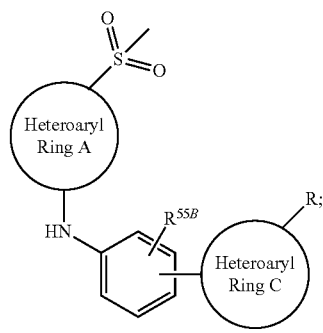

wherein:
R is the attachment point where Linker is attached;
Heteroaryl Ring A is a heteroaryl group optionally substituted with 1, 2, or 3 substituents selected from $R^{55A}$;
Heteroaryl Ring B is a heteroaryl group optionally substituted with 1, 2, or 3 substituents selected from $R^{55B}$;
Heteroaryl Ring C is a heteroaryl group optionally substituted with 1, 2, or 3 substituents selected from $R^{55C}$; and
$R^{55A}$, $R^{55B}$, and $R^{55C}$ are independently selected at each instance from alkyl, haloalkyl, halogen, cyano, —$NR^7R^8$, and —$OR^7$.

In certain embodiments Heteroaryl Ring A is pyridine.

In certain embodiments Heteroaryl Ring B is pyridine.

In certain embodiments Heteroaryl Ring C is pyridine.

In certain embodiments the Targeting Ligand is a SOS1 Targeting Ligand of Formula:

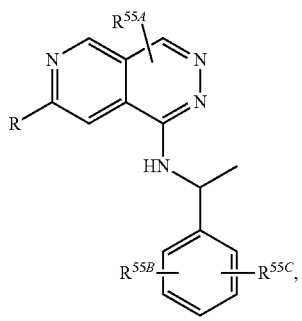

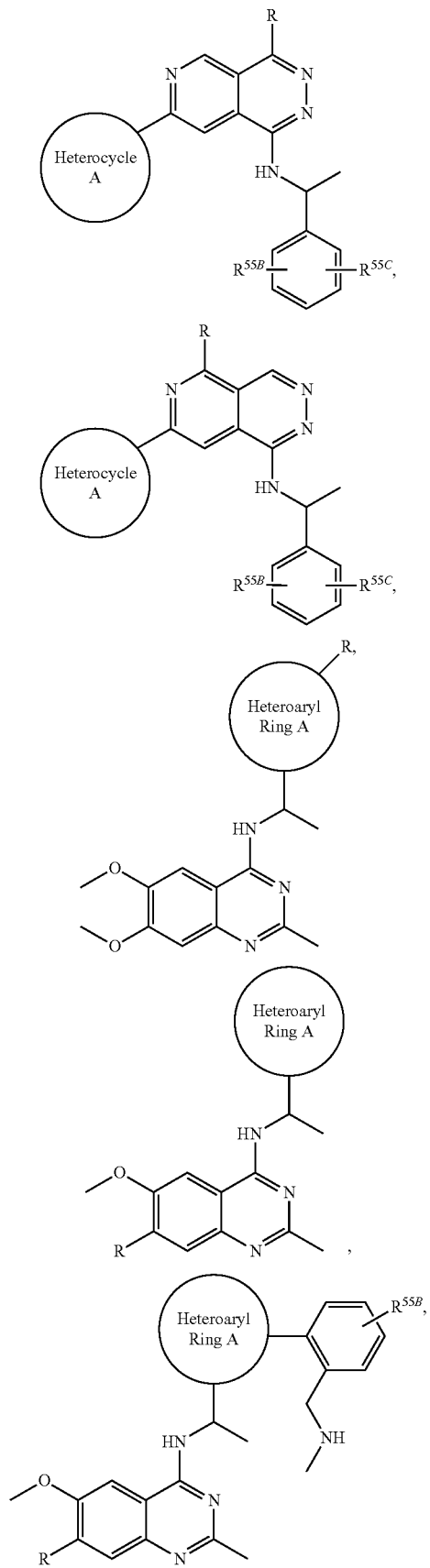

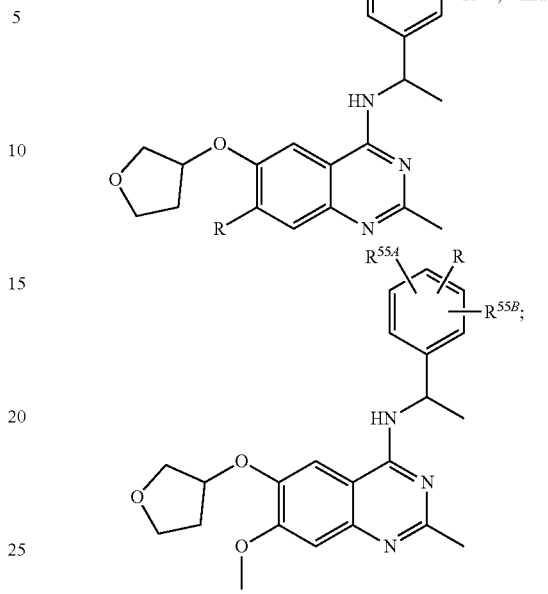

wherein:

Heterocycle A is a five or six membered heterocycle optionally substituted with an $R^7$ group and also optionally substituted with 1 or 2 substituents independently selected from alkyl, haloalkyl, hydroxyl, and halogen.

In certain embodiments, the Targeting Ligand is a Pax2 Targeting Ligand. For example a Targeting Ligand described in E. Grimley, et al. "Inhibition of Pax2 Transcription Activation with a Small Molecule that Targets the DNA Binding Domain." ACS Chem. Biol. 2017, 12, 724-734) or in S. T. J. Bradford, et al. "Identification of Pax protein inhibitors that suppress target gene expression and cancer cell proliferation." Cell Chem. Biol. 2022, 29, 1-11).

In certain embodiments the Pax2 Targeting Ligand is of Formula:

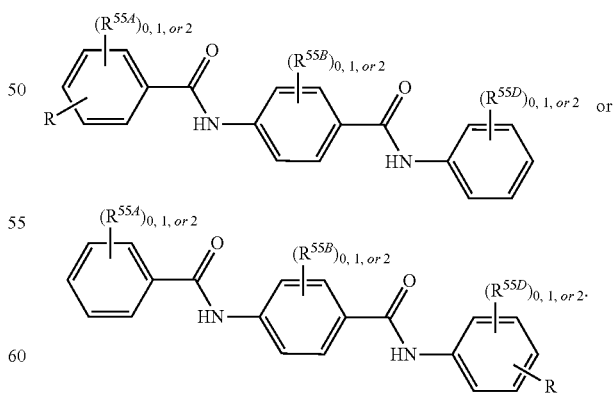

wherein $R^{55D}$ is independently selected at each instance from alkyl, haloalkyl, halogen, cyano, —C(O)NR$^7$R$^8$, —C(O)OR$^7$, —NR$^7$R$^8$, and —OR$^7$; and $R^{55A}$ and $R^{55B}$ are as defined above.

In certain embodiments the Pax2 Targeting Ligand is selected from:
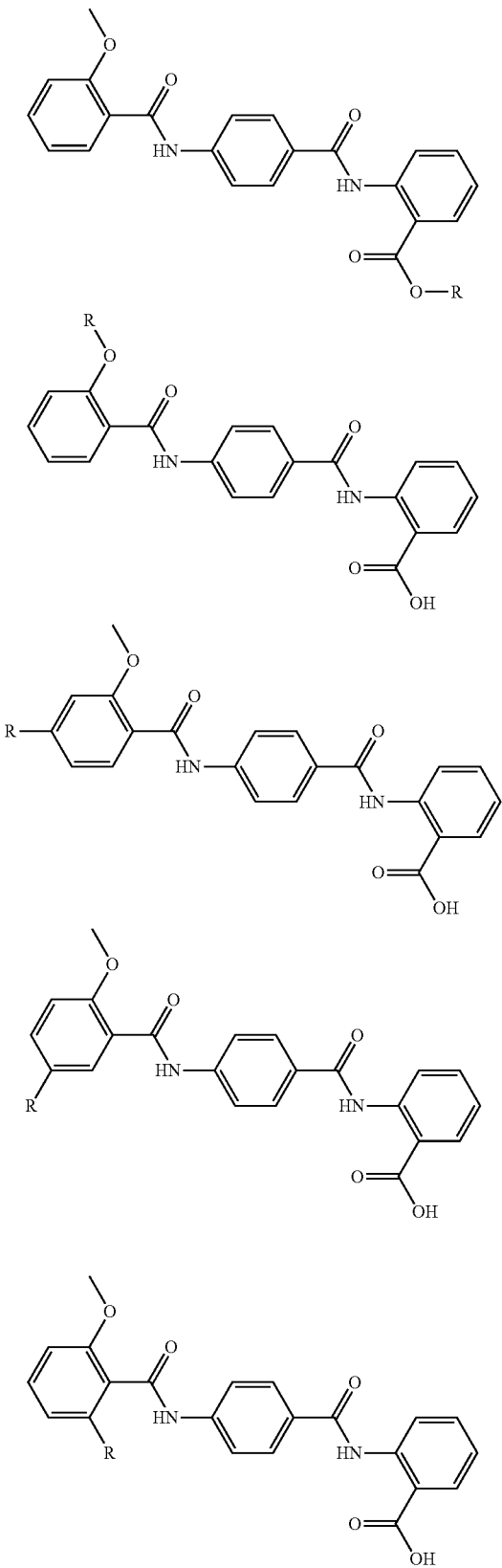
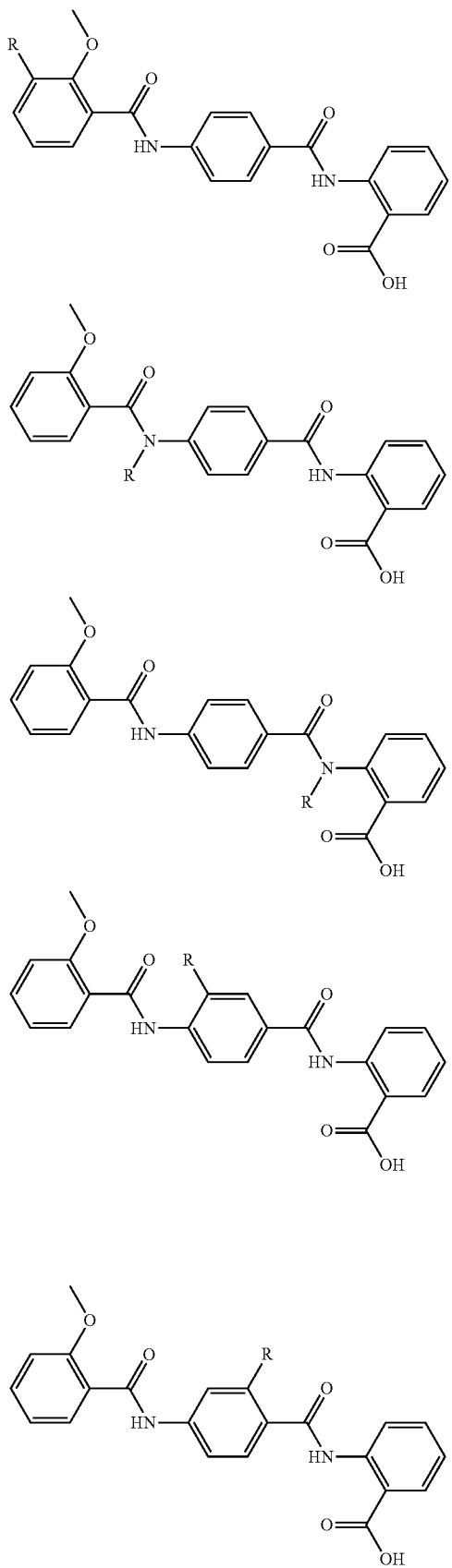

-continued
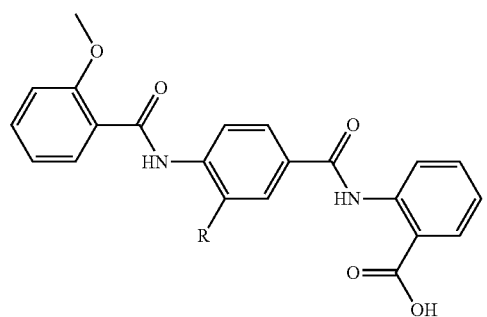
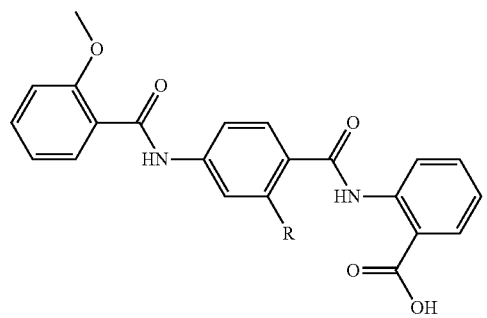
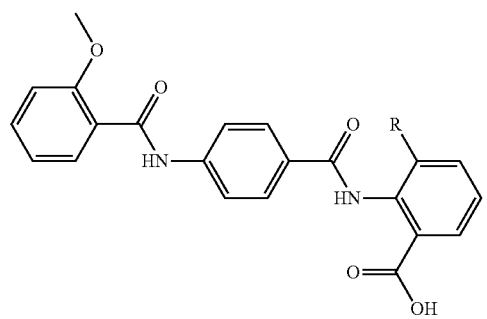
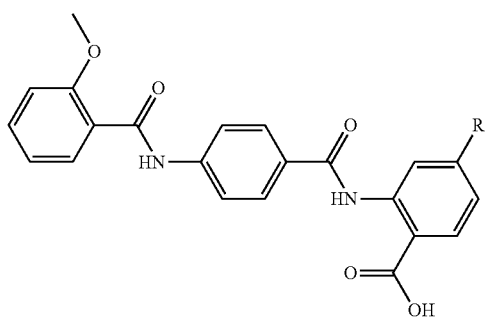
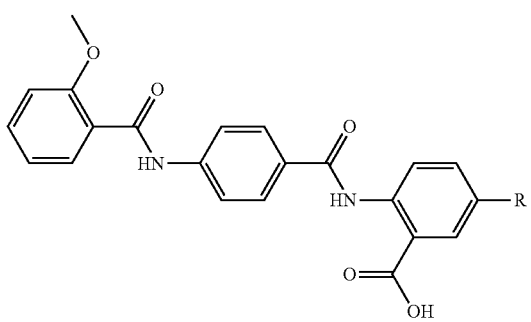
and
-continued
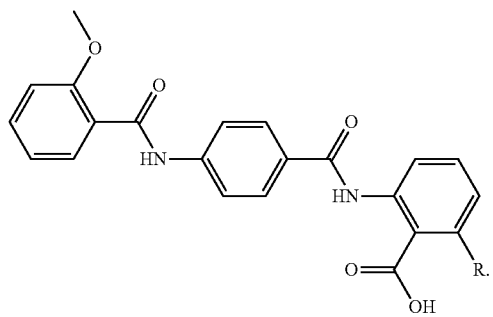
In certain embodiments the Pax2 Targeting Ligand is selected from:
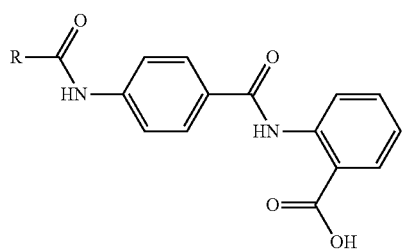
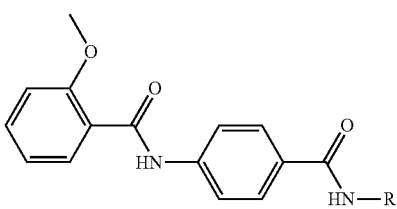
and
In certain embodiments the Pax2 Targeting Ligand is selected from:
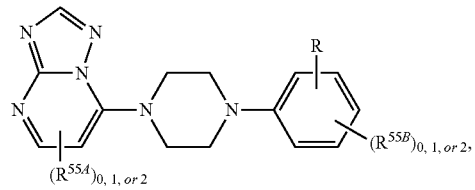
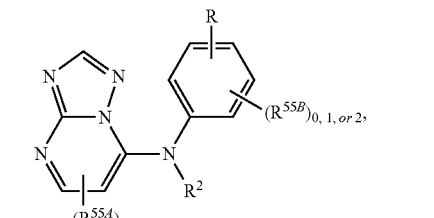
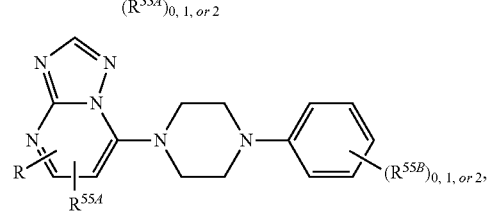

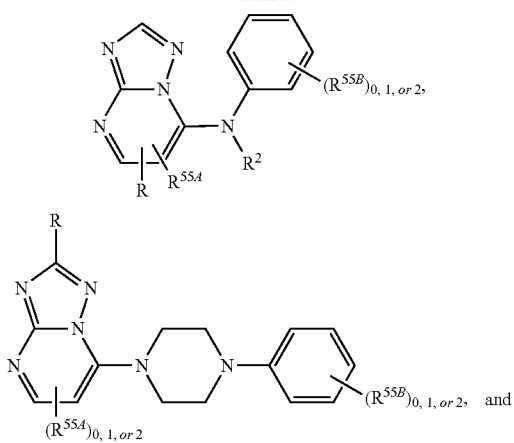

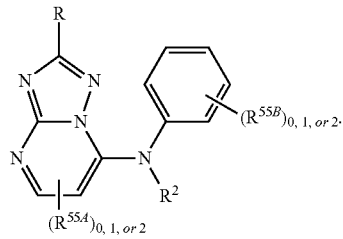

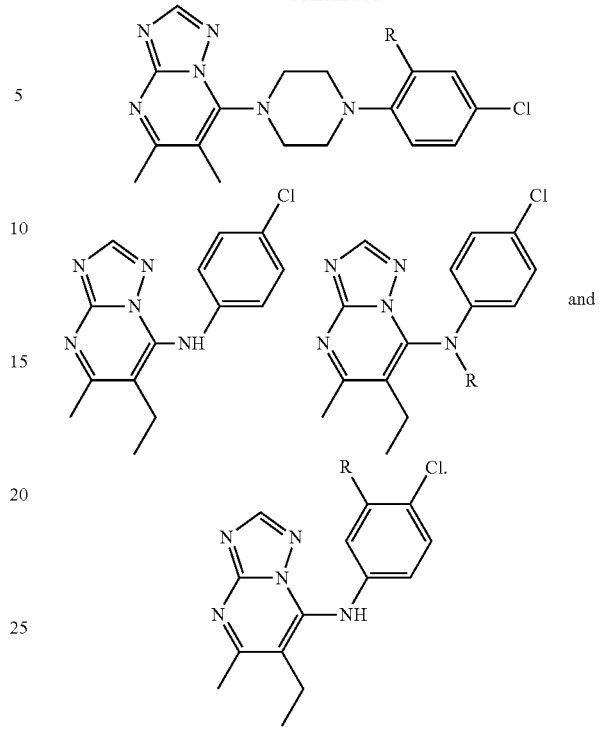

In certain embodiments the Pax2 Targeting Ligand is selected from:

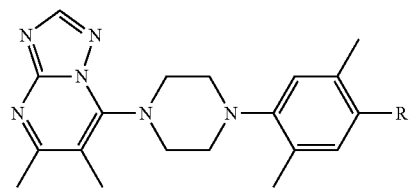

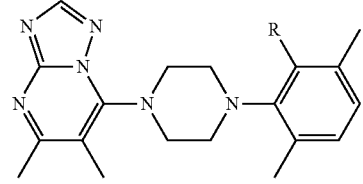

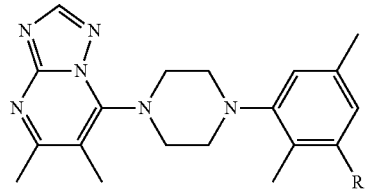

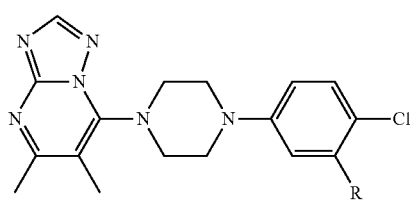

According to the present invention, the Targeting Ligand can be covalently bound to the Linker in any manner that achieves the desired results of the Degrader for therapeutic use. In certain non-limiting embodiments, the Targeting Ligand is bound to the Linker with a functional group that does not adversely affect the binding of the Ligand to the Target Protein. The attachment points below are exemplary in nature and one of ordinary skill in the art would be able to determine different appropriate attachment points.

The non-limiting compounds described below exemplify some of the members of these types of Targeting Ligands. In the Tables below, R is the point at which the Linker is attached to the Targeting Ligand.

In one embodiment, the Targeting Ligand binds to ASH1L. For example, the ASH1L small molecule inhibitor may be as described in WO2017/197240, the entirety of which is incorporated herein by reference. In one embodiment, the Targeting Ligand is

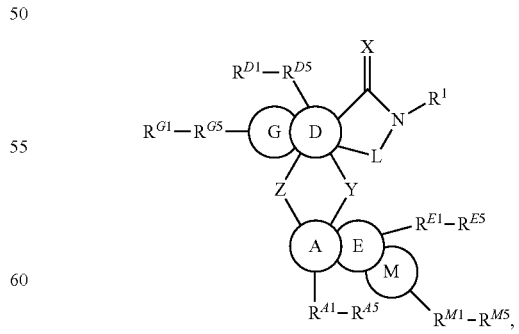

wherein all variables are as defined in WO2017/197240. As described in the '240 application, in some embodiments, any of formulas provided therein may be converted to bifunctional compounds composed of ASH1L inhibitor and an E3 ubiquitin ligase ligand connected with a linker, which function to bind ASH1L and recruit an E ubiquitin ligase (Cereblon, VHL ligase, etc.) complex to ubiquitinate and induce proteasome-mediated degradation of ASH1L. In the present invention, the linker is a Linker as defined herein covalently bound to a Degron as described herein.

In another embodiment, the Targeting Ligand is a deubiquitylating enzyme (DUB) inhibitor as described in WO2018/065768, WO2018/060742, WO2018/060691, WO2018/060689, WO2017/163078, WO2017/158388, WO2017/158381, WO2017/141036, WO2017/103614, WO2017/093718, WO2017/009650, WO2016/156816, or WO2016/046530.

In certain embodiments the Targeting Ligand is a WDR5 Targeting Ligand.

In certain embodiments the Targeting Ligand is a WDR5 Targeting Ligand selected from:

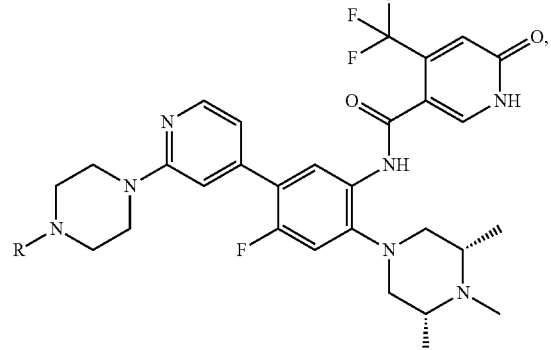

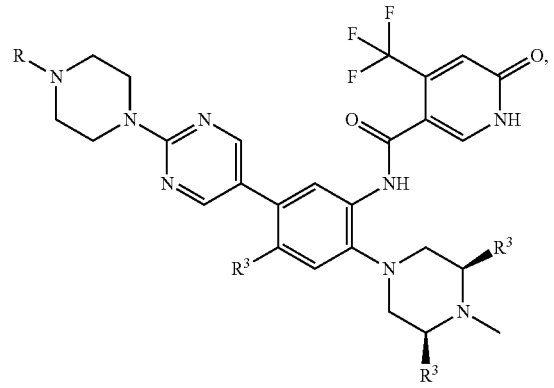

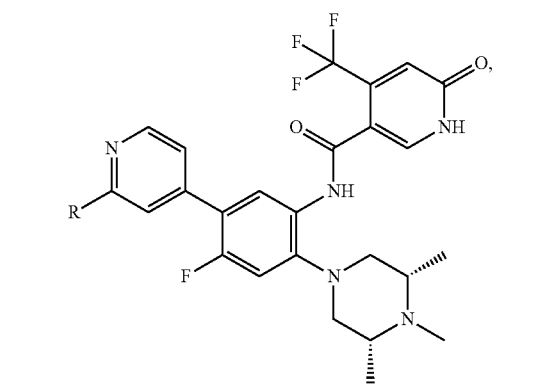

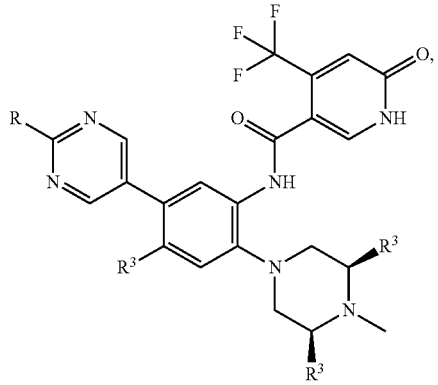

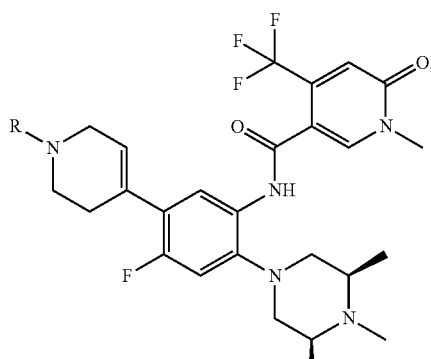

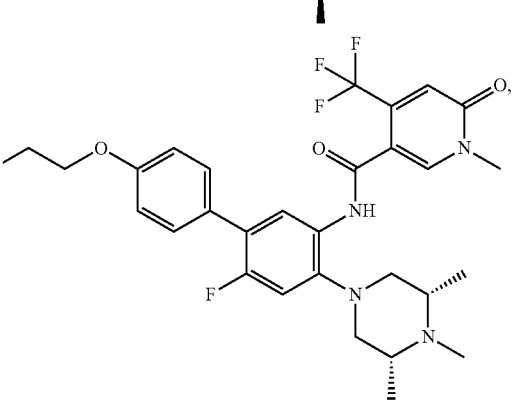

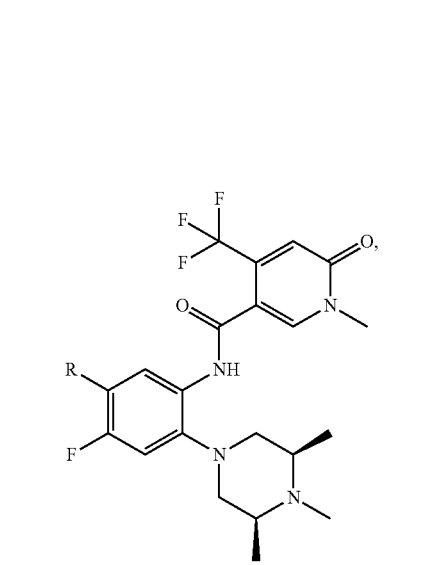

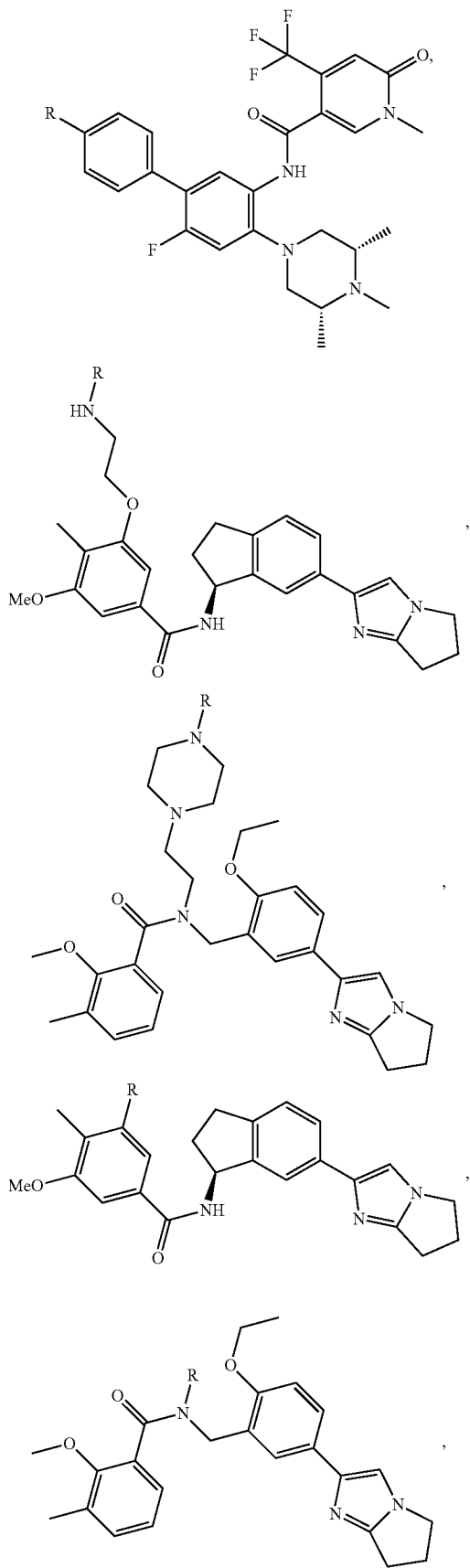

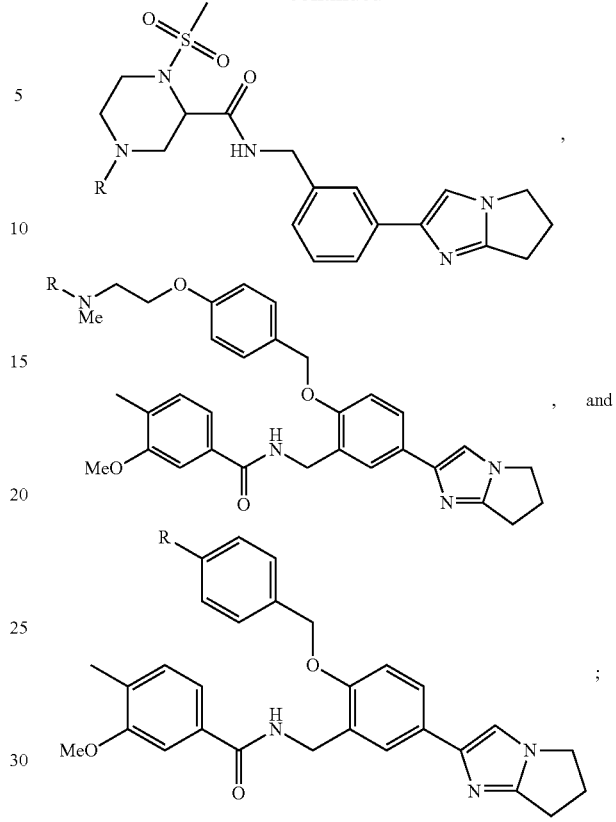

wherein R is the attachment point of the linker; and all other variables are defined as above.

In an alternative embodiment, any of the Targeting Ligands as described herein or in the figures may be optionally substituted with one or more, for example 1, 2, 3, 4, or 5, groups selected from $R^6$.

In certain embodiments $R^6$ is selected from halogen, $C_1$-$C_4$ alkyl, $C_1$-$C_4$ haloalkyl, $NH_2$, $NH(CH_3)$, $N(CH_3)_2$, hydroxyl, or methoxy.

VI. Methods of Treatment

In certain aspects a compound of the present invention is used in an effective amount to treat a host, including a human, in need thereof, optionally in a pharmaceutically acceptable carrier to treat a disorder described herein.

The terms "treat", "treating", and "treatment", etc., as used herein, refer to any action providing a benefit to a patient for which the present compounds may be administered, including the treatment of any disease state or condition which is modulated through the protein to which the present compounds bind. Illustrative non-limiting disease states or conditions, including cancer, which may be treated using compounds according to the present invention are set forth hereinabove.

The Degraders and compositions as described herein can be used to degrade a Target Protein which is a mediator of the disorder affecting the patient, such as a human. The control of protein level afforded by the Degraders of the present invention provides treatment of a disease state or condition, which is modulated through the Target Protein by lowering the level of that protein in the cell, e.g., cell of a patient. In certain embodiments, the method comprises administering an effective amount of the compound as described herein, optionally including a pharmaceutically acceptable excipient, carrier, or adjuvant, i.e., a pharmaceutically acceptable composition, optionally in combination with another bioactive agent or combination of agents.

The term "disease state or condition" when used in connection with a Degrader compound is meant to refer to any disease state or condition wherein protein dysregulation (i.e., the amount of protein expressed in a patient is elevated) occurs via a Target Protein and where degradation of such protein in a patient may provide beneficial therapy or relief of symptoms to a patient in need thereof.

In certain instances, the disease state or condition may be cured. The Degrader compounds are for example useful as therapeutic agents when administered in an effective amount to a host, including a human, to treat a myelo- or lymphoproliferative disorder such as B- or T-cell lymphomas, multiple myeloma, Waldenstrom's macroglobulinemia, Wiskott-Aldrich syndrome, or a post-transplant lymphoproliferative disorder; an immune disorder, including autoimmune disorders such as Addison disease, Celiac disease, dermatomyositis, Graves disease, thyroiditis, multiple sclerosis, pernicious anemia, reactive arthritis, lupus, or type I diabetes; a disease of cardiologic malfunction, including hypercholesterolemia; an infectious disease, including viral and/or bacterial infections; an inflammatory condition, including asthma, chronic peptic ulcers, tuberculosis, rheumatoid arthritis, periodontitis, ulcerative colitis, Crohn's disease, or hepatitis.

The term "disease state or condition" when used in connection with a Degron compound for example, refers to any therapeutic indication which can be treated by decreasing the activity of cereblon or a cereblon-containing E3 Ligase, including but not limited to uses known for the cereblon binders thalidomide, pomalidomide or lenalidomide.

Nonlimiting examples of uses for cereblon binders are multiple myeloma, a hematological disorder such as myelodysplastic syndrome, cancer, tumor, abnormal cellular proliferation, HIV/AIDS, HBV, HCV, SARS-CoV2, hepatitis, Crohn's disease, sarcoidosis, graft-versus-host disease, rheumatoid arthritis, Behcet's disease, tuberculosis, and myelofibrosis. Other indications include a myelo- or lymphoproliferative disorder such as B- or T-cell lymphomas, Waldenstrom's macroglobulinemia, Wiskott-Aldrich syndrome, or a post-transplant lymphoproliferative disorder; an immune disorder, including autoimmune disorders such as Addison disease, Celiac disease, dermatomyositis, Graves disease, thyroiditis, multiple sclerosis, pernicious anemia, arthritis, and in particular rheumatoid arthritis, lupus, or type I diabetes; a disease of cardiologic malfunction, including hypercholesterolemia; an infectious disease, including viral and/or bacterial infection, as described generally herein; an inflammatory condition, including asthma, chronic peptic ulcers, tuberculosis, rheumatoid arthritis, periodontitis and ulcerative colitis.

In certain embodiments, the present invention provides for administering a Degrader compound to a patient, for example, a human, having an infectious disease, wherein the therapy targets a protein of the infectious agent, optionally in combination with another bioactive agent. The disease state or condition may be a disease caused by a microbial agent or other exogenous agent such as a virus (as non-limiting examples, HIV, HBV, HCV, HSV, HPV, RSV, CMV, Ebola, SARS-CoV2, Flavivirus, Pestivirus, Rotavirus, Influenza, Coronavirus, EBV, viral pneumonia, drug-resistant viruses, Bird flu, RNA virus, DNA virus, adenovirus, poxvirus, Picornavirus, Togavirus, Orthomyxovirus, Retrovirus or Hepadnovirus), bacteria (Gram-negative, Gram-positive, fungus, protozoa, helminth, worms, prion, parasite, or other microbe or may be a disease state, which is caused by overexpression of a protein, which leads to a disease state and/or condition.

In certain embodiments, the condition treated with a compound of the present invention is a disorder related to abnormal cellular proliferation. Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells, and to be caused by autoantibodies produced against collagen and IgE.

Other disorders that can include an abnormal cellular proliferative component include Bechet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Cutaneous contact hypersensitivity and asthma are just two examples of immune responses that can be associated with significant morbidity. Others include atopic dermatitis, eczema, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, cutaneous lupus erythematosus, scleroderma, vaginitis, proctitis, and drug eruptions. These conditions may result in any one or more of the following symptoms or signs: itching, swelling, redness, blisters, crusting, ulceration, pain, scaling, cracking, hair loss, scarring, or oozing of fluid involving the skin, eye, or mucosal membranes.

In atopic dermatitis, and eczema in general, immunologically mediated leukocyte infiltration (particularly infiltration of mononuclear cells, lymphocytes, neutrophils, and eosinophils) into the skin importantly contributes to the pathogenesis of these diseases. Chronic eczema also is associated with significant hyperproliferation of the epidermis. Immunologically mediated leukocyte infiltration also occurs at sites other than the skin, such as in the airways in asthma and in the tear producing gland of the eye in keratoconjunctivitis sicca.

In one non-limiting embodiment compounds of the present invention are used as topical agents in treating contact dermatitis, atopic dermatitis, eczematous dermatitis, psoriasis, Sjogren's Syndrome, including keratoconjunctivitis sicca secondary to Sjogren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, and drug eruptions. The novel method may also be useful in reducing the infiltration of skin by malignant leukocytes in diseases such as mycosis fungoides. These compounds can also be used to treat an aqueous-deficient dry eye state (such as immune mediated keratoconjunctivitis) in a patient suffering therefrom, by administering the compound topically to the eye.

Disease states of conditions which may be treated using compounds according to the present invention include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease 1 (PKD1) or 2 (PKD2) Prader-Willi syndrome, Sickle-cell disease, Tay-Sachs disease, Turner syndrome.

Further disease states or conditions which may be treated by compounds according to the present invention include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barre syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present invention include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alstrom syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dube syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia-familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysylhydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, betathalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alstrom syndrome), Vrolik disease, Waardenburg syndrome, Warburg Sjo Fledelius Syndrome, Weissenbacher-Zweymuller syndrome, Wolf-Hirschhorn syndrome, Wolff Periodic disease, Weissenbacher-Zweymuller syndrome and Xeroderma pigmentosum, among others.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors.

Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present invention include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive CML.

Additional cancers which may be treated using the disclosed compounds according to the present invention include, for example, acute granulocytic leukemia, acute lymphocytic leukemia (ALL), acute myelogenous leukemia (AML), adenocarcinoma, adenosarcoma, adrenal cancer, adrenocortical carcinoma, anal cancer, anaplastic astrocytoma, angiosarcoma, appendix cancer, astrocytoma, Basal cell carcinoma, B-Cell lymphoma, bile duct cancer, bladder cancer, bone cancer, bone marrow cancer, bowel cancer, brain cancer, brain stem glioma, breast cancer, triple (estrogen, progesterone and HER-2) negative breast cancer, double negative breast cancer (two of estrogen, progesterone and HER-2 are negative), single negative (one of estrogen, progesterone and HER-2 is negative), estrogen-receptor positive, HER2-negative breast cancer, estrogen receptor-negative breast cancer, estrogen receptor positive breast cancer, metastatic breast cancer, luminal A breast cancer, luminal B breast cancer, Her2-negative breast cancer, HER2-positive or negative breast cancer, progesterone receptor-negative breast cancer, progesterone receptor-positive breast cancer, recurrent breast cancer, carcinoid tumors, cervical cancer, cholangiocarcinoma, chondrosarcoma, chronic lymphocytic leukemia (CLL), chronic myelogenous leukemia (CML), colon cancer, colorectal cancer, craniopharyngioma, cutaneous lymphoma, cutaneous melanoma, diffuse astrocytoma, ductal carcinoma in situ (DCIS), endometrial cancer, ependymoma, epithelioid sarcoma, esophageal cancer, ewing sarcoma, extrahepatic bile duct cancer, eye cancer, fallopian tube cancer, fibrosarcoma, gallbladder cancer, gastric cancer, gastrointestinal cancer, gastrointestinal carcinoid cancer, gastrointestinal stromal tumors (GIST), germ cell tumor glioblastoma multiforme (GBM), glioma, hairy cell leukemia, head and neck cancer, hemangioendothelioma, Hodgkin lymphoma, hypopharyngeal cancer, infiltrating ductal carcinoma (IDC), infiltrating lobular carcinoma (ILC), inflammatory breast cancer (IBC), intestinal Cancer, intrahepatic bile duct cancer, invasive/infiltrating breast cancer, Islet cell cancer, jaw cancer, Kaposi sarcoma, kidney cancer, laryngeal cancer, leiomyosarcoma, leptomeningeal metastases, leukemia, lip cancer, liposarcoma, liver cancer, lobular carcinoma in situ, low-grade astrocytoma, lung cancer, lymph node cancer, lymphoma, male breast cancer, medullary carcinoma, medulloblastoma, melanoma, meningioma, Merkel cell carcinoma, mesenchymal chondrosarcoma, mesenchymous, mesothelioma metastatic breast cancer, metastatic melanoma metastatic squamous neck cancer, mixed gliomas, monodermal teratoma, mouth cancer mucinous carcinoma, mucosal melanoma, multiple myeloma, Mycosis Fungoides, myelodysplastic syndrome, nasal cavity cancer, nasopharyngeal cancer, neck cancer, neuroblastoma, neuroendocrine tumors (NETs), non-Hodgkin's lymphoma, non-small cell lung cancer (NSCLC), oat cell cancer, ocular cancer, ocular melanoma, oligodendroglioma, oral cancer, oral cavity cancer, oropharyngeal cancer, osteogenic sarcoma, osteosarcoma, ovarian cancer, ovarian epithelial cancer ovarian germ cell tumor, ovarian primary peritoneal carcinoma, ovarian sex cord stromal tumor, Paget's disease, pancreatic cancer, papillary carcinoma, paranasal sinus cancer, parathyroid cancer, pelvic cancer, penile cancer, peripheral nerve cancer, peritoneal cancer, pharyngeal cancer, pheochromocytoma, pilocytic astrocytoma, pineal region tumor, pineoblastoma, pituitary gland cancer, primary central nervous system (CNS) lymphoma, prostate cancer, rectal cancer, renal cell carcinoma, renal pelvis cancer, rhabdomyosarcoma, salivary gland cancer, soft tissue sarcoma, bone sarcoma, sarcoma, sinus cancer, skin cancer, small cell lung cancer (SCLC), small intestine cancer, spinal cancer, spinal column cancer, spinal cord cancer, squamous cell carcinoma, stomach cancer, synovial sarcoma, T-cell lymphoma, testicular cancer, throat cancer, thymoma/thymic carcinoma, thyroid cancer, tongue cancer, tonsil cancer, transitional cell cancer, tubal cancer, tubular carcinoma, undiagnosed cancer, ureteral cancer, urethral cancer, uterine adenocarcinoma, uterine cancer, uterine sarcoma, vaginal cancer, vulvar cancer, T-cell lineage acute lymphoblastic leukemia (T-ALL), T-cell lineage lymphoblastic lymphoma (T-LL), peripheral T-cell lymphoma, Adult T-cell leukemia, Pre-B ALL, Pre-B lymphomas, large B-cell lymphoma, Burkitts lymphoma, B-cell ALL, Philadelphia chromosome positive ALL, Philadelphia chromosome positive CML, juvenile myelomonocytic leukemia (JMML), acute promyelocytic leukemia (a subtype of AML), large granular lymphocytic leukemia, Adult T-cell chronic leukemia, diffuse large B cell lymphoma, follicular lymphoma; Mucosa-Associated Lymphatic Tissue lymphoma (MALT), small cell lymphocytic lymphoma, mediastinal large B cell lymphoma, nodal marginal zone B cell lymphoma (NMZL); splenic marginal zone lymphoma (SMZL); intravascular large B-cell lymphoma; primary effusion lymphoma; or lymphomatoid granulomatosis; B-cell prolymphocytic leukemia; splenic lymphoma/leukemia, unclassifiable, splenic diffuse red pulp small B-cell lymphoma; lymphoplasmacytic lymphoma; heavy chain diseases, for example, Alpha heavy chain disease, Gamma heavy chain disease, Mu heavy chain disease, plasma cell myeloma, solitary plasmacytoma of bone; extraosseous plasmacytoma; primary cutaneous follicle center lymphoma, T cell/histocyte rich large B-cell lymphoma, DLBCL associated with chronic inflammation; Epstein-Barr virus (EBV)+ DLBCL of the elderly; primary mediastinal (thymic) large B-cell lymphoma, primary cutaneous DLBCL, leg type, ALK+ large B-cell lymphoma, plasmablastic lymphoma; large B-cell lymphoma arising in HHV8-associated multicentric, Castleman disease; B-cell lymphoma, unclassifiable, with features intermediate between diffuse large B-cell lymphoma, or B-cell lymphoma, unclassifiable, with features intermediate between diffuse large B-cell lymphoma and classical Hodgkin lymphoma.

In certain embodiments the cancer is an unresectable cancer.

Unresectable cancers are cancers that cannot be removed (resected) by surgery. Many cancers can be either resectable or unresectable depending on the site of the tumor and the size of the tumor.

In certain embodiments an unresectable cancer is treated with an effective amount of a compound described herein or a pharmaceutically acceptable salt thereof.

In other embodiments resectable cancer is treated with a compound described herein or a pharmaceutically acceptable salt thereof wherein the treatment additionally optionally includes surgically removing the tumor.

Locally advanced cancers are cancers that have grown outside of the body part where the tumor started but have not yet spread (metastasized) to other parts of the body.

In certain embodiments a locally advanced cancer is treated with an effective amount of a compound described herein or a pharmaceutically acceptable salt thereof.

In one embodiment the cancer is NUT midline cardinioma.

In one embodiment the cancer is adenoid cystic carcinoma.

The term "bioactive agent" is used to describe an agent, other than a compound according to the present invention, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

VII. Combination Therapy

The selected Degron or Degrader compound of the present invention can be used in an effective amount alone or in combination with another therapeutic or bioactive agent to treat a host such as a human with a disorder as described herein.

The term "bioactive agent" is used to describe an agent, other than the selected compound according to the present invention, which can be used in combination or alternation with a compound of the present invention to achieve a desired result of therapy. In one embodiment, the compound of the present invention and the bioactive agent are administered in a manner that they are active in vivo during overlapping time periods, for example, have time-period overlapping Cmax, Tmax, AUC or other pharmacokinetic parameter. In another embodiment, the compound of the present invention and the bioactive agent are administered to a host in need thereof that do not have overlapping pharmacokinetic parameter, however, one has a therapeutic impact on the therapeutic efficacy of the other.

In some aspects of this embodiment, the bioactive agent is an immune modulator, including but not limited to a checkpoint inhibitor, including as non-limiting examples, a PD-1 inhibitor, PD-L1 inhibitor, PD-L2 inhibitor, CTLA-4 inhibitor, LAG-3 inhibitor, TIM-3 inhibitor, V-domain Ig suppressor of T-cell activation (VISTA) inhibitors, small molecule, peptide, nucleotide, or other inhibitor. In certain aspects, the immune modulator is an antibody, such as a monoclonal antibody.

PD-1 inhibitors that blocks the interaction of PD-1 and PD-L1 by binding to the PD-1 receptor, and in turn inhibit immune suppression include, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-Li/VISTA inhibitor CA-170 (Curis Inc.). PD-L1 inhibitors that block the interaction of PD-1 and PD-L1 by binding to the PD-L1 receptor, and in turn inhibits immune suppression, include for example, atezolizumab (Tecentriq), durvalumab (AstraZeneca and MedImmune), KN035 (Alphamab), and BMS-936559 (Bristol-Myers Squibb). CTLA-4 checkpoint inhibitors that bind to CTLA-4 and inhibit immune suppression include, but are not limited to, ipilimumab, tremelimumab (AstraZeneca and MedImmune), AGEN1884 and AGEN2041 (Agenus). LAG-3 checkpoint inhibitors, include, but are not limited to, BMS-986016 (Bristol-Myers Squibb), GSK2831781 (GlaxoSmithKline), IMP321 (Prima BioMed), LAG525 (Novartis), and the dual PD-1 and LAG-3 inhibitor MGD013 (MacroGenics). An example of a TIM-3 inhibitor is TSR-022 (Tesaro).

In other embodiments, an active compounds described herein can be administered in an effective amount for the treatment of abnormal tissue of the female reproductive system such as breast, ovarian, endometrial, or uterine cancer, in combination or alternation with an effective amount of an estrogen inhibitor including but not limited to a SERM (selective estrogen receptor modulator), a SERD (selective estrogen receptor degrader), a complete estrogen receptor degrader, or another form of partial or complete estrogen antagonist or agonist. Partial anti-estrogens like raloxifene and tamoxifen retain some estrogen-like effects, including an estrogen-like stimulation of uterine growth, and also, in some cases, an estrogen-like action during breast cancer progression which actually stimulates tumor growth. In contrast, fulvestrant, a complete anti-estrogen, is free of estrogen-like action on the uterus and is effective in tamoxifen-resistant tumors.

Non-limiting examples of anti-estrogen compounds are provided in WO 2014/19176 assigned to Astra Zeneca, WO2013/090921, WO 2014/203129, WO 2014/203132, and US2013/0178445 assigned to Olema Pharmaceuticals, and U.S. Pat. Nos. 9,078,871, 8,853,423, and 8,703, 810, as well as US 2015/0005286, WO 2014/205136, and WO 2014/205138.

Additional non-limiting examples of anti-estrogen compounds include: SERMS such as anordrin, bazedoxifene, broparestriol, chlorotrianisene, clomiphene citrate, cyclofenil, lasofoxifene, ormeloxifene, raloxifene, tamoxifen, toremifene, and fulvestratnt; aromatase inhibitors such as aminoglutethimide, testolactone, anastrozole, exemestane, fadrozole, formestane, and letrozole; and antigonadotropins such as leuprorelin, cetrorelix, allylestrenol, chloromadi-none acetate, cyproterone acetate, delmadinone acetate, dydrogesterone, medroxyprogesterone acetate, megestrol acetate, nomegestrol acetate, norethisterone acetate, progesterone, and spironolactone.

Other estrogenic ligands that can be used according to the present invention are described in U.S. Pat. Nos. 4,418,068; 5,478,847; 5,393,763; and 5,457,117, WO2011/156518, U.S. Pat. Nos. 8,455,534 and 8,299,112, 9,078,871; 8,853, 423; 8,703,810; US 2015/0005286; and WO 2014/205138, US2016/0175289, US2015/0258080, WO 2014/191726, WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780, 497, 5,880,137, WO 2012/048058 and WO 2007/087684.

In another embodiment, an active compounds described herein can be administered in an effective amount for the treatment of abnormal tissue of the male reproductive system such as prostate or testicular cancer, in combination or alternation with an effective amount of an androgen (such as testosterone) inhibitor including but not limited to a selective androgen receptor modulator, a selective androgen receptor degrader, a complete androgen receptor degrader, or another form of partial or complete androgen antagonist. In one embodiment, the prostate or testicular cancer is androgen-resistant.

Non-limiting examples of anti-androgen compounds are provided in WO 2011/156518 and U.S. Pat. Nos. 8,455,534 and 8,299,112. Additional non-limiting examples of anti-androgen compounds include: enzalutamide, apalutamide, cyproterone acetate, chlormadinone acetate, spironolactone, canrenone, drospirenone, ketoconazole, topilutamide, abiraterone acetate, and cimetidine.

In one embodiment, the bioactive agent is an ALK inhibitor. Examples of ALK inhibitors include but are not limited to Crizotinib, Alectinib, ceritinib, TAE684 (NVP-TAE684), GSK1838705A, AZD3463, ASP3026, PF-06463922, entrectinib (RXDX-101), and AP26113.

In one embodiment, the bioactive agent is an EGFR inhibitor. Examples of EGFR inhibitors include erlotinib (Tarceva), gefitinib (Iressa), afatinib (Gilotrif), rociletinib (CO-1686), osimertinib (Tagrisso), olmutinib (Olita), naquotinib (ASP8273), nazartinib (EGF816), PF-06747775 (Pfizer), icotinib (BPI-2009), neratinib (HKI-272; PB272); avitinib (AC0010), EAI045, tarloxotinib (TH-4000; PR-610), PF-06459988 (Pfizer), tesevatinib (XL647; EXEL-7647; KD-019), transtinib, WZ-3146, WZ8040, CNX-2006, and dacomitinib (PF-00299804; Pfizer).

In one embodiment, the bioactive agent is an HER-2 inhibitor. Examples of HER-2 inhibitors include trastuzumab, lapatinib, ado-trastuzumab emtansine, and pertuzumab.

In one embodiment, the bioactive agent is a CD20 inhibitor. Examples of CD20 inhibitors include obinutuzumab, rituximab, fatumumab, ibritumomab, tositumomab, and ocrelizumab.

In one embodiment, the bioactive agent is a JAK3 inhibitor. Examples of JAK3 inhibitors include tasocitinib.

In one embodiment, the bioactive agent is a BCL-2 inhibitor. Examples of BCL-2 inhibitors include venetoclax, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy]benzamide), ABT-737 (4-[4-[[2-(4-chlorophenyl)phenyl]methyl]piperazin-1-yl]-N-[4-[[(2R)-4-(dimethylamino)-1-phenylsulfanylbutan-2-yl]amino]-3-nitrophenyl]sulfonylbenzamide) (navitoclax), ABT-263 ((R)-4-(4-((4'-chloro-4,4-dimethyl-3,4,5,6-tetrahydro-[1,1'-biphenyl]-2-yl)methyl)piperazin-1-yl)-N-((4-((4-morpholino-1-(phenylthio)butan-2-yl)amino)-3-((trifluoromethyl)sulfonyl)phenyl)sulfonyl)benzamide), GX15-070 (obatoclax mesylate, (2Z)-2-[(5Z)-5-[(3,5-dimethyl-1H-pyrrol-2-yl)methylidene]-4-methoxypyrrol-2-ylidene] indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl]benzamide), Apogossypolone (ApoG2), HA14-1, AT101, sabutoclax, gambogic acid, or G3139 (Oblimersen).

In one embodiment, the bioactive agent is a kinase inhibitor. In one embodiment, the kinase inhibitor is selected from a phosphoinositide 3-kinase (PI3K) inhibitor, a Bruton's tyrosine kinase (BTK) inhibitor, or a spleen tyrosine kinase (Syk) inhibitor, or a combination thereof.

Examples of PI3 kinase inhibitors include but are not limited to Wortmannin, demethoxyviridin, perifosine, idelalisib, Pictilisib, Palomid 529, ZSTK474, PWT33597, CUDC-907, and AEZS-136, duvelisib, GS-9820, BKM120, GDC-0032 (Taselisib) (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; orMethyl(oxo) {[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide) (omipalisib), TGX-221 ((+)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4-methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), Buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d]pyrimidine), GDC-0980 ((S)-1-(4-((2-(2-aminopyrimidin-5-yl)-7-methyl-4-morpholinothieno[3,2-d]pyrimidin-6-yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea) (gedatolisib), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile) (dactolisib), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3aR,6E,9S,9aR,10R,11aS)-6-[[bis(prop-2-enyl)amino]methylidene]-5-hydroxy-9-(methoxymethyl)-9a,11a-dimethyl-1,4,7-trioxo-2,3,3a,9,10,11-hexahydroindeno[4,5h]isochromen-l0-yl]acetate (also known as sonolisib)), LY294002, AZD8186, PF-4989216, pilaralisib, GNE-317, PI-3065, PI-103, NU7441 (KU-57788), HS 173, VS-5584 (SB2343), CZC24832, TG100-115, A66, YM201636, CAY10505, PIK-75, PIK-93, AS-605240, BGT226 (NVP-BGT226), AZD6482, voxtalisib, alpelisib, IC-87114, TGI100713, CH5132799, PKI-402, copanlisib (BAY 80-6946), XL 147, PIK-90, PIK-293, PIK-294, 3-MA (3-methyladenine), AS-252424, AS-604850, apitolisib (GDC-0980; RG7422), and the structure described in WO2014/071109.

Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 2011/0117073, incorporated herein in its entirety), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl)propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl)phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g] quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino) pyrimidine-5-carboxamide hydrochloride), QL-47 (1-(1-acryloylindolin-6-yl)-9-(1-methyl-1H-pyrazol-4-yl)benzo[h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et ah, Journal of Hematology & Oncology, 2013, 6:59, the entirety of which is incorporated herein by reference.

Syk inhibitors include, for example, Cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium (6-((5-fluoro-2-((3,4,5-trimethoxyphenyl)amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), $R^{09021}$ (6-[(1R,2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino)pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), $R^{112}$ (3,3'-((5-fluoropyrimidine-2,4-diyl)bis(azanediyl))diphenol), $R^{348}$ (3-Ethyl-4-methylpyridine), $R^{406}$ (6-((5-fluoro-2-((3,4,5-trimethoxyphenyl)amino)pyrimidin-4-yl)amino)-2,2-dimethyl-2H-pyrido[3,2-b][1,4]oxazin-3(4H)-one), piceatannol (3-Hydroxyresveratol), YM193306(see Singh et al. Discovery and Development of Spleen Tyrosine Kinase (SYK) Inhibitors, J. Med. Chem. 2012, 55, 3614-3643), 7-azaindole, piceatannol, ER-27319 (see Singh et al. Discovery and Development of Spleen Tyrosine Kinase (SYK) Inhibitors, J. Med. Chem. 2012, 55, 3614-3643 incorporated in its entirety herein), Compound D (see Singh et al. Discovery and Development of Spleen Tyrosine Kinase (SYK) Inhibitors, J. Med. Chem. 2012, 55, 3614-3643 incorporated in its entirety herein), PRT060318 (see Singh et al. Discovery and Development of Spleen Tyrosine Kinase (SYK) Inhibitors, J. Med. Chem. 2012, 55, 3614-3643 incorporated in its entirety herein), luteolin (see Singh et al. Discovery and Development of Spleen Tyrosine Kinase (SYK) Inhibitors, J. Med. Chem. 2012, 55, 3614-3643 incorporated in its entirety herein), apigenin (see Singh et al. Discovery and Development of Spleen Tyrosine Kinase (SYK) Inhibitors, J. Med. Chem. 2012, 55, 3614-3643 incorporated in its entirety herein), quercetin (see Singh et al. Discovery and Development of Spleen Tyrosine Kinase (SYK) Inhibitors, J. Med. Chem. 2012, 55, 3614-3643 incorporated in its entirety herein), fisetin (see Singh et al. Discovery and Development of Spleen Tyrosine Kinase (SYK) Inhibitors, J. Med. Chem. 2012, 55, 3614-3643 incorporated in its entirety herein), myricetin (see Singh et al. Discovery and Development of Spleen Tyrosine Kinase (SYK) Inhibitors, J. Med. Chem. 2012, 55, 3614-3643 incorporated in its entirety herein), morin (see Singh et al. Discovery and Development of Spleen Tyrosine Kinase (SYK) Inhibitors, *J. Med.* Chem. 2012, 55, 3614-3643 incorporated in its entirety herein).

In one embodiment, the bioactive agent is a MEK inhibitor. MEK inhibitors are well known, and include, for example, trametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl) acetamide), selumetinib (6-(4-bromo-2-chloroanilino)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol), refametinib/BAY869766/RDEA1 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3-d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6-carboxamide), $R^{05126766}$ (3-[[3-Fluoro-2-(methylsulfamoylamino)-4-pyridyl]methyl]-4-methyl-7-pyrimidin-2-yloxychromen-2-one), WX-554, $R^{04987655}$/CH4987655 (3,4-difluoro-2-((2-fluoro-4-iodophenyl)amino)-N-(2-hydroxyethoxy)-5-((3-oxo-1,2-oxazinan-2y1)methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide), U0126-EtOH, PD184352 (CI-1040), GDC-0623, BI-847325, cobimetinib, PD98059, BIX 02189, BIX 02188, binimetinib, SL-327, TAK-733, PD318088.

In one embodiment, the bioactive agent is a Raf inhibitor. Raf inhibitors are known and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino]phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl]pyridin-4-yl]oxy-N-[4-(trifluoromethyl)phenyl] benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), Sorafenib N-Oxide (4-[4-[[[[4-Chloro-3-(trifluoroMethyl)phenyl]aMino]carbonyl]aMino]phenoxy]-N-Methyl-2pyridinecarboxaMide 1-Oxide), PLX-4720, dabrafenib (GSK2118436), GDC-0879, RAF265, AZ 628, SB590885, ZM336372, GW5074, TAK-632, CEP-32496, LY3009120, and GX818 (Encorafenib).

In one embodiment, the bioactive agent is an AKT inhibitor, including but not limited to, MK-2206, GSK690693, Perifosine, (KRX-0401), GDC-0068, Triciribine, AZD5363, Honokiol, PF-04691502, and Miltefosine, a FLT-3 inhibitor, including but not limited to, P406, Dovitinib, Quizartinib (AC220), Amuvatinib (MP-470), Tandutinib (MLN518), ENMD-2076, and KW-2449, or a combination thereof.

In one embodiment, the bioactive agent is an mTOR inhibitor. Examples of mTOR inhibitors include but are not limited to rapamycin and its analogs, everolimus (Afinitor), temsirolimus, ridaforolimus, sirolimus, and deforolimus. Examples of MEK inhibitors include but are not limited to tametinib/GSK1120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl}phenyl)acetamide), selumetinob (6-(4-bromo-2-chloroanilino)-7- fluoro-N-(2-hydroxyethoxy)-3-methylbenzimidazole-5-carboxamide), pimasertib/AS703026/MSC1935369 ((S)—N-(2,3-dihydroxypropyl)-3-((2-fluoro-4-iodophenyl)amino) isonicotinamide), XL-518/GDC-0973 (1-({3,4-difluoro-2-[(2-fluoro-4-iodophenyl)amino]phenyl}carbonyl)-3-[(2S)-piperidin-2-yl]azetidin-3-ol) (cobimetinib), refametinib/BAY869766/RDEA119 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamino)-8-methylpyrido[2,3d]pyrimidine-4,7(3H,8H)-dione), MEK162/ARRY438162 (5-[(4-Bromo-2-fluorophenyl)amino]-4-fluoro-N-(2-hydroxyethoxy)-1-methyl-1H-benzimidazole-6 carboxamide), $R^{05126766}$ (3-[[3-Fluoro-2-(methylsulfamoylamino)-4-pyridyl]methyl]-4-methyl-7-pyrimidin-2-yloxy-chromen-2-one), WX-554, $R^{04987655}$/CH4987655 (3,4-difluoro-2-((2-fluoro-4-iodophenyl)amino)-N-(2-hydroxyethoxy)-5-((3-oxo-1,2-oxazinan-2-yl)methyl) benzamide), or AZD8330 (2-((2-fluoro-4-iodophenyl) amino)-N-(2-hydroxyethoxy)-1,5-dimethyl-6-oxo-1,6-dihydropyridine-3-carboxamide).

In one embodiment, the bioactive agent is a RAS inhibitor. Examples of RAS inhibitors include but are not limited to Reolysin and siG12D LODER.

In one embodiment, the bioactive agent is a HSP inhibitor. HSP inhibitors include but are not limited to Geldanamycin or 17-N-Allylamino-17-demethoxygeldanamycin (17AAG), and Radicicol.

Additional bioactive compounds include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, aFLT-3 inhibitor, a VEGFRinhibitor, an aurora kinase inhibitor, a PIK-1 modulator, an HDAC inhbitor, a c-MET inhibitor, a PARP inhibitor, a Cdk inhibitor, an IGFR-TK inhibitor, an anti-HGF antibody, a focal adhesion kinase inhibitor, a Map kinase kinase (mek) inhibitor, a VEGF trap antibody, pemetrexed, panitumumab, amrubicin, oregovomab, Lepetu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR₁ KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo [2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, *Bacillus* Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deoxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779,450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In one embodiment, the bioactive agent is selected from, but are not limited to, Imatinib mesylate (Gleevac®), Dasatinib (Sprycel®), Nilotinib (Tasigna®), Bosutinib (Bosulif®), Trastuzumab (Herceptin®), trastuzumab-DM1, Pertuzumab (Perjeta™), Lapatinib (Tykerb®), Gefitinib (Iressa®), Erlotinib (Tarceva®), Cetuximab (Erbitux®), Panitumumab (Vectibix®), Vandetanib (Caprelsa®), Vemurafenib (Zelboraf®), Vorinostat (Zolinza®), Romidepsin (Istodax®), Bexarotene (Tagretin®), Alitretinoin (Panretin®), Tretinoin (Vesanoid®), Carfilizomib (Kyprolis™), Pralatrexate (Folotyn®), Bevacizumab (Avastin®), Ziv-aflibercept (Zaltrap®), Sorafenib (Nexavar®), Sunitinib (Sutent®), Pazopanib (Votrient®), Regorafenib (Stivarga®), and Cabozantinib (Cometriq™).

In certain aspects, the bioactive agent is an anti-inflammatory agent, a chemotherapeutic agent, a radiotherapeutic, an additional therapeutic agent, or an immunosuppressive agent.

Suitable chemotherapeutic bioactive agents include, but are not limited to, a radioactive molecule, a toxin, also referred to as cytotoxin or cytotoxic agent, which includes any agent that is detrimental to the viability of cells, and liposomes or other vesicles containing chemotherapeutic compounds. General anticancer pharmaceutical agents include: Vincristine (Oncovin®) or liposomal vincristine (Marqibo®), Daunorubicin (daunomycin or Cerubidine®) or doxorubicin (Adriamycin®), Cytarabine (cytosine arabinoside, ara-C, or Cytosar®), L-asparaginase (Elspar®) or PEG-L-asparaginase (pegaspargase or Oncaspar®), Etoposide (VP-16), Teniposide (Vumon®), 6-mercaptopurine (6-MP or Purinethol®), Methotrexate, Cyclophosphamide (Cytoxan®), Prednisone, Dexamethasone (Decadron), imatinib (Gleevec®), dasatinib (Sprycel®), nilotinib (Tasigna®), bosutinib (Bosulif®), and ponatinib (Iclusig™)

Examples of additional suitable chemotherapeutic agents include but are not limited to 1-dehydrotestosterone, 5-fluorouracil decarbazine, 6-mercaptopurine, 6-thioguanine, actinomycin D, adriamycin, aldesleukin, an alkylating agent, allopurinol sodium, altretamine, amifostine, anastrozole, anthramycin (AMC)), an anti-mitotic agent, cis-dichlorodiamine platinum (II) (DDP) cisplatin), diamino dichloro platinum, anthracycline, an antibiotic, an antimetabolite, asparaginase, BCG live (intravesical), betamethasone sodium phosphate and betamethasone acetate, bicalutamide, bleomycin sulfate, busulfan, calcium leucouorin, calicheamicin, capecitabine, carboplatin, lomustine (CCNU), carmustine (BSNU), Chlorambucil, Cisplatin, Cladribine, Colchicin, conjugated estrogens, Cyclophosphamide, Cyclothosphamide, Cytarabine, Cytarabine, cytochalasin B, Cytoxan, Dacarbazine, Dactinomycin, dactinomycin (formerly actinomycin), daunirubicin HCL, daunorucbicin citrate, denileukin diftitox, Dexrazoxane, Dibromomannitol, dihydroxy anthracin dione, Docetaxel, dolasetron mesylate, doxorubicin HCL, dronabinol, E. coli L-asparaginase, emetine, epoetin-α, Erwinia L-asparaginase, esterified estrogens, estradiol, estramustine phosphate sodium, ethidium bromide, ethinyl estradiol, etidronate, etoposide citrororum factor, etoposide phosphate, filgrastim, floxuridine, fluconazole, fludarabine phosphate, fluorouracil, flutamide, folinic acid, gemcitabine HCL, glucocorticoids, goserelin acetate, gramicidin D, granisetron HCL, hydroxyurea, idarubicin HCL, ifosfamide, interferon α-2b, irinotecan HCL, letrozole, leucovorin calcium, leuprolide acetate, levamisole HCL, lidocaine, lomustine, maytansinoid, mechlorethamine HCL, medroxyprogesterone acetate, megestrol acetate, melphalan HCL, mercaptipurine, mesna, methotrexate, methyltestosterone, mithramycin, mitomycin C, mitotane, mitoxantrone, nilutamide, octreotide acetate, ondansetron HCL, paclitaxel, pamidronate disodium, pentostatin, pilocarpine HCL, plimycin, polifeprosan 20 with carmustine implant, porfimer sodium, procaine, procarbazine HCL, propranolol, rituximab, sargramostim, streptozotocin, tamoxifen, taxol, teniposide, tenoposide, testolactone, tetracaine, thioepa chlorambucil, thioguanine, thiotepa, topotecan HCL, toremifene citrate, trastuzumab, tretinoin, valrubicin, vinblastine sulfate, vincristine sulfate, and vinorelbine tartrate.

Additional therapeutic agents that can be administered in combination with a Degrader disclosed herein can include bevacizumab, sutinib, sorafenib, 2-methoxyestradiol or 2ME2, finasunate, vatalanib, vandetanib, aflibercept, volociximab, etaracizumab (MEDI-522), cilengitide, erlotinib, cetuximab, panitumumab, gefitinib, trastuzumab, dovitinib, figitumumab, atacicept, rituximab, alemtuzumab, aldesleukine, atlizumab, tocilizumab, temsirolimus, everolimus, lucatumumab, dacetuzumab, HLL1, huN901-DM1, atiprimod, natalizumab, bortezomib, carfilzomib, marizomib, tanespimycin, saquinavir mesylate, ritonavir, nelfinavir mesylate, indinavir sulfate, belinostat, panobinostat, mapatumumab, lexatumumab, dulanermin, ABT-737, oblimersen, plitidepsin, talmapimod, P276-00, enzastaurin, tipifarnib, perifosine, imatinib, dasatinib, lenalidomide, thalidomide, simvastatin, celecoxib, bazedoxifene, AZD4547, rilotumumab, oxaliplatin (Eloxatin), PD0332991, ribociclib (LEE011), amebaciclib (LY2835219), HDM201, fulvestrant (Faslodex), exemestane (Aromasin), PIM447, ruxolitinib (INC424), BGJ398, necitumumab, pemetrexed (Alimta), and ramucirumab (IMC-1121B).

In one aspect of the invention, the disclosed compound is administered in combination with an anti-infective agent, for example but not limited to an anti-HIV agent, anti-HCV agent, anti-HBV agent, or other anti-viral or anti-bacterial agent. In one embodiment, the anti-HIV agent can be, but is not limited to, for example, a nucleoside reverse transcriptase inhibitor (NRTI), other non-nucloeoside reverse transcriptase inhibitor, protease inhibitor, fusion inhibitor, among others.

Nucleoside/Nucleotide Reverse Transcriptase Inhibitors (NRTIs) include, but are not limited to, Abacavir or ABC (Ziagen), Didanosine or ddl (Videx), Emtricitabine or FTC (Emtriva), Lamivudine or 3TC (Epivir), ddC (zalcitabine), Stavudine or d4T (Zerit), Tenofovircor TDF (Viread), D-D4FC (Reverset), and Zidovudine or AZT or ZDV (Retrovir).

Non-nucleoside Reverse Transcriptase Inhibitors (NNRTIs) include, but are not limited to, Delavirdine (Rescriptor), Efavirenz (Sustiva), Etravirine (Intelence), Nevirapine (Viramune), and Rilpivirine (Edurant). Anti-HIV Protease Inhibitors (PIs) include, but are not limited to, Atazanavir or ATV (Reyataz), Darunavir or DRV (Prezista), Fosamprenavir or FPV (Lexiva), Indinavir or IDV (Crixivan), Lopinavir+ritonavir, or LPV/r (Kaletra), Nelfinavir or NFV (Viracept), Ritonavir or RTV (Norvir), Saquinavir or SQV (Invirase), Tipranavir, or TPV (Aptivus), Cobicistat (Tybost), Atazanavir+cobicistat, or ATV/COBI (Evotaz), Darunavir+cobicistat, or DRV/COBI (Prezcobix).

Anti-HIV Fusion Inhibitors include, but are not limited to, Enfuvirtide or ENF or T-20 (Fuzeon). Anti-HIV also include, but are not limited to, Maraviroc or MVC (Selzentry).

Anti-HIV Integrase Inhibitors include, but are not limited to Dolutegravir (Tivicay), Elvitegravir (Vitekta), Raltegravir (Isentress).

Anti-HIV combinations agents include Abacavir+Dolutegravir+lamivudine, or ABC/DTG/3TC (Triumeq), Abacavir+lamivudine or ABC/3TC (Epzicom), Abacavir+lamivudine+zidovudine, or ABC/3TC/ZDV (Trizivir), Efavirenz+emtricitabine+tenofovir or EFV/FTC/TDF (Atripla, Tribuss), elvitegravir, cobicistat, emtricitabine, tenofovir alafenamide or EVG/COBI/FTC/TAF or ECF/TAF (Genvoya; (Stribild), emtricitabine+rilpivirine+tenofovir or FTC/RPV/TAF (Odefsey); Emtricitabine+rilpivirine+tenofovir or FTC/RPV/TDF (Complera), Emtricitabine+tenofovir or TAF/FTC (Descovy), emtricitabine and tenofovir disoproxil fumarate (Truvada), and Lamivudine+zidovudine or 3TC/ZDV (Combivir).

Other anti-HIV compounds include, but are not limited to Racivir, L-FddC, L-FD4C, SQVM (Saquinavir mesylate), IDV (Indinavir), SQV (Saquinavir), APV (Amprenavir), LPV (Lopinavir), fusion inhibitors such as T20, among others, fuseon and mixtures thereof, including anti-HIV compounds presently in clinical trials or in development.

Other anti-HIV agents which may be used in co-administration with the disclosed compounds according to the present invention. NNRTIs may be selected from the group consisting of nevirapine (BI-R$^6$-587), delavirdine (U-90152S/T), efavirenz (DMP-266), UC-781 (N-[4-chloro-3-(3-methyl-2-butenyloxy)phenyl]-2methyl3-furan-carbothiamide), etravirine (TMC125), Trovirdine (Ly300046.HCl), HI-236, HI-240, HI-280, HI-281, rilpivirine (TMC-278), MSC-127, HBY 097, DMP266, Baicalin (TJN-151) ADAM-II (Methyl 3',3'-dichloro-4',4"-dimethoxy-5',5"-bis(methoxycarbonyl)-6,6-diphenylhexenoate), Methyl 3-Bromo-5-(1-5-bromo-4-methoxy-3-(methoxycarbonyl)phenyl)hept-1-enyl)-2-methoxybenzoate (Alkenyldiarylmethane analog, Adam analog), (5-chloro-3-(phenylsulfinyl)-2'-indolecarboxamide), AAP-BHAP (U-104489 or PNU-104489), Capravirine (AG-1549, 5-1153), atevirdine (U-87201E), aurin tricarboxylic acid (SD-095345), 1-[(6-cyano-2-indolyl)carbonyl]-4-[3-(isopropylamino)-2-pyridinyl]piperazine, 1-[5-[[N-(methyl)methylsulfonylamino]-2-indolylcarbonyl-4-[3-(isopropylamino)-2-pyridinyl]piperazine, 1-[3-(Ethylamino)-2-[pyridinyl]-4-[(5-hydroxy-2-indolyl)carbonyl]piperazine, 1-[(6-Formyl-2-indolyl)carbonyl]-4-[3-(isopropylamino)-2-pyridinyl]piperazine, 1-[[5-(Methylsulfonyloxy)-2-indoyly)carbonyl]-4-[3-(isopropylamino)-2-pyridinyl]piperazine, U88204E, Bis(2-nitrophenyl)sulfone (NSC 633001), Calanolide A (NSC675451), Calanolide B, 6-Benzyl-5-methyl-2-(cyclohexyloxy)pyrimidin-4-one (DABO-546), DPC 961, E-EBU, E-EBU-dm, E-EPSeU, E-EPU, Foscarnet (Foscavir), HEPT (1-[(2-Hydroxyethoxy)methyl]-6-(phenylthio)thymine), HEPT-M (1-[(2-Hydroxyethoxy)methyl]-6-(3-methylphenyl)thio)thymine), HEPT-S(1-[(2-Hydroxyethoxy)methyl]-6-(phenylthio)-2-thiothymine), Inophyllum P, L-737,126, Michellamine A (NSC650898), Michellamine B (NSC649324), Michellamine F, 6-(3,5-Dimethylbenzyl)-1-[(2-hydroxyethoxy)methyl]-5-isopropyluracil, 6-(3,5-Dimethylbenzyl)-1-(ethyoxymethyl)-5-isopropyluracil, NPPS, E-BPTU (NSC 648400), Oltipraz (4-Methyl-5-(pyrazinyl)-3H-1,2-dithiole-3-thione), N-{2-(2-Chloro-6-fluorophenethyl]-N'-(2-thiazolyl)thiourea (PETT Cl, F derivative), N-{2-(2,6-Difluorophenethyl]-N'-[2-(5-bromopyridyl)]thiourea (PETT derivative), N-{2-(2,6-Difluorophenethyl]-N'-[2-(5-methylpyridyl]thiourea {PETT Pyridyl derivative), N-[2-(3-Fluorofuranyl)ethyl]-N'-[2-(5-chloropyridyl)]thiourea, N-[2-(2-Fluoro-6-ethoxyphenethyl)]-N'-[2-(5-bromopyridyl)]thiourea, N-(2-Phenethyl)-N'-(2-thiazolyl)thiourea (LY-73497), L-697,639, L-697,593, L-697,661, 342-(4,7-Difluorobenzoxazol-2-yl)ethyl}-5-ethyl-6-methyl (pypridin-2(1H)-thione (2-Pyridinone Derivative), 3-[[(2-Methoxy-5,6-dimethyl-3-pyridyl)methyl]amine]-5-ethyl-6-methyl(pypridin-2(1H)-thione, R82150, R82913, R87232, R88703, R89439 (Loviride), R90385, 5-2720, Suramin Sodium, TBZ (Thiazolobenzimidazole, NSC 625487), Thiazoloisoindol-5-one, (+)(R)-9b-(3,5-Dimethylphenyl-2,3-dihydrothiazolo[2,3-a]isoindol-5 (9bH)-one, Tivirapine (R86183), UC-38 and UC-84, among others.

In one aspect of the invention, the disclosed compound when used to treat an HCV infection can be administered in combination with another anti-HCV agent. Anti-HCV agents are known in the art. To date, a number of fixed dose drug combinations have been approved for the treatment of HCV. Harvoni® (Gilead Sciences, Inc.) contains the NS5A inhibitor ledipasvir and the NS5B inhibitor sofosbuvir. Technivie™ (AbbVie, Inc.) is a fixed-dose combination containing ombitasvir, an NS5A inhibitor; paritaprevir, an NS3/4A protease inhibitor; and ritonavir, a CYP3A inhibitor. Daklinza™ (daclatasvir, Bristol-Myers Squibb) is an HCV NS5A inhibitor indicated for use with sofosbuvir for the treatment of chronic genotype 3 infection. Zepatier™ (Merck & Co.) has recently been approved for the treatment of chronic HCV genotypes 1 and 4. Zepatier™ is a fixed-dose combination product containing elbasvir, an HCV NS5A inhibitor, and grazoprevir, an HCV NS3/4A protease inhibitor. Zepatier™ is indicated with or without ribavirin. Epclusa® (Gilead Sciences, Inc.) is a fixed-dose combination tablet containing sofosbuvir and velpatasvir.

Additional anti-HCV agents and combinations thereof include those described in U. S. Pat. Nos. 9,382,218; 9,321,753; 9,249,176; 9,233,974; 9,221,833; 9,211,315; 9,194,873; 9,186,369; 9,180,193; 9,156,823; 9,138,442; 9,133,170; 9,108,999; 9,090,559; 9,079,887; 9,073,943; 9,073,942; 9,056,090; 9,051,340; 9,034,863; 9,029,413; 9,011,938; 8,987,302; 8,945,584; 8,940,718; 8,927,484; 8,921,341; 8,884,030; 8,841,278; 8,822,430; 8,772,022; 8,765,722; 8,742,101; 8,741,946; 8,674,085; 8,673,288; 8,669,234; 8,663,648; 8,618,275; 8,580,252; 8,575,195; 8,575,135; 8,575,118; 8,569,302; 8,524,764; 8,513,298; 8,501,714; 8,404,651; 8,273,341; 8,257,699; 8,197,861; 8,158,677; 8,105,586; 8,093,353; 8,088,368; 7,897,565; 7,871,607; 7,846,431; 7,829,081; 7,829,077; 7,824,851; 7,572,621; and 7,326,536; Patents assigned to Alios: U.S. Pat. Nos. 9,365,605; 9,346,848; 9,328,119; 9,278,990; 9,249,174; 9,243,022; 9,073,960; 9,012,427; 8,980,865; 8,895,723; 8,877,731; 8,871,737; 8,846,896 and 8,772,474; Achillion U.S. Pat. Nos. 9,273,082; 9,233,136; 9,227,952; 9,133,115; 9,125,904; 9,115,175; 9,085,607; 9,006,423; 8,946,422; 8,835,456; 8,809,313; 8,785,378; 8,614,180; 8,445,430; 8,435,984; 8,183,263; 8,173,636; 8,163,693; 8,138,346; 8,114,888; 8,106,209; 8,088,806; 8,044,204; 7,985,541; 7,906,619; 7,902,365; 7,767,706; 7,741,334; 7,718,671; 7,659,399; 7,476,686; 7,439,374; 7,365,068; 7,199,128; and 7,094,807; Cocrystal Pharma Inc. U.S. Pat. Nos. 9,181,227; 9,173,893; 9,040,479 and 8,771,665; Gilead Sciences U.S. Pat. Nos. 9,353,423; 9,346,841; 9,321,800; 9,296,782; 9,296,777; 9,284,342; 9,238,039; 9,216,996; 9,206,217; 9,161,934; 9,145,441; 9,139,604; 9,090,653; 9,090,642; 9,085,573; 9,062,092; 9,056,860; 9,045,520; 9,045,462; 9,029,534; 8,980,878; 8,969,588; 8,962,652; 8,957,046; 8,957,045; 8,946,238; 8,933,015; 8,927,741; 8,906,880; 8,889,159; 8,871,785; 8,841,275; 8,815,858; 8,809,330; 8,809,267; 8,809,266; 8,779,141; 8,765,710; 8,759,544; 8,759,510; 8,735,569; 8,735,372; 8,729,089; 8,722,677; 8,716,264; 8,716,263; 8,716,262; 8,697,861; 8,664,386; 8,642,756; 8,637,531; 8,633,309; 8,629,263; 8,618,076; 8,592,397; 8,580,765; 8,569,478; 8,563,530; 8,551,973; 8,536,187; 8,513,186; 8,513,184; 8,492,539; 8,486,938; 8,481,713; 8,476,225; 8,420,597; 8,415,322; 8,338,435; 8,334,270; 8,329,926; 8,329,727; 8,324,179; 8,283,442; 8,263,612; 8,232,278; 8,178,491; 8,173,621; 8,163,718; 8,143,394; patents assigned to Idenix, acquired by Merck, include U.S. Pat. Nos. 9,353,100; 9,309,275; 9,296,778; 9,284,307; 9,249,173; 9,243,025; 9,211,300; 9,187,515; 9,187,496, 9,109,001; 8,993,595; 8,951,985; 8,691,788; 8,680,071; 8,637,475; 8,507,460; 8,377,962; 8,362,068; 8,343,937; 8,299,038; 8,193, 372; 8,093,379; 7,951,789;

7,932,240; 7,902,202; 7,662,798; 7,635,689; 7,625,875; 7,608,600; 7,608,597; 7,582,618; 7,547,704; 7,456,155; 7,384,924; 7,365,057; 7,192,936; 7,169,766; 7,163,929; 7,157,441; 7,148,206; 7,138,376; 7,105,493; 6,914,054 and 6,812,219; patents assigned to Merck include U.S. Pat. Nos. 9,364,482; 9,339,541; 9,328,138; 9,265,773; 9,254,292; 9,243,002; 9,242,998; 9,242,988; 9,242,917; 9,238,604; 9,156,872; 9,150,603; 9,139,569; 9,120,818; 9,090,661; 9,073,825; 9,061,041; 8,987,195; 8,980,920; 8,927,569; 8,871,759; 8,828,930; 8,772,505; 8,715,638; 8,697,694; 8,637,449; 8,609,635; 8,557,848; 8,546,420; 8,541,434; 8,481,712; 8,470,834; 8,461,107; 8,404,845; 8,377,874; 8,377,873; 8,354,518; 8,309,540; 8,278,322; 8,216,999; 8,148,349; 8,138,164; 8,080,654; 8,071,568; 7,973,040; 7,935,812; 7,915,400; 7,879,815; 7,879,797; 7,632,821; 7,569,374; 7,534,767; 7,470,664 and 7,329,732; patent application publication US 2013/0029904 to Boehringer Ingelheim GMBH and US 2014/0113958 to Stella Aps.

In one embodiment, the additional therapy is a monoclonal antibody (MAb). Some MAbs stimulate an immune response that destroys cancer cells. Similar to the antibodies produced naturally by B cells, these MAbs may "coat" the cancer cell surface, triggering its destruction by the immune system. For example, bevacizumab targets vascular endothelial growth factor (VEGF), a protein secreted by tumor cells and other cells in the tumor's microenvironment that promotes the development of tumor blood vessels. When bound to bevacizumab, VEGF cannot interact with its cellular receptor, preventing the signaling that leads to the growth of new blood vessels. Similarly, cetuximab and panitumumab target the epidermal growth factor receptor (EGFR), and trastuzumab targets the human epidermal growth factor receptor 2 (HER-2). MAbs that bind to cell surface growth factor receptors prevent the targeted receptors from sending their normal growth-promoting signals. They may also trigger apoptosis and activate the immune system to destroy tumor cells.

In one aspect of the present invention, the bioactive agent is an immunosuppressive agent. The immunosuppressive agent can be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a SiP receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3@), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SEVIULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, aspirin and ibuprofen.

In certain embodiments a monotherapy or combination described herein additionally comprises administering one or more additional therapeutic agents to decrease side effects of the therapy. For example, in certain embodiments a compound described herein or a pharmaceutically acceptable salt thereof is administered concurrently, before, or after administration of an antineutropenia medication, antinausea medication, an antihistamine, and/or an antipain medication. Non-limiting examples of antineutropenia medications include growth factors for example a granulocyce colony stimulating factor (G-CSF). In certain embodiments a therapy in a table above is administered in combination with a G-CSF. G-CSF (or another active agent) can be given before, with after, or on different days than the compound of the present invention.

Non-limiting examples of granulocyte colony stimulating factors include filgrastim (in the form of neupogen, zarxio, nivestym, or another form), CG-10639, and PEGF.

In certain embodiments the granulocyte colony stimulating factor is pegfilgrastim. In certain embodiments the granulocyte colony stimulating factor is Neulasta. In certain embodiments the granulocyte colony stimulating factor is selected from Ristempa, Tezmota, Fulphila, Pelgraz, Udenyca, Udenyca, Pelmeg, Ziextenzo, Grasustek, Ziextenzo, Lapelga, Neutropeg, Cegfila, Nyvepria, and Stimufend.

In certain embodiments the therapy described herein further comprises an antinausea medication. Non-limiting examples of antinauasea medications include aprepitant, dolasetron, granisetron, ondansetron, palonosetron, proclorperazine, promethazine, netupitant-palonosetron, rolapitant, lorazepam, metoclopramide, famotidine, dexamethasone, and ranitidine.

In certain embodiments the therapy described herein further comprises an antihistamine medication. Non-limiting examples of antihistamine medications include benadryl, cetirizine, loratadine, and fexofenadine.

In certain embodiments the therapy described herein further comprises an antipain medication. Non-limiting examples of antipain medications include tramadol, hydromorphone, methadone, morphine, oxycodone, hydrocodone, oxymorphone, fentanyl, and tapentadol.

VIII. Pharmaceutical Compositions

The Degron compound or Degrader as disclosed herein can be administered as the neat chemical, but are more typically administered as a pharmaceutical composition, that includes an effective amount for a host, typically a human, in need of such treatment for any of the disorders described herein. Accordingly, the disclosure provides pharmaceutical compositions comprising an effective amount of compound or pharmaceutically acceptable salt together with at least one pharmaceutically acceptable carrier for any of the uses described herein. The pharmaceutical composition may contain a compound or salt as the only active agent, or, in an alternative embodiment, the compound and at least one additional active agent.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least 0.1, 1, 5, 10, 25, 50, 100, 200, 250, 300, 400, 500, 600, 700, or 750 mg of active compound, or its salt.

The pharmaceutical composition may also include a molar ratio of the active compound and an additional active agent. For example, the pharmaceutical composition may contain a molar ratio of about 0.5:1, about 1:1, about 2:1, about 3:1 or from about 1.5:1 to about 4:1 of an anti-inflammatory or immunosuppressing agent.

Compounds disclosed herein may be administered orally, topically, parenterally, by inhalation or spray, sublingually, via implant, including ocular implant, transdermally, via buccal administration, rectally, as an ophthalmic solution, injection, including ocular injection, intraveneous, intra-aortal, intracranial, subdermal, intraperitioneal, subcutaneous, transnasal, sublingual, or rectal or by other means, in dosage unit formulations containing conventional pharmaceutically acceptable carriers.

For ocular delivery, the compound can be administered, as desired, for example, via intravitreal, intrastromal, intracameral, sub-tenon, sub-retinal, retro-bulbar, peribulbar, suprachorodial, conjunctival, subconjunctival, episcleral, periocular, transscleral, retrobulbar, posterior juxtascleral, circumcorneal, or tear duct injections, or through a mucus, mucin, or a mucosal barrier, in an immediate or controlled release fashion or via an ocular device.

The pharmaceutical composition may be formulated as any pharmaceutically useful form, e.g., as an aerosol, a cream, a gel, a pill, an injection or infusion solution, a capsule, a tablet, a syrup, a transdermal patch, a subcutaneous patch, a dry powder, an inhalation formulation, in a medical device, suppository, buccal, or sublingual formulation, parenteral formulation, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions can contain any amount of active compound that achieves the desired result, for example between 0.1 and 99 weight % (wt. %) of the compound and usually at least about 5 wt. % of the compound. Some embodiments contain from about 25 wt. % to about 50 wt. % or from about 5 wt. % to about 75 wt. % of the compound.

Formulations suitable for rectal administration are typically presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

IX. General Synthesis

The compounds described herein can be prepared by methods known to those skilled in the art. In some non-limiting examples, the disclosed compounds can be made by the schemes provided below.

Compounds of the present invention with stereocenters may be drawn without stereochemistry for convenience. One skilled in the art will recognize that pure enantiomers and diastereomers can be prepared by methods known in the art. Examples of methods to obtain optically active materials include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separationsa—technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

xiv) simulated moving bed chromatography, is used in one embodiment. A wide variety of chiral stationary phases are commercially available.

The chemical synthesis of Degraders of the present invention may be carried out according to the following general Schemes 1-4 which differ in sequence of steps used for binding a degron, linker, and targeting ligand. As illustrated in these Shemes and Examples below, compounds for use in the present invention can readily be synthesized by one skilled in the art in a variety of methods and chemical reactions.

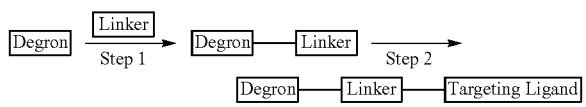

As shown in Scheme 1, compounds for use in the present invention can be prepared by chemically combining a Degron and a Linker followed by subsequent addition of a Targeting Ligand.

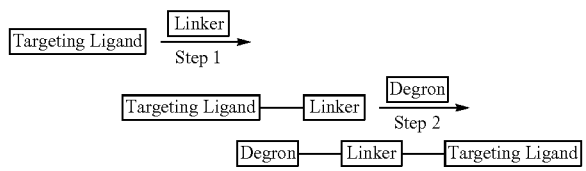

Similarly, in Scheme 2 compounds for use in the present invention are prepared by chemically combing a Targeting Ligand and Linker first, followed by subsequent addition of a Degron.

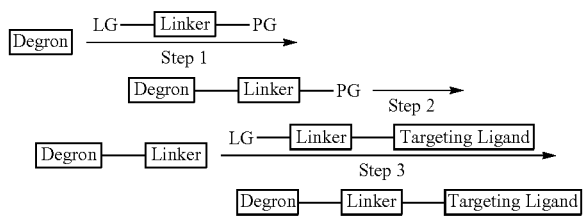

In Scheme 3, in Step 1, a nucleophilic Degron displaces a leaving group on the Linker to make a Degron Linker fragment. In Step 2, the protecting group is removed by methods known in the art to free a nucleophilic site on the linker. In Step 3, the nucleophilic Degron Linker fragment displaces a leaving group on the Targeting Ligand to form a compound for use in the present invention. In an alternative embodiment Step 1 and/or Step 2 is accomplished by a coupling reaction instead of a nucleophilic attack.

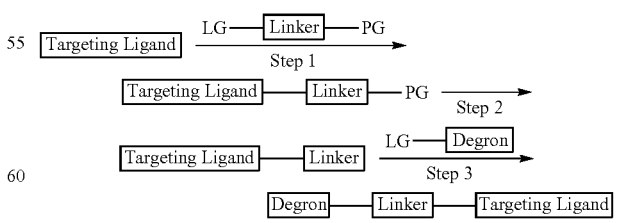

In Scheme 4, in Step 1, a nucleophilic Targeting Ligand displaces a leaving group on the Linker to make a Targeting Ligand Linker fragment. In Step 2, the protecting group is removed by methods known in the art to free a nucleophilic site on the linker. In Step 3, the nucleophilic Targeting Ligand Linker fragment displaces a leaving group on the Degron to form a compound for use in the present invention. In an alternative embodiment Step 1 and/or Step 2 is accomplished by a coupling reaction instead of a nucleophilic attack.

Hereinafter, the present invention will be illustrated by specific Examples of carrying out the present invention.

Experimental Examples of the Present Invention

Example 1. Synthesis of Representative Compounds

Benzomorpholine CRBN Binders

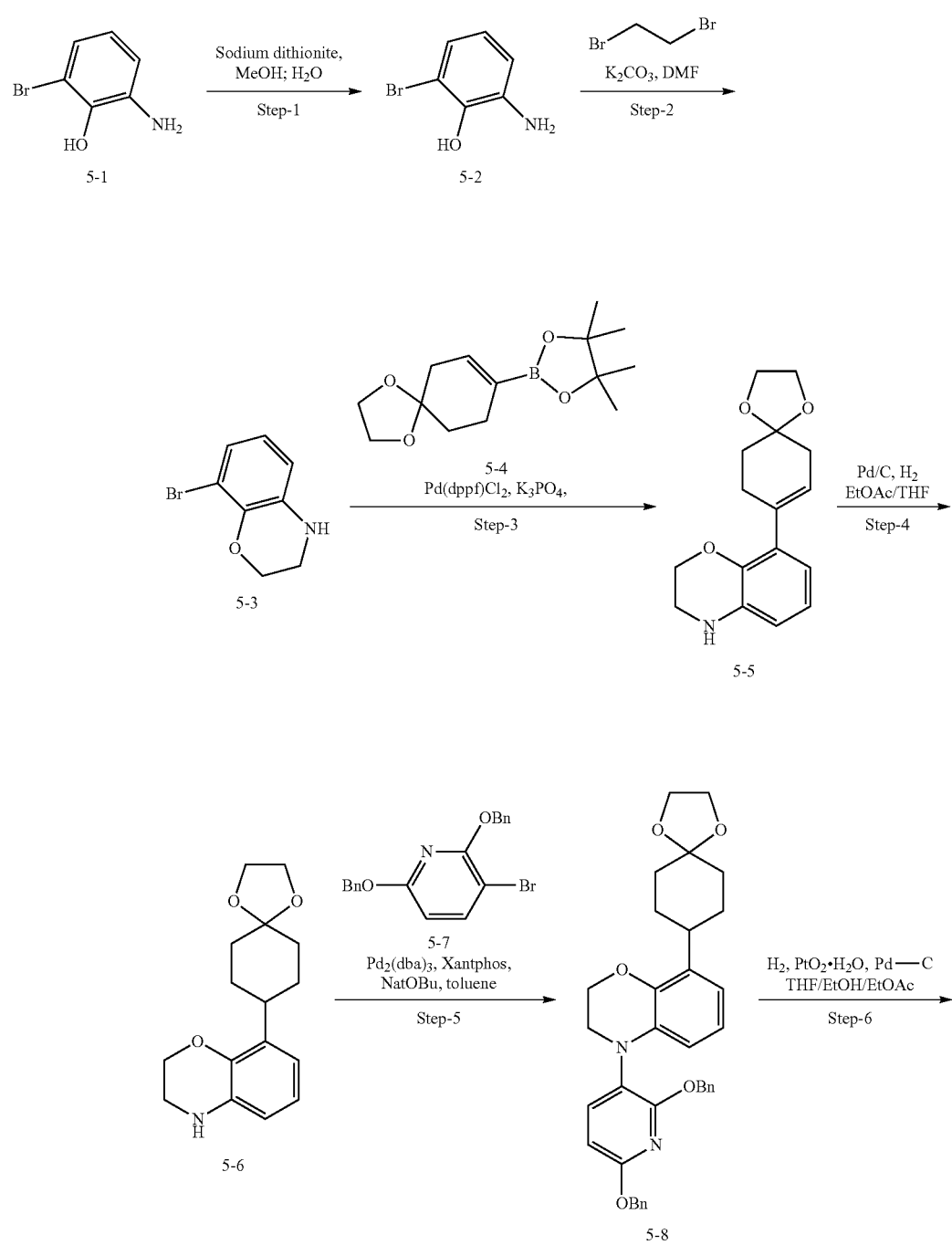

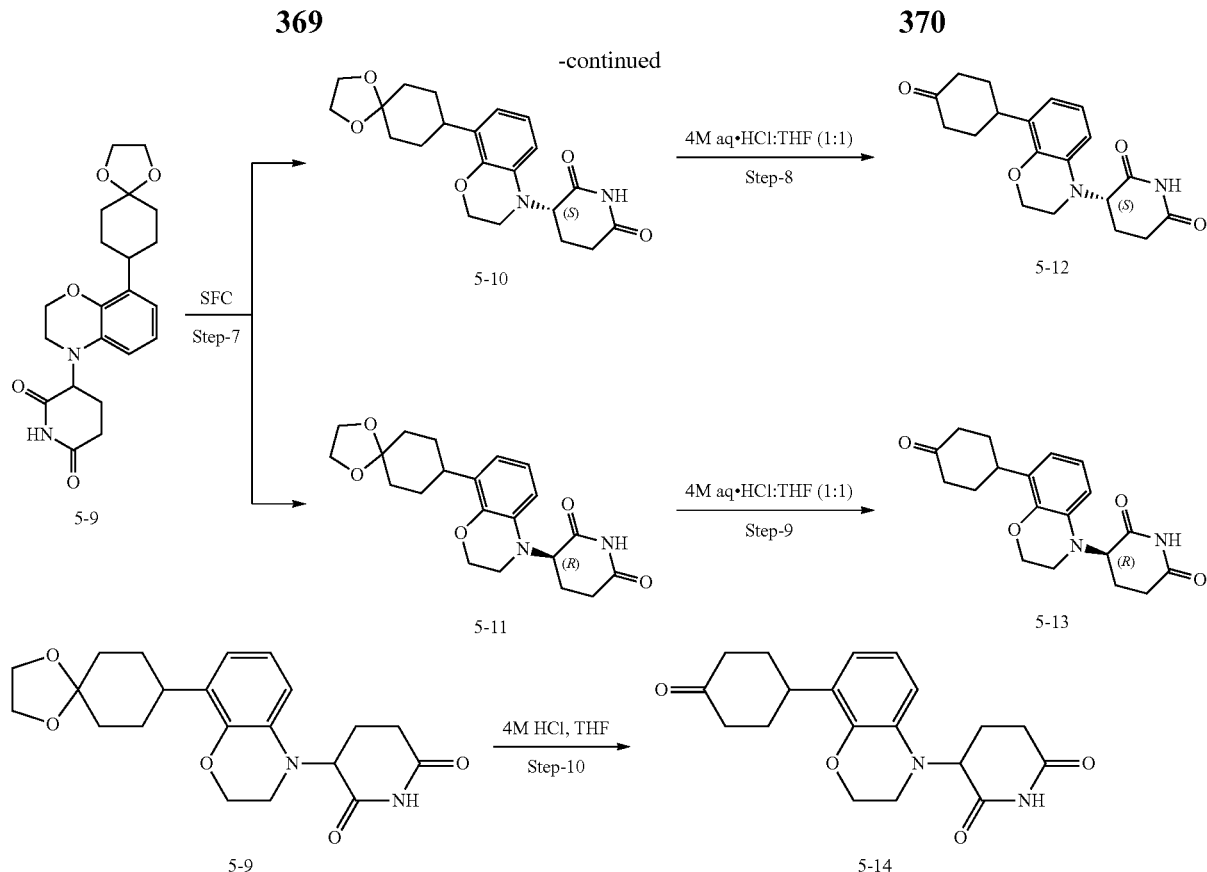

Step-1

A stirred solution of 2-bromo-6-nitro-phenol 5-1 (30 g, 137.61 mmol) in methanol (400 mL) was heated at 70° C. Then sodium dithionite (100 g, 574.36 mmol) was taken into water (360 mL) and added very slowly. Then the reaction mixture was stirred at same temp for 15 min. After completion of the reaction, solvent was filtered through celite and removed. Water was then added, and the mixture was extracted with DCM. The organic layer was dried over $Na_2SO_4$ and concentrated under reduced pressure to get 2-amino-6-bromo-phenol 5-2 (22 g, 111.60 mmol, 81.10% yield) as white solid product. LCMS (ES$^+$): m/z 189.98 [M+H]$^+$.

Step-2:

To a stirred solution of 2-amino-6-bromo-phenol 5-2 (28 g, 148.92 mmol) in DMF (551.32 mL), potassium carbonate (51.46 g, 372.30 mmol) and 1,2-dibromoethane (33.57 g, 178.70 mmol, 15.40 mL) were added. The reaction mixture was stirred at 100° C. for overnight. After completion of the reaction, the reaction mixture was diluted in water and extracted with ethyl acetate, combined organic layer was dried over $Na_2SO_4$ and concentrated under reduced pressure to get crude product, which was purified by column chromatography using 230-400 silica, product was eluted with 0-100% ethyl acetate and hexane to afford 8-bromo-3,4-dihydro-2H-1,4-benzoxazine 5-3 (20 g, 57.14 mmol, 38.37% yield) as a brown liquid. LCMS (ES$^+$): m/z 215.72 [M+H]$^+$.

Step-3:

To a solution of 8-bromo-3,4-dihydro-2H-benzo[b][1,4] oxazine 5-3 (20 g, 93.43 mmol) and 4,4,5,5-tetramethyl-2-(1,4-dioxaspiro[4.5]dec-7-en-8-yl)-1,3,2-dioxaborolane 5-4 (24.87 g, 93.43 mmol) in dioxane (250 mL) and water (50 mL), potassium phosphate tribasic anhydrous (49.58 g, 233.58 mmol) was added at room temperature. The reaction mixture was degassed with argon gas for 10 minutes and [1,1'-bis(diphenylphosphino)ferrocene]dichloropalladium (II)-dichloromethane (6.84 g, 9.34 mmol) was added. The reaction mixture was degassed with argon for additional 5 minutes and it was stirred at 95° C. for 16 h. After completion of the reaction the reaction mixture was poured in ice cold water and extracted in ethyl acetate, dried over $Na_2SO_4$ and concentrated in vacuo to get the crude product, which was purified by column chromatography using Davisil silica and 0 to 100 EtOAc in petroleum ether as eluent to afford 8-(1,4-dioxaspiro[4.5]dec-7-en-8-yl)-3,4-dihydro-2H-1,4-benzoxazine 5-5 (25 g, 90.61 mmol, 96.98% yield) as brown liquid. LCMS (ES$^+$): m/z 274.89 [M+H]$^+$.

Step-4:

To a stirred solution of 8-(1,4-dioxaspiro[4.5]dec-7-en-8-yl)-3,4-dihydro-2H-1,4-benzoxazine 5-5 (15 g, 54.88 mmol) in ethyl acetate (150 mL) and THF (150 mL), 10% palladium on carbon, type 487, dry (2.5 g, 23.49 mmol) was added at room temperature. The reaction mixture was stirred in hydrogen atmosphere in a Parr Shaker reactor for 16 h. Subsequently, it was filtered through a celite bed and washed with ethyl acetate. The filtrate was concentrated under reduced pressure to afford 8-(1,4-dioxaspiro[4.5]decan-8-yl)-3,4-dihydro-2H-1,4-benzoxazine 5-6 (14 g, 46.46 mmol, 84.65% yield) as brown liquid. LCMS (ES$^+$): m/z 276.37 [M+H]$^+$.

Step-5:

To a solution of 8-(1,4-dioxaspiro[4.5]decan-8-yl)-3,4-dihydro-2H-1,4-benzoxazine 5-6 (5 g, 18.16 mmol) and 2,6-dibenzyloxy-3-bromo-pyridine 5-7 (8.74 g, 23.61 mmol) in toluene (20 mL) and sodium tert-butoxide (5.24 g, 54.48 mmol) was added at room temperature. The reaction mixture was degassed with nitrogen gas for 10 minutes and tris(dibenzylideneacetone)dipalladium(0) (3.33 g, 3.63 mmol) and Xantphos (2.10 g, 3.63 mmol) was added. The reaction mixture was degassed with nitrogen gas for additional 5 mins and it was stirred at 110° C. for 16 h. The reaction mixture was diluted in water and extracted with ethyl acetate. Then it was dried over sodium sulfate, filtered and concentrated in vacuo to give the crude product, which was purified by column chromatography using 100-200 silica and 20% ethyl acetate in petroleum ether as eluent to afford 4-(2,6-dibenzyloxy-3-pyridyl)-8-(1,4-dioxaspiro[4.5]decan-8-yl)-2,3-dihydro-1,4-benzoxazine 5-8 (6 g, 7.88 mmol, 43.42% yield) as a brown liquid. LCMS (ES$^+$): m/z 565.39 [M+H]$^+$.

Step-6:

A stirred solution of 4-(2,6-dibenzyloxy-3-pyridyl)-8-(1,4-dioxaspiro[4.5]decan-8-yl)-2,3-dihydro-1,4-benzoxazine 5-8 (10 g, 17.71 mmol) in THE (150 mL) and ethyl acetate (150 mL) and ethanol (150 mL) was degassed with argon for 10 min. Then 10% palladium on carbon, type 487, dry (9 g, 84.57 mmol) was added to the reaction mixture and it was stirred for 16 h at room temperature under H$_2$ pressure. Upon completion of the reaction, it was filtered through celite bed, washed with THE and EtOAc. The filtrate was evaporated under reduced pressure to give 3-[8-(1,4-dioxaspiro[4.5]decan-8-yl)-2,3-dihydro-1,4-benzoxazin-4-yl]piperidine-2,6-dione 5-9 (3.6 g, 8.55 mmol, 48.28% yield) as off white solid. LCMS (ES$^+$): m/z 387.58 [M+H]$^+$.

Step-7:

Racemic 3-[8-(1,4-dioxaspiro[4.5]decan-8-yl)-2,3-dihydro-1,4-benzoxazin-4-yl]piperidine-2,6-dione 5-9 (5 g, 12.94 mmol) was submitted for SFC for the separation of isomers. The fractions obtained were concentrated and lyophilized to afford (3S)-3-[8-(1,4-dioxaspiro[4.5]decan-8-yl)-2,3-dihydro-1,4-benzoxazin-4-yl]piperidine-2,6-dione 5-10 (2.2 g, 5.61 mmol, 43.38% yield) (Early eluting peak, arbitrarily assigned S-isomer) and (3R)-3-[8-(1,4-dioxaspiro[4.5]decan-8-yl)-2,3-dihydro-1,4-benzoxazin-4-yl]piperidine-2,6-dione 5-11 (2.2 g, 5.64 mmol, 43.58% yield) (Late eluting peak, arbitrarily assigned R-isomer) as off white solids.

5-10: LCMS (ES$^+$): m/z 387.40 [M+H]$^+$.
5-11: LCMS (ES$^+$): m/z 387.40 [M+H]$^+$.

Preparative SFC conditions: column/dimensions: CHIRALCEL-OJ-H ((30×250) mm, 5µ; % CO$_2$: 60%; % co-solvent: 40% (ACETONITRILE)); Total Flow: 100 g/min; Back Pressure: 100 bar; Temperature: 30° C.; UV: 240 nm; Solubility: ACN+THF.

Step-8:

To a stirred solution of (3S)-3-[8-(1,4-dioxaspiro[4.5]decan-8-yl)-2,3-dihydro-1,4-benzoxazin-4-yl]piperidine-2,6-dione 5-10 (5.2 g, 13.46 mmol) in THF (63.33 mL) at room temperature was added 4 M HCl (4 M, 86.67 mL). The reaction mixture was stirred at room temperature for 1 hr. After completion of the reaction, reaction mixture was concentrated and diluted with water, and neutralized with sat. NaHCO$_3$ solution. The observed solid precipitate was separated by filtration, and dried to give (3S)-3-[8-(4-oxocyclohexyl)-2,3-dihydro-1,4-benzoxazin-4-yl]piperidine-2,6-dione 5-12 (4.5 g, 13.03 mmol, 96.80% yield) as an off white solid. LCMS (ES$^+$): m/z 343.31[M+H]$^+$.

Step-9:

A stirred solution of (3R)-3-[8-(1,4-dioxaspiro[4.5]decan-8-yl)-2,3-dihydro-1,4-benzoxazin-4-yl]piperidine-2,6-dione 5-11 (1 g, 2.59 mmol) in THE (20 mL) was added 4.0 M HCl in water (4 M, 20 mL) at 0° C. and reaction mixture stirred at 28° C. for 1 hr. Upon completion of reaction, the reaction mixture was concentrated and diluted with water, neutralized with sat. NaHCO$_3$ solution to form a precipitate, which was filtered through Buchner funnel, washed with cold water, and dried under vacuum to afford (3R)-3-[8-(4-oxocyclohexyl)-2,3-dihydro-1,4-benzoxazin-4-yl]piperidine-2,6-dione 5-13 (0.8 g, 2.31 mmol, 89.31% yield) as an off-white solid. LCMS (ES$^+$): m/z 343.30 [M+H]$^+$.

Step-10:

A stirred solution of 3-[8-(1,4-dioxaspiro[4.5]decan-8-yl)-2,3-dihydro-1,4-benzoxazin-4-yl]piperidine-2,6-dione 5-9 (1.00 g, 2.59 mmol) in THE (10 mL) was added 4 M HCl (10 mL) at room temperature, and the reaction mixture was stirred at 28° C. for 16 hr. Upon completion of reaction, the reaction mixture was concentrated, diluted with water, cooled to 0° C. and neutralized with sat. NaHCO$_3$ solution. The aqueous layer was extracted with EtOAc, and the combined organic layers were washed with water, brine, and concentrated under reduced pressure to give 3-[8-(4-oxocyclohexyl)-2,3-dihydro-1,4-benzoxazin-4-yl]piperidine-2,6-dione 5-14 (0.8 g, 2.10 mmol, 81.08% yield) as an off-white solid. LCMS (ES$^+$): m/z 343.5 [M+H]$^+$.

Scheme 6: Synthesis of (3S)-3-[8-(4-oxo-1-piperidyl)-2,3-dihydro-1,4-benzoxazin-4-yl]piperidine-2,6-dione, (3R)-3-[8-(4-oxo-1-piperidyl)-2,3-dihydro-1,4-benzoxazin-4-yl]piperidine-2,6-dione, and 3-[8-(1,4-dioxa-8-azaspiro[4.5]decan-8-yl)-2,3-dihydro-1,4-benzoxazin-4-yl]piperidine-2,6-dione
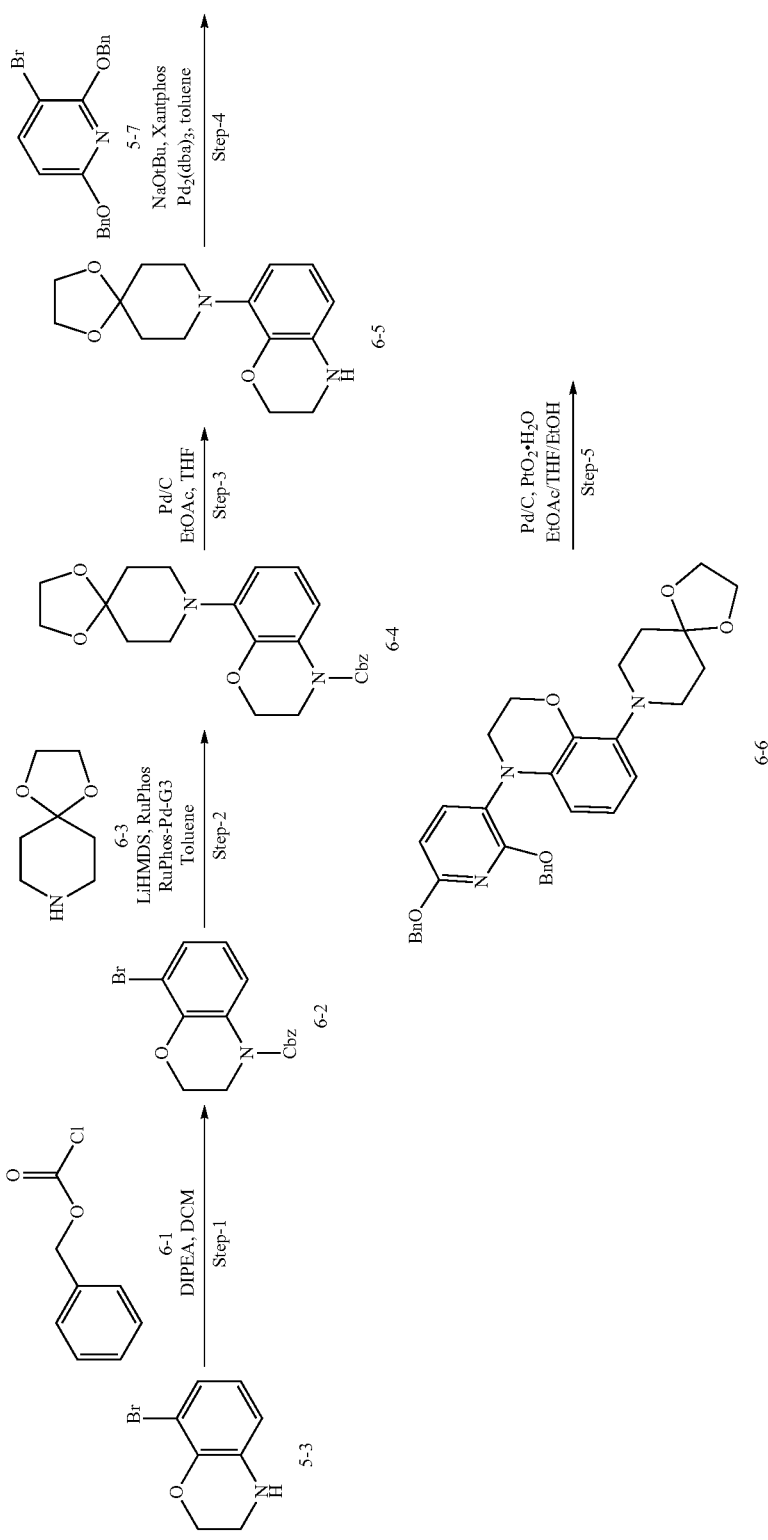

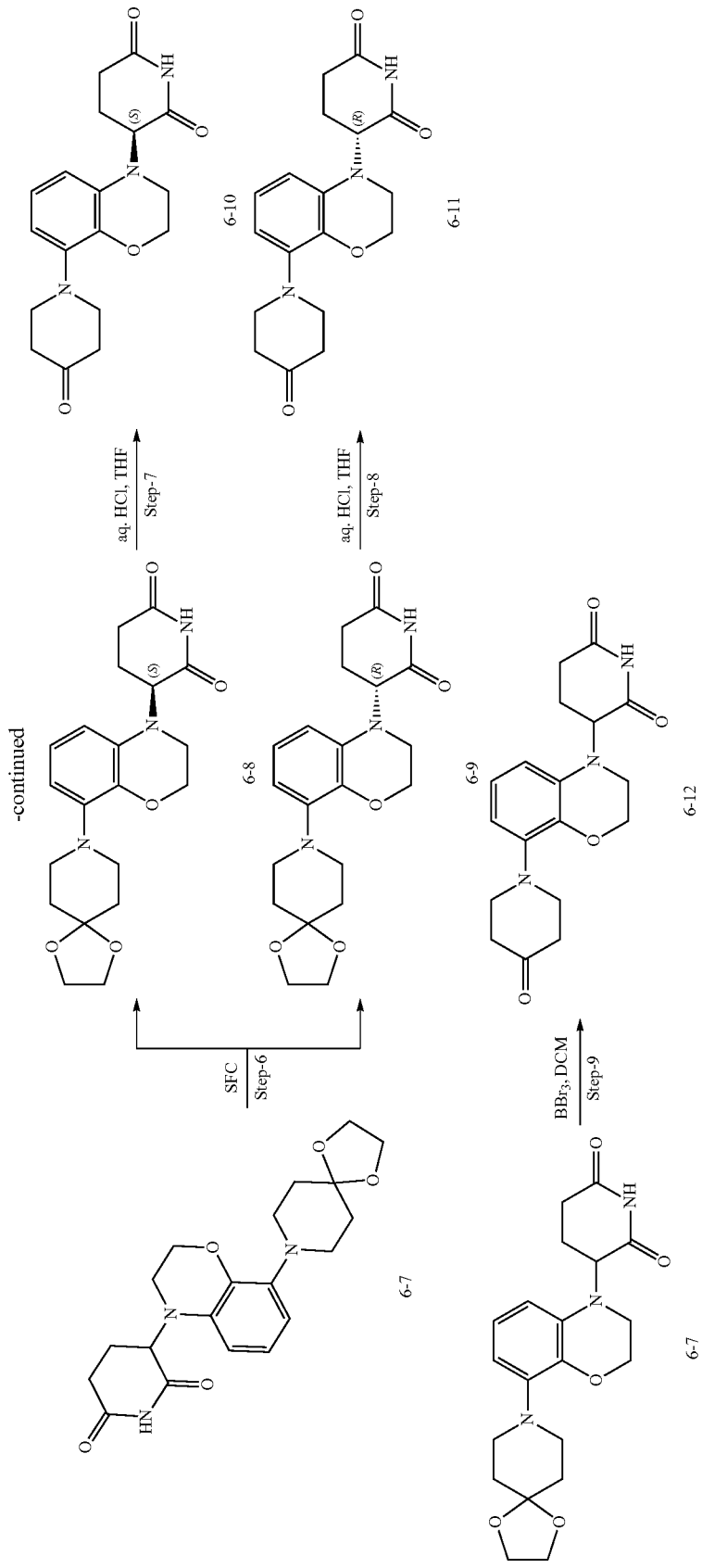

To a solution of 8-bromo-3,4-dihydro-2H-1,4-benzoxazine 5-3 (40.0 g, 186.86 mmol) and N-ethyl-N-isopropylpropan-2-amine (72.45 g, 560.59 mmol, 97.65 mL) in DCM (400 mL), cooled to 0° C., benzyl carbonochloridate 6-1 (38.25 g, 224.24 mmol) was added. The reaction mixture was stirred at room temperature for 16 h. Upon completion of the reaction, it was diluted with DCM and washed with saturated NaHCO$_3$ solution and brine. The organic layer was dried over Na$_2$SO$_4$, filtered and concentrated under reduced pressure to afford crude product. It was purified by flash chromatography over silica gel (230-400 mesh size) by using 10% ethyl acetate in petroleum ether as an eluent to afford benzyl 8-bromo-2,3-dihydro-1,4-benzoxazine-4-carboxylate 6-2 (48.5 g, 137.90 mmol, 73.80% yield) as a pale-yellow solid. LCMS (ES$^+$): m/z 348.33 M+H]$^+$.

Step-2:

To a solution of benzyl 8-bromo-2,3-dihydro-1,4-benzoxazine-4-carboxylate 6-2 (48.5 g, 139.29 mmol) and 1,4-dioxa-8-azaspiro[4.5]decane 6-3 (19.94 g, 139.29 mmol, 17.86 mL) in toluene (500 mL), lithium bis(trimethylsilyl) amide solution 1.4 M in THF (248.73 mL) was added at room temperature. The reaction mixture was degassed with nitrogen gas for 10 minutes and RuPhos (3.25 g, 6.96 mmol) and RuPhos Pd G3 (11.65 g, 13.93 mmol) were added. The reaction mixture was stirred at 100° C. for 2 h. The reaction mixture was filtered through a celite bed and washed with ethyl acetate (100 mL). The organic layer was washed with water (50 mL) and brine (50 mL), dried over sodium sulfate, filtered and concentrated in vacuo to get the crude product, which was purified by column chromatography using Davisil silica and 25% ethyl acetate in petroleum ether as an eluent to afford benzyl 8-(1,4-dioxa-8-azaspiro[4.5]decan-8-yl)-2,3-dihydro-1,4-benzoxazine-4-carboxylate 6-4 (42.7 g, 89.47 mmol, 64.23% yield) as a colorless gum. LCMS (ES$^+$): m/z 411.34 (M+H)+.

Step-3:

To a stirred solution of benzyl 8-(1,4-dioxa-8-azaspiro[4.5]decan-8-yl)-2,3-dihydro-1,4-benzoxazine-4-carboxylate 6-4 (42.7 g, 104.03 mmol) in EtOAc (300 mL) and THF (300 mL) was added 10% palladium on carbon, type 487, dry (11.07 g, 104.03 mmol) at room temperature. The reaction mixture was stirred in hydrogen atmosphere under balloon pressure for 16 h. Subsequently, it was filtered through a celite bed and washed with ethyl acetate (100 mL). The filtrate was concentrated under reduced pressure to afford 8-(3,4-dihydro-2H-1,4-benzoxazin-8-yl)-1,4-dioxa-8-azaspiro[4.5]decane 6-5 (25.4 g, 85.48 mmol, 82.17% yield) as a brown gummy substance. LCMS (ES$^+$): m/z 277.30 [M+H]$^+$.

Step-4:

To a solution of 8-(3,4-dihydro-2H-1,4-benzoxazin-8-yl)-1,4-dioxa-8-azaspiro[4.5]decane 6-5 (25.4 g, 91.92 mmol) and 2,6-dibenzyloxy-3-bromo-pyridine 5-7 (34.03 g, 91.92 mmol) in toluene (500 mL), sodium 2-methylpropan-2-olate (22.08 g, 229.80 mmol) was added at room temperature. The reaction mixture was degassed with nitrogen gas for 10 minutes and (5-diphenylphosphanyl-9,9-dimethyl-xanthen-4-yl)-diphenyl-phosphane (5.32 g, 9.19 mmol) and (1E,4E)-1,5-diphenylpenta-1,4-dien-3-one palladium (8.42 g, 9.19 mmol) were added. The reaction mixture was degassed with nitrogen gas for additional 5 mins and it was stirred at 100° C. for 2 h. The reaction mixture was filtered through a celite bed and washed with ethyl acetate (100 mL). The organic layer was washed with water (50 mL) and brine (50 mL), dried over sodium sulfate, filtered and concentrated in vacuo to get the crude product, which was purified by column chromatography using Davisil silica and 40% ethyl acetate in petroleum ether as eluent to afford 8-[4-(2,6-dibenzyloxy-3-pyridyl)-2,3-dihydro-1,4-benzoxazin-8-yl]-1,4-dioxa-8-azaspiro[4.5]decane 6-6 (40.1 g, 67.35 mmol, 73.27% yield) as a brown gum. LCMS (ES$^+$): m/z 566.94 [M+H]$^+$.

Step-5:

To a stirred solution of 8-[4-(2,6-dibenzyloxy-3-pyridyl)-2,3-dihydro-1,4-benzoxazin-8-yl]-1,4-dioxa-8-azaspiro[4.5] decane 6-6 (40.1 g, 70.89 mmol) in ethanol (400 mL), EtOAc (400 mL) and THF (400 mL), palladium, 10% on carbon, type 487, dry (7.54 g, 70.89 mmol) and dioxoplatinum hydrate (1.74 g, 7.09 mmol) were added at room temperature. The reaction mixture was stirred in hydrogen atmosphere under pressure for 16 h. Subsequently, the reaction mixture was filtered through a celite bed and washed with ethyl acetate (1000 mL). The filtrate was concentrated under reduced pressure to afford 3-[8-(1,4-dioxa-8-azaspiro[4.5]decan-8-yl)-2,3-dihydro-1,4-benzoxazin-4-yl]piperidine-2,6-dione 6-7 (14.2 g, 34.45 mmol, 48.60% yield) as an off white solid. LCMS (ES$^+$): m/z 388.35 [M+H]$^+$.

Step-6:

Racemic 3-(8-(1,4-dioxa-8-azaspiro[4.5]decan-8-yl)-2,3-dihydro-4H-benzo[b][1,4]oxazin-4-yl)piperidine-2,6-dione 6-7 (8.0 g) was separated by SFC to give 6-8 (Early-eluting peak arbitrarily assigned as S-isomer, 3.7 g) and 6-9 (Late eluting peak arbitrarily assigned as R-isomer, 3.9 g).

Preparative SFC conditions: column/dimensions: CHIRALPAK-IJ (30×250) mm, 5µ; % CO$_2$: 70%; % co-solvent: 30% (ACN); Total Flow: 100g/min; Back Pressure: 100 bar; Temperature: 30° C.; UV: 232 nm; Solubility: ACN.

Step-7:

To a stirred solution of (3S)-3-[8-(1,4-dioxa-8-azaspiro [4.5]decan-8-yl)-2,3-dihydro-1,4-benzoxazin-4-yl]piperidine-2,6-dione 6-8 (0.8 g, 2.06 mmol) in THF (4.91 mL) at room temperature was added hydrochloric acid, 36% w/w aq. soln. (75.29 mg, 2.06 mmol, 94.11 L). The reaction mass was stirred at 70° C. for 5 h. After completion of the reaction, the reaction mixture was concentrated in vacuo, diluted with sat. NaHCO$_3$ solution and extracted with EtOAc. The organic layer was then dried over Na$_2$SO$_4$ and concentrated under reduced pressure to give (3S)-3-[8-(4-oxo-1-piperidyl)-2,3-dihydro-1,4-benzoxazin-4-yl]piperidine-2,6-dione 6-10 (0.35 g, 937.75 mol, 45.41% yield) as a white solid. LCMS (ES$^+$): m/z 344.1 [M+H]$^+$.

Step-8:

To a stirred solution of (3R)-3-[8-(1,4-dioxa-8-azaspiro [4.5]decan-8-yl)-2,3-dihydro-1,4-benzoxazin-4-yl]piperidine-2,6-dione 6-9 (0.9 g, 2.32 mmol) in THF (4.89 mL) at room temperature was added hydrochloric acid, 36% w/w aq. soln. (84.70 mg, 2.32 mmol, 105.87 L). The reaction mass was stirred at 70° C. for 16 h. After completion of the reaction, the reaction mixture was concentrated in vacuo, diluted with sat. NaHCO$_3$ solution and extracted with EtOAc.

The organic layer was then dried over Na$_2$SO$_4$ and concentrated under reduced pressure to give (3R)-3-[8-(4-oxo-1-piperidyl)-2,3-dihydro-1,4-benzoxazin-4-yl]piperidine-2,6-dione 6-11 (0.3 g, 751.36 mol, 32.34% yield) as a white solid. LCMS (ES$^+$): m/z 344.1 [M+H]$^+$.

Step-9:

To a solution of 3-(8-(1,4-dioxa-8-azaspiro[4.5]decan-8-yl)-2H-benzo[b][1,4]oxazin-4(3H)-yl)piperidine-2,6-dione 6-7 (400 mg, 1.03 mmol) in DCM (10 mL) was added tribromoborane (1.29 g, 5.16 mmol) at 0° C., the mixture was stirred at 25° C. for 12 h. The reaction mixture was concentrated under reduced pressure to remove the solvent. The residue was purified by prep-HPLC (Waters Xbridge $C_{18}$ 150×50mm× 10 μm, water ($NH_4HCO_3$)-ACN). Compound 3-(8-(4-oxopiperidin-1-yl)-2,3-dihydro-4H-benzo[b][1,4]oxazin-4-yl)piperidine-2,6-dione 6-12 (100 mg, 258.11 mol, 25.00% yield) was obtained as a yellow solid. LCMS (ES$^+$): m/z 344.2 [M+H]$^+$.

Scheme 7: Synthesis of (3S)-3-[7-(4-oxocyclohexyl)-2,3-dihydro-1,4-benzoxazin-4-yl]piperidine-2,6-dione and (3R)-3-[7-(4-oxocyclohexyl)-2,3-dihydro-1,4-benzoxazin-4-yl]piperidine-2,6-dione

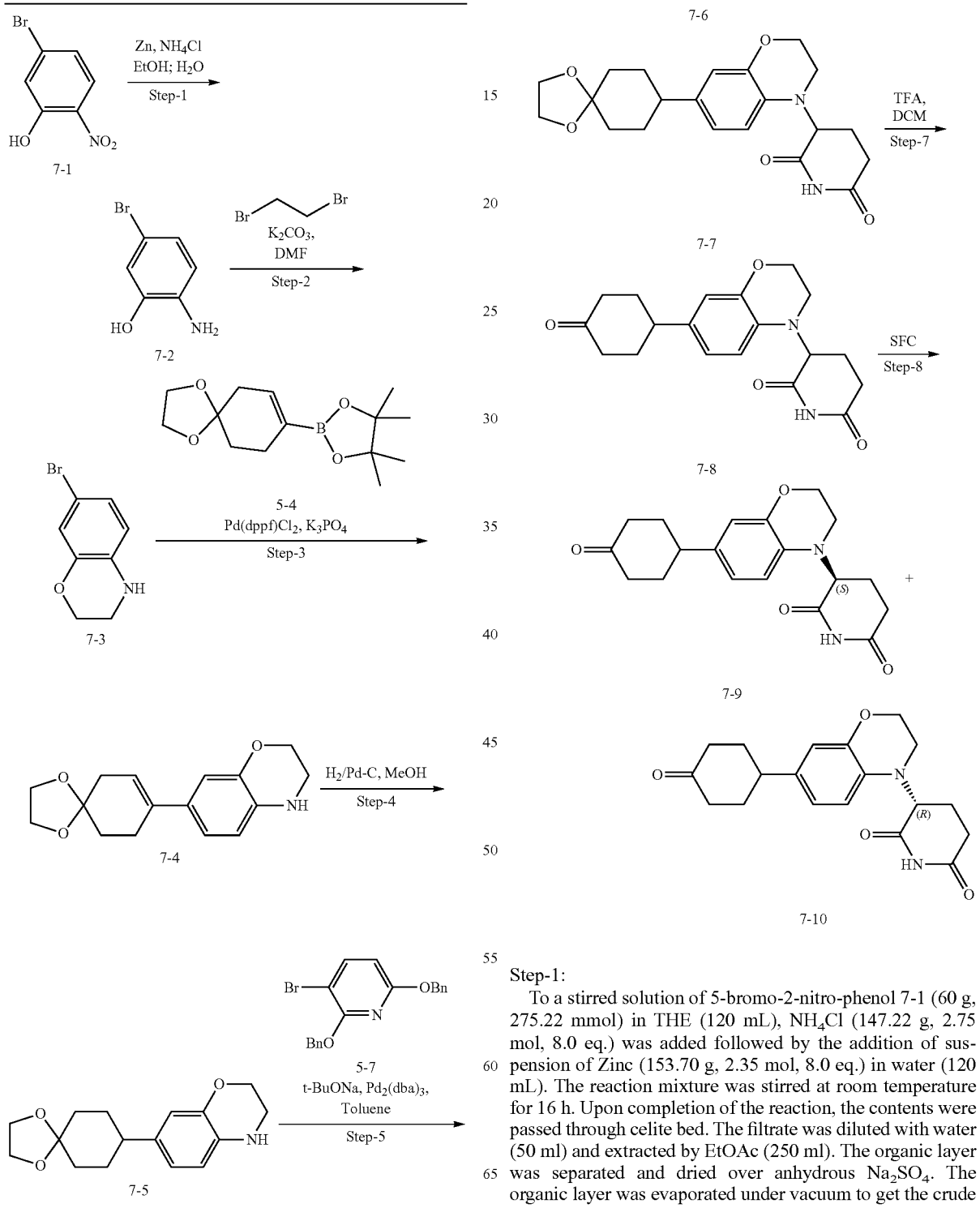

Step-1:

To a stirred solution of 5-bromo-2-nitro-phenol 7-1 (60 g, 275.22 mmol) in THF (120 mL), $NH_4Cl$ (147.22 g, 2.75 mol, 8.0 eq.) was added followed by the addition of suspension of Zinc (153.70 g, 2.35 mol, 8.0 eq.) in water (120 mL). The reaction mixture was stirred at room temperature for 16 h. Upon completion of the reaction, the contents were passed through celite bed. The filtrate was diluted with water (50 ml) and extracted by EtOAc (250 ml). The organic layer was separated and dried over anhydrous $Na_2SO_4$. The organic layer was evaporated under vacuum to get the crude compound, which was purified by column chromatography using Davisil silica (eluting solvent 0-70% EtOAc in petroleum ether) to get 2-amino-5-bromo-phenol 7-2 (35 g, 152.64 mmol, 55.46% yield) as a brown solid. LCMS (ES⁻): m/z 185.95 [M−H]⁻.

Step-2:

To a stirred solution of 2-amino-5-bromo-phenol 7-2 (35 g, 186.15 mmol) and 1,2-dibromoethane (34.97 g, 186.15 mmol, 16.04 mL) in DMF (15 mL) was added $K_2CO_3$ (51.45 g, 372.30 mmol). The reaction mixture was stirred at 100° C. for 16 h. Upon completion of reaction, reaction mixture was poured in ice cooled water. The product was extracted using EtOAc (100 mL). The organic layer was washed with cooled brine to get the crude product. It was purified by column chromatography on silica gel (Davisil silica gel) by using 0-100% EtOAc in petroleum ether as eluent to get 7-bromo-3,4-dihydro-2H-1,4-benzoxazine 7-3 (15 g, 31.97 mmol, 17.17% yield) as a light-yellow liquid. LCMS (ES⁻): m/z 185.95 [M−H]⁻.

Step-3:

To a solution of 7-bromo-3,4-dihydro-2H-1,4-benzoxazine 7-3 (15 g, 70.07 mmol) and 2-(1,4-dioxaspiro[4.5]dec-7-en-8-yl)-4,4,5,5-tetramethyl-1,3,2-dioxaborolane 5-4 (18.65 g, 70.07 mmol) in dioxane (120 mL) and water (10 mL) was added $K_3PO_4$ (29.75 g, 140.15 mmol, 2 eq.) at room temperature. The reaction mixture was degassed with argon for 10 min. Pd(dppf)Cl₂ (2.56 g, 3.50 mmol) was added and the reaction mixture was degassed with argon for additional 5 min and it was stirred at 95° C. for 4 h. Subsequently, the reaction mixture was concentrated in vacuo to get the crude product, which was purified by column chromatography using Davisil silica and 30% EtOAc in petroleum ether as eluent to afford 7-(1,4-dioxaspiro[4.5]dec-7-en-8-yl)-3,4-dihydro-2H-1,4-benzoxazine 7-4 (15 g, 38.42 mmol, 54.82% yield) as an orange colour liquid. LCMS (ES⁺): m/z 274.33 [M+H]⁺.

Step-4:

A stirred solution of 7-(1,4-dioxaspiro[4.5]dec-7-en-8-yl)-3,4-dihydro-2H-1,4-benzoxazine 7-4 (15 g, 54.88 mmol) in MeOH (150 mL) was degassed with argon for 10 min. 10% Palladium on carbon (15.18 g, 142.69 mmol) was added to the reaction mixture and it was stirred for 16 h under $H_2$-pressure in Parr Shaker apparatus (80 psi). Upon completion of the reaction, it was filtered through celite bed, washed with EtOAc (50 mL). The filtrate was evaporated in vacuo to get 7-(1,4-dioxaspiro[4.5]decan-8-yl)-3,4-dihydro-2H-1,4-benzoxazine 7-5 (15 g, 37.48 mmol, 68.30% yield) as a brown liquid. LCMS (ES⁺): m/z 276.78 [M+H]⁺.

Step-5:

To a solution of 7-(1,4-dioxaspiro[4.5]decan-8-yl)-3,4-dihydro-2H-1,4-benzoxazine 7-5 (15 g, 54.48 mmol) and 2,6-dibenzyloxy-3-bromo-pyridine 5-7 (20.17 g, 54.48 mmol) in toluene (15 mL) was added NaO'Bu (10.47 g, 108.96 mmol) at room temperature. The reaction mixture was degassed with nitrogen gas for 10 min and Pd₂(dba)₃ (2.49 g, 2.72 mmol, 0.05 eq.) and Xantphos (2.21 g, 3.81 mmol, 0.07 eq) was added. The reaction mixture was degassed with nitrogen gas for additional 5 min and it was stirred at 100° C. for 16 h. Upon completion, the reaction mixture was filtered through celite bed and washed with EtOAc (200 mL). The organic layer was washed with water (100 mL×3), brine (100 mL×3) and dried over $Na_2SO_4$, filtered and concentrated in vacuo to get the crude product, which was purified by column chromatography using Davisil silica and 20% EtOAc in petroleum ether as eluent to afford 4-(2,6-dibenzyloxy-3-pyridyl)-7-(1,4-dioxaspiro[4.5]decan-8-yl)-2,3-dihydro-1,4-benzoxazine 7-6 (20 g, 27.61 mmol, 50.67% yield) as a brown liquid. LCMS (ES⁺): m/z 565.42 [M+H]⁺.

Step-6:

A stirred solution of 4-(2,6-dibenzyloxy-3-pyridyl)-7-(1,4-dioxaspiro[4.5]decan-8-yl)-2,3-dihydro-1,4-benzoxazine 7-6 (20 g, 35.42 mmol) in MeOH (200 mL) was degassed with argon for 10 min. 10% Palladium on carbon (3.77 g, 35.42 mmol) was added to the reaction mixture and it was stirred at room temperature for 16 h. Upon completion of reaction, it was filtered through a celite bed and washed with EtOAc (50 mL). The filtrate was concentrated in vacuo and purified using column chromatography (silica, 30% EtOAc: petroleum ether) to give 3-[7-(1,4-dioxaspiro[4.5]decan-8-yl)-2,3-dihydro-1,4-benzoxazin-4-yl]piperidine-2,6-dione 7-7 (7 g, 14.83 mmol, 41.88% yield) as a brown liquid. LCMS (ES⁺): m/z 565.42 [M+H]⁺.

Step-7:

To a solution of 3-[7-(1,4-dioxaspiro[4.5]decan-8-yl)-2,3-dihydro-1,4-benzoxazin-4-yl]piperidine-2,6-dione 7-7 (7 g, 18.11 mmol) in DCM (4 mL) was added TFA (24.78 g, 217.37 mmol, 16.75 mL) at 0° C. and the reaction mixture was stirred at room temperature for 16 h. The reaction mixture was concentrated in vacuo to give the crude product, which was triturated with diethyl ether (50 mL) to afford 3-[7-(4-oxocyclohexyl)-2,3-dihydro-1,4-benzoxazin-4-yl]piperidine-2,6-dione 7-8 (4.6 g, 10.61 mmol, 58.59% yield) as a brown liquid. LCMS (ES⁺): m/z 343.47 [M+H]⁺.

Step-8:

Racemic 3-[7-(4-oxocyclohexyl)-2,3-dihydro-1,4-benzoxazin-4-yl]piperidine-2,6-dione 7-8 (2.6 g, 7.59 mmol) was separated by SFC to give (3S)-3-[7-(4-oxocyclohexyl)-2,3-dihydro-1,4-benzoxazin-4-yl]piperidine-2,6-dione 7-9 (Early eluting peak, 0.65 g, 1.89 mmol, 24.88% yield) and (3R)-3-[7-(4-oxocyclohexyl)-2,3-dihydro-1,4-benzoxazin-4-yl]piperidine-2,6-dione 7-10 (Late eluting peak, 0.65 g, 1.89 mmol, 24.83% yield) as off white solids.

Preparative SFC conditions: column/dimensions: CHIRALPAK IC-3 (30×250) mm, 5µ; % CO₂: 55%; % co-solvent: 45% (ACN:IPA); Total Flow: 110 g/min; Back Pressure: 100 bar; Temperature: 30° C.; UV: 220 nm; Solubility: ACN, IPA.

7-9: LCMS (ES⁻): m/z 341.42 [M−H]⁻.

7-10: LCMS (ES⁻): m/z 341.42 [M−H]⁻.

Scheme 8: Synthesis of 3-(8-(4-oxocyclohexyl)-2,3-dihydro-4H-pyrido[3,2-b][1,4]oxazin-4-yl)piperidine-2,6-dione

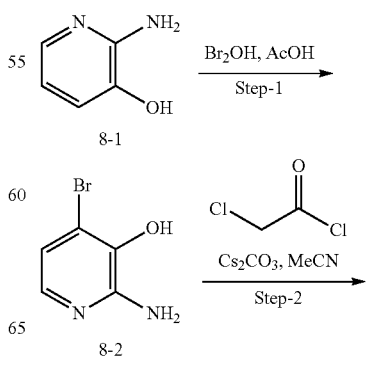

-continued

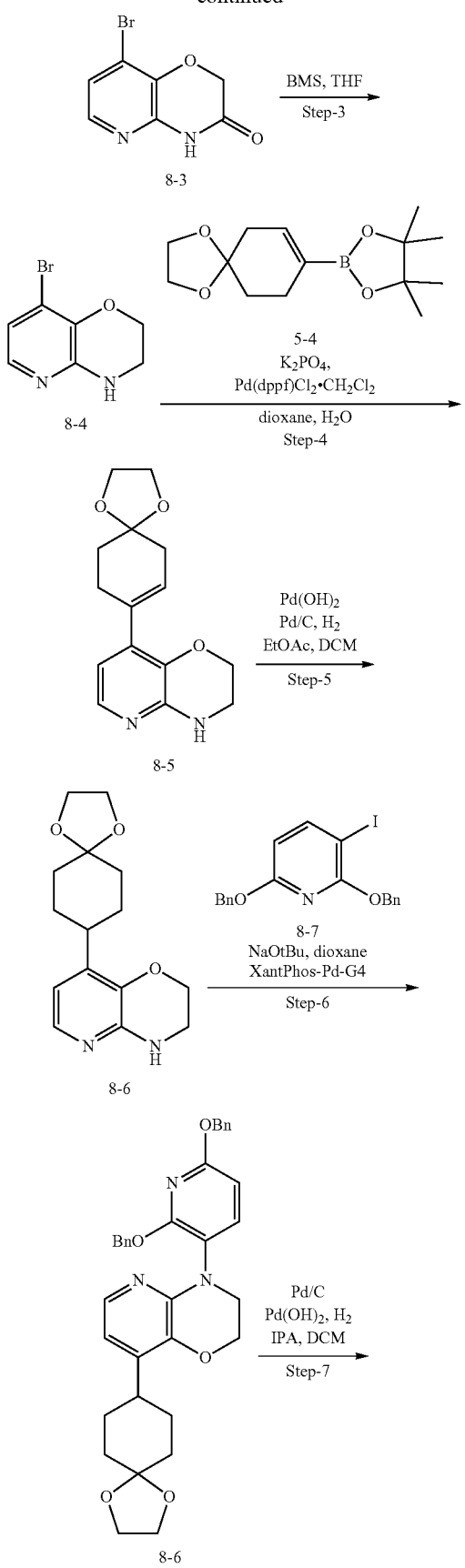

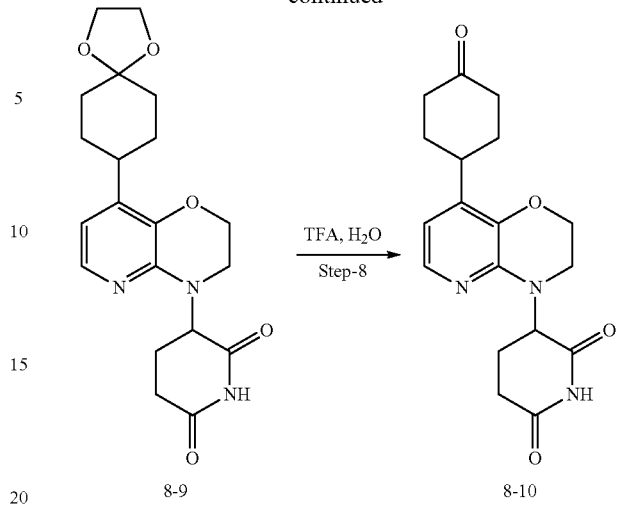

Step-1:
Molecular bromine (25.25 g, 158.02 mmol) was added dropwise to a suspension of 2-aminopyridin-3-ol 8-1 (15 g, 136.22 mmol) in acetic acid (200 mL) at 5-10° C. and then the reaction mixture was brought to room temperature. The reaction mixture was stirred at 120° C. for 12 h. The mixture was concentrated under reduced pressure to give a residue which was triturated with EtOAc (100 mL×2) and dried under vacuum to afford 2-amino-4-bromopyridin-3-ol 8-2 (38.8 g, 126.50 mmol, 92.86% yield, HBr salt) as a dark brown solid. LCMS (ES$^+$): m/z 189.0 [M+H]$^+$.

Step-2:
To a solution of 2-amino-4-bromo-pyridin-3-ol 8-2 (38.8 g, 126.50 mmol, HBr salt) in MeCN (500 mL) were added 2-chloroacetyl chloride (21.43 g, 189.74 mmol, 15.12 mL) at 0° C., and cesium carbonate (206.07 g, 632.48 mmol). The resulting mixture was stirred at 25° C. for 12 h. The reaction mixture was concentrated under reduced pressure. The residue was diluted with H$_2$O (500 mL), filtered and the filter cake was dried in vacuo to afford 8-bromo-2H-pyrido[3,2-b][1,4]oxazin-3(4H)-one 8-3 (15 g, 48.47 mmol, 38.31% yield) as a brown solid. LCMS (ES$^+$): m/z 229.0 [M+H]$^+$.

Step-3:
To a solution of 8-bromo-4H-pyrido[3,2-b][1,4]oxazin-3-one 8-3 (13 g, 42.00 mmol) in THF (150 mL) was added borane dimethyl sulfide complex (10 M, 8.40 mL) at 20° C. The mixture was stirred at 60° C. for 12 h. The reaction mixture was quenched by the addition of methyl alcohol (2 mL) and 1M HCl (20 mL) at 0° C. and stirred at 60° C. for 12 h. Then the mixture was concentrated to give a crude product, which was purified by flash silica gel chromatography (ISCO®; 40 g SepaFlash® Silica Flash Column, Eluent of 0-50% ethyl acetate/petroleum ether gradient @60 mL/min) to afford 8-bromo-3,4-dihydro-2H-pyrido[3,2-b][1,4]oxazine 8-4 (4.9 g, 20.51 mmol, 48.82% yield) as a yellow solid. LCMS (ES$^+$): m/z 215.0 [M+H]$^+$.

Step-4: A mixture of 8-bromo-3,4-dihydro-2H-pyrido[3,2-b][1,4]oxazine 8-4 (1.9 g, 8.84 mmol), 4,4,5,5-tetramethyl-2-(1,4-dioxaspiro[4.5]dec-7-en-8-yl)-1,3,2-dioxaborolane 5-4 (2.59 g, 9.72 mmol), potassium phosphate (5.63 g, 26.51 mmol) and Pd(dppf)$_2$Cl$_2$-dichloromethane (721.52 mg, 883.53 mol) in dioxane (30 mL) and water (6 mL) was degassed and purged with N$_2$ three times, and the mixture was stirred at 100° C. for 12 h under N$_2$ atmosphere. Upon completion of the reaction, the reaction mixture was cooled to room temperature, filtered and concentrated under reduced pressure to give a residue, which was purified by flash silica gel chromatography (ISCO®; 40 g SepaFlash® Silica Flash Column, Eluent of 0-50% petroleum ether/ethyl acetate gradient @60 mL/min) to give 8-(1,4-dioxaspiro[4.5]dec-7-en-8-yl)-3,4-dihydro-2H-pyrido[3,2-b][1,4]oxazine 8-5 (2.2 g, 7.78 mmol, 88.05% yield) as a yellow solid. LCMS (ES$^+$): m/z 275.2 [M+H]$^+$.

Step-5:

To a solution of 8-(1,4-dioxaspiro[4.5]dec-7-en-8-yl)-3,4-dihydro-2H-pyrido[3,2-b][1,4]oxazine 8-5 (2.2 g, 8.02 mmol) in EtOAc (30 mL) and DCM (20 mL) was added 20 wt. % Pd(OH)$_2$ (0.5 g) and 5 wt. % Pd/C (1 g). The suspension was degassed and purged with H$_2$ three times, and then stirred under H$_2$ (15 psi) at 30° C. for 12 h. The mixture was filtered and concentrated under reduced pressure to give a residue, which was purified by flash silica gel chromatography (ISCO®; 20 g SepaFlash® Silica Flash Column, Eluent of 0-30% dichloromethane/ethyl acetate gradient @60 mL/min) to afford 8-(1,4-dioxaspiro[4.5]decan-8-yl)-3,4-dihydro-2H-pyrido[3,2-b][1,4]oxazine 8-6 (2 g, 6.88 mmol, 85.73% yield) as a yellow solid. LCMS (ES$^+$): m/z 277.2 [M+H]$^+$.

Step-6:

A mixture of 8-(1,4-dioxaspiro[4.5]decan-8-yl)-3,4-dihydro-2H-pyrido[3,2-b][1,4]oxazine 8-6 (2 g, 7.24 mmol), 2,6-bis(benzyloxy)-3-iodopyridine 8-7 (3.93 g, 9.41 mmol), sodium 2-methylpropan-2-olate (2 M, 10.86 mL) and Xant-Phos-Pd-G4 (120 mg, 7.24 mmol) in dioxane (40 mL) was degassed and purged with N$_2$ 3 times, and then the mixture was stirred at 100° C. for 5 h under N$_2$ atmosphere. The mixture was cooled to room temperature and diluted with H$_2$O (100 mL) and extracted with DCM (100 mL×2). The combined organic layers were washed with brine (100 mL), dried over Na$_2$SO$_4$, filtered and concentrated under reduced pressure to give a residue, which was purified by flash silica gel chromatography (ISCO®; 12 g SepaFlash® Silica Flash Column, Eluent of 0-50% ethyl acetate/petroleum ether gradient @60 mL/min) to yield 4-(2,6-bis(benzyloxy)pyridin-3-yl)-8-(1,4-dioxaspiro[4.5]decan-8-yl)-3,4-dihydro-2H-pyrido[3,2-b][1,4]oxazine 8-8 (2 g, 3.29 mmol, 45.43% yield) as a yellow solid. LCMS (ES$^+$): m/z 566.3 [M+H]$^+$.

Step-7:

To a solution of 4-(2,6-dibenzyloxy-3-pyridyl)-8-(1,4-dioxaspiro[4.5]decan-8-yl)-2,3-dihydropyrido[3,2-b][1,4]oxazine 8-8 (2 g, 3.54 mmol) in IPA (10 mL) and DCM (30 mL) was added 5 wt. % Pd/C (1 g) and 20 wt. % Pd(OH)$_2$ (1 g). The suspension was degassed and purged 3 times with H$_2$. The mixture was stirred under H$_2$ (15 psi) at 30° C. for 12 h. The reaction mixture was filtered and concentrated under reduced pressure to afford 3-(8-(1,4-dioxaspiro[4.5]decan-8-yl)-2,3-dihydro-4H-pyrido[3,2-b][1,4]oxazin-4-yl)piperidine-2,6-dione 8-9 (1.3 g, 2.55 mmol, 72.13% yield) as a yellow solid. LCMS (ES$^+$): m/z 388.2 [M+H]$^+$.

Step-8:

To a solution of 3-[8-(1,4-dioxaspiro[4.5]decan-8-yl)-2,3-dihydropyrido[3,2-b][1,4]oxazin-4-yl]piperidine-2,6-dione 8-9 (1.1 g, 2.16 mmol) in water (8 mL) was added TFA (5.92 g, 51.92 mmol, 4 mL). After addition, the solution was stirred at 30° C. for 12 h. The reaction solution was poured into sat. NaHCO$_3$ (50 mL) and extracted with DCM (50 mL×2), then the organic layer was dried over Na$_2$SO$_4$ and concentrated under vacuum. The residue was purified by column chromatography (SiO$_2$, DCM/ethyl acetate=1/0 to 1/3) to give 3-(8-(4-oxocyclohexyl)-2,3-dihydro-4H-pyrido[3,2-b][1,4]oxazin-4-yl)piperidine-2,6-dione 8-10 (700 mg, 1.88 mmol, 86.92% yield) as an off-white solid. LCMS (ES$^+$): m/z 343.9 [M+H]$^+$.

Scheme 9: Synthesis of (3S)-3-[8-(4-piperidyl)-2,3-dihydro-1,4-benzoxazin-4-yl]piperidine-2,6-dione, (3R)-3-[8-(4-piperidyl)-2,3-dihydro-1,4-benzoxazin-4-yl]piperidine-2,6-dione and 3-[8-(4-piperidyl)-2,3-dihydro-1,4-benzoxazin-4-yl]piperidine-2,6-dione

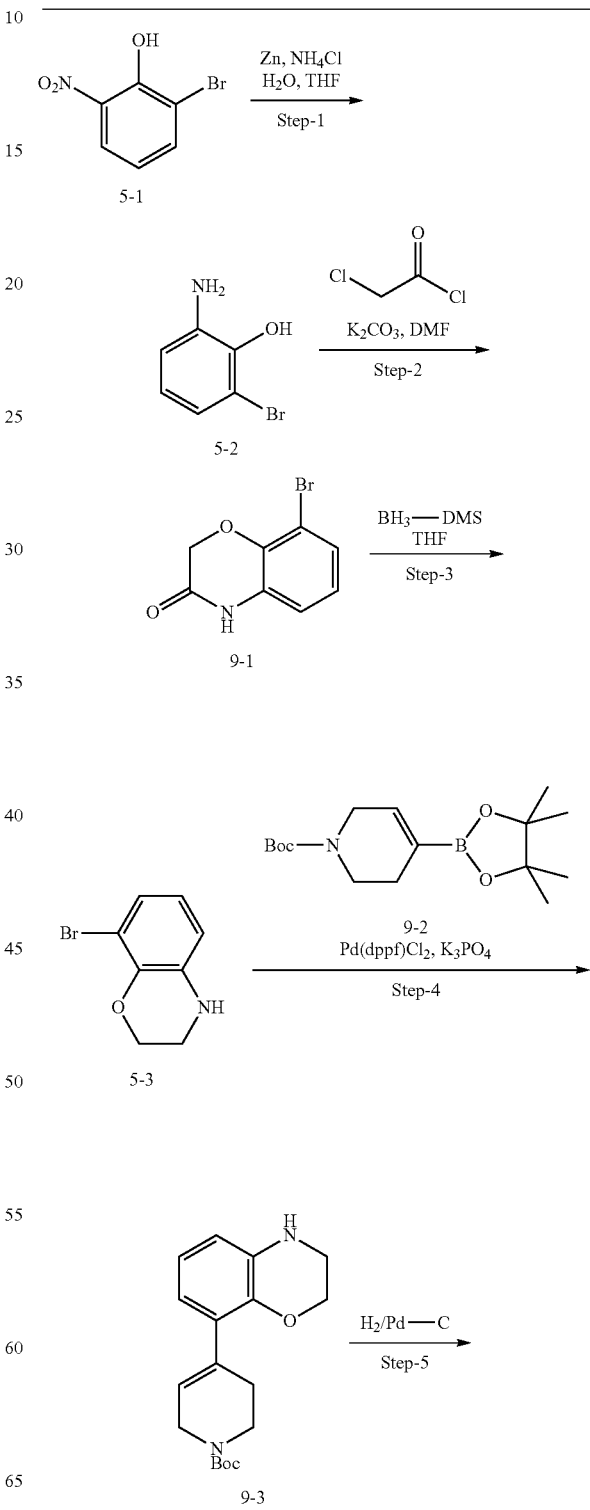

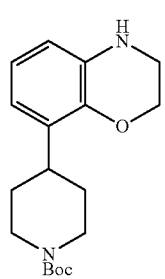
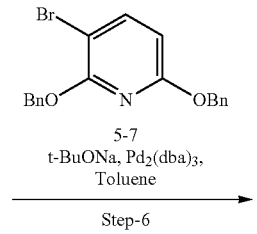
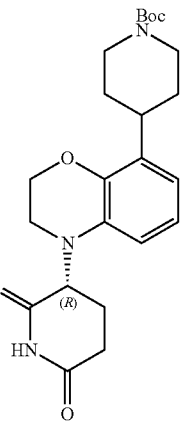
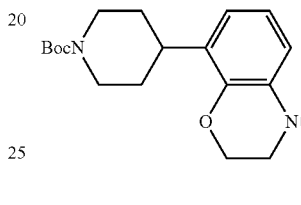
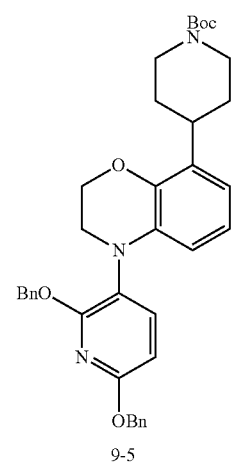
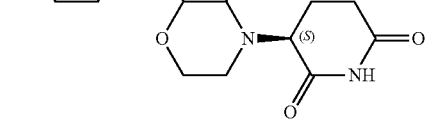
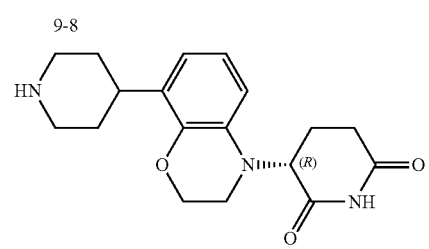
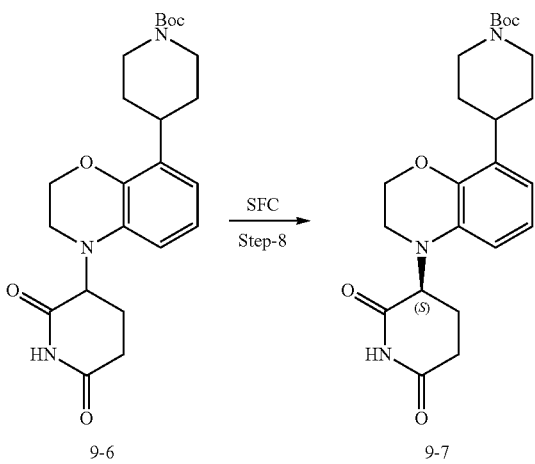
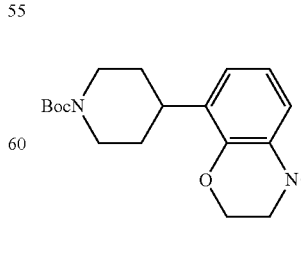

-continued

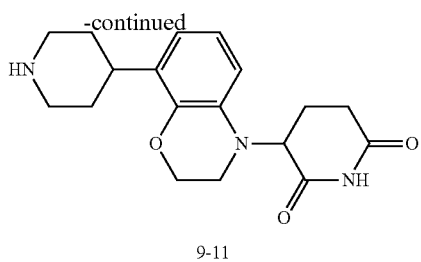

9-11

Step-1:
To a stirred solution of 2-bromo-6-nitro-phenol 5-1 (50 g, 229.35 mmol) in THF (200 mL) was added zinc (149.97 g, 2.29 mol) and the reaction mixture was cooled to 0° C. Then ammonium chloride (122.68 g, 2.29 mol) dissolved in water (100 mL) was added dropwise to the reaction mixture and the mixture was stirred for 1 h at room temperature. Upon the reaction completion, the reaction mixture was filtered through a celite bed, washed with EtOAc and concentrated. The crude material was washed with water and extracted with EtOAc (3×500 mL). The combined organic layers were dried and concentrated in vacuo and the crude material was triturated with pentane to afford 2-amino-6-bromo-phenol 5-2 (35 g, 109.31 mmol, 47.66% yield) as a black color solid. LCMS (ES$^+$): m/z 188.29 [M+H]$^+$.

Step-2:
To a stirred solution of 2-amino-6-bromo-phenol 5-2 (35 g, 186.15 mmol) in DMF (300 mL) was added potassium carbonate (64.32 g, 465.37 mmol). The mixture was cooled to 0° C. and 2-chloroacetyl chloride (23.13 g, 204.76 mmol, 16.29 mL) was added dropwise. The reaction was stirred at room temperature overnight. After completion of the reaction, the reaction mixture poured into ice and stirred for 1 h the solid was filtered and dried under vacuum to afford 8-bromo-4H-1,4-benzoxazin-3-one 9-1 (35 g, 101.74 mmol, 54.66% yield) as a dark brown solid. LCMS (ES$^+$): m/z 228.08 [M+H]$^+$.

Step-3:
To a stirred solution of 8-bromo-4H-1,4-benzoxazin-3-one 9-1 (20 g, 87.70 mmol) in THF (100 mL) at 0° C., was added borane methyl sulfanylmethane (67.28 g, 885.68 mmol, 84.00 mL) in a dropwise manner. The reaction mixture was heated at 78° C. for 1h. Upon completion, the reaction was quenched with saturated ammonium chloride solution and extracted with ethyl acetate. The organic layer was washed with brine and dried over sodium sulphate and concentrated. The crude product thus obtained was purified by column chromatography to afford 8-bromo-3,4-dihydro-2H-1,4-benzoxazine 5-3 (16 g, 65.92 mmol, 75.16% yield) as a white solid. LCMS (ES$^+$): m/z 213.83 [M+H]$^+$.

Step-4:
To a solution of 8-bromo-3,4-dihydro-2H-1,4-benzoxazine 5-3 (16 g, 74.75 mmol) and tert-butyl 4-(4,4,5,5-tetramethyl-1,3,2-dioxaborolan-2-yl)-3,6-dihydro-2H-pyridine-1-carboxylate 9-2 (23.11 g, 74.75 mmol) in 1,4-dioxane (80 mL) and water (10 mL) was added tripotassium phosphate (47.60 g, 224.24 mmol) at room temperature. The reaction mixture was degassed with argon purging, and Pd(dppf)Cl$_2$ (2.73 g, 3.74 mmol) was added. The reaction mixture was again degassed with argon for 5 min and it was stirred at 90° C. for 16 hr. After completion of the reaction, it was concentrated under reduced pressure to get the crude product, which was purified by column chromatography using Davisil silica and 30% EA in petroleum ether as eluent to afford tert-butyl 4-(3,4-dihydro-2H-1,4-benzoxazin-8-yl)-3,6-dihydro-2H-pyridine-1-carboxylate 9-3 (23 g, 62.09 mmol, 83.07% yield) as a colourless gum. LCMS (ES$^+$): m/z 217.02 [M−Boc+H]$^+$.

Step-5:
A solution of tert-butyl 4-(3,4-dihydro-2H-1,4-benzoxazin-8-yl)-3,6-dihydro-2H-pyridine-1-carboxylate 9-3 (23 g, 66.37 mmol) in methanol (500 mL) was degassed with N$_2$ for 10 min and 10% palladium on carbon (21 g, 66.37 mmol) was added. The reaction mixture was stirred for 16 h at 25° C. in a Par shaker under hydrogen pressure (80 psi). After completion of the reaction, it was filtered over a celite bed and washed with ethyl acetate. The volatiles were evaporated under reduced pressure to get the crude product, which was purified by column chromatography to afford tert-butyl 4-(3,4-dihydro-2H-1,4-benzoxazin-8-yl)piperidine-1-carboxylate 9-4 (22 g, 56.24 mmol, 84.73% yield). LCMS (ES$^+$): m/z 263.41 [M−tBu+H]$^+$.

Step-6:
To a solution of t-butyl 4-(3,4-dihydro-2H-1,4-benzoxazin-8-yl)piperidine-1-carboxylate 9-4 (22 g, 65.95 mmol) and 2,6-dibenzyloxy-3-bromo-pyridine 5-7 (24.42 g, 65.95 mmol) in toluene (420 mL) was added sodium tert-butoxide (12.68 g, 131.91 mmol) at room temperature. The reaction mixture was degassed with N$_2$ for 10 min and Pd$_2$(dba)$_3$ (3.02 g, 3.30 mmol) was added. Subsequently, Xantphos (7.63 g, 13.19 mmol) was added, and the reaction mixture was degassed with N$_2$ for 5 min. The reaction mixture was stirred at 110° C. for 16 h. After completion of the reaction, it was concentrated under reduced pressure to give the crude product, which was purified by column chromatography using Davisil silica and 10% EtOAc in petroleum ether as an eluent to afford t-butyl 4-[4-(2,4-dibenzyloxyphenyl)-2,3-dihydro-1,4-benzoxazin-8-yl]piperidine-1-carboxylate 9-5 (20 g, 26.26 mmol, 39.81% yield) as pale yellow colour gum. LCMS (ES$^+$): m/z 552.47 [M−tBu+H]$^+$.

Step-7:
A solution of tert-butyl 4-[4-(2,4-dibenzyloxyphenyl)-2,3-dihydro-1,4-benzoxazin-8-yl]piperidine-1-carboxylate 9-5 (20 g, 32.96 mmol) in ethanol (200 mL) and ethyl acetate (200 mL) was degassed with N$_2$ for 10 min and palladium, 10% on carbon (20 g, 32.96 mmol) was added. The reaction mixture was purged with H$_2$ gas for 5 min and the stirring was continued for 24 hr at room temperature under hydrogen atmosphere (70 psi) in a Parr shaker. The progress of the reaction was monitored by TLC. After completion of the reaction, it was filtered over celite bed and washed with ethyl acetate and 10% methanol in DCM. The volatiles were removed under reduced pressure to get the crude product, which was purified by column chromatography over Davisil silica, using 50% EtOAc in petroleum ether as eluent to afford tert-butyl 4-[4-(2,6-dioxo-3-piperidyl)-2,3-dihydro-1,4-benzoxazin-8-yl]piperidine-1-carboxylate 9-6 (7 g, 15.13 mmol, 45.90% yield) as a red solid. LCMS (ES$^+$): m/z 430.32 [M+H]$^+$.

Step-8:
1.5 g of tert-butyl 4-[4-(2,6-dioxo-3-piperidyl)-2,3-dihydro-1,4-benzoxazin-8-yl]piperidine-1-carboxylate 9-6 was separated by chiral SFC to afford tert-butyl 4-[4-[(3S)-2,6-dioxo-3-piperidyl]-2,3-dihydro-1,4-benzoxazin-8-yl]piperidine-1-carboxylate 9-7 (Early-eluting peak, 0.55 g) and tert-butyl 4-[4-[(3R)-2,6-dioxo-3-piperidyl]-2,3-dihydro-1,4-benzoxazin-8-yl]piperidine-1-carboxylate 9-8 (Late-eluting peak, 0.64 g).

Preparative SFC conditions: column/dimensions: CHIRALPAK-IC (30×250) mm, 5µ; % CO$_2$: 60%; % co-solvent:

40% (ACN:IPA) (1:1); Total Flow: 100 g/min; Back Pressure: 100 bar; Temperature: 30° C.; UV: 220 nm; Solubility: ACN.

9-7: LCMS (ES+): m/z 330.38 [M+H]+.

9-8: LCMS (ES+): m/z 330.34 [M+H]+.

Step-9:

To a solution of tert-butyl 4-[4-[(3S)-2,6-dioxo-3-piperidyl]-2,3-dihydro-1,4-benzoxazin-8-yl]piperidine-1-carboxylate 9-7 (0.55 g, 1.28 mmol) in DCM (3 mL) was added TFA (1.46 g, 12.81 mmol, 986.56 L) dropwise over 5 min at 0° C. under $N_2$ atmosphere. The reaction mixture was stirred at room temperature for 6 h. On completion, the crude product was concentrated under vacuum to get a crude product as an off-white solid. The crude product was washed with diethyl ether and dried under vacuum to afford (3S)-3-[8-(4-piperidyl)-2,3-dihydro-1,4-benzoxazin-4-yl]piperidine-2,6-dione 9-9 (0.510 g, 1.00 mmol, 78.14% yield, TFA salt). LCMS (ES+): m/z 330 [M+H]+.

Step-10:

To a solution of tert-butyl 4-[4-[(3R)-2,6-dioxo-3-piperidyl]-2,3-dihydro-1,4-benzoxazin-8-yl]piperidine-1-carboxylate 9-8 (0.640 g, 1.49 mmol) in DCM (5 mL) was added TFA (1.70 g, 14.90 mmol, 1.15 mL) dropwise over 5 min at 0° C. under $N_2$ atmosphere. The reaction mixture was stirred at room temperature for 6 h. On completion, the crude product was concentrated under vacuum to give the crude product, which was washed with diethyl ether solution and dried under vacuum to afford (3R)-3-[8-(4-piperidyl)-2,3-dihydro-1,4-benzoxazin-4-yl]piperidine-2,6-dione 9-10 (0.640 g, 1.21 mmol, 81.37% yield, TFA salt). LCMS (ES+): m/z 330.16 [M+H]+.

Step-11:

To a stirred solution of t-butyl 4-[4-(2,6-dioxo-3-piperidyl)-2,3-dihydro-1,4-benzoxazin-8-yl]piperidine-1-carboxylate 9-6 (7 g, 16.30 mmol) in DCM (100 mL) was added trifluoroacetic acid (14.80 g, 129.80 mmol, 10 mL) at 0° C. The reaction mixture was stirred at room temperature for 16 hr. Upon completion of the reaction, the solvents were removed under reduced pressure.

The crude product obtained was washed with diethyl ether and dried to afford 3-[8-(4-piperidyl)-2,3-dihydro-1,4-benzoxazin-4-yl]piperidine-2,6-dione 9-11 (7 g, 14.13 mmol, 86.67% yield, TFA salt). LCMS (ES+): m/z 330.27 [M+H]+.

Scheme 10: Synthesis of (3S)-3-(8-piperazin-1-yl-2,3-dihydro-1,4-benzoxazin-4-yl)piperidine-2,6-dione and (3R)-3-(8-piperazin-1-yl-2,3-dihydro-1,4-benzoxazin-4-yl)piperidine-2,6-dione and

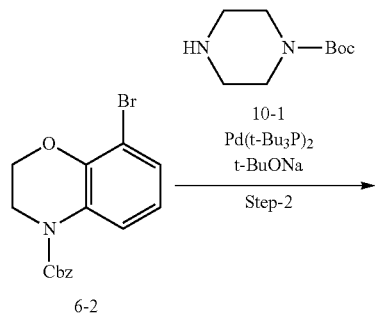

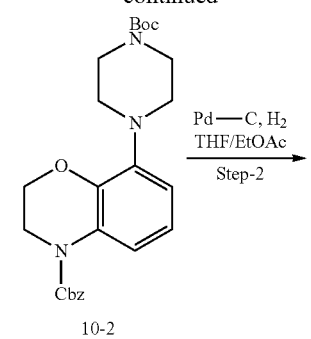

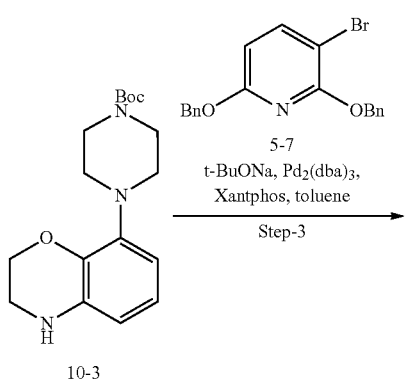

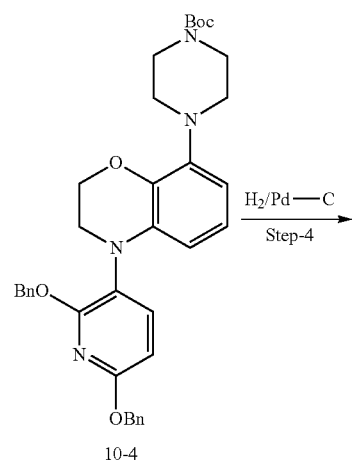

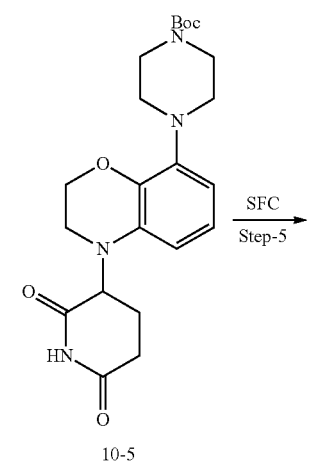

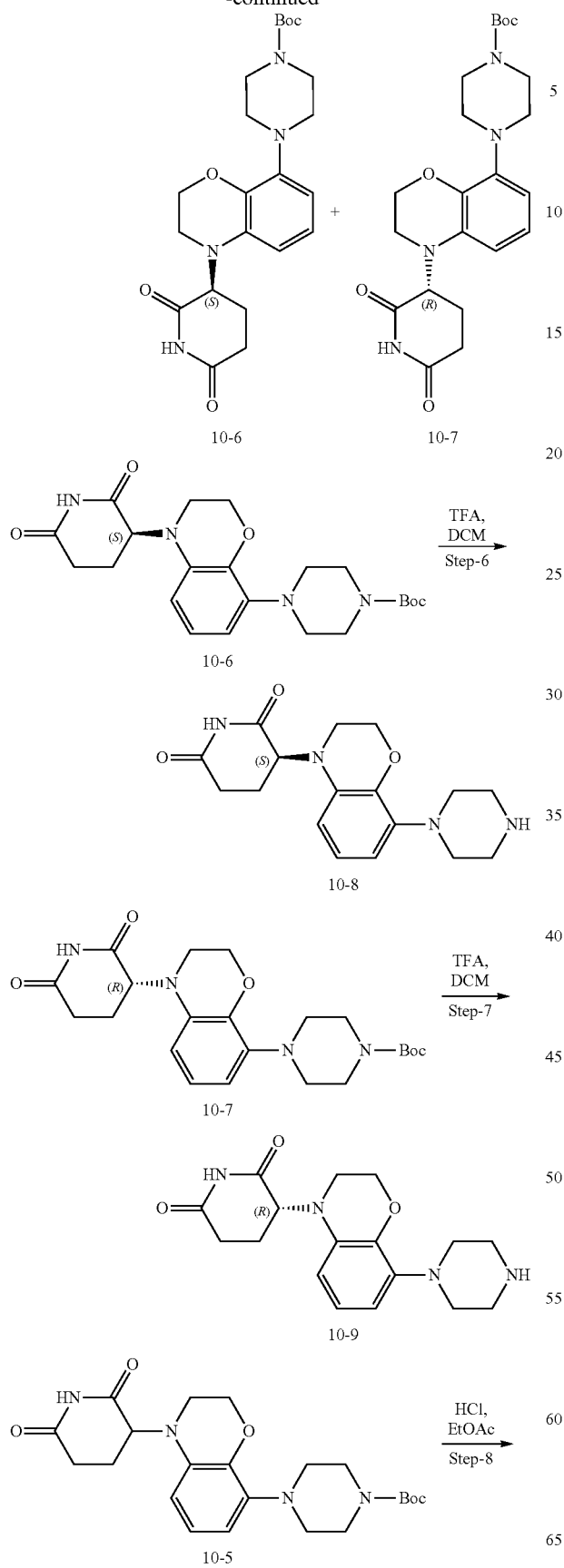

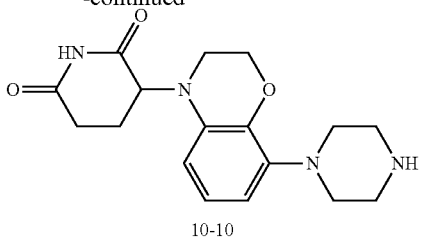

Step-1:

To a solution of benzyl 8-bromo-2,3-dihydro-1,4-benzoxazine-4-carboxylate 6-2 (25.0 g, 71.80 mmol) and tert-butyl piperazine-1-carboxylate 10-1 (14.71 g, 78.98 mmol) in toluene (75 mL) was added NaO$^t$Bu (17.25 g, 179.50 mmol) at room temperature. The reaction mixture was degassed with nitrogen gas for 10 min and Pd(t-Bu$_3$P)$_2$ (3.67 g, 7.18 mmol) was added. The reaction mixture was degassed with nitrogen gas for additional 5 min and it was stirred at 100° C. for 1 h. Upon completion, the reaction mixture was filtered through celite bed and washed with ethyl acetate (100 mL). The organic layer was washed with water (50 mL) and brine (50 mL), dried over Na$_2$SO$_4$, filtered and concentrated in vacuo to get the crude product, which was purified by column chromatography using Davisil silica and 25% ethyl acetate in petroleum ether as eluent to afford benzyl 8-(4-tert-butoxycarbonylpiperazin-1-yl)-2,3-dihydro-1,4-benzoxazine-4-carboxylate 10-2 (27.1 g, 56.77 mmol, 79.06% yield) as a colourless gum. LCMS (ES$^+$): m/z 454.67 [M+H]$^+$.

Step-2:

To a stirred solution of benzyl 8-(4-tert-butoxycarbonylpiperazin-1-yl)-2,3-dihydro-1,4-benzoxazine-4-carboxylate 10-2 (27.1 g, 59.75 mmol) in EtOAc (270 mL) and THF (270 mL) was added 10% palladium on carbon (6.36 g, 59.75 mmol) at room temperature. The reaction mixture was stirred in hydrogen atmosphere under balloon pressure for 16 h. Subsequently, it was filtered through celite bed and washed with ethyl acetate (100 mL). The filtrate was concentrated in vacuo to afford tert-butyl 4-(3,4-dihydro-2H-1,4-benzoxazin-8-yl)piperazine-1-carboxylate 10-3 (18.2 g, 55.84 mmol, 93.45% yield) as a colorless gel. LCMS (ES$^+$): m/z 320.55 [M+H]$^+$.

Step-3:

To a solution of tert-butyl 4-(3,4-dihydro-2H-1,4-benzoxazin-8-yl)piperazine-1-carboxylate 10-3 (18.2 g, 56.98 mmol) and 2,6-dibenzyloxy-3-bromo-pyridine 5-7 (21.10 g, 56.98 mmol) in toluene (200 mL) was added NaO$^t$Bu (13.69 g, 142.46 mmol) at room temperature. The reaction mixture was degassed with nitrogen gas for 10 min and Pd$_2$(dba)$_3$ (5.22 g, 5.70 mmol) and Xantphos (3.30 g, 5.70 mmol) were added. The reaction mixture was degassed with nitrogen gas for additional 5 min and it was stirred at 100° C. for 1 h. The reaction mixture was filtered through celite bed and washed with ethyl acetate (100 mL). The organic layer was washed with water (50 mL) and brine (50 mL), dried over Na$_2$SO$_4$, filtered and concentrated in vacuo to get the crude product, which was purified by column chromatography using Davisil silica and 40% ethyl acetate in petroleum ether as eluent to afford tert-butyl 4-[4-(2,6-dibenzyloxy-3-pyridyl)-2,3-dihydro-1,4-benzoxazin-8-yl]piperazine-1-carboxylate 10-4 (31.2 g, 45.10 mmol, 79.15% yield) as a colorless gum. LCMS (ES$^+$): m/z 609.54 [M+H]$^+$.

Step-4:

To a stirred solution of tert-butyl 4-[4-(2,6-dibenzyloxy-3-pyridyl)-2,3-dihydro-1,4-benzoxazin-8-yl]piperazine-1-carboxylate 10-4 (31.2 g, 51.25 mmol) in EtOH (300 mL), EtOAc (300 mL) and THF (300 mL) was added 10% palladium on carbon (16.36 g, 153.76 mmol) and Pt$_2$O (1.26 g, 5.13 mmol) at room temperature. The reaction mixture was stirred in hydrogen atmosphere under 60 psi for 16 h. Subsequently, it was filtered through celite bed and washed with ethyl acetate (1000 mL). The filtrate was concentrated under reduced pressure to afford tert-butyl 4-[4-(2,6-dioxo-3-piperidyl)-2,3-dihydro-1,4-benzoxazin-8-yl]piperazine-1-carboxylate 10-5 (14.5 g, 32.67 mmol, 63.74% yield) as off white solid. LCMS (ES$^+$): m/z 431.45 [M+H]$^+$.

Step-5:

Racemic tert-butyl N-[1-[4-(2,6-dioxo-3-piperidyl)-2,3-dihydro-1,4-benzoxazin-8-yl]-4-piperidyl]-N-methyl-carbamate 10-5 (6.0 g) was separated by SFC to give 4-[4-[(3S)-2,6-dioxo-3-piperidyl]-2,3-dihydro-1,4-benzoxazin-8-yl]piperazine-1-carboxylate 10-6 (2.5 g, Early eluting peak arbitrarily assigned as S-isomer) and 4-[4-[(3R)-2,6-dioxo-3-piperidyl]-2,3-dihydro-1,4-benzoxazin-8-yl]piperazine-1-carboxylate 10-7 (2.6 g, Late eluting peak arbitrarily assigned as R-isomer).

SFC Conditions: column/dimensions: Chiralpak IC-3 (4.6×250) mm, 5µ; % CO$_2$:60%; % co-solvent: 40% (ACN: IPA) (1:1); Total Flow: 3.00 g/min; Back Pressure: 1500PSI; Temperature: 30° C.

Step-6:

To a solution of tert-butyl 4-[4-[(3S)-2,6-dioxo-3-piperidyl]-2,3-dihydro-1,4-benzoxazin-8-yl]piperazine-1-carboxylate 10-6 (300.00 mg, 696.87 mol) in DCM (10 mL) was added TFA (794.59 mg, 6.97 mmol, 536.89 L) at 0° C. and the reaction mixture was stirred at room temperature for 2 h. Upon completion, the reaction mixture was concentrated in vacuo to give the crude product, which was triturated with diethyl ether (50 mL) to afford (3 S)-3-(8-piperazin-1-yl-2,3-dihydro-1,4-benzoxazin-4-yl)piperidine-2,6-dione 10-8 (0.2 g, 567.35 mol, 81.41% yield). LCMS (ES$^+$): m/z 331.12 [M+H]$^+$.

Step-7:

To a solution of tert-butyl 4-[4-[(3R)-2,6-dioxo-3-piperidyl]-2,3-dihydro-1,4-benzoxazin-8-yl]piperazine-1-carboxylate 10-7 (300.00 mg, 696.87 mol) was added TFA (158.92 mg, 1.39 mmol, 107.38 L) at 0° C. and the reaction mixture was stirred at room temperature for16 hr. The reaction mixture was concentrated in vacuo to get the crude product, which was triturated with diethyl ether (50 mL) to afford (3R)-3-(8-piperazin-1-yl-2,3-dihydro-1,4-benzoxazin-4-yl)piperidine-2,6-dione 10-9 (0.3 g, 654.81 mol, 93.96% yield, TFA salt). LCMS (ES$^+$): m/z 331.33 [M+H]$^+$.

Step-8:

To a solution of tert-butyl 4-(4-(2,6-dioxopiperidin-3-yl)-3,4-dihydro-2H-benzo[b][1,4]oxazin-8-yl)piperazine-1-carboxylate 10-5 (1.3 g, 3.02 mmol) in ethyl acetate (15 mL) was added HCl/EtOAc (4 M, 15 mL). The mixture was stirred at 20° C. for 2 hr. The reaction mixture was concentrated under reduced pressure to give 3-(8-(piperazin-1-yl)-2H-benzo[b][1,4]oxazin-4(3H)-yl)piperidine-2,6-dione 10-10 (1.36 g, 2.97 mmol, 98.21% yield, HCl salt). LCMS (ES$^+$): m/z 331.1 [M+H]$^+$.

Scheme 11: Synthesis of 3-[8-[(4S)-3,3-difluoro-4-piperidyl]-2,3-dihydro-1,4-benzoxazin-4-yl]piperidine-2,6-dione3-[8-[(4R)-3,3-difluoro-4-piperidyl]-2,3-dihydro-1,4-benzoxazin-4-yl]piperidine-2,6-dione

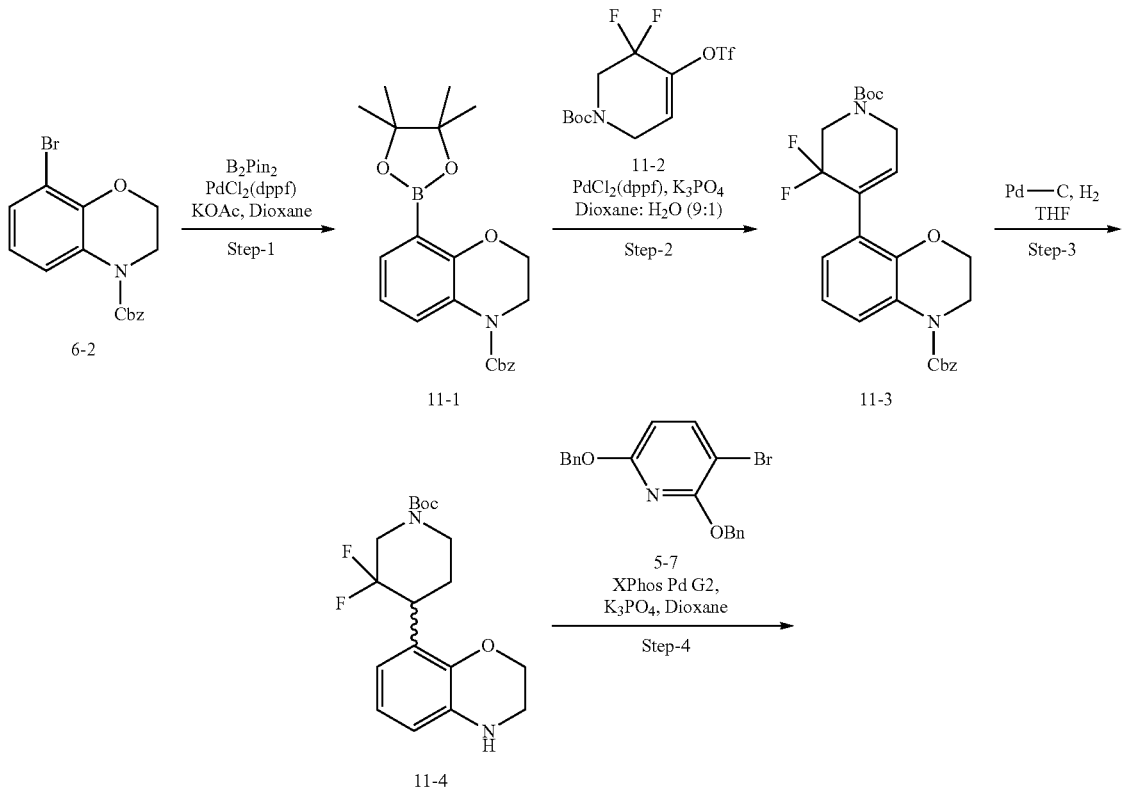

-continued
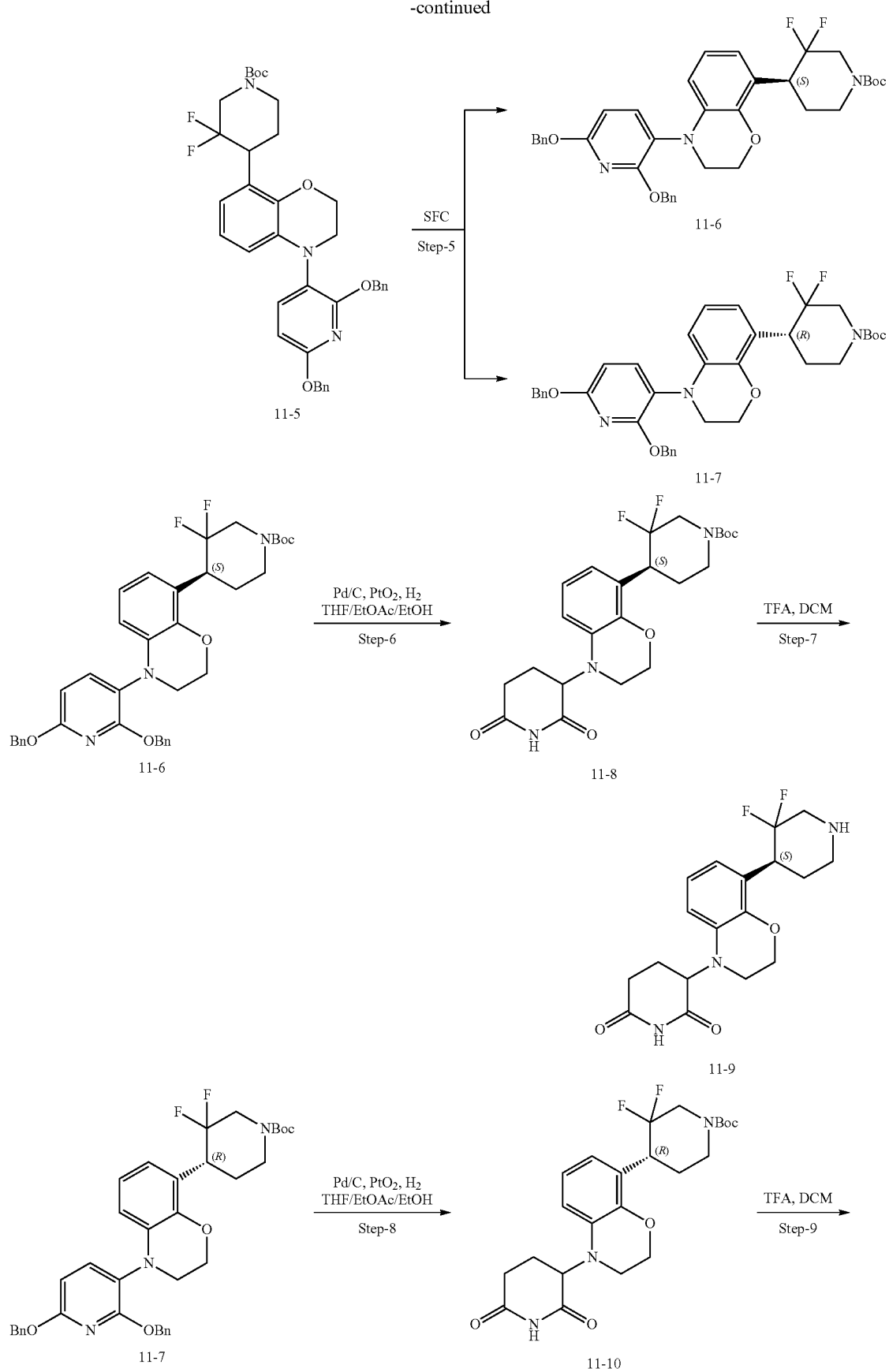

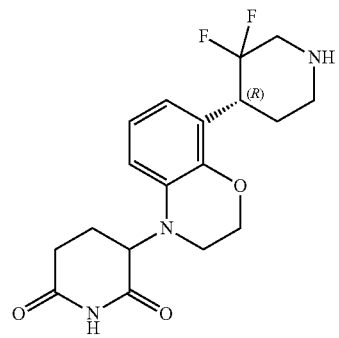

11-11

Step-1:

A stirred reaction mixture of benzyl 8-bromo-2,3-dihydro-1,4-benzoxazine-4-carboxylate 6-2 (20 g, 57.44 mmol) and 4,4,5,5-tetramethyl-2-(4,4,5,5-tetramethyl-1,3,2-dioxaborolan-2-yl)-1,3,2-dioxaborolane (21.88 g, 86.16 mmol), potassium acetate (11.27 g, 114.88 mmol, 7.18 mL) in dioxane (200 mL) was degassed with argon for 5 min and 1,1'-bis(diphenylphosphino)ferrocene]dichloropalladium (II) (4.69 g, 5.74 mmol) was added. The reaction mixture was heated at 100° C. for 16 h. Upon completion of the reaction, the reaction mixture was cooled to room temperature, then the reaction mixture was passing through celite bed and then the filtrate was dried over anhydrous $Na_2SO_4$, filtered and evaporated in vacuo to get the crude product, which was purified by column chromatogrphy using Davisil Silica, eluting solvent 15-20% EtOAc in n-hexane to afford benzyl 8-(4,4,5,5-tetramethyl-1,3,2-dioxaborolan-2-yl)-2,3-dihydro-1,4-benzoxazine-4-carboxylate 11-1 (19 g, 38.46 mmol, 66.95% yield) as light pink solid.

Step-2:

To a solution of benzyl 8-(4,4,5,5-tetramethyl-1,3,2-dioxaborolan-2-yl)-2,3-dihydro-1,4-benzoxazine-4-carboxylate 11-1 (10 g, 25.30 mmol) and tert-butyl 3,3-difluoro-4-(trifluoromethylsulfonyloxy)-2,6-dihydropyridine-1-carboxylate 11-2 (9.29 g, 25.30 mmol) in water (20 mL) and dioxane (80 mL) was added potassium phosphate tribasic (16.11 g, 75.90 mmol) at room temperature. The reaction mixture was degassed with argon gas for 10 minutes and bis(diphenylphosphino)ferrocene]dichloropalladium(II) (925.60 mg, 1.27 mmol) was added. The reaction mixture was degassed with argon for additional 5 minutes and it was stirred at 100° C. for 4 h in a sealed tube. Subsequently, the reaction mixture was concentrated in vacuo to give the crude product, which was purified by column chromatography using Davisil silica and 10-15% ethyl acetate in petroleum ether as eluent to afford benzyl 8-(1-tert-butoxycarbonyl-3,3-difluoro-2,6-dihydropyridin-4-yl)-2,3-dihydro-1,4-benzoxazine-4-carboxylate 11-3 (9.5 g, 18.34 mmol, 72.49% yield) as a light-yellow gum. LCMS (ES$^+$): m/z-431.25 [M−tBu+H]$^+$.

Step-3:

To a stirred solution of benzyl 8-(1-tert-butoxycarbonyl-3,3-difluoro-2,6-dihydropyridin-4-yl)-2,3-dihydro-1,4-benzoxazine-4-carboxylate 11-3 (10 g, 20.55 mmol) in THF (100 mL) and EtOAc (100 mL) was added palladium on carbon (4.37 g, 41.10 mmol) at room temperature. The reaction mixture was stirred in hydrogen atmosphere at balloon pressure for 16 h. Subsequently, it was filtered through celite bed and washed with ethyl acetate (30 mL). The filtrate was concentrated in vacuo to get the crude product. It was purified by column chromatography using Davisil silica gel 30% EtOAc in petroleum ether as eluent to get tert-butyl 4-(3,4-dihydro-2H-1,4-benzoxazin-8-yl)-3,3-difluoro-piperidine-1-carboxylate 11-4 (5.5 g, 12.66 mmol, 61.62% yield) as pale brown solid. LCMS (ES$^+$): 299.31 [M−tBu+H]$^+$.

Step-4:

To a solution of tert-butyl 4-(3,4-dihydro-2H-1,4-benzoxazin-8-yl)-3,3-difluoro-piperidine-1-carboxylate 11-4 (6.2 g, 17.49 mmol) and 2,6-dibenzyloxy-3-bromo-pyridine 5-7 (12.95 g, 34.99 mmol) in 1,4-dioxane (100 mL) was added anhydrous potassium phosphate tribasic (9.28 g, 43.74 mmol) at room temperature. The reaction mixture was degassed with argon gas for 10 minutes and XPhos Pd G2 (1.38 g, 1.75 mmol) was added. The reaction mixture was degassed with argon for an additional 5 minutes and it was stirred at 100° C. for 16 h. The reaction mixture was filtered through celite bed, washed with EtOAc. The filtrate was concentrated in vacuo to give the crude product, which was purified by column chromatography using Davisil silica gel and 30% EtOAc in petroleum ether as eluent to afford tert-butyl 4-[4-(2,6-dibenzyloxy-3-pyridyl)-2,3-dihydro-1,4-benzoxazin-8-yl]-3,3-difluoro-piperidine-1-carboxylate 11-5 (2.7 g, 3.77 mmol, 21.54% yield) as a pale brown solid. LCMS (ES$^+$): m/z 587.92 [M−tBu+H]$^+$.

Step-5:

Racemic tert-butyl 4-[4-(2,6-dibenzyloxy-3-pyridyl)-2,3-dihydro-1,4-benzoxazin-8-yl]-3,3-difluoro-piperidine-1-carboxylate 11-5 (2.7 g, 4.19 mmol) was separated by SFC. The fractions obtained were concentrated and lyophilized to afford tert-butyl 4-[4-(2,6-dibenzyloxy-3-pyridyl)-2,3-dihydro-1,4-benzoxazin-8-yl]-3,3-difluoro-piperidine-1-carboxylate 11-6 (1.0 g, 1.52 mmol, 36.21% yield) (Early eluting peak, arbitrarily assigned as S-isomer) and tert-butyl 4-[4-(2,6-dibenzyloxy-3-pyridyl)-2,3-dihydro-1,4-benzoxazin-8-yl]-3,3-difluoro-piperidine-1-carboxylate 11-7 (1.1 g, 1.67 mmol, 39.75% yield) (Late eluting peak, arbitrarily assigned as R-somer) as pale brown solids.

11-6: LCMS (ES$^+$): m/z 643.35 [M+H]$^+$.

11-7: LCMS (ES$^+$): m/z 643.55 [M+H]$^+$.

Step-6:

A stirred solution of tert-butyl (4S)-4-[4-(2,6-dibenzyloxy-3-pyridyl)-2,3-dihydro-1,4-benzoxazin-8-yl]-3,3-difluoro-piperidine-1-carboxylate 11-6 (1.0 g, 1.55 mmol) in ethanol (5 mL), ethyl acetate (20 mL) and THF (20 mL) was degassed with argon for 10 min. Palladium on carbon (165.32 mg, 1.55 mmol) and platinum (IV) oxide hydrate (380.74 mg, 1.55 mmol) were added and the mixture was stirred for 16 h at room temperature under hydrogen atmosphere at balloon pressure. Upon completion of reaction, the reaction mixture was filtered through celite bed and washed with EtOAc. The filtrate was concentrated in vacuo to get the crude product, which was triturated with diethyl ether (10 mL×2) to get 3-[8-[(4S)-3,3-difluoro-4-piperidyl]-2,3-dihydro-1,4-benzoxazin-4-yl]piperidine-2,6-dione 11-8 (0.4 g, 1.05 mmol, 93.45% yield) as a pale grey solid. LCMS (ES⁻): m/z 464.27 [M−H]⁻.

Step-7:

To a stirred solution of tert-butyl (4S)-4-[4-(2,6-dioxo-3-piperidyl)-2,3-dihydro-1,4-benzoxazin-8-yl]-3,3-difluoro-piperidine-1-carboxylate 11-8 (0.52 g, 1.12 mmol) in DCM (5 mL) at 0° C. was added trifluoroacetic acid (1.28 g, 11.20 mmol, 862.88 L). The reaction was stirred at room temperature for 4 h. The progress of reaction was monitored by TLC using bicarbonate workup. After completion of the reaction, the reaction mixture was evaporated under reduced pressure. The resulting product was dissolved with 10% methanol in DCM and washed with bicarbonate solution and brine. The organic layer was concentrated in vacuo to get the crude product, which was triturated with diethyl ether (20 mL×2) to give 3-[8-[(4S)-3,3-difluoro-4-piperidyl]-2,3-dihydro-1,4-benzoxazin-4-yl]piperidine-2,6-dione 11-9 (0.4 g, 1.05 mmol, 93.45% yield) as a pale grey solid. LCMS (ES⁺): m/z 366.14 [M+H]⁺.

Step 8 and Step-9:

The procedures were similar to those of Step-6 and Step-7. Compound 3-[8-[(4R)-3,3-difluoro-4-piperidyl]-2,3-dihydro-1,4-benzoxazin-4-yl]piperidine-2,6-dione 11-11 was obtained as a pale grey solid. LCMS (ES⁺): m/z 366.26 [M+H]⁺.

Scheme 12: Synthesis of 3-[8-(4-piperidyl)-2,3-dihydropyrido[4,3-b][1,4]oxazin-4-yl]piperidine-2,6-dione

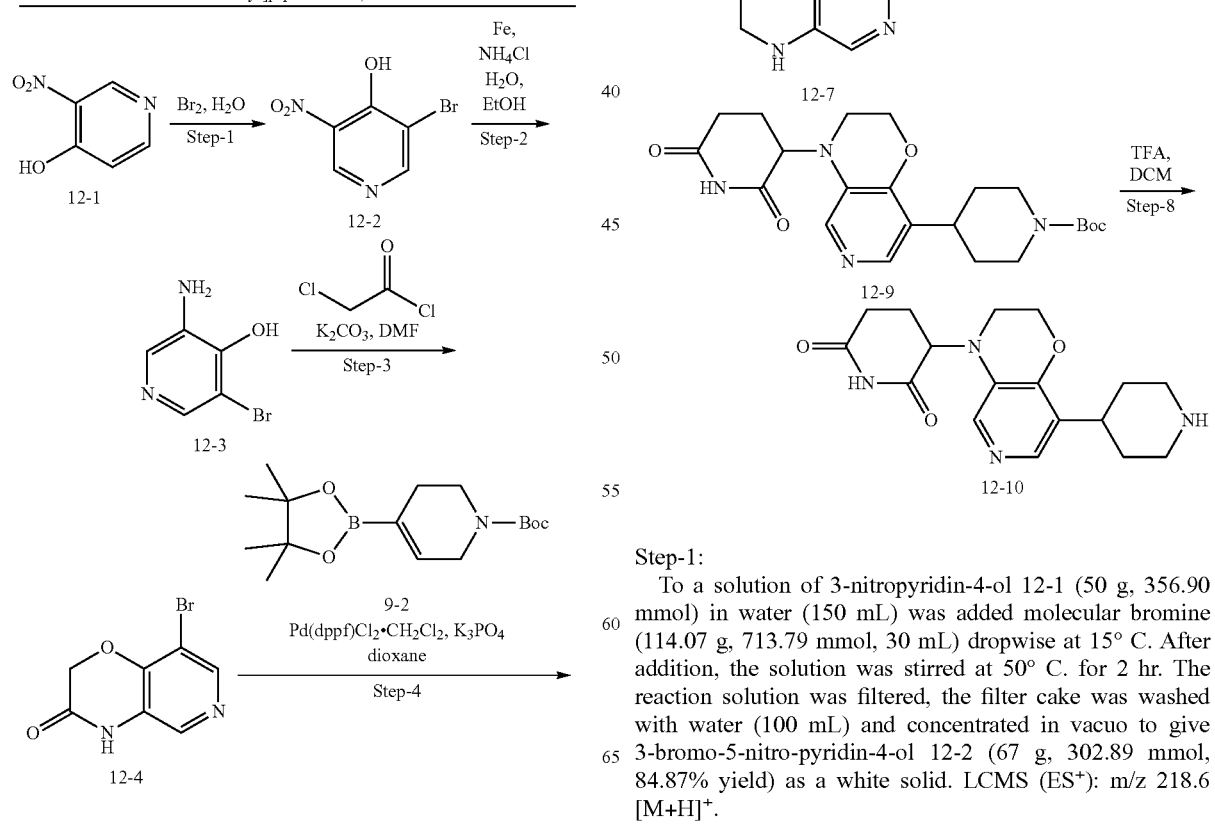

Step-1:

To a solution of 3-nitropyridin-4-ol 12-1 (50 g, 356.90 mmol) in water (150 mL) was added molecular bromine (114.07 g, 713.79 mmol, 30 mL) dropwise at 15° C. After addition, the solution was stirred at 50° C. for 2 hr. The reaction solution was filtered, the filter cake was washed with water (100 mL) and concentrated in vacuo to give 3-bromo-5-nitro-pyridin-4-ol 12-2 (67 g, 302.89 mmol, 84.87% yield) as a white solid. LCMS (ES⁺): m/z 218.6 [M+H]⁺.

Step-2:

A solution of 3-bromo-5-nitropyridin-4-ol 12-2 (30 g, 136.99 mmol) in water (4.48 mL) and ethanol (134.39 mL) was stirred at 15° C., then iron (30.60 g, 547.96 mmol, 3.89 mL) and ammonium chloride (29.31 g, 547.96 mmol, 19.16 mL) were added. After addition, the solution was stirred at 90° C. for 12 h under $N_2$ atmosphere. The reaction solution was filtered while it was hot, and the filter cake was washed with ethanol (100 mL) and concentrated under vacuum to give 3-bromo-5-nitro-pyridin-4-ol 12-3 (9.1 g, 39.48 mmol, 92.17% yield) as a brown solid. LCMS (ES$^+$): m/z 190.6 [M+H]$^+$.

Step-3:

To a solution of 3-amino-5-bromo-pyridin-4-ol 12-3 (5 g, 26.45 mmol) and potassium carbonate (10.97 g, 79.36 mmol) in DMF (15 mL) was added 2-chloroacetyl chloride (3.29 g, 29.10 mmol, 2.31 mL) at 0° C. for 30 min under $N_2$ atmosphere. The mixture was stirred at 100° C. for 12h. The reaction mixture was poured into water (60 mL) and MTBE (10 ml) at 15° C. and filtered. The filtered cake was concentrated to give 8-bromo-4H-pyrido[4,3-b][1,4]oxazin-3-one 12-4 (2.1 g, 4.58 mmol, 17.33% yield) was obtained as a brown solid. LCMS (ES$^+$): m/z 230.6 [M+H]$^+$.

Step-4:

To a solution of 8-bromo-2H-pyrido[4,3-b][1,4]oxazin-3 (4H)-one 12-4 (2.1 g, 9.17 mmol) and tert-butyl 4-(4,4,5,5-tetramethyl-1,3,2-dioxaborolan-2-yl)-5,6-dihydropyridine-1 (2H)-carboxylate 9-2 (2.84 g, 9.17 mmol) in dioxane (20 mL) was added Pd(dppf)$_2$Cl$_2$-dichloromethane (748.78 mg, 916.91 mol) and tripotassium phosphate (2 M, 9.19 mL) at 15° C. After addition, the solution was stirred under $N_2$ at 60° C. for 12 hr. The reaction solution was poured into water (60 mL) and extracted with ethyl acetate (50×3 mL), then the organic layer was dried with Na$_2$SO$_4$ and concentrated under vacuum. The yellow residue was purified by column chromatography (SiO$_2$, petroleum ether:EtOAc=90:1-84:16) to give tert-butyl 4-(3-oxo-3,4-dihydro-2H-pyrido[4,3-b][1,4]oxazin-8-yl)-5,6-dihydropyridine-1(2H)-carboxylate 12-5 (1.8 g, 5.27 mmol, 57.47% yield) as a white solid. LCMS (ES$^+$): m/z 331.9 [M+H]$^+$.

Step-5:

To a solution of tert-butyl 4-(3-oxo-3,4-dihydro-2H-pyrido[4,3-b][1,4]oxazin-8-yl)-5,6-dihydropyridine-1(2H)-carboxylate 12-5 (1.8 g, 5.43 mmol) in DMF (30 mL) and methanol (300 mL) was added 10 wt. % Pd/C and H$_2$ (80.55 mol) under $N_2$ atmosphere. The suspension was degassed and purged with H$_2$ three times. The mixture was stirred under H$_2$ (50 psi) at 25° C. for 12 hr. The reaction solution was filtered and concentrated in vacuo to give tert-butyl 4-(3-oxo-4H-pyrido[4,3-b][1,4]oxazin-8-yl)piperidine-1-carboxylate 12-6 (920 mg, 2.68 mmol, 49.28% yield) as a white solid. LCMS (ES$^+$): m/z 333.8 [M+H]$^+$.

Step-6:

To a solution of tert-butyl 4-(3-oxo-4H-pyrido[4,3-b][1,4]oxazin-8-yl)piperidine-1-carboxylate 12-6 (920 mg, 2.76 mmol) in THF (20 mL) was added borane methylsulfanylmethane (10 M, 551.92 μL). After addition, the solution was stirred at 60° C. for 2 hr. The reaction mixture was added drops of methanol and heated at 60° C. for three mins. Then the reaction mixture was concentrated to get a white residue, which was purified by Prep-TLC (petroleum ether: EtOAc=1:2) to afford tert-butyl 4-(3,4-dihydro-2H-pyrido [4,3-b][1,4]oxazin-8-yl)piperidine-1-carboxylate 12-7 (707 mg, 2.10 mmol, 76.20% yield) was obtained as a white solid. LCMS (ES$^+$): m/z 319.9 [M+H]$^+$.

Step-7:

To a solution of tert-butyl 4-(3,4-dihydro-2H-pyrido[4,3-b][1,4]oxazin-8-yl)piperidine-1-carboxylate 12-7 (700 mg, 2.19 mmol) and 3-bromopiperidine-2,6-dione 12-8 (631.22 mg, 3.29 mmol) in ACN (5 mL) was stirred at 15° C., then tetrabutylammonium iodide (404.76 mg, 1.10 mmol) and NaHCO$_3$ (552.33 mg, 6.57 mmol) was added. Then the solution was stirred at 90° C. for 12 h. The reaction solution was filtered and concentrated under vacuum to give the residue. The crude product was purified by Prep-HPLC (column: Phenomenex Luna C8 250×50 mm×10 um, mobile phase: [water (FA)-ACN]; 100% B Hold Time(min), 5 min, Flow rate: 20 ml/min) to afford tert-butyl 4-(4-(2,6-dioxipiperidin-3-yl)-3,4-dihydro-2H-pyrido[4,3-b][1,4]oxazin-8-yl)piperidine-1-carboxylate 12-9 (450 mg, 916.01 mol, 41.80% yield, formic acid salt) as a pink solid. LCMS (ES$^+$): m/z 431.0 [M+H]$^+$.

Step-8:

To a solution of tert-butyl 4-[4-(2,6-dioxo-3-piperidyl)-2,3-dihydropyrido[4,3-b][1,4]oxazin-8-yl]piperidine-1-carboxylate 12-9 (450 mg, 1.05 mmol) in DCM (913.89 L) was added TFA (119.19 mg, 1.05 mmol, 80.53 L) under $N_2$ atmosphere, then the mixture was stirred at 15° C. for 20 min. The reaction solution was filtered and concentrated under vacuum to give 3-[8-(4-piperidyl)-2,3-dihydropyrido [4,3-b][1,4]oxazin-4-yl]piperidine-2,6-dione 12-10 (464 mg, 1.04 mmol, 99.88% yield, TFA salt) as a yellow solid. LCMS (ES$^+$): m/z 330.9 [M+H]$^+$.

Scheme 13: Synthesis of 3-[8-[(3R)-3-piperidyl]-2,3-dihydro-1,4-benzoxazin-4-yl)piperidine-2,6-dione and 3-[8-[(3R)-3-piperidyl]-2,3-dihydro-1,4-benzoxazin-4-yl)piperidine-2,6-dione

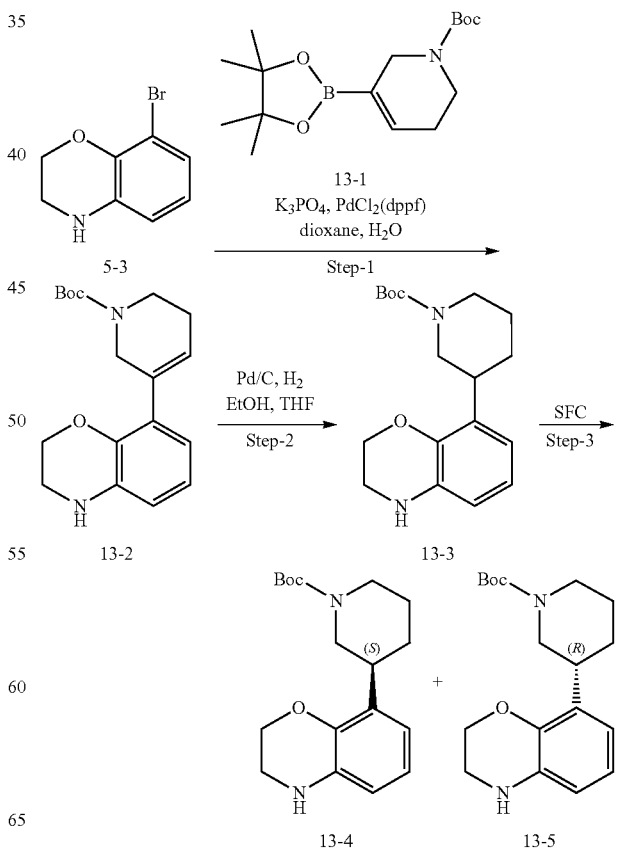

405
-continued

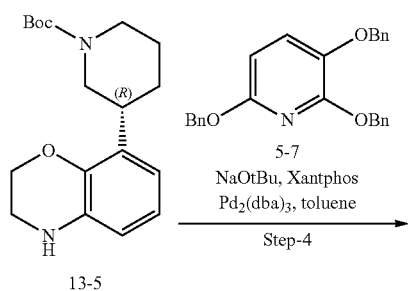

13-5

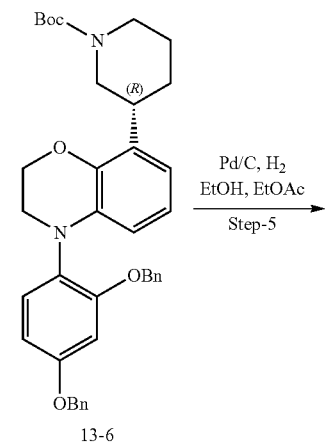

13-6

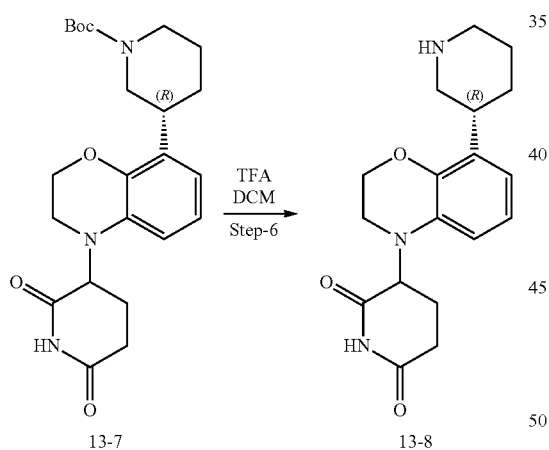

13-7    13-8

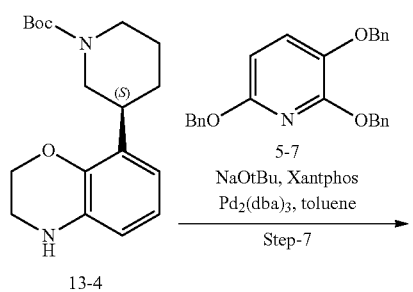

13-4

406
-continued

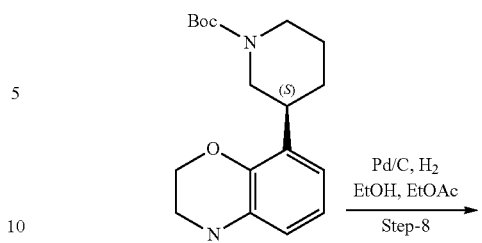

13-9

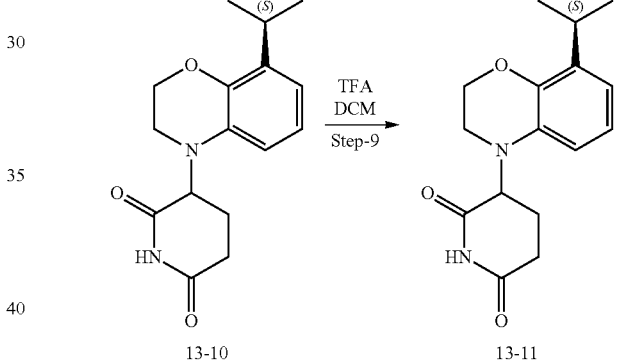

13-10    13-11

Step-1:
To a stirred solution of 8-bromo-3,4-dihydro-2H-1,4-benzoxazine 5-3 (3 g, 14.01 mmol) and tert-butyl 5-(4,4,5,5-tetramethyl-1,3,2-dioxaborolan-2-yl)-3,6-dihydro-2H-pyridine-1-carboxylate 13-1 (4.33 g, 14.01 mmol) in 1,4-dioxane (27 mL) and water (3 mL) was added potassium phosphate tribasic anhydrous (5.95 g, 28.03 mmol) at room temperature. The reaction mixture was degassed with argon for 10 minutes and Pd(dppf)$_2$Cl$_2$-dichloromethane (1.14 g, 1.40 mmol) was added. The reaction mixture was degassed with argon for an additional 5 minutes and was stirred at 90° C. for 12 hr. After completion of the reaction, the reaction mixture was purified by flash column chromatography with 30% EtOAc in petroleum ether as eluent to afford tert-butyl 5-(3,4-dihydro-2H-1,4-benzoxazin-8-yl)-3,6-dihydro-2H-pyridine-1-carboxylate 13-2 (2.89 g, 8.25 mmol, 58.87% yield) as an off-white solid. LCMS (ES$^+$): m/z 339.31 [M+H+23]$^+$.

Step-2:

To a stirred solution of tert-butyl 5-(3,4-dihydro-2H-1,4-benzoxazin-8-yl)-3,6-dihydro-2H-pyridine-1-carboxylate 13-2 (4.8 g, 15.17 mmol) in ethanol (15 mL) and THF (15 mL) was added 10% palladium on carbon wet (4.84 g, 45.51 mmol) in a dropwise manner at room temperature. The reaction mixture was stirred to 27° C. under $H_2$ atmosphere in 70 psi for 12 hr. The reaction mixture was filtered through celite bed, concentrated in vacuo, and triturated with n-pentane to give tert-butyl 3-(3,4-dihydro-2H-1,4-benzoxazin-8-yl)piperidine-1-carboxylate 13-3 (4.2 g, 12.97 mmol, 85.47% yield) as a brown solid. LCMS (ES$^+$): m/z 319.41 [M+H]$^+$.

Step-3:

Racemic tert-butyl 3-(3,4-dihydro-2H-1,4-benzoxazin-8-yl)piperidine-1-carboxylate 13-3 (5.2 g, 16.33 mmol) was submitted for SFC for the separation of isomers. The fractions obtained were concentrated to afford tert-butyl (3S)-3-(3,4-dihydro-2H-1,4-benzoxazin-8-yl)piperidine-1-carboxylate 13-4 (Early eluting peak, 2.7 g, 8.37 mmol, 51.25% yield) as off-white solid and tert-butyl (3R)-3-(3,4-dihydro-2H-1,4-benzoxazin-8-yl)piperidine-1-carboxylate 13-5 (Late eluting peak, 2.3 g, 7.14 mmol, 43.70% yield) as an off-white solid.

Preparative SFC conditions: column/dimensions: CHIRALPAK IC (30×250) mm, 5µ; % $CO_2$: 65%; % co-solvent: 35% (ACN); Total Flow: 100 g/min; Back Pressure: 100 bar; Temperature: 30° C.; UV: 220 nm; Solubility: ACN/THF.

Step-4:

To a solution of tert-butyl (3R)-3-(3,4-dihydro-2H-1,4-benzoxazin-8-yl)piperidine-1-carboxylate 13-5 (1.4 g, 4.40 mmol) and 2,6-dibenzyloxy-3-bromo-pyridine 5-7 (2.12 g, 5.72 mmol) in toluene (14 mL) was added sodium 2-methylpropan-2-olate (845.11 mg, 8.79 mmol) at room temperature. The reaction mixture was degassed with nitrogen gas for 10 minutes and (5-diphenylphosphanyl-9,9-dimethyl-xanthen-4-yl)-diphenyl-phosphane (254.41 mg, 439.69 mol) and (1E,4E)-1,5-diphenylpenta-1,4-dien-3-one palladium (402.63 mg, 439.69 mol) was added. The reaction mixture was degassed with nitrogen gas for additional 5 minutes and it was stirred at 100° C. for 16 h. The reaction mixture was filtered through a celite bed and washed with ethyl acetate. The organic layer was washed with water and brine, dried over sodium sulfate, filtered and concentrated in vacuo to get the crude product, which was purified by column chromatography using Davisil silica and 30% ethyl acetate in petroleum ether as eluent to afford tert-butyl (3R)-3-[4-(2,6-dibenzyloxy-3-pyridyl)-2,3-dihydro-1,4-benzoxazin-8-yl]piperidine-1-carboxylate 13-6 (1.7 g, 2.29 mmol, 52.08% yield) as a colorless gum. LCMS (ES$^+$): m/z 630.25 [M+Na]$^+$.

Step-5:

A stirred solution of tert-butyl (3R)-3-[4-(2,6-dibenzyloxy-3-pyridyl)-2,3-dihydro-1,4-benzoxazin-8-yl]piperidine-1-carboxylate 13-6 (2.2 g, 3.62 mmol) in ethanol (10 mL) and ethyl acetate (10 mL) was degassed with argon for 10 min. Palladium on carbon (1.16 g, 10.86 mmol) was added to the reaction mixture and it was stirred for 16 h at room temperature under $H_2$-pressure in a Parr Shaker reactor. Upon completion of reaction, it was filtered through a celite bed, washed with EtOH and EtOAc. The filtrate was evaporated under reduced pressure to give tert-butyl (3R)-3-[4-(2,6-dioxo-3-piperidyl)-2,3-dihydro-1,4-benzoxazin-8-yl]piperidine-1-carboxylate 13-7 (1.5 g, 2.58 mmol, 71.39% yield) as light blue solid. LCMS: m/z 428.426 (M−H)+.

Step-6:

To a stirred solution of tert-butyl (3R)-3-[4-(2,6-dioxo-3-piperidyl)-2,3-dihydro-1,4-benzoxazin-8-yl]piperidine-1-carboxylate 13-7 (0.5 g, 1.16 mmol) in DCM (5 mL) at 0° C. was added TFA (530.95 mg, 4.66 mmol, 358.75 L) dropwise. The reaction was stirred at room temperature for 2 h. After completion of the reaction mixture was concentrated under reduced pressure to give the crude, which was triturated with diethyl ether (20 mL×2) to afford 3-[8-[(3R)-3-piperidyl]-2,3-dihydro-1,4-benzoxazin-4-yl]piperidine-2,6-dione 13-8 (0.3 g, 646.64 mol, 55.55% yield) as an off white solid. LCMS (ES$^+$): m/z 330.9 [M+H]$^+$.

Step-7 to Step-9:

The procedures were substantially identical to those of Step-4 to Step-6. Compound 3-[8-[(3S)-3-piperidyl]-2,3-dihydro-1,4-benzoxazin-4-yl]piperidine-2,6-dione 13-11 was obtained as a yellow solid. LCMS (ES$^+$): m/z 330.2 [M+H]$^+$.

Scheme 14: Synthesis of 3-(8-((S)-pyrrolidin-3-yl)-2H-benzo[b][1,4]oxazin-4(3H)-yl)piperidine-2,6-dione and 3-(8-((R)-pyrrolidin-3-yl)-2H-benzo[b][1,4]oxazin-4(3H)-yl)piperidine-2-2,6-dione

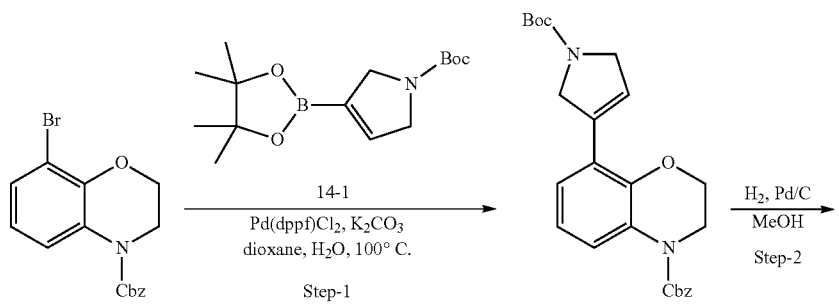

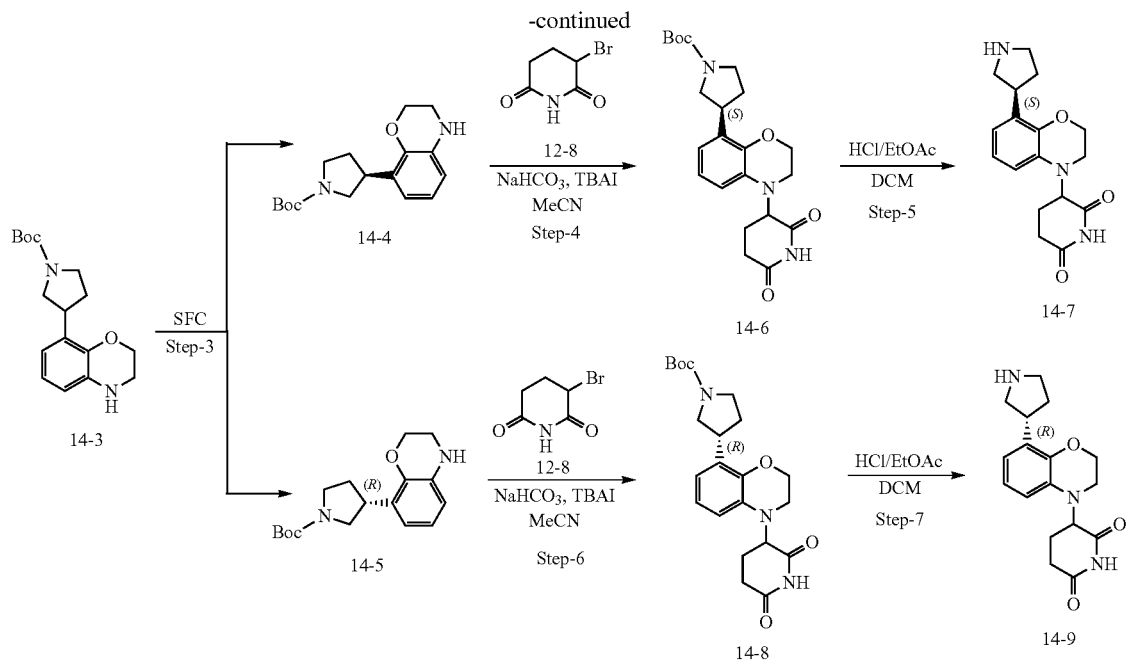

Step-1:

To a solution of tert-butyl 3-(4,4,5,5-tetramethyl-1,3,2-dioxaborolan-2-yl)-2,5-dihydro-1H-pyrrole-1-carboxylate 14-1 (3.73 g, 12.64 mmol) in a mixed solvent of water (10 mL) and dioxane (50 mL) was added benzyl 8-bromo-2H-benzo[b][1,4]oxazine-4(3H)-carboxylate 6-2 (4 g, 11.49 mmol), Pd(dppf)Cl$_2$ (938.15 mg, 1.15 mmol) and K$_2$CO$_3$ (4.88 g, 35.29 mmol). The mixture was stirred at 100° C. for 4 hr under N$_2$ atmosphere. The reaction mixture was diluted with H$_2$O (50 mL) and extracted with ethyl acetate (50 mL×2). The combined organic layers were washed with brine (50 mL), dried over anhydrous Na$_2$SO$_4$, filtered and concentrated under reduced pressure. The residue was purified by column chromatography (SiO$_2$, petroleum ether/ethyl acetate=10/1 to 2/1) to give benzyl 8-(1-(tert-butoxycarbonyl)-2,5-dihydro-1H-pyrrol-3-yl)-2H-benzo[b][1,4]oxazine-4(3H)-carboxylate 14-2 (4.6 g, 10.01 mmol, 87.15% yield) as a yellow oil. LCMS (ES$^+$). m/z 381.0 [M-56+H]$^+$.

Step-2:

To a solution of benzyl 8-(1-(tert-butoxycarbonyl)-2,5-dihydro-1H-pyrrol-3-yl)-2H-benzo[b][1,4]oxazine-4(3H)-carboxylate 14-2 (4.6 g, 10.54 mmol) in methanol (100 mL) was added 5% Pd/C (500 mg). The suspension was degassed and purged with H$_2$ three times. The mixture was stirred at 25° C. for 12 hr under H$_2$ (15 psi) atmosphere. The reaction mixture was filtered, and the filtrate was concentrated under reduced pressure. The residue was purified by column chromatography (SiO$_2$, petroleum ether/ethyl acetate=10/1 to 1/1) to give tert-butyl 3-(3,4-dihydro-2H-benzo[b][1,4]oxazin-8-yl)pyrrolidine-1-carboxylate 14-3 (3 g) as a white solid. LCMS (ES$^+$): m/z 305.1 [M+H]$^+$.

Step-3:

Tert-butyl 3-(3,4-dihydro-2H-benzo[b][1,4]oxazin-8-yl)pyrrolidine-1-carboxylate 14-3 (3 g) was separated by SFC (DAICELCHIRALPAK IC (250 mm×30 mm, 10 um); Condition: 0.1% NH$_3$H$_2$O IPA; B %: 25%-25%, Gradient time: 6.15 min) to give tert-butyl (S)-3-(3,4-dihydro-2H-benzo[b][1,4]oxazin-8-yl)pyrrolidine-1-carboxylate 14-4 (1.1 g, 3.41 mmol, 32.34% yield) as a yellow oil and tert-butyl (R)-3-(3,4-dihydro-2H-benzo[b][1,4]oxazin-8-yl)pyrrolidine-1-carboxylate 14-5 (1.1 g, 3.54 mmol, 33.61% yield) as a yellow oil. LCMS (ES$^+$): m/z 305.1 [M+H]$^+$.

Step-4:

To a solution of tert-butyl (S)-3-(3,4-dihydro-2H-benzo[b][1,4]oxazin-8-yl)pyrrolidine-1-carboxylate 14-4 (1.1 g, 3.61 mmol), 3-bromopiperidine-2,6-dione 12-8 (1.73 g, 9.03 mmol) in MeCN (2 mL) was added NaHCO$_3$ (607.18 mg, 7.23 mmol, 281.23 L) and TBAI (133.48 mg, 361.39 mol). The mixture was stirred at 90° C. for 12 hr. The reaction mixture was concentrated in vacuo and purified by column chromatography (4 g, Silica Flash Column, Eluent of 0-100% ethyl acetate/petroleum ether, 80 mL/min) to give (3S)-tert-butyl 3-(4-(2,6-dioxopiperidin-3-yl)-3,4-dihydro-2H-benzo[b][1,4]oxazin-8-yl)pyrrolidine-1-carboxylate 14-6 (450 mg, 1.08 mmol, 29.97% yield) as a white solid. LCMS (ES$^+$): m/z 360.1 [M-56+H]$^+$.

Step-5:

To a solution of (3S)-tert-butyl 3-(4-(2,6-dioxopiperidin-3-yl)-3,4-dihydro-2H-benzo[b][1,4]oxazin-8-yl)pyrrolidine-1-carboxylate 14-6 (400 mg, 962.74 mol) in DCM (2 mL) was added HCl/ethyl acetate (962.74 mol, 2 mL). The mixture was stirred at 25° C. for 12 hr.

The reaction mixture was concentrated under reduced pressure and triturated with DCM (10 mL) to give 3-(8-((S)-pyrrolidin-3-yl)-2H-benzo[b][1,4]oxazin-4(3H)-yl)piperidine-2,6-dione 14-7 (280 mg, 784.70 mol, 81.51% yield, HCl salt) as a white solid. LCMS (ES$^+$): m/z 316.1 [M+H]$^+$.

Step-6 and Step-7:

The procedures were identical to those of Step-4 and Step-5. Compound 3-(8-((R)-pyrrolidin-3-yl)-2H-benzo[b][1,4]oxazin-4(3H)-yl)piperidine-2,6-dione 14-9 was obtained as a white solid. LCMS (ES$^+$): m/z 316.1 [M+H]$^+$.

411

Scheme 15: Synthesis of 3-[7-(4-piperidyl)-2,3-dihydro-1,4-benzoxazin-4-yl]piperidine-2,6-dione

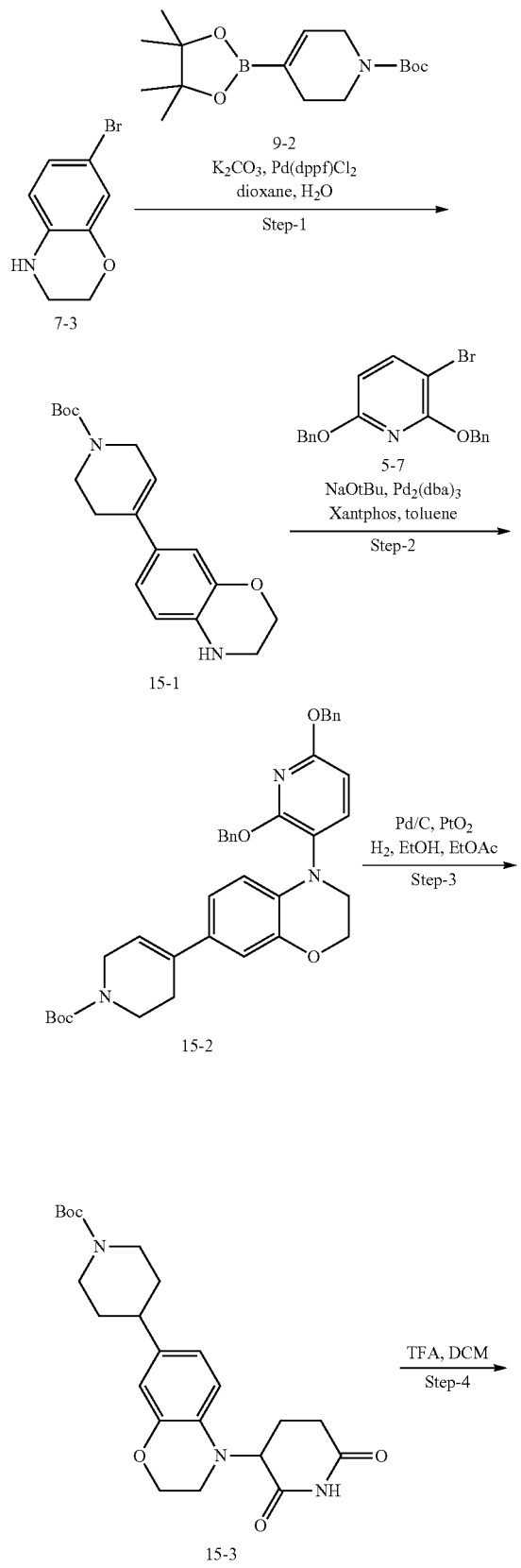

412

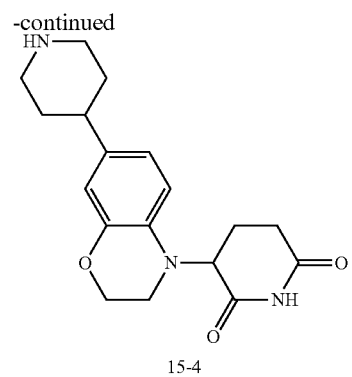

15-4

Step-1:

To a stirred solution of 7-bromo-3,4-dihydro-2H-1,4-benzoxazine 7-3 (1 g, 4.67 mmol) and tert-butyl 4-(4,4,5,5-tetramethyl-1,3,2-dioxaborolan-2-yl)-3,6-dihydro-2H-pyridine-1-carboxylate 9-2 (2.17 g, 7.01 mmol), in water (2 mL) and 1,4-dioxane (8 mL) was added potassium carbonate (1.94 g, 14.02 mmol) and [1,1'-bis(diphenylphosphino)ferrocene]dichloropalladium(II) (76.30 mg, 93.43 mol) at room temperature. The reaction mixture was degassed for 10 minutes using argon. The reaction mass was heated at 110° C. for 16 h. The progress of reaction was monitored by LCMS. After completion of reaction, the reaction mixture was filtered through a celite bed and washed with ethyl acetate. The combined organic layer was washed with brine, dried over anhydrous sodium sulfate and concentrated under reduced pressure at 45° C. to get crude product, which was purified with Davisil silica (eluting solvent 0-20% EtOAc in n-hexane) to afford tert-butyl 4-(3,4-dihydro-2H-1,4-benzoxazin-7-yl)-3,6-dihydro-2H-pyridine-1-carboxylate 15-1 (0.770 g, 2.24 mmol, 48.00% yield) as a light red gummy. LCMS (ES$^+$): m/z 317.52 [M+H]$^+$.

Step-2:

A stirred solution of tert-butyl 4-(3,4-dihydro-2H-1,4-benzoxazin-7-yl)-3,6-dihydro-2H-pyridine-1-carboxylate 15-1 (0.770 g, 2.43 mmol), 2,6-dibenzyloxy-3-bromo-pyridine 5-7 (1.08 g, 2.92 mmol) and toluene (10 mL) was prepared in a sealed tube at room temperature. The reaction mixture was degasified with argon for 5 minutes. To the reaction mixture, sodium tert-butoxide (701.65 mg, 7.30 mmol), (1E,4E)-1,5-diphenylpental,4-dien-3-one palladium (156.00 mg, 170.36 mol) and (5-diphenylphosphanyl-9,9-dimethylxanthen-4-yl)-diphenylphosphane (70.41 mg, 121.68 mol) were added at the same temperature. The reaction mixture was degassed with argon for 5 minutes, then stirred at 110° C. for 16 h. After completion of the reaction, the solvent was removed under reduced pressure to afford crude product. The crude product was quenched with water and extracted with ethyl acetate. The organic layer was washed with brine, dried over by sodium sulphate and concentrated under reduced pressure. The crude product was purified by chromatography on Davisil silica using 20% ethyl acetate in hexane as eluent to afford tert-butyl 4-[4-(2,6-dibenzyloxy-3-pyridyl)-2,3-dihydro-1,4-benzoxazin-7-yl]-3,6-dihydro-2H-pyridine-1-carboxylate 15-2 (0.380 g, 562.86 mol, 23.13% yield) as a yellow solid. LCMS (ES$^+$): m/z 606.53 [M+H]$^+$.

Step-3:

A stirred solution of tert-butyl 4-[4-(2,6-dibenzyloxy-3-pyridyl)-2,3-dihydro-1,4-benzoxazin-7-yl]-3,6-dihydro-2H-pyridine-1-carboxylate 15-2 (0.380 g, 627.35 mol) was prepared in ethanol (15 mL) and ethyl acetate (15 mL) at room temperature. The reaction mixture was degassed with nitrogen gas for 10 minutes. To the reaction mixture, 10% palladium on activated carbon (400.58 mg, 3.76 mmol), dioxoplatinum (28.49 mg, 125.47 mol) was added at the same temperature. The reaction mixture was then stirred under hydrogen atmosphere for 16 h at room temperature. After completion of reaction, the reaction mixture was filtered through celite bed and the filtrate was concentrated under reduced pressure to afford tert-butyl 4-[4-(2,6-dioxo-3-piperidyl)-2,3-dihydro-1,4-benzoxazin-7-yl]piperidine-1-carboxylate 15-3 (0.130 g, 301.85 mol, 48.12% yield) as an off-white solid. LCMS (ES+): m/z 452.56 [M+Na]+.

Step-4:

A stirred solution of tert-butyl 4-[4-(2,6-dioxo-3-piperidyl)-2,3-dihydro-1,4-benzoxazin-7-yl]piperidine-1-carboxylate 15-3 (0.130 g, 302.67 mol) in DCM (5 mL) was prepared at room temperature under nitrogen atmosphere. The reaction mixture was cooled to 0° C. before TFA (345.12 mg, 3.03 mmol, 233.19 L) was added, and the reaction mixture was stirred at room temperature for 1 hour. After completion of reaction the solvent was removed under reduced pressure to afford crude product, the crude product was triturated with diethyl ether to afford 3-[7-(4-piperidyl)-2,3-dihydro-1,4-benzoxazin-4-yl]piperidine-2,6-dione 15-4 (0.120 g, 248.25 mol, 82.02% yield, TFA salt) as an ash-colored solid. LCMS (ES+): m/z 330.34 [M+H]+.

Scheme 16: Synthesis of tert-butyl (S)-(1-(4-(2,6-dioxopiperidin-3-yl)-3,4-dihydro-2H-benzo[b][1,4]oxazin-8-yl)piperidin-4-yl)(methyl)carbamate and tert-butyl (R)-(1-(4-(2,6-dioxopiperidin-3-yl)-3,4-dihydro-2H-benzo[b][1,4]oxazin-8-yl)piperidin-4-yl)(methyl)carbamate

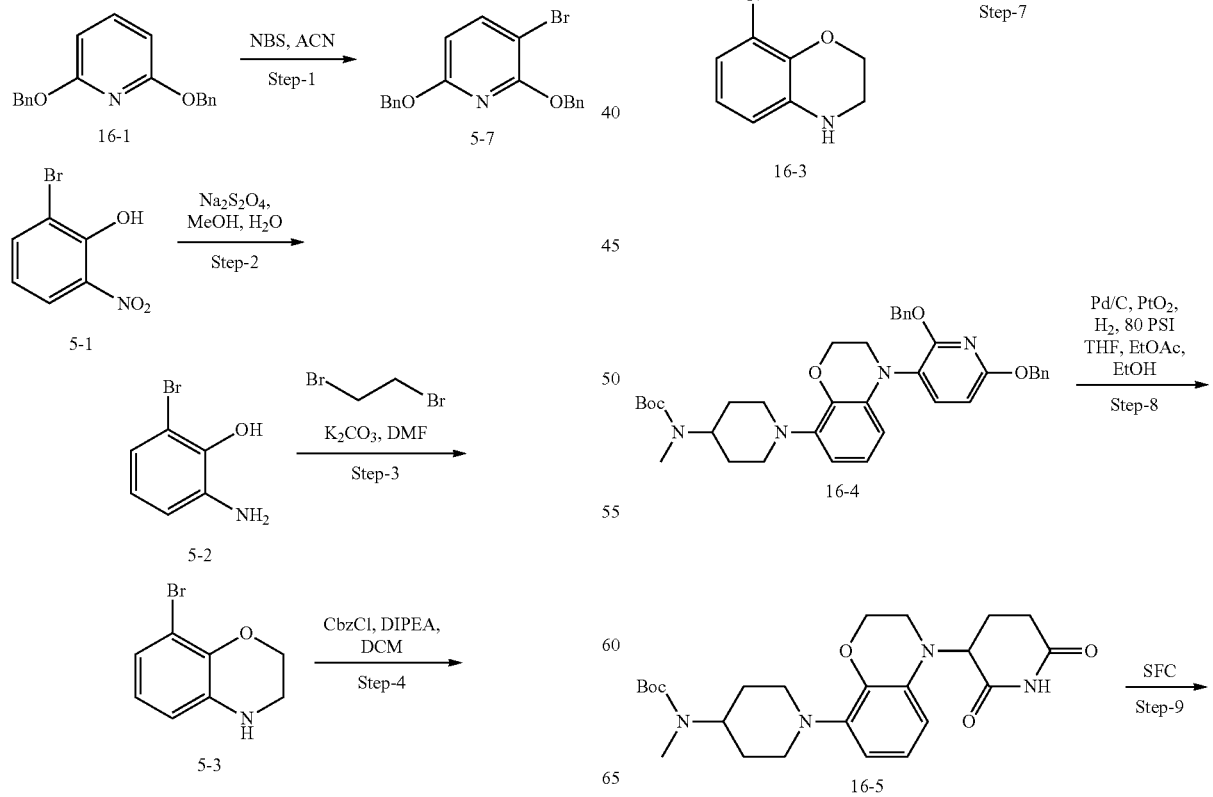

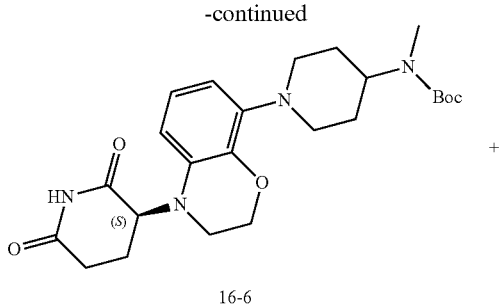

16-6

+

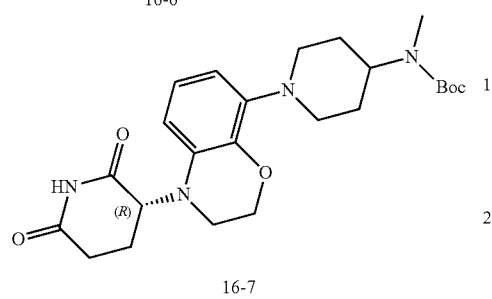

16-7

Step-1:

To a solution of 2,6-dibenzyloxypyridine 16-1 (20.0 g, 68.65 mmol) in ACN (300 mL) was added NBS (11.00 g, 61.78 mmol, 5.24 mL) at room temperature and the reaction mixture was stirred at 70° C. for 1 h. Upon completion of reaction, the reaction mixture was diluted with water (100 mL) and extracted with EtOAc (3×300 mL). The combined organic layer was washed with water (50 mL) and brine (50 mL), dried over $Na_2SO_4$, and concentrated in vacuo to get 2,6-dibenzyloxy-3-bromo-pyridine 5-7 (20.0 g, 45.38 mmol, 66% yield). LCMS ($ES^+$): m/z 370.40 $[M+H]^+$.

Step-2:

To a stirred solution of 2-bromo-6-nitro-phenol 5-1 (100.0 g, 458.71 mmol) in methanol (1400 mL) was added sodium dithionite (359.39 g, 2.06 mol) in water (1800 mL) at 70° C. Upon completion of the reaction, the reaction mixture was concentrated in vacuo. The resulting crude was dissolved in DCM, washed with water, dried over $Na_2SO_4$ and concentrated under reduced pressure to get 2-amino-6-bromo-phenol 5-2 (65.0 g, 328.42 mmol, 72% yield) as a white solid. LCMS ($ES^+$): m/z 188.27 $[M+H]^+$.

Step-3:

To a stirred solution of 2-amino-6-bromo-phenol 5-2 (52.0 g, 276.56 mmol) in DMF (504.26 mL) were added anhydrous potassium carbonate, 99% (114.67 g, 829.69 mmol, 50.07 mL) followed by 1,2-dibromoethane (51.96 g, 276.56 mmol, 23.83 mL) at room temperature. The reaction mixture was allowed to stirrer for 20 h at 100° C. After completion of reaction, the reaction mixture was diluted with EtOAc, washed with water, dried over $Na_2SO_4$ and concentrated in vacuo. The crude was purified by column chromatography (Davisil silica 230-400 mesh) using 10% ethyl acetate in petroleum ether as an eluent to afford 8-bromo-3,4-dihydro-2H-1,4-benzoxazine 5-3 (55.0 g, 218.40 mmol, 79% yield) as a brown solid. LCMS ($ES^+$): m/z 214.32 $[M+H]^+$.

Step-4:

To a solution of 8-bromo-3,4-dihydro-2H-1,4-benzoxazine 5-3 (55.0 g, 256.94 mmol) and N-ethyl-N-isopropyl-propan-2-amine (99.62 g, 770.82 mmol, 134.26 mL) in DCM (550 mL), was added benzyl carbonochloridate (52.60 g, 308.33 mmol) at 0° C., and the reaction mixture was stirred at room temperature for 12 h. Upon completion of the reaction, it was diluted with DCM and washed with saturated $NaHCO_3$ solution and brine. The organic layer was dried over $Na_2SO_4$, filtered and concentrated under reduced pressure. The resulting crude product was purified by flash chromatography silica gel (100-200 mesh) using 15% ethyl acetate in petroleum ether as an eluent to afford benzyl 8-bromo-2,3-dihydro-1,4-benzoxazine-4-carboxylate 6-2 (55.0 g, 156.38 mmol, 61% yield) as a pale brown solid. LCMS ($ES^+$): m/z 348.17 $[M+H]^+$.

Step-5:

To a solution of benzyl 8-bromo-2,3-dihydro-1,4-benzoxazine-4-carboxylate 6-2 (50.0 g, 143.60 mmol) and tert-butyl N-methyl-N-(4-piperidyl)carbamate 16-1 (30.77 g, 143.60 mmol) in toluene (250 mL) was added NaOtBu (34.50 g, 359.00 mmol) at room temperature. The reaction mixture was degassed with nitrogen gas for 10 minutes and bis(tri-tert-butylphosphine)palladium(0) (733.87 mg, 1.44 mmol) was added. The reaction mixture was degassed with nitrogen gas for an additional 5 minutes and stirred at 100° C. for 1 h. The reaction mixture was filtered through a celite bed and washed with ethyl acetate (200 mL). The organic layer was washed with water (150 mL), brine (150 mL), dried over $Na_2SO_4$, filtered and concentrated in vacuo to get the crude product, which was purified by column chromatography (Davisil silica 230-400 mesh) using 40% ethyl acetate in petroleum ether as an eluent to afford benzyl 8-[4-[tert-butoxycarbonyl(methyl)amino]-1-piperidyl]-2,3-dihydro-1,4-benzoxazine-4-carboxylate 16-2 (21.0 g, 40.12 mmol, 28% yield) as a yellow gummy solid. LCMS ($ES^+$): m/z 482.88 $[M+H]^+$.

Step-6:

A stirred solution of benzyl 8-[4-[tert-butoxycarbonyl(methyl)amino]-1-piperidyl]-2,3-dihydro-1,4-benzoxazine-4-carboxylate 16-2 (21.0 g, 43.61 mmol) in EtOAc (150 mL) and THF (150 mL) was degassed with argon for 10 minute before addition of 10 wt. % palladium on carbon, 50% water (6.12 g, 57.54 mmol). Then the reaction mixture was stirred for 20 h at room temperature under $H_2$ (60 Psi). Upon completion of reaction, the reaction mixture was filtered through celite bed, washed with DCM and EtOAc. The filtrate was evaporated under reduced pressure to get tert-butyl N-[1-(3,4-dihydro-2H-1,4-benzoxazin-8-yl)-4-piperidyl]-N-methyl-carbamate 16-3 (12.0 g, 32.47 mmol, 74% yield) as a white solid. LCMS ($ES^+$): m/z 348.81 $[M+H]^+$.

Step-7:

To a solution of tert-butyl N-[1-(3,4-dihydro-2H-1,4-benzoxazin-8-yl)-4-piperidyl]-N-methyl-carbamate 16-3 (11.0 g, 31.66 mmol) and 2,6-dibenzyloxy-3-bromo-pyridine 5-7 (11.72 g, 31.66 mmol) in toluene (150 mL) was added NaO$^t$Bu (9.13 g, 94.98 mmol) at room temperature. The reaction mixture was degassed with nitrogen gas for 10 minutes before addition of $Pd_2(dba)_3$ (2.90 g, 3.17 mmol) and Xantphos (1.83 g, 3.17 mmol). The reaction mixture was degassed with nitrogen gas for an additional 5 minutes and stirred at 100° C. for 2 h. The reaction mixture was filtered through celite bed and washed with ethyl acetate (100 mL). The organic layer was washed with water (50 mL) and brine (50 mL), dried over $Na_2SO_4$, filtered and concentrated in vacuo to get the crude product, which was purified by column chromatography (Davisil silica 230-400 mesh) using 24% ethyl acetate in petroleum ether as eluent to afford tert-butyl N-[1-[4-(2,6-dibenzyloxy-3-pyridyl)-2,3-dihydro-1,4-benzoxazin-8-yl]-4-piperidyl]-N-methyl-carbamate 16-4 (15.0 g, 20.49 mmol, 65% yield) as a yellow gum. LCMS ($ES^+$): m/z 637.61 $[M+H]^+$.

Step-8:

To a stirred solution of tert-butyl N-[1-[4-(2,6-dibenzyloxy-3-pyridyl)-2,3-dihydro-1,4-benzoxazin-8-yl]-4-piperidyl]-N-methyl-carbamate 16-4 (19.0 g, 29.84 mmol) in EtOAc (200 mL), ethanol (200 mL) and THF (200 mL) were added palladium on carbon, 20 wt. % 50% water (3.18 g, 29.84 mmol) and dioxoplatinum (677.55 mg, 2.98 mmol) at room temperature. The reaction mixture was stirred in hydrogen atmosphere under 80 psi for 16 hours at the same temperature. Then the reaction mixture was filtered through celite bed and washed with ethyl acetate (1000 mL). The filtrate was concentrated in vacuo to give the crude product, which was purified by column chromatography (Davisil silica 230-400 mesh) using 55% ethyl acetate in petroleum ether to get tert-butyl N-[1-[4-(2,6-dioxo-3-piperidyl)-2,3-dihydro-1,4-benzoxazin-8-yl]-4-piperidyl]-N-methyl-carbamate 16-5 (9.0 g, 18.25 mmol, 61% yield) as a white solid. LCMS (ES+): m/z 459.61 [M+H]+.

Step-9:

Racemic tert-butyl (1-(4-(2,6-dioxopiperidin-3-yl)-3,4-dihydro-2H-benzo[b][1,4]oxazin-8-yl)piperidin-4-yl)(methyl)carbamate 16-5 (6.0 g) was separated by SFC and concentrated in vacuo to give tert-butyl (S)-(1-(4-(2,6-dioxopiperidin-3-yl)-3,4-dihydro-2H-benzo[b][1,4]oxazin-8-yl)piperidin-4-yl)(methyl)carbamate 16-6 (Early eluting peak arbitrarily assigned as S-isomer, 2.9 g) and tert-butyl (R)-(1-(4-(2,6-dioxopiperidin-3-yl)-3,4-dihydro-2H-benzo[b][1,4]oxazin-8-yl)piperidin-4-yl)(methyl)carbamate 16-7 (Late eluting peak arbitrarily assigned as R-isomer, 2.9 g).

Preparative SFC conditions: column/dimensions: CHIRALPAK IG-H (30×250) mm, 5µ; % CO2: 60%; % co-solvent: 40% (ACN:IPA) (1:1); Total Flow: 100 g/min; Back Pressure: 100 bar; Temperature: 30° C.; UV: 235 nm; Solubility: ACN+THF+IPA.

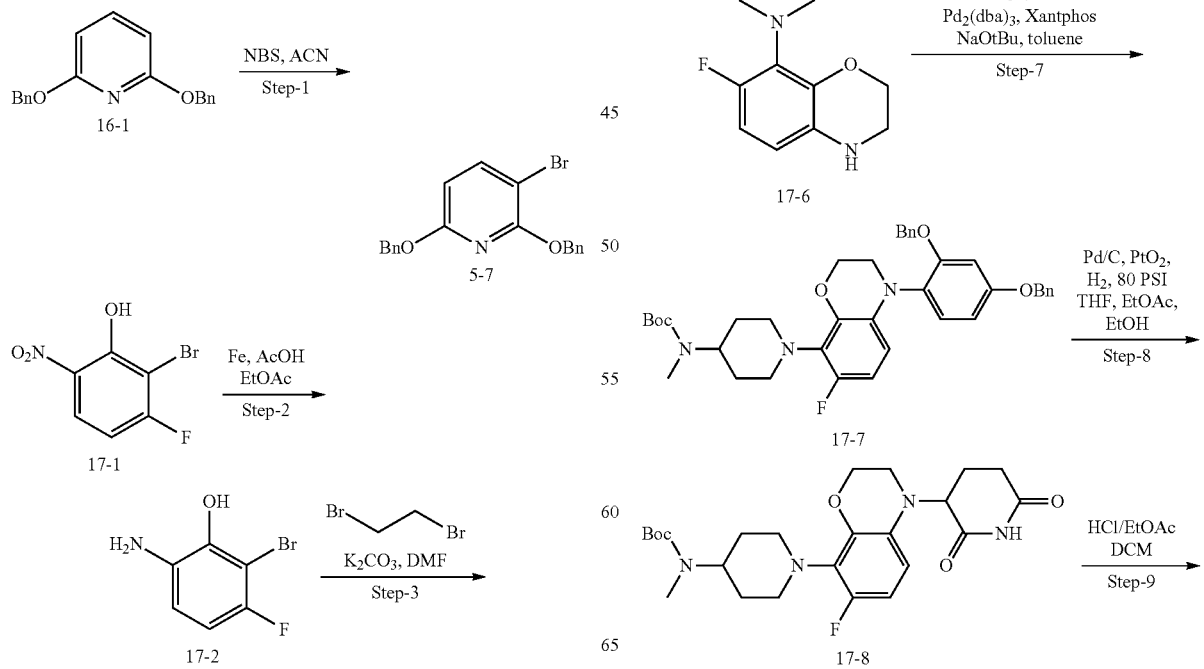

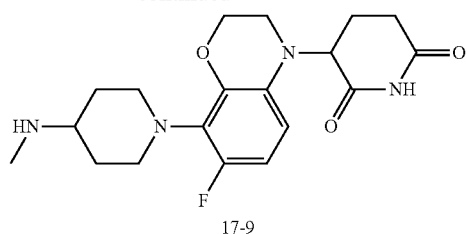

17-9

Intermediate 17-3 is prepared using the method described in the synthesis of 2-[4-[4-(2,6-dioxo-3-piperidyl)-7-fluoro-2,3-dihydro-1,4-benzoxazin-8-yl]-1-piperidyl]acetic acid (Scheme 25).

Step-4 to Step-8:

The procedures are identical to those of Step-4 to Step-8 in the synthesis of tert-butyl (S)-(1-(4-(2,6-dioxopiperidin-3-yl)-3,4-dihydro-2H-benzo[b][1,4]oxazin-8-yl)piperidin-4-yl)(methyl)carbamate 16-6.

Step-9:

To a mixture of tert-butyl (1-(4-(2,6-dioxopiperidin-3-yl)-7-fluoro-3,4-dihydro-2H-benzo[b][1,4]oxazin-8-yl)piperidin-4-yl)(methyl)carbamate 17-8 (1 eq.) in DCM (2.5 mL) is added HCl/EtOAc (4 M, 10 eq.), and the mixture is stirred at 20° C. for 1 h. Upon completion of the reaction, the reaction mixture is concentrated in vacuo to give 3-(7-fluoro-8-(4-(methylamino)piperidin-1-yl)-2,3-dihydro-4H-benzo[b][1,4]oxazin-4-yl)piperidine-2,6-dione 17-9.

Scheme 18: Synthesis of 3-[(2R)-2-methyl-8-[4-(methylamino)-1-piperidyl]-2,3-dihydro-1,4-benzoxazin-4-yl]piperidine-2,6-dione and 3-[(2S)-2-methyl-8-[4-(methylamino)-1-piperidyl]-2,3-dihydro-1,4-benzoxazin-4-yl]piperidine-2,6-dione

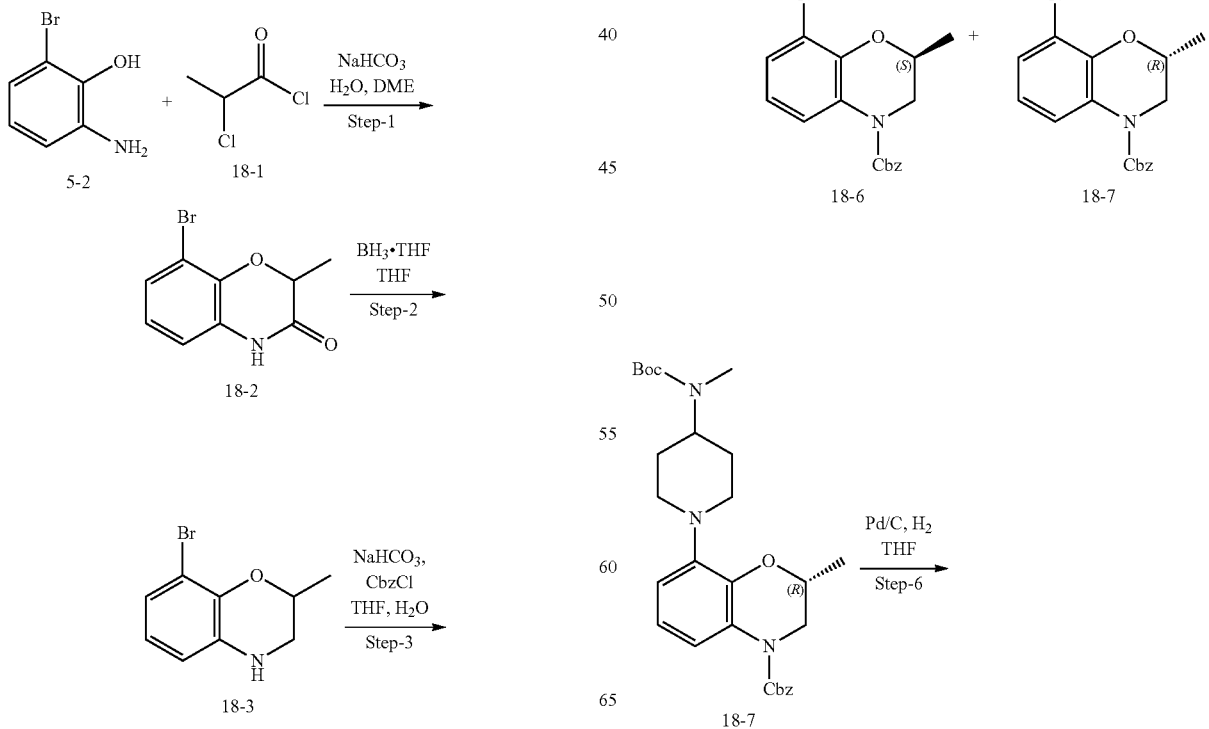

-continued

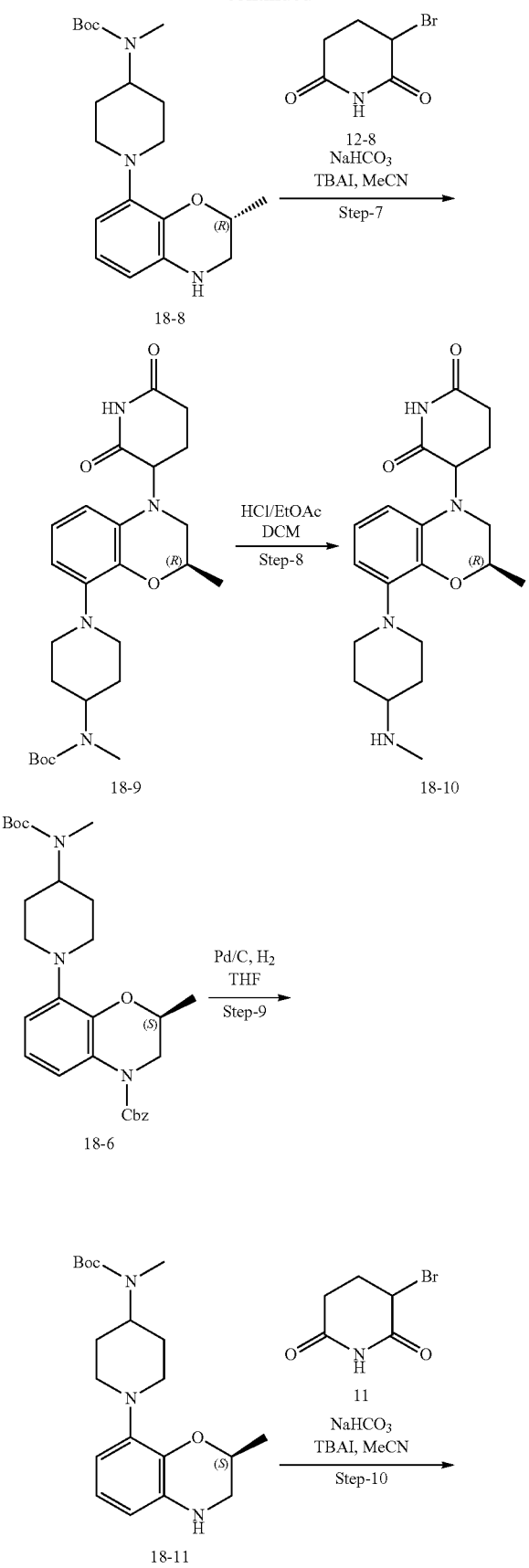

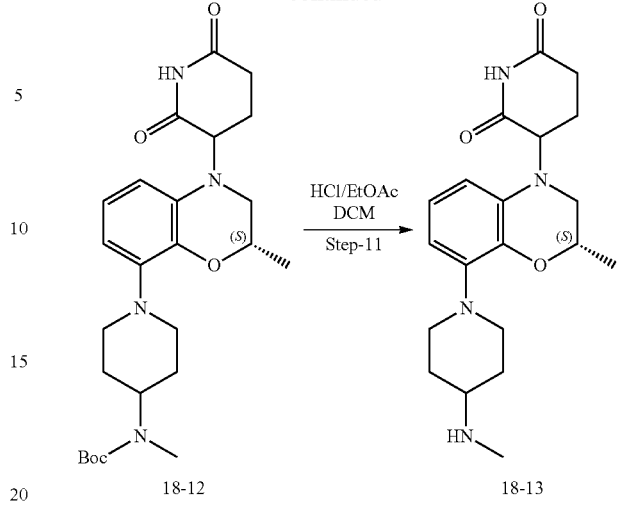

Step-1:
To a mixture of 2-amino-6-bromo-phenol 5-2 (1 g, 5.32 mmol), sodium bicarbonate (1.34 g, 15.96 mmol, 620.83 L) in water (2 mL) and DME (8 mL) was added 2-chloropropanoyl chloride 18-1 (810.35 mg, 6.38 mmol) at 25° C. The reaction mixture was stirred at 90° C. for 16 h. The reaction mixture was diluted with water (30 ml) and extracted with EtOAc (3×20 ml). The organics were dried (Na$_2$SO$_4$), filtered and concentrated under reduced pressure to give a residue. The residue was purified by flash silica gel chromatography (ISCO®; 20 g SepaFlash® Silica Flash Column, Eluent of 0-20% ethyl acetate/petroleum ether gradient @60 mL/min) to give 8-bromo-2-methyl-2H-benzo[b][1,4]oxazin-3(4H)-one 18-2 (1.1 g, 4.54 mmol, 85.43% yield) as a yellow solid. LCMS (ES$^+$): m/z 241.8 [M+H]$^+$.

Step-2:
To a solution of 8-bromo-2-methyl-4H-1,4-benzoxazin-3-one 18-2 (6.35 g, 26.23 mmol) in THF (127 mL), borane in THF (1 M, 78.70 mL) was added at 0° C. under N$_2$ atmosphere. The resulting mixture was refluxed at 70° C. for 2.5 h. After cooling, the reaction mixture was quenched with methanol (80 mL) slowly. All volatiles were removed under reduced pressure. A 1 N aqueous solution of hydrochloric acid (20 mL) was added to the liquid residue and the mixture was stirred at 25° C. for 30 minutes. After cooling, the reaction mixture was made alkaline using saturated sodium bicarbonate solution (50 mL) and extracted with ethyl acetate (50 mL×3), the combined organic layers were dried over Na$_2$SO$_4$, filtered and concentrated under reduced pressure to give a residue. The residue was purified by flash silica gel chromatography (ISCO®; 80 g SepaFlash® Silica Flash Column, Eluent of 0-20% ethyl acetate/petroleum ether gradient @100 mL/min) to give 8-bromo-2-methyl-3,4-dihydro-2H-1,4-benzoxazine 18-3 (5.67 g, 24.55 mmol, 93.57% yield) as a colorless oil. LCMS (ES$^+$): m/z 228.0 [M+H]$^+$.

Step-3:
To a solution of 8-bromo-2-methyl-3,4-dihydro-2H-1,4-benzoxazine 18-3 (5.67 g, 24.86 mmol) in THF (56 mL) and water (56 mL) was added NaHCO$_3$ (4.18 g, 49.72 mmol), then benzyl carbonochloridate (6.36 g, 37.29 mmol, 5.3 mL) was added at 0° C. After addition, the solution was stirred at 25° C. for 12 hr. The reaction mixture was poured into water (60 mL) and extracted with EtOAc (40 mL×3). The combined organic layer was washed with brine (40 mL), dried over Na$_2$SO$_4$, filtered and concentrated to give a residue. The residue was purified by flash silica gel chromatography (ISCO®; 80 g SepaFlash® Silica Flash Column, Eluent of 0-15% ethyl acetate/petroleum ether gradient @100 mL/min) to afford benzyl 8-bromo-2-methyl-2,3-dihydro-1,4-benzoxazine-4-carboxylate 18-4 (8.4 g, 23.07 mmol, 92.81% yield) as a yellow solid. LCMS (ES$^+$): m/z 362.1 [M+H]$^+$.

Step-4:

A mixture of benzyl 8-bromo-2-methyl-2,3-dihydro-1,4-benzoxazine-4-carboxylate 18-4 (4 g, 11.04 mmol), tert-butyl N-methyl-N-(4-piperidyl)carbamate 16-1 (2.60 g, 12.15 mmol), Pd-PEPPSI-IHeptCl (1.07 g, 1.10 mmol) and cesium carbonate (10.79 g, 33.13 mmol) in dioxane (40 mL) was degassed and purged with N$_2$ 3 times, and then the mixture was stirred at 90° C. for 12hs under N$_2$ atmosphere. Water (150 mL) was added to the mixture and extracted with EtOAc(2×100 mL). The combined organic layers were washed with brine (2×100 mL), dried over Na$_2$SO$_4$, filtered and concentrated under reduced pressure to give a residue. The residue was purified by flash silica gel chromatography (ISCO®; 80 g SepaFlash® Silica Flash Column, Eluent of 0-30% ethyl acetate/petroleum ether gradient at 100 mL/min) to afford benzyl 8-[4-[tert-butoxycarbonyl(methyl) amino]-1-piperidyl]-2-methyl-2,3-dihydro-1,4-benzoxazine-4-carboxylate 18-5 (2.9 g, 5.55 mmol, 50.22% yield) as a yellow oil. LCMS (ES$^+$): m/z 496.1 [M+H]$^+$.

Step-5:

Racemic benzyl 8-[4-[tert-butoxycarbonyl(methyl) amino]-1-piperidyl]-2-methyl-2,3-dihydro-1,4-benzoxazine-4-carboxylate 18-5 was purified by SFC (column: DAICEL CHIRALCEL OJ (250 mm×30 mm, 10 um); mobile phase: 0.10% oNH$_3$H$_2$O MEOH, 60 ml/min; 8.2 min) to give benzyl (2S)-8-[4-[tert-butoxycarbonyl(methyl) amino]-1-piperidyl]-2-methyl-2,3-dihydro-1,4-benzoxazine-4-carboxylate 18-6 (1.3 g, 2.62 mmol, 44.82% yield) and benzyl (2R)-8-[4-[tert-butoxycarbonyl(methyl)amino]-1-piperidyl]-2-methyl-2,3-dihydro-1,4-benzoxazine-4-carboxylate 18-7 (1.4 g, 2.82 mmol, 48.27% yield) as yellow oil.

SFC method: column: Chiralcel OJ-3 50×4.6 mm I. D., 3 um; Mobile phase: Phase A for CO$_2$, and Phase B for MEOH (0.05% DEA); Gradient elution: B in A from 5% to 20%; Flow rate: 3 mL/min; Detector: DAD; Column Temp: 35° C.; Back Pressure: 100 Bar. LCMS (ES$^+$): m/z 496.5 [M+H]$^+$.

Step-6:

A stirred solution of benzyl (2R)-8-[4-[tert-butoxycarbonyl(methyl)amino]-1-piperidyl]-2-methyl-2,3-dihydro-1,4-benzoxazine-4-carboxylate 18-7 (1.54 g, 3.11 mmol) in THF (30 mL) was degassed with N$_2$ for 5 min. Subsequently, 10% Pd/C (377.38 mg, 310.73 mol) added at 25° C. The reaction mixture was stirred under H$_2$ (3.11 mmol) atmosphere for 12 hrs. After completion of reaction, the reaction mixture was filtered through a celite bed and washed with EtOAc. The filtrate was concentrated in vacuo to afford a residue. Compound tert-butyl N-methyl-N-[1-[(2R)-2-methyl-3,4-dihydro-2H-1,4-benzoxazin-8-yl]-4-piperidyl]carbamate 18-8 (1.1 g, 2.98 mmol, 95.82% yield) was obtained as a yellow solid. LCMS (ES$^+$): m/z 362.1 [M+H]$^+$.

Step-7:

To a solution of tert-butyl N-methyl-N-[1-[(2R)-2-methyl-3,4-dihydro-2H-1,4-benzoxazin-8-yl]-4-piperidyl] carbamate 18-8 (600.00 mg, 1.66 mmol) in MeCN (6 mL) was added tetrabutylammonium iodide (61.31 mg, 165.99 mol), sodium hydrogen carbonate, 99% (278.89 mg, 3.32 mmol, 129.18 L) and 3-bromopiperidine-2,6-dione 12-8 (478.06 mg, 2.49 mmol). The mixture was stirred at 90° C. for 12 h under air atmosphere. Then 3-bromopiperidine-2,6-dione (478.06 mg, 2.49 mmol), sodium hydrogen carbonate, 99% (278.89 mg, 3.32 mmol, 129.18 L), tetrabutylammonium iodide (61.31 mg, 165.99 mol) was added, the mixture was stirred at 90° C. for 12 h. The mixture was cooled to room temperature and diluted with H$_2$O (30 mL) and extracted with DCM (20 mL×3). The combined organic layers were washed with brine (20 mL), dried over Na$_2$SO$_4$, filtered and concentrated under reduced pressure to give a residue. The residue was purified by flash silica gel chromatography (ISCO®; 12 g SepaFlash® Silica Flash Column, Eluent of 0-50% ethyl acetate/petroleum ether gradient at 40 mL/min) to give tert-butyl N-methyl-N-[1-[(2R)-4-(2, 6-dioxo-3-piperidyl)-2-methyl-2,3-dihydro-1,4-benzoxazin-8-yl]-4-piperidyl]carbamate 18-9 (330 mg, 666.56 mol, 40.16% yield) as a white solid. LCMS (ES$^+$): m/z 473.4 [M+H]$^+$.

Step-8:

To a mixture of tert-butyl N-methyl-N-[1-[(2R)-4-(2,6-dioxo-3-piperidyl)-2-methyl-2,3-dihydro-1,4-benzoxazin-8-yl]-4-piperidyl]carbamate 18-9 (250 mg, 529.02 mol) in DCM (2.5 mL) was added HCl/EtOAc (4 M, 1.25 mL), the mixture was stirred at 20° C. for 1 h. The reaction mixture was concentrated under reduced pressure to give a residue. Compound 3-[(2R)-2-methyl-8-[4-(methylamino)-1-piperidyl]-2,3-dihydro-1,4-benzoxazin-4-yl]piperidine-2,6-dione 18-10 (200 mg, 489.09 mol, 92.45% yield, HCl salt) was obtained as white solid. LCMS (ES$^+$): m/z 373.3 [M+H]$^+$.

Step-9 to Step-11:

The procedures were identical to those of Step-6 to Step-8. Compound 3-[(2S)-2-methyl-8-[4-(methylamino)-1-piperidyl]-2,3-dihydro-1,4-benzoxazin-4-yl]piperidine-2,6-dione 18-13 was obtained as a yellow solid. LCMS (ES$^+$): m/z 373.2 [M+H]$^+$.

Scheme 19: Synthesis of 3-[2,2-dimethyl-8-[4-(methylamino)-1-piperidyl]-3H-1,4-benzoxazin-4-yl]piperidine-2,6-dione

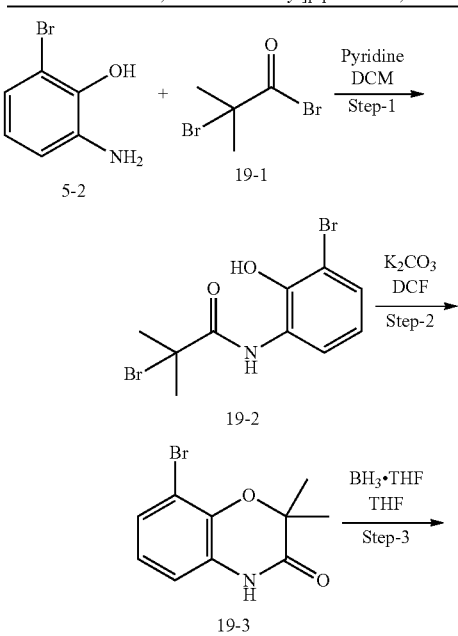

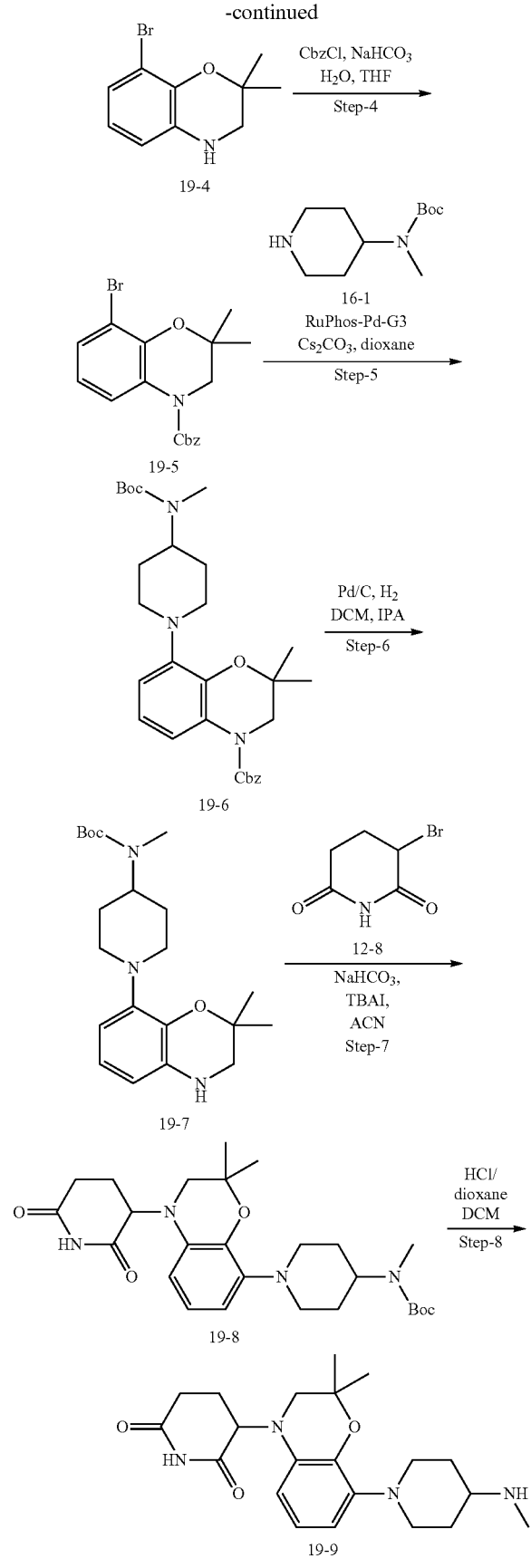

Step-1:
To a solution of 2-amino-6-bromophenol 5-2 (4 g, 21.27 mmol) in DCM (50 mL) was added pyridine (1.76 g, 22.26 mmol, 1.8 mL) under $N_2$. The mixture was cooled in ice and then a solution of 2-bromo-2-methylpropanoyl bromide 19-1 (5.21 g, 22.65 mmol, 2.8 mL) was added slowly. After addition, the solution was stirred at 25° C. under $N_2$ for 2 hours. The reaction mixture was poured into water (200 mL) and extracted with EtOAc (70 mL×4). The combined organic layer was washed with brine (30 mL), dried over $Na_2SO_4$, filtered and concentrated to give the crude product. Compound 2-bromo-N-(3-bromo-2-hydroxyphenyl)-2-methylpropanamide 19-2 (6.5 g, 17.74 mmol, 83.41% yield) was obtained as a brown oil. LCMS ($ES^+$): m/z 337.6 $[M+H]^+$.

Step-2:
To a solution of 2-bromo-N-(3-bromo-2-hydroxy-phenyl)-2-methyl-propanamide 19-2 (6.4 g, 18.99 mmol) in DMF (148.53 mL) was added $K_2CO_3$ (5.76 g, 41.68 mmol). After addition, the solution was stirred at 100° C. for 12 hours. The reaction mixture was poured into water (500 mL) and extracted with EtOAc (120 mL×5). The combined organic layer was washed with brine (70 mL), dried over $Na_2SO_4$, filtered and concentrated to give the crude product, which was purified by column chromatography ($SiO_2$, petroleum ether:EtOAc=99:1-95:5-85:15) to give 8-bromo-2,2-dimethyl-2H-benzo[b][1,4]oxazin-3(4H)-one 19-3 (4.88 g, 18.86 mmol, 99.34% yield) as a yellow solid. LCMS ($ES^+$): m/z 225.7 $[M+H]^+$.

Step-3:
To a solution of 8-bromo-2,2-dimethyl-2H-benzo[b][1,4]oxazin-3(4H)-one 19-3 (4.88 g, 19.06 mmol) in THF (10 mL), was added borane in tetrahydrofuran (1 M, 40 mL). The reaction mixture stirred at 70° C. for 2 hours. The reaction mixture was quenched with MeOH (15 mL) until there are no bubbles, the mixture was concentrated in vacuo. The residue was purified by column chromatography ($SiO_2$, petroleum ether:EtOAc=99:1-98:2) to give 8-bromo-2,2-dimethyl-3,4-dihydro-2H-benzo[b][1,4]oxazine 19-4 (4.5 g, 18.40 mmol, 96.56% yield) as an orange oil. LCMS ($ES^+$): m/z 241.7 $[M+H]^+$.

Step-4:
To a solution of 8-bromo-2,2-dimethyl-3,4-dihydro-2H-benzo[b][1,4]oxazine 19-4 (4.4 g, 18.17 mmol) in THF (25 mL) and water (25 mL) was added $NaHCO_3$ (3.05 g, 36.35 mmol) and benzyl carbonochloridate (10.91 g, 63.94 mmol, 9 mL). After addition, the solution was stirred at 25° C. for 24 hr. The reaction mixture was poured into water (200 mL) and extracted with EtOAc (70 mL×4). The combined organic layer was washed with brine (50 mL), dried over $Na_2SO_4$, filtered and concentrated to give a residue. The residue was purified by column chromatography ($SiO_2$, petroleum ether:EtOAc=99:1-91:9) to give benzyl 8-bromo-2,2-dimethyl-2,3-dihydro-4H-benzo[b][1,4]oxazine-4-carboxylate 19-5 (6.79 g, 17.51 mmol, 96.32% yield) as a yellow solid. LCMS ($ES^+$): m/z 375.7 $[M+H]^+$.

Step-5:
To a solution of benzyl 8-bromo-2,2-dimethyl-2,3-dihydro-4H-benzo[b][1,4]oxazine-4-carboxylate 19-5 (1 g, 2.66 mmol), tert-butyl N-methyl-N-(4-piperidyl)carbamate 16-1 (626.55 mg, 2.92 mmol) and $Cs_2CO_3$ (1.73 g, 5.32 mmol) in dioxane (10 mL) was added RuPhos PdG3 catalyst (111.15 mg, 132.89 mol) under $N_2$ at 25° C. After addition, the solution was stirred under $N_2$ at 90° C. for 12 hours. The reaction mixture was poured into water (40 mL), the mixture was extracted with EtOAc (20 mL×4). The combined organic layer was washed with brine (20 mL), dried over Na₂SO₄, filtered and concentrated to give a residue. The light-yellow residue was purified by column chromatography (SiO₂, petroleum ether:EtOAc=100:0-91:9-84:16) to give benzyl 8-(4-((tert-butoxycarbonyl)(methyl)amino)piperidin-1-yl)-2,2-dimethyl-2,3-dihydro-4H-benzo[b][1,4]oxazine-4-carboxylate 19-6 (355 mg, 606.02 mol, 22.80% yield) as an orange oil. LCMS (ES⁺): m/z 510.0 [M+H]⁺.

Step-6: To the solution of benzyl 8-[4-[tert-butoxycarbonyl(methyl)amino]-1-piperidyl]-2,2-dimethyl-3H-1,4-benzoxazine-4-carboxylate 19-6 (0.7 g, 1.37 mmol) in DCM (5 mL) and IPA (10 mL) was added 10% Pd/C (70 mg) under N₂. The suspension was degassed under vacuum and purged with H₂ for 3 times. The reaction mixture was stirred under H₂ (15 psi) at 20° C. for 12 hours. The residue was filtered, and the filtrate was concentrated to give tert-butyl N-[1-(2,2-dimethyl-3,4-dihydro-1,4-benzoxazin-8-yl)-4-piperidyl]-N-methyl-carbamate 19-7 (471 mg, 1.20 mmol, 87.67% yield) as a colorless oil. LCMS (ES⁺): m/z 375.9 [M+H]⁺.

Step-7:

To a solution of tert-butyl N-[1-(2,2-dimethyl-3,4-dihydro-1,4-benzoxazin-8-yl)-4-piperidyl]-N-methyl-carbamate 19-7 (470 mg, 1.25 mmol) and 3-bromopiperidine-2,6-dione 12-8 (360.50 mg, 1.88 mmol) in ACN (4 mL) was added NaHCO₃ (210.29 mg, 2.50 mmol) and tetrabutylammonium iodide (46.23 mg, 125.17 mol) at 15° C. After addition, the solution was stirred at 100° C. for 12 hours. The reaction mixture was diluted with water (20 mL). The mixture was filtered and the filter cake was washed with water (10 mL). The filter cake was concentrated under vacuum to get a residue, which was diluted with DCM:MeOH=10:1 (20 mL). The mixture was filtered and the filtrate was concentrated under vacuum. The residue was purified by Prep-TLC (DCM:MeOH=8:1). Compound tert-butyl (1-(4-(2,6-dioxopiperidin-3-yl)-2,2-dimethyl-3,4-dihydro-2H-benzo[b][1,4]oxazin-8-yl)piperidin-4-yl)(methyl)carbamate 19-8 (118 mg, 242.50 mol, 19.37% yield) was obtained as a gray solid.

Step-8:

To a solution of tert-butyl N-[1-[4-(2,6-dioxo-3-piperidyl)-2,2-dimethyl-3H-1,4-benzoxazin-8-yl]-4-piperidyl]-N-methyl-carbamate 19-8 (118 mg, 242.50 mol) in DCM was added HCl/dioxane (242.50 mol) at 15° C. After addition, the solution was stirred at 15° C. for 1 hour. The reaction mixture was concentrated in vacuo to give 3-[2,2-dimethyl-8-[4-(methylamino)-1-piperidyl]-3H-1,4-benzoxazin-4-yl]piperidine-2,6-dione 19-9 (102 mg, 229.11 mol, 94.48% yield, HCl salt) as a white solid. LCMS (ES⁺): m/z 387.2 [M+H]⁺.

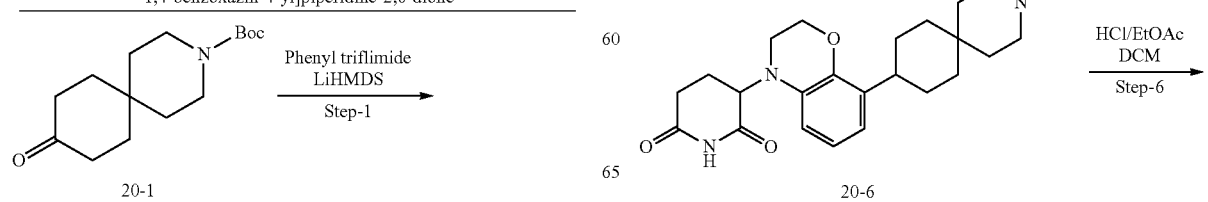

Scheme 20: Synthesis of 3-[8-(3-azaspiro[5.5]undecan-9-yl)-2,3-dihydro-1,4-benzoxazin-4-yl]piperidine-2,6-dione

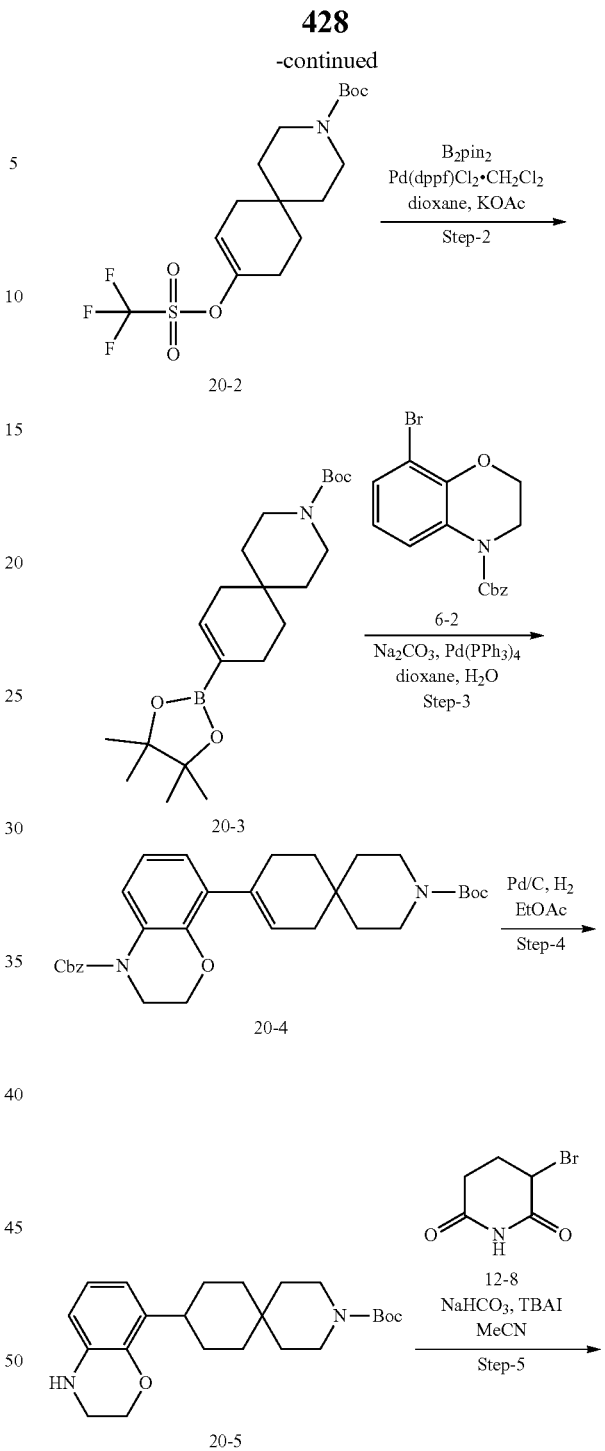

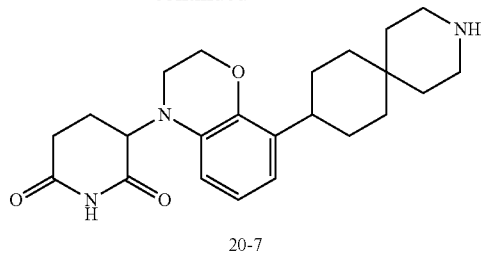 [SMILES: O=C1CCC(N2CCOc3c(C4CCC5(CCNCC5)CC4)cccc32)C(=O)N1]

20-7

Step-1:

Under a nitrogen atmosphere, to a solution of 9-oxo-3-azaspiro[5.5]undecane-3-carboxylic acid tert-butyl ester 20-1 (7 g, 26.18 mmol) in THF (30 mL) cooled to −78° C. was added lithium bis(trimethylsilyl)azanide (1 M, 31.42 mL) dropwise. The mixture was stirred at −78° C. for 45 min and 1,1,1-trifluoro-N-phenyl-N-(trifluoromethylsulfonyl)methanesulfonamide (10.29 g, 28.80 mmol) was added. The mixture was stirred at 30° C. for 12 h. The mixture was quenched by NH$_4$Cl (100 mL) at 0° C. and extracted with EtOAc (100 mL×3). The combined organic layers were washed with brine (100 mL), dried over Na$_2$SO$_4$, filtered and concentrated under reduced pressure to give a residue. The residue was purified by column chromatography (SiO$_2$, petroleum ether/ethyl acetate=1/0 to 10/1) to afford tert-butyl 9-(((trifluoromethyl)sulfonyl)oxy)-3-azaspiro[5.5]undec-8-ene-3-carboxylate 20-2 (12.1 g, 18.18 mmol, 69.42% yield) as a yellow oil.

$^1$H NMR (400 MHz, CDCl$_3$): δ ppm 5.69 (t, J=4.2 Hz, 1H), 3.42-3.53 (m, 2H), 3.28-3.39 (m, 2H), 2.34 (ddd, J=8.4, 4.4, 1.6 Hz, 2H), 2.07-2.11 (m, 2H), 1.65-1.69 (m, 2H), 1.46 (s, 9H), 1.39-1.45 (m, 4H).

Step-2:

Under a nitrogen atmosphere, to a solution of tert-butyl 9-(trifluoromethylsulfonyloxy)-3-azaspiro[5.5]undec-9-ene-3-carboxylate 20-2 (12.1 g, 18.18 mmol) in dioxane (100 mL) was added cyclopentyl(diphenyl)phosphane-dichloropalladium-iron (1.33 g, 1.82 mmol), potassium acetate (5.35 g, 54.53 mmol, 3.41 mL) and 4,4,5,5-tetramethyl-2-(4,4,5,5-tetramethyl-1,3,2-dioxaborolan-2-yl)-1,3,2-dioxaborolane (4.85 g, 19.08 mmol). The mixture was stirred at 80° C. for 12 h. The mixture was cooled to room temperature and diluted with H$_2$O (100 mL) and extracted with EtOAc (100 mL×3). The combined organic layers were washed with brine (100 mL), dried over Na$_2$SO$_4$, filtered and concentrated under reduced pressure to give a residue. The residue was purified by column chromatography (SiO$_2$, petroleum ether/ethyl acetate=1/0 to 10/1) to afford tert-butyl 9-(4,4,5,5-tetramethyl-1,3,2-dioxaborolan-2-yl)-3-azaspiro[5.5]undec-8-ene-3-carboxylate 20-3 (8.53 g, 18.09 mmol, 99.50% yield) as a yellow oil.

$^1$H NMR (400 MHz, CDCl$_3$): δ ppm 6.45-6.54 (m, 1H), 3.40-3.52 (m, 2H), 3.25-3.36 (m, 2H), 2.10-2.19 (m, 2H), 1.99 (br d, J=3.2 Hz, 2H), 1.46 (s, 11H), 1.37 (br t, J=5.6 Hz, 4H), 1.28 (s, 12H).

Step-3:

Under nitrogen atmosphere, to a solution of tert-butyl 9-(4,4,5,5-tetramethyl-1,3,2-dioxaborolan-2-yl)-3-azaspiro[5.5]undec-9-ene-3-carboxylate 20-3 (8.45 g, 22.40 mmol) in water (20 mL) and dioxane (80 mL) were added palladium triphenylphosphane (2.16 g, 1.87 mmol), sodium carbonate (5.94 g, 56.00 mmol) and benzyl 8-bromo-2H-benzo[b][1,4]oxazine-4(3H)-carboxylate 6-2 (6.5 g, 18.67 mmol). The mixture was stirred at 90° C. for 12 h. The mixture was cooled to room temperature and diluted with H$_2$O (100 mL) and extracted with EtOAc (100 mL×2). The combined organic layers were washed with brine (100 mL), dried over Na$_2$SO$_4$, filtered and concentrated under reduced pressure to give a residue. The residue was purified by column chromatography (SiO$_2$, petroleum ether/ethyl acetate=1/0 to 10/1) to afford benzyl 8-(3-(tert-butoxycarbonyl)-3-azaspiro[5.5]undec-8-en-9-yl)-2H-benzo[b][1,4]oxazine-4(3H)-carboxylate 20-4 (7.1 g, 13.28 mmol, 71.13% yield) as a yellow oil. LCMS (ES$^+$): m/z 463.2 [M−tBu+H]$^+$.

Step-4:

To a solution of benzyl 8-(3-tert-butoxycarbonyl-3-azaspiro[5.5]undec-9-en-9-yl)-2,3-dihydro-1,4-benzoxazine-4-carboxylate 20-4 (130 mg, 250.65 mol) in EtOAc (5 mL) was added Pd/C (5%, 50 mg) under N$_2$ atmosphere. The suspension was degassed and purged with H$_2$ three times. The mixture was stirred under H$_2$ (15 Psi) at 30° C. for 12 h. The reaction mixture was filtered and concentrated under reduced pressure to give tert-butyl 9-(3,4-dihydro-2H-1,4-benzoxazin-8-yl)-3-azaspiro[5.5]undecane-3-carboxylate 20-5 (90 mg, 232.84 mol, 92.89% yield) as a yellow solid. LCMS (ES$^+$): m/z 331.1 [M−tBu+H]$^+$.

Step-5:

To a solution of tert-butyl 9-(3,4-dihydro-2H-1,4-benzoxazin-8-yl)-3-azaspiro[5.5]undecane-3-carboxylate 20-5 (90 mg, 232.84 mol) in MeCN (0.5 mL) was added tetrabutylammonium iodide (8.60 mg, 23.28 mol), sodium hydrogen carbonate, 99% (39.12 mg, 465.69 mol) and 3-bromopiperidine-2,6-dione 12-8 (67.06 mg, 349.26 mol). The mixture was stirred at 90° C. for 12 h under air atmosphere. The mixture was cooled to room temperature and diluted with H$_2$O (20 mL) and extracted with DCM (30 mL×3). The combined organic layers were washed with brine (20 mL), dried over Na$_2$SO$_4$, filtered and concentrated under reduced pressure to give a residue. The residue was purified by prep-TLC (SiO$_2$, DCM/ethyl acetate=2/1) to give tert-butyl 9-(4-(2,6-dioxopiperidin-3-yl)-3,4-dihydro-2H-benzo[b][1,4]oxazin-8-yl)-3-azaspiro[5.5]undecane-3-carboxylate 20-6 (60 mg, 119.37 mol, 51.27% yield) as a yellow solid. LCMS (ES$^+$): m/z 498.3 [M+H]$^+$.

Step-6:

To a solution of tert-butyl 9-[4-(2,6-dioxo-3-piperidyl)-2,3-dihydro-1,4-benzoxazin-8-yl]-3-azaspiro[5.5]undecane-3-carboxylate 20-6 (60 mg, 120.57 mol) in DCM (13.82 mL) was added HCl/EtOAc (4 M, 184.62 L). The mixture was stirred at 30° C. for 12 h. The reaction mixture was concentrated under reduced pressure to afford 3-[8-(3-azaspiro[5.5]undecan-9-yl)-2,3-dihydro-1,4-benzoxazin-4-yl]piperidine-2,6-dione 20-7 (40.56 mg, 91.97 mol, 76.28% yield, HCl salt) as a yellow solid. LCMS (ES$^+$): m/z 398.1 [M+H]$^+$.

Scheme 21: 3-(8-(2-azaspiro[3.3]heptan-6-yl)-2,3-dihydro-4H-benzo[b][1,4]oxazin-4-yl)piperidine-2,6-dione 21-1

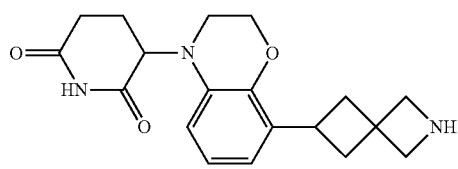

This compound is synthesized substantially following the synthesis of 3-[8-(3-azaspiro[5.5]undecan-9-yl)-2,3-dihydro-1,4-benzoxazin-4-yl]piperidine-2,6-dione 20-7, with 2-azaspiro[3.3]heptan-6-one as starting material.
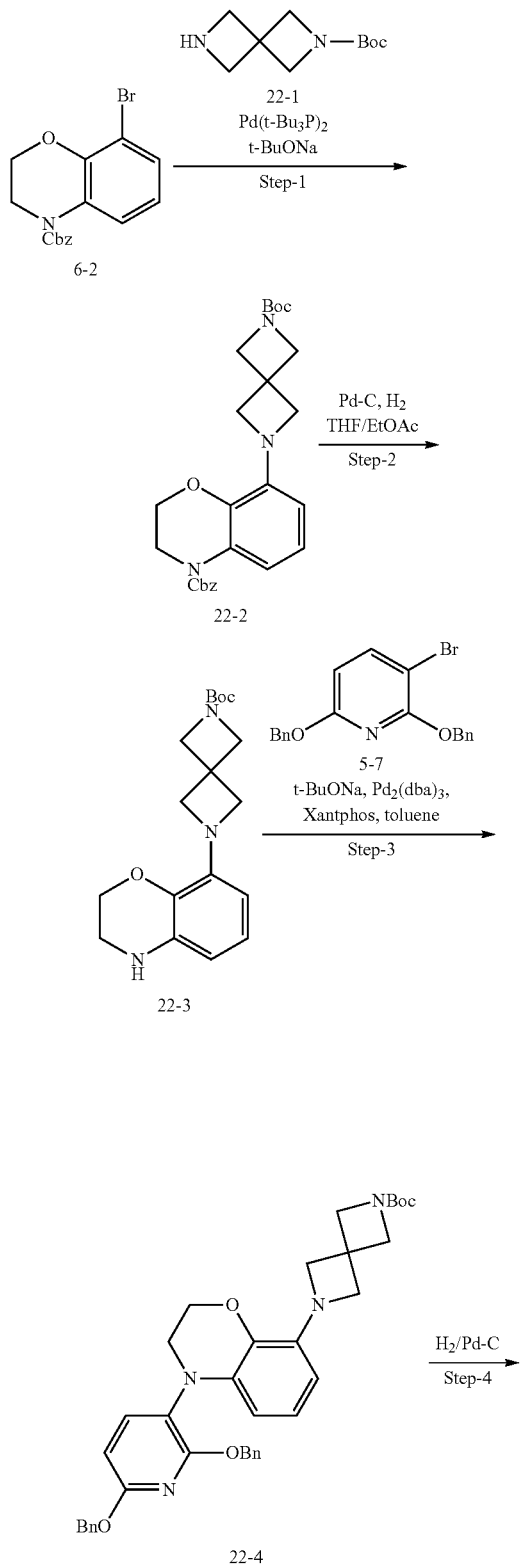
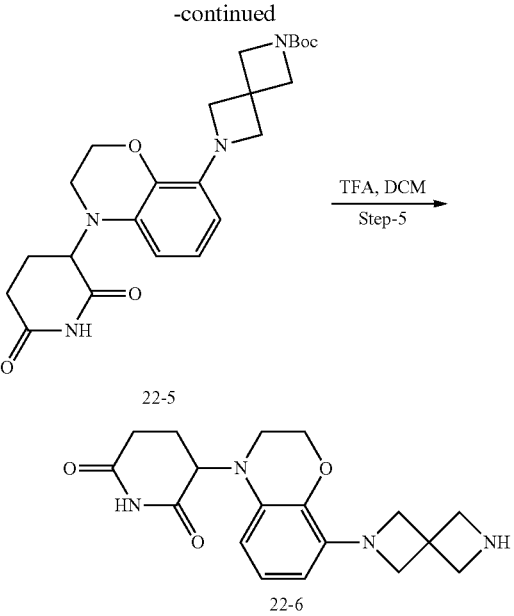
Compound 3-(8-(2,6-diazaspiro[3.3]heptan-2-yl)-2,3-dihydro-4H-benzo[b][1,4]oxazin-4-yl)piperidine-2,6-dione 22-6 is prepared using the method described in Step-1 to Step-4 and Step-6 in the synthesis of (3S)-3-(8-piperazin-1-yl-2,3-dihydro-1,4-benzoxazin-4-yl)piperidine-2,6-dione 10-10.
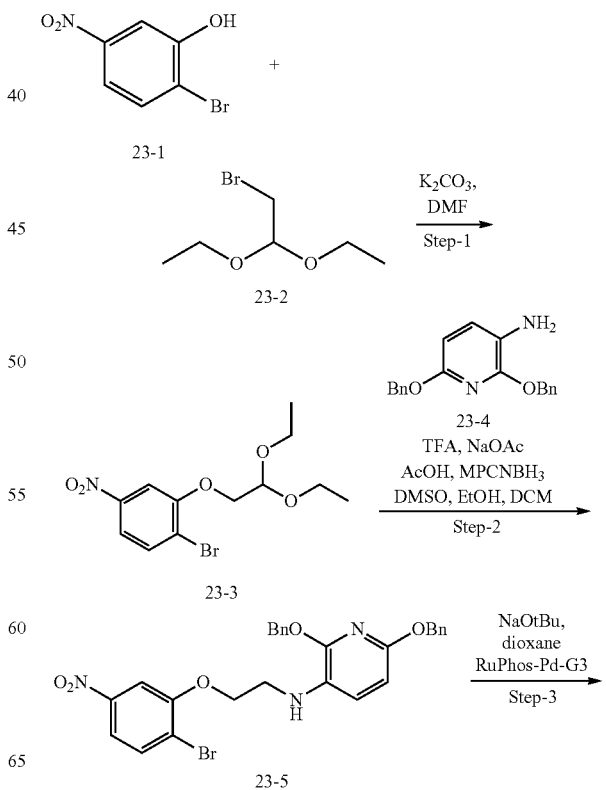

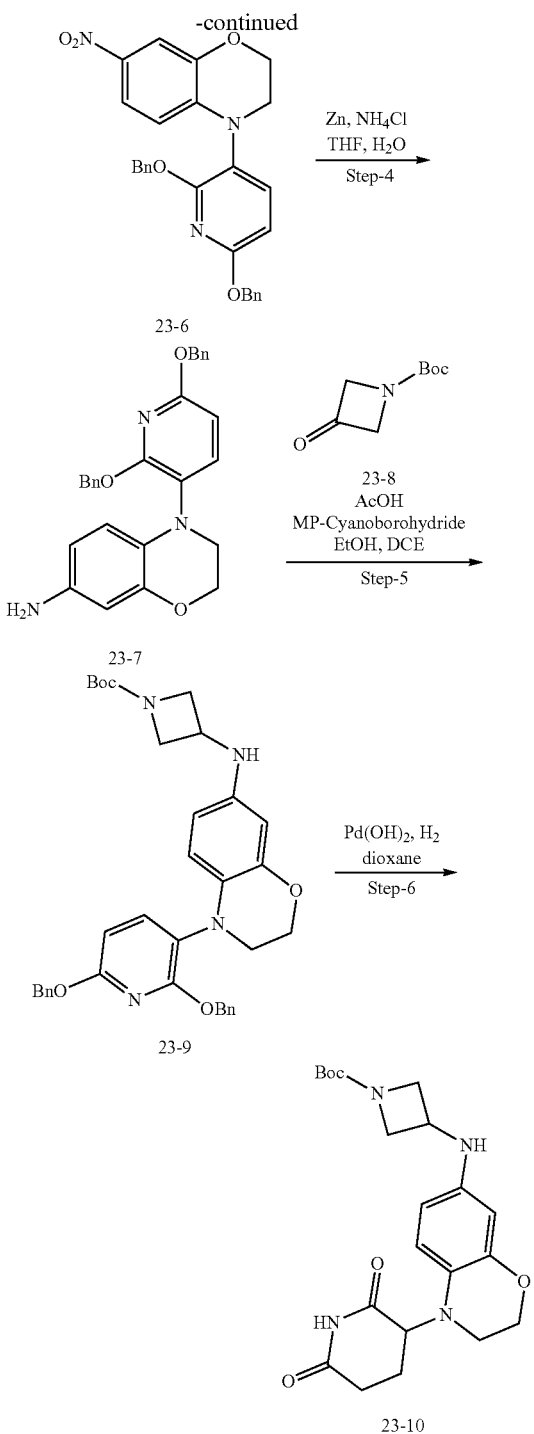

uct, which was purified by column chromatography (60-120 mesh silica gel, 50 g) using 0-10% ethyl acetate/petroleum ether as eluent to afford 1-bromo-2-(2,2-diethoxyethoxy)-4-nitro-benzene 23-3 (2.8 g, 8.38 mmol, 91.33% yield) as an off white solid.

$^1$H NMR (300 MHz, DMSO-$d_6$): δ=7.92-7.89 (m, 2H), 7.79-7.75 (m, 1H), 4.87 (t, J=5.1, 1H), 4.22 (d, J=5.1, 2H), 3.75-3.67 (m, 2H), 3.64-3.59 (m, 2H), 1.15 (t, J=7.05, 6H).

Step-2:

To a 10 mL single neck round bottom flask containing a well stirred solution of 1-bromo-2-(2,2-diethoxyethoxy)-4-nitro-benzene 23-3 (2 g, 5.99 mmol) in DCM (20 mL) was added trifluoroacetic acid (6.82 g, 59.85 mmol, 4.61 mL) at room temperature. The resultant reaction mixture was stirred for 15 h. Then the solvent was evaporated and the resulting pale solid was dissolved in DMSO (15 mL) and ethanol (15 mL). Anhydrous sodium acetate (1.47 g, 17.96 mmol, 962.66 µL), acetic acid (3.59 g, 59.85 mmol, 3.42 mL) and 2,6-dibenzyloxypyridin-3-amine 23-4 (1.83 g, 5.99 mmol) were then added into the reaction mixture and the reaction mixture was stirred for 1 h, and MPCNBH$_3$ (4.3 g, 8.98 mmol) was added and the stirring was continued for 15 h at room temperature. After completion of reaction, it was filtered through cotton and the filtrate was diluted with water and extracted with EtOAc (40 mL). The mixture was concentrated under reduced pressure and the crude residue was purified using flash silica gel (230-400 mesh) column chromatography (10-15% EtOAc/petroleum ether) to afford 2,6-dibenzyloxy-N-[2-(2-bromo-5-nitro-phenoxy)ethyl]pyridin-3-amine 23-5 (1.2 g, 1.87 mmol, 31.22% yield) as a brown solid. LCMS (ES$^+$): m/z 550.1 [M+H]$^+$.

Step-3:

To a 250 ml sealed tube containing a stirred solution of 2,6-dibenzyloxy-N-[2-(2-bromo-5-nitro-phenoxy)ethyl]pyridin-3-amine 23-5 (5.9 g, 10.72 mmol), sodium tert-butoxide (3.09 g, 32.16 mmol) in 1,4-dioxane (80 mL) was added. The reaction mixture was degassed with nitrogen for 10 min. Then RuPhos-Pd-G3 (448.07 mg, 535.97 mol) was added and the reaction mixture was heated at 85° C. for 4 hr. After completion of the reaction, the reaction mixture was filtered through celite and washed with ethyl acetate (100 mL). The organic layers were washed with water (100 mL) followed by brine (50 mL). It was then extracted with ethyl acetate(100 mL) and dried over Na$_2$SO$_4$ and concentrated under vacuum to give the crude compound, which was purified by 250 g silica gel column chromatography using EtOAc/n-hexane (10:90%) as eluent to afford 4-(2,6-dibenzyloxy-3-pyridyl)-7-nitro-2,3-dihydro-1,4-benzoxazine 23-6 (2.00 g, 3.54 mmol, 33.06% yield) as a yellow sticky solid. LCMS (ES$^+$): m/z 470 [M+H]$^+$.

Step-4:

To a 100 mL single neck round bottom flask containing a well stirred solution of 4-(2,6-dibenzyloxy-3-pyridyl)-7-nitro-2,3-dihydro-1,4-benzoxazine 23-6 (2.40 g, 4.26 mmol) in THF (15 mL) and water (15 mL) was added zinc (5.57 g, 85.20 mmol) at room temperature. The reaction mixture was cooled to 0° C. before ammonium chloride (4.56 g, 85.20 mmol, 2.98 mL) was added. The reaction mixture was warmed to room temperature and stirred for 15 h. After completion of reaction, the reaction mixture was filtered through a pad of celite. The solvent was then removed under reduced pressure and the crude was purified by silica gel (230-400 mesh) column chromatography using 20-35% EtOAc/petroleum ether as eluent to afford 4-(2,6-dibenzyloxy-3-pyridyl)-2,3-dihydro-1,4-benzoxazin-7-amine 23-7 (830 mg, 1.66 mmol, 39.01% yield). LCMS (ES$^+$): m/z 440.2 [M+H]$^+$.

Step-1:

To a 50 mL sealed tube containing a stirred solution of 2-bromo-5-nitro-phenol 23-1 (2.00 g, 9.17 mmol) in dry DMF (8 mL) were added potassium carbonate (2.54 g, 18.35 mmol) and 2-bromo-1,1-diethoxy-ethane 23-2 (2.71 g, 13.76 mmol). The reaction mixture was stirred at 100° C. for 16 h. After consumption of starting material, the reaction mixture was diluted with water (50 mL) and extracted with EtOAc (2×50 mL). The combined organic layers were washed with brine (10 mL), dried over Na$_2$SO$_4$, filtered and concentrated under reduced pressure to get the crude prod- Step-5:

To a 50 mL single neck round bottom flask containing a stirred solution of 4-(2,6-dibenzyloxy-3-pyridyl)-2,3-dihydro-1,4-benzoxazin-7-amine 23-7 (400 mg, 910.12 mol) in ethanol (4 mL), DCE (4 mL), acetic acid (163.96 mg, 2.73 mmol, 156.15 µL), tert-butyl 3-oxoazetidine-1-carboxylate 23-8 (233.71 mg, 1.37 mmol) were added and stirred for 1 hour. Then MP-Cyanoborohydride (800 mg, 6.83 mmol) was added. The reaction mixture was stirred at room temperature for 16 hours. After consumption of the starting material, the reaction mixture was filtered and washed with ethyl acetate (25 ml). The reaction mixture was concentrated under reduced pressure to get the crude product which was purified by column chromatography (50 g, 60-120 mesh silica gel) using 20-40% ethyl acetate/petroleum ether as eluent to afford tert-butyl 3-[[4-(2,6-dibenzyloxy-3-pyridyl)-2,3-dihydro-1,4-benzoxazin-7-yl]amino]azetidine-1-carboxylate 23-9 (200 mg, 326.85 mol, 35.91% yield) as a yellow solid. LCMS (ES$^+$): m/z 595 [M+H]$^+$.

Step-6:

To a 50 mL single neck round bottom flask containing a well stirred solution of tert-butyl 3-[[4-(2,6-dibenzyloxy-3-pyridyl)-2,3-dihydro-1,4-benzoxazin-7-yl]amino]azetidine-1-carboxylate 23-9 (200 mg, 326.79 mol) in 1,4-dioxane (3 mL) was added palladium hydroxide on carbon, 20 wt. % 50% water (388.68 mg, 2.77 mmol) under nitrogen atmosphere. The reaction mixture was stirred at room temperature for 24 h using H$_2$ balloon. After consumption of starting material, the reaction mixture was filtered through a celite pad, which was washed with ethyl acetate (100 mL). The combined organic layers were concentrated to obtain the crude product, which was purified by column chromatography (25 g neutral alumina) and using 2% methanol in DCM as an eluent to afford tert-butyl 3-[[4-(2,6-dioxo-3-piperidyl)-2,3-dihydro-1,4-benzoxazin-7-yl]amino]azetidine-1-carboxylate 23-10 (106 mg, 246.50 mol, 75.43% yield) as an off-white solid. LCMS (ES$^+$): m/z 416 [M+H]$^+$.

Scheme 24: Synthesis of 2-[4-[4-[(3S)-2,6-dioxo-3-piperidyl]-2,3-dihydro-1,4-benzoxazin-8-yl]-1-piperidyl]acetic acid and 2-[4-[4-[(3R)-2,6-dioxo-3-piperidyl]-2,3-dihydro-1,4-benzoxazin-8-yl]-1-piperidyl]acetic acid

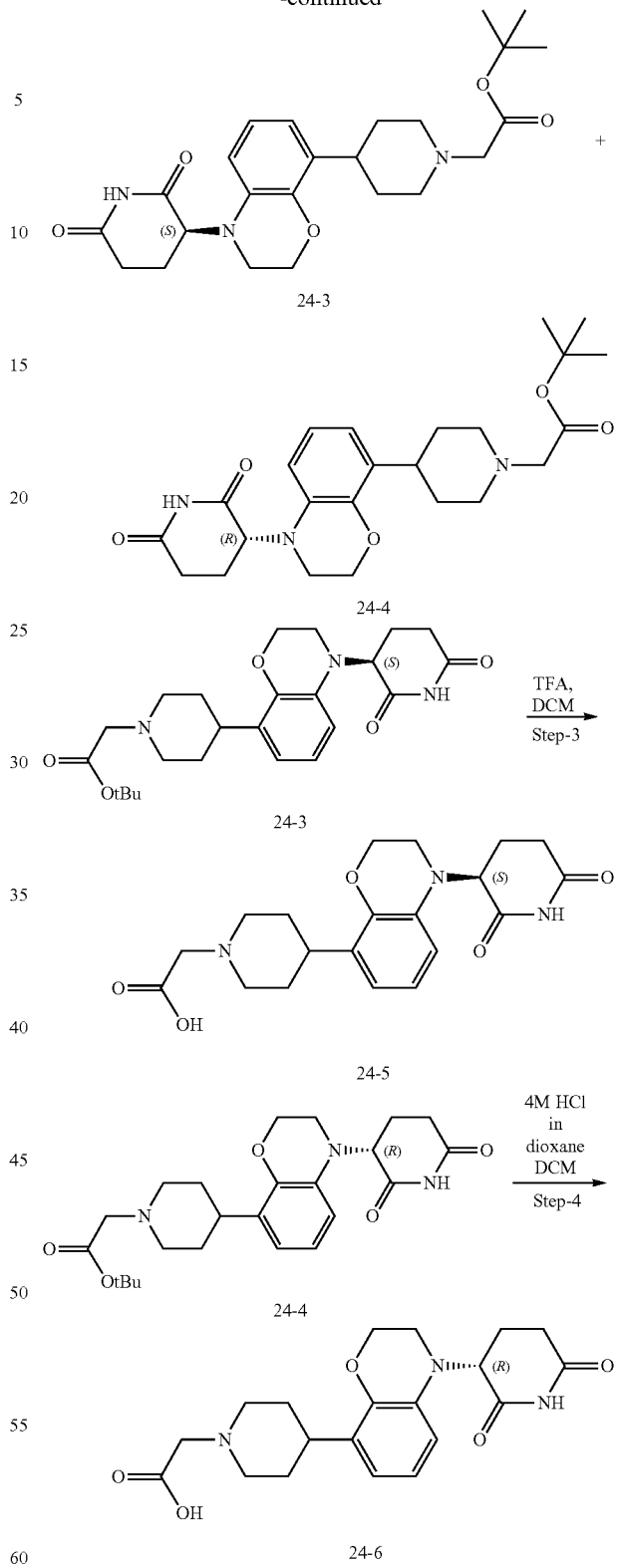

Step-1:

To a stirred solution of 3-[8-(4-piperidyl)-2,3-dihydro-1,4-benzoxazin-4-yl]piperidine-2,6-dione 9-11 (6 g, 13.53 mmol, TFA salt) in ACN (180 mL) was added N,N-diisopropyl ethylamine (3.50 g, 27.06 mmol, 4.71 mL) at 0° C.

After 10 minutes, t-butyl-2-bromoacetate 24-1 (791.80 mg, 4.06 mmol, 595.34 μL) was added at 0° C. The reaction mixture was stirred at room temperature for 24 h. After completion of the reaction, solvents were evaporated under vacuum. The crude product thus obtained was purified by column chromatography (0-5% methanol in DCM, Davisil silica) to afford tert-butyl 2-[4-[4-(2,6-dioxo-3-piperidyl)-2,3-dihydro-1,4-benzoxazin-8-yl]-1-piperidyl]acetate 24-2 (2.8 g, 6.31 mmol, 46.65%) as a light brown solid. LCMS (ES+): m/z 444.53 [M+H]+.

Step-2:

Racemic compound 24-2 (3 g) was separated by SFC to give compound 24-3 (Early eluting peak arbitrarily assigned as S-isomer, 1.02 g) and compound 24-4 (Late eluting peak arbitrarily assigned as R-isomer, 1.34 g).

Preparative SFC conditions: column/dimensions: CHIRALCEL-OD-H (30×250) mm, 5μ; % CO$_2$: 50%; % co-solvent: 50% (ACN); Total Flow: 100 g/min; Back Pressure: 100 bar; Temperature: 30° C.; UV: 215 nm; Solubility: ACN.

Step-3:

To a stirred solution of tert-butyl 2-[4-[4-[(3S)-2,6-dioxo-3-piperidyl]-2,3-dihydro-1,4-benzoxazin-8-yl]-1-piperidyl] acetate 24-3 (2.2 g, 4.96 mmol) in DCM (20 mL) was added trifluoracetic acid (6.79 g, 59.52 mmol, 4.59 mL) at 0° C. under N$_2$ atmosphere. The reaction mixture was stirred at room temperature for 12 h. Upon completion, the crude reaction mixture was evaporated under vacuum to afford the residue, which was washed with diethyl ether (50 mL) to afford 2-[4-[4-[(3S)-2,6-dioxo-3-piperidyl]-2,3-dihydro-1,4-benzoxazin-8-yl]-1-piperidyl]acetic acid 24-5 (2.4 g, 4.35 mmol, 87.62% yield, TFA salt) as an off-white solid. LCMS (ES+): m/z 387.43 [M+H]+.

Step-4:

To a stirred solution of tert-butyl 2-[4-[4-[(3R)-2,6-dioxo-3-piperidyl]-2,3-dihydro-1,4-benzoxazin-8-yl]-1-piperidyl] acetate 24-4 (35.00 mg, 78.91 mol) in DCM (2 mL) at room temperature was added HCl in dioxane (4 M, 197.28 L). The resulting reaction mixture was stirred at 26° C. for 2 hr. The reaction mixture was concentrated under reduced pressure to give 2-[4-[4-[(3R)-2,6-dioxo-3-piperidyl]-2,3-dihydro-1,4-benzoxazin-8-yl]-1-piperidyl]acetic acid 24-6 (35 mg, 73.46 mol, 93.09% yield, HCl salt) as yellow solid. LCMS (ES+): m/z 388.1 [M+H]+.

Scheme 25: Synthesis of 2-[4-[4-(2,6-dioxo-3-piperidyl)-7-fluoro-2,3-dihydro-1,4-benzoxazin-8-yl]-1-piperidyl]acetic acid

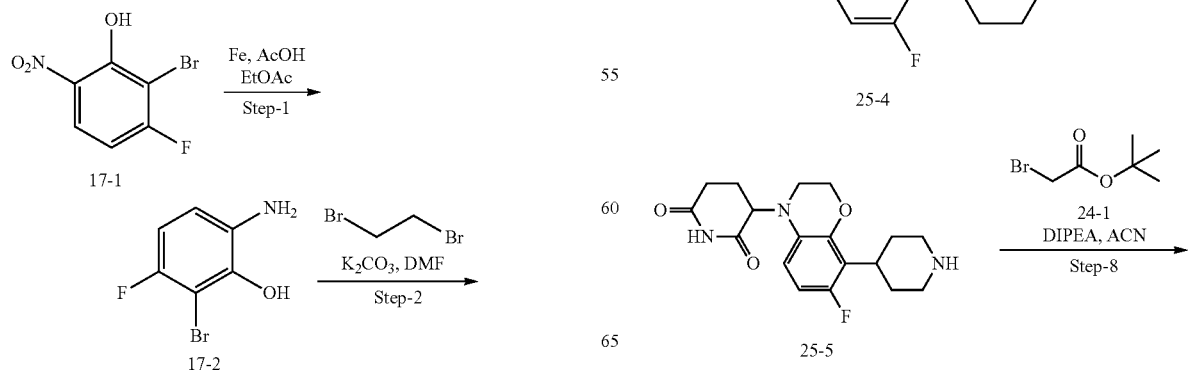

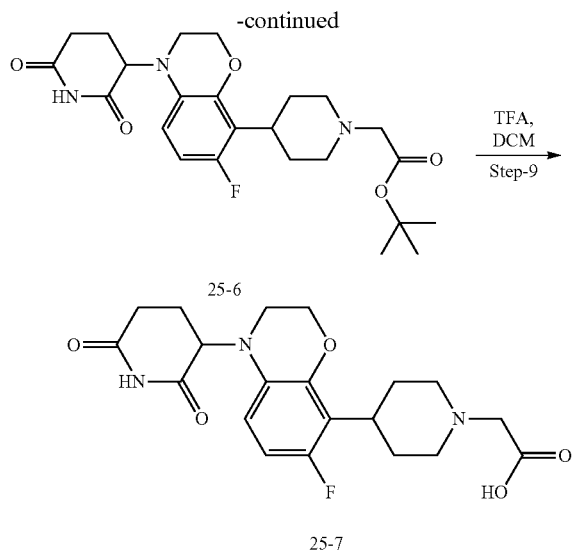

Step-1:

To a stirred solution of 2-bromo-3-fluoro-6-nitro-phenol 17-1 (10 g, 42.37 mmol) in ethyl acetate (50 mL) was added glacial acetic acid (100 g, 360.82 mmol, 100 mL) and reaction mixture was cooled to 0° C. Followed by addition of iron (18.93 g, 339 mmol) in reaction mixture at 0° C., the reaction mixture was allowed to react at 28° C. for 3 hr. Upon completion of reaction, the reaction mixture filtered through celite bed and washed with ethyl acetate, filtrate was extracted by EtOAc, and concentrated to get crude material. The crude material was triturated with diethyl ether to afford 6-amino-2-bromo-3-fluoro-phenol 17-2 (7 g, 33.98 mmol, 80.19% yield) as a black colored solid. LCMS (ES$^+$): m/z 208.04 [M+H]$^+$.

Step-2:

To a stirred solution of 6-amino-2-bromo-3-fluoro-phenol 17-2 (7 g, 33.98 mmol) in DMF (50 mL) was added anhydrous potassium carbonate, 99% (14.09 g, 101.94 mmol, 6.15 mL) and reaction mixture stirred for 10 min. Then 1,2-dibromoethane (7.02 g, 37.38 mmol, 3.22 mL) was added to the reaction mixture and the reaction mixture was heated at 125° C. for 16 hr. Upon completion of reaction, the reaction mixture was diluted with water and extracted by EtOAc, organic layer was concentrated under reduced pressure to obtain a crude material. The crude material was purified by column chromatography using Davisil silica and 0-30% EtOAc in petroleum ether as an eluent to afford 8-bromo-7-fluoro-3,4-dihydro-2H-1,4-benzoxazine 17-3 (4 g, 11.55 mmol, 33.99% yield) as a brown colored liquid. LCMS (ES$^+$): m/z 233.92 [M+H]$^+$.

Step-3:

A stirred solution of 8-bromo-7-fluoro-3,4-dihydro-2H-1,4-benzoxazine 17-3 (2.7 g, 11.64 mmol) and tert-butyl 4-(4,4,5,5-tetramethyl-1,3,2-dioxaborolan-2-yl)-3,6-dihydro-2H-pyridine-1-carboxylate 9-2 (3.60 g, 11.64 mmol) in dioxane (30 mL) and water (5 mL) was purged with argon for 10 min. Cyclopentyl(diphenyl)phosphane dichloropalladium iron (425.69 mg, 581.77 mol) was added to the reaction mixture and it was heated at 100° C. for 1 hr. Upon completion of reaction, the reaction mixture was filtered through a celite bed and washed with EtOAc, organic layer was washed with water and brine; organic layer was dried over anhydrous Na$_2$SO$_4$, filtered and concentrated to give a crude material. The crude material was purified by column chromatography using Davisil silica and 0-30% EtOAc in petroleum ether as eluent to afford tert-butyl 4-(7-fluoro-3,4-dihydro-2H-1,4-benzoxazin-8-yl)-3,6-dihydro-2H-pyridine-1-carboxylate 25-1 (1.8 g, 4.52 mmol, 38.86% yield) as an off-white solid. LCMS (ES$^+$): m/z 335.17 [M+H]$^+$.

Step-4:

A stirred solution of tert-butyl 4-(7-fluoro-3,4-dihydro-2H-1,4-benzoxazin-8-yl)-3,6-dihydro-2H-pyridine-1-carboxylate 25-1 (1.79 g, 5.35 mmol) in methanol (20 mL) was purged with nitrogen for 5 min. Palladium, 10% on carbon, type 487, dry (1.6 g, 15.03 mmol) was added to the reaction mixture, and the reaction mixture was stirred under H$_2$ at 28° C. for 16 hr. Upon completion of reaction, it was filtered through a celite bed, washed with EtOH and EtOAc. The filtrate was evaporated under reduced pressure to get tert-butyl 4-(7-fluoro-3,4-dihydro-2H-1,4-benzoxazin-8-yl)piperidine-1-carboxylate 25-2 (1.6 g, 3.66 mmol, 68.44% yield) as a white solid. LCMS (ES$^+$): m/z 337.17 [M+H]$^+$.

Step-5:

To a solution of tert-butyl 4-(7-fluoro-3,4-dihydro-2H-1,4-benzoxazin-8-yl)piperidine-1-carboxylate 25-2 (1.4 g, 4.16 mmol) and 2,4-dibenzyloxy-1-bromo-benzene 5-7 (1.54 g, 4.16 mmol) in toluene (5 mL) was added sodium tert-butoxide (1.20 g, 12.49 mmol) at room temperature. The reaction mixture was degassed with N$_2$ for 10 min and then (5-diphenylphosphanyl-9,9-dimethyl-xanthen-4-yl)-diphenyl-phosphane (481.61 mg, 832.34 mol) and (1E,4E)-1,5-diphenylpenta-1,4-dien-3-one palladium (190.55 mg, 208.09 mol) was added to the reaction mixture and the reaction mixture was degassed with N$_2$ for 5 min. Then reaction mixture was stirred for 16 h at 110° C. After completion of the reaction, the reaction mixture was filtered through celite bed and washed with ethyl acetate. The combined organic layer was dried over Na$_2$SO$_4$, filtered and concentrated under reduced pressure to get the crude material, which was purified by column chromatography using Davisil silica and 0-100% EtOAc in petroleum ether as an eluent to afford tert-butyl 4-[4-(2,6-dibenzyloxy-3-pyridyl)-7-fluoro-2,3-dihydro-1,4-benzoxazin-8-yl]piperidine-1-carboxylate 25-3 (1 g, 1.60 mmol, 38.40% yield) as an off white solid. LCMS (ES$^-$): m/z 624.67 [M–H]$^-$.

Step-6:

A stirred solution of tert-butyl 4-[4-(2,6-dibenzyloxy-3-pyridyl)-7-fluoro-2,3-dihydro-1,4-benzoxazin-8-yl]piperidine-1-carboxylate 25-3 (1 g, 1.60 mmol) in ethyl acetate (10 mL) and EtOH (10 mL) was degassed with nitrogen for 10 min, followed by addition of palladium, 10% on carbon, type 487, dry (1.00 g, 9.40 mmol). The reaction was stirred under H$_2$ atmosphere (balloon) for 16 hrs at room temperature. Upon completion of reaction, the reaction mixture was filtered through celite bed and washed with ethyl acetate. The filtrate was concentrated to afford tert-butyl 4-[4-(2,6-dioxo-3-piperidyl)-7-fluoro-2,3-dihydro-1,4-benzoxazin-8-yl]piperidine-1-carboxylate 25-4 (0.3 g, 469.28 mol, 29.36% yield) as a green colored solid. LCMS (ES$^+$): m/z 448.2 [M+H]$^+$.

Step-7:

A stirred solution of tert-butyl 4-[4-(2,6-dioxo-3-piperidyl)-7-fluoro-2,3-dihydro-1,4-benzoxazin-8-yl]piperidine-1-carboxylate 25-4 (0.3 g, 670.39 mol) in DCM (5 mL) was prepared. Then, trifluoroacetic acid, 99% (764.40 mg, 6.70 mmol, 516.49 µL) was added to reaction mixture at 0° C. Upon completion of reaction, reaction mixture was concentrated and triturated with diethyl ether to afford 3-[7-fluoro-8-(4-piperidyl)-2,3-dihydro-1,4-benzoxazin-4- yl]piperidine-2,6-dione 25-5 (0.250 g, 384.69 mol, 57.38% yield, TFA salt) as a brown solid. LCMS (ES+): m/z 348.43 [M+H]+.

Step-8:

The reaction was performed in a sealed tube. To a stirred solution of 3-[7-fluoro-8-(4-piperidyl)-2,3-dihydro-1,4-benzoxazin-4-yl]piperidine-2,6-dione 25-5 (0.250 g, 541.82 mol, TFA salt) in ACN (10 mL) was added N-ethyl-N-isopropyl-propan-2-amine (350.13 mg, 2.71 mmol, 471.88 µL), pH was checked to be equal -8, and after that tert-butyl 2-bromoacetate 24-1 (105.68 mg, 541.82 mol, 79.46 µL) was added. The reaction mixture was put in pre-heated oil bath at 70° C. for 1 h. Then, the reaction mixture was directly evaporated under reduced pressure, then purified by column chromatography using Davisil silica and 0 to 10% MeOH in DCM to give tert-butyl 2-[4-[4-(2,6-dioxo-3-piperidyl)-7-fluoro-2,3-dihydro-1,4-benzoxazin-8-yl]-1-piperidyl]acetate 25-6 (0.130 g, 256.32 mol, 47.31% yield). LCMS (ES+): m/z 462.22 [M+H]+.

Step-9:

To a stirred solution of tert-butyl 2-[4-[4-(2,6-dioxo-3-piperidyl)-7-fluoro-2,3-dihydro-1,4-benzoxazin-8-yl]-1-piperidyl]acetate 25-6 (0.130 g, 281.67 mol) in DCM (5 mL) was added trifluoroacetic acid (385.41 mg, 3.38 mmol, 260.41 µL) and reaction mixture was stirred at 28° C. for 16 hr. Upon completion of reaction, the reaction mixture was concentrated under reduced pressure and triturated with diethyl ether to afford 2-[4-[4-(2,6-dioxo-3-piperidyl)-7-fluoro-2,3-dihydro-1,4-benzoxazin-8-yl]-1-piperidyl]acetic acid 25-7 (0.120 g, 204.94 mol, 72.76% yield, TFA salt) as a brown solid. LCMS (ES+): m/z 406.13 [M+H]+.

Scheme 26: Synthesis of 2-[1-[4-(2,6-dioxo-3-piperidyl)-2,3-dihydro-1,4-benzoxazin-8-yl]-4-piperidyl]acetic acid

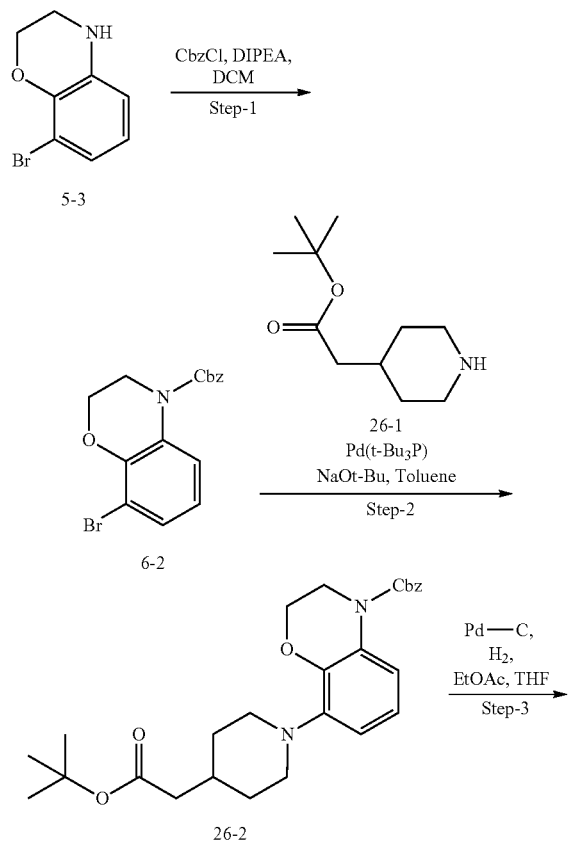

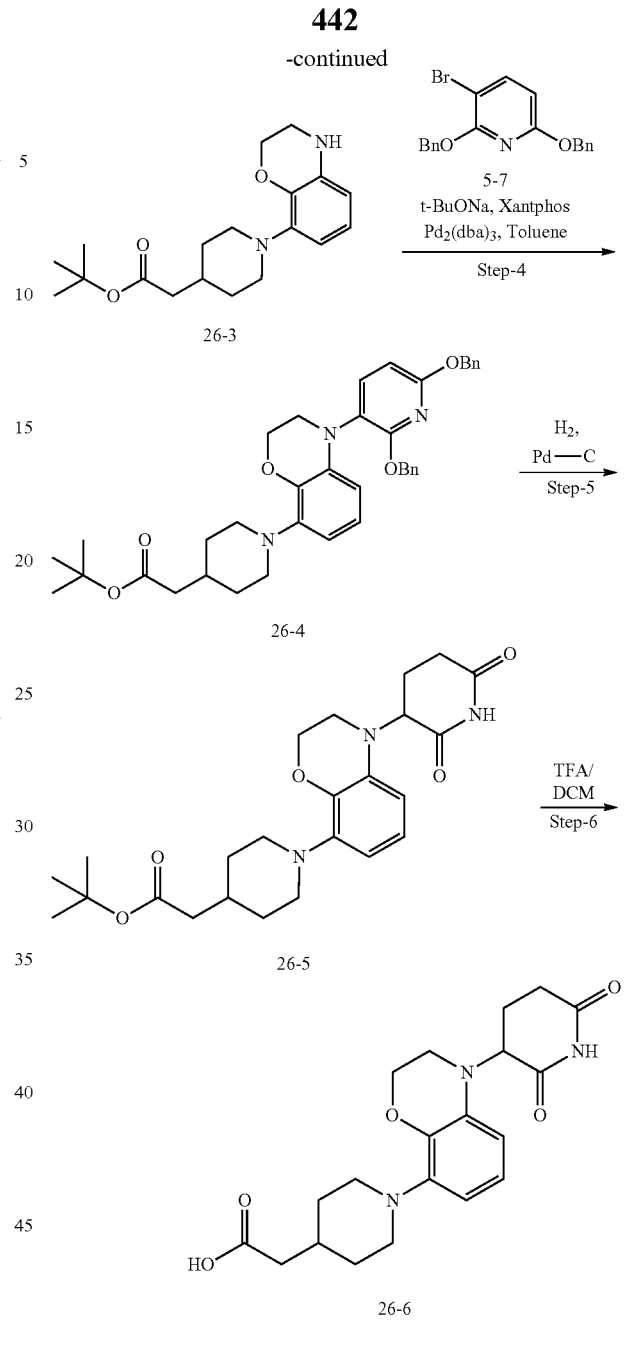

Step-1:

To a stirred solution of 8-bromo-3,4-dihydro-2H-1,4-benzoxazine 5-3 (15 g, 70.07 mmol) in DCM (150 mL), was added N,N-diisopropylethylamine (18.11 g, 140.15 mmol, 24.41 mL) at 0° C. To this solution, benzyl chloroformate (13.15 g, 77.08 mmol, 10.96 mL) was added. The reaction mixture stirred at room temperature for 16 h. Upon completion, the reaction mixture was extracted with dichloromethane. The organic layer was washed with brine, dried over with sodium sulphate and concentrated. The crude product thus obtained was purified by column chromatography (using Devisal silica, 0-20% ethyl acetate in petroleum ether) to afford benzyl 8-bromo-2,3-dihydro-1,4-benzoxazine-4-carboxylate 6-2 (20 g, 57.44 mmol, 81.97% yield) as an orange gum. LCMS (ES+). m/z 348.00 [M+H]+.

Step-2:

To a stirred solution of benzyl 8-bromo-2,3-dihydro-1,4-benzoxazine-4-carboxylate 6-2 (2.5 g, 7.18 mmol) and tert-butyl 2-(4-piperidyl)acetate 26-1 (2.03 g, 8.62 mmol, HCl salt) in toluene (50 mL) was added sodium tert-butoxide (2.07 g, 21.54 mmol) at room temperature. The reaction mixture was purged with argon gas for 10 min and bis(tri-tert-butyl phosphine)palladium(0) (36.69 mg, 71.80 mol) was added at room temperature with continues purging. The reaction mixture was stirred at 110° C. for 3 h. After completion of the reaction, it was concentrated and diluted with ethyl acetate and water. The organic layer was dried over sodium sulphate and concentrated. The crude product thus obtained was purified by column chromatography to afford benzyl 8-[4-(2-tert-butoxy-2-oxo-ethyl)-1-piperidyl]-2,3-dihydro-1,4-benzoxazine-4-carboxylate 26-2 (1 g, 2.10 mmol, 29.31% yield) as pale grey solid. LCMS (ES$^+$): m/z 468.09 [M+H]$^+$.

Step-3:

A stirred solution of benzyl 8-[4-(2-tert-butoxy-2-oxo-ethyl)-1-piperidyl]-2,3-dihydro-1,4-benzoxazine-4-carboxylate 26-2 (1.0 g, 2.14 mmol) in THF (20 mL) and ethyl acetate (20 mL) was degassed with nitrogen gas for 5 minutes. Subsequently, palladium, 10% on carbon, type 487, wet (1.0 g, 2.14 mmol) was added. The reaction mixture was degassed with nitrogen gas for additional 5 minutes. The reaction mixture was stirred under hydrogen atmosphere (using a balloon) at room temperature for 16 h. After completion of the reaction, it was filtered through celite pad and washed with ethyl acetate and concentrated. The crude product thus obtained was purified by column chromatography to afford tert-butyl 2-[1-(3, 4-dihydro-2H-1, 4-benzoxazin-8-yl)-4-piperidyl]acetate 26-3 (0.7 g, 2.11 mmol, 98.24% yield) as an off-white solid. The product formation was confirmed by LCMS. LCMS (ES$^+$): m/z 333.44 [M+H]$^+$.

Step-4:

To a solution of tert-butyl 2-[1-(3,4-dihydro-2H-1,4-benzoxazin-8-yl)-4-piperidyl]acetate 26-3 (600 mg, 1.80 mmol) and 2,6-dibenzyloxy-3-bromo-pyridine 5-7 (801.88 mg, 2.17 mmol) in toluene (12 mL), was added sodium tert-butoxide (520.36 mg, 5.41 mmol) at room temperature. The reaction mixture was degassed with N$_2$ gas for 10 min and tris(dibenzylideneacetone) di-palladium (0) (82.64 mg, 90.24 mol) and Xantphos (73.10 mg, 126.34 mol) were added. The reaction mixture was degassed with nitrogen gas for additional 5 min. It was stirred at 110° C. for 16 h. After completion of the reaction, it was diluted with ethyl acetate and water. The organic layer was separated, dried over with sodium sulphate and concentrated. The crude product thus obtained was purified by column chromatography to afford tert-butyl 2-[1-[4-(2,6-dibenzyloxy-3-pyridyl)-2,3-dihydro-1,4-benzoxazin-8-yl]-4-piperidyl]acetate 26-4 (670 mg, 862.06 mol, 47.76% yield) as dark brown gum. LCMS (ES$^+$): m/z 623.00 [M+H]$^+$.

Step-5:

A solution of tert-butyl 2-[1-[4-(2,6-dibenzyloxy-3-pyridyl)-2,3-dihydro-1,4-benzoxazin-8-yl]-4-piperidyl]acetate 26-4 (670 mg, 1.08 mmol) in ethanol (15 mL) and ethyl acetate (15 mL) was degassed with N$_2$ for 10 min and 10% palladium on carbon (670 mg, 1.08 mmol) was added. The reaction mixture was purged with H$_2$ gas for 5 min and it was stirred for 16 h at room temperature under hydrogen atmosphere (70 psi) in a Parr shaker reactor. After completion of the reaction, it was filtered over celite bed and washed with 10% methanol in DCM. The volatiles were removed under reduced pressure to get the crude product, which was purified by column chromatography over Davisil silica, using 50% EtOAc in petroleum ether as eluent to afford tert-butyl 2-[1-[4-(2,6-dioxo-3-piperidyl)-2,3-dihydro-1,4-benzoxazin-8-yl]-4-piperidyl]acetate 26-5 (255 mg, 539.28 mol, 50.05% yield) as a grey solid.

Step-6:

To a stirred solution of tert-butyl 2-[1-[4-(2,6-dioxo-3-piperidyl)-2,3-dihydro-1,4-benzoxazin-8-yl]-4-piperidyl] acetate 26-5 (75 mg, 169.10 mol) in DCM (3 mL), was added trifluoroacetic acid (289.21 mg, 2.54 mmol, 195.41 µL) at 0° C. under N$_2$ atmosphere. The reaction mixture was stirred at room temperature for 12 h. Upon completion, the crude reaction mixture was concentrated under vacuum and the residue was washed with diethyl ether (10 mL) to afford the 2-[1-[4-(2,6-dioxo-3-piperidyl)-2,3-dihydro-1,4-benzoxazin-8-yl]-4-piperidyl]acetic acid 26-6 (80 mg, 139.34 mol, 82.40% yield, TFA salt) as a dark green gum. LCMS (ES$^+$): m/z 388.73 [M+H]$^+$.

Scheme 27: Synthesis of 1-[4-(2,6-dioxo-3-piperidyl)--2,3-dihydro-1,4-benzoxazin-8-yl]-4-hydroxy-piperidine--4-carboxylic acid

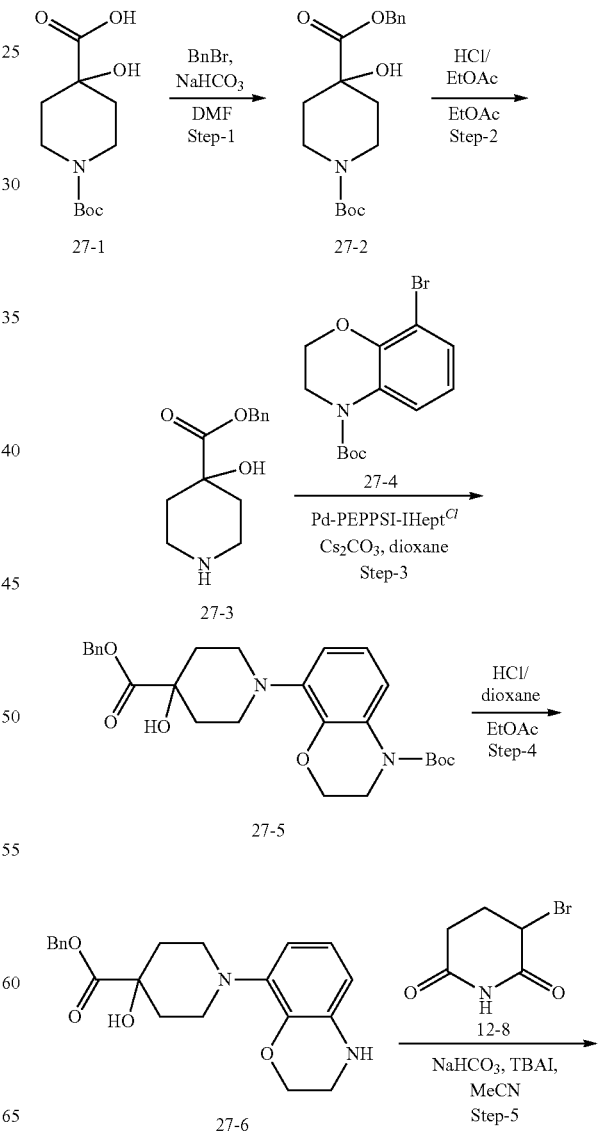

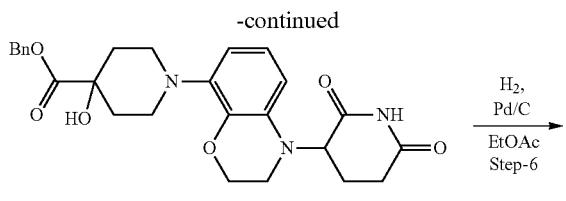

27-7

H₂,
Pd/C
─────→
EtOAc
Step-6

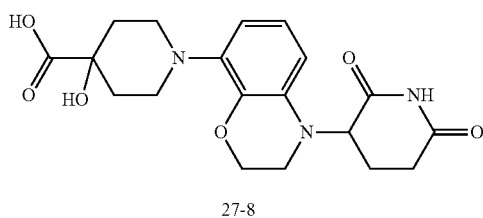 [SMILES: O=C1CCC(N2CCOc3c(N4CCC(O)(C(=O)O)CC4)cccc32)C(=O)N1]

27-8

Step 1:

To a solution of 1-(tert-butoxycarbonyl)-4-hydroxypiperidine-4-carboxylic acid 27-1 (1 g, 4.08 mmol) in DMF (10 mL) was added BnBr (1.05 g, 6.12 mmol, 727.39 μL) and NaHCO₃ (411.02 mg, 4.89 mmol) at 0° C., then the mixture was stirred at 20° C. for 12 hr. The reaction mixture was diluted with H₂O (50 mL) and extracted with MTBE (30 mL×3). The combined organic layers were washed with brine (50 mL×3), dried over anhydrous Na₂SO₄, filtered and concentrated under reduced pressure. The residue was purified by column chromatography (SiO₂, petroleum ether/ethyl acetate=5/1 to 3/1) to give 4-benzyl 1-tert-butyl 4-hydroxypiperidine-1,4-dicarboxylate 27-2 (1.39 g, 4.06 mmol, 99.62% yield). LCMS (ES⁺): m/z 236.1 [M−Boc+H]⁺.

Step 2:

To a solution of 4-benzyl 1-tert-butyl 4-hydroxypiperidine-1,4-dicarboxylate 27-2 (500 mg, 1.49 mmol) in EtOAc (5 mL) was added HCl/EtOAc (4 M, 5 mL). The mixture was stirred at 20° C. for 1 hr. The reaction mixture was concentrated under reduced pressure to give benzyl 4-hydroxypiperidine-4-carboxylate 27-3 (400 mg, 1.47 mmol, HCl salt).

¹H NMR (400 MHz, DMSO-d₆): δ=9.10-8.68 (m, 2H), 7.57-7.22 (m, 4H), 6.02-5.84 (m, 1H), 5.22-5.09 (m, 2H), 3.18-2.95 (m, 4H), 2.15-1.99 (m, 2H), 1.88-1.71 (m, 2H).

Step 3:

A mixture of benzyl 4-hydroxypiperidine-4-carboxylate 27-3 (920 mg, 3.39 mmol, 021), tert-butyl 8-bromo-2,3-dihydro-1,4-benzoxazine-4-carboxylate 27-4 (957.30 mg, 3.05 mmol), Cs₂CO₃ (3.31 g, 10.16 mmol) and Pd-PEPPSI-IHept^CI (329.34 mg, 338.56 μmol) in dioxane (10 mL) was degassed and purged with N₂ for 3 times, and then the mixture was stirred at 100° C. for 12 hr under N₂ atmosphere. The mixture was poured into water (50 mL) and then extracted with EtOAc (50 mL×3). The combined organic layers were washed with brine (50 mL), dried over anhydrous Na₂SO₄, filtered and concentrated under reduced pressure. The residue was purified by column chromatography (SiO₂, petroleum ether/ethyl acetate=3/1) to give tert-butyl 8-(4-benzyloxycarbonyl-4-hydroxy-1-piperidyl)-2,3-dihydro-1,4-benzoxazine-4-carboxylate 27-5 (310 mg, 654.35 μmol, 19.33% yield). LCMS (ES⁺): m/z 469.0 [M+H]⁺.

Step 4:

To a solution of tert-butyl 8-(4-benzyloxycarbonyl-4-hydroxy-1-piperidyl)-2,3-dihydro-1,4-benzoxazine-4-carboxylate 27-5 (630 mg, 1.34 mmol) in EtOAc (6 mL) was added HCl/dioxane (4 M, 6 mL). The mixture was stirred at 20° C. for 2 hr. The reaction mixture was concentrated under reduced pressure to give benzyl 1-(3,4-dihydro-2H-1,4-benzoxazin-8-yl)-4-hydroxy-piperidine-4-carboxylate 27-6 (493 mg, 1.34 mmol).

Step 5:

To a mixture of benzyl 1-(3,4-dihydro-2H-1,4-benzoxazin-8-yl)-4-hydroxy-piperidine-4-carboxylate 27-6 (493 mg, 1.34 mmol) and 3-bromopiperidine-2,6-dione 12-8 (770.80 mg, 4.01 mmol) in MeCN (2.5 mL) was added NaHCO₃ (449.65 mg, 5.35 mmol, 208.27 μL) and TBAI (49.43 mg, 133.81 μmol), then the mixture was stirred at 100° C. (oil bath) for 5 hr. The solvent was evaporated to dry. The reaction was quenched with water (20 mL) and filtered through celite bed. The filtrate was extracted with EtOAc (10 mL×2). The organic layer was dried over anhydrous Na₂SO₄, filtered and concentrated under reduced pressure. The residue was purified by column chromatography (SiO₂, petroleum ether/ethyl acetate=1/1) to give benzyl 1-(4-(2,6-dioxopiperidin-3-yl)-3,4-dihydro-2H-benzo[b][1,4]oxazin-8-yl)-4-hydroxypiperidine-4-carboxylate 27-7 (340 mg, 687.77 μmol, 51.40% yield). LCMS (ES⁺): m/z 480.1 [M+H]⁺.

Step 6:

A mixture of benzyl 1-[4-(2,6-dioxo-3-piperidyl)-2,3-dihydro-1,4-benzoxazin-8-yl]-4-hydroxy-piperidine-4-carboxylate 27-7 (340 mg, 709.04 μmol) in EtOAc (8 mL) was degassed and purged with N₂, then Pd/C (150 mg, 5%) was added to the mixture. The mixture was degassed and purged with H₂ for 3 times, and then stirred at 25° C. for 12 hrs under H₂ atmosphere (15 psi). The mixture was filtered and the filtrate was concentrated under reduced pressure to give 1-[4-(2,6-dioxo-3-piperidyl)-2,3-dihydro-1,4-benzoxazin-8-yl]-4-hydroxy-piperidine-4-carboxylic acid 27-8 (200 mg, 498.20 μmol, 70.26% yield). LCMS (ES⁺): m/z 389.9 [M+H]⁺.

Scheme 28: Synthesis of 2-(4-(4-(2,6-dioxopiperidin-3-yl)-3,4-dihydro-2H-benzo[b][1,4]oxazin-8-yl)piperazin-1-yl)acetic acid

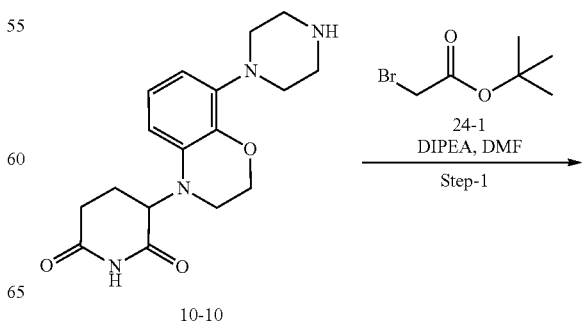

24-1
─────→
DIPEA, DMF
Step-1

10-10

-continued

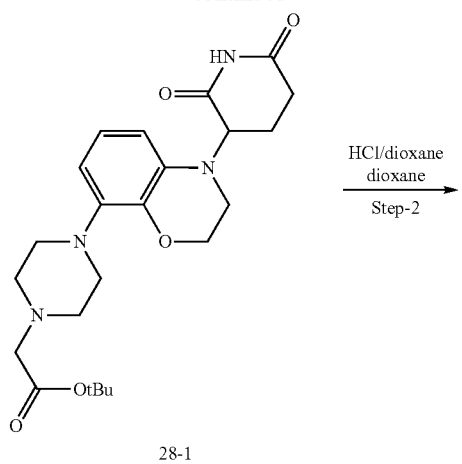

28-1

HCl/dioxane
dioxane
Step-2
→

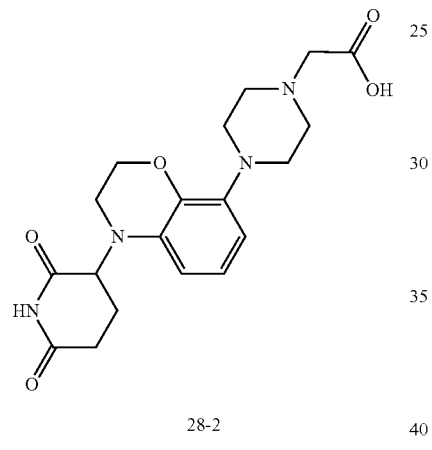

28-2

Scheme 29: Synthesis of 2-(4-(4-(2,6-dioxopiperidin-3-yl)-
3-oxo-3,4-dihydro-2H-benzo[b][1,4]oxazin-8-yl)
piperidin-1-yl)acetic acid

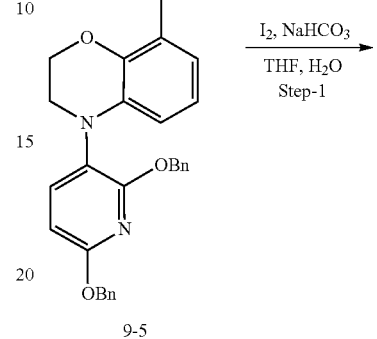

9-5

I₂, NaHCO₃
THF, H₂O
Step-1
→

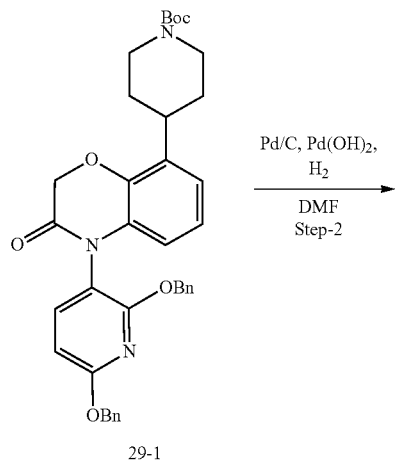

29-1

Pd/C, Pd(OH)₂,
H₂
DMF
Step-2
→

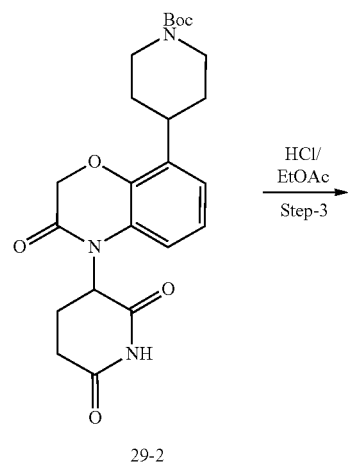

29-2

HCl/
EtOAc
Step-3
→

Step-1:

To a solution of 3-(8-(piperazin-1-yl)-2H-benzo[b][1,4] oxazin-4(3H)-yl)piperidine-2,6-dione 10-10 (1.9 g, 5.18 mmol, HCl salt) in DMF (19 mL) was added N-ethyl-N-isopropyl-propan-2-amine (1.34 g, 10.36 mmol, 1.80 mL) and tert-butyl 2-bromoacetate 24-1 (1.01 g, 5.18 mmol, 759.59 µL). The mixture was stirred at 25° C. for 3 hr. The residue was purified by prep-HPLC (TFA condition to give tert-butyl 2-(4-(4-(2,6-dioxopiperidin-3-yl)-3,4-dihydro-2H-benzo[b][1,4]oxazin-8-yl)piperazin-1-yl)acetate 28-1 (800 mg, 1.78 mmol, 34.40% yield) as a white solid. LCMS (ES⁺): m/z 445.2 [M+H]⁺.

Step-2:

A mixture of tert-butyl 2-(4-(4-(2,6-dioxopiperidin-3-yl)-3,4-dihydro-2H-benzo[b][1,4]oxazin-8-yl)piperazin-1-yl) acetate 28-1 (600 mg, 1.35 mmol) and HCl/dioxane (4 M, 6.00 mL) was stirred at 25° C. for 12 hr. The reaction mixture was concentrated under reduced pressure to give 2-(4-(4-(2,6-dioxopiperidin-3-yl)-3,4-dihydro-2H-benzo[b] [1,4]oxazin-8-yl)piperazin-1-yl)acetic acid 28-2 (510 mg, 1.31 mmol, 97.28% yield). LCMS (ES⁺): m/z 389.3 [M+H]⁺.

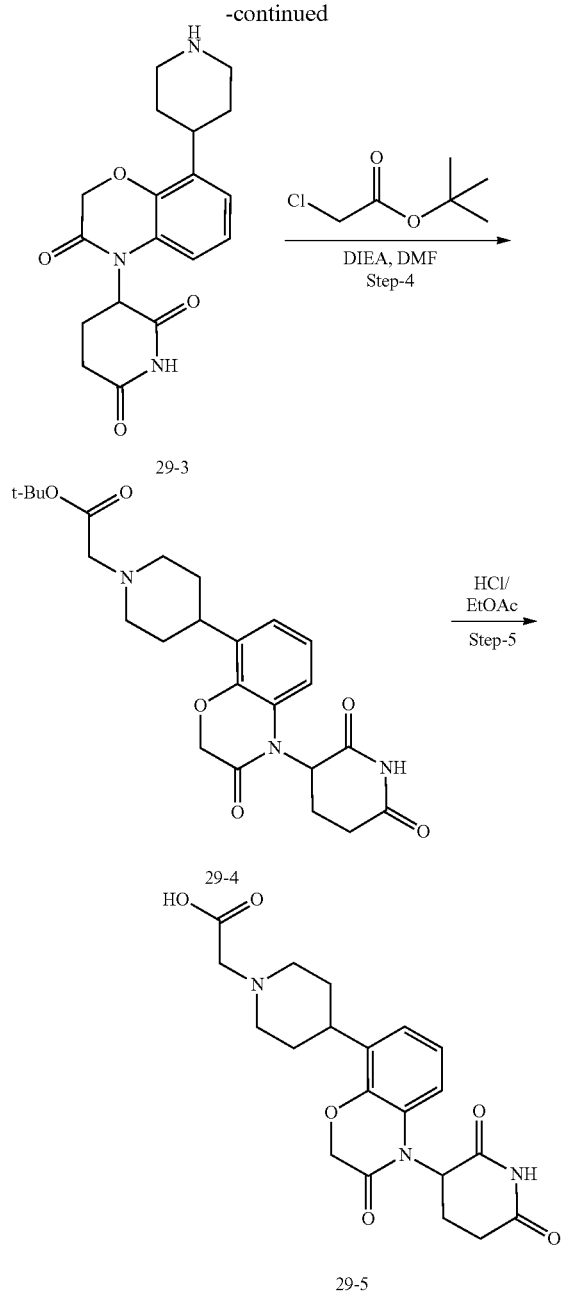

Step-2:

To a mixture of tert-butyl 4-(4-(2,6-bis(benzyloxy)pyridin-3-yl)-3-oxo-3,4-dihydro-2H-benzo[b][1,4]oxazin-8-yl)piperidine-1-carboxylate 29-1 (3.32 g, 5.34 mmol) in DMF (70 mL) was added 10% Pd/C (3.32 g) and 20% Pd(OH)$_2$/C (3.32 g). The suspension was degassed and purged with H$_2$ three times, then the mixture was stirred at 25° C. for 12 h under H$_2$ (50 psi) atmosphere. The reaction mixture was filtered and the filtrate was concentrated under reduced pressure. The residue was purified by flash silica gel chromatography (ISCO®; 4 g SepaFlash® Silica Flash Column, Eluent of 0~53% ethyl acetate/petroleum ether gradient @50 mL/min) to give tert-butyl 4-(4-(2,6-dioxopiperidin-3-yl)-3-oxo-3,4-dihydro-2H-benzo[b][1,4]oxazin-8-yl)piperidine-1-carboxylate 29-2 (2.5 g, 5.64 mmol) as a white solid.

Step-3:

A mixture of tert-butyl 4-(4-(2,6-dioxopiperidin-3-yl)-3-oxo-3,4-dihydro-2H-benzo[b][1,4]oxazin-8-yl)piperidine-1-carboxylate 29-2 (2.5 g, 5.64 mmol) in HCl/EtOAc (5.64 mmol, 30 mL) was stirred at 25° C. for 1 hr. The mixture was concentrated in vacuo to give 3-(3-oxo-8-(piperidin-4-yl)-2H-benzo[b][1,4]oxazin-4(3H)-yl)piperidine-2,6-dione 29-3 (2.24 g, 5.90 mmol, HCl salt) as a yellow solid.

Step-4:

To a mixture of 3-(3-oxo-8-(piperidin-4-yl)-2H-benzo[b][1,4]oxazin-4(3H)-yl)piperidine-2,6-dione 29-3 (2.24 g, 3.80 mmol, HCl salt) in DMF (30 mL) was added DIEA (2.95 g, 22.81 mmol, 3.97 mL) and tert-butyl 2-chloroacetate (629.91 mg, 4.18 mmol, 599.91 L). The mixture was stirred at 50° C. for 2 hr. The mixture was poured into water (80 mL) and extracted with EtOAc (60 mL×3). The combined organic layers were washed with brine (200 mL), dried over anhydrous Na$_2$SO$_4$, filtered and concentrated under reduced pressure to give tert-butyl 2-(4-(4-(2,6-dioxopiperidin-3-yl)-3-oxo-3,4-dihydro-2H-benzo[b][1,4]oxazin-8-yl)piperidin-1-yl)acetate 29-4 (1.4 g, 3.06 mmol, 80.48% yield) as a white solid.

Step-5:

A mixture of tert-butyl 2-(4-(4-(2,6-dioxopiperidin-3-yl)-3-oxo-3,4-dihydro-2H-benzo[b][1,4]oxazin-8-yl)piperidin-1-yl)acetate 29-4 (1.39 g, 3.04 mmol) and HCl/EtOAc (4 M, 30 mL) was stirred at 25° C. for 12 hr. The mixture was concentrated in vacuo. The residue was purified by prep-HPLC (FA condition) to give 2-(4-(4-(2,6-dioxopiperidin-3-yl)-3-oxo-3,4-dihydro-2H-benzo[b][1,4]oxazin-8-yl)piperidin-1-yl)acetic acid 29-5 (1.2 g, 2.67 mmol, 87.77% yield, formic acid salt) as a yellow solid. LCMS (ES$^+$): m/z 402.1 [M+H]$^+$.

Step-1:

To a mixture of tert-butyl 4-[4-(2,4-dibenzyloxyphenyl)-2,3-dihydro-1,4-benzoxazin-8-yl]piperidine-1-carboxylate 9-5 (6 g, 9.87 mmol) and NaHCO$_3$ (6.00 g, 71.42 mmol) in THF (100 mL) and water (50 mL) was added a solution of I$_2$ (15.01 g, 59.14 mmol) in THF (400 mL) dropwise at room temperature. The mixture was stirred at 25° C. for 12 hr. The mixture was poured into Na$_2$S$_2$O$_3$ (100 mL) and extracted with EtOAc (80 mL×3). The combined organic layers were washed with brine (200 mL), dried over anhydrous Na$_2$SO$_4$, filtered and concentrated under reduced pressure. The residue was purified by flash silica gel chromatography (8%~22% EtOAc in petroleum ather) to give tert-butyl 4-(4-(2,6-bis(benzyloxy)pyridin-3-yl)-3-oxo-3,4-dihydro-2H-benzo[b][1,4]oxazin-8-yl)piperidine-1-carboxylate 29-1 (3.32 g, 5.34 mmol, 54.09% yield) as a yellow solid.

Scheme 30: Synthesis of tert-butyl 2-[4-[1-(2,6-dioxo-3-piperidyl)-2,3-dihydropyrido[3,4-b][1,4]oxazin-5-yl]-1-piperidyl]acetate

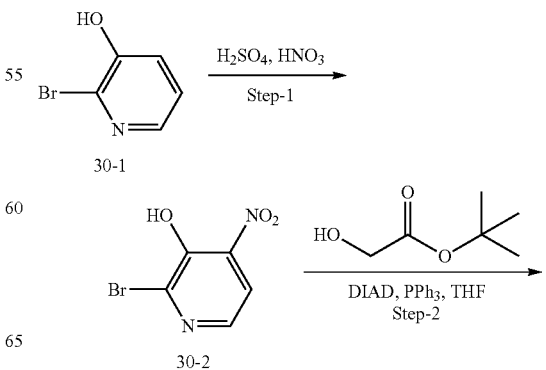

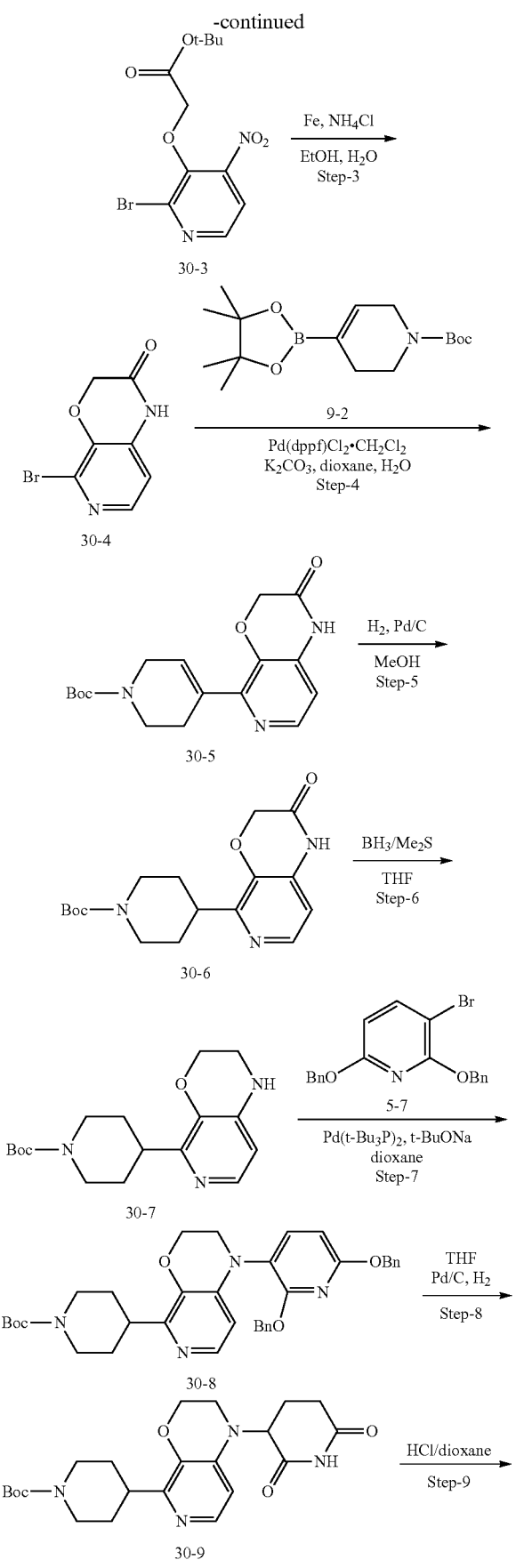
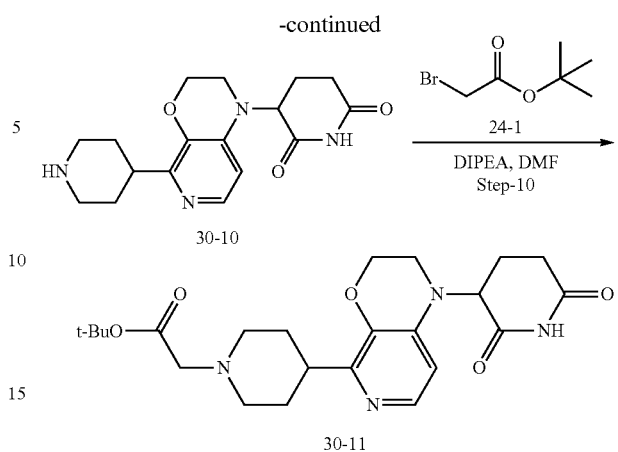

Step-1:

To a mixture of 2-bromopyridin-3-ol 30-1 (20 g, 114.95 mmol) in conc. $H_2SO_4$ (50 mL) was added conc. $HNO_3$ (12.26 g, 126.44 mmol, 8 mL) at 0° C. The mixture was stirred at 25° C. for 12 hr. The reaction mixture was poured into water (1 L) and extracted with EtOAc (500 mL×2). The combined organic layers were washed with brine (500 mL), dried over anhydrous $Na_2SO_4$, filtered and concentrated in vacuo. The residue was purified by column chromatography ($SiO_2$, petroleum ether/EtOAc=100/1 to 20/1) to give 2-bromo-4-nitro-pyridin-3-ol 30-2 (6.5 g, 27.19 mmol, 24% yield) as a yellow solid. LCMS (ES$^+$): m/z 220.9 [M+H]$^+$.

Step-2:

To a mixture of 2-bromo-4-nitro-pyridin-3-ol 30-2 (6.4 g, 29.22 mmol) and tert-butyl 2-hydroxyacetate (4.63 g, 35.07 mmol) in THF (70 mL) was added $PPh_3$ (11.50 g, 43.84 mmol) at 25° C. The mixture was stirred at this temperature for 10 min, and then a mixture of DIAD (8.86 g, 43.84 mmol, 8.61 mL) in THE (10 mL) was added dropwise at 0° C. The resulting mixture was stirred at 50° C. for 2 hr. The reaction mixture was concentrated under reduced pressure. The residue was purified by column chromatography ($SiO_2$, petroleum ether/EtOAc=100/1 to 30/1) to give tert-butyl 2-[(2-bromo-4-nitro-3-pyridyl)oxy]acetate 30-3 (9.5 g, 27.81 mmol, 95% yield) as a yellow solid. LCMS (ES$^+$): m/z 333.9 [M+H]$^+$.

Step-3:

To a mixture of tert-butyl 2-[(2-bromo-4-nitro-3-pyridyl) oxy]acetate 30-3 (9 g, 27.02 mmol) in a mixed solvent of EtOH (90 mL) and water (9 mL) was added Fe (powder, 15.09 g, 270.16 mmol) and $NH_4Cl$ (14.45 g, 270.16 mmol). The mixture was stirred at 80° C. for 2 hr. The reaction mixture was filtered and the filtrate was concentrated under reduced pressure. The residue was diluted with water (500 mL) and extracted with EtOAc (500 mL×2). The combined organic layers were washed with water (500 mL×2), dried over anhydrous $Na_2SO_4$, filtered and concentrated under reduced pressure. The residue was triturated with petroleum ether:EA=5:1 (10 mL) and dried under reduced pressure to give 5-bromo-1H-pyrido[3,4-b][1,4]oxazin-2-one 30-4 (5.1 g, 22.27 mmol, 82% yield) as a off-white solid. LCMS (ES$^+$): m/z 229.0 [M+H]$^+$.

Step-4:

A mixture of 5-bromo-1H-pyrido[3,4-b][1,4]oxazin-2-one 30-4 (5.1 g, 22.27 mmol), tert-butyl 4-(4,4,5,5-tetramethyl-1,3,2-dioxaborolan-2-yl)-3,6-dihydro-2H-pyridine-1-carboxylate 9-2 (8.26 g, 26.72 mmol), Pd(dppf)$Cl_2\cdot CH_2Cl_2$ (3.64 g, 4.45 mmol) and $K_2CO_3$ (9.23 g, 66.80 mmol) in a mixed solvent of dioxane (4 mL) and water (0.4 mL) was degassed and purged with $N_2$ for 3 times, and then the mixture was stirred at 90° C. for 12 hr under $N_2$ atmosphere. The reaction mixture was poured into water (500 mL) and extracted with EtOAc (500 mL×2). The combined organic layers were washed with brine (500 mL), dried over anhydrous $Na_2SO_4$, filtered and concentrated in vacuo. The residue was purified by column chromatography ($SiO_2$, petroleum ether:EtOAc=100:1 to 1:1) to give tert-butyl 4-(2-oxo-1H-pyrido[3,4-b][1,4]oxazin-5-yl)-3,6-dihydro-2H-pyridine-1-carboxylate 30-5 (5.6 g, 16.90 mmol, 76% yield) as a yellow solid. LCMS (ES⁺): m/z 332.2 [M+H]⁺.

Step-5:

To a mixture of tert-butyl 4-(2-oxo-1H-pyrido[3,4-b][1,4]oxazin-5-yl)-3,6-dihydro-2H-pyridine-1-carboxylate 30-5 (5.6 g, 16.90 mmol) in MeOH (100 mL) was added 5 wt. % Pd/C (2.05 g) under $N_2$ atmosphere. The suspension was degassed and purged with $H_2$ for 3 times. The mixture was stirred at 25° C. for 12 hr under $H_2$ (15 psi) atmosphere. The reaction mixture was filtered and the filtrate was concentrated under reduced pressure to give tert-butyl 4-(2-oxo-1H-pyrido[3,4-b][1,4]oxazin-5-yl)piperidine-1-carboxylate 30-6 (5.0 g, 15.00 mmol, 89% yield) as a gray solid. LCMS (ES⁺): m/z 334.1 [M+H]⁺.

Step-6:

To a mixture of tert-butyl 4-(2-oxo-1H-pyrido[3,4-b][1,4]oxazin-5-yl)piperidine-1-carboxylate 30-6 (3 g, 9.00 mmol) in THF (50 mL) was added $BH_3 \cdot SMe_2$ (1.37 g, 18.00 mmol, 1.71 mL) dropwise at 0° C. The mixture was stirred at 60° C. for 12 hr. The reaction mixture was quenched with MeOH (50 mL) at 20° C. Then the mixture was stirred at 60° C. for 12 hr. The reaction mixture was concentrated under reduced pressure. The residue was diluted with water (200 mL) then extracted with EtOAc (250 mL×2). The combined organic layers were washed with brine (250 mL×2), dried over anhydrous $Na_2SO_4$, filtered and concentrated under reduced pressure to give tert-butyl 4-(2,3-dihydro-1H-pyrido[3,4-b][1,4]oxazin-5-yl) piperidine-1-carboxylate 30-7 (3 g, 7.72 mmol, 86% yield) as a yellow solid. LCMS (ES⁺): m/z 320.2 [M+H]⁺.

Step-7:

A mixture of tert-butyl 4-(2,3-dihydro-1H-pyrido[3,4-b][1,4]oxazin-5-yl)piperidine-1-carboxylate 30-7 (2.6 g, 8.14 mmol), 2,6-dibenzyloxy-3-bromo-pyridine 5-7 (3.62 g, 9.77 mmol), Pd(t-bu₃P)₂ (832.02 mg, 1.63 mmol) and t-BuONa (2.35 g, 24.42 mmol) in dioxane (40 mL) was degassed and purged with $N_2$ for 3 times, and then the mixture was stirred at 80° C. for 12 hr under $N_2$ atmosphere. The reaction mixture was filtered and the filter cake was washed with DCM (250 mL×2) then the filtrate was concentrated under reduced pressure. The residue was purified by column chromatography ($SiO_2$, petroleum ether/EtOAc=100/1 to 1/1) to give tert-butyl 4-[1-(2,6-dibenzyloxy-3-pyridyl)-2,3-dihydropyrido[3,4-b][1,4]oxazin-5-yl]piperidine-1-carboxylate 30-8 (3.5 g, 5.72 mmol, 70% yield) as a yellow solid. LCMS (ES⁺): m/z 609.3 [M+H]⁺.

Step-8:

To a mixture of tert-butyl 4-[1-(2,6-dibenzyloxy-3-pyridyl)-2,3-dihydropyrido[3,4-b][1,4]oxazin-5-yl]piperidine-1-carboxylate 30-8 (1.5 g, 2.46 mmol) in THF (20 mL) was added 10 wt. % Pd/C (3.00 g) under $N_2$ atmosphere. The suspension was degassed and purged with $H_2$ for 3 times. The mixture was stirred at 50° C. for 12 hr under $H_2$ (15 psi) atmosphere. The reaction mixture was filtered and the filtrate was concentrated under reduced pressure. The residue was triturated with petroleum ether/EA=3/1 (20 mL) at 25° C. to give tert-butyl 4-[1-(2,6-dioxo-3-piperidyl)-2,3-dihydropyrido[3,4-b][1,4]oxazin-5-yl]piperidine-1-carboxylate 30-9 (760 mg, 1.71 mmol, 69% yield) as a blue solid. LCMS (ES⁺): m/z 431.2 [M+H]⁺.

Step-9:

A mixture of tert-butyl 4-[1-(2,6-dioxo-3-piperidyl)-2,3-dihydropyrido[3,4-b][1,4]oxazin-5-yl]piperidine-1-carboxylate 30-9 (850 mg, 1.97 mmol) in HCl/dioxane (4 M, 20 mL) was stirred at 25° C. for 2 hr. The reaction mixture was concentrated under reduced pressure to give 3-[5-(4-piperidyl)-2,3-dihydropyrido[3,4-b][1,4]oxazin-1-yl]piperidine-2,6-dione 30-10 (700 mg, 1.89 mmol, 96% yield, HCl salt) as a gray solid. LCMS (ES⁺): m/z 331.2 [M+H]⁺.

Step-10:

To a mixture of 3-[5-(4-piperidyl)-2,3-dihydropyrido[3,4-b][1,4]oxazin-1-yl]piperidine-2,6-dione 30-10 (700 mg, 1.91 mmol, HCl salt) and tert-butyl 2-bromoacetate 24-1 (409.42 mg, 2.10 mmol, 307.83 µL) in DMF (10 mL) was added DIEA (1.23 g, 9.54 mmol, 1.66 mL). The mixture was stirred at 60° C. for 2.5 hr. The reaction mixture was quenched with sat. $NH_4Cl$ (aq., 200 mL) at 20° C., and then extracted with EtOAc (100 mL×2). The combined organic layers were washed with $H_2O$ (100 mL×2), dried over anhydrous $Na_2SO_4$, filtered and concentrated under reduced pressure to give tert-butyl 2-[4-[1-(2,6-dioxo-3-piperidyl)-2,3-dihydropyrido[3,4-b][1,4]oxazin-5-yl]-1-piperidyl]acetate 30-11 (700 mg, 1.54 mmol, 81% yield) as a yellow solid. LCMS (ES⁺): m/z 445.1 [M+H]+

Scheme 31: Synthesis of 2-[4-[4-(2,6-dioxo-3-piperidyl)-2,3-dihydro-1,4-benzothiazin-8-yl]-1-piperidyl]acetic acid

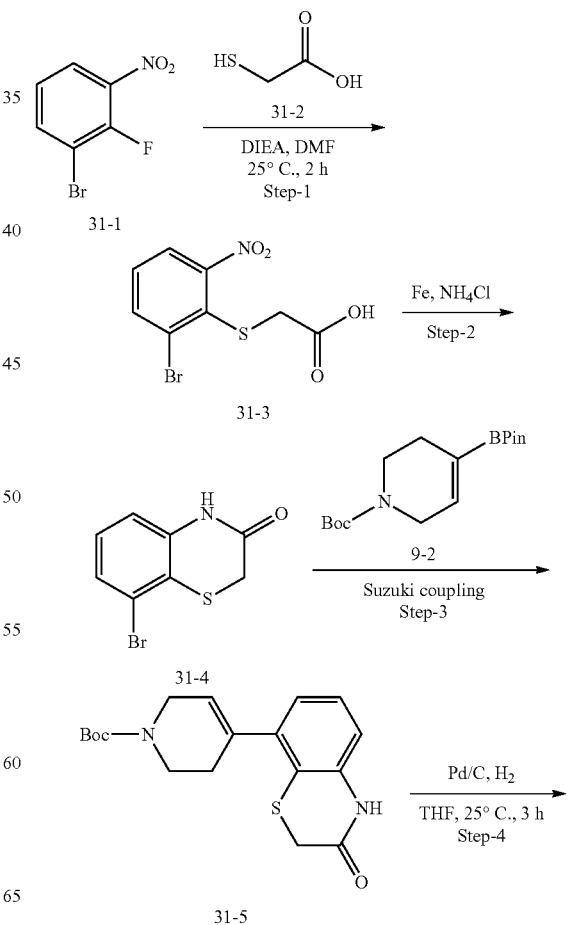

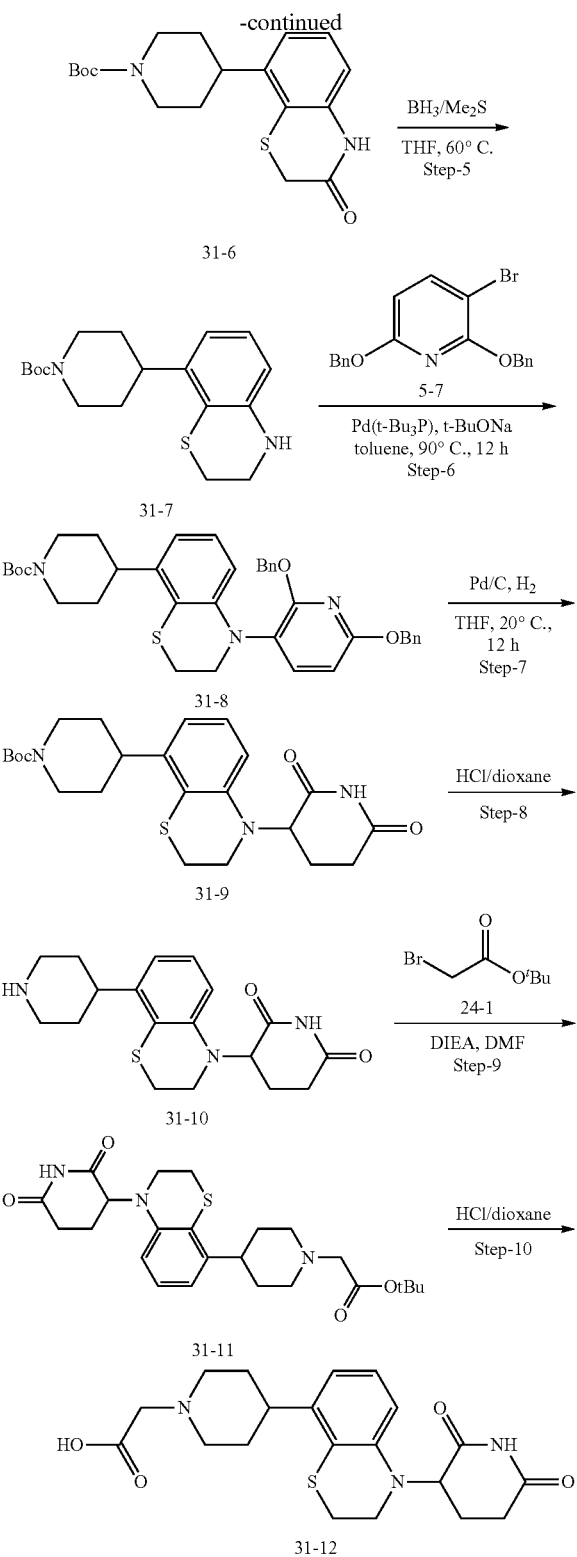

Then the mixture was extracted with ethyl acetate (200 mL×1). The aqueous phase was added HCl (250 ml, 1 M) dropwise until pH=4-5. Then the mixture was extracted with ethyl acetate (200 mL×2). The combined organic layers were washed with brine (150 mL), dried over $Na_2SO_4$, filtered and concentrated to give 2-(2-bromo-6-nitro-phenyl) sulfanylacetic acid 31-3 (15 g, 51.35 mmol, 75.31% yield) as a yellow solid.

Step-2:

To a solution of 2-(2-bromo-6-nitro-phenyl)sulfanylacetic acid 31-3 (5 g, 17.12 mmol) in ethanol (150 mL) and water (15 mL) was added iron powder (4.78 g, 85.59 mmol) and ammonium chloride (9.16 g, 171.17 mmol, 5.98 mL) at 20° C. The mixture was stirred at 60° C. for 12 h. The mixture was filtered to give a black oil, and the filter cake was washed with dichrolomethane (200 mL×4). The combined organics were concentrated to give a brown solid, which was dissolved in ethyl acetate (500 mL). The solution was then washed with water (300 mL×2), dried over anhydrous $Na_2SO_4$, filtered and concentrated to give 8-bromo-4H-1,4-benzothiazin-3-one 31-4 (8.5 g, 34.82 mmol, 67.81% yield) as a white solid.

Step-3:

To a solution of tert-butyl 4-(4,4,5,5-tetramethyl-1,3,2-dioxaborolan-2-yl)-3,6-dihydro-2H-pyridine-1-carboxylate 9-2 (12.16 g, 39.33 mmol) and 8-bromo-4H-1,4-benzothiazin-3-one 31-4 (8 g, 32.77 mmol) in water (16 mL) and dioxane (80 mL) was added $Pd(dppf)Cl_2 \cdot CH_2Cl_2$ (5.35 g, 6.55 mmol) and potassium carbonate (13.59 g, 98.32 mmol, 5.93 mL) at 20° C. under $N_2$ atmosphere. The mixture was stirred at 80° C. for 12 h. The reaction mixture was diluted with water (200 mL) and extracted with ethyl acetate (200 mL×3). The combined organic layers were washed with brine (200 mL), dried over anhydrous $Na_2SO_4$, filtered and concentrated to crude product, which was purified by column chromatography (petroleum ether/ethyl acetate=20/1 to 3/1) to afford tert-butyl 4-(3-oxo-4H-1,4-benzothiazin-8-yl)-3,6-dihydro-2H-pyridine-1-carboxylate 31-5 (10 g, 28.86 mmol, 88.08% yield) as a yellow solid. LCMS ($ES^+$): m/z 291.0 [M–tBu+H]$^+$.

Step-4:

To a solution of tert-butyl 4-(3-oxo-4H-1,4-benzothiazin-8-yl)-3,6-dihydro-2H-pyridine-1-carboxylate 31-5 (3.5 g, 10.10 mmol) in THF (50 mL) was added 10% Pd/C (2.45 g, 2.02 mmol) under $N_2$ atmosphere. The suspension was degassed and purged with $H_2$ 3 times. The mixture was stirred under $H_2$ (15 Psi) at 20° C. for 3 h. The mixture was filtered to give yellow oil. Then the oil was concentrated to give tert-butyl 4-(3-oxo-4H-1,4-benzothiazin-8-yl)piperidine-1-carboxylate 31-6 (6 g, 17.22 mmol, 85.22% yield) as a yellow solid. LCMS ($ES^+$): m/z 293.1 [M-56+H]$^+$.

Step-5:

To a solution of tert-butyl 4-(3-oxo-4H-1,4-benzothiazin-8-yl)piperidine-1-carboxylate 31-6 (4 g, 11.48 mmol) in THF (50 mL) was added borane methylsulfanylmethane complex (1.74 g, 22.96 mmol, 3.06 mL) at 20° C. The mixture was stirred at 60° C. for 12 h. The reaction mixture was quenched by addition of methyl alcohol (30 mL) at 60° C. and stirred for 3 h. Then the mixture was concentrated to give the crude product, which was purified by column chromatography (petroleum ether/ethyl acetate=30/1 to 5/1) to afford tert-butyl 4-(3,4-dihydro-2H-1,4-benzothiazin-8-yl)piperidine-1-carboxylate 31-7 (3 g, 8.97 mmol, 78.14% yield) as a yellow solid. LCMS ($ES^+$): m/z 279.0 [M–tBu+H]$^+$.

Step-1:

To a solution of 1-bromo-2-fluoro-3-nitro-benzene 31-1 (15 g, 68.18 mmol) in DMF (150 mL) was added 2-sulfanylacetic acid 31-2 (7.54 g, 81.82 mmol, 5.80 mL) and N-ethyl-N-isopropyl-propan-2-amine (26.44 g, 204.55 mmol, 35.63 mL) at 0-10° C. The mixture was stirred at 20° C. for 3 h. The mixture was poured into water (500 mL).

Step-6:
To a solution of 2,6-dibenzyloxy-3-bromo-pyridine 5-7 (4.65 g, 12.56 mmol) and tert-butyl 4-(3,4-dihydro-2H-1,4-benzothiazin-8-yl)piperidine-1-carboxylate 31-7 (2.8 g, 8.37 mmol) in toluene (100 mL) was added sodium tert-butoxide (2.41 g, 25.11 mmol) and bis(tri-tert-butylphosphine)palladium (830.56 mg, 1.67 mmol) at 20° C. under N$_2$ atmosphere. The mixture was stirred at 90° C. for 12 h. The reaction mixture was diluted with water (300 mL) and extracted with ethyl acetate (200 mL×3). The combined organic layers were washed with brine (300 mL), dried over anhydrous Na$_2$SO$_4$, filtered and concentrated to give the crude product, which was purified by column chromatography (petroleum ether/ethyl acetate=50/1 to 15/1) to afford tert-butyl 4-[4-(2,6-dibenzyloxy-3-pyridyl)-2,3-dihydro-1,4-benzothiazin-8-yl]piperidine-1-carboxylate 31-8 (2.2 g, 3.33 mmol, 39.83% yield) as a yellow solid. LCMS (ES$^+$): m/z 624.3 [M+H]+

Step-7:
To a solution of tert-butyl 4-[4-(2,6-dibenzyloxy-3-pyridyl)-2,3-dihydro-1,4-benzothiazin-8-yl]piperidine-1-carboxylate 31-8 (500 mg, 801.54 mol) in THF (15 mL) was added 10% Pd/C (194.70 mg, 160.31 mol) under N$_2$ atmosphere. The suspension was degassed and purged with H$_2$ 3 times. The mixture was stirred under H$_2$ (15 Psi) at 20° C. for 12 h. The mixture was filtered to give black oil, and the filter cake was washed with THF (50 mL×6). Then the combined organic layers were concentrated to give a black solid, which was purified by reverse-phase prep-HPLC (Column: 120g Flash Column Welch Ultimate XB_C18 20 40 μm; 120 A120g Flash Column Welch Ultimate XB_C18 20-40 μm; 120 A; Flow rate: 85 ml/min; Mobile phase: MeCN/H$_2$O; Gradient B %: 0-70% 55 min; 70% 15 min; Instrument: TELEDYNEISCO CombiFlashRfl50) to give tert-butyl 4-[4-(2,6-dioxo-3-piperidyl)-2,3-dihydro-1,4-benzothiazin-8-yl]piperidine-1-carboxylate 31-9 (550 mg, 1.23 mmol, 38.50% yield) as a black solid. LCMS (ES$^+$): m/z 390.1 [M−56+H]$^+$.

Step-8:
To a solution of tert-butyl 4-[4-(2,6-dioxo-3-piperidyl)-2,3-dihydro-1,4-benzothiazin-8-yl]piperidine-1-carboxylate 31-9 (500 mg, 1.12 mmol) in dioxane (5 mL) was added HCl/dioxane (4 M, 10 mL) at 0-10° C. The mixture was stirred at 20° C. for 3 h. The mixture was concentrated to give 3-[8-(4-piperidyl)-2,3-dihydro-1,4-benzothiazin-4-yl]piperidine-2,6-dione 31-10 (420 mg, 1.10 mmol, 98.00% yield) as an off-white solid. LCMS (ES$^-$): m/z 346.4 [M+H]$^+$.

Step-9:
To a solution of tert-butyl 2-bromoacetate 24-1 (102.14 mg, 523.67 mol, 76.80 L) and 3-[8-(4-piperidyl)-2,3-dihydro-1,4-benzothiazin-4-yl]piperidine-2,6-dione 31-10 (200 mg, 523.67 mol, HCl salt) in DMF (8 mL) was added diisopropylethylamine (338.40 mg, 2.62 mmol, 456.07 L) at 20° C. The mixture was stirred at 60° C. for 12 h. The mixture was diluted with water (60 mL) and extracted with ethyl acetate (20 mL×3). The combined organic layers were washed with brine (30 mL×3), dried over anhydrous Na$_2$SO$_4$, filtered and concentrated to give a crude product, which was purified by column chromatography (petroleum ether/ethyl acetate=10/1 to 1/1) to give tert-butyl 2-[4-[4-(2,6-dioxo-3-piperidyl)-2,3-dihydro-1,4-benzothiazin-8-yl]-1-piperidyl]acetate 31-11 (350 mg, 740.44 mol, 70.70% yield) as a brown solid. LCMS (ES$^+$): m/z 460.2 [M+H]$^+$.

Step-10:
To a solution of tert-butyl 2-[4-[4-(2,6-dioxo-3-piperidyl)-2,3-dihydro-1,4-benzothiazin-8-yl]-1-piperidyl]acetate 31-11 (200 mg, 435.16 mol) in dioxane (1 mL) was added HCl/dioxane (4 M, 108.79 L) at 20° C. The mixture was stirred at 20° C. for 3 h. The mixture was concentrated to give 2-[4-[4-(2,6-dioxo-3-piperidyl)-2,3-dihydro-1,4-benzothiazin-8-yl]-1-piperidyl]acetic acid 31-12 (170 mg, 386.40 mol, 88.80% yield) as a brown solid. LCMS (ES$^+$): m/z 404.1 [M+H]$^+$.

Scheme 32: Synthesis of methyl (7S)-2-benzyl-7-methyl-3-[(1S,3S)-3-[4-[4-(2,6-dioxo-3-piperidyl)-2,3-dihydro-1,4-benzoxazin-7-yl]piperidine-1-carbonyl]cyclohexyl]-8,9-dihydro-7H-imidazo[4,5-f]quinoline-6-carboxylate

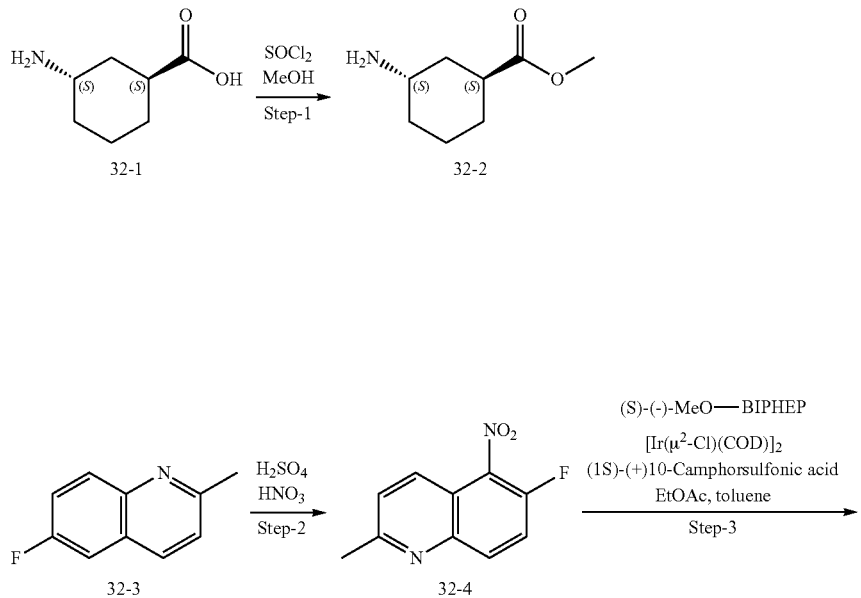

-continued
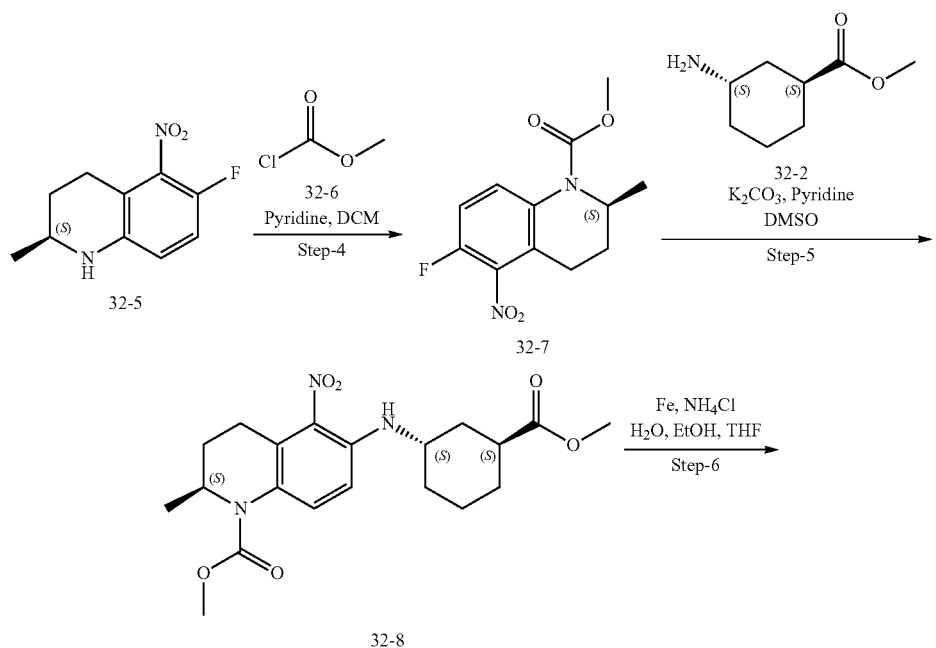
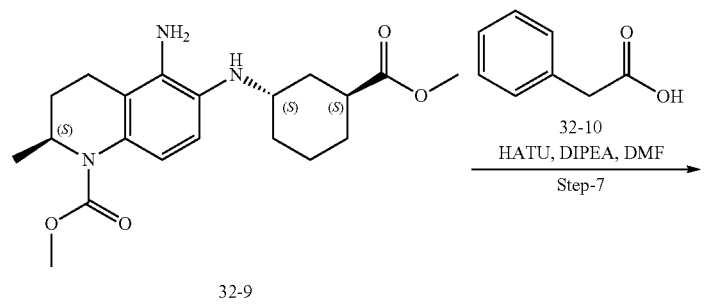
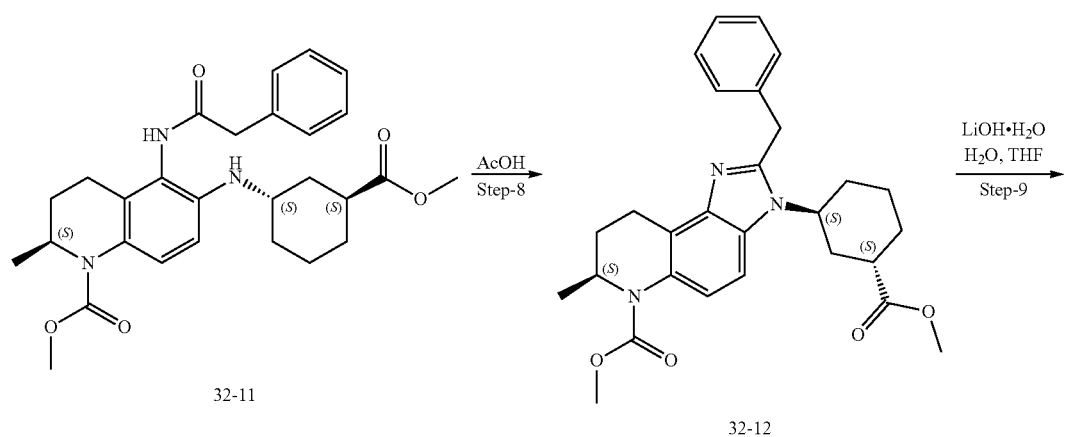

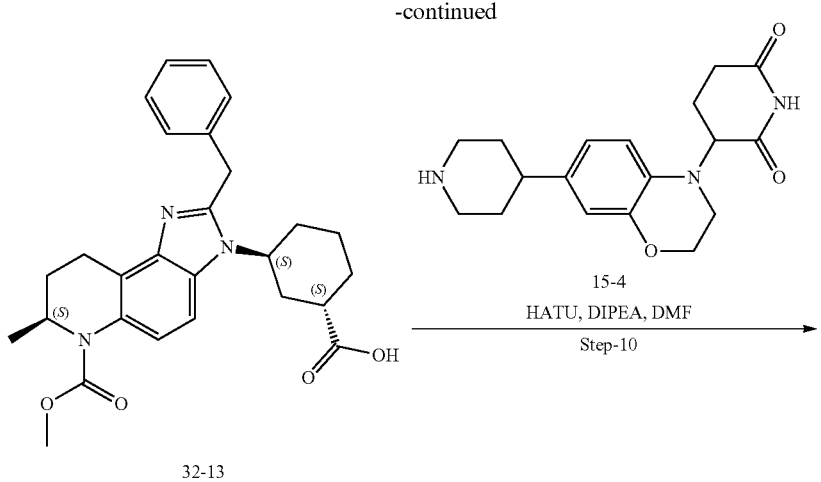

32-13

HATU, DIPEA, DMF
———————————→
Step-10

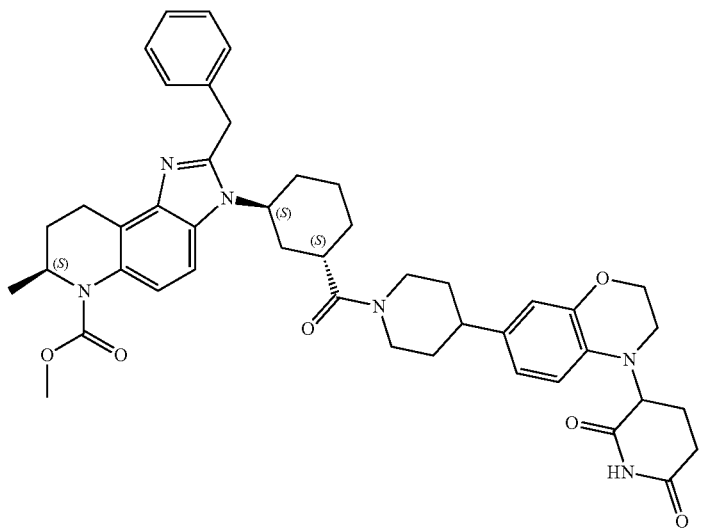

32-14

Step-1:

To a stirred solution of (1S,3S)-3-aminocyclohexanecarboxylic acid 32-1 (2.5 g, 13.92 mmol, HCl salt) in methanol (50 mL) was added thionyl chloride (3.31 g, 27.83 mmol, 2.02 mL), and the stirring was continued for 16 h at 80° C. in a sealed tube. After completion, the reaction mixture was concentrated under vacuum to obtain the crude product, which was washed with diethyl ether (30 mL) to afford methyl (1S,3S)-3-aminocyclohexanecarboxylate 32-2 (2.6 g, 12.75 mmol, 91.64% yield, HCl salt).

$^1$H NMR (401 MHz, MeOD): δ 3.70 (s, 3H), 3.40-3.44 (m, 1H), 2.83-2.92 (m, 1H), 2.28-2.32 (m, 1H), 1.96-2.04 (m, 2H), 1.58-1.75 (m, 3H), 1.43-1.49 (m, 2H).

Step-2:

To a stirred solution of sulfuric acid (60.85 g, 620.44 mmol, 114 mL) at 0° C. was added 6-fluoro-2-methyl-quinoline 32-3 (10 g, 62.04 mmol) portionwise, followed by addition of nitric acid (3.91 g, 62.04 mmol, 4.4 mL), and the stirring was continued for 4 h at room temperature. After completion, the reaction mixture poured into the aq. $Na_2CO_3$ solution and extracted with ethyl acetate (30 mL×2). The organic layer was washed with brine, dried over $Na_2SO_4$ and concentrated under vacuum. The crude material was purified by column chromatography using Dev-Silica (0-20% EtOAc/petroleum ether) to obtain 6-fluoro-2-methyl-5-nitro-quinoline 32-4 (7 g, 32.85 mmol, 52.94% yield) as a yellow solid. LCMS (ES$^+$): m/z 207.26 [M+H]$^+$.

Step-3:

In a Parr-shaker reactor, to a stirred solution of 6-fluoro-2-methyl-5-nitro-quinoline 32-4 (7 g, 33.95 mmol) in toluene (100 mL) was added molecular iodine (86.17 mg, 339.52 mol). To this solution was added a mixture of (S)-(−)-MeO-BIPHEP (217.59 mg, 373.47 mol) and chloro-cycloocatdiene-Ir-dimer (114.03 mg, 169.76 mol) and the reaction mixture was stirred for 1 h at 25° C. The reaction mixture was filtered through a column of Dev-Silica using 5% ethyl acetate in petroleum ether as an eluent to give a crude intermediate. This intermediate was dissolved in ethyl acetate, and (1S)-(+)-10-camphorsulfonic acid (7.89 g, 33.95 mmol) was added and stirred at 60° C. for 1 h. The reaction was then cooled to room temperature, and the obtained solid was collected by filtration, washed with ethyl acetate and dried well. The resulting solid was dissolved in water, neutralized with sodium bicarbonate until pH 8, and extracted with ethyl acetate. The organic layer was separated, dried over sodium sulfate, and concentrated under reduced pressure to afford (2S)-6-fluoro-2-methyl-5-nitro-1,2,3,4-tetrahydroquinoline 32-5 (5 g, 20.21 mmol, 59.54% yield) as an orange solid. LCMS (ES$^+$): m/z 211.33 [M+H]$^+$.

Step-4:

To a stirred solution of (2S)-6-fluoro-2-methyl-5-nitro-1,2,3,4-tetrahydroquinoline 32-5 (5 g, 23.79 mmol) in DCM (53.41 mL) was added pyridine (7.53 g, 95.15 mmol, 7.70 mL), and the reaction mixture was cooled to 0° C. and stirred for 5 mins, then methyl carbonochloridate 32-6 (4.50 g, 47.57 mmol, 3.68 mL) was added slowly and allowed to stir at 25° C. for 4 h. The reaction mixture was washed with water and extracted with ethyl acetate and the organic layer was separated, dried over sodium sulfate and concentrated under reduced pressure to afford methyl (2S)-6-fluoro-2-methyl-5-nitro-3,4-dihydro-2H-quinoline-1-carboxylate 32-7 (5 g, 17.19 mmol, 72.26% yield) as a yellow gummy liquid. LCMS (ES$^+$): m/z 269.38 [M+H]$^+$.

Step-5:

In a sealed tube, a stirred solution of methyl (2S)-6-fluoro-2-methyl-5-nitro-3,4-dihydro-2H-quinoline-1-carboxylate 32-7 (1.5 g, 5.59 mmol) and methyl (1S,3S)-3-aminocyclohexanecarboxylate 32-2 (1.41 g, 7.27 mmol, HCl salt) in DMSO (52.11 mL) was added pyridine (1.55 g, 19.57 mmol, 1.58 mL) and granular potassium carbonate (1.55 g, 11.18 mmol), and the stirring was continued for 16 h at 90° C. After completion, the reaction mixture was quenched with ice water and extracted with ethyl acetate (30 mL×2). The combined organic layer was dried over Na$_2$SO$_4$ and concentrated under vacuum to obtain crude compound, purified by Dev-silica and eluted with EtOAc:petroleum ether, (0-20%) to obtain methyl (2S)-6-[[(1S,3S)-3-methoxycarbonylcyclohexyl]amino]-2-methyl-5-nitro-3,4-dihydro-2H-quinoline-1-carboxylate 32-8 (1.5 g, 3.33 mmol, 59.49% yield) as red gummy liquid. LCMS (ES$^+$): m/z 406.48 [M+H]$^+$.

Step-6:

To a stirred solution of methyl (2S)-6-[[(1S,3S)-3-methoxycarbonylcyclohexyl]amino]-2-methyl-5-nitro-3,4-dihydro-2H-quinoline-1-carboxylate 32-8 (1.3 g, 3.21 mmol) in water (20.18 mL), ethanol (60.53 mL), THF (60.53 mL) were added iron powder (2.69 g, 48.10 mmol) and ammonium chloride (1.37 g, 25.65 mmol, 896.80 L), and the reaction mixture was stirred at 80° C. for 6 h. The reaction mixture was filtered through celite, the filtrate was collected and concentrated under reduced pressure to give the crude compound, which was washed with n-pentane and diethyl ether to afford methyl (2S)-5-amino-6-[[(1S,3 S)-3-methoxycarbonylcyclohexyl]amino]-2-methyl-3,4-dihydro-2H-quinoline-1-carboxylate 32-9 (1.1 g, 2.50 mmol, 77.84% yield) as off-brown gummy liquid. LCMS (ES$^+$): m/z 376.49 [M+H]$^+$.

Step-7:

To a stirred solution of methyl (2S)-5-amino-6-[[(1S,3S)-3-methoxycarbonylcyclohexyl]amino]-2-methyl-3,4-dihydro-2H-quinoline-1-carboxylate 32-9 (1.1 g, 2.93 mmol), 2-phenylacetic acid 32-10 (598.31 mg, 4.39 mmol, 543.92 L) in DMF (10.19 mL) was added DIPEA (1.14 g, 8.79 mmol, 1.53 mL), the reaction mixture was stirred for 5 mins, then HATU (1.67 g, 4.39 mmol) was added, and the reaction mixture was stirred at 25° C. for 4 h. Crushed ice was added to the reaction mixture and the stirring was continued for 10 mins. The obtained solid precipitate was filtered, washed with pentane and diethyl ether, and thoroughly dried to afford methyl (2S)-6-[[(1S,3S)-3-methoxycarbonylcyclohexyl]amino]-2-methyl-5-[(2-phenylacetyl)amino]-3,4-dihydro-2H-quinoline-1-carboxylate 32-11 (1.2 g, 2.16 mmol, 73.87% yield) as off-brown solid. LCMS (ES$^+$): m/z 494.51 [M+H]$^+$.

Step-8:

A solution of methyl (2S)-6-[[(1S,3S)-3-methoxycarbonylcyclohexyl]amino]-2-methyl-5-[(2-phenylacetyl)amino]-3,4-dihydro-2H-quinoline-1-carboxylate 32-11 (1.2 g, 2.43 mmol) in acetic acid (10 mL) was stirred at 80° C. for 16 hr. The reaction mixture was slowly added to an ice cold sat. NaHCO$_3$ solution, and the solid precipitate was extracted with ethyl acetate. The organic layer was separated dried over sodium sulfate and concentrated under reduced pressure to afford methyl (7S)-2-benzyl-3-[(1S,3S)-3-methoxycarbonylcyclohexyl]-7-methyl-8,9-dihydro-7H-imidazo[4,5-f]quinoline-6-carboxylate 32-12 (1 g, 2.10 mmol, 79.95% yield) as an off-white solid. LCMS (ES$^+$): m/z 476.46 [M+H]$^+$.

Step-9:

To a stirred solution of methyl (7S)-2-benzyl-3-[(1S,3S)-3-methoxycarbonylcyclohexyl]-7-methyl-8,9-dihydro-7H-imidazo[4,5-f]quinoline-6-carboxylate 32-12 (1 g, 2.10 mmol) in THF (10 mL) were added water (10 mL) and lithium hydroxide monohydrate, 98% (441.19 mg, 10.51 mmol, 292.18 L), and the reaction mixture was stirred at 25° C. for 16 h. The reaction mixture was concentrated under reduced pressure to remove THF and water, and the crude mixture was diluted with 1 ml of water and neutralized with 10% citric acid solution. The solid precipitate was filtered and thoroughly dried to afford (1S,3S)-3-[(7S)-2-benzyl-6-methoxycarbonyl-7-methyl-8,9-dihydro-7H-imidazo[4,5-f]quinolin-3-yl]cyclohexanecarboxylic acid 32-13 (850 mg, 1.69 mmol, 80.23% yield) as an off-yellow solid. LCMS (ES$^+$): m/z 462.47 [M+H]$^+$.

Step-10:

To a stirred solution of (1S,3S)-3-[(7S)-2-benzyl-6-methoxycarbonyl-7-methyl-8,9-dihydro-7H-imidazo[4,5-f]quinolin-3-yl]cyclohexanecarboxylic acid 32-13 (0.040 g, 86.66 mol), 3-[7-(4-piperidyl)-2,3-dihydro-1,4-benzoxazin-4-yl]piperidine-2,6-dione 15-4 (46.11 mg, 104.00 mol, TFA salt) in DMF (2 mL) was added DIPEA (56.00 mg, 433.32 mol, 75.48 L) dropwise at room temperature under nitrogen atmosphere. To the reaction mixture, HATU (49.43 mg, 130.00 mol) was added, and reaction mixture was stirred at room temperature for 2 h. After completion of the reaction, the reaction mixture was concentrated using GeneVac. The residue was purified by Prep HPLC to afford methyl (7S)-2-benzyl-7-methyl-3-[(1S,3S)-3-[4-[4-(2,6-dioxo-3-piperidyl)-2,3-dihydro-1,4-benzoxazin-7-yl]piperidine-i-carbonyl]cyclohexyl]-8,9-dihydro-7H-imidazo[4,5-f]quinoline-6-carboxylate 32-14 (0.022 g, 27.94 mol, 32.24% yield) as a pale pink solid.

Preparative HPLC method: column/dimensions: X-SELECT-C18(19×250, 5 um); Mobile phase A: 5 mM ammonium acetate in water; Mobile phase B: 100% ACN; Gradient (Time/% B): 0/10, 2/10, 10/65, 15/65, 16/100; Flow rate: 16 ml/min; Solubility: ACN+H$_2$O. LCMS (ES$^+$): m/z 773.40 [M+H]$^+$.

$^1$H NMR (401 MHz, DMSO-d$_6$): δ 10.80 (s, 1H), 7.47 (d, J=9.0 Hz, 1H), 7.29 (t, J=7.3 Hz, 5H), 6.73 (d, J=8.3 Hz, 1H), 6.60 (d, J=7.5 Hz, 1H), 5.28 (d, J=40.5 Hz, 1H), 4.8-4.9 (m, 1H), 4.64 (m, 2H), 4.05-4.4 (m, 4H), 3.65-4.0 (m, 1H), 3.66 (s, 3H), 2.95-3.25 (m, 5H), 2.65-2.9 (m, 2H), 2.59 (s, 3H), 2.24-2.34 (m, 2H), 2.0-2.19 (m, 2H), 1.3-1.9 (m, 14H), 1.07 (d, J=6.6 Hz, 3H).

Scheme 33: Synthesis of 3-(8-bromo-3-oxo-1,4-benzoxazin-4-yl)piperidine-2,6-dione

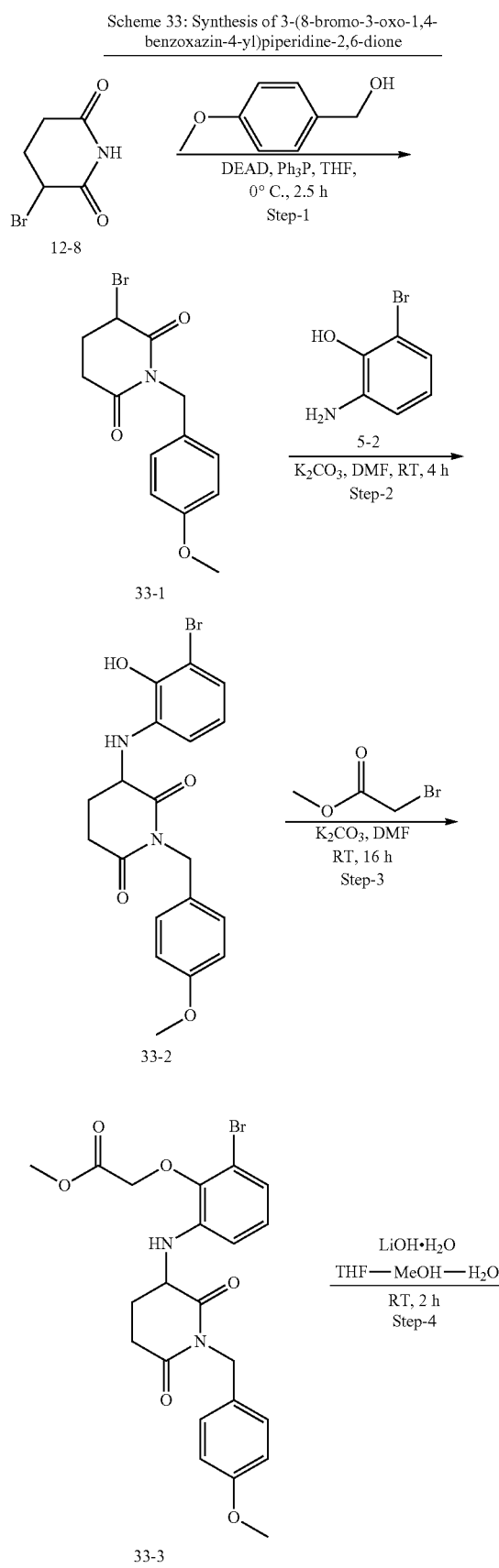

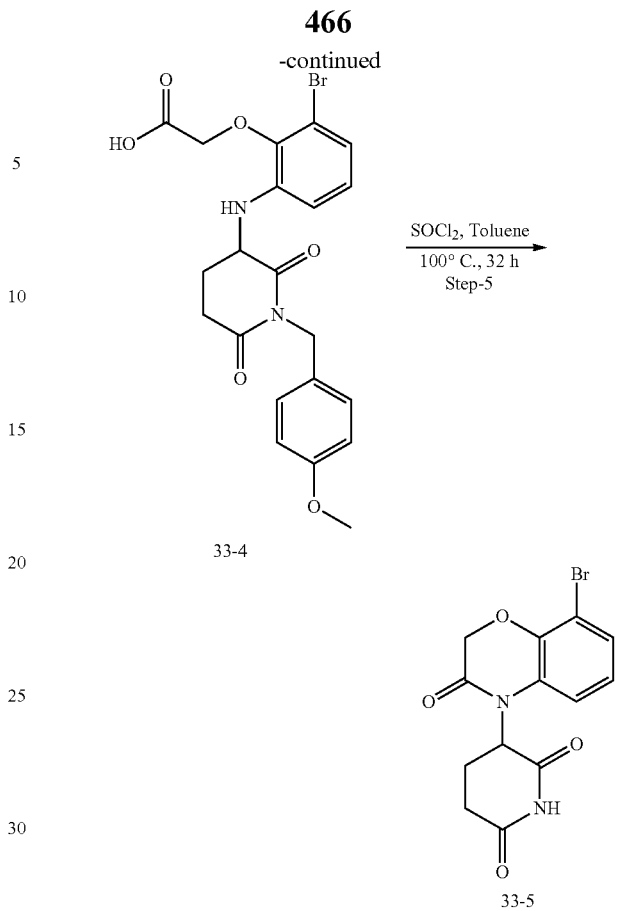

Step-1:
To a stirred solution of 3-bromopiperidine-2,6-dione 12-8 (4 g, 20.83 mmol) in dry THF (60 mL) under nitrogen atmosphere, were added (4-methoxyphenyl)methanol (3.17 g, 22.92 mmol, 2.85 mL), triphenylphosphine (6.56 g, 25.00 mmol) followed by ethyl (NE)-N-ethoxycarbonyliminocarbamate (4.35 g, 25.00 mmol, 3.92 mL) dropwise at 0° C. The resulting mixture was stirred at 0° C. for 2.5 h. The reaction mixture was quenched with water (100 mL) and extracted with ethyl acetate (3×200 mL). The combined organic layer was dried over $Na_2SO_4$, filtered, and concentrated under reduced pressure to get crude as pale-yellow liquid. The crude product was purified by column chromatography (230-400 mesh silica gel), where the desired product was eluted with 80-85% dichloromethane:hexane to afford 3-bromo-1-[(4-methoxyphenyl)methyl]piperidine-2,6-dione 33-1 (1.8 g, 5.77 mmol, 27.68% yield) as an off white solid. $^1$H NMR (400 MHz, DMSO-$d_6$): δ 7.16 (d, J=8.80 Hz, 2H), 6.86 (d, J=8.80 Hz, 2H), 5.09 (t, J=4.40 Hz, 1H), 4.77 (s, 2H), 3.72 (s, 3H), 2.88-2.73 (m, 2H), 2.58-2.53 (m, 1H), 2.19-2.11 (m, 1H).

Step 2:
To a stirred solution of 2-amino-6-bromo-phenol 5-2 (1 g, 5.32 mmol) in DMF (10 mL) was added 3-bromo-1-[(4-methoxyphenyl)methyl]piperidine-2,6-dione 33-1 (1.83 g, 5.85 mmol) followed by potassium carbonate (1.47 g, 10.64 mmol) at room temperature. The reaction mixture was stirred at room temperature for 4 h. After completion of the reaction, the reaction mixture was quenched with water (20 mL), the precipitated solid was filtered and dried under reduced pressure to obtain 3-(3-bromo-2-hydroxy-anilino)-1-[(4-methoxyphenyl)methyl]piperidine-2,6-dione 33-2 (1.5 g, 3.40 mmol, 63.84% yield) as a purple solid. LCMS (ES$^+$): m/z 419.2 [M+H]$^+$.

Step-3:

To a stirred solution of 3-(3-bromo-2-hydroxy-anilino)-1-[(4-methoxyphenyl)methyl]piperidine-2,6-dione 33-2 (1 g, 2.39 mmol) in DMF (10 mL) was added potassium carbonate (988.91 mg, 7.16 mmol) and methyl 2-bromoacetate (401.35 mg, 2.62 mmol) at room temperature. The reaction mixture was stirred at room temperature for 16 h. The reaction mixture was quenched with water (20 mL) and extracted with ethyl acetate (3×50 mL). The separated organic layers were combined and dried over anhydrous $Na_2SO_4$, filtered and concentrated under reduced pressure to obtain crude as a brown gum. The crude residue was purified by column chromatography (silica gel, 100-200 mesh) where the desired product was eluted at 40-45% ethyl acetate in hexane to afford methyl 2-[2-bromo-6-[[1-[(4-methoxyphenyl)methyl]-2,6-dioxo-3-piperidyl]amino]phenoxy]acetate 33-3 (1 g, 2.00 mmol, 83.75% yield) as a brown solid. LCMS (ES$^+$): m/z 491.2 [M+H]$^+$.

Step-4:

To a stirred solution of methyl 2-[2-bromo-6-[[1-[(4-methoxyphenyl)methyl]-2,6-dioxo-3-piperidyl]amino]phenoxy]acetate 33-3 (500 mg, 1.02 mmol) in methanol (0.5 mL), THF (0.5 mL) and water (0.5 mL) was added lithium hydroxide monohydrate (128.10 mg, 3.05 mmol) at room temperature. The reaction mixture was stirred at room temperature for 2 h. The reaction mixture was concentrated under reduced pressure, diluted with water (5 mL) and acidified with 1.5 N HCl solution (pH=3). The precipitated solid was filtered and dried under reduced pressure to afford 2-[2-bromo-6-[[1-[(4-methoxyphenyl)methyl]-2,6-dioxo-3-piperidyl]amino]phenoxy]acetic acid 33-4 (460 mg, 954.11 μmol, 93.76% yield) as a brown solid. LCMS (ES$^+$): m/z 477.0 [M+H]$^+$.

Step-5:

To a stirred solution of 2-[2-bromo-6-[[1-[(4-methoxyphenyl)methyl]-2,6-dioxo-3-piperidyl]amino]phenoxy]acetic acid 33-4 (250 mg, 523.77 μmol) in toluene (5 mL) was added thionyl chloride (311.57 mg, 2.62 mmol, 189.98 μL) at room temperature. The reaction mixture was stirred at 100° C. for 32 h. The reaction mixture was concentrated under reduced pressure and then the obtained crude residue was triturated with n-heptane (20 mL) to obtain crude product. The crude material was purified through reverse phase purification using 0.1% formic acid buffer in acetonitrile and the pure fractions were lyophilized to afford 3-(8-bromo-3-oxo-1,4-benzoxazin-4-yl)piperidine-2,6-dione 33-5 (20 mg, 57.91 μmol, 11.06% yield) as a brown solid. LCMS (ES$^-$): m/z 336.8 [M–H]$^-$. $^1$H NMR (400 MHz, DMSO-d6): δ 13.3 (br s, 1H), 7.34 (dd, J=1.20, 8.00 Hz, 1H), 7.12 (dd, J=1.60, 8.20 Hz, 1H), 7.03 (t, J=8.00 Hz, 1H), 4.84 (dd, J=4.40, 9.40 Hz, 1H), 4.63 (s, 2H), 2.72 (t, J=7.20 Hz, 2H), 2.27-2.18 (m, 1H), 2.12-2.03 (m, 1H).

Indoline CRBN binders

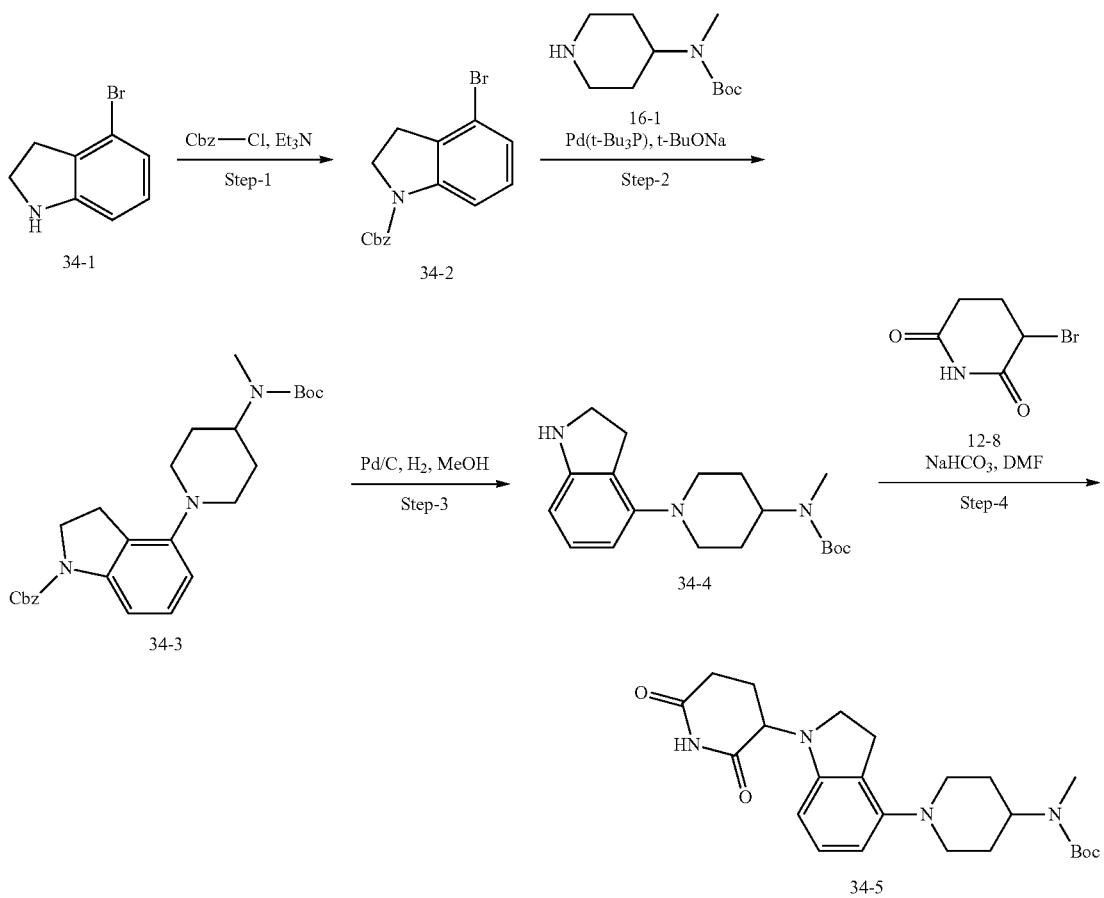

Scheme 34: Synthesis of (3S)-3-[4-(4-(methylamino)-1-piperidyl]indolin-1-yl]piperidine-2,6-dione, (3R)-3-[4-(4-(methylamino)-1-piperidyl]indolin-1-yl]piperidine-2,6-dione and 3-[4-(4-(methylamino)-1-piperidyl]indolin-1-yl]piperidine-2,6-dione

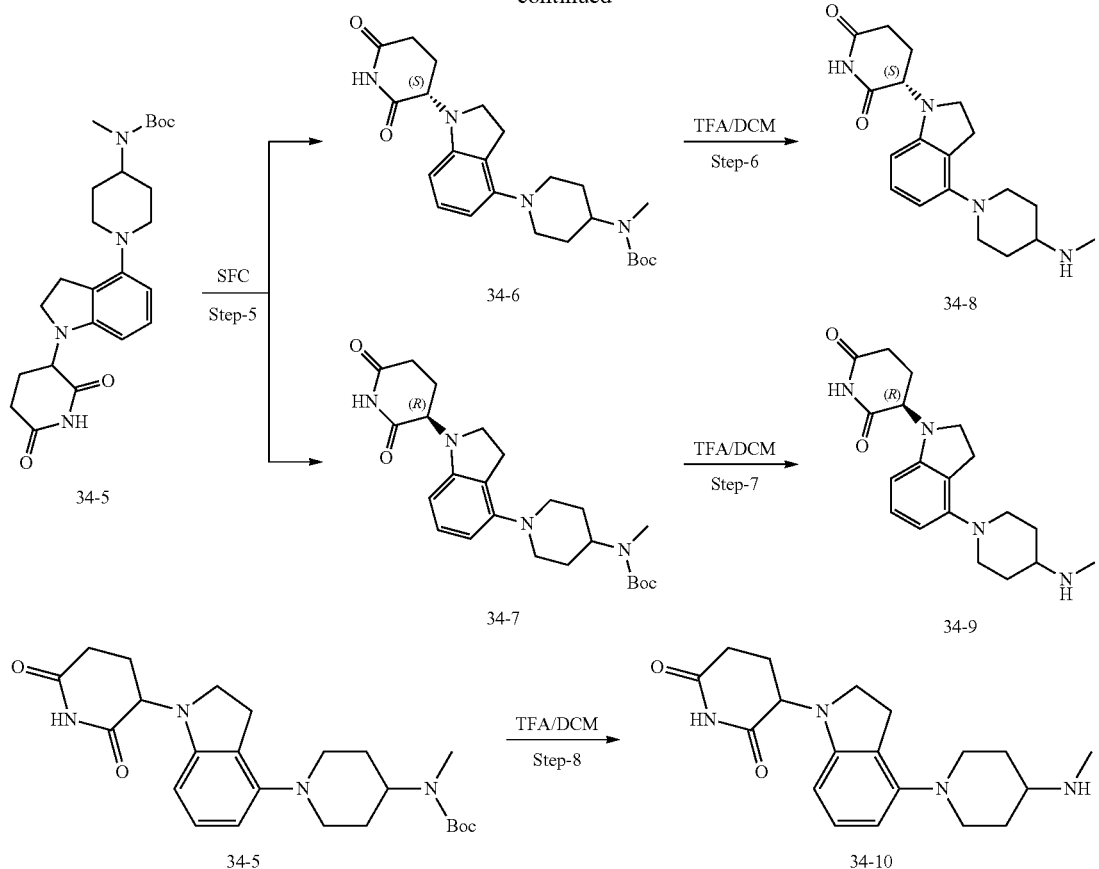

Step-1:

To a stirred solution of 4-bromoindoline 34-1 (5.0 g, 25.24 mmol) and Et₃N (5.11 g, 50.49 mmol, 7.04 mL) in DCM (40 mL) at 0° C. was added Cbz-Cl (5.17 g, 30.29 mmol) at under N₂ atmosphere and the reaction mixture was stirred at room temperature for 12 h. Upon completion of the reaction, the reaction mixture was quenched with sat. NaHCO₃ solution (200 ml) and extracted with EtOAc (200 mL×2). The combined organic layer was washed with brine (100 mL), dried over Na₂SO₄ and concentered in vacuo to give the crude material, which was purified by column chromatography using silica-gel and EtOAc in petroleum ether as an eluent to afford benzyl indoline-1-carboxylate 34-2 (4.0 g, 9.03 mmol, 35.77% yield) a sa light-yellow solid. LCMS (ES⁺): m/z 332.30 [M+H]⁺.

Step-2:

To a solution of tert-butyl N-methyl-N-(4-piperidyl)carbamate 16-1 (2.0 g, 9.33 mmol) and 2-benzyl 4-bromoindoline-1-carboxylate 34-2 (3.10 g, 9.33 mmol) in toluene (20 mL) was added NaO$^t$Bu (2.69 g, 28.00 mmol) at room temperature. The reaction mixture was degassed with nitrogen gas for 10 min and Pd(t-Bu₃P)₂ (238.47 mg, 466.63 mol, 0.2 eq.) was added. The reaction mixture was degassed with nitrogen gas for additional 5 min and it was stirred at 110° C. for 2 h. The reaction mixture was filtered through celite bed and washed with ethyl acetate (100 mL). The organic layer was washed with water (50 mL) and brine (50 mL), dried over Na₂SO₄ and concentrated in vacuo to give the crude product, which was purified by column chromatography using Davisil silica and 40% ethyl acetate in petroleum ether as eluent to afford benzyl 4-(4-((tert-butoxycarbonyl)(methyl)amino)piperidin-1-yl)indoline-1-carboxylate 34-3 (2.0 g, 3.26 mmol, 34.98% yield) as light yellow liquid. LCMS (ES⁺): m/z 466.88 [M+H]⁺.

Step-3:

To a solution of benzyl 4-[4-[tert-butoxycarbonyl(methyl)amino]-1-piperidyl]indoline-1-carboxylate 34-3 (2.0 g, 4.30 mmol) in EtOAc (10 mL) was added 10% palladium on carbon (1.83 g, 17.18 mmol) at room temperature under N₂ atmosphere. The reaction mixture was degassed with N₂ for 5 min and stirred at room temperature for 12 h under H₂ atmosphere (balloon). Upon completion of the reaction, the reaction mixture was passed through a celite bed and was washed with EtOAc (100 mL). The filtrate was washed with water (2×50 mL), brine (50 mL), and dried over Na₂SO₄. The crude product was concentrated in vacuo to get the crude, which was purified by column chromatography over Davisil silica using EtOAc in petroleum ether as eluent to afford the tert-butyl N-(1-indolin-4-yl-4-piperidyl)-N-methyl-carbamate 34-4 (0.6 g, 1.07 mmol, 24.86% yield). LCMS (ES⁺): m/z 332.47 [M+H]⁺.

Step-4:

To a stirred solution of tert-butyl N-(1-indolin-4-yl-4-piperidyl)-N-methyl-carbamate 34-4 (0.6 g, 1.81 mmol) and 3-bromopiperidine-2,6-dione 12-8 (2.09 g, 10.86 mmol) in DMF (20 mL) was added NaHCO₃ (1.52 g, 18.10 mmol, 704.03 μL) at room temperature in a sealed tube and the reaction mixture was stirred at 85° C. for 16h. Upon completion of reaction, the reaction mixture was poured in ice cold water and extracted using EtOAc (30 mL×3). The combined organic layer was washed with cold brine and dried over $Na_2SO_4$ to give the crude, which was purified by column chromatography using silica gel (230-400 mesh) and 0-100% EtOAc in petroleum ether as an eluent to afford tert-butyl (1-(1-(2,6-dioxopiperidin-3-yl)indolin-4-yl)piperidin-4-yl)(methyl)carbamate 34-5 (0.760 g, 1.58 mmol, 87.28% yield). LCMS (ES⁺): m/z 442.36 [M+H]⁺.

Step-5:

Racemic tert-butyl N-[1-[1-(2,6-dioxo-3-piperidyl)indolin-4-yl]-4-piperidyl]-N-methyl-carbamate 34-5 (4.0 g, 9.04 mmol) was submitted for SFC for the separation of isomers. The fractions obtained were concentrated and lyophilized to afford tert-butyl N-[1-[1-[(3S)-2,6-dioxo-3-piperidyl]indolin-4-yl]-4-piperidyl]-N-methyl-carbamate 34-6 (Early eluting peak arbitrarily assigned as S-isomer, 1.5 g, 3.22 mmol, 35.62% yield) and tert-butyl N-[1-[1-[(3R)-2,6-dioxo-3-piperidyl]indolin-4-yl]-4-piperidyl]-N-methyl-carbamate 34-7 (Late eluting peak arbitrarily assigned as R-isomer, 2.2 g, 4.47 mmol, 49.50% yield) as light-blue solids.

Preparative SFC conditions: column/dimensions: CHIRALCEL-OJ-H (30×250) mm, 5µ; % $CO_2$: 50%; % co-solvent: 50% (ACN); Total Flow: 100 g/min; Back Pressure: 100 bar; Temperature: 30° C.; UV: 237 nm; Solubility: ACN.

Step-6:

To a solution of tert-butyl N-[1-[1-[(3S)-2,6-dioxo-3-piperidyl]indolin-4-yl]-4-piperidyl]-N-methyl-carbamate 34-6 (2.0 g, 4.52 mmol) in DCM (5 mL) was added TFA (1.34 g, 11.76 mmol, 906.14 L) dropwise over 5 min at 0° C. under $N_2$ atmosphere. The reaction mixture was stirred at room temperature for 4 h. Upon completion of the reaction, the mixture was concentrated in vacuo to get a crude product, which was washed with diethyl ether and dried under vacuum to afford (3S)-3-[4-[4-(methylamino)-1-piperidyl]indolin-1-yl]piperidine-2,6-dione 34-8 (2.01 g, 4.32 mmol, 95.49% yield, TFA salt). LCMS (ES⁻): m/z 341.42 [M−H]⁻.

Step-7:

The procedure was similar to that of Step-6. Compound (3R)-3-[4-[4-(methylamino)-1-piperidyl]indolin-1-yl]piperidine-2,6-dione 34-9 was obtained as a TFA salt. LCMS (ES⁺): m/z 343.52 [M+H]⁺.

Step-8:

The procedure was similar to that of Step-6. Compound 3-[4-[4-(methylamino)-1-piperidyl]indolin-1-yl]piperidine-2,6-dione 34-10 was obtained as a TFA salt. LCMS (ES⁺): m/z 343.50 [M+H]⁺.

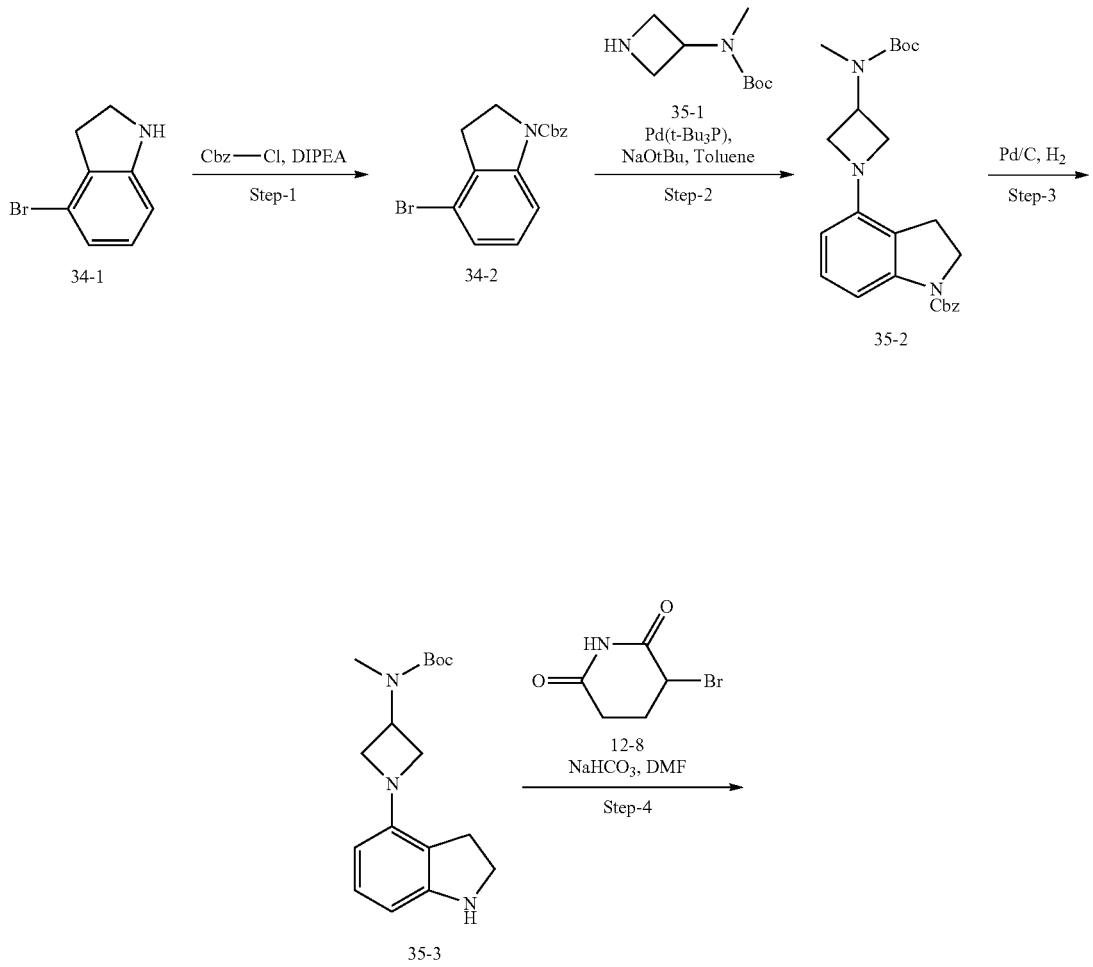

Scheme 35: Synthesis of tert-butyl (S)-(1-(1-(2,6-dioxopiperidin-3-yl)indolin-4-yl)azetidin-3-yl)(methyl)carbamate and tert-butyl (R)-(1-(1-(2,6-dioxopiperidin-3-yl)indolin-4-yl)azetidin-3-yl)(methyl)carbamate

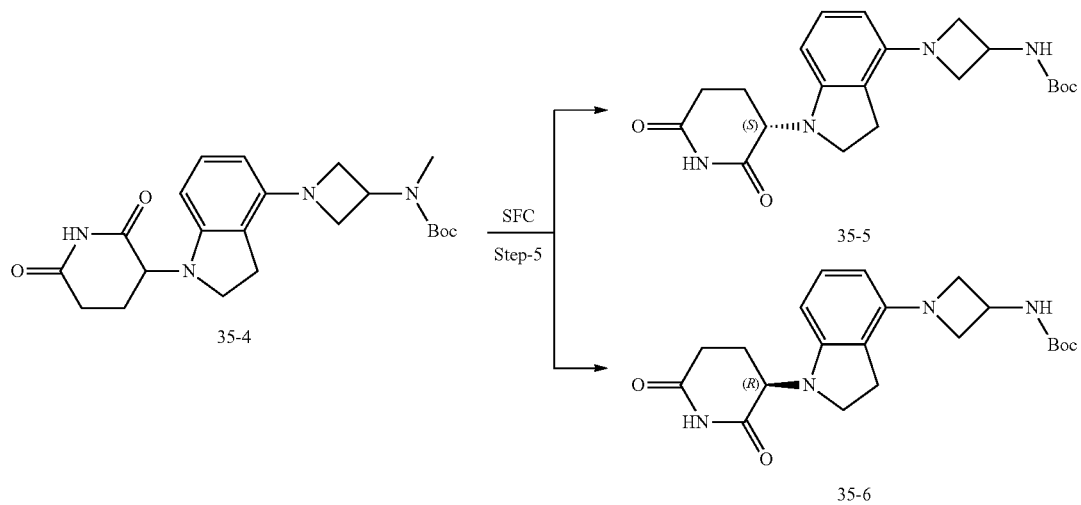

Step-1:

To a solution of 4-bromoindoline 34-1 (8 g, 40.39 mmol) in DCM (80 mL) was added DIPEA (8.17 g, 80.78 mmol, 11.26 mL), followed by dropwise addition of Cbz-Cl (8.27 g, 48.47 mmol, 6.89 mL) under $N_2$ atmosphere. The reaction mixture was stirred at room temperature for 16 h. After completion, the reaction mixture was diluted with water, extracted with DCM (30 mL×3). The organic layer was dried over $Na_2SO_4$ and concentrated in vacuo to get crude product. It was purified by column chromatography using Davisil silica and 10-20% EtOAc in petroleum ether as an eluent to afford the title compound, benzyl 4-bromoindoline-1-carboxylate 34-2 (7.5 g, 22.53 mmol, 55.78% yield) as a light-brown solid. LCMS (ES$^+$): m/z 332.35 [M+H]$^+$.

Step-2:

To a solution of benzyl 4-bromoindoline-1-carboxylate 34-2 (7.5 g, 22.58 mmol) and tert-butyl N-(azetidin-3-yl)-N-methyl-carbamate 35-1 (5.03 g, 22.58 mmol, HCl salt) in toluene (60 mL) was added NaO$^t$Bu (6.51 g, 67.73 mmol) at room temperature. The reaction mixture was degassed with $N_2$ for 10 min and then Pd(t-Bu$_3$P)$_2$ (230.74 mg, 451.55 mol) was added to the reaction mixture and the reaction mixture was again degassed with $N_2$ for additional 5 min and stirred at 90° C. for 1 h. After completion, the reaction mixture was filtered through a celite bed and washed with EtOAc (100 mL). The organic layer was washed with water (50 mL) and brine (50 mL), dried over $Na_2SO_4$ and concentrated in vacuo to get crude product. The product was purified by column chromatography using Davisil silica using 30% EtOAc in petroleum ether as an eluent to afford the title compound, benzyl 4-[3-[tert-butoxycarbonyl(methyl)amino]azetidin-1-yl]indoline-1-carboxylate 35-2 (5.2 g, 10.59 mmol, 46.90% yield) as na off-white solid. LCMS (ES$^+$): m/z 438.33 [M+H]$^+$.

Step-3:

A stirred solution of benzyl 4-[3-[tert-butoxycarbonyl (methyl)amino]azetidin-1-yl]indoline-1-carboxylate 35-2 (5.2 g, 11.88 mmol) in EtOAc (40 mL) and THF (40 mL) was degassed with argon for 10 min. 10% Palladium on carbon (5.20 g, 48.86 mmol) was added to the reaction mixture and it was stirred for 16 h at room temperature under $H_2$-balloon pressure. Upon completion of reaction, it was filtered through a celite bed, washed with EtOH (50 mL) and EtOAc (50 mL). The filtrate was concentrated under reduced pressure to get crude product. The crude residue was purified by column chromatography using 20% EtOAc in petroleum ether as eluent to afford tert-butyl N-(1-indolin-4-ylazetidin-3-yl)-N-methyl-carbamate 35-3 (2.2 g, 7.08 mmol, 59.56% yield) as a brown gum. LCMS (ES$^+$): m/z 304.46 [M+H]$^+$.

Step-4:

To a stirred solution of tert-butyl N-(1-indolin-4-ylazetidin-3-yl)-N-methyl-carbamate 35-3 (2.2 g, 7.25 mmol) and 3-bromopiperidine-2,6-dione 12-8 (6.96 g, 36.26 mmol) in DMF (15 mL) was added NaHCO$_3$ (6.09 g, 72.51 mmol, 2.82 mL). The reaction mixture was stirred in a sealed tube at 85° C. for 16 h. Upon completion of reaction, the reaction mixture was poured in ice cooled water. The product was extracted using EtOAc (50 mL×2). The organic layer was washed with cooled brine, dried over $Na_2SO_4$ to get the crude product, which was purified by column chromatography using silica gel (230-400 mesh) and 30% EtOAc in petroleum ether as an eluent to give tert-butyl N-[1-[1-(2, 6-dioxo-3-piperidyl)indolin-4-yl]azetidin-3-yl]-N-methyl-carbamate 35-4 (2 g, 4.00 mmol, 55.10% yield) as a brown solid. LCMS (ES$^+$): m/z 415.51 [M+H]$^+$.

Step-5:

Racemic tert-butyl N-[1-[1-(2,6-dioxo-3-piperidyl)indolin-4-yl]azetidin-3-yl]-N-methyl-carbamate 35-4 (1 g) was separated by SFC, followed by concentration in vacuo to afford tert-butyl (S)-(1-(1-(2,6-dioxopiperidin-3-yl)indolin-4-yl)azetidin-3-yl)(methyl)carbamate 35-5 (Early eluting peak arbitrarily assigned as S-isomer, 0.4 g) and tert-butyl (R)-(1-(1-(2,6-dioxopiperidin-3-yl)indolin-4-yl)azetidin-3-yl)(methyl)carbamate 35-6 (Late eluting peak arbitrarily assigned as R-isomer, 0.4 g).

Preparative SFC conditions: column/dimensions: CHI-RALCEL (4.6×250) mm, 5μ; % CO$_2$: 60%; % co-solvent: 40% (ACN); Total Flow: 110 g/min; Back Pressure: 100 bar; Temperature: 30° C.; UV: 215 nm; Solubility: ACN.

Scheme 36: Synthesis of (3R)-3-[4-[3-(methylaminomethyl) azetidin-1-yl]indolin-1-yl]piperidine-2,6-dione, (3S)-3-[4-[3-(methylaminomethyl)azetidin-1-yl]indolin-1-yl]piperidine-2,6-dione, and 3-[4-[3-(methylaminomethyl) azetidin-1-yl]indolin-1-yl]piperidine-2,6-dione
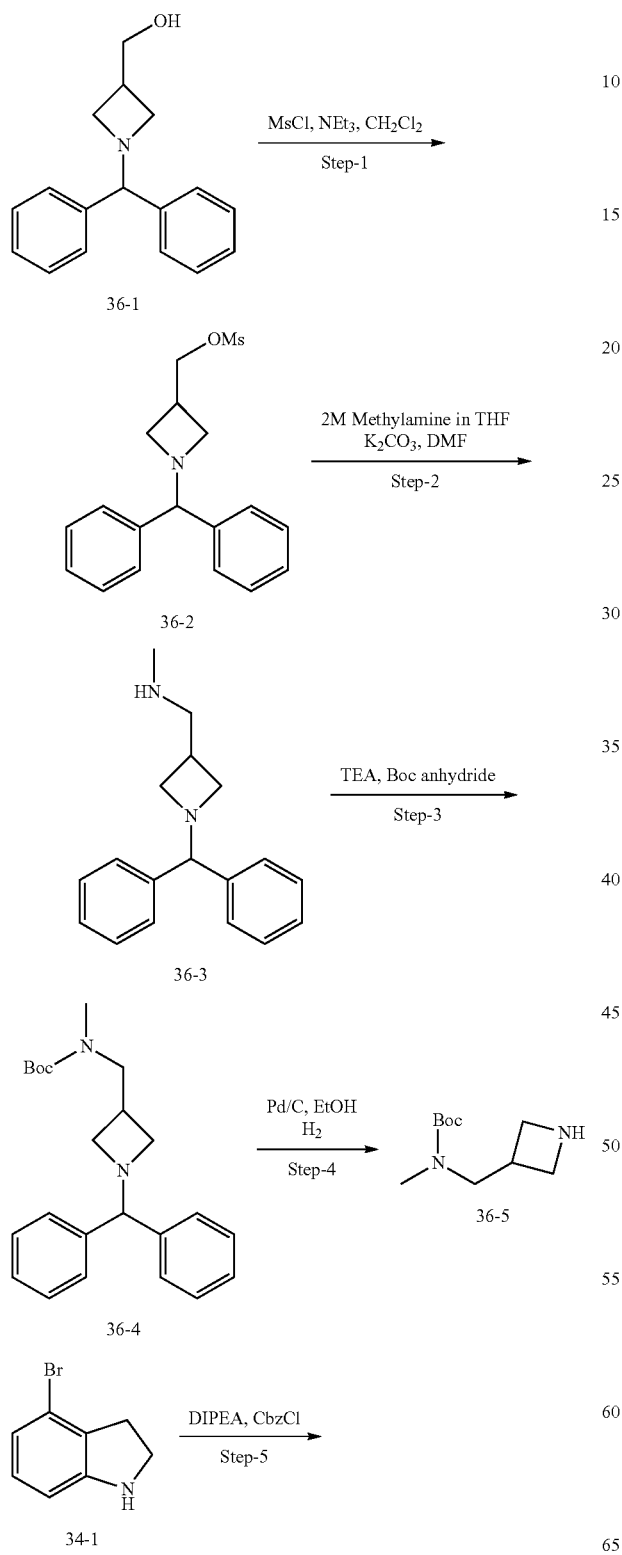
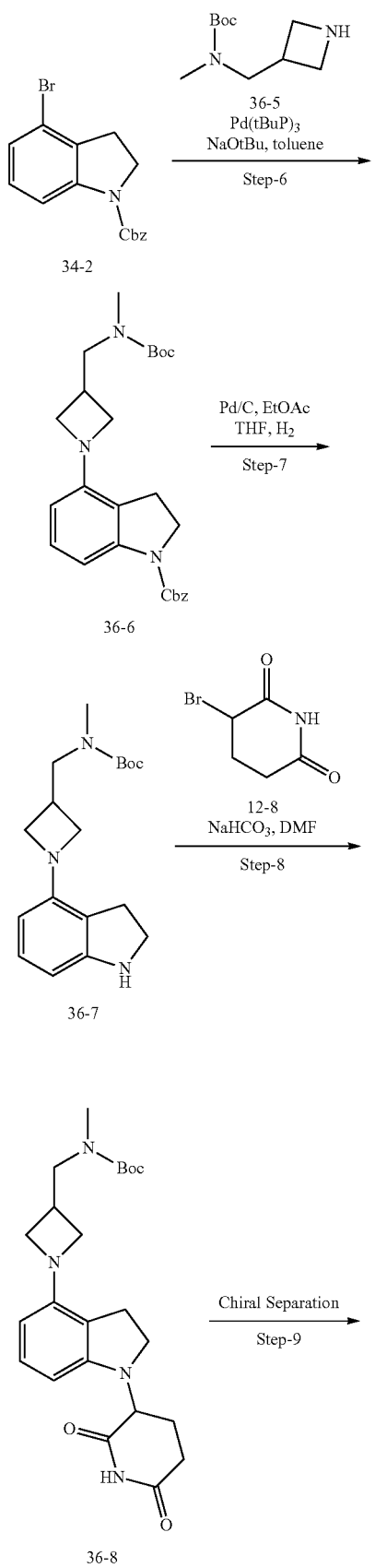

-continued

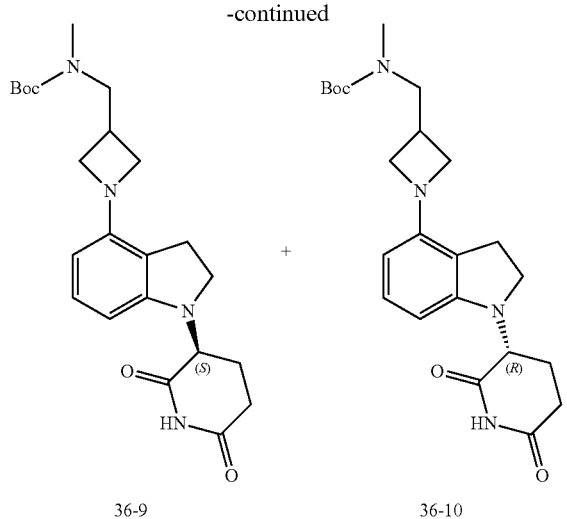

36-9    +    36-10

Step-1:

To a solution of (1-benzhydrylazetidin-3-yl)methanol 36-1 (13.0 g, 51.31 mmol) in DCM (130 mL) was added N,N-diethylethanamine (15.58 g, 153.94 mmol, 21.46 mL) at room temperature and the reaction mixture was cooled to 0° C. Then methanesulfonyl chloride (8.82 g, 76.97 mmol, 5.96 mL) was added dropwise, and the reaction mixture was stirred at room temperature for 2 h. The reaction mixture was diluted with DCM (200 mL) and washed with a saturated NaHCO$_3$ solution (100 mL) and brine (100 mL). The organic layer was dried over Na$_2$SO$_4$, and concentrated in vacuo to give (1-benzhydrylazetidin-3-yl)methyl methanesulfonate 36-2 (15.0 g, 42.09 mmol, 82.02% yield. LCMS (ES$^+$): m/z 332.39 [M+H]$^+$.

Step-2:

To a stirred solution of (1-benzhydrylazetidin-3-yl)methyl methanesulfonate 36-2 (12.5 g, 37.72 mmol) in DMF (150 mL) were added methylamine solution, 2.0 M in THF (5.86 g, 188.58 mmol) and K$_2$CO$_3$ (15.64 g, 113.15 mmol, 6.83 mL) at room temperature under N$_2$ atmosphere. The reaction mixture was heated at 80° C. for 16 h. Upon completion of the reaction, the reaction mixture was filtered. The filtrate was washed with pentane (50 mL) and concentrated in vacuo to afford 1-(1-benzhydrylazetidin-3-yl)-N-methyl-methanamine 36-3 (11.0 g, 34.69 mmol, 91.97% yield) as a brown gummy solid. LCMS (ES$^+$): m/z 267.45 [M+H]$^+$.

Step-3:

To a solution of 1-(1-benzhydrylazetidin-3-yl)-N-methyl-methanamine 36-3 (11.0 g, 41.29 mmol) and N, N-diethylethanamine (12.54 g, 123.88 mmol, 17.27 mL,) in DCM (100 mL), cooled to 0° C., tert-butoxycarbonyl tert-butyl carbonate (11.72 g, 53.68 mmol, 12.32 mL, 1.3 eq.) was added. The reaction mixture was stirred at room temperature for 12 h. The progress of the reaction was monitored by TLC and LCMS. Upon completion of the reaction, it was diluted with DCM and washed with saturated NaHCO$_3$ solution and brine. The organic layer was dried over Na$_2$SO$_4$, filtered and concentrated in vacuo to afford a crude product. It was purified by flash chromatography over silica gel (230-400 mesh size) by using 20-30% ethyl acetate in petroleum ether as eluent to afford tert-butyl N-[(1-benzhydrylazetidin-3-yl)methyl]-N-methyl-carbamate 36-4 (11.0 g, 15.91 mmol) as a brown gum. LCMS (ES$^+$): m/z 367.25 [M+H]$^+$.

Step-4:

A stirred solution of tert-butyl N-[(1-benzhydrylazetidin-3-yl)methyl]-N-methyl-carbamate 36-4 (10.0 g, 27.29 mmol) in methanol (80 mL) was degassed with argon for 10 min. Palladium hydroxide on carbon, 20 wt. % 50% water (11.50 g, 81.86 mmol) was added to the reaction mixture and it was stirred for 24 h at room temperature under H$_2$ atmosphere about 80 psi. Upon completion of the reaction, the reaction mixture was filtered through a celite bed and washed with EtOAc. The filtrate was concentrated in vacuo to get tert-butyl N-(azetidin-3-ylmethyl)-N-methyl-carbamate 36-5 (2.5 g, 7.49 mmol, 27.45% yield) as a brown oil.

Crude NMR of the unstable intermediate 35-5: $^1$H NMR (400 MHz, CDCl$_3$) δ: 3.43-3.34 (m, 4H), 2.83 (s, 3H), 2.68 (bs, 2H), 2.29 (bs, 1H), 1.45 (s, 9H).

Step-5:

To a solution of 4-bromoindoline 34-1 (2.0 g, 10.10 mmol) and N-ethyl-N-isopropyl-propan-2-amine (3.92 g, 30.29 mmol, 5.28 mL) in DCM (20 mL), was added benzyl carbonochloridate (2.58 g, 15.15 mmol) at 0° C. The reaction mixture was stirred at room temperature for 12 h. Upon completion of the reaction, it was diluted with DCM and washed with a saturated NaHCO$_3$ solution and brine. The organic layer was dried over Na$_2$SO$_4$, filtered and concentrated under reduced pressure to afford crude product. It was purified by flash chromatography over silica gel (230-400 mesh size) by using 10-20% ethyl acetate in petroleum ether as eluent to afford benzyl 4-bromoindoline-1-carboxylate 34-2 (2.5 g, 7.38 mmol, 73.04% yield) as a pale-yellow gum. LCMS (ES$^+$): m/z 334.14 [M+H]$^+$.

Step-6:

To a solution of benzyl 4-bromoindoline-1-carboxylate 34-2 (2.0 g, 6.02 mmol, 1 eq.) and tert-butyl N-(azetidin-3-ylmethyl)-N-methyl-carbamate 36-5 (1.21 g, 6.02 mmol, 1 eq.) in 1,4-dioxane (20 mL) was added sodium 2-methyl-propan-2-olate (1.16 g, 12.04 mmol, 2 eq.) at room temperature. The reaction mixture was degassed with nitrogen gas for 10 minutes and bis(tri-tert-butylphosphine)palladium (0) (30.77 mg, 60.21 mol, 0.01 eq.) was added. The reaction mixture was degassed with nitrogen gas for additional 5 minutes and stirred at 110° C. for 2 h. The reaction mixture was filtered through a celite bed and washed with ethyl acetate (100 mL). The organic layer was washed with water (50 mL) and brine (50 mL), dried over Na$_2$SO$_4$, filtered and concentrated in vacuo to get the crude product, which was purified by column chromatography using Davisil silica and 25% ethyl acetate in petroleum ether as an eluent to afford benzyl 4-[3-[[tert-butoxycarbonyl(methyl)amino]methyl]azetidin-1-yl]indoline-1-carboxylate 36-6 (1.78 g, 3.55 mmol, 58.93% yield) as a colourless gum. LCMS (ES$^+$): m/z 452.51 [M+H]$^+$.

Step-7:

To a stirred solution of benzyl 4-[3-[[tert-butoxycarbonyl (methyl)amino]methyl]azetidin-1-yl]indoline-1-carboxylate 36-6 (1.6 g, 3.54 mmol, 1 eq.) in EtOAc (10 mL) and THF (10 mL) was added palladium hydroxide on carbon, 20 wt. % 50% water (497.62 mg, 3.54 mmol, 20%) at room temperature, and the reaction mixture was degassed with argon for 5 min and stirred for 16 h at room temperature under H$_2$-balloon pressure. Upon completion of the reaction, the reaction mixture was filtered through a celite bed, washed with DCM and EtOAc. The filtrate was evaporated under reduced pressure to get tert-butyl N-[(1-indolin-4-ylazetidin-3-yl)methyl]carbamate 36-7 (0.90 g, 2.70 mmol, 76.18% yield) as a brown solid. LCMS (ES$^+$): m/z 318.74 [M+H]$^+$.

Step-8:

To a stirred solution of tert-butyl N-[(1-indolin-4-ylazetidin-3-yl)methyl]-N-methyl-carbamate 36-7 (0.90 g, 2.84 mmol, 1 eq.) and 3-bromopiperidine-2,6-dione 12-8 (1.63 g, 8.51 mmol, 3 eq.) in DMF (6 mL) was added sodium hydrogen carbonate, 99% (1.19 g, 14.18 mmol, 551.38 µL, 5 eq.). The reaction mixture was stirred in a sealed tube at 85° C. for 12 h. Upon completion of the reaction, the reaction mixture was poured in ice cooled water. The product was extracted using EtOAc. The organic layer was washed with cooled brine to get the crude product. It was purified by column chromatography over silica gel (230-400 mesh) by using 0-100% EtOAc in petroleum ether as an eluent to get tert-butyl N-[[1-[1-(2,6-dioxo-3-piperidyl)indolin-4-yl]azetidin-3-yl]methyl]-N-methyl-carbamate 36-8 (0.90 g, 2.06 mmol, 72.59% yield) as a light-yellow solid. The product was confirmed by LCMS. LCMS (ES+): m/z 429.34 [M+H]+.

Step-9:

Racemic tert-butyl tert-butyl N-[[1-[1-(2,6-dioxo-3-piperidyl)indolin-4-yl]azetidin-3-yl]methyl]-N-methyl-carbamate 36-8 (0.9 g) was separated by SFC, followed by concentration to give 36-9 (Early eluting peak arbitrarily assigned as S-isomer, 0.4 g) and 36-10 (Late eluting peak arbitrarily assigned as R-isomer, 0.4 g).

Preparative SFC Conditions: column/dimensions: CHIRALCEL OJ-H (30×250) mm, 5µ; % $CO_2$: 75%; % co-solvent: 25% (Acetonitrile); Total Flow: 100 g/min; Back Pressure: 100 bar; Temperature: 30° C.; UV: 234 nm; Solubility: Acetonitrile.

Scheme 37: Synthesis of 3-(4-piperazin-1-ylindolin-1-yl)piperidine-2,6-dione

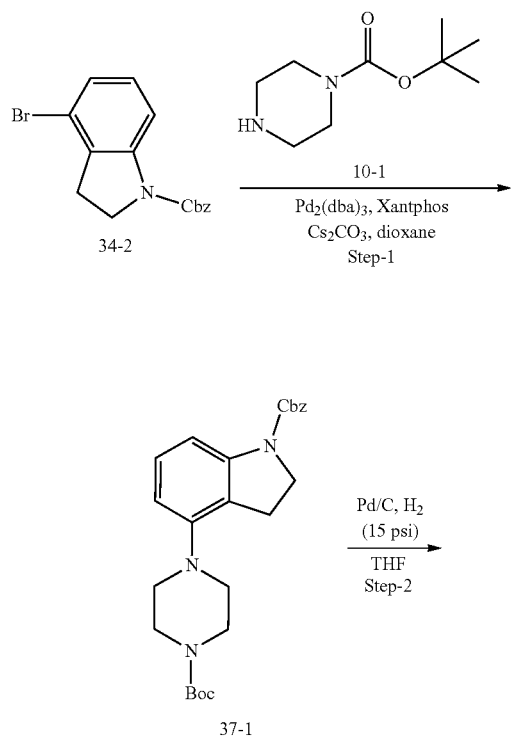

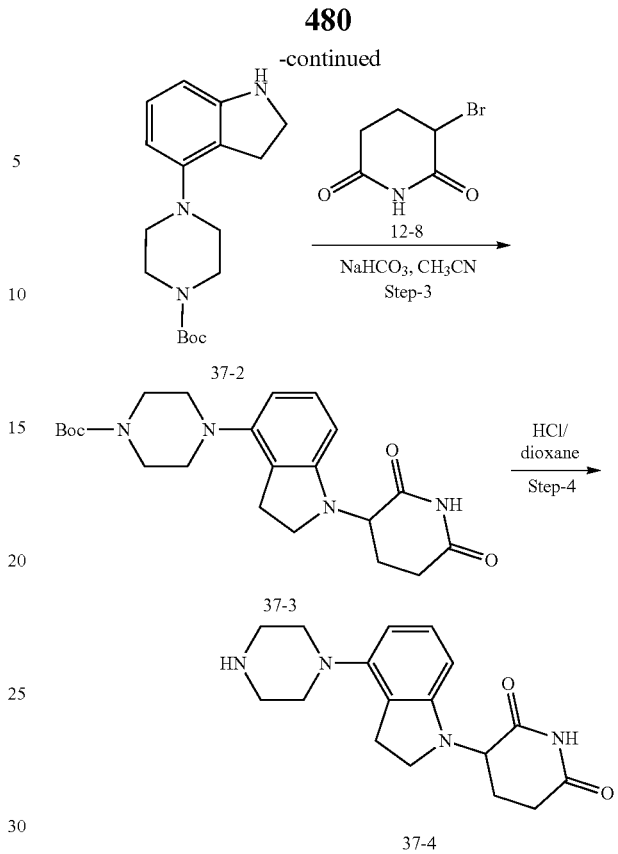

Step-1:

To a solution of tert-butyl piperazine-1-carboxylate 10-1 (672.81 mg, 3.61 mmol) and benzyl 4-bromoindoline-1-carboxylate 34-2 (1 g, 3.01 mmol) in dioxane (15 mL) was added cesium carbonate (1.96 g, 6.02 mmol) and (1E,4E)-1,5-diphenylpenta-1,4-dien-3-one palladium (275.66 mg, 301.03 mol) and (5-diphenylphosphanyl-9,9-dimethyl-xanthen-4-yl)-diphenyl-phosphane (348.36 mg, 602.06 mol) at 15° C. After addition, the solution was stirred under $N_2$ at 90° C. for 12 h. The reaction mixture was concentrated under reduced pressure and the residue was purified by column chromatography ($SiO_2$, petroleum ether/ethyl acetate=100/1 to 5/1) to afford benzyl 4-(4-(tert-butoxycarbonyl)piperazin-1-yl)indoline-1-carboxylate 37-1 (540 mg, 1.17 mmol, 38.95% yield) as a yellow oil. LCMS (ES+): m/z 438.2 [M+H]+.

Step-2:

To a solution of benzyl 4-(4-(tert-butoxycarbonyl)piperazin-1-yl)indoline-1-carboxylate 37-1 (500 mg, 1.14 mmol) in THF (10 mL) was added Pd/C (2.30 mg, 1.14 mmol). The mixture was purged with $H_2$ three times and stirred at 20° C. for 16 h under $H_2$ pressure (15 psi). Upon completion, the reaction mixture was filtered; and the filtrate was concentrated under vacuum to give tert-butyl 4-(indolin-4-yl)piperazine-1-carboxylate 37-2 (250 mg, 741.60 mol, 64.89% yield) as a yellow solid. LCMS (ES+): m/z 304.2 [M+H]+.

Step-3:

To a solution of tert-butyl 4-indolin-4-ylpiperazine-1-carboxylate 37-2 (250 mg, 824.00 mol) and 3-bromopiperidine-2,6-dione 12-8 (237.32 mg, 1.24 mmol) in $CH_3CN$ (0.5 mL) was added $NaHCO_3$ (207.66 mg, 2.47 mmol). The mixture was stirred at 90° C. for 12 h. Water (5 ml) and MBTE (2.5 ml) were added, and it was stirred at 20° C. for 0.5 h. The mixture was filtered and the filter cake was dried under vacuum to give tert-butyl 4-(1-(2,6-dioxopiperidin-3-yl)indolin-4-yl)piperazine-1-carboxylate 37-3 (200 mg, 434.26 mol, 52.70% yield) as a a green solid. LCMS (ES+): m/z 415.2 [M+H]+.

Step-4:

To a solution of tert-butyl 4-[1-(2,6-dioxo-3-piperidyl)indolin-4-yl]piperazine-1-carboxylate 37-3 (180 mg, 434.26 mol) in DCM (2 mL) was added HCl/dioxane (434.26 mol, 2 mL). The mixture was stirred at 25° C. for 0.5 h. The reaction mixture was concentrated under reduced pressure to afford 3-(4-piperazin-1-ylindolin-1-yl)piperidine-2,6-dione 37-4 (152 mg, 433.24 mol, 99.77% yield, HCl salt) as a green solid. LCMS (ES+): m/z 315.2 [M+H]+.

Scheme 38: Synthesis of tert-butyl 2-[1-[1-[(3S)-2,6-dioxo-3-piperidyl]indolin-4-yl]-4-hydroxy-4-piperidyl]acetate and tert-butyl 2-[1-[1-[(3R)-2,6-dioxo-3-piperidyl]indolin-4-yl]-4-hydroxy-4-piperidyl]acetate

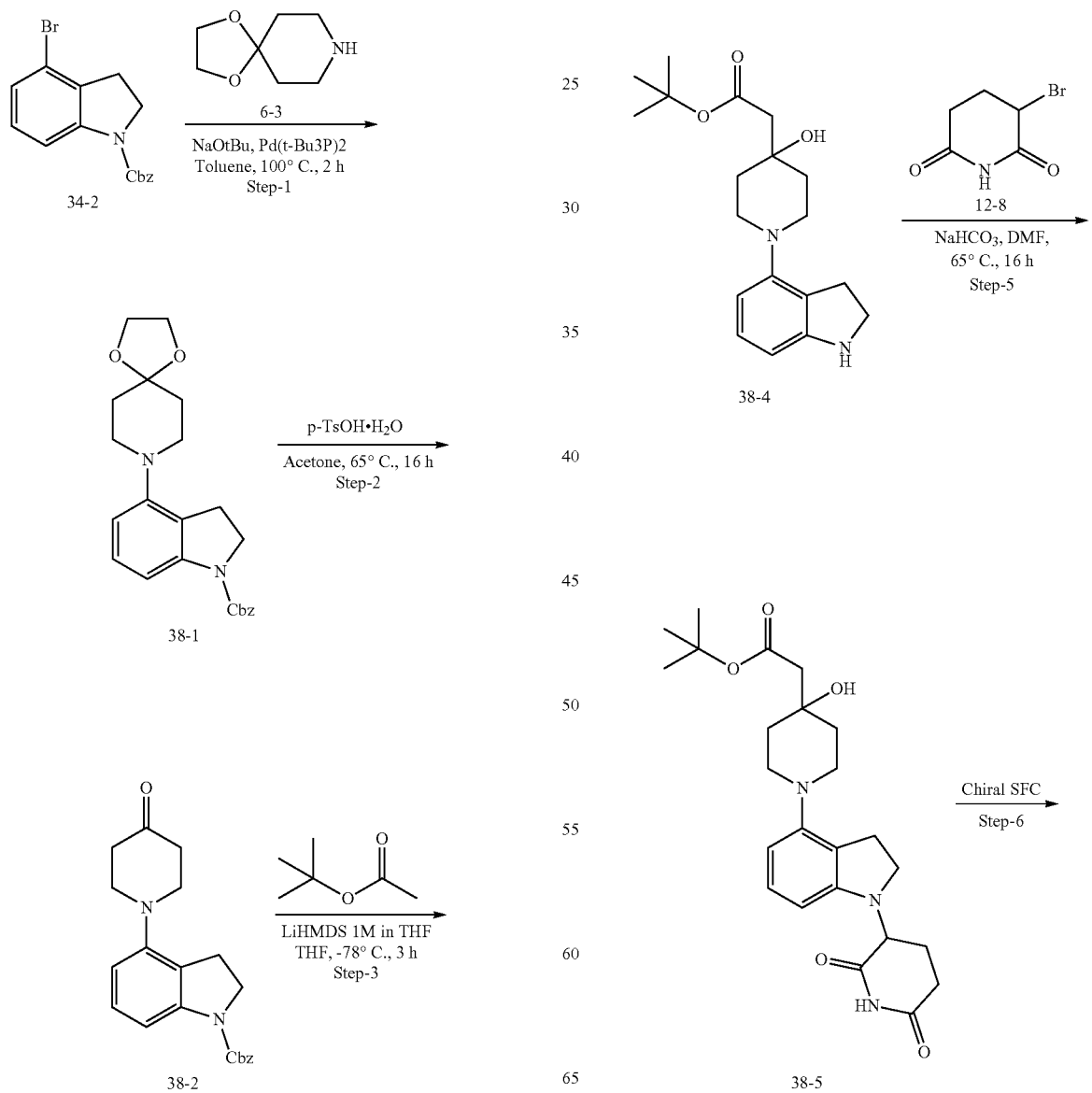

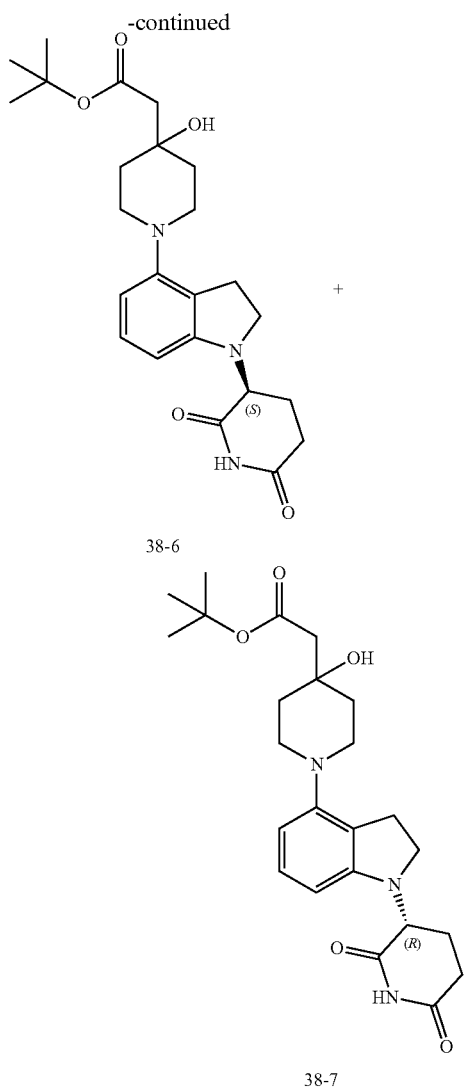

Step-1:

To a stirred solution of benzyl 4-bromoindoline-1-carboxylate 34-2 (7 g, 21.07 mmol) and 1,4-dioxa-8-azaspiro[4.5]decane 6-3 (3.02 g, 21.07 mmol, 2.69 mL) in toluene (60 mL) was added sodium tert-butoxide (5.06 g, 52.68 mmol) at 25° C. under nitrogen atmosphere. The reaction mixture was degassed with $N_2$ gas for 10 min. To the reaction mixture was added bis(tri-tert-butylphosphine)palladium (0) (107.69 mg, 210.72 mol) and again degassed with nitrogen for 5 min. The reaction mixture was stirred at 100° C. for 2 h. After consumption of the starting material as indicated by LCMS, the reaction mixture was cooled to room temperature and was diluted with ethyl acetate (150 mL) and filtered through a celite pad. The filtrate was concentrated under reduced pressure to get the crude which was purified through column chromatography (silica gel, 100-200 mesh) using 0 to 20% EtOAc in hexane as eluent to afford benzyl 4-(1,4-dioxa-8-azaspiro[4.5]decan-8-yl)indoline-1-carboxylate 38-1 (3.3 g, 8.19 mmol, 38.85% yield) as an off white solid. LCMS (ES$^+$): m/z 395.4 [M+H]$^+$.

Step-2:

To a stirred solution of benzyl 4-(1,4-dioxa-8-azaspiro[4.5]decan-8-yl)indoline-1-carboxylate 38-1 (3.3 g, 8.37 mmol) in acetone (30 mL) and water (10 mL), was added 4-methylbenzenesulfonic acid monohydrate (795.66 mg, 4.18 mmol) under nitrogen atmosphere at room temperature and the resulting reaction mixture was stirred at 65° C. for 16 h. After consumption of the starting material as indicated by LCMS, the reaction mixture was cooled to room temperature and was diluted with ethyl acetate (150 mL). The organic layer was washed with sat. aq. NaHCO$_3$ solution (50 mL), brine (50 mL) and dried over anhydrous sodium sulfate, filtered, and concentrated under reduced pressure to obtain crude roduct. The crude was purified by column chromatography (silica gel, 100-200 mesh) using 0-100% ethyl acetate in hexane as eluent to afford benzyl 4-(4-oxo-1-piperidyl)indoline-1-carboxylate 38-2 (2.5 g, 6.07 mmol, 72.50% yield) as a pale liquid. LCMS (ES$^+$): m/z 351.4 [M+H]$^+$.

Step-3:

To a stirred solution of tert-butyl acetate (2.29 g, 19.69 mmol, 2.65 mL) in THF (30 mL) at −78° C. was added dropwise a solution of LiHMDS (1M in THF, 9.85 mL) under nitrogen atmosphere at room temperature and the resulting reaction mixture was stirred at −78° C. for 1 h. Benzyl 4-(4-oxo-1-piperidyl)indoline-1-carboxylate 38-2 (2.3 g, 6.56 mmol) in THF (10 mL) was added to the reaction mixture at −78° C. The reaction mixture was stirred at −78° C. for 3 h. After consumption of the starting material as indicated by UPLC-MS, the reaction mixture was allowed warm to 0° C. and the reaction mixture was quenched with sat. aq. NH$_4$Cl (50 mL) and extracted with EtOAc (2×100 mL). The combined organic layer was washed with brine solution (150 mL), dried over anhydrous sodium sulfate, and concentrated under reduced pressure to obtain crude. The crude was purified by column chromatography (silica gel, 100-200 mesh) using 0-100% ethyl acetate in hexane as eluent to afford benzyl 4-[4-(2-tert-butoxy-2-oxo-ethyl)-4-hydroxy-1-piperidyl]indoline-1-carboxylate 38-3 (2.2 g, 4.51 mmol, 68.74% yield) as a white solid. LCMS (ES$^+$): m/z 467.2 [M+H]$^+$.

Step-4:

To a stirred solution of benzyl 4-[4-(2-tert-butoxy-2-oxo-ethyl)-4-hydroxy-1-piperidyl]indoline-1-carboxylate 38-3 (2 g, 4.29 mmol) in THF (30 mL) was added palladium, 10% on carbon wet (1.82 g, 17.15 mmol) at 25° C. under nitrogen atmosphere. The resulting suspension was stirred at room temperature under hydrogen atmosphere (balloon) for 16 h. After consumption of the starting material as indicated by UPLC-MS, the reaction mixture was diluted with THF (250 mL) and filtered through a pad of celite. The celite bed was washed with methanol thoroughly (100 mL). The combined filtrate was concentrated under reduced pressure to get tert-butyl 2-(4-hydroxy-1-indolin-4-yl-4-piperidyl)acetate 38-4 (1.32 g, 2.84 mmol, 66.29% yield) as a grey liquid. LCMS (ES$^+$): m/z 333.4 [M+H]$^+$.

Step-5:

To a stirred solution of tert-butyl 2-(4-hydroxy-1-indolin-4-yl-4-piperidyl)acetate 38-4 (1.3 g, 3.91 mmol) and 3-bromopiperidine-2,6-dione 12-8 (3.75 g, 19.55 mmol) in DMF (20 mL) was added NaHCO$_3$ (1.64 g, 19.55 mmol) and the reaction mixture was stirred at 65° C. for 16 h in a sealed tube. After consumption of the starting material as indicated by LCMS, the reaction mixture was poured into ice cold water (20 mL). The precipitated solid was filtered and dried under vacuum to afford tert-butyl 2-[1-[1-(2,6-dioxo-3-piperidyl)indolin-4-yl]-4-hydroxy-4-piperidyl]acetate 38-5 (1.6 g, 3.40 mmol, 86.83% yield) as grey solid. LCMS (ES$^+$): m/z 444.2 [M+H]$^+$.

Step-6:

Enantiomers of racemic tert-butyl 2-[1-[1-(2,6-dioxo-3-piperidyl) idolin-4-yl]-4-hydroxy-4-piperidyl]acetate 38-5 (1.6 g, 3.40 mmol) were separated by chiral SFC [SFC chiral purification method: column: I-cellulose B (250×30) mm, 5 um; mobile phase: 90:40 (CO$_2$: co-Solvent), co-solvent: acetonitrile; flow rate: 90 mL/min; wavelength: 210 nm]. The early eluting peak (arbitrarily assigned as S) tert-butyl 2-[1-[1-[(3S)-2,6-dioxo-3-piperidyl]indolin-4-yl]-4-hydroxy-4-piperidyl]acetate 38-6 (330 mg, 735.02 mol, 20.38% yield, 100% enantiopurity) isolated as an off white solid. LCMS (ES$^+$): m/z 444.2 [M+H]$^+$. $^1$H NMR (400 MHz, DMSO-d$_6$): δ 10.77 (s, 1H), 6.88 (t, J=8.00 Hz, 1H), 6.24 (d, J=8.00 Hz, 1H), 6.18 (d, J=7.60 Hz, 1H), 4.58 (dd, J=4.80, 13.20 Hz, 1H), 4.47 (s, 1H), 3.43-3.36 (m, 1H), 3.30-3.21 (m, 1H), 2.99-2.74 (m, 7H), 2.61-2.53 (m, 1H), 2.35 (s, 2H), 2.24-2.12 (m, 1H), 1.95-1.87 (m, 1H), 1.81-1.62 (m, 4H), 1.42 (s, 9H). The late eluting peak (arbitrarily assigned as R) tert-butyl 2-[1-[1-[(3R)-2,6-dioxo-3-piperidyl]indolin-4-yl]-4-hydroxy-4-piperidyl]acetate 38-7 (210 mg, 457.66 μmol, 12.69% yield, 100% enantiopurity) isolated as an off white solid. LCMS (ES$^+$): m/z 444.2 [M+H]$^+$. $^1$H NMR (400 MHz, DMSO-d$_6$): δ 10.77 (s, 1H), 6.88 (t, J=8.00 Hz, 1H), 6.24 (d, J=7.60 Hz, 1H), 6.18 (d, J=7.60 Hz, 1H), 4.58 (dd, J=4.80, 13.20 Hz, 1H), 4.47 (s, 1H), 3.42-3.35 (m, 1H), 3.30-3.21 (m, 1H), 2.99-2.90 (m, 3H), 2.89-2.75 (m, 4H), 2.60-2.53 (m, 1H), 2.35 (s, 2H), 2.24-2.13 (m, 1H), 1.94-1.88 (m, 1H), 1.81-1.64 (m, 4H), 1.42 (s, 9H).

Scheme 39: Synthesis of tert-butyl 2-[1-[1-[(3S)-2,6-dioxo-3-piperidyl]indolin-4-yl]-4-piperidyl]acetate and tert-butyl 2-[1-[1-[(3R)-2,6-dioxo-3-piperidyl]indolin-4-yl]-4-piperidyl]acetate

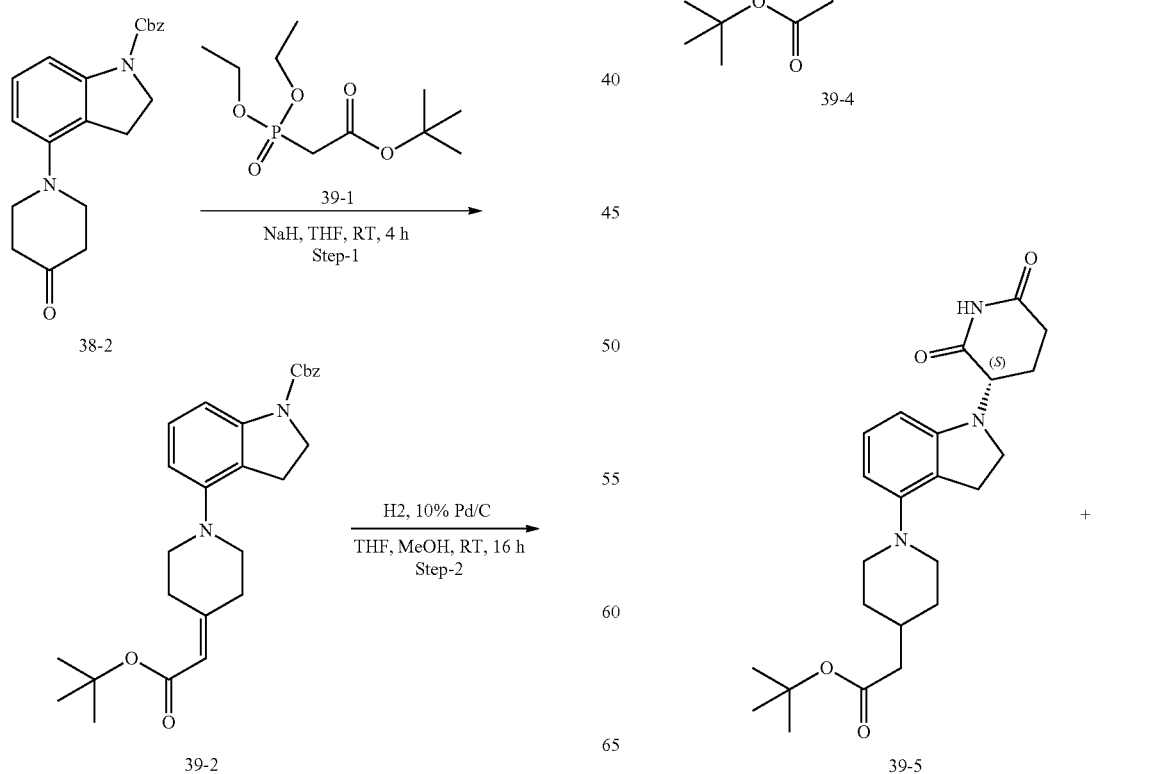

-continued

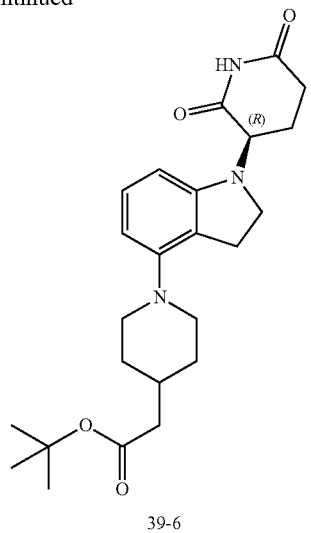

39-6

Step-1:

To a stirred solution of tert-butyl 2-diethoxyphosphorylacetate 39-1 (2.92 g, 11.56 mmol, 2.72 mL) in THF (30 mL) at 0° C., was added sodium hydride (60% dispersion in mineral oil, 177.14 mg, 7.71 mmol) portionwise, and then the reaction mixture was stirred at 0° C. for 30 min. A solution of benzyl 4-(4-oxo-1-piperidyl)indoline-1-carboxylate 38-2 (2.7 g, 7.71 mmol) in THF (10 mL) was added and the reaction mixture was stirred at room temperature for 4 h. The reaction mixture was quenched with water (20 mL) and extracted with ethyl acetate (50 mL). The organic layer was washed with brine solution (20 mL), dried over anhydrous sodium sulfate, and concentrated under reduced pressure to obtain crude product. The crude product was purified by column chromatography (silica gel, 100-200 mesh) using 0-100% ethyl acetate in hexane as an eluent to afford benzyl 4-[4-(2-tert-butoxy-2-oxo-ethylidene)-1-piperidyl]indoline-1-carboxylate 39-2 (3 g, 6.40 mmol, 83.03% yield) as an off white solid. LCMS (ES+): m/z 449.4 [M+H]+.

Step-2:

To a stirred solution of benzyl 4-[4-(2-tert-butoxy-2-oxo-ethylidene)-1-piperidyl]indoline-1-carboxylate 39-2 (2.5 g, 5.57 mmol) in THF (50 mL) and methanol (50 mL), was added 10% palladium on carbon (2.37 g, 22.29 mmol) at room temperature under nitrogen atmosphere. The resulting suspension was stirred at room temperature under hydrogen atmosphere (balloon pressure) for 16 h. The reaction mixture was filtered through celite bed and washed with THF (30 mL). The filtrate was concentrated under reduced pressure to obtain crude. The crude was purified by column chromatography (silica gel, 100-200 mesh) using 0-100% ethyl acetate in hexane as an eluent to afford tert-butyl 2-(1-indolin-4-yl-4-piperidyl)acetate 39-3 (510 mg, 1.45 mmol, 26.01% yield) as a grey liquid. LCMS (ES+): m/z 317.2 [M+H]+.

Step-3:

To a stirred solution of tert-butyl 2-(1-indolin-4-yl-4-piperidyl)acetate 39-3 (500 mg, 1.58 mmol), 3-bromopiperidine-2,6-dione 12-8 (1.52 g, 7.90 mmol) in DMF (5 mL), was added sodium hydrogen carbonate (663.69 mg, 7.90 mmol) and the reaction mixture was stirred at 65° C. for 16 h in a sealed tube. The reaction mixture was quenched with ice cold water (50 mL), the precipitated solids were filtered and dried, to obtain tert-butyl 2-[1-[1-(2,6-dioxo-3-piperidyl)indolin-4-yl]-4-piperidyl]acetate 39-4 (590 mg, 1.20 mmol, 75.83% yield) as a grey solid. LCMS (ES+): m/z 428.3 [M+H]+.

Step-4:

Enantiomers of racemic tert-butyl 2-[1-[1-(2,6-dioxo-3-piperidyl)indolin-4-yl]-4-piperidyl]acetate 39-4 (590 mg) were separated through chiral SFC [Chiral SFC purification method: column: I-cellulose B (250×30)mm, 5 um; flow rate: 90 mL/min; mobile phase: 90:40 ($CO_2$:co-solvent); co-solvent: acetonitrile; wavelength: 210 nm]. The early eluting peak (arbitrarily assigned as S) tert-butyl 2-[1-[1-[(3S)-2,6-dioxo-3-piperidyl]indolin-4-yl]-4-piperidyl]acetate 39-5 (140 mg, 327.00 mol, 23.70% yield, 100% enantiopurity) was isolated as an off white solid. LCMS (ES+): m/z 428.2 [M+H]+. $^1$H NMR (400 MHz, DMSO-$d_6$): δ 10.77 (s, 1H), 6.88 (t, J=7.60 Hz, 1H), 6.23 (d, J=8.00 Hz, 1H), 6.19 (d, J=8.00 Hz, 1H), 4.58 (dd, J=4.80, 12.80 Hz, 1H), 3.42-3.35 (m, 1H), 3.29-3.17 (m, 3H), 2.84-2.76 (m, 3H), 2.65-2.50 (m, 3H), 2.24-2.13 (m, 3H), 1.94-1.87 (m, 1H), 1.79-1.68 (m, 3H), 1.42 (s, 9H), 1.36-1.21 (m, 2H). The late eluting peak (arbitrarily assigned as R) tert-butyl 2-[1-[1-[(3R)-2,6-dioxo-3-piperidyl]indolin-4-yl]-4-piperidyl]acetate 39-6 (118 mg, 271.75 mol, 19.69% yield, 100% enantiopurity) was isolated as an off white solid. LCMS (ES+): m/z 428.2 [M+H]+. $^1$H NMR (400 MHz, DMSO-$d_6$): δ 10.77 (s, 1H), 6.88 (t, J=8.00 Hz, 1H), 6.23 (d, J=8.00 Hz, 1H), 6.19 (d, J=8.00 Hz, 1H), 4.58 (dd, J=4.80, 13.20 Hz, 1H), 3.42-3.35 (m, 1H), 3.31-3.18 (m, 4H), 2.86-2.75 (m, 3H), 2.62-2.52 (m, 2H), 2.24-2.13 (m, 3H), 1.94-1.88 (m, 1H), 1.79-1.68 (m, 3H), 1.42 (s, 9H), 1.38-1.21 (m, 2H).

Scheme 40: Synthesis of tert-butyl 4-[1-[(3R)-2,6-dioxo-3-piperidyl]indolin-5-yl]piperidine-1-carboxylate and tert-butyl 4-[1-[(3S)-2,6-dioxo-3-piperidyl]indolin-5-yl]piperidine-1-carboxylate

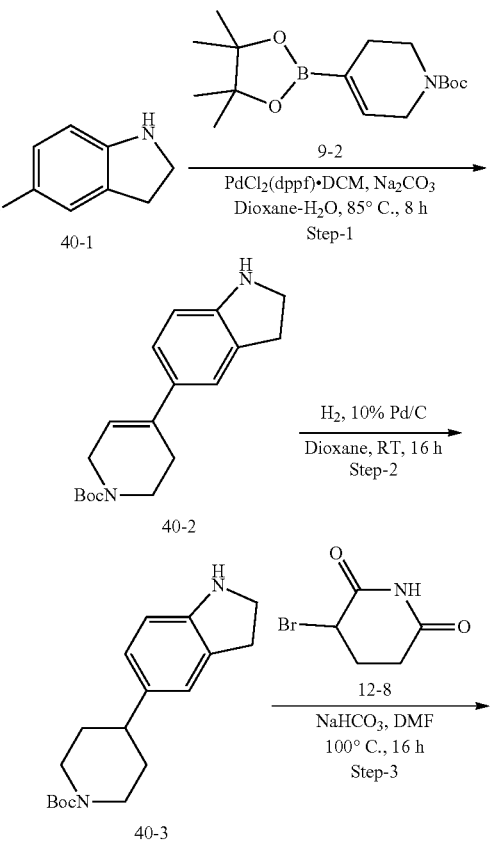

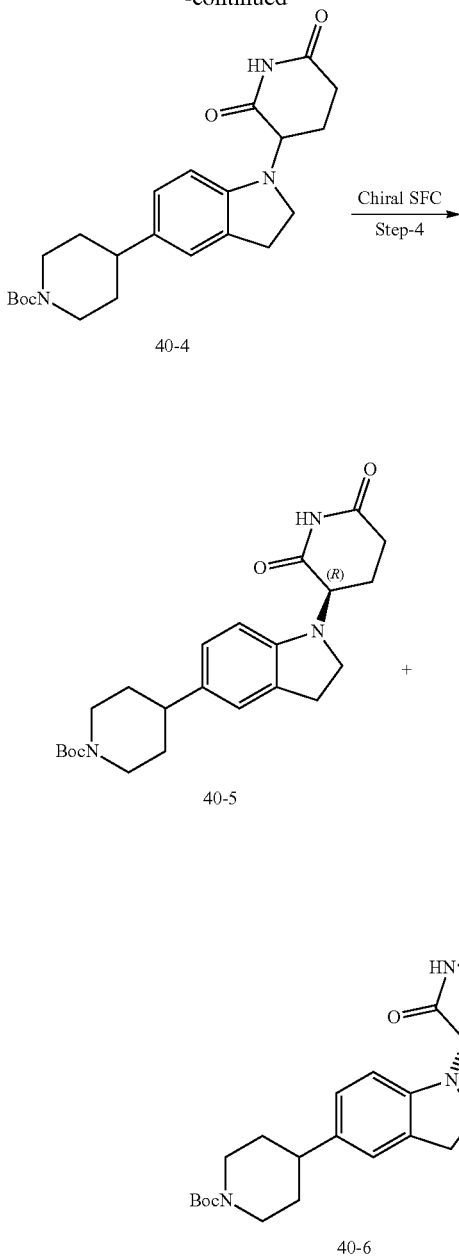

40-4

40-5

40-6

Step-1:

To a stirred solution of tert-butyl 4-(4,4,5,5-tetramethyl-1,3,2-dioxaborolan-2-yl)-3,6-dihydro-2H-pyridine-1-carboxylate 9-2 (15.61 g, 50.49 mmol) in 1,4-dioxane (60 mL) and water (40 mL), were added 5-bromoindoline 40-1 (10.00 g, 50.49 mmol) and sodium carbonate (14.23 g, 151.47 mmol) at room temperature under nitrogen atmosphere. The reaction mixture was degassed by bubbling with nitrogen for 5 min and then [1,1'-bis(diphenylphosphino)ferrocene]dichloropalladium(II), complex with dichloromethane (2.06 g, 2.52 mmol) was added to the reaction mixture at room temperature. The reaction mixture was again degassed for 5 min and stirred at 85° C. for 8 h. After completion of the reaction as indicated by TLC, the reaction mass was poured into ice water (20 mL). The aqueous layer was extracted with ethyl acetate (50 mL). The organic layer was dried over anhydrous sodium sulfate, filtered, and concentrated under reduced pressure to obtain crude. The crude was purified by flash silica gel column chromatography, using 0-100% ethyl acetate in hexane as eluent to afford tert-butyl 4-indolin-5-yl-3,6-dihydro-2H-pyridine-1-carboxylate 40-2 (9.8 g, 32.62 mmol, 64.61% yield) as an off-white solid. LCMS (ES$^+$): m/z 301.4 [M+H]$^+$.

Step-2:

To a stirred solution of tert-butyl 4-indolin-5-yl-3,6-dihydro-2H-pyridine-1-carboxylate 40-2 (8 g, 26.63 mmol) in 1,4-dioxane (100 mL) was added palladium, 10% on carbon (4 g, 26.63 mmol) at room temperature under nitrogen atmosphere. The reaction mixture was stirred under the pressure of hydrogen gas (balloon pressure) at room temperature for 16 h. After completion of the reaction, reaction mixture was diluted with MeOH (200 mL), filtered through celite bed and the resulting filtrate was concentrated under reduced pressure to obtain crude. The crude was purified by column chromatography (silica gel, 230-400 mesh), using 0-100% ethyl acetate in pet ether as eluent to afford tert-butyl 4-indolin-5-ylpiperidine-1-carboxylate 40-3 (4.8 g, 14.26 mmol, 53.55% yield) as a yellow solid. LCMS (ES$^+$): m/z 247.2 [M–tBu+H]$^+$.

Step-3:

To a stirred solution of tert-butyl 4-indolin-5-yl-3,6-dihydro-2H-pyridine-1-carboxylate 40-3 (5 g, 16.64 mmol) in DMF (50 mL) were added sodium bicarbonate (4.19 g, 49.93 mmol) and 3-bromopiperidine-2,6-dione 12-8 (4.79 g, 24.97 mmol) at room temperature under nitrogen atmosphere. The reaction mixture was stirred at 100° C. for 16 h. After completion of reaction, reaction mixture was concentrated under reduced pressure, dissolved in DCM (50 mL) and washed with water (2×50 mL). The organic layer was dried over anhydrous sodium sulfate, filtered, and concentrated under reduced pressure to obtain crude. The crude was purified by column chromatography (silica gel, 100-200 mesh), using 0-100% ethyl acetate in pet ether as eluent to afford tert-butyl 4-[1-(2,6-dioxo-3-piperidyl)indolin-5-yl]piperidine-1-carboxylate 40-4 (2.3 g, 5.10 mmol, 30.64% yield) as a brown solid. LCMS (ES$^+$): m/z 414.4 [M+H]$^+$.

Step-4:

Compound tert-butyl 4-[1-(2,6-dioxo-3-piperidyl)indolin-5-yl]piperidine-1-carboxylate 40-4 (1 g, 2.20 mmol) was purified by chiral SFC to separate R- and S-isomers [Column: I Cellulose J, flow rate: 4 mL/min, elution: 80:20 (CO$_2$:Co-solvent), Co-solvent: 0.2% formic acid in acetonitrile/isopropanol]. The early eluting peak (arbitrarily assigned as R) tert-butyl 4-[1-[(3R)-2,6-dioxo-3-piperidyl]indolin-5-yl]piperidine-1-carboxylate 40-5 (420 mg, 998.43 mol, 45.37% yield, 95.44% enantiopurity) was isolated as a light blue solid. LCMS (ES$^+$): m/z 358.2 [M–tBu+H]$^+$. $^1$H NMR (400 MHz, DMSO-d$_6$): δ 10.76 (brs, 1H), 6.90 (s, 1H), 6.80 (dd, J=1.20, 8.00 Hz, 1H), 6.40 (d, J=8.00 Hz, 1H), 4.58 (dd, J=4.80, 12.80 Hz, 1H), 4.12-4.01 (m, 2H), 3.83-3.73 (m, 1H), 3.44-3.38 (m, 1H), 3.31-3.22 (m, 1H), 2.96-2.68 (m, 5H), 2.62-2.53 (m, 1H), 2.25-2.11 (m, 1H), 1.93-1.85 (m, 1H), 1.72-1.66 (m, 2H), 1.47-1.35 (m, 11H). The late eluting peak (arbitrarily assigned as S) tert-butyl 4-[1-[(3S)-2,6-dioxo-3-piperidyl]indolin-5-yl]piperidine-1-carboxylate 40-6 (210 mg, 462.65 mol, 21.02% yield, 93.36% enantiopurity) was isolated as a brown solid. LCMS

491

(ES$^+$): m/z 358.2 [M−tBu+H]$^+$. $^1$H NMR (400 MHz, DMSO-d$_6$): δ 10.75 (brs, 1H), 6.90 (s, 1H), 6.80 (d, J=9.20 Hz, 1H), 6.40 (d, J=8.00 Hz, 1H), 4.58 (dd, J=4.80, 13.20 Hz, 1H), 4.11-4.02 (m, 2H), 3.43-3.22 (m, 3H), 2.94-2.70 (m, 5H), 2.61-2.53 (m, 1H), 2.24-2.12 (m, 1H), 1.95-1.86 (m, 1H), 1.74-1.65 (m, 2H), 1.46-1.34 (m, 11H).

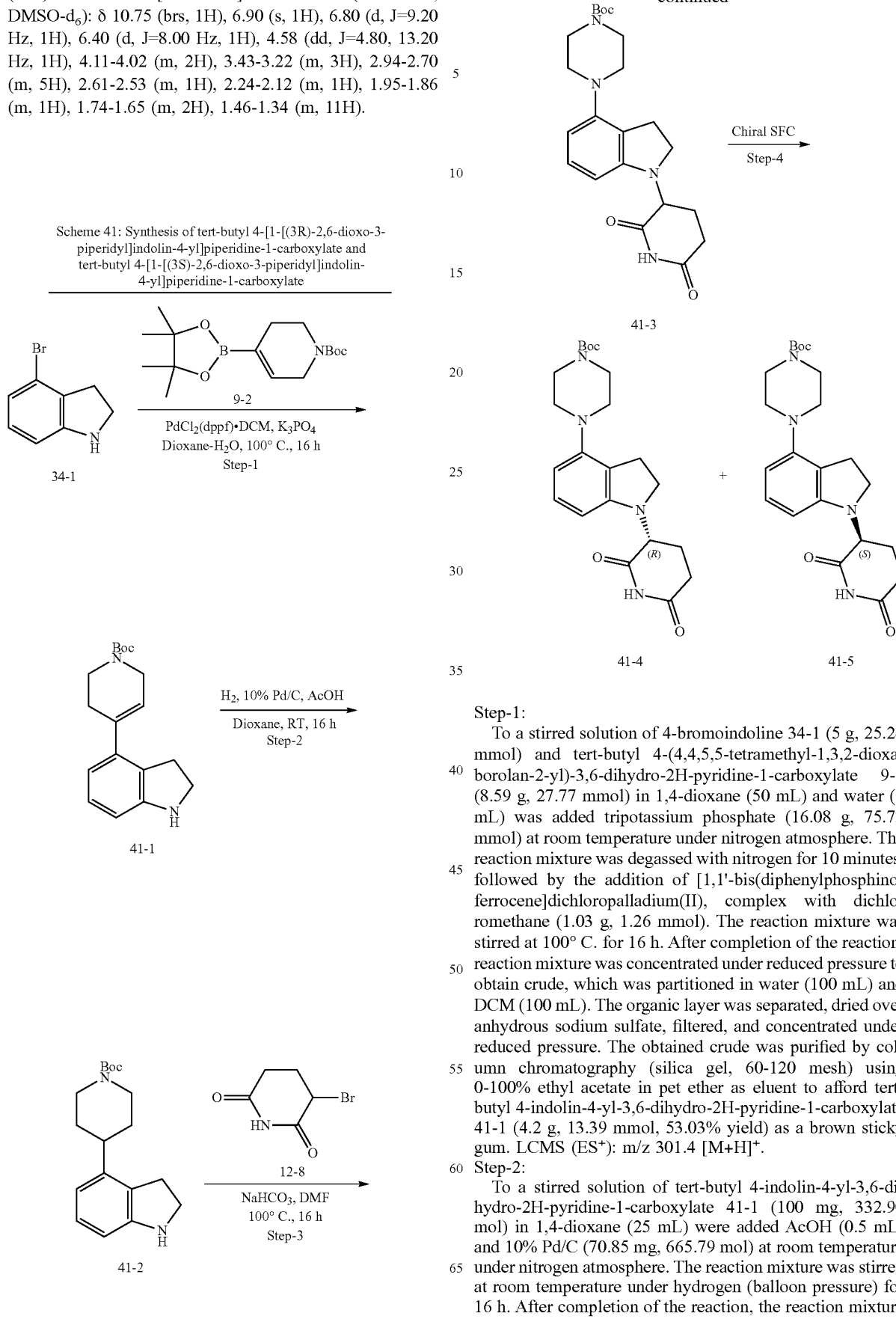

492

Step-1:

To a stirred solution of 4-bromoindoline 34-1 (5 g, 25.24 mmol) and tert-butyl 4-(4,4,5,5-tetramethyl-1,3,2-dioxaborolan-2-yl)-3,6-dihydro-2H-pyridine-1-carboxylate 9-2 (8.59 g, 27.77 mmol) in 1,4-dioxane (50 mL) and water (5 mL) was added tripotassium phosphate (16.08 g, 75.73 mmol) at room temperature under nitrogen atmosphere. The reaction mixture was degassed with nitrogen for 10 minutes, followed by the addition of [1,1'-bis(diphenylphosphino)ferrocene]dichloropalladium(II), complex with dichloromethane (1.03 g, 1.26 mmol). The reaction mixture was stirred at 100° C. for 16 h. After completion of the reaction, reaction mixture was concentrated under reduced pressure to obtain crude, which was partitioned in water (100 mL) and DCM (100 mL). The organic layer was separated, dried over anhydrous sodium sulfate, filtered, and concentrated under reduced pressure. The obtained crude was purified by column chromatography (silica gel, 60-120 mesh) using 0-100% ethyl acetate in pet ether as eluent to afford tert-butyl 4-indolin-4-yl-3,6-dihydro-2H-pyridine-1-carboxylate 41-1 (4.2 g, 13.39 mmol, 53.03% yield) as a brown sticky gum. LCMS (ES$^+$): m/z 301.4 [M+H]$^+$.

Step-2:

To a stirred solution of tert-butyl 4-indolin-4-yl-3,6-dihydro-2H-pyridine-1-carboxylate 41-1 (100 mg, 332.90 mol) in 1,4-dioxane (25 mL) were added AcOH (0.5 mL) and 10% Pd/C (70.85 mg, 665.79 mol) at room temperature under nitrogen atmosphere. The reaction mixture was stirred at room temperature under hydrogen (balloon pressure) for 16 h. After completion of the reaction, the reaction mixture was filtered through celite bed and washed with DCM (100 mL). The resulting filtrate was concentrated under reduced pressure and dried to afford tert-butyl 4-indolin-4-ylpiperidine-1-carboxylate 41-2 (70 mg, 192.12 mol, 57.71% yield) as an off-white solid. LCMS (ES⁺): m/z 247.2 [M–tBu+H]⁺.

Step-3:

To a stirred solution of tert-butyl 4-indolin-4-ylpiperidine-1-carboxylate 41-2 (1 g, 3.10 mmol) in DMF (10 mL) were added sodium hydrogen carbonate (781.29 mg, 9.30 mmol) and 3-bromopiperidine-2,6-dione 12-8 (892.88 mg, 4.65 mmol) at room temperature under nitrogen atmosphere. The reaction mixture was stirred at 100° C. for 16 h. After completion of the reaction, reaction mixture was concentrated under reduced pressure. The resulting crude was dissolved in DCM (50 mL) and washed with water (2×50 mL). The organic layer was separated, dried over anhydrous sodium sulfate, filtered, and concentrated under reduced pressure to obtain crude. The crude was purified by column chromatography (silica gel, 230-400 mesh) using 80% ethyl acetate in pet ether as eluent to afford 650 mg of the title product 41-3 as a brown solid.

Step-4:

Compound tert-butyl 4-indolin-4-ylpiperidine-1-carboxylate 41-3 (1 g, 3.10 mmol) was purified by chiral SFC to separate R- and S-isomers [Column: Cellulose-B (250*30 mm; 5.0 um), flow rate: 100 mL/min, Elution: 60:40 (CO₂: co-solvent), co-solvent: 0.2% formic acid in isopropanol: acetonitrile (50:50)]. The early eluting peak (arbitrarily assigned as R) tert-butyl 4-[1-[(3R)-2,6-dioxo-3-piperidyl]indolin-4-yl]piperidine-1-carboxylate 41-4 (330 mg, 702.97 mol, 22.68% yield, 100% enantiopurity) was obtained as an off white solid. LCMS (ES⁺): m/z 358.3 [M–tBu+H]⁺. ¹H NMR (400 MHz, DMSO-d₆): δ 10.78 (s, 1H), 6.91 (t, J=7.60 Hz, 1H), 6.43 (d, J=7.60 Hz, 1H), 6.33 (d, J=8.00 Hz, 1H), 4.61 (dd, J=4.80, 12.80 Hz, 1H), 4.14-4.04 (m, 2H), 3.46-3.39 (m, 1H), 3.35-3.24 (m, 1H), 3.01-2.72 (m, 5H), 2.65-2.52 (m, 2H), 2.25-2.14 (m, 1H), 1.95-1.88 (m, 1H), 1.74-1.64 (m, 2H), 1.55-1.37 (m, 11H). The late eluting peak (arbitrarily assigned as S) tert-butyl 4-[1-[(3S)-2,6-dioxo-3-piperidyl]indolin-4-yl]piperidine-1-carboxylate 41-5 (220 mg, 459.50 mol, 14.82% yield, 98.42% enantiopurity) was obtained as a brown solid. LCMS (ES⁺): m/z 358.2 [M–tBu+H]⁺. ¹H NMR (400 MHz, DMSO-d₆): δ 10.78 (s, 1H), 6.91 (t, J=7.60 Hz, 1H), 6.43 (d, J=7.60 Hz, 1H), 6.33 (d, J=8.00 Hz, 1H), 4.61 (dd, J=4.80, 12.80 Hz, 1H), 4.14-4.03 (m, 2H), 3.46-3.26 (m, 2H), 3.01-2.72 (m, 5H), 2.65-2.52 (m, 2H), 2.25-2.14 (m, 1H), 1.95-1.88 (m, 1H), 1.74-1.64 (m, 2H), 1.55-1.37 (m, 11H).

Scheme 42: Synthesis of 3-[4-[4-(2-hydroxyethyl)-1-piperidyl]indolin-1-yl]piperidine-2,6-dione, (3S)-3-[4-[4-(2-hydroxyethyl)-1-piperidyl]indolin-1-yl]piperidine-2,6-dione and (3R)-3-[4-[4-(2-hydroxyethyl)-1-piperidyl]indolin-1-yl]piperidine-2,6-dione

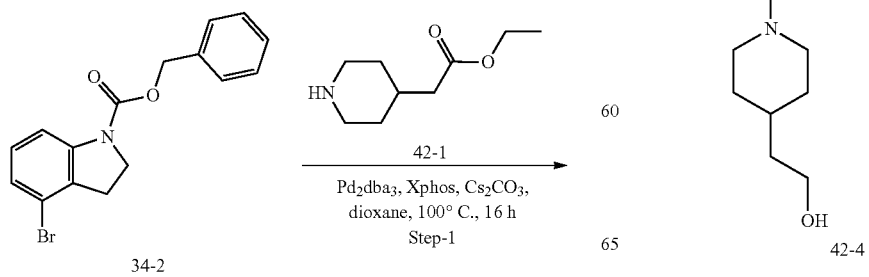

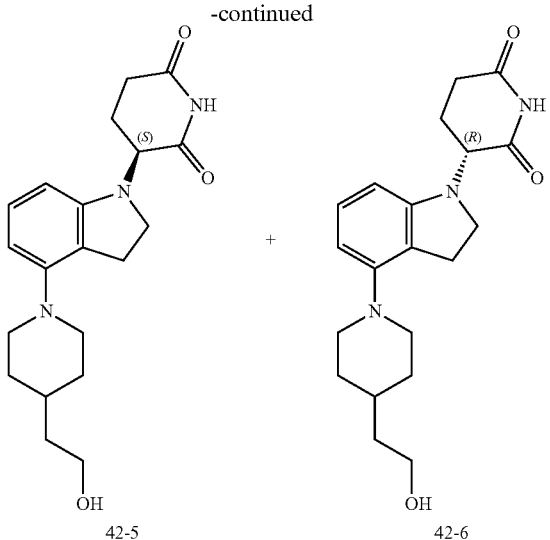

42-5 + 42-6

Step-1:

To a stirred solution of benzyl 4-bromoindoline-1-carboxylate 34-2 (3 g, 9.03 mmol) and ethyl 2-(4-piperidyl) acetate 42-1 (2.32 g, 13.55 mmol) in 1,4-dioxane (30 mL) were added cesium carbonate (8.83 g, 27.09 mmol) and dicyclohexyl-[2-(2,4,6-triisopropylphenyl)phenyl]phosphane (861.05 mg, 1.81 mmol) at room temperature in a sealed tube. The reaction mixture was degassed with nitrogen for 10 minutes, added (1E,4E)-1,5-diphenylpenta-1,4-dien-3-one; palladium (826.98 mg, 903.09 mol) and degassed again with nitrogen for 2 min. The resulting reaction mixture was stirred at 100° C. for 16 h. After completion of the reaction, the reaction mass was filtered through a celite pad, and the filtrate was concentrated under reduced pressure to get crude. The crude was purified by silica gel column chromatography (100-200 mesh) using 0-100% ethyl acetate as an eluent to afford benzyl 4-[4-(2-ethoxy-2-oxo-ethyl)-1-piperidyl]indoline-1-carboxylate 42-2 (2.1 g, 4.44 mmol, 49.21% yield) as a yellow solid. LCMS (ES$^+$): m/z 423.2 [M+H]$^+$.

Step-2:

To a stirred solution of benzyl 4-[4-(2-ethoxy-2-oxo-ethyl)-1-piperidyl]indoline-1-carboxylate 42-2 (1 g, 2.12 mmol) in THF (30 mL) was added lithium borohydride (2.0 M in THF, 3.17 mL) at 0° C. The reaction mixture was stirred at room temperature for 16 h. The reaction mixture was quenched with satd. aq. Na$_2$SO$_4$ solution (5 ml), diluted with ethyl acetate (100 mL), and the precipitated solid was filtered. The filtrate was dried over anhydrous Na$_2$SO$_4$, filtered and concentrated under reduced pressure to obtain crude. The crude was purified by column chromatography (silica gel, 100-200 mesh) using 0-100% ethyl acetate-hexane as an eluent to afford 2-(1-indolin-4-yl-4-piperidyl)ethanol 42-3 (380 mg, 1.46 mmol, 69.07% yield) as a pale yellow solid. LCMS (ES$^+$): m/z 247.2 [M+H]$^+$.

Step-3:

To a stirred solution of 2-(1-indolin-4-yl-4-piperidyl)ethanol 42-3 (350 mg, 1.35 mmol) in DMF (10 mL), was added sodium hydrogen carbonate (565.50 mg, 6.73 mmol) followed by 3-bromopiperidine-2,6-dione 12-8 (1.29 g, 6.73 mmol) at room temperature. The reaction mixture stirred at 65° C. for 16 h. The reaction mixture diluted with ethyl acetate (100 mL) and filtered through a celite pad. The filtrate was quenched with water (100 mL) and extracted with ethyl acetate (2×100 mL). The separated organic layers were combined, washed with brine solution (50 mL) and dried over anhydrous Na$_2$SO$_4$, filtered and concentrated under reduced pressure to obtain crude residue. The crude product was purified by silica gel column chromatography (100-200 mesh) using 0-100% ethyl acetate-hexane as eluent to afford 3-[4-[4-(2-hydroxyethyl)-1-piperidyl]indolin-1-yl]piperidine-2,6-dione 42-4 (450 mg, 1.18 mmol, 87.40% yield) as a brown solid. LCMS (ES$^+$): m/z 358.2 [M+H]$^+$.

Step 4:

Enantiomers of 3-[4-[4-(2-hydroxyethyl)-1-piperidyl]indolin-1-yl]piperidine-2,6-dione 42-4 (450 mg, 1.18 mmol) were separated by chiral SFC [SFC chiral purification method: Column: Reflect I-Cellulose B, co-solvent name: acetonitrile, co solvent: 45%; Flow rate: 5 ml/min, temperature: 35° C., outlet pressure: 100 bar]. The early eluting peak (arbitrarily assigned as S) (3S)-3-[4-[4-(2-hydroxyethyl)-1-piperidyl]indolin-1-yl]piperidine-2,6-dione 42-5 (150 mg, 413.31 mol, 35.12% yield, 100% enantiopurity) as a brown solid. LCMS (ES$^+$): m/z 358.2 [M+H]$^+$. $^1$H NMR (400 MHz, DMSO-d$_6$): δ 10.77 (s, 1H), 6.88 (t, J=8.00 Hz, 1H), 6 6.23 (d, J=8.00 Hz, 1H), 6.18 (d, J=7.60 Hz, 1H), 4.58 (dd, J=4.80, 13.20 Hz, 1H), 4.36 (t, J=4.80 Hz, 1H), 3.52-3.46 (m, 2H), 3.42-3.35 (m, 1H), 3.28-3.17 (m, 3H), 2.86-2.73 (m, 3H), 2.63-2.52 (m, 3H), 2.21-2.14 (m, 1H), 1.95-1.86 (m, 1H), 1.78-1.68 (m, 2H), 1.52-1.38 (m, 3H), 1.31-1.19 (m, 2H). The late eluting peak (arbitrarily assigned as R) (3R)-3-[4-[4-(2-hydroxyethyl)-1-piperidyl]indolin-1-yl]piperidine-2,6-dione 42-6 (160 mg, 446.64 mol, 37.96% yield, enantiopurity 100%) as a brown solid. LCMS (ES$^+$): m/z 358.2 [M+H]$^+$. $^1$H NMR (400 MHz, DMSO-d$_6$): δ 10.76 (s, 1H), 6.88 (t, J=8.00 Hz, 1H), 6 6.23 (d, J=8.00 Hz, 1H), 6.18 (d, J=7.60 Hz, 1H), 4.58 (dd, J=4.80, 12.80 Hz, 1H), 4.36 (t, J=4.80 Hz, 1H), 3.53-3.45 (m, 2H), 3.41-3.37 (m, 1H), 3.29-3.17 (m, 3H), 2.87-2.73 (m, 3H), 2.61-2.54 (m, 3H), 2.22-2.13 (m, 1H), 1.95-1.86 (m, 1H), 1.78-1.67 (m, 2H), 1.52-1.33 (m, 3H), 1.31-1.18 (m, 2H).

Scheme 43: Synthesis of (3S)-3-[4-[4-(hydroxy-1-piperidyl)indolin-1-yl]piperidine-2,6-dione and (3R)-3-[4-[4-(hydroxy-1-piperidyl)indolin-1-yl]piperidine-2,6-dione

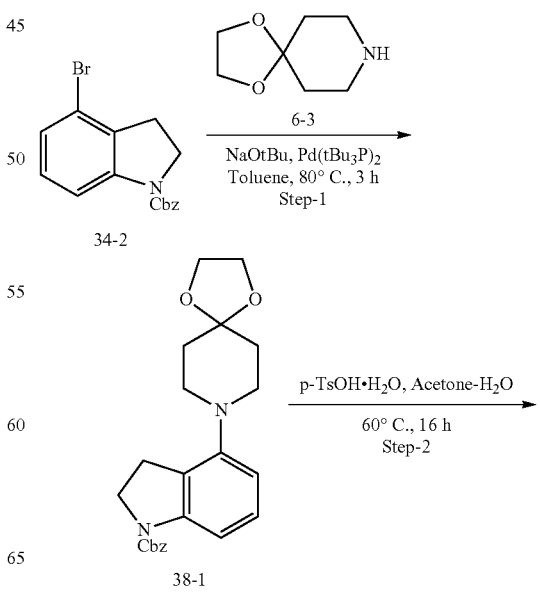

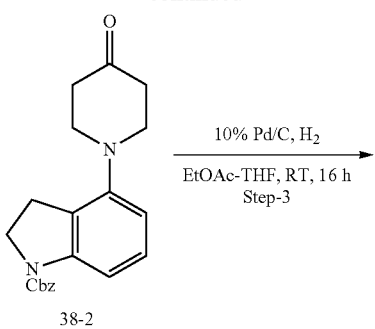

38-2

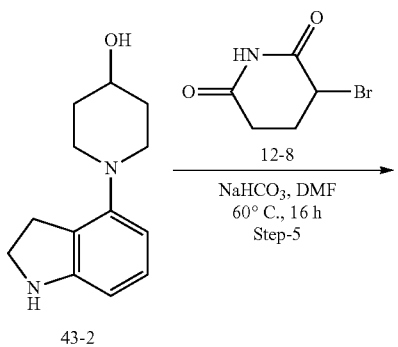

43-1

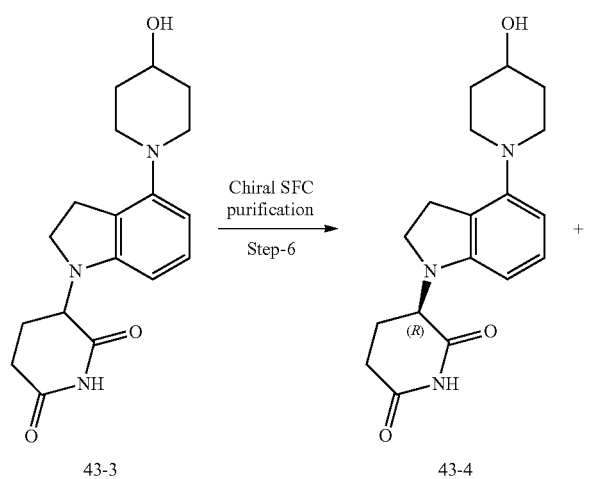

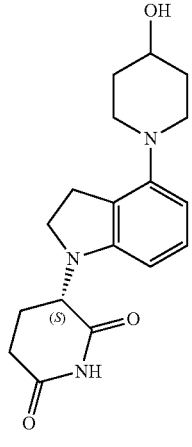

43-5

Step-1:
To a stirred solution of benzyl 4-bromo indoline-1-carboxylate 34-2 (5 g, 15.05 mmol) and 1,4-dioxa-8-azaspiro[4.5]decane 6-3 (2.80 g, 19.57 mmol, 2.51 mL) in toluene (150 mL) was added sodium tert-butoxide (48.35 mg, 503.06 mol) at room temperature under nitrogen atmosphere. The reaction mixture was purged with nitrogen for 10 min, followed by the addition of bis(tri-tert-butyl phosphine)palladium (0) (384.61 mg, 752.58 mol). The reaction mixture was stirred at 80° C. for 3 h. After completion of the reaction, the reaction mixture was cooled to room temperature, filtered through celite pad, and washed with ethyl acetate (100 mL). The resulting filtrate was washed with water (2×100 mL), dried over anhydrous sodium sulfate, filtered, and concentrated under reduced pressure to obtain crude. The crude was purified by column chromatography (silica gel, 230-400 mesh) using 0-100% ethyl acetate in hexane as eluent to afford benzyl 4-(1,4-dioxa-8-azaspiro[4.5]decan-8-yl)indoline-1-carboxylate 38-1 (5.5 g, 12.40 mmol, 82.38% yield) as a pale brown solid. LCMS (ES+): m/z 395.2 [M+H]+.

Step-2:
To a stirred solution of benzyl 4-(1,4-dioxa-8-azaspiro[4.5]decan-8-yl)indoline-1-carboxylate 38-1 (4 g, 10.14 mmol) in acetone (26.93 mL) and water (8.98 mL) was added 4-methylbenzenesulfonic acid, monohydrate (964.44 mg, 5.07 mmol) at room temperature. The reaction mixture was stirred at 60° C. for 16 h. After completion of the reaction, the reaction mixture was cooled to room temperature, diluted with water (40 mL) and extracted with ethyl acetate (3×80 mL). The combined organic layer was washed with satd. aq. sodium bicarbonate solution (50 mL), dried over anhydrous sodium sulfate, filtered, and concentrated under reduced pressure to obtain crude. The crude was purified by column chromatography (silica gel, 230-400 mesh) using 0-100% ethyl acetate in pet ether as eluent to afford benzyl 4-(4-oxo-1-piperidyl)indoline-1-carboxylate 38-2 (3 g, 8.19 mmol, 80.78% yield) as a colorless gum. LCMS (ES+): m/z 351.2 [M+H]+.

Step-3:
To a stirred solution of benzyl 4-(4-oxo-1-piperidyl)indoline-1-carboxylate 38-2 (1 g, 2.85 mmol) in THF (15 mL) and ethyl acetate (15 mL) was added palladium, 10% on carbon (607.40 mg, 5.71 mmol) at room temperature under nitrogen atmosphere. The reaction mixture was stirred under the hydrogen atmosphere (balloon pressure) at room temperature for 16 h. After completion of the reaction, the reaction mixture was filtered through celite pad, washed with ethyl acetate (100 mL), and the combined filtrate was concentrated under reduced pressure to obtain crude. The crude was purified by column chromatography (silica gel, 100-200 mesh) using 0-100% ethyl acetate in hexane as eluent to afford 1-indolin-4-ylpiperidin-4-one 43-1 (280 mg, 1.19 mmol, 41.74% yield) as a pale brown solid. LCMS (ES$^+$): m/z 217.2[M+2H]$^+$. $^1$H NMR (400 MHz, CDCl$_3$): δ 7.02 (t, J=8.00 Hz, 1H), 6.45-6.39 (m, 2H), 3.61 (t, J=8.00 Hz, 2H), 3.36 (t, J=6.40 Hz, 4H), 3.06 (t, J=8.40 Hz, 2H), 2.60 (t, J=6.00 Hz, 4H).

Step-4:

To a stirred solution of 1-indolin-4-ylpiperidin-4-one 43-1 (1 g, 4.62 mmol) in methanol (20 mL) was added sodium borohydride (349.83 mg, 9.25 mmol) at 0° C. under nitrogen atmosphere. The reaction mixture was stirred at room temperature for 2 h. After completion of the reaction, the reaction mixture was quenched sat. aq. ammonium chloride solution (10 mL), extracted with ethyl acetate (2×30 mL). The combined organic layer was dried over anhydrous sodium sulfate, filtered, and concentrated under reduced pressure to obtain crude. The crude was purified by column chromatography (silica gel, 230-400 mesh) using 0-100% ethyl acetate in hexane as eluent to afford 1-indolin-4-ylpiperidin-4-ol 43-2 (580 mg, 2.66 mmol, 57.46% yield) as an off-white solid. $^1$H NMR (400 MHz, DMSO-d$_6$): δ 6.81 (t, J=7.60 Hz, 1H), 6.21-6.16 (m, 2H), 5.29 (s, 1H), 4.63 (d, J=4.00 Hz, 1H), 3.62-3.55 (m, 1H), 3.38-3.33 (m, 2H), 3.16-3.11 (m, 2H), 2.79 (t, J=8.40 Hz, 2H), 2.67-2.59 (m, 2H), 1.85-1.79 (m, 2H), 1.54-1.44 (m, 2H).

Step-5:

To a stirred solution of 1-indolin-4-ylpiperidin-4-ol 43-2 (580 mg, 2.66 mmol) in DMF (6 mL) were added sodium bicarbonate (669.64 mg, 7.97 mmol) and 3-bromopiperidine-2,6-dione 12-8 (1.53 g, 7.97 mmol) at room temperature under nitrogen atmosphere. The reaction mixture was stirred at 60° C. for 16 h. After completion, the reaction mixture was quenched with water (20 mL) and extracted with ethyl acetate (2×50 mL). The combined organic layer was dried over anhydrous sodium sulfate, filtered, and concentrated under reduced pressure to obtain crude. The crude was purified by column chromatography (silica gel, 230-400 mesh) using 0-100% ethyl acetate in hexane as eluent to afford 3-[4-(4-hydroxy-1-piperidyl)indolin-1-yl] piperidine-2,6-dione 43-3 (440 mg, 1.18 mmol, 44.53% yield) as a pale green solid. UPLC-MS (ES$^+$): m/z 330.2 [M+H]$^+$.

Step-6:

3-[4-(4-hydroxy-1-piperidyl)indolin-1-yl]piperidine-2,6-dione 43-3 (60 mg, 161.35 mol) was purified by chiral SFC to separate R- and S-enantiomers [Chiral SFC purification method: Column: Cellulose-B, (250*30 mm, 5.0 u), flow rate: 100 mL/min, mobile phase: 60:40 (CO$_2$:co-solvent), co-solvent: 0.2% formic acid in isopropanol:acetonitrile (1:1)]. The early eluting peak (arbitrarily assigned as S) (3S)-3-[4-(4-hydroxy-1-piperidyl)indolin-1-yl]piperidine-2, 6-dione 43-5 (15 mg, 45.27 mol, 28.05% yield, 100% enantiopurity). UPLC-MS (ES$^+$): m/z 330.2 [M+H]$^+$. $^1$H NMR (400 MHz, DMSO-d$_6$): δ 10.77 (s, 1H), 6.87 (t, J=8.00 Hz, 1H), 6.25-6.16 (m, 2H), 4.64 (d, J=4.40 Hz, 1H), 4.58 (dd, J=4.80, 12.80 Hz, 1H), 3.62-3.56 (m, 1H), 3.42-3.38 (m, 1H), 3.29-3.23 (m, 1H), 3.18-3.09 (m, 2H), 2.85-2.73 (m, 3H), 2.68-2.53 (m, 3H), 2.23-2.12 (m, 1H), 1.94-1.79 (m, 3H), 1.55-1.46 (m, 2H). The late eluting peak (arbitrarily assigned as R) (3R)-3-[4-(4-hydroxy-1-piperidyl)indolin-1-yl]piperidine-2,6-dione 43-4 (14.5 mg, 43.99 mol, 27.26% yield, 100% enantiopurity). UPLC-MS (ES$^+$): m/z 330.2. $^1$H NMR (400 MHz, DMSO-d$_6$): δ 10.77 (s, 1H), 6.87 (t, J=8.00 Hz, 1H), 6.24-6.17 (m, 2H), 4.64 (d, J=4.40 Hz, 1H), 4.58 (dd, J=4.80, 12.80 Hz, 1H), 3.62-3.55 (m, 1H), 3.41-3.35 (m, 1H), 3.29-3.12 (m, 1H), 3.17-3.09 (m, 2H), 2.85-2.73 (m, 3H), 2.70-2.53 (m, 3H), 2.25-2.10 (m, 1H), 1.94-1.79 (m, 3H), 1.55-1.44 (m, 2H).

Scheme 44: Synthesis of tert-butyl N-[1-[5-fluoro-1-[(3S)-2,6-dioxo-3-piperidyl]indolin-4-yl]-4-piperidyl]-N-methylcarbamate and tert-butyl N-[1-[5-fluoro-1-[(3R)-2,6-dioxo-3-piperidyl]indolin-4-yl]-4-piperidyl]-N-methylcarbamate

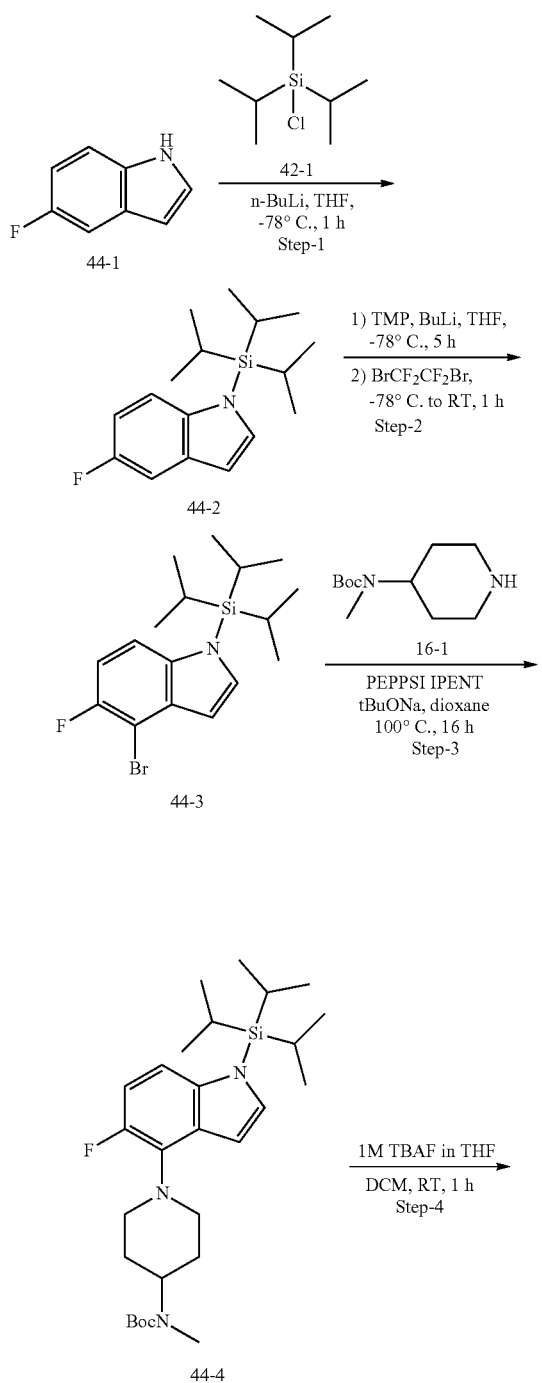

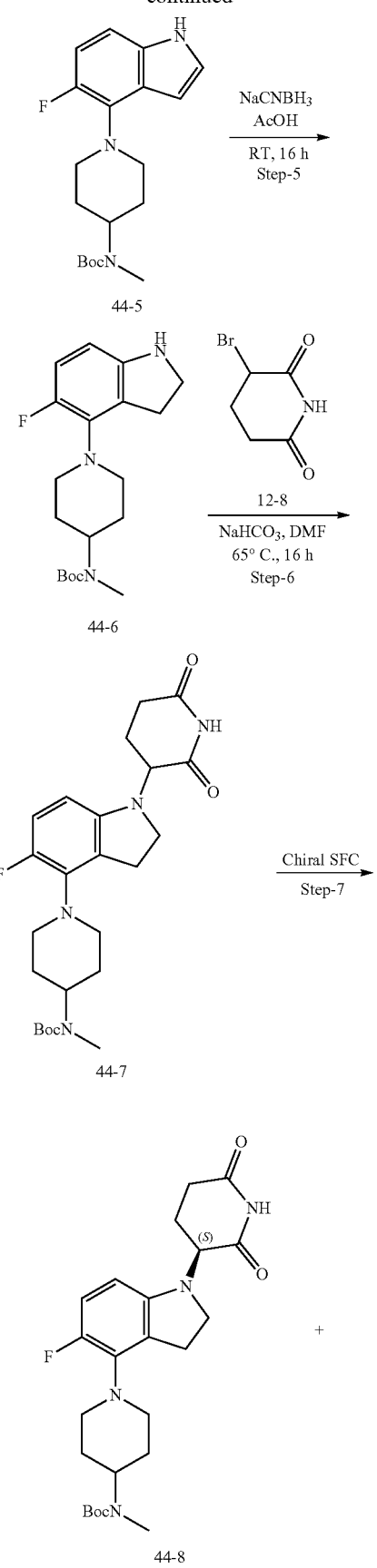

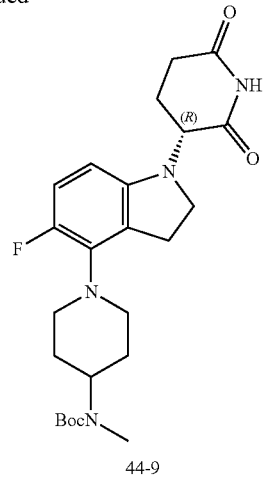

44-9

Step-1:

To a stirred solution of 5-fluoro-1H-indole 44-1 (2.5 g, 18.50 mmol) and chloro(triisopropyl)silane (3.92 g, 20.35 mmol) in THF (75 mL) was added dropwise a solution of n-butyl lithium (2.5 M in hexane, 8.88 mL) at −78° C. and stirred for 1 h. After completion of the reaction, the reaction mixture was quenched with ice water (50 mL) and extracted with ethyl acetate (100 mL). The organic layer was washed with brine (50 mL), dried over Na$_2$SO$_4$, filtered, and concentrated under reduced pressure to give (5-fluoroindol-1-yl)-triisopropyl-silane 44-2 (5 g, 16.59 mmol, 89.67% yield) as a pale-yellow oil. LCMS (ES$^+$): m/z 292.2 [M+H]$^+$.

Step-2: Into a two neck 250 mL round bottom flask, under N$_2$, taken THF (80 mL) and n-butyl lithium (2.5 M in hexane, 13.27 mL) and cooled to −78° C. To this stirred solution, 2,2,6,6-tetramethylpiperidine (TMP) (4.69 g, 33.18 mmol, 5.60 mL), N-[2-(dimethyl amino)ethyl]-N,N,N-trimethyl-ethane-1,2-diamine (5.75 g, 33.18 mmol) and (5-fluoroindol-1-yl)-triisopropyl-silane 44-2 (4 g, 13.27 mmol) were added and stirred for 5 h at −78° C. Then the reaction mixture was treated with 1,2-dibromo-1,1,2,2-tetrafluoro-ethane (3.79 g, 14.60 mmol) and allowed to stir for 1 h at room temperature. The reaction mixture was adsorbed on silica gel, purified by flash column chromatography (silica gel, 230-400 mesh), using 0-100% ethyl acetate in hexane as eluent to afford (4-bromo-5-fluoro-indol-1-yl)-triisopropyl-silane 44-3 (4 g, 8.64 mmol, 65.11% yield) as an off-white solid. $^1$H NMR (400 MHz, DMSO-d$_6$): δ 7.58-7.54 (m, 2H), 7.11 (t, J=9.20 Hz, 1H), 6.64 (d, J=3.20 Hz, 1H), 1.80-1.70 (m, 3H), 1.07 (d, J=7.60 Hz, 18H).

Step-3:

To a stirred solution of a mixture of (4-bromo-5-fluoro-indol-1-yl)-triisopropyl-silane 44-3 (3.5 g, 7.56 mmol) and tert-butyl N-methyl-N-(4-piperidyl)carbamate 16-1 (3.24 g, 15.12 mmol) in 1,4-dioxane (120 mL) in a sealed tube, was added sodium tert-butoxide (2.18 g, 22.68 mmol) at ambient temperature. The reaction mixture was degassed with nitrogen for 10 minutes and added PEPPSI™-IPent catalyst (299.25 mg, 378.00 mol). The resulting reaction mixture was heated to 100° C. and stirred for 16 h. After completion of reaction, the reaction mixture was diluted with ethyl acetate (250 mL), washed with water (2×100 mL). The organic layer was dried over anhydrous Na$_2$SO$_4$, filtered and concentrated under reduced pressure to get crude. The crude product was purified by flash chromatography (silica gel, 230-400 mesh), using 0-100% ethyl acetate in hexane as eluent to afford tert-butyl N-[1-(5-fluoro-1-triisopropylsilyl-indol-4-yl)-4-piperidyl]-N-methylcarbamate 44-4 (3.1 g, 5.89 mmol, 77.95% yield) as a colourless gummy solid. LCMS (ES+): m/z 504.4 [M+H]+.

Step-4:

To a stirred solution of tert-butyl N-[1-(5-fluoro-1-triisopropylsilyl-indol-4-yl)-4-piperidyl]-N-methylcarbamate 44-4 (3.1 g, 5.83 mmol) in DCM (30 mL) was added tetrabutylammonium fluoride (TBAF) (1 M in THF, 11.67 mL) at 0° C., the reaction mixture was allowed to stir at room temperature for 1 h. After completion of the reaction, the reaction mixture was concentrated under reduced pressure, and dissolved in ethyl acetate (100 mL). The organic layer was washed with water (2×50 mL), dried over anhydrous Na$_2$SO$_4$, filtered and concentrated under reduced pressure to afford crude. The crude was purified by flash column chromatography (silica gel, 230-400 mesh), using 0-100% ethyl acetate in hexane to afford tert-butyl N-[1-(5-fluoro-1H-indol-4-yl)-4-piperidyl]-N-methylcarbamate 44-5 (1.9 g, 5.39 mmol, 92.32% yield) as a pale brown solid. LCMS (ES+): m/z 348.2 [M+H]+.

Step-5:

To a stirred solution of tert-butyl N-[1-(5-fluoro-1H-indol-4-yl)-4-piperidyl]-N-methylcarbamate 44-5 (1.7 g, 4.80 mmol) in acetic acid (35 mL) was added sodium cyanoborohydride (904.03 mg, 14.39 mmol) at room temperature and stirred for 16 h. After completion of the reaction, the reaction mixture was basified with 10% aq. NaOH solution (pH-7), extracted with ethyl acetate (2×100 mL) and the organic layer was washed with satd. aq. NaHCO$_3$ solution, dried over anhydrous Na$_2$SO$_4$, filtered and concentrated under reduced pressure to afford crude. The crude was purified by silica gel flash column chromatography (230-400 mesh), using 0-100% ethyl acetate in hexane as eluent to afford tert-butyl N-[1-(5-fluoroindolin-4-yl)-4-piperidyl]-N-methylcarbamate 44-6 (1.1 g, 2.99 mmol, 62.42% yield) as a colourless gum. LCMS (ES+): m/z 350.2 [M+H]+.

Step-6:

To a stirred solution of tert-butyl N-[1-(5-fluoroindolin-4-yl)-4-piperidyl]-N-methylcarbamate 44-6 (1 g, 2.72 mmol) in DMF (10 mL) was added sodium bicarbonate (1.14 g, 13.59 mmol) followed by 3-bromopiperidine-2,6-dione 12-8 (2.61 g, 13.59 mmol) at room temperature. Then the reaction mixture was heated to 65° C. and stirred for 16 h. After completion of the reaction, the reaction mixture was filtered through a celite pad, washed with ethyl acetate (100 mL). The filtrate was washed with water (3×50 mL) and brine (50 mL), respectively. The organic layer was dried over anhydrous Na$_2$SO$_4$, filtered and concentrated under reduced pressure to afford the crude, which was purified by flash column chromatography (silica gel, 230-400 mesh), using 0-100% ethyl acetate in hexane to afford tert-butylN-[1-[1-(2,6-dioxo-3-piperidyl)-5-fluoro-indolin-4-yl]-4-piperidyl]-N-methyl-carbamate 44-7 (800 mg, 1.72 mmol, 63.19% yield) as an off-white solid. LCMS (ES+): m/z 461.4 [M+H]+.

Step-7: Enantiomers of tert-butyl N-[1-[1-(2,6-dioxo-3-piperidyl)-5-fluoro-indolin-4-yl]-4-piperidyl]-N-methyl-carbamate 44-7 (800 mg, 1.72 mmol) was separated by chiral SFC [Chiral SFC purification method: Column: R,R Whelk-O (250*30)mm; 5.0 um; mobile phase: CO$_2$:co-solvent [70:30]v/v, co-solvent name:isopropanol-acetonitrile [1:1]v/v; flow rate: 80 ml/min; temperature: 35° C.; outlet pressure: 100 bar; wavelength: 210 nm]. The early eluting peak (arbitrarily assigned as S) tert-butyl N-[1-[5-fluoro-1-[(3S)-2,6-dioxo-3-piperidyl]indolin-4-yl]-4-piperidyl]-N-methylcarbamate 44-8 (280 mg, 604.33 mol, 35.18% yield, 100% enantiopurity) was obtained as an off-white solid. LCMS (ES+): m/z 461.4 [M+H]+. $^1$H NMR (400 MHz, DMSO-d$_6$): δ 10.74 (br s, 1H), 6.70 (dd, J=8.40, 12.80 Hz, 1H), 6.11 (dd, J=3.20, 8.40 Hz, 1H), 4.50 (dd, J=4.80, 12.80 Hz, 1H), 3.45-3.35 (m, 1H), 3.29-3.10 (m, 4H), 3.05-2.90 (m, 4H), 2.81-2.71 (m, 1H), 2.69 (s, 3H), 2.60-2.52 (m, 1H), 2.22-2.06 (m, 1H), 1.98-1.82 (m, 1H), 1.80-1.66 (m, 2H), 1.64-1.50 (m, 2H), 1.39 (s, 9H). The late eluting peak (arbitrarily assigned as R) tert-butyl N-[1-[5-fluoro-1-[(3R)-2,6-dioxo-3-piperidyl]indolin-4-yl]-4-piperidyl]-N-methylcarbamate 44-9 (240 mg, 518.78 mol, 30.20% yield, 100% enantiopurity) as an off-white solid. LCMS (ES+): m/z 461.4 [M+H]+. $^1$H NMR (400 MHz, DMSO-d$_6$): δ 10.74 (s, 1H), 6.70 (dd, J=8.40, 12.80 Hz, 1H), 6.11 (dd, J=3.20, 8.40 Hz, 1H), 4.50 (dd, J=4.80, 12.80 Hz, 1H), 3.45-3.35 (m, 1H), 3.31-3.10 (m, 4H), 3.09-2.85 (m, 4H), 2.80-2.68 (m, 4H), 2.63-2.55 (m, 1H), 2.20-2.05 (m, 1H), 1.99-1.81 (m, 1H), 1.80-1.65 (m, 2H), 1.64-1.49 (m, 2H), 1.39 (s, 9H).

Scheme 45: Synthesis of (3S)-3-[4-(1,4-dioxa-8-azaspiro[4.5]decan-8-yl)indolin-1-yl]piperidi-ne-2,6-dione and (3R)-3-[4-(1,4-dioxa-8-azaspiro[4.5]decan-8-yl)indolin-1-yl]piperidi-ne-2,6-dione

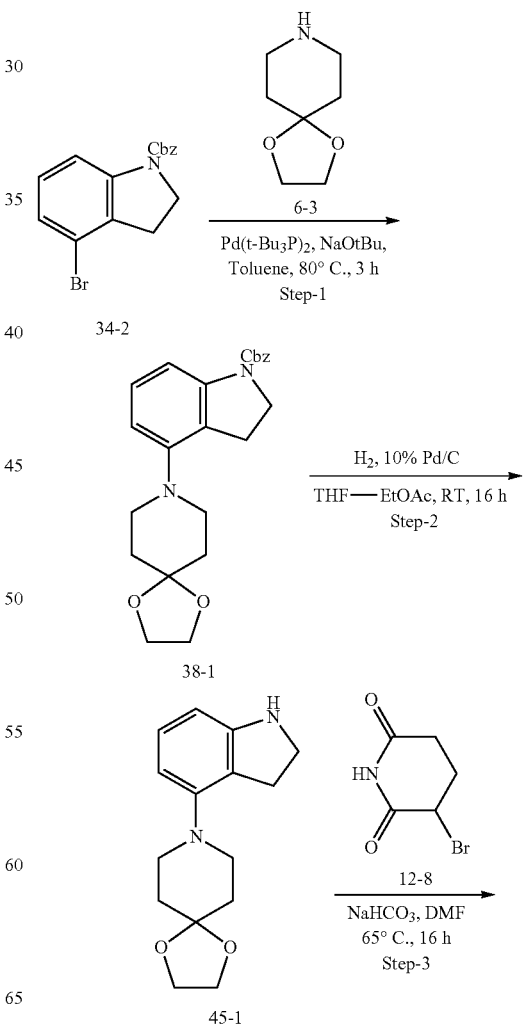

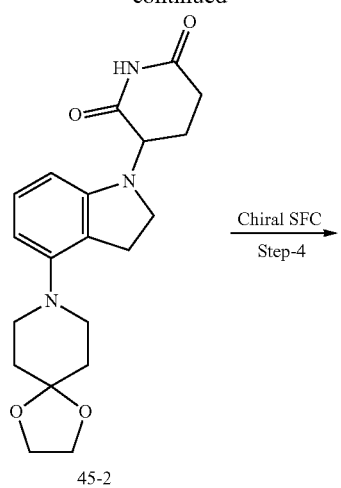

45-2

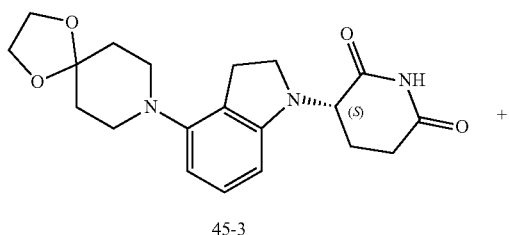

45-3

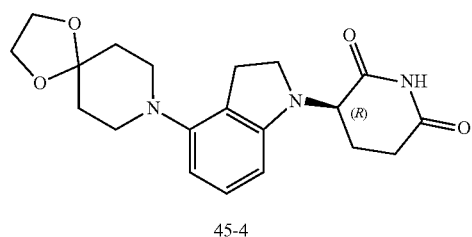

45-4

Step-1:

To a stirred solution of a mixture of benzyl 4-bromoindoline-1-carboxylate 34-2 (5 g, 15.05 mmol) and 1,4-dioxa-8-azaspiro[4.5]decane 6-3 (2.80 g, 19.57 mmol, 2.51 mL) in toluene (150 mL) was added sodium tert-butoxide (48.35 mg, 503.06 mol) at ambient temperature in a sealed tube. The reaction mixture was degassed under nitrogen atmosphere for 10 minutes and added bis(tri-tert-butylphosphine) palladium(0) (384.61 mg, 752.58 mol) into it. The resulting reaction mixture was stirred at 80° C. for 3 h. The reaction mixture was cooled to room temperature, quenched with water (200 mL), extracted with ethyl acetate (3×350 mL). The combined organic layer was dried over anhydrous sodium sulfate, filtered, and concentrated under reduced pressure to get crude. The crude was purified by column chromatography (silica gel, 230-400 mesh) using 0-100% ethyl acetate in hexane as eluent to afford benzyl 4-(1,4-dioxa-8-azaspiro[4.5]decan-8-yl) indoline-1-carboxylate 38-1 (5.5 g, 12.40 mmol, 82.38% yield) as a pale brown liquid. LCMS (ES$^+$): m/z 395.2 [M+H]$^+$.

Step-2:

To a stirred solution of benzyl 4-(1,4-dioxa-8-azaspiro[4.5]decan-8-yl)indoline-1-carboxylate 38-1 (1.4 g, 3.16 mmol) in ethyl acetate (20 mL) and THF (20 mL) was added, 10% Palladium on carbon wet (1.01 g, 946.87 mol) under inert atmosphere at room temperature. Later the reaction mass was stirred under hydrogen atmosphere (balloon pressure) for 16 h at room temperature. After consumption of the starting material by LCMS, the reaction mass was filtered through a pad of celite. The celite pad was washed with ethyl acetate (2×100 mL). The combined filtrate was concentrated under reduced pressure to get crude. The crude was purified by column chromatography (silica gel, 100-200 mesh) using 0-100% ethyl acetate in hexane as eluent to afford 8-indolin-4-yl-1,4-dioxa-8-azaspiro[4.5]decane 45-1 (850 mg, 2.73 mmol, 86.59% yield) as a pale brown solid. LCMS (ES$^+$): m/z 261.2[M+H]$^+$.

Step-3:

To a stirred solution of 8-indolin-4-yl-1,4-dioxa-8-azaspiro[4.5]decane 45-1 (850 mg, 2.73 mmol) in DMF (10.16 mL), were added 3-bromopiperidine-2,6-dione 12-8 (2.62 g, 13.66 mmol) and sodium bicarbonate (1.15 g, 13.66 mmol) under nitrogen atmosphere at room temperature. The reaction mixture was stirred at 65° C. for 16 h. After completion of the reaction, the reaction mixture was quenched with water (5 mL), extracted with ethyl acetate (2×10 mL). The combined organic extract was dried over anhydrous sodium sulfate, filtered, and concentrated under reduced pressure to get crude. The crude was purified by column chromatography (silica gel, 230-400 mesh) using 0-100% ethyl acetate in hexane as eluent to afford 3-[4-(1,4-dioxa-8-azaspiro[4.5]decan-8-yl)indolin-1-yl]piperidine-2,6-dione 45-2 (650 mg, 1.53 mmol, 55.86% yield) as a pale brown solid. LCMS (ES$^+$): m/z 372.2 [M+H]$^+$.

Step-4:

Enantiomers of racemic compound 3-[4-(1,4-dioxa-8-azaspiro[4.5]decan-8-yl)indolin-1-yl]piperidine-2,6-dione 45-2 (600 mg) were separated by chiral SFC [Chiral SFC purification method: column: I Cellulose-B (250*30)mm; 5.0 um; mobile phase: CO$_2$:co-solvent [60:40]v/v, co solvent: 0.5% isopropyl amine in isopropanol:acetonitrile [1:1] v/v; flow rate: 100 mL/min; wavelength: 210 nm]. The early eluting peak (arbitrarily assigned as S) (3S)-3-[4-(1,4-dioxa-8-azaspiro[4.5]decan-8-yl)indolin-1-yl]piperidi-ne-2,6-dione 45-3 (220 mg, 592.01 mol, 42.01% yield, 100% enantiopurity) was isolated as an off white solid. LCMS (ES$^+$): m/z 372.4 [M+H]$^+$. $^1$H NMR (400 MHz, DMSO-d$_6$): δ 10.77 (s, 1H), 6.88 (t, J=8.00 Hz, 1H), 6.24 (d, J=7.60 Hz, 1H), 6.20 (d, J=8.00 Hz, 1H), 4.59 (dd, J=4.80, 13.20 Hz, 1H), 3.91 (s, 4H), 3.43-3.38 (m, 1H), 3.30-3.23 (m, 1H), 3.03-2.91 (m, 4H), 2.88-2.75 (m, 3H), 2.61-2.50 (m, 1H), 2.25-2.12 (m, 1H), 1.94-1.88 (m, 1H), 1.78-1.59 (m, 4H). The late eluting peak (arbitrarily assigned as R) (3R)-3-[4-(1,4-dioxa-8-azaspiro[4.5]decan-8-yl)indolin-1-yl]piperi-dine-2,6-dione 45-4 (200 mg, 534.48 µmol, 37.93% yield, 98.7% enantiopurity) was isolated as an off white solid. LCMS (ES$^+$): m/z 372.4 [M+H]$^+$. $^1$H NMR (400 MHz, DMSO-d$_6$): δ 10.77 (s, 1H), 6.88 (t, J=7.60 Hz, 1H), 6.24 (d, J=8.00 Hz, 1H), 6.20 (d, J=8.00 Hz, 1H), 4.59 (dd, J=4.80, 13.20 Hz, 1H), 3.91 (s, 4H), 3.45-3.38 (m, 1H), 3.30-3.24 (m, 1H), 3.01-2.74 (m, 7H), 2.61-2.50 (m, 1H), 2.24-2.11 (m, 1H), 1.94-1.87 (m, 1H), 1.75-1.68 (m, 4H).

Scheme 46: Synthesis of tert-butyl ((1r,4r)-4-(1-(2,6-dioxopiperidin-3-yl)-5-fluoroindolin-4-yl)cyclohexyl)(methyl)carbamate and tert-butyl ((1s,4s)-4-(1-(2,6-dioxopiperidin-3-yl)-5-fluoroindolin-4-yl)cyclohexyl)(methyl)carbamate
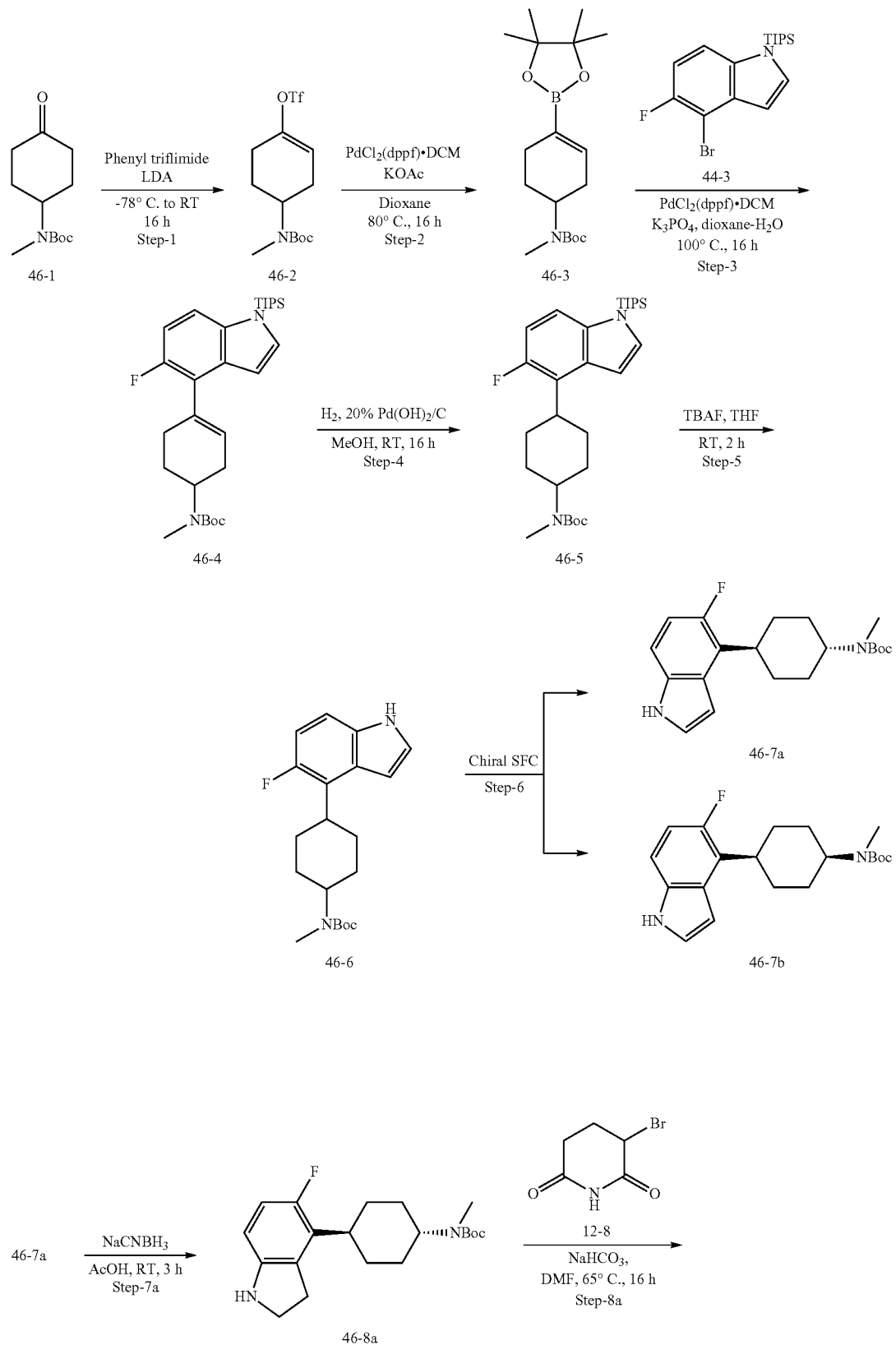

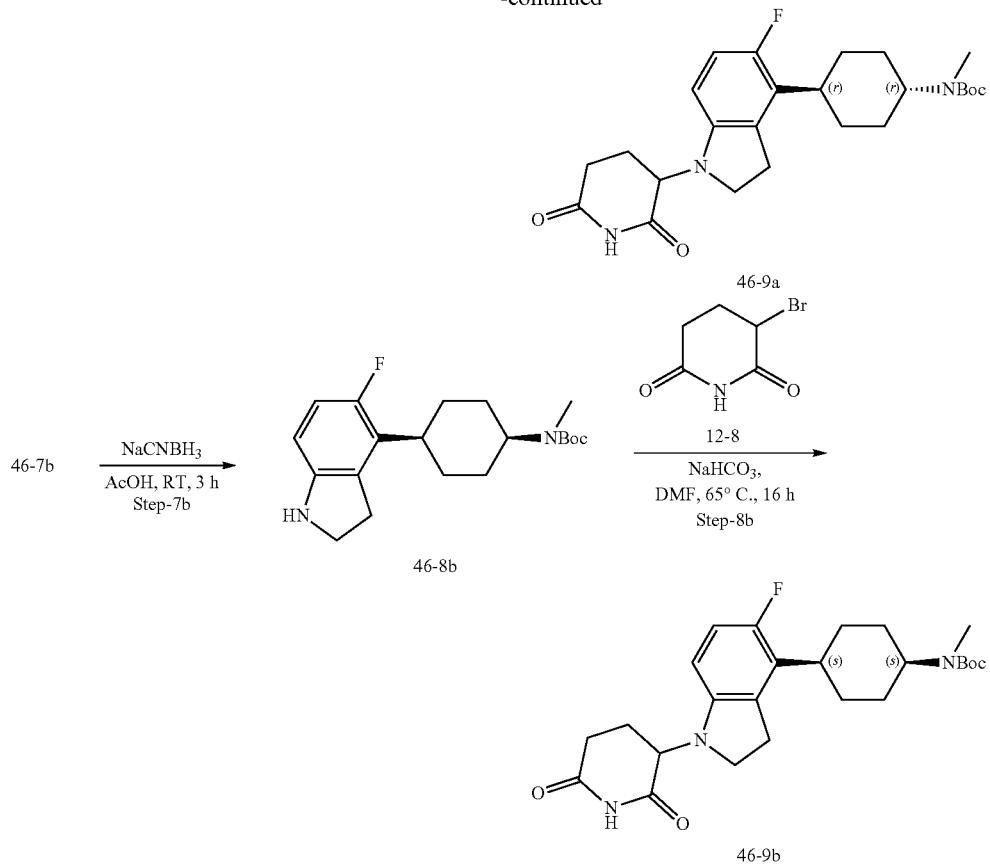

Step-1:

To a stirred solution of tert-butyl N-methyl-N-(4-oxocyclohexyl)carbamate 46-1 (5 g, 22.00 mmol) in THF (80 mL) was added (diisopropylamino)lithium (2 M in THF, 15.40 mL) dropwise at −78° C. and stirred for 30 min at the same temperature. Then a solution of 1,1,1-trifluoro-N-phenyl-N-(trifluoromethylsulfonyl)methanesulfonamide (11.00 g, 30.80 mmol) in THF (20 mL) was added at −78° C. and stirred for 15 min. The reaction temperature was warmed to room temperature and stirred for 16 h. After completion of the reaction, the reaction mixture was quenched with water (100 mL) and extracted with ethyl acetate (2×200 mL). The organic layer was washed with brine (50 mL), dried over anhydrous sodium sulfate, filtered and concentrated under reduced pressure to obtain crude, which was purified by column chromatography (silica gel, 230-400 mesh), using 0-100% ethyl acetate in hexane as eluent to afford [4-[tert-butoxycarbonyl(methyl)amino]cyclohexen-1-yl]trifluoromethanesulfonate 46-2 (6 g, 13.15 mmol, 59.76% yield) as a colourless oil. UPLC-MS (ES⁺): m/z 260.1 [M−Boc+H]⁺, 304.0 [M−tBu+H]⁺.

Step-2:

To a stirred solution of a mixture of [4-[tert-butoxycarbonyl(methyl)amino]cyclohexen-1-yl]trifluoromethanesulfonate 46-2 (7.5 g, 16.28 mmol) and 4,4,5,5-tetramethyl-2-(4,4,5,5-tetramethyl-1,3,2-dioxaborolan-2-yl)-1,3,2-dioxaborolane (6.20 g, 24.42 mmol) in 1,4-dioxane (80 mL), was added potassium acetate (3.99 g, 40.70 mmol) at ambient temperature. The reaction mixture was degassed under nitrogen atmosphere for 10 min and added [1,1'-bis(diphenylphosphino)ferrocene]dichloropalladium(II), complex with dichloromethane (930.58 mg, 1.14 mmol), the resulting reaction mixture was heated to 80° C. and stirred for 16 h. After completion, the reaction temperature was warmed to room temperature and filtered through a celite pad and washed with ethyl acetate (200 mL). The filtrate was concentrated under reduced pressure to obtain crude, which was purified by column chromatography (silica gel, 230-400 mesh), using 0-100% ethyl acetate in hexane as eluent to afford tert-butyl N-methyl-N-[4-(4,4,5,5-tetramethyl-1,3,2-dioxaborolan-2-yl)cyclohex-3-en-1-yl]carbamate 46-3 (4.3 g, 12.74 mmol, 78.28% yield) as a white solid. UPLC-MS (ES⁺): m/z 237.9 [M−Boc+H]⁺.

Step-3:

To a stirred solution of a mixture of tert-butyl N-methyl-N-[4-(4,4,5,5-tetramethyl-1,3,2-dioxaborolan-2-yl)cyclohex-3-en-1-yl]carbamate 46-3 (2 g, 5.93 mmol) and (4-bromo-5-fluoro-indol-1-yl)-triisopropylsilane 44-3 (2.74 g, 5.93 mmol) in 1,4-dioxane (60 mL) and water (10 mL) was added tripotassium phosphate (3.77 g, 17.78 mmol) at ambient temperature. The reaction mixture was degassed under nitrogen atmosphere for 10 min and [1,1'-bis(diphenylphosphino)ferrocene]dichloropalladium(II), complex with dichloromethane (242.02 mg, 296.36 mol) was added. The resulting reaction mixture was heated to 100° C. and stirred for 16 h at the same temperature. After completion of the reaction, the reaction mixture was diluted with ethyl acetate (200 ml), washed with water (2×50 mL). The organic layer was dried over anhydrous Na₂SO₄, filtered and concentrated under reduced pressure to obtain crude product, which was purified by column chromatography (silica gel, 230-400 mesh), using 0-100% ethyl acetate in hexane as eluent to afford tert-butyl N-[4-(5-fluoro-1-triisopropylsilyl-indol-4-yl)cyclohex-3-en-1-yl]-N-methylcarbamate 46-4 (1.5 g, 2.42 mmol, 40.77% yield) as a colorless gum. UPLC-MS (ES$^+$): m/z 401.4 [M−Boc+H]$^+$, 445.4 [M−tBu+H]$^+$.

Step-4:

To a stirred solution of tert-butyl N-[4-(5-fluoro-1-triisopropylsilyl-indol-4-yl)cyclohex-3-en-1-yl]-N-methyl-carbamate 46-4 (1.5 g, 3.00 mmol) in methanol (60 mL) was added palladium hydroxide on carbon, 20 wt. % 50% water (1.86 g, 13.24 mmol) at 25° C. and stirred for 16 h under hydrogen atmosphere. The reaction mixture was filtered through a celite pad and washed with ethyl acetate (2×100 mL). The filtrate was concentrated under reduced pressure to afford tert-butyl N-[4-(5-fluoro-1-triisopropylsilyl-indol-4-yl)cyclohexyl]-N-methylcarbamate 46-5 (1.4 g, 2.54 mmol, 84.65% yield, 91.06% (21.75%+69.31%; cis trans isomeric mixture) purity) as a colourless gummy product. UPLC-MS (ES$^+$): m/z 403.5 [M−Boc+H]$^+$, 447.4 [M−tBu+H]$^+$.

Step-5:

To a stirred solution of tert-butyl N-[4-(5-fluoro-1-triisopropylsilyl-indol-4-yl)cyclohexyl]-N-methylcarbamate 46-5 (1.4 g, 2.78 mmol) in THF (14 mL) was added tetrabutylammonium fluoride (1 M in THF, 5.57 mL) at 0° C., the reaction mixture was attired at room temperature for 2 h. The reaction mixture was concentrated under reduced pressure, hexane was added to the residue and stirred for 10 min. The precipitated solids were filtered and dried under vacuum to afford tert-butyl N-[4-(5-fluoro-1H-indol-4-yl)cyclohexyl]-N-methylcarbamate 46-6 (620 mg, 1.78 mmol, 64.09% yield) as an off white solid. UPLC-MS (ES$^+$): m/z 247.2 [M −Boc+H]$^+$.

Step-6:

The cis trans isomers of tert-butyl N-[4-(5-fluoro-1H-indol-4-yl)cyclohexyl]-N-methyl-carbamate 46-6 (800 mg, 2.31 mmol) were separated by chiral SFC [chiral SFC purification method: column: RR Whelk (250*30) mm, 5 μm; mobile phase: CO$_2$:isopropanol [80:20]; total flow: 120 mL/min, wavelength: 210 nm]. The early eluting peak (arbitrarily assigned as trans) tert-butyl N-[4-(5-fluoro-1H-indol-4-yl)cyclohexyl]-N-methyl-carbamate 46-7a (410 mg, 1.18 mmol, 50.97% yield, 100% enantiopurity) as an off-white solid. UPLC-MS (ES$^+$): m/z 247.4 [M Boc+H]$^+$. The late eluting peak (arbitrarily assigned as cis) tert-butyl N-[4-(5-fluoro-1H-indol-4-yl)cyclohexyl]-N-methyl-carbamate 46-7b (120 mg, 341.81 mol, 14.80% yield, 100% enantiopurity) as an off-white solid. UPLC-MS (ES$^+$): m/z 247.4 [M−Boc+H]$^+$.

Step-7a:

To a stirred solution of tert-butyl N-[4-(5-fluoro-1H-indol-4-yl)cyclohexyl]-N-methyl-carbamate 46-7a (360 mg, 1.04 mmol) in acetic acid (15 mL) was added sodium cyanoborohydride (195.91 mg, 3.12 mmol) and stirred at room temperature for 3 h. After completion of the reaction, the reaction mixture was diluted with ice water and adjusted pH-9 with 10% aq. NaOH solution, and then extracted with ethyl acetate (2×50 mL). The combined organic layer was washed with brine (20 mL), dried over anhydrous sodium sulfate, filtered and concentrated under reduced pressure to obtain crude, which was further triturated with hexane to afford tert-butyl N-[4-(5-fluoroindolin-4-yl)cyclohexyl]-N-methylcarbamate 46-8a (300 mg, 783.55 mol, 75.40% yield) as an off white solid. UPLC-MS (ES$^+$): m/z 293.2 [M−tBu+H]$^+$.

Step-8a:

To a stirred solution of tert-butyl N-[4-(5-fluoroindolin-4-yl)cyclohexyl]-N-methyl-carbamate 46-8a (300 mg, 860.95 mol) in DMF (10 mL) were added sodium bicarbonate (361.63 mg, 4.30 mmol) and 3-bromopiperidine-2,6-dione 12-8 (826.55 mg, 4.30 mmol) at room temperature, then the reaction mixture was heated to 65° C. and stirred for 16 h. After completion, the reaction mixture was diluted with ethyl acetate (80 mL) and washed with water (2×30 mL). The organic layer was dried over anhydrous sodium sulfate, filtered, and concentrated under reduced pressure to obtain crude. Methyl tertiary-butyl ether (MTBE) (10 mL) was added to the crude and stirred for 10 min, the precipitated solids were filtered and dried under vacuum to afford tert-butyl ((1r,4r)-4-(1-(2,6-dioxopiperidin-3-yl)-5-fluoroindolin-4-yl)cyclohexyl)(methyl)carbamate 46-9a (280 mg, 606.61 mol, 70.46% yield) as a light pink solid. UPLC-MS (ES$^+$): m/z 460.2 [M+H]$^+$. $^1$H NMR (400 MHz, DMSO-d$_6$): δ 10.79 (s, 1H), 6.71 (dd, J=8.40, 11.60 Hz, 1H), 6.30-6.25 (m, 1H), 4.57 (dd, J=4.80, 13.00 Hz, 1H), 4.02-3.65 (m, 1H), 3.45-3.20 (m, 2H), 3.17-2.85 (m, 2H), 2.82-2.66 (m, 4H), 2.65-2.50 (m, 2H), 2.22-2.13 (m, 1H), 1.94-1.55 (m, 9H), 1.41 (s, 9H).

Step-7b and Step-8b:

The procedures were identical to those of Step-7a and Step-8a. Compound tert-butyl ((1s,4s)-4-(1-(2,6-dioxopiperidin-3-yl)-5-fluoroindolin-4-yl)cyclohexyl)(methyl)carbamate 46-9b was obtained as an off-white solid. UPLC-MS (ES$^+$): m/z 460.2 [M+H]$^+$. $^1$H NMR (400 MHz, DMSO-d$_6$): δ 10.79 (s, 1H), 6.72 (dd, J=8.80, 12.00 Hz, 1H), 6.30-6.25 (m, 1H), 4.57 (dd, J=4.80, 12.80 Hz, 1H), 4.08-3.98 (m, 1H), 3.48-3.40 (m, 1H), 3.35-3.20 (m, 1H), 3.08-2.86 (m, 5H), 2.80-2.71 (m, 2H), 2.61-2.52 (m, 1H), 2.24-2.13 (m, 1H), 1.99-1.85 (m, 5H), 1.71-1.57 (m, 4H), 1.41 (s, 9H).

Scheme 47: Synthesis of tert-butyl 4-[4-fluoro-1-[(3S)-2,6-dioxo-3-piperidyl]indolin-5-yl]-piperidine-1-carboxylate and tert-butyl 4-[4-fluoro-1-[(3R)-2,6-dioxo-3-piperidyl]indolin-5-yl]-piperidine-1-carboxylate

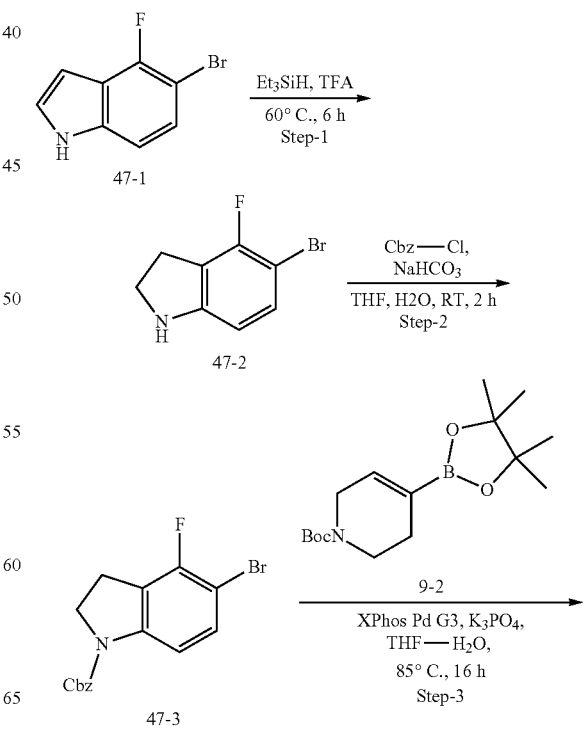

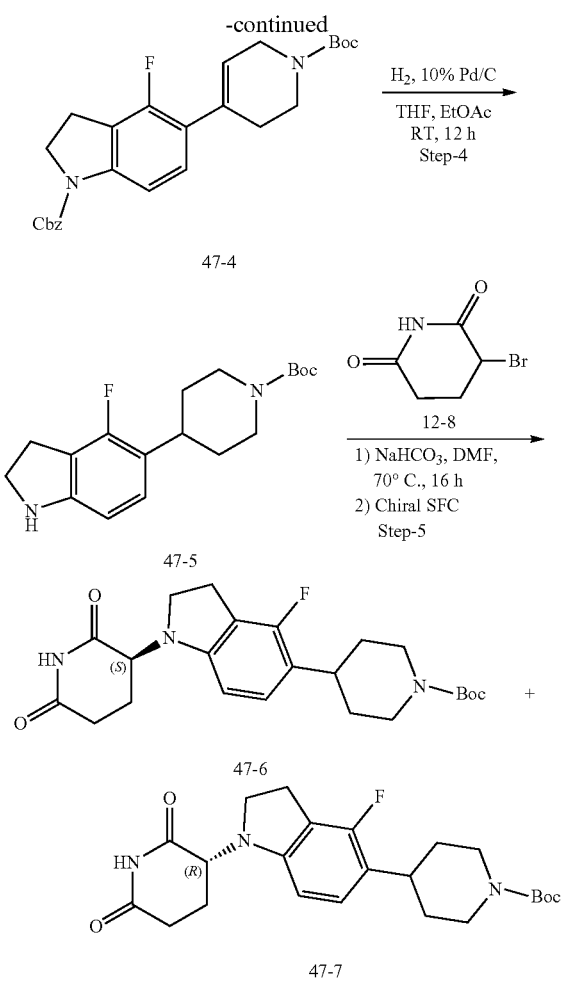

Step-1:

To a stirred solution of 5-bromo-4-fluoro-1H-indole 47-1 (2.8 g, 13.08 mmol) in trifluoroacetic acid (7.46 g, 65.41 mmol, 5.04 mL) at 0° C., was added triethylsilane (4.56 g, 39.25 mmol, 6.27 mL) and the reaction mixture was stirred at 60° C. for 16 h. After completion, the solvent was removed, and reaction mixture was basified with satd. aq. NaHCO₃ solution (10 mL) and extracted with DCM (2×100 mL). The combined organic layer was dried over anhydrous sodium sulfate, concentrated under reduced pressure to get crude. The crude was purified by column chromatography (silica gel, 60-120 mesh) where the product was eluted with 15-20% ethyl acetate in hexane as an eluent to afford 5-bromo-4-fluoro-indoline 47-2 (2.3 g, 9.58 mmol, 73.78% yield) as a brown gummy liquid. UPLC-MS (ES⁺): m/z 216.2 [M+H]⁺.

Step-2:

To a stirred solution of 5-bromo-4-fluoro-indoline 47-2 (2.5 g, 11.57 mmol) in THF (25 mL) and water (10 mL) at 0° C. was added sodium bicarbonate (2.92 g, 34.71 mmol) followed by benzyl chloroformate (2.37 g, 13.89 mmol, 1.97 mL) at 0° C. The reaction mixture was stirred at room temperature for 2 h. After reaction completion, the reaction mixture was diluted with water (50 mL) and extracted with ethyl acetate (2×100 mL). The combined organic layer was dried over anhydrous sodium sulfate, filtered, and concentrated under reduced pressure to get crude. The crude was purified by silica gel column chromatography (60-120 mesh) where product was eluted using 4-5% ethyl acetate in hexane as eluent to afford benzyl 5-bromo-4-fluoro-indoline-1-carboxylate 47-3 (2.3 g, 6.57 mmol, 56.76% yield) as a brown gummy liquid. ¹H NMR (400 MHz, DMSO-d₆): δ 7.58-7.31 (m, 7H), 5.25 (s, 2H), 4.10 (t, J=8.40 Hz, 2H), 3.17 (t, J=8.80 Hz, 2H).

Step-3:

To a stirred solution of benzyl 5-bromo-4-fluoro-indoline-1-carboxylate 47-3 (2.3 g, 6.57 mmol) and tert-butyl 4-(4,4,5,5-tetramethyl-1,3,2-dioxaborolan-2-yl)-3,6-dihydro-2H-pyridine-1-carboxylate 9-2 (2.44 g, 7.88 mmol) in THF (40 mL) and water (7 mL) was added potassium phosphate (4.18 g, 19.70 mmol) and the mixture was purged with nitrogen gas for 2-3 min. Then XPhos Pd G3 (555.95 mg, 656.80 mol) was added and purged again with nitrogen gas for 2-3 min. The reaction mixture was stirred at 85° C. for 16 h. After completion, the mixture was filtered through a celite pad and the obtained filtrate was extracted with ethyl acetate (2×100 mL). The combined organic layer was dried over anhydrous sodium sulfate, concentrated under reduced pressure to get crude. The crude was purified by column chromatography (silica gel, 60-120 mesh) where the product was eluted with 4-5% ethyl acetate in hexane as an eluent to afford benzyl 5-(1-tert-butoxycarbonyl-3,6-dihydro-2H-pyridin-4-yl)-4-fluoro-indoline-1-carboxylate 47-4 (1.5 g, 3.21 mmol, 48.87% yield) as a pale-yellow gummy liquid. UPLC-MS (ES⁺): m/z 397.2 [M−tBu+H]⁺, 353.2 [M−Boc+H]⁺.

Step-4:

To a stirred solution of benzyl 5-(1-tert-butoxycarbonyl-3,6-dihydro-2H-pyridin-4-yl)-4-fluoro-indoline-1-carboxylate 47-4 (1.5 g, 3.31 mmol) in THF (20 mL) and ethyl acetate (6 mL) was added palladium, 10% on carbon (705.52 mg, 6.63 mmol) under nitrogen carefully. The reaction mixture was stirred under hydrogen atmosphere (balloon pressure) at room temperature for 12 h. After completion, the reaction mixture was filtered through a celite pad and washed with ethyl acetate (150 mL). The filtrate was concentrated under reduced pressure to get crude. The crude was purified by silica gel column chromatography (60-120 mesh) where the product was eluted with 10-15% ethyl acetate in hexane as an eluent to afford tert-butyl 4-(4-fluoroindolin-5-yl)-piperidine-1-carboxylate 47-5 (900 mg, 2.12 mmol, 64.05% yield) as an off-white solid. LCMS (ES⁺): m/z 265.2 [M−tBu+H]⁺, 221.4 [M−Boc+H]⁺.

Step-5:

To a stirred solution of tert-butyl 4-(4-fluoroindolin-5-yl)-piperidine-1-carboxylate 47-5 (900 mg, 2.12 mmol) in DMF (10 mL) was added sodium bicarbonate (1.18 g, 14.04 mmol) and 3-bromopiperidine-2,6-dione 12-8 (2.70 g, 14.04 mmol). The reaction mixture was stirred at 70° C. for 16 h. After 16 h, while still unreacted starting material remained, additional sodium bicarbonate (1.18 g, 14.04 mmol) and 3-bromopiperidine-2,6-dione 12-8 (2.70 g, 14.04 mmol) were added and the reaction mixture was further stirred at 70° C. for 16 h. After completion of reaction, the reaction mixture was concentrated, and the crude residue was diluted with water (50 mL) followed by extraction with ethyl acetate (2×150 mL). The combined organic layer was dried over anhydrous sodium sulfate, filtered, concentrated under reduced pressure to obtain crude. The crude was purified by column chromatography (silica gel, 60-120 mesh) where the product was eluted with 40-50% ethyl acetate in hexane as an eluent to afford partially pure product, which was further purified by preparative HPLC (mobile phase: 0.1% formic acid in acetonitrile: H₂O (60:40). The pure product fractions were combined and lyophilized to obtain the racemic product, which was further purified by chiral SFC to separate the enantiomers [chiral SFC purification method: column: R,R-Whelk-O (250*30) mm, 5 μm; mobile phase: $CO_2$: 0.1% NH3 in isopropanol [80:20]; total flow: 120/min; back pressure: 100 bar; wavelength: 210 nm; cycle time: 6 min]. The early eluting peak (arbitrarily assigned as S) tert-butyl 4-[4-fluoro-1-[(3S)-2,6-dioxo-3-piperidyl]-indolin-5-yl]-piperidine-1-carboxylate 47-6 (20 mg, 46.30 mol, 1.65% yield, 100% enantiopurity) was isolated as off-white solid. UPLC-MS (ES$^+$): m/z 376.4 [M–tBu+H]$^+$. 1H NMR (400 MHz, DMSO-d$_6$): δ 10.81 (s, 1H), 6.88 (t, J=8.00 Hz, 1H), 6.28 (d, J=8.40 Hz, 1H), 4.62 (dd, J=4.80, 13.20 Hz, 1H), 4.12-3.97 (m, 2H), 3.53-3.46 (m, 1H), 3.03-2.88 (m, 2H), 2.85-2.72 (m, 4H), 2.60-2.52 (m, 1H), 2.26-2.14 (m, 1H), 1.94-1.88 (m, 1H), 1.71-1.64 (m, 2H), 1.52-1.43 (m, 3H), 1.42 (s, 9H). The late eluting peak (arbitrarily assigned as R) tert-butyl 4-[4-fluoro-1-[(3R)-2,6-dioxo-3-piperidyl]-indolin-5-yl]-piperidine-1-carboxylate 47-7 (20 mg, 45.93 mol, 1.64% yield, 100% enantiopurity) was isolated as an off-white solid. UPLC-MS (ES$^+$): m/z 376.2 [M–tBu+H]$^+$, 332.4 [M–Boc+H]$^+$. $^1$H NMR (400 MHz, DMSO-d$_6$): δ 10.81 (s, 1H), 6.88 (t, J=8.00 Hz, 1H), 6.28 (d, J=8.00 Hz, 1H), 4.62 (dd, J=4.80, 13.20 Hz, 1H), 4.12-4.00 (m, 2H), 3.53-3.45 (m, 1H), 3.04-2.88 (m, 2H), 2.85-2.73 (m, 4H), 2.62-2.52 (m, 1H), 2.27-2.13 (m, 1H), 1.96-1.88 (m, 1H), 1.71-1.63 (m, 2H), 1.53-1.43 (m, 3H), 1.42 (s, 9H).

Scheme 48: Synthesis of tert-butyl 1-[1-[(3S)-2,6-dioxo-3-piperidyl]indolin-4-yl]piperidine-4-carboxylate and tert-butyl 1-[1-[(3R-2,6-dioxo-3-piperidyl]indolin-4-yl]piperidine-4-carboxylate

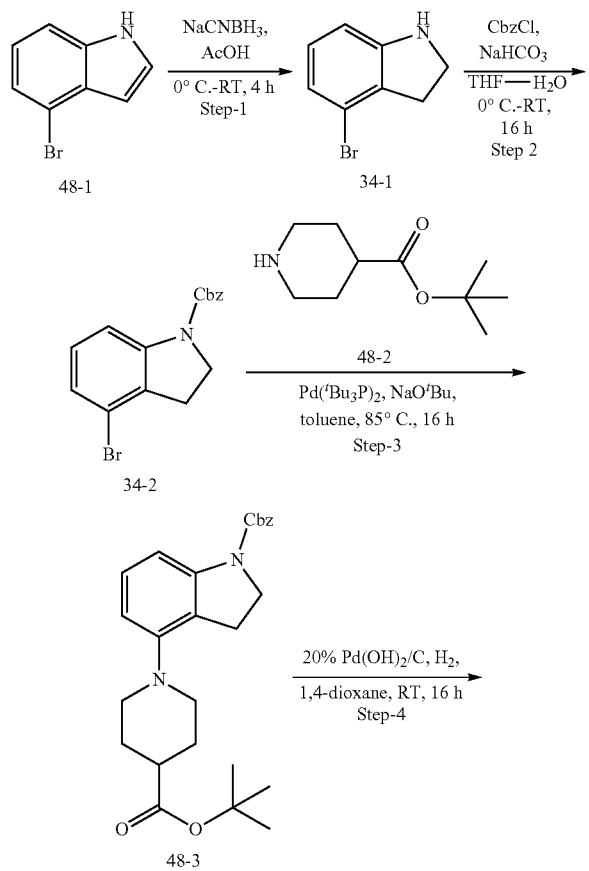

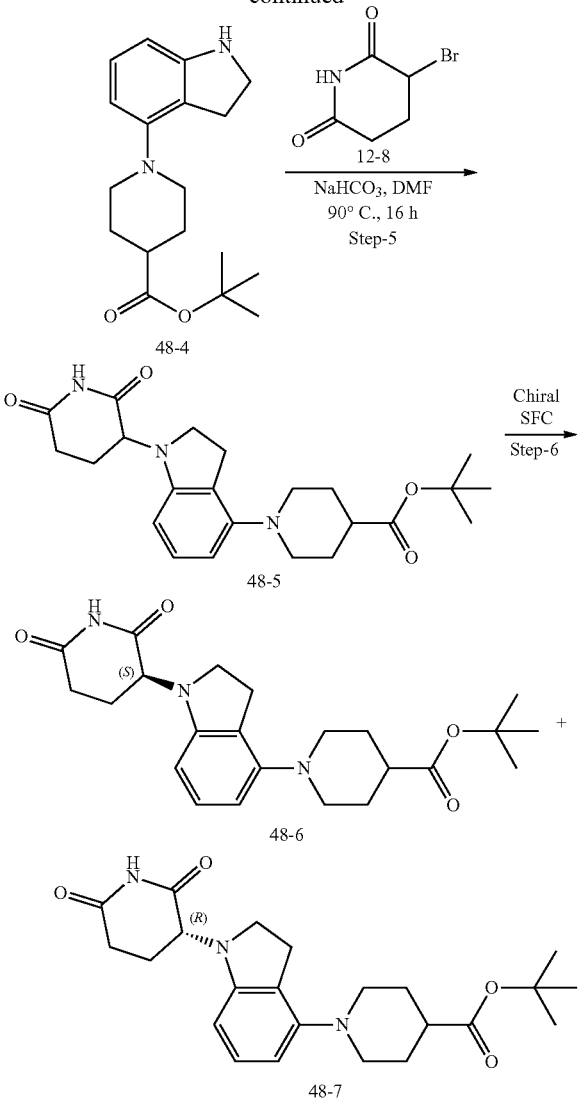

Step-1:

To stirred solution of 4-bromo-1H-indole 48-1 (25 g, 127.52 mmol, 15.99 mL) in AcOH (150 mL) was added sodium cyanoborohydride (12.02 g, 191.28 mmol) at 0° C. portionwise under nitrogen atmosphere. After completion of the addition, the reaction mixture was warmed to ambient temperature and stirred for 4 h. After completion of the starting material as indicated by TLC, the reaction mixture was poured into cold water (500 mL) and extracted with MTBE (methyl tertiary-butyl ether) (3×500 mL). The combined organic layer was washed with cold water (2×500 mL) and saturated aq. NaHCO$_3$ (2×500 mL), respectively. Finally, the organic layer was washed with brine (500 mL), dried over anhydrous sodium sulfate, and filtered. The filtrate was concentrated under reduced pressure to get crude, which was purified by flash column chromatography (silica gel, 230-400 mesh) where the desired compound was eluted at 5% EtOAc in hexane to afford 4-bromoindoline 34-1 (16 g, 74.61 mmol, 58.51% yield, 92.36% purity) as a light brown liquid. UPLC-MS (ES$^+$): m/z 200.0 [M+2H]$^+$. $^1$H NMR (400 MHz, CDCl$_3$): δ 6.91-6.82 (m, 2H), 6.54 (d, J=7.60 Hz, 1H), 3.95 (br, 1H), 3.62 (t, J=8.80 Hz, 2H), 3.08 (t, J=8.40 Hz, 2H).

Step-2:

To a stirred solution of 4-bromoindoline 34-1 (10 g, 46.77 mmol) in THF (100 mL) and water (200 mL) was added sodium bicarbonate (11.79 g, 140.32 mmol) at room temperature. Benzyl chloroformate (9.58 g, 56.13 mmol) was then added into it at 0° C. in a dropwise manner and the resulting reaction mixture was stirred at room temperature for 16 h. During the reaction solid was precipitated. After completion of the reaction as indicated by TLC, the reaction mixture was concentrated under reduced pressure to remove THF. Solids were filtered, washed with water (100 mL) and dried under vacuum to get the crude. The crude was triturated with n-hexane (100 mL) to afford benzyl 4-bromoindoline-1-carboxylate 34-2 (15 g, 45.15 mmol, 96.54% yield) as an off-white solid. $^1$H NMR (400 MHz, DMSO-$d_6$): δ 7.79-7.71 (m, 1H), 7.33-7.40 (m, 5H), 7.16-7.10 (m, 2H), 5.24 (s, 2H), 4.03 (t, J=8.40 Hz, 2H), 3.05 (t, J=8.80 Hz, 2H).

Step 3:

To a stirred mixture of benzyl 4-bromoindoline-1-carboxylate 34-2 (5 g, 15.05 mmol) and tert-butyl piperidine-4-carboxylate hydrochloride 48-2 (4 g, 18.06 mmol) in toluene (50 mL) was added sodium 2-methylpropan-2-olate (3.62 g, 37.63 mmol) at room temperature under nitrogen atmosphere and the resulting reaction contents were degassed by bubbling with nitrogen for 10 min. Later, bis(tri-tert-butylphosphine)palladium (0) (769.21 mg, 1.51 mmol) was added to the reaction mixture and the reaction was stirred at 85° C. for 16 h. After completion of reaction, the reaction mass was poured in water (150 mL) and extracted with EtOAc (250 mL). The organic layer was washed with brine solution (75 mL), dried over anhydrous sodium sulfate, and filtered. The filtrate was concentrated under reduced pressure to get the crude, which was purified by flash column chromatography (silica gel, 230-400 mesh) eluting the product fractions with 0-20% EtOAc in hexane to afford benzyl 4-(4-tert-butoxycarbonyl-1-piperidyl) indoline-1-carboxylate 48-3 (4 g, 9.03 mmol, 59.99% yield, 98.55% purity) as an off-white solid. UPLC-MS (ES$^+$): m/z 437.2 [M+H]$^+$. $^1$H NMR (400 MHz, DMSO-$d_6$): δ 7.34-7.40 (m, 6H), 7.10 (t, J=7.60 Hz, 1H), 6.60 (d, J=8.00 Hz, 1H), 5.22 (s, 2H), 3.99 (t, J=8.40 Hz, 2H), 3.19-3.16 (m, 2H), 2.99 (t, J=8.40 Hz, 2H), 2.67-2.61 (m, 2H), 2.39-2.28 (m, 1H), 1.90-1.86 (m, 2H), 1.70-1.63 (m, 2H), 1.42 (s, 9H).

Step-4:

To a stirred solution of benzyl 4-(4-tert-butoxycarbonyl-1-piperidyl)indoline-1-carboxylate 48-3 (8 g, 18.27 mmol) in 1,4-dioxane (80 mL) was added palladium hydroxide, Pd 20% on carbon, nominally 50% water (4.25 g, 6.05 mmol) at room temperature and the resulting reaction mixture was stirred at room temperature for 16 h under hydrogen atmosphere (balloon pressure). After completion of the starting material as indicated by UPLC-MS, the reaction mixture was diluted with methanol (250 mL) and filtered through a pad of celite. The celite bed was washed with methanol thoroughly (500 mL) and the filtrate was concentrated under reduced pressure to get the crude. The crude was purified by flash column chromatography (silica gel, 230-400 mesh) eluting the product with 60% EtOAc in hexane to afford tert-butyl 1-indolin-4-ylpiperidine-4-carboxylate 48-4 (4 g, 11.58 mmol, 63.40% yield) as a thick brown liquid. UPLC-MS (ES$^+$): m/z 303.2 [M+H]$^+$. $^1$H NMR (400 MHz, DMSO-$d_6$): δ 6.83 (t, J=7.60 Hz, 1H), 6.21-6.16 (m, 2H), 5.32 (s, 1H), 3.38-3.34 (m, 2H), 3.21-3.17 (m, 2H), 2.80 (t, J=8.40 Hz, 2H), 2.63-2.56 (m, 2H), 2.34-2.28 (m, 1H), 1.89-1.85 (m, 2H), 1.69-1.59 (m, 2H), 1.42 (s, 9H).

Step-5:

To a stirred solution of tert-butyl 1-indolin-4-ylpiperidine-4-carboxylate 48-4 (4.40 g, 12.73 mmol) in DMF (50 mL) was added anhydrous NaHCO$_3$ (4.28 g, 50.94 mmol) at room temperature under nitrogen atmosphere. After 5 min, 3-bromopiperidine-2,6-dione 12-8 (4.89 g, 25.47 mmol) was added to the reaction mixture and the reaction mixture was stirred at 90° C. for 16 h. After completion of the starting material as indicated by TLC, the reaction mixture was filtered through a pad of celite and the celite pad was washed with EtOAc (750 mL). The organic layer was washed with cold water (1 L) and brine solution (500 mL), respectively, then dried over anhydrous Na$_2$SO$_4$ and filtered. The filtrate was concentrated under reduced pressure to get crude (not completely dried) which was triturated with MTBE (25 mL) and n-pentane (50 mL), respectively, to afford tert-butyl 1-[1-(2,6-dioxo-3-piperidyl) indolin-4-yl]piperidine-4-carboxylate 48-5 (2.6 g, 6.09 mmol, 47.82% yield, 96.86% purity) as violet solid. UPLC-MS (ES$^+$): m/z 414.4 [M+H]$^+$.

Step-6:

Racemic compound tert-butyl 1-[1-[(3S)-2,6-dioxo-3-piperidyl]indolin-4-yl]piperidine-4-carboxylate 48-5 (700 mg, 1.69 mmol) were separated by chiral SFC [Chiral SFC purification method: Column: Chromega CCS (250*20) mm, 5 μm; Flow rate: 70 mL/min; Mobile phase: CO$_2$:0.2% formic acid in isopropanol:acetonitrile (65:35)]. The early eluting peak (arbitrarily assigned as S) tert-butyl 1-[1-[(3S)-2,6-dioxo-3-piperidyl]indolin-4-yl]piperidine-4-carboxylate 48-6 (215 mg, 514.07 mol, 30.37% yield, 98.87% UPLC-MS purity, 96.66% enantiopurity) was obtained as an off-white solid. UPLC-MS (ES$^+$): m/z 414.2 [M+H]$^+$. $^1$H NMR (400 MHz, DMSO-$d_6$): δ 10.77 (s, 1H), 6.89 (t, J=8.00 Hz, 1H), 6.21 (t, J=8.00 Hz, 2H), 4.59 (dd, J=4.80, 13.00 Hz, 1H), 3.43-3.36 (m, 1H), 3.29-3.20 (m, 1H), 3.20-3.16 (m, 2H), 2.87-2.73 (m, 3H), 2.69-2.66 (m, 1H), 2.60-2.53 (m, 2H), 2.37-2.28 (m, 1H), 2.25-2.21 (m, 1H), 1.93-1.82 (m, 3H), 1.70-1.57 (m, 2H), 1.42 (s, 9H). The late eluting peak (arbitrarily assigned as R) tert-butyl 1-[1-[(3R)-2,6-dioxo-3-piperidyl]indolin-4-yl]piperidine-4-carboxylate 48-7 (1.1 g, 2.39 mmol, 42.30% yield, 100% enantiopurity) was obtained as an off-white solid. UPLC-MS (ES$^+$): m/z 414.2 [M+H]$^+$. 1H NMR (400 MHz, DMSO-$d_6$): δ 10.77 (s, 1H), 6.89 (t, J=7.60 Hz, 1H), 6.21 (t, J=8.00 Hz, 2H), 4.59 (dd, J=4.80, 13.00 Hz, 1H), 3.42-3.38 (m, 1H), 3.29-3.22 (m, 1H), 3.20-3.15 (m, 2H), 2.86-2.72 (m, 3H), 2.69-2.53 (m, 3H), 2.35-2.28 (m, 1H), 2.22-2.12 (m, 1H), 1.93-1.82 (m, 3H), 1.69-1.58 (m, 2H), 1.42 (s, 9H).

Scheme 49: Synthesis of tert-butyl 4-[5-fluoro-1-[(3S)-2,6-dioxo-3-piperidyl]indolin-4-yl]piperidine-1-carboxylate and tert-butyl 4-[5-fluoro-1-[(3R)-2,6-dioxo-3-piperidyl] indolin-4-yl]piperidine-1-carboxylate

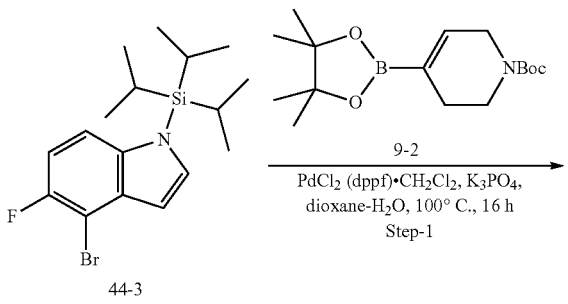

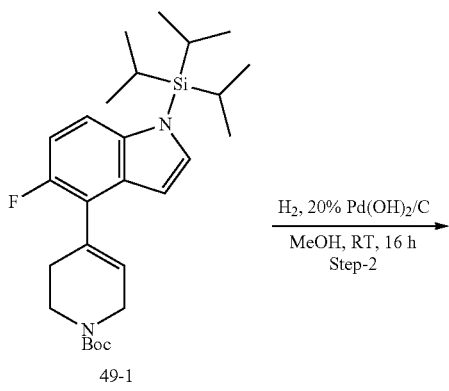

49-1

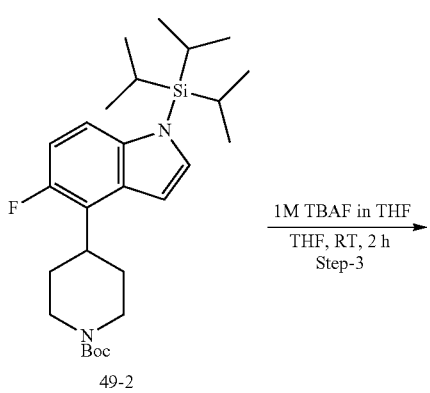

49-2

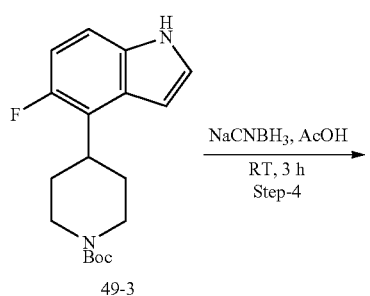

49-3

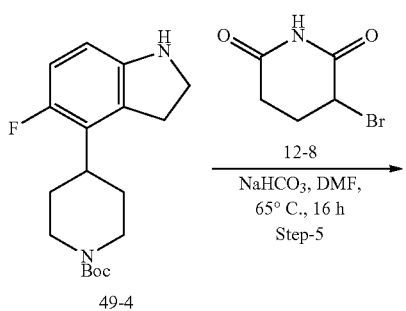

49-4

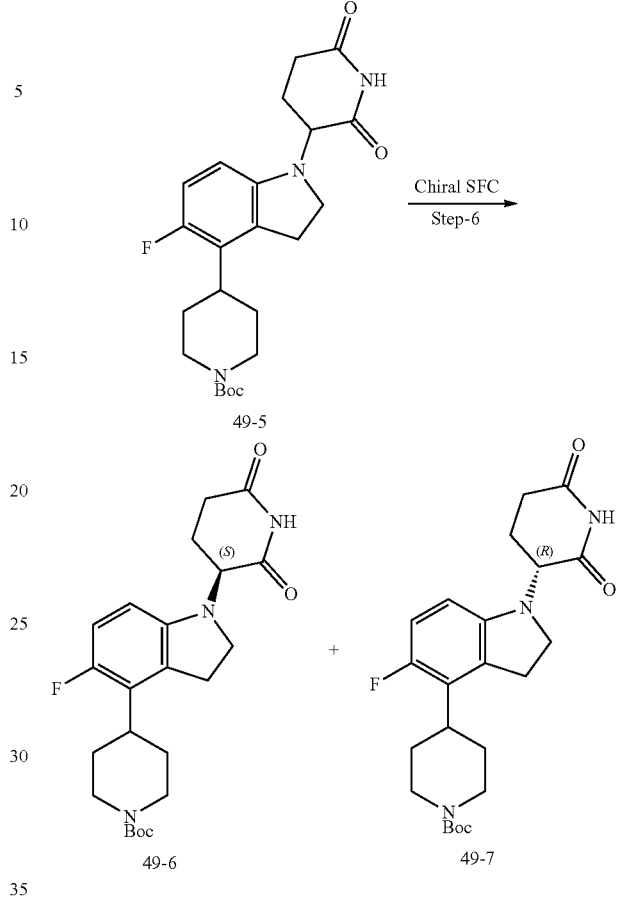

49-5

49-6  +  49-7

Step-1:

To a stirred solution of tert-butyl 4-(4,4,5,5-tetramethyl-1,3,2-dioxaborolan-2-yl)-3,6-dihydro-2H-pyridine-1-carboxylate 9-2 (5 g, 16.17 mmol) and (4-bromo-5-fluoro-indol-1-yl)-triisopropylsilane 44-3 (5.99 g, 16.17 mmol) in 1,4-dioxane (150 mL) and water (20 mL), was added anhydrous potassium phosphate tribasic (10.30 g, 48.51 mmol) at ambient temperature. The reaction mixture was degassed under nitrogen atmosphere for 10 minutes and added [1,1'-bis(diphenylphosphino)ferrocene]dichloropalladium(II), complex with dichloromethane (660.27 mg, 808.52 mol). The resulting reaction mixture was stirred at 100° C. for 16 h. After completion of the reaction, the reaction mixture was filtered through a celite pad. The filtrate was concentrated under reduced pressure, diluted with ethyl acetate (300 mL), and washed with water (2×100 mL). The organic layer was dried over anhydrous Na$_2$SO$_4$, filtered and concentrated under reduced pressure to get crude, which was purified by silica gel flash column chromatography (230-400 mesh), using 0-100% ethyl acetate in hexane as eluent to afford tert-butyl 4-(5-fluoro-1-triisopropylsilyl-indol-4-yl)-3,6-dihydro-2H-pyridine-1-carboxylate 49-1 (3.9 g, 7.79 mmol, 48.15% yield) as a colourless gummy solid. UPLC-MS (ES$^+$): m/z 373.2 [M−Boc+H]$^+$, 417.0 [M−tBu+H]$^+$.

Step-2:

To a stirred solution of tert-butyl 4-(5-fluoro-1-triisopropylsilyl-indol-4-yl)-3,6-dihydro-2H-pyridine-1-carboxylate 49-1 (4.1 g, 8.67 mmol) in methanol (90 mL) was added palladium hydroxide on carbon, 20 wt. % 50% water (3.15 g, 22.46 mmol) at room temperature and stirred for 16 h under hydrogen atmosphere (balloon pressure). After completion of the reaction, the reaction mixture was filtered through a celite pad and washed with ethyl acetate (500 mL). The filtrate was concentrated under reduced pressure to afford tert-butyl 4-(5-fluoro-1-triisopropylsilyl-indol-4-yl)piperidine-1-carboxylate 49-2 (3.8 g, 7.71 mmol, 88.85% yield) as a colourless gum. UPLC-MS (ES+): m/z 376.4 [M−Boc+H]+, 419.4 [M−tBu+H]+.

Step-3:

To a stirred solution of tert-butyl 4-(5-fluoro-1-triisopropylsilyl-indol-4-yl)piperidine-1-carboxylate 49-2 (3.7 g, 7.79 mmol) in THF (50 mL) was added tetrabutylammonium fluoride (TBAF) (1 M in THF, 15.59 mL) at 0° C. The reaction mixture was stirred at room temperature for 2 h. After completion of the reaction, the reaction mixture was concentrated under reduced pressure to afford crude, which was purified by flash column chromatography (silica gel, 230-400 mesh), using 0-100% ethyl acetate in hexane as eluent to afford tert-butyl 4-(5-fluoro-1H-indol-4-yl)piperidine-1-carboxylate 49-3 (2.1 g, 6.56 mmol, 84.15% yield) as a colourless gummy solid. UPLC-MS (ES+): m/z 219.2 [M−Boc+H]+, 263.2 [M−tBu+H]+.

Step-4:

To a stirred solution of tert-butyl 4-(5-fluoro-1H-indol-4-yl)piperidine-1-carboxylate 49-3 (2 g, 6.24 mmol) in acetic acid (40 mL) was added sodium cyanoborohydride (1.18 g, 18.73 mmol) and stirred at room temperature for 3 h. After completion of the reaction, ice cold water was added to the reaction mixture, adjusted to pH-9 with 10% aq. NaOH solution, and then extracted with ethyl acetate (2×150 mL). The combined organic phase was washed with satd. aq. NaHCO₃ solution (2×50 mL) and brine (50 mL), respectively. The organic layer was dried over anhydrous Na₂SO₄, filtered and concentrated under reduced pressure to afford tert-butyl 4-(5-fluoroindolin-4-yl)piperidine-1-carboxylate 49-4 (1.9 g, 4.70 mmol, 75.22% yield) as a colourless gummy solid. UPLC-MS (ES+): m/z 221.2 [M−Boc+H]+, 265.2 [M−tBu+H]+.

Step-5:

To a stirred solution of tert-butyl 4-(5-fluoroindolin-4-yl)piperidine-1-carboxylate 49-4 (1.8 g, 4.45 mmol) in DMF (70 mL) were added sodium bicarbonate (1.87 g, 22.25 mmol) and 3-bromopiperidine-2,6-dione 12-8 (4.27 g, 22.25 mmol) at room temperature, then the reaction mixture was heated to 65° C. and stirred for 16 h. After completion of the reaction, the reaction mixture was filtered through a celite pad, washed with ethyl acetate (300 mL). The filtrate was washed with water (3×100 mL) and brine (100 mL), respectively. The organic layer was dried over anhydrous sodium sulfate, filtered, and concentrated under reduced pressure to afford the crude, which was purified by flash column chromatography (silica gel, 230-400 mesh), using 0-100% ethyl acetate in hexane as eluent to afford tert-butyl 4-[1-(2,6-dioxo-3-piperidyl)-5-fluoro-indolin-4-yl]piperidine-1-carboxylate 49-5 (1.5 g, 3.45 mmol, 77.46% yield) as a light pink solid. UPLC-MS (ES+): m/z 332.2 [M−Boc+H]+, 376.2 [M−tBu+H]+.

Step-6:

Enantiomers of tert-butyl 4-[1-(2,6-dioxo-3-piperidyl)-5-fluoro-indolin-4-yl]piperidine-1-carboxylate 49-5 (1.5 g, 3.48 mmol) were separated by chiral SFC [Chiral SFC purification method: Column: I -Cellulose C (250*30) mm, 5 μm; mobile phase: CO₂:0.2% FA in isopropanol:acetonitrile (70:30); co-solvent name: isopropanol, co-solvent: 20%; flow rate: 120 ml/min; temperature: 35° C.; outlet pressure: 120 bar]. The SFC fractions were concentrated separately and further purified by normal phase column chromatography (silica gel, 230-400 mesh) separately using 45-50% ethyl acetate in hexane as eluent. The early eluting peak (arbitrarily assigned as S) tert-butyl 4-[5-fluoro-1-[(3S)-2,6-dioxo-3-piperidyl]indolin-4-yl]piperidine-1-carboxylate 49-6 (180 mg, 414.94 mol, 11.94% yield, 100% enantiopurity) as a bluish white solid. UPLC-MS (ES+): m/z 332.2 [M−Boc+H]+, 376.2 [M−tBu+H]+. ¹H NMR (400 MHz, DMSO-d₆): δ 10.79 (s, 1H), 6.72 (dd, J=8.40, 12.00 Hz, 1H), 6.29 (dd, J=3.60, 8.60 Hz, 1H), 4.57 (dd, J=4.80, 13.00 Hz, 1H), 4.12-3.99 (m, 2H), 3.50-3.38 (m, 1H), 3.31-3.20 (m, 1H), 3.10-2.90 (m, 2H), 2.85-2.70 (m, 4H), 2.60-2.52 (m, 1H), 2.25-2.10 (m, 1H), 1.95-1.85 (m, 1H), 1.82-1.72 (m, 2H), 1.70-1.55 (m, 2H), 1.42 (s, 9H). The late eluting peak (arbitrarily assigned as R) tert-butyl 4-[5-fluoro-1-[(3R)-2,6-dioxo-3-piperidyl]indolin-4-yl]piperidine-1-carboxylate 49-7 (240 mg, 554.75 μmol, 15.96% yield, 97.41% enantiopurity) as a bluish white solid. UPLC-MS (ES+): m/z 332.2 [M−Boc+H]+, 376.2 [M−tBu+H]+. ¹H NMR (400 MHz, DMSO-d₆): δ 10.79 (s, 1H), 6.72 (dd, J=8.40, 12.00 Hz, 1H), 6.29 (dd, J=3.60, 8.60 Hz, 1H), 4.57 (dd, J=4.80, 12.80 Hz, 1H), 4.14-3.99 (m, 2H), 3.50-3.38 (m, 1H), 3.31-3.20 (m, 1H), 3.10-2.70 (m, 6H), 2.61-2.53 (m, 1H), 2.25-2.11 (m, 1H), 1.95-1.88 (m, 1H), 1.83-1.72 (m, 2H), 1.70-1.55 (m, 2H), 1.42 (s, 9H).

Scheme 50: Synthesis of tert-butyl (S)-4-(1-(2,6-dioxopiperidin-3-yl)-4,6-difluoroindolin-5-yl)piperidine-1-carboxylate and tert-butyl (R)-4-(1-(2,6-dioxopiperidin-3-yl)-4,6-difluoroindolin-5-yl)piperidine-1-carboxylate

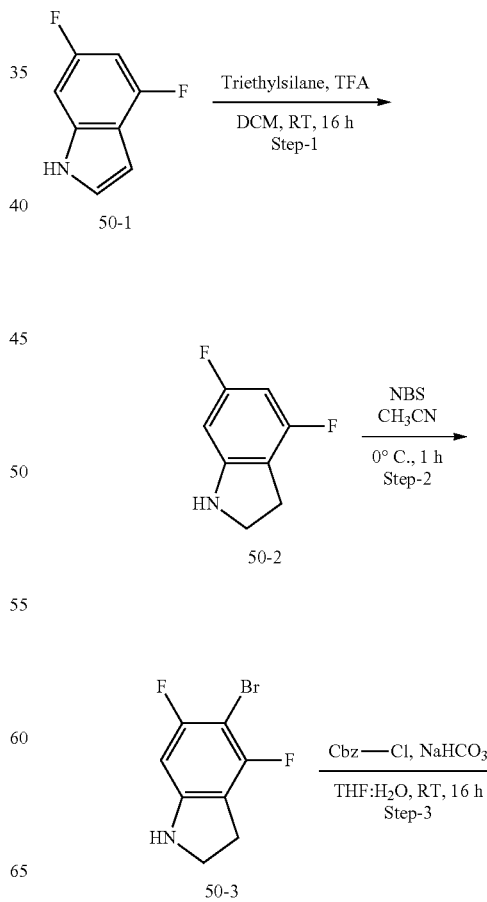

-continued

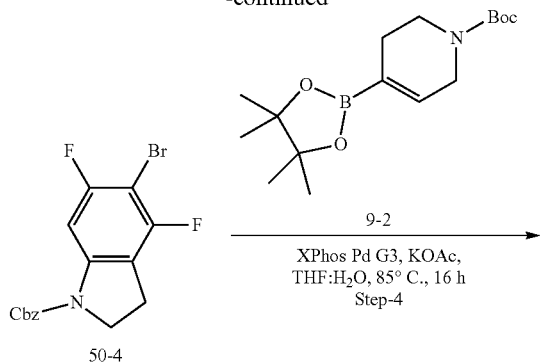

50-4

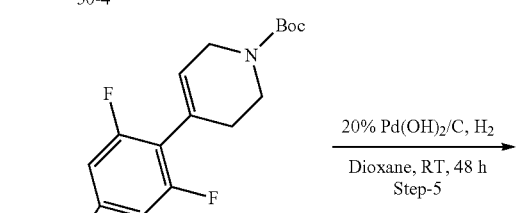

50-5

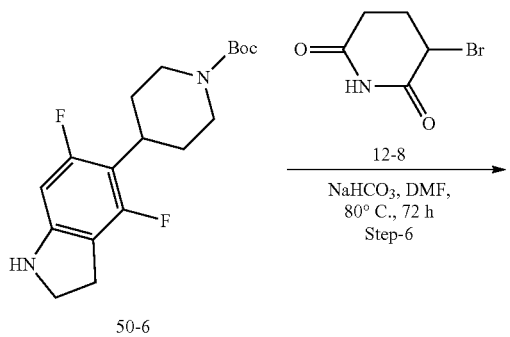

50-6

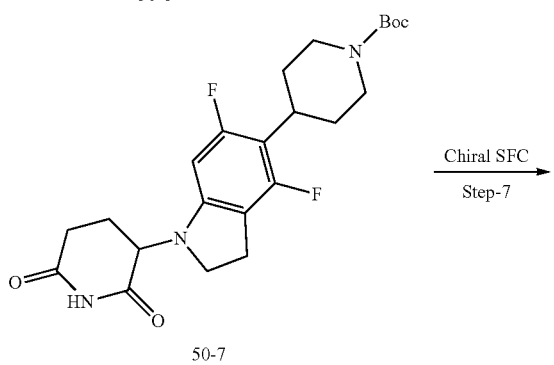

50-7

50-8

-continued

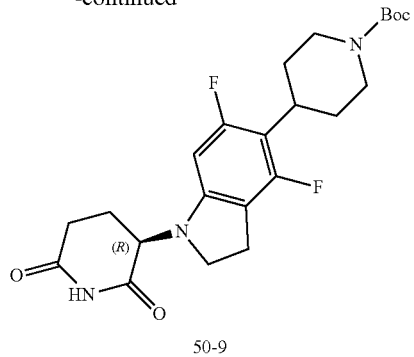

50-9

Step-1:

To a stirred solution of 4,6-difluoro-1H-indole 50-1 (4.5 g, 29.39 mmol) in CH₂Cl₂ (90 mL) was added triethylsilane (8.88 g, 76.41 mmol,) followed by trifluoroacetic acid (50.26 g, 440.81 mmol) at 0° C. The reaction mixture was stirred at room temperature for 16 h. After completion of the reaction, reaction mixture was evaporated to get a crude residue which was taken in ethyl acetate (500 mL) and washed with saturated sodium bicarbonate solution (500 mL) followed by brine solution (500 mL). The combined organic layer was dried over anhydrous sodium sulfate and concentrated under reduced pressure. The obtained crude material was purified by column chromatography (silica gel, 230-400 mesh) using 0-100% EtOAc in hexane as eluent to afford 4,6-difluoroindoline 50-2 (3.9 g, 25.01 mmol, 85.11% yield) as a brown color liquid. UPLC-MS (ES⁺): m/z 156.2 [M+H]⁺.

Step-2:

To a stirred solution of 4,6-difluoroindoline 50-2 (3.9 g, 25.14 mmol) in acetonitrile (80 mL) at 0° C. was added N-bromosuccinimide (3.13 g, 17.60 mmol). The reaction mixture was stirred at 0° C. for 1 h. After completion of the reaction, reaction mixture was quenched with satd. aq. sodium bicarbonate solution (500 mL) and diluted with ethyl acetate (300 mL). The organic layer was separated, dried over anhydrous sodium sulfate, filtered, and concentrated under reduced pressure to obtain crude, which was purified by column chromatography (silica gel, 230-400 mesh) using 0-100% EtOAc in hexane as eluent to afford 5-bromo-4,6-difluoro-indoline 50-3 (4.5 g, 17.88 mmol, 71.13% yield) as a brown color liquid. UPLC-MS (ES⁺): m/z 236.0 [M+2+H]⁺.

Step-3:

To a stirred solution of 5-bromo-4,6-difluoro-indoline 50-3 (4.5 g, 19.23 mmol) in THF (30 mL) and water (10 mL) was added sodium bicarbonate (4.85 g, 57.68 mmol) followed by benzyl chloroformate (3.94 g, 23.07 mmol) at 0° C. The reaction mixture was stirred at room temperature for 16 h. After completion of the reaction, reaction mixture was quenched with satd. aq. sodium bicarbonate solution (500 mL) and diluted with ethyl acetate (300 mL). The organic layer was separated, dried over anhydrous Na₂SO₄, filtered and concentrated under reduced pressure to obtain crude, which was purified by column chromatography (silica gel, 230-400 mesh) using-100% EtOAc in hexane as eluent to afford benzyl 5-bromo-4,6-difluoro-indoline-1-carboxylate 50-4 (5.5 g, 14.94 mmol, 77.69% yield) as a yellow solid. ¹H NMR (400 MHz, DMSO-d₆): δ 7.39 (m, 6H), 5.26 (s, 2H), 4.11 (t, J=8.80 Hz, 2H), 3.16 (t, J=8.40 Hz, 2H).

Step-4:

To a stirred solution of benzyl 5-bromo-4,6-difluoro-indoline-1-carboxylate 50-4 (4.5 g, 12.22 mmol) in THF (50 mL) and water (15 mL) were added tert-butyl 4-(4,4,5,5-tetramethyl-1,3,2-dioxaborolan-2-yl)-3,6-dihydro-2H-pyridine-1-carboxylate 9-2 (4.16 g, 13.44 mmol) and anhydrous potassium phosphate tribasic (7.78 g, 36.67 mmol), respectively. The mixture was purged with nitrogen gas for 10 minutes and added XPhos Pd G3 (620.71 mg, 733.35 mol). The purging was continued for another 5 minutes and then reaction mixture was stirred at 85° C. for 16 h. After completion of the reaction, water (200 mL) was added to the reaction mixture and extracted with ethyl acetate (2×200 mL). The combined organic fraction was dried over $Na_2SO_4$, filtered, and concentrated under reduced pressure to obtain crude. The crude material was purified by column chromatography (silica gel, 230-400 mesh) using 10% ethyl acetate in pet ether as eluent to afford benzyl 5-(1-tert-butoxycarbonyl-3,6-dihydro-2H-pyridin-4-yl)-4,6-difluoro-indoline-1-carboxylate 50-5 (4.5 g, 9.24 mmol, 72.91% yield) as a brown color liquid. UPLC-MS (ES$^+$): m/z 371.2 [M+−Boc+H]$^+$.

Step-5:

To a stirred solution of benzyl 5-(1-tert-butoxycarbonyl-3,6-dihydro-2H-pyridin-4-yl)-4,6-difluoro-indoline-1-carboxylate 50-5 (4.5 g, 9.56 mmol) in anhydrous 1,4-dioxane (60 mL) was added 20% palladium hydroxide on carbon (50% moisture) (2.7 g) at ambient temperature under nitrogen atmosphere. The mixture was stirred at room temperature under hydrogen atmosphere (balloon pressure) for 48 h. After completion of the reaction, the reaction mixture was filtered over celite bed and washed with ethyl acetate (500 mL). The filtrate was concentrated under reduced pressure to obtain crude, which was triturated with n-pentane (20 mL) to afford tert-butyl 4-(4,6-difluoroindolin-5-yl)piperidine-1-carboxylate 50-6 (3.0 g, 8.59 mmol, 89.82% yield) as an off-white solid. LCMS (ES$^+$): m/z 239.2 [M+−Boc+H]$^+$.

Step-6:

To a stirred solution of tert-butyl 4-(4,6-difluoroindolin-5-yl)piperidine-1-carboxylate 50-6 (3.2 g, 9.46 mmol) in anhydrous DMF (30 mL) was added 3-bromopiperidine-2,6-dione 12-8 (5.45 g, 28.37 mmol) followed by NaHCO$_3$ (3.18 g, 37.83 mmol) at ambient temperature under nitrogen atmosphere. The resulting mixture was stirred at 80° C. for 72 h. After completion, the reaction mixture was diluted with cold water (500 mL) and extracted with ethyl acetate (2×500 mL). The combined organic layer was washed with saturated brine solution (500 mL), dried over anhydrous sodium sulfate and concentrated under reduced pressure to obtain crude, which was purified by column chromatography (silica gel, 230-400 mesh) using 0-100% ethyl acetate in hexane as eluent to afford tert-butyl 4-[1-(2,6-dioxo-3-piperidyl)-4,6-difluoro-indolin-5-yl]piperidine-1-carboxylate 50-7 (1.4 g, 2.99 mmol, 31.62% yield) as off brown solid. UPLC-MS (ES$^+$): m/z 350.2 [M+−Boc+H]$^+$.

Step-7:

Enantiomers of racemic compound tert-butyl 4-[1-(2,6-dioxo-3-piperidyl)-4,6-difluoro-indolin-5-yl]piperidine-1-carboxylate 50-7 (200 mg) was separated by chiral SFC [chiral SFC purification method: Column: I Cellulose B (250*30) mm, 5 μm; Mobile phase: CO$_2$:isopropanol [74:36]; Total flow: 120/min; Wavelength: 210 nm]. The early eluting peak (arbitrarily assigned as S) tert-butyl (S)-4-(1-(2,6-dioxopiperidin-3-yl)-4,6-difluoroindolin-5-yl)piperidine-1-carboxylate 50-8 (80 mg, 177.45 mol, 39.88% yield, 100% enantiopurity) was obtained as off-white solid. UPLC-MS (ES$^+$): m/z 448.2 [M+H]$^+$. $^1$H NMR (400 MHz, DMSO-d$_6$): δ 10.86 (s, 1H), 6.25 (d, J=12.00 Hz, 1H), 4.64 (dd, J=4.80, 12.80 Hz, 1H), 4.05-4.02 (m, 2H), 3.53-3.50 (m, 1H), 3.23-3.31 (m, 1H), 2.98-2.91 (m, 6H), 2.61-2.60 (m, 1H), 2.24-2.19 (m, 1H), 1.95-1.92 (m, 1H), 1.76-1.73 (m, 2H), 1.61-1.58 (m, 2H), 1.42 (s, 9H). The late eluting peak (arbitrarily assigned as R) tert-butyl (R)-4-(1-(2,6-dioxopiperidin-3-yl)-4,6-difluoroindolin-5-yl)piperidine-1-carboxylate 50-9 (60 mg, 133.22 mol, 29.94% yield, 97.82% enantiopurity) was obtained as off-white solid. UPLC-MS (ES$^+$): m/z 350.2 [M+−Boc+H]$^+$. $^1$H NMR (400 MHz, DMSO-d$_6$): δ 10.86 (s, 1H), 6.25 (d, J=12.00 Hz, 1H), 4.64 (dd, J=4.80, 13.20 Hz, 1H), 4.05-4.02 (m, 2H), 3.53-3.50 (m, 1H), 3.23-3.31 (m, 1H), 2.94-2.73 (m, 6H), 2.61-2.57 (m, 1H), 2.24-2.19 (m, 1H), 1.95-1.94 (m, 1H), 1.76-1.73 (m, 2H), 1.61-1.58 (m, 2H), 1.42 (s, 9H).

Scheme 51: Synthesis of 3-[4-[4-(1,1-difluoro-2-hydroxy-ethyl)-1-piperidyl]indolin-1-yl]piperidine-2,6-dione

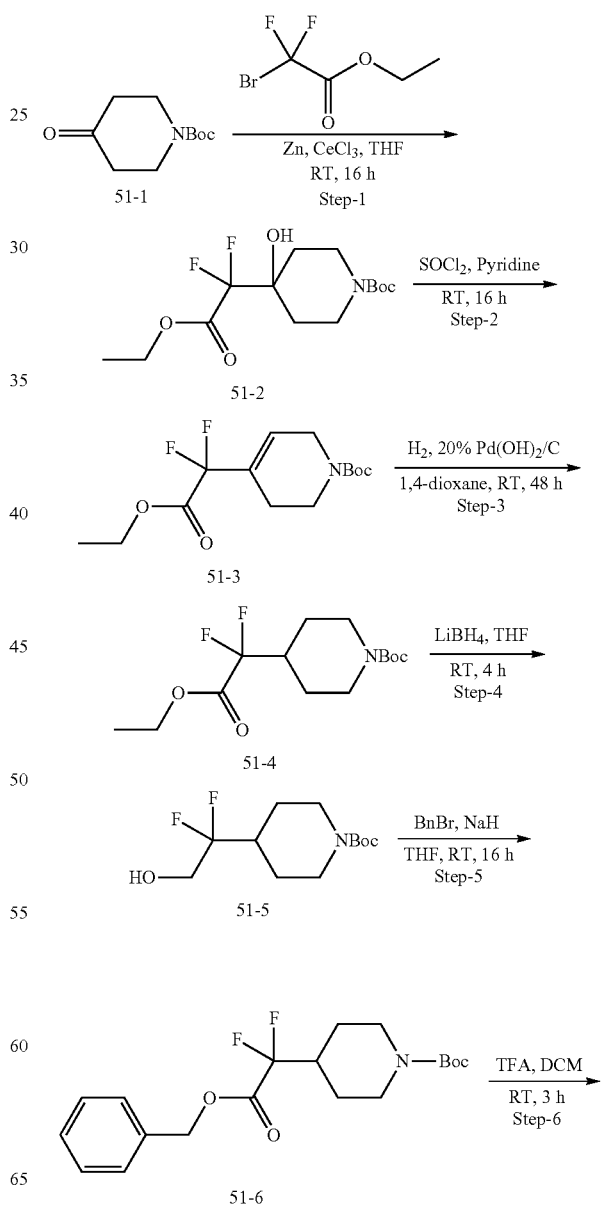

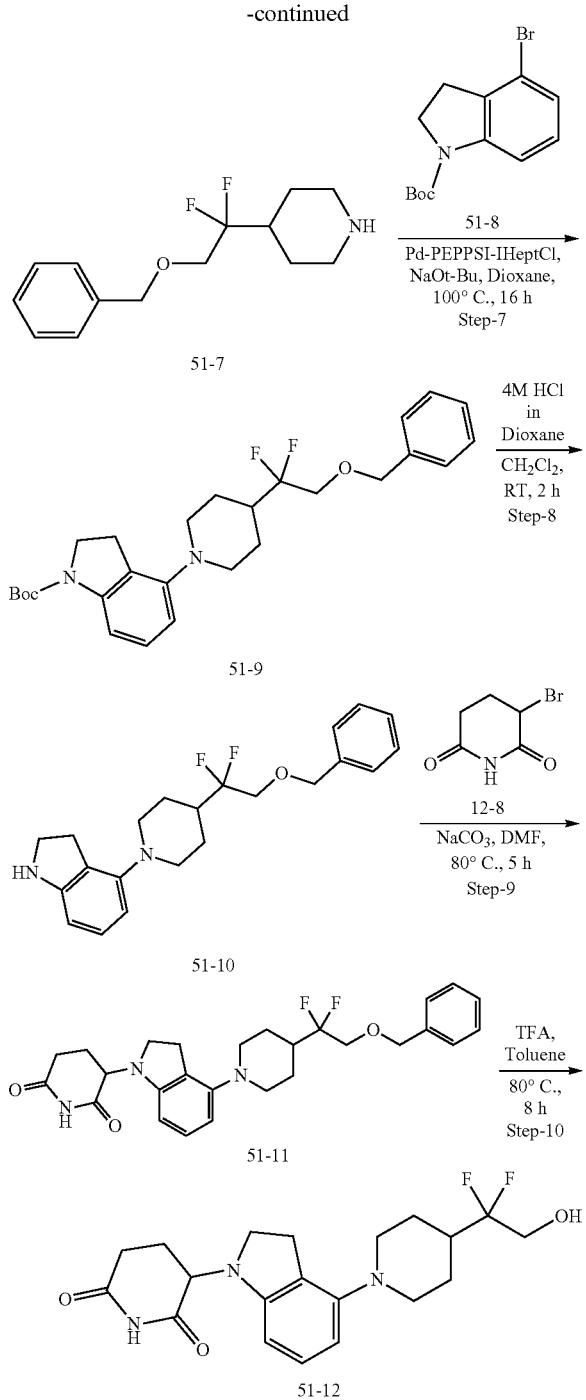

Step-1:

To a stirred solution of tert-butyl 4-oxopiperidine-1-carboxylate 51-1 (10 g, 50.19 mmol) in anhydrous THF (150 mL) was added cerium(III) chloride (2.47 g, 10.04 mmol) at 0° C. under nitrogen atmosphere. The reaction mixture was stirred for 5 minutes and was added zinc (6.56 g, 100.38 mmol) portionwise at same temperature and stirred for 10 minutes. To the above mixture ethyl 2-bromo-2,2-difluoroacetate (20.37 g, 100.38 mmol, 12.87 mL) was added dropwise and the resulting mixture was stirred at ambient temperature for 16 h. After completion of the reaction, reaction mixture was poured into water (500 mL). The precipitated solid was filtered over celite bed and washed with ethyl acetate (500 ml). Two layers in filtrate were separated and the aqueous layer was extracted with ethyl acetate (2×200 mL). The combined organic layer was dried over anhydrous sodium sulfate and concentrated under reduced pressure to get the crude residue which was purified by column chromatography (silica gel, 230-400 mesh) using 0-50% EtOAc in hexane as eluent to afford tert-butyl 4-(2-ethoxy-1,1-difluoro-2-oxo-ethyl)-4-hydroxy-piperidine-1-carboxylate 51-2 (10.1 g, 3.24 mmol, 62.24% yield) as a colorless gummy liquid. $^1$H NMR (400 MHz, DMSO-$d_6$): δ 5.83 (s, 1H), 4.30 (q, J=7.20 Hz, 2H), 3.87-3.84 (m, 2H), 2.98-2.92 (m, 2H), 1.69-1.66 (m, 2H), 1.55-1.47 (m, 2H), 1.43 (s, 9H), 1.18 (t, J=7.20 Hz, 3H).

Step-2:

To a stirred solution of tert-butyl 4-(2-ethoxy-1,1-difluoro-2-oxo-ethyl)-4-hydroxy-piperidine-1-carboxylate 51-2 (7.2 g, 22.27 mmol) in pyridine (150 mL) was added thionyl chloride (21.19 g, 178.15 mmol) dropwise at 0° C. under nitrogen atmosphere. The resulting mixture was stirred at ambient temperature for 16 h. After completion of the reaction, reaction mixture was diluted with water (500 mL) and poured into satd. aq. sodium bicarbonate solution (1000 mL) with stirring and extracted with ethyl acetate (2×500 mL). The combined organic layer was dried over anhydrous sodium sulfate and concentrated under reduced pressure to obtain a crude residue. The crude product was purified by column chromatography (silica gel, 230-400 mesh) using 0-50% EtOAc in hexane as eluent to afford tert-butyl 4-(2-ethoxy-1,1-difluoro-2-oxo-ethyl)-3,6-dihydro-2H-pyridine-1-carboxylate 51-3 (5.1 g, 16.70 mmol, 75.01% yield) as a colorless gummy liquid. $^1$H NMR (400 MHz, DMSO-$d_6$): δ 6.23 (s, 1H), 4.33 (q, J=6.80 Hz, 2H), 3.95-3.89 (m, 2H), 3.45 (t, J=5.60 Hz, 2H), 2.14-2.14 (m, 2H), 1.41 (s, 9H), 1.26 (t, J=7.20 Hz, 3H).

Step-3:

To a stirred solution of tert-butyl 4-(2-ethoxy-1,1-difluoro-2-oxo-ethyl)-3,6-dihydro-2H-pyridine-1-carboxylate 51-3 (5.1 g, 16.70 mmol) in anhydrous 1,4-doxane (100 mL) was added 20% palladium hydroxide on carbon (50% moisture, 3 g, 33.41 mmol) at ambient temperature under nitrogen atmosphere. The reaction mixture was stirred at room temperature under hydrogen pressure (80 psi) for 48 h. After completion of the reaction, reaction mixture was filtered over celite bed and washed with ethyl acetate (500 mL). The filtrate was concentrated under reduced pressure to obtain tert-butyl 4-(2-ethoxy-1,1-difluoro-2-oxo-ethyl)piperidine-1-carboxylate 51-4 (4.4 g, 14.32 mmol, 85.71% yield) as a colorless gummy liquid. $^1$H NMR (400 MHz, DMSO-$d_6$): δ 4.33 (q, J=7.20 Hz, 2H), 4.02-3.96 (m, 2H), 3.45-3.41 (m, 1H), 2.74-2.68 (m, 2H), 2.50 (m, 1H), 2.18-2.15 (m, 1H) 1.69-1.65 (m, 2H), 1.41 (s, 9H), 1.27 (t, J=3.60 Hz, 3H).

Step-4:

To a stirred solution of tert-butyl 4-(2-ethoxy-1,1-difluoro-2-oxo-ethyl)piperidine-1-carboxylate 51-4 (3.9 g, 12.69 mmol) in anhydrous THE (60 mL) was added lithium borohydride (2 M in THE, 12.69 mL, 25.38 mmol) dropwise at 0° C. under nitrogen atmosphere. The resulting mixture was stirred at room temperature for 4 h. After completion of the reaction, reaction mixture was cooled to 0° C. and quenched with saturated aq. NH$_4$Cl solution (100 mL). The mixture was stirred for 5 minutes, diluted with water (100 mL) and extracted with ethyl acetate (2×200 mL). The combined organic layer was washed with brine solution (100 mL), dried over anhydrous sodium sulfate and concentrated under reduced pressure to afford tert-butyl 4-(1,1-difluoro- 2-hydroxy-ethyl)piperidine-1-carboxylate 51-5 (3.1 g, 11.59 mmol, 91.35% yield) as a colorless gum.

Step-5:

To a stirred solution of tert-butyl 4-(1,1-difluoro-2-hydroxy-ethyl)piperidine-1-carboxylate 51-5 (2.0 g, 7.54 mmol) in anhydrous THF (30 mL) was added sodium hydride (60% dispersion in mineral oil) (433.29 mg, 18.85 mmol) portionwise at 0° C. under nitrogen atmosphere. The reaction mixture was stirred for 15 min. Benzyl bromide (1.81 g, 10.55 mmol) dissolved in anhydrous THF (5 mL) was added dropwise to above solution at 0° C. The resulting mixture was stirred at ambient temperature for 16 h. After completion of the reaction, reaction mixture was cooled to 0° C. and quenched with saturated aq. $NH_4Cl$ solution (100 mL), diluted with water (50 mL) and extracted with ethyl acetate (2×100 ml). The combined organic layer was washed with brine solution (100 mL), dried over anhydrous $Na_2SO_4$ and concentrated under reduced pressure to obtain crude. The crude material was purified by column chromatography (silica gel, 230-400 mesh) using 0-50% EtOAc in hexane as eluent to afford tert-butyl 4-(2-benzyloxy-1,1-difluoro-ethyl)piperidine-1-carboxylate 51-6 (1.9 g, 4.86 mmol, 64.53% yield) as a colorless gum.

Step-6:

To a stirred solution tert-butyl 4-(2-benzyloxy-1,1-difluoro-ethyl)piperidine-1-carboxylate 51-6 (1.9 g, 5.35 mmol) in anhydrous $CH_2Cl_2$ (20 mL) was added trifluoroacetic acid (4 g, 35.08 mmol, 2.70 mL) at 0° C. under nitrogen atmosphere. The resulting mixture was stirred at ambient temperature for 3 h. After completion of the reaction, reaction mixture was concentrated under reduced pressure to get a crude residue, which was diluted with ice-cold water (50 mL) and neutralized with saturated aq. $NaHCO_3$ solution (50 mL). Mixture was extracted with $CH_2Cl_2$ (2×50 mL). The combined organic layer was dried over anhydrous $Na_2SO_4$ and concentrated under reduced pressure to afford 4-(2-benzyloxy-1,1-difluoro-ethyl)piperidine 51-7 (1.2 g, 4.64 mmol, 86.78% yield) as a pale yellow gummy solid. UPLC-MS (ES$^+$): m/z 256.2 [M+H]$^+$.

Step-7:

To a stirred solution of tert-butyl 4-bromoindoline-1-carboxylate 51-8 (1.2 g, 4.02 mmol) in anhydrous 1,4-dioxane (15 mL) was added 4-(2-benzyloxy-1,1-difluoro-ethyl)piperidine 51-7 (1.13 g, 4.43 mmol) followed by sodium tert-butoxide (1.16 g, 12.07 mmol) at room temperature. Mixture was purged with nitrogen for 10 minutes and Pd-PEPPSI-IHeptCl (391.49 mg, 402.45 mol) was added at room temperature. Purging was continued for another 5 minutes, and reaction mixture was stirred at 100° C. for 16 h. After completion of the reaction, reaction mixture was diluted with ethyl acetate and filtered through celite bed. Filtrate was concentrated under reduced pressure to obtain crude residue, which was purified by column chromatography (silica gel, 230-400 mesh) using 10-20% ethyl acetate in hexane as eluent to afford tert-butyl 4-[4-(2-benzyloxy-1,1-difluoro-ethyl)-1-piperidyl]indoline-1-carboxylate 51-9 (1.2 g, 2.44 mmol, 60.51% yield) as brown color gummy solid. UPLC-MS (ES$^+$): m/z 473.2 [M+H]$^+$.

Step-8:

To a stirred solution of tert-butyl 4-[4-(2-benzyloxy-1,1-difluoro-ethyl)-1-piperidyl]indoline-1-carboxylate 51-9 (1 g, 2.12 mmol) in $CH_2Cl_2$ (10 mL) was added 4 M HCl in 1,4-dioxane (6 mL) dropwise at 0° C. under nitrogen atmosphere. The resulting mixture was stirred at ambient temperature for 2 h. After completion of the reaction, reaction mixture was concentrated under reduced pressure to obtain crude, which was triturated with n-pentane (20 mL) and dried under vacuum to afford 4-[4-(2-benzyloxy-1,1-difluoro-ethyl)-1-piperidyl]indoline hydrochloride 51-10 (800 mg, 1.70 mmol, 80.53% yield) as an off-white solid. UPLC-MS (ES$^+$): m/z 373.2 [M+H]$^+$.

Step-9:

To a stirred solution of 4-[4-(2-benzyloxy-1,1-difluoro-ethyl)-1-piperidyl]indoline 51-10 (800 mg, 1.96 mmol) in anhydrous DMF (10 mL) was added 3-bromopiperidine-2,6-dione 12-8 (1.13 g, 5.87 mmol) followed by $NaHCO_3$ (657.43 mg, 7.83 mmol) at ambient temperature under nitrogen atmosphere. The resulting mixture was stirred at 80° C. for 5 h. After completion of the reaction, reaction mixture was diluted with cold water (200 mL) and extracted with ethyl acetate (2×200 mL). The combined organic layer was washed with brine solution (200 mL), dried over anhydrous sodium sulfate, filtered, and concentrated under reduced pressure to obtain crude. The crude product was purified by column chromatography (silica gel, 230-400 mesh) using 0-100% ethyl acetate in hexane as eluent to afford 3-[4-[4-(2-benzyloxy-1,1-difluoro-ethyl)-1-piperidyl]indolin-1-yl]piperidine-2,6-dione 51-11 (500 mg, 985.42 mol, 50.37% yield) as off brown solid. UPLC-MS (ES$^+$): m/z 484.2 [M+H]$^+$.

Step-10:

To a stirred solution of 3-[4-[4-(2-benzyloxy-1,1-difluoro-ethyl)-1-piperidyl]indolin-1-yl]piperidine-2,6-dione 51-11 (370 mg, 765.18 mol) in toluene (5 mL) was added trifluoroacetic acid (872.48 mg, 7.65 mmol, 589.51 L) at ambient temperature under nitrogen atmosphere. The mixture was stirred at 80° C. for 8 h. After completion of the reaction, reaction mixture was diluted with cold water (100 mL) and basified by using satd. aq. $NaHCO_3$ solution (100 mL). The reaction mixture was extracted with ethyl acetate (2×50 mL). The combined organic layer was washed with saturated brine (50 mL), dried over anhydrous $Na_2SO_4$ and concentrated under reduced pressure to obtain crude, which was purified by column chromatography (silica gel, 230-400 mesh) using 0-100% ethyl acetate in hexane as eluent to afford 3-[4-[4-(1,1-difluoro-2-hydroxy-ethyl)-1-piperidyl]indolin-1-yl]piperidine-2,6-dione 51-12 (250 mg, 615.74 mol, 80.47% yield) as a violet color solid. UPLC-MS (ES$^+$): m/z 394.2 [M+H]$^+$. $^1$H NMR (400 MHz, DMSO-d$_6$): δ 10.77 (s, 1H), 6.90 (t, J=8.00 Hz, 1H), 6.25-6.20 (m, 2H), 5.48 (s, 1H), 4.59 (dd, J=4.80, 13.20 Hz, 1H), 3.68-3.61 (m, 2H), 3.41-3.37 (m, 1H), 3.29-3.27 (m, 3H), 2.85-2.68 (m, 3H), 2.60-2.50 (m, 3H), 2.20-2.08 (m, 2H), 1.93-1.80 (m, 3H), 1.54-1.51 (m, 2H).

Scheme 52: Synthesis of tert-butyl 4-[6-fluoro-1-[(3S)-2,6-dioxo-3-piperidyl]indolin-5-yl]piperidine-1-carboxylate and tert-butyl 4-[6-fluoro-1-[(3R)-2,6-dioxo-3-piperidyl]indolin-5-yl]piperidine-1-carboxylate

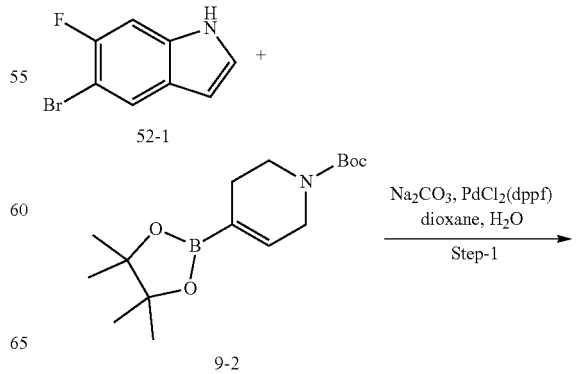

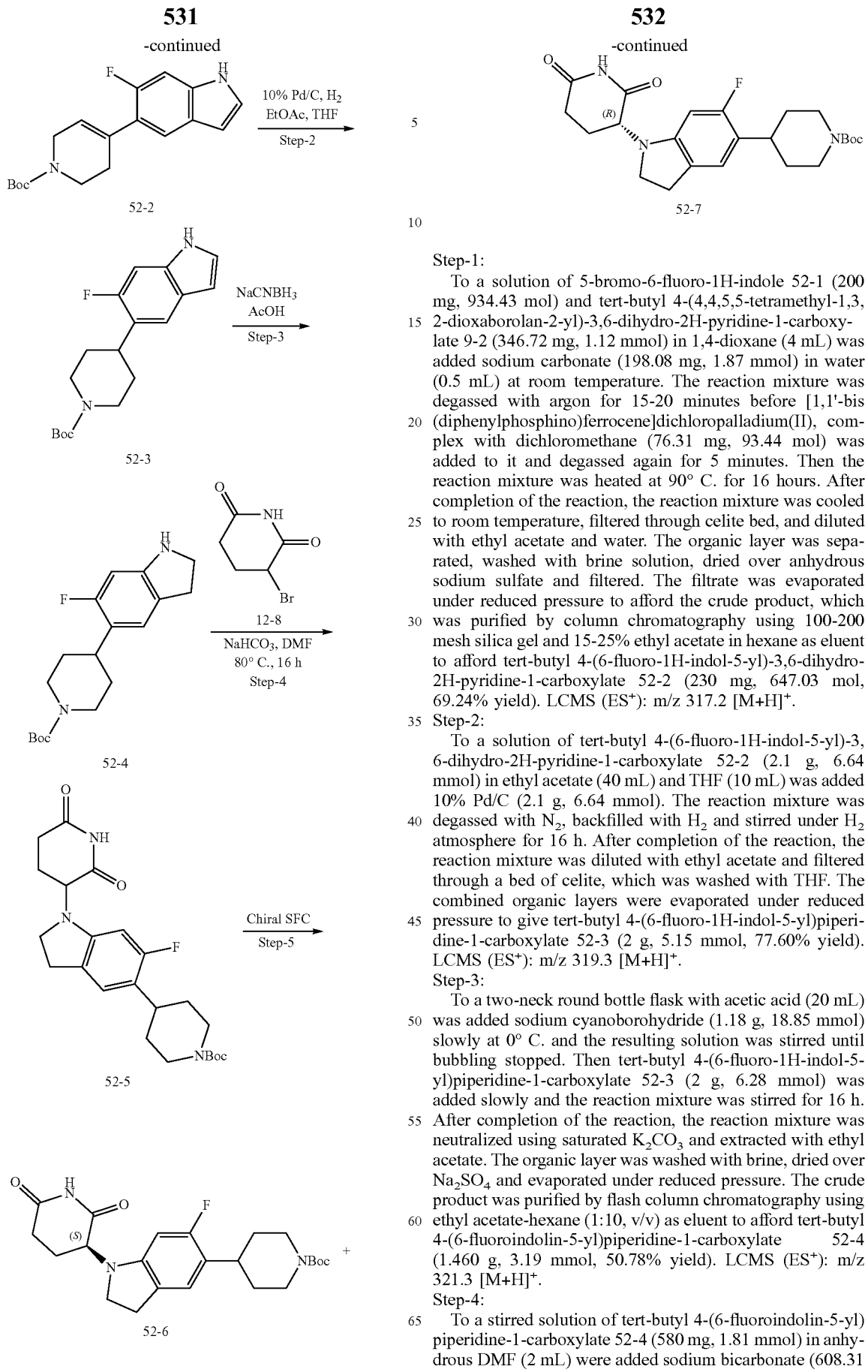

Step-1:
To a solution of 5-bromo-6-fluoro-1H-indole 52-1 (200 mg, 934.43 mol) and tert-butyl 4-(4,4,5,5-tetramethyl-1,3,2-dioxaborolan-2-yl)-3,6-dihydro-2H-pyridine-1-carboxylate 9-2 (346.72 mg, 1.12 mmol) in 1,4-dioxane (4 mL) was added sodium carbonate (198.08 mg, 1.87 mmol) in water (0.5 mL) at room temperature. The reaction mixture was degassed with argon for 15-20 minutes before [1,1'-bis (diphenylphosphino)ferrocene]dichloropalladium(II), complex with dichloromethane (76.31 mg, 93.44 mol) was added to it and degassed again for 5 minutes. Then the reaction mixture was heated at 90° C. for 16 hours. After completion of the reaction, the reaction mixture was cooled to room temperature, filtered through celite bed, and diluted with ethyl acetate and water. The organic layer was separated, washed with brine solution, dried over anhydrous sodium sulfate and filtered. The filtrate was evaporated under reduced pressure to afford the crude product, which was purified by column chromatography using 100-200 mesh silica gel and 15-25% ethyl acetate in hexane as eluent to afford tert-butyl 4-(6-fluoro-1H-indol-5-yl)-3,6-dihydro-2H-pyridine-1-carboxylate 52-2 (230 mg, 647.03 mol, 69.24% yield). LCMS (ES$^+$): m/z 317.2 [M+H]$^+$.

Step-2:
To a solution of tert-butyl 4-(6-fluoro-1H-indol-5-yl)-3,6-dihydro-2H-pyridine-1-carboxylate 52-2 (2.1 g, 6.64 mmol) in ethyl acetate (40 mL) and THF (10 mL) was added 10% Pd/C (2.1 g, 6.64 mmol). The reaction mixture was degassed with N$_2$, backfilled with H$_2$ and stirred under H$_2$ atmosphere for 16 h. After completion of the reaction, the reaction mixture was diluted with ethyl acetate and filtered through a bed of celite, which was washed with THF. The combined organic layers were evaporated under reduced pressure to give tert-butyl 4-(6-fluoro-1H-indol-5-yl)piperidine-1-carboxylate 52-3 (2 g, 5.15 mmol, 77.60% yield). LCMS (ES$^+$): m/z 319.3 [M+H]$^+$.

Step-3:
To a two-neck round bottle flask with acetic acid (20 mL) was added sodium cyanoborohydride (1.18 g, 18.85 mmol) slowly at 0° C. and the resulting solution was stirred until bubbling stopped. Then tert-butyl 4-(6-fluoro-1H-indol-5-yl)piperidine-1-carboxylate 52-3 (2 g, 6.28 mmol) was added slowly and the reaction mixture was stirred for 16 h. After completion of the reaction, the reaction mixture was neutralized using saturated K$_2$CO$_3$ and extracted with ethyl acetate. The organic layer was washed with brine, dried over Na$_2$SO$_4$ and evaporated under reduced pressure. The crude product was purified by flash column chromatography using ethyl acetate-hexane (1:10, v/v) as eluent to afford tert-butyl 4-(6-fluoroindolin-5-yl)piperidine-1-carboxylate 52-4 (1.460 g, 3.19 mmol, 50.78% yield). LCMS (ES$^+$): m/z 321.3 [M+H]$^+$.

Step-4:
To a stirred solution of tert-butyl 4-(6-fluoroindolin-5-yl)piperidine-1-carboxylate 52-4 (580 mg, 1.81 mmol) in anhydrous DMF (2 mL) were added sodium bicarbonate (608.31 mg, 7.24 mmol) and 3-bromopiperidine-2,6-dione 12-8 (695.17 mg, 3.62 mmol) at ambient temperature under nitrogen atmosphere. The reaction mixture was stirred at 80° C. for 16 h. After completion, the reaction mixture was diluted with water (20 mL) and extracted with ethyl acetate (3×30 mL). The combined organic layer was washed with water (2×50 mL) and brine (50 ml), respectively, dried over anhydrous sodium sulfate, filtered, and concentrated under reduced pressure to obtain crude. The crude was purified through column chromatography (silica gel, 100-200 mesh) using 0-100% ethyl acetate in hexane as eluentto afford tert-butyl 4-[1-(2,6-dioxo-3-piperidyl)-6-fluoro-indolin-5-yl]piperidine-1-carboxylate 52-5 (360 mg, 798.34 mol, 44.10% yield) as an off white solid. UPLC-MS (ES$^+$): m/z 376.2 [M−tBu+H]$^+$, 332.2 [M−Boc+H]$^+$.

Step-5:

Racemic compound tert-butyl 4-[1-(2,6-dioxo-3-piperidyl)-6-fluoro-indolin-5-yl]piperidine-1-carboxylate 52-5 (150 mg, 340.67 mol) was purified by chiral SFC to separate R/S enantiomers (Chiral SFC purification method: Column: I cellulose B (250*30) mm, 5 μm; mobile phase: CO$_2$: isopropanol [50:35]). The early eluting peak (arbitrarily assigned as S) tert-butyl 4-[6-fluoro-1-[(3S)-2,6-dioxo-3-piperidyl]indolin-5-yl]piperidine-1-carboxylate 52-6 (55 mg, 123.65 mol, 36.30% yield, 100% enantiopurity) was obtained as an off-white solid. UPLC-MS (ES$^-$): m/z 430.5 [M−H]$^-$. [α$_D$]$^-$ 43.27°, c=0.514, acetonitrile, Temp: 20.1° C. $^1$H NMR (400 MHz, DMSO-d$_6$): δ 10.82 (s, 1H), 6.91 (d, J=7.60 Hz, 1H), 6.31 (d, J=12.00 Hz, 1H), 4.60 (dd, J=4.80, 13.20 Hz, 1H), 4.11-4.02 (m, 2H), 3.48-3.41 (m, 1H), 3.32-3.27 (m, 1H), 2.91-2.70 (m, 5H), 2.61-2.52 (m, 1H), 2.26-2.15 (m, 1H), 1.94-1.87 (m, 1H), 1.66-1.60 (m, 2H), 1.51-1.42 (m, 12H). The late eluting peak (arbitrarily assigned as R) tert-butyl 4-[6-fluoro-1-[(3R)-2,6-dioxo-3-piperidyl]indolin-5-yl]piperidine-1-carboxylate 52-7 (60 mg, 135.53 mol, 39.78% yield, 100% enantiopurity) was obtained as an off white solid. UPLC-MS (ES$^-$): m/z 430.2 [M−H]$^-$. [α$_D$]29.45°, c=0.508, acetonitrile, Temp: 20.2° C. $^1$H NMR (400 MHz, DMSO-d$_6$): δ 10.82 (s, 1H), 6.91 (d, J=7.60 Hz, 1H), 6.31 (d, J=12.00 Hz, 1H), 4.60 (dd, J=4.80, 13.20 Hz, 1H), 4.10-4.03 (m, 2H), 3.48-3.41 (m, 1H), 3.32-3.26 (m, 1H), 2.91-2.67 (m, 5H), 2.61-2.52 (m, 1H), 2.25-2.16 (m, 1H), 1.94-1.87 (m, 1H), 1.67-1.63 (m, 2H), 1.51-1.39 (m, 12H).

Scheme 53: Synthesis of (3S)-3-[4-[4-(hydroxymethyl)-1-piperidyl]indolin-1-yl]piperidine-2,6-dione and (3R)-3-[4-[4-(hydroxymethyl)-1-piperidyl]indolin-1-yl]piperidine-2,6-dione

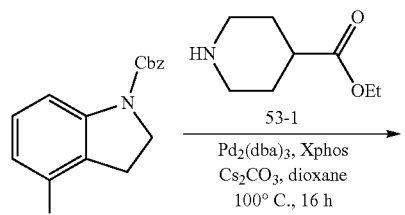

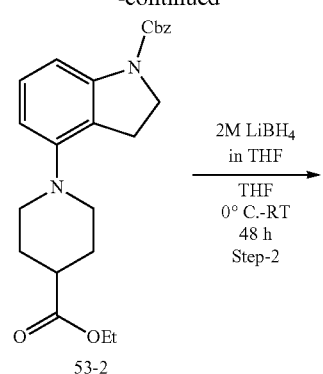

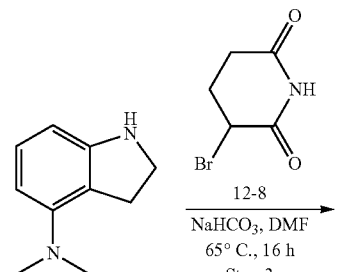

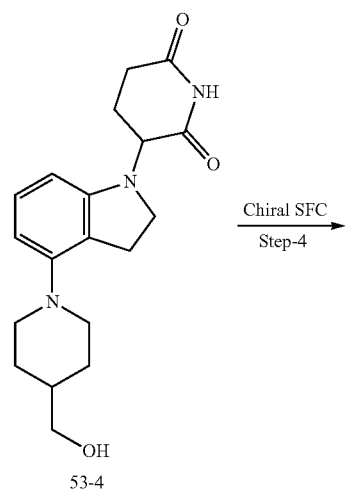

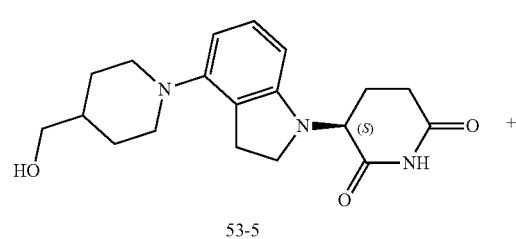

535

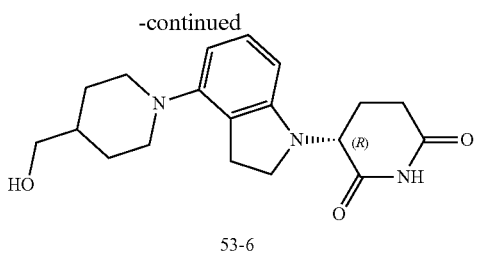

53-6

Step-1:
To a stirred solution of a mixture of benzyl 4-bromoindoline-1-carboxylate 34-2 (10 g, 30.10 mmol) and ethyl piperidine-4-carboxylate 53-1 (5.21 g, 33.11 mmol, 5.10 mL) in 1,4-dioxane (47.45 mL) were added cesium carbonate (29.42 g, 90.31 mmol and tris(dibenzylideneacetone)dipalladium(0) (2.76 g, 3.01 mmol) at room temperature. The reaction mixture was degassed with nitrogen gas for 10 minutes, then dicyclohexyl-[2-(2,4,6-triisopropylphenyl) phenyl]phosphane (2.87 g, 6.02 mmol) was added, again degassed with nitrogen for 2 min. The resulting reaction mixture was stirred at 100° C. for 16 h. After completion of the reaction, reaction mass was filtered through a pad of celite, filtrate was concentrated under reduced pressure to get the crude. The crude was purified by column chromatography (silica gel, 100-200 mesh) using 0-100% ethyl acetate in hexane as eluent to afford benzyl 4-(4-ethoxycarbonyl-1-piperidyl)indoline-1-carboxylate 53-2 (10 g, 23.12 mmol, 76.79% yield) as a brown liquid. UPLC-MS (ES$^+$): m/z 409.2 [M+H]$^+$.

Step-2:
To a stirred solution of benzyl 4-(4-ethoxycarbonyl-1-piperidyl)indoline-1-carboxylate 53-2 (4.82 g, 11.15 mmol) in THF (60 mL) was added lithium borohydride (2 M in THF, 27.86 mL) at 0° C. The reaction mixture was stirred at room temperature for 48 h. The reaction mixture was quenched with satd. aq. Na$_2$SO$_4$ solution (20 mL) and diluted with ethyl acetate (100 mL). The precipitated solid was filtered, the filtrate was dried over anhydrous Na$_2$SO$_4$, filtered again and the filtrate was concentrated under reduced pressure to obtain the crude residue. The crude residue was mixed with another batch (4.82 g scale) and purified by column chromatography (silica gel, 100-200 mesh) using 0-100% ethyl acetate in hexane as eluent to afford (1-indolin-4-yl-4-piperidyl)methanol 53-3 (2.1 g, 8.92 mmol, 40.01% combined yield) as a brown liquid. UPLC-MS (ES$^+$): m/z 233.1 [M+H]$^+$.

Step-3:
To a stirred solution of (1-indolin-4-yl-4-piperidyl)methanol 53-3 (1.5 g, 6.37 mmol) in DMF (10 mL) was added sodium bicarbonate (2.68 g, 31.85 mmol) followed by 3-bromopiperidine-2,6-dione 12-8 (3.67 g, 19.11 mmol) at room temperature. The reaction mixture stirred at 65° C. for 16 h. The reaction mixture diluted with ethyl acetate (1000 mL) and filtered through a pad of celite. The filtrate was quenched with water (300 mL) and then extracted with ethyl acetate (3×500 mL). The combined organic layer was washed with brine solution (50 mL), dried over anhydrous Na$_2$SO$_4$, filtered and concentrated under reduced pressure to obtain crude residue. The crude was mixed with another batch (600 mg scale) and purified by column chromatography (silica gel, 100-200 mesh) using ethyl acetate in CH$_2$Cl$_2$ as eluent to afford 3-[4-[4-(hydroxymethyl)-1-piperidyl]indolin-1-yl]piperidine-2,6-dione 53-4 (2.1 g, 6.07 mmol, 68.55% combined yield) as a brown solid. UPLC-MS (ES$^+$): m/z 344.1 [M+H]$^+$.

536

Step-4:
Enantiomers of 3-[4-[4-(hydroxymethyl)-1-piperidyl]indolin-1-yl]piperidine-2,6-dione 53-4 (2.1 g, 6.07 mmol) were separated by chiral SFC [Chiral SFC purification method: LUX A3 (250*30) mm, 5 µm; mobile phase: CO$_2$:0.1% NH$_3$ in isopropanol (65:35), total flow: 120 mL/min; backpressure: 120 bar; wavelength: 210 nm]. The early eluting peak (arbitrarily assigned as S) (3S)-3-[4-[4-(hydroxymethyl)-1-piperidyl]indolin-1-yl]piperidine-2,6-dione 53-5 (800 mg, 2.31 mmol, 38.01% yield, 99.31% enantiopurity) was isolated as a pale brown solid. UPLC-MS (ES$^+$): m/z 344.1 [M+H]$^+$. $^1$H NMR (400 MHz, DMSO-d$_6$): δ 10.76 (s, 1H), 6.88 (t, J=7.60 Hz, 1H), 6.23 (t, J=8.00 Hz, 1H), 6.18 (d, J=8.00 Hz, 1H), 4.58 (dd, J=4.80, 12.80 Hz, 1H), 4.46 (t, J=5.60 Hz, 1H), 3.42-3.36 (m, 1H), 3.27-3.20 (m, 4H), 2.85-2.76 (m, 3H), 2.61-2.46 (m, 4H), 2.24-2.11 (m, 1H), 1.94-1.88 (m, 1H), 1.77-1.70 (m, 2H), 1.51-1.42 (m, 1H), 1.30-1.19 (m, 2H). The late eluting peak (arbitrarily assigned as R) (3R)-3-[4-[4-(hydroxymethyl)-1-piperidyl]indolin-1-yl]piperidine-2,6-dione 53-6 (800 mg, 2.30 mmol, 37.88% yield, 99.28% enantiopurity) was isolated as a pale brown solid. UPLC-MS (ES$^+$): m/z 344.1 [M+H]$^+$. $^1$H NMR (400 MHz, DMSO-d$_6$): δ 10.76 (s, 1H), 6.88 (t, J=8.00 Hz, 1H), 6.23 (d, J=8.00 Hz, 1H), 6.18 (d, J=8.00 Hz, 1H), 4.58 (dd, J=4.80, 12.80 Hz, 1H), 4.46 (t, J=5.20 Hz, 1H), 3.42-3.35 (m, 1H), 3.27-3.20 (m, 4H), 2.85-2.74 (m, 3H), 2.61-2.44 (m, 4H), 2.22-2.12 (m, 1H), 1.92-1.88 (m, 1H), 1.79-1.72 (m, 2H), 1.52-1.42 (m, 1H), 1.31-1.19 (m, 2H).

Scheme 54: Synthesis of tert-butyl 1-[[1-(2,6-dioxo-3-piperidyl)indolin-4-yl]methyl]piperidine-4-carboxylate, tert-butyl 1-[[1-[(3S)-2,6-dioxo-3-piperidyl]indolin-4-yl]methyl]piperidine-4-carboxylate tert-butyl 1-[[1-[(3R)-2,6-dioxo-3-piperidyl]indolin-4-yl]methyl]piperidine-4-carboxylate

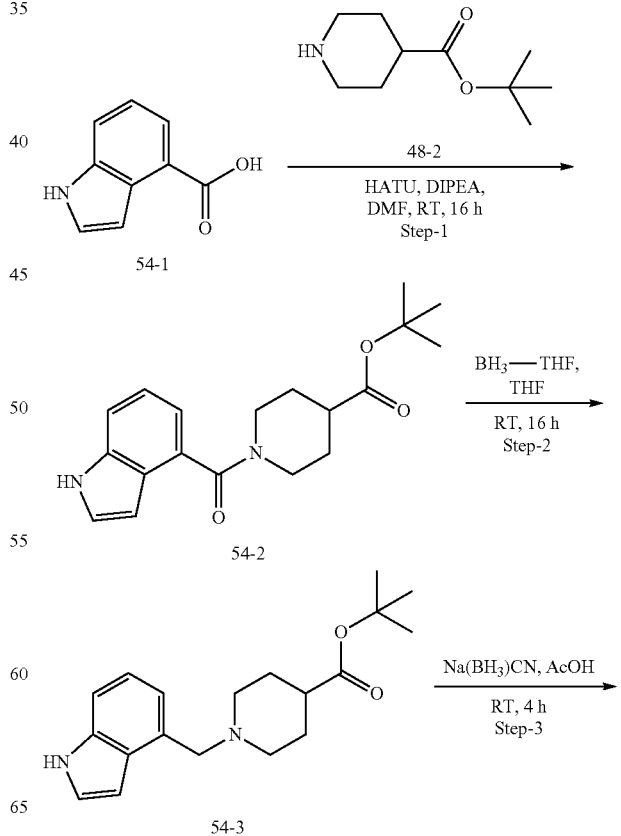

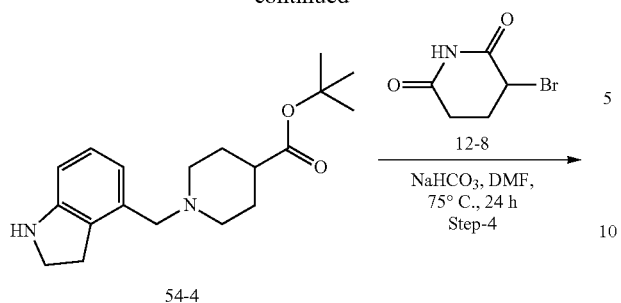

54-4

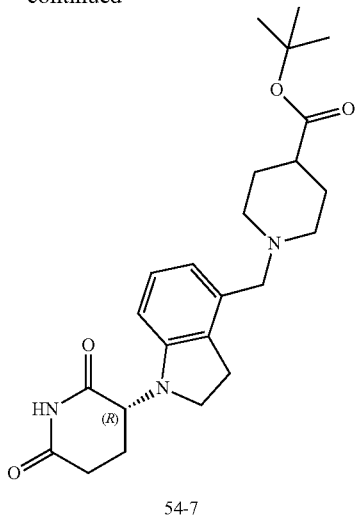

54-7

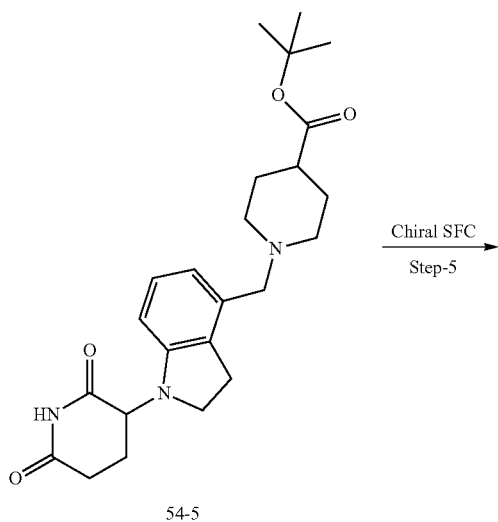

54-5

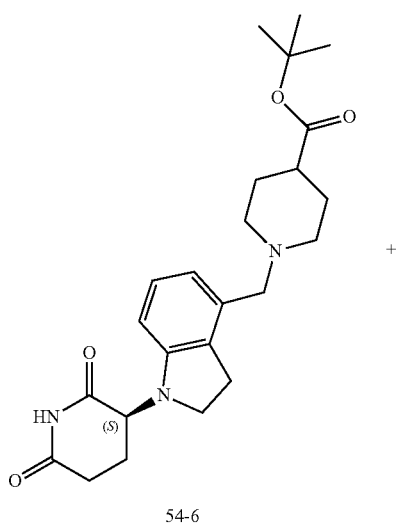

54-6

Step-1:

To a stirred solution of 1H-indole-4-carboxylic acid 54-1 (3 g, 18.62 mmol) and tert-butyl piperidine-4-carboxylate 48-2 (4.48 g, 20.22 mmol) in DMF (30 mL) were added HATU (10.62 g, 27.92 mmol) followed by DIPEA (7.22 g, 55.85 mmol, 9.73 mL) at room temperature under nitrogen atmosphere. The reaction mixture was stirred at room temperature for 16 h. After completion of the reaction, reaction mixture was cooled to 0° C. and the excess of the reagent was quenched with satd. aq. NH$_4$Cl solution (200 mL). The aqueous layer was extracted with EtOAc (2×300 mL). The combined organic layer was washed with water (300 mL) followed by brine solution (300 mL). The organic layer was separated, dried over anhydrous Na$_2$SO$_4$, filtered and concentrated to dryness under reduced pressure to obtain crude, which was purified by flash column chromatography (silica-gel, 230-400 mesh) using 0-100% EtOAc in pet ether as eluent to afford tert-butyl 1-(1H-indole-4-carbonyl)piperidine-4-carboxylate 54-2 (3 g, 8.08 mmol, 43.42% yield) as a colorless liquid. UPLC-MS (ES$^+$): m/z 329.2 [M+H]$^+$.

Step-2:

To a stirred solution of tert-butyl 1-(1H-indole-4-carbonyl)piperidine-4-carboxylate 54-2 (5 g, 15.23 mmol) in THF (50 mL) was added BH$_3$-THF (1 M in THF, 76.13 mL). The reaction mixture was stirred at room temperature for 16 h. After completion of the reaction, reaction mixture was cooled to 0° C. and the excess of the reagent was quenched with methanol (30 mL) and water (100 mL). The aqueous layer was extracted with EtOAc (2×400 mL). The combined organic layer was washed with water (400 mL) followed by brine (400 mL). The organic layer was dried over anhydrous Na$_2$SO$_4$, filtered, and concentrated to dryness under reduced pressure to obtain crude, which was purified by flash column chromatography (silica-gel, 230-400 mesh) using 0-100% EtOAc in pet ether as eluent to afford tert-butyl 1-(1H-indol-4-ylmethyl)piperidine-4-carboxylate 54-3 (2.7 g, 4.52 mmol, 29.71% yield) as a gummy liquid. UPLC-MS (ES$^+$): m/z 315.2 [M+H]$^+$.

Step-3:

To a stirred solution of tert-butyl 1-(1H-indol-4-ylmethyl)piperidine-4-carboxylate 54-3 (2.7 g, 8.59 mmol) in acetic acid (25 mL) was added sodium cyanoborohydride (809.46 mg, 12.88 mmol) at 0° C. The reaction mixture was stirred at room temperature for 4 h. The reaction was quenched with ice-water (200 mL) and the mixture was extracted with EtOAc (2×250 mL). The combined organic layer was washed with satd. aq. NaHCO₃ solution (2×150 mL) and brine (100 mL), dried over anhydrous Na₂SO₄, filtered and concentrated under reduced pressure to afford tert-butyl 1-(indolin-4-ylmethyl)piperidine-4-carboxylate 54-4 (1.7 g, 2.39 mmol, 25.78% yield) as a colorless gum. UPLC-MS (ES⁺): m/z 317.2 [M+H]⁺.

Step-4:

To a stirred solution of tert-butyl 1-(indolin-4-ylmethyl) piperidine-4-carboxylate 54-4 (200 mg, 632.04 mol) and 3-bromopiperidine-2,6-dione 12-8 (485.43 mg, 2.53 mmol) in anhydrous DMF (4.0 mL) was added NaHCO₃ (212.39 mg, 2.53 mmol) portionwise. The reaction mixture was stirred at 75° C. for 24 h. After 24 h, two more lots of 3-bromopiperidine-2,6-dione 12-8 (485.43 mg, 2.53 mmol) were added and reaction mixture was continued to stir additional 24 h. After completion of the reaction, reaction mixture was filtered through a cotton pad and the filtrate was concentrated under reduced pressure to obtain crude, which was purified by column chromatography (230-400 mesh silica gel, 0-100% ethyl acetate in pet ether) and further purified by reverse phase chromatography (RediSep Rf Gold® 40 g column following a method: mobile Phase A: 0.1% ammonium bicarbonate in milli-Q water; mobile phase B: acetonitrile; flow rate: 15 mL/min) to afford tert-butyl 1-[[1-(2,6-dioxo-3-piperidyl)indolin-4-yl]methyl]piperidine-4-carboxylate 54-5 (45 mg, 100.60 mol, 15.92% yield) as a pale brown solid. UPLC-MS (ES⁺): m/z 428.2 [M+H]⁺.

Step-5:

Racemic compound tert-butyl 1-[[1-(2,6-dioxo-3-piperidyl)indolin-4-yl]methyl]piperidine-4-carboxylate 54-5 (230 mg) was purified by chiral SFC to separate S— and R-isomers [Chiral SFC purification method: column: I Cellulose B (250*30) mm, 5 µm; mobile phase: CO₂: 0.5% isopropylamine in isopropanol (70:30); total flow: 100 mL/min; wavelength: 220 nm]. The early eluting peak (arbitrarily assigned as S) tert-butyl 1-[[1-[(3S)-2,6-dioxo-3-piperidyl]indolin-4-yl]methyl]piperidine-4-carboxylate 54-6 (35 mg, 79.96 mol, 14.86% yield, 100% enantiopurity) as a brown solid. UPLC-MS (ES⁺): m/z 428.2 [M+H]⁺. H NMR (400 MHz, DMSO-d₆): δ 10.78 (s, 1H), 6.90 (t, J=7.60 Hz, 1H), 6.48 (d, J=7.60 Hz, 1H), 6.37 (d, J=8.00 Hz, 1H), 4.61 (dd, J=4.80, 13.20 Hz, 1H), 3.43-3.41 (m, 1H), 3.31-3.27 (m, 3H), 2.97-2.72 (m, 5H), 2.60-2.53 (m, 1H), 2.21-2.17 (m, 2H), 1.96-1.92 (m, 3H), 1.75-1.73 (m, 2H), 1.53-1.49 (m, 2H), 1.39 (s, 9H). The late eluting peak (arbitrarily assigned as R) tert-butyl 1-[[1-[(3R)-2,6-dioxo-3-piperidyl]indolin-4-yl]methyl]piperidine-4-carboxylate 54-7 (80 mg, 184.24 µmol, 34.25% yield, 95.35% enantiopurity) as an off white solid. UPLC-MS (ES⁺): m/z 428.2 [M+H]⁺. ¹H NMR (400 MHz, DMSO-d₆): δ 10.78 (s, 1H), 6.90 (t, J=7.60 Hz, 1H), 6.48 (d, J=7.20 Hz, 1H), 6.37 (d, J=7.60 Hz, 1H), 4.61 (dd, J=4.80, 13.20 Hz, 1H), 3.34-3.31 (m, 1H), 3.29-3.26 (m, 3H), 2.97-2.90 (m, 5H), 2.61-2.60 (m, 1H), 2.21-2.17 (m, 2H), 1.97-1.91 (m, 3H), 1.75-1.72 (m, 2H), 1.57-1.49 (m, 2H), 1.39 (s, 9H).

Scheme 55: Synthesis of tert-butyl ((1S,4r)-4-(1-((S)-2,6-dioxopiperidin-3-yl)-4,6-difluoroindolin-5-yl)cyclohexyl) (methyl)carbamate, tert-butyl ((1R,4r)-4-(1-((R)-2,6-dioxopiperidin-3-yl)-4,6-difluoroindolin-5-yl)cyclohexyl) (methyl)carbamate, tert-butyl ((1R,4s)-4-(1-((S)-2,6-dioxopiperidin-3-yl)-4,6-difluoroindolin-5-yl)cyclohexyl) (methyl)carbamate, and tert-butyl ((1S,4s)-4-(1-((R)-2,6-dioxopiperidin-3-yl)-4,6-difluoroindolin-5-yl)cyclohexyl) (methyl)carbamate

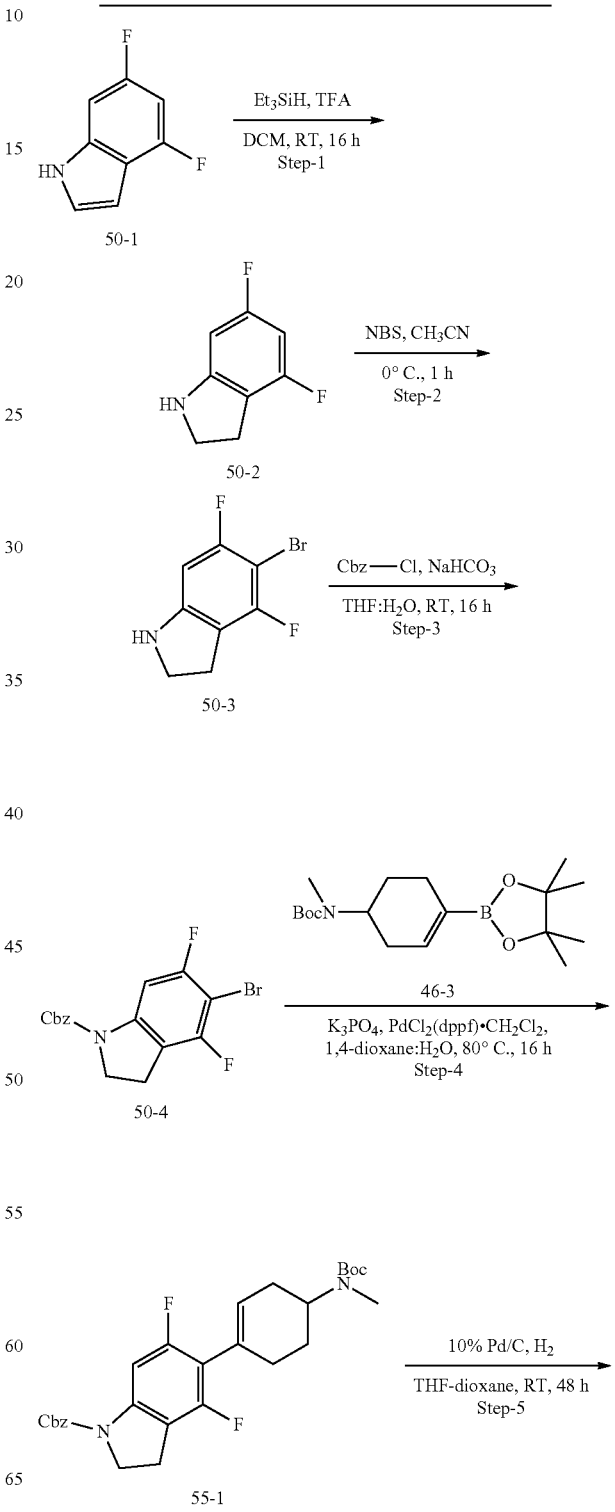

541

-continued

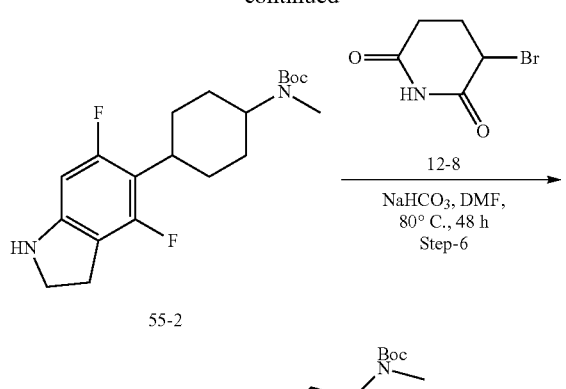

55-2

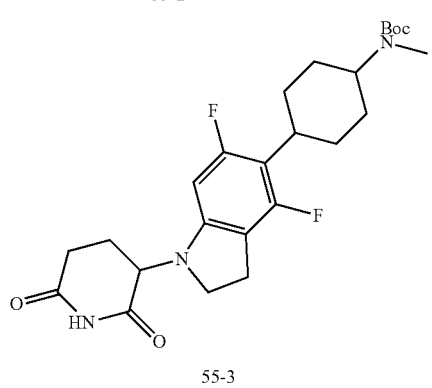

55-3

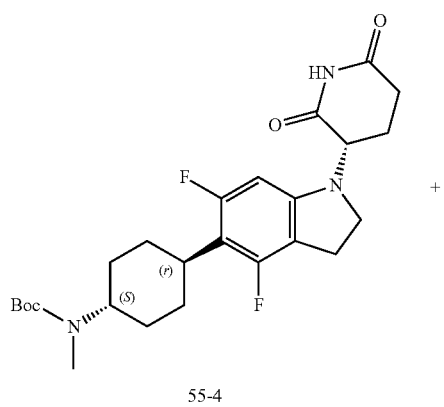

55-4

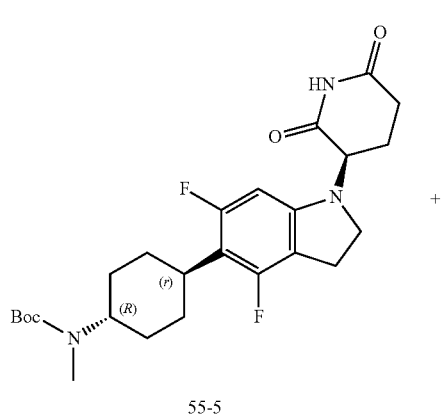

55-5

542

-continued

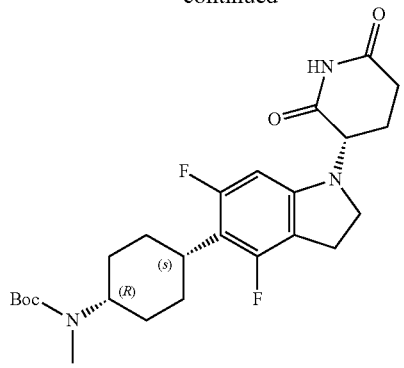

55-6

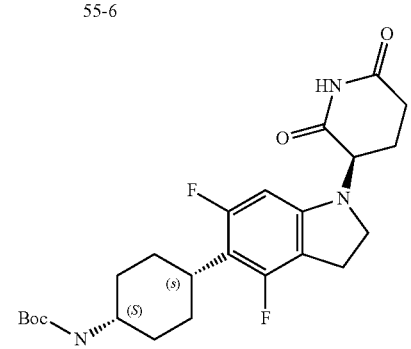

55-7

Step-1:

To a stirred solution of 4,6-difluoro-1H-indole 50-1 (1.0 g, 6.53 mmol) in $CH_2Cl_2$ (20 mL) at 0° C. was added triethylsilane (1.97 g, 16.98 mmol) and trifluoroacetic acid (11.17 g, 97.96 mmol). The reaction mixture was stirred at room temperature for 16 h. After completion, the reaction mixture was concentrated to obtain crude. The crude was dissolved in ethyl acetate (100 mL), washed with satd. aq. $NaHCO_3$ (100 mL) and brine solution (500 mL), respectively. The combined organic layer was dried over anhydrous $Na_2SO_4$, filtered, and concentrated under reduced pressure to obtain crude, which was purified by column chromatography (silica gel, 230-400 mesh) using 0-100% EtOAc in hexane as eluent to afford 4,6-difluoroindoline 50-2 (800 mg, 5.15 mmol, 78.92% yield) as a brown liquid. UPLC-MS ($ES^+$): m/z 156.2 $[M+H]^+$.

Step-2:

To a stirred solution of 4,6-difluoroindoline 50-2 (800 mg, 5.16 mmol) in acetonitrile (16 mL) at 0° C. was added N-bromosuccinimide (642.43 mg, 3.61 mmol). The reaction mixture was stirred at 0° C. for 1 h. After completion, the reaction mixture was quenched with satd. aq. $NaHCO_3$ (500 mL) and extracted with ethyl acetate (50 mL). The organic layer was dried over anhydrous $Na_2SO_4$, filtered and concentrated under reduced pressure to obtain crude, which was purified by column chromatography (silica gel, 230-400 mesh) using 0-100% EtOAc in hexane as eluent to afford 5-bromo-4,6-difluoro-indoline 50-3 (750 mg, 3.15 mmol, 61.18% yield) as a brown liquid. UPLC-MS ($ES^+$): m/z 236.2 $[M+2+H]^+$.

Step-3:

To a stirred solution of 5-bromo-4,6-difluoro-indoline 50-3 (750 mg, 3.20 mmol) in a mixture of THF (7 mL) and water (3 mL) was added $NaHCO_3$ (807.65 mg, 9.61 mmol)

and benzyl chloroformate (656.00 mg, 3.85 mmol), respectively, at 0° C. The reaction mixture was stirred at room temperature for 16 h. After completion, the reaction mixture was quenched with satd. aq. NaHCO$_3$ solution (50 mL) and extracted with ethyl acetate (50 mL). The organic layer was dried over anhydrous Na$_2$SO$_4$, filtered, and concentrated under reduced pressure to obtain crude. The crude was purified by column chromatography (silica gel, 230-400 mesh) using 0-100% EtOAc in hexane as eluent to afford benzyl 5-bromo-4,6-difluoro-indoline-1-carboxylate 50-4 (900 mg, 2.44 mmol, 76.28% yield) as a yellow solid. $^1$H NMR (400 MHz, DMSO-d$_6$): δ 7.46-735 (m, 6H), 5.21 (s, 2H), 4.11 (t, J=8.8 Hz, 2H), 3.15 (t, J=8.8 Hz, 2H).

Step-4:

To a stirred solution of benzyl 5-bromo-4,6-difluoro-indoline-1-carboxylate 50-4 (800 mg, 2.17 mmol) in 1,4-dioxane (8 mL) and H$_2$O (2 mL) were added tert-butyl N-methyl-N-[4-(4,4,5,5-tetramethyl-1,3,2-dioxaborolan-2-yl)cyclohex-3-en-1-yl]carbamate 46-3 (952.68 mg, 2.82 mmol), potassium phosphate tribasic anhydrous (1.38 g, 6.52 mmol), respectively. The reaction mixture was purged with nitrogen gas for 10 minutes and added [1,1'-bis(diphenylphosphino)ferrocene]dichloropalladium(II), complex with dichloromethane (177.44 mg, 217.29 mol) into it and again purged with nitrogen gas for 5 minutes. The reaction mixture was stirred at 80° C. for 16 h. After completion, water (20 mL) was added to the reaction mixture and extracted with ethyl acetate (2×50 mL). The combined organic layer was dried over anhydrous Na$_2$SO$_4$, filtered and concentrated under reduced pressure to obtain crude. The crude was purified by column chromatography (silica gel, 230-400 mesh) using 0-100% EtOAc in hexane as eluent to afford benzyl 5-[4-[tert-butoxycarbonyl(methyl)amino]cyclohexen-1-yl]-4,6-difluoro-indoline-1-carboxylate 55-1 (500 mg, 999.68 mol, 46.01% yield) as a brown solid. UPLC-MS (ES$^+$): m/z 399.2 [M−Boc+H]$^+$.

Step-5:

To a stirred solution of benzyl 5-[4-[tert-butoxycarbonyl(methyl)amino]cyclohexen-1-yl]-4,6-difluoro-indoline-1-carboxylate 55-1 (500 mg, 1.00 mmol) in anhydrous 1,4-dioxane (5 mL), THF (5 mL) was added 10% palladium on carbon (400 mg) at ambient temperature under nitrogen atmosphere. The reaction mixture was stirred at room temperature under hydrogen atmosphere (balloon pressure) for 48 h. After completion, the reaction mixture was filtered over a celite bed and washed with EtOAc/CH$_2$Cl$_2$/THF (500 mL). The combined filtrate was concentrated under reduced pressure to obtain crude, which was triturated with n-pentane (20 mL) to afford tert-butyl N-[4-(4,6-difluoroindolin-5-yl)cyclohexyl]-N-methyl-carbamate 55-2 (320 mg, 829.59 mol, 82.72% yield) as colorless gum. UPLC-MS (ES$^+$): m/z 267.2 [M−Boc+H]$^+$.

Step-6:

To a stirred solution of tert-butyl N-[4-(4,6-difluoroindolin-5-yl)cyclohexyl]-N-methyl-carbamate 55-2 (320 mg, 873.26 mol) in anhydrous DMF (5 mL) were added 3-bromopiperidine-2,6-dione 12-8 (670.70 mg, 3.49 mmol) and NaHCO$_3$ (293.44 mg, 3.49 mmol) at ambient temperature under nitrogen atmosphere. The reaction mixture was stirred at 80° C. for 48 h. After completion, the reaction mixture diluted with cold water (100 mL) and extracted with ethyl acetate (2×50 mL). The combined organic layer was washed with brine solution (50 mL), dried over anhydrous Na$_2$SO$_4$, filtered and concentrated under reduced pressure to obtain crude, which was purified by column chromatography (silica gel, 230-400 mesh) using 0-100% ethyl acetate in hexane as eluent to afford tert-butyl N-[4-[1-(2,6-dioxo-3-piperidyl)-4,6-difluoro-indolin-5-yl]cyclohexyl]-N-methyl-carbamate 55-3 (160 mg, 334.38 mol, 38.29% yield) as light brown solid. UPLC-MS (ES$^+$): m/z 378.2 [M−Boc+H]$^+$.

Step-7:

The diastereomeric mixture compound tert-butyl N-[4-[1-(2,6-dioxo-3-piperidyl)-4,6-difluoro-indolin-5-yl]cyclohexyl]-N-methylcarbamate 55-3 (160 mg) was purified by chiral SFC [Chiral SFC purification method: column: Lux A1 (250*30) mm, 5 μm; mobile phase: CO$_2$: 0.5% isopropyl amine in isopropanol (86:14); total flow: 70 mL/min; wavelength: 220 nm]. Peak-1 (arbitrarily assigned as the (S)-trans isomer): tert-butyl ((1S,4r)-4-(1-((S)-2,6-dioxopiperidin-3-yl)-4,6-difluoroindolin-5-yl)cyclohexyl)(methyl)carbamate 55-4 (18 mg, 37.24 mol, 11.11% yield, 98.45% enantiopurity) was obtained as an off-white solid. UPLC-MS (ES$^+$): m/z 378.2 [M−Boc+H]$^+$. $^1$H NMR (400 MHz, DMSO-d$_6$): δ 10.85 (s, 1H), 6.24 (d, J=12.00 Hz, 1H), 4.65-4.61 (m, 1H), 3.85-3.72 (m, 1H), 3.52-3.51 (m, 1H), 3.34-3.32 (m, 1H), 2.98-2.76 (m, 2H), 2.74-2.61 (m, 5H), 2.61-2.60 (m, 1H), 2.23-2.19 (m, 1H), 1.94-1.93 (m, 1H), 1.82-1.61 (m, 8H), 1.51 (s, 9H). Peak-2 (arbitrarily assigned as the (R)-trans isomer): tert-butyl ((1R,4r)-4-(1-((R)-2,6-dioxopiperidin-3-yl)-4,6-difluoroindolin-5-yl)cyclohexyl)(methyl)carbamate 55-5 (15 mg, 30.40 mol, 9.07% yield, 97.28% enantiopurity) was obtained as an off-white solid. UPLC-MS (ES$^+$): m/z 378.2 [M−Boc+H]$^+$. $^1$H NMR (400 MHz, DMSO-d$_6$): δ 10.85 (s, 1H), 6.24 (d, J=12.00 Hz, 1H), 4.65-4.61 (m, 1H), 3.86-3.72 (m, 1H), 3.52-3.50 (m, 1H), 3.36-3.34 (m, 1H), 3.29-2.91 (m, 2H), 2.78-2.71 (m, 5H), 2.61-2.60 (m, 1H), 2.23-2.19 (m, 1H), 1.95-1.93 (m, 1H), 1.82-1.72 (m, 8H), 1.41 (s, 9H). Peak-3 (arbitrarily assigned as the (S)-cis isomer): tert-butyl ((1R,4s)-4-(1-((S)-2,6-dioxopiperidin-3-yl)-4,6-difluoroindolin-5-yl)cyclohexyl)(methyl)carbamate 55-6 (13 mg, 26.04 mol, 7.77% yield, 97.56% enantiopurity) was obtained as an off-white solid. UPLC-MS (ES$^+$): m/z 378.2 [M−Boc+H]$^+$. $^1$H NMR (400 MHz, DMSO-d$_6$): δ 10.85 (s, 1H), 6.24 (d, J=12.00 Hz, 1H), 4.66-4.61 (m, 1H), 3.99-3.98 (m, 1H), 3.53-3.52 (m, 1H), 2.99-2.91 (m, 6H), 2.75-2.70 (m, 2H), 2.61-2.56 (m, 1H), 2.24-2.19 (m, 1H), 1.92-1.85 (m, 5H), 1.66-1.59 (m, 4H), 1.40 (s, 9H). Peak-4 (arbitrarily assigned as (R)-cis isomer): tert-butyl ((1S,4s)-4-(1-((R)-2,6-dioxopiperidin-3-yl)-4,6-difluoroindolin-5-yl)cyclohexyl)(methyl)carbamate 55-7 (5 mg, 10.16 mol, 3.03% yield, 97.78% enantiopurity) was obtained as an off-white solid. UPLC-MS (ES$^+$): m/z 378.2 [M−Boc+H]$^+$. $^1$H NMR (400 MHz, DMSO-d$_6$): δ 10.85 (s, 1H), 6.24 (d, J=12.00 Hz, 1H), 4.64 (dd, J=8.40, Hz, 1H), 3.99-3.98 (m, 1H), 3.52-3.48 (m, 1H), 3.36-3.34 (m, 1H), 2.96-2.91 (m, 6H), 2.73-2.65 (m, 2H), 2.25-2.15 (m, 1H), 1.95-1.85 (m, 5H), 1.65-1.59 (m, 4H), 1.40 (s, 9H).

Scheme 56A: Synthesis of tert-butyl (3aS,7aR)-5-(1-benzloxycarbonylindolin-4-yl)-3,3a,4,6,7,7a-hexahydro-2H-pyrrolo[3,2-c]pyridine-1-carboxylate and tert-butyl (3aR,7aS)-5-(1-benzyloxycarbonylindolin-4-yl)-3,3a,4,6,7,7a-hexahydro-2H-pyrrolo[3,2-c]pyridine-1-carboxylate

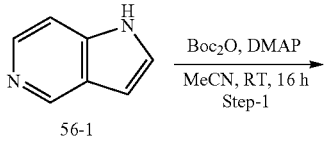

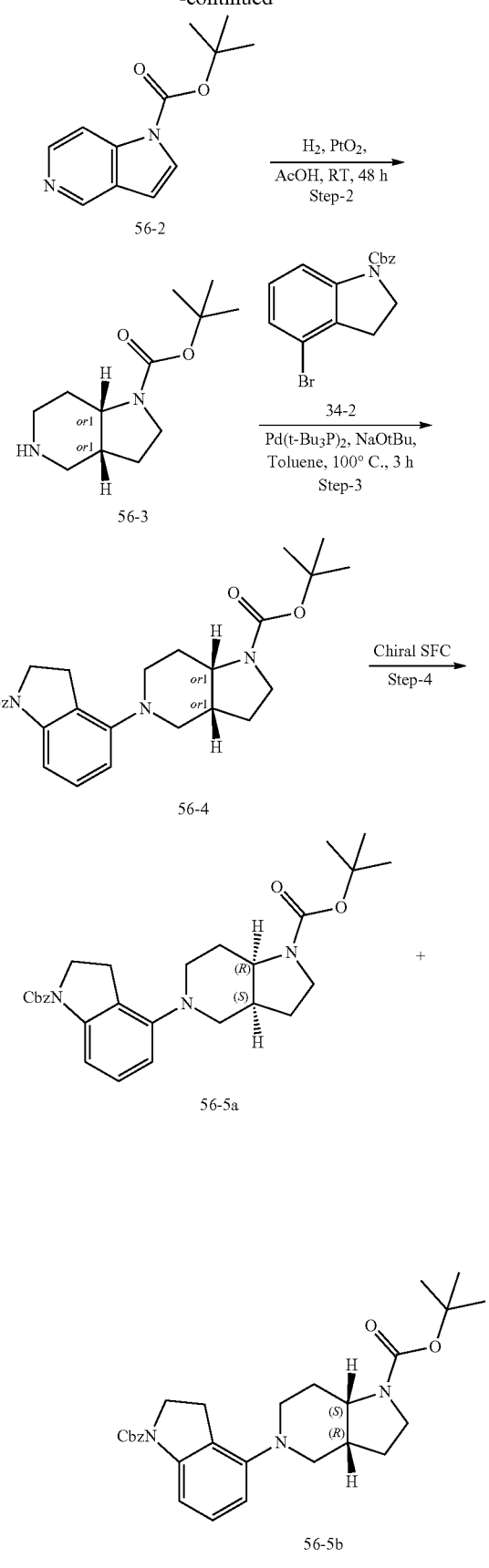

Step-1:

To a stirred solution of 1H-pyrrolo[3,2-c]pyridine 56-1 (10 g, 84.65 mmol) in acetonitrile (50 mL) were added di-tert-butyl dicarbonate (18.47 g, 84.65 mmol, 19.43 mL) and N,N-dimethylpyridin-4-amine (10.34 g, 84.65 mmol) at ambient temperature under nitrogen atmosphere. The reaction mixture was stirred at ambient temperature for 16 h. After completion of the reaction, the reaction mixture was concentrated under reduced pressure to obtain crude product. The crude compound was purified by column chromatography (silica gel, 230-400 mesh) using 0-100% of ethyl acetate in hexane as eluent to afford tert-butyl pyrrolo[3,2-c]pyridine-1-carboxylate 56-2 (11 g, 50.22 mmol, 59.33% yield) as a colorless oil. UPLC-MS (ES$^+$): m/z 219.2 [M+H]$^+$.

Step-2:

To a stirred solution of tert-butyl pyrrolo[3,2-c]pyridine-1-carboxylate 56-2 (3 g, 13.75 mmol) in acetic acid (70 mL) was added dioxoplatinum (624.27 mg, 2.75 mmol) at ambient temperature under nitrogen atmosphere. The resulting suspension was stirred at ambient temperature under hydrogen pressure for 48 h. After completion of the reaction, the reaction mixture was filtered through a pad of celite and washed with acetic acid (100 mL). The filtrate was concentrated under reduced pressure to obtain crude, which was basified with saturated sodium bicarbonate solution (500 mL), extracted with 10% MeOH in DCM (5×100 mL). The combined organic layer was dried over anhydrous sodium sulfate, filtered and concentrated to afford tert-butyl 2,3,3a,4,5,6,7,7a-octahydropyrrolo[3,2-c]pyridine-1-carboxylate 56-3 (2.5 g, 7.66 mmol, 55.72% yield) as a colorless liquid. UPLC-MS (ES$^+$): m/z 227.2 [M+H]$^+$.

Step-3:

A solution of benzyl 4-bromoindoline-1-carboxylate 34-2 (3.45 g, 10.39 mmol) and tert-butyl 2,3,3a,4,5,6,7,7a-octahydropyrrolo[3,2-c]pyridine-1-carboxylate 56-3 (3.06 g, 13.50 mmol) in toluene (70 mL) was added sodium 2-methylpropan-2-olate (2.00 g, 20.77 mmol) at ambient temperature under nitrogen atmosphere and the resulting reaction contents were degassed by bubbling of nitrogen for 10 min. Then, bis(tri-tert-butylphosphine)palladium (0) (530.76 mg, 1.04 mmol) was added to the reaction mixture and the reaction was stirred at 100° C. for 3 h. After completion of the reaction, the reaction mixture was diluted with ethyl acetate (100 mL) and filtered through celite pad. The filtrate was dried over anhydrous sodium sulfate, filtered, and concentrated under reduced pressure to obtain crude product. The crude product was purified by column chromatography (silica gel, 230-400 mesh) using 0-100% ethyl acetate in hexane as eluent to afford tert-butyl 5-(1-benzyloxycarbonylindolin-4-yl)-3,3a,4,6,7,7a-hexahydro-2H-pyrrolo[3,2-c]pyridine-1-carboxylate 56-4 (2.5 g, 5.14 mmol, 49.48% yield) as an off-white solid. UPLC-MS (ES$^+$): m/z 478.2 [M+H]$^+$.

Step-4:

Racemic compound tert-butyl 5-(1-benzyloxycarbonylindolin-4-yl)-3,3a,4,6,7,7a-hexahydro-2H-pyrrolo[3,2-c]pyridine-1-carboxylate 56-4 (3 g, 6.28 mmol) was purified by chiral SFC to separate the isomers (Chiral SFC purification method: Column: Lux-A3 (250*30) mm, 5 m; mobile phase CO$_2$:100% isopropanol [75:25] and flow rate 120 mL/min). The early eluting peak (stereochemistry arbitrarily assigned): tert-butyl (3aS,7aR)-5-(1-benzyloxycarbonylindolin-4-yl)-3,3a,4,6,7,7a-hexahydro-2H-pyrrolo[3,2-c]pyridine-1-carboxylate 56-5a (1.1 g, 2.29 mmol, 36.38% yield, 99.29% enantiopurity) was obtained as a light brown solid. UPLC-MS (ES$^+$): m/z 478.2 [M+H]$^+$. The late eluting peak (stereochemistry arbitrarily assigned): tert-butyl (3aR,7aS)-5-(1-benzyloxycarbonylindolin-4-yl)-3,3a,4,6,7,7a-hexahydro-2H-pyrrolo[3,2-c]pyridine-1-carboxylate 56-5b (1 g, 2.09 mmol, 33.21% yield, 95.83% enantiopurity) was obtained as a light brown solid. UPLC-MS (ES⁺): m/z 478.2 [M+H]⁺.

Scheme 56B: Synthesis of tert-butyl (3aS,7aR)-5-[1-[(3S)-2,6-dioxo-3-piperidyl]indolin-4-yl]-3,3a,4,6,7,7a-hexahydro-2H-pyrrolo[3,2-c]pyridine-1-carboxylate and tert-butyl (3aS,7aR)-5-[1-[(3R)-2,6-dioxo-3-piperidyl]indolin-4-yl]-3,3a,4,6,7,7a-hexahydro-2H-pyrrolo[3,2-c]pyridine-1-carboxylate

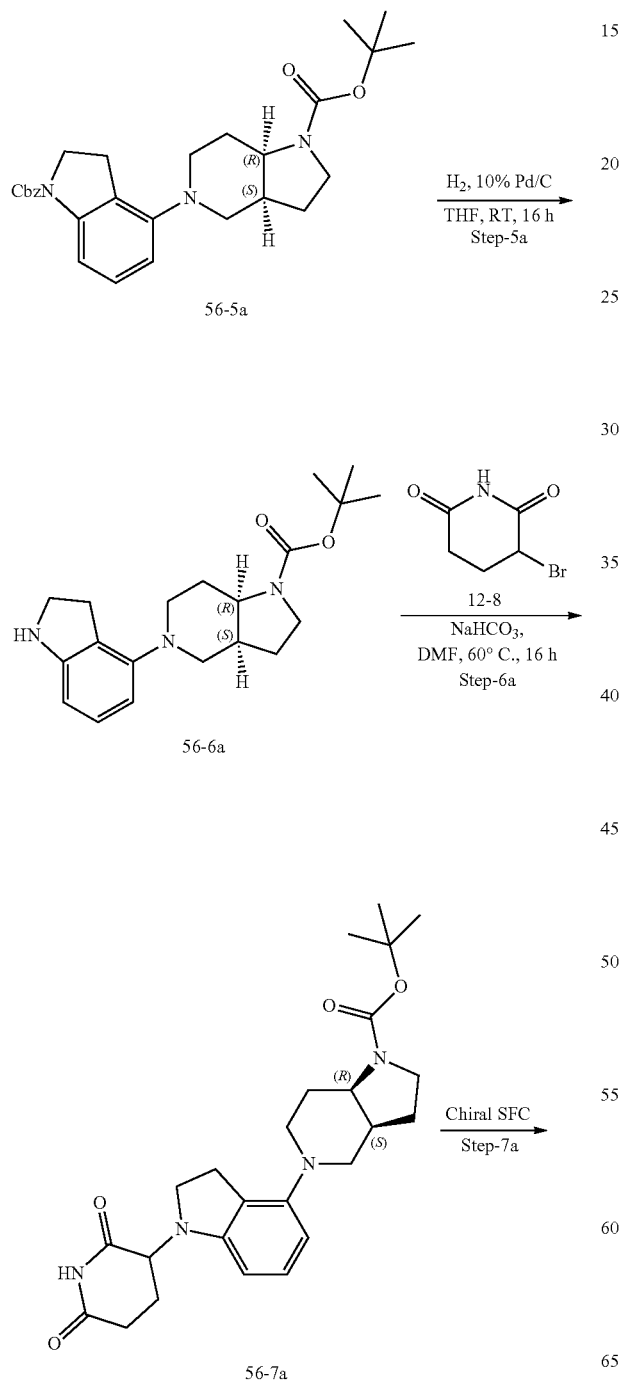

Step-5a:
To a stirred solution of tert-butyl (3aS,7aR)-5-(1-benzyloxycarbonylindolin-4-yl)-3,3a,4,6,7,7a-hexahydro-2H-pyrrolo[3,2-c]pyridine-1-carboxylate 56-5a (1 g, 2.09 mmol) in THF (20 mL) was added palladium, 10% on carbon (445.65 mg, 418.77 mol) at ambient temperature under nitrogen atmosphere. The resulting suspension was stirred at ambient temperature under hydrogen atmosphere (balloon pressure) for 16 h. After completion of the reaction, the reaction mixture was filtered through celite bed and washed with THF (200 mL). The filtrate was concentrated under reduced pressure to afford tert-butyl (3aS,7aR)-5-indolin-4-yl-3,3a,4,6,7,7a-hexahydro-2H-pyrrolo[3,2-c]pyridine-1-carboxylate 56-6a (700 mg, 1.47 mmol, 70.07% yield) as a light brown solid. UPLC-MS (ES⁺): m/z 344.2 [M+H]⁺.

Step-6a:
To a stirred solution of tert-butyl (3aS,7aR)-5-indolin-4-yl-3,3a,4,6,7,7a-hexahydro-2H-pyrrolo[3,2-c]pyridine-1-carboxylate 56-6a (700.00 mg, 2.04 mmol) in DMF (20 mL) was added sodium bicarbonate (856.06 mg, 10.19 mmol) followed by 3-bromopiperidine-2,6-dione 12-8 (1.17 g, 6.11 mmol) at ambient temperature under nitrogen atmosphere. The reaction mixture was stirred at 60° C. for 16 h. After completion of the reaction, reaction mixture was diluted with ethyl acetate (50 mL), quenched with water (50 mL), and extracted with ethyl acetate (2×50 mL). The combined organic layer was washed with brine solution (50 mL), dried over anhydrous sodium sulfate, filtered, and concentrated under reduced pressure to obtain crude. The crude was purified by column chromatography (silica gel, 230-400 mesh) using 0-100% ethyl acetate in hexane as eluent to afford tert-butyl rac-(3aS,7aR)-5-[1-(2,6-dioxo-3-piperidyl)indolin-4-yl]-3,3a,4,6,7,7a-hexahydro-2H-pyrrolo-[3,2-c]pyridine-1-carboxylate 56-7a (550 mg, 942.92 mol, 46.27% yield) as a light brown solid. UPLC-MS (ES+): m/z 455.2 [M+H]+.

Step-7a:

Compound tert-butyl rac-(3aS,7aR)-5-[1-(2,6-dioxo-3-piperidyl)indolin-4-yl]-3,3a,4,6,7,7a-hexahydro-2H-pyrrolo[3,2-c]pyridine-1-carboxylate 56-7a (550 mg, 1.21 mmol) was purified by chiral SFC to separate the isomers (chiral SFC purification method: column: I Cellulose B(250*30) mm, 5 μm; mobile phase: CO2:isopropanol [60:40] and flow rate 100 mL/min). The early eluting peak (stereochemistry arbitrarily assigned): tert-butyl (3aS,7aR)-5-[1-[(3S)-2,6-dioxo-3-piperidyl]indolin-4-yl]-3,3a,4,6,7,7a-hexahydro-2H-pyrrolo[3,2-c]pyridine-1-carboxylate 56-8a (101.41 mg, 221.06 mol, 18.27% yield, 99.06% enantiopurity) was obtained as an off-white solid. UPLC-MS (ES+): m/z 455.2 [M+H]+. 1H NMR (400 MHz, DMSO-d6): δ 10.77 (s, 1H), 6.89 (t, J=8.00 Hz, 1H), 6.24-6.18 (m, 2H), 4.59 (dd, J=4.80, 13.20 Hz, 1H), 3.78-3.64 (m, 1H), 3.45-3.38 (m, 2H), 3.41-3.25 (m, 2H), 3.23-3.12 (m, 1H), 3.10-2.99 (m, 1H), 2.95-2.74 (m, 4H), 2.62-2.53 (m, 2H), 2.38-2.28 (m, 1H), 2.25-2.11 (m, 2H), 2.05-1.95 (m, 1H), 1.94-1.76 (m, 2H), 1.68-1.55 (m, 1H), 1.41 (s, 9H). The late eluting peak (stereochemistry arbitrarily assigned): tert-butyl (3aS,7aR)-5-[1-[(3R)-2,6-dioxo-3-piperidyl]indolin-4-yl]-3,3a,4,6,7,7a-hexahydro-2H-pyrrolo[3,2-c]pyridine-1-carboxylate 56-9a (91.25 mg, 200.24 mol, 16.55% yield, 93.51% enantiopurity) obtained as a light brown solid. UPLC-MS (ES+): m/z 455.1 [M+H]+. 1H NMR (400 MHz, DMSO-d6): δ 10.77 (s, 1H), 6.89 (t, J=8.00 Hz, 1H), 6.24-6.18 (m, 2H), 4.59 (dd, J=4.80, 12.80 Hz, 1H), 3.75-3.65 (m, 1H), 3.45-3.37 (m, 2H), 3.32-3.28 (m, 1H), 3.23-3.02 (m, 3H), 2.88-2.74 (m, 4H), 2.68-2.53 (m, 2H), 2.33-2.11 (m, 3H), 2.06-1.98 (m, 1H), 1.95-1.77 (m, 2H), 1.65-1.55 (m, 1H), 1.41 (s, 9H).

Scheme 56C: Synthesis of tert-butyl (3aR,7aS)-5-[1-[(3S)-2,6-dioxo-3-piperidyl]indolin-4-yl]-3,3a,4,6,7,7a-hexahydro-2H-pyrrolo[3,2-c]pyridine-1-carboxylate and tert-butyl (3aR,7aS)-5-[1[(3R)-2,6-dioxo-3-piperidyl]indolin-4-yl]-3,3a,4,6,7,7a-hexahydro-2H-pyrrolo[3,2-c]pyridine-1-carboxylate

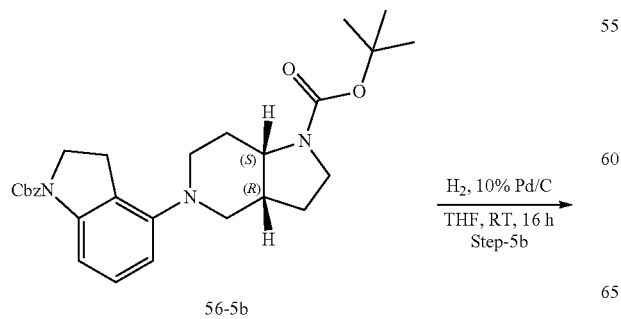

56-5b

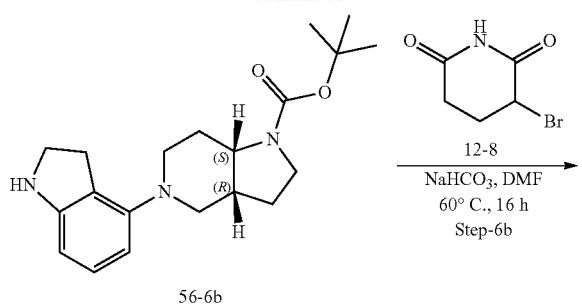

56-6b

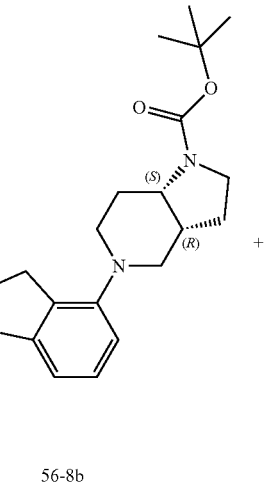

56-7b 56-8b

-continued

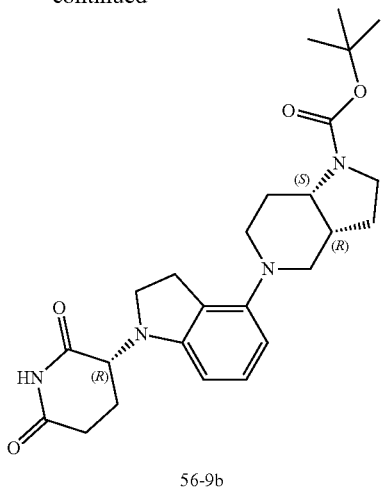

56-9b

Step-5b:

To a stirred solution of tert-butyl (3aS)-5-(1-benzyloxycarbonylindolin-4-yl)-3,3a,4,6,7,7a-hexahydro-2H-pyrrolo[3,2-c]pyridine-1-carboxylate 56-5b (900 mg, 1.88 mmol) in anhydrous THF (15 mL) was added 10% palladium on carbon (1.00 g, 4.71 mmol) at ambient temperature under nitrogen atmosphere. The resulting mixture was stirred at ambient temperature under hydrogen pressure (balloon pressure) for 16 h. After completion of the reaction, the reaction mixture was filtered over celite bed and washed with THF (50 mL). The filtrate was concentrated under reduced pressure to afford tert-butyl (3aR,7aS)-5-indolin-4-yl-3,3a,4,6,7,7a-hexahydro-2H-pyrrolo[3,2-c]pyridine-1-carboxylate 56-6b (680 mg, 1.86 mmol, 98.78% yield) as an off-white solid. UPLC-MS (ES$^+$): m/z 344.1 [M+H]$^+$.

Step-6b:

To a stirred solution of tert-butyl (3aR,7aS)-5-indolin-4-yl-3,3a,4,6,7,7a-hexahydro-2H-pyrrolo[3,2-c]pyridine-1-carboxylate 56-6b (680 mg, 1.86 mmol) in anhydrous DMF (5 mL) were added sodium hydrogen carbonate (780.87 mg, 9.30 mmol) and 3-bromopiperidine-2,6-dione 12-8 (1.07 g, 5.58 mmol) at ambient temperature under nitrogen atmosphere. The resulting mixture was stirred at 60° C. for 16 h. After completion of the reaction, reaction mixture was cooled to room temperature, diluted with water (100 mL), and extracted with ethyl acetate (3×100 mL). The combined organic layer was washed with water (200 mL), brine (50 mL), dried over anhydrous sodium sulphate, filtered, and concentrated under reduced pressure to obtain crude. The crude was purified by column chromatography (silica gel, 230-400 mesh) using 0-100% ethyl acetate in hexane as eluent to afford tert-butyl rac-(3aR,7aS)-5-[1-(2,6-dioxo-3-piperidyl)indolin-4-yl]-3,3a,4,6,7,7a-hexahydro-2H-pyrrolo-[3,2-c]pyridine-1-carboxylate 56-7b (550 mg, 1.17 mmol, 63.06% yield) as an off white solid. UPLC-MS (ES$^+$): m/z 455.2 [M+H]$^+$.

Step-7b:

Compound tert-butyl rac-(3aR,7aS)-5-[1-(2,6-dioxo-3-piperidyl)indolin-4-yl]-3,3a,4,6,7,7a-hexahydro-2H-pyrrolo[3,2-c]pyridine-1-carboxylate 56-7b (550 mg, 1.17 mmol) was purified by chiral SFC to separate isomers (Chiral SFC purification method: column: I Cellulose B (250*30) mm, 5 m, mobile phase: CO$_2$:isopropanol [60:40], flow rate: 100 mL/min). The early eluting peak (stereochemistry arbitrarily assigned): tert-butyl (3aR,7aS)-5-[1-[(3S)-2,6-dioxo-3-piperidyl]indolin-4-yl]-3,3a,4,6,7,7a-hexahydro-2H-pyrrolo[3, 2-c]pyridine-1-carboxylate 56-8b (90 mg, 189.16 mol, 16.14% yield, 100% enantiopurity) obtained as an off-white solid. UPLC-MS (ES$^+$): m/z 455.2 [M+H]$^+$. $^1$H NMR (400 MHz, DMSO-d$_6$): δ 10.77 (s, 1H), 6.89 (t, J=7.60 Hz, 1H), 6.23 (d, J=8.00 Hz, 1H), 6.20 (d, J=8.00 Hz, 1H), 4.59 (dd, J=4.80, 13.20 Hz, 1H), 3.75-3.67 (m, 1H), 3.44-3.38 (m, 2H), 3.32-2.98 (m, 4H), 2.89-2.75 (m, 4H), 2.65-2.53 (m, 2H), 2.34-2.13 (m, 3H), 2.06-1.98 (m, 1H), 1.95-1.79 (m, 2H), 1.65-1.54 (m, 1H), 1.41 (s, 9H). The late eluting peak (stereochemistry arbitrarily assigned): tert-butyl (3aR,7aS)-5-[1-[(3R)-2,6-dioxo-3-piperidyl]indolin-4-yl]-3,3a,4,6,7, 7a-hexahydro-2H-pyrrolo[3,2-c]pyridine-1-carboxylate 56-9b (85 mg, 185.87 mol, 15.85% yield, 97.45% enantiopurity) obtained as an off white solid. UPLC-MS (ES$^-$): m/z 453.2 [M–H]$^-$. $^1$H NMR (400 MHz, DMSO-d$_6$): δ 10.77 (s, 1H), 6.89 (t, J=7.60 Hz, 1H), 6.23 (d, J=8.00 Hz, 1H), 6.20 (d, J=8.00 Hz, 1H), 4.59 (dd, J=4.80, 13.20 Hz, 1H), 3.77-3.66 (m, 1H), 3.45-3.38 (m, 2H), 3.32-2.99 (m, 4H), 2.96-2.75 (m, 4H), 2.65-2.53 (m, 2H), 2.31-2.16 (m, 3H), 2.06-1.98 (m, 1H), 1.94-1.79 (m, 2H), 1.66-1.54 (m, 1H), 1.41 (s, 9H).

Tetrahydroquinoline CRBN Binders

Scheme 57: Synthesis of 3-(6-methoxy-3,4-dihydro-2H-quinolin-1-yl)piperidine-2,6-dione

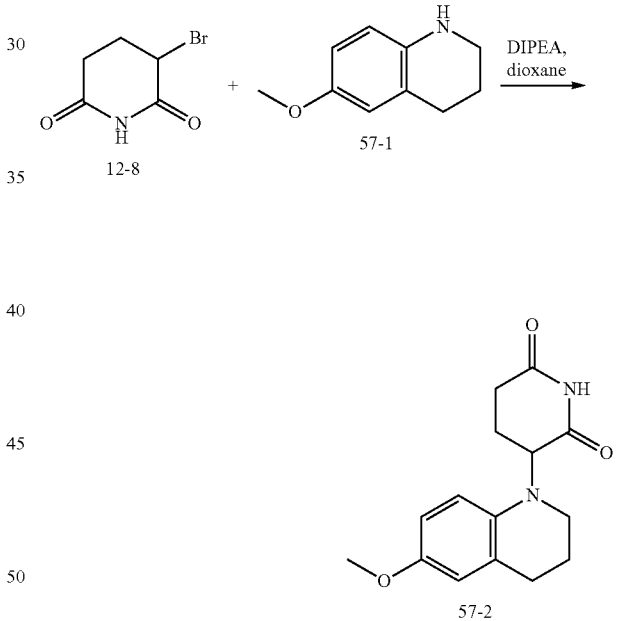

To a stirred solution of the 3-bromoglutarimide 12-8 (100 mg, 520.81 mol) in 1,4-dioxane (0.7 mL) was added 6-methoxy-1,2,3,4-tetrahydroquinoline 57-1 (42.50 mg, 260.40 mol) and DIPEA, and the reaction mixture was heated at 90° C. for 16 hours. After completion, the reaction product was purified by preparative HPLC to obtain 3-(6-methoxy-3,4-dihydro-2H-quinolin-1-yl)piperidine-2,6-dione 57-2 (29.12 mg, 20.4% yield). LCMS (ES$^-$): m/z 273.04 [M–H]$^-$.

Scheme 58: 3-(6-methyl-3,4-dihydro-2H-quinolin-1-yl)piperidine-2,6-dione

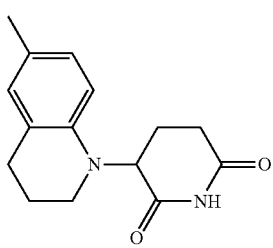

58-1

This compound was prepared substantially following the synthesis of 3-(6-methoxy-3,4-dihydro-2H-quinolin-1-yl)piperidine-2,6-dione 57-2. LCMS (ES+): m/z 259.11 [M+H]+.

Scheme 59: Synthesis of tert-butyl 4-[1-[(3R)-2,6-dioxo-3-piperidyl]-3,4-dihydro-2H-qunolin-5-yl]piperidine-1-carbocylate and tert-butyl 4-[1-[(3S)-2,6-dioxo-3-piperidyl]-3,4-dihydro-2H-quinolin-5-yl]piperidine-1-carboxylate

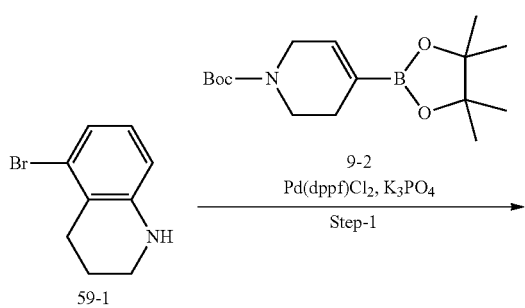

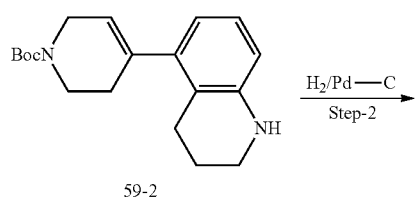

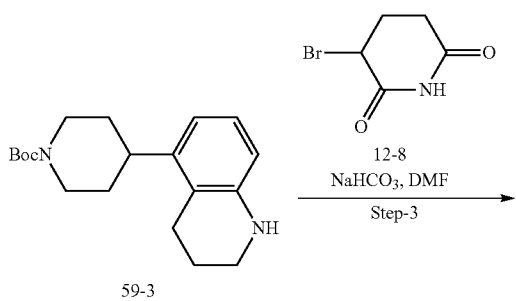

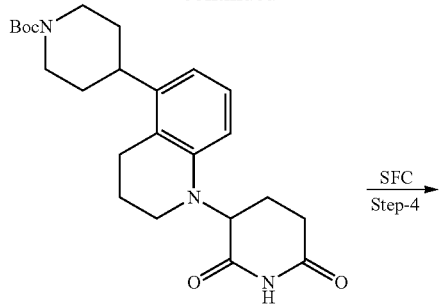

59-4

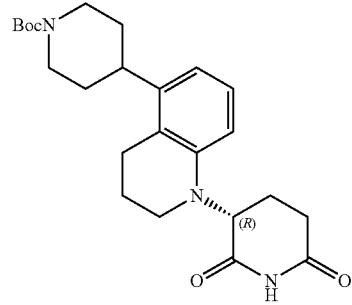

59-5

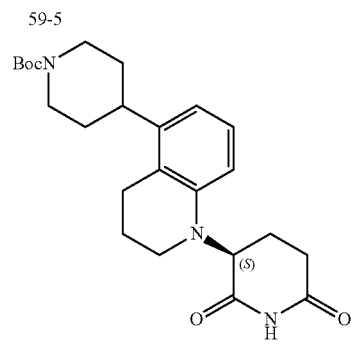

59-6

Step-1:
A mixture of 5-bromo-1,2,3,4-tetrahydroquinoline 59-1 (2 g, 9.43 mmol, 1.0 eq.) and tert-butyl 4-(4,4,5,5-tetramethyl-1,3,2-dioxaborolan-2-yl)-3,6-dihydro-2H-pyridine-1-carboxylate 9-2 (3.50 g, 11.32 mmol, 1.2 eq.) in 1,4-dioxane (40 mL) was degassed with nitrogen for 5 min. To the reaction mixture, tripotassium phosphate (6.01 g, 28.29 mmol, 3.0 eq.) in water (10 mL) was added and the mixture was degassed for an additional 5 min. Then Pd(dppf)Cl$_2$·CH$_2$Cl$_2$ (770.10 mg, 943.01 mol, 0.1 eq.) was added and the reaction mixture was heated at 95° C. for 16 h. Upon completion of the reaction, the reaction mixture was cooled to room temperature, filtered through a celite bed and washed with EtOAc. The filtrate was washed with water and brine, dried over anhydrous Na$_2$SO$_4$ and evaporated under vacuum to obtain the crude material, which was purified by column chromatography (Davisil Silica, elution solvent 0-30% EtOAc in n-hexane) to afford tert-butyl 4-(1,2,3,4-tetrahydroquinolin-5-yl)-3,6-dihydro-2H-pyridine-1-carboxylate 59-2 (2.2 g, 6.91 mmol, 73.31% yield) as an off white solid. LCMS (ES+): m/z 315.34 [M+H]+.

Step-2:
A solution of tert-butyl 4-(1,2,3,4-tetrahydroquinolin-5-yl)-3,6-dihydro-2H-pyridine-1-carboxylate 59-2 (2.2 g, 7.00 mmol, 1.0 eq.) in methanol (50 mL) was degassed with nitrogen gas for 15 min in a 250 mL Parr-Shaker vessel. Subsequently, 10% palladium on charcoal (2.23 g, 20.99 mmol, 3.0 eq.) was added to the reaction mixture and the reaction mixture was stirred under hydrogen atmosphere for 16 h at 25° C. at 70 psi. Upon completion of the reaction, it was filtered through celite bed, and washed with methanol. The filtrate was evaporated under vacuum to get the crude residue, which was purified by column chromatography (Davisil silica, 0-50% EtOAc in petroleum ether) to afford t-butyl 4-(1, 2, 3, 4-tetrahydroquinolin-5-yl)-piperidine-1-carboxylate 59-3 (1.8 g, 5.40 mmol, 77.23% yield) as a white solid. LCMS (ES$^+$): m/z 261.57 [M−tBu+H]$^+$.

Step-3:

To a solution of tert-butyl 4-(1,2,3,4-tetrahydroquinolin-5-yl)piperidine-1-carboxylate 59-3 (1 g, 3.16 mmol, 1.0 eq.) and 3-bromopiperidine-2,6-dione 12-8 (1.82 g, 9.48 mmol, 3.0 eq.) in DMF (10 mL) sodium hydrogen carbonate (2.65 g, 31.60 mmol, 1.23 mL, 10.0 eq.) was added under nitrogen atmosphere. The reaction mixture was heated at 80° C. for 16 h. Then the reaction mixture was cooled to room temp and diluted with EtOAc. The organic layer was washed with water, dried over anhydrous Na$_2$SO$_4$, and evaporated under vacuum to afford the crude compound which was purified by column chromatography (Davisil Silica, 0-50% ethyl acetate in petroleum ether) to afford tert-butyl 4-[1-(2,6-dioxo-3-piperidyl)-3,4-dihydro-2H-quinolin-5-yl]piperidine-1-carboxylate 59-4 (500 mg, 1.13 mmol, 35.90% yield) as a light green solid. LCMS (ES$^+$): m/z 428.78[M+H]$^+$.

Step-4:

The racemic tert-butyl 4-[1-(2,6-dioxo-3-piperidyl)-3,4-dihydro-2H-quinolin-5-yl]piperidine-1-carboxylate 59-4 (1.6 g) was separated by chiral SFC, and the fractions were concentrated in vacuo to give tert-butyl 4-[1-[(3S)-2,6-dioxo-3-piperidyl]-3,4-dihydro-2H-quinolin-5-yl]piperidine-1-carboxylate 59-6 (Early eluting peak, 550 mg) and tert-butyl 4-[1-[(3R)-2,6-dioxo-3-piperidyl]-3,4-dihydro-2H-quinolin-5-yl]piperidine-1-carboxylate 59-5 (Late eluting peak, 520 mg).

Preparative SFC conditions: instrument: PIC 175; Column: I Cellulose B (250×20) mm, 5 μm; Mobile Phase: CO$_2$:ACN [82:18]; Total Flow: 60 ml/min; Back pressure: 100 bar; Wavelength: 220 nm; Cycle time: 10 min.

59-5: LCMS (ES$^+$): m/z 428.2 [M+H]$^+$.

59-6: LCMS (ES$^+$): m/z 428.2 [M+H]$^+$.

Scheme 60: Synthesis of tert-butyl 2-[4-[1-[(3S)-2,6-dioxo-3-piperidyl]-3,4-dihydro-2H-quinolin-5-yl]-1-piperidyl]acetate and tert-butyl 2-[4-[1-[(3R)-2,6-dioxo-3-piperidyl]-3,4-dihydro-2H-quinolin-5-yl]-1-piperidyl]acetate

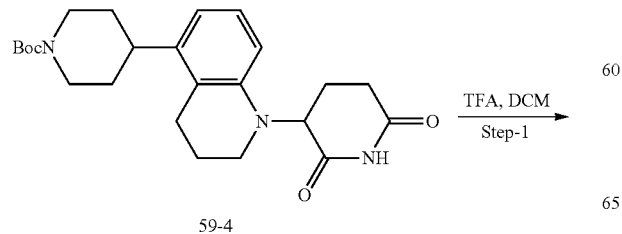

59-4

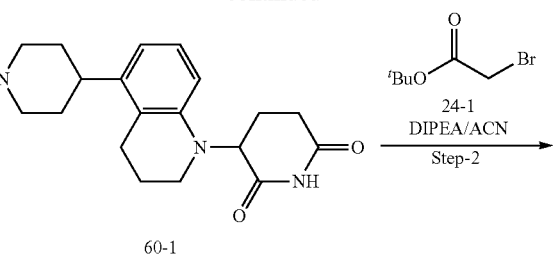

60-1

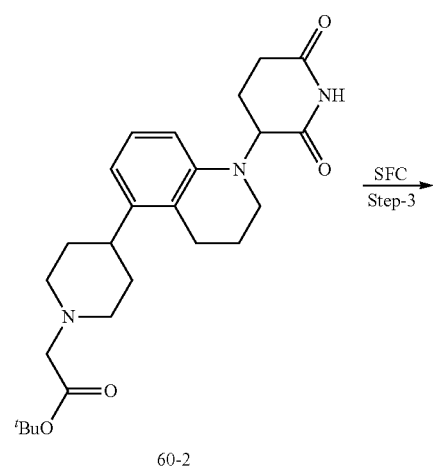

60-2

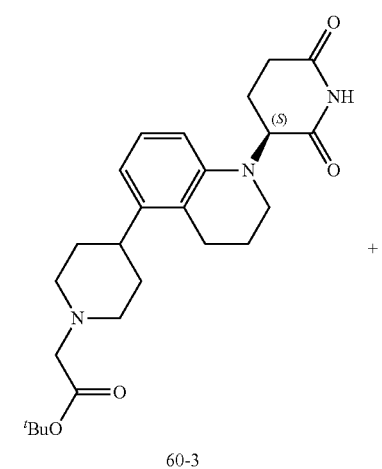

60-3

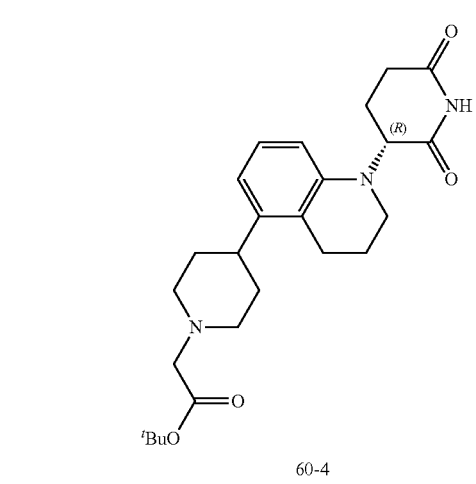

60-4

Step-1:

To a stirred solution of tert-butyl 4-[1-(2,6-dioxo-3-piperidyl)-3,4-dihydro-2H-quinolin-5-yl]piperidine-1-carboxylate 59-4 (500 mg, 1.17 mmol, 1.0 eq.) in DCM (4.5 mL), was added 2,2,2-trifluoroacetic acid (1.60 g, 14.03 mmol, 1.08 mL, 12.0 eq.) under nitrogen atmosphere and the reaction mixture was stirred at 25° C. for 2 h. Upon completion of the reaction, the solvent was evaporated under vacuum. The crude material was triturated with diethyl ether to obtain 3-[5-(4-piperidyl)-3,4-dihydro-2H-quinolin-1-yl]piperidine-2,6-dione 60-1 (350 mg, 626.36 mol, 53.56% yield) as a light-brown sticky solid. LCMS (ES$^+$): m/z 328.53 [M+H]$^+$.

Step-2:

To a stirred solution of 3-[5-(4-piperidyl)-3,4-dihydro-2H-quinolin-1-yl]piperidine-2,6-dione 60-1 (350 mg, 1.07 mmol, 1.0 eq.) in acetonitrile (4 mL), was added N-ethyl-N-isopropyl-propan-2-amine (1.11 g, 8.55 mmol, 1.49 mL, 8.0 eq.). The reaction mixture was stirred for 5 min and tert-butyl 2-bromoacetate 24-1 (208.51 mg, 1.07 mmol, 156.77 ptL, 1.0 eq.) was added. The contents were heated at 70° C. for 16 h. Upon completion of the reaction, the volatiles were evaporated under reduced pressure. The residue was washed with water and extracted with EtOAc. The organic layer was washed with brine and dried over anhydrous sodium sulphate, filtered and concentrated under reduced pressure to get the crude compound, which was triturated with n-pentane and diethyl ether to afford tert-butyl 2-[4-[1-(2,6-dioxo-3-piperidyl)-3,4-dihydro-2H-quinolin-5-yl]-1-piperidyl]acetate 60-2 (250 mg, 509.56 mol, 47.67% yield) as a brown gum. LCMS (ES$^+$): m/z 442.81 [M+H]$^+$.

Step-3: The racemic tert-butyl 2-[4-[1-(2,6-dioxo-3-piperidyl)-3,4-dihydro-2H-quinolin-5-yl]-1-piperidyl]acetate 60-2 (in two batches, 1.6 g and 2.1 g) was separated by chiral SFC and the fractions were concentrated in vacuo to give tert-butyl 2-[4-[1-[(3S)-2,6-dioxo-3-piperidyl]-3,4-dihydro-2H-quinolin-5-yl]-1-piperidyl]acetate 60-3 (Early eluting peak arbitrarily assigned as S— isomer, 1.05 g) and tert-butyl 2-[4-[1-[(3R)-2,6-dioxo-3-piperidyl]-3,4-dihydro-2H-quinolin-5-yl]-1-piperidyl]acetate 60-4 (Late eluting peak arbitrarily assigned as R-isomer, 1.05 g).

Preparative SFC conditions: column/dimensions: CHIRALCEL-OX-H (30×250) mm, 5µ; % CO$_2$: 55%; % co-solvent: 45% ACN: IPA (1:1); Total Flow: 100 g/min; Back Pressure: 100 bar; Temperature: 30° C.; UV: 215 nm; Instrument details: Make/Model: SFC-150-I.

60-3: LCMS (ES$^+$): m/z 442.35 [M+H]$^+$.

60-4: LCMS (ES$^+$): m/z 442.39 [M+H]$^+$.

Scheme 61: Synthesis of tert-butyl N-[1-1-[(3S)-2,6-dioxo-3-piperidyl]-3,4-dihydro-2H-quinolin-5-yl]-4-piperidyl]-N-methyl-carbamate and tert-butyl N-[1-1-[(3R)-2,6-dioxo-3-piperidyl]-3,4-dihydro-2H-quinolin-5-yl]-4-piperidyl]-N-methyl-carbamate

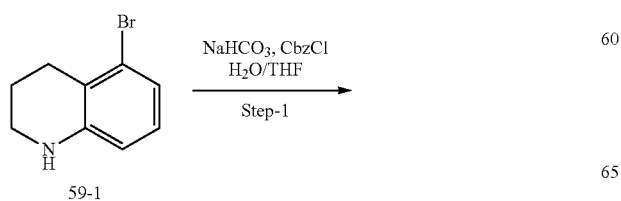

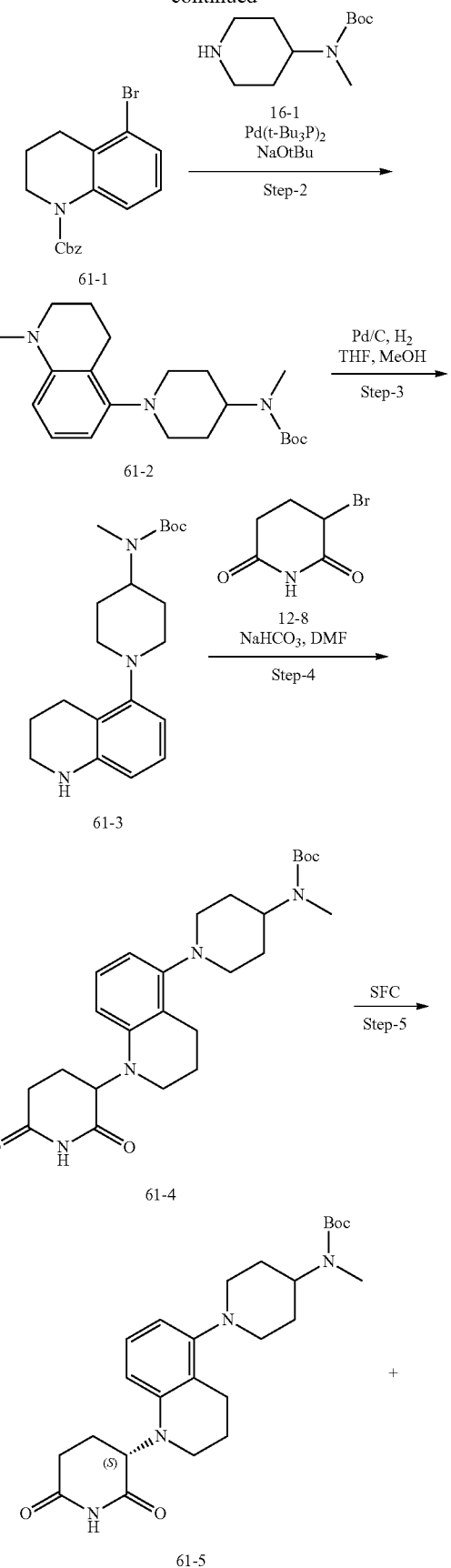

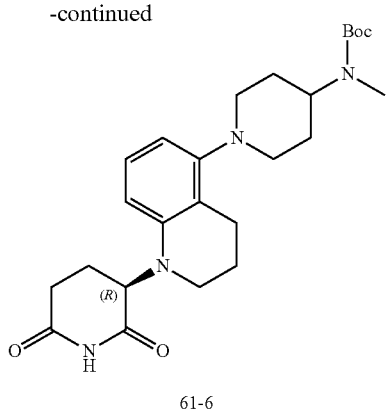

61-6

Step-1:

To a stirred mixture of 5-bromo-1,2,3,4-tetrahydroquinoline 59-1 (5 g, 23.58 mmol) and sodium bicarbonate (2.57 g, 30.65 mmol, 1.19 mL) in water (22.35 mL) and THF (22.35 mL), was added dropwise benzyl carbonochloridate (6.03 g, 35.36 mmol, 5.03 mL) at 0° C. Then the resulting reaction mixture was stirred at room temperature overnight. The reaction mixture was diluted with water (200 ml) and extracted with ethyl acetate (3×400 mL), and the combined organic layers were washed with saturated brine (300 mL) and dried over anhydrous sodium sulphate, filtered and concentrated under reduced pressure to get crude product. The crude product was purified by column chromatography using 50 g of silica gel and 0-100% EtOAc in petroleum ether as eluent to afford benzyl 5-bromo-3,4-dihydro-2H-quinoline-1-carboxylate 61-1 (7.2 g, 20.22 mmol, 85.77% yield) as a white solid. LCMS (ES+): m/z 347.1 [M+H]+.

Step-2:

To a solution of benzyl 5-bromo-3,4-dihydro-2H-quinoline-1-carboxylate 61-1 (12 g, 34.66 mmol) and tert-butyl-N-methyl-N-(4-piperidyl)carbamate 16-1 (7.43 g, 34.66 mmol) in toluene (100 mL) was added sodium tert-butoxide (9.99 g, 103.98 mmol) at room temperature. The reaction mixture was degassed with $N_2$ for 10 min and then bis(tri-tert-butylphosphine)palladium(0) (177.13 mg, 346.60 mol) was added to the reaction mixture and again degassed with $N_2$ for 5 min and stirred for 16 h at 110° C. After completion of the reaction, the reaction mixture was filtered through a celite bed and washed with ethyl acetate. The combined organic layer was dried over $Na_2SO_4$, filtered and concentrated under reduced pressure to give the crude product, which was purified by column chromatography using Davisil silica and 0-100% EtOAc in petroleum ether as an eluent to afford benzyl 5-[4-[tert-butoxycarbonyl(methyl)amino]-1-piperidyl]-3,4-dihydro-2H-quinoline-1-carboxylate 61-2 (12 g, 24.77 mmol, 71.47% yield) as an off-white solid. LCMS (ES+): m/z 380.71 [M–Boc+H]+.

Step-3:

To a stirred solution of benzyl 5-[4-[tert-butoxycarbonyl(methyl)amino]-1-piperidyl]-3,4-dihydro-2H-quinoline-1-carboxylate 61-2 (12 g, 25.02 mmol) in methanol (100 mL) and THF (100 mL) was added 10% palladium on carbon, type 487, dry (6.66 g, 62.55 mmol), and the reaction mixture was stirred in a Parr Shaker reactor at 40 psi pressure and 28° C. for 16 hr. Upon completion of reaction, the reaction mixture was filtered through celite bed and washed with ethyl acetate, filtrate was concentrated under reduced pressure to afford tert-butyl N-methyl-N-[1-(1,2,3,4-tetrahydroquinolin-5-yl)-4-piperidyl]carbamate 61-3 (8 g, 20.38 mmol, 81.44% yield) as an off-white solid. LCMS (ES+): m/z 346.76 [M+H]+.

Step-4:

To a stirred solution of tert-butyl N-methyl-N-[1-(1,2,3,4-tetrahydroquinolin-5-yl)-4-piperidyl]carbamate 61-3 (7 g, 20.26 mmol) and 3-bromopiperidine-2,6-dione 12-8 (23.34 g, 121.57 mmol) in DMF (70 mL) was added sodium bicarbonate (17.02 g, 202.62 mmol) in a sealed tube. The reaction mixture was stirred at 80° C. for 16 h. Upon completion of reaction, the reaction mixture was poured into ice cold water and extracted with EtOAc. The organic layer was then washed with cold brine to get the crude product, which was purified by column chromatography using silica gel (230-400 mesh) and 0-100% EtOAc in petroleum ether as an eluent to afford tert-butyl N-[1-[1-[(3S)-2,6-dioxo-3-piperidyl]-3,4-dihydro-2H-quinolin-5-yl]-4-piperidyl]-N-methyl-carbamate 61-4 (1.3 g, 2.83 mmol, 13.98% yield) as an off-white solid.

Step-5:

The racemic compound 61-4 (3 g) was separated by chiral SFC to give tert-butyl N-[1-[1-[(3S)-2,6-dioxo-3-piperidyl]-3,4-dihydro-2H-quinolin-5-yl]-4-piperidyl]-N-methyl-carbamate 61-5 (Early eluting peak arbitrarily assigned as S-isomer, 1.3 g) and tert-butyl N-[1-[1-[(3R)-2,6-dioxo-3-piperidyl]-3,4-dihydro-2H-quinolin-5-yl]-4-piperidyl]-N-methyl-carbamate 61-6 (Late eluting peak arbitrarily assigned as R-isomer, 1.3 g).

Preparative SFC conditions: column/dimensions: CHIRAL PAK-IC (4.6×250) mm, 5μ; % $CO_2$: 60%; % co-solvent: 40% (ACN-IPA) (1:1); Total Flow: 110 g/min; Back Pressure: 100 bar; Temperature: 30° C.; UV: 215 nm; Solubility: THF+ACN+IPA.

61-5: LCMS (ES−): m/z 455.30 [M–H]−.

61-6: LCMS (ES−): m/z 455.30 [M–H]−.

Scheme 62: Synthesis of 3-(4,4-difluoro-5-(4-(methylamino)piperidin-1-yl)-3,4-dihydroquinolin-1(2H)-yl)piperidine-2,6-dione

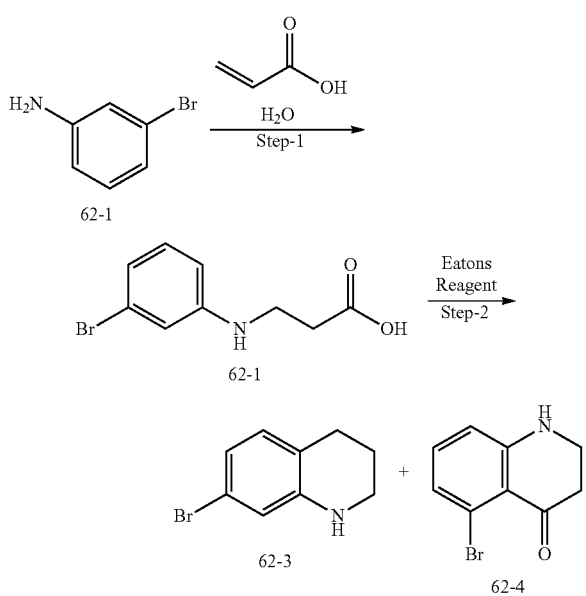

561
-continued

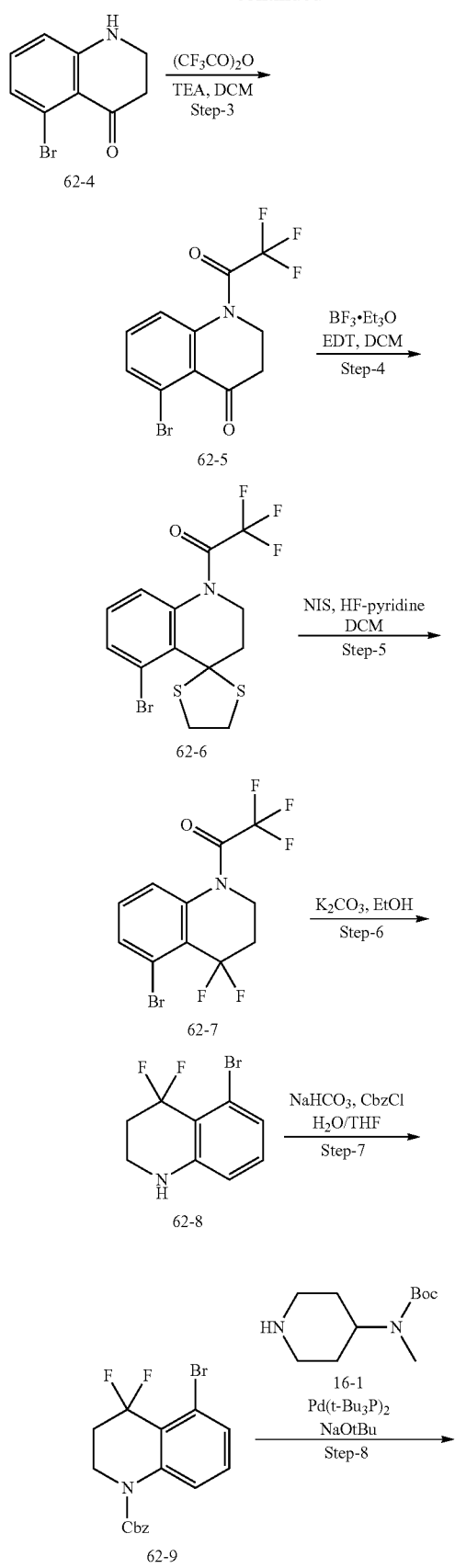

562
-continued

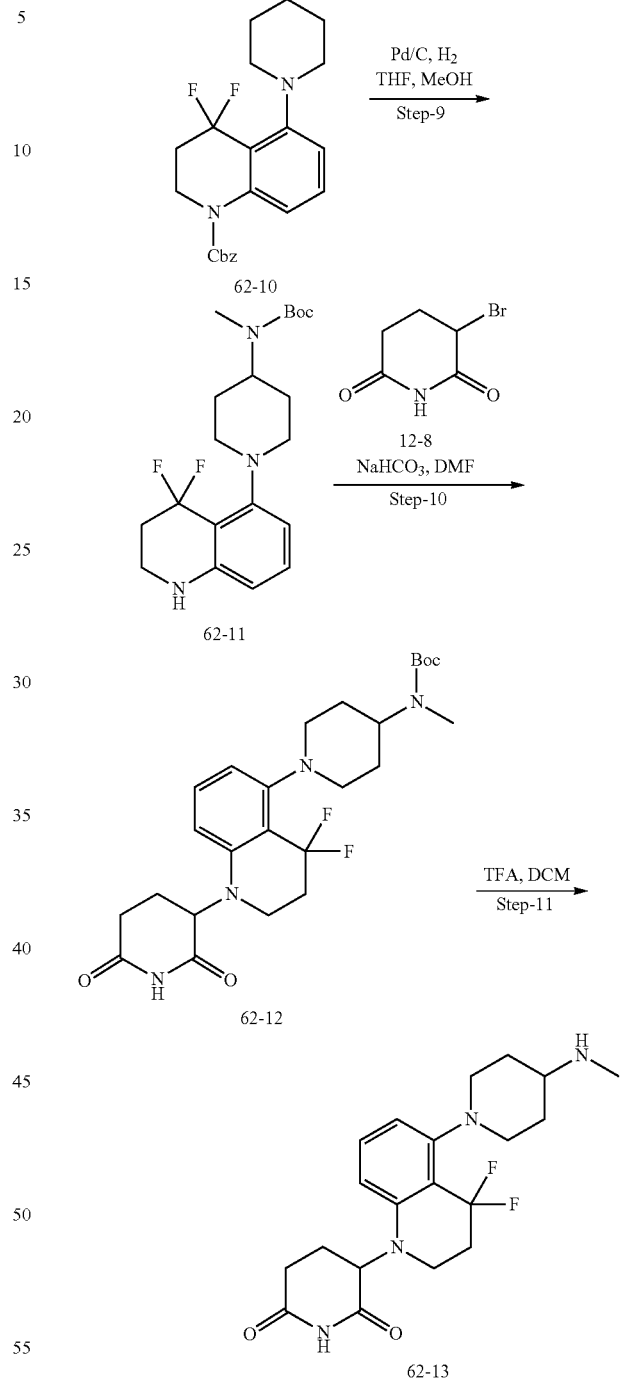

Step-1:
A stirred solution of 3-bromoaniline 62-1 (100 g, 581.32 mmol, 63.29 mL) and acrylic acid (46.08 g, 639.45 mmol, 43.84 mL) in water (996.02 mL) was heated at 100° C. for 16 hr. Upon completion of reaction, the reaction mixture was cooled to room temperature and extracted with ethyl acetate, washed with brine and concentrated to give the crude product, which was purified by column chromatography using Davisil silica and 5% MeOH in DCM to afford 3-(3-bromoanilino)propanoic acid 62-2 (45 g, 173.30 mmol, 29.81% yield). LCMS (ES+): m/z 246.2 [M+2H]+.

Step-2:

A mixture of 3-(3-bromoanilino)propanoic acid 62-2 (20 g, 81.94 mmol) and Eaton's reagent was prepared at room temperature. Then, the reaction mixture was stirred at 100° C. for 12 h. On completion, the crude product was neutralized with NaHCO$_3$ solution, and extracted with EtOAc. The organic layer was washed with brine, dried over Na$_2$SO$_4$, and concentrated in vacuo to give the crude product, which was purified by column chromatography using hexane and EtOAc as an eluent to afford 7-bromo-2,3-dihydro-1H-quinolin-4-one 62-3 (1.2 g, 4.78 mmol, 5.83% yield) and 5-bromo-2,3-dihydro-1H-quinolin-4-one 62-4 (5.2 g, 20.70 mmol, 25.26% yield). LCMS (ES+): m/z 226.37 [M+H]+.

Step-3:

To stirred solution of 5-bromo-2,3-dihydro-1H-quinolin-4-one 62-4 (2.5 g, 11.06 mmol) in DCM (20 mL) was added TEA (3.36 g, 33.18 mmol, 4.62 mL) at room temperature, and the reaction mixture was cooled to 0° C., followed by dropwise addition of (2,2,2-trifluoroacetyl) 2,2,2-trifluoroacetate (2.79 g, 13.27 mmol, 1.87 mL) and stirring at 25° C. for 2 hr. After completion of reaction, the reaction mixture was diluted with water and extracted with DCM, organic layer was washed with sat. NaHCO$_3$ solution, followed by washing with brine. The organic layer was evaporated under reduced pressure to obtain the crude product, which was purified by column chromatography using 230-400 mesh silica gel and 0-100% EtOAc in petroleum ether as an eluent to afford 5-bromo-1-(2,2,2-trifluoroacetyl)-2,3-dihydroquinolin-4-one 62-5 (3.0 g, 5.96 mmol, 53.91% yield) as a yellow solid. LCMS (ES+): m/z 322.34 [M+H]+.

Step-4:

To a stirred solution of 5-bromo-1-(2,2,2-trifluoroacetyl)-2,3-dihydroquinolin-4-one 62-5 (2.5 g, 7.76 mmol) in DCM (3.05 mL) was added boron trifluoride diethyl etherate (2.01 g, 20.96 mmol, 1.75 mL) and ethane-1,2-dithiol (1.68 g, 17.85 mmol, 1.50 mL) at 0° C. dropwise over a period of 10 min under N$_2$ atmosphere. The reaction mixture was stirred at 25° C. for 44 hr. After completion of reaction, the reaction mixture was diluted with water and extracted with DCM. The organic layer was washed with sat. NaHCO$_3$ solution, brine, and was concentrated under reduced pressure to give the crude product, which was purified by column chromatography using 230-400 silica gel and 0-100% EtOAc in petroleum ether as an eluent to afford 1-(5'-bromospiro[1,3-dithiolane-2,4'-2,3-dihydroquinoline]-1'-yl)-2,2,2-trifluoro-ethanone 62-6 (1.8 g, 2.67 mmol, 34.35% yield) as a yellow solid. LCMS (ES+): m/z 398.21[M+H]+.

Step-5:

To a stirred solution of 1-(5'-bromospiro[1,3-dithiolane-2,4'-2,3-dihydroquinoline]-1'-yl)-2,2,2-trifluoro-ethanone 62-6 (0.8 g, 2.01 mmol) in DCM (5 mL) was added N-iodosuccinimide (3.62 g, 16.07 mmol, 4.87 mL) at −78° C., and the reaction mixture was stirred for 10 min, followed by addition of hydrogen fluoride-pyridine (23.69 g, 239.04 mmol, 20.78 mL). After completion of reaction, it was diluted with NaHCO$_3$ solution and extracted with DCM. The organic layer was washed with brine and evaporated under reduced pressure to obtain the crude product, which was purified by column chromatography using 230-400 silica gel and 0-100% EtOAc in petroleum ether as an eluent to afford 1-(5-bromo-4,4-difluoro-2,3-dihydroquinolin-1-yl)-2,2,2-trifluoro-ethanone 62-7 (0.6 g, 993.97 mol, 49.48% yield) as a yellow solid. LCMS (ES+): m/z 343.29 [M+H]+.

Step-6:

To a stirred solution of 1-(5-bromo-4,4-difluoro-2,3-dihydroquinolin-1-yl)-2,2,2-trifluoro-ethanone 62-7 (0.05 g, 145.32 mol) in methanol (2 mL), potassium carbonate (30.13 mg, 217.98 mol) was added at 0° C. The reaction mixture was stirred at 0° C. for 20 mines. Upon completion of the reaction, a reaction was worked-up, and combined organic layers were washed with brine, dried over anhydrous Na$_2$SO$_4$ and evaporated under vacuum to give the crude compound, which was triturated with pentane to afford 5-bromo-4,4-difluoro-2,3-dihydro-1H-quinoline 62-8 (0.03 g, 95.54 mol, 65.74% yield) as a brown liquid. LCMS (ES+): m/z 228.05 [M−F+H]+.

Step-7 to Step-10:

The procedures are identical to those of Step-1 to Step-5 in the synthesis of tert-butyl N-[1-[1-[(3S)-2,6-dioxo-3-piperidyl]-3,4-dihydro-2H-quinolin-5-yl]-4-piperidyl]-N-methyl-carbamate 61-5.

Step-11:

To a stirred solution of tert-butyl (1-(1-(2,6-dioxopiperidin-3-yl)-4,4-difluoro-1,2,3,4-tetrahydroquinolin-5-yl)piperidin-4-yl)(methyl)carbamate 62-12 (1 eq.) in DCM (5 mL) at 0° C. is added TFA (5 eq.) dropwise. The reaction is stirred at room temperature for 2 h. After completion of the reaction, the mixture is concentrated under reduced pressure to give the crude product, which is triturated with diethyl ether to afford 3-(4,4-difluoro-5-(4-(methylamino)piperidin-1-yl)-3,4-dihydroquinolin-1(2H)-yl)piperidine-2,6-dione 62-13.

Scheme 63: Synthesis of tert-butyl [4-[4-[[1-[(3S)-2,6-dioxo-3-piperidyl]-3,4-dihydro-2H-quinolin-5-yl]oxy]-1-piperidyl] piperidine-1-carboxylate and tert-butyl [4-[4-[[1-[(3R)-2,6-dioxo-3-piperidyl]-3,4-dihydro-2H-quinolin-5-yl]oxy]-1-piperidyl] piperidine-1-carboxylate

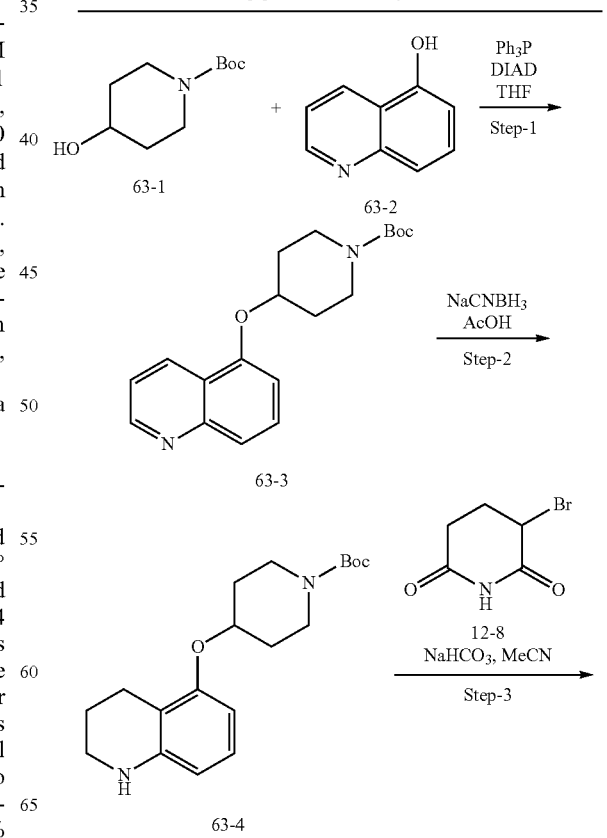

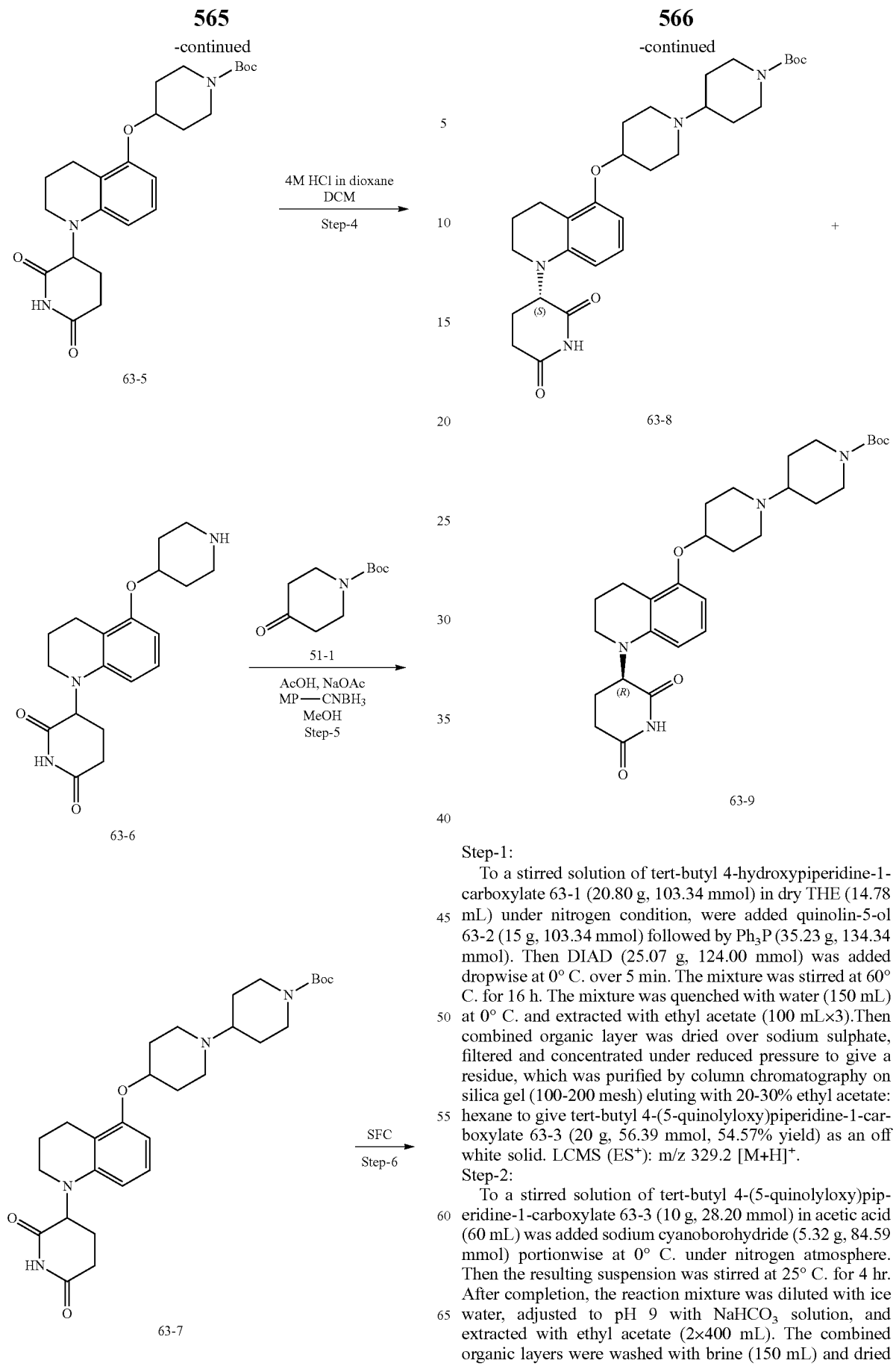

Step-1:
To a stirred solution of tert-butyl 4-hydroxypiperidine-1-carboxylate 63-1 (20.80 g, 103.34 mmol) in dry THF (14.78 mL) under nitrogen condition, were added quinolin-5-ol 63-2 (15 g, 103.34 mmol) followed by Ph₃P (35.23 g, 134.34 mmol). Then DIAD (25.07 g, 124.00 mmol) was added dropwise at 0° C. over 5 min. The mixture was stirred at 60° C. for 16 h. The mixture was quenched with water (150 mL) at 0° C. and extracted with ethyl acetate (100 mL×3).Then combined organic layer was dried over sodium sulphate, filtered and concentrated under reduced pressure to give a residue, which was purified by column chromatography on silica gel (100-200 mesh) eluting with 20-30% ethyl acetate: hexane to give tert-butyl 4-(5-quinolyloxy)piperidine-1-carboxylate 63-3 (20 g, 56.39 mmol, 54.57% yield) as an off white solid. LCMS (ES⁺): m/z 329.2 [M+H]⁺.

Step-2:
To a stirred solution of tert-butyl 4-(5-quinolyloxy)piperidine-1-carboxylate 63-3 (10 g, 28.20 mmol) in acetic acid (60 mL) was added sodium cyanoborohydride (5.32 g, 84.59 mmol) portionwise at 0° C. under nitrogen atmosphere. Then the resulting suspension was stirred at 25° C. for 4 hr. After completion, the reaction mixture was diluted with ice water, adjusted to pH 9 with NaHCO₃ solution, and extracted with ethyl acetate (2×400 mL). The combined organic layers were washed with brine (150 mL) and dried over anhydrous sodium sulphate, filtered and concentrated under reduced pressure. The crude product was purified by chromatography on an Isolera (230-400 silica gel) with 10%-15% ethyl acetate in petroleum ether as an eluent to afford tert-butyl 4-(1,2,3,4-tetrahydroquinolin-5-yloxy)piperidine-1-carboxylate 63-4 (2.6 g, 7.11 mmol, 25.23% yield) as a pale brown color liquid. LCMS (ES⁺): m/z 333.3 [M+H]⁺.

Step-3:

A well-stirred solution of tert-butyl 4-(1,2,3,4-tetrahydroquinolin-5-yloxy)piperidine-1-carboxylate 63-4 (1.6 g, 4.81 mmol) in acetonitrile (10 mL) was prepared in a 50 ml sealed tube. Sodium bicarbonate (2.02 g, 24.06 mmol) and 3-bromopiperidine-2,6-dione 12-8 (4.62 g, 24.06 mmol) were added into the tube at room temperature. The resulting reaction mixture was stirred at 80° C. for 48 hr. The reaction mixture was cooled to room temperature, quenched with water (30 mL) and extracted with ethyl acetate (150 mL×3). The combined organic layers were dried over anhydrous sodium sulphate, filtered and concentrated under reduced pressure. The obtained crude product was purified by column chromatography using 100 g silica gel (230-400 mesh) and a gradient of 0-100% EtOAc—hexane to afford tert-butyl 4-[[1-(2,6-dioxo-3-piperidyl)-3,4-dihydro-2H-quinolin-5-yl]oxy]piperidine-1-carboxylate 63-5 (3.8 g, 2.54 mmol, 52.79% yield) as a pale brown color solid. LCMS (ES⁺): m/z 444.2 [M+H]⁺.

Step-4:

To a stirred solution of tert-butyl 4-[[1-(2,6-dioxo-3-piperidyl)-3,4-dihydro-2H-quinolin-5-yl]oxy]piperidine-1-carboxylate 63-5 (3 g, 2.01 mmol) in DCM (20 mL) was added hydrogen chloride solution in dioxane (4 M, 8 mL) at 0° C. and the reaction mixture was stirred at 25° C. for 3 hr. After completion of the reaction, the reaction mixture was concentrated under reduced pressure to give the crude material, which was washed with MTBE (35 mL×2) and dried under reduced pressure to afford 3-[5-(4-piperidyloxy)-3,4-dihydro-2H-quinolin-1-yl]piperidine-2,6-dione 63-6 (600 mg, 1.46 mmol, 72.85% yield, HCl salt) as a pale yellow color solid. LCMS (ES⁺): m/z 344.2 [M+H]⁺.

Step-5:

To a stirred solution of 3-[5-(4-piperidyloxy)-3,4-dihydro-2H-quinolin-1-yl]piperidine-2,6-dione 63-6 (800 mg, 2.11 mmol, HCl salt) and tert-butyl 4-oxopiperidine-1-carboxylate 51-1 (629.40 mg, 3.16 mmol) in methanol (20 mL) was added acetic acid (632.30 mg, 10.53 mmol, 602.77 µL), followed by addition of anhydrous sodium acetate (518.25 mg, 6.32 mmol) and MPCNBH₃ (800 mg, 2.11 mmol) at ambient temperature. The resulting mixture was stirred at 25° C. for 16 h. Then the reaction mixture was heated to 60° C. for 2 h. After consumption of the starting material, the reaction mixture was filtered through a pad of celite, which was washed with DCM (15 mL). The filtrate was concentrated under reduced pressure. The obtained crude was purified by reverse phase chromatography (Column: Redisep Rf Gold® reversed-phase C18-teledyne ISCO, 100 g, mobile phase A: 0.1% FA in milli-Q water; mobile phase B: acetonitrile, flow rate: 15 mL/min; pure compound was eluted with 80% of mobile phase A: mobile phase B) to afford tert-butyl 4-[4-[[1-(2,6-dioxo-3-piperidyl)-3,4-dihydro-2H-quinolin-5-yl]oxy]-1-piperidyl]piperidine-1-carboxylate 63-7 (330 mg, 625.96 mol, 29.72% yield) as an off-white solid. LCMS (ES⁺): m/z 527.4 [M+H]⁺.

Step-6:

Racemic tert-butyl 4-[4-[[1-(2,6-dioxo-3-piperidyl)-3,4-dihydro-2H-quinolin-5-yl]oxy]-1-piperidyl]piperidine-1-carboxylate 63-7 (330 mg) was separated by SFC, and the fractions were concentrated under reduced pressure to give tert-butyl 4-[4-[[1-[(3S)-2,6-dioxo-3-piperidyl]-3,4-dihydro-2H-quinolin-5-yl]oxy]-1-piperidyl]piperidine-1-carboxylate 63-8 (Early eluting peak arbitrarily assigned as S-isomer, 55 mg) and tert-butyl 4-[4-[[1-[(3R)-2,6-dioxo-3-piperidyl]-3,4-dihydro-2H-quinolin-5-yl]oxy]-1-piperidyl]piperidine-1-carboxylate 63-9 (Late eluting peak arbitrarily assigned as R-isomer, 60 mg).

SFC method: instrument: PIC 175; column: RR-Whelk (250×30) mm, 5 µm; mobile phase: CO₂: 0.5% IPAm in IPA:ACN [65:35]; Total Flow: 100 ml/min; Back pressure: 100 bar; Wavelength: 220 nm; Cycle time: 6.5 min.

63-8: LCMS (ES⁺): m/z 527.2 [M+H]⁺.

63-9: LCMS (ES⁺): m/z 527.2 [M+H]⁺.

Scheme 64: Synthesis of tert-butyl 1-(2,6-dioxo-3-piperidyl)spiro[2,4-dihydroquinoline-3,4'-piperidine]-1'-carboxylate

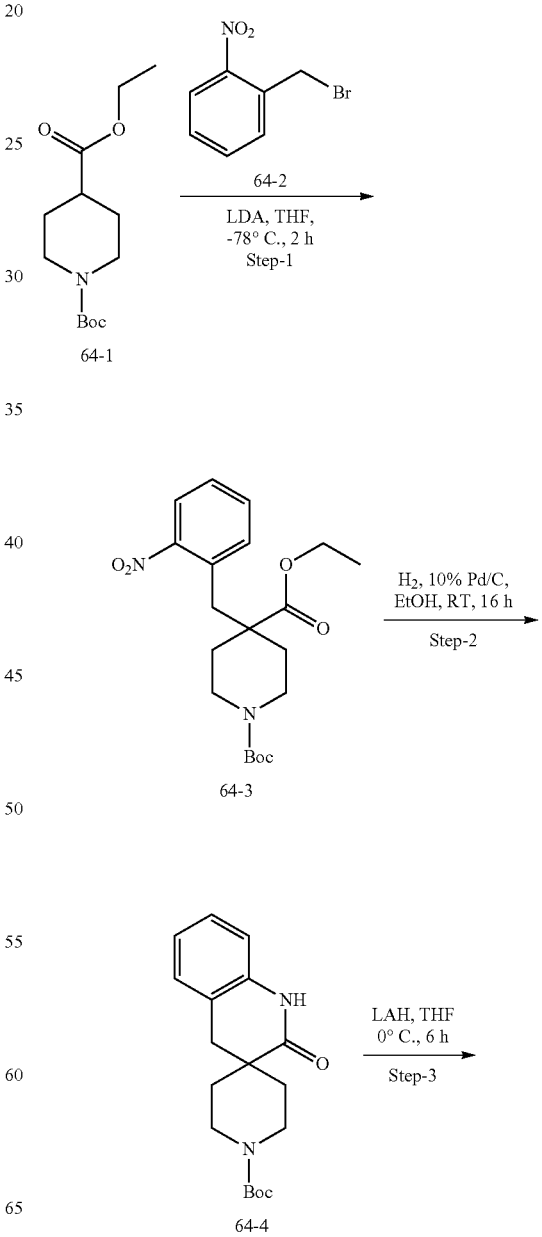

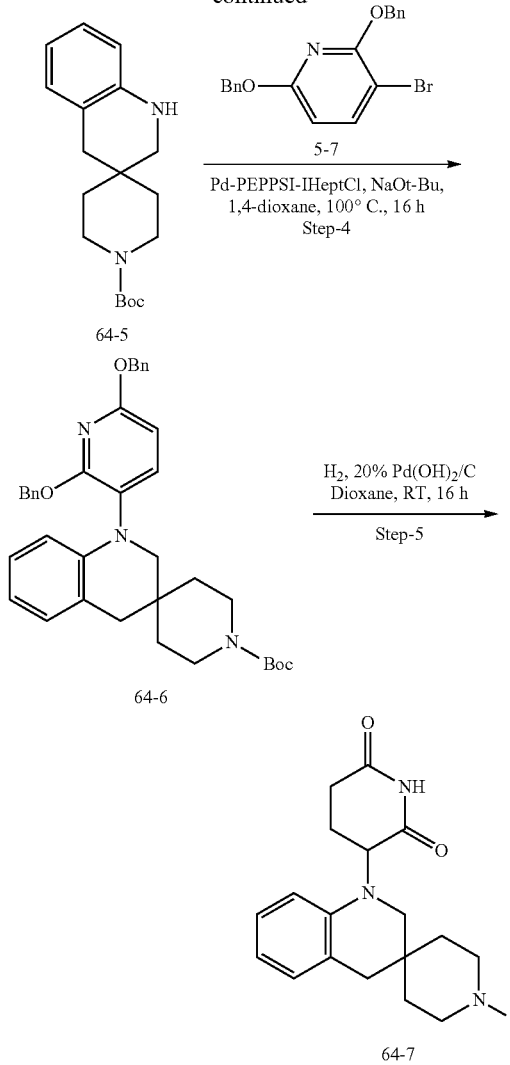

Step-1:

To a stirred solution of 1-(tert-butyl) 4-ethyl piperidine-1,4-dicarboxylate 64-1 (10.0 g, 38.86 mmol, 9.56 mL) in anhydrous THF (100 mL) in a 500 mL three-necked round bottomed flask was added lithium diisopropylamide (2.0 M in THF, 33.03 mL) dropwise at −78° C. under nitrogen atmosphere. The reaction mixture was stirred at same temperature for 1 h. A solution of 1-(bromomethyl)-2-nitrobenzene 64-2 (10.07 g, 46.63 mmol) in THF (50 mL) was added to the above mixture at −78° C. and the resulting brown suspension was stirred at same temperature for 2 h. After consumption of the starting material, the reaction mixture was quenched with saturated aqueous satd. NH$_4$Cl solution (100 mL) at 0° C. and mixture was extracted with EtOAc (2×80 mL). The organic layer was washed with water followed by brine solution, dried over anhydrous Na$_2$SO$_4$ and concentrated under reduced pressure to afford a crude residue which was purified by column chromatography (silica-gel, 230-400 mesh) using 0-100% EtOAc in pet ether as eluent to afford 1-(tert-butyl) 4-ethyl 4-(2-nitrobenzyl) piperidine-1,4-dicarboxylate 64-3 (6.3 g, 12.45 mmol, 32.05% yield) as a brown oil. UPLC-MS (ES$^+$): m/z: 293.1 [M−Boc+H]$^+$.

Step-2:

A solution of 1-(tert-butyl) 4-ethyl 4-(2-nitrobenzyl)piperidine-1,4-dicarboxylate 64-3 (6.3 g, 12.36 mmol) in anhydrous ethanol (100 mL) was purged with nitrogen and added 10% palladium on carbon (50% wet, 3.2 g) at ambient temperature. The resulting suspension was stirred at same temperature under hydrogen gas (balloon pressure) atmosphere for 16 h. After complete consumption of the starting material as indicated by UPLC-MS, the reaction mixture was filtered through a celite pad and washed with EtOAc (150 mL). The combined filtrate was concentrated under reduced pressure to afford a crude residue which was triturated with pet ether (2×40 mL) and dried under vacuum at room temperature for 3 h to afford tert-butyl 2'-oxo-1',4'-dihydro-2'H-spiro[piperidine-4,3'-quinoline]-1-carboxylate 64-4 (3.1 g, 9.45 mmol, 76.49% yield) as an off-white solid. UPLC-MS (ES$^−$): m/z 315.1 [M−H]$^−$.

Step-3:

To a solution of tert-butyl 2'-oxo-1',4'-dihydro-2'H-spiro [piperidine-4,3'-quinoline]-1-carboxylate 64-4 (3.1 g, 9.80 mmol) in anhydrous THF (60 mL) and was added lithium aluminum hydride (LAH) (2.0 M in THF, 7.35 mL) dropwise at 0° C. under nitrogen atmosphere. The reaction mixture was warmed to room temperature and stirred at the same temperature for 6 h. The reaction mixture was quenched (reverse quenching) slowly with ethyl acetate (20 mL) and saturated aq. Na$_2$SO$_4$ solution (40 mL) at 0° C. The reaction mixture was filtered through a celite bed and washed with ethyl acetate (100 mL). The layers were separated, and aqueous layer was extracted with ethyl acetate (2×50 ml). The combined organic layer was washed with brine (50 mL), dried over anhydrous sodium sulphate and concentrated under reduced pressure to afford crude, which was purified by column chromatography (silica-gel, 230-400 mesh) using 0-100% ethyl acetate in pet ether as eluent to afford tert-butyl 1',4'-dihydro-2'H-spiro[piperidine-4,3'-quinoline]-1-carboxylate 64-5 (1.2 g, 3.87 mmol, 39.49% yield) as an off white solid. UPLC-MS (ES$^+$): m/z 247.1 [M−tBu+H]$^+$.

Step-4:

To a stirred solution of tert-butyl 1',4'-dihydro-2'H-spiro [piperidine-4,3'-quinoline]-1-carboxylate 64-5 (900 mg, 2.98 mmol) and 2,6-dibenzyloxy-3-bromo-pyridine 5-7 (1.32 g, 3.57 mmol) in anhydrous 1,4 dioxane (18 mL), was added sodium tert-butoxide (572.00 mg, 5.95 mmol). The mixture was purged with nitrogen and was added Pd-PEPPSI-IHeptCl (231.60 mg, 238.09 mol) at room temperature. The reaction mixture was stirred at 100° C. for 16 h. After completion of the reaction, reaction mixture was diluted with ethyl acetate (40 mL) and filtered through celite bed and washed with ethyl acetate (60 mL). The filtrate was concentrated under reduced pressure to afford a crude residue which was purified by column chromatography (silica-gel, 230-400 mesh) using 0-100% ethyl acetate in pet ether as eluent to afford tert-butyl 1'-(2,6-bis(benzyloxy)pyridin-3-yl)-1',4'-dihydro-2'H-spiro[piperidine-4,3'-quinoline]-1-carboxylate 64-6 (1.2 g, 2.00 mmol, 67.05% yield) as an off-white solid. UPLC-MS (ES$^+$): m/z 592.3 [M+H]$^+$. Note: The reaction was performed in two batches (2×450 mg) using IKA stirrer.

Step-5:

A stirred solution of tert-butyl 1-(2,6-dibenzyloxy-3-pyridyl)spiro[2,4-dihydroquinoline-3,4'-piperidine]-1'-carboxylate 64-6 (1.2 g, 2.03 mmol) in anhydrous 1,4-dioxane (24 mL) was purged with nitrogen and added palladium hydroxide on carbon (20 wt. % dry basis) (840 mg, 2.03 mmol) at ambient temperature under nitrogen atmosphere.

The resulting suspension was stirred at same temperature under hydrogen atmosphere (balloon pressure) for 16 h. After complete consumption of the starting material as indicated by UPLC-MS, the reaction mixture was diluted with EtOAc (20 mL), filtered through a pad of celite and celite bed was washed with EtOAc (50 mL). The combined filtrate was concentrated under reduced pressure to afford a crude residue which was triturated with pet ether (20 mL). The obtained solid was purified through reverse phase by using RediSep Rf Gold® 120 g column and [mobile phase A: 10 mm ammonium bicarbonate in milliQ-water; mobile phase B: acetonitrile] to afford tert-butyl 1-(2,6-dioxo-3-piperidyl)spiro[2,4-dihydroquinoline-3,4'-piperidine]-1'-carboxylate 64-7 (250 mg, 603.37 mol, 29.75% yield) as off-white solid. LCMS (ES$^+$): m/z 358.2 [M−tBu+H]$^+$. $^1$H NMR (400 MHz, DMSO-d$_6$): δ 10.80 (s, 1H), 6.97-6.91 (m, 2H), 6.71 (d, J=7.20 Hz, 1H), 6.54-6.51 (m, 1H), 4.93 (d, J=8.80 Hz, 1H), 2.95-2.81 (m, 4H), 2.64-2.54 (m, 3H), 2.40-2.33 (m, 2H), 1.83-1.80 (m, 1H), 1.47-1.42 (m, 2H), 1.40 (s, 9H), 1.33-1.25 (m, 4H).

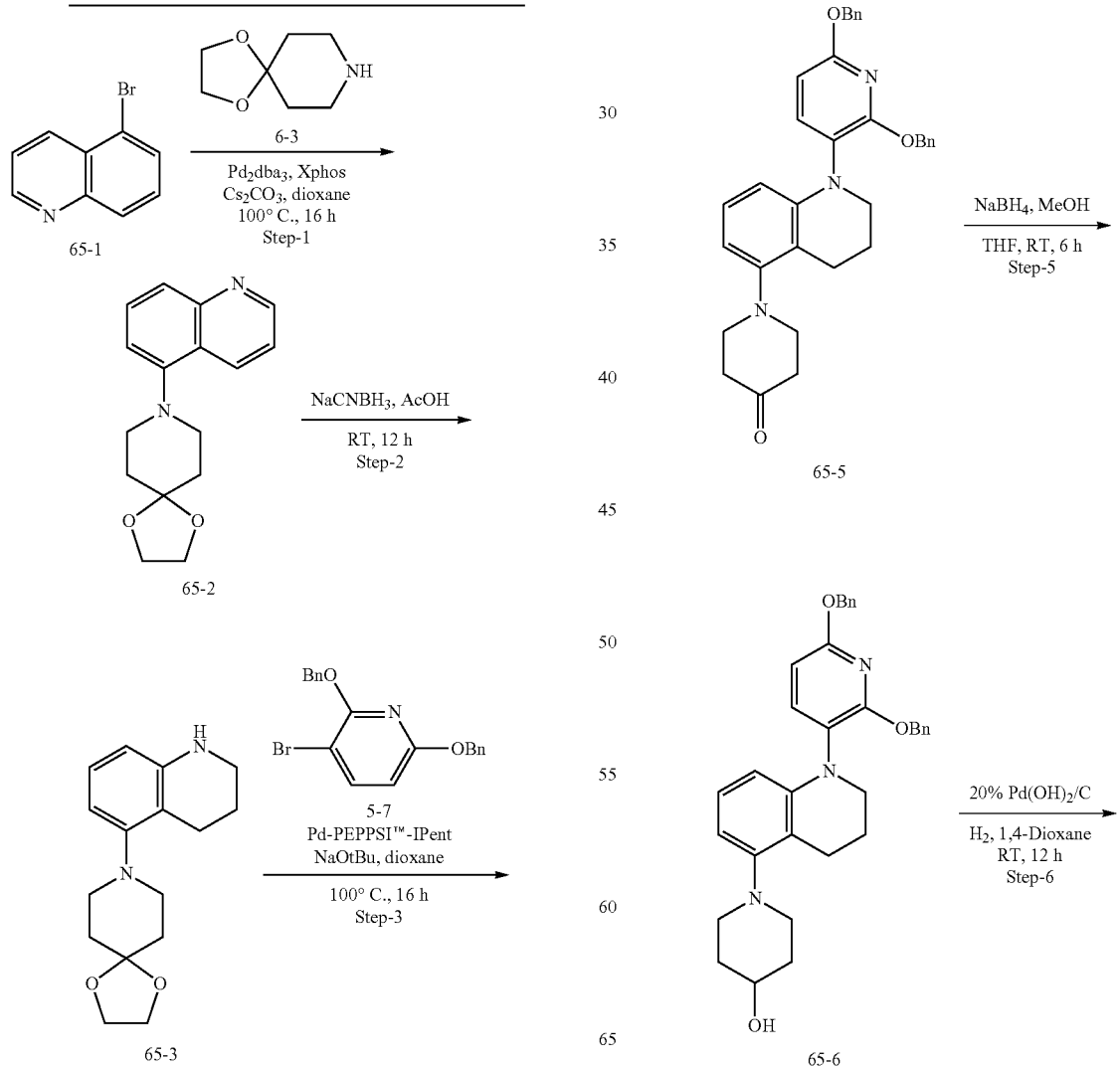

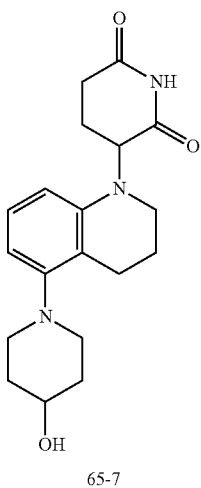

65-7

Step-1:

To a stirred solution of 5-bromoquinoline 65-1 (5 g, 24.03 mmol) and 1,4-dioxa-8-azaspiro[4.5]decane 6-3 (4.13 g, 28.84 mmol, 3.70 mL) in 1,4-dioxane (40 mL) in a sealed tube, was added $Cs_2CO_3$ (19.58 g, 60.08 mmol) and the reaction mixture was purged for 5 min with nitrogen gas. X-Phos (2.29 g, 4.81 mmol), followed by tris(dibenzylideneacetone)dipalladium (0) (2.20 g, 2.40 mmol) were added into it, and the reaction mixture was further purged with nitrogen gas for another 2 min. The reaction mixture was stirred at 100° C. for 16 h. The reaction mixture was filtered through celite pad and the filtrate was concentrated under reduced pressure to obtain crude. The crude product was purified by column chromatography (silica gel, 60-120 mesh) using 0-100% EtOAc in hexane as eluent to afford 8-(5-quinolyl)-1,4-dioxa-8-azaspiro[4.5]decane 65-2 (5 g, 18.31 mmol, 76.19% yield) as a brown solid. LCMS (ES$^+$): m/z 271.2 [M+H]$^+$.

Step-2:

To a stirred solution of 8-(5-quinolyl)-1,4-dioxa-8-azaspiro[4.5]decane 65-2 (5 g, 18.50 mmol) in acetic acid (250 mL) was added $NaCNBH_3$ (4.65 g, 73.98 mmol) portionwise at 0° C. The reaction mixture was stirred at room temperature for 12 h. The reaction mixture was diluted with ethyl acetate (400 mL), quenched with 10% aq. NaOH solution (pH-9). The organic layer was washed with brine (150 mL) and concentrated under reduced pressure to obtain crude. The crude was purified by column chromatography (silica gel, 100-200 mesh) using 0-100% EtOAc in hexane as eluent to afford 8-(1,2,3,4-tetrahydroquinolin-5-yl)-1,4-dioxa-8-azaspiro[4.5]decane 65-3 (2.4 g, 6.30 mmol, 34.05% yield) as light brown solid. LCMS (ES$^+$): m/z 275.2 [M+H]$^+$.

Step-3:

To a stirred solution of 8-(1,2,3,4-tetrahydroquinolin-5-yl)-1,4-dioxa-8-azaspiro [4.5]decane 65-3 (1.5 g, 5.47 mmol) and 2,6-dibenzyloxy-3-bromopyridine 5-7 (2.02 g, 5.47 mmol) in 1,4-dioxane (10 mL) was added sodium tert-butoxide (1.31 g, 13.67 mmol) at room temperature. The reaction mixture was purged with nitrogen gas for 2 min and then Pd-PEPPSI™-IPent (346.27 mg, 437.39 mol) was added into it. The reaction mixture was then stirred at 100° C. for 16 h. The reaction mixture was filtered through celite pad, the filtrate was concentrated under reduced pressure and the obtained crude was purified by column chromatography (silica gel, 60-120 mesh) using a 0-100% EtOAc in hexane as eluent to afford 8-[1-(2,6-dibenzyloxy-3-pyridyl)-3,4-dihydro-2H-quinolin-5-yl]-1,4-dioxa-8-azaspiro[4.5]decane 65-4 (900 mg, 1.28 mmol, 23.42% yield) as a red solid. UPLC-MS (ES$^+$): m/z 564.2 [M+H]$^+$.

Step-4:

To a stirred solution of 8-[1-(2,6-dibenzyloxy-3-pyridyl)-3,4-dihydro-2H-quinolin-5-yl]-1,4-dioxa-8-azaspiro[4.5] decane 65-4 (800 mg, 1.42 mmol) in acetone (22 mL) and water (8 mL), was added 4-methylbenzenesulfonic acid monohydrate (323.95 mg, 1.70 mmol) at room temperature. The reaction mixture was stirred at 65° C. for 16 h. The progress of the reaction was monitored by LCMS. The reaction mixture was diluted with ethyl acetate (300 mL) and quenched with 10% aq. NaOH solution (pH-9). The organic layer was washed with brine solution (100 mL) and concentrated under reduced pressure to obtain crude. The crude was purified by column chromatography (silica gel, 100-200 mesh) using 0-100% EtOAc in hexane as eluent to afford 1-[1-(2,6-dibenzyloxy-3-pyridyl)-3,4-dihydro-2H-quinolin-5-yl]piperidin-4-one 65-5 (300 mg, 410.48 mol, 28.92% yield) as a light yellow gum. LCMS (ES$^+$): m/z 520.3 [M+H]$^+$.

Step-5:

To a stirred solution of 1-[1-(2,6-dibenzyloxy-3-pyridyl)-3,4-dihydro-2H-quinolin-5-yl]piperidin-4-one 65-5 (300 mg, 577.33 mol) in methanol (8 mL) and THF (4 mL) was added sodium borohydride (54.60 mg, 1.44 mmol) at 0° C. Then reaction mixture was stirred at room temperature for 6 h. After completion of the reaction, the reaction mixture was quenched with ice cold water and then diluted with DCM (40 mL). The organic layer was separated, and the aqueous layer was extracted further with DCM (2×50 mL). The combined organic layer was dried over anhydrous sodium sulphate, filtered, and concentrated under reduced pressure to obtain crude. The crude was purified by column chromatography (silica gel, 100-200 mesh) using 0-100% EtOAc in hexane as eluent to afford 1-[1-(2,6-dibenzyloxy-3-pyridyl)-3,4-dihydro-2H-quinolin-5-yl]piperidin-4-ol 65-6 (200 mg, 353.50 mol, 61.23% yield) as a red gum. LCMS (ES$^+$): m/z 522.2 [M+H]$^+$.

Step-6:

To a stirred solution of 1-[1-(2,6-dibenzyloxy-3-pyridyl)-3,4-dihydro-2H-quinolin-5-yl]piperidin-4-ol 65-6 (200 mg, 383.40 mol) in 1,4-dioxane (8 mL) was added 20% Pd(OH)$_2$/C (107.69 mg, 766.80 mol) at room temperature under nitrogen atmosphere. The resulting suspension was stirred under hydrogen atmosphere (balloon pressure) at room temperature for 12 h. After completion of the starting material as indicated by TLC, the reaction mixture was filtered through a pad of celite and the celite bed was washed with 1,4-dioxane/THF (1:1) (80 mL). The combined filtrate was concentrated under reduced pressure to obtain crude, which was purified by column chromatography (silica gel, 100-200 mesh) using 0-100% EtOAc in hexane as eluent to afford 3-[5-(4-hydroxy-1-piperidyl)-3,4-dihydro-2H-quinolin-1-yl]piperidine-2,6-dione 65-7 (21 mg, 60.76 mol, 15.85% yield) as a brown solid. UPLC-MS (ES$^+$): m/z 344.4 [M+H]$^+$. $^1$H NMR (400 MHz, DMSO-d$_6$): δ 10.78 (s, 1H), 6.88 (t, J=8.40 Hz, 1H), 6.44 (d, J=8.40 Hz, 1H), 6.34 (d, J=7.60 Hz, 1H), 4.84 (dd, J=4.80, 12.40 Hz, 1H), 4.63 (d, J=4.00 Hz, 1H), 3.64-3.52 (m, 1H), 3.17-3.02 (m, 2H), 2.97-2.92 (m, 2H), 2.90-2.79 (m, 1H), 2.76-2.69 (m, 1H), 2.54-2.50 (m, 2H), 2.47-2.43 (m, 1H), 2.34-2.25 (m, 1H), 1.89-1.79 (m, 4H), 1.78-1.71 (m, 2H), 1.56-1.47 (m, 2H).

Scheme 66: Synthesis of (3S)-3-[5-[4-(2-hydroxyethyl)-1-piperidyl]-3,4-dihydro-2H-quinolin-1-yl]piperidine-2,6-dione and (3R)-3-[5-[4-(2-hydroxyethyl)-1-piperidyl]-3,4-dihydro-2H-quinolin-1-yl]piperidine-2,6-dione

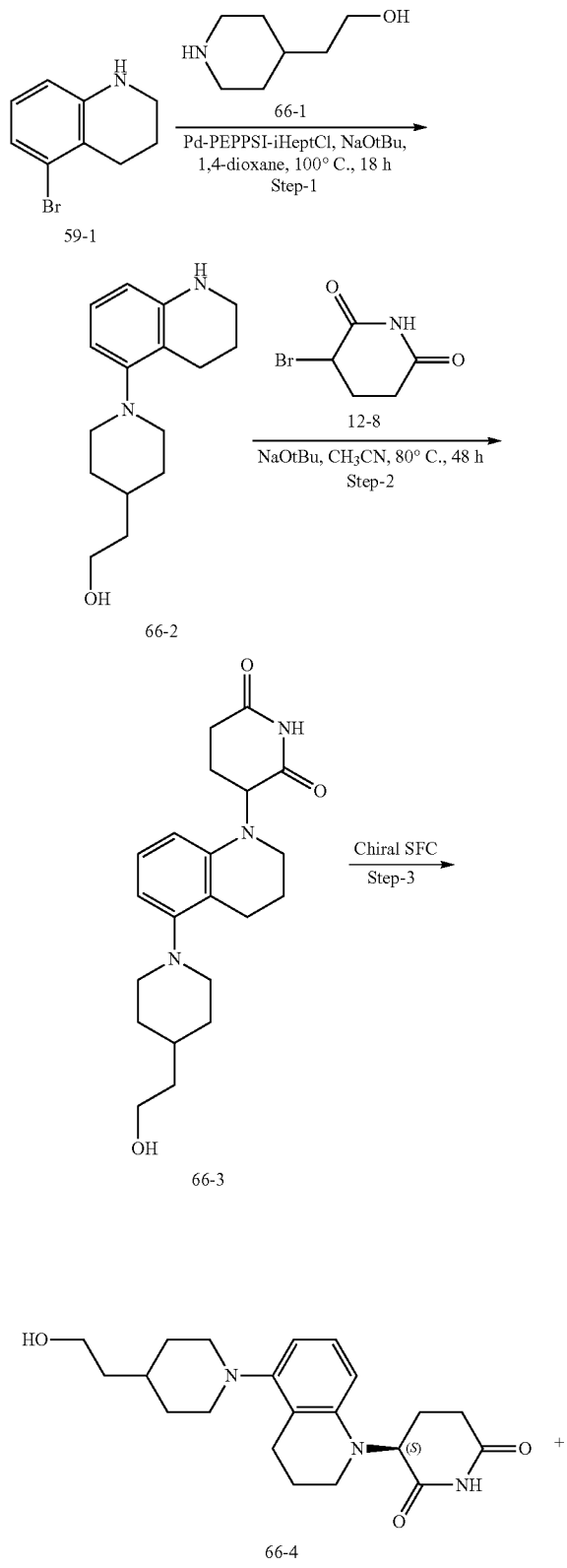

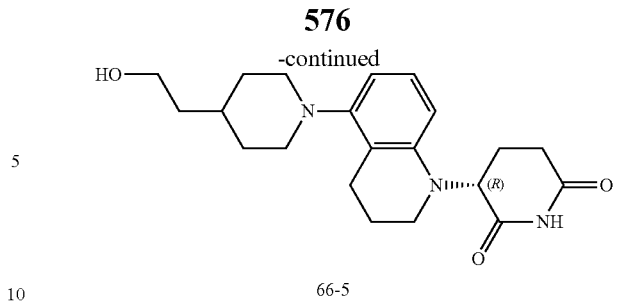

Step-1:

To the stirred solution of 5-bromo-1,2,3,4-tetrahydroquinoline 59-1 (3 g, 14.15 mmol) and 2-(4-piperidyl)ethanol 66-1 (3.66 g, 28.29 mmol) in 1,4-dioxane (50 mL) was added sodium 2-methylpropan-2-olate (2.04 g, 21.22 mmol) at room temperature under nitrogen atmosphere. The reaction mixture was degassed with nitrogen for 10 min, then added Pd-PEPPSI-iHeptCl (688.72 mg, 707.26 mol) at the same temperature. The reaction mixture was stirred at 100° C. for 18 h. The reaction mixture was filtered through a pad of celite and concentrated under reduced pressure to obtain crude. The crude was purified by column chromatography (silica gel, 100-200 mesh) using 0-100% ethyl acetate in pet ether as eluent to afford 2-[1-(1,2,3,4-tetrahydroquinolin-5-yl)-4-piperidyl]ethanol 66-2 (1 g, 3.65 mmol, 25.79% yield) as a yellow gum. UPLC-MS (ES+): m/z 261.2 [M+H]+.

Step-2:

To a stirred solution of 2-[1-(1,2,3,4-tetrahydroquinolin-5-yl)-4-piperidyl]ethanol 66-2 (1 g, 3.84 mmol) and 3-bromopiperidine-2,6-dione 12-8 (4.42 g, 23.04 mmol) in CH$_3$CN (10 mL) at room temperature was added sodium 2-methylpropan-2-olate (1.48 g, 15.36 mmol). The reaction mixture was stirred at 80° C. for 48 h. After completion, the reaction mixture was concentrated under reduced pressure to obtain crude. The crude was purified by column chromatography (silica gel, 100-200 mesh) using 0-100% of ethyl acetate in hexane as eluent to afford 3-[5-[4-(2-hydroxyethyl)-1-piperidyl]-3,4-dihydro-2H-quinolin-1-yl]piperidine-2,6-dione 66-3 (100 mg, 251.43 mol, 6.55% yield) as a brown solid. UPLC-MS (ES+): m/z 372.1 [M+H]+.

Step-3:

Enantiomers of racemic 3-[5-[4-(2-hydroxyethyl)-1-piperidyl]-3,4-dihydro-2H-quinolin-1-yl]piperidine-2,6-dione 66-3 (90 mg) were separated by chiral SFC [SFC chiral purification method: column: I-cellulose B (250×30) mm, 5 um; mobile phase: CO$_2$:isopropanol[60:40]; flow rate: 120 mL/min; wavelength: 210 nm]. The early eluting peak (3S)-3-[5-[4-(2-hydroxyethyl)-1-piperidyl]-3,4-dihydro-2H-quinolin-1-yl]piperidine-2,6-dione 66-4 (arbitrarily assigned as S, 30 mg, 32.41% yield, 100% enantiopurity) was isolated as an off-white solid. UPLC-MS (ES+): m/z 372.2 [M+H]+. $^1$H NMR (400 MHz, DMSO-d$_6$): δ 10.78 (s, 1H), 6.89 (t, J=8.00 Hz, 1H), 6.44 (d, J=8.80 Hz, 1H), 6.34 (d, J=7.60 Hz, 1H), 4.87-4.80 (m, 1H), 4.35 (t, J=5.20 Hz, 1H), 3.50-3.45 (m, 2H), 3.14-3.08 (m, 2H), 3.07-3.01 (m, 2H), 2.89-2.81 (m, 1H), 2.75-2.67 (m, 1H), 2.61-2.55 (m, 2H), 2.51-2.43 (m, 2H), 2.34-2.25 (m, 1H), 1.89-1.83 (m, 1H) 1.75-1.67 (m, 4H), 1.54-1.41 (m, 3H), 1.30-1.23 (m, 2H). The late eluting peak (3R)-3-[5-[4-(2-hydroxyethyl)-1-piperidyl]-3,4-dihydro-2H-quinolin-1-yl]piperidine-2,6-dione 66-5 (arbitrarily assigned as R, 30 mg, 33.25% yield, 99.3% enantiopurity) was isolated as an off-white solid. UPLC-MS (ES+): m/z 372.2 [M+H]+. $^1$H NMR (400 MHz, DMSO-d$_6$): δ 10.78 (s, 1H), 6.89 (t, J=8.00 Hz, 1H), 6.44 (d, J=8.80 Hz, 1H), 6.34 (d, J=7.60 Hz, 1H), 4.87-4.82 (m, 1H), 4.35 (t, J=5.20 Hz, 1H), 3.50-3.45 (m, 2H), 3.15-2.96 (m, 4H), 2.89-2.79 (m, 1H), 2.75-2.69 (m, 1H), 2.61-2.52 (m, 2H), 2.50-2.46 (m, 2H), 2.34-2.26 (m, 1H), 1.90-1.83 (m, 1H), 1.77-1.69 (m, 4H), 1.54-1.42 (m, 3H), 1.33-1.20 (m, 2H).

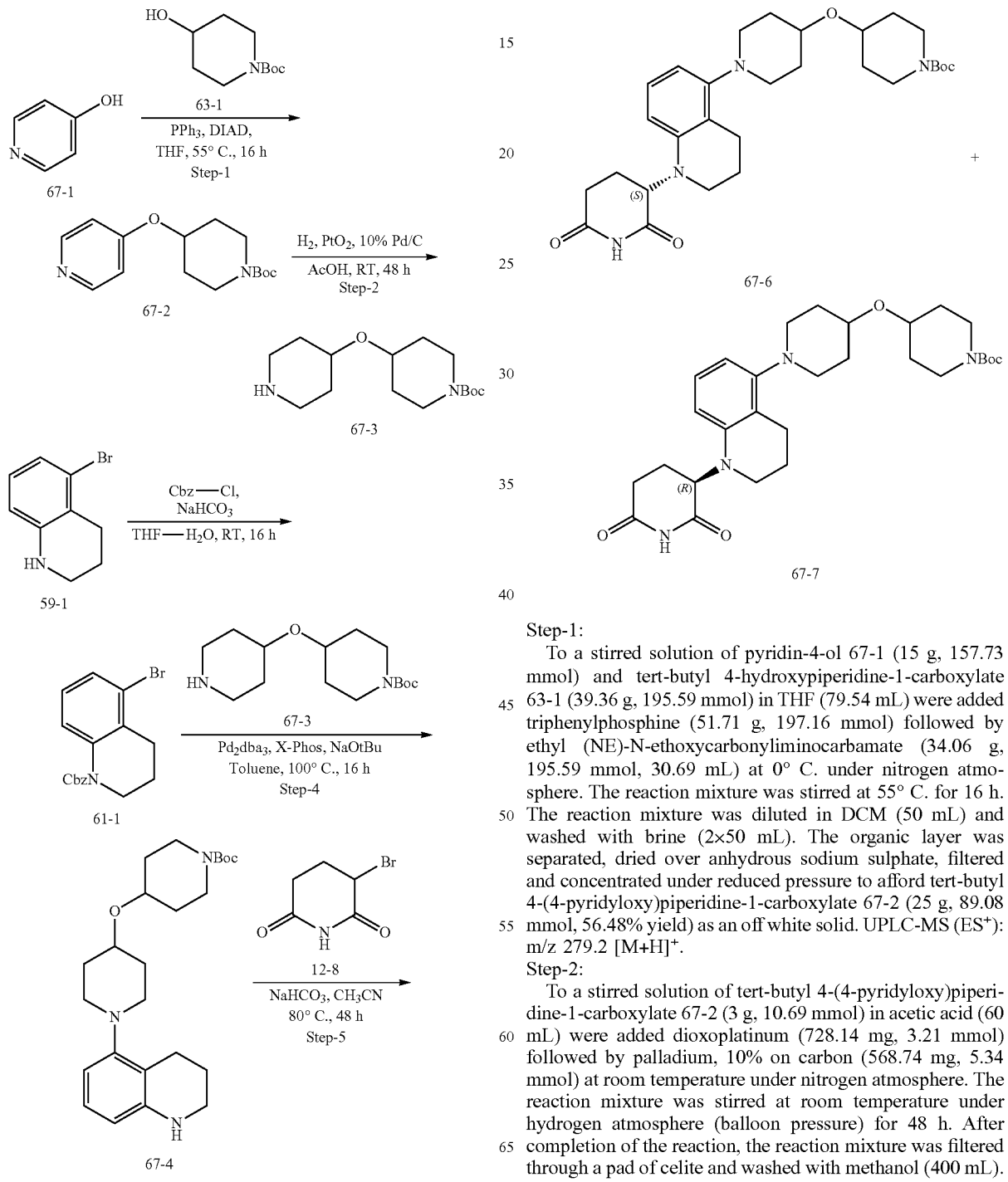

Step-1:

To a stirred solution of pyridin-4-ol 67-1 (15 g, 157.73 mmol) and tert-butyl 4-hydroxypiperidine-1-carboxylate 63-1 (39.36 g, 195.59 mmol) in THF (79.54 mL) were added triphenylphosphine (51.71 g, 197.16 mmol) followed by ethyl (NE)-N-ethoxycarbonyliminocarbamate (34.06 g, 195.59 mmol, 30.69 mL) at 0° C. under nitrogen atmosphere. The reaction mixture was stirred at 55° C. for 16 h. The reaction mixture was diluted in DCM (50 mL) and washed with brine (2×50 mL). The organic layer was separated, dried over anhydrous sodium sulphate, filtered and concentrated under reduced pressure to afford tert-butyl 4-(4-pyridyloxy)piperidine-1-carboxylate 67-2 (25 g, 89.08 mmol, 56.48% yield) as an off white solid. UPLC-MS (ES$^+$): m/z 279.2 [M+H]$^+$.

Step-2:

To a stirred solution of tert-butyl 4-(4-pyridyloxy)piperidine-1-carboxylate 67-2 (3 g, 10.69 mmol) in acetic acid (60 mL) were added dioxoplatinum (728.14 mg, 3.21 mmol) followed by palladium, 10% on carbon (568.74 mg, 5.34 mmol) at room temperature under nitrogen atmosphere. The reaction mixture was stirred at room temperature under hydrogen atmosphere (balloon pressure) for 48 h. After completion of the reaction, the reaction mixture was filtered through a pad of celite and washed with methanol (400 mL). The obtained filtrate was concentrated under reduced pressure to afford tert-butyl 4-(4-piperidyloxy)piperidine-1-carboxylate 67-3 (3.01 g, 10.58 mmol, 98.94% yield) as an off white solid. UPLC-MS (ES+): m/z 285.3 [M+H]+.

Step-3:

To a stirred solution of 5-bromo-1,2,3,4-tetrahydroquinoline 59-1 (5 g, 23.58 mmol) in THF (27.65 mL) and water (27.65 mL) were added sodium bicarbonate (2.57 g, 30.65 mmol, 1.19 mL) followed by benzyl carbonochloridate (5.63 g, 33.01 mmol, 4.69 mL) at 0° C. under nitrogen atmosphere. The reaction mixture was stirred at room temperature for 16 h. After completion of the reaction, the reaction mixture was quenched with 10% aq. sodium bicarbonate (100 mL) and extracted with ethyl acetate (3×150 mL). The combined organic layer was dried over anhydrous sodium sulfate, filtered, and concentrated under reduced pressure to obtain crude. The crude was purified by column chromatography (silica gel, 60-120 mesh) using 0-100% ethyl acetate in hexane as eluent to afford benzyl 5-bromo-3,4-dihydro-2H-quinoline-1-carboxylate 61-1 (8.10 g, 22.02 mmol, 93.38% yield) as a yellow gum. UPLC-MS (ES+): m/z 345.9 [M+H]+.

Step-4:

To a stirred solution of benzyl 5-bromo-3,4-dihydro-2H-quinoline-1-carboxylate 61-1 (1 g, 2.89 mmol) and tert-butyl 4-(4-piperidyloxy)piperidine-1-carboxylate 67-3 (1.09 g, 3.75 mmol) in toluene (10 mL) was added sodium 2-methylpropan-2-olate (832.74 mg, 8.67 mmol). The reaction mixture was degassed with nitrogen for 10 mins, followed by the addition of dicyclohexyl-[2-(2,4,6-triisopropylphenyl)phenyl]phosphane (275.39 mg, 577.67 mol) and tris(dibenzylideneacetone)dipalladium(0) (264.49 mg, 288.84 mol) at room temperature under nitrogen atmosphere. The reaction mixture was stirred at 100° C. for 16 h. After completion of the reaction, the reaction mixture was cooled to room temperature, filtered through celite bed, and washed with DCM (50 mL). The combined filtrate was concentrated under reduced pressure, and the obtained crude was purified by column chromatography (silica gel, 100-200 mesh) using a 0-100% ethyl acetate in hexane as eluent to afford tert-butyl 4-[[1-(1,2,3,4-tetrahydroquinolin-5-yl)-4-piperidyl]oxy]piperidine-1-carboxylate 67-4 (578 mg, 955.67 mol, 33.09% yield) as a brown semi solid. UPLC-MS (ES+): m/z 416.3 [M+H]+.

Step-5:

To a stirred solution of tert-butyl 4-[[1-(1,2,3,4-tetrahydroquinolin-5-yl)-4-piperidyl]oxy]piperidine-1-carboxylate 67-4 (570 mg, 942.44 mol) in acetonitrile (15 mL) was added sodium bicarbonate (237.51 mg, 2.83 mmol) followed by 3-bromopiperidine-2,6-dione 12-8 (361.92 mg, 1.88 mmol) at room temperature under nitrogen atmosphere. The reaction mixture was stirred at 80° C. for 48 h. After completion of the reaction, the reaction mixture was diluted with dichloromethane (50 mL), filtered through a celite bed, and washed with dichloromethane (50 mL). The combined filtrate was concentrated under reduced pressure and the obtained crude was purified by column chromatography (silica gel, 230-400 mesh) using a gradient of 0-100% ethyl acetate in hexane as eluent to afford tert-butyl 4-[[1-[1-(2,6-dioxo-3-piperidyl)-3,4-dihydro-2H-quinolin-5-yl]-4-piperidyl]oxy]piperi-dine-1-carboxylate 67-5 (120 mg, 225.05 mol, 23.88% yield) as a brown semi solid. UPLC-MS (ES+): m/z 527.2 [M+H]+.

Step-6:

Racemic tert-butyl 4-[[1-[1-(2,6-dioxo-3-piperidyl)-3,4-dihydro-2H-quinolin-5-yl]-4-piperidyl]-oxy]piperidine-1-carboxylate 67-5 (109 mg) was purified by chiral SFC to separate the R- and S-isomers [Column: Amylose -A (250*30) mm, 5 µm, mobile phase: CO2:0.2% formic acid in isopropanol:acetonitrile (70:30), total flow: 110 ml/min, back pressure: 100 bar, wavelength: 220 nm, cycle time: 10.5 min]. The early eluting peak tert-butyl 4-[[1-[1-[(3S)-2,6-dioxo-3-piperidyl]-3,4-dihydro-2H-quinolin-5-yl]-4-piperidyl]oxy]piperidine-1-carboxylate 67-6 (arbitrarily assigned as S, 20 mg, 37.18 mol, 18.19% yield, 99.0% enantiopurity) as a light brown solid. UPLC-MS (ES+): m/z 527.2 [M+H]+. 1H NMR (400 MHz, DMSO-d6): δ 10.78 (s, 1H), 6.89 (t, J=8.00 Hz, 1H), 6.45 (d, J=8.40 Hz, 1H), 6.34 (d, J=7.60 Hz, 1H), 4.89-4.84 (m, 1H), 3.70-3.52 (m, 4H), 3.18-3.09 (m, 1H), 3.08-2.90 (m, 5H), 2.88-2.78 (m, 1H), 2.77-2.67 (m, 1H), 2.64-2.55 (m, 3H), 2.35-2.23 (m, 1H), 1.95-1.83 (m, 3H), 1.81-1.72 (m, 4H), 1.63-149 (m, 2H), 1.44-1.28 (m, 12H). The late eluting peak tert-butyl 4-[[1-[1-[(3R)-2,6-dioxo-3-piperidyl]-3,4-dihydro-2H-quinolin-5-yl]-4-piperidyl]oxy]piperidine-I-carboxylate 67-7 (arbitrarily assigned as R, 23 mg, 43.43 mol, 21.24% yield, 98.2% enantiopurity) as a light brown solid. UPLC-MS (ES+): m/z 527.2 [M+H]+. 1H NMR (400 MHz, DMSO-d6): δ 10.77 (s, 1H), 6.89 (t, J=8.00 Hz, 1H), 6.45 (d, J=8.40 Hz, 1H), 6.34 (d, J=7.60 Hz, 1H), 4.84 (dd, J=4.80, 12.40 Hz, 1H), 3.69-3.53 (m, 4H), 3.18-3.09 (m, 1H), 3.08-2.91 (m, 5H), 2.90-2.80 (m, 1H), 2.77-2.67 (m, 1H), 2.66-2.55 (m, 3H), 2.32-2.24 (m, 1H), 1.95-1.82 (m, 3H), 1.81-1.71 (m, 4H), 1.63-1.50 (m, 2H), 1.40 (s, 9H), 1.37-1.27 (m, 3H).

Scheme 68: Synthesis of tert-butyl 4-[1-[(3S)-2,6-dioxo-3-piperidyl]-3,4-dihydro-2H-quinolin-5-yl]piperazine-1-carboxylate and tert-butyl 4-[1-[(3R)-2,6-dioxo-3-piperidyl]-3,4-dihydro-2H-quinolin-5-yl]piperazine-1-carboxylate

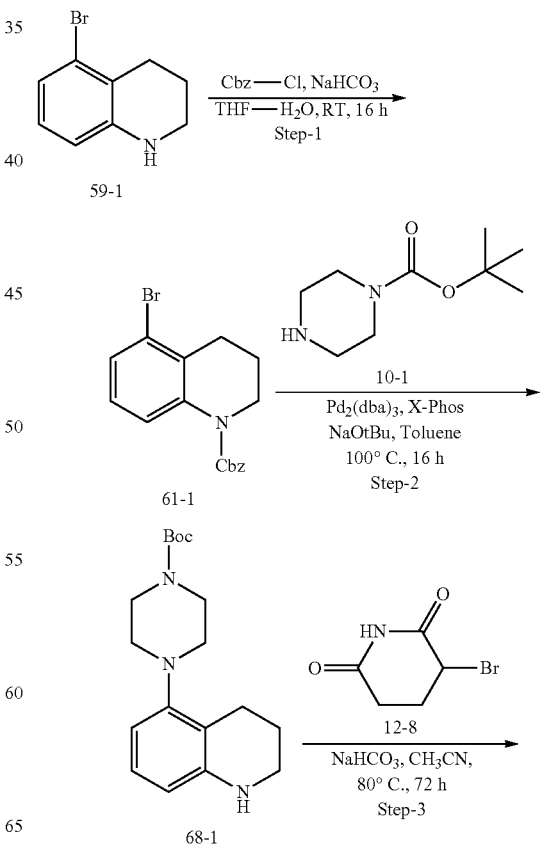

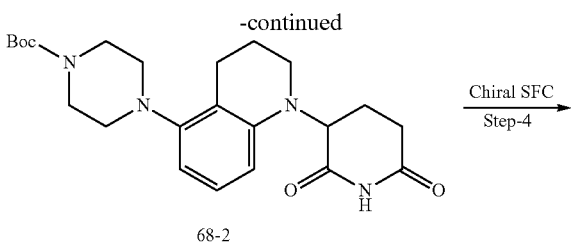

68-2

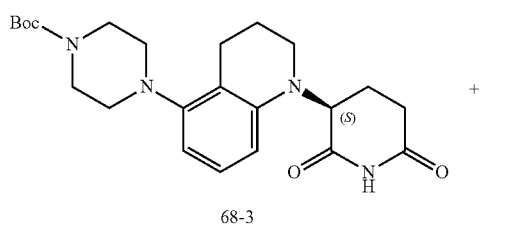

68-3

68-4

Step-1:

To a stirred mixture of 5-bromo-1,2,3,4-tetrahydroquinoline 59-1 (2 g, 9.43 mmol) and sodium bicarbonate (1.03 g, 12.26 mmol) in water (10 mL) and THF (10 mL) was added benzyl chlorocarbonate (2.25 g, 13.20 mmol, 1.88 mL) at 0° C. in a dropwise manner. Then the resulting reaction mixture was stirred at room temperature for 16 h. The reaction mixture was quenched with 10% aq. sodium bicarbonate (100 mL), extracted with ethyl acetate (2×250 mL), and the combined organic layer was dried over anhydrous sodium sulphate, filtered, and concentrated under reduced pressure to obtain crude. The crude was purified through column chromatography (silica gel, 60-120 mesh) using 0-30% EtOAc in hexane as eluent to afford benzyl 5-bromo-3,4-dihydro-2H-quinoline-1-carboxylate 61-1 (3.25 g, 8.64 mmol, 91.58% yield) as an off yellow gum. $^1$H NMR (400 MHz, DMSO-d$_6$): δ 7.62 (d, J=8.40 Hz, 1H), 7.45-7.32 (m, 6H), 7.10 (t, J=8.00 Hz, 1H), 5.20 (s, 2H), 3.76-3.70 (m, 2H), 2.74 (t, J=6.80 Hz, 2H), 1.95-1.88 (m, 2H).

Step-2:

A stirred solution of benzyl 5-bromo-3,4-dihydro-2H-quinoline-1-carboxylate 61-1 (1 g, 2.66 mmol) and tert-butyl piperazine-1-carboxylate 10-1 (593.91 mg, 3.19 mmol) in toluene (10 mL) was degassed with N$_2$ gas for 10 mins, then added sodium 2-methylpropan-2-olate (766.12 mg, 7.97 mmol), tris(dibenzylideneacetone)dipalladium(0) (243.33 mg, 265.73 mol), and dicyclohexyl-[2-(2,4,6-triisopropylphenyl)phenyl]phosphane (253.36 mg, 531.46 mol), respectively. The reaction mixture was stirred at 100° C. for 16 h. After completion of reaction, reaction mass was cooled to room temperature, filtered through a pad of celite, and washed with DCM (100 mL). The filtrate was concentrated under reduced pressure to obtain the crude product, which was purified by column chromatography (silica gel, 100-200 mesh) using 0-100% of EtOAc in hexane as eluent to afford tert-butyl 4-(1,2,3,4-tetrahydroquinolin-5-yl)piperazine-1-carboxylate 68-1 (680 mg, 1.84 mmol, 69.35% yield) as a brown semi solid. UPLC-MS (ES$^+$): m/z 318.2 [M+H]$^+$.

Step-3:

To a stirred solution of tert-butyl 4-(1,2,3,4-tetrahydroquinolin-5-yl)piperazine-1-carboxylate 68-1 (600 mg, 1.89 mmol) in acetonitrile (20 mL) was added sodium bicarbonate (635.19 mg, 7.56 mmol) and stirred for 15 minutes at room temperature. Then 3-bromopiperidine-2,6-dione 12-8 (907.35 mg, 4.73 mmol) was added to the reaction mixture. The reaction mixture was heated at 80° C. for 72 h. After completion, the reaction mixture was diluted with ethyl acetate (100 mL) and filtered through a pad of celite. The organic layer was dried over anhydrous Na$_2$SO$_4$, filtered, concentrated to obtain crude. The crude product was purified by column chromatography (silica gel, 230-400 mesh) using 0-100% EtOAc in hexane as eluent to afford tert-butyl 4-[1-(2,6-dioxo-3-piperidyl)-3,4-dihydro-2H-quinolin-5-yl]piperazine-1-carboxylate 68-2 (65 mg, 133.28 mol, 7.05% yield) as a brown solid. UPLC-MS (ES$^+$): m/z 429.1 [M+H]$^+$.

Step-4:

Enantiomers of racemic tert-butyl 4-[1-(2,6-dioxo-3-piperidyl)-3,4-dihydro-2H-quinolin-5-yl]piperazine-1-carboxylate 68-2 (65 mg, 133.28 mol) were separated through chiral SFC [chiral SFC purification method: column: Lux A1 (250*20) mm, 5 μm; mobile phase: CO$_2$:0.2% formic acid in isopropanol:acetonitrile (82:18); total flow: 60 mL/min; back pressure: 100 bar; wavelength: 220 nm]. The early eluting peak tert-butyl 4-[1-[(3S)-2,6-dioxo-3-piperidyl]-3,4-dihydro-2H-quinolin-5-yl]piperazine-1-carboxylate 68-3 (arbitrarily assigned as S, 7.5 mg, 17.39 mol, 13.05% yield, 99.6% enantiopurity) isolated as a brown solid. UPLC-MS (ES$^+$): m/z 429.1 [M+H]$^+$. $^1$H NMR (400 MHz, DMSO-d$_6$): δ 10.78 (s, 1H), 6.91 (t, J=8.00 Hz, 1H), 6.49 (d, J=8.40 Hz, 1H), 6.34 (d, J=8.00 Hz, 1H), 4.86 (dd, J=4.80, 12.80 Hz, 1H), 3.73-3.38 (m, 3H), 3.27-3.18 (m, 1H), 3.17-3.03 (m, 2H), 2.89-2.60 (m, 7H), 2.59-2.56 (m, 1H), 2.36-2.23 (m, 1H), 1.91-1.83 (m, 1H), 1.78-1.70 (m, 2H), 1.43 (s, 9H). The late eluting peak tert-butyl 4-[1-[(3R)-2,6-dioxo-3-piperidyl]-3,4-dihydro-2H-quinolin-5-yl]piperazine-1-carboxylate 68-4 (arbitrarily assigned as R, 6 mg, 13.45 μmol, 10.09% yield, 98.1% enantiopurity) isolated as a brown solid. 429.1. $^1$H NMR (400 MHz, DMSO-d$_6$): δ 10.78 (s, 1H), 6.91 (t, J=8.00 Hz, 1H), 6.49 (d, J=8.80 Hz, 1H), 6.34 (d, J=7.60 Hz, 1H), 4.86 (dd, J=4.80, 12.60 Hz, 1H), 3.80-3.35 (m, 3H), 3.28-3.02 (m, 3H), 2.90-2.61 (m, 7H), 2.60-2.55 (m, 1H), 2.37-2.26 (m, 1H), 1.91-1.84 (m, 1H), 1.80-1.68 (m, 2H), 1.43 (s, 9H).

TABLE 1
Representative Compounds of the Present Invention
| Compound | Structure |
|---|---|
| 5-12 | 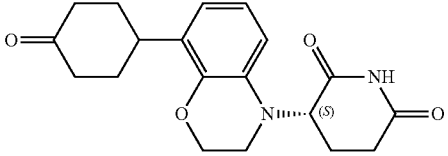 |
| 5-13 | 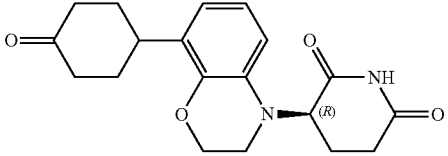 |
| 5-14 | 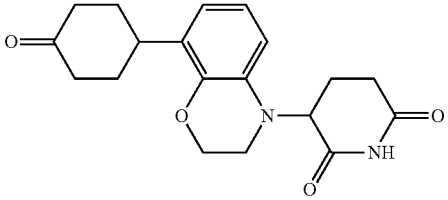 [SMILES: O=C1CCC(c2cccc3c2OCCN3C2CCC(=O)NC2=O)CC1] |
| 6-10 | 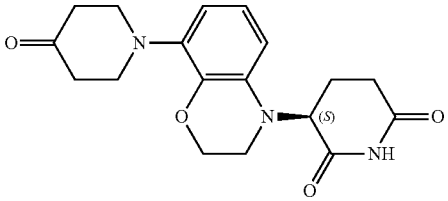 |
| 6-11 | 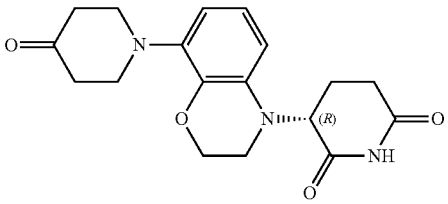 |
| 6-12 | 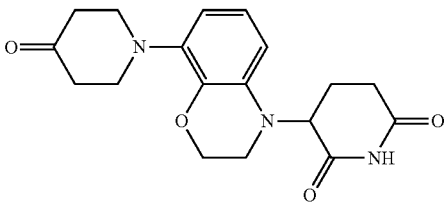 [SMILES: O=C1CCN(c2cccc3c2OCCN3C2CCC(=O)NC2=O)CC1] |
| 7-8 | 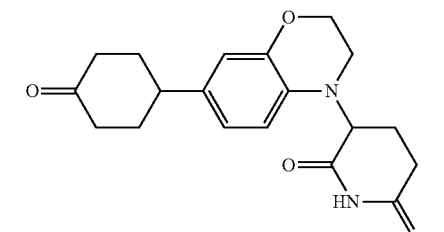 |

TABLE 1-continued

Representative Compounds of the Present Invention

| Compound | Structure |
|---|---|
| 7-9 | 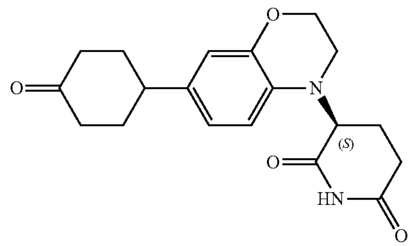 |
| 7-10 | 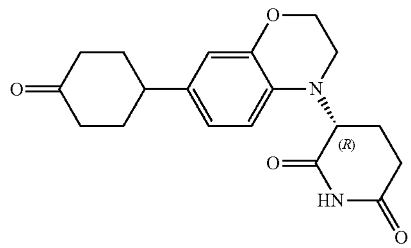 |
| 8-10 | 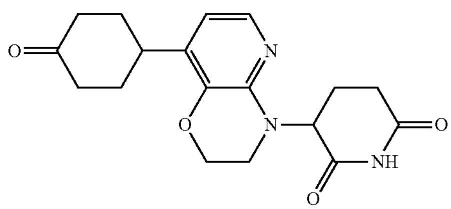 [SMILES: O=C1CCC(c2ccnc3c2OCCN3C2CCC(=O)NC2=O)CC1] |
| 9-6 | 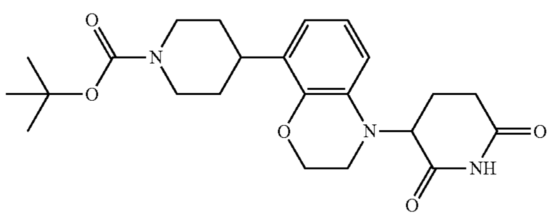 [SMILES: CC(C)(C)OC(=O)N1CCC(c2cccc3c2OCCN3C2CCC(=O)NC2=O)CC1] |
| 9-9 | 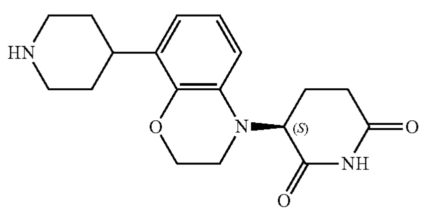 |
| 9-10 | 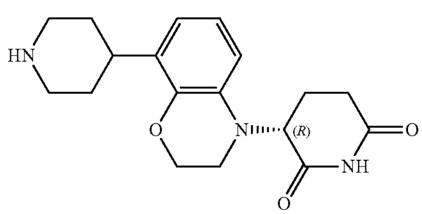 |
| 9-11 | 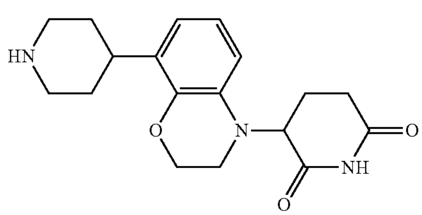 [SMILES: O=C1CCC(N2CCOc3c(C4CCNCC4)cccc32)C(=O)N1] |

TABLE 1-continued

Representative Compounds of the Present Invention

| Compound | Structure |
|---|---|
| 10-8 | 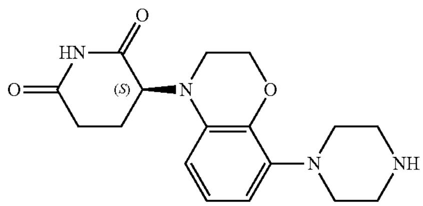 |
| 10-9 | 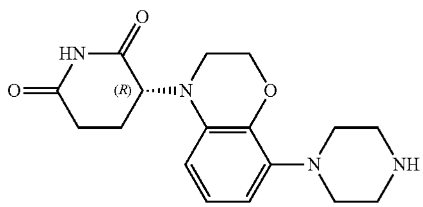 |
| 10-10 | 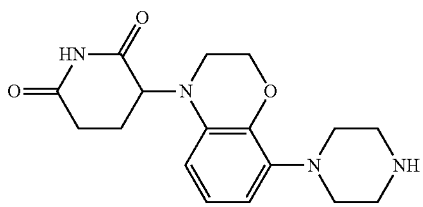 [SMILES: O=C1CCC(N2CCOc3c(N4CCNCC4)cccc32)C(=O)N1] |
| 11-9 | 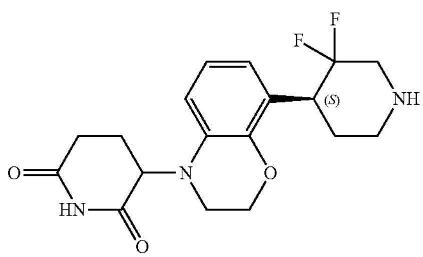 |
| 11-11 | 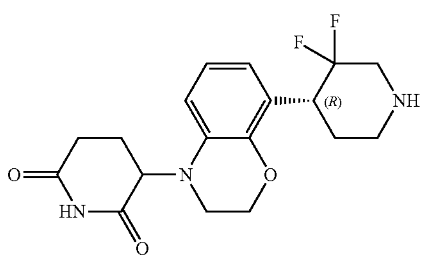 |
| 12-10 | 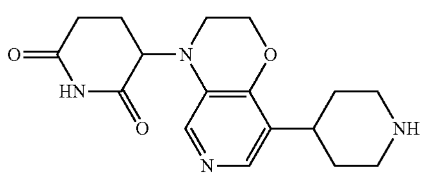 [SMILES: O=C1CCC(N2CCOc3c(C4CCNCC4)cncc32)C(=O)N1] |
| 13-8 | 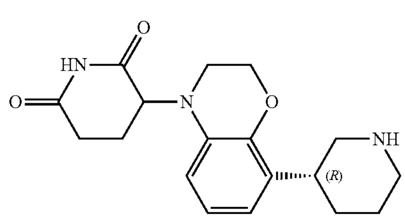 |

TABLE 1-continued

Representative Compounds of the Present Invention

| Compound | Structure |
|---|---|
| 13-11 | 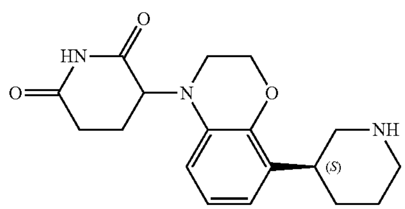 |
| 14-7 | 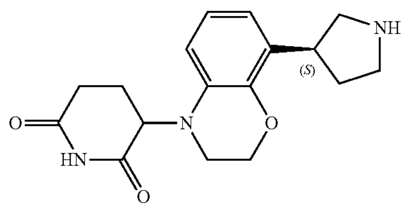 |
| 14-9 | 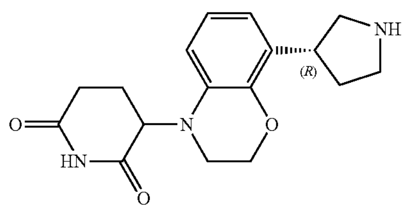 |
| 15-4 | 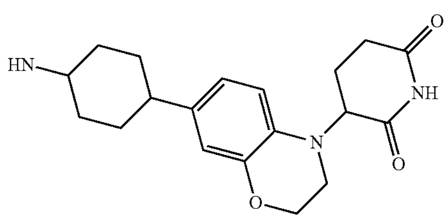 [SMILES: NC1CCC(c2ccc3c(c2)OCCN3C2CCC(=O)NC2=O)CC1] |
| 16-6 | 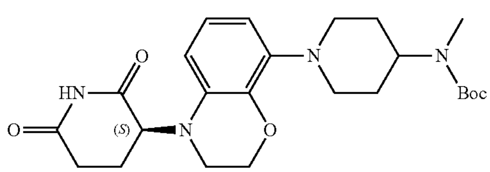 |
| 16-7 | 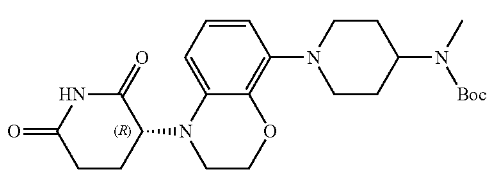 |
| 17-9 | 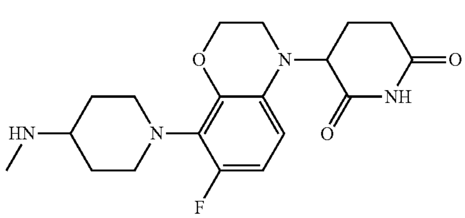 [SMILES: CNC1CCN(c2c(F)ccc3c2OCCN3C2CCC(=O)NC2=O)CC1] |

TABLE 1-continued

Representative Compounds of the Present Invention

| Compound | Structure |
|---|---|
| 18-10 | 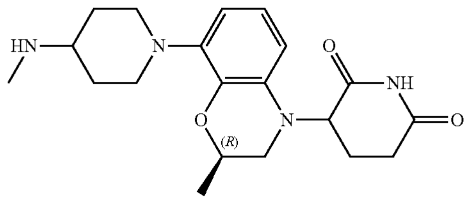 |
| 18-13 | 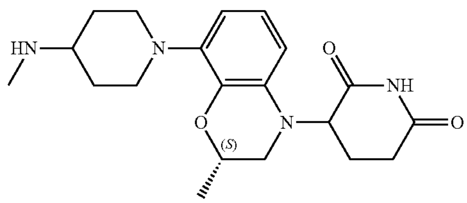 |
| 19-9 | 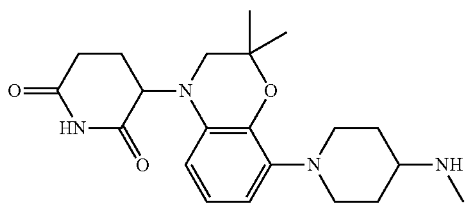 [SMILES: CNC1CCN(c2cccc3c2OC(C)(C)CN3C2CCC(=O)NC2=O)CC1] |
| 20-7 | 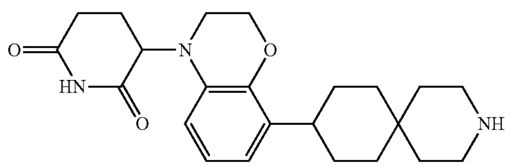 [SMILES: O=C1CCC(N2CCOc3c(C4CCC5(CCNCC5)CC4)cccc32)C(=O)N1] |
| 21-1 | 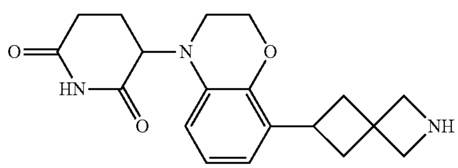 |
| 22-6 | 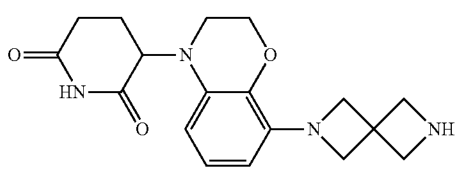 [SMILES: O=C1CCC(N2CCOc3c(C4CC5(CNC5)C4)cccc32)C(=O)N1] |
| 23-10 | 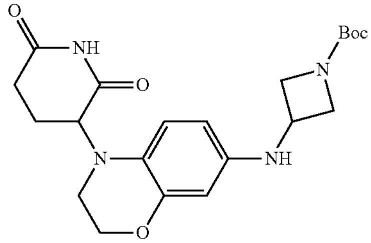 [SMILES: CC(C)(C)OC(=O)N1CC(Nc2ccc3c(c2)OCCN3C2CCC(=O)NC2=O)C1] |

TABLE 1-continued

Representative Compounds of the Present Invention

| Compound | Structure |
|---|---|
| 24-3 | (structure) |
| 24-4 | (structure) |
| 24-5 | (structure) |
| 24-6 | (structure) |
| 25-5 | (structure) |
| 25-6 | (structure) |

TABLE 1-continued

Representative Compounds of the Present Invention

| Compound | Structure |
|---|---|
| 26-6 | 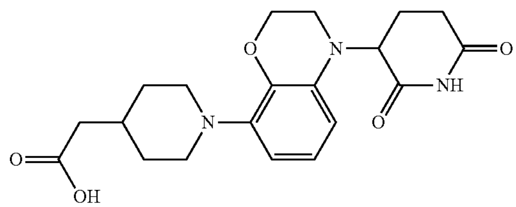 [SMILES: O=C(O)CC1CCN(c2cccc3c2OCCN3C2CCC(=O)NC2=O)CC1] |
| 27-8 | 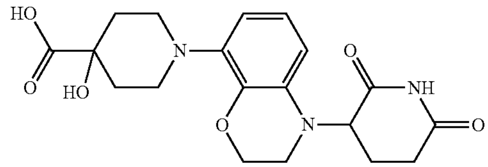 [SMILES: O=C1CCC(N2CCOc3c(N4CCC(O)(C(=O)O)CC4)cccc32)C(=O)N1] |
| 28-2 | 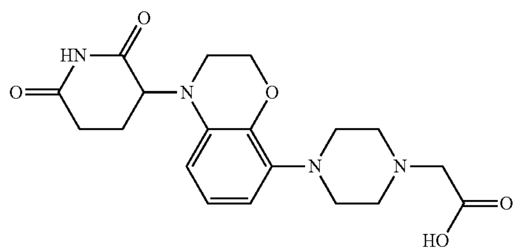 [SMILES: O=C(O)CN1CCN(c2cccc3c2OCCN3C2CCC(=O)NC2=O)CC1] |
| 29-5 | 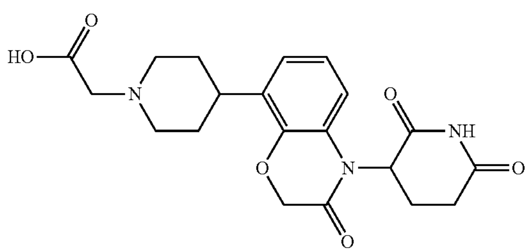 [SMILES: O=C(O)CN1CCC(c2cccc3c2OCC(=O)N3C2CCC(=O)NC2=O)CC1] |
| 30-10 | 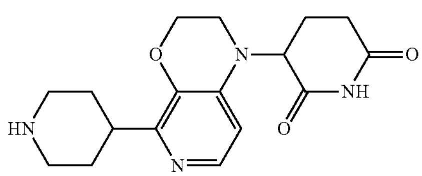 [SMILES: O=C1CCC(N2CCOc3c2ccnc3C2CCNCC2)C(=O)N1] |
| 30-11 | 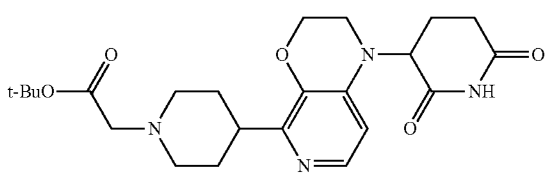 [SMILES: CC(C)(C)OC(=O)CN1CCC(c2nccc3c2OCCN3C2CCC(=O)NC2=O)CC1] |
| 31-10 | 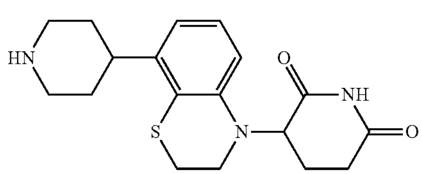 [SMILES: O=C1CCC(N2CCSc3c(C4CCNCC4)cccc32)C(=O)N1] |

TABLE 1-continued

Representative Compounds of the Present Invention

| Compound | Structure |
|---|---|
| 31-12 | 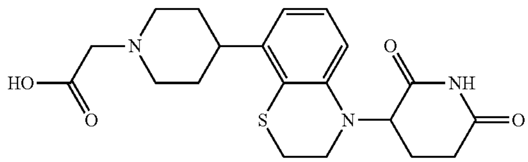 [SMILES: O=C(O)CN1CCC(c2cccc3c2SCCN3C2CCC(=O)NC2=O)CC1] |
| 32-14 | 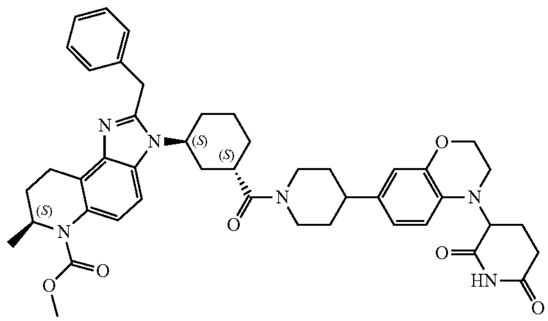 |
| 33-5 | 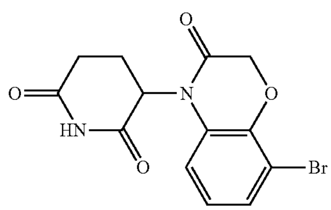 [SMILES: O=C1CCC(N2C(=O)COc3c(Br)cccc32)C(=O)N1] |
| 34-8 | 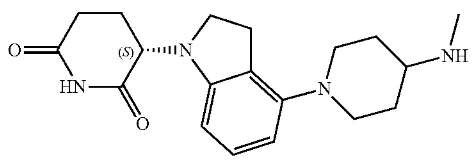 |
| 34-9 | 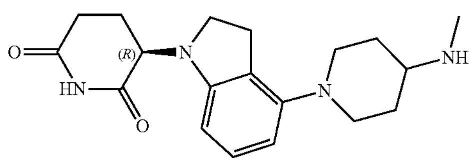 |
| 34-10 | 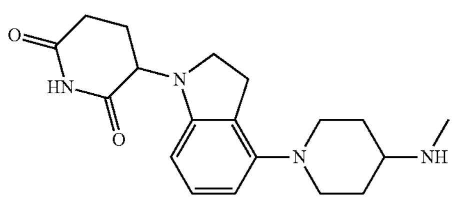 [SMILES: CNC1CCN(c2cccc3c2CCN3C2CCC(=O)NC2=O)CC1] |
| 35-5 | 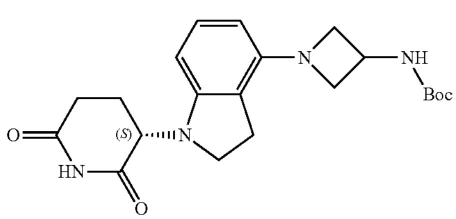 |

TABLE 1-continued

Representative Compounds of the Present Invention

| Compound | Structure |
|---|---|
| 35-6 | 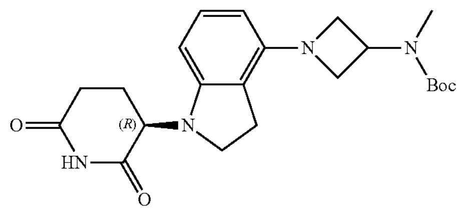 |
| 36-9 | 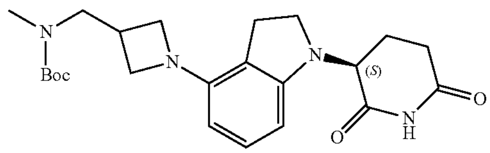 |
| 36-10 | 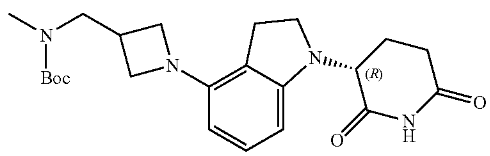 |
| 37-4 | 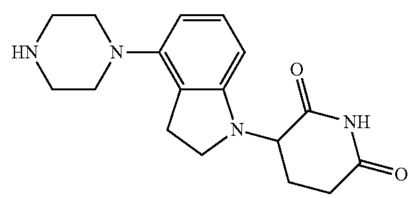 [SMILES: O=C1CCC(N2CCc3c(N4CCNCC4)cccc32)C(=O)N1] |
| 57-2 | 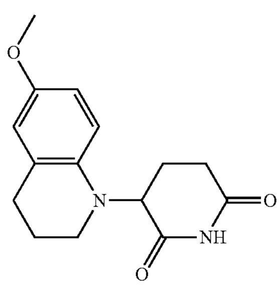 [SMILES: COc1ccc2c(c1)CCCN2C1CCC(=O)NC1=O] |
| 58-1 | 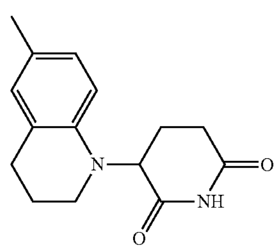 [SMILES: Cc1ccc2c(c1)CCCN2C1CCC(=O)NC1=O] |
| 59-5 | 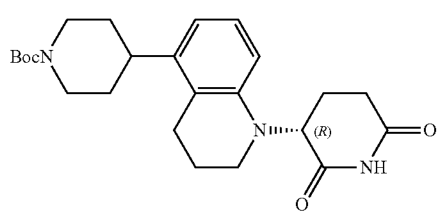 |

TABLE 1-continued

Representative Compounds of the Present Invention

| Compound | Structure |
|---|---|
| 59-6 | 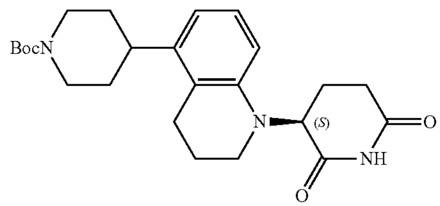 |
| 60-3 | 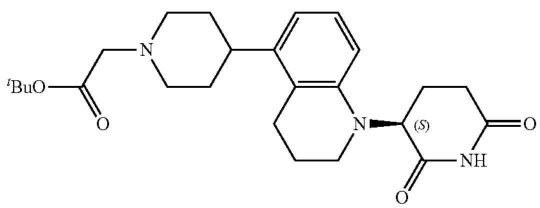 |
| 60-4 | 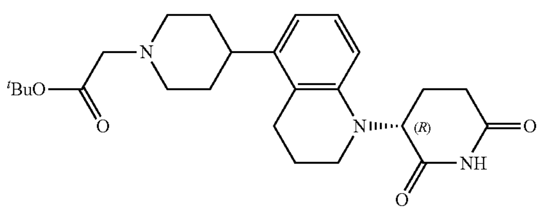 |
| 61-5 | 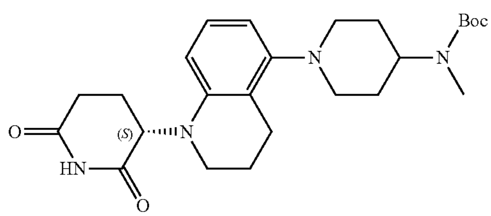 |
| 61-6 | 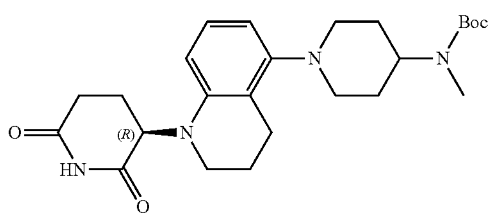 |
| 62-13 | 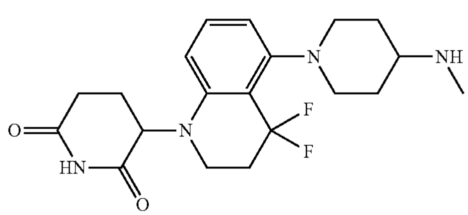 [SMILES: CNC1CCN(c2cccc3c2C(F)(F)CCN3C2CCC(=O)NC2=O)CC1] |
| 63-6 | 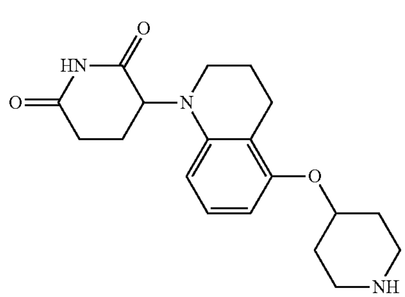 [SMILES: O=C1CCC(N2CCCc3c(OC4CCNCC4)cccc32)C(=O)N1] |

TABLE 1-continued

Representative Compounds of the Present Invention

| Compound | Structure |
|---|---|
| 63-8 | (S)-configured benzomorpholine-glutarimide with piperidinyloxy-N-Boc-piperidine substituent |
| 63-9 | (R)-configured benzomorpholine-glutarimide with piperidinyloxy-N-Boc-piperidine substituent |

Example 2: Fluorescence Polarization (FP) Assay for Screening Compound Ligand Binders of CRBN-DDB1

Measuring compound ligand binding to CRBN-DDB 1 was carried out using an established sensitive and quantitative in vitro fluorescence polarization (FP) based binding assay. (See, I. J. Enyedy et al, *J. Med. Chem.*, 44: 313-4324 [2001]). Compounds were dispensed from serially diluted DMSO stock into black 384-well compatible fluorescence polarization plates using an Echo acoustic dispenser. Compound binding to CRBN-DDB 1 was measured by displacement of an established CRBN binding ligand conjugated to an Alexa Fluor® dye (probe). A 20 L mixture containing 10nM CRBN-DDB1 and 5 nM probe in 50 mM Hepes, pH 7.4, 200 mM NaCl, 1% DMSO, 0.1% BSA and 0.05% o pluronic acid-127 acid was added to wells containing compound and incubated at room temperature for 60 min. Matching control wells excluding CRBN-DDB 1 were used to correct for background fluorescence. Plates were read on an Envision plate reader with appropriate FP filter sets. The corrected S (perpendicular) and P (parallel) values were used to calculate fluorescence polarization (FP) with the following equation:

$$FP=1000*(S-G*P)/(S+G*P).$$

The fractional amount of bound probe (FB) to CRBN-DDB 1 as a function of compound concentration was fitted according to Wang; FEBS Letters 360, (1995), 111-114 to obtain fits for parameter offsets and binding constant ($K_A$) of competitor compound.

TABLE 2

Benzomorpholine CRBN binders

| Sample | Formula | FP CRBN_DDB1.3 0.05% PA Ka nM | FP CRBN_DDB1.3 0.05% PA, 0.1% BSA Ka nM | FP CRBN_DDB1.7 0.05% PA, 0.1% BSA Ka nM |
|---|---|---|---|---|
| 10-10 | piperazinyl-benzomorpholine-glutarimide structure | | | ** |

TABLE 2-continued

Benzomorpholine CRBN binders

| Sample | Formula | FP CRBN_DDB1.3 0.05% PA Ka nM | FP CRBN_DDB1.3 0.05% PA, 0.1% BSA Ka nM | FP CRBN_DDB1.7 0.05% PA, 0.1% BSA Ka nM |
|---|---|---|---|---|
| 13-11 | | | ** | |
| 13-8 | | | ** | |
| 14-7 | | | ** | |

TABLE 2-continued

| | | Benzomorpholine CRBN binders | | |
|---|---|---|---|---|
| Sample | Formula | FP CRBN_DDB1.3 0.05% PA Ka nM | FP CRBN_DDB1.3 0.05% PA, 0.1% BSA Ka nM | FP CRBN_DDB1.7 0.05% PA, 0.1% BSA Ka nM |
| 14-9 | | | | |
| 16-6 | | | ** | |
| 16-7 | | | *** | |

TABLE 2-continued

| | | FP CRBN_DDB1.3 0.05% PA Ka nM | FP CRBN_DDB1.3 0.05% PA, 0.1% BSA Ka nM | FP CRBN_DDB1.7 0.05% PA, 0.1% BSA Ka nM |
|---|---|---|---|---|
| Sample | Formula | | | |
| 18-10 | | | ** | |
| 18-13 | | | ** | |
| 20-7 | | | ** | |

Benzomorpholine CRBN binders

TABLE 2-continued
| | | Benzomorpholine CRBN binders | | |
|---|---|---|---|---|
| Sample | Formula | FP CRBN_DDB1.3 0.05% PA Ka nM | FP CRBN_DDB1.3 0.05% PA, 0.1% BSA Ka nM | FP CRBN_DDB1.7 0.05% PA, 0.1% BSA Ka nM |
| 23-10 | 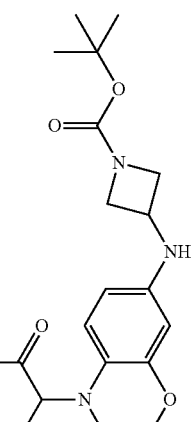 | | | |
| 24-3 | 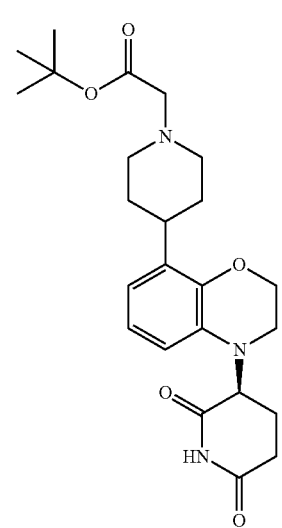 [SMILES: CC(C)(C)OC(=O)CN1CCC(c2cccc3c2OCCN3[C@H]2CCC(=O)NC2=O)CC1] | | ** | |
| 24-4 | 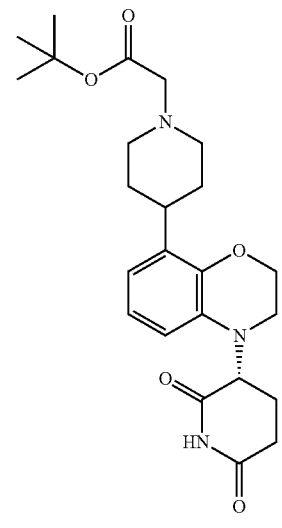 [SMILES: CC(C)(C)OC(=O)CN1CCC(c2cccc3c2OCCN3[C@@H]2CCC(=O)NC2=O)CC1] | | ** | |

TABLE 2-continued
| | | Benzomorpholine CRBN binders | | |
|---|---|---|---|---|
| Sample | Formula | FP CRBN_DDB1.3 0.05% PA Ka nM | FP CRBN_DDB1.3 0.05% PA, 0.1% BSA Ka nM | FP CRBN_DDB1.7 0.05% PA, 0.1% BSA Ka nM |
| 27-8 | 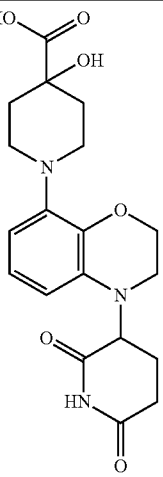 | | ** | |
| 29-5 | 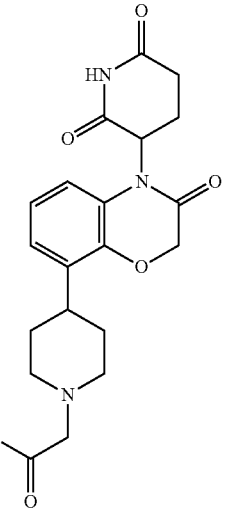 | | ** | |
| 30-11 | 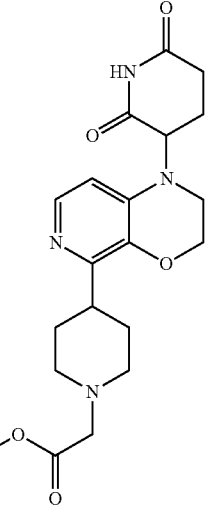 | | | |

TABLE 2-continued

| | Benzomorpholine CRBN binders | | | |
|---|---|---|---|---|
| Sample | Formula | FP CRBN_DDB1.3 0.05% PA Ka nM | FP CRBN_DDB1.3 0.05% PA, 0.1% BSA Ka nM | FP CRBN_DDB1.7 0.05% PA, 0.1% BSA Ka nM |
| 33-5 | | | | ** |
| 5-14 | | | | ** |
| 6-12 | | | | ** |

TABLE 2-continued

| | Benzomorpholine CRBN binders | | | |
|---|---|---|---|---|
| Sample | Formula | FP CRBN_DDB1.3 0.05% PA Ka nM | FP CRBN_DDB1.3 0.05% PA, 0.1% BSA Ka nM | FP CRBN_DDB1.7 0.05% PA, 0.1% BSA Ka nM |
| 8-10 | | | ** | |
| 9-11 | | | ** | |
| 9-6 | | ** | ** | |

TABLE 2-continued
| | | Benzomorpholine CRBN binders | | |
|---|---|---|---|---|
| Sample | Formula | FP CRBN_DDB1.3 0.05% PA Ka nM | FP CRBN_DDB1.3 0.05% PA, 0.1% BSA Ka nM | FP CRBN_DDB1.7 0.05% PA, 0.1% BSA Ka nM |
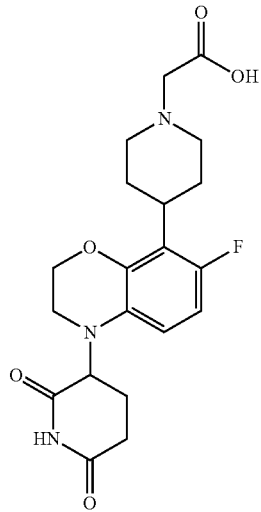 [SMILES: O=C(O)CN1CCC(c2c(F)ccc3c2OCCN3C2CCC(=O)NC2=O)CC1]
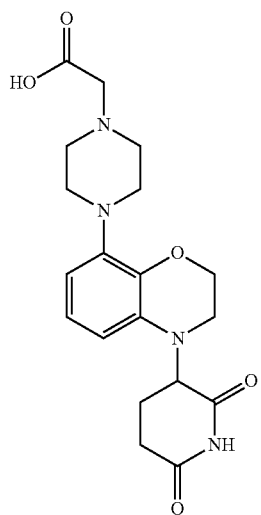 [SMILES: O=C(O)CN1CCN(c2cccc3c2OCCN3C2CCC(=O)NC2=O)CC1]

TABLE 2-continued
Benzomorpholine CRBN binders
| Sample | Formula | FP CRBN_DDB1.3 0.05% PA Ka nM | FP CRBN_DDB1.3 0.05% PA, 0.1% BSA Ka nM | FP CRBN_DDB1.7 0.05% PA, 0.1% BSA Ka nM |
|---|---|---|---|---|
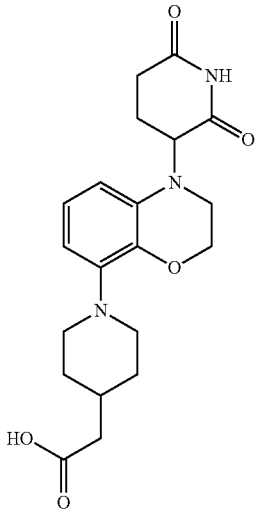 [SMILES: O=C(O)CC1CCN(c2cccc3c2OCCN3C2CCC(=O)NC2=O)CC1]
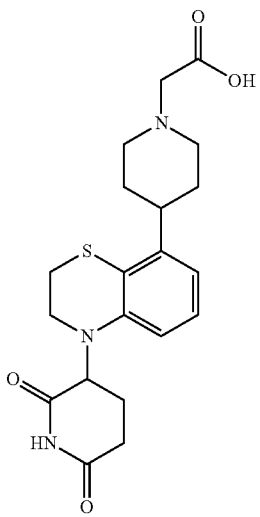 [SMILES: O=C(O)CN1CCC(c2cccc3c2SCCN3C2CCC(=O)NC2=O)CC1]
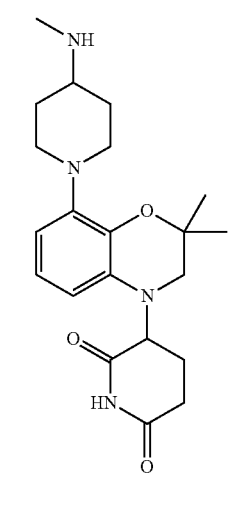 [SMILES: CNC1CCN(c2cccc3c2OC(C)(C)CN3C2CCC(=O)NC2=O)CC1]

TABLE 2-continued
Benzomorpholine CRBN binders
| Sample | Formula | FP CRBN_DDB1.3 0.05% PA Ka nM | FP CRBN_DDB1.3 0.05% PA, 0.1% BSA Ka nM | FP CRBN_DDB1.7 0.05% PA, 0.1% BSA Ka nM |
|---|---|---|---|---|
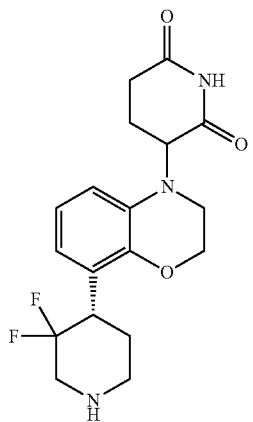 [SMILES: O=C1CCC(N2CCOc3c([C@@H]4CCNCC4(F)F)cccc32)C(=O)N1]
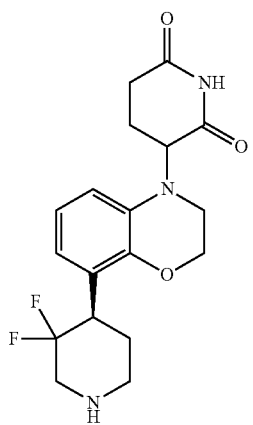 [SMILES: O=C1CCC(N2CCOc3c([C@H]4CCNCC4(F)F)cccc32)C(=O)N1]
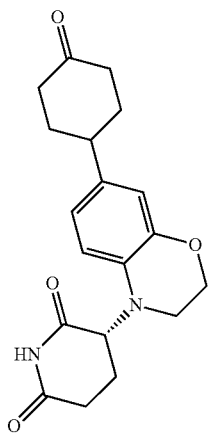 [SMILES: O=C1CCC(c2ccc3c(c2)OCCN3[C@@H]2CCC(=O)NC2=O)CC1]

TABLE 2-continued
Benzomorpholine CRBN binders
| Sample | Formula | FP CRBN_DDB1.3 0.05% PA Ka nM | FP CRBN_DDB1.3 0.05% PA, 0.1% BSA Ka nM | FP CRBN_DDB1.7 0.05% PA, 0.1% BSA Ka nM |
|---|---|---|---|---|
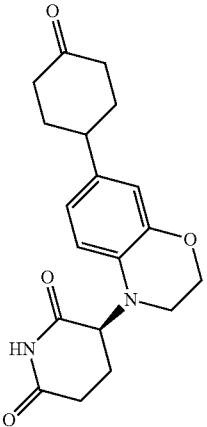 [SMILES: O=C1CCC(c2ccc3c(c2)OCCN3[C@H]2CCC(=O)NC2=O)CC1]
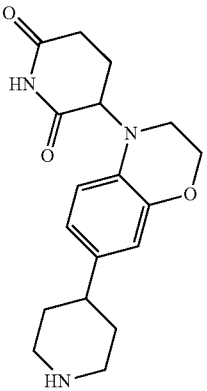 [SMILES: O=C1CCC(N2CCOc3cc(C4CCNCC4)ccc32)C(=O)N1]
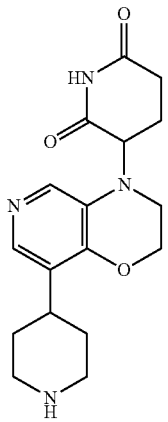 [SMILES: O=C1CCC(N2CCOc3c(C4CCNCC4)cncc32)C(=O)N1]

TABLE 2-continued

| | | Benzomorpholine CRBN binders | | |
|---|---|---|---|---|
| Sample | Formula | FP CRBN_DDB1.3 0.05% PA Ka nM | FP CRBN_DDB1.3 0.05% PA, 0.1% BSA Ka nM | FP CRBN_DDB1.7 0.05% PA, 0.1% BSA Ka nM |

TABLE 2-continued

Benzomorpholine CRBN binders

| Sample | Formula | FP CRBN_DDB1.3 0.05% PA Ka nM | FP CRBN_DDB1.3 0.05% PA, 0.1% BSA Ka nM | FP CRBN_DDB1.7 0.05% PA, 0.1% BSA Ka nM |
|---|---|---|---|---|
| | *(structure shown)* | | | |

In the table above >100 μM is *; ≤100 μM is ; ≤1 μM is * and CRBN_DDB1.3 and CRBN_DDB1.7 differ in the tagged portion of the construct which preceds CRBN-DDB1.

TABLE 3

Indoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 34-5 | *(structure shown)* | ** | ** |

TABLE 3-continued

Indoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 37-4 | 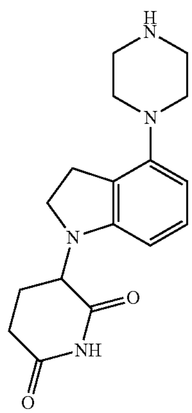 [SMILES: O=C1CCC(N2CCc3c(N4CCNCC4)cccc32)C(=O)N1] | | ** |
| 38-6 | 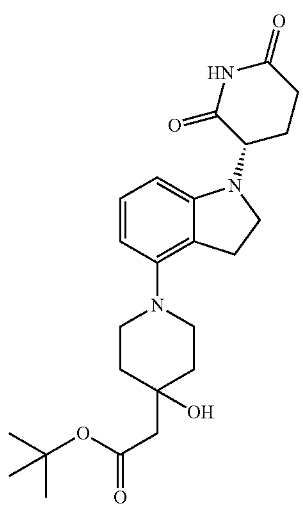 [SMILES: CC(C)(C)OC(=O)CC1(O)CCN(c2cccc3c2CCN3[C@H]2CCC(=O)NC2=O)CC1] | | ** |
| 38-7 | 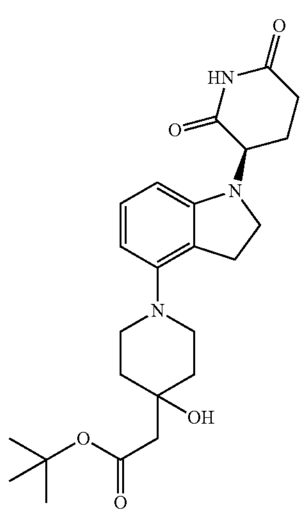 [SMILES: CC(C)(C)OC(=O)CC1(O)CCN(c2cccc3c2CCN3[C@@H]2CCC(=O)NC2=O)CC1] | | *** |

TABLE 3-continued

| | Indoline CRBN binders | | |
|---|---|---|---|
| Compound | Structure | FP CRBN_DDB1.3 0.05% PA, 0.1% BSA ka nM | FP CRBN_DDB1.7 0.05% PA, 0.1% BSA ka nM |
| 39-5 | | | ** |
| 39-6 | | | *** |
| 40-5 | | | *** |

TABLE 3-continued
| | Indoline CRBN binders | | |
|---|---|---|---|
| Compound | Structure | FP CRBN_DDB1.3 0.05% PA, 0.1% BSA ka nM | FP CRBN_DDB1.7 0.05% PA, 0.1% BSA ka nM |
| 40-6 | 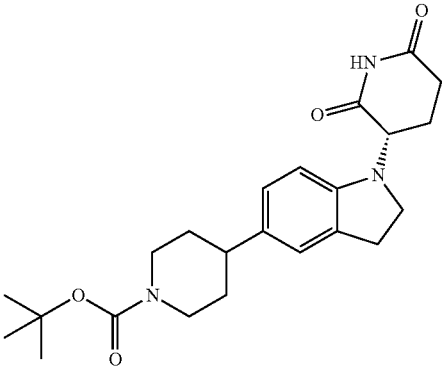 [SMILES: CC(C)(C)OC(=O)N1CCC(c2ccc3c(c2)CCN3[C@H]2CCC(=O)NC2=O)CC1] | | ** |
| 41-4 | 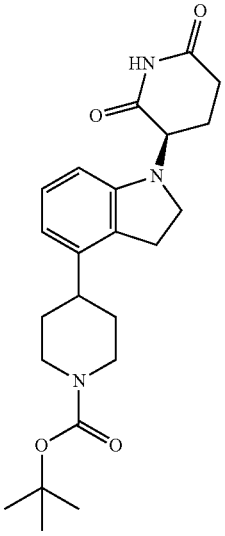 [SMILES: CC(C)(C)OC(=O)N1CCC(c2cccc3c2CCN3[C@@H]2CCC(=O)NC2=O)CC1] | | ** |
| 41-5 | 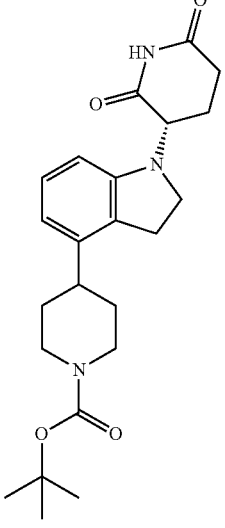 | | *** |

TABLE 3-continued

Indoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 42-4 | 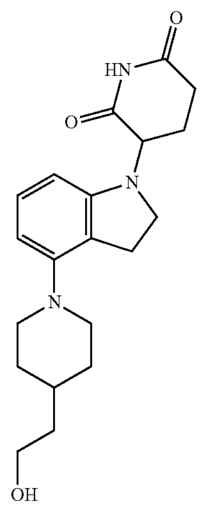 [SMILES: O=C1CCC(N2CCc3c(N4CCC(CCO)CC4)cccc32)C(=O)N1] | | ** |
| 42-5 | 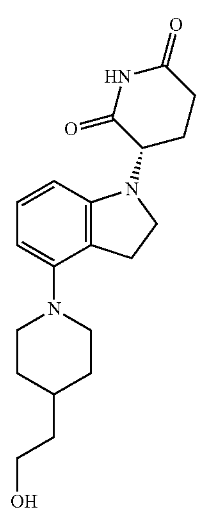 [SMILES: O=C1CC[C@H](N2CCc3c(N4CCC(CCO)CC4)cccc32)C(=O)N1] |  |  |

TABLE 3-continued

Indoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 42-6 | 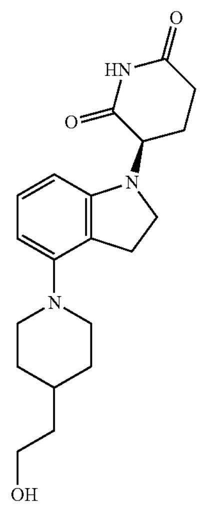 [SMILES: O=C1CC[C@@H](N2CCc3c(N4CCC(CCO)CC4)cccc32)C(=O)N1] | * | * |
| 43-4 | 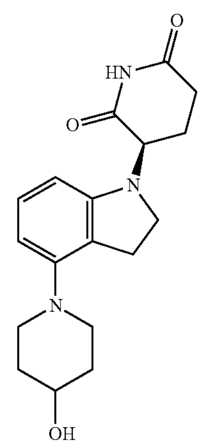 [SMILES: O=C1CC[C@@H](N2CCc3c(N4CCC(O)CC4)cccc32)C(=O)N1] | | *** |
| 43-5 | 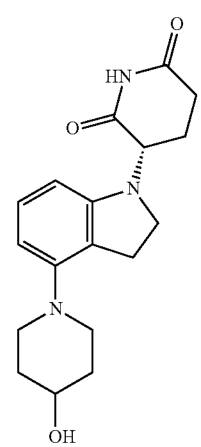 [SMILES: O=C1CC[C@H](N2CCc3c(N4CCC(O)CC4)cccc32)C(=O)N1] | | ** |

TABLE 3-continued

Indoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 44-8 | 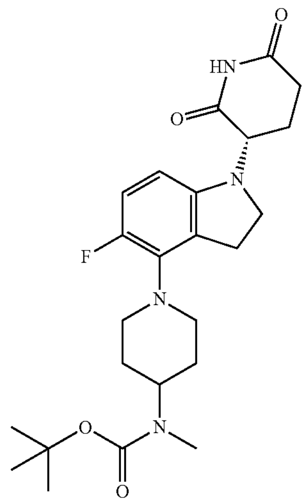 [SMILES: CN(C(=O)OC(C)(C)C)C1CCN(c2c(F)ccc3c2CCN3[C@H]2CCC(=O)NC2=O)CC1] | | ** |
| 44-9 | 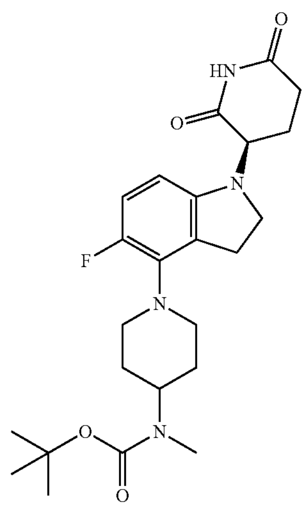 [SMILES: CN(C(=O)OC(C)(C)C)C1CCN(c2c(F)ccc3c2CCN3[C@@H]2CCC(=O)NC2=O)CC1] | | ** |
| 45-3 | 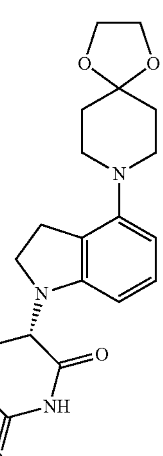 | * |  |

TABLE 3-continued

Indoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 45-4 | 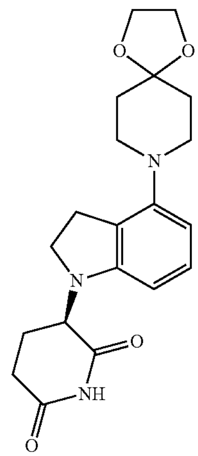 [SMILES: O=C1CC[C@@H](N2CCc3c(N4CCC5(CC4)OCCO5)cccc32)C(=O)N1] |  | * |
| 46-9a | 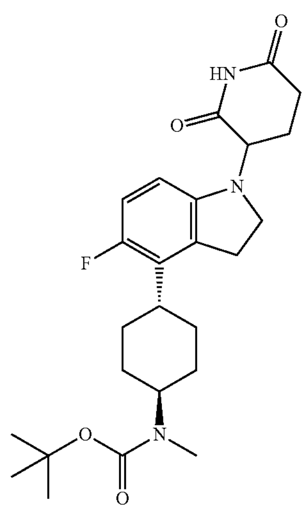 [SMILES: CN(C(=O)OC(C)(C)C)[C@H]1CC[C@H](c2c(F)ccc3c2CCN3C2CCC(=O)NC2=O)CC1] |  |  |
| 46-9b | 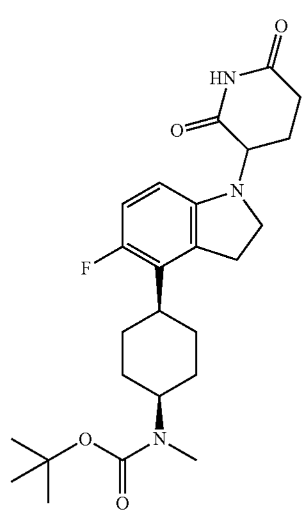 [SMILES: CN(C(=O)OC(C)(C)C)[C@H]1CC[C@@H](c2c(F)ccc3c2CCN3C2CCC(=O)NC2=O)CC1] |  |  |

TABLE 3-continued

Indoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 47-6 | 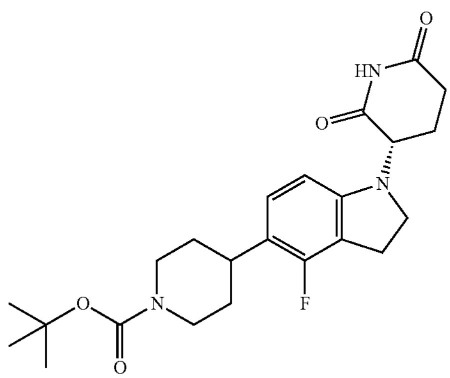 [SMILES: CC(C)(C)OC(=O)N1CCC(c2ccc3c(c2F)CCN3[C@H]2CCC(=O)NC2=O)CC1] |  |  |
| 47-7 | 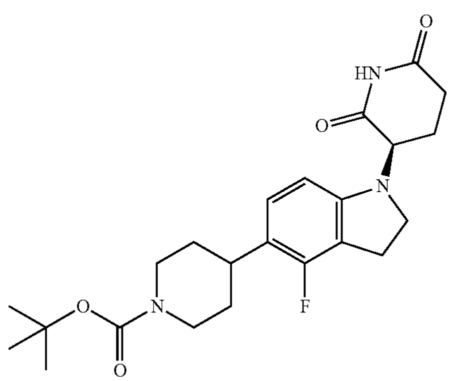 [SMILES: CC(C)(C)OC(=O)N1CCC(c2ccc3c(c2F)CCN3[C@@H]2CCC(=O)NC2=O)CC1] |  |  |
| 48-6 | 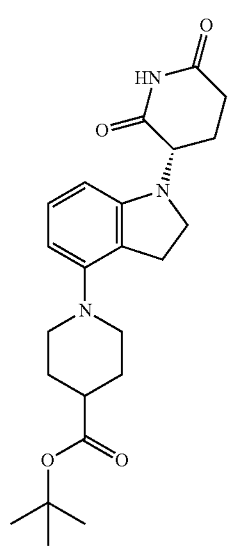 [SMILES: CC(C)(C)OC(=O)C1CCN(c2cccc3c2CCN3[C@H]2CCC(=O)NC2=O)CC1] | ** | |

TABLE 3-continued

Indoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 48-7 | 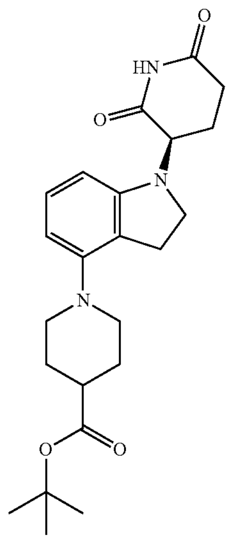 [SMILES: CC(C)(C)OC(=O)C1CCN(c2cccc3c2CCN3[C@@H]2CCC(=O)NC2=O)CC1] | | ** |
| 49-6 | 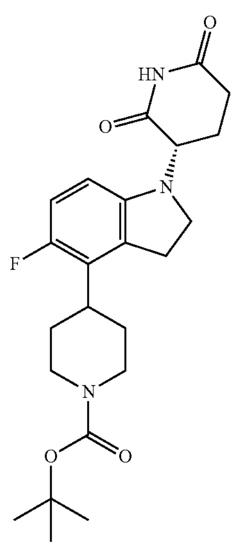 [SMILES: CC(C)(C)OC(=O)N1CCC(c2c(F)ccc3c2CCN3[C@H]2CCC(=O)NC2=O)CC1] |  |  |

TABLE 3-continued

Indoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 49-7 | 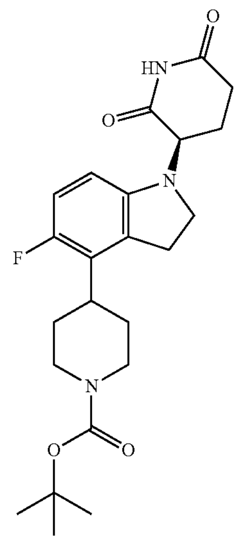 [SMILES: CC(C)(C)OC(=O)N1CCC(c2c(F)ccc3c2CCN3[C@@H]2CCC(=O)NC2=O)CC1] |  |  |
| 50-8 | 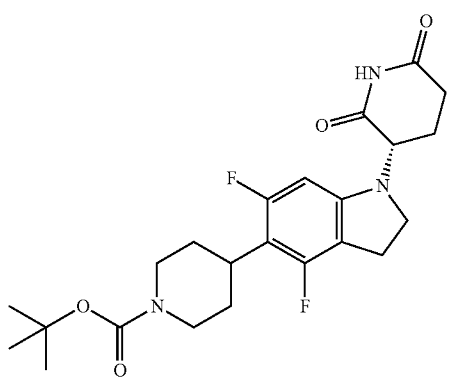 [SMILES: CC(C)(C)OC(=O)N1CCC(c2c(F)cc3c(c2F)CCN3[C@H]2CCC(=O)NC2=O)CC1] |  |  |
| 50-9 | 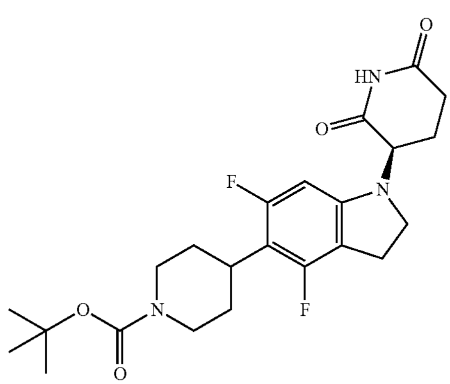 [SMILES: CC(C)(C)OC(=O)N1CCC(c2c(F)cc3c(c2F)CCN3[C@@H]2CCC(=O)NC2=O)CC1] |  |  |

TABLE 3-continued
Indoline CRBN binders
| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 51-12 | 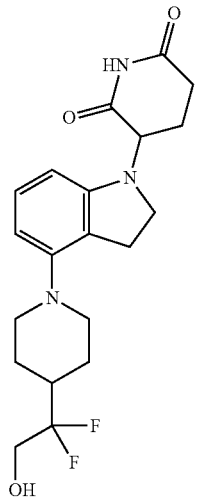 [SMILES: O=C1CCC(N2CCc3c(N4CCC(C(F)(F)CO)CC4)cccc32)C(=O)N1] | ** | |
| 52-6 | 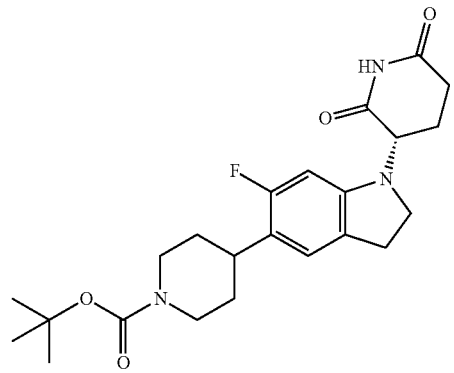 [SMILES: CC(C)(C)OC(=O)N1CCC(c2cc3c(cc2F)N([C@H]2CCC(=O)NC2=O)CC3)CC1] | *** | |
| 52-7 | 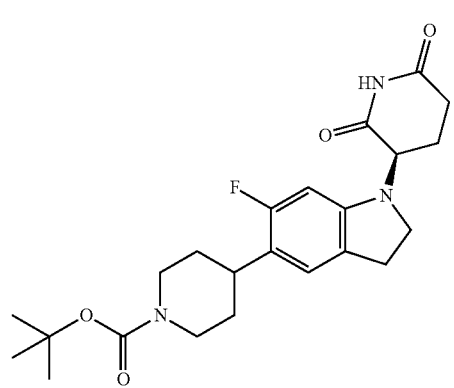 [SMILES: CC(C)(C)OC(=O)N1CCC(c2cc3c(cc2F)N([C@@H]2CCC(=O)NC2=O)CC3)CC1] | ** | |

TABLE 3-continued

Indoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 53-5 | 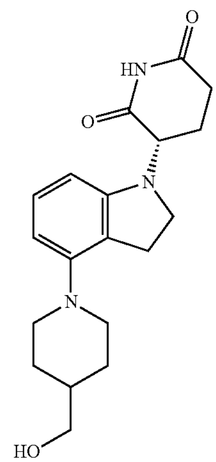 [SMILES: O=C1CC[C@H](N2CCc3c(N4CCC(CO)CC4)cccc32)C(=O)N1] | | *** |
| 53-6 | 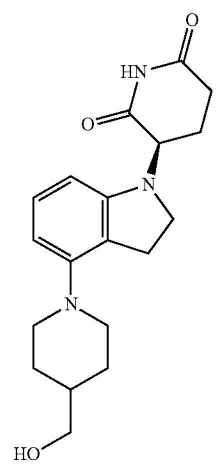 [SMILES: O=C1CC[C@@H](N2CCc3c(N4CCC(CO)CC4)cccc32)C(=O)N1] | | ** |
| 54-5 | 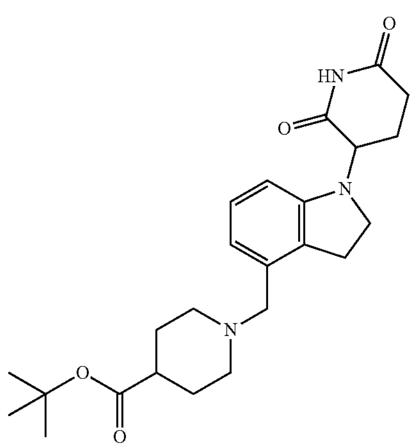 [SMILES: CC(C)(C)OC(=O)C1CCN(Cc2cccc3c2CCN3C2CCC(=O)NC2=O)CC1] | | ** |

TABLE 3-continued

Indoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 54-6 | 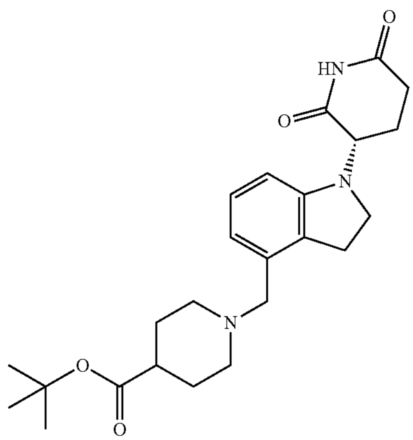 [SMILES: CC(C)(C)OC(=O)C1CCN(Cc2cccc3c2CCN3[C@H]2CCC(=O)NC2=O)CC1] | | ** |
| 54-7 | 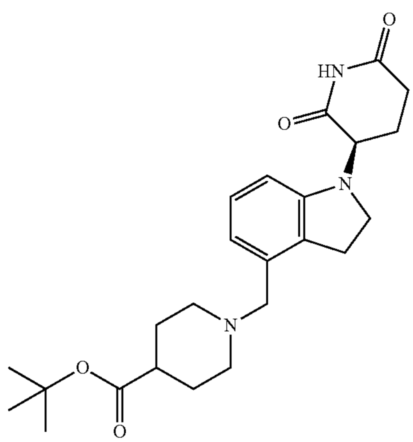 [SMILES: CC(C)(C)OC(=O)C1CCN(Cc2cccc3c2CCN3[C@@H]2CCC(=O)NC2=O)CC1] | | ** |
| 55-4 | 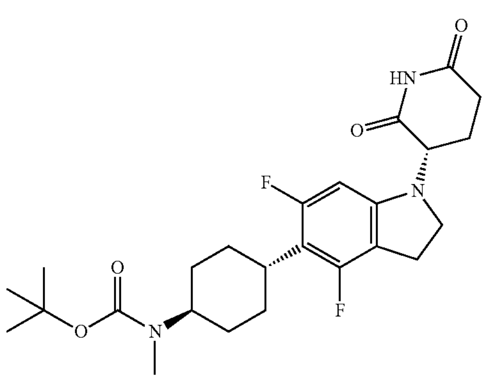 [SMILES: CN(C(=O)OC(C)(C)C)[C@H]1CC[C@H](c2c(F)cc3c(c2F)CCN3[C@H]2CCC(=O)NC2=O)CC1] | | ** |

TABLE 3-continued

Indoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 55-5 | 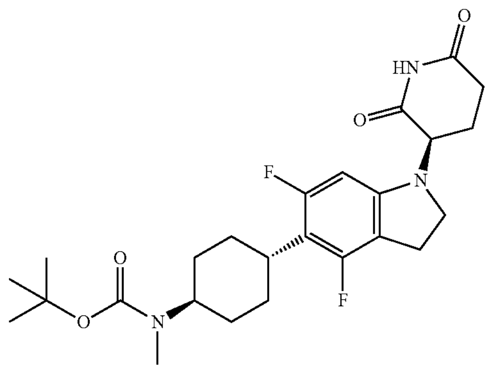 [SMILES: CN(C(=O)OC(C)(C)C)[C@H]1CC[C@H](c2c(F)cc3c(c2F)CCN3[C@@H]2CCC(=O)NC2=O)CC1] | | ** |
| 55-6 | 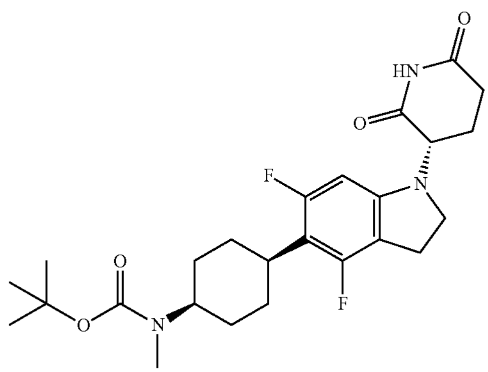 [SMILES: CN(C(=O)OC(C)(C)C)[C@H]1CC[C@@H](c2c(F)cc3c(c2F)CCN3[C@H]2CCC(=O)NC2=O)CC1] | | ** |
| 55-7 | 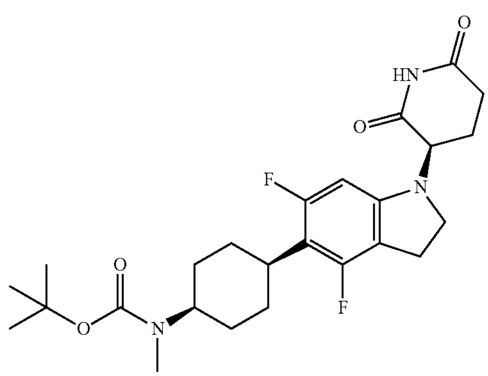 [SMILES: CN(C(=O)OC(C)(C)C)[C@H]1CC[C@@H](c2c(F)cc3c(c2F)CCN3[C@@H]2CCC(=O)NC2=O)CC1] | | ** |
| 56-8a | 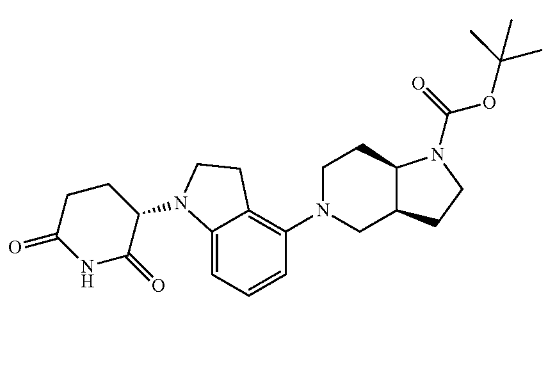 [SMILES: CC(C)(C)OC(=O)N1CC[C@H]2CN(c3cccc4c3CCN4[C@H]3CCC(=O)NC3=O)CC[C@H]21] | | ** |

TABLE 3-continued
| | Indoline CRBN binders | | |
|---|---|---|---|
| Compound | Structure | FP CRBN_DDB1.3 0.05% PA, 0.1% BSA ka nM | FP CRBN_DDB1.7 0.05% PA, 0.1% BSA ka nM |
| 56-8b | 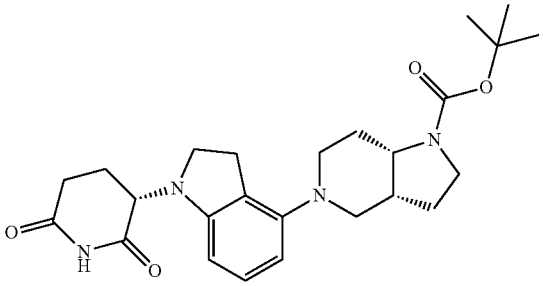 [SMILES: CC(C)(C)OC(=O)N1CC[C@@H]2CN(c3cccc4c3CCN4[C@H]3CCC(=O)NC3=O)CC[C@@H]21] | ** | |
| 56-9a | 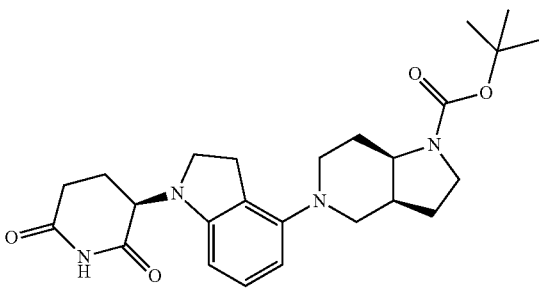 [SMILES: CC(C)(C)OC(=O)N1CC[C@H]2CN(c3cccc4c3CCN4[C@@H]3CCC(=O)NC3=O)CC[C@H]21] | ** | |
| 59-9b | 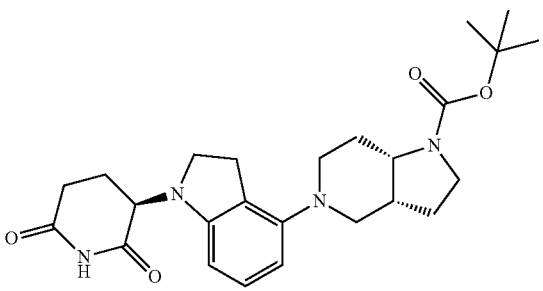 [SMILES: CC(C)(C)OC(=O)N1CC[C@@H]2CN(c3cccc4c3CCN4[C@@H]3CCC(=O)NC3=O)CC[C@@H]21] | *** | |
| | 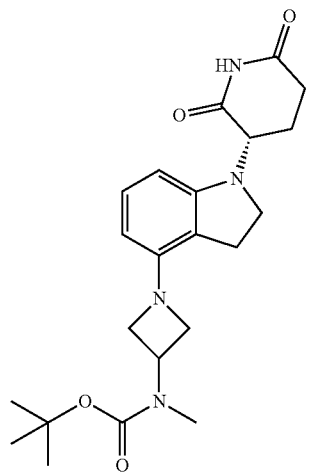 [SMILES: CN(C(=O)OC(C)(C)C)C1CN(c2cccc3c2CCN3[C@H]2CCC(=O)NC2=O)C1] | | |

TABLE 3-continued

Indoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|

TABLE 3-continued
Indoline CRBN binders
| Compound | Structure | FP CRBN_DDB1.3 0.05% PA, 0.1% BSA ka nM | FP CRBN_DDB1.7 0.05% PA, 0.1% BSA ka nM |
|---|---|---|---|
| | 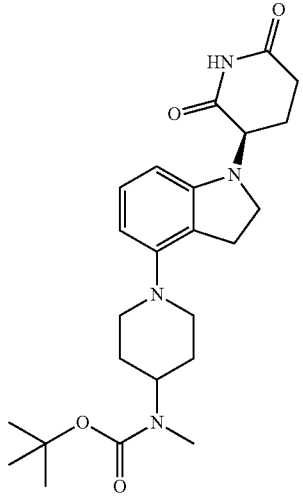 [SMILES: CN(C(=O)OC(C)(C)C)C1CCN(c2cccc3c2CCN3[C@@H]2CCC(=O)NC2=O)CC1] | | |
In the table above >100 µM is *; < = 100 µM is ; < = 1 µM is * and CRBN_DDB1.3 and CRBN_DDB1.7 differ in the tagged portion of the construct which precedes CRBN-DDB1.
TABLE 4
Tetrahydroquinoline CRBN binders
| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 57-2 | 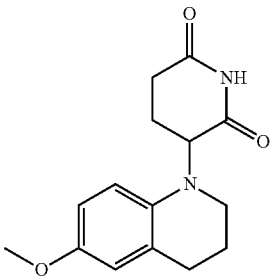 [SMILES: COc1ccc2c(c1)CCCN2C1CCC(=O)NC1=O] | | |
| 58-1 | 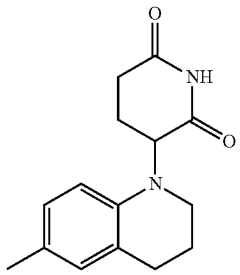 [SMILES: Cc1ccc2c(c1)CCCN2C1CCC(=O)NC1=O] | | |

TABLE 4-continued

Tetrahydroquinoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 60-3 | 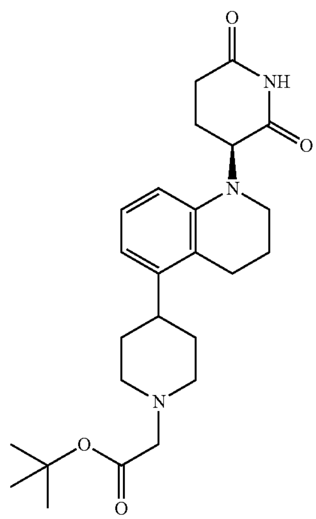 [SMILES: CC(C)(C)OC(=O)CN1CCC(c2cccc3c2CCCN3[C@H]2CCC(=O)NC2=O)CC1] | *** | |
| 60-4 | 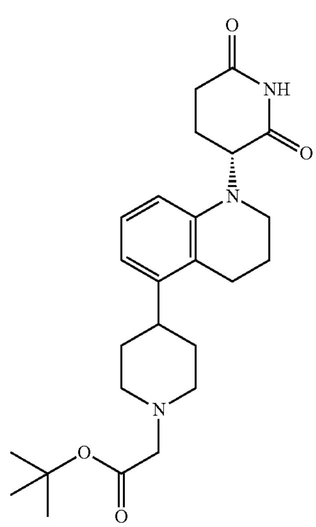 [SMILES: CC(C)(C)OC(=O)CN1CCC(c2cccc3c2CCCN3[C@@H]2CCC(=O)NC2=O)CC1] | ** | |

TABLE 4-continued

Tetrahydroquinoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 61-5 | 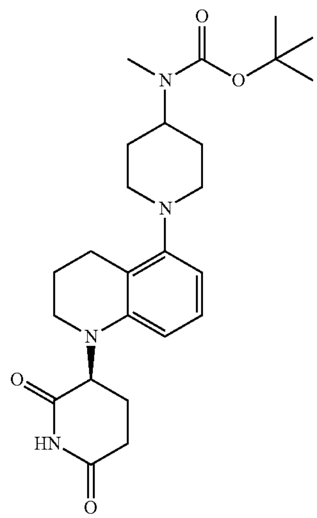 [SMILES: CN(C(=O)OC(C)(C)C)C1CCN(c2cccc3c2CCCN3[C@H]2CCC(=O)NC2=O)CC1] | ** | |
| 61-6 | 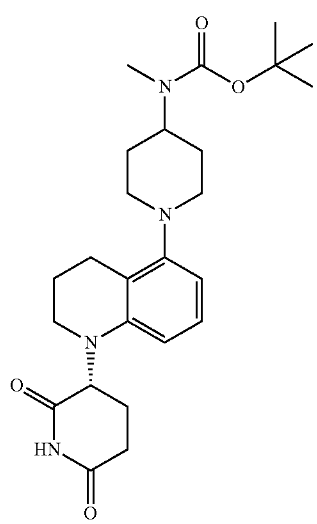 [SMILES: CN(C(=O)OC(C)(C)C)C1CCN(c2cccc3c2CCCN3[C@@H]2CCC(=O)NC2=O)CC1] | *** | |

TABLE 4-continued

Tetrahydroquinoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 59-5 | 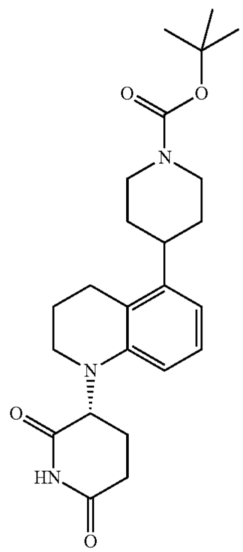 [SMILES: CC(C)(C)OC(=O)N1CCC(c2cccc3c2CCCN3[C@@H]2CCC(=O)NC2=O)CC1] |  |  |
| 59-6 | 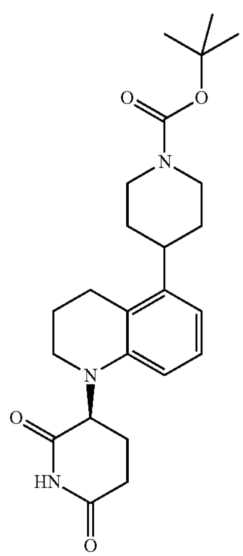 [SMILES: CC(C)(C)OC(=O)N1CCC(c2cccc3c2CCCN3[C@H]2CCC(=O)NC2=O)CC1] |  |  |
| 64-7 | 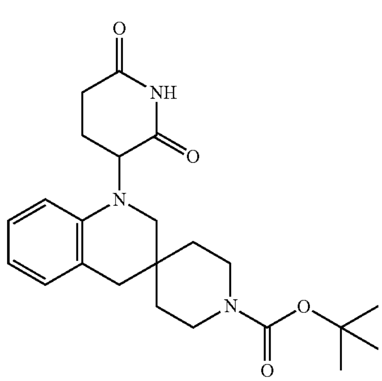 [SMILES: CC(C)(C)OC(=O)N1CCC2(CC1)Cc1ccccc1N(C1CCC(=O)NC1=O)C2] | | ** |

TABLE 4-continued

Tetrahydroquinoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 65-7 | 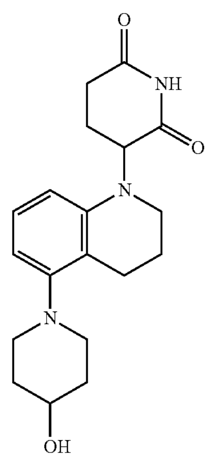 [SMILES: O=C1CCC(N2CCCc3c(N4CCC(O)CC4)cccc32)C(=O)N1] | | ** |
| 66-4 | 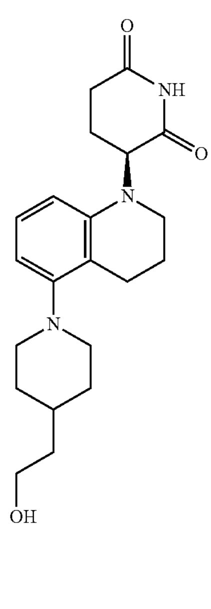 [SMILES: O=C1CC[C@H](N2CCCc3c(N4CCC(CCO)CC4)cccc32)C(=O)N1] | | *** |

TABLE 4-continued

Tetrahydroquinoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 66-5 | 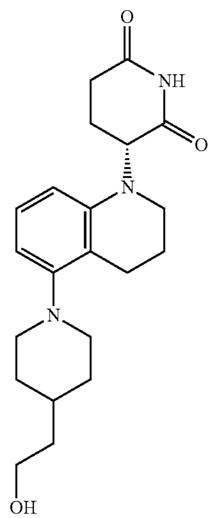 [SMILES: O=C1CC[C@@H](N2CCCc3c(N4CCC(CCO)CC4)cccc32)C(=O)N1] | | ** |
| 67-6 | 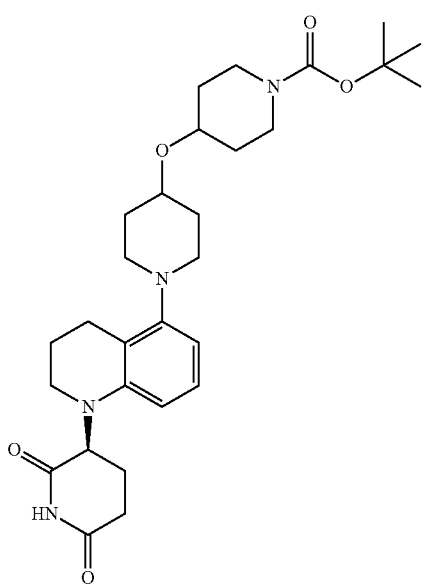 [SMILES: CC(C)(C)OC(=O)N1CCC(OC2CCN(c3cccc4c3CCCN4[C@H]3CCC(=O)NC3=O)CC2)CC1] | | ** |

TABLE 4-continued

Tetrahydroquinoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 67-7 | 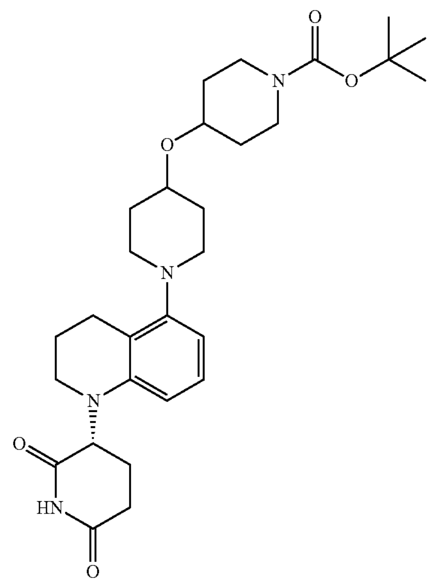 [SMILES: CC(C)(C)OC(=O)N1CCC(OC2CCN(c3cccc4c3CCCN4[C@@H]3CCC(=O)NC3=O)CC2)CC1] | *** | |
| 68-3 | 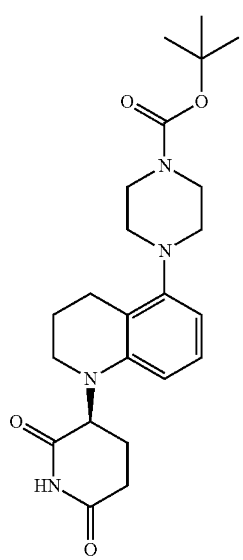 [SMILES: CC(C)(C)OC(=O)N1CCN(c2cccc3c2CCCN3[C@H]2CCC(=O)NC2=O)CC1] | ** | |

TABLE 4-continued

Tetrahydroquinoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 68-4 | 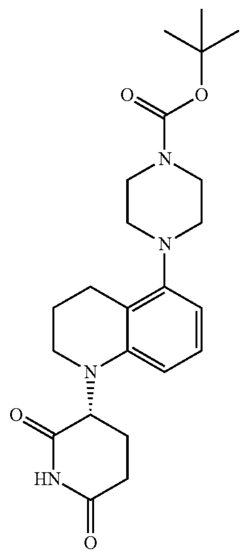 [SMILES: CC(C)(C)OC(=O)N1CCN(c2cccc3c2CCCN3[C@@H]2CCC(=O)NC2=O)CC1] | *** | |
| 63-9 | 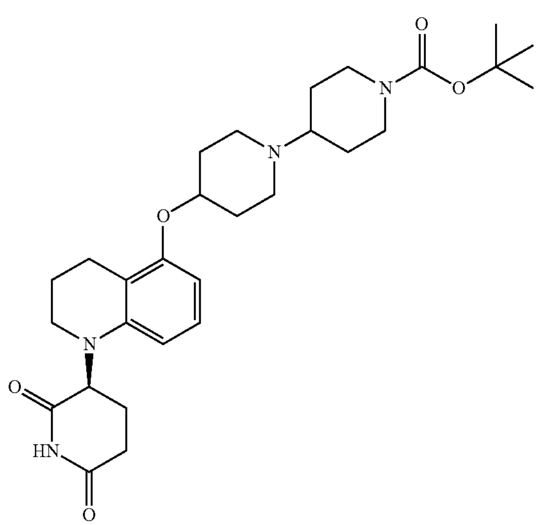 [SMILES: CC(C)(C)OC(=O)N1CCC(N2CCC(Oc3cccc4c3CCCN4[C@H]3CCC(=O)NC3=O)CC2)CC1] | | |

TABLE 4-continued

Tetrahydroquinoline CRBN binders

| Compound | Structure | FP CRBN_DDB1.3 0.05% PA, 0.1% BSA ka nM | FP CRBN_DDB1.7 0.05% PA, 0.1% BSA ka nM |
|---|---|---|---|
| 63-8 | 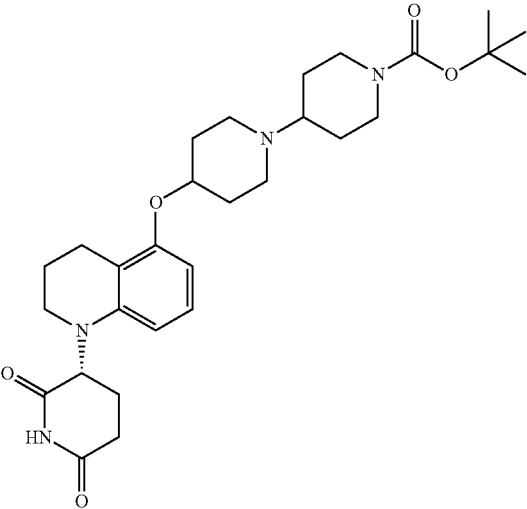 [SMILES: CC(C)(C)OC(=O)N1CCC(N2CCC(Oc3cccc4c3CCCN4[C@@H]3CCC(=O)NC3=O)CC2)CC1] | | |
| | 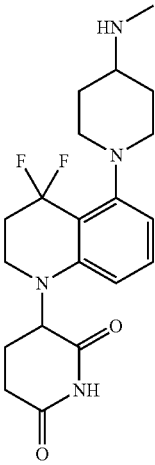 [SMILES: CNC1CCN(c2cccc3c2C(F)(F)CCN3C2CCC(=O)NC2=O)CC1] | | |

In the table above >100 μM is *; < = 100 μM is ; < = 1 μM is * and CRBN_DDB1.3 and CRBN_DDB1.7 differ in the tagged portion of the construct which precedes CRBN-DDB1.

Example 3: BRD4 HiBiT Method

Materials

Dulbecco's modified Eagle medium (DMEM) without phenol red and fetal bovine serum (FBS) were purchased from Gibco (Grand Island, NY, USA). Nano-Glo® HiBiT Lytic Assay System was purchased from Promega (Madison, WI, USA). 293T.92 (BRD4-HiBiT) cell line, endogenously expressing BRD4 with HiBiT fusion tag via CRISPR was made internally from the 293T human cell line acquired from American Type Culture Collection (Rockville, MD, USA). Cell culture flasks and 384-well microplates were acquired from VWR (Radnor, PA, USA) or Corning (Corning, NY, USA).

BRD4 Degradation Analysis

BRD4 degradation was determined based on quantification of luminescent signal using Nano-Glo® HiBiT Lytic Assay kit. Test compounds were added to the 384-well plate from a top concentration of 10 M with 11 points, half log titration in duplicates. 293T.92 cells were added into 384-well plates at a cell density of 15000 cells per well. The plates were kept at 37° C. with 5% $CO_2$ for 2 hours. The cells treated in the absence of the test compound were the negative control and the cells without Nano-Glo® HiBiT Lytic reagent were the positive control. After 24-hour incubation, Nano-Glo® HiBiT Lytic Assay reagents were added to the cells. Luminescence was acquired on EnVision™ Multilabel Reader (PerkinElmer, Santa Clara, CA, USA).

TABLE 5

| | BiDAC compound | | |
|---|---|---|---|
| Compound number | Structure | HiBiT-Degradation 293T.92 BRD4 24.0 hours (DC50) | HiBiT-Degradation 293T.92 BRD4 24.0 hours (Emax %) |
| 32-14 | 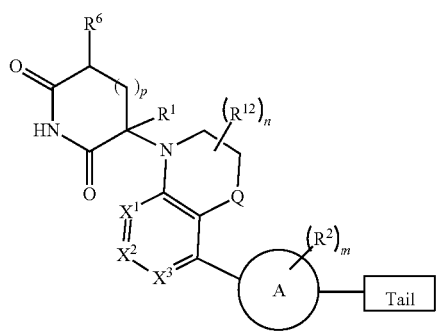 | *** | <30% |

In the table above >10 μM is *; < = 10 μM is ; < = 1 μM is *

All publications and patent applications cited in this specification are herein incorporated by reference as if each individual publication or patent application were specifically and individually indicated to be incorporated by reference.

Although the foregoing invention has been described in some detail by way of illustration and example for the purposes of clarity of understanding, it will be readily apparent to one of ordinary skill in the art in light of the teaching of this invention that certain changes and modification may be made thereto without departing from the spirit or scope of the invention as defined in the claims.

We claim:

1. A compound of Formula:

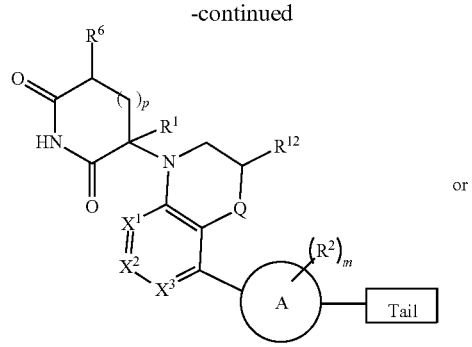

-continued

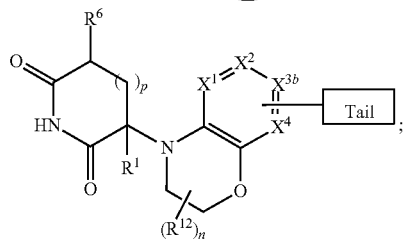

or a pharmaceutically acceptable salt thereof;
wherein:
m is 0, 1, 2, or 3;
n is 0, 1, or 2;
p is 1;
Q is O;

$X^1$, $X^2$, and $X^3$ are independently selected from the group consisting of CH and $CR^5$;

$X^4$ is CH or $CR^5$;

Ⓐ is a cycloalkyl, heterocycle, or heteroaryl;

$R^1$ and $R^6$ are independently selected from the group consisting of hydrogen, alkyl, alkenyl, alkynyl, and halogen;

or $R^1$ and $R^6$ are combined to form a $CH_2$ or $CH_2CH_2$ bridge;

each $R^2$ is independently selected from the group consisting of hydrogen, alkyl, haloalkyl, alkenyl, alkynyl, aryl, heteroaryl, heterocycle, and —$C(O)R^9$, each of which except hydrogen is optionally substituted with 1, 2, 3, or 4 substituents independently selected from the group consisting of $R^{10}$;

each $R^5$ is independently selected from the group consisting of hydrogen, alkyl, haloalkyl, alkenyl, alkynyl, halogen, aryl, heteroaryl, heterocycle, cyano, nitro, —$NR^7R^8$, —$OR^7$, —$SR^7$, —$C(O)R^9$, —$C(S)R^9$, —$S(O)R^9$, —$S(O)_2R^9$, —$OC(O)R^9$, —$OC(S)R^9$, —$OS(O)R^9$, —$OS(O)_2R^9$, —$SC(O)R^9$, —$OS(O)_2R^9$, —$NR^7C(O)R^9$, —$NR^7C(S)R^9$, —$NR^7S(O)R^9$, —$NR^7S(O)_2R^9$, —$P(O)(R^9)_2$, —$SP(O)(R^9)_2$, —$NR^7P(O)(R^9)_2$, and —$OP(O)(R^9)_2$; each of which except hydrogen, halogen, cyano, and nitro is optionally substituted with 1, 2, 3, or 4 substituents independently selected from the group consisting of $R^{10}$;

$R^7$ and $R^8$ at each instance are independently selected from the group consisting of hydrogen, alkyl, haloalkyl, alkenyl, alkynyl, aryl, heteroaryl, heterocycle, and $C(O)R^{14}$; each of which except hydrogen is optionally substituted with 1, 2, 3, or 4 substituents independently selected from the group consisting of $R^{16}$;

each $R^9$ is independently selected from the group consisting of hydrogen, alkyl, haloalkyl, alkenyl, alkynyl, aryl, heteroaryl, heterocycle, —$NR^7R^8$, —$OR^7$, and —$SR^7$; each of which except hydrogen is optionally substituted with 1, 2, 3, or 4 substituents independently selected from the group consisting of $R^{10}$;

each $R^{10}$ is independently selected from the group consisting of hydrogen, alkyl, haloalkyl, alkenyl, alkynyl, halogen, aryl, heteroaryl, heterocycle, cyano, nitro, —$NR^{11}R^{13}$, —$OR^{11}$, —$SR^{11}$, —$C(O)R^{14}$, —$C(S)R^{14}$, —$S(O)R^{14}$, —$S(O)_2R^{14}$, —$OC(O)R^{14}$, —$OC(S)R^{14}$, —$OS(O)R^{14}$, —$OS(O)_2R^{14}$, —$NR^{11}C(O)R^{14}$, —$NR^{11}C(S)R^{14}$, —$NR^{11}S(O)R^{14}$, —$NR^{11}S(O)_2R^{14}$, —$P(O)(R^{14})_2$, —$NR^1P(O)(R^{14})_2$, and —$OP(O)(R^{14})_2$; each of which except hydrogen, halogen, cyano, and nitro is optionally substituted with 1, 2, 3, or 4 substituents independently selected from the group consisting of $R^{15a}$;

$R^{11}$ and $R^{13}$ at each instance are independently selected from the group consisting of hydrogen, alkyl, haloalkyl, alkenyl, alkynyl, aryl, heteroaryl, heterocycle, —$C(O)R^{14}$, —$C(S)R^{14}$, —$S(S(O)_2R^{14}$, and —$P(O)(R^{14})_2$; each of which except hydrogen is optionally substituted with 1, 2, 3, or 4 substituents independently selected from the group consisting of $R^{15b}$;

each $R^{12}$ is independently selected from the group consisting of hydrogen, alkyl, haloalkyl, alkenyl, alkynyl, halogen, aryl, heteroaryl, heterocycle, cyano, nitro, —$NR^{11}R^{13}$, —$OR^{11}$, and —$SR^{11}$;

each of which except hydrogen, halogen, cyano, and nitro is optionally substituted with 1, 2, 3, or 4 substituents independently selected from the group consisting of $R^{15c}$;

each $R^{14}$ is independently selected from the group consisting of hydrogen, alkyl, haloalkyl, alkenyl, alkynyl, aryl, heteroaryl, heterocycle, amino, hydroxyl, alkoxy, —$N(H)(alkyl)$, and —$N(alkyl)_2$; each of which except hydrogen is optionally substituted with 1, 2, 3, or 4 substituents independently selected from the group consisting of $R^{15d}$;

$R^{15a}$, $R^{15b}$, $R^{15c}$, $R^{15d}$, and $R^{15e}$, at each instance are independently selected from the group consisting of hydrogen, alkyl, haloalkyl, alkenyl, alkynyl, halogen, aryl, heteroaryl, heterocycle, cyano, nitro, amino, hydroxyl, alkoxy, —$N(H)(alkyl)$, and —$N(alkyl)_2$;

each $R^{16}$ is independently selected from the group consisting of hydrogen, alkyl, haloalkyl, alkenyl, alkynyl, halogen, aryl, heteroaryl, heterocycle, cyano, nitro, —$NR^{11}R^{13}$, —$OR^{11}$, —$SR^{11}$, —$C(O)R^{14}$, —$C(S)R^{14}$, —$S(O)R^{14}$, —$S(O)_2R^{14}$, —$OC(O)R^{14}$, —$OC(S)R^{14}$, —$OS(O)R^{14}$, —$OS(O)_2R^{14}$, —$NR^{11}C(O)R^{14}$, —$NR^{11}C(S)R^{14}$, —$NR^{11}S(O)R^{14}$, —$NR^{11}S(O)_2R^{14}$, —$P(O)(R^{14})_2$, —$NR^{11}P(O)(R^{14})_2$, and —$OP(O)(R^{14})_2$; each of which except hydrogen, halogen, cyano, and nitro is optionally substituted with 1, 2, 3, or 4 substituents independently selected from the group consisting of $R^{15e}$;

$X^{3b}$ is CH or $CR^{5b}$;

$R^{5b}$ is selected from the group consisting of hydrogen, alkyl, alkenyl, alkynyl, aryl, heteroaryl, heterocycle, —$C(O)alkyl$, —$C(S)R^9$, —$S(O)R^9$, and —$S(O)_2R^9$; each of which except hydrogen is optionally substituted with 1, 2, 3, or 4 substituents independently selected from the group consisting of $R^{10}$;

Tail is selected from

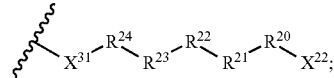

$X^{31}$ is selected from the group consisting of bond, heterocycle, aryl, heteroaryl, bicycle, —$NR^{27}$—, —$CR^{40}R^{41}$—, —O—, —$C(O)$—, —$C(NR^{27})$—, —$C(S)$—, —$S(O)$—, —$S(O)_2$— and —S—; each heterocycle, aryl, heteroaryl, and bicycle is substituted with 1, 2, 3, or 4 substituents independently selected from the group consisting of $R^{40}$;

$X^{22}$ is $R^5$;

$R^{20}$, $R^{21}$, $R^{22}$, $R^{23}$, and $R^{24}$ are independently at each occurrence selected from the group consisting of a bond, alkyl, —$C(O)$—, —$C(O)O$—, —$OC(O)$—, —$SO_2$—, —$S(O)$—, —$C(S)$—, —$C(O)NR^{27}$—, —$NR^{27}C(O)$—, —O—, —S—, —$NR^{27}$—, —$C(R^{40}R^{40})$—, —$P(O)(OR^{26})O$—, —$P(O)(OR^{26})$—, bicycle, alkenyl, alkynyl, haloalkyl, alkoxy, aryl, heterocycle, heteroaryl, lactic acid, glycolic acid, and carbocycle; each of which is optionally substituted with 1, 2, 3, or 4 substituents independently selected from the group consisting of $R^{40}$;

$R^{26}$ is independently at each occurrence selected from the group consisting of hydrogen, alkyl, arylalkyl, heteroarylalkyl, alkenyl, alkynyl, aryl, heteroaryl, and heterocycle;

$R^{27}$ is independently at each occurrence selected from the group consisting of hydrogen, alkyl, heterocycle, aryl, heteroaryl, —$C(O)(alkyl, aryl, or heteroaryl)$, —$C(O)O(alkyl, aryl, or heteroaryl)$, alkenyl, and alkynyl;

R⁴⁰ is independently at each occurrence selected from the group consisting of hydrogen, $R^{27}$, alkyl, alkenyl, alkynyl, fluoro, bromo, chloro, hydroxyl, alkoxy, azide, amino, cyano, —NH(alkyl), —N(alkyl)$_2$, —NHSO$_2$(alkyl), —N(alkyl)SO$_2$alkyl, —NHSO$_2$(aryl, heteroaryl or heterocycle), —N(alkyl)SO$_2$(aryl, heteroaryl or heterocycle), —NHSO$_2$alkenyl, —N(alkyl)SO$_2$alkenyl, —NHSO$_2$alkynyl, —N(alkyl)SO$_2$alkynyl, haloalkyl, aryl, heteroaryl, and heterocycle; and $R^{41}$ is aryl, heteroaryl, or hydrogen.

2. The compound of claim 1, wherein

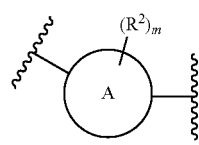

is

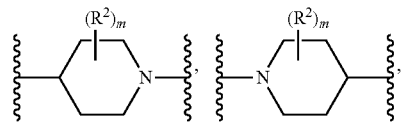

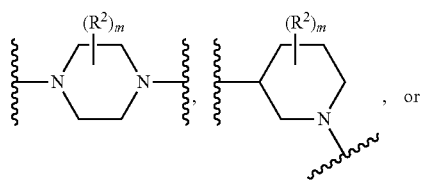

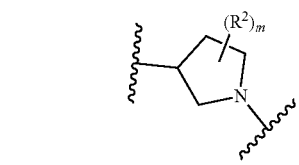

3. The compound of claim 2, wherein m is 0 or 1.

4. The compound of claim 3, wherein $X^{22}$ is heterocycle optionally substituted with 1, 2, 3, or 4 substituents independently selected from the group consisting of $R^{10}$.

5. The compound of claim 3, wherein $X^{22}$ is heteroaryl optionally substituted with 1, 2, 3, or 4 substituents independently selected from the group consisting of $R^{10}$.

6. The compound of claim 3, wherein $X^{22}$ is halogen.

7. The compound of claim 3, wherein $X^{22}$ is amino.

8. The compound of claim 3, wherein $X^{22}$ is hydroxyl.

9. The compound of claim 1, wherein each $R^2$ is alkyl.

10. The compound of claim 1, wherein $R^6$ and $R^1$ together form a CH$_2$ bridge.

11. The compound of claim 1, wherein $R^6$ and $R^1$ are hydrogen.

12. The compound of claim 1, selected from the group consisting of:

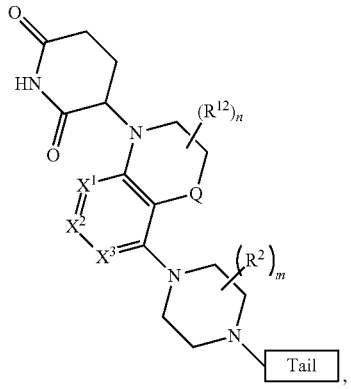

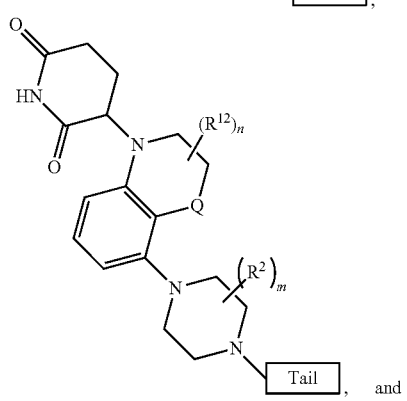

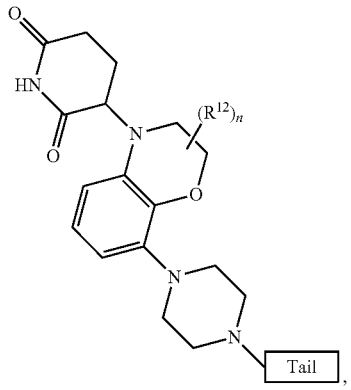

or a pharmaceutically acceptable salt thereof.

13. The compound of claim 1, selected from the group consisting of:

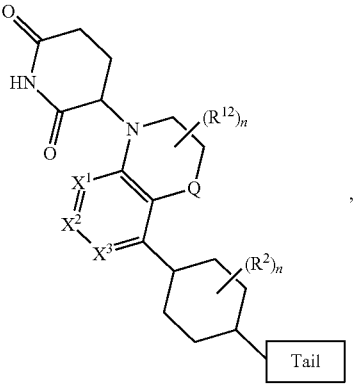

-continued
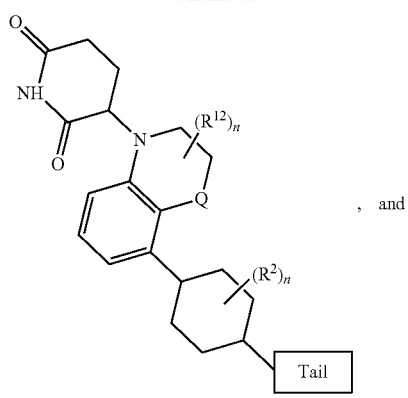
, and
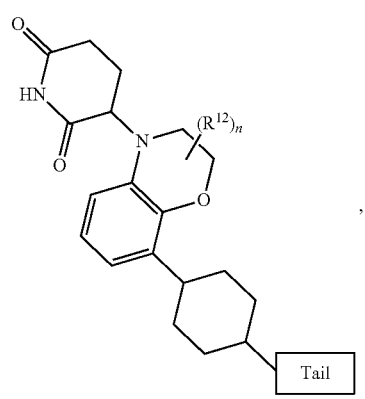
,
or a pharmaceutically acceptable salt thereof.
14. The compound of claim 1, wherein $X^1$ is CH.
15. The compound of claim 1, wherein $X^2$ is CH.
16. The compound of claim 1, wherein $X^3$ is CH.
17. A compound selected from the group consisting of:
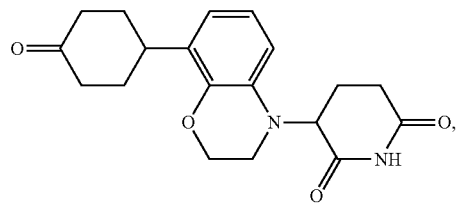
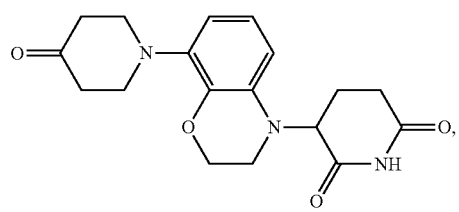
-continued
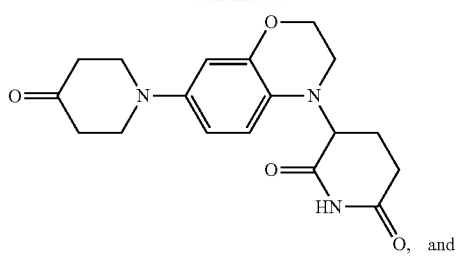
, and
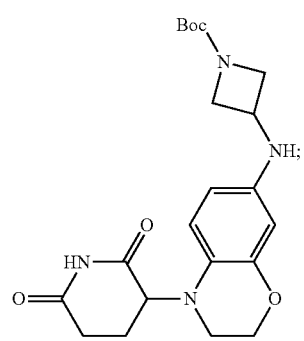
or a pharmaceutically acceptable salt thereof.
18. The compound of claim 1, selected from the group consisting of:
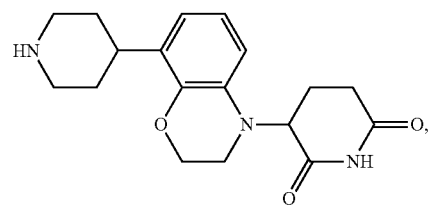
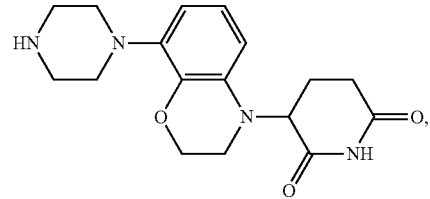
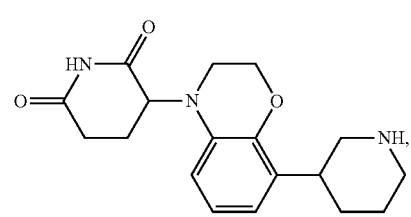

689
-continued
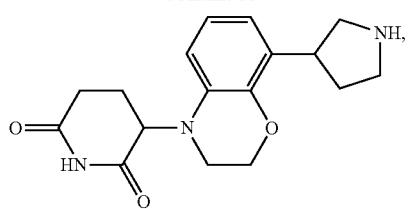
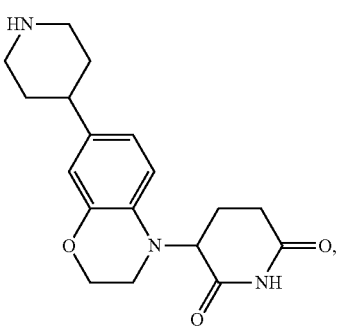
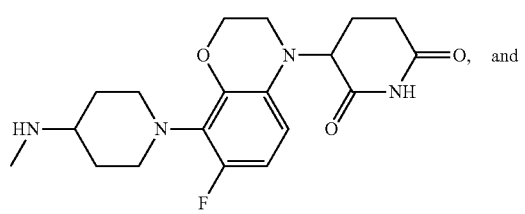
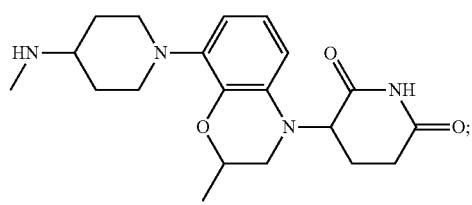
or a pharmaceutically acceptable salt thereof.
19. The compound of claim 1, selected from the group consisting of:
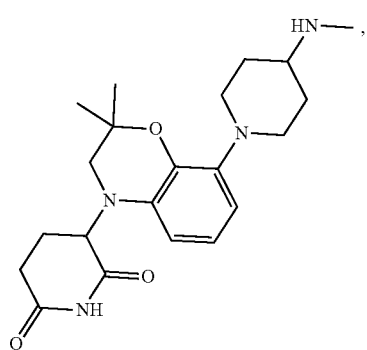
690
-continued
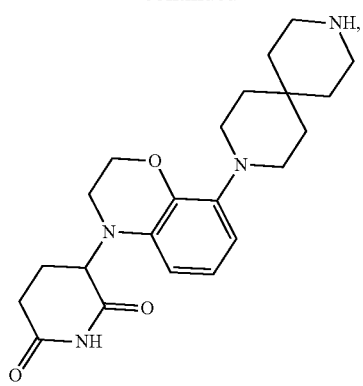
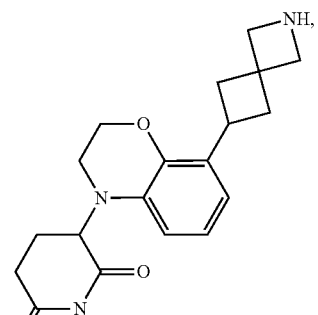
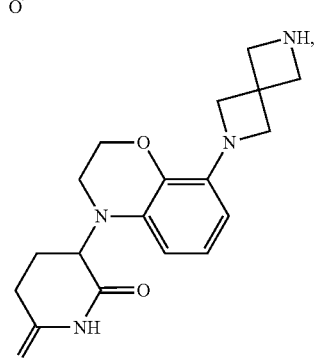
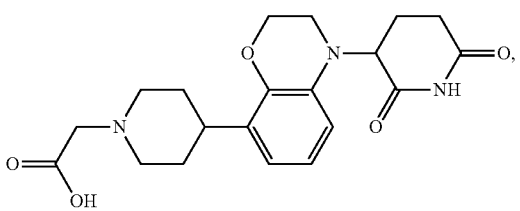
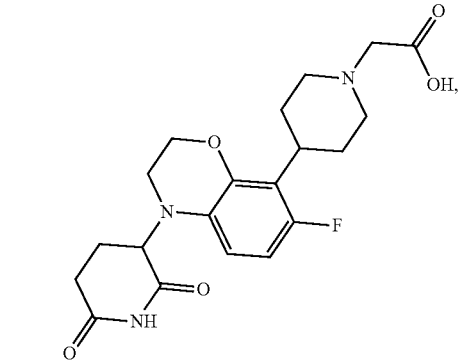

-continued
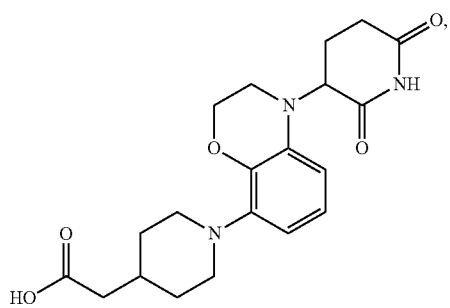
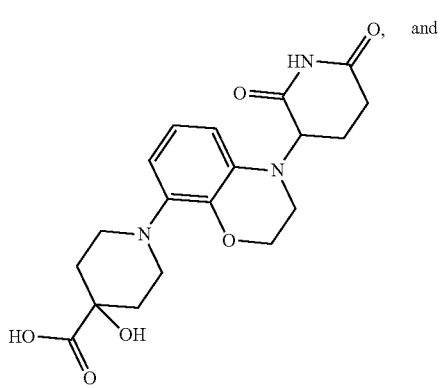
or a pharmaceutically acceptable salt thereof.
20. The compound of claim 1, wherein the compound is:
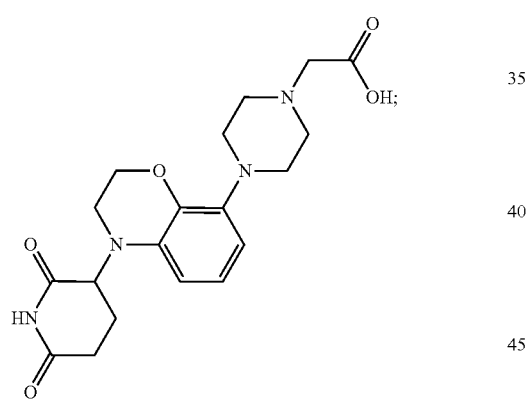
or a pharmaceutically acceptable salt thereof.
21. The compound of claim 1, wherein the compound is:
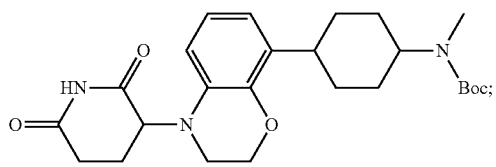
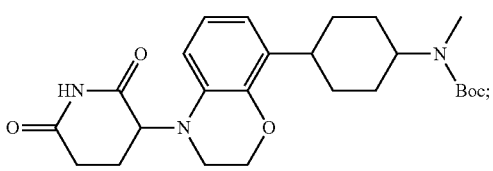
or a pharmaceutically acceptable salt thereof.

22. A pharmaceutical composition comprising a compound of claim 1 or a pharmaceutically acceptable salt thereof and a pharmaceutically acceptable carrier.

23. A method of treating a disorder that is mediated by a Target Protein in a human patient in need thereof comprising administering an effective amount of a compound of claim 1 or a pharmaceutically acceptable salt thereof to the human patient, wherein the Target Protein is degraded or down-regulated by the compound.

24. The method of claim 23, wherein the disorder is an abnormal cellular proliferation.

25. The method of claim 23, wherein the Target Protein is IKZF1.

26. The method of claim 23, wherein the Target Protein is IKZF3.

* * * * *